(12) United States Patent
Storch et al.

(10) Patent No.: US 12,091,719 B2
(45) Date of Patent: *Sep. 17, 2024

(54) COMPOSITIONS AND METHODS FOR DETECTING VIRUSES IN A SAMPLE

(71) Applicant: Washington University, St. Louis, MO (US)

(72) Inventors: Gregory Storch, St. Louis, MO (US); Todd Wylie, St. Louis, MO (US); Kristine Wylie, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/752,205

(22) Filed: Jan. 24, 2020

(65) Prior Publication Data

US 2020/0263263 A1  Aug. 20, 2020

Related U.S. Application Data

(63) Continuation of application No. 15/418,207, filed on Jan. 27, 2017, now Pat. No. 10,597,736.

(60) Provisional application No. 62/289,011, filed on Jan. 29, 2016.

(51) Int. Cl.
  *C12Q 1/70* (2006.01)
(52) U.S. Cl.
  CPC ....... *C12Q 1/701* (2013.01); *C12Q 2600/158* (2013.01)
(58) Field of Classification Search
  None
  See application file for complete search history.

(56) References Cited

U.S. PATENT DOCUMENTS

| | | | |
|---|---|---|---|
| 6,566,495 B1 | 5/2003 | Fodor et al. | |
| 10,597,736 B2* | 3/2020 | Storch | C12Q 1/701 |
| 2001/0053519 A1* | 12/2001 | Fodor | B82Y 30/00 536/24.1 |
| 2005/0244851 A1* | 11/2005 | Blume | C12Q 1/6876 435/6.11 |
| 2006/0210967 A1* | 9/2006 | Agan | C12Q 1/6893 435/5 |
| 2007/0092871 A1* | 4/2007 | Lodes | C12Q 1/705 435/6.12 |
| 2008/0003565 A1* | 1/2008 | Baptista | C12Q 1/70 435/5 |
| 2012/0164644 A1 | 6/2012 | Neely et al. | |
| 2017/0218465 A1 | 8/2017 | Storch et al. | |

OTHER PUBLICATIONS

Wylie et al., "Enhanced virome sequencing using targeted sequence capture", (2015), Genome Res: 1-34. (Year: 2015).*
Lecuit et al., "The human virome: new tools and concepts", (2013) Trends in Microbiol 21(10): pp. 510. (Year: 2013).*
NCBI, "'Roseolovirus' or 'influenza A'", Nucleotide Search (2015). (Year: 2015).*
Ahern, H., The Scientist 9(15) : 20 (Year: 1995).*
Breitbart and Rohwer, TRENDS in Microbiology 13(6) : 278 (Year: 2005).*
Edwards and Rohwer, Nature Reviews Microbiology 3(6) : 504-510 (Year: 2005).*
Virus, Wikipedia Entry (downloaded Jul. 11, 2023) (Year: 2023).*
Albert, T. et al., "Direct selection of human genomic loci by microarray hybridization," Nat. Methods, Nov. 2007, pp. 903-905, vol. 4, No. 11, with Corrigendum, 1 pg.
Allander, T. et al., "A virus discovery method incorporating DNase treatment and its application to the identification of two bovine parvovirus species," PNAS, Sep. 25, 2001, pp. 11609-11614, vol. 98, No. 20.
Altschul, S. et al., "Gapped BLAST and PSI-BLAST: a new generation of protein database search programs," Nucl. Acids Res., 1997, pp. 3389-3402, vol. 25, No. 17, Oxford University Press.
Arumugam, M. et al., "Enterotypes of the human gut microbiome," Europe PMC Funders Group Author Manuscript, Jul. 31, 2013, pp. 1-16, published in final edited form as: Nature, May 12, 2011, pp. 174-180, vol. 473, No. 7346.
Baldwin, D. et al., "Metagenomic Assay for Identification of Microbial Pathogens in Tumor Tissues," mBio., Sep./Oct. 2014, pp. 1-13, vol. 5, No. 5, e01714-14.
Bao, Y. et al., "National Center for Biotechnology Information Viral Genomes Project," J. Virol., Jul. 2004, pp. 7291-7298, vol. 78, No. 14.
Breitbart, M. et al., "Method for discovering novel DNA viruses in blood using viral particle selection and shotgun sequencing," BioTechniques, Nov. 2005, pp. 729-736, vol. 39, No. 5.
Chen, E. et al., "Using a Pan-Viral Microarray Assay (Virochip) to Screen Clinical Samples for Viral Pathogens," J. Vis. Exp., Apr. 2011, pp. 1-4, vol. 50, e2536.
Chiu, C., "Viral pathogen discovery," Curr. Opin. Microbiol., 2013, pp. 468-478, vol. 16, Elsevier.
Cleland, E. et al., "The fungal microbiome in chronic rhinosinusitis: richness, diversity, postoperative changes and patient outcomes," Int. Forum Allergy Rhinol., Apr. 1, 2014, pp. 259-265, vol. 4, No. 4, Wiley-Blackwell.
Colvin, J. et al., "Detection of Viruses in Young Children With Fever Without an Apparent Source," Pediatrics, Dec. 2012, pp. e1455-e1462, vol. 130, No. 6.
De Villiers, E-M. et al., "The Diversity of Torque Teno Viruses: In Vitro Replication Leads to the Formation of Additional Replication-Competent Subviral Molecules," J. Virol., Jul. 2011, pp. 7284-7295, vol. 85, No. 14.
De Vlaminck, I. et al., "Temporal Response of the Human Virome to Immunosuppression and Antiviral Therapy," Cell, Nov. 21, 2013, pp. 1178-1187, vol. 155, Elsevier Inc.
Depledge, D. et al., "Specific Capture and Whole-Genome Sequencing of Viruses from Clinical Samples, " PLoS One, Nov. 2011, pp. 1-7, vol. 6, No. 11, e27805.

(Continued)

*Primary Examiner* — Ethan C Whisenant
(74) *Attorney, Agent, or Firm* — Polsinelli PC

(57) ABSTRACT

The present disclosure provides a composition comprising a panel of probes for detecting one or more viruses in a sample. The panel of probes may be used to detect viruses in a biological sample obtained from a subject.

3 Claims, 14 Drawing Sheets

Specification includes a Sequence Listing.

(56) References Cited

OTHER PUBLICATIONS

Duhaime, M. et al., "Ocean viruses: Rigorously evaluating the metagenomic sample-to-sequence pipeline," Virology, 2012, pp. 181-186, vol. 434, Elsevier.
Duncavage, E. et al., "Hybrid Capture and Next-Generation Sequencing Identify Viral Integration Sites from Formalin-Fixed, Paraffin-Embedded Tissue," J. Mol. Diagn., May 2011, pp. 325-333, vol. 13, No. 3.
Edgar, R., "Search and clustering orders of magnitude faster than BLAST," Bioinformatics, 2010, pp. 2460-2461, vol. 26, No. 19, Oxford University Press.
Edgar, R. et al., "Gene Expression Omnibus: NCBI gene expression and hybridization array data repository," Nucleic Acids Res., 2002, pp. 207-210, vol. 30, No. 1, Oxford University Press.
Findley, K. et al., "Human Skin Fungal Diversity," HHS Public Access Author Manuscript, Dec. 20, 2013, pp. 1-16, published in final edited form as: "Topographic diversity of fungal and bacterial communities in human skin," Nature, Jun. 20, 2013, pp. 367-370, vol. 498, No. 7454.
Gajer, P. et al., "Temporal Dynamics of the Human Vaginal Microbiota," Sci. Transl. Med., May 2, 2012, pp. 1-12, vol. 4, No. 132; 132ra52.
GEO accession No. GPL 15905 entitled "Agilent-024283 Viro5AG-60k," Sep. 1, 2012, 2 pgs.
Hodges, E. et al., "Genome-wide in situ exon capture for selective resequencing," Nat. Genet., Dec. 2007, pp. 1522-1527, vol. 39, No. 12, Nature Publishing Group.
Holtz, L. et al., "Geographic variation in the eukaryotic virome of human diarrhea," Virology, 2014, pp. 556-564, vol. 468-470, Elsevier Inc.
Huttenhower, C. et al., "Structure, function and diversity of the healthy human microbiome," Nature, Jun. 14, 2012, pp. 207-214, vol. 486, Macmillan Publishers Limited.
Kircher, M., et al., "Double indexing overcomes inaccuracies in multiplex sequencing on the Illumina platform," Nucleic Acids Res., 2012, pp. 1-8, vol. 40, No. 1, e3, Oxford University Press.
Koehler, J. et al., "Development and Evaluation of a Panel of Filovirus Sequence Capture Probes for Pathogen Detection by Next-Generation Sequencing," PLoS One, Sep. 2014, pp. 1-9, vol. 9, No. 9, e107007.
Li, H., "A statistical framework for SNP calling, mutation discovery, association mapping and population genetical parameter estimation from sequencing data," Bioinformatics, 2011, pp. 2987-2993, vol. 27, No. 21, Oxford University Press.
Li, H. et al., "Fast and accurate short read alignment with Burrows-Wheeler transform," Bioinformatics, 2009, pp. 1754-1760, vol. 25, No. 14.
Lovett, M. et al., "Direct selection: A method for the isolation of cDNAs encoded by large genomic regions," PNAS, Nov. 1991, pp. 9628-9632, vol. 88.
Lysholm, F. et al., "Characterization of the Viral Microbiome in Patients with Severe Lower Respiratory Tract Infections, Using Metagenomic Sequencing," PLoS One, Feb. 2012, pp. 1-12, vol. 7, No. 2, e30875.
McElvania Tekippe, E. et al., "Increased Prevalence of Anellovirus in Pediatric Patients with Fever," PloS One, Nov. 2012, pp. 1-9, vol. 7, No. 11, e50937.
Minot, S. et al., "The human gut virome: Inter-individual variation and dynamic response to diet," Genome Res., Aug. 31, 2011, pp. 1616-1625, vol. 21, Cold Spring Harbor Laboratory Press.
Ning, Z. et al., "SSAHA: A Fast Search Method for Large DNA Databases," Genome Res., 2011, pp. 1725-1729, vol. 11, Cold Spring Harbor Laboratory Press.
Ninomiya, M., et al., "Analysis of the entire genomes of fifteen torque teno midi virus variants classifiable into a third group of genus Anellovirus," Arch. Virol., Oct. 2007, pp. 1961-1975, vol. 152, No. 11, Springer-Verlag.

Notice of Allowance dated Sep. 30, 2019 from related U.S. Appl. No. 15/418,207; 7 pgs.
Office Action dated Mar. 18, 2019 from related U.S. Appl. No. 15/418,207; 7 pgs.
Oh, J. et al., "Biogeography and individuality shape function in the human skin metagenome," HHS Public Access Author Manuscript, Apr. 1, 2015, pp. 1-34, published in final edited form as: Nature, Oct. 2, 2014, pp. 59-64, vol. 514, No. 7520.
Okou, D. et al., "Microarray-based genomic selection for high-throughput resequencing," Nat. Methods, Nov. 2007, pp. 907-909, vol. 4, No. 11, Nature Publishing Group.
Paulino, L. et al., "Molecular Analysis of Fungal Microbiota in Samples from Healthy Human Skin and Psoriatic Lesions," J. Clin. Microbiol., Aug. 2006, pp. 2933-2941, vol. 44, No. 8.
Peng, Y. et al., "IDBA-UD: a de novo assembler for single-cell and metagenomic sequencing data with highly uneven depth," Bioinformatics, 2012, pp. 1420-1428, vol. 28, No. 11, Oxford University Press.
Pruitt, K. et al., "RefSeq: an update on mammalian reference sequences," Nucleic Acids Res., 2014, pp. D756-D763, vol. 42, Database issue, Oxford University Press.
Quinlan, A. et al., "BEDTools: a flexible suite of utilities for comparing genomic features," Bioinformatics, 2010, pp. 841-842, vol. 26, No. 6, Oxford University Press.
Reyes, A. et al., "Viruses in the faecal microbiota of monozygotic twins and their mothers," Nature, Jul. 15, 2010, pp. 334-338, vol. 466, with Methods, 2 pgs., Macmillan Publishers Limited.
Rockett, J. et al., "DNA arrays: technology, options and toxicological applications," Xenobiotica, 2000, pp. 155-177, vol. 30, No. 2, Taylor & Francis Ltd., Great Britain.
Tatusova, T. et al., "RefSeq microbial genomes database: new representation and annotation strategy," Nucleic Acids Res., 2014, pp. D553-D559, vol. 42, Database issue.
Turnbaugh, P. et al., "A core gut microbiome in obese and lean twins," Nature, Jan. 22, 2009, pp. 480-484, vol. 457, with Methods Summary, 2 pgs., Macmillan Publishers Limited.
Wang, D. et al., "Microarray-based detection and genotyping of viral pathogens," PNAS, Nov. 26, 2002, pp. 15687-15692, vol. 99, No. 24.
Wang, D. et al., "Viral Discovery and Sequence Recovery Using DNA Microarrays," PLOS Biol., 2003, pp. 257-260, vol. 1, No. 2.
Willger, S. et al., "Characterization and quantification of the fungal microbiome in serial samples from individuals with cystic fibrosis," Microbiome, 2014, pp. 1-15, vol. 2, No. 40.
Wylie, K. et al., "Sequence Analysis of the Human Virome in Febrile and Afebrile Children," PloS ONE, Jun. 2012, pp. 1-10, vol. 7, No. 6, e27735.
Wylie, Detection of Viruses in Clinical Samples by Use of Metagenomic Sequencing and Targeted Sequence Capture, Journal of Clinical Microbiology, Dec. 2018, 10 pages, vol. 56, Issue 12.
Wylie, K. et al., "Metagenomic analysis of double-stranded DNA viruses in healthy adults," BMC Biol., 2014, pp. 1-10, vol. 12, No. 71.
Wylie, K. et al., "Genome sequence of enterovirus D68 from St. Louis, Missouri, USA," Emerging Infectious Disease, Jan. 2015, pp. 184-186, vol. 21, No. 1.
Wylie, T. et al., "Enhanced virome sequencing using targeted sequence capture," Genome Res., 2015, pp. 1910-1920, vol. 25, Cold Spring Harbor Laboratory Press.
Young, J. et al., "Viral Metagenomics Reveal Blooms of Anelloviruses in the Respiratory Tract of Lung Transplant Recipients," Am. J. Transplant., 2015, pp. 200-209, vol. 15.
Yu, G. et al., "Discovery of a Novel Polyomavirus in Acute Diarrheal Samples from Children," PLoS One, Nov. 2012, pp. 1-10, vol. 7, No. 11, e49449.

* cited by examiner

RefSeq and Genome Neighbor sequences are associated.

Genome Neighbor 100-mer sequences are generated.

Sequence clustering identifies homologous RefSeq 100-mers

COMPOSITIONS AND METHODS FOR DETECTING VIRUSES IN A SAMPLE

CROSS REFERENCE TO RELATED APPLICATIONS

This application is a continuation of U.S. application Ser. No. 15/418,207, filed Jan. 27, 2017 which claims the benefit of U.S. Provisional Application 62/289,011 filed Jan. 27, 2016, each of which are hereby incorporated by reference in their entirety.

GOVERNMENTAL RIGHTS

This invention was made with government support under R01 AI097213 awarded by the National Institutes of Health. The government has certain rights in the invention.

FIELD OF THE INVENTION

The present disclosure provides a composition comprising a panel of probes for detecting one or more viruses in a sample. The panel of probes may be used to detect viruses in a biological sample obtained from a subject.

BACKGROUND OF THE INVENTION

High-throughput, massively parallel nucleotide sequence analysis has made in-depth studies of the human microbiome feasible. Thus far, most microbiome studies have focused on bacteria, although some include fungi. Viruses are particularly understudied, in part due to the challenges of assessing their presence in clinical samples. Viruses as a group have highly variable genomes, with no gene shared among all viruses that can be surveyed by an amplicon-based sequencing strategy. Therefore, studies of viruses based on nucleotide sequencing require a metagenomic approach. Metagenomic shotgun sequencing (MSS) is a relatively unbiased, culture-independent method in which nucleic acid extracted from a sample is sequenced. Sequence reads are classified based on similarity to reference genomes. This approach allows comprehensive study of the viral component of the microbiome (the virome) and has led to the discovery of novel viruses and the characterization of viruses present in healthy and sick people. When adequate numbers of sequence reads are generated, viruses can be characterized with regard to taxonomy and the presence of genes associated with virulence and resistance to antiviral drugs.

A limitation of MSS as employed to date for virus detection is that the amount and proportion of viral nucleic acid in samples from humans may be very low, and in these cases, few viral sequences are generated. Additionally, it has been shown that viruses known to be present based on molecular assays are undetectable using MSS. These difficulties may reflect the small genome size of some viruses and/or low levels of virus in the sample. This can be a particular problem for studies of the virome of healthy, asymptomatic individuals, in whom virus levels may be low. Thus, there is a need for a method of enriching viral sequences in a metagenomic sample prior to sequencing.

SUMMARY OF THE INVENTION

In an aspect, the disclosure provides a method to detect one or more viruses in a sample. The method comprises: a) contacting a sample with a panel comprising probes capable of specifically hybridizing to greater than 10,000 viral nucleic acid sequences; b) isolating the probes that specifically hybridize to viral nucleic acid sequences within the sample; c) sequencing the viral nucleic acid sequences isolated; and d) comparing the sequences from (c) with a database comprising reference viral nucleic acid sequences to determine the identity of the viral nucleic acid in the sample.

In another aspect, the disclosure provides a kit for detecting viral nucleic acid. The kit comprises probes capable of specifically hybridizing to greater than 10,000 viral nucleic acid sequences.

In still another aspect, the disclosure provides a cohort of viral nucleic acid sequences. The cohort of viral nucleic acid sequences comprises viral nucleic acid sequences from NCBI's RefSeq collection, complementary representation of unique regions from Genome Neighbor targets, selected representation of NCBI Influenza Virus Resource sequences, and the entirety of the probe space represented on the Virochip microarray, GEO accession number GPL15905.

BRIEF DESCRIPTION OF THE FIGURES

The application file contains at least one drawing executed in color. Copies of this patent application publication with color drawing(s) will be provided by the Office upon request and payment of the necessary fee.

(FIG. 3A) The percentage identity of the top high-scoring segment pair (HSP) identified from the BLAST alignment of *anellovirus* contig sequences to the references used to design ViroCap is plotted on the y-axis. The x-axis represents the percentage of the length of the *anellovirus* contig covered after targeted sequence capture. (FIG. 3B) This coverage plot represents the sequence coverage of a divergent *anellovirus* contig sequence. The figure is designed as described in the figure legend for FIG. 2, with the following addition: The post-capture coverage plot is shaded to show regions of nucleotide sequence variation between the *anellovirus* contig and the most similar reference genome in the ViroCap panel. Dark shading represents areas of identical sequence, and each position with nucleotide mismatch between aligned sequences is shown in the lighter color. All of the HSPs are shown, rather than just the top HSP.

(FIG. 4A) Shown are the viral groups, families, and genera included in the ViroCap targeted sequence capture panel. (FIG. 4B) Shown are the viral groups, families and genera included in the samples used in ViroCap validation. Taxonomic assignments for FIG. 4A and FIG. 4B were obtained from the NCBI Taxonomy Viewer (www.ncbi.nlm.nih.gov/genomes/Genomes Group.cgi?opt=virus&taxid=10239).

DETAILED DESCRIPTION OF THE INVENTION

Figure 1:
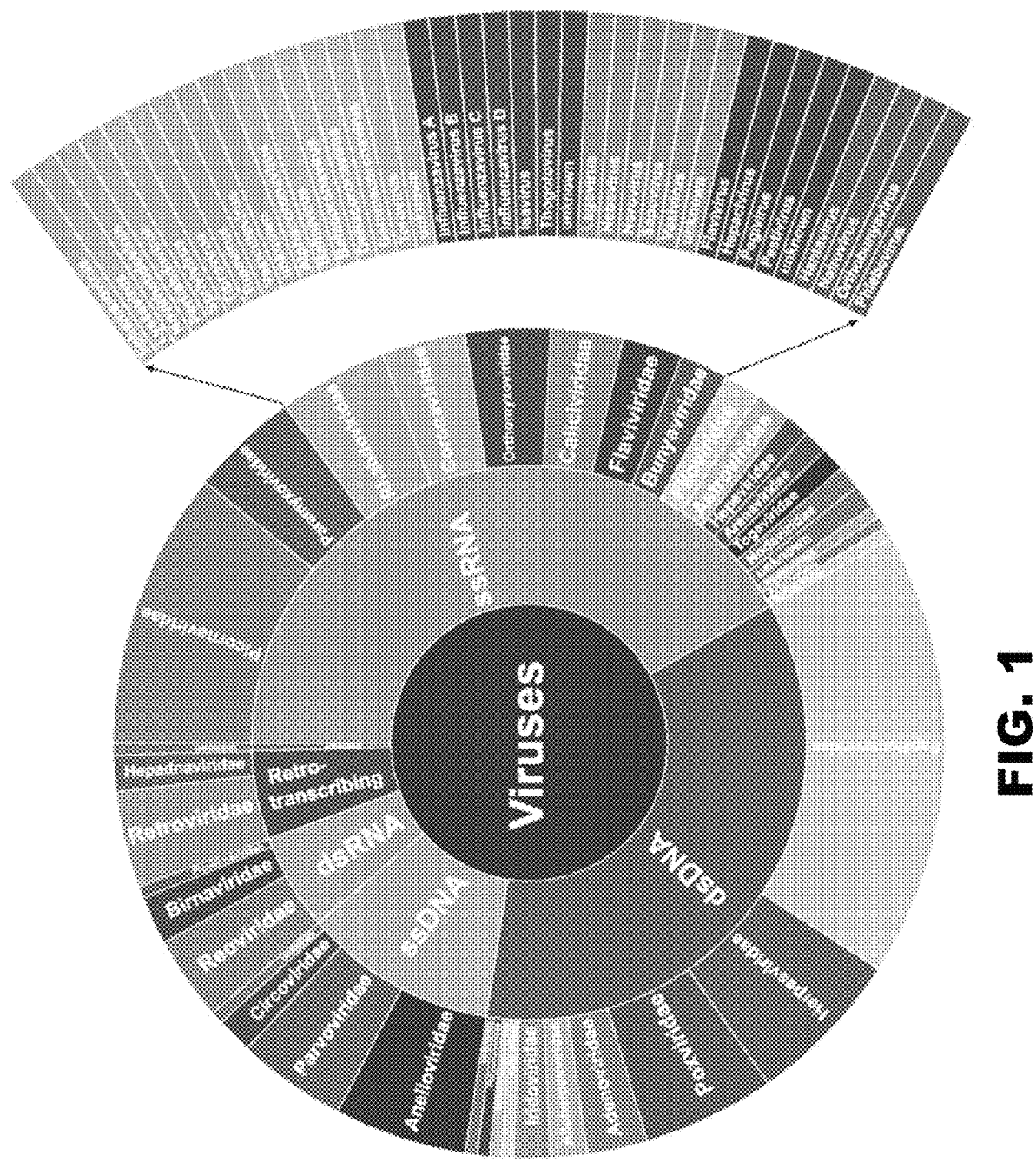
FIG. 1 depicts the taxonomic distribution of target genomes included in ViroCap. Shown are the viral groups and families included in the ViroCap targeted sequence capture panel. A highlighted subset illustrates underlying genera. To view complete genera for all families, see FIG. 4A. Taxonomic assignments were obtained from the NCBI Taxonomy Viewer (www.ncbi.nlm.nih.gov/genomes/Genomes Group.cgi?opt=virus&taxid=10239).
Figure 2A:
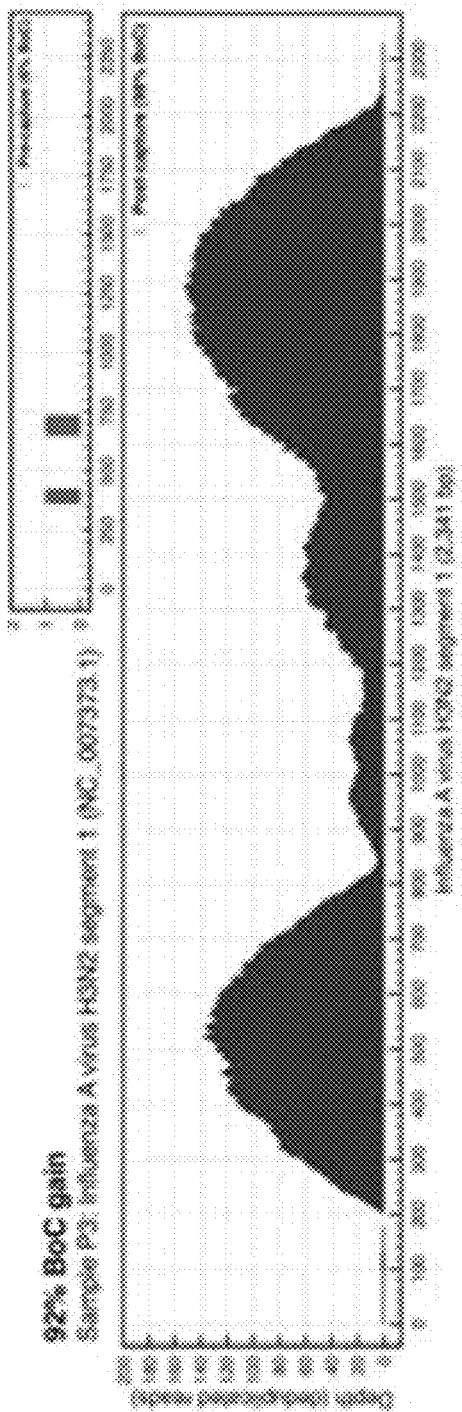
FIG. 2A, FIG. 2B, FIG. 2C, FIG. 2D, FIG. 2E, FIG. 2F, FIG. 2G, and FIG. 2H depict targeted sequence capture enrichment. Examples are given showing the impact of targeted sequence capture on breadth and depth of genome coverage for eight representative viral genomes. For illustrative purposes, all of the coverage panels in this figure have been normalized by removing (deduplicating) reads based on identical alignment start-sites. Nucleotide positions along the reference genome are shown on the x-axis. The depth of deduplicated reads is shown on the y-axis. The shaded portion indicates the sequence coverage (breadth and depth) for each virus. Post-capture sequence coverage is represented in the larger panels in blue; precapture sequence coverage is shown in the insets in red. Note that y-axis ranges are different for each panel. At the top of each panel is shown the breadth of coverage (BoC) for the sample. The header of each panel includes breadth of coverage gain (BoC gain), sample id, and reference genome name and NCBI version number. BoC gain is calculated by subtracting the percentage of the length of the reference genome that was covered by sequence reads in precapture MSS from the percentage of the length of the reference genome covered by post-capture sequence reads.
Figure 2B:
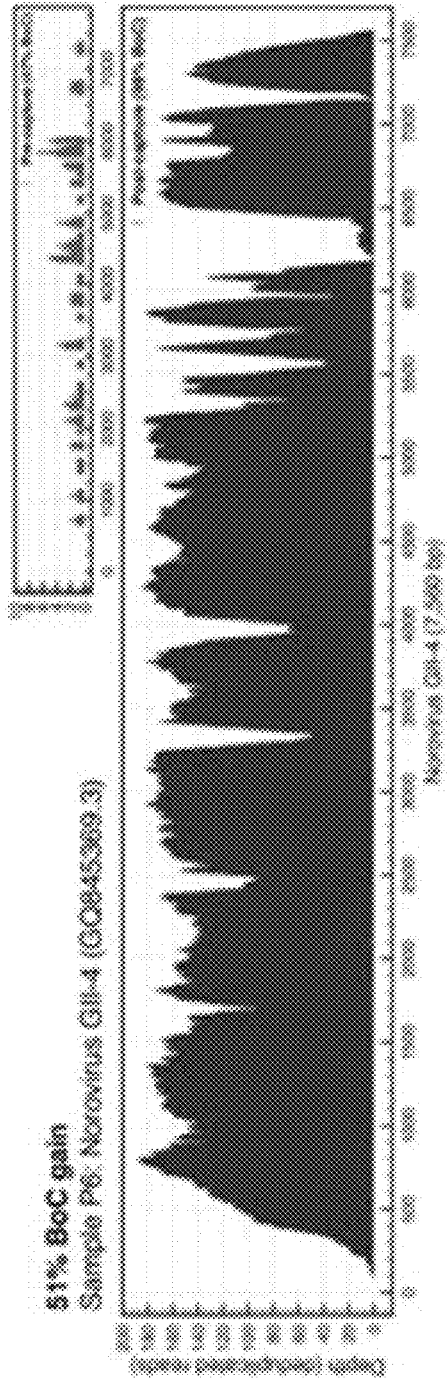
Figure 2C:
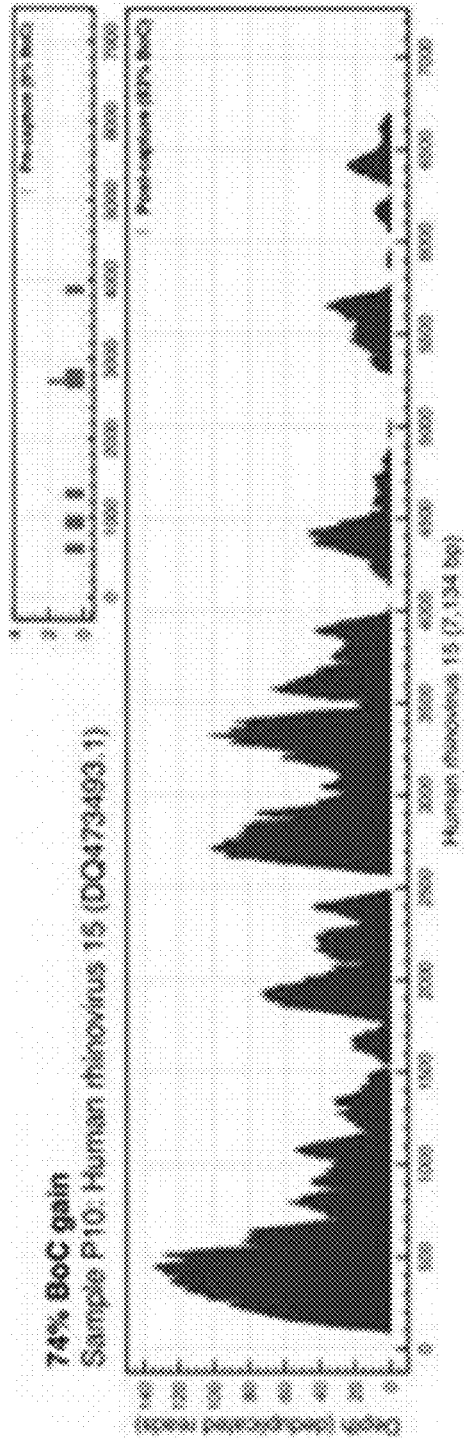
Figure 2D:
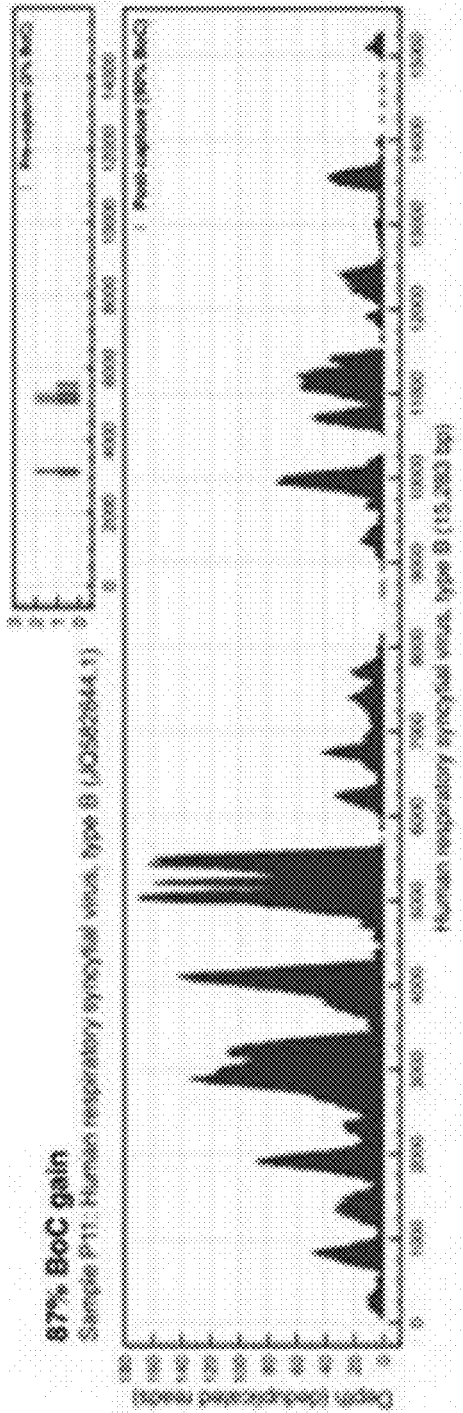
Figure 2E:
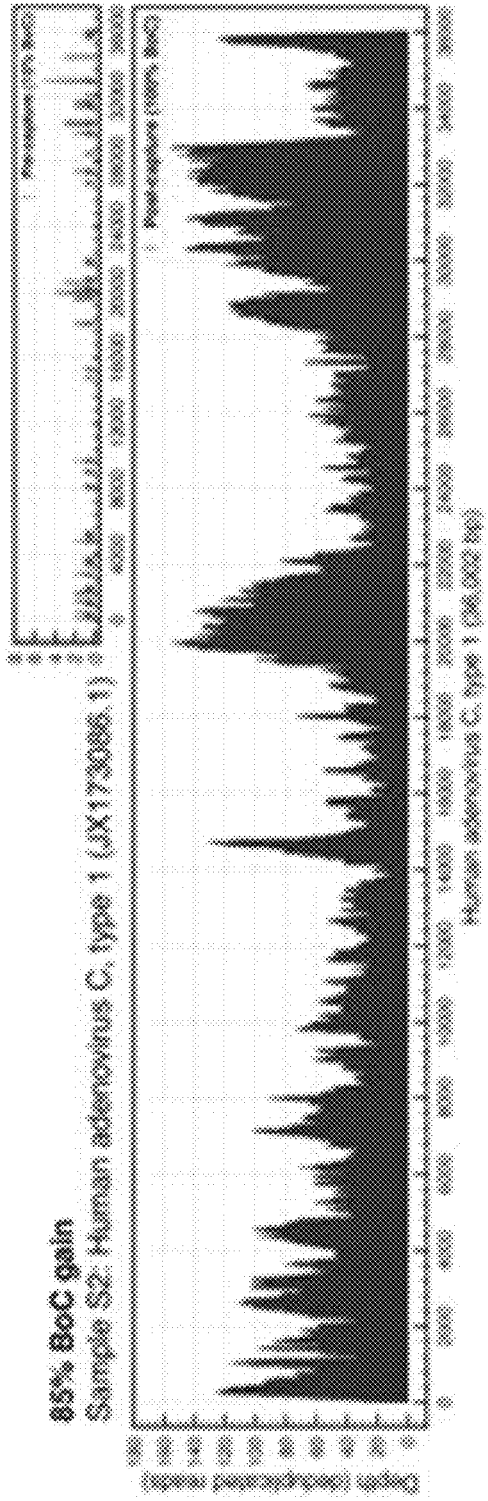
Figure 2F:
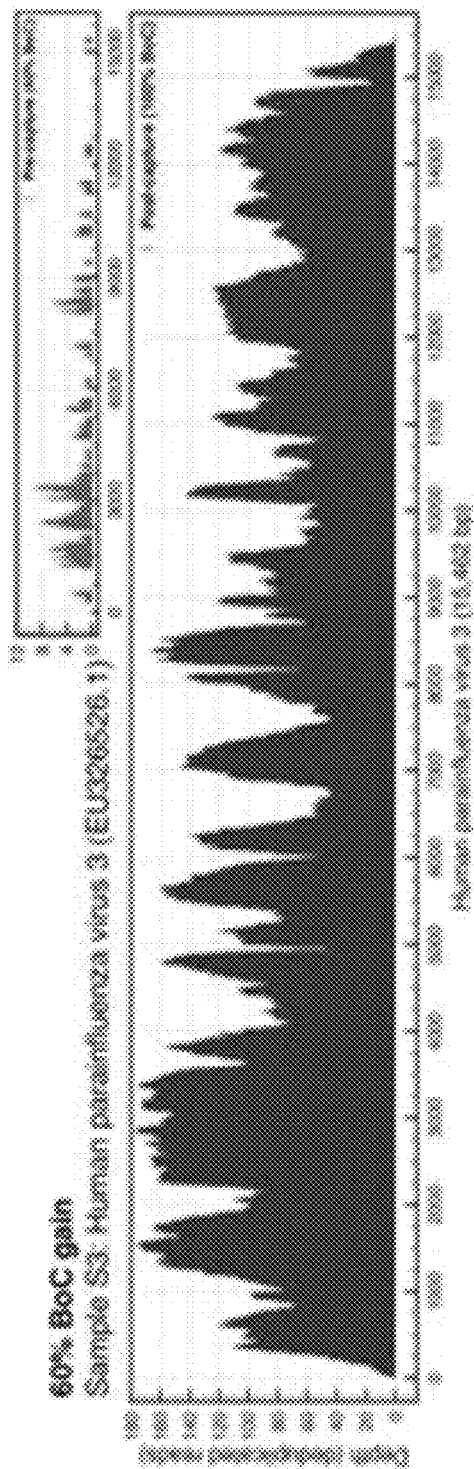
Figure 2G:
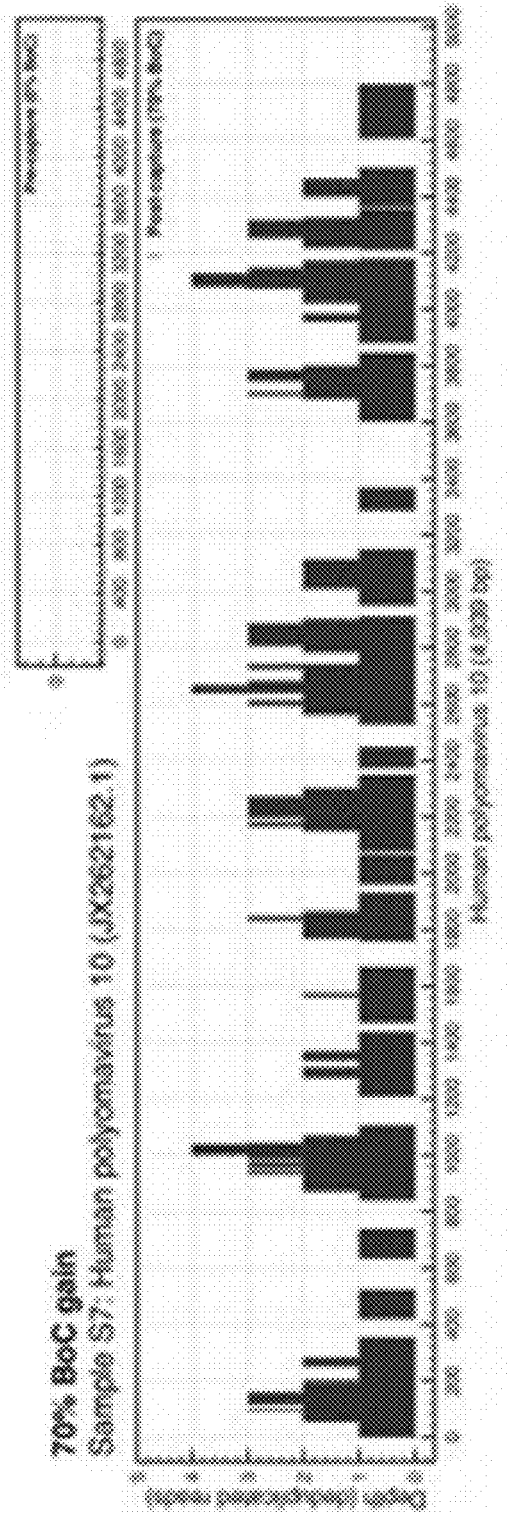
Figure 2H:
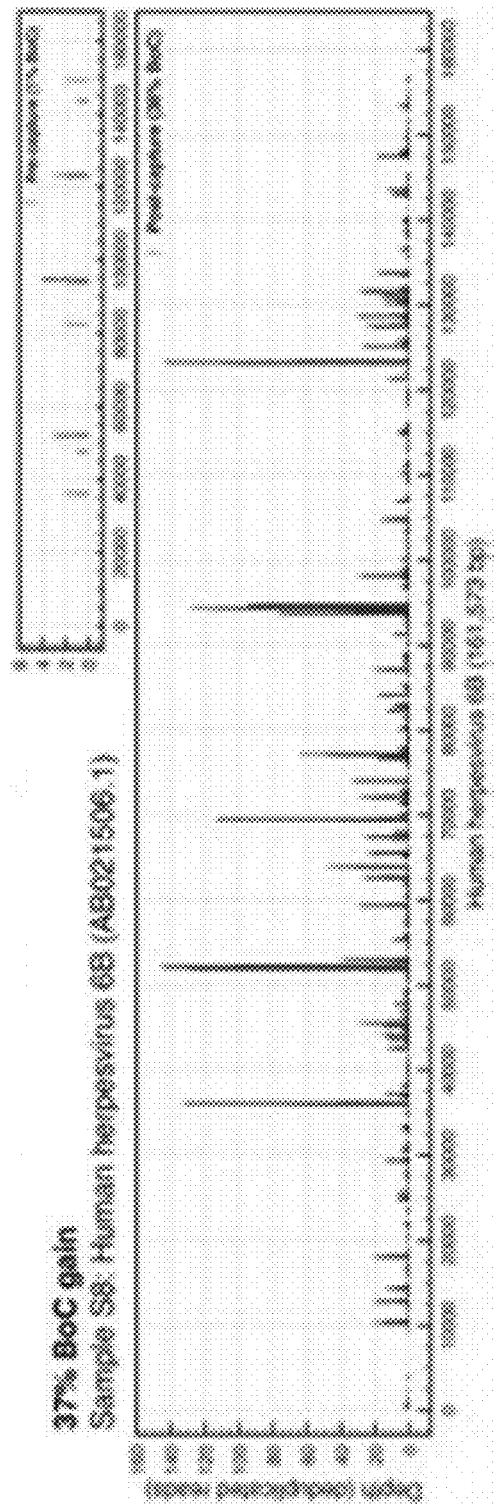

The inventors have designed a panel of probes that specifically hybridize to viral nucleic acid sequences (referred to herein as "the ViroCap panel") to enhance the sensitivity of metagenomic shotgun sequencing (MSS) for comprehensive detection of known vertebrate viruses, as well as to detect divergent viruses that have nucleotide sequence similarities to known viruses. The inventors have demonstrated that targeted sequence capture using ViroCap dramatically increases the amount of viral sequence obtained from human samples compared with conventional MSS, greatly enhancing the resolution of genomic characterization and increasing the number of viruses detected by >50%. Enhancement was demonstrated for DNA and RNA viruses from multiple diverse families. The increased sensitivity will be valuable in multiple research applications, including descriptions of the human virome, and will also improve the potential for MSS as a diagnostic tool in human and animal health.

The dramatic enrichment of viral nucleic acids present within the targeted sequence capture libraries offers important advantages. First, as the inventors demonstrate, MSS with ViroCap can be used to generate complete or nearly complete genome sequences directly from clinical samples, including those with very low proportions of viral nucleic acid, without culturing the viruses. Availability of extensive sequence data provides the opportunity to distinguish among closely related virus subtypes or even among viral strains, which might not be distinguished by other types of assays. Second, the use of ViroCap can reduce the depth of sequencing needed to detect viruses in samples. Because targeted sequence capture results in a large increase in the percentage of sequencing reads that are viral, ViroCap achieves better viral coverage while requiring the generation of fewer total sequence reads. This increased efficiency has the potential to lower sequencing costs.

I. Methods

The present disclosure provides a method to detect one or more viruses in a sample. The sample may be a sample from a subject, the environment, a laboratory, or any sample in which nucleic acid is present. When the sample is from a subject, the sample may be from a nasopharyngeal swab stool, sputum, urine, plasma, peripheral blood, serum, bone marrow, tissue, and other bodily fluids. In a specific embodiment, the sample is selected from the group consisting of nasopharyngeal swab, stool and plasma. The tissue sample may be a tissue biopsy. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract.

The sample may be used "as is", processed for cell lysis or disruption of viral particles, or the nucleic acid may be purified from the sample prior to sample preparation. Methods of isolating nucleic acid from a sample are known in the art. In certain embodiments, the isolated nucleic acid is reverse transcribed an amplified after isolation. This allows detection of both RNA and DNA viruses. Specifically, RNA in the total nucleic acid may be reverse transcribed with reverse transcriptase. Random nonomers may then be tagged with a conserved sequence to be used for subsequent amplification. Second strand synthesis may then be carried out using DNA polymerase to generate cDNA for the RNA viruses.

The DNA/cDNA mixture may then be amplified using DNA polymerase. In general, amplification is carried out using polymerase chain reaction (PCR). A PCR reaction may comprise nucleic acid, primers, polymerase, water, buffer, and deoxynucleotide triphosphates (dNTPs). PCR may be performed according to standard methods in the art. By way of non-limiting example, the PCR reaction may comprise denaturation, followed by about 5-10 cycles of denaturation, annealing and extension, followed by a final extension. In an exemplary embodiment, the PCR reaction comprises denaturation at about 98° C. for about 30 seconds, followed by about 5 to about 10 cycles of (about 98° C. for about 10 seconds, about 62-72° C. for about 30 seconds, about 72° C. for about 30 seconds), followed by a final extension at about 72° C. for about 5 minutes. Optionally, the amplified nucleic acid is then purified, for example, via column purification. The nucleic acid in the sample may then be sheared via methods known in the art to generate fragments. The fragments may be about 100 to about 2000 bp. For example, the fragments may be about 200 to about 1500 bp, about 400 to about 1000 bp, about 400 to about 800 bp, or about 500 bp.

If a sample is from a subject, the subject may be a rodent, a human, a livestock animal, a companion animal, a zoological animal, or an invertebrate vector. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. Non-limiting examples of suitable invertebrate vectors include mosquitoes, ticks, flies, and lice. In a preferred embodiment, the subject is a human.

A method of the disclosure comprises, in part, contacting a sample with a panel comprising probes capable of specifically hybridizing to greater than 10,000 viral nucleic acid sequences. As used herein, a "probe" is a nucleic acid probe, such as an oligonucleotide of at least 15, 30, 50, 100, 250, 500, 750 or more nucleotides in length, that specifically hybridizes under stringent conditions to a viral nucleic acid. For example, high stringency conditions, such as high hybridization temperature and low salt in hybridization buffers, permit only hybridization between nucleic acid sequences that are highly similar. In a specific embodiment, the probes may be about 50 to about 105 base pairs (bp). In another specific embodiment, the probes may be about 100 bp.

The probes for inclusion in the panel are designed based on a cohort of viral nucleic acid sequences. The cohort of viral nucleic acid sequences may be designed as set forth in the Examples. Specifically, the cohort of viral nucleic acid sequences comprises viral nucleic acid sequences from NCBI's RefSeq collection, complementary representation of unique regions from Genome Neighbor targets, selected representation of NCBI Influenza Virus Resource sequences, and the entirety of the probe space represented on the Virochip microarray (Yu et al. 2012), GEO accession number GPL15905. The cohort of viral nucleic acid sequences comprises viral nucleic acid sequences from all DNA and RNA viruses with sequenced genomes from vertebrate hosts, excluding human endogenous retroviruses and bacteriophages. The cohort of viral nucleic acid sequences comprises more than 150,000, more than 160,000, more than 170,000, or more than 180,000 viral nucleic acid sequences. Specifically, the cohort of viral nucleic acid sequences comprises 185,835 viral nucleic acid sequences. The cohort of viral nucleic acid sequences comprises greater than 150 Mb, greater than 160 Mb, greater than 170 Mb, greater than 180 Mb, or greater than 190 Mb of viral nucleic acid sequences. Specifically, the cohort of viral nucleic acid sequences comprises 198.9 Mb of viral nucleic acid sequences. Even more specifically, the cohort of viral nucleic acid sequences comprises about 27 Mb of viral nucleic acid sequences from RefSeq, about 153 Mb of viral nucleic acid sequences from Genome Neighbor targets, about 16 Mb from Influenza Virus Resource sequences, and about 3 Mb of viral nucleic acid sequences from Virochip microarray. The cohort of viral nucleic acid sequences is used to design a panel of probes that specifically hybridize to the viral nucleic acid sequences of the cohort of viral nucleic acid sequences.

A panel of the disclosure comprises greater than $1\times10^4$ probes capable of specifically hybridizing to the viral nucleic acid sequences of the cohort of viral nucleic acid sequences. For example, a panel of the disclosure comprises greater than $1\times10^4$ probes, greater than $2\times10^4$ probes, greater than $3\times10^4$ probes, greater than $4\times10^4$ probes, greater than $5\times10^4$ probes, greater than $6\times10^4$ probes, greater than $7\times10^4$ probes, greater than $8\times10^4$ probes, greater than $9\times10^4$ probes, greater than $1\times10^5$ probes, greater than $2\times10^5$ probes, greater than $3\times10^5$ probes, greater than $4\times10^5$ probes, greater than $5\times10^5$ probes, greater than $6\times10^5$ probes, greater than $7\times10^5$ probes, greater than $8\times10^5$ probes, greater than $9\times10^5$ probes, greater than $1\times10^6$ probes, greater than $2\times10^6$ probes, greater than $3\times10^6$ probes, greater than $4\times10^6$ probes, greater than $5\times10^6$ probes, greater than $6\times10^6$ probes, greater than $7\times10^6$ probes, greater than $8\times10^6$ probes, greater than $9\times10^6$ probes, or greater than $1\times10^7$ probes capable of specifically hybridizing to the viral nucleic acid sequences of the cohort of viral nucleic acid sequences. In a specific embodiment, a panel of the disclosure comprises about $2\times10^6$ probes capable of specifically hybridizing to the viral nucleic acid sequences of the cohort of viral nucleic acid sequences.

A panel of the disclosure comprises probes capable of specifically hybridizing to greater than 10,000 viral nucleic acid sequences. For example, a panel of the disclosure comprises probes capable of specifically hybridizing to greater than 10,000, greater than 15,000, greater than 20,000, greater than 25,000, greater than 30,000, greater than 35,000, greater than 40,000, greater than 45,000, greater than 50,000, greater than 55,000, greater than 60,000, greater than 65,000, greater than 70,000, greater than 75,000, greater than 80,000, greater than 85,000, greater than 90,000, greater than 95,000, greater than 100,000, greater than 110,000, greater than 120,000, greater than 130,000, greater than 140,000, greater than 150,000, greater than 160,000, greater than 170,000, greater than 180,000, greater than 190,000, or greater than 200,000 viral nucleic acid sequences. In an exemplary embodiment, a panel of the disclosure comprises probes capable of specifically hybridizing to 185,835 viral nucleic acid sequences. For a listing of all the sequences utilized in the ViroCap panel of the disclosure, see Wylie et al., Enhanced virome sequencing using targeted sequence capture. *Genome Res* 2015; 24(12):1910-20, the disclosure of which is hereby incorporated by reference in its entirety, including all supplemental information and zip files associated with the publication.

Additionally, a panel of the disclosure comprises probes capable of specifically hybridizing to greater than 50 Mb of viral nucleic acid sequences. For example, a panel of the disclosure comprises probes capable of specifically hybridizing to greater than 50 Mb, greater than 60 Mb, greater than 70 Mb, greater than 80 Mb, greater than 90 Mb, greater than 100 Mb, greater than 110 Mb, greater than 120 Mb, greater than 130 Mb, greater than 140 Mb, greater than 150 Mb, greater than 160 Mb, greater than 170 Mb, greater than 180 Mb, greater than 190 Mb, or greater than 200 Mb of viral nucleic acid sequences. In an exemplary embodiment, a panel of the disclosure comprises probes capable of specifically hybridizing to 198.9 Mb of viral nucleic acid sequences.

Further, a panel of the disclosure comprises probes capable of specifically hybridizing to viral nucleic acid sequences from all DNA and RNA viruses with sequenced genomes from vertebrate hosts, excluding human endogenous retroviruses and bacteriophages. In certain embodiments, a panel of the disclosure comprises probes capable of specifically hybridizing to viral nucleic acid sequences from NCBI's RefSeq collection, complementary representation of unique regions from NCBI Genome Neighbor targets, selected representation of NCBI Influenza Virus Resource sequences, and the entirety of the probe space represented on the Virochip microarray (Yu et al. 2012), GEO accession number GPL15905. The viral nucleic acid sequences may be consolidated via methods described in the Examples. In certain embodiments, a panel of the disclosure comprises probes capable of specifically hybridizing to about 27 Mb of viral nucleic acid sequences from RefSeq, about 153 Mb of viral nucleic acid sequences from Genome Neighbor targets, about 16 Mb from Influenza Virus Resource sequences, and about 3 Mb of viral nucleic acid sequences from Virochip microarray. Importantly, the panel of probes described herein may be continually updated via the methods described herein as new sequences become available.

More specifically, a panel of the disclosure comprises probes capable of specifically hybridizing to viral nucleic acid sequences from 34 viral families comprising 190 annotated viral genera and 337 species. Non-limiting examples of viral families with which the probes are capable of specifically hybridizing to include Adenoviridae, Alloherpesviridae, Asfarviridae, Herpesviridae, Iridoviridae, Malacoherpesviridae, Papillomaviridae, Polyomaviridae, Poxviridae, Birnaviridae, Picobirnaviridae, Reoviridae, Retroviridae, Hepadnaviridae, Parvoviridae, Anelloviridae, Circoviridae, Coronaviridae, Bunyaviridae, Flaviviridae, Orthomyxoviridae, Caliciviridae, Togaviridae, Arenaviridae, Arteriviridae, Astroviridae, Bornaviridae, Filoviridae, Hepeviridae, Paramyxoviridae, Picornaviridae, and Rhabdoviridae. In an exemplary embodiment, a panel of the disclosure comprises probes capable of specifically hybridizing to viral nucleic acid sequences from the viruses depicted in FIG. 4A. In an exemplary embodiment, a panel of the disclosure comprises probes capable of specifically hybridizing to viral nucleic acid sequences from the viruses listed in Table 10.

Hybridization of the probes to the nucleic acid may be done via methods standard in the art. For example, the nucleic acid may first be denatured such that it is single stranded and then the panel of probes and nucleic acid may be incubated at elevated temperature for about 1 to about 72 hours. More specifically, the nucleic acid may be denatured at >95° C. for about 20 minutes and then the panel of probes and nucleic acid may be incubated at about 47° C. for about 64 hours to about 72 hours.

Prior to, during or after hybridization an index sequence and adapter may be attached to the nucleic acid fragments. As used herein, an "adapter" is a sequence that permits universal amplification. A key feature of the adapter is to enable the unique amplification of the hybridized nucleic acid only without the need to remove existing template nucleic acid or purify the hybridized nucleic acid. This feature enables an "add only" reaction with fewer steps and ease of automation. The adapter is attached to the 5' and 3' end of the hybridized nucleic acid. The adapter may be Y-shaped, U-shaped, hairpin-shaped, or a combination thereof. In a specific embodiment, the adaptor is Y-shaped. In another specific embodiment, the adapter may be an Illumina adapter for Illumina sequencing. An index sequence may also be attached to each nucleic acid fragment. The addition of an index sequence allows pooling of multiple samples into a single sequencing run. This greatly increases experimental scalability, while maintaining extremely low error rates and conserving read length. The index sequence may be about 5 to about 10 nucleotides. Accordingly, the index sequence may be 5, 6, 7, 8, 9 or 10 or more nucleotides. In an embodiment, the index sequence is about 6 nucleotides.

A method of the disclosure further comprises, in part, isolating the probes that specifically hybridize to viral nucleic acid sequences within the sample. Methods of isolating probes are known in the art. In a specific embodiment, bead purification may be used to isolate the probes that specifically hybridize to viral nucleic acid sequences within the sample. For example, Streptavidin beads may be used. The Streptavidin beads may be incubated with the hybridized sample at about 47° C. for about 45 minutes. The sample may then be washed to remove unbound beads.

The isolated viral nucleic acid sequences may then be amplified. In general, amplification is carried out using polymerase chain reaction (PCR). A PCR reaction may comprise isolated viral nucleic acid, primers, polymerase, water, buffer, and deoxynucleotide triphosphates (dNTPs). PCR may be performed according to standard methods in the art. By way of non-limiting example, the PCR reaction may comprise denaturation, followed by about 10-20 cycles of denaturation, annealing and extension, followed by a final extension. In an exemplary embodiment, the PCR reaction comprises denaturation at about 98° C. for about 30 seconds, followed by about 10 to about 20 cycles of (about 98° C. for about 10 seconds, about 60-72° C. for about 30 seconds, about 72° C. for about 30 seconds), followed by a final extension at about 72° C. for about 5 minutes. Optionally, the amplified viral nucleic acid is then purified, for example, via column purification.

A method of the disclosure further comprises, in part, sequencing the isolated viral nucleic acid sequences. Sequencing may be performed according to standard methods in the art. Sequencing is preferably performed on a massively parallel sequencing platform, many of which are commercially available including, but not limited to Illumina, Roche/454, Ion Torrent, Oxford Nanopore Technologies and PacBio. In an exemplary embodiment, Illumina sequencing is used.

After sequencing of the viral nucleic acid, the sequences are compared with a database comprising reference viral nucleic acid sequences to determine the identity of the viral nucleic acid in the sample. Comparison of sequences generally involves aligning the experimentally determined sequence with a reference sequence. Methods of aligning sequences are known in the art. In a specific embodiment, the alignment algorithm utilized may be BWA-MEM. BWA-MEM is an alignment algorithm for aligning sequence reads or long query sequences against a large reference genome. It automatically chooses between local and end-to-end alignments, supports paired-end reads and performs chimeric alignment. The algorithm is robust to sequencing errors and applicable to a wide range of sequence lengths from 70 bp to a few megabases. For mapping 100 bp sequences, BWA-MEM shows better performance than several state-of-art read aligners to date. The sequence alignments may then be evaluated to determine the identity of the viral nucleic acid in the sample. Methods of evaluating sequence alignments are known in the art. In a specific embodiment, SAMtools is utilized to evaluate the sequence alignments. SAMtools is a set of utilities for interacting with and post-processing short DNA sequence read alignments in the SAM (=Sequence Alignment/Map), BAM (=Binary Alignment/Map) and CRAM formats. Both simple and advanced tools are provided, supporting complex tasks like variant calling and alignment viewing as well as sorting, indexing, data extraction and format conversion.

A method of detecting one or more viruses as described herein increases the number of viruses detected relative to MSS alone. For example, the method of detecting viruses described herein increases the number of viruses detected by greater than 40% relative to MSS alone. Accordingly, the method of detecting viruses described herein increases the number of viruses detected by greater than 40%, greater than 45%, greater than 50%, greater than 55%, greater than 60%, greater than 65%, greater than 70%, greater than 75%, greater than 80%, greater than 85%, greater than 90%, or greater than 95% relative to MSS alone. In a specific embodiment, the method of detecting viruses described herein increases the number of viruses detected by greater than 50% relative to MSS alone.

A method of detecting one or more viruses as described herein increases the breadth of coverage of viral genomes relative to MSS alone. For example, the method of detecting viruses described herein results in a breadth of coverage of greater than 40%. Accordingly, the method of detecting viruses described herein results in a breadth of coverage of greater than 40%, greater than 45%, greater than 50%, greater than 55%, greater than 60%, greater than 65%, greater than 70%, greater than 75%, greater than 80%, greater than 85%, greater than 90%, or greater than 95%. In a specific embodiment, the method of detecting viruses described herein results in a breadth of coverage of greater than 80%. In another specific embodiment, the method of detecting viruses described herein results in a breadth of coverage of greater than 90%.

In certain embodiments, if the sample is a biological sample obtained from a subject, the subject is treated based on the virus detected. Accordingly, a method of the disclosure may be used to diagnose, treat or prevent a disease in a subject. Identification of a virus in a subject could facilitate the diagnosis of a disease, enable the proper methodology, such as a therapeutic, to treat the disease, or prevent the onset of disease by administration of prophylactic therapies. Additionally, identification of anti-viral drug resistant strain could facilitate better treatment strategies.

Importantly, using the methods described herein, a panel of probes could comprise probes that specifically hybridize to bacteria and associated plasmids, fungi, protists, and other microbes. For bacteria, the probes may specifically hybridize to virulence genes such as toxin genes or antibiotic resistance genes. Using the methods described herein, specifically those detailed in the Examples, one of ordinary skill in the art would be able to design a panel of probes to detect a variety of human pathogens. Accordingly, the panel of probes of the disclosure may comprise a comprehensive set of probes to detect a variety of human pathogens. As such, a method of the disclosure may further comprise a method of detecting a pathogen in a sample. As described above, the sample may be environmental or a biological sample obtained from a subject. Additionally, a method of the disclosure may further comprise a method of detecting an infection in a subject. The term "infection" as used herein includes the presence of pathogens in or on a subject, which, if its growth were inhibited, would result in a benefit to the subject. As such, the term "infection" in addition to referring to the presence of pathogens also refers to normal flora which are not desirable. The term "pathogen" as used herein refers to an infectious agent that can produce disease. Non-limiting examples of an infectious agent include virus, bacterium, prion, fungus, viroid, or parasite that cause disease in a subject.

II. Kit

In another aspect, the disclosure provides a kit comprising a panel of the disclosure as described in Section I. More specifically, a kit comprises a panel of probes that specifically hybridize to viral nucleic acid sequences as described in Section I. The kit may also comprise detection agents that can detect hybridization of the probes to the viral nucleic acid sequences of the disclosure, and instructions for use. A person skilled in the art will appreciate that a number of detection agents can be used to detect hybridization of the probes to viral nucleic acid sequences. For example, the detection agent can be a label. The label is preferably capable of producing, either directly or indirectly, a detectable signal. For example, the label may be radio-opaque or a radioisotope, such as $^3$H, $^{14}$C; $^{32}$P, $^{35}$S; $^{123}$I; $^{125}$I; $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The kit can also include a control or reference standard and/or instructions for use thereof. In addition, the kit can include ancillary agents such as vessels for storing or transporting the detection agents and/or buffers or stabilizers.

In certain embodiments, the kit is a nucleic acid array. Such an array may be used to detect viral nucleic acid sequences in a biological sample. An array may be comprised of a substrate having disposed thereon probes of the disclosure capable of hybridizing to the viral nucleic acid sequences of the disclosure.

Several substrates suitable for the construction of arrays are known in the art. The substrate may be a material that may be modified to contain discrete individual sites appropriate for the attachment or association of the nucleic acid and is amenable to at least one detection method. Alternatively, the substrate may be a material that may be modified for the bulk attachment or association of the nucleic acid and is amenable to at least one detection method. Non-limiting examples of substrate materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. In an embodiment, the substrates may allow optical detection without appreciably fluorescing.

A substrate may be planar, a substrate may be a well, i.e. a 1534-, 384-, or 96-well plate, or alternatively, a substrate may be a bead. Additionally, the substrate may be the inner surface of a tube for flow-through sample analysis to minimize sample volume. Similarly, the substrate may be flexible, such as a flexible foam, including closed cell foams made of particular plastics. Other suitable substrates are known in the art.

The nucleic acid or biomolecules may be attached to the substrate in a wide variety of ways, as will be appreciated by those in the art. The nucleic acid may either be synthesized first, with subsequent attachment to the substrate, or may be directly synthesized on the substrate. The substrate and the nucleic acid may both be derivatized with chemical functional groups for subsequent attachment of the two. For example, the substrate may be derivatized with a chemical functional group including, but not limited to, amino groups, carboxyl groups, oxo groups or thiol groups. Using these functional groups, the nucleic acid may be attached using functional groups on the biomolecule either directly or indirectly using linkers.

The nucleic acid may also be attached to the substrate non-covalently. For example, a biotinylated nucleic acid can be prepared, which may bind to surfaces covalently coated with streptavidin, resulting in attachment. Alternatively, a nucleic acid or nucleic acids may be synthesized on the surface using techniques such as photopolymerization and photolithography. Additional methods of attaching biomolecules to arrays and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, each of which is hereby incorporated by reference in its entirety).

In one embodiment, the nucleic acid or nucleic acids attached to the substrate are located at a spatially defined address of the array. Arrays may comprise from about 1 to about several hundred thousand addresses. A nucleic acid may be represented more than once on a given array. In other words, more than one address of an array may be comprised of the same nucleic acid. In some embodiments, two, three, or more than three addresses of the array may be comprised of the same nucleic acid. In certain embodiments, the array may comprise control nucleic acids and/or control addresses. The controls may be internal controls, positive controls, negative controls, or background controls.

Furthermore, the nucleic acids used for the array may be labeled. One skilled in the art understands that the type of label selected depends in part on how the array is being used. Suitable labels may include fluorescent labels, chromagraphic labels, chemi-luminescent labels, FRET labels, etc. Such labels are well known in the art.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to the Examples

High-throughput, massively parallel nucleotide sequence analysis has made in-depth studies of the human microbiome feasible. Thus far, most microbiome studies have focused on bacteria, although some include fungi. Viruses are particularly understudied, in part due to the challenges of assessing their presence in clinical samples. Viruses as a group have highly variable genomes, with no gene shared among all viruses that can be surveyed by an amplicon-based sequencing strategy. Therefore, studies of viruses based on nucleotide sequencing require a metagenomic approach. Metagenomic shotgun sequencing (MSS) is a relatively unbiased, culture-independent method in which nucleic acid extracted from a sample is sequenced. Sequence reads are classified based on similarity to reference genomes. This approach allows comprehensive study of the viral component of the microbiome (the virome) and has led to the discovery of novel viruses and the characterization of viruses present in healthy and sick people. When adequate numbers of sequence reads are generated, viruses can be characterized with regard to taxonomy and the presence of genes associated with virulence and resistance to antiviral drugs.

A limitation of MSS as employed to date for virus detection is that the amount and proportion of viral nucleic acid in samples from humans may be very low, and in these cases, few viral sequences are generated. In our experience using MSS, we have detected fewer than 10 viral sequences per 25 million sequence reads generated for a virus that was detected in a sample by a molecular assay. In other instances, we have failed to detect viruses known to be present based on molecular assays. These difficulties may reflect the small genome size of some viruses and/or low levels of virus in the sample. This can be a particular problem for studies of the virome of healthy, asymptomatic individuals, in whom virus levels may be low. In efforts to increase the sequence yield, purification or enrichment procedures have been employed, including low-speed centrifugation and/or filtration to remove bacterial and host cells, sample treatment with nucleases to digest nucleic acid not protected within virions, or concentration of viral particles by high-speed gradient centrifugation (for review, see Duhaime and Sullivan 2012). Each of these procedures may bias against detection of some viruses (Breitbart and Rohwer 2005; Young et al. 2014).

An alternative method for enrichment of viral sequences in a metagenomic sample prior to sequencing is targeted sequence capture. Our aim was to develop a comprehensive viral targeted sequence capture panel that could be used to (1) assess all viruses known to infect vertebrate cells and (2) detect divergent viruses. To this end, we created ViroCap, a targeted sequence capture panel that enhances the detection of a comprehensive set of viruses with vertebrate hosts. Here we describe the first application of ViroCap to enrich a broad range of viruses from human clinical samples.

Example 1

Analysis of Clinical and Research Samples with ViroCap

ViroCap includes targets from 34 viral families, comprising 190 annotated viral genera and 337 species (FIG. 1).

Included viruses represent all DNA and RNA viruses with sequenced genomes from vertebrate hosts, except human endogenous retroviruses, which were excluded due to their prevalence within the human genome. Nearly 1 billion bp of viral genome sequences were condensed into <200 million bp of targets (Table 3) using k-mer and clustering analyses to define a unique set of reference sequences, as described in the Methods.

We evaluated the effectiveness of detecting DNA and RNA viruses in MSS data compared with ViroCap targeted sequence capture data in two sets of human samples. In experiment 1, the sample set consisted of clinical samples that had been found to be positive by molecular tests in the Diagnostic Virology Laboratory at St. Louis Children's Hospital. Nucleic acid extracts available in the Virology Laboratory were pooled, and a sequencing library was prepared from this pooled nucleic acid (see Methods). In experiment 2, eight patient samples from a research study of young children with fever (Colvin et al. 2012; Wylie et al. 2012) were selected for use in the present study because each had been found to be positive for one or more viruses when tested by batteries of PCR assays used in that study. Individual sequencing libraries were prepared from each of the eight samples as described in the Methods and pooled for sequencing. Experiments 1 and 2 were analyzed in separate sequencing runs. In each experiment, sequencing libraries were divided, and the same library was sequenced without targeted sequence capture (precapture) and following targeted sequence capture using ViroCap (post-capture).

In experiment 1, we detected 10 viruses in the precapture MSS data (Table 1). After targeted sequence capture using the same sequencing library, we detected the same 10 viruses plus four additional viruses. Targeted sequence capture resulted in dramatic improvements in all sequence coverage metrics (Table 1; Table 4), including number and percentage of viral reads, breadth and depth of coverage, and coverage gaps. In experiment 1, the median increase in percentage of viral reads was 674 (range, >13-9335), and the median breadth of coverage increased from 2.1% (range, 0%-89.8%) to 83.2% (range, 0.8%-100%). Illustrative examples are shown in FIG. 2A, FIG. 2B, FIG. 2C, FIG. 2D.

Figure 4A:
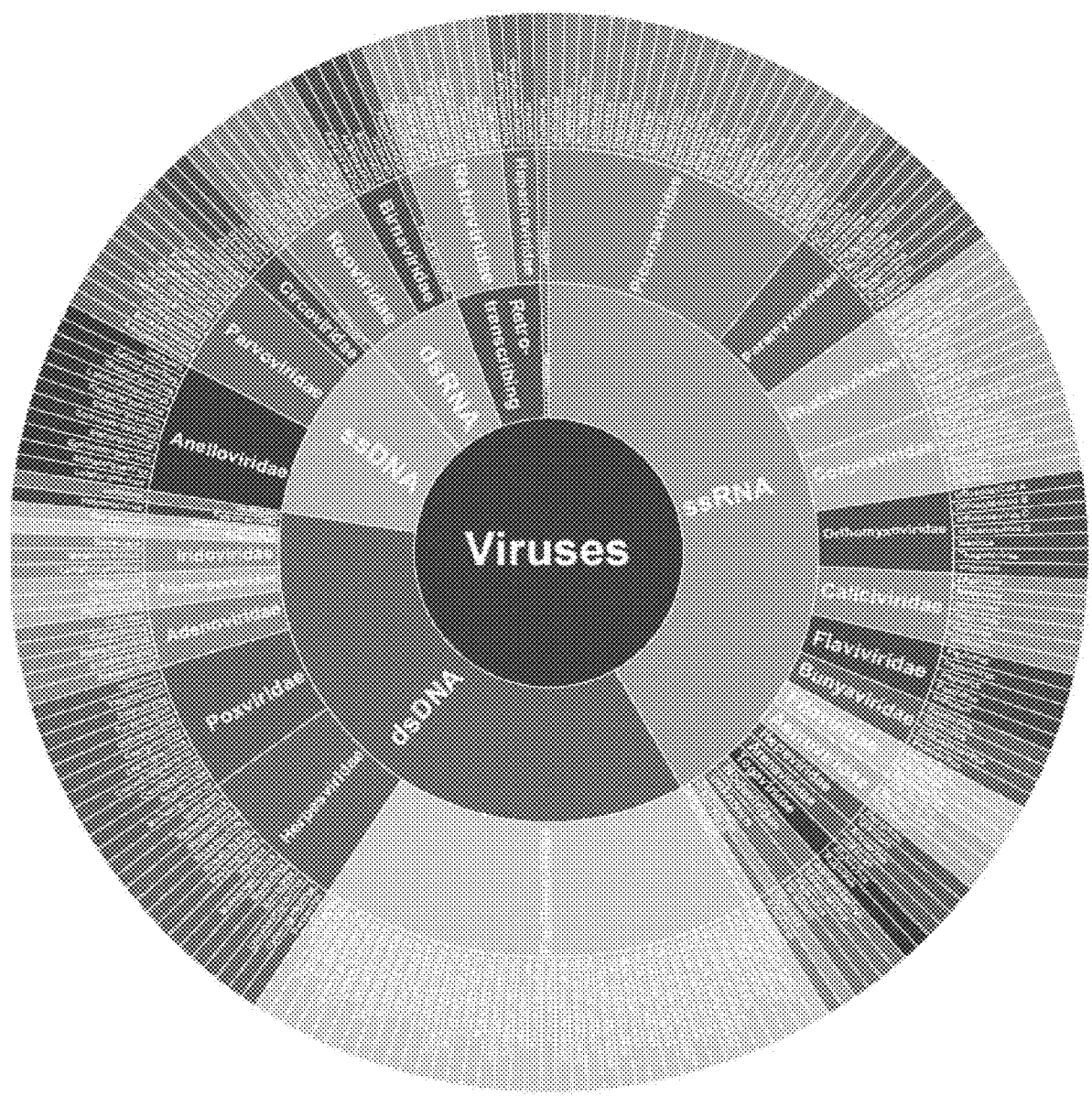
FIG. 4A and FIG. 4B depict the taxonomic distribution of target genomes.
Figure 4B:
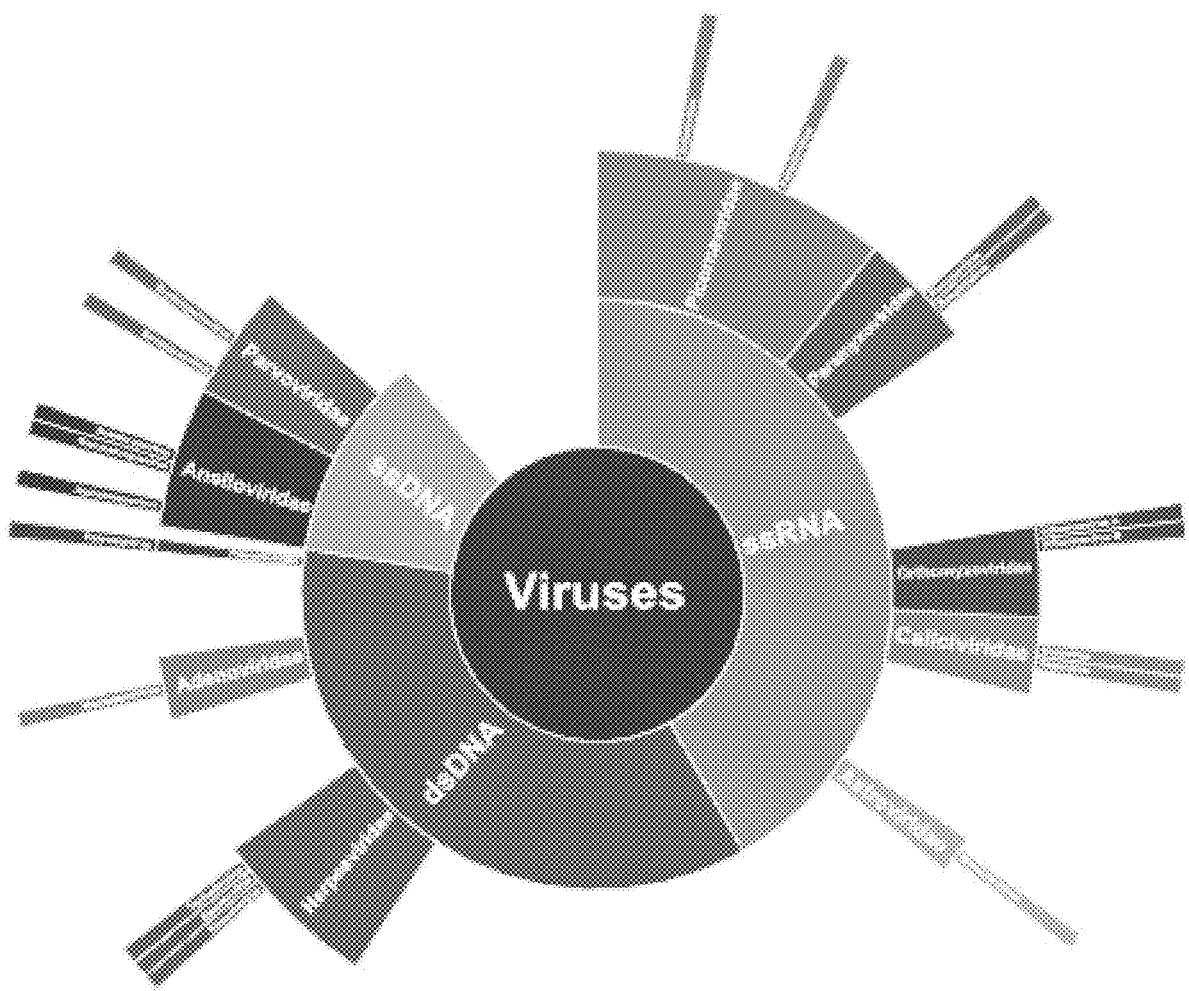

In experiment 2, 11 viruses were detected in the precapture MSS data (Table 2). After targeted sequence capture with ViroCap using the same sequencing libraries, we detected those 11 viruses plus seven additional viruses. Thus, in the two experiments together, the number of viruses detected went from 21 to 32, a 52% increase. All of the viruses detected in both experiments were confirmed by PCR assays except for a torque teno virus in the clinical pool, which was not evaluated by PCR (Table 1, Table 8, Table 9). Viruses detected encompassed 19 genera from 10 families (FIG. 4A, FIG. 4B). In experiment 2, we again found that targeted sequence capture resulted in dramatic improvements in sequencing parameters. In experiment 2, the median fold increase in percentage of viral reads was 296 (range, >56-2722), and the median breadth of coverage increased from 2.0% (range, 0%-99.9%) to 75.6% (range, 13.5%-100%). Illustrative examples are shown in FIG. 2E, FIG. 2F, FIG. 2G, FIG. 2H.

By use of targeted sequence capture, >80% breadth of coverage of the viral genomes was obtained for 16 of 32 viruses, including diverse DNA and RNA genomes of sizes ranging from 5-161 kb (Table 1, Table 2, Table 4, Table 5). Greater than 90% breadth of coverage was obtained for 12 of 32 viruses, and eight viruses had 100% coverage. Precapture, the median gap size in genome coverage was 1704 bp (range 4-152,261 bp), and post-capture, the median gap size was 82 bp (range 0-13,734 bp) (Table 4, Table 5). High genome representation was obtained for multiple viruses in the same capture reaction, as experiments 1 and 2 were each single, independent capture reactions encompassing multiple samples (see Methods).

Example 2

Targeted Sequence Capture Identifies Divergent Viral Sequences

Figure 3A:
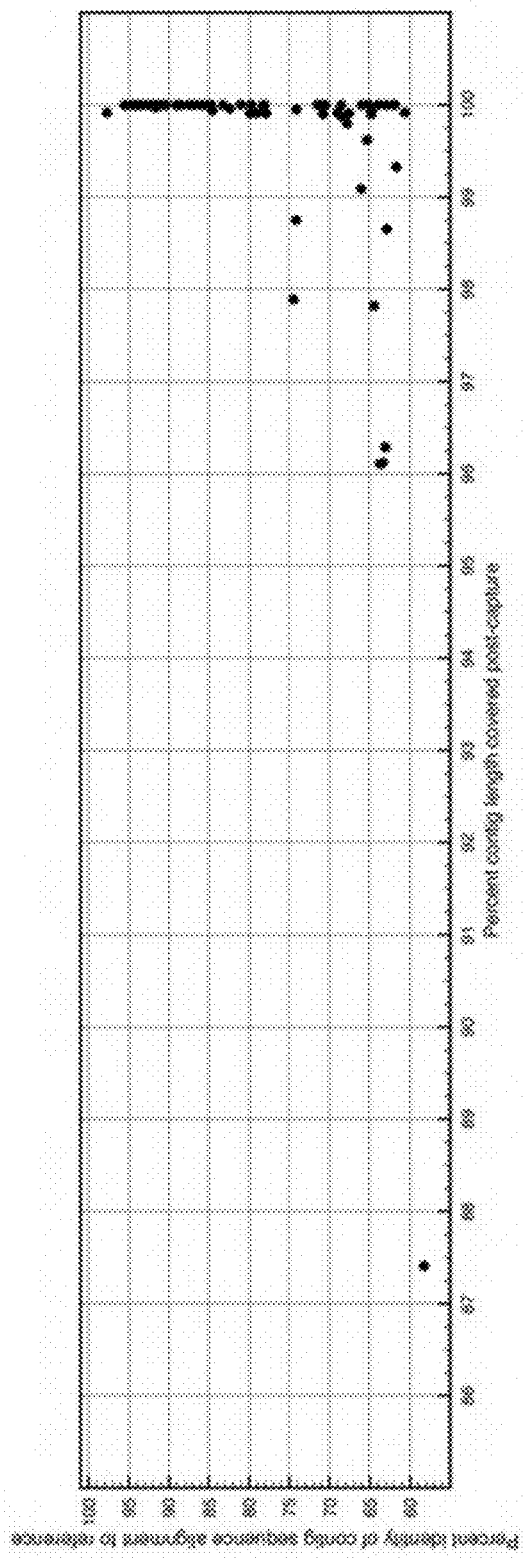
FIG. 3A and FIG. 3B depict targeted sequence capture identifies divergent sequences.
Figure 3B:
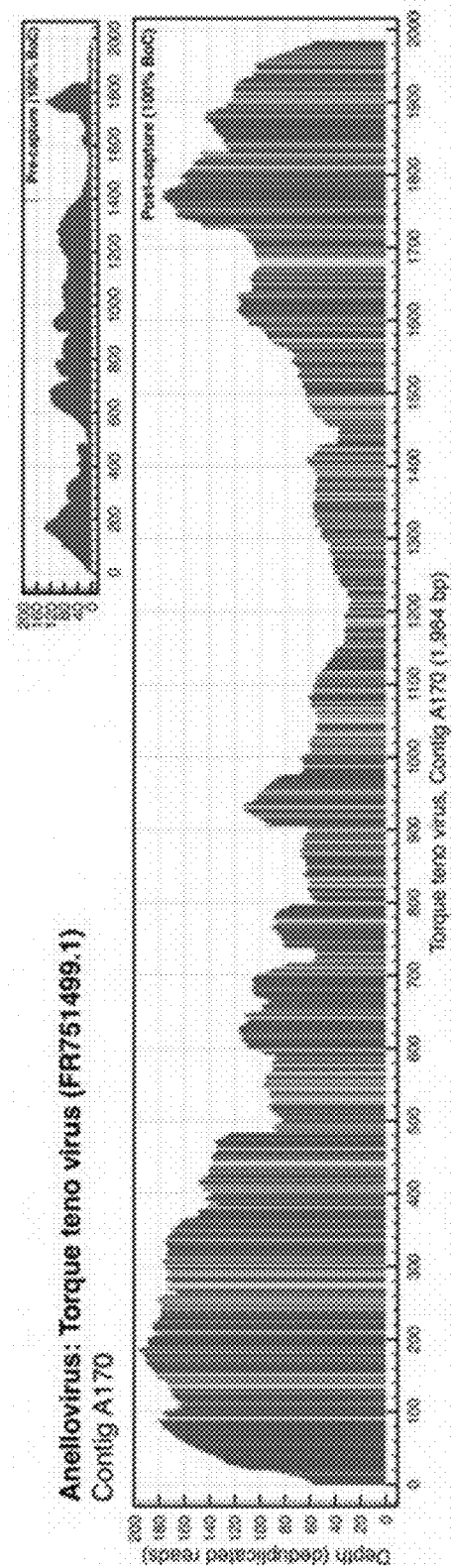

To determine whether or not divergent sequences could be identified using targeted sequence capture, we tested ViroCap on samples containing anelloviruses, a highly divergent group of ssDNA viruses that have a common genome structure but may have up to 30%-50% nucleotide sequence diversity among separate species (Ninomiya et al. 2007; de Villiers et al. 2011). We selected *anellovirus*-positive samples that we had previously characterized using multistrand displacement amplification followed by high-throughput sequencing. After assembling the precapture sequences to generate contiguous sequences (contigs), we identified *anellovirus* contigs>1 kb in length. The contigs had varying degrees of similarity to the reference genomes used in the ViroCap panel based on BLAST alignments, ranging from 58%-98% nucleotide sequence identity for the top high-scoring segment pair (HSP) alignment (FIG. 3A; Table 6). All of the contigs assembled using the precapture sequence data were also detected post-capture. The contig with 58% identity to the reference database was missing 13% of its length post-capture (FIG. 3A). The contig with the next lowest percentage identity to the reference database (62%) was fully sequenced (i.e., 100% breadth-of-coverage) (FIG. 3A, FIG. 3B). FIG. 3B illustrates the nucleotide sequence matches/mismatches between the contig and the most similar reference genome in the sequences used for the ViroCap design. These results demonstrate that targeted sequence capture using the ViroCap panel allows us to identify variant virus sequences having as low as 58% nucleotide sequence identity.

Example 3

Specificity of Targeted Sequence Capture

Figure 5:
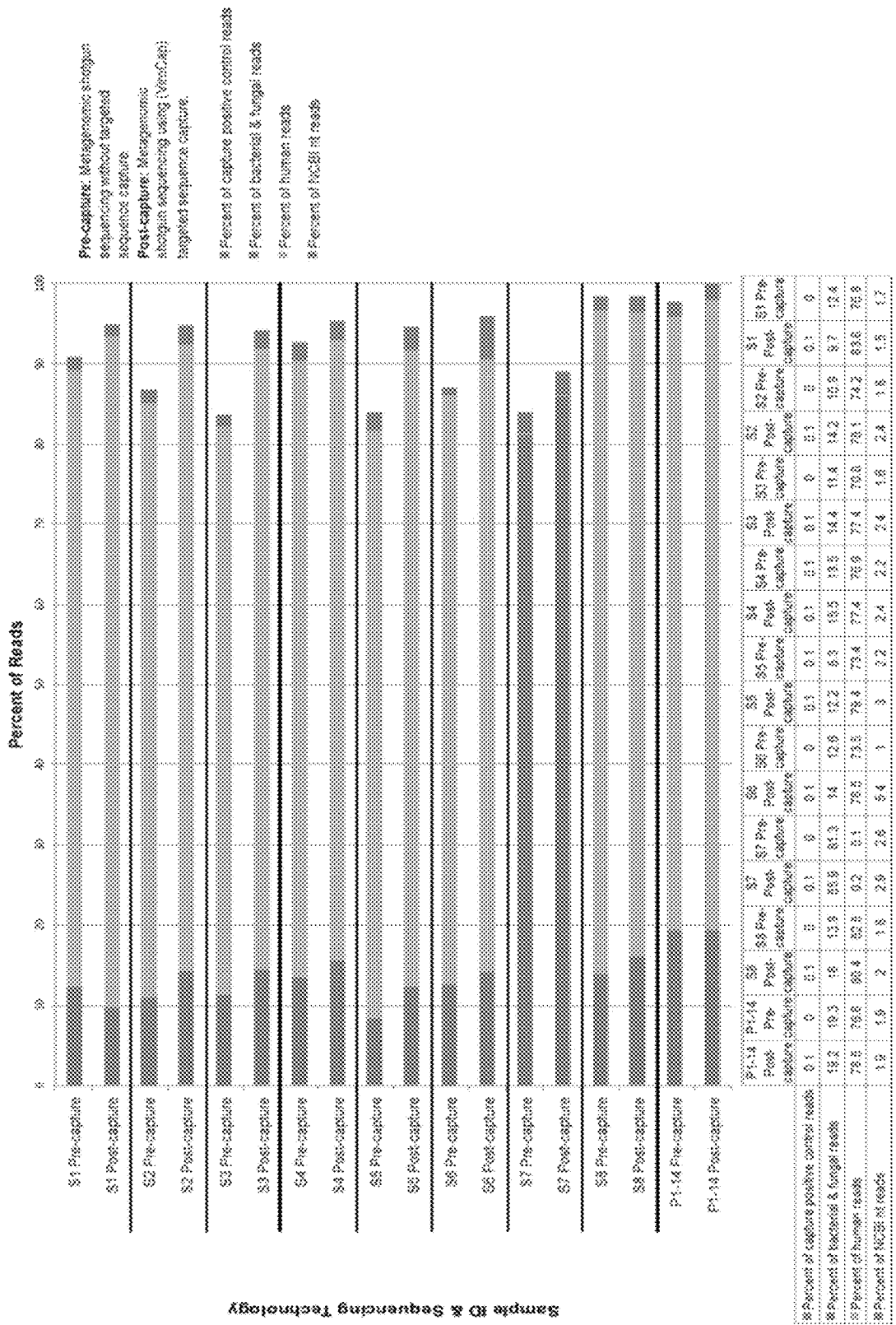
FIG. 5 depicts non-viral read classification based on metagenomic shotgun sequencing before and after viral targeted sequence capture. Classifications of non-viral reads were determined based on nucleotide sequence alignment against bacterial and fungal reference genomes, the human genome, NCBI nt, and capture positive control sequences (positive control probes targeting human genes as included by NimbleGen). The percentages of reads per category are shown on the stacked bar charts and in the data table. For each sample, a small percentage of non-viral reads did not map to any of the reference databases evaluated. Proportions of reads mapping to bacteria/fungi, human, and NCBI nt references was similar pre- and post-capture, indicating the viral capture probes did not consistently or strikingly enrich any other class of organisms expected to be found in these samples. As expected, the positive controls were enriched post-capture in each case.
Figure 6:
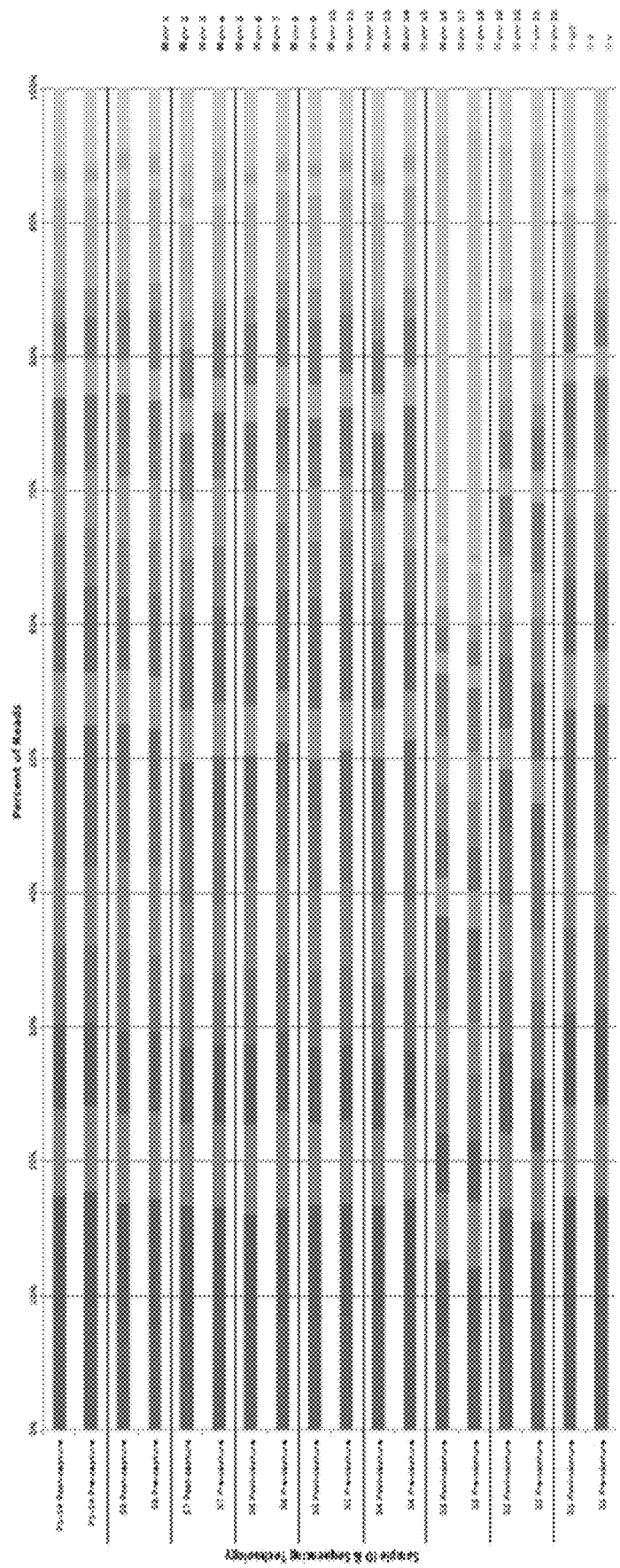
FIG. 6 depicts human chromosome identities based on metagenomic shotgun sequencing before and after viral targeted sequence capture. The proportions of sequences mapping to each human chromosome and mitochondria are plotted. Viral capture probes did not enrich sequences from human chromosomes. The percentages of human-mapped reads are shown on the stacked bar graphs and in the data table (Table 11).
Figure 7A:
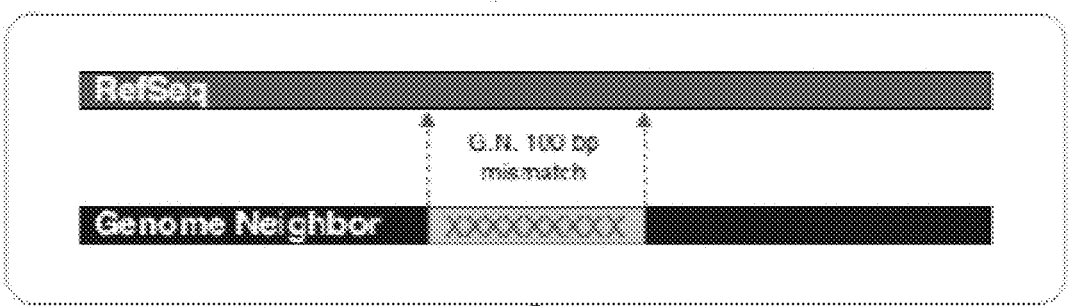
FIG. 7A, FIG. 7B, FIG. 7C and FIG. 7D depict Genome Neighbor target sequence selection. The general approach for Genome Neighbor target sequence selection is illustrated. While this process is performed on all viral RefSeqs, here we illustrate a small genomic region of a single RefSeq and Genome Neighbor pairing. First, all Genome Neighbor sequences related to a single RefSeq entry are located and associated. In this example, the single Genome Neighbor sequence shown, when compared to RefSeq, has a 100 bp span of alternative sequence (FIG. 7A). The Genome Neighbor sequence is used to generate k-mers of length 100 bp (i.e. capture probe analogs) by means of an exhaustive 1 bp sliding window algorithm, retaining genomic coordinate origin information for each k-mer (FIG. 7A). The resultant set of 100-mers accounts for all potential target sequences that could be used to capture this region. In this example, when comparing Genome Neighbor 100-mers to the corresponding RefSeq genome there is one 100-mer that is completely variant compared to RefSeq, and a set of other 100-mers containing both variant and conserved regions across their lengths due to the nature of the sliding window effect (FIG. 7B). We identify 100-mers that are not represented in the RefSeq genome by sequence clustering (FIG. 7C). Any 100-mers that have >=90% identity to the RefSeq genome are not added to the capture target sequence (Cluster 1, labeled within the figure as "Discarded"). Sequences with <90% identity to RefSeq will form clusters representing variant sequences (Clusters 2-10, labeled within the figure as "Retained"). 100-mers from the variant, non-RefSeq clusters are collected and merged based on genomic coordinates into single, contiguous Genome Neighbor sequence representations used for targeted sequence capture (FIG. 7D).
Figure 7A:
Figure 7A:
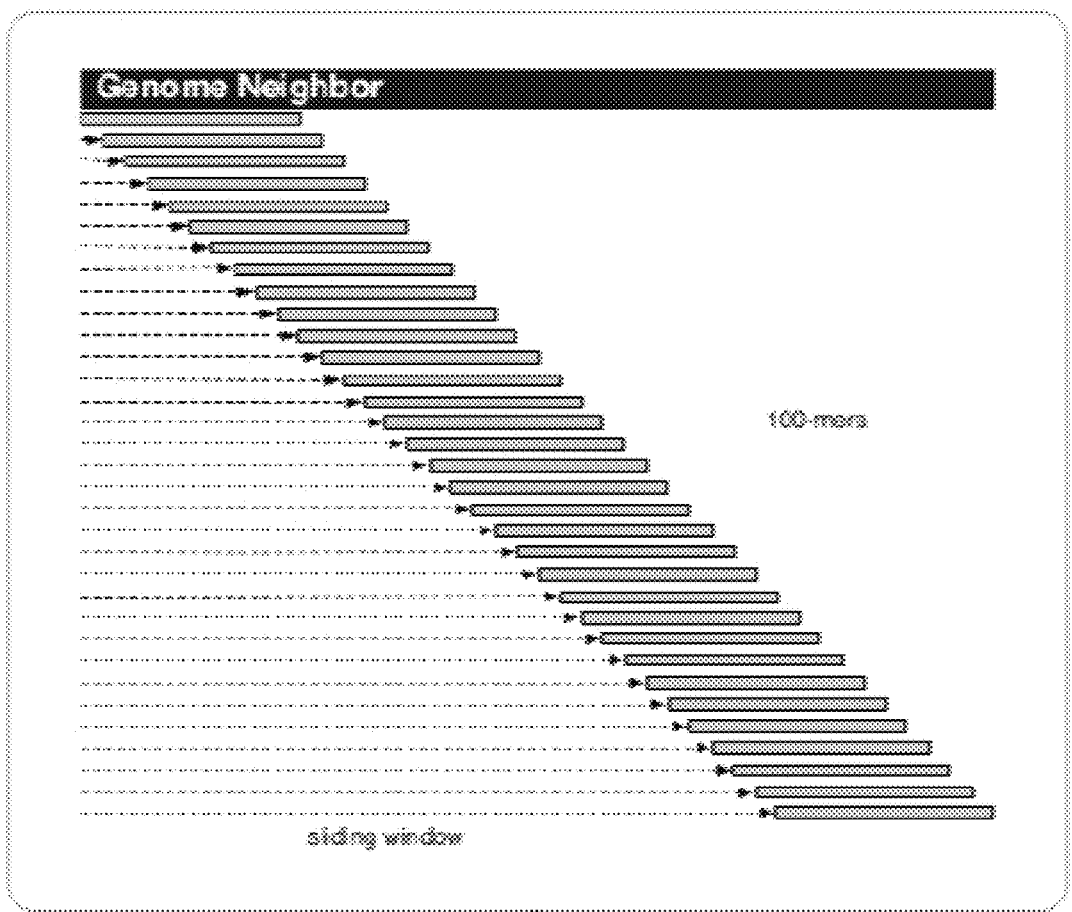
Figure 7A:
Figure 7B:
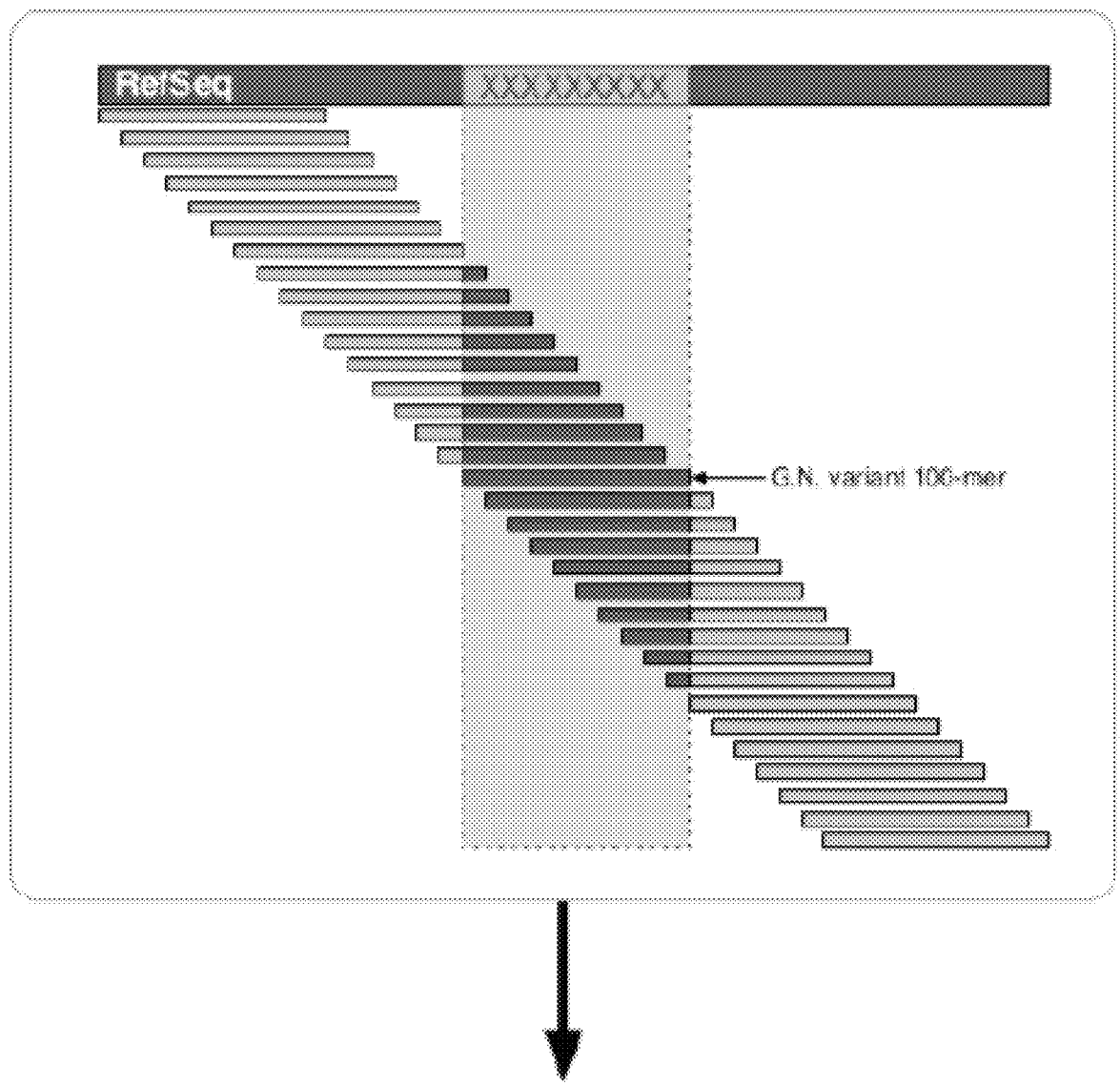
Figure 7C:
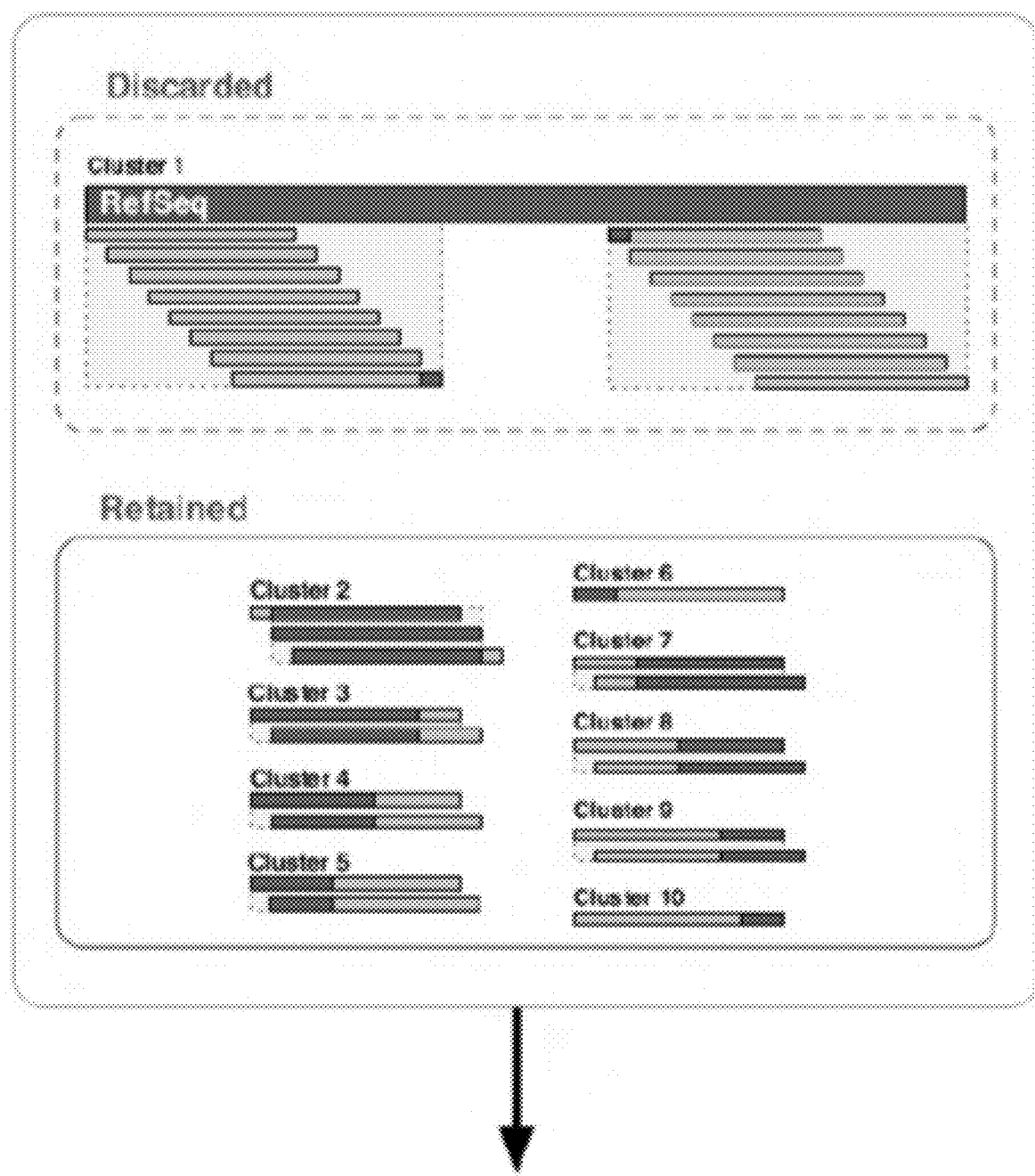
Figure 7D:
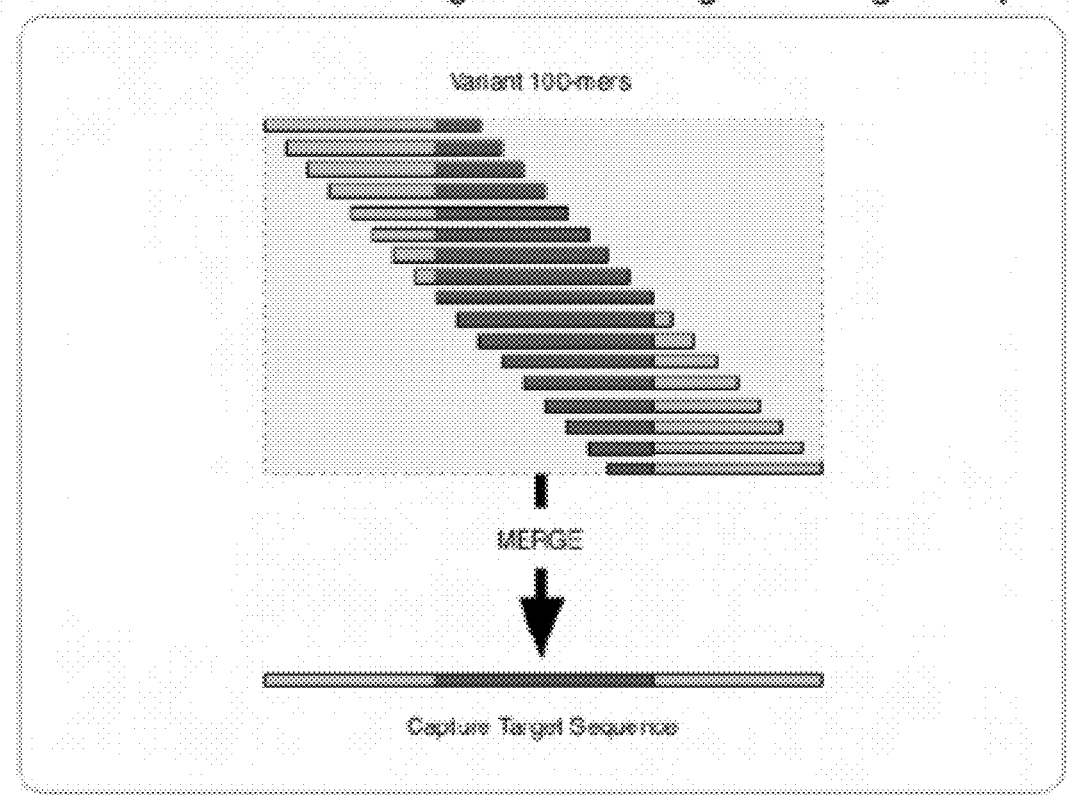

In order to determine whether ViroCap systematically enriched off-target sequences, we compared the filtering and classification statistics of the nonviral sequences in the precapture MSS and targeted sequence capture data (Table 7, FIG. 5, FIG. 6). If our probes were specific, we would not observe any systematic enrichment of specific human chromosomes or bacterial genomes post-capture. However, we anticipated a small amount of variation because the targeted sequence capture library had been through more sample handling in the form of incubations, dilutions, and amplifications. We found that the proportions of the nonviral sequences were strongly correlated (Pearson's correlation value: r=0.9881-0.9996) (Table 7, FIG. 5). A slightly higher percentage (mean, 5.8%; median, 5%; range, 0%-10.7%) of reads aligned to nonviral reference genomes in the post-capture data compared with precapture in all but one of the samples. However, the distribution of sequences among reference genomes did not show a systematic bias. This can be seen in the conserved distribution of sequences among human chromosomes (FIG. 6).

Discussion for the Examples

We designed the ViroCap panel to enhance the sensitivity of MSS for comprehensive detection of known vertebrate viruses, as well as to detect divergent viruses that have nucleotide sequence similarities to known viruses. Here we have demonstrated that targeted sequence capture using ViroCap dramatically increases the amount of viral sequence obtained from human samples compared with conventional MSS, greatly enhancing the resolution of genomic characterization and increasing the number of viruses detected by >50%. Enhancement was demonstrated for DNA and RNA viruses from multiple diverse families. The increased sensitivity will be valuable in multiple research applications, including descriptions of the human virome, and will also improve the potential for MSS as a diagnostic tool in human and animal health.

The dramatic enrichment of viral nucleic acids present within the targeted sequence capture libraries offers important advantages. First, as we demonstrate, MSS with Viro-Cap can be used to generate complete or nearly complete genome sequences directly from clinical samples, including those with very low proportions of viral nucleic acid, without culturing the viruses. Availability of extensive sequence data provides the opportunity to distinguish among closely related virus subtypes or even among viral strains, which might not be distinguished by other types of assays. In the data set presented here, we demonstrated the ability to type rhinoviruses and distinguish between human herpesvirus 6B and 6A, adenovirus types A and C, and polyomaviruses JC and BK. Notably, influenza A virus was identified precapture but could only be typed as an H3N2 virus post-capture. We used ViroCap to sequence the enterovirus D68 genome directly from clinical samples, and in that work, the extensive sequence data that we obtained allowed us carry out detailed comparative analysis of closely related strains that differed at a limited number of nucleotide positions. Second, the use of ViroCap can reduce the depth of sequencing needed to detect viruses in samples. Because targeted sequence capture results in a large increase in the percentage of sequencing reads that are viral (Table 1, Table 2, Table 4, Table 5, Table 6, FIG. 2), ViroCap achieves better viral coverage while requiring the generation of fewer total sequence reads. This increased efficiency has the potential to lower sequencing costs.

An important feature of ViroCap is the tiling of capture probes across genomes, including highly conserved regions that may allow detection of genomic fragments of divergent viruses that share little overall sequence homology with known viruses. We illustrated such capability using anelloviruses containing divergent nucleotide sequence (FIG. 3). In addition, the inclusion of Genome Neighbor targets enhanced our design not only by expanding beyond the tiled Reference Sequence (RefSeq) viruses but also by adding sensitivity for genomic regions where RefSeq capture probes alone might not have captured divergent strains (see Methods). ViroCap cannot detect viruses that do not share any nucleotide sequence similarity to known viruses; however, we note that because the enrichment of viral nucleic acids occurs after sequence library construction, the uncaptured portion of the library could subsequently be sequenced for additional attempts at pathogen discovery. Furthermore, the ViroCap panel is extensible and will be updated periodically with new viral sequences as they are added to RefSeq and the Genome Neighbors databases. Updates will be publicly available through our GitHub repository (see Data Access).

There were a few genomes (fewer than 10) in the NCBI reference databases that had been cloned into bacterial vectors prior to sequencing, and the deposited viral genome sequences contained bacterial vector sequence. We were not aware of this prior to probe design, so ViroCap includes capture probes that target these sequences. This resulted in enrichment of some sequences (on average 1.1% of total nonviral reads) that were subsequently recognized by our analysis pipeline as bacterial based on nucleotide sequence alignment. In subsequent versions of ViroCap, we will filter out these bacterial vector sequences.

In the experiments reported here, we pooled sequencing libraries prior to targeted sequence capture in order to reduce cost, but we still achieved enhanced detection of multiple viruses of varying abundance. As has been reported for strategies that involve sequencing indexed, pooled libraries (Kircher et al. 2012), we observed some sample cross-contamination. This cross-contamination is recognizable when a high number of viral sequences are detected in the truly positive sample, while few sequences (<0.05% of the viral sequences in the truly positive sample) of the same virus are detected in other samples in the pool. In a clinical setting, each sample would optimally be captured and sequenced independently to reduce the possibility of sample cross-contamination. However, future methodological improvements could allow pooling of clinical specimens.

The success of viral targeted sequence capture is affected by the representation of the virus in the sequencing library. In our sample preparation, total nucleic acid extracted from the sample was reverse transcribed and randomly amplified prior to library construction (Wang et al. 2003), allowing detection of DNA and RNA viral genomes within the same sequencing experiment. The uneven sequence representation observed for some genomes (FIG. 2) is likely due in part to detection of messenger RNA, whose abundance reflects patterns of gene expression, as well as to primer biases during the reverse transcription and amplification steps. Capture hybridization may also induce bias, in that sequences that diverge from target probe sequences may be captured less efficiently than those with exact or nearly exact matches to the probe. Taken together, these data suggest that further improvement in the performance of viral targeted sequence capture may be achievable by improving efficiency of reverse transcription, amplification, and library construction, while continuing to update the ViroCap panel as new, divergent genome sequences become available.

Methods other than genome sequencing have been used for virus characterization and discovery, including Virochip, a microarray-based method for detection/genotyping of viral pathogens (Wang et al. 2002; Chen et al. 2011), and Patho-Chip, a microarray designed to detect viruses and other microbial pathogens (Baldwin et al. 2014). While designed to detect known viruses by means of microarray probe spotting, this technology has also shown the ability to detect emerging viruses (Wang et al. 2003; Yu et al. 2012). The primary difference between the designs of these microarrays and ViroCap targeted sequence capture is that the latter approach targets complete viral genomes while the microarrays target smaller, discrete genomic regions. The results obtained from each approach also differ significantly. The microarray approach detects the presence of a virus but does not directly provide sequence information. In contrast, MSS enhanced by ViroCap targeted sequence capture provides sequence data, sometimes covering the entire genome.

In conclusion, ViroCap greatly enhances the sensitivity of MSS for nucleotide sequence-based virus detection. To our knowledge, ViroCap represents the first effort to apply a targeted sequence capture approach to the detection of a comprehensive set of viruses. Its research applications are far reaching, allowing a new, higher-resolution view of eukaryotic DNA and RNA viruses in the microbiome. Viro-Cap should also help realize the potential of MSS as a clinical diagnostic tool that can simultaneously detect viruses and provide immediate characterization, including taxonomic assignment, strain typing, virulence characteristics, and anti-viral drug resistance genotyping. ViroCap could also be modified into a tool for broader pathogen identification, which might include a comprehensive set of human pathogens: genes from viruses, bacteria (e.g., toxin genes, antibiotic resistance genes), fungi, protists, and other microbes.

Methods for the Examples

Taxonomy selection: At the time, we designed the Viro-Cap panel, NCBI GenBank had available for download a total of ~1 Gb of sequence representing 440 viral families, well beyond the 200 Mb of target space supported by the custom SeqCap EZ library format (NimbleGen). Therefore, we developed the following approach for selecting representative targeted sequence capture probes. Because we were interested in studying viral diseases of humans, we excluded bacteriophages and endogenous human retroviruses. We also specifically did not include references from the following NCBI viral reference genome database host categories: algae, archaea, bacteria, diatom, environment, fungi, invertebrates, plants, and protozoa. After filtering, our target list contained reference sequences from the following host categories: human, vertebrates, and "unknown." This list included viruses that could have both vertebrate and invertebrate hosts, such as vertebrate viruses with insect vectors. Based on these broad viral-host categories, we downloaded all of the associated viral reference sequences in each chosen category from NCBI (accessed Feb. 3, 2014). These sequences comprise the core reference database from which our capture library is designed. Our capture library includes targets from 34 viral families composed of 190 annotated viral genera and 337 species (FIG. 1; Supplemental Tables S6, S7 of Wylie et al., Enhanced virome sequencing using targeted sequence capture. *Genome Res* 2015; 24(12): 1910-20, the disclosure of which is hereby incorporated by reference in its entirety, including all supplemental information and zip files associated with the publication). Sources of viral sequences include complete representation of the viral genomes from NCBI's RefSeq collection, complementary representation of unique regions from Genome Neighbor targets, selected representation of NCBI Influenza Virus Resource sequences, and the entirety of the probe space represented on the Virochip microarray (Yu et al. 2012), GEO accession number GPL15905. The methods used to consolidate these database sequences follow.

RefSeq: NCBI's RefSeq (www.ncbi.nlm.nih.gov/refseq/) genome collection is a database of taxonomically diverse entries representing comprehensive, well-annotated genome sequences (Pruitt et al. 2014; Tatusova et al. 2014). As RefSeq entries are the most complete sequence representatives in terms of annotation and metadata consistency, we targeted selected viral RefSeqs by tiling of targeted sequence capture probes across the entire length of each RefSeq's genome, with the intention of capturing the entire viral genome. For our capture library, RefSeq nucleotide FASTA sequences were downloaded for desired viral-host categories (human; vertebrates; vertebrates, human; vertebrates, invertebrates; vertebrates, invertebrates, human; invertebrates, vertebrates; unknown) using both the online NCBI taxonomy viewer (www.ncbi.nlm.nih.gov/genomes/GenomesGroup.cgi?opt=virus&taxid=10239), as well as the RefSeq-specific FTP site (ftp.ncbi.nlm.nih.gov/refseq/release/viral). Entries were merged to avoid redundancy. RefSeq targets were pooled with the other sequence candidates (see Design Consolidation). A total of 1456 RefSeq FASTA entries (26.9 Mb) representing 190 viral genera were completely tiled for inclusion in the ViroCap library, accounting for 13.5% of the total capture library's target space.

Genome Neighbors: While RefSeq entries are single, canonical species representations, other complete or partial viral sequences also exist in DDBJ/EMBL/GenBank. In the case of viral sequences, there is extensive redundancy in these databases due to the large number of similar viral strains, isolates, and mutants. Therefore, non-RefSeq (e.g., DDBJ, EMBL, GenBank) nucleotide sequences of complete viral genomes that belong to the same species as a RefSeq sequence are classified as Genome Neighbors for that reference sequence, provided that they match all of the criteria that were used to select complete genomic sequences (Bao et al. 2004). At the time of our ViroCap panel design, Genome Neighbors (sequences downloaded from Entrez Genome link "Other genomes for species"; accessed Feb. 3, 2014) in total represented an additional 56,314 entries and 507.1 Mb of sequence, more than 2.5 times our SeqCap EZ capture target sequence space limit. Therefore, an alternative target selection approach was employed to add diversity to our RefSeq selections by selecting unique, complementary Genome Neighbor sequences.

RefSeq and Genome Neighbor sequence association: We began the process of variant sequence selection by identifying conserved regions in Genome Neighbors already represented by completely tiled RefSeq capture probes. First, we associated our viral RefSeq selections with corresponding Genome Neighbors. This was performed by downloading Genome Neighbor annotation files from NCBI (www.ncbi.nlm.nih.gov/genomes/GenomesGroup.cgi?opt=virus&taxid=10239) and associating the information with our RefSeq annotation files, by means of ad hoc Perl parsing and coupling scripts (for results, see Supplemental Tables S6, S7 of Wylie et al., Enhanced virome sequencing using targeted sequence capture. *Genome Res* 2015; 24(12): 1910-20, the disclosure of which is hereby incorporated by reference in its entirety, including all supplemental information and zip files associated with the publication). Once associated, the parent RefSeq sequences could be compared with related Genome Neighbor sequences to determine conserved and divergent nucleotide regions. Each viral RefSeq entry was individually reviewed, along with associated Genome Neighbor entries. FASTA sequences were collected for each RefSeq entry and its related Genome Neighbors for subsequent k-mer analysis.

K-mer analysis: Each of the Genome Neighbor sequences was split into 100-bp k-mers by means of an exhaustive 1-bp sliding window algorithm, as depicted in FIG. 7. The resultant output thus included all possible 100-bp sequences based on the combined Genome Neighbor sequence space. As our SeqCap EZ targeted sequence capture probe lengths are 100 bp, the sequences generated by the sliding window algorithm represent the total number of possible probe combinations based on the aggregate of Genome Neighbor sequences. Based on our conservative expectation of hybridization/homology at the capture probe level, we then clustered all of the Genome Neighbor 100-mers back to the parent RefSeq sequence at ≥90% sequence identity using length-sorted FASTA entries and the UCLUST (Edgar 2010) package (version 1.1.579; parameters: -rev-id 0.90). Given that all of our candidate sequences were 100 bp in length and all RefSeq entries are >100 bp, UCLUST always used the longer RefSeq as the first seed (centroid) in which to attempt folding of other sequences. As the parent RefSeq had complete probe tiling in our design, any Genome Neighbor 100-mer with ≥90% identity was considered already represented in our capture library and therefore discarded. Genome Neighbor 100-mers with <90% identity were chosen for inclusion in the capture library. As the sliding window approach produces 100-mers that overlapped one another, we merged overlapping 100-mers based on their Genome Neighbor genomic coordinates into single contiguous spans using BEDTools (Quinlan and Hall 2010) functions.

Genome Neighbor sub-sequences: Resultant subsequences were excised as FASTA entries from corresponding Genome Neighbor references using WU-BLAST's (blast.wustl.edu) xdget application and added to the ViroCap panel. These supplementary entries are easily identifiable in our final target design, as the FASTA headers for the entries list the original parent sequence ID with the excised span indicated in curly braces (e.g., gi|1249624|embl A28090.1|HPV42 [partial] genomic sequence {SQ 2444-2644}). In this manner, for each RefSeq species, we generated Genome Neighbor subsequences from 100 bp to 21 kb in length to add to our capture panel.

These processing steps reduced the aggregate input Genome Neighbors targeted sequence space from 507.1 Mb to 153.2 Mb (Table 3), and these sequences were pooled with our other targeted capture sequence targets (see Design Consolidation). A total of 130,808 partial Genome Neighbor FASTA entries (153.2 Mb) were added for capture in our ViroCap library, accounting for 77.1% of the total capture library's target space.

Influenza Virus Resource: We obtained reference sequences from NCBI's Influenza Virus Resource database (www.ncbi.nlm.nih.gov/genomes/FLU/FLU.html), which contains sequence data from the NIAID Influenza Genome Sequencing Project, as well as from GenBank. At the time of our capture panel design, the NCBI Influenza Virus Resource contained 305,524 influenza entries, representing 458.1 Mb of sequence. This is 17 times the size of our viral RefSeq selections and three times the size of our collapsed Genome Neighbor targets. Our selected RefSeq sequences included 29 influenza RefSeq entries (each influenza virus segment is represented as a separate entry), targeted in its entirety. These sequences served as the core of influenza reference genomes against which all other influenza sequences were compared. We directly clustered the long influenza sequences using length-sorted FASTA and the UCLUST package (version 1.1.579; parameters: -rev-id 0.90). In UCLUST, a cluster is defined by one sequence, known as the centroid or representative sequence. To lessen the computational burden and ensure that our core influenza RefSeq genomes were always the longest first seeds (centroids) in UCLUST's clustering process, we artificially concatenated the 29 parent RefSeq sequences into one linear sequence representation and then split this representation into six segments ranging in size from 18-26 kb. UCLUST preferentially seeded with the long RefSeq construct segments when clustering, ensuring that clustering was first attempted within the longer, canonical references. ULCUST was run with a requirement of ≥90% sequence identity to fold into a parent influenza RefSeq entries segment. Therefore, only sequences that (1) had <90% identity to influenza RefSeq entries and (2) were subsequent centroids in non-RefSeq clusters were chosen for inclusion in our capture panel. This process reduced the aggregate input Influenza Resource Database reference sequence from 458.1 Mb to 15.7 Mb (Table 3). Finally, supplementary influenza targets were pooled with the other sequence candidates (see Design Consolidation). A total of 9759 influenza FASTA entries (15.7 Mb) were added for targeted sequence capture in our ViroCap library, accounting for 7.9% of the total capture library's target space.

Virochip microarray: Considering the biologically important short sequence signatures represented on the Virochip panel (Yu et al. 2012), as well as the comparatively small footprint, we subsumed these sequences within our targeted sequence capture panel design. The probe sequences for the microarray are publicly available at NCBI's Gene Expression Omnibus (GEO) repository (Edgar et al. 2002). We downloaded this information for Platform GPL15905 (Viro5AG-60k) as a text file (www.ncbi.nlm.nih.gov/geo/query/acc.cgi?acc=GPL15905). This platform included more than 60,000 oligonucleotides of length 60-70 bp, corresponding to 3.1 Mb of probes (Table 3). Virochip targets were pooled with the other sequence candidates (see Design Consolidation). Upon review, 1.3 Mb of the probes were already directly represented by RefSeq, Genome Neighbor, and Influenza Viral Resource sequences during capture library design and synthesis. Therefore, the remaining 25,749 (60-70 bp) Virochip FASTA entries of 1.8-Mb total size were added to ViroCap, accounting for <1% of the total targeted sequence capture panel.

Design consolidation: All of our selected candidate target sequences from RefSeq, Genome Neighbors, Influenza Virus Resource, and the Virochip microarray were combined into a single FASTA sequence file. Human endogenous retroviruses were removed from inclusion by means of a two-part process: (1) Entries were filtered by taxonomic annotation indicating human endogenous retrovirus identity, and (2) the remaining entries were BLAST-aligned to the GRCh37-lite build of the human reference genome to remove sequences with high percentage identity (≥75%) at the 100-bp probe level. Finally, sequences were hard-masked (i.e., bases converted to N's) in low complexity regions using the DUST (R Tatusov and D J Lipman, unpubl.) software module. The final ViroCap targeted sequence capture panel consists of 185,835 FASTA sequences totaling 198.9 Mb (see Taxonomy Selection).

NimbleGen sequence capture design: Our consolidated target sequences were submitted to Roche NimbleGen for capture library design and synthesis. As our final ViroCap design required 198.9 Mb, manufacturing was implemented under the custom NimbleGen SeqCap EZ Developer Library format, which has a maximum capture space of 200 Mb of nonhuman sequence. NimbleGen's Sequence Capture design offered up to 2.1 million of 50-105mer sequence probes. It was at the discretion of NimbleGen, based on proprietary algorithms, to redistribute probes for better capture uniformity, redundancy, and comprehensive target base coverage. NimbleGen provided us with a proposed capture design accompanied by coordinate (GFF, BED) files and associated sequence coverage metrics. The design set contained probe representation generated by first masking all but one exact copy of each 100-mer in our original FASTA file, tiling the unmasked regions, screening the resulting probes against the (hg19) human genome, and finally selecting only those probes that had no matches in the human genome as determined by the SSAHA (Ning et al. 2001) algorithm. NimbleGen provides two metrics for assessing in silico targeted sequence capture design coverage: (1) Target bases covered with 0-bp-offset are determined by counting target bases directly represented in probe sequences, and (2)

target bases covered with 100-bp-offset are determined by counting all target bases within 100 bp of a probe. The capture design provided 95.9% 0-bp-offset coverage and 99.6% 100-bp-offset coverage of our initial 198.9-Mb target request. We approved the design for capture library synthesis and received our first 12 SeqCap EZ Library reactions for in-house Illumina sequencing and analysis.

Human subjects approval and sample selection: Samples were collected under protocols approved by the Human Research Protection Office at Washington University School of Medicine (IRB protocol nos. 201106177, 201102561, and 201102045). Samples were selected to represent a broad range of viruses that are commonly encountered in the clinical laboratory and in our research studies. Viruses were identified in samples based on clinical laboratory test results in the Diagnostic Virology Laboratory at St. Louis Children's Hospital or by PCR assays and sequencing results carried out in previous studies (Colvin et al. 2012; McElvania TeKippe et al. 2012; Wylie et al. 2012). Specimens of nasopharyngeal secretions, plasma, and stool were included.

Sequencing: Total nucleic acid was extracted from clinical samples using the EasyMag NucliSENS instrument (bioMerieux). Samples were processed in one of two ways. In experiment 1, nucleic acids from clinical specimens from the Diagnostic Virology Laboratory were combined, and the resulting pooled nucleic acid was used as input for a single sequencing library (constructed as described below). These samples are designated with a sample identification prefix of "P" in the various tables and figures. Alternatively, in experiment 2, individual sequencing libraries were made from each set of eight different specimens prior to combining the libraries for sequencing. These samples are designated with a sample identification prefix of "S" in the various tables.

For sequencing libraries, DNA and RNA viruses were assessed in the same assay as previously described (Wang et al. 2003). Specifically, the RNA in the total nucleic acid was reverse transcribed with reverse transcriptase (Promega) and random nonomers tagged with a conserved sequence (5'-GTTTCCCAGTCACGATA-3'-SEQ ID NO:1) to be used for subsequent amplification (Integrated DNA Technologies), and second strand synthesis was carried out with Sequenase V2.0 DNA polymerase (Affymetrix). DNA and RNA were subsequently amplified with Accuprime Taq (Life Technologies) using the conserved sequence on the ends of the random primers, and the DNA/cDNA mixture was sheared using the Qsonica Q800R instrument (Qsonica) to generate fragments with an average length of 500 bp. Dual-indexed sequencing libraries were constructed using the KAPA low throughput library construction kit (KAPA Biosystems).

For the *anellovirus* samples, DNA was amplified with the Illustra GenomiPhi V2 DNA amplification kit (GE Healthcare Life Sciences); RNA was not assessed. DNA was sheared, and libraries were constructed from each sample as described above. Sequencing libraries were pooled.

In each case, the libraries were divided, and part was directly sequenced (precapture) and part was subjected to targeted sequence capture with the custom ViroCap probes prior to sequencing (post-capture). Targeted sequence capture was carried out according to the manufacturer's specifications. We carried out 10, 10, and 16 cycles of post-capture linker-mediated PCR for experiments 1 (pooled clinical samples), 2 (individual samples from the research study), and 3 (*anellovirus* samples), respectively, prior to sequencing. The number of cycles was empirically determined to be the minimum number needed to obtain a 5 nM dilution of library material for qPCR and loading. Libraries were sequenced on the Illumina HiSeq 2000 or HiSeq 2500 instrument, generating 100-bp paired-end reads.

Sequence analysis: Viral sequences were identified based on nucleotide and translated protein sequence alignment against reference genomes. The pipeline is adapted from previously described methods (Wylie et al. 2014), except that nucleotide alignments were carried out using BWA-MEM with default settings (Li and Durbin 2009). Because many similar genomes are included in the reference database, we used the initial alignment statistics for each sample to choose a single reference from each species to calculate and report coverage statistics. References were chosen based on having the highest number of reference bases covered. Sequences were realigned to the selected references with BWA-MEM for calculation of coverage statistics and comparison of samples precapture and post-capture. Sequence alignments were evaluated with SAMtools (Li 2011), and sequence coverage was determined with RefCov (gmt.genome.wustl.edu/packages/refcov/) and visualized with Plot2 (plot2doc.micw.eu). For illustrative purposes, the genome coverage panels in FIG. 2 and FIG. 3 were normalized by removing (deduplicating) reads based on identical alignment start sites using the SAMtools rmdup command. For each alignment start site, only the highest-quality read was retained for forward and reverse alignment orientations. Therefore, for the 100-bp read data shown in each coverage panel, the theoretical maximum depth is 200×.

*Anellovirus* contigs were assembled from the precapture sequence data using IDBA-UD (Peng et al. 2012). Contigs were aligned against the sequence database used to design the ViroCap panel using BLAST (Altschul et al. 1997) with the following parameters to detect low-similarity sequences: -G 5 -E 2 -r 1 -q -1. The percentage identity of the top HSP is reported in Table 5.

REFERENCES FOR THE EXAMPLES

1. Albert T J, Molla M N, Muzny D M, Nazareth L, Wheeler O, Song X, Richmond T A, Middle C M, Rodesch M J, Packard C J, et al. 2007. Direct selection of human genomic loci by microarray hybridization. Nat Methods 4: 903-905.
2. Allander T, Emerson S U, Engle R E, Purcell R H, Bukh J. 2001. A virus discovery method incorporating DNase treatment and its application to the identification of two bovine parvovirus species. Proc Natl Acad Sci 98: 11609-11614.
3. Altschul S F, Madden T L, Schaffer A A, Zhang J, Zhang Z, Miller W, Lipman D J. 19 97. Gapped BLAST and PSI-BLAST: a new generation of protein database search programs. Nucleic Acids Res 25: 3389-3402.
4. Arumugam M, Raes J, Pelletier E, LePaslier D, Yamada T, Mende D R, Fernande s G R, Tap J, Bruls T, Batto J-M, et al. 2011. Enterotypes of the human gut microbiome. Nature 473: 174-180.
5. Baldwin D A, Feldman M, Alwine J C, Robertson E S. 2014. Metagenomic assay for identification of microbial pathogens in tumor tissues. MBio 5: e01714-14.
6. Bao Y, Federhen S, Leipe O, Pham V, Resenchuk S, Rozanov M, Tatusov R, Tat usova T. 2004. National center for biotechnology information viral genomes project. J Virol 78: 7291-7298.
7. Breitbart M, Rohwer F. 2005. Method for discovering novel DNA viruses in blood using viral particle selection and shotgun sequencing. Biotechniques 39:729-736.

8. Chen E C, Miller S A, DeRisi J L, Chiu C Y. 2011. Using a pan-viral microarray assay (Virochip) to screen clinical samples for viral pathogens. J Vis Exp 2536.
9. Chiu C Y. 2013. Viral pathogen discovery. Curr Opin Microbiol 16: 468-478.
10. Cleland E J, Bassioni A, Boase S, Dowd S, Vreugde S, Wormald P-J. 2014. The fungal microbiome in chronic rhinosinusitis: richness, diversity, postoperative changes and patient outcomes. Int Forum Allergy Rhinol 4: 259-265.
11. Colvin J M, Muenzer J T, Jaffe D M, Smason A, Deych E, Shannon W O, Arens M, Buller R S, Lee W M, Weinstock E J S, et al. 2012. Detection of viruses in young children with fever without an apparent source. Pediatrics 130: e1455-e1462.
12. de Villiers E-M, Borkosky S S, Kimmel R, Gunst K, Fei J-W. 2011. The diversity of torque teno viruses: in vitro replication leads to the formation of additional replication-competent subviral molecules. J Viral 85: 7284-7295.
13. DeVlaminck I, Khush K K, Strehl C, Kohli B, Luikart H. Neff N F, Okamoto J, Snyder T M, Cornfield O N, Nicolls M R, et al. 2013. Temporal response of the human virome to immunosuppression and antiviral therapy. Cell 155:1178-1187.
14. Depledge D P, Falser A L, Watson S J, Lai I Y C, Gray E R, Grant P, Kanda R K, Leproust E, Kellam P, Breuer J. 2011. Specific capture and whole-genome sequencing of viruses from clinical samples. PLoS One 6: e27805.
15. Duhaime M B, Sullivan M B. 2012. Ocean viruses: rigorously evaluating the metagenomic sample-to-sequence pipeline. Virology 434: 181-186.
16. Duncavage E J, Magrini V, Becker N, Armstrong J R, Demeter R T, Wylie T, Abel H J, Pfeifer J O. 2011. Hybrid capture and next-generation sequencing identify viral integration sites from formalin-fixed, paraffin-embedded tissue. J Mol Diagn 13:325-333.
17. Edgar R C. 2010. Search and clustering orders of magnitude faster than BLAST. Bioinformatics 26: 2460-2461.
18. Edgar R, Domrachev M, Lash A E. 2002. Gene Expression Omnibus: NCBI gene expression and hybridization array data repository. Nucleic Acids Res 30:207-210.
19. Findley K, Oh J, Yang J, Conlan S, Deming C, Meyer J A, Schoenfeld O, Nomicos E, Park M; NIH Intramural Sequencing Center Comparative Sequencing Program, et al. 2013. Topographic diversity of fungal and bacterial communities in human skin. Nature 498: 367-370.
20. Gajer P, Brotman R M, Bai G, Sakamoto J, Schutte U M E, Zhong X, Koenig S S K, FuL, Ma Z S, Zhou X, et al. 2012. Temporal dynamics of the human vaginal microbiota. Sci Transl Med 4: 132ra52.
21. Hodges E, Xuan Z, Balija V, Kramer M, Molla M N, Smith S W, Middle C M, Rodesc h M J, Albert T J, Hannon G J, et al. 2007. Genome-wide in situ exon capture for selective resequencing. Nat Genet 39: 1522-1527.
22. Holtz L R, Cao S, Zhao G, Bauer I K, Denno D M, Klein E J, Antonio M, Stine O C, S nelling T L, Kirkwood C D, et al. 2014. Geographic variation in the eukaryotic virome of human diarrhea. Virology 468-470: 556-564.
23. Human Microbiome Project Consortium. 2012. Structure, function and diversity of the healthy human microbiome. Nature 486: 207-214.
24. Kircher M, Sawyer S, Meyer M. 2012. Double indexing overcomes inaccuracies in multiplex sequencing on the lumina platform. Nucleic Acids Res 40: e3.
25. Koehler J W, Hall A T, Rolfe P A, Honko A N, Palacios G F, Fair J N, Muyembe J-J, Mulembekani P, Schoepp R J, Adesokan A, et al. 2014. Development and evaluation of a panel of filovirus sequence capture probes for pathogen detection by next-generation sequencing. PLoS One 9: e107007
26. Li H. 2011. A statistical framework for SNP calling, mutation discovery, association mapping and population genetical parameter estimation from sequencing data. Bioinformatics 27: 2987-2993.
27. Li H, Durbin R, 2009. Fast and accurate short read alignment with Burrows-Wheeler transform. Bioinformatics 25: 1754-1760.
28. Lovett M, Kere J, Hinton L M. 1991. Direct selection: a method for the isolation of cDNAs encoded by large genomic regions. Proc Natl Acad Sci 88: 9628-9632.
29. Lysholm F, Wetterbom A, Lindau C, Darban H, Bjerkner A, Fahlander K, Lindberg A M, Persson B, Allander T, Andersson B. 2012. Characterization of the viral microbiome in patients with severe lower respiratory tract infections, using metagenomic sequencing. PLoS One 7: e30875.
30. McElvaniaTeKippe E, Wylie K M, Deych E, Sodergren E, Weinstock G, Starch G A. 2012. Increased prevalence of *anellovirus* in pediatric patients with fever. PLoS One 7: e50937.
31. Minot S, Sinha R, Chen J, Li H, Keilbaugh S A, Wu G D, Lewis J D, Bushman F D. 2 011. The human gut virome: inter-individual variation and dynamic response to diet. Genome Res 21: 1616-1625.
32. Ning Z, Cox A J, Mullikin J C. 2001. SSAHA: a fast search method for large DNA databases. Genome Res 11: 1725-1729.
33. Ninomiya M, Takahashi M, Shimosegawa T, Okamoto H. 2007. Analysis of the entire genomes of fifteen torque tend midi virus variants classifiable into a third group of genus *Anellovirus*. Arch Viral 152: 1961-1975.
34. Oh J, Byrd A L, Deming C, Conlan S; NISC Comparative Sequencing Program, Kong H H, Segre J A. 2014. Biogeography and individuality shape function in the human skin metagenome. Nature 514: 59-64.
35. Okou D T, Steinberg K M, Middle C, Cutler D J, Albert T J, Zwick M E. 2007. Microar ray-based genomic selection for high-throughput resequencing. Nat Methods 4: 907-909.
36. Paulino L C, Tseng C-H, Strober B E, Blaser M J. 2006. Molecular analysis of fungal microbiota in samples from healthy human skin and psoriatic lesions. J Clin Microbial 44: 2933-2941.
37. Peng Y, Leung H C M, Yiu S M, Chin F Y L. 2012. IDBA-UD: a de novo assembler for single-cell and metagenomic sequencing data with highly uneven depth. Bioinformatics 28: 1420-1428.
38. Pruitt K D, Brown G R, Hiatt S M, ThibaudNissen F, Astashyn A, Ermolaeva O, Farrell C M, Hart J, Landrum M J, McGarvey K M, et al. 2014. RefSeq: an update on mammalian reference sequences. Nucleic Acids Res 42: D756-0763.
39. Quinlan A R, Hall I M. 2010. BEDTools: a flexible suite of utilities for comparing genomic features. Bioinformatics 26: 841-842.
40. Reyes A, Haynes M, Hanson N, Angly F E, Heath A C, Rohwer F, Gordon J I. 2010. Viruses in the faecal microbiota of monozygotic twins and their mothers. Nature 466: 334-338.

41. Tatusova T, Ciufo S, Fedorov B, O'Neill K, Tolstoy I. 2014. RefSeq microbial genomes database: new representation and annotation strategy. Nucleic Acids Res 42: 0553-D559.
42. Turnbaugh P J, Hamady M, Yatsunenko T, Cantarel B L, Duncan A, Ley R E, Sogi n M L, Jones W J, Roe B A, Affourtit J P, et al. 2009. A core gut microbiome in obese and lean twins. Nature 457: 480-484.
43. Wang O, Coscoy L, Zylberberg M, Avila P C, Boushey H A, Ganem D, DeRisi J L. 2 002. Microarray-based detection and genotyping of viral pathogens. Proc Natl Acad Sci 99: 15687-15692.
44. Wang D, Urisman A, Liu Y T, Springer M, Ksiazek T G, Erdman D D, Mardis E R, Hickenbotham M, Magrini V, Eldred J, et al. 2003. Viral discovery and sequence recovery using DNA microarrays. PLoS Biol 1: E2.
45. Willger S D, Grim S L, Dolben E L, Shipunova A, Hampton T H, Morrison H G, Filkin s L M, O'Toole G A, Moulton L A, Ashare A, et al. 2014. Characterization and quantification of the fungal microbiome in serial samples from individuals with cystic fibrosis. Microbiome 2: 40.
46. Wylie K M, Mihindukulasuriya K A, Sodergren E, Weinstock G M, Starch G A. 2012. Sequence analysis of the human virome in febrile and afebrile children. PLoS One 7: e27735.
47. Wylie K M, Mihindukulasuriya K A, Zhou Y, Sodergren E, Starch G A, Weinstock G M. 2014. Metagenomic analysis of double-stranded DNA viruses in healthy adults. BMC Biol 12: 71.
48. Wylie K M, Wylie T N, Orvedahl A, Buller R S, Herter B N, Magrini V, Wilson R K, Starch G A. 2015. Genome sequence of enterovirus D68 from St. Louis, Missouri, USA. Emerging Infect Dis 21: 184-186.
49. Young J O, Chehoud C, Bittinger K, Bailey A, Diamond J M, Cantu E, Haas A R, Ab bas A, Frye L, Christie J O, et al. 2014. Viral metagenomics reveal blooms of anelloviruses in the respiratory tract of lung transplant recipients. Am J Transplant 15: 200-209.
50. Yu G, Greninger A L, Isa P, Phan T G, Martinez M A, la Luz Sanchez de M, Contreras J F, Santos-Preciado J I, Parsonnet J, Miller S, et al. 2012. Discovery of a novel polyomavirus in acute diarrheal samples from children. PLoS One 7:e49449.

TABLE 1

Results of metagenomic shotgun sequencing for pooled specimens before and after viral targeted sequence capture.

| | | | Viral sequence reads | | | Genome coverage | | | |
| | | | | | | Breadth of coverage (%) | | Depth of coverage (mean [SD]) | |
| | | | Viral read count[b] | | | | | | |
| Virus[a] | Sample ID | Virus length (bp) | Pre-capture[c] | Post-capture[d] | PVR fold increase[e] | Pre-capture | Post-capture | Pre-capture | Post-capture |
|---|---|---|---|---|---|---|---|---|---|
| Human adenovirus B, type 35 | P1 | 34,794 | 5 | 8103 | 1300 | 0.9 | 83.6 | <0.1 (0.1) | 19.3 (52.7) |
| Human bocavirus 1 | P2 | 5299 | 110 | 15,277 | 111 | 68.6 | 100.0 | 1.8 (2.0) | 251.1 (122.1) |
| Influenza A virus (H3N2) | P3 | 13,267 | 4 | 46,540 | 9335 | 2.4 | 74.0 | <0.1 (0.3) | 263.0 (394.4) |
| Influenza B virus | P4 | 14,452 | 0 | 513 | >513[f] | 0 | 9.8 | 0 | 2.6 (0.7) |
| Human parvovirus B19 | P5 | 5596 | 1867 | 474,849 | 204 | 89.8 | 100.0 | 28.8 (17.9) | 7,367.9 (4,193.0) |
| Norovirus GII-4 | P6 | 7560 | 72 | 527,656 | 5,880 | 46.5 | 98.4 | 0.8 (1.1) | 5,870.4 (8,194.3) |
| Parechovirus 1 | P7 | 7339 | 0 | 13 | >13[f] | 0 | 8.0 | 0 | 0.2 (0.6) |
| BK polyomavirus | P8 | 5142 | 1 | 1520 | 1220 | 1.6 | 88.6 | <0.1 (0.1) | 24.9 (32.2) |
| JC polyomavirus | P9 | 5121 | 5 | 2760 | 443 | 8.6 | 98.5 | 0.1 (0.3) | 46.3 (54.0) |
| Human rhinovirus 15 | P10 | 7134 | 8 | 9624 | 965 | 8.8 | 82.9 | 0.1 (0.3) | 115.9 (170.3) |
| Human respiratory syncytial virus, type B | P11 | 15,283 | 9 | 67,778 | 6042 | 3.0 | 89.5 | <0.1 (0.3) | 350.1 (1,667.2) |
| Human herpesvirus 1 | P12 | 152,261 | 0 | 14 | >14[f] | 0 | 0.8 | 0 | <0.1 (0.1) |
| Torque teno virus | P13 | 3260 | 1 | 447 | 447 | 1.78 | 60.74 | 0.02 (0.13) | 10.4 (23.4) |
| Human herpesvirus 3 | P14 | 125,030 | 0 | 834 | >834[f] | 0 | 8.33 | 0 | 0.6 (3.5) |

Precapture indicates metagenomic shotgun sequencing without targeted sequence capture; post-capture, metagenomic shotgun sequencing using (ViroCap) targeted sequence capture.
[a] Viruses listed were incorporated into a viral pool that was subjected to MSS without and with targeted sequence capture, as described in the text.
[b] Viral reads per million sequences generated precapture and post-capture are statistically different ($P < 0.0001$, Wilcoxon test).
[c] MSS of the virus pool without targeted sequence capture yielded 7,458,192 total reads.
[d] MSS of the virus pool after targeted sequence capture yielded 9,295,438 total reads.
[e] PVR (percentage viral reads) fold increase indicates percentage of post-capture viral reads divided by percentage of precapture viral reads.
[f] PVR fold increase could not be calculated because the number of precapture reads was 0.

TABLE 2

Results of metagenomic shotgun sequencing for individual specimens before and after viral targeted sequence capture.

| Sample type | Sample ID | Total reads Pre-capture | Total reads Post-capture | Virus(es) detected | Virus length (bp) | Viral read count[a] Pre-capture | Viral read count[a] Post-capture | PVR fold increase[b] | Breadth of coverage (%) Pre-capture | Breadth of coverage (%) Post-capture | Depth of coverage (mean [SD]) Pre-capture | Depth of coverage (mean [SD]) Post-capture |
|---|---|---|---|---|---|---|---|---|---|---|---|---|
| Nasopharyngeal swab | S1 | 4,202,474 | 16,080,640 | Torque teno virus | 2736 | 0 | 231 | >231[c] | 0 | 74.4 | 0 | 5.2 (7.6) |
| | | | | Human adenovirus B, type 3 | 35,269 | 15,116 | 7,703,787 | 133 | 89.6 | 100.0 | 36.1 (213.8) | 19,097.4 (17,285.5) |
| Nasopharyngeal swab | S2 | 5,087,234 | 3,713,962 | TTV-like mini virus isolate | 2912 | 0 | 249 | >249[c] | 0 | 37.5 | 0 | 6.4 (18.1) |
| | | | | Human adenovirus C, type 1 | 36,002 | 87 | 116,502 | 1,834 | 15.3 | 100.0 | 0.2 (0.6) | 283.1 (422.3) |
| Nasopharyngeal swab | S3 | 5,139,462 | 4,094,568 | Torque teno mini virus | 2908 | 0 | 256 | >256[c] | 0 | 22.7 | 0 | 6.4 (21.8) |
| | | | | Human parainfluenza virus 3 | 15,462 | 172 | 262,806 | 1,918 | 39.5 | 99.9 | 1.0 (1.6) | 1,462.1 (1,767.0) |
| Nasopharyngeal swab | S4 | 6,124,424 | 5,659,554 | TTV-like mini virus isolate | 2915 | 1 | 887 | 960 | 2.8 | 13.5 | <0.1 (0.2) | 23.9 (105.7) |
| | | | | Human bocavirus 1 | 5543 | 4419 | 460,617 | 113 | 95.4 | 100.0 | 68.3 (94.1) | 7,294.7 (3,443.1) |
| Nasopharyngeal swab | S5 | 9,152,970 | 5,834,446 | Torque teno virus | 3741 | 0 | 56 | >56[c] | 0 | 14.9 | 0 | 1.0 (3.2) |
| Nasopharyngeal swab | S6 | 10,179,884 | 12,064,068 | Human adenovirus B, type 3A | 35,264 | 0 | 1071 | >1071[c] | 0 | 75.3 | 0 | 2.6 (2.8) |
| | | | | KI polyomavirus | 5040 | 1034 | 411,173 | 336 | 83.4 | 100.0 | 18.4 (20.5) | 7,373.2 (7,123.3) |
| | | | | Human rhinovirus 80 | 7138 | 19,232 | 3,120,184 | 137 | 65.0 | 75.9 | 238.2 (313.2) | 39,218.6 (102,545.7) |
| Stool | S7 | 3,691,496 | 4,104,534 | Human adenovirus C, type 1 | 36,006 | 3 | 9081 | 2,722 | 0.8 | 99.9 | <0.1 (0.1) | 22.9 (25.7) |
| | | | | Sapovirus | 7429 | 33 | 61,982 | 1,689 | 23.3 | 100.0 | 0.4 (0.8) | 740.1 (437.6) |
| | | | | Human astrovirus 1 | 6816 | 6,641 | 1,140,900 | 155 | 99.9 | 100.0 | 85.1 (135.6) | 14,725.6 (13,370.2) |
| | | | | Human polyomavirus 10 | 4939 | 0 | 81 | >81[c] | 0 | 70.4 | 0 | 1.6 (1.6) |
| Plasma | S8 | 10,875,448 | 7,088,360 | Torque teno virus | 3880 | 0 | 1817 | >1817[c] | 0 | 38.2 | 0 | 37.0 (105.0) |
| | | | | Human herpesvirus 6B | 161,573 | 38 | 27,523 | 1111 | 1.1 | 38.4 | <0.1 (0.2) | 14.2 (112.9) |

Precapture indicates metagenomic shotgun sequencing without targeted sequence capture; post capture, metagenomic shotgun sequencing using (ViroCap) targeted sequence capture.
[a]Viral reads per million sequences generated precapture and post-capture are statistically different (P = 0.0002, Wilcoxon test).
[b]PVR fold increase indicates percentage of post-capture viral reads divided by percentage of precapture viral reads.
[c]PVR fold increase could not be calculated because the number of precapture reads was zero.

TABLE 3

Viral reference genome database size representation in the ViroCap targeted sequence capture panel.

| Reference sequence database | Viral sequence representation (Mb) | | Fold reduction |
|---|---|---|---|
| | Before targeted sequence selection | After targeted sequence selection | |
| NCBI RefSeq | 26.9 | 26.9 | 0‡ |
| NCBI Genome Neighbors | 507.1 | 153.2 | 3.3 |
| NCBI Influenza Viral Resource | 458.1 | 15.7 | 29.2 |
| Virochip microarray | 4.2 | 3.1 | 1.4 |
| | 996.3 | 198.9 | 5 |

Sources of viral sequences included in the ViroCap panel include the complete representation of the viral genomes from NCBI's Reference Sequence (RefSeq) collection, complementary representation of unique regions from Genome Neighbor targets, selected representation of NCBI Influenza Virus Resource sequences, and the entirety of the probe space represented on the Virochip microarray (Guixia Yu et al. 2012), GEO accession number GPL15905
‡Fold reduction is 0 because reference genomes were completely targeted.

TABLE 4

Genome coverage results based on metagenomic shotgun sequencing before and after viral targeted sequence capture.

| Sample ID | Sample type | Virus | Virus length (bp) | GenBank defintion | GenBank version | GenBank GI |
|---|---|---|---|---|---|---|
| P1 | pooled | Human adenovirus B, type 35 | 34794 | Human adenovirus type 35 strain Holden | AY128640.2 | GI:38196041 |
| P2 | pooled | Human bocavirus 1 | 5299 | Human bocavirus DNA, strain: JP0006-077 | AB481073.1 | GI:223670841 |
| P3 | pooled | Influenza A virus (H3N2) | 2341 | Influenza A virus (A/New York/392/2004(H3N2)) segment 1 | NC_007373.1 | GI:73919059 |
| P4 | pooled | Influenza B virus | 2204 | Influenza B virus RNA-3 | NC_002206.1 | GI:8486150 |
| P5 | pooled | Human parvovirus B19 | 5596 | Human parvovirus B19 | NC_000883.2 | GI:356457872 |
| P6 | pooled | Norovirus GII-4 | 7560 | Norovirus Hu/GII.4/Armidale/NSW3901/2008/AU | GQ845369.3 | GI:374674593 |
| P7 | pooled | Parechovirus 1 | 7339 | Current classification: Parechovirus 1 (Former name: Echovirus 22 1AB, 1C, 1D, 2A, 2B, 2C, 3A, 3B, 3C, 3D proteins RNA) | LQ2971.1 | GI:323688 |
| P8 | pooled | BK polyomavirus | 5142 | BK polyomavirus DNA, isolate: KEN-1 | AB263926.1 | GI:119926680 |
| P9 | pooled | JC polyomavirus | 5121 | JC virus DNA isolate:N4 | AB048554.1 | GI:15823368 |
| P10 | pooled | Human rhinovirus 15 | 7134 | Human rhinovirus 15 | DQ473493.1 | GI:95102501 |
| P11 | pooled | Human respiratory syncytial virus, type B | 15283 | Human respiratory syncytial virus strain NH1067 | JQ582844.1 | GI:384872840 |
| P12 | pooled | Human herpesvirus 1 | 152261 | Human herpesvirus 1 | NC_001806.1 | GI:9629378 |
| P13 | pooled | Torque teno virus | 3260 | Torque teno virus strain SIA109 | FJ426280.1 | GI:217416834 |
| P14 | pooled | Human herpesvirus 3 | 125030 | Human herpesvirus 3 strain 36 | DQ479958.1 | GI:94482166 |
| S1 | single | Torque teno virus | 3736 | Torque teno virus 7 | NC_014080.1 | GI:295413954 |
| S1 | single | Human adenovirus B, type 3 | 35269 | Human adenovirus B strain Guangzhou02 | DQ105654.4 | GI:93308305 |
| S2 | single | TTV-like mini virus isolate | 2912 | TTV-like mini virus isolate TTMV_LY1 | NC_020498.1 | GI:470457049 |
| S2 | single | Human adenovirus C, type 1 | 36002 | Human adenovirus C strain human/USA/VT13862/2004/1[P1H1F1] | JX173086.1 | GI:406679291 |
| S3 | single | Torque teno mini virus | 2908 | Torque teno mini virus 5 | NC_014089.1 | GI:295441877 |
| S3 | single | Human parainfluenza virus 3 | 15462 | Human parainfluenza virus 3 strain ZHYMgz01 | EU326526.1 | GI:163866863 |
| S4 | single | TTV-like mini virus isolate | 2915 | TTV-like mini virus isolate TTMV_LY3 | JX134046.1 | GI:459958124 |
| S4 | single | Human bocavirus 1 | 5543 | Human bocavirus isolate Salvador1 | JQ923422.1 | GI:404159467 |
| S5 | single | Torque teno virus | 3741 | Torque teno virus, isolate tth21 | AJ620217.1 | GI:49202965 |
| S6 | single | Human adenovirus B, type 3A | 35264 | Human adenovirus B strain human/USA/ak32_AdV3a/2004/3[P3H3F3] | JX423380.1 | GI:402173169 |

TABLE 4-continued

Genome coverage results based on metagenomic shotgun sequencing before and after viral targeted sequence capture.

| Sample ID | | | | | | | | |
|---|---|---|---|---|---|---|---|---|
| S6 | single | KI polyomavirus | 5040 | K1 polyomavirus Stockholm 380 | | | EF127908.1 | GI:124366193 |
| S6 | single | Human rhinovirus 80 | 7138 | Human rhinovirus 80 strain ATCC VR-1190 | | | FJ445156.1 | GI:217316442 |
| S7 | single | Human adenovirus C, type 1 | 36006 | Human adenovirus C strain human/USA/VT2612/2003/1[P1H1F1] | | | JX173085.1 | GI:406679245 |
| S7 | single | Sapovirus | 7429 | Sapovirus Chanthaburi-74/Thailand | | | AY646854.2 | GI:380877195 |
| S7 | single | Human astrovirus 1 | 6816 | Human astrovirus 1 strain Hu/Nyergesujfalu/HUN4520/2010/HUN | | | HQ398856.2 | GI:313759913 |
| S7 | single | Human polyomavirus 10 | 4939 | Human polyomavirus 10 isolate 10ww | | | JX262162.1 | GI:394995074 |
| S8 | single | Torque teno virus | 3880 | Torque teno virus, isolate TTV-HD20d (ur0746) | | | FR751495.1 | GI:339511371 |
| S8 | single | Human herpesvirus 6B | 161573 | Human herpesvirus 6B DNA, strain: HST | | | AB021506.1 | GI:4995977 |

Pre-capture: Metagenomic shotgun sequencing without targeted sequence capture

| Sample ID | Percent of reference bases covered[a] | No. of reference bases | No. of covered bases | No. of Missing Bases | Ave. coverage depth[b] | Std dev of ave. coverage depth | Median coverage depth | No. of gaps[c] | Ave. gap length (bp) | Standard deviation of ave. gap length (bp) | Median gap length (bp) | No. of reads layered |
|---|---|---|---|---|---|---|---|---|---|---|---|---|
| P1 | 0.94 | 34794 | 328 | 34466 | 0.01 | 0.11 | 0 | 5 | 6893.2 | 6429.83 | 6259 | 5 |
| P2 | 68.64 | 5299 | 3637 | 1662 | 1.79 | 1.98 | 1 | 20 | 83.1 | 87.51 | 49 | 110 |
| P3 | 5.85 | 2341 | 137 | 2204 | 0.06 | 0.23 | 0 | 3 | 734.67 | 621.96 | 362 | 2 |
| P4 | 0 | 2204 | 0 | 2204 | 0 | NaN | 0 | 1 | 2204 | NaN | 2204 | 0 |
| P5 | 89.8 | 5596 | 5025 | 571 | 28.77 | 17.94 | 30 | 3 | 190.33 | 150.93 | 153 | 1867 |
| P6 | 46.48 | 7560 | 3514 | 4046 | 0.8 | 1.13 | 0 | 25 | 161.84 | 162.37 | 128 | 72 |
| P7 | 0 | 7339 | 0 | 7339 | 0 | NaN | 0 | 1 | 7339 | NaN | 7339 | 0 |
| P8 | 1.58 | 5142 | 81 | 5061 | 0.02 | 0.12 | 0 | 2 | 2530.5 | 2000.5 | 2530.5 | 1 |
| P9 | 8.59 | 5121 | 440 | 4681 | 0.09 | 0.28 | 0 | 6 | 780.17 | 1012.2 | 121 | 5 |
| P10 | 8.8 | 7134 | 628 | 6506 | 0.09 | 0.31 | 0 | 8 | 813.25 | 1006.85 | 401 | 8 |
| P11 | 3.04 | 15283 | 464 | 14819 | 0.04 | 0.27 | 0 | 6 | 2469.83 | 3426.67 | 985 | 9 |
| P12 | 0 | 152261 | 0 | 152261 | 0 | NaN | 0 | 1 | 152261 | NaN | 152261 | 0 |
| P13 | 1.78 | 3260 | 58 | 3202 | 0.02 | 0.13 | 0 | 2 | 1601 | 837 | 1601 | 1 |
| P14 | 0 | 125030 | 0 | 125030 | 0 | NaN | 0 | 1 | 125030 | NaN | 125030 | 0 |
| 51 | 0 | 3736 | 0 | 3736 | 0 | NaN | 0 | 1 | 3736 | NaN | 3736 | 0 |
| 51 | 89.56 | 35269 | 31587 | 3682 | 36.14 | 213.75 | 6 | 43 | 85.63 | 145.97 | 45 | 15116 |
| S2 | 0 | 2912 | 0 | 2912 | 0 | NaN | 0 | 1 | 2912 | NaN | 2912 | 0 |
| S2 | 15.32 | 36002 | 5515 | 30487 | 0.2 | 0.57 | 0 | 47 | 648.66 | 1049.02 | 223 | 87 |
| S3 | 0 | 2908 | 0 | 2908 | 0 | NaN | 0 | 1 | 2908 | NaN | 2908 | 0 |
| S3 | 39.54 | 15462 | 6114 | 9348 | 0.95 | 1.62 | 0 | 33 | 283.27 | 444.82 | 108 | 172 |
| S4 | 2.81 | 2915 | 82 | 2833 | 0.03 | 0.17 | 0 | 2 | 1416.5 | 1181.5 | 1416.5 | 1 |
| S4 | 95.4 | 5543 | 5288 | 255 | 68.3 | 94.09 | 41 | 3 | 85 | 65.87 | 73 | 4419 |
| S5 | 0 | 3741 | 0 | 3741 | 0 | NaN | 0 | 1 | 3741 | NaN | 3741 | 0 |
| S6 | 0 | 35264 | 0 | 35264 | 0 | NaN | 0 | 1 | 35264 | NaN | 35264 | 0 |
| S6 | 83.37 | 5040 | 4202 | 838 | 18.39 | 20.51 | 9 | 5 | 167.6 | 144.4 | 94 | 72 |
| S7 | 99.94 | 6816 | 6812 | 4 | 85.05 | 135.62 | 24 | 1 | 4 | NaN | 4 | 6641 |
| S7 | 0 | 4939 | 0 | 4939 | 0 | NaN | 0 | 1 | 4939 | NaN | 4939 | 0 |
| S8 | 0 | 3880 | 0 | 3880 | 0 | NaN | 0 | 1 | 3880 | NaN | 3880 | 0 |
| S8 | 1.1 | 161573 | 1771 | 159802 | 0.02 | 0.23 | 0 | 15 | 10653.47 | 11967.21 | 5510 | 38 |

Post-capture: Metagenomic shotgun sequencing using (ViroCap) targeted sequence capture

| Sample ID | Percent of reference bases covered[a] | No. of reference bases | No. of covered bases | No. of Missing Bases | Ave. coverage depth[b] | Std dev of ave. coverage depth | Median coverage depth | No. of gaps[c] | Ave. gap length (bp) | Std dev of ave. gap length (bp) | Median gap length (bp) | No. of reads layered | ΔBoC[d] |
|---|---|---|---|---|---|---|---|---|---|---|---|---|---|
| P1 | 83.57 | 34794 | 29076 | 5718 | 19.33 | 52.7 | 3 | 87 | 65.72 | 61.71 | 42 | 8103 | 82.63 |
| P2 | 100 | 5299 | 5299 | 0 | 251.09 | 122.05 | 233 | 0 | 0 | NaN | 0 | 15277 | 31.36 |
| P3 | 98.25 | 2341 | 2300 | 41 | 591.6 | 575.04 | 382 | 2 | 20.5 | 6.5 | 20.5 | 15528 | 92.4 |
| P4 | 30.35 | 2204 | 669 | 1535 | 13.19 | 30.71 | 0 | 4 | 383.75 | 357.82 | 294 | 338 | 30.35 |
| P5 | 100 | 5596 | 5596 | 0 | 7367.86 | 4193 | 7460 | 0 | 0 | NaN | 0 | 474849 | 10.2 |
| P6 | 98.35 | 7560 | 7435 | 125 | 5870.35 | 8194.3 | 4296 | 4 | 31.25 | 36.18 | 15.5 | 527656 | 51.87 |
| P7 | 7.97 | 7339 | 585 | 6754 | 0.15 | 0.58 | 0 | 6 | 1125.67 | 1545.22 | 94.5 | 13 | 7.97 |
| P8 | 88.64 | 5142 | 4558 | 584 | 24.88 | 32.24 | 13 | 7 | 83.43 | 67.22 | 80 | 1520 | 87.06 |
| P9 | 98.48 | 5121 | 5043 | 78 | 46.27 | 53.99 | 24 | 4 | 19.5 | 16.15 | 12 | 2760 | 89.89 |
| P10 | 82.86 | 7134 | 5911 | 1223 | 115.85 | 170.32 | 40 | 10 | 122.3 | 121.68 | 83.5 | 9624 | 74.06 |
| P11 | 89.45 | 15283 | 13671 | 1612 | 350.08 | 1667.22 | 30 | 20 | 80.6 | 96.83 | 43 | 67778 | 86.41 |
| P12 | 0.78 | 152261 | 1189 | 151072 | 0.01 | 0.1 | 0 | 11 | 13733.8 2 | 13953.16 | 7959 | 0 | 0.78 |
| P13 | 60.74 | 3260 | 1980 | 1280 | 10.41 | 23.43 | 2 | 10 | 128 | 139.87 | 51 | 447 | 58.96 |
| P14 | 8.33 | 125030 | 10410 | 114620 | 0.58 | 3.52 | 0 | 60 | 1910.33 | 3636.15 | 166.5 | 834 | 8.33 |
| S1 | 74.38 | 3736 | 2779 | 957 | 5.22 | 7.55 | 2 | 13 | 73.62 | 65.12 | 49 | 231 | 74.38 |
| S1 | 99.98 | 35269 | 35261 | 8 | 19097.35 | 17285.52 | 13455 | 2 | 4 | 2 | 4 | 7703787 | 10.42 |
| S2 | 37.5 | 2912 | 1092 | 1820 | 6.4 | 18.14 | 0 | 3 | 606.67 | 509.03 | 558 | 249 | 37.5 |

TABLE 4-continued

Genome coverage results based on metagenomic shotgun sequencing before and after viral targeted sequence capture.

| | | | | | | | | | | | | | | |
|---|---|---|---|---|---|---|---|---|---|---|---|---|---|---|
| S2 | 100 | 36002 | 36002 | 0 | 283.11 | 422.28 | 114 | 0 | 0 | NaN | 0 | 116502 | 84.68 | |
| S3 | 22.66 | 2908 | 659 | 2249 | 6.44 | 21.77 | 0 | 3 | 749.67 | 621.73 | 452 | 256 | 22.66 | |
| S3 | 99.89 | 15462 | 15445 | 17 | 1462.12 | 1766.97 | 768 | 1 | 17 | NaN | 17 | 262806 | 60.35 | |
| S4 | 13.52 | 2915 | 394 | 2521 | 23.9 | 105.69 | 0 | 3 | 840.33 | 1180.63 | 7 | 887 | 10.71 | |
| S4 | 100 | 5543 | 5543 | 0 | 7294.73 | 3443.14 | 7246 | 0 | 0 | NaN | 0 | 460617 | 4.6 | |
| S5 | 14.89 | 3741 | 557 | 3184 | 1.02 | 3.24 | 0 | 5 | 636.8 | 507.21 | 716 | 56 | 14.89 | |
| S6 | 75.3 | 35264 | 26555 | 8709 | 2.56 | 2.76 | 2 | 102 | 85.38 | 113.63 | 41.5 | 1071 | 75.3 | |
| S6 | 100 | 5040 | 5040 | 0 | 7373.19 | 7123.25 | 5338 | 0 | 0 | NaN | 0 | 411173 | 16.63 | |
| S6 | 75.89 | 7138 | 5417 | 1721 | 39218.6 | 102545.72 | 1785 | 15 | 114.73 | 144.23 | 61 | 3120184 | 10.94 | |
| S7 | 99.87 | 36006 | 35960 | 46 | 22.92 | 25.7 | 17 | 4 | 11.5 | 12.99 | 4 | 9081 | 99.1 | |
| S7 | 99.95 | 7429 | 7425 | 4 | 740.14 | 437.61 | 682 | 1 | 4 | NaN | 4 | 61982 | 76.69 | |
| S7 | 100 | 6816 | 6816 | 0 | 14725.63 | 13370.21 | 9613.5 | 0 | 0 | NaN | 0 | 1140900 | 0.06 | |
| S7 | 70.42 | 4939 | 3478 | 1461 | 1.57 | 1.57 | 1 | 19 | 76.89 | 57.73 | 70 | 81 | 70.42 | |
| S8 | 38.17 | 3880 | 1481 | 2399 | 36.98 | 104.85 | 0 | 9 | 266.56 | 261.22 | 131 | 1817 | 38.17 | |
| S8 | 38.4 | 161573 | 62045 | 99528 | 14.24 | 112.94 | 1 | 351 | 283.56 | 467.84 | 148 | 27523 | 37.3 | |

NA: Not applicable; NaN: Not a number
[a]Breadth-of coverage as a percent of total reference length (No. of covered bases divided by No. of reference bases).
[b]Mean depth-of coverage across the reference length; calculated across all positions in the reference, whether covered or uncovered.
[c]Number of gapped (uncovered) areas in context of the reference sequence.
[d]ABoC: Breadth of-coverage change calculated by subtracting percent of reference bases covered, targeted sequence capture- metagenomic shotgun sequencing.

TABLE 5

Segment-level genome coverage results for influenza A and B based on metagenomic shotgun sequencing before and after viral targeted sequence capture.

| Pre- or post-cap-ture | GenBank defintion | % of ref bases cover-ed[a] | No. of refer-ence bases | No. of covered bases | No. of Missing Bases | Ave. coverage depth[b] | Std dev of ave. coverage depth | Median coverage depth | No. of gaps[c] | Ave. gap length (bp) | Std dev gap length (bp) | Median gap length (bp) | No. of reads layered |
|---|---|---|---|---|---|---|---|---|---|---|---|---|---|
| | | | | | Influenza A (sample P3, pre-capture) | | | | | | | | |
| Pre-cap-ture | Influenza A virus H3N2 segment 1 (NC_007373.1) | 5.85 | 2341 | 137 | 2204 | 0.06 | 0.23 | 0 | 3 | 734.67 | 621.96 | 362 | 2 |
| Pre-cap-ture | Influenza A virus H3N2 segment 2 (NC_007372.1) | 0 | 2341 | 0 | 2341 | 0 | NaN | 0 | 1 | 2341 | NaN | 2341 | 0 |
| Pre-cap-ture | Influenza A virus H3N2 segment 3 (NC_007371.1) | 8.28 | 2233 | 185 | 2048 | 0.08 | 0.28 | 0 | 3 | 682.67 | 605.98 | 525 | 2 |
| Pre-cap-ture | Influenza A virus H3N2 segment 4 (NC_007366.1) | 0 | 1762 | 0 | 1762 | 0 | NaN | 0 | 1 | 1762 | NaN | 1762 | 0 |
| Pre-cap-ture | Influenza A virus H3N2 segment 5 (NC_007369.1) | 0 | 1566 | 0 | 1566 | 0 | NaN | 0 | 1 | 1566 | NaN | 1566 | 0 |
| Pre-cap-ture | Influenza A virus H3N2 segment 6 (NC_007368.1) | 0 | 1467 | 0 | 1467 | 0 | NaN | 0 | 1 | 1467 | NaN | 1467 | 0 |
| Pre-cap-ture | Influenza A virus H3N2 segment 7 (NC_007367.1) | 0 | 1027 | 0 | 1027 | 0 | NaN | 0 | 1 | 1027 | NaN | 1027 | 0 |
| Pre-cap-ture | Influenza A virus H3N2 segment 8 (NC_007370.1) | 0 | 890 | 0 | 890 | 0 | NaN | 0 | 1 | 890 | NaN | 890 | 0 |
| | | 2.36% | 13627 | 322 | 13305 | 0.0175 | 0.255 | 0 | 12 | 1308.7925 | 613.97 | 1242.5 | 4 |
| | | | | | Influenza A (sample P3, post-capture) | | | | | | | | |
| Post-cap-ture | Influenza A virus H3N2 segment 1 (NC_007373.1) | 98.25 | 2341 | 2300 | 41 | 591.6 | 575.04 | 382 | 2 | 20.5 | 6.5 | 20.5 | 15528 |

TABLE 5-continued

Segment-level genome coverage results for influenza A and B based on metagenomic shotgun sequencing before and after viral targeted sequence capture.

| Pre- or post-capture | GenBank defintion | % of ref bases covered[a] | No. of reference bases | No. of covered bases | No. of Missing Bases | Ave. coverage depth[b] | Std dev of ave. coverage depth | Median coverage depth | No. of gaps[c] | Ave. gap length (bp) | Std dev gap length (bp) | Median gap length (bp) | No. of reads layered |
|---|---|---|---|---|---|---|---|---|---|---|---|---|---|
| Post-capture | Influenza A virus H3N2 segment 2 (NC_007372.1) | 68.56 | 2341 | 1605 | 736 | 158.84 | 327.77 | 6 | 3 | 245.33 | 158.49 | 169 | 4243 |
| Post-capture | Influenza A virus H3N2 segment 3 (NC_007371.1) | 90.82 | 2233 | 2028 | 205 | 405.08 | 444.68 | 217 | 2 | 102.5 | 41.5 | 102.5 | 10482 |
| Post-capture | Influenza A virus H3N2 segment 4 (NC_007366.1) | 94.32 | 1762 | 1662 | 100 | 79.31 | 92.95 | 40 | 3 | 33.33 | 27.78 | 20 | 1602 |
| Post-capture | Influenza A virus H3N2 segment 5 (NC_007369.1) | 56.13 | 1566 | 879 | 687 | 254.47 | 437.74 | 2 | 5 | 137.4 | 216.83 | 33 | 4469 |
| Post-capture | Influenza A virus H3N2 segment 6 (NC_007368.1) | 97.82 | 1467 | 1435 | 32 | 614.1 | 881.33 | 137 | 3 | 10.67 | 4.64 | 9 | 10211 |
| Post-capture | Influenza A virus H3N2 segment 7 (NC_007367.1) | 0 | 1027 | 0 | 1027 | 0 | NaN | 0 | 1 | 1027 | NaN | 1027 | 0 |
| Post-capture | Influenza A virus H3N2 segment 8 (NC_007370.1) | 19.66 | 890 | 175 | 715 | 0.46 | 1.11 | 0 | 3 | 238.33 | 232.54 | 132 | 5 |
| | | 74.00% | 13627 | 10084 | 3543 | 262.9825 | 0.1586 | 98 | 22 | 226.8825 | 98.3257 | 189.125 | 46540 |
| | Influenza B (sample P4, pre-capture) | | | | | | | | | | | | |
| Pre-capture | Influenza B virus RNA 1 (NC_002204.1) | 0 | 2368 | 0 | 2368 | 0 | NaN | 0 | 1 | 2368 | NaN | 2368 | 0 |
| Pre-capture | Influenza B virus RNA 2 (NC_002205.1) | 0 | 2313 | 0 | 2313 | 0 | NaN | 0 | 1 | 2313 | NaN | 2313 | 0 |
| Pre-capture | Influenza B virus RNA 3 (NC_002206.1) | 0 | 2204 | 0 | 2204 | 0 | NaN | 0 | 1 | 2204 | NaN | 2204 | 0 |
| Pre-capture | Influenza B virus RNA 4 (NC_002207.1) | 0 | 1882 | 0 | 1882 | 0 | NaN | 0 | 1 | 1882 | NaN | 1882 | 0 |
| Pre-capture | Influenza B virus RNA 5 (NC_002208.1) | 0 | 1841 | 0 | 1841 | 0 | NaN | 0 | 1 | 1841 | NaN | 1841 | 0 |
| Pre-capture | Influenza B virus RNA 6 (NC_002209.1) | 0 | 1557 | 0 | 1557 | 0 | NaN | 0 | 1 | 1557 | NaN | 1557 | 0 |
| Pre-capture | Influenza B virus RNA 7 (NC_002210.1) | 0 | 1191 | 0 | 1191 | 0 | NaN | 0 | 1 | 1191 | NaN | 1191 | 0 |
| Pre-capture | Influenza B virus RNA 8 (NC_002211.1) | 0 | 1096 | 0 | 1096 | 0 | NaN | 0 | 1 | 1096 | NaN | 1096 | 0 |
| | | 0.00% | 14452 | 0 | 14452 | 0 | NaN | 0 | 8 | 1806.5 | NaN | 1806.5 | 0 |
| | Influenza B (sample P4, post-capture) | | | | | | | | | | | | |
| Post-capture | Influenza B virus RNA 1 (NC_002204.1) | 0 | 2368 | 0 | 2368 | 0 | NaN | 0 | 1 | 2368 | NaN | 2368 | 0 |
| Post-capture | Influenza B virus RNA 2 (NC_002205.1) | 15.56 | 2313 | 360 | 1953 | 2.08 | 6.42 | 0 | 2 | 976.5 | 275.5 | 976.5 | 58 |
| Post-capture | Influenza B virus RNA 3 (NC_002206.1) | 30.35 | 2204 | 669 | 1535 | 13.19 | 30.71 | 0 | 4 | 383.75 | 357.82 | 294 | 338 |
| Post-capture | Influenza B virus RNA 4 (NC_002207.1) | 14.24 | 1882 | 268 | 1614 | 4.6 | 11.57 | 0 | 2 | 807 | 195 | 807 | 99 |

TABLE 5-continued

Segment-level genome coverage results for influenza A and B based on metagenomic shotgun sequencing before and after viral targeted sequence capture.

| Pre- or post-capture | GenBank defintion | % of ref bases covered[a] | No. of reference bases | No. of covered bases | No. of Missing Bases | Ave. coverage depth[b] | Std dev of ave. coverage depth | Median coverage depth | No. of gaps[c] | Ave. gap length (bp) | Std dev gap length (bp) | Median gap length (bp) | No. of reads layered |
|---|---|---|---|---|---|---|---|---|---|---|---|---|---|
| Post-capture | Influenza B virus RNA 5 (NC_002208.1) | 0 | 1841 | 0 | 1841 | 0 | NaN | 0 | 1 | 1841 | NaN | 1841 | 0 |
| Post-capture | Influenza B virus RNA 6 (NC_002209.1) | 7.58 | 1557 | 118 | 1439 | 0.89 | 3.52 | 0 | 2 | 719.5 | 454.5 | 719.5 | 18 |
| Post-capture | Influenza B virus RNA 7 (NC_002210.1) | 0 | 1191 | 0 | 1191 | 0 | NaN | 0 | 1 | 1191 | NaN | 1191 | 0 |
| Post-capture | Influenza B virus RNA 8 (NC_002211.1) | 0 | 1096 | 0 | 1096 | 0 | NaN | 0 | 1 | 1096 | NaN | 1096 | 0 |
| | | 9.79% | 14452 | 1415 | 13037 | 2.595 | 0.6488 | 0 | 14 | 1172.84375 | 296.7109 | 1161.625 | 513 |

Pre-capture: Metagenomic shotgun sequencing without targeted sequence capture.
Post-capture: Metagenomic shotgun sequencing using (ViroCap) targeted sequence capture.
NA: Not applicable; NaN: Not a number
[a]Breadth-of-coverage as a percent of total reference length (No. of covered bases divided by No. of reference bases).
[b]Mean depth-of-coverage across the reference length; calculated across all positions in the reference, whether covered or uncovered.
[c]Number of gapped (uncovered) areas in context of the reference sequence.

TABLE 6

Anellovirus contig coverage results based on metagenomic shotgun sequencing before and after viral targeted sequence capture

| ID | Source | Pre-capture read count | Post-capture read count | Scaffold ID | Reference length (bp) | Virus group |
|---|---|---|---|---|---|---|
| A1 | SMAB-348-081811 | 34,752,298 | 79,300,498 | scaffold_0 | 1838 | Anellovirus |
| A9 | SMAB-349-081111 | 21,501,318 | 25,028,624 | scaffold_0 | 2710 | Anellovirus |
| A10 | SMAB-349-081111 | 21,501,318 | 25,028,624 | scaffold_1 | 2701 | Anellovirus |
| A11 | SMAB-349-081111 | 21,501,318 | 25,028,624 | scaffold_2 | 1514 | Anellovirus |
| A12 | SMAB-349-081111 | 21,501,318 | 25,028,624 | scaffold_3 | 1415 | Anellovirus |
| A13 | SMAB-349-081111 | 21,501,318 | 25,028,624 | scaffold_4 | 1397 | Anellovirus |
| A14 | SMAB-349-081111 | 21,501,318 | 25,028,624 | scaffold_5 | 1385 | Anellovirus |
| A15 | SMAB-349-081111 | 21,501,318 | 25,028,624 | scaffold_6 | 1055 | Anellovirus |
| A16 | SMAB-349-081111 | 21,501,318 | 25,028,624 | scaffold_7 | 1053 | Anellovirus |
| A17 | SMAB-349-081111 | 21,501,318 | 25,028,624 | scaffold_8 | 1042 | Anellovirus |
| A20 | SMAB-349-081111 | 21,501,318 | 25,028,624 | scaffold_11 | 1590 | Anellovirus |
| A48 | SMAB-349-081611 | 34,141,152 | 7,187,742 | scaffold_0 | 2991 | Anellovirus |
| A49 | SMAB-349-081611 | 34,141,152 | 7,187,742 | scaffold_1 | 2390 | Anellovirus |
| A50 | SMAB-349-081611 | 34,141,152 | 7,187,742 | scaffold_2 | 1747 | Anellovirus |
| A51 | SMAB-349-081611 | 34,141,152 | 7,187,742 | scaffold_3 | 2193 | Anellovirus |
| A52 | SMAB-349-081611 | 34,141,152 | 7,187,742 | scaffold_4 | 1040 | Anellovirus |
| A81 | SMAB-349-082311 | 36,651,918 | 14,426,400 | scaffold_0 | 3243 | Anellovirus |
| A82 | SMAB-349-082311 | 36,651,918 | 14,426,400 | scaffold_1 | 3164 | Anellovirus |
| A83 | SMAB-349-082311 | 36,651,918 | 14,426,400 | scaffold_2 | 3110 | Anellovirus |
| A84 | SMAB-349-082311 | 36,651,918 | 14,426,400 | scaffold_3 | 2923 | Anellovirus |
| A85 | SMAB-349-082311 | 36,651,918 | 14,426,400 | scaffold_4 | 2348 | Anellovirus |
| A86 | SMAB-349-082311 | 36,651,918 | 14,426,400 | scaffold_5 | 2301 | Anellovirus |
| A87 | SMAB-349-082311 | 36,651,918 | 14,426,400 | scaffold_6 | 1270 | Anellovirus |
| A88 | SMAB-349-082311 | 36,651,918 | 14,426,400 | scaffold_7 | 1247 | Anellovirus |
| A89 | SMAB-349-082311 | 36,651,918 | 14,426,400 | scaffold_8 | 1432 | Anellovirus |
| A110 | SMAB-353-081611 | 21,184,852 | 11,155,204 | scaffold_0 | 2628 | Anellovirus |
| A111 | SMAB-353-081611 | 21,184,852 | 11,155,204 | scaffold_1 | 2546 | Anellovirus |
| A112 | SMAB-353-081611 | 21,184,852 | 11,155,204 | scaffold_2 | 2334 | Anellovirus |
| A113 | SMAB-353-081611 | 21,184,852 | 11,155,204 | scaffold_3 | 1616 | Anellovirus |
| A114 | SMAB-353-081611 | 21,184,852 | 11,155,204 | scaffold_4 | 1672 | Anellovirus |
| A115 | SMAB-353-081611 | 21,184,852 | 11,155,204 | scaffold_5 | 1328 | Anellovirus |
| A116 | SMAB-353-081611 | 21,184,852 | 11,155,204 | scaffold_6 | 1116 | Anellovirus |
| A117 | SMAB-353-081611 | 21,184,852 | 11,155,204 | scaffold_7 | 1111 | Anellovirus |
| A118 | SMAB-353-081611 | 21,184,852 | 11,155,204 | scaffold_8 | 1019 | Anellovirus |
| A119 | SMAB-353-081611 | 21,184,852 | 11,155,204 | scaffold_9 | 1005 | Anellovirus |
| A149 | SMAB-357-081611 | 21,920,676 | 5,402,270 | scaffold_0 | 1290 | Anellovirus |
| A150 | SMAB-357-081611 | 21,920,676 | 5,402,270 | scaffold_1 | 1245 | Anellovirus |
| A151 | SMAB-357-081611 | 21,920,676 | 5,402,270 | scaffold_2 | 1231 | Anellovirus |
| A162 | SMAB-405-092711 | 21,502,312 | 16,696,432 | scaffold_0 | 2951 | Anellovirus |
| A163 | SMAB-405-092711 | 21,502,312 | 16,696,432 | scaffold_1 | 2736 | Anellovirus |
| A164 | SMAB-405-092711 | 21,502,312 | 16,696,432 | scaffold_2 | 2392 | Anellovirus |

TABLE 6-continued

Anellovirus contig coverage results based on metagenomic shotgun sequencing before and after viral targeted sequence capture

| | | | | | | |
|---|---|---|---|---|---|---|
| A165 | SMAB-405-092711 | 21,502,312 | 16,696,432 | scaffold_3 | 2323 | Anellovirus |
| A166 | SMAB-405-092711 | 21,502,312 | 16,696,432 | scaffold_4 | 2722 | Anellovirus |
| A167 | SMAB-405-092711 | 21,502,312 | 16,696,432 | scaffold_5 | 2166 | Anellovirus |
| A168 | SMAB-405-092711 | 21,502,312 | 16,696,432 | scaffold_6 | 2154 | Anellovirus |
| A169 | SMAB-405-092711 | 21,502,312 | 16,696,432 | scaffold_7 | 2078 | Anellovirus |
| A170 | SMAB-405-092711 | 21,502,312 | 16,696,432 | scaffold_8 | 1984 | Anellovirus |
| A171 | SMAB-405-092711 | 21,502,312 | 16,696,432 | scaffold_9 | 1751 | Anellovirus |
| A172 | SMAB-405-092711 | 21,502,312 | 16,696,432 | scaffold_10 | 1714 | Anellovirus |
| A173 | SMAB-405-092711 | 21,502,312 | 16,696,432 | scaffold_11 | 1711 | Anellovirus |
| A174 | SMAB-405-092711 | 21,502,312 | 16,696,432 | scaffold_12 | 1575 | Anellovirus |
| A175 | SMAB-405-092711 | 21,502,312 | 16,696,432 | scaffold_13 | 1550 | Anellovirus |
| A176 | SMAB-405-092711 | 21,502,312 | 16,696,432 | scaffold_14 | 1504 | Anellovirus |
| A177 | SMAB-405-092711 | 21,502,312 | 16,696,432 | scaffold_15 | 1091 | Anellovirus |
| A178 | SMAB-405-092711 | 21,502,312 | 16,696,432 | scaffold_16 | 1064 | Anellovirus |
| A179 | SMAB-405-092711 | 21,502,312 | 16,696,432 | scaffold_17 | 1041 | Anellovirus |
| A180 | SMAB-405-092711 | 21,502,312 | 16,696,432 | scaffold_18 | 1030 | Anellovirus |
| A181 | SMAB-405-092711 | 21,502,312 | 16,696,432 | scaffold_19 | 1024 | Anellovirus |
| A219 | SMAB-486-011712 | 32,045,168 | 12,929,988 | scaffold_0 | 3280 | Anellovirus |
| A220 | SMAB-486-011712 | 32,045,168 | 12,929,988 | scaffold_1 | 3230 | Anellovirus |
| A221 | SMAB-486-011712 | 32,045,168 | 12,929,988 | scaffold_2 | 3206 | Anellovirus |
| A222 | SMAB-486-011712 | 32,045,168 | 12,929,988 | scaffold_3 | 2694 | Anellovirus |
| A223 | SMAB-486-011712 | 32,045,168 | 12,929,988 | scaffold_4 | 2403 | Anellovirus |
| A224 | SMAB-486-011712 | 32,045,168 | 12,929,988 | scaffold_5 | 1346 | Anellovirus |
| A225 | SMAB-486-011712 | 32,045,168 | 12,929,988 | scaffold_6 | 1342 | Anellovirus |
| A226 | SMAB-486-011712 | 32,045,168 | 12,929,988 | scaffold_7 | 1259 | Anellovirus |
| A227 | SMAB-486-011712 | 32,045,168 | 12,929,988 | scaffold_8 | 1213 | Anellovirus |
| A228 | SMAB-486-011712 | 32,045,168 | 12,929,988 | scaffold_9 | 1135 | Anellovirus |

Pre-capture: Metagenomic shotgun sequencing using (ViroCap) targeted sequence capture

| ID | % of ref bases covered[a] | No. of ref bases | No. of covered bases | No. of Missing Bases | Ave. coverage depth[b] | Std dev of ave. coverage depth | Median coverage depth | No. of gaps[c] | Ave. gap length (bp) | Std dev ave. gap length (bp) | Median gap length (bp) | No. of reads layered | % Viral Reads |
|---|---|---|---|---|---|---|---|---|---|---|---|---|---|
| A1 | 100 | 1838 | 1838 | 0 | 12248.74 | 12913.66 | 5291 | 0 | 0 | NaN | 0 | 271871 | 0.782310856 |
| A9 | 100 | 2710 | 2710 | 0 | 38.46 | 22.66 | 40 | 0 | 0 | NaN | 0 | 1066 | 0.004957836 |
| A10 | 98.45 | 2701 | 2659 | 42 | 18.45 | 10.29 | 18 | 1 | 42 | NaN | 42 | 505 | 0.002348693 |
| A11 | 100 | 1514 | 1514 | 0 | 234.44 | 112.12 | 285 | 0 | 0 | NaN | 0 | 3619 | 0.016831526 |
| A12 | 100 | 1415 | 1415 | 0 | 8.68 | 5.52 | 7 | 0 | 0 | NaN | 0 | 124 | 0.000576709 |
| A13 | 100 | 1397 | 1397 | 0 | 9.54 | 5.44 | 9 | 0 | 0 | NaN | 0 | 135 | 0.000627868 |
| A14 | 100 | 1385 | 1385 | 0 | 209.25 | 115.06 | 184 | 0 | 0 | NaN | 0 | 3110 | 0.01446423 |
| A15 | 100 | 1055 | 1055 | 0 | 11.78 | 6.66 | 13 | 0 | 0 | NaN | 0 | 127 | 0.000590661 |
| A16 | 100 | 1053 | 1053 | 0 | 11.2 | 6.11 | 10 | 0 | 0 | NaN | 0 | 120 | 0.000558105 |
| A17 | 100 | 1042 | 1042 | 0 | 10.1 | 4.13 | 10 | 0 | 0 | NaN | 0 | 106 | 0.000492993 |
| A20 | 100 | 1590 | 1590 | 0 | 28.07 | 14.76 | 29 | 0 | 0 | NaN | 0 | 455 | 0.002116149 |
| A48 | 100 | 2991 | 2991 | 0 | 90.21 | 34.95 | 101 | 0 | 0 | NaN | 0 | 2747 | 0.008046009 |
| A49 | 100 | 2390 | 2390 | 0 | 11.34 | 6.9 | 11 | 0 | 0 | NaN | 0 | 275 | 0.00080548 |
| A50 | 99.94 | 1747 | 1746 | 1 | 60.14 | 31.43 | 60 | 1 | 1 | NaN | 1 | 1062 | 0.003110616 |
| A51 | 99.77 | 2193 | 2188 | 5 | 116.1 | 73.05 | 114 | 2 | 2.5 | 1.5 | 2.5 | 2654 | 0.00777361 |
| A52 | 100 | 1040 | 1040 | 0 | 10.25 | 5.19 | 10 | 0 | 0 | NaN | 0 | 109 | 0.000319263 |
| A81 | 100 | 3243 | 3243 | 0 | 223.26 | 105.02 | 266 | 0 | 0 | NaN | 0 | 7420 | 0.020244507 |
| A82 | 100 | 3164 | 3164 | 0 | 43.21 | 29.08 | 39 | 0 | 0 | NaN | 0 | 1384 | 0.003776064 |
| A83 | 100 | 3110 | 3110 | 0 | 17.08 | 9.62 | 18 | 0 | 0 | NaN | 0 | 539 | 0.001470592 |
| A84 | 100 | 2923 | 2923 | 0 | 25.61 | 44.93 | 19 | 0 | 0 | NaN | 0 | 813 | 0.002218165 |
| A85 | 100 | 2348 | 2348 | 0 | 15.72 | 9.48 | 14 | 0 | 0 | NaN | 0 | 378 | 0.001031324 |
| A86 | 100 | 2301 | 2301 | 0 | 256.54 | 200.42 | 226 | 0 | 0 | NaN | 0 | 5949 | 0.016231074 |
| A87 | 100 | 1270 | 1270 | 0 | 362.37 | 248.3 | 372.5 | 0 | 0 | NaN | 0 | 4672 | 0.012746945 |
| A88 | 100 | 1247 | 1247 | 0 | 9.39 | 3.98 | 9 | 0 | 0 | NaN | 0 | 117 | 0.000319219 |
| A89 | 100 | 1432 | 1432 | 0 | 246.68 | 230.34 | 153 | 0 | 0 | NaN | 0 | 3761 | 0.0102614 |
| A110 | 100 | 2628 | 2628 | 0 | 38.35 | 17.35 | 40 | 0 | 0 | NaN | 0 | 1022 | 0.004824202 |
| A111 | 100 | 2546 | 2546 | 0 | 10.76 | 4.39 | 10 | 0 | 0 | NaN | 0 | 280 | 0.001321699 |
| A112 | 100 | 2334 | 2334 | 0 | 27.37 | 11.34 | 27 | 0 | 0 | NaN | 0 | 658 | 0.003105993 |
| A113 | 100 | 1616 | 1616 | 0 | 9.73 | 4.33 | 9 | 0 | 0 | NaN | 0 | 158 | 0.000745816 |
| A114 | 99.94 | 1672 | 1671 | 1 | 30.06 | 14.42 | 29 | 1 | 1 | NaN | 1 | 509 | 0.00240266 |
| A115 | 99.92 | 1328 | 1327 | 1 | 39.71 | 14.57 | 42 | 1 | 1 | NaN | 1 | 537 | 0.00253483 |
| A116 | 100 | 1116 | 1116 | 0 | 12.86 | 8.16 | 13 | 0 | 0 | NaN | 0 | 144 | 0.000679731 |
| A117 | 100 | 1111 | 1111 | 0 | 11.58 | 7.3 | 11 | 0 | 0 | NaN | 0 | 130 | 0.000613646 |
| A118 | 100 | 1019 | 1019 | 0 | 5.3 | 2.24 | 6 | 0 | 0 | NaN | 0 | 56 | 0.00026434 |
| A119 | 100 | 1005 | 1005 | 0 | 9.85 | 5.42 | 10 | 0 | 0 | NaN | 0 | 100 | 0.000472035 |
| A149 | 100 | 1290 | 1290 | 0 | 18.25 | 12.6 | 17 | 0 | 0 | NaN | 0 | 237 | 0.001081171 |
| A150 | 100 | 1245 | 1245 | 0 | 16.98 | 13.02 | 13 | 0 | 0 | NaN | 0 | 213 | 0.000971603 |
| A151 | 100 | 1231 | 1231 | 0 | 5.52 | 3.87 | 4 | 0 | 0 | NaN | 0 | 69 | 0.000314771 |
| A162 | 100 | 2951 | 2951 | 0 | 10.33 | 7.19 | 9 | 0 | 0 | NaN | 0 | 312 | 0.001451007 |
| A163 | 100 | 2736 | 2736 | 0 | 18.7 | 8.15 | 19 | 0 | 0 | NaN | 0 | 521 | 0.002422995 |
| A164 | 100 | 2392 | 2392 | 0 | 19.92 | 11.08 | 21 | 0 | 0 | NaN | 0 | 484 | 0.002250921 |
| A165 | 100 | 2323 | 2323 | 0 | 54.48 | 30.95 | 67 | 0 | 0 | NaN | 0 | 1287 | 0.005985403 |

TABLE 6-continued

Anellovirus contig coverage results based on metagenomic shotgun sequencing before and after viral targeted sequence capture

| A166 | 100 | 2722 | 2722 | 0 | 115.96 | 80.55 | 122 | 0 | 0 | NaN | 0 | 3238 | 0.015058846 |
| A167 | 99.86 | 2166 | 2163 | 3 | 49.71 | 27.65 | 60 | 1 | 3 | NaN | 3 | 1088 | 0.005059921 |
| A168 | 100 | 2154 | 2154 | 0 | 88.06 | 55.06 | 95 | 0 | 0 | NaN | 0 | 1921 | 0.008933923 |
| A169 | 100 | 2078 | 2078 | 0 | 24.78 | 15.07 | 23 | 0 | 0 | NaN | 0 | 518 | 0.002409043 |
| A170 | 100 | 1984 | 1984 | 0 | 58.14 | 47.45 | 47 | 0 | 0 | NaN | 0 | 1168 | 0.005431974 |
| A171 | 100 | 1751 | 1751 | 0 | 680.23 | 480.19 | 606 | 0 | 0 | NaN | 0 | 11993 | 0.055775398 |
| A172 | 99.82 | 1714 | 1711 | 3 | 124.02 | 66.88 | 136 | 1 | 3 | NaN | 3 | 2153 | 0.010012877 |
| A173 | 100 | 1711 | 1711 | 0 | 100.11 | 53.73 | 116 | 0 | 0 | NaN | 0 | 1731 | 0.008050297 |
| A174 | 98.1 | 1575 | 1545 | 30 | 19.01 | 11.97 | 21 | 1 | 30 | NaN | 30 | 305 | 0.001418452 |
| A175 | 100 | 1550 | 1550 | 0 | 14.53 | 7.37 | 13 | 0 | 0 | NaN | 0 | 231 | 0.001074303 |
| A176 | 100 | 1504 | 1504 | 0 | 650.41 | 527.14 | 625 | 0 | 0 | NaN | 0 | 9916 | 0.046115971 |
| A177 | 100 | 1091 | 1091 | 0 | 26.88 | 17.14 | 36 | 0 | 0 | NaN | 0 | 297 | 0.001381247 |
| A178 | 100 | 1064 | 1064 | 0 | 19.61 | 14.92 | 16 | 0 | 0 | NaN | 0 | 218 | 0.001013844 |
| A179 | 97.12 | 1041 | 1011 | 30 | 17.21 | 10.57 | 21 | 1 | 30 | NaN | 30 | 180 | 0.000837119 |
| A180 | 100 | 1030 | 1030 | 0 | 14 | 10.33 | 12 | 0 | 0 | NaN | 0 | 144 | 0.000669695 |
| A181 | 100 | 1024 | 1024 | 0 | 21.46 | 15.13 | 27 | 0 | 0 | NaN | 0 | 221 | 0.001027796 |
| A219 | 100 | 3280 | 3280 | 0 | 318.79 | 234.86 | 325 | 0 | 0 | NaN | 0 | 10582 | 0.033022139 |
| A220 | 100 | 3230 | 3230 | 0 | 33.84 | 12.88 | 36 | 0 | 0 | NaN | 0 | 1106 | 0.003451378 |
| A221 | 100 | 3206 | 3206 | 0 | 68.26 | 47.05 | 62 | 0 | 0 | NaN | 0 | 2227 | 0.006949566 |
| A222 | 100 | 2694 | 2694 | 0 | 73.69 | 47.87 | 85 | 0 | 0 | NaN | 0 | 2003 | 0.006250552 |
| A223 | 100 | 2403 | 2403 | 0 | 23.89 | 12.49 | 27 | 0 | 0 | NaN | 0 | 585 | 0.001825548 |
| A224 | 100 | 1346 | 1346 | 0 | 16.09 | 10.97 | 14 | 0 | 0 | NaN | 0 | 218 | 0.00068029 |
| A225 | 98.81 | 1342 | 1326 | 16 | 28.36 | 20.66 | 21 | 1 | 16 | NaN | 16 | 387 | 0.00120767 |
| A226 | 100 | 1259 | 1259 | 0 | 59.12 | 53.31 | 39 | 0 | 0 | NaN | 0 | 753 | 0.002349808 |
| A227 | 100 | 1213 | 1213 | 0 | 39.08 | 24.64 | 41 | 0 | 0 | NaN | 0 | 486 | 0.001516609 |
| A228 | 100 | 1135 | 1135 | 0 | 20.51 | 10.74 | 22 | 0 | 0 | NaN | 0 | 240 | 0.000748943 |

Post-capture: Metagenomic shotgun sequencing using (ViroCap) targeted sequence capture

| ID | Scaffold ID | % of ref bases covered[a] | No. of ref bases | No. of covered bases | No. of Missing Bases | Ave. coverage depth[b] | Std dev of ave. coverage depth | Median coverage depth | No. of gaps[c] | Ave. gap length (bp) | Std dev ave. gap length (bp) | Median gap length (bp) | No. of reads layered | % Viral Reads | % Viral Reads Fold increase |
|---|---|---|---|---|---|---|---|---|---|---|---|---|---|---|---|
| A1 | scaffold_0 | 99.95 | 1838 | 1837 | 1 | 3382358.61 | 2960741.89 | 2099195 | 1 | 1 | NaN | 1 | 67437000 | 85.040 | 108.703 |
| A9 | scaffold_0 | 100 | 2710 | 2710 | 0 | 36255.34 | 56024.32 | 14982.5 | 0 | 0 | NaN | 0 | 1065198 | 4.256 | 858.423 |
| A10 | scaffold_1 | 100 | 2701 | 2701 | 0 | 20096.17 | 9868.2 | 18695 | 0 | 0 | NaN | 0 | 567237 | 2.266 | 964.942 |
| A11 | scaffold_2 | 100 | 1514 | 1514 | 0 | 426553.34 | 130908.42 | 4675349.5 | 0 | 0 | NaN | 0 | 6720533 | 26.851 | 1595.303 |
| A12 | scaffold_3 | 96.11 | 1415 | 1360 | 55 | 3160.58 | 9562.3 | 132 | 2 | 27.5 | 10.5 | 27.5 | 50800 | 0.203 | 351.941 |
| A13 | scaffold_4 | 100 | 1397 | 1397 | 0 | 1686.5 | 3654.17 | 201 | 0 | 0 | NaN | 0 | 26640 | 0.106 | 169.523 |
| A14 | scaffold_5 | 100 | 1385 | 1385 | 0 | 331418.92 | 143019 | 347953 | 0 | 0 | NaN | 0 | 4996996 | 19.965 | 1380.310 |
| A15 | scaffold_6 | 99.91 | 1055 | 1054 | 1 | 461.97 | 320.02 | 343 | 1 | 1 | NaN | 1 | 5520 | 0.022 | 37.339 |
| A16 | scaffold_7 | 99.91 | 1053 | 1052 | 1 | 1526.3 | 1159.63 | 1477 | 1 | 1 | NaN | 1 | 17794 | 0.071 | 127.386 |
| A17 | scaffold_8 | 99.9 | 1042 | 1041 | 1 | 116.94 | 81.59 | 90.5 | 1 | 1 | NaN | 1 | 1358 | 0.005 | 11.006 |
| A20 | scaffold_1 | 99.94 | 1590 | 1589 | 1 | 5521.42 | 2758.03 | 5455.5 | 1 | 1 | NaN | 1 | 90871 | 0.363 | 171.570 |
| A48 | scaffold_0 | 100 | 2991 | 2991 | 0 | 40395.71 | 15366.52 | 40940 | 0 | 0 | NaN | 0 | 1250081 | 17.392 | 2161.550 |
| A49 | scaffold_1 | 97.82 | 2390 | 2338 | 52 | 392.77 | 536.37 | 211 | 1 | 52 | NaN | 52 | 10560 | 0.147 | 182.397 |
| A50 | scaffold_2 | 100 | 1747 | 1747 | 0 | 3406.15 | 1892.25 | 3457 | 0 | 0 | NaN | 0 | 61553 | 0.856 | 275.303 |
| A51 | scaffold_3 | 100 | 2193 | 2193 | 0 | 19055.83 | 18186.6 | 14239 | 0 | 0 | NaN | 0 | 427884 | 5.953 | 765.792 |
| A52 | scaffold_4 | 100 | 1040 | 1040 | 0 | 361.5 | 259.79 | 258 | 0 | 0 | NaN | 0 | 3905 | 0.054 | 170.169 |
| A81 | scaffold_0 | 99.97 | 3243 | 3242 | 1 | 109940.23 | 71253.1 | 98517 | 1 | 1 | NaN | 1 | 3695472 | 25.616 | 1265.333 |
| A82 | scaffold_1 | 100 | 3164 | 3164 | 0 | 5835.68 | 9786.87 | 1623.5 | 0 | 0 | NaN | 0 | 193401 | 1.341 | 355.027 |
| A83 | scaffold_2 | 100 | 3110 | 3110 | 0 | 9782.48 | 22916.84 | 5727 | 0 | 0 | NaN | 0 | 349290 | 2.421 | 1646.403 |
| A84 | scaffold_3 | 100 | 2923 | 2923 | 0 | 13611.3 | 67753.26 | 593 | 0 | 0 | NaN | 0 | 505592 | 3.505 | 1579.968 |

TABLE 6-continued

Anellovirus contig coverage results based on metagenomic shotgun sequencing before and after viral targeted sequence capture

| | | | | | | | | | | | | | | | | |
|---|---|---|---|---|---|---|---|---|---|---|---|---|---|---|---|---|
| A85 | scaffold_4 | 100 | 2348 | 2348 | 0 | 675.07 | 1065.57 | 285 | 0 | 0 | NaN | 0 | 17758 | 0.123 | 119.355 |
| A86 | scaffold_5 | 100 | 2301 | 2301 | 0 | 32221.77 | 36026.86 | 16687 | 0 | 0 | NaN | 0 | 764059 | 5.296 | 326.303 |
| A87 | scaffold_6 | 100 | 1270 | 1270 | 0 | 94213.43 | 78979.25 | 57959 | 0 | 0 | NaN | 0 | 1223808 | 8.483 | 665.502 |
| A88 | scaffold_7 | 87.41 | 1247 | 1090 | 157 | 229.58 | 430.93 | 39 | 3 | 52.33 | 36.63 | 72 | 3587 | 0.025 | 77.890 |
| A89 | scaffold_8 | 100 | 1432 | 1432 | 0 | 182518.02 | 177308.43 | 129813 | 0 | 0 | NaN | 0 | 2826112 | 19.590 | 1909.083 |
| A110 | scaffold_0 | 100 | 2628 | 2628 | 0 | 28688.61 | 15711.83 | 24157 | 0 | 0 | NaN | 0 | 807302 | 7.237 | 1500.144 |
| A111 | scaffold_1 | 100 | 2546 | 2546 | 0 | 4164.39 | 4035.7 | 3192 | 0 | 0 | NaN | 0 | 120028 | 1.076 | 814.090 |
| A112 | scaffold_2 | 99.96 | 2334 | 2333 | 1 | 9257.96 | 12622.85 | 6241.5 | 1 | 1 | NaN | 1 | 244516 | 2.192 | 705.715 |
| A113 | scaffold_3 | 99.88 | 1616 | 1614 | 2 | 141.65 | 132.32 | 91 | 2 | 1 | NaN | 1 | 2523 | 0.023 | 30.326 |
| A114 | scaffold_4 | 100 | 1672 | 1672 | 0 | 25072.25 | 19058.74 | 20055 | 0 | 0 | NaN | 0 | 437526 | 3.922 | 1632.428 |
| A115 | scaffold_5 | 99.92 | 1328 | 1327 | 1 | 34536.53 | 16308.98 | 29254.5 | 1 | 1 | NaN | 1 | 469416 | 4.208 | 1660.090 |
| A116 | scaffold_6 | 100 | 1116 | 1116 | 0 | 3013.53 | 2124.7 | 2227 | 0 | 0 | NaN | 0 | 35526 | 0.318 | 468.524 |
| A117 | scaffold_7 | 100 | 1111 | 1111 | 0 | 11264.15 | 7881.43 | 11882 | 0 | 0 | NaN | 0 | 130883 | 1.173 | 1912.000 |
| A118 | scaffold_8 | 99.8 | 1019 | 1017 | 2 | 126.88 | 107.28 | 108 | 2 | 1 | NaN | 1 | 1483 | 0.013 | 50.292 |
| A119 | scaffold_9 | 99.9 | 1005 | 1004 | 1 | 672.23 | 554.79 | 501 | 1 | 1 | NaN | 1 | 7207 | 0.065 | 136.868 |
| A149 | scaffold_0 | 99.92 | 1290 | 1289 | 1 | 264.71 | 233.53 | 145 | 1 | 1 | NaN | 1 | 4272 | 0.079 | 73.141 |
| A150 | scaffold_1 | 99.92 | 1245 | 1244 | 1 | 10209.4 | 13621.97 | 1858 | 1 | 1 | NaN | 1 | 131870 | 2.441 | 2512.141 |
| A151 | scaffold_2 | 100 | 1231 | 1231 | 0 | 1735.51 | 1021.01 | 1651 | 0 | 0 | NaN | 0 | 22487 | 0.416 | 1322.392 |
| A162 | scaffold_0 | 98.75 | 2951 | 2914 | 37 | 6797.55 | 21769.05 | 450 | 3 | 12.33 | 8.06 | 17 | 214072 | 1.282 | 883.622 |
| A163 | scaffold_1 | 100 | 2736 | 2736 | 0 | 2520.44 | 2576.55 | 1932 | 0 | 0 | NaN | 0 | 73026 | 0.437 | 180.510 |
| A164 | scaffold_2 | 99.62 | 2392 | 2383 | 9 | 1404.45 | 3778.63 | 276 | 1 | 9 | NaN | 9 | 42446 | 0.254 | 112.941 |
| A165 | scaffold_3 | 100 | 2323 | 2323 | 0 | 5554.35 | 5104.61 | 3670 | 0 | 0 | NaN | 0 | 144832 | 0.867 | 144.926 |
| A166 | scaffold_4 | 100 | 2722 | 2722 | 0 | 63408.26 | 207855.91 | 1232 | 0 | 0 | NaN | 0 | 2548000 | 15.261 | 1013.407 |
| A167 | scaffold_5 | 99.91 | 2166 | 2164 | 2 | 5513.19 | 7021.36 | 3490 | 1 | 2 | NaN | 2 | 124695 | 0.747 | 147.598 |
| A168 | scaffold_6 | 100 | 2154 | 2154 | 0 | 11353.51 | 8844.18 | 9644.5 | 0 | 0 | NaN | 0 | 257501 | 1.542 | 172.629 |
| A169 | scaffold_7 | 99.09 | 2078 | 2059 | 19 | 254.76 | 327.1 | 116 | 2 | 9.5 | 0.5 | 9.5 | 6422 | 0.038 | 15.966 |
| A170 | scaffold_8 | 100 | 1984 | 1984 | 0 | 26353.3 | 71853.17 | 3449 | 0 | 0 | NaN | 0 | 659791 | 3.952 | 727.487 |
| A171 | scaffold_9 | 100 | 1751 | 1751 | 0 | 184578.07 | 259159.19 | 68402 | 0 | 0 | NaN | 0 | 3311416 | 19.833 | 355.588 |
| A172 | scaffold_10 | 100 | 1714 | 1714 | 0 | 18936.09 | 11003.95 | 21219 | 0 | 0 | NaN | 0 | 336384 | 2.015 | 201.211 |
| A173 | scaffold_11 | 100 | 1711 | 1711 | 0 | 11672.08 | 6609.58 | 12586 | 0 | 0 | NaN | 0 | 207222 | 1.241 | 154.170 |
| A174 | scaffold_12 | 100 | 1575 | 1575 | 0 | 52030.8 | 28720.38 | 66614 | 0 | 0 | NaN | 0 | 867748 | 5.197 | 3663.998 |
| A175 | scaffold_13 | 100 | 1550 | 1550 | 0 | 119679.86 | 384901.96 | 324 | 0 | 0 | NaN | 0 | 2130790 | 12.762 | 11879.281 |
| A176 | scaffold_14 | 100 | 1504 | 1504 | 0 | 238031.38 | 467196.25 | 22091 | 0 | 0 | NaN | 0 | 4445764 | 26.627 | 577.393 |
| A177 | scaffold_15 | 100 | 1091 | 1091 | 0 | 2427.26 | 2452.27 | 1354 | 0 | 0 | NaN | 0 | 30619 | 0.183 | 132.769 |
| A178 | scaffold_16 | 99.91 | 1064 | 1063 | 1 | 1392.61 | 1525 | 770 | 1 | 1 | NaN | 1 | 15820 | 0.095 | 93.457 |
| A179 | scaffold_17 | 97.89 | 1041 | 1019 | 22 | 1052.72 | 724.32 | 844 | 1 | 22 | NaN | 22 | 11506 | 0.069 | 82.322 |
| A180 | scaffold_18 | 100 | 1030 | 1030 | 0 | 6807.7 | 15349.44 | 306 | 0 | 0 | NaN | 0 | 87586 | 0.525 | 783.310 |
| A181 | scaffold_19 | 96.29 | 1024 | 986 | 38 | 235.2 | 148.88 | 212 | 1 | 38 | NaN | 38 | 2962 | 0.018 | 17.261 |

TABLE 6-continued

Anellovirus contig coverage results based on metagenomic shotgun sequencing before and after viral targeted sequence capture

| A219 | scaf-fold_0 | 100 | 3280 | 3280 | 0 | 99170.62 | 105634.57 | 62587 | 0 | 0 | NaN | 0 | 3429938 | 26.527 | 803.310 |
| A220 | scaf-fold_1 | 100 | 3230 | 3230 | 0 | 11741.54 | 5561.51 | 11319.5 | 0 | 0 | NaN | 0 | 390863 | 3.023 | 875.858 |
| A221 | scaf-fold_2 | 100 | 3206 | 3206 | 0 | 67579.79 | 33956.26 | 63616 | 0 | 0 | NaN | 0 | 2350955 | 18.182 | 2616.306 |
| A222 | scaf-fold_3 | 100 | 2694 | 2694 | 0 | 6039.02 | 14066.03 | 1075.5 | 0 | 0 | NaN | 0 | 173604 | 1.343 | 214.804 |
| A223 | scaf-fold_4 | 100 | 2403 | 2403 | 0 | 4739.73 | 2219.1 | 4485 | 0 | 0 | NaN | 0 | 119472 | 0.924 | 506.145 |
| A224 | scaf-fold_5 | 99.33 | 1346 | 1337 | 9 | 459.27 | 988.44 | 57 | 1 | 9 | NaN | 9 | 7976 | 0.062 | 90.676 |
| A225 | scaf-fold_6 | 100 | 1342 | 1342 | 0 | 10795.11 | 22495.63 | 238 | 0 | 0 | NaN | 0 | 157737 | 1.220 | 1010.153 |
| A226 | scaf-fold_7 | 98.65 | 1259 | 1242 | 17 | 13553.61 | 25814.24 | 1351 | 1 | 17 | NaN | 17 | 182082 | 1.408 | 599.289 |
| A227 | scaf-fold_8 | 99.92 | 1213 | 1212 | 1 | 653.52 | 880.84 | 148 | 1 | 1 | NaN | 1 | 9074 | 0.070 | 46.273 |
| A228 | scaf-fold_9 | 96.12 | 1135 | 1091 | 44 | 1600.57 | 2908.16 | 66 | 1 | 44 | NaN | 44 | 19359 | 0.150 | 199.911 |

Alignment to reference genomes

| ID | GenBank version and GI | Reference description | Significance | Bitscore of alignment/kb length | Percent ID of alignment |
|---|---|---|---|---|---|
| A1 | gi\|1295413947\|ref\|NC_014078.1\| | Torque teno virus 19, complete genome | 0 | 790 | 74.11 |
| A9 | gi\|217416834\|gb\|FJ426280.1\| | Torque teno virus strain SIA109, complete genome | 0 | 3353 | 90.32 |
| A10 | gi\|5616144\|gb\|AF122917.1\| | TT virus isolate JA4. complete genome | 0 | 3740 | 93.15 |
| A11 | gi\|1339511367\|emb\|FR751491.1\| | Torque teno virus complete genome, isolate TTV- HD19 (rheu242) | 0 | 2184 | 95.51 |
| A12 | gi\|295413947\|ref\|NC_014078.1\| | Torque teno virus 19. complete genome | 1E−126 | 453 | 63.76 |
| A13 | gi\|49203022\|emb\|AJ620231.1\| | Torque teno virus, isolate tth8. complete genome | 0 | 876 | 71.24 |
| A14 | gi\|7657957\|dbj\|AB028669.1\| | TT virus gene for ORF1 and ORF2. complete genome. isolate:TJN02 | 0 | 1624 | 92.03 |
| A15 | gi\|7415914\|dbj\|AB038628.1\| | TTV-like mini virus complete genome. isdate:TLMV-CLC205 | 0 | 874 | 79.90 |
| A16 | gi\|7415914\|dbj\|AB038628.1\| | TTV-like mini virus complete genome. isolate:TLMV-CLC205 | 0 | 919 | 77.89 |
| A17 | gi\|49203001\|emb\|AJ620226.1\| | Torque teno virus, isolate tth4, complete genome | 1E−102 | 375 | 64.84 |
| A20 | gi\|217416834\|gb\|FJ426280.1\| | Torque teno virus strain SIA109, complete genome | 0 | 943 | 84.54 |
| A48 | gi\|7657957\|dbj\|AB028669.1\| | TT virus gene for ORF1 and ORF2. complete genome. isolate:TJN02 | 0 | 3921 | 91.14 |
| A49 | gi\|381140099\|emb\|FR848323.1\| | Torque teno virus complete genome, isolate HD11 sle2037 | 1E−135 | 484 | 64.49 |
| A50 | gi\|217416834\|gb\|FJ426280.1\| | Torque teno virus strain SIA109, complete genome | 0 | 1798 | 83.23 |
| A51 | gi\|217416834\|gb\|FJ426280.1\| | Torque teno virus strain SIA109, complete genome | 0 | 2122 | 89.05 |
| A52 | gi\|17827196\|dbj\|AB064597.1\| | Torque teno virus DNA. complete genome, isolate: CT30F | 1E−169 | 597 | 70.92 |
| A81 | gi\|7657957\|dbj\|AB028669.1\| | TT virus gene for ORF1 and ORF2, complete genome, isolate:TJN02 | 0 | 4303 | 91.69 |
| A82 | gi\|17827189\|dbj\|AB064596.1\| | Torque teno virus DNA. complete genome, isolate: CT25F {SQ 1-3126} | 0 | 1220 | 63.94 |
| A83 | gi\|149203001\|emb\|AJ620226.1\| | Torque teno virus, isolate tth4, complete genome | 0 | 4035 | 90.53 |
| A84 | gi\|149203001\|emb\|AJ620226.1\| | Torque teno virus, isolate tth4, complete genome | 0 | 1440 | 70.50 |
| A85 | gi\|381140099\|emb\|FR848323.1\| | Torque teno virus complete genome, isolate HD11 sle2037 | 1E−143 | 511 | 65.15 |
| A86 | gi\|217416834\|gb\|FJ426280.1\| | Torque teno virus strain SIA109, complete genome | 0 | 2594 | 85.96 |
| A87 | gi\|217416834\|gb\|FJ426280.1\| | Torque teno virus strain SIA109, complete genome | 0 | 1779 | 93.93 |
| A88 | gi\|339511366\|emb\|FR751490.1\| | Torque teno virus complete genome, isolate TTV- HD18b (uro705) | 1E−101 | 370 | 58.28 |
| A89 | gi\|217416834\|gb\|FJ426280.1\| | Torque teno virus strain SIA109, complete genome | 0 | 1237 | 93.61 |
| A110 | gi\|339511375\|emb\|FR751499.1\| | Torque teno virus complete genome, isolate TTV- HD22 (rheul 12) | 0 | 3556 | 92.46 |
| A111 | gi\|295441905\|ref\|NC_014096.1\| | Torque teno virus 15. complete genome | 0 | 3418 | 91.98 |
| A112 | gi\|1339832375\|ref\|NC_015783.1\| | Torque teno virus, complete genome | 0 | 2326 | 82.40 |
| A113 | gi\|1339832375\|ref\|NC_015783.1\| | Torque teno virus, complete genome | 0 | 870 | 68.51 |
| A114 | gi\|339832375\|ref\|NC_015783.1\| | Torque teno virus, complete genome | 0 | 2073 | 95.47 |
| A115 | gi\|339832375\|ref\|NC_015783.1\| | Torque teno virus, complete genome | 0 | 1970 | 97.74 |
| A116 | gi\|217416834\|gb\|FJ426280.1\| | Torque teno virus strain SIA109, complete genome | 0 | 1267 | 87.44 |
| A117 | gi\|1339511369\|emb\|FR751493.1\| | Torque teno virus complete genome, isolate TTV- HD20b (uro742) | 0 | 1356 | 88.48 |
| A118 | gi\|381140099\|emb\|FR848323.1\| | Torque teno virus complete genome, isolate HD11 sle2037 | 1E−121 | 437 | 67.84 |
| A119 | gi\|339832375\|ref\|NC_015783.1\| | Torque teno virus, complete genome | 1E−170 | 599 | 70.81 |
| A149 | gi\|1134133206\|ref\|NC_009225.1\| | Torque teno midi virus 1, complete genome | 1E−111 | 405 | 64.80 |
| A150 | gi\|1295441891\|ref\|NC_014093.1\| | Torque teno midi virus 2, complete genome | 0 | 668 | 69.02 |
| A151 | gi\|17827243\|dbj\|AB064604.1\| | Torque teno virus DNA. complete genome, isolate: CT39F | 0 | 1233 | 85.50 |
| A162 | gi\|1295413928\|ref\|NC_014076.1\| | Torque teno virus 10. complete genome | 0 | 993 | 74.15 |
| A163 | gi\|339832375\|ref\|NC_015783.1\| | Torque teno virus, complete genome | 0 | 2624 | 81.00 |
| A164 | gi\|58613381\|gb\|AY823988.1\| | Torque teno virus isolate 2h, complete genome | 1E−104 | 381 | 65.35 |
| A165 | gi\|7415914\|dbj\|AB038628.1\| | TTV-like mini virus complete genome, isolate:TLMV-CLC205 | 0 | 1239 | 79.72 |
| A166 | gi\|58613386\|gb\|AY823989.1\| | Torque teno virus isolate 3h, complete genome | 2E−83 | 313 | 88.93 |
| A167 | gi\|58613386\|gb\|AY823989.1\| | Torque teno virus isolate 3h, complete genome | 0 | 1034 | 78.99 |
| A168 | gi\|1339511369\|emb\|FR751493.1\| | Torque teno virus complete genome, isolate TTV- HD20b <uro742) | 0 | 1898 | 78.30 |
| A169 | gi\|6463708\|dbj\|AB026930.1\| | TTV-like mini virus DNA, complete genome, isolate: TLMV-CBD231 | 1E−171 | 603 | 66.05 |
| A170 | gi\|1339511375\|emb\|FR751499.1\| | Torque teno virus complete genome, isolate TTV- HD22 (rheul 12) | 1E−123 | 446 | 61.87 |
| A171 | gi\|381140099\|emb\|FR848323.1\| | Torque teno virus complete genome, isolate HD11 sle2037 | 1E−111 | 405 | 61.95 |
| A172 | gi\|217416834\|gb\|FJ426280.1\| | Torque teno virus strain SIA109, complete genome | 0 | 1959 | 86.75 |

TABLE 6-continued

Anellovirus contig coverage results based on metagenomic shotgun sequencing before
and after viral targeted sequence capture

| | | | | | |
|---|---|---|---|---|---|
| A173 | gi\|217416834\|gb\|FJ426280.1\| | Torque teno virus strain SIA109, complete genome | 0 | 1848 | 84.69 |
| A174 | gi\|156104001\|emb\|AM711976.1\| | TT virus sle1957 complete genome | 0 | 2146 | 94.04 |
| A175 | gi\|295413928\|ref\|NC_014076.1\| | Torque teno virus 10, complete genome | 0 | 1020 | 71.48 |
| A176 | gi\|339511375\|emb\|FR751499.1\| | Torque teno virus complete genome, isolate TTV- HD22 (rheul 12) | 1E-122 | 442 | 62.00 |
| A177 | gi\|1339511369\|emb\|FR751493.1\| | Torque teno virus complete genome, isolate TTV- HD20b (uro742) | 0 | 973 | 78.07 |
| A178 | gi\|295441905\|ref\|NC_014096.1\| | Torque teno virus 15, complete genome | 1E-151 | 538 | 67.56 |
| A179 | gi\|1339511365\|emb\|FR751489.1\| | Torque teno virus complete genome, isolate TTV- HD18a (uro703) | 0 | 698 | 74.47 |
| A180 | gi\|1295441891\|ref\|NC_014093.1\| | Torque teno midi virus 2, complete genome | 1E-141 | 504 | 62.97 |
| A181 | gi\|1295441884\|ref\|NC_014091.1\| | Torque teno virus 16, complete genome | 1E-106 | 388 | 63.05 |
| A219 | gi\|217416834\|gb\|FJ426280.1\| | Torque teno virus strain SIA109, complete genome | 0 | 4059 | 90.67 |
| A220 | gi\|295441884\|ref\|NC_014091.1\| | Torque teno virus 16, complete genome | 0 | 4352 | 91.49 |
| A221 | gi\|49202965\|emb\|AJ620217.1\| | Torque teno virus, isolate tth21. complete genome | 0 | 4602 | 94.26 |
| A222 | gi\|1339511366\|emb\|FR751490.1\| | Torque teno virus complete genome, isolate TTV- HD18b (uro705) | 0 | 686 | 66.00 |
| A223 | gi\|17827196\|dbj\|AB064597.1\| | Torque teno virus DNA. complete genome, isolate: CT30F | 0 | 1855 | 94.64 |
| A224 | gi\|1295441884\|ref\|NC_014091.1\| | Torque teno virus 16, complete genome | 1E-110 | 402 | 61.71 |
| A225 | gi\|1134133206\|ref\|NC_009225.1\| | Torque teno midi virus 1, complete genome | 0 | 648 | 68.54 |
| A226 | gi\|52854167\|gb\|AY622909.1\| | Small anellovirus 2, complete genome | 1E-131 | 472 | 62.89 |
| A227 | gi\|295441891\|ref\|NC_014093.1\| | Torque teno midi virus 2, complete genome | 1E-113 | 412 | 60.65 |
| A228 | gi\|66391749\|ref\|NC_007013.1\| | Small anellovirus 1, complete genome | 1E-129 | 464 | 63.36 |

NA: Not applicable: NaN: Not a number

[a] Breadth-of-coverage as a percent of total reference length (No. of covered bases divided by No. of reference bases).

[b] Mean depth-of-coverage across the reference length; calculated across all positions in the reference, whether covered or uncovered.

[c] Number of gapped (uncovered) areas in context of the reference sequence.

TABLE 7

Non-viral read classification based on metagenomic shotgun sequencing before and after viral targeted sequence capture.

| Sample type | Sample ID | Virus(es) detected | Pre- or post-capture | Total reads | % viral reads (viral read count) | Total non-viral reads | Non-viral read filtering | | | | Non-viral read identities[a] | | | |
|---|---|---|---|---|---|---|---|---|---|---|---|---|---|---|
| | | | | | | | % of reads passing mask filter (read count) | % of reads passing mask and adaptor filters (read count) | % of reads passing mask, adaptor, and technical filters (read count) | % of capture positive control reads (read count) | % of bacterial & fungal reads (read count) | % of human reads (read count) | % of NCBInt reads (read count) | % of total non-viral reads mapped (read count)[b] |
| Naso-pharyngeal swab | S1 | Torque teno virus; Human adenovirus B, type 3 | Pre-capture | 4,202,474 | 0.4% (15,116) | 4,187,358 | 83.7% (3,503,645) | 79.7% (3,336,097) | 79.1% (3,314,130) | 0% (0) | 12.4% (409,536) | 76.8% (2,543,675) | 1.7% (57,503) | 90.9% (3,010,714) |
| | | | Post-capture | 16,080,640 | 47.9% (7,704,018) | 8,376,622 | 84.6% (7,084,765) | 81.3% (6,813,094) | 80.5% (6,746,513) | <0.1% (286) | 9.7% (656,181) | 83.6% (5,638,382) | 1.5% (99,944) | 94.8% (6,394,793) |
| Naso-pharyngeal swab | S2 | TTV-like mini virus isolate; Human adenovirus C, type 1 | Pre-capture | 5,087,234 | <0.1% (87) | 5,087,147 | 87.8% (4,466,890) | 81.9% (4,166,363) | 81.3% (4,138,127) | 0% (0) | 10.9% (451,687) | 74.2% (3,069,110) | 1.8% (74,979) | 86.9% (3,595,776) |
| | | | Post-capture | 3,713,962 | 3.1% (116,751) | 3,597,211 | 85.9% (3,090,139) | 82.7% (2,974,892) | 82.0% (2,948,339) | <0.1% (701) | 14.2% (417,605) | 78.1% (2,303,865) | 2.4% (70,786) | 94.7% (2,792,957) |
| Naso-pharyngeal swab | S3 | Torque teno mini virus; Human parainfluenza virus 3 | Pre-capture | 5,139,462 | <0.1% (172) | 5,139,290 | 82.9% (4,262,698) | 78.0% (4,007,111) | 77.4% (3,979,138) | 0% (0) | 11.4% (454,766) | 70.8% (2,816,455) | 1.6% (62,313) | 83.8% (3,333,534) |
| | | | Post-capture | 4,094,568 | 6.4% (263,062) | 3,831,506 | 80.2% (3,073,249) | 77% (2,950,353) | 76.1% (2,915,835) | <0.1% (931) | 14.4% (418,290) | 77.4% (2,255,930) | 2.4% (69,352) | 94.1% (2,744,503) |
| Naso-pharyngeal swab | S4 | TTV-like mini virus isolate; Human bocavirus 1 | Pre-capture | 6,124,424 | 0.7% (4,420) | 6,120,004 | 88.6% (5,424,487) | 84.7% (5,185,684) | 84.2% (5,153,877) | <0.1% (1) | 13.5% (693,606) | 76.9% (3,961,449) | 2.2% (110,525) | 92.5% (4,765,581) |
| | | | Post-capture | 5,659,554 | 8.2% (461,504) | 5,198,050 | 86.5% (4,496,347) | 83.5% (4,337,848) | 82.8% (4,302,342) | <0.1% (707) | 15.5% (665,350) | 77.4% (3,329,053) | 2.4% (103,954) | 95.3% (4,099,064) |
| Naso-pharyngeal swab | S5 | Torque teno virus | Pre-capture | 9,152,970 | 0% (0) | 9,152,970 | 84.5% (7,732,422) | 78.2% (7,161,848) | 77.7% (7,108,816) | <0.1% (1) | 8.3% (591,923) | 73.4% (5,214,849) | 2.2% (154,617) | 83.9% (5,961,390) |
| | | | Post-capture | 5,834,446 | <0.1% (117) | 5,834,329 | 81.5% (4,756,869) | 78.3% (4,565,673) | 77.4% (4,515,441) | <0.1% (1076) | 12.2% (550,019) | 79.4% (3,584,353) | 3.0% (133,939) | 94.6% (4,269,387) |
| Naso-pharyngeal swab | S6 | Human adenovirus 884 B, type 3A; KI polyomavirus; Human rhinovirus 80 | Pre-capture | 10,179,884 | 0.2% (20,266) | 10,159,618 | 81.6% (8,291,060) | 76.0% (7,724,167) | 74.7% (7,589,505) | 0% (0) | 12.6% (958,739) | 73.5% (5,580,948) | 1.0% (76,349) | 87.2% (6,616,036) |
| | | | Post-capture | 12,064,068 | 29.3% (3,532,428) | 8,531,640 | 81.6% (6,959,285) | 78.3% (6,676,571) | 78.2% (6,673,856) | <0.1% (21) | 14.2% (948,331) | 77.6% (5,180,714) | 5.5% (364,115) | 97.3% (6,493,181) |

TABLE 7-continued

Non-viral read classification based on metagenomic shotgun sequencing before and after viral targeted sequence capture.

| Sample type | Sample ID | Virus(es) detected | Pre- or post-capture | Total reads | % viral reads (viral read count) | Total non-viral reads | Non-viral red filtering ||||| Non-viral read identities[a] ||||
|---|---|---|---|---|---|---|---|---|---|---|---|---|---|---|
| | | | | | | | % of reads passing mask filter (read count) | % of reads passing mask and adaptor filters (read count) | % of reads passing mask, adaptor, and technical filters (read count) | % of capture positive control reads (read count) | % of bacterial & fungal reads (read count) | % of human reads (read count) | % of NCBInt reads (read count) | % of total non-viral reads mapped[b] (read count) |
| Stool | S7 | Human polyomavirus 10; Human adenovirus C, type 1; Sapovirus; Human astrovirus. | Pre-capture | 3,691,496 | 0.2% (6,677) | 3,684,819 | 94.9% (3,495,587) | 90.9% (3,347,941) | 90.0% (3,316,041) | 0% (0) | 81.3% (2,695,411) | 0.1% (4,197) | 2.6% (86,288) | 84.0% (2,,785,896) |
| | | | Post-capture | 4,104,534 | 29.5% (1,212,044) | 2,892,490 | 97.2% (2,810,676) | 94.1% (2,721,582) | 88.0% (2,544,964) | <0.1% (3) | 85.9% (2,185,234) | 0.2% (5,404) | 2.9% (74,491) | 89.0% (2,265,132) |
| Plasma | S8 | Torque teno virus; Human herpesvirus 6B | Pre-capture | 10,875,448 | <0.1% (38) | 10,875,410 | 90.8% (9,879,901) | 87.2% (9,484,536) | 86.7% (9,428,692) | 0% (0) | 13.9% (1,309,676) | 82.8% (7,804,535) | 1.8% (172,740) | 98.5% (9,286,951) |
| | | | Post-capture | 7,088,360 | 0.4% (29,340) | 7,059,020 | 88.6% (6,254,894) | 85.1% (6,006,307) | 84.5% (5,967,078) | <0.1% (569) | 16.0% (954,182) | 80.4% (4,798,804) | 2.0% (121,960) | 98.5% (5,875,515) |
| Pooled | P1-P14 | Human adenovirus B, type 35; Human bocavirus 1; Influenza A virus (H3N2); Influenza B virus; Human parvovirus B19; Norovirus GII-4; Parechovirus 1; BK polyomavirus; JC polyomavirus; Human rhinovirus 15; Human | Pre-capture | 7,458,192 | <0.1% (2,081) | 7,456,111 | 88.3% (6,584,766) | 84.2% (6,277,629) | 83.5% (6,224,995) | 0% (0) | 19.3% (1,203,117) | 76.6% (4,766,963) | 1.9% (118,491) | 97.8% (6,088,571) |
| | | | Post-capture | 9,295,438 | 12.4% (1,154,647) | 8,140,791 | 84.8% (6,901,118) | 80.8% (6,581,271) | 78.3% (6,376,862) | 0.1% (2,938) | 19.2% (1,224,264) | 78.8% (5,024,459) | 1.9% (121,258) | 99.9% (6,372,919) |

TABLE 7-continued

Non-viral read classification based on metagenomic shotgun sequencing before and after viral targeted sequence capture.

| Sample type | Sample ID | Virus(es) detected | Pre- or post-capture | Total reads | % viral reads (viral read count) | Total non-viral reads | Non-viral read filtering | | | Non-viral read identities[a] | | | |
|---|---|---|---|---|---|---|---|---|---|---|---|---|---|
| | | | | | | | % of reads passing mask filter (read count) | % of reads passing mask and adaptor filters (read count) | % of reads passing mask, adaptor, and technical filters (read count) | % of capture control reads positive (read count) | % of bacterial & fungal reads (read count) | % of human reads (read count) | % of NCBInt reads (read count) | % of total non-viral reads mapped (read count)[b] |
| | | respiratory syncytial virus, type B; Human herpesvirus 1; Torque teno virus; Human herpesvirus 3 | | | | | | | | | | | | |

Pre-capture: Metagenomic shotgun sequencing without targeted sequence capture.
Post-capture: Metagenomic shotgun sequencing using (ViroCap) targeted sequence capture.
[a]Non-viral read identities as percent of total reads passing mask, adaptor, and technical filters.
[b]The percentage of reads that mapped to the NCBI nt nucleotide database (ftp://ftp.ncbi.nlm.nih.gov/blast/db/)

TABLE 8

ViroCap and PCR correlations.

| Sample ID from Table 1 | Sample | Sample type | Virus identified in clinical laboratory prior to pooling | PCR results on pool | Sequencing results on pool |
|---|---|---|---|---|---|
| P1 | Pooled clinical samples | Pool | Adenovirus | + | + |
| P2 | Pooled clinical samples | Pool | Human Bocavirus | + | + |
| P3 | Pooled clinical samples | Pool | Influenza A | + | + |
| P4 | Pooled clinical samples | Pool | Influenza B | + | + |
| P5 | Pooled clinical samples | Pool | Parvovirus | + | + |
| P6 | Pooled clinical samples | Pool | Norovirus G2 | + | + |
| P7 | Pooled clinical samples | Pool | Parechovirus 1 | + | + |
| P8 | Pooled clinical samples | Pool | BK polyomavirus | + | + |
| P9 | Pooled clinical samples | Pool | JC polyomavirus | + | + |
| P10 | Pooled clinical samples | Pool | Rhinovirus | + | + |
| P11 | Pooled clinical samples | Pool | Respiratory syncytial virus | + | + |
| P12 | Pooled clinical samples | Pool | HSV-1 | + | + |
| P13 | Pooled clinical samples | Pool | Torque teno virus | Not tested | + |
| P14 | Pooled clinical samples | Pool | HHV-3 | − | + |
| NA | Pooled clinical samples | Pool | HHV-6 | − | − |
| NA | Pooled clinical samples | Pool | Enterovirus | − | − |
| NA | Pooled clinical samples | Pool | Parainfluenzavirus 1 | + | − |
| NA | Pooled clinical samples | Pool | Parainfluenzavirus 3 | | |
| NA | Pooled clinical samples | Pool | Parainfluenzavirus 4 | + | − |
| NA | Pooled clinical samples | Pool | Human metapneumovirus | − | − |
| NA | Pooled clinical samples | Pool | HHV-8 | − | − |
| NA | Pooled clinical samples | Pool | HHV-4 | − | − |

TABLE 9

Detection of viruses by PCR and ViroCap.

| | Number of viruses detected by: | | | |
|---|---|---|---|---|
| Experiment | Either PCR or ViroCap | Both PCR and ViroCap | PCR only | ViroCap only |
| 1 (pooled clinical specimens) | 15[a] | 12 | 2[b] | 1[c] |
| 2 (individual specimens) | 26 | 18 | 8[d,e] | 0 |
| Total | 41 | 30 | 10 | 1 |

[a] Table does not include a torque teno virus detected in the clinical pool but not tested for by PCR
[b] Parainfluenza virus types 1 and 4; These viruses were detected by PCR with high crossing threshold (Ct) values, indicating very low levels of virus.
[c] Varicella-zoster virus
[d] Rhinovirus; This virus was detected by PCR with high crossing threshold (Ct) values, indicating very low levels of virus.
[e] Of the 8 viruses detected in the samples by PCR but not by sequencing, 7 were not detected in the sequencing libraries, indicating that the failure to detect was attributable to library preparation rather than ViroCap.

TABLE 10

VmoCap-1.0 Taxonomy

| Taxonomy | Rep.Acc.ID | Host | # GN's | Lineage | Seg. Count | GN.Acc.IDs |
|---|---|---|---|---|---|---|
| Bovine ephemeral fever virus | NC_002526 | invertebrates,vertebrates | 1 | Rhabdoviridae,Ephemerovirus,Bovine ephemeral fever virus | -b | AF234533 |
| Kotonkan virus | NC_017714 | invertebrates,vertebrates | 1 | Rhabdoviridae,Ephemerovirus,Kotonkan virus | | HM474855 |
| Murrumbidgee virus | NC_022595 | invertebrates,vertebrates | 1 | Bunyaviridae,Orthobunyavirus,Murrumbidgee virus | seg. L | KF234253 |
| Murrumbidgee virus | NC_022596 | invertebrates,vertebrates | 1 | Bunyaviridae,Orthobunyavirus,Murrumbidgee virus | seg. M | KF234254 |
| Murrumbidgee virus | NC_022597 | invertebrates,vertebrates | 1 | Bunyavirusyaviridae,Orthobunyavirus,Murrumbidgee virus | seg. S | KF234255 |
| Ngaingan virus | NC_013955 | invertebrates,vertebrates | 1 | Rhabdoviridae,Ngaingan virus | | FJ715959 |
| Tibrogargan virus | NC_020804 | invertebrates,vertebrates | 1 | Rhabdoviridae,Tibrovirus,Tibrogargan virus | | GQ294472 |
| Circovirus-like genome BBC-A | NC_013020 | unknown | 1 | Circovirus-like genome BBC-A | | FJ959086 |
| Circovirus-like genome CB-A | NC_013028 | unknown | 1 | Circovirus-like genome CB-A | | FJ959082 |
| Circovirus-like genome CB-B | NC_013029 | unknown | 1 | Circovirus-like genome CB-B | | FJ959083 |
| Circovirus-like genome RW-A | NC_013023 | unknown | 1 | Circovirus-like genome RW-A | | FJ959077 |
| Circovirus-like genome RW-B | NC_013024 | unknown | 1 | Circovirus-like genome RW-B | | FJ959078 |
| Circovirus-like genome RW-C | NC_013025 | unknown | 1 | Circovirus-like genome RW-C | | FJ959079 |
| Circovirus-like genome RW-D | NC_013026 | unknown | 1 | Circovirus-like genome RW-D | | FJ959080 |
| Circovirus-like genome RW-E | NC_013027 | unknown | 1 | Circovirus-like genome RW-E | | FJ959081 |
| Circovirus-like genome SAR-A | NC_013030 | unknown | 1 | Circovirus-like genome SAR-A | | FJ959084 |
| Circovirus-like genome SAR-B | NC_013018 | unknown | 1 | Circovirus-like genome SAR-B | | FJ959085 |
| Dragonfly larvae associated circular virus-1 | NC_023427 | unknown | 1 | Dragonfly larvae associated circular virus-1 | | KF738873 |
| Dragonfly larvae associated circular virus-10 | NC_023436 | unknown | 2 | Dragonfly larvae associated circular virus-10 | | KF738885,KF738884 |
| Dragonfly larvae associated circular virus-2 | NC_023428 | unknown | 1 | Dragonfly larvae associated circular virus-2 | | KF738874 |
| Dragonfly larvae associated circular virus-3 | NC_023429 | unknown | 2 | Dragonfly larvae associated circular virus-3 | | KF738875,KF738876 |
| Dragonfly larvae associated circular virus-4 | NC_023430 | unknown | 1 | Dragonfly larvae associated circular virus-4 | | KF738877 |
| Dragonfly larvae associated circular virus-5 | NC_023431 | unknown | 2 | Dragonfly larvae associated circular virus-5 | | KF738878,KF738879 |
| Dragonfly larvae associated circular virus-6 | NC_023432 | unknown | 1 | Dragonfly larvae associated circular virus-6 | | KF738880 |
| Dragonfly larvae associated circular virus-7 | NC_023433 | unknown | 1 | Dragonfly larvae associated circular virus-7 | | KF738881 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Dragonfly larvae associated circular virus-8 | NC_023434 | unknown | 1 | Dragonfly larvae associated circular virus-8 | — | KF738882 |
| Dragonfly larvae associated circular virus-9 | NC_023435 | unknown | 1 | Dragonfly larvae associated circular virus-9 | — | KF738883 |
| Marine RNA virus JP-A | NC_009757 | unknown | 1 | Marine RNA virus JP-A | — | EF198241 |
| Marine RNA virus JP-B | NC_009758 | unknown | 1 | Marine RNA virus JP-B | — | EF198242 |
| Marine RNA virus SOG | NC_009756 | unknown | 1 | Marine RNA virus SOG | — | EF198240 |
| Ostreid herpesvirus 1 | NC_005881 | unknown | 1 | Malacoherpesviridae,Ostreavirus,Ostreid herpesvirus 1 | — | AY509253 |
| Pig stool associated circular ssDNA virus | NC_017916 | unknown | 8 | Pig stool associated circular ssDNA virus | — | JX305996,JX305993, JX305991,JX305997, JX305998,JX305992, JX305994,JX305995 |
| Pig stool associated circular ssDNA virus GER2011 | NC_017916 | unknown | 1 | Pig stool associated circular ssDNA virus | — | JQ023166 |
| Pithovirus sibericum | NC_023423 | unknown | 1 | Pithovirus sibericum | — | KF740664 |
| Porcine associated stool circular virus | NC_018617 | unknown | 1 | Porcine associated stool circular virus | — | JX274036 |
| Porcine stool-associated circular virus 2 | NC_021203 | unknown | 1 | Porcine stool-associated circular virus 2 | — | KC545226 |
| Porcine stool-associated circular virus 3 | NC_021204 | unknown | 4 | Porcine stool-associated circular virus 3 | — | KC545228,KC545229, KC545227,KC545230 |
| Sclerotinia sclerotiorum hypovirulence associated DNA virus 1 | NC_013116 | unknown | 5 | Sclerotinia sclerotiorum hypovirulence associated DNA virus 1 | — | KF268026,KF268027, KF268028,GQ365709, KF268025 |
| Wallerfield virus | NC_023440 | unknown | 1 | Negevirus,Wallerfield virus | — | KF042857 |
| AKR (endogenous) murine leukemia virus | NC_001702 ,NC_0013 9,NC_0013 62,NC_001 501 | vertebrates | 1 | Retroviridae,Gammaretrovirus,Murine leukemia virus | — | JQ1998 |
| ARV-138 | NC_015132 | vertebrates | 1 | Reoviridae,Orthoreovirus,Avian orthoreovirus | seg. S1 | AF218359 |
| ARV-176 | NC_015132 | vertebrates | 1 | Reoviridae,Orthoreovirus,Avian orthoreovirus | seg. S1 | AF218358 |
| Abelson murine leukemia virus | NC_001499 | vertebrates | 1 | Retroviridae,Gammaretrovirus,Abelson murine leukemia virus | — | AF033812 |
| Acartia tonsa copepod circovirus | NC_020099 | vertebrates | 1 | Circoviridae,Circovirus,Acartia tonsa copepod circovirus | — | JQ837277 |
| Adeno-associated virus-1 | NC_002077 | vertebrates | 1 | Parvoviridae,Dependovirus,Adeno-associated virus-1 | — | AF063497 |
| Adeno-associated virus-4 | NC_001829 | vertebrates | 1 | Parvoviridae,Dependovirus,Adeno-associated virus-4 | — | U89790 |
| Adeno-associated virus-6 | NC_002077 | vertebrates | 1 | Parvoviridae,Dependovirus,Adeno-associated virus-1 | — | AF028704 |
| Adeno-associated virus-7 | NC_006260 | vertebrates | 1 | Parvoviridae,Dependovirus,Adeno-associated virus-7 | — | AF513851 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Adeno-associated virus-8 | NC_006261 | vertebrates | 1 | Parvoviridae,Dependovirus,Adeno-associated virus-8 | — | AF513852 |
| African elephant polyomavirus 1 | NC_022519 | vertebrates | 1 | Polyomaviridae,Polyomavirus,African elephant polyomavirus 1 | — | KF147833 |
| African green monkey polyomavirus | NC_004763 | vertebrates | 1 | Polyomaviridae,Polyomavirus,African green monkey polyomavirus | — | K02562 |
| African green monkey simian foamy virus | NC_010820 | vertebrates | 1 | Retroviridae,Spumavirus,African green monkey simian foamy virus | — | M74895 |
| Aichi virus | NC_001918 | vertebrates | 10 | Picornaviridae,Kobuvirus,Aichivirus A | — | FJ890523,DQ028632, AY747174,GQ927704 ,JX564249,GQ92770 5,GQ927712,AB0407 49,GQ927706,GQ927 711 |
| Aichi virus 1 | NC_001918 | vertebrates | 1 | Picornaviridae,Kobuvirus,Aichivirus A | — | AB010145 |
| Alcelaphine herpesvirus 1 | NC_002531 | vertebrates | 1 | Herpesviridae,Macavirus,Alcelaphine herpesvirus 1 | — | AF005370 |
| Aleutian mink disease virus | NC_001662 | vertebrates | 6 | Parvoviridae,Amdovirus,Aleutian mink disease virus | — | GU269892,JN040434 ,Z18276,M20036,GU 183264,GU183265 |
| Ambystoma tigrinum virus | NC_005832 | vertebrates | 1 | Iridoviridae,Ranavirus,Ambystoma tigrinum virus | — | AY150217 |
| American bat vesiculovirus TFFN-2013 | NC_022755 | vertebrates | 1 | Rhabdoviridae,Vesiculovirus,American bat vesiculovirus TFFN-2013 | — | JX569193 |
| American grass carp reovirus | NC_010584 | vertebrates | 1 | Reoviridae,Aquareovirus,Aquareovirus G | seg. 1 | EF589098 |
| American grass carp reovirus | NC_010585 | vertebrates | 1 | Reoviridae,Aquareovirus,Aquareovirus G | seg. 2 | EF589099 |
| American grass carp reovirus | NC_010586 | vertebrates | 1 | Reoviridae,Aquareovirus,Aquareovirus G | seg. 3 | EF589100 |
| American grass carp reovirus | NC_010587 | vertebrates | 1 | Reoviridae,Aquareovirus,Aquareovirus G | seg. 4 | EF589101 |
| American grass carp reovirus | NC_010588 | vertebrates | 1 | Reoviridae,Aquareovirus,Aquareovirus G | seg. 5 | EF589102 |
| American grass carp reovirus | NC_010589 | vertebrates | 1 | Reoviridae,Aquareovirus,Aquareovirus G | seg. 6 | EF589103 |
| American grass carp reovirus | NC_010590 | vertebrates | 1 | Reoviridae,Aquareovirus,Aquareovirus G | seg. 7 | EF589104 |
| American grass carp reovirus | NC_010591 | vertebrates | 1 | Reoviridae,Aquareovirus,Aquareovirus G | seg. 8 | EF589105 |
| American grass carp reovirus | NC_010592 | vertebrates | 1 | Reoviridae,Aquareovirus,Aquareovirus G | seg. 9 | EF589106 |
| American grass carp reovirus | NC_010593 | vertebrates | 1 | Reoviridae,Aquareovirus,Aquareovirus G | seg. 10 | EF589107 |
| American grass carp reovirus | NC_010594 | vertebrates | 1 | Reoviridae,Aquareovirus,Aquareovirus G | seg. 11 | EF589108 |
| Amphotropic murine leukemia virus | NC_001702 ,NC_00181 | vertebrates | 1 | Retroviridae,Gammaretrovirus,Murine leukemia virus | — | AF411814 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Anatid herpesvirus 1 | 9,NC_0013 62,NC_001 501 | | | | | |
| | NC_013036 | vertebrates | Herpesviridae,Mardivirus,Anatid herpesvirus 1 | 6 | — | JQ673560,KF487736, JF999965,KF263690, EU082088,JQ647509 |
| Andrias davidianus | NC_005946 | vertebrates | Incloviridae,Ranavirus,Frog virus 3 ranavirus | 1 | — | KC865735 |
| Anguilla anguilla circovirus | NC_023421 | vertebrates | Circoviridae,Circovirus,Anguilla anguilla circovirus | 1 | — | KC469701 |
| Anguillid herpesvirus 1 | NC_013668 | vertebrates | Alloherpesviridae,Cyprinivirus,Anguillid herpesvirus 1 | 1 | — | FJ940765 |
| Aotine herpesvirus 1 | NC_016447 | vertebrates | Herpesviridae,Cytomegalovirus,Aotine herpesvirus 1 | 1 | — | FJ483970 |
| Aquareovirus A | NC_007582 | vertebrates | Reoviridae,Aquareovirus,Aquareovirus A | 1 | seg. 1 | AF418294 |
| Aquareovirus A | NC_007583 | vertebrates | Reoviridae,Aquareovirus,Aquareovirus A | 1 | seg. 2 | AF418295 |
| Aquareovirus A | NC_007584 | vertebrates | Reoviridae,Aquareovirus,Aquareovirus A | 1 | seg. 3 | AF418296 |
| Aquareovirus A | NC_007585 | vertebrates | Reoviridae,Aquareovirus,Aquareovirus A | 1 | seg. 4 | AF418297 |
| Aquareovirus A | NC_007588 | vertebrates | Reoviridae,Aquareovirus,Aquareovirus A | 1 | seg. 8 | AF418301 |
| Aquareovirus A | NC_007589 | vertebrates | Reoviridae,Aquareovirus,Aquareovirus A | 1 | seg. 9 | AF418302 |
| Aquareovirus A | NC_007590 | vertebrates | Reoviridae,Aquareovirus,Aquareovirus A | 1 | seg. 10 | AF418303 |
| Aquareovirus A | NC_007591 | vertebrates | Reoviridae,Aquareovirus,Aquareovirus A | 1 | seg. 11 | AF418304 |
| Aquareovirus A | NC_007592 | vertebrates | Reoviridae,Aquareovirus,Aquareovirus A | 1 | seg. 6 | AF418299 |
| Aquareovirus C | NC_005166 | vertebrates | Reoviridae,Aquareovirus,Aquareovirus C | 1 | seg. 1 | AF403398 |
| Aquareovirus C | NC_005167 | vertebrates | Reoviridae,Aquareovirus,Aquareovirus C | 1 | seg. 2 | AF403399 |
| Aquareovirus C | NC_005168 | vertebrates | Reoviridae,Aquareovirus,Aquareovirus C | 1 | seg. 3 | AF403400 |
| Aquareovirus C | NC_005169 | vertebrates | Reoviridae,Aquareovirus,Aquareovirus C | 1 | seg. 4 | AF403401 |
| Aquareovirus C | NC_005170 | vertebrates | Reoviridae,Aquareovirus,Aquareovirus C | 1 | seg. 5 | AF403402 |
| Aquareovirus C | NC_005171 | vertebrates | Reoviridae,Aquareovirus,Aquareovirus C | 1 | seg. 6 | AF403403 |
| Aquareovirus C | NC_005172 | vertebrates | Reoviridae,Aquareovirus,Aquareovirus C | 1 | seg. 7 | AF403404 |
| Aquareovirus C | NC_005173 | vertebrates | Reoviridae,Aquareovirus,Aquareovirus C | 1 | seg. 8 | AF403405 |
| Aquareovirus C | NC_005174 | vertebrates | Reoviridae,Aquareovirus,Aquareovirus C | 1 | seg. 9 | AF403406 |
| Aquareovirus C | NC_005175 | vertebrates | Reoviridae,Aquareovirus,Aquareovirus C | 1 | seg. 10 | AF403407 |
| Aquareovirus C | NC_005176 | vertebrates | Reoviridae,Aquareovirus,Aquareovirus C | 1 | seg. 11 | AF403408 |
| Arctic ground squirrel hepatitis B virus | NC_001484 | vertebrates | Hepadnaviridae,Orthohepadnavirus,Ground squirrel hepatitis virus | 1 | — | U29144 |
| Artibeus jamaicensis parvovirus 1 | NC_016752 | vertebrates | Parvoviridae, Artibeus jamaicensis parvovirus 1 | 1 | — | JQ037754 |
| Astrovirus MLB1 | NC_011400 | vertebrates | Astroviridae,Astrovirus MLB1 | 5 | — | JQ086552,AB823732, AB823731,FJ402983, FJ222451 |
| Astrovirus MLB1 HK05 | NC_011400 | vertebrates | Astroviridae,Astrovirus MLB1 | 1 | — | HM450380 |
| Astrovirus MLB2 | NC_016155 | vertebrates | Astroviridae,Astrovirus MLB2 | 2 | — | JF742759,AB829252 |
| Astrovirus MLB3 | NC_019028 | vertebrates | Astroviridae,Astrovirus MLB3 | 1 | — | JX857870 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Astrovirus VA1 | NC_013060 | vertebrates | 1 | Astroviridae,Astrovirus VA1 | — | FJ973620 |
| Astrovirus VA2 | NC_018669 | vertebrates | 1 | Astroviridae,Astrovirus VA2 | — | GQ502193 |
| Astrovirus VA3 | NC_019026 | vertebrates | 1 | Astroviridae,Astrovirus VA3 | — | JX857868 |
| Astrovirus VA4 | NC_019027 | vertebrates | 1 | Astroviridae,Astrovirus VA4 | — | JX857869 |
| Astrovirus wild boar/W BAstV-1/2011/HUN | NC_016896 | vertebrates | 1 | Astroviridae,Mamastrovirus,Astrovirus wild boar/W BAstV-1/2011/HU N | — | JQ340310 |
| Ateles paniscus polyomavirus 1 | NC_019853 | vertebrates | 1 | Polyomaviridae,Polyomavirus,Ateles paniscus polyomavirus 1 | — | JX159987 |
| Ateline herpesvirus 3 | NC_001987 | vertebrates | 1 | Herpesviridae,Rhadinovirus,Ateline herpesvirus 3 | — | AF083424 |
| Atlantic salmon reovirus TS | NC_007583 | vertebrates | 1 | Reoviridae,Aquareovirus,Aquareovirus A | seg. 2 | EF434978 |
| Atlantic salmon reovirus TS | NC_007590 | vertebrates | 1 | Reoviridae,Aquareovirus,Aquareovirus A | seg. 10 | EF434979 |
| Atlantic salmon swim bladder sarcoma virus | NC_007654 | vertebrates | 1 | Retroviridae,Atlantic salmon swim bladder sarcoma virus | — | DQ174103 |
| Avian adeno-associated virus | NC_006263 | vertebrates | 1 | Parvoviridae,Dependovirus,Avian adeno-associated virus | — | GQ368252 |
| Avian adeno-associated virus ATCC VR-865 | NC_004828 | vertebrates | 2 | Parvoviridae,Dependovirus,Avian adeno-associated virus ATCC VR-865 | — | AY186198,AY629582 |
| Avian adeno-associated virus strain DA-1 | NC_006263 | vertebrates | 1 | Parvoviridae,Dependovirus,Avian adeno-associated virus | — | AY629583 |
| Avian carcinoma virus | NC_001402 | vertebrates | 1 | Retroviridae,Alpharetrovirus,Avian carcinoma virus | — | M14008 |
| Avian encephalomyelitis virus | NC_003990 | vertebrates | 3 | Picornaviridae,Tremovirus,Avian encephalomyelitis virus | — | AJ225173,AY275539, AY517471 |
| Avian endogenous retrovirus EAV-HP | NC_005947 | vertebrates | 7 | Retroviridae, Avian endogenous retrovirus EAV-HP | — | AJ623291,AJ238124, AJ238125,AJ623292, AJ623289,AJ292966, AJ623290 |
| Avian gyrovirus 2 | NC_015396 | vertebrates | 2 | Circoviridae,Gyrovirus,Avian gyrovirus 2 | — | HM590588,JQ690763 |
| Avian infectious bronchitis virus (strain Beaudette CK) | NC_010800 ,NC_001451 | vertebrates | 1 | Coronaviridae,Gammacoronavirus,Avian coronavirus | — | AJ311317 |
| Avian infectious bronchitis virus partridge/GD/S14/2003 | NC_010800 ,NC_001451 | vertebrates | 1 | Coronaviridae,Gammacoronavirus,Avian coronavirus | — | AY646283 |
| Avian leukemia virus | NC_015116 ,NC_001408 | vertebrates | 1 | Retroviridae,Alpharetrovirus,Avian leukosis virus | — | HQ425636 |
| Avian leukosis virus | NC_015116 ,NC_001408 | vertebrates | 59 | Retroviridae,Alpharetrovirus,Avian leukosis virus | — | KF562374,JF932001, JF932004,HQ148555, AY01303,AB669569 JF931999,HM58265 7,AB669897,AB6694 33,AB670314,AB764 104,AB303223,EU07 0900,JF826241,JX25 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | 4901,JF932002,HM4 52340,HM235667,KF 738251,KF562373,H M235669,EU070902, JF932003,DQ365814, JN389518,AB764106, FJ216405,AB669896, HM452342,HM23566 8,HM452339,JN6248 80,JF932000,AB7641 07,GU982310,JN389 517,HQ148554,HM45 2341,GU982308,EU0 70901,AB682778,HQ 900844,EF467236,JN 624879,HM235670,K F562375,HM582658, JF951728,AB112960, JX855935,AY013304, JX453210,AB670312, DQ115805,HM23566 5,HM776937,JN6248 78,AB669568 |
| Avian leukosis virus HPRS103 | NC_015116 ,NC_001408 | vertebrates | Retroviridae,Alpharetrovirus,Avian leukosis virus | 1 | — | Z46390 |
| Avian leukosis virus LR-9 | NC_015116 ,NC_001408 | vertebrates | Retroviridae,Alpharetrovirus,Avian leukosis virus | 1 | — | AY350569 |
| Avian myelocytomatosis virus | NC_001866 | vertebrates | Retroviridae,Alpharetrovirus,Avian myelocytomatosis virus | 2 | — | M11784,AF033809 |
| Avian orthoreovirus | NC_015126 | vertebrates | Reoviridae,Orthoreovirus,Avian orthoreovirus | 8 | seg. L1 | FR694191,DQ238093 ,DQ238094,EU61673 9,EU616735,HM2229 78,AY547458,KC183 748 |
| Avian orthoreovirus | NC_015127 | vertebrates | Reoviridae,Orthoreovirus,Avian orthoreovirus | 2 | seg. L2 | HM222980,FR694192 |
| Avian orthoreovirus | NC_015128 | vertebrates | Reoviridae,Orthoreovirus,Avian orthoreovirus | 14 | seg. L3 | AY652695,AY652698 ,AY652700,DQ30017 5,AY652694,EU6167 38,FR694193,HM222 979,AY652699,AY65 2697,AY652696,AY6 52701,EU616737,AY 652693 |
| Avian orthoreovirus | NC_015129 | vertebrates | Reoviridae,Orthoreovirus,Avian orthoreovirus | 19 | seg. M | AY639620,AY639614 ,AY557188,EU61673 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Avian orthoreovirus | | | | | | 6,AY639612,AY5571 89,AY639619,AY639 617,AY639621,AY63 9613,AY639616,FR6 94194,AY639611,AY 639618,AY639615,E U616740,HM222977, DQ300176,AY639610 |
| Avian orthoreovirus | NC_015130 | vertebrates | 19 | Reoviridae,Orthoreovirus,Avian orthoreovirus | seg. M | AY635940,AY635938 2,EU61674l,HM22297 6,AY635936,DQ3001 77,AY635943,AY635 935,AY635945,AY63 5944,EU61674 2,AY6 35941,AY635934,AY 635939,AY750053,A Y635937,AY635942,F R694195,AY750052 |
| Avian orthoreovirus | NC_015131 | vertebrates | 21 | Reoviridae,Orthoreovirus,Avian orthoreovirus | seg. M3 | AY573911,FR694196 ,AY573912,AY57391 3,AY573908,AY5739 07,AY557191,AY573 909,EU616744,AY57 3905,AY573910,KC8 65791,AY573914,AY 608700,AY557190,A Y573904,AY573915, EU616743,HM222297 5,AY303993,AY5739 06 |
| Avian orthoreovirus | NC_015132 | vertebrates | 15 | Reoviridae,Orthoreovirus,Avian orthoreovirus | seg. S1 | AF004857,JN559377, L39002, HM222974,D 0525419,JN559375,F R694197,DQ643974, DQ868790, DQ86879 1,DQ643975,EF0573 97,DQ868789,EF057 398,EU526387 |
| Avian orthoreovirus | NC_015133 | vertebrates | 6 | Reoviridae,Orthoreovirus,Avian orthoreovirus | seg. S2 | AF059717,FR694198, AF104311,JN559376, AF059716,HM222973 |
| Avian orthoreovirus | NC_015134 | vertebrates | 12 | Reoviridae,Orthoreovirus,Avian orthoreovirus | seg. S3 | EF030496,JQ924284, AF059720,EF030498, AF059721,EF030497, HM222972,AF004856 ,EF030499,JQ916907 ,DQ415659,FR69419 9 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Avian orthoreovirus | NC_015135 | vertebrates | Reoviridae,Orthoreovirus,Avian orthoreovirus | 6 | seg. S4 | HM222971,AF059725,EF122838,JN559378,AF059724,FR694200 |
| Avian orthoreovirus strain 1017-1 | NC_015126 | vertebrates | Reoviridae,Orthoreovirus,Avian orthoreovirus | 1 | seg. L1 | AY641740 |
| Avian orthoreovirus strain 2408 | NC_015126 | vertebrates | Reoviridae,Orthoreovirus,Avian orthoreovirus | 1 | seg. L1 | AY641742 |
| Avian orthoreovirus strain 601G | NC_015126 | vertebrates | Reoviridae,Orthoreovirus,Avian orthoreovirus | 1 | seg. L1 | AY641736 |
| Avian orthoreovirus strain 916 | NC_015126 | vertebrates | Reoviridae,Orthoreovirus,Avian orthoreovirus | 1 | seg. L1 | AY641737 |
| Avian orthoreovirus strain 918 | NC_015126 | vertebrates | Reoviridae,Orthoreovirus,Avian orthoreovirus | 1 | seg. L1 | AY641738 |
| Avian orthoreovirus strain 919 | NC_015126 | vertebrates | Reoviridae,Orthoreovirus,Avian orthoreovirus | 1 | seg. L1 | AY641739 |
| Avian orthoreovirus strain OS161 | NC_015126 | vertebrates | Reoviridae,Orthoreovirus,Avian orthoreovirus | 1 | seg. L1 | AY641743 |
| Avian orthoreovirus strain R2/TW | NC_015126 | vertebrates | Reoviridae,Orthoreovirus,Avian orthoreovirus | 1 | seg. L1 | AY641744 |
| Avian reovirus strain 1733 | NC_015126 | vertebrates | Reoviridae,Orthoreovirus,Avian orthoreovirus | 1 | seg. L1 | AY641741 |
| Avian reovirus strain 1733 | NC_015128 | vertebrates | Reoviridae,Orthoreovirus,Avian orthoreovirus | 1 | seg. L3 | AF384171 |
| Avian reovirus strain S1133 | NC_015126 | vertebrates | Reoviridae,Orthoreovirus,Avian orthoreovirus | 1 | seg. L1 | AY641735 |
| Avian reovirus strain S1133 | NC_015132 | vertebrates | Reoviridae,Orthoreovirus,Avian orthoreovirus | 1 | seg. S1 | AF330703 |
| Avian sapelovirus | NC_006553 | vertebrates | Picornaviridae,Sapelovirus,Avian sapelovirus | 1 | — | AY563023 |
| Avirulent turkey hemorrhagic enteritis virus | NC_001958 | vertebrates | Adenoviridae,Siadenovirus,Turkey adenovirus A | 1 | — | AY849321 |
| Baboon enterovirus | NC_010415 | vertebrates | Picornaviridae,Enterovirus,Enterovirus J | 1 | — | AF326766 |
| Baboon orthoreovirus | NC_015877 | vertebrates | Reoviridae,Orthoreovirus,Baboon orthoreovirus | 1 | seg. L1 | HQ847903 |
| Baboon orthoreovirus | NC_015878 | vertebrates | Reoviridae,Orthoreovirus,Baboon orthoreovirus | 1 | seg. L2 | HQ847904 |
| Baboon orthoreovirus | NC_015879 | vertebrates | Reoviridae,Orthoreovirus,Baboon orthoreovirus | 1 | seg. L3 | HQ847905 |
| Baboon orthoreovirus | NC_015880 | vertebrates | Reoviridae,Orthoreovirus,Baboon orthoreovirus | 1 | seg. M1 | HQ847906 |
| Baboon orthoreovirus | NC_015881 | vertebrates | Reoviridae,Orthoreovirus,Baboon orthoreovirus | 1 | seg. M2 | HQ847907 |
| Baboon orthoreovirus | NC_015882 | vertebrates | Reoviridae,Orthoreovirus,Baboon orthoreovirus | 1 | seg. M3 | HQ847908 |
| Baboon orthoreovirus | NC_015883 | vertebrates | Reoviridae,Orthoreovirus,Baboon orthoreovirus | 1 | seg. S1 | AF059719 |
| Baboon orthoreovirus | NC_015884 | vertebrates | Reoviridae,Orthoreovirus,Baboon orthoreovirus | 1 | seg. S2 | AF059723 |
| Baboon orthoreovirus | NC_015885 | vertebrates | Reoviridae,Orthoreovirus,Baboon orthoreovirus | 1 | seg. | AF406787 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Baboon orthoreovirus | NC_015886 | vertebrates | 1 | Reoviridae,Orthoreovirus,Baboon orthoreovirus | S4 | AF059727 |
| Bandicoot papillomatosis carcinomatosis virus type 1 | NC_010107 | vertebrates | 1 | Papillomaviridae,Bandicoot papillomatosis carcinomatosis virus type 1 | seg. S3 | EU069819 |
| Bandicoot papillomatosis carcinomatosis virus type 2 | NC_010817 | vertebrates | 1 | Papillomaviridae,Bandicoot papillomatosis carcinomatosis virus type 2 | — | EU277647 |
| Barbel circovirus | NC_015399 | vertebrates | 2 | Circoviridae,Circovirus,Barbel circovirus | — | JF279961,GU799606 |
| Barfin flounder nervous necrosis virus | NC_013458 | vertebrates | 1 | Nodaviridae,Betanodavirus,Barfin flounder nervous necrosis virus | seg. RNA 1 | EU236146 |
| Barfin flounder nervous necrosis virus | NC_013459 | vertebrates | 1 | Nodaviridae,Betanodavirus,Barfin flounder nervous necrosis virus | seg. RNA 2 | EU236147 |
| Barfin flounder virus BF93Hok | NC_011063 | vertebrates | 1 | Nodaviridae,Betanodavirus,Barfin flounder virus BF93Hok | seg. RNA 1 | EU826137 |
| Barfin flounder virus BF93Hok | NC_011064 | vertebrates | 1 | Nodaviridae,Betanodavirus,Barfin flounder virus BF93Hok | seg. RNA 2 | EU826138 |
| Bat adeno-associated virus YNM | NC_014468 | vertebrates | 1 | Parvoviridae,Dependovirus,Bat adeno-associated virus YNM | — | GU226971 |
| Bat adenovirus 2 | NC_015932 | vertebrates | 1 | Adenoviridae,Mastadenovirus,Bat adenovirus B | — | JN252129 |
| Bat adenovirus TJM | NC_016895 | vertebrates | 1 | Adenoviridae,Mastadenovirus,Bat adenovirus A | — | GU226970 |
| Bat circovirus | NC_021206 | vertebrates | 2 | Circoviridae,Circovirus,Bat circovirus | — | KC339249,JX863737 |
| Bat coronavirus (BtCoV/133/2005) | NC_008315 | vertebrates | 1 | Coronaviridae,Betacoronavirus,Bat coronavirus (BtCoV/133/2005) | — | DQ648794 |
| Bat coronavirus 1A | NC_010437 | vertebrates | 1 | Coronaviridae,Alphacoronavirus,Bat coronavirus 1A | — | EU420138 |
| Bat coronavirus 1B | NC_010436 | vertebrates | 1 | Coronaviridae,Alphacoronavirus,Bat coronavirus 1B | — | EU420137 |
| Bat coronavirus BM48-31/BG R/2008 | NC_014470 | vertebrates | 1 | Coronaviridae,Betacoronavirus,Bat coronavirus BM48-31/BG R/2008 | — | GU190215 |
| Bat coronavirus CDPHE15/USA/2006 | NC_022103 | vertebrates | 1 | Coronaviridae,Alphacoronavirus,Bat coronavirus CDPHE15/USA/2006 | — | KF430219 |
| Bat coronavirus HKU4-2 | NC_009019 | vertebrates | 1 | Coronaviridae,Betacoronavirus,Tylonycteris bat coronavirus HKU4 | — | EF065506 |
| Bat coronavirus HKU4-3 | NC_009019 | vertebrates | 1 | Coronaviridae,Betacoronavirus,Tylonycteris bat coronavirus HKU4 | — | EF065507 |
| Bat coronavirus HKU4-4 | NC_009019 | vertebrates | 1 | Coronaviridae,Betacoronavirus,Tylonycteris bat coronavirus HKU4 | — | EF065508 |
| Bat coronavirus HKU5-2 | NC_009020 | vertebrates | 1 | Coronaviridae,Betacoronavirus,Pipistrellus bat coronavirus HKU5 | — | EF065510 |
| Bat coronavirus HKU5-3 | NC_009020 | vertebrates | 1 | Coronaviridae,Betacoronavirus,Pipistrellus bat coronavirus HKU5 | — | EF065511 |
| Bat coronavirus HKU5-5 | NC_009020 | vertebrates | 1 | Coronaviridae,Betacoronavirus,Pipistrellus bat coronavirus HKU5 | — | EF065512 |
| Bat coronavirus HKU9-10-1 | NC_009021 | vertebrates | 1 | Coronaviridae,Betacoronavirus,Rousettus bat coronavirus HKU9 | — | HM211100 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bat coronavirus HKU9-10-2 | NC_009021 | vertebrates | 1 | Coronaviridae,Betacoronavirus,Rousettus bat coronavirus HKU9 | — | HM211101 |
| Bat coronavirus HKU9-2 | NC_009021 | vertebrates | 1 | Coronaviridae,Betacoronavirus,Rousettus bat coronavirus HKU9 | — | EF065514 |
| Bat coronavirus HKU9-3 | NC_009021 | vertebrates | 1 | Coronaviridae,Betacoronavirus,Rousettus bat coronavirus HKU9 | — | EF065515 |
| Bat coronavirus HKU9-4 | NC_009021 | vertebrates | 1 | Coronaviridae,Betacoronavirus,Rousettus bat coronavirus HKU9 | — | EF065516 |
| Bat coronavirus HKU9-5-1 | NC_009021 | vertebrates | 1 | Coronaviridae,Betacoronavirus,Rousettus bat coronavirus HKU9 | — | HM211098 |
| Bat coronavirus HKU9-5-2 | NC_009021 | vertebrates | 1 | Coronaviridae,Betacoronavirus,Rousettus bat coronavirus HKU9 | — | HM211099 |
| Bat hepatitis virus | NC_020881 | vertebrates | 3 | Hepadnaviridae,Bat hepatitis virus | — | JX941466,JX941467,JX941468 |
| Bat picornavirus 1 | NC_015940 | vertebrates | 2 | Picornaviridae,Bat picornavirus 1 | — | HQ595341,HQ595340 |
| Bat picornavirus 2 | NC_015941 | vertebrates | 2 | Picornaviridae,Bat picornavirus 2 | — | HQ595342,HQ595343 |
| Bat picornavirus 3 | NC_015934 | vertebrates | 2 | Picornaviridae,Bat picornavirus 3 | — | HQ595345,HQ595344 |
| Beak and feather disease virus | NC_001944 | vertebrates | 205 | Circoviridae,Circovirus,Beak and feather disease virus | — | JQ782201,GU936294,JX221005,JX221002,GU936287,JQ782197,GQ396655,JX221003,AY521238,KF188694,AF311297,JXQ49204,JX221025,GQ165756,GU015021,JX221014,AY450436,GUO15014,HM748920,JX25014,HM748920,JX221001,HM748922,GU936289,AY521236,JX049195,GU936291,GU015015,JF519618,JX221031,JX221030,AB277750,GQ396653,GU936290,HM748927,HM748935,AF311299,JX221007,GU015023,KC980909,AB277747,JX221011,HM748924,GQ120621,JX221006,JXQ49198,AY450441,JX221004,GQ396652,AB277746,JX221040,HM748925,KF188684,KF467254,JXQ49197,DQ397818 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | ,JXQ49199,AB277751,JX221016,JQ782199,GU047347,KC693651,KF188685,FJ685980,GU015012,AF071878,AF311296,JX221012,GQ386944,KF188687,JQ782196,EF457975,GU015018,JX221032,GU015016,JX221021,JXQ49216,AY450438,AY450440,AF311302,JXQ49219,JX221008,GU015019,GU936295,HM748932,EU810208,FJ685989,AF311301,JXQ49200,KF188683,JXQ49218,JXQ49209,GU015022,KF188689,JX221024,JXQ49217,JX221010,JXQ49220,HM748919,JX221037,KF188681,JQ782200,HM748934,HM748928,JXQ49204,KF188690,JXQ49205,JXQ49208,JX221036,JF519619,AB514568,GQ165757,FJ685979,JX221038,HM748931,JQ782208,AY450442,JXQ49214,JX221035,JX221039,JQ782204,KF188693,JX221018,JX221043,JXQ49203,AY450434,AY450439,KF188686,GQ165758,KF188682,G0396656,JX221022,JX221013,JQ782206,HM748929,AY521237,GU936292,KF673335,JX221019,GU936296,KF673337,KF467252,AY450435,AB277748,FJ685985,JX221026,JX221034,HM748938,JX221041,HM7 |

TABLE 10-continued

| Taxonomy | Rep.Acc.ID | Host | ViroCap-1.0 Taxonomy ‖ # GN's | Lineage | Seg. Count | GN.Acc.IDs |
|---|---|---|---|---|---|---|
| Beluga Whale coronavirus SW1 | NC_010646 | vertebrates | 1 | Coronaviridae,Gammacoronavirus,Beluga Whale coronavirus SW1 | — | 48933,EF445974,AY450443,JXQ49211,HM748930,JXQ49207,JX221027,JXQ49207,AF221027,JXQ49207,AF311300,HM748926,KF67336,GU015013,JX221020,JXQ49213,AF311298,JXQ49202,JX221023,GU936293,JQ782198,JXQ49196,GQ329705,JX221017,HM748937,KF56125 0,HM748921,JX221029,JX221033,GU015017,KF850537,HM748936,HM748918,JQ782205,EU810207,JXQ49215,GU936288,AF080560,GQ396654,JXQ49210,AB277749,KF188688,JXQ49201,GU015020,HM748923,KC510146,KF188692,JXQ49212,AF311295,GU936297,HM748939,KF467251,JXQ49221,KF188691,JX221009,JX221028,AY450437,FJ685978,KF467253,JX221015 |
| Betacoronavirus England 1 | NC_019843 | vertebrates | 1 | Coronaviridae,Betacoronavirus,Middle East respiratory syndrome coronavirus | — | EU111742 |
| Betacoronavirus Erinaceus/VMC/DEU/2012 | NC_022643 | vertebrates | 2 | Coronaviridae,Betacoronavirus,Betacoronavirus Erinaceus/VMC/D EU/2012 | — | KC545383,KC545386 |
| Bettongia penicillata papillomavirus 1 | NC_014143 | vertebrates | 1 | Papillomaviridae,Bettongia penicillata papillomavirus 1 | — | GU220391 |
| Blotched snakehead virus | NC_005982 | vertebrates | 1 | Birnaviridae,Blosnavirus,Blotched snakehead virus | seg. A | AJ459382 |
| Blotched snakehead virus | NC_005983 | vertebrates | 1 | Birnaviridae,Blosnavirus,Blotched snakehead virus | seg. B | AJ459383 |
| Bluegill picornavirus | NC_018506 | vertebrates | 1 | Bluegill picornavirus | — | JX134222 |
| Bocavirus gorilla/GBoV1/2009 | NC_014358 | vertebrates | 1 | Parvoviridae,Bocavirus,Bocavirus gorilla/GBoV1/2009 | — | HM145750 |
| Border disease virus | NC_003679 | vertebrates | 5 | Flaviviridae,Pestivirus,Border disease virus | — | KC963426,KF925348,AF037405,GU270877,GQ902940 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Border disease virus-BD31 | NC_003679 | vertebrates | 1 | Flaviviridae,Pestivirus,Border disease virus | — | U70263 |
| Bos grunniens papillomavirus type 1 | NC_001522 | vertebrates | 6 | Papillomaviridae,Deltapapillomavirus,Deltapapillomavirus 4 | — | JX174438,JX174439,JX174441,JX174442,JX174437,JX174440 |
| Bottlenose dolphin coronavirus HKU22 | NC_010646 | vertebrates | 3 | Coronaviridae,Gammacoronavirus,Beluga Whale coronavirus SW1 | — | KF793824,KF793825,KF793826 |
| Bovine adeno-associated virus | NC_005889 | vertebrates | 1 | Parvoviridae,Dependovirus,Bovine adeno-associated virus | — | AY388617 |
| Bovine adenovirus 3 | NC_001876 | vertebrates | 1 | Adenoviridae,Mastadenovirus,Bovine adenovirus B | — | JN381195 |
| Bovine adenovirus 6 | NC_020074 | vertebrates | 1 | Adenoviridae,Atadenovirus,Bovine adenovirus E | — | JQ345700 |
| Bovine adenovirus B | NC_001876 | vertebrates | 1 | Adenoviridae, Mastadenovirus, Bovine adenovirus B | — | AF030154 |
| Bovine adenovirus D | NC_002685 | vertebrates | 1 | Adenoviridae,Atadenovirus,Bovine adenovirus D | — | AF036092 |
| Bovine calicivirus | NC_002551 | vertebrates | 1 | Caliciviridae,Vesivirus,Vesicular exanthema of swine virus | — | AJQ11099 |
| Bovine circovirus | NC_005148 | vertebrates | 1 | Circoviridae,Circovirus,Porcine circovirus 2 | — | AF109397 |
| Bovine coronavirus | NC_010327,NC_00773 2,NC_0051 47,NC_003 045 | vertebrates | 4 | Coronaviridae,Betacoronavirus,Betacoronavir | — | AF391542,AF220295,U00735,AB354579 |
| Bovine coronavirus DB2 | NC_010327,NC_00773 2,NC_0051 47,NC_003 045 | vertebrates | 1 | Coronaviridae,Betacoronavirus, Betacoronavirus 1 | — | DQ811784 |
| Bovine coronavirus E-AH187 | NC_010327,NC_00773 2,NC_0051 47,NC_003 045 | vertebrates | 1 | Coronaviridae,Betacoronavirus, Betacoronavirus 1 | — | EF424619 |
| Bovine coronavirus E-AH187-TC | NC_010327,NC_00773 2,NC_0051 47,NC_003 045 | vertebrates | 1 | Coronaviridae,Betacoronavirus, Betacoronavirus 1 | — | FJ938064 |
| Bovine coronavirus E-AH65 | NC_010327,NC_00773 2,NC_0051 47,NC_003 045 | vertebrates | 1 | Coronaviridae,Betacoronavirus, Betacoronavirus 1 | — | EF424615 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Bovine coronavirus E-AH65-TC | NC_010327,NC_007732,NC_0051 47,NC_003045 | vertebrates | Coronaviridae,Betacoronavirus, Betacoronavirus 1 | 1 | — | EF424616 |
| Bovine coronavirus E-DB2-TC | NC_010327,NC_007732,NC_0051 47,NC_003045 | vertebrates | Coronaviridae,Betacoronavirus, Betacoronavirus 1 | 1 | — | FJ938063 |
| Bovine coronavirus R-AH187 | NC_010327,NC_007732,NC_0051 47,NC_003045 | vertebrates | Coronaviridae,Betacoronavirus, Betacoronavirus 1 | 1 | — | EF424620 |
| Bovine coronavirus R-AH65 | NC_010327,NC_007732,NC_0051 47,NC_003045 | vertebrates | Coronaviridae,Betacoronavirus, Betacoronavirus 1 | 1 | — | EF424617 |
| Bovine coronavirus R-AH65-TC | NC_010327,NC_007732,NC_0051 47,NC_003045 | vertebrates | Coronaviridae,Betacoronavirus, Betacoronavirus 1 | 1 | — | EF424618 |
| Bovine coronavirus isolate Alpaca | NC_010327,NC_007732,NC_0051 47,NC_003045 | vertebrates | Coronaviridae,Betacoronavirus, Betacoronavirus 1 | 1 | — | DQ915164 |
| Bovine enterovirus | NC_001859 | vertebrates | Picornaviridae,Enterovirus,Enterovirus E | 4 | — | DQ092769,DQ092771,DQ092792,DQ092793 |
| Bovine enterovirus strain K2577 | NC_001859 | vertebrates | Picornaviridae,Enterovirus,Enterovirus E | 1 | — | AF123432 |
| Bovine enterovirus strain SL305 | NC_001859 | vertebrates | Picornaviridae,Enterovirus,Enterovirus E | 1 | — | AF123433 |
| Bovine enterovirus type 2 | NC_021220 | vertebrates | Picornaviridae,Enterovirus,Enterovirus F | 4 | — | HQ663846,AY508696,HQ917060,AY508697 |
| Bovine foamy virus Y134750,JX307862 | NC_001831 | vertebrates | Retroviridae,Spumavirus,Bovine foamy virus | 4 | — | U94514,JX307861,A |
| Bovine herpesvirus 1 | NC_001847 | vertebrates | Herpesviridae,Varicellovirus,Bovine herpesvirus 1 | 1 | — | AJQ04801 |
| Bovine herpesvirus 4 | NC_002665 | vertebrates | Herpesviridae,Rhadinovirus,Bovine herpesvirus 4 | 2 | — | AF318573,JN133502 |
| Bovine herpesvirus 5 | NC_005261 | vertebrates | Herpesviridae,Varicellovirus,Bovine herpesvirus 5 | 1 | — | AY261359 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bovine herpesvirus type 1.1 | NC_001847 | vertebrates | 1 | Herpesviridae,Varicellovirus,Bovine herpesvirus 1 | — | JX898220 |
| Bovine hungarovirus 1 | NC_018668 | vertebrates | 1 | Picornaviridae,Hunnivirus,Hunnivirus A | — | JQ941880 |
| Bovine immunodeficiency virus | NC_001413 | vertebrates | 1 | Retroviridae,Lentivirus,Bovine immunodeficiency virus | — | M32690 |
| Bovine kobuvirus | NC_004421 | vertebrates | 1 | Picornaviridae,Kobuvirus,Aichivirus B | — | AB084788 |
| Bovine leukemia virus | NC_001414 | vertebrates | 9 | Retroviridae,Deltaretrovirus,Bovine leukemia virus | — | AF033818,FJ914764, DQ0647,AF257515,H E967301,K02120,HE 967303,EF600696,H E967302 |
| Bovine papillomavirus-1 | NC_001522 | vertebrates | 1 | Papillomaviridae,Deltapapillomavirus,Deltapap illomavirus 4 | — | XQ2346 |
| Bovine papillomavirus-3 | NC_004197 | vertebrates | 1 | Papillomaviridae,Xipapillomavirus,Xipapilloma virus 1 | — | AJ620207 |
| Bovine papillomavirus-4 | NC_004197 | vertebrates | 1 | Papillomaviridae,Xipapillomavirus,Xipapilloma virus 1 | — | XQ5817 |
| Bovine papillomavirus-5 | NC_004195 | vertebrates | 1 | Papillomaviridae,Epsilonpapillomavirus,Epsilo npapillomavirus 1 | — | AJ620206 |
| Bovine papillomavirus-6 | NC_004197 | vertebrates | 1 | Papillomaviridae,Xipapillomavirus,Xipapilloma virus 1 | — | AJ620208 |
| Bovine papillomavirus 3 | NC_004197 | vertebrates | 1 | Papillomaviridae,Xipapillomavirus, Xipapillomavirus 1 | — | AF486184 |
| Bovine papillomavirus 7 | NC_007612 | vertebrates | 1 | Papillomaviridae,Bovine papillomavirus 7 | — | DQ217793 |
| Bovine papillomavirus 8 | NC_004195 | vertebrates | 1 | Papillomaviridae,Epsilonpapillomavirus,Epsilo npapillomavirus 1 | — | DQ098913 |
| Bovine papillomavirus BAA5-Japan | NC_004197 | vertebrates | 1 | Papillomaviridae,Xipapillomavirus, Xipapillomavirus 1 | — | EU360723 |
| Bovine papillomavirus type 1 | NC_001522 | vertebrates | 2 | Papillomaviridae,Deltapapillomavirus,Deltapap illomavirus 4 | — | JX678969,AB626705 |
| Bovine papillomavirus type 10 | NC_004197 | vertebrates | 2 | Papillomaviridae,Xipapillomavirus, Xipapillomavirus 1 | — | AB331651,KF017607 |
| Bovine papillomavirus type 11 | NC_004197 | vertebrates | 1 | Papillomaviridae,Xipapillomavirus, Xipapillomavirus 1 | — | AB543507 |
| Bovine papillomavirus type 8-EB | NC_004197 | vertebrates | 2 | Papillomaviridae,Xipapillomavirus, Xipapillomavirus 1 | — | JF834524,JF834523 |
| Bovine papillomavirus type 12 | NC_001522 | vertebrates | 1 | Papillomaviridae,Deltapapillomavirus,Deltapap illomavirus type | — | JQ798171 |
| Bovine papillomavirus type 13 | NC_001522 | vertebrates | 2 | Papillomaviridae,Deltapapillomavirus,Deltapap illomavirus 4 | — | M20219,KC878306 |
| Bovine papillomavirus type 9 | NC_004195 | vertebrates | 1 | Papillomaviridae,Epsilonpapillomavirus,Epsilo npapillomavirus 1 | — | DQ098917 |
| Bovine papillomavirus type 8 | NC_004197 | vertebrates | 1 | Papillomaviridae,Xipapillomavirus, Xipapillomavirus 1 | — | AB331650 |
| Bovine papular stomatitis virus | NC_005337 | vertebrates | 1 | Poxviridae,Parapoxvirus,Bovine papular stomatitis virus | — | AY386265 |
| Bovine parvovirus | NC_001540 | vertebrates | 1 | Parvoviridae,Bocavirus,Bovine parvovirus | — | M14363 |
| Bovine parvovirus-2 | NC_006259 | vertebrates | 1 | Parvoviridae,Dependovirus,Bovine parvovirus-2 | — | AF406966 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bovine parvovirus-1 | NC_001540 | vertebrates | 1 | Parvoviridae,Bocavirus,Bovine parvovirus | — | DQ335247 |
| Bovine polyomavirus polyomavirus | NC_001442 | vertebrates | 1 | Polyomaviridae,Polyomavirus,Bovine polyomavirus | — | D13942 |
| Bovine respiratory coronavirus AH187 | NC_012948 | vertebrates | 1 | Coronaviridae, Bovine respiratory coronavirus AH187 | — | FJ938065 |
| Bovine respiratory coronavirus bovine/US/OH-440-TC/1996 | NC_012949 | vertebrates | 1 | Coronaviridae, Bovine respiratory coronavirus bovine/US/OH-440-TC/1996 | — | FJ938066 |
| Bovine rhinitis B virus | NC_010354 | vertebrates | 1 | Picornaviridae,Aphthovirus,Bovine rhinitis B virus | — | EU236594 |
| Bovine viral diarrhea virus 1 | NC_001461 | vertebrates | 17 | Flaviviridae,Pestivirus,Bovine viral diarrhea virus 1 | — | JX419397,U86599,AJ133739,KC963967,AF041040,KC757383,M31182,AJ133738,EF101530,KF772785,U86600,AF268278,DQ088995,JN400273,AF220247,JX419398,JQ799141 |
| Bovine viral diarrhea virus 1 strain ZM-95 | NC_001461 | vertebrates | 1 | Flaviviridae,Pestivirus,Bovine viral diarrhea virus 1 | — | AF526381 |
| Bovine viral diarrhea virus 2 | NC_002032 | vertebrates | 8 | Flaviviridae,Pestivirus,Bovine viral diarrhea virus 2 | — | AB567658,AF002227,GQ888686,FJ527854,AY149215,HQ258810,KC963968,AF145967 |
| Bovine viral diarrhea virus 2-New York'93 virus 2 | NC_002032 | vertebrates | 1 | Flaviviridae,Pestivirus,Bovine viral diarrhea virus 2 | — | AF502399 |
| Bovine viral diarrhea virus 3 | NC_012812 | vertebrates | 8 | Flaviviridae,Pestivirus,Bovine viral diarrhea virus 3 | — | JX469119,JX985409,JQ612704,AB871953,KC297709,HQ231763,JQ612705,KC788748 |
| Bovine viral diarrhea virus 3 Th/04 KhonKaen | NC_012812 | vertebrates | 1 | Flaviviridae,Pestivirus,Bovine viral diarrhea virus 3 | — | FJQ40215 |
| Bovine viral diarrhea virus VEDEVAC | NC_001461 | vertebrates | 1 | Flaviviridae,Pestivirus,Bovine viral diarrhea virus 1 | — | AJ585412 |
| Bovine viral diarrhea virus strain Oregon C24V | NC_001461 | vertebrates | 1 | Flaviviridae,Pestivirus,Bovine viral diarrhea virus 1 | — | AF091605 |
| Bovine viral diarrhea virus type 1a | NC_001461 | vertebrates | 3 | Flaviviridae,Pestivirus,Bovine viral diarrhea virus 1 | — | HQ174293,HQ174292,JN380080 |
| Bovine viral diarrhea virus type 1b | NC_001461 | vertebrates | 6 | Flaviviridae,Pestivirus,Bovine viral diarrhea virus 1 | — | HQ174296,JN644055,JN380089,JN380088,JN704144,HQ174294 |
| Breda virus | NC_007447 | vertebrates | 1 | Coronaviridae,Torovirus,Bovine torovirus | — | AY427798 |
| Broome virus | NC_014236 | vertebrates | 1 | Reoviridae,Orthoreovirus,Broome virus | seg. L1 | GQ258977 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Broome virus | NC_014237 | vertebrates | Reoviridae,Orthoreovirus,Broome virus | 1 | seg. L2 | GQ258978 |
| Broome virus | NC_014238 | vertebrates | Reoviridae,Orthoreovirus,Broome virus | 1 | seg. L3 | GQ258979 |
| Broome virus | NC_014239 | vertebrates | Reoviridae,Orthoreovirus,Broome virus | 1 | seg. M1 | GQ258980 |
| Broome virus | NC_014240 | vertebrates | Reoviridae,Orthoreovirus,Broome virus | 1 | seg. M2 | GQ258981 |
| Broome virus | NC_014241 | vertebrates | Reoviridae,Orthoreovirus,Broome virus | 1 | seg. M3 | GQ258982 |
| Broome virus | NC_014242 | vertebrates | Reoviridae,Orthoreovirus,Broome virus | 1 | seg. S1 | GQ258983 |
| Broome virus | NC_014243 | vertebrates | Reoviridae,Orthoreovirus,Broome virus | 1 | seg. S2 | GQ258984 |
| Broome virus | NC_014244 | vertebrates | Reoviridae,Orthoreovirus,Broome virus | 1 | seg. S3 | GQ258985 |
| Broome virus | NC_014245 | vertebrates | Reoviridae,Orthoreovirus,Broome virus | 1 | seg. S4 | GQ258986 |
| Budgerigar fledgling disease polyomavirus | NC_004764 | vertebrates | Polyomaviridae,Polyomavirus,Budgerigar fledgling disease polyomavirus | 14 | — | AB453165,AF118150,AB453166,M20775,AB453162,GU452537,AB477106,AB453160,AB453161,FJ385773,AY672646,AB453159,AB453164,AB453163 |
| Budgerigar fledgling disease virus-1 | NC_004764 | vertebrates | Polyomaviridae,Polyomavirus,Budgerigar fledgling disease polyomavirus | 1 | — | AF241168 |
| Budgerigar fledgling disease virus-4 | NC_004764 | vertebrates | Polyomaviridae,Polyomavirus,Budgerigar fledgling disease polyomavirus | 1 | — | AF241169 |
| Budgerigar fledgling disease virus-5 | NC_004764 | vertebrates | Polyomaviridae,Polyomavirus,Budgerigar fledgling disease polyomavirus | 1 | — | AF241170 |
| Butcherbird polyomavirus | NC_023008 | vertebrates | Polyomaviridae,Polyomavirus,Butcherbird polyomavirus | 1 | — | KF360862 |
| Calf-giraffe coronavirus US/OH3/2006 | NC_010327, NC_007732, NC_005147, NC_003045 | vertebrates | Coronaviridae,Betacoronavirus,Betacoronavirus 1 | 1 | — | EF424624 |
| Calicivirus isolate Allston 2008/US | NC_004542 | vertebrates | Caliciviridae,Canine calicivirus | 1 | — | GQ475302 |
| Calicivirus isolate Allston 2009/US | NC_004542 | vertebrates | Caliciviridae,Canine calicivirus | 1 | — | GQ475301 |
| Calicivirus isolate TCG | NC_006875 | vertebrates | Caliciviridae,Calicivirus isolate TCG | 1 | — | AB117797 |
| Calicivirus pig/AB104/CAN | NC_012699 | vertebrates | Caliciviridae,St-Valerien swine virus | 1 | — | FJ355930 |
| Calicivirus pig/AB90/CAN | NC_012699 | vertebrates | Caliciviridae,St-Valerien swine virus | 1 | — | FJ355928 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Calicivirus pig/F15-10/CAN | NC_012699 | vertebrates | 1 | Caliciviridae,St-Valerien swine virus | — | FJ355929 |
| Calicivirus pig/NC-WGP93C/USA/2009 | NC_012699 | vertebrates | 1 | Caliciviridae,St-Valerien swine virus | — | GU592498 |
| Calicivirus strain NB | NC_004064, NC_007916 | vertebrates | 1 | Caliciviridae,Nebovirus,Newbury-1 virus | — | AY082891 |
| California sea lion polyomavirus 1 | NC_013796 | vertebrates | 1 | Polyomaviridae,Polyomavirus,California sea lion polyomavirus 1 | — | GQ331138 |
| Callitrichine herpesvirus 3 | NC_004367 | vertebrates | 1 | Herpes viridae,Lymphocryptovirus,Callitrichine herpesvirus 3 | — | AF319782 |
| Camelpox virus | NC_003391 | vertebrates | 1 | Poxviridae,Orthopoxvirus,Camelpox virus | — | AF438165 |
| Camelpox virus CMS | NC_003391 | vertebrates | 1 | Poxviridae,Orthopoxvirus,Camelpox virus | — | AY009089 |
| Camelus dromedarius papillomavirus type 1 | NC_015267 | vertebrates | 1 | Papillomaviridae,Deltapapillomavirus,Camelus dromedarius papillomavirus type 1 | — | HQ912790 |
| Camelus dromedarius papillomavirus type 2 | NC_015268 | vertebrates | 1 | Papillomaviridae,Deltapapillomavirus,Camelus dromedarius papillomavirus type 2 | — | HQ912791 |
| Canary circovirus | NC_003410 | vertebrates | 1 | Circoviridae,Circovirus,Canary circovirus | — | AJ301633 |
| Canary polyomavirus | NC_017085 | vertebrates | 1 | Polyomaviridae,Polyomavirus,Canary polyomavirus | — | GU345044 |
| Canarypox virus | NC_005309 | vertebrates | 1 | Poxviridae,Avipoxvirus,Canarypox virus | — | AY318871 |
| Canine adenovirus | NC_001734 | vertebrates | 1 | Adenoviridae,Mast ad enovirus,Canine adenovirus A | — | Y07760 |
| Canine adenovirus 1 | NC_001734 | vertebrates | 1 | Adenoviridae,Mast ad enovirus,Canine adenovirus A | — | U55001 |
| Canine adenovirus 2 | NC_001734 | vertebrates | 1 | Adenoviridae,Mast ad enovirus,Canine adenovirus A | — | U77082 |
| Canine bocavirus | NC_020499 | vertebrates | 5 | Parvoviridae,Bocavirus,Canine bocavirus | — | JQ692588,JN648103, JQ692591,JQ692590, JQ692589 |
| Canine calicivirus | NC_004542 | vertebrates | 1 | Caliciviridae,Canine calicivirus | — | AB070225 |
| Canine circovirus | NC_020904 | vertebrates | 3 | Circoviridae,Circovirus,Canine circovirus | — | KC241982,KC241983, KC241984 |
| Canine coronavirus | NC_002306 | vertebrates | 4 | Coronaviridae,Alphacoronavirus,Alphacoronavirus 1 | — | GQ477367,JQ404409 JQ404410,JN856008 |
| Canine kobuvirus 1 | NC_001918 | vertebrates | 1 | Picornaviridae, Kobuvirus, Aichivirus A | — | KC161964 |
| Canine kobuvirus US- PC0082 | NC_001918 | vertebrates | 1 | Picornaviridae, Kobuvirus, Aichivirus A | — | JN088541 |
| Canine minute virus | NC_004442 | vertebrates | 6 | Parvoviridae,Bocavirus,Canine minute virus | — | FJ214110,AB518884, AF495467,AB518883, FJ899734,AB158475 |
| Canine oral papillomavirus | NC_001619 | vertebrates | 2 | Papillomaviridae,Lambdapapillomavirus, Lamb dapapillomavirus 2 | — | D55633,L22695 |
| Canine papillomavirus 10 | NC_016075 | vertebrates | 1 | Papillomaviridae,Canine papillomavirus 10 | — | JF800657 |
| Canine papillomavirus 11 | NC_008297 | vertebrates | 1 | Papillomaviridae,Chipapillomavirus,Chipapillomavirus 1 | — | JF800658 |
| Canine papillomavirus 12 | NC_016074 | vertebrates | 1 | Papillomaviridae Canine papillomavirus 9 | — | JQ754321 |
| Canine papillomavirus 14 | NC_019852 | vertebrates | 1 | Papillomaviridae Canine papillomavirus 14 | — | JQ701802 |
| Canine papillomavirus 2 | NC_006564 | vertebrates | 1 | Papillomaviridae,Taupapillomavirus,Taupapillomavirus 1 | — | AY722648 |
| Canine papillomavirus 3 | NC_008297 | vertebrates | 1 | Papillomaviridae,Chipapillomavirus,Chipapillomavirus 1 | — | DQ295066 |

TABLE 10-continued

| Taxonomy | Rep.Acc.ID | Host | ViroCap-1.0 Taxonomy | | Seg. Count | GN.Acc.IDs |
|---|---|---|---|---|---|---|
| | | | # GN's | Lineage | | |
| Canine papillomavirus 4 | NC_010226 | vertebrates | 1 | Papillomaviridae,Chipapillomavirus,Chipapillomavirus 2 | — | EF584537 |
| Canine papillomavirus 5 | NC_008297 | vertebrates | 1 | Papillomaviridae,Chipapillomavirus,Chipapillomavirus 1 | — | FJ492743 |
| Canine papillomavirus 7 | NC_006564 | vertebrates | 1 | Papillomaviridae,Taupapillomavirus,Taupapillomavirus 1 | — | FJ492742 |
| Canine papillomavirus 8 | NC_016014 | vertebrates | 1 | Papillomaviridae,Canine papillomavirus 8 | — | HQ262536 |
| Canine papillomavirus 9 | NC_016074 | vertebrates | 1 | Papillomaviridae,Canine papillomavirus 9 | — | JF800656 |
| Canine parvovirus | NC_001539 | vertebrates | 4 | Parvoviridae,Parvovirus,Feline panleukopenia virus | — | EU310373,M19296,JN033694,D26079 |
| Canine parvovirus 2b | NC_001539 | vertebrates | 1 | Parvoviridae,Parvovirus,Feline panleukopenia virus | — | JQ268284 |
| Canine picodicistrovirus | NC_021178 | vertebrates | 3 | Picornaviridae,Dicipivirus,Cadicivirus A | — | JN819202,JN819203,JN819204 |
| Canine picornavirus | NC_016964 | vertebrates | 1 | Canine picornavirus | — | JN831356 |
| Capra hircus papillomavirus type 1 | NC_008032 | vertebrates | 1 | Papillomaviridae,Phipapillomavirus,Phipapillomavirus 1 | — | DQ091200 |
| Capreolus capreolus papillomavirus 1 | NC_011051 | vertebrates | 1 | Papillomaviridae,Deltapapillomavirus,Deltapapillomavirus 5 | — | EF680235 |
| Caprine arthritis encephalitis virus | NC_001463 | vertebrates | 6 | Retroviridae,Lentivirus,Caprine arthritis encephalitis virus | — | GQ381130,JF502416,M33677,AF322109,GU120138,AY900630 |
| Caprine arthritis encephalitis virus 0v496 | NC_001463 | vertebrates | 1 | Retroviridae,Lentivirus,Caprine arthritis encephalitis virus | — | FJ195346 |
| Caprine arthritis encephalitis virus Roccaverano | NC_001463 | vertebrates | 1 | Retroviridae,Lentivirus,Caprine arthritis encephalitis virus | — | EU293537 |
| Caprine kobuvirus | NC_023422 | vertebrates | 1 | Picornaviridae,Kobuvirus,Caprine kobuvirus | — | KF793927 |
| Cardioderma polyomavirus | NC_020067 | vertebrates | 1 | Polyomaviridae,Polyomavirus,Cardioderma polyomavirus | — | JX520659 |
| Cardiovirus BR/118/2006 | NC_009448,NC_001366,NC_010810 | vertebrates | 1 | Picornaviridae,Cardiovirus,Theilovirus | — | EU681177 |
| Cardiovirus D/VI2223/2004 | NC_009448,NC_001366,NC_010810 | vertebrates | 1 | Picornaviridae,Cardiovirus,Theilovirus | — | EU681179 |
| Cardiovirus D/VI2229/2004 | NC_009448,NC_001366,NC_010810 | vertebrates | 1 | Picornaviridae,Cardiovirus,Theilovirus | — | EU681176 |
| Cardiovirus D/VI2273/2004 | NC_009448,NC_001366,NC_010810 | vertebrates | 1 | Picornaviridae,Cardiovirus,Theilovirus | — | EU681178 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Caretta caretta papillomavirus 1 | NC_011530 | vertebrates | 1 | Papillomaviridae,Dyozetapapillomavirus,Dyozetapapillomavirus 1 | — | EU493092 |
| Carp picornavirus 1 | NC_023162 | vertebrates | 1 | Carp picornavirus 1 | — | KF306267 |
| Cas-Br-E murine leukemia virus | NC_001702,NC_001819,NC_001362,NC_001501 | vertebrates | 1 | Retroviridae,Gammaretrovirus,Murine leukemia virus | — | X57540 |
| Castor canadensis papillomavirus type 1 | NC_023178 | vertebrates | 1 | Papillomaviridae,Castor canadensis papillomavirus type 1 | — | KCO20689 |
| Caviid herpesvirus 2 | NC_020231 | vertebrates | 2 | Herpesviridae,Caviid herpesvirus 2 | — | AB592928,KC503762 |
| Caviid herpesvirus 2 str, CIDMTR | NC_020231 | vertebrates | 1 | Herpesviridae,Caviid herpesvirus 2 | — | HG531783 |
| Cebus albifrons polyomavirus 1 | NC_019854 | vertebrates | 1 | Polyomaviridae,Polyomavirus,Cebus albifrons polyomavirus 1 | — | JX159988 |
| Cercopithecine herpesvirus 2 | NC_006560 | vertebrates | 1 | Herpesviridae,Simplexvirus,Cercopithecine herpesvirus 2 | — | AY714813 |
| Cercopithecine herpesvirus 5 | NC_012783 | vertebrates | 2 | Herpesviridae,Cytomegalovirus,Cercopithecine herpesvirus 5 | — | FJ483968,FJ483969 |
| Cercopithecine herpesvirus 9 | NC_002686 | vertebrates | 1 | Herpesviridae,Varicellovirus,Cercopithecine herpesvirus 9 | — | AF275348 |
| Chaerephon polyomavirus 1 | NC_020065 | vertebrates | 1 | Polyomaviridae,Polyomavirus,Chaerephon polyomavirus 1 | — | JX520657 |
| Chelonia mydas papillomavirus 1 | NC_011530 | vertebrates | 1 | Papillomaviridae,Dyozetapapillomavirus,Dyozetapapillomavirus 1 | — | EU493091 |
| Chicken anemia virus | NC_001427 | vertebrates | 52 | Circoviridae,Gyrovirus,Chicken anemia virus | — | KF224936,DQ217400,KF224938,DQ124936,KF224935,AF311900,JX964755,DQ141673,KC41406,KF224929,AY999018,AY839944,KF224934,DQ217401,AJ297685,AB027470,KF224937,DQ141670,DQ141672,KF224926,AF311892,D0141671,AF390102,EF176599,KF224931,U66304,AF390038,AY040632,JF507715,D0124935,FJ172347,D0991394,M55918,D10068,KF224933,DQ124934,A48606,AF285882,AB119448,L14767,KF224932,KF224928,JQ690762,AF395114,JX26042,U65414, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Chicken astrovirus | NC_003790 | vertebrates | 1 | Astroviridae,Avastrovirus,Chicken astrovirus | — | AY843527,AJ297684, AY846844,AF475908, KF224930,KF224927 |
| Chimpanzee polyomavirus | NC_014743 | vertebrates | 3 | Polyomaviridae,Polyomavirus,Chimpanzee polyomavirus | — | AB033998 FR692336,FR692334 ,FR692335 |
| Cimodo virus | NC_023420 | vertebrates | 1 | Reoviridae, Cimodo virus | seg. 1 | KF880772 |
| Circovirus NGchicken38/NGA/2009 | NC_002361 | vertebrates | 1 | Circoviridae,Circovirus,Columbid circovirus | | HQ738642 |
| Citrus endogenous pararetrovirus | NC_023153 | vertebrates | 3 | Retroviridae,Citrus endogenous pararetrovirus | | KF800045,KF800044, KF800043 |
| Classical swine fever virus | NC_002657 | vertebrates | 59 | Flaviviridae,Pestivirus,Classical swine fever virus | — | U45477,HQ148063,A 47690,JQ268754,EU 915211,GQ902941,K C851953,D49532,JX2 62391,AY775178,AY 578687,AF099102,E U857642,AF333000, GU324242,L49347,A Y259122,AF352565, GU233731,FJ529205, A16790,AF091507,G 0923951,AY646427, HQ380231,AX191158 ,EU789580,AF09244 8,D49533,AY382481, GU233733,EU497410 ,U45478,A77196,AY5 78688,X96550,AY568 569,AY663656,AY36 7767,GU233732,GQ1 22383,HM237795,AF 091661,AY805221,U9 0951,GU592790,JX2 18094,HQ148062,FJ2 65020,DQ127910,CQ 867021,GU233734,A F326963,AF531433,H 0148061,JQ595295, AY072924,HM175885 ,EU490425 |
| Classical swine fever virus - Alf ort/187 | NC_002657 | vertebrates | 1 | Flaviviridae,Pestivirus,Classical swine fever virus | — | X87939 |
| Classical swine fever virus - Alfort/Tuebingen | NC_002657 | vertebrates | 1 | Flaviviridae,Pestivirus,Classical swine fever virus | — | JQ4358 |
| Classical swine fever virus - Brescia | NC_002657 | vertebrates | 1 | Flaviviridae,Pestivirus,Classical swine fever virus | — | M31768 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Classical swine fever virus - C | NC_002657 | vertebrates | 1 | Flaviviridae,Pestivirus,Classical swine fever virus | — | Z46258 |
| Classical swine fever virus 39 | NC_002657 | vertebrates | 1 | Flaviviridae,Pestivirus,Classical swine fever virus | — | AF407339 |
| Classical swine fever virus 96TD | NC_002657 | vertebrates | 1 | Flaviviridae,Pestivirus,Classical swine fever virus | — | AY554397 |
| Colobus guereza papillomavirus 1 | NC_004104 | vertebrates | 1 | Papillomaviridae,Alphapapillomavirus,Alphapa pillomavirus 14 | — | GU014532 |
| Columbid circovirus | NC_002361 | vertebrates | 16 | Circoviridae,Circovirus,Columbid circovirus | — | DQ915950,DQ915959,EU840176,DQ915957,DQ090944,DQ090945,AF252610,DQ915958,AJ298230,JX901125,AJ298229,JN183455,DQ915961,DQ915962,DQ915956,DQ915960 |
| Common chimpanzee papillomavirus 1 | NC_001355 | vertebrates | 1 | Papillomaviridae,Alphapapillomavirus,Alphapa pillomavirus 10 | — | AF020905 |
| Common marmoset foamy virus | NC_001364 | vertebrates | 1 | Retroviridae,Spumavirus,Simian foamy virus | — | GU356395 |
| Common midwife toad ranavirus | NC_005946 | vertebrates | 1 | Iridoviridae,Ranavirus,Frog virus 3 | — | JQ231222 |
| Common-moorhen coronavirus HKU21 | NC_016996 | vertebrates | 1 | Coronaviridae,Deltacoronavirus,Common-moorhen coronavirus H KU21 | — | JQ065049 |
| Cosavirus A | NC_012800 | vertebrates | 2 | Picornaviridae,Cosavirus,Cosavirus A | — | FJ438902,GU968209 |
| Cotia virus SPAn232 | NC_016924 | vertebrates | 1 | Poxviridae,Cotia virus | — | HQ647181 |
| Cottontail rabbit papillomavirus | NC_001541 | vertebrates | 4 | Papillomaviridae,Kappapapillomavirus,Kappap apillomavirus 2 | — | AJ404003,JF303889,AJ243287,K02708 |
| Cowpox virus | NC_003663 | vertebrates | 34 | Poxviridae,Orthopoxvirus,Cowpox virus | — | KC813499,HQ420896,KC813496,KC813500,KC813492,DQ437593,HQ420895,HQ420897,KC813505,X94355,HQ407377,KC813512,KC813501,KC813493,KC813494,HQ420894,HQ420899,HQ420900,KC813510,KC813491,KC813502,KC813495,KC813509,KC813511,AF482758,KC813503,HQ420893,KC813507,HQ420898,KC813506,KC813508,KC813504,KC813498,KC813497 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Crocuta crocuta papillomavirus 1 | NC_018575 | vertebrates | Papillomaviridae,Lambdapapillomavirus,Crocuta crocuta papillomavirus 1 | 1 | — | HQ585856 |
| Crow polyomavirus | NC_007922 | vertebrates | Polyomaviridae,Polyomavirus,Crow polyomavirus | 1 | — | DQ192570 |
| Cyclovirus NGchicken15/NGA/2009 | NC_014930 | vertebrates | Circoviridae,Cyclovirus NGchicken15/NGA/2009 | 1 | — | HQ738644 |
| Cyclovirus NGchicken8/NGA/2009 | NC_014930 | vertebrates | Circoviridae,Cyclovirus NGchicken15/NGA/2009 | 1 | — | HQ738643 |
| Cyclovirus PKbeef23/PAK/2009 | NC_014927 | vertebrates | Circoviridae,Cyclovirus PKgoat21/PAK/2009 | 1 | — | HQ738634 |
| Cyclovirus PKgoat11/PAK/2009 | NC_014928 | vertebrates | Circoviridae,Cyclovirus PKgoat11/PAK/2009 | 1 | — | HQ738636 |
| Cyclovirus PKgoat21/PAK/2009 | NC_014927 | vertebrates | Circoviridae,Cyclovirus PKgoat21/PAK/2009 | 1 | — | HQ738635 |
| Cyclovirus VN | NC_021707 | vertebrates | Circoviridae,Cyclovirus VN | 8 | — | KF031491,KF031469, KF031467,KF031471, KF031466,KF031465, KF031468,KF031470 |
| Cyclovirus bat/USA/2009 | NC_014929 | vertebrates | Circoviridae,Cyclovirus bat/USA/2009 | 1 | — | HQ738637 |
| Cynomolgus macaque cytomegalovirus strain Ottawa | NC_016154 | vertebrates | Herpesviridae,Cytomegalovirus,Cynomolgus macaque cytomegalovirus strain Ottawa | 1 | — | JN227533 |
| Cyprinid herpesvirus 1 | NC_019491 | vertebrates | Alloherpesviridae,Cyprinivirus,Cyprinid herpesvirus 1 | 1 | — | JQ815363 |
| Cyprinid herpesvirus 2 | NC_019495 | vertebrates | Alloherpesviridae,Cyprinivirus,Cyprinid herpesvirus 2 | 1 | — | JQ815364 |
| Cyprinid herpesvirus 3 | NC_009127 | vertebrates | Alloherpesviridae,Cyprinivirus,Cyprinid herpesvirus 3 | 3 | — | DQ657948,AP008984 ,DQ177346 |
| DG-75 Murine leukemia virus | NC_001702 ,NC_00181 9,NC_0013 62,NC_001 501 | vertebrates | Retroviridae,Gammaretrovirus,Murine leukemia virus | 1 | — | AF221065 |
| Deer papillomavirus | NC_001523 | vertebrates | Papillomaviridae,Deltapapillomavirus,Deltapap illomavirus 2 | 1 | — | M11910 |
| Deerpox virus W-1170-84 | NC_006967 | vertebrates | Poxviridae,Cervidpoxvirus,Deerpox virus W-1170-84 | 1 | — | AY689437 |
| Deerpox virus W-848-83 | NC_006966 | vertebrates | Poxviridae,Cervidpoxvirus,Deerpox virus W-848-83 | 1 | — | AY689436 |
| Delphinus delphis papillomavirus | NC_011109 | vertebrates | Papillomaviridae,Upsilonpapillomavirus,Upsilon papillomavirus 1 | 1 | — | GU117620 |
| Duck adenovirus 1 | NC_001813 | vertebrates | Adenoviridae,Atadenovirus,Duck adenovirus A | 1 | — | KF286430 |
| Duck adenovirus A | NC_001813 | vertebrates | Adenoviridae,Atadenovirus,Duck adenovirus A | 1 | — | Y09598 |
| Duck astrovirus 1 FJ919227 | NC_012437 | vertebrates | Astroviridae,Avastrovirus,Duck astrovirus GH,A | 5 | — | JX439643,FJ919225, FJ919228,FJ919226, FJ919227 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Duck astrovirus C-NGB | NC_012437 | vertebrates | 1 | Astroviridae,Avastrovirus,Duck astrovirus GII,A | — | FJ434664 |
| Duck circovirus | NC_005053,NC_007220,NC_006561 | vertebrates | 47 | Circoviridae,Circovirus,Duck circovirus | — | KC460533,HG532019,GU131340,EU499309,EU344803,HM162348,EU022375,HM162351,KC460528,JX241046,EU344805,GU131343,JX241045,EU344804,EU499310,JQ740360,KC460530,HM162349,HM162352,KC460527,GU131341,JQ740361,KC460532,KC460526,KC460525,HM162347,KC460524,HM162345,KC460529,KF726087,JQ740362,KC460535,GU131342,EU499311,GQ423740,HM162353,GU014543,GQ423747,HM162350,JQ740363,EU344806,HM162346,KC460534,EU344802,EU022374,KC460531,EU344807 |
| Duck coronavirus | NC_010800,NC_001451 | vertebrates | 1 | Coronaviridae,Gammacoronavirus,Avian coronavirus | — | JF705860 |
| Duck hepatitis A virus | NC_008250 | vertebrates | 13 | Picornaviridae,Avihepatovirus,Duck hepatitis A virus | — | JX235698,JQ301467,GU066820,EU352805,HQ654774,GU066824,GU066825,GU066823,GU944671,GU066822,GU066819,KC893553,GU066821 |
| Duck hepatitis A virus 1 | NC_008250 | vertebrates | 30 | Picornaviridae,Avihepatovirus,Duck hepatitis A virus | — | JF828983,JF828984,DQ249299,JF914945,JQ316452,JF828989,JF828992,JF828996,JF829000,KC904272,JF828985,JF828987,JF828998,JF828994,JF828986,JF828997,JF828991,JF828993,JF828982,JF828999,DQ226541,JQ031262 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Duck hepatitis A virus 3 | NC_008250 | vertebrates | 6 | Picornaviridae,Avihepatovirus,Duck hepatitis A virus | — | JF828990,JQ804521,JF828988,JF828995,JX390984,JQ804522,JX390982,JX390983 |
| Duck hepatitis B virus | NC_001344 | vertebrates | 43 | Hepadnaviridae,Avihepadnavirus,Duck hepatitis B virus | — | DQ256132,KC993890,JQ409566,JF835025,JF914944,JX312194 |
| Duck hepatitis virus 1 | NC_008250 | vertebrates | 44 | Picornaviridae,Avihepatovirus,Duck hepatitis A virus | — | DQ195079,AY494850,AF404406,AF047045,M6O677,EU429326,X60213,JX469898,KO1834,AY433937,X58567,HM043822,AY250904,AY250901,HQ214130,AY494851,X58568,X58569,AF493986,M32990,X74623,AY294028,EU429324,JX469896,AY250902,AY392760,AY294656,H0132730,AJQ06350,M32991,HM590411,D0276978, M21953,AY536371,AF505512,AY521226,AY294029,AY521227,HQ328779,X12798,JX469897,EU429325,AY250903 |
|  |  |  |  |  |  | FJ157172,FJ157179,EU395435,EU888310,JF436047,FJ157173,EU841005,DQ864514,FJ157174,EU371557,JF496339,EU395436,JF496344,DQ249301,EU395439,EF58520,0,EF427899,EF15131,2,EU395438,EU2640,72,FJ496341,EF3827,78,FJ157177,EF1513,13,FJ496340,FJ1571,76,DQ219396,EU877,916,EU395440,GQ13,0377,FJ496343,EF427900,EF093502,DQ886445,FJ15178,FJ496342,EU747874,FJ157175,EU753359,FJ9 |

TABLE 10-continued

VireCap-1.0 Taxonomy

| Taxonomy | Rep.Acc.ID | Host | # GN's | Lineage | Seg. Count | GN.Acc.IDs |
|---|---|---|---|---|---|---|
| Duck hepatitis virus 1 strain 04G | NC_008250 | vertebrates | 1 | Picornaviridae,Orthoreovirus,Duck hepatitis A virus | — | 71623,EU395437,FJ157180,EF417871,DQ249300 |
| Duck hepatitis virus 1 strain 90D | NC_008250 | vertebrates | 1 | Picornaviridae,Avihepatovirus,Duck hepatitis A virus | — | EF067923 |
| Duck hepatitis virus AP-04009 | NC_008250 | vertebrates | 1 | Picornaviridae,Avihepatovirus,Duck hepatitis A virus | — | EF067924 |
| Duck hepatitis virus AP-04203 | NC_008250 | vertebrates | 1 | Picornaviridae,Avihepatovirus,Duck hepatitis A virus | — | DQ256133 |
| Duck hepatitis virus DHV-HS | NC_008250 | vertebrates | 1 | Picornaviridae,Avihepatovirus,Duck hepatitis A virus | — | DQ256134 |
| Duck hepatitis virus DHV-HSS | NC_008250 | vertebrates | 1 | Picornaviridae,Avihepatovirus,Duck hepatitis A virus | — | DQ812094 |
| Duck hepatitis virus FC64/CHN/2009 | NC_008250 | vertebrates | 1 | Picornaviridae,Avihepatovirus,Duck hepatitis A virus | — | DQ812092 |
| Duck hepatitis virus G | NC_008250 | vertebrates | 1 | Picornaviridae,Avihepatovirus,Duck hepatitis A virus | — | HQ232302 |
| Duck hepatitis virus GD | NC_008250 | vertebrates | 1 | Picornaviridae,Avihepatovirus,Duck hepatitis A virus | — | EU755009 |
| Duck hepatitis virus SDQ1 | NC_008250 | vertebrates | 1 | Picornaviridae,Avihepatovirus,Duck hepatitis A virus | — | GQ122332 |
| Duck hepatitis virus SDQ2 | NC_008250 | vertebrates | 1 | Picornaviridae,Avihepatovirus,Duck hepatitis A virus | — | GQ485310 |
| Duck hepatitis virus YYF-2008 | NC_008250 | vertebrates | 1 | Picornaviridae,Avihepatovirus,Duck hepatitis A virus | — | GQ485311 |
| Duck hepatitis virus YYF-2008 | NC_008250 | vertebrates | 1 | Picornaviridae,Avihepatovirus,Duck hepatitis A virus | — | DQ812093 |
| Duck reovirus | NC_015126 | vertebrates | 3 | Reoviridae,Orthoreovirus,Avian orthoreovirus | seg. L1 | KF154110,KC493572,JX478250 |
| Duck reovirus | NC_015127 | vertebrates | 3 | Reoviridae,Orthoreovirus,Avian orthoreovirus | seg. L2 | KF154111,JX478251,KC493573 |
| Duck reovirus | NC_015128 | vertebrates | 3 | Reoviridae,Orthoreovirus,Avian orthoreovirus | seg. L3 | KF154112,KC493574,JX478252 |
| Duck reovirus | NC_015129 | vertebrates | 3 | Reoviridae,Orthoreovirus,Avian orthoreovirus | seg. M1 | KF154113,JX478253,JX440513 |
| Duck reovirus | NC_015130 | vertebrates | 3 | Reoviridae,Orthoreovirus,Avian orthoreovirus | seg. M2 | KF154114,JX478254,JX440514 |
| Duck reovirus | NC_015131 | vertebrates | 3 | Reoviridae,Orthoreovirus,Avian orthoreovirus | seg. M3 | JX478255,JX440512,KF154115 |
| Duck reovirus | NC_015132 | vertebrates | 1 | Reoviridae,Orthoreovirus,Avian orthoreovirus | seg. S1 | KF689545 |
| Duck reovirus | NC_015133 | vertebrates | 8 | Reoviridae,Orthoreovirus,Avian orthoreovirus | seg. S2 | JX852430,KF154117,JX852432,JX852431,JX852434,JQ863359,JX852433,JX478257 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Duck reovirus | NC_015134 | vertebrates | Reoviridae,Orthoreovirus,Avian orthoreovirus | 8 | seg. S3 | KF154118,JX826588, KF163096,KF163098, JX478258,KF163097, KF163099,KF163095 |
| Duck reovirus | NC_015135 | vertebrates | Reoviridae,Orthoreovirus,Avian orthoreovirus | 9 | seg. S4 | JX826589,KF163100, KF163104,KF163102, JX478259,KF154119, KF163103,JQ922269, KF163101 |
| Duck reovirus NP03/CHN/2009 | NC_015126 | vertebrates | Reoviridae,Orthoreovirus,Avian orthoreovirus | 1 | seg. L1 | KC312700 |
| Duck reovirus NP03/CHN/2009 | NC_015127 | vertebrates | Reoviridae,Orthoreovirus,Avian orthoreovirus | 1 | seg. L2 | KC312701 |
| Duck reovirus NP03/CHN/2009 | NC_015128 | vertebrates | Reoviridae,Orthoreovirus,Avian orthoreovirus | 1 | seg. L3 | KC312702 |
| Ectromelia virus | NC_004105 | vertebrates | Poxviridae,Orthopoxvirus,Ectromelia virus | 2 | — | JQ410350,AF012825 |
| Eel picornavirus 1 | NC_022332 | vertebrates | Picornaviridae, Eel picornavirus 1 | 1 | — | KC843627 |
| Eel virus European X rhabdovirus | NC_022581 | vertebrates | Rhabdoviridae,Perhabdovirus,Anguillid rhabdovirus | 1 | — | FN557213 |
| Eidolon helvum parvovirus 1 | NC_016744 | vertebrates | Parvoviridae,Eidolon helvum parvovirus 1 | 1 | — | JQ037753 |
| Eidolon polyomavirus 1 | NC_020068 | vertebrates | Polyomaviridae,Polyomavirus,Eidolon polyomavirus 1 | 1 | — | JX520660 |
| Elephant endotheliotropic herpesvirus 1A | NC_020474 | vertebrates | Herpesviridae,Proboscivirus,Elephantid herpesvirus 1 | 1 | — | KC618527 |
| Elephantid herpesvirus 1 | NC_020474 | vertebrates | Herpesviridae,Proboscivirus,Elephantid herpesvirus 1 | 2 | — | KC462165,KC462164 |
| Encephalomyocarditis virus | NC_001479 | vertebrates | Picornaviridae,Cardiovirus,Encephalomyocard itis virus | 16 | — | M37588,AY296731,K F293299,FJ897755,E U780149,X87335,DQ 288856,M22458,M22 457,EU780148,AF35 6822,X74312,DQ464 062,KF709977,M818 61,DQ464063 |
| Endogenous mouse mammary tumor virus Mtv1 | NC_001503 | vertebrates | Retroviridae,Betaretrovirus,Mouse mammary tumor virus | 1 | — | AF228550 |
| Enterovirus 103 | NC_010415 | vertebrates | Picornaviridae,Enterovirus,Enterovirus J | 1 | — | FJQ07373 |
| Enterovirus 103 | NC_013695 | vertebrates | Picornaviridae,Enterovirus,Enterovirus J | 1 | — | FJQ07373 |
| Enterovirus E | NC_001859 | vertebrates | Picornaviridae,Enterovirus,Enterovirus E | 1 | — | DQ0214 |
| Enterovirus E | NC_021220 | vertebrates | Picornaviridae,Enterovirus,Enterovirus F | 2 | — | DQ09279,DQ09279 4 |
| Enterovirus F | NC_021220 | vertebrates | Picornaviridae,Enterovirus,Enterovirus F | 2 | — | KC748420,DQ092770 |
| Enterovirus J | NC_010415 | vertebrates | Picornaviridae,Enterovirus,Enterovirus J | 1 | — | AF414372 |
| Enterovirus J | NC_013695 | vertebrates | Picornaviridae,Enterovirus,Enterovirus J | 2 | — | AF414372,AF414373 |
| Enzootic nasal tumor virus | NC_007015 | vertebrates | Retroviridae,Betaretrovirus,Ovine enzootic nasal tumor virus | 5 | — | FJ744146,FJ744150, FJ744148,FJ744147, FJ744149 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Enzootic nasal tumour virus of goats | NC_004994 | vertebrates | 2 | Retroviridae,Betaretrovirus,Enzootic nasal tumour virus of goats | — | HM104174,AY197548 |
| Epinephelus tauvina nervous necrosis virus | NC_004136 | vertebrates | 2 | Nodaviridae,Betanodavirus,Epinephelus tauvina nervous necrosis virus | seg. RNA 2 | AF281657,AF318942 |
| Epinephelus tauvina nervous necrosis virus | NC_004137 | vertebrates | 2 | Nodaviridae,Betanodavirus,Epinephelus tauvina nervous necrosis virus | seg. RNA 1 | AF326776,AF319555 |
| Epsilonpapillomavirus 1 | NC_004195 | vertebrates | 1 | Papillomaviridae,Epsilonpapillomavirus,Epsilonpapillomavirus 1 | — | AF457465 |
| Equid herpesvirus 1 | NC_001491 | vertebrates | 3 | Herpesviridae,Varicellovirus,Equid herpesvirus 1 | — | AP012321,AY665713,AY464052 |
| Equid herpesvirus 2 | NC_001650 | vertebrates | 1 | Herpesviridae,Percavirus,Equid herpesvirus 2 | — | U20824 |
| Equid herpesvirus 4 | NC_001844 | vertebrates | 1 | Herpesviridae,Varicellovirus,Equid herpesvirus 4 | — | AF030027 |
| Equid herpesvirus 8 | NC_017826 | vertebrates | 1 | Herpesviridae,Varicellovirus,Equid herpesvirus 8 | — | JQ343919 |
| Equid herpesvirus 9 | NC_011644 | vertebrates | 1 | Herpesviridae,Varicellovirus,Equid herpesvirus 9 | — | AP010838 |
| Equine arteritis virus | NC_002532 | vertebrates | 33 | Arteriviridae,Arterivirus,Equine arteritis virus | — | GQ903801,X53459,AY349168,GQ903807,JN211318,EU586274,EU252114,GQ903806,GQ903800,EU252113,GQ903798,GQ903805,GQ903811,JN211316,GQ903795,GQ903810,EU586275,GQ903804,GQ903809,G0903802,A45589,JN211320,EU586273,AY349167,JN211319,JN211317,GQ903799,DQ846750,GQ903797,GQ903808,GQ903803,GQ903794,GQ903796 |
| Equine coronavirus | NC_010327,NC_007732,NC_005147,NC_003045 | vertebrates | 1 | Coronaviridae,Betacoronavirus,Betacoronavirus 1 | — | EF446615 |
| Equine foamy virus | NC_002201 | vertebrates | 1 | Retroviridae,Spumavirus,Equine foamy virus | — | AF201902 |
| Equine infectious anemia virus | NC_001450 | vertebrates | 26 | Retroviridae,Lentivirus,Equine infectious anemia virus | — | M87581,U01866,HM141912,HM141917,HM141921,AF327877,HM141915,HM141918,HM141913,HM141914,HM141916,HM141919,AF32787,HM141420,JXQ03263,AF016314,JXQ03263,AF0163 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Equine papillomavirus 2 | NC_012123 | vertebrates | 2 | Papillomaviridae,Dyoiotapapillomavirus,Equine papillomavirus 2 | — | 16,HM141909,HM141922,AF028231,HM141920,AF033820,M16575,HM141911,HM141910,AF028232,HM141916,AF247394,HM141923 |
| Equine papillomavirus 3 | NC_017862 | vertebrates | 1 | Papillomaviridae,Equine papillomavirus 3 | — | EU503122,HM461973 |
| Equine papillomavirus type 6 | NC_020500 | vertebrates | 1 | Papillomaviridae,Equine papillomavirus type 6 | — | GU384895 |
| Equine pegivirus 1 | NC_020902 | vertebrates | 1 | Flaviviridae,Pegivirus,Equine pegivirus 1 | — | JQ965698 |
| Equine polyomavirus | NC_017982 | vertebrates | 1 | Polyomaviridae,Polyomavirus,Equine polyomavirus | — | KC410872 |
| Equine rhinitis A virus | NC_003982 | vertebrates | 8 | Picornaviridae,Aphthovirus,Equine rhinitis A virus | — | JQ412134 |
| Equine rhinitis B virus 1 | NC_003983 | vertebrates | 1 | Picornaviridae,Erbovirus,Equine rhinitis B virus | — | DQ268580,DQ272128,DQ272577,X96870,DQ272127,JX294351,DQ272578,L43052 |
| Equine rhinitis B virus 2 | NC_003983 | vertebrates | 1 | Picornaviridae,Erbovirus,Equine rhinitis B virus | — | X96871 |
| Equus caballus papillomavirus 1 | NC_003748 | vertebrates | 1 | Papillomaviridae,Zetapapillomavirus,Zetapapillomavirus 1 | — | AF361253 |
| Equus ferus caballus papillomavirus type 4 | NC_020085 | vertebrates | 1 | Papillomaviridae,Equus ferus caballus papillomavirus type 4 | — | AF498323 |
| Equus ferus caballus papillomavirus type 5 | NC_020084 | vertebrates | 1 | Papillomaviridae,Equus ferus caballus papillomavirus type 5 | — | JQ031032 |
| Equus ferus caballus papillomavirus type 7 | NC_020501 | vertebrates | 1 | Papillomaviridae,Equus ferus caballus papillomavirus type 7 | — | JQ031033 |
| Erethizon dorsatum papillomavirus type 1 | NC_006951 | vertebrates | 1 | Papillomaviridae,Sigmapapillomavirus,Sigmapapillomavirus 1 | — | JXQ35935 |
| Erinaceus europaeus papillomavirus 1 | NC_011765 | vertebrates | 1 | Papillomaviridae,Dyoetapapillomavirus,Dyoetapapillomavirus 1 | — | AY684126 |
| Espirito Santo virus | NC_016517 | vertebrates | 1 | Birnaviridae,Espirito Santo virus | seg. B | FJ379293 |
| Espirito Santo virus | NC_016518 | vertebrates | 1 | Birnaviridae,Espirito Santo virus | seg. A | JN589002 |
| European brown hare syndrome virus | NC_002615 | vertebrates | 3 | Caliciviridae,Lagovirus,European brown hare syndrome virus | — | JN589003 |
| European catfish virus | NC_017940 | vertebrates | 1 | Iridoviridae,Ranavirus,European catfish virus | — | KC832838,KC832839,Z69620 |
| European elk papillomavirus | NC_001524 | vertebrates | 1 | Papillomaviridae,Deltapapillomavirus,Deltapapillomavirus 1 | — | JQ724856 |
| Exogenous mouse mammary tumor virus | NC_001503 | vertebrates | 2 | Retroviridae,Betaretrovirus,Mouse mammary tumor virus | — | M15953 |
| FBR murine osteosarcoma virus | NC_001506 | vertebrates | 1 | Retroviridae,Gammaretrovirus,Murine osteosarcoma virus | — | AF228551,AF228552 |
| Fathead minnow picornavirus | NC_023437 | vertebrates | 1 | Picornaviridae,Fathead minnow picornavirus | — | K02712 |
| | | | | | — | KC465953 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Felid herpesvirus 1 | NC_013590 | vertebrates | 1 | Herpesviridae,Varicellovirus,Felid herpesvirus 1 | — | FJ478159 |
| Feline astrovirus 2 | NC_022249 | vertebrates | 1 | Astroviridae,Mamastrovirus,Feline astrovirus 2 | — | KF499111 |
| Feline astrovirus Viseu | NC_022249 | vertebrates | 1 | Astroviridae,Mamastrovirus,Feline astrovirus 2 | — | KF374704 |
| Feline bocavirus | NC_017823 | vertebrates | 3 | Parvoviridae,Bocavirus,Feline bocavirus | — | JQ692586,JQ692585, JQ692587 |
| Feline bocavirus 2 | NC_022800 | vertebrates | 1 | Parvoviridae,Bocavirus,Feline bocavirus 2 | — | KF792837 |
| Feline calicivirus | NC_001481 | vertebrates | 28 | Caliciviridae,Vesivirus,Feline calicivirus | — | KC835209,AY560117,JX519213,JX519209, JN210884,JN210886, AY560118,M86379,L40021,JX519211,AY560113,JN210890,U13992,GU214989,JN210889,AY560114,JN210888,DQ424892,JX519214,JN210887,AY560116,AF479590,JN210885,JX519212,D31836,JX519210,AY560115,AF109465 |
| Feline coronavirus | NC_002306 | vertebrates | 8 | Coronaviridae,Alphacoronavirus, Alphacoronavirus 1 | — | JQ408980,GQ152141,KF530123,DQ010921,JN634064, DQ286389,DQ848678,EU186072 |
| Feline coronavirus RM | NC_002306 | vertebrates | 1 | Coronaviridae,Alphacoronavirus, Alphacoronavirus 1 | — | FJ938051 |
| Feline coronavirus UU10 | NC_002306 | vertebrates | 1 | Coronaviridae,Alphacoronavirus, Alphacoronavirus 1 | — | FJ938059 |
| Feline coronavirus UU11 | NC_002306 | vertebrates | 1 | Coronaviridae,Alphacoronavirus, Alphacoronavirus 1 | — | FJ938052 |
| Feline coronavirus UU15 | NC_002306 | vertebrates | 1 | Coronaviridae,Alphacoronavirus, Alphacoronavirus 1 | — | FJ938057 |
| Feline coronavirus UU16 | NC_002306 | vertebrates | 1 | Coronaviridae,Alphacoronavirus, Alphacoronavirus 1 | — | FJ938058 |
| Feline coronavirus UU17 | NC_002306 | vertebrates | 1 | Coronaviridae,Alphacoronavirus, Alphacoronavirus 1 | — | HQ012367 |
| Feline coronavirus UU18 | NC_002306 | vertebrates | 1 | Coronaviridae,Alphacoronavirus, Alphacoronavirus 1 | — | HQ012368 |
| Feline coronavirus UU19 | NC_002306 | vertebrates | 1 | Coronaviridae,Alphacoronavirus, Alphacoronavirus 1 | — | HQ392470 |
| Feline coronavirus UU2 | NC_002306 | vertebrates | 1 | Coronaviridae,Alphacoronavirus, Alphacoronavirus 1 | — | FJ938060 |
| Feline coronavirus UU20 | NC_002306 | vertebrates | 1 | Coronaviridae,Alphacoronavirus, Alphacoronavirus 1 | — | HQ392471 |
| Feline coronavirus UU21 | NC_002306 | vertebrates | 1 | Coronaviridae,Alphacoronavirus, Alphacoronavirus 1 | — | HQ012369 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Feline coronavirus UU22 | NC_002306 | vertebrates | 1 | Coronaviridae,Alphacoronavirus, Alphacoronavirus 1 | — | GU553361 |
| Feline coronavirus UU23 | NC_002306 | vertebrates | 1 | Coronaviridae,Alphacoronavirus, Alphacoronavirus 1 | — | GU553362 |
| Feline coronavirus UU24 | NC_002306 | vertebrates | 1 | Coronaviridae,Alphacoronavirus, Alphacoronavirus 1 | — | HQ012370 |
| Feline coronavirus UU3 | NC_002306 | vertebrates | 1 | Coronaviridae,Alphacoronavirus, Alphacoronavirus 1 | — | FJ938061 |
| Feline coronavirus UU30 | NC_002306 | vertebrates | 1 | Coronaviridae,Alphacoronavirus, Alphacoronavirus 1 | — | HQ392472 |
| Feline coronavirus UU31 | NC_002306 | vertebrates | 1 | Coronaviridae,Alphacoronavirus, Alphacoronavirus 1 | — | HQ012371 |
| Feline coronavirus UU34 | NC_002306 | vertebrates | 1 | Coronaviridae,Alphacoronavirus, Alphacoronavirus 1 | — | HQ012372 |
| Feline coronavirus UU4 | NC_002306 | vertebrates | 1 | Coronaviridae,Alphacoronavirus, Alphacoronavirus 1 | — | FJ938054 |
| Feline coronavirus UU40 | NC_002306 | vertebrates | 1 | Coronaviridae,Alphacoronavirus, Alphacoronavirus 1 | — | HQ392469 |
| Feline coronavirus UU47 | NC_002306 | vertebrates | 1 | Coronaviridae,Alphacoronavirus, Alphacoronavirus 1 | — | JN183882 |
| Feline coronavirus UU5 | NC_002306 | vertebrates | 1 | Coronaviridae,Alphacoronavirus, Alphacoronavirus 1 | — | FJ938056 |
| Feline coronavirus UU54 | NC_002306 | vertebrates | 1 | Coronaviridae,Alphacoronavirus, Alphacoronavirus 1 | — | JN183883 |
| Feline coronavirus UU7 | NC_002306 | vertebrates | 1 | Coronaviridae,Alphacoronavirus, Alphacoronavirus 1 | — | FJ938053 |
| Feline coronavirus UU8 | NC_002306 | vertebrates | 1 | Coronaviridae,Alphacoronavirus, Alphacoronavirus 1 | — | FJ938055 |
| Feline coronavirus UU9 | NC_002306 | vertebrates | 1 | Coronaviridae,Alphacoronavirus, Alphacoronavirus 1 | — | FJ938062 |
| Feline foamy virus | NC_001871 | vertebrates | 8 | Retroviridae,Spumavirus,Feline foamy virus | — | AJ564746,KC292055, U85043,AJ223851,K C292054,AB052797, Y08851,AJ564745 |
| Feline immunodeficiency virus | NC_001482 | vertebrates | 27 | Retroviridae,Lentivirus,Feline immunodeficiency virus | — | EF455611,EF455612, EF455609,EU117991 ,EF455608,EF455603 ,M36968,AY713445,E U117992,M25381,AY 600517,X57002,U569 28,AF474246,DQ192 583,EF455607,DDQ2 9017,EF455606,EF45 5614, E43300,EF4556 13,EF455615,EF4556 10,EF455605, M5941 8,U11820,EF455604 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Feline infectious peritonitis virus | NC_002306 | vertebrates | 5 | Coronaviridae,Alphacoronavirus,Alphacoronavirus 1 | — | JQ408981,KC461236,KC461237,KC461235,AY994055 |
| Feline leukemia virus | NC_001940 | vertebrates | 3 | Retroviridae,Gammaretrovirus,Feline leukemia virus | — | AB060732,M18247,AF052723 |
| Feline papillomavirus dapapillomavirus 1 | NC_004765 | vertebrates | 1 | Papillomaviridae,Lambdapapillomavirus,Lambdapapillomavirus 1 | — | AF377865 |
| Feline picornavirus | NC_016156 | vertebrates | 5 | Picornaviridae,Feline picornavirus | — | JN572118,JN572117,JN572116,JN572115,JN572119 |
| Feline sakobuvirus A | NC_022802 | vertebrates | 1 | Picornaviridae,Feline sakobuvirus A | — | KF387721 |
| Felis catus papillomavirus 4 | NC_022373 | vertebrates | 1 | Papillomaviridae,Taupapillomavirus,Felis catus papillomavirus 4 | — | KF147892 |
| Felis catus papillomavirus-3 | NC_021472 | vertebrates | 1 | Papillomaviridae,Taupapillomavirus,Felis catus papillomavirus 3 | — | JX972168 |
| Felis domesticus papillomavirus type 1 | NC_004765 | vertebrates | 1 | Papillomaviridae,Lambdapapillomavirus,Lambdapapillomavirus 1 | — | AF480454 |
| Ferret papillomavirus | NC_022253 | vertebrates | 1 | Papillomaviridae,Ferret papillomavirus | — | KF006988 |
| Finch circovirus | NC_008522 | vertebrates | 1 | Circoviridae,Circovirus,Finch circovirus | — | DQ845075 |
| Finch polyomavirus | NC_007923 | vertebrates | 1 | Polyom aviridae, Polyomavirus,Finch polyomavirus | — | DQ192571 |
| Florida woods cockroach-associated cyclovirus | NC_020206 | vertebrates | 1 | Circoviridae,Florida woods cockroach-associated cyclovirus | — | JX569794 |
| Foot-and-mouth disease virus | NC_004004 | vertebrates | 8 | Picornaviridae,Aphthovirus,Foot-and-mouth disease virus | — | AM503966,XQ0871,AM409190,AM503965,M10975,AJQ07572,AJ007347,AF154271 |
| Foot-and-mouth disease virus-type A | NC_004004 | vertebrates | 86 | Picornaviridae,Aphthovirus,Foot-and-mouth disease virus | — | KC440881,HQ832576,AY593784,AY593802,HQ832585,HQ832579,HQ832582,JF749843,AY593770,AY593765,HQ832581,KC588943,AY593753,AY593788,AY593793,AY593803,HQ632773,AY593760,AY593774,AY593769,HQ832587,AY593776,AY593757,AY593751,AY593754,HQ832588,HQ832592,AY593780,AY593758,KC440882,X748312,JF749841,HQ832591,AY593779,JN006722,HQ832586,AY593783,AY593771,AY593759,AY593762,AY5 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 93772,HM854025,HM854023,HQ832583,H0832589,GQ406250, AY593789,HQ832584,HM854024,AY593791,AY593756,GQ406252,AY593764,HQ832580,GQ406249,AY593790,HQ832578,AY593773,AY593794,AY593786,AY593778,AY593767,AY593792,HQ268509,AY593785,HQ832577,AY593775,AY593761,AY593782,AY593763,GQ406251,JF749848,AY593768,GQ406248,AY593801,AY593777,HM854022,HQ832590,AY593755,AY593766,AY593781,GQ406247,EF117837,AY593752,HM854021,AY593787 |
| Foot-and-mouth disease virus-type Asia 1 | NC_004004 | vertebrates | 46 | Picornaviridae,Aphthovirus,Foot-and-mouth disease virus | — | GU125646,AY593798,DQ989320,DQ989314,EF149009,DQ5334283,DQ989312,DQ989308,DQ989319,DQ989311,DQ989309,KC462884,DQ989322,AY593796,DQ989307,D0989310,EF149010, AY593799,HQ632774,GU125645,AY304994,DQ989317,DQ989303,JN006719,DQ989305,DQ989313,DQ989323,AY390432,DQ989316,AY593800,JF739177,DQ989315,JN006720,AY687333,D0989306,HQ631363,DQ989318,GU93168 2,AY593795,FJ906802,DQ989321,AY687321 |

TABLE 10-continued

| Taxonomy | Rep.Acc.ID | Host | ViroCap-1.0 Taxonomy | | Seg. Count | GN.Acc.IDs |
|---|---|---|---|---|---|---|
| | | | # GN's | Lineage | | |
| Foot-and-mouth disease virus-type C | NC_004004 | vertebrates | 16 | Picorn TABLE 10-continued ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 112879,FJ175661,JX570642,DQ404176,DQ404179,JXQ40501,AJ539140,KF112886,AY598317,KF694733,JXQ40492,JXQ40494,EU448371,AY593832,JX869187,KF501487,AY593824,GU125647,DQ404161,JXQ40497,AY593819,JXQ40488,JX869177,DQ40416 8,JX869180,DQ40417 1,AY593822,JX570645,GU125650,DQ40404 5,HQ412603,AF026168,AJ539139,GU125649,FJ175664,AY593823,JX869188,AY333431,JX570651,AY593825,JX570648,KF694736,AY593811,JX869186,EU448375,AF511039,DQ404162,JN998086,AF308157,EF614457,JXQ40499,HQ632769,JX570638,KF985189,FJ542371,AJ539138,EU448378,DQ404175,EU448374,AY593829,DQ404178,DQ478937,AY593827,JQ900581,AY593834,KF112881,JX570655,JX570643,JX869185,AB079061,AY593813,HQ632771,DQ404180,DQ404163,KF501488,JX570639,FJ542365,JF749851,JX869182,JXQ40495,EU448370,JXQ40493,DQ404177,JQ973889,JXQ40496,AY593828,AY593836,AY593820,KF112882,EU448368,FJ542372,KF112885,KF694744,GU384 6 |

TABLE 10-continued

| Taxonomy | Rep.Acc.ID | Host | ViroCap-1.0 Taxonomy | | Seg. Count | GN.Acc.IDs |
|---|---|---|---|---|---|---|
| | | | # GN's | Lineage | | |
| | | | | | | 82,JX570650,KF1128 84,EU448369,DQ248 888,JXQ40489,AY593 831,DQ404166,DQ11 9643,EF175732,JX57 0653,AY593837,FJ17 5663,KC503937,JXQ6 6665,JX869184,DQ4 04172,JX869179,KF6 94745,AY593826,KF6 94741,EU448379,HM 008917,KF112880,JX 040498,FJ542367,AY 593814,KF694740,JX 570652,FJ175665,AY 593818,FJ542368,DQ 478936,HQ632768,K F694735,KC440883,J XQ40500 |
| Foot-and-mouth disease virus-type SAT 1 | NC_004004 | vertebrates | 10 | Picorn TABLE 10-continued ViroCap-1.0 Taxonomy

| Taxonomy | Rep.Acc.ID | Host | # GN's | Lineage | Seg. Count | GN.Acc.IDs |
|---|---|---|---|---|---|---|
| Foot-and-mouth disease virus 0/UKG/3952/2001 | NC_004004 | vertebrates | 1 | Picornaviridae,Aphthovirus,Foot-and-mouth disease virus | — | EF552688 |
| Foot-and-mouth disease virus 0/UKG/4014/2001 | NC_004004 | vertebrates | 1 | Picornaviridae,Aphthovirus,Foot-and-mouth disease virus | — | EF552693 |
| Foot-and-mouth disease virus 0/UKG/4141/2001 | NC_004004 | vertebrates | 1 | Picornaviridae,Aphthovirus,Foot-and-mouth disease virus | — | EF552689 |
| Foot-and-mouth disease virus 0/UKG/4998/2001 | NC_004004 | vertebrates | 1 | Picornaviridae,Aphthovirus,Foot-and-mouth disease virus | — | EF552694 |
| Foot-and-mouth disease virus 0/UKG/5470/2001 | NC_004004 | vertebrates | 1 | Picornaviridae,Aphthovirus,Foot-and-mouth disease virus | — | EF552696 |
| Foot-and-mouth disease virus 0/UKG/5681/2001 | NC_004004 | vertebrates | 1 | Picornaviridae,Aphthovirus,Foot-and-mouth disease virus | — | EF552697 |
| Foot-and-mouth disease virus 0/UKG/7039/2001 | NC_004004 | vertebrates | 1 | Picornaviridae,Aphthovirus,Foot-and-mouth disease virus | — | EF552690 |
| Foot-and-mouth disease virus 0/UKG/7299/2001 | NC_004004 | vertebrates | 1 | Picornaviridae,Aphthovirus,Foot-and-mouth disease virus | — | EF552692 |
| Foot-and-mouth disease virus 0/UKG/9161/2001 | NC_004004 | vertebrates | 1 | Picornaviridae,Aphthovirus,Foot-and-mouth disease virus | — | EF552691 |
| Foot-and-mouth disease virus 0/UKG/9443/2001 | NC_004004 | vertebrates | 1 | Picornaviridae,Aphthovirus,Foot-and-mouth disease virus | — | EF552695 |
| Fowl adenovirus B | NC_021221 | vertebrates | 1 | Adenoviridae,Aviadenovirus,Fowl adenovirus B | — | KC493646 |
| Fowl adenovirus A | NC_001720 | vertebrates | 1 | Adenoviridae,Aviadenovirus,Fowl adenovirus A | — | U46933 |
| Fowl adenovirus C | NC_015323 | vertebrates | 2 | Adenoviridae,Aviadenovirus,Fowl adenovirus C | — | HE608152,GU188428 |
| Fowl adenovirus D | NC_000899 | vertebrates | 1 | Adenoviridae,Aviadenovirus,Fowl adenovirus D | — | AF083975 |
| Fowl adenovirus E | NC_014969 | vertebrates | 1 | Adenoviridae,Aviadenovirus,Fowl adenovirus E | — | GU734104 |
| Fowlpox virus | NC_002188 | vertebrates | 1 | Poxviridae,Avipoxvirus,Fowlpox virus | — | AF198100 |
| Fowlpox virus (isolate HP-438[Munich]) | NC_002188 | vertebrates | 1 | Poxviridae,Avipoxvirus,Fowlpox virus | — | AJ581527 |
| Francolinus leucoscepus papillomavirus 1 | NC_013117 | vertebrates | 1 | Papillomaviridae,Dyoepsilonpapillomavirus,Dyoepsilonpapillomavirus 1 | — | EU188799 |
| Friend murine leukemia virus | NC_001702,NC_00181 9,NC_0013 62,NC_001 501 | vertebrates | 4 | Retroviridae,Gammaretrovirus,Murine leukemia virus | — | D88386,XQ2794,A420 90,M93134 |
| Fringilla coelebs papillomavirus | NC_004068 | vertebrates | 1 | Papillomaviridae,Etapapillomavirus,Etapapillomavirus 1 | — | AY057109 |
| Frog adenovirus 1 | NC_002501 | vertebrates | 1 | Adenoviridae,Siadenovirus,Frog adenovirus A | — | AF224336 |
| Frog virus 3 | NC_005946 | vertebrates | 1 | Incloviridae,Ranavirus,Frog virus 3 | — | AY548484 |
| Fujinami sarcoma virus | NC_001403 | vertebrates | 2 | Retroviridae,Alpharetrovirus,Fujinami sarcoma virus | — | AF033810,JQ2194 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| GB virus A F023424 | NC_001837 | vertebrates | 3 | Flaviviridae,Pegivirus,Pegivirus A | — | U22303,AF023425,A |
| Gallid herpesvirus 1 | NC_006623 | vertebrates | 21 | Herpesviridae,Iltovirus,Gallid herpesvirus 1 | — | JX458822,JN596962,JN580317,JN542533,JX646898,JN804826,JN580312,U80762,H0630064,JN804827,JN580313,JX646899,JN580315,JN580314,JN542535,JQ083494,JN542534,JN596963,JQ083493,JN542536,JN580316 |
| Gallid herpesvirus 2 | NC_002229 | vertebrates | 14 | Herpesviridae,Mardivirus,Gallid herpesvirus 2 | — | AF147806,AF243438,JQ806362,JQ809692,AY510475,JQ836662,JQ820250,EU499381,JX844666,DQ53034 8,JQ809691,EF52339 0,JQ314003,JQ80636 1 |
| Gallid herpesvirus 2 strain 814 | NC_002229 | vertebrates | 1 | Herpesviridae,Mardivirus,Gallid herpesvirus 2 | — | JF742597 |
| Gallid herpesvirus 3 | NC_002577 | vertebrates | 2 | Herpesviridae,Mardivirus,Gallid herpesvirus 3 | — | AB049735,HQ840738 |
| Gammapapillomavirus HPV127 | NC_014469 | vertebrates | 1 | Papillomaviridae,Gammapapillomavirus,Gammapapillomavirus HPV127 | — | HM011570 |
| Gibbon ape leukemia virus | NC_001885 | vertebrates | 2 | Retroviridae,Gammaretrovirus,Gibbon ape leukemia virus | — | U60065,M26927 |
| Giraffe coronavirus US/0H3-TC/2006 | NC_010327,NC_007732,NC_005147,NC_003045 | vertebrates | 1 | Coronaviridae,Betacoronavirus,Betacoronavirus 1 | — | EF424622 |
| Giraffe coronavirus US/0H3/2003 | NC_010327,NC_007732,NC_005147,NC_003045 | vertebrates | 1 | Coronaviridae,Betacoronavirus,Betacoronavirus 1 | — | EF424623 |
| Goatpox virus G20-LKV | NC_004003 | vertebrates | 1 | Poxviridae,Capripoxvirus,Goatpox virus | — | AY077836 |
| Goatpox virus Pellor | NC_004003 | vertebrates | 1 | Poxviridae,Capripoxvirus,Goatpox virus | — | AY077835 |
| Golden ide reovirus | NC_010588 | vertebrates | 1 | Reoviridae,Aquareovirus,Aquareovirus G | seg. 5 | AF450324 |
| Goose adenovirus 4 | NC_017979 | vertebrates | 1 | Adenoviridae,Aviadenovirus,Goose adenovirus A | — | JF510462 |
| Goose circovirus | NC_003054 | vertebrates | 24 | Circoviridae,Circovirus,Goose circovirus | — | DQ192283,DQ192279,AY633653,DQ192282,AF536933,GU320569,DQ192285,AF536934,AF536932,AF53 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Goose hemorrhagic polyomavirus | NC_004800 | vertebrates | 6 | Polyomaviridae,Polyomavirus,Goose hemorrhagic polyomavirus | — | 6939,AF536941,AF536940,AF536936,DQ192287,DQ192280,AJ304456,AF536935,AF536931,AF536938,AF536937,AF418552,DQ192281,DQ192286,DQ192284 |
| Goose orthoreovirus | NC_015126 | vertebrates | 1 | Reoviridae,Orthoreovirus,Avian orthoreovirus | seg. L1 | HQ681904,HQ681903,AY140894,HQ681905,JF304775,HQ681902 |
| Goose orthoreovirus | NC_015127 | vertebrates | 1 | Reoviridae,Orthoreovirus,Avian orthoreovirus | seg. L2 | JX145328 |
| Goose orthoreovirus | NC_015128 | vertebrates | 1 | Reoviridae,Orthoreovirus,Avian orthoreovirus | seg. L3 | JX145329 |
| Goose orthoreovirus | NC_015129 | vertebrates | 1 | Reoviridae,Orthoreovirus,Avian orthoreovirus | seg. M1 | JX145330 |
| Goose orthoreovirus | NC_015130 | vertebrates | 1 | Reoviridae,Orthoreovirus,Avian orthoreovirus | seg. M2 | JX145331 |
| Goose orthoreovirus | NC_015131 | vertebrates | 1 | Reoviridae,Orthoreovirus,Avian orthoreovirus | seg. M3 | JX145332 |
| Goose orthoreovirus | NC_015132 | vertebrates | 1 | Reoviridae,Orthoreovirus,Avian orthoreovirus | seg. S1 | JX145333 |
| Goose orthoreovirus | NC_015133 | vertebrates | 1 | Reoviridae,Orthoreovirus,Avian orthoreovirus | seg. S2 | JX145334 |
| Goose orthoreovirus | NC_015134 | vertebrates | 1 | Reoviridae,Orthoreovirus,Avian orthoreovirus | seg. S3 | JX145335 |
| Goose orthoreovirus | NC_015135 | vertebrates | 1 | Reoviridae,Orthoreovirus,Avian orthoreovirus | seg. S4 | JX145336 |
| Goose parvovirus | NC_001701 | vertebrates | 12 | Parvoviridae,Dependovirus,Goose parvovirus | — | JX145337 |
| | | | | | | EU583390,KC178571,EU583389,JF333590,KC184133,KC996730,U25749,EU583391,EU583392,KC996729,HQ891825,KC478066 |
| Grass carp hemorrhagic virus | NC_005167 | vertebrates | 1 | Reoviridae,Aquareovirus,Aquareovirus C | seg. 2 | AF284502 |
| Grass carp hemorrhagic virus | NC_005168 | vertebrates | 1 | Reoviridae,Aquareovirus,Aquareovirus C | seg. 3 | AF284503 |
| Grass carp hemorrhagic virus | NC_005170 | vertebrates | 1 | Reoviridae,Aquareovirus,Aquareovirus C | seg. 5 | AF251262 |
| Grass carp hemorrhagic virus | NC_005171 | vertebrates | 1 | Reoviridae,Aquareovirus,Aquareovirus C | seg. 6 | AF239175 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Grass carp hemorrhagic virus | NC_005172 | vertebrates | 1 | Reoviridae,Aquareovirus,Aquareovirus C | seg. 7 | AF239174 |
| Grass carp hemorrhagic virus | NC_005174 | vertebrates | 1 | Reoviridae,Aquareovirus,Aquareovirus C | seg. 9 | AF284504 |
| Grass carp hemorrhagic virus | NC_005175 | vertebrates | 1 | Reoviridae,Aquareovirus,Aquareovirus C | seg. 10 | AF236688 |
| Grass carp hemorrhagic virus | NC_005176 | vertebrates | 1 | Reoviridae,Aquareovirus,Aquareovirus C | seg. 11 | AF234321 |
| Grass carp reovirus | NC_005166 | vertebrates | 4 | Reoviridae,Aquareovirus,Aquareovirus C | seg. 1 | AF260511,GQ896334,KC847320,HQ231198 |
| Grass carp reovirus | NC_005167 | vertebrates | 4 | Reoviridae,Aquareovirus,Aquareovirus C | seg. 2 | HQ231199,AF260512,GQ896335,KC847321 |
| Grass carp reovirus | NC_005168 | vertebrates | 4 | Reoviridae,Aquareovirus,Aquareovirus C | seg. 3 | AF260513,HQ231200,GU350742,KC847322 |
| Grass carp reovirus | NC_005169 | vertebrates | 4 | Reoviridae,Aquareovirus,Aquareovirus C | seg. 4 | KC847323,HQ231201,GU350743,AF403390 |
| Grass carp reovirus | NC_005170 | vertebrates | 4 | Reoviridae,Aquareovirus,Aquareovirus C | seg. 5 | AF403391,GQ896336,HQ231202,KC847324 |
| Grass carp reovirus | NC_005171 | vertebrates | 5 | Reoviridae,Aquareovirus,Aquareovirus C | seg. 6 | JN206664,AF403392,GQ896337,KC847325,HQ231208 |
| Grass carp reovirus | NC_005172 | vertebrates | 4 | Reoviridae,Aquareovirus,Aquareovirus C | seg. 7 | HQ231203,AF403393,GU350744,KC847326 |
| Grass carp reovirus | NC_005173 | vertebrates | 5 | Reoviridae,Aquareovirus,Aquareovirus C | seg. 8 | AF403394,AF259053,GU350745,HQ231204,KC847327 |
| Grass carp reovirus | NC_005174 | vertebrates | 4 | Reoviridae,Aquareovirus,Aquareovirus C | seg. 9 | GU350746,KC847328,AF403395,HQ231205 |
| Grass carp reovirus | NC_005175 | vertebrates | 5 | Reoviridae,Aquareovirus,Aquareovirus C | seg. 10 | GU350747,HQ231206,KC847329,AF403396,JN206665 |
| Grass carp reovirus | NC_005176 | vertebrates | 4 | Reoviridae,Aquareovirus,Aquareovirus C | seg. 11 | KC847330,HQ231207,AF403397,GU35074 |
| Ground squirrel hepatitis virus | NC_001484 | vertebrates | 8 | Hepadnaviridae,Orthohepadnavirus,Ground squirrel hepatitis virus | — | K02715 |
| Grouper iridovirus | NC_006549 | vertebrates | 1 | Iridoviridae,Ranavirus,Singapore grouper iridovirus | — | AY666015 |
| Gull circovirus | NC_008521 | vertebrates | 2 | Circoviridae,Circovirus,Gull circovirus | — | DQ845074,IQ685854 |
| Gyrovirus 4 | NC_018401 | vertebrates | 1 | Circoviridae,Gyrovirus,Gyrovirus 4 | — | JX310702 |
| Gyrovirus GyV3 | NC_017091 | vertebrates | 1 | Circoviridae,Gyrovirus,Gyrovirus GyV3 | — | JQ308210 |
| Gyrovirus Tu243 | NC_022788 | vertebrates | 1 | Circoviridae,Gyrovirus,Gyrovirus Tu243 | — | KF294861 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Gyrovirus Tu789 | NC_022789 | vertebrates | 1 | Circoviridae,Gyrovirus,Gyrovirus Tu789 | — | KF294862 |
| H-1 parvovirus | NC_001358 | vertebrates | 1 | Parvoviridae,Parvovirus,H-1 parvovirus | — | XQ1457 |
| HMO Astrovirus A | NC_013443 | vertebrates | 1 | Astroviridae,Mamastrovirus,HMO Astrovirus A | — | GQ415660 |
| Halastavi arva RNA virus | NC_016418 | vertebrates | 1 | Halastavi arva RNA virus | — | JN000306 |
| Hamster polyomavirus | NC_001663 | vertebrates | 8 | Polyomaviridae,Polyomavirus,Hamster polyomavirus | — | JXQ36360,JX416850,M26281,XQ2449,JX416853,JX416852,JX416849,JX416851 |
| Hepatitis A virus | NC_001489 | vertebrates | 77 | Picornaviridae,Hepatovirus,Hepatitis A virus | — | AB839696,AY644337,EU526089,X75215,M20273,X75214,AB618529,FJ360733,AB839694,HQ437707,AB279732,EF406359,DQ991030,AB020565,KC182588,X75216,EF406363,AB793726,AB279734,EU251188,JQ655151,AB279733,AB258387,AB839692,AB839693,KC182589,EF406358,AF314208,DQ991029,FJ360731,HM769724,AB793725,EU011791,AB819870,K02990,AB020566,AB020568,FJ360734,KC182590,FJ360735,JQ425480,AY644670,EF207320,AF268396,KC182587,AF51253,AB618531,EU1313,M59809,AB839695,AJ299464,EF40636,AB300205,KF773842,AF357222,AF485328,AB020564,M14707,AB819869,AB425339,DQ646426,EF406361,AB020569,AB02057,AB839697,AB279735,FJ360730,FJ360732,KF569906,M16632,EU526088,M59808,EF406357,AY644676,X83302,EF406362,M59810 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Hepatitis GB virus B | NC_001655 | vertebrates | 10 | Flaviviridae,Hepatitis GB virus B | — | AB630364,AF179612, AB630361,AB630360, J22304,AB630359,A J277947,AB630363,A B630362,AB630358 |
| Heron hepatitis B virus | NC_001486 | vertebrates | 1 | Hepadnaviridae,Avihepadnavirus,Heron hepatitis B virus | — | M22056 |
| Hipposideros bat coronavirus H KU10 | NC_018871 | vertebrates | 6 | Coronaviridae,Alphacoronavirus,Bat coronavirus H KU10 | — | JQ989266,JQ989272, JQ989269,JQ989273, JQ989267,JQ989268 |
| Hirame rhabdovirus | NC_005093 | vertebrates | 2 | Rhabdoviridae,Novirhabdovirus,Hirame rhabdovirus | — | AF104985,FJ376982 |
| Human T-cell lymphotropic virus type 2b | NC_001815,NC_001488 | vertebrates | 1 | Retroviridae,Deltaretrovirus,Primate T-lymphotropic virus 2 | — | Y13051 |
| Human T-lymphotropic virus 1 | NC_000858,NC_001436 | vertebrates | 18 | Retroviridae,Deltaretrovirus,Primate T-lymphotropic virus 1 | — | JX891479,L36905,AF 259264,JQ2029,HQ60 6138,D13784,JX8914 78,AF042071,AF1391 70,U19949,HQ60613 7,AY563954,AY5639 53,KC807984,L03561 ,L02534,AB51134,L 03562 |
| Human T-lymphotropic virus 2 | NC_001815,NC_001488 | vertebrates | 10 | Retroviridae,Deltaretrovirus,Primate T-lymphotropic virus 2 | — | GU212854,AF074965 ,AF139382,L20734,A F326584,X89270, L11 456,AF412314,AF326 583, Y14365 |
| Human T-lymphotropic virus 3 | NC_003323 | vertebrates | 4 | Retroviridae,Deltaretrovirus,Primate T-lymphotropic virus 3 | — | EU64782,DQ093792 ,DQ462191,GQ46360 |
| Human T-lymphotropic virus 4 | NC_011800 | vertebrates | 2 | Retroviridae,Deltaretrovirus,Human T-lymphotropic virus 4 | — | EF488483 |
| Human TMEV-like cardiovirus | NC_009448,NC_001366,NC_010810 | vertebrates | 1 | Picornaviridae,Cardiovirus,Theilovirus | — | GU595289 |
| Human adenovirus 4 | NC_003266,NC_017825 | vertebrates | 6 | Adenoviridae,Mastadenovirus,Human adenovirus E | — | AY594254,KF006344, AY594253,AY599837 ,AY599835,AY45865 |
| Human adenovirus 41 | NC_001454 | vertebrates | 3 | Adenoviridae,Mastadenovirus,Human adenovirus F | — | DQ315364,AB728839 ,HM565136 |
| Human adenovirus 52 | NC_006879 | vertebrates | 1 | Adenoviridae,Mastadenovirus,Human adenovirus G | — | DQ923122 |
| Human adenovirus E | NC_003266,NC_017825 | vertebrates | 2 | Adenoviridae,Mastadenovirus,Human adenovirus E | — | AY487947,EF371058 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Human adenovirus F | NC_001454 | vertebrates | Adenoviridae,Mastadenovirus,Human adenovirus F | 1 | — | L19443 |
| Human betacoronavirus 2c EMC/2012 | NC_019843 | vertebrates | Coronaviridae,Betacoronavirus,Middle East respiratory syndrome coronavirus | 1 | — | JX869059 |
| Human betacoronavirus 2c England-Qatar/2012 | NC_019843 | vertebrates | Coronaviridae,Betacoronavirus,Middle East respiratory syndrome coronavirus | 1 | — | KC667074 |
| Human betacoronavirus 2c Jordan-N 3/2012 | NC_019843 | vertebrates | Coronaviridae,Betacoronavirus,Middle East respiratory syndrome coronavirus | 1 | — | KC776174 |
| Human bocavirus 4 | NC_007018 | vertebrates | Parvoviridae,Parvovirus,Human parvovirus 4 | 1 | — | HQ113143 |
| Human coronavirus OC43 | NC_010327,NC_00773 2,NC_0051 47,NC_003 045 | vertebrates | Coronaviridae,Betacoronavirus, Betacoronavirus 1 | 6 | — | AY903459,AY585229,AY585228,JN129835,JN129834,AY903460 |
| Human cosavirus A2 | NC_012800 | vertebrates | Picornaviridae,Cosavirus,Cosavirus A | 1 | — | FJ438903 |
| Human cosavirus B | NC_012801 | vertebrates | Picornaviridae,Cosavirus,Human cosavirus B | 1 | — | FJ438907 |
| Human cosavirus D | NC_012802 | vertebrates | Picornaviridae,Cosavirus,Human cosavirus D | 1 | — | FJ438908 |
| Human cosavirus E | NC_012798 | vertebrates | Picornaviridae,Cosavirus,Human cosavirus E | 1 | — | FJ555055 |
| Human cyclovirus | NC_021568 | vertebrates | Circoviridae,Human cyclovirus VS5700009 | 1 | — | KC771281 VS5700009 |
| Human enteric coronavirus 4408 | NC_010327,NC_00773 2,NC_0051 47,NC_003 045 | vertebrates | Coronaviridae,Betacoronavirus,Betacoronavirus 1 | 1 | — | FJ415324 |
| Human erythrovirus V9 | NC_004295 | vertebrates | Parvoviridae,Erythrovirus,Human erythrovirus V9 | 1 | — | AJ249437 |
| Human foamy virus | NC_001364 | vertebrates | Retroviridae,Spumavirus,Simian foamy virus | 2 | — | Y07724,Y07725 |
| Human gyrovirus type 1 | NC_015630 | vertebrates | Circoviridae,Gyrovirus,Human gyrovirus type 1 | 1 | — | FR823283 |
| Human herpesvirus 6A | NC_001664 | vertebrates | Herpesviridae,Roseolovirus,Human herpesvirus 6A | 2 | — | KC465951,X83413 |
| Human herpesvirus 6B | NC_000898 | vertebrates | Herpesviridae,Roseolovirus,Human herpesvirus 6B | 2 | — | AB021506,AF157706 |
| Human papillomavirus | NC_001457 | vertebrates | Papillomaviridae,Gammapapillomavirus,Gammapapillomavirus 1 | 1 | — | JX413107 |
| Human papillomavirus | NC_012485 | vertebrates | Papillomaviridae,Gammapapillomavirus,Gammapapillomavirus 7 | 1 | — | JX413110 |
| Human papillomavirus | NC_012486 | vertebrates | Papillomaviridae,Gammapapillomavirus,Gammapapillomavirus 8 | 1 | — | JX413106 |
| Human papillomavirus | NC_014955 | vertebrates | Papillomaviridae,Gammapapillomavirus,Human papillomavirus 132-like viruses | 1 | — | JX444072 |
| Human papillomavirus-1 | NC_001356 | vertebrates | Papillomaviridae,Mupapillomavirus,Mupapillomavirus 1 | 1 | — | V01116 |
| Human papillomavirus-18 | NC_001357 | vertebrates | Papillomaviridae,Alphapapillomavirus,Alphapapillomavirus 7 | 1 | — | XQ5015 |
| Human papillomavirus-2 | NC_001352 | vertebrates | Papillomaviridae,Alphapapillomavirus,Alphapapillomavirus 4 | 1 | — | X55964 |

TABLE 10-continued

VíroCap-1.0 Taxonomy

| Taxonomy | Rep.Acc.ID | Host | # GN's | Lineage | Seg. Count | GN.Acc.IDs |
|---|---|---|---|---|---|---|
| Human papillomavirus-54 | NC_001676 | vertebrates | 1 | Papillomaviridae,Alphapapillomavirus,Alphapapillomavirus 13 | — | AF436129 |
| Human papillomavirus-72 | NC_001694 | vertebrates | 1 | Papillomaviridae,Alphapapillomavirus,Alphapapillomavirus 3 | — | X94164 |
| Human papillomavirus-81 | NC_001694 | vertebrates | 1 | Papillomaviridae,Alphapapillomavirus,Alphapapillomavirus 3 | — | AJ620209 |
| Human papillomavirus-83 | NC_001694 | vertebrates | 1 | Papillomaviridae,Alphapapillomavirus,Alphapapillomavirus 3 | — | AF151983 |
| Human papillomavirus-cand62 | NC_001676 | vertebrates | 1 | Papillomaviridae,Alphapapillomavirus,Alphapapillomavirus 13 | — | AY395706 |
| Human papillomavirus-cand85 | NC_001357 | vertebrates | 1 | Papillomaviridae,Alphapapillomavirus,Alphapapillomavirus 7 | — | AF131950 |
| Human papillomavirus-cand86 | NC_001694 | vertebrates | 1 | Papillomaviridae,Alphapapillomavirus,Alphapapillomavirus 3 | — | AF349909 |
| Human papillomavirus-cand87 | NC_001694 | vertebrates | 1 | Papillomaviridae,Alphapapillomavirus,Alphapapillomavirus 3 | — | AJ400628 |
| Human papillomavirus-cand89 | NC_001694 | vertebrates | 1 | Papillomaviridae,Alphapapillomavirus,Alphapapillomavirus 3 | — | AF436128 |
| Human papillomavirus-cand91 | NC_001595 | vertebrates | 1 | Papillomaviridae,Alphapapillomavirus,Alphapapillomavirus 8 | — | AF419318 |
| Human papillomavirus 109 | NC_012485 | vertebrates | 1 | Papillomaviridae,Gammapapillomavirus,Gammapapillomavirus 7 | — | EU541441 |
| Human papillomavirus 112 | NC_012486 | vertebrates | 1 | Papillomaviridae,Gammapapillomavirus,Gammapapillomavirus 8 | — | EU541442 |
| Human papillomavirus 116 | NC_013035 | vertebrates | 1 | Papillomaviridae,Gammapapillomavirus,Gammapapillomavirus 9 | — | FJ804072 |
| Human papillomavirus 121 | NC_014185 | vertebrates | 1 | Papillomaviridae,Gammapapillomavirus,Gammapapillomavirus 10 | — | GQ845443 |
| Human papillomavirus 54 | NC_001676 | vertebrates | 1 | Papillomaviridae,Alphapapillomavirus,Alphapapillomavirus 13 | — | U37488 |
| Human papillomavirus 61 | NC_001694 | vertebrates | 1 | Papillomaviridae,Alphapapillomavirus,Alphapapillomavirus 3 | — | U31793 |
| Human papillomavirus SIBX9 | NC_001576 | vertebrates | 1 | Papillomaviridae,Alphapapillomavirus,Alphapapillomavirus 2 | — | FN547152 |
| Human papillomavirus type 10 | NC_001576 | vertebrates | 1 | Papillomaviridae,Alphapapillomavirus,Alphapapillomavirus 2 | — | X74465 |
| Human papillomavirus type 102 | NC_001694 | vertebrates | 1 | Papillomaviridae,Alphapapillomavirus,Alphapapillomavirus 3 | — | DQ080083 |
| Human papillomavirus type 106 | NC_004104 | vertebrates | 1 | Papillomaviridae,Alphapapillomavirus,Alphapapillomavirus 14 | — | DQ080082 |
| Human papillomavirus type 108 | NC_012213,NC_008188,NC_008189 | vertebrates | 1 | Papillomaviridae,Gammapapillomavirus,Gammapapillomavirus 6 | — | FM212639 |
| Human papillomavirus type 11 | NC_001355 | vertebrates | 49 | Papillomaviridae,Alphapapillomavirus,Alphapapillomavirus 10 | — | FN907959,FN907964,HE574703,FN87002 1,HE611271,HE6112 63,HE611259,HE611 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 273,HE962365,HE61 1264,JN644142,FN87 0022,HE611267,JQ7 73412,EU918768,HE 611260,HE962023,H E574704,HE611268, HE962366,FN907963 ,M14119,JQ773409,H E574701,FN907961,J N64414,FN907957, FN907960,HE962024 ,HE611270,JQ77341 1,FR872717,HE6112 66,HE611274,HE574 705,JQ773410,HE61 1272,HE611269,HE9 62368,HE611265,HE 611258,FN907958,H E611261,JQ773408, HE962367,HE611262 ,FN907962,HE57470 2,HE962025 |
| Human papillomavirus type 114 | NC_001694 | vertebrates | 1 | Papillomaviridae,Alphapapillomavirus,Alphapapillomavirus 3 | — | GQ244463 |
| Human papillomavirus type 117 | NC_001576 | vertebrates | 1 | Papillomaviridae,Alphapapillomavirus,Alphapapillomavirus 2 | — | GQ246950 |
| Human papillomavirus type 119 | NC_012486 | vertebrates | 1 | mapapillomavirus 8 | — | GQ845441 |
| Human papillomavirus type 123 | NC_012485 | vertebrates | 1 | Papillomaviridae,Gammapapillomavirus,Gammapapillomavirus 7 | — | GQ845445 |
| Human papillomavirus type 128 | NC_014952 | vertebrates | 1 | Papillomaviridae,Gammapapillomavirus,Human papillomavirus type 128 | — | GU225708 |
| Human papillomavirus type 129 | NC_014953 | vertebrates | 1 | Papillomaviridae,Gammapapillomavirus,Human papillomavirus type 129 | — | GU233853 |
| Human papillomavirus type 13 | NC_001355 | vertebrates | 2 | Papillomaviridae,Alphapapillomavirus,Alphapapillomavirus 10 | — | X62843,DQ344807 |
| Human papillomavirus type 130 | NC_014185 | vertebrates | 1 | Papillomaviridae,Gammapapillomavirus,Gammapapillomavirus 10 | — | GU117630 |
| Human papillomavirus type 131 | NC_014954 | vertebrates | 1 | Papillomaviridae,Gammapapillomavirus,Human papillomavirus type 131 | — | GU117631 |
| Human papillomavirus type 132 | NC_014955 | vertebrates | 1 | Papillomaviridae,Gammapapillomavirus,Human papillomavirus 132-like viruses | — | GU117632 |
| Human papillomavirus type 133 | NC_014185 | vertebrates | 1 | Papillomaviridae,Gammapapillomavirus,Gammapapillomavirus 10 | — | GU117633 |
| Human papillomavirus type 134 | NC_014956 | vertebrates | 1 | Papillomaviridae,Gammapapillomavirus,Human papillomavirus type 134 | — | GU117634 |
| Human papillomavirus type 148 | NC_014955 | vertebrates | 1 | Papillomaviridae,Gammapapillomavirus,Human papillomavirus 132-like viruses | — | GU129016 |

TABLE 10-continued

VrioCap-1.0 Taxonomy

| Taxonomy | Rep.Acc.ID | Host | # GN's | Lineage | Seg. Count | GN.Acc.IDs |
|---|---|---|---|---|---|---|
| Human papillomavirus type 149 | NC_012485 | vertebrates | 1 | Papillomaviridae,Gammapapillomavirus,Gammapapillomavirus 7 | — | GU117629 |
| Human papillomavirus type 16 | NC_001526 | vertebrates | 119 | Papillomaviridae,Alphapapillomavirus,Alphapapillomavirus 9 | — | HQ644258,HQ644259,HQ644243,AB186287,JQ004097,HQ644262,HQ644298,FJ610149,HQ644249,FJ610152,HQ644264,AB889490,HQ644263,AF536179,HQ644283,HQ644292,HQ644261,H064273,AY686580,HQ644296,JQ004096,AB818688,AB818690,JQ004094,AF472509,FJ610146,JN565302,HQ644239,AB889492,HQ644240,HQ644250,HQ644286,HQ644269,HQ644278,HQ644280,HQ644288,FJ610151,HQ644294,HQ644248,HQ644241,H064238,HQ644236,HQ644265,HQ644287,HQ644268,HQ644427,AF402678,AY686581,FJ610147,HQ644253,AF534061,HQ644254,HM057182,HQ644293,FJ610150,HQ644284,HQ644260,HQ644242,JQ004093,HQ644291,FJ006723,AB889489,JQ004095,H0644276,HQ644247,HQ644277,HQ644424,HQ644281,HQ644427,HQ644275,AF536180,JQ004099,JQ067944,HQ644289,FJ610148,HQ644234,JN565303,AB889491,HQ644257,HQ644255,AB889494,AY686579,H0644272,AB818689,AY686582,HQ644245,AF472508,HQ644287 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 5,AF125673,HQ6442 70,HQ644295,HQ644 290,HQ644266,HQ64 4252,HQ644251,HQ6 44267,AB818693,JQO 67943,HQ644271,HQ 644237,AB889488,H 0644256,HQ644235, JQ004092,HQ644246 ,JQ004098,AB889493 ,U89348,HQ644282,A B818692,AX800450, HQ644274,AY686583 ,KO2718,AY686584,E U918764,AB818691, EU118173,HQ644297 |
| Human papillomavirus type 167 | NC_022892 | vertebrates | 1 | Papillomaviridae,Gammapapillomavirus,Human papillomavirus type 167 | — | KC862318 |
| Human papillomavirus type 168 | NC_012486 | vertebrates | 1 | Papillomaviridae,Gammapapillomavirus,Gammapapillomavirus 8 | — | KC862317 |
| Human papillomavirus type 18 | NC_001357 | vertebrates | 46 | Papillomaviridae,Alphapapillomavirus,Alphapapillomavirus 7 | — | GQ180792,EF202155 ,EF202149,EF202148 ,KC470211,KC47021 6,EF202150,KC47022 30,EF202153,GQ180 788,KC470214,GQ18 0786,KC470221,KC4 70218,KC470228,GQ 180784,KC470227,K C470229,KC470226, KC470217,KC470213 ,GQ180790,KC47020 9,GQ180791,EF2021 43,EF202145,GQ180 789,KC470222,KC47 0215,KC470220,EF2 02152,EF202154,AY2 62282,EF202151,KC 470225,GQ180787,E F202147,GQ180785, KC470212,KC470219 ,KC470210,EF20214 4,KC470223,EF2021 46,KC470224,KC470 208 |
| Human papillomavirus type 1a | NC_001356 | vertebrates | 1 | Papillomaviridae,Mupapillomavirus,Mupapillomavirus 1 | — | U06714 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human papillomavirus type 2 | NC_001352 | vertebrates | 4 | Papillomaviridae,Alphapapillomavirus,Alphapapillomavirus 4 | — | EF362755,EF362754, EF117891,EF117890 |
| Human papillomavirus type 26 | NC_001583 | vertebrates | 1 | Papillomaviridae,Alphapapillomavirus,Alphapapillomavirus 5 | — | X74472 |
| Human papillomavirus type 27 | NC_001352 | vertebrates | 1 | Papillomaviridae,Alphapapillomavirus,Alphapapillomavirus 4 | — | X74473 |
| Human papillomavirus type 27b | NC_001352 | vertebrates | 1 | Papillomaviridae,Alphapapillomavirus,Alphapapillomavirus 4 | — | AB211993 |
| Human papillomavirus type 28 | NC_001576 | vertebrates | 1 | Papillomaviridae,Alphapapillomavirus,Alphapapillomavirus 2 | — | U31783 |
| Human papillomavirus type 29 | NC_001576 | vertebrates | 1 | Papillomaviridae,Alphapapillomavirus,Alphapapillomavirus 2 | — | U31784 |
| Human papillomavirus type 3 | NC_001576 | vertebrates | 1 | Papillomaviridae,Alphapapillomavirus,Alphapapillomavirus 2 | — | X74462 |
| Human papillomavirus type 30 | NC_001593 | vertebrates | 1 | Papillomaviridae,Alphapapillomavirus,Alphapapillomavirus 6 | — | X74474 |
| Human papillomavirus type 31 | NC_001526 | vertebrates | 23 | Papillomaviridae,Alphapapillomavirus,Alphapapillomavirus 9 | — | JQ4353,HQ537667,HQ537678,HQ537674,HQ537669,HQ537666,HQ537679,HQ537670,HQ537671,HQ537681,HQ537673,HQ537687,HQ537666,HQ537677,HQ537685,HQ537682,HQ537683,HQ537680,HQ537672,HQ537676,HQ537767,HQ537684,HQ53765,HQ537686 |
| Human papillomavirus type 32 | NC_001586 | vertebrates | 1 | Papillomaviridae,Alphapapillomavirus,Alphapapillomavirus 1 | — | X74475 |
| Human papillomavirus type 33 | NC_001526 | vertebrates | 23 | Papillomaviridae,Alphapapillomavirus,Alphapapillomavirus 9 | — | HQ537700,HQ537706,HQ537702,HQ537701,HQ537698,M12732,HQ537694,HQ537696,HQ537707,HQ537692,HQ537688,HQ537697,HQ537689,HQ537703,EU918766,HQ537693,HQ537700,HQ537704,HQ537690,HQ537691,HQ537695,HQ537769,HQ537705,A12360 |
| Human papillomavirus type 34 | NC_001587 | vertebrates | 1 | Papillomaviridae,Alphapapillomavirus,Alphapapillomavirus 11 | — | X74476 |
| Human papillomavirus type 35 | NC_001526 | vertebrates | 28 | Papillomaviridae,Alphapapillomavirus,Alphapapillomavirus 9 | — | HQ537725,HQ537708,HQ537715,HQ537730,HQ537711,HQ537 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human papillomavirus type 35H | NC_001526 | vertebrates | 1 | Papillomaviridae,Alphapapillomavirus,Alphapapillomavirus 9 | — | 726,JX129488,HQ537720,HQ537718,HQ537713,HQ537717,HQ537729,HQ537723,H0537714, HQ537722,M74117,HQ537710,H0537716, HQ537719,JX129486,HQ537728,HQ537721 ,HQ537712,HQ537727,HQ537709,HQ537724,JX129487,JX129485 |
| Human papillomavirus 39 | NC_001357 | vertebrates | 20 | Papillomaviridae,Alphapapillomavirus,Alphapapillomavirus 7 | — | X74477 |
| Human papillomavirus type 4 | NC_001457 | vertebrates | 1 | Papillomaviridae,Gammapapillomavirus,Gammapapillomavirus 1 | — | KC470243,KC470238,KC470239,KC470247,KC470241,KC470236,M62849,KC470242,KC470232,KC470244,KC470246,KC470237,KC470235,KC470249,KC470234,KC470245,KC470248,KC470233 |
| Human papillomavirus type 40 | NC_001595 | vertebrates | 1 | Papillomaviridae,Alphapapillomavirus,Alphapapillomavirus 8 | — | X70827 |
| Human papillomavirus type 41 | NC_001354 | vertebrates | 1 | Papillomaviridae,Nupapillomavirus,Nupapillomavirus 1 | — | X74478 |
| Human papillomavirus type 42 | NC_001586 | vertebrates | 3 | Papillomaviridae,Alphapapillomavirus,Alphapapillomavirus 1 | — | X56147 |
| Human papillomavirus type 43 | NC_001595 | vertebrates | 1 | Papillomaviridae,Alphapapillomavirus,Alphapapillomavirus 8 | — | GQ472847,A28090,M73236 |
| Human papillomavirus type 44 | NC_001355 | vertebrates | 1 | Papillomaviridae,Alphapapillomavirus,Alphapapillomavirus 10 | — | AJ620205 |
| Human papillomavirus type 45 | NC_001357 | vertebrates | 24 | Papillomaviridae,Alphapapillomavirus,Alphapapillomavirus 7 | — | U31788 |
| | | | | | | EF202158,EF202157,KC470251,EF202165,EF202162,KC470255,EF202167,EF202161,KC470252,KC470250,X74479,EF202163,KC470256,EF202166,EF202160,KC470259,KC470258,EF202156,KC470253,KC470254 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human papillomavirus type 48 | NC_001690 | vertebrates | 1 | Papillomaviridae,Gammapapillomavirus,Gammapapillomavirus 2 | — | 0260,KC470257,EF202159,EF202164,KC470254 |
| Human papillomavirus type 50 | NC_001691 | vertebrates | 1 | Papillomaviridae,Gammapapillomavirus,Gammapapillomavirus 3 | — | U31789 |
| Human papillomavirus type 51 | NC_001583 | vertebrates | 1 | Papillomaviridae,Alphapapillomavirus,Alphapapillomavirus 5 | — | U31790 |
| Human papillomavirus type 52 | NC_001526 | vertebrates | 26 | Papillomaviridae,Alphapapillomavirus,Alphapapillomavirus 9 | — | M62877 |
| Human papillomavirus type 53 | NC_001593 | vertebrates | 16 | Papillomaviridae,Alphapapillomavirus,Alphapapillomavirus 6 | — | HQ537751,HQ537736,HQ537734,HQ537742,HQ537732,AB819274,HQ537732,HQ537745,AB819273,HQ537738,HQ537743,HQ537819272,HQ537733,H0537740,GQ472848,HQ537750,HQ537741,HQ537735,HQ537774,7,HQ537735,HQ537749,HQ537739,HQ537737,X744,81,HQ537744,HQ537731,HQ537748 |
| | | | | | | EF546474,EF546479,EF546469,EF546470,X74482,EF546478,EF546480,EF546473,EF546482,EF546475,EF546472,EF546481,EF546471,EF546477,GQ472849,EF546476 |
| Human papillomavirus type 55 | NC_001355 | vertebrates | 1 | Papillomaviridae,Alphapapillomavirus,Alphapapillomavirus 10 | — | U31791 |
| Human papillomavirus type 56 | NC_001593 | vertebrates | 7 | Papillomaviridae,Alphapapillomavirus,Alphapapillomavirus 6 | — | EF177178,EF177181,EF177177,EF177179,X74483,EF177176,EF177180 |
| Human papillomavirus type 57 | NC_001352 | vertebrates | 1 | Papillomaviridae,Alphapapillomavirus,Alphapapillomavirus 4 | — | X55965 |
| Human papillomavirus type 57b | NC_001352 | vertebrates | 1 | Papillomaviridae,Alphapapillomavirus,Alphapapillomavirus 4 | — | U37537 |
| Human papillomavirus type 57c | NC_001352 | vertebrates | 1 | Papillomaviridae,Alphapapillomavirus,Alphapapillomavirus 4 | — | AB361563 |
| Human papillomavirus type 58 | NC_001526 | vertebrates | 45 | Papillomaviridae,Alphapapillomavirus,Alphapapillomavirus 9 | — | KC860271,HQ537758,HQ537757,EU91876,AB819278,HQ537775,AB819278,HQ537753,FJ385267,HQ537763,HQ537775,HQ537 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 769,FJ385261,FJ385265,GQ472850,HQ537768,AB819279,HQ537771,HQ53755,HQ537760,HQ53762,D90400,HQ53770,AB819276,FJ385268,HQ537759,FJ385266,KC860269,HQ537754,FJ385262,AB819277,H0537777,HQ537766,HQ537765,HQ537764,HQ53761,AB81924,HQ53767,FJ385275,HQ53767,FJ385263,HQ537756,HQ537752,FJ385264,HQ537776,HQ537773,HQ537774,HQ537772,KC860270 |
| Human papillomavirus type 59 | NC_001357 | vertebrates | 8 | Papillomaviridae,Alphapapillomavirus,Alphapillomavirus 7 | — | KC470262,KC470261,X77858,KC470266,KC470265,KC470263,KC470264,EU918767 |
| Human papillomavirus type 6 | NC_001355 | vertebrates | 168 | Papillomaviridae,Alphapapillomavirus,Alphapillomavirus 10 | — | HG793909,HE962032,HG793933,HG793917,HG793935,HG793938,1,HG793851,HG793906,JN252321,HG793918,HG793900,HG793875,HG793847,HG793852,HG793908,HG793868,HG793878,HG793890,HG793883,HG793879,HG793890,HG793838,9,FR751329,HG793826,HG793843,HG793821,FR751324,JN252320,HG793874,HG793856,HG793925,HG793937,HG793840,HG793849,HG793894,HG793882,HG793866,HG793896,HG793888,6,HG793865,HG793838,69,FR751320,HG793844,HG793905,FR751322,HE962028,HG793902,FR751325,HG793885,HG793887,H |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | G79815,HG793888,HG793841,HG793858,HG793860,HG793939,29,FR751328,HG793829,FR751328,HG793870,HG793863,HG793919,HG793811,HG793897,HG793936,H793838,HG793895,FR751323,HG793810,HG793879,HG793853,JN252318,HG793927,HG793912,HG793922,HG793837,HG793824,FR751331,HG793848,HG793873,HG793939,JN252323,HG793842,HG793931,JN252319,HG793823,HG793889,HG793816,FR751327,AF092932,HG793827,FR751326,HG793845,HG793884,HG793817,HG793924,HG793813,HG793859,HG793893,HG793830,JN252314,HG793836,FR751336,HG793818,HG793792,HG793877,HG793939,HG793862,HG793901,HG793892,HG793911,HE962026,FR751337,HG793861,HG793910,HG793828,HG793867,HG793832,HG793857,HG793393,HG793903,HG793939,HG751338,HG793864,HG793822,HG793914,HG793898,HG793876,HG793920,HE962029,HG793814,FR751332,JN252322,HG793871,FR751335,HG793928,HG793834,JN252317,HG793833,HG793915,HG793 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 835,FR751334,HG79 3916,HG793921,HG7 93904,HG793872,JN 252315,HG793812,H E962031,HE962027, HG793846,HG79390 7,HG793934,HG7938 55,HG793831,HE962 030,HG793880,FR75 1321,HG793891,HG7 93899,HG793938,FR 751330,HG793820,H G793809,JN252316, HG793819,HG79388 3,HG793850,FR7513 33,HG793854,HG793 825 |
| Human papillomavirus type 60 | NC_001693 | vertebrates | 1 | Papillomaviridae,Gammapapillomavirus,Gam mapapillomavirus 4 | — | U31792 |
| Human papillomavirus type 63 | NC_001458 | vertebrates | 1 | Papillomaviridae,Mupapillomavirus,Mupapillo mavirus 2 | — | X70828 |
| Human papillomavirus type 65 | NC_001457 | vertebrates | 1 | Papillomaviridae,Gammapapillomavirus,Gam mapapillomavirus 1 | — | X70829 |
| Human papillomavirus type 66 | NC_001593 | vertebrates | 11 | Papillomaviridae,Alphapapillomavirus,Alphapa pillomavirus 6 | — | EF177186,U31794,E F177184,EF177188,E F177185,EF177183,E F177191,EF177187,E F177182,EF177189,E F177190 |
| Human papillomavirus type 67 | NC_001526 | vertebrates | 8 | Papillomaviridae,Alphapapillomavirus,Alphapa pillomavirus 9 | — | HQ537781,HQ53778 2,HQ537778,HQ5377 84,HQ537780,HQ537 783,HQ537779,D212 08 |
| Human papillomavirus type 68 | NC_001357 | vertebrates | 19 | Papillomaviridae,Alphapapillomavirus,Alphapa pillomavirus 7 | — | KC470277,KC470271 ,KC470276,EU91876 9,KC470270,KC4702 82,KC470274,KC470 278,KC470267,KC47 0275,KC470272,KC4 70279,KC470268,KC 470273,KC470269,K C470283,GQ472851, KC470281,KC470280 |
| Human papillomavirus type 68a | NC_001357 | vertebrates | 1 | Papillomaviridae,Alphapapillomavirus,Alphapa pillomavirus 7 | — | DQ080079 |
| Human papillomavirus type 68b | NC_001357 | vertebrates | 1 | Papillomaviridae,Alphapapillomavirus,Alphapa pillomavirus 7 | — | FR751039 |

TABLE 10-continued

| Taxonomy | Rep.Acc.ID | Host | # GN's | Lineage | Seg. Count | GN.Acc.IDs |
|---|---|---|---|---|---|---|
| Human papillomavirus type 69 | NC_001583 | vertebrates | 1 | Papillomaviridae,Alphapapillomavirus,Alphapapillomavirus 5 | — | AB027020 |
| Human papillomavirus type 6a | NC_001355 | vertebrates | 1 | Papillomaviridae,Alphapapillomavirus,Alphapapillomavirus 10 | — | L41216 |
| Human papillomavirus type 6b | NC_001355 | vertebrates | 1 | Papillomaviridae,Alphapapillomavirus,Alphapapillomavirus 10 | — | XQ0203 |
| Human papillomavirus type 7 | NC_001595 | vertebrates | 1 | Papillomaviridae,Alphapapillomavirus,Alphapapillomavirus 8 | — | X74463 |
| Human papillomavirus type 70 | NC_001357 | vertebrates | 9 | Papillomaviridae,Alphapapillomavirus,Alphapapillomavirus 7 | — | KC470289,KC470290,KC470291,U21941,KC470288,KC470287,KC470286,KC470284,KC470285 |
| Human papillomavirus type 71 | NC_004104 | vertebrates | 5 | Papillomaviridae,Alphapapillomavirus,Alphapapillomavirus 14 | — | AB040456,AY330623,AY330620,AY330622,AY330621 |
| Human papillomavirus type 73 | NC_001587 | vertebrates | 1 | Papillomaviridae,Alphapapillomavirus,Alphapapillomavirus 11 | — | X94165 |
| Human papillomavirus type 74 | NC_001355 | vertebrates | 1 | Papillomaviridae,Alphapapillomavirus,Alphapapillomavirus 10 | — | AF436130 |
| Human papillomavirus type 77 | NC_001576 | vertebrates | 1 | Papillomaviridae,Alphapapillomavirus,Alphapapillomavirus 2 | — | Y15175 |
| Human papillomavirus type 82 | NC_001583 | vertebrates | 2 | Papillomaviridae,Alphapapillomavirus,Alphapapillomavirus 5 | — | AB027021,AF293961 |
| Human papillomavirus type 84 | NC_001694 | vertebrates | 1 | Papillomaviridae,Alphapapillomavirus,Alphapapillomavirus 3 | — | AF293960 |
| Human papillomavirus type 88 | NC_010329 | vertebrates | 1 | Papillomaviridae,Gammapapillomavirus,Gammapapillomavirus 5 | — | EF467176 |
| Human papillomavirus type 90 | NC_004104 | vertebrates | 2 | Papillomaviridae,Alphapapillomavirus,Alphapapillomavirus 14 | — | AY057438,AB542808 |
| Human papillomavirus type 94 | NC_001576 | vertebrates | 3 | Papillomaviridae,Alphapapillomavirus,Alphapapillomavirus 2 | — | AB201226,GU117628,AJ620211 |
| Human papillomavirus type 95 | NC_001457 | vertebrates | 1 | Papillomaviridae,Gammapapillomavirus,Gammapapillomavirus 1 | — | AJ620210 |
| Human papillomavirus type 97 | NC_001357 | vertebrates | 3 | Papillomaviridae,Alphapapillomavirus,Alphapapillomavirus 7 | — | DQ080080,EF202168,EF436229 |
| Human papillomavirus type XS2 | NC_001576 | vertebrates | 1 | Papillomaviridae,Alphapapillomavirus,Alphapapillomavirus 2 | — | KC138720 |
| Human parechovirus | NC_001897 | vertebrates | 3 | Picornaviridae, Parechovirus,Human parechovirus | — | EU022171,KJ152442,AJQ05695 |
| Human parechovirus 1 | NC_001897 | vertebrates | 18 | Picornaviridae, Parechovirus,Human parechovirus | — | EF051629,S45208,GQ183021,GQ183035,GQ183023,FJ840477,GQ183019,JX44135,GQ183022,FM178558,KC769584,GQ183018,GQ183024,JX57... |

TABLE 10-continued

VidoCap-1.0 Taxonomy

| Taxonomy | Rep.Acc.ID | Host | # GN's | Lineage | Seg. Count | GN.Acc.IDs |
|---|---|---|---|---|---|---|
| Human parechovirus 2 | NC_001897 | vertebrates | 1 | Picornaviridae, Parechovirus,Human parechovirus | — | 5746,GQ183020,GQ183025,L02971,GQ183034 |
| Human parechovirus 3 | NC_001897 | vertebrates | 13 | Picornaviridae, Parechovirus,Human parechovirus | — | GQ183031,AJ889918,GQ183026,JX82660 7,GQ183027,AB6680 29,GQ183032,GQ183028,JX682576,AB084 913,GQ183030,GQ183033,GQ183029 |
| Human parechovirus 4 | NC_001897 | vertebrates | 3 | Picornaviridae, Parechovirus,Human parechovirus | — | DQ315670,AM235750,AB433629 |
| Human parechovirus 5 | NC_001897 | vertebrates | 2 | Picornaviridae, Parechovirus,Human parechovirus | — | AM235749,JXQ50181 |
| Human parechovirus 6 | NC_001897 | vertebrates | 4 | Picornaviridae, Parechovirus,Human parechovirus | — | AB252582,EU077518,FJ888592,EU024629 |
| Human parechovirus 7 | NC_001897 | vertebrates | 1 | Picornaviridae, Parechovirus,Human parechovirus | — | EU556224 |
| Human parechovirus 8 | NC_001897 | vertebrates | 1 | Picornaviridae, Parechovirus,Human parechovirus | — | EU716175 |
| Human parechovirus type 1 PicoBank/HPeV1/a | NC_001897 | vertebrates | 1 | Picornaviridae, Parechovirus,Human parechovirus | — | FM242866 |
| Human parvovirus 4 | NC_007018 | vertebrates | 7 | Parvoviridae,Parvovirus,Human parvovirus 4 | — | DQ87387,DQ87338 8,EU175856,EU1758 55,AY622943,EU874 248,DQ873389 |
| Human polyomavirus 10 | NC_018102 | vertebrates | 1 | Polyomaviridae,Polyomavirus,MW polyomavirus | — | JX262162 |
| Human polyomavirus 12 | NC_020890 | vertebrates | 1 | Polyom avi ridae, Polyomavirus,Human polyomavirus 12 | — | JX308829 |
| Human polyomavirus 9 | NC_015150 | vertebrates | 2 | Polyom avi ridae, Polyom avi rus,Human polyomavirus 9 | — | KC831440,HQ696595 |
| Human rhinovirus C | NC_009996 | vertebrates | 16 | Picornaviridae,Enterovirus,Rhinovirus C | — | JF317015,JN798567, JF317014,JF317016, JN205461,JX291115, GU219984,EU840952 ,JF317013,JF317017, JQ245968,EF582386, JN837688,EF582385, DQ875932,EF582387 |
| Human rhinovirus C strain QCE | NC_009996 | vertebrates | 1 | Picornaviridae,Enterovirus,Rhinovirus C | — | GQ323774 |
| Human rhinovirus C3 | NC_009996 | vertebrates | 1 | Picornaviridae,Enterovirus,Rhinovirus C | — | EF186077 |
| Human rhinovirus C35 | NC_009996 | vertebrates | 1 | Picornaviridae,Enterovirus,Rhinovirus C | — | JF436925 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human spumaretrovirus | NC_001364 | vertebrates | 1 | Retroviridae,Spumavirus,Simian foamy virus | — | U21247 |
| Ictalurid herpesvirus 1 | NC_001493 | vertebrates | 1 | Alloherpesviridae,Ictalurivirus,Ictalurid herpesvirus 1 | — | M75136 |
| Infectious bronchitis virus | NC_010800,NC_001451 | vertebrates | 71 | Coronaviridae,Gammacoronavirus,Avian coronavirus | — | DQ288927,DQ001339,AY338732,GU393335,GU399333,FJ904717,FJ904723,JQ977698,FJ904720,GU393937,EU714028,FJ904716,HM245924,JF274479,GQ504720,GU393332,GU393334,FJ904721,FJ904713,JX195175,JX195177,JF828981,JF893452,AY514485,GQ504723,FJ888351,JX195178,GU393331,GU393338,FJ807652,GQ504722,EU526388,GQ504721,DQ64405,JX195176,FJ904722,KF574761,KF377577,EU637854,JF330899,JX897900,DQ834384,AY641576,DQ001338,AY851295,EU817497,GQ504725,KC013541,EU418975,HM245923,FJ904719,JF330898,KC136209,JF828980,AY319651,JQ977697,EU418976,FJ904714,GU393336,KC506155,EU714029,KC008600,KF411040,FJ904715,HQ850618,KF411041,KC119407,FJ904718,AY692454,GQ504724,HQ848267 |
| Infectious bronchitis virus ITA/90254/2005 | NC_010800,NC_001451 | vertebrates | 1 | Coronaviridae,Gammacoronavirus,Avian coronavirus | — | FN430414 |
| Infectious bronchitis virus NGA/A116E7/2006 | NC_010800,NC_001451 | vertebrates | 1 | Coronaviridae,Gammacoronavirus,Avian coronavirus | — | FN430415 |
| Infectious bursal disease virus | NC_004178 | vertebrates | 93 | Birnaviridae,Avibirnavirus, Infectious bursal disease virus | seg. A | EF418034,AF051837,GQ166970,DQ40324 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 8,AF533670,AF09217 1,AF165150,JQ41101 2,EU162089,JF90770 2,EF418036,DQ0499, AF240686,GQ451330 ,EU595669,JX134483 ,DQ0867,AI427340,A Y598356,EU595670, AJ310185,EF418035, AY099456,AM167550 ,AY462026,AF140705 ,EU595667,EU59566 8,AY319768,AF36277 6,EU184687,FJ69513 8,AY134874,Z21971, X84034,AY323952,A F321054,AF527039,E U595672,DQ906921, D83985,EF646853,D 00869,DQ927040,AY 444873,AF092943,AF 194428,EU162088,AJ 879932,AY368653,D 0088175,AY665672, XQ3993,AF165151,A Y918950,AF109154,E U595671,JX134485, M97346,AF508176,A Y918948,EF517528,A F247006,AF499929,A F362773,AF443294,D 0927042,AF322444,J 0403646,FJ695139,J F811920,L42284,AF3 62747,AF133904,AF3 21055,AF362771,AY0 29166,AF321056,DQ 778035,EU184689,A F165149,JN585293,D 49706,AJ318896,EF4 18033,M66722,AY46 2027,EU184685,U30 818,JF907703,X9276 0,AM111353,GQ1669 72 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Infectious bursal disease virus | NC_004179 | vertebrates | Birnaviridae,Avibirnavirus,Infectious bursal disease virus | 87 | seg. B | AY598355,EU162092,AM167551,AJ318897,JQ403647,AF499397,9,EU162093,AY459320,AY459321,AF322445,GQ166971,JX134484,AY134875,U30819,EU162095,EU595675,EU595677,AF092944,EF576658,EU162091,JF907704,AB368971,AF362748,AJ1880090,AB368969,M19336,AY103464,X92761,EU595676,AF133905,AF203880,EU162094,JQ411013,GQ451331,AF083092,AF362774,X84035,U62661,EF688065,AY654284,AM111354,JF907705,AF499930,AF083093,AJ496637,D49707,AF194429,EU595678,AF362772,DQ906922,JF646854,EU162090,AF083094,DQ679811,EU595674,EF517529,U20950,AF527038,DQ118374,FJQ40159,JF811921,DQ679813,GQ452269,AY099457,DQ927041,DQ679814,DQ403249,AY918949,EU595673,DQ679812,AF527040,JX134486,EU184690,AJ310186,AY705393,AY918947,JN411134,AF362770,AF362775,AF240687,DQ166818,EU184686,AY368654,AY029165,DQ927043,L19502,EU184688 |
| Infectious bursal disease virus CU-1 | NC_004178 | vertebrates | Birnaviridae,Avibirnavirus, Infectious bursal disease virus | 1 | seg. A | X16107 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Infectious hematopoietic necrosis virus | NC_001652 | vertebrates | Rhabdoviridae,Novirhabdovirus, Infectious hematopoietic necrosis virus | 5 | — | GQ413939,JX649101,X89213,L40883,HM461966 |
| Infectious pancreatic necrosis virus | NC_001915 | vertebrates | Birnaviridae,Aquabirnavirus,Infectious pancreatic necrosis virus | 29 | seg. A | DQ536090,AY780919,AJ622822,AY780923,AY780921,M18049,AY374435,AY379738,AY780918,AY354519,AY379737,DQ0701,AY379736,AY780922,AY379742,DQ536091,AY83632,AY35452,0,AY379744,AY283780,AF078668,AY780924,U56907,D26526,EF493156,AY780920,AY354521,AY379735,AY379740 |
| Infectious pancreatic necrosis virus | NC_001916 | vertebrates | Birnaviridae,Aquabirnavirus,Infectious pancreatic necrosis virus | 20 | seg. B | AY379741,AY379739,AY780930,AY379743,AY823633,M58756,AY129664,AY354522,AY780927,AY354523,AY354524,M58757,AY780929,AY780931,AY780925,AY780926,AY780928,D26527,AJ622823,AF078669 |
| Infectious pancreatic necrosis virus-Mexico | NC_001916 | vertebrates | Birnaviridae,Aquabirnavirus,Infectious pancreatic necrosis virus | 1 | seg. B | EU665685 |
| Infectious salmon anemia virus | NC_006497 | vertebrates | Orthomyxoviridae,Isavirus,Infectious salmon anemia virus | 44 | seg. B | DQ022085,DQ785283,DQ785275,DQ785286,DQ003603,DQ785276,DQ003600,AF262386,EU118822,AF315063,DQ785278,AF404340,DQ785281,D0003601,AF262382,DQ785279,AF262388,AF262380,DQ003607,AF262383,AY744395,DQ785285,AJQ122,85,DQ785277,AF262389,DQ058660,DQ003602,DQ785274,AF312317,Y10404,AF312315,DQ003606,DQ785280,AF262384,DQO |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 03605,AF262381,DQ 785284,AF262387,D 078582,DQ003604, DQ785273,AJ242016 ,AF262385,AF312316 |
| Infectious salmon anemia virus | NC_006498 | vertebrates | 8 | Orthomyxoviridae,Isavirus,Infectious salmon anemia virus | seg. 7 | AY044132,AJ306487, AF404341,AF429990, AF328627,DQ673253 ,AF429989,DQ67325 4 |
| Infectious salmon anemia virus | NC_006499 | vertebrates | 9 | Orthomyxoviridae,Isavirus,Infectious salmon anemia virus | seg. 6 | AF404342,JN711062, AF220607,JN711065, AY059402,JN711074, JN711093,JN711096, JN711060 |
| Infectious salmon anemia virus | NC_006500 | vertebrates | 38 | Orthomyxoviridae,Isavirus,Infectious salmon anemia virus | seg. 5 | JN711056,JN711023, DQ465047,JN711047 ,JN711040,AF429986 ,JN711041,JN711021 ,JN711054,DQ46504 3,JN711030,JN711102 4,JN711019,DQ46650 44,AJ277461,DQ440 507,JN711043,AF404 343,AF429988,JN711 044,DQ440508,AF42 9987,JN711053,JN71 1026,JN711055,JN71 1049,DQ465045,JN7 11045,JN711042,JN7 11050,JN711033,JN7 11046,JN711036,DQ 465046,JN711022,JN 711051,DQ440506,J N711031 |
| Infectious salmon anemia virus | NC_006501 | vertebrates | 25 | Orthomyxoviridae,Isavirus,Infectious salmon anemia virus | seg. 4 | DQ785227,DQ785222 3,DQ785221,DQ52206 00,DQ785218,DQ785 224,AY744391,DQ78 5217,HM172539,DQ7 85222,DQ520601,DQ 785229,DQ785219,D 785228,DQ520602, DQ520598,AF404344 DQ520597,DQ78522 5,DQ785220,DQ7852 |

TABLE 10-continued

| Taxonomy | Rep.Acc.ID | Host | VrioCap-1.0 Taxonomy | | Seg. Count | GN.Acc.IDs |
|---|---|---|---|---|---|---|
| | | | # GN's | Lineage | | |
| Infectious salmon anemia virus | NC_006502 | vertebrates | 92 | Orthomyxoviridae,Isavirus,Infectious salmon anemia virus | seg. 3 | 26,EU118818,DQ785230,AF306548,DQ520599 JN710910,JN710861, JN710908,JN710864, JN710894,JN710866, JN710854,JN710843, JN710915,JN710889, JN710839,JN710871, JN710846,JN710904, JN710918,JN710907, JN710840,JN710913, JN710881,JN710916, JN710858,JN710853, JN710919,JN710872, JN710844,JN710883, JN710903,AJ276858, JN710887,JN710906, JN710835,JN710842, HM172538,JN710837 AF404345,JN710873 JN710914,JN710867 JXQ70881,JN710890 JN710905,JN710879 JN710896,JN710841 JN710851,JN710891 JN710859,JN710836 JN710885,JN710880 JN710895,JN710878 JN710869,JN710874 JN710850,JN710865 JN710870,JN710900 JN710884,JN710882 JN710849,JN710875 JN710888,JN710902 JN710886,JN710911 JN710838,JN710857 AF306549,JN710899 JN710898,JN710897 JN710921,JN710920 JN710856,JN710912 JN710845,JN710917 JN710848,JN710847 JN710901,JN710892 JN710909,JN710876 JN710862,JN710893 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Infectious salmon anemia virus | NC_006503 | vertebrates | 23 | Orthomyxoviridae,Isavirus,Infectious salmon anemia virus | seg. 2 | JN710852,JN710860,JN710868,JN710863,JN710877,JN710855,DQ676937,DQ785200,DQ785198,DQ785195,DQ785191,DQ785199,DQ785194,DQ520596,DQ785190,HM172537,AJ242808,EU118816,DQ785189,DQ520595, DQ785197,D785192,AF404346, AJQ02475,AY744389, DQ785202, DQ785196,DQ785193,DQ785201 |
| Infectious salmon anemia virus | NC_006505 | vertebrates | 32 | Orthomyxoviridae,Isavirus,Infectious salmon anemia virus | seg. 1 | DQ785181,AY860813,AY168787,DQ785188,AY860812,AY954528,AY373381,DQ785183,DQ785176,DQ785186,AY373379,AY373380,DQ785175,AY860811,DQ785185,D785182,AY860808, AY373382,DQ785180,DQ785187,AY860809,AY860810,AJ514403,DQ785179,AY744388,EU118815,DQ785178,AY954527,HM172536,DQ785184,DQ785177,AY954526 |
| Infectious spleen and kidney necrosis virus | NC_003494 | vertebrates | 1 | Indoviridae,Megalocytivirus,Infectious spleen and kidney necrosis virus | — | AF371960 |
| Jaagsiekte sheep retrovirus F357971,M80216 | NC_001494 | vertebrates | 6 | Retroviridae,Betaretrovirus,Jaagsiekte sheep retrovirus | — | AF105220,DQ838494,A27950,C0964469,A |
| Japanese eel endothelial cells-infecting virus | NC_015123 | vertebrates | 1 | Japanese eel endothelial cells-infecting virus | — | AB543063 |
| Jembrana disease virus | NC_001413 | vertebrates | 1 | Retroviridae,Lentivirus,Bovine immunodeficiency virus | — | U21603 |
| Koala retrovirus | NC_021704 | vertebrates | 1 | Retroviridae,Gammaretrovirus,Koala retrovirus | — | KC779547 |
| Kobuvirus pig/JY-2010a/CHN | NC_011829,NC_016769 | vertebrates | 1 | Picornaviridae,Kobuvirus,Aichivirus C | — | GU292559 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Kobuvirus sewage Kathmandu | NC_001918 | vertebrates | 1 | Picornaviridae,Kobuvirus,Aichivirus A | — | JQ898342 |
| Labidocera aestiva circovirus | NC_017843 | vertebrates | 1 | Circoviridae,Circovirus,Labidocera aestiva circovirus | — | JF912805 |
| Lactate dehydrogenase-elevating virus | NC_001639 | vertebrates | 2 | Arteriviridae,Arterivirus, Lactate dehydrogenase-elevating virus | — | U15146,L13298 |
| Lagenorhynchus acutus papillomavirus 1 | NC_011109 | vertebrates | 1 | Papillomaviridae,Upsilonpapillomavirus,Upsilonpapillomavirus 1 | — | GU117624 |
| Lambdapapillomavirus 3 | NC_013237 | vertebrates | 1 | Papillomaviridae,Lambdapapillomavirus,Lambdapapillomavirus 3 | — | FJ492744 |
| Large yellow croaker iridovirus | NC_003494 | vertebrates | 1 | Iridoviridae,Megalocytivirus,Infectious spleen and kidney necrosis virus | — | AY779031 |
| Lelystad virus | NC_001961 | vertebrates | 1 | Arteriviridae,Arterivirus,Porcine reproductive and respiratory syndrome virus | — | M96262 |
| Ljungan virus | NC_003976 | vertebrates | 3 | Picornaviridae,Parechovirus,Ljungan virus | — | AF538689,EF202833, AF327920 |
| Ljungan virus strain 145SL | NC_003976 | vertebrates | 2 | Picornaviridae,Parechovirus,Ljungan virus | — | AF327922,FJ384560 |
| Ljungan virus strain 174F | NC_003976 | vertebrates | 1 | Picornaviridae,Parechovirus,Ljungan virus | — | AF327921 |
| LuIII virus | NC_004713 | vertebrates | 1 | Parvoviridae,Parvovirus,LuIII virus | — | M81888 |
| Lumpy skin disease virus | NC_003027 | vertebrates | 1 | Poxviridae,Capripoxvirus,Lumpy skin disease virus | — | AF409138 |
| Lumpy skin disease virus | NC_003027 | vertebrates | 1 | Poxviridae,Capripoxvirus,Lumpy skin disease NI-2490 virus | — | AF325528 |
| Lumpy skin disease virus | NC_003027 | vertebrates | 1 | Poxviridae,Capripoxvirus,Lumpy skin disease NW-LW virus | — | AF409137 |
| Lymphocystis disease virus-isolate China | NC_005902 | vertebrates | 1 | Iridoviridae,Lymphocystivirus,Lymphocystis disease virus-isolate China | — | AY380826 |
| Lymphocystis disease virus 1 | NC_001824 | vertebrates | 1 | Iridoviridae,Lymphocystivirus,Lymphocystis disease virus 1 | — | L63545 |
| Lynx rufus papillomavirus type 1 | NC_004765 | vertebrates | 1 | Papillomaviridae,Lambdapapillomavirus,Lambdapapillomavirus 1 | — | AY904722 |
| MW polyomavirus | NC_018102 | vertebrates | 11 | Polyomaviridae,Polyomavirus,MW polyomavirus | — | JQ898292,KC549591,KC549588,JQ898291,KC549590,KC549587,KC549589,KC549593,KC549594,KC549592,KC549586 |
| Macaca fascicularis papillomavirus type 10 | NC_001678 | vertebrates | 1 | Papillomaviridae,Alphapapillomavirus,Alphapapillomavirus 12 | — | EU490515 |
| Macaca fascicularis papillomavirus type 11 | NC_001678 | vertebrates | 1 | Papillomaviridae,Alphapapillomavirus,Alphapapillomavirus 12 | — | GQ227670 |
| Macaca fascicularis papillomavirus type 3 | NC_001678 | vertebrates | 1 | Papillomaviridae,Alphapapillomavirus,Alphapapillomavirus 12 | — | EF558839 |
| Macaca fascicularis papillomavirus type 3b | NC_001678 | vertebrates | 1 | Papillomaviridae,Alphapapillomavirus,Alphapapillomavirus 12 | — | EF591299 |
| Macaca fascicularis papillomavirus type 4 | NC_001678 | vertebrates | 1 | Papillomaviridae,Alphapapillomavirus,Alphapapillomavirus 12 | — | EF558841 |

TABLE 10-continued

VivoCap-1.0 Taxonomy

| Taxonomy | Rep.Acc.ID | Host | # GN's | Lineage | Seg. Count | GN.Acc.IDs |
|---|---|---|---|---|---|---|
| Macaca fascicularis papillomavirus types | NC_001678 | vertebrates | 1 | Papillomaviridae,Alphapapillomavirus,Alphapapillomavirus 12 | — | EF558843 |
| Macaca fascicularis papillomavirus type 6 | NC_001678 | vertebrates | 1 | Papillomaviridae,Alphapapillomavirus,Alphapapillomavirus 12 | — | EF558840 |
| Macaca fascicularis papillomavirus type 7 | NC_001678 | vertebrates | 1 | Papillomaviridae,Alphapapillomavirus,Alphapapillomavirus 12 | — | EF558838 |
| Macaca fascicularis papillomavirus type 8 | NC_001678 | vertebrates | 1 | Papillomaviridae,Alphapapillomavirus,Alphapapillomavirus 12 | — | EF558842 |
| Macaca fascicularis papillomavirus type 9 | NC_001678 | vertebrates | 1 | Papillomaviridae,Alphapapillomavirus,Alphapapillomavirus 12 | — | EU490516 |
| Macaca fascicularis polyomavirus 1 | NC_019851 | vertebrates | 1 | Polyomaviridae,Polyomavirus,Macaca fascicularis polyomavirus 1 | — | JX159986 |
| Macaca fuscata rhadinovirus | NC_003401 | vertebrates | 3 | Herpesviridae,Rhadinovirus,Macacine herpesvirus 5 | — | JN885137,AY528864, JN885136 |
| Macacine herpesvirus 1 | NC_004812 | vertebrates | 1 | Herpesviridae,Simplexvirus,Macacine herpesvirus 1 | — | AF533768 |
| Macacine herpesvirus 3 | NC_006150 | vertebrates | 3 | Herpesviridae,Cytomegalovirus,Macacine herpesvirus 3 | — | DQ120516,JQ795930 ,AY186194 |
| Macacine herpesvirus 4 | NC_006146 | vertebrates | 1 | Herpesviridae,Lymphocryptovirus,Macacine herpesvirus 4 | — | AY037858 |
| Macacine herpesvirus 5 | NC_003401 | vertebrates | 1 | Herpesviridae,Rhadinovirus,Macacine herpesvirus 5 | — | AF083501 |
| Macaque simian foamy virus | NC_010819 | vertebrates | 2 | Retroviridae,Spumavirus,Macaque simian foamy virus | — | X54482,JN801175 |
| Magpie-robin coronavirus HKU18 | NC_016993 | vertebrates | 1 | Coronaviridae,Deltacoronavirus,Magpie-robin coronavirus HKU18 | — | JQ065046 |
| Mamastrovirus 10 | NC_004579 | vertebrates | 1 | Astroviridae,Mamastrovirus,Mamastrovirus 10 | — | AY179509 |
| Mamastrovirus 13 | NC_002469 | vertebrates | 1 | Astroviridae,Mamastrovirus,Mamastrovirus 13 | — | Y15937 |
| Mammalian Orthoreovirus strain T3/Bat/Germany/342/08 | NC_004274 | vertebrates | 1 | Reoviridae,Orthoreovirus,Mammalian orthoreovirus | seg. L3 | JQ412757 |
| Mammalian Orthoreovirus strain T3/Bat/Germany/342/08 | NC_004275 | vertebrates | 1 | Reoviridae,Orthoreovirus,Mammalian orthoreovirus | seg. L2 | JQ412756 |
| Mammalian Orthoreovirus strain T3/Bat/Germany/342/08 | NC_004276 | vertebrates | 1 | Reoviridae,Orthoreovirus,Mammalian orthoreovirus | seg. S4 | JQ412764 |
| Mammalian Orthoreovirus strain T3/Bat/Germany/342/08 | NC_004277 | vertebrates | 1 | Reoviridae,Orthoreovirus,Mammalian orthoreovirus | seg. Si | JQ412761 |
| Mammalian Orthoreovirus strain T3/Bat/Germany/342/08 | NC_004278 | vertebrates | 1 | Reoviridae,Orthoreovirus,Mammalian orthoreovirus | seg. M2 | JQ412759 |
| Mammalian Orthoreovirus strain T3/Bat/Germany/342/08 | NC_004279 | vertebrates | 1 | Reoviridae,Orthoreovirus,Mammalian orthoreovirus | seg. S2 | JQ412762 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Mammalian Orthoreovirus T3/Bat/Germany/342/08 strain | NC_004280 | vertebrates | Reoviridae,Orthoreovirus,Mammalian orthoreovirus | 1 | seg. M1 | JQ412758 |
| Mammalian Orthoreovirus T3/Bat/Germany/342/08 strain | NC_004281 | vertebrates | Reoviridae,Orthoreovirus,Mammalian orthoreovirus | 1 | seg. M3 | JQ412760 |
| Mammalian Orthoreovirus T3/Bat/Germany/342/08 strain | NC_004282 | vertebrates | Reoviridae,Orthoreovirus,Mammalian orthoreovirus | 1 | seg. L1 | JQ412755 |
| Mammalian Orthoreovirus T3/Bat/Germany/342/08 strain | NC_004283 | vertebrates | Reoviridae,Orthoreovirus,Mammalian orthoreovirus | 1 | seg. S3 | JQ412763 |
| Mammalian Orthoreovirus T3/Bat/Germany/342/08 strain | NC_013228 | vertebrates | Reoviridae,Orthoreovirus,Mammalian orthoreovirus | 1 | seg. M2 | JQ412759 |
| Mammalian Orthoreovirus T3/Bat/Germany/342/08 strain | NC_013230 | vertebrates | Reoviridae,Orthoreovirus,Mammalian orthoreovirus | 1 | seg. M3 | JQ412760 |
| Mammalian Orthoreovirus T3/Bat/Germany/342/08 strain | NC_013232 | vertebrates | Reoviridae,Orthoreovirus,Mammalian orthoreovirus | 1 | seg. S2 | JQ412762 |
| Mammalian Orthoreovirus T3/Bat/Germany/342/08 strain | NC_013234 | vertebrates | Reoviridae,Orthoreovirus,Mammalian orthoreovirus | 1 | seg. S4 | JQ412764 |
| Mammalian orthoreovirus | NC_004274 | vertebrates | Reoviridae,Orthoreovirus,Mammalian orthoreovirus | 2 | seg. L3 | EF029088,JN799428 |
| Mammalian orthoreovirus | NC_004275 | vertebrates | Reoviridae,Orthoreovirus,Mammalian orthoreovirus | 3 | seg. L2 | DQ885990,HQ642277 0,JN799427 |
| Mammalian orthoreovirus | NC_004276 | vertebrates | Reoviridae,Orthoreovirus,Mammalian orthoreovirus | 2 | seg. S4 | DQ396806,JN799422 |
| Mammalian orthoreovirus | NC_004277 | vertebrates | Reoviridae,Orthoreovirus,Mammalian orthoreovirus | 3 | seg. Si | DQ911244,HQ642277 5,JN799419 |
| Mammalian orthoreovirus | NC_004278 | vertebrates | Reoviridae,Orthoreovirus,Mammalian orthoreovirus | 3 | seg. M2, | JN799424,HQ642772 DQ482462 |
| Mammalian orthoreovirus | NC_004279 | vertebrates | Reoviridae,Orthoreovirus,Mammalian orthoreovirus | 3 | seg. S2 | JN799420,DQ396805 ,HQ642776 |
| Mammalian orthoreovirus | NC_004280 | vertebrates | Reoviridae,Orthoreovirus,Mammalian orthoreovirus | 3 | seg. M1, | HQ642773,JN799423 DQ396804 |
| Mammalian orthoreovirus | NC_004281 | vertebrates | Reoviridae,Orthoreovirus,Mammalian orthoreovirus | 2 | seg. M3 | JN799425,DQ403254 |
| Mammalian orthoreovirus | NC_004282 | vertebrates | Reoviridae,Orthoreovirus,Mammalian orthoreovirus | 3 | seg. L1 | JN799426,HQ642771 ,DQ997719 |
| Mammalian orthoreovirus | NC_004283 | vertebrates | Reoviridae,Orthoreovirus,Mammalian orthoreovirus | 3 | seg. S3 | JN799421,HQ642777 ,DQ411553 |
| Mammalian orthoreovirus | NC_013228 | vertebrates | Reoviridae,Orthoreovirus,Mammalian orthoreovirus | 3 | seg. M2 | JN799424,HQ642772 ,DQ482462 |
| Mammalian orthoreovirus | NC_013230 | vertebrates | Reoviridae,Orthoreovirus,Mammalian orthoreovirus | 2 | seg. M3 | JN799425,DQ403254 |

TABLE 10-continued

VrioCap-1.0 Taxonomy

| Taxonomy | Rep.Acc.ID | Host | # GN's | Lineage | Seg. Count | GN.Acc.IDs |
|---|---|---|---|---|---|---|
| Mammalian orthoreovirus 1 | NC_013232 | vertebrates | 3 | Reoviridae,Orthoreovirus,Mammalian orthoreovirus | seg. S2 | JN799420,DQ396805,HQ642776 |
| Mammalian orthoreovirus 1 | NC_013234 | vertebrates | 2 | Reoviridae,Orthoreovirus,Mammalian orthoreovirus | seg. S4 | DQ396806,JN799422 |
| Mammalian orthoreovirus 1 | NC_004274 | vertebrates | 1 | Reoviridae,Orthoreovirus,Mammalian orthoreovirus | seg. L3 | AF129820 |
| Mammalian orthoreovirus 1 | NC_004275 | vertebrates | 1 | Reoviridae,Orthoreovirus,Mammalian orthoreovirus | seg. L2 | AF378004 |
| Mammalian orthoreovirus 1 | NC_004276 | vertebrates | 2 | Reoviridae,Orthoreovirus,Mammalian orthoreovirus | seg. S4 | X61586,M13139 |
| Mammalian orthoreovirus 1 | NC_004277 | vertebrates | 8 | Reoviridae,Orthoreovirus,Mammalian orthoreovirus | seg. S1 | AY862136,EF494445,M10260,AY862135,M35963,M14779,AY862133,AY862134 |
| Mammalian orthoreovirus 1 | NC_004278 | vertebrates | 2 | Reoviridae,Orthoreovirus,Mammalian orthoreovirus | seg. M2 | M19345,M19407 |
| Mammalian orthoreovirus 1 | NC_004279 | vertebrates | 2 | Reoviridae,Orthoreovirus,Mammalian orthoreovirus | seg. S2 | M17598,L19774 |
| Mammalian orthoreovirus 1 | NC_004280 | vertebrates | 4 | Reoviridae,Orthoreovirus,Mammalian orthoreovirus | seg. M1 | AY428872,X59945,AY428870,AY428871 |
| Mammalian orthoreovirus 1 | NC_004281 | vertebrates | 1 | Reoviridae,Orthoreovirus,Mammalian orthoreovirus | seg. M3 | AF174382 |
| Mammalian orthoreovirus 1 | NC_004283 | vertebrates | 2 | Reoviridae,Orthoreovirus,Mammalian orthoreovirus | seg. S3 | M14325,M18389 |
| Mammalian orthoreovirus 1 | NC_013228 | vertebrates | 2 | Reoviridae,Orthoreovirus,Mammalian orthoreovirus | seg. M2 | M19345,M19407 |
| Mammalian orthoreovirus 1 | NC_013230 | vertebrates | 1 | Reoviridae,Orthoreovirus,Mammalian orthoreovirus | seg. M3 | AF174382 |
| Mammalian orthoreovirus 1 | NC_013232 | vertebrates | 2 | Reoviridae,Orthoreovirus,Mammalian orthoreovirus | seg. S2 | M17598,L19774 |
| Mammalian orthoreovirus 1 | NC_013234 | vertebrates | 2 | Reoviridae,Orthoreovirus,Mammalian orthoreovirus | seg. S4 | X61586,M13139 |
| Mammalian orthoreovirus 2 | NC_004274 | vertebrates | 3 | Reoviridae,Orthoreovirus,Mammalian orthoreovirus | seg. L3 | AF129821,GU196308,DQ664186 |
| Mammalian orthoreovirus 2 | NC_004275 | vertebrates | 3 | Reoviridae,Orthoreovirus,Mammalian orthoreovirus | seg. L2 | DQ664185,GU196307,AF378006 |
| Mammalian orthoreovirus 2 | NC_004276 | vertebrates | 2 | Reoviridae,Orthoreovirus,Mammalian orthoreovirus | seg. S4 | DQ318037,GU196313 |
| Mammalian orthoreovirus 2 | NC_004277 | vertebrates | 10 | Reoviridae,Orthoreovirus,Mammalian orthoreovirus | seg. S1 | EU049605,AY862137,EU049607,EU049604,EU049603,M35964,GU196315,AY862138,EU049606,DQ312301 |
| Mammalian orthoreovirus 2 | NC_004278 | vertebrates | 2 | Reoviridae,Orthoreovirus,Mammalian orthoreovirus | seg. M2 | DQ664188,GU196310 |
| Mammalian orthoreovirus 2 | NC_004279 | vertebrates | 2 | Reoviridae,Orthoreovirus,Mammalian orthoreovirus | seg. S2 | GU196311,DQ664190 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Mammalian orthoreovirus 2 | NC_004280 | vertebrates | 4 | Reoviridae,Orthoreovirus,Mammalian orthoreovirus | seg. M1 | AY428873,DQ664187,GU196309,AY428874 |
| Mammalian orthoreovirus 2 | NC_004281 | vertebrates | 3 | Reoviridae,Orthoreovirus,Mammalian orthoreovirus | seg. M3 | GU196314,DQ66418 9,AF174383 |
| Mammalian orthoreovirus 2 | NC_004282 | vertebrates | 2 | Reoviridae,Orthoreovirus,Mammalian orthoreovirus | seg. L1 | DQ664184,GU196306 |
| Mammalian orthoreovirus 2 | NC_004283 | vertebrates | 3 | Reoviridae,Orthoreovirus,Mammalian orthoreovirus | seg. S3 | GU196312,M18390,D0664191 |
| Mammalian orthoreovirus 2 | NC_013228 | vertebrates | 2 | Reoviridae,Orthoreovirus,Mammalian orthoreovirus | seg. M2 | DQ664188,GU196310 |
| Mammalian orthoreovirus 2 | NC_013230 | vertebrates | 3 | Reoviridae,Orthoreovirus,Mammalian orthoreovirus | seg. M3 | GU196314,DQ66418 9,AF174383 |
| Mammalian orthoreovirus 2 | NC_013232 | vertebrates | 2 | Reoviridae,Orthoreovirus,Mammalian orthoreovirus | seg. S2 | GU196311,DQ664190 |
| Mammalian orthoreovirus 2 | NC_013234 | vertebrates | 2 | Reoviridae,Orthoreovirus,Mammalian orthoreovirus | seg. S4 | DQ318037,GU1963133 |
| Mammalian orthoreovirus 2 | NC_004276 | vertebrates | 1 | Reoviridae,Orthoreovirus,Mammalian orthoreovirus D5/Jones orthoreovirus | seg. S4 | X60066 |
| Mammalian orthoreovirus 2 | NC_013234 | vertebrates | 1 | Reoviridae,Orthoreovirus,Mammalian orthoreovirus D5/Jones orthoreovirus | seg. S4 | X60066 |
| Mammalian orthoreovirus 3 | NC_004274 | vertebrates | 8 | Reoviridae,Orthoreovirus,Mammalian orthoreovirus | seg. L3 | GU991661,JX486059,JQ599141,EF494437,M23747,AF129822,GU991671,GU589579 |
| Mammalian orthoreovirus 3 | NC_004275 | vertebrates | 11 | Reoviridae,Orthoreovirus,Mammalian orthoreovirus | seg. L2 | JQ599139,AF378008,GU991660,AF378007,JX486058,EF494436,GU991670,AF37801 0,AF378009,GU5895 78,JQ3488 |
| Mammalian orthoreovirus 3 | NC_004276 | vertebrates | 12 | Reoviridae,Orthoreovirus,Mammalian orthoreovirus | seg. S4 | GU991678,K02739,D 0004471,DQ004472, DQ004473,GU58958 6,JX486066,DQ0044 70,DQ004474,EF494 444,DQ004475,GU99 1668 |
| Mammalian orthoreovirus 3 | NC_004277 | vertebrates | 24 | Reoviridae,Orthoreovirus,Mammalian orthoreovirus | seg. S1 | JQ979280,JQ979277, GU991675,JQ599138, JQ979273,GU991166 5,AY302467,JQ97927 2,JQ979275,JQ97928 4,EF494441,JQ97928 2,GU589583,JQ9792 74,JX486063,JQ9792 71,JQ979281,XQ1161 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Mammalian orthoreovirus 3 | NC_004278 | vertebrates | Reoviridae,Orthoreovirus,Mammalian orthoreovirus | 8 | seg. M2 | ,JQ979283,JQ979278,JQ979285,M10262,J0979279,JQ979276,GU991663,GU58958,1,M20161,EF494439,GU991673,JX486061,M19408,U24260 |
| Mammalian orthoreovirus 3 | NC_004279 | vertebrates | Reoviridae,Orthoreovirus,Mammalian orthoreovirus | 8 | seg. S2 | GU589584,JX486064,GU991666,L19776,GU991676,EF494442,J02327,M25780 |
| Mammalian orthoreovirus 3 | NC_004280 | vertebrates | Reoviridae,Orthoreovirus,Mammalian orthoreovirus | 13 | seg. M1 | GU991672,GU58958 0,GU991662,AY42888 78,M27261,AY42887 5,AY551083,EF49443 8,AY428876,AF46168 3,AY428877,JX48606 0,AF461684 |
| Mammalian orthoreovirus 3 | NC_004281 | vertebrates | Reoviridae,Orthoreovirus,Mammalian orthoreovirus | 7 | seg. M3 | GU991664,AF174384,JX486062,EF494440,M27262,GU589582,GU991674 |
| Mammalian orthoreovirus 3 | NC_004282 | vertebrates | Reoviridae,Orthoreovirus,Mammalian orthoreovirus | 7 | seg. L1 | M31058,GU991669,J0599140.GU589577,EF494435,JX486057,GU991659 |
| Mammalian orthoreovirus 3 | NC_004283 | vertebrates | Reoviridae,Orthoreovirus,Mammalian orthoreovirus | 6 | seg. S3 | JX486065,XQ1627,GU991667,GU991677,GU589585,EF494443 |
| Mammalian orthoreovirus 3 | NC_013225 | vertebrates | Reoviridae,Orthoreovirus,Mammalian orthoreovirus | 1 | seg. L1 | GQ468266 |
| Mammalian orthoreovirus 3 | NC_013226 | vertebrates | Reoviridae,Orthoreovirus,Mammalian orthoreovirus | 1 | seg. L2 | GQ468267 |
| Mammalian orthoreovirus 3 | NC_013227 | vertebrates | Reoviridae,Orthoreovirus,Mammalian orthoreovirus | 1 | seg. M1 | GQ468268 |
| Mammalian orthoreovirus 3 | NC_013228 | vertebrates | Reoviridae,Orthoreovirus,Mammalian orthoreovirus | 8 | seg. M2 | GU991663,GU58958 1,M20161,EF494439,GU991673,GQ446826 9,JX486061,U24260 |
| Mammalian orthoreovirus 3 | NC_013229 | vertebrates | Reoviridae,Orthoreovirus,Mammalian orthoreovirus | 1 | seg. L3 | GQ468270 |
| Mammalian orthoreovirus 3 | NC_013230 | vertebrates | Reoviridae,Orthoreovirus,Mammalian orthoreovirus | 7 | seg. M3 | GU991664,AF174384,JX486062,EF494440,GU589582,GU99167 4,GQ468271 |
| Mammalian orthoreovirus 3 | NC_013231 | vertebrates | Reoviridae,Orthoreovirus,Mammalian orthoreovirus | 1 | seg. Si | GQ468272 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Mammalian orthoreovirus 3 | NC_013232 | vertebrates | Reoviridae,Orthoreovirus,Mammalian orthoreovirus | 8 | seg. S2 | GU589584,JX486064,GU991666,L19776,GU991676,EF494442,GQ468273,JQ2327 |
| Mammalian orthoreovirus 3 | NC_013233 | vertebrates | Reoviridae,Orthoreovirus,Mammalian orthoreovirus | 1 | seg. S3 | GQ468274 |
| Mammalian orthoreovirus 3 | NC_013234 | vertebrates | Reoviridae,Orthoreovirus,Mammalian orthoreovirus | 12 | seg. S4 | GU991678,DQ004471,DQ004472,DQ004473,GU589586,JX486066,GQ468275,DQ004470,DQ004474,EF494444,DQ004475,GU991668 |
| Mammalian orthoreovirus 3 | NC_004274 | vertebrates | Reoviridae,Orthoreovirus,Mammalian orthoreovirus Dearing orthoreovirus | 1 | seg. L3 | HM159615 |
| Mammalian orthoreovirus 3 | NC_004275 | vertebrates | Reoviridae,Orthoreovirus,Mammalian orthoreovirus Dearing orthoreovirus | 1 | seg. L2 | HM159614 |
| Mammalian orthoreovirus 3 | NC_004276 | vertebrates | Reoviridae,Orthoreovirus,Mammalian orthoreovirus Dearing orthoreovirus | 4 | seg. S4 | AF332135,HM159622,AF332136,AF332137 |
| Mammalian orthoreovirus 3 | NC_004277 | vertebrates | Reoviridae,Orthoreovirus,Mammalian orthoreovirus Dearing orthoreovirus | 1 | seg. S1 | HM159619 |
| Mammalian orthoreovirus 3 | NC_004278 | vertebrates | Reoviridae,Orthoreovirus,Mammalian orthoreovirus Dearing orthoreovirus | 1 | seg. M2 | HM159617 |
| Mammalian orthoreovirus 3 | NC_004279 | vertebrates | Reoviridae,Orthoreovirus,Mammalian orthoreovirus Dearing orthoreovirus | 1 | seg. S2 | HM159620 |
| Mammalian orthoreovirus 3 | NC_004280 | vertebrates | Reoviridae,Orthoreovirus,Mammalian orthoreovirus Dearing orthoreovirus | 1 | seg. M1 | HM159616 |
| Mammalian orthoreovirus 3 | NC_004281 | vertebrates | Reoviridae,Orthoreovirus,Mammalian orthoreovirus Dearing orthoreovirus | 1 | seg. M3 | HM159618 |
| Mammalian orthoreovirus 3 | NC_004282 | vertebrates | Reoviridae,Orthoreovirus,Mammalian orthoreovirus Dearing orthoreovirus | 1 | seg. L1 | HM159613 |
| Mammalian orthoreovirus 3 | NC_004283 | vertebrates | Reoviridae,Orthoreovirus,Mammalian orthoreovirus Dearing orthoreovirus | 1 | seg. S3 | HM159621 |
| Mammalian orthoreovirus 3 | NC_013228 | vertebrates | Reoviridae,Orthoreovirus,Mammalian orthoreovirus Dearing orthoreovirus | 1 | seg. M2 | HM159617 |
| Mammalian orthoreovirus 3 | NC_013230 | vertebrates | Reoviridae,Orthoreovirus,Mammalian orthoreovirus Dearing orthoreovirus | 1 | seg. M3 | HM159618 |
| Mammalian orthoreovirus 3 | NC_013232 | vertebrates | Reoviridae,Orthoreovirus,Mammalian orthoreovirus Dearing orthoreovirus | 1 | seg. S2 | HM159620 |
| Mammalian orthoreovirus 3 | NC_013234 | vertebrates | Reoviridae,Orthoreovirus,Mammalian orthoreovirus Dearing orthoreovirus | 4 | seg. S4 | AF332135,HM159622,AF332136,AF332137 |
| Mammalian orthoreovirus 4 Ndelle | NC_004276 | vertebrates | Reoviridae,Orthoreovirus,Mammalian orthoreovirus | 1 | seg. S4 | AF368037 |
| Mammalian orthoreovirus 4 Ndelle | NC_004277 | vertebrates | Reoviridae,Orthoreovirus,Mammalian orthoreovirus | 1 | seg. S1 | AF368035 |
| Mammalian orthoreovirus 4 Ndelle | NC_004278 | vertebrates | Reoviridae,Orthoreovirus,Mammalian orthoreovirus | 1 | seg. M2 | AF368034 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Mammalian orthoreovirus 4 Ndelle | NC_004279 | vertebrates | 1 | Reoviridae,Orthoreovirus,Mammalian orthoreovirus | seg. S2 | AF368036 |
| Mammalian orthoreovirus 4 Ndelle | NC_004282 | vertebrates | 1 | Reoviridae,Orthoreovirus,Mammalian orthoreovirus | seg. L1 | AF368033 |
| Mammalian orthoreovirus 4 Ndelle | NC_013228 | vertebrates | 1 | Reoviridae,Orthoreovirus,Mammalian orthoreovirus | seg. M2 | AF368034 |
| Mammalian orthoreovirus 4 Ndelle | NC_013232 | vertebrates | 1 | Reoviridae,Orthoreovirus,Mammalian orthoreovirus | seg. S2 | AF368036 |
| Mammalian orthoreovirus 4 Ndelle | NC_013234 | vertebrates | 1 | Reoviridae,Orthoreovirus,Mammalian orthoreovirus | seg. S4 | AF368037 |
| Marine birnavirus | NC_008019 | vertebrates | 5 | Birnaviridae,Aquabirnavirus,Marine birnavirus | seg. A | AY283785,AY064396,AY283781,AY283782,AY283784 |
| Marine birnavirus | NC_008026 | vertebrates | 3 | Birnaviridae,Aquabirnavirus,Marine birnavirus | seg. B | AY123970,AY129665,AY129666 |
| Marine birnavirus-H1 | NC_008019 | vertebrates | 1 | Birnaviridae,Aquabirnavirus,Marine birnavirus | seg. A | AY283783 |
| Mason-Pfizer monkey virus | NC_001550 | vertebrates | 2 | Retroviridae,Betaretrovirus,Mason-Pfizer monkey virus | — | AF033815,M12349 |
| Mastomys coucha papillomavirus 2 | NC_008519 | vertebrates | 1 | Papillomaviridae,Pipapillomavirus,Pipapillomavirus 1 | — | DQ664501 |
| Mastomys natalensis papillomavirus | NC_001605 | vertebrates | 1 | Papillomaviridae,Iotapapillomavirus,Iotapapillomavirus 1 | — | U01834 |
| Melaka orthoreovirus | NC_020439 | vertebrates | 1 | Reoviridae,Orthoreovirus,Melaka orthoreovirus | seg. L1 | F342660 |
| Melaka orthoreovirus | NC_020440 | vertebrates | 1 | Reoviridae,Orthoreovirus,Melaka orthoreovirus | seg. L3 | F342662 |
| Melaka orthoreovirus | NC_020441 | vertebrates | 1 | Reoviridae,Orthoreovirus,Melaka orthoreovirus | seg. M1 | F342663 |
| Melaka orthoreovirus | NC_020442 | vertebrates | 1 | Reoviridae,Orthoreovirus,Melaka orthoreovirus | seg. M2 | F342664 |
| Melaka orthoreovirus | NC_020443 | vertebrates | 1 | Reoviridae,Orthoreovirus,Melaka orthoreovirus | seg. M3 | F342665 |
| Melaka orthoreovirus | NC_020444 | vertebrates | 1 | Reoviridae,Orthoreovirus,Melaka orthoreovirus | seg. S2 | EF026044 |
| Melaka orthoreovirus | NC_020445 | vertebrates | 1 | Reoviridae,Orthoreovirus,Melaka orthoreovirus | seg. S3 | EF026045 |
| Melaka orthoreovirus | NC_020446 | vertebrates | 1 | Reoviridae,Orthoreovirus,Melaka orthoreovirus | seg. S4 | EF026046 |
| Melaka orthoreovirus | NC_020447 | vertebrates | 1 | Reoviridae,Orthoreovirus,Melaka orthoreovirus | seg. L2 | F342661 |
| Melaka orthoreovirus | NC_020448 | vertebrates | 1 | Reoviridae,Orthoreovirus,Melaka orthoreovirus | seg. S1 | EF026043 |
| Meleagrid herpesvirus 1 | NC_002641 | vertebrates | 2 | Herpesviridae,Mardivirus,Meleagrid herpesvirus 1 | — | AF282130,AF291866 |
| Mengo virus | NC_001479 | vertebrates | 2 | Picornaviridae,Cardiovirus,Encephalomyocarditis virus | — | L22089, DQ294633 |
| Mesocricetus auratus papillomavirus 1 | NC_022647 | vertebrates | 1 | Papillomaviridae,Mesocricetus auratus papillomavirus 1 | — | HG530538 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Middle East respiratory syndrome coronavirus | NC_019843 | vertebrates | 30 | Coronaviridae,Betacoronavirus,Middle East respiratory syndrome coronavirus | — | KF600645,KF192507, KJ156944,KJ156952, KJ156869,KF600630, KF600652,KF600634, KJ156934,KF600620, KF600651,KF600644, KF600612,KF600627, KF600628,KF961221, KF961222,KF600613, KF186565,KF745068, KF186564,KF186566, KF600647,KF186567, KJ156910,KJ156881, KF600632,KJ156881, KJ156866,KJ156949 |
| Miniopterus bat coronavirus HKU8 | NC_010438 | vertebrates | 1 | Coronaviridae,Alphacoronavirus,Miniopterus bat coronavirus HKU8 | — | EU420139 |
| Miniopterus polyomavirus | NC_020069 | vertebrates | 1 | Polyomaviridae,Polyomavirus,Miniopterus polyomavirus | — | JX520661 |
| Mink astrovirus | NC_004579 | vertebrates | 1 | Astroviridae,Mamastrovirus,Mamastrovirus 10 | — | GU985458 |
| Mink calicivirus | NC_019712 | vertebrates | 1 | Caliciviridae,Vesivirus,Mink calicivirus | — | JX847605 |
| Minute virus of mice | NC_001510 | vertebrates | 3 | Parvoviridae,Parvovirus,Minute virus of mice | — | M12032,JQ2275,DQ196317 |
| Molluscum contagiosum virus subtype 1 | NC_001731 | vertebrates | 1 | Poxviridae,Molluscipoxvirus,Molluscum contagiosum virus | — | U60315 |
| Moloney murine leukemia virus | NC_001702,NC_0013 9,NC_0013 62,NC_001 501 | vertebrates | 2 | Retroviridae,Gammaretrovirus,Murine leukemia virus | — | AF462057,CS272315 |
| Moloney murine sarcoma virus | NC_001502 | vertebrates | 4 | Retroviridae,Gammaretrovirus,Moloney murine sarcoma virus | — | JQ2266,V01185,V01184,AF033813 |
| Monkey B-lymphotropic papovavirus | NC_004763 | vertebrates | 1 | Polyomaviridae,Polyomavirus,African green monkey polyomavirus | — | M30540 |
| Monkeypox virus | NC_003310 | vertebrates | 36 | Poxviridae,Orthopoxvirus,Monkeypox virus | — | JX878427,AY741551, JX878415,JX878410, JX878416,JX878422, DQ011156,JX878419, HQ857562,JX878407, JX878414,DQ011154, JX878408,JX878428, AY753185,DQ011155, JX878409,JX878420, JX878426,JX878417, JX878429,HM172544, JX878412,JX878423, DQ011157,JX878425, DQ011153,JX878425 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Monkeypox virus Zaire-96-1-16 | NC_003310 | vertebrates | 1 | Poxviridae,Orthopoxvirus,Monkeypox virus | — | 878421,KC257459,JX878424,KC257460,AY603973,HQ857563,JX878411,JX878413,JX878418 |
| Morelia spilota papillomavirus 1 | NC_016013 | vertebrates | 1 | Papillomaviridae,Morelia spilota papillomavirus 1 | — | AF380138 |
| Mouse astrovirus M-52/USA/2008 | NC_015935 | vertebrates | 1 | Astroviridae,Mouse astrovirus M-52/USA/2008 | — | HQ262535 |
| Mouse kobuvirus M-5/USA/2010 | NC_015936 | vertebrates | 1 | Picornaviridae,Kobuvirus,Mouse kobuvirus M-5/USA/2010 | — | JF755422 |
| Mouse mammary tumor virus | NC_001503 | vertebrates | 3 | Retroviridae,Betaretrovirus,Mouse mammary tumor virus | — | JF755427 |
| Mouse parvovirus 1 | NC_001630 | vertebrates | 1 | Parvoviridae,Parvovirus,Mouse parvovirus 1 | — | AF033807,M15122,D16249 |
| Mouse parvovirus 1e | NC_001630 | vertebrates | 1 | Parvoviridae,Parvovirus,Mouse parvovirus 1 | — | U12469 |
| Mouse parvovirus 2 | NC_008186 | vertebrates | 1 | Parvoviridae,Parvovirus,Mouse parvovirus 2 | — | DQ898166 |
| Mouse parvovirus 3 | NC_008185 | vertebrates | 1 | Parvoviridae,Parvovirus,Mouse parvovirus 3 | — | DQ196319 |
| Mouse parvovirus 4a | NC_011619 | vertebrates | 1 | Parvoviridae,Parvovirus,Mouse parvovirus 4 | — | DQ196318 |
| Mouse parvovirus 4b | NC_011619 | vertebrates | 1 | Parvoviridae,Parvovirus,Mouse parvovirus 4 | — | FJ440683 |
| Mouse parvovirus 5a | NC_011618 | vertebrates | 1 | Parvoviridae,Parvovirus,Mouse parvovirus 5a | — | FJ445512 |
| Mouse polyomavirus (strain Crawford small-plaque) | NC_001515 | vertebrates | 1 | Polyomaviridae,Polyomavirus,Murine polyomavirus | — | FJ441297 |
| | | | | | | K02737 |
| Mulard duck circovirus | NC_005053,NC_007220,NC_006561 | vertebrates | 2 | Circoviridae,Circovirus,Duck circovirus | — | HQ180266,AY228555 |
| Munia coronavirus HKU13-3514 | NC_011550 | vertebrates | 1 | Coronaviridae, Deltacoronavirus, Munia coronavirus HKU13 | — | FJ376622 |
| Murid herpesvirus 1 | NC_004065 | vertebrates | 8 | Herpesviridae,Muromegalovirus,Murid herpesvirus 1 | — | GU305914,U68299,HE610452,HE610456,HE610455,HE610454,HE610451,HE610453 |
| Murid herpesvirus 2 | NC_002512 | vertebrates | 1 | Herpesviridae,Muromegalovirus,Murid herpesvirus 2 | — | AF232689 |
| Murid herpesvirus 4 | NC_001826 | vertebrates | 2 | Herpesviridae,Rhadinovirus,Murid herpesvirus 4 | — | U97553,AF105037 |
| Murid herpesvirus 8 | NC_019559 | vertebrates | 1 | Herpesviridae,Muromegalovirus,Murid herpesvirus 8 | — | JX867617 |
| Murine adenovirus 2 | NC_014899 | vertebrates | 1 | Adenoviridae,Mastadenovirus,Murine adenovirus B | — | HM049560 |
| Murine adenovirus 3 | NC_012584 | vertebrates | 1 | Adenoviridae,Mastadenovirus,Murine adenovirus C | — | EU835513 |
| Murine adenovirus A | NC_000942 | vertebrates | 1 | Adenoviridae,Mastadenovirus,Murine adenovirus A | — | M22245 |

TABLE 10-continued

VíroCap-1.0 Taxonomy

| Taxonomy | Rep.Acc.ID | Host | Lineage | # GN's | Seg. Count | GN.Acc.IDs |
|---|---|---|---|---|---|---|
| Murine astrovirus | NC_018702 | vertebrates | Astroviridae,Murine astrovirus | 2 | — | JX544744,JX544743 |
| Murine coronavirus | NC_012936 NC_001846 | vertebrates | Coronaviridae, Betacoronavirus, Murine coronavirus | 6 | — | JX169866,KF268338, KF268337,KF268339, KF268336,JX169867 |
| Murine coronavirus MHV-1 | NC_012936 ,NC_001846 | vertebrates | Coronaviridae,Betacoronavirus,Murine coronavirus | 1 | — | FJ647223 |
| Murine coronavirus MHV-3 | NC_012936 ,NC_001846 | vertebrates | Coronaviridae,Betacoronavirus,Murine coronavirus | 1 | — | FJ647224 |
| Murine coronavirus MHV-JHM,IA | NC_012936 ,NC_001846 | vertebrates | Coronaviridae,Betacoronavirus,Murine coronavirus | 1 | — | FJ647226 |
| Murine coronavirus RA59/R13 | NC_012936 ,NC_001846 | vertebrates | Coronaviridae,Betacoronavirus,Murine coronavirus | 1 | — | FJ647218 |
| Murine coronavirus RA59/SJHM | NC_012936 ,NC_001846 | vertebrates | Coronaviridae,Betacoronavirus,Murine coronavirus | 1 | — | FJ647220 |
| Murine coronavirus RJHM/A | NC_012936 ,NC_001846 | vertebrates | Coronaviridae,Betacoronavirus,Murine coronavirus | 1 | — | FJ647219 |
| Murine coronavirus SA59/RJHM | NC_012936 ,NC_001846 | vertebrates | Coronaviridae,Betacoronavirus,Murine coronavirus | 1 | — | FJ647222 |
| Murine coronavirus inf-MHV-A59 | NC_012936 ,NC_001846 | vertebrates | Coronaviridae,Betacoronavirus,Murine coronavirus | 1 | — | FJ647225 |
| Murine coronavirus repA59/RJHM | NC_012936 ,NC_001846 | vertebrates coronavirus | Coronaviridae,Betacoronavirus,Murine coronavirus | 1 | — | FJ647221 |
| Murine coronavirus repJHM/RA59 | NC_012936 ,NC_001846 | vertebrates | Coronaviridae,Betacoronavirus,Murine coronavirus | 1 | — | FJ647227 |
| Murine cytomegalovirus (strain K181) | NC_004065 | vertebrates | Herpesviridae,Muromegalovirus,Murid herpesvirus 1 | 1 | — | AM886412 |
| Murine hepatitis virus | NC_012936 ,NC_001846 | vertebrates | Coronaviridae,Betacoronavirus,Murine coronavirus | 5 | — | AY700211,AF208067, AB551247,AF208066, GU593319 |
| Murine hepatitis virus strain 2 | NC_012936 ,NC_001846 | vertebrates | Coronaviridae,Betacoronavirus,Murine coronavirus | 1 | — | AF201929 |
| Murine hepatitis virus strain A59 | NC_012936 | vertebrates | Coronaviridae,Betacoronavirus,Murine coronavirus | 2 | — | FJ884686,FJ884687 |
| Murine hepatitis virus strain ML-11 | NC_001846 NC_012936 | vertebrates | Coronaviridae,Betacoronavirus,Murine coronavirus | 1 | — | AF207902 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Murine hepatitis virus strain S/3239-17 | NC_012936,NC_001846 | vertebrates | Coronaviridae,Betacoronavirus,Murine coronavirus | 1 | — | JQ173883 |
| Murine leukemia virus | NC_001702,NC_001819,NC_001362,NC_001501 | vertebrates | Retroviridae,Gammaretrovirus,Murine leukemia virus | 12 | — | AB187566,Y13893,M87750,DQ366149,AY252102,AF019230,AB187565,AY818896,AF169256,K03363,U13766,JQ2255 |
| Murine leukemia virus N417 | NC_001702,NC_001811,NC_001362,NC_001501 | vertebrates | Retroviridae,Gammaretrovirus,Murine eukemia virus | 1 | — | HQ246218 |
| Murine norovirus | NC_008311 | vertebrates | Caliciviridae,Norovirus,Murine norovirus | 8 | — | EF531291,AB435514,AB435515,JXQ48594,DQ911368,EF531290,HQ317203,AB601769 |
| Murine norovirus 1 | NC_008311 | vertebrates | Caliciviridae,Norovirus,Murine norovirus | 13 | — | EU004660,EU004654,EF014462,EU004662,EU004661,EU004659,AY228235,EU004656,EU004657,DQ285629,EU004655,EU004658,KC782764 |
| Murine norovirus 2 | NC_008311 | vertebrates | Caliciviridae,Norovirus,Murine norovirus | 1 | — | DQ223041 |
| Murine norovirus 3 | NC_008311 | vertebrates | Caliciviridae,Norovirus,Murine norovirus | 4 | — | KC792553,DQ223042,JF446720,JQ658375 |
| Murine norovirus 4 | NC_008311 | vertebrates | Caliciviridae,Norovirus,Murine norovirus | 2 | — | DQ223043,FJ446719 |
| Murine norovirus GV/C R1/2005/USA | NC_008311 | vertebrates | Caliciviridae,Norovirus,Murine norovirus | 1 | — | EU004672 |
| Murine norovirus GV/CR10/2005/USA | NC_008311 | vertebrates | Caliciviridae,Norovirus,Murine norovirus | 1 | — | EU004678 |
| Murine norovirus GV/CR11/2005/USA | NC_008311 | vertebrates | Caliciviridae,Norovirus,Murine norovirus | 1 | — | EU004679 |
| Murine norovirus GV/CR13/2005/USA | NC_008311 | vertebrates | Caliciviridae,Norovirus,Murine norovirus | 1 | — | EU004680 |
| Murine norovirus GV/CR15/2005/USA | NC_008311 | vertebrates | Caliciviridae,Norovirus,Murine norovirus | 1 | — | EU004681 |
| Murine norovirus GV/CR17/2005/USA | NC_008311 | vertebrates | Caliciviridae,Norovirus,Murine norovirus | 1 | — | EU004682 |
| Murine norovirus GV/CR18/2005/DEU | NC_008311 | vertebrates | Caliciviridae,Norovirus,Murine norovirus | 1 | — | EU004683 |
| Murine norovirus GV/CR3/2005/USA | NC_008311 | vertebrates | Caliciviridae,Norovirus,Murine norovirus | 1 | — | EU004673 |
| Murine norovirus GV/CR4/2005/USA | NC_008311 | vertebrates | Caliciviridae,Norovirus,Murine norovirus | 1 | — | EU004674 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Murine norovirus GV/CRS/2005/USA | NC_008311 | vertebrates | Caliciviridae,Norovirus,Murine norovirus | 1 | — | EU004675 |
| Murine norovirus GV/CR6/2005/USA | NC_008311 | vertebrates | Caliciviridae,Norovirus,Murine norovirus | 2 | — | EU004676,JQ237823 |
| Murine norovirus GV/CR7/2005/USA | NC_008311 | vertebrates | Caliciviridae,Norovirus,Murine norovirus | 1 | — | EU004677 |
| Murine norovirus GV/NIH-2409/2005/USA | NC_008311 | vertebrates | Caliciviridae,Norovirus,Murine norovirus | 1 | — | JF320644 |
| Murine norovirus GV/NIH-2410/2005/USA | NC_008311 | vertebrates | Caliciviridae,Norovirus,Murine norovirus | 1 | — | JF320645 |
| Murine norovirus GV/NIH-2411/2005/USA | NC_008311 | vertebrates | Caliciviridae,Norovirus,Murine norovirus | 1 | — | JF320646 |
| Murine norovirus GV/NIH-2747/2005/USA | NC_008311 | vertebrates | Caliciviridae,Norovirus,Murine norovirus | 1 | — | JF320647 |
| Murine norovirus GV/NIH-2750/2005/USA | NC_008311 | vertebrates | Caliciviridae,Norovirus,Murine norovirus | 1 | — | JF320648 |
| Murine norovirus GV/NIH-4421/2005/USA | NC_008311 | vertebrates | Caliciviridae,Norovirus,Murine norovirus | 1 | — | JF320649 |
| Murine norovirus GV/NIH-4428/2005/USA | NC_008311 | vertebrates | Caliciviridae,Norovirus,Murine norovirus | 1 | — | JF320650 |
| Murine norovirus GV/NIH-4431/2005/USA | NC_008311 | vertebrates | Caliciviridae,Norovirus,Murine norovirus | 1 | — | JF320651 |
| Murine norovirus GV/NIH-A114/2006/USA | NC_008311 | vertebrates | Caliciviridae,Norovirus,Murine norovirus | 1 | — | JF320652 |
| Murine norovirus GV/NIH-D220/2007/USA | NC_008311 | vertebrates | Caliciviridae,Norovirus,Murine norovirus | 1 | — | JF320653 |
| Murine norovirus GV/W U11/2005/U SA | NC_008311 | vertebrates | Caliciviridae,Norovirus,Murine norovirus | 1 | — | EU004663 |
| Murine norovirus GV/WU12/2005/USA | NC_008311 | vertebrates | Caliciviridae,Norovirus,Murine norovirus | 1 | — | EU004664 |
| Murine norovirus GV/WU20/2005/USA | NC_008311 | vertebrates | Caliciviridae,Norovirus,Murine norovirus | 1 | — | EU004665 |
| Murine norovirus GV/WU21/2005/USA | NC_008311 | vertebrates | Caliciviridae,Norovirus,Murine norovirus | 1 | — | EU004666 |
| Murine norovirus GV/WU22/2005/USA | NC_008311 | vertebrates | Caliciviridae,Norovirus,Murine norovirus | 1 | — | EU004667 |
| Murine norovirus GV/WU23/2005/USA | NC_008311 | vertebrates | Caliciviridae,Norovirus,Murine norovirus | 1 | — | EU004668 |
| Murine norovirus GV/WU24/2005/USA | NC_008311 | vertebrates | Caliciviridae,Norovirus,Murine norovirus | 1 | — | EU004669 |
| Murine norovirus GV/WU25/2005/USA | NC_008311 | vertebrates | Caliciviridae,Norovirus,Murine norovirus | 1 | — | EU004670 |
| Murine norovirus GV/WU26/2005/USA | NC_008311 | vertebrates | Caliciviridae,Norovirus,Murine norovirus | 1 | — | EU004671 |
| Murine osteosarcoma virus osteosarcoma virus | NC_001506 | vertebrates | Retroviridae,Gammaretrovirus,Murine | 1 | — | AF033814 |
| Murine pneumotropic virus pneumotropic virus | NC_001505 | vertebrates | Polyomaviridae,Polyomavirus,Murine | 2 | — | M55904, EF186666 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Murine polyomavirus polyomavirus | NC_001515 88 | vertebrates | 3 | Polyomaviridae,Polyomavirus,Murine polyomavirus | — | U27812,U27813,JQ22 |
| Murine polyomavirus strain A3 | NC_001515 | vertebrates | 1 | Polyomaviridae,Polyomavirus,Murine polyomavirus | — | JQ2289 |
| Murine polyomavirus strain BG | NC_001515 | vertebrates | 1 | Polyomaviridae,Polyomavirus,Murine polyomavirus | — | AF442959 |
| Murine type C retrovirus | NC_001702,NC_00181 9,NC_0013 62,NC_001 501 | vertebrates | 1 | Retroviridae,Gammaretrovirus,Murine leukemia virus | — | X94150 |
| Muromegalovirus C4A | NC_004065 | vertebrates | 1 | Herpesviridae,Muromegalovirus,Murid herpesvirus 1 | — | EU579861 |
| Muromegalovirus G4 | NC_004065 | vertebrates | 1 | Herpesviridae,Muromegalovirus,Murid herpesvirus 1 | — | EU579859 |
| Muromegalovirus WP15B | NC_004065 | vertebrates | 1 | Herpesviridae,Muromegalovirus,Murid herpesvirus 1 | — | EU579860 |
| Mus dunniendogenous virus | NC_001702,NC_00181 9,NC_0013 62,NC_001 501 | vertebrates | 1 | Retroviridae,Gammaretrovirus,Murine leukemia virus | — | AF053745 |
| Muscovy duck circovirus | NC_005053,NC_00722 0,NC_0065 61 | vertebrates | 17 | Circoviridae,Circovirus,Duck circovirus | — | GQ423743,GQ86875 7,GQ423746,HQ1802 65,GU 168779,EF370 476,DQ166836,DQ16 6838,GQ423742,DQ1 66837,GQ423744,GQ 334371,FJ554673,G 0423741,EF451157,J X499186,GQ423745 |
| Muscovy duck parvovirus 22967 | NC_006147 | vertebrates | 3 | Parvoviridae,Dependovirus,Duck parvovirus | — | KC171936,X75093,U |
| Muscovy duck reovirus | NC_015126 | vertebrates | 3 | Reoviridae,Orthoreovirus,Avian orthoreovirus | seg. L1 | KC508647,KF306082,JX478260 |
| Muscovy duck reovirus | NC_015127 | vertebrates | 3 | Reoviridae,Orthoreovirus,Avian orthoreovirus | seg. L2 | KC508648,JX478261,KF306083 |
| Muscovy duck reovirus | NC_015128 | vertebrates | 3 | Reoviridae,Orthoreovirus,Avian orthoreovirus | seg. L3 | KC508649,JX478262,KF306084 |
| Muscovy duck reovirus | NC_015129 | vertebrates | 3 | Reoviridae,Orthoreovirus,Avian orthoreovirus | seg. M1 | KC508650,KF306085,JX478263 |
| Muscovy duck reovirus | NC_015130 | vertebrates | 4 | Reoviridae,Orthoreovirus,Avian orthoreovirus | seg. M2 | KF306086,KC756359,KC508651,JX478264 |
| Muscovy duck reovirus | NC_015131 | vertebrates | 3 | Reoviridae,Orthoreovirus,Avian orthoreovirus | seg. M3 | KC508652,JX478265,KF306087 |
| Muscovy duck reovirus | NC_015132 | vertebrates | 4 | Reoviridae,Orthoreovirus,Avian orthoreovirus | seg. S1 | DQ198854,KC508653,KF306088,DQ19136 3 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Muscovy duck reovirus | NC_015133 | vertebrates | 4 | Reoviridae,Orthoreovirus,Avian orthoreovirus | seg. S2 | DQ198857,KC508654,KF306089,JX478267 |
| Muscovy duck reovirus | NC_015134 | vertebrates | 3 | Reoviridae,Orthoreovirus,Avian orthoreovirus | seg. S3 | KC508655,JX478268,KF306090 |
| Muscovy duck reovirus | NC_015135 | vertebrates | 2 | Reoviridae,Orthoreovirus,Avian orthoreovirus | seg. S4 | KF306091,JX478269 |
| Muscovy duck reovirus 89330 | NC_015131 | vertebrates | 1 | Reoviridae,Orthoreovirus,Avian orthoreovirus | seg. M3 | AJ293969 |
| Muscovy duck reovirus S14 | NC_015130 | vertebrates | 1 | Reoviridae,Orthoreovirus,Avian orthoreovirus | seg. M2 | DQ989557 |
| Myotis polyomavirus VM-2008 | NC_011310 | vertebrates | 1 | Polyomaviridae,Polyomavirus,Bat polyomavirus | — | FJ188392 |
| Myxoma virus | NC_001132 | vertebrates | 34 | Poxviridae,Leporipoxvirus,Myxoma virus | — | JX565567,EU552530,JX565566,JX565573,KC660080,KC660082,JX565565,JX565574,JX565568,JX565580,JX565564,JX565569,KC660083,KC660079,KC660084,AF170726,KC660081,JX565571,JX565570,JX565572,KF148065,JX565558,JX565579,GQ409969,JX565575,JX565578,JX565563,KC660085,JX565584,JX565577,JX565583,JX565562,JX565581,JX565576 |
| Night-heron coronavirus HKU19 | NC_016994 | vertebrates | 1 | Coronaviridae, Deltacoronavirus, Night-heron coronavirus H KU19 | — | JQ065047 |
| Nile crocodilepox virus | NC_008030 | vertebrates | 1 | Poxviridae,Crocodylidpoxvirus,Nile crocodilepox virus | — | DQ356948 |
| Old World harvest mouse papillomavirus | NC_008582,NC_01432 | vertebrates | 1 | Papillomaviridae,Pipapillomavirus,Pipapillomavirus 2 | — | DQ269468 |
| Orange-spotted grouper iridovirus | NC_003494 | vertebrates | 1 | Incloviridae,Megalocytivirus,Infectious spleen and kidney necrosis virus | — | AY894343 |
| Orangutan polyomavirus | NC_013439 | vertebrates | 2 | Polyomaviridae,Polyomavirus,Orangutan polyomavirus | — | FN356900,FN356901 |
| Orf virus | NC_005336 | vertebrates | 4 | Poxviridae,Parapoxvirus,Orf virus | — | DQ184476,AY386263,HM133903,AY384264 |
| Otomops polyomavirus 1 | NC_020071 | vertebrates | 1 | Polyomaviridae,Polyomavirus,Otomops polyomavirus 1 | — | JX520664 |
| Otomops polyomavirus 2 | NC_020066 | vertebrates | 1 | Polyomaviridae,Polyomavirus,Otomops polyomavirus 2 | — | JX520658 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Ovine adenovirus A | NC_002513 | vertebrates | 1 | Adenoviridae,Mastadenovirus,Ovine adenovirus A | — | AF252854 |
| Ovine adenovirus D | NC_004037 | vertebrates | 1 | Adenoviridae,Atadenovirus,Ovine adenovirus D | — | U40839 |
| Ovine enterovirus | NC_004441 | vertebrates | 1 | Picornaviridae,Enterovirus,Enterovirus G | — | JQ277724 |
| Ovine enzootic nasal tumor virus | NC_007015 | vertebrates | 6 | Retroviridae,Betaretrovirus,Ovine enzootic nasal tumor virus | — | GU292317,GU292315,KC189895,GU292314,GU292318,GU292316 |
| Ovine enzootic nasal tumour virus | NC_007015 | vertebrates | 1 | Retroviridae,Betaretrovirus,Ovine enzootic nasal tumor virus | — | Y16627 |
| Ovine herpesvirus 2 | NC_007646 | vertebrates | 2 | Herpesviridae,Macavirus,Ovine herpesvirus 2 | — | AY839756,DQ198083 |
| Ovine lentivirus | NC_001511 | vertebrates | 3 | Retroviridae,Lentivirus,Ovine lentivirus | — | AF479638,M31646,M34193 |
| Ovine papillomavirus-1 | NC_001789 | vertebrates | 1 | Papillomaviridae,Deltapapillomavirus,Deltapapillomavirus 3 | — | U83594 |
| Ovine papillomavirus type 2 | NC_001789 | vertebrates | 1 | Papillomaviridae,Deltapapillomavirus,Deltapapillomavirus 3 | — | U83595 |
| PRCV ISU-1 | NC_002306 | vertebrates | 1 | Coronaviridae,Alphacoronavirus,Alphacoronavirus 1 | — | DQ811787 |
| PRRSV HB-1(sh)/2002 | NC_001961 | vertebrates | 1 | Arteriviridae,Arterivirus,Porcine reproductive and respiratory syndrome virus | — | AY150312 |
| PRRSV HB-2(sh)/2002 | NC_001961 | vertebrates | 1 | Arteriviridae,Arterivirus,Porcine reproductive and respiratory syndrome virus | — | AY262352 |
| PRRSV HN1 | NC_001961 | vertebrates | 1 | Arteriviridae,Arterivirus,Porcine reproductive and respiratory syndrome virus | — | AY457635 |
| PRRSV LV4.2.1 | NC_001961 | vertebrates | 1 | Arteriviridae,Arterivirus,Porcine reproductive and respiratory syndrome virus | — | AY588319 |
| Pan troglodytes schweinfurthii polyomavirus 2 | NC_019858 | vertebrates | 1 | Polyomaviridae,Polyomavirus,Pan troglodytes schweinfurthii polyomavirus 2 | — | JX159983 |
| Pan troglodytes verus polyomavirus 3 | NC_019855 | vertebrates | 1 | Polyomaviridae,Polyomavirus,Pan troglodytes verus polyomavirus 3 | — | JX159980 |
| Pan troglodytes verus polyomavirus 4 | NC_019856 | vertebrates | 1 | Polyomaviridae,Polyomavirus,Pan troglodytes verus polyomavirus 4 | — | JX159981 |
| Pan troglodytes verus polyomavirus 5 | NC_019857 | vertebrates | 1 | Polyomaviridae,Polyomavirus,Pan troglodytes verus polyomavirus 5 | — | JX159982 |
| Panine herpesvirus 2 | NC_003521 | vertebrates | 1 | Herpesviridae,Cytomegalovirus,Panine herpesvirus 2 | — | AF480884 |
| Panthera leo persica papillomavirus type 1 | NC_004765 | vertebrates | 1 | Papillomaviridae,Lambdapapillomavirus,Lambdapapillomavirus 1 | — | AY904724 |
| Papiine herpesvirus 2 | NC_007653 | vertebrates | 1 | Herpesviridae,Simplexvirus,Papiine herpesvirus 2 | — | DQ149153 |
| Papio hamadryas papillomavirus type 1 | NC_017716 | vertebrates | 1 | Papillomaviridae,Papio hamadryas papillomavirus type 1 | — | JF304764 |
| Paralichthys olivaceus birnavirus | NC_009923 | vertebrates | 1 | Birnaviridae,Aquabirnavirus,Paralichthys olivaceus birnavirus | seg. A | EU161285 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Paralichthys olivaceus birnavirus | NC_009924 | vertebrates | 1 | Birnaviridae,Aquabirnavirus,Paralichthys olivaceus birnavirus | seg. B | EU161286 |
| Parrot hepatitis B virus | NC_016561 | vertebrates | 19 | Hepadnaviridae,Avihepadnavirus,Parrot hepatitis B virus | — | JX274035,JX274023, JX274021,JX274029, JX274030,JX274019, JN565944,JX274032, JX274034,JX274033, JX274027,JX274026, JX274018,JX274024, JX274020,JX274022, JX274031,JX274028, JX274025 |
| Parvo-like hybrid virus UC1 | NC_022089 | vertebrates | 1 | Parvoviridae, Parvovirus NIH-CQV | — | KF170373 |
| Parvo-like hybrid virus UC11 | NC_022089 | vertebrates | 1 | Parvoviridae,Parvovirus NIH-COV | — | KF214638 |
| Parvo-like hybrid virus UC4 | NC_022089 | vertebrates | 1 | Parvoviridae,Parvovirus NIH-COV | — | KF214645 |
| Parvo-like hybrid virus UC9 | NC_022089 | vertebrates | 1 | Parvoviridae,Parvovirus NIH-COV | — | KF214640 |
| Parvovirus NIH-COV | NC_022089 | vertebrates | 1 | Parvoviridae,Parvovirus NIH-COV | — | KC617868 |
| Pegivirus A | NC_001837 | vertebrates | 1 | Flaviviridae,Pegivirus,Pegivirus A | — | U94421 |
| Penaeus monodon circovirus VN11 | NC_022897 | vertebrates | 1 | Circoviridae,Circovirus,Penaeus monodon circovirus VN11 | — | KF481961 |
| Penaeus monodon hepatopancreatic parvovirus | NC_011545 | vertebrates | 1 | Parvoviridae,Parvovirus,Penaeus monodon hepatopancreatic parvovirus | — | FJ410797 |
| Perch rhabdovirus | NC_020803 | vertebrates | 1 | Rhabdoviridae,Perhabdovirus,Perch rhabdovirus | — | JX679246 |
| Pestivirus Giraffe-1 | NC_003678 | vertebrates | 1 | Flaviviridae,Pestivirus,Pestivirus Giraffe-1 | — | AF144617 |
| Pestivirus reindeer-1 V60-Krefeld | NC_003679 | vertebrates | 1 | Flaviviridae,Pestivirus,Border disease virus | — | AF144618 |
| Pestivirus strain Aydin/04-TR | NC_018713 | vertebrates | 1 | Flaviviridae,Pestivirus,Pestivirus strain Aydin/04-TR | — | JX428945 |
| Phocoena phocoena papillomavirus 1 | NC_018074 | vertebrates | 1 | Papillomaviridae,Phocoena phocoena papillomavirus 1 | — | GU117621 |
| Phocoena phocoena papillomavirus 2 | NC_018075 | vertebrates | 1 | Papillomaviridae,Phocoena phocoena papillomavirus 2 | — | GU117622 |
| Phocoena phocoena papillomavirus 4 | NC_018076 | vertebrates | 1 | Papillomaviridae,Phocoena phocoena papillomavirus 4 | — | GU117623 |
| Phocoena spinipinnis papillomavirus 1 | NC_003348 | vertebrates | 1 | Papillomaviridae,Omikronpapillomavirus,Omikronpapillomavirus 1 | — | AJ238373 |
| Pigeon picornavirus B | NC_015626 | vertebrates | 2 | Picornaviridae, Pigeon picornavirus B | — | KC560801,FR727144 |
| Piliocolobus rufomitratus polyomavirus 1 | NC_019850 | vertebrates | 1 | Polyomaviridae,Polyomavirus,Piliocolobus rufomitratus polyomavirus 1 | — | JX159984 |
| Pipistrellus bat coronavirus HKU5 | NC_009020 | vertebrates | 1 | Coronaviridae,Betacoronavirus,Pipistrellus bat coronavirus HKU5 | — | EF065509 |
| Polyomavirus HPyV6 | NC_014406 | vertebrates | 6 | Polyomaviridae,Polyomavirus,Polyomavirus HPyV6 | — | HM011559,HM011558,HM011560,HM011562,HM011561,HM011563 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Polyomavirus HPyV7 HPyV7 | NC_014407 | vertebrates | 6 | Polyomaviridae,Polyomavirus,Polyomavirus | — | HM011566,HM011568,HM011565,HM011569,HM011564,HM011567 |
| Porcine adenovirus C adenovirus C | NC_002702 | vertebrates | 1 | Adenoviridae, Mastadenovirus, Porcine | — | AF289262 |
| Porcine astrovirus 3 | NC_019494 | vertebrates | 1 | Astroviridae,Mamastrovirus,Porcine astrovirus 3 | — | JX556691 |
| Porcine bocavirus 3 | NC_016031 | vertebrates | 4 | Parvoviridae,Bocavirus,Porcine bocavirus 3 | — | JF713715,JF429834,JF713714,KC473563 |
| Porcine bocavirus 3C | NC_016031 | vertebrates | 1 | Parvoviridae,Bocavirus,Porcine bocavirus 3 | — | JN681175 |
| Porcine bocavirus 4-1 | NC_016032 | vertebrates | 1 | Parvoviridae,Bocavirus,Porcine bocavirus 4 | — | JF429835 |
| Porcine bocavirus 4-2 | NC_016032 | vertebrates | 1 | Parvoviridae,Bocavirus,Porcine bocavirus 4 | — | JF429836 |
| Porcine bocavirus 5/JS677 5/JS677 | NC_016647 | vertebrates | 1 | Parvoviridae,Bocavirus,Porcine bocavirus | — | JN831651 |
| Porcine circovirus 1/2a | NC_013774 | vertebrates | 2 | Circoviridae,Circovirus,Porcine circovirus type | — | FJ790425,FJ655419 |
| Porcine circovirus 1 | NC_001792 | vertebrates | 51 | Circoviridae,Circovirus,Porcine circovirus 1 | — | DQ472013,DQ472012,FJ475129,GU79957 5,AY099501,DQ47205,AY099501,DQ47205,AY099501,DQ472014,AF012107,KC924758,FJ159689,JX566507,EF533941,DQ472016,DQ659153,GU371908,DQ659154,AY754012,DQ494787,JN398656,KC878437,JN133302,AY660574,KC527543,AY699796,DQ650650,FJ159693,KC733436,FJ159690,Y09921,AY184287,KC990120,AY193712,DQ472015,AY754013,AF071879,GU72233 4,FJ159692,EF49384 3,KC894933,KC4474 55,KF732857,AY2198 36,DQ358813,FJ1596 91,JN133303,DQ648 032,AY754015,GQ44 9671,U49186,AY7540 14,HM143844,DQ494 788 |
| Porcine circovirus 2 | NC_005148 | vertebrates | 1115 | Circoviridae,Circovirus,Porcine circovirus 2 | — | JX912914,KC800642,FJ660970,EF524519,DQ910865,KC800640,JX948775,FJ870971, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | FJ948167,EU148504,EF452350,JX982222,FJ905468,EF524528,HQ831529,HM000100,EF524517,EF565347,AY484409,AY099496,EU450590,EF565343,AY682996,HM009338,HQ738639,EF421969,DQ220736,JQ390467,DQ861899,JF690914,KF850458,GU370064,HQ148879,HM009337,DQ201640,AY256459,EF565359,KF850460,FJ870967,KF027494,JQ809463,FJ667585,AF264041,KF742549,KC800635,EU136718,FJ426398,EU274311,AY424402,JX512853,KF850466,AY682992,JQ181586,DQ915586,FJ447482,HQ202966,EU148507,FJ667589,EF675238,EU747085,JF690911,FN687850,EF421970,EF524542,AY596823,HM038025,AY321986,KC821781,AY484413,EU521707,FJ608542,FJ388889,GU325770,KC688418,H0395027,JF317567,HM776445,HQ395040,HM038027,HM776448,KF850464,KF742548,HM038029,FJ594471,JF827599,HQ202947,AY847748,AY035820,AY510375,AB072301,KC823058,AY122275,AY325495,FJ660968,GU370063,JX982227,FJ233905,DQ195679,AF118095,HQ020952,HQ591372, |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | EU727546,JN133304, FJ667588,HQ395030, FJ660971,GU083583, HM776446,KC75376 9,HQ395042,DQ8619 01,HQ395025,GU247 991,JX982221,EF675 240,EF565342,DQ86 1895,HQ831539,EF9 89713,KF732649,HQ 202964,EU547460,A Y556473,AY686765,F J608544,EU521709,H 0395046,EF675229, EU909686,EU450584 ,HQ831530,AF16652 8,HM161711,HQ5913 73,AY188355,AY641 542,GU450330,EF56 5349,EF675233,JF31 7572,JQ956679,FJ21 8002,EF565366,JX94 8779,FN687841,AF40 8635,HQ831535,HQ3 95031,FJ608547,DQ2 20739,JF290418,GU0 49340,GU325762,HM 003569,GQ449670,D 0201639,AF055391, EU503034,AY874168 ,EF524541,HM14289 6,JX512855,FJ66096 7,FJ712215,KC53381 2,FJ667582,EF39477 6,JQ181602,EU1367 19,DQ910866,HQ395 022,KC800638,EU54 5542,AY099500,EU5 47456,EF565365,EU 656143,KF871067,JF 317579,EU257516,K C823059,EU257515, EU780074,HQ395019 ,HQ831534,HQ39502 3,EF421972,GQ3590 05,KF742546,JN1192 55,FJ667592,KC8594 51,EF524520,JX5128 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 60,FJ905461,JF3175 65,JQ181594,JF6827 92,GU325766,JX512 859,FJ644930,GU450 328,HQ395054,HQ83 1522,FJ158602,AY32 1997,JX193799,KC80 0637,HQ378158,EF4 52352,HQ591370,DQ 629118,JX506730,G U325764,EU594440, HM038020,JX948773 ,HQ591367,KF37470 5,JX406420,HM6417 52,EU386606,HQ395 037,EU545550,HQ20 2955,DQ104419,HM7 76437,JX512857,EF5 65355,KF850468,AY4 84412,HQ831521,GU 083582,JF277497,HQ 395028,GQ358994,E F421973,AF364094,H M102350,EF592576, DQ220729,JX948784 ,FJ644558,HQ378159 ,EF394774,FN687857 ,HM003570,FR82345 1,EU136711,EF5653 63,FJ667586,KF8504 65,AY682990,HM038 028,EU148503,EF56 5350,EF452353,AF26 4038,EF524530,GQ3 58992,AY291318,AY 682995,EF565344,AY 943819,HQ113118,A Y536756,EF565364, DQ997816,JF690921, HQ395051,EU909688 ,EF524527,JX406425 ,FN687842,JQ181601 ,HQ202973,HM03801 9,KF695388,FN68785 5,EU391637,EU1367 14,EF524535,JN6398 57,HQ202961,FJ6445 61,JX945575,KC8217 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 84,EF565351,AB0723 03,HQ202950,AF154 679,AY291316,KF850 467,HM161710,JX94 8770,GQ358999,AY7 13470,KF027497,EF5 24515,JQ809462,AF2 01307,KF742553,GQ 404853,AF520783,AY 484416,JX948771,D 0180392,FJ716704,E F524540,HQ591381, GU808525,HQ59137 9,KF742547,HQ2029 44,FJ905460,JQ1816 05,JXQ99780,KC7537 71,EF210106,EU545 546,FN398025,EF458 306,EU136715,HQ20 2948,HQ395045,AF3 00643,AY321993,AF3 81177,AY686763,KC 823055,HQ113119,A F264040,AY849938, HQ395026,JQ181593 ,GQ358996,AY39172 9,AY916791,GU3257 67,EU594438,HQ591 366,FJ644562,JF690 923,AY424401,EF524 523,AF201309,FJ660 969,HM038018,KC47 3167,JXQ99781,FJ87 0973,EU503036,DQ3 63860,HQ591380,HQ 591376,EF565356,JX 982223,FN398027,H M776439,EU503031, HM038026,GQ35900 9,FJ667593,AY75402 1,KC153106,JX40641 9,HM776447,FJ9054 71,JF690915,JQ1815 87,EF421968,HM038 032,KF742542,HQ83 1519,HQ395041,HQ3 95043,FJ598044,DQ9 15583,FJQ41151,EU1 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 48505,KC821783,JF690920,DQ220738,HM038024,JF317566,AY682994,AF381176,KF926650,JF311571,DQ629119,HQ831531,JF690922,JQ002671,EU503033,FJ667584,KC533811,FJ608538,H0202957,FJ608539,EU450587,DQ870484,JF682794,JF272499,AY874166,JF317581,GQ359006,HQ395060,FJ644923,FJ608546,GU325753,JX948772,AY256458,EF565361,EU545548,GQ359004,HQ378161,FJ158603,HQ395039,HQ395048,JX948783,KF027493,EF565358,AY604430,AM086384,AY321988,FJ483938,KC788504,HM038022,GU244507,FJ644926,EF524431,DQ233257,J0094268,DQ220732,EF493840,FJ644919,EU921257,JF317577,GU325765,DQ141322,DQ478947,AY146992,DQ629116,HM623764,EF524516,KC835193,AY099499,EU340258,JQ181592,AY321999,GQ359007,KC447454,EU921255,FJ644931,HQ202953,EF565345,EU647557,HQ395038,JF928003,HM142895,HM142897,JF682791,HQ202958,JF690912,EU366324,DQ923524,KF850461,DQ220733,FJ905466,AY146991,EU503037,FN687844,FJ644 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 928,EF675235,JXQ99785,FJ712216,DQ206444,FJ644920,EF565362,HQ395032,AY536755,AB426905,HQ402903,AF085695,HQ591368,FJ644925,HQ831524,JF928006,JX948780,AY256457,D09978l5,JN639856,DQ915587,DQ648031,KF850469,HQ831520,HQ831526,HM038030,EF524529,HQ395029,EU366323,AY146993,FJ158607,FN398022,EU302141,EU418626,JQ181597,AY321985,HQ395036,AY754019,JF272498,AF147751,DQ017036,FJ667594,HQ202965,AY754017,HQ591378,JX948768,FJ501957,KC753770,GU325758,AF264039,AY288134,GQ359008,AY68299l,HQ202945,KF027492,FJ608548,JF682793,EU547458,AY094619,HQ395021,JX982226,HQ395056,AF264043,HM038016,EF675239,EU886637,FJ905469,HQ395052,AY874164,DQ220730,AY484407,FN398023,AY322002,GU325756,EU274310,HM038031,KF742551,AY699793,AY322000,GU049341,HQ395020,AY180397,HM776452,GU252370,JF690919,GU233804,HQ395035,AY484411,HF542107,GU001710,KF027495,HQ831527,FJ905464, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | AY556475,EU545549,JF928004,EF394777,FF67242,FJ598045,AF538325,KC80064 6,AF465211,JQ18159 8,EF515839,JQ18160 4,EU500338,JX94877 6,AJ293868,JX98222 5,EU366325,DQ8618 96,HQ202954,AY874 165,DQ923523,AY25 6456,EF565352,AY32 2003,KC835192,JQ9 94270,EU450585,AY 291317,FN687845,JX 53423 7,EF524532,G 0449672,GU938303, EF394779,DQ915588 ,EU257513,JF317585 ,AY484415,HQ39504 9,FJ644555,HQ20296 8,HM776443,JX9455 77,AY682993,AY556 474,AY217743,JF317 586,AY256455,GQ35 8995,JF317582,AY29 4310,AY613854,FN6 87846,JQ692110,FJ6 44924,KC860786,AJ2 23185,KC800645,HQ 395058,JQ413808,AF 201306,DQ629117,H 0831523,FJ870975,K C336418,JQ002672, AY321984,EU257514 ,EU340257,EF52453 7,FJ870968,EU52170 8,KC835194,EU2743 9,KC821782,FJ6445 57,JN615187,GQ359 010,KC800639,HM03 8033,KC684978,FN6 87843,FJ667587,JX9 48786,DQ180393,HQ 202956,HM038023,D 0104422,AB072302,J 0181591,FJ870976,A Y651850,EF524538, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | DQ915584,AY556477,FN687854,AY69167 9,DQ201642,EF5653 67,FJ64492l,FJ4403 38,HQ202960,EF394 778,EU545545,EU30 2139,AY874167,DQ8 61900,AY099498,AF0 55393,KF742541,KC 78850S,EU136713,H 020962,FJ667583,A Y754022,AY732494, GU247989,KC907703 ,EF394775,HQ59137 4,FJ644932,EF56535 3,EU545543,JX29471 7,EU274312,AY1776 26,JQ181606,EU547 457,EF524533,GU93 8304,HQ395061,FJ187 0972,AY099497,EF67 5236,GU325763,HQ2 02959,EU148506,JF9 28005,EU302140,EU 418627,AY754018,EF 675244,HQ20946,H 0831540,EF421971,J N60055,AY678532, HQ591369,HM77645 3,AY181947,JQ18160 3,EU503035,FJ90546 7,DQ346683,AY2881 33,DQ104421,KF742 552,JF317570,JX948 777,EF493839,JX982 224,KC823054,JX982 219,JF711784,HQ395 057,GU001709,FJ667 596,AY321982,JX945 576,EF565357,EF524 534,HQ113120,HQ39 5034,HQ831525,FN6 87856,GQ174519,EF 524526,AY321991,H 0831536,JF317569,J N388690,JF317574,D 0355153,FJ667591,H M776438,GQ359002, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | HQ202970,JQ181590,AF201308,AY969004,HQ113117,HM77645 0,KF742540,HQ2029 67,EF493838,JX5352 97,JF317575,AF3811 75,JX534236,JX9487 82,EU503032,FJ2339 10,KC336417,EU450 588,AY874163,JXQ99 782,FJ667595,HQ738 641,EU136716,JF317 580,GU325769,AY48 4410,DQ861897,KC4 73168,AY321992,KC 835191,EF675230,FN 398026,AY874169,G 0358998,KC835190, JQ181589,JQ181599, GU247988,AY754016 ,EF592575,HQ20294 9,FJ644559,EF56535 4,FN687847,AF20189 7,EF493837,JX94878 5,FN687849,JX91291 5,AF201311,AY32199 4,EF524522,JX94878 1,AY181948,GU3257 61,AF055392,GU325 757,EF675243,JQ181 600,JXQ99786,FJ218 000,DQ201641,EU78 0073,HQ202969,EF6 75234,JF690916,KC2 49977,GQ359003,JX 948769,JF928002,G 0404852,JX519293,A Y099495,JN176181,K C835189,JQ181585, DQ997817,FJ667590, JX406421,EF675237, GU017735,DQ62911 3,FJ644556,AY59682 2,FJ998185,HQ83153 2,HQ650833,AY4844 08,FJ608543,JX2043 86,FJ644922,DQ2207 31,FN687840,FJ6449 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 29,HM027580,KF742550,GU124593,DQ220727,EU45086,KC618389,JF317588,FJ158604,AY181946,FJ608540,FN687851,GQ449669,HQ831533,EU283329,KC800636,AF264042,GQ915288,EU594439,HQ395047,EF421967,JF317584,JQ809464,HQ831537,FJ870969,EU555439,JQ181596,EF675241,JF690917,FN687852,FJ644563,AY321989,KF742543,KF027496,GQ911590,HM776451,HM038021,HQ395050,AY579893,JF317583,EU921254,HM776444,HM776449,EF524524,FJ608541,FJ644560,GQ227412,HQ202951,HQ591377,KC788503,JQ181588,JF317587,KF742544,JF899334,HQ202971,JX982228,JX406423,GU247992,AY321996,GQ359011,HQ693092,GQ359000,AF086836,JX274295,EF565346,DQ220737,DQ629115,JQ181595,DQ104420,HM142898,FJ158606,JX982220,HQ202963,AF201310,KC188796,AJ293867,EF524518,AY578327,HQ395053,AJ293869,HQ395024,EU450589,AY322001,KC800641,DQ861898,HM142894,KF742545,DQ861902,JF317573,HQ591371,JF317576,FJ608545,EU545551,GU3 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 25759,EF675231,FN687848,JQ994269,EU095020,EU420015,JX406422,DQ220728,HM027579,GU325760,HQ591375,EU346945,EU594437,AY321998,KC751546,EF493841,JXQ99783,JQ653449,DQ915585,AY686762,EU589463,HQ395059,FJ905462,EU503039,GU247990,FJ233906,EF565348,EU450592,EU547459,HQ713495,EU257511,AF454546,AF201305,GQ915289,HQ831528,GU938302,GQ358993,EF675232,KC753772,FJ233909,AY321983,EF565360,JX512858,JXQ99784,EU126887,KC823056,AY322004,EU408780,FJ905463,JX406426,EU684164,FJ233907,EU545547,AY691169,KC753768,DQ629114,AY484414,KC733435,KF850463,HM142899,FJ233908,GQ358997,GU252369,KC473165,AF118097,AY180396,FJ623185,EU136712,AY424404,HQ378160,KC688419,EF524536,KC527542,JX948778,DQ220734,EU136720,KC823053,JX406424,AY288135,EF524521,JX948774,HQ395033,HQ202972,EU450591,EF524539,EF565368,DQ364650,D0151643,DQ322701,FJ608549,GU325754,AY424403,FJ935780, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | KF027491,HM776442,JF317568,KC821785,KF850462,GU325755,FJ158605,EF61903,7,JX512856,JF69091,8,FJ870970,FN39802,4,EU545544,KC8006,34,HM142900,AY256460,FJ905465,AY682997,AF027217,FJ644927,HM038034,AY321990,FJ905459,HQ738640,HM776441,AY686764,EU503040,JX512854,FN687853,EFS24525,EU136717,EF452351,GU247987,AF086835,JQ181607,EU909687,KC823057,AY321987,KF850459,HQ113121,JN119257,KF871068,HQ83153,8,DQ220735,AF0868 34,KC800644,AY754020,FJ948168,DQ104423,JF317578,AY556476,HQ693093,FJ905470,GU450327,EU921256,HQ591365,AY321995,KC473166,EU257512,GQ996404,GQ359001,EU366326,FJ870974,HQ395055,GU244506,HM776440,EU86638,AF05539,4,JX535296,JN1192 56,GU450329,HM038017,FJ716703,AF544024,JF317589,FJ218001,AY181945,AY424405,JF690913,EF493842,GU325768,GUO49342,FJ804417,HQ395044,HM009336 |
| Porcine circovirus 2 P0404c/03 | NC_005148 | vertebrates | 1 | Circoviridae,Circovirus,Porcine circovirus 2 | — | EU057185 |
| Porcine circovirus 2 R0255/209/03 | NC_005148 | vertebrates | 1 | Circoviridae,Circovirus,Porcine circovirus 2 | — | EU057189 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Porcine circovirus 2 S0255/210/03 | NC_005148 | vertebrates | 1 | Circoviridae,Circovirus,Porcine circovirus 2 | — | EU057188 |
| Porcine circovirus 2 T0181c/03 | NC_005148 | vertebrates | 1 | Circoviridae,Circovirus,Porcine circovirus 2 | — | EU057186 |
| Porcine circovirus 2 U0168/03 | NC_005148 | vertebrates | 1 | Circoviridae,Circovirus,Porcine circovirus 2 | — | EU057187 |
| Porcine circovirus 2 Z0161 b/03 | NC_005148 | vertebrates | 1 | Circoviridae,Circovirus,Porcine circovirus 2 | — | EU057184 |
| Porcine circovirus 2 strain SD3 | NC_005148 | vertebrates | 1 | Circoviridae,Circovirus,Porcine circovirus 2 | — | DQ218419 |
| Porcine circovirus 2 strain SD5 | NC_005148 | vertebrates | 1 | Circoviridae,Circovirus,Porcine circovirus 2 | — | DQ218420 |
| Porcine circovirus 2 strain SD6 | NC_005148 | vertebrates | 1 | Circoviridae,Circovirus,Porcine circovirus 2 | — | DQ218421 |
| Porcine circovirus type 1/2a | NC_013774 | vertebrates | 1 | Circoviridae,Circovirus,Porcine circovirus type 1/2a | — | FJ655418 |
| Porcine circovirus type 2-B | NC_005148 | vertebrates | 4 | Circoviridae,Circovirus,Porcine circovirus 2 | — | KC261601,KC261600,AF112862,GU799576 |
| Porcine circovirus type 2-C | NC_005148 | vertebrates | 1 | Circoviridae,Circovirus,Porcine circovirus 2 | — | AF109398 |
| Porcine circovirus type 2-D | NC_005148 | vertebrates | 1 | Circoviridae,Circovirus,Porcine circovirus 2 | — | AF117753 |
| Porcine circovirus type 2-E | NC_005148 | vertebrates | 1 | Circoviridae,Circovirus,Porcine circovirus 2 | — | AF109399 |
| Porcine coronavirus HKU15 | NC_016990 | vertebrates | 2 | Coronaviridae, Deltacoronavirus, Porcine coronavirus HKU15 | — | JQ065043,JQ065042 |
| Porcine cytomegalovirus | NC_022233 | vertebrates | 1 | Herpesviridae,Cytomegalovirus, Porcine cytomegalovirus | — | KF017583 |
| Porcine encephalomyocarditis virus | NC_001479 | vertebrates | 2 | Picornaviridae,Cardiovirus,Encephalomyocarditis virus | — | DQ517424,HM641897 |
| Porcine endogenous retrovirus | NC_003059 | vertebrates | 5 | Retroviridae,Gammaretrovirus,Porcine type-C oncovirus | — | EU523109,A66553,AXQ52638,A66552,AX175461 |
| Porcine endogenous retrovirus C | NC_003059 | vertebrates | 2 | Retroviridae,Gammaretrovirus,Porcine type-C oncovirus | — | EF133960,HM159246 |
| Porcine endogenous retrovirus C/A | NC_003059 | vertebrates | 2 | Retroviridae,Gammaretrovirus,Porcine type-C oncovirus | — | AY953542,AY570980 |
| Porcine endogenous retrovirus E | NC_003059 | vertebrates | 1 | Retroviridae,Gammaretrovirus,Porcine type-C oncovirus | — | AF356697 |
| Porcine enterovirus 10 | NC_004441 | vertebrates | 1 | Picornaviridae,Enterovirus,Enterovirus G | — | AF363455 |
| Porcine enterovirus 15 | NC_004441 | vertebrates | 1 | Picornaviridae,Enterovirus,Enterovirus G | — | JN807387 |
| Porcine enterovirus 3H | NC_004441 | vertebrates | 1 | Picornaviridae,Enterovirus,Enterovirus G | — | HQ702854 |
| Porcine enterovirus 9 | NC_004441 | vertebrates | 2 | Picornaviridae,Enterovirus,Enterovirus G | — | Y14459,HM131607 |
| Porcine enterovirus B | NC_004441 | vertebrates | 2 | Picornaviridae,Enterovirus,Enterovirus G | — | AF363453,JQ818253 |
| Porcine epidemic diarrhea virus | NC_003436 | vertebrates | 32 | Coronaviridae,Alphacoronavirus,Porcine epidemic diarrhea virus | — | KF272920,KF650374,KF650372,KC140102,JQ282909,EF185992,KC210145,KF46875 2,KC210147,KF6503 71,KC109141,JN5472 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 28,JX112709,KF4687 53,JX524137,JX5607 61,KC196276,KC189 944,JX188454,KC210 146,JX489155,JXQ88 695,KF650370,KF384 500,JX261936,KF650 375,AF353511,KF650 373,KF468754,JN825 712,GU937797,KF26 7450 |
| Porcine kobuvirus | NC_011829 ,NC_01676 9 | vertebrates | 9 | Picornaviridae,Kobuvirus,Aichivirus C | — | KC424638,JX401523, JX177612,KC424639, KF695124,KC204684 ,JQ692069,KC42464 0,JX827598 |
| Porcine kobuvirus swine/K-30-HUN/2008/HUN | NC_011829 ,NC_01676 9 | vertebrates | 1 | Picornaviridae,Kobuvirus,Aichivirus C | — | GQ249161 |
| Porcine kobuvirus swine/S-1-HUN/2007/H ungary | NC_011829 ,NC_01676 9 | vertebrates | 1 | Picornaviridae,Kobuvirus,Aichivirus C | — | EU787450 |
| Porcine partetravirus | NC_022104 | vertebrates | 1 | Parvoviridae,Porcine partetravirus | — | KC992732 |
| Porcine parvovirus | NC_001718 | vertebrates | 26 | Parvoviridae,Parvovirus,Porcine parvovirus | — | KF913346,KF913348, KF429253,AY684869, EU790641,JN872448, M38367,L23427,JX99 2846,KF913345,KF91 3349,U44978,KF9133 47,KF913351,AY5833 18,KF429252,EU790 642,FJ822038,DQ675 456,KF913350,DQ062 3,JN968975,KF42925 5,KF742500,HM9890 09,KF429254 |
| Porcine parvovirus 4 | NC_014665 | vertebrates | 9 | Parvoviridae,Parvovirus,Porcine parvovirus 4 | — | GQ387500,GU97896 5,GU978968,HM0311 34,GU978966,GU978 967,GQ387499,GU97 8964,HM031135 |
| Porcine parvovirus 5 | NC_023020 | vertebrates | 6 | Parvoviridae,Parvovirus,Porcine parvovirus 5 | — | JX896320,KF661535, JX896322,JX896319, JX896321,JX896318 |
| Porcine pestivirus isolate Bungowannah | NC_023176 | vertebrates | 1 | Flaviviridae,Pestivirus,Porcine pestivirus isolate Bungowannah | — | EF100713 |
| Porcine reovirus SHR-A | NC_004274 | vertebrates | 1 | Reoviridae,Orthoreovirus,Mammalian orthoreovirus | seg. L3 | JX415472 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Porcine reovirus SHR-A | NC_004275 | vertebrates | 1 | Reoviridae,Orthoreovirus,Mammalian orthoreovirus | seg. L2 | JX415467 |
| Porcine reovirus SHR-A | NC_004276 | vertebrates | 1 | Reoviridae,Orthoreovirus,Mammalian orthoreovirus | seg. S4 | JX415473 |
| Porcine reovirus SHR-A | NC_004277 | vertebrates | 1 | Reoviridae,Orthoreovirus,Mammalian orthoreovirus | seg. S1 | JX415469 |
| Porcine reovirus SHR-A | NC_004278 | vertebrates | 1 | Reoviridae,Orthoreovirus,Mammalian orthoreovirus | seg. M2 | JX415471 |
| Porcine reovirus SHR-A | NC_004279 | vertebrates | 1 | Reoviridae,Orthoreovirus,Mammalian orthoreovirus | seg. S2 | JX415465 |
| Porcine reovirus SHR-A | NC_004280 | vertebrates | 1 | Reoviridae,Orthoreovirus,Mammalian orthoreovirus | seg. M1 | JX415468 |
| Porcine reovirus SHR-A | NC_004281 | vertebrates | 1 | Reoviridae,Orthoreovirus,Mammalian orthoreovirus | seg. M3 | JX415474 |
| Porcine reovirus SHR-A | NC_004282 | vertebrates | 1 | Reoviridae,Orthoreovirus,Mammalian orthoreovirus | seg. L1 | JX415466 |
| Porcine reovirus SHR-A | NC_004283 | vertebrates | 1 | Reoviridae,Orthoreovirus,Mammalian orthoreovirus | seg. S3 | JX415470 |
| Porcine reovirus SHR-A | NC_013228 | vertebrates | 1 | Reoviridae,Orthoreovirus,Mammalian orthoreovirus | seg. M2 | JX415471 |
| Porcine reovirus SHR-A | NC_013230 | vertebrates | 1 | Reoviridae,Orthoreovirus,Mammalian orthoreovirus | seg. M3 | JX415474 |
| Porcine reovirus SHR-A | NC_013232 | vertebrates | 1 | Reoviridae,Orthoreovirus,Mammalian orthoreovirus | seg. S2 | JX415465 |
| Porcine reovirus SHR-A | NC_013234 | vertebrates | 1 | Reoviridae,Orthoreovirus,Mammalian orthoreovirus | seg. S4 | JX415473 |
| Porcine reproductive and respiratory syndrome virus | NC_001961 | vertebrates | 327 | Arteriviridae,Arterivirus, Porcine reproductive and respiratory syndrome virus | — | HQ843178,JQ663542,JQ663545,GU73726 4,FJ950746,EU26260 3,KF287142,EF51796 2,EU200962,JQ3098 22,JQ308798,FJ9507 47,HQ699067,KC422 730,KC862570,DQ17 6020,KC862567,HM2 14915,JX192638,GU 047344,EU880438,J 0326271,KF287133, GU168568,EU187484 ,JN660150,JX192637 ,GU143913,JX31764 8,EU880436,EF5360 00,JQ663561,EU200 961,JF268681,DQ459 471,KC862574,GQ47 5526,HQ315836,EU1 06888,KC492506,JQ 663541,EU864232,E |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | U09707,EF484031,KC422725,GU168567,GQ914997,KF28713 4,JN662424,FJ39345 8,AY612613,KF28713 9,JF800911,JQ66355 8,JQ663544,AF32569 1,JQ663563,EU8804 37,EF532802,GU454 850,FJ393456,JQ663 547,JQ663568,FJ349 261,JX215553,JX878 379,EF536001,JX215 554,KC862573,KF28 7135,KF555450,KF28 7137,EU880435,EU7 08726,JF796180,JX2 58843,JQ663546,KF2 87132,EF532805,KC 422729,JQ955657,D 0176021,JQ715698, GU23273 8,HM18967 6,KC862577,KC4227 28,FJ548855,FJ3934 59,HQ843180,EF532 801,EF484033,EU88 0434,EF535999,JQ66 3566,EU807840,EF5 36002,JQ663567,EU 880442,KC469618,J 0804986,JF268674,E F112445,DQ473474, KC862566,EU109503 ,EF532806,EF641008 ,EU864231,KC49250 5,JQ663553,EU2362 59,EF488739,DQ864 705,JQ663551,JX192 635,EU880431,JQ66 3549,JX235365,FJ17 5687,AF184212,JX17 7644,EU360130,JX31 7649,KC862579,EU1 09502,EF112446,EF5 32810,EF532813,KC 862584,AF494042,EF 532819,EU939312,A Y42271,HM016158, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | AF066183,KF203132,EF153486,GQ359108,JQ663555,JN864948,GU169411,JF268673,DQ988080,JQ66356 4,AY032626,KC8625 75,JF268683,KC8625 76,FJ895329,AY3665 25,JQ663540,GQ374 441,DQ056373,EU07 6704,HQ223604,JQ6 63556,GQ374442,KF 63217,JN654459,JQ 309823,GU269541,FJ 548851,EU678352,JX 215552,JX217036,FJ 950744,JF268680,JX 857698,EU880433,E F075945,JX512910,J X235367,JQ087873,K F555451,JQ663565,K C862583,EF532804, EU360129,EU860249 ,FJ393457,JN387272, GQ351601,AY150564 ,KF611905,JQ663562 ,GU232737,JN62628 7,HM011104,GU1685 69,KC862581,EF532 807,EF532811,JX192 633,HQ233605,GU23 2735,JN387274,DQ2 17415,EU860248,JF2 68676,JQ663543,DQ 779791,EF532818,EF 532808,KF287138,KF 815525,FJ950745,AB 288356,GQ461593,G U232736,GU461292, JXQ87437,JQ663560, JX235370,JQ663548, KC862572,HM01615 9,KF287136,FJ54885 4,EU880439,KC8625 69,EF635006,AY5459 85,JX215551,FJ8891 29,DQ489311,JF2686 78,AF159149,JF2686 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 72,EU880443,KC422727,GQ499193,AF331831,FJ524376,EU864233,JN387273,DQ176019,JQ663559,HQ315835,FJ548852,JF268684,FJ175689,HM853673,KC862585,EU880441,KC527830,EF532816,JF268677,FJ899592,EF112447,HM214913,U87392,KC862568,GQ499196,FJ536165,JF26868 2,KC445138,EF532809,JF268675,GQ857656,JF802085,JX878380,EU825724,JX192634,JX235366,HQ843179,JN256115,KC422731,JQ743666,JX192639,FJ797690,KC862571,HQ315837,FJ889130,EU097706,HQ843181,FJ548853,EF536003,KF287143,GQ499195,EF532812,KC492504,JN387271,KC862580,JN654458,JX192636,JQ663554,EF532815,JXQ44140,AF176348,GU067771,J0663550,JF748717,J0663552,KC422726,EF532817,JX912249,HM214914,JX880029,JX192632,JF268679,EU144079,JQ955658,EU825723,GQ499194,EF488048,JQ71569 7,EU360128,KF2871 41,AY585241,FJ524377,FJ394029,KC862578,FJ175688,KC862582,EU880432,AF046869,EF532803,JF748718,GQ330474,EF532814,EU880440,KF2 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Porcine sapelovirus | NC_003987 | vertebrates | 3 | Picornaviridae,Sapelovirus,Porcine sapelovirus | — | 87140,GU047345,HQ401282,JQ663557,EU624117 |
| Porcine sapelovirus 1 | NC_003987 | vertebrates | 1 | Picornaviridae,Sapelovirus,Porcine sapelovirus | — | HQ875059,KF539414,JX286666 |
| Porcine teschovirus | NC_003985 | vertebrates | 30 | Picornaviridae,Teschovirus, Porcine teschovirus | — | AF406813 AF296102,GQ914053,AF231769,AF296118,AF296111,AF296112,AF296113,HQ020378,AF296107,AF296109 2,AF296103,AF296115,KC667563,JQ4294 05,AF296089,AF2960 91,GU446660,AF231 767,AF296090,AF296 109,AF296104,AF231 768,AIQ11380,AF296 100,DQ355222,AF29 6087,AF296088,AF29 6117,KC667562,AF2 96108 |
| Porcine teschovirus 1 | NC_003985 | vertebrates | 1 | Picornaviridae,Teschovirus, Porcine teschovirus | — | AB038528 |
| Porcine teschovirus 10 | NC_003985 | vertebrates | 2 | Picornaviridae,Teschovirus, Porcine teschovirus | — | AF296119,AF296095 |
| Porcine teschovirus 11 | NC_003985 | vertebrates | 1 | Picornaviridae,Teschovirus, Porcine teschovirus | — | AF296096 |
| Porcine teschovirus 4 | NC_003985 | vertebrates | 1 | Picornaviridae,Teschovirus, Porcine teschovirus | — | JQ975417 |
| Porcine teschovirus 8 | NC_003985 | vertebrates | 5 | Picornaviridae,Teschovirus, Porcine teschovirus | — | JQ664746,GQ293092,KC757344,AF296093,JN710381 |
| Porcine teschovirus 9 | NC_003985 | vertebrates | 1 | Picornaviridae,Teschovirus, Porcine teschovirus | — | AF296094 |
| Porcine torovirus | NC_022787 | vertebrates | 1 | Coronaviridae,Torovirus,Porcine torovirus | — | JQ860350 |
| Possum enterovirus W1 | NC_008714 | vertebrates | 1 | Picornaviridae,Enterovirus,Possum enterovirus W1 | — | AY462106 |
| Possum enterovirus W6 | NC_008715 | vertebrates | 1 | Picornaviridae,Enterovirus,Possum enterovirus W6 | — | AY462107 |
| PreXMRV-1 | NC_007815 | vertebrates | 1 | Retroviridae,Gammaretrovirus,Murine leukemia-related retroviruses | — | FR871849 |
| Procyon lotor papillomavirus 1 | NC_007150 | vertebrates | 1 | Papillomaviridae,Lambdapapillomavirus,Lambdapapillomavirus 4 | — | AY763115 |
| Pseudocowpox virus | NC_013804 | vertebrates | 2 | Poxviridae,Parapoxvirus,Pseudocowpox virus | — | GQ329670,GQ32966 9 |

TABLE 10-continued

VıroCap-1.0 Taxonomy

| Taxonomy | Rep.Acc.ID | Host | # GN's | Lineage | Seg. Count | GN.Acc.IDs |
|---|---|---|---|---|---|---|
| Psittacid herpesvirus 1 | NC_005264 | vertebrates | 1 | Herpesviridae,Iltovirus,Psittacid herpesvirus 1 | — | AY372243 |
| Psittacus erithacus timneh papillomavirus | NC_003973 | vertebrates | 2 | Papillomaviridae,Thetapapillomavirus,Thetapapillomavirus 1 | — | AF502599,AF420235 |
| Pteronotus polyomavirus | NC_020070 | vertebrates | 1 | Polyomaviridae,Polyomavirus,Pteronotus polyomavirus | — | JX520662 |
| Puma concolor papillomavirus type 1 | NC_004765 | vertebrates | 1 | Papillomaviridae,Lambdapapillomavirus,Lambdapapillomavirus 1 | — | AY904723 |
| Pygmy chimpanzee papillomavirus type 1 | NC_001355 | vertebrates | 1 | Papillomaviridae,Alphapapillomavirus,Alphapapillomavirus 10 | — | X62844 |
| Quail picornavirus QPV1/HUN/2010 | NC_016403 | vertebrates | 1 | Picornaviridae, Quail picornavirus QPV1/HUN/2010 | — | JN674502 |
| RD114 retrovirus | NC_009889 | vertebrates | 2 | Retroviridae,Gammaretrovirus,RD114 retrovirus | — | AB559882,EU030001 |
| Rabbit calicivirus Australia 1 MIC-07 | NC_011704 | vertebrates | 1 | Caliciviridae,Lagovirus,Rabbit calicivirus Australia 1 MIC-07 | — | EU871528 |
| Rabbit coronavirus HKU14 | NC_017083 | vertebrates | 4 | Coronaviridae,Betacoronavirus,Rabbit coronavirus HKU14 | — | JN874559,JN874562, JN874561,JN874560 |
| Rabbit fibroma virus | NC_001266 | vertebrates | 1 | Poxviridae,Leporipoxvirus,Rabbit fibroma virus | — | AF170722 |
| Rabbit hemorrhagic disease virus | NC_001543 | vertebrates | 35 | Caliciviridae,Lagovirus,Rabbit hemorrhagic disease virus | — | DQ280493,EF363035 ,EF558586,DQ18907 7,JX886001,AB30069 3,EF558576,EF55858 2,M67473,KC595270, DQ189078,EU003579 ,EF558572,EF558578 ,EF558580,EF558574 ,AF295785,EF558577 ,AY523410,HM62330 9,EU003582,EF5585 85,EU003578,AF258 618,DQ205345,EU00 3581,EF558584,EU0 03580,EF558579,JF4 12629,EF558575,EF5 58581,EF558573,EF5 58583,JX886002 |
| Rabbit hemorrhagic disease virus-AST89 | NC_001543 | vertebrates | 1 | Caliciviridae,Lagovirus,Rabbit hemorrhagic disease virus | — | Z49271 |
| Rabbit hemorrhagic disease virus-BS89 | NC_001543 | vertebrates | 1 | Caliciviridae,Lagovirus,Rabbit hemorrhagic disease virus | — | X87607 |
| Rabbit hemorrhagic disease virus-SD | NC_001543 | vertebrates | 1 | Caliciviridae,Lagovirus,Rabbit hemorrhagic disease virus | — | Z29514 |
| Rabbit hemorrhagic disease virus-V351 | NC_001543 | vertebrates | 1 | Caliciviridae,Lagovirus,Rabbit hemorrhagic disease virus | — | U54983 |
| Rabbit oral papillomavirus | NC_002232 | vertebrates | 1 | Papillomaviridae,Kappapapillomavirus,Kappapapillomavirus 1 | — | AF227240 |
| Rabbit vesivirus | NC_008580 | vertebrates | 1 | Caliciviridae,Vesivirus,Rabbit vesivirus | — | AJ866991 |
| Rana grylio iridovirus | NC_005946 | vertebrates | 1 | Iridoviridae,Ranavirus,Frog virus 3 | — | JQ654586 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rangifer tarandus papillomavirus 2 | NC_021930 | vertebrates | 1 | Papillomaviridae,Rangifer tarandus papillomavirus 2 | — | KC810012 |
| Ranid herpesvirus 1 | NC_008211 | vertebrates | 1 | Alloherpesviridae,Batrachovirus,Ranid herpesvirus 1 | — | DQ665917 |
| Ranid herpesvirus 2 | NC_008210 | vertebrates | 1 | Alloherpesviridae,Batrachovirus,Ranid herpesvirus 2 | — | DQ665652 |
| Raptor adenovirus A | NC_015455 | vertebrates | 1 | Adenoviridae,Siadenovirus,Raptor adenovirus A | — | EU715130 |
| Rat coronavirus | NC_012936,NC_001846 | vertebrates | 2 | Coronaviridae,Betacoronavirus,Murine coronavirus | — | JF792616,JF792617 |
| Rat coronavirus Parker | NC_012936,NC_001846 | vertebrates | 1 | Coronaviridae,Betacoronavirus,Murine coronavirus | — | FJ938068 |
| Rat theilovirus 1 | NC_009448,NC_001366,NC_010810 | vertebrates | 2 | Picornaviridae,Cardiovirus,Theilovirus | — | EU542581,EU815052 |
| Rattus norvegicus papillomavirus 1 EES-2009 | NC_008519 | vertebrates | 1 | Papillomaviridae,Pipapillomavirus,Pipapillomavirus 1 | — | GQ180114 |
| Raven circovirus | NC_008375 | vertebrates | 1 | Circoviridae,Circovirus,Raven circovirus | — | DQ146997 |
| Redspotted grouper nervous necrosis virus | NC_008040 | vertebrates | 5 | Nodaviridae,Betanodavirus,Redspotted grouper nervous necrosis virus | seg. RNA 1 | GQ402010,AY324869,AY369136,GQ402012,EF558368 |
| Redspotted grouper nervous necrosis virus | NC_008041 | vertebrates | 6 | Nodaviridae,Betanodavirus,Redspotted grouper nervous necrosis virus | seg. RNA 2 | AY744705,AY324870,GQ402011,EF55836 9,AY690596,GQ40202 13 |
| Reindeer papillomavirus | NC_001524 | vertebrates | 1 | Papillomaviridae,Deltapapillomavirus,Deltapapillomavirus 1 | — | AF443292 |
| Reovirus sp.T2W | NC_004276 | vertebrates | 1 | Reoviridae,Orthoreovirus,Mammalian orthoreovirus | seg. S4 | DQ220019 |
| Reovirus sp.T2W | NC_004277 | vertebrates | 1 | Reoviridae,Orthoreovirus,Mammalian orthoreovirus | seg. S1 | DQ220017 |
| Reovirus sp.T2W | NC_004279 | vertebrates | 1 | Reoviridae,Orthoreovirus,Mammalian orthoreovirus | seg. S2 | DQ220020 |
| Reovirus sp.T2W | NC_004283 | vertebrates | 1 | Reoviridae,Orthoreovirus,Mammalian orthoreovirus | seg. S3 | DQ220018 |
| Reovirus sp.T2W | NC_013232 | vertebrates | 1 | Reoviridae,Orthoreovirus,Mammalian orthoreovirus | seg. S2 | DQ220020 |
| Reovirus sp.T2W | NC_013234 | vertebrates | 1 | Reoviridae,Orthoreovirus,Mammalian orthoreovirus | seg. S4 | DQ220019 |
| Reovirus sp.T3C43-MA | NC_004277 | vertebrates | 1 | Reoviridae,Orthoreovirus,Mammalian orthoreovirus | seg. S1 | U74293 |
| Reovirus sp.T3C44-MA | NC_004277 | vertebrates | 1 | Reoviridae,Orthoreovirus,Mammalian orthoreovirus | seg. S1 | U74292 |
| Reovirus sp.T3C84-MA | NC_004277 | vertebrates | 1 | Reoviridae,Orthoreovirus,Mammalian orthoreovirus | seg. S1 | U74291 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Reptile vesivirus Cro1 | NC_002551 | vertebrates | Caliciviridae,Vesivirus,Vesicular exanthema of swine virus | 1 | — | JXQ47864 |
| Reticuloendotheliosis virus | NC_006934 | vertebrates | Retroviridae,Gammaretrovirus,Reticuloendotheliosis virus | 10 | — | FJ496333,FJ439119,DQ00359l,DQ38745 0,FJ439120,JX91271 0,GQ375848,GQ4156 46,KF305089,AY8429 51 |
| Rhesus monkey papillomavirus 1 | NC_001678 | vertebrates | Papillomaviridae,Alphapapillomavirus,Alphapapillomavirus 12 | 1 | — | M60184 |
| Rhesus monkey rhadinovirus H26-95 | NC_003401 | vertebrates | Herpesviridae,Rhadinovirus,Macacine herpesvirus 5 | 1 | — | AF210726 |
| Rhesus papillomavirus type 1b | NC_001678 | vertebrates | Papillomaviridae,Alphapapillomavirus,Alphapapillomavirus 12 | 2 | — | EF591300,FJ598133 |
| Rhinolophus bat coronavirus HKU2 | NC_009988 | vertebrates | Coronaviridae,Alphacoronavirus,Rhinolophus bat coronavirus HKU2 | 4 | — | EF203066,EF203065,EF203067,EF203064 |
| Rhinovirus C | NC_009996 | vertebrates | Picornaviridae,Enterovirus,Rhinovirus C | 3 | — | GQ223228,JXQ74056 ,GQ223227 |
| Rock bream iridovirus | NC_003494 | vertebrates | Incloviridae,Megalocytivirus,Infectious spleen and kidney necrosis virus | 2 | — | KC244182,AY532606 |
| Rodent herpesvirus Peru 3 | NC_015049 | vertebrates | Herpesviridae,Rodent herpesvirus Peru | 2 | — | HQ698924,HQ22196 |
| Rodent pegivirus | NC_021154 | vertebrates | Flaviviridae,Pegivirus,Rodent pegivirus | 1 | — | KC815311 |
| Ross's goose hepatitis B virus | NC_005888 ,NC_005950 | vertebrates | Hepadnaviridae, Ross's goose hepatitis B virus | 3 | — | AY494849,AY494848 ,M95589 |
| Rotavirus D chicken/05V0049/DEU/2005 | NC_014511 | vertebrates | Reoviridae,Rotavirus,Rotavirus D | 1 | seg. 1 | GU733443 |
| Rotavirus D chicken/05V0049/DEU/2005 | NC_014512 | vertebrates | Reoviridae,Rotavirus,Rotavirus D | 1 | seg. 2 | GU733444 |
| Rotavirus D chicken/05V0049/DEU/2005 | NC_014513 | vertebrates | Reoviridae,Rotavirus,Rotavirus D | 1 | seg. 3 | GU733445 |
| Rotavirus D chicken/05V0049/DEU/2005 | NC_014514 | vertebrates | Reoviridae,Rotavirus,Rotavirus D | 1 | seg. 4 | GU733446 |
| Rotavirus D chicken/05V0049/DEU/2005 | NC_014515 | vertebrates | Reoviridae,Rotavirus,Rotavirus D | 1 | seg. 5 | GU733447 |
| Rotavirus D chicken/05V0049/DEU/2005 | NC_014516 | vertebrates | Reoviridae,Rotavirus,Rotavirus D | 1 | seg. 6 | GU733448 |
| Rotavirus D chicken/05V0049/DEU/2005 | NC_014517 | vertebrates | Reoviridae,Rotavirus,Rotavirus D | 1 | seg. 7 | GU733449 |
| Rotavirus D chicken/05V0049/DEU/2005 | NC_014518 | vertebrates | Reoviridae,Rotavirus,Rotavirus D | 1 | seg. 8 | GU733450 |
| Rotavirus D chicken/05V0049/DEU/2005 | NC_014519 | vertebrates | Reoviridae,Rotavirus,Rotavirus D | 1 | seg. 9 | GU733451 |
| Rotavirus D chicken/05V0049/DEU/2005 | NC_014520 | vertebrates | Reoviridae,Rotavirus,Rotavirus D | 1 | seg. 10 | GU733452 |
| Rotavirus D chicken/05V0049/DEU/2005 | NC_014521 | vertebrates | Reoviridae,Rotavirus,Rotavirus D | 1 | seg. 11 | GU733453 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rous sarcoma virus | NC_001407 | vertebrates | 3 | Retroviridae,Alpharetrovirus,Rous sarcoma virus | — | V01197,X68524,AF033808 |
| Rous sarcoma virus-Prague C | NC_001407 | vertebrates | 1 | Retroviridae,Alpharetrovirus,Rous sarcoma virus | — | JQ2342 |
| Rous sarcoma virus-Schmidt-Ruppin B | NC_001407 | vertebrates | 1 | Retroviridae,Alpharetrovirus,Rous sarcoma virus | — | AF052428 |
| Rous sarcoma virus-Schmidt-Ruppin D | NC_001407 | vertebrates | 1 | Retroviridae,Alpharetrovirus,Rous sarcoma virus | — | D10652 |
| Rousettus aegyptiacus papillomavirus type 1 | NC_008298 | vertebrates | 1 | Papillomaviridae,Psipapillomavirus,Psipapillomavirus 1 | — | DQ366842 |
| Rousettus bat coronavirus HKU10 | NC_018871 | vertebrates | 2 | Coronaviridae,Alphacoronavirus,Bat coronavirus HKU10 | — | JQ989271,JQ989270 |
| Rousettus bat coronavirus HKU9 | NC_009021 | vertebrates | 1 | Coronaviridae,Betacoronavirus,Rousettus bat coronavirus HKU9 | — | EF065513 |
| SIVcpz Ptt-04Cam155 | NC_001549,NC_004455 | vertebrates | 1 | Retroviridae,Lentivirus,Simian immunodeficiency virus | — | FR686510 |
| SIVcpz Ptt-09Cam155 | NC_001549,NC_004455 | vertebrates | 1 | Retroviridae,Lentivirus,Simian immunodeficiency virus | — | FR686511 |
| STL polyomavirus | NC_020106 | vertebrates | 3 | Polyomaviridae,Polyomavirus,STL polyomavirus | — | KF525270,JX463184,JX463183 |
| Sable antelope coronavirus U S/OH 1/2003 | NC_010327,NC_007732,NC_005147,NC_003045 | vertebrates | 1 | Coronaviridae,Betacoronavirus,Betacoronavirus 1 | — | EF424621 |
| Saffold virus | NC_009448,NC_001366,NC_010810 | vertebrates | 11 | Picornaviridae,Cardiovirus,Theilovirus | — | HM181998,FM207487,JF813004,HM181997,HM181996,HQ902242,HM181999,HQ162476,EF165067,GU943513,FN999911 |
| Saimiriine herpesvirus 1 | NC_014567 | vertebrates | 1 | Herpesviridae,Simplexvirus,Saimiriine herpesvirus 1 | — | HM625781 |
| Saimiriine herpesvirus 2 | NC_001350 | vertebrates | 2 | Herpesviridae,Rhadinovirus,Saimiriine herpesvirus 2 | — | AJ410493,X64346 |
| Saimiriine herpesvirus 3 | NC_016448 | vertebrates | 1 | Herpesviridae,Cytomegalovirus,Saimiriine herpesvirus 3 | — | FJ483967 |
| Salivirus | NC_012957,NC_012986 | vertebrates | 1 | Picornaviridae,Salivirus,Salivirus A | — | JN379039 |
| Salivirus A | NC_012957,NC_012986 | vertebrates | 1 | Picornaviridae,Salivirus,Salivirus A | — | GU245894 |
| Salivirus NG-J1 | NC_012957,NC_012986 | vertebrates | 1 | Picornaviridae,Salivirus,Salivirus A | — | GQ179640 |

TABLE 10-continued

| Taxonomy | Rep.Acc.ID | Host | ViroCap-1.0 Taxonomy | | Seg. Count | GN.Acc.IDs |
|---|---|---|---|---|---|---|
| | | | # GN's | Lineage | | |
| Sambar deer coronavirus US/OH-WD388-TC/1994 | NC_010327,NC_00773 2,NC_0051 47,NC_003 045 | vertebrates | 2 | Coronaviridae,Betacoronavirus,Betacoronavirus 1 | — | FJ425188,FJ425190 |
| Sambar deer coronavirus US/OH-W D388/1994 | NC_010327,NC_00773 2,NC_0051 47,NC_003 045 | vertebrates | 1 | Coronaviridae,Betacoronavirus,Betacoronavirus 1 | — | FJ425189 |
| San Miguel sea lion virus | NC_002551 | vertebrates | 1 | Caliciviridae,Vesivirus,Vesicular exanthema of swine virus | — | U15301 |
| Scotophilus bat coronavirus 512 | NC_009657 | vertebrates | 1 | Coronaviridae,Alphacoronavirus,Scotophilus bat coronavirus 512 | — | DQ648858 |
| Sea turtle tornovirus 1 | NC_012094 | vertebrates | 9 | Sea turtle tornovirus 1 | — | EU867817,EU867823,EU867821,EU86782 2,EU867816,EU8678 20,EU867818,EU867 824,EU867819 |
| Seal picornavirus type 1 | NC_009891 | vertebrates | 1 | Picornaviridae,Aquamavirus,Aquamavirus A | — | EU142040 |
| Sebokele virus 1 | NC_021482 | vertebrates | 1 | Picornaviridae,Parechovirus,Sebokele virus 1 | — | HF677705 |
| Seneca valley virus | NC_011349 | vertebrates | 2 | Picornaviridae,Senecavirus,Seneca valley virus | — | DQ641257,KC667560 |
| Sevenband grouper nervous necrosis virus | NC_008040 | vertebrates | 1 | Nodaviridae,Betanodavirus,Redspotted grouper nervous necrosis virus | seg. RNA 1 | AB373028 |
| Sevenband grouper nervous necrosis virus | NC_008041 | vertebrates | 1 | Nodaviridae,Betanodavirus,Redspotted grouper nervous necrosis virus | seg. RNA 2 | AB373029 |
| Sheeppox virus | NC_004002 | vertebrates | 1 | Poxviridae,Capripoxvirus,Sheeppox virus | — | AY077832 |
| Sheeppox virus A | NC_004002 | vertebrates | 1 | Poxviridae,Capripoxvirus,Sheeppox virus | — | AY077833 |
| Sheeppox virus NISKHI | NC_004002 | vertebrates | 1 | Poxviridae,Capripoxvirus,Sheeppox virus | — | AY077834 |
| Sheldgoose hepatitis B virus | NC_005890 | vertebrates | 2 | Hepadnaviridae, Sheldgoose hepatitis B virus | — | AY494853,AY494852 |
| Simian T-cell lymphotropic virus 6 | NC_011546 | vertebrates | 1 | Retroviridae,Deltaretrovirus,Simian T-cell lymphotropic virus 6 | — | EU231644 |
| Simian T-lymphotropic virus 1 | NC_000858,NC_00143 6 | vertebrates | 4 | Retroviridae,Deltaretrovirus,Primate T-lymphotropic virus 1 | — | Z46900,AF074966,JX 987040,AY590142 |
| Simian T-lymphotropic virus 2 | NC_001815,NC_00148 8 | vertebrates | 2 | Retroviridae,Deltaretrovirus,Primate T-lymphotropic virus 2 | — | Y14570,U90557 |
| Simian T-lymphotropic virus 3 | NC_003323 | vertebrates | 5 | Retroviridae,Deltaretrovirus,Primate T-lymphotropic virus 3 | — | AY217650,Y07616,A F391797,AF517775,A Y222339 |
| Simian adenovirus 1 | NC_006879 | vertebrates | 1 | Adenoviridae,Mastadenovirus,Human adenovirus G | — | AY771780 |
| Simian adenovirus 18 | NC_022266 | vertebrates | 1 | Adenoviridae,Mastadenovirus,Simian adenovirus 18 | — | FJQ25931 |

TABLE 10-continued

VrioCap-1.0 Taxonomy

| Taxonomy | Rep.Acc.ID | Host | # GN's | Lineage | Seg. Count | GN.Acc.IDs |
|---|---|---|---|---|---|---|
| Simian adenovirus 20 | NC_020485 | vertebrates | 1 | Adenoviridae,Mastadenovirus,Simian adenovirus 20 | — | HQ605912 |
| Simian adenovirus 22 | NC_003266,NC_017825 | vertebrates | 1 | Adenoviridae,Mastadenovirus,Human adenovirus E | — | AY530876 |
| Simian adenovirus 23 | NC_003266,NC_017825 | vertebrates | 1 | Adenoviridae,Mastadenovirus,Human adenovirus E | — | AY530877 |
| Simian adenovirus 24 | NC_003266,NC_017825 | vertebrates | 1 | Adenoviridae,Mastadenovirus,Human adenovirus E | — | AY530878 |
| Simian adenovirus 25 | NC_003266,NC_017825 | vertebrates | 1 | Adenoviridae,Mastadenovirus,Human adenovirus E | — | AF394196 |
| Simian adenovirus 25.2 | NC_003266,NC_017825 | vertebrates | 1 | Adenoviridae,Mastadenovirus,Human adenovirus E | — | FJ025918 |
| Simian adenovirus 26 | NC_003266,NC_017825 | vertebrates | 1 | Adenoviridae,Mastadenovirus,Human adenovirus E | — | FJ025923 |
| Simian adenovirus 3 | NC_006144 | vertebrates | 1 | Adenoviridae,Mastadenovirus,Simian adenovirus A | — | AY598782 |
| Simian adenovirus 30 | NC_003266,NC_017825 | vertebrates | 1 | Adenoviridae,Mastadenovirus,Human adenovirus E | — | FJ025920 |
| Simian adenovirus 36 | NC_003266,NC_017825 | vertebrates | 1 | Adenoviridae,Mastadenovirus,Human adenovirus E | — | FJ025917 |
| Simian adenovirus 37.1 | NC_003266,NC_017825 | vertebrates | 1 | Adenoviridae,Mastadenovirus,Human adenovirus E | — | FJ025921 |
| Simian adenovirus 37.2 | NC_003266,NC_017825 | vertebrates | 1 | Adenoviridae,Mastadenovirus,Human adenovirus E | — | FJ025919 |
| Simian adenovirus 38 | NC_003266,NC_017825 | vertebrates | 1 | Adenoviridae,Mastadenovirus,Human adenovirus E | — | FJ025922 |
| Simian adenovirus 39 | NC_003266,NC_017825 | vertebrates | 1 | Adenoviridae,Mastadenovirus,Human adenovirus E | — | FJ025924 |
| Simian adenovirus 49 | NC_015225 | vertebrates | 1 | Adenoviridae,Mastadenovirus,Simian adenovirus B | — | HQ241819 |
| Simian adenovirus 50 | NC_015225 | vertebrates | 1 | Adenoviridae,Mastadenovirus,Simian adenovirus B | — | HQ241820 |
| Simian adenovirus 6 | NC_006144 | vertebrates | 1 | Adenoviridae,Mastadenovirus,Simian adenovirus A | — | JQ776547 |
| Simian adenovirus A1139 | NC_015225 | vertebrates | 1 | Adenoviridae,Mastadenovirus,Simian adenovirus B | — | JN880448 |

TABLE 10-continued

VisoCap-1.0 Taxonomy

| Taxonomy | Rep.Acc.ID | Host | # GN's | Lineage | Seg. Count | GN.Acc.IDs |
|---|---|---|---|---|---|---|
| Simian adenovirus A1163 | NC_015225 | vertebrates | 1 | Adenoviridae,Mastadenovirus,Simian adenovirus B | — | JN880449 |
| Simian adenovirus A1173 | NC_015225 | vertebrates | 1 | Adenoviridae,Mastadenovirus,Simian adenovirus B | — | JN880450 |
| Simian adenovirus A1258 | NC_015225 | vertebrates | 1 | Adenoviridae,Mastadenovirus,Simian adenovirus B | — | JN880451 |
| Simian adenovirus A1285 | NC_015225 | vertebrates | 1 | Adenoviridae,Mastadenovirus,Simian adenovirus B | — | JN880452 |
| Simian adenovirus A1296 | NC_015225 | vertebrates | 1 | Adenoviridae,Mastadenovirus,Simian adenovirus B | — | JN880453 |
| Simian adenovirus A1312 | NC_015225 | vertebrates | 1 | Adenoviridae,Mastadenovirus,Simian adenovirus B | — | JN880454 |
| Simian adenovirus A1327 | NC_015225 | vertebrates | 1 | Adenoviridae,Mastadenovirus,Simian adenovirus B | — | JN880455 |
| Simian adenovirus A1335 | NC_015225 | vertebrates | 1 | Adenoviridae,Mastadenovirus,Simian adenovirus B | — | JN880456 |
| Simian adenovirus B | NC_015225 | vertebrates | 1 | Adenoviridae,Mastadenovirus,Simian adenovirus B | — | KC693021 |
| Simian adenovirus C | NC_021168 | vertebrates | 3 | Adenoviridae,Mastadenovirus,Simian adenovirus C | — | KC693024,KC693023,KC693022 |
| Simian endogenous retrovirus vero ATCC CCL-81 | NC_001550 | vertebrates | 1 | Retroviridae,Betaretrovirus,Mason-Pfizer monkey virus | — | JN134185 |
| Simian enterovirus A | NC_003988 | vertebrates | 1 | Picornaviridae,Enterovirus,Enterovirus H | — | AF201894 |
| Simian enterovirus SV4 | NC_003988 | vertebrates | 1 | Picornaviridae,Enterovirus,Enterovirus H | — | AF326759 |
| Simian foamy virus | NC_001364 | vertebrates | 5 | Retroviridae,Spumavirus,Simian foamy virus | — | JQ867465,JQ867462,JQ867464,U04327,J0867463 |
| Simian foamy virus-gorilla | NC_001364 | vertebrates | 1 | Retroviridae,Spumavirus,Simian foamy virus | — | HM245790 |
| Simian foamy virus-orangutan | NC_001364 | vertebrates | 1 | Retroviridae,Spumavirus,Simian foamy virus | — | AJ544579 |
| Simian hemorrhagic fever virus | NC_003092 | vertebrates | 1 | Arteriviridae,Arterivirus,Simian hemorrhagic fever virus | — | AF180391 |
| Simian hepatitis A virus | NC_001489 | vertebrates | 2 | Picornaviridae,Hepatovirus,Hepatitis A virus | — | EU140838,DQ0924 |
| Simian immunodeficiency virus | NC_001549,NC_004455 | vertebrates | 109 | Retroviridae,Lentivirus,Simian immunodeficiency virus | — | JN091690,AY597209,AB253736,AY340700,AF328295,DQ37306 3,EU280804,AF0752 69,EF070331,EF5359 93,EF394357,M3132 5,U79412,AY611486, M27470,AY169968,E F070330,AY603959,A Y576480,M19499,EU 280805,AY599198,D 0201174,JN835461, AY611488,AY607702 ,AJ271369,AY599201 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | ,AY159322,AY523866,AY576481,DQ374658,AY588945,DQ201173,AY611494,AB177846,AF103818,AM713177,EF070329,X52154,AY588946,M32741,FJ424863,DQ374657,M30931,EF394358,JQ866001,AY611491,M58410,JQ864084,M33262,M29975,AF382829,EF535994,AF077017,FR751162,M66437,FJ424865,AF468658,EU280806,AY607703,AY340701,FJ424871,FJ424864,FJ424866,AY607701,AY611487,AY611492,AF468659,AF301156,AY611489,AY523865,M76764,JN091691,AY599200,JQ864086,EF394356,AF131870,M83293,AY611495,JQ864087,DQ373064,AF115393,JN835462,EU280803,DQ201172,AY655744,AY587015,L06042,JN835460,AY600249,AF334679,U72748,XQ7805,L03295,AJ580407,DQ373066,AY611493,AM745105,AY159321,AY523867,DQ373065,AY607704,AY599199,AM182197,JQ864085,AF382828,AY611490,AF447763 |
| Simian immunodeficiency virus-agm.sab-1 | NC_001549,NC_004455 | vertebrates | 1 | Retroviridae,Lentivirus,Simian immunodeficiency virus | — | U04005 |
| Simian immunodeficiency virus-agm.tan-1 | NC_001549,NC_004455 | vertebrates | 1 | Retroviridae,Lentivirus,Simian immunodeficiency virus | — | U58991 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Simian immunodeficiency virus 17E-CI | NC_001549,NC_004455 | vertebrates | 1 | Retroviridae,Lentivirus,Simian immunodeficiency virus | — | AY033233 |
| Simian immunodeficiency virus 17E-Fr | NC_001549,NC_004455 | vertebrates | 1 | Retroviridae,Lentivirus,Simian immunodeficiency virus | — | AY033146 |
| Simian retrovirus 1 | NC_001550 | vertebrates | 2 | Retroviridae,Betaretrovirus,Mason-Pfizer monkey virus | — | M11841,U85505 |
| Simian retrovirus 2 | NC_001550 | vertebrates | 3 | Retroviridae,Betaretrovirus,Mason-Pfizer monkey virus | — | M16605,AF126467,AF126468 |
| Simian retrovirus 4 | NC_014474 | vertebrates | 3 | Retroviridae,Betaretrovirus,Simian retrovirus 4 | — | FJ979639,FJ971077,FJ979638 |
| Simian sapelovirus 1 | NC_004451 | vertebrates | 1 | Picornaviridae,Sapelovirus,Simian sapelovirus | — | AY064708 |
| Simian virus 12 | NC_007611 | vertebrates | 2 | Polyomaviridae,Polyomavirus,Simian virus 12 | — | DQ435829,AY614708 |
| Singapore grouper iridovirus | NC_006549 | vertebrates | 1 | Iridoviridae,Ranavirus,Singapore grouper iridovirus | — | AY521625 |
| Siniperca chuatsi rhabdovirus | NC_008514 | vertebrates | 1 | Rhabdoviridae, Siniperca chuatsi rhabdovirus | — | DQ399789 |
| Small ruminant lentivirus | NC_001463 | vertebrates | 1 | Retroviridae,Lentivirus,Caprine arthritis encephalitis virus | — | HM210570 |
| Snake adenovirus 1 | NC_009989 | vertebrates | 1 | Adenoviridae,Atadenovirus,Snake adenovirus A | — | DQ106414 |
| Snake parvovirus 1 | NC_006148 | vertebrates | 1 | Parvoviridae,Dependovirus,Snake parvovirus 1 | — | AY349010 |
| Snakehead retrovirus | NC_001724 | vertebrates | 1 | Retroviridae, Snakehead retrovirus | — | U26458 |
| Snakehead rhabdovirus | NC_000903 | vertebrates | 1 | Rhabdoviridae,Novirhabdovirus,Snakehead virus | — | AF147498 |
| Snow goose hepatitis B virus | NC_005888,NC_005950 | vertebrates | 4 | Hepadnaviridae, Ross's goose hepatitis B virus | — | AF110999,AF111000,AF110997,AF110998 |
| Soft-shelled turtle iridovirus | NC_005946 | vertebrates | 1 | Iridoviridae,Ranavirus,Frog virus 3 | — | EU627010 |
| South polar skua adenovirus-1 | NC_016437 | vertebrates | 1 | Adenoviridae,Siadenovirus,Skua adenovirus A | — | HM585353 |
| Sparrow coronavirus HKU17 | NC_016992 | vertebrates | 1 | Coronaviridae,Deltacoronavirus,Sparrow coronavirus HKU17 | — | JQ065045 |
| Spider monkey foamy virus | NC_001364 | vertebrates | 1 | Retroviridae,Spumavirus,Simian foamy virus | — | EU010385 |
| Spissistilus festinus reovirus | NC_016874 | vertebrates | 1 | Reoviridae,Spissistilus festinus reovirus | seg. 2 | JF773383 |
| Spissistilus festinus reovirus | NC_016875 | vertebrates | 1 | Reoviridae,Spissistilus festinus reovirus | seg. 4 | JF773385 |
| Spissistilus festinus reovirus | NC_016876 | vertebrates | 1 | Reoviridae,Spissistilus festinus reovirus | seg. 6 | JF773387 |
| Spissistilus festinus reovirus | NC_016877 | vertebrates | 1 | Reoviridae,Spissistilus festinus reovirus | seg. 8 | JF773389 |
| Spissistilus festinus reovirus | NC_016878 | vertebrates | 1 | Reoviridae,Spissistilus festinus reovirus | seg. 10 | JF773391 |
| Spissistilus festinus reovirus | NC_016879 | vertebrates | 1 | Reoviridae,Spissistilus festinus reovirus | seg. 1 | JF773382 |

TABLE 10-continued

VircCap-1.0 Taxonomy

| Taxonomy | Rep.Acc.ID | Host | Lineage | # GN's | Seg. Count | GN.Acc.IDs |
|---|---|---|---|---|---|---|
| Spissistilus festinus reovirus | NC_016880 | vertebrates | Reoviridae,Spissistilus festinus reovirus | 1 | seg. 3 | JF773384 |
| Spissistilus festinus reovirus | NC_016881 | vertebrates | Reoviridae,Spissistilus festinus reovirus | 1 | seg. 5 | JF773386 |
| Spissistilus festinus reovirus | NC_016882 | vertebrates | Reoviridae,Spissistilus festinus reovirus | 1 | seg. 7 | JF773388 |
| Spissistilus festinus reovirus | NC_016883 | vertebrates | Reoviridae,Spissistilus festinus reovirus | 1 | seg. 9 | JF773390 |
| Spleen focus-forming virus | NC_001500 | vertebrates | Retroviridae,Gammaretrovirus,Spleen focus-forming virus | 1 | — | K00021 |
| Spring viraemia of carp virus | NC_002803 | vertebrates | Rhabdoviridae,Vesiculovirus,Spring viraemia of carp virus | 4 | — | U18101,AJ318079,E U177782,DQ491000 |
| Spring viremia of carp virus | NC_002803 | vertebrates | Rhabdoviridae,Vesiculovirus,Spring viraemia of carp virus | 1 | — | DQ097384 |
| Squirrel monkey foamy virus | NC_001364 | vertebrates | Retroviridae,Spumavirus,Simian foamy virus | 1 | — | GU356394 |
| Squirrel monkey polyomavirus | NC_009951 | vertebrates | Polyomaviridae,Polyomavirus,Squirrel monkey polyomavirus | 1 | — | AM748741 |
| Squirrel monkey retrovirus | NC_001514 | vertebrates | Retroviridae,Betaretrovirus,Squirrel monkey retrovirus | 1 | — | M23385 |
| Squirrelpox virus | NC_022563 | vertebrates | Poxviridae,Squirrelpox virus | 1 | — | HE601899 |
| St-Valerien swine virus | NC_012699 | vertebrates | Caliciviridae,St-Valerien swine virus | 1 | — | AB863586 |
| Starling circovirus | NC_008033 | vertebrates | Circoviridae,Circovirus,Starling circovirus | 1 | — | DQ172906 |
| Steller sea lion vesivirus | NC_011050 | vertebrates | Caliciviridae,Vesivirus,Steller sea lion vesivirus | 2 | — | EF193004,EF195384 |
| Stork hepatitis B virus | NC_001486 | vertebrates | Hepadnaviridae,Avihepadnavirus,Heron hepatitis B virus | 4 | — | AJ251937,AJ251935, AJ251936,AJ251934 |
| Striped Jack nervous necrosis virus | NC_003448 | vertebrates | Nodaviridae,Betanodavirus,Striped Jack nervous necrosis virus | 2 | seg. RNA 1 | AB025018,AB056571 |
| Striped Jack nervous necrosis virus | NC_003449 | vertebrates | Nodaviridae,Betanodavirus,Striped Jack nervous necrosis virus | 2 | seg. RNA 2 | AB056572,D30814 |
| Striped bass reovirus | NC_007588 | vertebrates | Reoviridae,Aquareovirus,Aquareovirus A | 1 | seg. 8 | AF450321 |
| Striped bass reovirus | NC_007590 | vertebrates | Reoviridae,Aquareovirus,Aquareovirus A | 2 | seg. 10 | U83396,AF450322 |
| Suid herpesvirus 1 | NC_006151 | vertebrates | Herpesviridae,Varicellovirus,Suid herpesvirus 1 | 6 | — | JF797217,BK001744, JQ809330,JQ809329, JF797219,JF797218 |
| Sus scrofa papillomavirus type 1 | NC_011280 | vertebrates | Papillomaviridae,Dyodeltapapillomavirus,Dyod eltapapillomavirus 1 | 2 | — | EF395819,EF395818 |
| Swine pasivirus 1 | NC_018226 | vertebrates | Picornaviridae,Swine pasivirus 1 | 1 | — | JQ316470 |
| Swinepox virus | NC_003389 | vertebrates | Poxviridae,Suipoxvirus,Swinepox virus | 1 | — | AF410153 |
| TGEV Miller M6 | NC_002306 | vertebrates | Coronaviridae,Alphacoronavirus,Alphacoronav irus 1 | 1 | — | DQ811785 |
| TGEV Miller M60 | NC_002306 | vertebrates | Coronaviridae,Alphacoronavirus,Alphacoronav irus 1 | 1 | — | DQ811786 |
| TGEV Purdue P115 | NC_002306 | vertebrates | Coronaviridae,Alphacoronavirus,Alphacoronav irus 1 | 1 | — | DQ811788 |

TABLE 10-continued

VlroCap-1.0 Taxonomy

| Taxonomy | Rep.Acc.ID | Host | Lineage | # GN's | Seg. Count | GN.Acc.IDs |
|---|---|---|---|---|---|---|
| TGEV virulent Purdue | NC_002306 | vertebrates | Coronaviridae,Alphacoronavirus,Alphacoronavirus 1 | 1 | — | DQ811789 |
| Tanapox virus | NC_002642,NC_009888 | vertebrates | Poxviridae,Yatapoxvirus,Tanapox virus | 1 | — | EF420157 |
| Taterapox virus | NC_008291 | vertebrates | Poxviridae,Orthopoxvirus,Taterapox virus | 1 | — | DQ437594 |
| Theiler's encephalomyelitis virus | NC_009448,NC_001366,NC_010810 | vertebrates | Picornaviridae,Cardiovirus,Theilovirus | 9 | — | M16020,EU723238,EU718732,HQ652539,EU718733,M20301,D0401688,M20562,JX443418 |
| Theiler's-like virus of rats | NC_009448,NC_001366,NC_010810 | vertebrates | Picornaviridae,Cardiovirus,Theilovirus | 1 | — | AB090161 |
| Threadfin reovirus | NC_007590 | vertebrates | Reoviridae,Aquareovirus,Aquareovirus A | 1 | seg. 10 | AY236219 |
| Threadfin reovirus | NC_007591 | vertebrates | Reoviridae,Aquareovirus,Aquareovirus A | 1 | seg. 11 | AF524892 |
| Threadfin reovirus | NC_007592 | vertebrates | Reoviridae,Aquareovirus,Aquareovirus A | 1 | seg. 6 | AY235428 |
| Thrush coronavirus HKU12-600 | NC_011549 | vertebrates | Coronaviridae,Deltacoronavirus,Thrush coronavirus HKU12 | 1 | — | FJ376621 |
| Tiger frog virus | NC_005946 | vertebrates | Iridoviridae,Ranavirus,Frog virus 3 | 1 | — | AF389451 |
| Tiger puffer nervous necrosis virus | NC_013460 | vertebrates | Nodaviridae,Betanodavirus,Tiger puffer nervous necrosis virus | 1 | seg. RNA 1 | EU236148 |
| Tiger puffer nervous necrosis virus | NC_013461 | vertebrates | Nodaviridae,Betanodavirus,Tiger puffer nervous necrosis virus | 1 | seg. RNA 2 | EU236149 |
| Titi monkey adenovirus ECC-2011 | NC_020487 | vertebrates | Adenoviridae, Titi monkey adenovirus ECC-2011 | 1 | — | HQ913600 |
| Transmissible gastroenteritis virus | NC_002306 | vertebrates | Coronaviridae,Alphacoronavirus,Alphacoronavirus 1 | 10 | — | HQ462571,DQ201447,AJ271965,AX154950,KC962433,EU074218,C087O486,DQ443743,HM776941,FJ755618 |
| Trichechus manatus latirostris papillomavirus 1 | NC_006563 | vertebrates | Papillomaviridae,Rhopapillomavirus,Rhopapillomavirus 1 | 1 | — | AY609301 |
| Trichechus manatus latirostris papillomavirus 2 | NC_016898 | vertebrates | Papillomaviridae,Trichechus manatus latirostris papillomavirus 2 | 1 | — | JN709473 |
| Trichodysplasia spinulosa-associated polyomavirus | NC_014361 | vertebrates | Polyomaviridae,Polyomavirus,Trichodysplasia spinulosa-associated polyomavirus | 3 | — | GU989205,AB873001,JQ723730 |
| Tupaia virus | NC_007020 | vertebrates | Rhabdoviridae, Tupaia virus | 1 | — | AY840978 |
| Tupaiid herpesvirus 1 | NC_002794 | vertebrates | Herpesviridae, Tupaiid herpesvirus 1 | 1 | — | AF281817 |
| Turdivirus 1 | NC_014411 | vertebrates | Picornaviridae,Orthoturdivirus,Turdivirus 1 | 2 | — | GU182406,GU182407 |
| Turdivirus 2 | NC_014412 | vertebrates | Picornaviridae,Paraturdivirus,Turdivirus 2 | 2 | — | GU182409,GU182408 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Turdivirus 3 | NC_014413 | vertebrates | 2 | Picornaviridae,Paraturdivirus,Turdivirus 3 | — | GU182411,GU182410 |
| Turkey adenovirus 1 | NC_014564 | vertebrates | 1 | Adenoviridae,Aviadenovirus,Turkey adenovirus B | — | GU936707 |
| Turkey adenovirus 4 | NC_022612 | vertebrates | 1 | Adenoviridae,Aviadenovirus,Turkey adenovirus 4 | — | KF477312 |
| Turkey adenovirus 5 | NC_022613 | vertebrates | 1 | Adenoviridae,Aviadenovirus,Turkey adenovirus 5 | — | KF477313 |
| Turkey adenovirus A | NC_001958 | vertebrates | 1 | Adenoviridae,Siadenovirus,Turkey adenovirus A | — | AF074946 |
| Turkey astrovirus | NC_002470 | vertebrates | 8 | Astroviridae,Avastrovirus,Turkey astrovirus | — | EU143850,EU143845,EU143848,EU143849,EU143846,EU143847,EU143844,Y15936 |
| Turkey astrovirus 2 | NC_005790 | vertebrates | 2 | Astroviridae,Avastrovirus,Avastrovirus 3 | — | EU143843,AF206663 |
| Turkey coronavirus | NC_010800,NC_001451 | vertebrates | 7 | Coronaviridae,Gammacoronavirus,Avian coronavirus | — | GQ427175,EU022252 6,GQ427174,GQ427173,GQ427176,EU022525,EU095850 |
| Turkey gallivirus | NC_018400 | vertebrates | 1 | Picornaviridae, Turkey gallivirus | — | JQ691613 |
| Turkey hepatitis virus 2993D | NC_021201 | vertebrates | 1 | Picornaviridae,Megrivirus,Melegrivirus A | — | HM751199 |
| Tursiops truncatus papillomavirus 1 | NC_011109 | vertebrates | 1 | Papillomaviridae,Upsilonpapillomavirus,Upsilonpapillomavirus 1 | — | EU240894 |
| Tursiops truncatus papillomavirus 2 | NC_008184 | vertebrates | 1 | Papillomaviridae,Upsilonpapillomavirus,Upsilonpapillomavirus 2 | — | AY956402 |
| Tursiops truncatus papillomavirus type 3 | NC_011109 | vertebrates | 1 | Papillomaviridae,Upsilonpapillomavirus,Upsilonpapillomavirus 1 | — | EU240895 |
| Tylonycteris bat coronavirus HKU4 | NC_009019 | vertebrates | 1 | Coronaviridae,Betacoronavirus,Tylonycteris bat coronavirus HKU4 | — | EF065505 |
| UR2 sarcoma virus | NC_001618 | vertebrates | 1 | Retroviridae,Alpharetrovirus,UR2 sarcoma virus | — | M10455 |
| Uncia uncia papillomavirus type 1 | NC_004765 | vertebrates | 1 | Papillomaviridae,Lambdapapillomavirus,Lambdapapillomavirus 1 | — | DQ180494 |
| Ursus maritimus papillomavirus 1 | NC_010739 | vertebrates | 1 | Papillomaviridae,Omegapapillomavirus,Omegapapillomavirus 1 | — | EF536349 |
| VESV-like calicivirus | NC_002551 | vertebrates | 1 | Caliciviridae,Vesivirus,Vesicular exanthema of swine virus | — | AF091736 |
| Vervet monkey polyomavirus 1 | NC_019844 | vertebrates | 1 | Polyomaviridae,Polyomavirus,Vervet monkey polyomavirus 1 | — | AB767298 |
| Vesicular exanthema of swine virus | NC_002551 | vertebrates | 1 | Caliciviridae,Vesivirus,Vesicular exanthema of swine virus | — | U76874 |
| Viral hemorrhagic septicemia virus | NC_000855 | vertebrates | 16 | Rhabdoviridae,Novirhabdovirus,Viral hemorrhagic septicemia virus | — | AB672614,EU481506,FJ460590,AF143862,AF143863,FJ362510,GQ385941,FN66578 8,JF792424,Z93412,KF477302,FJ460591, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Viral hemorrhagic septicemia virus (STRAIN 07-71) | NC_000855 | vertebrates | 1 | Rhabdoviridae,Novirhabdovirus,Viral hemorrhagic septicemia virus | — | Z93414,AB179621,AB490792,KC778774,AJ233396 |
| Viral hemorrhagic septicemia virus Fil3 | NC_000855 | vertebrates | 1 | Rhabdoviridae,Novirhabdovirus,Viral hemorrhagic septicemia virus | — | Y18263 |
| Visna/Maedi virus | NC_001452 | vertebrates | 7 | Retroviridae,Lentivirus,Visna/maedi virus | — | M10608,M60610,M60609,L06906,M51543,555323,A15114 |
| Visna/maedi virus | NC_001452 | vertebrates | 1 | Retroviridae,Lentivirus,Visna/maedi virus | — | HQ848062 |
| Walleye dermal sarcoma virus | NC_001867 | vertebrates | 3 | Retroviridae,Epsilonretrovirus,Walleye dermal sarcoma virus | — | AF033822,L41838,EF428979 |
| Walrus calicivirus | NC_004541 | vertebrates | 1 | Caliciviridae, Walrus calicivirus | — | AF321298 |
| Waterbuck coronavirus US/OH-WD358-GnC/1994 | NC_010327,NC_007732,NC_0051 47,NC_003045 | vertebrates | 1 | Coronaviridae,Betacoronavirus,Betacoronavirus 1 | — | FJ425185 |
| Waterbuck coronavirus US/OH-WD358-TC/1994 | NC_010327,NC_007732,NC_0051 47,NC_003045 | vertebrates | 1 | Coronaviridae,Betacoronavirus,Betacoronavirus 1 | — | FJ425184 |
| Waterbuck coronavirus US/OH-W D358/1994 | NC_010327,NC_007732,NC_0051 47,NC_003045 | vertebrates | 1 | Coronaviridae,Betacoronavirus,Betacoronavirus 1 | — | FJ425186 |
| White bream virus | NC_008516 | vertebrates | 1 | Coronaviridae,Bafinivirus,White bream virus | — | DQ898157 |
| White-eye coronavirus HKU16 | NC_016991 | vertebrates | 1 | Coronaviridae,Deltacoronavirus,White-eye coronavirus HKU16 | — | JQ065044 |
| White-tailed deer coronavirus US/OH-WD470/1994 | NC_010327,NC_007732,NC_0051 47,NC_003045 | vertebrates | 1 | Coronaviridae,Betacoronavirus,Betacoronavirus 1 | — | FJ425187 |
| Wigeon coronavirus HKU20 | NC_016995 | vertebrates | 1 | Coronaviridae,Deltacoronavirus,Wigeon coronavirus HKU20 | — | JQ065048 |
| Wood mouse herpesvirus | NC_001826 | vertebrates | 1 | Herpesviridae,Rhadinovirus,Murid herpesvirus 4 | — | GQ169129 |
| Woodchuck hepatitis virus | NC_004107 | vertebrates | 19 | Hepadnaviridae,Orthohepadnavirus,Woodchuck hepatitis virus | — | KF874491,M11082,M19183,M18752,GU734791,JQ4514,AY33404 77,KF874493,AY3340 75,AY334076,AY628 100,JQ2442,AY62809 7,AY628099,AY6280 |

TABLE 10-continued

| Taxonomy | Rep.Acc.ID | Host | # GN's | Lineage | Seg. Count | GN.Acc.IDs |
|---|---|---|---|---|---|---|
| Woolly monkey sarcoma virus | NC_009424 | vertebrates | 1 | Retroviridae,Gammaretrovirus,Woolly monkey sarcoma virus | — | 98,KF874492,AY6280 95,AY628096,M9052 0 |
| XMRV | NC_007815 | vertebrates | 1 | Retroviridae,Gammaretrovirus,Murine leukemia-related retroviruses | — | V01201 |
| XMRV-like mouse endogenous retrovirus mERV-XL | NC_007815 | vertebrates | 1 | Retroviridae,Gammaretrovirus,Murine leukemia-related retroviruses | — | FR872816 |
| Xenopus laevis endogenous retrovirus Xen1 | NC_010955 | vertebrates | 1 | Retroviridae, Xenopus laevis endogenous retrovirus Xen1 | — | JF714652 |
| Xenotropic MuLV-related virus | NC_007815 | vertebrates | 4 | Retroviridae,Gammaretrovirus,Murine leukemia-related retroviruses | — | AJ506107 |
| Xenotropic MuLV-related virus VP35 | NC_007815 | vertebrates | 1 | Retroviridae,Gammaretrovirus,Murine leukemia-related retroviruses | — | HQ154630,GQ49734 3,GQ497344,FN6920 43 |
| Xenotropic MuLV-related virus VP42 | NC_007815 | vertebrates | 1 | Retroviridae,Gammaretrovirus,Murine leukemia-related retroviruses | — | DQ241301 |
| Xenotropic MuLV-related virus VP62 | NC_007815 | vertebrates | 2 | Retroviridae,Gammaretrovirus,Murine leukemia-related retroviruses | — | DQ241302 |
| Xenotropic murine leukemia virus | NC_001702 ,NC_00181 9,NC_0013 62,NC_001 501 | vertebrates | 2 | Retroviridae,Gammaretrovirus,Murine leukemia virus | — | EF185282,DQ399707 |
| | | | | | | JF908816,JF908815 |
| Y73 sarcoma virus | NC_008094 | vertebrates | 2 | Retroviridae,Alpharetrovirus,Y73 sarcoma virus | — | V01170,L21974 |
| Yaba monkey tumor virus | NC_005179 | vertebrates | 1 | Poxviridae,Yatapoxvirus,Yaba monkey tumor virus | — | AY386371 |
| Yaba-like disease virus | NC_002642 ,NC_00988 8 | vertebrates | 1 | Poxviridae,Yatapoxvirus,Tanapox virus | — | AJ293568 |
| Yellowtail ascites virus | NC_004168 | vertebrates | 3 | Birnaviridae,Aquabirnavirus,Yellowtail ascites virus RNA | seg. A | AB281673,AB011440 ,AB006783 |
| Yellowtail ascites virus | NC_004176 | vertebrates | 2 | Birnaviridae,Aquabirnavirus,Yellowtail ascites virus | seg. RNA B | AY129662,AB281674 |
| Yellowtail ascites virus-YT-01A | NC_004176 | vertebrates | 1 | Birnaviridae,Aquabirnavirus,Yellowtail ascites virus | seg. RNA B | AY129663 |
| Yoka poxvirus | NC_015960 | vertebrates | 1 | Poxviridae,Orthopoxvirus,Yoka poxvirus | — | HQ849551 |
| Zalophus californianus papillomavirus 1 | NC_015325 | vertebrates | 1 | Papillomaviridae,Zalophus californianus papillomavirus 1 | — | HQ293213 |
| Zetapapillomavirus 1 | NC_003748 | vertebrates | 1 | Papillomaviridae,Zetapapillomavirus,Zetapapillomavirus 1 | — | AF394740 |
| Adeno-associated virus-2 | NC_001401 | vertebrates,human | 2 | Parvoviridae,Dependovirus,Adeno-associated virus-2 | — | AF043303,JQ1901 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Adeno-associated virus-3 | NC_001729 | vertebrates,human | 1 | Parvoviridae,Dependovirus,Adeno-associated virus-3 | — | U48704 |
| Adeno-associated virus-5 | NC_006152 | vertebrates,human | 2 | Parvoviridae,Dependovirus,Adeno-associated virus-5 | — | AF085716,Y18065 |
| Adeno-associated virus 3B | NC_001729 | vertebrates,human | 1 | Parvoviridae,Dependovirus,Adeno-associated virus-3 | — | AF028705 |
| Adeno-associated virus-Go.1 | NC_006152 | vertebrates,human | 1 | Parvoviridae,Dependovirus,Adeno-associated virus-5 | — | DQ335246 |
| Adult diarrheal rotavirus strain J19 | NC_007548 | vertebrates,human | 1 | Reoviridae,Rotavirus,Rotavirus H | seg. 1 | DQ113897 |
| Adult diarrheal rotavirus strain J19 | NC_007549 | vertebrates,human | 1 | Reoviridae,Rotavirus,Rotavirus H | seg. 2 | DQ113898 |
| Adult diarrheal rotavirus strain J19 | NC_007550 | vertebrates,human | 1 | Reoviridae,Rotavirus,Rotavirus H | seg. 4 | DQ113899 |
| Adult diarrheal rotavirus strain J19 | NC_007551 | vertebrates,human | 1 | Reoviridae,Rotavirus,Rotavirus H | seg. 3 | DQ113900 |
| Adult diarrheal rotavirus strain J19 | NC_007552 | vertebrates,human | 1 | Reoviridae,Rotavirus,Rotavirus H | seg. 5 | DQ113901 |
| Adult diarrheal rotavirus strain J19 | NC_007553 | vertebrates,human | 1 | Reoviridae,Rotavirus,Rotavirus H | seg. 6 | DQ113902 |
| Adult diarrheal rotavirus strain J19 | NC_007554 | vertebrates,human | 1 | Reoviridae,Rotavirus,Rotavirus H | seg. 8 | DQ113903 |
| Adult diarrheal rotavirus strain J19 | NC_007555 | vertebrates,human | 1 | Reoviridae,Rotavirus,Rotavirus H | seg. 7 | DQ113904 |
| Adult diarrheal rotavirus strain J19 | NC_007556 | vertebrates,human | 1 | Reoviridae,Rotavirus,Rotavirus H | seg. 9 | DQ113905 |
| Adult diarrheal rotavirus strain J19 | NC_007557 | vertebrates,human | 1 | Reoviridae,Rotavirus,Rotavirus H | seg. 10 | DQ113906 |
| Adult diarrheal rotavirus strain J19 | NC_007558 | vertebrates,human | 1 | Reoviridae,Rotavirus,Rotavirus H | seg. 11 | DQ113907 |
| Allpahuayo virus | NC_010249 | vertebrates,human | 1 | Arenaviridae,Arenavirus,Allpahuayo virus | seg. L | AY216502 |
| Allpahuayo virus | NC_010253,AY012687 | vertebrates,human | 3 | Arenaviridae,Arenavirus,Allpahuayo virus | seg. S | AY012686,AY081210 |
| Alpaca respiratory coronavirus | NC_002645 | vertebrates,human | 1 | Coronaviridae,Alphacoronavirus,Human coronavirus 229E | — | JQ410000 |
| Amapari virus | NC_010247 | vertebrates,human | 2 | Arenaviridae,Arenavirus,Amapari virus | seg. S | AF485256,AF512834 |
| Amapari virus | NC_010251 | vertebrates,human | 2 | Arenaviridae,Arenavirus,Amapari virus | seg. L | AY924389,AY216517 |
| Andes virus | NC_003466 | vertebrates,human | 5 | Bunyaviridae,Hantavirus,Andes virus | seg. S | AF291702,AF004660,AF324902,AY228237,AF325966 |
| Andes virus | NC_003467 | vertebrates,human | 3 | Bunyaviridae,Hantavirus,Andes virus | seg. M | AF291703,AF324901,AY228238 |
| Andes virus | NC_003468 | vertebrates,human | 2 | Bunyaviridae,Hantavirus,Andes virus | seg. L | AY228239,AF291704 |
| Araraquara-like virus strain P5/Cajuru | NC_003466 | vertebrates,human | 1 | Bunyaviridae,Hantavirus,Andes virus | seg. S | EF571895 |
| Aravan virus | NC_020808 | vertebrates,human | 1 | Rhabdoviridae,Lyssavirus,Aravan virus | — | EF614259 |
| Arenavirus AV 96010025 | NC_010700 | vertebrates,human | 1 | Arenaviridae,Arenavirus,Whitewater Arroyo virus | seg. S | EU486820 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Arenavirus HQ380005 | NC_010700 | vertebrates,human | 1 | Arenaviridae,Arenavirus,Whitewater Arroyo virus | seg. S | EU910959 |
| Australian bat lyssavirus | NC_003243 | vertebrates,human | 2 | Rhabdoviridae,Lyssavirus,Australian bat lyssavirus | — | AF418014,AF081020 |
| Avian hepatitis E virus | NC_023425 | vertebrates,human | 3 | Hepeviridae,Avian hepatitis E virus | — | AM943646,AY535004,KC454286 |
| Avian metapneumovirus | NC_007652 | vertebrates,human | 10 | Paramyxoviridae,Metapneumovirus,Avian metapneumovirus | — | DQ009484,EF199772,AY640317,JF424833,DQ666911,AB54842 8,EF199771,AY59068 8,FJ977568,AY57978 0 |
| Avian paramyxovirus 4 | NC_019531 | vertebrates,human | 5 | Paramyxoviridae,Avulavirus,Avian paramyxovirus 4 | — | JX987283,EU877976,FJ177514,JN571485,JX133079 |
| Avian paramyxovirus 6 | NC_003043 | vertebrates,human | 7 | Paramyxoviridae,Avulavirus,Avian paramyxovirus 6 | — | EU622637,JX522537,KF267717,AY029299,AB759118,EF569970,GQ406232 |
| Avian rotavirus A | NC_011508 | vertebrates,human | 1 | Reoviridae,Rotavirus,Rotavirus A | seg. 3 | AY277923 |
| Avian rotavirus A | NC_011509 | vertebrates,human | 1 | Reoviridae,Rotavirus,Rotavirus A | seg. 6 | DQ096805 |
| Avian rotavirus CH2 | NC_011509 | vertebrates,human | 1 | Reoviridae,Rotavirus,Rotavirus A | seg. 6 | EF687020 |
| Avian rotavirus P0-13 | NC_011506 | vertebrates,human | 1 | Reoviridae,Rotavirus,Rotavirus A | seg. 2 | AB009630 |
| Avian rotavirus P0-13 | NC_011507 | vertebrates,human | 1 | Reoviridae,Rotavirus,Rotavirus A | seg. 1 | AB009629 |
| Avian rotavirus P0-13 | NC_011508 | vertebrates,human | 1 | Reoviridae,Rotavirus,Rotavirus A | seg. 3 | AB009631 |
| BK polyomavirus | NC_001538 | vertebrates,human | 282 | Polyomaviridae,Polyomavirus,BK polyomavirus | — | KF055891,AB211388,AB269835,AB269836,AB263928,AB29894 1,AB464960,AB4649 63,JN192434,V01108 ,AB263918,AB26986 4,AB301093,AB2179 18,AB464955,AB365 166,JN192439,JN192 431,AB263925,AB26 3912,AB369091,AB3 65164,AY628237,AB 263926,FR720317,A B485697,AB464957, AB269868,FR720309 ,AB263938,AB26982 3,AB269840,AB2698 31,V01109,AB365163 ,FR720314,AB30109 5,AB369089,AB4856 96,AB269852,AB269 834,FR720312,AB26 9863,AB263934,FR7 |

TABLE 10-continued

VireCap-1.0 Taxonomy

| Taxonomy | Rep.Acc.ID | Host | # GN's | Lineage | Seg. Count | GN.Acc.IDs |
|---|---|---|---|---|---|---|
| | | | | | | 20321,AB299944,AB211371,AB211391,AB298945,FR720322,AB263922,AB269847,AB365158,AB36516 1,AB269827,AB3651 48,JN192438,AY6282 29,AB365139,AB301 087,AB263916,AB26 3920,M23122,AY628 235,AB365135,AY62 8233,AB217920,AB2 69855,AB485706,AB 269851,KF055892,AB 365171,AB365175,A B485709,AB369096, AY628225,AB269866 ,AB365151,AB26984 1,AB485707,AB2698 25,AB211387,AB365 132,AB269832,AY62 8231,AB260029,AB2 69848,AB365170,AB 365130,AB269844,A B269830,AB485712, AB269856,AB269853 ,AB301089,AB26984 5,AB365136,AB3651 55,AB301102,AB263 914,AB485703,JN192 432,FR720318,AB26 9861,AB365174,AB2 63933,AB301091,AB 269865,AB365134,A B301097,AB213487, AB301099,AB369094 ,AY628226,AB36909 3,AB217917,AB3651 69,AB269837,AB365 146,AY628227,JQ713 822,EF376992,AB260 033,AB263936,AB21 1373,AB211389,AB4 64958,AB464953,AB 365137,AB269839,A B211390,AB485698,J N192437,AB260031, AB365167,AB269842 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | ,FR720319,AB365168,AB269829,AB263917,AB365159,FR720320,AB301086,AB263937,AB365176,JN192440,AB269849,AB269838,AB211370,AB263919,AB365172,AB365144,AB260028,AB485708,JN192435,AB298947,AB269824,AB269857,AB269843,AB269846,AB365133,AB211381,AB365156,AY628234,AB369098,AB211385,AB263935,AB369100,AB365177,FR720323,AB301100,AB464962,AB365157,AB485705,AB485711,AB269867,FR720311,KF055893,AB365141,AB211377,AB365173,AB485701,AB260030,AB485700,AB211375,AB365140,AB217919,AB301092,AB369095,AB369087,AB263927,AB211374,AB464956,AB301103,AB365165,AB269833,AB365138,AY628230,AB269860,AB485699,AB211376,AB365147,AB369092,AB464954,AB269826,AB365143,AB365145,FR720310,AB369090,AB263924,AB369101,AB301101,AY628238,AB263913,AB485702,AB298946,AB365154,AB263930,AB301088,AB369088,AB365150,AB269826,AB260032,AB365149,AB211379,AY628228,AY628224 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Baboon enterovirus | NC_001612 | vertebrates,human | 1 | Picornaviridae,Enterovirus,Enterovirus A | — | AF326750 |
| Bat Coy 273/2005 | NC_004718 | vertebrates,human | 1 | Coronaviridae,Betacoronavirus,Severe acute respiratory syndrome-related coronavirus | — | DQ648856 |
| Bat Coy 279/2005 | NC_004718 | vertebrates,human | 1 | Coronaviridae,Betacoronavirus,Severe acute respiratory syndrome-related coronavirus | — | DQ648857 |
| Bat Hepatitis B virus | NC_003977 | vertebrates,human | 1 | Hepadnaviridae,Orthohepadnavirus,Hepatitis B virus | — | KC790377 |
| Bat SARS Coy Rf1/2004 | NC_004718 | vertebrates,human | 1 | Coronaviridae,Betacoronavirus,Severe acute respiratory syndrome-related coronavirus | — | DQ412042 |
| Bat SARS Coy Rm1/2004 | NC_004718 | vertebrates,human | 1 | Coronaviridae,Betacoronavirus,Severe acute respiratory syndrome-related coronavirus | — | DQ412043 |
| Bat SARS Coy Rp3/2004 | NC_004718 | vertebrates,human | 1 | Coronaviridae,Betacoronavirus,Severe acute respiratory syndrome-related coronavirus | — | DQ071615 |
| Bat SARS coronavirus HKU3-10 | NC_004718 | vertebrates,human | 1 | Coronaviridae,Betacoronavirus,Severe acute respiratory syndrome-related coronavirus | — | GQ153545 |
| Bat SARS coronavirus HKU3-11 | NC_004718 | vertebrates,human | 1 | Coronaviridae,Betacoronavirus,Severe acute respiratory syndrome-related coronavirus | — | GQ153546 |
| Bat SARS coronavirus HKU3-12 | NC_004718 | vertebrates,human | 1 | Coronaviridae,Betacoronavirus,Severe acute respiratory syndrome-related coronavirus | — | GQ153547 |

GN.Acc.IDs (first row, continued): AB298940,AB269859,AB301098,AB369097,AB485710,AB211382,AB269858,DQ305492,AB485695,AB263921,AB301094,JN192433,AB263932,AB369099,AB365153,AB365131,FR720316,AB301090,AB211372,AB211386,AB298943,AB365160,AB365142,AB263931,AB485704,AB269862,FR720313,AB217921,AB269828,AB269854,AB485694,AB269850,JN192436,FR720315,JN192441,AB269822,AB365152,AB298942,AB263915,AB263923,AB269869,AB365162,AB365178,AY628236,AB260034,AB211383,FR720308,AB211384,AY628232,AB211378,AB211380,AB211369,AB464959,AB263929,AB301096

TABLE 10-continued

VioCap-1.0 Taxonomy

| Taxonomy | Rep.Acc.ID | Host | # GN's | Lineage | Seg. Count | GN.Acc.IDs |
|---|---|---|---|---|---|---|
| Bat SARS coronavirus HKU3-13 | NC_004718 | vertebrates,human | 1 | Coronaviridae,Betacoronavirus,Severe acute respiratory syndrome-related coronavirus | —

TABLE 10-continued

VIroCap-1.0 Taxonomy

| Taxonomy | Rep.Acc.ID | Host | Lineage | # GN's | Seg. Count | GN.Acc.IDs |
|---|---|---|---|---|---|---|
| Bovine respiratory syncytial virus | NC_001989 | vertebrates,human | Paramyxoviridae,Pneumovirus,Bovine respiratory syncytial virus | 1 | — | 4,HQ530153,AF178655,JX969001,D84095,AXQ73600,AF178654,AB770485 |
| Bovine respiratory syncytial virus ATCC51908 | NC_001989 | vertebrates,human | Paramyxoviridae,Pneumovirus,Bovine respiratory syncytial virus | 1 | — | AF092942 |
| Bovine rotavirus | NC_011500 | vertebrates,human | Reoviridae,Rotavirus,Rotavirus A | 1 | seg. 5 | HM363560 |
| Bovine rotavirus | NC_011501 | vertebrates,human | Reoviridae,Rotavirus,Rotavirus A | 42 | seg. 7 | FJ206164,EU542719,HM363562,EU542716,K02170,FJ206188,EU542714,EU542715,FJ206180,FJ206176,EU542718,FJ206174,FJ206181,FJ206184,DQ494403,EU542717,FJ206189,FJ206172,FJ206165,FJ206179,FJ206166,FJ206192,FJ206185,FJ206178,DQ494404,FJ206182,FJ206171,FJ206191,FJ206167,FJ206190,FJ206186,FJ206175,FJ206187,FJ206173,FJ206226,FJ206168,FJ206183,JX971577,FJ206193,FJ206169,FJ206170,FJ206177 |
| Bovine rotavirus | NC_011502 | vertebrates,human | Reoviridae,Rotavirus,Rotavirus A | 41 | seg. 8 | EU542713,FJ206158,FJ206139,DQ494402,FJ206120,FJ206133,FJ206148,FJ206116,EU542711,FJ206136,HM363561,FJ206118,FJ206146,FJ206143,EU542708,FJ206138,FJ206130,FJ206131,FJ206152,FJ206110,FJ206122,FJ206123,FJ206126,FJ206157,FJ206108,FJ206134,JX971576,FJ206128,FJ206141,FJ206114,FJ206125,EU542712,FJ206150,EU542709,FJ206155,EU542710, |

TABLE 10-continued

VirCap-1.0 Taxonomy

| Taxonomy | Rep.Acc.ID | Host | #GN's | Lineage | Seg. Count | GN.Acc.IDs |
|---|---|---|---|---|---|---|
| Bovine rotavirus | NC_011503 | vertebrates,human | 49 | Reoviridae,Rotavirus,Rotavirus A | seg. 9 | DQ494401,FJ206154, FJ206160,FJ206145, FJ206112 FJ206037,FJ217204, FJ206039,EU873014, FJ206073,FJ206082, GQ352366,FJ217205 ,FJ206047,EU143711 ,HQ199897,AB07705 4,FJ206057,FJ206606 8,FJ206079,FJ206605 8,AB077056,FJ20607 7,HM591496,HM2355 10,GQ352364,U5033 2,FJ206055,FJ206608 7,GQ352362,JX9715 74,AB077058,EU873 015,FJ206048,FJ206 072,FJ206085,FJ545 658,DQ494393,X526 50,AB077053,FJ2060 84,EU828784,EU873 013,FJ206088,FJ206 044,DQ494394,AB07 7055,FJ206049,FJ20 6070,AB077057,FJ20 6041,FJ206064,FJ20 6080,FJ206075 |
| Bovine rotavirus | NC_011504 | vertebrates,human | 51 | Reoviridae,Rotavirus,Rotavirus A | seg. 10 | EU542721,FJ206109, FJ206137,JX971578, FJ206147,AF166354, FJ206117,EU542722, FJ206113,FJ206140, FJ206111,FJ206144, EU542723,DQ494398 ,EU873006,DQ49439 7,FJ206135,EU82878 6,EU542720,FJ20612 7,FJ206151,FJ206610 7,AF166353,FJ20610 1,FJ206103,HM5914 94,FJ206129,EU5427 25,FJ206162,HM363 563,FJ206156,FJ206 115,FJ206132,EU542 724,FJ206161,EU873 007,FJ206119,EU873 105,FJ206142,HM59 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | 1492,FJ206121,EU873008,FJ206124,FJ206149,FJ206106,FJ206163,HM591493,FJ206159,FJ206155,FJ1972713,FJ206104 |
| Bovine rotavirus | NC_011505 | vertebrates,human | Reoviridae,Rotavirus,Rotavirus A | 41 | seg. 11 | FJ206045,FJ206050, FJ206076,FJ206054, FJ206071,FJ206061, FJ206052,FJ206078, EU542729,EU542731 ,FJ206091,FJ206046, EU542730,FJ206099, FJ206059,FJ206083, HM363564,FJ206096 ,FJ206093,FJ206067, DQ494399,FJ206069, FJ206074,FJ206081, FJ206056,FJ206090, FJ206060,DQ494400, FJ206065,EU542727, FJ206092,EU542726, FJ206089,FJ206100, FJ206097,FJ206086, FJ206063,FJ206094, FJ206098,JX971579, EU542728 |
| Bovine rotavirus | NC_011506 | vertebrates,human | Reoviridae,Rotavirus,Rotavirus A | 2 | seg. 2 | X52589,JX971570 |
| Bovine rotavirus | NC_011507 | vertebrates,human | Reoviridae,Rotavirus,Rotavirus A | 3 | seg. 1 | JX971569,X55444,JQ4346 |
| Bovine rotavirus | NC_011508 | vertebrates,human | Reoviridae,Rotavirus,Rotavirus A | 1 | seg. 3 | JX971571 |
| Bovine rotavirus | NC_011509 | vertebrates,human | Reoviridae,Rotavirus,Rotavirus A | 5 | seg. 6 | EU873010,EU873011 ,EU873012,K02254,JX971573 |
| Bovine rotavirus A | NC_011510 | vertebrates,human | Reoviridae,Rotavirus,Rotavirus A | 2 | seg. 4 | JX971572,EU873009 |
| Bovine rotavirus A | NC_011500 | vertebrates,human | Reoviridae,Rotavirus,Rotavirus A | 3 | seg. 5 | JF693063,JF693041, JF693030 |
| Bovine rotavirus A | NC_011501 | vertebrates,human | Reoviridae,Rotavirus,Rotavirus A | 3 | seg. 7 | JF693065,AB513838, JF693043 |
| Bovine rotavirus A | NC_011502 | vertebrates,human | Reoviridae,Rotavirus,Rotavirus A | 2 | seg. 8 | JF693066,JF693044 |
| Bovine rotavirus A | NC_011503 | vertebrates,human | Reoviridae,Rotavirus,Rotavirus A | 26 | seg. 9 | JX470523,JF720877, JF742652,AB513837, JF693045,JF720878, JX470522,JX470514, JX470516,EF200563, AB454421,JF693067, EF200560,JX470519, EF200549,JF689835, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bovine rotavirus A | NC_011504 | vertebrates,human | 11 | Reoviridae,Rotavirus,Rotavirus A | seg. 10 | JX470518,EF199501, GU144587,JX470515 ,JX470521,JX470517, JF720882,JX470520, AB486011,DQ487203 JF693046,EF200578, GU181282,EF200575 ,EF200574,AY293829 ,EF200576,EF200573 ,EF592592,JF693068 ,EF200572 |
| Bovine rotavirus A | NC_011505 | vertebrates,human | 7 | Reoviridae,Rotavirus,Rotavirus A | seg. 11 | JF693047,EF200582, JF693069,EF200580, GU937876,EF200581 ,EF200579 |
| Bovine rotavirus A | NC_011506 | vertebrates,human | 3 | Reoviridae,Rotavirus,Rotavirus A | seg. 2 | JF693060,JF693027, JF693038 |
| Bovine rotavirus A | NC_011507 | vertebrates,human | 3 | Reoviridae,Rotavirus,Rotavirus A | seg. 1 | JF693059,JF693037, JF693026 |
| Bovine rotavirus A | NC_011508 | vertebrates,human | 4 | Reoviridae,Rotavirus,Rotavirus A | seg. 3 | AY300923,JF693061, JF693039,JF693028 |
| Bovine rotavirus A | NC_011509 | vertebrates,human | 11 | Reoviridae,Rotavirus,Rotavirus A | seg. 6 | JF720875,EF200569, JF693064,EF200568, JF742649,EF200873, JF693042,JF720879, EF200565,JF742650, EF200567 |
| Bovine rotavirus A | NC_011510 | vertebrates,human | 7 | Reoviridae,Rotavirus,Rotavirus A | seg. 4 | JF693040,JF693029, AB513836,DQ838596 ,AB454420,AB48601 0,JF693062 |
| Bovine rotavirus B-11 | NC_011510 | vertebrates,human | 1 | Reoviridae,Rotavirus,Rotavirus A | seg. 4 | AY047488 |
| Bovine rotavirus G10 | NC_011504 | vertebrates,human | 1 | Reoviridae,Rotavirus,Rotavirus A | seg. 10 | AY527227 |
| Bovine rotavirus G15P11 | NC_011505 | vertebrates,human | 1 | Reoviridae,Rotavirus,Rotavirus A | seg. 11 | EU682404 |
| Bovine rotavirus G15P21 | NC_011504 | vertebrates,human | 1 | Reoviridae,Rotavirus,Rotavirus A | seg. 10 | AY527226 |
| Bovine rotavirus G6 | NC_011501 | vertebrates,human | 4 | Reoviridae,Rotavirus,Rotavirus A | seg. 7 | AB748598,AB748600 ,AB748597,AB74859 9 |
| Bovine rotavirus G6 | NC_011502 | vertebrates,human | 4 | Reoviridae,Rotavirus,Rotavirus A | seg. 8 | AB748594,AB748595 ,AB748592,AB74859 3 |
| Bovine rotavirus G6 | NC_011504 | vertebrates,human | 4 | Reoviridae,Rotavirus,Rotavirus A | seg. 10 | AB748604,AB748603 ,AB748605,AB74860 2 |

TABLE 10-continued

VifoCap-1.0 Taxonomy

| Taxonomy | Rep.Acc.ID | Host | # GN's | Lineage | Seg. Count | GN.Acc.IDs |
|---|---|---|---|---|---|---|
| Bovine rotavirus strain BRV033 | NC_011504 | vertebrates,human | 1 | Reoviridae,Rotavirus,Rotavirus A | seg. 10 | AF144804 |
| Bovine rotavirus strain RF | NC_011504 | vertebrates,human | 1 | Reoviridae,Rotavirus,Rotavirus A | seg. 10 | AY116593 |
| Bovine rotavirus strain RF | NC_011508 | vertebrates,human | 1 | Reoviridae,Rotavirus,Rotavirus A | seg. 3 | AY116592 |
| Buffalo rotavirus A 10733 | NC_011503 | vertebrates,human | 1 | Reoviridae,Rotavirus,Rotavirus A | seg. 9 | AY281360 |
| Buffalo rotavirus A 10733 | NC_011505 | vertebrates,human | 1 | Reoviridae,Rotavirus,Rotavirus A | seg. 11 | EU659853 |
| Bundibugyo ebolavirus | NC_014373 | vertebrates,human | 5 | Filoviridae,Ebolavirus,Bundibugyo ebolavirus | — | KC545394,KC545393,KC545396,FJ217161,KC545395 |
| CAS virus | NC_018481 | vertebrates,human | 1 | Arenaviridae,CAS virus | seg. S | JQ717262 |
| CAS virus | NC_018484 | vertebrates,human | 1 | Arenaviridae,CAS virus | seg. L | JQ717261 |
| Camberwell virus | NC_001959 | vertebrates,human | 1 | Caliciviridae,Norovirus,Norwalk virus | — | AF145896 |
| Canine distemper virus | NC_001921 | vertebrates,human | 43 | Paramyxoviridae,Morbillivirus,Canine distemper virus | — | AB490680,AB475099,EU726268,AB82370 7,AB490672,AB6877 21,AB490674,AX453 976,AB753775,AY46 6011,KF914669,AF01 4953,EU716337,AF3 05419,AB476401,AB 475097,AB490676,A Y386316,JN896331,A B462810,AF164967,A B823706,AB490678, AB476402,AB490681 ,GU138403,AY44335 0,AX453975,AB4906 70,AY386315,AY649 446,AB490679,AY44 5077,HM852904,AY5 42312,AX453977,HM 063009,HM046486,A B753776,AB474397,J N896987,AB687720, KC427278 |
| Canine distemper virus strain Onderstepoort | NC_001921 | vertebrates,human | 1 | Paramyxoviridae,Morbillivirus,Canine distemper virus | — | AF378705 |
| Canine rotavirus A79-10/G3P[3] | NC_011500 | vertebrates,human | 1 | Reoviridae,Rotavirus,Rotavirus A | seg. 5 | EU708940 |
| Canine rotavirus A79-10/G3P[3] | NC_011501 | vertebrates,human | 1 | Reoviridae,Rotavirus,Rotavirus A | seg. 7 | EU708941 |
| Canine rotavirus A79-10/G3P[3] | NC_011502 | vertebrates,human | 1 | Reoviridae,Rotavirus,Rotavirus A | seg. 8 | EU708942 |
| Canine rotavirus A79-10/G3P[3] | NC_011503 | vertebrates,human | 1 | Reoviridae,Rotavirus,Rotavirus A | seg. 9 | EU708939 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Canine rotavirus A79-10/G3P[3] | NC_011504 | vertebrates,human | Reoviridae,Rotavirus,Rotavirus A | 1 | seg. 10 | EU708943 |
| Canine rotavirus A79-10/G3P[3] | NC_011505 | vertebrates,human | Reoviridae,Rotavirus,Rotavirus A | 1 | seg. 11 | EU708944 |
| Canine rotavirus A79-10/G3P[3] | NC_011506 | vertebrates,human | Reoviridae,Rotavirus,Rotavirus A | 1 | seg. 2 | EU708935 |
| Canine rotavirus A79-10/G3P[3] | NC_011507 | vertebrates,human | Reoviridae,Rotavirus,Rotavirus A | 1 | seg. 1 | EU708934 |
| Canine rotavirus A79-10/G3P[3] | NC_011508 | vertebrates,human | Reoviridae,Rotavirus,Rotavirus A | 1 | seg. 3 | EU708936 |
| Canine rotavirus A79-10/G3P[3] | NC_011509 | vertebrates,human | Reoviridae,Rotavirus,Rotavirus A | 1 | seg. 6 | EU708938 |
| Canine rotavirus A79-10/G3P[3] | NC_011510 | vertebrates,human | Reoviridae,Rotavirus,Rotavirus A | 1 | seg. 4 | EU708937 |
| Canine rotavirus CU-1 | NC_011500 | vertebrates,human | Reoviridae,Rotavirus,Rotavirus A | 1 | seg. 5 | EU708918 |
| Canine rotavirus CU-1 | NC_011501 | vertebrates,human | Reoviridae,Rotavirus,Rotavirus A | 1 | seg. 7 | EU708919 |
| Canine rotavirus CU-1 | NC_011502 | vertebrates,human | Reoviridae,Rotavirus,Rotavirus A | 1 | seg. 8 | EU708920 |
| Canine rotavirus CU-1 | NC_011503 | vertebrates,human | Reoviridae,Rotavirus,Rotavirus A | 1 | seg. 9 | EU708917 |
| Canine rotavirus CU-1 | NC_011504 | vertebrates,human | Reoviridae,Rotavirus,Rotavirus A | 2 | seg. 10 | AF144806,EU708921 |
| Canine rotavirus CU-1 | NC_011505 | vertebrates,human | Reoviridae,Rotavirus,Rotavirus A | 1 | seg. 11 | EU708922 |
| Canine rotavirus CU-1 | NC_011506 | vertebrates,human | Reoviridae,Rotavirus,Rotavirus A | 1 | seg. 2 | EU708913 |
| Canine rotavirus CU-1 | NC_011507 | vertebrates,human | Reoviridae,Rotavirus,Rotavirus A | 1 | seg. 1 | EU708912 |
| Canine rotavirus CU-1 | NC_011508 | vertebrates,human | Reoviridae,Rotavirus,Rotavirus A | 1 | seg. 3 | EU708914 |
| Canine rotavirus CU-1 | NC_011509 | vertebrates,human | Reoviridae,Rotavirus,Rotavirus A | 1 | seg. 6 | EU708916 |
| Canine rotavirus CU-1 | NC_011510 | vertebrates,human | Reoviridae,Rotavirus,Rotavirus A | 3 | seg. 4 | EU708915,D13401,L20876 |
| Canine rotavirus K9 | NC_011500 | vertebrates,human | Reoviridae,Rotavirus,Rotavirus A | 2 | seg. 5 | AF111946,EU708929 |
| Canine rotavirus K9 | NC_011501 | vertebrates,human | Reoviridae,Rotavirus,Rotavirus A | 1 | seg. 7 | EU708930 |
| Canine rotavirus K9 | NC_011502 | vertebrates,human | Reoviridae,Rotavirus,Rotavirus A | 1 | seg. 8 | EU708931 |
| Canine rotavirus K9 | NC_011503 | vertebrates,human | Reoviridae,Rotavirus,Rotavirus A | 1 | seg. 9 | EU708928 |
| Canine rotavirus K9 | NC_011504 | vertebrates,human | Reoviridae,Rotavirus,Rotavirus A | 1 | seg. 10 | EU708932 |
| Canine rotavirus K9 | NC_011505 | vertebrates,human | Reoviridae,Rotavirus,Rotavirus A | 1 | seg. 11 | EU708933 |
| Canine rotavirus K9 | NC_011506 | vertebrates,human | Reoviridae,Rotavirus,Rotavirus A | 1 | seg. 2 | EU708924 |
| Canine rotavirus K9 | NC_011507 | vertebrates,human | Reoviridae,Rotavirus,Rotavirus A | 1 | seg. 1 | EU708923 |
| Canine rotavirus K9 | NC_011508 | vertebrates,human | Reoviridae,Rotavirus,Rotavirus A | 1 | seg. 3 | EU708925 |
| Canine rotavirus K9 | NC_011509 | vertebrates,human | Reoviridae,Rotavirus,Rotavirus A | 1 | seg. 6 | EU708927 |
| Canine rotavirus K9 | NC_011510 | vertebrates,human | Reoviridae,Rotavirus,Rotavirus A | 2 | seg. 4 | EU708926,D13400 |
| Canine rotavirus RV198/95 | NC_011503 | vertebrates,human | Reoviridae,Rotavirus,Rotavirus A | 1 | seg. 9 | AF271089 |
| Canine rotavirus RV52/96 | NC_011503 | vertebrates,human | Reoviridae,Rotavirus,Rotavirus A | 1 | seg. 9 | AF271090 |
| Caprine rotavirus A | NC_011500 | vertebrates,human | Reoviridae,Rotavirus,Rotavirus A | 1 | seg. 5 | GU937883 |
| Caprine rotavirus A | NC_011501 | vertebrates,human | Reoviridae,Rotavirus,Rotavirus A | 2 | seg. 7 | JQ004978,GU937885 |
| Caprine rotavirus A | NC_011502 | vertebrates,human | Reoviridae,Rotavirus,Rotavirus A | 2 | seg. 8 | GU937884,JQ004977 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Caprine rotavirus A | NC_011503 | vertebrates,human | 5 | Reoviridae,Rotavirus,Rotavirus A | seg. 9 | GU937882,GU937889,GU937891,JQ004979,AY128708 |
| Caprine rotavirus A | NC_011504 | vertebrates,human | 2 | Reoviridae,Rotavirus,Rotavirus A | seg. 10 | GU937886,JQ004979 |
| Caprine rotavirus A | NC_011505 | vertebrates,human | 2 | Reoviridae,Rotavirus,Rotavirus A | seg. 11 | JQ004980,GU937887 |
| Caprine rotavirus A | NC_011506 | vertebrates,human | 2 | Reoviridae,Rotavirus,Rotavirus A | seg. 2 | JQ004971,GU937878 |
| Caprine rotavirus A | NC_011507 | vertebrates,human | 2 | Reoviridae,Rotavirus,Rotavirus A | seg. 1 | JQ004970,GU937877 |
| Caprine rotavirus A | NC_011508 | vertebrates,human | 2 | Reoviridae,Rotavirus,Rotavirus A | seg. 3 | JQ004972,GU937879 |
| Caprine rotavirus A | NC_011509 | vertebrates,human | 2 | Reoviridae,Rotavirus,Rotavirus A | seg. 6 | GU937881,JQ004974 |
| Caprine rotavirus A | NC_011510 | vertebrates,human | 2 | Reoviridae,Rotavirus,Rotavirus A | seg. 4 | GU937880,JQ004973 |
| Chandipura virus | NC_020805 | vertebrates,human | 2 | Rhabdoviridae,Vesiculovirus,Chandipura virus | — | GU212858,GU2128586 |
| Chandipura virus Dak AR D 111125 | NC_020805 | vertebrates,human | 1 | Rhabdoviridae,Vesiculovirus,Chandipura virus | — | HM627187 |
| Chandipura virus IB An 9978 | NC_020805 | vertebrates,human | 1 | Rhabdoviridae,Vesiculovirus,Chandipura virus | — | HM627186 |
| Chapare virus | NC_010562 | vertebrates,human | 1 | Arenaviridae,Arenavirus,Chapare virus | seg. S | EU260463 |
| Chapare virus | NC_010563 | vertebrates,human | 1 | Arenaviridae,Arenavirus,Chapare virus | seg. L | EU260464 |
| Chiba virus | NC_001959 | vertebrates,human | 1 | Caliciviridae,Norovirus,Norwalk virus | — | AB042808 |
| Civet SARS Coy 007/2004 | NC_004718 | vertebrates,human | 1 | Coronaviridae,Betacoronavirus,Severe acute respiratory syndrome-related coronavirus | — | AY572034 |
| Civet SARS Coy SZ16/2003 | NC_004718 | vertebrates,human | 1 | Coronaviridae,Betacoronavirus,Severe acute respiratory syndrome-related coronavirus | — | AY304488 |
| Civet SARS Coy SZ3/2003 | NC_004718 | vertebrates,human | 1 | Coronaviridae,Betacoronavirus,Severe acute respiratory syndrome-related coronavirus | — | AY304486 |
| Colobus guereza papillomavirus type 2 | NC_015692 | vertebrates,human | 1 | Papillomaviridae,Betapapillomavirus,Colobus monkey papillomavirus | — | GU014533 |
| Convict Creek 107 virus | NC_005215 | vertebrates,human | 2 | Bunyaviridae,Hantavirus,Sin Nombre virus | seg. M | L33684,L33474 |
| Convict Creek 107 virus | NC_005216 | vertebrates,human | 2 | Bunyaviridae,Hantavirus,Sin Nombre virus | seg. S | U47135,L33816 |
| Convict Creek 107 virus | NC_005217 | vertebrates,human | 1 | Bunyaviridae,Hantavirus,Sin Nombre virus | seg. L | AF425256 |
| Cote d'Ivoire ebolavirus | NC_014372 | vertebrates,human | 1 | Filoviridae,Ebolavirus,Taï Forest ebolavirus | — | FJ217162 |
| Coxsackievirus A16 | NC_001612 | vertebrates,human | 22 | Picornaviridae,Enterovirus,Enterovirus A | — | KC755235,KF193630,KF193622,KF193629,KC755234,KC755222,KF193628,KF193620,KC755232,KF193624,KF193625,KC755230,KF193621,KF193631,KC755233,KF1935229,KF193632,KC507895,KF193623,KC755231,KF193627,KF193626 |
| Coxsackievirus A2 | NC_001612 | vertebrates,human | 4 | Picornaviridae,Enterovirus,Enterovirus A | — | JX867332,JX867331,JX867333,JX867330 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Coxsackievirus A24 | NC_002058 | vertebrates,human | 1 | Picornaviridae,Enterovirus,Enterovirus C | — | KF725085 |
| Coxsackievirus A7 | NC_001612 | vertebrates,human | 4 | Picornaviridae,Enterovirus,Enterovirus A | — | GU942820,GU942823,GU942821,GU942822 |
| Cupixi virus | NC_010252 | vertebrates,human | 1 | Arenaviridae,Arenavirus,Cupixi virus | seg. L | AY216519 |
| Cupixi virus | NC_010254 | vertebrates,human | 1 | Arenaviridae,Arenavirus,Cupixi virus | seg. S | AF512832 |
| Cutthroat trout virus | NC_015521 | vertebrates,human | 1 | Hepeviridae,Cutthroat trout virus | — | HQ731075 |
| Dobrava-Belgrade virus | NC_005233 | vertebrates,human | 15 | Bunyaviridae,Hantavirus,Dobrava-Belgrade virus | seg. S | AY961615,AY533120,AY961618,AY533118,AJQ09775,JQ02620 4,AJQ09773,AJ41061 5,AF44622,AJ13167 3,JF920150,AY16857 6,AJ131672,L41916, AJ410619 |
| Dobrava-Belgrade virus | NC_005234 | vertebrates,human | 8 | Bunyaviridae,Hantavirus,Dobrava-Belgrade virus | seg. M | AY961616,AY168577,AIQ09774,AY168578,JQ026205,JF920149,AI410616,L33685 |
| Dobrava-Belgrade virus | NC_005235 | vertebrates,human | 3 | Bunyaviridae,Hantavirus,Dobrava-Belgrade virus | seg. L | AI410617,IQ026206,JF920148 |
| Dolphin morbillivirus | NC_005283 | vertebrates,human | 1 | Paramyxoviridae,Morbillivirus,Cetacean morbillivirus | — | AJ608288 |
| Duvenhage virus | NC_020810 | vertebrates,human | 4 | Rhabdoviridae,Lyssavirus,Duvenhage virus | — | EU293120,EU293119,EU623444,JN986749 |
| Ebola virus-Mayinga, Zaire, 1976 | NC_002549 | vertebrates,human | 1 | Filoviridae,Ebolavirus,Zaire ebolavirus | — | AF086833 |
| Echovirus 1 (strain Farouk! ATCC VR-1038) | NC_001472 | vertebrates,human | 1 | Picornaviridae,Enterovirus,Enterovirus B | — | AF029859 |
| Echovirus 9 (strain Barty) | NC_001472 | vertebrates,human | 1 | Picornaviridae,Enterovirus,Enterovirus B | — | X92886 |
| Echovirus 9 (strain Hill) | NC_001472 | vertebrates,human | 1 | Picornaviridae,Enterovirus,Enterovirus B | — | X84981 |
| Echovirus E25 | NC_001472 | vertebrates,human | 1 | Picornaviridae,Enterovirus,Enterovirus B | — | JX976772 |
| Echovirus E30 | NC_001472 | vertebrates,human | 6 | Picornaviridae,Enterovirus,Enterovirus B | — | KC897073,JX854435,JX976773,EF066392,EF066391,AY948442 |
| Echovirus E6 | NC_001472 | vertebrates,human | 9 | Picornaviridae,Enterovirus,Enterovirus B | — | JQ929657,JX976771,KF042343,AB705309,KF042342,AB705311,AB705308,AB705310,JQ801 739 |
| Echovirus E9 | NC_001472 | vertebrates,human | 4 | Picornaviridae,Enterovirus,Enterovirus B | — | KC238668,JN596587,KC238669,KC238667 |
| Enterovirus 5666/5in/002209 | NC_001612 | vertebrates,human | 1 | Picornaviridae,Enterovirus,Enterovirus A | — | AF352027 |
| Enterovirus 5865/5in/000009 | NC_001612 | vertebrates,human | 1 | Picornaviridae,Enterovirus,Enterovirus A | — | AF316321 |
| Enterovirus A | NC_001612 | vertebrates,human | 1 | Picornaviridae,Enterovirus,Enterovirus A | — | U05876 |
| Enterovirus A71 | NC_001612 | vertebrates,human | 28 | Picornaviridae,Enterovirus,Enterovirus A | — | AB747374,AB747373 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | ,KC296444,KF13448 6,KF142412,KF31245 7,KC296445,KF1424 11,KF142413,AB7473 75,KC436270,KF668 443,KC954664,KF15 4355,KC954662,KC4 36271,KC436268,KC 436272,KC570452,K C436269,KC296443, KC436266,KC954663 ,KC570453,KC43626 7,KC436265,JQ5147 85,KF501389 |
| Enterovirus B | NC_001472 | vertebrates,human | 5 | Picornaviridae,Enterovirus,Enterovirus B | — | KC568448,KC568449 ,KC568447,KC56844 6,M16560 |
| Enterovirus B87 | NC_001472 | vertebrates,human | 1 | Picornaviridae,Enterovirus,Enterovirus B | — | KC292019 |
| Enterovirus B97 | NC_001472 | vertebrates,human | 1 | Picornaviridae,Enterovirus,Enterovirus B | — | GU550508 |
| Enterovirus CA55-1988 | NC_001472 | vertebrates,human | 1 | Picornaviridae,Enterovirus,Enterovirus B | — | AF241359 |
| Enterovirus Yanbian 96-83csf | NC_001472 | vertebrates,human | 1 | Picornaviridae,Enterovirus,Enterovirus B | — | AF230973 |
| Equine rotavirus A | NC_011500 | vertebrates,human | 1 | Reoviridae,Rotavirus,Rotavirus A | seg. 5 | JXQ36371 |
| Equine rotavirus A | NC_011501 | vertebrates,human | 6 | Reoviridae,Rotavirus,Rotavirus A | seg. 7 | KC815700,JXQ36373, JQ309143,KC815677 ,KC815688,KC81566 6 |
| Equine rotavirus A | NC_011502 | vertebrates,human | 6 | Reoviridae,Rotavirus,Rotavirus A | seg. 8 | JQ309142,KC815665 ,KC815687,KC81567 6,JXQ36372,KC81569 9 |
| Equine rotavirus A | NC_011503 | vertebrates,human | 14 | Reoviridae,Rotavirus,Rotavirus A | seg. 9 | KC815674,AB595975 ,AY750925,AB59597 6,AB595979,AB5959 78,AB595977,L49042 ,JXQ36370,L49043,A B595974,AY750924, KC815685,KC815663 |
| Equine rotavirus A | NC_011504 | vertebrates,human | 5 | Reoviridae,Rotavirus,Rotavirus A | seg. 10 | KC815689,KC815667 ,JXQ36374,KC815701 ,KC815678 |
| Equine rotavirus A | NC_011505 | vertebrates,human | 3 | Reoviridae,Rotavirus,Rotavirus A | seg. 11 | KC815668,JXQ36375, JQ309144 |
| Equine rotavirus A | NC_011506 | vertebrates,human | 6 | Reoviridae,Rotavirus,Rotavirus A | seg. 2 | KC815681,JXQ36366, JQ309139,KC815695 ,KC815659,KC815667 0 |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| Equine rotavirus A | NC_011507 | vertebrates,human | 6 | Reoviridae,Rotavirus,Rotavirus A | seg. 1 | KC815680,JQ309138,KC815694,KC815666,KC815658,JXQ36369,KC815658,JXQ36365 |
| Equine rotavirus A | NC_011508 | vertebrates,human | 7 | Reoviridae,Rotavirus,Rotavirus A | seg. 3 | KC815696,JXQ36367,KC815660,KC815671,KC815682,JQ30914 0,AY277922 |
| Equine rotavirus A | NC_011509 | vertebrates,human | 5 | Reoviridae,Rotavirus,Rotavirus A | seg. 6 | KC815697,KC815662,JXQ36369,KC815673,KC815684 |
| Equine rotavirus A | NC_011510 | vertebrates,human | 3 | Reoviridae,Rotavirus,Rotavirus A | seg. 4 | KC815672,KC815661,KC815683 |
| European bat lyssavirus 1 | NC_009527 | vertebrates,human | 8 | Rhabdoviridae,Lyssavirus,European bat lyssavirus 1 | — | KF042301,EU626551,KF042302,EF157976,EU293112,KF15500 3,EU626552,EU2931 09 |
| European bat lyssavirus 2 | NC_009528 | vertebrates,human | 3 | Rhabdoviridae,Lyssavirus,European bat lyssavirus 2 | — | KF155004,EF157977, EU293114 |
| Fer-de-lance virus | NC_005084 | vertebrates,human | 1 | Paramyxoviridae,Ferlavirus,Fer-de-Lance paramyxovirus | — | AY141760 |
| Ferret hepatitis E virus | NC_001434 | vertebrates,human | 2 | Hepeviridae,Hepevirus,Hepatitis E virus | — | JN998606,JN998607 |
| Flexal virus | NC_010757 | vertebrates,human | 2 | Arenaviridae,Arenavirus,Flexal virus | seg. S | AF512831,AF485257 |
| Flexal virus | NC_010759 | vertebrates,human | 1 | Arenaviridae,Arenavirus,Flexal virus | seg. L | EU627611 |
| GB virus C | NC_001710 | vertebrates,human | 48 | Flaviviridae,Pegivirus,GB virus C | — | KC618398,AB013500,JN127373,D87710,A Y949771,U45966,D8 7712,AF031828,U444 02,D87263,AB003293,U75356,D90600,AF0 06500,AB008335,D87 711,AF121950,U3638 0,HQ331233,AB0135 01,AB003289,AB0O8 342,D87708,AF08178 2,KC618399,AB0186 67,AB008336,KC618 401,AF031827,AF031 829,AF104403,AB003 288,U63715,HQ3312 35,AB003292,D87255 ,D87715,KC618400,U 94695,D90601 ,D8771 3,AB003290,D87262, HQ331234,AB021287 ,D87714,D87709,AY1 96904 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| GB virus C variant troglodytes | NC_001710 | vertebrates,human | 1 | Flaviviridae,Pegivirus,GB virus C | — | AF070476 |
| Giant panda rotavirus A | NC_011502 | vertebrates,human | 1 | Reoviridae,Rotavirus,Rotavirus A | seg. 8 | GU188281 |
| Giant panda rotavirus A | NC_011504 | vertebrates,human | 1 | Reoviridae,Rotavirus,Rotavirus A | seg. 10 | GU188282 |
| Giant panda rotavirus A | NC_011505 | vertebrates,human | 1 | Reoviridae,Rotavirus,Rotavirus A | seg. 11 | GU329526 |
| Giant panda rotavirus A | NC_011506 | vertebrates,human | 1 | Reoviridae,Rotavirus,Rotavirus A | seg. 2 | HQ641294 |
| Golden Gate virus | NC_018482 | vertebrates,human | 1 | Arenaviridae,Golden Gate virus | seg. L | JQ717263 |
| Golden Gate virus | NC_018483 | vertebrates,human | 1 | Arenaviridae,Golden Gate virus | seg. S | JQ717264 |
| Goose paramyxovirus SF02 | NC_005036 | vertebrates,human | 1 | Paramyxoviridae,Avulavirus,Goose paramyxovirus SF02 | — | AF473851 |
| Guanarito virus | NC_005077 | vertebrates,human | 3 | Arenaviridae,Arenavirus,Guanarito virus | seg. S | AY129247,AY497548,AF485258 |
| Guanarito virus | NC_005082 | vertebrates,human | 2 | Arenaviridae,Arenavirus,Guanarito virus | seg. L | AY216504,AY358024 |
| HBV genotype A | NC_003977 | vertebrates,human | 1 | Hepadnaviridae,Orthohepadnavirus,Hepatitis B virus | — | AP007263 |
| HBV genotype A1 | NC_003977 | vertebrates,human | 6 | Hepadnaviridae,Orthohepadnavirus,Hepatitis B virus | — | HE974375,HE974381,HE974365,HE974370,HE974436,HE974362 |
| HBV genotype A2 | NC_003977 | vertebrates,human | 6 | Hepadnaviridae,Orthohepadnavirus,Hepatitis B virus | — | HE974383,HE974364,HE974371,HE974437,HE974376,HE974374,HE974367 |
| HBV genotype B | NC_003977 | vertebrates,human | 3 | Hepadnaviridae,Orthohepadnavirus,Hepatitis B virus | — | AB602818,AB554017,AB540582 |
| HBV genotype C | NC_003977 | vertebrates,human | 19 | Hepadnaviridae,Orthohepadnavirus,Hepatitis B virus | — | AB554020,AB540585,AB644286,AB64428 7,AB644280,AB554021,AB644281,AB560 662,AB644284,AB55 4014,AB560661,AB5 54019,AB644283,AB 554025,AB540584,A B554022,AB554015, AB540583,AB554018 |
| HBV genotype D | NC_003977 | vertebrates,human | 4 | Hepadnaviridae,Orthohepadnavirus,Hepatitis B virus | — | HE815465,AB554016,AB554024,AB55402 3 |
| HBV genotype D3 | NC_003977 | vertebrates,human | 2 | Hepadnaviridae,Orthohepadnavirus,Hepatitis B virus | — | HE974377,HE974379 |
| HBV genotype D4 | NC_003977 | vertebrates,human | 4 | Hepadnaviridae,Orthohepadnavirus,Hepatitis B virus | — | HE974372,HE974378,HE974373,HE97438 2 |
| HBV genotype E | NC_003977 | vertebrates,human | 3 | Hepadnaviridae,Orthohepadnavirus,Hepatitis B virus | — | HE974384,HE974380,AP007262 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| HBV genotype F2 | NC_003977 | vertebrates,human | Hepadnaviridae,Orthohepadnavirus,Hepatitis B virus | 2 | — | HE974366,HE974369 |
| HBV genotype F4 | NC_003977 | vertebrates,human | Hepadnaviridae,Orthohepadnavirus,Hepatitis B virus | 1 | — | HE974368 |
| HBV genotype G | NC_003977 | vertebrates,human | Hepadnaviridae,Orthohepadnavirus,Hepatitis B virus | 1 | — | AP007264 |
| HBV genotype H | NC_003977 | vertebrates,human | Hepadnaviridae,Orthohepadnavirus,Hepatitis B virus | 6 | — | AB516393,AB516395,AP007261,AB516394,AB846650,AB298362 |
| HBV recombinant B/C | NC_003977 | vertebrates,human | Hepadnaviridae,Orthohepadnavirus,Hepatitis B virus | 1 | — | AB644282 |
| HBV recombinant C/G | NC_003977 | vertebrates,human | Hepadnaviridae,Orthohepadnavirus,Hepatitis B virus | 1 | — | AB644285 |
| HIV-1 CRF03_AB | NC_001802 | vertebrates,human | Retroviridae,Lentivirus,Human immunodeficiency virus 1 | 1 | — | AF193276 |
| HIV-1 CRF04_cpx | NC_001802 | vertebrates,human | Retroviridae,Lentivirus,Human immunodeficiency virus 1 | 1 | — | AF049337 |
| HIV-1 M_02CD,KS069 | NC_001802 | vertebrates,human | Retroviridae,Lentivirus,Human immunodeficiency virus 1 | 1 | — | FM877780 |
| HIV-1 M_02CD,LBTB032 | NC_001802 | vertebrates,human | Retroviridae,Lentivirus,Human immunodeficiency virus 1 | 1 | — | FM877779 |
| HIV-1 M_02CD,LBTB084 | NC_001802 | vertebrates,human | Retroviridae,Lentivirus,Human immunodeficiency virus 1 | 1 | — | FM877781 |
| HIV-1 M_02CD,MBTB047 | NC_001802 | vertebrates,human | Retroviridae,Lentivirus,Human immunodeficiency virus 1 | 1 | — | FM877782 |
| HIV-1 M_97CD,KFE267 | NC_001802 | vertebrates,human | Retroviridae,Lentivirus,Human immunodeficiency virus 1 | 1 | — | FM877778 |
| HIV-1 M_97CD,KTB119 | NC_001802 | vertebrates,human | Retroviridae,Lentivirus,Human immunodeficiency virus 1 | 1 | — | FM877777 |
| HIV-1 M_97CD,MBFE250 | NC_001802 | vertebrates,human | Retroviridae,Lentivirus,Human immunodeficiency virus 1 | 1 | — | FM877783 |
| Hantaan virus | NC_005218 | vertebrates,human | Bunyaviridae,Hantavirus,Hantaan virus | 25 | seg. S | AF427322,AF427324,JQ665905,AY748309,AF321094,D25533,AY017064,U37768,M14626,EF595840,HQ611981,AF427318,AB620031,JQ665906,AF427320,AB127998,D25530,AF427319,AB027111,AB027097,AF321095,AB027101,DQ658415,AF427323,AY839871 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Hantaan virus | NC_005219 | vertebrates,human | Bunyaviridae,Hantavirus,Hantaan virus | 16 | seg. M | JQ665881,AB027115,EU074224,AB127995,AB030232,AB62003,2,U37729,D25532,Y00386,L08753,EU074672,U38177,AF345636,M14627,D25529,JQ665882 |
| Hantaan virus | NC_005222 | vertebrates,human | Bunyaviridae,Hantavirus,Hantaan virus | 6 | seg. L | D25528,AB620033,D25531,X55901,DQ989237,AF336826 |
| Hantaan virus 84FLi | NC_005218 | vertebrates,human | Bunyaviridae,Hantavirus,Hantaan virus | 1 | seg. S | AF366568 |
| Hantaan virus 84FLi | NC_005219 | vertebrates,human | Bunyaviridae,Hantavirus,Hantaan virus | 1 | seg. M | AF366569 |
| Hantaan virus A16 | NC_005218 | vertebrates,human | Bunyaviridae,Hantavirus,Hantaan virus | 1 | seg. S | AF288646 |
| Hantaan virus A16 | NC_005219 | vertebrates,human | Bunyaviridae,Hantavirus,Hantaan virus | 1 | seg. M | AF288645 |
| Hantaan virus A9 | NC_005218 | vertebrates,human | Bunyaviridae,Hantavirus,Hantaan virus | 1 | seg. S | AF035831 |
| Hantaan virus CA09082007 | NC_005218 | vertebrates,human | Bunyaviridae,Hantavirus,Hantaan virus | 1 | seg. S | HQ834499 |
| Hantaan virus CA10081109 | NC_005218 | vertebrates,human | Bunyaviridae,Hantavirus,Hantaan virus | 1 | seg. S | HQ834500 |
| Hantaan virus CA10081113 | NC_005218 | vertebrates,human | Bunyaviridae,Hantavirus,Hantaan virus | 1 | seg. S | HQ834501 |
| Hantaan virus CA10081203 | NC_005218 | vertebrates,human | Bunyaviridae,Hantavirus,Hantaan virus | 1 | seg. S | HQ834502 |
| Hantaan virus CA10081206 | NC_005218 | vertebrates,human | Bunyaviridae,Hantavirus,Hantaan virus | 1 | seg. S | HQ834503 |
| Hantaan virus CA10081708 | NC_005218 | vertebrates,human | Bunyaviridae,Hantavirus,Hantaan virus | 1 | seg. S | HQ834504 |
| Hantaan virus CA10081905 | NC_005218 | vertebrates,human | Bunyaviridae,Hantavirus,Hantaan virus | 1 | seg. S | HQ834505 |
| Hantaan virus E142 | NC_005218 | vertebrates,human | Bunyaviridae,Hantavirus,Hantaan virus | 1 | seg. S | AF288644 |
| Hantaan virus H10150 | NC_005218 | vertebrates,human | Bunyaviridae,Hantavirus,Hantaan virus | 1 | seg. S | HQ834506 |
| Hantaan virus Lee | NC_005222 | vertebrates,human | Bunyaviridae,Hantavirus,Hantaan virus | 1 | seg. L | DQ0377 |
| Hantaan virus N8 | NC_005219 | vertebrates,human | Bunyaviridae,Hantavirus,Hantaan virus | 1 | seg. M | EF077656 |
| Hantaan virus P09072 | NC_005218 | vertebrates,human | Bunyaviridae,Hantavirus,Hantaan virus | 1 | seg. S | HQ834507 |
| Hantaan virus 032 | NC_005219 | vertebrates,human | Bunyaviridae,Hantavirus,Hantaan virus | 1 | seg. M | DQ371905 |
| Hantaan virus 032 | NC_005222 | vertebrates,human | Bunyaviridae,Hantavirus,Hantaan virus | 1 | seg. L | DQ371906 |
| Hantaanvirus CGAa1011 | NC_005218 | vertebrates,human | Bunyaviridae,Hantavirus,Hantaan virus | 1 | seg. S | EF990913 |
| Hantaanvirus CGAa1011 | NC_005219 | vertebrates,human | Bunyaviridae,Hantavirus,Hantaan virus | 1 | seg. M | EF990927 |
| Hantaanvirus CGAa1015 | NC_005218 | vertebrates,human | Bunyaviridae,Hantavirus,Hantaan virus | 1 | seg. S | EF990912 |
| Hantaanvirus CGAa1015 | NC_005219 | vertebrates,human | Bunyaviridae,Hantavirus,Hantaan virus | 1 | seg. M | EF990926 |
| Hantaanvirus CGAa2 | NC_005218 | vertebrates,human | Bunyaviridae,Hantavirus,Hantaan virus | 1 | seg. S | EU092219 |
| Hantaanvirus CGAa2 | NC_005219 | vertebrates,human | Bunyaviridae,Hantavirus,Hantaan virus | 1 | seg. M | EU092223 |
| Hantaanvirus CGAa31MP7 | NC_005218 | vertebrates,human | Bunyaviridae,Hantavirus,Hantaan virus | 1 | seg. S | EF990911 |
| Hantaanvirus CGAa31MP7 | NC_005219 | vertebrates,human | Bunyaviridae,Hantavirus,Hantaan virus | 1 | seg. M | EF990925 |
| Hantaanvirus CGAa31P9 | NC_005218 | vertebrates,human | Bunyaviridae,Hantavirus,Hantaan virus | 1 | seg. S | EF990910 |
| Hantaanvirus CGAa31P9 | NC_005219 | vertebrates,human | Bunyaviridae,Hantavirus,Hantaan virus | 1 | seg. M | EF990924 |
| Hantaanvirus CGAa4MP9 | NC_005218 | vertebrates,human | Bunyaviridae,Hantavirus,Hantaan virus | 1 | seg. S | EF990915 |
| Hantaanvirus CGAa4MP9 | NC_005219 | vertebrates,human | Bunyaviridae,Hantavirus,Hantaan virus | 1 | seg. M | EF990929 |
| Hantaanvirus CGAa4P15 | NC_005218 | vertebrates,human | Bunyaviridae,Hantavirus,Hantaan virus | 1 | seg. S | EF990914 |
| Hantaanvirus CGAa4P15 | NC_005219 | vertebrates,human | Bunyaviridae,Hantavirus,Hantaan virus | 1 | seg. M | EF990928 |
| Hantaanvirus CGAa75 | NC_005218 | vertebrates,human | Bunyaviridae,Hantavirus,Hantaan virus | 1 | seg. S | EU092220 |
| Hantaanvirus CGAa75 | NC_005219 | vertebrates,human | Bunyaviridae,Hantavirus,Hantaan virus | 1 | seg. M | EU092224 |
| Hantaanvirus CGHu1 | NC_005218 | vertebrates,human | Bunyaviridae,Hantavirus,Hantaan virus | 1 | seg. S | EU092218 |
| Hantaanvirus CGHu1 | NC_005219 | vertebrates,human | Bunyaviridae,Hantavirus,Hantaan virus | 1 | seg. M | EU092222 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Hantaanvirus CGHu3612 | NC_005218 | vertebrates,human | 1 | Bunyaviridae,Hantavirus,Hantaan virus | seg. S | EF990909 |
| Hantaanvirus CGHu3612 | NC_005219 | vertebrates,human | 1 | Bunyaviridae,Hantavirus,Hantaan virus | seg. M | EF990923 |
| Hantaanvirus CGHu3614 | NC_005218 | vertebrates,human | 1 | Bunyaviridae,Hantavirus,Hantaan virus | seg. S | EF990908 |
| Hantaanvirus CGHu3614 | NC_005219 | vertebrates,human | 1 | Bunyaviridae,Hantavirus,Hantaan virus | seg. M | EF990922 |
| Hantaanvirus CGRn45 | NC_005218 | vertebrates,human | 1 | Bunyaviridae,Hantavirus,Hantaan virus | seg. S | EU092221 |
| Hantaanvirus CGRn45 | NC_005219 | vertebrates,human | 1 | Bunyaviridae,Hantavirus,Hantaan virus | seg. M | EU092225 |
| Hantaanvirus CGRn53 | NC_005218 | vertebrates,human | 1 | Bunyaviridae,Hantavirus,Hantaan virus | seg. S | EF990907 |
| Hantaanvirus CGRn53 | NC_005219 | vertebrates,human | 1 | Bunyaviridae,Hantavirus,Hantaan virus | seg. M | EF990921 |
| Hantaanvirus CGRn5310 | NC_005218 | vertebrates,human | 1 | Bunyaviridae,Hantavirus,Hantaan virus | seg. S | EF990906 |
| Hantaanvirus CGRn5310 | NC_005219 | vertebrates,human | 1 | Bunyaviridae,Hantavirus,Hantaan virus | seg. M | EF990920 |
| Hantaanvirus CGRn93MP8 | NC_005218 | vertebrates,human | 1 | Bunyaviridae,Hantavirus,Hantaan virus | seg. S | EF990905 |
| Hantaanvirus CGRn93MP8 | NC_005219 | vertebrates,human | 1 | Bunyaviridae,Hantavirus,Hantaan virus | seg. M | EF990919 |
| Hantaanvirus CGRn93P8 | NC_005218 | vertebrates,human | 1 | Bunyaviridae,Hantavirus,Hantaan virus | seg. S | EF990904 |
| Hantaanvirus CGRn93P8 | NC_005219 | vertebrates,human | 1 | Bunyaviridae,Hantavirus,Hantaan virus | seg. M | EF990918 |
| Hantavirus CJAp93 | NC_005218 | vertebrates,human | 1 | Bunyaviridae,Hantavirus,Hantaan virus | seg. S | EF208929 |
| Hantavirus CJAp93 | NC_005219 | vertebrates,human | 1 | Bunyaviridae,Hantavirus,Hantaan virus | seg. M | EF208930 |
| Hantavirus Gou3-v9 | NC_005236 | vertebrates,human | 1 | Bunyaviridae,Hantavirus,Seoul virus | seg. S | AF288651 |
| Hantavirus LR1 | NC_005218 | vertebrates,human | 1 | Bunyaviridae,Hantavirus,Hantaan virus | seg. S | AF288294 |
| Hantavirus LR1 | NC_005219 | vertebrates,human | 1 | Bunyaviridae,Hantavirus,Hantaan virus | seg. M | AF288293 |
| Hantavirus LR1 | NC_005222 | vertebrates,human | 1 | Bunyaviridae,Hantavirus,Hantaan virus | seg. L | AF288292 |
| Hantavirus RG9 | NC_005218 | vertebrates,human | 1 | Bunyaviridae,Hantavirus,Hantaan virus | seg. S | AF288296 |
| Hantavirus S85-46 | NC_005218 | vertebrates,human | 1 | Bunyaviridae,Hantavirus,Hantaan virus | seg. S | AF288659 |
| Hantavirus S85-46 | NC_005219 | vertebrates,human | 1 | Bunyaviridae,Hantavirus,Hantaan virus | seg. M | AF288658 |
| Hantavirus SN7 | NC_005218 | vertebrates,human | 1 | Bunyaviridae,Hantavirus,Hantaan virus | seg. S | AF288657 |
| Hantavirus SN7 | NC_005219 | vertebrates,human | 1 | Bunyaviridae,Hantavirus,Hantaan virus | seg. M | AF288656 |
| Hantavirus Z10 | NC_006433 | vertebrates,human | 2 | Bunyaviridae,Hantavirus,Hantavirus Z10 | seg. S | EF533944,AF184987 |
| Hantavirus Z10 | NC_006435 | vertebrates,human | 1 | Bunyaviridae,Hantavirus,Hantavirus Z10 | seg. L | AF189155 |
| Hantavirus Z10 | NC_006437 | vertebrates,human | 2 | Bunyaviridae,Hantavirus,Hantavirus Z10 | seg. M | AF276987,AF143675 |
| Hantavirus Z37 | NC_005236 | vertebrates,human | 1 | Bunyaviridae,Hantavirus,Seoul virus | seg. S | AF187082 |
| Hantavirus Z37 | NC_005237 | vertebrates,human | 2 | Bunyaviridae,Hantavirus,Seoul virus | seg. M | AF187081,AF190119 |
| Hantavirus Z37 | NC_005238 | vertebrates,human | 1 | Bunyaviridae,Hantavirus,Seoul virus | seg. L | AF285266 |
| Hantavirus strain CJIiIin93 | NC_005219 | vertebrates,human | 1 | Bunyaviridae,Hantavirus,Hantaan virus | seg. M | AY748307 |
| Hantavirus strain YU61 | NC_005218 | vertebrates,human | 1 | Bunyaviridae,Hantavirus,Hantaan virus | seg. S | AY748308 |
| Hawaii calicivirus | NC_001959 | vertebrates,human | 1 | Caliciviridae,Norovirus,Norwalk virus | | U07611 |
| Hendra virus | NC_001906 | vertebrates,human | 13 | Paramyxoviridae,Henipavirus,Hendra virus | | HM044318,HM044432 1,JN255801,HM04443 20,JN255802,JN2558 06,JN255800,HM044 317,JN255805,HM04 4319,JN255803,AF01 7149,JN255804 |
| Hepatitis B virus | NC_003977 | vertebrates,human | 5003 | Hepadnaviridae,Orthohepadnavirus,Hepatitis B virus | | GQ377610,X59795,J 0040171,JN257172, EU306678,EU916228 ,AB014372,JN040759 ,GU456658,JXQ2687 7,AF418690,AY80039 1,AY738144,AB1959 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 42,DQ823093,AB205 191,GQ183474,AB33 0372,JN792915,AB01 4389,DQ089760,JN6 42143,AB900109,FJ3 86642,EU306702,JQ 801498,EU306680,H M750150,HQ700441, DQ993702,JN040762 ,AB287317,AB67441 1,GU815656,JX5072 13,AJ627218,KC5106 56,DQ975273,EU939 675,HM750147,FJ34 9240,JF828932,FN59 4754,GQ161801,AF2 23960,JN040772,HM 011478,GU456681,A B036918,FJ562245,G U815755,GU815599, GQ161785,DQ46379 6,GU456648,KC8753 22,EU564825,AJ1315 71,HM011497,FJ787 447,GU815746,EU57 9443,JN040805,L139 94,AB670307,FJ1514 13,GQ377584,GQ183 468,GQ924621,AB36 7425,GU815632,EU9 16204,AB675683,AB 036915,EU871978,D 0448619,JXQ96952,F J904419,EU717212,D 0304551,JN257179,F JQ32334,AY934763,G U815620,GQ377632, EU787444,HQ646553 ,GQ205379,FJ34920 9,AB670273,EU7172 15,EU522067,AB111 113,EU916206,JN664 919,JN257189,AB670 265,HM117851,GQ47 5320,GU456640,AY8 62868,FJ692559,FJ7 87482,GU815726,HM 750136,GQ377556,A |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | B116693,HM585196, AB670244,AF143302, GQ924647,AY040627, GQ477455,AB11111 5,JQ429079,AY09045 8,GQ477497,EU8719 95,AB119252,AB270 535,FJ709459,JF440 004,GU815657,DQ08 9794,AB073840,FJ56 2297,GU815565,FJ56 2308,GQ161829,FN5 94763,AM494700,GU 815692,AY167092,E U305540,JX429903,A Y161150,FJQ23659,A B485808,AB900106, HQ603073,JXQ79936 ,DQ089804,FJ386613 ,EU871973,AB48580 9,AB670305,JQ02732 9,AB198081,AY6415 63,AB112408,HQ700 504,FJ349211,FJ904 435,FJ899761,D5052 0,AY217366,HQ7005 18,AB674423,FJ5622 62,GQ377561,AB010 292,FJ692568,AB367 409,X97849,JN63046 3,GU332696,JQ0401 39,FJ904430,HM363 576,JX898690,JN040 775,DQ089768,FJ349 237,DQ089782,AB01 4378,FJ562231,JQ68 7533,AY330913,FJ34 9222,AB219427,AY8 00249,HM363603,FJ 562328,EU306694,FJ 562320,JX898686,FJ 386630,JN040787,AB 480041,AB198077,AF 418686,AM494716,FJ 692298,EU414137,FJ 023670,HQ700522,A Y738140,AB670261,J F491450,JN792900,J |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | N040758,EF473977, AY090460,JF754611, DQ993697,FJ899785, AB048705,AB367429, HM363573,FJ89976 4,FJ787471,AB67443 4,AB453982,EU3066 81,JX504545,AB2463 40,GQ377614,EU939 632,DQ478885,AB49 3836,AJ627228,AY64 1559,GU815575,JQO 40132,JN642167,HQ 700482,AF461357,G U815627,AB116079,J F491454,KC875342, EU859949,FJ692579, AB105173,FJ904425, HM750156,JN040815 ,EU366118,EU30554 4,GQ377585,AB0738 49,AY596111,AB032 431,FJ562220,JX898 699,HQ700463,KC49 4400,EU859899,AY0 57948,AM494689,AY 661792,EU414140,G 0183461,EU939593, FJ787465,KF679994, GQ475330,GQ92463 8,AY217358,EU5944 27,GQ924643,GU815 595,JN792898,GQ18 3459,HQ231885,FJO3 2354,JXQ26882,FJ38 6643,AB086397,GQ3 77517,HM622135,JQ 801483,EU859915,G 0475334,GU815718, GQ183475,GQ37761 1,AB042283,AY2173 76,DQ060827,FJQ236 53,FJ562271,GQ161 824,DQ478894,FJ386 594,AB330367,JQ023 661,EU589344,AB27 0541,EU747320,JF75 4594,JX898689,EU85 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 9910,AY247032,GU8 15649,JN040797,FJ7 87450,FJ349232,GU8 15559,FJ562339,JN8 27425,GU563561,AM 421534,AY090454,KF 373035,FJ899776,FJ 899787,AJ131568,AY 167099,EU939570,G 0924633,EU919169, AY373429,JN040790, KC875310,JQ040145 ,GQ161787,HM01149 5,AB453989,EU7874 47,FJ178472,AB2987 21,HQ700461,KC875 279,GU815568,FJQ32 342,FJ386586,JF754 629,AB031267,AB03 1265,JQ040174,HQ7 00480,FJ709465,JN2 57204,GQ924614,JF 754613,EU717216,E F464097,AB674429,J N827419,DQ823090, GQ372968,AB014397 ,FJ692611,JN040818, FJ518813,GQ475327 ,EU306728,AB67441 0,GU815623,EU5545 39,EU939555,JF8993 36,JN827420,JQ0236 60,AF121240,GQ377 527,EU594395,GQ37 7618,GQ377588,DQ4 63801,JQ027310,GQ 377534,EU916238,H M011487,Z35717,GQ 227692,GQ475309,E U522075,JX429915,A B270550,FJ692596,A Y090459,AF461363, HQ700445,FN594752 ,GU815686,JN64214 4,AB493840,AJ62721 9,JN400087,AY23327 9,HM066946,JX8986 97,KC875295,GQ924 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 628,AY741798,AB697488,GQ183483,AB112066,EU155822,EU560440,GQ183448,G0358157,FJ904400,GU815572,JN664942,FJ692588,FJQ23641,GQ477460,EU91621 7,AB375159,EU939603,GU815679,AB090268,JN642135,GQ924651,HQ833467,DQ315777,JN664914,AB300365,FJ562334,KC875328,DQ993706,EU939595,FJ562329,KC494401,AB109479,KC494405,JQ801519, EU859916,HQ700487,DQ463791,AB367426,EU939565,EU939625,AB67026 9,AY596110,EU414136,AB697502,JN664917,GU815634,HQ700497,FJ562302,GQ377530,GQ924636,GQ161832,AB219532,JN040828,JN040774,FJ386597,FJ386574,AF462041,AB367410,GU815781,JQ040164,KC875318,AB104710,KF495606,JF828938,JQ027333,FJ386579,EU871990,GU563547,AB241115,JN040824,GQ924660,GU815584,X14193,AB367434,EU872006,EU678471,GU456678,AB555500,HQ231884,JN040800,GQ161757,HM750139,EU939563,GQ477490,J0664508,AP011095,EU939644,GQ475348,AB670288,DQ089792,JN257164,GQ183 |

| Taxonomy | Rep.Acc.ID | Host | # GN's | Lineage | Seg. Count | GN.Acc.IDs |
|---|---|---|---|---|---|---|
| | | | | | | 462,GU815676,EU660233,HM363571,EU787443,GU815582,HQ700495,GU456651,FJ562279,AY934772,FJ899773,FJ562310,HM535205,JF440012,JF828923,GQ924639,JN664909,KF679991,FJ562254,AB205190,JX429905,AB111118,HM011490,AB241112,AF223965,GU565217,FR714493,AY217359,FJ878461,GQ377605,JF754615,JF754606,DQ463800,AB205192,EU872002,JX429912,EU306677,GQ377540,KC875326,EU882002,EU594401,AY902775,FN545823,FJ386640,JF440005,AM421529,EU919163,AB367400,AY206390,AY148342,DQ995805,AJ131572,DQ315781,HQ700477,KC875265,FJ386590,AB106895,EF103281,EU939658,GQ161830,EU939598,EU570068,JN792903,AB675682,FJ386578,FJ349208,AM494695,DQ478892,AP011085,EU554535,AB115418,EU872011,AB246338,EU594433,GU815573,EU594432,KF373056,AF143298,FJ386614,AM494707,AB900104,EU305548,JF754618,GU815767,HE981177,FJ562304,GU815580,FJ386637,GU815728,HE981175,FJ787441,FJQ32335,GQ161837,GQ16 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 1754,EU871985,AB274970,HQ700536,JF754590,JN664932,GQ377569,JN257175,G0377637,FJ386628,KC875278,EU859924,JN257200,AB300368,AB073837,HQ231882,DQ089795,AM295800,EU589336,HQ603081,EU547563,AB014366,EU939640,JF754586,FJ798095,AJ131133,HQ700459,GU815779,V01460,EU939600,FJ904410,KF373034,AY721608,JF754612,GU815770,GU815555,GU815590,GU815633,GQ377601,GQ183473,FJQ23643,FJ562233,AB106564,AB246336,GQ358140,JN257196,AY233282,KF679993,AB231908,HE981182,JF440017,AY161158,HQ603061,JD23677,JX429900,AB642099,GQ161795,DQ207798,DQ060823,KC875281,HQ833468,GU815729,AB188243,EU306688,FJ899794,HQ231877,GQ377526,EU562218,JQO27319,JX898695,AB036909,DQ377162,EU939543,HQ646554,G0377580,HQ646556,AY161151,FJ692583,AB059659,DQ993684,AB300372,FJ787485,FJ904433,AB365451,JF754604,HE981184,AY796031,EU872001,EU939664,AY163870,JN257201,JN040803,FJQ23646,FJ6925 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 82,FJ692574,JN2571 54,FJ562246,GQ377 533,EU330995,JXQ26 878,JX869999,HM53 5200,JN040764,HM3 63597,GU815631,GQ 377523,DQ991753,JF 754622,HM750155,A Y862869,GU815611, AY161146,AF363961, GU815640,GQ47749 9,DQ060829,AY2173 62,AB014369,FN594 765,FR714492,JN642 152,FJ349214,FJ562 293,EU939592,GU81 5665,FJQ23666,AM49 4703,AB493846,EU4 39011,EU916225,AB 042282,FJ882618,EU 916235,KC510659,G Q161826,AY161141, AY641562,AB198080 ,KF199901,JQ027331 ,JQ040131,AB116078 ,AB117759,JQ801487 ,JQ801481,AB026812 ,GU332698,AB01438 0,AB367412,AB3674 27,AB90096,AJ6272 26,AY741796,AB073 836,EU939642,AB11 1120,FN594758,KC8 75293,GQ161793,AB 367397,EU410080,JX 429907,FJ562307,G 0358151,GQ477474, AB713530,AB642100 ,AB195932,GQ37757 3,EU594385,EF1572 91,AY233291,HM011 498,AB219529,EU87 1974,GQ475351,EUS 94428,AB195930,EU 350409,AB642098,A B674432,GQ358158, AP011089,GU815766 ,GU815682,HM58518 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 6,GQ337544,JXQ268 81,DQ298162,GQ477 467,EU522070,EF10 3280,AB493837,JF82 8925,KF373038,EF53 6066,GQ477462,EU9 39547,FJQ32350,AJ1 32335,DQ315783,AM 494696,JQ801484,G U815594,AY179735, DQ788727,EU410081 ,HQ700447,HM01147 6,AY211378,EU5943 83,DQ486023,GQ183 486,AB6975512,JN182 331,EU594431,GQ16 1828,JX422901,AF09 0840,FJQ23661,EU58 9341,KF061169,EU9 39546,EU155824,HM 363595,EU939599,G 0161768,GQ475307, EF473971,DQ463797 ,GQ358159,AB27054 5,FJQ23632,GQ4774 53,EU919167,AY077 735,AB073827,AY37 3430,Z35716,HQ700 540,JN792899,GU45 6677,AB670253,EU9 39609,FJ589067,KC8 75287,DQ315779,EU 589339,EU594416,F N594766,AB048702, KC875305,FJ562306, AF241410,EU185780 ,GQ161761,KC87526 8,JN257206,FJ89978 6,EU305541,D28880, GU815563,HQ70052 0,GQ924642,JQ0401 35,AB670245,EU859 940,AB670284,AB27 0536,JQ272886,EU8 82004,HM750149,JX 079937,AB697509,JN 257165,EU871992,J 0801494,AY341335, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | AY161156,AF537371, EU547758,FM199976, AY233292,JN664948, EU306699,EU43901 8,FJQ32340,HM3635 74,EU564824,AY206 373,JF491448,EU939 556,EU859955,EU52 2069,EU410082,DQ0 89775,GQ47498,AB 36417,D23684,GQ4 75350,FJ562223,AY1 67097,AB640730,GQ 377608,KF679998,FN 594760,AB241109,A B246348,EU859946, AB050018,EU305546 ,JN257197,AB073841 ,GQ184323,AB90009 8,AB287315,DQ0898 00,GU815677,AM421 535,AB033554,JF754 616,FJ562330,JN040 791,GQ161762,EU93 9568,FJ562298,EU93 9574,FJ562287,KF17 0740,AB900108,FJ78 7452,JQ027314,DQ0 89756,AB670239,GU 815625,EU871991,JX 429917,JF828910,EU 939569,KF356417,K C836877,FJ386583,G U815662,JQ801489, EU306671,GQ37759 2,FJ709463,AY16709 5,AF143306,FJ89979 6,EU366133,FJ38664 1,GQ477482,KC8752 55,JQ801515,FJ5623 25,KC492739,AB205 120,AF282917,JN182 319,FJ692573,AB670 260,AY781187,GU45 6682,EU939662,DQ8 23089,HM011472,AB 270534,EU939654,G 0377542,FJ349219,D |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0448625,KC875300, GU815688,GQ92464 9,EU589335,FJ38663 8,AF121242,AY93476 94,JN040807,EU9162 24,GU815693,KC494 395,KF679996,GU33 2702,AB674415,JF82 8931,AB115551,GQ1 83467,FJ692578,JQO 40152,FJ386605,AB1 16092,AY862861,AB 670295,HQ603071,FJ 562327,GQ184325,A B670292,FN545822, DQ463802,FR714502 ,FJQ23671,JN257202, AB014388,AF418683, AB042285,FJ787442, GU815598,JF899335, JN664923,FJ386585, EU916237,JN182322, JN792922,GU815592 ,EU939620,FJ899779 ,FJ349212,X80924,G 0377626,AB033550, FJ386632,EU939665, DQ478896,EU678474 ,AB674404,DQ08976 7,X65259,AB670270, GQ475346,JN827414 ,DQ463788,JX87000 0,EF137802,FJ56231 4,GQ377539,JN2571 58,KC875297,KC875 263,JN040792,DQ78 8835,AB033556,EU5 94424,EU859952,HM 011473,GQ922002,A B116550,AF043580,A B188245,JQ801471,F J904437,EU859951,J 0801518,AB2744969, EU589338,JN664918, KF425557,FJ386686, AY781180,EU859932 ,GQ227695,AY81751 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0,FJ386658,FJ79809 8,AB036919,EF13494 5,DQ486021,FJ56229 6,EU414135,EU9162 41,JF828913,AF2425 85,AY206381,HM585 193,AB014383,GU8l 5725,JQ040161,FJO3 2332,AB274982,AY7 21606,EF103279,EU 589337,DQ089762,A Y596104,AM421530, AB697499,EU939610 ,HM363581,HQ23187 9,AF242586,EU4872 56,GQ161827,AF121 247,AF533983,EU33 1000,AF461362,KC4 94399,EU859934,FJ9 04395,GQ377586,HM 585200,GQ924656,J 0801509,AM421537, GU815761,HM58518 7,AF297622,EU4982 27,HQ60308,GU456 672,AB014398,EU88 2001,AY220701,GU8 15641,AB642093,EU 670261,FJQ32336,FM 209512,GU815660,G U456647,HQ833465, AF090839,KF485390, EU939669,V00866,H E576988,FJ386636,G 0475338,GQ924620, EU564821,JN182320, FJ899767,EU919162, JF828935,AB116076, HM750142,GQ92200 3,GQ477504,JX8986 91,DQ993707,JQ801 504,DQ776247,FJ562 248,EU678472,EU88 2003,EU439012,AB2 46339,JX154580,AB0 10291,HQ622095,AB 182589,GQ475312,H 0700502,AB205122, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | FJ657519,EU306682, FM209515,GU81561 3,AB246335,AB6702 42,EU859913,GQ924 615,AY206374,JN792 904,AB365446,EU83 3890,GQ477496,GQ3 77563,AY233295,FJO 32341,AP011094,JQ8 01516,HQ700519,EU 594396,JF828914,JN 257180,KF679992,G 0924637,EU717213, JN182332,JX504546, DQ478901,JN040802 ,FN545834,JN040821 ,FJQ23665,JN642128, EU717211,JX898694, DQ020003,AB032432 ,AB287324,FN54584 2,HQ638218,GQ4753 13,AB330370,GQ161 818,EU239222,GU81 5735,DQ361535,JN2 57155,FJ386680,AB1 11112,FJ709460,GU8 15667,AB302943,AB 362933,AB112348,A B453985,FJ562337,E U859911,FI692613,J F440016,EU939536,F M199979,HQ700542, JF754620,GQ377567 ,JF386666,AB367424 ,JN664936,FJ386684, AB274980,AB670267 ,AB073822,KC87531 2,EU796070,AY0904 57,AB900097,EU939 601,AB059661,KC87 5252,X97851,EU9162 29,HM750135,FJ386 624,AY220699,EU30 6704,KC875339,GQ3 77631,AB670287,AB 014377,JQ027324,D 0486022,GQ161759, AB246341,JN257173, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | EU939634,AB642091,AY738142,AB056516,KF170739,AY167093,DQ089773,JF828933,AJ131575,JF754589,AY373431,AF223961,AB014379,DQ399006,AF090842,JN257188,AB195948,FJ386575,GU456663,HM011465,AB274984,GQ161769,FJ386676,GQ377521,GQ161803,DQ986376,JN182321,G0358144,GU815772,EU916218,JN040801,AB090269,GQ475315,HM750154,GU456637,AB064311,DQ993708,EF494378,EU594387,FJ709458,DQ298161,AB453980,GU815589,EU594384,AB367398,GQ183452,JQ429080,JQ027311,AB205119,DQ975272,G0924629,EU185788,AB073845,EU871988,JEF208114,HQ700479,HM011471,HQ700458,FN594750,DQ089803,EU158263,GU456661,FJ787474,AY206388,EU872009,AB010290,FJ798099,AM494693,EF103285,HM363580,GU357843,AF411412,GU434374,FJ904406,AB073835,GU815604,FJ386683,X51970,HM363602,HM750134,FJ349210,AB210822,AY373428,GQ161775,GQ183454,DQ788726,Z72479,X75658,AB116077,FJ023651,KC875266,JF754626,AB201290,AF |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 143305,DQ377158,JN040783,AB471849,AB073844,GQ358153,AB091256,AB549213,AB775199,EU859918,AB073853,EU306686,AF286594,GU563546,FJQ23668,DQ089785,EU939591,FJ692591,FN594748,AF223957,GU563555,JF828917,FJ562263,FJ562269,GQ924632,FJ798097,DQ089757,GQ475308,AY077736,AB202072,X75657,JX429910,AB116080,GU563557,EU306698,S75184,EU414132,EU939558,AB365453,AB026815,FJ904414,AB674414,JN040823,G0161820,GU815616,AB205189,JX504533,FJ562243,AB241111,AY161157,GQ161782,GU456674,JX429898,AY161159,AY206385,AB031266,FJ7874439,AB900114,EU881998,JX504539,EU414138,AB274978,GU456652,GU456638,EU306710,EU939631,GQ924635,DQ089766,KC836879,AB219426,GU815574,JQ000008,JQ040167,EU91623,6,GQ161789,GU815675,KC774178,FJ899793,GQ167302,EU414142,JN792905,KC875311,FJ787445,DQ089784,JN182329,GQ183455,KF170742,FJO32344,JN257152,GQ161819,AB032433,KF373040,AF143307,AF4 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 11409,AJ309370,AF143304,GQ377629,AB195945,JF754605,AB078031,EF494379,G0924611,AB036906,KC875336,EU595031,AB367392,AY123424,JF754598,AM421532,AY781183,AB674437,JQ040149,HE981183,GU815727,GQ475345,GU815601,AB302945,GQ475357,GQ358147,EU796071,JF436923,AY161152,KF679995,FN594753,AB073831,AB697496,AB367404,FJ386623,FJQ32357,HM011474,DQ298163,EU306729,JQ027328,JN040776,GQ377570,AF305327,GQ161776,GU815570,AB116083,FJ386581,FJ562285,EU787436,FJ386689,HQ700534,AB073858,AF330110,IQ801499,AY217374,FJ904409,DQ304550,AY217369,JXQ26880,FJ904436,JQ023666,JN642161,JF754587,AF121245,GU815642,KC875288,FJ562276,FJ349221,EU787440,DQ377164,JN664916,JXQ96953,AB195950,X68292,EU939582,EU859945,GQ377593,GQ205377,AB109477,GU815765,GQ377627,EU594407,D50517,FJ787486,GQ161833,FJ709464,JQ027318,HM363613,AY596106,EU916230,AB675677,AY800389,JN182334,EU939588 |

TABLE 10-continued

| Taxonomy | Rep.Acc.ID | Host | ViroCap-1.0 Taxonomy # GN's | Lineage | Seg. Count | GN.Acc.IDs |
|---|---|---|---|---|---|---|
| | | | | | | ,JN811655,HQ70048 5,D50522,KC875324, JQ040146,GU815583 ,EU306717,JN642139 ,GQ377519,AY70708 7,GU815744,AB7135 31,JN257198,FJ3866 27,HQ700486,FJ3492 34,GQ161800,DQ922 649,JQ801520,AB064 315,GQ477475,JN82 7422,FN545838,AB2 05129,HQ700537,AB 119253,FJ787469,GU 815606,AB270537,H 0646552,JQ040126, AB675679,GQ477493 ,FJQ322349,AF100309 ,EU919168,DQ99368 5,AB642101,EU3066 72,KC875314,FJ5188 10,HM363575,JN257 174,JQ000009,FN545 836,EF103283,JN257 161,JF754617,AF121 244,FJ904438,EU939 677,AB713529,AB49 3827,FN594756,AB3 67394,JF828929,JQO 40172,FJ692532,JQ8 01485,EF634481,JXQ 96956,JF440000,GU8 15694,FJ386681,AB2 87328,FJ562261,FJ5 62242,AB367405,AY 161138,FJQ23676,AB 674403,AB198083,A B106885,GQ183478, GU456665,GQ47748 3,GU456653,FJ70946 2,DQ890381,AB6702 38,AP011102,GU815 579,FJ562274,EU306 691,JN642153,GU33 2707,AB287318,GQ4 77465,FJ562292,GQ 477461,AB205128,H M585192,EU859947, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | JX429896,FJ562301, JQ801505,GU815704, AF461358,AY206380, EU939581,HQ70054 3,GQ16176,HQ7005 35,DQ478886,EF103 284,FJ692563,JN792 914,AB367423,DQ99 3710,FJ562311,GU81 5751,JN257190,GQ9 24625,JN040768,EU9 16231,AM421536,X6 5257,FN594755,FJ90 4408,X97848,AF3843 71,FJ882614,EU9396 28,AB471852,JQ0401 53,GU815722,X7565 6,FJ562278,JN25716 0,EU871986,EU8352 40,X98072,FJQ23634, EU366132,HM36357 8,AB670252,DQ0897 65,AY233285,GU434 372,AB367407,FJ562 266,JXQ26887,GQ37 7600,AB480040,GU8 15768,GU456669,EU 872008,GQ377604,G 0161755,AB110075, GU815643,GU81556 0,GU815630,GQ9246 10,EU564823,JN0408 08,GQ358150,GQ183 471,FJ692577,KC875 285,JQ027330,AB367 399,DQ980549,AB36 8296,GU815564,AB0 14373,AB014370,FN 545835,FJ562318,H M363565,AY217377, AB900100,FJ787437, Y18858,AB036920,H 0700472,FJ787484,A Y862865,AY934764, GQ184322,GU81573 8,AB330371,GQ2053 88,GU456676,AB266 536,GU815668,GQ37 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | 7516,GQ924623,EU306693,AY330914,GQ358145,EU331001,GU815681,AB073851,KC87299,GQ47530 6,AY781184,GU8157 52,JQ801488,AY7960 30,AB195952,GU815 762,JF754597,EU330 992,AB365449,JF754 593,EU882000,KC87 5269,AB014361,DQ9 75271,EU939651,JN0 40798,AB367413,FN 545839,HM011467,A B365447,GU815648, AB274972,HM363572 ,AB064316,DQ47888 3,GU815600,EU9396 13,AB670277,GQ475 332,JF754625,EU871 980,AB367395,GQ18 3477,FJQ23675,GQ3 77596,GQ377529,DQ 823088,FJ904403,JN 664947,GQ205385,F JQ23662,AB55496,A B241114,EU881997, EU919165,DQ089802 ,JN257194,EU155825 ,GQ377559,JN66493 9,AB674407,EU9395 97,JN040777,GU456 646,KC494397,JQ68 7532,GQ377547,FJ3 86596,HM011492,AB 670282,KC875316,K C875335,AF418685, AB241110,FN545832 ,KC172106,AB21451 6,FN594764,DQ9805 50,FJ562319,JN2572 10,EU939580,FJ6925 65,AB014363,DQ986 375,EU439024,AY64 1560,AB1I9256,AY2 06391,FJ657529,KC8 75280,FJ787480,EF1 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 03276,HQ700464,JX898693,AB670250,EU43901 5,FJ386673,JF44001 3,AB073848,GU815645,AY800392,EU570075,JQ04014 2,AB300359,FJQ3235 9,JF754601,FJ56232 3,AF241411,GQ4774 52,EU306709,AB195 947,AB074756,AB11 1117,FJ882615,GQ1 83451,AY721605,EU 939653,JN642165,EU 939607,AB900101,G 0414522,JF491449,J J131573,GQ377525, HM750133,AY738147 ,AY161154,GU56355 9,FJ151414,KC83688 0,AB270548,AY7381 43,EU330993,AF043 560,GU815731,FJ562 239,FJ562324,AB670 271,HM585195,AB20 6817,GU815635,EU5 94422,KC875327,GQ 477473,FR714505,G 0161778,HM750144, EU939656,FJ386591, JQ027313,EU859933 ,EU939539,FJ562309 ,JN040817,AY217357 ,AB367416,JN257170 ,FJ787487,FN545821 ,FJ904413,GQ47534 2,AB073838,EU3067 12,FJ178476,AB1959 57,FJQ23658,EU9395 94,GU332705,JN040 757,AB670296,D2368 1,AB375170,KC8753 17,AY902769,JX5045 35,GQ377557,AJ131 570,AY233288,AJ344 115,EU939643,EU93 9562,AB198079,KC5 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 10645,GQ205381,GQ377621,AB073856,GU815776,GQ377591,AY033073,AB493845,FJ657525,AB900115,DQ993704,EU330990,JF828922,JF754632,FJ899790,FJ388608,AB367414,DQ993703,JN257207,AB670243,DQ478881,JF754623,GQ161797,GU815709,JF899338,AB375160,FJ692605,FJ562225,GQ475352,AB675680,AB241116,JQ664507,JN642146,KC510649,GQ161835,X72702,GU815708,AY167098,FJQ23637,HQ700526,GQ377571,AB900099,JF828927,AB670266,EU939648,GQ477501,FJ562326,AB670294,GQ477476,AB046525,GU815651,EU859944,AP011088,FF688062,AM421543,JF828909,EU939605,FJ692570,AB111125,JN040750,GQ924655,EU916227,AB300369,JQ040144,AB109478,AB471855,AM295798,AB048704,KC875306,JN792917,GQ358155,GQ377568,FJ899795,EU330998,AB219428,JN257211,AB287316,EU939615,JF754624,HM750153,EU589346,JN040827,DQ922651,AF473543,DQ089758,HQ700460,AM421533,KF767452,FJ386672,AB302944,DQ448621,JN257153,HQ603072,AB22 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 2710,AP011093,JN040781,JN400089,EU306721,AB036908,HQ603069,HM011504,AF384372,JN040806,D0993692,AB367428,AB219429,HQ231881,FJ692599,GQ924624,FJ562273,EU919175,GQ205380,AF043593,GU456654,GQ377624,JN040804,JQ023665,AY206389,KC510650,HQ700532,EU660229,GQ922000,AB194952,EU859937,AB116081,EU859908,AF418692,AB670279,JQ801491,FJ562305,AB073843,JN040825,KF679990,GQ477472,EU939553,EU547560,AM494690,GU815705,EU871982,DQ089764,X85254,EU554542,DQ478893,GU456641,AY217365,AB453987,AB194947,GU815663,FJ787444,AY781177,GQ475319,D23683,AB900107,AB471851,FJ562272,EU919197,AB112471,KC875271,FJ562253,AB287314,EU564820,FJ904424,GU815699,AY373432,GU815710,EU594430,GQ377548,AB674426,JN257171,AY090461,GU815716,GU815639,EU871994,AB014371,FJ904427,KC875303,AB471850,JQ664503,AF461361,JF828924,GU815673,KF373033,AB036910,GU456642,EU939649,EU939590,GU81 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 5773,FJ386661,EU939663,HQ236014,GU563554,FN545825,EU871983,AB674435,AB064313,EU939639,DQ089774,FJ787489,FJ349224,GQ183472,GU815674,GU815578,AY161163,FJ904418,FN545826,JF412801,AB042284,FJ349220,HM363591,FJ904416,AB367415,DQ823092,AB270540,FJQ32352,GQ161777,EU594425,EF103282,AY721612,KC494404,D12980,AB205125,AB675674,JX429914,JQ040173,JQ801495,JN664937,AB287329,FN594762,X75664,HQ700491,AB274971,AB697505,GU357845,GQ161823,FJ562303,DQ377165,EU859925,AJ627215,GQ358143,FJ562333,FJ386617,AB697492,AB674430,JN664911,EU939578,AP011092,JN040813,JQ040150,AF418679,EU939538,EU939641,FJQ23673,EU594436,EU155829,HQ700512,JN642137,FJ787458,GQ161811,AY206382,AB246344,EU306726,HM011480,DQ089776,AB453988,EU939573,AY236163,EU439023,EU330999,FJ386622,AB471857,EU366116,JN257167,EU939638,KC875258,AB119251,HQ603079,AX155589,KC510651,FN594761,JN18232 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 8,JN040765,FJQ2364 9,AB036912,EU5700 74,JN182318,GQ377 551,JQ801475,FJ349 231,FJ562275,DQ060 825,GQ377638,AB01 4387,JN64 2163,AB11 7758,AB775201,JQ80 1479,DQ993687,FJ56 2240,FN594751,DQ0 89788,KC510643,FJO 23660,GU815666,JF8 28907,EU916216,JN8 27416,AB111122,FJ13 86635,EU872017,GQ 358136,JF440008,EU 439019,EU939660,FJ 562321,JX429906,AB 471848,X75663,HQ6 03067,GQ924648,AF 121249,GU815763,A B073830,HQ700531, DQ995801,FJ904422, JN040770,FJ787470, AB036905,AF223962, FJ386588,FJ692560, JN257208,EU660226, FJ784782,GU815672, FN594749,AP011106 ,AY057947,EU85994 8,GQ183484,FJ5622 82,AB453981,AB330 368,AY862864,GQ37 7574,FJ787477,HM3 63609,GQ331048,AY 206377,GU815553,A Y738145,DQ377160, AY233274,EU306711 ,AB367420,GU81563 7,FJ562256,EU59439 0,EU939622,GQ9246 12,EU562219,FJ9044 39,AB274975,AB367 433,EU871997,FJ562 244,AB670249,JQ687 530,EU670263,KF06 1170,GU721029,AB6 70300,AY741794,AB |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 675676,GU332699,AB014382,JX429897,J0027315,DQ993709,AJ309371,AY739675,GQ377553,GU56355 3,AM184125,FR7144 98,JQ801514,AB6420 96,EU594393,AF297 621,GQ477459,JN79 2897,AY167091,AY1 61155,AF223959,JN6 42156,V00867,FN545 827,AB074755,EU85 9928,FJ386606,GQ3 77628,AM494705,HE 981176,EU859914,G 0924616,AF411411, GQ183463,AB112065 ,GQ161831,EU30668 7,GQ161780,EU5893 43,GU815654,AM494 711,FJ386601,AB219 430,JN257212,EF137 803,JF439999,FJ692 592,KC510655,AY20 6375,GU815720,JN7 92921,KC875320,AB 270538,GU815741,G U456635,AB493847, DQ377163,JQ040127 ,AF418691,JQ027323 ,HQ700528,DQ89914 7,HM363567,JXQ969 58,GQ377520,AB375 168,DQ478899,EU58 9345,EU155826,AY8 17512,EU670262,D1 6667,HM363612,HQ6 03078,EU939587,JX5 07210,AY934774,GQ 477494,FJ899777,EU 871987,AF182804,FJ 386660,HM363588,A B670262,EU185786, AF479684,FN545824, AB113876,JN664913, AB205152,EU921418 ,AF090838,JQ801500 |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| | | | | | | ,EU560439,U87742,AM494702,GQ358138,DQ089779,FJQ32338,AY934766,JX898696,GQ477458,FJ518812,GQ477486,AM117395,EU859900,EU579441,EU939549,AB300367,EU787442,FJ899775,X98073,AB105172,GQ377576,FJ9044 31,AB059660,FJ3492 25,GQ377595,AB194 951,EU939619,GQ47 7491,AP011098,EU9 39627,AB674504,AB 674418,FJ562290,GU 815661,GU332703,G U815697,EU562217,J N64213,FJ386645,A B453979,JN792919,H 0603075,JN400088, D23680,DQ089787,G U815671,GU563545, HM363605,HM363604,AB270549,JN64214 7,HQ700483,DQ4637 92,HQ603076,AB367 802,GQ475347,EU87 1999,AM295796,GQ3 77528,GQ167301,EU 498228,HQ700442,FJ 386646,EU939650,G U332700,GU451682, HQ700444,JN257176 ,JN257215,FJ386638, FJ386675,AB367408, KC012653,EU939584 ,GQ377558,AB69750 0,AY781185,FJ89976 6,HM590471,EU6784 70,AB670297,AB362 931,GQ161809,GQ16 1817,FJ787463,GQ1 83485,AB453983,AY 817514,AY738139,A M494699,FM209513, JQ040140,AB900102, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | FJ386577,AB670290,KC875331,EU594397,GQ358149,AB073855,JN792911,HQ700507,JN257178,AB116091,AB300373,AB367402,HQ700511,JF440001,AB485810,JQ927384,HQ231878,EU594406,JF491447,HQ700499,AY206393,DQ304548,FJ386664,GQ161770,AY220700,D0315778,JF828906,EU871989,AY161153,EU594388,DQ478900,AB201287,JN642166,JN040789,AB014392,HM011481,JN257157,AP011104,JF828926,EU660231,GQ377602,EU330996,KC875264,JN257187,JN040778,EU939629,FJ562250,GU815652,FM199977,EU589342,FJ386584,FJ562267,GU815562,JF828921,GU815685,FJ562255,EU939681,FJ692569,EU579442,GU815659,AF280817,AB697508,EF103275,GU815759,JX470760,FJ787473,KC875334,JQ027325,EU939636,JN827418,KC875304,KC494394,FJ692554,GQ358154,JX429904,GQ377545,JQ801506,JF491453,AY217370,DQ975274,AB367431,AY596103,AB493841,GU815717,JX898688,HMO11475,FR714501,JX504538,HM011503,AF182802,HQ700454,H0700469,AB033551, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | EU522071,EU916219,JN040753,AB116266,FJ562336,FJ349226,EU833889,EU916239,EU939554,JQ80147 0,AB375163,JF44001 0,EU787439,AF4186 87,GQ331046,AY518 556,JF439996,GU456 664,AB670283,Z7247 8,HQ700448,FJ69256 7,DQ361534,FJ69253 6,AB179747,AB0379 27,AF121243,EU239 223,AY766463,AM49 4710,JN664930,FJ89 9792,FJ562291,AY23 3287,FJ899772,EU87 1969,AM295795,GU8 15680,AB064310,AY 233296,HM590473,F J562226,EU439025,J N664921,FN545837, GU815758,FJQ32356, AM421546,GQ92460 6,GQ161804,FJ5623 35,EU155821,GU434 373,EU939672,EF46 4098,AF297623,EU9 39617,GQ183453,AB 697497,EF536065,AB 697507,AY233278,G 0475336,Y18855,EU 570070,FJ899765,AY 217373,HQ700506,G 0922005,GU815609, AP011103,FJQ32339, JN040812,GU815602 ,EU939589,GQ47534 0,AY903452,GU3327 06,EU916214,X98076 ,JX504540,DQ08979 9,JF754614,DQ08977 8,GQ377555,HQ7004 98,AY206386,JN6421 51,AF151735,GU456 656,AB270544,AY21 7355,JN040814,DQ8 |

TABLE 10-continued

VoroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 23091,AB670241,EU859954,FJ787462,FJ787454,JN040826,AB188242,AB674428,FJ386595,EF473972,D0089772,JQ664506,FJ386654,EU306715,JXQ26885,GQ924646,GQ161812,GU456680,KC875313,EU9396978,FJ904415,EU939575,FJ899791,AP011084,FJ386589,GQ161756,EU859905,AB353764,GU815581,AM494718,JQ040157,AB219531,FJ899780,FJ386665,DQ993693,JN182327,JN642160,FJ349215,EF494376,GU815777,AY311369,EU594423,FJ386609,GQ183465,KC315399,JN257163,FJ657528,EU939655,EU835242,JF754603,AB201288,EU594399,GU815558,XQ24615,AB111946,AB674413,AB713528,AB212626,FJ349239,AB111121,JX504534,JX560519,GU815690,JQ040151,JQ687531,EU871972,HM363596,AB014362,HQ603059,AY167089,GQ205441,AM410963,HM585191,FJ562340,AY661793,GU815626,EU560438,JN642155,HM363582,HM363599,DQ536414,AB375165,AB670256,FJ562228,AP011099,M32138,HQ700492,FJ3865692,AB670298,AY781182,AB375166,FR714506,GQ377546,X756 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 65,FJQ23648,AB1094 75,GU815549,Y0758 7,EU787434,AB3674 19,JQ040134,AB6702 58,JF439997,HQ6030 63,EU305542,JF4369 20,EU594435,AB300 364,JF754610,DQ993 689,FJ899769,FJ692 585,AB246337,JN257 149,GU332701,AJ74 8098,EU594421,EU7 96072,FJ562332,EU9 39668,EU562216,FJ6 92507,Y18856,FJ904 396,AM117397,X978 50,GQ377589,EU939 542,AB120308,KC51 0654,AY161144,GQ9 24619,X80926,GQ47 7481,AM494713,JQ7 32168,GU815783,EU 522073,FJ692600,JQ 801482,FJ692556,JF 828919,AB048701,A B11387,FJ356715,A B64209?,HQ700471, AF143303,FJ899789, FJ386655,HM585194 ,GQ377609,EU66022 7,AB073829,GQ1617 86,JF439994,FJ9044 28,GU815695,GQ161 825,FJQ32333,AB367 396,FJ904401,GU563 551,HQ700450,KF06 1167,AB014364,AF41 8676,GQ183457,HM3 63590,DQ448627,AY 817509,JN040830,JN 040761,FJ349233,JF 754600,AB195941,E U796067,KC510657, GQ183466,EU85995 0,FJ562265,AB67024 6,GQ205384,DQ9937 05,HM363568,AM421 542,AY217361,JN257 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 182,EU366129,JN315779,FJ349229,EU916220,GQ477478,DQ304549,AM422939,AB195935,DQ478897,AB116088,AY233283,EU439021,GQ477454,EU522072,EU306697,FJQ23642,GU456649,EU919174,DQ99368,2,AY330916,GU815608,AP011096,AB493838,JF828934,EU939540,EU859930,KC875262,AY206376,AB367411,FJQ32331,FJ882611,EU547562,AY781179,AB675681,H0700524,AY233286,JF754591,EU239218,AY161145,HM011477,AJ627223,EU939680,JQ040129,JN664922,EU939626,AF41868,FN545840,FJ56229,HQ700514,AB3674,06,FJ386674,FJ899774,HE981172,KC875259,KC875325,HQ700503,AF121241,DQ995803,AB674431,GU456673,GU815569,AB202071,EU594434,EU554538,EU939596,EU306724,EU305543,EU717214,AY206387,EU796066,FJ386603,FJ349296,FJ904432,HM011488,FJ787436,HM585188,HQ700470,XQ2496,JF828915,KF679988,AY238972,HQ231883,AM494691,HM363592,JN664925,AB274981,GQ377560,KC492740,GU815778,AB670280,G0161790,DQ486024, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | FJ386620,HQ700510,AB116551,FJ349205,JQ040155,AB116082,EU859909,HM01150 2,DQ899149,HE9811 78,GQ377613,EU239 217,AF223954,GU81 5714,JQ027334,DQ2 98164,JXQ96954,FJ7 87438,HQ700440,GU 815621,FR714499,A B078033,JN040819,A B014374,EU306700, FJ692558,AB583681, AM494692,HE981174 ,FJ904399,FJ386625, AB201289,AF182805, HM585190,EU59438 9,JX504536,HM0114 94,GQ377639,AY236 164,EU939606,JN040 793,AB697503,DQ08 9777,JQ040130,EU0 86721,GU456667,EU 939550,AB367432,A Y902776,GQ161802, AJ627216,FJ562260, AB073828,JQ801517, FJQ23667,AB583679, GU357846,EU410079 ,JF828912,AY206378 ,GU815591,DQ44862 2,JX504544,AB67442 2,AB246346,JQ04016 0,FJ386618,GQ3775 77,GU815670,AB115 417,FJ562322,HQ700 505,EU594408,FJ904 398,FJ562281,AB368 295,JN257214,AF121 251,AY167102,FJ709 494,DQ899148,JN25 7177,AM421531,JF75 4621,EU859941,FJ56 2222,AB210818,JN04 0766,FJ386576,AB01 4390,M38454,FN594 771,JN400086,EF473 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 975,GQ183481,EU93 9557,FJQ32355,AB03 6907,XQ1587,EU2392 25,FM199980,FN545 831,JF754602,GU168 596,AB697489,KF373 041,GU815619,AB77 5200,JQ801486,HQ7 00496,AB219534,JQO 27312,U87747,AB091 255,KC875275,GQ16 1794,DQ315785,GQ1 61773,AB493833,AB 480036,JF828936,AB 697494,JQ040138,K C875292,FJ386653,G 0183479,FJ904446,A M494701,GU815658, HM363589,GQ92464 4,JN642149,GQ3775 99,AB195936,JQ8014 90,JN257166,EF1349 46,GU815629,AY217 360,HQ700500,FJ562 283,FJ386602,DQ993 683,FJ386619,GU815 587,FJ386659,HM36 3579,JN792909,JN04 0820,JF828905,EU93 9671,JX504543,AB03 6916,JN040751,DQ4 48620,GU815617,HM 011466,EU939585,A F418680,EU239220, AB367393,AB375169 ,EU306695,HQ70050 9,AB674417,GU4566 84,GQ475311,FJ787 481,EU155823,KC87 5270,GU456671,AB1 95954,GQ475331,GU 815715,AB274985,A B205123,GQ475326, JN642134,AM180623 ,FJQ32346,EU522066 ,EU414141,AIQ12207 ,AB195943,DQ82308 7,AY217375,EU3067 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 20,HM750140,JX154 579,AM421547,AY90 2774,GU357844,GU8 15734,FJQ23633,FJ3 86669,EU670260,FJ3 49235,AB056514,FJ8 99762,AM421539,AB 078032,AB493831,D 0315782,JQ429081, AB222711,AB210819 ,AB036911,FN54584 1,HQ231880,JQ0401 33,AF418675,GQ924 604,AB036913,KC51 0644,EU939623,HQ7 00513,AY206384,GQ 924641,KC875284,A Y233280,GQ358146, AB205010,JQ023664, GU456662,GQ18345 0,JN182325,EU93965 2,FJ787451,FJ56222 9,GU456644,AB9001 10,GQ377536,AB426 467,JN792920,HQ70 0446,AY220704,JF75 4627,FJ386612,AY15 2726,DQ478882,GU1 77079,JN642145,DQ 993680,AY161161,FJ 692555,JX869998,D2 3678,GQ358141,AB2 46347,GQ161774,GQ 475316,AB113875,JQ 027320,AB362932,G U815653,FJ899781,F J349217,EU872013, GQ377564,GU81556 6,AB104711,JN04081 1,AB274983,JQ044014 1,DQ089763,GQ2276 94,AF418689,KC510 646,AY862867,DQ063 0,JF754595,FJ56223 0,EU833891,FJ69250 6,EU155895,EU7960 69,JF828937,FN5947 59,JX507080,JN6421 |

TABLE 10-continued

ViroCap-1.0 Taxonomy

| Taxonomy | Rep.Acc.ID | Host | #GN's | Lineage | Seg. Count | GN.Acc.IDs |
|---|---|---|---|---|---|---|
| | | | | | | 27,GQ924622,KC875286,HM153811,EU660225,AB555499,AB287323,FJQ32361,DQ298165,JQ023662,FJ692584,GU815638,GQ477489,JQ801508,AY738146,D50489,GQ184326,DQ922650,HE981179,AB900112,AY233284,GQ161810,EU872003,FJ562221,AF223964,EU564826,AY217367,JQ801522,AM117396,AB033553,KC875302,AB222715,AY641558,KC875296,FJ386633,GQ377515,GQ377582,FJ692609,JN664945,AB555497,EU306689,AB367435,GQ477487,EU872015,EU787446,GU815702,KC875274,KC875329,HQ700474,GU456660,EU787441,JF440002,AY217363,DQ089759,GQ161764,EU554540,FJ562249,FIQ23652,AB036914,HE981181,Y188857,FN594768,GQ377562,FJ904420,HM750143,EU306707,AB219530,AF143300,FJO23631,GU168594,GQ161798,AB166850,AB073850,JN040760,D0020002,EU678475,EU872004,GU815655,EU594405,EU155828,JQ801497,JN792895,GQ924603,AY596108,GU815739,FJ904434,AB246345,AB287321,HM011493,FJO23639,FJ692586,EU871993,AB112472,AB4 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 80039,JQ801496,GU456675,AY161143,JN792902,AB493844,KC494402,JQ040158,JX154581,AB073854,GQ922004,EU330997,AB064314,DQ060828,KF373037,JN642158,FJ787455,AB073839,JF82911,EU306703,AB014385,GU815706,GU456670,JN664912,HQ700517,JQO40162,DQ448025,AB010289,KC875261,AF418677,HQ603068,HM363601,AB674424,EU594426,DQ448624,EU919176,EU93964,JQ801523,HQ684848,FJQ32351,JN664946,DQ089770,JQ801511,AY293309,EU239219,HM585199,AB697506,EU859935,GU815605,GQ183460,AB670306,FJQ32360,GU815707,GQ474749,AJ627227,JF754596,AB471854,AF121239,FJ386678,EU570072,AB116089,FJ904423,KF485389,EU439008,GU332693,GQ922001,EU859936,FJ692610,GQ475317,GQ477471,GQ161813,JQ688405,HM750148,GQ924631,EU872005,D0329356,GU357842,EU414143,EU594415,FJQ23645,GU815585,EU859898,EU939604,AB116549,GU563562,FJ692571,AY741797,AF241407,GQ377552,FJ562288,DQ536413,JF44014,AB188 |

| Taxonomy | Rep.Acc.ID | Host | # GN's | Lineage | Seg. Count | GN.Acc.IDs |
|---|---|---|---|---|---|---|
| | | | | | | 241,KC510641,FJ386652,AB375161,DQ089796,JN257186,FJ787449,FJ692603,FJ349206,EU859912,JF754609,AB222714,KF767450,HM011468,GQ183458,AB205188,EU916209,JQ027322,AB026813,HM750145,GU815696,AY220698,EU881995,EU859901,AB674419,GQ377587,KC836878,EU919164,GU815711,KC875289,AB205121,EU939624,EU916226,JN257181,AF418684,AB493828,AB014399,GQ377579,EU939612,AF068756,HM363611,EU939614,AB674412,AJ131569,AB116086,AY721607,GU815646,KC875273,AB076678,AM494697,AB330366,FN545833,JX429916,FJ562316,JN642140,DQ089781,AF143308,HQ700516,FJ904402,HQ700462,AJ627224,DJ50519,FJ798096,GU815610,AB274973,AB195938,AB116094,AY247030,GU456668,FJ562258,JN257168,AY233290,HM750141,GQ183476,FJ386593,GQ477503,GQ205387,FJ349236,KF170741,JF754619,GU815775,JN792894,EU859927,EU916211,GU168595,AB116085,JX978431,EU594394,EU306714,JN792907,JQ040165,JQ664505,FR714500,FJ904 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 417,GQ377575,AY596105,EU872012,GU815747,AF405706,DQ683578,AB119255,EU595030,EU916207,GQ475354,JQ687529,AY902770,HQ603070,GQ477464,EU939645,KC875272,EU939564,FJ692594,AB049610,GQ377612,JX429909,JN792916,FJ386682,AF418674,DQ899142,AB471853,AY902773,GU563349,JN040771,JQ801480,EF576808,AB287327,GQ161783,AM421540,AP011090,JN182333,HQ700456,GQ475321,AJ131567,GQ377541,FJ562237,GU332704,EU939635,EU939611,KC875341,HM750152,GQ872211,EU939586,AY233289,FJ386615,FJ386626,DQ089771,AB206816,G0477466,FN594770,DQ448628,KC494398,FJ657522,FJ904412,JN664934,JN792913,EU916232,AB674421,FJ562299,AJ627222,X69798,GU815753,GU815622,AB300366,KC875330,FJ787460,GQ924630,KC875251,HQ700443,FJ562313,FJ692604,GU811573,AB014365,JX429902,EU939602,AB670310,FJ349230,EU859903,HM011482,HM011500,EU564822,JX429908,GQ161792,GU815664,AB493830,JQ801524,AB674427,DQO |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 89786,AB104709,JN040785,GQ377607,EU085921,DQ478884,KC875254,AB674408,AP011097,EU859943,AB367803,EU23922 1,GQ205382,AY0904 53,GU815650,FJQ323 48,GU456636,JF7546 30,FJ589066,AB3003 60,GU332695,FJ3866 51,AY862866,HM363 577,FJ787456,FJ386 610,EU871977,HQ60 3066,EU919171,AM4 21541,KC875337,JF8 99337,FJQ32345,AB2 22707,AB365448,GU 815760,FJ386649,AM 494712,AB287320,JN 257151,EU330994,JN 182330,KC875301,J 0664504,HQ700455, FJ899784,GQ477484 ,EU939630,AP01110 8,U46935,AF461359, GU385774,JQ027321 ,AB205126,KC51065 2,EU871971,AB1980 84,GQ377619,M3863 6,DQ089793,HM3635 84,AY330915,GQ924 605,AB670281,GQ47 5337,HQ603082,AY1 79734,GU815689,AY 217372,X65258,FJ38 6604,JX898692,JX50 7214,FJ386687,GU45 6655,AB471856,AF29 7620,GU456657,EU4 39020,KC875291,FJ7 87488,EU306716,X98 075,FJ692533,AY161 148,HQ833470,EU93 9661,FJ692564,AF29 7619,AB900113,FJ56 2331,GQ477456,AB4 53984,KF37039,AB5 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 55498,GQ183482,EU939579,FJ787467,FM199978,FJ904426,FJ349213,GQ475322,AB198082,AB014381,AB246317,GQ377636,AY233293,EU855929,EU859956,AM421538,JQ801472,EU594382,GU815687,EU594409,EF103277,EU594402,EU939566,DQ377161,DQ089791,FR714496,JN040784,JN257217,AB014376,JN792896,AY781178,GQ377565,EU570073,JQ801512,JQ664502,FJ562264,EU594386,DQ315780,HM363586,JN040755,AB302942,JX507211,AB074047,HQ236016,AJ627221,KF679997,AB014391,AB670263,AB222712,AM421545,FJ1023647,JN040754,EU939621,FJ349238,FJ904440,GU815750,AB670257,JXQ26886,JF491452,EU939674,FJ386667,AY236160,GQ924640,HM750131,FJ899783,KF425554,JF828916,HM363593,JN664933,GU332697,AB195940,EU882005,AB493842,AB195934,JQ272887,DQ899143,AY800390,AB198078,DQ478888,JN827423,AJ627217,EU835241,D0823095,JXQ26879,DQ993699,FJ562218,AF121250,EU939647,EU594403,HM363608,FJ787479,EU239224,AY817513,AB674406,AB368297,EU554541,FJ692589,EU414134,FJ904407,KC875260,FR714491,JQ801492,FJ386607,EF103278,AB104712,FJ904421,EU939551,EU305547,AB105174,KC875323,JN040767,FJ562234,JQ801503,GQ92462 |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| | | | | | | 7,AB375167,GQ377620,FJ787457,KC875309,KC875283,EU939567,AB014375,JN642164,JQ040136,X52939,AB195931,GU815701,KC875290,JQ027317,GQ358142,KC875282,FJ386582,FJ349228,HE981185,GQ475339,EU859907,JN642141,GQ377572,FJ692557,JN257184,X98077,GQ183449,FM199974,AB241117,GQ227693,FJ386631,FJ692593,JN827415,JN257213,JN792918,FJ787440,HQ646555,GU815756,GQ161766,AB365452,HM590474,EU859922,FJ386668,JQ272888,JN182323,HQ684849,DQ089761,GQ475349,DQ464379,DQ478898,EU305545,EU916208,GQ475328,EU787437,JN642132,AB493843,AF222322,GU168597,DQ089769,AB670247,GU815615,DQ0220,JQ040166,JQ801473,FJ787490,EU939667,GQ377537,AB194949,EU678473,GU815724,HQ700488,DQ448626,DQ304547,JXQ26888,GU815713,EU306705,FJ562286,EU439007,GQ161807,GU815737,HM011479,X70185,EU660230,DQ899146,AB670259,EU594410,HQ378247,GQ161760,AB073824,EU939560,EU139543,HM363606,JQ040148,DQ089789,AB670301,FJ386671,EU859931,HQ700465,L27106,EU919166,EU939670,M54923,JF754628,FR714490,AB195949,JN792906,AF411408,AY206392,KC875333,DQ089780,AB048703,GQ92465 4,AF121248,GU815754,HM011486,GU815749,FJ90 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 4441,EU939633,GU563550,GQ161772,GU815618,D23679,AB126580,FJ386587,EU939659,GU815607,JX504531,FJ904405,EU872014,GQ161767,JXQ96955,FJ562224,EU414133,EU881999,DQ463799,FJ787466,GQ377524,DQ904357,GU815712,EU306713,EU939571,GU815624,EF208113,FJ349216,JN664944,AF223955,EU939541,GQ184324,JN18324,DQ089801,KF767451,HQ603065,JN642162,FJ349241,HQ700541,AM421544,AB073846,GU815723,AJ131574,GQ183456,GQ227696,FR714504,GU456639,GQ183469,GU815764,HM363607,DQ478891,AB241113,FJ787475,JN040752,FR714503,EU562215,GU563556,AY330912,AY167100,JQ040159,DQ377715,9,HM585189,AB367401,KC315400,GQ358152,JN040780,EU554536,HQ700449,AB246342,AB270539,FJ386685,DQ463787,GU815719,FJ386677,AB049609,JN406371,DQ315786,JQ040175,EU859942,KC875308,JQ42982,JF754599,GQ377630,GQ475335,AY721610,AB205124,GU815628,EU871970,GQ358156,JX504537,EU872010,JF754634,GU456645,KC510648,EU871998,GU815612,EU916212,EU594391,DQ993701,EU859917,FJ386644,FJ386688,GQ358148,GQ477485,KC87298,DQ993695,HQ700508,AB111124,JN257148,AY236161,EU570071,GU815567,FJQ32358,HE576989,GQ161836,EU054331, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | GQ377622,GQ475323,JN040799,EF473973,HQ700484,GQ475318,AB674416,G0924634,DQ993181,AB014396,HM011483,EU439022,FJ386648,HQ700478,EU594398,FJ692601,AB014368,GQ924659,AB697493,J0040170,AB014393,AB073826,EF208115,DQ111987,AY817515,AB300370,AB367418,AY781186,JX50453 2,JN792908,FJ386634,AY330911,KF219922,AF223963,GQ924618,JQ801476,EU306723,AB037928,KC875277,AB670254,FJ386650,AF418688,AP011101,JN257203,GQ161822,GQ377623,DQ463793,FJ692587,AB6702289,FJ899782,EU871984,GQ161779,EU916223,APO11091,AB713532,JX898687,FJ562289,AF100308,JF754633,DQ993711,AP011087,AB670274,AY233294,EU330989,EU916240,AF143299,FJ692608,JF491451,D0478895,DQ329357,L08805,EU306719,JN040782,AM494717,JN642159,FJ349223,GQ924652,FJ356716,AM295799,GU332692,KC494396,AB674420,FJ692597,GQ377625,AB073842,H0700490,KC875319,EU717217,EF473976,AB900095,GQ924617,GQ924613,AY167101,GU815557,GU815596,AF297624,JF440011,GQ475325,FJQ23669,JQ040143,AY721609,KC494403,EU306725,GU815636,EU859939,JN040816,DQ089797,EU594400,AJ309369,JN792910,DQ993688,EF634480,AB250109,JQ801521,AB014360,AY220702,AB0 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 36917,JQ040128,KC875315,AY236162,AB697498,AB126581,HQ700473,GQ331047,EU916222,JF828930,EU916233,GQ377640,N642148,AB195955,EU306684,EU859906,JN257199,AF537372,AB674405,EU185787,GQ161814,GQ924607,EU939679,HM750132,EU871979,GQ161815,FJ562268,AB697504,GQ377644,AB300361,GU815736,JX560520,JF440006,FJ562241,AB116087,AB247916,HM750137,AY217356,GU815748,AB195939,GQ475324,GU563552,AY161139,GQ377550,EU439016,EU306683,AB116084,EF494382,DQ246215,AY796032,AY128092,AB210821,GQ377518,EU439010,AY247031,EU882006,GU815769,FJ562257,KC836881,JN642150,AB493834,GQ377554,EU787445,EU594392,FJ386599,HM363570,FJ386629,JN257162,JN664924,JX154582,EU306706,HQ603060,FJQ23656,AB583680,AM421548,AB212625,DQ899144,EU306673,AY090455,EF464099,AB033558,FJ899770,FJ692562,AB670309,GU815548,JN827424,FJQ23664,AB330369,DQ060824,FJ562219,GU815745,EU439005,EU859904,GU815603,JX429911,AB014367,AM117394,GU815551,GU815576,GU456683,AB697495,AB270542,AY066028,GU815647,AB670237,KF425553,AB493829,AY233281,JQ040169,JQ040154,M57663,FJ904443,AB274974,HQ700527,JN6 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | 64935,FJ899778,EU87200 0,GU815550,JQ040168,JF 436919,AF182803,U95551 ,EU796068,AF090841,AB0 33555,AF461043,FJ78744 6,GQ161838,EU919161,G U815780,AB222709,FJ562 252,AF498266,AB231909, GQ924653,GQ377590,EU8 59920,EF473974,DQ08979 0,AY934770,AB674425,JF 440003,EU939572,DQ536 411,GQ377583,HM363600, EU939548,JF754592,AB05 6513,JN642142,GQ205378 ,AB116654,GQ161781,AB2 74979,HQ603074,AB1949 50,JN642131,FJ904397,FN 545830,DQ788725,GQ377 535,EU439009,HM011496, JF754607,HQ700523,GQ4 75341,GQ924650,JN04082 9,HQ700466,AB675678,AP 011100,D50518,EU939616 ,AB287319,FJ882617,JN66 4927,AB014386,JQ040147 ,GQ205389,KC875294,JN0 40796,EU916215,JX42991 8,GQ377594,FJ349227,AY 034878,EU306675,HQ700 538,GU332691,AY817511, EU939608,FJ562270,JX87 0001,AY233275,GQ47535 3,DQ823086,AB287326,AB 642095,FJQ32337,DQ7887 29,AB900103,FJ692606,FJ 692576,AB287322,GU815 678,GQ377633,AB697510, FR714497,JF754588,AB36 7804,AJ131956,HE981171 ,EU881996,AB064312,AY9 34767,AB112063,GQ3775 98,EU547559,AB900111,A B775198,GU815700,FJ562 317,JN664926,JX504542,F J882612,DQ536412,GQ37 7617,AB222713,AF363962 ,KC510660,JN811656,GQ4 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 75329,HQ700530,AB3674 03,JN792912,AB670272,J N664938,AB073834,AJ627 225,AF223958,JF433995,A B298720,GU815691,DQ06 0822,HM011485,AB11387 8,GQ161799,JN257159,AF 411410,AY217364,EU7874 38,FJ882610,AP011107,G 0924658,EU859919,AJ627 220,GQ377642,D16666,AB 031262,AY902768,JN8274 21,DQ060830,DQ899145,E U872007,JQ040125,AB106 884,GQ477477,DQ315784, GU815554,DQ463798,GU5 63560,JN642130,FJ78746 4,EU871981,HM585198,AF 233236,AB670264,AB2749 76,AB195944,HM363598,G 0161805,FJ787468,JN040 756,AB670291,HQ603077, DQ899150,DQ993698,JN0 40786,EU859902,AB03355 7,GQ377616,AB713527,G 0377603,AY596102,GU81 5742,AY123041,AB697511 ,AB555501,AB033552,AB0 73821,GU815593,AB1111 16,GQ477495,EU660228,J F444009,HM011469,GQ92 4608,AY934765,AM49469 8,FJ904429,AB275308,FJ6 92575,AY033072,GU8157 82,EU939576,JQ801513,F J562284,JF754635,JN7929 01,FJ692561,AY739674,A B674433,FJ709457,AB670 255,DQ995804,JN257205, KC875267,AB176643,AB2 22708,GU815703,JX50721 2,EU859923,GQ205386,H 0236015,FJ562251,AY306 136,EU939637,EU859953, GU815597,FJ562236,GQ4 77488,GQ161765,AB0902 70,DQ995802,FJQ23672,J N664941,AY090456,DQ53 |

| Taxonomy | Rep.Acc.ID | Host | # GN's | ViroCap-1.0 Taxonomy Lineage | Seg. Count | GN.Acc.IDs |
|---|---|---|---|---|---|---|
| | | | | | | 6410,GU563558,JN040794,JN257191,GQ477492,GQ377581,AF418682,FJ904394,EF576812,GQ475343,JN257156,AB111114,EU939676,EU939552,FJ562315,GQ377643,JF440015,AY781181,GU815757,FJQ23654,AB195956,GQ475333,HM363566,JN64212 6,FJ787483,FJ787453,AB375164,HM117850,EU306670,AY161142,GQ377532,JN040773,AB270547,JX429913,HE981173,FJQ23636,AB375162,AB111123,HM363587,JF828920,AP011086,HQ700525,AY862860,AY167094,GQ259588,FJ562232,FJ787443,GQ477469,JN664929,KC875332,EU487257,JQ027326,AB113879,AB195951,FJQ23644,JX504541,D0993681,D50521,HM011499,FN545828,AB562462,AB367421,EU306674,FJ882613,AJ344117,JQ801502,AB195933,AY935700,AB670240,AF043594,JF436922,AB073823,AB367430,GU332690,EU306690,JXQ96957,GQ377641,JN040810,AB675675,AB116552,JXQ26883,GQ161834,FJ386580,GU456643,X98074,FN594767,JF440007,FJ562338,HM011491,S50225,FJ692595,JX898698,EU919172,FN545829,AM494709,GU815586,GU815669,EU939583,JN040822,AP011105,GU815743,EU939577,AB697491,JQ027327,AB488012,AB365445,FJ386656,AF121246,JQ801478,JN257209,HM750146,AB670308,GQ205383,AF143301,AF241409,AB026811,AB670278,AB2 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 70543,GQ205440,AB6703 11,GQ377543,JF828908,E U554537,JQ040163,JQ801 474,AB300362,EU939537, EU871975,FJQ32353,DQ9 93686,AB493839,EF49438 0,JN040788,AB119254,JQ 023663,AY161149,HQ700 533,GQ475344,JN642129, FJQ23638,FJ349218,AF22 3956,JN664931,HQ833466 ,GQ183464,EU306708,JQ 27332,JF439998,EU78743 5,GU815698,FJQ32347,AY 163869,DQ478889,DQ448 623,FJ692590,EU871976, EU717218,DQ980551,AY9 02772,GQ377538,FJ38661 6,AY934769,JN182326,HM 363583,GU456666,GQ475 355,FJ904445,AY862862, AY233276,GQ161816,AB3 02095,FJ562280,JQ02731 6,GU815774,KC510642,H M363610,JQ801477,FJ562 259,AY862863,GQ377635, HQ700501,GQ358139,FJ5 62277,GQ924657,EU1558 27,KC875257,DQ463795,J N642154,JN257183,KC510 653,AY090452,JQ688403, JN257169,GQ924645,JN6 64943,FJ692572,GU81568 3,EU916234,FJ900442,FJO 23635,JN664928,AB07382 5,GU815552,FJQ23655,HM 011489,FJQ23674,EU4141 39,AB014384,GU815721,E U306685,AM494694,EU93 9657,GU815644,JN642157 ,EF494377,XQ2763,AB194 948,JQ040156,GQ161808, FJ386600,AY167090,AB64 2094,AY596107,EU921419 ,GQ161753,KC875340,GU 815732,DQ089783,AB900 105,AM494706,AY330917, AB493835,AY206379,GQ1 |

| Taxonomy | Rep.Acc.ID | Host | # GN's | Lineage | Seg. Count | GN.Acc.IDs |
|---|---|---|---|---|---|---|
| | | | | | | 83480,JN827417,FJ56231 2,AB073852,EU916213,AY 596109,FJ349207,AB1160 90,FM209514,AY934771,A Y596112,AB493832,EU93 9545,EU916221,GU81558 8,AB670302,AY311370,AM 494714,AY217371,GQ377 634,AY161147,EU155893, JX507215,AB367801,AF46 1360,EU570069,KF679989 ,GQ475305,AF363963,EU9 19170,HQ833469,JN25719 3,DQ980548,AJ344116,AB 219533,KC875253,AB3678 00,AY721611,KF425556,K C875276,AB246343,DQ47 8890,AB674436,JN664940 ,AF458665,GQ477463,AM 184126,EU594404,FJ9044 11,AB697487,HM585197,E U306722,AF222323,JN257 192,FJ386663,HM011484, JN664915,GQ377566,AB6 42092,FJ562247,JFN59475 7,EU560441,KC875307,AB 300371,FJ692580,EU8720 16,GQ161806,GU815684, AB67030,GQ477502,AB1 95953,GQ377522,AY7381 41,JQ040137,FJ692566,E U859938,FJ386662,FJ904 404,FJ562295,EU306696, HQ603064,FJ386598,AB36 7422,DQ315776,DQ99369 0,JN040769,AY233277,EU 522068,EU306718,AY1670 96,FJ692607,GU456650,A B697501,FJ386611,AB287 325,AB562463,FJ386670, GQ161821,AB014395,AF4 18678,EF494381,AY93477 3,AB205127,HQ700481,FJ 904444,GU332694,AB670 276,AB480038,JQ801510, AB033559,AB195937,DQO 60826,HE981180,FJ38662 1,AB188244,FJQ23663,JN6 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 42136,GU815561,FJ562300,GQ16179l,HM750151,EU939666,JF828918,AM494708,AB365450,DQ993691,EU660224,JF436921,KC510647,FR714495,GQ358137,JQ429078,AB076679,FJ023650,EU916210,EU439006,KC875256,DQ980547,DQ089798,GQ377615,DQ478887,JF754631,JQ801493,AB073857,FJ386679,GQ477457,DQ993696,D16665,HM750138,JX429899,DQ993700,EU939618,AM494715,JQ688404,JF754608,GU815740,JF828928,AF282918,GQ477500,DQ111986,AB453986,EU158262,FJ589065,EU589340,AB0738339,GU815771,EU306701,EU871996,AB300363,AB073847,GQ161758,FM209516,AY741795,EU859926,EU939561,AB056515,AB674409,FJ899763,AB900116,GQ3477606,EU306727,GQ183470,DQ788728,HQ700521,GQ477468,EU306692,JN040763,HM627320,GQ3775l4,JN257216,KC875321,G0475356,FJ787459,AF458664,AB274977,FJ899771,FJ562235,HM363569,JN040795,AY902777,AY206383,EU660232,U87746,GQ924609,AF297625,GU815730,HQ700494,FJ692612,AY217368,HM011470,EU939673,GQ477480,D23682,GQ377597,AB288026,JN040779,FJ562238,GQ475314,JN642138,X80925,GQ475310,EU939559,GU815614,EU547561,JXQ26884,GU45669,JN664910,FJ386647,FJ023640,KF061168,AB073832,EU91917,GQ161771,H |

TABLE 10-continued

ViroCap-1.0 Taxonomy

| Taxonomy | Rep.Acc.

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Hepatitis B virus subtype adw2 | NC_003977 | vertebrates,human | Hepadnaviridae,Orthohepadnavirus,Hepatitis B virus | 1 | — | AM282986 |
| Hepatitis C virus | NC_009827,NC_009826,NC_009825,NC_009824,NC_004102,NC_009823 | vertebrates,human | Flaviviridae,Hepacivirus,Hepatitis C virus | 269 | — | HQ738645,EU362892,EU362907,JXQ14307,KC155254,JX183554,FJ407092,FJ462433,AB047645,HQ850284,AB049096,DQ41878 5,EF407480,JF73511 3,EF407418,AB08029 9,D89815,KC197235,EF407451,EF407438,EU246930,EU362903,D13558,EU362881,D 45172,EU246933,DQ 988075,FJ462441,AB 049093,JF735117,AM 408911,KC248196,E U362895,FJ462436,A B049098,EF407460,A B559564,JX183557,D 0988076,AJQ00009,K C197227,EU158186, EU362876,EF407465 ,JF735120,AJ278830, KF700370,EF407440, FJ462440,EF407469, AB049094,EU362897 ,D50481,JF735123,E U362893,EF407431, EF632071,KC197236 ,JF735116,EF026073 ,D11168,EF632069,A B047643,JF735112,K C197232,EU362883, X61596,FJ839869,FN 666428,D63857,EF40 7444,EU362887,EF4 07482,DQ988077,JF7 35110,EF407422,AB0 49099,EU246939,D8 9872,DQ988073,DQ2 78892,EF407504,EF4 07502,EF407428,KC 197228,EU362877,D 30613,JX183558,D50 484,AB049100,EU36 2885,EU362901,EF4 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 07425,AB049101,EU362898,EF407476,EF407488,JX183553,EF407436,EF407457,KC197237,D90208,EF407445,AF511950,FJ462438,KC197238,D85516,D50485,KC197240,EF407471,AB677529,EF407472,FJ462434,HQ850285,DQ988078,AB677527,JX183555,EF407449,JF735115,KC248194,EF407415,KC197229,JQ745651,EU362902,EF407432,JF735114,KC197234,EF407417,EF407427,JX183556,EF407470,EF407456,EF407454,D10750,KC248199,EU362891,JF735119,AB435162,AF511949,EF407447,KC197239,EF407423,,AI851228,AB677531,EF407446,EU362880,JX183551,KC967478,KC197233,EU362890,FJ462439,EF407449,7,AB049090,EU643834,JF735122,HQ850287,EF407492,EF407455,DQ0944,FJQ258855,KC197231,KC967476,EU246935,AB049092,JF735125,AB049089,EU362896,AB016785,D11355,JF735111,AB047644,EF407421,EF632070,EF407413,EF407452,FJ462431,EF407479,EF407485,DQ437509,AB191333,FJ435090,EF407503,EF407441,HQ850290,GU294484,EF407483,AB049087,AB4 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Hepatitis C virus (isolate 6a33) | NC_009827,NC_009826,NC_009825,NC_009824,NC_004102,NC_009823 | vertebrates,human | 1 | Flaviviridae,Hepacivirus,Hepatitis C virus | — | 29050,DQ988074,FJ839870,EU643836,D50482,EF407487,AB049091,HQ850283,HQ850282,EF407439,AB047640,KC248198,KC197230,EU362884,EF407437,AB622121,D10934,EF407442,KC248195,FJ462432,KC967479,JX183552,EU362894,EF407493,EF407435,EF407414,FJ462437,EF407453,FJ462435,KC197226,HQ850286,AB049088,D50480,EF407426,EF407443,EF407501,HM777359,EF407450,DQ988079,EF407461,X76918,JF735121,KC248197,EF407448,AJ132997,AB677533,D10988,AY651061,AB047641,AB049095,EU408327,FJQ25856,EF407411,EF407434,AB049097,EF407419,EU362886,D10749,HM850288,D14484,FJO25854,JF735118,EU362890,AJ132996,EF407475,AY587845,KC248193,JX183549,AF511948,EF407424,EU362899,JF735124,EU362879,EU362878,EU362882,KC967477,JX183550,EF407433,EU408326,EU64383 5,AB047642,D50483 AY859526 |

TABLE 10-continued

VíroCap-1.0 Taxonomy

| Taxonomy | Rep.Acc.ID | Host | Lineage | # GN's | Seg. Count | GN.Acc.IDs |
|---|---|---|---|---|---|---|
| Hepatitis C virus (isolate BEBE1) | NC_009827,NC_009826,NC_009825,NC_009824,NC_009823 | vertebrates,human | Flaviviridae,Hepacivirus,Hepatitis C virus | 1 | — | D50409 |
| Hepatitis C virus (isolate D54) | NC_009827,NC_009826,NC_009825,NC_009824,NC_009823 | vertebrates,human | Flaviviridae,Hepacivirus,Hepatitis C virus | 1 | — | DQ155561 |
| Hepatitis C virus (isolate EUHK2) | NC_009827,NC_009826,NC_009825,NC_009824,NC_009823 | vertebrates,human | Flaviviridae,Hepacivirus,Hepatitis C virus | 1 | — | Y12083 |
| Hepatitis C virus (isolate H77) | NC_009827,NC_009826,NC_009825,NC_009824,NC_009823 | vertebrates,human | Flaviviridae,Hepacivirus,Hepatitis C virus | 3 | — | AF011752,AF011753,AF011751 |
| Hepatitis C virus (isolate HC-G9) | NC_009827,NC_009826,NC_009825,NC_009824,NC_009823 | vertebrates,human | Flaviviridae,Hepacivirus,Hepatitis C virus | 1 | — | D14853 |
| Hepatitis C virus (isolate HCV-K3a/650) | NC_009827,NC_009826,NC_009825,NC_009824,NC_009823 | vertebrates,human | Flaviviridae,Hepacivirus,Hepatitis C virus | 1 | — | D28917 |
| Hepatitis C virus (isolate India) | NC_009827,NC_009826,NC_009825,NC_009824 | vertebrates,human | Flaviviridae,Hepacivirus,Hepatitis C virus | 1 | — | AY051292 |

TABLE 10-continued

| | | | VicoCap-1.0 Taxonomy | | | |
|---|---|---|---|---|---|---|
| Taxonomy | Rep.Acc.ID | Host | # GN's | Lineage | Seg. Count | GN.Acc.IDs |
| Hepatitis C virus (isolate JK046) | 4102,NC_0 09823 | vertebrates,human | 1 | Flaviviridae,Hepacivirus,Hepatitis C virus | — | D63822 |
| Hepatitis C virus (isolate JK049) | NC_009827 ,NC_00982 6,NC_0098 25,NC_009 824,NC_00 4102,NC_0 09823 | vertebrates,human | 1 | Flaviviridae,Hepacivirus,Hepatitis C virus | — | D63821 |
| Hepatitis C virus (isolate JPUT971017) | NC_009827 ,NC_00982 6,NC_0098 25,NC_009 824,NC_00 4102,NC_0 09823 | vertebrates,human | 1 | Flaviviridae,Hepacivirus,Hepatitis C virus | — | AB030907 |
| Hepatitis C virus (isolate Tr Kj) | NC_009827 ,NC_00982 6,NC_0098 25,NC_009 824,NC_00 4102,NC_0 09823 | vertebrates,human | 1 | Flaviviridae,Hepacivirus,Hepatitis C virus | — | D49374 |
| Hepatitis C virus (isolate VAT96) | NC_009827 ,NC_00982 6,NC_0098 25,NC_009 824,NC_00 4102,NC_0 09823 | vertebrates,human | 1 | Flaviviridae,Hepacivirus,Hepatitis C virus | — | AB031663 |
| Hepatitis C virus (isolate VN004) | NC_009827 ,NC_00982 6,NC_0098 25,NC_009 824,NC_00 4102,NC_0 09823 | vertebrates,human | 1 | Flaviviridae,Hepacivirus,Hepatitis C virus | — | D84265 |
| Hepatitis C virus (isolate VN235) | NC_009827 ,NC_00982 6,NC_009 | vertebrates,human | 1 | Flaviviridae,Hepacivirus,Hepatitis C virus | — | D84263 |

TABLE 10-continued

| | | | ViroCap-1.0 Taxonomy | | | |
|---|---|---|---|---|---|---|
| Taxonomy | Rep.Acc.ID | Host | # GN's | Lineage | Seg. Count | GN.Acc.IDs |
| Hepatitis C virus (isolate VN405) | NC_009827, NC_009824, NC_004102, NC_009825, NC_009826, NC_009823, NC_009827, NC_009826, NC_009826, NC_009826, NC_009826, NC_009827, NC_009827, NC_009827, NC_009827, NC_009827, NC_009828, NC_009823, NC_009826, NC_009826, NC_009826, NC_009826 | vertebrates,human | 1 | Flaviviridae,Hepacivirus,Hepatitis C virus | — | D84264 |
| Hepatitis C virus ED43 | NC_009827, NC_009982, NC_009826, NC_009825, NC_009824, NC_004102, NC_009823 | vertebrates,human | 1 | Flaviviridae,Hepacivirus,Hepatitis C virus | — | GU814265 |
| Hepatitis C virus JFH-1 | NC_009827, NC_009982, NC_009826, NC_009825, NC_009824, NC_004102, NC_009823 | vertebrates,human | 1 | Flaviviridae,Hepacivirus,Hepatitis C virus | — | AB047639 |
| Hepatitis C virus S52 | NC_009827, NC_009982, NC_009826, NC_009825, NC_009824, NC_004102, NC_009823 | vertebrates,human | 1 | Flaviviridae,Hepacivirus,Hepatitis C virus | — | GU814263 |
| Hepatitis C virus SA13 | NC_009827, NC_009982, NC_009826, NC_009825, NC_009824, NC_004102, NC_009823 | vertebrates,human | 1 | Flaviviridae,Hepacivirus,Hepatitis C virus | — | AF064490 |
| Hepatitis C virus genotype 3 | NC_009827, NC_009982, NC_009826, NC_009825, NC_009824, NC_004102, NC_009823 | vertebrates,human | 1 | Flaviviridae,Hepacivirus,Hepatitis C virus | — | JN588558 |
| Hepatitis C virus genotype 6 | NC_009827, NC_009982, NC_009826 | vertebrates,human | 3 | Flaviviridae,Hepacivirus,Hepatitis C virus | — | D84262,KC844040,KC844039 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | 25,NC_009 824,NC_00 4102,NC_0 09823 | | | | | |
| Hepatitis C virus isolate M2123 | NC_009827 ,NC_00982 6,NC_0098 25,NC_009 824,NC_00 4102,NC_0 09823 | vertebrates,human | 1 | Flaviviridae,Hepacivirus,Hepatitis C virus | — | AB558135 |
| Hepatitis C virus strain M21-2k/1b | NC_009827 ,NC_00982 6,NC_0098 25,NC_009 824,NC_00 4102,NC_0 09823 | vertebrates,human | 1 | Flaviviridae,Hepacivirus,Hepatitis C virus | — | FJ821465 |
| Hepatitis C virus subtype 1a | NC_009827 ,NC_00982 6,NC_0098 25,NC_009 824,NC_00 4102,NC_0 09823 | vertebrates,human | 435 | Flaviviridae,Hepacivirus,Hepatitis C virus | — | EU255991,EU256013 ,EU155295,EU86282 8,EU256053,EU1552 85,EU155323,EU781 773,EU660384,EU66 0385,EU256028,EU2 39716,EU255993,EU 155237,FJ390399,EU 155344,EU155252,FJ 024278,EU255965,E U482862,FJQ24280,E U256003,EU660383, EU155349,EU255975 ,JX463550,EU155314 ,EU255937,EU25598 9,JX463563,EU48286 7,EU255994,FJQ2408 7,EU255945,EU2560 97,EU781781,EU256 106,EU482843,EU78 1790,EU256024,EU4 82836,EU781767,FJ3 90394,EU862823,FJ1 81999,AF271632,EU 155297,EU155268,E U155270,JX463640,E U155342,EU155213, EU862836,EU255981 ,EU255980,JX463599 ,FJ205867,EU255943 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | ,EU781774,EU781813,EU260396,EU78181761,EU862834,EU482841,EU482852,EU155215,EU256105,EU256086,EU256047,EU781818,EU255964,EU255946,EU155273,U255946,EU155273,EU482884,EU781805,EU781754,EU482870,EU256096,EU255949,EU155293,EU482838,EU529677,EU781780,EU256036,EU781814,EU256044,EU862826,EU255976,EU155238,U862824,EU155238,EU155283,EU482844,EF032886,EU781819,EU482889,EU155252,67,EU155243,EU155348,M62321,FJ391039,5,EU256057,FJ41017,2,EU862827,EU255984,EU781783,EU15749,EU687193,EU155378,EU482854,EU482863,EU255954,EU155350,EU155313,EU256050,EU256021,EU155346,EU781806,EU781810,EU255952,EU482832,EU781762,EU482856,EU255959,EU155245,EU155355,EU781753,EU255938,EU781776,EU155321,EU255929,EF032890,EU482834,EU255998,EU155343,GQ149768,EU155223,EU255934,EU256058,EU255931,EU155266,EU595697,EU260395,EU234064,EU482869,EU256033,EU256071,EU155286,EU155312,EU781820, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | EU781816,EU256051,EU781760,EU155310,EF621489,EU255985,EU781755,EU482831,EU155244,EU256056,EU255958,EU155250,EU781765,EU781800,EU529680,JX46361,EU781792,EU256049,EU256032,EU256070,EU256025,EU250017,EU155275,EU155248,EU256060,EU155288,EU78112,EU155296,EU48809,AF290978,EU482848,JX463547,EU155236,EU781756,EU862839,EU155296,EU256068,EF032900,EU781823,EU482842,JX463549,EU482840,EU482882,EU256052,EU256069,EU482850,EU781775,EU781795,EU256038,EU595699,EU862841,JX463596,EU781804,EU781778,EU781789,EU482858,EU482865,EU256004,EU781768,AB520610,EU255970,EU155284,EU687194,EU482872,EU482847,EU155271,EU256027,EU781779,EU155354,EU482861,EU155352,EU256029,EU234065,EU256094,EU255997,EU255977,FJ024276,EU862838,EU256008,EU155240,EU862831,EU687195,EU781808,EF032884,EU482878,EU482846,EU781796,EU155233,EU256009,EU255942,EF032888,EU529678,EU255944,EU |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 155274,EU482855,E U781803,EU155242, EU155338,EU256014 ,EU569723,EU48284 5,EU255992,EU2560 19,EU255978,EU781 794,EU256023,FJ205 869,EU781812,EU78 1822,EU255995,EU1 55345,EU256087,EU 255930,EF032885,E U155353,EU255968, EU255973,EU660387 ,EU256040,FJ182000 ,EU155347,EU78177 7,EU256011,EU7817 88,FJ205868,EU2561 07,FJQ24282,EU8628 32,EU255947,EU482 866,EU255967,EU25 6002,EU255927,EU1 55216,EU255990,EU 256104,EU781782,E F032883,EU155379, EU482835,EU256041 ,EU482887,EU25600 6,EU256005,EU5956 98,EU255966,EU155 351,EU256037,EU48 2871,EU781784,EU2 56074,EU781769,EU 155339,EU781748,E U781802,EU256034, EU781807,EF032889 ,EU155272,EU48287 3,EU255950,KC8440 49,EU781764,EU255 996,EU781770,EU25 5948,EU256048,EU2 55974,EU781791,EU 155277,EU781817,E U155311,EU781793, EU155291,EU256018 ,EU781747,EU78176 3,EU256017,EU7817 87,EU256010,EU781 766,EU529681,EU78 1801,EU781752,EU2 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 55951,EU155269,EU781772,EU256060,EU155251,EU256043,EU255936,EU155265,EU781824,EU48286 8,EU256072,EU8628 40,EU155249,EU256 067,EU255928,EU25 5986,EU255939,EU7 81759,EU255941,EU 255982,EU155292,EU482853,FJ182001,EU256055,JX463616,EU155278,EU255935,JX463627,EU256095, EU255987,EU155290 ,EU781746,EU15531 9,EU155340,EU2559 40,EU529679,FJQ242 81,EU781751,EU155 282,EU569722,EU78 1798,EU256031,EU2 34063,EU155320,EU 255955,EU781757,EU239715,FJQ24275,EU781771,EU155380, EU155247,EU255932 ,EU255933,EU15529 4,EU781786,EF0328 87,EU155276,FJQ242 74,EU239713,EU781 785,EU529676,EU25 6026,EU256035,M67 463,JX463634,JX463 574,EU155322,EU78 1797,EU255957,EU4 82857,EU155299,JX4 63540,EU255963,EU 255953,EU255988,EU256022,EU155341, EU155214,EU255979 ,EU155241,EU78175 0,EU255956,EU4828 64,EU256020,EU256 007,EU781821,EU25 6039,EU482876,EU2 56015,EU255999,EU 482837,EU781758,E |

TABLE 10-continued

VirоCap-1.0 Taxonomy

| Taxonomy | Rep.Acc.ID | Host | Lineage | # GN's | Seg. Count | GN.Acc.IDs |
|---|---|---|---|---|---|---|
| | | | | | | U155289,EU155246, EU155280,EU155309, FU781815,EU25603 0,EU155287,EU2559 83,EU155298,EU781 799,EU256046,EU25 5969 |
| Hepatitis C virus subtype 1b | NC_009827, NC_00982 6,NC_0098 25, NC_009 824,NC_00 4102,NC_0 09823 | vertebrates,human | Flaviviridae,Hepacivirus,Hepatitis C virus | 269 | — | AF356827,AF165060, EU482880,EU155280 ,AF165045,EU15536 2,AB154206,AF17657 3,EU155372,EU1552 20,EU660386,EU256 065,EU155324,EU25 6099,EU155369,AB1 54185,AB154202,EU 155303,M96362,M84 754,EU256103,AB44 2222,EU256092,AB1 54182,AF165063,EU 155307,AB154191,K C844051,AF483269, EU256001,EU155279 ,DQ071885,EU48288 5,EU155360,AB1541 92,AF207753,AB1541 86,EU155308,EU155 229,EU256054,EF03 2893,AF207763,AB15 4203,EU155356,EU2 56081,EU155264,AF 054250,AF207770,AF 165053,EU482886,A B154181,EU256101, EU256102,EU239714 ,EU155221,AF33332 4,EU256077,EU2560 80,AB442221,EU155 262,AB154190,EU23 4061,EU155359,AF2 07755,EU255962,EU 155375,AF207771,E U155230,EU255961, AF207762,AB154187, AB154200,EU155231 ,AB442219,EU15522 6,EU155331,AF2077 56,EU155326,EU155 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 334,U16362,EU1553 16,EU256079,AF165 064,EU155367,U890 19,EU482877,AB442 220,AF208024,EU25 6100,EU256061,EU1 55332,AF207758,EU 155325,AY045702,E U155258,AF165046, EU781829,EU256082 ,AF165048,AB154201 ,AF207757,EU78182 6,EU155306,AF0542 48,AB691953,AF1650 54,EU781825,AF207 768,EU234062,EU48 2879,EU862837,EU2 56078,S62220,EU155 357,AF207774,EU25 6075,FJQ24277,AB15 4189,EU155368,AF1 65062,EU155257,AF 207769,EU256062,E U256084,EU155364, AF165050,FN435993, EU155333,EU256090 ,EU155259,AF20776 6,EU155373,AF2077 73,EF032892,AB1541 78,EU155281,AF207 759,EU256000,EU15 5318,EU155219,EU4 82881,FJ390396,AF1 65047,EU155366,M5 8335,EU482849,AF1 65051,EU256098,EU 482859,AF207760,AF 165056,EU155222,E U256045,EU857431, EU482839,AB154179 ,AB154177,EU15536 1,AF165049,FJ47845 3,AF207754,EU1552 25,AF165052,FJQ240 86,EU529682,EU155 329,EU155365,EU25 6088,FJQ24279,EU15 5223,HQ912956,EU4 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 82875,AB426117,EU155232,EU256076,EU155376,AB154198,EU155260,EU155302,EU256066,EU155337,EU155337,L02836,EU155377,AB154204,EU155336,AF207776,EU155317,EU155521,EU155301,AF207767,EU155328,AB779679,AF139594,EU155234,U45476,AF207765,EU155304,EU781827,EU482883,AF054247,EU256083,EU781831,AF165057,EU482874,GU133617,AF207752,EU155224,AB154194,EU155526,EU155255,AY5878443,EU155327,HQ912958,EU255960,EU862835,AF054249,EU155330,EU155358,EU155300,EU155218,EU482860,EU155381,EU155228,AF207772,EU155261,EU155537,EU155261,EU15537,FJ390397,AB154194,EU781830,AF207764,EU155305,AF165058,AY460204,EU256089,EF638081,AF165061,AB154180,EU781832,EU155227,AJ238799,EU155254,EU256085,EU155335,KC844052,EU482888,AJ238800,EU155315,AB154205,EU155363,EU660388,AF165059,EU155371,HQ912959,EU482833,EU155235,AB779562,EU256059,AB154183,EU781828,EU256064,EU155256,EU155217,A |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| Hepatitis C virus subtype 1c | NC_009827,NC_009826,NC_009825,NC_009824,NC_004102,NC_009823 | vertebrates,human | 1 | Flaviviridae,Hepacivirus,Hepatitis C virus | — | B249644,EU256091,U01214,AF165055,FJ390398,EU155382 |
| Hepatitis C virus subtype 1g | NC_009827,NC_009826,NC_009825,NC_009824,NC_004102,NC_009823 | vertebrates,human | 1 | Flaviviridae,Hepacivirus,Hepatitis C virus | — | KC844047
AM910652 |
| Hepatitis C virus subtype 2a | NC_009827,NC_009826,NC_009825,NC_009824,NC_004102,NC_009823 | vertebrates,human | 15 | Flaviviridae,Hepacivirus,Hepatitis C virus | — | KF676351,AF169004,AF238484,AB690461,AF238485,AF169003,AF238482,KC844043,AF238481,AB690460,AF238483,AF169002,KF676352,AF169005,AY746460 |
| Hepatitis C virus subtype 2b | NC_009827,NC_009826,NC_009825,NC_009824,NC_004102,NC_009823 | vertebrates,human | 22 | Flaviviridae,Hepacivirus,Hepatitis C virus | — | KC844048,AY232738,AY232745,AY232273 3,AY232746,AY232327 42,AY232735,AY232 749,AY232747,AY23 2743,AY232734,AY2 32740,AY232737,AF2 38486,AY232732,AY 232731,AY232744,A Y232730,AY232739, AY232741,AY232736 ,AY232748 |
| Hepatitis C virus subtype 2f | NC_009827,NC_009826,NC_009825,NC_009824,NC_004102,NC_009823 | vertebrates,human | 2 | Flaviviridae,Hepacivirus,Hepatitis C virus | — | KC844042,KC844050 |
| Hepatitis C virus subtype 3a | NC_009827,NC_009826,NC_009825 | vertebrates,human | 19 | Flaviviridae,Hepacivirus,Hepatitis C virus | — | KF035124,AB792683,JQ717255,KF035125,KF035123,KC844041,JQ717256,JQ717258 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | 824,NC_004102,NC_009823 | | | | | ,GQ275355,JQ717259,AF046866,JQ717257,JN714194,KF035127,JQ717254,KF035126,AB691595,AB691596,JQ717260 |
| Hepatitis C virus subtype 3b | NC_009827,NC_009826,NC_009825,NC_009824,NC_004102,NC_009823 | vertebrates,human | 1 | Flaviviridae,Hepacivirus,Hepatitis C virus | — | KC844044 |
| Hepatitis C virus subtype 4a | NC_009827,NC_009826,NC_009825,NC_009824,NC_004102,NC_009823 | vertebrates,human | 8 | Flaviviridae,Hepacivirus,Hepatitis C virus | — | DQ418784,DQ418788,DQ418787,DQ516084,DQ418789,AB795432,DQ418783,DQ418782 |
| Hepatitis C virus subtype 4d | NC_009827,NC_009826,NC_009825,NC_009824,NC_004102,NC_009823 | vertebrates,human | 3 | Flaviviridae,Hepacivirus,Hepatitis C virus | — | KC844045,DQ516083,DQ418786 |
| Hepatitis C virus subtype 4f | NC_009827,NC_009826,NC_009825,NC_009824,NC_004102,NC_009823 | vertebrates,human | 2 | Flaviviridae,Hepacivirus,Hepatitis C virus | — | EF589161,EF589160 |
| Hepatitis C virus subtype 5a | NC_009827,NC_009826,NC_009825,NC_009824,NC_004102,NC_009823 | vertebrates,human | 1 | Flaviviridae,Hepacivirus,Hepatitis C virus | — | KC844046 |
| Hepatitis C virus subtype 6a | NC_009827,NC_009826,NC_009825,NC_009824,NC_004102,NC_009823 | vertebrates,human | 15 | Flaviviridae,Hepacivirus,Hepatitis C virus | — | DQ480519,DQ480521,DQ480518,DQ480520,KC844037,DQ480515,DQ480512,DQ480514,DQ480523,DQ4 |

TABLE 10-continued

VíroCap-1.0 Taxonomy

| Taxonomy | Rep.Acc.ID | Host | Lineage | # GN's | Seg. Count | GN.Acc.IDs |
|---|---|---|---|---|---|---|
| Hepatitis C virus subtype 6c | 4102,NC_0 09823 | vertebrates,human | Flaviviridae,Hepacivirus,Hepatitis C virus | 1 | — | 80513,KC84038,DQ 480516,DQ480524,D 0480522,DQ480517 EF424629 |
| Hepatitis C virus subtype 6e | NC_009827 ,NC_00982 6,NC_0098 25,NC_009 824,NC_00 4102,NC_0 09823 | vertebrates,human | Flaviviridae,Hepacivirus,Hepatitis C virus | 1 | — | DQ314805 |
| Hepatitis C virus subtype 6f ,NC_00982 | NC_009827 0 | vertebrates,human | Flaviviridae,Hepacivirus,Hepatitis C virus | 2 | — | DQ835764,DQ83576 |
| Hepatitis C virus subtype 6g | NC_009827 ,NC_00982 6,NC_0098 25,NC_009 824,NC_00 4102,NC_0 09823 | vertebrates,human | Flaviviridae,Hepacivirus,Hepatitis C virus | 1 | — | DQ314806 |
| Hepatitis C virus subtype 6i | NC_009827 ,NC_00982 6,NC_0098 25,NC_009 824,NC_00 4102,NC_0 09823 | vertebrates,human | Flaviviridae,Hepacivirus,Hepatitis C virus | 2 | — | DQ835762,DQ83577 0 |
| Hepatitis C virus subtype 6j | NC_009827 ,NC_00982 6,NC_0098 25,NC_009 824,NC_00 4102,NC_0 09823 | vertebrates,human | Flaviviridae,Hepacivirus,Hepatitis C virus | 2 1 | — | DQ835769,DQ83576 |

TABLE 10-continued

| Taxonomy | Rep.Acc.ID | Host | VivoCap-1.0 Taxonomy # GN's | Lineage | Seg. Count | GN.Acc.IDs |
|---|---|---|---|---|---|---|
| Hepatitis C virus subtype 6k | NC_009827,NC_009826,NC_009825,NC_009824,NC_009823,NC_004102,NC_009823 | vertebrates,human 0 | 4 | Flaviviridae,Hepacivirus,Hepatitis C virus | — | DQ278893,AY878651,DQ278891,AY87865 |
| Hepatitis C virus subtype 6l | NC_009827,NC_009826,NC_009825,NC_009824,NC_004102,NC_009823 | vertebrates,human | 1 | Flaviviridae,Hepacivirus,Hepatitis C virus | — | EF424628 |
| Hepatitis C virus subtype 6m | NC_009827,NC_009826,NC_009825,NC_009824,NC_004102,NC_009823 | vertebrates,human | 4 | Flaviviridae,Hepacivirus,Hepatitis C virus | — | DQ835767,DQ835763,DQ835766,DQ835765 |
| Hepatitis C virus subtype 6n | NC_009827,NC_009826,NC_009825,NC_009824,NC_004102,NC_009823 | vertebrates,human | 3 | Flaviviridae,Hepacivirus,Hepatitis C virus | — | DQ835768,DQ278894,AY878652 |
| Hepatitis C virus subtype 6o | NC_009827,NC_009826,NC_009825,NC_009824,NC_004102,NC_009823 | vertebrates,human | 1 | Flaviviridae,Hepacivirus,Hepatitis C virus | — | EF424627 |
| Hepatitis C virus subtype 6p | NC_009827,NC_009826,NC_009825,NC_009824,NC_004102,NC_009823 | vertebrates,human | 1 | Flaviviridae,Hepacivirus,Hepatitis C virus | — | EF424626 |
| Hepatitis C virus subtype 6q | NC_009827,NC_009826,NC_009825,NC_009824,NC_004102,NC_009823 | vertebrates,human | 1 | Flaviviridae,Hepacivirus,Hepatitis C virus | — | EF424625 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Hepatitis C virus subtype 6v | 824,NC_009824,NC_009823 NC_004102,NC_0 | vertebrates,human | 2 | Flaviviridae,Hepacivirus,Hepatitis C virus | — | EU798761,EU798760 |
| Hepatitis E virus | NC_009827,NC_009826,NC_009825,NC_009824,NC_004102,NC_009823 | vertebrates,human | 189 | Hepeviridae,Hepevirus,Hepatitis E virus | — | AB189074,AB291963,AB248521,AB78045 1,JF443719,DQ45007 2,AB222184,D11092, AF051830,AB291966, AB220971,AY575858 ,JF653660,AB369689 ,AB290313,AF455784 ,AB193177,AB07491 5,AF076239,X98292, AB448025,AY723745 ,JN906976,AB301710 ,L08816,AB437316,J F443725,JX121233,J X565469,AB291967, EF077630,M94177,E F570133,AB291953,J 0953665,AB521805,J 0953664,AB443624, AB362840,AB099347 ,JQ655734,AB698654 ,AB189073,M73218,J F443721,AB443623, HM439284,AB740220 ,M80581,AB291952,J F915746,AB630970,A B291959,AB189072, AB369688,AB222182 ,KC492825,AB29195 7,AB443625,D11093, JN906975,JN167537, AB602441,AB220975 ,JN906974,AY575859 ,L25595,AB780452,A B362839,JQ655733,A B220972,JF443726,A B856243,AB369690, AB740221,FJ906895, |
| | NC_001434 | vertebrates,human | | Hepeviridae,Hepevirus,Hepatitis E virus | — | |

TABLE 10-continued

| Taxonomy | Rep.Acc.ID | Host | # GN's | Lineage | Seg. Count | GN.Acc.IDs |
|---|---|---|---|---|---|---|
| | | | | | | AB602440,AB189071,AB291954,AB437317,AB220976,AB591733,AF444002,AB074917,AB573435,AB291958,AB197673,JQ740781,HQ709170,DQ459342,HQ389543,EU495148,AB591734,AB425831,JQ953666,JQ655735,AB291962,AF185822,AB369687,FJ527832,AB291965,AY204877,AB089824,HQ634346,AB220978,EU360977,AB740232,AB362842,AF459438,JF443724,AB369691,AB220973,AJ272108,JN167538,EU375463,AB220979,HQ389544,AB291955,AB236320,GU937805,AB091395,AB602439,EU366959,AB108537,AB091394,JF443723,AB222183,AF060669,AB074918,AB290312,D10330,AY575857,AB189075,AF444003,AB443627,AB437318,KC618402,AB193176,GU206559,AB291964,AB074920,AB780453,AB720035,JQ993308,AB248520,AB437319,AB080575,JF443720,AB780450,AB248522,AB200239,AB246676,JQ655736,JQ768717,FJ906896,JQ768461,AB291951,L25547,AB291968,AB220977,FJ956757,AB097812,AY230202,AB630971,FJ457024,AB291956,AB720034,AB189070,FJ763142,JF449 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 3718,AB253420,AB2 20974,AB521806,AB 362843,AB291960,A B425830,AB740222, AB291961,FJ705359, JF443722,AB362841, AB197674,JN837481, KC618403,AB193178 ,AP003430,X99441,A B443626,JX109834 |
| Hepatitis E virus type 3 | NC_001434 | vertebrates,human | 1 | Hepeviridae,Hepevirus,Hepatitis E virus | — | AB593690 |
| Hepatitis G virus isolate PEI | NC_001710 | vertebrates,human | 1 | Flaviviridae,Pegivirus,GB virus C | — | AF309966 |
| Hepatitis delta virus | NC_001653 | vertebrates,human | 108 | Deltavirus,Hepatitis delta virus | — | HQ005370,AM18332 9,HQ005365,AB0379 49,AB118842,M8491 7,AJ584849,AJ58484 4,HM046802,AB1188 49,AY633627,AB118 821,AB118839,AB11 8837,AB118829,AB1 18829,M28 267,M92448,KF6605 98,AM183332,HQ005 364,AB118820,AB11 8832,EF514905,DQ10 75,M58629,AB11881 8,AB118833,AJ30707 7,AB037948,U81989, HQ005366,AB118827 ,AY648956,HQ00537 1,AM183331,HF6794 05,AY648958,AB118 844,HQ005367,AY26 1460,GU177114,AJ5 84845,AB118846,AB 118845,AB118826,A B118840,AY648953, X85253,AB037947,A B118836,AB118838, AY648957,AF104263, AY648959,AB118830 ,AB118819,AY64895 5,AB088679,AB1188 41,AJ584848,EF5149 07,AB118843,XQ4451 ,KF660602,AB118822 ,KC590319,EF51490 4,L22066,AF104264, |

TABLE 10-continued

| Taxonomy | Rep.Acc.ID | Host | VirocCap-1.0 Taxonomy Lineage | # GN's | Seg. Count | GN.Acc.IDs |
|---|---|---|---|---|---|---|
| Hepatitis delta virus dFr2012 | NC_001653 | vertebrates,human | | | | HQ005369,AM18332 7,EF514906,AB11884 8,AM183330,U81988, AB118824,AY261458 ,AJ584847,AB118823 ,M21012,KF660599, M55042,HF679406,A M183333,AB118847, AY261459,HQ005368 ,AB118828,X77627,A M183328,AJ584846, AY261457,AJQ00558, KF660600,AF098261, AM183326,AB118831 ,HQ005372,AB11882 5,AY648952,EF51490 3,AB118835,AF42564 5,HF679404,AY6489 54,KF660601,AB1188 34,AF425644 |
| Hepatitis delta virus dFr2040 | NC_001653 | vertebrates,human | Deltavirus,Hepatitis delta virus | 1 | — | AM902177 |
| Hepatitis delta virus dFr2042 | NC_001653 | vertebrates,human | Deltavirus,Hepatitis delta virus | 1 | — | AM902178 |
| Hepatitis delta virus dFr2043 | NC_001653 | vertebrates,human | Deltavirus,Hepatitis delta virus | 1 | — | AM902179 |
| Hepatitis delta virus dFr2045 | NC_001653 | vertebrates,human | Deltavirus,Hepatitis delta virus | 1 | — | AM902180 |
| Hepatitis delta virus dFr2046 | NC_001653 | vertebrates,human | Deltavirus,Hepatitis delta virus | 1 | — | AM902168 |
| Hepatitis delta virus dFr2067 | NC_001653 | vertebrates,human | Deltavirus,Hepatitis delta virus | 1 | — | AM779580 |
| Hepatitis delta virus dFr2119 | NC_001653 | vertebrates,human | Deltavirus,Hepatitis delta virus | 1 | — | AM902163 |
| Hepatitis delta virus dFr2137 | NC_001653 | vertebrates,human | Deltavirus,Hepatitis delta virus | 1 | — | AM779575 |
| Hepatitis delta virus dFr2172 | NC_001653 | vertebrates,human | Deltavirus,Hepatitis delta virus | 1 | — | AM902164 |
| Hepatitis delta virus dFr2189 | NC_001653 | vertebrates,human | Deltavirus,Hepatitis delta virus | 1 | — | AM902165 |
| Hepatitis delta virus dFr2201 | NC_001653 | vertebrates,human | Deltavirus,Hepatitis delta virus | 1 | — | AM902166 |
| Hepatitis delta virus dFr2210 | NC_001653 | vertebrates,human | Deltavirus,Hepatitis delta virus | 1 | — | AM902167 |
| Hepatitis delta virus dFr2236 | NC_001653 | vertebrates,human | Deltavirus,Hepatitis delta virus | 1 | — | AM902181 |
| Hepatitis delta virus dFr2236 | NC_001653 | vertebrates,human | Deltavirus,Hepatitis delta virus | 1 | — | AM902169 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Hepatitis delta virus dFr2239b | NC_001653 | vertebrates,human | Deltavirus,Hepatitis delta virus | 1 | — | AM779578 |
| Hepatitis delta virus dFr2244 | NC_001653 | vertebrates,human | Deltavirus,Hepatitis delta virus | 1 | — | AM902170 |
| Hepatitis delta virus dFr2258 | NC_001653 | vertebrates,human | Deltavirus,Hepatitis delta virus | 1 | — | AM902171 |
| Hepatitis delta virus dFr2264 | NC_001653 | vertebrates,human | Deltavirus,Hepatitis delta virus | 1 | — | AM902172 |
| Hepatitis delta virus dFr2284 | NC_001653 | vertebrates,human | Deltavirus,Hepatitis delta virus | 1 | — | AM779577 |
| Hepatitis delta virus dFr2380 | NC_001653 | vertebrates,human | Deltavirus,Hepatitis delta virus | 1 | — | AM902173 |
| Hepatitis delta virus dFr2395 | NC_001653 | vertebrates,human | Deltavirus,Hepatitis delta virus | 1 | — | AM779579 |
| Hepatitis delta virus dFr2404 | NC_001653 | vertebrates,human | Deltavirus,Hepatitis delta virus | 1 | — | AM902174 |
| Hepatitis delta virus dFr2406 | NC_001653 | vertebrates,human | Deltavirus,Hepatitis delta virus | 1 | — | AM902175 |
| Hepatitis delta virus dFr2411 | NC_001653 | vertebrates,human | Deltavirus,Hepatitis delta virus | 1 | — | AM902176 |
| Hepatitis delta virus dFr2544 | NC_001653 | vertebrates,human | Deltavirus,Hepatitis delta virus | 1 | — | AM779576 |
| Hepatitis delta virus dFr508 | NC_001653 | vertebrates,human | Deltavirus,Hepatitis delta virus | 1 | — | AM779574 |
| Hepatitis delta virus dTk1 | NC_001653 | vertebrates,human | Deltavirus,Hepatitis delta virus | 1 | — | AM779581 |
| Hepatitis delta virus dTk10 | NC_001653 | vertebrates,human | Deltavirus,Hepatitis delta virus | 1 | — | AM779583 |
| Hepatitis delta virus dTk12 | NC_001653 | vertebrates,human | Deltavirus,Hepatitis delta virus | 1 | — | AM779595 |
| Hepatitis delta virus dTk13 | NC_001653 | vertebrates,human | Deltavirus,Hepatitis delta virus | 1 | — | AM779593 |
| Hepatitis delta virus dTk2 | NC_001653 | vertebrates,human | Deltavirus,Hepatitis delta virus | 1 | — | AM779597 |
| Hepatitis delta virus dTk21 | NC_001653 | vertebrates,human | Deltavirus,Hepatitis delta virus | 1 | — | AM779596 |
| Hepatitis delta virus dTk27 | NC_001653 | vertebrates,human | Deltavirus,Hepatitis delta virus | 1 | — | AM779594 |
| Hepatitis delta virus dTk28 | NC_001653 | vertebrates,human | Deltavirus,Hepatitis delta virus | 1 | — | AM779586 |
| Hepatitis delta virus dTk3 | NC_001653 | vertebrates,human | Deltavirus,Hepatitis delta virus | 1 | — | AM779589 |
| Hepatitis delta virus dTk34 | NC_001653 | vertebrates,human | Deltavirus,Hepatitis delta virus | 1 | — | AM779582 |
| Hepatitis delta virus dTk35 | NC_001653 | vertebrates,human | Deltavirus,Hepatitis delta virus | 1 | — | AM779590 |
| Hepatitis delta virus dTk38 | NC_001653 | vertebrates,human | Deltavirus,Hepatitis delta virus | 1 | — | AM779584 |
| Hepatitis delta virus dTk4 | NC_001653 | vertebrates,human | Deltavirus,Hepatitis delta virus | 1 | — | AM779591 |
| Hepatitis delta virus dTk5 | NC_001653 | vertebrates,human | Deltavirus,Hepatitis delta virus | 1 | — | AM779585 |
| Hepatitis delta virus dTk6 | NC_001653 | vertebrates,human | Deltavirus,Hepatitis delta virus | 1 | — | AM779587 |
| Hepatitis delta virus dTk7 | NC_001653 | vertebrates,human | Deltavirus,Hepatitis delta virus | 1 | — | AM779592 |
| Hepatitis delta virus dTk8 | NC_001653 | vertebrates,human | Deltavirus,Hepatitis delta virus | 1 | — | AM779592 |
| HoJo virus | NC_005219 | vertebrates,human | Bunyaviridae,Orthopoxvirus,Hantaan virus | 1 | seg. M | DQ0376 |
| Horsepox virus | NC_006998 | vertebrates,human | Poxviridae,Orthopoxvirus,Vaccinia virus | 1 | — | DQ792504 |
| Hu39694 virus | NC_003467 | vertebrates,human | Bunyaviridae,Hantavirus,Andes virus | 1 | seg. M | AF028023 |
| Human Respiratory syncytial virus 9320 | NC_001781 | vertebrates,human | Paramyxoviridae,Pneumovirus,Human respiratory syncytial virus | 1 | — | AY353550 |
| Human adenovirus 1 | NC_001405 | vertebrates,human | Adenoviridae,Mastadenovirus,Human adenovirus C | 3 | — | KF429744,KF268331, AF534906 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human adenovirus 11 | NC_011202 | vertebrates,human | 2 | Adenoviridae,Mastadenovirus,Human adenovirus B | — | FJ643676,AF532578 |
| Human adenovirus 11 | NC_011203 | vertebrates,human | 2 | Adenoviridae,Mastadenovirus,Human adenovirus B | — | FJ643676,AF532578 |
| Human adenovirus 11a | NC_011202 | vertebrates,human | 1 | Adenoviridae,Mastadenovirus,Human adenovirus B | — | FJ597732 |
| Human adenovirus 11a | NC_011203 | vertebrates,human | 1 | Adenoviridae,Mastadenovirus,Human adenovirus B | — | FJ597732 |
| Human adenovirus 14 | NC_011202 | vertebrates,human | 4 | Adenoviridae,Mastadenovirus,Human adenovirus B | — | FJ822614,JX892927, AY803294,JN032132 |
| Human adenovirus 14 | NC_011203 | vertebrates,human | 4 | Adenoviridae,Mastadenovirus,Human adenovirus B | — | FJ822614,JX892927, AY803294,JN032132 |
| Human adenovirus 15 | NC_010956 ,NC_012959 | vertebrates,human | 3 | Adenoviridae,Mastadenovirus,Human adenovirus D | — | AB562586,KF268201, KF268329 |
| Human adenovirus 16 | NC_011202 | vertebrates,human | 2 | Adenoviridae,Mastadenovirus,Human adenovirus B | — | JN860680,AY601636 |
| Human adenovirus 16 | NC_011203 | vertebrates,human | 2 | Adenoviridae,Mastadenovirus,Human adenovirus B | — | JN860680,AY601636 |
| Human adenovirus 17 | NC_010956 ,NC_012959 | vertebrates,human | 3 | Adenoviridae,Mastadenovirus,Human adenovirus D | — | KF268330,HQ910407 ,AF108105 |
| Human adenovirus 18 | NC_001460 | vertebrates,human | 1 | Adenoviridae,Mastadenovirus,Human adenovirus A | — | GU191019 |
| Human adenovirus 19 | NC_010956 ,NC_012959 | vertebrates,human | 7 | Adenoviridae,Mastadenovirus,Human adenovirus D | — | KF268323,EF121005, AB448773,AB448774 ,AB448772,AB44877 1,JQ326209 |
| Human adenovirus 2 | NC_001405 | vertebrates,human | 1 | Adenoviridae,Mastadenovirus,Human adenovirus C | — | KF268310 |
| Human adenovirus 20 | NC_010956 ,NC_012959 | vertebrates,human | 1 | Adenoviridae,Mastadenovirus,Human adenovirus D | — | KF268207 |
| Human adenovirus 21 | NC_011202 | vertebrates,human | 1 | Adenoviridae,Mastadenovirus,Human adenovirus B | — | AY601633 |
| Human adenovirus 21 | NC_011203 | vertebrates,human | 1 | Adenoviridae,Mastadenovirus,Human adenovirus B | — | AY601633 |
| Human adenovirus 22 | NC_010956 ,NC_012959 | vertebrates,human | 2 | Adenoviridae,Mastadenovirus,Human adenovirus D | — | FJ619037,FJ404771 |
| Human adenovirus 23 | NC_010956 ,NC_012959 | vertebrates,human | 1 | Adenoviridae,Mastadenovirus,Human adenovirus D | — | KF279629 |
| Human adenovirus 26 | NC_010956 ,NC_012959 | vertebrates,human | 1 | Adenoviridae,Mastadenovirus,Human adenovirus D | — | EF153474 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human adenovirus 28 | NC_010956, NC_012959 | vertebrates,human | 2 | Adenoviridae,Mastadenovirus,Human adenovirus D | — | KF268320,FJ824826 |
| Human adenovirus 29 | NC_010956, NC_012959 | vertebrates,human | 1 | Adenoviridae,Mastadenovirus,Human adenovirus D | — | AB562587 |
| Human adenovirus 3 | NC_011202 | vertebrates,human | 7 | Adenoviridae,Mastadenovirus,Human adenovirus B | — | KF268212,KF268210, KF268202,AY599834, AY599836,KF268315, KF429752 |
| Human adenovirus 3 | NC_011203 | vertebrates,human | 7 | Adenoviridae,Mastadenovirus,Human adenovirus B | — | KF268212,KF268210, KF268202,AY599834, AY599836,KF268315, KF429752 |
| Human adenovirus 3+11p | NC_011202 | vertebrates,human | 2 | Adenoviridae,Mastadenovirus,Human adenovirus B | — | EF564600,EF564601 |
| Human adenovirus 3+11p | NC_011203 | vertebrates,human | 2 | Adenoviridae,Mastadenovirus,Human adenovirus B | — | EF564600,EF564601 |
| Human adenovirus 3+7 | NC_011202 | vertebrates,human | 1 | Adenoviridae,Mastadenovirus,Human adenovirus B | — | JN860679 |
| Human adenovirus 3+7 | NC_011203 | vertebrates,human | 1 | Adenoviridae,Mastadenovirus,Human adenovirus B | — | JN860679 |
| Human adenovirus 3-16 | NC_011202 | vertebrates,human | 1 | Adenoviridae,Mastadenovirus,Human adenovirus B | — | JN860678 |
| Human adenovirus 3-16 | NC_011203 | vertebrates,human | 1 | Adenoviridae,Mastadenovirus,Human adenovirus B | — | JN860678 |
| Human adenovirus 30 | NC_010956, NC_012959 | vertebrates,human | 1 | Adenoviridae,Mastadenovirus,Human adenovirus D | — | KF268335 |
| Human adenovirus 31 | NC_001460 | vertebrates,human | 1 | Adenoviridae,Mastadenovirus,Human adenovirus A | — | AM749299 |
| Human adenovirus 32 | NC_010956, NC_012959 | vertebrates,human | 2 | Adenoviridae,Mastadenovirus,Human adenovirus D | — | KF268325,KF268327 |
| Human adenovirus 33 | NC_010956, NC_012959 | vertebrates,human | 1 | Adenoviridae,Mastadenovirus,Human adenovirus D | — | KF268322 |
| Human adenovirus 34 | NC_011202 | vertebrates,human | 2 | Adenoviridae,Mastadenovirus,Human adenovirus B | — | KF268328,AY737797 |
| Human adenovirus 34 | NC_011203 | vertebrates,human | 2 | Adenoviridae,Mastadenovirus,Human adenovirus B | — | KF268328,AY737797 |
| Human adenovirus 35 | NC_011202 | vertebrates,human | 2 | Adenoviridae,Mastadenovirus,Human adenovirus B | — | AY128640,AY271307 |
| Human adenovirus 35 | NC_011203 | vertebrates,human | 2 | Adenoviridae,Mastadenovirus,Human adenovirus B | — | AY128640,AY271307 |
| Human adenovirus 36 | NC_010956, NC_012959 | vertebrates,human | 1 | Adenoviridae,Mastadenovirus,Human adenovirus D | — | GQ384080 |

TABLE 10-continued

| Taxonomy | Rep.Acc.ID | Host | # GN's | Lineage | Seg. Count | GN.Acc.IDs |
|---|---|---|---|---|---|---|
| Human adenovirus 37 | NC_010956, NC_012959 | vertebrates,human | 9 | Adenoviridae,Mastadenovirus,Human adenovirus D | — | AB448775,KF268208, KF268324,AB448778, AB448777,AB448776 ,KF268203,DQ90090 0,KF268334 |
| Human adenovirus 38 | NC_010956, NC_012959 | vertebrates,human | 1 | Adenoviridae,Mastadenovirus,Human adenovirus D | — | KF268312 |
| Human adenovirus 4 | NC_010956, NC_012959 | vertebrates,human | 1 | Adenoviridae,Mastadenovirus,Human adenovirus D | — | KF268313 |
| Human adenovirus 4 | NC_011202 | vertebrates,human | 1 | Adenoviridae,Mastadenovirus,Human adenovirus B | — | KF429748 |
| Human adenovirus 4 | NC_011203 | vertebrates,human | 1 | Adenoviridae,Mastadenovirus,Human adenovirus B | — | KF429748 |
| Human adenovirus 43 | NC_010956, NC_012959 | vertebrates,human | 1 | Adenoviridae,Mastadenovirus,Human adenovirus D | — | KC529648 |
| Human adenovirus 46 | NC_010956, NC_012959 | vertebrates,human | 3 | Adenoviridae,Mastadenovirus,Human adenovirus D | — | KF268332,AY875648, KF268211 |
| Human adenovirus 48 | NC_010956, NC_012959 | vertebrates,human | 1 | Adenoviridae,Mastadenovirus,Human adenovirus D | — | EF153473 |
| Human adenovirus 49 | NC_010956, NC_012959 | vertebrates,human | 1 | Adenoviridae,Mastadenovirus,Human adenovirus D | — | DQ393829 |
| Human adenovirus 5 | NC_001405 | vertebrates,human | 2 | Adenoviridae,Mastadenovirus,Human adenovirus C | — | AY601635,M73260 |
| Human adenovirus 50 | NC_011202 | vertebrates,human | 1 | Adenoviridae,Mastadenovirus,Human adenovirus B | — | AY737798 |
| Human adenovirus 50 | NC_011203 | vertebrates,human | 1 | Adenoviridae,Mastadenovirus,Human adenovirus B | — | AY737798 |
| Human adenovirus 53 | NC_010956, NC_012959 | vertebrates,human | 1 | Adenoviridae,Mastadenovirus,Human adenovirus D | — | FJ169625 |
| Human adenovirus 54 | NC_010956, NC_012959 | vertebrates,human | 1 | Adenoviridae,Mastadenovirus,Human adenovirus D | — | AB448770 |
| Human adenovirus 55 | NC_011202 | vertebrates,human | 3 | Adenoviridae,Mastadenovirus,Human adenovirus B | — | JX123028,JX123029, JX123027 |
| Human adenovirus 55 | NC_011203 | vertebrates,human | 3 | Adenoviridae,Mastadenovirus,Human adenovirus B | — | JX123028,JX123029, JX123027 |
| Human adenovirus 56 | NC_010956, NC_012959 | vertebrates,human | 1 | Adenoviridae,Mastadenovirus,Human adenovirus D | — | KF268209 |
| Human adenovirus 6 | NC_001405 | vertebrates,human | 2 | Adenoviridae,Mastadenovirus,Human adenovirus C | — | FJ349096,HQ413315 |

TABLE 10-continued

| Taxonomy | Rep.Acc.ID | Host | ViroCap-1.0 Taxonomy | | Seg. Count | GN.Acc.IDs |
|---|---|---|---|---|---|---|
| | | | # GN's | Lineage | | |
| Human adenovirus 60 MPW-2011 | NC_010956, NC_012959 | vertebrates,human | 1 | Adenoviridae,Mastadenovirus,Human adenovirus D | — | HQ007053 |
| Human adenovirus 64 | NC_010956, NC_012959 | vertebrates,human | 4 | Adenoviridae,Mastadenovirus,Human adenovirus D | — | JQ326206,JQ326207, JQ326208,KF268213 |
| Human adenovirus 67 | NC_010956, NC_012959 | vertebrates,human | 1 | Adenoviridae,Mastadenovirus,Human adenovirus D | — | AP012302 |
| Human adenovirus 7 | NC_011202 | vertebrates,human | 10 | Adenoviridae,Mastadenovirus,Human adenovirus B | — | AY601634,JF800905, AY594256,HQ659699, KF268314,AY594255, AY495969,KF268316, GQ478341,JX62513 |
| Human adenovirus 7 | NC_011203 | vertebrates,human | 10 | Adenoviridae,Mastadenovirus,Human adenovirus B | — | AY601634,JF800905, AY594256,HQ659699, KF268314,AY594255, AY495969,KF268316, GQ478341,JX62513 |
| Human adenovirus 7a2 | NC_011202 | vertebrates,human | 1 | Adenoviridae,Mastadenovirus,Human adenovirus B | — | JN860677 |
| Human adenovirus 7a2 | NC_011203 | vertebrates,human | 1 | Adenoviridae,Mastadenovirus,Human adenovirus B | — | JN860677 |
| Human adenovirus 7h | NC_011202 | vertebrates,human | 1 | Adenoviridae,Mastadenovirus,Human adenovirus B | — | JN860676 |
| Human adenovirus 7h | NC_011203 | vertebrates,human | 1 | Adenoviridae,Mastadenovirus,Human adenovirus B | — | JN860676 |
| Human adenovirus 8 | NC_010956, NC_012959 | vertebrates,human | 14 | Adenoviridae,Mastadenovirus,Human adenovirus D | — | KF268333,KF429743, KF429746,AB448768, AB448767,KF429750, KF429747,KF429745, KF429751,KF268205, AB448769,KF429749, KF268321,KF429753 |
| Human adenovirus 9 | NC_010956, NC_012959 | vertebrates,human | 1 | Adenoviridae,Mastadenovirus,Human adenovirus D | — | KF268206 |
| Human adenovirus A | NC_001460 | vertebrates,human | 2 | Adenoviridae,Mastadenovirus,Human adenovirus A | — | KF268119,X73487 |
| Human adenovirus B | NC_011202 | vertebrates,human | 31 | Adenoviridae,Mastadenovirus,Human adenovirus B | — | JX423384,KF633445, AY163756,JX423385, JX491639,JX423386, KF268311,KF268133, JX423380,KF268120, DQ099432,KF268125, KF268124,KF268134 |

TABLE 10-continued

| Taxonomy | Rep.Acc.ID | Host | # GN's | Lineage | Seg. Count | GN.Acc.IDs |
|---|---|---|---|---|---|---|
| | | | | ViroCap-1.0 Taxonomy | | |
| | | | | | | JX423382,KF268121,KF268117,KF268128,KF268196,JX423383,KF268132,KF268123,KF268135,KF268126,JX423388,AY598970,EF011630,JX423387,DQ105654,KF268131,JX423381 |
| Human adenovirus B | NC_011203 | vertebrates,human | 31 | Adenoviridae,Mastadenovirus,Human adenovirus B | — | JX423384,KF633445,JX423385,JX491639,JX423386,KF268311,KF268133,JX423380,KF268120,DQ099432,KF268125,DQ08646 6,KF268124,KF268813 4,JX423382,KF26812 1,KF268117,KF26812 8,KF268196,JX42338 3,KF268132,KF26812 6,JX423388,AY59897 0,EF011630,JX42338 7,DQ105654,KF2681 31,JX423381 |
| Human adenovirus C | NC_001405 | vertebrates,human | 18 | Adenoviridae,Mastadenovirus,Human adenovirus C | — | KF268199,JX173086,JX173085,KF268130,JX173080,JX423389,KF429754,JX173079,JX173083,JQ1917,AY 339865,JX173078,KF 268129,JX173082,KF 268127,JX173084,JX 173077,JX173081 |
| Human adenovirus CR/France/2008 | NC_010956,NC_012959 | vertebrates,human | 1 | Adenoviridae,Mastadenovirus,Human adenovirus D | — | HM770721 |
| Human adenovirus D | NC_010956,NC_012959 | vertebrates,human | 15 | Adenoviridae,Mastadenovirus,Human adenovirus D | — | KF268197,JN162672,AB605242,AB605240,KF268122,AB605243,AB605244,AB60524 5,AB605246,KF26811 8,AB605241,AJ85448 6,KF268198,AB56258 8,JN162671 |
| Human adenovirus D B172/Dhaka City 9 | NC_010956,NC_012959 | vertebrates,human | 1 | Adenoviridae,Mastadenovirus,Human adenovirus D | — | AP012285 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human adenovirus JJS-2010 | NC_001405 | vertebrates,human | 1 | Adenoviridae,Mastadenovirus,Human adenovirus C | — | HQ003817 |
| Human adenovirus MZ | NC_001460 | vertebrates,human | 1 | Adenoviridae,Mastadenovirus,Human adenovirus A | — | JF964962 |
| Human astrovirus | NC_001943 | vertebrates,human | 5 | Astroviridae,Mamastrovirus,Mamastrovirus 1 | — | FJ375759,JF327666,AF141381,AB308374,L13745 |
| Human astrovirus 1 | NC_001943 | vertebrates,human | 5 | Astroviridae,Mamastrovirus,Mamastrovirus 1 | — | L23513,AY720892,H0398856,KF211475,JN887820 |
| Human astrovirus 1 Beijing/128/2005/CH N | NC_001943 | vertebrates,human | 1 | Astroviridae,Mamastrovirus,Mamastrovirus 1 | — | FJ755402 |
| Human astrovirus 1 Beijing/176/2006/CH N | NC_001943 | vertebrates,human | 1 | Astroviridae,Mamastrovirus,Mamastrovirus 1 | — | FJ755403 |
| Human astrovirus 1 Beijing/291/2007/CH N | NC_001943 | vertebrates,human | 1 | Astroviridae,Mamastrovirus,Mamastrovirus 1 | — | FJ755404 |
| Human astrovirus 1 Beijing/293/2007/CH N | NC_001943 | vertebrates,human | 1 | Astroviridae,Mamastrovirus,Mamastrovirus 1 | — | FJ755405 |
| Human astrovirus 2 | NC_001943 | vertebrates,human | 2 | Astroviridae,Mamastrovirus,Mamastrovirus 1 | — | KF039911,KF039910 |
| Human astrovirus 4 | NC_001943 | vertebrates,human | 5 | Astroviridae,Mamastrovirus,Mamastrovirus 1 | — | KF039913,DQ070852,AY720891,DQ34402 7,KF039912 |
| Human astrovirus 5 | NC_001943 | vertebrates,human | 2 | Astroviridae,Mamastrovirus,Mamastrovirus 1 | — | JQ403108,DQ028633 |
| Human astrovirus 6 | NC_001943 | vertebrates,human | 2 | Astroviridae,Mamastrovirus,Mamastrovirus 1 | — | GQ495608,HM23736 3 |
| Human astrovirus 8 | NC_001943 | vertebrates,human | 1 | Astroviridae,Mamastrovirus,Mamastrovirus 1 | — | AF260508 |
| Human bocavirus | NC_007455 | vertebrates,human | 123 | Parvoviridae,Bocavirus,Human bocavirus | — | JN387081,EF450736,GQ455987,JF327789,EU984236,JN387079,EF450731,FJ560720,AB481071,EF450722,AB481080,EF450739,AB481073,EU26297 8,AB480171,EF45072 9,JX887481,AB48108 5,AB480175,JN12895 4,DQ457413,JN1289 55,JN632515,FJ6954 72,DQ988934,JN086 998,JN387083,AB481 084,EF450727,EU98 4239,JQ411251,EF45 0717,JQ964115,EU9 84245,JN387080,EF4 50733,AB481082,EU 984235,EU984243,JN 632514,JN632511,AB 480176,EF450718,JN |

TABLE 10-continued

| Taxonomy | Rep.Acc.ID | Host | ViroCap-1.0 Taxonomy | | Seg. Count | GN.Acc.IDs |
|---|---|---|---|---|---|---|
| | | | # GN's | Lineage | | |
| | | | | | | 632213,EF450724,AB481077,EF450732,EF450737,JF699044,HQ585888,DQ000495,EF450738,AB481083,EF450735,EF203921,AB481076,EU984231,JN632519,EF450734,AB480170,EF450726,GQ925675,JQ964116,AB480172,JF327788,AB480174,AB551032,EF450728,EF450720,EU984238,EF450721,JN387084,EF450730,GQ926981,JX887480,JQ923422,JF327786,EF203922,EU262979,DQ340570,KC823115,JN794566,JN387085,GQ926983,EU984233,JN794565,FJ496754,AB481081,EU984241,AB481074,EU984244,DQ988933,JN632518,AB481075,EF450723,GU13942 3,GQ45 5988,EU984240,JX887482,EF450719,EU984242,EF450740,EU984237,EF450725,GU338055,FJ858259,AB481072,JN128953,GQ926982,JN632516,EF203920,JQ964114,JF327787,JN632517,DQ000496,JN387082,AB480173,EU984232,AB481078,AB481079,JN128956,EU984234,JN632512 |
| Human bocavirus 2 | NC_012042 | vertebrates,human | 15 | Parvoviridae,Bocavirus,Human bocavirus 2 | — | FJ973560,FJ170278,FJ948860,GU048664,GU301645,EU082213,GU048662,FJ170279,FJ170280,EU082214,GU301644,FJ973558 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human bocavirus 3 | NC_012564 | vertebrates,human | 7 | Parvoviridae,Bocavirus,Human bocavirus 3 | — | FJ973559,GQ200737,GU048663,HM132056,GQ86766,7,EU918736,GU048665,FJ973562,FJ94886 1,GQ867666 |
| Human bocavirus 4 | NC_012729 | vertebrates,human | 1 | Parvoviridae,Bocavirus,Human bocavirus 4 | — | FJ973561 |
| Human bocavirus WLL-1 | NC_007455 | vertebrates,human | 1 | Parvoviridae,Bocavirus,Human bocavirus | — | DQ778300 |
| Human bocavirus WLL-2 | NC_007455 | vertebrates,human | 1 | Parvoviridae,Bocavirus,Human bocavirus | — | EF441262 |
| Human bocavirus WLL-3 | NC_007455 | vertebrates,human | 1 | Parvoviridae,Bocavirus,Human bocavirus | — | EF584447 |
| Human bocavirus isolate SH1 | NC_007455 | vertebrates,human | 1 | Parvoviridae,Bocavirus,Human bocavirus | — | FJ375127 |
| Human bocavirus isolate SH2 | NC_007455 | vertebrates,human | 1 | Parvoviridae,Bocavirus,Human bocavirus | — | FJ375128 |
| Human bocavirus isolate SH3 | NC_012042 | vertebrates,human | 1 | Parvoviridae,Bocavirus,Human bocavirus 2 | — | FJ375129 |
| Human calicivirus Hu/NLV/G11/MD145-12/1987/US | NC_001959 | vertebrates,human | 1 | Caliciviridae,Norovirus,Norwalk virus | — | AY032605 |
| Human calicivirus Hu/NLV/Oxford/B5522/2003/UK | NC_001959 | vertebrates,human | 1 | Caliciviridae,Norovirus,Norwalk virus | — | AY581254 |
| Human calicivirus N LV/G11/Langen 1061/2002/DE | NC_001959 | vertebrates,human | 1 | Caliciviridae,Norovirus,Norwalk virus | — | AY485642 |
| Human calicivirus strain Mc37 | NC_001959 | vertebrates,human | 1 | Caliciviridae,Norovirus,Norwalk virus | — | AY237415 |
| Human coronavirus 229E | NC_002645 | vertebrates,human | 6 | Coronaviridae,Alphacoronavirus,Human coronavirus 229E | — | KF514430,AF304460,JX503060,KF514433,JX503061,KF514432 |
| Human coronavirus HKU1 | NC_006577 | vertebrates,human | 36 | Coronaviridae,Betacoronavirus,Human coronavirus HKU1 | — | KF430202,DQ415901,AY597011,KF686343,HM034837,KF68633 9,AY884001,DQ4159 09,DQ415904,KF686 342,KF686340,DQ41 5907,KF850450,DQ4 15902,KF686344,KF4 30199,DQ415903,KF 686341,DQ415908,D 0415914,DQ339101, DQ415900,DQ41590 6,KF686338,KF68634 6,DQ415905,DQ4158 98,KF430201,DQ415 899,DQ415913,DQ41 5912,KF686345,DQ4 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human coronavirus NL63 | NC_005831 | vertebrates,human | 24 | Coronaviridae,Alphacoronavirus,Human coronavirus NL63 | — | 15896,DQ415897,DQ415911,DQ415910,JQ765572,JX104161,JQ900257,JQ765569,JQ765566,JQ765575,JQ765564,JQ900256,JQ765570,JQ900259,JQ765563,JQ765574,DQ445911,CS124012,JQ765565,JX504050,JQ765567,DQ44591,2,JQ765573,JX52417,1,JQ765568,AY56748,7,JQ765571,JQ900255 |
| Human coxsackievirus A1 | NC_002058 | vertebrates,human | 3 | Picornaviridae,Enterovirus,Enterovirus C | — | JX174177,AF499635,JX174176 |
| Human coxsackievirus A10 | NC_001612 | vertebrates,human | 2 | Picornaviridae,Enterovirus,Enterovirus A | — | AY421767,HQ728262 |
| Human coxsackievirus A11 | NC_002058 | vertebrates,human | 6 | Picornaviridae,Enterovirus,Enterovirus C | — | DQ995634,DQ99563 3,JF260917,JF26091 9,AF499636,JF26091 8 |
| Human coxsackievirus A12 | NC_001612 | vertebrates,human | 1 | Picornaviridae,Enterovirus,Enterovirus A | — | AY421768 |
| Human coxsackievirus A13 | NC_002058 | vertebrates,human | 16 | Picornaviridae,Enterovirus,Enterovirus C | — | DQ995642,DQ99564 0,DQ995637,DQ99956 36,DQ995635,DQ995 641,JF260920,AF465 511,AF499637,DQ99 5638,JF260923,JF26 0922,JF260921,DQ99 5644,DQ995639,DQ9 95643 |
| Human coxsackievirus A14 | NC_001612 | vertebrates,human | 1 | Picornaviridae,Enterovirus,Enterovirus A | — | AY421769 |
| Human coxsackievirus A15 | NC_002058 | vertebrates,human | 2 | Picornaviridae,Enterovirus,Enterovirus C | — | AF465512,AF499638 |
| Human coxsackievirus A16 | NC_001612 | vertebrates,human | 34 | Picornaviridae,Enterovirus,Enterovirus A | — | JXQ68827,JQ746666,JX481738,JF738003,JX986740,KC695830,JN674176,JF738004,EU812514,JQ316639,KC117318,AF17791 1,JX986741,KC11731 7,KC342228,JQ0341 49,EU262658,JXQ688 30,J XQ68833,JQ7466 60,AY790926,HQ423 141,JXQ68828,JXQ68 832,HQ269389,J XQ6 8829,JX507808,JX83 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human coxsackievirus A17 | NC_002058 | vertebrates,human | 6 | Picornaviridae,Enterovirus,Enterovirus C | — | 9965,JXQ68831,GQ279368,JQ746661,JX986742,FJ198212,GQ279371 |
| Human coxsackievirus A18 | NC_002058 | vertebrates,human | 3 | Picornaviridae,Enterovirus,Enterovirus C | — | JF260924,DQ995645,JF260925,FM955278,DQ995646,AF499639 |
| Human coxsackievirus A19 | NC_002058 | vertebrates,human | 1 | Picornaviridae,Enterovirus,Enterovirus C | — | AF465513,AB205396,AF499640 |
| Human coxsackievirus A2 | NC_001612 | vertebrates,human | 2 | Picornaviridae,Enterovirus,Enterovirus A | — | AF499641 |
| Human coxsackievirus A20 | NC_002058 | vertebrates,human | 3 | Picornaviridae,Enterovirus,Enterovirus C | — | AY421760,HQ728259 DQ358078,AF499642,AF465514 |
| Human coxsackievirus A21 | NC_002058 | vertebrates,human | 2 | Picornaviridae,Enterovirus,Enterovirus C | — | AF546702,AF465515 |
| Human coxsackievirus A21 Coe | NC_002058 | vertebrates,human | 1 | Picornaviridae,Enterovirus,Enterovirus C | — | DQ0538 |
| Human coxsackievirus A22 | NC_002058 | vertebrates,human | 4 | Picornaviridae,Enterovirus,Enterovirus C | — | DQ995647,JN542510,AF499643,DQ995648 |
| Human coxsackievirus A24 | NC_002058 | vertebrates,human | 19 | Picornaviridae,Enterovirus,Enterovirus C | — | EF026081,JF742578,D90457,AB769160,JN228097,AB769154,DQ443001,AB769159,AB769162,AB769165,AB769164,JF742577,AB769161,JF742579,JF742576,AB769163,AB769156,DQ443002,AB769152 |
| Human coxsackievirus A3 | NC_001612 | vertebrates,human | 1 | Picornaviridae,Enterovirus,Enterovirus A | — | AY421761 |
| Human coxsackievirus A4 | NC_001612 | vertebrates,human | 2 | Picornaviridae,Enterovirus,Enterovirus A | — | HQ728260,AY421762 |
| Human coxsackievirus A5 | NC_001612 | vertebrates,human | 2 | Picornaviridae,Enterovirus,Enterovirus A | — | AY421763,HQ728261 |
| Human coxsackievirus A6 | NC_001612 | vertebrates,human | 9 | Picornaviridae,Enterovirus,Enterovirus A | — | JQ946053,AB678778,JQ946051,JQ946054,JQ964234,JQ946055,JQ946052,AY421764,JQ946050 |
| Human coxsackievirus A7 | NC_001612 | vertebrates,human | 2 | Picornaviridae,Enterovirus,Enterovirus A | — | AY421765,JQ041367 |
| Human coxsackievirus A8 | NC_001612 | vertebrates,human | 1 | Picornaviridae,Enterovirus,Enterovirus A | — | AY421766 |
| Human coxsackievirus A9 | NC_001472 | vertebrates,human | 1 | Picornaviridae,Enterovirus,Enterovirus B | — | DQ0627 |
| Human coxsackievirus B1 | NC_001472 | vertebrates,human | 7 | Picornaviridae,Enterovirus,Enterovirus B | — | AY186745,JN596588,AY186748,AY186746,AY186747,JX976769,EU147493 |
| Human coxsackievirus B2 | NC_001472 | vertebrates,human | 4 | Picornaviridae,Enterovirus,Enterovirus B | — | AF081485,EF174468,AF085363,EF174469 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Human coxsackievirus B3 | NC_001472 | vertebrates,human | Picornaviridae,Enterovirus,Enterovirus B | 20 | — | U57056,AF231764,AF231763,JX976770,AY752945,AY752944,M88483,AY752946,M16572,GU109481,M33854,FJQ00001,FJ357838,JN979570,GQ141875,EU144042,KC481610,AY673831,JX312064,AF231765 |
| Human coxsackievirus B4 | NC_001472 | vertebrates,human | Picornaviridae,Enterovirus,Enterovirus B | 6 | — | AF311939,DQ480420,S76772,XQ5690,JX308222,AF328683 |
| Human coxsackievirus B5 | NC_001472 | vertebrates,human | Picornaviridae,Enterovirus,Enterovirus B | 13 | — | AY875692,GU376747,HQ998851,JXQ17380,X67706,JXQ17382,JX276378,JN580070,JN695050,AF114383,JN695051,JXQ17383,JXQ17381 |
| Human coxsackievirus B6 | NC_001472 | vertebrates,human | Picornaviridae,Enterovirus,Enterovirus B | 4 | — | JQ041368,AF114384,AF105342,AF039205 |
| Human echovirus 11 | NC_001472 | vertebrates,human | Picornaviridae,Enterovirus,Enterovirus B | 6 | — | EF634316,X80059,AJ276224,AJ577594,AJ577590,AJ577589 |
| Human echovirus 12 | NC_001472 | vertebrates,human | Picornaviridae,Enterovirus,Enterovirus B | 2 | — | X79047,X77708 |
| Human echovirus 13 | NC_001472 | vertebrates,human | Picornaviridae,Enterovirus,Enterovirus B | 5 | — | AB501332,AB501329,AB501330,AB501331,AY302539 |
| Human echovirus 14 | NC_001472 | vertebrates,human | Picornaviridae,Enterovirus,Enterovirus B | 1 | — | AY302540 |
| Human echovirus 15 | NC_001472 | vertebrates,human | Picornaviridae,Enterovirus,Enterovirus B | 1 | — | AY302541 |
| Human echovirus 16 | NC_001472 | vertebrates,human | Picornaviridae,Enterovirus,Enterovirus B | 1 | — | AY302542 |
| Human echovirus 17 | NC_001472 | vertebrates,human | Picornaviridae,Enterovirus,Enterovirus B | 1 | — | AY302543 |
| Human echovirus 18 | NC_001472 | vertebrates,human | Picornaviridae,Enterovirus,Enterovirus B | 2 | — | AF317694,HM777023 |
| Human echovirus 19 | NC_001472 | vertebrates,human | Picornaviridae,Enterovirus,Enterovirus B | 1 | — | AY302544 |
| Human echovirus 2 | NC_001472 | vertebrates,human | Picornaviridae,Enterovirus,Enterovirus B | 2 | — | AY302545,AF465518 |
| Human echovirus 20 | NC_001472 | vertebrates,human | Picornaviridae,Enterovirus,Enterovirus B | 1 | — | AY302546 |
| Human echovirus 21 | NC_001472 | vertebrates,human | Picornaviridae,Enterovirus,Enterovirus B | 1 | — | AY302547 |
| Human echovirus 24 | NC_001472 | vertebrates,human | Picornaviridae,Enterovirus,Enterovirus B | 1 | — | AY302548 |
| Human echovirus 25 | NC_001472 | vertebrates,human | Picornaviridae,Enterovirus,Enterovirus B | 2 | — | AY302549,HM031191 |
| Human echovirus 26 | NC_001472 | vertebrates,human | Picornaviridae,Enterovirus,Enterovirus B | 1 | — | AY302550 |
| Human echovirus 27 | NC_001472 | vertebrates,human | Picornaviridae,Enterovirus,Enterovirus B | 1 | — | AY302551 |
| Human echovirus 29 | NC_001472 | vertebrates,human | Picornaviridae,Enterovirus,Enterovirus B | 1 | — | AY302552 |
| Human echovirus 3 | NC_001472 | vertebrates,human | Picornaviridae,Enterovirus,Enterovirus B | 13 | — | AB647324,AB647318,AB647326,AB647320,AB647325,AB6473 19,AY302553,AJ8499 42,AB647322,AB647 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human echovirus 30 | NC_001472 | vertebrates,human | 5 | Picornaviridae,Enterovirus,Enterovirus B | — | 317,AB647321,AB647323,AB647316 JN704615,DQ246620 ,AF311938,DQ53420 5,AF162711 |
| Human echovirus 31 | NC_001472 | vertebrates,human | 1 | Picornaviridae,Enterovirus,Enterovirus B | — | AY302554 |
| Human echovirus 32 | NC_001472 | vertebrates,human | 1 | Picornaviridae,Enterovirus,Enterovirus B | — | AY302555 |
| Human echovirus 33 | NC_001472 | vertebrates,human | 1 | Picornaviridae,Enterovirus,Enterovirus B | — | AY302556 |
| Human echovirus 4 | NC_001472 | vertebrates,human | 2 | Picornaviridae,Enterovirus,Enterovirus B | — | AY302557,FJ172447 |
| Human echovirus 5 | NC_001472 | vertebrates,human | 2 | Picornaviridae,Enterovirus,Enterovirus B | — | HM775882,AF083069 |
| Human echovirus 6 | NC_001472 | vertebrates,human | 5 | Picornaviridae,Enterovirus,Enterovirus B | — | U16283,AY302558,AF465517,HM185055,JQ729993 |
| Human echovirus 7 | NC_001472 | vertebrates,human | 4 | Picornaviridae,Enterovirus,Enterovirus B | — | AY036578,AF465516,AY302559,AY036579 |
| Human echovirus 9 | NC_001472 | vertebrates,human | 2 | Picornaviridae,Enterovirus,Enterovirus B | — | AF524867,AF524866 |
| Human endogenous retrovirus K113 | NC_022518 | vertebrates,human | 1 | Retroviridae,Human endogenous retrovirus K | — | AY037928 |
| Human endogenous retrovirus K115 | NC_022518 | vertebrates,human | 1 | Retroviridae,Human endogenous retrovirus K | — | AY037929 |
| Human enteric coronavirus strain 4408 | NC_012950 | vertebrates,human | 1 | Coronaviridae,Human enteric coronavirus strain 4408 | — | FJ938067 |
| Human enterovirus 100 | NC_001472 | vertebrates,human | 1 | Picornaviridae,Enterovirus,Enterovirus B | — | DQ902713 |
| Human enterovirus 101 | NC_001472 | vertebrates,human | 1 | Picornaviridae,Enterovirus,Enterovirus B | — | AY843308 |
| Human enterovirus 102 | NC_002058 | vertebrates,human | 1 | Picornaviridae,Enterovirus,Enterovirus C | — | EF555645 |
| Human enterovirus 104 | NC_002058 | vertebrates,human | 1 | Picornaviridae,Enterovirus,Enterovirus C | — | AB686524 |
| Human enterovirus 107 | NC_001472 | vertebrates,human | 1 | Picornaviridae,Enterovirus,Enterovirus B | — | AB426609 |
| Human enterovirus 68 | NC_001430 | vertebrates,human | 8 | Picornaviridae,Enterovirus,Enterovirus D | — | JX101846,EF107098,JXQ70222,AB601883,AB601884,AY426531,AB601885,AB601882 |
| Human enterovirus 69 | NC_001472 | vertebrates,human | 1 | Picornaviridae,Enterovirus,Enterovirus B | — | AY302560 |
| Human enterovirus 70 | NC_001430 | vertebrates,human | 1 | Picornaviridae,Enterovirus,Enterovirus D | — | DQ201177 |
| Human enterovirus 71 | NC_001612 | vertebrates,human | 281 | Picornaviridae,Enterovirus,Enterovirus A | — | DQ341365,JX244183,AB575917,HQ88218 ,AB575917,HQ88218 2,HM053669,AF1363 79,GU396280,JX678 880,HM245928,GQ23 1931,HQ647177,GU3 66191,JQ074188,AB4 69182,EU414333,GQ 231928,JX678885,JF 820315,JQ639384,JX 111890,AF176044,D 0341362,HQ891928, AB550336,HQ647171 ,HM807310,EU86450 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 7,JQ074190,EU4143 |
| | | | | | | 35,FJ194965,JN9646 |
| | | | | | | 86,JX678875,FJ6064 |
| | | | | | | 48,JX678886,EF3735 |
| | | | | | | 75,HQ694986,HM002 |
| | | | | | | 486,GU198368,JX24 |
| | | | | | | 4182,GQ231925,JQ2 |
| | | | | | | 80307,HM002489,FJ |
| | | | | | | 828519,JQ708209,G |
| | | | | | | 0279369,FJ607338,J |
| | | | | | | X986738,AB575935,J |
| | | | | | | N992285,JX111891, |
| | | | | | | GQ231934,HQ32585 |
| | | | | | | 2,AB550339,HQ8919 |
| | | | | | | 23,JN020147,HQ423 |
| | | | | | | 142,JQ319054,HQ64 |
| | | | | | | 7170,JF738002,JN99 |
| | | | | | | 2284,GU459070,JQ7 |
| | | | | | | 36684,JX678879,HQ |
| | | | | | | 694982,FJ607334,JX |
| | | | | | | 678883,HQ647176,H |
| | | | | | | 0647169,AB575936, |
| | | | | | | AB575913,GU198367 |
| | | | | | | ,JX111893,EU376004 |
| | | | | | | ,FJ606449,DQ381846 |
| | | | | | | ,AM396586,JF738001 |
| | | | | | | ,GU198369,EU70381 |
| | | | | | | 4,AM396587,JN2560 |
| | | | | | | 64,JQ708210,AF3044 |
| | | | | | | 57,JX244186,HQ891 |
| | | | | | | 925,HQ828086,GU19 |
| | | | | | | 8370,AB575928,EU3 |
| | | | | | | 76005,JXQ25561,JX1 |
| | | | | | | 11892,JX678874,FJ6 |
| | | | | | | 06450,HM053671,HQ |
| | | | | | | 647174,JQ950555,AY |
| | | | | | | 465356,AB550333,H |
| | | | | | | 0647179,JN544419, |
| | | | | | | AB575937,EU414334 |
| | | | | | | ,HQ647175,HQ64716 |
| | | | | | | 8,AB575914,JX67888 |
| | | | | | | 2,HQ891927,JX9867 |
| | | | | | | 39,GQ231936,FJ360 |
| | | | | | | 546,HM003207,JN99 |
| | | | | | | 2283,GQ994990,U22 |
| | | | | | | 521,AB575918,DQ34 |
| | | | | | | 1364,JF738000,HQ18 |
| | | | | | | 8292,AB575915,AM3 |

| Taxonomy | Rep.Acc.ID | Host | # GN's | Lineage | Seg. Count | GN.Acc.IDs |
|---|---|---|---|---|---|---|
| | | | | | | 96588,EU812515,FJ607336,GQ231932,JQ639383,HQ647172,EF063152,GQ231927,JXQ17384,AB550335,JN256060,AB469183,AB550341,U22522,H0891926,HM002487,HQ64717,JX678877,GQ231942,AB57591,1,FJ158601,AF304458,DQ341363,HM002484,HM245927,AB550340,DQ060149,DQ341358,FJ713137,GQ994991,JN256059,HQ426649,AB550337,AB575916,AF119796,AB575941,JN992282,H0129932,HQ825317,JX111888,DQ341367,FJ606447,HQ694983,JX678884,GQ89283 0,JN256061,FJ172159,AB575912,HM0024 85,AB575939,JQ681218,FJ158600,FJ607335,AB575927,JF830007,JN001860,DQ341357,AM396584,AF302996,AB575948,GQ231930,JF820314,AM396585,FJ360544,AJ586873,JX678881,HQ407557,DQ341368,JN256063,HQ891929,JX244187,JF894382,HQ891924,JQ742001,DQ341359,GQ994992,AF304459,JQ316638,AB575942,HQ189392,DQ133459,GU198371,JN052925,JQ074189,JN256062,JQ806378,HM053670,GQ231929,AB204853,JF820316,JX678876,JQ074187,EU703812,FJ60 |

TABLE 10-continued

VisoCap-1.0 Taxonomy

| Taxonomy | Rep.Acc.ID | Host | # GN's | Lineage | Seg. Count | GN.Acc.IDs |
|---|---|---|---|---|---|---|
| Human enterovirus 71 HZ08/Hangzhou/2008 | NC_001612 | vertebrates,human | 1 | Picornaviridae, Enterovirus, Enterovirus A | — | 7337,HM002488,EF3 73576,AB482183,HQ 694985,GU459071,J XQ25559,JF894381,H 0998852,GQ231926, FJ194964,AF119795, GQ994989,DQ13345 8,FJ360545,HQ71202 0,JQ742002,GQ2793 70,AB550334,GU196 833,JF820313,DQ341 360,AB550338,JN835 312,JF894383,JX678 878,HQ611148,GQ23 1941,JX986737,GQ2 31933,HQ647180,DQ 341355,EU364841,K C109780,AB575938, DQ452074,GQ231938, 9,GU43467,DQ23193 61,HQ423143,GQ231 940,GQ231935,HQ69 4984,JF913464,EU70 3813,DQ341366,JX2 44184,AB204852,FJ4 61781,JX244185,GQ 994988,HQ647173,E U414331,GQ231938, AB550332,JN544418, HQ647167,JQ804832 ,AB575923,GQ23194 3,GQ231937,JX1118 89,FJ439769,DQ3413 56,JF820312,DQ3413 54,KC414134,EU131 776,JF799986 |
| Human enterovirus 74 | NC_001472 | vertebrates,human | 2 | Picornaviridae, Enterovirus, Enterovirus B | — | JQ397329,AY556057 |
| Human enterovirus 75 | NC_001472 | vertebrates,human | 1 | Picornaviridae,Enterovirus,Enterovirus B | — | AY556070 |
| Human enterovirus 76 | NC_001612 | vertebrates,human | 2 | Picornaviridae, Enterovirus, Enterovirus A | — | JF905564,AY697458 |
| Human enterovirus 77 | NC_001472 | vertebrates,human | 1 | Picornaviridae,Enterovirus,Enterovirus B | — | AY843302 |
| Human enterovirus 79 | NC_001472 | vertebrates,human | 2 | Picornaviridae, Enterovirus, Enterovirus B | — | AY843297,AB426610 |
| Human enterovirus 80 | NC_001472 | vertebrates,human | 2 | Picornaviridae, Enterovirus, Enterovirus B | — | JX644073,AY843298 |
| Human enterovirus 81 | NC_001472 | vertebrates,human | 1 | Picornaviridae,Enterovirus,Enterovirus B | — | AY843299 |
| Human enterovirus 82 | NC_001472 | vertebrates,human | 1 | Picornaviridae,Enterovirus,Enterovirus B | — | AY843300 |
| Human enterovirus 83 | NC_001472 | vertebrates,human | 1 | Picornaviridae,Enterovirus,Enterovirus B | — | AY843301 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human enterovirus 84 | NC_001472 | vertebrates,human | 1 | Picornaviridae,Enterovirus,Enterovirus B | — | DQ902712 |
| Human enterovirus 85 | NC_001472 | vertebrates,human | 6 | Picornaviridae, Enterovirus, Enterovirus B | — | AY843303,JX898905, JX899908,JX898907, JX898906,JX898909 |
| Human enterovirus 86 | NC_001472 | vertebrates,human | 1 | Picornaviridae,Enterovirus,Enterovirus B | — | AY843304 |
| Human enterovirus 87 | NC_001472 | vertebrates,human | 1 | Picornaviridae,Enterovirus,Enterovirus B | — | AY843305 |
| Human enterovirus 88 | NC_001430 | vertebrates,human | 1 | Picornaviridae,Enterovirus,Enterovirus B | — | AY843306 |
| Human enterovirus 89 | NC_001612 | vertebrates,human | 1 | Picornaviridae,Enterovirus,Enterovirus A | — | AY697459 |
| Human enterovirus 90 | NC_001612 | vertebrates,human | 6 | Picornaviridae, Enterovirus, Enterovirus A | — | JX390655,AB192877, JX390654,AY697460, JX390656,AY773285 |
| Human enterovirus 91 | NC_001612 | vertebrates,human | 1 | Picornaviridae,Enterovirus,Enterovirus A | — | AY697461 |
| Human enterovirus 92 | NC_001612 | vertebrates,human | 1 | Picornaviridae,Enterovirus,Enterovirus A | — | EF667344 |
| Human enterovirus 94 | NC_001430 | vertebrates,human | 2 | Picornaviridae,Enterovirus, Enterovirus D | — | DQ916376,EF107097 |
| Human enterovirus 96 | NC_002058 | vertebrates,human | 1 | Picornaviridae,Enterovirus,Enterovirus C | — | EF015886 |
| Human enterovirus 97 | NC_001472 | vertebrates,human | 2 | Picornaviridae,Enterovirus,Enterovirus B | — | AY843307,AB426611 |
| Human enterovirus 98 | NC_001472 | vertebrates,human | 1 | Picornaviridae,Enterovirus,Enterovirus B | — | AB426608 |
| Human enterovirus 99 | NC_002058 | vertebrates,human | 2 | Picornaviridae,Enterovirus,Enterovirus C | — | EF555644,JF260926 |
| Human enterovirus A | NC_001612 | vertebrates,human | 9 | Picornaviridae, Enterovirus, Enterovirus A | — | HQ456312,HQ45630 7,HQ456313,HQ4563 08,HQ456306,HQ456 309,HQ456311,HQ45 6310,HQ456305 |
| Human enterovirus B | NC_001472 | vertebrates,human | 6 | Picornaviridae, Enterovirus, Enterovirus B | — | AY896765,EF371880, AY896762,AJ493062, AY896763,HM185056 |
| Human enterovirus C | NC_002058 | vertebrates,human | 22 | Picornaviridae,Enterovirus,Enterovirus C | — | HQ738302,HQ738301,HQ738290,HQ73830 1,HQ738290,HQ7382 86,HQ738291,HQ738 298,JX393301,HQ73 8294,HQ738297,V01 149,HQ738300,HQ73 8296,HQ738299,HQ7 38293,HQ738288,JX 393302,HQ738289,H 0738292,HQ738287, HQ738303,AB205395 ,H Q738295 |
| Human enterovirus C104 | NC_002058 | vertebrates,human | 7 | Picornaviridae,Enterovirus,Enterovirus C | — | JX982256,JX982254, JX982253,JX982255, JX982259,JX982258, JX982257 |
| Human enterovirus C105 | NC_002058 | vertebrates,human | 1 | Picornaviridae,Enterovirus,Enterovirus C | — | JX514943 |
| Human enterovirus C109 | NC_002058 | vertebrates,human | 1 | Picornaviridae,Enterovirus,Enterovirus C | — | GQ865517 |
| Human enterovirus C116 | NC_002058 | vertebrates,human | 1 | Picornaviridae,Enterovirus,Enterovirus C | — | JX514942 |
| Human enterovirus C117 | NC_002058 | vertebrates,human | 1 | Picornaviridae,Enterovirus,Enterovirus C | — | JX262382 |
| Human enterovirus C118 | NC_002058 | vertebrates,human | 3 | Picornaviridae,Enterovirus,Enterovirus C | — | JX961709,JX678288, JX961708 |

TABLE 10-continued

VíroCap-1.0 Taxonomy

| Taxonomy | Rep.Acc.ID | Host | # GN's | Lineage | Seg. Count | GN.Acc.IDs |
|---|---|---|---|---|---|---|
| Human enterovirus C96 | NC_002058 | vertebrates,human | 5 | Picornaviridae,Enterovirus,Enterovirus C | — | HQ415759,FJ751915, FJ751914,KF495604, HQ415758 |
| Human enterovirus C99 | NC_002058 | vertebrates,human | 7 | Picornaviridae,Enterovirus,Enterovirus C | — | KF129411,EF015012, KF129412,EF015011, EF015010,EF015009, EF015008 |
| Human enterovirus D | NC_001430 | vertebrates,human | 1 | Picornaviridae,Enterovirus,Enterovirus D | — | DQ0820 |
| Human enterovirus Hangzhou13-02 | NC_002058 | vertebrates,human | 1 | Picornaviridae,Enterovirus,Enterovirus C | — | AY876913 |
| Human enterovirus Ningbo3-02 | NC_002058 | vertebrates,human | 1 | Picornaviridae,Enterovirus,Enterovirus C | — | AY876912 |
| Human group 1 coronavirus associated with pneumonia | NC_005831 | vertebrates,human | 1 | Coronaviridae,Alphacoronavirus,Human coronavirus NL63 | — | AY518894 |
| Human herpesvirus 1 | NC_001806 | vertebrates,human | 8 | Herpesviridae,Simplexvirus,Human herpesvirus 1 | — | KF498959,JQ673480, GU734772,X14112,FJ593289,GU734771,JN555585,JQ780693 |
| Human herpesvirus 2 | NC_001798 | vertebrates,human | 2 | Herpesviridae,Simplexvirus,Human herpesvirus 2 | — | Z86099,KF781518 |
| Human herpesvirus 3 | NC_001348 | vertebrates,human | 47 | Herpesviridae,Varicellovirus,Human herpesvirus 3 | — | DQ479962,JN704700,DQ479956,DQ452050,JN704703,JN704705,JN704708,KC84729,JN704698,DQ00834,AY548171,JN704691,JN704695,AB097933,DQ674250,DQ479961,JN704709,JN704694,DQ479959,JN704710,JN704690,DQ479958,DQ479957,JN704706,JN704704,D00835,JN704696, KC112914,DQ479954,DQ479953,JN704697,JN704701,DQ479955,EU154348,DQ479960,JF306641,DQ479963,JN704699,AB097932,DQ457052,JN704707,JN704692,AY548170,JN704702,XQ438171403,JN704693 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Human herpesvirus 4 | NC_007605 NC_009334 | vertebrates,human | Herpesviridae,Lymphocryptovirus,Human herpesvirus 4 | 5 | — | AJ507799,KC207813, KC207814,AY961628 ,KF373730 |
| Human herpesvirus 5 | NC_006273 | vertebrates,human | Herpesviridae,Cytomegalovirus,Human herpesvirus 5 | 46 | — | JX512200,GU179290 ,GU179291,GQ22197 4,FJ527563,GU93774 2,GQ396662,KC5193 19,GU179001,AC146 999,JX512204,GQ22 1973,KF297339,JX51 2205,AC146906,JX51 2199,HQ380895,GQ2 21975,GU179288,JX 512203,AY315197,JX 512202,KC519321,FJ 616285,JX512197,G 0121041,EF999921, AC146851,JX512208, KC519323,JX512201, AC146904,AY446894 ,JX512206,JX512207, GQ466044,AC14690 5,KC519320,GU1792 89,GQ396663,GU980 198,X17403,KC51932 2,JX512198,AC14690 7,KF021605 |
| Human herpesvirus 7 | NC_001716 | vertebrates,human | Herpesviridae,Roseolovirus,Human herpesvirus 7 | 2 | — | AF037218,U43400 |
| Human herpesvirus 8 | NC_009333 | vertebrates,human | Herpesviridae,Rhadinovirus,Human herpesvirus 8 | 3 | — | AF148805,HQ404500 ,JQ619843 |
| Human herpesvirus 8 type P | NC_009333 | vertebrates,human | Herpesviridae,Rhadinovirus,Human herpesvirus 8 | 1 | — | GQ994935 |
| Human immunodeficiency virus 1 | NC_001802 | vertebrates,human | Retroviridae,Lentivirus,Human immunodeficiency virus 1 | 1815 | — | K02013,DQ676887,E U697905,GQ372988, AF408631,AF042103, EU110097,DQ020274 ,AB253705,DQ39638 0,DQ314731,AY7795 51,KC899015,FJ66234 91,FJ670519,GU7337 15,AF069140,AB2536 90,AB253679,KC156 213,AB253676,EF637 057,U63632,FJ62349 4,FJ771010,DQ16410 5,GQ999983,AF4430 76,AB253686,AB231 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 898,AF119820,KC89898,AY819715,FJ496163,JX574663,AF256211,AF107771,KC156129,U69585,EF495062,AB231896,GQ999973,DQ487190,AB098331,EU110085,AF490974,AY771591,EU293450,EU735535,AY586542,AB565503,AB287003,AB253707,AY463229,AF259954,AB286863,EF363125,AY352655,DQ351222,AB565500,DQ011177,AY331293,FJ495822,AY536235,AY308762,AJ251056,FJ495826,AY586544,FJ496085,U69589,AB286857,FJ62348 2,EF178366,AF197338,FJ4960 82,AY463235,AY835758,EU616643,AB253693,AY878055,AF110966,JF804806,KC898993,AB287370,AY900572,DQ164121,EU697906,EU735536,AB287363,DQ853445,FJ185228,KC898988,AY455785,AF075701,KC156218,HM026460,EU110086,FJ495941,AF005494,AY125894,DQ886033,KC898976,AB485656,DQ093591,JX503074,GU362013,FJ670525,AF067157,DQ207943,U69586,AB254154,FJ185238,AY560108,AY901971,KC522034,AF110961,AY835761,DQ358799,AB565502,EU786675,AY771589,AF190127,AB253640, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | DQ445635,EU735539,AJ291718,DQ369977,EU743964,GU733713,AF067155,AY781127,DQ396386,AF443077,FJ496189,FJ623485,FJ496156,KC503855,DQ853451,AB253421,FJ670516,DQ854716,AF450098,EU110092,EU786680,DQ351217,EF514699,AF067159,DQ351231,AY771593,AY878064,EU697904,AY835763,GU647197,GQ365652,AB565504,U51190,AY586546,FJ623493,U39362,EU786673,D0295195,AY463236,AJ866555,AY835751,AB286956,AY586545,FJ496074,EU697908,A07867,DQ886036,D0912822,AF119819,AF423756,DQ358808,DQ396384,AB25370 6,AY945709,DQ3963 69,AY314046,FJ8646 79,GQ999975,AF289 548,FJ855622,DQ990 880,AY970950,AB73 1663,FJ496076,DQ39 6382,AB428555,AB7 31665,AY586548,AF4 08630,JQ341411,KC 156215,EU110087,K0 2007,AY455779,AF44 3074,AJ276595,FJ67 0531,DQ164116,FJ18 5245,DQ007903,AF0 69671,AY968312,EU 446022,AY455782,FJ 195091,AY332236,A B253712,AY771588, AB253644,DQ164110 ,FJ460501,DQ164112 ,AY779558,AB25364 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 9,DQ054367,AY9005 75,AY772692,JX5030 75,AY901980,AB231 895,FJ623479,GU177 863,KC899011,FJ496 200,AY46233,HM02 6459,JQ316136,AY00 8714,FJ185254,GU73 3714,DQ358802,AF4 84515,D10112,DQ88 6034,DQ351221,AF4 43099,AB253681,AY 093605,AY773338,FJ 496214,DQ093585,A F107770,DQ085872, KC899007,DQ396400 ,AB098332,DQ85344 1,FJ496194,AB28737 7,AB253714,DQ8534 38,AF443092,FJ6234 77,FJ185239,AB2873 67,XQ1762,AF110974 ,DQ351235,DQ32223 9,DQ085875,AF1109 75,AM000054,AP005 206,FJ496181,AY835 773,GU647196,KC15 6126,DQ853465,HM4 69972,JX503080,DQ 396364,AF197341,JN 860764,AY818644,FJ 195088,AF443107,FJ 670521,DQ295193,FJ 496151,AB480301,D 0853455,AB746345, AB097868,FJ496183, AY772535,DQ056418 ,AY835770,EU00050 7,DQ676871,D86068, AB485639,AF411967, JQ316130,AB485657, AY314053,AY901976 ,KC898984,JX503076 ,AB286856,EF363124 ,AF075702,AY423384 ,AF290028,FJ496191 ,AY779560,EU03191 3,DQ36997,AF2895 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 50,AY773340,AF0421 |
| | | | | | | 02,AF061642,AF0043 |
| | | | | | | 94,EF545108,EU786 |
| | | | | | | 671,AB254147,FJ496 |
| | | | | | | 193,AY322190,AY87 |
| | | | | | | 8067,FJ185233,FJ49 |
| | | | | | | 6147,FJ460499,DQ35 |
| | | | | | | 8801,AJ866554,AF11 |
| | | | | | | 0959,FN392874,U211 |
| | | | | | | 35,AB253429,AB565 |
| | | | | | | 498,EU000511,KC89 |
| | | | | | | 8985,GQ999974,AB0 |
| | | | | | | 97867,AY835778,FJ1 |
| | | | | | | 85255,FJ495823,AF4 |
| | | | | | | 60972,AB253653,U43 |
| | | | | | | 141,FJ185249,JF804 |
| | | | | | | 808,AF192135,AF110 |
| | | | | | | 971,FJ496213,AB253 |
| | | | | | | 657,M38429,AB4800 |
| | | | | | | 48,AB485637,DQ056 |
| | | | | | | 407,FJ211782,AB485 |
| | | | | | | 635,GU237072,DQ85 |
| | | | | | | 3450,KC898979,M22 |
| | | | | | | 639,DQ295194,FJ495 |
| | | | | | | 938,AB253674,DQ44 |
| | | | | | | 5632,EU000510,DQO |
| | | | | | | 56410,AY585264,DQ |
| | | | | | | 854715,FJ496166,AB |
| | | | | | | 480695,DQ886032,A |
| | | | | | | Y314057,DQ676882, |
| | | | | | | AY900571,FJ496202, |
| | | | | | | AY008717,AB547464 |
| | | | | | | ,AY037282,FJ185244 |
| | | | | | | ,DQ164120,AJ24548 |
| | | | | | | 1,KC898991,AY1698 |
| | | | | | | 14,U46016,AF184155 |
| | | | | | | ,KF766537,GU59514 |
| | | | | | | 9,AY838567,HM4699 |
| | | | | | | 74,AY331296,DQ369 |
| | | | | | | 979,GQ175881,GQ99 |
| | | | | | | 9981,EU110094,FJ49 |
| | | | | | | 6199,U88826,AY4632 |
| | | | | | | 27,AY500393,FJ4959 |
| | | | | | | 42,DQ164117,FJ6471 |
| | | | | | | 45,AB253721,DQ445 |
| | | | | | | 634,AY772691,KC89 |
| | | | | | | 8977,AF110960,AJ25 |
| | | | | | | 1057,DQ351234,AY9 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 00574,EU000516,EU 293444,AB253719,A Y771590,AY773339, AF286365,DQ358812 ,FF029067,DQ85471 4,FJ495824,DQ35880 9,FJ496212,AB25369 2,DQ351232,AB2536 62,FJ496003,EU6166 39L31963,AY169807 ,AF067154,U51188,A Y585265,AF443083,A F286236,FJ185259,G 0999980,DQ853457, FJ670515,DQ396396, AB253684,AY322193 ,AY586543,AY83576 5,U71182,KC898982, DQ369998,DQ36998 3,DQ358800,JX5030 82,FJ623484,AY9019 74,AJ866553,AB2870 04,AJ508597,AB4800 47,FJ496073,AB4856 53,DQ369996,AF484 480,AY838565,AP00 5207,AB253697,DQO 11178,AY463217,AB 253659,HM026455,A Y772700,AJ288981,A F450097,KC156115, DQ369978,AB428557 ,AY331297,JQ316127 ,DQ396371,FJ623492 ,A07116,EU293445,K C156220,AF082394, AF443103,AB253685, EU293448,DQ676874 ,AB253638,AY87805 9,AY049711,AB6049 47,FJ496206,HM026 457,FJ670523,FJ6670 522,AB547463,AF443 105,AB070353,AY31 4052,FJ496075,AY77 2696,KC898996,DQ8 53456,AB641836,AY 237167,FJ496148,KC |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 898992,AY623602,AB221125,AB253708, AY682547,AF423760, EF178405,AY835771, AF484485,AB428560, AF286223,FJ195089, AF516184,EF637055, AY779550,AB485660, AF538303,FJ185232, DQ164118,AB485664, AB070352,KC503853, DQ093607,AF042104, DQ314732,DQ056414, FJ185235,DQ823367, EU786674,AB731669, FJ195087,FJ185260, GQ372986,AB287372, AB480697,D0445633, AB273779,AY445524, FJ185234,AY169810, DQ396370,FJ185230, DQ011180,AF110969, FJ213780,AB253673, AY835756,AF443082, DQ093601,AB485659, GQ845125,AF443108, AY314055,AF538302, EF178323,AB286850, AY835779,DQ351237, DQ366662,DQ093589, FJ496006,AB480045, AB253694,AB253431, D0351219,EF514713, KC156127,GQ999990, AF179368,GQ845126, DQ093590,EU735540, DQ207942,AY423381, DQ853439,AB098333, M17451,FJ495820, DQ853460,AB253639, JQ316126,AY463222, FJ496198,AF450096, EU000509,AY463224, FJ496081,AY878068, KC156118,EU000512, EF514711,AF44307, AF286237,AB |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 253672,U51189,DQ366665,AY536233,EF637056,FJ496164,DQ853448,EF637048,FJ496178,FJ670518,AY835757,DQ366659,AB485633,AY167123,FJ496171,AF110970,EF514704,AB286859,D0396391,DQ351236,AF408628,EF637050,AY322189,AY169813,EU884501,M62320,AY173955,AB485655,AB220947,KF766538,AY423383,AF004885,AY046058,AJ320484,AF443115,AY227107,EU786670,DQ396393,AB253656,L20571,AF193253,JQ316132,AY352657,JQ429433,AJQ06022,DQ853436,FJ771006,EF363127,AY901966,DQ093592,FJ496195,AB746343,AF110978,DQ164104,AY314056,AB428554,EF637054,AB253688,AB254153,XQ4415,AY835774,AB253720,GU595154,AB287368,AJ404325,AB428553,EU000514,FJ496152,AY751407,FJ670530,DQ085876,DQ676877,FJ71171703,AY049709,JQ316134,AF408627,FJ496197,U37270,AB253677,AY322191,FJ670524,FJ496185,DQ912823,AY463221,AF460974,AY772699,AB646691,DQ396378,AB253647,AB253682,EF514710,AB485662,DQ396385,DQ845388,Z11530,AB220 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 946,AB253703,FJ195090,AY878057,AF193275,AY772695,AY835754,EF192592,EF514712,GU595158,AB253652,AF110963,KC156119,EF368372,FJ623495,EU616649,AF443084,AB253699,AF385935,KC898986,AB286854,AB254156,FJ623480,DQ396388,AB254155,AB485645,DQ358811,AY901965,AB480694,AY173957,DQ351238,AF286238,DQ351223,AB253716,AY455784,EU448295,AB287371,AF443112,AB480698,FJ213781,AY162225,AY352654,AB485663,FJ771007,AB253423,AB253671,AB253635,AY532635,AY835769,AB485651,AY878065,AB254149,DQ351230,AB253687,AY536237,EF637053,JN860767,EF091932,AB604951,DQ358805,AY901975,AJ271445,U34603,K03454,U26546,AB746342,FJ496160,JX503073,KC899009,AF086817,AF286235,FJ495819,AF443086,K03455,AY835767,EU786672,AB220944,FJ623476,GQ999985,EF514708,AB286849,AY586640,DQ056404,DQ396398,AY455781,M17449,AB485641,AB485634,KC156121,AY314049,AF443111,KC522033,AB286860,KC156120,DQ09 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 3597,DQ164122,AY5 35659,AY331289,AY 560109,DQ230841,K C935957,DQ445637, AF443089,EF192591, AB731667,EU110088 DQ093596,EU78667 8,AB604949,HM4699 83,EU616642,DQ093 600,AY585268,EU61 6641,AY463223,AB2 54143,DQ853454,AY 838568,FJ623488,DQ 853447,AY322187,D 0011175,AY818643, AF164485,HM215250 ,DQ056411,AY33128 2,AB731666,AB2536 37,AF224507,DQ011 165,AF443088,KC89 8975,AB253670,AB2 86862,AB286861,AF4 43079,FN392876,DQ 886031,KC852172,A Y703910,DQ093606, FJ771008,DQ853458, AF443075,DQ487191 ,AB287364,AF490973 ,AY779559,HM02645 6,HM469981,GQ9999 78,AY169808,AY423 385,AY901979,AY35 2656,HM776939,AY8 78060,AY772693,AB 485642,AY901967,A B731670,AY878054, DQ445636,KC898983 ,AF423755,AB428556 ,AB480692,AY53111 6,AY781126,AF44308 7,GQ372989,AB2211 26,AF110976,AY3140 61,AY049710,AB097 ,869,DQ396394,AY31 4054,GU595153,FJ49 5937,FJ496174,AB28 6853,JQ316128,AB56 5501,AB253709,AB0 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 97866,AY835759,GQ999991,DQ295192,D0093602,AF377958,AB485654,AF443114,AJ866558,AY162224,DQ085867,AB480044,AB485647,DQ164129,AF321523,AY162223,AB746344,GQ175883,AY455780,FJ185258,AB289589,M27323,HM026458,AF484511,AF286227,AB253689,HM776938,AF290029,DQ383750,FJ496170,KC156130,U86780,AY314063,AB254142,FJ185246,AF110980,FJ496157,U88823,JF804810,AB253648,M15654,DQ853443,FN392877,EF036527,AB253643,FJ460500,GQ999979,GQ999986,FJ185240,KC852174,AF361873,AB253669,AF411964,AB428558,M38431,AB485648,AB253723,DQ234790,DQ164113,FJ185236,AB485632,AB097871,AY173951,KC503852,AF005495,EF036531,DQ396399,FJ496207,EF420986,AY314062,EF175209,JQ316131,AF443085,FJ853620,EF036532,AF443090,DQ396372,AM000055,AB052867,AB480300,AB253651,DQ164114,AY835762,AB289588,AB253717,AJ276596,AF256205,EU697909,AB253658,AY818641,EU031915,AF256206,DQ164109,EU000513,AB4856 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 66,DQ859180,AB254141,GQ372987,AF408629,AY588970,DQ164127,AY158534,FJ495943,DQ837381,DQ358803,FJ623481,EU293446,AB231897,AF110977,DQ011179,AB20948,FJ496001,FJ18229,AF407418,AF413987,AY835780,EU786681,AF385934,KC156221,AY838566,AB428551,AY878066,FJ185253,AB485667,DQ396389,GU111555,AY314059,DQ093593,AY901977,AF457058,AY237165,DQ093587,AJ508596,FJ185250,AF256207,AJ866557,FJ670527,AF049495,DQ011166,K02083,FJ496188,AY703908,AY835749,KC899014,KC156217,DQ369993,AF110964,AY751406,FJ496000,KC899012,DQ369995,DQ354118,DQ853452,DQ396387,FJ496149,AY008718,EU786677,DQ396377,AY331283,AB023804,AF110981,EF514707,DQ351233,KC156216,AY586547,U34604,AB287369,U23487,AY779557,FJ496175,AB253428,EF078278,AB049811,FJ623475,DQ676878,FJ670517,DQ886037,AB253691,L39106,AB253680,EU000515,AB485661,DQ978981,EU547186,DQ164106,DQ853449,DQ676880,AF443080,EF4209 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 87,AY463230,AB253636,KC898987,AF077336,AB604950,EF637046,AF082395,AY901978,AF003887,KC156123,AY586549,AY878063,AY463228,EF029069,AB097865,AY901969,JX503072,AF286229,AY331292,DQ351228,GQ999998 2,DQ164111,DQ085870,KC899013,DQ011173,AJ271370,AY901968,FJ853621,KC156125,FJ496159,AY173954,AY835777,DQ853440,AF443110,AB253665,AY169803,AY835750,FJ496187,DQ351218,DQ011171,HM469982,KC156124,EF637051,EU110095, EF368370,AF110962,GU595151,EU786676,AY173953,AY835772,AF042101,DQ445631,AB254144,EU616645,DQ093594,AY878070,GU595150,AF042106,JN571034,FJ496184,AY082968,GU595155,HM215252,GQ099976,AY314045, ,AF290030,AY423386,AB289590,AF423758,JN188292,AY463219,DQ351224,AB485638,AJ508595,AY118166 ,AF289549,JN860769,AB564746,EF363126,DQ396373,KC156116,AF067156,KF766541,FJ185243,AF061640,AF067158,AB254152,JX574661,HM469975,AY331288,EF036529,AB286851,EF51465 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 98,AB253425,KC492738,AF443104,KF766542,AB286864,FJ623490,DQ853453,EU000508,DQ011172,KC156211,DQ369990,FJ185237,AY169816,DQ396392,AY779556,AB480299,AY805330,HM469980,AY901973,KC156212,AF286231,AY779553,AF411965,DQ351216,EU2934 47,DQ007902,DQ007901,AY779564,FJ185257,AB253424,U69590,AB428559,DQ164115,AB485650,EF078279,AB485643,AY779561,AF049494,AF407419,DQ295196,AF075703,AY772694,AY074891,AB253663,AF076475,U12055,GQ999988,EU110089,DQ396365,AJ237565,EFS14700,AJ239083,AF286226,AY560110,GQ372990,AF286232,L02317,AB253426,DQ351227,FJ496196,DQ979024,AB731664,AY463226,EF036533,D0853464,DQ011169,AF414006,AB485664,FJ670526,AB253713,AY352275,FJ185248,EF363122,AB254148,FJ496158,DQ396366,JN860768,AY901972,FJ496208,M93259,D0369991,GU595157,AB253642,AY158533,EF029066,AB253655,DQ487189,AY772698,EF514702,AY53623 4,KF766540,HM215249,DQ369981,FJ1950 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 86,AY771592,FJ496072,DQ369986,FJ496153,AF286233,EU693240,FJ496007,FJ496079,JN860766,FJ771009,FJ496080,JX503081,D86069,AF110973,FJ185252,U52953,FJ623489,AY169805,DQ369994,AF443109,AF468970,JN860762,U54771,DQ351229,AF063224,AY093603,DQ369982,FJ623486,AB097870,FJ496192,EU616640,AY093604,DQ093599,AB641837,AB032740,DQ369984,FJ213783,EU220698,GQ365649,AF443081,AY118165,FJ185241,GU207884,KC898994,AB253702,AB731668,FJ495939,AY173958,FJ496169,AY585267,FJ496083,AB485669,DQ056408,FJ358521,FJ185231,AB287378,KC522032,AY455783,KF766539,D03588806,DQ369976,EF368371,AB254150,AF286225,AF061641,DQ093586,AB253427,DQ487188,AB253704,AB097872,AF110968,HM469977,GQ175882,DQ369988,FJ496201,AY900576,EU735538,DQ017382,AY331284,AB253667,AY463218,AY463237,FJ496005,EF036534,AY878058,EF036536,AB565496,AY835748,AB253432,AB564745,AF443096,HM469973,AY970946,EU110090, |

| Taxonomy | Rep.Acc.ID | Host | # GN's | Lineage | Seg. Count | GN.Acc.IDs |
|---|---|---|---|---|---|---|
| | | | | | | DQ853444,AF197339,KC522031,FJ496190,AB646289,EF514701,AB287376,AY97094 7,FJ496176,DQ01117 0,DQ085873,DD4099 79,AY331286,EF0365 35,DQ859178,GQ999 989,AY618998,AY97 0949,AB221005,AB0 98330,U69591,DQ01 7383,U69584,AY6126 37,JF804807,DQ8534 37,U26942,FJ495818 ,FJ496177,KC899006 ,EU786679,AY00871 5,AB286852,AY5362 36,AY560107,AB485 668,HM469978,AY17 3956,AB253668,DQO 93598,DQ164108,DQ 39638l,JX503071,FJ 496146,DQ093595,L2 0587,AF193277,AF07 5719,DQ011167,JF80 4813,AY586541,FJ49 6204,AY158535,JF80 4812,AB097873,EU0 31914,AY901970,AY 878056,AB254146,AF 408626,FJ185242,DQ 366666,JQ316138,D 0164124,AB480696,J X503078,AB253422, AY703909,AJ866556, DQ396390,AB253641 ,AY314050,FJ496150 ,DQ358804,AB28958 7,KC156219,GQ9999 77,JX503083,FJ6234 83,GQ290462,EU293 449,U69587,JN86076 3,DQ056416,AB2536 61,AY314058,AB287 365,DQ164125,AY77 9554,GQ845124,AB4 85652,DQ093605,AY 835781,AF259955,K |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | C852173,GU733717, U88825,AB052995,AY169802,AY772690,FJ496168,KC156214,FJ496155,U69588,AB286855,KC935959,DQ400856,JN860765,KC156114,FR846409,AY169806,AF286239,GQ999987,AB231894,DQ853462,GQ277610,AJQ06287,DQ056413,AY463232,AF443078,AF332867,DQ676886,AY169809,AF064699,DQ366661,AB565497,FJ496154,AMOO0053,AF529572,KC899008,AB565499,EU110096,AB220945,FJ496004,AY835775,FR846408,DQ164107,AY773341,AB253664,DQ676875,FJ185256,HM215251,DQ853461,AY423382,AB253715,U88822,EF637052,DQ354116,GQ365651,DQ056412,AF042105,DQ366663,AY878062,EF175211,EF175212,FJ495825,DQ085871,AY228557,FJ496161,AF443098,JQ316133,AY308761,DQ396383,JX574662,EU884500,AY314060,AY271690,EU616644,GQ999972,M26727,AB253683,EU743963,GU647198,FJ496084,AB485665,FJ495821,JF719818,GU595148,D0676870,EU697907,JN860761,GU230139,AB604948,AY835766,AF070521,FJ496210,FJ496078,EF17521 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0,AB253650,AF44310 2,AY169812,DQ3699 85,DQ358807,FJ4961 79,AY535660,AY835 753,AY314044,JF804 814,AB480693,AF443 093,AJ288982,AF385 936,EF514705,AY818 642,AF443100,AY463 225,U69592,EF63704 7,AJ302646,GU2301 37,U69593,DQ09360 4,AB564744,AF41196 6,AB286955,DQ0564 09,AY779555,AY835 760,EU110093,AB25 3701,JQ316129,DQ6 76879,KC898990,AB 253654,JF719819,AF 443094,EF514697,AY 779563,DQ369980,A B286858,AB253696, EF514703,DQ979023 ,EF633445,AF529573 ,AF076998,AF530576 ,AF286230,AY308760 ,FJ670520,AY779552 ,DQ676872,FJ623478 ,AF005496,AB428562 ,AY322185,AB25343 0,AY835764,AF06322 3,DQ085869,AY4557 78,DQ351220,AY008 716,AY314051,AY33 1285,DQ886038,DQ3 69987,KC492737,AY 87807l,HM469979,A ,Y322184,DQ366664, KC898989,AF503396 ,FJ496162,AB253695 ,FR846410,DQ39637 4,FJ496203,AB56547 8,DQ056417,AY9019 81,EF029068,AB2536 75,DQ354123,KC914 396,FJ185247,AY781 125,DQ164123,DQ39 6397,EU110091,AF1 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 10967,AJ291720,FJ623487,AB254151,AF443113,AB253724,FJ496173,FJ670529,AY878072,AB253711,AB604946,KC156128,AB428561,DQ369992,DQ056405,A04321,AF133821,DQ164126,FJ496002,DQ845386,DQ676873,DQ845387,AB078005,FJ496180,AF286234,EF637049,A34828,DQ083238,AF003888,AF110979,AF443101,JQ316135,FJ670528,DQ093603,AB485658,AB253722,AJ302647,DQ056406,HM100716,AF286224,KC156117,AY331290,DQ676884,AY882421,AY169804,DQ853442,EF363123,AB253700,DQ396375,M93258,EF057102,AY331287,DQ396367,AF286228,EF036530,FJ496145,AB485649,AF033819,EF178358,KC156210,DQ164119,AF197340,AB480046,EU541617,KC503854,DQ085874,AF408632,KC898981,GU595159,EU448296,AY173952,AY169811,M199921,JQ316137,AB253678,KC156122,AB253698,EU000506,FJ496172,AY463231,DQ011174,GQ999984,A07108,AY878061,AY180905,AB253660,U43096,EF514709,AB253710,DQ396368,EU086177,DQ853463,DQ853446,AY314048,JF804 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 805,DQ676883,DQ369989,GU733716,AY423387,FJ496165,DQ358810,AB480298,AF423757,AB565495,AY585266,AY228556,AB287366,DQ366660,AB253725,AB032741,GQ365650,AY835755,DQ676885,JF804811,DQ011168,KC898995,AB485646,AY237166,EF469243,AB253666,FJ496167,AY463220,AY169815,AF316544,AB253718,AF290027,AB231893,DQ396376,JX503077,FJ496182,FJ495940,FJ496211,DQ011176,HM469976,DQ676876,FN392875,AF492624,HM067748,AB565479,DQ859179,DQ853459,DQ383746,DQ351225,AB485640,AF111095,JF804809,EF514706,FJ496209,AF084936,AF443095,U88824,DQ164128,FJ496077,AY049708,AY779562,AJ291719,AF423759,DQ676881,AF443091,KC899010,DQ396395,AB485636,AF076474,DQ979025,DQ351226,AF042100,AB254145,AY588971,AY314047,AY970948,KC935958,AY463234,AY536238,AB253646,DQ056415,FJ185251,DQ886035,DQ093588,FJ496205,AF110972,EU735537,AB253645,AY835776,A141161,AB428552,AY703911,EF036528,AF492622 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human immunodeficiency virus 2 | NC_001722 | vertebrates,human | 41 | Retroviridae,Lentivirus,Human immunodeficiency virus 2 | — | 3,AY781128,FJ49618 6,GU595152 AY509260,M15390,M 30895,AB499695,AF2 08027,EU028345,AB 48567I,JQ4542,U220 47,AB731745,AB731 744,AB485670,AB49 9693,AB731742,AB7 31743,L36874,U3829 3,JQ4498,EU980602, AY509259,AB731741 ,AB731739,L07625,X 52223,AY530889,U27 200,Z48731,M31113, DQ0835,JQ3654,DQ3 07022,XQ5291,AB731 738,AB499694,A0999 5,X61240,AB731740, AF082339,AB100245, E02138,M30502 |
| Human metapneumovirus | NC_004148 | vertebrates,human | 69 | Paramyxoviridae,Metapneumovirus,Human metapneumovirus | — | HM197719,KC40397 2,DQ843659,KF5301 85,KC403975,KC562 219,KC562222,KC40 3980,KC562228,FJ16 8778,KC562232,KF5 30163,AF371337,KC 562221,EF535506,K C40398?,JN184400,K C40398?,KF530165, KC562223,KC562224 ,KC562240,JN184399 ,KC562230,KF53017 8,KF530183,KC4039 79,KF530177,GQ153 651,KC562229,KC56 2241,KC562231,KC5 62234,KC403981,KF 530171,KC403978,K C562233,KF530179, KC403976,KC562238 ,AY297748,KC40397 3,KC562242,KC4039 74,KC562226,KC562 235,KC562244,JN184 401,KF530166,KC56 2239,KC403977,KF5 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human papillomavirus | NC_016157 | vertebrates,human | 1 | Papillomaviridae,Human papillomavirus 126-like viruses | — | 30167,C0840316,KC562220,KF530173,KF53018l,KF530164,JN184402,KC403971,AY525843,KC562243,KC562225,KC562227,AB503857,AY297749,KC403983,FJ168779,DQ84365,KC562237 |
| Human papillomavirus | NC_019023 | vertebrates,human | 2 | Papillomaviridae,Human papillomavirus 161-like viruses | — | JX413108,JX413109 |
| Human papillomavirus FA75/KI88-03 | NC_022095 | vertebrates,human | 2 | Papillomaviridae,Human papillomavirus | — | JX444073,HG421739 |
| Human papillomavirus RTRX7 | NC_001596 | vertebrates,human | 1 | Papillomaviridae,Betapapillomavirus,Betapapillomavirus 2 | — | EU410347 |
| Human papillomavirus SIBX-3a | NC_001531 | vertebrates,human | 1 | Papillomaviridae,Betapapillomavirus,Betapapillomavirus 1 | — | U85660 |
| Human papillomavirus SIBX1 | NC_001596 | vertebrates,human | 1 | Papillomaviridae,Betapapillomavirus,Betapapillomavirus 2 | — | FN598907 |
| Human papillomavirus SIBX2 | NC_005134 | vertebrates,human | 1 | Papillomaviridae,Betapapillomavirus,Betapapillomavirus 5 | — | FN677755 |
| Human papillomavirus SIBX8 | NC_001596 | vertebrates,human | 1 | Papillomaviridae,Betapapillomavirus,Betapapillomavirus 2 | — | FN677756 |
| Human papillomavirus type 100 | NC_001596 | vertebrates,human | 1 | Papillomaviridae,Betapapillomavirus,Betapapillomavirus 2 | — | HE963025 |
| Human papillomavirus type 104 | NC_001596 | vertebrates,human | 1 | Papillomaviridae,Betapapillomavirus,Betapapillomavirus 2 | — | FM955839 |
| Human papillomavirus type 105 | NC_001531 | vertebrates,human | 1 | Papillomaviridae,Betapapillomavirus,Betapapillomavirus 1 | — | FM955840 |
| Human papillomavirus type 107 | NC_001596 | vertebrates,human | 1 | Papillomaviridae,Betapapillomavirus,Betapapillomavirus 2 | — | FM955841 |
| Human papillomavirus type 110 | NC_001596 | vertebrates,human | 1 | Papillomaviridae,Betapapillomavirus,Betapapillomavirus 2 | — | EF422221 |
| Human papillomavirus type 111 | NC_001596 | vertebrates,human | 1 | Papillomaviridae,Betapapillomavirus,Betapapillomavirus 2 | — | EU410348 |
| Human papillomavirus type 113 | NC_001596 | vertebrates,human | 1 | Papillomaviridae,Betapapillomavirus,Betapapillomavirus 2 | — | EU410349 |
| Human papillomavirus type 115 | NC_001591 | vertebrates,human | 1 | Papillomaviridae,Betapapillomavirus,Betapapillomavirus 3 | — | FM955842 |
| Human papillomavirus type 118 | NC_001531 | vertebrates,human | 1 | Papillomaviridae,Betapapillomavirus,Betapapillomavirus 1 | — | FJ947080 |
| Human papillomavirus type 12 | NC_001531 | vertebrates,human | 1 | Papillomaviridae,Betapapillomavirus,Betapapillomavirus 1 | — | GQ246951 |
| | | | | | | X74466 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Human papillomavirus type 120 | NC_001596 | vertebrates,human | Papillomaviridae,Betapapillomavirus,Betapapillomavirus 2 | 3 | — | GQ845442,JQ963484,JQ963485 |
| Human papillomavirus type 122 | NC_001596 | vertebrates,human | Papillomaviridae,Betapapillomavirus,Betapapillomavirus 2 | 1 | — | GQ845444 |
| Human papillomavirus type 124 | NC_001531 | vertebrates,human | Papillomaviridae,Betapapillomavirus,Betapapillomavirus 1 | 1 | — | GQ845446 |
| Human papillomavirus type 126 | NC_016157 | vertebrates,human | Papillomaviridae,Human papillomavirus 126-like viruses | 1 | — | AB646346 |
| Human papillomavirus type 135 | NC_017993 | vertebrates,human | Papillomaviridae,Human papillomavirus type 135 | 1 | — | HM999987 |
| Human papillomavirus type 136 | NC_017994 | vertebrates,human | Papillomaviridae,Human papillomavirus type 136 | 1 | — | HM999988 |
| Human papillomavirus type 137 | NC_017995 | vertebrates,human | Papillomaviridae,Human papillomavirus type 137 | 1 | — | HM999989 |
| Human papillomavirus type 140 | NC_017996 | vertebrates,human | Papillomaviridae,Human papillomavirus type 140 | 1 | — | HM999992 |
| Human papillomavirus type 144 | NC_017997 | vertebrates,human | Papillomaviridae,Human papillomavirus type 144 | 1 | — | HM999996 |
| Human papillomavirus type 14D | NC_001531 | vertebrates,human | Papillomaviridae,Betapapillomavirus,Betapapillomavirus 1 | 1 | — | X74467 |
| Human papillomavirus type 15 | NC_001596 | vertebrates,human | Papillomaviridae,Betapapillomavirus,Betapapillomavirus 2 | 1 | — | X74468 |
| Human papillomavirus type 154 | NC_021483 | vertebrates,human | Papillomaviridae,Human papillomavirus type 154 | 1 | — | JN211193 |
| Human papillomavirus type 166 | NC_019023 | vertebrates,human | Papillomaviridae,Human papillomavirus 161-like viruses | 1 | — | JX413104 |
| Human papillomavirus type 17 | NC_001596 | vertebrates,human | Papillomaviridae,Betapapillomavirus,Betapapillomavirus 2 | 2 | — | X74469,JN211195 |
| Human papillomavirus type 19 | NC_001531 | vertebrates,human | Papillomaviridae,Betapapillomavirus,Betapapillomavirus 1 | 1 | — | X74470 |
| Human papillomavirus type 20 | NC_001531 | vertebrates,human | Papillomaviridae,Betapapillomavirus,Betapapillomavirus 1 | 1 | — | U31778 |
| Human papillomavirus type 21 | NC_001531 | vertebrates,human | Papillomaviridae,Betapapillomavirus,Betapapillomavirus 1 | 1 | — | U31779 |
| Human papillomavirus type 22 | NC_001596 | vertebrates,human | Papillomaviridae,Betapapillomavirus,Betapapillomavirus 2 | 1 | — | U31780 |
| Human papillomavirus type 23 | NC_001596 | vertebrates,human | Papillomaviridae,Betapapillomavirus,Betapapillomavirus 2 | 1 | — | U31781 |
| Human papillomavirus type 24 | NC_001531 | vertebrates,human | Papillomaviridae,Betapapillomavirus,Betapapillomavirus 1 | 1 | — | U31782 |
| Human papillomavirus type 25 | NC_001531 | vertebrates,human | Papillomaviridae,Betapapillomavirus,Betapapillomavirus 1 | 1 | — | X74471 |
| Human papillomavirus type 36 | NC_001531 | vertebrates,human | Papillomaviridae,Betapapillomavirus,Betapapillomavirus 1 | 1 | — | U31785 |
| Human papillomavirus type 37 | NC_001596 | vertebrates,human | Papillomaviridae,Betapapillomavirus,Betapapillomavirus 2 | 1 | — | U31786 |
| Human papillomavirus type 38 | NC_001596 | vertebrates,human | Papillomaviridae,Betapapillomavirus,Betapapillomavirus 2 | 2 | — | JN211196,U31787 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Human papillomavirus type 38b | NC_001596 | vertebrates,human | Papillomaviridae,Betapapillomavirus,Betapapillomavirus 2 | 1 | — | DQ090005 |
| Human papillomavirus type 47 | NC_001531 | vertebrates,human | Papillomaviridae,Betapapillomavirus,Betapapillomavirus 1 | 1 | — | M32305 |
| Human papillomavirus type 49 | NC_001591 | vertebrates,human | Papillomaviridae,Betapapillomavirus,Betapapillomavirus 3 | 1 | — | X74480 |
| Human papillomavirus type 5 | NC_001531 | vertebrates,human | Papillomaviridae,Betapapillomavirus,Betapapillomavirus 1 | 3 | — | M17463,M22961,JN211194 |
| Human papillomavirus type 5b | NC_001531 | vertebrates,human | Papillomaviridae,Betapapillomavirus,Betapapillomavirus 1 | 1 | — | D90252 |
| Human papillomavirus type 75 | NC_001591 | vertebrates,human | Papillomaviridae,Betapapillomavirus,Betapapillomavirus 3 | 1 | — | Y15173 |
| Human papillomavirus type 76 | NC_001591 | vertebrates,human | Papillomaviridae,Betapapillomavirus,Betapapillomavirus 3 | 1 | — | Y15174 |
| Human papillomavirus type 8 | NC_001531 | vertebrates,human | Papillomaviridae,Betapapillomavirus,Betapapillomavirus 1 | 1 | — | M12737 |
| Human papillomavirus type 80 | NC_001596 | vertebrates,human | Papillomaviridae,Betapapillomavirus,Betapapillomavirus 2 | 1 | — | Y15176 |
| Human papillomavirus type 9 | NC_001596 | vertebrates,human | Papillomaviridae,Betapapillomavirus,Betapapillomavirus 2 | 1 | — | X74464 |
| Human papillomavirus type 92 | NC_004500 | vertebrates,human | Papillomaviridae,Betapapillomavirus,Betapapillomavirus 4 | 1 | — | AF531420 |
| Human papillomavirus type 93 | NC_001531 | vertebrates,human | Papillomaviridae,Betapapillomavirus,Betapapillomavirus 1 | 1 | — | AY382778 |
| Human papillomavirus type 96 | NC_005134 | vertebrates,human | Papillomaviridae,Betapapillomavirus,Betapapillomavirus 5 | 1 | — | AY382779 |
| Human papillomavirus type 98 | NC_001531 | vertebrates,human | Papillomaviridae,Betapapillomavirus,Betapapillomavirus 1 | 1 | — | FM955837 |
| Human papillomavirus type 99 | NC_001531 | vertebrates,human | Papillomaviridae,Betapapillomavirus,Betapapillomavirus 1 | 1 | — | FM955838 |
| Human parainfluenza virus 1 | NC_003461 | vertebrates,human | Paramyxoviridae,Respirovirus,Human parainfluenza virus 1 | 21 | — | KF687315,KF687307, KF687312,KF687217, KF687314,KF530205, KF530215,KF687316, KF530212,KF530220, KF687308,KF530202, KF530221,KF687310, KF530203,KF687311, KF530209,AF457102, KF530198,KF687313, KF687309 |
| Human parainfluenza virus 2 | NC_003443 | vertebrates,human | Paramyxoviridae,Rubulavirus,Human parainfluenza virus 2 | 5 | — | X57559,AF533012,AB176531,AF533010,AF533011 |
| Human parainfluenza virus 3 | NC_001796 | vertebrates,human | Paramyxoviridae,Respirovirus,Human parainfluenza virus 3 | 47 | — | KF530242,KF530231, KF530230,KF530228, KF530229,KF530241, KF687355,KF687319, |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| | | | | | | KF687342,KF530234, KF530251,KF530233, KF687338,KF530232, KF687317,AB012132, KF687321,KF530257, KF687356,KF687331, KF687350,KF687318, KF530245,KF530225, KF530253,KF530237, KF687341,U51116,E U424062,KF687329, KF530249,KF530252, KF530256,KF687335, KF687336,KF687340, KF530236,EU326526 ,KF687337,KF530243 ,Z11575,KF530247,K F530239,FJ455842,K F687346,KF530250,K F530226 |
| Human parainfluenza virus 4a | NC_021928 | vertebrates,human | Paramyxoviridae,Rubulavirus,Human parainfluenza virus 4 | 2 | — | KF483663,AB543336 |
| Human parainfluenza virus 4b | NC_021928 | vertebrates,human | Paramyxoviridae,Rubulavirus,Human parainfluenza virus 4 | 3 | — | EU627591,JQ241176 ,AB543337 |
| Human parvovirus B19 | NC_000883 | vertebrates,human | Parvoviridae,Erythrovirus,Human parvovirus B19 | 8 | — | AY504945,FJ591158, AY386330,AY083234 ,AF162273,FN598218 ,FN598217,AB55033 1 |
| Human picobirnavirus | NC_007026 | vertebrates,human | Picobirnaviridae,Picobirnavirus,Human picobirnavirus | 1 | seg. 1 | AB186897 |
| Human picobirnavirus | NC_007027 | vertebrates,human | Picobirnaviridae,Picobirnavirus,Human picobirnavirus | 1 | seg. 2 | AB186898 |
| Human poliovirus 1 | NC_002058 | vertebrates,human | Picornaviridae,Enterovirus,Enterovirus C | 126 | — | AF111984,KC880377 ,AB180072,AF405667 ,KC880375,AF40568 7,EF682358,AB18007 0,AF405679,AF46241 9,AJ132960,GQ9841 41,KF537633,AY9283 85,AY928387,AF4056 88,KC880382,KC880 370,EF682359,EF682 356,AF405683,FJ769 379,EF682357,AY278 553,FJ859063,AF111 961,FJ859059,EU794 955,AF111982,EF682 |

| Taxonomy | Rep.Acc.ID | Host | # GN's | Lineage | Seg. Count | GN.Acc.IDs |
|---|---|---|---|---|---|---|
| | | | | | | 345,AJ430385,AF405666,KC880366,AF405673,AF538840,FJ859058,KC880368,AF405677,EU794961,EF682355,FJ769380,EU794960,FJ859062,KC880379,AF405674,V01148,AF111966,FJ769381,EF682346,AF405680,AF405669,KC880367,FJ769385,EU794962,AF405676,FJ769383,AF405668,AF416342,EU794954,AF405689,EU794953,KC880378,AF405671,AY560657,AF458333,AF405682,AF405684,FJ859061,FJ769378,FJ769384,EU794964,EF682343,AF405664,KC880369,AF405678,FJ859064,AJ416942,EU794956,EF682348,AF538841,AB180071,EU794958,KC880716,AB180073,KC880373,EF682344,AF405665,EF682354,AF405675,EF682351,AF111983,FJ859060,KC880371,AF111953,AF538843,EU794959,EU794957,KC880380,AY928386,AF538842,EF682349,KC880381,AF405685,EF682353,EF682347,EF456706,KC880372,AF405662,EF682350,AF462418,AF405672,AY184219,AF405670,AF405686,KC880365,EF682352,EU794963,KC880374,AF405663,FJ769382,AY928383,AJ132961,AY928384,AF405690 |

TABLE 10-continued

VipoCap-1.0 Taxonomy

| Taxonomy | Rep.Acc.ID | Host | # GN's | Lineage | Seg. Count | GN.Acc.IDs |
|---|---|---|---|---|---|---|
| Human poliovirus 1 strain Sabin | NC_002058 | vertebrates,human | 1 | Picornaviridae,Enterovirus,Enterovirus C | — | AF405681,AF111981,V01150 |
| Human poliovirus 2 | NC_002058 | vertebrates,human | 66 | Picornaviridae,Enterovirus,Enterovirus C | — | JX274984,AY278549,JX275380,AM884185,HM107833,JX275085,JX275238,JX275140,JX275147,HM107835,JX275266,AY278552,FJ898290,AM084224,AM040037,AM884184,DQ890388,JX275184,HM107832,HM107834,JX274993,DQ890387,FJ460224,AY184220,DQ205099,M12197,JX274983,AY278550,KC784368,DQ890385,AM084225,FJ460225,AY238473,AM040039,DQ0625,KC784367,DQ890386,AY278551,JX274985,FJ517649,AM040038,XQ0595,JX275015,AM084223,JX274980,AY948201,AM040035,FJ460223,JX274999,JX274991,JX274982,AJ544513,JX275008,JX274995,AY177685,JX275352,AM040036,JX274981,AF448782,JF517648,JX275032,JX275071,JX275162,JX274987,AF448783,GU390707 |
| Human poliovirus 3 | NC_002058 | vertebrates,human | 18 | Picornaviridae,Enterovirus,Enterovirus C | — | FJ914252,EF456707,FJ842159,K01392,KC784372,FJ460226,XQ0925,FJ842158,AY184221,GU180608,GU256222,XQ4468,AJ293918,AF541919,XQ0596,EU684056,EU684057,FJ460227 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Human respiratory syncytial virus | NC_001781 | vertebrates,human | Paramyxoviridae,Pneumovirus,Human respiratory syncytial virus | 122 | — | JXQ15498,JQ901450, GU591771,GU59176 8,JX576739,JX57674 5,JQ901456,JF92006 1,JQ901447,KF53026 1,JX576750,JX57674 1,JX576742,JX57675 6,GU591769,GU5917 59,JQ901457,JXQ154 99,JX576730,JXQ154 80,KF530268,JX5767 40,JXQ15484,JQ9014 58,JX627336,M74568 ,JX576736,JXQ69803, JXQ69801,JXQ15489, JF920052,AF013255, JXQ15494,JX576738, JX576759,JF920058, JXQ15491,JXQ15496, JQ901449,JXQ15490, JX576751,JXQ69800, JQ901453,KF530269, JF920049,JX576735, JX576733,JQ901448, JX576737,JXQ15486, GU591767,JQ901455 ,JXQ15481,AB846662 ,GU591761,JF920062 ,AF013254,JXQ69798 ,GU591758,JXQ15548 5,JX576753,JX576675 7,JX576732,JX57674 9,JX576731,U63644, JX576743,JX576754, GU591760,JXQ69802 ,JXQ69799,JQ901454 ,JQ582844,GU59177 0,GU591764,JX5767 55,JF920053,GU5917 66,JXQ15483,JX5767 46,JX576734,U50362 ,FJ948820,JQ901452 ,JXQ15488,KC978856 ,JX576758,KF530260 ,JF920050,JF920047, JQ901451,JF920046, JF920054,JX576762, GU591762,JQ582843 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Human respiratory syncytial virus S2 | NC_001781 | vertebrates,human | Paramyxoviridae,Pneumovirus,Human respiratory syncytial virus | 1 | — | KC731483,AY91126 2,JX576729,KC73148 2,U50363,JXQ15493, JF920057,GU591763, JX576752,JF920059, JXQ15482,JXQ15487, JX576747,JF920051, JX576760,JF920069, AF035006,JXQ15497, ,JXQ15495,GU591765 ,JX576744,JX576761, JF920048,JXQ15479, JXQ15492,JX576748 U39662 |
| Human rhinovirus 1 | NC_001617 | vertebrates,human | Picornaviridae,Enterovirus,Rhinovirus A | 1 | — | FJ445111 |
| Human rhinovirus 10 | NC_001617 | vertebrates,human | Picornaviridae,Enterovirus,Rhinovirus A | 2 | — | DQ473498,FJ445178 |
| Human rhinovirus 100 | NC_001617 | vertebrates,human | Picornaviridae,Enterovirus,Rhinovirus A | 1 | — | FJ445175 |
| Human rhinovirus 11 | NC_001617 | vertebrates,human | Picornaviridae,Enterovirus,Rhinovirus A | 1 | — | EF173414 |
| Human rhinovirus 12 | NC_001617 | vertebrates,human | Picornaviridae,Enterovirus,Rhinovirus A | 1 | — | EF173415 |
| Human rhinovirus 13 | NC_001617 | vertebrates,human | Picornaviridae,Enterovirus,Rhinovirus A | 2 | — | FJ445116,FJ445117 |
| Human rhinovirus 14 | NC_001490 | vertebrates,human | Picornaviridae,Enterovirus,Rhinovirus B | 2 | — | L05355,K02121 |
| Human rhinovirus 15 | NC_001617 | vertebrates,human | Picornaviridae,Enterovirus,Rhinovirus A | 1 | — | DQ473493 |
| Human rhinovirus 16 | NC_001617 | vertebrates,human | Picornaviridae,Enterovirus,Rhinovirus A | 1 | — | L24917 |
| Human rhinovirus 17 | NC_001617 | vertebrates,human | Picornaviridae,Enterovirus,Rhinovirus A | 1 | — | EF173420 |
| Human rhinovirus 18 | NC_001617 | vertebrates,human | Picornaviridae,Enterovirus,Rhinovirus A | 1 | — | FJ445118 |
| Human rhinovirus 19 | NC_001617 | vertebrates,human | Picornaviridae,Enterovirus,Rhinovirus A | 1 | — | FJ445119 |
| Human rhinovirus 1B | NC_001617 | vertebrates,human | Picornaviridae,Enterovirus,Rhinovirus A | 1 | — | DQ0239 |
| Human rhinovirus 2 | NC_001617 | vertebrates,human | Picornaviridae,Enterovirus,Rhinovirus A | 1 | — | XQ2316 |
| Human rhinovirus 20 | NC_001617 | vertebrates,human | Picornaviridae,Enterovirus,Rhinovirus A | 1 | — | FJ445120 |
| Human rhinovirus 21 | NC_001617 | vertebrates,human | Picornaviridae,Enterovirus,Rhinovirus A | 1 | — | FJ445121 |
| Human rhinovirus 22 | NC_001617 | vertebrates,human | Picornaviridae,Enterovirus,Rhinovirus A | 1 | — | FJ445122 |
| Human rhinovirus 23 | NC_001617 | vertebrates,human | Picornaviridae,Enterovirus,Rhinovirus A | 1 | — | DQ473497 |
| Human rhinovirus 24 | NC_001617 | vertebrates,human | Picornaviridae,Enterovirus,Rhinovirus A | 2 | — | FJ445190,EF173416 |
| Human rhinovirus 25 | NC_001617 | vertebrates,human | Picornaviridae,Enterovirus,Rhinovirus A | 1 | — | FJ445123 |
| Human rhinovirus 26 | NC_001617 | vertebrates,human | Picornaviridae,Enterovirus,Rhinovirus A | 1 | — | FJ445124 |
| Human rhinovirus 27 | NC_001490 | vertebrates,human | Picornaviridae,Enterovirus,Rhinovirus B | 2 | — | FJ445186,EF173421 |
| Human rhinovirus 28 | NC_001617 | vertebrates,human | Picornaviridae,Enterovirus,Rhinovirus A | 1 | — | DQ473508 |
| Human rhinovirus 29 | NC_001617 | vertebrates,human | Picornaviridae,Enterovirus,Rhinovirus A | 1 | — | FJ445125 |
| Human rhinovirus 3 | NC_001490 | vertebrates,human | Picornaviridae,Enterovirus,Rhinovirus B | 2 | — | DQ473485,EF173422 |
| Human rhinovirus 30 | NC_001490 | vertebrates,human | Picornaviridae,Enterovirus,Rhinovirus B | 2 | — | FJ445179,DQ473512 |
| Human rhinovirus 31 | NC_001617 | vertebrates,human | Picornaviridae,Enterovirus,Rhinovirus A | 1 | — | FJ445126 |
| Human rhinovirus 32 | NC_001617 | vertebrates,human | Picornaviridae,Enterovirus,Rhinovirus A | 1 | — | FJ445127 |
| Human rhinovirus 33 | NC_001617 | vertebrates,human | Picornaviridae,Enterovirus,Rhinovirus A | 1 | — | FJ445128 |
| Human rhinovirus 34 | NC_001617 | vertebrates,human | Picornaviridae,Enterovirus,Rhinovirus A | 2 | — | FJ445189,DQ473501 |
| Human rhinovirus 35 | NC_001490 | vertebrates,human | Picornaviridae,Enterovirus,Rhinovirus B | 2 | — | FJ445187,DQ473487 |
| Human rhinovirus 36 | NC_001617 | vertebrates,human | Picornaviridae,Enterovirus,Rhinovirus A | 1 | — | DQ473505 |
| Human rhinovirus 37 | NC_001490 | vertebrates,human | Picornaviridae,Enterovirus,Rhinovirus B | 1 | — | EF173423 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human rhinovirus 38 | NC_001617 | vertebrates,human | 2 | Picornaviridae,Enterovirus,Rhinovirus A | — | DQ473495,FJ445180 |
| Human rhinovirus 39 | NC_001617 | vertebrates,human | 1 | Picornaviridae,Enterovirus,Rhinovirus A | — | AY751783 |
| Human rhinovirus 4 | NC_001490 | vertebrates,human | 1 | Picornaviridae,Enterovirus,Rhinovirus B | — | DQ473490 |
| Human rhinovirus 40 | NC_001617 | vertebrates,human | 1 | Picornaviridae,Enterovirus,Rhinovirus A | — | FJ445129 |
| Human rhinovirus 41 | NC_001617 | vertebrates,human | 1 | Picornaviridae,Enterovirus,Rhinovirus A | — | DQ473491 |
| Human rhinovirus 42 | NC_001490 | vertebrates,human | 1 | Picornaviridae,Enterovirus,Rhinovirus B | — | FJ445130 |
| Human rhinovirus 43 | NC_001617 | vertebrates,human | 1 | Picornaviridae,Enterovirus,Rhinovirus A | — | FJ445131 |
| Human rhinovirus 44 | NC_001617 | vertebrates,human | 1 | Picornaviridae,Enterovirus,Rhinovirus A | — | DQ473499 |
| Human rhinovirus 45 | NC_001617 | vertebrates,human | 1 | Picornaviridae,Enterovirus,Rhinovirus A | — | FJ445132 |
| Human rhinovirus 46 | NC_001617 | vertebrates,human | 1 | Picornaviridae,Enterovirus,Rhinovirus A | — | DQ473506 |
| Human rhinovirus 47 | NC_001617 | vertebrates,human | 1 | Picornaviridae,Enterovirus,Rhinovirus A | — | FJ445133 |
| Human rhinovirus 48 | NC_001490 | vertebrates,human | 1 | Picornaviridae,Enterovirus,Rhinovirus B | — | DQ473488 |
| Human rhinovirus 49 | NC_001617 | vertebrates,human | 2 | Picornaviridae,Enterovirus,Rhinovirus A | — | FJ445134,DQ473496 |
| Human rhinovirus 5 | NC_001490 | vertebrates,human | 1 | Picornaviridae,Enterovirus,Rhinovirus B | — | FJ445112 |
| Human rhinovirus 50 | NC_001617 | vertebrates,human | 1 | Picornaviridae,Enterovirus,Rhinovirus A | — | FJ445135 |
| Human rhinovirus 51 | NC_001617 | vertebrates,human | 1 | Picornaviridae,Enterovirus,Rhinovirus A | — | FJ445136 |
| Human rhinovirus 52 | NC_001490 | vertebrates,human | 3 | Picornaviridae,Enterovirus,Rhinovirus B | — | FJ445137,EF173424,FJ445188 |
| Human rhinovirus 53 | NC_001617 | vertebrates,human | 1 | Picornaviridae,Enterovirus,Rhinovirus A | — | DQ473507 |
| Human rhinovirus 54 | NC_001617 | vertebrates,human | 2 | Picornaviridae,Enterovirus,Rhinovirus A | — | FJ445138,FJ445139 |
| Human rhinovirus 55 | NC_001617 | vertebrates,human | 1 | Picornaviridae,Enterovirus,Rhinovirus A | — | DQ473511 |
| Human rhinovirus 56 | NC_001617 | vertebrates,human | 1 | Picornaviridae,Enterovirus,Rhinovirus A | — | FJ445140 |
| Human rhinovirus 57 | NC_001617 | vertebrates,human | 1 | Picornaviridae,Enterovirus,Rhinovirus A | — | FJ445141 |
| Human rhinovirus 58 | NC_001617 | vertebrates,human | 1 | Picornaviridae,Enterovirus,Rhinovirus A | — | FJ445142 |
| Human rhinovirus 59 | NC_001617 | vertebrates,human | 1 | Picornaviridae,Enterovirus,Rhinovirus A | — | DQ473500 |
| Human rhinovirus 6 | NC_001490 | vertebrates,human | 1 | Picornaviridae,Enterovirus,Rhinovirus B | — | DQ473486 |
| Human rhinovirus 60 | NC_001617 | vertebrates,human | 1 | Picornaviridae,Enterovirus,Rhinovirus A | — | FJ445143 |
| Human rhinovirus 61 | NC_001617 | vertebrates,human | 1 | Picornaviridae,Enterovirus,Rhinovirus A | — | FJ445144 |
| Human rhinovirus 62 | NC_001617 | vertebrates,human | 1 | Picornaviridae,Enterovirus,Rhinovirus A | — | FJ445145 |
| Human rhinovirus 63 | NC_001617 | vertebrates,human | 1 | Picornaviridae,Enterovirus,Rhinovirus A | — | FJ445146 |
| Human rhinovirus 64 | NC_001617 | vertebrates,human | 2 | Picornaviridae,Enterovirus,Rhinovirus A | — | EF173417,FJ445181 |
| Human rhinovirus 65 | NC_001617 | vertebrates,human | 1 | Picornaviridae,Enterovirus,Rhinovirus A | — | FJ445147 |
| Human rhinovirus 66 | NC_001617 | vertebrates,human | 1 | Picornaviridae,Enterovirus,Rhinovirus A | — | FJ445148 |
| Human rhinovirus 67 | NC_001617 | vertebrates,human | 1 | Picornaviridae,Enterovirus,Rhinovirus A | — | FJ445149 |
| Human rhinovirus 68 | NC_001617 | vertebrates,human | 1 | Picornaviridae,Enterovirus,Rhinovirus A | — | FJ445150 |
| Human rhinovirus 69 | NC_001490 | vertebrates,human | 1 | Picornaviridae,Enterovirus,Rhinovirus B | — | FJ445151 |
| Human rhinovirus 7 | NC_001617 | vertebrates,human | 2 | Picornaviridae,Enterovirus,Rhinovirus A | — | DQ473503,FJ445176 |
| Human rhinovirus 70 | NC_001490 | vertebrates,human | 1 | Picornaviridae,Enterovirus,Rhinovirus B | — | DQ473489 |
| Human rhinovirus 71 | NC_001617 | vertebrates,human | 1 | Picornaviridae,Enterovirus,Rhinovirus A | — | FJ445152 |
| Human rhinovirus 72 | NC_001490 | vertebrates,human | 1 | Picornaviridae,Enterovirus,Rhinovirus B | — | FJ445153 |
| Human rhinovirus 73 | NC_001617 | vertebrates,human | 1 | Picornaviridae,Enterovirus,Rhinovirus A | — | DQ473492 |
| Human rhinovirus 74 | NC_001617 | vertebrates,human | 1 | Picornaviridae,Enterovirus,Rhinovirus A | — | DQ473494 |
| Human rhinovirus 75 | NC_001617 | vertebrates,human | 1 | Picornaviridae,Enterovirus,Rhinovirus A | — | DQ473510 |
| Human rhinovirus 76 | NC_001617 | vertebrates,human | 2 | Picornaviridae,Enterovirus,Rhinovirus A | — | FJ445182,DQ473502 |
| Human rhinovirus 77 | NC_001617 | vertebrates,human | 1 | Picornaviridae,Enterovirus,Rhinovirus A | — | FJ445154 |
| Human rhinovirus 78 | NC_001490 | vertebrates,human | 2 | Picornaviridae,Enterovirus,Rhinovirus B | — | FJ445183,EF173418 |
| Human rhinovirus 79 | NC_001617 | vertebrates,human | 1 | Picornaviridae,Enterovirus,Rhinovirus A | — | FJ445155 |
| Human rhinovirus 8 | NC_001617 | vertebrates,human | 1 | Picornaviridae,Enterovirus,Rhinovirus A | — | FJ445113 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human rhinovirus 80 | NC_001617 | vertebrates,human | 1 | Picornaviridae,Enterovirus,Rhinovirus A | — | FJ445156 |
| Human rhinovirus 81 | NC_001617 | vertebrates,human | 3 | Picornaviridae,Enterovirus,Rhinovirus A | — | FJ445159,FJ445158, FJ445157 |
| Human rhinovirus 82 | NC_001617 | vertebrates,human | 1 | Picornaviridae,Enterovirus,Rhinovirus A | — | FJ445160 |
| Human rhinovirus 83 | NC_001490 | vertebrates,human | 1 | Picornaviridae,Enterovirus,Rhinovirus B | — | FJ445161 |
| Human rhinovirus 84 | NC_001490 | vertebrates,human | 1 | Picornaviridae,Enterovirus,Rhinovirus B | — | FJ445162 |
| Human rhinovirus 85 | NC_001617 | vertebrates,human | 1 | Picornaviridae,Enterovirus,Rhinovirus A | — | FJ445163 |
| Human rhinovirus 86 | NC_001490 | vertebrates,human | 1 | Picornaviridae,Enterovirus,Rhinovirus B | — | FJ445164 |
| Human rhinovirus 87 | NC_001617 | vertebrates,human | 1 | Picornaviridae,Enterovirus,Rhinovirus A | — | DQ473504 |
| Human rhinovirus 88 | NC_001617 | vertebrates,human | 1 | Picornaviridae,Enterovirus,Rhinovirus A | — | FJ445166,M16248,FJ 445165,FJ445184 |
| Human rhinovirus 89 | NC_001617 | vertebrates,human | 4 | Picornaviridae,Enterovirus,Rhinovirus A | — | FJ445114,FJ445177, FJ445115 |
| Human rhinovirus 9 | NC_001617 | vertebrates,human | 3 | Picornaviridae,Enterovirus,Rhinovirus A | — | FJ445167 |
| Human rhinovirus 90 | NC_001617 | vertebrates,human | 1 | Picornaviridae,Enterovirus,Rhinovirus A | — | FJ445168 |
| Human rhinovirus 91 | NC_001490 | vertebrates,human | 1 | Picornaviridae,Enterovirus,Rhinovirus B | — | FJ445169 |
| Human rhinovirus 92 | NC_001490 | vertebrates,human | 1 | Picornaviridae,Enterovirus,Rhinovirus B | — | EF173425 |
| Human rhinovirus 93 | NC_001490 | vertebrates,human | 1 | Picornaviridae,Enterovirus,Rhinovirus B | — | EF173419,FJ445185 |
| Human rhinovirus 94 | NC_001617 | vertebrates,human | 2 | Picornaviridae,Enterovirus,Rhinovirus A | — | FJ445170 |
| Human rhinovirus 95 | NC_001617 | vertebrates,human | 1 | Picornaviridae,Enterovirus,Rhinovirus A | — | FJ445171 |
| Human rhinovirus 96 | NC_001617 | vertebrates,human | 1 | Picornaviridae,Enterovirus,Rhinovirus A | — | FJ445172 |
| Human rhinovirus 97 | NC_001490 | vertebrates,human | 1 | Picornaviridae,Enterovirus,Rhinovirus B | — | FJ445173 |
| Human rhinovirus 98 | NC_001617 | vertebrates,human | 1 | Picornaviridae,Enterovirus,Rhinovirus A | — | FJ445174 |
| Human rhinovirus 99 | NC_001490 | vertebrates,human | 1 | Picornaviridae,Enterovirus,Rhinovirus B | — | |
| Human rhinovirus A | NC_001617 | vertebrates,human | 17 | Picornaviridae,Enterovirus,Rhinovirus A | — | GQ415051,JF285322, JF285324,JN837692, JF285321,JN798589, JN815250,JF285323, JQ747751,DQ473509, JN798583,JN798561, GQ415052,A10937, JN837697,JF285329, JN798556 |
| Human rhinovirus B | NC_001490 | vertebrates,human | 9 | Picornaviridae,Enterovirus,Rhinovirus B | — | JN815239,JN798573, JF285330, JF285308, JF285309, JN 798588, JQ994497,JF285331, JQ245969 |
| Human rhinovirus B72 | NC_001490 | vertebrates,human | 1 | Picornaviridae,Enterovirus,Rhinovirus B | — | GU968948 |
| Human rotavirus (SEROTYPE 2/ STRAIN S2) | NC_011504 | vertebrates,human | 1 | Reoviridae,Rotavirus,Rotavirus A | seg. 10 | U59104 |
| Human rotavirus (STRAIN L26) | NC_011500 | vertebrates,human | 1 | Reoviridae,Rotavirus,Rotavirus A | seg. 5 | D38150 |
| Human rotavirus (STRAIN RV5) | NC_011504 | vertebrates,human | 1 | Reoviridae,Rotavirus,Rotavirus A | seg. 10 | U59103 |
| Human rotavirus (strain US1205) | NC_011504 | vertebrates,human | 1 | Reoviridae,Rotavirus,Rotavirus A | seg. 10 | AF079358 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Human rotavirus (strain US1205) | NC_011509 | vertebrates,human | Reoviridae,Rotavirus,Rotavirus A | 1 | seg. 6 | AF079357 |
| Human rotavirus (strain US1205) | NC_011510 | vertebrates,human | Reoviridae,Rotavirus,Rotavirus A | 1 | seg. 4 | AF079356 |
| Human rotavirus 1 strain RV4 | NC_011504 | vertebrates,human | Reoviridae,Rotavirus,Rotavirus A | 1 | seg. 10 | U59108 |
| Human rotavirus A | NC_011500 | vertebrates,human | Reoviridae,Rotavirus,Rotavirus A | 20 | seg. 5 | EF672557,JF766584, FJ423117,EF672620, FJ423139,AF190169, GU189555,Z32552, JF766595,EF672613, EF672592,U11492, FJ423156,JF766573, JF421981,L18943, D38151,HM627559, EF672564,FJ423128 |
| Human rotavirus A | NC_011501 | vertebrates,human | Reoviridae,Rotavirus,Rotavirus A | 95 | seg. 7 | JN706641,JF304934, FJ423141,EU984100, EF672572,EF672580, JN869275,JF304923, AY787648,EU520416, JN706640,AB741657, JN706620, JX946176,AB741657, JX946176,JN706620, FJ747622,JN706624, AF506014,JN706633, DQ005107,GU18955 7,JN706628,JN70662 3,JX946165,JN70663 9,JF766574,EF67258 6,AB748601,KC1397 87,AF506018,KC149 936,EF672579,JQ863 317,EF672622,EF672 615,JN706622,JX416 216,AF506293,EF672 607,JQ087442,JN869 276,EF554133,EF672 573,EF672600,HQ64 1361,JN706638,JQ71 3650,JQ087431,EF55 4100,EF672594,EU2 00800,JN706625,JN8 69272,AB022770,EF6 72601,JN706627,JF8 04986,JX307623,JX3 07626,EF554089,DQ 005118,FJ423151,JF 421983,JF766585,G |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0414548,FJ423119,FJ747633,JX567766,JX416224,JX307624,HM627560,KC149929,JQ087453,EF672608,EU520415,FJ423130,JN104617,JN706626,EF672566,JN706634,EF554122,JX307625,EF554111,JN869274,EF554111,HQ641370,JN869277,JN706637,JX416209,JF766596,JX509932,EF672587,JN869273,EF672559,JN706621,JN706635,JN706631 |
| Human rotavirus A | NC_011502 | vertebrates,human | 113 | Reoviridae,Rotavirus,Rotavirus A | seg. 8 | JX307619,EF554090,JQ715661,AB022771,JF421982,JN706613,JX307621,FJ423120,FJ747621,AF338246,JN706605,JN706619,HQ702225,EF672593,EF672565,JN706614,FJ423131,AF338248,AB748596,JN104624,EF672621,AF190172,HQ025982,HQ64136 0,EF672614,AF19017 0,EF554123,HQ7022 47,FJ423152,JX5677 65,AF190171,X81435,AB771768,EF554112,JN706603,JQ898159,JX416208,HQ02598 1,GU189556,JX9461 75,JQ713649,JX4162 23,JN706606,HQ670 643,HQ702258,HQ64 1369,EU984099,JN70 6598,JN706616,AB77 1753,JN706604,JX94 6164,KC149935,AY7 87649,KC139786,JQ 715664,JF304922,JN 706601,HM627561,J F766597,JN706617,E U200801,,AF506015, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | DQ005117,JN706610,JN706602,JX307620,JX416215,EU868888,DQ005106,JQ86331 6,HQ702236,FJ42314 2,HQ702214,X81428,JF766575,JQ715662,HQ670636,GQ41454 7,JN706611,JN706661 5,AB771770,JN70659 9,JF766586,AB77176 4,X81433,X76645,X8 1425,JN706609,JX30 7622,X81434,JN7066 12,JN706608,JN1046 16,AB741656,EF5541 01,JF304933,EF6725 58,JQ715663,EF5541 34,KC149928,AF506 019,JQ715660,AF338 247,AF541920,X8142 7,FJ747632,JN706660 0,X81437,JX509931,J N706607,JN706618,X 81436 |
| Human rotavirus A | NC_011503 | vertebrates,human | 622 | Reoviridae,Rotavirus,Rotavirus A | seg. 9 | JF965002,JN706202,JX458968,JQ710665,GQ414545,GQ99689 6,JN706564,DQ8736 78,JN706267,AB5345 36,JX946173,FJ4475 67,JN706204,JN7065 54,AF260949,JN7065 66,JXQ88016,JF9650 04,AB527037,JN7062 12,JXQ88013,HQ702 259,AB527030,FJ948 854,JX509940,JN706 275,JXQ88018,AB534 532,JN706251,JN706 346,JN706559,AB527 009,JQ043268,JN706 227,FJ152132,AB527 023,HQ738627,FJ529 386,JN706238,GU37 7172,FJ948849,JN70 6210,JF965010,AB18 0969,JQ043273,JN70 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 6218,AJ278254,JN706352,JN706327,JN706334,AB527027,AB534530,FJ948843,GQ996882,JX458962,JN706215,JN706270,X63156,DQ923801,EU679389,JN706345,JQQ43276,JX458955,JN706377,AB527034,JN706299,DQ062126,AB530270,JQ253576,JN706230,JN706304,AB527033,AB527014,JF965000,DQ440616,GU377151,JXQ88009,JX470504,JQ289117,JX470511,DQ062128,DQ099750,JX567752,AB527019,EF672595,JN706310,FJ529395,EU791924,AB534535,JN706278,AB527029,JN706338,FJ747618,JF766605,JQ043267,EF672574,JF813102,AB118024,HQ537522,JN706367,JN706563,JN706203,JQ043277,DQ873679,AF17083 7,AB530268,EF672602,JN706336,JN706249,JF965005,HQ53751 7,HQ702237,AY629560,FJ948833,JQ253567,DQ873672,AB527015,JQ710675,JN706262,AB527035,HQ738621,FJ447570,JN706229,EU679390,JN706351,GU377136,JQ253573,JN706309,AF260939,GQ398012,JF964999,EF672609,JN706370,JX470508,JQ710671,FJ948836,JN706348,JN706295,AF260942,JX458964,AF |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 260941,FJ423132,FJ423143,AF260958,JN706224,GU377144,JN706353,FJ747630,EF077484,AB527025,JX458966,AF260943,JN706317,AF170834,JN706306,JQ710662,DQ099748,JX103956,JN706302,JN706341,AY787646,JN706231,JX470510,EF672567,EU679391,JN706291,JN706556,KC242226,GQ117003,AF386915,EU805775,JN706328,AF274971,JF813106,JN706319,JQ253572,AB527041,DQ873673,GQ452924,FJ423121,JN706240,JN706232,JN706258,JF964998,JQ710676,AF260936,JN706314,JQ253574,DQ099753,GU377148,JX567748,JX470506,AB534526,JN706378,GU377133,JX470513,HQ702248,L21666,JN706308,JX103957,JQ253564,JN706343,HQ738577,JN706361,GQ996884,JQO43270,AY206861,JN706364,JN706245,FJ948829,JN706558,GQ996892,JF304931,JF965009,JN706239,AF143690,FJ915079,AB527006,GQ996890,KC841471,AB534533,AB530267,JN706255,AB534520,EU679392,AB527022,JX567750,DQ122400,JXQ8801 9,JN706359,AB527040,AF143689,JQ253563,JN706329,GU3771 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 74,AY856443,JXQ880 12,JN706305,DQ099 749,DQ873670,JN70 6199,AF274969,AB52 7043,DQ099751,GQ3 98018,HQ537521,JN 706219,JN706266,JN 706294,JX458958,JQ 710669,JN706344,G 0117005,JN706372,J N706246,AB669005, AB527028,JN706318, JN706326,AY456382, JX470512,AF143688, FJ948838,JXQ88020, JN706248,EF554109, JN706300,JQ818169, DQ017650,JQ710673 ,JN706303,JX567753 ,DQ873676,JQ04327 1,JN706313,JN70636 0,AB527020,JN70623 3,DQ111868,AB5270 21,AF260948,JX4705 05,DQ062123,FJ7476 19,AB534522,JX4589 54,GU377164,JQ253 569,JN706254,JXQ88 015,EF672616,JN706 311,EU200798,AB52 7042,JN706339,HQ7 02226,JF965008,GU3 77142,JN706222,DQ 099746,AB530266,AF 260935,JN706366,JN 706369,GQ996849,G 0452923,JX567751,J 0043278,JF742651,J N706574,GQ996891, JN706358,HQ738583 ,JN706330,JQ710677 ,JN706337,AB530269 ,AB530274,JN706312 ,AB527031,JN706323 ,HQ537513,JN706637 3,JN706321,JN70626 8,AB534531,JQ71066 4,JN706217,AB18097 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0,JN706264,AB741654,AB534523,GQ9996867,AF500235,DQ062130,JX458959,JQ863314,JX307591,GQ452926,JN706253,JN706237,HQ702215,JN706206,GU377135,EF088831,AB534521,FJ152121,JN706261,FJ915078,JN706211,GU377166,JN706220,HM627558,JN706247,JF719063,DQ062124,JN706276,FJ948839,JQ253570,GQ996925,JX458965,AF438228,JN706228,JN706208,JN706567,EF159575,JN706242,JN706315,JF965001,JQ710666,HQ537514,EF672560,AB534534,JQ710674,JF965006,HQ537512,JN706292,AB527016,FJ915077,AF159610,JQ710670,HQ738620,FJ948837,AB527024,JN706322,JN706331,AB527011,JF965003,AJ311738,AB527017,AB527038,AB530273,JN706201,JN706252,DQ099747,AF260934,JN706565,AB527045,AY631125,GU3771169,JN706221,JXQ88014,FJ423153,FJ529385,JQ710667,JN706560,AB669013,FJ948831,JN706307,JN706347,AF260959,GQ996894,AF260957,AF450293,FJ948853,JN706374,JN706250,JN706257,JX307594,GU377145,AB527008,JN706320,JN706223,A |

| Taxonomy | Rep.Acc.ID | Host | # GN's | Lineage | Seg. Count | GN.Acc.IDs |
|---|---|---|---|---|---|---|
| | | | | | | F260940,EU984109,JN706362,FJ529383,D0099754,EF672623,AF260937,JX470507,JN706335,JN706357,JQ253571,AB534527,AB534524,JX458956,JN706333,JN706355,JN706324,JN706236,GQ996883,JN706259,JF304920,AB527044,GQ996885,JN706620 7,JQ253575,JN706637 9,JN706562,GQ99968 87,JX458960,JN7062 43,JN706214,JN7063 63,EU679394,DQ062 127,JN706575,JN706 568,JX458953,JX307 593,HQ738579,JN70 6296,JN706569,AB53 4528,EF088832,AB52 7007,JN706256,AF50 1580,AB669009,JQ71 0672,GQ996889,AF1 70836,JN706279,FJ9 48845,HQ738622,AF 260946,FJ915094,U0 4350,AB527018,JN70 6350,JN706325,DQ0 62129,AF260933,FJ9 48847,JQ043269,DQ 099752,HQ537519,A F260938,JN706200,J N706293,JN706265,J 0253566,GQ996893, GU377155,JN706571 ,JX567749,AB530271 ,FJ948832,AB527039 ,DQ873669,DQ87367 1,DQ117937,JQ2535 68,JQ253562,GQ117 006,JX110838,JX458 967,JN706557,JN706 572,JN706356,AB530 272,JXQ88011,JN706 375,JN706301,GU37 7159,GQ996886,AB5 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 27012,KC139779,JQ710668,JQ713096,JX458961,AB534525,JX470509,AB669017,G0117002,DQ873677,JN706235,AF409087,DQ117938,JN706332,JN706561,JN706371,JN706244,AY003871,GQ996888,JN706620 5,JN706365,FJ44756 8,JN706213,AF17083 5,JN706354,JQ34321 9,JQ043274,GQ3980 14,AF260947,JN7063 68,JF421980,FJ9488 51,AF260944,FJ9488 48,JN706573,JN7065 70,JF965007,JX3075 92,JN706225,JN7063 49,AF274970,GQ996 926,EF672588,AB180 974,JX458957,AB527 013,AF260945,JN706 263,AJ278257,JN706 555,JF766594,FJ152 110,M58290,JN706620 9,JN706226,DQ0176 49,GQ117004,JX458 963,JF766583,GU377 143,JXQ88017,EF159 576,JN706269,JN706 340,HQ738628,EU67 9393,JN706216,DQ1 17939,AY630924,AB 527046,JQ043275,JN 70627l,JXQ88008,D 0062125,JQ710663,J N706376,JQ043272, AF438227,GQ452927 ,JN706297,AB527010 ,GQ996895,JQ04326 6,GQ117001,JN7063 42,JN706198,GU377 147,JXQ88010,AB527 036,JN706260,DQ92 3797,HQ537518,JN7 06316,JN706298,JQ2 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | 53565,AB527032,AB534529,AB527026,EF672581,GU377134,FJ948830,FJ948855,GU377150,JN706234,G0996847 |
| Human rotavirus A | NC_011504 | vertebrates,human | Reoviridae,Rotavirus,Rotavirus A | 294 | seg. 10 | EF672596,JQ043306,AJ236783,GQ465013,AJ400644,AF469676,AJ236755,AJ311732,GQ465018,GQ465502,4,JX307628,AY787654,AJ236750,AB232700,JX458984,AB326962,GQ465019,AB361276,JF766576,AY601542,EF554113,EF672568,GQ465021,AJ400634,EF159572,AB196491,AB741658,GQ465037,JQ043300,HQ641371,AF170833,AB326337,FJ915085,AJ427314,AY576606,JQO43311,JN706655,JF766587,AY601545,AJ236756,JN706657,AJ236784,AJ236749,GQ465034,JF304935,AF284778,AB022772,JF813103,AB748606,JX458977,AB361279,JX946177,EF159573,D0299876,FJ152114,EU679381,AB211988,AJ400636,JN706644,D89873,GQ465020,JX307629,AJ236777,HM235509,GQ465028,JN706646,EU679378,FJ152136,GQ465026,AB326336,EF672575,JQ043302,AF541921,EF672603,DQ92380 3,AB762778,AB1969 59,EU659855,AB0O8 217,FJ423144,JN706 650,JX458980,AF469 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | 679,GU189558,AF260928,AF284777,AJ400638,AF170831,JQ043308,JX458982,JF421984,AJ278252,AJ400635,JX307630,JF804998,JQ898161,GQ465015,AJ236775,FJ423133,AB196958,AB201459,GQ465006,JX307627,AB361282,AB326343,HM627562,JN706642,AB213392,EF159574,JN104626,GQ465017,AJ236771,GQ465036,AB196492,FJ915088,AJ427316,JN706653,AF170830,JN706660,EU679377,AY629562,JX458969,GQ465031,AB326339,AF200225,AY601540,U59106,AJ236776,EF089269,JN104618,FJ423154,JN706668,JX458975,JX458970,GQ465032,JQ863318,EF672589,GQ465007,KC139788,AJ236778,FJ685615,GQ465022,EU791925,AB211992,AF506291,JQ043312,JF813107,GQ465005,AJ427313,AB213391,AF506016,JN706648,EU984101,AJ236770,JQ043304,G0414549,AB326334,JX458978,JX416225,AY601544,AJ400637,EF554135,JN706662,GU138211,AB326348,JN706658,AB303218,AB326340,EU679382,FJ152125,JN706645,DQ005116,KC890886,U59107,D88830,GQ465023,EU679379,JX |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 458974,JQ713651,AJ400641,D10772,KC890884,JN706647,HQ641362,EU679380,G0465035,DQ639954,AF469678,JX458976,JQ043305,AB326297,KC890885,AB211987,JQ898160,FJ915087,GQ465025,GQ465010,EF672624,JX458981,JF766598,AB21199,AB763972,D88829,GQ465009,JN706663,JX458973,KC890882,JN706651,AY601541,AJ236752,AJ236765,AF260929,AB361284,KC890883,AF200224,FJ747634,EF672561,KC890887,AJ400640,AB326969,JX458983,FJ423122,EF672617,JN706643,AB361289,GQ465016,DQ92379,9,GQ465014,AB3262 86,JN706659,AF469677,AJ400643,AJ2367 79,AJ400639,JN7066 54,JQ043310,AJ2367 85,EF554091,JN7066 56,GU592516,JQ043 309,GQ465011,JN70 6652,AF284780,AJ42 7315,FJ747623,AJ23 6753,EF672582,AJ23 6781,JX458972,GQ4 65008,GQ465030,DO 005105,AB326965,AF 260930,JX458971,AB 326338,JX567767,EF 672610,GQ465029,G 0465033,AF284776, AJ400642,GQ465012 ,U59110,AJ236780,G 0465027,JF804987,A J236751,AB211989,A B361288,JQ043303,A |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | B32642,JN706649,AB32645,AY601543,AJ236754,AJ236782,JX458979,EF554124,EF554102,D10771,AB326344,JF805008,AF170832,AB211990,JQ043301,EU200802,JF304924,FJ915086,AB361277,AJ278255,JX946166,JQ043307 |
| Human rotavirus A | NC_011505 | vertebrates,human | 126 | Reoviridae,Rotavirus,Rotavirus A | seg. 11 | EF590982,GQ414550,JN872347,AB008659,EF590987,JN706677,JX946167,EF672569,KC139789,AB04521 8,EU200803,AB0086 62,JN706673,HM627 563,U54772,FJ42312 3,JQ043322,EF67259 0,JQ043320,JN70667 5,FJ747635,EF59098 8,EF672576,JF76658 8,JN869288,JQ71568 0,FJ423145,JN70667 8,EF590983,JQ04332 3,KC149937,AB0086 63,JX946178,FJ7476 24,AB035708,EF6725 83,GU189559,AB008 657,EF590981,JN706 680,JN706664,JN869 287,AF508732,AB763 974,AB008664,AB00 8656,EF554114,U547 73,AY841126,JN7066 85,AB008658,AY033 396,EF554136,JN706 679,AB045219,JN706 665,AF338245,HQ02 5986,AY787651,AB0 08660,KC149930,HQ 670638,U96698,FJ42 3134,EF590990,AF33 8244,M33607,EF590 991,AY803730,AB04 5217,JN706681,EF59 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0989,JN706683,JN869284,EF590985,JX416210,AB045220,JN869289,EF590986,AB763975,EF672562,AY769694,EU984102,JF766577,JN706672,JQ043315,JN706674,AB008655,EF672625,JX509934,JN706684,JF804999,AB741659,JX416226,EF554103,EF590984,AB022773,X76779,AF306494,FJ423155,JQ043313,AB748611,JQ043319,EU791926,JN706682,EF672604,EF672618,JN869285,JN869286,JQ043318,EF672597,HQ670645,AY770974,JN706676,EF672611,JX567768,JF766599,JQ043321,AY601548,AB008661,HQ025985,AY769695,JF804988,JF421985 |
| Human rotavirus A | NC_011506 | vertebrates,human | 73 | Reoviridae,Rotavirus,Rotavirus A | seg. 2 | HQ025976,JF766579,GQ414541,HM627554,EF583050,GU189552,JN706476,EU984104,FJ423125,FJ747614,JX567761,DQ480724,DQ005113,EF554083,EF583026,HQ670633,JX416219,JN706469,EF583034,EF583022,EF583030,JN706487,JF421976,JN706477,JX416212,JF766590,FJ423114,EF583014,EU200794,JX946169,EF583038,JN706483,JN706478,JN706467,EF554116,DQ862063,AB022766,JX416205,JN706468,JF766601,EF583046,FJ |

TABLE 10-continued

VíroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 422147,FJ423136,JX946160,JX509936,EF583042,EF554127,JN104612,JN706471,JN706484,JN706473,JN706486,EF583018,FJ747626,JQ713646,JN706485,JN706480,AY787652,JN706470,JN706479,JN706481,EF554094,AB741650,D0005124,JN706474,KC139782,JN706466,HQ025975,EF554105,JQ863310,JN706475,JN706482,JN706472 |
| Human rotavirus A | NC_011507 | vertebrates,human | 81 | Reoviridae,Rotavirus,Rotavirus A | seg. 1 | JX946159,JN706448,EF583017,JQ713645,EF583037,HQ702218,JN706449,JX416204,JF421975,JN706444,DQ005125,EU200793,EU984103,JN706445,HQ702229,FJ747625,HM627553,JF76658 9,JN706453,JX56776 0,JN706465,EF55412 6,JN706451,HQ7022 51,AY787653,JN7064 61,HQ702240,HQ025 973,JN706462,JN706 454,HQ025974,JF766 578,JN706452,HQ67 0639,JN706457,FJ42 3146,JN706460,FJ42 3113,JF766600,JQ86 3309,KC139781,JN70 6464,AB022765,JN70 6459,HQ702207,JF30 4915,EF554104,JX41 6218,JN104619,JN10 4611,JN706450,DQO 05114,EF583033,JN7 06447,AB741649,FJ4 23135,HQ641355,FJ4 23124,HQ670632,JN 706458,GU189551,E F583041,JX416211,J |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | JN706455,FJ747613,EF554082,EF554093,HQ641364,JN706456,JN706446,EF583021,EF583045,GQ414540,JX946168,EF554115,EF583029,JN706463,JX509935,EF583049,EF583025,JF304926 |
| Human rotavirus A | NC_011508 | vertebrates,human | 86 | Reoviridae,Rotavirus,Rotavirus A | seg. 3 | EF554117,JN706489,AY277919,JX946170,JF766602,FJ747627,JF421977,EF554095,AY277918,EF583035,JF766591,HQ670634,AB022767,AY277914,JQ863311,JX416213,EF554084,HQ64135 7,JN104613,AY277791 7,EF583015,DQ0051 12,JN706509,HQ670 641,KC139783,JN706 494,HQ641366,FJ423 115,JN706503,JX946 161,DQ005123,JN70 6491,JN706502,HQ0 25977,FJ423126,EF5 83039,EF583031,JN7 06488,EU984105,EF 583023,JN706493,FJ 747615,AY277915,JN 706496,JN706499,EF 554106,JN706504,EF 583019,JF304917,HQ 025978,JN706506,JN 104621,JN706490,EF 583047,AY277920,EF 583051,AB733135,EF 583027,JF766580,JX 567762,AY277916,EF 583043,JN706501,JX 416220,AY267335,EF 554128,GQ414542,H M627555,JQ713647,J N706498,JF304928,J X416206,EU200795,J N706500,JN706492,J N706497,JX509937,F |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | J423137,GU189553,JN706495,JN706507,JN706508,F1423148,AB741651,AY787654,JN706505 |
| Human rotavirus A | NC_011509 | vertebrates,human | 315 | Reoviridae,Rotavirus,Rotavirus A | seg. 6 | JQ818154,JN706538,GU390418,HM627557,JF421979,GU390452,EU372724,JQ230099,JQ230080,FJ152109,JQ043298,GU390443,EU372726,JX307599,JN706544,HQ738601,JQ230065,FJ685614,EU372746,GU390414,EF426129,JQ230082,JQ230070,EF426136,GU390438,AY601554,EF583040,EU556221,EU372748,EF426139,HQ445977,GU390425,KC149926,FJ747617,JF304919,EU372745,GU390453,HQ445975,JQ230083,JN706535,EF583016,JQ230066,HQ611018,AY787645,AY601552,AY601550,JX567763,JQ863313,EU372732,JQ230090,KC890877,EU984108,FJ152120,GU390448,AF260931,JQ818153,GU390432,EF426137,GU390440,JX946172,EF426124,EU372725,EU372738,HQ611009,JX307600,JQ230086,JQ230101,AF531912,HQ611032,JN706546,GU390423,HQ610999,HQ611022,JQ818168,EF583028,H0738589,HQ611003,AY601551,HQ611006,EU679384,JQ230064,JQ230068,GU390904 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 50,EF426122,JQ043294,GU390416,JQ230072,JQ230061,JQ230089,GU390445,EF426126,FJ423118,GU390422,JQ230081,HQ611014,HQ611021,JN104614,EU372743,EU679385,AB022768,JQ818166,JN706547,JQ230093,DQ873675,EF426120,EF426130,JN706532,HQ738584,JQ230088,DQ092380,EU372730,GU390442,EU372727,JQ230078,HQ738586,HQ611001,EU805774,JF766593,JQ230063,DQO05110,JQ230092,GU390415,EU372750,HQ738598,GU390426,HQ611005,JQ230100,EU372747,JX509939,HQ738597,EF426138,GU390441,EF426128,EF426119,JN706543,HQ611013,EF583036,JQ230102,JQ230097,JQ087427,HQ611020,JQ230077,GU390417,EF426131,HQ611011,EF426140,JQ230094,JX416207,HQ611017,GU390430,JQ043296,JQ230059,JQ230084,HQ738595,JF766604,KC890878,JQ818151,HQ611027,EU372736,HQ738599,HQ611019,HQ611016,HQ738591,EU679388,EU372742,AF309652,EU372731,JN706550,JN706536,JF304930,EU372728,GU390427,EU679383,AY601549,JQ230095,J |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | N706542,HQ445978,EU372733,HQ611033,JN706551,JQ230085,EF426125,HQ61100 0,DQ005121,JQ2300 79,JN706548,HQ738 593,HQ611008,JQ23 0073,JQ230071,GU3 90454,GU390429,EF 426134,HQ611010,G U390449,JQ230062,J N706533,JQ818152, EF583048,JX946162, EU372739,JN706545, JQ818155,HQ611007 ,HQ738594,HQ61099 8,JQ230060,HQ7385 88,EF426132,AB7416 53,KC139784,HQ738 596,GU390433,HQ64 1358,DQ923796,EF5 54108,EU372737,GU 390444,JQ230069,G U390460,X94617,GQ 414544,FJ423140,EU 372741,GU390431,E F426135,GU390447,J 0230087,JN706552,J F766582,GU390428,J 0230096,JQ230074,J N706541,EF426121, HQ611024,EF554119 ,GU390434,EU20079 7,EU372740,HQ7385 92,HQ738585,EF583 044,HQ611002,AY60 1553,GU390455,JN7 06534,EU372729,KC 890881,EF583052,E U372749,U04741,JN 104622,JQ087449,E U372734,JQ230098, EU372735,EU679386 ,EF583032,EF426127 ,GU390446,HQ64136 7,JN706553,FJ74762 9,GU390436,FJ42312 9,JN706540,HQ6110 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | 30,JX307601,GU390458,HQ611012,JQ230091,KC890879,JN706549,JQ230067,JQ230075,EF554086,EF426123,EU791923,EF583024,EU556222,EU556223,FJ152131,JN706537,JQ043293,H0738600,GU390457,EF554130,KC890876,HQ738590,HQ611004,JX307602,EF554097,AF531913,GU390456,X94618,GU592515,FJ423150,HQ611015,JQ087438,EU372744,EF583020,GU390435,GU390459,JQ818167,JX416221,EF426133,EU679387,KC890880,JQ230058,HO445976,GU390437,EU330646,JN706539,J0230076 |
| Human rotavirus A | NC_011510 | vertebrates,human | Reoviridae,Rotavirus,Rotavirus A | 68 | seg. 4 | AY787644,FJ423116,EF672577,KC139780,EU679398,HQ445967,EF554118,EF672612,HM627556,HQ445969,JF766581,EF554129,L33895,EU679399,L19712,JF421978,D0887060,JF766592,EU679395,D14032,GQ398013,EF672591,GU320751,FJ435210,EF672584,JQ863312,U16299,EF672570,FJ423127,EU984107,D38054,EF554096,JF766603,GU189554,M60600,L34161,GQ414543,FJ747628,GQ453422,AB741652,FJ435205,AF531909,FJ423138,FJ423149,EF672563,M58292,HM6275 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human rotavirus A RMC/G60 | NC_011503 | vertebrates,human | 1 | Reoviridae,Rotavirus,Rotavirus A | seg. 9 | 45,D38052,EF672605,GQ452950,EF67255 6,EF554107,EU8057 73,FJ747616,EF6725 98,EU984106,HQ445 970,AF260932,EF672 619,U07753,JN70651 0,GQ452951,EU6793 96,AB077766,HQ738 572,AF523677,EU67 9397,EU679400 |
| Human rotavirus A RMC/G66 | NC_011503 | vertebrates,human | 1 | Reoviridae,Rotavirus,Rotavirus A | seg. 9 | AY603151 |
| Human rotavirus A RMC/G7 | NC_011503 | vertebrates,human | 1 | Reoviridae,Rotavirus,Rotavirus A | seg. 9 | AY603152 |
| Human rotavirus A RMC437 | NC_011503 | vertebrates,human | 1 | Reoviridae,Rotavirus,Rotavirus A | seg. 9 | AY603150 |
| Human rotavirus A RMC61 | NC_011503 | vertebrates,human | 1 | Reoviridae,Rotavirus,Rotavirus A | seg. 9 | AY603153 |
| Human rotavirus A strain CMH222 | NC_011504 | vertebrates,human | 1 | Reoviridae,Rotavirus,Rotavirus A | seg. 10 | DQ288660 |
| Human rotavirus A strain CMH222 | NC_011509 | vertebrates,human | 1 | Reoviridae,Rotavirus,Rotavirus A | seg. 6 | DQ288659 |
| Human rotavirus AU-1 | NC_011505 | vertebrates,human | 1 | Reoviridae,Rotavirus,Rotavirus A | seg. 11 | AF373605 |
| Human rotavirus B RMC100 | NC_011510 | vertebrates,human | 1 | Reoviridae,Rotavirus,Rotavirus B | seg. 4 | D10970 |
| Human rotavirus B | NC_021541 | vertebrates,human | 1 | Reoviridae,Rotavirus,Rotavirus B | seg. 1 | EU490415 |
| Human rotavirus B | NC_021542 | vertebrates,human | 1 | Reoviridae,Rotavirus,Rotavirus B | seg. 9 | AY238385 |
| Human rotavirus B | NC_021543 | vertebrates,human | 1 | Reoviridae,Rotavirus,Rotavirus B | seg. 4 | AY238388 |
| Human rotavirus B | NC_021544 | vertebrates,human | 1 | Reoviridae,Rotavirus,Rotavirus B | seg. 6 | AY238389 |
| Human rotavirus B | NC_021545 | vertebrates,human | 1 | Reoviridae,Rotavirus,Rotavirus B | seg. 2 | AY238390 |
| Human rotavirus B | NC_021546 | vertebrates,human | 1 | Reoviridae,Rotavirus,Rotavirus B | seg. 5 | AY238391 |
| Human rotavirus B | NC_021547 | vertebrates,human | 1 | Reoviridae,Rotavirus,Rotavirus B | seg. 7 | AY238392 |
| Human rotavirus B | NC_021548 | vertebrates,human | 1 | Reoviridae,Rotavirus,Rotavirus B | seg. 8 | AY238393 |
| Human rotavirus B | NC_021549 | vertebrates,human | 1 | Reoviridae,Rotavirus,Rotavirus B | seg. 11 | AY238394 |
| Human rotavirus B | NC_021550 | vertebrates,human | 1 | Reoviridae,Rotavirus,Rotavirus B | seg. 10 | AY238384 |
| Human rotavirus B | NC_021551 | vertebrates,human | 1 | Reoviridae,Rotavirus,Rotavirus B | seg. 3 | EU490418 |
| Human rotavirus C | NC_007543 | vertebrates,human | 3 | Reoviridae,Rotavirus,Rotavirus C | seg. 6 | AY941780,AY941782,AY941781 |
| Human rotavirus C | NC_007544 | vertebrates,human | 3 | Reoviridae,Rotavirus,Rotavirus C | seg. 7 | AY820180,AY770977,AY820181 |
| Human rotavirus C | NC_007545 | vertebrates,human | 4 | Reoviridae,Rotavirus,Rotavirus C | seg. 9 | AY781283,JN969078,AY781284,AY770979 |
| Human rotavirus C | NC_007569 | vertebrates,human | 3 | Reoviridae,Rotavirus,Rotavirus C | seg. 10 | AY803727,AY803729,AY770978 |

TABLE 10-continued

VireCap-1.0 Taxonomy

| Taxonomy | Rep.Acc.ID | Host | Lineage | # GN's | Seg. Count | GN.Acc.IDs |
|---|---|---|---|---|---|---|
| Human rotavirus C | NC_007570 | vertebrates,human | Reoviridae,Rotavirus,Rotavirus C | 22 | seg. 5 | AB499614,AM118019,AF325806,AB008672,AB533509,GU592519,AY795898,AY770980,AB533508,AF325805,AB533510,AB648915,M94156,AM118020,AB533511,M94155,EF641110,AY786571,AB533512,AB533513,AY786570,AM118018 |
| Human rotavirus C | NC_007571 | vertebrates,human | Reoviridae,Rotavirus,Rotavirus C | 44 | seg. 8 | AB086963,AF225563,AF225557,AB086968,AB086962,AF225555,AY803724,AF225553,AF225554,AF225561,D87543,AB004250,AF225552,AF225558,AB648916,AM118022,AF225556,AB086969,AF225560,AF323982,AB281654,AB281655,AY803726,AF225559,AM118021,AB086966,M61100,AY392446,AY803725,AF323979,AB499615,AB086964,AB281652,AB00867,AB086967,AF120471,AB086967,AF120478,EF641111,D87544,AB281651,AB281653,AY392447,AF225562,AM118023,AB086965 |
| Human rotavirus C | NC_007572 | vertebrates,human | Reoviridae,Rotavirus,Rotavirus C | 20 | seg. 3 | AY395070,AB533526,AB008670,AM118025,AB533523,AB648917,AB533524,X79441,AB533521,AF323981,AB795897,AM118024,AY795896,AF323980,AY795895,AY395069,AB533525,AB499613,AB533522,AM118026 |

TABLE 10-continued

VíroCap-1.0 Taxonomy

| Taxonomy | Rep.Acc.ID | Host | Lineage | # GN's | Seg. Count | GN.Acc.IDs |
|---|---|---|---|---|---|---|
| Human rotavirus C | NC_007573 | vertebrates,human | Reoviridae,Rotavirus,Rotavirus C | 6 | seg. 11 | AB499612,AB008673,AY941784,D88353,AY770976,AY941783 |
| Human rotavirus G10P11 | NC_011504 | vertebrates,human | Reoviridae,Rotavirus,Rotavirus A | 1 | seg. 10 | AY527229 |
| Human rotavirus G10P[8] | NC_011502 | vertebrates,human | Reoviridae,Rotavirus,Rotavirus A | 1 | seg. 8 | AB714265 |
| Human rotavirus G10P[8] | NC_011506 | vertebrates,human | Reoviridae,Rotavirus,Rotavirus A | 1 | seg. 2 | AB714259 |
| Human rotavirus G10P[8] | NC_011508 | vertebrates,human | Reoviridae,Rotavirus,Rotavirus A | 1 | seg. 3 | AB714260 |
| Human rotavirus G12P[6] | NC_011510 | vertebrates,human | Reoviridae,Rotavirus,Rotavirus A | 3 | seg. 4 | EU839947,EU839946,EU839948 |
| Human rotavirus G1P6 | NC_011504 | vertebrates,human | Reoviridae,Rotavirus,Rotavirus A | 22 | seg. 10 | AF173181,AF173180,AF173182,AF173194,AF173183,AF173184,AF173191,AF173192,AF173179,AF173199,AF173187,AF173197,AF173188,AF173198,AF173193,AF173186,AF173189,AF173190,AF173195,AF173196,AF173200,AF173185 |
| Human rotavirus G1P8 | NC_011504 | vertebrates,human | Reoviridae,Rotavirus,Rotavirus A | 7 | seg. 10 | AF173207,AF173205,AF173201,AF173202,AF173203,AF173204,AF173206 |
| Human rotavirus G1P[8] | NC_011503 | vertebrates,human | Reoviridae,Rotavirus,Rotavirus A | 34 | seg. 9 | GU358423,HQ650876,HQ650871,GU377204,HQ650886,GU377203,GU358420,GU358446,GU358438,HQ650872,GU377196,HQ650882,GU358422,HQ650884,GU358441,HQ650878,GU358844,GU377198,GU358440,GU377201,HQ650881,GU358436,GU358429,GU377200,GU358443,GU358444,GU358442,HQ650879,GU358437,HQ650877,GU358845,GU358843,GU377205,HQ650883 |
| Human rotavirus G1P[8] | NC_011510 | vertebrates,human | Reoviridae,Rotavirus,Rotavirus A | 4 | seg. 4 | EU839957,EU839956,EU839955,EU839958 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human rotavirus G2P4 | NC_011504 | vertebrates,human | 9 | Reoviridae,Rotavirus,Rotavirus A | seg. 10 | AF174298,AF174299, AF174304,AF174300, AF174301,AF174305, AF174302,AY527228, AF174303 |
| Human rotavirus G2P[4] | NC_011510 | vertebrates,human | 4 | Reoviridae,Rotavirus,Rotavirus A | seg. 4 | EU839950,EU839949 ,EU839951,EU83994 5 |
| Human rotavirus G2P[8] | NC_011510 | vertebrates,human | 1 | Reoviridae,Rotavirus,Rotavirus A | seg. 4 | EU839954 |
| Human rotavirus G3P[6] | NC_011504 | vertebrates,human | 1 | Reoviridae,Rotavirus,Rotavirus A | seg. 10 | EU734177 |
| Human rotavirus G3P[8] | NC_011504 | vertebrates,human | 5 | Reoviridae,Rotavirus,Rotavirus A | seg. 10 | AF173210,AF173212, AF173209,AF173211, AF173208 |
| Human rotavirus G4 strain St. Thomas 3 | NC_011503 | vertebrates,human | 1 | Reoviridae,Rotavirus,Rotavirus A | seg. 9 | X13603 |
| Human rotavirus G4 strain VA70 | NC_011504 | vertebrates,human | 1 | Reoviridae,Rotavirus,Rotavirus A | seg. 10 | U83798 |
| Human rotavirus G4P[8] | NC_011504 | vertebrates,human | 4 | Reoviridae,Rotavirus,Rotavirus A | seg. 10 | AF173214,EF011980, AF173215,AF173213 |
| Human rotavirus G5P[6] | NC_011503 | vertebrates,human | 1 | Reoviridae,Rotavirus,Rotavirus A | seg. 9 | AB257126 |
| Human rotavirus G9P6 | NC_011501 | vertebrates,human | 1 | Reoviridae,Rotavirus,Rotavirus A | seg. 7 | EU753969 |
| Human rotavirus G9P6 | NC_011502 | vertebrates,human | 1 | Reoviridae,Rotavirus,Rotavirus A | seg. 8 | EU753970 |
| Human rotavirus G9P6 | NC_011503 | vertebrates,human | 9 | Reoviridae,Rotavirus,Rotavirus A | seg. 9 | AF529871,AF529869, AF529868,AF529865, AF529870,AF529872, AF529867,AF529866, AF529864 |
| Human rotavirus G9P6 | NC_011504 | vertebrates,human | 1 | Reoviridae,Rotavirus,Rotavirus A | seg. 10 | EU753968 |
| Human rotavirus G9P6 | NC_011505 | vertebrates,human | 1 | Reoviridae,Rotavirus,Rotavirus A | seg. 11 | EU753967 |
| Human rotavirus G9P[6] | NC_011501 | vertebrates,human | 1 | Reoviridae,Rotavirus,Rotavirus A | seg. 7 | FJ183359 |
| Human rotavirus G9P[6] | NC_011502 | vertebrates,human | 1 | Reoviridae,Rotavirus,Rotavirus A | seg. 8 | FJ183361 |
| Human rotavirus G9P[6] | NC_011503 | vertebrates,human | 5 | Reoviridae,Rotavirus,Rotavirus A | seg. 9 | FJ183360,AB364381, AB364371,AB364368 ,AB364372 |
| Human rotavirus G9P[6] | NC_011504 | vertebrates,human | 1 | Reoviridae,Rotavirus,Rotavirus A | seg. 10 | FJ183363 |
| Human rotavirus G9P[6] | NC_011505 | vertebrates,human | 1 | Reoviridae,Rotavirus,Rotavirus A | seg. 11 | FJ183362 |
| Human rotavirus G9P[6] | NC_011506 | vertebrates,human | 1 | Reoviridae,Rotavirus,Rotavirus A | seg. 2 | FJ183354 |
| Human rotavirus G9P[6] | NC_011507 | vertebrates,human | 1 | Reoviridae,Rotavirus,Rotavirus A | seg. 1 | FJ183353 |
| Human rotavirus G9P[6] | NC_011508 | vertebrates,human | 1 | Reoviridae,Rotavirus,Rotavirus A | seg. 3 | FJ183355 |
| Human rotavirus G9P[6] | NC_011509 | vertebrates,human | 1 | Reoviridae,Rotavirus,Rotavirus A | seg. 6 | FJ183358 |
| Human rotavirus G9P[6] | NC_011510 | vertebrates,human | 3 | Reoviridae,Rotavirus,Rotavirus A | seg. 4 | FJ183356,EU839952, EU839953 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Human rotavirus G9P[8] | NC_011503 | vertebrates,human | Reoviridae,Rotavirus,Rotavirus A | 11 | seg. 9 | AB364378,AB364370,AB364384,AB364383,AB364382,AB364377,AB364379,AB364373,AB364374,AB364376,AB364375 |
| Human rotavirus G9P[8] | NC_011510 | vertebrates,human | Reoviridae,Rotavirus,Rotavirus A | 4 | seg. 4 | EU839960,EU839961,EU839962,EU839959 |
| Human rotavirus HCR3A | NC_011500 | vertebrates,human | Reoviridae,Rotavirus,Rotavirus A | 1 | seg. 5 | EU708907 |
| Human rotavirus HCR3A | NC_011501 | vertebrates,human | Reoviridae,Rotavirus,Rotavirus A | 1 | seg. 7 | EU708908 |
| Human rotavirus HCR3A | NC_011502 | vertebrates,human | Reoviridae,Rotavirus,Rotavirus A | 1 | seg. 8 | EU708909 |
| Human rotavirus HCR3A | NC_011503 | vertebrates,human | Reoviridae,Rotavirus,Rotavirus A | 1 | seg. 9 | EU708906 |
| Human rotavirus HCR3A | NC_011504 | vertebrates,human | Reoviridae,Rotavirus,Rotavirus A | 1 | seg. 10 | EU708910 |
| Human rotavirus HCR3A | NC_011505 | vertebrates,human | Reoviridae,Rotavirus,Rotavirus A | 1 | seg. 11 | EU708911 |
| Human rotavirus HCR3A | NC_011506 | vertebrates,human | Reoviridae,Rotavirus,Rotavirus A | 1 | seg. 2 | EU708902 |
| Human rotavirus HCR3A | NC_011507 | vertebrates,human | Reoviridae,Rotavirus,Rotavirus A | 1 | seg. 1 | EU708901 |
| Human rotavirus HCR3A | NC_011508 | vertebrates,human | Reoviridae,Rotavirus,Rotavirus A | 1 | seg. 3 | EU708903 |
| Human rotavirus HCR3A | NC_011509 | vertebrates,human | Reoviridae,Rotavirus,Rotavirus A | 1 | seg. 6 | EU708905 |
| Human rotavirus HCR3A | NC_011510 | vertebrates,human | Reoviridae,Rotavirus,Rotavirus A | 1 | seg. 4 | EU708904 |
| Human rotavirus HMGQ35 | NC_011510 | vertebrates,human | Reoviridae,Rotavirus,Rotavirus A | 1 | seg. 4 | AF361438 |
| Human rotavirus II type 1 | NC_011510 | vertebrates,human | Reoviridae,Rotavirus,Rotavirus A | 1 | seg. 4 | D90260 |
| Human rotavirus MP409 | NC_011500 | vertebrates,human | Reoviridae,Rotavirus,Rotavirus A | 1 | seg. 4 | AF143408 |
| Human rotavirus Ro1845 | NC_011501 | vertebrates,human | Reoviridae,Rotavirus,Rotavirus A | 1 | seg. 5 | EU708896 |
| Human rotavirus Ro1845 | NC_011502 | vertebrates,human | Reoviridae,Rotavirus,Rotavirus A | 1 | seg. 7 | EU708897 |
| Human rotavirus Ro1845 | NC_011503 | vertebrates,human | Reoviridae,Rotavirus,Rotavirus A | 1 | seg. 8 | EU708898 |
| Human rotavirus Ro1845 | NC_011504 | vertebrates,human | Reoviridae,Rotavirus,Rotavirus A | 1 | seg. 9 | EU708895 |
| Human rotavirus Ro1845 | NC_011505 | vertebrates,human | Reoviridae,Rotavirus,Rotavirus A | 1 | seg. 10 | EU708899 |
| Human rotavirus Ro1845 | NC_011506 | vertebrates,human | Reoviridae,Rotavirus,Rotavirus A | 1 | seg. 11 | EU708900 |
| Human rotavirus Ro1845 | NC_011507 | vertebrates,human | Reoviridae,Rotavirus,Rotavirus A | 1 | seg. 2 | EU708891 |
| Human rotavirus Ro1845 | NC_011508 | vertebrates,human | Reoviridae,Rotavirus,Rotavirus A | 1 | seg. 1 | EU708890 |
| Human rotavirus Ro1845 | NC_011509 | vertebrates,human | Reoviridae,Rotavirus,Rotavirus A | 1 | seg. 3 | EU708892 |
| Human rotavirus Ro1845 | NC_011510 | vertebrates,human | Reoviridae,Rotavirus,Rotavirus A | 1 | seg. 6 | EU708894 |
| Human rotavirus Ro1845 | NC_011504 | vertebrates,human | Reoviridae,Rotavirus,Rotavirus A | 1 | seg. 4 | EU708893 |
| Human rotavirus serotype 1 strain M37 | NC_011504 | vertebrates,human | Reoviridae,Rotavirus,Rotavirus A | 1 | seg. 10 | U59109 |
| Human rotavirus serotype 2 strain 1076 | NC_011500 | vertebrates,human | Reoviridae,Rotavirus,Rotavirus A | 1 | seg. 10 | U59105 |
| Human rotavirus strain MP409 | NC_011502 | vertebrates,human | Reoviridae,Rotavirus,Rotavirus A | 1 | seg. 5 | AF141916 |
| Human rotavirus strain MP409 | NC_011503 | vertebrates,human | Reoviridae,Rotavirus,Rotavirus A | 1 | seg. 8 | AF141917 |
| Human rotavirus strain MP409 | NC_011503 | vertebrates,human | Reoviridae,Rotavirus,Rotavirus A | 1 | seg. 9 | AF141918 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Human rotavirus strain NnB1 | NC_011510 | vertebrates,human | 1 | Reoviridae,Rotavirus,Rotavirus A | seg. 4 | AF076926 |
| Human rotavirus strain S12/85 | NC_011510 | vertebrates,human | 1 | Reoviridae,Rotavirus,Rotavirus A | seg. 4 | AF076925 |
| IDIR agent X16949 | NC_021551 | vertebrates,human | 1 | Reoviridae,Rotavirus,Rotavirus B | seg. 3 | |
| Ikoma lyssavirus | NC_018629 | vertebrates,human | 1 | Rhabdoviridae, Lyssavirus, I koma lyssavirus | seg. 3 | JX193798 |
| Influenza A virus (A/Puerto Rico/8/1934(H1N1)) | NC_002022 | vertebrates,human | 1 | Orthomyxoviridae,Influenzavirus A,Influenza A virus | seg. 3 | V01106 |
| Influenza A virus (A/Puerto Rico/8/34(H1N1)) | NC_002016 | vertebrates,human | 1 | Orthomyxoviridae,Influenzavirus A,Influenza A virus | seg. 7 | V01099 |
| Influenza A virus (A/Puerto Rico/8/34(H1N1)) | NC_002017 | vertebrates,human | 1 | Orthomyxoviridae,Influenzavirus A,Influenza A virus | seg. 4 | V01088 |
| Influenza A virus (A/Puerto Rico/8/34(H1N1)) | NC_002018 | vertebrates,human | 1 | Orthomyxoviridae,Influenzavirus A,Influenza A virus | seg. 6 | JQ2146 |
| Influenza A virus (A/Puerto Rico/8/34(H1N1)) | NC_002019 | vertebrates,human | 1 | Orthomyxoviridae,Influenzavirus A,Influenza A virus | seg. 5 | JQ2147 |
| Influenza A virus (A/Puerto Rico/8/34(H1N1)) | NC_002020 | vertebrates,human | 1 | Orthomyxoviridae,Influenzavirus A,Influenza A virus | seg. 8 | JQ2150 |
| Influenza A virus (A/Puerto Rico/8/34(H1N1)) | NC_002021 | vertebrates,human | 1 | Orthomyxoviridae,Influenzavirus A,Influenza A virus | seg. 2 | JQ2151 |
| Influenza A virus (A/Puerto Rico/8/34(H1N1)) | NC_002023 | vertebrates,human | 1 | Orthomyxoviridae,Influenzavirus A,Influenza A virus | seg. 1 | V00603 |
| Influenza B virus | NC_002204 | vertebrates,human | 1 | Orthomyxoviridae,Influenzavirus B,Influenza B virus | seg. RNA 1 | M14880 |
| Influenza B virus | NC_002205 | vertebrates,human | 1 | Orthomyxoviridae,Influenzavirus B,Influenza B virus | seg. RNA 2 | AF101982 |
| Influenza B virus | NC_002206 | vertebrates,human | 1 | Orthomyxoviridae,Influenzavirus B,Influenza B virus | seg. RNA 3 | AF102017 |
| Influenza B virus | NC_002207 | vertebrates,human | 1 | Orthomyxoviridae,Influenzavirus B,Influenza B virus | seg. RNA 4 | K00423 |
| Influenza B virus | NC_002208 | vertebrates,human | 1 | Orthomyxoviridae,Influenzavirus B,Influenza B virus | seg. RNA 5 | K01395 |
| Influenza B virus | NC_002209 | vertebrates,human | 1 | Orthomyxoviridae,Influenzavirus B,Influenza B virus | seg. RNA 6 | JQ2095 |
| Influenza B virus | NC_002210 | vertebrates,human | 1 | Orthomyxoviridae,Influenzavirus B,Influenza B virus | seg. RNA 7 | JQ2094 |
| Influenza B virus | NC_002211 | vertebrates,human | 1 | Orthomyxoviridae,Influenzavirus B,Influenza B virus | seg. RNA 8 | JQ2096 |
| Influenza C virus | NC_006306 | vertebrates,human | 29 | Orthomyxoviridae,Influenzavirus C,Influenza C virus | seg. 7 | AB034181,AB034170,AB034165,AB034174,AB034157,DQ0028,AB034161,AB034169,AB034173,AB034180,AB034168,AB034156,AB035367,AB034179,AB034159,AB034166,AB034160,AB0 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Influenza C virus | NC_006307 | vertebrates,human | 2 | Orthomyxoviridae,Influenzavirus C,Influenza C virus | seg. 1 | 34172,AB035366,AB034164,AB034178,AB034158,AB034163,AB034176,AB034177,AB034175,AB034176,AB034167,AB034171 |
| Influenza C virus | NC_006308 | vertebrates,human | 1 | Orthomyxoviridae,Influenzavirus C,Influenza C virus | seg. 2 | M28061,U20228 |
| Influenza C virus | NC_006309 | vertebrates,human | 1 | Orthomyxoviridae,Influenzavirus C,Influenza C virus | seg. 3 | M28060 |
| Influenza C virus | NC_006310 | vertebrates,human | 14 | Orthomyxoviridae,Influenzavirus C,Influenza C virus | seg. 4 | M11643,M11642,M25363,M11639,M11638,M11645,K01689,M11637, M11640,M17868, M25361,M11644, M11641,M25362 |
| Influenza C virus | NC_006312 | vertebrates,human | 2 | Orthomyxoviridae,Influenzavirus C,Influenza C virus | seg. 6 | M17700,M22038 |
| Influenza C virus (C/Aichi/1/81) | NC_006312 | vertebrates,human | 1 | Orthomyxoviridae,Influenzavirus C,Influenza C virus | seg. 6 | D16260 |
| Influenza C virus (C/Ann Arbor/1/50) | NC_006306 | vertebrates,human | 1 | Orthomyxoviridae,Influenzavirus C,Influenza C virus | seg. 7 | AB283001 |
| Influenza C virus (C/Ann Arbor/1/50) | NC_006307 | vertebrates,human | 1 | Orthomyxoviridae,Influenzavirus C,Influenza C virus | seg. 1 | AB126191 |
| Influenza C virus (C/Ann Arbor/1/50) | NC_006308 | vertebrates,human | 1 | Orthomyxoviridae,Influenzavirus C,Influenza C virus | seg. 2 | AB126192 |
| Influenza C virus (C/Ann Arbor/1/50) | NC_006309 | vertebrates,human | 1 | Orthomyxoviridae,Influenzavirus C,Influenza C virus | seg. 3 | AB126193 |
| Influenza C virus (C/Ann Arbor/1/50) | NC_006310 | vertebrates,human | 1 | Orthomyxoviridae,Influenzavirus C,Influenza C virus | seg. 4 | AB126194 |
| Influenza C virus (C/Ann Arbor/1/50) | NC_006311 | vertebrates,human | 1 | Orthomyxoviridae,Influenzavirus C,Influenza C virus | seg. 5 | AB126195 |
| Influenza C virus (C/Ann Arbor/1/50) | NC_006312 | vertebrates,human | 1 | Orthomyxoviridae,Influenzavirus C,Influenza C virus | seg. 6 | AB126196 |
| Influenza C virus (C/Aomori/74) | NC_006310 | vertebrates,human | 1 | Orthomyxoviridae,Influenzavirus C,Influenza C virus | seg. 4 | D63469 |
| Influenza C virus (C/Aomori/74) | NC_006312 | vertebrates,human | 1 | Orthomyxoviridae,Influenzavirus C,Influenza C virus | seg. 6 | D16259 |
| Influenza C virus (C/California/78) | NC_006306 | vertebrates,human | 2 | Orthomyxoviridae,Influenzavirus C,Influenza C virus | seg. 7 | M10087,AB099625 |
| Influenza C virus (C/California/78) | NC_006312 | vertebrates,human | 1 | Orthomyxoviridae,Influenzavirus C,Influenza C virus | seg. 6 | AB000608 |
| Influenza C virus (C/England/83) | NC_006312 | vertebrates,human | 1 | Orthomyxoviridae,Influenzavirus C,Influenza C virus | seg. 6 | AB000725 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Influenza C virus (C/Greece/79) | NC_006306 | vertebrates,human | Orthomyxoviridae,Influenzavirus C,Influenza C virus | 1 | seg. 7 | AB099627 |
| Influenza C virus (C/Hiroshima/246/2000) | NC_006306 | vertebrates,human | Orthomyxoviridae,Influenzavirus C,Influenza C virus | 1 | seg. 7 | AB099619 |
| Influenza C virus (C/Hiroshima/247/2000) | NC_006306 | vertebrates,human | Orthomyxoviridae,Influenzavirus C,Influenza C virus | 1 | seg. 7 | AB099620 |
| Influenza C virus (C/Hiroshima/248/2000) | NC_006306 | vertebrates,human | Orthomyxoviridae,Influenzavirus C,Influenza C virus | 1 | seg. 7 | AB099621 |
| Influenza C virus (C/Hiroshima/249/2000) | NC_006306 | vertebrates,human | Orthomyxoviridae,Influenzavirus C,Influenza C virus | 1 | seg. 7 | AB099618 |
| Influenza C virus (C/Hiroshima/250/2000) | NC_006306 | vertebrates,human | Orthomyxoviridae,Influenzavirus C,Influenza C virus | 1 | seg. 7 | AB099622 |
| Influenza C virus (C/Hiroshima/251/2000) | NC_006306 | vertebrates,human | Orthomyxoviridae,Influenzavirus C,Influenza C virus | 1 | seg. 7 | AB099623 |
| Influenza C virus (C/Hiroshima/252/99) | NC_006306 | vertebrates,human | Orthomyxoviridae,Influenzavirus C,Influenza C virus | 1 | seg. 7 | AB099617 |
| Influenza C virus (C/Hiroshima/290/99) | NC_006312 | vertebrates,human | Orthomyxoviridae,Influenzavirus C,Influenza C virus | 1 | seg. 7 | AB099616 |
| Influenza C virus (C/Hyogo/1/83) | NC_006312 | vertebrates,human | Orthomyxoviridae,Influenzavirus C,Influenza C virus | 1 | seg. 6 | AB000610 |
| Influenza C virus (C/Johannesburg/66) | NC_006310 | vertebrates,human | Orthomyxoviridae,Influenzavirus C,Influenza C virus | 1 | seg. 6 | AB000604 |
| Influenza C virus (C/Kanagawa/1/76) | NC_006312 | vertebrates,human | Orthomyxoviridae,Influenzavirus C,Influenza C virus | 1 | seg. 4 | D63470 |
| Influenza C virus (C/Kanagawa/1/76) | NC_006310 | vertebrates,human | Orthomyxoviridae,Influenzavirus C,Influenza C virus | 1 | seg. 6 | AB000606 |
| Influenza C virus (C/Kansas/1/79) | NC_006306 | vertebrates,human | Orthomyxoviridae,Influenzavirus C,Influenza C virus | 1 | seg. 7 | AB099626 |
| Influenza C virus (C/Kyoto/1/79) | NC_006312 | vertebrates,human | Orthomyxoviridae,Influenzavirus C,Influenza C virus | 1 | seg. 4 | D63472 |
| Influenza C virus (C/Kyoto/1/79) | NC_006306 | vertebrates,human | Orthomyxoviridae,Influenzavirus C,Influenza C virus | 1 | seg. 6 | AB000609 |
| Influenza C virus (C/Kyoto/41/82) | NC_006312 | vertebrates,human | Orthomyxoviridae,Influenzavirus C,Influenza C virus | 1 | seg. 6 | AB000724 |
| Influenza C virus (C/Mississippi/80) | NC_006312 | vertebrates,human | Orthomyxoviridae,Influenzavirus C,Influenza C virus | 1 | seg. 6 | AB000720 |
| Influenza C virus (C/Miyagi/1/93) | NC_006306 | vertebrates,human | Orthomyxoviridae,Influenzavirus C,Influenza C virus | 1 | seg. 7 | AB086790 |
| Influenza C virus (C/Miyagi/1/94) | NC_006306 | vertebrates,human | Orthomyxoviridae,Influenzavirus C,Influenza C virus | 1 | seg. 7 | AB086797 |
| Influenza C virus (C/Miyagi/1/97) | NC_006306 | vertebrates,human | Orthomyxoviridae,Influenzavirus C,Influenza C virus | 1 | seg. 7 | AB086806 |
| Influenza C virus (C/Miyagi/1/99) | NC_006306 | vertebrates,human | Orthomyxoviridae,Influenzavirus C,Influenza C virus | 1 | seg. 7 | AB086809 |
| Influenza C virus (C/Miyagi/2/2000) | NC_006306 | vertebrates,human | Orthomyxoviridae,Influenzavirus C,Influenza C virus | 1 | seg. 7 | AB099609 |
| Influenza C virus (C/Miyagi/2/92) | NC_006306 | vertebrates,human | Orthomyxoviridae,Influenzavirus C,Influenza C virus | 1 | seg. 7 | AB086789 |

TABLE 10-continued

VirоCap-1.0 Taxonomy

| Taxonomy | Rep.Acc.ID | Host | Lineage | # GN's | Seg. Count | GN.Acc.IDs |
|---|---|---|---|---|---|---|
| Influenza C virus (C/Miyagi/2/93) | NC_006306 | vertebrates,human | Orthomyxoviridae,Influenzavirus C,Influenza C virus | 1 | seg. 7 | AB086791 |
| Influenza C virus (C/Miyagi/2/93) | NC_006306 | vertebrates,human | Orthomyxoviridae,Influenzavirus C,Influenza C virus | 1 | seg. 7 | AB086798 |
| Influenza C virus (C/Miyagi/2/94) | NC_006306 | vertebrates,human | Orthomyxoviridae,Influenzavirus C,Influenza C virus | 1 | seg. 7 | AB086800 |
| Influenza C virus (C/Miyagi/2/96) | NC_006306 | vertebrates,human | Orthomyxoviridae,Influenzavirus C,Influenza C virus | 1 | seg. 7 | AB086807 |
| Influenza C virus (C/Miyagi/2/98) | NC_006306 | vertebrates,human | Orthomyxoviridae,Influenzavirus C,Influenza C virus | 1 | seg. 7 | AB099610 |
| Influenza C virus (C/Miyagi/3/2000) | NC_006306 | vertebrates,human | Orthomyxoviridae,Influenzavirus C,Influenza C virus | 1 | seg. 7 | AB086792 |
| Influenza C virus (C/Miyagi/3/93) | NC_006306 | vertebrates,human | Orthomyxoviridae,Influenzavirus C,Influenza C virus | 1 | seg. 7 | AB086799 |
| Influenza C virus (C/Miyagi/3/94) | NC_006306 | vertebrates,human | Orthomyxoviridae,Influenzavirus C,Influenza C virus | 1 | seg. 7 | AB086811 |
| Influenza C virus (C/Miyagi/3/99) | NC_006306 | vertebrates,human | Orthomyxoviridae,Influenzavirus C,Influenza C virus | 1 | seg. 7 | AB099611 |
| Influenza C virus (C/Miyagi/4/2000) | NC_006306 | vertebrates,human | Orthomyxoviridae,Influenzavirus C,Influenza C virus | 1 | seg. 7 | AB086793 |
| Influenza C virus (C/Miyagi/4/93) | NC_006306 | vertebrates,human | Orthomyxoviridae,Influenzavirus C,Influenza C virus | 1 | seg. 7 | AB086801 |
| Influenza C virus (C/Miyagi/4/96) | NC_006306 | vertebrates,human | Orthomyxoviridae,Influenzavirus C,Influenza C virus | 1 | seg. 7 | AB086808 |
| Influenza C virus (C/Miyagi/4/98) | NC_006306 | vertebrates,human | Orthomyxoviridae,Influenzavirus C,Influenza C virus | 1 | seg. 7 | AB099612 |
| Influenza C virus (C/Miyagi/5/2000) | NC_006306 | vertebrates,human | Orthomyxoviridae,Influenzavirus C,Influenza C virus | 1 | seg. 7 | AB086794 |
| Influenza C virus (C/Miyagi/5/93) | NC_006306 | vertebrates,human | Orthomyxoviridae,Influenzavirus C,Influenza C virus | 1 | seg. 7 | AB086795 |
| Influenza C virus (C/Miyagi/6/93) | NC_006306 | vertebrates,human | Orthomyxoviridae,Influenzavirus C,Influenza C virus | 1 | seg. 7 | AB086802 |
| Influenza C virus (C/Miyagi/6/96) | NC_006306 | vertebrates,human | Orthomyxoviridae,Influenzavirus C,Influenza C virus | 1 | seg. 7 | AB086796 |
| Influenza C virus (C/Miyagi/7/93) | NC_006306 | vertebrates,human | Orthomyxoviridae,Influenzavirus C,Influenza C virus | 1 | seg. 7 | AB086803 |
| Influenza C virus (C/Miyagi/7/96) | NC_006310 | vertebrates,human | Orthomyxoviridae,Influenzavirus C,Influenza C virus | 1 | seg. 4 | D63471 |
| Influenza C virus (C/Miyagi/77) | NC_006312 | vertebrates,human | Orthomyxoviridae,Influenzavirus C,Influenza C virus | 1 | seg. 6 | AB000607 |
| Influenza C virus (C/Miyagi/77) | NC_006306 | vertebrates,human | Orthomyxoviridae,Influenzavirus C,Influenza C virus | 1 | seg. 7 | AB086804 |
| Influenza C virus (C/Miyagi/8/96) | NC_006312 | vertebrates,human | Orthomyxoviridae,Influenzavirus C,Influenza C virus | 1 | seg. 6 | AB000614 |
| Influenza C virus (C/Miyagi/9/91) | NC_006306 | vertebrates,human | Orthomyxoviridae,Influenzavirus C,Influenza C virus | 1 | seg. 7 | AB086805 |
| Influenza C virus (C/Nara/1/85) | NC_006312 | vertebrates,human | Orthomyxoviridae,Influenzavirus C,Influenza C virus | 1 | seg. 6 | AB000726 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Influenza C virus (C/Nara/2/85) | NC_006310 | vertebrates,human | Orthomyxoviridae,Influenzavirus C,Influenza C virus | 1 | seg. 4 | D30697 |
| Influenza C virus (C/Nara/2/85) | NC_006312 | vertebrates,human | Orthomyxoviridae,Influenzavirus C,Influenza C virus | 1 | seg. 6 | AB000727 |
| Influenza C virus (C/Nara/82) | NC_006312 | vertebrates,human | Orthomyxoviridae,Influenzavirus C,Influenza C virus | 1 | seg. 6 | AB000723 |
| Influenza C virus (C/NewJersey/76) | NC_006306 | vertebrates,human | Orthomyxoviridae,Influenzavirus C,Influenza C virus | 1 | seg. 7 | AB099624 |
| Influenza C virus (C/Saitama/1/2000) | NC_006306 | vertebrates,human | Orthomyxoviridae,Influenzavirus C,Influenza C virus | 1 | seg. 7 | AB099613 |
| Influenza C virus (C/Saitama/2/2000) | NC_006306 | vertebrates,human | Orthomyxoviridae,Influenzavirus C,Influenza C virus | 1 | seg. 7 | AB099614 |
| Influenza C virus (C/Saitama/3/2000) | NC_006306 | vertebrates,human | Orthomyxoviridae,Influenzavirus C,Influenza C virus | 1 | seg. 7 | AB099615 |
| Influenza C virus (C/Sapporo/71) | NC_006310 | vertebrates,human | Orthomyxoviridae,Influenzavirus C,Influenza C virus | 1 | seg. 4 | D63468 |
| Influenza C virus (C/Sapporo/71) | NC_006312 | vertebrates,human | Orthomyxoviridae,Influenzavirus C,Influenza C virus | 1 | seg. 6 | AB000605 |
| Influenza C virus (C/Shizuoka/79) | NC_006306 | vertebrates,human | Orthomyxoviridae,Influenzavirus C,Influenza C virus | 1 | seg. 7 | AB086788 |
| Influenza C virus (C/Yamagata/1/86) | NC_006312 | vertebrates,human | Orthomyxoviridae,Influenzavirus C,Influenza C virus | 1 | seg. 6 | AB000611 |
| Influenza C virus (C/Yamagata/1/86) | NC_006306 | vertebrates,human | Orthomyxoviridae,Influenzavirus C,Influenza C virus | 1 | seg. 7 | AB002469 |
| Influenza C virus (C/Yamagata/1/86) | NC_006312 | vertebrates,human | Orthomyxoviridae,Influenzavirus C,Influenza C virus | 1 | seg. 6 | D16261 |
| Influenza C virus (C/Yamagata/10/89) | NC_006312 | vertebrates,human | Orthomyxoviridae,Influenzavirus C,Influenza C virus | 1 | seg. 6 | AB000613 |
| Influenza C virus (C/Yamagata/13/98) | NC_006306 | vertebrates,human | Orthomyxoviridae,Influenzavirus C,Influenza C virus | 1 | seg. 7 | AB064445 |
| Influenza C virus (C/Yamagata/2/2000) | NC_006306 | vertebrates,human | Orthomyxoviridae,Influenzavirus C,Influenza C virus | 1 | seg. 7 | AB099605 |
| Influenza C virus (C/Yamagata/2/98) | NC_006306 | vertebrates,human | Orthomyxoviridae,Influenzavirus C,Influenza C virus | 1 | seg. 7 | AB064443 |
| Influenza C virus (C/Yamagata/2/99) | NC_006306 | vertebrates,human | Orthomyxoviridae,Influenzavirus C,Influenza C virus | 1 | seg. 7 | AB099603 |
| Influenza C virus (C/Yamagata/20/96) | NC_006306 | vertebrates,human | Orthomyxoviridae,Influenzavirus C,Influenza C virus | 1 | seg. 7 | AB064442 |
| Influenza C virus (C/Yamagata/26/81) | NC_006306 | vertebrates,human | Orthomyxoviridae,Influenzavirus C,Influenza C virus | 1 | seg. 7 | AB000721 |
| Influenza C virus (C/Yamagata/3/2000) | NC_006306 | vertebrates,human | Orthomyxoviridae,Influenzavirus C,Influenza C virus | 1 | seg. 7 | AB099606 |
| Influenza C virus (C/Yamagata/3/86) | NC_006310 | vertebrates,human | Orthomyxoviridae,Influenzavirus C,Influenza C virus | 1 | seg. 4 | D63473 |
| Influenza C virus (C/Yamagata/3/96) | NC_006306 | vertebrates,human | Orthomyxoviridae,Influenzavirus C,Influenza C virus | 1 | seg. 7 | AB064439 |
| Influenza C virus (C/Yamagata/4/86) | NC_006310 | vertebrates,human | Orthomyxoviridae,Influenzavirus C,Influenza C virus | 1 | seg. 4 | D63503 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Influenza C virus (C/Yamagata/6/2000) | NC_006306 | vertebrates,human | Orthomyxoviridae,Influenzavirus C,Influenza C virus | 1 | seg. 7 | AB099607 |
| Influenza C virus (C/Yamagata/6/98) | NC_006306 | vertebrates,human | Orthomyxoviridae,Influenzavirus C,Influenza C virus | 1 | seg. 7 | AB064444 |
| Influenza C virus (C/Yamagata/64) | NC_006310 | vertebrates,human | Orthomyxoviridae,Influenzavirus C,Influenza C virus | 1 | seg. 4 | D63467 |
| Influenza C virus (C/Yamagata/64) | NC_006312 | vertebrates,human | Orthomyxoviridae,Influenzavirus C,Influenza C virus | 1 | seg. 6 | D16258 |
| Influenza C virus (C/Yamagata/8/2000) | NC_006306 | vertebrates,human | Orthomyxoviridae,Influenzavirus C,Influenza C virus | 1 | seg. 7 | AB099608 |
| Influenza C virus (C/Yamagata/8/86) | NC_006306 | vertebrates,human | Orthomyxoviridae,Influenzavirus C,Influenza C virus | 1 | seg. 6 | AB000612 |
| Influenza C virus (C/Yamagata/8/96) | NC_006306 | vertebrates,human | Orthomyxoviridae,Influenzavirus C,Influenza C virus | 1 | seg. 7 | AB064440 |
| Influenza C virus (C/Yamagata/9/2000) | NC_006306 | vertebrates,human | Orthomyxoviridae,Influenzavirus C,Influenza C virus | 1 | seg. 7 | AB099604 |
| Influenza C virus (C/Yamagata/9/86) | NC_006312 | vertebrates,human | Orthomyxoviridae,Influenzavirus C,Influenza C virus | 1 | seg. 6 | AB000728 |
| Influenza C virus (C/Yamagata/9/96) | NC_006306 | vertebrates,human | Orthomyxoviridae,Influenzavirus C,Influenza C virus | 1 | seg. 7 | AB064441 |
| Influenza C virus (C/pig/Beijing/115/81) | NC_006312 | vertebrates,human | Orthomyxoviridae,Influenzavirus C,Influenza C virus | 1 | seg. 6 | AB000722 |
| Influenza C virus (STRAIN C/BERLIN/1/85) | NC_006307 | vertebrates,human | Orthomyxoviridae,Influenzavirus C,Influenza C virus | 1 | seg. 1 | X55992 |
| Influenza C virus (STRAIN C/TAYLOR/1233/47) | NC_006312 | vertebrates,human | Orthomyxoviridae,Influenzavirus C,Influenza C virus | 1 | seg. 6 | D26546 |
| Ippy virus | NC_007905 | vertebrates,human | Arenaviridae,Arenavirus,Ippy virus | 1 | seg. S | DQ328877 |
| Ippy virus | NC_007906 | vertebrates,human | Arenaviridae,Arenavirus,Ippy virus | 1 | seg. L | DQ328878 |
| Irkut virus | NC_020809 | vertebrates,human | Rhabdoviridae,Lyssavirus,Irkut virus | 2 | — | JX442979,EF614260 |
| Italian lapine rotavirus 30/96 | NC_011500 | vertebrates,human | Reoviridae,Rotavirus,Rotavirus A | 1 | seg. 5 | DQ205225 |
| Italian lapine rotavirus 30/96 | NC_011501 | vertebrates,human | Reoviridae,Rotavirus,Rotavirus A | 1 | seg. 7 | DQ205227 |
| Italian lapine rotavirus 30/96 | NC_011502 | vertebrates,human | Reoviridae,Rotavirus,Rotavirus A | 1 | seg. 8 | DQ205228 |
| Italian lapine rotavirus 30/96 | NC_011503 | vertebrates,human | Reoviridae,Rotavirus,Rotavirus A | 1 | seg. 9 | DQ205229 |
| Italian lapine rotavirus 30/96 | NC_011504 | vertebrates,human | Reoviridae,Rotavirus,Rotavirus A | 1 | seg. 10 | DQ205230 |
| Italian lapine rotavirus 30/96 | NC_011505 | vertebrates,human | Reoviridae,Rotavirus,Rotavirus A | 1 | seg. 11 | DQ205231 |
| Italian lapine rotavirus 30/96 | NC_011506 | vertebrates,human | Reoviridae,Rotavirus,Rotavirus A | 1 | seg. 2 | DQ205222 |
| Italian lapine rotavirus 30/96 | NC_011507 | vertebrates,human | Reoviridae,Rotavirus,Rotavirus A | 1 | seg. 1 | DQ205221 |
| Italian lapine rotavirus 30/96 | NC_011508 | vertebrates,human | Reoviridae,Rotavirus,Rotavirus A | 1 | seg. 3 | DQ205223 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Italian lapine rotavirus 30/96 | NC_011509 | vertebrates,human | Reoviridae,Rotavirus,Rotavirus A | 1 | seg. 6 | DQ205226 |
| Italian lapine rotavirus 30/96 | NC_011510 | vertebrates,human | Reoviridae,Rotavirus,Rotavirus A | 1 | seg. 4 | DQ205224 |
| J-virus | NC_007454 | vertebrates,human | Paramyxoviridae,J-virus | 1 | — | AY900001 |
| JC polyomavirus | NC_001699 | vertebrates,human | Polyomaviridae,Polyomavirus,JC polyomavirus | 592 | — | AB262401,JF424911, AB092584,AB074591, AB127013,AB11312 1,AY366359,AB1182 33,AB127350,AB126 983,AB077869,AB18 3152,AB127346,AY5 36242,AB077859,JF4 24922,AB092582,AB 081007,JF424869,JF 424874,JF424877,AF 363833,AB081612,A B127006,AB077864,J F424835,AB048553,A Y536239,JF424859,A B362360,AB118652, AB118234,JF424952, JF425504,JF424875, JF424837,AB372036, AB262397,AY121908 ,AB113142,AY38637 7,AB038254,JF42495 8,AB113137,JF42548 9,AB048568,AF28161 7,AY121913,AB1989 46,JF425556,AB0382 52,AB103404,JF4248 85,JF424954,AB2209 41,AB048580,JF4255 51,AB081654,AB113 131,AB077866,AB12 7011,AB077879,JF42 4909,AB126991,AB2 20940,AB081018,AB 113135,AF396430,AF 300964,AB074581,A B118657,AB198940, AB074588,AY382187 ,AB048572,AB04857 6,AB081608,AB3623 63,AB127023,JF4249 42,JF424855,JF4249 08,AB048569,JF4248 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 43,AB103421,AB198947,JF424880,AY121914,JQ237146,AF363834,AB048574,JF425494,AB362351,AB262410,AY386776,AB127343,AF396435,AB092587,AB081604,JF424857,AB185020,AF281624,JF424923,JF425493,JF424939,AB081022,AB081013,AB092579,JF424860,AB081602,AB103387,AB262399,JF424894,AB048561,AB077873,AB127026,JF424936,AB262413,JF424864,AF300959,AB198944,AB262402,AB081030,AB103418,AB262412,AB081027,JF424876,AB048566,JF424900,AB103411,AF004350,AB081603,AB127342,AF396429,AB118653,AB127344,AB118651,AB113123,AB081016,AB038253,AB077863,JF424917,AB081005,JF425498,AF281625,AB198949,JF424863,JF424951,JF424886,AB077874,JF424885,AY536241,JQ823124,AB118231,AF300963,JF424926,JF424960,JF424910,AB103419,AY378084,JF424845,AB081015,AB048577,AB127347,AB198942,AB127352,JF424851,JF424919,AB126994,AB113118,JF424870,AB081021,AB126984,AF300953,JF424883,AB081024,AB127348,JF424892,J |

TABLE 10-continued

VicoCap-1.0 Taxonomy

| Taxonomy | Rep.Acc.ID | Host | # GN's | Lineage | Seg. Count | GN.Acc.IDs |
|---|---|---|---|---|---|---|
| | | | | | | F42930,AB113139,AB26403,AB126993,AB127003,JF424918,JF424941,AB127002,AF36832,AB127025,AB126982,JF425490,AB103409,AB048548,JF424920,AF300955,AB074577,AB08160 5,AB081020,AY3565 39,AB212954,AB113 138,AB113126,JF424 890,JF424937,JF424 953,JF424949,AB074 585,AB113133,AB04 8554,U61771,JF4249 28,JF424938,JF4248 61,AB048557,AB212 953,AB081008,AB12 7345,AB262404,AY3 42299,JF424878,AB2 62405,AF396428,AB0 74576,AB113143,JX2 73163,AF300951,AB1 27000,AY536240,AB 262408,AB118654,AF 281626,JF424856,AB 048558,U73501,AB04 8565,AB362366,JF42 4850,AF281623,AB12 7024,AB081012,AB1 18656,JF424962,JF4 25499,AB126998,JF4 24933,AF396433,AB3 62356,AB081006,AB 074582,AB081613,A B074583,AB262396, AB092583,AF300947, AF300952,AB198943, AB081601,AY386373 ,AB081023,AB12701 8,AB198953,AB0778 75,JF425501,AB1273 51,AB126996,AB127 016,AB118235,AB09 2578,AB077860,JF42 4848,AB048575,JF42 4873,AB220943,AY3 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 76830,AB077872,DQ 875212,AF300954,AB 048582,JF424853,JF 425491,AB103406,JF 424893,JF424913,AY 376831,AB103405,A B077861,AF295732,J F424881,AB127021,J F424842,AB127001,J 02226,AB077857,AB 362352,AB048571,A B048547,AB113124, AB103417,AF004349, JF424945,AB198945, JF424897,AB126988, AB372037,AB048552 ,AB074589,JF424961 ,AF396432,JF424891 ,AB077871,JF424865 ,JF424935,AB126981 ,JF424879,AB081616 ,AF396427,JF424895 ,AF300957,AB127007 ,AY378086,JF424866 ,AB220942,JF424839 ,AY378087,AB10342 2,AB081025,AB1131 19,AF300946,AB1132 17,AB103412,AB081 019,AB113122,AF300 960,JF425554,AB077 855,JF424959,AB104 487,AB081614,AB04 8564,AB103415,AB1 13140,AB092585,AB 198952,AB077877,A B126999,JF424957,A B362357,AB048560, AB198954,AB081611 ,JF425503,JF424882, AB113129,JF424905, JF424871,JF425552, AB048559,DQ875211 ,AB118232,AB07786 7,AB113130,AB1270 22,JF424947,AF3964 24,AB113216,AY121 912,AB048567,AB08 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 1615,AF300948,AF300962,AB362355,AY349147,JF424862,AB077865,JF424852,AB195639,JF424899,JF424906,AB126985,AY382184,JF424844,JF424925,JF424903,AB103414,AB127004,AB074575,AB103407,AB118658,AB262406,AB103413,JF424916,JF424931,AB081017,AF363831,JF424944,AB103403,AB048563,AB077862,AF363830,JF424898,AB081011,AB127015,JF424929,JF424927,AB077868,AF396434,AB081010,AY328376,AB048562,AB038251,U73500,AB103402,AB220939,AB126990,AB081029,JF424902,AF300965,JF424849,AB081607,JF424921,JF424868,AB077858,JF424932,JF424872,JF424948,AF396426,AB362362,AF396423,JF424904,AF281615,AF300949,JF424896,AB081610,AB127008,AY376828,JF424950,AB081009,AF300958,AF295731,AB262400,AB262398,AY376829,AB127012,JF425502,AB126987,AB081606,AY386378,AB048570,AB118655,AB048546,AY121915,AB113132,AB372038,AB038255,AY378085,JF424888,AB081618,AB362353,AY536243,AB126992,AB092580,AB07 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 7856,JF424924,AB36 2364,JF425492,JF42 4955,AB048556,AB0 77870,AB126989,JF4 24907,AY364314,AF0 30085,AB262411,AB 127349,AB126986,A Y121909,AY386374,J F422854,AB074586,J F424847,AY121907,A B074579,JF425555,A B113141,AB077876, AB103423,AB118659 ,AB113144,AB19564 0,AB103420,AB2624 07,JF424901,AF2816 16,JF424858,AB1131 34,JF425500,AY1219 11,AB362359,U73502 ,AB081600,AB11313 6,AB113125,AB1131 45,JF424834,AF3964 22,AY382188,AY386 375,AB092581,AB10 3416,JF425488,JF42 4943,AB198948,AB2 12952,AF300967,AB0 48545,AB081617,AB 113120,EU835194,JF 424841,AB048581,A B074590,JF424956,J F424912,AB048579,A B081028,AB048549, AB074578,AB362361 ,JF425495,AB126997 ,AB198941,AY38218 5,AB038250,JF42549 7,JF424846,JF42491 4,AB198951,AB1270 10,AF300956,JF4248 67,AB362358,AB262 409,AY382186,AB03 8249,JF424934,AB04 8550,JF424884,AB04 8573,JF424838,AB07 4584,AY373463,AB0 74580,AB127017,AB 048851,AF300945,AB |

TABLE 10-continued

VircCap-1.0 Taxonomy

| Taxonomy | Rep.Acc.ID | Host | # GN's | Lineage | Seg. Count | GN.Acc.IDs |
|---|---|---|---|---|---|---|
| | | | | | | 362365,AB081609,JF424946,AB113127,AB113128,AB048555,AB127353,AB077878,JF424915,AF295738,AB092586,AF300950,JF424889,AB127027,AY121910,AB127020,AB103408,JF424840,AB127005,AB362354,JF424836,AB081026,AB126995,JF425496,AF396431,AF300961,AB127014,AB103410,AF300966,AF396425,AB198950,AB081014,JF424887,AB127019,AB048578,AB074587,AB127009,JF424940 |
| Junin virus | NC_005080 | vertebrates,human | 16 | Arenaviridae,Arenavirus,Junin virus | seg. L | JF799

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| K1 polyomavirus | NC_009238 | vertebrates,human | 6 | Polyomaviridae,Polyomavirus,KI polyomavirus | — | EU358767,EF520287,EF520288,EU358766,EF127906,EF520289 |
| K1 polyomavirus Stockholm 350 | NC_009238 | vertebrates,human | 1 | Polyomaviridae,Polyomavirus,KI polyomavirus | — | EF127907 |
| K1 polyomavirus Stockholm 380 | NC_009238 | vertebrates,human | 1 | Polyomaviridae,Polyomavirus,KI polyomavirus | — | EF127908 |
| Lagos bat virus | NC_020807 | vertebrates,human | 5 | Rhabdoviridae,Lyssavirus,Lagos bat virus | — | EU259198,GU170202,EU293108,EU293110,JX901139 |
| Lake Victoria marburgvirus | NC_001608 | vertebrates,human | 14 | Filoviridae,Marburgvirus,Marburg marburgvirus | — | FJ750954,FJ750953,Z29337,AY358025,Z12132,FJ750956,FJ750957,AY430365,FJ750959,AY430366,DQ217792,FJ750958,FJ750955,GQ433353 |
| Lake Victoria marburgvirus-Angola2005 | NC_001608 | vertebrates,human | 8 | Filoviridae,Marburgvirus,Marburg marburgvirus | — | DQ447658,DQ447659,DQ447654,DQ447660,DQ447656,DQ447653,DQ447657,DQ447655 |
| Lake Victoria marburgvirus-Ci67 | NC_001608 | vertebrates,human | 1 | Filoviridae,Marburgvirus,Marburg marburgvirus | — | EF446132 |
| Lake Victoria marburgvirus-DRC1999 | NC_001608 | vertebrates,human | 3 | Filoviridae,Marburgvirus,Marburg marburgvirus | — | DQ447650,DQ447652,DQ447765 |
| Lake Victoria marburgvirus-Leiden | NC_001608 | vertebrates,human | 1 | Filoviridae,Marburgvirus,Marburg marburgvirus | — | JN408064 |
| Lake Victoria marburgvirus-Ravn | NC_001608 | vertebrates,human | 2 | Filoviridae,Marburgvirus,Marburg marburgvirus | — | DQ447649,EF446131 |
| Lamb rotavirus | NC_011500 | vertebrates,human | 2 | Reoviridae,Rotavirus,Rotavirus A | seg. 5 | HQ834202,FJQ31019 |
| Lamb rotavirus | NC_011501 | vertebrates,human | 2 | Reoviridae,Rotavirus,Rotavirus A | seg. 7 | HQ834204,FJQ31020 |
| Lamb rotavirus | NC_011502 | vertebrates,human | 3 | Reoviridae,Rotavirus,Rotavirus A | seg. 8 | HQ834203,FJQ31021,JQ031147 |
| Lamb rotavirus | NC_011503 | vertebrates,human | 2 | Reoviridae,Rotavirus,Rotavirus A | seg. 9 | HQ834201,FJQ31029 |
| Lamb rotavirus | NC_011504 | vertebrates,human | 4 | Reoviridae,Rotavirus,Rotavirus A | seg. 10 | HQ834205,JQ031148,FJQ31022,AY219873 |
| Lamb rotavirus | NC_011505 | vertebrates,human | 4 | Reoviridae,Rotavirus,Rotavirus A | seg. 11 | FJQ31023,HQ834206,JQ031151,AY622998 |
| Lamb rotavirus | NC_011506 | vertebrates,human | 3 | Reoviridae,Rotavirus,Rotavirus A | seg. 2 | HQ834198,JQ013503,FJQ31025 |
| Lamb rotavirus | NC_011507 | vertebrates,human | 3 | Reoviridae,Rotavirus,Rotavirus A | seg. 1 | JQ013502,HQ834197,FJQ31024 |
| Lamb rotavirus | NC_011508 | vertebrates,human | 3 | Reoviridae,Rotavirus,Rotavirus A | seg. 3 | HQ834207,FJQ31026,JQ013504 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Lamb rotavirus | NC_011509 | vertebrates,human | 6 | Reoviridae,Rotavirus,Rotavirus A | seg. 6 | JQ031150,L11602,L11595,HQ834200,FJQ31028,L11596 |
| Lamb rotavirus | NC_011510 | vertebrates,human | 3 | Reoviridae,Rotavirus,Rotavirus A | seg. 4 | HQ834199,FJQ31027,L11599 |
| Lapine rotavirus | NC_011500 | vertebrates,human | 4 | Reoviridae,Rotavirus,Rotavirus A | seg. 5 | AF084549,AF084550,JQ423897,AF084551 |
| Lapine rotavirus | NC_011501 | vertebrates,human | 1 | Reoviridae,Rotavirus,Rotavirus A | seg. 7 | JQ423899 |
| Lapine rotavirus | NC_011502 | vertebrates,human | 1 | Reoviridae,Rotavirus,Rotavirus A | seg. 8 | JQ423898 |
| Lapine rotavirus | NC_011503 | vertebrates,human | 2 | Reoviridae,Rotavirus,Rotavirus A | seg. 9 | U62153,JQ423907 |
| Lapine rotavirus | NC_011504 | vertebrates,human | 1 | Reoviridae,Rotavirus,Rotavirus A | seg. 10 | JQ423900 |
| Lapine rotavirus | NC_011505 | vertebrates,human | 1 | Reoviridae,Rotavirus,Rotavirus A | seg. 11 | JQ423901 |
| Lapine rotavirus | NC_011506 | vertebrates,human | 1 | Reoviridae,Rotavirus,Rotavirus A | seg. 2 | JQ423903 |
| Lapine rotavirus | NC_011507 | vertebrates,human | 1 | Reoviridae,Rotavirus,Rotavirus A | seg. 1 | JQ423902 |
| Lapine rotavirus | NC_011508 | vertebrates,human | 1 | Reoviridae,Rotavirus,Rotavirus A | seg. 3 | JQ423904 |
| Lapine rotavirus | NC_011509 | vertebrates,human | 1 | Reoviridae,Rotavirus,Rotavirus A | seg. 6 | JQ423906 |
| Lapine rotavirus | NC_011510 | vertebrates,human | 5 | Reoviridae,Rotavirus,Rotavirus A | seg. 4 | U62150,JQ423905,U62151,U62152,U62149 |
| Lapine rotavirus strain BAP (wildtype) | NC_011504 | vertebrates,human | 1 | Reoviridae,Rotavirus,Rotavirus A | seg. 10 | AF144796 |
| Lapine rotavirus strain BAP-2 | NC_011504 | vertebrates,human | 1 | Reoviridae,Rotavirus,Rotavirus A | seg. 10 | AF144795 |
| Lapine rotavirus strain C-11 | NC_011504 | vertebrates,human | 1 | Reoviridae,Rotavirus,Rotavirus A | seg. 10 | AF144793 |
| Lapine rotavirus strain R-2 | NC_011504 | vertebrates,human | 1 | Reoviridae,Rotavirus,Rotavirus A | seg. 10 | AF144794 |
| Lassa virus | NC_004296 | vertebrates,human | 16 | Arenaviridae,Arenavirus,Lassa virus | seg. S | AY628208,X52400,AF181854,AY628201,AF333969,AY628207,AY628206,HQ688672,AF246121,AY628205,AY628203,HQ688673,AF181853,JQ4324,AY179173,FR832711 |
| Lassa virus | NC_004297 | vertebrates,human | 11 | Arenaviridae,Arenavirus,Lassa virus | seg. L | HQ688675,AY179172,AY628204,U63094,AY179171,AY179174,FR832710,AY628200,U73034,HQ688674,AY628202 |
| Latino virus | NC_010758 | vertebrates,human | 2 | Arenaviridae,Arenavirus,Latino virus | seg. S | AF485259,AF512830 |
| Latino virus | NC_010760 | vertebrates,human | 1 | Arenaviridae,Arenavirus,Latino virus | seg. L | EU627612 |
| Lechiguanas virus | NC_003466 | vertebrates,human | 1 | Bunyaviridae,Hantavirus,Andes virus | seg. S | AF482714 |
| Lechiguanas virus | NC_003467 | vertebrates,human | 1 | Bunyaviridae,Hantavirus,Andes virus | seg. M | AF028022 |
| Lloviu virus | NC_016144 | vertebrates,human | 1 | Filoviridae,Lloviu virus | — | JF828358 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Lordsdale virus | NC_001959 | vertebrates,human | 1 | Caliciviridae,Norovirus,Norwalk virus | — | X86557 |
| Lujo virus | NC_012776 | vertebrates,human | 2 | Arenaviridae,Arenavirus,Lujo virus | seg. S | JXQ17360,FJ952384 |
| Lujo virus | NC_012777 | vertebrates,human | 2 | Arenaviridae,Arenavirus,Lujo virus | seg. L | JXQ17362,FJ952385 |
| Luna virus | NC_016152 | vertebrates,human | 5 | Arenaviridae,Arenavirus,Luna virus | seg. S | AB586644,AB697691,AB586646,AB70294 0,AB693148 |
| Luna virus | NC_016153 | vertebrates,human | 5 | Arenaviridae,Arenavirus,Luna virus | seg. L | AB693149,AB586645,AB586647,AB70294 1,AB697692 |
| Lunk virus NKS-1 | NC_018710 | vertebrates,human | 1 | Arenaviridae,Arenavirus,Lunk virus NKS-1 | — | AB693150 |
| Lunk virus NKS-1 | NC_018711 | vertebrates,human | 1 | Arenaviridae,Arenavirus,Lunk virus NKS-1 | — | AB693151 |
| Lymphocytic choriomeningitis virus | NC_004291 | vertebrates,human | 16 | Arenaviridae,Arenavirus,Lymphocytic choriomeningitis virus | seg. L | JN872494,EU480451, DQ868488,EU195889 ,JQ4331,AB627954,E U480453,DQ868484, DQ286932,DQ868486 6,AB627956,AB4775 30,DQ361066,GQ862 981,AB627955,AF004 519 |
| Lymphocytic choriomeningitis virus | NC_004294 | vertebrates,human | 25 | Arenaviridae,Arenavirus,Lymphocytic choriomeningitis virus | seg. S | JN872495,AY847351, EU480452,AB627952 ,AB261991,DQ86848 5,DQ361065,FJ89588 2,DQ286931,DQ8684 87,FJ895883,AF3252 14,AF325215,M2213 8,FJ895884,AB26199 0,GQ862982,DQ1189 59,AB627951,JN6879 49,AB627953,EU480 450,M20869,AY8473 50,DQ868483 |
| Macaca fascicularis papillomavirus 2 | NC_015691 | vertebrates,human | 1 | Papillomaviridae,Betapapillomavirus,Betapapil lomavirus 6 | — | GU014531 |
| Macaca fascicularis papillomavirus type 1 | NC_001531 | vertebrates,human | 1 | Papillomaviridae,Betapapillomavirus,Betapapil lomavirus 1 | — | EF028290 |
| Machupo virus | NC_005078 | vertebrates,human | 3 | Arenaviridae,Arenavirus,Machupo virus | seg. S | JN794584,AY129248, JN794586 |
| Machupo virus | NC_005079 | vertebrates,human | 3 | Arenaviridae,Arenavirus,Machupo virus | seg. L | AY358021,JN794583, JN794585 |
| Maciel virus | NC_003466 | vertebrates,human | 1 | Bunyaviridae,Hantavirus,Andes virus | seg. S | AF482716 |
| Mamastrovirus 1 | NC_001943 | vertebrates,human | 1 | Astroviridae,Mamastrovirus,Mamastrovirus 1 | — | Z25771 |
| Maporal virus | NC_003466 | vertebrates,human | 1 | Bunyaviridae,Hantavirus,Andes virus | seg. S | AY267347 |
| Maporal virus | NC_003467 | vertebrates,human | 1 | Bunyaviridae,Hantavirus,Andes virus | seg. M | AY363179 |
| Mapuera virus | NC_009489 | vertebrates,human | 1 | Paramyxoviridae,Rubulavirus,Mapuera virus | — | EF095490 |
| Marburg marburgvirus | NC_001608 | vertebrates,human | 36 | Filoviridae,Marburgvirus,Marburg marburgvirus | — | JX458844,JX458854, JX458858,JX458852, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Measles virus | NC_001498 | vertebrates,human | 50 | Paramyxoviridae,Morbillivirus,Measles virus | — | JX458847,JX458827,JX458843,JX458830,JX458833,JX458850,JX458857,JX458849,JX458842,JX458831,JX458835,JX458826,JX458836,JX458851,JX458825,KC545388,JX458856,JX458845,JX458838,JX458834,JX458846,JX458829,JX458848,JX458837,JX458828,JX458832,JX458841,JX458853,JX458839,KC545387,JX458855,JX458840,EU433017,DQ345721,AB481088,EU29355 0,K01711,EF04903,DQ 227318,BD137596,B D137590,EU293551, AY730614,AB254456,FJ416067,AB016162,AB046218,DQ222732,1,AB591381,JF72765 0,BD137593,AF2662 88,FJ161211,JF7276 49,FJ211590,DQ3457 22,HM439386,Z6651 7,DQ227320,FJ21158 3,BD137595,AB0129 49,EU293552,DQ211 902,AB481087,GQ37 6027,EU293549,GQ3 76026,BD137592,AB 032167,BD137591,D 345723,BD137597, FJ416068,S58435,JF 791787,EF03307 1,E U293548,BD137594, DQ227319,AB012948,FJ211589 |
| Measles virus genotype D4 | NC_001498 | vertebrates,human | 1 | Paramyxoviridae,Morbillivirus,Measles virus | — | KC164757 |
| Measles virus genotype G3 | NC_001498 | vertebrates,human | 1 | Paramyxoviridae,Morbillivirus,Measles virus | — | KC164758 |
| Measles virus strain AIK-C | NC_001498 | vertebrates,human | 1 | Paramyxoviridae,Morbillivirus,Measles virus | — | AF266286 |
| Measles virus strain Edmonston-Zagreb | NC_001498 | vertebrates,human | 3 | Paramyxoviridae,Morbillivirus,Measles virus | — | AY486083,AY486084,AF266290 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Measles virus strain MVi/Arizona,USA/11,08/2 | NC_001498 | vertebrates,human | 1 | Pa TABLE 10-continued ViroCap-1.0 Taxonomy

| Taxonomy | Rep.Acc.ID | Host | # GN's | Lineage | Seg. Count | GN.Acc.IDs |
|---|---|---|---|---|---|---|
| Mobala virus | NC_007903 | vertebrates,human | 1 | Arenaviridae,Arenavirus,Mobala virus | seg. S | 11551,HM01545,JQ479317,JF813003,HM011549,HM011539,JQ479316,HM011541,JQ479318 |
| Mobala virus | NC_007904 | vertebrates,human | 1 | Arenaviridae,Arenavirus,Mobala virus | seg. L | AY342390 |
| Mokola virus | NC_006429 | vertebrates,human | 7 | Rhabdoviridae,Lyssavirus,Mokola virus | — | DQ328876,KF155007,EU293117,KF155008,Y09762,KF155005,KF155006,EU293118 |
| Mopeia Lassa reassortant 29 | NC_006572 | vertebrates,human | 1 | Arenaviridae,Arenavirus,Mopeia Lassa virus reassortant 29 | seg. L | AY772167 |
| Mopeia Lassa reassortant 29 | NC_006573 | vertebrates,human | 1 | Arenaviridae,Arenavirus,Mopeia Lassa virus reassortant 29 | seg. S | AY772168 |
| Mopeia virus | NC_006574 | vertebrates,human | 1 | Arenaviridae,Arenavirus,Mopeia virus | seg. L | DQ328875 |
| Mopeia virus | NC_006575 | vertebrates,human | 2 | Arenaviridae,Arenavirus,Mopeia virus | seg. S | DQ328874,M33879 |
| Mopeia virus AN20410 | NC_006574 | vertebrates,human | 1 | Arenaviridae,Arenavirus,Mopeia virus | seg. L | AY772169 |
| Mopeia virus AN20410 | NC_006575 | vertebrates,human | 1 | Arenaviridae,Arenavirus,Mopeia virus | seg. S | AY772170 |
| Morogoro virus | NC_013057 | vertebrates,human | 1 | Arenaviridae,Arenavirus,Morogoro virus | seg. S | EU914103 |
| Morogoro virus | NC_013058 | vertebrates,human | 1 | Arenaviridae,Arenavirus,Morogoro virus | seg. L | EU914104 |
| Mossman virus | NC_005339 | vertebrates,human | 1 | Paramyxoviridae, Mossman virus | — | AY286409 |
| Mumps virus | NC_002200 | vertebrates,human | 50 | Paramyxoviridae,Rubulavirus,Mumps virus | — | AF314560,AB000386,JX287385,AB744048,DQ649478,FJ375178,FJ211584,AXQ81123,JX287387,HQ416906,HQ416907,JF727652,AF314559,AXQ81134,AB470486,AB57676 4,AF201473,AY309060,FJ375177,AY68149 5,JX287390,AF28079 9,AF314562,EU3702 06,AB600942,FJ2115 85,JN012242,AB0003 87,AB60843,AB744 049,JF727651,GU980 052,AXQ81133,FJ211 586,AB040874,AB0O 0388,JN635498,AF46 7767,AF314561,EU3 70207,FJ556896,EU8 84413,AF314558,AB8 27968,JX287389,JX2 87388,AY669145,JX2 87386,AY508995,JX2 87391 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Mumps virus strain Jeryl Lynn | NC_002200 | vertebrates,human | 3 | Paramyxoviridae,Rubulavirus,Mumps virus | — | FN431985,AF345290,AF338106 |
| Mumps virus strain L-Zagreb | NC_002200 | vertebrates,human | 2 | Paramyxoviridae,Rubulavirus,Mumps virus | — | AY685920,AY685921 |
| Murine pneumonia virus | NC_006579 | vertebrates,human | 1 | Paramyxoviridae,Pneumovirus,Murine pneumonia virus | — | AY729016 |
| Nariva virus | NC_017937 | vertebrates,human | 1 | Paramyxoviridae,Nariva virus | — | FJ362497 |
| Newcastle disease virus | NC_002617 | vertebrates,human | 216 | Paramyxoviridae,Avulavirus,Newcastle disease virus | — | KC542892,KC152049,JN986838,KC542900,JF966387,KC920893,KC542904,HM117720,JQ979176,HQ412767,JX443519,JX193074,JF343539,FJ430160,GQ338309,GQ849007,KC542897,AY935495,FJ436302,HM357251,HM125898,JQ013039,FJ386392,BD218398,JX532092,JX193081,DQ485231,JF343538,HQ697254,AY562986,GQ994433,KC894391,EU293914,AY935493,KC84423,5,HQ902590,GQ288378,DQ486859,JX401403,GQ918280,HQ317395,AY935496,HQ717357,FJ766527,JX401404,JN653340,JX193079,AB524406,KC542902,JN800306,FJ754271,JF950510,AY935499,JX390609,D0659677,JQ015296,HM063424,JX316216,AB534205,Y18898,FJ436305,HM063425,KC542896,AY935494,HQ697255,KC55196,7,FJ794269,KC542893,JQ993431,KC54529,13,HQ266602,JX193083,AY225110,AY935489,GQ288389,JF827027,HM063423,FJ751918,GU187941,J |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | N599167,GQ288391,FJ872531,GQ994434,AY741404,HM063422,AY935497,HQ008337,GQ338310,JXQ12096,KC542914,AY935492,KC934169,FJ1386393,JX393313,KF771883,HM188399,JF950509,EU289028,AY562987,AY562985,JX193078,FJ436303,JN688863,AY865652,JN400896,KF727980,G0288390,KC542908,JF893453,AY935498,GU143550,KC152048,KC542901,JQ015295,JN400895,KC906188,IN688862,FJ986192,KC542905,EU289029,FJ386396,JN618349,EU140955,FJ143636,GU978777,JX524203,JX401405,JN653339,FJ766529,JN682211,JF827026,JX193082,JN682210,GQ288392,HQ839733,AF060053,AB524405,KC542911,KF740478,DQ839397,KC461214,KC542906,JQ713944,JN986837,GU564399,AY562990,GQ288380,GQ338311,AY562989,FJ766526,GU585905,AXQ08510,KC934170,FJ386395,JF966385,KC542903,AY845400,JF340367,JQ015297,FJ430159,KC542907,KC542910,EU167540,DQ485229,KC246549,AY935491,AY562991,JX193075,HQ317394,JF966386 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | JX193080,FJ933313, DQ485230,JX854452 ,FF065682,JX974435 ,GQ429293,JX11063 5,FJ754272,FJ75191 9,KC542898,FJ76653 0,FJ386394,AF43174 4,EU546165,FJ75427 3,DQ097394,EF2018 05,AY935500,FJ7665 28,FJ436304,GQ288 379,JQ247691,JN400 897,JN986839,JX119 193,JX193076,KC542 894,KC542912,HQ26 6603,JX193077,JN68 8864,FJ1766531,JF79 5531,KC542895,GQ2 88377,KC542909,DQ 097393,AY562988.A Y935490,JN631747,J N618348,JX519467,K C542899 |
| Newcastle disease virus B1 | NC_002617 | vertebrates,human | Paramyxoviridae,Avulavirus,Newcastle disease virus | 2 | — | AF375823,AF309418 |
| Nipah virus | NC_002728 | vertebrates,human | Paramyxoviridae,Henipavirus,Nipah virus | 11 | — | AJ627196,JN808857, AJ564621,AY029768, FJ513078,AF212302, JN808863,AJ564622, AJ564623,AY988601, AY029767 |
| Norovirus Bo/Newbury2/1976/UK | NC_001959 | vertebrates,human | Caliciviridae,Norovirus,Norwalk virus | 1 | — | AF097917 |
| Norovirus Hu/8533/Maizuru/08/JPN | NC_001959 | vertebrates,human | Caliciviridae,Norovirus,Norwalk virus | 1 | — | GU017903 |
| Norovirus Hu/Chiba/04-1050/2005/JP | NC_001959 | vertebrates,human | Caliciviridae,Norovirus,Norwalk virus | 1 | — | AB220921 |
| Norovirus Hu/GI.1/8CKII Ic/1974/USA | NC_001959 | vertebrates,human | Caliciviridae,Norovirus,Norwalk virus | 1 | — | KF429773 |
| Norovirus Hu/GI.1/8FI 1a/1968/USA | NC_001959 | vertebrates,human | Caliciviridae,Norovirus,Norwalk virus | 1 | — | JXQ23285 |
| Norovirus Hu/GI.1/8K/1979/USA | NC_001959 | vertebrates,human | Caliciviridae,Norovirus,Norwalk virus | 1 | — | KF429783 |
| Norovirus Hu/GI.1/8MC/1978/USA | NC_001959 | vertebrates,human | Caliciviridae,Norovirus,Norwalk virus | 1 | — | KF429789 |
| Norovirus Hu/GI.1/8McI1/1973/USA | NC_001959 | vertebrates,human | Caliciviridae,Norovirus,Norwalk virus | 1 | — | KF429770 |

TABLE 10-continued

| Taxonomy | Rep.Acc.ID | Host | Lineage | # GN's | Seg. Count | GN.Acc.IDs |
|---|---|---|---|---|---|---|
| Norovirus Hu/GI.1/8MoII I L/1972/USA | NC_001959 | vertebrates,human | Caliciviridae,Norovirus,Norwalk virus | 1 | — | KF429761 |
| Norovirus Hu/GI,1,1/8U111f/1973/USA | NC_001959 | vertebrates,human | Caliciviridae,Norovirus,Norwalk virus | 1 | — | KF429774 |
| Norovirus Hu/GI,1/8W/1951/USA | NC_001959 | vertebrates,human | Caliciviridae,Norovirus,Norwalk virus | 1 | — | KF429765 |
| Norovirus Hu/GI,1/CH4XQ533/2009/USA | NC_001959 | vertebrates,human | Caliciviridae,Norovirus,Norwalk virus | 1 | — | KF039731 |
| Norovirus Hu/GI,1/CHA2A014/2008/USA | NC_001959 | vertebrates,human | Caliciviridae,Norovirus,Norwalk virus | 1 | — | KF039728 |
| Norovirus Hu/GI,1/CHA3A007/2008/USA | NC_001959 | vertebrates,human | Caliciviridae,Norovirus,Norwalk virus | 1 | — | KF039735 |
| Norovirus Hu/GI,1/CHA5A010/2009/USA | NC_001959 | vertebrates,human | Caliciviridae,Norovirus,Norwalk virus | 1 | — | KF039732 |
| Norovirus Hu/GI,1/CHA6A003_20091 028/2009/U SA | NC_001959 | vertebrates,human | Caliciviridae,Norovirus,Norwalk virus | 1 | — | KF039727 |
| Norovirus Hu/GI,1/CHA6A003_20091 031/2009/U SA | NC_001959 | vertebrates,human | Caliciviridae,Norovirus,Norwalk virus | 1 | — | KF039726 |
| Norovirus Hu/GI,1/CHA6A003_20091 104/2009/U SA | NC_001959 | vertebrates,human | Caliciviridae,Norovirus,Norwalk virus | 1 | — | KF039737 |
| Norovirus Hu/GI,1/CHA6A007/2010/USA | NC_001959 | vertebrates,human | Caliciviridae,Norovirus,Norwalk virus | 1 | — | KF039729 |
| Norovirus Hu/GI,1/CHA6A014/2009/USA | NC_001959 | vertebrates,human | Caliciviridae,Norovirus,Norwalk virus | 1 | — | KF039734 |
| Norovirus Hu/GI,1/CHA7A009/2010/USA | NC_001959 | vertebrates,human | Caliciviridae,Norovirus,Norwalk virus | 1 | — | KF039725 |
| Norovirus Hu/GI,1/CHA7A011/2010/USA | NC_001959 | vertebrates,human | Caliciviridae,Norovirus,Norwalk virus | 1 | — | KF039736 |
| Norovirus Hu/GI,1/CHA9A004_20110 419/2011/USA | NC_001959 | vertebrates,human | Caliciviridae,Norovirus,Norwalk virus | 1 | — | KF039730 |
| Norovirus Hu/GI,1/CHA9A004_20110 426/2011/USA | NC_001959 | vertebrates,human | Caliciviridae,Norovirus,Norwalk virus | 1 | — | KF039733 |
| Norovirus Hu/G1,2/Jingzhou/2013401/CHN | NC_001959 | vertebrates,human | Caliciviridae,Norovirus,Norwalk virus | 1 | — | KF306212 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Norovirus Hu/GI.2/Leuven/2003/BEL | NC_001959 | vertebrates,human | Caliciviridae,Norovirus,Norwalk virus | 1 | — | FJ515294 |
| Norovirus Hu/G1.6/Kingston/ACT160D/2010/AU | NC_001959 | vertebrates,human | Caliciviridae,Norovirus,Norwalk virus | 1 | — | JQ388274 |
| Norovirus Hu/GI/10360/2010/VNM | NC_001959 | vertebrates,human | Caliciviridae,Norovirus,Norwalk virus | 1 | — | JQ911594 |
| Norovirus Hu/G1/30257/2009/VNM | NC_001959 | vertebrates,human | Caliciviridae,Norovirus,Norwalk virus | 1 | — | KC409317 |
| Norovirus Hu/GI/Otof uke/1979/JP | NC_001959 | vertebrates,human | Caliciviridae,Norovirus,Norwalk virus | 1 | — | AB187514 |
| Norovirus Hu/GII-4/Aichi1/2007/JP | NC_001959 | vertebrates,human | Caliciviridae,Norovirus,Norwalk virus | 1 | — | AB541201 |
| Norovirus Hu/GII-4/Aichi1/2008/JP | NC_001959 | vertebrates,human | Caliciviridae,Norovirus,Norwalk virus | 1 | — | AB541202 |
| Norovirus Hu/GII-4/Aichi2/2007/JP | NC_001959 | vertebrates,human | Caliciviridae,Norovirus,Norwalk virus | 1 | — | AB541203 |
| Norovirus Hu/GII-4/Aichi2/2008/JP | NC_001959 | vertebrates,human | Caliciviridae,Norovirus,Norwalk virus | 1 | — | AB541204 |
| Norovirus Hu/GII-4/Aichi3/2006/JP | NC_001959 | vertebrates,human | Caliciviridae,Norovirus,Norwalk virus | 1 | — | AB447446 |
| Norovirus Hu/GII-4/Aichi3/2007/JP | NC_001959 | vertebrates,human | Caliciviridae,Norovirus,Norwalk virus | 1 | — | AB541205 |
| Norovirus Hu/GII-4/Aichi3/2008/JP | NC_001959 | vertebrates,human | Caliciviridae,Norovirus,Norwalk virus | 1 | — | AB541206 |
| Norovirus Hu/GII-4/Aichi4/2006/JP | NC_001959 | vertebrates,human | Caliciviridae,Norovirus,Norwalk virus | 1 | — | AB447447 |
| Norovirus Hu/GII-4/Aichi4/2007/JP | NC_001959 | vertebrates,human | Caliciviridae,Norovirus,Norwalk virus | 1 | — | AB541207 |
| Norovirus Hu/GII-4/Aichi4/2008/JP | NC_001959 | vertebrates,human | Caliciviridae,Norovirus,Norwalk virus | 1 | — | AB541208 |
| Norovirus Hu/GII-4/Aichi5/2007/JP | NC_001959 | vertebrates,human | Caliciviridae,Norovirus,Norwalk virus | 1 | — | AB541209 |
| Norovirus Hu/GII-4/Aichi5/2008/JP | NC_001959 | vertebrates,human | Caliciviridae,Norovirus,Norwalk virus | 1 | — | AB541210 |
| Norovirus Hu/GII-4/Akita1/2006/JP | NC_001959 | vertebrates,human | Caliciviridae,Norovirus,Norwalk virus | 1 | — | AB447436 |
| Norovirus Hu/GII-4/Akita1/2007/JP | NC_001959 | vertebrates,human | Caliciviridae,Norovirus,Norwalk virus | 1 | — | AB541211 |
| Norovirus Hu/GII-4/Akita2/2006/JP | NC_001959 | vertebrates,human | Caliciviridae,Norovirus,Norwalk virus | 1 | — | AB447437 |
| Norovirus Hu/GII-4/Akita2/2007/JP | NC_001959 | vertebrates,human | Caliciviridae,Norovirus,Norwalk virus | 1 | — | AB541213 |
| Norovirus Hu/GII-4/Akita2/2008/JP | NC_001959 | vertebrates,human | Caliciviridae,Norovirus,Norwalk virus | 1 | — | AB541214 |
| Norovirus Hu/GII-4/Akita3/2007/JP | NC_001959 | vertebrates,human | Caliciviridae,Norovirus,Norwalk virus | 1 | — | AB541215 |
| Norovirus Hu/GII-4/Akita3/2008/JP | NC_001959 | vertebrates,human | Caliciviridae,Norovirus,Norwalk virus | 1 | — | |

TABLE 10-continued

| Taxonomy | Rep.Acc.ID | Host | # GN's | ViroCap-1.0 Taxonomy Lineage | Seg. Count | GN.Acc.IDs |
|---|---|---|---|---|---|---|
| Norovirus Hu/GII-4/Akita4/2006/JP | NC_001959 | vertebrates,human | 1 | Caliciviridae,Norovirus,Norwalk virus | — | AB447438 |
| Norovirus Hu/GII-4/Akita4/2006/JP | NC_001959 | vertebrates,human | 1 | Caliciviridae,Norovirus,Norwalk virus | — | AB541216 |
| Norovirus Hu/GII-4/Akita4/2008/JP | NC_001959 | vertebrates,human | 1 | Caliciviridae,Norovirus,Norwalk virus | — | AB447439 |
| Norovirus Hu/GII-4/Akita5/2006/JP | NC_001959 | vertebrates,human | 1 | Caliciviridae,Norovirus,Norwalk virus | — | AB541217 |
| Norovirus Hu/GII-4/Akita5/2007/JP | NC_001959 | vertebrates,human | 1 | Caliciviridae,Norovirus,Norwalk virus | — | AB447432 |
| Norovirus Hu/GII-4/Aomori1/2006/JP | NC_001959 | vertebrates,human | 1 | Caliciviridae,Norovirus,Norwalk virus | — | AB541218 |
| Norovirus Hu/GII-4/Aomori1/2007/JP | NC_001959 | vertebrates,human | 1 | Caliciviridae,Norovirus,Norwalk virus | — | AB541219 |
| Norovirus Hu/GII-4/Aomori1/2008/JP | NC_001959 | vertebrates,human | 1 | Caliciviridae,Norovirus,Norwalk virus | — | AB447433 |
| Norovirus Hu/GII-4/Aomori2/2006/JP | NC_001959 | vertebrates,human | 1 | Caliciviridae,Norovirus,Norwalk virus | — | AB541220 |
| Norovirus Hu/GII-4/Aomori2/2007/JP | NC_001959 | vertebrates,human | 1 | Caliciviridae,Norovirus,Norwalk virus | — | AB541222 |
| Norovirus Hu/GII-4/Aomori3/2007/JP | NC_001959 | vertebrates,human | 1 | Caliciviridae,Norovirus,Norwalk virus | — | AB541223 |
| Norovirus Hu/GII-4/Aomori3/2008/JP | NC_001959 | vertebrates,human | 1 | Caliciviridae,Norovirus,Norwalk virus | — | AB447434 |
| Norovirus Hu/GII-4/Aomori4/2006/JP | NC_001959 | vertebrates,human | 1 | Caliciviridae,Norovirus,Norwalk virus | — | AB541224 |
| Norovirus Hu/GII-4/Aomori4/2007/JP | NC_001959 | vertebrates,human | 1 | Caliciviridae,Norovirus,Norwalk virus | — | AB541225 |
| Norovirus Hu/GII-4/Aomori4/2008/JP | NC_001959 | vertebrates,human | 1 | Caliciviridae,Norovirus,Norwalk virus | — | AB447435 |
| Norovirus Hu/GII-4/Aomori5/2006/JP | NC_001959 | vertebrates,human | 1 | Caliciviridae,Norovirus,Norwalk virus | — | AB541226 |
| Norovirus Hu/GII-4/Aomori5/2007/JP | NC_001959 | vertebrates,human | 1 | Caliciviridae,Norovirus,Norwalk virus | — | AB541227 |
| Norovirus Hu/GII-4/CBNU2/2008/JP | NC_001959 | vertebrates,human | 1 | Caliciviridae,Norovirus,Norwalk virus | — | JQ622197 |
| Norovirus Hu/GII-4/CGMHQ1/2007/KR | NC_001959 | vertebrates,human | 1 | Caliciviridae,Norovirus,Norwalk virus | — | JN400599 |
| Norovirus Hu/GII-4/CGMHQ2/2006/TW | NC_001959 | vertebrates,human | 1 | Caliciviridae,Norovirus,Norwalk virus | — | JN400600 |
| Norovirus Hu/GII-4/CGMHQ3/2006/TW | NC_001959 | vertebrates,human | 1 | Caliciviridae,Norovirus,Norwalk virus | — | JN400601 |
| Norovirus Hu/GII-4/CGMHQ4/2006/TW | NC_001959 | vertebrates,human | 1 | Caliciviridae,Norovirus,Norwalk virus | — | JN400602 |
| Norovirus Hu/GII-4/CGMHQ5/2006/TW | NC_001959 | vertebrates,human | 1 | Caliciviridae,Norovirus,Norwalk virus | — | JN400603 |
| Norovirus Hu/GII-4/CGMHQ6/2006/TW | NC_001959 | vertebrates,human | 1 | Caliciviridae,Norovirus,Norwalk virus | — | JN400604 |

TABLE 10-continued

| Taxonomy | Rep.Acc.ID | Host | ViroCap-1.0 Taxonomy | | | Seg. Count | GN.Acc.IDs |
|---|---|---|---|---|---|---|---|
| | | | # GN's | Lineage | | | |
| Norovirus Hu/GII-4/CGMHQ7/2006/TW | NC_001959 | vertebrates,human | 1 | Caliciviridae,Norovirus,Norwalk virus | | — | JN400605 |
| Norovirus Hu/GII-4/CGMHQ8/2006/TW | NC_001959 | vertebrates,human | 1 | Caliciviridae,Norovirus,Norwalk virus | | — | JN400606 |
| Norovirus Hu/GII-4/CGMHQ9/2006/TW | NC_001959 | vertebrates,human | 1 | Caliciviridae,Norovirus,Norwalk virus | | — | JN400607 |
| Norovirus Hu/GII-4/CGMH10/2006/TW | NC_001959 | vertebrates,human | 1 | Caliciviridae,Norovirus,Norwalk virus | | — | JN400608 |
| Norovirus Hu/GII-4/CGMH11/2006/TW | NC_001959 | vertebrates,human | 1 | Caliciviridae,Norovirus,Norwalk virus | | — | JN400609 |
| Norovirus Hu/GII-4/CGMH12/2007/TW | NC_001959 | vertebrates,human | 1 | Caliciviridae,Norovirus,Norwalk virus | | — | JN400610 |
| Norovirus Hu/GII-4/CGMH13/2007/TW | NC_001959 | vertebrates,human | 1 | Caliciviridae,Norovirus,Norwalk virus | | — | JN400611 |
| Norovirus Hu/GII-4/CGMH14/2007/TW | NC_001959 | vertebrates,human | 1 | Caliciviridae,Norovirus,Norwalk virus | | — | JN400612 |
| Norovirus Hu/GII-4/CGMH15/2007/TW | NC_001959 | vertebrates,human | 1 | Caliciviridae,Norovirus,Norwalk virus | | — | JN400613 |
| Norovirus Hu/GII-4/CGMH16/2007/TW | NC_001959 | vertebrates,human | 1 | Caliciviridae,Norovirus,Norwalk virus | | — | JN400614 |
| Norovirus Hu/GII-4/CGMH17/2007/TW | NC_001959 | vertebrates,human | 1 | Caliciviridae,Norovirus,Norwalk virus | | — | JN400615 |
| Norovirus Hu/GII-4/CGMH18/2008/TW | NC_001959 | vertebrates,human | 1 | Caliciviridae,Norovirus,Norwalk virus | | — | JN400616 |
| Norovirus Hu/GII-4/CGMH19/2009/TW | NC_001959 | vertebrates,human | 1 | Caliciviridae,Norovirus,Norwalk virus | | — | JN400617 |
| Norovirus Hu/GII-4/CGMH20/2009/TW | NC_001959 | vertebrates,human | 1 | Caliciviridae,Norovirus,Norwalk virus | | — | JN400618 |
| Norovirus Hu/GII-4/CGMH21/2010/TW | NC_001959 | vertebrates,human | 1 | Caliciviridae,Norovirus,Norwalk virus | | — | JN400619 |
| Norovirus Hu/GII-4/CGMH22/2010/TW | NC_001959 | vertebrates,human | 1 | Caliciviridae,Norovirus,Norwalk virus | | — | JN400620 |
| Norovirus Hu/GII-4/CGMH23/2010/TW | NC_001959 | vertebrates,human | 1 | Caliciviridae,Norovirus,Norwalk virus | | — | JN400621 |
| Norovirus Hu/GII-4/CGMH24/2010/TW | NC_001959 | vertebrates,human | 1 | Caliciviridae,Norovirus,Norwalk virus | | — | JN400622 |
| Norovirus Hu/GII-4/CGMH25/2010/TW | NC_001959 | vertebrates,human | 1 | Caliciviridae,Norovirus,Norwalk virus | | — | JN400623 |
| Norovirus Hu/GII-4/CGMH26/2010/TW | NC_001959 | vertebrates,human | 1 | Caliciviridae,Norovirus,Norwalk virus | | — | JN400624 |
| Norovirus Hu/GII-4/CGMH27/2010/TW | NC_001959 | vertebrates,human | 1 | Caliciviridae,Norovirus,Norwalk virus | | — | JN400625 |
| Norovirus Hu/GII-4/CGMH28/2010/TW | NC_001959 | vertebrates,human | 1 | Caliciviridae,Norovirus,Norwalk virus | | — | JN400626 |
| Norovirus Hu/GII-4/CUK-3/2008/KR | NC_001959 | vertebrates,human | 1 | Caliciviridae,Norovirus,Norwalk virus | | — | FJ514242 |
| Norovirus Hu/GII-4/Chiba1/2007/JP | NC_001959 | vertebrates,human | 1 | Caliciviridae,Norovirus,Norwalk virus | | — | AB541228 |

TABLE 10-continued

| Taxonomy | Rep.Acc.ID | Host | # GN's | VíroCap-1.0 Taxonomy Lineage | Seg. Count | GN.Acc.IDs |
|---|---|---|---|---|---|---|
| Norovirus Hu/GII-4/Chiba1/2008/JP | NC_001959 | vertebrates,human | 1 | Caliciviridae,Norovirus,Norwalk virus | — | AB541229 |
| Norovirus Hu/GII-4/Chiba2/2007/JP | NC_001959 | vertebrates,human | 1 | Caliciviridae,Norovirus,Norwalk virus | — | AB541230 |
| Norovirus Hu/GII-4/Chiba2/2008/JP | NC_001959 | vertebrates,human | 1 | Caliciviridae,Norovirus,Norwalk virus | — | AB541231 |
| Norovirus Hu/GII-4/Chiba4/2007/JP | NC_001959 | vertebrates,human | 1 | Caliciviridae,Norovirus,Norwalk virus | — | AB541232 |
| Norovirus Hu/GII-4/Chiba4/2008/JP | NC_001959 | vertebrates,human | 1 | Caliciviridae,Norovirus,Norwalk virus | — | AB541233 |
| Norovirus Hu/GII-4/Chiba5/2007/JP | NC_001959 | vertebrates,human | 1 | Caliciviridae,Norovirus,Norwalk virus | — | AB541234 |
| Norovirus Hu/GII-4/Chiba5/2008/JP | NC_001959 | vertebrates,human | 1 | Caliciviridae,Norovirus,Norwalk virus | — | AB541235 |
| Norovirus Hu/GII-4/Ehime1/2006/JP | NC_001959 | vertebrates,human | 1 | Caliciviridae,Norovirus,Norwalk virus | — | AB447453 |
| Norovirus Hu/GII-4/Ehime1/2007/JP | NC_001959 | vertebrates,human | 1 | Caliciviridae,Norovirus,Norwalk virus | — | AB541236 |
| Norovirus Hu/GII-4/Ehime1/2008/JP | NC_001959 | vertebrates,human | 1 | Caliciviridae,Norovirus,Norwalk virus | — | AB541237 |
| Norovirus Hu/GII-4/Ehime2/2006/JP | NC_001959 | vertebrates,human | 1 | Caliciviridae,Norovirus,Norwalk virus | — | AB447454 |
| Norovirus Hu/GII-4/Ehime2/2007/JP | NC_001959 | vertebrates,human | 1 | Caliciviridae,Norovirus,Norwalk virus | — | AB541238 |
| Norovirus Hu/GII-4/Ehime2/2008/JP | NC_001959 | vertebrates,human | 1 | Caliciviridae,Norovirus,Norwalk virus | — | AB541239 |
| Norovirus Hu/GII-4/Ehime3/2007/JP | NC_001959 | vertebrates,human | 1 | Caliciviridae,Norovirus,Norwalk virus | — | AB541240 |
| Norovirus Hu/GII-4/Ehime3/2008/JP | NC_001959 | vertebrates,human | 1 | Caliciviridae,Norovirus,Norwalk virus | — | AB541241 |
| Norovirus Hu/GII-4/Ehime4/2007/JP | NC_001959 | vertebrates,human | 1 | Caliciviridae,Norovirus,Norwalk virus | — | AB541242 |
| Norovirus Hu/GII-4/Ehime4/2008/JP | NC_001959 | vertebrates,human | 1 | Caliciviridae,Norovirus,Norwalk virus | — | AB447455 |
| Norovirus Hu/GII-4/Ehime5/2006/JP | NC_001959 | vertebrates,human | 1 | Caliciviridae,Norovirus,Norwalk virus | — | AB541243 |
| Norovirus Hu/GII-4/Ehime5/2008/JP | NC_001959 | vertebrates,human | 1 | Caliciviridae,Norovirus,Norwalk virus | — | AB543808 |
| Norovirus Hu/GII-4/FUMI/2010/JP | NC_001959 | vertebrates,human | 1 | Caliciviridae,Norovirus,Norwalk virus | — | AB541244 |
| Norovirus Hu/GII-4/Fukui1/2008/JP | NC_001959 | vertebrates,human | 1 | Caliciviridae,Norovirus,Norwalk virus | — | AB541245 |
| Norovirus Hu/GII-4/Fukui2/2007/JP | NC_001959 | vertebrates,human | 1 | Caliciviridae,Norovirus,Norwalk virus | — | AB541246 |
| Norovirus Hu/GII-4/Fukui2/2008/JP | NC_001959 | vertebrates,human | 1 | Caliciviridae,Norovirus,Norwalk virus | — | AB541247 |
| Norovirus Hu/GII-4/Fukui4/2007/JP | NC_001959 | vertebrates,human | 1 | Caliciviridae,Norovirus,Norwalk virus | — | AB541248 |
| Norovirus Hu/GII-4/Fukui4/2008/JP | NC_001959 | vertebrates,human | 1 | Caliciviridae,Norovirus,Norwalk virus | — | |

TABLE 10-continued

| Taxonomy | Rep.Acc.ID | Host | Lineage | # GN's | Seg. Count | GN.Acc.IDs |
|---|---|---|---|---|---|---|
| Norovirus Hu/GII-4/Fukui5/2007/JP | NC_001959 | vertebrates,human | Caliciviridae,Norovirus,Norwalk virus | 1 | — | AB541249 |
| Norovirus Hu/GII-4/Fukui5/2008/JP | NC_001959 | vertebrates,human | Caliciviridae,Norovirus,Norwalk virus | 1 | — | AB541250 |
| Norovirus Hu/GII-4/Hiroshima1/2006/JP | NC_001959 | vertebrates,human | Caliciviridae,Norovirus,Norwalk virus | 1 | — | AB447451 |
| Norovirus Hu/GII-4/Hiroshima1/2007/JP | NC_001959 | vertebrates,human | Caliciviridae,Norovirus,Norwalk virus | 1 | — | AB541251 |
| Norovirus Hu/GII-4/Hiroshima1/2008/JP | NC_001959 | vertebrates,human | Caliciviridae,Norovirus,Norwalk virus | 1 | — | AB541252 |
| Norovirus Hu/GII-4/Hiroshima2/2006/JP | NC_001959 | vertebrates,human | Caliciviridae,Norovirus,Norwalk virus | 1 | — | AB447452 |
| Norovirus Hu/GII-4/Hiroshima2/2007/JP | NC_001959 | vertebrates,human | Caliciviridae,Norovirus,Norwalk virus | 1 | — | AB541253 |
| Norovirus Hu/GII-4/Hiroshima2/2008/JP | NC_001959 | vertebrates,human | Caliciviridae,Norovirus,Norwalk virus | 1 | — | AB541254 |
| Norovirus Hu/GII-4/Hiroshima3/2007/JP | NC_001959 | vertebrates,human | Caliciviridae,Norovirus,Norwalk virus | 1 | — | AB541255 |
| Norovirus Hu/GII-4/Hiroshima3/2008/JP | NC_001959 | vertebrates,human | Caliciviridae,Norovirus,Norwalk virus | 1 | — | AB541256 |
| Norovirus Hu/GII-4/Hiroshima4/2007/JP | NC_001959 | vertebrates,human | Caliciviridae,Norovirus,Norwalk virus | 1 | — | AB541257 |
| Norovirus Hu/GII-4/Hiroshima4/2008/JP | NC_001959 | vertebrates,human | Caliciviridae,Norovirus,Norwalk virus | 1 | — | AB541258 |
| Norovirus Hu/GII-4/Hiroshima5/2008/JP | NC_001959 | vertebrates,human | Caliciviridae,Norovirus,Norwalk virus | 1 | — | AB541259 |
| Norovirus Hu/GII-4/Hokkaido1/2006/JP | NC_001959 | vertebrates,human | Caliciviridae,Norovirus,Norwalk virus | 1 | — | AB447427 |
| Norovirus Hu/GII-4/Hokkaido1/2007/JP | NC_001959 | vertebrates,human | Caliciviridae,Norovirus,Norwalk virus | 1 | — | AB541260 |
| Norovirus Hu/GII-4/Hokkaido1/2008/JP | NC_001959 | vertebrates,human | Caliciviridae,Norovirus,Norwalk virus | 1 | — | AB541261 |
| Norovirus Hu/GII-4/Hokkaido2/2006/JP | NC_001959 | vertebrates,human | Caliciviridae,Norovirus,Norwalk virus | 1 | — | AB447428 |
| Norovirus Hu/GII-4/Hokkaido2/2007/JP | NC_001959 | vertebrates,human | Caliciviridae,Norovirus,Norwalk virus | 1 | — | AB541262 |
| Norovirus Hu/GII-4/Hokkaido2/2008/JP | NC_001959 | vertebrates,human | Caliciviridae,Norovirus,Norwalk virus | 1 | — | AB541263 |
| Norovirus Hu/GII-4/Hokkaido3/2006/JP | NC_001959 | vertebrates,human | Caliciviridae,Norovirus,Norwalk virus | 1 | — | AB447429 |
| Norovirus Hu/GII-4/Hokkaido3/2008/JP | NC_001959 | vertebrates,human | Caliciviridae,Norovirus,Norwalk virus | 1 | — | AB541264 |
| Norovirus Hu/GII-4/Hokkaido4/2006/JP | NC_001959 | vertebrates,human | Caliciviridae,Norovirus,Norwalk virus | 1 | — | AB447430 |
| Norovirus Hu/GII-4/Hokkaido4/2007/JP | NC_001959 | vertebrates,human | Caliciviridae,Norovirus,Norwalk virus | 1 | — | AB541265 |
| Norovirus Hu/GII-4/Hokkaido4/2008/JP | NC_001959 | vertebrates,human | Caliciviridae,Norovirus,Norwalk virus | 1 | — | AB541266 |

TABLE 10-continued

| Taxonomy | Rep.Acc.ID | Host | VirCap-1.0 Taxonomy Lineage | # GN's | Seg. Count | GN.Acc.IDs |
|---|---|---|---|---|---|---|
| Norovirus Hu/GII-4/Hokkaido5/2006/JP | NC_001959 | vertebrates,human | Caliciviridae,Norovirus,Norwalk virus | 1 | — | AB447431 |
| Norovirus Hu/GII-4/Hokkaido5/2007/JP | NC_001959 | vertebrates,human | Caliciviridae,Norovirus,Norwalk virus | 1 | — | AB541267 |
| Norovirus Hu/GII-4/Hokkaido5/2008/JP | NC_001959 | vertebrates,human | Caliciviridae,Norovirus,Norwalk virus | 1 | — | AB541268 |
| Norovirus Hu/GII-4/Iwate1/2008/JP | NC_001959 | vertebrates,human | Caliciviridae,Norovirus,Norwalk virus | 1 | — | AB541269 |
| Norovirus Hu/GII-4/Iwate2/2007/JP | NC_001959 | vertebrates,human | Caliciviridae,Norovirus,Norwalk virus | 1 | — | AB541270 |
| Norovirus Hu/GII-4/Iwate3/2007/JP | NC_001959 | vertebrates,human | Caliciviridae,Norovirus,Norwalk virus | 1 | — | AB541271 |
| Norovirus Hu/GII-4/Iwate3/2008/JP | NC_001959 | vertebrates,human | Caliciviridae,Norovirus,Norwalk virus | 1 | — | AB541272 |
| Norovirus Hu/GII-4/Iwate4/2007/JP | NC_001959 | vertebrates,human | Caliciviridae,Norovirus,Norwalk virus | 1 | — | AB541273 |
| Norovirus Hu/GII-4/Iwate4/2008/JP | NC_001959 | vertebrates,human | Caliciviridae,Norovirus,Norwalk virus | 1 | — | AB541274 |
| Norovirus Hu/GII-4/Iwate5/2007/JP | NC_001959 | vertebrates,human | Caliciviridae,Norovirus,Norwalk virus | 1 | — | AB541275 |
| Norovirus Hu/GII-4/Iwate5/2008/JP | NC_001959 | vertebrates,human | Caliciviridae,Norovirus,Norwalk virus | 1 | — | AB541276 |
| Norovirus Hu/GII-4/Kumamoto1/2006/JP | NC_001959 | vertebrates,human | Caliciviridae,Norovirus,Norwalk virus | 1 | — | AB447459 |
| Norovirus Hu/GII-4/Kumamoto1/2007/JP | NC_001959 | vertebrates,human | Caliciviridae,Norovirus,Norwalk virus | 1 | — | AB541277 |
| Norovirus Hu/GII-4/Kumamoto2/2006/JP | NC_001959 | vertebrates,human | Caliciviridae,Norovirus,Norwalk virus | 1 | — | AB447460 |
| Norovirus Hu/GII-4/Kumamoto2/2007/JP | NC_001959 | vertebrates,human | Caliciviridae,Norovirus,Norwalk virus | 1 | — | AB541278 |
| Norovirus Hu/GII-4/Kumamoto3/2006/JP | NC_001959 | vertebrates,human | Caliciviridae,Norovirus,Norwalk virus | 1 | — | AB447461 |
| Norovirus Hu/GII-4/Kumamoto3/2007/JP | NC_001959 | vertebrates,human | Caliciviridae,Norovirus,Norwalk virus | 1 | — | AB541279 |
| Norovirus Hu/GII-4/Kumamoto4/2006/JP | NC_001959 | vertebrates,human | Caliciviridae,Norovirus,Norwalk virus | 1 | — | AB447462 |
| Norovirus Hu/GII-4/Kumamoto4/2007/JP | NC_001959 | vertebrates,human | Caliciviridae,Norovirus,Norwalk virus | 1 | — | AB541280 |
| Norovirus Hu/GII-4/Kumamoto5/2006/JP | NC_001959 | vertebrates,human | Caliciviridae,Norovirus,Norwalk virus | 1 | — | AB447463 |
| Norovirus Hu/GII-4/Kumamoto5/2007/JP | NC_001959 | vertebrates,human | Caliciviridae,Norovirus,Norwalk virus | 1 | — | AB541281 |
| Norovirus Hu/GII-4/Miyagi1/2007/JP | NC_001959 | vertebrates,human | Caliciviridae,Norovirus,Norwalk virus | 1 | — | AB447440 |
| Norovirus Hu/GII-4/Miyagi2/2006/JP | NC_001959 | vertebrates,human | Caliciviridae,Norovirus,Norwalk virus | 1 | — | AB541282 |
| Norovirus Hu/GII-4/Miyagi2/2007/JP | NC_001959 | vertebrates,human | Caliciviridae,Norovirus,Norwalk virus | 1 | — | AB541283 |
| Norovirus Hu/GII-4/Miyagi3/2007/JP | NC_001959 | vertebrates,human | Caliciviridae,Norovirus,Norwalk virus | 1 | — | |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Norovirus Hu/GII-4/Miyagi4/2006/JP | NC_001959 | vertebrates,human | Caliciviridae,Norovirus,Norwalk virus | 1 | — | AB447441 |
| Norovirus Hu/GII-4/Miyagi5/2006/JP | NC_001959 | vertebrates,human | Caliciviridae,Norovirus,Norwalk virus | 1 | — | AB447442 |
| Norovirus Hu/GII-4/Miyagi5/2008/JP | NC_001959 | vertebrates,human | Caliciviridae,Norovirus,Norwalk virus | 1 | — | AB541284 |
| Norovirus Hu/GII-4/Miyazaki1/2007/JP | NC_001959 | vertebrates,human | Caliciviridae,Norovirus,Norwalk virus | 1 | — | AB541288 |
| Norovirus Hu/GII-4/Miyazaki1/2008/JP | NC_001959 | vertebrates,human | Caliciviridae,Norovirus,Norwalk virus | 1 | — | AB541289 |
| Norovirus Hu/GII-4/Miyazaki10/2008/JP | NC_001959 | vertebrates,human | Caliciviridae,Norovirus,Norwalk virus | 1 | — | AB541285 |
| Norovirus Hu/GII-4/Miyazaki12/2008/JP | NC_001959 | vertebrates,human | Caliciviridae,Norovirus,Norwalk virus | 1 | — | AB541286 |
| Norovirus Hu/GII-4/Miyazaki13/2008/JP | NC_001959 | vertebrates,human | Caliciviridae,Norovirus,Norwalk virus | 1 | — | AB541287 |
| Norovirus Hu/GII-4/Miyazaki2/2007/JP | NC_001959 | vertebrates,human | Caliciviridae,Norovirus,Norwalk virus | 1 | — | AB541290 |
| Norovirus Hu/GII-4/Miyazaki2/2008/JP | NC_001959 | vertebrates,human | Caliciviridae,Norovirus,Norwalk virus | 1 | — | AB541291 |
| Norovirus Hu/GII-4/Miyazaki3/2007/JP | NC_001959 | vertebrates,human | Caliciviridae,Norovirus,Norwalk virus | 1 | — | AB541292 |
| Norovirus Hu/GII-4/Miyazaki3/2008/JP | NC_001959 | vertebrates,human | Caliciviridae,Norovirus,Norwalk virus | 1 | — | AB541293 |
| Norovirus Hu/GII-4/Miyazaki4/2007/JP | NC_001959 | vertebrates,human | Caliciviridae,Norovirus,Norwalk virus | 1 | — | AB541294 |
| Norovirus Hu/GII-4/Miyazaki4/2008/JP | NC_001959 | vertebrates,human | Caliciviridae,Norovirus,Norwalk virus | 1 | — | AB541295 |
| Norovirus Hu/GII-4/Miyazaki5/2007/JP | NC_001959 | vertebrates,human | Caliciviridae,Norovirus,Norwalk virus | 1 | — | AB541296 |
| Norovirus Hu/GII-4/Miyazaki6/2008/JP | NC_001959 | vertebrates,human | Caliciviridae,Norovirus,Norwalk virus | 1 | — | AB541297 |
| Norovirus Hu/GII-4/Miyazaki7/2008/JP | NC_001959 | vertebrates,human | Caliciviridae,Norovirus,Norwalk virus | 1 | — | AB541298 |
| Norovirus Hu/GII-4/Miyazaki8/2008/JP | NC_001959 | vertebrates,human | Caliciviridae,Norovirus,Norwalk virus | 1 | — | AB541299 |
| Norovirus Hu/GII-4/Nagano1/2007/JP | NC_001959 | vertebrates,human | Caliciviridae,Norovirus,Norwalk virus | 1 | — | AB541301 |
| Norovirus Hu/GII-4/Nagano1/2008/JP | NC_001959 | vertebrates,human | Caliciviridae,Norovirus,Norwalk virus | 1 | — | AB541302 |
| Norovirus Hu/GII-4/Nagano2/2007/JP | NC_001959 | vertebrates,human | Caliciviridae,Norovirus,Norwalk virus | 1 | — | AB541303 |
| Norovirus Hu/GII-4/Nagano2/2008/JP | NC_001959 | vertebrates,human | Caliciviridae,Norovirus,Norwalk virus | 1 | — | AB541304 |
| Norovirus Hu/GII-4/Nagano3/2007/JP | NC_001959 | vertebrates,human | Caliciviridae,Norovirus,Norwalk virus | 1 | — | AB541305 |
| Norovirus Hu/GII-4/Nagano3/2008/JP | NC_001959 | vertebrates,human | Caliciviridae,Norovirus,Norwalk virus | 1 | — | AB541306 |

TABLE 10-continued

| Taxonomy | Rep.Acc.ID | Host | Lineage | # GN's | Seg. Count | GN.Acc.IDs |
|---|---|---|---|---|---|---|
| Norovirus Hu/GII-4/Nagan04/2008/JP | NC_001959 | vertebrates,human | Caliciviridae,Norovirus,Norwalk virus | 1 | — | AB541307 |
| Norovirus Hu/GII-4/Nagano5/2007/JP | NC_001959 | vertebrates,human | Caliciviridae,Norovirus,Norwalk virus | 1 | — | AB541308 |
| Norovirus Hu/GII-4/Niigata1/2007/JP | NC_001959 | vertebrates,human | Caliciviridae,Norovirus,Norwalk virus | 1 | — | AB541309 |
| Norovirus Hu/GII-4/Niigata1/2008/JP | NC_001959 | vertebrates,human | Caliciviridae,Norovirus,Norwalk virus | 1 | — | AB541310 |
| Norovirus Hu/GII-4/Niigata2/2007/JP | NC_001959 | vertebrates,human | Caliciviridae,Norovirus,Norwalk virus | 1 | — | AB541311 |
| Norovirus Hu/GII-4/Niigata2/2008/JP | NC_001959 | vertebrates,human | Caliciviridae,Norovirus,Norwalk virus | 1 | — | AB541312 |
| Norovirus Hu/GII-4/Niigata3/2007/JP | NC_001959 | vertebrates,human | Caliciviridae,Norovirus,Norwalk virus | 1 | — | AB541313 |
| Norovirus Hu/GII-4/Niigata3/2008/JP | NC_001959 | vertebrates,human | Caliciviridae,Norovirus,Norwalk virus | 1 | — | AB541314 |
| Norovirus Hu/GII-4/Niigata4/2007/JP | NC_001959 | vertebrates,human | Caliciviridae,Norovirus,Norwalk virus | 1 | — | AB541315 |
| Norovirus Hu/GII-4/Niigata4/2008/JP | NC_001959 | vertebrates,human | Caliciviridae,Norovirus,Norwalk virus | 1 | — | AB541316 |
| Norovirus Hu/GII-4/Niigata5/2007/JP | NC_001959 | vertebrates,human | Caliciviridae,Norovirus,Norwalk virus | 1 | — | AB541317 |
| Norovirus Hu/GII-4/Niigata5/2008/JP | NC_001959 | vertebrates,human | Caliciviridae,Norovirus,Norwalk virus | 1 | — | AB541318 |
| Norovirus Hu/GII-4/0saka1/2007/JP | NC_001959 | vertebrates,human | Caliciviridae,Norovirus,Norwalk virus | 1 | — | AB541319 |
| Norovirus Hu/GII-4/0saka1/2008/JP | NC_001959 | vertebrates,human | Caliciviridae,Norovirus,Norwalk virus | 1 | — | AB541320 |
| Norovirus Hu/GII-4/0saka2/2007/JP | NC_001959 | vertebrates,human | Caliciviridae,Norovirus,Norwalk virus | 1 | — | AB541321 |
| Norovirus Hu/GII-4/0saka2/2008/JP | NC_001959 | vertebrates,human | Caliciviridae,Norovirus,Norwalk virus | 1 | — | AB541322 |
| Norovirus Hu/GII-4/0saka3/2007/JP | NC_001959 | vertebrates,human | Caliciviridae,Norovirus,Norwalk virus | 1 | — | AB541323 |
| Norovirus Hu/GII-4/0saka3/2008/JP | NC_001959 | vertebrates,human | Caliciviridae,Norovirus,Norwalk virus | 1 | — | AB541324 |
| Norovirus Hu/GII-4/0saka4/2007/JP | NC_001959 | vertebrates,human | Caliciviridae,Norovirus,Norwalk virus | 1 | — | AB541325 |
| Norovirus Hu/GII-4/0saka4/2008/JP | NC_001959 | vertebrates,human | Caliciviridae,Norovirus,Norwalk virus | 1 | — | AB541326 |
| Norovirus Hu/GII-4/0saka5/2007/JP | NC_001959 | vertebrates,human | Caliciviridae,Norovirus,Norwalk virus | 1 | — | AB541327 |
| Norovirus Hu/GII-4/0saka5/2008/JP | NC_001959 | vertebrates,human | Caliciviridae,Norovirus,Norwalk virus | 1 | — | AB541328 |
| Norovirus Hu/GII-4/0saka6/2008/JP | NC_001959 | vertebrates,human | Caliciviridae,Norovirus,Norwalk virus | 1 | — | AB541329 |
| Norovirus Hu/GII-4/Saga1/2006/JP | NC_001959 | vertebrates,human | Caliciviridae,Norovirus,Norwalk virus | 1 | — | AB447456 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Norovirus Hu/GII-4/Saga1/2007/JP | NC_001959 | vertebrates,human | Caliciviridae,Norovirus,Norwalk virus | 1 | — | AB541330 |
| Norovirus Hu/GII-4/Saga1/2008/JP | NC_001959 | vertebrates,human | Caliciviridae,Norovirus,Norwalk virus | 1 | — | AB541331 |
| Norovirus Hu/GII-4/Saga2/2007/JP | NC_001959 | vertebrates,human | Caliciviridae,Norovirus,Norwalk virus | 1 | — | AB541332 |
| Norovirus Hu/GII-4/Saga2/2008/JP | NC_001959 | vertebrates,human | Caliciviridae,Norovirus,Norwalk virus | 1 | — | AB541333 |
| Norovirus Hu/GII-4/Saga3/2008/JP | NC_001959 | vertebrates,human | Caliciviridae,Norovirus,Norwalk virus | 1 | — | AB541334 |
| Norovirus Hu/GII-4/Saga4/2006/JP | NC_001959 | vertebrates,human | Caliciviridae,Norovirus,Norwalk virus | 1 | — | AB447457 |
| Norovirus Hu/GII-4/Saga4/2007/JP | NC_001959 | vertebrates,human | Caliciviridae,Norovirus,Norwalk virus | 1 | — | AB541335 |
| Norovirus Hu/GII-4/Saga4/2008/JP | NC_001959 | vertebrates,human | Caliciviridae,Norovirus,Norwalk virus | 1 | — | AB541336 |
| Norovirus Hu/GII-4/Saga5/2006/JP | NC_001959 | vertebrates,human | Caliciviridae,Norovirus,Norwalk virus | 1 | — | AB447458 |
| Norovirus Hu/GII-4/Saga5/2007/JP | NC_001959 | vertebrates,human | Caliciviridae,Norovirus,Norwalk virus | 1 | — | AB541337 |
| Norovirus Hu/GII-4/Saga5/2008/JP | NC_001959 | vertebrates,human | Caliciviridae,Norovirus,Norwalk virus | 1 | — | AB541338 |
| Norovirus Hu/GII-4/Sakai 1/2007/JP | NC_001959 | vertebrates,human | Caliciviridae,Norovirus,Norwalk virus | 1 | — | AB541339 |
| Norovirus Hu/GII-4/Sakai 1/2008/JP | NC_001959 | vertebrates,human | Caliciviridae,Norovirus,Norwalk virus | 1 | — | AB541340 |
| Norovirus H u/GII-4/Sakai2/2006/JP | NC_001959 | vertebrates,human | Caliciviridae,Norovirus,Norwalk virus | 1 | — | AB447448 |
| Norovirus H u/GII-4/Sakai2/2007/JP | NC_001959 | vertebrates,human | Caliciviridae,Norovirus,Norwalk virus | 1 | — | AB541341 |
| Norovirus H u/GII-4/Sakai3/2006/JP | NC_001959 | vertebrates,human | Caliciviridae,Norovirus,Norwalk virus | 1 | — | AB447449 |
| Norovirus H u/GII-4/Sakai3/2007/JP | NC_001959 | vertebrates,human | Caliciviridae,Norovirus,Norwalk virus | 1 | — | AB541342 |
| Norovirus H u/GII-4/Sakai3/2008/JP | NC_001959 | vertebrates,human | Caliciviridae,Norovirus,Norwalk virus | 1 | — | AB541343 |
| Norovirus H u/GII-4/Sakai4/2006/JP | NC_001959 | vertebrates,human | Caliciviridae,Norovirus,Norwalk virus | 1 | — | AB447450 |
| Norovirus H u/GII-4/Sakai4/2007/JP | NC_001959 | vertebrates,human | Caliciviridae,Norovirus,Norwalk virus | 1 | — | AB541344 |
| Norovirus H u/GII-4/Sakai4/2008/JP | NC_001959 | vertebrates,human | Caliciviridae,Norovirus,Norwalk virus | 1 | — | AB541345 |
| Norovirus H u/GII-4/Shimane1/2007/JP | NC_001959 | vertebrates,human | Caliciviridae,Norovirus,Norwalk virus | 1 | — | AB541346 |
| Norovirus H u/GII-4/Shimane2/2007/JP | NC_001959 | vertebrates,human | Caliciviridae,Norovirus,Norwalk virus | 1 | — | AB541347 |
| Norovirus H u/GII-4/Shimane3/2007/JP | NC_001959 | vertebrates,human | Caliciviridae,Norovirus,Norwalk virus | 1 | — | AB541349 |

TABLE 10-continued

Vir oCap-1.0 Taxonomy

| Taxonomy | Rep.Acc.ID | Host | Lineage | # GN's | Seg. Count | GN.Acc.IDs |
|---|---|---|---|---|---|---|
| Norovirus Hu/GII-4/Shimane3/2008/JP | NC_001959 | vertebrates,human | Caliciviridae,Norovirus,Norwalk virus | 1 | — | AB541350 |
| Norovirus Hu/GII-4/Shimane4/2007/JP | NC_001959 | vertebrates,human | Caliciviridae,Norovirus,Norwalk virus | 1 | — | AB541351 |
| Norovirus Hu/GII-4/Shimane5/2007/JP | NC_001959 | vertebrates,human | Caliciviridae,Norovirus,Norwalk virus | 1 | — | AB541352 |
| Norovirus Hu/GII-4/Shimane5/2008/JP | NC_001959 | vertebrates,human | Caliciviridae,Norovirus,Norwalk virus | 1 | — | AB541353 |
| Norovirus Hu/GII-4/Toyama1/2006/JP | NC_001959 | vertebrates,human | Caliciviridae,Norovirus,Norwalk virus | 1 | — | AB447443 |
| Norovirus Hu/GII-4/Toyama1/2007/JP | NC_001959 | vertebrates,human | Caliciviridae,Norovirus,Norwalk virus | 1 | — | AB541354 |
| Norovirus Hu/GII-4/Toyama2/2007/JP | NC_001959 | vertebrates,human | Caliciviridae,Norovirus,Norwalk virus | 1 | — | AB541355 |
| Norovirus Hu/GII-4/Toyama2/2008/JP | NC_001959 | vertebrates,human | Caliciviridae,Norovirus,Norwalk virus | 1 | — | AB541356 |
| Norovirus Hu/GII-4/Toyama3/2007/JP | NC_001959 | vertebrates,human | Caliciviridae,Norovirus,Norwalk virus | 1 | — | AB541357 |
| Norovirus Hu/GII-4/Toyama3/2008/JP | NC_001959 | vertebrates,human | Caliciviridae,Norovirus,Norwalk virus | 1 | — | AB541358 |
| Norovirus Hu/GII-4/Toyama4/2006/JP | NC_001959 | vertebrates,human | Caliciviridae,Norovirus,Norwalk virus | 1 | — | AB447444 |
| Norovirus Hu/GII-4/Toyama4/2007/JP | NC_001959 | vertebrates,human | Caliciviridae,Norovirus,Norwalk virus | 1 | — | AB541359 |
| Norovirus Hu/GII-4/Toyama4/2008/JP | NC_001959 | vertebrates,human | Caliciviridae,Norovirus,Norwalk virus | 1 | — | AB541360 |
| Norovirus Hu/GII-4/Toyama5/2006/JP | NC_001959 | vertebrates,human | Caliciviridae,Norovirus,Norwalk virus | 1 | — | AB447445 |
| Norovirus Hu/GII-4/Toyama5/2007/JP | NC_001959 | vertebrates,human | Caliciviridae,Norovirus,Norwalk virus | 1 | — | AB541361 |
| Norovirus Hu/GII-4/Toyama5/2008/JP | NC_001959 | vertebrates,human | Caliciviridae,Norovirus,Norwalk virus | 1 | — | AB541362 |
| Norovirus Hu/GII,12/HS206/2010/USA | NC_001959 | vertebrates,human | Caliciviridae,Norovirus,Norwalk virus | 1 | — | HQ664990 |
| Norovirus Hu/GII,12/HS210/2010/USA | NC_001959 | vertebrates,human | Caliciviridae,Norovirus,Norwalk virus | 1 | — | HQ449728 |
| Norovirus Hu/GII,3/C BN U1/2006/KOR | NC_001959 | vertebrates,human | Caliciviridae,Norovirus,Norwalk virus | 1 | — | GU980585 |
| Norovirus Hu/GII,3/Jingzhou/2013402/CHN | NC_001959 | vertebrates,human | Caliciviridae,Norovirus,Norwalk virus | 1 | — | KF306213 |
| Norovirus Hu/GII,4/5M/USA/2004 | NC_001959 | vertebrates,human | Caliciviridae,Norovirus,Norwalk virus | 1 | — | JQ798158 |
| Norovirus Hu/GII,4/Armidale/NSW390I/2008/AU | NC_001959 | vertebrates,human | Caliciviridae,Norovirus,Norwalk virus | 1 | — | GQ845369 |

TABLE 10-continued

| | | | | ViroCap-1.0 Taxonomy | | | |
|---|---|---|---|---|---|---|---|
| Taxonomy | Rep.Acc.ID | Host | # GN's | Lineage | Seg. Count | GN.Acc.IDs |
| Norovirus Hu/GII,4/Beecroft/NSW305P/2009/AUS | NC_001959 | vertebrates,human | 1 | Caliciviridae,Norovirus,Norwalk virus | — | HM748971 |
| Norovirus Hu/G II ,4/CH DC2094/1974/US | NC_001959 | vertebrates,human | 1 | Caliciviridae,Norovirus,Norwalk virus | — | FJ537135 |
| Norovirus Hu/G II ,4/CH DC3967/1988/US | NC_001959 | vertebrates,human | 1 | Caliciviridae,Norovirus,Norwalk virus | — | FJ537136 |
| Norovirus Hu/GII,4/CHDC4108/1987/US | NC_001959 | vertebrates,human | 1 | Caliciviridae,Norovirus,Norwalk virus | — | FJ537137 |
| Norovirus Hu/GII,4/CHDC4871/1977/US | NC_001959 | vertebrates,human | 1 | Caliciviridae,Norovirus,Norwalk virus | — | FJ537138 |
| Norovirus Hu/GII,4/CHDC5191/1974/US | NC_001959 | vertebrates,human | 1 | Caliciviridae,Norovirus,Norwalk virus | — | FJ537134 |
| Norovirus Hu/GII,4/CHDC5191/1974/USA | NC_001959 | vertebrates,human | 1 | Caliciviridae,Norovirus,Norwalk virus | — | JXQ23286 |
| Norovirus Hu/GII,4/GP13111/2011/USA | NC_001959 | vertebrates,human | 1 | Caliciviridae,Norovirus,Norwalk virus | — | KC576912 |
| Norovirus Hu/GII,4/GP2411/2011/USA | NC_001959 | vertebrates,human | 1 | Caliciviridae,Norovirus,Norwalk virus | — | KC576909 |
| Norovirus Hu/GII,4/HS194/2009/US | NC_001959 | vertebrates,human | 1 | Caliciviridae,Norovirus,Norwalk virus | — | GU325839 |
| Norovirus Hu/GII,4/Hunter504D/040/AU | NC_001959 | vertebrates,human | 1 | Caliciviridae,Norovirus,Norwalk virus | — | DQ078814 |
| Norovirus Hu/GII,4/JB-15/KOR/2008 | NC_001959 | vertebrates,human | 1 | Caliciviridae,Norovirus,Norwalk virus | — | HQ009513 |
| Norovirus Hu/GII,4/Jiangsu1/2011/CHN | NC_001959 | vertebrates,human | 1 | Caliciviridae,Norovirus,Norwalk virus | — | KC577174 |
| Norovirus Hu/GII,4/Jiangsu2/2012/CHN | NC_001959 | vertebrates,human | 1 | Caliciviridae,Norovirus,Norwalk virus | — | KC577175 |
| Norovirus Hu/GII,4/Jingzhou/2013403/CHN | NC_001959 | vertebrates,human | 1 | Caliciviridae,Norovirus,Norwalk virus | — | KF306214 |
| Norovirus Hu/GII,4/Kenepuru/NZ327/2006/NZL | NC_001959 | vertebrates,human | 1 | Caliciviridae,Norovirus,Norwalk virus | — | EF187497 |
| Norovirus Hu/GII,4/MD-2004/2004/US | NC_001959 | vertebrates,human | 1 | Caliciviridae,Norovirus,Norwalk virus | — | DQ658413 |

TABLE 10-continued

| Taxonomy | Rep.Acc.ID | Host | Lineage | # GN's | Seg. Count | GN.Acc.IDs |
|---|---|---|---|---|---|---|
| Norovirus Hu/GII,4/NIHIC1,16/2012/USA | NC_001959 | vertebrates,human | Caliciviridae,Norovirus,Norwalk virus | 1 | — | KF712499 |
| Norovirus Hu/GII,4/NIHIC11,3/2013/USA | NC_001959 | vertebrates,human | Caliciviridae,Norovirus,Norwalk virus | 1 | — | KF712504 |
| Norovirus Hu/GII,4/NIHIC17,6/2012/USA | NC_001959 | vertebrates,human | Caliciviridae,Norovirus,Norwalk virus | 1 | — | KF712501 |
| Norovirus Hu/GII,4/NIHIC17,8/2013/USA | NC_001959 | vertebrates,human | Caliciviridae,Norovirus,Norwalk virus | 1 | — | KF712491 |
| Norovirus Hu/GII,4/NIHIC17,9/2013/USA | NC_001959 | vertebrates,human | Caliciviridae,Norovirus,Norwalk virus | 1 | — | KF712498 |
| Norovirus Hu/GII,4/NIHIC2,2/2010/USA | NC_001959 | vertebrates,human | Caliciviridae,Norovirus,Norwalk virus | 1 | — | KF712510 |
| Norovirus Hu/GII,4/NIHIC2,3/2010/USA | NC_001959 | vertebrates,human | Caliciviridae,Norovirus,Norwalk virus | 1 | — | KF712496 |
| Norovirus Hu/GII,4/NIHIC27,2/2012/USA | NC_001959 | vertebrates,human | Caliciviridae,Norovirus,Norwalk virus | 1 | — | KF712497 |
| Norovirus Hu/GII,4/NIHIC28,6/2012/USA | NC_001959 | vertebrates,human | Caliciviridae,Norovirus,Norwalk virus | 1 | — | KF712508 |
| Norovirus Hu/GII,4/NIHIC35/2013/USA | NC_001959 | vertebrates,human | Caliciviridae,Norovirus,Norwalk virus | 1 | — | KF712502 |
| Norovirus H u/G II, 4/N SW 123B/2010/AU | NC_001959 | vertebrates,human | Caliciviridae,Norovirus,Norwalk virus | 1 | — | JQ613552 |
| Norovirus Hu/GII,4/New Orleans1805/2009/USA | NC_001959 | vertebrates,human | Caliciviridae,Norovirus,Norwalk virus | 1 | — | GU445325 |
| Norovirus Hu/G11,4/Ohio/7G/2012/USA | NC_001959 | vertebrates,human | Caliciviridae,Norovirus,Norwalk virus | 1 | — | JX126913 |
| Norovirus Hu/G11,4/Ohio/71/2012/USA | NC_001959 | vertebrates,human | Caliciviridae,Norovirus,Norwalk virus | 1 | — | JX126912 |
| Norovirus Hu/G11,4/Orange/NSW001P/2008/AU | NC_001959 | vertebrates,human | Caliciviridae,Norovirus,Norwalk virus | 1 | — | GQ845367 |
| Norovirus 87R/2007/Hu/GII,4/Rathmines/NSW2 AUS | NC_001959 | vertebrates,human | Caliciviridae,Norovirus,Norwalk virus | 1 | — | GQ845024 |

TABLE 10-continued

| Taxonomy | Rep.Acc.ID | Host | VuroCap-1.0 Taxonomy | | Seg. | |
| --- | --- | --- | --- | --- | --- | --- |
| | | | # GN's | Lineage | Count | GN.Acc.IDs |
| Norovirus Hu/GII,4/Shellharbour/NSW 696T/2006/AUS | NC_001959 | vertebrates,human | 1 | Caliciviridae,Norovirus,Norwalk virus | — | EF684915 |
| Norovirus Hu/GII,4/Sutherland/NSW 05G/2007/AUS | NC_001959 | vertebrates,human | 1 | Caliciviridae,Norovirus,Norwalk virus | — | GQ845368 |
| Norovirus Hu/G II_4/Teralba/NSW881Z/2009/AUS | NC_001959 | vertebrates,human | 1 | Caliciviridae,Norovirus,Norwalk virus | — | HM748972 |
| Norovirus Hu/GII,4/Turramurra/NSW892U/2009/AUS | NC_001959 | vertebrates,human | 1 | Caliciviridae,Norovirus,Norwalk virus | — | HM748973 |
| Norovirus Hu/GII,4/Westmead/NSW3 639/2008/AUS | NC_001959 | vertebrates,human | 1 | Caliciviridae,Norovirus,Norwalk virus | — | GQ845366 |
| Norovirus Hu/GII,6/NIHIC34.1/2013/USA | NC_001959 | vertebrates,human | 1 | Caliciviridae,Norovirus,Norwalk virus | — | KF712509 |
| Norovirus Hu/GII,e-GII.12/StGeorge/NSW/2008/AU | NC_001959 | vertebrates,human | 1 | Caliciviridae,Norovirus,Norwalk virus 199U | — | GQ845370 |
| Norovirus Hu/GII/10002/2009/VNM | NC_001959 | vertebrates,human | 1 | Caliciviridae,Norovirus,Norwalk virus | — | JQ911595 |
| Norovirus Hu/GII/10003/2009/VNM | NC_001959 | vertebrates,human | 1 | Caliciviridae,Norovirus,Norwalk virus | — | JQ911596 |
| Norovirus Hu/GII/10012/2009/VNM | NC_001959 | vertebrates,human | 1 | Caliciviridae,Norovirus,Norwalk virus | — | JQ911597 |
| Norovirus Hu/GII/10037/2009/VNM | NC_001959 | vertebrates,human | 1 | Caliciviridae,Norovirus,Norwalk virus | — | JQ911598 |
| Norovirus Hu/GII/10101/2009/VNM | NC_001959 | vertebrates,human | 1 | Caliciviridae,Norovirus,Norwalk virus | — | KC409238 |
| Norovirus Hu/GII/10127/2009/VNM | NC_001959 | vertebrates,human | 1 | Caliciviridae,Norovirus,Norwalk virus | — | KC409239 |
| Norovirus Hu/GII/10370/2010/VNM | NC_001959 | vertebrates,human | 1 | Caliciviridae,Norovirus,Norwalk virus | — | KC409240 |
| Norovirus Hu/GII/10405/2010/VNM | NC_001959 | vertebrates,human | 1 | Caliciviridae,Norovirus,Norwalk virus | — | KC409241 |
| Norovirus Hu/GII/10406/2010/VNM | NC_001959 | vertebrates,human | 1 | Caliciviridae,Norovirus,Norwalk virus | — | KC409242 |
| Norovirus Hu/GII/10411/2010/VNM | NC_001959 | vertebrates,human | 1 | Caliciviridae,Norovirus,Norwalk virus | — | KC409243 |
| Norovirus Hu/GII/10420/2010/VNM | NC_001959 | vertebrates,human | 1 | Caliciviridae,Norovirus,Norwalk virus | — | KC409244 |
| Norovirus Hu/GII/20048/2009/VNM | NC_001959 | vertebrates,human | 1 | Caliciviridae,Norovirus,Norwalk virus | — | KC409245 |
| Norovirus Hu/GII/20064/2009/VNM | NC_001959 | vertebrates,human | 1 | Caliciviridae,Norovirus,Norwalk virus | — | KC409246 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Norovirus Hu/GII/20079/2009/VNM | NC_001959 | vertebrates,human | Caliciviridae,Norovirus,Norwalk virus | 1 | — | KC409247 |
| Norovirus Hu/GII/20107/2009/VNM | NC_001959 | vertebrates,human | Caliciviridae,Norovirus,Norwalk virus | 1 | — | KC409248 |
| Norovirus Hu/GII/20108/2009/VNM | NC_001959 | vertebrates,human | Caliciviridae,Norovirus,Norwalk virus | 1 | — | KC409249 |
| Norovirus Hu/GII/20144/2009/VNM | NC_001959 | vertebrates,human | Caliciviridae,Norovirus,Norwalk virus | 1 | — | KC409250 |
| Norovirus Hu/GII/20146/2009/VNM | NC_001959 | vertebrates,human | Caliciviridae,Norovirus,Norwalk virus | 1 | — | KC409251 |
| Norovirus Hu/GII/20150/2009/VNM | NC_001959 | vertebrates,human | Caliciviridae,Norovirus,Norwalk virus | 1 | — | KC409252 |
| Norovirus Hu/GII/20151/2009/VNM | NC_001959 | vertebrates,human | Caliciviridae,Norovirus,Norwalk virus | 1 | — | KC409253 |
| Norovirus Hu/GII/20153/2009/VNM | NC_001959 | vertebrates,human | Caliciviridae,Norovirus,Norwalk virus | 1 | — | KC409254 |
| Norovirus Hu/GII/20154/2009/VNM | NC_001959 | vertebrates,human | Caliciviridae,Norovirus,Norwalk virus | 1 | — | KC409255 |
| Norovirus Hu/GII/20156/2009/VNM | NC_001959 | vertebrates,human | Caliciviridae,Norovirus,Norwalk virus | 1 | — | KC409256 |
| Norovirus Hu/GII/20159/2009/VNM | NC_001959 | vertebrates,human | Caliciviridae,Norovirus,Norwalk virus | 1 | — | KC409257 |
| Norovirus Hu/GII/20161/2009/VNM | NC_001959 | vertebrates,human | Caliciviridae,Norovirus,Norwalk virus | 1 | — | KC409258 |
| Norovirus Hu/GII/20162/2009/VNM | NC_001959 | vertebrates,human | Caliciviridae,Norovirus,Norwalk virus | 1 | — | KC409259 |
| Norovirus Hu/GII/20164/2009/VNM | NC_001959 | vertebrates,human | Caliciviridae,Norovirus,Norwalk virus | 1 | — | KC409260 |
| Norovirus Hu/GII/20171/2009/VNM | NC_001959 | vertebrates,human | Caliciviridae,Norovirus,Norwalk virus | 1 | — | KC409261 |
| Norovirus Hu/GII/20172/2009/VNM | NC_001959 | vertebrates,human | Caliciviridae,Norovirus,Norwalk virus | 1 | — | KC409262 |
| Norovirus Hu/GII/20173/2009/VNM | NC_001959 | vertebrates,human | Caliciviridae,Norovirus,Norwalk virus | 1 | — | KC409263 |
| Norovirus Hu/GII/20176/2009/VNM | NC_001959 | vertebrates,human | Caliciviridae,Norovirus,Norwalk virus | 1 | — | KC409264 |
| Norovirus Hu/GII/20180/2009/VNM | NC_001959 | vertebrates,human | Caliciviridae,Norovirus,Norwalk virus | 1 | — | KC409265 |
| Norovirus Hu/GII/20182/2009/VNM | NC_001959 | vertebrates,human | Caliciviridae,Norovirus,Norwalk virus | 1 | — | KC409266 |
| Norovirus Hu/GII/20184/2009/VNM | NC_001959 | vertebrates,human | Caliciviridae,Norovirus,Norwalk virus | 1 | — | KC409267 |
| Norovirus Hu/GII/20185/2009/VNM | NC_001959 | vertebrates,human | Caliciviridae,Norovirus,Norwalk virus | 1 | — | KC409268 |
| Norovirus Hu/GII/20187/2009/VNM | NC_001959 | vertebrates,human | Caliciviridae,Norovirus,Norwalk virus | 1 | — | KC409269 |
| Norovirus Hu/GII/20189/2009/VNM | NC_001959 | vertebrates,human | Caliciviridae,Norovirus,Norwalk virus | 1 | — | KC409270 |

TABLE 10-continued

| Taxonomy | Rep.Acc.ID | Host | VireCap-1.0 Taxonomy Lineage | # GN's | Seg. Count | GN.Acc.IDs |
|---|---|---|---|---|---|---|
| Norovirus Hu/GII/20190/2009/VNM | NC_001959 | vertebrates,human | Caliciviridae,Norovirus,Norwalk virus | 1 | — | KC409271 |
| Norovirus Hu/GII/20192/2009/VNM | NC_001959 | vertebrates,human | Caliciviridae,Norovirus,Norwalk virus | 1 | — | KC409272 |
| Norovirus Hu/GII/20196/2009/VNM | NC_001959 | vertebrates,human | Caliciviridae,Norovirus,Norwalk virus | 1 | — | KC409273 |
| Norovirus Hu/GII/20198/2009/VNM | NC_001959 | vertebrates,human | Caliciviridae,Norovirus,Norwalk virus | 1 | — | KC409274 |
| Norovirus Hu/GII/20202/2009/VNM | NC_001959 | vertebrates,human | Caliciviridae,Norovirus,Norwalk virus | 1 | — | KC409275 |
| Norovirus Hu/GII/20205/2009/VNM | NC_001959 | vertebrates,human | Caliciviridae,Norovirus,Norwalk virus | 1 | — | KC409276 |
| Norovirus Hu/GII/20206/2009/VNM | NC_001959 | vertebrates,human | Caliciviridae,Norovirus,Norwalk virus | 1 | — | KC409277 |
| Norovirus Hu/GII/20208/2009/VNM | NC_001959 | vertebrates,human | Caliciviridae,Norovirus,Norwalk virus | 1 | — | KC409278 |
| Norovirus Hu/GII/20215/2009/VNM | NC_001959 | vertebrates,human | Caliciviridae,Norovirus,Norwalk virus | 1 | — | KC409279 |
| Norovirus Hu/GII/20217/2009/VNM | NC_001959 | vertebrates,human | Caliciviridae,Norovirus,Norwalk virus | 1 | — | KC409280 |
| Norovirus Hu/GII/20229/2009/VNM | NC_001959 | vertebrates,human | Caliciviridae,Norovirus,Norwalk virus | 1 | — | KC409281 |
| Norovirus Hu/GII/20230/2009/VNM | NC_001959 | vertebrates,human | Caliciviridae,Norovirus,Norwalk virus | 1 | — | KC409282 |
| Norovirus Hu/GII/20233/2009/VNM | NC_001959 | vertebrates,human | Caliciviridae,Norovirus,Norwalk virus | 1 | — | KC409283 |
| Norovirus Hu/GII/20248/2009/VNM | NC_001959 | vertebrates,human | Caliciviridae,Norovirus,Norwalk virus | 1 | — | KC409284 |
| Norovirus Hu/GII/20258/2009/VNM | NC_001959 | vertebrates,human | Caliciviridae,Norovirus,Norwalk virus | 1 | — | KC409285 |
| Norovirus Hu/GII/20263/2009/VNM | NC_001959 | vertebrates,human | Caliciviridae,Norovirus,Norwalk virus | 1 | — | KC409286 |
| Norovirus Hu/GII/20271/2009/VNM | NC_001959 | vertebrates,human | Caliciviridae,Norovirus,Norwalk virus | 1 | — | KC409287 |
| Norovirus Hu/GII/20276/2009/VNM | NC_001959 | vertebrates,human | Caliciviridae,Norovirus,Norwalk virus | 1 | — | KC409288 |
| Norovirus Hu/GII/20302/2009/VNM | NC_001959 | vertebrates,human | Caliciviridae,Norovirus,Norwalk virus | 1 | — | KC409289 |
| Norovirus Hu/GII/20344/2009/VNM | NC_001959 | vertebrates,human | Caliciviridae,Norovirus,Norwalk virus | 1 | — | KC409290 |
| Norovirus Hu/GII/20350/2009/VNM | NC_001959 | vertebrates,human | Caliciviridae,Norovirus,Norwalk virus | 1 | — | KC409291 |
| Norovirus Hu/GII/20357/2009/VNM | NC_001959 | vertebrates,human | Caliciviridae,Norovirus,Norwalk virus | 1 | — | KC409292 |
| Norovirus Hu/GII/20365/2010/VNM | NC_001959 | vertebrates,human | Caliciviridae,Norovirus,Norwalk virus | 1 | — | KC409293 |
| Norovirus Hu/GII/20373/2010/VNM | NC_001959 | vertebrates,human | Caliciviridae,Norovirus,Norwalk virus | 1 | — | KC409294 |

TABLE 10-continued

| Taxonomy | Rep.Acc.ID | Host | ViroCap-1.0 Taxonomy | | Seg. Count | GN.Acc.IDs |
|---|---|---|---|---|---|---|
| | | | Lineage | # GN's | | |
| Norovirus Hu/GII/20407/2010/VNM | NC_001959 | vertebrates,human | Caliciviridae,Norovirus,Norwalk virus | 1 | — | KC409295 |
| Norovirus Hu/GII/20413/2010/VNM | NC_001959 | vertebrates,human | Caliciviridae,Norovirus,Norwalk virus | 1 | — | KC409296 |
| Norovirus Hu/GII/20424/2010/VNM | NC_001959 | vertebrates,human | Caliciviridae,Norovirus,Norwalk virus | 1 | — | KC409297 |
| Norovirus Hu/GII/20448/2010/VNM | NC_001959 | vertebrates,human | Caliciviridae,Norovirus,Norwalk virus | 1 | — | KC409298 |
| Norovirus Hu/GII/20457/2010/VNM | NC_001959 | vertebrates,human | Caliciviridae,Norovirus,Norwalk virus | 1 | — | KC409299 |
| Norovirus Hu/GII/20460/2010/VNM | NC_001959 | vertebrates,human | Caliciviridae,Norovirus,Norwalk virus | 1 | — | KC409300 |
| Norovirus Hu/GII/20469/2010/VNM | NC_001959 | vertebrates,human | Caliciviridae,Norovirus,Norwalk virus | 1 | — | KC409301 |
| Norovirus Hu/GII/20477/2010/VNM | NC_001959 | vertebrates,human | Caliciviridae,Norovirus,Norwalk virus | 1 | — | KC409302 |
| Norovirus Hu/GII/20478/2010/VNM | NC_001959 | vertebrates,human | Caliciviridae,Norovirus,Norwalk virus | 1 | — | KC409303 |
| Norovirus Hu/GII/30017/2009/VNM | NC_001959 | vertebrates,human | Caliciviridae,Norovirus,Norwalk virus | 1 | — | KC409304 |
| Norovirus Hu/GII/30026/2009/VNM | NC_001959 | vertebrates,human | Caliciviridae,Norovirus,Norwalk virus | 1 | — | KC409305 |
| Norovirus Hu/GII/30040/2009/VNM | NC_001959 | vertebrates,human | Caliciviridae,Norovirus,Norwalk virus | 1 | — | KC409306 |
| Norovirus Hu/GII/30045/2009/VNM | NC_001959 | vertebrates,human | Caliciviridae,Norovirus,Norwalk virus | 1 | — | KC409307 |
| Norovirus Hu/GII/30113/2009/VNM | NC_001959 | vertebrates,human | Caliciviridae,Norovirus,Norwalk virus | 1 | — | KC409309 |
| Norovirus Hu/GII/30129/2009/VNM | NC_001959 | vertebrates,human | Caliciviridae,Norovirus,Norwalk virus | 1 | — | KC409310 |
| Norovirus Hu/GII/30199/2009/VNM | NC_001959 | vertebrates,human | Caliciviridae,Norovirus,Norwalk virus | 1 | — | KC409311 |
| Norovirus Hu/GII/30201/2009/VNM | NC_001959 | vertebrates,human | Caliciviridae,Norovirus,Norwalk virus | 1 | — | KC409312 |
| Norovirus Hu/GII/30206/2009/VNM | NC_001959 | vertebrates,human | Caliciviridae,Norovirus,Norwalk virus | 1 | — | KC409313 |
| Norovirus Hu/GII/30211/2009/VNM | NC_001959 | vertebrates,human | Caliciviridae,Norovirus,Norwalk virus | 1 | — | KC409315 |
| Norovirus Hu/GII/30212/2009/VNM | NC_001959 | vertebrates,human | Caliciviridae,Norovirus,Norwalk virus | 1 | — | KC409316 |
| Norovirus Hu/GII/30266/2009/VNM | NC_001959 | vertebrates,human | Caliciviridae,Norovirus,Norwalk virus | 1 | — | KC409318 |
| Norovirus Hu/G11/8610/Saga/2008/JPN | NC_001959 | vertebrates,human | Caliciviridae,Norovirus,Norwalk virus | 1 | — | GU594162 |
| Norovirus Hu/GII/Carlow/2002/Ire | NC_001959 | vertebrates,human | Caliciviridae,Norovirus,Norwalk virus | 1 | — | DQ415279 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Norovirus Hu/Guangzhou/NVgz01/CHN | NC_001959 | vertebrates,human | Caliciviridae,Norovirus,Norwalk virus | 1 | — | DQ369797 |
| Norovirus Hu/Houston/TCH186/2002/US | NC_001959 | vertebrates,human | Caliciviridae,Norovirus,Norwalk virus | 1 | — | EU310927 |
| Norovirus Hu/MK04/2004/JP | NC_001959 | vertebrates,human | Caliciviridae,Norovirus,Norwalk virus | 1 | — | DQ456824 |
| Norovirus Hu/NLV/Dresden174/pUS-Nor11/1997/GE | NC_001959 | vertebrates,human | Caliciviridae,Norovirus,Norwalk virus | 1 | — | AY741811 |
| Norovirus Hu/NLV/GII/Neustrelitz260/2000/DE | NC_001959 | vertebrates,human | Caliciviridae,Norovirus,Norwalk virus | 1 | — | AY772730 |
| Norovirus Hu/NLV/Oxford/B2S16/2002/UK | NC_001959 | vertebrates,human | Caliciviridae,Norovirus,Norwalk virus | 1 | — | AY587989 |
| Norovirus Hu/NLV/Oxford/B4S1/2002/UK | NC_001959 | vertebrates,human | Caliciviridae,Norovirus,Norwalk virus | 1 | — | AY587988 |
| Norovirus Hu/NLV/Oxford/B452/2002/UK | NC_001959 | vertebrates,human | Caliciviridae,Norovirus,Norwalk virus | 1 | — | AY587983 |
| Norovirus Hu/NLV/Oxford/B454/2002/UK | NC_001959 | vertebrates,human | Caliciviridae,Norovirus,Norwalk virus | 1 | — | AY587986 |
| Norovirus Hu/NLV/Oxford/B455/2002/UK | NC_001959 | vertebrates,human | Caliciviridae,Norovirus,Norwalk virus | 1 | — | AY587984 |
| Norovirus Hu/NLV/Oxford/B456/2002/UK | NC_001959 | vertebrates,human | Caliciviridae,Norovirus,Norwalk virus | 1 | — | AY587985 |
| Norovirus Hu/NLV/Oxford/B457/2002/UK | NC_001959 | vertebrates,human | Caliciviridae,Norovirus,Norwalk virus | 1 | — | AY587987 |
| Norovirus Hu/OsakaNI/2004/JP | NC_001959 | vertebrates,human | Caliciviridae,Norovirus,Norwalk virus | 1 | — | DQ366347 |
| Norovirus Hu/Pune/PC15/2006/India | NC_001959 | vertebrates,human | Caliciviridae,Norovirus,Norwalk virus | 1 | — | EU921344 |
| Norovirus Hu/Pune/PC51/2007/India | NC_001959 | vertebrates,human | Caliciviridae,Norovirus,Norwalk virus | 1 | — | EU921388 |
| Norovirus Hu/Pune/PC52/2007/India | NC_001959 | vertebrates,human | Caliciviridae,Norovirus,Norwalk virus | 1 | — | EU921389 |
| Norovirus Hu/Texas/TCHQ4-577/2004/US | NC_001959 | vertebrates,human | Caliciviridae,Norovirus,Norwalk virus | 1 | — | AB365435 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Norovirus genogroup 2 | NC_001959 | vertebrates,human | 2 | Caliciviridae,Norovirus,Norwalk virus | — | AY502020,AY502023 |
| Norovirus genogroup 3 | NC_001959 | vertebrates,human | 1 | Caliciviridae,Norovirus,Norwalk virus | — | JX145650 |
| Norovirus mouse/Hannover1/2007/DEU | NC_001959 | vertebrates,human | 1 | Caliciviridae,Norovirus,Norwalk virus | — | EU854589 |
| Norovirus pig/GII/Ch6/China/2009 | NC_001959 | vertebrates,human | 1 | Caliciviridae,Norovirus,Norwalk virus | — | HQ392821 |
| Norovirus swine/GII/OH-QW 125/03/US | NC_001959 | vertebrates,human | 1 | Caliciviridae,Norovirus,Norwalk virus | — | AY823305 |
| North American arenavirus | NC_010700 | vertebrates,human | 3 | Arenaviridae,Arenavirus,Whitewater Arroyo virus | seg. S | EU123331,EU123330,EU123329 |
| Norwalk virus | NC_001959 | vertebrates,human | 3 | Caliciviridae,Norovirus,Norwalk virus | — | AF093797,AF504671,M87661 |
| Norwalk-like virus | NC_001959 | vertebrates,human | 17 | Caliciviridae,Norovirus,Norwalk virus | — | AB039780,AB083780,AB039782,AB039779,AY126474,AB039777,AB044366,AB126320,AB039776,AB083781,AB081723,AB045603,AB039774,AB039778,AB084071,AB039781,AB039775 |
| Oliveros virus | NC_010248 | vertebrates,human | 1 | Arenaviridae,Arenavirus,Oliveros virus | seg. S | U34248 |
| Oliveros virus | NC_010250 | vertebrates,human | 1 | Arenaviridae,Arenavirus,Oliveros virus | seg. L | AY216514 |
| Oran virus | NC_003466 | vertebrates,human | 1 | Bunyaviridae,Hantavirus,Andes virus | seg. S | AF482715 |
| Oran virus | NC_003467 | vertebrates,human | 1 | Bunyaviridae,Hantavirus,Andes virus | seg. M | AF028024 |
| Orangutan hepadnavirus | NC_003977 | vertebrates,human | 2 | Hepadnaviridae,Orthohepadnavirus,Hepatitis B virus | — | AF193863,AF193864 |
| Parainfluenza virus 5 | NC_006430 | vertebrates,human | 13 | Paramyxoviridae,Rubulavirus,Parainfluenza virus 5 | — | JQ743322,JQ743319,JQ743321,KC852177,JQ743327,JQ743328,JQ743318,JQ743325,JQ743324,JQ743323,AF052755,JQ743326,JQ743320 |
| Parana virus | NC_010756 | vertebrates,human | 2 | Arenaviridae,Arenavirus,Parana virus | seg. S | AF485261,AF512829 |
| Parana virus | NC_010761 | vertebrates,human | 1 | Arenaviridae,Arenavirus,Parana virus | seg. L | EU627613 |
| Pergamino virus | NC_003466 | vertebrates,human | 1 | Bunyaviridae,Hantavirus,Andes virus | seg. S | AF482717 |
| Peste-des-petits-ruminants virus | NC_006383 | vertebrates,human | 11 | Paramyxoviridae,Morbillivirus,Peste-des-petits-ruminants virus | — | HQ197753,JX217850,AJ849636,KF727981,AY560591,EU267274,KC594074,X74443,EU267273,FJ905304,JF939201 |
| Pichinde virus | NC_006439 | vertebrates,human | 3 | Arenaviridae,Arenavirus,Pichinde virus | seg. L | AF427517,EF529745,EF529747 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Pichinde virus | NC_006447 | vertebrates,human | Arenaviridae,Arenavirus,Pichinde virus | 10 | seg. S | U77602,EF529746,M16734,EF529744,AF081552,K02734,AF081553,AF081554,AF081555,M16735 |
| Pigeon paramyxovirus 1 | NC_002617 | vertebrates,human | Paramyxoviridae,Avulavirus,Newcastle disease virus | 18 | — | GQ429292,JX486557,JX901121,JX901120,JX486555,JX486556,FJ410145,JX901119,JX486551,FJ410147,JX901110,JX486552,JX486554,JX901123,JX486553,JX901122,JX486550,JX901109 |
| Pigeon paramyxovirus-1 | NC_002617 | vertebrates,human | Paramyxoviridae,Avulavirus,Newcastle disease virus | 1 | — | AJ880277 |
| Pirital virus | NC_005894 | vertebrates,human | Arenaviridae,Arenavirus,Pirital virus | 9 | seg. S | AF485262,AY574571,AF277659,AY573923,AY574572,EU542420,AY574573,AY573921,AY575850 |
| Pirital virus | NC_005897 | vertebrates,human | Arenaviridae,Arenavirus,Pirital virus | 2 | seg. L | AY216505,AY494081 |
| Pneumonia virus of mice 15 | NC_006579 | vertebrates,human | Paramyxoviridae,Pneumovirus,Murine pneumonia virus | 1 | — | AY743910 |
| Pneumonia virus of mice J3666 | NC_006579 | vertebrates,human | Paramyxoviridae,Pneumovirus,Murine pneumonia virus | 1 | — | AY743909 |
| Porcine enteric sapovirus | NC_000940,NC_010624,NC_006269,NC_006554 | vertebrates,human | Caliciviridae,Sapovirus,Sapporo virus | 3 | — | AF182760,AB221130,AY425671 |
| Porcine rotavirus | NC_007543 | vertebrates,human | Reoviridae,Rotavirus,Rotavirus C | 3 | seg. 6 | EU169871,EU169870,EU169869 |
| Porcine rotavirus | NC_007544 | vertebrates,human | Reoviridae,Rotavirus,Rotavirus C | 1 | seg. 7 | X60546 |
| Porcine rotavirus | NC_007545 | vertebrates,human | Reoviridae,Rotavirus,Rotavirus C | 2 | seg. 9 | EU169873,EU169872 |
| Porcine rotavirus | NC_007569 | vertebrates,human | Reoviridae,Rotavirus,Rotavirus C | 3 | seg. | EU169874,DQ003298,10,DQ003299 |
| Porcine rotavirus | NC_007570 | vertebrates,human | Reoviridae,Rotavirus,Rotavirus C | 10 | seg. 5 | L29184,DQ534018,FJ494692,M29287,FJ494691,DQ003294,AB576626,FJ494690,DQO03295,L29186 |
| Porcine rotavirus | NC_007571 | vertebrates,human | Reoviridae,Rotavirus,Rotavirus C | 101 | seg. 8 | EF474079,FJ807879,FJ807796,DQ003292,FJ807870,DQ534015,FJ807815,FJ807854,FJ807868,FJ807873,FJ807840,FJ807874, |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| | | | | | | FJ807844,FJ807793, FJ807823,FJ807817, FJ807792,FJ807819, FJ807803,FJ807797, FJ807871,FJ807788, FJ807790,FJ807836, FJ807820,FJ807843, FJ807829,FJ807863, FJ807798,FJ807837, FJ807839,FJ807825, FJ807794,FJ807853, FJ807808,FJ807842, FJ807869,FJ807838, FJ807809,FJ807867, FJ807795,FJ807816, FJ807806,FJ807822, FJ807801,FJ807855, FJ807833,AF192267, FJ807835,FJ807802, FJ807818,FJ807847, FJ807789,FJ807810, FJ807828,FJ807862, FJ807832,FJ807851, FJ807866,FJ807813, FJ807831,FJ807848, FJ807845,DQ003293, FJ807877,FJ807852, FJ807858,FJ807826, FJ807859,FJ807811, FJ807799,AY766085, FJ807849,FJ807807, FJ807830,FJ807878, FJ807846,FJ807791, FJ807861,FJ807821, FJ807857,FJ807800, FJ807865,FJ807856, FJ807805,FJ807812, FJ807860,EU445113, FJ807804,FJ807824, FJ807841,FJ807864, FJ807876,FJ807875, FJ807850,FJ807827, FJ807834,FJ807814, L10361,FJ807872,L10360 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Porcine rotavirus | NC_007572 | vertebrates,human | 8 | Reoviridae,Rotavirus,Rotavirus C | seg. 3 | L10358,DQ003290,Li0359,DQ536362,DQ786578,DQ003291,DQ534016,AB576625 |
| Porcine rotavirus | NC_007573 | vertebrates,human | 6 | Reoviridae,Rotavirus,Rotavirus C | seg. 11 | DQ000296,DQ0474,D0003297,AB576628,DQ534017,DQ82341 6 |
| Porcine rotavirus A | NC_011501 | vertebrates,human | 7 | Reoviridae,Rotavirus,Rotavirus A | seg. 7 | JF796709,JF796698,AB779644,AB779643,JF796720,AB779642,AB779645 |
| Porcine rotavirus A | NC_011502 | vertebrates,human | 9 | Reoviridae,Rotavirus,Rotavirus A | seg. 8 | AB779639,AB779641,JF796719,JF796697,AB779638,JF796708,JF781165,AB779640,JF796730 |
| Porcine rotavirus A | NC_011503 | vertebrates,human | 26 | Reoviridae,Rotavirus,Rotavirus A | seg. 9 | AB176680,AB779619,DQ515961,JF796728,DQ204743,AY70778 8,AB573873,DQ7865 77,AB176677,AY707 787,DQ786576,JF781 163,AB176678,DQ25 6502,AB573875,JF79 6739,AB573879,AB5 73877,AB176681,AB 176683,JF796706,KC 292205,DQ256503,JF 796717,AB605258,A B176679 |
| Porcine rotavirus A | NC_011504 | vertebrates,human | 11 | Reoviridae,Rotavirus,Rotavirus A | seg. 10 | JF796699,JF796721,D88831,JF781167,JF 796710,JF796732,JN 650610,FJ492833,DQ 204740,FJ492834,JN 650611 |
| Porcine rotavirus A | NC_011505 | vertebrates,human | 13 | Reoviridae,Rotavirus,Rotavirus A | seg. 11 | KC117150,DQ204739 ,JF796733,JF781168, JF796722,KC117151, KC117152,JF796700, KC117147,KC117149 ,DQ916134,KC11714 8,JF796711 |
| Porcine rotavirus A | NC_011506 | vertebrates,human | 5 | Reoviridae,Rotavirus,Rotavirus A | seg. 2 | AB779627,JF781159, AB779628,AB779629 ,AB779626 |

TABLE 10-continued

VireCap-1.0 Taxonomy

| Taxonomy | Rep.Acc.ID | Host | # GN's | Lineage | Seg. Count | GN.Acc.IDs |
|---|---|---|---|---|---|---|
| Porcine rotavirus A | NC_011507 | vertebrates,human | 9 | Reoviridae,Rotavirus,Rotavirus A | seg. 1 | AB779622,JF796712, JF796701,AB779625, JF781158,JF796723, AB779624,JF796734, AB779623 |
| Porcine rotavirus A | NC_011508 | vertebrates,human | 11 | Reoviridae,Rotavirus,Rotavirus A | seg. 3 | AB779632,JF781160, AB779631,JF796714, AB779630,AY300922 ,AB779633,AY27792 1,JF796703,JF79672 5,JF796736 |
| Porcine rotavirus A | NC_011509 | vertebrates,human | 59 | Reoviridae,Rotavirus,Rotavirus A | seg. 6 | EU372751,EU372791 ,EU372765,EU372751 3,EU372789,AB7796 21,EU372776,EU372 793,EU372764,EU37 2795,EU372797,EU3 72783,EU372774,JF7 96705,EU372787,KC 855062,EU372773,D 0119822,EU372756, JF796716,EU372781, EU372755,EU372772 ,EU372785,JF796727 ,EU372766,EU372776 2,EU372761,EU3727 63,EU372798,EU372 786,EU372767,EU37 2770,KC855061,EU3 72779,EU372799,EU 372768,EU372757,E U372771,EU372796, EU372777,EU372752 ,EU372782,EU37278 0,EU372790,KC8550 60,EU372754,EU372 758,EU372794,EU37 2784,EU372769,EU3 72760,EU372759,EU 372792,AB779620,E U372788,EU372778, |
| Porcine rotavirus A | NC_011510 | vertebrates,human | 10 | Reoviridae,Rotavirus,Rotavirus A | seg. 4 | JF781161,JF796737, AB573878,DQ118979 ,AB573876,JF796726 ,JF796715,AB573874 ,JF796704,FJ492835 |
| Porcine rotavirus A A411/G3P[7] | NC_011504 | vertebrates,human | 1 | Reoviridae,Rotavirus,Rotavirus A | seg. 10 | AF144799 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Porcine rotavirus A strain 134/04-15 | NC_011503 | vertebrates,human | 1 | Reoviridae,Rotavirus,Rotavirus A | seg. 9 | DQ062572 |
| Porcine rotavirus A strain 134/04-15 | NC_011510 | vertebrates,human | 1 | Reoviridae,Rotavirus,Rotavirus A | seg. 4 | DQ061053 |
| Porcine rotavirus A34 | NC_007573 | vertebrates,human | 1 | Reoviridae,Rotavirus,Rotavirus C | seg. 11 | AF165219 |
| Porcine rotavirus B | NC_021542 | vertebrates,human | 1 | Reoviridae,Rotavirus,Rotavirus B | seg. 9 | AB490417 |
| Porcine rotavirus B | NC_021546 | vertebrates,human | 15 | Reoviridae,Rotavirus,Rotavirus B | seg. 5 | AB646359,AB646363,AB646364,AB646354,AB646360,AB646361,AB646350,AB646351,AB646353,AB646358,AB646352,AB646356,AB646357,AB646355,AB646362 |
| Porcine rotavirus C | NC_007543 | vertebrates,human | 1 | Reoviridae,Rotavirus,Rotavirus C | seg. 6 | M69115 |
| Porcine rotavirus C | NC_007546 | vertebrates,human | 1 | Reoviridae,Rotavirus,Rotavirus C | seg. 2 | M74217 |
| Porcine rotavirus C | NC_007547 | vertebrates,human | 1 | Reoviridae,Rotavirus,Rotavirus C | seg. 1 | M74216 |
| Porcine rotavirus C | NC_007570 | vertebrates,human | 2 | Reoviridae,Rotavirus,Rotavirus C | seg. 5 | HQ323754,M94157 |
| Porcine rotavirus C | NC_007571 | vertebrates,human | 14 | Reoviridae,Rotavirus,Rotavirus C | seg. 8 | EF464648,EF464656,EF464654,EF464651,U31749,EF464652,EF464653,EF464655,EF464650,U31748,HQ323753,EF464649,M61101,EF464657 |
| Porcine rotavirus C | NC_007573 | vertebrates,human | 2 | Reoviridae,Rotavirus,Rotavirus C | seg. 11 | AF093202,AF093203 |
| Porcine rotavirus C | NC_007574 | vertebrates,human | 1 | Reoviridae,Rotavirus,Rotavirus C | seg. 4 | M74219 |
| Porcine rotavirus CN86 | NC_007570 | vertebrates,human | 1 | Reoviridae,Rotavirus,Rotavirus C | seg. 5 | U10031 |
| Porcine rotavirus strain 344/04-1 | NC_007571 | vertebrates,human | 1 | Reoviridae,Rotavirus,Rotavirus C | seg. 8 | DQ813658 |
| Porcine rotavirus strain A131 | NC_007573 | vertebrates,human | 1 | Reoviridae,Rotavirus,Rotavirus C | seg. 11 | AF144798 |
| Porcine rotavirus strain A253 | NC_007573 | vertebrates,human | 1 | Reoviridae,Rotavirus,Rotavirus C | seg. 11 | AF144797 |
| Porcine rubullavirus | NC_009640 | vertebrates,human | 1 | Paramyxoviridae,Rubulavirus,Porcine rubulavirus | — | BK005918 |
| Porcine torque teno virus 1 | NC_014070 | vertebrates,human | 2 | Anelloviridae,Iotatorquevirus,Torque teno sus virus 1a | — | JX173482,JX173481 |
| Puumala virus | NC_005223 | vertebrates,human | 25 | Bunyaviridae,Hantavirus,Puumala virus | seg. M | JQ319172,JQ319174,X61034,JQ319173,U14136,AF442617,AF442614,JQ319175,AF367061,AB433850,AF442616,L08754,JN831944,Z49214,M29979,Z84205,AB433852,LO... |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Puumala virus | NC_005224 | vertebrates,human | 56 | Bunyaviridae,Hantavirus,Puumala virus | seg. S | 8755,HE801634,JN831948,JN831951,AY521636218,AF442615,U22418,AB297666 AJ314597,FN377822,X61035,AF367069,AJ238788,AF367070,HE801633,U22423,AF367068,JQ319170,JN696371,JQ319163,JQ319164,Z30708,JN831943,AB297665,AJ238790,JQ319166,Z69985,JQ319162,Z30705,AB433845,AJ314598,JQ319168,AJ223371,Z30707,Z30706,JQ319171,JN831950,Z30703,AF442613,AJ314599,JQ319161,AF367064,JQ319167,AF367071,JN696376,JN831947,AF367066,AB433843,Z84204,Z30702,J03319169,JN696373,AF367065,AF367067,Z46942,JN696375,AY526219,JQ319165,FN377821,JN696372,Z21497,Z30704,AJ238789,JN696374 |
| Puumala virus | NC_005225 | vertebrates,human | 12 | Bunyaviridae,Hantavirus,Puumala virus | seg. L | JN831945,AB574183,JN831946,M63194,HE801635,AB574184,AY526217,AB297667,JN831952,JN831949,EF405801,Z66548 |
| Puumala-like virus isolate Fusong-Cr-247 | NC_005224 | vertebrates,human | 1 | Bunyaviridae,Hantavirus,Rotavirus A | seg. S | EF442087 |
| Rabbit rotavirus | NC_011503 | vertebrates,human | 4 | Reoviridae,Rotavirus,Rotavirus A | seg. 9 | AF528202,AF528201,AF528203,AF528204 |
| Rabbit rotavirus | NC_011504 | vertebrates,human | 4 | Reoviridae,Rotavirus,Rotavirus A | seg. 10 | AF533536,AF533534,AF533537,AF533535 |
| Rabbit rotavirus | NC_011505 | vertebrates,human | 1 | Reoviridae,Rotavirus,Rotavirus A | seg. 11 | JQ4361 |
| Rabbit rotavirus strain Alabama | NC_011504 | vertebrates,human | 1 | Reoviridae,Rotavirus,Rotavirus A | seg. 10 | AF144792 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rabbitpox virus | NC_006998 | vertebrates,human | Poxviridae,Orthopoxvirus,Vaccinia virus | 1 | — | AY484669 |
| Rabies TABLE 10-continued ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | DQ875051,GU358653,KF154998,GQ918139,JQ685951,JQ730682,JQ685921,EF206709,JQ685902,EU877071,JQ685937,AB519642,JQ685910,AB128149,JQ944707,JQ685952,KC171643,JQ944708,EF206707,AB699220,JQ685928,AB517660,JQ685931,JQ685933,JQ685900,EF206710,JQ685974,EU311738,JQ423952,AB362483,JQ685913,JQ685977,JQ685903,AB517659,JQ685953,JX276550,JQ685914,FJ712194,JQ685911,JQ685906,JQ685915,AB608731,JQ685908,JQ685922,JQ685947,JQ685935,AB519641,HE802676,JQ685956,EU182346,JQ685976,JQ685950,EF206712,JQ685925,EU643590,FJ866836,EU293113,FJ866835,JQ685939,AB009663,DQ875050,KC395280,EF206711,EU877070,JQ685944,JQ685955,EF206716,JQ685929,EU549783,EF206717,JQ685961,JQ944704,JQ685971,KF155002,GU345748,KC762941,JQ685918,JQ685920,JQ685970,JQ685969,JQ685936,HQ891318,JQ685960,JQ685943,JQ685896,JQ685927,JQ685938,EF206715,JQ647510,KF154996,FJ712196,EU293111,JX473840,KC595282,J |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Ravn virus-Ravn,Kenya, 1987 | NC_001608 | vertebrates,human | 3 | Filoviridae,Marburgvirus,Marburg marburgvirus | — | 0685907,JQ946087, KC196743,JX473838, JN786877,JQ685972, JQ685949,JN234411, JQ944705,EU877067 ,JQ944706,JQ685904 ,JQ685899,HQ45038 5,M13215,EU877069, JQ685923,KF155001 |
| Recombinant Hepatitis C Virus S TABLE 10-continued ViroCap-1.0 Taxonomy

| Taxonomy | Rep.Acc.ID | Host | Lineage | # GN's | Seg. Count | GN.Acc.IDs |
|---|---|---|---|---|---|---|
| Recombinant Hepatitis C virus DH6-JFH1 | NC_009827,NC_009826,NC_009825,NC_009824,NC_009823 | vertebrates,human | Flaviviridae,Hepacivirus,Hepatitis C virus | 1 | — | HQ852454 |
| Recombinant Hepatitis C virus ED43(5'UTR-NS2)/JFH1_T827A,T977S | NC_009827,NC_009826,NC_009825,NC_009824,NC_009823 | vertebrates,human | Flaviviridae,Hepacivirus,Hepatitis C virus | 1 | — | JF343785 |
| Recombinant Hepatitis C virus H77(5'UTR-NS2)/JFH1_V787A,Q1247L | NC_009827,NC_009826,NC_009825,NC_009824,NC_009823 | vertebrates,human | Flaviviridae,Hepacivirus,Hepatitis C virus | 1 | — | JF343780 |
| Recombinant Hepatitis C virus H77C/JFH1 | NC_009827,NC_009826,NC_009825,NC_009824,NC_009823 | vertebrates,human | Flaviviridae,Hepacivirus,Hepatitis C virus | 1 | — | EU363761 |
| Recombinant Hepatitis C virus HK6a(5'UTR-NS2)/JFH1_F350S,N417T | NC_009827,NC_009826,NC_009825,NC_009824,NC_009823 | vertebrates,human | Flaviviridae,Hepacivirus,Hepatitis C virus | 1 | — | JF343787 |
| Recombinant Hepatitis C virus HK6a/JFH-1 | NC_009827,NC_009826,NC_009825,NC_009824,NC_009823 | vertebrates,human | Flaviviridae,Hepacivirus,Hepatitis C virus | 1 | — | FJ230883 |

TABLE 10-continued

| Taxonomy | Rep.Acc.ID | Host | ViroCap-1.0 Taxonomy | | Seg. Count | GN.Acc.IDs |
| --- | --- | --- | --- | --- | --- | --- |
| | | | # GN's | Lineage | | |
| Recombinant Hepatitis C virus J4(5'UTR-NS2)/JFH1_F886L_01496L | NC_009827,NC_009826,NC_009825,NC_009824,NC_004102,NC_009823 | vertebrates,human |

TABLE 10-continued

| Taxonomy | Rep.Acc.ID | Host | Lineage | # GN's | Seg. Count | GN.Acc.IDs |
|---|---|---|---|---|---|---|
| Recombinant Hepatitis C virus J6(5'UTR(Cell-U3WTS1)-NS2)/JFH1 | NC_009827,NC_009826,NC_009825,NC_009824,NC_009823 | vertebrates,human | Flaviviridae,Hepacivirus,Hepatitis C virus | 1 | — | JF343

TABLE 10-continued

| Taxonomy | Rep.Acc.ID | Host | ViroCap-1.0 Taxonomy | | | | |
| --- | --- | --- | --- | --- | --- | --- | --- |
| | | | # GN's | Lineage | Seg. Count | GN.Acc.IDs |
| Recombinant Hepatitis C virus J6/JFH1(HCV1-NS5A) | NC_009827,NC_00982 6,NC_0098 25,NC_009 824,NC_00 4102,NC_0 09823 | vertebrates,human | 1 | Flaviviridae,Hepacivirus,Hepatitis C virus | — | HQ852468 |
| Recombinant Hepatitis C virus J6/JFH1(HK6a-NS5A) | NC_009827,NC_00982 6,NC_0098 25,NC_009 824,NC_00 4102,NC_0 09823 | vertebrates,human | 1 | Flaviviridae,Hepacivirus,Hepatitis C virus | — | HQ852465 |
| Recombinant Hepatitis C virus J6/JFH1(J1-NS5A) | NC_009827,NC_00982 6,NC_0098 25,NC_009 824,NC_00 4102,NC_0 09823 | vertebrates,human | 1 | Flaviviridae,Hepacivirus,Hepatitis C virus | — | HQ852469 |
| Recombinant Hepatitis C virus J6/JFH1(J4-NS5A) | NC_009827,NC_00982 6,NC_0098 25,NC_009 824,NC_00 4102,NC_0 09823 | vertebrates,human | 1 | Flaviviridae,Hepacivirus,Hepatitis C virus | — | HQ852460 |
| Recombinant Hepatitis C virus J6/JFH1(J6-NS5A) | NC_009827,NC_00982 6,NC_0098 25,NC_009 824,NC_00 4102,NC_0 09823 | vertebrates,human | 1 | Flaviviridae,Hepacivirus,Hepatitis C virus | — | HQ852461 |
| Recombinant Hepatitis C virus J6/JFH1(0C69-NS5A) | NC_009827,NC_00982 6,NC_0098 25,NC_009 824,NC_00 4102,NC_0 09823 | vertebrates,human | 1 | Flaviviridae,Hepacivirus,Hepatitis C virus | — | HQ852466 |

TABLE 10-continued

| | | | | ViroCap-1.0 Taxonomy | | |
|---|---|---|---|---|---|---|
| Taxonomy | Rep.Acc.ID | Host | # GN's | Lineage | Seg. Count | GN.Acc.IDs |
| Recombinant Hepatitis C virus J6/JFH1(S52-NS5A) | NC_009827,NC_009826,NC_009825,NC_009824,NC_004102,NC_009823 | vertebrates,human | 1 | Flaviviridae,Hepacivirus,Hepatitis C virus | — | HQ852462 |
| Recombinant Hepatitis C virus J6/JFH1(SA13-NS5A) | NC_009827,NC_009826,NC_009825,NC_009824,NC_004102,NC_009823 | vertebrates,human | 1 | Flaviviridae,Hepacivirus,Hepatitis C virus | — | HQ852464 |
| Recombinant Hepatitis C virus J6/JFH1(TN-NS5A) | NC_009827,NC_009826,NC_009825,NC_009824,NC_004102,NC_009823 | vertebrates,human | 1 | Flaviviridae,Hepacivirus,Hepatitis C virus | — | HQ852459 |
| Recombinant Hepatitis C virus J6/JFH1 1-452 | NC_009827,NC_009826,NC_009825,NC_009824,NC_004102,NC_009823 | vertebrates,human | 1 | Flaviviridae,Hepacivirus,Hepatitis C virus | — | JN180456 |
| Recombinant Hepatitis C virus J6/JFH1 1-H K6a | NC_009827,NC_009826,NC_009825,NC_009824,NC_004102,NC_009823 | vertebrates,human | 1 | Flaviviridae,Hepacivirus,Hepatitis C virus | — | JN180455 |
| Recombinant Hepatitis C virus J6/JFH1 1-J6 | NC_009827,NC_009826,NC_009825,NC_009824,NC_004102,NC_009823 | vertebrates,human | 1 | Flaviviridae,Hepacivirus,Hepatitis C virus | — | JN180452 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Recombinant Hepatitis C virus J6/JFH1-JCH2 | NC_009827,NC_009826,NC_009825,NC_009824,NC_004102,NC_009823 | vertebrates,human | Flaviviridae,Hepacivirus,Hepatitis C virus | 1 | — | JN180459 |
| Recombinant Hepatitis C virus J6/JFH1-JCH4 | NC_009827,NC_009826,NC_009825,NC_009824,NC_004102,NC_009823 | vertebrates,human | Flaviviridae,Hepacivirus,Hepatitis C virus | 1 | — | JN180460 |
| Recombinant Hepatitis C virus J6/JFH1-K3a,650 | NC_009827,NC_009826,NC_009825,NC_009824,NC_004102,NC_009823 | vertebrates,human | Flaviviridae,Hepacivirus,Hepatitis C virus | 1 | — | JN180457 |
| Recombinant Hepatitis C virus J6/JFH1-NZL1 | NC_009827,NC_009826,NC_009825,NC_009824,NC_004102,NC_009823 | vertebrates,human | Flaviviridae,Hepacivirus,Hepatitis C virus | 1 | — | JN180458 |
| Recombinant Hepatitis C virus J6/JFH 1-S52 | NC_009827,NC_009826,NC_009825,NC_009824,NC_004102,NC_009823 | vertebrates,human | Flaviviridae,Hepacivirus,Hepatitis C virus | 1 | — | JN180453 |
| Recombinant Hepatitis C virus J6/JFH 1-SA13 | NC_009827,NC_009826,NC_009825,NC_009824,NC_004102,NC_009823 | vertebrates,human | Flaviviridae,Hepacivirus,Hepatitis C virus | 1 | — | JN180454 |

TABLE 10-continued

| Taxonomy | Rep.Acc.ID | Host | # GN's | Lineage | Seg. Count | GN.Acc.IDs |
|---|---|---|---|---|---|---|
| Recombinant Hepatitis C virus J8(5UTR-NS2)/JFH1 | NC_009827,NC_009826,NC_009825,NC_009824,NC_004102,NC_009823 | vertebrates,human | 1 | Flaviviridae,Hepacivirus,Hepatitis C virus | — | JF343783 |
| Recombinant Hepatitis C virus J8/JFH1 | NC_009827,NC_009826,NC_009825,NC_009824,NC_004102,NC_009823 | vertebrates,human | 1 | Flaviviridae,Hepacivirus,Hepatitis C virus | — | FJ230882 |
| Recombinant Hepatitis C virus 0C69/JFH1 | NC_009827,NC_009826,NC_009825,NC_009824,NC_004102,NC_009823 | vertebrates,human | 1 | Flaviviridae,Hepacivirus,Hepatitis C virus | — | FJ230884 |
| Recombinant Hepatitis C virus S52(5UTR-NS2)/JFH1_1793S, K14040 | NC_009827,NC_009826,NC_009825,NC_009824,NC_004102,NC_009823 | vertebrates,human | 1 | Flaviviridae,Hepacivirus,Hepatitis C virus | — | JF343784 |
| Recombinant Hepatitis C virus S52/JFH1 | NC_009827,NC_009826,NC_009825,NC_009824,NC_004102,NC_009823 | vertebrates,human | 1 | Flaviviridae,Hepacivirus,Hepatitis C virus | — | EU204645 |
| Recombinant Hepatitis C virus SA13(5UTR-NS2)/JFH1_A1022G,K1119R | NC_009827,NC_009826,NC_009825,NC_009824,NC_004102,NC_009823 | vertebrates,human | 1 | Flaviviridae,Hepacivirus,Hepatitis C virus | — | JF343786 |

TABLE 10-continued

| Taxonomy | Rep.Acc.ID | Host | ViroCap-1.0 Taxonomy | | | GN.Acc.IDs |
| --- | --- | --- | --- | --- | --- | --- |
| | | | # GN's | Lineage | Seg. Count | |
| Recombinant Hepatitis C virus TN-JFH1 | NC_009827, NC_009826, NC_009825, NC_009824, NC_009823, NC_004102 | vertebrates,human | 1 | Flaviviridae,Hepacivirus,Hepatitis C virus | — | HQ852453 |
| Recombinant chimeric Hepatitis C virus 1b/2a 432/JFH-1 | NC_009827, NC_009826, NC_009825, NC_009824, NC_009823, NC_004102 | vertebrates,human | 1 | Flaviviridae,Hepacivirus,Hepatitis C virus | — | HM049503 |
| Respiratory syncytial virus | NC_001803 | vertebrates,human | 24 | Paramyxoviridae,Pneumovirus,Respiratory syncytial virus | — | BD137600,BDQ81927,BDQ91237,BDQ81928,FJ614813,JN032119,U39661,BD137603,BD137598,BDQ81930,JX503100,BDQ81932,BD137602,JX503101,BD137601,BD271636,JN032116,BDQ81931,BD27163 5,BDQ81929,JN032117,BD137599,JN032120 |
| Reston ebolavirus | NC_004161 | vertebrates,human | 4 | Filoviridae,Ebolavirus,Reston ebolavirus | — | AF522874,JX477166,AY769362,JX477165 |
| Reston ebolavirus-Reston | NC_004161 | vertebrates,human | 4 | Filoviridae,Ebolavirus,Reston ebolavirus | — | AB050936,FJ621585,FJ621583,FJ621584 |
| Retroperitoneal fibromatosis-associated herpesvirus | NC_009333 | vertebrates,human | 1 | Herpesviridae,Rhadinovirus,Human herpesvirus 8 | — | KF703446 |
| Rhesus rotavirus | NC_011500 | vertebrates,human | 8 | Reoviridae,Rotavirus,Rotavirus A | seg. 5 | AY117051,AY117052,AY117049,AY117050,U08433,AY117053,HQ665465,AY117048 |
| Rhesus rotavirus | NC_011502 | vertebrates,human | 1 | Reoviridae,Rotavirus,Rotavirus A | seg. 8 | AY065842 |
| Rhesus rotavirus | NC_011503 | vertebrates,human | 3 | Reoviridae,Rotavirus,Rotavirus A | seg. 9 | HQ665466,M21650,AF295303 |
| Rhesus rotavirus | NC_011505 | vertebrates,human | 1 | Reoviridae,Rotavirus,Rotavirus A | seg. 11 | HQ665467 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rhesus rotavirus | NC_011510 | vertebrates,human | 2 | Reoviridae,Rotavirus,Rotavirus A | seg. 4 | M18736,AY033150 |
| Rhinovirus A | NC_001617 | vertebrates,human | 2 | Picornaviridae,Enterovirus,Rhinovirus A | — | JXQ74050,GQ223329 |
| Rhinovirus B | NC_001490 | vertebrates,human | 1 | Picornaviridae,Enterovirus,Rhinovirus B | — | JX193795 |
| Rinderpest virus | NC_006296 | vertebrates,human | 7 | Paramyxoviridae,Morbillivirus,Rinderpest virus | — | JN234008,GU168576,JN234010,AB547190,Z30697,JN234009,AB547189 |
| Rinderpest virus (strain Kabete O) | NC_006296 | vertebrates,human | 1 | Paramyxoviridae,Morbillivirus,Rinderpest virus | — | X98291 |
| Rodent hepacivirus | NC_021153 | vertebrates,human | 1 | Flaviviridae,Hepacivirus,Rodent hepacivirus | — | KC815310 |
| Rotavirus A | NC_011500 | vertebrates,human | 94 | Reoviridae,Rotavirus,Rotavirus A | seg. 5 | JN258352,JN258790,JXQ2770,JN651781,JN258907,JXQ27881,JN651846,JXQ27738,HQ657144,JXQ27782,JXQ27866,JXQ27902,JXQ27662,JXQ27760,JN258407,JN635549,JXQ27837,JN651748,JN258810,JN635538,JN258951,JN635527,JXQ27892,JN827248,JXQ27811,JF521476,JXQ27943,JXQ27815,JN651857,JXQ27847,JN258862,JN651813,JXQ27756,HQ657133,JN258944,JN651792,JN258892,JN258337,JN258833,JN872871,JN258355,HQ65715 5,JXQ27947,JN258884 5,JXQ27672,JXQ2771 3,JN651879,JXQ2792 4,JN831204,JXQ2772 1,JN258395,JQ68867 7,JXQ27651,GU5650 69,JN831226,JXQ276 95,JN013975,JXQ276 91,JXQ27870,JXQ279 14,FN665692,JN2588 54,GU565047,JXQ27 966,GU827412,JN65 1803,JN651759,JN25 8801,GU565091,GU5 65058,JXQ27832,FN6 65681,JN831215,JXQ 27644,JXQ27726,JN6 |

TABLE 10-continued

VivoCap-1.0 Taxonomy

| Taxonomy | Rep.Acc.ID | Host | # GN's | Lineage | Seg. Count | GN.Acc.IDs |
|---|---|---|---|---|---|---|
| | | | | | | 51770,JN258377,JN651824,JXQ27793,JN651835,FJ169857,JN258372,JN258821,JN013974,JN258878,GU565080,JN651874,JF521465,JN258914,JN258925,DQ838599,JXQ27968,JN651890,JN258887 |
| Rotavirus A | NC_011501 | vertebrates,human | 387 | Reoviridae,Rotavirus,Rotavirus A | seg. 7 | KC443781,KC579550,JN258391,KC579943,EF990696,KC443292,5,KC443562,KC834692,KC580442,FJ793979,KC580343,KC580465,KC443364,KC579572,KC443595,KC579710,KC443661,KC580548,JXQ40431,KC174896,KC580534,KC769324,KC443617,FJ793988,JX406753,KC443342,KC579778,KC443683,HQ661131,KC579925,JN605456,KC443771,KC175222,KC580035,KC175255,EF990692,KC579495,EF990710,KCS79627,KC579991,KC769302,KC443716,JN258358,KC580275,KC769445,KC215570,DQ492676,KC443551,JN258334,KC175069,JN258929,FJ793984,JN258929,FJ793984,KC443153,GU82741,JN258929,FJ793985,KC174940,KC580094,JN258840,KC443738,JN651750,KC580354,KC443529,KC579957,KC579661,KC442971,KC580620,KC834691,DQ838610,KC174874,KC443353,KC443186,JQ688679,KC580024,KC195766 |

TABLE 10-continued

| Taxonomy | ViroCap-1.0 Taxonomy | | | | |
|---|---|---|---|---|---|
| | Rep.Acc.ID | Host | # GN's | Lineage | Seg. Count | GN.Acc.IDs |
| | | | | | | ,KC175244,JX965152,KC769357,KC579754,KC769335,KC443606,KC579528,KC443463,JN258881,KC580105,HQ657135,KC175123,JF521467,KC579767,KC175047,FJ793976,DQ146678,KC580162,KC442948,KC215526,KC443584,KC175233,KC579483,KC579594,KC442889,KC834690,KC580251,KC580586,KC443452,KC175134,KC769467,KC579944,KC580575,HQ661120,HQ661142,KC174929,KC443419,JN258905,KC443015,KC443518,KC769478,HQ846860,FJ793975,KC579605,KC175189,FJ793990,KC174863,KC580128,KC579506,KC769401,JN258871,DQ490534,KC174972,KC175266,HQ657146,KC443208,FN665684,GU199518,KC215537,KC579877,JN651761,GU565059,KC175112,JN651881,KC443441,JN258381,KC579811,KC579660,KC580240,KC175003,GU565081,KC443230,KC193620,KC443650,EF554155,KC579688,KC443386,KC443573,JN258947,KC215494,FJ793973,KC580523,JN651868,JN651826,KC443639,JN831217,FJ793981,KC443252,JN872873,KC443296,KC443131,KC215516,KC |

TABLE 10-continued

VidoCap-1.0 Taxonomy

| Taxonomy | Rep.Acc.ID | Host | # GN's | Lineage | Seg. Count | GN.Acc.IDs |
|---|---|---|---|---|---|---|
| | | | | | | 580207,FJ793969,KC443285,KC580420,KC175091,KC579822,KC175025,KC443263,KC175156,KC174907,KC769390,KC175167,KC442878,JN605445,KC579472,KC443727,KC579911,KC580398,KC443219,KC579924,FJ793992,KC769379,KC443375,KC443026,KC579699,KC193609,JN258369,KC580598,KC580276,EF554144,KC580229,KC443540,FJ793974,GU565070,KC580150,FJ793971,JN651794,KC580319,KC579836,KC580185,KC174962,GU565092,JN258828,KC580431,JX965151,KC442993,JN651805,KC580409,HQ657157,KC443672,KC579616,KC580218,KC579539,FJ169859,KC175102,FJ793980,KC579517,KC580365,JN258859,KC579968,KC174918,JN258896,KC579583,KC580013,JN635540,KC579852,JN258402,HQ084687,KC443749,KC580609,KC174885,JN831206,KC580196,KC580511,EF990700,KC443705,KC443408,KC579721,KC443004,JX271009,JQ988896,JX271006,KC175058,FJ793987,KC174993,JN605434,KC175036,FJ793978,DQ146703,KC443485,DQ146645,EF990688,JN651837,KC |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| | | | | | | C442867,KC769346,JN258781,KC443397,KC580547,KC443197,KC579835,JN013979,KC580500,JN651859,KC140595,KC175014,KC769423,GU296415,KC443331,KC174951,FJ793983,KC443496,KC580173,JN827250,JN635551,KC443175,JX965153,KC175080,FJ793984,KC579800,KC580071,JN258938,HQ846882,KC580332,JN258848,KC443142,FJ793972,JN605423,KC580488,KC175178,KC580294,KC442937,KC215474,KC580631,KC579789,FJ793986,JN258806,KC579641,KC769456,KC579677,KC769368,KC579561,JN635529,KC443760,JN013980,KC579743,GU199500,JN651783,KC580464,KC175145,KC443164,KC769412,KC215483,FJ793977,KC175211,KC769313,KC579732,DQ146689,KC769434,KC580053,KC442900,KC443694,JN651897,KC580453,KC215548,KC215505,KC580387,DQ146656,FJ793982,KC579888,DQ490558,KC579980,DQ490541,KC580083,EF990704,JF835114,JN605412,KC443507,KC195757,JN258918,KC175277,KC443628,FJ793991,JN831228,KC442911,FJ793970,KC579640,KC5 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 80476,FJ793989,KC442960,KC579865,KC580318,JN651848,JN258815,HQ846849,KC580305,FN665695,KC174982,KC443320,JN258793,KC580564,JN651815,KC580052,DQ146696,KC17520 0,KC580376,KC442982,GU296414,KC580002,KC443241,KC580262,JN651772,KC440263,JN258347,KC580117,KC443308,DQ146667,KC443430,GU565048,JF521478,KC579900,KC193630,KC443474 |
| Rotavirus A | NC_011502 | vertebrates,human | 410 | Reoviridae,Rotavirus,Rotavirus A | seg. 8 | KC579687,KC443528,KC175243,KC580608,KC579582,JN635558,HQ846850,JXQ27869,KC580353,JXQ40428,KC442959,KC175057,KC579482,JXQ27640,KC579941,DQ146690,JN258782,KC579720,KC193608,KC175155,KC175133,JN651793,KC580206,KC175232,KC175046,KC443284,KC580161,JF521468,KC175090,JN258365,KC195765,GU565082,KC174950,DQ490559,KC442970,KC443141,KC580023,JXQ27665,KC443163,DQ490542,KC443484,JN258945,JN651858,KC769466,KC580463,JN651771,KC580574,JN258902,JN651836,KC580184,EF554145,JX406754,KC580138,KC443374,KC443395,DQ146697,K |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | C443605,JXQ27956,JX683000,HQ846861, KC442888,KC580149,HQ657145,JXQ2775 9,KC580487,JN83121 6,JXQ27715,KC175110 1,KC579639,KC4431 85,GU565093,KC215 536,KC175068,GU56 5071,KC443352,KC1 75013,DQ146704,KC 174884,JX965148,KC 443660,KC579777,JN 605455,KC193629,JX 027781,KC443473,JX 027825,KC443341,K C834693,KC769400, KC443273,GU199489 ,KC442936,JN377717 ,KC580522,KCO2003 3,KC579899,KC4437 37,KC443451,KC443 385,JXQ277967,GU19 9517,KC195754,KC1 74971,KC443003,FJ1 69860,KC174906,FN 665694,KC443363,K C174992,JN872872,E F990705,JN635528,K C580342,KC442924, KC175122,KC175276 ,KC579659,GU19949 9,DQ146646,EF9906 89,KC442992,JX6829 98,KC442866,KC580 239,KC579788,KC58 0375,GU296413,KC5 79676,JN651891,KC5 79864,JXQ27836,JN2 58860,JN651782,KC4 43014,DQ492677,KC 020021,KC579942,K C443726,KC140594,J N651875,JXQ27923,K C443262,JXQ27846,J N258873,KC443407, KC175166,KC769334 ,KC580585,DQ14667 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 9,KC579887,JXQ27748,EF990693,KC443429,KC579922,KC175079,JXQ27891,HQ661119,KC580012,KC443440,JN258387,JN258816,KC175177,JN651880,KC580316,JX271008,KC579799,JXQ27698,KC579876,JXQ27737,JXQ27814,KC580475,KC580317,KC443693,JX965150,JN605422,KC579834,KC579990,JN377719,JN258802,KC579604,JF521479,HQ846883,KC443152,DQ146668,JN377721,KCO20031,KC443561,KC769356,JN013977,KC580364,JN651847,KC442899,JF712584,KC579742,KC580273,KC580051,KC579753,JN258398,JN258824,KC580430,JN831205,KC443396,KC174939,KC443748,KC443229,KC443025,KC580001,KC443196,JN258924,KC443462,KC579979,KC443759,KC579731,JN651749,KC443306,KC174862,KC579810,KC175265,GU565060,KC443780,JQ988889,KC579494,JXQ27880,JXQ27946,KC580070,KC769323,JN258343,KC579910,KCO20020,KC443616,KC443638,KC580250,GU296412,KC580082,KC769345,JXQ27687,JXQ27671,KC443506,JN827252,KC175002,JXQ27703,KC579821,KC |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 442947,KC443251,KC174961,KC579833,GU199510,KC769433,KC442877,EF136660,KC579549,JN377718,JXQ27858,KC834694,JN651814,KC579851,EF990711,KC443682,KC443517,JX965149,KC579560,KC579967,KC580116,JN258836,KC769422,EF554156,HQ657156,JXQ27792,KC579626,JXQ40429,GU565049,KC579709,JX682999,JN258913,JN258354,KC769455,KC580533,KC174895,KC769411,KC579956,JN651760,JN258794,KC174917,KC175111,KC834695,KC580093,KC443418,KC580408,KC769444,KC175024,KC769378,KC443671,JN258849,KC579863,KC443330,JN258882,KC580386,KC580050,KCO20022,KC580034,KC769301,HQ661130,KC443715,JN651804,EF990697,KC174873,JN651825,GU827413,JN605433,KC769389,KC579471,KC175221,JN258935,KC193619,KC174981,KC579950,KC580172,JQ688680,JN258376,JN831227,JXQ27913,JN377720,KC580195,KC443649,KC580499,KC579538,KC580510,KC175035,KC443572,KC443704,JN635539,KC443240,KC579766,KC443130,HQ846872, |

TABLE 10-continued

VircCap-1.0 Taxonomy

| Taxonomy | Rep.Acc.ID | Host | Lineage | # GN's | Seg. Count | GN.Acc.IDs |
|---|---|---|---|---|---|---|
| | | | | | | KC175210,KC580261,KC579593,KC443770,KC175199,HQ65710,JF712573,JN013934,JN258891,KC443495,JXQ27769,KC443207,KC579923,KC579571,HQ661141,JN605444,KC580274,JXQ27725,KCO20028,DQ838615,KC580452,KC580127,KC442981,JN013976,KC579527,KC443627,KC580217,KCO20032,KC580597,KC174928,KC175254,KC442910,KC76944,KC443174,JX682977,JN258332,KC580104,KC580630,KC580441,KC443594,KC175188,KC443307,KC579615,KC580228,DQ449035,DQ146657,KC443583,EF990701,KC443539,JXQ27803,KC443562,KC580545,JF712562,KC580545,KC443319,KC579698,KC443218,JXQ27934,KC579516,KCO20027,KC580304,KC580619,KC580546,KC580293,KC175144,KC769367,KC580563,KC769312,FN665683,KC580419,JXQ27654,KC580397,KC215493,JN605411,JXQ27901,KC443550,KC579638 |
| Rotavirus A | NC_011503 | vertebrates,human | Reoviridae,Rotavirus,Rotavirus A | 429 | seg. 9 | KC442875,JX841120,JN651889,AB081787,KC580102,GU565068,KC579977,KC580639,EF079066,KC834637,KC580313,KC443249,KC579696,KC769332,JN258874,KC175230,KC580473,KC1 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 75241,KC175000,KC580595,JN651845,JX965176,AB081793,AY773003,HQ846862,KC579613,AB526247,KC175033,AB081794,KC834638,KC175109,GU296431,KC580237,U26386,AB081795,KC580226,KC579591,JN258941,KC443614,JX965166,JN258917,KC579547,JN651802,AB081777,U26395,KC443172,KC443636,KC443361,KC443416,KC174871,AB081790,AB081798,AB081792,KC769321,KC443394,AB081780,KC443304,KC580362,JN258401,EF079069,AB571046,KC580080,AB081801,KC443227,HQ846884,DQ478582,KC443647,KC443603,KC580204,FJ169861,KC579808,KC443150,HE646643,JX965177,KC174926,JN258844,KC443449,JN831236,U26388,KC579764,AB526249,JN013998,KC443161,KC580170,AB081776,KC443724,AB081774,KC580561,JN258805,KC175208,U26387,KC834641,KC443702,HQ661117,JN635559,KC579751,KC174948,KC443194,KC580091,KC834635,JN258846,HQ846873,KC580450,JF712571,KC769398,KC443789,KC580259,KC769475,JN827253,AB081785,KC1957 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 63,JN258338,JN651758,KC175285,KC443293,KC443757,KC442886,DQ492674,JX965164,KC580182,KC580485,AB081593,GU565079,KC442968,KC579685,KC443471,KC443548,JN605453,JX965174,KC174990,JN014001,JN258390,KC175022,KC443205,KC175044,KC580032,KC443328,JN258791,KC579707,KC174915,KC442934,AB573651,KC175077,U26389,JX965167,AB081775,KC580136,KC580519,KC443183,JQ988904,U26382,KC580125,JX965180,JX965173,KC580340,KC769343,KC579849,AB081779,KC443023,KC769365,KC580351,KC174882,JXQ40425,KC175263,KC769354,KC579480,JX841124,KC579635,KC443427,KC175274,KC442948,KC769453,EF121951,AB621363,KC443504,KC443680,JX965175,JQ688681,KC580531,KC175153,JXQ40424,KC579503,KC443592,KC175131,KC580572,EF079065,KC175197,AB081799,JN831225,AB081782,JN258362,KC579558,KC580606,KC174893,U263390,KC579965,KC174904,FN665696,AB573647,JX841123,HQ661139,KC579797,JX965160,DQ3214 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 97,JN651873,KC4435 70,JN605442,JN6054 9,KC443405,U2639 2,JN651780,KC57998 8,DQ321493,GU2964 30,KC443438,JN2588 27,KC443669,JX9651 79,KC579897,JN6355 48,JF521469,JX9651 71,JN258908,AB0817 81,JN651769,AB0817 89,DQ490550,U2638 0U26393,GU199497, JN872870,KC443034, KC579718,KC579939 ,KC579536,EF07906 8,KC442957,KC1749 37,KC443625,KC215 545,KC442990,JN258 368,KC443515,FN66 5685,AB081797,KC5 80248,KC175088,KC 175142,KC443383,JN 013999,KC443526,K C580079,KC579624, KC44328 2,KC580147 ,KC174979,JN258813 ,JX965170,KC443372 ,KC579514,KC44376 8,KC579580,KC5798 85,AB081786,KC443 735,KC769387,KC58 0215,KC443746,KC5 80021,AB081594,GU 565090,KC580302,JN 258895,KC579860,G U565057,KC443779,J N635537,KC579999,J N258380,JX841122,K C580068,JN014000,K C443012,DQ478583, KC443658,KC175252 ,KC769486,HQ65714 3,KC580159,KC5800 10,KC443460,KC442 919,AB081784,DQ32 1495,U26383,KC443 260,KC443581,JX965 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | 181,KC443713,KC579729,KC579674,JX969729,KC443139,AB05169,KC443238,AB081791,KC443238,AB573649,JF835112,KC44371,KC580583,KC580291,AB081796,U26381,KC580114,KC215502,JN651856,U36242,JN605420,KC579908,U36241,JN258928,KC579830,KC579919,KC443339,KC769442,KC215513,L14072,JX965178,KC443216,KC580628,JX406755,JN651896,KC580497,KC579491,JF712582,KC579786,KC769464,JN651834,KC443691,KC579525,KC580373,AB081783,AB081800,KC580617,KC175055,KC442897,KC443035,KC769310,KC580428,HQ657154,GU565046,KC443350,DQ478584,KC579656,EF079067,KC579819,KC580406,KC195774,KC442945,KC174959,HQ657165,KC442979,JX841119,KC579874,KC175186,KC174969,KC580542,JX841121,KC769409,KC175164,JX965182,U26384,U263949,GU199508,AB081788,KC175219,JN258346,KC580193,KC579775,KC443317,KC579492,U26379,JN377709,KC580384,KC769376,KC579569,KC580395,DQ490556,DQ838620,HQ661128,KC579602,JN831214,AB5 |

TABLE 10-continued

| Taxonomy | Rep.Acc.ID | Host | # GN's | Lineage | Seg. Count | GN.Acc.IDs |
|---|---|---|---|---|---|---|
| | | | | | | 73645,KC769431,JN258953,HE646646,KC140587,KC580417,JN258786,KC580047,JN651791,JF521480,KC443537,EF990708,KC769420,KC580439,KC580461,JN605431,KC443001,KC580270,EF079064,KC57974 0,KC580520,JF71256 0,KC443493,HQ8468 51,JN258857,KC5803 29,KC175099,KC443 559,JN651823,JN651 867,KC579954,KC83 4646,KC580508,AB0 81778,JN258879,KC4 43482,GU827411,U2 6385 |
| Rotavirus A | NC_011504 | vertebrates,human | 399 | Reoviridae,Rotavirus,Rotavirus A | seg. 10 | JN605446,KC689359,JN377716,KC443309,JXQ27849,KC580014,EF990712,JN831229,DQ270114,GU19950 1,GU565072,KC5797 68,JN258894,KC5803 06,KC580095,KC579 722,KC175223,KC57 9853,JN258367,KC58 0477,JN258345,KC58 0621,JXQ29832,HQ8 46885,JXQ278I7,KC4 43629,KC580524,DQ 490543,KC443497,D 0146658,JN258804, KC174897,KC443332 ,JN258400,KC579867 ,KC580025,KC17527 8,JXQ29831,KC44365 1,KC443354,KC1750 15,KC579912,KC443 607,KC443242,KC17 5037,KC580003,JN25 8339,KC579484,KC5 79473,KC443027,JN0 13982,KC580037,KC 443353,KC579606,K |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | C580174,GU199490, KC174952,KC443508 ,KC193621,KC44287 9,KC443431,JN25892 7,JXQ27904,KC58032 1,KC443563,HQ8468 63,JN63541,KC5803 44,KC579866,DQ492 678,JF521481,KC443 782,JXQ27689,JXQ27 827,KC769457,JN013 984,JXQ27705,KC580 054,KC580535,KC17 5092,KC580466,KC7 69336,KC579678,DQ 146680,JN605457,KC 580599,KC579662,J 0688682,KC443739, DQ270104,KC580333 ,JN605413,KC580295 ,JN258838,KC579790 ,KC175146,JXQ27949 ,KC769314,JXQ29834 ,AF093199,JN258389 ,KC579507,KC17499 4,JN635552,KC44359 6,KC443154,KC1936 31,KC579733,KC769 347,KC175267,KC57 9969,KC443695,GU5 65050,KC443376,KC 175168,KC580355,K C175081,KC195767, KC443409,KC579992 ,KC174930,KC44290 1,KC579889,KC4437 28,GU827415,KC442 912,JN651860,KC443 398,HQ657147,KC57 9981,KC442983,KC5 79755,KC175113,KC 579901,DQ270108,K C442961,KC769468, KC443750,KC443321 ,KC443297,JXQ29835 ,DQ838625,KC58054 9,KC442949,KC4430 16,KC580197,KC175 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 004,HQ661132,KC769435,DQ270103,KC175026,KC443253,KC580277,KC579643,GU565061,KC443618,KC443275,KC580208,KC580084,JXQ27860,JXQ27728,JN258870,KC443662,KC17494,JXQ27643,JN65177,JN651838,JN87287,JN651892,JX40675,JXQ27700,KC58025,JXQ27970,KC68935,JN258885,KC76944,KC580410,KC5804,KC443143,KC44243,JXQ27883,JF712586,KC443264,KC689361,JXQ27740,JXQ27772,JXQ27762,KC580278,KC579711,EF554146,KC215538,KC579779,KC579812,KC175212,KC579595,KC174973,KC579642,JQ988897,KC76935,KC442994,JF521478,KC443343,KC579529,KC580377,KC769402,KC443552,JN651816,HQ661143,KC769413,JXQ27958,KC580399,EU483088,KC579496,KC579837,KC580512,KC579958,JX027750,DQ449655,KC580320,KC580241,KC580118,KC580388,KC442890,KC579663,JN651849,KC175203,JN651806,KC174901,KC443706,DQ270108,FJ169862,JN651701,JN651784,DQ146669,KC443187,JN651751,KC443640,KC140596,KC580501,KC50 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 80421,JN258852,KC580565,JN605435,KC443574,FN666697,KC579838,JXQ27674,JX965155,KC580576,KC195756,DQ490560,HQ657136,KC175157,JF712575,KC769391,JXQ27839,JN827254,KC579617,KC580587,KC769380,KC175179,JN635530,HQ661121,JXQ29836,KC443365,KC579927,KC579801,KC580230,KC579573,KC443541,JN258357,FN665686,DQ270102,JXQ27894,D0270117,KC443486,KC443220,KC175190,KC175234,KC443442,JN651795,KC174864,JN013981,KC577974,KC580366,JN258882,0,JX271010,JN258379,KC175070,JXQ27667,JXQ27936,JN258916,JN258867,JXQ27765,KC443585,JXQ27795,KC579518,KC174919,KC769303,KC579823,JX965156,KC443761,KC580151,KC580454,JN258904,JN605424,GU565094,JN258826,KC175059,KC443005,KC442972,KC175245,KC580432,KC579926,KC580055,EF554157,KC174875,KC443198,KC443464,KC174983,JXQ27784,JXQ27872,JXQ27805,KC443475,KC769424,KC580550,KC580036,KC193610,KC443519,KC580632,KC579951,KC689360,K |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | C175135,KC580072, KC443231,KC443530 ,JXQ29833,KC769369 ,KC175048,KC58016 3,KC579584,KC4431 76,JN258785,JN6518 69,KC580140,KC175 124,HQ657158,KC58 0107,GU566083,KC5 79700,KC580489,KC 769479,KC579628,A F093200,KC443209,J N831207,JX965154,K C579945,JN831218,K C580186,KC442938, KC443286,KC443165 ,JXQ27717,KC174963 ,KC175103,JN258952 ,DQ146691,GU19951 2,KC580263,KC5806 10,KC442868,KC443 684,KC580219,KC44 3132,KC443420,JXQ2 7916,JN651827,JXQ2 7926,HQ846874,KC1 75256,KC580129,JN6 51882,JN258937,KC4 43717,DQ146647,KC 579689,DQ492655,K C443772,KC580106, KC174886,HQ846852 ,KC579540,JN013983 ,KC579562,KC57987 8,JN258797,KC44367 3,KC443387 |
| Rotavirus A | NC_011505 | vertebrates,human | 374 | Reoviridae,Rotavirus,Rotavirus A | seg. 11 | KC579679,KC443674 ,KC195768,DQ83863 0,JN831219,KC19363 2,KC580490,KC7693 37,KC443783,JN6054 58,KC580334,FJ7940 20,KC580400,KC769 326,KC140597,KC57 9959,KC580096,JN25 8850,KC580323,KC5 79618,KC442880,KC 579530,KC443487,K C769381,KC443188, |

| Taxonomy | Rep.Acc.ID | Host | # GN's | Lineage | Seg. Count | GN.Acc.IDs |
|---|---|---|---|---|---|---|
| | | | | | | KC443355,KC769348,DQ492679,KC44291 3,KC175224,JX27101 1,KC443310,KC5800 73,JXQ27948,KC5802 80,JXQ27826,KC5803 67,KC580085,KC443 166,KC442995,KC44 3641,KC443155,JN65 1828,JXQ27668,KC44 3421,JX406757,KC57 9508,KC443586,KC5 80322,KC443465,KC 579868,KC195755,JN 605425,KC174876,K C579813,KC175268, DQ146648,JN258333 ,KC580187,KC58035 6,KC443696,KC4435 97,KC443254,KC579 723,JN651774,KC174 887,KC580455,KC57 9552,JF521482,JN25 8803,JF794021,KC57 9701,JN258926,KC44 3006,KC442984,FJ79 4025,KC579645,KC4 43575,KC443432,DQ 146670,JXQ277848,JN 605414,KC580038,JN 258936,JN258388,KC 443564,EF990694,K C580264,JN258837,E F554147,KC443399, HQ657137,KC579802 ,KC580220,FJ794017 ,KC580209,KC44376 2,JN258883,KC44333 3,KC579474,KC1750 82,KC579585,KC443 663,HQ657159,KC58 0015,HQ661133,JF71 2587,HQ846864,KC5 79824,KC579946,FJ7 94033,DQ490544,KC 443542,FJ794039,KC 580108,JN827255,KC 579690,JN258869,KC |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 769315,KC443210,G U565073,JXQ27739, GU827416,JN651817 ,KC442869,KC58050 2,HQ661144,KC4432 87,KC579563,KC769 447,FJ169863,JN872 875,GU565084,KC58 0536,KC443553,KC5 80307,KC579607,JN8 31230,JN651861,KC5 80152,FJ794018,JN8 31208,KC580566,JXQ 27657,KC580345,JXQ 27704,JXQ27771,KC5 79791,EF990702,FJ7 94016,JN258344,KC5 80551,KC443454,JN2 58946,JN258893,FJ7 94019,JXQ27727,KC5 80026,JXQ27761,KC5 79879,KC579596,JF7 12576,FJ794034,KC4 43017,KC580525,KC 443729,KC580198,K C579485,JXQ27816,J N013986,KC769370, KC580600,JXQ27642, KC769425,JXQ27673, GU565095,HQ84685 3,JXQ27804,JF52147 1,JN635542,JN65176 3,KC443133,JN25837 8,KC579734,JXQ2785 9,KC580231,JN60543 6,KC769403,KC4435 09,FJ794027,JXQ278 71,DQ146698,KC579 541,KC442973,KC57 9756,KC443276,KC4 42939,KC580389,KC 580478,KC443344,K C580175,KC443740,J XQ27783,KC769392,J XQ27903,JN651752,J N013985,JXQ27701,J XQ27749,JXQ27969,G U565051,KC443144, |

TABLE 10-continued

VoiroCap-1.0 Taxonomy

| Taxonomy | Rep.Acc.ID | Host | # GN's | Lineage | Seg. Count | GN.Acc.IDs |
|---|---|---|---|---|---|---|
| | | | | | | KC580253,FJ794022, KC193622,KC579891 ,DQ146681,DQ146706 ,JXQ27690,JN65183 9,KC580119,GU1995 13,KC579970,KC443 718,JXQ27882,KC580 378,JQ988898,FJ794 026,KC579712,KC17 5235,KC769480,KC5 79902,KC443443,FJ7 94036,JN651796,FJ7 94031,KC579928,HQ 661122,KC579745,K C580577,FJ794024,G U199502,KC769414, KC579664,JN258356, JXQ27716,JXQ08870, JXQ27893,FJ794032, KC443685,KC443322 ,KC580422,KC76946 9,GU296418,KC5804 33,KC580279,KC443 298,KC769304,KC44 2928,HQ846875,JN6 35553,KC580164,KC 443652,KC580004,K C579574,JN258818,K C580411,JXQ27915,K C443476,KC443608, KC769458,FJ794035, KC579839,KC579497 ,DQ146659,JN25836 6,EF990698,KC5806 11,KC443751,KC580 039,KC579913,KC44 3232,JXQ27838,KC44 3773,JXQ27925,JN25 8399,KC769359,KC5 80513,EF554158,GU 296419,KC443377,K C174984,KC443366,J X682996,KC443265, KC443520,KC579993 ,DQ490561,KC44322 1,KC769436,KC5797 80,KC442927,JN6054 47,FJ794037,KC4429 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| | | | | | | 50,KC580467,FN665687,HQ846886,FJ794029,JN258825,HQ657148,FJ794038,JN651870,KC580056,KC580588,GU565062,KC580633,KC443177,JN258915,KC175213,JN651883,KC580444,KC579929,JN258796,KC579769,KC579854,JC579769,KC579854,JF712565,KC443630,FJ794028,KC579519,KC442902,JXQ27935,KC443388,KC579982,KC442891,KC193611,JN651807,JQ688683,KC443410,KC443707,JN258903,FN66569 8,KC443199,KC580057,JN651893,KC579629,KC443531,FJ794023,EF990690,JXQ27794,KC442962,JXQ27957,JN258864,KC579890,JN258784,JXQ40434,KC443498,KC443619,KC580141,JN651850,KC580622,EF990713,JN635531,KC579644,KC580242,KC580296,GU199491,KC174865,KC580130,KC175125,KC443243,JN651785,KC443028,FJ794030 |
| Rotavirus A | NC_011506 | vertebrates,human | Reoviridae,Rotavirus,Rotavirus A | 388 | seg. 2 | KC443168,KC175062,JXQ27660,KC443289,KC442893,KC580446,KC443643,KC443753,KC580121,HQ846844,KC580347,JN605438,JN258406,JN831221,KC580568,KC834709,JXQ27680,JN605416,KC579648,KC579487,KC580028,KC769372,KC579598,K |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | C580527,KC580061, KC443665,JN013989, KC580255,KC443632 ,KC579782,KC57999 5,KC579842,KC5795 43,EF560616,KC443 500,KC769317,KC21 5563,KC175259,KC4 43698,KC443179,KC 193634,JN258900,KC 175116,KC580017,G U296423,KC580006, KC443434,KC175051 ,JF712567,JN651754, KC443357,KC443731 ,KC579692,KC17522 6,KC579666,GU5650 42,KC580538,DQ838 634,KC579932,JN258 385,KC579620,JXQ27 788,DQ492670,KC57 9949,DQ146661,KC1 74996,KC175193,KC 580060,JXQ27647,KC 443742,KC834708,JN 651819,KC769394,K C443157,JXQ27777,K C443522,KC769416, KC443456,KC769306 ,JN651898,KC443445 ,KC175171,JXQ27745 ,DQ146639,JF521462 ,KC579499,KC58015 4,KC443764,KC4429 52,KC442882,JN2589 49,KC580624,KC579 631,HQ846877,DQ14 6700,KC579725,JN25 8350,KC579565,KC5 79649,JXQ27682,JX2 71002,JXQ27909,JX9 65138,KC174975,KC 579681,KC442941,K C579736,KC579826,J N258831,KC579826,J XQ27855,JN651809,K C580613,JN651877,J N258911,KC442975,J |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | XQ27658,JN258374,KC175248,KC579961,KC769471,KC580166,KC769405,KC443544,JQ98900,KC175095,KC580380,KC579576,KC443533,DQ870486,JX406748,HQ661113,KC443346,KC769427,KC175160,KC769482,JXQ27801,JXQ27693,KC140591,KC443223,KC580391,KC769350,KC580189,KC175182,FN665689,KC442930,KC442964,KC579804,KC443008,KC443146,KC580244,KC580110,DQ490536,EF554149,KC580635,KC580480,JQ688674,EF560622,GU565053,KC442997,KC580283,KC175084,KC834710,KC580041,KC443676,JXQ27712,KC443019,KC443212,JXQ27977,JXQ27863,KC580554,KC580435,KC579771,KC174933,JN651841,DQ870498,JXQ27878,KC443478,KC443785,KC579904,KC769460,HQ846855,KC175237,KC579984,KC580266,JN831232,KC195770,KC443368,KC580309,KC579667,JN651863,JN651776,KC580298,KC443390,JN258921,KC580504,KC579476,JN605405,GU827407,JXQ27889,JN872866,EF554138,KC195761,KC443379,KC443775,KC443312,EF560619,K |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | C76938,DQ146672, JN258800,KC443335, KC580284,KC193624 ,JXQ27735,JN651765 ,HQ657150,KC17521 5,KC443610,KC1752 81,KC580492,DQ146 683,JN651787,KC443 234,DQ146650,JN63 5533,JX965137,KC58 0336,KC174922,KC4 43300,KC443030,KC 769339,HQ657161,K C579609,KC443201, KC580469,KC175018 ,KC175073,KC58042 4,JN258396,JXQ2783 4,GU199519,KC1752 04,KC443588,KC579 554,JN258943,KC580 098,KC580325,GU19 9515,KC443467,KC4 43566,KC442986,KC 44341,2,KC175007,K C580178,KC579793, KC579714,KC580602 ,KC769361,KC58008 7,KC579587,KC5798 93,DQ490546,JN258 865,JXQ277810,KC443 687,JN258789,KC175 270,JXQ27754,KC443 324,DQ870494,KC17 4889,KC174965,KC5 80042,KC443511,KC 174944,KC580402,K C580413,JXQ27724, GU565075,KC579747 ,JN651798,JXQ27768 ,KC580591,KC44327 8,KC174986,DQ4905 52,KC174911,JN2588 77,KC580369,KC579 841,KC579703,KC44 2904,KC175040,DQ8 38633,KC442915,KC 769449,HQ846866,D 0838631,JN258823, |

TABLE 10-continued

| Taxonomy | Rep.Acc.ID | Host | ViroCap-1.0 Taxonomy # GN's | Lineage | Seg. Count | GN.Acc.IDs |
|---|---|---|---|---|---|---|
| | | | | | | DQ870506,KC174900,GU199504,JXQ27931,KC193613,KC443654,DQ870490,KC442871,JN651852,KC175029,JXQ27921,KC580200,JN827245,KC579521,KC579532,JN635544,JX965136,JN651830,KC443720,JN605449,KC443555,JN258843,KC443245,KC580457,KC443709,FN665678,KC174867,KC175127,JN635555,JX027955,KC580132,JN258889,JF521473,KC769328,KC443621,JF712556,KC443401,GU565086,KC175105,JN605427,KC174955,KC579856,GU199493,JN258932,KC443489,KC443577,KC579815,KC579915,KC443190,JN013990,DQ870502,JN258363,KC579510,KC443267,DQ838632,JN258812,KC579972,GU565064,DQ146694,DQ838635,KC580358,FJ169854,KC579933,KC443423,KC769438,KC580233,KC175149,HQ657139,JN258341,JN831210,KC443256,KC580579,JF712578,JN258851,KC580222,KC580211,JXQ27900,JXQ279164,KC443135,JN651885,KC443599,JXQ279142,KC175138,JXQ278145,KC580515,KC579881,KC174878,EF560613 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A | NC_011507 | vertebrates,human | Reoviridae,Rotavirus,Rotavirus A | 383 | seg. 1 | JN635532,KC443029,KC580188,KC580005,KC580390,KC580553,KC579665,JN635543,KC443708,KC44281,KC769382,EF554148,KC174899,JN651818,DQ490545,KC580040,KC580058,KC579792,KC175061,JN651829,KC140590,JX406747,KC443576,KC175236,KC580434,KC580601,JN258364,KC579630,KC579803,DQ146671,KC443389,KC580165,KC58047,KC442951,KC5794,KC443189,DQ87098,JN605404,JN258493,JXQ27714,KC443835,DQ870485,KC175159,KC443367,KC580401,JXQ27736,JX965134,KC579647,KC443334,KC580297,GU827406,JXQ27857,KC174974,KC443730,JXQ27758,KC579892,JN258386,JN258795,JXQ27681,KC443543,KC579680,KC443167,GU565063,JXQ27659,KC443222,KC443752,JN651775,KC580120,HQ657149,KC580526,KC579619,GU565041,KC580254,KC580634,JN258950,KC580590,JXQ27641,KC580109,KC769338,JX965133,KC175203,KC769415,KC769360,JN827244,DQ838601,JXQ27912,KC443422,GU565052,JN258808,KC579553,KC443510,KC579691,KC4431 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 78,JN831209,KC175072,JN872865,DQ838639,JXQ27824,KC769459,KC579542,KC443697,KC579713,KC579586,HQ846865,KC579983,DQ146660,KC579702,KC443784,KC175258,JXQ27692,JN651797,KC175269,KC580176,KC443565,JN651876,KC175104,KC580086,DQ870497,JXQ27747,KC579814,JN605448,HQ661112,KC443598,KC580612,KC195769,KC443675,KC443763,HQ657138,KC579735,KC580552,KC580503,JX027965,HQ846876,KC174877,JN258901,FJ169853,GU296421,JXQ27974,KC580265,KC834711,KC443288,KC443774,JN651894,HQ846854,JXQ27930,JF712566,KC443554,JN651884,KC769349,KC579960,KC769448,KC579931,KC579840,DQ870489,KC442892,KC175280,KC175225,KC175214,KC769437,KC443609,KC579509,JN258830,KC443499,JX271001,JXQ27945,KC193633,DQ870505,JN258375,KC580059,KC174932,KC443200,GU565074,KC580537,DQ146693,KC443477,KC195753,DQ870501,EFS60612,KC580346,JF521461,KC443719,KC579948,KC580623,KC769481,KC443686, |

TABLE 10-continued

| Taxonomy | Rep.Acc.ID | Host | ViroCap-1.0 Taxonomy # GN's | Lineage | Seg. Count | GN.Acc.IDs |
|---|---|---|---|---|---|---|
| | | | | | | KC443411,DQ492669,JXQ27648,KC580210,JN651764,KC580282,KC579869,JXQ27813,KC443018,JN258342,KC580368,KC443488,KC175181,EF56068,JXQ27802,KC580221,KC579724,KC443741,JN258853,KC580357,JXQ27732,KC769404,JN605426,JN258912,JXQ27791,KC580589,JXQ27944,KC579475,KC579597,JXQ27780,KC443134,JQ988899,KC580221,KC174888,GU565085,KC442985,KC443277,JN651840,KC175192,JF521472,KC580412,JN605437,KC175115,KC580177,EF560615,JN258331,KC580324,KC442903,KC193623,JN013988,EF554137,KC579746,KC579930,DQ838638,DQ838636,KC443642,KC579971,KC443233,KC580074,KC579564,KC443311,JF712555,JN605415,KC442974,KC580016,KC443400,KC443356,EF576937,JXQ27890,JN258861,KC193612,KC769470,KC443620,JXQ27908,DQ146682,KC579903,JN258868,KC443299,KC443444,KC44287,JXQ27778,KC58037,JX965135,KC44324,KC579520,KC834712,KC580567,JN831231,KC769316,KC442963,JXQ27670,KC769327,KC834713,KC44 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 3433,DQ146699,KC442996,HQ661134,KC443466,KC580456,JN258934,FN665677,KC443156,DQ146638,KC579947,KC579575,JN258397,KC580468,KC174866,KC579646,DQ490551,KC769305,GU199514,DQ838637,KC443532,KC443255,KC580423,KC175126,KC443266,KC580153,KC580232,KC175148,GU199492,JN635554,JN258886,KC579880,DQ838640,KC174985,JF712577,KC579770,JN258783,KC580027,KC443455,JN013987,JN258817,JXQ27708,KC443521,KC442940,KC579825,KC579914,DQ490533,KC579757,JXQ27868,KC579855,KC442929,KC175083,JN651851,HQ661123,JN651786,KC443345,HQ846843,HQ657160,KC443587,KC580131,JXQ27856,KC579608,DQ146649,KC443664,JN258353,JN651862,KC580335,KC443631,KC443653,KC442914,KC769393,JN651808,KC580097,DQ490539,KC175039,KC443211,JXQ27835,KC443145,KC580308,DQO05109,EF560618,JN258923,JN651753,KC579531,KC579781,KC769426,KC175028,KC443007,KC580281,JXQ27879,GU199503,KC579994,KC580491 |

TABLE 10-continued

| Taxonomy | Rep.Acc.ID | Host | # GN's | Lineage | Seg. Count | GN.Acc.IDs |
|---|---|---|---|---|---|---|
| | | | | | | ,JN831220,KC769371,KC580578,JQ688673,KC444323,FN665688,GU296420,KC580445,KC579486,JN258890,KC580199,KC580514 |
| Rotavirus A | NC_011508 | vertebrates,human | 392 | Reoviridae,Rotavirus,Rotavirus A | seg. 3 | JXQ27954,KC175128,KC579844,KC579805,KC580425,JN651777,KC579772,KC443567,JQ688675,KC580088,KC443699,KC580190,KC174868,GU565054,JXQ27844,KC580625,JN258842,KC443501,DQ838641,JXQ27646,JN831222,DQ146640,KC175260,JN258888,KC443402,KC579477,JN013991,KC579588,KC580044,KC443490,KC443479,JXQ27694,JN258942,JXQ27746,KC443457,KC580493,DQ146684,KC580528,KC443202,KC580099,KC769329,KC442942,KC769307,HQ661136,KC579794,KC443633,JXQ27767,KC579816,JN258834,KC443677,JN605428,KC193614,KC579748,KC579650,JX027976,KC580267,KC769461,GU565043,HQ657151,KC579488,KC769384,JXQ27649,JXQ27711,EF554150,JEF560620,JN258384,KC442965,JN605439,KC580285,HQ657162,KC580029,KC579651,KC580370,KC580337,KC442953,DQ870499,KC580470,KC580555,JN651831,FN680514 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 65690,DQ838642,JN651895,KC769318,KC580111,JXQ27833,KC580245,KC580256,KC443721,KC195771,KC443732,KC443180,KC769351,HQ846878,KC174912,KC580179,KC769340,JXQ27922,KC175117,JN258955,KC579843,KC769439,DQ870503,JXQ27962,KC580359,KC579950,JN258405,KC443413,JN258394,KC769395,HQ661125,KC580539,KC174879,KC580286,KC580603,DQ492671,KC580234,KC443688,KC443191,KC580155,KC174956,GU565087,KC174890,KC579871,JN651886,JN013993,JN258822,KC443644,JN635556,KC443391,KC175216,KC580580,KC579882,KC175238,D0490547,KC195760,KC175205,JXQ27683,KC443743,JN635545,KC580212,KC579632,HQ846856,KC577959,JN258910,KC174923,KC769472,KC174945,JXQ27941,KC577995,KC175249,JXQ27822,KC579610,KC579682,KC175161,KC443347,KC443358,JN872867,KC579500,KC580447,JXQ27877,KC175030,JXQ27790,KC193635,KC769483,KC175074,KC580018,KC443600,KC175052,KC443512,KC769428,KC580392,HQ657714 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | KC580614,KC442840,KC215499,JXQ27794,KC579715,KC443257,EF560614,KC443765,DQ146673,KC43290,KC579704,KC43224,KC443776,E174901,KC580201,F560617,KC579934,JXQ27809,KC579737,KC579996,KC579533,KC443325,JN258931,JQ98890,JN827246,KC580041,KC580458,KC17523,KC443786,KC44327,KC442998,KC58158,KC579962,KC10122,KC175063,HQ75019,JXQ277776,KC846867,JN651788,KC580505,KC580133,KC443435,FJ169855,KC443589,KC174934,C443147,KC579522,KC443369,KC577976,KC834706,JN25878,KC175085,KC5796,KC443301,KC57921,KC580414,DQ83511,KC579974,KC174997,KC18645,KC175150,FN75172,KC443268,KC665679,JN258373,KC579857,KC175106,DQ838644,GU19949,JN258811,KC7694,KC443556,KC58036,JXQ27723,KC579648,JN258863,KC44269,KC443020,GU8272,KC580076,KC447408,JXQ27854,KC443622,JF712557,KC443313,JXQ27679,KC769450,KC579916,HQ61114,KC442987,DQ870487,KC579555,JN258799,KC443169,JN258351,JN635534,D |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0146701,KC443611, DQ870491,KC443523 ,JN258922,JF712568, JN605450,KC443136, KC175041,KC442905 ,KC442916,KC58015 6,JN258856,DQ8704 95,KC443710,JN6054 17,KC443534,JN2588 76,KC579544,GU565 065,JN013992,JN651 820,KC443468,KC14 0592,KC580223,KC5 80556,KC580381,KC 443446,KC443336,K C174966,GU296424, DQ838643,KC443246 ,KC580481,JXQ27867 ,KC175194,KC58000 7,KC580636,KC8347 05,JN258361,KC5805 92,KC443279,KC580 326,KC580516,KC58 0436,JXQ27899,KC17 5139,JN651871,JX96 5140,KC443666,KC7 69373,EF554139,KC 175271,JN831233,JN 605406,KC579985,JX 027734,KC174976,JN 651810,KC175008,K C579577,KC443655, KC579566,KC579894 ,JXQ27888,KC580403 ,JX271003,KC579668 ,JN831211,KC579827 ,KC580299,DQ14666 2,KC579905,DQ8386 00,JXQ27932,KC4434 24,JX965139,KC4432 57,HQ846845,JN258 336,KC443380,KC44 2883,KC580569,KC1 75282,JF712579,KC4 42976,DQ490537,GU 296425,KC443754,K C44931,KC769362,J N651853,JN651864,K |

TABLE 10-continued

VrioCap-1.0 Taxonomy

| Taxonomy | Rep.Acc.ID | Host | # GN's | Lineage | Seg. Count | GN.Acc.IDs |
|---|---|---|---|---|---|---|
| | | | | | | C579951,DQ490553, KC580167,KC174987, KC443545,KC19362 5,JN651766,JXQ2780 0,KC215510,KC4432 35,JX965141,JN6517 99,JX406749,KC5800 62,GU199488,KC579 693,KC580310,KC17 5183,GU565076,EF5 60623,JXQ27669,JN6 51842,KC443578,KC 769417,KC443009,K C579783,KC580063, DQ146651,JF521463, JXQ27910,JN258899, JF521474,KC443213, KC579726,JN651755 |
| Rotavirus A | NC_011509 | vertebrates,human | 366 | Reoviridae,Rotavirus,Rotavirus A | seg. 6 | JX965142,KC443668, KC580192,KC580301 ,AB040055,KC57960 1,KC174925,KC4430 00,KC769353,DQ146 702,KC215544,KC57 9987,KC442907,JN63 5547,HQ846870,KC4 43591,KC580571,KC 579774,KC580066,K C193616,JN651768,K C443646,KC579847,J X271005,JN258814,J XQ40422,KC769397, KC443679,KC442874 ,JN651757,JN258872 ,HQ846881,KC58060 5,KC443393,JX84114 4,JF521466,KC17489 2,KC443270,KC5805 07,KC443481,JN6054 30,KC834700,JN2587 80,JF712581,KC4429 18,JN258335,KC4437 45,KC579976,GU199 496,JN831213,DQ49 2673,AY456527,KC1 75108,DQ870504,KC 175021,KC580372,K C443378,KC580627, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | KC834699,JN872869, KC175240,KC580135 ,JN014004,KC195758 ,JN014006,KC175043 ,JX965143,KC443690 ,KC443248,JQ98890 3,KC443514,HQ8468 48,KC580638,KC579 579,KC174989,KC44 3580,KC580289,KC1 74958,GU565056,KC 140589,JN827249,JN 651812,KC579859,G U296428,KC580582, KC769474,KC175130 ,KC579873,KC17516 3,KC443360,KC5797 63,KC579998,KC442 896,DQ146695,KC58 0101,KC443437,KC5 79818,KC443602,DQ 870492,KC579568,K C443734,KC443503, KC580383,JX841180, KC174999,JN651844, JN635536,KC769419, KC175152,KC580339 ,DQ490538,KC44320 4,KC443149,KC5798 07,KC443492,JN2589 48,KC443316,KC442 944,KC579634,KC44 3303,KC443635,JN25 8392,JN258906,KC58 0078,JF712570,KC44 3657,KC579896,DQ1 46686,KC443404,KC 580616,KC443292,JN 258839,KC579717,H 0661116,KC443448, KC580438,KC580594 ,KC443237,GU56507 8,KC174870,DQ8705 00,KC443701,JN6518 22,KC579654,JF7125 59,KC580541,KC175 119,EF554152,KC58 0427,KC580560,KC1 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 75284,KC579623,KC834701,KC580203,KC442956,JN258370,DQ870507,KC580472,KC175087,KC193627,HQ661127,JX841143,JN831224,KC579502,KC174914,KC580046,KC443022,DQ490555,KC579590,KC579938,KC580405,KC580225,KC175273,KC580124,KC580394,KC443011,KC443193,KC175141,KC175010,JN605441,JN831235,KC580361,JN605419,KC580031,KC580236,JN014003,KC579964,KC443788,JN258897,KC443426,JX9651844,GU565045,KC443569,KC443536,FJ169858,JN651866,KC443171,KC579655,KC769430,KC175185,JN651900,KC580484,JF521477,KC442933,KC579907,HQ657142,KC580158,KC579953,KC580269,JN258359,KC579937,KC580518,HQ661138,KC579796,KC579728,KC580113,KC443138,KC443767,KC193637,KC580020,KC443160,JN651801,KC769331,KC579918,KC443226,KC579695,DQ146675,KC579829,KC579490,KC579672,KC175207,KC579750,JN258847,KC443281,JN651779,KC769463,JN651855,KC579524,JN605408,JN258880,JN605090,KC174936,KC580247 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | ,KC443338,JN014005,KC580169,JN651888,KC580312,KC44354 7,DQ870488,JN2589 19,JQ688678,KC443 349,KC579546,KC19 5773,JX406752,KC17 4903,JN651872,KC44 3215,KC175065,JN25 8348,KC769408,KC7 69309,HQ657164,KC 44382,KC769342,K C175076,KC174881,J N651790,KC443624, KC443415,KC175262 ,KC579513,KC76945 2,KC580067,KC4433 27,KC175218,KC579 479,KC175196,KC76 9364,KC175098,KC5 80496,KC443712,JN6 35558,JX841142,KC5 79673,KC580416,KC 580460,AY456528,K C443259,GU565067, KC215501,DQ870496 ,GU827410,KC58032 8,KC443558,KC5798 48,JN258807,KC5797 39,KC580559,KC175 229,KC443756,KC17 5251,DQ146664,KC4 42885,U36240,EF554 141,KC580530,GU29 6429,KC580495,KC4 43459,FN665682,KC 443723,DQ146642,K C580214,HQ846859, KC175054,KC442989 ,KC579535,KC58025 8,KC580483,JN25882 9,KC580449,KC4430 33,KC769375,KC579 684,FN665693,HQ65 7153,KC580181,KC5 79557,KC442978,KC 443182,DQ146653,K C769386,KC769441, |

TABLE 10-continued

| Taxonomy | Rep.Acc.ID | Host | ViroCap-1.0 Taxonomy # GN's | Lineage | Seg. Count | GN.Acc.IDs |
|---|---|---|---|---|---|---|
| | | | | | | KC215512,JN605452, GU565089,JN014002, U85998,DQ490549,JN258382,KC579706, KC442967,KC443470, DQ838650,KC44361 3,KC580290,KC4433 71,JN258403,KC1751 74,JN258858,KC5800 09,KC175032,KC174 947,KC579884,JN258 930,JN258792,JN651 833,KC443525,KC57 9785,JN258939,KC76 9485,KC769320,KC5 80350,KC579612 |
| Rotavirus A | NC_011510 | vertebrates,human | 352 | Reoviridae,Rotavirus,Rotavirus A | seg. 4 | JN258809,JN605451, JXQ27799,KC175042, JN635546,JN872868, KC443348,KC174988, KC579556,KC57969 4,KC580168,KC5802 02,AB526248,JN6518 78,JXQ27744,GU565 044,KC580134,KC57 9895,KC580180,DQ3 21496,KC443546,KC 580123,KC579761,K C580581,JN258349,K C174902,KC442906, KC580287,KC769418 ,KC443021,KC57954 5,KC174967,JXQ2793 3,KC579589,KC4437 87,JN258875,KC1749 13,JN258832,JN6518 65,KC769440,KC443 214,GU565077,AB52 6246,KC443159,KC4 43436,KC193636,KC 443524,JN651887,JX 027702,KC579986,F N665680,JN013997,K C443590,KC580626, KC579762,KC443579 ,KC443733,JN831223 ,KC443667,KC57951 2,KC443370,KC5798 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 17,KC443315,KC443414,KC443645,HQ661126,IN258383,JN651811,KC443568,JN258340,JN258360,JXQ27887,JN605407,JXQ27975,JN635535,KC579653,KC443403,KC580517,KC175206,KC579795,KC443634,KC443744,KC769396,JN651767,JN258884,JXQ27953,DQ838602,AB573650,GU565066,KC80557,HQ657152,KC442943,JXQ27776,JN013995,KC579501,KC580257,KC443766,KC443010,JXQ27722,KC769385,HQ657163,KC443032,JN258787,KC579716,KC443225,KC579936,KC580448,U65924,KC769462,KC580570,KC579975,JN258855,KC580008,AB573872,JN635557,JN258404,AB573648,KC580371,KC579846,KC580349,KC175184,KC580604,KC579611,KC769363,DQ841262,KC579872,KC579534,KC442988,KC442954,JXQ27645,KC580338,KC443236,KC174924,JN258798,KC443148,JXQ27898,GU565055,KC580157,KC443326,JQ688676,JN651756,KC769484,KC580540,KC580482,KC579567,KC443678,KC443623,HQ846857,KC580246,KC579652,KC443469,KC579952,JXQ27821,KC580593,GU565050 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 88,JX271004,KC769330,JXQ27789,JXQ27684,JN651800,KC579749,DQ492672,KC580235,DQ490548,JXQ27831,KC579845,KC579683,KC443557,JXQ27853,JN651854,KC580089,FJ169856,KCS79633,JN258866,JN258954,JF521475,KC193615,JN258371,JN831212,KC579727,KC443247,KC769429,KC443535,JXQ27940,JN258920,JXQ27779,KC443137,KC443337,KC579705,AB571047,DQ838604,JXQ27755,JN258898,KC579489,KC442884,KC443392,KC443689,JXQ27911,KC442977,JN651778,KC580112,JXQ27963,KC580100,KC580637,FN665691,JN258819,KC580393,KC175020,KC579828,KC579523,KC579738,KC580224,JXQ27661,KC769473,KC580558,KC579963,JN651832,KC580426,KC175097,JXQ27843,EF990707,KC443302,KC579806,KC769308,KC580360,KC579478,JN831234,KC175151,KC580191,KC769451,KC580459,KC579773,KC580382,KC443491,KC580494,KC580415,KC443269,JN258841,JN651789,KC580030,KC443425,KC579917,JN605418,KC174946,KC579671,HQ846879,KC580404,KC443447 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | ,JF521464,HQ661137 ,JXQ27733,KC580506 ,KC580437,JXQ27812 ,KC443612,DQ242 61 ,KC443170,KC4437 55, KC443722,KC443 513,KC579670,HQ84 6868,KC442955,KC4 43777,KC174977,KC 580065,JN651821,JX 027876, KC442966,K C579906,EF554151, J N258839,KC443181,KC 442873,KC443291 ,KC193626,JXQ27920, KC579622, KC58061 5,JQ988902,AB57364 6,KC442917,KC5804 71, KC174957, DQ490 554,JXQ27650,AY773 004,EF554140,KC44 3359,KC769374,KC5 79578, JN651843,KC5 79883,KC195759,KC 442895,KC580045,D Q321494,JXQ27707, DQ321492,KC579997 ,KC769319,KC44331 4,AB055967,KC7693 41, KC580311 ,JN2589 40, KC579858,KC769 352,JN013994,JN258 933,KC443203,KC44 3700,KC443601 ,KC5 80064, KC443502, HQ 657141 ,KC443280,D Q838603, KC579784, KC443192,KC442999 , DQ838605, J XQ2786 5,KC175195,KC5803 00,JN827247,KC5800 19, KC443711 ,JN6054 40,JX406750,KC5802 88, KC443656,HQ846 846,KC443480,HQ66 1115,GU827409,KC4 42932,KC579600,KC 580077,JN258909,KC |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A 1290xU K reassortant (UKg91290) | | | | | | 580529, KC443458,JX 027678, KC580327,JN 013996, KC443381, KC580268,KC580213, KC443258,KC175250 ,JN605429,JN651899 |
| Rotavirus A 1290xUK reassortant (UKg91290) | NC_011500 | vertebrates,human | Reoviridae,Rotavirus,Rotavirus A | 3 | seg. 5 | JF693219,J F693184, JF693118 |
| Rotavirus A 1290xUK reassortant (UKg91290) | NC_011501 | vertebrates,human | Reoviridae,Rotavirus,Rotavirus A | 2 | seg. 7 | JF693121 ,JF693187 |
| Rotavirus A 1290x11 K reassortant (UKg91290) | NC_011502 | vertebrates,human | Reoviridae,Rotavirus,Rotavirus A | 3 | seg. 8 | JF693186,JF693120, JF693220 |
| Rotavirus A 1290xUK reassortant (UKg91290) | NC_011503 | vertebrates,human | Reoviridae,Rotavirus,Rotavirus A | 3 | seg. 9 | JF693188,JF693122, JF693221 |
| Rotavirus A 1290xUK reassortant (UKg91290) | NC_011504 | vertebrates,human | Reoviridae,Rotavirus,Rotavirus A | 2 | seg. 10 | JF693123,JF693189 |
| Rotavirus A 1290xUK reassortant (UKg91290) | NC_011505 | vertebrates,human | Reoviridae,Rotavirus,Rotavirus A | 2 | seg. 11 | JF693124,JF693190 |
| Rotavirus A 1290xUK reassortant (UKg91290) | NC_011506 | vertebrates,human | Reoviridae,Rotavirus,Rotavirus A | 2 | seg. 2 | JF693181 ,JF693115 |
| Rotavirus A 1290xUK reassortant (UKg91290) | NC_011507 | vertebrates,human | Reoviridae,Rotavirus,Rotavirus A | 2 | seg. 1 | JF693180,JF693114 |
| Rotavirus A 1290xUK reassortant (UKg91290) | NC_011508 | vertebrates,hum | Reoviridae,Rotavirus,Rotavirus A | 2 | seg. 3 | JF693182,JF693116 |
| Rotavirus A 1290xUK reassortant (UKg91290) | NC_011509 | vertebrates,human | Reoviridae,Rotavirus,Rotavirus A | 3 | seg. 5 | JF693219,J F693184, JF693118 |
| Rotavirus A 1290xUK reassortant (UKg91290) | NC_011510 | vertebrates,human | Reoviridae,Rotavirus,Rotavirus A | 2 | seg. 6 | JF693119,JF693185 |
| Rotavirus A 1290xUK reassortant (UKg91290) | NC_011500 | vertebrates,human | Reoviridae,Rotavirus,Rotavirus A | 3 | seg. 4 | JF693117,JF693183, JF693218 |
| Rotavirus A AU32xUK reassortant (UKg9AU32) | NC_011501 | vertebrates,human | Reoviridae,Rotavirus,Rotavirus A | 3 | seg. 5 | JF693129,JF693223, JF693195 |
| Rotavirus A AU32xUK reassortant (UKg9AU32) | NC_011502 | vertebrates,human | Reoviridae,Rotavirus,Rotavirus A | 2 | seg. 7 | JF693198,JF693132 |
| Rotavirus A AU32xUK reassortant (UKg9AU32) | NC_011503 | vertebrates,human | Reoviridae,Rotavirus,Rotavirus A | 3 | seg. 8 | JF693131,JF693224, JF693197 |
| Rotavirus A AU32xUK reassortant (UKg9AU32) | NC_011504 | vertebrates,human | Reoviridae,Rotavirus,Rotavirus A | 3 | seg. 9 | JF693199,JF693133, JF693225 |
| Rotavirus A AU32xUK reassortant (UKg9AU32) | NC_011505 | vertebrates,human | Reoviridae,Rotavirus,Rotavirus A | 2 | seg. 10 | JF693134,JF693200 |
| Rotavirus A AU32xUK reassortant (UKg9AU32) | NC_011506 | vertebrates,human | Reoviridae,Rotavirus,Rotavirus A | 2 | seg. 11 | JF693201,JF693135 |
| Rotavirus A AU32xUK reassortant (UKg9AU32) | NC_011507 | vertebrates,human | Reoviridae,Rotavirus,Rotavirus A | 2 | seg. 2 | JF693192,JF693126 |
| Rotavirus A AU32xUK reassortant (UKg9AU32) | NC_011508 | vertebrates,human | Reoviridae,Rotavirus,Rotavirus A | 2 | seg. 1 | JF693191,JF693125 |
| Rotavirus A AU32xUK reassortant (UKg9AU32) | NC_011508 | vertebrates,human | Reoviridae,Rotavirus,Rotavirus A | 2 | seg. 3 | JF693127,JF693193 |

TABLE 10-continued

| Taxonomy | Rep.Acc.ID | Host | ViroCap-1.0 Taxonomy | | Seg. Count | GN.Acc.IDs |
| --- | --- | --- | --- | --- | --- | --- |
| | | | # GN's | Lineage | | |
| Rotavirus A AU32xUK reassortant (UKg9AU32) | NC_011509 | vertebrates,human | 2 | Reoviridae,Rotavirus,Rotavirus A | seg. 6 | JF693130,JF693196 |
| Rotavirus A AU32xUK reassortant (UKg9AU32) | NC_011510 | vertebrates,human | 3 | Reoviridae,Rotavirus,Rotavirus A | seg. 4 | JF693194,JF693128, JF693222 |
| Rotavirus A DS-1xUK reassortant (UKg9DS-1) | NC_011500 | vertebrates,human | 3 | Reoviridae,Rotavirus,Rotavirus A | seg. 5 | JF693207,JF693151, JF693085 |
| Rotavirus A DS-1xUK reassortant (UKg9DS-1) | NC_011501 | vertebrates,human | 2 | Reoviridae,Rotavirus,Rotavirus A | seg. 7 | JF693154,JF693088 |
| Rotavirus A DS-1xUK reassortant (UKg9DS-1) | NC_011502 | vertebrates,human | 3 | Reoviridae,Rotavirus,Rotavirus A | seg. 8 | JF693087,JF693208, JF693153 |
| Rotavirus A DS-1xUK reassortant (UKg9DS-1) | NC_011503 | vertebrates,human | 3 | Reoviridae,Rotavirus,Rotavirus A | seg. 9 | JF693089,JF693209, JF693155 |
| Rotavirus A DS-1xUK reassortant (UKg9DS-1) | NC_011504 | vertebrates,human | 2 | Reoviridae,Rotavirus,Rotavirus A | seg. 10 | JF693156,JF693090 |
| Rotavirus A DS-1xUK reassortant (UKg9DS-1) | NC_011505 | vertebrates,human | 2 | Reoviridae,Rotavirus,Rotavirus A | seg. 11 | JF693091,JF693157 |
| Rotavirus A DS-1xUK reassortant (UKg9DS-1) | NC_011506 | vertebrates,human | 2 | Reoviridae,Rotavirus,Rotavirus A | seg. 2 | JF693082,JF693148 |
| Rotavirus A DS-1xUK reassortant (UKg9DS-1) | NC_011507 | vertebrates,human | 2 | Reoviridae,Rotavirus,Rotavirus A | seg. 1 | JF693147,JF693081 |
| Rotavirus A DS-1xUK reassortant (UKg9DS-1) | NC_011508 | vertebrates,human | 2 | Reoviridae,Rotavirus,Rotavirus A | seg. 3 | JF693149,JF693083 |
| Rotavirus A DS-1xUK reassortant (UKg9DS-1) | NC_011509 | vertebrates,human | 2 | Reoviridae,Rotavirus,Rotavirus A | seg. 6 | JF693152,JF693086 |
| Rotavirus A DS-1xUK reassortant (UKg9DS-1) | NC_011510 | vertebrates,human | 3 | Reoviridae,Rotavirus,Rotavirus A | seg. 4 | JF693150,JF693206, JF693084 |
| Rotavirus A DxUK reassortant (UKg9D) | NC_011500 | vertebrates,human | 3 | Reoviridae,Rotavirus,Rotavirus A | seg. 5 | JF693140,JF693203, JF693074 |
| Rotavirus A DxUK reassortant (UKg9D) | NC_011501 | vertebrates,human | 2 | Reoviridae,Rotavirus,Rotavirus A | seg. 7 | JF693143,JF693077 |
| Rotavirus A DxUK reassortant (UKg9D) | NC_011502 | vertebrates,human | 3 | Reoviridae,Rotavirus,Rotavirus A | seg. 8 | JF693142,JF693076, JF693204 |
| Rotavirus A DxUK reassortant (UKg9D) | NC_011503 | vertebrates,human | 3 | Reoviridae,Rotavirus,Rotavirus A | seg. 9 | JF693205,JF693144, JF693078 |
| Rotavirus A DxUK reassortant (UKg9D) | NC_011504 | vertebrates,human | 2 | Reoviridae,Rotavirus,Rotavirus A | seg. 10 | JF693079,JF693145 |
| Rotavirus A DxUK reassortant (UKg9D) | NC_011505 | vertebrates,human | 2 | Reoviridae,Rotavirus,Rotavirus A | seg. 11 | JF693080,JF693146 |
| Rotavirus A DxUK reassortant (UKg9D) | NC_011506 | vertebrates,human | 2 | Reoviridae,Rotavirus,Rotavirus A | seg. 2 | JF693137,JF693071 |
| Rotavirus A DxUK reassortant (UKg9D) | NC_011507 | vertebrates,human | 2 | Reoviridae,Rotavirus,Rotavirus A | seg. 1 | JF693136,JF693070 |
| Rotavirus A DxUK reassortant (UKg9D) | NC_011508 | vertebrates,human | 2 | Reoviridae,Rotavirus,Rotavirus A | seg. 3 | JF693072,JF693138 |
| Rotavirus A DxUK reassortant (UKg9D) | NC_011509 | vertebrates,human | 2 | Reoviridae,Rotavirus,Rotavirus A | seg. 6 | JF693141,JF693075 |
| Rotavirus A DxUK reassortant (UKg9D) | NC_011510 | vertebrates,human | 3 | Reoviridae,Rotavirus,Rotavirus A | seg. 4 | JF693139,JF693202, JF693073 |

TABLE 10-continued

VivoCap-1.0 Taxonomy

| Taxonomy | Rep.Acc.ID | Host | Lineage | # GN's | Seg. Count | GN.Acc.IDs |
|---|---|---|---|---|---|---|
| Rotavirus A EC2184/ECU/G11P[6] | NC_011501 | vertebrates,human | Reoviridae,Rotavirus,Rotavirus A | 1 | seg. 7 | GQ149098 |
| Rotavirus A EC2184/ECU/G11P[6] | NC_011502 | vertebrates,human | Reoviridae,Rotavirus,Rotavirus A | 1 | seg. 8 | GQ149101 |
| Rotavirus A EC2184/ECU/G11P[6] | NC_011504 | vertebrates,human | Reoviridae,Rotavirus,Rotavirus A | 1 | seg. 10 | GQ149099 |
| Rotavirus A EC2184/ECU/G11P[6] | NC_011505 | vertebrates,human | Reoviridae,Rotavirus,Rotavirus A | 1 | seg. 11 | GQ149100 |
| Rotavirus A EC2184/ECU/G11P[6] | NC_011509 | vertebrates,human | Reoviridae,Rotavirus,Rotavirus A | 1 | seg. 6 | GQ149095 |
| Rotavirus A Hu/1290/Kenya/1991/G8 | NC_011503 | vertebrates,human | Reoviridae,Rotavirus,Rotavirus A | 1 | seg. 9 | EU488721 |
| Rotavirus A Hu/BE UBE2001/2009/G9P[6] | NC_011502 | vertebrates,human | Reoviridae,Rotavirus,Rotavirus A | 1 | seg. 8 | JQ993325 |
| Rotavirus A Hu/BE UBE2001/2009/G9P[6] | NC_011503 | vertebrates,human | Reoviridae,Rotavirus,Rotavirus A | 1 | seg. 9 | JQ993318 |
| Rotavirus A Hu/BE UBE2001/2009/G9P[6] | NC_011504 | vertebrates,human | Reoviridae,Rotavirus,Rotavirus A | 1 | seg. 10 | JQ993327 |
| Rotavirus A Hu/BE UBE2001/2009/G9P[6] | NC_011506 | vertebrates,human | Reoviridae,Rotavirus,Rotavirus A | 1 | seg. 2 | JQ993322 |
| Rotavirus A Hu/BE UBE2001/2009/G9P[6] | NC_011507 | vertebrates,human | Reoviridae,Rotavirus,Rotavirus A | 1 | seg. 1 | JQ993321 |
| Rotavirus A Hu/BE UBE2001/2009/G9P[6] | NC_011508 | vertebrates,human | Reoviridae,Rotavirus,Rotavirus A | 1 | seg. 3 | JQ993323 |
| Rotavirus A Hu/BEUF01322/2009/G3P[6] | NC_011500 | vertebrates,human | Reoviridae,Rotavirus,Rotavirus A | 1 | seg. 5 | JF460829 |
| Rotavirus A Hu/BEUF01322/2009/G3P[6] | NC_011501 | vertebrates,human | Reoviridae,Rotavirus,Rotavirus A | 1 | seg. 7 | JF460831 |
| Rotavirus A Hu/BEUF01322/2009/G3P[6] | NC_011502 | vertebrates,human | Reoviridae,Rotavirus,Rotavirus A | 1 | seg. 8 | JF460830 |
| Rotavirus A Hu/BEUF01322/2009/G3P[6] | NC_011503 | vertebrates,human | Reoviridae,Rotavirus,Rotavirus A | 1 | seg. 9 | JF460828 |
| Rotavirus A Hu/BEUF01322/2009/G3P[6] | NC_011504 | vertebrates,human | Reoviridae,Rotavirus,Rotavirus A | 1 | seg. 10 | JF460832 |
| Rotavirus A Hu/BEUF01322/2009/G3P[6] | NC_011505 | vertebrates,human | Reoviridae,Rotavirus,Rotavirus A | 1 | seg. 11 | JF460833 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A Hu/BEUF01322/2009/G3P[6] | NC_011506 | vertebrates,human | Reoviridae,Rotavirus,Rotavirus A | 1 | seg. 2 | JF460824 |
| Rotavirus A Hu/BEUF01322/2009/G3P[6] | NC_011507 | vertebrates,human | Reoviridae,Rotavirus,Rotavirus A | 1 | seg. 1 | JF460823 |
| Rotavirus A Hu/BEUF01322/2009/G3P[6] | NC_011508 | vertebrates,human | Reoviridae,Rotavirus,Rotavirus A | 1 | seg. 3 | JF460825 |
| Rotavirus A Hu/BEUF01322/2009/G3P[6] | NC_011509 | vertebrates,human | Reoviridae,Rotavirus,Rotavirus A | 1 | seg. 6 | JF460827 |
| Rotavirus A Hu/BEUF01322/2009/G3P[6] | NC_011510 | vertebrates,human | Reoviridae,Rotavirus,Rotavirus A | 1 | seg. 4 | JF460826 |
| Rotavirus A Hu/BEUF01498/2009/G3P[6] | NC_011500 | vertebrates,human | Reoviridae,Rotavirus,Rotavirus A | 1 | seg. 5 | JF460840 |
| Rotavirus A Hu/BEUF01498/2009/G3P[6] | NC_011501 | vertebrates,human | Reoviridae,Rotavirus,Rotavirus A | 1 | seg. 7 | JF460842 |
| Rotavirus A Hu/BEUF01498/2009/G3P[6] | NC_011502 | vertebrates,human | Reoviridae,Rotavirus,Rotavirus A | 1 | seg. 8 | JF460841 |
| Rotavirus A Hu/BEUF01498/2009/G3P[6] | NC_011503 | vertebrates,human | Reoviridae,Rotavirus,Rotavirus A | 1 | seg. 9 | JF460839 |
| Rotavirus A Hu/BEUF01498/2009/G3P[6] | NC_011504 | vertebrates,human | Reoviridae,Rotavirus,Rotavirus A | 1 | seg. 10 | JF460843 |
| Rotavirus A Hu/BEUF01498/2009/G3P[6] | NC_011505 | vertebrates,human | Reoviridae,Rotavirus,Rotavirus A | 1 | seg. 11 | JF460844 |
| Rotavirus A Hu/BEUF01498/2009/G3P[6] | NC_011506 | vertebrates,human | Reoviridae,Rotavirus,Rotavirus A | 1 | seg. 2 | JF460835 |
| Rotavirus A Hu/BEUF01498/2009/G3P[6] | NC_011507 | vertebrates,human | Reoviridae,Rotavirus,Rotavirus A | 1 | seg. 1 | JF460834 |
| Rotavirus A Hu/BEUF01498/2009/G3P[6] | NC_011508 | vertebrates,human | Reoviridae,Rotavirus,Rotavirus A | 1 | seg. 3 | JF460836 |
| Rotavirus A Hu/BEUF01498/2009/G3P[6] | NC_011509 | vertebrates,human | Reoviridae,Rotavirus,Rotavirus A | 1 | seg. 6 | JF460838 |
| Rotavirus A Hu/BEUF01498/2009/G3P[6] | NC_011510 | vertebrates,human | Reoviridae,Rotavirus,Rotavirus A | 1 | seg. 4 | JF460837 |

TABLE 10-continued

| Taxonomy | Rep.Acc.ID | Host | # GN's | VirоCap-1.0 Taxonomy Lineage | Seg. Count | GN.Acc.IDs |
|---|---|---|---|---|---|---|
| Rotavirus A Hu/CI-81/2011/KOR | NC_011501 | vertebrates,human | 1 | Reoviridae,Rotavirus,Rotavirus A | seg. 7 | JN887815 |
| Rotavirus A Hu/CI-81/2011/KOR | NC_011503 | vertebrates,human | 1 | Reoviridae,Rotavirus,Rotavirus A | seg. 9 | JN887818 |
| Rotavirus A Hu/CI-81/2011/KOR | NC_011504 | vertebrates,human | 2 | Reoviridae,Rotavirus,Rotavirus A | seg. 10 | JN887814,JN887816 |
| Rotavirus A Hu/CI-81/2011/KOR | NC_011505 | vertebrates,human | 1 | Reoviridae,Rotavirus,Rotavirus A | seg. 11 | JN887813 |
| Rotavirus A Hu/CI-81/2011/KOR | NC_011506 | vertebrates,human | 1 | Reoviridae,Rotavirus,Rotavirus A | seg. 2 | JN887811 |
| Rotavirus A Hu/CI-81/2011/KOR | NC_011507 | vertebrates,human | 1 | Reoviridae,Rotavirus,Rotavirus A | seg. 1 | JN887812 |
| Rotavirus A Hu/CI-81/2011/KOR | NC_011508 | vertebrates,human | 1 | Reoviridae,Rotavirus,Rotavirus A | seg. 3 | JN887810 |
| Rotavirus A Hu/CI-81/2011/KOR | NC_011509 | vertebrates,human | 1 | Reoviridae,Rotavirus,Rotavirus A | seg. 6 | JN887819 |
| Rotavirus A Hu/Cm15/2008/Cuba/G9P [8] | NC_011503 | vertebrates,human | 1 | Reoviridae,Rotavirus,Rotavirus A | seg. 9 | FJ348353 |
| Rotavirus A Hu/Cm42/2008/Cuba/G9P [8] | NC_011503 | vertebrates,human | 1 | Reoviridae,Rotavirus,Rotavirus A | seg. 9 | FJ348352 |
| Rotavirus A Hu/DC706/USA/1980/G9 | NC_011503 | vertebrates,human | 1 | Reoviridae,Rotavirus,Rotavirus A | seg. 9 | EU153553 |
| Rotavirus A Hu/Dhaka6/BGD/2001/G11 P25 | NC_011501 | vertebrates,human | 1 | Reoviridae,Rotavirus,Rotavirus A | seg. 7 | EF560709 |
| Rotavirus A Hu/Dhaka6/BGD/2001/G11 P25 | NC_011502 | vertebrates,human | 1 | Reoviridae,Rotavirus,Rotavirus A | seg. 8 | EF560710 |
| Rotavirus A Hu/Dhaka6/BGD/2001/G11 P25 | NC_011504 | vertebrates,human | 1 | Reoviridae,Rotavirus,Rotavirus A | seg. 10 | EF560711 |
| Rotavirus A Hu/Dhaka6/BGD/2001/G11 P25 | NC_011505 | vertebrates,human | 1 | Reoviridae,Rotavirus,Rotavirus A | seg. 11 | EF560712 |
| Rotavirus A Hu/Dhaka6/BGD/2001/G11 P25 | NC_011507 | vertebrates,human | 1 | Reoviridae,Rotavirus,Rotavirus A | seg. 1 | EF560705 |
| Rotavirus A Hu/Dhaka6/BGD/2001/G11 P25 | NC_011508 | vertebrates,human | 1 | Reoviridae,Rotavirus,Rotavirus A | seg. 3 | EF560706 |
| Rotavirus A Hu/Dhaka6/BGD/2001/G11 P25 | NC_011509 | vertebrates,human | 1 | Reoviridae,Rotavirus,Rotavirus A | seg. 6 | EF560707 |
| Rotavirus A Hu/G2275/USA/1980/G9 | NC_011503 | vertebrates,human | 1 | Reoviridae,Rotavirus,Rotavirus A | seg. 9 | EU153554 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A Hu/HK69/CN/1978/G5 | NC_011503 | vertebrates,human | Reoviridae,Rotavirus,Rotavirus A | 1 | seg. 9 | JN699034 |
| Rotavirus A Hu/HK75/CN/1978/G9 | NC_011503 | vertebrates,human | Reoviridae,Rotavirus,Rotavirus A | 1 | seg. 9 | JN699033 |
| Rotavirus A Hu/Ha1/2006/Cuba/G1P[6] | NC_011503 | vertebrates,human | Reoviridae,Rotavirus,Rotavirus A | 1 | seg. 9 | FJ348346 |
| Rotavirus A Hu/Ha100/2008/Cuba/G9P[8] | NC_011503 | vertebrates,human | Reoviridae,Rotavirus,Rotavirus A | 1 | seg. 9 | FJ348355 |
| Rotavirus A Hu/Ha16/2006/Cuba/G9P[8] | NC_011503 | vertebrates,human | Reoviridae,Rotavirus,Rotavirus A | 1 | seg. 9 | FJ348351 |
| Rotavirus A Hu/Ha21/2006/Cuba/G9P[8] | NC_011503 | vertebrates,human | Reoviridae,Rotavirus,Rotavirus A | 1 | seg. 9 | FJ348354 |
| Rotavirus A Hu/Ha45/2006/Cuba/G1P[8] | NC_011503 | vertebrates,human | Reoviridae,Rotavirus,Rotavirus A | 1 | seg. 9 | FJ348348 |
| Rotavirus A Hu/Ha5/2006/Cuba/G1P[6] | NC_011503 | vertebrates,human | Reoviridae,Rotavirus,Rotavirus A | 1 | seg. 9 | FJ348347 |
| Rotavirus A Hu/Ha67/2007/Cuba/G1P[8] | NC_011503 | vertebrates,human | Reoviridae,Rotavirus,Rotavirus A | 1 | seg. 9 | FJ348349 |
| Rotavirus A Hu/Ha95/2008/Cuba/G1P[8] | NC_011503 | vertebrates,human | Reoviridae,Rotavirus,Rotavirus A | 1 | seg. 9 | FJ348350 |
| Rotavirus A Hu/NhaTrang/V141/2006/VNM/G3 | NC_011503 | vertebrates,human | Reoviridae,Rotavirus,Rotavirus A | 1 | seg. 9 | AB525798 |
| Rotavirus A Hu/NhaTrang/V152/2006/VNM/G3 | NC_011503 | vertebrates,human | Reoviridae,Rotavirus,Rotavirus A | 1 | seg. 9 | AB525799 |
| Rotavirus A Hu/NhaTrang/V17/2006/VNM | NC_011503 | vertebrates,human | Reoviridae,Rotavirus,Rotavirus A | 1 | seg. 9 | AB605602 |
| Rotavirus A Hu/NhaTrang/V17/2006/VNM | NC_011509 | vertebrates,human | Reoviridae,Rotavirus,Rotavirus A | 1 | seg. 6 | AB605598 |
| Rotavirus A Hu/NhaTrang/V173/2006/VNM/G3 | NC_011503 | vertebrates,human | Reoviridae,Rotavirus,Rotavirus A | 1 | seg. 9 | AB525800 |
| Rotavirus A Hu/NhaTrang/V182/2006/VNM/G3 | NC_011503 | vertebrates,human | Reoviridae,Rotavirus,Rotavirus A | 1 | seg. 9 | AB525801 |
| Rotavirus A Hu/NhaTrang/V20/2006/VNM | NC_011503 | vertebrates,human | Reoviridae,Rotavirus,Rotavirus A | 1 | seg. 9 | AB605603 |
| Rotavirus A Hu/NhaTrang/V20/2006/VNM | NC_011509 | vertebrates,human | Reoviridae,Rotavirus,Rotavirus A | 1 | seg. 6 | AB605599 |
| Rotavirus A Hu/NhaTrang/V30/2006/VNM | NC_011503 | vertebrates,human | Reoviridae,Rotavirus,Rotavirus A | 1 | seg. 9 | AB605604 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A Hu/NhaTrang/V30/2006/VN M | NC_011509 | vertebrates,human | Reoviridae,Rotavirus,Rotavirus A | 1 | seg. 6 | AB605600 |
| Rotavirus A Hu/NhaTrang/V32/2006/VN M | NC_011503 | vertebrates,human | Reoviridae,Rotavirus,Rotavirus A | 1 | seg. 9 | AB605605 |
| Rotavirus A Hu/NhaTrang/V32/2006/VN M | NC_011509 | vertebrates,human | Reoviridae,Rotavirus,Rotavirus A | 1 | seg. 6 | AB605601 |
| Rotavirus A Hu/NhaTrang/V88/2006/VN M/G3 | NC_011503 | vertebrates,human | Reoviridae,Rotavirus,Rotavirus A | 1 | seg. 9 | AB525797 |
| Rotavirus A Hu/SA3426DGM04/G12P [6] | NC_011503 | vertebrates,human | Reoviridae,Rotavirus,Rotavirus A | 1 | seg. 9 | EU284736 |
| Rotavirus A Hu/USA/06-242/2006/G2P[6] | NC_011500 | vertebrates,human | Reoviridae,Rotavirus,Rotavirus A | 1 | seg. 5 | JF460818 |
| Rotavirus A Hu/USA/06-242/2006/G2P[6] | NC_011501 | vertebrates,human | Reoviridae,Rotavirus,Rotavirus A | 1 | seg. 7 | JF460820 |
| Rotavirus A Hu/USA/06-242/2006/G2P[6] | NC_011502 | vertebrates,human | Reoviridae,Rotavirus,Rotavirus A | 1 | seg. 8 | JF460819 |
| Rotavirus A Hu/USA/06-242/2006/G2P[6] | NC_011503 | vertebrates,human | Reoviridae,Rotavirus,Rotavirus A | 1 | seg. 9 | JF460817 |
| Rotavirus A Hu/USA/06-242/2006/G2P[6] | NC_011504 | vertebrates,human | Reoviridae,Rotavirus,Rotavirus A | 1 | seg. 10 | JF460821 |
| Rotavirus A Hu/USA/06-242/2006/G2P[6] | NC_011505 | vertebrates,human | Reoviridae,Rotavirus,Rotavirus A | 1 | seg. 11 | JF460822 |
| Rotavirus A Hu/USA/06-242/2006/G2P[6] | NC_011506 | vertebrates,human | Reoviridae,Rotavirus,Rotavirus A | 1 | seg. 2 | JF460813 |
| Rotavirus A Hu/USA/06-242/2006/G2P[6] | NC_011507 | vertebrates,human | Reoviridae,Rotavirus,Rotavirus A | 1 | seg. 1 | JF460812 |
| Rotavirus A Hu/USA/06-242/2006/G2P[6] | NC_011508 | vertebrates,human | Reoviridae,Rotavirus,Rotavirus A | 1 | seg. 3 | JF460814 |
| Rotavirus A Hu/USA/06-242/2006/G2P[6] | NC_011509 | vertebrates,human | Reoviridae,Rotavirus,Rotavirus A | 1 | seg. 6 | JF460816 |
| Rotavirus A Hu/USA/06-242/2006/G2P[6] | NC_011510 | vertebrates,human | Reoviridae,Rotavirus,Rotavirus A | 1 | seg. 4 | JF460815 |
| Rotavirus A IAL28xUK reassortant (UKg9IAL28) | NC_011506 | vertebrates,human | Reoviridae,Rotavirus,Rotavirus A | 1 | seg. 2 | JF990818 |
| Rotavirus A IAL28xUK reassortant (UKg9IAL28) | NC_011507 | vertebrates,human | Reoviridae,Rotavirus,Rotavirus A | 1 | seg. 1 | JF990817 |
| Rotavirus A IAL28xUK reassortant (UKg9IAL28) | NC_011508 | vertebrates,human | Reoviridae,Rotavirus,Rotavirus A | 1 | seg. 3 | JF990819 |
| Rotavirus A Ind/Bo/HR/B85 | NC_011502 | vertebrates,human | Reoviridae,Rotavirus,Rotavirus A | 1 | seg. 8 | JF831950 |
| Rotavirus A Ind/Bo/HR/B85 | NC_011505 | vertebrates,human | Reoviridae,Rotavirus,Rotavirus A | 1 | seg. 11 | JF831951 |
| Rotavirus A Ind/HR/B111 | NC_011504 | vertebrates,human | Reoviridae,Rotavirus,Rotavirus A | 1 | seg. 10 | JF831958 |

TABLE 10-continued

| Taxonomy | Rep.Acc.ID | Host | # GN's | ViroCap-1.0 Taxonomy Lineage | Seg. Count | GN.Acc.IDs |
|---|---|---|---|---|---|---|
| Rotavirus A Ind/HR/B91 | NC_011504 | vertebrates,human | 1 | Reoviridae,Rotavirus,Rotavirus A | seg. 10 | JF831955 |
| Rotavirus A Ind/MP/13100 | NC_011503 | vertebrates,human | 1 | Reoviridae,Rotavirus,Rotavirus A | seg. 9 | JF831944 |
| Rotavirus A Ind/MP/Buffalo/6212 | NC_011504 | vertebrates,human | 1 | Reoviridae,Rotavirus,Rotavirus A | seg. 10 | JF831954 |
| Rotavirus A Ind/MP/C1 | NC_011504 | vertebrates,human | 1 | Reoviridae,Rotavirus,Rotavirus A | seg. 10 | JF831956 |
| Rotavirus A Ind/UKD/C5 | NC_011504 | vertebrates,human | 1 | Reoviridae,Rotavirus,Rotavirus A | seg. 10 | JF831947 |
| Rotavirus A Ind/UP/13E4 | NC_011504 | vertebrates,human | 1 | Reoviridae,Rotavirus,Rotavirus A | seg. 10 | JF831945 |
| Rotavirus A PxUK reassortant (UKg9P) | NC_011500 | vertebrates,human | 3 | Reoviridae,Rotavirus,Rotavirus A | seg. 5 | JF693096,JF693162, JF693211 |
| Rotavirus A PxUK reassortant (UKg9P) | NC_011501 | vertebrates,human | 2 | Reoviridae,Rotavirus,Rotavirus A | seg. 7 | JF693099,JF693165 |
| Rotavirus A PxUK reassortant (UKg9P) | NC_011502 | vertebrates,human | 3 | Reoviridae,Rotavirus,Rotavirus A | seg. 8 | JF693212,JF693164, JF693098 |
| Rotavirus A PxUK reassortant (UKg9P) | NC_011503 | vertebrates,human | 3 | Reoviridae,Rotavirus,Rotavirus A | seg. 9 | JF693166,JF693213, JF693100 |
| Rotavirus A PxUK reassortant (UKg9P) | NC_011504 | vertebrates,human | 2 | Reoviridae,Rotavirus,Rotavirus A | seg. 10 | JF693101,JF693167 |
| Rotavirus A PxUK reassortant (UKg9P) | NC_011505 | vertebrates,human | 2 | Reoviridae,Rotavirus,Rotavirus A | seg. 11 | JF693102,JF693168 |
| Rotavirus A PxUK reassortant (UKg9P) | NC_011506 | vertebrates,human | 2 | Reoviridae,Rotavirus,Rotavirus A | seg. 2 | JF693159,JF693093 |
| Rotavirus A PxUK reassortant (UKg9P) | NC_011507 | vertebrates,human | 2 | Reoviridae,Rotavirus,Rotavirus A | seg. 1 | JF693092,JF693158 |
| Rotavirus A PxUK reassortant (UKg9P) | NC_011508 | vertebrates,human | 2 | Reoviridae,Rotavirus,Rotavirus A | seg. 3 | JF693094,JF693160 |
| Rotavirus A PxUK reassortant (UKg9P) | NC_011509 | vertebrates,human | 2 | Reoviridae,Rotavirus,Rotavirus A | seg. 6 | JF693097,JF693163 |
| Rotavirus A PxUK reassortant (UKg9P) | NC_011510 | vertebrates,human | 3 | Reoviridae,Rotavirus,Rotavirus A | seg. 4 | JF693095,JF693161, JF693210 |
| Rotavirus A RVA/Human-tc/USA/DS-1/1976/G2P[4] | NC_011500 | vertebrates,human | 1 | Reoviridae,Rotavirus,Rotavirus A | seg. 5 | HQ650120 |
| Rotavirus A RVA/Human-tc/USA/DS-1/1976/G2P[4] | NC_011501 | vertebrates,human | 1 | Reoviridae,Rotavirus,Rotavirus A | seg. 7 | HQ650122 |
| Rotavirus A RVA/Human-tc/USA/DS-1/1976/G2P[4] | NC_011502 | vertebrates,human | 1 | Reoviridae,Rotavirus,Rotavirus A | seg. 8 | HQ650123 |
| Rotavirus A RVA/Human-tc/USA/DS-1/1976/G2P[4] | NC_011503 | vertebrates,human | 1 | Reoviridae,Rotavirus,Rotavirus A | seg. 9 | HQ650124 |
| Rotavirus A RVA/Human-tc/USA/DS-1/1976/G2P[4] | NC_011504 | vertebrates,human | 1 | Reoviridae,Rotavirus,Rotavirus A | seg. 10 | HQ650125 |
| Rotavirus A RVA/Human-tc/USA/DS-1/1976/G2P[4] | NC_011505 | vertebrates,human | 1 | Reoviridae,Rotavirus,Rotavirus A | seg. 11 | HQ650126 |
| Rotavirus A RVA/Human-tc/USA/DS-1/1976/G2P[4] | NC_011506 | vertebrates,human | 1 | Reoviridae,Rotavirus,Rotavirus A | seg. 2 | HQ650117 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rotavirus A RVA/Human-tc/USA/DS-1/1976/G2P[4] | NC_011507 | vertebrates,human | 1 | Reoviridae,Rotavirus,Rotavirus A | seg. 1 | HQ650116 |
| Rotavirus A RVA/Human-tc/USA/DS-1/1976/G2P[4] | NC_011508 | vertebrates,human | 1 | Reoviridae,Rotavirus,Rotavirus A | seg. 3 | HQ650118 |
| Rotavirus A RVA/Human-tc/USA/DS-1/1976/G2P[4] | NC_011509 | vertebrates,human | 1 | Reoviridae,Rotavirus,Rotavirus A | seg. 6 | HQ650121 |
| Rotavirus A RVA/Human-tc/USA/DS-1/1976/G2P[4] | NC_011510 | vertebrates,human | 1 | Reoviridae,Rotavirus,Rotavirus A | seg. 4 | HQ650119 |
| Rotavirus A RVA/Human-wt/ITA/ASTI23/2007/G9P8 | NC_011501 | vertebrates,human | 1 | Reoviridae,Rotavirus,Rotavirus A | seg. 7 | JX185766 |
| Rotavirus A RVA/Human-wt/ITA/ASTI23/2007/G9P8 | NC_011502 | vertebrates,human | 1 | Reoviridae,Rotavirus,Rotavirus A | seg. 8 | JX185765 |
| Rotavirus A RVA/Human-wt/ITA/ASTI23/2007/G9P8 | NC_011503 | vertebrates,human | 1 | Reoviridae,Rotavirus,Rotavirus A | seg. 9 | JX185763 |
| Rotavirus A RVA/Human-wt/ITA/ASTI23/2007/G9P8 | NC_011504 | vertebrates,human | 1 | Reoviridae,Rotavirus,Rotavirus A | seg. 10 | JX185767 |
| Rotavirus A RVA/Human-wt/ITA/ASTI23/2007/G9P8 | NC_011505 | vertebrates,human | 1 | Reoviridae,Rotavirus,Rotavirus A | seg. 11 | JX185768 |
| Rotavirus A RVA/Human-wt/ITA/ASTI23/2007/G9P8 | NC_011506 | vertebrates,human | 1 | Reoviridae,Rotavirus,Rotavirus A | seg. 2 | JX185759 |
| Rotavirus A RVA/Human-wt/ITA/ASTI23/2007/G9P8 | NC_011507 | vertebrates,human | 1 | Reoviridae,Rotavirus,Rotavirus A | seg. 1 | JX185758 |
| Rotavirus A RVA/Human-wt/ITA/ASTI23/2007/G9P8 | NC_011508 | vertebrates,human | 1 | Reoviridae,Rotavirus,Rotavirus A | seg. 3 | JX185760 |
| Rotavirus A RVA/Human-wt/ITA/ASTI23/2007/G9P8 | NC_011509 | vertebrates,human | 1 | Reoviridae,Rotavirus,Rotavirus A | seg. 6 | JX185762 |
| Rotavirus A RVA/Human-wt/ITA/ASTI23/2007/G9P8 | NC_011510 | vertebrates,human | 1 | Reoviridae,Rotavirus,Rotavirus A | seg. 4 | JX185761 |
| Rotavirus A RVA/Human-wt/ITA/AV21/2010/G9P8 | NC_011501 | vertebrates,human | 1 | Reoviridae,Rotavirus,Rotavirus A | seg. 7 | JX195071 |
| Rotavirus A RVA/Human-wt/ITA/AV21/2010/G9P8 | NC_011502 | vertebrates,human | 1 | Reoviridae,Rotavirus,Rotavirus A | seg. 8 | JX195070 |
| Rotavirus A RVA/Human-wt/ITA/AV21/2010/G9P8 | NC_011503 | vertebrates,human | 1 | Reoviridae,Rotavirus,Rotavirus A | seg. 9 | JX195068 |
| Rotavirus A RVA/Human-wt/ITA/AV21/2010/G9P8 | NC_011504 | vertebrates,human | 1 | Reoviridae,Rotavirus,Rotavirus A | seg. 10 | JX195072 |
| Rotavirus A RVA/Human-wt/ITA/AV21/2010/G9P8 | NC_011505 | vertebrates,human | 1 | Reoviridae,Rotavirus,Rotavirus A | seg. 11 | JX195073 |
| Rotavirus A RVA/Human-wt/ITA/AV21/2010/G9P8 | NC_011506 | vertebrates,human | 1 | Reoviridae,Rotavirus,Rotavirus A | seg. 2 | JX195064 |
| Rotavirus A RVA/Human-wt/ITA/AV21/2010/G9P8 | NC_011507 | vertebrates,human | 1 | Reoviridae,Rotavirus,Rotavirus A | seg. 1 | JX195063 |
| Rotavirus A RVA/Human-wt/ITA/AV21/2010/G9P8 | NC_011508 | vertebrates,human | 1 | Reoviridae,Rotavirus,Rotavirus A | seg. 3 | JX195065 |
| Rotavirus A RVA/Human-wt/ITA/AV21/2010/G9P8 | NC_011509 | vertebrates,human | 1 | Reoviridae,Rotavirus,Rotavirus A | seg. 6 | JX195067 |
| Rotavirus A RVA/Human-wt/ITA/AV21/2010/G9P8 | NC_011510 | vertebrates,human | 1 | Reoviridae,Rotavirus,Rotavirus A | seg. 4 | JX195066 |

TABLE 10-continued

| Taxonomy | Rep.Acc.ID | Host | # GN's | ViroCap-1.0 Taxonomy Lineage | Seg. Count | GN.Acc.IDs |
|---|---|---|---|---|---|---|
| Rotavirus A RVA/Human-wt/ITA/AV28/2010/G9P8 | NC_011501 | vertebrates,human | 1 | Reoviridae,Rotavirus,Rotavirus A | seg. 7 | JX195082 |
| Rotavirus A RVA/Human-wt/ITA/AV28/2010/G9P8 | NC_011502 | vertebrates,human | 1 | Reoviridae,Rotavirus,Rotavirus A | seg. 8 | JX195081 |
| Rotavirus A RVA/Human-wt/ITA/AV28/2010/G9P8 | NC_011503 | vertebrates,human | 1 | Reoviridae,Rotavirus,Rotavirus A | seg. 9 | JX195079 |
| Rotavirus A RVA/Human-wt/ITA/AV28/2010/G9P8 | NC_011504 | vertebrates,human | 1 | Reoviridae,Rotavirus,Rotavirus A | seg. 10 | JX195083 |
| Rotavirus A RVA/Human-wt/ITA/AV28/2010/G9P8 | NC_011505 | vertebrates,human | 1 | Reoviridae,Rotavirus,Rotavirus A | seg. 11 | JX195084 |
| Rotavirus A RVA/Human-wt/ITA/AV28/2010/G9P8 | NC_011506 | vertebrates,human | 1 | Reoviridae,Rotavirus,Rotavirus A | seg. 2 | JX195075 |
| Rotavirus A RVA/Human-wt/ITA/AV28/2010/G9P8 | NC_011507 | vertebrates,human | 1 | Reoviridae,Rotavirus,Rotavirus A | seg. 1 | JX195074 |
| Rotavirus A RVA/Human-wt/ITA/AV28/2010/G9P8 | NC_011508 | vertebrates,human | 1 | Reoviridae,Rotavirus,Rotavirus A | seg. 3 | JX195076 |
| Rotavirus A RVA/Human-wt/ITA/AV28/2010/G9P8 | NC_011509 | vertebrates,human | 1 | Reoviridae,Rotavirus,Rotavirus A | seg. 6 | JX195078 |
| Rotavirus A RVA/Human-wt/ITA/AV28/2010/G9P8 | NC_011510 | vertebrates,human | 1 | Reoviridae,Rotavirus,Rotavirus A | seg. 4 | JX195077 |
| Rotavirus A RVA/Human-wt/ITA/JES11/2010/G9P8 | NC_011501 | vertebrates,human | 1 | Reoviridae,Rotavirus,Rotavirus A | seg. 7 | JX195093 |
| Rotavirus A RVA/Human-wt/ITA/JES11/2010/G9P8 | NC_011502 | vertebrates,human | 1 | Reoviridae,Rotavirus,Rotavirus A | seg. 8 | JX195092 |
| Rotavirus A RVA/Human-wt/ITA/JES11/2010/G9P8 | NC_011503 | vertebrates,human | 1 | Reoviridae,Rotavirus,Rotavirus A | seg. 9 | JX195090 |
| Rotavirus A RVA/Human-wt/ITA/JES11/2010/G9P8 | NC_011504 | vertebrates,human | 1 | Reoviridae,Rotavirus,Rotavirus A | seg. 10 | JX195094 |
| Rotavirus A RVA/Human-wt/ITA/JES11/2010/G9P8 | NC_011505 | vertebrates,human | 1 | Reoviridae,Rotavirus,Rotavirus A | seg. 11 | JX195095 |
| Rotavirus A RVA/Human-wt/ITA/JES11/2010/G9P8 | NC_011506 | vertebrates,human | 1 | Reoviridae,Rotavirus,Rotavirus A | seg. 2 | JX195086 |
| Rotavirus A RVA/Human-wt/ITA/JES11/2010/G9P8 | NC_011507 | vertebrates,human | 1 | Reoviridae,Rotavirus,Rotavirus A | seg. 1 | JX195085 |
| Rotavirus A RVA/Human-wt/ITA/JES11/2010/G9P8 | NC_011508 | vertebrates,human | 1 | Reoviridae,Rotavirus,Rotavirus A | seg. 3 | JX195087 |
| Rotavirus A RVA/Human-wt/ITA/JES11/2010/G9P8 | NC_011509 | vertebrates,human | 1 | Reoviridae,Rotavirus,Rotavirus A | seg. 6 | JX195089 |
| Rotavirus A RVA/Human-wt/ITA/JES11/2010/G9P8 | NC_011510 | vertebrates,human | 1 | Reoviridae,Rotavirus,Rotavirus A | seg. 4 | JX195088 |
| Rotavirus A RVA/Human/NCA/125L/20 10/G3P[8] | NC_011500 | vertebrates,human | 1 | Reoviridae,Rotavirus,Rotavirus A | seg. 5 | JN128984 |
| Rotavirus A RVA/Human/NCA/125L/20 10/G3P[8] | NC_011501 | vertebrates,human | 1 | Reoviridae,Rotavirus,Rotavirus A | seg. 7 | JN129012 |

TABLE 10-continued

VifoCap-1.0 Taxonomy

| Taxonomy | Rep.Acc.ID | Host | # GN's | Lineage | Seg. Count | GN.Acc.IDs |
|---|---|---|---|---|---|---|
| Rotavirus A RVA/Human/NCA/125L/20 10/G3P[8] | NC_011502 | vertebrates,human | 1 | Reoviridae,Rotavirus,Rotavirus A | seg. 8 | JN128998 |
| Rotavirus A RVA/Human/NCA/125L/20 10/G3P[8] | NC_011503 | vertebrates,human | 1 | Reoviridae,Rotavirus,Rotavirus A | seg. 9 | JN129124 |
| Rotavirus A RVA/Human/NCA/125L/20 10/G3P[8] | NC_011504 | vertebrates,human | 1 | Reoviridae,Rotavirus,Rotavirus A | seg. 10 | JN129026 |
| Rotavirus A RVA/Human/NCA/125L/20 10/G3P[8] | NC_011505 | vertebrates,human | 1 | Reoviridae,Rotavirus,Rotavirus A | seg. 11 | JN129040 |
| Rotavirus A RVA/Human/NCA/125L/20 10/G3P[8] | NC_011506 | vertebrates,human | 1 | Reoviridae,Rotavirus,Rotavirus A | seg. 2 | JN129068 |
| Rotavirus A RVA/Human/NCA/125L/20 10/G3P[8] | NC_011507 | vertebrates,human | 1 | Reoviridae,Rotavirus,Rotavirus A | seg. 1 | JN129054 |
| Rotavirus A RVA/Human/NCA/125L/20 10/G3P[8] | NC_011508 | vertebrates,human | 1 | Reoviridae,Rotavirus,Rotavirus A | seg. 3 | JN129082 |
| Rotavirus A RVA/Human/NCA/125L/20 10/G3P[8] | NC_011509 | vertebrates,human | 1 | Reoviridae,Rotavirus,Rotavirus A | seg. 6 | JN129110 |
| Rotavirus A RVA/Human/NCA/125L/20 10/G3P[8] | NC_011510 | vertebrates,human | 1 | Reoviridae,Rotavirus,Rotavirus A | seg. 4 | JN129096 |
| Rotavirus A RVA/Human/NCA/18J/201 0/G1P[8] | NC_011500 | vertebrates,human | 1 | Reoviridae,Rotavirus,Rotavirus A | seg. 5 | JN128974 |
| Rotavirus A RVA/Human/NCA/18J/201 0/G1P[8] | NC_011501 | vertebrates,human | 1 | Reoviridae,Rotavirus,Rotavirus A | seg. 7 | JN129002 |
| Rotavirus A RVA/Human/NCA/18J/201 0/G1P[8] | NC_011502 | vertebrates,human | 1 | Reoviridae,Rotavirus,Rotavirus A | seg. 8 | JN128988 |
| Rotavirus A RVA/Human/NCA/18J/201 0/G1P[8] | NC_011503 | vertebrates,human | 1 | Reoviridae,Rotavirus,Rotavirus A | seg. 9 | JN129114 |
| Rotavirus A RVA/Human/NCA/18J/201 0/G1P[8] | NC_011504 | vertebrates,human | 1 | Reoviridae,Rotavirus,Rotavirus A | seg. 10 | JN129016 |
| Rotavirus A RVA/Human/NCA/18J/201 0/G1P[8] | NC_011505 | vertebrates,human | 1 | Reoviridae,Rotavirus,Rotavirus A | seg. 11 | JN129030 |
| Rotavirus A RVA/Human/NCA/18J/201 0/G1P[8] | NC_011506 | vertebrates,human | 1 | Reoviridae,Rotavirus,Rotavirus A | seg. 2 | JN129058 |

TABLE 10-continued

VircCap-1.0 Taxonomy

| Taxonomy | Rep.Acc.ID | Host | Lineage | # GN's | Seg. Count | GN.Acc.IDs |
|---|---|---|---|---|---|---|
| Rotavirus A RVA/Human/NCA/18J/2010/G1P[8] | NC_011507 | vertebrates,human | Reoviridae,Rotavirus,Rotavirus A | 1 | seg. 1 | JN129044 |
| Rotavirus A RVA/Human/NCA/18J/2010/G1P[8] | NC_011508 | vertebrates,human | Reoviridae,Rotavirus,Rotavirus A | 1 | seg. 3 | JN129072 |
| Rotavirus A RVA/Human/NCA/18J/2010/G1P[8] | NC_011509 | vertebrates,human | Reoviridae,Rotavirus,Rotavirus A | 1 | seg. 6 | JN129100 |
| Rotavirus A RVA/Human/NCA/18J/2010/G1P[8] | NC_011510 | vertebrates,human | Reoviridae,Rotavirus,Rotavirus A | 1 | seg. 4 | JN129086 |
| Rotavirus A RVA/Human/NCA/22J/2010/G1P[8] | NC_011500 | vertebrates,human | Reoviridae,Rotavirus,Rotavirus A | 1 | seg. 5 | JN128975 |
| Rotavirus A RVA/Human/NCA/22J/2010/G1P[8] | NC_011501 | vertebrates,human | Reoviridae,Rotavirus,Rotavirus A | 1 | seg. 7 | JN129003 |
| Rotavirus A RVA/Human/NCA/22J/2010/G1P[8] | NC_011502 | vertebrates,human | Reoviridae,Rotavirus,Rotavirus A | 1 | seg. 8 | JN128989 |
| Rotavirus A RVA/Human/NCA/22J/2010/G1P[8] | NC_011503 | vertebrates,human | Reoviridae,Rotavirus,Rotavirus A | 1 | seg. 9 | JN129115 |
| Rotavirus A RVA/Human/NCA/22J/2010/G1P[8] | NC_011504 | vertebrates,human | Reoviridae,Rotavirus,Rotavirus A | 1 | seg. 10 | JN129017 |
| Rotavirus A RVA/Human/NCA/22J/2010/G1P[8] | NC_011505 | vertebrates,human | Reoviridae,Rotavirus,Rotavirus A | 1 | seg. 11 | JN129031 |
| Rotavirus A RVA/Human/NCA/22J/2010/G1P[8] | NC_011506 | vertebrates,human | Reoviridae,Rotavirus,Rotavirus A | 1 | seg. 2 | JN129059 |
| Rotavirus A RVA/Human/NCA/22J/2010/G1P[8] | NC_011507 | vertebrates,human | Reoviridae,Rotavirus,Rotavirus A | 1 | seg. 1 | JN129045 |
| Rotavirus A RVA/Human/NCA/22J/2010/G1P[8] | NC_011508 | vertebrates,human | Reoviridae,Rotavirus,Rotavirus A | 1 | seg. 3 | JN129073 |
| Rotavirus A RVA/Human/NCA/22J/2010/G1P[8] | NC_011509 | vertebrates,human | Reoviridae,Rotavirus,Rotavirus A | 1 | seg. 6 | JN129101 |
| Rotavirus A RVA/Human/NCA/22J/2010/G1P[8] | NC_011510 | vertebrates,human | Reoviridae,Rotavirus,Rotavirus A | 1 | seg. 4 | JN129087 |
| Rotavirus A RVA/Human/NCA/24J/2010/G1P[8] | NC_011500 | vertebrates,human | Reoviridae,Rotavirus,Rotavirus A | 1 | seg. 5 | JN128976 |

TABLE 10-continued

VrioCap-1.0 Taxonomy

| Taxonomy | Rep.Acc.ID | Host | # GN's | Lineage | Seg. Count | GN.Acc.IDs |
|---|---|---|---|---|---|---|
| Rotavirus A RVA/Human/NCA/24J/2010/G1P[8] | NC_011501 | vertebrates,human | 1 | Reoviridae,Rotavirus,Rotavirus A | seg. 7 | JN129004 |
| Rotavirus A RVA/Human/NCA/24J/2010/G1P[8] | NC_011502 | vertebrates,human | 1 | Reoviridae,Rotavirus,Rotavirus A | seg. 8 | JN128990 |
| Rotavirus A RVA/Human/NCA/24J/2010/G1P[8] | NC_011503 | vertebrates,human | 1 | Reoviridae,Rotavirus,Rotavirus A | seg. 9 | JN129116 |
| Rotavirus A RVA/Human/NCA/24J/2010/G1P[8] | NC_011504 | vertebrates,human | 1 | Reoviridae,Rotavirus,Rotavirus A | seg. 10 | JN129018 |
| Rotavirus A RVA/Human/NCA/24J/2010/G1P[8] | NC_011505 | vertebrates,human | 1 | Reoviridae,Rotavirus,Rotavirus A | seg. 11 | JN129032 |
| Rotavirus A RVA/Human/NCA/24J/2010/G1P[8] | NC_011506 | vertebrates,human | 1 | Reoviridae,Rotavirus,Rotavirus A | seg. 2 | JN129060 |
| Rotavirus A RVA/Human/NCA/24J/2010/G1P[8] | NC_011507 | vertebrates,human | 1 | Reoviridae,Rotavirus,Rotavirus A | seg. 1 | JN129046 |
| Rotavirus A RVA/Human/NCA/24J/2010/G1P[8] | NC_011508 | vertebrates,human | 1 | Reoviridae,Rotavirus,Rotavirus A | seg. 3 | JN129074 |
| Rotavirus A RVA/Human/NCA/24J/2010/G1P[8] | NC_011509 | vertebrates,human | 1 | Reoviridae,Rotavirus,Rotavirus A | seg. 6 | JN129102 |
| Rotavirus A RVA/Human/NCA/24J/2010/G1P[8] | NC_011510 | vertebrates,human | 1 | Reoviridae,Rotavirus,Rotavirus A | seg. 4 | JN129088 |
| Rotavirus A RVA/Human/NCA/24J/2010/G1P[8] | NC_011500 | vertebrates,human | 1 | Reoviridae,Rotavirus,Rotavirus A | seg. 5 | JN128977 |
| Rotavirus A RVA/Human/NCA/25J/2010/G1P[8] | NC_011501 | vertebrates,human | 1 | Reoviridae,Rotavirus,Rotavirus A | seg. 7 | JN129005 |
| Rotavirus A RVA/Human/NCA/25J/2010/G1P[8] | NC_011502 | vertebrates,human | 1 | Reoviridae,Rotavirus,Rotavirus A | seg. 8 | JN128991 |
| Rotavirus A RVA/Human/NCA/25J/2010/G1P[8] | NC_011503 | vertebrates,human | 1 | Reoviridae,Rotavirus,Rotavirus A | seg. 9 | JN129117 |
| Rotavirus A RVA/Human/NCA/25J/2010/G1P[8] | NC_011504 | vertebrates,human | 1 | Reoviridae,Rotavirus,Rotavirus A | seg. 10 | JN129019 |
| Rotavirus A RVA/Human/NCA/25J/2010/G1P[8] | NC_011505 | vertebrates,human | 1 | Reoviridae,Rotavirus,Rotavirus A | seg. 11 | JN129033 |

TABLE 10-continued

| Taxonomy | Rep.Acc.ID | Host | # GN's | VirCap-1.0 Taxonomy Lineage | Seg. Count | GN.Acc.IDs |
|---|---|---|---|---|---|---|
| Rotavirus A RVA/Human/NCA/25J/2010/G1P[8] | NC_011506 | vertebrates,human | 1 | Reoviridae,Rotavirus,Rotavirus A | seg. 2 | JN129061 |
| Rotavirus A RVA/Human/NCA/25J/2010/G1P[8] | NC_011507 | vertebrates,human | 1 | Reoviridae,Rotavirus,Rotavirus A | seg. 1 | JN129047 |
| Rotavirus A JN129075 RVA/Human/NCA/25J/2010/G1P[8] | NC_011508 | vertebrates,human | 1 | Reoviridae,Rotavirus,Rotavirus A | seg. 3 | |
| Rotavirus A RVA/Human/NCA/25J/2010/G1P[8] | NC_011509 | vertebrates,human | 1 | Reoviridae,Rotavirus,Rotavirus A | seg. 6 | JN129103 |
| Rotavirus A RVA/Human/NCA/25J/2010/G1P[8] | NC_011510 | vertebrates,human | 1 | Reoviridae,Rotavirus,Rotavirus A | seg. 4 | JN129089 |
| Rotavirus A RVA/Human/NCA/25J/2010/G1P[8] | NC_011500 | vertebrates,human | 1 | Reoviridae,Rotavirus,Rotavirus A | seg. 5 | JN128978 |
| Rotavirus A RVA/Human/NCA/26J/2010/G1P[8] | NC_011501 | vertebrates,human | 1 | Reoviridae,Rotavirus,Rotavirus A | seg. 7 | JN129006 |
| Rotavirus A RVA/Human/NCA/26J/2010/G1P[8] | NC_011502 | vertebrates,human | 1 | Reoviridae,Rotavirus,Rotavirus A | seg. 8 | JN128992 |
| Rotavirus A RVA/Human/NCA/26J/2010/G1P[8] | NC_011503 | vertebrates,human | 1 | Reoviridae,Rotavirus,Rotavirus A | seg. 9 | JN129118 |
| Rotavirus A RVA/Human/NCA/26J/2010/G1P[8] | NC_011504 | vertebrates,human | 1 | Reoviridae,Rotavirus,Rotavirus A | seg. 10 | JN129020 |
| Rotavirus A RVA/Human/NCA/26J/2010/G1P[8] | NC_011505 | vertebrates,human | 1 | Reoviridae,Rotavirus,Rotavirus A | seg. 11 | JN129034 |
| Rotavirus A RVA/Human/NCA/26J/2010/G1P[8] | NC_011506 | vertebrates,human | 1 | Reoviridae,Rotavirus,Rotavirus A | seg. 2 | JN129062 |
| Rotavirus A RVA/Human/NCA/26J/2010/G1P[8] | NC_011507 | vertebrates,human | 1 | Reoviridae,Rotavirus,Rotavirus A | seg. 1 | JN129048 |
| Rotavirus A RVA/Human/NCA/26J/2010/G1P[8] | NC_011508 | vertebrates,human | 1 | Reoviridae,Rotavirus,Rotavirus A | seg. 3 | JN129076 |
| Rotavirus A RVA/Human/NCA/26J/2010/G1P[8] | NC_011509 | vertebrates,human | 1 | Reoviridae,Rotavirus,Rotavirus A | seg. 6 | JN129104 |

TABLE 10-continued

VireCap-1.0 Taxonomy

| Taxonomy | Rep.Acc.ID | Host | Lineage | # GN's | Seg. Count | GN.Acc.IDs |
|---|---|---|---|---|---|---|
| Rotavirus A RVA/Human/NCA/26J/2010/G1P[8] | NC_011510 | vertebrates,human | Reoviridae,Rotavirus,Rotavirus A | 1 | seg. 4 | JN129090 |
| Rotavirus A RVA/Human/NCA/28J/2010/G1P[8] | NC_011500 | vertebrates,human | Reoviridae,Rotavirus,Rotavirus A | 1 | seg. 5 | JN128979 |
| Rotavirus A RVA/Human/NCA/28J/2010/G1P[8] | NC_011501 | vertebrates,human | Reoviridae,Rotavirus,Rotavirus A | 1 | seg. 7 | JN129007 |
| Rotavirus A RVA/Human/NCA/28J/2010/G1P[8] | NC_011502 | vertebrates,human | Reoviridae,Rotavirus,Rotavirus A | 1 | seg. 8 | JN128993 |
| Rotavirus A RVA/Human/NCA/28J/2010/G1P[8] | NC_011503 | vertebrates,human | Reoviridae,Rotavirus,Rotavirus A | 1 | seg. 9 | JN129119 |
| Rotavirus A RVA/Human/NCA/28J/2010/G1P[8] | NC_011504 | vertebrates,human | Reoviridae,Rotavirus,Rotavirus A | 1 | seg. 10 | JN129021 |
| Rotavirus A RVA/Human/NCA/28J/2010/G1P[8] | NC_011505 | vertebrates,human | Reoviridae,Rotavirus,Rotavirus A | 1 | seg. 11 | JN129035 |
| Rotavirus A RVA/Human/NCA/28J/2010/G1P[8] | NC_011506 | vertebrates,human | Reoviridae,Rotavirus,Rotavirus A | 1 | seg. 2 | JN129063 |
| Rotavirus A RVA/Human/NCA/28J/2010/G1P[8] | NC_011507 | vertebrates,human | Reoviridae,Rotavirus,Rotavirus A | 1 | seg. 1 | JN129049 |
| Rotavirus A RVA/Human/NCA/28J/2010/G1P[8] | NC_011508 | vertebrates,human | Reoviridae,Rotavirus,Rotavirus A | 1 | seg. 3 | JN129077 |
| Rotavirus A RVA/Human/NCA/28J/2010/G1P[8] | NC_011509 | vertebrates,human | Reoviridae,Rotavirus,Rotavirus A | 1 | seg. 6 | JN129105 |
| Rotavirus A RVA/Human/NCA/28J/2010/G1P[8] | NC_011510 | vertebrates,human | Reoviridae,Rotavirus,Rotavirus A | 1 | seg. 4 | JN129091 |
| Rotavirus A RVA/Human/NCA/41J/2010/G1P[8] | NC_011500 | vertebrates,human | Reoviridae,Rotavirus,Rotavirus A | 1 | seg. 5 | JN128980 |
| Rotavirus A RVA/Human/NCA/41J/2010/G1P[8] | NC_011501 | vertebrates,human | Reoviridae,Rotavirus,Rotavirus A | 1 | seg. 7 | JN129008 |
| Rotavirus A RVA/Human/NCA/41J/2010/G1P[8] | NC_011502 | vertebrates,human | Reoviridae,Rotavirus,Rotavirus A | 1 | seg. 8 | JN128994 |
| Rotavirus A RVA/Human/NCA/41J/2010/G1P[8] | NC_011503 | vertebrates,human | Reoviridae,Rotavirus,Rotavirus A | 1 | seg. 9 | JN129120 |

TABLE 10-continued

VitoCap-1.0 Taxonomy

| Taxonomy | Rep.Acc.ID | Host | Lineage | # GN's | Seg. Count | GN.Acc.IDs |
|---|---|---|---|---|---|---|
| Rotavirus A RVA/Human/NCA/41J/2010/G1P[8] | NC_011504 | vertebrates,human | Reoviridae,Rotavirus,Rotavirus A | 1 | seg. 10 | JN129022 |
| Rotavirus A RVA/Human/NCA/41J/2010/G1P[8] | NC_011505 | vertebrates,human | Reoviridae,Rotavirus,Rotavirus A | 1 | seg. 11 | JN129036 |
| Rotavirus A RVA/Human/NCA/41J/2010/G1P[8] | NC_011506 | vertebrates,human | Reoviridae,Rotavirus,Rotavirus A | 1 | seg. 2 | JN129064 |
| Rotavirus A RVA/Human/NCA/41J/2010/G1P[8] | NC_011507 | vertebrates,human | Reoviridae,Rotavirus,Rotavirus A | 1 | seg. 1 | JN129050 |
| Rotavirus A RVA/Human/NCA/41J/2010/G1P[8] | NC_011508 | vertebrates,human | Reoviridae,Rotavirus,Rotavirus A | 1 | seg. 3 | JN129078 |
| Rotavirus A RVA/Human/NCA/41J/2010/G1P[8] | NC_011509 | vertebrates,human | Reoviridae,Rotavirus,Rotavirus A | 1 | seg. 6 | JN129106 |
| Rotavirus A RVA/Human/NCA/41J/2010/G1P[8] | NC_011510 | vertebrates,human | Reoviridae,Rotavirus,Rotavirus A | 1 | seg. 4 | JN129092 |
| Rotavirus A RVA/Human/NCA/45J/2010/G1P[8] | NC_011500 | vertebrates,human | Reoviridae,Rotavirus,Rotavirus A | 1 | seg. 5 | JN128981 |
| Rotavirus A RVA/Human/NCA/45J/2010/G1P[8] | NC_011501 | vertebrates,human | Reoviridae,Rotavirus,Rotavirus A | 1 | seg. 7 | JN129009 |
| Rotavirus A RVA/Human/NCA/45J/2010/G1P[8] | NC_011502 | vertebrates,human | Reoviridae,Rotavirus,Rotavirus A | 1 | seg. 8 | JN128995 |
| Rotavirus A RVA/Human/NCA/45J/2010/G1P[8] | NC_011503 | vertebrates,human | Reoviridae,Rotavirus,Rotavirus A | 1 | seg. 9 | JN129121 |
| Rotavirus A RVA/Human/NCA/45J/2010/G1P[8] | NC_011504 | vertebrates,human | Reoviridae,Rotavirus,Rotavirus A | 1 | seg. 10 | JN129023 |
| Rotavirus A RVA/Human/NCA/45J/2010/G1P[8] | NC_011505 | vertebrates,human | Reoviridae,Rotavirus,Rotavirus A | 1 | seg. 11 | JN129037 |
| Rotavirus A RVA/Human/NCA/45J/2010/G1P[8] | NC_011506 | vertebrates,human | Reoviridae,Rotavirus,Rotavirus A | 1 | seg. 2 | JN129065 |
| Rotavirus A RVA/Human/NCA/45J/2010/G1P[8] | NC_011507 | vertebrates,human | Reoviridae,Rotavirus,Rotavirus A | 1 | seg. 1 | JN129051 |
| Rotavirus A RVA/Human/NCA/45J/2010/G1P[8] | NC_011508 | vertebrates,human | Reoviridae,Rotavirus,Rotavirus A | 1 | seg. 3 | JN129079 |

TABLE 10-continued

VíroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A RVA/Human/NCA/45J/2010/G1P[8] | NC_011509 | vertebrates,human | Reoviridae,Rotavirus,Rotavirus A | 1 | seg. 6 | JN129107 |
| Rotavirus A RVA/Human/NCA/45J/2010/G1P[8] | NC_011510 | vertebrates,human | Reoviridae,Rotavirus,Rotavirus A | 1 | seg. 4 | JN129093 |
| Rotavirus A RVA/Human/NCA/64J/2010/G3P[8] | NC_011500 | vertebrates,human | Reoviridae,Rotavirus,Rotavirus A | 1 | seg. 5 | JN128982 |
| Rotavirus A RVA/Human/NCA/64J/2010/G3P[8] | NC_011501 | vertebrates,human | Reoviridae,Rotavirus,Rotavirus A | 1 | seg. 7 | JN129010 |
| Rotavirus A RVA/Human/NCA/64J/2010/G3P[8] | NC_011502 | vertebrates,human | Reoviridae,Rotavirus,Rotavirus A | 1 | seg. 8 | JN128996 |
| Rotavirus A RVA/Human/NCA/64J/2010/G3P[8] | NC_011503 | vertebrates,human | Reoviridae,Rotavirus,Rotavirus A | 1 | seg. 9 | JN129122 |
| Rotavirus A RVA/Human/NCA/64J/2010/G3P[8] | NC_011504 | vertebrates,human | Reoviridae,Rotavirus,Rotavirus A | 1 | seg. 10 | JN129024 |
| Rotavirus A RVA/Human/NCA/64J/2010/G3P[8] | NC_011505 | vertebrates,human | Reoviridae,Rotavirus,Rotavirus A | 1 | seg. 11 | JN129038 |
| Rotavirus A RVA/Human/NCA/64J/2010/G3P[8] | NC_011506 | vertebrates,human | Reoviridae,Rotavirus,Rotavirus A | 1 | seg. 2 | JN129066 |
| Rotavirus A RVA/Human/NCA/64J/2010/G3P[8] | NC_011507 | vertebrates,human | Reoviridae,Rotavirus,Rotavirus A | 1 | seg. 1 | JN129052 |
| Rotavirus A RVA/Human/NCA/64J/2010/G3P[8] | NC_011508 | vertebrates,human | Reoviridae,Rotavirus,Rotavirus A | 1 | seg. 3 | JN129080 |
| Rotavirus A RVA/Human/NCA/64J/2010/G3P[8] | NC_011509 | vertebrates,human | Reoviridae,Rotavirus,Rotavirus A | 1 | seg. 6 | JN129108 |
| Rotavirus A RVA/Human/NCA/64J/2010/G3P[8] | NC_011510 | vertebrates,human | Reoviridae,Rotavirus,Rotavirus A | 1 | seg. 4 | JN129094 |
| Rotavirus A RVA/Human/NCA/72J/2010/G1P[8] | NC_011500 | vertebrates,human | Reoviridae,Rotavirus,Rotavirus A | 1 | seg. 5 | JN128983 |
| Rotavirus A RVA/Human/NCA/72J/2010/G1P[8] | NC_011501 | vertebrates,human | Reoviridae,Rotavirus,Rotavirus A | 1 | seg. 7 | JN129011 |
| Rotavirus A RVA/Human/NCA/72J/2010/G1P[8] | NC_011502 | vertebrates,human | Reoviridae,Rotavirus,Rotavirus A | 1 | seg. 8 | JN128997 |

TABLE 10-continued

| Taxonomy | Rep.Acc.ID | Host | VíroCap-1.0 Taxonomy Lineage | # GN's | Seg. Count | GN.Acc.IDs |
|---|---|---|---|---|---|---|
| Rotavirus A RVA/Human/NCA/72J/2010/G1P[8] | NC_011503 | vertebrates,human | Reoviridae,Rotavirus,Rotavirus A | 1 | seg. 9 | JN129123 |
| Rotavirus A RVA/Human/NCA/72J/2010/G1P[8] | NC_011504 | vertebrates,human | Reoviridae,Rotavirus,Rotavirus A | 1 | seg. 10 | JN129025 |
| Rotavirus A RVA/Human/NCA/72J/2010/G1P[8] | NC_011505 | vertebrates,human | Reoviridae,Rotavirus,Rotavirus A | 1 | seg. 11 | JN129039 |
| Rotavirus A RVA/Human/NCA/72J/2010/G1P[8] | NC_011506 | vertebrates,human | Reoviridae,Rotavirus,Rotavirus A | 1 | seg. 2 | JN129067 |
| Rotavirus A RVA/Human/NCA/72J/2010/G1P[8] | NC_011507 | vertebrates,human | Reoviridae,Rotavirus,Rotavirus A | 1 | seg. 1 | JN129053 |
| Rotavirus A RVA/Human/NCA/72J/2010/G1P[8] | NC_011508 | vertebrates,human | Reoviridae,Rotavirus,Rotavirus A | 1 | seg. 3 | JN129081 |
| Rotavirus A RVA/Human/NCA/72J/2010/G1P[8] | NC_011509 | vertebrates,human | Reoviridae,Rotavirus,Rotavirus A | 1 | seg. 6 | JN129109 |
| Rotavirus A RVA/Human/NCA/72J/2010/G1P[8] | NC_011510 | vertebrates,human | Reoviridae,Rotavirus,Rotavirus A | 1 | seg. 4 | JN129095 |
| Rotavirus A RVA/Human/NCA/72J/2010/G1P[8] | NC_011500 | vertebrates,human | Reoviridae,Rotavirus,Rotavirus A | 1 | seg. 5 | JN128972 |
| Rotavirus A RVA/Human/NCA/7J/2010/G1P[8] | NC_011501 | vertebrates,human | Reoviridae,Rotavirus,Rotavirus A | 1 | seg. 7 | JN129000 |
| Rotavirus A RVA/Human/NCA/7J/2010/G1P[8] | NC_011502 | vertebrates,human | Reoviridae,Rotavirus,Rotavirus A | 1 | seg. 8 | JN128986 |
| Rotavirus A RVA/Human/NCA/7J/2010/G1P[8] | NC_011503 | vertebrates,human | Reoviridae,Rotavirus,Rotavirus A | 1 | seg. 9 | JN129112 |
| Rotavirus A RVA/Human/NCA/7J/2010/G1P[8] | NC_011504 | vertebrates,human | Reoviridae,Rotavirus,Rotavirus A | 1 | seg. 10 | JN129014 |
| Rotavirus A RVA/Human/NCA/7J/2010/G1P[8] | NC_011505 | vertebrates,human | Reoviridae,Rotavirus,Rotavirus A | 2 | seg. 11 | JN129028,JN129042 |
| Rotavirus A RVA/Human/NCA/7J/2010/G1P[8] | NC_011506 | vertebrates,human | Reoviridae,Rotavirus,Rotavirus A | 1 | seg. 2 | JN129056 |
| Rotavirus A RVA/Human/NCA/7J/2010/G1P[8] | NC_011508 | vertebrates,human | Reoviridae,Rotavirus,Rotavirus A | 1 | seg. 3 | JN129070 |

TABLE 10-continued

| Taxonomy | Rep.Acc.ID | Host | # GN's | VIroCap-1.0 Taxonomy Lineage | Seg. Count | GN.Acc.IDs |
|---|---|---|---|---|---|---|
| Rotavirus A RVA/Human/NCA/7J/2010/ G1P[8] | NC_011509 | vertebrates,human | 1 | Reoviridae,Rotavirus,Rotavirus A | seg. 6 | JN129098 |
| Rotavirus A RVA/Human/NCA/7J/2010/ G1P[8] | NC_011510 | vertebrates,human | 1 | Reoviridae,Rotavirus,Rotavirus A | seg. 4 | JN129084 |
| Rotavirus A RVA/Human/NCA/9J/2010/ G1P[8] | NC_011500 | vertebrates,human | 1 | Reoviridae,Rotavirus,Rotavirus A | seg. 5 | JN128973 |
| Rotavirus A RVA/Human/NCA/9J/2010/ G1P[8] | NC_011501 | vertebrates,human | 1 | Reoviridae,Rotavirus,Rotavirus A | seg. 7 | JN129001 |
| Rotavirus A RVA/Human/NCA/9J/2010/ G1P[8] | NC_011502 | vertebrates,human | 1 | Reoviridae,Rotavirus,Rotavirus A | seg. 8 | JN128987 |
| Rotavirus A RVA/Human/NCA/9J/2010/ G1P[8] | NC_011503 | vertebrates,human | 1 | Reoviridae,Rotavirus,Rotavirus A | seg. 9 | JN129113 |
| Rotavirus A RVA/Human/NCA/9J/2010/ G1P[8] | NC_011504 | vertebrates,human | 1 | Reoviridae,Rotavirus,Rotavirus A | seg. 10 | JN129015 |
| Rotavirus A RVA/Human/NCA/9J/2010/ G1P[8] | NC_011505 | vertebrates,human | 1 | Reoviridae,Rotavirus,Rotavirus A | seg. 11 | JN129029 |
| Rotavirus A RVA/Human/NCA/9J/2010/ G1P[8] | NC_011506 | vertebrates,human | 1 | Reoviridae,Rotavirus,Rotavirus A | seg. 2 | JN129057 |
| Rotavirus A RVA/Human/NCA/9J/2010/ G1P[8] | NC_011507 | vertebrates,human | 1 | Reoviridae,Rotavirus,Rotavirus A | seg. 1 | JN129043 |
| Rotavirus A RVA/Human/NCA/9J/2010/ G1P[8] | NC_011508 | vertebrates,human | 1 | Reoviridae,Rotavirus,Rotavirus A | seg. 3 | JN129071 |
| Rotavirus A RVA/Human/NCA/9J/2010/ G1P[8] | NC_011509 | vertebrates,human | 1 | Reoviridae,Rotavirus,Rotavirus A | seg. 6 | JN129099 |
| Rotavirus A RVA/Human/NCA/9J/2010/ G1P[8] | NC_011510 | vertebrates,human | 1 | Reoviridae,Rotavirus,Rotavirus A | seg. 4 | JN129085 |
| Rotavirus A RVA/Human/NCA/0U2010/ G4P[6] | NC_011500 | vertebrates,human | 1 | Reoviridae,Rotavirus,Rotavirus A | seg. 5 | JN128985 |
| Rotavirus A RVA/Human/NCA/0U2010/ G4P[6] | NC_011501 | vertebrates,human | 1 | Reoviridae,Rotavirus,Rotavirus A | seg. 7 | JN129013 |
| Rotavirus A RVA/Human/NCA/0U2010/ G4P[6] | NC_011502 | vertebrates,human | 1 | Reoviridae,Rotavirus,Rotavirus A | seg. 8 | JN128999 |

TABLE 10-continued

| Taxonomy | Rep.Acc.ID | Host | # GN's | ViroCap-1.0 Taxonomy Lineage | Seg. Count | GN.Acc.IDs |
|---|---|---|---|---|---|---|
| Rotavirus A RVA/Human/NCA/0U2010/G4P[6] | NC_011503 | vertebrates,human | 1 | Reoviridae,Rotavirus,Rotavirus A | seg. 9 | JN129125 |
| Rotavirus A RVA/Human/NCA/0U2010/G4P[6] | NC_011504 | vertebrates,human | 1 | Reoviridae,Rotavirus,Rotavirus A | seg. 10 | JN129027 |
| Rotavirus A RVA/Human/NCA/0U2010/G4P[6] | NC_011505 | vertebrates,human | 1 | Reoviridae,Rotavirus,Rotavirus A | seg. 11 | JN129041 |
| Rotavirus A RVA/Human/NCA/0U2010/G4P[6] | NC_011506 | vertebrates,human | 1 | Reoviridae,Rotavirus,Rotavirus A | seg. 2 | JN129069 |
| Rotavirus A RVA/Human/NCA/0U2010/G4P[6] | NC_011507 | vertebrates,human | 1 | Reoviridae,Rotavirus,Rotavirus A | seg. 1 | JN129055 |
| Rotavirus A RVA/Human/NCA/0U2010/G4P[6] | NC_011508 | vertebrates,human | 1 | Reoviridae,Rotavirus,Rotavirus A | seg. 3 | JN129083 |
| Rotavirus A RVA/Human/NCA/0U2010/G4P[6] | NC_011509 | vertebrates,human | 1 | Reoviridae,Rotavirus,Rotavirus A | seg. 6 | JN129111 |
| Rotavirus A RVA/Human/NCA/0U2010/G4P[6] | NC_011510 | vertebrates,human | 1 | Reoviridae,Rotavirus,Rotavirus A | seg. 4 | JN129097 |
| Rotavirus A ST3xUK reassortant (UKg9ST3) | NC_011500 | vertebrates,human | 3 | Reoviridae,Rotavirus,Rotavirus A | seg. 5 | JF693215,JF693107,JF693173 |
| Rotavirus A ST3xUK reassortant (UKg9ST3) | NC_011501 | vertebrates,human | 2 | Reoviridae,Rotavirus,Rotavirus A | seg. 7 | JF693176,JF693110 |
| Rotavirus A ST3xUK reassortant (UKg9ST3) | NC_011502 | vertebrates,human | 3 | Reoviridae,Rotavirus,Rotavirus A | seg. 8 | JF693109,JF693175,JF693216 |
| Rotavirus A ST3xUK reassortant (UKg9ST3) | NC_011503 | vertebrates,human | 3 | Reoviridae,Rotavirus,Rotavirus A | seg. 9 | JF693217,JF693111,JF693177 |
| Rotavirus A ST3xUK reassortant (UKg9ST3) | NC_011504 | vertebrates,human | 2 | Reoviridae,Rotavirus,Rotavirus A | seg. 10 | JF693112,JF693178 |
| Rotavirus A ST3xUK reassortant (UKg9ST3) | NC_011505 | vertebrates,human | 2 | Reoviridae,Rotavirus,Rotavirus A | seg. 11 | JF693113,JF693179 |
| Rotavirus A ST3xUK reassortant (UKg9ST3) | NC_011506 | vertebrates,human | 2 | Reoviridae,Rotavirus,Rotavirus A | seg. 2 | JF693104,JF693170 |
| Rotavirus A ST3xUK reassortant (UKg9ST3) | NC_011507 | vertebrates,human | 2 | Reoviridae,Rotavirus,Rotavirus A | seg. 1 | JF693169,JF693103 |
| Rotavirus A ST3xUK reassortant (UKg9ST3) | NC_011508 | vertebrates,human | 2 | Reoviridae,Rotavirus,Rotavirus A | seg. 3 | JF693171,JF693105 |
| Rotavirus A ST3xUK reassortant (UKg9ST3) | NC_011509 | vertebrates,human | 2 | Reoviridae,Rotavirus,Rotavirus A | seg. 6 | JF693174,JF693108 |
| Rotavirus A ST3xUK reassortant (UKg9ST3) | NC_011510 | vertebrates,human | 3 | Reoviridae,Rotavirus,Rotavirus A | seg. 4 | JF693214,JF693106,JF693172 |
| Rotavirus A UK WT BR-3 | NC_011506 | vertebrates,human | 1 | Reoviridae,Rotavirus,Rotavirus A | seg. 2 | JF990806 |
| Rotavirus A UK WT BR-3 | NC_011507 | vertebrates,human | 1 | Reoviridae,Rotavirus,Rotavirus A | seg. 1 | JF990805 |

TABLE 10-continued

VirоCap-1.0 Taxonomy

| Taxonomy | Rep.Acc.ID | Host | # GN's | Lineage | Seg. Count | GN.Acc.IDs |
|---|---|---|---|---|---|---|
| Rotavirus A UK WT BR-3 | NC_011508 | vertebrates,human | 1 | Reoviridae,Rotavirus,Rotavirus A | seg. 3 | JF990807 |
| Rotavirus A WaxUK reassortant (UKg4Wa) | NC_011506 | vertebrates,human | 1 | Reoviridae,Rotavirus,Rotavirus A | seg. 2 | JF990829 |
| Rotavirus A WaxUK reassortant (UKg4Wa) | NC_011507 | vertebrates,human | 1 | Reoviridae,Rotavirus,Rotavirus A | seg. 1 | JF990828 |
| Rotavirus A WaxUK reassortant (UKg4Wa) | NC_011508 | vertebrates,human | 1 | Reoviridae,Rotavirus,Rotavirus A | seg. 3 | JF990830 |
| Rotavirus A bovine/Arg/B383/1998 | NC_011501 | vertebrates,human | 1 | Reoviridae,Rotavirus,Rotavirus A | seg. 7 | FJ347119 |
| Rotavirus A bovine/Arg/B383/1998 | NC_011502 | vertebrates,human | 1 | Reoviridae,Rotavirus,Rotavirus A | seg. 8 | FJ347118 |
| Rotavirus A bovine/Arg/B383/1998 | NC_011503 | vertebrates,human | 1 | Reoviridae,Rotavirus,Rotavirus A | seg. 9 | FJ347116 |
| Rotavirus A bovine/Arg/B383/1998 | NC_011504 | vertebrates,human | 1 | Reoviridae,Rotavirus,Rotavirus A | seg. 10 | FJ347120 |
| Rotavirus A bovine/Arg/B383/1998 | NC_011505 | vertebrates,human | 1 | Reoviridae,Rotavirus,Rotavirus A | seg. 11 | FJ347121 |
| Rotavirus A bovine/Arg/B383/1998 | NC_011506 | vertebrates,human | 1 | Reoviridae,Rotavirus,Rotavirus A | seg. 2 | FJ347112 |
| Rotavirus A bovine/Arg/B383/1998 | NC_011507 | vertebrates,human | 1 | Reoviridae,Rotavirus,Rotavirus A | seg. 1 | FJ347111 |
| Rotavirus A bovine/Arg/B383/1998 | NC_011508 | vertebrates,human | 1 | Reoviridae,Rotavirus,Rotavirus A | seg. 3 | FJ347113 |
| Rotavirus A bovine/Arg/B383/1998 | NC_011509 | vertebrates,human | 1 | Reoviridae,Rotavirus,Rotavirus A | seg. 6 | FJ347115 |
| Rotavirus A bovine/B223/G10 | NC_011504 | vertebrates,human | 1 | Reoviridae,Rotavirus,Rotavirus A | seg. 10 | AF144805 |
| Rotavirus A guanaco/Arg/Chubut/1999 | NC_011501 | vertebrates,human | 1 | Reoviridae,Rotavirus,Rotavirus A | seg. 7 | FJ347108 |
| Rotavirus A guanaco/Arg/Chubut/1999 | NC_011502 | vertebrates,human | 1 | Reoviridae,Rotavirus,Rotavirus A | seg. 8 | FJ347107 |
| Rotavirus A guanaco/Arg/Chubut/1999 | NC_011503 | vertebrates,human | 1 | Reoviridae,Rotavirus,Rotavirus A | seg. 9 | FJ347105 |
| Rotavirus A guanaco/Arg/Chubut/1999 | NC_011504 | vertebrates,human | 1 | Reoviridae,Rotavirus,Rotavirus A | seg. 1 | FJ347109 |
| Rotavirus A guanaco/Arg/Chubut/1999 | NC_011505 | vertebrates,human | 1 | Reoviridae,Rotavirus,Rotavirus A | seg. 10 | FJ347110 |
| Rotavirus A guanaco/Arg/Chubut/1999 | NC_011506 | vertebrates,human | 1 | Reoviridae,Rotavirus,Rotavirus A | seg. 11 | FJ347101 |
| Rotavirus A guanaco/Arg/Chubut/1999 | NC_011507 | vertebrates,human | 1 | Reoviridae,Rotavirus,Rotavirus A | seg. 2 | FJ347100 |
| Rotavirus A guanaco/Arg/Chubut/1999 | NC_011508 | vertebrates,human | 1 | Reoviridae,Rotavirus,Rotavirus A | seg. 3 | FJ347102 |
| Rotavirus A guanaco/Arg/Chubut/1999 | NC_011509 | vertebrates,human | 1 | Reoviridae,Rotavirus,Rotavirus A | seg. 6 | FJ347104 |
| Rotavirus A guanaco/Arg/Chubut/1999 | NC_011510 | vertebrates,human | 1 | Reoviridae,Rotavirus,Rotavirus A | seg. 4 | FJ347103 |

TABLE 10-continued

VireCap-1.0 Taxonomy

| Taxonomy | Rep.Acc.ID | Host | # GN's | Lineage | Seg. Count | GN.Acc.IDs |
|---|---|---|---|---|---|---|
| Rotavirus A guanaco/Arg/Rio Negro/1998 | NC_011501 | vertebrates,human | 1 | Reoviridae,Rotavirus,Rotavirus A | seg. 7 | FJ347130 |
| Rotavirus A guanaco/Arg/Rio Negro/1998 | NC_011502 | vertebrates,human | 1 | Reoviridae,Rotavirus,Rotavirus A | seg. 8 | FJ347129 |
| Rotavirus A guanaco/Arg/Rio Negro/1998 | NC_011503 | vertebrates,human | 1 | Reoviridae,Rotavirus,Rotavirus A | seg. 9 | FJ347127 |
| Rotavirus A guanaco/Arg/Rio Negro/1998 | NC_011504 | vertebrates,human | 1 | Reoviridae,Rotavirus,Rotavirus A | seg. 10 | FJ347131 |
| Rotavirus A guanaco/Arg/Rio Negro/1998 | NC_011505 | vertebrates,human | 1 | Reoviridae,Rotavirus,Rotavirus A | seg. 11 | FJ347132 |
| Rotavirus A guanaco/Arg/Rio Negro/1998 | NC_011506 | vertebrates,human | 1 | Reoviridae,Rotavirus,Rotavirus A | seg. 2 | FJ347123 |
| Rotavirus A guanaco/Arg/Rio Negro/1998 | NC_011507 | vertebrates,human | 1 | Reoviridae,Rotavirus,Rotavirus A | seg. 1 | FJ347122 |
| Rotavirus A guanaco/Arg/Rio Negro/1998 | NC_011508 | vertebrates,human | 1 | Reoviridae,Rotavirus,Rotavirus A | seg. 3 | FJ347124 |
| Rotavirus A guanaco/Arg/Rio Negro/1998 | NC_011509 | vertebrates,human | 1 | Reoviridae,Rotavirus,Rotavirus A | seg. 6 | FJ347126 |
| Rotavirus A guanaco/Arg/Rio Negro/1998 | NC_011510 | vertebrates,human | 1 | Reoviridae,Rotavirus,Rotavirus A | seg. 4 | FJ347125 |
| Rotavirus A human-wt/USA/LB1562/2010/G9P4 | NC_011503 | vertebrates,human | 1 | Reoviridae,Rotavirus,Rotavirus A | seg. 9 | KC782524 |
| Rotavirus A human-wt/USA/LB1562/2010/G9P4 | NC_011506 | vertebrates,human | 1 | Reoviridae,Rotavirus,Rotavirus A | seg. 2 | KC782520 |
| Rotavirus A human-wt/USA/LB1562/2010/G9P4 | NC_011507 | vertebrates,human | 1 | Reoviridae,Rotavirus,Rotavirus A | seg. 1 | KC782519 |
| Rotavirus A human-wt/USA/LB1562/2010/G9P4 | NC_011508 | vertebrates,human | 1 | Reoviridae,Rotavirus,Rotavirus A | seg. 3 | KC782521 |
| Rotavirus A human/Bethesda/CH5446/1991/G3P[8] | NC_011500 | vertebrates,human | 1 | Reoviridae,Rotavirus,Rotavirus A | seg. 5 | FJ947432 |
| Rotavirus A human/Bethesda/CH5446/1991/G3P[8] | NC_011501 | vertebrates,human | 1 | Reoviridae,Rotavirus,Rotavirus A | seg. 7 | FJ947434 |

TABLE 10-continued

| Taxonomy | Rep.Acc.ID | Host | VirоCap-1.0 Taxonomy Lineage | # GN's | Seg. Count | GN.Acc.IDs |
|---|---|---|---|---|---|---|
| Rotavirus A human/Bethesda/CH5446/1991/G3P[8] | NC_011502 | vertebrates,human | Reoviridae,Rotavirus,Rotavirus A | 1 | seg. 8 | FJ947435 |
| Rotavirus A human/Bethesda/CH5446/1991/G3P[8] | NC_011504 | vertebrates,human | Reoviridae,Rotavirus,Rotavirus A | 1 | seg. 10 | FJ947437 |
| Rotavirus A human/Bethesda/CH5446/1991/G3P[8] | NC_011505 | vertebrates,human | Reoviridae,Rotavirus,Rotavirus A | 1 | seg. 11 | FJ947438 |
| Rotavirus A human/Bethesda/CH5446/1991/G3P[8] | NC_011506 | vertebrates,human | Reoviridae,Rotavirus,Rotavirus A | 1 | seg. 2 | FJ947429 |
| Rotavirus A human/Bethesda/CH5446/1991/G3P[8] | NC_011508 | vertebrates,human | Reoviridae,Rotavirus,Rotavirus A | 1 | seg. 3 | FJ947430 |
| Rotavirus A human/Bethesda/CH5446/1991/G3P[8] | NC_011509 | vertebrates,human | Reoviridae,Rotavirus,Rotavirus A | 1 | seg. 6 | FJ947433 |
| Rotavirus A human/Bethesda/CH5446/1991/G3P[8] | NC_011510 | vertebrates,human | Reoviridae,Rotavirus,Rotavirus A | 1 | seg. 4 | FJ947431 |
| Rotavirus A human/Bethesda/CH5455/1991/G3P[8] | NC_011500 | vertebrates,human | Reoviridae,Rotavirus,Rotavirus A | 1 | seg. 5 | FJ947896 |
| Rotavirus A human/Bethesda/CH5455/1991/G3P[8] | NC_011501 | vertebrates,human | Reoviridae,Rotavirus,Rotavirus A | 1 | seg. 7 | FJ947898 |
| Rotavirus A human/Bethesda/CH5455/1991/G3P[8] | NC_011502 | vertebrates,human | Reoviridae,Rotavirus,Rotavirus A | 1 | seg. 8 | FJ947899 |
| Rotavirus A human/Bethesda/CH5455/1991/G3P[8] | NC_011504 | vertebrates,human | Reoviridae,Rotavirus,Rotavirus A | 1 | seg. 10 | FJ947901 |
| Rotavirus A human/Bethesda/CH5455/1991/G3P[8] | NC_011505 | vertebrates,human | Reoviridae,Rotavirus,Rotavirus A | 1 | seg. 11 | FJ947902 |
| Rotavirus A human/Bethesda/CH5455/1991/G3P[8] | NC_011506 | vertebrates,human | Reoviridae,Rotavirus,Rotavirus A | 1 | seg. 2 | FJ947893 |
| Rotavirus A human/Bethesda/CH5455/1991/G3P[8] | NC_011508 | vertebrates,human | Reoviridae,Rotavirus,Rotavirus A | 1 | seg. 3 | FJ947894 |
| Rotavirus A human/Bethesda/CH5455/1991/G3P[8] | NC_011509 | vertebrates,human | Reoviridae,Rotavirus,Rotavirus A | 1 | seg. 6 | FJ947897 |
| Rotavirus A human/Bethesda/CH5455/1991/G3P[8] | NC_011510 | vertebrates,human | Reoviridae,Rotavirus,Rotavirus A | 1 | seg. 4 | FJ947895 |

TABLE 10-continued

| Taxonomy | Rep.Acc.ID | Host | VircoCap-1.0 Taxonomy Lineage | # GN's | Seg. Count | GN.Acc.IDs |
|---|---|---|---|---|---|---|
| Rotavirus A human/Bethesda/CH5459/ 1991/G3P[8] | NC_011500 | vertebrates,human | Reoviridae,Rotavirus,Rotavirus A | 1 | seg. 5 | FJ947443 |
| Rotavirus A human/Bethesda/CH5459/ 1991/G3P[8] | NC_011501 | vertebrates,human | Reoviridae,Rotavirus,Rotavirus A | 1 | seg. 7 | FJ947445 |
| Rotavirus A human/Bethesda/CH5459/ 1991/G3P[8] | NC_011502 | vertebrates,human | Reoviridae,Rotavirus,Rotavirus A | 1 | seg. 8 | FJ947446 |
| Rotavirus A human/Bethesda/CH5459/ 1991/G3P[8] | NC_011504 | vertebrates,human | Reoviridae,Rotavirus,Rotavirus A | 1 | seg. 10 | FJ947448 |
| Rotavirus A human/Bethesda/CH5459/ 1991/G3P[8] | NC_011505 | vertebrates,human | Reoviridae,Rotavirus,Rotavirus A | 1 | seg. 11 | FJ947449 |
| Rotavirus A human/Bethesda/CH5459/ 1991/G3P[8] | NC_011508 | vertebrates,human | Reoviridae,Rotavirus,Rotavirus A | 1 | seg. 3 | FJ947441 |
| Rotavirus A human/Bethesda/CH5459/ 1991/G3P[8] | NC_011509 | vertebrates,human | Reoviridae,Rotavirus,Rotavirus A | 1 | seg. 4 | FJ947444 |
| Rotavirus A human/Bethesda/CH5459/ 1991/G3P[8] | NC_011510 | vertebrates,human | Reoviridae,Rotavirus,Rotavirus A | 1 | seg. 7 | FJ947442 |
| Rotavirus A human/Bethesda/CH5470/ 1991/G3P[8] | NC_011501 | vertebrates,human | Reoviridae,Rotavirus,Rotavirus A | 1 | seg. 8 | FJ947909 |
| Rotavirus A human/Bethesda/CH5470/ 1991/G3P[8] | NC_011502 | vertebrates,human | Reoviridae,Rotavirus,Rotavirus A | 1 | seg. 10 | FJ947910 |
| Rotavirus A human/Bethesda/CH5470/ 1991/G3P[8] | NC_011504 | vertebrates,human | Reoviridae,Rotavirus,Rotavirus A | 1 | seg. 11 | FJ947912 |
| Rotavirus A human/Bethesda/CH5470/ 1991/G3P[8] | NC_011505 | vertebrates,human | Reoviridae,Rotavirus,Rotavirus A | 1 | seg. 3 | FJ947913 |
| Rotavirus A human/Bethesda/CH5470/ 1991/G3P[8] | NC_011508 | vertebrates,human | Reoviridae,Rotavirus,Rotavirus A | 1 | seg. 6 | FJ947905 |
| Rotavirus A human/Bethesda/CH5470/ 1991/G3P[8] | NC_011509 | vertebrates,human | Reoviridae,Rotavirus,Rotavirus A | 1 | seg. 4 | FJ947908 |
| Rotavirus A human/Bethesda/CH5470/ 1991/G3P[8] | NC_011510 | vertebrates,human | Reoviridae,Rotavirus,Rotavirus A | 1 | seg. 5 | FJ947906 |
| Rotavirus A human/Bethesda/CH5475/ 1991/G3P[8] | NC_011500 | vertebrates,human | Reoviridae,Rotavirus,Rotavirus A | 1 |  | FJ947454 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/CH5475/ 1991/G3P[8] | NC_011501 | vertebrates,human | Reoviridae,Rotavirus,Rotavirus A | 1 | seg. 7 | FJ947456 |
| Rotavirus A human/Bethesda/CH5475/ 1991/G3P[8] | NC_011502 | vertebrates,human | Reoviridae,Rotavirus,Rotavirus A | 1 | seg. 8 | FJ947457 |
| Rotavirus A human/Bethesda/CH5475/ 1991/G3P[8] | NC_011504 | vertebrates,human | Reoviridae,Rotavirus,Rotavirus A | 1 | seg. 10 | FJ947459 |
| Rotavirus A human/Bethesda/CH5475/ 1991/G3P[8] | NC_011505 | vertebrates,human | Reoviridae,Rotavirus,Rotavirus A | 1 | seg. 11 | FJ947460 |
| Rotavirus A human/Bethesda/CH5475/ 1991/G3P[8] | NC_011508 | vertebrates,human | Reoviridae,Rotavirus,Rotavirus A | 1 | seg. 3 | FJ947452 |
| Rotavirus A human/Bethesda/CH5475/ 1991/G3P[8] | NC_011509 | vertebrates,human | Reoviridae,Rotavirus,Rotavirus A | 1 | seg. 6 | FJ947455 |
| Rotavirus A human/Bethesda/CH5475/ 1991/G3P[8] | NC_011510 | vertebrates,human | Reoviridae,Rotavirus,Rotavirus A | 1 | seg. 4 | FJ947453 |
| Rotavirus A human/Bethesda/CH5477/ 1991/G3P[8] | NC_011501 | vertebrates,human | Reoviridae,Rotavirus,Rotavirus A | 1 | seg. 7 | FJ947467 |
| Rotavirus A human/Bethesda/CH5477/ 1991/G3P[8] | NC_011502 | vertebrates,human | Reoviridae,Rotavirus,Rotavirus A | 1 | seg. 8 | FJ947468 |
| Rotavirus A human/Bethesda/CH5477/ 1991/G3P[8] | NC_011504 | vertebrates,human | Reoviridae,Rotavirus,Rotavirus A | 1 | seg. 10 | FJ947470 |
| Rotavirus A human/Bethesda/CH5477/ 1991/G3P[8] | NC_011505 | vertebrates,human | Reoviridae,Rotavirus,Rotavirus A | 1 | seg. 11 | FJ947471 |
| Rotavirus A human/Bethesda/CH5477/ 1991/G3P[8] | NC_011506 | vertebrates,human | Reoviridae,Rotavirus,Rotavirus A | 1 | seg. 2 | FJ947462 |
| Rotavirus A human/Bethesda/CH5477/ 1991/G3P[8] | NC_011508 | vertebrates,human | Reoviridae,Rotavirus,Rotavirus A | 1 | seg. 3 | FJ947463 |
| Rotavirus A human/Bethesda/CH5477/ 1991/G3P[8] | NC_011509 | vertebrates,human | Reoviridae,Rotavirus,Rotavirus A | 1 | seg. 6 | FJ947466 |
| Rotavirus A human/Bethesda/CH5477/ 1991/G3P[8] | NC_011510 | vertebrates,human | Reoviridae,Rotavirus,Rotavirus A | 1 | seg. 4 | FJ947464 |
| Rotavirus A human/Bethesda/CH5483/ 1991/G3P[8] | NC_011501 | vertebrates,human | Reoviridae,Rotavirus,Rotavirus A | 1 | seg. 7 | FJ947920 |

TABLE 10-continued

| Taxonomy | Rep.Acc.ID | Host | Lineage | # GN's | Seg. Count | GN.Acc.IDs |
|---|---|---|---|---|---|---|
| Rotavirus A human/Bethesda/CH5483/ 1991/G3P[8] | NC_011502 | vertebrates,human | Reoviridae,Rotavirus,Rotavirus A | 1 | seg. 8 | FJ947921 |
| Rotavirus A human/Bethesda/CH5483/ 1991/G3P[8] | NC_011504 | vertebrates,human | Reoviridae,Rotavirus,Rotavirus A | 1 | seg. 10 | FJ947923 |
| Rotavirus A human/Bethesda/CH5483/ 1991/G3P[8] | NC_011505 | vertebrates,human | Reoviridae,Rotavirus,Rotavirus A | 1 | seg. 11 | FJ947924 |
| Rotavirus A human/Bethesda/CH5483/ 1991/G3P[8] | NC_011508 | vertebrates,human | Reoviridae,Rotavirus,Rotavirus A | 1 | seg. 3 | FJ947916 |
| Rotavirus A human/Bethesda/CH5483/ 1991/G3P[8] | NC_011509 | vertebrates,human | Reoviridae,Rotavirus,Rotavirus A | 1 | seg. 6 | FJ947919 |
| Rotavirus A human/Bethesda/CH5483/ 1991/G3P[8] | NC_011510 | vertebrates,human | Reoviridae,Rotavirus,Rotavirus A | 1 | seg. 4 | FJ947917 |
| Rotavirus A human/Bethesda/CH5484/ 1991/G3P[8] | NC_011500 | vertebrates,human | Reoviridae,Rotavirus,Rotavirus A | 1 | seg. 5 | FJ947476 |
| Rotavirus A human/Bethesda/CH5484/ 1991/G3P[8] | NC_011501 | vertebrates,human | Reoviridae,Rotavirus,Rotavirus A | 1 | seg. 7 | FJ947478 |
| Rotavirus A human/Bethesda/CH5484/ 1991/G3P[8] | NC_011502 | vertebrates,human | Reoviridae,Rotavirus,Rotavirus A | 1 | seg. 8 | FJ947479 |
| Rotavirus A human/Bethesda/CH5484/ 1991/G3P[8] | NC_011504 | vertebrates,human | Reoviridae,Rotavirus,Rotavirus A | 1 | seg. 10 | FJ947481 |
| Rotavirus A human/Bethesda/CH5484/ 1991/G3P[8] | NC_011505 | vertebrates,human | Reoviridae,Rotavirus,Rotavirus A | 1 | seg. 11 | FJ947482 |
| Rotavirus A human/Bethesda/CH5484/ 1991/G3P[8] | NC_011508 | vertebrates,human | Reoviridae,Rotavirus,Rotavirus A | 1 | seg. 3 | FJ947474 |
| Rotavirus A human/Bethesda/CH5484/ 1991/G3P[8] | NC_011509 | vertebrates,human | Reoviridae,Rotavirus,Rotavirus A | 1 | seg. 6 | FJ947477 |
| Rotavirus A human/Bethesda/CH5484/ 1991/G3P[8] | NC_011510 | vertebrates,human | Reoviridae,Rotavirus,Rotavirus A | 1 | seg. 4 | FJ947475 |
| Rotavirus A human/Bethesda/CH5488/ 1991/G3P[8] | NC_011500 | vertebrates,human | Reoviridae,Rotavirus,Rotavirus A | 1 | seg. 5 | FJ947487 |
| Rotavirus A human/Bethesda/CH5488/ 1991/G3P[8] | NC_011501 | vertebrates,human | Reoviridae,Rotavirus,Rotavirus A | 1 | seg. 7 | FJ947489 |

TABLE 10-continued

| Taxonomy | Rep.Acc.ID | Host | VíroCap-1.0 Taxonomy ||| Seg. Count | GN.Acc.IDs |
| --- | --- | --- | --- | --- | --- | --- | --- |
| | | | # GN's | Lineage | | | |
| Rotavirus A human/Bethesda/CH5488/ 1991/G3P[8] | NC_011502 | vertebrates,human | 1 | Reoviridae,Rotavirus,Rotavirus A | seg. 8 | FJ947490 |
| Rotavirus A human/Bethesda/CH5488/ 1991/G3P[8] | NC_011504 | vertebrates,human | 1 | Reoviridae,Rotavirus,Rotavirus A | seg. 10 | FJ947492 |
| Rotavirus A human/Bethesda/CH5488/ 1991/G3P[8] | NC_011505 | vertebrates,human | 1 | Reoviridae,Rotavirus,Rotavirus A | seg. 11 | FJ947493 |
| Rotavirus A human/Bethesda/CH5488/ 1991/G3P[8] | NC_011508 | vertebrates,human | 1 | Reoviridae,Rotavirus,Rotavirus A | seg. 3 | FJ947485 |
| Rotavirus A human/Bethesda/CH5488/ 1991/G3P[8] | NC_011509 | vertebrates,human | 1 | Reoviridae,Rotavirus,Rotavirus A | seg. 6 | FJ947488 |
| Rotavirus A human/Bethesda/CH5488/ 1991/G3P[8] | NC_011510 | vertebrates,human | 1 | Reoviridae,Rotavirus,Rotavirus A | seg. 4 | FJ947486 |
| Rotavirus A human/Bethesda/CH5498/ 1991/G3P[8] | NC_011501 | vertebrates,human | 1 | Reoviridae,Rotavirus,Rotavirus A | seg. 7 | FJ947931 |
| Rotavirus A human/Bethesda/CH5498/ 1991/G3P[8] | NC_011502 | vertebrates,human | 1 | Reoviridae,Rotavirus,Rotavirus A | seg. 8 | FJ947932 |
| Rotavirus A human/Bethesda/CH5498/ 1991/G3P[8] | NC_011504 | vertebrates,human | 1 | Reoviridae,Rotavirus,Rotavirus A | seg. 10 | FJ947934 |
| Rotavirus A human/Bethesda/CH5498/ 1991/G3P[8] | NC_011505 | vertebrates,human | 1 | Reoviridae,Rotavirus,Rotavirus A | seg. 11 | FJ947935 |
| Rotavirus A human/Bethesda/CH5498/ 1991/G3P[8] | NC_011506 | vertebrates,human | 1 | Reoviridae,Rotavirus,Rotavirus A | seg. 2 | FJ947926 |
| Rotavirus A human/Bethesda/CH5498/ 1991/G3P[8] | NC_011508 | vertebrates,human | 1 | Reoviridae,Rotavirus,Rotavirus A | seg. 3 | FJ947927 |
| Rotavirus A human/Bethesda/CH5498/ 1991/G3P[8] | NC_011509 | vertebrates,human | 1 | Reoviridae,Rotavirus,Rotavirus A | seg. 6 | FJ947930 |
| Rotavirus A human/Bethesda/CH5498/ 1991/G3P[8] | NC_011510 | vertebrates,human | 1 | Reoviridae,Rotavirus,Rotavirus A | seg. 4 | FJ947928 |
| Rotavirus A human/Bethesda/DC1208/ 1980/G4P[8] | NC_011500 | vertebrates,human | 1 | Reoviridae,Rotavirus,Rotavirus A | seg. 5 | HM773858 |
| Rotavirus A human/Bethesda/DC1208/ 1980/G4P[8] | NC_011501 | vertebrates,human | 1 | Reoviridae,Rotavirus,Rotavirus A | seg. 7 | HM773860 |

TABLE 10-continued

VioCap-1.0 Taxonomy

| Taxonomy | Rep.Acc.ID | Host | # GN's | Lineage | Seg. Count | GN.Acc.IDs |
|---|---|---|---|---|---|---|
| Rotavirus A human/Bethesda/DC1208/1980/G4P[8] | NC_011502 | vertebrates,human | 1 | Reoviridae,Rotavirus,Rotavirus A | seg. 8 | HM773861 |
| Rotavirus A human/Bethesda/DC1208/1980/G4P[8] | NC_011503 | vertebrates,human | 1 | Reoviridae,Rotavirus,Rotavirus A | seg. 9 | HM773862 |
| Rotavirus A human/Bethesda/DC1208/1980/G4P[8] | NC_011504 | vertebrates,human | 1 | Reoviridae,Rotavirus,Rotavirus A | seg. 10 | HM773863 |
| Rotavirus A human/Bethesda/DC1208/1980/G4P[8] | NC_011505 | vertebrates,human | 1 | Reoviridae,Rotavirus,Rotavirus A | seg. 11 | HM773864 |
| Rotavirus A human/Bethesda/DC1208/1980/G4P[8] | NC_011506 | vertebrates,human | 1 | Reoviridae,Rotavirus,Rotavirus A | seg. 2 | HM773855 |
| Rotavirus A human/Bethesda/DC1208/1980/G4P[8] | NC_011507 | vertebrates,human | 1 | Reoviridae,Rotavirus,Rotavirus A | seg. 1 | HM773854 |
| Rotavirus A human/Bethesda/DC1208/1980/G4P[8] | NC_011508 | vertebrates,human | 1 | Reoviridae,Rotavirus,Rotavirus A | seg. 3 | HM773856 |
| Rotavirus A human/Bethesda/DC1208/1980/G4P[8] | NC_011509 | vertebrates,human | 1 | Reoviridae,Rotavirus,Rotavirus A | seg. 6 | HM773859 |
| Rotavirus A human/Bethesda/DC1208/1980/G4P[8] | NC_011510 | vertebrates,human | 1 | Reoviridae,Rotavirus,Rotavirus A | seg. 4 | HM773857 |
| Rotavirus A human/Bethesda/DC1285/1980/G4P[8] | NC_011500 | vertebrates,human | 1 | Reoviridae,Rotavirus,Rotavirus A | seg. 5 | FJ947168 |
| Rotavirus A human/Bethesda/DC1285/1980/G4P[8] | NC_011501 | vertebrates,human | 1 | Reoviridae,Rotavirus,Rotavirus A | seg. 7 | FJ947170 |
| Rotavirus A human/Bethesda/DC1285/1980/G4P[8] | NC_011502 | vertebrates,human | 1 | Reoviridae,Rotavirus,Rotavirus A | seg. 8 | FJ947171 |
| Rotavirus A human/Bethesda/DC1285/1980/G4P[8] | NC_011503 | vertebrates,human | 1 | Reoviridae,Rotavirus,Rotavirus A | seg. 9 | FJ947172 |
| Rotavirus A human/Bethesda/DC1285/1980/G4P[8] | NC_011504 | vertebrates,human | 1 | Reoviridae,Rotavirus,Rotavirus A | seg. 10 | FJ947173 |
| Rotavirus A human/Bethesda/DC1285/1980/G4P[8] | NC_011505 | vertebrates,human | 1 | Reoviridae,Rotavirus,Rotavirus A | seg. 11 | FJ947174 |
| Rotavirus A human/Bethesda/DC1285/1980/G4P[8] | NC_011506 | vertebrates,human | 1 | Reoviridae,Rotavirus,Rotavirus A | seg. 2 | FJ947165 |

TABLE 10-continued

| Taxonomy | Rep.Acc.ID | Host | VicCap-1.0 Taxonomy | | Seg. Count | GN.Acc.IDs |
|---|---|---|---|---|---|---|
| | | | # GN's | Lineage | | |
| Rotavirus A human/Bethesda/DC1285/ 1980/G4P[8] | NC_011507 | vertebrates,human | 1 | Reoviridae,Rotavirus,Rotavirus A | seg. 1 | FJ947164 |
| Rotavirus A human/Bethesda/DC1285/ 1980/G4P[8] | NC_011508 | vertebrates,human | 1 | Reoviridae,Rotavirus,Rotavirus A | seg. 3 | FJ947166 |
| Rotavirus A human/Bethesda/DC1285/ 1980/G4P[8] | NC_011509 | vertebrates,human | 1 | Reoviridae,Rotavirus,Rotavirus A | seg. 6 | FJ947169 |
| Rotavirus A human/Bethesda/DC1285/ 1980/G4P[8] | NC_011510 | vertebrates,human | 1 | Reoviridae,Rotavirus,Rotavirus A | seg. 4 | FJ947167 |
| Rotavirus A human/Bethesda/DC129/1 976/G3P[8] | NC_011500 | vertebrates,human | 1 | Reoviridae,Rotavirus,Rotavirus A | seg. 5 | FJ947234 |
| Rotavirus A human/Bethesda/DC129/1 976/G3P[8] | NC_011501 | vertebrates,human | 1 | Reoviridae,Rotavirus,Rotavirus A | seg. 7 | FJ947236 |
| Rotavirus A human/Bethesda/DC129/1 976/G3P[8] | NC_011502 | vertebrates,human | 1 | Reoviridae,Rotavirus,Rotavirus A | seg. 8 | FJ947237 |
| Rotavirus A human/Bethesda/DC129/1 976/G3P[8] | NC_011504 | vertebrates,human | 1 | Reoviridae,Rotavirus,Rotavirus A | seg. 10 | FJ947239 |
| Rotavirus A human/Bethesda/DC129/1 976/G3P[8] | NC_011505 | vertebrates,human | 1 | Reoviridae,Rotavirus,Rotavirus A | seg. 11 | FJ947240 |
| Rotavirus A human/Bethesda/DC129/1 976/G3P[8] | NC_011506 | vertebrates,human | 1 | Reoviridae,Rotavirus,Rotavirus A | seg. 2 | FJ947231 |
| Rotavirus A human/Bethesda/DC129/1 976/G3P[8] | NC_011508 | vertebrates,human | 1 | Reoviridae,Rotavirus,Rotavirus A | seg. 3 | FJ947232 |
| Rotavirus A human/Bethesda/DC129/1 976/G3P[8] | NC_011509 | vertebrates,human | 1 | Reoviridae,Rotavirus,Rotavirus A | seg. 6 | FJ947235 |
| Rotavirus A human/Bethesda/DC129/1 976/G3P[8] | NC_011510 | vertebrates,human | 1 | Reoviridae,Rotavirus,Rotavirus A | seg. 4 | FJ947233 |
| Rotavirus A human/Bethesda/DC130/1 976/G3P[8] | NC_011500 | vertebrates,human | 1 | Reoviridae,Rotavirus,Rotavirus A | seg. 5 | FJ947245 |
| Rotavirus A human/Bethesda/DC130/1 976/G3P[8] | NC_011501 | vertebrates,human | 1 | Reoviridae,Rotavirus,Rotavirus A | seg. 7 | FJ947247 |
| Rotavirus A human/Bethesda/DC130/1 976/G3P[8] | NC_011502 | vertebrates,human | 1 | Reoviridae,Rotavirus,Rotavirus A | seg. 8 | FJ947248 |

TABLE 10-continued

VIroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC130/1 976/G3P[8] | NC_011504 | vertebrates,human | Reoviridae,Rotavirus,Rotavirus A | 1 | seg. 10 | FJ947250 |
| Rotavirus A human/Bethesda/DC130/1 976/G3P[8] | NC_011505 | vertebrates,human | Reoviridae,Rotavirus,Rotavirus A | 1 | seg. 11 | FJ947251 |
| Rotavirus A human/Bethesda/DC130/1 976/G3P[8] | NC_011506 | vertebrates,human | Reoviridae,Rotavirus,Rotavirus A | 1 | seg. 2 | FJ947242 |
| Rotavirus A human/Bethesda/DC130/1 976/G3P[8] | NC_011508 | vertebrates,human | Reoviridae,Rotavirus,Rotavirus A | 1 | seg. 3 | FJ947243 |
| Rotavirus A human/Bethesda/DC130/1 976/G3P[8] | NC_011509 | vertebrates,human | Reoviridae,Rotavirus,Rotavirus A | 1 | seg. 6 | FJ947246 |
| Rotavirus A human/Bethesda/DC130/1 976/G3P[8] | NC_011510 | vertebrates,human | Reoviridae,Rotavirus,Rotavirus A | 1 | seg. 4 | FJ947244 |
| Rotavirus A human/Bethesda/DC131/1 976/G3P[8] | NC_011500 | vertebrates,human | Reoviridae,Rotavirus,Rotavirus A | 1 | seg. 5 | FJ947256 |
| Rotavirus A human/Bethesda/DC131/1 976/G3P[8] | NC_011501 | vertebrates,human | Reoviridae,Rotavirus,Rotavirus A | 1 | seg. 7 | FJ947258 |
| Rotavirus A human/Bethesda/DC131/1 976/G3P[8] | NC_011502 | vertebrates,human | Reoviridae,Rotavirus,Rotavirus A | 1 | seg. 8 | FJ947259 |
| Rotavirus A human/Bethesda/DC131/1 976/G3P[8] | NC_011503 | vertebrates,human | Reoviridae,Rotavirus,Rotavirus A | 1 | seg. 9 | FJ947260 |
| Rotavirus A human/Bethesda/DC131/1 976/G3P[8] | NC_011504 | vertebrates,human | Reoviridae,Rotavirus,Rotavirus A | 1 | seg. 10 | FJ947261 |
| Rotavirus A human/Bethesda/DC131/1 976/G3P[8] | NC_011505 | vertebrates,human | Reoviridae,Rotavirus,Rotavirus A | 1 | seg. 11 | FJ947262 |
| Rotavirus A human/Bethesda/DC131/1 976/G3P[8] | NC_011508 | vertebrates,human | Reoviridae,Rotavirus,Rotavirus A | 1 | seg. 3 | FJ947254 |
| Rotavirus A human/Bethesda/DC131/1 976/G3P[8] | NC_011509 | vertebrates,human | Reoviridae,Rotavirus,Rotavirus A | 1 | seg. 6 | FJ947257 |
| Rotavirus A human/Bethesda/DC131/1 976/G3P[8] | NC_011510 | vertebrates,human | Reoviridae,Rotavirus,Rotavirus A | 1 | seg. 4 | FJ947255 |
| Rotavirus A human/Bethesda/DC133/1 976/G3P[8] | NC_011500 | vertebrates,human | Reoviridae,Rotavirus,Rotavirus A | 1 | seg. 5 | FJ947267 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC133/1 976/G3P[8] | NC_011501 | vertebrates,human | Reoviridae,Rotavirus,Rotavirus A | 1 | seg. 7 | FJ947269 |
| Rotavirus A human/Bethesda/DC133/1 976/G3P[8] | NC_011502 | vertebrates,human | Reoviridae,Rotavirus,Rotavirus A | 1 | seg. 8 | FJ947270 |
| Rotavirus A human/Bethesda/DC133/1 976/G3P[8] | NC_011504 | vertebrates,human | Reoviridae,Rotavirus,Rotavirus A | 1 | seg. 10 | FJ947272 |
| Rotavirus A human/Bethesda/DC133/1 976/G3P[8] | NC_011505 | vertebrates,human | Reoviridae,Rotavirus,Rotavirus A | 1 | seg. 11 | FJ947273 |
| Rotavirus A human/Bethesda/DC133/1 976/G3P[8] | NC_011506 | vertebrates,human | Reoviridae,Rotavirus,Rotavirus A | 1 | seg. 2 | FJ947264 |
| Rotavirus A human/Bethesda/DC133/1 976/G3P[8] | NC_011508 | vertebrates,human | Reoviridae,Rotavirus,Rotavirus A | 1 | seg. 3 | FJ947265 |
| Rotavirus A human/Bethesda/DC133/1 976/G3P[8] | NC_011509 | vertebrates,human | Reoviridae,Rotavirus,Rotavirus A | 1 | seg. 6 | FJ947268 |
| Rotavirus A human/Bethesda/DC133/1 976/G3P[8] | NC_011510 | vertebrates,human | Reoviridae,Rotavirus,Rotavirus A | 1 | seg. 4 | FJ947266 |
| Rotavirus A human/Bethesda/DC135/1 979/G3P[8] | NC_011501 | vertebrates,human | Reoviridae,Rotavirus,Rotavirus A | 1 | seg. 7 | FJ947311 |
| Rotavirus A human/Bethesda/DC135/1 979/G3P[8] | NC_011502 | vertebrates,human | Reoviridae,Rotavirus,Rotavirus A | 1 | seg. 8 | FJ947313 |
| Rotavirus A human/Bethesda/DC135/1 979/G3P[8] | NC_011504 | vertebrates,human | Reoviridae,Rotavirus,Rotavirus A | 1 | seg. 10 | FJ947314 |
| Rotavirus A human/Bethesda/DC135/1 979/G3P[8] | NC_011505 | vertebrates,human | Reoviridae,Rotavirus,Rotavirus A | 1 | seg. 11 | FJ947316 |
| Rotavirus A human/Bethesda/DC135/1 979/G3P[8] | NC_011506 | vertebrates,human | Reoviridae,Rotavirus,Rotavirus A | 1 | seg. 2 | FJ947317 |
| Rotavirus A human/Bethesda/DC135/1 979/G3P[8] | NC_011509 | vertebrates,human | Reoviridae,Rotavirus,Rotavirus A | 1 | seg. 6 | FJ947308 |
| Rotavirus A human/Bethesda/DC135/1 979/G3P[8] | NC_011510 | vertebrates,human | Reoviridae,Rotavirus,Rotavirus A | 1 | seg. 4 | FJ947312 |
| | | | | | | FJ947310 |

TABLE 10-continued

| Taxonomy | Rep.Acc.ID | Host | VirCap-1.0 Taxonomy Lineage | # GN's | Seg. Count | GN.Acc.IDs |
|---|---|---|---|---|---|---|
| Rotavirus A human/Bethesda/DC1359/ 1980/G4P[8] | NC_011500 | vertebrates,human | Reoviridae,Rotavirus,Rotavirus A | 1 | seg. 5 | HM773869 |
| Rotavirus A human/Bethesda/DC1359/ 1980/G4P[8] | NC_011501 | vertebrates,human | Reoviridae,Rotavirus,Rotavirus A | 1 | seg. 7 | HM773871 |
| Rotavirus A human/Bethesda/DC1359/ 1980/G4P[8] | NC_011502 | vertebrates,human | Reoviridae,Rotavirus,Rotavirus A | 1 | seg. 8 | HM773872 |
| Rotavirus A human/Bethesda/DC1359/ 1980/G4P[8] | NC_011503 | vertebrates,human | Reoviridae,Rotavirus,Rotavirus A | 1 | seg. 9 | HM773873 |
| Rotavirus A human/Bethesda/DC1359/ 1980/G4P[8] | NC_011504 | vertebrates,human | Reoviridae,Rotavirus,Rotavirus A | 1 | seg. 10 | HM773874 |
| Rotavirus A human/Bethesda/DC1359/ 1980/G4P[8] | NC_011505 | vertebrates,human | Reoviridae,Rotavirus,Rotavirus A | 1 | seg. 11 | HM773875 |
| Rotavirus A human/Bethesda/DC1359/ 1980/G4P[8] | NC_011506 | vertebrates,human | Reoviridae,Rotavirus,Rotavirus A | 1 | seg. 2 | HM773866 |
| Rotavirus A human/Bethesda/DC1359/ 1980/G4P[8] | NC_011507 | vertebrates,human | Reoviridae,Rotavirus,Rotavirus A | 1 | seg. 1 | HM773865 |
| Rotavirus A human/Bethesda/DC1359/ 1980/G4P[8] | NC_011508 | vertebrates,human | Reoviridae,Rotavirus,Rotavirus A | 1 | seg. 3 | HM773867 |
| Rotavirus A human/Bethesda/DC1359/ 1980/G4P[8] | NC_011509 | vertebrates,human | Reoviridae,Rotavirus,Rotavirus A | 1 | seg. 6 | HM773870 |
| Rotavirus A human/Bethesda/DC1359/ 1980/G4P[8] | NC_011510 | vertebrates,human | Reoviridae,Rotavirus,Rotavirus A | 1 | seg. 4 | HM773868 |
| Rotavirus A human/Bethesda/DC139/1 976/G3P[8] | NC_011500 | vertebrates,human | Reoviridae,Rotavirus,Rotavirus A | 1 | seg. 5 | FJ947223 |
| Rotavirus A human/Bethesda/DC139/1 976/G3P[8] | NC_011501 | vertebrates,human | Reoviridae,Rotavirus,Rotavirus A | 1 | seg. 7 | FJ947225 |
| Rotavirus A human/Bethesda/DC139/1 976/G3P[8] | NC_011502 | vertebrates,human | Reoviridae,Rotavirus,Rotavirus A | 1 | seg. 8 | FJ947226 |
| Rotavirus A human/Bethesda/DC139/1 976/G3P[8] | NC_011504 | vertebrates,human | Reoviridae,Rotavirus,Rotavirus A | 1 | seg. 10 | FJ947228 |
| Rotavirus A human/Bethesda/DC139/1 976/G3P[8] | NC_011505 | vertebrates,human | Reoviridae,Rotavirus,Rotavirus A | 1 | seg. 11 | FJ947229 |

TABLE 10-continued

VíroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC139/1976/G3P[8] | NC_011506 | vertebrates,human | Reoviridae,Rotavirus,Rotavirus A | 1 | seg. 2 | FJ947220 |
| Rotavirus A human/Bethesda/DC139/1976/G3P[8] | NC_011508 | vertebrates,human | Reoviridae,Rotavirus,Rotavirus A | 1 | seg. 3 | FJ947221 |
| Rotavirus A human/Bethesda/DC139/1976/G3P[8] | NC_011509 | vertebrates,human | Reoviridae,Rotavirus,Rotavirus A | 1 | seg. 6 | FJ947224 |
| Rotavirus A human/Bethesda/DC139/1976/G3P[8] | NC_011510 | vertebrates,human | Reoviridae,Rotavirus,Rotavirus A | 1 | seg. 4 | FJ947222 |
| Rotavirus A human/Bethesda/DC140/1975/G3P[8] | NC_011500 | vertebrates,human | Reoviridae,Rotavirus,Rotavirus A | 1 | seg. 5 | FJ947742 |
| Rotavirus A human/Bethesda/DC140/1975/G3P[8] | NC_011501 | vertebrates,human | Reoviridae,Rotavirus,Rotavirus A | 1 | seg. 7 | FJ947744 |
| Rotavirus A human/Bethesda/DC140/1975/G3P[8] | NC_011502 | vertebrates,human | Reoviridae,Rotavirus,Rotavirus A | 1 | seg. 8 | FJ947745 |
| Rotavirus A human/Bethesda/DC140/1975/G3P[8] | NC_011503 | vertebrates,human | Reoviridae,Rotavirus,Rotavirus A | 1 | seg. 9 | FJ947746 |
| Rotavirus A human/Bethesda/DC140/1975/G3P[8] | NC_011504 | vertebrates,human | Reoviridae,Rotavirus,Rotavirus A | 1 | seg. 10 | FJ947747 |
| Rotavirus A human/Bethesda/DC140/1975/G3P[8] | NC_011505 | vertebrates,human | Reoviridae,Rotavirus,Rotavirus A | 1 | seg. 11 | FJ947748 |
| Rotavirus A human/Bethesda/DC140/1975/G3P[8] | NC_011507 | vertebrates,human | Reoviridae,Rotavirus,Rotavirus A | 1 | seg. 1 | FJ947738 |
| Rotavirus A human/Bethesda/DC140/1975/G3P[8] | NC_011508 | vertebrates,human | Reoviridae,Rotavirus,Rotavirus A | 1 | seg. 3 | FJ947740 |
| Rotavirus A human/Bethesda/DC140/1975/G3P[8] | NC_011510 | vertebrates,human | Reoviridae,Rotavirus,Rotavirus A | 1 | seg. 4 | FJ947741 |
| Rotavirus A human/Bethesda/DC1455/1975/G3P[8] | NC_011500 | vertebrates,human | Reoviridae,Rotavirus,Rotavirus A | 1 | seg. 5 | FJ947190 |
| Rotavirus A human/Bethesda/DC1455/1975/G3P[8] | NC_011501 | vertebrates,human | Reoviridae,Rotavirus,Rotavirus A | 1 | seg. 7 | FJ947192 |
| Rotavirus A human/Bethesda/DC1455/1975/G3P[8] | NC_011502 | vertebrates,human | Reoviridae,Rotavirus,Rotavirus A | 1 | seg. 8 | FJ947193 |

TABLE 10-continued

VirCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC1455/1975/G3P[8] | NC_011504 | vertebrates,human | Reoviridae,Rotavirus,Rotavirus A | 1 | seg. 10 | FJ947195 |
| Rotavirus A human/Bethesda/DC1455/1975/G3P[8] | NC_011505 | vertebrates,human | Reoviridae,Rotavirus,Rotavirus A | 1 | seg. 11 | FJ947196 |
| Rotavirus A human/Bethesda/DC1455/1975/G3P[8] | NC_011506 | vertebrates,human | Reoviridae,Rotavirus,Rotavirus A | 1 | seg. 2 | FJ947187 |
| Rotavirus A human/Bethesda/DC1455/1975/G3P[8] | NC_011507 | vertebrates,human | Reoviridae,Rotavirus,Rotavirus A | 1 | seg. 1 | FJ947186 |
| Rotavirus A human/Bethesda/DC1455/1975/G3P[8] | NC_011508 | vertebrates,human | Reoviridae,Rotavirus,Rotavirus A | 1 | seg. 3 | FJ947188 |
| Rotavirus A human/Bethesda/DC1455/1975/G3P[8] | NC_011509 | vertebrates,human | Reoviridae,Rotavirus,Rotavirus A | 1 | seg. 6 | FJ947191 |
| Rotavirus A human/Bethesda/DC1455/1975/G3P[8] | NC_011510 | vertebrates,human | Reoviridae,Rotavirus,Rotavirus A | 1 | seg. 4 | FJ947189 |
| Rotavirus A human/Bethesda/DC1494/1976/G3P[8] | NC_011500 | vertebrates,human | Reoviridae,Rotavirus,Rotavirus A | 1 | seg. 5 | FJ947278 |
| Rotavirus A human/Bethesda/DC1494/1976/G3P[8] | NC_011501 | vertebrates,human | Reoviridae,Rotavirus,Rotavirus A | 1 | seg. 7 | FJ947280 |
| Rotavirus A human/Bethesda/DC1494/1976/G3P[8] | NC_011502 | vertebrates,human | Reoviridae,Rotavirus,Rotavirus A | 1 | seg. 8 | FJ947281 |
| Rotavirus A human/Bethesda/DC1494/1976/G3P[8] | NC_011504 | vertebrates,human | Reoviridae,Rotavirus,Rotavirus A | 1 | seg. 10 | FJ947283 |
| Rotavirus A human/Bethesda/DC1494/1976/G3P[8] | NC_011505 | vertebrates,human | Reoviridae,Rotavirus,Rotavirus A | 1 | seg. 11 | FJ947284 |
| Rotavirus A human/Bethesda/DC1494/1976/G3P[8] | NC_011506 | vertebrates,human | Reoviridae,Rotavirus,Rotavirus A | 1 | seg. 2 | FJ947275 |
| Rotavirus A human/Bethesda/DC1494/1976/G3P[8] | NC_011508 | vertebrates,human | Reoviridae,Rotavirus,Rotavirus A | 1 | seg. 3 | FJ947276 |
| Rotavirus A human/Bethesda/DC1494/1976/G3P[8] | NC_011509 | vertebrates,human | Reoviridae,Rotavirus,Rotavirus A | 1 | seg. 6 | FJ947279 |
| Rotavirus A human/Bethesda/DC1494/1976/G3P[8] | NC_011510 | vertebrates,human | Reoviridae,Rotavirus,Rotavirus A | 1 | seg. 4 | FJ947277 |

TABLE 10-continued

| Taxonomy | Rep.Acc.ID | Host | VicroCap-1.0 Taxonomy | | Seg. Count | GN.Acc.IDs |
| --- | --- | --- | --- | --- | --- | --- |
| | | | # GN's | Lineage | | |
| Rotavirus A human/Bethesda/DC1496/ 1976/G3P[8] | NC_011500 | vertebrates,human | 1 | Reoviridae,Rotavirus,Rotavirus A | seg. 5 | FJ947289 |
| Rotavirus A human/Bethesda/DC1496/ 1976/G3P[8] | NC_011501 | vertebrates,human | 1 | Reoviridae,Rotavirus,Rotavirus A | seg. 7 | FJ947291 |
| Rotavirus A human/Bethesda/DC1496/ 1976/G3P[8] | NC_011502 | vertebrates,human | 1 | Reoviridae,Rotavirus,Rotavirus A | seg. 8 | FJ947292 |
| Rotavirus A human/Bethesda/DC1496/ 1976/G3P[8] | NC_011504 | vertebrates,human | 1 | Reoviridae,Rotavirus,Rotavirus A | seg. 10 | FJ947294 |
| Rotavirus A human/Bethesda/DC1496/ 1976/G3P[8] | NC_011505 | vertebrates,human | 1 | Reoviridae,Rotavirus,Rotavirus A | seg. 11 | FJ947295 |
| Rotavirus A human/Bethesda/DC1496/ 1976/G3P[8] | NC_011506 | vertebrates,human | 1 | Reoviridae,Rotavirus,Rotavirus A | seg. 2 | FJ947286 |
| Rotavirus A human/Bethesda/DC1496/ 1976/G3P[8] | NC_011508 | vertebrates,human | 1 | Reoviridae,Rotavirus,Rotavirus A | seg. 3 | FJ947287 |
| Rotavirus A human/Bethesda/DC1496/ 1976/G3P[8] | NC_011509 | vertebrates,human | 1 | Reoviridae,Rotavirus,Rotavirus A | seg. 6 | FJ947290 |
| Rotavirus A human/Bethesda/DC1496/ 1976/G3P[8] | NC_011510 | vertebrates,human | 1 | Reoviridae,Rotavirus,Rotavirus A | seg. 4 | FJ947288 |
| Rotavirus A human/Bethesda/DC1497/ 1976/G3P[8] | NC_011500 | vertebrates,human | 1 | Reoviridae,Rotavirus,Rotavirus A | seg. 5 | FJ947344 |
| Rotavirus A human/Bethesda/DC1497/ 1976/G3P[8] | NC_011501 | vertebrates,human | 1 | Reoviridae,Rotavirus,Rotavirus A | seg. 7 | FJ947346 |
| Rotavirus A human/Bethesda/DC1497/ 1976/G3P[8] | NC_011502 | vertebrates,human | 1 | Reoviridae,Rotavirus,Rotavirus A | seg. 8 | FJ947347 |
| Rotavirus A human/Bethesda/DC1497/ 1976/G3P[8] | NC_011504 | vertebrates,human | 1 | Reoviridae,Rotavirus,Rotavirus A | seg. 10 | FJ947349 |
| Rotavirus A human/Bethesda/DC1497/ 1976/G3P[8] | NC_011505 | vertebrates,human | 1 | Reoviridae,Rotavirus,Rotavirus A | seg. 11 | FJ947350 |
| Rotavirus A human/Bethesda/DC1497/ 1976/G3P[8] | NC_011507 | vertebrates,human | 1 | Reoviridae,Rotavirus,Rotavirus A | seg. 1 | FJ947340 |
| Rotavirus A human/Bethesda/DC1497/ 1976/G3P[8] | NC_011508 | vertebrates,human | 1 | Reoviridae,Rotavirus,Rotavirus A | seg. 3 | FJ947342 |

TABLE 10-continued

| Taxonomy | Rep.Acc.ID | Host | VoroCap-1.0 Taxonomy | | # GN's | Seg. Count | GN.Acc.IDs |
| --- | --- | --- | --- | --- | --- | --- | --- |
| | | | Lineage | | | | |
| Rotavirus A human/Bethesda/DC1497/ 1976/G3P[8] | NC_011509 | vertebrates,human | Reoviridae,Rotavirus,Rotavirus A | | 1 | seg. 6 | F TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Rotavirus A human/Bethesda/DC1563/ 1974/G3P[8] | NC_011506 | vertebrates,human | Reoviridae,Rotavirus,Rotavirus A | 1 | seg. 2 | FJ947176 |
| Rotavirus A human/Bethesda/DC1563/ 1974/G3P[8] | NC_011508 | vertebrates,human | Reoviridae,Rotavirus,Rotavirus A | 1 | seg. 3 | FJ947177 |
| Rotavirus A human/Bethesda/DC1563/ 1974/G3P[8] | NC_011509 | vertebrates,human | Reoviridae,Rotavirus,Rotavirus A | 1 | seg. 6 | FJ947180 |
| Rotavirus A human/Bethesda/DC1563/ 1974/G3P[8] | NC_011510 | vertebrates,human | Reoviridae,Rotavirus,Rotavirus A | 1 | seg. 4 | FJ947178 |
| Rotavirus A human/Bethesda/DC1600/ 1980/G3P[8] | NC_011500 | vertebrates,human | Reoviridae,Rotavirus,Rotavirus A | 1 | seg. 5 | FJ947775 |
| Rotavirus A human/Bethesda/DC1600/ 1980/G3P[8] | NC_011501 | vertebrates,human | Reoviridae,Rotavirus,Rotavirus A | 1 | seg. 7 | FJ947777 |
| Rotavirus A human/Bethesda/DC1600/ 1980/G3P[8] | NC_011502 | vertebrates,human | Reoviridae,Rotavirus,Rotavirus A | 1 | seg. 8 | FJ947778 |
| Rotavirus A human/Bethesda/DC1600/ 1980/G3P[8] | NC_011504 | vertebrates,human | Reoviridae,Rotavirus,Rotavirus A | 1 | seg. 10 | FJ947780 |
| Rotavirus A human/Bethesda/DC1600/ 1980/G3P[8] | NC_011505 | vertebrates,human | Reoviridae,Rotavirus,Rotavirus A | 1 | seg. 11 | FJ947781 |
| Rotavirus A human/Bethesda/DC1600/ 1980/G3P[8] | NC_011506 | vertebrates,human | Reoviridae,Rotavirus,Rotavirus A | 1 | seg. 2 | FJ947772 |
| Rotavirus A human/Bethesda/DC1600/ 1980/G3P[8] | NC_011507 | vertebrates,human | Reoviridae,Rotavirus,Rotavirus A | 1 | seg. 1 | FJ947771 |
| Rotavirus A human/Bethesda/DC1600/ 1980/G3P[8] | NC_011508 | vertebrates,human | Reoviridae,Rotavirus,Rotavirus A | 1 | seg. 3 | FJ947773 |
| Rotavirus A human/Bethesda/DC1600/ 1980/G3P[8] | NC_011509 | vertebrates,human | Reoviridae,Rotavirus,Rotavirus A | 1 | seg. 6 | FJ947776 |
| Rotavirus A human/Bethesda/DC1600/ 1980/G3P[8] | NC_011510 | vertebrates,human | Reoviridae,Rotavirus,Rotavirus A | 1 | seg. 4 | FJ947774 |
| Rotavirus A human/Bethesda/DC168/1 976/G3P[8] | NC_011500 | vertebrates,human | Reoviridae,Rotavirus,Rotavirus A | 1 | seg. 5 | FJ947753 |
| Rotavirus A human/Bethesda/DC168/1 976/G3P[8] | NC_011501 | vertebrates,human | Reoviridae,Rotavirus,Rotavirus A | 1 | seg. 7 | FJ947755 |

TABLE 10-continued

| Taxonomy | Rep.Acc.ID | Host | # GN's | VíroCap-1.0 Taxonomy Lineage | Seg. Count | GN.Acc.IDs |
|---|---|---|---|---|---|---|
| Rotavirus A human/Bethesda/DC168/1976/G3P[8] | NC_011502 | vertebrates,human | 1 | Reoviridae,Rotavirus,Rotavirus A | seg. 8 | FJ947756 |
| Rotavirus A human/Bethesda/DC168/1976/G3P[8] | NC_011503 | vertebrates,human | 1 | Reoviridae,Rotavirus,Rotavirus A | seg. 9 | FJ947757 |
| Rotavirus A human/Bethesda/DC168/1976/G3P[8] | NC_011504 | vertebrates,human | 1 | Reoviridae,Rotavirus,Rotavirus A | seg. 10 | FJ947758 |
| Rotavirus A human/Bethesda/DC168/1976/G3P[8] | NC_011505 | vertebrates,human | 1 | Reoviridae,Rotavirus,Rotavirus A | seg. 11 | FJ947759 |
| Rotavirus A human/Bethesda/DC168/1976/G3P[8] | NC_011508 | vertebrates,human | 1 | Reoviridae,Rotavirus,Rotavirus A | seg. 3 | FJ947751 |
| Rotavirus A human/Bethesda/DC168/1976/G3P[8] | NC_011509 | vertebrates,human | 1 | Reoviridae,Rotavirus,Rotavirus A | seg. 6 | FJ947754 |
| Rotavirus A human/Bethesda/DC168/1976/G3P[8] | NC_011510 | vertebrates,human | 1 | Reoviridae,Rotavirus,Rotavirus A | seg. 4 | FJ947752 |
| Rotavirus A human/Bethesda/DC1730/1979/G3P[8] | NC_011500 | vertebrates,human | 1 | Reoviridae,Rotavirus,Rotavirus A | seg. 5 | FJ947322 |
| Rotavirus A human/Bethesda/DC1730/1979/G3P[8] | NC_011501 | vertebrates,human | 1 | Reoviridae,Rotavirus,Rotavirus A | seg. 7 | FJ947324 |
| Rotavirus A human/Bethesda/DC1730/1979/G3P[8] | NC_011502 | vertebrates,human | 1 | Reoviridae,Rotavirus,Rotavirus A | seg. 8 | FJ947325 |
| Rotavirus A human/Bethesda/DC1730/1979/G3P[8] | NC_011504 | vertebrates,human | 1 | Reoviridae,Rotavirus,Rotavirus A | seg. 10 | FJ947327 |
| Rotavirus A human/Bethesda/DC1730/1979/G3P[8] | NC_011505 | vertebrates,human | 1 | Reoviridae,Rotavirus,Rotavirus A | seg. 11 | FJ947328 |
| Rotavirus A human/Bethesda/DC1730/1979/G3P[8] | NC_011509 | vertebrates,human | 1 | Reoviridae,Rotavirus,Rotavirus A | seg. 6 | FJ947323 |
| Rotavirus A human/Bethesda/DC1730/1979/G3P[8] | NC_011510 | vertebrates,human | 1 | Reoviridae,Rotavirus,Rotavirus A | seg. 4 | FJ947321 |
| Rotavirus A human/Bethesda/DC1898/1976/G3P[8] | NC_011500 | vertebrates,human | 1 | Reoviridae,Rotavirus,Rotavirus A | seg. 5 | FJ947300 |
| Rotavirus A human/Bethesda/DC1898/1976/G3P[8] | NC_011501 | vertebrates,human | 1 | Reoviridae,Rotavirus,Rotavirus A | seg. 7 | FJ947302 |

TABLE 10-continued

VimCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC1898/1976/G3P[8] | NC_011502 | vertebrates,human | Reoviridae,Rotavirus,Rotavirus A | 1 | seg. 8 | FJ947303 |
| Rotavirus A human/Bethesda/DC1898/1976/G3P[8] | NC_011504 | vertebrates,human | Reoviridae,Rotavirus,Rotavirus A | 1 | seg. 10 | FJ947305 |
| Rotavirus A human/Bethesda/DC1898/1976/G3P[8] | NC_011505 | vertebrates,human | Reoviridae,Rotavirus,Rotavirus A | 1 | seg. 11 | FJ947306 |
| Rotavirus A human/Bethesda/DC1898/1976/G3P[8] | NC_011508 | vertebrates,human | Reoviridae,Rotavirus,Rotavirus A | 1 | seg. 3 | FJ947298 |
| Rotavirus A human/Bethesda/DC1898/1976/G3P[8] | NC_011509 | vertebrates,human | Reoviridae,Rotavirus,Rotavirus A | 1 | seg. 6 | FJ947301 |
| Rotavirus A human/Bethesda/DC1898/1976/G3P[8] | NC_011510 | vertebrates,human | Reoviridae,Rotavirus,Rotavirus A | 1 | seg. 4 | FJ947299 |
| Rotavirus A human/Bethesda/DC2069/1976/G3P[8] | NC_011500 | vertebrates,human | Reoviridae,Rotavirus,Rotavirus A | 1 | seg. 5 | FJ947808 |
| Rotavirus A human/Bethesda/DC2069/1976/G3P[8] | NC_011501 | vertebrates,human | Reoviridae,Rotavirus,Rotavirus A | 1 | seg. 7 | FJ947810 |
| Rotavirus A human/Bethesda/DC2069/1976/G3P[8] | NC_011502 | vertebrates,human | Reoviridae,Rotavirus,Rotavirus A | 1 | seg. 8 | FJ947811 |
| Rotavirus A human/Bethesda/DC2069/1976/G3P[8] | NC_011504 | vertebrates,human | Reoviridae,Rotavirus,Rotavirus A | 1 | seg. 10 | FJ947813 |
| Rotavirus A human/Bethesda/DC2069/1976/G3P[8] | NC_011505 | vertebrates,human | Reoviridae,Rotavirus,Rotavirus A | 1 | seg. 11 | FJ947814 |
| Rotavirus A human/Bethesda/DC2069/1976/G3P[8] | NC_011507 | vertebrates,human | Reoviridae,Rotavirus,Rotavirus A | 1 | seg. 1 | FJ947804 |
| Rotavirus A human/Bethesda/DC2069/1976/G3P[8] | NC_011508 | vertebrates,human | Reoviridae,Rotavirus,Rotavirus A | 1 | seg. 3 | FJ947806 |
| Rotavirus A human/Bethesda/DC2069/1976/G3P[8] | NC_011509 | vertebrates,human | Reoviridae,Rotavirus,Rotavirus A | 1 | seg. 6 | FJ947809 |
| Rotavirus A human/Bethesda/DC2069/1976/G3P[8] | NC_011510 | vertebrates,human | Reoviridae,Rotavirus,Rotavirus A | 1 | seg. 4 | FJ947807 |
| Rotavirus A human/Bethesda/DC2081/1976/G3P[8] | NC_011500 | vertebrates,human | Reoviridae,Rotavirus,Rotavirus A | 1 | seg. 5 | FJ947819 |

TABLE 10-continued

VipoCap-1.0 Taxonomy

| Taxonomy | Rep.Acc.ID | Host | # GN's | Lineage | Seg. Count | GN.Acc.IDs |
|---|---|---|---|---|---|---|
| Rotavirus A human/Bethesda/DC2081/ 1976/G3P[8] | NC_011501 | vertebrates,human | 1 | Reoviridae,Rotavirus,Rotavirus A | seg. 7 | FJ947821 |
| Rotavirus A human/Bethesda/DC2081/ 1976/G3P[8] | NC_011502 | vertebrates,human | 1 | Reoviridae,Rotavirus,Rotavirus A | seg. 8 | FJ947822 |
| Rotavirus A human/Bethesda/DC2081/ 1976/G3P[8] | NC_011504 | vertebrates,human | 1 | Reoviridae,Rotavirus,Rotavirus A | seg. 10 | FJ947824 |
| Rotavirus A human/Bethesda/DC2081/ 1976/G3P[8] | NC_011505 | vertebrates,human | 1 | Reoviridae,Rotavirus,Rotavirus A | seg. 11 | FJ947825 |
| Rotavirus A human/Bethesda/DC2081/ 1976/G3P[8] | NC_011508 | vertebrates,human | 1 | Reoviridae,Rotavirus,Rotavirus A | seg. 3 | FJ947817 |
| Rotavirus A human/Bethesda/DC2081/ 1976/G3P[8] | NC_011509 | vertebrates,human | 1 | Reoviridae,Rotavirus,Rotavirus A | seg. 6 | FJ947820 |
| Rotavirus A human/Bethesda/DC2081/ 1976/G3P[8] | NC_011510 | vertebrates,human | 1 | Reoviridae,Rotavirus,Rotavirus A | seg. 4 | FJ947818 |
| Rotavirus A human/Bethesda/DC2102/ 1976/G3P[8] | NC_011500 | vertebrates,human | 1 | Reoviridae,Rotavirus,Rotavirus A | seg. 5 | FJ947830 |
| Rotavirus A human/Bethesda/DC2102/ 1976/G3P[8] | NC_011501 | vertebrates,human | 1 | Reoviridae,Rotavirus,Rotavirus A | seg. 7 | FJ947832 |
| Rotavirus A human/Bethesda/DC2102/ 1976/G3P[8] | NC_011502 | vertebrates,human | 1 | Reoviridae,Rotavirus,Rotavirus A | seg. 8 | FJ947833 |
| Rotavirus A human/Bethesda/DC2102/ 1976/G3P[8] | NC_011504 | vertebrates,human | 1 | Reoviridae,Rotavirus,Rotavirus A | seg. 10 | FJ947835 |
| Rotavirus A human/Bethesda/DC2102/ 1976/G3P[8] | NC_011505 | vertebrates,human | 1 | Reoviridae,Rotavirus,Rotavirus A | seg. 11 | FJ947836 |
| Rotavirus A human/Bethesda/DC2102/ 1976/G3P[8] | NC_011506 | vertebrates,human | 1 | Reoviridae,Rotavirus,Rotavirus A | seg. 2 | FJ947827 |
| Rotavirus A human/Bethesda/DC2102/ 1976/G3P[8] | NC_011508 | vertebrates,human | 1 | Reoviridae,Rotavirus,Rotavirus A | seg. 3 | FJ947828 |
| Rotavirus A human/Bethesda/DC2102/ 1976/G3P[8] | NC_011509 | vertebrates,human | 1 | Reoviridae,Rotavirus,Rotavirus A | seg. 6 | FJ947831 |
| Rotavirus A human/Bethesda/DC2102/ 1976/G3P[8] | NC_011510 | vertebrates,human | 1 | Reoviridae,Rotavirus,Rotavirus A | seg. 4 | FJ947829 |

TABLE 10-continued

VIroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC2106/ 1976/G3P[8] | NC_011500 | vertebrates,human | Reoviridae,Rotavirus,Rotavirus A | 1 | seg. 5 | FJ947841 |
| Rotavirus A human/Bethesda/DC2106/ 1976/G3P[8] | NC_011501 | vertebrates,human | Reoviridae,Rotavirus,Rotavirus A | 1 | seg. 7 | FJ947843 |
| Rotavirus A human/Bethesda/DC2106/ 1976/G3P[8] | NC_011502 | vertebrates,human | Reoviridae,Rotavirus,Rotavirus A | 1 | seg. 8 | FJ947844 |
| Rotavirus A human/Bethesda/DC2106/ 1976/G3P[8] | NC_011504 | vertebrates,human | Reoviridae,Rotavirus,Rotavirus A | 1 | seg. 10 | FJ947846 |
| Rotavirus A human/Bethesda/DC2106/ 1976/G3P[8] | NC_011505 | vertebrates,human | Reoviridae,Rotavirus,Rotavirus A | 1 | seg. 11 | FJ947847 |
| Rotavirus A human/Bethesda/DC2106/ 1976/G3P[8] | NC_011506 | vertebrates,human | Reoviridae,Rotavirus,Rotavirus A | 1 | seg. 2 | FJ947838 |
| Rotavirus A human/Bethesda/DC2106/ 1976/G3P[8] | NC_011507 | vertebrates,human | Reoviridae,Rotavirus,Rotavirus A | 1 | seg. 1 | FJ947837 |
| Rotavirus A human/Bethesda/DC2106/ 1976/G3P[8] | NC_011508 | vertebrates,human | Reoviridae,Rotavirus,Rotavirus A | 1 | seg. 3 | FJ947839 |
| Rotavirus A human/Bethesda/DC2106/ 1976/G3P[8] | NC_011509 | vertebrates,human | Reoviridae,Rotavirus,Rotavirus A | 1 | seg. 6 | FJ947842 |
| Rotavirus A human/Bethesda/DC2106/ 1976/G3P[8] | NC_011510 | vertebrates,human | Reoviridae,Rotavirus,Rotavirus A | 1 | seg. 4 | FJ947840 |
| Rotavirus A human/Bethesda/DC2109/ 1976/G3P[8] | NC_011500 | vertebrates,human | Reoviridae,Rotavirus,Rotavirus A | 1 | seg. 5 | FJ947377 |
| Rotavirus A human/Bethesda/DC2109/ 1976/G3P[8] | NC_011501 | vertebrates,human | Reoviridae,Rotavirus,Rotavirus A | 1 | seg. 7 | FJ947379 |
| Rotavirus A human/Bethesda/DC2109/ 1976/G3P[8] | NC_011502 | vertebrates,human | Reoviridae,Rotavirus,Rotavirus A | 1 | seg. 8 | FJ947380 |
| Rotavirus A human/Bethesda/DC2109/ 1976/G3P[8] | NC_011504 | vertebrates,human | Reoviridae,Rotavirus,Rotavirus A | 1 | seg. 10 | FJ947382 |
| Rotavirus A human/Bethesda/DC2109/ 1976/G3P[8] | NC_011505 | vertebrates,human | Reoviridae,Rotavirus,Rotavirus A | 1 | seg. 11 | FJ947383 |
| Rotavirus A human/Bethesda/DC2109/ 1976/G3P[8] | NC_011506 | vertebrates,human | Reoviridae,Rotavirus,Rotavirus A | 1 | seg. 2 | FJ947374 |

TABLE 10-continued

VirOCap-1.0 Taxonomy

| Taxonomy | Rep.Acc.ID | Host | # GN's | Lineage | Seg. Count | GN.Acc.IDs |
|---|---|---|---|---|---|---|
| Rotavirus A human/Bethesda/DC2109/ 1976/G3P[8] | NC_011509 | vertebrates,human | 1 | Reoviridae,Rotavirus,Rotavirus A | seg. 6 | FJ947378 |
| Rotavirus A human/Bethesda/DC2109/ 1976/G3P[8] | NC_011510 | vertebrates,human | 1 | Reoviridae,Rotavirus,Rotavirus A | seg. 4 | FJ947376 |
| Rotavirus A human/Bethesda/DC2114/ 1976/G3P[8] | NC_011500 | vertebrates,human | 1 | Reoviridae,Rotavirus,Rotavirus A | seg. 5 | FJ947388 |
| Rotavirus A human/Bethesda/DC2114/ 1976/G3P[8] | NC_011501 | vertebrates,human | 1 | Reoviridae,Rotavirus,Rotavirus A | seg. 7 | FJ947390 |
| Rotavirus A human/Bethesda/DC2114/ 1976/G3P[8] | NC_011502 | vertebrates,human | 1 | Reoviridae,Rotavirus,Rotavirus A | seg. 8 | FJ947391 |
| Rotavirus A human/Bethesda/DC2114/ 1976/G3P[8] | NC_011504 | vertebrates,human | 1 | Reoviridae,Rotavirus,Rotavirus A | seg. 10 | FJ947393 |
| Rotavirus A human/Bethesda/DC2114/ 1976/G3P[8] | NC_011505 | vertebrates,human | 1 | Reoviridae,Rotavirus,Rotavirus A | seg. 11 | FJ947394 |
| Rotavirus A human/Bethesda/DC2114/ 1976/G3P[8] | NC_011506 | vertebrates,human | 1 | Reoviridae,Rotavirus,Rotavirus A | seg. 2 | FJ947385 |
| Rotavirus A human/Bethesda/DC2114/ 1976/G3P[8] | NC_011508 | vertebrates,human | 1 | Reoviridae,Rotavirus,Rotavirus A | seg. 3 | FJ947386 |
| Rotavirus A human/Bethesda/DC2114/ 1976/G3P[8] | NC_011509 | vertebrates,human | 1 | Reoviridae,Rotavirus,Rotavirus A | seg. 6 | FJ947389 |
| Rotavirus A human/Bethesda/DC2114/ 1976/G3P[8] | NC_011510 | vertebrates,human | 1 | Reoviridae,Rotavirus,Rotavirus A | seg. 4 | FJ947387 |
| Rotavirus A human/Bethesda/DC2119/ 1976/G3P[8] | NC_011500 | vertebrates,human | 1 | Reoviridae,Rotavirus,Rotavirus A | seg. 5 | FJ947399 |
| Rotavirus A human/Bethesda/DC2119/ 1976/G3P[8] | NC_011501 | vertebrates,human | 1 | Reoviridae,Rotavirus,Rotavirus A | seg. 7 | FJ947401 |
| Rotavirus A human/Bethesda/DC2119/ 1976/G3P[8] | NC_011502 | vertebrates,human | 1 | Reoviridae,Rotavirus,Rotavirus A | seg. 8 | FJ947402 |
| Rotavirus A human/Bethesda/DC2119/ 1976/G3P[8] | NC_011504 | vertebrates,human | 1 | Reoviridae,Rotavirus,Rotavirus A | seg. 10 | FJ947404 |
| Rotavirus A human/Bethesda/DC2119/ 1976/G3P[8] | NC_011505 | vertebrates,human | 1 | Reoviridae,Rotavirus,Rotavirus A | seg. 11 | FJ947405 |

TABLE 10-continued

| Taxonomy | Rep.Acc.ID | Host | VrioCap-1.0 Taxonomy | | Seg. Count | GN.Acc.IDs |
|---|---|---|---|---|---|---|
| | | | # GN's | Lineage | | |
| Rotavirus A human/Bethesda/DC2119/1976/G3P[8] | NC_011508 | vertebrates,human | 1 | Reoviridae,Rotavirus,Rotavirus A | seg. 3 | FJ947397 |
| Rotavirus A human/Bethesda/DC2119/1976/G3P[8] | NC_011509 | vertebrates,human | 1 | Reoviridae,Rotavirus,Rotavirus A | seg. 6 | FJ947400 |
| Rotavirus A human/Bethesda/DC2119/1976/G3P[8] | NC_011510 | vertebrates,human | 1 | Reoviridae,Rotavirus,Rotavirus A | seg. 4 | FJ947398 |
| Rotavirus A human/Bethesda/DC2171/1976/G3P[8] | NC_011500 | vertebrates,human | 1 | Reoviridae,Rotavirus,Rotavirus A | seg. 5 | FJ947410 |
| Rotavirus A human/Bethesda/DC2171/1976/G3P[8] | NC_011501 | vertebrates,human | 1 | Reoviridae,Rotavirus,Rotavirus A | seg. 7 | FJ947412 |
| Rotavirus A human/Bethesda/DC2171/1976/G3P[8] | NC_011502 | vertebrates,human | 1 | Reoviridae,Rotavirus,Rotavirus A | seg. 8 | FJ947413 |
| Rotavirus A human/Bethesda/DC2171/1976/G3P[8] | NC_011504 | vertebrates,human | 1 | Reoviridae,Rotavirus,Rotavirus A | seg. 10 | FJ947415 |
| Rotavirus A human/Bethesda/DC2171/1976/G3P[8] | NC_011505 | vertebrates,human | 1 | Reoviridae,Rotavirus,Rotavirus A | seg. 11 | FJ947416 |
| Rotavirus A human/Bethesda/DC2171/1976/G3P[8] | NC_011508 | vertebrates,human | 1 | Reoviridae,Rotavirus,Rotavirus A | seg. 3 | FJ947408 |
| Rotavirus A human/Bethesda/DC2171/1976/G3P[8] | NC_011509 | vertebrates,human | 1 | Reoviridae,Rotavirus,Rotavirus A | seg. 6 | FJ947411 |
| Rotavirus A human/Bethesda/DC2171/1976/G3P[8] | NC_011510 | vertebrates,human | 1 | Reoviridae,Rotavirus,Rotavirus A | seg. 4 | FJ947409 |
| Rotavirus A human/Bethesda/DC2212/1976/G3P[8] | NC_011500 | vertebrates,human | 1 | Reoviridae,Rotavirus,Rotavirus A | seg. 5 | FJ947852 |
| Rotavirus A human/Bethesda/DC2212/1976/G3P[8] | NC_011501 | vertebrates,human | 1 | Reoviridae,Rotavirus,Rotavirus A | seg. 7 | FJ947854 |
| Rotavirus A human/Bethesda/DC2212/1976/G3P[8] | NC_011502 | vertebrates,human | 1 | Reoviridae,Rotavirus,Rotavirus A | seg. 8 | FJ947855 |
| Rotavirus A human/Bethesda/DC2212/1976/G3P[8] | NC_011504 | vertebrates,human | 1 | Reoviridae,Rotavirus,Rotavirus A | seg. 10 | FJ947857 |
| Rotavirus A human/Bethesda/DC2212/1976/G3P[8] | NC_011505 | vertebrates,human | 1 | Reoviridae,Rotavirus,Rotavirus A | seg. 11 | FJ947858 |

TABLE 10-continued

VrioCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC2212/ 1976/G3P[8] | NC_011506 | vertebrates,human | Reoviridae,Rotavirus,Rotavirus A | 1 | seg. 2 | FJ947849 |
| Rotavirus A human/Bethesda/DC2212/ 1976/G3P[8] | NC_011508 | vertebrates,human | Reoviridae,Rotavirus,Rotavirus A | 1 | seg. 3 | FJ947850 |
| Rotavirus A human/Bethesda/DC2212/ 1976/G3P[8] | NC_011509 | vertebrates,human | Reoviridae,Rotavirus,Rotavirus A | 1 | seg. 6 | FJ947853 |
| Rotavirus A human/Bethesda/DC2212/ 1976/G3P[8] | NC_011510 | vertebrates,human | Reoviridae,Rotavirus,Rotavirus A | 1 | seg. 4 | FJ947851 |
| Rotavirus A human/Bethesda/DC2238/ 1976/G3P[8] | NC_011500 | vertebrates,human | Reoviridae,Rotavirus,Rotavirus A | 1 | seg. 5 | FJ947421 |
| Rotavirus A human/Bethesda/DC2238/ 1976/G3P[8] | NC_011501 | vertebrates,human | Reoviridae,Rotavirus,Rotavirus A | 1 | seg. 7 | FJ947423 |
| Rotavirus A human/Bethesda/DC2238/ 1976/G3P[8] | NC_011502 | vertebrates,human | Reoviridae,Rotavirus,Rotavirus A | 1 | seg. 8 | FJ947424 |
| Rotavirus A human/Bethesda/DC2238/ 1976/G3P[8] | NC_011504 | vertebrates,human | Reoviridae,Rotavirus,Rotavirus A | 1 | seg. 10 | FJ947426 |
| Rotavirus A human/Bethesda/DC2238/ 1976/G3P[8] | NC_011505 | vertebrates,human | Reoviridae,Rotavirus,Rotavirus A | 1 | seg. 11 | FJ947427 |
| Rotavirus A human/Bethesda/DC2238/ 1976/G3P[8] | NC_011508 | vertebrates,human | Reoviridae,Rotavirus,Rotavirus A | 1 | seg. 3 | FJ947419 |
| Rotavirus A human/Bethesda/DC2238/ 1976/G3P[8] | NC_011509 | vertebrates,human | Reoviridae,Rotavirus,Rotavirus A | 1 | seg. 6 | FJ947422 |
| Rotavirus A human/Bethesda/DC2238/ 1976/G3P[8] | NC_011510 | vertebrates,human | Reoviridae,Rotavirus,Rotavirus A | 1 | seg. 4 | FJ947420 |
| Rotavirus A human/Bethesda/DC2239/ 1976/G3P[8] | NC_011500 | vertebrates,human | Reoviridae,Rotavirus,Rotavirus A | 1 | seg. 5 | FJ947863 |
| Rotavirus A human/Bethesda/DC2239/ 1976/G3P[8] | NC_011501 | vertebrates,human | Reoviridae,Rotavirus,Rotavirus A | 1 | seg. 7 | FJ947865 |
| Rotavirus A human/Bethesda/DC2239/ 1976/G3P[8] | NC_011502 | vertebrates,human | Reoviridae,Rotavirus,Rotavirus A | 1 | seg. 8 | FJ947866 |
| Rotavirus A human/Bethesda/DC2239/ 1976/G3P[8] | NC_011504 | vertebrates,human | Reoviridae,Rotavirus,Rotavirus A | 1 | seg. 10 | FJ947868 |

TABLE 10-continued

| Taxonomy | Rep.Acc.ID | Host | ViroCap-1.0 Taxonomy | | Seg. Count | GN.Acc.IDs |
| --- | --- | --- | --- | --- | --- | --- |
| | | | # GN's | Lineage | | |
| Rotavirus A human/Bethesda/DC2239/ 1976/G3P[8] | NC_011505 | vertebrates,human | 1 | Reoviridae,Rotavirus,Rotavirus A | seg. 11 | FJ947869 |
| Rotavirus A human/Bethesda/DC2239/ 1976/G3P[8] | NC_011506 | vertebrates,human | 1 | Reoviridae,Rotavirus,Rotavirus A | seg. 2 | FJ947860 |
| Rotavirus A human/Bethesda/DC2239/ 1976/G3P[8] | NC_011508 | vertebrates,human | 1 | Reoviridae,Rotavirus,Rotavirus A | seg. 3 | FJ947861 |
| Rotavirus A human/Bethesda/DC2239/ 1976/G3P[8] | NC_011509 | vertebrates,human | 1 | Reoviridae,Rotavirus,Rotavirus A | seg. 6 | FJ947864 |
| Rotavirus A human/Bethesda/DC2239/ 1976/G3P[8] | NC_011510 | vertebrates,human | 1 | Reoviridae,Rotavirus,Rotavirus A | seg. 4 | FJ947862 |
| Rotavirus A human/Bethesda/DC2241/ 1977/G4P[8] | NC_011500 | vertebrates,human | 1 | Reoviridae,Rotavirus,Rotavirus A | seg. 5 | HM773880 |
| Rotavirus A human/Bethesda/DC2241/ 1977/G4P[8] | NC_011501 | vertebrates,human | 1 | Reoviridae,Rotavirus,Rotavirus A | seg. 7 | HM773882 |
| Rotavirus A human/Bethesda/DC2241/ 1977/G4P[8] | NC_011502 | vertebrates,human | 1 | Reoviridae,Rotavirus,Rotavirus A | seg. 8 | HM773883 |
| Rotavirus A human/Bethesda/DC2241/ 1977/G4P[8] | NC_011503 | vertebrates,human | 1 | Reoviridae,Rotavirus,Rotavirus A | seg. 9 | HM773884 |
| Rotavirus A human/Bethesda/DC2241/ 1977/G4P[8] | NC_011504 | vertebrates,human | 1 | Reoviridae,Rotavirus,Rotavirus A | seg. 10 | HM773885 |
| Rotavirus A human/Bethesda/DC2241/ 1977/G4P[8] | NC_011505 | vertebrates,human | 1 | Reoviridae,Rotavirus,Rotavirus A | seg. 11 | HM773886 |
| Rotavirus A human/Bethesda/DC2241/ 1977/G4P[8] | NC_011506 | vertebrates,human | 1 | Reoviridae,Rotavirus,Rotavirus A | seg. 2 | HM773877 |
| Rotavirus A human/Bethesda/DC2241/ 1977/G4P[8] | NC_011507 | vertebrates,human | 1 | Reoviridae,Rotavirus,Rotavirus A | seg. 1 | HM773876 |
| Rotavirus A human/Bethesda/DC2241/ 1977/G4P[8] | NC_011508 | vertebrates,human | 1 | Reoviridae,Rotavirus,Rotavirus A | seg. 3 | HM773878 |
| Rotavirus A human/Bethesda/DC2241/ 1977/G4P[8] | NC_011509 | vertebrates,human | 1 | Reoviridae,Rotavirus,Rotavirus A | seg. 6 | HM773881 |
| Rotavirus A human/Bethesda/DC2241/ 1977/G4P[8] | NC_011510 | vertebrates,human | 1 | Reoviridae,Rotavirus,Rotavirus A | seg. 4 | HM773879 |

TABLE 10-continued

VirocCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC2262/1976/G3P[8] | NC_011500 | vertebrates,human | Reoviridae,Rotavirus,Rotavirus A | 1 | seg. 5 | FJ947874 |
| Rotavirus A human/Bethesda/DC2262/1976/G3P[8] | NC_011501 | vertebrates,human | Reoviridae,Rotavirus,Rotavirus A | 1 | seg. 7 | FJ947876 |
| Rotavirus A human/Bethesda/DC2262/1976/G3P[8] | NC_011502 | vertebrates,human | Reoviridae,Rotavirus,Rotavirus A | 1 | seg. 8 | FJ947877 |
| Rotavirus A human/Bethesda/DC2262/1976/G3P[8] | NC_011504 | vertebrates,human | Reoviridae,Rotavirus,Rotavirus A | 1 | seg. 10 | FJ947879 |
| Rotavirus A human/Bethesda/DC2262/1976/G3P[8] | NC_011505 | vertebrates,human | Reoviridae,Rotavirus,Rotavirus A | 1 | seg. 11 | FJ947880 |
| Rotavirus A human/Bethesda/DC2262/1976/G3P[8] | NC_011506 | vertebrates,human | Reoviridae,Rotavirus,Rotavirus A | 1 | seg. 2 | FJ947871 |
| Rotavirus A human/Bethesda/DC2262/1976/G3P[8] | NC_011508 | vertebrates,human | Reoviridae,Rotavirus,Rotavirus A | 1 | seg. 3 | FJ947872 |
| Rotavirus A human/Bethesda/DC2262/1976/G3P[8] | NC_011509 | vertebrates,human | Reoviridae,Rotavirus,Rotavirus A | 1 | seg. 6 | FJ947875 |
| Rotavirus A human/Bethesda/DC2262/1976/G3P[8] | NC_011510 | vertebrates,human | Reoviridae,Rotavirus,Rotavirus A | 1 | seg. 4 | FJ947873 |
| Rotavirus A human/Bethesda/DC2266/1976/G3P[8] | NC_011500 | vertebrates,human | Reoviridae,Rotavirus,Rotavirus A | 1 | seg. 5 | FJ947885 |
| Rotavirus A human/Bethesda/DC2266/1976/G3P[8] | NC_011501 | vertebrates,human | Reoviridae,Rotavirus,Rotavirus A | 1 | seg. 7 | FJ947887 |
| Rotavirus A human/Bethesda/DC2266/1976/G3P[8] | NC_011502 | vertebrates,human | Reoviridae,Rotavirus,Rotavirus A | 1 | seg. 8 | FJ947888 |
| Rotavirus A human/Bethesda/DC2266/1976/G3P[8] | NC_011504 | vertebrates,human | Reoviridae,Rotavirus,Rotavirus A | 1 | seg. 10 | FJ947890 |
| Rotavirus A human/Bethesda/DC2266/1976/G3P[8] | NC_011505 | vertebrates,human | Reoviridae,Rotavirus,Rotavirus A | 1 | seg. 11 | FJ947891 |
| Rotavirus A human/Bethesda/DC2266/1976/G3P[8] | NC_011508 | vertebrates,human | Reoviridae,Rotavirus,Rotavirus A | 1 | seg. 3 | FJ947883 |
| Rotavirus A human/Bethesda/DC2266/1976/G3P[8] | NC_011509 | vertebrates,human | Reoviridae,Rotavirus,Rotavirus A | 1 | seg. 6 | FJ947886 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Bethesda/DC2266/1976/G3P[8] | NC_011510 | vertebrates,human | 1 | Reoviridae,Rotavirus,Rotavirus A | seg. 4 | FJ947884 |
| Rotavirus A human/Bethesda/DC23/19 76/G3P[8] | NC_011500 | vertebrates,human | 1 | Reoviridae,Rotavirus,Rotavirus A | seg. 5 | FJ947212 |
| Rotavirus A human/Bethesda/DC23/19 76/G3P[8] | NC_011501 | vertebrates,human | 1 | Reoviridae,Rotavirus,Rotavirus A | seg. 7 | FJ947214 |
| Rotavirus A human/Bethesda/DC23/19 76/G3P[8] | NC_011502 | vertebrates,human | 1 | Reoviridae,Rotavirus,Rotavirus A | seg. 8 | FJ947215 |
| Rotavirus A human/Bethesda/DC23/19 76/G3P[8] | NC_011503 | vertebrates,human | 1 | Reoviridae,Rotavirus,Rotavirus A | seg. 9 | FJ947216 |
| Rotavirus A human/Bethesda/DC23/19 76/G3P[8] | NC_011504 | vertebrates,human | 1 | Reoviridae,Rotavirus,Rotavirus A | seg. 10 | FJ947217 |
| Rotavirus A human/Bethesda/DC23/19 76/G3P[8] | NC_011505 | vertebrates,human | 1 | Reoviridae,Rotavirus,Rotavirus A | seg. 11 | FJ947218 |
| Rotavirus A human/Bethesda/DC23/19 76/G3P[8] | NC_011507 | vertebrates,human | 1 | Reoviridae,Rotavirus,Rotavirus A | seg. 1 | FJ947208 |
| Rotavirus A human/Bethesda/DC23/19 76/G3P[8] | NC_011509 | vertebrates,human | 1 | Reoviridae,Rotavirus,Rotavirus A | seg. 6 | FJ947213 |
| Rotavirus A human/Bethesda/DC23/19 76/G3P[8] | NC_011510 | vertebrates,human | 1 | Reoviridae,Rotavirus,Rotavirus A | seg. 4 | FJ947211 |
| Rotavirus A human/Bethesda/DC4320/1988/G4P[8] | NC_011500 | vertebrates,human | 1 | Reoviridae,Rotavirus,Rotavirus A | seg. 5 | HM773891 |
| Rotavirus A human/Bethesda/DC4320/1988/G4P[8] | NC_011501 | vertebrates,human | 1 | Reoviridae,Rotavirus,Rotavirus A | seg. 7 | HM773893 |
| Rotavirus A human/Bethesda/DC4320/1988/G4P[8] | NC_011502 | vertebrates,human | 1 | Reoviridae,Rotavirus,Rotavirus A | seg. 8 | HM773894 |
| Rotavirus A human/Bethesda/DC4320/1988/G4P[8] | NC_011503 | vertebrates,human | 1 | Reoviridae,Rotavirus,Rotavirus A | seg. 9 | HM773895 |
| Rotavirus A human/Bethesda/DC4320/1988/G4P[8] | NC_011504 | vertebrates,human | 1 | Reoviridae,Rotavirus,Rotavirus A | seg. 10 | HM773896 |
| Rotavirus A human/Bethesda/DC4320/1988/G4P[8] | NC_011505 | vertebrates,human | 1 | Reoviridae,Rotavirus,Rotavirus A | seg. 11 | HM773897 |

TABLE 10-continued

VircCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC4320/1988/G4P[8] | NC_011506 | vertebrates,human | Reoviridae,Rotavirus,Rotavirus A | 1 | seg. 2 | HM773888 |
| Rotavirus A human/Bethesda/DC4320/1988/G4P[8] | NC_011507 | vertebrates,human | Reoviridae,Rotavirus,Rotavirus A | 1 | seg. 1 | HM773887 |
| Rotavirus A human/Bethesda/DC4320/1988/G4P[8] | NC_011508 | vertebrates,human | Reoviridae,Rotavirus,Rotavirus A | 1 | seg. 3 | HM773889 |
| Rotavirus A human/Bethesda/DC4320/1988/G4P[8] | NC_011509 | vertebrates,human | Reoviridae,Rotavirus,Rotavirus A | 1 | seg. 6 | HM773892 |
| Rotavirus A human/Bethesda/DC4320/1988/G4P[8] | NC_011510 | vertebrates,human | Reoviridae,Rotavirus,Rotavirus A | 1 | seg. 4 | HM773890 |
| Rotavirus A human/Bethesda/DC4608/1980/G4P[8] | NC_011500 | vertebrates,human | Reoviridae,Rotavirus,Rotavirus A | 1 | seg. 5 | HM773902 |
| Rotavirus A human/Bethesda/DC4608/1980/G4P[8] | NC_011501 | vertebrates,human | Reoviridae,Rotavirus,Rotavirus A | 1 | seg. 7 | HM773904 |
| Rotavirus A human/Bethesda/DC4608/1980/G4P[8] | NC_011502 | vertebrates,human | Reoviridae,Rotavirus,Rotavirus A | 1 | seg. 8 | HM773905 |
| Rotavirus A human/Bethesda/DC4608/1980/G4P[8] | NC_011503 | vertebrates,human | Reoviridae,Rotavirus,Rotavirus A | 1 | seg. 9 | HM773906 |
| Rotavirus A human/Bethesda/DC4608/1980/G4P[8] | NC_011504 | vertebrates,human | Reoviridae,Rotavirus,Rotavirus A | 1 | seg. 10 | HM773907 |
| Rotavirus A human/Bethesda/DC4608/1980/G4P[8] | NC_011505 | vertebrates,human | Reoviridae,Rotavirus,Rotavirus A | 1 | seg. 11 | HM773908 |
| Rotavirus A human/Bethesda/DC4608/1980/G4P[8] | NC_011506 | vertebrates,human | Reoviridae,Rotavirus,Rotavirus A | 1 | seg. 2 | HM773899 |
| Rotavirus A human/Bethesda/DC4608/1980/G4P[8] | NC_011507 | vertebrates,human | Reoviridae,Rotavirus,Rotavirus A | 1 | seg. 1 | HM773898 |
| Rotavirus A human/Bethesda/DC4608/1980/G4P[8] | NC_011508 | vertebrates,human | Reoviridae,Rotavirus,Rotavirus A | 1 | seg. 3 | HM773900 |
| Rotavirus A human/Bethesda/DC4608/1980/G4P[8] | NC_011509 | vertebrates,human | Reoviridae,Rotavirus,Rotavirus A | 1 | seg. 6 | HM773903 |
| Rotavirus A human/Bethesda/DC4608/1980/G4P[8] | NC_011510 | vertebrates,human | Reoviridae,Rotavirus,Rotavirus A | 1 | seg. 4 | HM773901 |

TABLE 10-continued

VirоCap-1.0 Taxonomy

| Taxonomy | Rep.Acc.ID | Host | # GN's | Lineage | Seg. Count | GN.Acc.IDs |
|---|---|---|---|---|---|---|
| Rotavirus A human/Bethesda/DC4613/1980/G4P[8] | NC_011500 | vertebrates,human | 1 | Reoviridae,Rotavirus,Rotavirus A | seg. 5 | HM773913 |
| Rotavirus A human/Bethesda/DC4613/1980/G4P[8] | NC_011501 | vertebrates,human | 1 | Reoviridae,Rotavirus,Rotavirus A | seg. 7 | HM773915 |
| Rotavirus A human/Bethesda/DC4613/1980/G4P[8] | NC_011502 | vertebrates,human | 1 | Reoviridae,Rotavirus,Rotavirus A | seg. 8 | HM773916 |
| Rotavirus A human/Bethesda/DC4613/1980/G4P[8] | NC_011503 | vertebrates,human | 1 | Reoviridae,Rotavirus,Rotavirus A | seg. 9 | HM773917 |
| Rotavirus A human/Bethesda/DC4613/1980/G4P[8] | NC_011504 | vertebrates,human | 1 | Reoviridae,Rotavirus,Rotavirus A | seg. 10 | HM773918 |
| Rotavirus A human/Bethesda/DC4613/1980/G4P[8] | NC_011505 | vertebrates,human | 1 | Reoviridae,Rotavirus,Rotavirus A | seg. 11 | HM773919 |
| Rotavirus A human/Bethesda/DC4613/1980/G4P[8] | NC_011506 | vertebrates,human | 1 | Reoviridae,Rotavirus,Rotavirus A | seg. 2 | HM773910 |
| Rotavirus A human/Bethesda/DC4613/1980/G4P[8] | NC_011507 | vertebrates,human | 1 | Reoviridae,Rotavirus,Rotavirus A | seg. 1 | HM773909 |
| Rotavirus A human/Bethesda/DC4613/1980/G4P[8] | NC_011508 | vertebrates,human | 1 | Reoviridae,Rotavirus,Rotavirus A | seg. 3 | HM773911 |
| Rotavirus A human/Bethesda/DC4613/1980/G4P[8] | NC_011509 | vertebrates,human | 1 | Reoviridae,Rotavirus,Rotavirus A | seg. 6 | HM773914 |
| Rotavirus A human/Bethesda/DC4613/1980/G4P[8] | NC_011510 | vertebrates,human | 1 | Reoviridae,Rotavirus,Rotavirus A | seg. 4 | HM773912 |
| Rotavirus A human/Bethesda/DC4772/1976/G3P[8] | NC_011500 | vertebrates,human | 1 | Reoviridae,Rotavirus,Rotavirus A | seg. 5 | FJ947366 |
| Rotavirus A human/Bethesda/DC4772/1976/G3P[8] | NC_011501 | vertebrates,human | 1 | Reoviridae,Rotavirus,Rotavirus A | seg. 7 | FJ947368 |
| Rotavirus A human/Bethesda/DC4772/1976/G3P[8] | NC_011502 | vertebrates,human | 1 | Reoviridae,Rotavirus,Rotavirus A | seg. 8 | FJ947369 |
| Rotavirus A human/Bethesda/DC4772/1976/G3P[8] | NC_011504 | vertebrates,human | 1 | Reoviridae,Rotavirus,Rotavirus A | seg. 10 | FJ947371 |
| Rotavirus A human/Bethesda/DC4772/1976/G3P[8] | NC_011505 | vertebrates,human | 1 | Reoviridae,Rotavirus,Rotavirus A | seg. 11 | FJ947372 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Bethesda/DC4772/ 1976/G3P[8] | NC_011506 | vertebrates,human | 1 | Reoviridae,Rotavirus,Rotavirus A | seg. 2 | FJ947363 |
| Rotavirus A human/Bethesda/DC4772/ 1976/G3P[8] | NC_011507 | vertebrates,human | 1 | Reoviridae,Rotavirus,Rotavirus A | seg. 1 | FJ947362 |
| Rotavirus A human/Bethesda/DC4772/ 1976/G3P[8] | NC_011508 | vertebrates,human | 1 | Reoviridae,Rotavirus,Rotavirus A | seg. 3 | FJ947364 |
| Rotavirus A human/Bethesda/DC4772/ 1976/G3P[8] | NC_011509 | vertebrates,human | 1 | Reoviridae,Rotavirus,Rotavirus A | seg. 6 | FJ947367 |
| Rotavirus A human/Bethesda/DC4772/ 1976/G3P[8] | NC_011510 | vertebrates,human | 1 | Reoviridae,Rotavirus,Rotavirus A | seg. 4 | FJ947365 |
| Rotavirus A human/Bethesda/DC4996/ 1977/G4P[8] | NC_011500 | vertebrates,human | 1 | Reoviridae,Rotavirus,Rotavirus A | seg. 5 | HM773924 |
| Rotavirus A human/Bethesda/DC4996/ 1977/G4P[8] | NC_011501 | vertebrates,human | 1 | Reoviridae,Rotavirus,Rotavirus A | seg. 7 | HM773926 |
| Rotavirus A human/Bethesda/DC4996/ 1977/G4P[8] | NC_011502 | vertebrates,human | 1 | Reoviridae,Rotavirus,Rotavirus A | seg. 8 | HM773927 |
| Rotavirus A human/Bethesda/DC4996/ 1977/G4P[8] | NC_011503 | vertebrates,human | 1 | Reoviridae,Rotavirus,Rotavirus A | seg. 9 | HM773928 |
| Rotavirus A human/Bethesda/DC4996/ 1977/G4P[8] | NC_011504 | vertebrates,human | 1 | Reoviridae,Rotavirus,Rotavirus A | seg. 10 | HM773929 |
| Rotavirus A human/Bethesda/DC4996/ 1977/G4P[8] | NC_011505 | vertebrates,human | 1 | Reoviridae,Rotavirus,Rotavirus A | seg. 11 | HM773930 |
| Rotavirus A human/Bethesda/DC4996/ 1977/G4P[8] | NC_011506 | vertebrates,human | 1 | Reoviridae,Rotavirus,Rotavirus A | seg. 2 | HM773921 |
| Rotavirus A human/Bethesda/DC4996/ 1977/G4P[8] | NC_011507 | vertebrates,human | 1 | Reoviridae,Rotavirus,Rotavirus A | seg. 1 | HM773920 |
| Rotavirus A human/Bethesda/DC4996/ 1977/G4P[8] | NC_011508 | vertebrates,human | 1 | Reoviridae,Rotavirus,Rotavirus A | seg. 3 | HM773922 |
| Rotavirus A human/Bethesda/DC4996/ 1977/G4P[8] | NC_011509 | vertebrates,human | 1 | Reoviridae,Rotavirus,Rotavirus A | seg. 6 | HM773925 |
| Rotavirus A human/Bethesda/DC4996/ 1977/G4P[8] | NC_011510 | vertebrates,human | 1 | Reoviridae,Rotavirus,Rotavirus A | seg. 4 | HM773923 |

TABLE 10-continued

| Taxonomy | Rep.Acc.ID | Host | ViroCap-1.0 Taxonomy | | Seg. Count | GN.Acc.IDs |
| --- | --- | --- | --- | --- | --- | --- |
| | | | # GN's | Lineage | | |
| Rotavirus A human/Bethesda/DC5064/ 1977/G4P[8] | NC_011500 | vertebrates,human | 1 | Reoviridae,Rotavirus,Rotavirus A | seg. 5 | HM773935 |
| Rotavirus A human/Bethesda/DC5064/ 1977/G4P[8] | NC_011501 | vertebrates,human | 1 | Reoviridae,Rotavirus,Rotavirus A | seg. 7 | HM773937 |
| Rotavirus A human/Bethesda/DC5064/ 1977/G4P[8] | NC_011502 | vertebrates,human | 1 | Reoviridae,Rotavirus,Rotavirus A | seg. 8 | HM773938 |
| Rotavirus A human/Bethesda/DC5064/ 1977/G4P[8] | NC_011503 | vertebrates,human | 1 | Reoviridae,Rotavirus,Rotavirus A | seg. 9 | HM773939 |
| Rotavirus A human/Bethesda/DC5064/ 1977/G4P[8] | NC_011504 | vertebrates,human | 1 | Reoviridae,Rotavirus,Rotavirus A | seg. 10 | HM773940 |
| Rotavirus A human/Bethesda/DC5064/ 1977/G4P[8] | NC_011505 | vertebrates,human | 1 | Reoviridae,Rotavirus,Rotavirus A | seg. 11 | HM773941 |
| Rotavirus A human/Bethesda/DC5064/ 1977/G4P[8] | NC_011506 | vertebrates,human | 1 | Reoviridae,Rotavirus,Rotavirus A | seg. 2 | HM773932 |
| Rotavirus A human/Bethesda/DC5064/ 1977/G4P[8] | NC_011507 | vertebrates,human | 1 | Reoviridae,Rotavirus,Rotavirus A | seg. 1 | HM773931 |
| Rotavirus A human/Bethesda/DC5064/ 1977/G4P[8] | NC_011508 | vertebrates,human | 1 | Reoviridae,Rotavirus,Rotavirus A | seg. 3 | HM773933 |
| Rotavirus A human/Bethesda/DC5064/ 1977/G4P[8] | NC_011509 | vertebrates,human | 1 | Reoviridae,Rotavirus,Rotavirus A | seg. 6 | HM773936 |
| Rotavirus A human/Bethesda/DC5064/ 1977/G4P[8] | NC_011510 | vertebrates,human | 1 | Reoviridae,Rotavirus,Rotavirus A | seg. 4 | HM773934 |
| Rotavirus A human/Bethesda/DC5115/ 1977/G4P[8] | NC_011500 | vertebrates,human | 1 | Reoviridae,Rotavirus,Rotavirus A | seg. 5 | HM773946 |
| Rotavirus A human/Bethesda/DC5115/ 1977/G4P[8] | NC_011501 | vertebrates,human | 1 | Reoviridae,Rotavirus,Rotavirus A | seg. 7 | HM773948 |
| Rotavirus A human/Bethesda/DC5115/ 1977/G4P[8] | NC_011502 | vertebrates,human | 1 | Reoviridae,Rotavirus,Rotavirus A | seg. 8 | HM773949 |
| Rotavirus A human/Bethesda/DC5115/ 1977/G4P[8] | NC_011503 | vertebrates,human | 1 | Reoviridae,Rotavirus,Rotavirus A | seg. 9 | HM773950 |
| Rotavirus A human/Bethesda/DC5115/ 1977/G4P[8] | NC_011504 | vertebrates,human | 1 | Reoviridae,Rotavirus,Rotavirus A | seg. 10 | HM773951 |

TABLE 10-continued

| Taxonomy | Rep.Acc.ID | Host | # GN's | ViroCap-1.0 Taxonomy Lineage | Seg. Count | GN.Acc.IDs |
|---|---|---|---|---|---|---|
| Rotavirus A human/Bethesda/DC5115/ 1977/G4P[8] | NC_011505 | vertebrates,human | 1 | Reoviridae,Rotavirus,Rotavirus A | seg. 11 | HM773952 |
| Rotavirus A human/Bethesda/DC5115/ 1977/G4P[8] | NC_011506 | vertebrates,human | 1 | Reoviridae,Rotavirus,Rotavirus A | seg. 2 | HM773943 |
| Rotavirus A human/Bethesda/DC5115/ 1977/G4P[8] | NC_011507 | vertebrates,human | 1 | Reoviridae,Rotavirus,Rotavirus A | seg. 1 | HM773942 |
| Rotavirus A human/Bethesda/DC5115/ 1977/G4P[8] | NC_011508 | vertebrates,human | 1 | Reoviridae,Rotavirus,Rotavirus A | seg. 3 | HM773944 |
| Rotavirus A human/Bethesda/DC5115/ 1977/G4P[8] | NC_011509 | vertebrates,human | 1 | Reoviridae,Rotavirus,Rotavirus A | seg. 6 | HM773947 |
| Rotavirus A human/Bethesda/DC5115/ 1977/G4P[8] | NC_011510 | vertebrates,human | 1 | Reoviridae,Rotavirus,Rotavirus A | seg. 4 | HM773945 |
| Rotavirus A human/Bethesda/DC5142/ 1975/G3P[8] | NC_011500 | vertebrates,human | 1 | Reoviridae,Rotavirus,Rotavirus A | seg. 5 | FJ947201 |
| Rotavirus A human/Bethesda/DC5142/ 1975/G3P[8] | NC_011501 | vertebrates,human | 1 | Reoviridae,Rotavirus,Rotavirus A | seg. 7 | FJ947203 |
| Rotavirus A human/Bethesda/DC5142/ 1975/G3P[8] | NC_011502 | vertebrates,human | 1 | Reoviridae,Rotavirus,Rotavirus A | seg. 8 | FJ947204 |
| Rotavirus A human/Bethesda/DC5142/ 1975/G3P[8] | NC_011503 | vertebrates,human | 1 | Reoviridae,Rotavirus,Rotavirus A | seg. 9 | FJ947205 |
| Rotavirus A human/Bethesda/DC5142/ 1975/G3P[8] | NC_011504 | vertebrates,human | 1 | Reoviridae,Rotavirus,Rotavirus A | seg. 10 | FJ947206 |
| Rotavirus A human/Bethesda/DC5142/ 1975/G3P[8] | NC_011505 | vertebrates,human | 1 | Reoviridae,Rotavirus,Rotavirus A | seg. 11 | FJ947207 |
| Rotavirus A human/Bethesda/DC5142/ 1975/G3P[8] | NC_011507 | vertebrates,human | 1 | Reoviridae,Rotavirus,Rotavirus A | seg. 1 | FJ947197 |
| Rotavirus A human/Bethesda/DC5142/ 1975/G3P[8] | NC_011508 | vertebrates,human | 1 | Reoviridae,Rotavirus,Rotavirus A | seg. 3 | FJ947199 |
| Rotavirus A human/Bethesda/DC5142/ 1975/G3P[8] | NC_011509 | vertebrates,human | 1 | Reoviridae,Rotavirus,Rotavirus A | seg. 6 | FJ947202 |
| Rotavirus A human/Bethesda/DC5142/ 1975/G3P[8] | NC_011510 | vertebrates,human | 1 | Reoviridae,Rotavirus,Rotavirus A | seg. 4 | FJ947200 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Bethesda/DC5491/ 1991/G3P[8] | NC_011500 | vertebrates,human | 1 | Reoviridae,Rotavirus,Rotavirus A | seg. 5 | FJ947498 |
| Rotavirus A human/Bethesda/DC5491/ 1991/G3P[8] | NC_011501 | vertebrates,human | 1 | Reoviridae,Rotavirus,Rotavirus A | seg. 7 | FJ947500 |
| Rotavirus A human/Bethesda/DC5491/ 1991/G3P[8] | NC_011502 | vertebrates,human | 1 | Reoviridae,Rotavirus,Rotavirus A | seg. 8 | FJ947501 |
| Rotavirus A human/Bethesda/DC5491/ 1991/G3P[8] | NC_011504 | vertebrates,human | 1 | Reoviridae,Rotavirus,Rotavirus A | seg. 10 | FJ947503 |
| Rotavirus A human/Bethesda/DC5491/ 1991/G3P[8] | NC_011505 | vertebrates,human | 1 | Reoviridae,Rotavirus,Rotavirus A | seg. 11 | FJ947504 |
| Rotavirus A human/Bethesda/DC5491/ 1991/G3P[8] | NC_011506 | vertebrates,human | 1 | Reoviridae,Rotavirus,Rotavirus A | seg. 2 | FJ947495 |
| Rotavirus A human/Bethesda/DC5491/ 1991/G3P[8] | NC_011508 | vertebrates,human | 1 | Reoviridae,Rotavirus,Rotavirus A | seg. 3 | FJ947496 |
| Rotavirus A human/Bethesda/DC5491/ 1991/G3P[8] | NC_011509 | vertebrates,human | 1 | Reoviridae,Rotavirus,Rotavirus A | seg. 6 | FJ947499 |
| Rotavirus A human/Bethesda/DC5491/ 1991/G3P[8] | NC_011510 | vertebrates,human | 1 | Reoviridae,Rotavirus,Rotavirus A | seg. 4 | FJ947497 |
| Rotavirus A human/Bethesda/DC5544/ 1991/G3P[8] | NC_011500 | vertebrates,human | 1 | Reoviridae,Rotavirus,Rotavirus A | seg. 5 | FJ947509 |
| Rotavirus A human/Bethesda/DC5544/ 1991/G3P[8] | NC_011501 | vertebrates,human | 1 | Reoviridae,Rotavirus,Rotavirus A | seg. 7 | FJ947511 |
| Rotavirus A human/Bethesda/DC5544/ 1991/G3P[8] | NC_011502 | vertebrates,human | 1 | Reoviridae,Rotavirus,Rotavirus A | seg. 8 | FJ947512 |
| Rotavirus A human/Bethesda/DC5544/ 1991/G3P[8] | NC_011504 | vertebrates,human | 1 | Reoviridae,Rotavirus,Rotavirus A | seg. 10 | FJ947514 |
| Rotavirus A human/Bethesda/DC5544/ 1991/G3P[8] | NC_011505 | vertebrates,human | 1 | Reoviridae,Rotavirus,Rotavirus A | seg. 11 | FJ947515 |
| Rotavirus A human/Bethesda/DC5544/ 1991/G3P[8] | NC_011506 | vertebrates,human | 1 | Reoviridae,Rotavirus,Rotavirus A | seg. 2 | FJ947506 |
| Rotavirus A human/Bethesda/DC5544/ 1991/G3P[8] | NC_011507 | vertebrates,human | 1 | Reoviridae,Rotavirus,Rotavirus A | seg. 1 | FJ947505 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Rotavirus A human/Bethesda/DC5544/ 1991/G3P[8] | NC_011508 | vertebrates,human | Reoviridae,Rotavirus,Rotavirus A | 1 | seg. 3 | FJ947507 |
| Rotavirus A human/Bethesda/DC5544/ 1991/G3P[8] | NC_011509 | vertebrates,human | Reoviridae,Rotavirus,Rotavirus A | 1 | seg. 6 | FJ947510 |
| Rotavirus A human/Bethesda/DC5544/ 1991/G3P[8] | NC_011510 | vertebrates,human | Reoviridae,Rotavirus,Rotavirus A | 1 | seg. 4 | FJ947508 |
| Rotavirus A human/Bethesda/DC5549/ 1991/G3P[8] | NC_011500 | vertebrates,human | Reoviridae,Rotavirus,Rotavirus A | 1 | seg. 5 | FJ947520 |
| Rotavirus A human/Bethesda/DC5549/ 1991/G3P[8] | NC_011501 | vertebrates,human | Reoviridae,Rotavirus,Rotavirus A | 1 | seg. 7 | FJ947522 |
| Rotavirus A human/Bethesda/DC5549/ 1991/G3P[8] | NC_011502 | vertebrates,human | Reoviridae,Rotavirus,Rotavirus A | 1 | seg. 8 | FJ947523 |
| Rotavirus A human/Bethesda/DC5549/ 1991/G3P[8] | NC_011504 | vertebrates,human | Reoviridae,Rotavirus,Rotavirus A | 1 | seg. 10 | FJ947525 |
| Rotavirus A human/Bethesda/DC5549/ 1991/G3P[8] | NC_011505 | vertebrates,human | Reoviridae,Rotavirus,Rotavirus A | 1 | seg. 11 | FJ947526 |
| Rotavirus A human/Bethesda/DC5549/ 1991/G3P[8] | NC_011506 | vertebrates,human | Reoviridae,Rotavirus,Rotavirus A | 1 | seg. 2 | FJ947517 |
| Rotavirus A human/Bethesda/DC5549/ 1991/G3P[8] | NC_011507 | vertebrates,human | Reoviridae,Rotavirus,Rotavirus A | 1 | seg. 1 | FJ947516 |
| Rotavirus A human/Bethesda/DC5549/ 1991/G3P[8] | NC_011508 | vertebrates,human | Reoviridae,Rotavirus,Rotavirus A | 1 | seg. 3 | FJ947518 |
| Rotavirus A human/Bethesda/DC5549/ 1991/G3P[8] | NC_011509 | vertebrates,human | Reoviridae,Rotavirus,Rotavirus A | 1 | seg. 6 | FJ947521 |
| Rotavirus A human/Bethesda/DC5549/ 1991/G3P[8] | NC_011510 | vertebrates,human | Reoviridae,Rotavirus,Rotavirus A | 1 | seg. 4 | FJ947519 |
| Rotavirus A human/Bethesda/DC5553/ 1991/G3P[8] | NC_011500 | vertebrates,human | Reoviridae,Rotavirus,Rotavirus A | 1 | seg. 5 | FJ947940 |
| Rotavirus A human/Bethesda/DC5553/ 1991/G3P[8] | NC_011501 | vertebrates,human | Reoviridae,Rotavirus,Rotavirus A | 1 | seg. 7 | FJ947942 |
| Rotavirus A human/Bethesda/DC5553/ 1991/G3P[8] | NC_011502 | vertebrates,human | Reoviridae,Rotavirus,Rotavirus A | 1 | seg. 8 | FJ947943 |

| Taxonomy | Rep.Acc.ID | Host | # GN's | Lineage | Seg. Count | GN.Acc.IDs |
|---|---|---|---|---|---|---|
| Rotavirus A human/Bethesda/DC5553/1991/G3P[8] | NC_011504 | vertebrates,human | 1 | Reoviridae,Rotavirus,Rotavirus A | seg. 10 | FJ947945

TABLE 10-continued

| Taxonomy | Rep.Acc.ID | Host | ViroCap-1.0 Taxonomy | | Seg. Count | GN.Acc.IDs |
| --- | --- | --- | --- | --- | --- | --- |
| | | | Lineage | # GN's | | |
| Rotavirus A human/Bethesda/DC5710/ 1991/G3P[8] | NC_011510 | vertebrates,human | Reoviridae,Rotavirus,Rotavirus A | 1 | seg. 4 | FJ947785 |
| Rotavirus A human/Bethesda/DC5728/ 1991/G3P[8] | NC_011500 | vertebrates,human | Reoviridae,Rotavirus,Rotavirus A | 1 | seg. 5 | FJ947333 |
| Rotavirus A human/Bethesda/DC5728/ 1991/G3P[8] | NC_011501 | vertebrates,human | Reoviridae,Rotavirus,Rotavirus A | 1 | seg. 7 | FJ947335 |
| Rotavirus A human/Bethesda/DC5728/ 1991/G3P[8] | NC_011502 | vertebrates,human | Reoviridae,Rotavirus,Rotavirus A | 1 | seg. 8 | FJ947336 |
| Rotavirus A human/Bethesda/DC5728/ 1991/G3P[8] | NC_011504 | vertebrates,human | Reoviridae,Rotavirus,Rotavirus A | 1 | seg. 10 | FJ947338 |
| Rotavirus A human/Bethesda/DC5728/ 1991/G3P[8] | NC_011505 | vertebrates,human | Reoviridae,Rotavirus,Rotavirus A | 1 | seg. 11 | FJ947339 |
| Rotavirus A human/Bethesda/DC5728/ 1991/G3P[8] | NC_011506 | vertebrates,human | Reoviridae,Rotavirus,Rotavirus A | 1 | seg. 2 | FJ947330 |
| Rotavirus A human/Bethesda/DC5728/ 1991/G3P[8] | NC_011507 | vertebrates,human | Reoviridae,Rotavirus,Rotavirus A | 1 | seg. 1 | FJ947329 |
| Rotavirus A human/Bethesda/DC5728/ 1991/G3P[8] | NC_011509 | vertebrates,human | Reoviridae,Rotavirus,Rotavirus A | 1 | seg. 6 | FJ947334 |
| Rotavirus A human/Bethesda/DC5728/ 1991/G3P[8] | NC_011510 | vertebrates,human | Reoviridae,Rotavirus,Rotavirus A | 1 | seg. 4 | FJ947332 |
| Rotavirus A human/Bethesda/DC5751/ 1991/G3P[8] | NC_011500 | vertebrates,human | Reoviridae,Rotavirus,Rotavirus A | 1 | seg. 5 | FJ947797 |
| Rotavirus A human/Bethesda/DC5751/ 1991/G3P[8] | NC_011501 | vertebrates,human | Reoviridae,Rotavirus,Rotavirus A | 1 | seg. 7 | FJ947799 |
| Rotavirus A human/Bethesda/DC5751/ 1991/G3P[8] | NC_011502 | vertebrates,human | Reoviridae,Rotavirus,Rotavirus A | 1 | seg. 8 | FJ947800 |
| Rotavirus A human/Bethesda/DC5751/ 1991/G3P[8] | NC_011503 | vertebrates,human | Reoviridae,Rotavirus,Rotavirus A | 1 | seg. 9 | FJ947801 |
| Rotavirus A human/Bethesda/DC5751/ 1991/G3P[8] | NC_011504 | vertebrates,human | Reoviridae,Rotavirus,Rotavirus A | 1 | seg. 10 | FJ947802 |
| Rotavirus A human/Bethesda/DC5751/ 1991/G3P[8] | NC_011505 | vertebrates,human | Reoviridae,Rotavirus,Rotavirus A | 1 | seg. 11 | FJ947803 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC5751/1991/G3P[8] | NC_011507 | vertebrates,human | Reoviridae,Rotavirus,Rotavirus A | 1 | seg. 1 | FJ947793 |
| Rotavirus A human/Bethesda/DC5751/1991/G3P[8] | NC_011508 | vertebrates,human | Reoviridae,Rotavirus,Rotavirus A | 1 | seg. 3 | FJ947795 |
| Rotavirus A human/Bethesda/DC5751/1991/G3P[8] | NC_011509 | vertebrates,human | Reoviridae,Rotavirus,Rotavirus A | 1 | seg. 6 | FJ947798 |
| Rotavirus A human/Bethesda/DC5751/1991/G3P[8] | NC_011510 | vertebrates,human | Reoviridae,Rotavirus,Rotavirus A | 1 | seg. 4 | FJ947796 |
| Rotavirus A human/Bethesda/DC792/1 980/G3P[8] | NC_011500 | vertebrates,human | Reoviridae,Rotavirus,Rotavirus A | 1 | seg. 5 | FJ947764 |
| Rotavirus A human/Bethesda/DC792/1 980/G3P[8] | NC_011501 | vertebrates,human | Reoviridae,Rotavirus,Rotavirus A | 1 | seg. 7 | FJ947766 |
| Rotavirus A human/Bethesda/DC792/1 980/G3P[8] | NC_011502 | vertebrates,human | Reoviridae,Rotavirus,Rotavirus A | 1 | seg. 8 | FJ947767 |
| Rotavirus A human/Bethesda/DC792/1 980/G3P[8] | NC_011504 | vertebrates,human | Reoviridae,Rotavirus,Rotavirus A | 1 | seg. 10 | FJ947769 |
| Rotavirus A human/Bethesda/DC792/1 980/G3P[8] | NC_011505 | vertebrates,human | Reoviridae,Rotavirus,Rotavirus A | 1 | seg. 11 | FJ947770 |
| Rotavirus A human/Bethesda/DC792/1 980/G3P[8] | NC_011506 | vertebrates,human | Reoviridae,Rotavirus,Rotavirus A | 1 | seg. 2 | FJ947761 |
| Rotavirus A human/Bethesda/DC792/1 980/G3P[8] | NC_011507 | vertebrates,human | Reoviridae,Rotavirus,Rotavirus A | 1 | seg. 1 | FJ947760 |
| Rotavirus A human/Bethesda/DC792/1 980/G3P[8] | NC_011508 | vertebrates,human | Reoviridae,Rotavirus,Rotavirus A | 1 | seg. 3 | FJ947762 |
| Rotavirus A human/Bethesda/DC792/1 980/G3P[8] | NC_011509 | vertebrates,human | Reoviridae,Rotavirus,Rotavirus A | 1 | seg. 6 | FJ947765 |
| Rotavirus A human/Bethesda/DC792/1 980/G3P[8] | NC_011510 | vertebrates,human | Reoviridae,Rotavirus,Rotavirus A | 1 | seg. 4 | FJ947763 |
| Rotavirus A human/Bethesda/DC827/1 978/G4P[8] | NC_011500 | vertebrates,human | Reoviridae,Rotavirus,Rotavirus A | 1 | seg. 5 | HM773957 |
| Rotavirus A human/Bethesda/DC827/1 978/G4P[8] | NC_011501 | vertebrates,human | Reoviridae,Rotavirus,Rotavirus A | 1 | seg. 7 | HM773959 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Bethesda/DC827/1 978/G4P[8] | NC_011502 | vertebrates,human | Reoviridae,Rotavirus,Rotavirus A | 1 | seg. 8 | HM773960 |
| Rotavirus A human/Bethesda/DC827/1 978/G4P[8] | NC_011503 | vertebrates,human | Reoviridae,Rotavirus,Rotavirus A | 1 | seg. 9 | HM773961 |
| Rotavirus A human/Bethesda/DC827/1 978/G4P[8] | NC_011504 | vertebrates,human | Reoviridae,Rotavirus,Rotavirus A | 1 | seg. 10 | HM773962 |
| Rotavirus A human/Bethesda/DC827/1 978/G4P[8] | NC_011505 | vertebrates,human | Reoviridae,Rotavirus,Rotavirus A | 1 | seg. 11 | HM773963 |
| Rotavirus A human/Bethesda/DC827/1 978/G4P[8] | NC_011506 | vertebrates,human | Reoviridae,Rotavirus,Rotavirus A | 1 | seg. 2 | HM773954 |
| Rotavirus A human/Bethesda/DC827/1 978/G4P[8] | NC_011507 | vertebrates,human | Reoviridae,Rotavirus,Rotavirus A | 1 | seg. 1 | HM773953 |
| Rotavirus A human/Bethesda/DC827/1 978/G4P[8] | NC_011508 | vertebrates,human | Reoviridae,Rotavirus,Rotavirus A | 1 | seg. 3 | HM773955 |
| Rotavirus A human/Bethesda/DC827/1 978/G4P[8] | NC_011509 | vertebrates,human | Reoviridae,Rotavirus,Rotavirus A | 1 | seg. 6 | HM773958 |
| Rotavirus A human/Bethesda/DC827/1 978/G4P[8] | NC_011510 | vertebrates,human | Reoviridae,Rotavirus,Rotavirus A | 1 | seg. 4 | HM773956 |
| Rotavirus A human/USA/2007719698/2 0071G1P[8] | NC_011500 | vertebrates,human | Reoviridae,Rotavirus,Rotavirus A | 1 | seg. 5 | HM773770 |
| Rotavirus A human/USA/2007719698/2 007/G1P[8] | NC_011501 | vertebrates,human | Reoviridae,Rotavirus,Rotavirus A | 1 | seg. 7 | HM773772 |
| Rotavirus A human/USA/2007719698/2 007/G1P[8] | NC_011502 | vertebrates,human | Reoviridae,Rotavirus,Rotavirus A | 1 | seg. 8 | HM773773 |
| Rotavirus A human/USA/2007719698/2 007/G1P[8] | NC_011503 | vertebrates,human | Reoviridae,Rotavirus,Rotavirus A | 1 | seg. 9 | HM773774 |
| Rotavirus A human/USA/2007719698/2 007/G1P[8] | NC_011504 | vertebrates,human | Reoviridae,Rotavirus,Rotavirus A | 1 | seg. 10 | HM773775 |
| Rotavirus A human/USA/2007719698/2 007/G1P[8] | NC_011505 | vertebrates,human | Reoviridae,Rotavirus,Rotavirus A | 1 | seg. 11 | HM773776 |
| Rotavirus A human/USA/2007719698/2 007/G1P[8] | NC_011506 | vertebrates,human | Reoviridae,Rotavirus,Rotavirus A | 1 | seg. 2 | HM773767 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/USA/2007719698/2007/G1P[8] | NC_011507 | vertebrates,human | 1 | Reoviridae,Rotavirus,Rotavirus A | seg. 1 | HM773766 |
| Rotavirus A human/USA/2007719698/2007/G1P[8] | NC_011508 | vertebrates,human | 1 | Reoviridae,Rotavirus,Rotavirus A | seg. 3 | HM773768 |
| Rotavirus A human/USA/2007719698/2007/G1P[8] | NC_011509 | vertebrates,human | 1 | Reoviridae,Rotavirus,Rotavirus A | seg. 6 | HM773771 |
| Rotavirus A human/USA/2007719698/2007/G1P[8] | NC_011510 | vertebrates,human | 1 | Reoviridae,Rotavirus,Rotavirus A | seg. 4 | HM773769 |
| Rotavirus A human/USA/2007719739/2007/G1P[8] | NC_011500 | vertebrates,human | 1 | Reoviridae,Rotavirus,Rotavirus A | seg. 5 | HM773759 |
| Rotavirus A human/USA/2007719739/2007/G1P[8] | NC_011501 | vertebrates,human | 1 | Reoviridae,Rotavirus,Rotavirus A | seg. 7 | HM773761 |
| Rotavirus A human/USA/2007719739/2007/G1P[8] | NC_011502 | vertebrates,human | 1 | Reoviridae,Rotavirus,Rotavirus A | seg. 8 | HM773762 |
| Rotavirus A human/USA/2007719739/2007/G1P[8] | NC_011503 | vertebrates,human | 1 | Reoviridae,Rotavirus,Rotavirus A | seg. 9 | HM773763 |
| Rotavirus A human/USA/2007719739/2007/G1P[8] | NC_011504 | vertebrates,human | 1 | Reoviridae,Rotavirus,Rotavirus A | seg. 10 | HM773764 |
| Rotavirus A human/USA/2007719739/2007/G1P[8] | NC_011505 | vertebrates,human | 1 | Reoviridae,Rotavirus,Rotavirus A | seg. 11 | HM773765 |
| Rotavirus A human/USA/2007719739/2007/G1P[8] | NC_011506 | vertebrates,human | 1 | Reoviridae,Rotavirus,Rotavirus A | seg. 2 | HM773756 |
| Rotavirus A human/USA/2007719739/2007/G1P[8] | NC_011507 | vertebrates,human | 1 | Reoviridae,Rotavirus,Rotavirus A | seg. 1 | HM773755 |
| Rotavirus A human/USA/2007719739/2007/G1P[8] | NC_011508 | vertebrates,human | 1 | Reoviridae,Rotavirus,Rotavirus A | seg. 3 | HM773757 |
| Rotavirus A human/USA/2007719739/2007/G1P[8] | NC_011509 | vertebrates,human | 1 | Reoviridae,Rotavirus,Rotavirus A | seg. 6 | HM773760 |
| Rotavirus A human/USA/2007719739/2007/G1P[8] | NC_011510 | vertebrates,human | 1 | Reoviridae,Rotavirus,Rotavirus A | seg. 4 | HM773758 |
| Rotavirus A human/USA/2007719825/2007/G1P[8] | NC_011500 | vertebrates,human | 1 | Reoviridae,Rotavirus,Rotavirus A | seg. 5 | HM773748 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/USA/2007719825/2 007/G1P[8] | NC_011501 | vertebrates,human | Reoviridae,Rotavirus,Rotavirus A | 1 | seg. 7 | HM773750 |
| Rotavirus A human/USA/2007719825/2 007/G1P[8] | NC_011502 | vertebrates,human | Reoviridae,Rotavirus,Rotavirus A | 1 | seg. 8 | HM773751 |
| Rotavirus A human/USA/2007719825/2 007/G1P[8] | NC_011503 | vertebrates,human | Reoviridae,Rotavirus,Rotavirus A | 1 | seg. 9 | HM773752 |
| Rotavirus A human/USA/2007719825/2 007/G1P[8] | NC_011504 | vertebrates,human | Reoviridae,Rotavirus,Rotavirus A | 1 | seg. 10 | HM773753 |
| Rotavirus A human/USA/2007719825/2 007/G1P[8] | NC_011505 | vertebrates,human | Reoviridae,Rotavirus,Rotavirus A | 1 | seg. 11 | HM773754 |
| Rotavirus A human/USA/2007719825/2 007/G1P[8] | NC_011506 | vertebrates,human | Reoviridae,Rotavirus,Rotavirus A | 1 | seg. 2 | HM773745 |
| Rotavirus A human/USA/2007719825/2 007/G1P[8] | NC_011507 | vertebrates,human | Reoviridae,Rotavirus,Rotavirus A | 1 | seg. 1 | HM773744 |
| Rotavirus A human/USA/2007719825/2 007/G1P[8] | NC_011508 | vertebrates,human | Reoviridae,Rotavirus,Rotavirus A | 1 | seg. 3 | HM773746 |
| Rotavirus A human/Victoria/CK00026/2 005/G1P[8] | NC_011508 | vertebrates,human | Reoviridae,Rotavirus,Rotavirus A | 1 | seg. 3 | JF490334 |
| Rotavirus A human/Victoria/CK00026/2 005/G1P[8] | NC_011509 | vertebrates,human | Reoviridae,Rotavirus,Rotavirus A | 1 | seg. 6 | JF490332 |
| Rotavirus A human/Victoria/CK00026/2 005/G1P[8] | NC_011510 | vertebrates,human | Reoviridae,Rotavirus,Rotavirus A | 1 | seg. 4 | JF490333 |
| Rotavirus A human/Victoria/CK00027/2 054/G1P[8] | NC_011500 | vertebrates,human | Reoviridae,Rotavirus,Rotavirus A | 1 | seg. 5 | JF490338 |
| Rotavirus A human/Victoria/CK00027/2 054/G1P[8] | NC_011501 | vertebrates,human | Reoviridae,Rotavirus,Rotavirus A | 1 | seg. 7 | JF490342 |
| Rotavirus A human/Victoria/CK00027/2 054/G1P[8] | NC_011502 | vertebrates,human | Reoviridae,Rotavirus,Rotavirus A | 1 | seg. 8 | JF490337 |
| Rotavirus A human/Victoria/CK00027/2 054/G1P[8] | NC_011503 | vertebrates,human | Reoviridae,Rotavirus,Rotavirus A | 1 | seg. 9 | JF490341 |
| Rotavirus A human/Victoria/CK00027/2 054/G1P[8] | NC_011504 | vertebrates,human | Reoviridae,Rotavirus,Rotavirus A | 1 | seg. 10 | JF490340 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Victoria/CK00027/2054/G1P[8] | NC_011505 | vertebrates,human | 1 | Reoviridae,Rotavirus,Rotavirus A | seg. 11 | JF490339 |
| Rotavirus A human/Victoria/CK00027/2054/G1P[8] | NC_011506 | vertebrates,human | 1 | Reoviridae,Rotavirus,Rotavirus A | seg. 2 | JF490345 |
| Rotavirus A human/Victoria/CK00027/2054/G1P[8] | NC_011507 | vertebrates,human | 1 | Reoviridae,Rotavirus,Rotavirus A | seg. 1 | JF490336 |
| Rotavirus A human/Victoria/CK00027/2054/G1P[8] | NC_011508 | vertebrates,human | 1 | Reoviridae,Rotavirus,Rotavirus A | seg. 3 | JF490346 |
| Rotavirus A human/Victoria/CK00027/2054/G1P[8] | NC_011509 | vertebrates,human | 1 | Reoviridae,Rotavirus,Rotavirus A | seg. 6 | JF490343 |
| Rotavirus A human/Victoria/CK00027/2054/G1P[8] | NC_011510 | vertebrates,human | 1 | Reoviridae,Rotavirus,Rotavirus A | seg. 4 | JF490344 |
| Rotavirus A human/Victoria/CK00028/2005/G1P[8] | NC_011500 | vertebrates,human | 1 | Reoviridae,Rotavirus,Rotavirus A | seg. 5 | JF490357 |
| Rotavirus A human/Victoria/CK00028/2005/G1P[8] | NC_011501 | vertebrates,human | 1 | Reoviridae,Rotavirus,Rotavirus A | seg. 7 | JF490352 |
| Rotavirus A human/Victoria/CK00028/2005/G1P[8] | NC_011502 | vertebrates,human | 1 | Reoviridae,Rotavirus,Rotavirus A | seg. 8 | JF490348 |
| Rotavirus A human/Victoria/CK00028/2005/G1P[8] | NC_011503 | vertebrates,human | 1 | Reoviridae,Rotavirus,Rotavirus A | seg. 9 | JF490351 |
| Rotavirus A human/Victoria/CK00028/2005/G1P[8] | NC_011504 | vertebrates,human | 1 | Reoviridae,Rotavirus,Rotavirus A | seg. 10 | JF490350 |
| Rotavirus A human/Victoria/CK00028/2005/G1P[8] | NC_011505 | vertebrates,human | 1 | Reoviridae,Rotavirus,Rotavirus A | seg. 11 | JF490349 |
| Rotavirus A human/Victoria/CK00028/2005/G1P[8] | NC_011506 | vertebrates,human | 1 | Reoviridae,Rotavirus,Rotavirus A | seg. 2 | JF490356 |
| Rotavirus A human/Victoria/CK00028/2005/G1P[8] | NC_011507 | vertebrates,human | 1 | Reoviridae,Rotavirus,Rotavirus A | seg. 1 | JF490347 |
| Rotavirus A human/Victoria/CK00028/2005/G1P[8] | NC_011508 | vertebrates,human | 1 | Reoviridae,Rotavirus,Rotavirus A | seg. 3 | JF490355 |
| Rotavirus A human/Victoria/CK00028/2005/G1P[8] | NC_011509 | vertebrates,human | 1 | Reoviridae,Rotavirus,Rotavirus A | seg. 6 | JF490353 |

TABLE 10-continued

| Taxonomy | Rep.Acc.ID | Host | # GN's | VıroCap-1.0 Taxonomy Lineage | Seg. Count | GN.Acc.IDs |
|---|---|---|---|---|---|---|
| Rotavirus A human/Victoria/CK00028/2 005/G1P[8] | NC_011510 | vertebrates,human | 1 | Reoviridae,Rotavirus,Rotavirus A | seg. 4 | JF490354 |
| Rotavirus A human/Victoria/CK00029/2 006/G1P[8] | NC_011500 | vertebrates,human | 1 | Reoviridae,Rotavirus,Rotavirus A | seg. 5 | JF490360 |
| Rotavirus A human/Victoria/CK00029/2 006/G1P[8] | NC_011501 | vertebrates,human | 1 | Reoviridae,Rotavirus,Rotavirus A | seg. 7 | JF490363 |
| Rotavirus A human/Victoria/CK00029/2 006/G1P[8] | NC_011502 | vertebrates,human | 1 | Reoviridae,Rotavirus,Rotavirus A | seg. 8 | JF490359 |
| Rotavirus A human/Victoria/CK00029/2 006/G1P[8] | NC_011503 | vertebrates,human | 1 | Reoviridae,Rotavirus,Rotavirus A | seg. 9 | JF490368 |
| Rotavirus A human/Victoria/CK00029/2 006/G1P[8] | NC_011504 | vertebrates,human | 1 | Reoviridae,Rotavirus,Rotavirus A | seg. 10 | JF490362 |
| Rotavirus A human/Victoria/CK00029/2 006/G1P[8] | NC_011505 | vertebrates,human | 1 | Reoviridae,Rotavirus,Rotavirus A | seg. 11 | JF490361 |
| Rotavirus A human/Victoria/CK00029/2 006/G1P[8] | NC_011506 | vertebrates,human | 1 | Reoviridae,Rotavirus,Rotavirus A | seg. 2 | JF490367 |
| Rotavirus A human/Victoria/CK00029/2 006/G1P[8] | NC_011507 | vertebrates,human | 1 | Reoviridae,Rotavirus,Rotavirus A | seg. 1 | JF490358 |
| Rotavirus A human/Victoria/CK00029/2 006/G1P[8] | NC_011508 | vertebrates,human | 1 | Reoviridae,Rotavirus,Rotavirus A | seg. 3 | JF490366 |
| Rotavirus A human/Victoria/CK00029/2 006/G1P[8] | NC_011509 | vertebrates,human | 1 | Reoviridae,Rotavirus,Rotavirus A | seg. 6 | JF490364 |
| Rotavirus A human/Victoria/CK00029/2 006/G1P[8] | NC_011510 | vertebrates,human | 1 | Reoviridae,Rotavirus,Rotavirus A | seg. 4 | JF490365 |
| Rotavirus A human/Victoria/CK00030/2 006/G1P[8] | NC_011500 | vertebrates,human | 1 | Reoviridae,Rotavirus,Rotavirus A | seg. 5 | JF490371 |
| Rotavirus A human/Victoria/CK00030/2 006/G1P[8] | NC_011501 | vertebrates,human | 1 | Reoviridae,Rotavirus,Rotavirus A | seg. 7 | JF490375 |
| Rotavirus A human/Victoria/CK00030/2 006/G1P[8] | NC_011502 | vertebrates,human | 1 | Reoviridae,Rotavirus,Rotavirus A | seg. 8 | JF490370 |
| Rotavirus A human/Victoria/CK00030/2 006/G1P[8] | NC_011503 | vertebrates,human | 1 | Reoviridae,Rotavirus,Rotavirus A | seg. 9 | JF490374 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Victoria/CK00030/2 006/G1P[8] | NC_011504 | vertebrates,human | Reoviridae,Rotavirus,Rotavirus A | 1 | seg. 10 | JF490373 |
| Rotavirus A human/Victoria/CK00030/2 006/G1P[8] | NC_011505 | vertebrates,human | Reoviridae,Rotavirus,Rotavirus A | 1 | seg. 11 | JF490372 |
| Rotavirus A human/Victoria/CK00030/2 006/G1P[8] | NC_011506 | vertebrates,human | Reoviridae,Rotavirus,Rotavirus A | 1 | seg. 2 | JF490379 |
| Rotavirus A human/Victoria/CK00030/2 006/G1P[8] | NC_011507 | vertebrates,human | Reoviridae,Rotavirus,Rotavirus A | 1 | seg. 1 | JF490369 |
| Rotavirus A human/Victoria/CK00030/2 006/G1P[8] | NC_011508 | vertebrates,human | Reoviridae,Rotavirus,Rotavirus A | 1 | seg. 3 | JF490377 |
| Rotavirus A human/Victoria/CK00030/2 006/G1P[8] | NC_011509 | vertebrates,human | Reoviridae,Rotavirus,Rotavirus A | 1 | seg. 6 | JF490376 |
| Rotavirus A human/Victoria/CK00030/2 006/G1P[8] | NC_011510 | vertebrates,human | Reoviridae,Rotavirus,Rotavirus A | 1 | seg. 4 | JF490378 |
| Rotavirus A human/Victoria/CK00032/2 006/G1P[8] | NC_011500 | vertebrates,human | Reoviridae,Rotavirus,Rotavirus A | 1 | seg. 5 | JF490382 |
| Rotavirus A human/Victoria/CK00032/2 006/G1P[8] | NC_011501 | vertebrates,human | Reoviridae,Rotavirus,Rotavirus A | 1 | seg. 7 | JF490386 |
| Rotavirus A human/Victoria/CK00032/2 006/G1P[8] | NC_011502 | vertebrates,human | Reoviridae,Rotavirus,Rotavirus A | 1 | seg. 8 | JF490381 |
| Rotavirus A human/Victoria/CK00032/2 006/G1P[8] | NC_011503 | vertebrates,human | Reoviridae,Rotavirus,Rotavirus A | 1 | seg. 9 | JF490385 |
| Rotavirus A human/Victoria/CK00032/2 006/G1P[8] | NC_011504 | vertebrates,human | Reoviridae,Rotavirus,Rotavirus A | 1 | seg. 10 | JF490384 |
| Rotavirus A human/Victoria/CK00032/2 006/G1P[8] | NC_011505 | vertebrates,human | Reoviridae,Rotavirus,Rotavirus A | 1 | seg. 11 | JF490383 |
| Rotavirus A human/Victoria/CK00032/2 006/G1P[8] | NC_011506 | vertebrates,human | Reoviridae,Rotavirus,Rotavirus A | 1 | seg. 2 | JF490390 |
| Rotavirus A human/Victoria/CK00032/2 006/G1P[8] | NC_011507 | vertebrates,human | Reoviridae,Rotavirus,Rotavirus A | 1 | seg. 1 | JF490380 |
| Rotavirus A human/Victoria/CK00032/2 006/G1P[8] | NC_011508 | vertebrates,human | Reoviridae,Rotavirus,Rotavirus A | 1 | seg. 3 | JF490389 |

TABLE 10-continued

| Taxonomy | Rep.Acc.ID | Host | # GN's | VisCap-1.0 Taxonomy Lineage | Seg. Count | GN.Acc.IDs |
|---|---|---|---|---|---|---|
| Rotavirus A human/Victoria/CK00032/2006/G1P[8] | NC_011509 | vertebrates,human | 1 | Reoviridae,Rotavirus,Rotavirus A | seg. 6 | JF490387 |
| Rotavirus A human/Victoria/CK00032/2006/G1P[8] | NC_011510 | vertebrates,human | 1 | Reoviridae,Rotavirus,Rotavirus A | seg. 4 | JF490388 |
| Rotavirus A human/Victoria/CK00033/2007/G1P[8] | NC_011500 | vertebrates,human | 1 | Reoviridae,Rotavirus,Rotavirus A | seg. 5 | JF490393 |
| Rotavirus A human/Victoria/CK00033/2007/G1P[8] | NC_011501 | vertebrates,human | 1 | Reoviridae,Rotavirus,Rotavirus A | seg. 7 | JF490397 |
| Rotavirus A human/Victoria/CK00033/2007/G1P[8] | NC_011502 | vertebrates,human | 1 | Reoviridae,Rotavirus,Rotavirus A | seg. 8 | JF490392 |
| Rotavirus A human/Victoria/CK00033/2007/G1P[8] | NC_011503 | vertebrates,human | 1 | Reoviridae,Rotavirus,Rotavirus A | seg. 9 | JF490396 |
| Rotavirus A human/Victoria/CK00033/2007/G1P[8] | NC_011504 | vertebrates,human | 1 | Reoviridae,Rotavirus,Rotavirus A | seg. 10 | JF490395 |
| Rotavirus A human/Victoria/CK00033/2007/G1P[8] | NC_011505 | vertebrates,human | 1 | Reoviridae,Rotavirus,Rotavirus A | seg. 11 | JF490394 |
| Rotavirus A human/Victoria/CK00033/2007/G1P[8] | NC_011506 | vertebrates,human | 1 | Reoviridae,Rotavirus,Rotavirus A | seg. 2 | JF490401 |
| Rotavirus A human/Victoria/CK00033/2007/G1P[8] | NC_011507 | vertebrates,human | 1 | Reoviridae,Rotavirus,Rotavirus A | seg. 1 | JF490391 |
| Rotavirus A human/Victoria/CK00033/2007/G1P[8] | NC_011508 | vertebrates,human | 1 | Reoviridae,Rotavirus,Rotavirus A | seg. 3 | JF490400 |
| Rotavirus A human/Victoria/CK00033/2007/G1P[8] | NC_011509 | vertebrates,human | 1 | Reoviridae,Rotavirus,Rotavirus A | seg. 6 | JF490398 |
| Rotavirus A human/Victoria/CK00033/2007/G1P[8] | NC_011510 | vertebrates,human | 1 | Reoviridae,Rotavirus,Rotavirus A | seg. 4 | JF490399 |
| Rotavirus A human/Victoria/CK00034/2007/G1P[8] | NC_011500 | vertebrates,human | 1 | Reoviridae,Rotavirus,Rotavirus A | seg. 5 | JF490410 |
| Rotavirus A human/Victoria/CK00034/2007/G1P[8] | NC_011501 | vertebrates,human | 1 | Reoviridae,Rotavirus,Rotavirus A | seg. 7 | JF490407 |
| Rotavirus A human/Victoria/CK00034/2007/G1P[8] | NC_011502 | vertebrates,human | 1 | Reoviridae,Rotavirus,Rotavirus A | seg. 8 | JF490403 |

TABLE 10-continued

VisoCap-1.0 Taxonomy

| Taxonomy | Rep.Acc.ID | Host | # GN's | Lineage | Seg. Count | GN.Acc.IDs |
|---|---|---|---|---|---|---|
| Rotavirus A human/Victoria/CK00034/2007/G1P[8] | NC_011503 | vertebrates,human | 1 | Reoviridae,Rotavirus,Rotavirus A | seg. 9 | JF490406 |
| Rotavirus A human/Victoria/CK00034/2007/G1P[8] | NC_011504 | vertebrates,human | 1 | Reoviridae,Rotavirus,Rotavirus A | seg. 10 | JF490405 |
| Rotavirus A human/Victoria/CK00034/2007/G1P[8] | NC_011505 | vertebrates,human | 1 | Reoviridae,Rotavirus,Rotavirus A | seg. 11 | JF490404 |
| Rotavirus A human/Victoria/CK00034/2007/G1P[8] | NC_011506 | vertebrates,human | 1 | Reoviridae,Rotavirus,Rotavirus A | seg. 2 | JF490412 |
| Rotavirus A human/Victoria/CK00034/2007/G1P[8] | NC_011507 | vertebrates,human | 1 | Reoviridae,Rotavirus,Rotavirus A | seg. 1 | JF490402 |
| Rotavirus A human/Victoria/CK00034/2007/G1P[8] | NC_011508 | vertebrates,human | 1 | Reoviridae,Rotavirus,Rotavirus A | seg. 3 | JF490411 |
| Rotavirus A human/Victoria/CK00034/2007/G1P[8] | NC_011509 | vertebrates,human | 1 | Reoviridae,Rotavirus,Rotavirus A | seg. 6 | JF490408 |
| Rotavirus A human/Victoria/CK00034/2007/G1P[8] | NC_011510 | vertebrates,human | 1 | Reoviridae,Rotavirus,Rotavirus A | seg. 4 | JF490409 |
| Rotavirus A human/Victoria/CK00035/2005/G1P[8] | NC_011500 | vertebrates,human | 1 | Reoviridae,Rotavirus,Rotavirus A | seg. 5 | JF490415 |
| Rotavirus A human/Victoria/CK00035/2005/G1P[8] | NC_011501 | vertebrates,human | 1 | Reoviridae,Rotavirus,Rotavirus A | seg. 7 | JF490419 |
| Rotavirus A human/Victoria/CK00035/2005/G1P[8] | NC_011502 | vertebrates,human | 1 | Reoviridae,Rotavirus,Rotavirus A | seg. 8 | JF490414 |
| Rotavirus A human/Victoria/CK00035/2005/G1P[8] | NC_011503 | vertebrates,human | 1 | Reoviridae,Rotavirus,Rotavirus A | seg. 9 | JF490418 |
| Rotavirus A human/Victoria/CK00035/2005/G1P[8] | NC_011504 | vertebrates,human | 1 | Reoviridae,Rotavirus,Rotavirus A | seg. 10 | JF490417 |
| Rotavirus A human/Victoria/CK00035/2005/G1P[8] | NC_011505 | vertebrates,human | 1 | Reoviridae,Rotavirus,Rotavirus A | seg. 11 | JF490416 |
| Rotavirus A human/Victoria/CK00035/2005/G1P[8] | NC_011506 | vertebrates,human | 1 | Reoviridae,Rotavirus,Rotavirus A | seg. 2 | JF490423 |
| Rotavirus A human/Victoria/CK00035/2005/G1P[8] | NC_011507 | vertebrates,human | 1 | Reoviridae,Rotavirus,Rotavirus A | seg. 1 | JF490413 |

TABLE 10-continued

| | | | | ViroCap-1.0 Taxonomy | | | |
|---|---|---|---|---|---|---|---|
| Taxonomy | Rep.Acc.ID | Host | # GN's | Lineage | Seg. Count | GN.Acc.IDs | |
| Rotavirus A human/Victoria/CK00035/2 005/G1P[8] | NC_011508 | vertebrates,human | 1 | Reoviridae,Rotavirus,Rotavirus A | seg. 3 | JF490422 | |
| Rotavirus A human/Victoria/CK00035/2 005/G1P[8] | NC_011509 | vertebrates,human | 1 | Reoviridae,Rotavirus,Rotavirus A | seg. 6 | JF490420 | |
| Rotavirus A human/Victoria/CK00035/2 005/G1P[8] | NC_011510 | vertebrates,human | 1 | Reoviridae,Rotavirus,Rotavirus A | seg. 4 | JF490421 | |
| Rotavirus A human/Victoria/CK00036/2 005/G1P[8] | NC_011500 | vertebrates,human | 1 | Reoviridae,Rotavirus,Rotavirus A | seg. 5 | JF490434 | |
| Rotavirus A human/Victoria/CK00036/2 005/G1P[8] | NC_011501 | vertebrates,human | 1 | Reoviridae,Rotavirus,Rotavirus A | seg. 7 | JF490429 | |
| Rotavirus A human/Victoria/CK00036/2 005/G1P[8] | NC_011502 | vertebrates,human | 1 | Reoviridae,Rotavirus,Rotavirus A | seg. 8 | JF490425 | |
| Rotavirus A human/Victoria/CK00036/2 005/G1P[8] | NC_011503 | vertebrates,human | 1 | Reoviridae,Rotavirus,Rotavirus A | seg. 9 | JF490428 | |
| Rotavirus A human/Victoria/CK00036/2 005/G1P[8] | NC_011504 | vertebrates,human | 1 | Reoviridae,Rotavirus,Rotavirus A | seg. 10 | JF490427 | |
| Rotavirus A human/Victoria/CK00036/2 005/G1P[8] | NC_011505 | vertebrates,human | 1 | Reoviridae,Rotavirus,Rotavirus A | seg. 11 | JF490426 | |
| Rotavirus A human/Victoria/CK00036/2 005/G1P[8] | NC_011506 | vertebrates,human | 1 | Reoviridae,Rotavirus,Rotavirus A | seg. 2 | JF490433 | |
| Rotavirus A human/Victoria/CK00036/2 005/G1P[8] | NC_011507 | vertebrates,human | 1 | Reoviridae,Rotavirus,Rotavirus A | seg. 1 | JF490424 | |
| Rotavirus A human/Victoria/CK00036/2 005/G1P[8] | NC_011508 | vertebrates,human | 1 | Reoviridae,Rotavirus,Rotavirus A | seg. 3 | JF490432 | |
| Rotavirus A human/Victoria/CK00036/2 005/G1P[8] | NC_011509 | vertebrates,human | 1 | Reoviridae,Rotavirus,Rotavirus A | seg. 6 | JF490430 | |
| Rotavirus A human/Victoria/CK00036/2 005/G1P[8] | NC_011510 | vertebrates,human | 1 | Reoviridae,Rotavirus,Rotavirus A | seg. 4 | JF490431 | |
| Rotavirus A human/Victoria/CK00037/2 006/G1P[8] | NC_011500 | vertebrates,human | 1 | Reoviridae,Rotavirus,Rotavirus A | seg. 5 | JF490443 | |
| Rotavirus A human/Victoria/CK00037/2 006/G1P[8] | NC_011501 | vertebrates,human | 1 | Reoviridae,Rotavirus,Rotavirus A | seg. 7 | JF490439 | |

TABLE 10-continued

| Taxonomy | Rep.Acc.ID | Host | # GN's | VIroCap-1.0 Taxonomy Lineage | Seg. Count | GN.Acc.IDs |
|---|---|---|---|---|---|---|
| Rotavirus A human/Victoria/CK00037/2006/G1P[8] | NC_011502 | vertebrates,human | 1 | Reoviridae,Rotavirus,Rotavirus A | seg. 8 | JF490436 |
| Rotavirus A human/Victoria/CK00037/2006/G1P[8] | NC_011503 | vertebrates,human | 1 | Reoviridae,Rotavirus,Rotavirus A | seg. 9 | JF490444 |
| Rotavirus A human/Victoria/CK00037/2006/G1P[8] | NC_011504 | vertebrates,human | 1 | Reoviridae,Rotavirus,Rotavirus A | seg. 10 | JF490438 |
| Rotavirus A human/Victoria/CK00037/2006/G1P[8] | NC_011505 | vertebrates,human | 1 | Reoviridae,Rotavirus,Rotavirus A | seg. 11 | JF490437 |
| Rotavirus A human/Victoria/CK00037/2006/G1P[8] | NC_011506 | vertebrates,human | 1 | Reoviridae,Rotavirus,Rotavirus A | seg. 2 | JF490445 |
| Rotavirus A human/Victoria/CK00037/2006/G1P[8] | NC_011507 | vertebrates,human | 1 | Reoviridae,Rotavirus,Rotavirus A | seg. 1 | JF490435 |
| Rotavirus A human/Victoria/CK00037/2006/G1P[8] | NC_011508 | vertebrates,human | 1 | Reoviridae,Rotavirus,Rotavirus A | seg. 3 | JF490442 |
| Rotavirus A human/Victoria/CK00037/2006/G1P[8] | NC_011509 | vertebrates,human | 1 | Reoviridae,Rotavirus,Rotavirus A | seg. 6 | JF490440 |
| Rotavirus A human/Victoria/CK00037/2006/G1P[8] | NC_011510 | vertebrates,human | 1 | Reoviridae,Rotavirus,Rotavirus A | seg. 4 | JF490441 |
| Rotavirus A human/Victoria/CK00039/2006/G1P[8] | NC_011500 | vertebrates,human | 1 | Reoviridae,Rotavirus,Rotavirus A | seg. 5 | JF490448 |
| Rotavirus A human/Victoria/CK00039/2006/G1P[8] | NC_011501 | vertebrates,human | 1 | Reoviridae,Rotavirus,Rotavirus A | seg. 7 | JF490452 |
| Rotavirus A human/Victoria/CK00039/2006/G1P[8] | NC_011502 | vertebrates,human | 1 | Reoviridae,Rotavirus,Rotavirus A | seg. 8 | JF490447 |
| Rotavirus A human/Victoria/CK00039/2006/G1P[8] | NC_011503 | vertebrates,human | 1 | Reoviridae,Rotavirus,Rotavirus A | seg. 9 | JF490451 |
| Rotavirus A human/Victoria/CK00039/2006/G1P[8] | NC_011504 | vertebrates,human | 1 | Reoviridae,Rotavirus,Rotavirus A | seg. 10 | JF490450 |
| Rotavirus A human/Victoria/CK00039/2006/G1P[8] | NC_011505 | vertebrates,human | 1 | Reoviridae,Rotavirus,Rotavirus A | seg. 11 | JF490449 |
| Rotavirus A human/Victoria/CK00039/2006/G1P[8] | NC_011506 | vertebrates,human | 1 | Reoviridae,Rotavirus,Rotavirus A | seg. 2 | JF490456 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Victoria/CK00039/2006/G1P[8] | NC_011507 | vertebrates,human | 1 | Reoviridae,Rotavirus,Rotavirus A | seg. 1 | JF490446 |
| Rotavirus A human/Victoria/CK00039/2006/G1P[8] | NC_011508 | vertebrates,human | 1 | Reoviridae,Rotavirus,Rotavirus A | seg. 3 | JF490455 |
| Rotavirus A human/Victoria/CK00039/2006/G1P[8] | NC_011509 | vertebrates,human | 1 | Reoviridae,Rotavirus,Rotavirus A | seg. 6 | JF490453 |
| Rotavirus A human/Victoria/CK00039/2006/G1P[8] | NC_011510 | vertebrates,human | 1 | Reoviridae,Rotavirus,Rotavirus A | seg. 4 | JF490454 |
| Rotavirus A human/Victoria/CK00040/2006/G1P[8] | NC_011500 | vertebrates,human | 1 | Reoviridae,Rotavirus,Rotavirus A | seg. 5 | JF490459 |
| Rotavirus A human/Victoria/CK00040/2006/G1P[8] | NC_011501 | vertebrates,human | 1 | Reoviridae,Rotavirus,Rotavirus A | seg. 7 | JF490463 |
| Rotavirus A human/Victoria/CK00040/2006/G1P[8] | NC_011502 | vertebrates,human | 1 | Reoviridae,Rotavirus,Rotavirus A | seg. 8 | JF490458 |
| Rotavirus A human/Victoria/CK00040/2006/G1P[8] | NC_011503 | vertebrates,human | 1 | Reoviridae,Rotavirus,Rotavirus A | seg. 9 | JF490462 |
| Rotavirus A human/Victoria/CK00040/2006/G1P[8] | NC_011504 | vertebrates,human | 1 | Reoviridae,Rotavirus,Rotavirus A | seg. 10 | JF490461 |
| Rotavirus A human/Victoria/CK00040/2006/G1P[8] | NC_011505 | vertebrates,human | 1 | Reoviridae,Rotavirus,Rotavirus A | seg. 11 | JF490460 |
| Rotavirus A human/Victoria/CK00040/2006/G1P[8] | NC_011506 | vertebrates,human | 1 | Reoviridae,Rotavirus,Rotavirus A | seg. 2 | JF490467 |
| Rotavirus A human/Victoria/CK00040/2006/G1P[8] | NC_011507 | vertebrates,human | 1 | Reoviridae,Rotavirus,Rotavirus A | seg. 1 | JF490457 |
| Rotavirus A human/Victoria/CK00040/2006/G1P[8] | NC_011508 | vertebrates,human | 1 | Reoviridae,Rotavirus,Rotavirus A | seg. 3 | JF490466 |
| Rotavirus A human/Victoria/CK00040/2006/G1P[8] | NC_011509 | vertebrates,human | 1 | Reoviridae,Rotavirus,Rotavirus A | seg. 6 | JF490464 |
| Rotavirus A human/Victoria/CK00040/2006/G1P[8] | NC_011510 | vertebrates,human | 1 | Reoviridae,Rotavirus,Rotavirus A | seg. 4 | JF490465 |
| Rotavirus A human/Victoria/CK00041/2006/G1P[8] | NC_011500 | vertebrates,human | 1 | Reoviridae,Rotavirus,Rotavirus A | seg. 5 | JF490470 |

TABLE 10-continued

| Taxonomy | Rep.Acc.ID | Host | Lineage | ViroCap-1.0 Taxonomy # GN's | Seg. Count | GN.Acc.IDs |
|---|---|---|---|---|---|---|
| Rotavirus A human/Victoria/CK00041/2006/G1P[8] | NC_011501 | vertebrates,human | Reoviridae,Rotavirus,Rotavirus A | 1 | seg. 7 | JF490474 |
| Rotavirus A human/Victoria/CK00041/2006/G1P[8] | NC_011502 | vertebrates,human | Reoviridae,Rotavirus,Rotavirus A | 1 | seg. 8 | JF490469 |
| Rotavirus A human/Victoria/CK00041/2006/G1P[8] | NC_011503 | vertebrates,human | Reoviridae,Rotavirus,Rotavirus A | 1 | seg. 9 | JF490473 |
| Rotavirus A human/Victoria/CK00041/2006/G1P[8] | NC_011504 | vertebrates,human | Reoviridae,Rotavirus,Rotavirus A | 1 | seg. 10 | JF490472 |
| Rotavirus A human/Victoria/CK00041/2006/G1P[8] | NC_011505 | vertebrates,human | Reoviridae,Rotavirus,Rotavirus A | 1 | seg. 11 | JF490471 |
| Rotavirus A human/Victoria/CK00041/2006/G1P[8] | NC_011506 | vertebrates,human | Reoviridae,Rotavirus,Rotavirus A | 1 | seg. 2 | JF490478 |
| Rotavirus A human/Victoria/CK00041/2006/G1P[8] | NC_011507 | vertebrates,human | Reoviridae,Rotavirus,Rotavirus A | 1 | seg. 1 | JF490468 |
| Rotavirus A human/Victoria/CK00041/2006/G1P[8] | NC_011508 | vertebrates,human | Reoviridae,Rotavirus,Rotavirus A | 1 | seg. 3 | JF490477 |
| Rotavirus A human/Victoria/CK00041/2006/G1P[8] | NC_011509 | vertebrates,human | Reoviridae,Rotavirus,Rotavirus A | 1 | seg. 6 | JF490475 |
| Rotavirus A human/Victoria/CK00041/2006/G1P[8] | NC_011510 | vertebrates,human | Reoviridae,Rotavirus,Rotavirus A | 1 | seg. 4 | JF490476 |
| Rotavirus A human/Victoria/CK00043/2006/G1P[8] | NC_011500 | vertebrates,human | Reoviridae,Rotavirus,Rotavirus A | 1 | seg. 5 | JF490481 |
| Rotavirus A human/Victoria/CK00043/2006/G1P[8] | NC_011501 | vertebrates,human | Reoviridae,Rotavirus,Rotavirus A | 1 | seg. 7 | JF490485 |
| Rotavirus A human/Victoria/CK00043/2006/G1P[8] | NC_011502 | vertebrates,human | Reoviridae,Rotavirus,Rotavirus A | 1 | seg. 8 | JF490480 |
| Rotavirus A human/Victoria/CK00043/2006/G1P[8] | NC_011503 | vertebrates,human | Reoviridae,Rotavirus,Rotavirus A | 1 | seg. 9 | JF490484 |
| Rotavirus A human/Victoria/CK00043/2006/G1P[8] | NC_011504 | vertebrates,human | Reoviridae,Rotavirus,Rotavirus A | 1 | seg. 10 | JF490483 |
| Rotavirus A human/Victoria/CK00043/2006/G1P[8] | NC_011505 | vertebrates,human | Reoviridae,Rotavirus,Rotavirus A | 1 | seg. 11 | JF490482 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Victoria/CK00043/2006/G1P[8] | NC_011506 | vertebrates,human | 1 | Reoviridae,Rotavirus,Rotavirus A | seg. 2 | JF490489 |
| Rotavirus A human/Victoria/CK00043/2006/G1P[8] | NC_011507 | vertebrates,human | 1 | Reoviridae,Rotavirus,Rotavirus A | seg. 1 | JF490479 |
| Rotavirus A human/Victoria/CK00043/2006/G1P[8] | NC_011508 | vertebrates,human | 1 | Reoviridae,Rotavirus,Rotavirus A | seg. 3 | JF490488 |
| Rotavirus A human/Victoria/CK00043/2006/G1P[8] | NC_011509 | vertebrates,human | 1 | Reoviridae,Rotavirus,Rotavirus A | seg. 6 | JF490486 |
| Rotavirus A human/Victoria/CK00043/2006/G1P[8] | NC_011510 | vertebrates,human | 1 | Reoviridae,Rotavirus,Rotavirus A | seg. 4 | JF490487 |
| Rotavirus A human/Victoria/CK00045/2006/G1P[8] | NC_011500 | vertebrates,human | 1 | Reoviridae,Rotavirus,Rotavirus A | seg. 5 | JF490495 |
| Rotavirus A human/Victoria/CK00045/2006/G1P[8] | NC_011501 | vertebrates,human | 1 | Reoviridae,Rotavirus,Rotavirus A | seg. 7 | JF490499 |
| Rotavirus A human/Victoria/CK00045/2006/G1P[8] | NC_011502 | vertebrates,human | 1 | Reoviridae,Rotavirus,Rotavirus A | seg. 8 | JF490494 |
| Rotavirus A human/Victoria/CK00045/2006/G1P[8] | NC_011503 | vertebrates,human | 1 | Reoviridae,Rotavirus,Rotavirus A | seg. 9 | JF490498 |
| Rotavirus A human/Victoria/CK00045/2006/G1P[8] | NC_011504 | vertebrates,human | 1 | Reoviridae,Rotavirus,Rotavirus A | seg. 10 | JF490497 |
| Rotavirus A human/Victoria/CK00045/2006/G1P[8] | NC_011505 | vertebrates,human | 1 | Reoviridae,Rotavirus,Rotavirus A | seg. 11 | JF490496 |
| Rotavirus A human/Victoria/CK00045/2006/G1P[8] | NC_011506 | vertebrates,human | 1 | Reoviridae,Rotavirus,Rotavirus A | seg. 2 | JF490493 |
| Rotavirus A human/Victoria/CK00045/2006/G1P[8] | NC_011507 | vertebrates,human | 1 | Reoviridae,Rotavirus,Rotavirus A | seg. 1 | JF490490 |
| Rotavirus A human/Victoria/CK00045/2006/G1P[8] | NC_011508 | vertebrates,human | 1 | Reoviridae,Rotavirus,Rotavirus A | seg. 3 | JF490492 |
| Rotavirus A human/Victoria/CK00045/2006/G1P[8] | NC_011509 | vertebrates,human | 1 | Reoviridae,Rotavirus,Rotavirus A | seg. 6 | JF490500 |
| Rotavirus A human/Victoria/CK00045/2006/G1P[8] | NC_011510 | vertebrates,human | 1 | Reoviridae,Rotavirus,Rotavirus A | seg. 4 | JF490491 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Victoria/CK00046/2006/G1P[8] | NC_011500 | vertebrates,human | 1 | Reoviridae,Rotavirus,Rotavirus A | seg. 5 | JF490503 |
| Rotavirus A human/Victoria/CK00046/2006/G1P[8] | NC_011501 | vertebrates,human | 1 | Reoviridae,Rotavirus,Rotavirus A | seg. 7 | JF490507 |
| Rotavirus A human/Victoria/CK00046/2006/G1P[8] | NC_011502 | vertebrates,human | 1 | Reoviridae,Rotavirus,Rotavirus A | seg. 8 | JF490502 |
| Rotavirus A human/Victoria/CK00046/2006/G1P[8] | NC_011503 | vertebrates,human | 1 | Reoviridae,Rotavirus,Rotavirus A | seg. 9 | JF490506 |
| Rotavirus A human/Victoria/CK00046/2006/G1P[8] | NC_011504 | vertebrates,human | 1 | Reoviridae,Rotavirus,Rotavirus A | seg. 10 | JF490505 |
| Rotavirus A human/Victoria/CK00046/2006/G1P[8] | NC_011505 | vertebrates,human | 1 | Reoviridae,Rotavirus,Rotavirus A | seg. 11 | JF490504 |
| Rotavirus A human/Victoria/CK00046/2006/G1P[8] | NC_011506 | vertebrates,human | 1 | Reoviridae,Rotavirus,Rotavirus A | seg. 2 | JF490511 |
| Rotavirus A human/Victoria/CK00046/2006/G1P[8] | NC_011507 | vertebrates,human | 1 | Reoviridae,Rotavirus,Rotavirus A | seg. 1 | JF490501 |
| Rotavirus A human/Victoria/CK00046/2006/G1P[8] | NC_011508 | vertebrates,human | 1 | Reoviridae,Rotavirus,Rotavirus A | seg. 3 | JF490510 |
| Rotavirus A human/Victoria/CK00046/2006/G1P[8] | NC_011509 | vertebrates,human | 1 | Reoviridae,Rotavirus,Rotavirus A | seg. 6 | JF490508 |
| Rotavirus A human/Victoria/CK00046/2006/G1P[8] | NC_011510 | vertebrates,human | 1 | Reoviridae,Rotavirus,Rotavirus A | seg. 4 | JF490509 |
| Rotavirus A human/Victoria/CK00047/2006/G1P[8] | NC_011500 | vertebrates,human | 1 | Reoviridae,Rotavirus,Rotavirus A | seg. 5 | JF490514 |
| Rotavirus A human/Victoria/CK00047/2006/G1P[8] | NC_011501 | vertebrates,human | 1 | Reoviridae,Rotavirus,Rotavirus A | seg. 7 | JF490518 |
| Rotavirus A human/Victoria/CK00047/2006/G1P[8] | NC_011502 | vertebrates,human | 1 | Reoviridae,Rotavirus,Rotavirus A | seg. 8 | JF490513 |
| Rotavirus A human/Victoria/CK00047/2006/G1P[8] | NC_011503 | vertebrates,human | 1 | Reoviridae,Rotavirus,Rotavirus A | seg. 9 | JF490517 |
| Rotavirus A human/Victoria/CK00047/2006/G1P[8] | NC_011504 | vertebrates,human | 1 | Reoviridae,Rotavirus,Rotavirus A | seg. 10 | JF490516 |

TABLE 10-continued

VrioCap-1.0 Taxonomy

| Taxonomy | Rep.Acc.ID | Host | # GN's | Lineage | Seg. Count | GN.Acc.IDs |
|---|---|---|---|---|---|---|
| Rotavirus A human/Victoria/CK00047/2 006/G1P[8] | NC_011505 | vertebrates,human | 1 | Reoviridae,Rotavirus,Rotavirus A | seg. 11 | JF490515 |
| Rotavirus A human/Victoria/CK00047/2 006/G1P[8] | NC_011506 | vertebrates,human | 1 | Reoviridae,Rotavirus,Rotavirus A | seg. 2 | JF490522 |
| Rotavirus A human/Victoria/CK00047/2 006/G1P[8] | NC_011507 | vertebrates,human | 1 | Reoviridae,Rotavirus,Rotavirus A | seg. 1 | JF490512 |
| Rotavirus A human/Victoria/CK00047/2 006/G1P[8] | NC_011508 | vertebrates,human | 1 | Reoviridae,Rotavirus,Rotavirus A | seg. 3 | JF490521 |
| Rotavirus A human/Victoria/CK00047/2 006/G1P[8] | NC_011509 | vertebrates,human | 1 | Reoviridae,Rotavirus,Rotavirus A | seg. 6 | JF490519 |
| Rotavirus A human/Victoria/CK00047/2 006/G1P[8] | NC_011510 | vertebrates,human | 1 | Reoviridae,Rotavirus,Rotavirus A | seg. 4 | JF490520 |
| Rotavirus A human/Victoria/CK00048/2 004/G1P[8] | NC_011500 | vertebrates,human | 1 | Reoviridae,Rotavirus,Rotavirus A | seg. 5 | JF490525 |
| Rotavirus A human/Victoria/CK00048/2 004/G1P[8] | NC_011501 | vertebrates,human | 1 | Reoviridae,Rotavirus,Rotavirus A | seg. 7 | JF490529 |
| Rotavirus A human/Victoria/CK00048/2 004/G1P[8] | NC_011502 | vertebrates,human | 1 | Reoviridae,Rotavirus,Rotavirus A | seg. 8 | JF490524 |
| Rotavirus A human/Victoria/CK00048/2 004/G1P[8] | NC_011503 | vertebrates,human | 1 | Reoviridae,Rotavirus,Rotavirus A | seg. 9 | JF490528 |
| Rotavirus A human/Victoria/CK00048/2 004/G1P[8] | NC_011504 | vertebrates,human | 1 | Reoviridae,Rotavirus,Rotavirus A | seg. 10 | JF490527 |
| Rotavirus A human/Victoria/CK00048/2 004/G1P[8] | NC_011505 | vertebrates,human | 1 | Reoviridae,Rotavirus,Rotavirus A | seg. 11 | JF490526 |
| Rotavirus A human/Victoria/CK00048/2 004/G1P[8] | NC_011506 | vertebrates,human | 1 | Reoviridae,Rotavirus,Rotavirus A | seg. 2 | JF490533 |
| Rotavirus A human/Victoria/CK00048/2 004/G1P[8] | NC_011507 | vertebrates,human | 1 | Reoviridae,Rotavirus,Rotavirus A | seg. 1 | JF490523 |
| Rotavirus A human/Victoria/CK00048/2 004/G1P[8] | NC_011508 | vertebrates,human | 1 | Reoviridae,Rotavirus,Rotavirus A | seg. 3 | JF490532 |
| Rotavirus A human/Victoria/CK00048/2 004/G1P[8] | NC_011509 | vertebrates,human | 1 | Reoviridae,Rotavirus,Rotavirus A | seg. 6 | JF490530 |

TABLE 10-continued

| Taxonomy | Rep.Acc.ID | Host | Lineage | # GN's | Seg. Count | GN.Acc.IDs |
|---|---|---|---|---|---|---|
| Rotavirus A human/Victoria/CK00048/2 004/G1P[8] | NC_011510 | vertebrates,human | Reoviridae,Rotavirus,Rotavirus A | 1 | seg. 4 | JF490531 |
| Rotavirus A human/Victoria/CK00049/2 004/G1P[8] | NC_011500 | vertebrates,human | Reoviridae,Rotavirus,Rotavirus A | 1 | seg. 5 | JF490536 |
| Rotavirus A human/Victoria/CK00049/2 004/G1P[8] | NC_011501 | vertebrates,human | Reoviridae,Rotavirus,Rotavirus A | 1 | seg. 7 | JF490540 |
| Rotavirus A human/Victoria/CK00049/2 004/G1P[8] | NC_011502 | vertebrates,human | Reoviridae,Rotavirus,Rotavirus A | 1 | seg. 8 | JF490535 |
| Rotavirus A human/Victoria/CK00049/2 004/G1P[8] | NC_011503 | vertebrates,human | Reoviridae,Rotavirus,Rotavirus A | 1 | seg. 9 | JF490539 |
| Rotavirus A human/Victoria/CK00049/2 004/G1P[8] | NC_011504 | vertebrates,human | Reoviridae,Rotavirus,Rotavirus A | 1 | seg. 10 | JF490538 |
| Rotavirus A human/Victoria/CK00049/2 004/G1P[8] | NC_011505 | vertebrates,human | Reoviridae,Rotavirus,Rotavirus A | 1 | seg. 11 | JF490537 |
| Rotavirus A human/Victoria/CK00049/2 004/G1P[8] | NC_011506 | vertebrates,human | Reoviridae,Rotavirus,Rotavirus A | 1 | seg. 2 | JF490544 |
| Rotavirus A human/Victoria/CK00049/2 004/G1P[8] | NC_011507 | vertebrates,human | Reoviridae,Rotavirus,Rotavirus A | 1 | seg. 1 | JF490534 |
| Rotavirus A human/Victoria/CK00049/2 004/G1P[8] | NC_011508 | vertebrates,human | Reoviridae,Rotavirus,Rotavirus A | 1 | seg. 3 | JF490542 |
| Rotavirus A human/Victoria/CK00049/2 004/G1P[8] | NC_011509 | vertebrates,human | Reoviridae,Rotavirus,Rotavirus A | 1 | seg. 6 | JF490541 |
| Rotavirus A human/Victoria/CK00049/2 004/G1P[8] | NC_011510 | vertebrates,human | Reoviridae,Rotavirus,Rotavirus A | 1 | seg. 4 | JF490543 |
| Rotavirus A human/Victoria/CK00050/2 005/G1P[8] | NC_011500 | vertebrates,human | Reoviridae,Rotavirus,Rotavirus A | 1 | seg. 5 | JF490553 |
| Rotavirus A human/Victoria/CK00050/2 005/G1P[8] | NC_011501 | vertebrates,human | Reoviridae,Rotavirus,Rotavirus A | 1 | seg. 7 | JF490550 |
| Rotavirus A human/Victoria/CK00050/2 005/G1P[8] | NC_011502 | vertebrates,human | Reoviridae,Rotavirus,Rotavirus A | 1 | seg. 8 | JF490546 |
| Rotavirus A human/Victoria/CK00050/2 005/G1P[8] | NC_011503 | vertebrates,human | Reoviridae,Rotavirus,Rotavirus A | 1 | seg. 9 | JF490549 |

TABLE 10-continued

| | | | ViroCap-1.0 Taxonomy | | | |
|---|---|---|---|---|---|---|
| Taxonomy | Rep.Acc.ID | Host | # GN's | Lineage | Seg. Count | GN.Acc.IDs |
| Rotavirus A human/Victoria/CK00050/2005/G1P[8] | NC_011504 | vertebrates,human | 1 | Reoviridae,Rotavirus,Rotavirus A | seg. 10 | JF490548 |
| Rotavirus A human/Victoria/CK00050/2005/G1P[8] | NC_011505 | vertebrates,human | 1 | Reoviridae,Rotavirus,Rotavirus A | seg. 11 | JF490547 |
| Rotavirus A human/Victoria/CK00050/2005/G1P[8] | NC_011506 | vertebrates,human | 1 | Reoviridae,Rotavirus,Rotavirus A | seg. 2 | JF490555 |
| Rotavirus A human/Victoria/CK00050/2005/G1P[8] | NC_011507 | vertebrates,human | 1 | Reoviridae,Rotavirus,Rotavirus A | seg. 1 | JF490545 |
| Rotavirus A human/Victoria/CK00050/2005/G1P[8] | NC_011508 | vertebrates,human | 1 | Reoviridae,Rotavirus,Rotavirus A | seg. 3 | JF490552 |
| Rotavirus A human/Victoria/CK00050/2005/G1P[8] | NC_011509 | vertebrates,human | 1 | Reoviridae,Rotavirus,Rotavirus A | seg. 6 | JF490551 |
| Rotavirus A human/Victoria/CK00050/2005/G1P[8] | NC_011510 | vertebrates,human | 1 | Reoviridae,Rotavirus,Rotavirus A | seg. 4 | JF490554 |
| Rotavirus A pheasant-tc/GER/10V0112H5/2010/G23P[37] | NC_011502 | vertebrates,human | 1 | Reoviridae,Rotavirus,Rotavirus A | seg. 8 | JX204816 |
| Rotavirus A pheasant-tc/GER/10V0112H5/2010/G23P[37] | NC_011503 | vertebrates,human | 1 | Reoviridae,Rotavirus,Rotavirus A | seg. 9 | JX204818 |
| Rotavirus A pheasant-tc/GER/10V0112H5/2010/G23P[37] | NC_011506 | vertebrates,human | 1 | Reoviridae,Rotavirus,Rotavirus A | seg. 2 | JX204812 |
| Rotavirus A pheasant-tc/GER/10V0112H5/2010/G23P[37] | NC_011507 | vertebrates,human | 1 | Reoviridae,Rotavirus,Rotavirus A | seg. 1 | JX204811 |
| Rotavirus A pheasant-tc/GER/10V0112H5/2010/G23P[37] | NC_011508 | vertebrates,human | 1 | Reoviridae,Rotavirus,Rotavirus A | seg. 3 | JX204813 |
| Rotavirus A pheasant-tc/GER/10V0112H5/2010/G23P[37] | NC_011509 | vertebrates,human | 1 | Reoviridae,Rotavirus,Rotavirus A | seg. 6 | JX204815 |
| Rotavirus A pheasant-tc/GER/10V0112H5/2010/G23P[37] | NC_011510 | vertebrates,human | 1 | Reoviridae,Rotavirus,Rotavirus A | seg. 4 | JX204814 |
| Rotavirus A pheasant/HUN/2008 | NC_011503 | vertebrates,human | 3 | Reoviridae,Rotavirus,Rotavirus A | seg. 9 | FN393054,FN393055,FN393056 |
| Rotavirus A sable antelope/G6P[14] | NC_011500 | vertebrates,human | 1 | Reoviridae,Rotavirus,Rotavirus A | seg. 5 | FJ495130 |
| Rotavirus A sable antelope/G6P[14] | NC_011501 | vertebrates,human | 1 | Reoviridae,Rotavirus,Rotavirus A | seg. 7 | FJ495134 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Rotavirus A sable antelope/G6P[14] | NC_011502 | vertebrates,human | Reoviridae,Rotavirus,Rotavirus A | 1 | seg. 8 | FJ495132 |
| Rotavirus A sable antelope/G6P[14] | NC_011503 | vertebrates,human | Reoviridae,Rotavirus,Rotavirus A | 1 | seg. 9 | FJ495133 |
| Rotavirus A sable antelope/G6P[14] | NC_011504 | vertebrates,human | Reoviridae,Rotavirus,Rotavirus A | 1 | seg. 10 | FJ495135 |
| Rotavirus A sable antelope/G6P[14] | NC_011505 | vertebrates,human | Reoviridae,Rotavirus,Rotavirus A | 1 | seg. 11 | FJ495136 |
| Rotavirus A sable antelope/G6P[14] | NC_011506 | vertebrates,human | Reoviridae,Rotavirus,Rotavirus A | 1 | seg. 2 | FJ495127 |
| Rotavirus A sable antelope/G6P[14] | NC_011507 | vertebrates,human | Reoviridae,Rotavirus,Rotavirus A | 1 | seg. 1 | FJ495126 |
| Rotavirus A sable antelope/G6P[14] | NC_011508 | vertebrates,human | Reoviridae,Rotavirus,Rotavirus A | 1 | seg. 3 | FJ495128 |
| Rotavirus A sable antelope/G6P[14] | NC_011509 | vertebrates,human | Reoviridae,Rotavirus,Rotavirus A | 1 | seg. 6 | FJ495131 |
| Rotavirus A sable antelope/G6P[14] | NC_011510 | vertebrates,human | Reoviridae,Rotavirus,Rotavirus A | 1 | seg. 4 | FJ495129 |
| Rotavirus A strain 116E/AG | NC_011500 | vertebrates,human | Reoviridae,Rotavirus,Rotavirus A | 1 | seg. 5 | FJ361205 |
| Rotavirus A strain 116E/AG | NC_011501 | vertebrates,human | Reoviridae,Rotavirus,Rotavirus A | 1 | seg. 7 | FJ361207 |
| Rotavirus A strain 116E/AG | NC_011502 | vertebrates,human | Reoviridae,Rotavirus,Rotavirus A | 1 | seg. 8 | FJ361208 |
| Rotavirus A strain 116E/AG | NC_011503 | vertebrates,human | Reoviridae,Rotavirus,Rotavirus A | 1 | seg. 9 | FJ361209 |
| Rotavirus A strain 116E/AG 10 | NC_011504 | vertebrates,human | Reoviridae,Rotavirus,Rotavirus A | 1 | seg. | FJ361210 |
| Rotavirus A strain 116E/AG 11 | NC_011505 | vertebrates,human | Reoviridae,Rotavirus,Rotavirus A | 1 | seg. | FJ361211 |
| Rotavirus A strain 116E/AG | NC_011506 | vertebrates,human | Reoviridae,Rotavirus,Rotavirus A | 1 | seg. 2 | FJ361202 |
| Rotavirus A strain 116E/AG | NC_011507 | vertebrates,human | Reoviridae,Rotavirus,Rotavirus A | 1 | seg. 1 | FJ361201 |
| Rotavirus A strain 116E/AG | NC_011508 | vertebrates,human | Reoviridae,Rotavirus,Rotavirus A | 1 | seg. 3 | FJ361203 |
| Rotavirus A strain 116E/AG | NC_011509 | vertebrates,human | Reoviridae,Rotavirus,Rotavirus A | 1 | seg. 6 | FJ361206 |
| Rotavirus A strain 116E/AG | NC_011510 | vertebrates,human | Reoviridae,Rotavirus,Rotavirus A | 1 | seg. 4 | FJ361204 |
| Rotavirus A turkey-tc/GER/03V0002E10/2003/G22P[35] | NC_011502 | vertebrates,human | Reoviridae,Rotavirus,Rotavirus A | 1 | seg. 8 | JX204827 |
| Rotavirus A turkey-tc/GER/03V0002E10/2003/G22P[35] | NC_011503 | vertebrates,human | Reoviridae,Rotavirus,Rotavirus A | 1 | seg. 9 | JX204829 |
| Rotavirus A turkey-tc/GER/03V0002E10/2003/G22P[35] | NC_011506 | vertebrates,human | Reoviridae,Rotavirus,Rotavirus A | 1 | seg. 2 | JX204823 |
| Rotavirus A turkey-tc/GER/03V0002E10/2003/G22P[35] | NC_011507 | vertebrates,human | Reoviridae,Rotavirus,Rotavirus A | 1 | seg. 1 | JX204822 |
| Rotavirus A turkey-tc/GER/03V0002E10/2003/G22P[35] | NC_011508 | vertebrates,human | Reoviridae,Rotavirus,Rotavirus A | 1 | seg. 3 | JX204824 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A turkey-tc/GER/03V0002E10/2003/G22P[35] | NC_011509 | vertebrates,human | Reoviridae,Rotavirus,Rotavirus A | 1 | seg. 6 | JX204826 |
| Rotavirus A turkey-tc/GER/03V0002E10/2003/G22P[35] | NC_011510 | vertebrates,human | Reoviridae,Rotavirus,Rotavirus A | 1 | seg. 4 | JX204825 |
| Rotavirus B | NC_021541 | vertebrates,human | Reoviridae,Rotavirus,Rotavirus B | 1 | seg. 1 | M97203 |
| Rotavirus B | NC_021544 | vertebrates,human | Reoviridae,Rotavirus,Rotavirus B | 1 | seg. 6 | AF079157 |
| Rotavirus B | NC_021549 | vertebrates,human | Reoviridae,Rotavirus,Rotavirus B | 1 | seg. 11 | AF079158 |
| Rotavirus C | NC_007543 | vertebrates,human | Reoviridae,Rotavirus,Rotavirus C | 1 | seg. 6 | AJ132203 |
| Rotavirus C | NC_007544 | vertebrates,human | Reoviridae,Rotavirus,Rotavirus C | 1 | seg. 7 | AJ132204 |
| Rotavirus C | NC_007545 | vertebrates,human | Reoviridae,Rotavirus,Rotavirus C | 1 | seg. 9 | AJ132205 |
| Rotavirus C | NC_007546 | vertebrates,human | Reoviridae,Rotavirus,Rotavirus C | 1 | seg. 2 | AJ303139 |
| Rotavirus C | NC_007547 | vertebrates,human | Reoviridae,Rotavirus,Rotavirus C | 1 | seg. 1 | AJ304859 |
| Rotavirus C | NC_007569 | vertebrates,human | Reoviridae,Rotavirus,Rotavirus C | 1 | seg. 10 | M81488 |
| Rotavirus C | NC_007570 | vertebrates,human | Reoviridae,Rotavirus,Rotavirus C | 4 | seg. 5 | AF162434,M88768,EF528570,X59843 |
| Rotavirus C | NC_007571 | vertebrates,human | Reoviridae,Rotavirus,Rotavirus C | 15 | seg. 8 | U20990,U20989,U20994,U20991,U20993,X77257,U20992,X77258,EF528571,X77256,AJ549087,U20996,U20987,U20995,U20988 |
| Rotavirus C | NC_007572 | vertebrates,human | Reoviridae,Rotavirus,Rotavirus C | 1 | seg. 3 | X79442 |
| Rotavirus C | NC_007573 | vertebrates,human | Reoviridae,Rotavirus,Rotavirus C | 1 | seg. 11 | X83967 |
| Rotavirus C | NC_007574 | vertebrates,human | Reoviridae,Rotavirus,Rotavirus C | 1 | seg. 4 | X96697 |
| Rotavirus F chicken/03V0568/DEU/2003 | NC_021625 | vertebrates,human | Reoviridae,Rotavirus,Rotavirus F | 1 | seg. 1 | JN596591 |
| Rotavirus F chicken/03V0568/DEU/2003 | NC_021626 | vertebrates,human | Reoviridae,Rotavirus,Rotavirus F | 1 | seg. 2 | JQ919995 |
| Rotavirus F chicken/03V0568/DEU/2003 | NC_021627 | vertebrates,human | Reoviridae,Rotavirus,Rotavirus F | 1 | seg. 9 | JQ919998 |
| Rotavirus F chicken/03V0568/DEU/2003 | NC_021628 | vertebrates,human | Reoviridae,Rotavirus,Rotavirus F | 1 | seg. 8 | JQ920000 |
| Rotavirus F chicken/03V0568/DEU/2003 | NC_021629 | vertebrates,human | Reoviridae,Rotavirus,Rotavirus F | 1 | seg. 10 | JQ920003 |
| Rotavirus F chicken/03V0568/DEU/2003 | NC_021630 | vertebrates,human | Reoviridae,Rotavirus,Rotavirus F | 1 | seg. 4 | JQ919996 |
| Rotavirus F chicken/03V0568/DEU/2003 | NC_021631 | vertebrates,human | Reoviridae,Rotavirus,Rotavirus F | 1 | seg. 3 | JQ919997 |
| Rotavirus F chicken/03V0568/DEU/2003 | NC_021632 | vertebrates,human | Reoviridae,Rotavirus,Rotavirus F | 1 | seg. 5 | JQ919999 |
| Rotavirus F chicken/03V0568/DEU/2003 | NC_021633 | vertebrates,human | Reoviridae,Rotavirus,Rotavirus F | 1 | seg. 7 | JQ920001 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus F chicken/03V0568/DEU/2003 | NC_021634 | vertebrates,human | Reoviridae,Rotavirus,Rotavirus F | 1 | seg. 11 | JQ920002 |
| Rotavirus F chicken/03V0568/DEU/2003 | NC_021635 | vertebrates,human | Reoviridae,Rotavirus,Rotavirus F | 1 | seg. 6 | HQ403603 |
| Rotavirus G chicken/03V0567/DEU/2003 | NC_021580 | vertebrates,human | Reoviridae,Rotavirus,Rotavirus G | 1 | — | JQ920004 |
| Rotavirus G chicken/03V0567/DEU/2003 | NC_021581 | vertebrates,human | Reoviridae,Rotavirus,Rotavirus G | 1 | — | JQ920006 |
| Rotavirus G chicken/03V0567/DEU/2003 | NC_021582 | vertebrates,human | Reoviridae,Rotavirus,Rotavirus G | 1 | — | JQ920007 |
| Rotavirus G chicken/03V0567/DEU/2003 | NC_021583 | vertebrates,human | Reoviridae,Rotavirus,Rotavirus G | 1 | — | JQ920008 |
| Rotavirus G chicken/03V0567/DEU/2003 | NC_021584 | vertebrates,human | Reoviridae,Rotavirus,Rotavirus G | 1 | — | JQ920009 |
| Rotavirus G chicken/03V0567/DEU/2003 | NC_021585 | vertebrates,human | Reoviridae,Rotavirus,Rotavirus G | 1 | — | JQ920010 |
| Rotavirus G chicken/03V0567/DEU/2003 | NC_021586 | vertebrates,human | Reoviridae,Rotavirus,Rotavirus G | 1 | — | JQ920011 |
| Rotavirus G chicken/03V0567/DEU/2003 | NC_021587 | vertebrates,human | Reoviridae,Rotavirus,Rotavirus G | 1 | — | JQ920012 |
| Rotavirus G chicken/03V0567/DEU/2003 | NC_021588 | vertebrates,human | Reoviridae,Rotavirus,Rotavirus G | 1 | — | HQ403604 |
| Rotavirus G chicken/03V0567/DEU/2003 | NC_021589 | vertebrates,human | Reoviridae,Rotavirus,Rotavirus G | 1 | — | JQ920005 |
| Rotavirus G chicken/03V0567/DEU/2003 | NC_021590 | vertebrates,human | Reoviridae,Rotavirus,Rotavirus G | 1 | — | JN596592 |
| Rotavirus G1 | NC_011503 | vertebrates,human | Reoviridae,Rotavirus,Rotavirus A | 11 | seg. 9 | EU839916,EU839911,EU839909,EU839913,EU839912,EU839910,EU839915,EU839908,EU839907,EU839906,EU839914 |
| Rotavirus G1 | NC_011504 | vertebrates,human | Reoviridae,Rotavirus,Rotavirus A | 1 | seg. 10 | 19 |
| Rotavirus G10 | NC_011503 | vertebrates,human | Reoviridae,Rotavirus,Rotavirus A | 7 | seg. 9 | AY159645,AY159638,AY159631,AY159636,AY159632,AY159646,AY159633,AY159642,AY159643,AY159634,AY159644,AY159641,AY159640,AY159630,AY159637,AY159639,AY159648,AY159635,AY159647,AY816181,JF681943,AY843333,AY816182,AY855063,JF681941,AY843332 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rotavirus G10 | NC_011504 | vertebrates,human | 1 | Reoviridae,Rotavirus,Rotavirus A | seg. 10 | AY855068 |
| Rotavirus G12 | NC_011501 | vertebrates,human | 2 | Reoviridae,Rotavirus,Rotavirus A | seg. 7 | EU839967,EU839973 |
| Rotavirus G12 | NC_011502 | vertebrates,human | 2 | Reoviridae,Rotavirus,Rotavirus A | seg. 8 | EU839968,EU839974 |
| Rotavirus G12 | NC_011503 | vertebrates,human | 18 | Reoviridae,Rotavirus,Rotavirus A | seg. 9 | AB436818,AB436813,EU839943,EU83993 4,AB436814,EU8399 44,AB436815,EU839 942,EF059916,AB436 816,AB306271,AB43 6817,AB306270,EF05 9917,AB306268,EU8 39935,AB306269,AB 436819 |
| Rotavirus G12 | NC_011504 | vertebrates,human | 4 | Reoviridae,Rotavirus,Rotavirus A | seg. 10 | EU839969,EF059919,EU839975,EF059918 |
| Rotavirus G12 | NC_011505 | vertebrates,human | 2 | Reoviridae,Rotavirus,Rotavirus A | seg. 11 | EU839970,EU839976 |
| Rotavirus G12 | NC_011509 | vertebrates,human | 2 | Reoviridae,Rotavirus,Rotavirus A | seg. 6 | EU839965,EU839971 |
| Rotavirus G12 | NC_011510 | vertebrates,human | 2 | Reoviridae,Rotavirus,Rotavirus A | seg. 4 | EF059921,EF059920 |
| Rotavirus G2 | NC_011503 | vertebrates,human | 16 | Reoviridae,Rotavirus,Rotavirus A | seg. 9 | AY707784,EU839925,EU839919,EU83992 1,AY707785,EU8399 17,EU839926,EU839 918,EU839923,DQ47 8581,EU839924,EU8 39920,EU839922,EU 839928,AY707786,EU839927 |
| Rotavirus G2 | NC_011504 | vertebrates,human | 3 | Reoviridae,Rotavirus,Rotavirus A | seg. 10 | AY159649,AF401756,EU839964 |
| Rotavirus G2 | NC_011509 | vertebrates,human | 1 | Reoviridae,Rotavirus,Rotavirus A | seg. 6 | EU839963 |
| Rotavirus G3 | NC_011500 | vertebrates,human | 1 | Reoviridae,Rotavirus,Rotavirus A | seg. 5 | AY740735 |
| Rotavirus G3 | NC_011501 | vertebrates,human | 1 | Reoviridae,Rotavirus,Rotavirus A | seg. 7 | AY740734 |
| Rotavirus G3 | NC_011502 | vertebrates,human | 2 | Reoviridae,Rotavirus,Rotavirus A | seg. 8 | JQ358771,AY740733 |
| Rotavirus G3 | NC_011503 | vertebrates,human | 51 | Reoviridae,Rotavirus,Rotavirus A | seg. 9 | EF495119,EF495124,AY707791,D86276,E F495121,EF495127,D 0904498,D86266,D8 6280,D86264,D86282,JQ358764,D86269,D 86265,AY707789,AY 70792,EF495122,D 0904499,DQ995488,DQ995489,D86283,D 0904503,EF495118,DQ904500,DQ90450 5,AY870661,DQ9045 |

TABLE 10-continued

VirCap-1.0 Taxonomy

| Taxonomy | Rep.Acc.ID | Host | Lineage | # GN's | Seg. Count | GN.Acc.IDs |
|---|---|---|---|---|---|---|
| | | | | | | 06,EF495120,D86284,D86281,DQ904502,D86279,DQ904501,D86271,DQ995490,D8272,AY900173,AY707794,EF495126,D86627 8,D86268,D86267,D86274,EF495123,AY740736,DQ904504,AY707793,EF495125,D86275 |
| Rotavirus G3 | NC_011504 | vertebrates,human | Reoviridae,Rotavirus,Rotavirus A | 21 | seg. 10 | AB008240,AB008236,AB008234,AB008246,AB008230,AB008233,AB008237,AY740732,AB008242,AB008238,AB008243,AB008231,AB008244,AB008232,AB008245,AB008248,AB008247,AB008241,AB008239,AB008229,AB008235 |
| Rotavirus G3 | NC_011505 | vertebrates,human | Reoviridae,Rotavirus,Rotavirus A | 2 | seg. 11 | JQ358774,AY740731 |
| Rotavirus G3 | NC_011506 | vertebrates,human | Reoviridae,Rotavirus,Rotavirus A | 1 | seg. 2 | AY740740 |
| Rotavirus G3 | NC_011507 | vertebrates,human | Reoviridae,Rotavirus,Rotavirus A | 1 | seg. 1 | AY740741 |
| Rotavirus G3 | NC_011508 | vertebrates,human | Reoviridae,Rotavirus,Rotavirus A | 1 | seg. 3 | AY740739 |
| Rotavirus G3 | NC_011509 | vertebrates,human | Reoviridae,Rotavirus,Rotavirus A | 1 | seg. 6 | AY740737 |
| Rotavirus G3 | NC_011510 | vertebrates,human | Reoviridae,Rotavirus,Rotavirus A | 20 | seg. 4 | AY740738,AB008277,AB008279,AB008278,AB008290,AB008282,AB008289,AB008281,AB008272,AB008273,AB008274,AB008285,AB008275,AB008284,AB008286,AB008283,AB008280,AB008276,AB008288 |
| Rotavirus G4 | NC_011503 | vertebrates,human | Reoviridae,Rotavirus,Rotavirus A | 33 | seg. 9 | AB012066,AB012074,AF161822,AB039035,AB012075,AB03902 6,AB039027,AB012071,AB039025,AB012078,AF161821,AB039029,AF161823,AB012069,AF161817,AB012 |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| | | | | | | 065,AB012079,AB039028,AB012072,AF161818,AB039032,AB012077,AB012067,AB012076,AB012073,AB039031,AB012068,AB012070,AF161820,AB039030,AF161819,AB039034,AB039033 |
| Rotavirus G4 | NC_011504 | vertebrates,human | 33 | Reoviridae,Rotavirus,Rotavirus A | seg. 10 | AB008255,AB008261,AF161810,AB043069,AF161815,AB043026,AB008251,AB008260,AB008253,AB008262,AB008249,AF161811,AB043072,AB043075,AF161813,AB008258,AB043076,AF161816,AB008259,AB008252,AB008263,AB043077,AB008256,AB043073,AB043070,AB043078,AB043074,AF161814,AB008250,AB008254,AF161812 |
| Rotavirus G6 | NC_011503 | vertebrates,human | 1 | Reoviridae,Rotavirus,Rotavirus A | seg. 9 | AF532202 |
| Rotavirus G8 | NC_011503 | vertebrates,human | 1 | Reoviridae,Rotavirus,Rotavirus A | seg. 9 | AY855064 |
| Rotavirus G8 | NC_011510 | vertebrates,human | 1 | Reoviridae,Rotavirus,Rotavirus A | seg. 4 | AF045228 |
| Rotavirus G9 | NC_011503 | vertebrates,human | 156 | Reoviridae,Rotavirus,Rotavirus A | seg. 9 | AY253834,AJ250544,AB436831,AJ250276,EF199728,AB436820,AY699298,AB436832,AY262748,AY699302,AY307092,AY307088,AY307094,AB436833,AY866500,AY879296,AY699301,EF199729,AY253835,AY699291,FJ695604,EF199735,AJ250275,AY211065,AJ250270,EU839936,AJ250269,DQ647423,EU839929,EU839939,EF199736,AB436821,DQ056298,AY699292,AB091752,EF532837,AY699929 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0,AB436822,EF199738,AB091755,EU839937,AY262747,AY211067,AJ250268,AB364369,EU839933,AY253836,AB436834,AJ250274,EU839932,AY699293,DQ056299,AJ250277,DQ056300,EF199737,HQ018933,JF703095,DQ096290,AY695811,AY211068,HQ018932,AY253833,AY866504,EU839940,AY699294,AJ491179,DQ056297,EF199730,AB091750,AJ491177,AB436826,DQ056296,AY699297,AJ250272,EU839930,AB091751,JF703094,DQO96288,EF199732,EF199726,AB091748,EF199734,AY253838,DQ990318,AY262746,AY253839,EF687001,EU839938,AY699296,AY184813,AY307087,AB436824,AJ491184,AY699299,AB364380,AB045372,DQ096293,EF199727,AJ250273,EF059922,DQ096292,AB436835,AY307086,AB436830,AB091754,AY307093,DQ096289,AY699304,AY695809,AB091749,AY262749,EF199725,AB091756,DQ990319,AY307091,AJ491175,AY866502,AB436827,AB436825,AB045373,HQ018934,DQ096294,AY699303,DQ990317,DQ096291,AB436829,AY866505,AY253837,EU753963,A |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rotavirus G9 | NC_011504 | vertebrates,human | 4 | Reoviridae,Rotavirus,Rotavirus A | seg. 10 | B436823,AY866501,AY866503,AB091747,EU839941,EF19973 1,AB436828,AY3070 85,JF703096,AB0917 53,AF359358,AJ2505 40,AY307090,DQ490 173,EF199733,AB091 746,AY816184,AB04 5374,AJ250271,EU83 9931,AJ491172,AJ25 0545,AY699300,AY3 07089,AY699295,AY 211066,JF703097 |
| Rotavirus G9 | NC_011509 | vertebrates,human | 1 | Reoviridae,Rotavirus,Rotavirus A | seg. 6 | EF033203,EF059924, EF033202,EF033204 |
| Rotavirus G9 | NC_011510 | vertebrates,human | 1 | Reoviridae,Rotavirus,Rotavirus A | seg. 4 | EU753964 |
| Rotavirus RVA/G1/Human/India/UK-HLD/2011/H14 | NC_011503 | vertebrates,human | 1 | Reoviridae,Rotavirus,Rotavirus A | seg. 9 | EF059923 |
| Rotavirus RVA/G1/Human/India/UK-HLD/2011/H180 | NC_011503 | vertebrates,human | 1 | Reoviridae,Rotavirus,Rotavirus A | seg. 9 | JX411969 |
| Rotavirus RVA/G9/Human/India/UK-HLD/2011/H140 | NC_011503 | vertebrates,human | 1 | Reoviridae,Rotavirus,Rotavirus A | seg. 9 | JX411970 |
| Rotavirus str,US1205 | NC_011503 | vertebrates,human | 1 | Reoviridae,Rotavirus,Rotavirus A | seg. 9 | JX411968 |
| Rotavirus strain TUCH | NC_011509 | vertebrates,human | 1 | Reoviridae,Rotavirus,Rotavirus A | seg. 9 | AF060487 |
| Rotavirus strain TUCH | NC_011510 | vertebrates,human | 1 | Reoviridae,Rotavirus,Rotavirus A | seg. 6 | AY594670 |
| Rotavirus subgroup 1 | NC_011503 | vertebrates,human | 2 | Reoviridae,Rotavirus,Rotavirus A | seg. 4 | AY596189 |
| Rotavirus subgroup 1 | NC_011504 | vertebrates,human | 1 | Reoviridae,Rotavirus,Rotavirus A | seg. 9 | K02028,L11605 |
| Rotavirus subgroup 1 | NC_011505 | vertebrates,human | 1 | Reoviridae,Rotavirus,Rotavirus A | seg. | K03384 |
| Rotavirus subgroup 1 | NC_011505 10 | vertebrates,human | 1 | Reoviridae,Rotavirus,Rotavirus A | seg. | K03385 |
| Rotavirus subgroup 2 | NC_011509 | vertebrates,human | 1 | Reoviridae,Rotavirus,Rotavirus A | seg. 6 | DQ0325 |
| Rotavirus subgroup 2 | NC_011501 | vertebrates,human | 1 | Reoviridae,Rotavirus,Rotavirus A | seg. 7 | X57944 |
| Rotavirus subgroup 2 | NC_011503 | vertebrates,human | 1 | Reoviridae,Rotavirus,Rotavirus A | seg. 9 | K02033 |
| Rotavirus subgroup 2 | NC_011504 10 | vertebrates,human | 1 | Reoviridae,Rotavirus,Rotavirus A | seg. | K02032 |
| Rotavirus subgroup 2 | NC_011509 | vertebrates,human | 2 | Reoviridae,Rotavirus,Rotavirus A | seg. 6 | X57943,K02086 |
| Rubella virus | NC_001545 | vertebrates,human | 47 | Togaviridae,Rubivirus,Rubella virus | — | AY258323,JN635281, JN635282,JN635292, JN635285,AF435866, JN635296,DQ085341 ,AB047329,AF435865 ,AB588193,DQ08534 0,L78917,JN635290, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| SARS Coronavirus CDC#200301157 | NC_004718 | vertebrates,human | 1 | Coronaviridae, TABLE 10-continued ViroCap-1.0 Taxonomy

| Taxonomy | Rep.Acc.ID | Host | Lineage | # GN's | Seg. Count | GN.Acc.IDs |
|---|---|---|---|---|---|---|
| SARS coronavirus BJ182-12 | NC_004718 | vertebrates,human | Co TABLE 10-continued ViroCap-1.0 Taxonomy

| Taxonomy | Rep.Acc.ID | Host | Lineage | # GN's | Seg. Count | GN.Acc.IDs |
|---|---|---|---|---|---|---|
| SARS coronavirus GDH-BJHO1 | NC_004718 | vertebrates,human | Coronaviridae,Betacoronavirus,Severe acute respiratory syndrome-related coronavirus | 1 | — | DQ640652 |
| SARS coronavirus GZ-A | NC_004718 | vertebrates,human | Coronaviridae,Betacoronavirus,Severe acute respiratory syndrome-related coronavirus | 1 | — | AY394977 |
| SARS coronavirus GZ-B | NC_004718 | vertebrates,human | Coronaviridae,Betacoronavirus,Severe acute respiratory syndrome-related coronavirus | 1 | — | AY394978 |
| SARS coronavirus GZ-C | NC_004718 | vertebrates,human | Coronaviridae,Betacoronavirus,Severe acute respiratory syndrome-related coronavirus | 1 | — | AY394979 |
| SARS coronavirus GZ-D | NC_004718 | vertebrates,human | Coronaviridae,Betacoronavirus,Severe acute respiratory syndrome-related coronavirus | 1 | — | AY394980 |
| SARS coronavirus GZO2 | NC_004718 | vertebrates,human | Coronaviridae,Betacoronavirus,Severe acute respiratory syndrome-related coronavirus | 1 | — | AY390556 |
| SARS coronavirus GZ0401 | NC_004718 | vertebrates,human | Coronaviridae,Betacoronavirus,Severe acute respiratory syndrome-related coronavirus | 1 | — | AY568539 |
| SARS coronavirus GZ0402 | NC_004718 | vertebrates,human | Coronaviridae,Betacoronavirus,Severe acute respiratory syndrome-related coronavirus | 1 | — | AY613947 |
| SARS coronavirus GZ50 | NC_004718 | vertebrates,human | Coronaviridae,Betacoronavirus,Severe acute respiratory syndrome-related coronavirus | 1 | — | AY304495 |
| SARS coronavirus HC/SZ/61/03 | NC_004718 | vertebrates,human | Coronaviridae,Betacoronavirus,Severe acute respiratory syndrome-related coronavirus | 1 | — | AY515512 |
| SARS coronavirus HGZ8L1-A | NC_004718 | vertebrates,human | Coronaviridae,Betacoronavirus,Severe acute respiratory syndrome-related coronavirus | 1 | — | AY394981 |
| SARS coronavirus HGZ8L1-B | NC_004718 | vertebrates,human | Coronaviridae,Betacoronavirus,Severe acute respiratory syndrome-related coronavirus | 1 | — | AY394982 |
| SARS coronavirus HGZ8L2 | NC_004718 | vertebrates,human | Coronaviridae,Betacoronavirus,Severe acute respiratory syndrome-related coronavirus | 1 | — | AY394993 |
| SARS coronavirus HKU-39849 | NC_004718 | vertebrates,human | Coronaviridae,Betacoronavirus,Severe acute respiratory syndrome-related coronavirus | 6 | — | JQ316196,JN854286,GU553365,AY278491,GU553363,GU553364 |
| SARS coronavirus HSR 1 | NC_004718 | vertebrates,human | Coronaviridae,Betacoronavirus,Severe acute respiratory syndrome-related coronavirus | 1 | — | AY323977 |
| SARS coronavirus HSZ-A | NC_004718 | vertebrates,human | Coronaviridae,Betacoronavirus,Severe acute respiratory syndrome-related coronavirus | 1 | — | AY394984 |
| SARS coronavirus HSZ-Bb | NC_004718 | vertebrates,human | Coronaviridae,Betacoronavirus,Severe acute respiratory syndrome-related coronavirus | 1 | — | AY394985 |
| SARS coronavirus HSZ-Bc | NC_004718 | vertebrates,human | Coronaviridae,Betacoronavirus,Severe acute respiratory syndrome-related coronavirus | 1 | — | AY394994 |
| SARS coronavirus HSZ-Cb | NC_004718 | vertebrates,human | Coronaviridae,Betacoronavirus,Severe acute respiratory syndrome-related coronavirus | 1 | — | AY394986 |
| SARS coronavirus HSZ-Cc | NC_004718 | vertebrates,human | Coronaviridae,Betacoronavirus,Severe acute respiratory syndrome-related coronavirus | 1 | — | AY394995 |
| SARS coronavirus HZS2-A | NC_004718 | vertebrates,human | Coronaviridae,Betacoronavirus,Severe acute respiratory syndrome-related coronavirus | 1 | — | AY394983 |
| SARS coronavirus HZS2-Bb | NC_004718 | vertebrates,human | Coronaviridae,Betacoronavirus,Severe acute respiratory syndrome-related coronavirus | 1 | — | AY395004 |
| SARS coronavirus HZS2-C | NC_004718 | vertebrates,human | Coronaviridae,Betacoronavirus,Severe acute respiratory syndrome-related coronavirus | 1 | — | AY394992 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| SARS coronavirus HZS2-D | NC_004718 | vertebrates,human | 1 | Coronaviridae,Betacoronavirus,Severe acute respiratory syndrome-related coronavirus | — | AY394989 |
| SARS coronavirus HZS2-E | NC_004718 | vertebrates,human | 1 | Coronaviridae,Betacoronavirus,Severe acute respiratory syndrome-related coronavirus | — | AY394990 |
| SARS coronavirus HZS2-Fb | NC_004718 | vertebrates,human | 1 | Coronaviridae,Betacoronavirus,Severe acute respiratory syndrome-related coronavirus | — | AY394987 |
| SARS coronavirus HZS2-Fc | NC_004718 | vertebrates,human | 1 | Coronaviridae,Betacoronavirus,Severe acute respiratory syndrome-related coronavirus | — | AY394991 |
| SARS coronavirus JMD | NC_004718 | vertebrates,human | 1 | Coronaviridae,Betacoronavirus,Severe acute respiratory syndrome-related coronavirus | — | AY394988 |
| SARS coronavirus LC1 | NC_004718 | vertebrates,human | 1 | Coronaviridae,Betacoronavirus,Severe acute respiratory syndrome-related coronavirus | — | AY394998 |
| SARS coronavirus LC2 | NC_004718 | vertebrates,human | 1 | Coronaviridae,Betacoronavirus,Severe acute respiratory syndrome-related coronavirus | — | AY394999 |
| SARS coronavirus LC3 | NC_004718 | vertebrates,human | 1 | Coronaviridae,Betacoronavirus,Severe acute respiratory syndrome-related coronavirus | — | AY395000 |
| SARS coronavirus LC4 | NC_004718 | vertebrates,human | 1 | Coronaviridae,Betacoronavirus,Severe acute respiratory syndrome-related coronavirus | — | AY395001 |
| SARS coronavirus LC5 | NC_004718 | vertebrates,human | 1 | Coronaviridae,Betacoronavirus,Severe acute respiratory syndrome-related coronavirus | — | AY395002 |
| SARS coronavirus LU-2004 | NC_004718 | vertebrates,human | 1 | Coronaviridae,Betacoronavirus,Severe acute respiratory syndrome-related coronavirus | — | AY595412 |
| SARS coronavirus MA15 | NC_004718 | vertebrates,human | 26 | Coronaviridae,Betacoronavirus,Severe acute respiratory syndrome-related coronavirus | — | FJ882958,JF292910, FJ882961,JF292912, FJ882948,JF292914, JF292911,JF292908, FJ882952,JF292915, JF292918,HQ890546, HQ890542,JF292917, FJ882945,JF292913, HQ890543,HQ890544,H TABLE 10-continued ViroCap-1.0 Taxonomy

| Taxonomy | Rep.Acc.ID | Host | #GN's | Lineage | Seg. Count | GN.Acc.IDs |
|---|---|---|---|---|---|---|
| SARS coronavirus NS-1 | NC_004718 | vertebrates,human | 1 | Coronaviridae,Betacoronavirus,Severe acute respiratory syndrome-related coronavirus | — | 90534,HQ890528,JF292906,JF292905,FJ1882962 |
| SARS coronavirus P2 | NC_004718 | vertebrates,human | 1 | Coronaviridae,Betacoronavirus,Severe acute respiratory syndrome-related coronavirus | — | AY508724 |
| SARS coronavirus PC4-13 | NC_004718 | vertebrates,human | 1 | Coronaviridae,Betacoronavirus,Severe acute respiratory syndrome-related coronavirus | — | FJ882963 |
| SARS coronavirus PC4-136 | NC_004718 | vertebrates,human | 1 | Coronaviridae,Betacoronavirus,Severe acute respiratory syndrome-related coronavirus | — | AY613948 |
| SARS coronavirus PC4-227 | NC_004718 | vertebrates,human | 1 | Coronaviridae,Betacoronavirus,Severe acute respiratory syndrome-related coronavirus | — | AY613949 |
| SARS coronavirus PUMC01 | NC_004718 | vertebrates,human | 1 | Coronaviridae,Betacoronavirus,Severe acute respiratory syndrome-related coronavirus | — | AY613950 |
| SARS coronavirus PUMC02 | NC_004718 | vertebrates,human | 1 | Coronaviridae,Betacoronavirus,Severe acute respiratory syndrome-related coronavirus | — | AY350750 |
| SARS coronavirus PUMC03 | NC_004718 | vertebrates,human | 1 | Coronaviridae,Betacoronavirus,Severe acute respiratory syndrome-related coronavirus | — | AY357075 |
| SARS coronavirus Rs_672/2006 | NC_004718 | vertebrates,human | 1 | Coronaviridae,Betacoronavirus,Severe acute respiratory syndrome-related coronavirus | — | AY357076 |
| SARS coronavirus ShanghaiQXC1 | NC_004718 | vertebrates,human | 1 | Coronaviridae,Betacoronavirus,Severe acute respiratory syndrome-related coronavirus | — | FJ588686 |
| SARS coronavirus ShanghaiQXC2 | NC_004718 | vertebrates,human | 1 | Coronaviridae,Betacoronavirus,Severe acute respiratory syndrome-related coronavirus | — | AY463059 |
| SARS coronavirus Sin2500 | NC_004718 | vertebrates,human | 1 | Coronaviridae,Betacoronavirus,Severe acute respiratory syndrome-related coronavirus | — | AY463060 |
| SARS coronavirus Sin2677 | NC_004718 | vertebrates,human | 1 | Coronaviridae,Betacoronavirus,Severe acute respiratory syndrome-related coronavirus | — | AY283794 |
| SARS coronavirus Sin2679 | NC_004718 | vertebrates,human | 1 | Coronaviridae,Betacoronavirus,Severe acute respiratory syndrome-related coronavirus | — | AY283795 |
| SARS coronavirus Sin2748 | NC_004718 | vertebrates,human | 1 | Coronaviridae,Betacoronavirus,Severe acute respiratory syndrome-related coronavirus | — | AY283796 |
| SARS coronavirus Sin2774 | NC_004718 | vertebrates,human | 1 | Coronaviridae,Betacoronavirus,Severe acute respiratory syndrome-related coronavirus | — | AY283797 |
| SARS coronavirus Sin3408 | NC_004718 | vertebrates,human | 1 | Coronaviridae,Betacoronavirus,Severe acute respiratory syndrome-related coronavirus | — | AY283798 |
| SARS coronavirus Sin3408L | NC_004718 | vertebrates,human | 1 | Coronaviridae,Betacoronavirus,Severe acute respiratory syndrome-related coronavirus | — | AY559083 |
| SARS coronavirus Sin3725V | NC_004718 | vertebrates,human | 1 | Coronaviridae,Betacoronavirus,Severe acute respiratory syndrome-related coronavirus | — | AY559097 |
| SARS coronavirus Sin3765V | NC_004718 | vertebrates,human | 1 | Coronaviridae,Betacoronavirus,Severe acute respiratory syndrome-related coronavirus | — | AY559087 |
| SARS coronavirus Sin842 | NC_004718 | vertebrates,human | 1 | Coronaviridae,Betacoronavirus,Severe acute respiratory syndrome-related coronavirus | — | AY559084 |
| SARS coronavirus Sin845 | NC_004718 | vertebrates,human | 1 | Coronaviridae,Betacoronavirus,Severe acute respiratory syndrome-related coronavirus | — | AY559081 |
| SARS coronavirus Sin845 | NC_004718 | vertebrates,human | 1 | Coronaviridae,Betacoronavirus,Severe acute respiratory syndrome-related coronavirus | — | AY559093 |

TABLE 10-continued

| Taxonomy | Rep.Acc.ID | Host | # GN's | Lineage | Seg. Count | GN.Acc.IDs |
|---|---|---|---|---|---|---|
| SARS coronavirus Sin846 | NC_004718 | vertebrates,human | 1 | Coronaviridae,Betacoronavirus,Severe acute respiratory syndrome-related coronavirus | — | AY559094 |
| SARS coronavirus Sin847 | NC_004718 | vertebrates,human | 1 | Coronaviridae,Betacoronavirus,Severe acute respiratory syndrome-related coronavirus | — | AY559095 |
| SARS coronavirus Sin848 | NC_004718 | vertebrates,human | 1 | Coronaviridae,Betacoronavirus,Severe acute respiratory syndrome-related coronavirus | — | AY559085 |
| SARS coronavirus Sin849 | NC_004718 | vertebrates,human | 1 | Coronaviridae,Betacoronavirus,Severe acute respiratory syndrome-related coronavirus | — | AY559086 |
| SARS coronavirus Sin850 | NC_004718 | vertebrates,human | 1 | Coronaviridae,Betacoronavirus,Severe acute respiratory syndrome-related coronavirus | — | AY559096 |
| SARS coronavirus Sin852 | NC_004718 | vertebrates,human | 1 | Coronaviridae,Betacoronavirus,Severe acute respiratory syndrome-related coronavirus | — | AY559082 |
| SARS coronavirus SinP1 | NC_004718 | vertebrates,human | 1 | Coronaviridae,Betacoronavirus,Severe acute respiratory syndrome-related coronavirus | — | AY559088 |
| SARS coronavirus SinP2 | NC_004718 | vertebrates,human | 1 | Coronaviridae,Betacoronavirus,Severe acute respiratory syndrome-related coronavirus | — | AY559089 |
| SARS coronavirus SinP3 | NC_004718 | vertebrates,human | 1 | Coronaviridae,Betacoronavirus,Severe acute respiratory syndrome-related coronavirus | — | AY559090 |
| SARS coronavirus SinP4 | NC_004718 | vertebrates,human | 1 | Coronaviridae,Betacoronavirus,Severe acute respiratory syndrome-related coronavirus | — | AY559091 |
| SARS coronavirus SinP5 | NC_004718 | vertebrates,human | 1 | Coronaviridae,Betacoronavirus,Severe acute respiratory syndrome-related coronavirus | — | AY559092 |
| SARS coronavirus Sino1-11 | NC_004718 | vertebrates,human | 1 | Coronaviridae,Betacoronavirus,Severe acute respiratory syndrome-related coronavirus | — | AY485277 |
| SARS coronavirus Sino3-11 | NC_004718 | vertebrates,human | 1 | Coronaviridae,Betacoronavirus,Severe acute respiratory syndrome-related coronavirus | — | AY485278 |
| SARS coronavirus SoD | NC_004718 | vertebrates,human | 1 | Coronaviridae,Betacoronavirus,Severe acute respiratory syndrome-related coronavirus | — | AY461660 |
| SARS coronavirus TJF | NC_004718 | vertebrates,human | 1 | Coronaviridae,Betacoronavirus,Severe acute respiratory syndrome-related coronavirus | — | AY654624 |
| SARS coronavirus TW1 | NC_004718 | vertebrates,human | 1 | Coronaviridae,Betacoronavirus,Severe acute respiratory syndrome-related coronavirus | — | AY291451 |
| SARS coronavirus TW10 | NC_004718 | vertebrates,human | 1 | Coronaviridae,Betacoronavirus,Severe acute respiratory syndrome-related coronavirus | — | AY502923 |
| SARS coronavirus TW11 | NC_004718 | vertebrates,human | 1 | Coronaviridae,Betacoronavirus,Severe acute respiratory syndrome-related coronavirus | — | AY502924 |
| SARS coronavirus TW2 | NC_004718 | vertebrates,human | 1 | Coronaviridae,Betacoronavirus,Severe acute respiratory syndrome-related coronavirus | — | AY502925 |
| SARS coronavirus TW3 | NC_004718 | vertebrates,human | 1 | Coronaviridae,Betacoronavirus,Severe acute respiratory syndrome-related coronavirus | — | AY502926 |
| SARS coronavirus TW4 | NC_004718 | vertebrates,human | 1 | Coronaviridae,Betacoronavirus,Severe acute respiratory syndrome-related coronavirus | — | AY502927 |
| SARS coronavirus TW5 | NC_004718 | vertebrates,human | 1 | Coronaviridae,Betacoronavirus,Severe acute respiratory syndrome-related coronavirus | — | AY502928 |
| SARS coronavirus TW6 | NC_004718 | vertebrates,human | 1 | Coronaviridae,Betacoronavirus,Severe acute respiratory syndrome-related coronavirus | — | AY502929 |
| SARS coronavirus TW7 | NC_004718 | vertebrates,human | 1 | Coronaviridae,Betacoronavirus,Severe acute respiratory syndrome-related coronavirus | — | AY502930 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| SARS coronavirus TW8 | NC_004718 | vertebrates,human | 1 | Coronaviridae,Betacoronavirus,Severe acute respiratory syndrome-related coronavirus | — | AY502931

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| SARS coronavirus civet020 | NC_004718 | vertebrates,human | 1 | Coronaviridae,Betacoronavirus,Severe acute respiratory syndrome-related coronavirus | — | AY572038 |
| SARS coronavirus wtic-MB | NC_004718 | vertebrates,human | 31 | Coronaviridae,Betacoronavirus,Severe acute respiratory syndrome-related coronavirus | — | KF514421,FJ882932, FJ882937,KF514413, KF514400,KF514392, KF514399,JF292921, KF514415,FJ882927, KF514398,KF514408, KF514419,FJ882938, KF514423,FJ882934, KF514418,FJ882939, KF514396,KF514397, FJ882936,FJ882949, FJ882946,FJ882933, FJ882947,KF514394, KF514409,KF514422, KF514388,FJ882935, KF514404 |
| Sabia virus | NC_006313 | vertebrates,human | 3 | Arenaviridae,Arenavirus,Sabia virus | seg. L | JN801475,AY358026, AY216506 |
| Sabia virus | NC_006317 | vertebrates,human | 2 | Arenaviridae,Arenavirus,Sabia virus | seg. S | U41071,JN801474 |
| Sapovirus Chanthaburi-74/Thailand | NC_000940,NC_01062 4,NC_0062 69,NC_006 554 | vertebrates,human | 1 | Caliciviridae,Sapovirus,Sapporo virus | — | AY646854 |
| Sapovirus Ehime1107/2002/JP | NC_000940,NC_01062 4,NC_0062 69,NC_006 554 | vertebrates,human | 1 | Caliciviridae,Sapovirus,Sapporo virus | — | DQ058829 |
| Sapovirus Hu/Angelholm/SW278/200 4/SE | NC_000940,NC_01062 4,NC_0062 69,NC_006 554 | vertebrates,human | 1 | Caliciviridae,Sapovirus,Sapporo virus | — | DQ125333 |
| Sapovirus Hu/Angelholm/SW314/200 4/SE | NC_000940,NC_01062 4,NC_0062 69,NC_006 554 | vertebrates,human | 1 | Caliciviridae,Sapovirus,Sapporo virus | — | DQ125334 |
| Sapovirus Hu/Bristol/1998/UK | NC_000940,NC_01062 4,NC_0062 69,NC_006 554 | vertebrates,human | 1 | Caliciviridae,Sapovirus,Sapporo virus | — | AJ249939 |

TABLE 10-continued

| Taxonomy | Rep.Acc.ID | Host | ViroCap-1.0 Taxonomy | | Seg. Count | GN.Acc.IDs |
| --- | --- | --- | --- | --- | --- | --- |
| | | | # GN's | Lineage | | |
| Sapovirus Hu/Chiba/000671/1999/JP | NC_000940, NC_010624, NC_006269, NC_006554 | vertebrates,human | 1 | Caliciviridae,Sapovirus,Sapporo virus | — | AJ786349 |
| Sapovirus Hu/Ehime1596/1999/JP | NC_000940, NC_010624, NC_006269, NC_006554 | vertebrates,human | 1 | Caliciviridae,Sapovirus,Sapporo virus | — | DQ366346 |
| Sapovirus Hu/Ehime475/2004/JP | NC_000940, NC_010624, NC_006269, NC_006554 | vertebrates,human | 1 | Caliciviridae,Sapovirus,Sapporo virus | — | DQ366344 |
| Sapovirus Hu/Ehime6643/March 2000/JP | NC_000940, NC_010624, NC_006269, NC_006554 | vertebrates,human | 1 | Caliciviridae,Sapovirus,Sapporo virus | — | DQ366345 |
| Sapovirus Hu/G L2/BR-DF01/BRA/2009 | NC_000940, NC_010624, NC_006269, NC_006554 | vertebrates,human | 1 | Caliciviridae,Sapovirus,Sapporo virus | — | AB614356 |
| Sapovirus Hu/GI/Sapporo/MT-2010/1982 | NC_000940, NC_010624, NC_006269, NC_006554 | vertebrates,human | 1 | Caliciviridae,Sapovirus,Sapporo virus | — | HM002617 |
| Sapovirus Mc114 | NC_000940, NC_010624, NC_006269, NC_006554 | vertebrates,human | 1 | Caliciviridae,Sapovirus,Sapporo virus | — | AY237422 |
| Sapovirus Mc2 | NC_000940, NC_010624, NC_006269, NC_006554 | vertebrates,human | 1 | Caliciviridae,Sapovirus,Sapporo virus | — | AY237419 |
| Sapovirus N21 | NC_000940, NC_010624, NC_006269, NC_006554 | vertebrates,human | 1 | Caliciviridae,Sapovirus,Sapporo virus | — | AY237423 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Sapovirus NongKhai-24/Thailand | NC_000940,NC_010624,NC_006269,NC_006554 | vertebrates,human | 1 | Caliciviridae,Sapovirus,Sapporo virus | — | AY646856 |
| Sapovirus NongKhai-50/Thailand | NC_000940,NC_010624,NC_006269,NC_006554 | vertebrates,human | 1 | Caliciviridae,Sapovirus,Sapporo virus | — | AY646853 |
| Sapovirus SaKaeo-15/Thailand | NC_000940,NC_010624,NC_006269,NC_006554 | vertebrates,human | 1 | Caliciviridae,Sapovirus,Sapporo virus | — | AY646855 |
| Sapovirus pig/Gansu/CH430/2012/CHN | NC_000940,NC_010624,NC_006269,NC_006554 | vertebrates,human | 1 | Caliciviridae,Sapovirus,Sapporo virus | — | KF204570 |
| Sapovirus pig/sav1/2008/CHN | NC_000940,NC_010624,NC_006269,NC_006554 | vertebrates,human | 1 | Caliciviridae,Sapovirus,Sapporo virus | — | FJ387164 |
| Sapporo rat virus | NC_005236 | vertebrates,human | 1 | Bunyaviridae,Hantavirus,Seoul virus | seg. S | M34881 |
| Sapporo rat virus | NC_005237 | vertebrates,human | 1 | Bunyaviridae,Hantavirus,Seoul virus | seg. M | M34882 |
| Sapporo virus-Manchester | NC_000940,NC_010624,NC_006269,NC_006554 | vertebrates,human | 1 | Caliciviridae,Sapovirus,Sapporo virus | — | X86560 |
| Seal anellovirus TFFN/USA/2006 | NC_015212 | vertebrates,human | 1 | Anelloviridae,Seal anellovirus TFFN/USA/2006 | — | HQ287751 |
| Sendai virus | NC_001552 | vertebrates,human | 20 | Paramyxoviridae,Respirovirus,Sendai virus | — | AB855653,AB005795,AB005796,AB065187,M69046,M30204,D0219803,AB195967,AB855655,EF679198,AB275417,AB065188,AB855654,AB03965 8,AB195968,AB2754 16,M30203,AB06518 9,AB065186,M30202 |
| Seoul virus | NC_005236 | vertebrates,human | 13 | Bunyaviridae,Hantavirus,Seoul virus | seg. S | AF406965,KC626089,JX853575,JX879769,JQ665912,HQ611980,AY006465,EF192308 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Seoul virus | NC_005237 | vertebrates,human | 11 | Bunyaviridae,Hantavirus,Seoul virus | seg. M | AY766368,AY273791,JQ898106,JN377553,AY750171 D17593,D17592,547716,JN377554,JQ665888,JX853576,D17594,DQ159911,JX879768,AB027521,EF117248 |
| Seoul virus | NC_005238 | vertebrates,human | 5 | Bunyaviridae,Hantavirus,Seoul virus | seg. L | JX879770,EF190551,X56492,JX853574,EF581094 |
| Seoul virus 5CSG | NC_005237 | vertebrates,human | 1 | Bunyaviridae,Hantavirus,Seoul virus | seg. M | AB618130 |
| Seoul virus B-1 | NC_005237 | vertebrates,human | 1 | Bunyaviridae,Hantavirus,Seoul virus | seg. M | X53861 |
| Seoul virus BjHDQ1 | NC_005236 | vertebrates,human | 1 | Bunyaviridae,Hantavirus,Seoul virus | seg. S | AY627049 |
| Seoul virus BjHDQ1 | NC_005237 | vertebrates,human | 1 | Bunyaviridae,Hantavirus,Seoul virus | seg. M | DQ133505 |
| Seoul virus CSG5 | NC_005236 | vertebrates,human | 1 | Bunyaviridae,Hantavirus,Seoul virus | seg. S | AB618112 |
| Seoul virus Gou3-e5 | NC_005236 | vertebrates,human | 1 | Bunyaviridae,Hantavirus,Seoul virus | seg. S | AF288650 |
| Seoul virus Hb8610 | NC_005236 | vertebrates,human | 1 | Bunyaviridae,Hantavirus,Seoul virus | seg. S | AF288643 |
| Seoul virus K24-e7 | NC_005236 | vertebrates,human | 1 | Bunyaviridae,Hantavirus,Seoul virus | seg. S | AF288653 |
| Seoul virus K24-e7 | NC_005237 | vertebrates,human | 1 | Bunyaviridae,Hantavirus,Seoul virus | seg. M | AF288652 |
| Seoul virus K24-v2 | NC_005236 | vertebrates,human | 1 | Bunyaviridae,Hantavirus,Seoul virus | seg. S | AF288655 |
| Seoul virus K24-v2 | NC_005237 | vertebrates,human | 1 | Bunyaviridae,Hantavirus,Seoul virus | seg. M | AF288654 |
| Seoulvirus Gou3 | NC_005236 | vertebrates,human | 1 | Bunyaviridae,Hantavirus,Seoul virus | seg. S | AF184988 |
| Seoulvirus Gou3 | NC_005237 | vertebrates,human | 1 | Bunyaviridae,Hantavirus,Seoul virus | seg. M | AF145977 |
| Seoulvirus HB55 | NC_005236 | vertebrates,human | 1 | Bunyaviridae,Hantavirus,Seoul virus | seg. S | AF035832 |
| Seoulvirus IR461 | NC_005237 | vertebrates,human | 1 | Bunyaviridae,Hantavirus,Seoul virus | seg. M | AF329388 |
| Seoulvirus IR461 | NC_005236 | vertebrates,human | 1 | Bunyaviridae,Hantavirus,Seoul virus | seg. S | AF458104 |
| Seoulvirus L99 | NC_005237 | vertebrates,human | 1 | Bunyaviridae,Hantavirus,Seoul virus | seg. M | AF288299 |
| Seoulvirus L99 | NC_005236 | vertebrates,human | 2 | Bunyaviridae,Hantavirus,Seoul virus | seg. S | AF288298,AF035833 |
| Seoulvirus L99 | NC_005238 | vertebrates,human | 1 | Bunyaviridae,Hantavirus,Seoul virus | seg. L | AF288297 |
| Seoulvirus R22 | NC_005236 | vertebrates,human | 2 | Bunyaviridae,Hantavirus,Seoul virus | seg. S | AF488707,AF288295 |
| Seoulvirus tchoupitoulas | NC_005236 | vertebrates,human | 1 | Bunyaviridae,Hantavirus,Seoul virus | seg. S | AF329389 |
| Simian Agent 10 | NC_001796 | vertebrates,human | 1 | Paramyxoviridae,Respirovirus,Human parainfluenza virus 3 | — | HM583801 |
| Simian adenovirus 27,1 | NC_011202 | vertebrates,human | 1 | Adenoviridae,Mastadenovirus,Human adenovirus B | — | FJQ25909 |
| Simian adenovirus 27,1 | NC_011203 | vertebrates,human | 1 | Adenoviridae,Mastadenovirus,Human adenovirus B | — | FJQ25909 |
| Simian adenovirus 27,2 | NC_011202 | vertebrates,human | 1 | Adenoviridae,Mastadenovirus,Human adenovirus B | — | FJQ25928 |
| Simian adenovirus 27,2 | NC_011203 | vertebrates,human | 1 | Adenoviridae,Mastadenovirus,Human adenovirus B | — | FJQ25928 |
| Simian adenovirus 28,1 | NC_011202 | vertebrates,human | 1 | Adenoviridae,Mastadenovirus,Human adenovirus B | — | FJQ25914 |
| Simian adenovirus 28,1 | NC_011203 | vertebrates,human | 1 | Adenoviridae,Mastadenovirus,Human adenovirus B | — | FJQ25914 |

TABLE 10-continued

| Taxonomy | Rep.Acc.ID | Host | ViroCap-1.0 Taxonomy | | Seg. Count | GN.Acc.IDs |
| --- | --- | --- | --- | --- | --- | --- |
| | | | Lineage | # GN's | | |
| Simian adenovirus 28,2 | NC_011202 | vertebrates,human | Adenoviridae,Mastadenovirus,Human adenovirus B | 1 | — | FJQ25915 |
| Simian adenovirus 28,2 | NC_011203 | vertebrates,human | Adenoviridae,Mastadenovirus,Human adenovirus B | 1 | — | FJQ25915 |
| Simian adenovirus 29 | NC_011202 | vertebrates,human | Adenoviridae,Mastadenovirus,Human adenovirus B | 1 | — | FJQ25916 |
| Simian adenovirus 29 | NC_011203 | vertebrates,human | Adenoviridae,Mastadenovirus,Human adenovirus B | 1 | — | FJQ25916 |
| Simian adenovirus 31,1 | NC_001405 | vertebrates,human | Adenoviridae,Mastadenovirus,Human adenovirus C | 1 | — | FJQ25906 |
| Simian adenovirus 31,2 | NC_001405 | vertebrates,human | Adenoviridae,Mastadenovirus,Human adenovirus C | 1 | — | FJQ25904 |
| Simian adenovirus 32 | NC_011202 | vertebrates,human | Adenoviridae,Mastadenovirus,Human adenovirus B | 1 | — | FJQ25911 |
| Simian adenovirus 32 | NC_011203 | vertebrates,human | Adenoviridae,Mastadenovirus,Human adenovirus B | 1 | — | FJQ25911 |
| Simian adenovirus 33 | NC_011202 | vertebrates,human | Adenoviridae,Mastadenovirus,Human adenovirus B | 1 | — | FJQ25908 |
| Simian adenovirus 33 | NC_011203 | vertebrates,human | Adenoviridae,Mastadenovirus,Human adenovirus B | 1 | — | FJQ25908 |
| Simian adenovirus 34 | NC_001405 | vertebrates,human | Adenoviridae,Mastadenovirus,Human adenovirus C | 1 | — | FJQ25905 |
| Simian adenovirus 35,1 | NC_011202 | vertebrates,human | Adenoviridae,Mastadenovirus,Human adenovirus B | 1 | — | FJQ25912 |
| Simian adenovirus 35,1 | NC_011203 | vertebrates,human | Adenoviridae,Mastadenovirus,Human adenovirus B | 1 | — | FJQ25912 |
| Simian adenovirus 35,2 | NC_011202 | vertebrates,human | Adenoviridae,Mastadenovirus,Human adenovirus B | 1 | — | FJQ25910 |
| Simian adenovirus 35,2 | NC_011203 | vertebrates,human | Adenoviridae,Mastadenovirus,Human adenovirus B | 1 | — | FJQ25910 |
| Simian adenovirus 40,1 | NC_001405 | vertebrates,human | Adenoviridae,Mastadenovirus,Human adenovirus C | 1 | — | FJQ25907 |
| Simian adenovirus 40,2 | NC_001405 | vertebrates,human | Adenoviridae,Mastadenovirus,Human adenovirus C | 1 | — | FJQ25926 |
| Simian adenovirus 41,1 | NC_011202 | vertebrates,human | Adenoviridae,Mastadenovirus,Human adenovirus B | 1 | — | FJQ25913 |
| Simian adenovirus 41,1 | NC_011203 | vertebrates,human | Adenoviridae,Mastadenovirus,Human adenovirus B | 1 | — | FJQ25913 |
| Simian adenovirus 41,2 | NC_011202 | vertebrates,human | Adenoviridae,Mastadenovirus,Human adenovirus B | 1 | — | FJQ25927 |
| Simian adenovirus 41,2 | NC_011203 | vertebrates,human | Adenoviridae,Mastadenovirus,Human adenovirus B | 1 | — | FJQ25927 |
| Simian adenovirus 42,1 | NC_001405 | vertebrates,human | Adenoviridae,Mastadenovirus,Human adenovirus C | 1 | — | FJQ25903 |
| Simian adenovirus 42,2 | NC_001405 | vertebrates,human | Adenoviridae,Mastadenovirus,Human adenovirus C | 1 | — | FJQ25902 |
| Simian adenovirus 42,3 | NC_001405 | vertebrates,human | Adenoviridae,Mastadenovirus,Human adenovirus C | 1 | — | FJQ25925 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Simian adenovirus 43 | NC_001405 | vertebrates,human | Adenoviridae,Mastadenovirus,Human adenovirus C | 1 | — | FJQ25900 |
| Simian adenovirus 44 | NC_001405 | vertebrates,human | Adenoviridae,Mastadenovirus,Human adenovirus C | 1 | — | FJQ25899 |
| Simian adenovirus 45 | NC_001405 | vertebrates,human | Adenoviridae,Mastadenovirus,Human adenovirus C | 1 | — | FJQ25901 |
| Simian adenovirus 46 | NC_011202 | vertebrates,human | Adenoviridae,Mastadenovirus,Human adenovirus B | 1 | — | FJQ25930 |
| Simian adenovirus 46 | NC_011203 | vertebrates,human | Adenoviridae,Mastadenovirus,Human adenovirus B | 1 | — | FJQ25930 |
| Simian adenovirus 47 | NC_011202 | vertebrates,human | Adenoviridae,Mastadenovirus,Human adenovirus B | 1 | — | FJQ25929 |
| Simian adenovirus 47 | NC_011203 | vertebrates,human | Adenoviridae,Mastadenovirus,Human adenovirus B | 1 | — | FJQ25929 |
| Simian agents | NC_001472 | vertebrates,human | Picornaviridae,Enterovirus,Enterovirus B | 1 | — | AF326751 |
| Simian enterovirus 19 | NC_001612 | vertebrates,human | Picornaviridae,Enterovirus,Enterovirus A | 1 | — | AF326754 |
| Simian enterovirus 43 | NC_001612 | vertebrates,human | Picornaviridae,Enterovirus,Enterovirus A | 1 | — | AF326761 |
| Simian enterovirus 46 | NC_001612 | vertebrates,human | Picornaviridae,Enterovirus,Enterovirus A | 2 | — | EF667343,AF326764 |
| Simian rotavirus | NC_011500 | vertebrates,human | Reoviridae,Rotavirus,Rotavirus A | 6 | seg. 5 | AF290884,AF290883,AF290882,Z32535,AF290881,FJ422135 |
| Simian rotavirus | NC_011501 | vertebrates,human | Reoviridae,Rotavirus,Rotavirus A | 2 | seg. 7 | GU550506,FJ422137 |
| Simian rotavirus | NC_011502 | vertebrates,human | Reoviridae,Rotavirus,Rotavirus A | 2 | seg. 8 | X81426,FJ422138 |
| Simian rotavirus | NC_011503 | vertebrates,human | Reoviridae,Rotavirus,Rotavirus A | 4 | seg. 9 | X66158,V01546,V01190,FJ422139 |
| Simian rotavirus | NC_011504 | vertebrates,human | Reoviridae,Rotavirus,Rotavirus A | 2 | seg. 10 | FJ422140,L41247 |
| Simian rotavirus | NC_011505 | vertebrates,human | Reoviridae,Rotavirus,Rotavirus A | 4 | seg. 11 | AF306493,XQ7831,FJ422141,M28347 |
| Simian rotavirus | NC_011506 | vertebrates,human | Reoviridae,Rotavirus,Rotavirus A | 3 | seg. 2 | AF474406,L33364,FJ422132 |
| Simian rotavirus | NC_011507 | vertebrates,human | Reoviridae,Rotavirus,Rotavirus A | 1 | seg. 1 | FJ422131 |
| Simian rotavirus | NC_011508 | vertebrates,human | Reoviridae,Rotavirus,Rotavirus A | 1 | seg. 3 | FJ422133 |
| Simian rotavirus | NC_011509 | vertebrates,human | Reoviridae,Rotavirus,Rotavirus A | 5 | seg. 6 | L15384,FJ422136,L33365,XQ0421,M27824 |
| Simian rotavirus 4 | NC_011510 | vertebrates,human | Reoviridae,Rotavirus,Rotavirus A | 5 | seg. 4 | M23188,FJ422134,D16345,D16346,X1420 |
| Simian rotavirus A strain RRV | NC_011506 | vertebrates,human | Reoviridae,Rotavirus,Rotavirus A | 2 | seg. 2 | EF583007,EU636925 |
| Simian rotavirus A strain RRV | NC_011507 | vertebrates,human | Reoviridae,Rotavirus,Rotavirus A | 2 | seg. 1 | EU636924,EF583006 |
| Simian rotavirus A strain RRV | NC_011508 | vertebrates,human | Reoviridae,Rotavirus,Rotavirus A | 2 | seg. 3 | EU636926,EF583008 |
| Simian rotavirus A strain RRV | NC_011509 | vertebrates,human | Reoviridae,Rotavirus,Rotavirus A | 1 | seg. 6 | EF583009 |
| Simian rotavirus A strain TUCH | NC_011500 | vertebrates,human | Reoviridae,Rotavirus,Rotavirus A | 1 | seg. 5 | FJ816612 |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| Simian rotavirus A strain TUCH | NC_011501 | vertebrates,human | 1 | Reoviridae,Rotavirus,Rotavirus A | seg. 7 | FJ816613 |
| Simian rotavirus A strain TUCH | NC_011502 | vertebrates,human | 1 | Reoviridae,Rotavirus,Rotavirus A | seg. 8 | FJ816614 |
| Simian rotavirus A strain TUCH | NC_011503 | vertebrates,human | 1 | Reoviridae,Rotavirus,Rotavirus A | seg. 9 | FJ816615 |
| Simian rotavirus A strain TUCH | NC_011504 | vertebrates,human | 1 | Reoviridae,Rotavirus,Rotavirus A | seg. 10 | FJ816616 |
| Simian rotavirus A strain TUCH | NC_011505 | vertebrates,human | 1 | Reoviridae,Rotavirus,Rotavirus A | seg. 11 | FJ816617 |
| Simian rotavirus A strain TUCH | NC_011506 | vertebrates,human | 1 | Reoviridae,Rotavirus,Rotavirus A | seg. 2 | EF583011 |
| Simian rotavirus A strain TUCH | NC_011507 | vertebrates,human | 1 | Reoviridae,Rotavirus,Rotavirus A | seg. 1 | EF583010 |
| Simian rotavirus A strain TUCH | NC_011508 | vertebrates,human | 1 | Reoviridae,Rotavirus,Rotavirus A | seg. 3 | EF583012 |
| Simian rotavirus A strain TUCH | NC_011509 | vertebrates,human | 1 | Reoviridae,Rotavirus,Rotavirus A | seg. 6 | EF583013 |
| Simian rotavirus A strain TUCH | NC_011510 | vertebrates,human | 1 | Reoviridae,Rotavirus,Rotavirus A | seg. 4 | FJ816611 |
| Simian rotavirus A/SA11 | NC_011500 | vertebrates,human | 1 | Reoviridae,Rotavirus,Rotavirus A | seg. 5 | X14914 |
| Simian rotavirus A/SA11 | NC_011501 | vertebrates,human | 1 | Reoviridae,Rotavirus,Rotavirus A | seg. 7 | JQ2353 |
| Simian rotavirus A/SA11 | NC_011502 | vertebrates,human | 2 | Reoviridae,Rotavirus,Rotavirus A | seg. 8 | XQ0355 |
| Simian rotavirus A/SA11 | NC_011504 | vertebrates,human | 2 | Reoviridae,Rotavirus,Rotavirus A | seg. 10 | AF087678,K01138 |
| Simian rotavirus A/SA11 | NC_011506 | vertebrates,human | 1 | Reoviridae,Rotavirus,Rotavirus A | seg. 2 | X16831 |
| Simian rotavirus A/SA11 | NC_011507 | vertebrates,human | 1 | Reoviridae,Rotavirus,Rotavirus A | seg. 1 | X16830 |
| Simian rotavirus A/SA11 | NC_011508 | vertebrates,human | 2 | Reoviridae,Rotavirus,Rotavirus A | seg. 3 | X16062,X16387 |
| Simian rotavirus A/SA11 | NC_011509 | vertebrates,human | 1 | Reoviridae,Rotavirus,Rotavirus A | seg. 6 | AY187029 |
| Simian rotavirus A/SA11 | NC_011510 | vertebrates,human | 1 | Reoviridae,Rotavirus,Rotavirus A | seg. 4 | Y00036 |
| Simian rotavirus A/SA11- C14 | NC_011502 | vertebrates,human | 1 | Reoviridae,Rotavirus,Rotavirus A | seg. 8 | AY065843 |
| Simian rotavirus A/SA11-L2 | NC_011502 | vertebrates,human | 1 | Reoviridae,Rotavirus,Rotavirus A | seg. 8 | EF460843 |
| Simian virus 40 | NC_001669 | vertebrates,human | 35 | Polyomaviridae,Polyomavirus,Simian virus 40 | seg. 8 | EF579662,EF579804, AY271816,EF579661, FN812745,AF155358, AF156105,AY120890, AF345345,JQ2400,AF 316141,EF579665,AF 345344,EF579663,AF 316140,EF579664,AF 156107,EF579659,AY 538779,EF579660,AF 180737,EF579667,AY 271817,AF156108,AF 332562,DQ660375,E F579658,EF579666,A |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Simian virus 41 | NC_006428 | vertebrates,human | 1 | Paramyxoviridae,Rubulavirus,Simian virus 41 | — | F332699,DQ218418,EF579803,AF155359,AF316139,AF168994,AF038616 |
| Sin Nombre virus | NC_005215 | vertebrates,human | 6 | Bunyaviridae,Hantavirus,Sin Nombre virus | seg. M | X64275 JQ690283,JQ690280,JQ690279,JQ690284,L25783,L37903 |
| Sin Nombre virus | NC_005216 | vertebrates,human | 8 | Bunyaviridae,Hantavirus,Sin Nombre virus | seg. S | L25784,JQ690281,JQ690277,JQ690282,JQ690278,JQ690276,AF281851,L37904 |
| Sin Nombre virus | NC_005217 | vertebrates,human | 2 | Bunyaviridae,Hantavirus,Sin Nombre virus | seg. L | L37902,L37901 |
| Small anellovirus 2 | NC_007014,NC_007013 | vertebrates,human | 1 | Anelloviridae,Small anellovirus | — | AY622909 |
| Snow Mountain virus | NC_001959 | vertebrates,human | 1 | Caliciviridae,Norovirus,Norwalk virus | — | AY134748 |
| Southampton virus | NC_001959 | vertebrates,human | 1 | Caliciviridae,Norovirus,Norwalk virus | — | L07418 |
| Sudan ebolavirus | NC_006432 | vertebrates,human | 9 | Filoviridae,Ebolavirus,Sudan ebolavirus | — | KC545391,EU338380,KC589025,KC24278 3,FJ968794,KC54539 0,AY729654,KC5453 89,KC545392 |
| Sudan ebolavirus-Nakisamata | NC_006432 | vertebrates,human | 1 | Filoviridae,Ebolavirus,Sudan ebolavirus | — | JN638998 |
| Swine hepatitis E virus | NC_001434 | vertebrates,human | 26 | Hepeviridae,Hepevirus,Hepatitis E virus | — | GU361892,FJ998008,GU188851,AB481228,EU723514,AY59419 9,GU119961,FJ61023 2,GU119960,KF1763 51,AB097811,AB073 912,AB481227,EU72 3512,EU676172,EU7 23515,AY115488,EU 723513,AF082843,D 0279091,FJ426403,F J426404,AB481229,J X855794,EU723516,AB481226 |
| Swine vesicular disease virus | NC_001472 | vertebrates,human | 4 | Picornaviridae,Enterovirus,Enterovirus B | — | AY429470,AF268065,D16364,X54521 |
| Swine vesicular disease virus (STRAIN H/3 '76) | NC_001472 | vertebrates,human | 1 | Picornaviridae,Enterovirus,Enterovirus B | — | DQ0435 |
| TT virus 51e1931 | NC_015783 | vertebrates,human | 1 | Anelloviridae,Torque teno virus | — | AM712003 |
| TT virus 51e1932 | NC_015783 | vertebrates,human | 1 | Anelloviridae,Torque teno virus | — | AM712004 |
| TT virus 51e1957 | NC_015783 | vertebrates,human | 1 | Anelloviridae,Torque teno virus | — | AM711976 |
| TT virus 51e2057 | NC_015783 | vertebrates,human | 1 | Anelloviridae,Torque teno virus | — | AM712030 |
| TT virus 51e2058 | NC_015783 | vertebrates,human | 1 | Anelloviridae,Torque teno virus | — | AM712031 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| TT virus 51e2061 | NC_015783 | vertebrates,human | Anelloviridae,Torque teno virus | 1 | — | AM712033 |
| TT virus 51e2065 | NC_015783 | vertebrates,human | Anelloviridae,Torque teno virus | 1 | — | AM712034 |
| TT virus 51e2072 | NC_015783 | vertebrates,human | Anelloviridae,Torque teno virus | 1 | — | AM712032 |
| TTV-like mini virus | NC_020498 | vertebrates,human | Anelloviridae,TTV-like mini virus | 8 | — | KF764702,JX134046, AB026930,JX134044, AB038628,AB038626 ,KF764701,JX134045 |
| Tacaribe virus | NC_004292 | vertebrates,human | Arenaviridae,Arenavirus,Tacaribe virus | 1 | seg. L | JQ4340 |
| Tacaribe virus | NC_004293 | vertebrates,human | Arenaviridae,Arenavirus,Tacaribe virus | 1 | seg. S | M20304 |
| Tamiami virus | NC_010701 | vertebrates,human | Arenaviridae,Arenavirus,Tamiami virus | 3 | seg. S | AF512828,AF485263, EU486821 |
| Tamiami virus | NC_010702 | vertebrates,human | Arenaviridae,Arenavirus,Tamiami virus | 2 | seg. L | AY924393,EU627614 |
| Thottapalayam virus | NC_010704 | vertebrates,human | Bunyaviridae,Hantavirus,Thottapalayam virus | 1 | seg. S | AY526097 |
| Thottapalayam virus | NC_010707 | vertebrates,human | Bunyaviridae,Hantavirus,Thottapalayam virus | 2 | seg. L | EU001330,DQ825770 |
| Thottapalayam virus | NC_010708 | vertebrates,human | Bunyaviridae,Hantavirus,Thottapalayam virus | 2 | seg. M | EU001329,DQ825771 |
| Tioman virus | NC_004074 | vertebrates,human | Paramyxoviridae,Rubulavirus,Tioman virus | 1 | — | AF298895 |
| Torque teno canis virus | NC_014071 | vertebrates,human | Anelloviridae,Thetatorquevirus,Torque teno canis virus | 3 | — | AB076002,GU951508 ,HM855265 |
| Torque teno douroucouli virus | NC_014087 | vertebrates,human | Anelloviridae,Zetatorquevirus,Torque teno douroucouli virus | 1 | — | AB041961 |
| Torque teno felis virus | NC_014072 | vertebrates,human | Anelloviridae,Etatorquevirus,Torque teno felis virus | 3 | — | HM142589,HM14258 8,AB076003 |
| Torque teno midi virus 1 | NC_009225 | vertebrates,human | Anelloviridae,Gammatorquevirus,Torque teno midi virus 1 | 2 | — | AB290918,AB290917 |
| Torque teno midi virus 2 | NC_014093 | vertebrates,human | Anelloviridae,Gammatorquevirus,Torque teno midi virus 2 | 1 | — | AB290919 |
| Torque teno mini virus 1 | NC_014097 | vertebrates,human | Anelloviridae,Betatorquevirus,Torque teno mini virus 1 | 1 | — | AB026931 |
| Torque teno mini virus 2 | NC_014086 | vertebrates,human | Anelloviridae,Betatorquevirus,Torque teno mini virus 2 | 1 | — | AB038629 |
| Torque teno mini virus 3 | NC_014088 | vertebrates,human | Anelloviridae,Betatorquevirus,Torque teno mini virus 3 | 1 | — | AB038630 |
| Torque teno mini virus 4 | NC_014090 | vertebrates,human | Anelloviridae,Betatorquevirus,Torque teno mini virus 4 | 1 | — | AB041963 |
| Torque teno mini virus 5 | NC_014089 | vertebrates,human | Anelloviridae,Betatorquevirus,Torque teno mini virus 5 | 1 | — | AB041962 |
| Torque teno mini virus 6 | NC_014095 | vertebrates,human | Anelloviridae,Betatorquevirus,Torque teno mini virus 6 | 1 | — | AB026929 |
| Torque teno mini virus 7 | NC_014082 | vertebrates,human | Anelloviridae,Betatorquevirus,Torque teno mini virus 7 | 1 | — | AB038627 |
| Torque teno mini virus 8 | NC_014068 | vertebrates,human | Anelloviridae,Betatorquevirus,Torque teno mini virus 8 | 1 | — | AF291073 |
| Torque teno mini virus 9 | NC_002195 | vertebrates,human | Anelloviridae,Betatorquevirus,Torque teno mini virus 9 | 2 | — | AB038631,AB038625 |
| Torque teno sus virus 1 | NC_014070 | vertebrates,human | Anelloviridae,Iotatorquevirus,Torque teno sus virus 1a | 13 | — | HM633256,AB076001 ,JF937662,JF937660, JF937661,HM633251 ,JN688927,AY823990 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | JF694117,HM63324 9,HM633245,HM6332 43,JF694116 |
| Torque teno sus virus 1a | NC_014070 | vertebrates,human | 3 | Anelloviridae,Iotatorquevirus,Torque teno sus virus 1a | — | JX535326,JX535327, JQ933527 |
| Torque teno sus virus k2 | NC_014092 | vertebrates,human | 1 | Anelloviridae,Kappatorquevirus,Torque teno sus virus k2 | — | AY823991 |
| Torque teno sus virus k2b | NC_014092 | vertebrates,human | 3 | Anelloviridae,Kappatorquevirus,Torque teno sus virus k2 | — | JQ406846,JQ406844, JQ406845 |
| Torque teno tamarin virus | NC_014085 | vertebrates,human | 1 | Anelloviridae,Epsilontorquevirus,Torque teno tamarin virus | — | AB041960 |
| Torque teno virus | NC_014070 | vertebrates,human | 4 | Anelloviridae,Iotatorquevirus,Torque teno sus virus 1a | — | GQ120664,GU45638 3,GU456384,GU1880 45 |
| Torque teno virus | NC_015783 | vertebrates,human | 114 | Anelloviridae,Torque teno virus | — | AF351132,FR751478, AF247138,FR751507, FR751483,FR751485 ,FR751472,AJ620233 ,FR751470,AB02866 9,AB064603,FR7515 06,AF122915,FR7514 71,AB064597,FR751 463,AJ620216,FR751 495,AY823989,FR84 8325,AB054648,AF12 2916,AJ620228,AJ62 0212,FR848327,FR7 51479,FR751500,AF1 22914,AJ620224,FR7 51477,AJ620235,AB0 64599,FR751465,FR 751491,FR848323,F R751502,AB017610, FR751504,AB064606 ,AJ620218,FR751493 ,AJ620227,AF122917 ,AJ620231,FR751480 ,DQ003344,FR75147 5,AY823988,FR7514 69,AJ620219,AB0386 19,AF116842,FR7514 68,FR751490,FR751 501,AB064602,AJ620 221,AF298585,AJ620 226,AB038620,FR75 1503,FR751509,FR7 51481,AJ620214,FR7 51497,DQ003341,DO |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 00343,FR751476,AJ620232,AJ620230,FR751487,AJ620229,AB064600,AF247137,AF122921,FR751492,AF122918,FR751508,AF122920,FR426280,FR751484,AF122913,FR751511,FR751489,FR751496,AJ620234,AF079173,FR751482,FR751494,AB064601,AB064596,AJ620223,AJ620225,FR751510,FR751486,AF129887,AJ620213,DQ003342,AJ620220,FR751473,FR848324,AJ620222,FR751505,FR751146 6,FR848326,FR751474,AB064604,FR751498,FR751467,AJ620215,AJ620217,FR751464,FR751488,FR751499 |
| Torque teno virus 1 | NC_002076 | vertebrates,human | 2 | Anelloviridae,Alphatorquevirus,Torque teno virus 1 | — | AB041007,AB008394 |
| Torque teno virus 1 | NC_014070 | vertebrates,human | 5 | Anelloviridae,Iotatorquevirus,Torque teno sus virus 1a | — | GU570202,GU570199,GU570201,GU570198,GU570200 |
| Torque teno virus 10 | NC_014076 | vertebrates,human | 2 | Anelloviridae,Alphatorquevirus,Torque teno virus 10 | — | AB064607,GU797360 |
| Torque teno virus 12 | NC_014075 | vertebrates,human | 1 | Anelloviridae,Alphatorquevirus,Torque teno virus 12 | — | AB064605 |
| Torque teno virus 14 | NC_014077 | vertebrates,human | 1 | Anelloviridae,Alphatorquevirus,Torque teno virus 14 | — | AB037926 |
| Torque teno virus 15 | NC_014096 | vertebrates,human | 1 | Anelloviridae,Alphatorquevirus,Torque teno virus 15 | — | AB028668 |
| Torque teno virus 16 | NC_014091 | vertebrates,human | 1 | Anelloviridae,Alphatorquevirus,Torque teno virus 16 | — | AB017613 |
| Torque teno virus 19 | NC_014078 | vertebrates,human | 1 | Anelloviridae,Alphatorquevirus,Torque teno virus 19 | — | AB025946 |
| Torque teno virus 2 | NC_014480 | vertebrates,human | 1 | Anelloviridae,Alphatorquevirus,Torque teno virus 2 | — | AB049608 |
| Torque teno virus 25 | NC_014083 | vertebrates,human | 1 | Anelloviridae,Alphatorquevirus,Torque teno virus 25 | — | AB041959 |
| Torque teno virus 26 | NC_014079 | vertebrates,human | 1 | Anelloviridae,Alphatorquevirus,Torque teno virus 26 | — | AB041958 |

TABLE 10-continued

| Taxonomy | Rep.Acc.ID | Host | Lineage | # GN's | Seg. Count | GN.Acc.IDs |
|---|---|---|---|---|---|---|
| Torque teno virus 27 | NC_014074 | vertebrates,human | Anelloviridae,Alphatorquevirus,Torque teno virus 27 | 1 | — | AB064595 |
| Torque teno virus 28 | NC_014073 | vertebrates,human | Anelloviridae,Alphatorquevirus,Torque teno virus 28 | 1 | — | AB064598 |
| Torque teno virus 3 | NC_014081 | vertebrates,human | Anelloviridae,Alphatorquevirus,Torque teno virus 3 | 1 | — | AY666122 |
| Torque teno virus 4 | NC_014069 | vertebrates,human | Anelloviridae,Alphatorquevirus,Torque teno virus 4 | 1 | — | AB041957 |
| Torque teno virus 6 | NC_014094 | vertebrates,human | Anelloviridae,Alphatorquevirus,Torque teno virus 6 | 1 | — | AF435014 |
| Torque teno virus 7 | NC_014080 | vertebrates,human | Anelloviridae,Alphatorquevirus,Torque teno virus 7 | 1 | — | AF261761 |
| Torque teno virus 8 | NC_014084 | vertebrates,human | Anelloviridae,Alphatorquevirus,Torque teno virus 8 | 1 | — | AB054647 |
| Torque teno zalophus virus 1 | NC_012126 | vertebrates,human | Anelloviridae,Lambdatorquevirus,Torque teno zalophus virus 1 | 1 | — | FJ459582 |
| Tula virus | NC_005226 | vertebrates,human | Bunyaviridae,Hantavirus,Tula virus | 1 | seg. L | AJQ05637 |
| Tula virus | NC_005227 | vertebrates,human | Bunyaviridae,Hantavirus,Tula virus | 18 | seg. S | AM945877,Z30945,AJ223600,AF017659,Z30943,Z30944,Y13980,AF164094,AJ223601,AF164093,Z30942,AF442621,Z48573,Y13979,Z30941,Z48741,Z48574,Z49915 |
| Rotavirus A human/Victoria/CK00026/2 005/G1P[8] | NC_011508 | vertebrates,human | Reoviridae,Rotavirus,Rotavirus A | 1 | seg. 3 | JF490334 |
| Rotavirus A human/Victoria/CK00026/2 005/G1P[8] | NC_011509 | vertebrates,human | Reoviridae,Rotavirus,Rotavirus A | 1 | seg. 6 | JF490332 |
| Rotavirus A human/Victoria/CK00026/2 005/G1P[8] | NC_011510 | vertebrates,human | Reoviridae,Rotavirus,Rotavirus A | 1 | seg. 4 | JF490333 |
| Rotavirus A human/Victoria/CK00027/2 054/G1P[8] | NC_011500 | vertebrates,human | Reoviridae,Rotavirus,Rotavirus A | 1 | seg. 5 | JF490338 |
| Rotavirus A human/Victoria/CK00027/2 054/G1P[8] | NC_011501 | vertebrates,human | Reoviridae,Rotavirus,Rotavirus A | 1 | seg. 7 | JF490342 |
| Rotavirus A human/Victoria/CK00027/2 054/G1P[8] | NC_011502 | vertebrates,human | Reoviridae,Rotavirus,Rotavirus A | 1 | seg. 8 | JF490337 |
| Rotavirus A human/Victoria/CK00027/2 054/G1P[8] | NC_011503 | vertebrates,human | Reoviridae,Rotavirus,Rotavirus A | 1 | seg. 9 | JF490341 |

TABLE 10-continued

| Taxonomy | Rep.Acc.ID | Host | # GN's | VirOCap-1.0 Taxonomy Lineage | Seg. Count | GN.Acc.IDs |
|---|---|---|---|---|---|---|
| Rotavirus A human/Victoria/CK00027/2 054/G1P[8] | NC_011504 | vertebrates,human | 1 | Reoviridae,Rotavirus,Rotavirus A | seg. 10 | JF490340 |
| Rotavirus A human/Victoria/CK00027/2 054/G1P[8] | NC_011505 | vertebrates,human | 1 | Reoviridae,Rotavirus,Rotavirus A | seg. 11 | JF490339 |
| Rotavirus A human/Victoria/CK00027/2 054/G1P[8] | NC_011506 | vertebrates,human | 1 | Reoviridae,Rotavirus,Rotavirus A | seg. 2 | JF490345 |
| Rotavirus A human/Victoria/CK00027/2 054/G1P[8] | NC_011507 | vertebrates,human | 1 | Reoviridae,Rotavirus,Rotavirus A | seg. 1 | JF490336 |
| Rotavirus A human/Victoria/CK00027/2 054/G1P[8] | NC_011508 | vertebrates,human | 1 | Reoviridae,Rotavirus,Rotavirus A | seg. 3 | JF490346 |
| Rotavirus A human/Victoria/CK00027/2 054/G1P[8] | NC_011509 | vertebrates,human | 1 | Reoviridae,Rotavirus,Rotavirus A | seg. 6 | JF490343 |
| Rotavirus A human/Victoria/CK00027/2 054/G1P[8] | NC_011510 | vertebrates,human | 1 | Reoviridae,Rotavirus,Rotavirus A | seg. 4 | JF490344 |
| Rotavirus A human/Victoria/CK00027/2 054/G1P[8] | NC_011500 | vertebrates,human | 1 | Reoviridae,Rotavirus,Rotavirus A | seg. 5 | JF490357 |
| Rotavirus A human/Victoria/CK00028/2 005/G1P[8] | NC_011501 | vertebrates,human | 1 | Reoviridae,Rotavirus,Rotavirus A | seg. 7 | JF490352 |
| Rotavirus A human/Victoria/CK00028/2 005/G1P[8] | NC_011502 | vertebrates,human | 1 | Reoviridae,Rotavirus,Rotavirus A | seg. 8 | JF490348 |
| Rotavirus A human/Victoria/CK00028/2 005/G1P[8] | NC_011503 | vertebrates,human | 1 | Reoviridae,Rotavirus,Rotavirus A | seg. 9 | JF490351 |
| Rotavirus A human/Victoria/CK00028/2 005/G1P[8] | NC_011504 | vertebrates,human | 1 | Reoviridae,Rotavirus,Rotavirus A | seg. 10 | JF490350 |
| Rotavirus A human/Victoria/CK00028/2 005/G1P[8] | NC_011505 | vertebrates,human | 1 | Reoviridae,Rotavirus,Rotavirus A | seg. 11 | JF490349 |
| Rotavirus A human/Victoria/CK00028/2 005/G1P[8] | NC_011506 | vertebrates,human | 1 | Reoviridae,Rotavirus,Rotavirus A | seg. 2 | JF490356 |
| Rotavirus A human/Victoria/CK00028/2 005/G1P[8] | NC_011507 | vertebrates,human | 1 | Reoviridae,Rotavirus,Rotavirus A | seg. 1 | JF490347 |
| Rotavirus A human/Victoria/CK00028/2 005/G1P[8] | NC_011508 | vertebrates,human | 1 | Reoviridae,Rotavirus,Rotavirus A | seg. 3 | JF490355 |

TABLE 10-continued

| Taxonomy | Rep.Acc.ID | Host | VirCap-1.0 Taxonomy Lineage | # GN's | Seg. Count | GN.Acc.IDs |
|---|---|---|---|---|---|---|
| Rotavirus A human/Victoria/CK00028/2005/G1P[8] | NC_011509 | vertebrates,human | Reoviridae,Rotavirus,Rotavirus A | 1 | seg. 6 | JF490353 |
| Rotavirus A human/Victoria/CK00028/2005/G1P[8] | NC_011510 | vertebrates,human | Reoviridae,Rotavirus,Rotavirus A | 1 | seg. 4 | JF490354 |
| Rotavirus A human/Victoria/CK00029/2006/G1P[8] | NC_011500 | vertebrates,human | Reoviridae,Rotavirus,Rotavirus A | 1 | seg. 5 | JF490360 |
| Rotavirus A human/Victoria/CK00029/2006/G1P[8] | NC_011501 | vertebrates,human | Reoviridae,Rotavirus,Rotavirus A | 1 | seg. 7 | JF490363 |
| Rotavirus A human/Victoria/CK00029/2006/G1P[8] | NC_011502 | vertebrates,human | Reoviridae,Rotavirus,Rotavirus A | 1 | seg. 8 | JF490359 |
| Rotavirus A human/Victoria/CK00029/2006/G1P[8] | NC_011503 | vertebrates,human | Reoviridae,Rotavirus,Rotavirus A | 1 | seg. 9 | JF490368 |
| Rotavirus A human/Victoria/CK00029/2006/G1P[8] | NC_011504 | vertebrates,human | Reoviridae,Rotavirus,Rotavirus A | 1 | seg. 10 | JF490362 |
| Rotavirus A human/Victoria/CK00029/2006/G1P[8] | NC_011505 | vertebrates,human | Reoviridae,Rotavirus,Rotavirus A | 1 | seg. 11 | JF490361 |
| Rotavirus A human/Victoria/CK00029/2006/G1P[8] | NC_011506 | vertebrates,human | Reoviridae,Rotavirus,Rotavirus A | 1 | seg. 2 | JF490367 |
| Rotavirus A human/Victoria/CK00029/2006/G1P[8] | NC_011507 | vertebrates,human | Reoviridae,Rotavirus,Rotavirus A | 1 | seg. 1 | JF490358 |
| Rotavirus A human/Victoria/CK00029/2006/G1P[8] | NC_011508 | vertebrates,human | Reoviridae,Rotavirus,Rotavirus A | 1 | seg. 3 | JF490366 |
| Rotavirus A human/Victoria/CK00029/2006/G1P[8] | NC_011509 | vertebrates,human | Reoviridae,Rotavirus,Rotavirus A | 1 | seg. 6 | JF490364 |
| Rotavirus A human/Victoria/CK00029/2006/G1P[8] | NC_011510 | vertebrates,human | Reoviridae,Rotavirus,Rotavirus A | 1 | seg. 4 | JF490365 |
| Rotavirus A human/Victoria/CK00030/2006/G1P[8] | NC_011500 | vertebrates,human | Reoviridae,Rotavirus,Rotavirus A | 1 | seg. 5 | JF490371 |
| Rotavirus A human/Victoria/CK00030/2006/G1P[8] | NC_011501 | vertebrates,human | Reoviridae,Rotavirus,Rotavirus A | 1 | seg. 7 | JF490375 |
| Rotavirus A human/Victoria/CK00030/2006/G1P[8] | NC_011502 | vertebrates,human | Reoviridae,Rotavirus,Rotavirus A | 1 | seg. 8 | JF490370 |

TABLE 10-continued

| Taxonomy | Rep.Acc.ID | Host | ViroCap-1.0 Taxonomy Lineage | # GN's | Seg. Count | GN.Acc.IDs |
|---|---|---|---|---|---|---|
| Rotavirus A human/Victoria/CK00030/2 006/G1P[8] | NC_011503 | vertebrates,human | Reoviridae,Rotavirus,Rotavirus A | 1 | seg. 9 | JF490374 |
| Rotavirus A human/Victoria/CK00030/2 006/G1P[8] | NC_011504 | vertebrates,human | Reoviridae,Rotavirus,Rotavirus A | 1 | seg. 10 | JF490373 |
| Rotavirus A human/Victoria/CK00030/2 006/G1P[8] | NC_011505 | vertebrates,human | Reoviridae,Rotavirus,Rotavirus A | 1 | seg. 11 | JF490372 |
| Rotavirus A human/Victoria/CK00030/2 006/G1P[8] | NC_011506 | vertebrates,human | Reoviridae,Rotavirus,Rotavirus A | 1 | seg. 2 | JF490379 |
| Rotavirus A human/Victoria/CK00030/2 006/G1P[8] | NC_011507 | vertebrates,human | Reoviridae,Rotavirus,Rotavirus A | 1 | seg. 1 | JF490369 |
| Rotavirus A human/Victoria/CK00030/2 006/G1P[8] | NC_011508 | vertebrates,human | Reoviridae,Rotavirus,Rotavirus A | 1 | seg. 3 | JF490377 |
| Rotavirus A human/Victoria/CK00030/2 006/G1P[8] | NC_011509 | vertebrates,human | Reoviridae,Rotavirus,Rotavirus A | 1 | seg. 6 | JF490376 |
| Rotavirus A human/Victoria/CK00030/2 006/G1P[8] | NC_011510 | vertebrates,human | Reoviridae,Rotavirus,Rotavirus A | 1 | seg. 4 | JF490378 |
| Rotavirus A human/Victoria/CK00032/2 006/G1P[8] | NC_011500 | vertebrates,human | Reoviridae,Rotavirus,Rotavirus A | 1 | seg. 5 | JF490382 |
| Rotavirus A human/Victoria/CK00032/2 006/G1P[8] | NC_011501 | vertebrates,human | Reoviridae,Rotavirus,Rotavirus A | 1 | seg. 7 | JF490386 |
| Rotavirus A human/Victoria/CK00032/2 006/G1P[8] | NC_011502 | vertebrates,human | Reoviridae,Rotavirus,Rotavirus A | 1 | seg. 8 | JF490381 |
| Rotavirus A human/Victoria/CK00032/2 006/G1P[8] | NC_011503 | vertebrates,human | Reoviridae,Rotavirus,Rotavirus A | 1 | seg. 9 | JF490385 |
| Rotavirus A human/Victoria/CK00032/2 006/G1P[8] | NC_011504 | vertebrates,human | Reoviridae,Rotavirus,Rotavirus A | 1 | seg. 10 | JF490384 |
| Rotavirus A human/Victoria/CK00032/2 006/G1P[8] | NC_011505 | vertebrates,human | Reoviridae,Rotavirus,Rotavirus A | 1 | seg. 11 | JF490383 |
| Rotavirus A human/Victoria/CK00032/2 006/G1P[8] | NC_011506 | vertebrates,human | Reoviridae,Rotavirus,Rotavirus A | 1 | seg. 2 | JF490390 |
| Rotavirus A human/Victoria/CK00032/2 006/G1P[8] | NC_011507 | vertebrates,human | Reoviridae,Rotavirus,Rotavirus A | 1 | seg. 1 | JF490380 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Victoria/CK00032/2006/G1P[8] | NC_011508 | vertebrates,human | 1 | Reoviridae,Rotavirus,Rotavirus A | seg. 3 | JF490389 |
| Rotavirus A human/Victoria/CK00032/2006/G1P[8] | NC_011509 | vertebrates,human | 1 | Reoviridae,Rotavirus,Rotavirus A | seg. 6 | JF490387 |
| Rotavirus A human/Victoria/CK00032/2006/G1P[8] | NC_011510 | vertebrates,human | 1 | Reoviridae,Rotavirus,Rotavirus A | seg. 4 | JF490388 |
| Rotavirus A human/Victoria/CK00033/2007/G1P[8] | NC_011500 | vertebrates,human | 1 | Reoviridae,Rotavirus,Rotavirus A | seg. 5 | JF490393 |
| Rotavirus A human/Victoria/CK00033/2007/G1P[8] | NC_011501 | vertebrates,human | 1 | Reoviridae,Rotavirus,Rotavirus A | seg. 7 | JF490397 |
| Rotavirus A human/Victoria/CK00033/2007/G1P[8] | NC_011502 | vertebrates,human | 1 | Reoviridae,Rotavirus,Rotavirus A | seg. 8 | JF490392 |
| Rotavirus A human/Victoria/CK00033/2007/G1P[8] | NC_011503 | vertebrates,human | 1 | Reoviridae,Rotavirus,Rotavirus A | seg. 9 | JF490396 |
| Rotavirus A human/Victoria/CK00033/2007/G1P[8] | NC_011504 | vertebrates,human | 1 | Reoviridae,Rotavirus,Rotavirus A | seg. 10 | JF490395 |
| Rotavirus A human/Victoria/CK00033/2007/G1P[8] | NC_011505 | vertebrates,human | 1 | Reoviridae,Rotavirus,Rotavirus A | seg. 11 | JF490394 |
| Rotavirus A human/Victoria/CK00033/2007/G1P[8] | NC_011506 | vertebrates,human | 1 | Reoviridae,Rotavirus,Rotavirus A | seg. 2 | JF490401 |
| Rotavirus A human/Victoria/CK00033/2007/G1P[8] | NC_011507 | vertebrates,human | 1 | Reoviridae,Rotavirus,Rotavirus A | seg. 1 | JF490391 |
| Rotavirus A human/Victoria/CK00033/2007/G1P[8] | NC_011508 | vertebrates,human | 1 | Reoviridae,Rotavirus,Rotavirus A | seg. 3 | JF490400 |
| Rotavirus A human/Victoria/CK00033/2007/G1P[8] | NC_011509 | vertebrates,human | 1 | Reoviridae,Rotavirus,Rotavirus A | seg. 6 | JF490398 |
| Rotavirus A human/Victoria/CK00033/2007/G1P[8] | NC_011510 | vertebrates,human | 1 | Reoviridae,Rotavirus,Rotavirus A | seg. 4 | JF490399 |
| Rotavirus A human/Victoria/CK00034/2007/G1P[8] | NC_011500 | vertebrates,human | 1 | Reoviridae,Rotavirus,Rotavirus A | seg. 5 | JF490410 |
| Rotavirus A human/Victoria/CK00034/2007/G1P[8] | NC_011501 | vertebrates,human | 1 | Reoviridae,Rotavirus,Rotavirus A | seg. 7 | JF490407 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Victoria/CK00034/2007/G1P[8] | NC_011502 | vertebrates,human | 1 | Reoviridae,Rotavirus,Rotavirus A | seg. 8 | JF490403 |
| Rotavirus A human/Victoria/CK00034/2007/G1P[8] | NC_011503 | vertebrates,human | 1 | Reoviridae,Rotavirus,Rotavirus A | seg. 9 | JF490406 |
| Rotavirus A human/Victoria/CK00034/2007/G1P[8] | NC_011504 | vertebrates,human | 1 | Reoviridae,Rotavirus,Rotavirus A | seg. 10 | JF490405 |
| Rotavirus A human/Victoria/CK00034/2007/G1P[8] | NC_011505 | vertebrates,human | 1 | Reoviridae,Rotavirus,Rotavirus A | seg. 11 | JF490404 |
| Rotavirus A human/Victoria/CK00034/2007/G1P[8] | NC_011506 | vertebrates,human | 1 | Reoviridae,Rotavirus,Rotavirus A | seg. 2 | JF490412 |
| Rotavirus A human/Victoria/CK00034/2007/G1P[8] | NC_011507 | vertebrates,human | 1 | Reoviridae,Rotavirus,Rotavirus A | seg. 1 | JF490402 |
| Rotavirus A human/Victoria/CK00034/2007/G1P[8] | NC_011508 | vertebrates,human | 1 | Reoviridae,Rotavirus,Rotavirus A | seg. 3 | JF490411 |
| Rotavirus A human/Victoria/CK00034/2007/G1P[8] | NC_011509 | vertebrates,human | 1 | Reoviridae,Rotavirus,Rotavirus A | seg. 6 | JF490408 |
| Rotavirus A human/Victoria/CK00034/2007/G1P[8] | NC_011510 | vertebrates,human | 1 | Reoviridae,Rotavirus,Rotavirus A | seg. 4 | JF490409 |
| Rotavirus A human/Victoria/CK00035/2007/G1P[8] | NC_011500 | vertebrates,human | 1 | Reoviridae,Rotavirus,Rotavirus A | seg. 5 | JF490415 |
| Rotavirus A human/Victoria/CK00035/2007/G1P[8] | NC_011501 | vertebrates,human | 1 | Reoviridae,Rotavirus,Rotavirus A | seg. 7 | JF490419 |
| Rotavirus A human/Victoria/CK00035/2007/G1P[8] | NC_011502 | vertebrates,human | 1 | Reoviridae,Rotavirus,Rotavirus A | seg. 8 | JF490414 |
| Rotavirus A human/Victoria/CK00035/2007/G1P[8] | NC_011503 | vertebrates,human | 1 | Reoviridae,Rotavirus,Rotavirus A | seg. 9 | JF490418 |
| Rotavirus A human/Victoria/CK00035/2007/G1P[8] | NC_011504 | vertebrates,human | 1 | Reoviridae,Rotavirus,Rotavirus A | seg. 10 | JF490417 |
| Rotavirus A human/Victoria/CK00035/2007/G1P[8] | NC_011505 | vertebrates,human | 1 | Reoviridae,Rotavirus,Rotavirus A | seg. 11 | JF490416 |
| Rotavirus A human/Victoria/CK00035/2007/G1P[8] | NC_011506 | vertebrates,human | 1 | Reoviridae,Rotavirus,Rotavirus A | seg. 2 | JF490423 |

TABLE 10-continued

| Taxonomy | Rep.Acc.ID | Host | Lineage | # GN's | Seg. Count | GN.Acc.IDs |
|---|---|---|---|---|---|---|
| Rotavirus A human/Victoria/CK00035/2 005/G1P[8] | NC_011507 | vertebrates,human | Reoviridae,Rotavirus,Rotavirus A | 1 | seg. 1 | JF490413 |
| Rotavirus A human/Victoria/CK00035/2 005/G1P[8] | NC_011508 | vertebrates,human | Reoviridae,Rotavirus,Rotavirus A | 1 | seg. 3 | JF490422 |
| Rotavirus A human/Victoria/CK00035/2 005/G1P[8] | NC_011509 | vertebrates,human | Reoviridae,Rotavirus,Rotavirus A | 1 | seg. 6 | JF490420 |
| Rotavirus A human/Victoria/CK00035/2 005/G1P[8] | NC_011510 | vertebrates,human | Reoviridae,Rotavirus,Rotavirus A | 1 | seg. 4 | JF490421 |
| Rotavirus A human/Victoria/CK00036/2 005/G1P[8] | NC_011500 | vertebrates,human | Reoviridae,Rotavirus,Rotavirus A | 1 | seg. 5 | JF490434 |
| Rotavirus A human/Victoria/CK00036/2 005/G1P[8] | NC_011501 | vertebrates,human | Reoviridae,Rotavirus,Rotavirus A | 1 | seg. 7 | JF490429 |
| Rotavirus A human/Victoria/CK00036/2 005/G1P[8] | NC_011502 | vertebrates,human | Reoviridae,Rotavirus,Rotavirus A | 1 | seg. 8 | JF490425 |
| Rotavirus A human/Victoria/CK00036/2 005/G1P[8] | NC_011503 | vertebrates,human | Reoviridae,Rotavirus,Rotavirus A | 1 | seg. 9 | JF490428 |
| Rotavirus A human/Victoria/CK00036/2 005/G1P[8] | NC_011504 | vertebrates,human | Reoviridae,Rotavirus,Rotavirus A | 1 | seg. 10 | JF490427 |
| Rotavirus A human/Victoria/CK00036/2 005/G1P[8] | NC_011505 | vertebrates,human | Reoviridae,Rotavirus,Rotavirus A | 1 | seg. 11 | JF490426 |
| Rotavirus A human/Victoria/CK00036/2 005/G1P[8] | NC_011506 | vertebrates,human | Reoviridae,Rotavirus,Rotavirus A | 1 | seg. 2 | JF490433 |
| Rotavirus A human/Victoria/CK00036/2 005/G1P[8] | NC_011507 | vertebrates,human | Reoviridae,Rotavirus,Rotavirus A | 1 | seg. 1 | JF490424 |
| Rotavirus A human/Victoria/CK00036/2 005/G1P[8] | NC_011508 | vertebrates,human | Reoviridae,Rotavirus,Rotavirus A | 1 | seg. 3 | JF490432 |
| Rotavirus A human/Victoria/CK00036/2 005/G1P[8] | NC_011509 | vertebrates,human | Reoviridae,Rotavirus,Rotavirus A | 1 | seg. 6 | JF490430 |
| Rotavirus A human/Victoria/CK00036/2 005/G1P[8] | NC_011510 | vertebrates,human | Reoviridae,Rotavirus,Rotavirus A | 1 | seg. 4 | JF490431 |
| Rotavirus A human/Victoria/CK00037/2 006/G1P[8] | NC_011500 | vertebrates,human | Reoviridae,Rotavirus,Rotavirus A | 1 | seg. 5 | JF490443 |

TABLE 10-continued

| Taxonomy | Rep.Acc.ID | Host | # GN's | VrioCap-1.0 Taxonomy Lineage | Seg. Count | GN.Acc.IDs |
|---|---|---|---|---|---|---|
| Rotavirus A human/Victoria/CK00037/2006/G1P[8] | NC_011501 | vertebrates,human | 1 | Reoviridae,Rotavirus,Rotavirus A | seg. 7 | JF490439 |
| Rotavirus A human/Victoria/CK00037/2006/G1P[8] | NC_011502 | vertebrates,human | 1 | Reoviridae,Rotavirus,Rotavirus A | seg. 8 | JF490436 |
| Rotavirus A human/Victoria/CK00037/2006/G1P[8] | NC_011503 | vertebrates,human | 1 | Reoviridae,Rotavirus,Rotavirus A | seg. 9 | JF490444 |
| Rotavirus A human/Victoria/CK00037/2006/G1P[8] | NC_011504 | vertebrates,human | 1 | Reoviridae,Rotavirus,Rotavirus A | seg. 10 | JF490438 |
| Rotavirus A human/Victoria/CK00037/2006/G1P[8] | NC_011505 | vertebrates,human | 1 | Reoviridae,Rotavirus,Rotavirus A | seg. 11 | JF490437 |
| Rotavirus A human/Victoria/CK00037/2006/G1P[8] | NC_011506 | vertebrates,human | 1 | Reoviridae,Rotavirus,Rotavirus A | seg. 2 | JF490445 |
| Rotavirus A human/Victoria/CK00037/2006/G1P[8] | NC_011507 | vertebrates,human | 1 | Reoviridae,Rotavirus,Rotavirus A | seg. 1 | JF490435 |
| Rotavirus A human/Victoria/CK00037/2006/G1P[8] | NC_011508 | vertebrates,human | 1 | Reoviridae,Rotavirus,Rotavirus A | seg. 3 | JF490442 |
| Rotavirus A human/Victoria/CK00037/2006/G1P[8] | NC_011509 | vertebrates,human | 1 | Reoviridae,Rotavirus,Rotavirus A | seg. 6 | JF490440 |
| Rotavirus A human/Victoria/CK00037/2006/G1P[8] | NC_011510 | vertebrates,human | 1 | Reoviridae,Rotavirus,Rotavirus A | seg. 4 | JF490441 |
| Rotavirus A human/Victoria/CK00037/2006/G1P[8] | NC_011500 | vertebrates,human | 1 | Reoviridae,Rotavirus,Rotavirus A | seg. 5 | JF490448 |
| Rotavirus A human/Victoria/CK00039/2006/G1P[8] | NC_011501 | vertebrates,human | 1 | Reoviridae,Rotavirus,Rotavirus A | seg. 7 | JF490452 |
| Rotavirus A human/Victoria/CK00039/2006/G1P[8] | NC_011502 | vertebrates,human | 1 | Reoviridae,Rotavirus,Rotavirus A | seg. 8 | JF490447 |
| Rotavirus A human/Victoria/CK00039/2006/G1P[8] | NC_011503 | vertebrates,human | 1 | Reoviridae,Rotavirus,Rotavirus A | seg. 9 | JF490451 |
| Rotavirus A human/Victoria/CK00039/2006/G1P[8] | NC_011504 | vertebrates,human | 1 | Reoviridae,Rotavirus,Rotavirus A | seg. 10 | JF490450 |
| Rotavirus A human/Victoria/CK00039/2006/G1P[8] | NC_011505 | vertebrates,human | 1 | Reoviridae,Rotavirus,Rotavirus A | seg. 11 | JF490449 |

TABLE 10-continued

| Taxonomy | Rep.Acc.ID | Host | # GN's | Lineage | Seg. Count | GN.Acc.IDs |
|---|---|---|---|---|---|---|
| Rotavirus A human/Victoria/CK00039/2006/G1P[8] | NC_011506 | vertebrates,human | 1 | Reoviridae,Rotavirus,Rotavirus A | seg. 2 | JF490456 |
| Rotavirus A human/Victoria/CK00039/2006/G1P[8] | NC_011507 | vertebrates,human | 1 | Reoviridae,Rotavirus,Rotavirus A | seg. 1 | JF490446 |
| Rotavirus A human/Victoria/CK00039/2006/G1P[8] | NC_011508 | vertebrates,human | 1 | Reoviridae,Rotavirus,Rotavirus A | seg. 3 | JF490455 |
| Rotavirus A human/Victoria/CK00039/2006/G1P[8] | NC_011509 | vertebrates,human | 1 | Reoviridae,Rotavirus,Rotavirus A | seg. 6 | JF490453 |
| Rotavirus A human/Victoria/CK00039/2006/G1P[8] | NC_011510 | vertebrates,human | 1 | Reoviridae,Rotavirus,Rotavirus A | seg. 4 | JF490454 |
| Rotavirus A human/Victoria/CK00040/2006/G1P[8] | NC_011500 | vertebrates,human | 1 | Reoviridae,Rotavirus,Rotavirus A | seg. 5 | JF490459 |
| Rotavirus A human/Victoria/CK00040/2006/G1P[8] | NC_011501 | vertebrates,human | 1 | Reoviridae,Rotavirus,Rotavirus A | seg. 7 | JF490463 |
| Rotavirus A human/Victoria/CK00040/2006/G1P[8] | NC_011502 | vertebrates,human | 1 | Reoviridae,Rotavirus,Rotavirus A | seg. 8 | JF490458 |
| Rotavirus A human/Victoria/CK00040/2006/G1P[8] | NC_011503 | vertebrates,human | 1 | Reoviridae,Rotavirus,Rotavirus A | seg. 9 | JF490462 |
| Rotavirus A human/Victoria/CK00040/2006/G1P[8] | NC_011504 | vertebrates,human | 1 | Reoviridae,Rotavirus,Rotavirus A | seg. 10 | JF490461 |
| Rotavirus A human/Victoria/CK00040/2006/G1P[8] | NC_011505 | vertebrates,human | 1 | Reoviridae,Rotavirus,Rotavirus A | seg. 11 | JF490460 |
| Rotavirus A human/Victoria/CK00040/2006/G1P[8] | NC_011506 | vertebrates,human | 1 | Reoviridae,Rotavirus,Rotavirus A | seg. 2 | JF490467 |
| Rotavirus A human/Victoria/CK00040/2006/G1P[8] | NC_011507 | vertebrates,human | 1 | Reoviridae,Rotavirus,Rotavirus A | seg. 1 | JF490457 |
| Rotavirus A human/Victoria/CK00040/2006/G1P[8] | NC_011508 | vertebrates,human | 1 | Reoviridae,Rotavirus,Rotavirus A | seg. 3 | JF490466 |
| Rotavirus A human/Victoria/CK00040/2006/G1P[8] | NC_011509 | vertebrates,human | 1 | Reoviridae,Rotavirus,Rotavirus A | seg. 6 | JF490464 |
| Rotavirus A human/Victoria/CK00040/2006/G1P[8] | NC_011510 | vertebrates,human | 1 | Reoviridae,Rotavirus,Rotavirus A | seg. 4 | JF490465 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rotavirus A human/Victoria/CK00041/2 006/G1P[8] | NC_011500 | vertebrates,human | 1 | Reoviridae,Rotavirus,Rotavirus A | seg. 5 | JF490470 |
| Rotavirus A human/Victoria/CK00041/2 006/G1P[8] | NC_011501 | vertebrates,human | 1 | Reoviridae,Rotavirus,Rotavirus A | seg. 7 | JF490474 |
| Rotavirus A human/Victoria/CK00041/2 006/G1P[8] | NC_011502 | vertebrates,human | 1 | Reoviridae,Rotavirus,Rotavirus A | seg. 8 | JF490469 |
| Rotavirus A human/Victoria/CK00041/2 006/G1P[8] | NC_011503 | vertebrates,human | 1 | Reoviridae,Rotavirus,Rotavirus A | seg. 9 | JF490473 |
| Rotavirus A human/Victoria/CK00041/2 006/G1P[8] | NC_011504 | vertebrates,human | 1 | Reoviridae,Rotavirus,Rotavirus A | seg. 10 | JF490472 |
| Rotavirus A human/Victoria/CK00041/2 006/G1P[8] | NC_011505 | vertebrates,human | 1 | Reoviridae,Rotavirus,Rotavirus A | seg. 11 | JF490471 |
| Rotavirus A human/Victoria/CK00041/2 006/G1P[8] | NC_011506 | vertebrates,human | 1 | Reoviridae,Rotavirus,Rotavirus A | seg. 2 | JF490478 |
| Rotavirus A human/Victoria/CK00041/2 006/G1P[8] | NC_011507 | vertebrates,human | 1 | Reoviridae,Rotavirus,Rotavirus A | seg. 1 | JF490468 |
| Rotavirus A human/Victoria/CK00041/2 006/G1P[8] | NC_011508 | vertebrates,human | 1 | Reoviridae,Rotavirus,Rotavirus A | seg. 3 | JF490477 |
| Rotavirus A human/Victoria/CK00041/2 006/G1P[8] | NC_011509 | vertebrates,human | 1 | Reoviridae,Rotavirus,Rotavirus A | seg. 6 | JF490475 |
| Rotavirus A human/Victoria/CK00041/2 006/G1P[8] | NC_011510 | vertebrates,human | 1 | Reoviridae,Rotavirus,Rotavirus A | seg. 4 | JF490476 |
| Rotavirus A human/Victoria/CK00043/2 006/G1P[8] | NC_011500 | vertebrates,human | 1 | Reoviridae,Rotavirus,Rotavirus A | seg. 5 | JF490481 |
| Rotavirus A human/Victoria/CK00043/2 006/G1P[8] | NC_011501 | vertebrates,human | 1 | Reoviridae,Rotavirus,Rotavirus A | seg. 7 | JF490485 |
| Rotavirus A human/Victoria/CK00043/2 006/G1P[8] | NC_011502 | vertebrates,human | 1 | Reoviridae,Rotavirus,Rotavirus A | seg. 8 | JF490480 |
| Rotavirus A human/Victoria/CK00043/2 006/G1P[8] | NC_011503 | vertebrates,human | 1 | Reoviridae,Rotavirus,Rotavirus A | seg. 9 | JF490484 |
| Rotavirus A human/Victoria/CK00043/2 006/G1P[8] | NC_011504 | vertebrates,human | 1 | Reoviridae,Rotavirus,Rotavirus A | seg. 10 | JF490483 |

TABLE 10-continued

VireCap-1.0 Taxonomy

| Taxonomy | Rep.Acc.ID | Host | # GN's | Lineage | Seg. Count | GN.Acc.IDs |
|---|---|---|---|---|---|---|
| Rotavirus A human/Victoria/CK00043/2 006/G1P[8] | NC_011505 | vertebrates,human | 1 | Reoviridae,Rotavirus,Rotavirus A | seg. 11 | JF490482 |
| Rotavirus A human/Victoria/CK00043/2 006/G1P[8] | NC_011506 | vertebrates,human | 1 | Reoviridae,Rotavirus,Rotavirus A | seg. 2 | JF490489 |
| Rotavirus A human/Victoria/CK00043/2 006/G1P[8] | NC_011507 | vertebrates,human | 1 | Reoviridae,Rotavirus,Rotavirus A | seg. 1 | JF490479 |
| Rotavirus A human/Victoria/CK00043/2 006/G1P[8] | NC_011508 | vertebrates,human | 1 | Reoviridae,Rotavirus,Rotavirus A | seg. 3 | JF490488 |
| Rotavirus A human/Victoria/CK00043/2 006/G1P[8] | NC_011509 | vertebrates,human | 1 | Reoviridae,Rotavirus,Rotavirus A | seg. 6 | JF490486 |
| Rotavirus A human/Victoria/CK00043/2 006/G1P[8] | NC_011510 | vertebrates,human | 1 | Reoviridae,Rotavirus,Rotavirus A | seg. 4 | JF490487 |
| Rotavirus A human/Victoria/CK00045/2 006/G1P[8] | NC_011500 | vertebrates,human | 1 | Reoviridae,Rotavirus,Rotavirus A | seg. 5 | JF490495 |
| Rotavirus A human/Victoria/CK00045/2 006/G1P[8] | NC_011501 | vertebrates,human | 1 | Reoviridae,Rotavirus,Rotavirus A | seg. 7 | JF490499 |
| Rotavirus A human/Victoria/CK00045/2 006/G1P[8] | NC_011502 | vertebrates,human | 1 | Reoviridae,Rotavirus,Rotavirus A | seg. 8 | JF490494 |
| Rotavirus A human/Victoria/CK00045/2 006/G1P[8] | NC_011503 | vertebrates,human | 1 | Reoviridae,Rotavirus,Rotavirus A | seg. 9 | JF490498 |
| Rotavirus A human/Victoria/CK00045/2 006/G1P[8] | NC_011504 | vertebrates,human | 1 | Reoviridae,Rotavirus,Rotavirus A | seg. 10 | JF490497 |
| Rotavirus A human/Victoria/CK00045/2 006/G1P[8] | NC_011505 | vertebrates,human | 1 | Reoviridae,Rotavirus,Rotavirus A | seg. 11 | JF490496 |
| Rotavirus A human/Victoria/CK00045/2 006/G1P[8] | NC_011506 | vertebrates,human | 1 | Reoviridae,Rotavirus,Rotavirus A | seg. 2 | JF490493 |
| Rotavirus A human/Victoria/CK00045/2 006/G1P[8] | NC_011507 | vertebrates,human | 1 | Reoviridae,Rotavirus,Rotavirus A | seg. 1 | JF490490 |
| Rotavirus A human/Victoria/CK00045/2 006/G1P[8] | NC_011508 | vertebrates,human | 1 | Reoviridae,Rotavirus,Rotavirus A | seg. 3 | JF490492 |
| Rotavirus A human/Victoria/CK00045/2 006/G1P[8] | NC_011509 | vertebrates,human | 1 | Reoviridae,Rotavirus,Rotavirus A | seg. 6 | JF490500 |

TABLE 10-continued

| Taxonomy | Rep.Acc.ID | Host | Lineage | # GN's | Seg. Count | GN.Acc.IDs |
|---|---|---|---|---|---|---|
| Rotavirus A human/Victoria/CK00045/2 006/G1P[8] | NC_011510 | vertebrates,human | Reoviridae,Rotavirus,Rotavirus A | 1 | seg. 4 | JF490491 |
| Rotavirus A human/Victoria/CK00046/2 006/G1P[8] | NC_011500 | vertebrates,human | Reoviridae,Rotavirus,Rotavirus A | 1 | seg. 5 | JF490503 |
| Rotavirus A human/Victoria/CK00046/2 006/G1P[8] | NC_011501 | vertebrates,human | Reoviridae,Rotavirus,Rotavirus A | 1 | seg. 7 | JF490507 |
| Rotavirus A human/Victoria/CK00046/2 006/G1P[8] | NC_011502 | vertebrates,human | Reoviridae,Rotavirus,Rotavirus A | 1 | seg. 8 | JF490502 |
| Rotavirus A human/Victoria/CK00046/2 006/G1P[8] | NC_011503 | vertebrates,human | Reoviridae,Rotavirus,Rotavirus A | 1 | seg. 9 | JF490506 |
| Rotavirus A human/Victoria/CK00046/2 006/G1P[8] | NC_011504 | vertebrates,human | Reoviridae,Rotavirus,Rotavirus A | 1 | seg. 10 | JF490505 |
| Rotavirus A human/Victoria/CK00046/2 006/G1P[8] | NC_011505 | vertebrates,human | Reoviridae,Rotavirus,Rotavirus A | 1 | seg. 11 | JF490504 |
| Rotavirus A human/Victoria/CK00046/2 006/G1P[8] | NC_011506 | vertebrates,human | Reoviridae,Rotavirus,Rotavirus A | 1 | seg. 2 | JF490511 |
| Rotavirus A human/Victoria/CK00046/2 006/G1P[8] | NC_011507 | vertebrates,human | Reoviridae,Rotavirus,Rotavirus A | 1 | seg. 1 | JF490501 |
| Rotavirus A human/Victoria/CK00046/2 006/G1P[8] | NC_011508 | vertebrates,human | Reoviridae,Rotavirus,Rotavirus A | 1 | seg. 3 | JF490510 |
| Rotavirus A human/Victoria/CK00046/2 006/G1P[8] | NC_011509 | vertebrates,human | Reoviridae,Rotavirus,Rotavirus A | 1 | seg. 6 | JF490508 |
| Rotavirus A human/Victoria/CK00046/2 006/G1P[8] | NC_011510 | vertebrates,human | Reoviridae,Rotavirus,Rotavirus A | 1 | seg. 4 | JF490509 |
| Rotavirus A human/Victoria/CK00047/2 006/G1P[8] | NC_011500 | vertebrates,human | Reoviridae,Rotavirus,Rotavirus A | 1 | seg. 5 | JF490514 |
| Rotavirus A human/Victoria/CK00047/2 006/G1P[8] | NC_011501 | vertebrates,human | Reoviridae,Rotavirus,Rotavirus A | 1 | seg. 7 | JF490518 |
| Rotavirus A human/Victoria/CK00047/2 006/G1P[8] | NC_011502 | vertebrates,human | Reoviridae,Rotavirus,Rotavirus A | 1 | seg. 8 | JF490513 |
| Rotavirus A human/Victoria/CK00047/2 006/G1P[8] | NC_011503 | vertebrates,human | Reoviridae,Rotavirus,Rotavirus A | 1 | seg. 9 | JF490517 |

TABLE 10-continued

VidoCap-1.0 Taxonomy

| Taxonomy | Rep.Acc.ID | Host | Lineage | # GN's | Seg. Count | GN.Acc.IDs |
|---|---|---|---|---|---|---|
| Rotavirus A human/Victoria/CK00047/2 006/G1P[8] | NC_011504 | vertebrates,human | Reoviridae,Rotavirus,Rotavirus A | 1 | seg. 10 | JF490516 |
| Rotavirus A human/Victoria/CK00047/2 006/G1P[8] | NC_011505 | vertebrates,human | Reoviridae,Rotavirus,Rotavirus A | 1 | seg. 11 | JF490515 |
| Rotavirus A human/Victoria/CK00047/2 006/G1P[8] | NC_011506 | vertebrates,human | Reoviridae,Rotavirus,Rotavirus A | 1 | seg. 2 | JF490522 |
| Rotavirus A human/Victoria/CK00047/2 006/G1P[8] | NC_011507 | vertebrates,human | Reoviridae,Rotavirus,Rotavirus A | 1 | seg. 1 | JF490512 |
| Rotavirus A human/Victoria/CK00047/2 006/G1P[8] | NC_011508 | vertebrates,human | Reoviridae,Rotavirus,Rotavirus A | 1 | seg. 3 | JF490521 |
| Rotavirus A human/Victoria/CK00047/2 006/G1P[8] | NC_011509 | vertebrates,human | Reoviridae,Rotavirus,Rotavirus A | 1 | seg. 6 | JF490519 |
| Rotavirus A human/Victoria/CK00047/2 006/G1P[8] | NC_011510 | vertebrates,human | Reoviridae,Rotavirus,Rotavirus A | 1 | seg. 4 | JF490520 |
| Rotavirus A human/Victoria/CK00048/2 004/G1P[8] | NC_011500 | vertebrates,human | Reoviridae,Rotavirus,Rotavirus A | 1 | seg. 5 | JF490525 |
| Rotavirus A human/Victoria/CK00048/2 004/G1P[8] | NC_011501 | vertebrates,human | Reoviridae,Rotavirus,Rotavirus A | 1 | seg. 7 | JF490529 |
| Rotavirus A human/Victoria/CK00048/2 004/G1P[8] | NC_011502 | vertebrates,human | Reoviridae,Rotavirus,Rotavirus A | 1 | seg. 8 | JF490524 |
| Rotavirus A human/Victoria/CK00048/2 004/G1P[8] | NC_011503 | vertebrates,human | Reoviridae,Rotavirus,Rotavirus A | 1 | seg. 9 | JF490528 |
| Rotavirus A human/Victoria/CK00048/2 004/G1P[8] | NC_011504 | vertebrates,human | Reoviridae,Rotavirus,Rotavirus A | 1 | seg. 10 | JF490527 |
| Rotavirus A human/Victoria/CK00048/2 004/G1P[8] | NC_011505 | vertebrates,human | Reoviridae,Rotavirus,Rotavirus A | 1 | seg. 11 | JF490526 |
| Rotavirus A human/Victoria/CK00048/2 004/G1P[8] | NC_011506 | vertebrates,human | Reoviridae,Rotavirus,Rotavirus A | 1 | seg. 2 | JF490533 |
| Rotavirus A human/Victoria/CK00048/2 004/G1P[8] | NC_011507 | vertebrates,human | Reoviridae,Rotavirus,Rotavirus A | 1 | seg. 1 | JF490523 |
| Rotavirus A human/Victoria/CK00048/2 004/G1P[8] | NC_011508 | vertebrates,human | Reoviridae,Rotavirus,Rotavirus A | 1 | seg. 3 | JF490532 |

TABLE 10-continued

| Taxonomy | Rep.Acc.ID | Host | # GN's | VrioCap-1.0 Taxonomy Lineage | Seg. Count | GN.Acc.IDs |
|---|---|---|---|---|---|---|
| Rotavirus A human/Victoria/CK00048/2 004/G1P[8] | NC_011509 | vertebrates,human | 1 | Reoviridae,Rotavirus,Rotavirus A | seg. 6 | JF490530 |
| Rotavirus A human/Victoria/CK00048/2 004/G1P[8] | NC_011510 | vertebrates,human | 1 | Reoviridae,Rotavirus,Rotavirus A | seg. 4 | JF490531 |
| Rotavirus A human/Victoria/CK00049/2 004/G1P[8] | NC_011500 | vertebrates,human | 1 | Reoviridae,Rotavirus,Rotavirus A | seg. 5 | JF490536 |
| Rotavirus A human/Victoria/CK00049/2 004/G1P[8] | NC_011501 | vertebrates,human | 1 | Reoviridae,Rotavirus,Rotavirus A | seg. 7 | JF490540 |
| Rotavirus A human/Victoria/CK00049/2 004/G1P[8] | NC_011502 | vertebrates,human | 1 | Reoviridae,Rotavirus,Rotavirus A | seg. 8 | JF490535 |
| Rotavirus A human/Victoria/CK00049/2 004/G1P[8] | NC_011503 | vertebrates,human | 1 | Reoviridae,Rotavirus,Rotavirus A | seg. 9 | JF490539 |
| Rotavirus A human/Victoria/CK00049/2 004/G1P[8] | NC_011504 | vertebrates,human | 1 | Reoviridae,Rotavirus,Rotavirus A | seg. 10 | JF490538 |
| Rotavirus A human/Victoria/CK00049/2 004/G1P[8] | NC_011505 | vertebrates,human | 1 | Reoviridae,Rotavirus,Rotavirus A | seg. 11 | JF490537 |
| Rotavirus A human/Victoria/CK00049/2 004/G1P[8] | NC_011506 | vertebrates,human | 1 | Reoviridae,Rotavirus,Rotavirus A | seg. 2 | JF490544 |
| Rotavirus A human/Victoria/CK00049/2 004/G1P[8] | NC_011507 | vertebrates,human | 1 | Reoviridae,Rotavirus,Rotavirus A | seg. 1 | JF490534 |
| Rotavirus A human/Victoria/CK00049/2 004/G1P[8] | NC_011508 | vertebrates,human | 1 | Reoviridae,Rotavirus,Rotavirus A | seg. 3 | JF490542 |
| Rotavirus A human/Victoria/CK00049/2 004/G1P[8] | NC_011509 | vertebrates,human | 1 | Reoviridae,Rotavirus,Rotavirus A | seg. 6 | JF490541 |
| Rotavirus A human/Victoria/CK00049/2 004/G1P[8] | NC_011510 | vertebrates,human | 1 | Reoviridae,Rotavirus,Rotavirus A | seg. 4 | JF490543 |
| Rotavirus A human/Victoria/CK00050/2 005/G1P[8] | NC_011500 | vertebrates,human | 1 | Reoviridae,Rotavirus,Rotavirus A | seg. 5 | JF490553 |
| Rotavirus A human/Victoria/CK00050/2 005/G1P[8] | NC_011501 | vertebrates,human | 1 | Reoviridae,Rotavirus,Rotavirus A | seg. 7 | JF490550 |
| Rotavirus A human/Victoria/CK00050/2 005/G1P[8] | NC_011502 | vertebrates,human | 1 | Reoviridae,Rotavirus,Rotavirus A | seg. 8 | JF490546 |

TABLE 10-continued

| Taxonomy | Rep.Acc.ID | Host | # GN's | ViroCap-1.0 Taxonomy Lineage | Seg. Count | GN.Acc.IDs |
|---|---|---|---|---|---|---|
| Rotavirus A human/Victoria/CK00050/2005/G1P[8] | NC_011503 | vertebrates,human | 1 | Reoviridae,Rotavirus,Rotavirus A | seg. 9 | JF490549 |
| Rotavirus A human/Victoria/CK00050/2005/G1P[8] | NC_011504 | vertebrates,human | 1 | Reoviridae,Rotavirus,Rotavirus A | seg. 10 | JF490548 |
| Rotavirus A human/Victoria/CK00050/2005/G1P[8] | NC_011505 | vertebrates,human | 1 | Reoviridae,Rotavirus,Rotavirus A | seg. 11 | JF490547 |
| Rotavirus A human/Victoria/CK00050/2005/G1P[8] | NC_011506 | vertebrates,human | 1 | Reoviridae,Rotavirus,Rotavirus A | seg. 2 | JF490555 |
| Rotavirus A human/Victoria/CK00050/2005/G1P[8] | NC_011507 | vertebrates,human | 1 | Reoviridae,Rotavirus,Rotavirus A | seg. 1 | JF490545 |
| Rotavirus A human/Victoria/CK00050/2005/G1P[8] | NC_011508 | vertebrates,human | 1 | Reoviridae,Rotavirus,Rotavirus A | seg. 3 | JF490552 |
| Rotavirus A human/Victoria/CK00050/2005/G1P[8] | NC_011509 | vertebrates,human | 1 | Reoviridae,Rotavirus,Rotavirus A | seg. 6 | JF490551 |
| Rotavirus A human/Victoria/CK00050/2005/G1P[8] | NC_011510 | vertebrates,human | 1 | Reoviridae,Rotavirus,Rotavirus A | seg. 4 | JF490554 |
| Rotavirus A pheasant-tc/GER/10V0112H5/2010/G23P[37] | NC_011502 | vertebrates,human | 1 | Reoviridae,Rotavirus,Rotavirus A | seg. 8 | JX204816 |
| Rotavirus A pheasant-tc/GER/10V0112H5/2010/G23P[37] | NC_011503 | vertebrates,human | 1 | Reoviridae,Rotavirus,Rotavirus A | seg. 9 | JX204818 |
| Rotavirus A pheasant-tc/GER/10V0112H5/2010/G23P[37] | NC_011506 | vertebrates,human | 1 | Reoviridae,Rotavirus,Rotavirus A | seg. 2 | JX204812 |
| Rotavirus A pheasant-tc/GER/10V0112H5/2010/G23P[37] | NC_011507 | vertebrates,human | 1 | Reoviridae,Rotavirus,Rotavirus A | seg. 1 | JX204811 |
| Rotavirus A pheasant-tc/GER/10V0112H5/2010/G23P[37] | NC_011508 | vertebrates,human | 1 | Reoviridae,Rotavirus,Rotavirus A | seg. 3 | JX204813 |
| Rotavirus A pheasant-tc/GER/10V0112H5/2010/G23P[37] | NC_011509 | vertebrates,human | 1 | Reoviridae,Rotavirus,Rotavirus A | seg. 6 | JX204815 |
| Rotavirus A pheasant-tc/GER/10V0112H5/2010/G23P[37] | NC_011510 | vertebrates,human | 1 | Reoviridae,Rotavirus,Rotavirus A | seg. 4 | JX204814 |
| Rotavirus A pheasant/HUN/2008 | NC_011503 | vertebrates,human | 3 | Reoviridae,Rotavirus,Rotavirus A | seg. 9 | FN393054,FN393055,FN393056 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Rotavirus A sable antelope/G6P[14] | NC_011500 | vertebrates,human | Reoviridae,Rotavirus,Rotavirus A | 1 | seg. 5 | FJ495130 |
| Rotavirus A sable antelope/G6P[14] | NC_011501 | vertebrates,human | Reoviridae,Rotavirus,Rotavirus A | 1 | seg. 7 | FJ495134 |
| Rotavirus A sable antelope/G6P[14] | NC_011502 | vertebrates,human | Reoviridae,Rotavirus,Rotavirus A | 1 | seg. 8 | FJ495132 |
| Rotavirus A sable antelope/G6P[14] | NC_011503 | vertebrates,human | Reoviridae,Rotavirus,Rotavirus A | 1 | seg. 9 | FJ495133 |
| Rotavirus A sable antelope/G6P[14] | NC_011504 | vertebrates,human | Reoviridae,Rotavirus,Rotavirus A | 1 | seg. 10 | FJ495135 |
| Rotavirus A sable antelope/G6P[14] | NC_011505 | vertebrates,human | Reoviridae,Rotavirus,Rotavirus A | 1 | seg. 11 | FJ495136 |
| Rotavirus A sable antelope/G6P[14] | NC_011506 | vertebrates,human | Reoviridae,Rotavirus,Rotavirus A | 1 | seg. 2 | FJ495127 |
| Rotavirus A sable antelope/G6P[14] | NC_011507 | vertebrates,human | Reoviridae,Rotavirus,Rotavirus A | 1 | seg. 1 | FJ495126 |
| Rotavirus A sable antelope/G6P[14] | NC_011508 | vertebrates,human | Reoviridae,Rotavirus,Rotavirus A | 1 | seg. 3 | FJ495128 |
| Rotavirus A sable antelope/G6P[14] | NC_011509 | vertebrates,human | Reoviridae,Rotavirus,Rotavirus A | 1 | seg. 6 | FJ495131 |
| Rotavirus A sable antelope/G6P[14] | NC_011510 | vertebrates,human | Reoviridae,Rotavirus,Rotavirus A | 1 | seg. 4 | FJ495129 |
| Rotavirus A strain 116E/AG | NC_011500 | vertebrates,human | Reoviridae,Rotavirus,Rotavirus A | 1 | seg. 5 | FJ361205 |
| Rotavirus A strain 116E/AG | NC_011501 | vertebrates,human | Reoviridae,Rotavirus,Rotavirus A | 1 | seg. 7 | FJ361207 |
| Rotavirus A strain 116E/AG | NC_011502 | vertebrates,human | Reoviridae,Rotavirus,Rotavirus A | 1 | seg. 8 | FJ361208 |
| Rotavirus A strain 116E/AG | NC_011503 | vertebrates,human | Reoviridae,Rotavirus,Rotavirus A | 1 | seg. 9 | FJ361209 |
| Rotavirus A strain 116E/AG | NC_011504 | vertebrates,human | Reoviridae,Rotavirus,Rotavirus A | 1 | seg. 10 | FJ361210 |
| Rotavirus A strain 116E/AG | NC_011505 | vertebrates,human | Reoviridae,Rotavirus,Rotavirus A | 1 | seg. 11 | FJ361211 |
| Rotavirus A strain 116E/AG | NC_011506 | vertebrates,human | Reoviridae,Rotavirus,Rotavirus A | 1 | seg. 2 | FJ361202 |
| Rotavirus A strain 116E/AG | NC_011507 | vertebrates,human | Reoviridae,Rotavirus,Rotavirus A | 1 | seg. 1 | FJ361201 |
| Rotavirus A strain 116E/AG | NC_011508 | vertebrates,human | Reoviridae,Rotavirus,Rotavirus A | 1 | seg. 3 | FJ361203 |
| Rotavirus A strain 116E/AG | NC_011509 | vertebrates,human | Reoviridae,Rotavirus,Rotavirus A | 1 | seg. 6 | FJ361206 |
| Rotavirus A strain 116E/AG | NC_011510 | vertebrates,human | Reoviridae,Rotavirus,Rotavirus A | 1 | seg. 4 | FJ361204 |
| Rotavirus A strain 116E/AG | NC_011502 | vertebrates,human | Reoviridae,Rotavirus,Rotavirus A | 1 | seg. 8 | JX204827 |
| Rotavirus A turkey-tc/GER/03V0002E10/2003/G22P[35] | NC_011503 | vertebrates,human | Reoviridae,Rotavirus,Rotavirus A | 1 | seg. 9 | JX204829 |
| Rotavirus A turkey-tc/GER/03V0002E10/2003/G22P[35] | NC_011506 | vertebrates,human | Reoviridae,Rotavirus,Rotavirus A | 1 | seg. 2 | JX204823 |
| Rotavirus A turkey-tc/GER/03V0002E10/2003/G22P[35] | NC_011507 | vertebrates,human | Reoviridae,Rotavirus,Rotavirus A | 1 | seg. 1 | JX204822 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rotavirus A turkey-tc/GER/03V0002E10/2003/G22P[35] | NC_011508 | vertebrates,human | 1 | Reoviridae,Rotavirus,Rotavirus A | seg. 3 | JX204824 |
| Rotavirus A turkey-tc/GER/03V0002E10/2003/G22P[35] | NC_011509 | vertebrates,human | 1 | Reoviridae,Rotavirus,Rotavirus A | seg. 6 | JX204826 |
| Rotavirus A turkey-tc/GER/03V0002E10/2003/G22P[35] | NC_011510 | vertebrates,human | 1 | Reoviridae,Rotavirus,Rotavirus A | seg. 4 | JX204825 |
| Rotavirus B | NC_021541 | vertebrates,human | 1 | Reoviridae,Rotavirus,Rotavirus B | seg. 1 | M97203 |
| Rotavirus B | NC_021544 | vertebrates,human | 1 | Reoviridae,Rotavirus,Rotavirus B | seg. 6 | AF079157 |
| Rotavirus B | NC_021549 | vertebrates,human | 1 | Reoviridae,Rotavirus,Rotavirus B | seg. 11 | AF079158 |
| Rotavirus C | NC_007543 | vertebrates,human | 1 | Reoviridae,Rotavirus,Rotavirus C | seg. 6 | AJ132203 |
| Rotavirus C | NC_007544 | vertebrates,human | 1 | Reoviridae,Rotavirus,Rotavirus C | seg. 7 | AJ132204 |
| Rotavirus C | NC_007545 | vertebrates,human | 1 | Reoviridae,Rotavirus,Rotavirus C | seg. 9 | AJ132205 |
| Rotavirus C | NC_007546 | vertebrates,human | 1 | Reoviridae,Rotavirus,Rotavirus C | seg. 2 | AJ303139 |
| Rotavirus C | NC_007547 | vertebrates,human | 1 | Reoviridae,Rotavirus,Rotavirus C | seg. 1 | AJ304859 |
| Rotavirus C | NC_007569 | vertebrates,human | 1 | Reoviridae,Rotavirus,Rotavirus C | seg. 10 | M81488 |
| Rotavirus C | NC_007570 | vertebrates,human | 4 | Reoviridae,Rotavirus,Rotavirus C | seg. 5 | AF162434,M88768,EF528570,X59843 |
| Rotavirus C | NC_007571 | vertebrates,human | 15 | Reoviridae,Rotavirus,Rotavirus C | seg. 8 | U20990,U20989,U20994,U20991,U20993,X77257,U20992,X77258,EF528571,X77256,AJ549087,U20996,U20987,U20995,U20988 |
| Rotavirus C | NC_007572 | vertebrates,human | 1 | Reoviridae,Rotavirus,Rotavirus C | seg. 3 | X79442 |
| Rotavirus C | NC_007573 | vertebrates,human | 1 | Reoviridae,Rotavirus,Rotavirus C | seg. 11 | X83967 |
| Rotavirus C | NC_007574 | vertebrates,human | 1 | Reoviridae,Rotavirus,Rotavirus C | seg. 4 | X96697 |
| Rotavirus F chicken/03V0568/DEU/2003 | NC_021625 | vertebrates,human | 1 | Reoviridae,Rotavirus,Rotavirus F | seg. 1 | JN596591 |
| Rotavirus F chicken/03V0568/DEU/2003 | NC_021626 | vertebrates,human | 1 | Reoviridae,Rotavirus,Rotavirus F | seg. 2 | JQ919995 |
| Rotavirus F chicken/03V0568/DEU/2003 | NC_021627 | vertebrates,human | 1 | Reoviridae,Rotavirus,Rotavirus F | seg. 9 | JQ919998 |
| Rotavirus F chicken/03V0568/DEU/2003 | NC_021628 | vertebrates,human | 1 | Reoviridae,Rotavirus,Rotavirus F | seg. 8 | JQ920000 |
| Rotavirus F chicken/03V0568/DEU/2003 | NC_021629 | vertebrates,human | 1 | Reoviridae,Rotavirus,Rotavirus F | seg. 10 | JQ920003 |
| Rotavirus F chicken/03V0568/DEU/2003 | NC_021630 | vertebrates,human | 1 | Reoviridae,Rotavirus,Rotavirus F | seg. 4 | JQ919996 |
| Rotavirus F chicken/03V0568/DEU/2003 | NC_021631 | vertebrates,human | 1 | Reoviridae,Rotavirus,Rotavirus F | seg. 3 | JQ919997 |

TABLE 10-continued

VifoCap-1.0 Taxonomy

| Taxonomy | Rep.Acc.ID | Host | Lineage | # GN's | Seg. Count | GN.Acc.IDs |
|---|---|---|---|---|---|---|
| Rotavirus F chicken/03V0568/DEU/2003 | NC_021632 | vertebrates,human | Reoviridae,Rotavirus,Rotavirus F | 1 | seg. 5 | JQ919999 |
| Rotavirus F chicken/03V0568/DEU/2003 | NC_021633 | vertebrates,human | Reoviridae,Rotavirus,Rotavirus F | 1 | seg. 7 | JQ920001 |
| Rotavirus F chicken/03V0568/DEU/2003 | NC_021634 | vertebrates,human | Reoviridae,Rotavirus,Rotavirus F | 1 | seg. 11 | JQ920002 |
| Rotavirus F chicken/03V0568/DEU/2003 | NC_021635 | vertebrates,human | Reoviridae,Rotavirus,Rotavirus F | 1 | seg. 6 | HQ403603 |
| Rotavirus G chicken/03V0567/DEU/2003 | NC_021580 | vertebrates,human | Reoviridae,Rotavirus,Rotavirus G | 1 | — | JQ920004 |
| Rotavirus G chicken/03V0567/DEU/2003 | NC_021581 | vertebrates,human | Reoviridae,Rotavirus,Rotavirus G | 1 | — | JQ920006 |
| Rotavirus G chicken/03V0567/DEU/2003 | NC_021582 | vertebrates,human | Reoviridae,Rotavirus,Rotavirus G | 1 | — | JQ920007 |
| Rotavirus G chicken/03V0567/DEU/2003 | NC_021583 | vertebrates,human | Reoviridae,Rotavirus,Rotavirus G | 1 | — | JQ920008 |
| Rotavirus G chicken/03V0567/DEU/2003 | NC_021584 | vertebrates,human | Reoviridae,Rotavirus,Rotavirus G | 1 | — | JQ920009 |
| Rotavirus G chicken/03V0567/DEU/2003 | NC_021585 | vertebrates,human | Reoviridae,Rotavirus,Rotavirus G | 1 | — | JQ920010 |
| Rotavirus G chicken/03V0567/DEU/2003 | NC_021586 | vertebrates,human | Reoviridae,Rotavirus,Rotavirus G | 1 | — | JQ920011 |
| Rotavirus G chicken/03V0567/DEU/2003 | NC_021587 | vertebrates,human | Reoviridae,Rotavirus,Rotavirus G | 1 | — | JQ920012 |
| Rotavirus G chicken/03V0567/DEU/2003 | NC_021588 | vertebrates,human | Reoviridae,Rotavirus,Rotavirus G | 1 | — | HQ403604 |
| Rotavirus G chicken/03V0567/DEU/2003 | NC_021589 | vertebrates,human | Reoviridae,Rotavirus,Rotavirus G | 1 | — | JQ920005 |
| Rotavirus G chicken/03V0567/DEU/2003 | NC_021590 | vertebrates,human | Reoviridae,Rotavirus,Rotavirus G | 1 | — | JN596592 |
| Rotavirus G1 | NC_011503 | vertebrates,human | Reoviridae,Rotavirus,Rotavirus A | 11 | seg. 9 | EU839916,EU839911,EU839909,EU839913,EU839912,EU839910,EU839915,EU839908,EU839907,EU839906,EU839914 |
| Rotavirus G1 | NC_011504 | vertebrates,human | Reoviridae,Rotavirus,Rotavirus A | 1 | seg. 10 | AY159645,AY159638,AY159631,AY159636,AY159632,AY159646,AY159633,AY159642,AY159643,AY159634,AY159644,AY159641,AY159640,AY159630,AY159637,AY159639,AY159648,AY159635,AY159647 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rotavirus G10 | NC_011503 | vertebrates,human | 7 | Reoviridae,Rotavirus,Rotavirus A | seg. 9 | AY816181,JF681943, AY843333,AY816182 ,AY855063,JF681941 ,AY843332 |
| Rotavirus G10 | NC_011504 | vertebrates,human | 1 | Reoviridae,Rotavirus,Rotavirus A | seg. 10 | AY855068 |
| Rotavirus G12 | NC_011501 | vertebrates,human | 2 | Reoviridae,Rotavirus,Rotavirus A | seg. 7 | EU839967,EU839973 |
| Rotavirus G12 | NC_011502 | vertebrates,human | 2 | Reoviridae,Rotavirus,Rotavirus A | seg. 8 | EU839968,EU839974 |
| Rotavirus G12 | NC_011503 | vertebrates,human | 18 | Reoviridae,Rotavirus,Rotavirus A | seg. 9 | AB436818,AB436813 ,EU839943,EU83993 4,AB436814,EU8399 44,AB436815,EU839 942,EF059916,AB436 816,AB306271,AB43 6817,AB306270,EF05 9917,AB306268,EU8 39935,AB306269,AB 436819 |
| Rotavirus G12 | NC_011504 | vertebrates,human | 4 | Reoviridae,Rotavirus,Rotavirus A | seg. 10 | EU839969,EF059919 ,EU839975,EF05991 8 |
| Rotavirus G12 | NC_011505 | vertebrates,human | 2 | Reoviridae,Rotavirus,Rotavirus A | seg. 11 | EU839970,EU839976 |
| Rotavirus G12 | NC_011509 | vertebrates,human | 2 | Reoviridae,Rotavirus,Rotavirus A | seg. 6 | EU839965,EU839971 |
| Rotavirus G12 | NC_011510 | vertebrates,human | 2 | Reoviridae,Rotavirus,Rotavirus A | seg. 4 | EF059921,EF059920 |
| Rotavirus G2 | NC_011503 | vertebrates,human | 16 | Reoviridae,Rotavirus,Rotavirus A | seg. 9 | AY707784,EU839925 ,EU839919,EU83992 1,AY707785,EU8399 17,EU839926,EU839 918,EU839923,DQ47 8581,EU839924,EU8 39920,EU839922,EU 839928,AY707786,E U839927 |
| Rotavirus G2 | NC_011504 | vertebrates,human | 3 | Reoviridae,Rotavirus,Rotavirus A | seg. 10 | AY159649,AF401756, EU839964 |
| Rotavirus G2 | NC_011509 | vertebrates,human | 1 | Reoviridae,Rotavirus,Rotavirus A | seg. 6 | EU839963 |
| Rotavirus G3 | NC_011500 | vertebrates,human | 1 | Reoviridae,Rotavirus,Rotavirus A | seg. 5 | AY740735 |
| Rotavirus G3 | NC_011501 | vertebrates,human | 1 | Reoviridae,Rotavirus,Rotavirus A | seg. 7 | AY740734 |
| Rotavirus G3 | NC_011502 | vertebrates,human | 2 | Reoviridae,Rotavirus,Rotavirus A | seg. 8 | JQ358771,AY740733 |
| Rotavirus G3 | NC_011503 | vertebrates,human | 51 | Reoviridae,Rotavirus,Rotavirus A | seg. 9 | EF495119,EF495124, AY707791,D86276,E F495121,EF495127,D 0904498,D86266,D8 6280,D86264,D86282 ,JQ358764,D86269,D 86265,AY707789,AY 707792,EF495122,D |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0904499,DQ995488, DQ995489,D86283,D 0904503,EF495118, DQ904500,DQ904450 5,AY870661,DQ9045 06,EF495120,D86284 ,D86281,DQ904502, D86279,DQ904501,D 86271,DQ995490,D8 6272,AY900173,AY707 794,EF495126,D86627 8,D86268,D86267,D8 6274,EF495123,AY74 0736,DQ904504,AY7 07793,EF495125,D86 275 |
| Rotavirus G3 | NC_011504 | vertebrates,human | 21 | Reoviridae,Rotavirus,Rotavirus A | seg. 10 | AB008240,AB008236 ,AB008234,AB00824 6,AB008230,AB0082 33,AB008237,AY740 732,AB008242,AB00 8238,AB008243,AB0 08231,AB008244,AB 008232,AB008245,A B008248,AB008247, AB008241,AB008239 ,AB008229,AB00823 5 |
| Rotavirus G3 | NC_011505 | vertebrates,human | 2 | Reoviridae,Rotavirus,Rotavirus A | seg. 11 | JQ358774,AY740731 |
| Rotavirus G3 | NC_011506 | vertebrates,human | 1 | Reoviridae,Rotavirus,Rotavirus A | seg. 2 | AY740740 |
| Rotavirus G3 | NC_011507 | vertebrates,human | 1 | Reoviridae,Rotavirus,Rotavirus A | seg. 1 | AY740741 |
| Rotavirus G3 | NC_011508 | vertebrates,human | 1 | Reoviridae,Rotavirus,Rotavirus A | seg. 3 | AY740739 |
| Rotavirus G3 | NC_011509 | vertebrates,human | 1 | Reoviridae,Rotavirus,Rotavirus A | seg. 6 | AY740737 |
| Rotavirus G3 | NC_011510 | vertebrates,human | 20 | Reoviridae,Rotavirus,Rotavirus A | seg. 4 | AY740738,AB008277 ,AB008279,AB008278 8,AB008290,AB0082 91,AB008282,AB0O8 289,AB008281,AB0O 8272,AB008273,AB0 08274,AB008285,AB 008275,AB008284,A B008286,AB008283, AB008280,AB008276 ,AB008288 |
| Rotavirus G4 | NC_011503 | vertebrates,human | 33 | Reoviridae,Rotavirus,Rotavirus A | seg. 9 | AB012066,AB012074 ,AF161822,AB039035 ,AB012075,AB03902 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rotavirus G4 | NC_011504 | vertebrates,human | 33 | Reoviridae,Rotavirus,Rotavirus A | seg. 10 | 6,AB039027,AB0120 71,AB039025,AB012 078,AF161821,AB039 029,AF161823,AB012 069,AF161817,AB012 065,AB012079,AB03 9028,AB012072,AF16 1818,AB039032,AB0 12077,AB012067,AB 012076,AB012073,A B039031,AB012068, AB012070,AF161820, AB039030,AF161819, AB039034,AB039033 AB008255,AB008261 ,AF161810,AB043069 ,AF161815,AB043026 ,AB008251,AB00826 0,AB008253,AB0082 62,AB008249,AF1618 11,AB043072,AB043 075,AF161813,AB0O8 258,AB043076,AF161 816,AB008259,AB0O 8252,AB008263,AB0 43077,AB008256,AB 043073,AB043070,A B04307 8,AB043074, AF161814,AB008250, AB043071,AB008257 ,AB008254,AF161812 |
| Rotavirus G6 | NC_011503 | vertebrates,human | 1 | Reoviridae,Rotavirus,Rotavirus A | seg. 9 | AF532202 |
| Rotavirus G8 | NC_011503 | vertebrates,human | 1 | Reoviridae,Rotavirus,Rotavirus A | seg. 9 | AY855064 |
| Rotavirus G8 | NC_011510 | vertebrates,human | 1 | Reoviridae,Rotavirus,Rotavirus A | seg. 4 | AF045228 |
| Rotavirus G9 | NC_011503 | vertebrates,human | 156 | Reoviridae,Rotavirus,Rotavirus A | seg. 9 | AY253834,AJ250544, AB436831,AJ250276, EF199728,AB436820, AY699298,AB436832 ,AY262748,AY69930 2,AY307092,AY3070 88,AY307094,AB436 833,AY866500,AY87 9296,AY699301,EF19 9729,AY253835,AY6 99291,FJ695604,EF1 99735,AJ250275,AY2 11065,AJ250270,EU8 39936,AJ250269,DQ |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 647423,EU839929,EU839939,EF199736,AB436821,DQ056298,AY699292,AB091752,EF532837,AY699290,AB436822,EF199738,AB091755,EU839937,AY262747,AY211067,AJ250268,AB364369,EU839933,AY253836,AB436834,AJ250274,EU839932,AY699293,DQ056299,AJ250277,DQ056300,EF199737,HQ018933,JF703095,DQ096290,AY695811,AY211068,HQ018932,AY253833,AY866504,EU839940,AY699294,AJ491179,DQ056297,EF199730,AB091750,AJ491177,AB436826,DQ056296,AY699297,AJ250272,EU839930,AB091751,JF703094,DQ096288,EF199732,EF199726,AB091748,EF199734,AY253838,DQ990318,AY262746,AY253839,EF687001,EU839938,AY699296,AY184813,AY307087,AB436824,AJ491184,AY699299,AB364380,AB045372,DQ096293,EF199727,AJ250273,EF059922,DQ096292,AB436835,AY307086,AB436830,AB091754,AY307093,DQ096289,AY699304,AY695809,AB091749,AY262749,EF199725,AB091756,DQ990319,AY307091,AJ491175,AY866502,AB436827,AB436825,AB0453 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rotavirus G9 | NC_011504 | vertebrates,human | 4 | Reoviridae,Rotavirus,Rotavirus A | seg. 10 | 73,HQ018934,DQ096294,AY699303,DQ990317,DQ096291,AB436829,AY866505,AY253837,EU753963,AB436823,AY866501,AY866503,AB091747,EU839941,EF199731,AB436828,AY30701,AB436828,AY3070185,JF703096,AB091753,AF359358,AJ250540,AY307090,DQ490173,EF199733,AB091746,AY816184,AB045374,AJ250271,EU839931,AJ491172,AJ250545,AY699300,AY307089,AY699295,AY211066,JF703097 |
| Rotavirus G9 | NC_011509 | vertebrates,human | 1 | Reoviridae,Rotavirus,Rotavirus A | seg. 6 | EF033203,EF059924,EF033202,EF033204 |
| Rotavirus G9 | NC_011510 | vertebrates,human | 1 | Reoviridae,Rotavirus,Rotavirus A | seg. 4 | EU753964 |
| Rotavirus RVA/G1/Human/India/UK-HLD/2011/H14 | NC_011503 | vertebrates,human | 1 | Reoviridae,Rotavirus,Rotavirus A | seg. 9 | EF059923 |
| Rotavirus RVA/G1/Human/India/UK-HLD/2011/H180 | NC_011503 | vertebrates,human | 1 | Reoviridae,Rotavirus,Rotavirus A | seg. 9 | JX411969 |
| Rotavirus RVA/G9/Human/India/UK-HLD/2011/H140 | NC_011503 | vertebrates,human | 1 | Reoviridae,Rotavirus,Rotavirus A | seg. 9 | JX411970 |
| Rotavirus str.US1205 | NC_011503 | vertebrates,human | 1 | Reoviridae,Rotavirus,Rotavirus A | seg. 9 | JX411968 |
| Rotavirus strain TUCH | NC_011509 | vertebrates,human | 1 | Reoviridae,Rotavirus,Rotavirus A | seg. 6 | AF060487 |
| Rotavirus strain TUCH | NC_011510 | vertebrates,human | 1 | Reoviridae,Rotavirus,Rotavirus A | seg. 4 | AY594670 |
| Rotavirus subgroup 1 | NC_011503 | vertebrates,human | 2 | Reoviridae,Rotavirus,Rotavirus A | seg. 9 | AY596189 |
| Rotavirus subgroup 1 | NC_011504 | vertebrates,human | 1 | Reoviridae,Rotavirus,Rotavirus A | seg. 10 | K02028,L11605 |
| Rotavirus subgroup 1 | NC_011505 | vertebrates,human | 1 | Reoviridae,Rotavirus,Rotavirus A | seg. 11 | K03384 |
| Rotavirus subgroup 2 | NC_011509 | vertebrates,human | 1 | Reoviridae,Rotavirus,Rotavirus A | seg. 6 | K03385 |
| Rotavirus subgroup 2 | NC_011501 | vertebrates,human | 1 | Reoviridae,Rotavirus,Rotavirus A | seg. 7 | DQ0325 |
| Rotavirus subgroup 2 | NC_011503 | vertebrates,human | 1 | Reoviridae,Rotavirus,Rotavirus A | seg. 9 | X57944 |
| Rotavirus subgroup 2 | NC_011504 | vertebrates,human | 1 | Reoviridae,Rotavirus,Rotavirus A | seg. 10 | K02033 |
| | | | | | | K02032 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Rotavirus subgroup 2 | NC_011509 | vertebrates,human | 2 | Reoviridae,Rotavirus,Rotavirus A | seg. 6 | X57943,K02086 |
| Rubella virus | NC_001545 | vertebrates,human | 47 | Togaviridae,Rubivirus,Rubella virus | — | AY258323,JN635281, JN635282,JN635292, JN635285,AF435866, JN635296,DQ085341 ,AB047329,AF435865 ,AB588193,DQ085340 ,L78917,JN635290, AB588188,AB047330 ,JN635293,JN635288 ,AB222608,JN635284 ,DQ388281,JN635529 1,JF727653,FJ21158 8,JN635287,AB22260 9,KF201674,AB58819 1,JN635295,JN635528 3,AB588192,JN635528 9,AF188704,AY25832 2,AB588189,JN635529 4,DQ388280,JF72765 4,DQ085342,AB5881 90,M15240,DQ085534 3,FJ211587,DQ085533 9,JN635286,DQ08535 38,DQ388279 |
| SARS Coronavirus CDC#200301157 | NC_004718 | vertebrates,human | 1 | Coronaviridae,Betacoronavirus,Severe acute respiratory syndrome-related coronavirus | — | AY714217 |
| SARS coronavirus | NC_004718 | vertebrates,human | 25 | Coronaviridae,Betacoronavirus,Severe acute respiratory syndrome-related coronavirus | — | AY545914,JX163925, AY545917,CS569493 ,C0918585,DQ89817 4,JX163923,C09185 84,CS079026,CS079 027,JX163924,JX163 926,AY545916,JX163 928,DQ497008,CS07 9029,JX163927,CS07 9028,CS254197,AY5 45918,C0918598,FJ9 59407,AY274119,AY 545919,AY545915 |
| SARS coronavirus A022 | NC_004718 | vertebrates,human | 1 | Coronaviridae,Betacoronavirus,Severe acute respiratory syndrome-related coronavirus | — | AY686863 |
| SARS coronavirus AS | NC_004718 | vertebrates,human | 1 | Coronaviridae,Betacoronavirus,Severe acute respiratory syndrome-related coronavirus | — | AY427439 |
| SARS coronavirus B039 | NC_004718 | vertebrates,human | 1 | Coronaviridae,Betacoronavirus,Severe acute respiratory syndrome-related coronavirus | — | AY686864 |
| SARS coronavirus BIQ1 | NC_004718 | vertebrates,human | 1 | Coronaviridae,Betacoronavirus,Severe acute respiratory syndrome-related coronavirus | — | AY278488 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| SARS coronavirus BJ02 | NC_004718 | vertebrates,human | 1 | Coronaviridae,Betacoronavirus,Severe acute respiratory syndrome-related coronavirus | — | AY278487

TABLE 10-continued

| Taxonomy | Rep.Acc.ID | Host | # GN's | Lineage | Seg. Count | GN.Acc.IDs |
|---|---|---|---|---|---|---|
| SARS coronavirus FRA | NC_004718 | vertebrates,human | 1 | Coronaviridae,Betacoronavirus,Severe acute respiratory syndrome-related coronavirus | — | AY310120 |
| SARS coronavirus Frankfurt 1 | NC_004718 | vertebrates,human | 2 | Coronaviridae,Betacoronavirus,Severe acute respiratory syndrome-related coronavirus | — | AB257344,AY291315 |
| SARS coronavirus GDQ1 | NC_004718 | vertebrates,human | 1 | Coronaviridae,Betacoronavirus,Severe acute respiratory syndrome-related coronavirus | — | AY278489 |
| SARS coronavirus GD69 | NC_004718 | vertebrates,human | 1 | Coronaviridae,Betacoronavirus,Severe acute respiratory syndrome-related coronavirus | — | AY313906 |
| SARS coronavirus GDH-BJH01 | NC_004718 | vertebrates,human | 1 | Coronaviridae,Betacoronavirus,Severe acute respiratory syndrome-related coronavirus | — | DQ640652 |
| SARS coronavirus GZ-A | NC_004718 | vertebrates,human | 1 | Coronaviridae,Betacoronavirus,Severe acute respiratory syndrome-related coronavirus | — | AY394977 |
| SARS coronavirus GZ-B | NC_004718 | vertebrates,human | 1 | Coronaviridae,Betacoronavirus,Severe acute respiratory syndrome-related coronavirus | — | AY394978 |
| SARS coronavirus GZ-C | NC_004718 | vertebrates,human | 1 | Coronaviridae,Betacoronavirus,Severe acute respiratory syndrome-related coronavirus | — | AY394979 |
| SARS coronavirus GZ-D | NC_004718 | vertebrates,human | 1 | Coronaviridae,Betacoronavirus,Severe acute respiratory syndrome-related coronavirus | — | AY394980 |
| SARS coronavirus GZ02 | NC_004718 | vertebrates,human | 1 | Coronaviridae,Betacoronavirus,Severe acute respiratory syndrome-related coronavirus | — | AY390556 |
| SARS coronavirus GZ0401 | NC_004718 | vertebrates,human | 1 | Coronaviridae,Betacoronavirus,Severe acute respiratory syndrome-related coronavirus | — | AY568539 |
| SARS coronavirus GZ0402 | NC_004718 | vertebrates,human | 1 | Coronaviridae,Betacoronavirus,Severe acute respiratory syndrome-related coronavirus | — | AY613947 |
| SARS coronavirus GZ50 | NC_004718 | vertebrates,human | 1 | Coronaviridae,Betacoronavirus,Severe acute respiratory syndrome-related coronavirus | — | AY304495 |
| SARS coronavirus HC/SZ/61/03 | NC_004718 | vertebrates,human | 1 | Coronaviridae,Betacoronavirus,Severe acute respiratory syndrome-related coronavirus | — | AY515512 |
| SARS coronavirus HGZ8L1-A | NC_004718 | vertebrates,human | 1 | Coronaviridae,Betacoronavirus,Severe acute respiratory syndrome-related coronavirus | — | AY394981 |
| SARS coronavirus HGZ8L1-B | NC_004718 | vertebrates,human | 1 | Coronaviridae,Betacoronavirus,Severe acute respiratory syndrome-related coronavirus | — | AY394982 |
| SARS coronavirus HGZ8L2 | NC_004718 | vertebrates,human | 1 | Coronaviridae,Betacoronavirus,Severe acute respiratory syndrome-related coronavirus | — | AY394993 |
| SARS coronavirus HKU-39849 | NC_004718 | vertebrates,human | 6 | Coronaviridae,Betacoronavirus,Severe acute respiratory syndrome-related coronavirus | — | JQ316196,JN854286,GU553365,AY278491,GU553363,GU553364 |
| SARS coronavirus HSR 1 | NC_004718 | vertebrates,human | 1 | Coronaviridae,Betacoronavirus,Severe acute respiratory syndrome-related coronavirus | — | AY323977 |
| SARS coronavirus HSZ-A | NC_004718 | vertebrates,human | 1 | Coronaviridae,Betacoronavirus,Severe acute respiratory syndrome-related coronavirus | — | AY394984 |
| SARS coronavirus HSZ-Bb | NC_004718 | vertebrates,human | 1 | Coronaviridae,Betacoronavirus,Severe acute respiratory syndrome-related coronavirus | — | AY394985 |
| SARS coronavirus HSZ-Bc | NC_004718 | vertebrates,human | 1 | Coronaviridae,Betacoronavirus,Severe acute respiratory syndrome-related coronavirus | — | AY394994 |
| SARS coronavirus HSZ-Cb | NC_004718 | vertebrates,human | 1 | Coronaviridae,Betacoronavirus,Severe acute respiratory syndrome-related coronavirus | — | AY394986 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| SARS coronavirus HSZ-Cc | NC_004718 | vertebrates,human | 1 | Coronaviridae,Betacoronavirus,Severe acute respiratory syndrome-related coronavirus | — | AY394995 |
| SARS coronavirus HSZ2-A | NC_004718 | vertebrates,human | 1 | Coronaviridae,Betacoronavirus,Severe acute respiratory syndrome-related coronavirus | — | AY394983 |
| SARS coronavirus HZS2-Bb | NC_004718 | vertebrates,human | 1 | Coronaviridae,Betacoronavirus,Severe acute respiratory syndrome-related coronavirus | — | AY395004 |
| SARS coronavirus HZS2-C | NC_004718 | vertebrates,human | 1 | Coronaviridae,Betacoronavirus,Severe acute respiratory syndrome-related coronavirus | — | AY394992 |
| SARS coronavirus HZS2-D | NC_004718 | vertebrates,human | 1 | Coronaviridae,Betacoronavirus,Severe acute respiratory syndrome-related coronavirus | — | AY394989 |
| SARS coronavirus HZS2-E | NC_004718 | vertebrates,human | 1 | Coronaviridae,Betacoronavirus,Severe acute respiratory syndrome-related coronavirus | — | AY394990 |
| SARS coronavirus HZS2-Fb | NC_004718 | vertebrates,human | 1 | Coronaviridae,Betacoronavirus,Severe acute respiratory syndrome-related coronavirus | — | AY394987 |
| SARS coronavirus HZS2-Fc | NC_004718 | vertebrates,human | 1 | Coronaviridae,Betacoronavirus,Severe acute respiratory syndrome-related coronavirus | — | AY394991 |
| SARS coronavirus JMD | NC_004718 | vertebrates,human | 1 | Coronaviridae,Betacoronavirus,Severe acute respiratory syndrome-related coronavirus | — | AY394988 |
| SARS coronavirus LC1 | NC_004718 | vertebrates,human | 1 | Coronaviridae,Betacoronavirus,Severe acute respiratory syndrome-related coronavirus | — | AY394998 |
| SARS coronavirus LC2 | NC_004718 | vertebrates,human | 1 | Coronaviridae,Betacoronavirus,Severe acute respiratory syndrome-related coronavirus | — | AY394999 |
| SARS coronavirus LC3 | NC_004718 | vertebrates,human | 1 | Coronaviridae,Betacoronavirus,Severe acute respiratory syndrome-related coronavirus | — | AY395000 |
| SARS coronavirus LC4 | NC_004718 | vertebrates,human | 1 | Coronaviridae,Betacoronavirus,Severe acute respiratory syndrome-related coronavirus | — | AY395001 |
| SARS coronavirus LC5 | NC_004718 | vertebrates,human | 1 | Coronaviridae,Betacoronavirus,Severe acute respiratory syndrome-related coronavirus | — | AY395002 |
| SARS coronavirus LU-2004 | NC_004718 | vertebrates,human | 1 | Coronaviridae,Betacoronavirus,Severe acute respiratory syndrome-related coronavirus | — | AY595412 |
| SARS coronavirus MA15 | NC_004718 | vertebrates,human | 26 | Coronaviridae,Betacoronavirus,Severe acute respiratory syndrome-related coronavirus | — | FJ882958,JF292910,FJ882961,JF292912,FJ882948,JF292914,JF292911,JF292908,FJ882952,JF292915,JF292918,HQ890546,HQ890542,JF292917,FJ882945,JF292913,HQ890543,HQ890544,HQ890545,HQ890541,JF292916,JF292919,JF292909,JF292907,FJ882957,JF292920 |
| SARS coronavirus MA15 ExoN1 | NC_004718 | vertebrates,human | 26 | Coronaviridae,Betacoronavirus,Severe acute respiratory syndrome-related coronavirus | — | FJ882953,HQ890539,JF292904,FJ882942,HQ890527,HQ890529,HQ890538,HQ890528 |

TABLE 10-continued

| Taxonomy | Rep.Acc.ID | Host | ViroCap-1.0 Taxonomy | | Seg. Count | GN.Acc.IDs |
| --- | --- | --- | --- | --- | --- | --- |
| | | | Lineage | # GN's | | |
| SARS coronavirus NS-1 | NC_004718 | vertebrates,human | Coronaviridae,Betacoronavirus,Severe acute respiratory syndrome-related coronavirus | 1 | — | 36,HQ890540,JF2929 03,HQ890526,HQ890 537,FJ882959,FJ882 943,FJ882951,HQ890 530,HQ890535,JF292 902,HQ890532,HQ89 0533,HQ890531,HQ8 90534,HQ890528,JF2 92906,JF292905,FJ8 82962 |
| SARS coronavirus P2 | NC_004718 | vertebrates,human | Coronaviridae,Betacoronavirus,Severe acute respiratory syndrome-related coronavirus | 1 | — | AY508724 |
| SARS coronavirus PC4-13 | NC_004718 | vertebrates,human | Coronaviridae,Betacoronavirus,Severe acute respiratory syndrome-related coronavirus | 1 | — | FJ882963 |
| SARS coronavirus PC4-136 | NC_004718 | vertebrates,human | Coronaviridae,Betacoronavirus,Severe acute respiratory syndrome-related coronavirus | 1 | — | AY613948 |
| SARS coronavirus PC4-227 | NC_004718 | vertebrates,human | Coronaviridae,Betacoronavirus,Severe acute respiratory syndrome-related coronavirus | 1 | — | AY613949 |
| SARS coronavirus PUMC01 | NC_004718 | vertebrates,human | Coronaviridae,Betacoronavirus,Severe acute respiratory syndrome-related coronavirus | 1 | — | AY613950 |
| SARS coronavirus PUMC02 | NC_004718 | vertebrates,human | Coronaviridae,Betacoronavirus,Severe acute respiratory syndrome-related coronavirus | 1 | — | AY350750 |
| SARS coronavirus PUMC03 | NC_004718 | vertebrates,human | Coronaviridae,Betacoronavirus,Severe acute respiratory syndrome-related coronavirus | 1 | — | AY357075 |
| SARS coronavirus Rs_672/2006 | NC_004718 | vertebrates,human | Coronaviridae,Betacoronavirus,Severe acute respiratory syndrome-related coronavirus | 1 | — | AY357076 |
| SARS coronavirus ShanghaiQXC1 | NC_004718 | vertebrates,human | Coronaviridae,Betacoronavirus,Severe acute respiratory syndrome-related coronavirus | 1 | — | FJ588686 |
| SARS coronavirus ShanghaiQXC2 | NC_004718 | vertebrates,human | Coronaviridae,Betacoronavirus,Severe acute respiratory syndrome-related coronavirus | 1 | — | AY463059 |
| SARS coronavirus Sin2500 | NC_004718 | vertebrates,human | Coronaviridae,Betacoronavirus,Severe acute respiratory syndrome-related coronavirus | 1 | — | AY463060 |
| SARS coronavirus Sin2677 | NC_004718 | vertebrates,human | Coronaviridae,Betacoronavirus,Severe acute respiratory syndrome-related coronavirus | 1 | — | AY283794 |
| SARS coronavirus Sin2679 | NC_004718 | vertebrates,human | Coronaviridae,Betacoronavirus,Severe acute respiratory syndrome-related coronavirus | 1 | — | AY283795 |
| SARS coronavirus Sin2748 | NC_004718 | vertebrates,human | Coronaviridae,Betacoronavirus,Severe acute respiratory syndrome-related coronavirus | 1 | — | AY283796 |
| SARS coronavirus Sin2774 | NC_004718 | vertebrates,human | Coronaviridae,Betacoronavirus,Severe acute respiratory syndrome-related coronavirus | 1 | — | AY283797 |
| SARS coronavirus Sin3408 | NC_004718 | vertebrates,human | Coronaviridae,Betacoronavirus,Severe acute respiratory syndrome-related coronavirus | 1 | — | AY283798 |
| SARS coronavirus Sin3408L | NC_004718 | vertebrates,human | Coronaviridae,Betacoronavirus,Severe acute respiratory syndrome-related coronavirus | 1 | — | AY559083 |
| SARS coronavirus Sin3725V | NC_004718 | vertebrates,human | Coronaviridae,Betacoronavirus,Severe acute respiratory syndrome-related coronavirus | 1 | — | AY559097 |
| | NC_004718 | vertebrates,human | Coronaviridae,Betacoronavirus,Severe acute respiratory syndrome-related coronavirus | 1 | — | AY559087 |

TABLE 10-continued

| Taxonomy | Rep.Acc.ID | Host | # GN's | Lineage | Seg. Count | GN.Acc.IDs |
|---|---|---|---|---|---|---|
| SARS coronavirus Sin3765V | NC_004718 | vertebrates,human | 1 | Coronaviridae,Betacoronavirus,Severe acute respiratory syndrome-related coronavirus | — | AY559084 |
| SARS coronavirus Sin842 | NC_004718 | vertebrates,human | 1 | Coronaviridae,Betacoronavirus,Severe acute respiratory syndrome-related coronavirus | — | AY559081 |
| SARS coronavirus Sin845 | NC_004718 | vertebrates,human | 1 | Coronaviridae,Betacoronavirus,Severe acute respiratory syndrome-related coronavirus | — | AY559093 |
| SARS coronavirus Sin846 | NC_004718 | vertebrates,human | 1 | Coronaviridae,Betacoronavirus,Severe acute respiratory syndrome-related coronavirus | — | AY559094 |
| SARS coronavirus Sin847 | NC_004718 | vertebrates,human | 1 | Coronaviridae,Betacoronavirus,Severe acute respiratory syndrome-related coronavirus | — | AY559095 |
| SARS coronavirus Sin848 | NC_004718 | vertebrates,human | 1 | Coronaviridae,Betacoronavirus,Severe acute respiratory syndrome-related coronavirus | — | AY559085 |
| SARS coronavirus Sin849 | NC_004718 | vertebrates,human | 1 | Coronaviridae,Betacoronavirus,Severe acute respiratory syndrome-related coronavirus | — | AY559086 |
| SARS coronavirus Sin850 | NC_004718 | vertebrates,human | 1 | Coronaviridae,Betacoronavirus,Severe acute respiratory syndrome-related coronavirus | — | AY559096 |
| SARS coronavirus Sin852 | NC_004718 | vertebrates,human | 1 | Coronaviridae,Betacoronavirus,Severe acute respiratory syndrome-related coronavirus | — | AY559082 |
| SARS coronavirus SinP1 | NC_004718 | vertebrates,human | 1 | Coronaviridae,Betacoronavirus,Severe acute respiratory syndrome-related coronavirus | — | AY559088 |
| SARS coronavirus SinP2 | NC_004718 | vertebrates,human | 1 | Coronaviridae,Betacoronavirus,Severe acute respiratory syndrome-related coronavirus | — | AY559089 |
| SARS coronavirus SinP3 | NC_004718 | vertebrates,human | 1 | Coronaviridae,Betacoronavirus,Severe acute respiratory syndrome-related coronavirus | — | AY559090 |
| SARS coronavirus SinP4 | NC_004718 | vertebrates,human | 1 | Coronaviridae,Betacoronavirus,Severe acute respiratory syndrome-related coronavirus | — | AY559091 |
| SARS coronavirus SinP5 | NC_004718 | vertebrates,human | 1 | Coronaviridae,Betacoronavirus,Severe acute respiratory syndrome-related coronavirus | — | AY559092 |
| SARS coronavirus Sino1-11 | NC_004718 | vertebrates,human | 1 | Coronaviridae,Betacoronavirus,Severe acute respiratory syndrome-related coronavirus | — | AY485277 |
| SARS coronavirus Sino3-11 | NC_004718 | vertebrates,human | 1 | Coronaviridae,Betacoronavirus,Severe acute respiratory syndrome-related coronavirus | — | AY485278 |
| SARS coronavirus SoD | NC_004718 | vertebrates,human | 1 | Coronaviridae,Betacoronavirus,Severe acute respiratory syndrome-related coronavirus | — | AY461660 |
| SARS coronavirus TJF | NC_004718 | vertebrates,human | 1 | Coronaviridae,Betacoronavirus,Severe acute respiratory syndrome-related coronavirus | — | AY654624 |
| SARS coronavirus TW1 | NC_004718 | vertebrates,human | 1 | Coronaviridae,Betacoronavirus,Severe acute respiratory syndrome-related coronavirus | — | AY291451 |
| SARS coronavirus TW10 | NC_004718 | vertebrates,human | 1 | Coronaviridae,Betacoronavirus,Severe acute respiratory syndrome-related coronavirus | — | AY502923 |
| SARS coronavirus TW11 | NC_004718 | vertebrates,human | 1 | Coronaviridae,Betacoronavirus,Severe acute respiratory syndrome-related coronavirus | — | AY502924 |
| SARS coronavirus TW2 | NC_004718 | vertebrates,human | 1 | Coronaviridae,Betacoronavirus,Severe acute respiratory syndrome-related coronavirus | — | AY502925 |
| SARS coronavirus TW3 | NC_004718 | vertebrates,human | 1 | Coronaviridae,Betacoronavirus,Severe acute respiratory syndrome-related coronavirus | — | AY502926 |
| SARS coronavirus TW4 | NC_004718 | vertebrates,human | 1 | Coronaviridae,Betacoronavirus,Severe acute respiratory syndrome-related coronavirus | — | AY502927 |

TABLE 10-continued

| Taxonomy | Rep.Acc.ID | Host | # GN's | Lineage | Seg. Count | GN.Acc.IDs |
|---|---|---|---|---|---|---|
| SARS coronavirus TW5 | NC_004718 | vertebrates,human | 1 | Coronaviridae,Betacoronavirus,Severe acute respiratory syndrome-related coronavirus | — | AY502928 |
| SARS coronavirus TW6 | NC_004718 | vertebrates,human | 1 | Coronaviridae,Betacoronavirus,Severe acute respiratory syndrome-related coronavirus | — | AY502929 |
| SARS coronavirus TW7 | NC_004718 | vertebrates,human | 1 | Coronaviridae,Betacoronavirus,Severe acute respiratory syndrome-related coronavirus | — | AY502930 |
| SARS coronavirus TW8 | NC_004718 | vertebrates,human | 1 | Coronaviridae,Betacoronavirus,Severe acute respiratory syndrome-related coronavirus | — | AY502931 |
| SARS coronavirus TW9 | NC_004718 | vertebrates,human | 1 | Coronaviridae,Betacoronavirus,Severe acute respiratory syndrome-related coronavirus | — | AY502932 |
| SARS coronavirus TWC | NC_004718 | vertebrates,human | 1 | Coronaviridae,Betacoronavirus,Severe acute respiratory syndrome-related coronavirus | — | AY321118 |
| SARS coronavirus TWC2 | NC_004718 | vertebrates,human | 1 | Coronaviridae,Betacoronavirus,Severe acute respiratory syndrome-related coronavirus | — | AY362698 |
| SARS coronavirus TWC3 | NC_004718 | vertebrates,human | 1 | Coronaviridae,Betacoronavirus,Severe acute respiratory syndrome-related coronavirus | — | AY362699 |
| SARS coronavirus TWH | NC_004718 | vertebrates,human | 1 | Coronaviridae,Betacoronavirus,Severe acute respiratory syndrome-related coronavirus | — | AP006557 |
| SARS coronavirus TWJ | NC_004718 | vertebrates,human | 1 | Coronaviridae,Betacoronavirus,Severe acute respiratory syndrome-related coronavirus | — | AP006558 |
| SARS coronavirus TWK | NC_004718 | vertebrates,human | 1 | Coronaviridae,Betacoronavirus,Severe acute respiratory syndrome-related coronavirus | — | AP006559 |
| SARS coronavirus TWS | NC_004718 | vertebrates,human | 1 | Coronaviridae,Betacoronavirus,Severe acute respiratory syndrome-related coronavirus | — | AP006560 |
| SARS coronavirus TWY | NC_004718 | vertebrates,human | 1 | Coronaviridae,Betacoronavirus,Severe acute respiratory syndrome-related coronavirus | — | AP006561 |
| SARS coronavirus Taiwan TC1 | NC_004718 | vertebrates,human | 1 | Coronaviridae,Betacoronavirus,Severe acute respiratory syndrome-related coronavirus | — | AY338174 |
| SARS coronavirus Taiwan TC2 | NC_004718 | vertebrates,human | 1 | Coronaviridae,Betacoronavirus,Severe acute respiratory syndrome-related coronavirus | — | AY338175 |
| SARS coronavirus Taiwan TC3 | NC_004718 | vertebrates,human | 1 | Coronaviridae,Betacoronavirus,Severe acute respiratory syndrome-related coronavirus | — | AY348314 |
| SARS coronavirus Urbani | NC_004718 | vertebrates,human | 1 | Coronaviridae,Betacoronavirus,Severe acute respiratory syndrome-related coronavirus | — | AY278741 |
| SARS coronavirus W H20 | NC_004718 | vertebrates,human | 1 | Coronaviridae,Betacoronavirus,Severe acute respiratory syndrome-related coronavirus | — | AY772062

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| SARS coronavirus ZS-B | NC_004718 | vertebrates,human | 1 | Coronaviridae,Betacoronavirus,Severe acute respiratory syndrome-related coronavirus | — | AY394996 |
| SARS coronavirus ZS-C | NC_004718 | vertebrates,human | 1 | Coronaviridae,Betacoronavirus,Severe acute respiratory syndrome-related coronavirus | — | AY395003 |
| SARS coronavirus civet010 | NC_004718 | vertebrates,human | 1 | Coronaviridae,Betacoronavirus,Severe acute respiratory syndrome-related coronavirus | — | AY572035 |
| SARS coronavirus civet020 | NC_004718 | vertebrates,human | 1 | Coronaviridae,Betacoronavirus,Severe acute respiratory syndrome-related coronavirus | — | AY572038 |
| SARS coronavirus wtic-MB | NC_004718 | vertebrates,human | 31 | Coronaviridae,Betacoronavirus,Severe acute respiratory syndrome-related coronavirus | — | KF514421,FJ882932, FJ882937,KF514413, KF514400,KF514392, KF514399,JF292921, KF514415,FJ882927, KF514398,KF514408, KF514419,FJ882938, KF514423,FJ882934, KF514418,FJ882939, KF514396,KF514397, FJ882936,FJ882949, FJ882946,FJ882933, FJ882947,KF514394, KF514409,KF514422, KF514388,FJ882935, KF514404 |
| Sabia virus | NC_006313 | vertebrates,human | 3 | Arenaviridae,Arenavirus,Sabia virus | seg. L | JN801475,AY358026, AY216506 |
| Sabia virus | NC_006317 | vertebrates,human | 2 | Arenaviridae,Arenavirus,Sabia virus | seg. S | U41071,JN801474 |
| Sapovirus Chanthaburi-74/Thailand | NC_000940,NC_010624,NC_006269,NC_006554 | vertebrates,human | 1 | Caliciviridae,Sapovirus,Sapporo virus | — | AY646854 |
| Sapovirus Ehime1107/2002/JP | NC_000940,NC_010624,NC_006269,NC_006554 | vertebrates,human | 1 | Caliciviridae,Sapovirus,Sapporo virus | — | DQ058829 |
| Sapovirus Hu/Angelholm/SW278/2004/SE | NC_000940,NC_010624,NC_006269,NC_006554 | vertebrates,human | 1 | Caliciviridae,Sapovirus,Sapporo virus | — | DQ125333 |
| Sapovirus Hu/Angelholm/SW314/2004/SE | NC_000940,NC_010624,NC_006269,NC_006554 | vertebrates,human | 1 | Caliciviridae,Sapovirus,Sapporo virus | — | DQ125334 |

TABLE 10-continued

| | | | VIroCap-1.0 Taxonomy | | | |
|---|---|---|---|---|---|---|
| Taxonomy | Rep.Acc.ID | Host | Lineage | # GN's | Seg. Count | GN.Acc.IDs |
| Sapovirus Hu/Bristol1/1998/UK | NC_000940, NC_01062, 4,NC_0062, 69,NC_006554 | vertebrates,human | Caliciviridae,Sapovirus,Sapporo virus | 1 | — | AJ249939 |
| Sapovirus Hu/Chiba/000671/1999/JP | NC_000940, NC_01062, 4,NC_0062, 69,NC_006554 | vertebrates,human | Caliciviridae,Sapovirus,Sapporo virus | 1 | — | AJ786349 |
| Sapovirus Hu/Ehime1596/1999/JP | NC_000940, NC_01062, 4,NC_0062, 69,NC_006554 | vertebrates,human | Caliciviridae,Sapovirus,Sapporo virus | 1 | — | DQ366346 |
| Sapovirus Hu/Ehime475/2004/JP | NC_000940, NC_01062, 4,NC_0062, 69,NC_006554 | vertebrates,human | Caliciviridae,Sapovirus,Sapporo virus | 1 | — | DQ366344 |
| Sapovirus Hu/Ehime643/March 2000/JP | NC_000940, NC_01062, 4,NC_0062, 69,NC_006554 | vertebrates,human | Caliciviridae,Sapovirus,Sapporo virus | 1 | — | DQ366345 |
| Sapovirus Hu/G I,2/BR-DF01/BRA/2009 | NC_000940, NC_01062, 4,NC_0062, 69,NC_006554 | vertebrates,human | Caliciviridae,Sapovirus,Sapporo virus | 1 | — | AB614356 |
| Sapovirus Hu/GI/Sapporo/MT-2010/1982 | NC_000940, NC_01062, 4,NC_0062, 69,NC_006554 | vertebrates,human | Caliciviridae,Sapovirus,Sapporo virus | 1 | — | HM002617 |
| Sapovirus Mc114 | NC_000940, NC_01062, 4,NC_0062, 69,NC_006554 | vertebrates,human | Caliciviridae,Sapovirus,Sapporo virus | 1 | — | AY237422 |
| Sapovirus Mc2 | NC_000940, NC_01062, 4,NC_0062, 69,NC_006554 | vertebrates,human | Caliciviridae,Sapovirus,Sapporo virus | 1 | — | AY237419 |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| Sapovirus N21 | NC_000940,NC_010624,NC_006269,NC_006554 | vertebrates,human | 1 | Caliciviridae,Sapovirus,Sapporo virus | — | AY237423 |
| Sapovirus NongKhai-24/Thailand | NC_000940,NC_010624,NC_006269,NC_006554 | vertebrates,human | 1 | Caliciviridae,Sapovirus,Sapporo virus | — | AY646856 |
| Sapovirus NongKhai-50/Thailand | NC_000940,NC_010624,NC_006269,NC_006554 | vertebrates,human | 1 | Caliciviridae,Sapovirus,Sapporo virus | — | AY646853 |
| Sapovirus SaKaeo-15/Thailand | NC_000940,NC_010624,NC_006269,NC_006554 | vertebrates,human | 1 | Caliciviridae,Sapovirus,Sapporo virus | — | AY646855 |
| Sapovirus pig/Gansu/CH430/2012/CHN | NC_000940,NC_010624,NC_006269,NC_006554 | vertebrates,human | 1 | Caliciviridae,Sapovirus,Sapporo virus | — | KF204570 |
| Sapovirus pig/sav1/2008/CHN | NC_000940,NC_010624,NC_006269,NC_006554 | vertebrates,human | 1 | Caliciviridae,Sapovirus,Sapporo virus | — | FJ387164 |
| Sapporo rat virus | NC_005236 | vertebrates,human | 1 | Bunyaviridae,Hantavirus,Seoul virus | seg. S | M34881 |
| Sapporo rat virus | NC_005237 | vertebrates,human | 1 | Bunyaviridae,Hantavirus,Seoul virus | seg. M | M34882 |
| Sapporo virus-Manchester | NC_000940,NC_010624,NC_006269,NC_006554 | vertebrates,human | 1 | Caliciviridae,Sapovirus,Sapporo virus | | X86560 |
| Seal anellovirus TFFN/USA/2006 | NC_015212 | vertebrates,human | 1 | Anelloviridae,Seal anellovirus TFFN/USA/2006 | — | HQ287751 |
| Sendai virus | NC_001552 | vertebrates,human | 20 | Paramyxoviridae,Respirovirus,Sendai virus | — | AB855653,AB005795,AB005796,AB065187,M69046,M30204,D0219803,AB195967,AB855655,EF679198,AB275417,AB065188,AB855654,AB03965 |

TABLE 10-continued

| Taxonomy | Rep.Acc.ID | Host | # GN's | Lineage | Seg. Count | GN.Acc.IDs |
|---|---|---|---|---|---|---|
| Seoul virus | NC_005236 | vertebrates,human | 13 | Bunyaviridae,Hantavirus,Seoul virus | seg. S | 8,AB195968,AB2754 16,M30203,AB06518 9,AB065186,M30202 AF406965,KC626089 ,JX853575,JX879769, JQ665912,HQ611980 ,AY006465,EF192308 ,AY766368,AY27379 1,JQ898106,JN37755 3,AY750171 |
| Seoul virus | NC_005237 | vertebrates,human | 11 | Bunyaviridae,Hantavirus,Seoul virus | seg. M | D17593,D17592,547 716,JN377554,JQ665 888,JX853576,D1759 4,DQ159911,JX8797 68,AB027521,EF1172 48 |
| Seoul virus | NC_005238 | vertebrates,human | 5 | Bunyaviridae,Hantavirus,Seoul virus | seg. L | JX879770,EF190551, X56492,JX853574,EF 581094 |
| Seoul virus 5CSG | NC_005237 | vertebrates,human | 1 | Bunyaviridae,Hantavirus,Seoul virus | seg. M | AB618130 |
| Seoul virus B-1 | NC_005236 | vertebrates,human | 1 | Bunyaviridae,Hantavirus,Seoul virus | seg. S | X53861 |
| Seoul virus BjHDQ1 | NC_005237 | vertebrates,human | 1 | Bunyaviridae,Hantavirus,Seoul virus | seg. S | AY627049 |
| Seoul virus BjHDQ1 | NC_005236 | vertebrates,human | 1 | Bunyaviridae,Hantavirus,Seoul virus | seg. M | DQ133505 |
| Seoul virus CSG5 | NC_005237 | vertebrates,human | 1 | Bunyaviridae,Hantavirus,Seoul virus | seg. S | AB618112 |
| Seoul virus Gou3-e5 | NC_005237 | vertebrates,human | 1 | Bunyaviridae,Hantavirus,Seoul virus | seg. M | AF288650 |
| Seoul virus Hb8610 | NC_005236 | vertebrates,human | 1 | Bunyaviridae,Hantavirus,Seoul virus | seg. S | AF288643 |
| Seoul virus K24-e7 | NC_005236 | vertebrates,human | 1 | Bunyaviridae,Hantavirus,Seoul virus | seg. S | AF288653 |
| Seoul virus K24-e7 | NC_005237 | vertebrates,human | 1 | Bunyaviridae,Hantavirus,Seoul virus | seg. M | AF288652 |
| Seoul virus K24-v2 | NC_005236 | vertebrates,human | 1 | Bunyaviridae,Hantavirus,Seoul virus | seg. S | AF288655 |
| Seoul virus K24-v2 | NC_005237 | vertebrates,human | 1 | Bunyaviridae,Hantavirus,Seoul virus | seg. M | AF288654 |
| Seoulvirus Gou3 | NC_005237 | vertebrates,human | 1 | Bunyaviridae,Hantavirus,Seoul virus | seg. M | AF184988 |
| Seoulvirus Gou3 | NC_005237 | vertebrates,human | 1 | Bunyaviridae,Hantavirus,Seoul virus | seg. M | AF145977 |
| Seoulvirus HB55 | NC_005237 | vertebrates,human | 1 | Bunyaviridae,Hantavirus,Seoul virus | seg. M | AF035832 |
| Seoulvirus IR461 | NC_005236 | vertebrates,human | 1 | Bunyaviridae,Hantavirus,Seoul virus | seg. S | AF329388 |
| Seoulvirus IR461 | NC_005237 | vertebrates,human | 1 | Bunyaviridae,Hantavirus,Seoul virus | seg. M | AF458104 |
| Seoulvirus L99 | NC_005236 | vertebrates,human | 1 | Bunyaviridae,Hantavirus,Seoul virus | seg. S | AF288299 |
| Seoulvirus L99 | NC_005237 | vertebrates,human | 2 | Bunyaviridae,Hantavirus,Seoul virus | seg. M | AF288298,AF035833 |
| Seoulvirus L99 | NC_005238 | vertebrates,human | 1 | Bunyaviridae,Hantavirus,Seoul virus | seg. L | AF288297 |
| Seoulvirus R22 | NC_005236 | vertebrates,human | 2 | Bunyaviridae,Hantavirus,Seoul virus | seg. S | AF488707,AF288295 |
| Seoulvirus tchoupitoulas | NC_005236 | vertebrates,human | 1 | Bunyaviridae,Hantavirus,Seoul virus | seg. S | AF329389 |
| Simian Agent 10 | NC_001796 | vertebrates,human | 1 | Paramyxoviridae,Respirovirus,Human parainfluenza virus 3 | — | HM583801 |
| Simian adenovirus 27,1 | NC_011202 | vertebrates,human | 1 | Adenoviridae,Mastadenovirus,Human adenovirus B | — | FJQ25909 |
| Simian adenovirus 27,1 | NC_011203 | vertebrates,human | 1 | Adenoviridae,Mastadenovirus,Human adenovirus B | — | FJQ25909 |
| Simian adenovirus 27,2 | NC_011202 | vertebrates,human | 1 | Adenoviridae,Mastadenovirus,Human adenovirus B | — | FJQ25928 |

TABLE 10-continued

| Taxonomy | Rep.Acc.ID | Host | # GN's | Lineage | Seg. Count | GN.Acc.IDs |
|---|---|---|---|---|---|---|
| Simian adenovirus 27.2 | NC_011203 | vertebrates,human | 1 | Adenoviridae,Mastadenovirus,Human adenovirus B | — | FJQ25928 |
| Simian adenovirus 28.1 | NC_011202 | vertebrates,human | 1 | Adenoviridae,Mastadenovirus,Human adenovirus B | — | FJQ25914 |
| Simian adenovirus 28.1 | NC_011203 | vertebrates,human | 1 | Adenoviridae,Mastadenovirus,Human adenovirus B | — | FJQ25914 |
| Simian adenovirus 28.2 | NC_011202 | vertebrates,human | 1 | Adenoviridae,Mastadenovirus,Human adenovirus B | — | FJQ25915 |
| Simian adenovirus 28.2 | NC_011203 | vertebrates,human | 1 | Adenoviridae,Mastadenovirus,Human adenovirus B | — | FJQ25915 |
| Simian adenovirus 28.2 | NC_011202 | vertebrates,human | 1 | Adenoviridae,Mastadenovirus,Human adenovirus B | — | FJQ25916 |
| Simian adenovirus 29 | NC_011203 | vertebrates,human | 1 | Adenoviridae,Mastadenovirus,Human adenovirus B | — | FJQ25916 |
| Simian adenovirus 29 | NC_001405 | vertebrates,human | 1 | Adenoviridae,Mastadenovirus,Human adenovirus C | — | FJQ25906 |
| Simian adenovirus 31.1 | NC_001405 | vertebrates,human | 1 | Adenoviridae,Mastadenovirus,Human adenovirus C | — | FJQ25904 |
| Simian adenovirus 31.2 | NC_011202 | vertebrates,human | 1 | Adenoviridae,Mastadenovirus,Human adenovirus B | — | FJQ25911 |
| Simian adenovirus 32 | NC_011203 | vertebrates,human | 1 | Adenoviridae,Mastadenovirus,Human adenovirus B | — | FJQ25911 |
| Simian adenovirus 32 | NC_011202 | vertebrates,human | 1 | Adenoviridae,Mastadenovirus,Human adenovirus B | — | FJQ25908 |
| Simian adenovirus 33 | NC_011203 | vertebrates,human | 1 | Adenoviridae,Mastadenovirus,Human adenovirus B | — | FJQ25908 |
| Simian adenovirus 33 | NC_001405 | vertebrates,human | 1 | Adenoviridae,Mastadenovirus,Human adenovirus C | — | FJQ25905 |
| Simian adenovirus 34 | NC_011202 | vertebrates,human | 1 | Adenoviridae,Mastadenovirus,Human adenovirus B | — | FJQ25912 |
| Simian adenovirus 35.1 | NC_011203 | vertebrates,human | 1 | Adenoviridae,Mastadenovirus,Human adenovirus B | — | FJQ25912 |
| Simian adenovirus 35.1 | NC_011202 | vertebrates,human | 1 | Adenoviridae,Mastadenovirus,Human adenovirus B | — | FJQ25910 |
| Simian adenovirus 35.2 | NC_011203 | vertebrates,human | 1 | Adenoviridae,Mastadenovirus,Human adenovirus B | — | FJQ25910 |
| Simian adenovirus 35.2 | NC_001405 | vertebrates,human | 1 | Adenoviridae,Mastadenovirus,Human adenovirus C | — | FJQ25907 |
| Simian adenovirus 40.1 | NC_001405 | vertebrates,human | 1 | Adenoviridae,Mastadenovirus,Human adenovirus C | — | FJQ25926 |
| Simian adenovirus 40.2 | NC_011202 | vertebrates,human | 1 | Adenoviridae,Mastadenovirus,Human adenovirus B | — | FJQ25913 |
| Simian adenovirus 41.1 | NC_011203 | vertebrates,human | 1 | Adenoviridae,Mastadenovirus,Human adenovirus B | — | FJQ25913 |
| Simian adenovirus 41.1 | NC_011202 | vertebrates,human | 1 | Adenoviridae,Mastadenovirus,Human adenovirus B | — | FJQ25927 |
| Simian adenovirus 41.2 | NC_011203 | vertebrates,human | 1 | Adenoviridae,Mastadenovirus,Human adenovirus B | — | FJQ25927 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Simian adenovirus 42.1 | NC_001405 | vertebrates,human | 1 | Adenoviridae,Mastadenovirus,Human adenovirus C | — | FJQ25903 |
| Simian adenovirus 42.2 | NC_001405 | vertebrates,human | 1 | Adenoviridae,Mastadenovirus,Human adenovirus C | — | FJQ25902 |
| Simian adenovirus 42.3 | NC_001405 | vertebrates,human | 1 | Adenoviridae,Mastadenovirus,Human adenovirus C | — | FJQ25925 |
| Simian adenovirus 43 | NC_001405 | vertebrates,human | 1 | Adenoviridae,Mastadenovirus,Human adenovirus C | — | FJQ25900 |
| Simian adenovirus 44 | NC_001405 | vertebrates,human | 1 | Adenoviridae,Mastadenovirus,Human adenovirus C | — | FJQ25899 |
| Simian adenovirus 45 | NC_001405 | vertebrates,human | 1 | Adenoviridae,Mastadenovirus,Human adenovirus C | — | FJQ25901 |
| Simian adenovirus 46 | NC_011202 | vertebrates,human | 1 | Adenoviridae,Mastadenovirus,Human adenovirus B | — | FJQ25930 |
| Simian adenovirus 46 | NC_011203 | vertebrates,human | 1 | Adenoviridae,Mastadenovirus,Human adenovirus B | — | FJQ25930 |
| Simian adenovirus 47 | NC_011202 | vertebrates,human | 1 | Adenoviridae,Mastadenovirus,Human adenovirus B | — | FJQ25929 |
| Simian adenovirus 47 | NC_011203 | vertebrates,human | 1 | Adenoviridae,Mastadenovirus,Human adenovirus B | — | FJQ25929 |
| Simian agents | NC_001472 | vertebrates,human | 1 | Picornaviridae,Enterovirus,Enterovirus B | — | AF326751 |
| Simian enterovirus 19 | NC_001612 | vertebrates,human | 1 | Picornaviridae,Enterovirus,Enterovirus A | — | AF326754 |
| Simian enterovirus 43 | NC_001612 | vertebrates,human | 1 | Picornaviridae,Enterovirus,Enterovirus A | — | AF326761 |
| Simian enterovirus 46 | NC_001612 | vertebrates,human | 2 | Picornaviridae,Enterovirus,Enterovirus A | — | EF667343,AF326764 |
| Simian rotavirus | NC_011500 | vertebrates,human | 6 | Reoviridae,Rotavirus,Rotavirus A | seg. 5 | AF290884,AF290883,AF290882,Z32535,AF290881,FJ422135 |
| Simian rotavirus | NC_011501 | vertebrates,human | 2 | Reoviridae,Rotavirus,Rotavirus A | seg. 7 | GU550506,FJ422137 |
| Simian rotavirus | NC_011502 | vertebrates,human | 2 | Reoviridae,Rotavirus,Rotavirus A | seg. 8 | X81426,FJ422138 |
| Simian rotavirus | NC_011503 | vertebrates,human | 4 | Reoviridae,Rotavirus,Rotavirus A | seg. 9 | X66158,V01546,V01190,FJ422139 |
| Simian rotavirus | NC_011504 | vertebrates,human | 2 | Reoviridae,Rotavirus,Rotavirus A | seg. 10 | FJ422140,L41247 |
| Simian rotavirus | NC_011505 | vertebrates,human | 4 | Reoviridae,Rotavirus,Rotavirus A | seg. 11 | AF306493,XQ7831,FJ422141,M28347 |
| Simian rotavirus | NC_011506 | vertebrates,human | 3 | Reoviridae,Rotavirus,Rotavirus A | seg. 2 | AF474406,L33364,FJ422132 |
| Simian rotavirus | NC_011507 | vertebrates,human | 1 | Reoviridae,Rotavirus,Rotavirus A | seg. 1 | FJ422131 |
| Simian rotavirus | NC_011508 | vertebrates,human | 1 | Reoviridae,Rotavirus,Rotavirus A | seg. 3 | FJ422133 |
| Simian rotavirus | NC_011509 | vertebrates,human | 5 | Reoviridae,Rotavirus,Rotavirus A | seg. 6 | L15384,FJ422136,L33365,XQ0421,M27824 |
| Simian rotavirus 4 | NC_011510 | vertebrates,human | 5 | Reoviridae,Rotavirus,Rotavirus A | seg. 4 | M23188,FJ422134,D16345,D16346,X1420 |
| Simian rotavirus A strain RRV | NC_011506 | vertebrates,human | 2 | Reoviridae,Rotavirus,Rotavirus A | seg. 2 | EF583007,EU636925 |
| Simian rotavirus A strain RRV | NC_011507 | vertebrates,human | 2 | Reoviridae,Rotavirus,Rotavirus A | seg. 1 | EU636924,EF583006 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Simian rotavirus A strain RRV | NC_011508 | vertebrates,human | 2 | Reoviridae,Rotavirus,Rotavirus A | seg. 3 | EU636926,EF583008 |
| Simian rotavirus A strain RRV | NC_011509 | vertebrates,human | 1 | Reoviridae,Rotavirus,Rotavirus A | seg. 6 | EF583009 |
| Simian rotavirus A strain TUCH | NC_011500 | vertebrates,human | 1 | Reoviridae,Rotavirus,Rotavirus A | seg. 5 | FJ816612 |
| Simian rotavirus A strain TUCH | NC_011501 | vertebrates,human | 1 | Reoviridae,Rotavirus,Rotavirus A | seg. 7 | FJ816613 |
| Simian rotavirus A strain TUCH | NC_011502 | vertebrates,human | 1 | Reoviridae,Rotavirus,Rotavirus A | seg. 8 | FJ816614 |
| Simian rotavirus A strain TUCH | NC_011503 | vertebrates,human | 1 | Reoviridae,Rotavirus,Rotavirus A | seg. 9 | FJ816615 |
| Simian rotavirus A strain TUCH | NC_011504 | vertebrates,human | 1 | Reoviridae,Rotavirus,Rotavirus A | seg. 10 | FJ816616 |
| Simian rotavirus A strain TUCH | NC_011505 | vertebrates,human | 1 | Reoviridae,Rotavirus,Rotavirus A | seg. 11 | FJ816617 |
| Simian rotavirus A strain TUCH | NC_011506 | vertebrates,human | 1 | Reoviridae,Rotavirus,Rotavirus A | seg. 2 | EF583011 |
| Simian rotavirus A strain TUCH | NC_011507 | vertebrates,human | 1 | Reoviridae,Rotavirus,Rotavirus A | seg. 1 | EF583010 |
| Simian rotavirus A strain TUCH | NC_011508 | vertebrates,human | 1 | Reoviridae,Rotavirus,Rotavirus A | seg. 3 | EF583012 |
| Simian rotavirus A strain TUCH | NC_011509 | vertebrates,human | 1 | Reoviridae,Rotavirus,Rotavirus A | seg. 6 | EF583013 |
| Simian rotavirus A strain TUCH | NC_011510 | vertebrates,human | 1 | Reoviridae,Rotavirus,Rotavirus A | seg. 4 | FJ816611 |
| Simian rotavirus A/SA11 | NC_011500 | vertebrates,human | 1 | Reoviridae,Rotavirus,Rotavirus A | seg. 5 | X14914 |
| Simian rotavirus A/SA11 | NC_011501 | vertebrates,human | 1 | Reoviridae,Rotavirus,Rotavirus A | seg. 7 | JQ2353 |
| Simian rotavirus A/SA11 | NC_011502 | vertebrates,human | 1 | Reoviridae,Rotavirus,Rotavirus A | seg. 8 | XQ0355 |
| Simian rotavirus A/SA11 | NC_011504 | vertebrates,human | 2 | Reoviridae,Rotavirus,Rotavirus A | seg. 10 | AF087678,K01138 |
| Simian rotavirus A/SA11 | NC_011506 | vertebrates,human | 1 | Reoviridae,Rotavirus,Rotavirus A | seg. 2 | X16831 |
| Simian rotavirus A/SA11 | NC_011507 | vertebrates,human | 1 | Reoviridae,Rotavirus,Rotavirus A | seg. 1 | X16830 |
| Simian rotavirus A/SA11 | NC_011508 | vertebrates,human | 2 | Reoviridae,Rotavirus,Rotavirus A | seg. 3 | X16062,X16387 |
| Simian rotavirus A/SA11 | NC_011509 | vertebrates,human | 1 | Reoviridae,Rotavirus,Rotavirus A | seg. 6 | AY187029 |
| Simian rotavirus A/SA11 | NC_011510 | vertebrates,human | 1 | Reoviridae,Rotavirus,Rotavirus A | seg. 4 | Y00336 |
| Simian rotavirus A/SA11-C14 | NC_011502 | vertebrates,human | 1 | Reoviridae,Rotavirus,Rotavirus A | seg. 8 | AY065843 |
| Simian rotavirus A/SA11-L2 | NC_011502 | vertebrates,human | 1 | Reoviridae,Rotavirus,Rotavirus A | seg. 8 | EF460843 |
| Simian virus 40 | NC_001669 | vertebrates,human | 35 | Polyomaviridae,Polyomavirus,Simian virus 40 | seg. 8 | EF579662,EF579804, AY271816,EF579661, FN812745,AF155358, AF156105,AY120890, AF345345,JQ2400,AF 316141,EF579665,AF 345344,EF579663,AF 316140,EF579664,AF 156107,EF579659,AY |

TABLE 10-continued

| Taxonomy | Rep.Acc.ID | Host | ViroCap-1.0 Taxonomy | | Seg. Count | GN.Acc.IDs |
|---|---|---|---|---|---|---|
| | | | # GN's | Lineage | | |
| | | | | | | 538779,EF579660,AF 180737,EF579667,AY 271817,AF156108,AF 332562,DQ660375,E F579658,EF579666,A F332699,DQ218418, EF579803,AF155359, AF316139,AF168994, AF038616 |
| Simian virus 41 | NC_006428 | vertebrates,human | 1 | Paramyxoviridae,Rubulavirus,Simian virus 41 | — | X64275 |
| Sin Nombre virus | NC_005215 | vertebrates,human | 6 | Bunyaviridae,Hantavirus,Sin Nombre virus | seg. M | JQ690283,JQ690280, JQ690279,JQ690284, L25783, L37903 |
| Sin Nombre virus | NC_005216 | vertebrates,human | 8 | Bunyaviridae,Hantavirus,Sin Nombre virus | seg. S | L25784,JQ690281,JQ 690277,JQ690282,JQ 690278,JQ690276,AF 281851,L37904 |
| Sin Nombre virus | NC_005217 | vertebrates,human | 2 | Bunyaviridae,Hantavirus,Sin Nombre virus | seg. L | L37902,L37901 |
| Small anellovirus 2 | NC_007014 ,NC_00701 3 | vertebrates,human | 1 | Anelloviridae,Small anellovirus | — | AY622909 |
| Snow Mountain virus | NC_001959 | vertebrates,human | 1 | Caliciviridae,Norovirus,Norwalk virus | — | AY134748 |
| Southampton virus | NC_001959 | vertebrates,human | 1 | Caliciviridae,Norovirus,Norwalk virus | — | L07418 |
| Sudan ebolavirus | NC_006432 | vertebrates,human | 9 | Filoviridae,Ebolavirus,Sudan ebolavirus | — | KC545391,EU338380 ,KC589025,KC24278 3,FJ968794,KC54539 0,AY729654,KC5453 89,KC545392 |
| Sudan ebolavirus- Nakisamata | NC_006432 | vertebrates,human | 1 | Filoviridae,Ebolavirus,Sudan ebolavirus | — | JN638998 |
| Swine hepatitis E virus | NC_001434 | vertebrates,human | 26 | Hepeviridae,Hepevirus,Hepatitis E virus | — | GU361892,FJ998008, GU188851,AB481228 ,EU723514,AY59419 9,GU119961,FJ61023 2,GU119960,KF1763 51,AB097811,AB073 912,AB481227,EU72 3512,EU676172,EU7 23515,AY115488,EU 723513,AF082843,D 0279091,FJ426403,F J426404,AB481229,J X855794,EU723516, AB481226 |
| Swine vesicular disease virus | NC_001472 | vertebrates,human | 4 | Picornaviridae,Enterovirus,Enterovirus B | — | AY429470,AF268065, D16364,X54521 |
| Swine vesicular disease virus (STRAIN H/3 '76) | NC_001472 | vertebrates,human | 1 | Picornaviridae,Enterovirus,Enterovirus B | — | DQ0435 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| TT virus 51e1931 | NC_015783 | vertebrates,human | 1 | Anelloviridae,Torque teno virus | — | AM712003 |
| TT virus 51e1932 | NC_015783 | vertebrates,human | 1 | Anelloviridae,Torque teno virus | — | AM712004 |
| TT virus 51e1957 | NC_015783 | vertebrates,human | 1 | Anelloviridae,Torque teno virus | — | AM711976 |
| TT virus 51e2057 | NC_015783 | vertebrates,human | 1 | Anelloviridae,Torque teno virus | — | AM712030 |
| TT virus 51e2058 | NC_015783 | vertebrates,human | 1 | Anelloviridae,Torque teno virus | — | AM712031 |
| TT virus 51e2061 | NC_015783 | vertebrates,human | 1 | Anelloviridae,Torque teno virus | — | AM712033 |
| TT virus 51e2065 | NC_015783 | vertebrates,human | 1 | Anelloviridae,Torque teno virus | — | AM712034 |
| TT virus 51e2072 | NC_015783 | vertebrates,human | 1 | Anelloviridae,Torque teno virus | — | AM712032 |
| TTV-like mini virus | NC_020498 | vertebrates,human | 8 | Anelloviridae,TTV-like mini virus | — | KF764702,JX134046, AB026930,JX134044, AB038628,AB038626 ,KF764701,JX134045 |
| Tacaribe virus | NC_004292 | vertebrates,human | 1 | Arenaviridae,Arenavirus,Tacaribe virus | seg. L | JQ4340 |
| Tacaribe virus | NC_004293 | vertebrates,human | 1 | Arenaviridae,Arenavirus,Tacaribe virus | seg. S | M20304 |
| Tamiami virus | NC_010701 | vertebrates,human | 3 | Arenaviridae,Arenavirus,Tamiami virus | seg. S | AF512828,AF485263, EU486821 |
| Tamiami virus | NC_010702 | vertebrates,human | 2 | Arenaviridae,Arenavirus,Tamiami virus | seg. L | AY924393,EU627614 |
| Thottapalayam virus | NC_010704 | vertebrates,human | 1 | Bunyaviridae,Hantavirus,Thottapalayam virus | seg. S | AY526097 |
| Thottapalayam virus | NC_010707 | vertebrates,human | 2 | Bunyaviridae,Hantavirus,Thottapalayam virus | seg. L | EU001330,DQ825770 |
| Thottapalayam virus | NC_010708 | vertebrates,human | 2 | Bunyaviridae,Hantavirus,Thottapalayam virus | seg. M | EU001329,DQ825771 |
| Tioman virus | NC_004074 | vertebrates,human | 1 | Paramyxoviridae,Rubulavirus,Tioman virus | — | AF298895 |
| Torque teno canis virus | NC_014071 | vertebrates,human | 3 | Anelloviridae,Thetatorquevirus,Torque teno canis virus | — | AB076002,GU951508 ,HM855265 |
| Torque teno douroucouli virus | NC_014087 | vertebrates,human | 1 | Anelloviridae,Zetatorquevirus,Torque teno douroucouli virus | — | AB041961 |
| Torque teno felis virus | NC_014072 | vertebrates,human | 3 | Anelloviridae,Etatorquevirus,Torque teno felis virus | — | HM142589,HM14258 8,AB076003 |
| Torque teno midi virus 1 | NC_009225 | vertebrates,human | 2 | Anelloviridae,Gammatorquevirus,Torque teno midi virus 1 | — | AB290918,AB290917 |
| Torque teno midi virus 2 | NC_014093 | vertebrates,human | 1 | Anelloviridae,Gammatorquevirus,Torque teno midi virus 2 | — | AB290919 |
| Torque teno mini virus 1 | NC_014097 | vertebrates,human | 1 | Anelloviridae,Betatorquevirus,Torque teno mini virus 1 | — | AB026931 |
| Torque teno mini virus 2 | NC_014086 | vertebrates,human | 1 | Anelloviridae,Betatorquevirus,Torque teno mini virus 2 | — | AB038629 |
| Torque teno mini virus 3 | NC_014088 | vertebrates,human | 1 | Anelloviridae,Betatorquevirus,Torque teno mini virus 3 | — | AB038630 |
| Torque teno mini virus 4 | NC_014090 | vertebrates,human | 1 | Anelloviridae,Betatorquevirus,Torque teno mini virus 4 | — | AB041963 |
| Torque teno mini virus 5 | NC_014089 | vertebrates,human | 1 | Anelloviridae,Betatorquevirus,Torque teno mini virus 5 | — | AB041962 |
| Torque teno mini virus 6 | NC_014095 | vertebrates,human | 1 | Anelloviridae,Betatorquevirus,Torque teno mini virus 6 | — | AB026929 |
| Torque teno mini virus 7 | NC_014082 | vertebrates,human | 1 | Anelloviridae,Betatorquevirus,Torque teno mini virus 7 | — | AB038627 |
| Torque teno mini virus 8 | NC_014068 | vertebrates,human | 1 | Anelloviridae,Betatorquevirus,Torque teno mini virus 8 | — | AF291073 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Torque teno mini virus 9 | NC_002195 | vertebrates,human | 2 | Anelloviridae,Betatorquevirus,Torque teno mini virus 9 | — | AB038631,AB038625 |
| Torque teno sus virus 1 | NC_014070 | vertebrates,human | 13 | Anelloviridae,Iotatorquevirus,Torque teno sus virus 1a | — | HM633256,AB076001,JF937662,JF937660,JF937661,HM633251,JN688927,AY823990,JF694117,HM63324 9,HM633245,HM6332 43,JF694116 |
| Torque teno sus virus 1a | NC_014070 | vertebrates,human | 3 | Anelloviridae,Iotatorquevirus,Torque teno sus virus 1a | — | JX535326,JX535327, JQ933527 |
| Torque teno sus virus k2 | NC_014092 | vertebrates,human | 1 | Anelloviridae,Kappatorquevirus,Torque teno sus virus k2 | — | AY823991 |
| Torque teno sus virus k2b | NC_014092 | vertebrates,human | 3 | Anelloviridae,Kappatorquevirus,Torque teno sus virus k2 | — | JQ406846,JQ406844, JQ406845 |
| Torque teno tamarin virus | NC_014085 | vertebrates,human | 1 | Anelloviridae,Epsilontorquevirus,Torque teno tamarin virus | — | AB041960 |
| Torque teno virus | NC_014070 | vertebrates,human | 4 | Anelloviridae,Iotatorquevirus,Torque teno sus virus 1a | — | GQ120664,GU45638 3,GU456384,GU1880 45 |
| Torque teno virus | NC_015783 | vertebrates,human | 114 | Anelloviridae,Torque teno virus | — | AF351132,FR751478, AF247138,FR751507, FR751483,FR751485 ,FR751472,AJ620233 ,FR751470,AB02866 9,AB064603,FR7515 06,AF122915,FR7514 71,AB064597,FR751 463,AJ620216,FR751 495,AY823989,FR84 8325,AB054648,AF12 2916,AJ620228,AJ62 0212,FR848327,FR7 51479,FR751500,AF1 22914,AJ620224,FR7 51477,AJ620235,AB0 64599,FR751465,FR 751491,FR848323,F R751502,AB017610, FR751504,AB064606 ,AJ620218,FR751493 ,AJ620227,AF122917 ,AJ620231,FR751480 ,DQ003344,FR751147 5,AY823988,FR7514 69,AJ620219,AB0386 19,AF116842,FR7514 68,FR751490,FR751 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Torque teno virus 1 | NC_002076 | vertebrates,human | 2 | Anelloviridae,Alphatorquevirus,Torque teno virus 1 | — | 501,AB064602,AJ620221,AF298585,AJ620226,AB038620,FR751503,FR751509,FR751481,AJ620214,FR751497,DQ003341,DQ00343,FR751476,AJ620232,AJ620230,FR751487,AJ620229,AB064600,AF247137,AF122921,FR751492,AF122918,FR751508,AF122920,FJ426280,FR751484,AF122913,FR751511,FR751489,FR751496,AJ620234,AF079173,FR751482,FR751494,AB064601,AB064596,AJ620223,AJ620225,FR751510,FR751486,AF129887,AJ620213,DQ003342,AJ620220,FR751473,FR848324,AJ620222,FR751505,FR751146,FR848326,FR751474,AB064604,FR751498,FR751467,AJ620215,AJ620217,FR751464,FR751488,FR751499 |
| Torque teno virus 1 | NC_014070 | vertebrates,human | 5 | Anelloviridae,Iotatorquevirus,Torque teno sus virus 1a | — | GU570202,GU570198,GU570201,GU570199,GU570200 |
| Torque teno virus 10 | NC_014076 | vertebrates,human | 2 | Anelloviridae,Alphatorquevirus,Torque teno virus 10 | — | AB064607,GU797360 |
| Torque teno virus 12 | NC_014075 | vertebrates,human | 1 | Anelloviridae,Alphatorquevirus,Torque teno virus 12 | — | AB064605 |
| Torque teno virus 14 | NC_014077 | vertebrates,human | 1 | Anelloviridae,Alphatorquevirus,Torque teno virus 14 | — | AB037926 |
| Torque teno virus 15 | NC_014096 | vertebrates,human | 1 | Anelloviridae,Alphatorquevirus,Torque teno virus 15 | — | AB028668 |
| Torque teno virus 16 | NC_014091 | vertebrates,human | 1 | Anelloviridae,Alphatorquevirus,Torque teno virus 16 | — | AB017613 |
| Torque teno virus 19 | NC_014078 | vertebrates,human | 1 | Anelloviridae,Alphatorquevirus,Torque teno virus 19 | — | AB025946 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Torque teno virus 2 | NC_014480 | vertebrates,human | 1 | Anelloviridae,Alphatorquevirus,Torque teno virus 2 | — | AB049608 |
| Torque teno virus 25 | NC_014083 | vertebrates,human | 1 | Anelloviridae,Alphatorquevirus,Torque teno virus 25 | — | AB041959 |
| Torque teno virus 26 | NC_014079 | vertebrates,human | 1 | Anelloviridae,Alphatorquevirus,Torque teno virus 26 | — | AB041958 |
| Torque teno virus 27 | NC_014074 | vertebrates,human | 1 | Anelloviridae,Alphatorquevirus,Torque teno virus 27 | — | AB064595 |
| Torque teno virus 28 | NC_014073 | vertebrates,human | 1 | Anelloviridae,Alphatorquevirus,Torque teno virus 28 | — | AB064598 |
| Torque teno virus 3 | NC_014081 | vertebrates,human | 1 | Anelloviridae,Alphatorquevirus,Torque teno virus 3 | — | AY666122 |
| Torque teno virus 4 | NC_014069 | vertebrates,human | 1 | Anelloviridae,Alphatorquevirus,Torque teno virus 4 | — | AB041957 |
| Torque teno virus 6 | NC_014094 | vertebrates,human | 1 | Anelloviridae,Alphatorquevirus,Torque teno virus 6 | — | AF435014 |
| Torque teno virus 7 | NC_014080 | vertebrates,human | 1 | Anelloviridae,Alphatorquevirus,Torque teno virus 7 | — | AF261761 |
| Torque teno virus 8 | NC_014084 | vertebrates,human | 1 | Anelloviridae,Alphatorquevirus,Torque teno virus 8 | — | AB054647 |
| Torque teno zalophus virus 1 | NC_012126 | vertebrates,human zalophus virus 1 | 1 | Anelloviridae,Lambdatorquevirus,Torque teno zalophus virus 1 | — | FJ459582 |
| Tula virus | NC_005226 | vertebrates,human | 1 | Bunyaviridae,Hantavirus,Tula virus | seg. L | AJQ05637 |
| Tula virus | NC_005227 | vertebrates,human | 18 | Bunyaviridae,Hantavirus,Tula virus | seg. S | AM945877,Z30945,AJ223600,AF164093,Z30942,AF017659,Z30943,Z30944,Y13980,AF164094,AJ223601,AF44621,Z48573,Y13979,Z30941,Z48741,Z48574,Z49915 |
| Bluetongue virus 1 | NC_006014 | vertebrates,invertebrates | 11 | Reoviridae,Orbivirus,Bluetongue virus | seg. 3 | DQ186807,JN848761,JN881987,DQ186822,DQ186811,AF529048,DQ186818,AF529044,DQ186816,DQ186792,DQ186820 |
| Bluetongue virus 1 | NC_006015 | vertebrates,invertebrates | 13 | Reoviridae,Orbivirus,Bluetongue virus | seg. 10 | AF512912,JX272388,AF512911,JN848768,KJQ19214,KC879624,AF529057,FJ437561,JN881994,AF135223,AF529049,AF529052,AF512910 |
| Bluetongue virus 1 | NC_006022 | vertebrates,invertebrates | 6 | Reoviridae,Orbivirus,Bluetongue virus | seg. 7 | AY789967,AY776331,FJ437558,FJ437562,FJ437562,JN881991,JN848765 |

TABLE 10-continued

VirCap-1.0 Taxonomy

| Taxonomy | Rep.Acc.ID | Host | # GN's | Lineage | Seg. Count | GN.Acc.IDs |
|---|---|---|---|---|---|---|
| Bluetongue virus 1 | NC_006023 | vertebrates,invertebrates | 2 | Reoviridae,Orbivirus,Bluetongue virus | seg. 1 | JN881

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bluetongue virus 13 | NC_006007 | vertebrates,invertebrates | 1 | Reoviridae,Orbivirus,Bluetongue virus | seg. 8 | AY855289 |
| Bluetongue virus 13 | NC_006010 | vertebrates,invertebrates | 2 | Reoviridae,Orbivirus,Bluetongue virus | seg. 6 | AY855280,AJ586713 |
| Bluetongue virus 13 | NC_006013 | vertebrates,invertebrates | 2 | Reoviridae,Orbivirus,Bluetongue virus | seg. 2 | L11874,L11741 |
| Bluetongue virus 13 | NC_006014 | vertebrates,invertebrates | 1 | Reoviridae,Orbivirus,Bluetongue virus | seg. 3 | L19969 |
| Bluetongue virus 13 | NC_006015 | vertebrates,invertebrates | 1 | Reoviridae,Orbivirus,Bluetongue virus | seg. 10 | JX272498 |
| Bluetongue virus 13 | NC_006022 | vertebrates,invertebrates | 1 | Reoviridae,Orbivirus,Bluetongue virus | seg. 7 | AY855283 |
| Bluetongue virus 13 | NC_006023 | vertebrates,invertebrates | 2 | Reoviridae,Orbivirus,Bluetongue virus | seg. 1 | L20446,JX272489 |
| Bluetongue virus 13 | NC_006024 | vertebrates,invertebrates | 2 | Reoviridae,Orbivirus,Bluetongue virus | seg. 4 | AY855274,L08640 |
| Bluetongue virus 13 | NC_006025 | vertebrates,invertebrates | 1 | Reoviridae,Orbivirus,Bluetongue virus | seg. 5 | M97762 |
| Bluetongue virus 14 | NC_006010 | vertebrates,invertebrates | 2 | Reoviridae,Orbivirus,Bluetongue virus | seg. 6 | AJ586714,AJ586715 |
| Bluetongue virus 14 | NC_006015 | vertebrates,invertebrates | 1 | Reoviridae,Orbivirus,Bluetongue virus | seg. 10 | JX272488 |
| Bluetongue virus 15 | NC_006007 | vertebrates,invertebrates | 2 | Reoviridae,Orbivirus,Bluetongue virus | seg. 8 | JQ086228,AM900379 |
| Bluetongue virus 15 | NC_006008 | vertebrates,invertebrates | 1 | Reoviridae,Orbivirus,Bluetongue virus | seg. 9 | JQ086229 |
| Bluetongue virus 15 | NC_006010 | vertebrates,invertebrates | 4 | Reoviridae,Orbivirus,Bluetongue virus | seg. 6 | AJ586716,AJ586717, AJ586718,JQ086226 |
| Bluetongue virus 15 | NC_006013 | vertebrates,invertebrates | 1 | Reoviridae,Orbivirus,Bluetongue virus | seg. 2 | JQ086222 |
| Bluetongue virus 15 | NC_006014 | vertebrates,invertebrates | 1 | Reoviridae,Orbivirus,Bluetongue virus | seg. 3 | JQ086223 |
| Bluetongue virus 15 | NC_006015 | vertebrates,invertebrates | 3 | Reoviridae,Orbivirus,Bluetongue virus | seg. 10 | AF135228,JX272478, JQ086230 |
| Bluetongue virus 15 | NC_006022 | vertebrates,invertebrates | 2 | Reoviridae,Orbivirus,Bluetongue virus | seg. 7 | L11724,JQ086227 |
| Bluetongue virus 15 | NC_006023 | vertebrates,invertebrates | 1 | Reoviridae,Orbivirus,Bluetongue virus | seg. 1 | JQ086221 |
| Bluetongue virus 15 | NC_006024 | vertebrates,invertebrates | 1 | Reoviridae,Orbivirus,Bluetongue virus | seg. 4 | JQ086224 |
| Bluetongue virus 15 | NC_006025 | vertebrates,invertebrates | 1 | Reoviridae,Orbivirus,Bluetongue virus | seg. 5 | JQ086225 |
| Bluetongue virus 15 | NC_006007 | vertebrates,invertebrates | 3 | Reoviridae,Orbivirus,Bluetongue virus | seg. 8 | JQ086238,AM900386 JQ924827 |
| Bluetongue virus 16 | NC_006008 | vertebrates,invertebrates | 2 | Reoviridae,Orbivirus,Bluetongue virus | seg. 9 | JQ086239,JQ924828 |
| Bluetongue virus 16 | NC_006010 | vertebrates,invertebrates | 10 | Reoviridae,Orbivirus,Bluetongue virus | seg. 6 | AJ586693,AJ586691, AJ586692,AJ586689, JQ924825,AJ586694, JN572918,AJ586690, AJ586719,JQ086236 |
| Bluetongue virus 16 | NC_006013 | vertebrates,invertebrates | 4 | Reoviridae,Orbivirus,Bluetongue virus | seg. 2 | JQ086232,DQ191260 JQ924821,DQ191259 |
| Bluetongue virus 16 | NC_006014 | vertebrates,invertebrates | 11 | Reoviridae,Orbivirus,Bluetongue virus | seg. 3 | DQ186821,DQ186798, DQ186828,DQ186827, DQ186812,DQ186814,DQ186819,JQ086233,JQ924822,DQ186796,DQ186791 |
| Bluetongue virus 16 | NC_006015 | vertebrates,invertebrates | 5 | Reoviridae,Orbivirus,Bluetongue virus | seg. 10 | JQ924829,JX272468, KF387530,AF135229, JQ086240 |
| Bluetongue virus 16 | NC_006022 | vertebrates,invertebrates | 2 | Reoviridae,Orbivirus,Bluetongue virus | seg. 7 | JQ086237,JQ924826 |
| Bluetongue virus 16 | NC_006023 | vertebrates,invertebrates | 2 | Reoviridae,Orbivirus,Bluetongue virus | seg. 1 | JQ086231,JQ924820 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bluetongue virus 16 | NC_006024 | vertebrates,invertebrates | 2 | Reoviridae,Orbivirus,Bluetongue virus | seg. 4 | JQ

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bluetongue virus 2 | NC_006013 | vertebrates,invertebrates | 23 | Reoviridae,Orbivirus,Bluetongue virus | seg. 2 | DQ191275,JN255873,DQ191273,JN255592,DQ191272,DQ191273,M21946,JQ08624 2,JN255933,DQ191912 66,DQ191263,AF481 096,DQ191267,DQ19 1274,DQ191261,DQ1 91265,AF356601,DQ 191264,DQ191271,D 0191268,DQ191262, JN255863,DQ191269 |
| Bluetongue virus 2 | NC_006014 | vertebrates,invertebrates | 11 | Reoviridae,Orbivirus,Bluetongue virus | seg. 3 | L19967,JN255864,D 0186826,JN255934,J N255924,JQ086243, DQ186815,JN255874 ,JQ713558,DQ18679 3,S78452 |
| Bluetongue virus 2 | NC_006015 | vertebrates,invertebrates | 15 | Reoviridae,Orbivirus,Bluetongue virus | seg. 10 | AF512913,JN255881, AY438033,AF512916, AF481094,AF135224, JN255941,AF135230, JQ240330,JQ086250, JQ713563,JN255931, AF512920,JX272608, JN255871 |
| Bluetongue virus 2 | NC_006022 | vertebrates,invertebrates | 10 | Reoviridae,Orbivirus,Bluetongue virus | seg. 7 | JQ086247,M64997,D 0399837,JN255938,J N255868,JN255878,A Y85528,JN255928,J 0713561,AF481095 |
| Bluetongue virus 2 | NC_006023 | vertebrates,invertebrates | 8 | Reoviridae,Orbivirus,Bluetongue virus | seg. 1 | JN255872,JQ713557, JQ240321,JQ086241, L20508,JN255922,JN 255932,JN255862 |
| Bluetongue virus 2 | NC_006024 | vertebrates,invertebrates | 14 | Reoviridae,Orbivirus,Bluetongue virus | seg. 4 | AY855272,AY134477 ,AY855271,L08637,J N255865,JN255875,J 0240324,AY855273,J N255925,JQ086244, AY855270,JQ713559, AY129085,JN255935 |
| Bluetongue virus 2 | NC_006025 | vertebrates,invertebrates | 15 | Reoviridae,Orbivirus,Bluetongue virus | seg. 5 | AM773687,AY138895 ,AM773686,JQ24032 5,JQ086245,JQ71356 0,AM773689,M97680, AM773685,JN255866 ,JN255936,AM77368 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bluetongue virus 20 | NC_006007 | vertebrates,invertebrates | 2 | Reoviridae,Orbiv TABLE 10-continued ViroCap-1.0 Taxonomy

| Taxonomy | Rep.Acc.ID | Host | # GN's | Lineage | Seg. Count | GN.Acc.IDs |
|---|---|---|---|---|---|---|
| Bluetongue virus 24 | NC_006010 | vertebrates,invertebrates | 1 | Reoviridae,Orbivirus,Bluetongue virus | seg. 6 | AJ586730 |
| Bluetongue virus 24 | NC_006013 | vertebrates,invertebrates | 1 | Reoviridae,Orbivirus,Bluetongue virus | seg. 2 | AJ585145 |
| Bluetongue virus 24 | NC_006015 | vertebrates,invertebrates | 1 | Reoviridae,Orbivirus,Bluetongue virus | seg. 10 | JX272378 |
| Bluetongue virus 3 | NC_006007 | vertebrates,invertebrates | 1 | Reoviridae,Orbivirus,Bluetongue virus | seg. 8 | JQ086288 |
| Bluetongue virus 3 | NC_006008 | vertebrates,invertebrates | 1 | Reoviridae,Orbivirus,Bluetongue virus | seg. 9 | JQ086289 |
| Bluetongue virus 3 | NC_006010 | vertebrates,invertebrates | 3 | Reoviridae,Orbivirus,Bluetongue virus | seg. 6 | AJ586698,JQ086286,AJ586697 |
| Bluetongue virus 3 | NC_006013 | vertebrates,invertebrates | 2 | Reoviridae,Orbivirus,Bluetongue virus | seg. 2 | JQ086282,L42168 |
| Bluetongue virus 3 | NC_006014 | vertebrates,invertebrates | 2 | Reoviridae,Orbivirus,Bluetongue virus | seg. 3 | JQ086283,AF529045 |
| Bluetongue virus 3 | NC_006015 | vertebrates,invertebrates | 7 | Reoviridae,Orbivirus,Bluetongue virus | seg. 10 | AF135225,AF512917,AF512918,JQ086290,AF529050,JX272598,AF512906 |
| Bluetongue virus 3 | NC_006022 | vertebrates,invertebrates | 1 | Reoviridae,Orbivirus,Bluetongue virus | seg. 7 | JQ086287 |
| Bluetongue virus 3 | NC_006023 | vertebrates,invertebrates | 1 | Reoviridae,Orbivirus,Bluetongue virus | seg. 1 | JQ086281 |
| Bluetongue virus 3 | NC_006024 | vertebrates,invertebrates |  | Reoviridae,Orbivirus,Bluetongue virus | seg. 4 | JQ086284 |
| Bluetongue virus 3 | NC_006025 | vertebrates,invertebrates | 1 | Reoviridae,Orbivirus,Bluetongue virus | seg. 5 | JQ086285 |
| Bluetongue virus 4 | NC_006007 | vertebrates,invertebrates | 5 | Reoviridae,Orbivirus,Bluetongue virus | seg. 8 | JN255889,JN255899,AM900373,JN255949,AM900372 |
| Bluetongue virus 4 | NC_006008 | vertebrates,invertebrates | 3 | Reoviridae,Orbivirus,Bluetongue virus | seg. 9 | JN255900,JN255950,JN255890 |
| Bluetongue virus 4 | NC_006010 | vertebrates,invertebrates | 13 | Reoviridae,Orbivirus,Bluetongue virus | seg. 6 | JN255887,AJ586680,AJ586682,AJ586677,AJ586679,AJ586699,AJ783909,AJ586678,AJ783908,JN255947,AJ586676,AJ586681,JN255897 |
| Bluetongue virus 4 | NC_006013 | vertebrates,invertebrates | 11 | Reoviridae,Orbivirus,Bluetongue virus | seg. 2 | EF434176,JN255943,DQ191276,JN255883,DQ191281,DQ191277,AJ585125,DQ191280,DQ191279,DQ191278,JN255893 |
| Bluetongue virus 4 | NC_006014 | vertebrates,invertebrates | 17 | Reoviridae,Orbivirus,Bluetongue virus | seg. 3 | JN255894,DQ186803,DQ186801,DQ186813,DQ186806,DQ186800,DQ186809,DQ186794,DQ186804,DQ186799,DQ186824,DQ186825,DQ186802,DQ186817,JN255884,D0186823,JN255944 |

TABLE 10-continued

ViroCap-1.0 Taxonomy

| Taxonomy | Rep.Acc.

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bluetongue virus 8 | NC_006024 | vertebrates,invertebrates | 3 | Reoviridae,Orbivirus,Bluetongue virus | seg. 4 | FJ183377,AM498054, JX680450 |
| Bluetongue virus 8 | NC_006025 | vertebrates,invertebrates | 3 | Reoviridae,Orbivirus,Bluetongue virus | seg. 5 | FJ183378,AM498055, AM498056 |
| Bluetongue virus 8 | NC_006007 | vertebrates,invertebrates | 12 | Reoviridae,Orbivirus,Bluetongue virus | seg. 8 | JN255919,AM900375 ,AM900374,JQ08630 8,JF443164,JN25596 9,AM900388,JN2559 09,AM900377,AM900 385,JN255959,AM90 0376 |
| Bluetongue virus 9 | NC_006008 | vertebrates,invertebrates | 11 | Reoviridae,Orbivirus,Bluetongue virus | seg. 9 | JF443161,JQ086309, JN255960,JN2565970, JN255910,JN255920 |
| Bluetongue virus 9 | NC_006010 | vertebrates,invertebrates | 14 | Reoviridae,Orbivirus,Bluetongue virus | seg. 6 | AJ586685,JN255967, AJ586686,JF443160, JQ086306,JN255957, AJ586688,JN255917, JN579709,AJ586683, JN255907,AJ586684, AJ586687,AJ586708 |
| Bluetongue virus 9 | NC_006013 | vertebrates,invertebrates | 13 | Reoviridae,Orbivirus,Bluetongue virus | seg. 2 | JF443157,JN255953, DQ191285,DQ19128 4,JQ086302,JF44315 6,JN255913,DQ1912 82,JF443167,JN2559 63,JF443155,DQ1912 83,JN255903 |
| Bluetongue virus 9 | NC_006014 | vertebrates,invertebrates | 11 | Reoviridae,Orbivirus,Bluetongue virus | seg. 3 | DQ186797,DQ18680 5,JN255954,DQ1867 95,JQ086303,JN2559 04,JN255964,JF4431 58,DQ186808,DQ186 790,JN255914 |
| Bluetongue virus 9 | NC_006015 | vertebrates,invertebrates | 8 | Reoviridae,Orbivirus,Bluetongue virus | seg. 10 | JQ086310,JF443165, AY438034,JN255961, JX272538,JN255911, JN255971,JN255921 |
| Bluetongue virus 9 | NC_006022 | vertebrates,invertebrates | 6 | Reoviridae,Orbivirus,Bluetongue virus | seg. 7 | JN255908,JQ086307, JN255968,JN255918, JN255958,JF443162 |
| Bluetongue virus 9 | NC_006023 | vertebrates,invertebrates | 6 | Reoviridae,Orbivirus,Bluetongue virus | seg. 1 | JN255902,JQ086301, JN255952,JN255962, JN255912,JF443166 |
| Bluetongue virus 9 | NC_006024 | vertebrates,invertebrates | 6 | Reoviridae,Orbivirus,Bluetongue virus | seg. 4 | JN255965,JN255905, JN255955,JQ086304, JN255915,JF443159 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Bluetongue virus 9 | NC_006025 | vertebrates,invertebrates | 10 | Reoviridae,Orbivirus,Bluetongue virus | seg. 5 | AM778443,JN255916,AM778444,JN255956,JF443163,AM778442,JN255906,JQ08630S,JN255966,AM778445 |
| Boolarra virus | NC_004142 | vertebrates,invertebrates | 1 | Nodaviridae,Alphanodavirus,Boolarra virus | seg. 2 | AF329080 |
| Boolarra virus | NC_004145 | vertebrates,invertebrates | 1 | Nodaviridae,Alphanodavirus,Boolarra virus | RNA 2 | X15960 |
| Buggy Creek virus | NC_013528 | vertebrates,invertebrates | 1 | Togaviridae,Alphavirus,Fort Morgan virus | — | HM147986 |
| Changuinola virus | NC_022633 | vertebrates,invertebrates | 1 | Reoviridae,Orbivirus,Changuinola virus | seg. 2 | KF624615 |
| Changuinola virus | NC_022634 | vertebrates,invertebrates | 1 | Reoviridae,Orbivirus,Changuinola virus | seg. 3 | KF624616 |
| Changuinola virus | NC_022635 | vertebrates,invertebrates | 1 | Reoviridae,Orbivirus,Changuinola virus | seg. 5 | KF624618 |
| Changuinola virus | NC_022636 | vertebrates,invertebrates | 1 | Reoviridae,Orbivirus,Changuinola virus | seg. 7 | KF624620 |
| Changuinola virus | NC_022637 | vertebrates,invertebrates | 1 | Reoviridae,Orbivirus,Changuinola virus | seg. 8 | KF624621 |
| Changuinola virus | NC_022638 | vertebrates,invertebrates | 1 | Reoviridae,Orbivirus,Changuinola virus | seg. 10 | KF624623 |
| Changuinola virus | NC_022639 | vertebrates,invertebrates | 1 | Reoviridae,Orbivirus,Changuinola virus | seg. 1 | KF624614 |
| Changuinola virus | NC_022640 | vertebrates,invertebrates | 1 | Reoviridae,Orbivirus,Changuinola virus | seg. 4 | KF624617 |
| Changuinola virus | NC_022641 | vertebrates,invertebrates | 1 | Reoviridae,Orbivirus,Changuinola virus | seg. 6 | KF624619 |
| Changuinola virus | NC_022642 | vertebrates,invertebrates | 1 | Reoviridae,Orbivirus,Changuinola virus | seg. 9 | KF624622 |
| Chuzan virus | NC_005986 | vertebrates,invertebrates | 4 | Reoviridae,Orbivirus,Palyam virus | seg. 2 | AB177635,AB177632,AB177634,AB177637 |
| Chuzan virus | NC_005988 | vertebrates,invertebrates | 2 | Reoviridae,Orbivirus,Palyam virus | seg. 7 | AY078469,AY078470 |
| Corsican bluetongue virus | NC_006007 | vertebrates,invertebrates | 1 | Reoviridae,Orbivirus,Bluetongue virus | seg. 8 | AY124372 |
| Corsican bluetongue virus | NC_006008 | vertebrates,invertebrates | 1 | Reoviridae,Orbivirus,Bluetongue virus | seg. 9 | AY124373 |
| Corsican bluetongue virus | NC_006014 | vertebrates,invertebrates | 1 | Reoviridae,Orbivirus,Bluetongue virus | seg. 3 | AY124371 |
| Corsican bluetongue virus | NC_006015 | vertebrates,invertebrates | 2 | Reoviridae,Orbivirus,Bluetongue virus | seg. 10 | AF481092,AF481093 |
| Corsican bluetongue virus | NC_006022 | vertebrates,invertebrates | 1 | Reoviridae,Orbivirus,Bluetongue virus | seg. 7 | AY079124 |
| Corsican bluetongue virus | NC_006023 | vertebrates,invertebrates | 1 | Reoviridae,Orbivirus,Bluetongue virus | seg. 1 | AY154458 |
| Eastern equine encephalitis virus | NC_003899 | vertebrates,invertebrates | 10 | Togaviridae,Alphavirus,Eastern equine encephalitis virus | — | DQ241303,DQ241304,EF151503,AY705240,AY722102,U01034,EF151502,AY705241,X63135,EF568607 |
| Eilat virus | NC_018615 | vertebrates,invertebrates | 1 | Togaviridae,Alphavirus,Eilat virus | — | JX678730 |
| Epizootic hemorrhagic disease of deer virus | NC_013398 | vertebrates,invertebrates | 1 | Reoviridae,Orbivirus,Epizootic hemorrhagic disease virus | seg. 3 | S68010 |
| Epizootic hemorrhagic disease of deer virus | NC_013402 | vertebrates,invertebrates | 3 | Reoviridae,Orbivirus,Epizootic hemorrhagic disease virus | seg. 7 | AY386683,U43560,AF188643 |
| Epizootic hemorrhagic disease virus | NC_013396 | vertebrates,invertebrates | 3 | Reoviridae,Orbivirus,Epizootic hemorrhagic disease virus | seg. 1 | HM641772,HM63689 7,HM636907 |
| Epizootic hemorrhagic NC_013397 | | vertebrates,invertebrates | 3 | Reoviridae,Orbivirus,Epizootic hemorrhagic | seg. 2 | AB030735,HM641773 |

TABLE 10-continued

| Taxonomy | Rep.Acc.ID | Host | # GN's | VirCap-1.0 Taxonomy Lineage | Seg. Count | GN.Acc.IDs |
|---|---|---|---|---|---|---|
| disease virus | | | | disease virus | | ,D10767 |
| Epizootic hemorrhagic disease virus | NC_013398 | vertebrates,invertebrates | 6 | Reoviridae,Orbivirus,Epizootic hemorrhagic disease virus | seg. 3 | X61589,HM636909,H M641774,AB041933, EU856069,HM663689 |
| Epizootic hemorrhagic disease virus | NC_013399 | vertebrates,invertebrates | 9 | Reoviridae,Orbivirus,Epizootic hemorrhagic disease virus | seg. 4 | HM641775,HM63690 0,HM636910 |
| Epizootic hemorrhagic disease virus | NC_013400 | vertebrates,invertebrates | 3 | Reoviridae,Orbivirus,Epizootic hemorrhagic disease virus | seg. 5 | HM641776,AB030736 ,X55782 |
| Epizootic hemorrhagic disease virus | NC_013401 | vertebrates,invertebrates | 2 | Reoviridae,Orbivirus,Epizootic hemorrhagic disease virus | seg. 6 | X59000,HM641777 |
| Epizootic hemorrhagic disease virus | NC_013402 | vertebrates,invertebrates | 9 | Reoviridae,Orbivirus,Epizootic hemorrhagic disease virus | seg. 7 | EF213556,D10766,E U856070,HM641778, AF484250,AY351653, AB041934,HM636913 ,HM636903 |
| Epizootic hemorrhagic disease virus | NC_013403 | vertebrates,invertebrates | 3 | Reoviridae,Orbivirus,Epizootic hemorrhagic disease virus | seg. 8 | HM636914,HM64177 9,HM636904 |
| Epizootic hemorrhagic disease virus | NC_013404 | vertebrates,invertebrates | 1 | Reoviridae,Orbivirus,Epizootic hemorrhagic disease virus | seg. 9 | HM641780 |
| Epizootic hemorrhagic disease virus | NC_013405 | vertebrates,invertebrates | 4 | Reoviridae,Orbivirus,Epizootic hemorrhagic disease virus | seg. 10 | AY351654,HM636906 ,HM641781,HM63691 6 |
| Epizootic hemorrhagic disease virus (serotype 1/ strain IbAr22619) | NC_013396 | vertebrates,invertebrates | 2 | Reoviridae,Orbivirus,Epizootic hemorrhagic disease virus | seg. 1 | AM745007,AM74501 0 |
| Epizootic hemorrhagic disease virus (serotype 1/ strain IbAr22619) | NC_013397 | vertebrates,invertebrates | 1 | Reoviridae,Orbivirus,Epizootic hemorrhagic disease virus | seg. 2 | AM745008 |
| Epizootic hemorrhagic disease virus (serotype 1/ strain IbAr22619) | NC_013398 | vertebrates,invertebrates | 1 | Reoviridae,Orbivirus,Epizootic hemorrhagic disease virus | seg. 3 | AM745009 |
| Epizootic hemorrhagic disease virus (serotype 1/ strain IbAr22619) | NC_013400 | vertebrates,invertebrates | 1 | Reoviridae,Orbivirus,Epizootic hemorrhagic disease virus | seg. 5 | AM745011 |
| Epizootic hemorrhagic disease virus (serotype 1/ strain IbAr22619) | NC_013401 | vertebrates,invertebrates | 1 | Reoviridae,Orbivirus,Epizootic hemorrhagic disease virus | seg. 6 | AM745012 |
| Epizootic hemorrhagic disease virus (serotype 1/ strain IbAr22619) | NC_013402 | vertebrates,invertebrates | 1 | Reoviridae,Orbivirus,Epizootic hemorrhagic disease virus | seg. 7 | AM745013 |
| Epizootic hemorrhagic disease virus (serotype 1/ strain IbAr22619) | NC_013403 | vertebrates,invertebrates | 1 | Reoviridae,Orbivirus,Epizootic hemorrhagic disease virus | seg. 8 | AM745014 |
| Epizootic hemorrhagic disease virus (serotype 1/ strain IbAr22619) | NC_013404 | vertebrates,invertebrates | 1 | Reoviridae,Orbivirus,Epizootic hemorrhagic disease virus | seg. 9 | AM745015 |

TABLE 10-continued

| Taxonomy | Rep.Acc.ID | Host | # GN's | Lineage | Seg. Count | GN.Acc.IDs |
|---|---|---|---|---|---|---|
| Epizootic hemorrhagic disease virus (serotype 1/ strain IbAr22619) | NC_013405 | vertebrates,invertebrates | 1 | Reoviridae,Orbivirus,Epizootic hemorrhagic disease virus | seg. 10 | AM745016 |
| Epizootic hemorrhagic disease virus (serotype 1/ strain New Jersey) | NC_013396 | vertebrates,invertebrates | 1 | Reoviridae,Orbivirus,Epizootic hemorrhagic disease virus | seg. 1 | AM744977 |
| Epizootic hemorrhagic disease virus (serotype 1/ strain New Jersey) | NC_013397 | vertebrates,invertebrates | 1 | Reoviridae,Orbivirus,Epizootic hemorrhagic disease virus | seg. 2 | AM744978 |
| Epizootic hemorrhagic disease virus (serotype 1/ strain New Jersey) | NC_013398 | vertebrates,invertebrates | 1 | Reoviridae,Orbivirus,Epizootic hemorrhagic disease virus | seg. 3 | AM744979 |
| Epizootic hemorrhagic disease virus (serotype 1/ strain New Jersey) | NC_013399 | vertebrates,invertebrates | 1 | Reoviridae,Orbivirus,Epizootic hemorrhagic disease virus | seg. 4 | AM744980 |
| Epizootic hemorrhagic disease virus (serotype 1/ strain New Jersey) | NC_013400 | vertebrates,invertebrates | 1 | Reoviridae,Orbivirus,Epizootic hemorrhagic disease virus | seg. 5 | AM744981 |
| Epizootic hemorrhagic disease virus (serotype 1/ strain New Jersey) | NC_013401 | vertebrates,invertebrates | 1 | Reoviridae,Orbivirus,Epizootic hemorrhagic disease virus | seg. 6 | AM744982 |
| Epizootic hemorrhagic disease virus (serotype 1/ strain New Jersey) | NC_013402 | vertebrates,invertebrates | 1 | Reoviridae,Orbivirus,Epizootic hemorrhagic disease virus | seg. 7 | AM744983 |
| Epizootic hemorrhagic disease virus (serotype 1/ strain New Jersey) | NC_013403 | vertebrates,invertebrates | 1 | Reoviridae,Orbivirus,Epizootic hemorrhagic disease virus | seg. 8 | AM744984 |
| Epizootic hemorrhagic disease virus (serotype 1/ strain New Jersey) | NC_013404 | vertebrates,invertebrates | 1 | Reoviridae,Orbivirus,Epizootic hemorrhagic disease virus | seg. 9 | AM744985 |
| Epizootic hemorrhagic disease virus (serotype 1/ strain New Jersey) | NC_013405 | vertebrates,invertebrates | 1 | Reoviridae,Orbivirus,Epizootic hemorrhagic disease virus | seg. 10 | AM744986 |
| Epizootic hemorrhagic disease virus (serotype 2/ strain 439) | NC_013396 | vertebrates,invertebrates | 1 | Reoviridae,Orbivirus,Epizootic hemorrhagic disease virus | seg. 1 | AM744987 |
| Epizootic hemorrhagic disease virus (serotype 2/ strain 439) | NC_013397 | vertebrates,invertebrates | 1 | Reoviridae,Orbivirus,Epizootic hemorrhagic disease virus | seg. 2 | AM744988 |
| Epizootic hemorrhagic disease virus (serotype 2/ strain 439) | NC_013398 | vertebrates,invertebrates | 1 | Reoviridae,Orbivirus,Epizootic hemorrhagic disease virus | seg. 3 | AM744989 |
| Epizootic hemorrhagic disease virus (serotype 2/ strain 439) | NC_013399 | vertebrates,invertebrates | 1 | Reoviridae,Orbivirus,Epizootic hemorrhagic disease virus | seg. 4 | AM744990 |
| Epizootic hemorrhagic disease virus (serotype 2/ strain 439) | NC_013400 | vertebrates,invertebrates | 1 | Reoviridae,Orbivirus,Epizootic hemorrhagic disease virus | seg. 5 | AM744991 |

TABLE 10-continued

VyroCap-1.0 Taxonomy

| Taxonomy | Rep.Acc.ID | Host | Lineage | # GN's | Seg. Count | GN.Acc.IDs |
|---|---|---|---|---|---|---|
| Epizootic hemorrhagic disease virus (serotype 2/ strain 439) | NC_013401 | vertebrates,invertebrates | Reoviridae,Orbivirus,Epizootic hemorrhagic disease virus | 1 | seg. 6 | AM744992 |
| Epizootic hemorrhagic disease virus (serotype 2/ strain 439) | NC_013402 | vertebrates,invertebrates | Reoviridae,Orbivirus,Epizootic hemorrhagic disease virus | 1 | seg. 7 | AM744993 |
| Epizootic hemorrhagic disease virus (serotype 2/ strain 439) | NC_013403 | vertebrates,invertebrates | Reoviridae,Orbivirus,Epizootic hemorrhagic disease virus | 1 | seg. 8 | AM744994 |
| Epizootic hemorrhagic disease virus (serotype 2/ strain 439) | NC_013404 | vertebrates,invertebrates | Reoviridae,Orbivirus,Epizootic hemorrhagic disease virus | 1 | seg. 9 | AM744995 |
| Epizootic hemorrhagic disease virus (serotype 2/ strain 439) | NC_013405 | vertebrates,invertebrates | Reoviridae,Orbivirus,Epizootic hemorrhagic disease virus | 1 | seg. 10 | AM744996 |
| Epizootic hemorrhagic disease virus (serotype 2/ strain Alberta) | NC_013396 | vertebrates,invertebrates | Reoviridae,Orbivirus,Epizootic hemorrhagic disease virus | 1 | seg. 1 | AM744997 |
| Epizootic hemorrhagic disease virus (serotype 2/ strain Alberta) | NC_013397 | vertebrates,invertebrates | Reoviridae,Orbivirus,Epizootic hemorrhagic disease virus | 1 | seg. 2 | AM744998 |
| Epizootic hemorrhagic disease virus (serotype 2/ strain Alberta) | NC_013398 | vertebrates,invertebrates | Reoviridae,Orbivirus,Epizootic hemorrhagic disease virus | 1 | seg. 3 | AM744999 |
| Epizootic hemorrhagic disease virus (serotype 2/ strain Alberta) | NC_013399 | vertebrates,invertebrates | Reoviridae,Orbivirus,Epizootic hemorrhagic disease virus | 1 | seg. 4 | AM745000 |
| Epizootic hemorrhagic disease virus (serotype 2/ strain Alberta) | NC_013400 | vertebrates,invertebrates | Reoviridae,Orbivirus,Epizootic hemorrhagic disease virus | 1 | seg. 5 | AM745001 |
| Epizootic hemorrhagic disease virus (serotype 2/ strain Alberta) | NC_013401 | vertebrates,invertebrates | Reoviridae,Orbivirus,Epizootic hemorrhagic disease virus | 1 | seg. 6 | AM745002 |
| Epizootic hemorrhagic disease virus (serotype 2/ strain Alberta) | NC_013402 | vertebrates,invertebrates | Reoviridae,Orbivirus,Epizootic hemorrhagic disease virus | 1 | seg. 7 | AM745003 |
| Epizootic hemorrhagic disease virus (serotype 2/ strain Alberta) | NC_013403 | vertebrates,invertebrates | Reoviridae,Orbivirus,Epizootic hemorrhagic disease virus | 1 | seg. 8 | AM745004 |
| Epizootic hemorrhagic disease virus (serotype 2/ strain Alberta) | NC_013404 | vertebrates,invertebrates | Reoviridae,Orbivirus,Epizootic hemorrhagic disease virus | 1 | seg. 9 | AM745005 |
| Epizootic hemorrhagic disease virus (serotype 2/ strain Alberta) | NC_013405 | vertebrates,invertebrates | Reoviridae,Orbivirus,Epizootic hemorrhagic disease virus | 1 | seg. 10 | AM745006 |
| Epizootic hemorrhagic disease virus (serotype 2/ strain Ibaraki) | NC_013396 | vertebrates,invertebrates | Reoviridae,Orbivirus,Epizootic hemorrhagic disease virus | 1 | seg. 1 | AM745077 |

TABLE 10-continued

| Taxonomy | Rep.Acc.ID | Host | # GN's | ViroCap-1.0 Taxonomy Lineage | Seg. Count | GN.Acc.IDs |
|---|---|---|---|---|---|---|
| Epizootic hemorrhagic disease virus (serotype 2/ strain Ibaraki) | NC_013397 | vertebrates,invertebrates | 1 | Reoviridae,Orbivirus,Epizootic hemorrhagic disease virus | seg. 2 | AM745078 |
| Epizootic hemorrhagic disease virus (serotype 2/ strain Ibaraki) | NC_013398 | vertebrates,invertebrates | 1 | Reoviridae,Orbivirus,Epizootic hemorrhagic disease virus | seg. 3 | AM745079 |
| Epizootic hemorrhagic disease virus (serotype 2/ strain Ibaraki) | NC_013399 | vertebrates,invertebrates | 1 | Reoviridae,Orbivirus,Epizootic hemorrhagic disease virus | seg. 4 | AM745080 |
| Epizootic hemorrhagic disease virus (serotype 2/ strain Ibaraki) | NC_013400 | vertebrates,invertebrates | 1 | Reoviridae,Orbivirus,Epizootic hemorrhagic disease virus | seg. 5 | AM745081 |
| Epizootic hemorrhagic disease virus (serotype 2/ strain Ibaraki) | NC_013401 2/ | vertebrates,invertebrates | 1 | Reoviridae,Orbivirus,Epizootic hemorrhagic disease virus | seg. 6 | AM745082 |
| Epizootic hemorrhagic disease virus (serotype 2/ strain Ibaraki) | NC_013402 | vertebrates,invertebrates | 1 | Reoviridae,Orbivirus,Epizootic hemorrhagic disease virus | seg. 7 | AM745083 |
| Epizootic hemorrhagic disease virus (serotype 2/ strain Ibaraki) | NC_013403 | vertebrates,invertebrates | 1 | Reoviridae,Orbivirus,Epizootic hemorrhagic disease virus | seg. 8 | AM745084 |
| Epizootic hemorrhagic disease virus (serotype 2/ strain Ibaraki) | NC_013404 | vertebrates,invertebrates | 1 | Reoviridae,Orbivirus,Epizootic hemorrhagic disease virus | seg. 9 | AM745085 |
| Epizootic hemorrhagic disease virus (serotype 2/ strain Ibaraki) | NC_013405 | vertebrates,invertebrates | 1 | Reoviridae,Orbivirus,Epizootic hemorrhagic disease virus | seg. 10 | AM745086 |
| Epizootic hemorrhagic disease virus (serotype 4/ strain IbAr 33853) | NC_013396 | vertebrates,invertebrates | 1 | Reoviridae,Orbivirus,Epizootic hemorrhagic disease virus | seg. 1 | AM745017 |
| Epizootic hemorrhagic disease virus (serotype 4/ strain IbAr 33853) | NC_013397 | vertebrates,invertebrates | 1 | Reoviridae,Orbivirus,Epizootic hemorrhagic disease virus | seg. 2 | AM745018 |
| Epizootic hemorrhagic disease virus (serotype 4/ strain IbAr 33853) | NC_013398 | vertebrates,invertebrates | 1 | Reoviridae,Orbivirus,Epizootic hemorrhagic disease virus | seg. 3 | AM745019 |
| Epizootic hemorrhagic disease virus (serotype 4/ strain IbAr 33853) | NC_013399 | vertebrates,invertebrates | 1 | Reoviridae,Orbivirus,Epizootic hemorrhagic disease virus | seg. 4 | AM745020 |
| Epizootic hemorrhagic disease virus (serotype 4/ strain IbAr 33853) | NC_013400 | vertebrates,invertebrates | 1 | Reoviridae,Orbivirus,Epizootic hemorrhagic disease virus | seg. 5 | AM745021 |
| Epizootic hemorrhagic disease virus (serotype 4/ strain IbAr 33853) | NC_013401 | vertebrates,invertebrates | 1 | Reoviridae,Orbivirus,Epizootic hemorrhagic disease virus | seg. 6 | AM745022 |
| Epizootic hemorrhagic disease virus (serotype 4/ strain IbAr 33853) | NC_013402 | vertebrates,invertebrates | 1 | Reoviridae,Orbivirus,Epizootic hemorrhagic disease virus | seg. 7 | AM745023 |

TABLE 10-continued

| Taxonomy | Rep.Acc.ID | Host | # GN's | Lineage | Seg. Count | GN.Acc.IDs |
|---|---|---|---|---|---|---|
| Epizootic hemorrhagic disease virus (serotype 4/ strain IbAr 33853) | NC_013403 | vertebrates,invertebrates | 1 | Reoviridae,Orbivirus,Epizootic hemorrhagic disease virus | seg. 8 | AM745024 |
| Epizootic hemorrhagic disease virus (serotype 4/ strain IbAr 33853) | NC_013404 | vertebrates,invertebrates | 1 | Reoviridae,Orbivirus,Epizootic hemorrhagic disease virus | seg. 9 | AM745025 |
| Epizootic hemorrhagic disease virus (serotype 4/ strain IbAr 33853) | NC_013405 | vertebrates,invertebrates | 1 | Reoviridae,Orbivirus,Epizootic hemorrhagic disease virus | seg. 10 | AM745026 |
| Epizootic hemorrhagic disease virus (serotype 5/ strain CSIRO 157) | NC_013396 | vertebrates,invertebrates | 2 | Reoviridae,Orbivirus,Epizootic hemorrhagic disease virus | seg. 1 | AM745028,AM745027 |
| Epizootic hemorrhagic disease virus (serotype 5/ strain CSIRO 157) | NC_013397 | vertebrates,invertebrates | 1 | Reoviridae,Orbivirus,Epizootic hemorrhagic disease virus | seg. 2 | AM745029 |
| Epizootic hemorrhagic disease virus (serotype 5/ strain CSIRO 157) | NC_013398 | vertebrates,invertebrates | 1 | Reoviridae,Orbivirus,Epizootic hemorrhagic disease virus | seg. 3 | AM745030 |
| Epizootic hemorrhagic disease virus (serotype 5/ strain CSIRO 157) | NC_013400 | vertebrates,invertebrates | 1 | Reoviridae,Orbivirus,Epizootic hemorrhagic disease virus | seg. 5 | AM745031 |
| Epizootic hemorrhagic disease virus (serotype 5/ strain CSIRO 157) | NC_013401 | vertebrates,invertebrates | 1 | Reoviridae,Orbivirus,Epizootic hemorrhagic disease virus | seg. 6 | AM745032 |
| Epizootic hemorrhagic disease virus (serotype 5/ strain CSIRO 157) | NC_013402 | vertebrates,invertebrates | 1 | Reoviridae,Orbivirus,Epizootic hemorrhagic disease virus | seg. 7 | AM745033 |
| Epizootic hemorrhagic disease virus (serotype 5/ strain CSIRO 157) | NC_013403 | vertebrates,invertebrates | 1 | Reoviridae,Orbivirus,Epizootic hemorrhagic disease virus | seg. 8 | AM745034 |
| Epizootic hemorrhagic disease virus (serotype 5/ strain CSIRO 157) | NC_013404 | vertebrates,invertebrates | 1 | Reoviridae,Orbivirus,Epizootic hemorrhagic disease virus | seg. 9 | AM745035 |
| Epizootic hemorrhagic disease virus (serotype 5/ strain CSIRO 157) | NC_013405 | vertebrates,invertebrates | 1 | Reoviridae,Orbivirus,Epizootic hemorrhagic disease virus | seg. 10 | AM745036 |
| Epizootic hemorrhagic disease virus (serotype 6/ strain 318) | NC_013396 | vertebrates,invertebrates | 1 | Reoviridae,Orbivirus,Epizootic hemorrhagic disease virus | seg. 1 | AM745067 |
| Epizootic hemorrhagic disease virus (serotype 6/ strain 318) | NC_013397 | vertebrates,invertebrates | 1 | Reoviridae,Orbivirus,Epizootic hemorrhagic disease virus | seg. 2 | AM745068 |
| Epizootic hemorrhagic disease virus (serotype 6/ strain 318) | NC_013398 | vertebrates,invertebrates | 1 | Reoviridae,Orbivirus,Epizootic hemorrhagic disease virus | seg. 3 | AM745069 |
| Epizootic hemorrhagic disease virus (serotype 6/ strain 318) | NC_013399 | vertebrates,invertebrates | 1 | Reoviridae,Orbivirus,Epizootic hemorrhagic disease virus | seg. 4 | AM745070 |

TABLE 10-continued

| Taxonomy | Rep.Acc.ID | Host | # GN's | ViroCap-1.0 Taxonomy Lineage | Seg. Count | GN.Acc.IDs |
|---|---|---|---|---|---|---|
| Epizootic hemorrhagic disease virus (serotype 6/ strain 318) | NC_013400 | vertebrates,invertebrates | 1 | Reoviridae,Orbivirus,Epizootic hemorrhagic disease virus | seg. 5 | AM745071 |
| Epizootic hemorrhagic disease virus (serotype 6/ strain 318) | NC_013401 | vertebrates,invertebrates | 1 | Reoviridae,Orbivirus,Epizootic hemorrhagic disease virus | seg. 6 | AM745072 |
| Epizootic hemorrhagic disease virus (serotype 6/ strain 318) | NC_013402 | vertebrates,invertebrates | 1 | Reoviridae,Orbivirus,Epizootic hemorrhagic disease virus | seg. 7 | AM745073 |
| Epizootic hemorrhagic disease virus (serotype 6/ strain 318) | NC_013403 | vertebrates,invertebrates | 1 | Reoviridae,Orbivirus,Epizootic hemorrhagic disease virus | seg. 8 | AM745074 |
| Epizootic hemorrhagic disease virus (serotype 6/ strain 318) | NC_013404 | vertebrates,invertebrates | 1 | Reoviridae,Orbivirus,Epizootic hemorrhagic disease virus | seg. 9 | AM745075 |
| Epizootic hemorrhagic disease virus (serotype 6/ strain 318) | NC_013405 | vertebrates,invertebrates | 1 | Reoviridae,Orbivirus,Epizootic hemorrhagic disease virus | seg. 10 | AM745076 |
| Epizootic hemorrhagic disease virus (serotype 6/ strain CSIRO 753) | NC_013396 | vertebrates,invertebrates | 2 | Reoviridae,Orbivirus,Epizootic hemorrhagic disease virus | seg. 1 7 | AM745038,AM74503 |
| Epizootic hemorrhagic disease virus (serotype 6/ strain CSIRO 753) | NC_013397 | vertebrates,invertebrates | 1 | Reoviridae,Orbivirus,Epizootic hemorrhagic disease virus | seg. 2 | AM745039 |
| Epizootic hemorrhagic disease virus (serotype 6/ strain CSIRO 753) | NC_013398 | vertebrates,invertebrates | 1 | Reoviridae,Orbivirus,Epizootic hemorrhagic disease virus | seg. 3 | AM745040 |
| Epizootic hemorrhagic disease virus (serotype 6/ strain CSIRO 753) | NC_013400 | vertebrates,invertebrates | 1 | Reoviridae,Orbivirus,Epizootic hemorrhagic disease virus | seg. 5 | AM745041 |
| Epizootic hemorrhagic disease virus (serotype 6/ strain CSIRO 753) | NC_013401 | vertebrates,invertebrates | 1 | Reoviridae,Orbivirus,Epizootic hemorrhagic disease virus | seg. 6 | AM745042 |
| Epizootic hemorrhagic disease virus (serotype 6/ strain CSIRO 753) | NC_013402 | vertebrates,invertebrates | 1 | Reoviridae,Orbivirus,Epizootic hemorrhagic disease virus | seg. 7 | AM745043 |
| Epizootic hemorrhagic disease virus (serotype 6/ strain CSIRO 753) | NC_013403 | vertebrates,invertebrates | 1 | Reoviridae,Orbivirus,Epizootic hemorrhagic disease virus | seg. 8 | AM745044 |
| Epizootic hemorrhagic disease virus (serotype 6/ strain CSIRO 753) | NC_013404 | vertebrates,invertebrates | 1 | Reoviridae,Orbivirus,Epizootic hemorrhagic disease virus | seg. 9 | AM745045 |
| Epizootic hemorrhagic disease virus (serotype 6/ strain CSIRO 753) | NC_013405 | vertebrates,invertebrates | 1 | Reoviridae,Orbivirus,Epizootic hemorrhagic disease virus | seg. 10 | AM745046 |
| Epizootic hemorrhagic disease virus (serotype 7/ strain CSIRO 775) | NC_013396 | vertebrates,invertebrates | 1 | Reoviridae,Orbivirus,Epizootic hemorrhagic disease virus | seg. 1 | AM745047 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Epizootic hemorrhagic disease virus (serotype 7/ strain CSIRO 775) | NC_013397 | vertebrates,invertebrates | 1 | Reoviridae,Orbivirus,Epizootic hemorrhagic disease virus | seg. 2 | AM745048 |
| Epizootic hemorrhagic disease virus (serotype 7/ strain CSIRO 775) | NC_013398 | vertebrates,invertebrates | 1 | Reoviridae,Orbivirus,Epizootic hemorrhagic disease virus | seg. 3 | AM745049 |
| Epizootic hemorrhagic disease virus (serotype 7/ strain CSIRO 775) | NC_013399 | vertebrates,invertebrates | 1 | Reoviridae,Orbivirus,Epizootic hemorrhagic disease virus | seg. 4 | AM745050 |
| Epizootic hemorrhagic disease virus (serotype 7/ strain CSIRO 775) | NC_013400 | vertebrates,invertebrates | 1 | Reoviridae,Orbivirus,Epizootic hemorrhagic disease virus | seg. 5 | AM745051 |
| Epizootic hemorrhagic disease virus (serotype 7/ strain CSIRO 775) | NC_013401 | vertebrates,invertebrates | 1 | Reoviridae,Orbivirus,Epizootic hemorrhagic disease virus | seg. 6 | AM745052 |
| Epizootic hemorrhagic disease virus (serotype 7/ strain CSIRO 775) | NC_013402 | vertebrates,invertebrates | 1 | Reoviridae,Orbivirus,Epizootic hemorrhagic disease virus | seg. 7 | AM745053 |
| Epizootic hemorrhagic disease virus (serotype 7/ strain CSIRO 775) | NC_013403 | vertebrates,invertebrates | 1 | Reoviridae,Orbivirus,Epizootic hemorrhagic disease virus | seg. 8 | AM745054 |
| Epizootic hemorrhagic disease virus (serotype 7/ strain CSIRO 775) | NC_013404 | vertebrates,invertebrates | 1 | Reoviridae,Orbivirus,Epizootic hemorrhagic disease virus | seg. 9 | AM745055 |
| Epizootic hemorrhagic disease virus (serotype 7/ strain CSIRO 775) | NC_013405 | vertebrates,invertebrates | 1 | Reoviridae,Orbivirus,Epizootic hemorrhagic disease virus | seg. 10 | AM745056 |
| Epizootic hemorrhagic disease virus (serotype 8/ strain CPR 3961A) | NC_013396 | vertebrates,invertebrates | 1 | Reoviridae,Orbivirus,Epizootic hemorrhagic disease virus | seg. 1 | AM745057 |
| Epizootic hemorrhagic disease virus (serotype 8/ strain CPR 3961A) | NC_013397 | vertebrates,invertebrates | 1 | Reoviridae,Orbivirus,Epizootic hemorrhagic disease virus | seg. 2 | AM745058 |
| Epizootic hemorrhagic disease virus (serotype 8/ strain CPR 3961A) | NC_013398 | vertebrates,invertebrates | 1 | Reoviridae,Orbivirus,Epizootic hemorrhagic disease virus | seg. 3 | AM745059 |
| Epizootic hemorrhagic disease virus (serotype 8/ strain CPR 3961A) | NC_013399 | vertebrates,invertebrates | 1 | Reoviridae,Orbivirus,Epizootic hemorrhagic disease virus | seg. 4 | AM745060 |
| Epizootic hemorrhagic disease virus (serotype 8/ strain CPR 3961A) | NC_013400 | vertebrates,invertebrates | 1 | Reoviridae,Orbivirus,Epizootic hemorrhagic disease virus | seg. 5 | AM745061 |
| Epizootic hemorrhagic disease virus (serotype 8/ strain CPR 3961A) | NC_013401 | vertebrates,invertebrates | 1 | Reoviridae,Orbivirus,Epizootic hemorrhagic disease virus | seg. 6 | AM745062 |
| Epizootic hemorrhagic disease virus (serotype 8/ strain CPR 3961A) | NC_013402 | vertebrates,invertebrates | 1 | Reoviridae,Orbivirus,Epizootic hemorrhagic disease virus | seg. 7 | AM745063 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Epizootic hemorrhagic disease virus (serotype 8/ strain CPR 3961A) | NC_013403 | vertebrates,invertebrates | 1 | Reoviridae,Orbivirus,Epizootic hemorrhagic disease virus | seg. 8 | AM745064 |
| Epizootic hemorrhagic disease virus (serotype 8/ strain CPR 3961A) | NC_013404 | vertebrates,invertebrates | 1 | Reoviridae,Orbivirus,Epizootic hemorrhagic disease virus | seg. 9 | AM745065 |
| Epizootic hemorrhagic disease virus (serotype 8/ strain CPR 3961A) | NC_013405 | vertebrates,invertebrates | 1 | Reoviridae,Orbivirus,Epizootic hemorrhagic disease virus | seg. 10 | AM745066 |
| Epizootic hemorrhagic disease virus 1 | NC_013398 | vertebrates,invertebrates | 1 | Reoviridae,Orbivirus,Epizootic hemorrhagic disease virus | seg. 3 | M76616 |
| Epizootic hemorrhagic disease virus 1 | NC_013401 | vertebrates,invertebrates | 1 | Reoviridae,Orbivirus,Epizootic hemorrhagic disease virus | seg. 6 | L27647 |
| Epizootic hemorrhagic disease virus 1 | NC_013402 | vertebrates,invertebrates | 6 | Reoviridae,Orbivirus,Epizootic hemorrhagic disease virus | seg. 7 | AY261511,AY261510,AY261509,AY261507,AY261508,AY261506 |
| Epizootic hemorrhagic disease virus 1 | NC_013403 | vertebrates,invertebrates | 1 | Reoviridae,Orbivirus,Epizootic hemorrhagic disease virus | seg. 8 | L31764 |
| Epizootic hemorrhagic disease virus 1 | NC_013405 | vertebrates,invertebrates disease virus | 1 | Reoviridae,Orbivirus,Epizootic hemorrhagic disease virus | seg. 10 | L29023 |
| Epizootic hemorrhagic disease virus 2 | NC_013397 | vertebrates,invertebrates | 11 | Reoviridae,Orbivirus,Epizootic hemorrhagic disease virus | seg. 2 | AB078624,L33824,L33821,L33825,AB078632,L33823,AB078620,L33818,AB078628,L33822,L33826 |
| Epizootic hemorrhagic disease virus 2 | NC_013398 | vertebrates,invertebrates | 5 | Reoviridae,Orbivirus,Epizootic hemorrhagic disease virus | seg. 3 | AB078629,L33820,L33819,AB078621,AB078625 |
| Epizootic hemorrhagic disease virus 2 | NC_013400 | vertebrates,invertebrates | 1 | Reoviridae,Orbivirus,Epizootic hemorrhagic disease virus | seg. 5 | AB078633 |
| Epizootic hemorrhagic disease virus 2 | NC_013401 | vertebrates,invertebrates | 5 | Reoviridae,Orbivirus,Epizootic hemorrhagic disease virus | seg. 6 | AB078626,L27648,M69085,AB078622,AB078630 |
| Epizootic hemorrhagic disease virus 2 | NC_013402 | vertebrates,invertebrates | 40 | Reoviridae,Orbivirus,Epizootic hemorrhagic disease virus | seg. 7 | AY261505,AY261492,AY261480,AY261149,8,AY261500,AY261496,AY261491,AY261486,AB078623,AY261489,AY261485,AY261490,AY261502,AY261494,AB078631,AY261475,AY261497,AY261487,AY261495,AY261476,AY261146,AY261504,AY261159,AY261503,AY261488,AY261482,AY261477,AY26 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Epizootic hemorrhagic disease virus 2 | | | | | | 1479,AY261471,AY261483,AY261473,AY261481,AY261478,AY261499,AY261470,AY261472,AB078627,AY261474,AY261493,AY261501,AY261484 |
| Epizootic hemorrhagic disease virus 2 | NC_013403 | vertebrates,invertebrates | 3 | Reoviridae,Orbivirus,Epizootic hemorrhagic disease virus | seg. 8 | M69091,AB084285,L31765 |
| Epizootic hemorrhagic disease virus 2 | NC_013405 | vertebrates,invertebrates | 1 | Reoviridae,Orbivirus,Epizootic hemorrhagic disease virus | seg. 10 | L29022 |
| Epizootic hemorrhagic disease virus 6 | NC_013398 | vertebrates,invertebrates | 1 | Reoviridae,Orbivirus,Epizootic hemorrhagic disease virus | seg. 3 | KC986825 |
| Epizootic hemorrhagic disease virus 6 | NC_013401 | vertebrates,invertebrates | 1 | Reoviridae,Orbivirus,Epizootic hemorrhagic disease virus | seg. 6 | KC986823 |
| Epizootic hemorrhagic disease virus 6 | NC_013402 | vertebrates,invertebrates | 1 | Reoviridae,Orbivirus,Epizootic hemorrhagic disease virus | seg. 7 | KC986824 |
| Fort Morgan virus | NC_013528 | vertebrates,invertebrates | 1 | Togaviridae,Alphavirus,Fort Morgan virus | — | GQ281603 |
| Getah virus | NC_006558 | vertebrates,invertebrates | 7 | Togaviridae,Alphavirus,Getah virus | — | EU01506,AY702913,EF631998,EU01506,AB859822,EU0150,EF631999 |
| Highlands J virus | NC_012561 | vertebrates,invertebrates | 3 | Togaviridae,Alphavirus,Highlands J virus | — | GU167952,GQ22778,FJ827631 |
| Ibaraki virus | NC_013396 | vertebrates,invertebrates | 1 | Reoviridae,Orbivirus,Epizootic hemorrhagic disease virus | seg. 1 | AB186040 |
| Midway virus | NC_012702 | vertebrates,invertebrates | 1 | Midway virus | — | FJ554525 |
| Mobuck virus | NC_022620 | vertebrates,invertebrates | 1 | Reoviridae,Orbivirus,Mobuck virus | segment 2 | KF296323 |
| Mobuck virus | NC_022621 | vertebrates,invertebrates | 1 | Reoviridae,Orbivirus,Mobuck virus | seg. segment 4 | KF296325 |
| Mobuck virus | NC_022622 | vertebrates,invertebrates | 1 | Reoviridae,Orbivirus,Mobuck virus | seg. n6 | KF296327 |
| Mobuck virus | NC_022623 | vertebrates,invertebrates | 1 | Reoviridae,Orbivirus,Mobuck virus | seg. segment 7 | KF296328 |
| Mobuck virus | NC_022624 | vertebrates,invertebrates | 1 | Reoviridae,Orbivirus,Mobuck virus | seg. segment 9 | KF296330 |
| Mobuck virus | NC_022625 | vertebrates,invertebrates | 1 | Reoviridae,Orbivirus,Mobuck virus | seg. 10 | KF296331 |
| Mobuck virus | NC_022626 | vertebrates,invertebrates | 1 | Reoviridae,Orbivirus,Mobuck virus | seg. segment 1 | KF296322 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Mobuck virus | NC_022627 | vertebrates,invertebrates | 1 | Reoviridae,Orbivirus,Mobuck virus | seg. segment n3 | KF296324 |
| Mobuck virus | NC_022628 | vertebrates,invertebrates | 1 | Reoviridae,Orbivirus,Mobuck virus | seg. segment n5 | KF296326 |
| Mobuck virus | NC_022629 | vertebrates,invertebrates | 1 | Reoviridae,Orbivirus,Mobuck virus | seg. segment n8 | KF296329 |
| Ndumu virus | NC_016959 | vertebrates,invertebrates | 1 | Togaviridae,Alphavirus,Ndumu virus | — | HM147989 |
| Nodamura virus | NC_002690 | vertebrates,invertebrates | 1 | Nodaviridae,Alphanodavirus,Nodamura virus | seg. RNA 1 | AF174533 |
| Nodamura virus | NC_002691 | vertebrates,invertebrates | 2 | Nodaviridae,Alphanodavirus,Nodamura virus | seg. RNA 2 | AF174534,X15961 |
| Nyamanini virus | NC_012703 | vertebrates,invertebrates | 1 | Nyamanini virus | — | FJ554526 |
| Ockelbo virus | NC_001547 | vertebrates,invertebrates | 1 | Togaviridae,Alphavirus,Sindbis virus | — | M69205 |
| Palyam virus | NC_005986 | vertebrates,invertebrates | 1 | Reoviridae,Orbivirus,Palyam virus | seg. 2 | AB014725 |
| Palyam virus | NC_005987 | vertebrates,invertebrates | 1 | Reoviridae,Orbivirus,Palyam virus | seg. 6 | AB014726 |
| Palyam virus | NC_005988 | vertebrates,invertebrates | 1 | Reoviridae,Orbivirus,Palyam virus | seg. 7 | AB014727 |
| Palyam virus | NC_005989 | vertebrates,invertebrates | 1 | Reoviridae,Orbivirus,Palyam virus | seg. 3 | AB014728 |
| Palyam virus | NC_005990 | vertebrates,invertebrates | 1 | Reoviridae,Orbivirus,Palyam virus | seg. 1 | AB018086 |
| Palyam virus | NC_005991 | vertebrates,invertebrates | 1 | Reoviridae,Orbivirus,Palyam virus | seg. 4 | AB018087 |
| Palyam virus | NC_005992 | vertebrates,invertebrates | 1 | Reoviridae,Orbivirus,Palyam virus | seg. 9 | AB018088 |
| Palyam virus | NC_005993 | vertebrates,invertebrates | 1 | Reoviridae,Orbivirus,Palyam virus | seg. 5 | AB018089 |
| Palyam virus | NC_005994 | vertebrates,invertebrates | 1 | Reoviridae,Orbivirus,Palyam virus | seg. 8 | AB018090 |
| Palyam virus | NC_005995 | vertebrates,invertebrates | 1 | Reoviridae,Orbivirus,Palyam virus | seg. 10 | AB018091 |
| Peruvian horse sickness virus | NC_007748 | vertebrates,invertebrates | 1 | Reoviridae,Orbivirus,Peruvian horse sickness virus | seg. 1 | DQ248057 |
| Peruvian horse sickness virus | NC_007749 | vertebrates,invertebrates | 1 | Reoviridae,Orbivirus,Peruvian horse sickness virus | seg. 2 | DQ248058 |
| Peruvian horse sickness virus | NC_007750 | vertebrates,invertebrates | 1 | Reoviridae,Orbivirus,Peruvian horse sickness virus | seg. 3 | DQ248059 |
| Peruvian horse sickness virus | NC_007751 | vertebrates,invertebrates | 1 | Reoviridae,Orbivirus,Peruvian horse sickness virus | seg. 4 | DQ248060 |
| Peruvian horse sickness virus | NC_007752 | vertebrates,invertebrates | 1 | Reoviridae,Orbivirus,Peruvian horse sickness virus | seg. 6 | DQ248061 |
| Peruvian horse sickness virus | NC_007753 | vertebrates,invertebrates | 2 | Reoviridae,Orbivirus,Peruvian horse sickness virus | seg. 9 | DQ248062,FJ225398 |
| Peruvian horse sickness virus | NC_007754 | vertebrates,invertebrates | 1 | Reoviridae,Orbivirus,Peruvian horse sickness virus | seg. 8 | DQ248063 |
| Peruvian horse sickness virus | NC_007755 | vertebrates,invertebrates | 1 | Reoviridae,Orbivirus,Peruvian horse sickness virus | seg. 5 | DQ248064 |
| Peruvian horse sickness virus | NC_007756 | vertebrates,invertebrates | 1 | Reoviridae,Orbivirus,Peruvian horse sickness virus | seg. 7 | DQ248065 |
| Peruvian horse sickness virus | NC_007757 | vertebrates,invertebrates | 2 | Reoviridae,Orbivirus,Peruvian horse sickness virus | seg. 10 | FJ225399,DQ248066 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Salmon pancreas disease virus | NC_003930, NC_003433 | vertebrates,invertebrates | 1 | Togaviridae,Alphavirus,Salmon pancreas disease virus | — | AJ316244 |
| Salmonid alphavirus subtype 3 | NC_003930, NC_003433 | vertebrates,invertebrates | 9 | Togaviridae,Alphavirus,Salmon pancreas disease virus | — | KC122926,KC122919,KC122923,KC122918,KC122920,KC122925,KC122922,KC122924,KC122921 |
| Semliki forest virus | NC_003215 | vertebrates,invertebrates | 7 | Togaviridae,Alphavirus,Semliki forest virus | — | DQ189084,XQ4129,DQ189086,Z48163,DQ189082,EU350586,AY112987 |
| Sindbis virus | NC_001547 | vertebrates,invertebrates | 14 | Togaviridae,Alphavirus,Sindbis virus | — | AF429428,KF737350,JQ771793,JQ771797,JQ771798,JQ771795,JX570540,GU361116,JQ2363,GU361118,AF103728,JQ771794,J0771799,JQ771796 |
| Sindbis-like virus | NC_001547 | vertebrates,invertebrates | 2 | Togaviridae,Alphavirus,Sindbis virus | — | U38304,U38305 |
| Sindbis-like virus YN87448 | NC_001547 | vertebrates,invertebrates | 1 | Togaviridae,Alphavirus,Sindbis virus | — | AF103734 |
| Southern elephant seal virus | NC_016960 | vertebrates,invertebrates | 1 | Togaviridae,Alphavirus,Southern elephant seal virus | — | HM147990 |
| St Croix River virus | NC_005997 | vertebrates,invertebrates | 1 | Reoviridae,Orbivirus,St Croix River virus | seg. 1 | AF133431 |
| St Croix River virus | NC_005998 | vertebrates,invertebrates | 1 | Reoviridae,Orbivirus,St Croix River virus | seg. 2 | AF133432 |
| St Croix River virus | NC_005999 | vertebrates,invertebrates | 1 | Reoviridae,Orbivirus,St Croix River virus | seg. 3 | AF145400 |
| St Croix River virus | NC_006000 | vertebrates,invertebrates | 1 | Reoviridae,Orbivirus,St Croix River virus | seg. 4 | AF145401 |
| St Croix River virus | NC_006001 | vertebrates,invertebrates | 1 | Reoviridae,Orbivirus,St Croix River virus | seg. 5 | AF145402 |
| St Croix River virus | NC_006002 | vertebrates,invertebrates | 1 | Reoviridae,Orbivirus,St Croix River virus | seg. 6 | AF145403 |
| St Croix River virus | NC_006003 | vertebrates,invertebrates | 1 | Reoviridae,Orbivirus,St Croix River virus | seg. 7 | AF145404 |
| St Croix River virus | NC_006004 | vertebrates,invertebrates | 1 | Reoviridae,Orbivirus,St Croix River virus | seg. 8 | AF145405 |
| St Croix River virus | NC_006005 | vertebrates,invertebrates | 1 | Reoviridae,Orbivirus,St Croix River virus | seg. 9 | AF145406 |
| St Croix River virus | NC_006006 | vertebrates,invertebrates | 1 | Reoviridae,Orbivirus,St Croix River virus | seg. 10 | AF145407 |
| Stretch Lagoon orbivirus | NC_012754 | vertebrates,invertebrates | 1 | Reoviridae,Orbivirus,Stretch Lagoon orbivirus | seg. 1 | EU718676 |
| Stretch Lagoon orbivirus | NC_012755 | vertebrates,invertebrates | 1 | Reoviridae,Orbivirus,Stretch Lagoon orbivirus | seg. 2 | EU718677 |
| Venezuelan equine encephalitis virus | NC_001449 | vertebrates,invertebrates | 132 | Togaviridae,Alphavirus,Venezuelan equine encephalitis virus | — | U55362,KC344436,U55360,KC344447,AF075255,AF375051,KC344486,L01442,KC344510,KC344519,KC344486,U55345,JQ4332,KC344475,AF075251,KC344501,KC344471,AF069903,KC344491,KC344490,KC344430,U55350,KC344455,KC344431,K |

TABLE 10-continued

VivoCap-1.0 Taxonomy

| Taxonomy | Rep.Acc.ID | Host | # GN's | Lineage | Seg. Count | GN.Acc.IDs |
|---|---|---|---|---|---|---|
| | | | | | | C344469,KC344478, KC344446,KC344509 ,KC344482,KC344446 2,AF075254,AF10056 6,AF00472,KC3445 26,KC344438,KC344 429,KC344498,KC34 4458,AF075259,KC3 44433,KC344450,KC 344443,KC344522,K C344439,KC344485, KC344483,U55347,K C344467,AF075252, KC344466,KC344441 ,KC344484,KC34452 4,KC344503,KC3444 93,AY823299,KC344 495,KC344465,KC34 4474,AF004458,KC3 44513,KC344525,KC 344461,KC344442,K C344473,KC344440, KC344487,AF075257 ,AF075258,KC34450 5,KC344437,KC3445 27,AF075256,KC344 489,KC344457,KC34 4445,KC344502,KC3 44460,KC344518,KC 344528,KC344453,K C344515,KC344506, AY986475,KC344444 ,KC344468,KC34447 9,KC344464,KC3444 72,L04653,KC344463 ,U55342,AY741139,D 0390224,KC344435, AF075253,KC344432 ,KC344499,KC34445 1,L01443,KC344452, KC344496,KC344481 ,KC344508,KC34445 6,KC344523,KC3444 88,KC345517,KC344 511,KC344494,KC34 4448,KC344514,KC3 44507,KC344480,AY 973944,KC344504,K |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Wallal virus | NC_022553 | vertebrates,invertebrates | 1 | Reoviridae,Orbivirus,Wallal virus | seg. 1 | C344521,KC344470, KC344492,KC344454 ,KC344476,KC344450 ,KC344512,KC3445 20,AF004459,KC344 459,KC344516,KC34 4497,KC344477,KC3 44434,KF985959,L00 930 |
| Wallal virus | NC_022554 | vertebrates,invertebrates | 1 | Reoviridae,Orbivirus,Wallal virus | seg. 2 | KF234259 |
| Wallal virus | NC_022555 | vertebrates,invertebrates | 1 | Reoviridae,Orbivirus,Wallal virus | segment 2 | KF234260 |
| Wallal virus | NC_022556 | vertebrates,invertebrates | 1 | Reoviridae,Orbivirus,Wallal virus | seg. 3 | KF234261 |
| Wallal virus | NC_022557 | vertebrates,invertebrates | 1 | Reoviridae,Orbivirus,Wallal virus | seg. 5 | KF234263 |
| Wallal virus | NC_022558 | vertebrates,invertebrates | 1 | Reoviridae,Orbivirus,Wallal virus | segment 5 | KF234265 |
| Wallal virus | NC_022559 | vertebrates,invertebrates | 1 | Reoviridae,Orbivirus,Wallal virus | seg. 7 | KF234267 |
| Wallal virus | NC_022560 | vertebrates,invertebrates | 1 | Reoviridae,Orbivirus,Wallal virus | segment 9 | KF234268 |
| Wallal virus | NC_022561 | vertebrates,invertebrates | 1 | Reoviridae,Orbivirus,Wallal virus | seg. 10 | KF234262 |
| Wallal virus | NC_022562 | vertebrates,invertebrates | 1 | Reoviridae,Orbivirus,Wallal virus | seg. 4 | KF234264 |
| Wallal virus | | vertebrates,invertebrates | 1 | Reoviridae,Orbivirus,Wallal virus | seg. 6 | KF234266 |
| Wallal virus | | vertebrates,invertebrates | 1 | Reoviridae,Orbivirus,Wallal virus | segment 8 | |
| Western equine encephalomyelitis virus | NC_003908 | vertebrates,invertebrates | 9 | Togaviridae,Alphavirus,Western equine encephalitis virus | — | AF214040,GQ287640 ,GQ287641,GQ28764 5,GQ287643,GQ2876 44,GQ287642,GQ287 647,GQ287646 |
| Whataroa virus | NC_016961 | vertebrates,invertebrates | 1 | Togaviridae,Alphavirus,Whataroa virus | — | HM147993 |
| Yunnan orbivirus | NC_007656 | vertebrates,invertebrates | 1 | Reoviridae,Orbivirus,Yunnan orbivirus | seg. 1 | AY701509 |
| Yunnan orbivirus | NC_007657 | vertebrates,invertebrates | 1 | Reoviridae,Orbivirus,Yunnan orbivirus | seg. 2 | AY701510 |
| Yunnan orbivirus | NC_007658 | vertebrates,invertebrates | 1 | Reoviridae,Orbivirus,Yunnan orbivirus | seg. 3 | AY701511 |
| Yunnan orbivirus | NC_007659 | vertebrates,invertebrates | 1 | Reoviridae,Orbivirus,Yunnan orbivirus | seg. 4 | AY701512 |
| Yunnan orbivirus | NC_007660 | vertebrates,invertebrates | 1 | Reoviridae,Orbivirus,Yunnan orbivirus | seg. 5 | AY701513 |
| Yunnan orbivirus | NC_007661 | vertebrates,invertebrates | 1 | Reoviridae,Orbivirus,Yunnan orbivirus | seg. 6 | AY701514 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Yunnan orbivirus | NC_007662 | vertebrates,invertebrates | 1 | Reoviridae,Orbivirus,Yunnan orbivirus | seg. 7 | AY701515 |
| Yunnan orbivirus | NC_007663 | vertebrates,invertebrates | 1 | Reoviridae,Orbivirus,Yunnan orbivirus | seg. 8 | AY701516 |
| Yunnan orbivirus | NC_007664 | vertebrates,invertebrates | 2 | Reoviridae,Orbivirus,Yunnan orbivirus | seg. 9 | AY701517,FJ225402 |
| Yunnan orbivirus | NC_007665 | vertebrates,invertebrates | 1 | Reoviridae,Orbivirus,Yunnan orbivirus | seg. 10 | AY701518 |
| Aedes flavivirus | NC_012932 | vertebrates,invertebrates, human | 2 | Flaviviridae,Flavivirus,Aedes flavivirus | — | KC181923,AB488408 |
| Aguacate virus | NC_015450 | vertebrates,invertebrates, human | 1 | Bunyaviridae,Phlebovirus,Aguacate virus | seg. M | HM566137 |
| Aguacate virus | NC_015451 | vertebrates,invertebrates, human | 1 | Bunyaviridae,Phlebovirus,Aguacate virus | seg. L | HM566138 |
| Aguacate virus | NC_015452 | vertebrates,invertebrates, human | 1 | Bunyaviridae,Phlebovirus,Aguacate virus | seg. S | HM566139 |
| Aino virus | NC_018459 | vertebrates,invertebrates, human | 1 | Bunyaviridae,Orthobunyavirus,Shuni virus | seg. M | HE795088 |
| Aino virus | NC_018460 | vertebrates,invertebrates, human | 1 | Bunyaviridae,Orthobunyavirus,Shuni virus | seg. S | HE795089 |
| Aino virus | NC_018465 | vertebrates,invertebrates, human | 1 | Bunyaviridae,Orthobunyavirus,Shuni virus | seg. L | HE795087 |
| Akabane virus | NC_009894 | vertebrates,invertebrates, human | 2 | Bunyaviridae,Orthobunyavirus,Akabane virus | seg. L | JQ308779,AB190458 |
| Akabane virus | NC_009895 | vertebrates,invertebrates, human | 42 | Bunyaviridae,Orthobunyavirus,Akabane virus | seg. M | AB297833,AB289324,AB297822,AB297837,AB297831,AB297819,AB297844,AB297839,AB426282,AB297834,AB297827,AB297821,AB297841,AB297838,AB297824,AB297842,AB297823,AB297825,AB297845,AB297829,AB297785,AB436954,AB297835,AB297828,AB297850,AB297826,AB297832,AB297840,AB373233,AB297847,AB297843,AB289323,AB426281,AB100604,AB297820,AB297846,AB297836,AB297781,AB297849,AB2893,AB297848,AB426822,AB297830 |
| Akabane virus | NC_009896 | vertebrates,invertebrates, human | 21 | Bunyaviridae,Orthobunyavirus,Akabane virus | seg. S | AB289319,AB426275,AB426277,AB426274,AB289320,AB00084,AB426278,AB426251 |

TABLE 10-continued

VitoCap-1.0 Taxonomy

| Taxonomy | Rep.Acc.ID | Host | # GN's | Lineage | Seg. Count | GN.Acc.IDs |
|---|---|---|---|---|---|---|
| | | | | | | 272,AF034939,AB373232,AB373234,AB426279,AB426276,AF529883,AB426273,AB426271,AB426280,AF034942,AF034941,AF034940,AB289321 |
| Alenquer virus | NC_015373 | vertebrates,invertebrates,human | 1 | Bunyaviridae,Phlebovirus,Candiru virus | seg. M | HM119402 |
| Alenquer virus | NC_015374 | vertebrates,invertebrates,human | 1 | Bunyaviridae,Phlebovirus,Candiru virus | seg. L | HM119401 |
| Alenquer virus | NC_015375 | vertebrates,invertebrates,human | 1 | Bunyaviridae,Phlebovirus,Candiru virus | seg. S | HM119403 |
| Alfuy virus | NC_000943 | vertebrates,invertebrates,human | 1 | Flaviviridae,Flavivirus,Murray Valley encephalitis virus | — | AY898809 |
| Alkhurma hemorrhagic fever virus | NC_004355 | vertebrates,invertebrates,human | 19 | Flaviviridae,Flavivirus,Kyasanur forest disease virus | — | JF416955,JF416950,JF416963,JF416956,JX271893,JF416954,JF416951,JN860200,JF416961,JF416964,JF416957,JF416967,JF416949,JF416966,JF416953,JF416965,JX271892,JF416962,JF416952 |
| Alkhurma hemorrhagic fever virus | NC_004355 | vertebrates,invertebrates,human | 1 | Flaviviridae,Flavivirus,Kyasanur forest disease virus | — | AF331718 |
| Alphavirus M1 | NC_001544 | vertebrates,invertebrates,human | 1 | Togaviridae,Alphavirus,Ross River virus | — | EF011023 |
| Apoi virus | NC_003676 | vertebrates,invertebrates,human | 1 | Flaviviridae,Flavivirus,Apoi virus | — | AF160193 |
| Ariquemes virus | NC_015373 | vertebrates,invertebrates,human | 1 | Bunyaviridae,Phlebovirus,Candiru virus | seg. M | HM119405 |
| Ariquemes virus | NC_015374 | vertebrates,invertebrates,human | 1 | Bunyaviridae,Phlebovirus,Candiru virus | seg. L | HM119404 |
| Ariquemes virus | NC_015375 | vertebrates,invertebrates,human | 1 | Bunyaviridae,Phlebovirus,Candiru virus | seg. S | HM119406 |
| Armero virus | NC_015450 | vertebrates,invertebrates,human | 1 | Bunyaviridae,Phlebovirus,Aguacate virus | seg. M | HQ661806 |
| Armero virus | NC_015451 | vertebrates,invertebrates,human | 2 5 | Bunyaviridae,Phlebovirus,Aguacate virus | seg. L | HM566140,HQ66180 |
| Armero virus | NC_015452 | vertebrates,invertebrates,human | 2 7 | Bunyaviridae,Phlebovirus,Aguacate virus | seg. S | HM566142,HQ66180 |
| Aroa virus | NC_009026 | vertebrates,invertebrates,human | 1 | Flaviviridae,Flavivirus,Aroa virus | — | AY632536 |
| Bagaza virus | NC_012534 | vertebrates,invertebrates,human | 4 | Flaviviridae,Flavivirus,Bagaza virus | — | AY632545,EU684972,HQ644143,HQ644144 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Banna virus | NC_004211 | vertebrates,invertebrates, human | 2 | Reoviridae,Seadornavirus,Banna virus | seg. 1 | AF133430,AF168005 |
| Banna virus | NC_004217 | vertebrates,invertebrates, human | 3 | Reoviridae,Seadornavirus,Banna virus | seg. 2 | AF134528,AF134526, AF134514 |
| Banna virus | NC_004218 | vertebrates,invertebrates, human | 2 | Reoviridae,Seadornavirus,Banna virus | seg. 3 | AF134515,AY549307 |
| Banna virus | NC_004219 | vertebrates,invertebrates, human | 3 | Reoviridae,Seadornavirus,Banna virus | seg. 4 | EU265698,AY549308 ,AF134516 |
| Banna virus | NC_004220 | vertebrates,invertebrates, human | 2 | Reoviridae,Seadornavirus,Banna virus | seg. 5 | AF134517,AY549309 |
| Banna virus 5 | NC_004221 | vertebrates,invertebrates, human | 1 | Reoviridae,Seadornavirus,Banna virus | seg. 6 | AF134521,AF168006, |
| AF134518 | | | | | | AF134527,AF134524, |
| Batai virus | NC_001926 | vertebrates,invertebrates, human | 1 | Bunyaviridae,Orthobunyavirus,Bunyamwera virus | seg. M | DQ436460 |
| Batai virus | NC_001927 | vertebrates,invertebrates, human | 1 | Bunyaviridae,Orthobunyavirus,Bunyamwera virus | seg. S | X73464 |
| Birao virus | NC_001927 | vertebrates,invertebrates, human | 1 | Bunyaviridae,Orthobunyavirus,Bunyamwera virus | seg. S | AM711131 |
| Bozo virus | NC_001927 | vertebrates,invertebrates, human | 1 | Bunyaviridae,Orthobunyavirus,Bunyamwera virus | seg. S | AM711132 |
| Brazoran virus | NC_022037 | vertebrates,invertebrates, human | 1 | Bunyaviridae,Orthobunyavirus,Brazoran virus | seg. S | KC854416 |
| Brazoran virus | NC_022038 | vertebrates,invertebrates, human | 1 | Bunyaviridae,Orthobunyavirus,Brazoran virus | seg. M | KC854417 |
| Brazoran virus | NC_022039 | vertebrates,invertebrates, human | 1 | Bunyaviridae,Orthobunyavirus,Brazoran virus | seg. L | KC854418 |
| Bunyamwera virus | NC_001925 | vertebrates,invertebrates, human | 1 | Bunyaviridae,Orthobunyavirus,Bunyamwera virus | seg. L | X14383 |
| Bunyamwera virus | NC_001926 | vertebrates,invertebrates, human | 1 | Bunyaviridae,Orthobunyavirus,Bunyamwera virus | seg. M | M11852 |
| Bunyamwera virus | NC_001927 | vertebrates,invertebrates, human | 4 | Bunyaviridae,Orthobunyavirus,Bunyamwera virus | seg. S | DQ0353,AM711130,A M709778,AF325122 |
| Cache Valley virus | NC_001926 | vertebrates,invertebrates, human | 2 | Bunyaviridae,Orthobunyavirus,Bunyamwera virus | seg. M | AF082739,AF082576 |
| Cache Valley virus | NC_001927 | vertebrates,invertebrates, human | 1 | Bunyaviridae,Orthobunyavirus,Bunyamwera virus | seg. S | X73465 |
| California encephalitis virus | NC_004109 | vertebrates,invertebrates, human | 1 | Bunyaviridae,Orthobunyavirus,California encephalitis virus | seg. M | AF123483 |
| California encephalitis virus | NC_004110 | vertebrates,invertebrates, human | 2 | Bunyaviridae,Orthobunyavirus,California encephalitis virus | seg. S | U12797,U12800 |
| Candiru virus | NC_015373 | vertebrates,invertebrates, human | 1 | Bunyaviridae,Phlebovirus,Candiru virus | seg. M | HM119408 |
| Candiru virus | NC_015374 | vertebrates,invertebrates, human | 1 | Bunyaviridae,Phlebovirus,Candiru virus | seg. L | HM119407 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Candiru virus | NC_015375 | vertebrates,invertebrates, human | 1 | Bunyaviridae,Phlebovirus,Candiru virus | seg. S | HM119409 |
| Cell fusing agent virus | NC_001564 | vertebrates,invertebrates, human | 1 | Flaviviridae,Flavivirus,Cell fusing agent virus | — | M91671 |
| Chaoyang virus | NC_017086 | vertebrates,invertebrates, human | 2 | Flaviviridae,Flavivirus,Chaoyang virus | — | JQ068102,JQ308185 |
| Chatanga virus | NC_004108 | vertebrates,invertebrates, human | 1 | Bunyaviridae,Orthobunyavirus,California encephalitis virus | seg. L | EU616903 |
| Chatanga virus | NC_004109 | vertebrates,invertebrates, human | 1 | Bunyaviridae,Orthobunyavirus,California encephalitis virus | seg. M | EU621834 |
| Chikungunya virus | NC_004162 | vertebrates,invertebrates, human | 161 | Togaviridae,Alphavirus,Chikungunya virus | — | GQ428211,FR717336,HM045789,JQ06762 4,FJ445510,FJ51365 4,GU301781,GU1993 51,FN295485,HM045 819,FJ445463,HM04 5787,HM045796,JQ8 61256,AM258994,FJ8 07899,HM045812,HM 045814,HE806461,J 0861253,HQ456253, HM045803,EF027137 ,EF027139,HM045479 0,FJ513637,AY72673 2,AM258991,EU7037 60,HM045820,GU301 780,JF274082,HM04 5816,FJ445431,HQ84 6357,HM045802,EU5 64335,GU301779,HM 045821,GU199350,H 0846356,FJQ00066,F J513632,FJ445428,F JQ00069,KC862329,J 0861260,FJ445433,F J513629,HM045811, HM045807,GU01352 9,FR717337,HM0458 13,HM045797,AM258 995,GU199352,FJ513 635,AM258992,HM04 5798,FJ513645,HQ84 6358,FJ445427,DQ44 3544,EF027136,EU7 03759,HQ456251,AF 369024,FJ513628,EF 452493,FJ445432,FN 295483,FJQ00062,GU |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 18961,HM045795,EU703761,HQ846359,FJQ00067,GQ428214,HQ456252,GU199353,FJQ00064,HM045810,HM045822,HM045823,FJ513673,FN295487,JQ861254,EF210157,HM045791,JQ861257,FJ445443,EF027141,JN558836,HMO45805,FJQ00063,HM045806,HM045786,EF027135,GQ428215,HM045817,HM045815,FN295484,FJ80789 8,EU372006,GQ428213,EF452494,FJ513675,HM045818,JN558835,HM045801,GQ428212,GQ905863,HMO45784,AF490259,EFO27134,HQ456255,GU013528,FJ959103,JQ861258,FJ513679,HM045793,EU703762,HM045785,FJQ00068,FJQ00065,FJ445430,HM045804,FJ445426,HM045809,AM258993,FJ807896,HM04573,FJ807896,HM045799,HM045808,L37661,FJ445502,FJ445484,FJ807897,JN558834,AB455493,EF012359,EU244823,HM045800,FJ445511,HQ456254,HM045792,FJ513657,GQ428210,HMO45788,GU908223,FJ445445,EF027140,KF318729,AM258990,EU564334,GU013530,JX088705,HM045794,EF027138,AB455494,J0861255 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Chikungunya virus Wuerzburg | NC_004162 | vertebrates,invertebrates,human | 1 | Togaviridae,Alphavirus,Chikungunya virus | | EU037962 |
| Chize virus | NC_005214 | vertebrates,invertebrates,human | 1 | Bunyaviridae,Phlebovirus,Uukuniemi virus | seg. L | JF838324 |
| Chize virus | NC_005220 | vertebrates,invertebrates,human | 1 | Bunyaviridae,Phlebovirus,Uukuniemi virus | seg. M | JF838325 |
| Chize virus | NC_005221 | vertebrates,invertebrates,human | 1 | Bunyaviridae,Phlebovirus,Uukuniemi virus | seg. S | JF838326 |
| Colorado tick fever virus | NC_004180 | vertebrates,invertebrates,human | 1 | Reoviridae,Coltivirus,Colorado tick fever virus | seg. 9 | AF000720 |
| Colorado tick fever virus | NC_004181 | vertebrates,invertebrates,human | 1 | Reoviridae,Coltivirus,Colorado tick fever virus | seg. 1 | AF133428 |
| Colorado tick fever virus | NC_004182 | vertebrates,invertebrates,human | 1 | Reoviridae,Coltivirus,Colorado tick fever virus | seg. 2 | AF139758 |
| Colorado tick fever virus | NC_004183 | vertebrates,invertebrates,human | 1 | Reoviridae,Coltivirus,Colorado tick fever virus | seg. 3 | AF139759 |
| Colorado tick fever virus | NC_004184 | vertebrates,invertebrates,human | 1 | Reoviridae,Coltivirus,Colorado tick fever virus | seg. 4 | AF139760 |
| Colorado tick fever virus | NC_004185 | vertebrates,invertebrates,human | 1 | Reoviridae,Coltivirus,Colorado tick fever virus | seg. 5 | AF139761 |
| Colorado tick fever virus | NC_004186 | vertebrates,invertebrates,human | 1 | Reoviridae,Coltivirus,Colorado tick fever virus | seg. 6 | AF139762 |
| Colorado tick fever virus | NC_004187 | vertebrates,invertebrates,human | 1 | Reoviridae,Coltivirus,Colorado tick fever virus | seg. 7 | AF139763 |
| Colorado tick fever virus | NC_004188 | vertebrates,invertebrates,human | 1 | Reoviridae,Coltivirus,Colorado tick fever virus | seg. 8 | AF139764 |
| Colorado tick fever virus | NC_004189 | vertebrates,invertebrates,human | 1 | Reoviridae,Coltivirus,Colorado tick fever virus | seg. 10 | AF139765 |
| Colorado tick fever virus | NC_004190 | vertebrates,invertebrates,human | 1 | Reoviridae,Coltivirus,Colorado tick fever virus | seg. 12 | U53227 |
| Colorado tick fever virus | NC_004191 | vertebrates,invertebrates,human | 1 | Reoviridae,Coltivirus,Colorado tick fever virus | seg. 11 | U72694 |
| Crimean-Congo Hemorrhagic Fever virus strain China | NC_005302 | vertebrates,invertebrates,human | 4 | Bunyaviridae,Nairovirus,Crimean-Congo hemorrhagic fever virus | seg. S | AF358784,AF354296,AF362080,AY029157 |
| Crimean-Congo hemorrhagic fever virus | NC_005300 | vertebrates,invertebrates,human | 50 | Bunyaviridae,Nairovirus,Crimean-Congo hemorrhagic fever virus | seg. M | DQ211634,DQ211637,DQ206448,HQ378185,HQ378187,AB069675,AF350448,AB069672,DQ094832,AB069670,JN572085,AF469769,DQ157174,DQ211625,AY900145,AJ538199,AB069673,DQ211631,AY900144,AB069671,DQ211630,AB069669,DQ157175,AY900143,AY22347 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 6,DQ211635,AY9001 41,DQ211632,AF467 768,AF350449,AY900 142,DQ21 1626,DQ44 6216,JN572086,AB06 9674,DQ211627,EU0 37902,DQ211628,JN 572084,AJ538197,JN 572083,DQ21 1633,U 39455,AY675511,AY 179962,HQ378184,A Y179961,DQ211636, DQ446215,DQ211162 9 |
| Crimean-Congo hemorrhagic fever virus | NC

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Crimean-Congo hemorrhagic fever virus strain BA88166 | | | | | | 58,AF415236,DQ TABLE 10-continued VictoCap-1.0 Taxonomy

| Taxonomy | Rep.Acc.ID | Host | # GN's | Lineage | Seg. Count | GN.Acc.IDs |
|---|---|---|---|---|---|---|
| | | | | | | FJ410274,GU131834, GQ868505,GQ199800, FJ432746,FJ410206, FJ410213,EU482789, GU131695,GU131839, GU131820,FJQ24447, FJ639683,FJQ24439, GQ199849 , FJ850099, FJ898408, GU131716, GU131756,JQ915077, GU131926,DQ672557, GU131749,JQ045664, GQ199772,FJ410201, FJ898418, JQ045642, FJ461340,FJ432727, HM181953,FJ639806, JQ045658,GU131835, FJ882531 ,AY732480, KJ189303, FJ898420, KF921911 ,JQ048541 , FJ850114,GQ199823, HM181949 ,AY732482, JN819417,AY145122, EU482615,GU131863, EU081248,FJ639693, FJ687433, FJ882533, FJ882557,JQ045650, FJ410204,EU482529, AV732476,FJ882558, FJ410179,GQ199797 , FJ410267,GU131770 , EF025110,FJ410194 , HQ891315,HM1819936, JQ045628,FJ37329 7,FJ639812,EU66039 7,GQ868539,EU66604 18,GQ868633,FJ639 685,EU596501,FJ461 308,JF937606,FJ205 874,AB195673,EU08 1241,AB608787,EU0 81276,KJ189354,FJ4 10181,KJ189336,JN6 97058,GQ199840,JQ 045631,EF457905,AF 514889,DQ285558,G 0199806,FJ882579,F J882543,GQ868520, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | EU081251,GU131893,EU482795,EU081257,GU131751,FJ410236,GQ199814,GQ868612,EU677161,EU677152,GU131681,KJ189321,GU131718,FJ850071,EU081250,GU131971,EU677160,GU131779,HM63185O,EU482480,GQ199788,FJQ24455,FJQ24472,FJ432737,HM181945,EU081263,GU131685,EU482534,FJQ24434,KF184975,FJ88255,FJ461324,EU48281O,HM181965,EU081228,FJ906963,GU131379,FJ384655,GQ199832,EU482478,GU131792,JF937598,KJ189325,FJ176780,FJ410254,FJ410214,GQ199785,GU131742,FJ182003,HQ332177,GU131748,FJ898433,FJ850073,FJ410209,EU482804,GU131895,D0672560,GQ199853,GU131773,FJ810419,FJ882528,FJ205881,GQ199815,FJ432719,JN205310,AB189120,GU131782,FJQ244336,GQ868632,FJ41021,6,GU131713,GU131958,GU131734,FJ89842,8,FJ410225,HG3164,82,FJ410180,KJ189368,GQ868537,HM181937,FJ469908,EU660419,KJ189302,FJQ24431,EU482527,FJ410248,FJ410175,FJ882522,FJ547088,EU081274,GU131964,EU482616,FJ410187,JN63 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 8341,EU482711,FJ410207,GU131833,EU677155,GQ868506,GQ199808,EU081267,FJ410238,KJ189342,EU677164,FJ898384,KJ189357,EU482528,GU131706,KJ189335,FJ410220,GU131831, EU081240,JQ045656 ,FJ882555,FJQ24425, FJ882536,GU056033, GU131890,FJ182024, JF937645,FJ882524, EU081232,JQ045666 ,HQ624983,GU131178 8,GU131762,EU4827 14,FJ461317,FJ8825 49,GU131961,GU131 714,HM469968,EU67 7170,EU482801,GU1 31772,GU131760,DQ 285562,GU131694,A F311956,AY726552,F J410230,FJ850103,J 0287662,GQ199802, JF937597,EU596503, JF937603,FJ182036, FJ461307,HQ332182, GU131682,EU482493 ,FJ882518,HM18196 8,FJ205875,AY71347 3,GU131811,HM1819 55,FIQ24423,AY7324 79,FJ850090,FJ8984 31,FJ410253,EU6771 39,FJ410276,EU0812 49,GU131755,GU131 746,GQ868529,FJ88 2529,JQ915076,FJ88 2521,GU131704,FJ63 9677,AB608788,JF93 7612,GQ199851,FJ4 10182,FJ373305,FJ8 50102,DQ672562,FJO 24435,EU677174,GU 131806,EF122231,E U482536,HM181966, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | FJ410245,JF937651,AY732481,GU131740,KJ189334,FJ205882,GU131744,AF350498,KJ189341,EU482797,GQ199833,GQ199811,DQ672558,FJ410264,FJ882554,JQ04565,FJ898398,FJ39038,JF937618,KJ18930,EU677150,GQ8685,FJ410240,FJQ244,FJ882559,GQ868,GQ868610,FJ410235,EU677176,EU482790,GU131699,EU482824,JQ045662,AF514883,FJ882538,HM181944,GQ199786,GQ199828,GU131957,EU596502,GQ8686,JN819423,FJ8983,FJ432744,FJ4613,KJ189322,GQ199839,FJ182022,GQ199812,AY722803,FJO24444,GU131697,FJ898383,FJ182034,GU056032,HM181947,EU482812,GQ868561,FJ639673,FJ410231,GU131790,AF298808,HG316481,FJ898382,GQ868607,EU48248,FJ639687,EU48279,FJ547068,HQ33218,FJ410289,GU131681,FJ639691,GU131960,JF937602,AF51311,JN819415,GU131766,JQ675358,FJ4327,EU482591,AB178040,FJ898416,GU131803,FJ461327,FJ410239,FJ898430,KF955446,FJ639821,KJ189367,JQ045648,FJ873810,EU081246,GU13 |

TABLE 10-continued

| Taxonomy | ViroCap-1.0 Taxonomy | | | | |
|---|---|---|---|---|---|
| | Rep.Acc.ID | Host | # GN's | Lineage | Seg. Count | GN.Acc.IDs |
| | | | | | | 1759,EU482715,FJ882526,GQ868605,GU131715,FJ185077,GU131810,FJ639688,FJ432732,GU131977,FJ461339,EU081226,GU131817,GU131778,FJ898429,EU482507,AY713476,FJ390383,HM181961,JQ287663,FJ639797,EU677172,FJ898379,GQ199859,FJ850100,GU131750,HM469966,FJ547065,GQ199777,JF937614,GU131757,FJ461306,GQ868524,GU131894,GQ199844,EU081270,FJ461336,JN638344,GQ199807,EU677154,GU131727,DQ285559,EU660403,EU677163,FJ205873,FJQ24480,GU131919,FJQ24445,EU482540,GQ199816,FJ461316,FJ898388,EU482793,EU081231,JQ04566 7,GU131805,GU131784,FJ461313,FJ410234,JQ045638,EU081265,FJ410188,AY835999,FJ898413,HM181950,GQ199850,GU131722,KF921935,FJ898419,FJQ24436,FJ390381,FJQ24479,EU482491,AB074760,FJ898392,JF937650,KC131141,JQ915075,GU131796,EU687251,EU677173,GQ199781,EU482809,FJ898397,AF514885,EU677171,FJ478458,FJ410275,GU131783,EU482511,GU131826,GQ86851 4,FJ410281,JQ04566 |

TABLE 10-continued

| Taxonomy | Rep.Acc.ID | Host | ViroCap-1.0 Taxonomy # GN's | Lineage | Seg. Count | GN.Acc.IDs |
|---|---|---|---|---|---|---|
| | | | | | | 0,FJ882556,GU131708,GQ868535,HM469967,GQ199783,FJ432723,FJ898422,EU482828,GU131693,FJ562106,GQ199771,GU131753,EU726779,GQ199846,FJ882515,FJ410174,GQ199792,EU280167,FJ850093,HQ166035,GQ199829,G0868500,GU131728,KJ189346,FJ432734,FJ390374,JQ045636,DQ672563,JQ045647,FJ898376,FJQ24441,GQ868618,JN658342,GU131696,FJ882520,FJ639735,HM181967,EU482817,GQ199831,JF937611,FJ469909,GQ199775,FJ410192,JQ045626,FJ410263,KJ189318,FJ182027,GU131822,GQ868637,GQ868522,JF937619,FJ687428,GU131921,FJ410290,EU482592,FJ898374,GQ868502,EU677140,GU131764,EU482520,GQ199824,GQ199821,FJ882516,GQ868614,GU131836,FJ898426,JF937609,EU482531,JQ915072,FJ639679,GU131980,GQ868512,FJQ24485,KJ189329,GU131687,FJ639820,FJ410262,JQ045649,AF514878,EU726777,JQ045668,EU081234,GQ199773,FJ639678,FJ410198,KJ189359,GU131963,G0868525,FJ432739,GQ199827,AB519681,AY713475,FJ882563 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | ,JQ045643,FJ639811,FJQ24427,EU482820,KJ189338,EU081262,FJ410232,FJ461303,FJ639672,FJ687430,AY732474,JN903581,FJ410279,GQ868639,FJ461332,GU O56029,EU482476,GQ19979 1,GU131889,GQ19998 43,JQ287664,EU081 260,KJ189332,FJ906 965,JQ045644,GU13 1769,EU249492,EU4 82516,JN819411,GQ 199799,JQ287660,JF 937613,AY726551,FJ 182031,DQ285560,G U131798,GU131922, GQ199836,KJ189327 ,KJ189339,EU482796 ,GQ199798,AY72280 2,FJ639676,GU13195 6,EU482823,EU4828 03,GU131774,HM181 954,AY708047,EU66 0394,EU482619,GQ1 99793,JN000935,GQ 868519,FJ410227,G 0868532,GQ868517, GQ868560,FJ410255 ,KJ189344,EU482537 ,EU081271,FJ410185 ,GQ868564,EU72678 1,KJ189337,FJ87380 9,EU081253,GU1318 18,HM181948,JQ045 665,FJ639694,FJ410 286,GU131887,GU13 1829,FJ882570,FJ63 9823,FJ461312,FJ88 2568,EU482501,FJ41 0273,JQ045630,GQ1 99805,GQ868513,FJ 410282,EU482819,FJ 410197,GU131786,K J189345,GU131733,F J898403,HQ891314,F |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | JQ24457,EU081238,KJ189348,FJ898377,EU726780,HQ166036,FJ898411,FJ410242,FJ882540,GQ199810,FJ882517,KJ189364,JF937610,GU131812,GQ868504,FJ410256,GU131807,HM181964,AY722801,FJ182032,JQ045637,FJ432742,EU081256,FJ898399,GQ868501,FJ898389,EU482611,EU660390,KJ189340,GU131698,GQ868530,FJO24442,EU482490,FJO24478,EU482513,GU131830,FJ898400,G0199780,GQ868559,FJ898371,FJ461331,FJ410284,JF937601,FJQ24429,GQ868563,FJ898423,GU131966,GU131741,GU131823,GU131730,FJQ24445,EU179860,KJ189358,EU249494,JN697056,FJ547060,GU131842,GU131752,EU482806,GU131802,DQ672559,EU482521,EU482815,KJ189366,KJ189347,EU081264,FJ882551,GU131809,FJ205876,GU131720,FJ205883,KC759167,GU131972,GQ868619,GU131703,HM631855,KC131140,HM181959,AF514876,FJ432725,JN638343,GQ199787,EU482811,FJQ24437,EF032590,FJ882542,FJ461325,EU482525,GU131799,JF937616,FJ639681,DQ672556,FJ182020,FJ898401, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | JQ287661,FJ410247, EU482822,EU482517 ,EU660412,JQ04563 5,FJ859029,HM6318 52,JN903580,GQ199 803,EU081259,EU08 1273,HQ332178,FJ18 2033,GU131725,GU1 31808,KJ189349,FJ5 47063,AB189121,EU 482483,FJQ24463,GU 131692,GQ199852,F J639675,GU131819,J F937608,EU081279, GQ199819,FJ882548 ,EU482518,FJ410261 ,GU131981,FJ687426 ,EU677165,FJQ24432 ,GQ868499,KJ18931 6,GU131777,KJ1893 56,FJ639796,FJ4102 78,FJ182025,KJ1893 52,EU081233,GQ868 611,EU482538,GU13 1962,KF955427,JN81 9405,AF300641,HQ8 91313,FJ898381,EU4 82712,GU131960,AB 608786,GU131723,E U081277,EU482800, FJ850104,EU081252, FJQ24430,EU726782, KJ189331,FJ898417, EU596504,GU131678 ,GU131838,EU48250 0,HQ332183,GU1319 67,JF937604,FJ4613 18,FJ182030,FJ1820 18,FJ432729,FJ4102 50,GU131739,AY726 550,KF921942,JN819 410,KF921933,EU48 2530,GQ199796,GU1 31712,AY726554,FJO 24440,FJ461319,EU2 49491,EU482509,GQ 868536,FJQ24426,GU 131795,GU131781,E |

| Taxonomy | Rep.Acc.ID | Host | # GN's | Lineage | Seg. Count | GN.Acc.IDs |
|---|---|---|---|---|---|---|
| | | | | | | U60393,KJ189343, GU131735,EU482713 ,FU482482,FJ410226 ,EU081239,GQ86851 1,FJQ24453,HM1819 63,FJ882560,JF9376 44,FJ547086,FJ8825 44,GQ199834,GQ199 779,EU482514,GQ86 8508,EF122232,FJ89 8391,EU482505,JN81 9425,FJ639670,FJ20 5884,GU131804,FJ89 8404,FJ410190,FJ41 0196,GU131732,AY1 45123,FJ687431,EU0 81278,FJ810415,EU4 82503,FJ873814,FJ8 98410,FJ882525,EU0 81235,GQ199809,FJ 639680,FJ410257,KF 955444,JF937635,EU 482717,FJQ24481,FJ 882539,JF937617,FJ 410243,AF180818,JQ 045661,GQ199873,J 0045640,FJ882530,F J182002,FJ882562,J N819412,GU131828, JN19402,GU131738 ,HM181958,EU67715 1,GU131888,JQ0456 54,EU482526,EU482 535,KJ189317,FJQ24 438,EU677167,EU48 2489,KJ189365,GQ8 68601,FJ898407,HM 181951,EU081275,A Y732478,JQ287667,F J410277,AY762084,F J639696,FJ410283,E U482502,JQ045653,F J639674,EU482610,F J898414,FJ882535,G U131710,FJQ24462,F J898373,GQ868538, EU482807,EU482827 ,FJQ24449,A75711,E |

| Taxonomy | Rep.Acc.ID | Host | # GN's | Lineage | Seg. Count | GN.Acc.IDs |
|---|---|---|---|---|---|---|
| | | | | | | U48484,FJQ24446,FJ898375,KJ189313,FJ882569,GQ868570,AY732477,EU081280,EU482805,EU48251 9,FJ43 2748,FJ54708 9,GU131763,GQ199848,EU677157,FJ2058 72,FJ410280,EU4827 94,FJ882545,KJ1893 06,FJ639814,U88535 ,GQ86852 1,JF93 7 5 9 9,EU482816,EU4825 39,GU131707,GU131 976,HM181970,GQ86 8566,GU131758,FJ18 2021,GU131690,JQO 45651,FJQ24460,GQ 199822,FJ373298,EU 081261,JQ915080,E U081255,GU131891, HM181946,GU13172 6,GU131691,JN6383 38,JQ915074,GU131 982,GQ868528,FJ41 0244,EU482792,HM1 81957,FJ850081,GU1 31785,FJ882519,JQO 45641,GU131700,FJ8 98406,FJ373296,GU1 31825,AY726555,EU 179861,FJ410260,FJ 461330,FJ882565,FJ 432733,GU131736,G 0199856,FJ390379,F J882537,KJ189333,E U081243,FJ410210,A Y145121,GQ199801, JN903579,KJ189350, AF226687,JN093516, FJ89393,GQ868526 ,FJ461335,KJ189360, EU249495,HM63185 3,GQ868523,FJ8983 80,GQ868636,EU482 567,FJ687432,FJ182 019,M87512,JN63833 6,GQ199867,EU6603 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 92,FJ850070,EU6603 96,JQ045659,GU131 780,FJ182035,GQ19 9784,GQ199854,DQ6 72561,GU131949,GU 131768,EU482494,KJ 189361,EU482813,K F955443,EU081272, GQ868533,KJ189320 ,GU131761,GQ86863 0,FJ639818,FJ43273 8,FJ898386,FJ88254 1,FJ432749,EU67716 2,GQ199778,GU1317 02,GU131771,FJ4101 89,DQ285561,EU081 269,JN638339,FJ882 523,KJ189353,EU081 281,GU131923,EU48 2523,JF937605,JF93 7649,HQ891316,FJO2 4459,EU660402,FJ41 0191,GQ199820,AB2 04803,GU056030,HM 181939,FJQ24482,GU 13171,FJ687429,FJ 410258,GU131747,G 019974,FJ182028,E U482512,EU482532, FJQ24456,KJ189323, JN819413,AF180817, FJ639740,GQ199835 ,GQ199789,FJ63974 3,EU677166,JQ0456 39,FJ882550,JQ0456 34,EU482496,KJ1893 69,AY726549,EU482 488,KF921949,GQ19 9841,GQ868609,GQ8 68569,EU482709,FJ8 50087,GQ868509,GU 131686,FJ898396,EU 482821,JQ915071,E U848545,FJ461333,G 0868565,EU677169, EU726778,FJ639824, EU482617,FJQ24484, FJ850084,FJ410268, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | FJ89395,GQ199790,GU131719,JQ04564 5,GQ199825,GU1318 01,JQ287665,EU677 175,FJ882564,EU482 826,FJ410265,EU249 493,FJ461320,FJ882 546,GU131813,EU35 9008,GU131684,FJ63 9813,HM181938,FJO 24428,FJ850069,HQ6 24984,AF311957,GU 131688,EU482477,E U482492,EU482707, FJ461328,GU131925, FJ410249,GQ868531 ,FJ850075,FJ898409, FJ390378,JN903578, GU131767,AF298807 ,EU482710,FJ882547 ,FJ898390,EU482485 ,GQ868527,FJ41027 2,GQ199847,EU0812 68,JN697057,HM631 851,GQ199817,FJ41 0287,FJ432747,EU67 7178,JQ915073,GU1 31983,GU131729,GU 131683,KF921934,FJ 898425,FJ639815,EU 482508,EU677158,FJ 390380,KJ189314,FJ 882553,HM181956,G 0199855,AB074761, FJ182023,FJ898415, KJ189326,EU482618, EU482499,EU660391 ,FJ898378,FJ639695, GU131814,FJ898402, HM181943,GU13179 1,FJ882566,DQ19357 2,GU131840,JN81194 14,GU131832,EU482 524,EU482706,GU13 1775,HM181960,FJ7 44702,FJ906964,EU4 82818,AF226686,EU 482497,JQ045629,G |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0868635,JF937600,E U081237,GU131824, FJQ24450,GU131701, FJ410252,GQ199794 ,EU660395,AY27766 4,GQ868498,KJ1893 19,HQ166037,FJ8825 27,GQ868534,GQ868 503,KJ189315,GQ19 9875,EU482825,GU1 31737,FJ390388,FJ8 98421,FJ850068,FJ5 62101,GU131800,KJ 189330,FJ410211,FJ 432745,AB608789,E U081266,AY732475, AY277666,GQ199838 ,GU131776,FJ882552 ,GU131743,GU13197 8,FJ410246,EU48249 5,AF311958,EU4825 15,FJ639671,AY7134 74,JN63837,GQ868 608,FJ882532,FJQ24 483,GU131689,EU66 0401,FJ89840S,HM1 81940,KF955442,GU 131973,EU482814,FJ 898437,EU482791,A Y206457,FJ687427,F J898385,FJ639669,G 0199818,KJ189355, U88537,FJ639692,E U081227,KJ189324,F J898372,GQ398255, GQ868606,EU48271 6,AY726553,GQ1998 04,JQ287666,FJ8984 24,GU131821,FJ1820 26,HM181952,GU131 797,FJ461341,JQ045 663,FJ410183,EU482 486,JQ045633,EU08 1245,AF226685,EU4 82799,FJ432735,JQO 45646,GQ199837,FJ 390386,FJ562105,EU 482718,GU131968,FJ |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 639690,FJ906728,FJ410269,EU677168,H0332180,GQ868562,FJ547087,FJ432730,JQ045657,GQ199845,EU249490,GU131711,EU863650,GQ19971,95,FJ898394,EU081247,FJ639684,GQ199782,GU131920,FJ410251,FJ410203,FJ432721,FJ469907,GU131969,FJ882561,FJ410266,GU131841,EU677159,HQ332179,EU482498,KJ189328,GQ199813,GU131754,G0199858,FJ850101,KJ189351,FJ850113,GU131794,EU081230,HM181962,GU131892,FJ410205,KJ189363,GU131837,EU482506,JF937607,FJ182029,FJ410285,FJ639819,HM181941,GU131709,GQ199776,FJ410173,EU482479,EU482510,GU131731,FJ410222,EU687247,GQ868518,FJ461323,EU482504,GU131679,GQ868613,GU131984,EU482609,GU131970,FJ882567,GQ199826,FJQ24464,FJ176779,EU677153,GU131319,48,GU131724,HM181942,FJ432720,FJ639741,FJ410270,FJ562104,FJ898448,GQ199877,JF937596,EU482802,FJ410212,GQ868507,EU677177,KJ189312,EU081242,FJ478457,GU131793,GU131787,GU131816,FJ410184,GU131705,E |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | U081258,GQ199830, EU677156,GU131765 ,GQ199872,FJ41021 8,EU482522,JN81940 3,AY732483,EU0812 36,JF937615,EU4824 81,JF459993,GU1318 15,KJ189307,GU131 789,FJ410199,AY277 665,FJ461315,HM48 8256,FJ898427,FJ63 9808,FJ639689,JQ04 5655,FJ432740,GQ8 68615,FJ639686,GU1 31745,DQ672564,EU 482533,FJ639794,G 0868568,GQ199857, EU482808 |
| Dengue virus 2 | NC_002640 ,NC_00147 5,NC_0014 74,NC_001 477 | vertebrates,invertebrates, human | 1024 | Flaviviridae,Flavivirus,Dengue virus | — | FJ850074,JF730051, EU596490,EU482725 ,EU482622,JN819407 ,GU131931,EU48276 2,FM210226,GU1318 64,GU131896,EU677 148,EU687246,EU59 6500,EU482444,EU5 29701,GQ868552,EU 660398,GQ398270,F J744716,EU482675,F J744705,EU482548,F J639718,GQ868557, EU569695,EU569699 ,GQ868604,GQ86864 6,KC294212,EU4825 90,EU596488,FJQ244 74,FM210237,EU482 772,GQ398296,JN81 9408,GQ398299,GU1 31900,EU482761,EF 105381,EU920836,E U482647,FJ639709,H 0541788,AF100459, FJ882602,EU482606, KF041237,EU482573 ,FJ898454,EU482560 ,JXQ79688,HQ33218 5,EU920834,FJ18201 4,EU482679,FJ89846 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 7,AB479042,FJ90695 8,EU920849,EU5697 02,EU596489,EU596 498,FJ898435,EU482 623,HM582103,EU48 2643,EU687225,HQ7 05624,EU482569,EU 482472,FJ906969,FJ 850119,FJ639700,EU 482673,EU482664,FJ 024452,GQ398310,E U677142,GU131902, KF041235,FJ639837, FJ410215,AB122022, AF022439,FM210223 ,EF105387,JN819418 ,FJ687439,GQ86855 0,AF038402,FJ43272 6,FJ639828,EU48265 7,GQ868591,EU4827 48,EU482585,FJ6397 88,FJ639710,EU4825 72,AF169679,EF1053 84,HM582109,FJ850 085,EU482554,EU48 2542,EU482691,GQ3 98285,AF359579,KC 294206,FJ461321,EU 482759,AF204178,D 0181800,KF955360, FJ205885,FJ850064, GQ868515,EU48258 4,EU687242,FJ74471 0,FJ687445,FJ63983 1,EU482694,FJ89845 0,FJ744721,EU48254 4,EU482698,EU4826 29,FJ205880,EU4824 64,GU131959,EU596 487,GQ398261,EU48 2579,GU131899,GQ1 99894,GQ199890,GU 131880,GU131883,E U687228,EU482471,J X966380,FJ898460,G Q398268,GU131974, FJ744719,EU569694, EU482631,GQ39827 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 5,FJ639705,FJ89843 |
| | | | | | | 8,GQ199866,EU6771 |
| | | | | | | 38,GQ868603,EU920 |
| | | | | | | 845,EU482665,GU13 |
| | | | | | | 1885,EU660406,EU5 |
| | | | | | | 96499,FJ744709,JN8 |
| | | | | | | 19421,JX286525,AY7 |
| | | | | | | 44147,FJ906967,AY0 |
| | | | | | | 37116,JF730045,FM2 |
| | | | | | | 10227,KF041232,JF3 |
| | | | | | | 57906,EU677149,EU |
| | | | | | | 482697,GQ398259,A |
| | | | | | | F169685,EU482734,F |
| | | | | | | J639699,AB479041,E |
| | | | | | | U482449,EU660404, |
| | | | | | | EU482742,GQ86855 |
| | | | | | | 8,EU677144,KC2942 |
| | | | | | | 18,GQ398295,FM210 |
| | | | | | | 221,KF955359,GQ86 |
| | | | | | | 8631,EU920840,KC2 |
| | | | | | | 94215,FJ850076,M19 |
| | | | | | | 197,EU482670,JF327 |
| | | | | | | 392,GQ252677,FJ74 |
| | | | | | | 4704,EU482550,JN81 |
| | | | | | | 9416,EU482752,JQO |
| | | | | | | 45684,GQ398265,EU |
| | | | | | | 482787,GQ868588,A |
| | | | | | | F100464,GQ868545, |
| | | | | | | EU482553,GQ39830 |
| | | | | | | 0,EU920835,EU4825 |
| | | | | | | 71,GQ252676,GQ868 |
| | | | | | | 600,EU482722,FJ850 |
| | | | | | | 121,EU920838,JXQ79 |
| | | | | | | 690,EU482660,GQ39 |
| | | | | | | 8308,GQ398258,EU4 |
| | | | | | | 82668,GU131884,FJ6 |
| | | | | | | 39698,HQ332184,KF |
| | | | | | | 360005,KC294213,A |
| | | | | | | F100460,AF169682, |
| | | | | | | GQ398314,FJ687434 |
| | | | | | | ,GQ868624,AY70203 |
| | | | | | | 5,FJ687438,FJ89843 |
| | | | | | | 4,EU482620,EU4824 |
| | | | | | | 63,EU482650,EU179 |
| | | | | | | 858,KJ189309,EU482 |
| | | | | | | 751,HM582113,EU48 |
| | | | | | | 2754,HQ332190,KF9 |
| | | | | | | 55362,KJ189308,AY7 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 02034,FJ810418,DQ181797,EU854294,GQ139291,FM210216,AF100466,EU482784,FJ390391,EU482758,EU529706,GQ398289,FJ639704,AF169688,HQ733861,FJ639834,GQ398271,KJ189311,GU131886,GQ868540,FJ898432,FM210225,HQ634199,EU482599,FJ373301,EU687241,GQ868549,FM210245,GQ199899,FJ744714,GU131901,FJ906956,FJ850067,EU482474,EU482729,EU482628,EU687214,FJ810409,EU482705,FJ850105,EU482700,FM210210,GU131975,G0868598,JX475906,FJ744712,EF105383,EU596497,FJ639706,G039298,FJ639734, GQ398260,EU920829,EU482782,EU482721,HQ541794,KC294210,EU482704,AB122021,EU920847,GQ199895,EU677145,FJ461305,EU482576,EU726776,FJ410228,EU482666,EU482582,FM210233,GU131929,JQ045686,FJ850117,EU482773,EU482723,FM210220,EU482685,AY702037,FJ432724,FJ850112,U87412,AB122020,FJQ24461,EU569715,DQ181801,EU482446,GQ868551,GQ199898,KC294221,EU482658,FJ850053,JX286526,FJ687444,EU687240,EU920 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 846,M84727,KC2942 02,AF100463,FJ8501 06,EU482669,FJ3903 90,EU569718,EU726 767,EU482785,HQ54 1798,EU482601,EU5 96496,FJ850088,EU5 69713,JX470186,FJ4 10224,FJ687443,EU4 82547,FJ687447,EU6 60416,FJ906962,DQ4 48231,GQ199892,FJ 906968,JF730046,G 0868599,FJ182012,E U482763,KC294205, EU569698,EU482625 ,FJ547067,JF730053, FJQ24477,EU482775, EU482781,FJ850091, EU569720,EU482737 ,DQ181798,EU66039 9,EU569706,EU6872 49,GQ398272,JX286 521,FJ461314,DQ181 802,GQ398305,EU48 2568,GQ868620,EU9 20839,HM582114,FJ 898453,FJ687437,EU 482473,GQ868625,F J850120,EU726775,E U482634,EU1799859, FJ850082,FJ410221, EU482770,FJ639732, HM631867,GQ86859 6,FM210207,HM5821 11,FM210224,GQ398 266,GQ398278,FM21 0215,KC294219,EU6 87217,EU482451,FM 210218,EU726770,E U482468,GQ868556, EU482788,EU569708 ,GU131927,EU48258 0,EU482637,EU4827 43,KC294209,AF169 680,FJ850054,GQ39 8280,FJ639809,FJ39 0384,FJQ24475,GQ3 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 98293,GU369819,EU482570,AY858035,EU56972I,FJ410219,EU056812,HQ541787,EF105382,EU482726,EU482672,EU68724 5,FJ687435,AF16968 6,EU569703,KJ18937 0,KC294222,KC2942 07,EU920843,FJ8501 08,JF357905,GQ868 543,EU482638,EU48 2541,FM210211,GQ3 98309,AF100461,EU 687238,FJ373300,KC 294201,GQ868590,E U596495,EU482701, KF955369,AB543624, JX286517,EU003591, EU482769,EU482749 ,EF051521,EF105385 ,EU482688,FJ639697 ,JF730050,GQ39828 8,FJ410200,GU13192 8,JN796245,FJ41020 8,FJ850118,DQ18179 9,FJ850060,FJ37329 9,GQ398311,GQ8685 42,EU482552,EU482 760,FJ639836,EU687 236,EU482602,GQ39 8273,EU482577,FM2 10208,KF955364,DQ 181805,EU687212,FJ 850065,EU920844,FJ 478459,EU687224,E U482662,AY702040, EU920833,GQ19989 6,GQ398302,HQ5417 99,EU482624,FJ2058 79,JQ955623,AF0224 37,FJ639703,AB1891 23,GQ868555,EU482 699,EU179857,GQ86 8516,EU482583,FJ74 4706,EU482450,EU4 82603,EU920831,FJ6 87436,EU569701,EU |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 482243,GQ398284,E U660414,FJ744722,G U13182,FJ410233,E U482695,FJ390385,K C13142,JN819420,F M210219,EU482730, GQ398279,EU67714 1,EU482475,GQ8686 38,FM210244,HM488 257,FJ639717,FJ639 833,EU482696,EU48 2744,FJ906957,HM5 82107,EU482587,KF 955372,FJQ24454,EU 677147,FJ744720,EU 482633,EU687216,FJ 898461,EU677137,G 0398290,GQ398276, EU687237,EU056810 ,HM631868,FJ56209 8,GU131930,GQ3982 63,EU482739,EU482 465,HM582101,FJ89 8479,EU482741,FJ68 7441,GQ868641,FJ7 44723,EF455904,EU 482702,EU482671,E U596486,EU482467, EU482551,EU482667 ,HQ999999,GQ39828 1,EU482656,KC9640 94,EU677143,EU569 707,EU482755,HM63 1865,EU482632,FM2 10231,GQ199868,FJ 744718,FJ639707,AJ 968413,FJ410217,EU 920841,HM582116,A F169681,EU482687,F J744743,KC294214,K C964093,EU687235, FJ226066,FJ205877, FJ810410,FJ850116, FJ639711,GQ398283 ,EU482649,FJ744724 ,FM210240,GQ39831 2,EU920832,GQ3983 01,KC294217,FJ6397 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 02,AF100465,FJ8500 63,KC294223,KF955 363,FJQ24458,AY776 328,GU131881,JQ04 5670,FJ850061,GU28 9914,FJ898477,EU08 1179,GQ868554,AF0 22435,FJ410241,EU5 69716,EU569711,EU 482783,M84728,KC2 94211,FJ898436,EU4 82466,EU482677,FJ7 44713,GQ398257,EU 660413,AY85036,E U482642,EU621672, GU131947,EU482779 ,GQ199897,EU48273 5,FJ744715,AB18912 4,KC294200,EU5696 96,AF169683,EU596 483,FJ906959,KF955 366,GQ199900,EU48 2682,GQ398304,HQ5 41792,EU482678,FJ8 98439,EU596485,EF 105389,DQ18 1806,F M210232,EU482674, FM210213,EU359009 ,EU482626,KC29420 3,GU131879,HQ7056 25,EU482757,JX2865 23,EU687222,AB189 122,EU482684,HQ02 6763,EU482605,GQ8 68592,FJ850051,GU1 31924,EU482581,EU 482646,HM582106,E U482445,EF105386, EU920830,JX286519, EU482676,EU482644 ,FJ547064,FJ410288, EU569700,GQ39828 2,GQ398297,FJ4101 93,EU687215,EU482 689,GU131898,FM21 0238,FJ639708,JX28 6518,FJQ24473,KC29 4216,AF204177,FJ89 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 8465,JF730049,EU48 2724,HM582104,EU4 82659,EU482720,AF 100467,KF955373,G 0199893,FJ687446,E U482586,FJ744725,E U482641,EU660417, KF041234,EU569697 ,FJ906960,EU687227 ,EU482747,FJ390389 ,FJ639701,EU482776 ,HM582108,FM21023 9,GQ868622,EU4827 80,FJ744708,EU5296 93,KF041236,GQ868 621,EU482556,GQ86 8640,EU687231,FJ20 5878,EU482774,FJ85 0072,KF955401,EU6 87243,FJ639829,EU4 82654,FJ744703,AF0 38403,EU482578,EU 482766,AF169678,G 0398262,GQ868595, AF208496,EU482777 ,EU687250,GQ86855 3,KF955365,EU4824 70,JF730054,EU6871 99,GQ398267,EU482 594,HQ332188,EU92 0850,HM582115,EU4 82745,FM210202,FJ6 39822,FJ850050,FJ4 78455,JX286524,EU4 82627,FJ390387,EF1 05378,FJ687440,AF0 22436,EF105390,HM 582112,EU569705,JX 286520,EU482719,JX 286516,EU482448,E F105379,FM210217, FJ850066,JF730044, EU482630,HQ541793 ,EU482645,EU05681 1,EU482469,EU4827 33,EU482636,FJ4102 91,GQ199901,JX286 522,GU131932,FJ898 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 451,JF730047,EU482557,KJ189310,AY702039,EU482639,FM210212,EU482683,GQ199874,FM210209,FJ639832,HM582102,KC294204,KF041233,HM582105,EU687248,FJ461311,FJ744745,FM210228,AF022441,KF955395,EU569719,FM210246,JF730048,EU482588,EU660405,HQ891023,GQ398292,AF100468,GQ398274,FM210242,KC294208,GQ398294,EU482652,EU482690,HM582099,JX966379,EU081180,JN819422,EU482600,JN819424,HQ332187,HQ891024,EU482562,EU687232,FJ906966,EU660415,EU687213,HM181971,EU482546,KF955402,GQ398264,EU687244,AY702036,EU482753,EU482621,FJ547090,AY702038,FM210206,EU529694,FM210229,JQ955624,FJ898478,EU482640,FJ882594,EU482661,FJ744741,GQ868623,EU482608,GQ398307,FJ859028,JXQ79694,AF169687,GU131897,EU569692,AJ487271,EU920828,EU482593,GQ868589,FJ744707,FM210203,FJ639783,EU482655,EU482728,FJ639835,DQ181804,M29095,EU687223,EU920837,FM210234,FJ898466,EU482750,GQ398303,F |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | M210243,EU569709,EU854293,EU482653,FU482746,FJ410259,EU081177,EU48265 1,FJ850062,GQ8685 44,HQ332189,EU677 146,EU482736,EU68 7230,GQ868597,EU4 82575,EU482738,EU 482740,FM210236,E U482604,AF489932,F J898449,HQ541786, EU482731,EU569704 ,FJ687442,EF105380 ,FJ639733,EU781135 ,FJ850078,FJ410202, JF730052,FJ410195, EU529700,AF022438 ,AF100469,EU48270 3,GQ398269,FJ7447 17,EU482598,JN3684 76,HM582100,FM210 230,FM210241,AF11 9661,HM631866,EU4 82680,GU131843,EU 482589,FM210204,E U687220,GQ199869, EU596484,AF100462 ,GU131955,EU48266 3,EU482607,FJ87380 8,EU482686,GQ3982 87,GQ868541,FJ906 961,EU569714,EU48 2549,EU482447,EU4 82574,EU920848,EU 920842,FJ410223,EU 482648,FM210235,E U529695,EU081178, KC294220,FM210214 ,EU482756,FJ410237 ,EU482692,FJ744742 ,JF357907,EU569717 ,FJ850107,FJ461309, EU482786,EU482732 ,EU482693,FJ744744 ,DQ181803,AF27661 9,EU569710,EU5964 91,FJ850115,EU4826 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 35,EU569712,HQ332186,FJ639830,HM582117,EU482597,EU660400,FJ873811,HM582110,FJ467493,JF730055,GQ868497,FJ810412,EU482565,GQ398286,FM210205,GQ398277,EU482545,GQ398313,GQ398306,M20558,EU482778,EU482727,EU482681,EU687229,AF169684,FJ810411,AF022434,EU569693,EU482561,JN819419,FJ882593,KC964095,FJ898452,FJ744711,EF105388,EU482771,FM210222,AF022440 |
| Dengue virus 3 | NC_002640,NC_001475,NC_001474,NC_001477 | vertebrates,invertebrates,human | 785 | Flaviviridae,Flavivirus,Dengue virus | — | HQ705619,KF955479,GQ199887,EU482558,EU081202,FJ882578,FJ639714,KJ189293,EU081219,FJ461338,KF955457,EU687239,GU131954,FJ639724,EU660407,EU529704,AB214882,FJ639779,KF041258,FJ850080,AB189125,FJ639760,EU687221,GQ868617,EU482460,HM631859,JF937624,FJ182040,KF955463,GQ868572,GU131867,FJ850086,HM181977,AY67651,EU660408,EU081221,AY855043,HQ541791,EU482457,JF937643,FJ182005,JF937631,JF937633,FJ639789,M93130,FJ547074,JQ045691,GU131933,FJ432743,FJ547069,FJ373302,GQ868629,KJ189299,JQ045693,FJ639762 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | ,JF808126,GU131873,EU482596,JF920408,FJ432731,FJ744726,KF955333,FJ639758,FJ639803,GU131859,HQ705611,FJ432741,FJ205871,JF937636,FJ639798,KJ189265,JQ920482,FJ639793,EU529692,FJ639713,EU529705,AY662691,GU131937,FJ850049,JF937625,KF955473,AY676348,EF629370,EU529688,AY67914 7,JF937648,AY49687 1,EU081214,AY8580 47,HG316483,JQ920 484,FJ882571,GQ86 8627,KJ189296,FJ54 7081,FJ182041,FJ63 9801,FJ547083,GQ8 68574,EU081190,KF 955461,EF629368,FJ 547062,GU131907,H M631864,EU482563, FJ639769,JN000936, FJ410229,FJ182015, FJ639761,KJ189283, HQ705621,KJ189273 ,KJ189269,GU13195 3,FJ639795,FJ63972 3,FJ182038,KJ18925 8,HQ671178,JQ0456 92, FJ898459,GU13319 11,HM756277,GU131 870,GU131905,FJ882 572,KJ189262,FJ8850 098,GQ199862,JF93 7630,JF920399,JF80 8121,HM756282,JF8 08118,JF808119,HQ5 41789,FJ639720,EU0 81220,JQ920485,KF9 55458,KJ189280,EU4 82453,GU131857,EU 08181,DQ675519,E U660411,JQ920488,F |

TABLE 10-continued

VireCap-1.0 Taxonomy

| Taxonomy | Rep.Acc.ID | Host | # GN's | Lineage | Seg. Count | GN.Acc.IDs |
|---|---|---|---|---|---|---|
| | | | | | | J547076,AY770511,JQ920487,JF937634,JF937637,GU131872,EU081189,EU726774,FJ873813,HM18193,5,FJ547066,GU13194,4,FJ639731,FJ54707,7,EU482461,FJ85007,9,HM631854,GQ8685,78,JF937646,FJQ244,65,EU081215,AY858,041,FJ913015,HQ705,615,AY496873,GU13,1853,KF824902,GU1,31862,JQ920476,FJ5,62107,KJ189263,FJ7,44740,EU687219,KJ1,89292,AY744682,KJ1,89277,JN093517,EU4,82454,FJ562102,EU0,81223,EU081203,FJ6,39774,GU131869,EU,529703,HQ705623,FJ,744727,JF937626,AB,214881,AY858044,EF,629369,EF629373,FJ,390375,FJ898470,KJ,189268,JN093515,FJ,898445,JQ920478,H,M631861,HM756281,EU529690,GU131904,KJ189298,FJ639750,FJ547061,KJ189256,FJ882577,DQ675528,FJ562097,KJ189278,FJ898446,GU131951,KJ189271,GU131848,FJ898462,EU081195,,DQ675520, HQ70562,2,EU529698,KJ18926,6,FJ639784,FJ63979,2,GQ868593,AY7446,83,FJ898444,GU1318,76,FJ639778,FJ432722,FJ639755,EU081186,HQ705617,GU131847,FJ639770,EU529 699,EU726769,FJ850097, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | JQ920480,EU596494, EU081192,KF9 55466,FJ898472,,AB2 14880,HQ166032,KF 921916,JF808122,DQ 863638,FJ744734,GU 131915,JF937647,JF 295012,GQ199886,F J850094,JF808120,E U482613,EU529686,J F920404,FJ639768,H 016603,HQ332170, JF920396,FJ744729, DQ675525,EU081196 ,KJ189274,EU529683 ,EU482559,HM18193 3,HM181934,FJ5470 78,EU081194,FJ6397 76,GQ868548,FJ4461 334,KJ189291,HQ70 5610,GQ252678,GU1 31913,GU131871,JF8 08124,FJ639805,GQ 868577,GU131934,E U081206,HQ705613, JQ045694,AB189127, FJ639756,FJ744735, EU482566,GU131941 ,EU081208,EU72677 2,JF937638,FJ88257 4,EU854298,DQ4016 90,EU687218,HM181 975,FJ461326,FJ898 457,HM631857,JF93 7620,FJ644564,FJ74 4737,GU131939,KF9 55471,AY744677,HM 631869,FJ562099,KJ 189288,FJ898475,G 0466079,JF937623,J 0920486,EU081205, GU131855,GU13185 6,FJQ24466,GQ8685 47,AY744684,FJ4613 37,HM631862,AY676 352,GU131952,HM18 1972,FJ182006,GU13 1877,GU131846,HM6 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 31860,JF920402,KJ189270,FJ205870,KJ189285,GU131938,JF937632,FJ182013,FJ82575,AY923865,HM631858,JQ045690,EU482614,JF920405,FJ639751,FJ898469,FJ744731,KJ189260,AY496874,FJ432728,DQ675531,EU482452,EF643017,EU482595,EU596493,EU660409,EU726773,FJ850096,FJ898464,EU569691,FJ810416,FJ898463,GU131861,KF955476,FJ547085,EU081225,JF920409,GU131866,EU854291,EU932688,JF808127,JQ045689,AY858042,EU081212,GQ199891,JF937639,FJ898476,DQ401692,AY744679,DQ675527,JF808128,JF920393,FJ639763,FJ461322,FJ547079,G0868626,KJ189289,JF920407,HQ541796,FJ182037,KJ189259,EU687198,GQ086854,GQ199861,EU529702,FJ898458,JF504679,HQ705609,AY676350,HM631863,FJ744732,AY099337,FJ639817,JF937621,KJ189261,EU482612,EU482564,GU131874,EU482459,KJ189300,AY496879,JF937640,JF920401,FJ850056,KJ189290,EU081201,FJ898441,FJ390377,HM756276,EU081204,GU131903,GQ199889,EU569690,GQ199989 |

TABLE 10-continued

VirocCap-1.0 Taxonomy

| Taxonomy | Rep.Acc.ID | Host | # GN's | Lineage | Seg. Count | GN.Acc.IDs |
|---|---|---|---|---|---|---|
| | | | | | | 63,JN662391,FJ850089,DQ401693,JF920398,FJ639826,GQ199870,FJ898468,EU081198,FJ639721,KJ189282,KF955332,DQ675523,EU781136,FJ547072,FJ373306,GQ868587,EU482455,FJ562103,AY744685,FJ639827,FJ898456,EU660410,FJ390376,GU131860,GU131852,GU131850,FJ898474,EU932687,GU131878,HM181978,EU081182,GU131942,FJ182007,EU081210,KF041257,EU081224,KJ189276,FJ639730,HQ166031,KF955487,EU081184,GU131844,EU482458,JN093513,JQ045688,JF920406,EU529696,FJ873812,AY858038,KF955472,GQ199864,KJ189272,HQ541806,EU596492,DQ675529,FJ850109,KF955465,AY858040,FJ547075,FJ744700,EU569689,JF937641,FJ547082,EU687197,HQ671177,FJ639804,AY858045,HQ541797,KF824903,HQ705618,FJ639753,FJ390372,JF937629,GU131908,FJ639716,GU131865,JQ411814,FJ639790,KF041254,EU529684,KJ189301,HM181976,FJ639725,FJ189845,FJ639754,FJ639816,FJ639759,GQ868628,HQ332171,JQ920483,FJ182008,AY858039,EU081197,AY67 |

| Taxonomy | Rep.Acc.ID | Host | # GN's | Lineage | Seg. Count | GN.Acc.IDs |
|---|---|---|---|---|---|---|
| | | | | | | 6353,DQ675524,FJ63 9799,AY744681,EU6 87233,KF955451,JF8 08129,HQ891025,FJ6 39727,EU081191,JF9 37652,HQ705612,FJ8 50111,FJ639787,HM 756279,JQ920489,H 0166030,FJ898440, GU131943,JF920395, FJ182011,FJ639782, AY858046,FJ850048, FJ639786,GU131916, HQ705614,EU687196 ,EU529697,JF920400 ,FJ639757,EU081207 ,FJ744736,KC425219 ,FJ373303,EU529685 ,KJ189297,EU081209 ,FJ639752,KF955453 ,FJ639749,EU726771 ,HQ166034,KF95550 7,DQ675521,FJQ2447 0,EU081185,KJ18925 7,JQ920481,FJQ2446 8,GU131854,EU3679 62,AY766104,FJ6397 19,FJ639722,EU5296 87,DQ675526,JF8081 25,FJQ24467,HQ5417 85,GU131918,GU131 945,GU131912,GU13 1946,HQ705620,HM7 56274,HM756278,FJ 850083,GQ868571,J N183884,EF629367, DQ401695,KF955454 ,FJ744738,EU660420 ,DQ401691,GU13191 4,AY744678,HQ6711 76,FJ461329,FJ6397 15,AY776329,FJ7447 30,FJ687448,KF9554 77,GU131851,FJ3733 04,KF955456,KJ1892 95,FJ639766,JF9204 03,FJ639781,DQ6755 30,JN368477,FJ8500 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 55,AY858048,HM181 973,FJ562100,FJ850 052,KF041255,JF808 123,GQ252674,EU68 7234,FJ639726,FJ63 9772,FJ410176,EU48 2555,GU131868,JF92 0394,JF937622,FJ47 8456,FJ639780,EU48 2462,FJ182010,KJ18 9284,KF955505,EUS 69688,AY648961,KF9 55468,GU131849,EU 081188,EU687226,G U131950,JF937628,J N000938,KF955459,F J547080,FJ898442,F J182039,GU189648,F J547084,EU854292,K J189267,EU081216, GQ868616,EU08121 3,FJ639785,EF62936 6,FJ810413,JN40651 5,KJ189286,GU1319 40,EU529691,FJ1820 09,FJ639746,KJ1892 64,AY744680,FJ5470 71,FJQ24469,CS8053 42,FJ898473,GU1318 58,FJ744733,KF0412 59,FJ639765,FJ7447 39,JQ045687,EU529 689,FJ898471,FJ639 1137,FJ639800,GQ1 99860,JN093514,AY6 76349,KF955460,EU 081218,FJ390373,KJ 189294,HM756280,K F041256,GQ868586, GU131906,KJ189279 ,GQ199888,JQ92047 9,EU081222,GU3635 49,AY496877,FJ6397 67,JN000937,DQ675 532,FJ410178,EU081 187,DQ675522,HQ54 1790,EU081199,GQ1 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 99871,GQ86634,FJ882576,FJ547073,AF317645,GU131910,FJ898443,AY858037,JQ920477,FJ639807,FJ639971,FJ850110,AY876494,KF955464,GU131909,HQ705616,FJ810414,HM756275,EU081193,AB214879,GU131935,AB1891 28,JF937627,FJ639791,JF920397,FJ639825,KF955462,FJ639775,GQ868573,FJ639747,GQ199865,HM631856,FJ182004,FJO24471,EU081183,FJ547070,EU482456,EU726768,DQ401694,GU131845,GU131875,FJ744728,JF937642,JQ045695,KJ189287,GU131936,JN406514,KF955474,HQ235027,KF955449,EU081217,KJ189275,KJ189281,FJ898447,FJ639810,FJ639712,EU081200,FJ850092,DQ401689,GQ868575,FJ639777,FJ882573,KF955486,FJ639729,FJ390371,HM181974,JN697379,FJ410177,DQ675533,AB189126,GU131917,GQ868576,HG316484,HQ541795 |
| Dengue virus 4 | NC_002640,NC_001475,NC_001477 | vertebrates,invertebrates, human | 134 | Flaviviridae,Flavivirus,Dengue virus | | FJ882587,FJQ24476,FJ882589,AY618992,EU854295,KF041260,JQ513333,FJ639745,GQ199880,JQ513345,JN819409,AY618991,JQ513339,JN559741,JQ915087,FJ810417,JQ513332,JQ513337,FJ882581,JQ513334 |

TABLE 10-continued

VoroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0,JN819406,JQ51334 |
| | | | | | | 2,JF262780,FJ63973 |
| | | | | | | 6,FJ882583,GQ1998 |
| | | | | | | 79,GQ398256,GQ868 |
| | | | | | | 585,JQ513344,FJ882 |
| | | | | | | 595,JQ915089,FJ882 |
| | | | | | | 592,JQ513341,HQ33 |
| | | | | | | 2176,JQ915082,FJ63 |
| | | | | | | 9738,JQ513331,JQ51 |
| | | | | | | 3343,AF375822,EF45 |
| | | | | | | 7906,JXQ24758,FJ88 |
| | | | | | | 2585,FJQ24424,GQ8 |
| | | | | | | 68594,GQ868581,AY |
| | | | | | | 947539,EU854297,G |
| | | | | | | 0199885,FJ882591, |
| | | | | | | GQ868579,FJ882598 |
| | | | | | | ,EU854301,GQ86858 |
| | | | | | | 0,AY618990,FJ22606 |
| | | | | | | 7,HQ332172,JQ9150 |
| | | | | | | 84,AF326825,FJ8500 |
| | | | | | | 59,GQ199882,KC333 |
| | | | | | | 651,JQ513338,FJ639 |
| | | | | | | 744,GQ199884,AY85 |
| | | | | | | 8050,FJ882584,FJ63 |
| | | | | | | 9773,JQ513330,JF74 |
| | | | | | | 1967,FJ882588,FJ63 |
| | | | | | | 9737,JF262782,GQ8 |
| | | | | | | 68584,FJ882590,FJ8 |
| | | | | | | 50095,HQ332173,FJ8 |
| | | | | | | 82596,GQ868643,FJ |
| | | | | | | 882600,GQ199883,G |
| | | | | | | 0868583,FJ882580,F |
| | | | | | | J639748,FJ882599,J |
| | | | | | | 0915081,AY618993, |
| | | | | | | GQ868644,AF289029 |
| | | | | | | ,GQ252675,JQ91508 |
| | | | | | | 5,GQ199876,M14931 |
| | | | | | | ,GQ868642,GQ86858 |
| | | | | | | 2,JN559741,JQ91508 |
| | | | | | | 6,FJ882582,JXQ2475 |
| | | | | | | 7,AF326827,EU8542 |
| | | | | | | 96,FJ639764,FJ1820 |
| | | | | | | 16,JF262779,GU2899 |
| | | | | | | 13,GQ199881,AF326 |
| | | | | | | 826,AY618988,FJ882 |
| | | | | | | 601,JQ513336,FJ850 |
| | | | | | | 058,GQ868645,EU85 |
| | | | | | | 4300,GQ199878,JF2 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Donggang virus | NC_016997 | vertebrates,invertebrates, human | 1 | Flaviviridae,Flavivirus,Donggang virus | — | 62783,JQ915088,HQ 332175,FJ639742,FJ 639739,JQ915090,AF 326573,JQ915083,FJ 850057,F1182017,JQ 513334,FJ882586,AY 618989,FJ882597,JQ 513335,EU854299,JN 983813,JF262781,HQ 332174,AY776330,A Y762085 |
| Douglas virus | NC_018461 | vertebrates,invertebrates, human | 1 | Bunyaviridae,Orthobunyavirus,Sathuperi virus | seg. L | JQ086551 |
| Douglas virus | NC_018462 | vertebrates,invertebrates, human | 1 | Bunyaviridae,Orthobunyavirus,Sathuperi virus | seg. S | HE795090 |
| Douglas virus | NC_018466 | vertebrates,invertebrates, human | 1 | Bunyaviridae,Orthobunyavirus,Sathuperi virus | seg. M | HE795092 |
| Duck Tembusu virus | NC_015843 | vertebrates,invertebrates, human | 6 | Flaviviridae,Flavivirus,Tembusu virus | — | HE795091 |
| Duck egg-drop syndrome virus | NC_015843 | vertebrates,invertebrates, human | 7 | Flaviviridae,Flavivirus,Tembusu virus | — | KC990541,KC990544,KC990545,KC99054 3,KC990542,KC9905 40 |
| Duck flavivirus TA | NC_015843 | vertebrates,invertebrates, human | 1 | Flaviviridae,Flavivirus,Tembusu virus | — | JQ920426,JQ920421, JQ920423,JQ920425, JQ920424,JQ920420, JQ920422 |
| Dugbe virus | NC_004157 | vertebrates,invertebrates, human | 6 | Bunyaviridae,Nairovirus,Dugbe virus | seg. S | JQ289550 |
| Dugbe virus | NC_004158 | vertebrates,invertebrates, human | 1 | Bunyaviridae,Nairovirus,Dugbe virus | seg. M | M25150,AF434161,A F434164,AF434163,A F434165,AF434162 |
| Dugbe virus | NC_004159 | vertebrates,invertebrates, human | 1 | Bunyaviridae,Nairovirus,Dugbe virus | seg. L | M94133 |
| Durania virus | NC_015450 | vertebrates,invertebrates, human | 1 | Bunyaviridae,Phlebovirus,Aguacate virus | seg. M | U15018 |
| Durania virus | NC_015451 | vertebrates,invertebrates, human | 1 | Bunyaviridae,Phlebovirus,Aguacate virus | seg. L | HM566157 |
| Durania virus | NC_015452 | vertebrates,invertebrates, human | 1 | Bunyaviridae,Phlebovirus,Aguacate virus | seg. S | HM566155 |
| Echarate virus | NC_015373 | vertebrates,invertebrates, human | 1 | Bunyaviridae,Phlebovirus,Candiru virus | seg. M | HM566156 |
| Echarate virus | NC_015374 | vertebrates,invertebrates, human | 1 | Bunyaviridae,Phlebovirus,Candiru virus | seg. L | HM119411 |
| Echarate virus | NC_015375 | vertebrates,invertebrates, human | 1 | Bunyaviridae,Phlebovirus,Candiru virus | seg. S | HM119410 |
| | | | | | | HM119412 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Entebbe bat virus | NC_008718 | vertebrates,invertebrates,human | 2 | Flaviviridae,Flavivirus,Entebbe bat virus | seg. S | DQ837641,AY632537 |
| Eyach virus | NC_003696 | vertebrates,invertebrates,human | 1 | Reoviridae,Coltivirus,Eyach virus | seg. 1 | AF282467 |
| Eyach virus | NC_003697 | vertebrates,invertebrates,human | 1 | Reoviridae,Coltivirus,Eyach virus | seg. 2 | AF282468 |
| Eyach virus | NC_003698 | vertebrates,invertebrates,human | 1 | Reoviridae,Coltivirus,Eyach virus | seg. 3 | AF282469 |
| Eyach virus | NC_003699 | vertebrates,invertebrates,human | 1 | Reoviridae,Coltivirus,Eyach virus | seg. 4 | AF282470 |
| Eyach virus | NC_003700 | vertebrates,invertebrates,human | 1 | Reoviridae,Coltivirus,Eyach virus | seg. 5 | AF282471 |
| Eyach virus | NC_003701 | vertebrates,invertebrates,human | 1 | Reoviridae,Coltivirus,Eyach virus | seg. 6 | AF282472 |
| Eyach virus | NC_003702 | vertebrates,invertebrates,human | 1 | Reoviridae,Coltivirus,Eyach virus | seg. 7 | AF282473 |
| Eyach virus | NC_003703 | vertebrates,invertebrates,human | 1 | Reoviridae,Coltivirus,Eyach virus | seg. 8 | AF282474 |
| Eyach virus | NC_003704 | vertebrates,invertebrates,human | 1 | Reoviridae,Coltivirus,Eyach virus | seg. 9 | AF282475 |
| Eyach virus | NC_003705 | vertebrates,invertebrates,human | 1 | Reoviridae,Coltivirus,Eyach virus | seg. 10 | AF282476 |
| Eyach virus | NC_003706 | vertebrates,invertebrates,human | 1 | Reoviridae,Coltivirus,Eyach virus | seg. 11 | AF282477 |
| Eyach virus | NC_003707 | vertebrates,invertebrates,human | 1 | Reoviridae,Coltivirus,Eyach virus | seg. 12 | AF282478 |
| Flavivirus White Kaiya duck/WR/China/2010 | NC_015843 | vertebrates,invertebrates,human | 1 | Flaviviridae,Flavivirus,Tembusu virus | — | JX196334 |
| Flavivirus muscovy/SD/China/2011 | NC_015843 | vertebrates,invertebrates,human | 1 | Flaviviridae,Flavivirus,Tembusu virus | — | JN232077 |
| Fort Sherman virus | NC_001927 | vertebrates,invertebrates,human | 1 | Bunyaviridae,Orthobunyavirus,Bunyamwera virus | seg. S | EU564829 |
| Germiston virus | NC_001926 | vertebrates,invertebrates,human | 1 | Bunyaviridae,Orthobunyavirus,Bunyamwera virus | seg. M | M21951 |
| Grand Arbaud virus | NC_005214 | vertebrates,invertebrates,human | 1 | Bunyaviridae,Phlebovirus,Uukuniemi virus | seg. L | JF833327 |
| Grand Arbaud virus | NC_005220 | vertebrates,invertebrates,human | 1 | Bunyaviridae,Phlebovirus,Uukuniemi virus | seg. M | JF833328 |
| Great Island virus | NC_014522 | vertebrates,invertebrates,human | 1 | Reoviridae,Orbivirus,Great Island virus | seg. 1 | HM543465 |
| Great Island virus | NC_014523 | vertebrates,invertebrates,human | 1 | Reoviridae,Orbivirus,Great Island virus | seg. 2 | HM543466 |
| Great Island virus | NC_014524 | vertebrates,invertebrates,human | 1 | Reoviridae,Orbivirus,Great Island virus | seg. 3 | HM543467 |
| Great Island virus | NC_014525 | vertebrates,invertebrates,human | 1 | Reoviridae,Orbivirus,Great Island virus | seg. 4 | HM543468 |
| Great Island virus | NC_014526 | vertebrates,invertebrates,human | 1 | Reoviridae,Orbivirus,Great Island virus | seg. 5 | HM543469 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Great Island virus | NC_014527 | vertebrates,invertebrates,human | 1 | Reoviridae,Orbivirus,Great Island virus | seg. 6 | HM543470 |
| Great Island virus | NC_014528 | vertebrates,invertebrates,human | 1 | Reoviridae,Orbivirus,Great Island virus | seg. 7 | HM543471 |
| Great Island virus | NC_014529 | vertebrates,invertebrates,human | 1 | Reoviridae,Orbivirus,Great Island virus | seg. 8 | HM543472 |
| Great Island virus | NC_014530 | vertebrates,invertebrates,human | 1 | Reoviridae,Orbivirus,Great Island virus | seg. 9 | HM543473 |
| Great Island virus | NC_014531 | vertebrates,invertebrates,human | 1 | Reoviridae,Orbivirus,Great Island virus | seg. 10 | HM543474 |
| Hazara virus | NC_005300 | vertebrates,invertebrates,human | 1 | Bunyaviridae,Nairovirus,Crimean-Congo hemorrhagic fever virus | seg. M | DQ813514 |
| Hazara virus | NC_005301 | vertebrates,invertebrates,human | 1 | Bunyaviridae,Nairovirus,Crimean-Congo hemorrhagic fever virus | seg. L | DQ076419 |
| Hazara virus | NC_005302 | vertebrates,invertebrates,human | 1 | Bunyaviridae,Nairovirus,Crimean-Congo hemorrhagic fever virus | seg. S | M86624 |
| Huaiyangshan virus | NC_018136 | vertebrates,invertebrates,human | 1 | Bunyaviridae,Phlebovirus,Severe fever with thrombocytopenia syndrome virus | seg. L | JF906056 |
| Huaiyangshan virus | NC_018137 | vertebrates,invertebrates,human | 1 | Bunyaviridae,Phlebovirus,Severe fever with thrombocytopenia syndrome virus | seg. S | JF906058 |
| Huaiyangshan virus | NC_018138 | vertebrates,invertebrates,human | 3 | Bunyaviridae,Phlebovirus,Severe fever with thrombocytopenia syndrome virus | seg. M | JF951394,JF906057,JF951393 |
| Igbo Ora virus | NC_001512 | vertebrates,invertebrates,human | 1 | Togaviridae,Alphavirus,O nyong-nyong virus | — | AF079457 |
| Iguape virus | NC_009026 | vertebrates,invertebrates,human | 1 | Flaviviridae,Flavivirus,Aroa virus | — | AY632538 |
| Ilesha virus | NC_001926 | vertebrates,invertebrates,human | 1 | Bunyaviridae,Orthobunyavirus,Bunyamwera virus | seg. M | AY859372 |
| Ilesha virus | NC_001927 | vertebrates,invertebrates,human | 3 | Bunyaviridae,Orthobunyavirus,Bunyamwera virus | seg. S | AM709780,AM709779,AY729651 |
| Ilheus virus | NC_009028 | vertebrates,invertebrates,human | 2 | Flaviviridae,Flavivirus,Ilheus virus | | KC481679,AY632539 |
| Inkoo virus | NC_004108 | vertebrates,invertebrates,human | 1 | Bunyaviridae,Orthobunyavirus,California encephalitis virus | seg. L | EU789573 |
| Inkoo virus | NC_004109 | vertebrates,invertebrates,human | 2 | Bunyaviridae,Orthobunyavirus,California encephalitis virus | seg. M | U88059,U88060 |
| Inkoo virus | NC_004110 | vertebrates,invertebrates,human | 2 | Bunyaviridae,Orthobunyavirus,California encephalitis virus | seg. S | U47137,U47138 |
| Israel turkey meningoencephalomyelitis virus | NC_012534 | vertebrates,invertebrates,human | 5 | Flaviviridae,Flavivirus,Bagaza virus | seg. M | KC734553,KC734550,KC734552,KC734549,KC734551 |
| Itaituba virus | NC_015373 | vertebrates,invertebrates,human | 1 | Bunyaviridae,Phlebovirus,Candiru virus | seg. M | HM119417 |
| Itaituba virus | NC_015374 | vertebrates,invertebrates,human | 1 | Bunyaviridae,Phlebovirus,Candiru virus | seg. L | HM119416 |
| Itaituba virus | NC_015375 | vertebrates,invertebrates,human | 1 | Bunyaviridae,Phlebovirus,Candiru virus | seg. S | HM119418 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Ixcanal virus | NC_015450 | vertebrates,invertebrates,human | 1 | Bunyaviridae,Phlebovirus,Aguacate virus | seg. M | HM566163 |
| Ixcanal virus | NC_015451 | vertebrates,invertebrates,human | 1 | Bunyaviridae,Phlebovirus,Aguacate virus | seg. L | HM566162 |
| Ixcanal virus | NC_015452 | vertebrates,invertebrates,human | 1 | Bunyaviridae,Phlebovirus,Aguacate virus | seg. S | HM566161 |
| Jacunda virus | NC_015373 | vertebrates,invertebrates,human | 1 | Bunyaviridae,Phlebovirus,Candiru virus | seg. M | HM466935 |
| Jacunda virus | NC_015374 | vertebrates,invertebrates,human | 1 | Bunyaviridae,Phlebovirus,Candiru virus | seg. L | HM466934 |
| Jacunda virus | NC_015375 | vertebrates,invertebrates,human | 1 | Bunyaviridae,Phlebovirus,Candiru virus | seg. S | HM466936 |
| Jamestown Canyon virus | NC_004109 | vertebrates,invertebrates,human | 1 | Bunyaviridae,Orthobunyavirus,California encephalitis virus | seg. M | U88058 |
| Jamestown Canyon virus | NC_004110 | vertebrates,invertebrates,human | 1 | Bunyaviridae,Orthobunyavirus,California encephalitis virus | seg. S | U12796 |
| Japanese encephalitis virus | NC_001437 | vertebrates,invertebrates,human | 171 | Flaviviridae,Flavivirus,Japanese encephalitis virus | — | JN381857,JF706274,AB551990,AF254452,JN381837,M18370,KF299715,IQ086763,JN381858,KC915016,JN381855,JN381861,JXQ72965,JF706281,JN381862,D90195,JF706278,FJ185037,JXQ50179,U14163,AY84939,JN381869,JN381832,AB698906,AB698907,JF706269,AB051292,JN381849,JN381870,EF571853,JN381859,JF499790,JF706282,JN381831,M55506,JN381851,JF706280,JN711458,AY585242,JN381844,GQ902061,JN381863,AY303798,JF706272,HQ652538,AF075723,JF706270,JF706283,AY508813,JN381840,JN381830,JN381850,AF221500,AY303792,AB241118,AF254453,AB551991,AY508812,JN644310,AB241119,AF486638,AB830335,JN381864,JN381847,KF29 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 7916,HM22921,JF706284,AF315119,JF706277,JN381860,AF416457,AF069076,GU205163,GQ918133,AF221499,JF706267,JN381833,JN381843,JN381871,JF706286,AB698905,JN381854,JN381873,JN381848,JF706275,FJ495189,AY316157,EF623987,JF706268,HM366552,AF014161,GU556217,JN381834,JN381842,AY303794,JN381853,JF499788,JX131374,AF014160,HM596272,AY585243,JN711459,AF098735,AF045551,AF098737,GQ90205 9,AB196926,JN60498 6,AY303796,AF21762 0,AY303797,EF62398 8,JN381841,GQ9020 60,JN381856,JN3818 52,JF706273,JQ0867 62,JF706276,D90194 ,EU429297,AY30379 1,AB196925,KC5174 97,JN381866,JN8640 64,JF706279,AB5948 29,L48961,FJ185036, AB698908,JN381846, AB853904,AF080251, JF499789,JN381845, JN381867,AB196924, JN381872,HE861351, GQ902062,EF623989 ,EU880214,HQ89354 5,GQ199609,AY3037 93,JN381836,KC1961 15,JN381835,U15763 ,AB196923,EF543861 ,AB698909,EU69389 9,JF706271,JF70628 5,JN381838,L78128,J N381839,GU187972, |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Jerry Slough virus | NC_004109 | vertebrates,invertebrates,human | Bunyaviridae,Orthobunyavirus,California encephalitis virus | 1 | seg. M | AY30795,U47032,GQ90205 8,EF107523,JF915894,AB551992,GQ902063,JN381868,AY184212,JN381865,AF098736,AF123487 |
| Kadipiro virus | NC_004199 | vertebrates,invertebrates,human | Reoviridae,Seadornavirus,Kadipiro virus | 2 | seg. 12 | AF019909,FJ159105 |
| Kadipiro virus | NC_004205 | vertebrates,invertebrates,human | Reoviridae,Seadornavirus,Kadipiro virus | 1 | seg. 11 | AF052019 |
| Kadipiro virus | NC_004206 | vertebrates,invertebrates,human | Reoviridae,Seadornavirus,Kadipiro virus | 1 | seg. 10 | AF052020 |
| Kadipiro virus | NC_004207 | vertebrates,invertebrates,human | Reoviridae,Seadornavirus,Kadipiro virus | 1 | seg. 9 | AF052021 |
| Kadipiro virus | NC_004208 | vertebrates,invertebrates,human | Reoviridae,Seadornavirus,Kadipiro virus | 1 | seg. 8 | AF052022 |
| Kadipiro virus | NC_004209 | vertebrates,invertebrates,human | Reoviridae,Seadornavirus,Kadipiro virus | 1 | seg. 7 | AF052023 |
| Kadipiro virus | NC_004210 | vertebrates,invertebrates,human | Reoviridae,Seadornavirus,Kadipiro virus | 1 | seg. 1 | AF133429 |
| Kadipiro virus | NC_004212 | vertebrates,invertebrates,human | Reoviridae,Seadornavirus,Kadipiro virus | 1 | seg. 2 | AF134509 |
| Kadipiro virus | NC_004213 | vertebrates,invertebrates,human | Reoviridae,Seadornavirus,Kadipiro virus | 1 | seg. 3 | AF134510 |
| Kadipiro virus | NC_004214 | vertebrates,invertebrates,human | Reoviridae,Seadornavirus,Kadipiro virus | 1 | seg. 4 | AF134511 |
| Kadipiro virus | NC_004215 | vertebrates,invertebrates,human | Reoviridae,Seadornavirus,Kadipiro virus | 1 | seg. 5 | AF134512 |
| Kadipiro virus | NC_004216 | vertebrates,invertebrates,human | Reoviridae,Seadornavirus,Kadipiro virus | 1 | seg. 6 | AF134513 |
| Kamra virus | NC_023439 | vertebrates,invertebrates,human | Flaviviridae,Flavivirus,Kamra virus | 1 | — | KF815940 |
| Kamiti River virus | NC_005064 | vertebrates,invertebrates,human | Flaviviridae,Flavivirus,Kamiti River virus | 2 | — | AY149905,AY149904 |
| Karshi virus | NC_006947 | vertebrates,invertebrates,human | Flaviviridae,Flavivirus,Royal Farm virus | 3 | — | DQ235147,AY863002,DQ462443,AY632540 |
| Kedougou virus | NC_012533 | vertebrates,invertebrates,human | Flaviviridae,Flavivirus,Kedougou virus | 1 | — | |
| Kemerovo virus | NC_014522 | vertebrates,invertebrates,human | Reoviridae,Orbivirus,Great Island virus | 2 | seg. 1 | HQ266591,HM54348 1 |
| Kemerovo virus | NC_014523 | vertebrates,invertebrates,human | Reoviridae,Orbivirus,Great Island virus | 2 | seg. 2 | HQ266592,HM54348 |
| Kemerovo virus | NC_014524 | vertebrates,invertebrates,human | Reoviridae,Orbivirus,Great Island virus | 1 | seg. 3 | HQ266593 |
| Kemerovo virus | NC_014525 | vertebrates,invertebrates,human | Reoviridae,Orbivirus,Great Island virus | 1 | seg. 4 | HQ266594 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Kemerovo virus | NC_014526 | vertebrates,invertebrates,human | 2 | Reoviridae,Orbivirus,Great Island virus | seg. 5 | HQ266596,HQ26659 |
| Kemerovo virus | NC_014527 | vertebrates,invertebrates,human | 5 | Reoviridae,Orbivirus,Great Island virus | seg. 6 | HM543483 |
| Kemerovo virus | NC_014528 | vertebrates,invertebrates,human | 1 | Reoviridae,Orbivirus,Great Island virus | seg. 7 | HQ266597 |
| Kemerovo virus | NC_014529 | vertebrates,invertebrates,human | 1 | Reoviridae,Orbivirus,Great Island virus | seg. 8 | HQ266598 |
| Kemerovo virus | NC_014530 | vertebrates,invertebrates,human | 1 | Reoviridae,Orbivirus,Great Island virus | seg. 9 | HQ266599 |
| Kemerovo virus | NC_014531 | vertebrates,invertebrates,human | 1 | Reoviridae,Orbivirus,Great Island virus | seg. 10 | HQ266600 |
| Keystone virus | NC_004109 | vertebrates,invertebrates,human | 1 | Bunyaviridae,Orthobunyavirus,California encephalitis virus | seg. M | AF123489 |
| Keystone virus | NC_004110 | vertebrates,invertebrates,human | 1 | Bunyaviridae,Orthobunyavirus,California encephalitis virus | seg. S | U12801 |
| Kokobera virus | NC_009029 | vertebrates,invertebrates,human | 1 | Flaviviridae,Flavivirus,Kokobera virus | — | AY632541 |
| Kunjin virus | NC_001563 | vertebrates,invertebrates,human | 3 | Flaviviridae,Flavivirus,West Nile virus | — | DQ0246,AY274505,AY274504 |
| Kunjin virus | NC_009942 | vertebrates,invertebrates,human | 3 | Flaviviridae,Flavivirus,West Nile virus | — | DQ0246,AY274505,AY274504 |
| Kyasanur forest disease virus | NC_004355 | vertebrates,invertebrates,human | 6 | Flavi

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Liao ning virus | NC_007739 | vertebrates,invertebrates,human | 1 | Reoviridae,Seadornavirus,Liao ning virus | seg. 4 | AY701342 |
| Liao ning virus | NC_007740 | vertebrates,invertebrates,human | 1 | Reoviridae,Seadornavirus,Liao ning virus | seg. 5 | AY701343 |
| Liao ning virus | NC_007741 | vertebrates,invertebrates,human | 1 | Reoviridae,Seadornavirus,Liao ning virus | seg. 6 | AY701344 |
| Liao ning virus | NC_007742 | vertebrates,invertebrates,human | 1 | Reoviridae,Seadornavirus,Liao ning virus | seg. 7 | AY701345 |
| Liao ning virus | NC_007743 | vertebrates,invertebrates,human | 1 | Reoviridae,Seadornavirus,Liao ning virus | seg. 8 | AY701346 |
| Liao ning virus | NC_007744 | vertebrates,invertebrates,human | 1 | Reoviridae,Seadornavirus,Liao ning virus | seg. 9 | AY701347 |
| Liao ning virus | NC_007745 | vertebrates,invertebrates,human | 1 | Reoviridae,Seadornavirus,Liao ning virus | seg. 10 | AY701348 |
| Liao ning virus | NC_007746 | vertebrates,invertebrates,human | 1 | Reoviridae,Seadornavirus,Liao ning virus | seg. 11 | AY701349 |
| Liao ning virus | NC_007747 | vertebrates,invertebrates,human | 1 | Reoviridae,Seadornavirus,Liao ning virus | seg. 12 | AY701350 |
| Lipovnik virus | NC_014522 | vertebrates,invertebrates,human | 1 | Reoviridae,Orbivirus,Great Island virus | seg. 1 | HM543475 |
| Lipovnik virus | NC_014523 | vertebrates,invertebrates,human | 1 | Reoviridae,Orbivirus,Great Island virus | seg. 2 | HM543476 |
| Louping ill virus | NC_001809 | vertebrates,invertebrates,human | 2 | Flaviviridae,Flavivirus,Louping ill virus | — | Y07863,KF056331 |
| Lumbo virus | NC_004109 | vertebrates,invertebrates,human | 1 | Bunyaviridae,Orthobunyavirus,California encephalitis virus | seg. M | AF123484 |
| Lumbo virus | NC_004110 | vertebrates,invertebrates,human | 1 | Bunyaviridae,Orthobunyavirus,California encephalitis virus | seg. S | X73468 |
| Maguari virus | NC_001926 | vertebrates,invertebrates,human | 4 | Bunyaviridae,Orthobunyavirus,Bunyamwera virus | seg. M | AY286444,AY286443,AY286445,AY286446 |
| Maldonado virus | NC_015373 | vertebrates,invertebrates,human | 1 | Bunyaviridae,Phlebovirus,Candiru virus | seg. M | HM119414 |
| Maldonado virus | NC_015374 | vertebrates,invertebrates,human | 1 | Bunyaviridae,Phlebovirus,Candiru virus | seg. L | HM119413 |
| Maldonado virus | NC_015375 | vertebrates,invertebrates,human | 1 | Bunyaviridae,Phlebovirus,Candiru virus | seg. S | HM119415 |
| Massilia virus | NC_006318 | vertebrates,invertebrates,human | 1 | Bunyaviridae,Phlebovirus,Sandfly fever Naples virus | seg. S | EU725773 |
| Massilia virus | NC_006319 | vertebrates,invertebrates,human | 1 | Bunyaviridae,Phlebovirus,Sandfly fever Naples virus | seg. L | EU725771 |
| Massilia virus | NC_006320 | vertebrates,invertebrates,human | 1 | Bunyaviridae,Phlebovirus,Sandfly fever Naples virus | seg. M | EU725772 |
| Mayaro virus | NC_003417 | vertebrates,invertebrates,human | 2 | Togaviridae,Alphavirus,Mayaro virus | — | DQ001069,AF237947 |
| Mboke virus | NC_001927 | vertebrates,invertebrates,human | 1 | Bunyaviridae,Orthobunyavirus,Bunyamwera virus | seg. S | AY593727 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Melao virus | NC_004109 | vertebrates,invertebrates,human | 1 | Bunyaviridae,Orthobunyavirus,California encephalitis virus | seg. M | U88057 |
| Modoc virus | NC_003635 | vertebrates,invertebrates,human | 1 | Flaviviridae,Flavivirus,Modoc virus | — | AJ242984 |
| Montana myotis leukoencephalitis virus | NC_004119 | vertebrates,invertebrates,human | 1 | Flaviviridae,Flavivirus,Montana myotis leukoencephalitis virus | — | AJ299445 |
| Morro Bay virus | NC_004110 | vertebrates,invertebrates,human | 1 | Bunyaviridae,Orthobunyavirus,California encephalitis virus | seg. S | U31989 |
| Morumbi virus | NC_015373 | vertebrates,invertebrates,human | 1 | Bunyaviridae,Phlebovirus,Candiru virus | seg. M | HM119423 |
| Morumbi virus | NC_015374 | vertebrates,invertebrates,human | 1 | Bunyaviridae,Phlebovirus,Candiru virus | seg. L | HM119422 |
| Morumbi virus | NC_015375 | vertebrates,invertebrates,human | 1 | Bunyaviridae,Phlebovirus,Candiru virus | seg. S | HM119424 |
| Mosquito flavivirus | NC_021069 | vertebrates,invertebrates, 1 human | | Flaviviridae,Flavivirus,Mosquito flavivirus | — | KC464457 |
| Mucura virus | NC_015373 | vertebrates,invertebrates,human | 1 | Bunyaviridae,Phlebovirus,Candiru virus | seg. M | HM119420 |
| Mucura virus | NC_015374 | vertebrates,invertebrates,human | 1 | Bunyaviridae,Phlebovirus,Candiru virus | seg. L | HM119419 |
| Mucura virus | NC_015375 | vertebrates,invertebrates,human | 1 | Bunyaviridae,Phlebovirus,Candiru virus | seg. S | HM119421 |
| Murray Valley encephalitis virus | NC_000943 | vertebrates,invertebrates,human | 10 | Flaviviridae,Flavivirus,Murray Valley encephalitis virus | — | KC852193,JX123032,AF161266,KC852192,KC852194,KC852195,KC852189,KC852190,KC852191,KC852196 |
| Murre virus | NC_005214 | vertebrates,invertebrates,human | 1 | Bunyaviridae,Phlebovirus,Uukuniemi virus | seg. L | JF838330 |
| Murre virus | NC_005220 | vertebrates,invertebrates,human | 1 | Bunyaviridae,Phlebovirus,Uukuniemi virus | seg. M | JF838331 |
| Ngari virus | NC_001926 | vertebrates,invertebrates,human | 1 | Bunyaviridae,Orthobunyavirus,Bunyamwera virus | seg. M | AY593725 |
| Ngari virus | NC_001927 | vertebrates,invertebrates,human | 1 | Bunyaviridae,Orthobunyavirus,Bunyamwera virus | seg. S | AY593729 |
| Nique virus | NC_015373 | vertebrates,invertebrates,human | 1 | Bunyaviridae,Phlebovirus,Candiru virus | seg. M | HM119426 |
| Nique virus | NC_015374 | vertebrates,invertebrates,human | 1 | Bunyaviridae,Phlebovirus,Candiru virus | seg. L | HM119425 |
| Nique virus | NC_015375 | vertebrates,invertebrates,human | 1 | Bunyaviridae,Phlebovirus,Candiru virus | seg. S | HM119427 |
| Northway virus | NC_001927 | vertebrates,invertebrates,human | 1 | Bunyaviridae,Orthobunyavirus,Bunyamwera virus | seg. S | X73470 |
| Ntaya virus | NC_018705 | vertebrates,invertebrates,human | 1 | Flaviviridae,Flavivirus,Ntaya virus | — | JX236040 |
| O'nyong-nyong virus | NC_001512 | vertebrates,invertebrates,human | 2 | Togaviridae,,Alphavirus,O'nyong-nyong virus | — | AF079456,M20303 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Omsk hemorrhagic fever virus | NC_005062 | vertebrates,invertebrates, human | 4 | Flaviviridae,Flavivirus,Omsk hemorrhagic fever virus | — | AY323489,AB507800,AY438626,AY193805 |
| Oriximina virus | NC_015373 | vertebrates,invertebrates, human | 1 | Bunyaviridae,Phlebovirus,Candiru virus | seg. M | HM119435 |
| Oriximina virus | NC_015374 | vertebrates,invertebrates, human | 1 | Bunyaviridae,Phlebovirus,Candiru virus | seg. L | HM119434 |
| Oriximina virus | NC_015375 | vertebrates,invertebrates, human | 1 | Bunyaviridae,Phlebovirus,Candiru virus | seg. S | HM119436 |
| Oropouche virus | NC_005775 | vertebrates,invertebrates, human | 2 | Bunyaviridae,Orthobunyavirus,Oropouche virus | seg. M | AF312381,AF441119 |
| Oropouche virus | NC_005776 | vertebrates,invertebrates, human | 1 | Bunyaviridae,Orthobunyavirus,Oropouche virus | seg. L | AF484424 |
| Oropouche virus | NC_005777 | vertebrates,invertebrates, human | 2 | Bunyaviridae,Orthobunyavirus,Oropouche virus | seg. S | AY237111,AY117135 |
| Orthobunyavirus BX-2010/Henan/CHN | NC_018136 | vertebrates,invertebrates, human | 3 | Bunyaviridae,Phlebovirus,Severe fever with thrombocytopenia syndrome virus | seg. L | HQ642766,JF682773,JF682776 |
| Orthobunyavirus BX-2010/Henan/CHN | NC_018137 | vertebrates,invertebrates, human | 3 | Bunyaviridae,Phlebovirus,Severe fever with thrombocytopenia syndrome virus | seg. S | HQ642768,JF682778,JF682775 |
| Orthobunyavirus BX-2010/Henan/CHN | NC_018138 | vertebrates,invertebrates, human | 3 | Bunyaviridae,Phlebovirus,Severe fever with thrombocytopenia syndrome virus | seg. M | JF682774,JF682777,HQ642767 |
| Peaton virus | NC_018463 | vertebrates,invertebrates, human | 1 | Bunyaviridae,Orthobunyavirus,Shamonda virus | seg. L | HE795093 |
| Peaton virus | NC_018464 | vertebrates,invertebrates, human | 1 | Bunyaviridae,Orthobunyavirus,Shamonda virus | seg. S | HE795095 |
| Peaton virus | NC_018467 | vertebrates,invertebrates, human | 1 | Bunyaviridae,Orthobunyavirus,Shamonda virus | seg. M | HE795094 |
| Phlebovirus JS2007-01 | NC_018136 | vertebrates,invertebrates, human | 1 | Bunyaviridae,Phlebovirus,Severe fever with thrombocytopenia syndrome virus | seg. L | JF837593 |
| Phlebovirus JS2007-01 | NC_018138 | vertebrates,invertebrates, human | 1 | Bunyaviridae,Phlebovirus,Severe fever with thrombocytopenia syndrome virus | seg. M | JF837594 |
| Phlebovirus JS2010-014 | NC_018136 | vertebrates,invertebrates, human | 1 | Bunyaviridae,Phlebovirus,Severe fever with thrombocytopenia syndrome virus | seg. L | JQ317169 |
| Phlebovirus JS2010-014 | NC_018137 | vertebrates,invertebrates, human | 1 | Bunyaviridae,Phlebovirus,Severe fever with thrombocytopenia syndrome virus | seg. S | JQ317171 |
| Phlebovirus JS2010-014 | NC_018138 | vertebrates,invertebrates, human | 1 | Bunyaviridae,Phlebovirus,Severe fever with thrombocytopenia syndrome virus | seg. M | JQ317170 |
| Phlebovirus JS2010-015 | NC_018136 | vertebrates,invertebrates, human | 1 | Bunyaviridae,Phlebovirus,Severe fever with thrombocytopenia syndrome virus | seg. L | JQ317172 |
| Phlebovirus JS2010-015 | NC_018137 | vertebrates,invertebrates, human | 1 | Bunyaviridae,Phlebovirus,Severe fever with thrombocytopenia syndrome virus | seg. S | JQ317174 |
| Phlebovirus JS2010-015 | NC_018138 | vertebrates,invertebrates, human | 1 | Bunyaviridae,Phlebovirus,Severe fever with thrombocytopenia syndrome virus | seg. M | JQ317173 |
| Phlebovirus JS2010-018 | NC_018136 | vertebrates,invertebrates, human | 1 | Bunyaviridae,Phlebovirus,Severe fever with thrombocytopenia syndrome virus | seg. L | JQ317175 |
| Phlebovirus JS2010-018 | NC_018137 | vertebrates,invertebrates, human | 1 | Bunyaviridae,Phlebovirus,Severe fever with thrombocytopenia syndrome virus | seg. S | JQ317177 |

TABLE 10-continued

VifoCap-1.0 Taxonomy

| Taxonomy | Rep.Acc.ID | Host | Lineage | # GN's | Seg. Count | GN.Acc.IDs |
|---|---|---|---|---|---|---|
| Phlebovirus JS2010-018 | NC_018138 | vertebrates,invertebrates,human TABLE 10-continued ViroCap-1.0 Taxonomy

| Taxonomy | Rep.Acc.ID | Host | # GN's | Lineage | Seg. Count | GN.Acc.IDs |
|---|---|---|---|---|---|---|
| Razdan virus | NC_022631 | vertebrates,invertebrates, human | 1 | Bunyaviridae,Phlebovirus,Razdan virus | seg. M | KC335497 |
| Razdan virus | NC_022632 | vertebrates,invertebrates, human | 1 | Bunyaviridae,Phlebovirus,Razdan virus | seg. S | KC335498 |
| Rift Valley fever virus | NC_014395 | vertebrates,invertebrates, human | 50 | Buny TABLE 10-continued ViroCap-1.0 Taxonomy

| Taxonomy | Rep.Acc.ID | Host | # GN's | Lineage | Seg. Count | GN.Acc.IDs |
|---|---|---|---|---|---|---|
| Rift Valley fever virus | NC_014397 | vertebrates,invertebrates,human | 50 | Bun TABLE 10-continued ViroCap-1.0 Taxonomy

| Taxonomy | Rep.Acc.ID | Host | # GN's | Lineage | Seg. Count | GN.Acc.IDs |
|---|---|---|---|---|---|---|
| Royal Farm virus | NC_006947 | vertebrates,invertebrates, human | 1 | Flaviviridae,Flavivirus,Royal Farm virus | — | DQ235149 |
| SFTS virus AH12 | NC_018136 | vertebrates,invertebrates, human | 1 | Bunyaviridae,Phlebovirus,Severe fever with thrombocytopenia syndrome virus | seg. L | HQ116417 |
| SFTS virus AH12 | NC_018137 | vertebrates,invertebrates, human | 1 | Bunyaviridae,Phlebovirus,Severe fever with thrombocytopenia syndrome virus | seg. S | HQ141591 |
| SFTS virus AH12 | NC_018138 | vertebrates,invertebrates, human | 1 | Bunyaviridae,Phlebovirus,Severe fever with thrombocytopenia syndrome virus | seg. M | HQ141590 |
| SFTS virus AH15 | NC_018136 | vertebrates,invertebrates, human | 1 | Bunyaviridae,Phlebovirus,Severe fever with thrombocytopenia syndrome virus | seg. L | HQ141592 |
| SFTS virus AH15 | NC_018137 | vertebrates,invertebrates, human | 1 | Bunyaviridae,Phlebovirus,Severe fever with thrombocytopenia syndrome virus | seg. S | HQ141594 |
| SFTS virus AH15 | NC_018138 | vertebrates,invertebrates, human | 1 | Bunyaviridae,Phlebovirus,Severe fever with thrombocytopenia syndrome virus | seg. M | HQ141593 |
| SFTS virus HB29 | NC_018136 | vertebrates,invertebrates, human | 1 | Bunyaviridae,Phlebovirus,Severe fever with thrombocytopenia syndrome virus | seg. L | HM745930 |
| SFTS virus HB29 | NC_018137 | vertebrates,invertebrates, human | 1 | Bunyaviridae,Phlebovirus,Severe fever with thrombocytopenia syndrome virus | seg. S | HM745932 |
| SFTS virus HB29 | NC_018138 | vertebrates,invertebrates, human | 1 | Bunyaviridae,Phlebovirus,Severe fever with thrombocytopenia syndrome virus | seg. M | HM745931 |
| SFTS virus HN13 | NC_018136 | vertebrates,invertebrates, human | 1 | Bunyaviridae,Phlebovirus,Severe fever with thrombocytopenia syndrome virus | seg. L | HQ141598 |
| SFTS virus HN13 | NC_018137 | vertebrates,invertebrates, human | 1 | Bunyaviridae,Phlebovirus,Severe fever with thrombocytopenia syndrome virus | seg. S | HQ141600 |
| SFTS virus HN13 | NC_018138 | vertebrates,invertebrates, human | 1 | Bunyaviridae,Phlebovirus,Severe fever with thrombocytopenia syndrome virus | seg. M | HQ141599 |
| SFTS virus HN6 | NC_018136 | vertebrates,invertebrates, human | 1 | Bunyaviridae,Phlebovirus,Severe fever with thrombocytopenia syndrome virus | seg. L | HQ141595 |
| SFTS virus HN6 | NC_018137 | vertebrates,invertebrates, human | 1 | Bunyaviridae,Phlebovirus,Severe fever with thrombocytopenia syndrome virus | seg. S | HQ141597 |
| SFTS virus HN6 | NC_018138 | vertebrates,invertebrates/ human | 1 | Bunyaviridae,Phlebovirus,Severe fever with thrombocytopenia syndrome virus | seg. M | HQ141596 |
| SFTS virus HNXY_115 | NC_018136 | vertebrates,invertebrates, human | 1 | Bunyaviridae,Phlebovirus,Severe fever with thrombocytopenia syndrome virus | seg. L | KC292338 |
| SFTS virus HNXY_115 | NC_018137 | vertebrates,invertebrates, human | 1 | Bunyaviridae,Phlebovirus,Severe fever with thrombocytopenia syndrome virus | seg. S | KC292285 |
| SFTS virus HNXY_115 | NC_018138 | vertebrates,invertebrates, human | 1 | Bunyaviridae,Phlebovirus,Severe fever with thrombocytopenia syndrome virus | seg. M | KC292312 |
| SFTS virus HNXY_130 | NC_018136 | vertebrates,invertebrates, human | 1 | Bunyaviridae,Phlebovirus,Severe fever with thrombocytopenia syndrome virus | seg. L | KC292342 |
| SFTS virus HNXY_130 | NC_018137 | vertebrates,invertebrates, human | 1 | Bunyaviridae,Phlebovirus,Severe fever with thrombocytopenia syndrome virus | seg. S | KC292289 |
| SFTS virus HNXY_130 | NC_018138 | vertebrates,invertebrates, human | 1 | Bunyaviridae,Phlebovirus,Severe fever with thrombocytopenia syndrome virus | seg. M | KC292316 |
| SFTS virus HNXY_144 | NC_018136 | vertebrates,invertebrates, human | 1 | Bunyaviridae,Phlebovirus,Severe fever with thrombocytopenia syndrome virus | seg. L | KC292333 |
| SFTS virus HNXY_144 | NC_018137 | vertebrates,invertebrates, human | 1 | Bunyaviridae,Phlebovirus,Severe fever with thrombocytopenia syndrome virus | seg. S | KC292280 |

TABLE 10-continued

VidCap-1.0 Taxonomy

| Taxonomy | Rep.Acc.ID | Host | # GN's | Lineage | Seg. Count | GN.Acc.IDs |
|---|---|---|---|---|---|---|
| SFTS virus HNXY_144 | NC_018138 | vertebrates,invertebrates, human | 1 | Bunyaviridae,Phlebovirus,Severe fever with thrombocytopenia syndrome virus | seg. M | KC292307 |
| SFTS virus HNXY_157 | NC_018136 | vertebrates,invertebrates, human | 1 | Bunyaviridae,Phlebovirus,Severe fever with thrombocytopenia syndrome virus | seg. L | KC292331 |
| SFTS virus HNXY_157 | NC_018137 | vertebrates,invertebrates, human | 1 | Bunyaviridae,Phlebovirus,Severe fever with thrombocytopenia syndrome virus | seg. S | KC292278 |
| SFTS virus HNXY_157 | NC_018138 | vertebrates,invertebrates, human | 1 | Bunyaviridae,Phlebovirus,Severe fever with thrombocytopenia syndrome virus | seg. M | KC292305 |
| SFTS virus HNXY_164 | NC_018136 | vertebrates,invertebrates, human | 1 | Bunyaviridae,Phlebovirus,Severe fever with thrombocytopenia syndrome virus | seg. L | KC292340 |
| SFTS virus HNXY_164 | NC_018137 | vertebrates,invertebrates, human | 1 | Bunyaviridae,Phlebovirus,Severe fever with thrombocytopenia syndrome virus | seg. S | KC292287 |
| SFTS virus HNXY_164 | NC_018138 | vertebrates,invertebrates, human | 1 | Bunyaviridae,Phlebovirus,Severe fever with thrombocytopenia syndrome virus | seg. M | KC292314 |
| SFTS virus HNXY_170 | NC_018136 | vertebrates,invertebrates, human | 1 | Bunyaviridae,Phlebovirus,Severe fever with thrombocytopenia syndrome virus | seg. L | KC292353 |
| SFTS virus HNXY_170 | NC_018137 | vertebrates,invertebrates, human | 1 | Bunyaviridae,Phlebovirus,Severe fever with thrombocytopenia syndrome virus | seg. S | KC292277 |
| SFTS virus HNXY_170 | NC_018138 | vertebrates,invertebrates, human | 1 | Bunyaviridae,Phlebovirus,Severe fever with thrombocytopenia syndrome virus | seg. M | KC292304 |
| SFTS virus HNXY_174 | NC_018136 | vertebrates,invertebrates, human | 1 | Bunyaviridae,Phlebovirus,Severe fever with thrombocytopenia syndrome virus | seg. L | KC292332 |
| SFTS virus HNXY_174 | NC_018137 | vertebrates,invertebrates, human | 1 | Bunyaviridae,Phlebovirus,Severe fever with thrombocytopenia syndrome virus | seg. S | KC292279 |
| SFTS virus HNXY_174 | NC_018138 | vertebrates,invertebrates, human | 1 | Bunyaviridae,Phlebovirus,Severe fever with thrombocytopenia syndrome virus | seg. M | KC292306 |
| SFTS virus HNXY_182 | NC_018136 | vertebrates,invertebrates, human | 1 | Bunyaviridae,Phlebovirus,Severe fever with thrombocytopenia syndrome virus | seg. L | KC292350 |
| SFTS virus HNXY_182 | NC_018137 | vertebrates,invertebrates, human | 1 | Bunyaviridae,Phlebovirus,Severe fever with thrombocytopenia syndrome virus | seg. S | KC292297 |
| SFTS virus HNXY_182 | NC_018138 | vertebrates,invertebrates, human | 1 | Bunyaviridae,Phlebovirus,Severe fever with thrombocytopenia syndrome virus | seg. M | KC292324 |
| SFTS virus HNXY_186 | NC_018136 | vertebrates,invertebrates, human | 1 | Bunyaviridae,Phlebovirus,Severe fever with thrombocytopenia syndrome virus | seg. L | KC292334 |
| SFTS virus HNXY_186 | NC_018137 | vertebrates,invertebrates, human | 1 | Bunyaviridae,Phlebovirus,Severe fever with thrombocytopenia syndrome virus | seg. S | KC292281 |
| SFTS virus HNXY_186 | NC_018138 | vertebrates,invertebrates, human | 1 | Bunyaviridae,Phlebovirus,Severe fever with thrombocytopenia syndrome virus | seg. M | KC292308 |
| SFTS virus HNXY_188 | NC_018136 | vertebrates,invertebrates, human | 1 | Bunyaviridae,Phlebovirus,Severe fever with thrombocytopenia syndrome virus | seg. M | KC292328 |
| SFTS virus HNXY_188 | NC_018137 | vertebrates,invertebrates, human | 1 | Bunyaviridae,Phlebovirus,Severe fever with thrombocytopenia syndrome virus | seg. L | KC292274 |
| SFTS virus HNXY_188 | NC_018138 | vertebrates,invertebrates, human | 1 | Bunyaviridae,Phlebovirus,Severe fever with thrombocytopenia syndrome virus | seg. S | KC292301 |
| SFTS virus HNXY_191 | NC_018136 | vertebrates,invertebrates, human | 1 | Bunyaviridae,Phlebovirus,Severe fever with thrombocytopenia syndrome virus | seg. M | KC292349 |
| SFTS virus HNXY_191 | NC_018137 | vertebrates,invertebrates, human | 1 | Bunyaviridae,Phlebovirus,Severe fever with thrombocytopenia syndrome virus | seg. S | KC292296 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| SFTS virus HNXY_191 | NC_018138 | vertebrates,invertebrates, human | Bunyaviridae,Phlebovirus,Severe fever with thrombocytopenia syndrome virus | 1 | seg. M | KC292323 |
| SFTS virus HNXY_195 | NC_018136 | vertebrates,invertebrates, human | Bunyaviridae,Phlebovirus,Severe fever with thrombocytopenia syndrome virus | 1 | seg. L | KC292352 |
| SFTS virus HNXY_195 | NC_018137 | vertebrates,invertebrates, human | Bunyaviridae,Phlebovirus,Severe fever with thrombocytopenia syndrome virus | 1 | seg. S | KC292299 |
| SFTS virus HNXY_195 | NC_018138 | vertebrates,invertebrates, human | Bunyaviridae,Phlebovirus,Severe fever with thrombocytopenia syndrome virus | 1 | seg. M | KC292326 |
| SFTS virus HNXY_2 | NC_018136 | vertebrates,invertebrates, human | Bunyaviridae,Phlebovirus,Severe fever with thrombocytopenia syndrome virus | 1 | seg. L | KC292344 |
| SFTS virus HNXY_2 | NC_018137 | vertebrates,invertebrates, human | Bunyaviridae,Phlebovirus,Severe fever with thrombocytopenia syndrome virus | 1 | seg. S | KC292291 |
| SFTS virus HNXY_2 | NC_018138 | vertebrates,invertebrates, human | Bunyaviridae,Phlebovirus,Severe fever with thrombocytopenia syndrome virus | 1 | seg. M | KC292318 |
| SFTS virus HNXY_202 | NC_018136 | vertebrates,invertebrates, human | Bunyaviridae,Phlebovirus,Severe fever with thrombocytopenia syndrome virus | 1 | seg. L | KC292351 |
| SFTS virus HNXY_202 | NC_018137 | vertebrates,invertebrates, human | Bunyaviridae,Phlebovirus,Severe fever with thrombocytopenia syndrome virus | 1 | seg. S | KC292298 |
| SFTS virus HNXY_202 | NC_018138 | vertebrates,invertebrates, human | Bunyaviridae,Phlebovirus,Severe fever with thrombocytopenia syndrome virus | 1 | seg. M | KC292325 |
| SFTS virus HNXY_206 | NC_018136 | vertebrates,invertebrates, human | Bunyaviridae,Phlebovirus,Severe fever with thrombocytopenia syndrome virus | 1 | seg. L | KC292329 |
| SFTS virus HNXY_206 | NC_018137 | vertebrates,invertebrates, human | Bunyaviridae,Phlebovirus,Severe fever with thrombocytopenia syndrome virus | 1 | seg. S | KC292275 |
| SFTS virus HNXY_206 | NC_018138 | vertebrates,invertebrates, human | Bunyaviridae,Phlebovirus,Severe fever with thrombocytopenia syndrome virus | 1 | seg. M | KC292302 |
| SFTS virus HNXY_207 | NC_018136 | vertebrates,invertebrates, human | Bunyaviridae,Phlebovirus,Severe fever with thrombocytopenia syndrome virus | 1 | seg. L | KC292341 |
| SFTS virus HNXY_207 | NC_018137 | vertebrates,invertebrates, human | Bunyaviridae,Phlebovirus,Severe fever with thrombocytopenia syndrome virus | 1 | seg. S | KC292288 |
| SFTS virus HNXY_207 | NC_018138 | vertebrates,invertebrates, human | Bunyaviridae,Phlebovirus,Severe fever with thrombocytopenia syndrome virus | 1 | seg. M | KC292315 |
| SFTS virus HNXY_212 | NC_018136 | vertebrates,invertebrates, human | Bunyaviridae,Phlebovirus,Severe fever with thrombocytopenia syndrome virus | 1 | seg. L | KC292327 |
| SFTS virus HNXY_212 | NC_018137 | vertebrates,invertebrates, human | Bunyaviridae,Phlebovirus,Severe fever with thrombocytopenia syndrome virus | 1 | seg. S | KC292273 |
| SFTS virus HNXY_212 | NC_018138 | vertebrates,invertebrates, human | Bunyaviridae,Phlebovirus,Severe fever with thrombocytopenia syndrome virus | 1 | seg. M | KC292300 |
| SFTS virus HNXY_224 | NC_018136 | vertebrates,invertebrates, human | Bunyaviridae,Phlebovirus,Severe fever with thrombocytopenia syndrome virus | 1 | seg. L | KC292343 |
| SFTS virus HNXY_224 | NC_018137 | vertebrates,invertebrates, human | Bunyaviridae,Phlebovirus,Severe fever with thrombocytopenia syndrome virus | 1 | seg. S | KC292290 |
| SFTS virus HNXY_224 | NC_018138 | vertebrates,invertebrates, human | Bunyaviridae,Phlebovirus,Severe fever with thrombocytopenia syndrome virus | 1 | seg. M | KC292317 |
| SFTS virus HNXY_231 | NC_018136 | vertebrates,invertebrates, human | Bunyaviridae,Phlebovirus,Severe fever with thrombocytopenia syndrome virus | 1 | seg. L | KC292339 |
| SFTS virus HNXY_231 | NC_018137 | vertebrates,invertebrates, human | Bunyaviridae,Phlebovirus,Severe fever with thrombocytopenia syndrome virus | 1 | seg. S | KC292286 |

TABLE 10-continued

VíroCap-1.0 Taxonomy

| Taxonomy | Rep.Acc.ID | Host | # GN's | Lineage | Seg. Count | GN.Acc.IDs |
|---|---|---|---|---|---|---|
| SFTS virus HNXY_231 | NC_018138 | vertebrates,invertebrates, human | 1 | Bunyaviridae,Phlebovirus,Severe fever with thrombocytopenia syndrome virus | seg. M | KC292

TABLE 10-continued

| Taxonomy | Rep.Acc.ID | Host | ViroCap-1.0 Taxonomy | | Seg. Count | GN.Acc.IDs |
| | | | # GN's | Lineage | | |
|---|---|---|---|---|---|---|
| SFTS virus HNXY_93 | NC_018138 | vertebrates,invertebrates,human | 1 | Bunyaviridae,Phlebovirus,Severe fever with thrombocytopenia syndrome virus | seg. M | KC292311 |
| SFTS virus JS3 | NC_018136 | vertebrates,invertebrates,human | 1 | Bunyaviridae,Phlebovirus,Severe fever with thrombocytopenia syndrome virus | seg. L | HQ141601 |
| SFTS virus JS3 | NC_018137 | vertebrates,invertebrates,human | 1 | Bunyaviridae,Phlebovirus,Severe fever with thrombocytopenia syndrome virus | seg. S | HQ141603 |
| SFTS virus JS3 | NC_018138 | vertebrates,invertebrates,human | 1 | Bunyaviridae,Phlebovirus,Severe fever with thrombocytopenia syndrome virus | seg. M | HQ141602 |
| SFTS virus JS4 | NC_018136 | vertebrates,invertebrates,human | 1 | Bunyaviridae,Phlebovirus,Severe fever with thrombocytopenia syndrome virus | seg. L | HQ141604 |
| SFTS virus JS4 | NC_018137 | vertebrates,invertebrates,human | 1 | Bunyaviridae,Phlebovirus,Severe fever with thrombocytopenia syndrome virus | seg. S | HQ141606 |
| SFTS virus JS4 | NC_018138 | vertebrates,invertebrates,human | 1 | Bunyaviridae,Phlebovirus,Severe fever with thrombocytopenia syndrome virus | seg. M | HQ141605 |
| SFTS virus LN2 | NC_018136 | vertebrates,invertebrates,human | 1 | Bunyaviridae,Phlebovirus,Severe fever with thrombocytopenia syndrome virus | seg. L | HQ141607 |
| SFTS virus LN2 | NC_018137 | vertebrates,invertebrates,human | 1 | Bunyaviridae,Phlebovirus,Severe fever with thrombocytopenia syndrome virus | seg. S | HQ141609 |
| SFTS virus LN2 | NC_018138 | vertebrates,invertebrates,human | 1 | Bunyaviridae,Phlebovirus,Severe fever with thrombocytopenia syndrome virus | seg. M | HQ141608 |
| SFTS virus LN3 | NC_018136 | vertebrates,invertebrates,human | 1 | Bunyaviridae,Phlebovirus,Severe fever with thrombocytopenia syndrome virus | seg. L | HQ141610 |
| SFTS virus LN3 | NC_018137 | vertebrates,invertebrates,human | 1 | Bunyaviridae,Phlebovirus,Severe fever with thrombocytopenia syndrome virus | seg. S | HQ141612 |
| SFTS virus LN3 | NC_018138 | vertebrates,invertebrates,human | 1 | Bunyaviridae,Phlebovirus,Severe fever with thrombocytopenia syndrome virus | seg. M | HQ141611 |
| SFTS virus SD24 | NC_018136 | vertebrates,invertebrates,human | 1 | Bunyaviridae,Phlebovirus,Severe fever with thrombocytopenia syndrome virus | seg. L | HM802200 |
| SFTS virus SD24 | NC_018137 | vertebrates,invertebrates,human | 1 | Bunyaviridae,Phlebovirus,Severe fever with thrombocytopenia syndrome virus | seg. S | HM802205 |
| SFTS virus SD24 | NC_018138 | vertebrates,invertebrates,human | 1 | Bunyaviridae,Phlebovirus,Severe fever with thrombocytopenia syndrome virus | seg. M | HM802201 |
| SFTS virus SD4 | NC_018136 | vertebrates,invertebrates,human | 1 | Bunyaviridae,Phlebovirus,Severe fever with thrombocytopenia syndrome virus | seg. L | HM802202 |
| SFTS virus SD4 | NC_018137 | vertebrates,invertebrates,human | 1 | Bunyaviridae,Phlebovirus,Severe fever with thrombocytopenia syndrome virus | seg. S | HM802204 |
| SFTS virus SD4 | NC_018138 | vertebrates,invertebrates,human | 1 | Bunyaviridae,Phlebovirus,Severe fever with thrombocytopenia syndrome virus | seg. M | HM802203 |
| Sabo virus | NC_009894 | vertebrates,invertebrates,human | 1 | Bunyaviridae,Orthobunyavirus,Akabane virus | seg. L | HE795096 |
| Sabo virus | NC_009895 | vertebrates,invertebrates,human | 1 | Bunyaviridae,Orthobunyavirus,Akabane virus | seg. M | HE795097 |
| Sabo virus | NC_009896 | vertebrates,invertebrates,human | 1 | Bunyaviridae,Orthobunyavirus,Akabane virus | seg. S | HE795098 |
| Sagiyama virus | NC_001544 | vertebrates,invertebrates,human | 1 | Togaviridae,Alphavirus,Ross River virus | — | AB032553 |
| San Angelo virus | NC_004109 | vertebrates,invertebrates,human | 1 | Bunyaviridae,Orthobunyavirus,California encephalitis virus | seg. M | AF123486 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| San Angelo virus | NC_004110 | vertebrates,invertebrates,human | 1 | Bunyaviridae,Orthobunyavirus,California encephalitis virus | seg. S | U47139 |
| Sand fever Naples-like virus | NC_006318 | vertebrates,invertebrates,human | 2 | Bunyaviridae,Phlebovirus,Sandfly fever Naples virus | seg. S | HM566182,HM566617 8 |
| Sand fever Naples-like virus | NC_006319 | vertebrates,invertebrates,human | 2 | Bunyaviridae,Phlebovirus,Sandfly fever Naples virus | seg. L | HM566176,HM56618 |
| Sand fever Naples-like virus | NC_006320 | vertebrates,invertebrates,human | 1 | Bunyaviridae,Phlebovirus,Sandfly fever Naples virus | seg. M | HM566177 |
| Sandfly Sicilian Turkey virus | NC_015411 | vertebrates,invertebrates,human | 1 | Bunyaviridae,Phlebovirus,Sandfly fever Sicilian virus | seg. M | GQ847512 |
| Sandfly Sicilian Turkey virus | NC_015412 | vertebrates,invertebrates,human | 1 | Bunyaviridae,Phlebovirus,Sandfly fever Sicilian virus | seg. L | GQ847513 |
| Sandfly Sicilian Turkey virus | NC_015413 | vertebrates,invertebrates,human | 1 | Bunyaviridae,Phlebovirus,Sandfly fever Sicilian virus | seg. S | GQ847511 |
| Sandfly fever Naples virus | NC_006318 | vertebrates,invertebrates,human | 8 | Bunyaviridae,Phlebovirus,Sandfly fever Naples virus | seg. S | EF201831,HM566170,HM566168,EF20182 8,EF201832,X53794, EF201829,EF201830 |
| Sandfly fever Naples virus | NC_006319 | vertebrates,invertebrates,human | 3 | Bunyaviridae,Phlebovirus,Sandfly fever Naples virus | seg. L | HM566172,X68414,HM566167 |
| Sandfly fever Naples virus | NC_006320 | vertebrates,invertebrates,human | 3 | Bunyaviridae,Phlebovirus,Sandfly fever Naples virus | seg. M | HM566171,HM56616 9,X89628 |
| Sandfly fever sicilian virus | NC_015411 | vertebrates,invertebrates,human | 1 | Bunyaviridae,Phlebovirus,Sandfly fever Sicilian virus | seg. M | U30500 |
| Sandfly fever sicilian virus | NC_015413 | vertebrates,invertebrates,human | 9 | Bunyaviridae,Phlebovirus,Sandfly fever Sicilian virus | seg. S | EF201826,AJ811547, EF201825,EF201822, JQ4418,EF201824,EF 201823,EF201827,G U119908 |
| Sango virus | NC_018463 | vertebrates,invertebrates,human | 1 | Bunyaviridae,Orthobunyavirus,Shamonda virus | seg. L | HE795099 |
| Sango virus | NC_018464 | vertebrates,invertebrates,human | 1 | Bunyaviridae,Orthobunyavirus,Shamonda virus | seg. S | HE795101 |
| Sango virus | NC_018467 | vertebrates,invertebrates,human | 1 | Bunyaviridae,Orthobunyavirus,Shamonda virus | seg. M | HE795100 |
| Sathuperi virus | NC_018461 | vertebrates,invertebrates,human | 1 | Bunyaviridae,Orthobunyavirus,Sathuperi virus | seg. L | HE795102 |
| Sathuperi virus | NC_018462 | vertebrates,invertebrates,human | 1 | Bunyaviridae,Orthobunyavirus,Sathuperi virus | seg. S | HE795104 |
| Sathuperi virus | NC_018466 | vertebrates,invertebrates,human | 1 | Bunyaviridae,Orthobunyavirus,Sathuperi virus | seg. M | HE795103 |
| Sepik virus | NC_008719 | vertebrates,invertebrates,human | 2 | Flaviviridae,Flavivirus,Sepik virus | — | DQ837642,AY632543 |
| Serra Norte virus | NC_015373 | vertebrates,invertebrates,human | 1 | Bunyaviridae,Phlebovirus,Candiru virus | seg. M | HM119429 |
| Serra Norte virus | NC_015374 | vertebrates,invertebrates,human | 1 | Bunyaviridae,Phlebovirus,Candiru virus | seg. L | HM119428 |

TABLE 10-continued

VrioCap-1.0 Taxonomy

| Taxonomy | Rep.Acc.ID | Host | # GN's | Lineage | Seg. Count | GN.Acc.IDs |
|---|---|---|---|---|---|---|
| Serra Norte virus | NC_015375 | vertebrates,invertebrates, human | 1 | Bunyaviridae,Phlebovirus,Candiru virus | seg. S | HM119430 |
| Serra do Navio virus | NC_004110 | vertebrates,invertebrates, human | 1 | Bunyaviridae,Orthobunyavirus,California encephalitis virus | seg. S | U47140 |
| Severe fever with thrombocytopenia syndrome virus | NC_018136 | vertebrates,invertebrates, human | 24 | Bunyaviridae,Phlebovirus,Severe fever with thrombocytopenia syndrome virus | seg. L | KC505123,JQ733561,KC505126,AB817985,AB817984,JQ733564,JQ733567,JQ67093 4,KC505129,AB817983,KC473540,JQ684871,KC505135,KC505132,AB817982,AB817979,AB817981,KC505138,JQ670929,KC505141,AB817980,KC505144,KC473537,AB817986 |
| Severe fever with thrombocytopenia syndrome virus | NC_018137 | vertebrates,invertebrates, human | 36 | Bunyaviridae,Phlebovirus,Severe fever with thrombocytopenia syndrome virus | seg. S | AB817997,KC505131,JQ693005,JQ693008,AB817996,KC505134,JQ670933,AB818002,KC505146,JQ693006,KC473539,JQ670932,KC505140,KC505125,JQ733565,JQ693007,AB817998,JQ733562,AB818000,JQ733568,KC473542,JQ693010,AB817995,AB818001,JQ693011,JQ693002,KC505128,JQ693009,KC505143,JQ693003,JQ693001,JQ693012,AB817999,JQ684873,JQ693004,JQ693013 |
| Severe fever with thrombocytopenia syndrome virus | NC_018138 | vertebrates,invertebrates, human | 24 | Bunyaviridae,Phlebovirus,Severe fever with thrombocytopenia syndrome virus | seg. M | KC473538,KC505136,KC505145,JQ733356,KC473541,KC505139,AB817992,AB817994,JQ670930,AB817990,AB817988,KC505142,AB817993,AB817989,JQ684872,JQ733563,KC505127,KC505130,JQ733560,AB... |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| Shamonda virus | NC_018463 | vertebrates,invertebrates,human | Bunyaviridae,Orthobunyavirus,Shamonda virus | 1 | seg. L | 817987,AB817991,KC505133,KC505124,J0670931 |
| Shamonda virus | NC_018464 | vertebrates,invertebrates,human | Bunyaviridae,Orthobunyavirus,Shamonda virus | 1 | seg. S | HE795105 |
| Shamonda virus | NC_018467 | vertebrates,invertebrates,human | Bunyaviridae,Orthobunyavirus,Shamonda virus | 1 | seg. M | HE795107 |
| Shokwe virus | NC_001927 | vertebrates,invertebrates,human | Bunyaviridae,Orthobunyavirus,Bunyamwera virus | 1 | seg. S | HE795106 |
| Simbu virus | NC_018476 | vertebrates,invertebrates,human | Bunyaviridae,Orthobunyavirus,Simbu virus | 1 | seg. L | EU564831 |
| Simbu virus | NC_018477 | vertebrates,invertebrates,human | Bunyaviridae,Orthobunyavirus,Simbu virus | 1 | seg. S | HE795108 |
| Simbu virus | NC_018478 | vertebrates,invertebrates,human | Bunyaviridae,Orthobunyavirus,Simbu virus | 1 | seg. M | HE795110 |
| Sitiawan virus | NC_015843 | vertebrates,invertebrates,human | Flaviviridae,Flavivirus,Tembusu virus | 1 | — | HE795109 |
| Snowshoe hare virus | NC_004108 | vertebrates,invertebrates,human | Bunyaviridae,Orthobunyavirus,California encephalitis virus | 1 | seg. L | JX477686 |
| Snowshoe hare virus | NC_004109 | vertebrates,invertebrates,human | Bunyaviridae,Orthobunyavirus,California encephalitis virus | 2 | seg. M | EU203678 |
| Snowshoe hare virus | NC_004110 | vertebrates,invertebrates,human | Bunyaviridae,Orthobunyavirus,California encephalitis virus | 2 | seg. S | K02539,EU262553 |
| South River virus | NC_004109 | vertebrates,invertebrates,human | Bunyaviridae,Orthobunyavirus,California encephalitis virus | 1 | seg. M | EU294510,JQ2390 |
| St.Louis encephalitis virus | NC_007580 | vertebrates,invertebrates,human | Flaviviridae,Flavivirus,St.Louis encephalitis virus | 9 | — | JQ957868,FJ753287,FJ753286,JF460774,DQ359217,JQ957869,EU566860,AY632544,DQ525916 |
| Tahyna virus | NC_004109 | vertebrates,invertebrates,human | Bunyaviridae,Orthobunyavirus,California encephalitis virus | 2 | seg. M | AF123485,AF229129 |
| Tahyna virus | NC_004110 | vertebrates,invertebrates,human | Bunyaviridae,Orthobunyavirus,California encephalitis virus | 2 | seg. S | U47142,Z68497 |
| Tamana bat virus | NC_003996 | vertebrates,invertebrates,human | Flaviviridae,Flavivirus,Tamana bat virus | 2 | — | AF285080,AF346759 |
| Tembusu virus | NC_015843 | vertebrates,invertebrates,human | Flaviviridae,Flavivirus,Tembusu virus | 18 | — | KF557894,KF192951,JQ595407,JX477685,JQ314464,JF895923,KC333867,JX549382,JX965381,JQ928189,JN811558,JX273153,JF270480,JF459991,JQ314466,KF557893,KC136210,JN811559 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Thogoto virus | NC_006495 | vertebrates,invertebrates,human | 1 | Orthomyxoviridae,Thogotovirus,Thogoto virus | seg. 2 | AF004985 |
| Thogoto virus | NC_006496 | vertebrates,invertebrates,human | 2 | Orthomyxoviridae,Thogotovirus,Thogoto virus | seg. 3 | AF006073,DQ0540 |
| Thogoto virus | NC_006504 | vertebrates,invertebrates,human | 4 | Orthomyxoviridae,Thogotovirus,Thogoto virus | seg. 6 | AF527531,AF527529,AF236794,AF527530 |
| Thogoto virus | NC_006506 | vertebrates,invertebrates,human | 1 | Orthomyxoviridae,Thogotovirus,Thogoto virus | seg. 4 | M77280 |
| Thogoto virus | NC_006507 | vertebrates,invertebrates,human | 1 | Orthomyxoviridae,Thogotovirus,Thogoto virus | seg. 5 | X96872 |
| Thogoto virus | NC_006508 | vertebrates,invertebrates,human | 1 | Orthomyxoviridae,Thogotovirus,Thogoto virus | seg. 1 | Y17873 |
| Tick-borne encephalitis virus | NC_001672 | vertebrates,invertebrates,human | 78 | Flaviviridae,Flavivirus,Tick-borne encephalitis virus | — | JQ825149,FJ402886,EU816454,EU816452,JQ825163,JF316707,GQ228395,EU81645 3,U27495,KC422663,EU816451,JQ825160,FJ572210,GU183383,KC414090,JQ82515 0,AY169390,AF52741 5,JQ654701,HM1208 75,HM535611,JN229 223,JQ650522,FJ968 751,GU183379,JQ82 5161,AB062064,HQ9 01366,EF469661,EF4 69662,JF316708,FJ4 02885,KC835596,FJ9 06622,JQ825146,GQ 266392,JX534167,FJ 997899,JQ825152,K C422667,GU121642, EU816450,L40361,K C835595,JQ825147, AB062063,HM859895 ,AB753012,JQ825151 ,JQ825145,JQ825144 ,DQ401140,JQ82514 8,JQ650523,U39292, JQ825159,GU183381 ,KF151173,JQ825164 ,HM535610,JQ82516 2,KC835597,JN00320 7,HQ20103,JQ8251 56,JQ825158,AF0690 66,AY182009,JQ8251 53,JQ825157,HM859 |

TABLE 10-continued

| Taxonomy | Rep.Acc.ID | Host | # GN's | ViroCap-1.0 Taxonomy Lineage | Seg. Count | GN.Acc.IDs |
|---|---|---|---|---|---|---|
| Tinaroo virus | NC_009895 | vertebrates,invertebrates,human | 1 | Bunyaviridae,Orthobunyavirus,Akabane virus | seg. M | 894,JQ825154,EU816455,JQ27491,JQ825155,GU183380,JF819648,HQ901367 |
| Tinaroo virus | NC_009896 | vertebrates,invertebrates,human | 1 | Bunyaviridae,Orthobunyavirus,Akabane virus | seg. S | AB208700 |
| Toscana virus | NC_006318 | vertebrates,invertebrates,human | 9 | Bunyaviridae,Phlebovirus,Sandfly fever Naples virus | seg. S | EU327772,EF120631,EF201833,JF330274,KC776214,JF330275,JX867536,FJ153285,FJ153286 |
| Toscana virus | NC_006319 | vertebrates,invertebrates,human | 2 | Bunyaviridae,Phlebovirus,Sandfly fever Naples virus | seg. L | JX867534,KC776216 |
| Toscana virus | NC_006320 | vertebrates,invertebrates,human | 12 | Bunyaviridae,Phlebovirus,Sandfly fever Naples virus | seg. M | JF330280,EU003178,EU003175,EU003179,EU003180,EU003177,EU003174,JF330279,EU003176,KC776215,EU003173,JX867535 |
| Tribec virus | NC_014522 | vertebrates,invertebrates,human | 2 | Reoviridae,Orbivirus,Great Island virus | seg. 1 | HQ266581,HM543478 |
| Tribec virus | NC_014523 | vertebrates,invertebrates,human | 2 | Reoviridae,Orbivirus,Great Island virus | seg. 2 | HQ266582,HM543479 |
| Tribec virus | NC_014524 | vertebrates,invertebrates,human | 1 | Reoviridae,Orbivirus,Great Island virus | seg. 3 | HQ266583 |
| Tribec virus | NC_014525 | vertebrates,invertebrates,human | 1 | Reoviridae,Orbivirus,Great Island virus | seg. 4 | HQ266584 |
| Tribec virus | NC_014526 | vertebrates,invertebrates,human | 1 | Reoviridae,Orbivirus,Great Island virus | seg. 5 | HQ266585 |
| Tribec virus | NC_014527 | vertebrates,invertebrates,human | 2 | Reoviridae,Orbivirus,Great Island virus | seg. 6 | HM543480,HQ266586 |
| Tribec virus | NC_014528 | vertebrates,invertebrates,human | 1 | Reoviridae,Orbivirus,Great Island virus | seg. 7 | HQ266587 |
| Tribec virus | NC_014529 | vertebrates,invertebrates,human | 1 | Reoviridae,Orbivirus,Great Island virus | seg. 8 | HQ266588 |
| Tribec virus | NC_014530 | vertebrates,invertebrates,human | 1 | Reoviridae,Orbivirus,Great Island virus | seg. 9 | HQ266589 |
| Tribec virus | NC_014531 | vertebrates,invertebrates,human | 1 | Reoviridae,Orbivirus,Great Island virus | seg. 10 | HQ266590 |
| Trivittatus virus | NC_004109 | vertebrates,invertebrates,human | 1 | Bunyaviridae,Orthobunyavirus,California encephalitis virus | seg. M | AF123491 |
| Trivittatus virus | NC_004110 | vertebrates,invertebrates,human | 1 | Bunyaviridae,Orthobunyavirus,California encephalitis virus | seg. S | U12803 |
| Turuna virus | NC_015373 | vertebrates,invertebrates,human | 1 | Bunyaviridae,Phlebovirus,Candiru virus | seg. M | HM119432 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| Turuna virus | NC_015374 | vertebrates,invertebrates,human | 1 | Bunyaviridae,Phlebovirus,Candiru virus | seg. L | HM119431 |
| Turuna virus | NC_015375 | vertebrates,invertebrates,human | 1 | Bunyaviridae,Phlebovirus,Candiru virus | seg. S | HM119433 |
| Tyuleniy virus | NC_023424 | vertebrates,invertebrates,human | 1 | Flaviviridae,Flavivirus,Tyuleniy virus | | KF815939 |
| Usutu virus | NC_006551 | vertebrates,invertebrates,human | 10 | Flaviviridae,Flavivirus,Usutu virus | | KC754957,EF206350,KC754955,JF266698,KC754958,AY45341 1,AY453412,JQ21984 3,KC754954,KC7549 56 |
| Uukuniemi virus | NC_005214 | vertebrates,invertebrates,human | 1 | Bunyaviridae,Phlebovirus,Uukuniemi virus | seg. L | D10759 |
| Uukuniemi virus | NC_005220 | vertebrates,invertebrates,human | 1 | Bunyaviridae,Phlebovirus,Uukuniemi virus | seg. M | M17417 |
| Uukuniemi virus | NC_005221 | vertebrates,invertebrates,human | 1 | Bunyaviridae,Phlebovirus,Uukuniemi virus | seg. S | M33551 |
| Wesselsbron virus | NC_012735 | vertebrates,invertebrates,human | 2 | Flaviviridae,Flavivirus,Wesselsbron virus | — | EU707555,JN226796 |
| West Nile virus | NC_001563 | vertebrates,invertebrates,human | 681 | Flaviviridae,Flavivirus,West Nile virus | — | JN819317,FJ425721,HQ671721,JN858069,DQ080059,HQ67169 9,HM488219,JX5030 87,GQ507482,JF899 537,CS568918,JX503 084,HM488220,HM48 8126,DQ080062,DQ4 31701,JF957169,JF9 20749,EU068667,DQ 16418 7,JQ928174,H M488211,JF920754,J F415922,KF647249,J F957167,HQ671688, DQ080070,JF957180, JF357960,JF899530, KF588365,JF920746, JF415927,HQ671670, DQ411030,AF196835 ,JF488096,HM48820 1,HQ671673,JF48808 7,HM488165,AF4047 56,GQ379156,JF730 043,HM488173,JF48 8086,HQ671718,HQ6 71720,KC736498,HM 488129,KC736486,M 12294,JF415919,HM |

TABLE 10-continued

VoroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 488181,AY262283,JF920752,HQ671679,JF920759,KC711059,HM488132,GQ903680,KC711057,GQ37915 8,HM756672,JF9571 62,DQ080067,JF9207 33,HM488156,DQ431 712,HM488135,JN81 9311,HM756649,HM4 88160,HQ705670,JF8 99534,JN819319,JF9 57182,JF920307,DQ4 31693,KC736493,HM 756656,JX503092,H M488235,HM756663, JN183885,JF415930, JN819323,JXQ41628, HM756664,HM75665 1,DQ080069,JF41592 6,JQ700439,HM4881 79,JF957185,KC7364 89,KJ145832,HM488 209,DQ411035,AB18 5916,JXQ155220,HQ6 71722,JF920747,HM 488207,HQ705671,H M488170,GQ379161, KC736487,HM48825 0,DQ374653,JF92073 8,JN819320,HQ6716 96,DQ411032,HQ671 700,HM488164,HQ67 1707,HQ671687,GQ5 07473,KC736492,DQ 080065,HQ705674,JF 415918,JX503093,H M488233,HM488218, AY795965,HQ671692 ,HM488172,DQ37717 8,FJ151394,HM7566 57,AF260967,KC407 673,DQ431694,HQ67 1691,JF415929,HM4 88185,DQ116961,HM 488195,JF488089,JF 957171,HM756677,F J527738,HQ671702,J |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | F899532,HM488197,GQ507484,JF357958,HM488159,DQ37718 0,HM488144,JQ7004 41,HQ67173l,DQ431 708,DQ411031,JF957 176,JN183886,JXQ15 519,HM488131,KF64 7251,HM488230,DQO 80068,HM488232,DO 983578,HM756671,H M488124,JF415925, HQ671727,DQ37465 0,KC736501,DQ0800 51,JN819310,AF4047 53,HM488148,JF703 162,HM488134,DQ43 1703,HM756660,HM7 56648,JF730042,JF7 19068,HM488182,JF 415924,JF957184,H M488163,HQ705675, AY712945,JF920735, HM488251,HM48824 5,JF920729,HQ70567 2,JN716371,HM1478 23,JF920739,HM488 189,HM488242,HM48 8246,DQ164204,HQ7 05660,HQ671719,GQ 507472,JF719067,JX 015521,FJ159129,JF 957175,HQ671671,D 0164198,HQ671695, DQ411034,KC407666 ,GQ507470,GQ50747 8,HM488217,HM4881 71,JX123031,HQ671 708,AF206518,HQ67 1681,HM488118,JF9 20731,DQ374652,DQ 164200,HQ671684,E U081844,JN819305,J F920744,AY278442,J XQ15516,JF899536,K C736495,DQ431702, HM488137,DQ43171 0,HM488213,AY5326 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 65,HM488125,JX503088,HM756654,JF415915,HQ705569,JF957179,HQ671728,JN819307,GQ507477,JN183387,KC736500,HM488149,0891013,HM488149,HQ537483,JQ700438,GQ507481,JF73004 0,AY277252,JF957164,HM488123,EF571854,HM756668,HQ671732,JF957186,HM488130,AY268132,DQ164206,DQ431707,HQ671677,HM147822,AF404757,HQ671680,GU828002,JF920740,HM756670,EF657887,JF957168,JXQ41632,HQ671705,AY701413,AY660002,GU011992,AF404755,HM488210,JF784158,HM488154,HQ671694,JF920757,HM488150,JX503089,CS568919,DQO80054,JF920750,AY712946,AF260969,HM488192,CS568917,HM488147,KF179639,DQ411033,HM488183,HQ671689,HM488205,HM488252,JF920745,HQ671711,EF530047,GU828000,HQ671682,KF647253,HQ671683,JN183888,HM488157,JF415920,HM488157,JF957161,HM488216,JF411043,GQ507480,JX503094,JF957181,HQ891012,HM756667,HQ671713,HM488136,HQ671733,JF488091,HM488187,HQ671674,AB185915,JF48 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 8093,GQ379159,HQ705677,DQ164195,HM488248,KC736502,D0164202,JF957165,HM488184,HQ671730,JF899533,DQ164186,JQ700442,HM488228,DQ176637,AF40475 4,JXQ15522,DQ176636,HM488146,AB185917,KC601756,HM488222,HM756675,GU828003,HM756665,HM48815,HM488115,H0671706,GQ507474, GU828001,EU249803,AF533540,JXQ41631,AF260968,KC73649 0,DQ431699,DQ080064,HM488234,DQ164190,JN183896,HM488198,HM488253,JF707789,JF920737,HM488208,JXQ70655,H Q671717,JN183892, HQ671693,FJ159131, HM756652,DQ411029,DQ080060,KF179640,DQ666449,JX556213,HQ891010,HM488249,HM488119,JN183894,HM488204,DO080052,HM488145,J0700440,HM488193, HM488116,HM488817 4,JF920753,DQ080072,DQ377179,HM756666,GU827999,AY289214,HM488229,HM488186,CS568914,HM756661,HM756678,JF703161,HM488227,H M756659,AF202541, EU155484,DQ431695,HQ671716,AF31720 3,DQ431709,JF92074 1,DQ431697,HM488177,HM488221,JX503 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 099,GQ507475,JXQ15523,DQ164194,HQ671703,HM488140,HQ671669,HM488231,D0164205,FJ159130,HM488196,DQ164189,HM488190,JF920748,HQ671724,JN81931 6,HM488141,JX5030 95,DQ080061,JF9203 06,HQ671698,JN819 309,HM488226,HM48 8247,JF920728,JF89 9529,HM488254,DQ3 18020,JF920758,HM 488202,JF415914,HQ 671678,JF957166,DQ 431706,HQ671685,H M488127,JF488088, HM488117,JF488090 ,HM488212,KF64725 0,JF357959,JF95717 4,JF920755,GQ5074 79,KC736497,JN1838 97,AY701412,HM488 139,HM488239,DQ08 0056,DQ256376,HM4 88152,JF488095,DQ6 66450,GQ507469,KC 736499,HQ671672,JF 920743,HM488120,D 0164188,JN819321,J F920734,JXQ15515,D 0164192,JF899535,H M488180,JN858070, DQ786573,GU82799 8,JX503090,AY68894 8,JN39308,HQ6717 04,KF234080,JN8193 24,DQ080066,JF9207 42,JF703164,JXQ416 34,AY278441,HM756 662,DQ666452,HM48 8240,HM488199,KC7 36494,DQ786572,JF9 57183,HM756658,HM 488162,JN183889,H M488155,JF920756,J |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | F899528,DQ666448,JN183893,HM488225,JN819313,HM488169,GQ379160,HQ67166 8,DQ318019,JF48809 7,HM488167,HM4881 38,HQ671723,CS543 188,JN819315,HM75 6673,HM488153,HQ6 71690,HQ671697,HM 488238,HM488194,F J483549,JX503091,H M488158,JF719065,J F415917,DQ080057, HQ671729,DQ08005 5,JXQ41629,JX50309 6,DQ374651,HM0514 16,KC407667,DQ431 705,JF957170,JF957 178,JF920751,DQ431 711,HM488121,HM48 8191,HM488215,HQ6 71726,HQ891011,JF7 19069,DQ005530,DQ 164193,GQ507483,H 0671714,JF703163,D 0666451,HM488114, JF488094,HM488142 ,AB185914,HM48823 7,HQ671675,DQ1641 97,GQ507468,JF415 928,HQ671701,JX50 3085,AY765264,HM4 88223,JN183891,JF7 30041,DQ164203,JF9 57173,HM488241,AY 268133,KC736488,H M488176,HQ671686, JXQ15518,HML47824 JF957177,HM48818 8,DQ164201,AY4902 40,KF647252,AY6036 54,HM756676,HM488 200,JF972636,HM48 8243,HM488178,HQ7 05678,CS568916,JN3 67277,HM488166,JF 957172,HQ705676,D |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 0431700,AY712947,J0700437,AY712948,JF415923,DQ080058,JN819312,JF719066,JF415916,HM488122,JN183895,JX503098,HM488244,JXQ41630,JX123030,HQ705659,GQ50747l,HM756653,KC736491,DQ164191,HQ891009,HQ671710,JF920732,HM488168,JQ928175,DQ080063,JF415921,DQ164199,JF899531,HQ671712,HQ705673,JF488092,FJ483548,JF920730,DQ431704,JF920760,HM488206,D0164196,HQ671709,JX503097,JX503086,AF481864,HQ671676,JF957163,JXQ15517,JN819306,HM488133,GQ379157,HQ671725,DQ080053,HM488203,KC736496,KF647248,DQ118127,HM756650,KC954092,HM488214,HM488175,JN183890,DQ080071,D0431696,DQ431698,GU828004,GQ507476,HM488236,HM488224,HM488143,HQ671715,HQ596519,HQ705663,JF920736,HM488161,AY646354,HM488128,HM756669,JN819318 |
| West Nile virus | NC_009942 | vertebrates,invertebrates,human | 681 | Flaviviridae,Flavivirus,West Nile virus | — | JN819317,FJ425721,HQ671721,JN858069,DQ080059,HQ671699,HM488219,JX503087,GQ507482,JF899537,CS568918,JX503084,HM488220,HM488126,DQ080062,DQ4 |

TABLE 10-continued

ViroCap-1.0 Taxonomy

| Taxonomy | Rep.Acc.ID | Host | Lineage | # GN's | Seg. Count | GN.Acc.IDs |
|---|---|---|---|---|---|---|
| | | | | | | 31701,JF957169,JF920749,EU068667,DQ164187,JQ928174,HM448211,JF920754,JF415922,KF647249,JF957167,HQ671688,DQ080070,JF957180,JF357960,JF899530,KF588365,JF920746,JF415927,HQ671670,DQ411030,AF196835,JF488096,HM448820,HQ671673,JF488808,HM448165,AF404756,GQ379156,JF730043,HM488173,JF488086,HQ671718,HQ671720,KC736498,HM488129,KC736486,JF415919,HM488181,AY262283,JF920752,HQ671679,JF920759,KC711059,HM488132,GQ903680,KC710567,GQ379158,HM756672,JF957162,DQ080067,JF920733,HM488156,DQ431712,HM488135,JN819311,HM756649,HM488160,HQ705670,JF899534,JN819319,JF957182,JF920307,DQ431693,KC736493,HM756656,JX503092,HM488235,HM756663,JN18388S,JF415930,JN819323,JXQ41628,HM756664,HM756651,DQ080069,JF415926,JQ700439,HM488179,JF957185,KC736489,KJ145832,HM488209,DQ411035,AB185916,JXQ15520,HQ671722,JF920747,HM488207,HQ705671,HM488170,G0379161,KC736487, |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | HM488250,DQ374653,JF920738,JN819320,HQ671696,DQ411032,HQ671700,HM488164,HQ671707,HQ671687,GQ507473,KC736492,DQ080065,HQ705674,JF415918,JX503093,HM488233,HM488218,AY795965,HQ671692,HM488817 2,DQ377178,FJ151394,HM756657,AF260967,KC407673,DQ431694,HQ671691,JF415929,HM488185,DQ116961,HM488195,JF488089,JF957171,HM756677,FJ527738,HQ671702,JF899532,HM488197,GQ507484,JF357958,HM488159,DQ377180,HM488814,JQ700441,HQ671731,DQ431708,DQ411031,JF957176,JN183886,JXQ15519,HM488131,KF647251,HM488230,DQ080068,HM488232,DQ983578,HM756671,HM488124,JF415925,HQ671727,DQ374650,KC736501,DQ080051,JN81931 0,AF404753,HM488148,JF703162,HM488134,DQ431703,HM756660,HM756648,JF730042,JF719068,HM488182,JF415924,JF957184,HM488163,H0705675,AY712945,JF920735,HM488251,HM488245,JF920729,HQ705672,JN716371,HM147823,JF920739,HM488189,HM488242,HM488246,DQ16 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 4204,HQ705660,HQ671719,GQ507472,JF719067,JXQ15521,FJ159129,JF957175,HQ671671,DQ164198,H0671695,DQ411034,KC407666,GQ507470,GQ507478,HM488217,HM488171,JX123031,HQ671708,AF206518,HQ671681,HM488118,JF920731,DQ374652,DQ164200,HQ671684,EU081844,JN819305,JF920744,AY278442,JXQ15516,JF899536,KC736495,D0431702,HM488137,DQ431710,HM488213,AY532665,HM488125,JX503088,HM756654,JF415915,HQ705669,JF957179,HQ671728,JN819307,GQ507477,JN183887,KC736500,HQ891013,HM488149,HQ537483,JQ700438,GQ507481,JF730040,AY277252,JF957164,HM488123,EF571854,HM756668,HQ671732,JF957186,HM488130,AY268132,DQ164206,DQ431707,HQ671677,HM147822,AF404757,HQ671680,GU828002,JF920740,HM756670,EF657887,JF957168,JXQ41632,HQ671705,AY701413,AY660002,GU011992,AF404755,HM488210,JF784158,HM488154,HQ671694,JF920757,HM488150,JX503089,CS568919,DQ080054,JF920750,AY712946,AF260950 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 69,HM488192,CS568 917,HM488147,KF17 9639,DQ411033,HM4 88183,HQ671689,HM 488205,HM488252,J F920745,HQ671711, EF530047,GU828000 ,HQ671682,KF64725 3,HQ671683,JN1838 88,HQ671742,JF4159 20,HM488157,AY277 251,JF957161,HM48 8216,FJ411043,GQ5 07480,JX503094,JF9 57181,HQ891012,HM 756667,HQ671713,H M488136,HQ671733, JF488091,HM488187 ,HQ671674,AB18591 5,JF488093,GQ3791 59,HQ705677,DQ164 195,HM488248,KC73 6502,DQ164202,JF95 7165,HM488184,HQ6 71730,JF899533,DQ1 64186,JQ700442,HM 488228,DQ176637,A F404754,JXQ15522,D 0176636,HM488146, AB185917,KC601756 ,HM488222,HM75667 5,GU828003,HM7566 65,HM488151,HM488 115,HQ671706,GQ50 7474,GU828001,EU2 49803,AF533540,JXQ 41631,AF260968,KC 736490,DQ431699,D 0080064,HM488234, DQ164190,JN183896 ,HM488198,HM48825 3,JF707789,JF92073 7,HM488208,JXQ706 55,HQ671717,JN183 892,HQ671693,FJ159 131,HM756652,DQ41 1029,DQ080060,KF1 79640,DQ666449,JX |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 556213,HQ891010,HM488249,HM488119,JN183894,HM488204,DQ080052,HM488814 5,JQ700440,HM488193,HM488116,HM488174,JF920753,DQ080072,DQ377179,HM756666,GU827999,AY289214,HM488229,HM488186,CS568914,HM756661,HM756678,JF703161,HM488227,HM756659,AF202541,EU155484,DQ431695,HQ671716,AF317203,DQ431709,JF920741,DQ431697,HM488177,HM488221,JX503099,GQ507475,JX015523,DQ164194,HM0671703,HM488140,HQ671669,HM4888231,DQ164205,FJ15913 0,HM488196,DQ164189,HM488190,JF920748,HQ671724,JN819316,HM488141,JX503095,DQ080061,JF920306,HQ671698,JN819309,HM488226,HM488247,JF920728,JF899529,HM488254,DQ318020,JF920758,HM488202,JF415914,HQ671678,JF957166,DQ431706,HQ671685,HM488127,JF488088,HM488117,JF488090,HM488212,KF647250,JF357959,JF957174,JF920755,GQ507479,KC736497,JN183897,AY701412,HM488139,HM488239,D0080056,DQ256376,HM488152,JF488095,DQ666450,GQ507460,GQ50746 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 9,KC736499,HQ671672,JF920743,HM488120,DQ164188,JN819321,JF920734,JXQ15515,DQ164192,JF899535,HM488180,JN858070,DQ786573,GU827998,JX503090,AY688948,JN393308,H0671704,KF234080,JN819324,DQ080066,JF920742,JF703164,JXQ41634,AY278441,HM756662,DQ666452,HM488240,HM488199,KC736494,DQ786572,JF957183,HM756658,HM488162,JN183889,HM488155,JF920756,JF899528,DQ666448,JN183893,HM488225,JN819313,HM488169,GQ379160,HQ671668,DQ318019,JF488097,HM488167,HM488138,HQ671723,CS543188,JN819315,HM756673,HM488153,HQ671690,HQ671697,HM488238,HM488194,FJ483549,JX503091,HM488158,JF719065,JF415917,DQ080057,HQ671729,DQ080055,JXQ41629,JX503096,DQ374651,HM051416,KC407667,DQ431705,JF957170,JF957178,JF920751,DQ431711,HM488121,HM488191,DQ211652,HM488215,H0671726,HQ891011,JF719069,DQ005530,DQ164193,GQ507483,HQ671714,JF703163,DQ666451,HM488114,JF488094,HM488 |

TABLE 10-continued

ViroCap-1.0 Taxonomy

| Taxonomy | Rep.Acc.ID | Host | # GN's | Lineage | Seg. Count | GN.Acc.IDs |
|---|---|---|---|---|---|---|
| | | | | | | 142,AB185914,HM488237,HQ671675,DQ164197,GQ507468,JF415928,HQ671701,JX503085,AY765264,HM488223,JN183891,JF730041,DQ164203,JF957173,HM488241,AY268133,KC736488,HM488176,HQ671686,JXQ15518,HM147824,JF957177,HM488188,DQ164201,AY490240,KF647252,AY603654,HM756676,HM488200,JF972636,HM488243,HM488178,HQ705678,CS56898,JN367277,HM488166,JF957172,HQ705676,DQ431700,AY712947,JQ700437,AY712948,JF415923,DQ080058,JN819312,JF719066,JF415916,HM488122,JN183895,JX503098,HM488244,JX041630,JX123030,H0705659,GQ507471,HM756653,KC736491,DQ164191,HQ891009,HQ671710,JF920732,HM488168,JQ928175,DQ080063,JF415921,DQ164199,JF899531,HQ671712,HQ705673,JF488092,FJ483548,JF920730,DQ431704,JF920760,HM488206,DQ164196,HQ671709,JX503097,JX503086,AF481864,H0671676,JF957163,JXQ15517,JN819306,HM488133,GQ379157,HQ671725,DQ080053,HM488203,KC736496,KF647248,DQ118 |

TABLE 10-continued

VrioCap-1.0 Taxonomy

| Taxonomy | Rep.Acc.ID | Host | Lineage | # GN's | Seg. Count | GN.Acc.IDs |
|---|---|---|---|---|---|---|
| West Nile virus H442 | NC_001563 | vertebrates,invertebrates, human | | | | 127,H TABLE 10-continued VíroCap-1.0 Taxonomy

| Taxonomy | Rep.Acc.ID | Host | # GN's | Lineage | Seg. Count | GN.Acc.IDs |
|---|---|---|---|---|---|---|
| Yellow fever virus | NC_002031 | vertebrates,invertebrates, human | 61 | Flaviviridae,Flavivirus,Yellow fever virus | — | JN81143,JF912190, JF912189,AY968064, JX898877,JF912186, U21056,JF912182,JF 91218,JN81142,JF 912179,AY968065,JF 912180,JX898875,JX 898880,JF912183,JX 898870,U17066,JN62 8281,JX898872,DQ1 18157,JX503529,AF0 52439,U21055,JX898 871,JF912188,JF912 187,KF769015,DQ23 5229,JX898868,AF05 2444,JF912184,JX89 8874,JX898879,GQ3 79162,JN811140,JX8 98876,JX898878,AF0 52438,JF912185,JN8 11141,JN628280,AY6 03338,GQ379163,JX 898881,AF052446,D 0100292,X15062,KF 769016,AF052437,AY 640589,XQ3700,JN62 0362,JX898869,U547 98,AF052445,JN6282 79,U17067,AY572535 ,JX898873,AF094612 |
| Yellow fever virus 17D/Tiantan | NC_002031 | vertebrates,invertebrates, human | 1 | Flaviviridae,Flavivirus,Yellow fever virus | — | FJ654700 |
| Yokose virus | NC_005039 | vertebrates,invertebrates, human | 1 | Flaviviridae,Flavivirus,Yokose virus | — | AB114858 |
| Zaliv Terpenia virus | NC_005214 | vertebrates,invertebrates, human | 1 | Bunyaviridae,Phlebovirus,Uukuniemi virus | seg. L | HM566191 |
| Zaliv Terpenia virus | NC_005220 | vertebrates,invertebrates, human | 1 | Bunyaviridae,Phlebovirus,Uukuniemi virus | seg. M | HM566193 |
| Zaliv Terpenia virus | NC_005221 | vertebrates,invertebrates, human | 1 | Bunyaviridae,Phlebovirus,Uukuniemi virus | seg. S | HM566192 |
| Zika virus | NC_012532 | vertebrates,invertebrates, human | 1 | Flaviviridae,Flavivirus,Zika virus | — | AY632535 |

TABLE 11

| | \multicolumn{10}{c|}{Percentages of human-mapped reads} |
|---|---|---|---|---|---|---|---|---|---|---|
| | S1 Pre-capture | S1 Post-capture | S2 Pre-capture | S2 Post-capture | S3 Pre-capture | S3 Post-capture | S4 Pre-capture | S4 Post-capture | S5 Pre-capture | S5 Post-capture |
| chr 1 | 8.22% | 8.29% | 7.93% | 7.74% | 5.56% | 6.06% | 9.30% | 8.40% | 8.10% | 7.95% |
| chr 2 | 8.86% | 8.75% | 7.17% | 8.33% | 5.01% | 5.22% | 7.24% | 7.61% | 8.35% | 8.29% |
| chr 3 | 6.64% | 6.51% | 4.98% | 5.42% | 4.29% | 4.39% | 5.84% | 5.46% | 6.06% | 5.89% |
| chr 4 | 6.91% | 6.83% | 5.41% | 5.85% | 4.00% | 4.11% | 5.02% | 5.23% | 5.60% | 5.59% |
| chr 5 | 6.16% | 6.10% | 5.60% | 5.94% | 4.39% | 4.47% | 5.40% | 5.22% | 5.64% | 5.51% |
| chr 6 | 5.85% | 5.74% | 4.91% | 4.81% | 3.35% | 3.45% | 5.60% | 5.60% | 5.93% | 5.70% |
| chr 7 | 5.28% | 5.25% | 4.93% | 5.53% | 3.18% | 3.29% | 7.11% | 6.20% | 5.04% | 5.01% |
| chr 8 | 5.00% | 4.95% | 4.26% | 4.22% | 2.96% | 3.03% | 4.41% | 4.30% | 4.57% | 4.52% |
| chr 9 | 3.89% | 3.89% | 3.10% | 2.94% | 2.43% | 2.59% | 3.52% | 3.57% | 3.63% | 3.67% |
| chr 10 | 5.78% | 5.76% | 5.72% | 5.40% | 2.95% | 3.24% | 6.39% | 6.48% | 8.00% | 7.99% |
| chr 11 | 4.26% | 4.28% | 4.72% | 3.15% | 3.07% | 3.14% | 3.88% | 3.95% | 4.40% | 4.21% |
| chr 12 | 4.11% | 4.10% | 3.10% | 4.02% | 2.98% | 2.99% | 3.42% | 3.61% | 3.75% | 3.78% |
| chr 13 | 3.15% | 3.05% | 2.60% | 2.05% | 2.54% | 2.46% | 2.69% | 2.47% | 2.42% | 2.45% |
| chr 14 | 2.72% | 2.71% | 2.50% | 2.20% | 1.74% | 1.74% | 4.17% | 3.26% | 2.65% | 2.60% |
| chr 15 | 2.20% | 2.15% | 2.22% | 1.92% | 1.39% | 1.42% | 2.87% | 2.61% | 2.46% | 2.38% |
| chr 16 | 2.62% | 2.70% | 3.17% | 2.92% | 1.66% | 1.79% | 3.49% | 3.94% | 4.47% | 4.76% |
| chr 17 | 1.65% | 1.65% | 1.69% | 2.17% | 1.14% | 1.21% | 2.16% | 2.21% | 2.35% | 2.37% |
| chr 18 | 2.95% | 2.89% | 2.29% | 2.20% | 1.58% | 1.60% | 3.51% | 3.57% | 2.82% | 2.74% |
| chr 19 | 1.35% | 1.49% | 2.10% | 1.81% | 0.74% | 0.89% | 1.98% | 2.23% | 1.91% | 2.05% |
| chr 20 | 1.44% | 1.42% | 1.69% | 1.78% | 0.96% | 0.95% | 1.86% | 1.84% | 1.91% | 1.83% |
| chr 21 | 1.20% | 1.22% | 1.24% | 1.37% | 0.83% | 0.86% | 1.09% | 1.21% | 1.21% | 1.28% |
| chr 22 | 0.52% | 0.53% | 0.93% | 1.15% | 0.43% | 0.44% | 1.12% | 1.08% | 0.93% | 0.91% |
| MT | 0.22% | 0.22% | 10.65% | 10.07% | 27.65% | 26.51% | 0.79% | 0.95% | 0.44% | 0.37% |
| X | 6.57% | 6.68% | 2.76% | 2.63% | 1.87% | 2.00% | 2.41% | 2.61% | 2.71% | 2.73% |
| Y | 0.27% | 0.33% | 1.10% | 1.52% | 0.87% | 1.16% | 1.62% | 2.26% | 1.96% | 2.36% |

| | S6 Pre-capture | S6 Post-capture | S7 Pre-capture | S7 Post-capture | S8 Pre-capture | S8 Post-capture | P1-14 Pre-capture | P1-14 Post-capture |
|---|---|---|---|---|---|---|---|---|
| chr 1 | 7.58% | 7.54% | 8.37% | 8.13% | 7.45% | 7.80% | 8.80% | 8.67% |
| chr 2 | 8.53% | 8.11% | 7.76% | 8.07% | 9.40% | 8.89% | 8.56% | 8.44% |
| chr 3 | 7.00% | 6.47% | 6.04% | 5.88% | 6.27% | 6.42% | 6.22% | 6.30% |
| chr 4 | 5.91% | 5.93% | 5.72% | 5.57% | 5.99% | 6.12% | 6.09% | 6.18% |
| chr 5 | 5.50% | 5.37% | 5.19% | 5.32% | 5.63% | 5.93% | 5.72% | 5.84% |
| chr 6 | 6.46% | 6.20% | 4.82% | 4.95% | 6.34% | 6.43% | 5.66% | 5.71% |
| chr 7 | 4.72% | 4.87% | 5.62% | 5.54% | 5.44% | 5.36% | 5.46% | 5.39% |
| chr 8 | 4.36% | 4.34% | 5.16% | 4.76% | 4.52% | 4.80% | 4.84% | 4.82% |
| chr 9 | 3.53% | 3.63% | 3.80% | 3.72% | 3.72% | 3.89% | 3.86% | 3.90% |
| chr 10 | 7.38% | 7.31% | 7.02% | 6.94% | 6.22% | 5.46% | 6.26% | 5.87% |
| chr 11 | 4.87% | 4.48% | 4.43% | 4.05% | 3.84% | 4.23% | 4.28% | 4.33% |
| chr 12 | 3.65% | 3.76% | 4.74% | 4.13% | 4.35% | 4.45% | 4.15% | 4.22% |
| chr 13 | 2.34% | 2.45% | 2.49% | 2.52% | 3.20% | 3.26% | 2.82% | 2.83% |
| chr 14 | 2.43% | 2.56% | 2.35% | 2.44% | 2.65% | 2.84% | 2.77% | 2.80% |
| chr 15 | 2.97% | 2.62% | 2.50% | 2.36% | 2.31% | 2.55% | 2.50% | 2.54% |
| chr 16 | 4.18% | 4.46% | 3.57% | 3.59% | 4.23% | 3.64% | 3.08% | 3.04% |
| chr 17 | 2.04% | 2.10% | 2.01% | 2.13% | 2.05% | 2.28% | 2.20% | 2.41% |
| chr 18 | 2.67% | 2.59% | 2.75% | 2.88% | 3.27% | 2.98% | 2.66% | 2.60% |
| chr 19 | 1.67% | 1.99% | 1.89% | 2.01% | 1.77% | 1.82% | 2.13% | 2.13% |
| chr 20 | 2.13% | 2.01% | 2.22% | 1.98% | 1.71% | 1.92% | 1.81% | 1.84% |
| chr 21 | 1.34% | 1.34% | 1.08% | 1.21% | 1.17% | 1.24% | 1.20% | 1.24% |
| chr 22 | 0.88% | 0.90% | 1.02% | 1.01% | 1.24% | 1.28% | 0.88% | 0.90% |
| MT | 0.42% | 0.49% | 1.87% | 2.10% | 0.29% | 0.32% | 0.43% | 0.42% |
| X | 2.49% | 2.70% | 2.50% | 2.68% | 2.46% | 2.72% | 4.55% | 4.62% |
| Y | 2.33% | 2.86% | 2.00% | 2.79% | 2.17% | 1.68% | 0.82% | 0.94% |

What is claimed is:

1. A kit for detecting viral nucleic acid, the kit comprising a panel of probes capable of specifically hybridizing to greater than 100,000 viral nucleic acid sequences, wherein the panel of probes targets regions across complete viral genomes such that the full-length, complete viral genome sequences from a plurality of viruses can be detected, wherein the probes cannot hybridize to a sequence in a human genome, and wherein the plurality of viruses is:

| Taxonomy | NCBI Reference Sequence ID | Host | No. of Genomes | Lineage | Segment Count | Genbank Accession ID |
|---|---|---|---|---|---|---|
| Bovine ephemeral fever virus | NC_002526 | invertebrates,vertebrates | 1 | Rhabdoviridae,Ephemerovirus,Bovine ephemeral fever virus | -b | AF234533 |
| Kotonkan virus | NC_017714 | invertebrates,vertebrates | 1 | Rhabdoviridae,Ephemerovirus,Kotonkan virus | — | HM474855 |
| Murrumbidgee virus | NC_022595 | invertebrates,vertebrates | 1 | Bunyaviridae,Orthobunyavirus,Murrumbidgee virus | seg. L | KF234253 |
| Murrumbidgee virus | NC_022596 | invertebrates,vertebrates | 1 | Bunyaviridae,Orthobunyavirus,Murrumbidgee virus | seg. M | KF234254 |
| Murrumbidgee virus | NC_022597 | invertebrates,vertebrates | 1 | Bunyavirusyaviridae,Orthobunyavirus,Murrumbidgee virus | seg. S | KF234255 |
| Ngaingan virus | NC_013955 | invertebrates,vertebrates | 1 | Rhabdoviridae,Ngaingan virus | — | FJ715959 |
| Tibrogargan virus | NC_020804 | invertebrates,vertebrates | 1 | Rhabdoviridae,Tibrovirus,Tibrogargan virus | — | GQ294472 |
| Circovirus-like genome BBC-A | NC_013020 | unknown | 1 | Circovirus-like genome BBC-A | — | FJ959086 |
| Circovirus-like genome CB-A | NC_013028 | unknown | 1 | Circovirus-like genome CB-A | — | FJ959082 |
| Circovirus-like genome CB-B | NC_013029 | unknown | 1 | Circovirus-like genome CB-B | — | FJ959083 |
| Circovirus-like genome RW-A | NC_013023 | unknown | 1 | Circovirus-like genome RW-A | — | FJ959077 |
| Circovirus-like genome RW-B | NC_013024 | unknown | 1 | Circovirus-like genome RW-B | — | FJ959078 |
| Circovirus-like genome RW-C | NC_013025 | unknown | 1 | Circovirus-like genome RW-C | — | FJ959079 |
| Circovirus-like genome RW-D | NC_013026 | unknown | 1 | Circovirus-like genome RW-D | — | FJ959080 |
| Circovirus-like genome RW-E | NC_013027 | unknown | 1 | Circovirus-like genome RW-E | — | FJ959081 |
| Circovirus-like genome SAR-A | NC_013030 | unknown | 1 | Circovirus-like genome SAR-A | — | FJ959084 |
| Circovirus-like genome SAR-B | NC_013018 | unknown | 1 | Circovirus-like genome SAR-B | — | FJ959085 |
| Dragonfly larvae associated circular virus-1 | NC_023427 | unknown | 1 | Dragonfly larvae associated circular virus-1 | — | KF738873 |
| Dragonfly larvae associated circular virus-10 | NC_023436 | unknown | 2 | Dragonfly larvae associated circular virus-10 | — | KF738885,KF738884 |
| Dragonfly larvae associated circular virus-2 | NC_023428 | unknown | 1 | Dragonfly larvae associated circular virus-2 | — | KF738874 |
| Dragonfly larvae associated circular virus-3 | NC_023429 | unknown | 2 | Dragonfly larvae associated circular virus-3 | — | KF738875,KF738876 |
| Dragonfly larvae associated circular virus-4 | NC_023430 | unknown | 1 | Dragonfly larvae associated circular virus-4 | — | KF738877 |
| Dragonfly larvae associated circular virus-5 | NC_023431 | unknown | 2 | Dragonfly larvae associated circular virus-5 | — | KF738878,KF738879 |
| Dragonfly larvae associated circular virus-6 | NC_023432 | unknown | 1 | Dragonfly larvae associated circular virus-6 | — | KF738880 |
| Dragonfly larvae associated circular virus-7 | NC_023433 | unknown | 1 | Dragonfly larvae associated circular virus-7 | — | KF738881 |

| Taxonomy | NCBI Reference Sequence ID | Host | No. of Genomes | Lineage | Segment Count | Genbank Accession ID |
|---|---|---|---|---|---|---|
| Dragonfly larvae associated circular virus-8 | NC_023434 | unknown | 1 | Dragonfly larvae associated circular virus-8 | — | KF738882 |
| Dragonfly larvae associated circular virus-9 | NC_023435 | unknown | 1 | Dragonfly larvae associated circular virus-9 | — | KF738883 |
| Marine RNA virus JP-A | NC_009757 | unknown | 1 | Marine RNA virus JP-A | — | EF198241 |
| Marine RNA virus JP-B | NC_009758 | unknown | 1 | Marine RNA virus JP-B | — | EF198242 |
| Marine RNA virus SOG | NC_009756 | unknown | 1 | Marine RNA virus SOG | — | EF198240 |
| Ostreid herpesvirus 1 | NC_005881 | unknown | 1 | Malacoherpesviridae,Ostreavirus,Ostreid herpesvirus 1 | — | AY509253 |
| Pig stool associated circular ssDNA virus | NC_017916 | unknown | 8 | Pig stool associated circular ssDNA virus | — | JX305996,JX305993, JX305991,JX305997, JX305998,JX305992, JX305994,JX305995 |
| Pig stool associated circular ssDNA virus GER2011 | NC_017916 | unknown | 1 | Pig stool associated circular ssDNA virus | — | JQ023166 |
| Pithovirus sibericum | NC_023423 | unknown | 1 | Pithovirus sibericum | — | KF740664 |
| Porcine associated stool circular virus | NC_018617 | unknown | 1 | Porcine associated stool circular virus | — | JX274036 |
| Porcine stool-associated circular virus 2 | NC_021203 | unknown | 1 | Porcine stool-associated circular virus 2 | — | KC545226 |
| Porcine stool-associated circular virus 3 | NC_021204 | unknown | 4 | Porcine stool-associated circular virus 3 | — | KC545228,KC545229, KC545227,KC545230 |
| Sclerotinia sclerotiorum hypovirulence associated DNA virus 1 | NC_013116 | unknown | 5 | Sclerotinia sclerotiorum hypovirulence associated DNA virus 1 | — | KF268026,KF268027, KF268028,GQ365709, KF268025 |
| Wallerfield virus | NC_023440 | unknown | 1 | Negevirus,Wallerfield virus | — | KF042857 |
| AKR (endogenous) murine leukemia virus | NC_001702,NC_00181 9,NC_0013 62,NC_001 501 | vertebrates | 1 | Retroviridae,Gammaretrovirus,Murine leukemia virus | — | JQ1998 |
| ARV-138 | NC_015132 | vertebrates | 1 | Reoviridae,Orthoreovirus,Avian orthoreovirus | seg. S1 | AF218359 |
| ARV-176 | NC_015132 | vertebrates | 1 | Reoviridae,Orthoreovirus,Avian orthoreovirus | seg. S1 | AF218358 |
| Abelson murine leukemia virus | NC_001499 | vertebrates | 1 | Retroviridae,Gammaretrovirus,Abelson murine leukemia virus | — | AF033812 |
| Acartia tonsa copepod circovirus | NC_020099 | vertebrates | 1 | Circoviridae,Circovirus,Acartia tonsa copepod circovirus | — | JQ837277 |
| Adeno-associated virus-1 | NC_002077 | vertebrates | 1 | Parvoviridae,Dependovirus,Adeno-associated virus-1 | — | AF063497 |
| Adeno-associated virus-4 | NC_001829 | vertebrates | 1 | Parvoviridae,Dependovirus,Adeno-associated virus-4 | — | U89790 |
| Adeno-associated virus-6 | NC_002077 | vertebrates | 1 | Parvoviridae,Dependovirus,Adeno-associated virus-1 | — | AF028704 |
| Adeno-associated virus-7 | NC_006260 | vertebrates | 1 | Parvoviridae,Dependovirus,Adeno-associated virus-7 | — | AF513851 |

| Taxonomy | NCBI Reference Sequence ID | Host | No. of Genomes | Lineage | Segment Count | Genbank Accession ID |
|---|---|---|---|---|---|---|
| Adeno-associated virus-8 | NC_006261 | vertebrates | 1 | Parvoviridae,Dependovirus,Adeno-associated virus-8 | — | AF513852 |
| African elephant polyomavirus 1 | NC_022519 | vertebrates | 1 | Polyomaviridae,Polyomavirus,African elephant polyomavirus 1 | — | KF147833 |
| African green monkey polyomavirus | NC_004763 | vertebrates | 1 | Polyomaviridae,Polyomavirus,African green monkey polyomavirus | — | K02562 |
| African green monkey simian foamy virus | NC_010820 | vertebrates | 1 | Retroviridae,Spumavirus,African green monkey simian foamy virus | — | M74895 |
| Aichi virus | NC_001918 | vertebrates | 10 | Picornaviridae,Kobuvirus,Aichivirus A | — | FJ890523,DQ028632,AY747174,GQ927704,JX564249,GQ927705,GQ927712,AB040749,GQ927706,GQ927711 |
| Aichi virus 1 | NC_001918 | vertebrates | 1 | Picornaviridae,Kobuvirus,Aichivirus A | — | AB010145 |
| Alcelaphine herpesvirus 1 | NC_002531 | vertebrates | 1 | Herpesviridae,Macavirus,Alcelaphine herpesvirus 1 | — | AF005370 |
| Aleutian mink disease virus | NC_001662 | vertebrates | 6 | Parvoviridae,Amdovirus,Aleutian mink disease virus | — | GU269892,JN040434,Z18276,M20036,GU183264,GU183265 |
| Ambystoma tigrinum virus | NC_005832 | vertebrates | 1 | Iridoviridae,Ranavirus,Ambystoma tigrinum virus | — | AY150217 |
| American bat vesiculovirus TFFN-2013 | NC_022755 | vertebrates | 1 | Rhabdoviridae,Vesiculovirus,American bat vesiculovirus TFFN-2013 | — | JX569193 |
| American grass carp reovirus | NC_010584 | vertebrates | 1 | Reoviridae,Aquareovirus,Aquareovirus G | seg. 1 | EF589098 |
| American grass carp reovirus | NC_010585 | vertebrates | 1 | Reoviridae,Aquareovirus,Aquareovirus G | seg. 2 | EF589099 |
| American grass carp reovirus | NC_010586 | vertebrates | 1 | Reoviridae,Aquareovirus,Aquareovirus G | seg. 3 | EF589100 |
| American grass carp reovirus | NC_010587 | vertebrates | 1 | Reoviridae,Aquareovirus,Aquareovirus G | seg. 4 | EF589101 |
| American grass carp reovirus | NC_010588 | vertebrates | 1 | Reoviridae,Aquareovirus,Aquareovirus G | seg. 5 | EF589102 |
| American grass carp reovirus | NC_010589 | vertebrates | 1 | Reoviridae,Aquareovirus,Aquareovirus G | seg. 6 | EF589103 |
| American grass carp reovirus | NC_010590 | vertebrates | 1 | Reoviridae,Aquareovirus,Aquareovirus G | seg. 7 | EF589104 |
| American grass carp reovirus | NC_010591 | vertebrates | 1 | Reoviridae,Aquareovirus,Aquareovirus G | seg. 8 | EF589105 |
| American grass carp reovirus | NC_010592 | vertebrates | 1 | Reoviridae,Aquareovirus,Aquareovirus G | seg. 9 | EF589106 |
| American grass carp reovirus | NC_010593 | vertebrates | 1 | Reoviridae,Aquareovirus,Aquareovirus G | seg. 10 | EF589107 |
| American grass carp reovirus | NC_010594 | vertebrates | 1 | Reoviridae,Aquareovirus,Aquareovirus G | seg. 11 | EF589108 |

| Taxonomy | NCBI Reference Sequence ID | Host | No. of Genomes | Lineage | Segment Count | Genbank Accession ID |
|---|---|---|---|---|---|---|
| Amphotropic murine leukemia virus | NC_001702, NC_001819, NC_001362, NC_001501 | vertebrates | 1 | Retroviridae,Gammaretrovirus,Murine leukemia virus | — | AF411814 |
| Anatid herpesvirus 1 | NC_013036 | vertebrates | 6 | Herpesviridae,Mardivirus,Anatid herpesvirus 1 | — | JQ673560,KF487736, JF999965,KF263690, EU082088,JQ647509 |
| Andrias davidianus | NC_005946 | vertebrates | 1 | Incloviridae,Ranavirus,Frog virus 3 ranavirus | — | KC865735 |
| Anguilla anguilla circovirus | NC_023421 | vertebrates | 1 | Circoviridae,Circovirus,Anguilla anguilla circovirus | — | KC469701 |
| Anguillid herpesvirus 1 | NC_013668 | vertebrates | 1 | Alloherpesviridae,Cyprinivirus,Anguillid herpesvirus 1 | — | FJ940765 |
| Aotine herpesvirus 1 | NC_016447 | vertebrates | 1 | Herpesviridae,Cytomegalovirus,Aotine herpesvirus 1 | — | FJ483970 |
| Aquareovirus A | NC_007582 | vertebrates | 1 | Reoviridae,Aquareovirus,Aquareovirus A | seg. 1 | AF418294 |
| Aquareovirus A | NC_007583 | vertebrates | 1 | Reoviridae,Aquareovirus,Aquareovirus A | seg. 2 | AF418295 |
| Aquareovirus A | NC_007584 | vertebrates | 1 | Reoviridae,Aquareovirus,Aquareovirus A | seg. 3 | AF418296 |
| Aquareovirus A | NC_007585 | vertebrates | 1 | Reoviridae,Aquareovirus,Aquareovirus A | seg. 4 | AF418297 |
| Aquareovirus A | NC_007588 | vertebrates | 1 | Reoviridae,Aquareovirus,Aquareovirus A | seg. 8 | AF418301 |
| Aquareovirus A | NC_007589 | vertebrates | 1 | Reoviridae,Aquareovirus,Aquareovirus A | seg. 9 | AF418302 |
| Aquareovirus A | NC_007590 | vertebrates | 1 | Reoviridae,Aquareovirus,Aquareovirus A | seg. 10 | AF418303 |
| Aquareovirus A | NC_007591 | vertebrates | 1 | Reoviridae,Aquareovirus,Aquareovirus A | seg. 11 | AF418304 |
| Aquareovirus C | NC_007592 | vertebrates | 1 | Reoviridae,Aquareovirus,Aquareovirus A | seg. 6 | AF418299 |
| Aquareovirus C | NC_005166 | vertebrates | 1 | Reoviridae,Aquareovirus,Aquareovirus C | seg. 1 | AF403398 |
| Aquareovirus C | NC_005167 | vertebrates | 1 | Reoviridae,Aquareovirus,Aquareovirus C | seg. 2 | AF403399 |
| Aquareovirus C | NC_005168 | vertebrates | 1 | Reoviridae,Aquareovirus,Aquareovirus C | seg. 3 | AF403400 |
| Aquareovirus C | NC_005169 | vertebrates | 1 | Reoviridae,Aquareovirus,Aquareovirus C | seg. 4 | AF403401 |
| Aquareovirus C | NC_005170 | vertebrates | 1 | Reoviridae,Aquareovirus,Aquareovirus C | seg. 5 | AF403402 |
| Aquareovirus C | NC_005171 | vertebrates | 1 | Reoviridae,Aquareovirus,Aquareovirus C | seg. 6 | AF403403 |
| Aquareovirus C | NC_005172 | vertebrates | 1 | Reoviridae,Aquareovirus,Aquareovirus C | seg. 7 | AF403404 |
| Aquareovirus C | NC_005173 | vertebrates | 1 | Reoviridae,Aquareovirus,Aquareovirus C | seg. 8 | AF403405 |
| Aquareovirus C | NC_005174 | vertebrates | 1 | Reoviridae,Aquareovirus,Aquareovirus C | seg. 9 | AF403406 |
| Aquareovirus C | NC_005175 | vertebrates | 1 | Reoviridae,Aquareovirus,Aquareovirus C | seg. 10 | AF403407 |
| Aquareovirus C | NC_005176 | vertebrates | 1 | Reoviridae,Aquareovirus,Aquareovirus C | seg. 11 | AF403408 |
| Arctic ground squirrel hepatitis B virus | NC_001484 | vertebrates | 1 | Hepadnaviridae,Orthohepadnavirus,Ground squirrel hepatitis virus | — | U29144 |
| Artibeus jamaicensis parvovirus 1 | NC_016752 | vertebrates | 1 | Parvoviridae, Artibeus jamaicensis parvovirus 1 | — | JQ037754 |
| Astrovirus MLB1 | NC_011400 | vertebrates | 5 | Astroviridae,Astrovirus MLB1 | — | JQ086552,AB823732, AB823731,FJ402983, FJ222451 |

| Taxonomy | NCBI Reference Sequence ID | Host | Lineage | No. of Genomes | Segment Count | Genbank Accession ID |
|---|---|---|---|---|---|---|
| Astrovirus MLB1 HK05 | NC_011400 | vertebrates | Astroviridae,Astrovirus MLB1 | 1 | — | HM450380 |
| Astrovirus MLB2 | NC_016155 | vertebrates | Astroviridae,Astrovirus MLB2 | 2 | — | JF742759,AB829252 |
| Astrovirus MLB3 | NC_019028 | vertebrates | Astroviridae,Astrovirus MLB3 | 1 | — | JX857870 |
| Astrovirus VA1 | NC_013060 | vertebrates | Astroviridae,Astrovirus VA1 | 1 | — | FJ973620 |
| Astrovirus VA2 | NC_018669 | vertebrates | Astroviridae,Astrovirus VA2 | 1 | — | GQ502193 |
| Astrovirus VA3 | NC_019026 | vertebrates | Astroviridae,Astrovirus VA3 | 1 | — | JX857868 |
| Astrovirus VA4 | NC_019027 | vertebrates | Astroviridae,Astrovirus VA4 | 1 | — | JX857869 |
| Astrovirus wild boar/W BAstV-1/2011/HUN | NC_016896 | vertebrates | Astroviridae,Mamastrovirus,Astrovirus wild boar/W BAstV-1/2011/HU N | 1 | — | JQ340310 |
| Ateles paniscus polyomavirus 1 | NC_019853 | vertebrates | Polyomaviridae,Polyomavirus,Ateles paniscus polyomavirus 1 | 1 | — | JX159987 |
| Ateline herpesvirus 3 | NC_001987 | vertebrates | Herpesviridae,Rhadinovirus,Ateline herpesvirus 3 | 1 | — | AF083424 |
| Atlantic salmon reovirus TS | NC_007583 | vertebrates | Reoviridae,Aquareovirus,Aquareovirus A | 1 | seg. 2 | EF434978 |
| Atlantic salmon reovirus TS | NC_007590 | vertebrates | Reoviridae,Aquareovirus,Aquareovirus A | 1 | seg. 10 | EF434979 |
| Atlantic salmon swim bladder sarcoma virus | NC_007654 | vertebrates | Retroviridae,Atlantic salmon swim bladder sarcoma virus | 1 | — | DQ174103 |
| Avian adeno-associated virus | NC_006263 | vertebrates | Parvoviridae,Dependovirus,Avian adeno-associated virus | 1 | — | GQ368252 |
| Avian adeno-associated virus ATCC VR-865 | NC_004828 | vertebrates | Parvoviridae,Dependovirus,Avian adeno-associated virus ATCC VR-865 | 2 | — | AY186198,AY629582 |
| Avian adeno-associated virus strain DA-1 | NC_006263 | vertebrates | Parvoviridae,Dependovirus,Avian adeno-associated virus | 1 | — | AY629583 |
| Avian carcinoma virus | NC_001402 | vertebrates | Retroviridae,Alpharetrovirus,Avian carcinoma virus | 1 | — | M14008 |
| Avian encephalomyelitis virus | NC_003990 | vertebrates | Picornaviridae,Tremovirus,Avian encephalomyelitis virus | 3 | — | AJ225173,AY275539, AY517471 |
| Avian endogenous retrovirus EAV-HP | NC_005947 | vertebrates | Retroviridae, Avian endogenous retrovirus EAV-HP | 7 | — | AJ623291,AJ238124, AJ238125,AJ623292, AJ623289,AJ292966, AJ623290 |
| Avian gyrovirus 2 | NC_015396 | vertebrates | Circoviridae,Gyrovirus,Avian gyrovirus 2 | 2 | — | HM590588,JQ690763 |
| Avian infectious bronchitis virus (strain Beaudette CK) | NC_010800 ,NC_00145 1 | vertebrates | Coronaviridae,Gammacoronavirus,Avian coronavirus | 1 | — | AJ311317 |
| Avian infectious bronchitis virus partridge/GD/S14/2003 | NC_010800 ,NC_00145 1 | vertebrates | Coronaviridae,Gammacoronavirus,Avian coronavirus | 1 | — | AY646283 |
| Avian leukemia virus | NC_015116 ,NC_00140 8 | vertebrates | Retroviridae,Alpharetrovirus,Avian leukosis virus | 1 | — | HQ425636 |
| Avian leukosis virus | NC_015116 ,NC_00140 8 | vertebrates | Retroviridae,Alpharetrovirus,Avian leukosis virus | 59 | — | KF562374,JF932001, JF932004,HQ148555, AY013303,AB669569 JF931999,HM58265 7,AB669897,AB6694 |

| Taxonomy | NCBI Reference Sequence ID | Host | No. of Genomes | Lineage | Segment Count | Genbank Accession ID |
|---|---|---|---|---|---|---|
| Avian leukosis virus HPRS103 | NC_015116, NC_001408 | vertebrates | 1 | Retroviridae,Alpharetrovirus,Avian leukosis virus | — | 33,AB670314,AB764104,AB303223,EU070900,JF826241,JX254901,JF932002,HM452340,HM235667,KF738251,KF562373,HM235669,EU070902,JF932003,DQ365814,JN389518,AB764106,FJ216405,AB669896,HM452342,HM235668,HM452339,JN624880,JF932000,AB764107,GU982310,JN389517,HQ148554,HM452341,GU982308,EU070901,AB682778,HQ900844,EF467236,JN624879,HM235670,KF562375,HM582658,JF951728,AB112960,JX855935,AY013304,JX453210,AB670312,DQ115805,HM235665,HM776937,JN624878,AB669568 |
| Avian leukosis virus LR-9 | NC_015116, NC_001408 | vertebrates | 1 | Retroviridae,Alpharetrovirus,Avian leukosis virus | — | Z46390 |
| Avian myelocytomatosis virus | NC_001866 | vertebrates | 2 | Retroviridae,Alpharetrovirus,Avian myelocytomatosis virus | — | AY350569 |
| Avian orthoreovirus | NC_015126 | vertebrates | 8 | Reoviridae,Orthoreovirus,Avian orthoreovirus | seg. L1 | M11784,AF033809 |
| Avian orthoreovirus | NC_015127 | vertebrates | 2 | Reoviridae,Orthoreovirus,Avian orthoreovirus | seg. L2 | FR694191,DQ238093,DQ238094,EU61673 9,EU616735,HM222978,AY547458,KC183748 |
| Avian orthoreovirus | NC_015128 | vertebrates | 14 | Reoviridae,Orthoreovirus,Avian orthoreovirus | seg. L3 | HM222980,FR694192 |
| | | | | | | AY652695,AY652698,AY652700,DQ30017 5,AY652694,EU6167 38,FR694193,HM222979,AY652699,AY65 |

| Taxonomy | NCBI Reference Sequence ID | Host | No. of Genomes | Lineage | Segment Count | Genbank Accession ID |
|---|---|---|---|---|---|---|
| Avian orthoreovirus | NC_015129 | vertebrates | 19 | Reoviridae,Orthoreovirus,Avian orthoreovirus | seg. M | 2697,AY652696,AY652701,EU616737,AY652693 |
| Avian orthoreovirus | NC_015130 | vertebrates | 19 | Reoviridae,Orthoreovirus,Avian orthoreovirus | seg. M | AY639620,AY639614,AY557188,EU61673 6,AY639612,AY5571 89,AY639619,AY639 617,AY639621,AY63 9613,AY639616,FR6 94194,AY639611,AY 639618,AY639615,E U616740,HM222977, DQ300176,AY639610 |
| Avian orthoreovirus | NC_015131 | vertebrates | 21 | Reoviridae,Orthoreovirus,Avian orthoreovirus | seg. M3 | AY635940,AY635938 2,EU61674l,HM22297 6,AY635936,DQ3001 77,AY635943,AY635 935,AY635945,AY63 5944,EU616742,AY6 35941,AY635934,AY 635939,AY750053,A Y635937,AY635942,F R694195,AY750052 |
| Avian orthoreovirus | NC_015132 | vertebrates | 15 | Reoviridae,Orthoreovirus,Avian orthoreovirus | seg. S1 | AY573911,FR694196 ,AY573912,AY57391 3,AY573908,AY5739 07,AY557191,AY573 909,EU616744,AY57 3905,AY573910,KC8 65791,AY573914,AY 608700,AY557190,A Y573904,AY573915, EU616743,HM22297 5,AY303993,AY5739 06 |
| Avian orthoreovirus | NC_015133 | vertebrates | 6 | Reoviridae,Orthoreovirus,Avian orthoreovirus | seg. S2 | AF004857,JN559377, L39002, HM222974,D 0525419,JN559375,F R694197,DQ643974, DQ868790, DQ86879 1,DQ643975,EF0573 97,DQ868789,EF057 398,EU526387 |
| Avian orthoreovirus | | vertebrates | | Reoviridae,Orthoreovirus,Avian orthoreovirus | | AF059717,FR694198, AF104311,JN559376, AF059716,HM222973 |

-continued

| Taxonomy | NCBI Reference Sequence ID | Host | No. of Genomes | Lineage | Segment Count | Genbank Accession ID |
|---|---|---|---|---|---|---|
| Avian orthoreovirus | NC_015134 | vertebrates | 12 | Reoviridae,Orthoreovirus,Avian orthoreovirus | seg. S3 | EF030496,JQ924284, AF059720,EF030498, AF059721,EF030497, HM222972,AF004856 ,EF030499,JQ916907 ,DQ415659,FR69419 9 |
| Avian orthoreovirus | NC_015135 | vertebrates | 6 | Reoviridae,Orthoreovirus,Avian orthoreovirus | seg. S4 | HM222971,AF059725 ,EF122838,JN559378 ,AF059724,FR694200 |
| Avian orthoreovirus strain 1017-1 | NC_015126 | vertebrates | 1 | Reoviridae,Orthoreovirus,Avian orthoreovirus | seg. L1 | AY641740 |
| Avian orthoreovirus strain 2408 | NC_015126 | vertebrates | 1 | Reoviridae,Orthoreovirus,Avian orthoreovirus | seg. L1 | AY641742 |
| Avian orthoreovirus strain 601G | NC_015126 | vertebrates | 1 | Reoviridae,Orthoreovirus,Avian orthoreovirus | seg. L1 | AY641736 |
| Avian orthoreovirus strain 916 | NC_015126 | vertebrates | 1 | Reoviridae,Orthoreovirus,Avian orthoreovirus | seg. L1 | AY641737 |
| Avian orthoreovirus strain 918 | NC_015126 | vertebrates | 1 | Reoviridae,Orthoreovirus,Avian orthoreovirus | seg. L1 | AY641738 |
| Avian orthoreovirus strain 919 | NC_015126 | vertebrates | 1 | Reoviridae,Orthoreovirus,Avian orthoreovirus | seg. L1 | AY641739 |
| Avian orthoreovirus strain OS161 | NC_015126 | vertebrates | 1 | Reoviridae,Orthoreovirus,Avian orthoreovirus | seg. L1 | AY641743 |
| Avian orthoreovirus strain R2/TW | NC_015126 | vertebrates | 1 | Reoviridae,Orthoreovirus,Avian orthoreovirus | seg. L1 | AY641744 |
| Avian reovirus strain 1733 | NC_015126 | vertebrates | 1 | Reoviridae,Orthoreovirus,Avian orthoreovirus | seg. L1 | AY641741 |
| Avian reovirus strain 1733 | NC_015128 | vertebrates | 1 | Reoviridae,Orthoreovirus,Avian orthoreovirus | seg. L3 | AF384171 |
| Avian reovirus strain S1133 | NC_015126 | vertebrates | 1 | Reoviridae,Orthoreovirus,Avian orthoreovirus | seg. L1 | AY641735 |
| Avian reovirus strain S1133 | NC_015132 | vertebrates | 1 | Reoviridae,Orthoreovirus,Avian orthoreovirus | seg. S1 | AF330703 |
| Avian sapelovirus | NC_006553 | vertebrates | 1 | Picornaviridae,Sapelovirus,Avian sapelovirus | — | AY563023 |
| Avirulent turkey hemorrhagic enteritis virus | NC_001958 | vertebrates | 1 | Adenoviridae,Siadenovirus,Turkey adenovirus A | — | AY849321 |
| Baboon enterovirus | NC_010415 | vertebrates | 1 | Picornaviridae,Enterovirus,Enterovirus J | — | AF326766 |
| Baboon orthoreovirus | NC_015877 | vertebrates | 1 | Reoviridae,Orthoreovirus,Baboon orthoreovirus | seg. L1 | HQ847903 |
| Baboon orthoreovirus | NC_015878 | vertebrates | 1 | Reoviridae,Orthoreovirus,Baboon orthoreovirus | seg. L2 | HQ847904 |
| Baboon orthoreovirus | NC_015879 | vertebrates | 1 | Reoviridae,Orthoreovirus,Baboon orthoreovirus | seg. L3 | HQ847905 |
| Baboon orthoreovirus | NC_015880 | vertebrates | 1 | Reoviridae,Orthoreovirus,Baboon orthoreovirus | seg. M1 | HQ847906 |
| Baboon orthoreovirus | NC_015881 | vertebrates | 1 | Reoviridae,Orthoreovirus,Baboon orthoreovirus | seg. M2 | HQ847907 |

-continued

| Taxonomy | NCBI Reference Sequence ID | Host | No. of Genomes | Lineage | Segment Count | Genbank Accession ID |
|---|---|---|---|---|---|---|
| Baboon orthoreovirus | NC_015882 | vertebrates | 1 | Reoviridae,Orthoreovirus,Baboon orthoreovirus | seg. M3 | HQ847908 |
| Baboon orthoreovirus | NC_015883 | vertebrates | 1 | Reoviridae,Orthoreovirus,Baboon orthoreovirus | seg. S1 | AF059719 |
| Baboon orthoreovirus | NC_015884 | vertebrates | 1 | Reoviridae,Orthoreovirus,Baboon orthoreovirus | seg. S2 | AF059723 |
| Baboon orthoreovirus | NC_015885 | vertebrates | 1 | Reoviridae,Orthoreovirus,Baboon orthoreovirus | seg. S4 | AF406787 |
| Baboon orthoreovirus | NC_015886 | vertebrates | 1 | Reoviridae,Orthoreovirus,Baboon orthoreovirus | seg. S3 | AF059727 |
| Bandicoot papillomatosis carcinomatosis virus type 1 | NC_010107 | vertebrates | 1 | Papillomaviridae,Bandicoot papillomatosis carcinomatosis virus type 1 | — | EU069819 |
| Bandicoot papillomatosis carcinomatosis virus type 2 | NC_010817 | vertebrates | 1 | Papillomaviridae,Bandicoot papillomatosis carcinomatosis virus type 2 | — | EU277647 |
| Barbel circovirus | NC_015399 | vertebrates | 2 | Circoviridae,Circovirus,Barbel circovirus | — | JF279961,GU799606 |
| Barfin flounder nervous necrosis virus | NC_013458 | vertebrates | 1 | Nodaviridae,Betanodavirus,Barfin flounder nervous necrosis virus | seg. RNA 1 | EU236146 |
| Barfin flounder nervous necrosis virus | NC_013459 | vertebrates | 1 | Nodaviridae,Betanodavirus,Barfin flounder nervous necrosis virus | seg. RNA 2 | EU236147 |
| Barfin flounder virus BF93Hok | NC_011063 | vertebrates | 1 | Nodaviridae,Betanodavirus,Barfin flounder virus BF93Hok | seg. RNA 1 | EU826137 |
| Barfin flounder virus BF93Hok | NC_011064 | vertebrates | 1 | Nodaviridae,Betanodavirus,Barfin flounder virus BF93Hok | seg. RNA 2 | EU826138 |
| Bat adeno-associated virus YNM | NC_014468 | vertebrates | 1 | Parvoviridae,Dependovirus,Bat adeno-associated virus YNM | — | GU226971 |
| Bat adenovirus 2 | NC_015932 | vertebrates | 1 | Adenoviridae,Mastadenovirus,Bat adenovirus B | — | JN252129 |
| Bat adenovirus TJM | NC_016895 | vertebrates | 1 | Adenoviridae,Mastadenovirus,Bat adenovirus A | — | GU226970 |
| Bat circovirus | NC_021206 | vertebrates | 2 | Circoviridae,Circovirus,Bat circovirus | — | KC339249,JX863737 |
| Bat coronavirus (BtCoV/133/2005) | NC_008315 | vertebrates | 1 | Coronaviridae,Betacoronavirus,Bat coronavirus (BtCoV/133/2005) | — | DQ648794 |
| Bat coronavirus 1A | NC_010437 | vertebrates | 1 | Coronaviridae,Alphacoronavirus,Bat coronavirus 1A | — | EU420138 |
| Bat coronavirus 1B | NC_010436 | vertebrates | 1 | Coronaviridae,Alphacoronavirus,Bat coronavirus 1B | — | EU420137 |
| Bat coronavirus BM48-31/BG R/2008 | NC_014470 | vertebrates | 1 | Coronaviridae,Bat coronavirus BM48-31/BG R/2008 | — | GU190215 |
| Bat coronavirus CDPHE15/USA/2006 | NC_022103 | vertebrates | 1 | Coronaviridae,Alphacoronavirus,Bat coronavirus CDPHE15/USA/2006 | — | KF430219 |
| Bat coronavirus HKU4-2 | NC_009019 | vertebrates | 1 | Coronaviridae,Betacoronavirus,Tylonycteris bat coronavirus HKU4 | — | EF065506 |
| Bat coronavirus HKU4-3 | NC_009019 | vertebrates | 1 | Coronaviridae,Betacoronavirus,Tylonycteris bat coronavirus HKU4 | — | EF065507 |
| Bat coronavirus HKU4-4 | NC_009019 | vertebrates | 1 | Coronaviridae,Betacoronavirus,Tylonycteris bat coronavirus HKU4 | — | EF065508 |
| Bat coronavirus HKU5-2 | NC_009020 | vertebrates | 1 | Coronaviridae,Betacoronavirus,Pipistrellus bat coronavirus HKU5 | — | EF065510 |

| Taxonomy | NCBI Reference Sequence ID | Host | No. of Genomes | Lineage | Segment Count | Genbank Accession ID |
|---|---|---|---|---|---|---|
| Bat coronavirus HKU5-3 | NC_009020 | vertebrates | 1 | Coronaviridae,Betacoronavirus,Pipistrellus bat coronavirus HKU5 | — | EF065511 |
| Bat coronavirus HKU5-5 | NC_009020 | vertebrates | 1 | Coronaviridae,Betacoronavirus,Pipistrellus bat coronavirus HKU5 | — | EF065512 |
| Bat coronavirus HKU9-10-1 | NC_009021 | vertebrates | 1 | Coronaviridae,Betacoronavirus,Rousettus bat coronavirus HKU9 | — | HM211100 |
| Bat coronavirus HKU9-10-2 | NC_009021 | vertebrates | 1 | Coronaviridae,Betacoronavirus,Rousettus bat coronavirus HKU9 | — | HM211101 |
| Bat coronavirus HKU9-2 | NC_009021 | vertebrates | 1 | Coronaviridae,Betacoronavirus,Rousettus bat coronavirus HKU9 | — | EF065514 |
| Bat coronavirus HKU9-3 | NC_009021 | vertebrates | 1 | Coronaviridae,Betacoronavirus,Rousettus bat coronavirus HKU9 | — | EF065515 |
| Bat coronavirus HKU9-4 | NC_009021 | vertebrates | 1 | Coronaviridae,Betacoronavirus,Rousettus bat coronavirus HKU9 | — | EF065516 |
| Bat coronavirus HKU9-5-1 | NC_009021 | vertebrates | 1 | Coronaviridae,Betacoronavirus,Rousettus bat coronavirus HKU9 | — | HM211098 |
| Bat coronavirus HKU9-5-2 | NC_009021 | vertebrates | 1 | Coronaviridae,Betacoronavirus,Rousettus bat coronavirus HKU9 | — | HM211099 |
| Bat hepatitis virus | NC_020881 | vertebrates | 3 | Hepadnaviridae,Bat hepatitis virus | — | JX941466,JX941467,JX941468 |
| Bat picornavirus 1 | NC_015940 | vertebrates | 2 | Picornaviridae,Bat picornavirus 1 | — | HQ59534l,HQ59534 0 |
| Bat picornavirus 2 | NC_015941 | vertebrates | 2 | Picornaviridae,Bat picornavirus 2 | — | HQ59534 2,HQ59534 3 |
| Bat picornavirus 3 | NC_015934 | vertebrates | 2 | Picornaviridae,Bat picornavirus 3 | — | HQ59534 5,HQ59534 4 |
| Beak and feather disease virus | NC_001944 | vertebrates | 205 | Circoviridae,Circovirus,Beak and feather disease virus | — | JQ782201,GU936294,JX221005,JX221002,GU936287,JQ782197,GQ396655,JX221100 3,AY521238,KF18869 4,AF311297,JXQ4920 6,JX221025,GQ1657 56,GU015021,JX221 014,AY450436,GUO1 5014,HM748920,JX2 21001,HM748922,GU 936289,AY521236,JX 049195,GU936291,G U015015,JF519618,J X221031,JX221030,A B277750,GQ396653, GU936290,HM74892 7,HM748935,AF3112 99,JX221007,GU015 023,KC980909,AB27 7747,JX221011,HM7 48924,GQ120621,JX |

| Taxonomy | NCBI Reference Sequence ID | Host | No. of Genomes | Lineage | Segment Count | Genbank Accession ID |
|---|---|---|---|---|---|---|
| | | | | | | 221006,JXQ49198,AY450441,JX221004,G0396652,AB277746,JX221040,HM748925,KF188684,KF467254,JXQ49197,DQ397818,JXQ49199,AB277751,JX221016,JQ782199,GU047347,KC69365,1,KF188685,FJ685981,KF188685,FJ68598,0,GU015012,AF07178,AF311296,JX221012,GQ386944,KF188687,JQ782196,EF457975,GU015018,JX21032,GU015016,JX221021,JXQ49216,AY450438,AY450440,AF311302,JXQ49219,JX221008,GU015019,GU936295,HM748932,EU810208,FJ685989,AF311301,JXQ49200,KF188683,JXQ49218,JXQ49209,GU015022,KF188689,JX221024,JXQ49217,JX221010,JXQ49220,HM748919,JX221037,KF188681,JQ782200,HM748934,HM748928,JXQ49204,KF188690,JXQ49205,JXQ49208,JX221036,JF519619,AB514568,GQ165757,FJ685979,JX221038,HM748931,JQ782208,AY450442,JXQ49214,JX221035,JX221039,JQ782204,KF188693,JX221018,JX221043,JXQ49203,AY450434,AY450439,KF188686,GQ165758,KF188682,G0396656,JX221022,JX221013,JQ782206,HM748929,AY521237,GU936292,KF67333 |

| Taxonomy | NCBI Reference Sequence ID | Host | No. of Genomes | Lineage | Segment Count | Genbank Accession ID |
|---|---|---|---|---|---|---|
| Beluga Whale coronavirus SW1 | NC_010646 | vertebrates | 1 | Coronaviridae,Gammacoronavirus,Beluga Whale coronavirus SW1 | — | 5,JX221019,GU9362 96,KF673337,KF4672 52,AY450435,AB277 748,FJ685985,JX221 026,JX221034,HM74 8938,JX221041,HM7 48933,EF457974,AY4 50443,JXQ49211,HM 748930,JX221042,JX 221027,JXQ49207,AF 311300,HM748926,K F673336,GU015013,J X221020,JXQ49213,A F311298,JXQ49202,J X221023,GU936293, JQ782198,JXQ49196, GQ329705,JX221017 ,HM748937,KF56125 0,HM748921,JX2210 29,JX221033,GU015 017,KF850537,HM74 8936,HM748918,JQ7 82205,EU810207,JXQ 49215,GU936288,AF 080560,GQ396654,J XQ49210,AB277749, KF188688,JXQ49201, GU015020,HM74892 3,KC510146,KF1886 92,JXQ49212,AF3112 95,GU936297,HM748 939,KF467251,JXQ49 221,KF188691,JX221 009,JX221028,AY450 437,FJ685978,KF467 253,JX221015 |
| Betacoronavirus England 1 | NC_019843 | vertebrates | 1 | Coronaviridae,Betacoronavirus,Middle East respiratory syndrome coronavirus | — | EU111742 |
| Betacoronavirus Erinaceus/VMC/DEU/2012 | NC_022643 | vertebrates | 2 | Coronaviridae,Betacoronavirus,Betacoronavirus Erinaceus/VMC/D EU/2012 | — | KC164505 |
| Bettongia penicillata papillomavirus 1 | NC_014143 | vertebrates | 1 | Papillomaviridae,Bettongia penicillata papillomavirus 1 | — | KC545383,KC545386 |
| Blotched snakehead virus | NC_005982 | vertebrates | 1 | Birnaviridae,Blosnavirus,Blotched snakehead virus | seg. A | GU220391 |
| Blotched snakehead virus | NC_005983 | vertebrates | 1 | Birnaviridae,Blosnavirus,Blotched snakehead virus | seg. B | AJ459382 |
| | | | | | | AJ459383 |

| Taxonomy | NCBI Reference Sequence ID | Host | No. of Genomes | Lineage | Segment Count | Genbank Accession ID |
|---|---|---|---|---|---|---|
| Bluegill picornavirus | NC_018506 | vertebrates | 1 | Bluegill picornavirus | — | JX134222 |
| Bocavirus gorilla/GBoV1/2009 | NC_014358 | vertebrates | 1 | Parvoviridae,Bocavirus,Bocavirus gorilla/GBoV1/2009 | — | HM145750 |
| Border disease virus | NC_003679 | vertebrates | 5 | Flaviviridae,Pestivirus,Border disease virus | — | KC963426,KF925348,AF037405,GU270877,GQ902940 |
| Border disease virus-BD31 | NC_003679 | vertebrates | 1 | Flaviviridae,Pestivirus,Border disease virus | — | U70263 |
| Bos grunniens papillomavirus type 1 | NC_001522 | vertebrates | 6 | Papillomaviridae,Deltapapillomavirus,Deltapapillomavirus 4 | — | JX174438,JX174439,JX174441,JX174442,JX174437,JX174440 |
| Bottlenose dolphin coronavirus HKU22 | NC_010646 | vertebrates | 3 | Coronaviridae,Gammacoronavirus,Beluga Whale coronavirus SW1 | — | KF793824,KF793825,KF793826 |
| Bovine adeno-associated virus | NC_005889 | vertebrates | 1 | Parvoviridae,Dependovirus,Bovine adeno-associated virus | — | AY388617 |
| Bovine adenovirus 3 | NC_001876 | vertebrates | 1 | Adenoviridae,Mastadenovirus, Bovine adenovirus B | — | JN381195 |
| Bovine adenovirus 6 | NC_020074 | vertebrates | 1 | Adenoviridae,Atadenovirus,Bovine adenovirus E | — | JQ345700 |
| Bovine adenovirus B | NC_001876 | vertebrates | 1 | Adenoviridae, Mastadenovirus, Bovine adenovirus B | — | AF030154 |
| Bovine adenovirus D | NC_002685 | vertebrates | 1 | Adenoviridae,Atadenovirus,Bovine adenovirus D | — | AF036092 |
| Bovine calicivirus | NC_002551 | vertebrates | 1 | Caliciviridae,Vesivirus,Vesicular exanthema of swine virus | — | AJQ11099 |
| Bovine circovirus | NC_005148 | vertebrates | 1 | Circoviridae,Circovirus,Porcine circovirus 2 | — | AF109397 |
| Bovine coronavirus | NC_010327,NC_00773 2,NC_0051 47,NC_003 045 | vertebrates | 4 | Coronaviridae,Betacoronavirus,Betacoronavir | — | AF391542,AF220295,U00735,AB354579 |
| Bovine coronavirus DB2 | NC_010327,NC_00773 2,NC_0051 47,NC_003 045 | vertebrates | 1 | Coronaviridae,Betacoronavirus, Betacoronavirus 1 | — | DQ811784 |
| Bovine coronavirus E-AH187 | NC_010327,NC_00773 2,NC_0051 47,NC_003 045 | vertebrates | 1 | Coronaviridae,Betacoronavirus, Betacoronavirus 1 | — | EF424619 |
| Bovine coronavirus E-AH187-TC | NC_010327,NC_00773 2,NC_0051 47,NC_003 045 | vertebrates | 1 | Coronaviridae,Betacoronavirus, Betacoronavirus 1 | — | FJ938064 |

-continued

| Taxonomy | NCBI Reference Sequence ID | Host | No. of Genomes | Lineage | Segment Count | Genbank Accession ID |
|---|---|---|---|---|---|---|
| Bovine coronavirus E-AH65 | NC_010327,NC_007732,NC_005147,NC_003045 | vertebrates | 1 | Coronaviridae,Betacoronavirus, Betacoronavirus 1 | — | EF424615 |
| Bovine coronavirus E-AH65-TC | NC_010327,NC_007732,NC_005147,NC_003045 | vertebrates | 1 | Coronaviridae,Betacoronavirus, Betacoronavirus 1 | — | EF424616 |
| Bovine coronavirus E-DB2-TC | NC_010327,NC_007732,NC_005147,NC_003045 | vertebrates | 1 | Coronaviridae,Betacoronavirus, Betacoronavirus 1 | — | FJ938063 |
| Bovine coronavirus R-AH187 | NC_010327,NC_007732,NC_005147,NC_003045 | vertebrates | 1 | Coronaviridae,Betacoronavirus, Betacoronavirus 1 | — | EF424620 |
| Bovine coronavirus R-AH65 | NC_010327,NC_007732,NC_005147,NC_003045 | vertebrates | 1 | Coronaviridae,Betacoronavirus, Betacoronavirus 1 | — | EF424617 |
| Bovine coronavirus R-AH65-TC | NC_010327,NC_007732,NC_005147,NC_003045 | vertebrates | 1 | Coronaviridae,Betacoronavirus, Betacoronavirus 1 | — | EF424618 |
| Bovine coronavirus isolate Alpaca | NC_010327,NC_007732,NC_005147,NC_003045 | vertebrates | 1 | Coronaviridae,Betacoronavirus, Betacoronavirus 1 | — | DQ915164 |
| Bovine enterovirus | NC_001859 | vertebrates | 4 | Picornaviridae,Enterovirus,Enterovirus E | — | DQ092769,DQ092771,DQ092792,DQ092793 |
| Bovine enterovirus strain K2577 | NC_001859 | vertebrates | 1 | Picornaviridae,Enterovirus,Enterovirus E | — | AF123432 |
| Bovine enterovirus strain SL305 | NC_001859 | vertebrates | 1 | Picornaviridae,Enterovirus,Enterovirus E | — | AF123433 |
| Bovine enterovirus type 2 | NC_021220 | vertebrates | 4 | Picornaviridae,Enterovirus,Enterovirus F | — | HQ663846,AY508696,HQ917060,AY508697 |
| Bovine foamy virus Y134750,JX307862 | NC_001831 | vertebrates | 4 | Retroviridae,Spumavirus,Bovine foamy virus | — | U94514,JX307861,A |

| Taxonomy | NCBI Reference Sequence ID | Host | No. of Genomes | Lineage | Segment Count | Genbank Accession ID |
|---|---|---|---|---|---|---|
| Bovine herpesvirus 1 | NC_001847 | vertebrates | 1 | Herpesviridae,Varicellovirus,Bovine herpesvirus 1 | — | AJQ04801 |
| Bovine herpesvirus 4 | NC_002665 | vertebrates | 2 | Herpesviridae,Rhadinovirus,Bovine herpesvirus 4 | — | AF318573,JN133502 |
| Bovine herpesvirus 5 | NC_005261 | vertebrates | 1 | Herpesviridae,Varicellovirus,Bovine herpesvirus 5 | — | AY261359 |
| Bovine herpesvirus type 1.1 | NC_001847 | vertebrates | 1 | Herpesviridae,Varicellovirus,Bovine herpesvirus 1 | — | JX898220 |
| Bovine hungarovirus 1 | NC_018668 | vertebrates | 1 | Picornaviridae,Hunnivirus,Hunnivirus A | — | JQ941880 |
| Bovine immunodeficiency virus | NC_001413 | vertebrates | 1 | Retroviridae,Lentivirus,Bovine immunodeficiency virus | — | M32690 |
| Bovine kobuvirus | NC_004421 | vertebrates | 1 | Picornaviridae,Kobuvirus,Aichivirus B | — | AB084788 |
| Bovine leukemia virus | NC_001414 | vertebrates | 9 | Retroviridae,Deltaretrovirus,Bovine leukemia virus | — | AF033818,FJ914764,DQ0647,AF257515,HE967301,K02120,HE967303,EF600696,HE967302 |
| Bovine papillomavirus-1 | NC_001522 | vertebrates | 1 | Papillomaviridae,Deltapapillomavirus,Deltapapillomavirus 4 | — | XQ2346 |
| Bovine papillomavirus-3 | NC_004197 | vertebrates | 1 | Papillomaviridae,Xipapillomavirus,Xipapillomavirus 1 | — | AJ620207 |
| Bovine papillomavirus-4 | NC_004197 | vertebrates | 1 | Papillomaviridae,Xipapillomavirus,Xipapillomavirus 1 | — | XQ5817 |
| Bovine papillomavirus-5 | NC_004195 | vertebrates | 1 | Papillomaviridae,Epsilonpapillomavirus,Epsilonpapillomavirus 1 | — | AJ620206 |
| Bovine papillomavirus-6 | NC_004197 | vertebrates | 1 | Papillomaviridae,Xipapillomavirus,Xipapillomavirus 1 | — | AJ620208 |
| Bovine papillomavirus 3 | NC_004197 | vertebrates | 1 | Papillomaviridae,Xipapillomavirus,Xipapillomavirus 1 | — | AF486184 |
| Bovine papillomavirus 7 | NC_007612 | vertebrates | 1 | Papillomaviridae,Bovine papillomavirus 7 | — | DQ217793 |
| Bovine papillomavirus 8 | NC_004195 | vertebrates | 1 | Papillomaviridae,Epsilonpapillomavirus,Epsilonpapillomavirus 1 | — | DQ098913 |
| Bovine papillomavirus BAA5-Japan | NC_004197 | vertebrates | 1 | Papillomaviridae,Xipapillomavirus,Xipapillomavirus 1 | — | EU360723 |
| Bovine papillomavirus type 1 | NC_001522 | vertebrates | 2 | Papillomaviridae,Deltapapillomavirus,Deltapapillomavirus 4 | — | JX678969,AB626705 |
| Bovine papillomavirus type 10 | NC_004197 | vertebrates | 2 | Papillomaviridae,Xipapillomavirus,Xipapillomavirus 1 | — | AB331651,KF017607 |
| Bovine papillomavirus type 11 | NC_004197 | vertebrates | 1 | Papillomaviridae,Xipapillomavirus,Xipapillomavirus 1 | — | AB543507 |
| Bovine papillomavirus type 12 | NC_004197 | vertebrates | 2 | Papillomaviridae,Xipapillomavirus,Xipapillomavirus type 1 | — | JF834524,JF834523 |
| Bovine papillomavirus type 13 | NC_001522 | vertebrates | 1 | Papillomaviridae,Deltapapillomavirus,Deltapapillomavirus 4 | — | JQ798171 |
| Bovine papillomavirus type 2 | NC_001522 | vertebrates | 2 | Papillomaviridae,Deltapapillomavirus,Deltapapillomavirus 4 | — | M20219,KC878306 |
| Bovine papillomavirus type 8-EB | NC_004195 | vertebrates | 1 | Papillomaviridae,Epsilonpapillomavirus,Epsilonpapillomavirus 1 | — | DQ098917 |

| Taxonomy | NCBI Reference Sequence ID | Host | Lineage | No. of Genomes | Segment Count | Genbank Accession ID |
|---|---|---|---|---|---|---|
| Bovine papillomavirus type 9 | NC_004197 | vertebrates | Papillomaviridae,Xipapillomavirus, Xipapillomavirus 1 | 1 | — | AB331650 |
| Bovine papular stomatitis virus | NC_005337 | vertebrates | Poxviridae,Parapoxvirus,Bovine papular stomatitis virus | 1 | — | AY386265 |
| Bovine parvovirus | NC_001540 | vertebrates | Parvoviridae,Bocavirus,Bovine parvovirus | 1 | — | M14363 |
| Bovine parvovirus-2 | NC_006259 | vertebrates | Parvoviridae,Bocavirus,Bovine parvovirus-2 | 1 | — | AF406966 |
| Bovine parvovirus-1 | NC_001540 | vertebrates | Parvoviridae,Dependovirus,Bovine parvovirus-2 | 1 | — | DQ335247 |
| Bovine polyomavirus polyomavirus | NC_001442 | vertebrates | Polyomaviridae,Polyomavirus,Bovine polyomavirus | 1 | — | D13942 |
| Bovine respiratory coronavirus AH187 | NC_012948 | vertebrates | Coronaviridae, Bovine respiratory coronavirus AH187 | 1 | — | FJ938065 |
| Bovine respiratory coronavirus bovine/US/OH-440-TC/1996 | NC_012949 | vertebrates | Coronaviridae, Bovine respiratory coronavirus bovine/US/OH-440-TC/1996 | 1 | — | FJ938066 |
| Bovine rhinitis B virus | NC_010354 | vertebrates | Picornaviridae,Aphthovirus,Bovine rhinitis B virus | 1 | — | EU236594 |
| Bovine viral diarrhea virus 1 | NC_001461 | vertebrates | Flaviviridae,Pestivirus,Bovine viral diarrhea virus 1 | 17 | — | JX419397,U86599,AJ133739,KC963967,AF041040,KC757383,M31182,AJ133738,EF101530,KF772785,U86600,AF268278,DQ088995,JN400273,AF220247,JX419398,JQ799141 |
| Bovine viral diarrhea virus 1 strain ZM-95 | NC_001461 | vertebrates | Flaviviridae,Pestivirus,Bovine viral diarrhea virus 1 | 1 | — | AF526381 |
| Bovine viral diarrhea virus 2 | NC_002032 | vertebrates | Flaviviridae,Pestivirus,Bovine viral diarrhea virus 2 | 8 | — | AB567658,AF002227,GQ888686,FJ527854,AY149215,HQ258810,KC963968,AF145967 |
| Bovine viral diarrhea virus 2-New York'93 virus 2 | NC_002032 | vertebrates | Flaviviridae,Pestivirus,Bovine viral diarrhea virus 2 | 1 | — | AF502399 |
| Bovine viral diarrhea virus 3 | NC_012812 | vertebrates | Flaviviridae,Pestivirus,Bovine viral diarrhea virus 3 | 8 | — | JX469119,JX985409,JQ612704,AB871953,KC297709,HQ231763,JQ612705,KC78874 |
| Bovine viral diarrhea virus 3 Th/04_KhonKaen | NC_012812 | vertebrates | Flaviviridae,Pestivirus,Bovine viral diarrhea virus 3 | 1 | — | FJQ40215 |
| Bovine viral diarrhea virus VEDEVAC | NC_001461 | vertebrates | Flaviviridae,Pestivirus,Bovine viral diarrhea virus 1 | 1 | — | AJ585412 |
| Bovine viral diarrhea virus strain Oregon C24V | NC_001461 | vertebrates | Flaviviridae,Pestivirus,Bovine viral diarrhea virus 1 | 1 | — | AF091605 |
| Bovine viral diarrhea virus type 1a | NC_001461 | vertebrates | Flaviviridae,Pestivirus,Bovine viral diarrhea virus 1 | 3 | — | HQ174293,HQ17429 2,JN380080 |

-continued

| Taxonomy | NCBI Reference Sequence ID | Host | No. of Genomes | Lineage | Segment Count | Genbank Accession ID |
|---|---|---|---|---|---|---|
| Bovine viral diarrhea virus type 1b | NC_001461 | vertebrates | 6 | Flaviviridae,Pestivirus,Bovine viral diarrhea virus 1 | — | HQ174296,JN644055 ,JN380089,JN380088 ,JN704144,HQ17429 4 |
| Breda virus | NC_007447 | vertebrates | 1 | Coronaviridae,Torovirus,Bovine torovirus | — | AY427798 |
| Broome virus | NC_014236 | vertebrates | 1 | Reoviridae,Orthoreovirus,Broome virus | seg. L1 | GQ258977 |
| Broome virus | NC_014237 | vertebrates | 1 | Reoviridae,Orthoreovirus,Broome virus | seg. L2 | GQ258978 |
| Broome virus | NC_014238 | vertebrates | 1 | Reoviridae,Orthoreovirus,Broome virus | seg. L3 | GQ258979 |
| Broome virus | NC_014239 | vertebrates | 1 | Reoviridae,Orthoreovirus,Broome virus | seg. M1 | GQ258980 |
| Broome virus | NC_014240 | vertebrates | 1 | Reoviridae,Orthoreovirus,Broome virus | seg. M2 | GQ258981 |
| Broome virus | NC_014241 | vertebrates | 1 | Reoviridae,Orthoreovirus,Broome virus | seg. M3 | GQ258982 |
| Broome virus | NC_014242 | vertebrates | 1 | Reoviridae,Orthoreovirus,Broome virus | seg. S1 | GQ258983 |
| Broome virus | NC_014243 | vertebrates | 1 | Reoviridae,Orthoreovirus,Broome virus | seg. S2 | GQ258984 |
| Broome virus | NC_014244 | vertebrates | 1 | Reoviridae,Orthoreovirus,Broome virus | seg. S3 | GQ258985 |
| Broome virus | NC_014245 | vertebrates | 1 | Reoviridae,Orthoreovirus,Broome virus | seg. S4 | GQ258986 |
| Budgerigar fledgling disease polyomavirus | NC_004764 | vertebrates | 14 | Polyom aviridae,Polyomavirus,Budgerigar fledgling disease polyomavirus | — | AB453165,AF118150, AB453166,M20775,A B453162,GU452537, AB477106,AB453160 ,AB453161,FJ385773 ,AY672646,AB45315 9,AB453164,AB4531 63 |
| Budgerigar fledgling disease virus-1 | NC_004764 | vertebrates | 1 | Polyom aviridae,Polyomavirus,Budgerigar fledgling disease polyomavirus | — | AF241168 |
| Budgerigar fledgling disease virus-4 | NC_004764 | vertebrates | 1 | Polyom aviridae,Polyomavirus,Budgerigar fledgling disease polyomavirus | — | AF241169 |
| Budgerigar fledgling disease virus-5 | NC_004764 | vertebrates | 1 | Polyom aviridae,Polyomavirus,Budgerigar fledgling disease polyomavirus | — | AF241170 |
| Butcherbird polyomavirus | NC_023008 | vertebrates | 1 | Polyomaviridae,Polyomavirus,Butcherbird polyomavirus | — | KF360862 |
| Calf-giraffe coronavirus US/OH3/2006 | NC_010327, NC_007732, NC_005147, NC_003045 | vertebrates | 1 | Coronaviridae,Betacoronavirus, Betacoronavirus 1 | — | EF424624 |
| Calicivirus isolate Allston 2008/US | NC_004542 | vertebrates | 1 | Caliciviridae,Canine calicivirus | — | GQ475302 |

| Taxonomy | NCBI Reference Sequence ID | Host | No. of Genomes | Lineage | Segment Count | Genbank Accession ID |
|---|---|---|---|---|---|---|
| Calicivirus isolate Allston 2009/US | NC_004542 | vertebrates | 1 | Caliciviridae,Canine calicivirus | — | GQ475301 |
| Calicivirus isolate TCG | NC_006875 | vertebrates | 1 | Caliciviridae,Calicivirus isolate TCG | — | AB117797 |
| Calicivirus pig/AB104/CAN | NC_012699 | vertebrates | 1 | Caliciviridae,St-Valerien swine virus | — | FJ355930 |
| Calicivirus pig/AB90/CAN | NC_012699 | vertebrates | 1 | Caliciviridae,St-Valerien swine virus | — | FJ355928 |
| Calicivirus pig/F15-10/CAN | NC_012699 | vertebrates | 1 | Caliciviridae,St-Valerien swine virus | — | FJ355929 |
| Calicivirus pig/NC-WGP93C/USA/2009 | NC_012699 | vertebrates | 1 | Caliciviridae,St-Valerien swine virus | — | GU592498 |
| Calicivirus strain NB | NC_004064, NC_007916 | vertebrates | 1 | Caliciviridae,Nebovirus,Newbury-1 virus | — | AY082891 |
| California sea lion polyomavirus 1 | NC_013796 | vertebrates | 1 | Polyomaviridae,Polyomavirus,California sea lion polyomavirus 1 | — | GQ331138 |
| Callitrichine herpesvirus 3 | NC_004367 | vertebrates | 1 | Herpesviridae,Lymphocryptovirus, Callitrichine herpesvirus 3 | — | AF319782 |
| Camelpox virus | NC_003391 | vertebrates | 1 | Poxviridae,Orthopoxvirus,Camelpox virus | — | AF438165 |
| Camelpox virus CMS | NC_003391 | vertebrates | 1 | Poxviridae,Orthopoxvirus,Camelpox virus | — | AY009089 |
| Camelus dromedarius papillomavirus type 1 | NC_015267 | vertebrates | 1 | Papillomaviridae,Deltapapillomavirus,Camelus dromedarius papillomavirus type 1 | — | HQ912790 |
| Camelus dromedarius papillomavirus type 2 | NC_015268 | vertebrates | 1 | Papillomaviridae,Deltapapillomavirus,Camelus dromedarius papillomavirus type 2 | — | HQ912791 |
| Canary circovirus | NC_003410 | vertebrates | 1 | Circoviridae,Circovirus,Canary circovirus | — | AJ301633 |
| Canary polyomavirus | NC_017085 | vertebrates | 1 | Polyomaviridae,Polyomavirus,Canary polyomavirus | — | GU345044 |
| Canarypox virus | NC_005309 | vertebrates | 1 | Poxviridae,Avipoxvirus,Canarypox virus | — | AY318871 |
| Canine adenovirus | NC_001734 | vertebrates | 1 | Adenoviridae,Mastadenovirus,Canine adenovirus A | — | Y07760 |
| Canine adenovirus 1 | NC_001734 | vertebrates | 1 | Adenoviridae,Mastadenovirus,Canine adenovirus A | — | U55001 |
| Canine adenovirus 2 | NC_001734 | vertebrates | 1 | Adenoviridae,Mastadenovirus,Canine adenovirus A | — | U77082 |
| Canine bocavirus | NC_020499 | vertebrates | 5 | Parvoviridae,Bocavirus,Canine bocavirus | — | JQ692588,JN648103, JQ692591,JQ692590, JQ692589 |
| Canine calicivirus | NC_004542 | vertebrates | 1 | Caliciviridae,Canine calicivirus | — | AB070225 |
| Canine circovirus | NC_020904 | vertebrates | 3 | Circoviridae,Circovirus,Canine circovirus | — | KC241982,KC241983, KC241984 |
| Canine coronavirus | NC_002306 | vertebrates | 4 | Coronaviridae,Alphacoronavirus,Alphacoronavirus 1 | — | GQ477367,JQ404409 JQ404410,JN856008 |
| Canine kobuvirus 1 | NC_001918 | vertebrates | 1 | Picornaviridae, Kobuvirus,Aichivirus A | — | KC161964 |
| Canine kobuvirus US- PC0082 | NC_001918 | vertebrates | 1 | Picornaviridae, Kobuvirus,Aichivirus A | — | JN088541 |
| Canine minute virus | NC_004442 | vertebrates | 6 | Parvoviridae,Bocavirus,Canine minute virus | — | FJ214110,AB518884, AF495467,AB518883, FJ899734,AB158475 |
| Canine oral papillomavirus | NC_001619 | vertebrates | 2 | Papillomaviridae,Lambdapapillomavirus, Lamb dapapillomavirus 2 | — | D55633,L22695 |

| Taxonomy | NCBI Reference Sequence ID | Host | Lineage | No. of Genomes | Segment Count | Genbank Accession ID |
|---|---|---|---|---|---|---|
| Canine papillomavirus 10 | NC_016075 | vertebrates | Papillomaviridae,Canine papillomavirus 10 | 1 | — | JF800657 |
| Canine papillomavirus 11 | NC_008297 | vertebrates | Papillomaviridae,Chipapillomavirus,Chipapillomavirus 1 | 1 | — | JF800658 |
| Canine papillomavirus 12 | NC_016074 | vertebrates | PapillomaviridaeCanine papillomavirus 9 | 1 | — | JQ754321 |
| Canine papillomavirus 14 | NC_019852 | vertebrates | Papillomaviridae,Canine papillomavirus 14 | 1 | — | JQ701802 |
| Canine papillomavirus 2 | NC_006564 | vertebrates | Papillomaviridae,Taupapillomavirus,Taupapillomavirus 1 | 1 | — | AY722648 |
| Canine papillomavirus 3 | NC_008297 | vertebrates | Papillomaviridae,Chipapillomavirus,Chipapillomavirus 1 | 1 | — | DQ295066 |
| Canine papillomavirus 4 | NC_010226 | vertebrates | Papillomaviridae,Chipapillomavirus,Chipapillomavirus 2 | 1 | — | EF584537 |
| Canine papillomavirus 5 | NC_008297 | vertebrates | Papillomaviridae,Chipapillomavirus,Chipapillomavirus 1 | 1 | — | FJ492743 |
| Canine papillomavirus 7 | NC_006564 | vertebrates | Papillomaviridae,Taupapillomavirus,Taupapillomavirus 1 | 1 | — | FJ492742 |
| Canine papillomavirus 8 | NC_016014 | vertebrates | Papillomaviridae,Canine papillomavirus 8 | 1 | — | HQ262536 |
| Canine papillomavirus 9 | NC_016074 | vertebrates | Papillomaviridae,Canine papillomavirus 9 | 1 | — | JF800656 |
| Canine parvovirus | NC_001539 | vertebrates | Parvoviridae,Parvovirus,Feline panleukopenia virus | 4 | — | EU310373,M19296,JN033694,D26079 |
| Canine parvovirus 2b | NC_001539 | vertebrates | Parvoviridae,Parvovirus,Feline panleukopenia virus | 1 | — | JQ268284 |
| Canine picodicistrovirus | NC_021178 | vertebrates | Picornaviridae,Dicipivirus,Cadicivirus A | 3 | — | JN819202,JN819203,JN819204 |
| Canine picornavirus | NC_016964 | vertebrates | Canine picornavirus | 1 | — | JN831356 |
| Capra hircus papillomavirus type 1 | NC_008032 | vertebrates | Papillomaviridae,Phipapillomavirus,Phipapillomavirus 1 | 1 | — | DQ091200 |
| Capreolus capreolus papillomavirus 1 | NC_011051 | vertebrates | Papillomaviridae,Deltapapillomavirus,Deltapapillomavirus 5 | 1 | — | EF680235 |
| Caprine arthritis encephalitis virus | NC_001463 | vertebrates | Retroviridae,Lentivirus,Caprine arthritis encephalitis virus | 6 | — | GQ381130,JF502416,M33677,AF322109,GU120138,AY900630 |
| Caprine arthritis encephalitis virus 0v496 | NC_001463 | vertebrates | Retroviridae,Lentivirus,Caprine arthritis encephalitis virus | 1 | — | FJ195346 |
| Caprine arthritis encephalitis virus Roccaverano | NC_001463 | vertebrates | Retroviridae,Lentivirus,Caprine arthritis encephalitis virus | 1 | — | EU293537 |
| Caprine kobuvirus | NC_023422 | vertebrates | Picornaviridae,Kobuvirus,Caprine kobuvirus | 1 | — | KF793927 |
| Cardioderma polyomavirus | NC_020067 | vertebrates | Polyomaviridae,Polyomavirus,Cardioderma polyomavirus | 1 | — | JX520659 |
| Cardiovirus BR/118/2006 | NC_009448,NC_001366,NC_010810 | vertebrates | Picornaviridae,Cardiovirus,Theilovirus | 1 | — | EU681177 |
| Cardiovirus D/VI223/2004 | NC_009448,NC_001366,NC_010810 | vertebrates | Picornaviridae,Cardiovirus,Theilovirus | 1 | — | EU681179 |

-continued

| Taxonomy | NCBI Reference Sequence ID | Host | No. of Genomes | Lineage | Segment Count | Genbank Accession ID |
|---|---|---|---|---|---|---|
| Cardiovirus D/VI2229/2004 | NC_009448,NC_001366,NC_010810 | vertebrates | 1 | Picornaviridae,Cardiovirus,Theilovirus | — | EU681176 |
| Cardiovirus D/VI2273/2004 | NC_009448,NC_001366,NC_010810 | vertebrates | 1 | Picornaviridae,Cardiovirus,Theilovirus | — | EU681178 |
| Caretta caretta papillomavirus 1 | NC_011530 | vertebrates | 1 | Papillomaviridae,Dyozetapapillomavirus,Dyozetapapillomavirus 1 | — | EU493092 |
| Carp picornavirus 1 | NC_023162 | vertebrates | 1 | Carp picornavirus 1 | — | KF306267 |
| Cas-Br-E murine leukemia virus | NC_001702 | vertebrates | 1 | Retroviridae,Gammaretrovirus,Murine leukemia virus | — | X57540 |
| CIDMTR | NC_001819,NC_001362,NC_001501 | vertebrates | | | | |
| Castor canadensis papillomavirus type 1 | NC_023178 | vertebrates | 1 | Papillomaviridae,Castor canadensis papillomavirus type 1 | — | KC020689 |
| Caviid herpesvirus 2 | NC_020231 | vertebrates | 2 | Herpesviridae,Caviid herpesvirus 2 | — | AB592928,KC503762 |
| Caviid herpesvirus 2 str. CIDMTR | NC_020231 | vertebrates | 1 | Herpesviridae,Caviid herpesvirus 2 | — | HG531783 |
| Cebus albifrons polyomavirus 1 | NC_019854 | vertebrates | 1 | Polyomaviridae,Polyomavirus,Cebus albifrons polyomavirus 1 | — | JX159988 |
| Cercopithecine herpesvirus 2 | NC_006560 | vertebrates | 1 | Herpesviridae,Simplexvirus,Cercopithecine herpesvirus 2 | — | AY714813 |
| Cercopithecine herpesvirus 5 | NC_012783 | vertebrates | 2 | Herpesviridae,Cytomegalovirus,Cercopithecine herpesvirus 5 | — | FJ483968,FJ483969 |
| Cercopithecine herpesvirus 9 | NC_002686 | vertebrates | 1 | Herpesviridae,Varicellovirus,Cercopithecine herpesvirus 9 | — | AF275348 |
| Chaerephon polyomavirus 1 | NC_020065 | vertebrates | 1 | Polyomaviridae,Polyomavirus,Chaerephon polyomavirus 1 | — | JX520657 |
| Chelonia mydas papillomavirus 1 | NC_011530 | vertebrates | 1 | Papillomaviridae,Dyozetapapillomavirus,Dyozetapapillomavirus 1 | — | EU493091 |
| Chicken anemia virus | NC_001427 | vertebrates | 52 | Circoviridae,Gyrovirus,Chicken anemia virus | — | KF224936,DQ217400,KF224938,DQ124936,KF224935,AF311190,KF224935,AF311190,JX964755,DQ141673,KC414026,KF224929,AY999018,AY839944,KF224934,DQ217401,AJ297685,AB027470,KF224937,DQ141670,DQ141672,KF224926,AF311892,DQ141671,AF390102,EF176599,KF224931,U66304,AF390038,AY04632,JF507715,D |

| Taxonomy | NCBI Reference Sequence ID | Host | No. of Genomes | Lineage | Segment Count | Genbank Accession ID |
|---|---|---|---|---|---|---|
| Chicken astrovirus | NC_003790 | vertebrates | 1 | Astroviridae,Avastrovirus,Chicken astrovirus | — | AB033998 |
| Chimpanzee polyomavirus | NC_014743 | vertebrates | 3 | Polyomaviridae,Polyomavirus,Chimpanzee polyomavirus | — | FR692336,FR692334,FR692335 |
| Cimodo virus | NC_023420 | vertebrates | 1 | Reoviridae, Cimodo virus | seg. 1 | KF880772 |
| Circovirus NGchicken38/NGA/2009 | NC_002361 | vertebrates | 1 | Circoviridae,Circovirus,Columbid circovirus | — | HQ738642 |
| Citrus endogenous pararetrovirus | NC_023153 | vertebrates | 3 | Retroviridae,Citrus endogenous pararetrovirus | — | KF800045,KF800044,KF800043 |
| Classical swine fever virus | NC_002657 | vertebrates | 59 | Flaviviridae,Pestivirus,Classical swine fever virus | — | U45477,HQ148063,AY647690,JQ268754,EU915211,GQ902941,KC851953,D49532,JX262391,AY775178,AY578687,AF099102,EU857642,AF333000,GU324242,L49347,AY259122,AF352565,GU233731,FJ529205,AI6790,AF091507,GQ923951,AY646427,HQ380231,AX191158,EU789580,AF092448,D49533,AY382481,GU233733,EU497410,U45478,AY77196,AY578688,X96550,AY568569,AY663656,AY367767,GU233732,GQ122383,HM237795,AF091661,AY805221,U90951,GU592790,JX218094,HQ148062,FJ265020,DQ127910,CQ867021,GU233734,A0124935,FJ172347,D0991394,M55918,D10068,KF224933,DQ124934,A48606,AF285882,AB119448,L11476 7,KF224932,KF224928,JQ690762,AF39511 4,JX260426,U65414, AY843527,AJ297684, AY846844,AF475908, KF224930,KF224927 |

-continued

| Taxonomy | NCBI Reference Sequence ID | Host | No. of Genomes | Lineage | Segment Count | Genbank Accession ID |
|---|---|---|---|---|---|---|
| | | | | | | F326963,AF531433,H 0148061,JQ595295, AY072924,HM175885 ,EU490425 |
| Classical swine fever virus - Alf ort/187 | NC_002657 | vertebrates | 1 | Flaviviridae,Pestivirus,Classical swine fever virus | — | X87939 |
| Classical swine fever virus - Alfort/Tuebingen | NC_002657 | vertebrates | 1 | Flaviviridae,Pestivirus,Classical swine fever virus | — | JQ4358 |
| Classical swine fever virus - Brescia | NC_002657 | vertebrates | 1 | Flaviviridae,Pestivirus,Classical swine fever virus | — | M31768 |
| Classical swine fever virus - C | NC_002657 | vertebrates | 1 | Flaviviridae,Pestivirus,Classical swine fever virus | — | Z46258 |
| Classical swine fever virus 39 | NC_002657 | vertebrates | 1 | Flaviviridae,Pestivirus,Classical swine fever virus | — | AF407339 |
| Classical swine fever virus 96TD | NC_002657 | vertebrates | 1 | Flaviviridae,Pestivirus,Classical swine fever virus | — | AY554397 |
| Colobus guereza papillomavirus type 1 | NC_004104 | vertebrates | 1 | Papillomaviridae,Alphapapillomavirus,Alphapa pillomavirus 14 | — | GU014532 |
| Columbid circovirus | NC_002361 | vertebrates | 16 | Circoviridae,Circovirus,Columbid circovirus | — | DQ915950,DQ91595 9,EU840176,DQ9159 57,DQ090944,DQ090 945,AF252610,DQ91 5958,AJ298230,JX90 1125,AJ298229,JN18 3455,DQ915961,DQ9 15962,DQ915956,DQ 915960 |
| Common chimpanzee papillomavirus 1 | NC_001355 | vertebrates | 1 | Papillomaviridae,Alphapapillomavirus,Alphapa pillomavirus 10 | — | AF020905 |
| Common marmoset foamy virus | NC_001364 | vertebrates | 1 | Retroviridae,Spumavirus,Simian foamy virus | — | GU356395 |
| Common midwife toad ranavirus | NC_005946 | vertebrates | 1 | Iridoviridae,Ranavirus,Frog virus 3 | — | JQ231222 |
| Common-moorhen coronavirus HKU21 | NC_016996 | vertebrates | 1 | Coronaviridae,Deltacoronavirus,Common-moorhen coronavirus H KU21 | — | JQ065049 |
| Cosavirus A | NC_012800 | vertebrates | 2 | Picornaviridae,Cosavirus,Cosavirus A | — | FJ438902,GU968209 |
| Cotia virus SPAn232 | NC_016924 | vertebrates | 1 | Poxviridae,Cotia virus | — | HQ6471 81 |
| Cottontail rabbit papillomavirus | NC_001541 | vertebrates | 4 | Papillomaviridae,Kappapapillomavirus,Kappap apillomavirus 2 | — — | AJ404003,JF303889, AJ243287,K02708 |
| Cowpox virus | NC_003663 | vertebrates | 34 | Poxviridae,Orthopoxvirus,Cowpox virus | — | KC813499,HQ420896 ,KC813496,KC81350 0,KC813492,DQ4375 93,HQ420895,HQ420 897,KC813505,X9435 5,HQ407377,KC8135 12,KC813501,KC813 493,KC813494,HQ42 0894,HQ420899,HQ4 |

| Taxonomy | NCBI Reference Sequence ID | Host | No. of Genomes | Lineage | Segment Count | Genbank Accession ID |
|---|---|---|---|---|---|---|
| | | | | | | 20900,KC813510,KC813491,KC813502,KC813495,KC813509, KC813511,AF482758,KC813503,HQ42089 3,KC813507,HQ4208 98,KC813506,KC813 508,KC813504,KC81 3498,KC813497 |
| Crocuta crocuta papillomavirus 1 | NC_018575 | vertebrates | 1 | Papillomaviridae,Lambdapapillomavirus,Crocuta crocuta papillomavirus 1 | — | HQ585856 |
| Crow polyomavirus | NC_007922 | vertebrates | 1 | Polyomaviridae,Polyomavirus,Crow polyomavirus | — | DQ192570 |
| Cyclovirus NGchicken15/NGA/2009 | NC_014930 | vertebrates | 1 | Circoviridae,Cyclovirus NGchicken15/NGA/2009 | — | HQ738644 |
| Cyclovirus NGchicken8/NGA/2009 | NC_014930 | vertebrates | 1 | Circoviridae,Cyclovirus NGchicken15/NGA/2009 | — | HQ738643 |
| Cyclovirus PKbeef23/PAK/2009 | NC_014927 | vertebrates | 1 | Circoviridae,Cyclovirus PKgoat21/PAK/2009 | — | HQ738634 |
| Cyclovirus PKgoat11/PAK/2009 | NC_014928 | vertebrates | 1 | Circoviridae,Cyclovirus PKgoat11/PAK/2009 | — | HQ738636 |
| Cyclovirus PKgoat21/PAK/2009 | NC_014927 | vertebrates | 1 | Circoviridae,Cyclovirus PKgoat21/PAK/2009 | — | HQ738635 |
| Cyclovirus VN | NC_021707 | vertebrates | 8 | Circoviridae,Cyclovirus VN | — | KF031491,KF031469, KF031467,KF031471, KF031466,KF031465, KF031468,KF031470 |
| Cyclovirus bat/USA/2009 | NC_014929 | vertebrates | 1 | Circoviridae,Cyclovirus bat/USA/2009 | — | HQ738637 |
| Cynomolgus macaque cytomegalovirus strain Ottawa | NC_016154 | vertebrates | 1 | Herpesviridae,Cytomegalovirus,Cynomolgus macaque cytomegalovirus strain Ottawa | — | JN227533 |
| Cyprinid herpesvirus 1 | NC_019491 | vertebrates | 1 | Alloherpesviridae,Cyprinivirus,Cyprinid herpesvirus 1 | — | JQ815363 |
| Cyprinid herpesvirus 2 | NC_019495 | vertebrates | 1 | Alloherpesviridae,Cyprinivirus,Cyprinid herpesvirus 2 | — | JQ815364 |
| Cyprinid herpesvirus 3 | NC_009127 | vertebrates | 3 | Alloherpesviridae,Cyprinivirus,Cyprinid herpesvirus 3 | — | DQ657948,AP008984 ,DQ177346 |
| DG-75 Murine leukemia virus | NC_001702 ,NC_00181 9,NC_0013 62,NC_001 501 | vertebrates | 1 | Retroviridae,Gammaretrovirus,Murine leukemia virus | — | AF221065 |
| Deer papillomavirus | NC_001523 | vertebrates | 1 | Papillomaviridae,Deltapapillomavirus,Deltapap illomavirus 2 | — | M11910 |
| Deerpox virus W-1170-84 | NC_006967 | vertebrates | 1 | Poxviridae,Cervidpoxvirus,Deerpox virus W-1170-84 | — | AY689437 |
| Deerpox virus W-848-83 | NC_006966 | vertebrates | 1 | Poxviridae,Cervidpoxvirus,Deerpox virus W-848-83 | — | AY689436 |

| Taxonomy | NCBI Reference Sequence ID | Host | No. of Genomes | Lineage | Segment Count | Genbank Accession ID |
|---|---|---|---|---|---|---|
| Delphinus delphis papillomavirus | NC_011109 | vertebrates | 1 | Papillomaviridae,Upsilonpapillomavirus,Upsilon papillomavirus 1 | — | GU117620 |
| Duck adenovirus 1 | NC_001813 | vertebrates | 1 | Adenoviridae,Atadenovirus,Duck adenovirus A | — | KF286430 |
| Duck adenovirus A | NC_001813 | vertebrates | 1 | Adenoviridae,Atadenovirus,Duck adenovirus A | — | Y09598 |
| Duck astrovirus 1 | NC_012437 | vertebrates | 5 | Astroviridae,Avastrovirus,Duck astrovirus GH,A | — | JX439643,FJ919225, FJ919228,FJ919226, FJ919227 |
| Duck astrovirus C-NGB | NC_012437 | vertebrates | 1 | Astroviridae,Avastrovirus,Duck astrovirus GH,A | — | FJ434664 |
| Duck circovirus | NC_005053,NC_007220,NC_006561 | vertebrates | 47 | Circoviridae,Circovirus,Duck circovirus | — | KC460533,HG532019,GU131340,EU499309,EU344803,HM162348,EU022375,HM162351,KC460528,JX241046,EU344805,GU131343,JX241045,EU344804,EU499310,JQ740360,KC460530,HM162349,HM162352,KC460527,GU131341,JQ740361,KC460532,KC460526,KC460525,HM162347,KC460524,HM162345,KC460529,KF726087,JQ740362,KC460535,GU131342,EU499311,GQ423740,HM162353,GU014543,GQ423747,HM162350,JQ740363,EU344806,HM162346,KC460534,EU344802,EU022374,KC460531,EU344807 |
| Duck coronavirus | NC_010800,NC_001451 | vertebrates | 1 | Coronaviridae,Gammacoronavirus,Avian coronavirus | — | JF705860 |
| Duck hepatitis A virus | NC_008250 | vertebrates | 13 | Picornaviridae,Avihepatovirus,Duck hepatitis A virus | — | JX235698,JQ301467,GU066820,EU352805,HQ654774,GU06682,4,GU066825,GU066823,GU944671,GU066822,GU066819,KC893553,GU066821 |
| Duck hepatitis A virus 1 | NC_008250 | vertebrates | 30 | Picornaviridae,Avihepatovirus,Duck hepatitis A virus | — | JF828983,JF828984, DQ249299,JF914945, JQ316452,JF828989, JF828992,JF828996, |

| Taxonomy | NCBI Reference Sequence ID | Host | No. of Genomes | Lineage | Segment Count | Genbank Accession ID |
|---|---|---|---|---|---|---|
| Duck hepatitis A virus 3 | NC_008250 | vertebrates | 6 | Picornaviridae,Avihepatovirus,Duck hepatitis A virus | — | JF829000,KC904272, JF828985,JF828987, JF828998,JF828994, JF828986,JF828997, JF828991,JF828993, JF828982,JF828999, DQ226541,JQ031262 ,JF828990,JQ804521 ,JF828988,JF828995, JX390984,JQ804522, JX390982,JX390983 DQ256132,KC993890 ,JQ409566,JF835025 ,JF914944,JX312194 |
| Duck hepatitis B virus | NC_001344 | vertebrates | 43 | Hepadnaviridae,Avihepadnavirus,Duck hepatitis B virus | — | DQ195079,AY494850 ,AF404406,AF047045 ,M6O677,EU429326,X 60213,JX469898,KO1 834,AY433937,X5856 7,HM043822,AY2509 04,AY250901,HQ214 130,AY494851,X5856 8,X58569,AF493986, M32990,X74623,AY2 94028,EU429324,JX4 69896,AY250902,AY 392760,AY294656,H 0132730,AJQ06350, M32991,HM590411,D 0276978, M21953,AY 536371,AF505512,AY 521226,AY294029,A Y521227,HQ328779, X12798,JX469897,E U429325,AY250903 |
| Duck hepatitis virus 1 | NC_008250 | vertebrates | 44 | Picornaviridae,Avihepatovirus,Duck hepatitis A virus | — | FJ157172,FJ157179, EU395435,EU888310 ,FJ436047,FJ157173, EU841005,DQ864514 ,FJ157174,EU371557 ,FJ496339,EU395436 ,FJ496344,DQ249301 ,EU395439,EF58520 0,EF427899,EF15131 2,EU395438,EU2640 72,FJ496341,EF3827 78,FJ157177,EF1513 13,FJ496340,FJ1571 |

-continued

| Taxonomy | NCBI Reference Sequence ID | Host | No. of Genomes | Lineage | Segment Count | Genbank Accession ID |
|---|---|---|---|---|---|---|
| | | | | | | 76,DQ219396,EU877916,EU395440,GQ130377,FJ496343,EF427900,EF093502,DQ886445,FJ157178,FJ496342,EU747874,FJ157175,EU753359,FJ971623,EU395437,FJ157180,EF417871,DQ249300 |
| Duck hepatitis virus 1 strain 04G | NC_008250 | vertebrates | 1 | Picornaviridae,Avihepatovirus,Duck hepatitis A virus | — | EF067923 |
| Duck hepatitis virus 1 strain 90D | NC_008250 | vertebrates | 1 | Picornaviridae,Avihepatovirus,Duck hepatitis A virus | — | EF067924 |
| Duck hepatitis virus AP-04009 | NC_008250 | vertebrates | 1 | Picornaviridae,Avihepatovirus,Duck hepatitis A virus | — | DQ256133 |
| Duck hepatitis virus AP-04203 | NC_008250 | vertebrates | 1 | Picornaviridae,Avihepatovirus,Duck hepatitis A virus | — | DQ256134 |
| Duck hepatitis virus DHV-HS | NC_008250 | vertebrates | 1 | Picornaviridae,Avihepatovirus,Duck hepatitis A virus | — | DQ812094 |
| Duck hepatitis virus DHV-HSS | NC_008250 | vertebrates | 1 | Picornaviridae,Avihepatovirus,Duck hepatitis A virus | — | DQ812092 |
| Duck hepatitis virus FC64/CHN/2009 | NC_008250 | vertebrates | 1 | Picornaviridae,Avihepatovirus,Duck hepatitis A virus | — | HQ232302 |
| Duck hepatitis virus G | NC_008250 | vertebrates | 1 | Picornaviridae,Avihepatovirus,Duck hepatitis A virus | — | EU755009 |
| Duck hepatitis virus GD | NC_008250 | vertebrates | 1 | Picornaviridae,Avihepatovirus,Duck hepatitis A virus | — | GQ122332 |
| Duck hepatitis virus SDQ1 | NC_008250 | vertebrates | 1 | Picornaviridae,Avihepatovirus,Duck hepatitis A virus | — | GQ485310 |
| Duck hepatitis virus SDQ2 | NC_008250 | vertebrates | 1 | Picornaviridae,Avihepatovirus,Duck hepatitis A virus | — | GQ485311 |
| Duck hepatitis virus YYF-2008 | NC_008250 | vertebrates | 1 | Picornaviridae,Avihepatovirus,Duck hepatitis A virus | — | DQ812093 |
| Duck reovirus | NC_015126 | vertebrates | 3 | Reoviridae,Orthoreovirus,Avian orthoreovirus | seg. L1 | KF154110,KC493572,JX478250 |
| Duck reovirus | NC_015127 | vertebrates | 3 | Reoviridae,Orthoreovirus,Avian orthoreovirus | seg. L2 | KF154111,JX478251,KC493573 |
| Duck reovirus | NC_015128 | vertebrates | 3 | Reoviridae,Orthoreovirus,Avian orthoreovirus | seg. L3 | KF154112,KC493574,JX478252 |
| Duck reovirus | NC_015129 | vertebrates | 3 | Reoviridae,Orthoreovirus,Avian orthoreovirus | seg. M1 | KF154113,JX478253,JX440513 |
| Duck reovirus | NC_015130 | vertebrates | 3 | Reoviridae,Orthoreovirus,Avian orthoreovirus | seg. M2 | KF154114,JX478254,JX440514 |
| Duck reovirus | NC_015131 | vertebrates | 3 | Reoviridae,Orthoreovirus,Avian orthoreovirus | seg. M3 | JX478255,JX440512,KF154115 |
| Duck reovirus | NC_015132 | vertebrates | 1 | Reoviridae,Orthoreovirus,Avian orthoreovirus | seg. S1 | KF689545 |

| Taxonomy | NCBI Reference Sequence ID | Host | No. of Genomes | Lineage | Segment Count | Genbank Accession ID |
|---|---|---|---|---|---|---|
| Duck reovirus | NC_015133 | vertebrates | 8 | Reoviridae,Orthoreovirus,Avian orthoreovirus | seg. S2 | JX852430,KF154117, JX852432,JX852431, JX852434,JQ863359, JX852433,JX478257 |
| Duck reovirus | NC_015134 | vertebrates | 8 | Reoviridae,Orthoreovirus,Avian orthoreovirus | seg. S3 | KF154118,JX826588, KF163096,KF163098, JX478258,KF163097, KF163099,KF163095 |
| Duck reovirus | NC_015135 | vertebrates | 9 | Reoviridae,Orthoreovirus,Avian orthoreovirus | seg. S4 | JX826589,KF163100, KF163104,KF163102, JX478259,KF154119, KF163103,JQ922269, KF163101 |
| Duck reovirus NP03/CHN/2009 | NC_015126 | vertebrates | 1 | Reoviridae,Orthoreovirus,Avian orthoreovirus | seg. L1 | KC312700 |
| Duck reovirus NP03/CHN/2009 | NC_015127 | vertebrates | 1 | Reoviridae,Orthoreovirus,Avian orthoreovirus | seg. L2 | KC312701 |
| Duck reovirus NP03/CHN/2009 | NC_015128 | vertebrates | 1 | Reoviridae,Orthoreovirus,Avian orthoreovirus | seg. L3 | KC312702 |
| Ectromelia virus | NC_004105 | vertebrates | 2 | Poxviridae,Orthopoxvirus,Ectromelia virus | — | JQ410350,AF012825 |
| Eel picornavirus 1 | NC_022332 | vertebrates | 1 | Picornaviridae,Eel picornavirus 1 | — | KC843627 |
| Eel virus European X | NC_022581 | vertebrates | 1 | Rhabdoviridae,Perhabdovirus,Anguillid rhabdovirus | — | FN557213 |
| Eidolon helvum parvovirus 1 | NC_016744 | vertebrates | 1 | Parvoviridae,Eidolon helvum parvovirus 1 | — | JQ037753 |
| Eidolon polyomavirus 1 | NC_020068 | vertebrates | 1 | Polyomaviridae,Polyomavirus,Eidolon polyomavirus 1 | — | JX520660 |
| Elephant endotheliotropic herpesvirus 1A | NC_020474 | vertebrates | 1 | Herpesviridae,Proboscivirus,Elephantid herpesvirus 1 | — | KC618527 |
| Elephantid herpesvirus 1 | NC_020474 | vertebrates | 2 | Herpesviridae,Proboscivirus,Elephantid herpesvirus 1 | — | KC462165,KC462164 |
| Encephalomyocarditis virus | NC_001479 | vertebrates | 16 | Picornaviridae,Cardiovirus,Encephalomyocarditis virus | — | M37588,AY296731,KF 293299,FJ897755,E U780149,X87335,DO 288856,M22458,M22 457,EU780148,AF35 6822,X74312,DQ464 062,KF709977,M818 61,DQ464063 |
| Endogenous mouse mammary tumor virus Mtv1 | NC_001503 | vertebrates | 1 | Retroviridae,Betaretrovirus,Mouse mammary tumor virus | — | AF228550 |
| Enterovirus 103 | NC_010415 | vertebrates | 1 | Picornaviridae,Enterovirus,Enterovirus J | — | FJQ07373 |
| Enterovirus 103 | NC_013695 | vertebrates | 1 | Picornaviridae,Enterovirus,Enterovirus J | — | FJQ07373 |
| Enterovirus E | NC_001859 | vertebrates | 1 | Picornaviridae,Enterovirus,Enterovirus E | — | DQ0214 |
| Enterovirus E | NC_021220 | vertebrates | 2 | Picornaviridae,Enterovirus,Enterovirus F | — | DQ092795,DQ09279 4 |

| Taxonomy | NCBI Reference Sequence ID | Host | No. of Genomes | Lineage | Segment Count | Genbank Accession ID |
|---|---|---|---|---|---|---|
| Enterovirus F | NC_021220 | vertebrates | 2 | Picornaviridae,Enterovirus,Enterovirus F | — | KC748420,DQ092770 |
| Enterovirus J | NC_010415 | vertebrates | 1 | Picornaviridae,Enterovirus,Enterovirus J | — | AF414372 |
| Enterovirus J | NC_013695 | vertebrates | 2 | Picornaviridae,Enterovirus,Enterovirus J | — | AF414372,AF414373 |
| Enzootic nasal tumor virus | NC_007015 | vertebrates | 5 | Retroviridae,Betaretrovirus,Ovine enzootic nasal tumor virus | — | FJ744146,FJ744150, FJ744148,FJ744147, FJ744149 |
| Enzootic nasal tumour virus of goats | NC_004994 | vertebrates | 2 | Retroviridae,Betaretrovirus,Enzootic nasal tumour virus of goats | — | HM104174,AY197548 |
| Epinephelus tauvina nervous necrosis virus | NC_004136 | vertebrates | 2 | Nodaviridae,Betanodavirus,Epinephelus tauvina nervous necrosis virus | seg. RNA 2 | AF281657,AF318942 |
| Epinephelus tauvina nervous necrosis virus | NC_004137 | vertebrates | 2 | Nodaviridae,Betanodavirus,Epinephelus tauvina nervous necrosis virus | seg. RNA 1 | AF326776,AF319555 |
| Epsilonpapillomavirus 1 | NC_004195 | vertebrates | 1 | Papillomaviridae,Epsilonpapillomavirus,Epsilonpapillomavirus 1 | — | AF457465 |
| Equid herpesvirus 1 | NC_001491 | vertebrates | 3 | Herpesviridae,Varicellovirus,Equid herpesvirus 1 | — | AP012321,AY665713,AY464052 |
| Equid herpesvirus 2 | NC_001650 | vertebrates | 1 | Herpesviridae,Percavirus,Equid herpesvirus 2 | — | U20824 |
| Equid herpesvirus 4 | NC_001844 | vertebrates | 1 | Herpesviridae,Varicellovirus,Equid herpesvirus 4 | — | AF030027 |
| Equid herpesvirus 8 | NC_017826 | vertebrates | 1 | Herpesviridae,Varicellovirus,Equid herpesvirus 8 | — | JQ343919 |
| Equid herpesvirus 9 | NC_011644 | vertebrates | 1 | Herpesviridae,Varicellovirus,Equid herpesvirus 9 | — | AP010838 |
| Equine arteritis virus | NC_002532 | vertebrates | 33 | Arteriviridae,Arterivirus,Equine arteritis virus | — | GQ903801,X53459,AY349168,GQ903807, JN211318,EU586274, EU252114,GQ90380 6,GQ903800,EU2521 13,GQ903798,GQ903 805,GQ903811,JN21 1316,GQ903795,GQ9 03810,EU586275,GQ 903804,GQ903809,G 0903802,A45589,JN 211320,EU586273,A Y349167,JN211319,J N211317,GQ903799, DQ846750,GQ90379 7,GQ903808,GQ9038 03,GQ903794,GQ903 796 |
| Equine coronavirus | NC_010327,NC_00773 2,NC_0051 47,NC_003 045 | vertebrates | 1 | Coronaviridae,Betacoronavirus,Betacoronavirus 1 | — | EF446615 |

| Taxonomy | NCBI Reference Sequence ID | Host | No. of Genomes | Lineage | Segment Count | Genbank Accession ID |
|---|---|---|---|---|---|---|
| Equine foamy virus | NC_002201 | vertebrates | 1 | Retroviridae,Spumavirus,Equine foamy virus | — | AF201902 |
| Equine infectious anemia virus | NC_001450 | vertebrates | 26 | Retroviridae,Lentivirus,Equine infectious anemia virus | — | M87581,U01866,HM141912,HM141917,HM141921,AF327877,HM141915,HM141918,HM141913,HM141919,AF327878,HM141914,JXQ03263,AF016316,HM141909,HM141922,AF028231,HM141920,AF033820,M16575,HM141911,HM141910,AF028232,HM141916,AF247394,HM141923 |
| Equine papillomavirus 2 | NC_012123 | vertebrates | 2 | Papillomaviridae,Dyoiotapapillomavirus,Equine papillomavirus 2 | — | EU503122,HM461973 |
| Equine papillomavirus 3 | NC_017862 | vertebrates | 1 | Papillomaviridae,Equine papillomavirus 3 | — | GU384895 |
| Equine papillomavirus type 6 | NC_020500 | vertebrates | 1 | Papillomaviridae,Equine papillomavirus type 6 | — | JQ965698 |
| Equine pegivirus 1 | NC_020902 | vertebrates | 1 | Flaviviridae,Pegivirus,Equine pegivirus 1 | — | KC410872 |
| Equine polyomavirus | NC_017982 | vertebrates | 1 | Polyomaviridae,Polyomavirus,Equine polyomavirus | — | JQ412134 |
| Equine rhinitis A virus | NC_003982 | vertebrates | 8 | Picornaviridae,Aphthovirus,Equine rhinitis A virus | — | DQ268580,DQ272128,DQ272577,X96870,DQ272127,JX294351,DQ272578,L43052 |
| Equine rhinitis B virus 1 | NC_003983 | vertebrates | 1 | Picornaviridae,Erbovirus,Equine rhinitis B virus | — | X96871 |
| Equine rhinitis B virus 2 | NC_003983 | vertebrates | 1 | Picornaviridae,Erbovirus,Equine rhinitis B virus | — | AF361253 |
| Equus caballus papillomavirus 1 | NC_003748 | vertebrates | 1 | Papillomaviridae,Zetapapillomavirus,Zetapapillomavirus 1 | — | AF498323 |
| Equus ferus caballus papillomavirus type 4 | NC_020085 | vertebrates | 1 | Papillomaviridae,Equus ferus caballus papillomavirus type 4 | — | JQ031032 |
| Equus ferus caballus papillomavirus type 5 | NC_020084 | vertebrates | 1 | Papillomaviridae,Equus ferus caballus papillomavirus type 5 | — | JQ031033 |
| Equus ferus caballus papillomavirus type 7 | NC_020501 | vertebrates | 1 | Papillomaviridae,Equus ferus caballus papillomavirus type 7 | — | JXQ35935 |
| Erethizon dorsatum papillomavirus type 1 | NC_006951 | vertebrates | 1 | Papillomaviridae,Sigmapapillomavirus,Sigmapapillomavirus 1 | — | AY684126 |
| Erinaceus europaeus papillomavirus | NC_011765 | vertebrates | 1 | Papillomaviridae,Dyoetapapillomavirus,Dyoetapapillomavirus 1 | — | FJ379293 |
| Espirito Santo virus | NC_016517 | vertebrates | 1 | Birnaviridae,Espirito Santo virus | seg. B | JN589002 |
| Espirito Santo virus | NC_016518 | vertebrates | 1 | Birnaviridae,Espirito Santo virus | seg. A | JN589003 |
| European brown hare syndrome virus | NC_002615 | vertebrates | 3 | Caliciviridae,Lagovirus,European brown hare syndrome virus | — | KC832838,KC832839,Z69620 |
| European catfish virus | NC_017940 | vertebrates | 1 | Incloviridae,Ranavirus,European catfish virus | — | JQ724856 |

| Taxonomy | NCBI Reference Sequence ID | Host | No. of Genomes | Lineage | Segment Count | Genbank Accession ID |
|---|---|---|---|---|---|---|
| European elk papillomavirus | NC_001524 | vertebrates | 1 | Papillomaviridae,Deltapapillomavirus,Deltapapillomavirus 1 | — | M15953 |
| Exogenous mouse mammary tumor virus | NC_001503 | vertebrates | 2 | Retroviridae,Betaretrovirus,Mouse mammary tumor virus | — | AF228551,AF228552 |
| FBR murine osteosarcoma virus | NC_001506 | vertebrates | 1 | Retroviridae,Gammaretrovirus,Murine osteosarcoma virus | — | K02712 |
| Fathead minnow picornavirus | NC_023437 | vertebrates | 1 | Picornaviridae,Fathead minnow picornavirus | — | KC465953 |
| Felid herpesvirus 1 | NC_013590 | vertebrates | 1 | Herpesviridae,Varicellovirus,Felid herpesvirus 1 | — | FJ478159 |
| Feline astrovirus 2 | NC_022249 | vertebrates | 1 | Astroviridae,Mamastrovirus,Feline astrovirus 2 | — | KF499111 |
| Feline astrovirus Viseu | NC_022249 | vertebrates | 1 | Astroviridae,Mamastrovirus,Feline astrovirus 2 | — | KF374704 |
| Feline bocavirus | NC_017823 | vertebrates | 3 | Parvoviridae,Bocavirus,Feline bocavirus | — | JQ692586,JQ692585,JQ692587 |
| Feline bocavirus 2 | NC_022800 | vertebrates | 1 | Parvoviridae,Bocavirus,Feline bocavirus 2 | — | KF792837 |
| Feline calicivirus | NC_001481 | vertebrates | 28 | Caliciviridae,Vesivirus,Feline calicivirus | — | KC835209,AY560117,JX519213,JX519209,JN210884,JN210886,AY560118,M86379,L40021,JX519211,AY560113,JN210890,U13992,GU214989,JN210889,AY560114,JN210888,DQ424892,JX519214,JN210887,AY560116,AF479590,JN210885,JX519212,D31836,JX519210,AY560115,AF109465 |
| Feline coronavirus | NC_002306 | vertebrates | 8 | Coronaviridae,Alphacoronavirus,Alphacoronavirus 1 | — | JQ408980,GQ152141,KF530123,DQ010921,JN634064,DQ286389,DQ848678,EU186072 |
| Feline coronavirus RM | NC_002306 | vertebrates | 1 | Coronaviridae,Alphacoronavirus,Alphacoronavirus 1 | — | FJ938051 |
| Feline coronavirus UU10 | NC_002306 | vertebrates | 1 | Coronaviridae,Alphacoronavirus,Alphacoronavirus 1 | — | FJ938059 |
| Feline coronavirus UU11 | NC_002306 | vertebrates | 1 | Coronaviridae,Alphacoronavirus,Alphacoronavirus 1 | — | FJ938052 |
| Feline coronavirus UU15 | NC_002306 | vertebrates | 1 | Coronaviridae,Alphacoronavirus,Alphacoronavirus 1 | — | FJ938057 |
| Feline coronavirus UU16 | NC_002306 | vertebrates | 1 | Coronaviridae,Alphacoronavirus,Alphacoronavirus 1 | — | FJ938058 |
| Feline coronavirus UU17 | NC_002306 | vertebrates | 1 | Coronaviridae,Alphacoronavirus,Alphacoronavirus 1 | — | HQ012367 |
| Feline coronavirus UU18 | NC_002306 | vertebrates | 1 | Coronaviridae,Alphacoronavirus,Alphacoronavirus 1 | — | HQ012368 |

| Taxonomy | NCBI Reference Sequence ID | Host | No. of Genomes | Lineage | Segment Count | Genbank Accession ID |
|---|---|---|---|---|---|---|
| Feline coronavirus UU19 | NC_002306 | vertebrates | 1 | Coronaviridae,Alphacoronavirus,Alphacoronavirus 1 | — | HQ392470 |
| Feline coronavirus UU2 | NC_002306 | vertebrates | 1 | Coronaviridae,Alphacoronavirus,Alphacoronavirus 1 | — | FJ938060 |
| Feline coronavirus UU20 | NC_002306 | vertebrates | 1 | Coronaviridae,Alphacoronavirus,Alphacoronavirus 1 | — | HQ392471 |
| Feline coronavirus UU21 | NC_002306 | vertebrates | 1 | Coronaviridae,Alphacoronavirus,Alphacoronavirus 1 | — | HQ012369 |
| Feline coronavirus UU22 | NC_002306 | vertebrates | 1 | Coronaviridae,Alphacoronavirus,Alphacoronavirus 1 | — | GU553361 |
| Feline coronavirus UU23 | NC_002306 | vertebrates | 1 | Coronaviridae,Alphacoronavirus,Alphacoronavirus 1 | — | GU553362 |
| Feline coronavirus UU24 | NC_002306 | vertebrates | 1 | Coronaviridae,Alphacoronavirus,Alphacoronavirus 1 | — | HQ012370 |
| Feline coronavirus UU3 | NC_002306 | vertebrates | 1 | Coronaviridae,Alphacoronavirus,Alphacoronavirus 1 | — | FJ938061 |
| Feline coronavirus UU30 | NC_002306 | vertebrates | 1 | Coronaviridae,Alphacoronavirus,Alphacoronavirus 1 | — | HQ392472 |
| Feline coronavirus UU31 | NC_002306 | vertebrates | 1 | Coronaviridae,Alphacoronavirus,Alphacoronavirus 1 | — | HQ012371 |
| Feline coronavirus UU34 | NC_002306 | vertebrates | 1 | Coronaviridae,Alphacoronavirus,Alphacoronavirus 1 | — | HQ012372 |
| Feline coronavirus UU4 | NC_002306 | vertebrates | 1 | Coronaviridae,Alphacoronavirus,Alphacoronavirus 1 | — | FJ938054 |
| Feline coronavirus UU40 | NC_002306 | vertebrates | 1 | Coronaviridae,Alphacoronavirus,Alphacoronavirus 1 | — | HQ392469 |
| Feline coronavirus UU47 | NC_002306 | vertebrates | 1 | Coronaviridae,Alphacoronavirus,Alphacoronavirus 1 | — | JN183882 |
| Feline coronavirus UU5 | NC_002306 | vertebrates | 1 | Coronaviridae,Alphacoronavirus,Alphacoronavirus 1 | — | FJ938056 |
| Feline coronavirus UU54 | NC_002306 | vertebrates | 1 | Coronaviridae,Alphacoronavirus,Alphacoronavirus 1 | — | JN183883 |
| Feline coronavirus UU7 | NC_002306 | vertebrates | 1 | Coronaviridae,Alphacoronavirus,Alphacoronavirus 1 | — | FJ938053 |
| Feline coronavirus UU8 | NC_002306 | vertebrates | 1 | Coronaviridae,Alphacoronavirus,Alphacoronavirus 1 | — | FJ938055 |
| Feline coronavirus UU9 | NC_002306 | vertebrates | 1 | Coronaviridae,Alphacoronavirus,Alphacoronavirus 1 | — | FJ938062 |
| Feline foamy virus | NC_001871 | vertebrates | 8 | Retroviridae,Spumavirus,Feline foamy virus | — | AJ564746,KC292055,U85043,AJ223851,KC292054,AB052797,Y08851,AJ564745 |
| Feline immunodeficiency virus | NC_001482 | vertebrates | 27 | Retroviridae,Lentivirus,Feline immunodeficiency virus | — | EF455611,EF455612,EF455609,EU117991,EF455608,EF455603,M36968,AY713445,EU117992,M25381,AY600517,X57002,U569 |

| Taxonomy | NCBI Reference Sequence ID | Host | No. of Genomes | Lineage | Segment Count | Genbank Accession ID |
|---|---|---|---|---|---|---|
| Feline infectious peritonitis virus | NC_002306 | vertebrates | 5 | Coronaviridae,Alphacoronavirus,Alphacorona virus 1 | — | 28,AF474246,DQ192 583,EF455607,DDQ2 9017,EF455606,EF45 5614, E43300,EF4556 13,EF455615,EF4556 10,EF455605, M5941 8,U11820,EF455604 |
| Feline leukemia virus | NC_001940 | vertebrates | 3 | Retroviridae,Gammaretrovirus,Feline leukemia virus | — | JQ408981,KC461236 ,KC461237,KC46123 5,AY994055 |
| Feline papillomavirus dapapillomavirus 1 | NC_004765 | vertebrates | 1 | Papillomaviridae,Lambdapapillomavirus,Lamb | — | AB060732,M18247,A F052723 |
| Feline picornavirus | NC_016156 | vertebrates | 5 | Picornaviridae,Feline picornavirus | — | AF377865 |
| Feline sakobuvirus A | NC_022802 | vertebrates | 1 | Picornaviridae,Feline sakobuvirus A | — | JN572118,JN572117, JN572116,JN572115, JN572119 |
| Felis catus papillomavirus 4 | NC_022373 | vertebrates | 1 | Papillomaviridae,Taupapillomavirus,Felis catus papillomavirus 4 | — | KF387721 |
| Felis catus papillomavirus-3 | NC_021472 | vertebrates | 1 | Papillomaviridae,Taupapillomavirus,Felis catus papillomavirus 3 | — | KF147892 |
| Felis domesticus papillomavirus type 1 | NC_004765 | vertebrates | 1 | Papillomaviridae,Lambdapapillomavirus,Lamb dapapillomavirus 1 | — | JX972168 |
| Ferret papillomavirus | NC_022253 | vertebrates | 1 | Papillomaviridae,Ferret papillomavirus | — | AF480454 |
| Finch circovirus | NC_008522 | vertebrates | 1 | Circoviridae,Circovirus,Finch circovirus | — | KF006988 |
| Finch polyomavirus | NC_007923 | vertebrates | 1 | Polyom aviridae, Polyomavirus,Finch polyomavirus | — | DQ845075 |
| Florida woods cockroach-associated cyclovirus | NC_020206 | vertebrates | 1 | Circoviridae,Florida woods cockroach-associated cyclovirus | — | DQ192571 |
| Foot-and-mouth disease virus | NC_004004 | vertebrates | 8 | Picornaviridae,Aphthovirus,Foot-and-mouth disease virus | — | JX569794 |
| Foot-and-mouth disease virus-type A | NC_004004 | vertebrates | 86 | Picornaviridae,Aphthovirus,Foot-and-mouth disease virus | — | AM503966,XQ0871,A M409190,AM503965, M10975,AJQ07572,AJ 007347,AF154271 KC440881,HQ832576 ,AY593784,AY59380 2,HQ832585,HQ8325 79,HQ832582,JF7498 43,AY593770,AY593 765,HQ832581,KC58 8943,AY593753,AY5 93788,AY593793,AY 59803,HQ632773,A Y593760,AY593774, AY593769,HQ832587 ,AY593776,AY59375 7,AY593751,AY5937 54,HQ832588,HQ832 |

-continued

| Taxonomy | NCBI Reference Sequence ID | Host | No. of Genomes | Lineage | Segment Count | Genbank Accession ID |
|---|---|---|---|---|---|---|
| | | | | | | 592,AY593780,AY593758,KC440882,X74812,JF749841,HQ832591,AY593779,JN006722,HQ832586,AY593783,AY593771,AY593759,AY593762,AY593772,HM854025,HM854023,HQ832583,H0832589,GQ406250,AY593789,HQ832584,HM854024,AY593791,AY593756,GQ406252,AY593764,HQ832580,GQ406249,AY593790,HQ832578,AY593773,AY593794,AY593786,AY593778,AY593767,AY593792,HQ268509,AY593785,HQ832577,AY593775,AY593761,AY593782,AY593763,GQ406251,JF749848,AY593768,GQ406248,AY593801,AY593777,HM854022,HQ832590,AY593755,AY593766,AY593781,GQ406247,EF117837,AY593752,HM854021,AY593787 |
| Foot-and-mouth disease virus-type Asia 1 | NC_004004 | vertebrates | 46 | Picornaviridae,Aphthovirus,Foot-and-mouth disease virus | — | GU125646,AY593798,DQ989320,DQ989314,EF149009,DQ533483,DQ989312,DQ989308,DQ989319,DQ989311,DQ989309,KC462884,DQ989322,AY593796,DQ989307,D0989310,EF149010,AY593799,HQ632774,GU125645,AY304994,DQ989317,DQ989303,JN006719,DQ989305,DQ989313,DQ989323,AY390432,DQ989316,AY593800,JF739177,DQ989315,JN |

| Taxonomy | NCBI Reference Sequence ID | Host | No. of Genomes | Lineage | Segment Count | Genbank Accession ID |
|---|---|---|---|---|---|---|
| | | | | | | 006720,AY687333,D0989306,HQ631363,DQ989318,GU93168 2,AY593795,FJ90680 2,DQ989321,AY6873 34,KC412634,EF614 458,AY593797,DQ98 9304 |
| Foot-and-mouth disease virus-type C | NC_004004 | vertebrates | 16 | Picornaviridae,Aph

| Taxonomy | NCBI Reference Sequence ID | Host | No. of Genomes | Lineage | Segment Count | Genbank Accession ID |
|---|---|---|---|---|---|---|
| | | | | | | 641,FJ542366,AY593835,KF694734,AJ539136,AY593812,HQ632772,JX570640,HQ009509,DQ404164,KF112879,FJ175661,JX570642,DQ404176,D0404179,JXQ40501,AJ539140,KF112886,AY593817,KF694733,JXQ40492,JXQ40494,EU448371,AY593832,JX869187,KF501487,AY593824,GU125647,DQ404161,JXQ40497,AY593819,JXQ40488,JX869177,DQ40416 8,JX869180,DQ404171,AY593822,JX570645,GU125650,DQ404165,HQ412603,AF026168,AJ539139,GU125649,FJ175664,AY593823,JX869188,AY333431,JX570651,AY593825,JX570648,KF694736,AY593811,JX869186,EU448375,AF511039,DQ404162,JN998086,AF308157,EF614457,JXQ40499,HQ632769,JX570638,KF985189,FJ542371,AJ539138,EU448378,DQ404175,EU448374,AY593829,DQ404178,DQ478937,AY593827,JQ900581,DQ404180,KF112881,JX570634,KF112881,JX570643,JX869185,AB079061,AY593813,HQ632771,DQ404180,DQ404163,KF501488,JX570639,FJ542365,JF749851,JX869182,JXQ40495,EU448370,JXQ40493,D0404177,JQ973889,J |

-continued

| Taxonomy | NCBI Reference Sequence ID | Host | No. of Genomes | Lineage | Segment Count | Genbank Accession ID |
|---|---|---|---|---|---|---|
| Foot-and-mouth disease virus-type SAT 1 | NC_004004 | vertebrates | 10 | Picornaviridae,Aphthovirus,Foot-and-mouth disease virus | — | AY593838,AY593845,AY593839,AY593841,AY593844,JF749986,AY593840,AY593843,AY593842,AY593846 |
| Foot-and-mouth disease virus-type SAT 2 | NC_004004 | vertebrates | 11 | Picornaviridae,Aphthovirus,Foot-and-mouth disease virus | — | AY593849,JXQ14256,AF540910,JF749862,AY593848,KC440884,JF749861,AY593847,AJ251473,JF749864,JXQ14255 |
| Foot-and-mouth disease virus-type SAT 3 | NC_004004 | vertebrates | 4 | Picornaviridae,Aphthovirus,Foot-and-mouth disease virus | — | AY593852,AY593851,AY593850,AY593853 |
| Foot-and-mouth disease virus C1 | NC_004004 | vertebrates | 2 | Picornaviridae,Aphthovirus,Foot-and-mouth disease virus | — | AY593804,AY593805 |
| Foot-and-mouth disease virus C3 | NC_004004 | vertebrates | 2 | Picornaviridae,Aphthovirus,Foot-and-mouth disease virus | — | AY593806,AY593807 |
| Foot-and-mouth disease virus C4 | NC_004004 | vertebrates | 1 | Picornaviridae,Aphthovirus,Foot-and-mouth disease virus | — | AY593808 |
| Foot-and-mouth disease virus C5 | NC_004004 | vertebrates | 1 | Picornaviridae,Aphthovirus,Foot-and-mouth disease virus | — | AY593809 |

(Preceding row, continued Genbank Accession IDs): XQ40496,AY593828,AY593836,AY593820,KF112882,EU44836 8,FJ542372,KF11288 5,KF694744,GU3846 82,JX570650,KF1128 84,EU448369,DQ248 888,JXQ40489,AY593 831,DQ404166,DQ11 9643,EF175732,JX57 0653,AY593837,FJ17 5663,KC503937,JXQ6 6665,JX869184,DQ4 04172,JX869179,KF6 94745,AY593826,KF6 94741,EU448379,HM 008917,KF112880,JX 040498,FJ542367,AY 593814,KF694740,JX 570652,FJ175665,AY 593818,FJ542368,DQ 478936,HQ62768,K F694735,KC440883,J XQ40500

-continued

| Taxonomy | NCBI Reference Sequence ID | Host | No. of Genomes | Lineage | Segment Count | Genbank Accession ID |
|---|---|---|---|---|---|---|
| Foot-and-mouth disease virus HKN/2002 | NC_004004 | vertebrates | 1 | Picornaviridae,Aphthovirus,Foot-and-mouth disease virus | — | AY317098 |
| Foot-and-mouth disease virus 0/ES/2001 | NC_004004 | vertebrates | 1 | Picornaviridae,Aphthovirus,Foot-and-mouth disease virus | — | AY686687 |
| Foot-and-mouth disease virus 0/SKR/2000 | NC_004004 | vertebrates | 1 | Picornaviridae,Aphthovirus,Foot-and-mouth disease virus | — | AF377945 |
| Foot-and-mouth disease virus 0/UKG/3952/2001 | NC_004004 | vertebrates | 1 | Picornaviridae,Aphthovirus,Foot-and-mouth disease virus | — | EF552688 |
| Foot-and-mouth disease virus 0/UKG/4014/2001 | NC_004004 | vertebrates | 1 | Picornaviridae,Aphthovirus,Foot-and-mouth disease virus | — | EF552693 |
| Foot-and-mouth disease virus 0/UKG/4141/2001 | NC_004004 | vertebrates | 1 | Picornaviridae,Aphthovirus,Foot-and-mouth disease virus | — | EF552689 |
| Foot-and-mouth disease virus 0/UKG/4998/2001 | NC_004004 | vertebrates | 1 | Picornaviridae,Aphthovirus,Foot-and-mouth disease virus | — | EF552694 |
| Foot-and-mouth disease virus 0/UKG/5470/2001 | NC_004004 | vertebrates | 1 | Picornaviridae,Aphthovirus,Foot-and-mouth disease virus | — | EF552696 |
| Foot-and-mouth disease virus 0/UKG/5681/2001 | NC_004004 | vertebrates | 1 | Picornaviridae,Aphthovirus,Foot-and-mouth disease virus | — | EF552697 |
| Foot-and-mouth disease virus 0/UKG/7039/2001 | NC_004004 | vertebrates | 1 | Picornaviridae,Aphthovirus,Foot-and-mouth disease virus | — | EF552690 |
| Foot-and-mouth disease virus 0/UKG/7299/2001 | NC_004004 | vertebrates | 1 | Picornaviridae,Aphthovirus,Foot-and-mouth disease virus | — | EF552692 |
| Foot-and-mouth disease virus 0/UKG/9161/2001 | NC_004004 | vertebrates | 1 | Picornaviridae,Aphthovirus,Foot-and-mouth disease virus | — | EF552691 |
| Foot-and-mouth disease virus 0/UKG/9443/2001 | NC_004004 | vertebrates | 1 | Picornaviridae,Aphthovirus,Foot-and-mouth disease virus | — | EF552695 |
| Fowl adenovirus B | NC_021221 | vertebrates | 1 | Adenoviridae,Aviadenovirus,Fowl adenovirus B | — | KC493646 |
| Fowl adenovirus A | NC_001720 | vertebrates | 1 | Adenoviridae,Aviadenovirus,Fowl adenovirus A | — | U46933 |
| Fowl adenovirus C | NC_015323 | vertebrates | 2 | Adenoviridae,Aviadenovirus,Fowl adenovirus C | — | HE608152,GU188428 |
| Fowl adenovirus D | NC_000899 | vertebrates | 1 | Adenoviridae,Aviadenovirus,Fowl adenovirus D | — | AF083975 |
| Fowl adenovirus E | NC_014969 | vertebrates | 1 | Adenoviridae,Aviadenovirus,Fowl adenovirus E | — | GU734104 |
| Fowlpox virus | NC_002188 | vertebrates | 1 | Poxviridae,Avipoxvirus,Fowlpox virus | — | AF198100 |
| Fowlpox virus (isolate HP-438[Munich]) | NC_002188 | vertebrates | 1 | Poxviridae,Avipoxvirus,Fowlpox virus | — | AJ581527 |
| Francolinus leucoscepus papillomavirus 1 | NC_013117 | vertebrates | 1 | Papillomaviridae,Dyoepsilonpapillomavirus,Dyoepsilonpapillomavirus 1 | — | EU188799 |
| Friend murine leukemia virus | NC_001702,NC_001819,NC_001362,NC_001501 | vertebrates | 4 | Retroviridae,Gammaretrovirus,Murine leukemia virus | — | D88386,XQ2794,A42090,M93134 |

-continued

| Taxonomy | NCBI Reference Sequence ID | Host | No. of Genomes | Lineage | Segment Count | Genbank Accession ID |
|---|---|---|---|---|---|---|
| Fringilla coelebs papillomavirus | NC_004068 | vertebrates | 1 | Papillomaviridae,Etapapillomavirus,Etapapillomavirus 1 | — | AY057109 |
| Frog adenovirus 1 | NC_002501 | vertebrates | 1 | Adenoviridae,Siadenovirus,Frog adenovirus A | — | AF224336 |
| Frog virus 3 | NC_005946 | vertebrates | 1 | Incloviridae,Ranavirus,Frog virus 3 | — | AY548484 |
| Fujinami sarcoma virus | NC_001403 | vertebrates | 2 | Retroviridae,Alpharetrovirus,Fujinami sarcoma virus | — | AF033810,JQ2194 |
| GB virus A F023424 | NC_001837 | vertebrates | 3 | Flaviviridae,Pegivirus,Pegivirus A | — | U22303,AF023425,AF023424 |
| Gallid herpesvirus 1 | NC_006623 | vertebrates | 21 | Herpesviridae,Iltovirus,Gallid herpesvirus 1 | — | JX458822,JN596962,JN580317,JN542533,JX646898,JN804826,JN580312,U80762,H0630064,JN804827,JN580313,JX646899,JN580315,JN580314,JN542535,JQ083494,JN542534,JN596963,J0083493,JN542536,JN580316 |
| Gallid herpesvirus 2 | NC_002229 | vertebrates | 14 | Herpesviridae,Mardivirus,Gallid herpesvirus 2 | — | AF147806,AF243438,JQ806362,JQ809692,AY510475,JQ836662,JQ820250,EU499381,JX844666,DQ53034 8,JQ809691,EF52339 0,JQ314003,JQ80636 1 |
| Gallid herpesvirus 2 strain 814 | NC_002229 | vertebrates | 1 | Herpesviridae,Mardivirus,Gallid herpesvirus 2 | — | JF742597 |
| Gallid herpesvirus 3 | NC_002577 | vertebrates | 2 | Herpesviridae,Mardivirus,Gallid herpesvirus 3 | — | AB049735,HQ840738 |
| Gammapapillomavirus HPV127 | NC_014469 | vertebrates | 1 | Papillomaviridae,Gammapapillomavirus,Gammapapillomavirus HPV127 | — | HM011570 |
| Gibbon ape leukemia virus | NC_001885 | vertebrates | 2 | Retroviridae,Gammaretrovirus,Gibbon ape leukemia virus | — | U60065,M26927 |
| Giraffe coronavirus US/0H3-TC/2006 | NC_010327,NC_00773 2,NC_0051 47,NC_003 045 | vertebrates | 1 | Coronaviridae,Betacoronavirus,Betacoronavirus 1 | — | EF424622 |
| Giraffe coronavirus US/0H3/2003 | NC_010327,NC_00773 2,NC_0051 47,NC_003 045 | vertebrates | 1 | Coronaviridae,Betacoronavirus,Betacoronavirus 1 | — | EF424623 |

| Taxonomy | NCBI Reference Sequence ID | Host | No. of Genomes | Lineage | Segment Count | Genbank Accession ID |
|---|---|---|---|---|---|---|
| Goatpox virus G20-LKV | NC_004003 | vertebrates | 1 | Poxviridae,Capripoxvirus,Goatpox virus | — | AY077836 |
| Goatpox virus Pellor | NC_004003 | vertebrates | 1 | Poxviridae,Capripoxvirus,Goatpox virus | — | AY077835 |
| Golden ide reovirus | NC_010588 | vertebrates | 1 | Reoviridae,Aquareovirus,Aquareovirus G | seg. 5 | AF450324 |
| Goose adenovirus 4 | NC_017979 | vertebrates | 1 | Adenoviridae,Aviadenovirus,Goose adenovirus A | — | JF510462 |
| Goose circovirus | NC_003054 | vertebrates | 24 | Circoviridae,Circovirus,Goose circovirus | — | DQ192283,DQ192279,AY663653,DQ192282,AF536933,GU320569,DQ192285,AF536934,AF536932,AF536939,AF536941,AF536940,AF536936,DQ192287,DQ192280,AJ304456,AF536935,AF536931,AF536938,AF536937,AF418552,DQ192281,DQ192286,DQ192284 |
| Goose hemorrhagic polyomavirus | NC_004800 | vertebrates | 6 | Polyomaviridae,Polyomavirus,Goose hemorrhagic polyomavirus | — | HQ681904,HQ681903,AY140894,HQ681905,JF304775,HQ681902 |
| Goose orthoreovirus | NC_015126 | vertebrates | 1 | Reoviridae,Orthoreovirus,Avian orthoreovirus | seg. L1 | JX145328 |
| Goose orthoreovirus | NC_015127 | vertebrates | 1 | Reoviridae,Orthoreovirus,Avian orthoreovirus | seg. L2 | JX145329 |
| Goose orthoreovirus | NC_015128 | vertebrates | 1 | Reoviridae,Orthoreovirus,Avian orthoreovirus | seg. L3 | JX145330 |
| Goose orthoreovirus | NC_015129 | vertebrates | 1 | Reoviridae,Orthoreovirus,Avian orthoreovirus | seg. M1 | JX145331 |
| Goose orthoreovirus | NC_015130 | vertebrates | 1 | Reoviridae,Orthoreovirus,Avian orthoreovirus | seg. M2 | JX145332 |
| Goose orthoreovirus | NC_015131 | vertebrates | 1 | Reoviridae,Orthoreovirus,Avian orthoreovirus | seg. M3 | JX145333 |
| Goose orthoreovirus | NC_015132 | vertebrates | 1 | Reoviridae,Orthoreovirus,Avian orthoreovirus | seg. S1 | JX145334 |
| Goose orthoreovirus | NC_015133 | vertebrates | 1 | Reoviridae,Orthoreovirus,Avian orthoreovirus | seg. S2 | JX145335 |
| Goose orthoreovirus | NC_015134 | vertebrates | 1 | Reoviridae,Orthoreovirus,Avian orthoreovirus | seg. S3 | JX145336 |
| Goose orthoreovirus | NC_015135 | vertebrates | 1 | Reoviridae,Orthoreovirus,Avian orthoreovirus | seg. S4 | JX145337 |
| Goose parvovirus | NC_001701 | vertebrates | 12 | Parvoviridae,Dependovirus,Goose parvovirus | — | EU583390,KC178571,EU583389,JF333590,EU583391,KC184133,KC99673,U25749,EU583391, |

-continued

| Taxonomy | NCBI Reference Sequence ID | Host | No. of Genomes | Lineage | Segment Count | Genbank Accession ID |
|---|---|---|---|---|---|---|
| Grass carp hemorrhagic virus | NC_005167 | vertebrates | 1 | Reoviridae,Aquareovirus,Aquareovirus C | seg. 2 | EU583392,KC996729,HQ891825,KC478066 |
| Grass carp hemorrhagic virus | NC_005168 | vertebrates | 1 | Reoviridae,Aquareovirus,Aquareovirus C | seg. 3 | AF284502 |
| Grass carp hemorrhagic virus | NC_005170 | vertebrates | 1 | Reoviridae,Aquareovirus,Aquareovirus C | seg. 5 | AF284503 |
| Grass carp hemorrhagic virus | NC_005171 | vertebrates | 1 | Reoviridae,Aquareovirus,Aquareovirus C | seg. 6 | AF251262 |
| Grass carp hemorrhagic virus | NC_005172 | vertebrates | 1 | Reoviridae,Aquareovirus,Aquareovirus C | seg. 7 | AF239175 |
| Grass carp hemorrhagic virus | NC_005174 | vertebrates | 1 | Reoviridae,Aquareovirus,Aquareovirus C | seg. 9 | AF239174 |
| Grass carp hemorrhagic virus | NC_005175 | vertebrates | 1 | Reoviridae,Aquareovirus,Aquareovirus C | seg. 10 | AF284504 |
| Grass carp hemorrhagic virus | NC_005176 | vertebrates | 1 | Reoviridae,Aquareovirus,Aquareovirus C | seg. 11 | AF236688 |
| Grass carp hemorrhagic virus | | | | | | AF234321 |
| Grass carp reovirus | NC_005166 | vertebrates | 4 | Reoviridae,Aquareovirus,Aquareovirus C | seg. 1 | AF260511,GQ896334,KC847320,HQ231198 |
| Grass carp reovirus | NC_005167 | vertebrates | 4 | Reoviridae,Aquareovirus,Aquareovirus C | seg. 2 | HQ231199,AF260512,GQ896335,KC847321 |
| Grass carp reovirus | NC_005168 | vertebrates | 4 | Reoviridae,Aquareovirus,Aquareovirus C | seg. 3 | AF260513,HQ231200,GU350742,KC847322 |
| Grass carp reovirus | NC_005169 | vertebrates | 4 | Reoviridae,Aquareovirus,Aquareovirus C | seg. 4 | KC847323,HQ231201,GU350743,AF403390 |
| Grass carp reovirus | NC_005170 | vertebrates | 4 | Reoviridae,Aquareovirus,Aquareovirus C | seg. 5 | AF403391,GQ896336,HQ231202,KC847324 |
| Grass carp reovirus | NC_005171 | vertebrates | 5 | Reoviridae,Aquareovirus,Aquareovirus C | seg. 6 | JN206664,AF403392,GQ896337,KC847325,HQ231208 |
| Grass carp reovirus | NC_005172 | vertebrates | 4 | Reoviridae,Aquareovirus,Aquareovirus C | seg. 7 | HQ231203,AF403393,GU350744,KC847326 |
| Grass carp reovirus | NC_005173 | vertebrates | 5 | Reoviridae,Aquareovirus,Aquareovirus C | seg. 8 | AF403394,AF259053,GU350745,HQ231204,KC847327 |
| Grass carp reovirus | NC_005174 | vertebrates | 4 | Reoviridae,Aquareovirus,Aquareovirus C | seg. 9 | GU350746,KC847328,AF403395,HQ231205 |

| Taxonomy | NCBI Reference Sequence ID | Host | No. of Genomes | Lineage | Segment Count | Genbank Accession ID |
|---|---|---|---|---|---|---|
| Grass carp reovirus | NC_005175 | vertebrates | 5 | Reoviridae,Aquareovirus,Aquareovirus C | seg. 10 | GU350747,HQ23120 6,KC847329,AF4033 96,JN206665 |
| Grass carp reovirus | NC_005176 | vertebrates | 4 | Reoviridae,Aquareovirus,Aquareovirus C | seg. 11 | KC847330,HQ231207 ,AF403397,GU35074 |
| Ground squirrel hepatitis virus | NC_001484 | vertebrates | 8 | Hepadnaviridae,Orthohepadnavirus,Ground squirrel hepatitis virus | — | K02715 |
| Grouper iridovirus | NC_006549 | vertebrates | 1 | Iridoviridae,Ranavirus,Singapore grouper iridovirus | — | AY666015 |
| Gull circovirus | NC_008521 | vertebrates | 2 | Circoviridae,Circovirus,Gull circovirus | — | DQ845074,JQ685854 |
| Gyrovirus 4 | NC_018401 | vertebrates | 1 | Circoviridae,Gyrovirus,Gyrovirus 4 | — | JX310702 |
| Gyrovirus GyV3 | NC_017091 | vertebrates | 1 | Circoviridae,Gyrovirus,Gyrovirus GyV3 | — | JQ308210 |
| Gyrovirus Tu243 | NC_022788 | vertebrates | 1 | Circoviridae,Gyrovirus,Gyrovirus Tu243 | — | KF294861 |
| Gyrovirus Tu789 | NC_022789 | vertebrates | 1 | Circoviridae,Gyrovirus,Gyrovirus Tu789 | — | KF294862 |
| H-1 parvovirus | NC_001358 | vertebrates | 1 | Parvoviridae,Parvovirus,H-1 parvovirus | — | XQ1457 |
| HMO Astrovirus A | NC_013443 | vertebrates | 1 | Astroviridae,Mamastrovirus,HMO Astrovirus A | — | GQ415660 |
| Halastavi arva RNA virus | NC_016418 | vertebrates | 1 | Halastavi arva RNA virus | — | JN00306 |
| Hamster polyomavirus | NC_001663 | vertebrates | 8 | Polyomaviridae,Polyomavirus,Hamster polyomavirus | — | JXQ36360,JX416850, M26281,XQ2449,JX4 16853,JX416852,JX4 16849,JX416851 |
| Hepatitis A virus | NC_001489 | vertebrates | 77 | Picornaviridae,Hepatovirus,Hepatitis A virus | — | AB839696,AY644337 ,EU526089,X75215,M 20273,X75214,AB618 529,FJ360733,AB839 694,HQ437707,AB27 9732,EF406359,DQ9 91030,AB020565,KC 182588,X75216,EF40 6363,AB793726,AB2 79734,EU25118,JQ 655151,AB279733,A B258387,AB839692, AB839693,KC182589 ,EF406358,AF314208 ,DQ991029,FJ360731 ,HM769724,AB79372 5,EU01179l,AB8198 70,K02990,AB020566 ,AB020568,FJ360734 ,KC182590,FJ360735 ,JQ425480,AY644670 ,EF207320,AF268396 ,KC182587,AF51253 6,AB618531,EU1313 73,M59809,AB83969 5,AJ299464,EF40636 0,AB30205,KF77384 |

| Taxonomy | NCBI Reference Sequence ID | Host | No. of Genomes | Lineage | Segment Count | Genbank Accession ID |
|---|---|---|---|---|---|---|
| Hepatitis GB virus B | NC_001655 | vertebrates | 10 | Flaviviridae,Hepatitis GB virus B | — | 2,AF357222,AF48532 8,AB020564,M14707, AB819869,AB425339 ,DQ644426,EF40636 1,AB020569,AB0205 67,AB839697,AB279 735,FJ360730,FJ360 732,KF569906,M166 32,EU526088,M5980 8,EF406357,AY64467 6,X83302,EF406362, M59810 |
| Heron hepatitis B virus | NC_001486 | vertebrates | 1 | Hepadnaviridae,Avihepadnavirus,Heron hepatitis B virus | — | AB630364,AF179612, AB630361,AB630360 ,U22304,AB630359,A J277947,AB630363,A B630362,,AB630358 |
| Hipposideros bat coronavirus H KU10 | NC_018871 | vertebrates | 6 | Coronaviridae,Alphacoronavirus,Bat coronavirus H KU10 | — | M22056 |
| Hirame rhabdovirus | NC_005093 | vertebrates | 2 | Rhabdoviridae,Novirhabdovirus,Hirame rhabdovirus | — | JQ989266,JQ989272, JQ989269,JQ989273, JQ989267,JQ989268 |
| Human T-cell lymphotropic virus type 2b | NC_001815, NC_001488 | vertebrates | 1 | Retroviridae,Deltaretrovirus,Primate T-lymphotropic virus 2 | — | AF104985,FJ376982 |
| Human T-lymphotropic virus 1 | NC_000858, NC_001436 | vertebrates | 18 | Retroviridae,Deltaretrovirus,Primate T-lymphotropic virus 1 | — | Y13051 |
| Human T-lymphotropic virus 2 | NC_001815, NC_001488 | vertebrates | 10 | Retroviridae,Deltaretrovirus,Primate T-lymphotropic virus 2 | — | JX891479,L36905,AF 259264,JQ2029,HQ60 6138,D13784,JX8914 78,AF042071,AF1391 70,U19949,HQ60613 7,AY563954,AY5639 53,KC807984,L03561 ,L02534,AB513134,L 03562 |
| Human T-lymphotropic virus 3 | NC_003323 | vertebrates | 4 | Retroviridae,Deltaretrovirus,Primate T-lymphotropic virus 3 | — | GU212854,AF074965 ,AF139382,L20734,A F326584,X89270, L11 456,AF412314,AF326 583, Y14365 |
| Human T-lymphotropic virus 4 | NC_011800 | vertebrates | 2 | Retroviridae,Deltaretrovirus,Human T-lymphotropic virus 4 | — | EU649782,DQ093792 ,DQ462191,GQ46360 EF488483 |

| Taxonomy | NCBI Reference Sequence ID | Host | No. of Genomes | Lineage | Segment Count | Genbank Accession ID |
|---|---|---|---|---|---|---|
| Human TMEV-like cardiovirus | NC_009448,NC_001366,NC_010810 | vertebrates | 1 | Picornaviridae,Cardiovirus,Theilovirus | — | GU595289 |
| Human adenovirus 4 | NC_003266,NC_017825 | vertebrates | 6 | Adenoviridae,Mastadenovirus,Human adenovirus E | — | AY594254,KF006344,AY594253,AY599837,AY599835,AY45865 |
| Human adenovirus 41 | NC_001454 | vertebrates | 3 | Adenoviridae,Mastadenovirus,Human adenovirus F | — | DQ315364,AB728839,HM565136 |
| Human adenovirus 52 | NC_006879 | vertebrates | 1 | Adenoviridae,Mastadenovirus,Human adenovirus G | — | DQ923122 |
| Human adenovirus E | NC_003266,NC_017825 | vertebrates | 2 | Adenoviridae,Mastadenovirus,Human adenovirus E | — | AY487947,EF371058 |
| Human adenovirus F | NC_001454 | vertebrates | 1 | Adenoviridae,Mastadenovirus,Human adenovirus F | — | L19443 |
| Human betacoronavirus 2c EMC/2012 | NC_019843 | vertebrates | 1 | Coronaviridae,Betacoronavirus,Middle East respiratory syndrome coronavirus | — | JX869059 |
| Human betacoronavirus 2c England-Qatar/2012 | NC_019843 | vertebrates | 1 | Coronaviridae,Betacoronavirus,Middle East respiratory syndrome coronavirus | — | KC667074 |
| Human betacoronavirus 2c Jordan-N 3/2012 | NC_019843 | vertebrates | 1 | Coronaviridae,Betacoronavirus,Middle East respiratory syndrome coronavirus | — | KC776174 |
| Human bocavirus 4 | NC_007018 | vertebrates | 1 | Parvoviridae,Parvovirinae,Human parvovirus 4 | — | HQ113143 |
| Human coronavirus 0C43 | NC_010327,NC_007732,NC_005147,NC_003045 | vertebrates | 6 | Coronaviridae,Betacoronavirus,Betacoronavirus 1 | — | AY903459,AY585229,AY585228,JN129835,JN129834,AY903460 |
| Human cosavirus A2 | NC_012800 | vertebrates | 1 | Picornaviridae,Cosavirus,Cosavirus A | — | FJ438903 |
| Human cosavirus B | NC_012801 | vertebrates | 1 | Picornaviridae,Cosavirus,Human cosavirus B | — | FJ438907 |
| Human cosavirus D | NC_012802 | vertebrates | 1 | Picornaviridae,Cosavirus,Human cosavirus D | — | FJ438908 |
| Human cosavirus E | NC_012798 | vertebrates | 1 | Picornaviridae,Cosavirus,Human cosavirus E | — | FJ555055 |
| Human cyclovirus | NC_021568 | vertebrates | 1 | Circoviridae,Human cyclovirus VS5700009 | — | KC771281,VS5700009 |
| Human enteric coronavirus 4408 | NC_010327,NC_007732,NC_005147,NC_003045 | vertebrates | 1 | Coronaviridae,Betacoronavirus,Betacoronavirus 1 | — | FJ415324 |
| Human erythrovirus V9 | NC_004295 | vertebrates | 1 | Parvoviridae,Erythrovirus,Human erythrovirus V9 | — | AJ249437 |
| Human foamy virus | NC_001364 | vertebrates | 2 | Retroviridae,Spumavirus,Simian foamy virus | — | Y07724,Y07725 |
| Human gyrovirus type 1 | NC_015630 | vertebrates | 1 | Circoviridae,Gyrovirus,Human gyrovirus type 1 | — | FR823283 |
| Human herpesvirus 6A | NC_001664 | vertebrates | 2 | Herpesviridae,Roseolovirus,Human herpesvirus 6A | — | KC465951,X83413 |
| Human herpesvirus 6B | NC_000898 | vertebrates | 2 | Herpesviridae,Roseolovirus,Human herpesvirus 6B | — | AB021506,AF157706 |

| Taxonomy | NCBI Reference Sequence ID | Host | No. of Genomes | Lineage | Segment Count | Genbank Accession ID |
|---|---|---|---|---|---|---|
| Human papillomavirus | NC_001457 | vertebrates | 1 | Papillomaviridae,Gammapapillomavirus,Gammapapillomavirus 1 | — | JX413107 |
| Human papillomavirus | NC_012485 | vertebrates | 1 | Papillomaviridae,Gammapapillomavirus,Gammapapillomavirus 7 | — | JX413110 |
| Human papillomavirus | NC_012486 | vertebrates | 1 | Papillomaviridae,Gammapapillomavirus,Gammapapillomavirus 8 | — | JX413106 |
| Human papillomavirus | NC_014955 | vertebrates | 1 | Papillomaviridae,Gammapapillomavirus,Human papillomavirus 132-like viruses | — | JX444072 |
| Human papillomavirus-1 | NC_001356 | vertebrates | 1 | Papillomaviridae,Mupapillomavirus,Mupapillomavirus 1 | — | V01116 |
| Human papillomavirus-18 | NC_001357 | vertebrates | 1 | Papillomaviridae,Alphapapillomavirus,Alphapapillomavirus 7 | — | XQ5015 |
| Human papillomavirus-2 | NC_001352 | vertebrates | 1 | Papillomaviridae,Alphapapillomavirus,Alphapapillomavirus 4 | — | X55964 |
| Human papillomavirus-54 | NC_001676 | vertebrates | 1 | Papillomaviridae,Alphapapillomavirus,Alphapapillomavirus 13 | — | AF436129 |
| Human papillomavirus-72 | NC_001694 | vertebrates | 1 | Papillomaviridae,Alphapapillomavirus,Alphapapillomavirus 3 | — | X94164 |
| Human papillomavirus-81 | NC_001694 | vertebrates | 1 | Papillomaviridae,Alphapapillomavirus,Alphapapillomavirus 3 | — | AJ620209 |
| Human papillomavirus-83 | NC_001694 | vertebrates | 1 | Papillomaviridae,Alphapapillomavirus,Alphapapillomavirus 3 | — | AF151983 |
| Human papillomavirus-cand62 | NC_001694 | vertebrates | 1 | Papillomaviridae,Alphapapillomavirus,Alphapapillomavirus 3 | — | AY395706 |
| Human papillomavirus-cand85 | NC_001357 | vertebrates | 1 | Papillomaviridae,Alphapapillomavirus,Alphapapillomavirus 7 | — | AF131950 |
| Human papillomavirus-cand86 | NC_001694 | vertebrates | 1 | Papillomaviridae,Alphapapillomavirus,Alphapapillomavirus 3 | — | AF349909 |
| Human papillomavirus-cand87 | NC_001694 | vertebrates | 1 | Papillomaviridae,Alphapapillomavirus,Alphapapillomavirus 3 | — | AJ400628 |
| Human papillomavirus-cand89 | NC_001694 | vertebrates | 1 | Papillomaviridae,Alphapapillomavirus,Alphapapillomavirus 3 | — | AF436128 |
| Human papillomavirus-cand91 | NC_001595 | vertebrates | 1 | Papillomaviridae,Alphapapillomavirus,Alphapapillomavirus 8 | — | AF419318 |
| Human papillomavirus 109 | NC_012485 | vertebrates | 1 | Papillomaviridae,Gammapapillomavirus,Gammapapillomavirus 7 | — | EU541441 |
| Human papillomavirus 112 | NC_012486 | vertebrates | 1 | Papillomaviridae,Gammapapillomavirus,Gammapapillomavirus 8 | — | EU541442 |
| Human papillomavirus 116 | NC_013035 | vertebrates | 1 | Papillomaviridae,Gammapapillomavirus,Gammapapillomavirus 9 | — | FJ804072 |
| Human papillomavirus 121 | NC_014185 | vertebrates | 1 | Papillomaviridae,Gammapapillomavirus,Gammapapillomavirus 10 | — | GQ845443 |
| Human papillomavirus 54 | NC_001676 | vertebrates | 1 | Papillomaviridae,Alphapapillomavirus,Alphapapillomavirus 13 | — | U37488 |
| Human papillomavirus 61 | NC_001694 | vertebrates | 1 | Papillomaviridae,Alphapapillomavirus,Alphapapillomavirus 3 | — | U31793 |
| Human papillomavirus SIBX9 | NC_001576 | vertebrates | 1 | Papillomaviridae,Alphapapillomavirus,Alphapapillomavirus 2 | — | FN547152 |

-continued

| Taxonomy | NCBI Reference Sequence ID | Host | No. of Genomes | Lineage | Segment Count | Genbank Accession ID |
|---|---|---|---|---|---|---|
| Human papillomavirus type 10 | NC_001576 | vertebrates | 1 | Papillomaviridae,Alphapapillomavirus,Alphapapillomavirus 2 | — | X74465 |
| Human papillomavirus type 102 | NC_001694 | vertebrates | 1 | Papillomaviridae,Alphapapillomavirus,Alphapapillomavirus 3 | — | DQ080083 |
| Human papillomavirus type 106 | NC_004104 | vertebrates | 1 | Papillomaviridae,Alphapapillomavirus,Alphapapillomavirus 14 | — | DQ080082 |
| Human papillomavirus type 108 | NC_012213,NC_008188,NC_008189 | vertebrates | 1 | Papillomaviridae,Gammapapillomavirus,Gammapapillomavirus 6 | — | FM212639 |
| Human papillomavirus type 11 | NC_001355 | vertebrates | 49 | Papillomaviridae,Alphapapillomavirus,Alphapapillomavirus 10 | — | FN907959,FN907964,HE574703,FN870021,HE611271,HE611259,HE611263,HE962365,HE611273,HE962365,HE611264,JN644142,FN870022,HE611267,JQ773412,EU918768,HE611260,HE962023,HE574704,HE611268,HE962366,FN907963,M14119,JQ773409,HE574701,FN907961,JN644141,FN907957,FN907960,HE962024,HE611270,JQ773411,FR872717,HE611266,HE611274,HE574705,JQ773410,HE611272,HE611269,HE962368,HE611265,HE611258,FN907958,HE611261,JQ773408,HE962367,HE611262,FN907962,HE574702,HE962025 |
| Human papillomavirus type 114 | NC_001694 | vertebrates | 1 | Papillomaviridae,Alphapapillomavirus,Alphapapillomavirus 3 | — | GQ244463 |
| Human papillomavirus type 117 | NC_001576 | vertebrates | 1 | Papillomaviridae,Alphapapillomavirus,Alphapapillomavirus 2 | — | GQ246950 |
| Human papillomavirus type 119 | NC_012486 | vertebrates | 1 | mapapillomavirus 8 | — | GQ845441 |
| Human papillomavirus type 123 | NC_012485 | vertebrates | 1 | Papillomaviridae,Gammapapillomavirus,Gammapapillomavirus 7 | — | GQ845445 |
| Human papillomavirus type 128 | NC_014952 | vertebrates | 1 | Papillomaviridae,Gammapapillomavirus,Human papillomavirus type 128 | — | GU225708 |
| Human papillomavirus type 129 | NC_014953 | vertebrates | 1 | Papillomaviridae,Gammapapillomavirus,Human papillomavirus type 129 | — | GU233853 |

| Taxonomy | NCBI Reference Sequence ID | Host | No. of Genomes | Lineage | Segment Count | Genbank Accession ID |
|---|---|---|---|---|---|---|
| Human papillomavirus type 13 | NC_001355 | vertebrates | 2 | Papillomaviridae,Alphapapillomavirus,Alphapapillomavirus 10 | — | X62843,DQ344807 |
| Human papillomavirus type 130 | NC_014185 | vertebrates | 1 | Papillomaviridae,Gammapapillomavirus,Gammapapillomavirus 10 | — | GU117630 |
| Human papillomavirus type 131 | NC_014954 | vertebrates | 1 | Papillomaviridae,Gammapapillomavirus,Human papillomavirus type 131 | — | GU117631 |
| Human papillomavirus type 132 | NC_014955 | vertebrates | 1 | Papillomaviridae,Gammapapillomavirus,Human papillomavirus 132-like viruses | — | GU117632 |
| Human papillomavirus type 133 | NC_014185 | vertebrates | 1 | Papillomaviridae,Gammapapillomavirus,Gammapapillomavirus 10 | — | GU117633 |
| Human papillomavirus type 134 | NC_014956 | vertebrates | 1 | Papillomaviridae,Gammapapillomavirus,Human papillomavirus type 134 | — | GU117634 |
| Human papillomavirus type 148 | NC_014955 | vertebrates | 1 | Papillomaviridae,Gammapapillomavirus,Human papillomavirus 132-like viruses | — | GU129016 |
| Human papillomavirus type 149 | NC_012485 | vertebrates | 1 | Papillomaviridae,Gammapapillomavirus,Gammapapillomavirus 7 | — | GU117629 |
| Human papillomavirus type 16 | NC_001526 | vertebrates | 119 | Papillomaviridae,Alphapapillomavirus,Alphapapillomavirus 9 | — | HQ644258,HQ644259,HQ644243,AB18687,JQ004097,HQ644262,HQ644298,FJ610149,HQ644249,FJ610152,HQ644264,AB889490,HQ644263,AF536179,HQ644283,HQ644292,HQ644261,H0644273,AY686580,HQ644296,JQ004096,AB816688,AB818690,JQ004094,AF472509,FJ610146,JN565302,HQ644239,AB889492,HQ644240,HQ644250,HQ644286,HQ644269,HQ644278,HQ644280,HQ644288,FJ610151,HQ644294,HQ644248,HQ644241,H0644238,HQ644236,HQ644265,HQ644428,HQ644268,HQ644427,AF402678,AY686581,FJ610147,HQ644253,AF534061,HM057182,HQ644254,FJ610150,HQ644293,FJ610150,HQ644284,HQ644260,HQ644242,JQ004093,HQ644291,FJQ06723,AB |

-continued

| Taxonomy | NCBI Reference Sequence ID | Host | No. of Genomes | Lineage | Segment Count | Genbank Accession ID |
|---|---|---|---|---|---|---|
| | | | | | | 889489,JQ004095,H0644276,HQ644247,HQ644277,HQ644424,HQ644281,HQ644279,HQ644275,AF536180,JQ004099,JQ067944,HQ644289,FJ610148,HQ644234,JN565303,AB889491,HQ644257,HQ644255,AB889494,AY686579,H0644272,AB818689,AY686582,HQ644245,AF472508,HQ644285,AF125673,HQ644270,HQ644295,HQ644290,HQ644266,HQ644252,HQ644251,HQ644267,AB818693,JQ067943,HQ644271,HQ644237,AB889488,HQ0644256,HQ644235,JQ004092,HQ644246,JQ004098,AB889493,U89348,HQ644282,AB818692,AX800450,HQ644274,AY686583,K02718,AY686584,EK02718,AY686584,EU918764,AB818691,EU118173,HQ644297 |
| Human papillomavirus type 167 | NC_022892 | vertebrates | 1 | Papillomaviridae,Gammapapillomavirus,Human papillomavirus type 167 | — | KC862318 |
| Human papillomavirus type 168 | NC_012486 | vertebrates | 1 | Papillomaviridae,Gammapapillomavirus,Gammapapillomavirus 8 | — | KC862317 |
| Human papillomavirus type 18 | NC_001357 | vertebrates | 46 | Papillomaviridae,Alphapapillomavirus,Alphapapillomavirus 7 | — | GQ180792,EF202155,EF202149,EF202148,KC470211,KC470216,EF202150,KC470230,EF202153,GQ180788,KC470214,GQ180786,KC470221,KC470218,KC470228,GQ180784,KC470227,KC470229,KC470226,KC470217,KC470213,GQ180790,KC470220,GQ180791,EF202149,GQ180791,EF202145,GQ180 |

| Taxonomy | NCBI Reference Sequence ID | Host | No. of Genomes | Lineage | Segment Count | Genbank Accession ID |
|---|---|---|---|---|---|---|
| Human papillomavirus type 1a | NC_001356 | vertebrates | 1 | Papillomaviridae,Mupapillomavirus,Mupapillomavirus 1 | — | U06714 |
| Human papillomavirus type 2 | NC_001352 | vertebrates | 4 | Papillomaviridae,Alphapapillomavirus,Alphapapillomavirus 4 | — | EF362755,EF362754,EF117891,EF117890 |
| Human papillomavirus type 26 | NC_001583 | vertebrates | 1 | Papillomaviridae,Alphapapillomavirus,Alphapapillomavirus 5 | — | X74472 |
| Human papillomavirus type 27 | NC_001352 | vertebrates | 1 | Papillomaviridae,Alphapapillomavirus,Alphapapillomavirus 4 | — | X74473 |
| Human papillomavirus type 27b | NC_001352 | vertebrates | 1 | Papillomaviridae,Alphapapillomavirus,Alphapapillomavirus 4 | — | AB211993 |
| Human papillomavirus type 28 | NC_001576 | vertebrates | 1 | Papillomaviridae,Alphapapillomavirus,Alphapapillomavirus 2 | — | U31783 |
| Human papillomavirus type 29 | NC_001576 | vertebrates | 1 | Papillomaviridae,Alphapapillomavirus,Alphapapillomavirus 2 | — | U31784 |
| Human papillomavirus type 3 | NC_001576 | vertebrates | 1 | Papillomaviridae,Alphapapillomavirus,Alphapapillomavirus 2 | — | X74462 |
| Human papillomavirus type 30 | NC_001593 | vertebrates | 1 | Papillomaviridae,Alphapapillomavirus,Alphapapillomavirus 6 | — | X74474 |
| Human papillomavirus type 31 | NC_001526 | vertebrates | 23 | Papillomaviridae,Alphapapillomavirus,Alphapapillomavirus 9 | — | JQ4353,HQ537667,HQ537678,HQ537674,HQ537669,HQ537668,HQ537679,HQ537670,HQ537671,HQ537681,HQ537673,HQ537687,HQ537666,HQ537677,HQ537685,HQ537682,HQ537683,HQ537680,HQ537672,HQ537676,HQ537675,HQ537684,HQ53767586 |
| Human papillomavirus type 32 | NC_001586 | vertebrates | 1 | Papillomaviridae,Alphapapillomavirus,Alphapapillomavirus 1 | — | X74475 |
| Human papillomavirus type 33 | NC_001526 | vertebrates | 23 | Papillomaviridae,Alphapapillomavirus,Alphapapillomavirus 9 | — | HQ537706,HQ537702,HQ537701,HQ537698,M12732,HQ537694,HQ537696,HQ53777 |

| Taxonomy | NCBI Reference Sequence ID | Host | No. of Genomes | Lineage | Segment Count | Genbank Accession ID |
|---|---|---|---|---|---|---|
| Human papillomavirus type 34 | NC_001587 | vertebrates | 1 | Papillomaviridae,Alphapapillomavirus,Alphapapillomavirus 11 | — | 07,HQ537692,HQ537688,HQ537697,HQ537689,HQ537703,EU918766,HQ537693,HQ537700,HQ537704,H0537690,HQ537691,HQ537695,HQ537769,HQ537705,A12360 X74476 |
| Human papillomavirus type 35 | NC_001526 | vertebrates | 28 | Papillomaviridae,Alphapapillomavirus,Alphapapillomavirus 9 | — | HQ537725,HQ5377708,HQ537715,HQ537730,HQ537711,HQ537726,JX129488,HQ537720,HQ537718,HQ537713,HQ537717,HQ537729,HQ537723,H0537714, HQ537722, M74117,HQ537710,H0537716, HQ537719, JX129486,HQ537728,HQ537721 ,HQ5377712,HQ537727,HQ537709,HQ537724,JX129487,JX129485 |
| Human papillomavirus type 35H | NC_001357 | vertebrates | 1 | Papillomaviridae,Alphapapillomavirus,Alphapapillomavirus 9 | — | X74477 |
| Human papillomavirus type 39 | | vertebrates | 20 | Papillomaviridae,Alphapapillomavirus,Alphapapillomavirus 7 | — | KC470243,KC470238,KC470239,KC470240,KC470247,KC470231,KC470241,KC470236,M62849,KC470242,KC470232,KC470244,KC470246,KC470237,KC470235,KC470249,KC470234,KC470245,KC470248,KC470233 |
| Human papillomavirus type 4 | NC_001457 | vertebrates | 1 | Papillomaviridae,Gammapapillomavirus,Gammapapillomavirus 1 | — | X70827 |
| Human papillomavirus type 40 | NC_001595 | vertebrates | 1 | Papillomaviridae,Alphapapillomavirus,Alphapapillomavirus 8 | — | X74478 |
| Human papillomavirus type 41 | NC_001354 | vertebrates | 1 | Papillomaviridae,Nupapillomavirus,Nupapillomavirus 1 | — | X56147 |
| Human papillomavirus type 42 | NC_001586 | vertebrates | 3 | Papillomaviridae,Alphapapillomavirus,Alphapapillomavirus 1 | — | GQ472847,A28090,M73236 |
| Human papillomavirus type 43 | NC_001595 | vertebrates | 1 | Papillomaviridae,Alphapapillomavirus,Alphapapillomavirus 8 | — | AJ620205 |

-continued

| Taxonomy | NCBI Reference Sequence ID | Host | No. of Genomes | Lineage | Segment Count | Genbank Accession ID |
|---|---|---|---|---|---|---|
| Human papillomavirus type 44 | NC_001355 | vertebrates | 1 | Papillomaviridae,Alphapapillomavirus,Alphapapillomavirus 10 | — | U31788 |
| Human papillomavirus type 45 | NC_001357 | vertebrates | 24 | Papillomaviridae,Alphapapillomavirus,Alphapapillomavirus 7 | — | EF202158,EF202157, KC470251,EF202165 ,EF202162,KC47025 5,EF202167,EF20216 1,KC470252,KC4702 50,X74479,EF202163 ,KC470256,EF202216 6,EF202160,KC4702 59,KC470258,EF202 156,KC470253,KC47 0260,KC470257,EF2 02159,EF202164,KC 470254 |
| Human papillomavirus type 48 | NC_001690 | vertebrates | 1 | Papillomaviridae,Gammapapillomavirus,Gammapapillomavirus 2 | — | U31789 |
| Human papillomavirus type 50 | NC_001691 | vertebrates | 1 | Papillomaviridae,Gammapapillomavirus,Gammapapillomavirus 3 | — | U31790 |
| Human papillomavirus type 51 | NC_001583 | vertebrates | 1 | Papillomaviridae,Alphapapillomavirus,Alphapapillomavirus 5 | — | M62877 |
| Human papillomavirus type 52 | NC_001526 | vertebrates | 26 | Papillomaviridae,Alphapapillomavirus,Alphapapillomavirus 9 | — | HQ537751,HQ53773 6,HQ537734,HQ5377 42,HQ537746,AB819 274,HQ537732,HQ53 7745,AB819273,HQ5 37738,HQ537743,AB 819272,HQ537733,H 0537740,GQ472848, HQ537750,HQ53774 7,HQ537735,HQ5377 41,HQ537749,HQ537 739,HQ537737,X744 81,HQ537744,HQ537 731,HQ537748 |
| Human papillomavirus type 53 | NC_001593 | vertebrates | 16 | Papillomaviridae,Alphapapillomavirus,Alphapapillomavirus 6 | — | EF546474,EF546479, EF546469,EF546470, X74482,EF546478,E F546480,EF546473,E F546482,EF546475,E F546472,EF546481,E F546471,EF546477, GQ472849,EF546476 |
| Human papillomavirus type 55 | NC_001355 | vertebrates | 1 | Papillomaviridae,Alphapapillomavirus,Alphapapillomavirus 10 | — | U31791 |

| Taxonomy | NCBI Reference Sequence ID | Host | No. of Genomes | Lineage | Segment Count | Genbank Accession ID |
|---|---|---|---|---|---|---|
| Human papillomavirus type 56 | NC_001593 | vertebrates | 7 | Papillomaviridae,Alphapapillomavirus,Alphapapillomavirus 6 | — | EF177178,EF177181, EF177177,EF177179, X74483,EF177176, EF177180 |
| Human papillomavirus type 57 | NC_001352 | vertebrates | 1 | Papillomaviridae,Alphapapillomavirus,Alphapapillomavirus 4 | — | X55965 |
| Human papillomavirus type 57b | NC_001352 | vertebrates | 1 | Papillomaviridae,Alphapapillomavirus,Alphapapillomavirus 4 | — | U37537 |
| Human papillomavirus type 57c | NC_001352 | vertebrates | 1 | Papillomaviridae,Alphapapillomavirus,Alphapapillomavirus 4 | — | AB361563 |
| Human papillomavirus type 58 | NC_001526 | vertebrates | 45 | Papillomaviridae,Alphapapillomavirus,Alphapapillomavirus 9 | — | KC860271,HQ537758, HQ537757,EU91876 5,AB819278,HQ5377 53,FJ385267,HQ5377 63,HQ537775,HQ537 769,FJ385261,FJ3852 65,GQ472850,HQ53 7768,AB819279,HQ5 37771,HQ537755,HQ 537760,HQ537762,D 90400,HQ537770,AB 819276,FJ385268,HQ 537759,FJ385266,KC 860269,HQ537754,FJ 385262,AB819277,H 0537777,HQ537766, HQ537765,HQ53776 4,HQ537761,AB8192 75,HQ537767,FJ3852 63,HQ537756,HQ537 752,FJ385264,HQ537 776,HQ537773,HQ53 7774,HQ537772,KC8 60270 |
| Human papillomavirus type 59 | NC_001357 | vertebrates | 8 | Papillomaviridae,Alphapapillomavirus,Alphapapillomavirus 7 | — | KC470262,KC470261 ,X77858,KC470266,K C470265,KC470263, KC470264,EU918767 |
| Human papillomavirus type 6 | NC_001355 | vertebrates | 168 | Papillomaviridae,Alphapapillomavirus,Alphapapillomavirus 10 | — | HG793909,HE962032 ,HG793933,HG79391 7,HG793935,HG7938 81,HG793851,HG793 906,JN252321,HG79 3918,HG793900,HG7 93875,HG793847,HG 793852,HG793908,H G793868,HG793878, HG793890,HG79383 |

| Taxonomy | NCBI Reference Sequence ID | Host | No. of Genomes | Lineage | Segment Count | Genbank Accession ID |
|---|---|---|---|---|---|---|
| | | | | | | 9,FR751329,HG793826,HG793843,HG793821,FR751324,JN252320,HG793874,HG793856,HG793925,HG793937,HG793840,HG793849,HG793894,HG793882,HG793866,HG793896,HG793388,HG793865,HG793866,HG793938,69,FR751320,HG793844,HG793905,FR751322,HE962028,HG793902,FR751325,HG793885,HG793887,HG793815,HG793888,HG793841,HG793385,8,HG793860,HG793939,29,HG793926,HG793829,FR751328,HG793870,HG793863,HG793919,HG793811,HG793897,HG793936,HG793838,HG793895,FR751323,HG793810,HG793879,HG793385,3,JN252318,HG793939,27,HG793912,HG793922,HG793837,HG793793,3824,FR751331,HG793848,HG793873,HG793939,JN252323,HG793842,HG793931,JN252319,HG793823,HG793889,HG793381,6,FR751327,AF092932,HG793827,FR751326,HG793845,HG793884,HG793817,HG793793,3924,HG793813,HG793793,93859,HG793893,HG793830,JN252314,HG793836,FR751336,HG793818,HG793792,3,HG793877,HG793939,13,HG793862,HG793793,901,HG793892,HG793793,3911,HE962026,FR7 |

| Taxonomy | NCBI Reference Sequence ID | Host | No. of Genomes | Lineage | Segment Count | Genbank Accession ID |
|---|---|---|---|---|---|---|
| | | | | | | 51337,HG793861,HG793910,HG793828,HG793867,HG793832,HG793857,HG793933,HG793903,HG793939,FR751338,HG79330,HG793864,HG793822,HG793793914,HG793898,HG793876,HG793920,HE962029,HG793814,FR751332,JN252322,HG793871,FR751335,HG793928,HG7938384,JN252317,HG7938333,HG793915,HG793835,FR751334,HG793916,HG793921,HG793904,HG793872,JN252315,HG793812,HE962031,HE962027,HG793846,HG793907,HG793934,HG7938355,HG793831,HE962030,HG793880,FR751321,HG793891,HG793899,HG793938,FR751330,HG793820,HG793809,JN252316,HG793819,HG793888,HG793850,FR751513,HG793854,HG793825 |
| Human papillomavirus type 60 | NC_001693 | vertebrates | 1 | Papillomaviridae,Gammapapillomavirus,Gammapapillomavirus 4 | — | U31792 |
| Human papillomavirus type 63 | NC_001458 | vertebrates | 1 | Papillomaviridae,Mupapillomavirus,Mupapillomavirus 2 | — | X70828 |
| Human papillomavirus type 65 | NC_001457 | vertebrates | 1 | Papillomaviridae,Gammapapillomavirus,Gammapapillomavirus 1 | — | X70829 |
| Human papillomavirus type 66 | NC_001593 | vertebrates | 11 | Papillomaviridae,Alphapapillomavirus,Alphapapillomavirus 6 | — | EF177186,U31794,EF177184,EF177188,EF177185,EF177183,EF177191,EF177187,EF177182,EF177189,EF177190 |

| Taxonomy | NCBI Reference Sequence ID | Host | No. of Genomes | Lineage | Segment Count | Genbank Accession ID |
|---|---|---|---|---|---|---|
| Human papillomavirus type 67 | NC_001526 | vertebrates | 8 | Papillomaviridae,Alphapapillomavirus,Alphapapillomavirus 9 | — | HQ537781,HQ537782,HQ537778,HQ537784,HQ537780,HQ537783,HQ537779,D21208 |
| Human papillomavirus type 68 | NC_001357 | vertebrates | 19 | Papillomaviridae,Alphapapillomavirus,Alphapapillomavirus 7 | — | KC470277,KC470271,KC470276,EU91876 9,KC470270,KC470282,KC470274,KC470278,KC470267,KC470275,KC470272,KC470273,KC470268,KC470273,KC470269,KC470283,GQ472851,KC470281,KC470280 |
| Human papillomavirus type 68a | NC_001357 | vertebrates | 1 | Papillomaviridae,Alphapapillomavirus,Alphapapillomavirus 7 | — | DQ080079 |
| Human papillomavirus type 68b | NC_001357 | vertebrates | 1 | Papillomaviridae,Alphapapillomavirus,Alphapapillomavirus 7 | — | FR751039 |
| Human papillomavirus type 69 | NC_001583 | vertebrates | 1 | Papillomaviridae,Alphapapillomavirus,Alphapapillomavirus 5 | — | AB027020 |
| Human papillomavirus type 6a | NC_001355 | vertebrates | 1 | Papillomaviridae,Alphapapillomavirus,Alphapapillomavirus 10 | — | L41216 |
| Human papillomavirus type 6b | NC_001355 | vertebrates | 1 | Papillomaviridae,Alphapapillomavirus,Alphapapillomavirus 10 | — | XQ0203 |
| Human papillomavirus type 7 | NC_001595 | vertebrates | 1 | Papillomaviridae,Alphapapillomavirus,Alphapapillomavirus 8 | — | X74463 |
| Human papillomavirus type 70 | NC_001357 | vertebrates | 9 | Papillomaviridae,Alphapapillomavirus,Alphapapillomavirus 7 | — | KC470289,KC470290,KC470291,U21941,KC470288,KC470287,KC470286,KC470284,KC470285 |
| Human papillomavirus type 71 | NC_004104 | vertebrates | 5 | Papillomaviridae,Alphapapillomavirus,Alphapapillomavirus 14 | — | AB040456,AY330623,AY330620,AY330622,AY330621 |
| Human papillomavirus type 73 | NC_001587 | vertebrates | 1 | Papillomaviridae,Alphapapillomavirus,Alphapapillomavirus 11 | — | X94165 |
| Human papillomavirus type 74 | NC_001355 | vertebrates | 1 | Papillomaviridae,Alphapapillomavirus,Alphapapillomavirus 10 | — | AF436130 |
| Human papillomavirus type 77 | NC_001576 | vertebrates | 1 | Papillomaviridae,Alphapapillomavirus,Alphapapillomavirus 2 | — | Y15175 |
| Human papillomavirus type 82 | NC_001583 | vertebrates | 2 | Papillomaviridae,Alphapapillomavirus,Alphapapillomavirus 5 | — | AB027021,AF293961 |
| Human papillomavirus type 84 | NC_001694 | vertebrates | 1 | Papillomaviridae,Alphapapillomavirus,Alphapapillomavirus 3 | — | AF293960 |
| Human papillomavirus type 88 | NC_010329 | vertebrates | 1 | Papillomaviridae,Gammapapillomavirus,Gammapapillomavirus 5 | — | EF467176 |

| Taxonomy | NCBI Reference Sequence ID | Host | No. of Genomes | Lineage | Segment Count | Genbank Accession ID |
|---|---|---|---|---|---|---|
| Human papillomavirus type 90 | NC_004104 | vertebrates | 2 | Papillomaviridae,Alphapapillomavirus,Alphapapillomavirus 14 | — | AY057438,AB542808 |
| Human papillomavirus type 94 | NC_001576 | vertebrates | 3 | Papillomaviridae,Alphapapillomavirus,Alphapapillomavirus 2 | — | AB201226,GU117628,AJ620211 |
| Human papillomavirus type 95 | NC_001457 | vertebrates | 1 | Papillomaviridae,Gammapapillomavirus,Gammapapillomavirus 1 | — | AJ620210 |
| Human papillomavirus type 97 | NC_001357 | vertebrates | 3 | Papillomaviridae,Alphapapillomavirus,Alphapapillomavirus 7 | — | DQ080080,EF202168,FF436229 |
| Human papillomavirus type XS2 | NC_001576 | vertebrates | 1 | Papillomaviridae,Alphapapillomavirus,Alphapapillomavirus 2 | — | KC138720 |
| Human parechovirus | NC_001897 | vertebrates | 3 | Picornaviridae, Parechovirus,Human parechovirus | — | EU022171,KJ152442,AJQ05695 |
| Human parechovirus 1 | NC_001897 | vertebrates | 18 | Picornaviridae, Parechovirus,Human parechovirus | — | EF051629,S45208,GQ183021,GQ183035,GQ183023,FJ840477,GQ183019,JX44135,GQ183022, FM178558,KC769584,GQ183018,GQ183024,JX575746,GQ183020,GQ183025,L02971 ,GQ183034 |
| Human parechovirus 2 | NC_001897 | vertebrates | 1 | Picornaviridae, Parechovirus,Human parechovirus | — | AF055846 |
| Human parechovirus 3 | NC_001897 | vertebrates | 13 | Picornaviridae, Parechovirus,Human parechovirus | — | GQ183031,AJ889918,GQ183026,JX82660,GQ183027,AB6680,GQ183032,GQ183029,JX682576,AB084913,GQ183030,GQ183033,GQ183029 |
| Human parechovirus 4 | NC_001897 | vertebrates | 3 | Picornaviridae, Parechovirus,Human parechovirus | — | DQ315670,AM235750,AB433629 |
| Human parechovirus 5 | NC_001897 | vertebrates | 2 | Picornaviridae, Parechovirus,Human parechovirus | — | AM235749,JXQ50181 |
| Human parechovirus 6 | NC_001897 | vertebrates | 4 | Picornaviridae, Parechovirus,Human parechovirus | — | AB252582,EU077518,FJ888592,EU024629 |
| Human parechovirus 7 | NC_001897 | vertebrates | 1 | Picornaviridae, Parechovirus,Human parechovirus | — | EU556224 |
| Human parechovirus 8 | NC_001897 | vertebrates | 1 | Picornaviridae, Parechovirus,Human parechovirus | — | EU716175 |
| Human parechovirus type 1 PicoBank/HPeV1/a | NC_001897 | vertebrates | 1 | Picornaviridae, Parechovirus,Human parechovirus | — | FM242866 |
| Human parvovirus 4 | NC_007018 | vertebrates | 7 | Parvoviridae,Parvovirus,Human parvovirus 4 | — | DQ873387,DQ87338,EU175856,EU1758,AY622943,EU874248,DQ873389 |

| Taxonomy | NCBI Reference Sequence ID | Host | No. of Genomes | Lineage | Segment Count | Genbank Accession ID |
|---|---|---|---|---|---|---|
| Human polyomavirus 10 | NC_018102 | vertebrates | 1 | Polyomaviridae,Polyomavirus,MW polyomavirus | — | JX262162 |
| Human polyomavirus 12 | NC_020890 | vertebrates | 1 | Polyom avi ridae, Polyomavirus,Human polyomavirus 12 | — | JX308829 |
| Human polyomavirus 9 | NC_015150 | vertebrates | 2 | Polyom avi ridae, Polyom avi rus,Human polyomavirus 9 | — | KC831440,HQ696595 |
| Human rhinovirus C | NC_009996 | vertebrates | 16 | Picornaviridae,Enterovirus,Rhinovirus C | — | JF317015,JN798567, JF317014,JF317016, JN205461,JX291115, GU219984,EU840952 JF317013,JF317017, JQ245968,EF582386, JN837688,EF582385, DQ875932,EF582387 |
| Human rhinovirus C strain QCE | NC_009996 | vertebrates | 1 | Picornaviridae,Enterovirus,Rhinovirus C | — | GQ323774 |
| Human rhinovirus C3 | NC_009996 | vertebrates | 1 | Picornaviridae,Enterovirus,Rhinovirus C | — | EF186077 |
| Human rhinovirus C35 | NC_009996 | vertebrates | 1 | Picornaviridae,Enterovirus,Rhinovirus C | — | JF436925 |
| Human spumaretrovirus | NC_001364 | vertebrates | 1 | Retroviridae,Spumavirus,Simian foamy virus | — | U21247 |
| Ictalurid herpesvirus 1 | NC_001493 | vertebrates | 1 | Alloherpesviridae,Ictalurivirus,Ictalurid herpesvirus 1 | — | M75136 |
| Infectious bronchitis virus | NC_010800 ,NC_001451 | vertebrates | 71 | Coronaviridae,Gammacoronavirus,Avian coronavirus | — | DQ288927,DQ001339,AY338732,GU393335,GU393333,FJ904717,FJ904723,JQ977698,FJ904720,GU393337,EU714028,FJ904716,HM245924,JF274479,GQ504720,GU393332,GU393334,FJ904721,FJ904713,JX195175,JX195177,JF828981,JF893452,AY514485,GQ504723,FJ888351,JX195178,GU393331,GU393338,FJ807652,GQ504722,EU526388,GQ504721,DQ64405,JX195176,FJ904722,KF574761,KF377577,EU637854,JF330899,JX897900,DQ834384,AY641576,DQ001338,AY851295,EU817497,GQ504725,KC013541,EU418975,HM245923,FJ904719,JF330898,KC904719 |

-continued

| Taxonomy | NCBI Reference Sequence ID | Host | No. of Genomes | Lineage | Segment Count | Genbank Accession ID |
|---|---|---|---|---|---|---|
| | | | | | | 136209,JF828980,AY319651,JQ977697,EU418976,FJ904714,GU393336,KC506155,EU714029,KC008600,KF411040,FJ904715,HQ850618,KF411041,KC119407,FJ904718,AY692454,GQ504724,HQ848267 |
| Infectious bronchitis virus ITA/90254/2005 | NC_010800,NC_001451 | vertebrates | 1 | Coronaviridae,Gammacoronavirus,Avian coronavirus | — | FN430414 |
| Infectious bronchitis virus NGA/A116E7/2006 | NC_010800,NC_001451 | vertebrates | 1 | Coronaviridae,Gammacoronavirus,Avian coronavirus | — | FN430415 |
| Infectious bursal disease virus | NC_004178 | vertebrates | 93 | Birnaviridae,Avibirnavirus, Infectious bursal disease virus | seg. A | EF418034,AF051837,GQ166970,DQ403248,AF533670,AF092171,AF165150,JQ411012,EU162089,JF907702,EF418036,DQ0499,AF240686,GQ451330,EU595669,JX134483,DQ0867,AJ427340,AY598356,EU595670,AJ310185,EF418035,AY099456,AM167550,AY462026,AF140705,EU595667,EU595668,AY319768,AF362776,EU184687,FJ695138,AY134874,Z21971,X84034,AY323952,AF321054,AF527039,EU595672,DQ906921,D83985,EF646853,D00869,DQ927040,AY444873,AF092943,AF194428,EU162088,AJ879932,AY368653,D0088175,AY665672,XQ3993,AF165151,AY918950,AF109154,EU595671,JX134485,M97346,AF508176,AY918948,EF517528,AF247006,AF499929,A |

| Taxonomy | NCBI Reference Sequence ID | Host | No. of Genomes | Lineage | Segment Count | Genbank Accession ID |
|---|---|---|---|---|---|---|
| | | | | | | F36773,AF443294,D0927042,AF322444,J0403646,FJ695139,JF811920,L42284,AF362747,AF133904,AF321055,AF362771,AY029166,AF321056,DQ778035,EU184689,AF165149,JN585293,D49706,AJ318896,EF418033,M66722,AY462027,EU184685,U30818,JF907703,X92760,AM111353,GQ166972 |
| Infectious bursal disease virus | NC_004179 | vertebrates | 87 | Birnaviridae,Avibirnavirus,Infectious bursal disease virus | seg. B | AY598355,EU162092,AM167551,AJ318897,JQ403647,AF493979

-continued

| Taxonomy | NCBI Reference Sequence ID | Host | No. of Genomes | Lineage | Segment Count | Genbank Accession ID |
|---|---|---|---|---|---|---|
| | | | | | | 814,DQ403249,AY918949,EU595673,DQ679812,AF527040,JX134486,EU184690,AJ310186,AY705393,AY918947,JN411134,AF362770,AF362775,AF240687,DQ166818,EU184686,AY368654,AY029165,DQ927043,L19502,EU184688 |
| Infectious bursal disease virus CU-1 | NC_004178 | vertebrates | 1 | Birnaviridae,Avibirnavirus, Infectious bursal disease virus | seg. A | X16107 |
| Infectious hematopoietic necrosis virus | NC_001652 | vertebrates | 5 | Rhabdoviridae,Novirhabdovirus, Infectious hematopoietic necrosis virus | — | GQ413939,JX649101,X89213,L40883,HM461966 |
| Infectious pancreatic necrosis virus | NC_001915 | vertebrates | 29 | Birnaviridae,Aquabirnavirus,Infectious pancreatic necrosis virus | seg. A | DQ536090,AY780919,AJ622822,AY780923,AY780921,M18049,AY374435,AY379738,AY780918,AY354519,AY379737,DQ0701,AY379736,AY780922,AY379742,DQ536091,AY823632,AY35452 0,AY379744,AY2837 80,AF078668,AY78809 24,U56907,D26526,EF49156,AY780920,AY354521,AY379735,AY379740 |
| Infectious pancreatic necrosis virus | NC_001916 | vertebrates | 20 | Birnaviridae,Aquabirnavirus,Infectious pancreatic necrosis virus | seg. B | AY379741,AY379739,AY780930,AY379743,AY823633,M58756,AY129664,AY354522,AY780927,AY35452 3,AY354524,M58757,AY780929,AY780931,AY780925,AY780926,AY780928,D26527,AJ622823,AF078669 |
| Infectious pancreatic necrosis virus-Mexico | NC_001916 | vertebrates | 1 | Birnaviridae,Aquabirnavirus,Infectious pancreatic necrosis virus | seg. B | EU665685 |
| Infectious salmon anemia virus | NC_006497 | vertebrates | 44 | Orthomyxoviridae,Isavirus,Infectious salmon anemia virus | seg. B | DQ022085,DQ785283,DQ785275,DQ785286,DQ003603,DQ785276,DQ003600,AF262386,EU118822,AF3 |

-continued

| Taxonomy | NCBI Reference Sequence ID | Host | No. of Genomes | Lineage | Segment Count | Genbank Accession ID |
|---|---|---|---|---|---|---|
| | | | | | | 15063,DQ785278,AF404340,DQ785281,D0003601,AF262382,DQ785279,AF262388,AF262380,DQ003607,AF262383,AY744395,DQ785285,AJQ12285,DQ785277,AF262389,DQ058660,DQ003602,DQ785274,AF312317,Y10404,AF312315,DQ003606,DQ785280,AF262384,DQO03605,AF262381,DQ785284,AF262387,D0785282,DQ003604,DQ785273,AJ242016,AF262385,AF312316 |
| Infectious salmon anemia virus | NC_006498 | vertebrates | 8 | Orthomyxoviridae,Isavirus,Infectious salmon anemia virus | seg. 7 | AY044132,AJ306487,AF404341,AF429990,AF328627,DQ673253,AF429989,DQ673254 |
| Infectious salmon anemia virus | NC_006499 | vertebrates | 9 | Orthomyxoviridae,Isavirus,Infectious salmon anemia virus | seg. 6 | AF404342,JN711062,AF220607,JN711065,AY059402,JN711074,JN711093,JN711096,JN711060 |
| Infectious salmon anemia virus | NC_006500 | vertebrates | 38 | Orthomyxoviridae,Isavirus,Infectious salmon anemia virus | seg. 5 | JN711056,JN711023,DQ465047,JN711047,JN711040,AF429986,JN711041,JN711021,JN711054,DQ465043,JN711030,JN711024,JN711019,DQ465044,AJ277461,DQ440507,JN711043,AF404343,AF429988,JN711044,DQ440508,AF429987,JN711053,JN711026,JN711055,JN711049,DQ465045,JN711045,JN711042,JN711050,JN711033,JN711046,JN711036,DQ465046,JN711022,JN711051,DQ440506,JN711031 |

-continued

| Taxonomy | NCBI Reference Sequence ID | Host | No. of Genomes | Lineage | Segment Count | Genbank Accession ID |
|---|---|---|---|---|---|---|
| Infectious salmon anemia virus | NC_006501 | vertebrates | 25 | Orthomyxoviridae,Isavirus,Infectious salmon anemia virus | seg. 4 | DQ785227,DQ785223,DQ785221,DQ520600,DQ785218,DQ785224,AY744391,DQ785217,HM172539,DQ785222,DQ520601,DQ785229,DQ785219,D0785228,DQ520602, DQ520598,AF404344 DQ520597,DQ785225,DQ785220,DQ785226,EU118818,DQ785230,AF306548,DQ520599 |
| Infectious salmon anemia virus | NC_006502 | vertebrates | 92 | Orthomyxoviridae,Isavirus,Infectious salmon anemia virus | seg. 3 | JN710910,JN710861, JN710908,JN710864, JN710894,JN710866, JN710854,JN710843, JN710915,JN710889, JN710839,JN710871, JN710846,JN710904, JN710918,JN710907, JN710840,JN710913, JN710881,JN710916, JN710858,JN710853, JN710919,JN710872, JN710844,JN710883, JN710903,AJ276858, JN710887,JN710906, JN710835,JN710842, HM172538,JN710837,AF404345,JN710873,JN710914,JN710867,JXQ70881,JN710890,JN710905,JN710879,JN710896,JN710841,JN710851,JN710891,JN710859,JN710836,JN710885,JN710880,JN710895,JN710878,JN710869,JN710874,JN710850,JN710865,JN710870,JN710900,JN710884,JN710882,JN710849,JN710875,JN710888,JN710902,JN710886,JN710911,JN710838,JN710857 |

-continued

| Taxonomy | NCBI Reference Sequence ID | Host | No. of Genomes | Lineage | Segment Count | Genbank Accession ID |
|---|---|---|---|---|---|---|
| | | | | | | ,AF306549,JN710899,JN710898,JN710897,JN710921,JN710920,JN710856,JN710912,JN710845,JN710917,JN710848,JN710847,JN710901,JN710892,JN710909,JN710876,JN710862,JN710893,JN710852,JN710860,JN710868,JN710863,JN710877,JN710855 |
| Infectious salmon anemia virus | NC_006503 | vertebrates | 23 | Orthomyxoviridae,Isavirus,Infectious salmon anemia virus | seg. 2 | DQ676937,DQ785200,DQ785198,DQ785195,DQ785191,DQ785199,DQ785194,DQ520596,DQ785190,HM172537,AJ242808,EU118816,DQ785189,DQ520595, DQ785197,D0785192,AF404346,AJQ02475,AY744389,DQ785202, DQ785196,DQ785193,DQ785201 |
| Infectious salmon anemia virus | NC_006505 | vertebrates | 32 | Orthomyxoviridae,Isavirus,Infectious salmon anemia virus | seg. 1 | DQ785181,AY860813,AY168787,DQ785188,AY860812,AY954528,AY373381,DQ785183,DQ785176,DQ785186,AY373379,AY373380,DQ785175,AY860811,DQ785185,D0785182,AY860808,AY373382,DQ785180,DQ785187,AY860809,AY860810,AJ514403,DQ785179,AY744388,EU118815,DQ785178,AY954527,HM172536,DQ785184,DQ785177,AY954526 |
| Infectious spleen and kidney necrosis virus | NC_003494 | vertebrates | 1 | Indoviridae,Megalocytivirus,Infectious spleen and kidney necrosis virus | — | AF371960 |
| Jaagsiekte sheep retrovirus | NC_001494 | vertebrates | 6 | Retroviridae,Betaretrovirus,Jaagsiekte sheep retrovirus | — | AF105220,DQ838494,A27950,C0964469,A |

F357971,M80216

-continued

| Taxonomy | NCBI Reference Sequence ID | Host | No. of Genomes | Lineage | Segment Count | Genbank Accession ID |
|---|---|---|---|---|---|---|
| Japanese eel endothelial cells-infecting virus | NC_015123 | vertebrates | 1 | Japanese eel endothelial cells-infecting virus | — | AB543063 |
| Jembrana disease virus | NC_001413 | vertebrates | 1 | Retroviridae,Lentivirus,Bovine immunodeficiency virus | — | U21603 |
| Koala retrovirus | NC_021704 | vertebrates | 1 | Retroviridae,Gammaretrovirus,Koala retrovirus | — | KC779547 |
| Kobuvirus pig/JY-2010a/CHN 9 | NC_011829 ,NC_01676 | vertebrates | 1 | Picornaviridae,Kobuvirus,Aichivirus C | — | GU292559 |
| Kobuvirus sewage Kathmandu | NC_001918 | vertebrates | 1 | Picornaviridae,Kobuvirus,Aichivirus A | — | JQ898342 |
| Labidocera aestiva circovirus | NC_017843 | vertebrates | 1 | Circoviridae,Circovirus,Labidocera aestiva circovirus | — | JF912805 |
| Lactate dehydrogenase-elevating virus | NC_001639 | vertebrates | 2 | Arteriviridae,Arterivirus, Lactate dehydrogenase-elevating virus | — | U15146,L13298 |
| Lagenorhynchus acutus papillomavirus | NC_011109 | vertebrates | 1 | Papillomaviridae,Upsilonpapillomavirus,Upsilonpapillomavirus 1 | — | GU117624 |
| Lambdapapillomavirus 3 | NC_013237 | vertebrates | 1 | Papillomaviridae,Lambdapapillomavirus,Lambdapapillomavirus 3 | — | FJ492744 |
| Large yellow croaker iridovirus | NC_003494 | vertebrates | 1 | Iridoviridae,Megalocytivirus,Infectious spleen and kidney necrosis virus | — | AY779031 |
| Lelystad virus | NC_001961 | vertebrates | 1 | Arteriviridae,Arterivirus,Porcine reproductive and respiratory syndrome virus | — | M96262 |
| Ljungan virus | NC_003976 | vertebrates | 3 | Picornaviridae,Parechovirus,Ljungan virus | — | AF538689,EF202833, AF327920 |
| Ljungan virus strain 145SL | NC_003976 | vertebrates | 2 | Picornaviridae,Parechovirus,Ljungan virus | — | AF327922,FJ384560 |
| Ljungan virus strain 174F | NC_003976 | vertebrates | 1 | Picornaviridae,Parechovirus,Ljungan virus | — | AF327921 |
| Lulll virus | NC_004713 | vertebrates | 1 | Parvoviridae,Parvovirus,Lulll virus | — | M81888 |
| Lumpy skin disease virus | NC_003027 | vertebrates | 1 | Poxviridae,Capripoxvirus,Lumpy skin disease virus | — | AF409138 |
| Lumpy skin disease virus | NC_003027 | vertebrates | 1 | Poxviridae,Capripoxvirus,Lumpy skin disease NI-2490 virus | — | AF325528 |
| Lumpy skin disease virus | NC_003027 | vertebrates | 1 | Poxviridae,Capripoxvirus,Lumpy skin disease NW-LW virus | — | AF409137 |
| Lymphocystis disease virus-isolate China | NC_005902 | vertebrates | 1 | Iridoviridae,Lymphocystivirus,Lymphocystis disease virus-isolate China | — | AY380826 |
| Lymphocystis disease virus 1 | NC_001824 | vertebrates | 1 | Iridoviridae,Lymphocystivirus,Lymphocystis disease virus 1 | — | L63545 |
| Lynx rufus papillomavirus type 1 | NC_004765 | vertebrates | 1 | Papillomaviridae,Lambdapapillomavirus,Lambdapapillomavirus 1 | — | AY904722 |
| MW polyomavirus | NC_018102 | vertebrates | 11 | Polyomaviridae,Polyomavirus,MW polyomavirus | — | JQ898292,KC549591 ,KC549588,JQ89829 1,KC549590,KC549587,KC549589,KC549593,KC549594,KC549592,KC549586 |

| Taxonomy | NCBI Reference Sequence ID | Host | No. of Genomes | Lineage | Segment Count | Genbank Accession ID |
|---|---|---|---|---|---|---|
| Macaca fascicularis papillomavirus type 10 | NC_001678 | vertebrates | 1 | Papillomaviridae,Alphapapillomavirus,Alphapapillomavirus 12 | — | EU490515 |
| Macaca fascicularis papillomavirus type 11 | NC_001678 | vertebrates | 1 | Papillomaviridae,Alphapapillomavirus,Alphapapillomavirus 12 | — | GQ227670 |
| Macaca fascicularis papillomavirus type 3 | NC_001678 | vertebrates | 1 | Papillomaviridae,Alphapapillomavirus,Alphapapillomavirus 12 | — | EF558839 |
| Macaca fascicularis papillomavirus type 3b | NC_001678 | vertebrates | 1 | Papillomaviridae,Alphapapillomavirus,Alphapapillomavirus 12 | — | EF591299 |
| Macaca fascicularis papillomavirus type 4 | NC_001678 | vertebrates | 1 | Papillomaviridae,Alphapapillomavirus,Alphapapillomavirus 12 | — | EF558841 |
| Macaca fascicularis papillomavirus types | NC_001678 | vertebrates | 1 | Papillomaviridae,Alphapapillomavirus,Alphapapillomavirus 12 | — | EF558843 |
| Macaca fascicularis papillomavirus type 6 | NC_001678 | vertebrates | 1 | Papillomaviridae,Alphapapillomavirus,Alphapapillomavirus 12 | — | EF558840 |
| Macaca fascicularis papillomavirus type 7 | NC_001678 | vertebrates | 1 | Papillomaviridae,Alphapapillomavirus,Alphapapillomavirus 12 | — | EF558838 |
| Macaca fascicularis papillomavirus type 8 | NC_001678 | vertebrates | 1 | Papillomaviridae,Alphapapillomavirus,Alphapapillomavirus 12 | — | EF558842 |
| Macaca fascicularis papillomavirus type 9 | NC_001678 | vertebrates | 1 | Papillomaviridae,Alphapapillomavirus,Alphapapillomavirus 12 | — | EU490516 |
| Macaca fascicularis polyomavirus 1 | NC_019851 | vertebrates | 1 | Polyomaviridae,Polyomavirus,Macaca fascicularis polyomavirus 1 | — | JX159986 |
| Macaca fuscata rhadinovirus | NC_003401 | vertebrates | 3 | Herpesviridae,Rhadinovirus,Macacine herpesvirus 5 | — | JN885137,AY528864,JN885136 |
| Macacine herpesvirus 1 | NC_004812 | vertebrates | 1 | Herpesviridae,Simplexvirus,Macacine herpesvirus 1 | — | AF533768 |
| Macacine herpesvirus 3 | NC_006150 | vertebrates | 3 | Herpesviridae,Cytomegalovirus,Macacine herpesvirus 3 | — | DQ120516,JQ795930,AY186194 |
| Macacine herpesvirus 4 | NC_006146 | vertebrates | 1 | Herpesviridae,Lymphocryptovirus,Macacine herpesvirus 4 | — | AY037858 |
| Macacine herpesvirus 5 | NC_003401 | vertebrates | 1 | Herpesviridae,Rhadinovirus,Macacine herpesvirus 5 | — | AF083501 |
| Macaque simian foamy virus | NC_010819 | vertebrates | 2 | Retroviridae,Spumavirus,Macaque simian foamy virus | — | X54482,JN801175 |
| Magpie-robin coronavirus HKU18 | NC_016993 | vertebrates | 1 | Coronaviridae,Deltacoronavirus,Magpie-robin coronavirus HKU18 | — | JQ065046 |
| Mamastrovirus 10 | NC_004579 | vertebrates | 1 | Astroviridae,Mamastrovirus,Mamastrovirus 10 | — | AY179509 |
| Mamastrovirus 13 | NC_002469 | vertebrates | 1 | Astroviridae,Mamastrovirus,Mamastrovirus 13 | — | Y15937 |
| Mammalian Orthoreovirus strain T3/Bat/Germany/342/08 | NC_004274 | vertebrates | 1 | Reoviridae,Orthoreovirus,Mammalian orthoreovirus | seg. L3 | JQ412757 |
| Mammalian Orthoreovirus strain T3/Bat/Germany/342/08 | NC_004275 | vertebrates | 1 | Reoviridae,Orthoreovirus,Mammalian orthoreovirus | seg. L2 | JQ412756 |
| Mammalian Orthoreovirus strain T3/Bat/Germany/342/08 | NC_004276 | vertebrates | 1 | Reoviridae,Orthoreovirus,Mammalian orthoreovirus | seg. S4 | JQ412764 |

| Taxonomy | NCBI Reference Sequence ID | Host | No. of Genomes | Lineage | Segment Count | Genbank Accession ID |
|---|---|---|---|---|---|---|
| Mammalian Orthoreovirus T3/Bat/Germany/342/08 | NC_004277 | vertebrates | 1 | Reoviridae,Orthoreovirus,Mammalian orthoreovirus | seg. S1 | JQ412761 |
| Mammalian Orthoreovirus T3/Bat/Germany/342/08 | NC_004278 | vertebrates | 1 | Reoviridae,Orthoreovirus,Mammalian orthoreovirus | seg. M2 | JQ412759 |
| Mammalian Orthoreovirus T3/Bat/Germany/342/08 | NC_004279 | vertebrates | 1 | Reoviridae,Orthoreovirus,Mammalian orthoreovirus | seg. S2 | JQ412762 |
| Mammalian Orthoreovirus T3/Bat/Germany/342/08 | NC_004280 | vertebrates | 1 | Reoviridae,Orthoreovirus,Mammalian orthoreovirus | seg. M1 | JQ412758 |
| Mammalian Orthoreovirus T3/Bat/Germany/342/08 | NC_004281 | vertebrates | 1 | Reoviridae,Orthoreovirus,Mammalian orthoreovirus | seg. M3 | JQ412760 |
| Mammalian Orthoreovirus T3/Bat/Germany/342/08 | NC_004282 | vertebrates | 1 | Reoviridae,Orthoreovirus,Mammalian orthoreovirus | seg. L1 | JQ412755 |
| Mammalian Orthoreovirus T3/Bat/Germany/342/08 | NC_004283 | vertebrates | 1 | Reoviridae,Orthoreovirus,Mammalian orthoreovirus | seg. S3 | JQ412763 |
| Mammalian Orthoreovirus T3/Bat/Germany/342/08 | NC_013228 | vertebrates | 1 | Reoviridae,Orthoreovirus,Mammalian orthoreovirus | seg. M2 | JQ412759 |
| Mammalian Orthoreovirus T3/Bat/Germany/342/08 | NC_013230 | vertebrates | 1 | Reoviridae,Orthoreovirus,Mammalian orthoreovirus | seg. M3 | JQ412760 |
| Mammalian Orthoreovirus T3/Bat/Germany/342/08 | NC_013232 | vertebrates | 1 | Reoviridae,Orthoreovirus,Mammalian orthoreovirus | seg. S2 | JQ412762 |
| Mammalian Orthoreovirus T3/Bat/Germany/342/08 | NC_013234 | vertebrates | 1 | Reoviridae,Orthoreovirus,Mammalian orthoreovirus | seg. S4 | JQ412764 |
| Mammalian orthoreovirus | NC_004274 | vertebrates | 2 | Reoviridae,Orthoreovirus,Mammalian orthoreovirus | seg. L3 | EF029088,JN799428 |
| Mammalian orthoreovirus | NC_004275 | vertebrates | 3 | Reoviridae,Orthoreovirus,Mammalian orthoreovirus | seg. L2 | DQ885990,HQ642770,JN799427 |
| Mammalian orthoreovirus | NC_004276 | vertebrates | 2 | Reoviridae,Orthoreovirus,Mammalian orthoreovirus | seg. S4 | DQ396806,JN799422 |
| Mammalian orthoreovirus | NC_004277 | vertebrates | 3 | Reoviridae,Orthoreovirus,Mammalian orthoreovirus | seg. S1 | DQ911244,HQ642775,JN799419 |
| Mammalian orthoreovirus | NC_004278 | vertebrates | 3 | Reoviridae,Orthoreovirus,Mammalian orthoreovirus | seg. M2 | JN799424,HQ642772,DQ482462 |
| Mammalian orthoreovirus | NC_004279 | vertebrates | 3 | Reoviridae,Orthoreovirus,Mammalian orthoreovirus | seg. S2 | JN799420,DQ396805,HQ642776 |
| Mammalian orthoreovirus | NC_004280 | vertebrates | 3 | Reoviridae,Orthoreovirus,Mammalian orthoreovirus | seg. M1, | HQ642773,JN799423 DQ396804 |

| Taxonomy | NCBI Reference Sequence ID | Host | No. of Genomes | Lineage | Segment Count | Genbank Accession ID |
|---|---|---|---|---|---|---|
| Mammalian orthoreovirus | NC_004281 | vertebrates | 2 | Reoviridae,Orthoreovirus,Mammalian orthoreovirus | seg. M3 | JN799425,DQ403254 |
| Mammalian orthoreovirus | NC_004282 | vertebrates | 3 | Reoviridae,Orthoreovirus,Mammalian orthoreovirus | seg. L1 | JN799426,HQ642771 ,DQ997719 |
| Mammalian orthoreovirus | NC_004283 | vertebrates | 3 | Reoviridae,Orthoreovirus,Mammalian orthoreovirus | seg. S3 | JN799421,HQ642777 ,DQ411553 |
| Mammalian orthoreovirus | NC_013228 | vertebrates | 3 | Reoviridae,Orthoreovirus,Mammalian orthoreovirus | seg. M2 | JN799424,HQ642772 ,DQ482462 |
| Mammalian orthoreovirus | NC_013230 | vertebrates | 2 | Reoviridae,Orthoreovirus,Mammalian orthoreovirus | seg. M3 | JN799425,DQ403254 |
| Mammalian orthoreovirus | NC_013232 | vertebrates | 3 | Reoviridae,Orthoreovirus,Mammalian orthoreovirus | seg. S2 | JN799420,DQ396805 ,HQ642776 |
| Mammalian orthoreovirus | NC_013234 | vertebrates | 2 | Reoviridae,Orthoreovirus,Mammalian orthoreovirus | seg. S4 | DQ396806,JN799422 |
| Mammalian orthoreovirus 1 | NC_004274 | vertebrates | 1 | Reoviridae,Orthoreovirus,Mammalian orthoreovirus | seg. L3 | AF129820 |
| Mammalian orthoreovirus 1 | NC_004275 | vertebrates | 1 | Reoviridae,Orthoreovirus,Mammalian orthoreovirus | seg. L2 | AF378004 |
| Mammalian orthoreovirus 1 | NC_004276 | vertebrates | 2 | Reoviridae,Orthoreovirus,Mammalian orthoreovirus | seg. S4 | X61586,M13139 |
| Mammalian orthoreovirus 1 | NC_004277 | vertebrates | 8 | Reoviridae,Orthoreovirus,Mammalian orthoreovirus | seg. S1 | AY862136,EF494445, M10260,AY862135,M 35963,M14779,AY86 2133,AY862134 |
| Mammalian orthoreovirus 1 | NC_004278 | vertebrates | 2 | Reoviridae,Orthoreovirus,Mammalian orthoreovirus | seg. M2 | M19345,M19407 |
| Mammalian orthoreovirus 1 | NC_004279 | vertebrates | 2 | Reoviridae,Orthoreovirus,Mammalian orthoreovirus | seg. S2 | M17598,L19774 |
| Mammalian orthoreovirus 1 | NC_004280 | vertebrates | 4 | Reoviridae,Orthoreovirus,Mammalian orthoreovirus | seg. M1 | AY428872,X59945,A Y428870,AY428871 |
| Mammalian orthoreovirus 1 | NC_004281 | vertebrates | 1 | Reoviridae,Orthoreovirus,Mammalian orthoreovirus | seg. M3 | AF174382 |
| Mammalian orthoreovirus 1 | NC_004283 | vertebrates | 2 | Reoviridae,Orthoreovirus,Mammalian orthoreovirus | seg. S3 | M14325,M18389 |
| Mammalian orthoreovirus 1 | NC_013228 | vertebrates | 2 | Reoviridae,Orthoreovirus,Mammalian orthoreovirus | seg. M2 | M19345,M19407 |
| Mammalian orthoreovirus 1 | NC_013230 | vertebrates | 1 | Reoviridae,Orthoreovirus,Mammalian orthoreovirus | seg. M3 | AF174382 |
| Mammalian orthoreovirus 1 | NC_013232 | vertebrates | 2 | Reoviridae,Orthoreovirus,Mammalian orthoreovirus | seg. S2 | M17598,L19774 |
| Mammalian orthoreovirus 1 | NC_013234 | vertebrates | 2 | Reoviridae,Orthoreovirus,Mammalian orthoreovirus | seg. S4 | X61586,M13139 |
| Mammalian orthoreovirus 2 | NC_004274 | vertebrates | 3 | Reoviridae,Orthoreovirus,Mammalian orthoreovirus | seg. L3 | AF129821,GU196308 ,DQ664186 |
| Mammalian orthoreovirus 2 | NC_004275 | vertebrates | 3 | Reoviridae,Orthoreovirus,Mammalian orthoreovirus | seg. L2 | DQ664185,GU19630 7,AF378006 |
| Mammalian orthoreovirus 2 | NC_004276 | vertebrates | 2 | Reoviridae,Orthoreovirus,Mammalian orthoreovirus | seg. S4 | DQ318037,GU19631 3 |

-continued

| Taxonomy | NCBI Reference Sequence ID | Host | No. of Genomes | Lineage | Segment Count | Genbank Accession ID |
|---|---|---|---|---|---|---|
| Mammalian orthoreovirus 2 | NC_004277 | vertebrates | 10 | Reoviridae,Orthoreovirus,Mammalian orthoreovirus | seg. S1 | EU049605,AY862137,EU049607,EU049960 4,EU049603,M35964, GU196315,AY862138 ,EU049606,DQ31230 1 |
| Mammalian orthoreovirus 2 | NC_004278 | vertebrates | 2 | Reoviridae,Orthoreovirus,Mammalian orthoreovirus | seg. M2 | DQ664188,GU19631 0 |
| Mammalian orthoreovirus 2 | NC_004279 | vertebrates | 2 | Reoviridae,Orthoreovirus,Mammalian orthoreovirus | seg. S2 | GU196311,DQ66419 0 |
| Mammalian orthoreovirus 2 | NC_004280 | vertebrates | 4 | Reoviridae,Orthoreovirus,Mammalian orthoreovirus | seg. M1 | AY428873,DQ664187 ,GU196309,AY42887 4 |
| Mammalian orthoreovirus 2 | NC_004281 | vertebrates | 3 | Reoviridae,Orthoreovirus,Mammalian orthoreovirus | seg. M3 | GU196314,DQ66418 9,AF174383 |
| Mammalian orthoreovirus 2 | NC_004282 | vertebrates | 2 | Reoviridae,Orthoreovirus,Mammalian orthoreovirus | seg. L1 | DQ664184,GU19630 6 |
| Mammalian orthoreovirus 2 | NC_004283 | vertebrates | 3 | Reoviridae,Orthoreovirus,Mammalian orthoreovirus | seg. S3 | GU196312,M18390,D 0664191 |
| Mammalian orthoreovirus 2 | NC_013228 | vertebrates | 2 | Reoviridae,Orthoreovirus,Mammalian orthoreovirus | seg. M2 | DQ664188,GU19631 0 |
| Mammalian orthoreovirus 2 | NC_013230 | vertebrates | 3 | Reoviridae,Orthoreovirus,Mammalian orthoreovirus | seg. M3 | GU196314,DQ66418 9,AF174383 |
| Mammalian orthoreovirus 2 | NC_013232 | vertebrates | 2 | Reoviridae,Orthoreovirus,Mammalian orthoreovirus | seg. S2 | GU196311,DQ66419 0 |
| Mammalian orthoreovirus 2 | NC_013234 | vertebrates | 2 | Reoviridae,Orthoreovirus,Mammalian orthoreovirus | seg. S4 | DQ318037,GU19631 3 |
| Mammalian orthoreovirus 2 | NC_004276 | vertebrates | 1 | Reoviridae,Orthoreovirus,Mammalian orthoreovirus D5/Jones orthoreovirus | seg. S4 | X60066 |
| Mammalian orthoreovirus 2 | NC_013234 | vertebrates | 1 | Reoviridae,Orthoreovirus,Mammalian orthoreovirus D5/Jones orthoreovirus | seg. S4 | X60066 |
| Mammalian orthoreovirus 3 | NC_004274 | vertebrates | 8 | Reoviridae,Orthoreovirus,Mammalian orthoreovirus | seg. L3 | GU991661,JX486059 ,JQ599141,EF494437 ,M23747,AF129822,G U991671,GU589579 |
| Mammalian orthoreovirus 3 | NC_004275 | vertebrates | 11 | Reoviridae,Orthoreovirus,Mammalian orthoreovirus | seg. L2 | JQ599139,AF378008, GU991660,AF378007 ,JX486058,EF494436 ,GU991670,AF37801 0,AF378009,GU5895 78,JQ3488 |
| Mammalian orthoreovirus 3 | NC_004276 | vertebrates | 12 | Reoviridae,Orthoreovirus,Mammalian orthoreovirus | seg. S4 | GU991678,K02739,D 0004471,DQ004472, DQ004473,GU58958 6,JX486066,DQ0044 70,DQ004474,EF494 444,DQ004475,GU99 1668 |

-continued

| Taxonomy | NCBI Reference Sequence ID | Host | No. of Genomes | Lineage | Segment Count | Genbank Accession ID |
|---|---|---|---|---|---|---|
| Mammalian orthoreovirus 3 | NC_004277 | vertebrates | 24 | Reoviridae,Orthoreovirus,Mammalian orthoreovirus | seg. S1 | JQ979280,JQ979277, GU991675,JQ599138, JQ979273,GU991665, AY302467,JQ979272, JQ979275,JQ979284, EF494441,JQ979282, GU589583,JQ979274, JX486063,JQ979271, JQ979281,XQ1161, JQ979283,JQ979278, JQ979285,M10262,J0979279,JQ979276 |
| Mammalian orthoreovirus 3 | NC_004278 | vertebrates | 8 | Reoviridae,Orthoreovirus,Mammalian orthoreovirus | seg. M2 | GU991663,GU58958 1,M20161,EF494439, GU991673,JX486061, M19408,U24260 |
| Mammalian orthoreovirus 3 | NC_004279 | vertebrates | 8 | Reoviridae,Orthoreovirus,Mammalian orthoreovirus | seg. S2 | GU589584,JX486064 ,GU991666,L19776,GU991676,EF494442,J02327,M25780 |
| Mammalian orthoreovirus 3 | NC_004280 | vertebrates | 13 | Reoviridae,Orthoreovirus,Mammalian orthoreovirus | seg. M1 | GU991672,GU58958 0,GU991662,AY4288 78,M27261,AY42887 5,AY551083,EF49443 8,AY428876,AF46168 3,AY428877,JX48606 0,AF461684 |
| Mammalian orthoreovirus 3 | NC_004281 | vertebrates | 7 | Reoviridae,Orthoreovirus,Mammalian orthoreovirus | seg. M3 | GU991664,AF174384 ,JX486062,EF494440 ,M27262,GU589582, GU991674 |
| Mammalian orthoreovirus 3 | NC_004282 | vertebrates | 7 | Reoviridae,Orthoreovirus,Mammalian orthoreovirus | seg. L1 | M31058,GU991669,J0599140,GU589577, EF494435,JX486057, GU991659 |
| Mammalian orthoreovirus 3 | NC_004283 | vertebrates | 6 | Reoviridae,Orthoreovirus,Mammalian orthoreovirus | seg. S3 | JX486065,XQ1627,G U991667,GU991677, GU589585,EF494443 |
| Mammalian orthoreovirus 3 | NC_013225 | vertebrates | 1 | Reoviridae,Orthoreovirus,Mammalian orthoreovirus | seg. L1 | GQ468266 |
| Mammalian orthoreovirus 3 | NC_013226 | vertebrates | 1 | Reoviridae,Orthoreovirus,Mammalian orthoreovirus | seg. L2 | GQ468267 |
| Mammalian orthoreovirus 3 | NC_013227 | vertebrates | 1 | Reoviridae,Orthoreovirus,Mammalian orthoreovirus | seg. M1 | GQ468268 |
| Mammalian orthoreovirus 3 | NC_013228 | vertebrates | 8 | Reoviridae,Orthoreovirus,Mammalian orthoreovirus | seg. M2 | GU991663,GU58958 1,M20161,EF494439, GU991673,GQ46826 9,JX486061,U24260 |

| Taxonomy | NCBI Reference Sequence ID | Host | No. of Genomes | Lineage | Segment Count | Genbank Accession ID |
|---|---|---|---|---|---|---|
| Mammalian orthoreovirus 3 | NC_013229 | vertebrates | 1 | Reoviridae,Orthoreovirus,Mammalian orthoreovirus | seg. L3 | GQ468270 |
| Mammalian orthoreovirus 3 | NC_013230 | vertebrates | 7 | Reoviridae,Orthoreovirus,Mammalian orthoreovirus | seg. M3 | GU991664,AF174384,JX486062,EF494440,GU589582,GU991674,GQ468271 |
| Mammalian orthoreovirus 3 | NC_013231 | vertebrates | 1 | Reoviridae,Orthoreovirus,Mammalian orthoreovirus | seg. Si | GQ468272 |
| Mammalian orthoreovirus 3 | NC_013232 | vertebrates | 8 | Reoviridae,Orthoreovirus,Mammalian orthoreovirus | seg. S2 | GU589584,JX486064,GU991666,L19776,GU991676,EF494442,GQ468273,JQ2327 |
| Mammalian orthoreovirus 3 | NC_013233 | vertebrates | 1 | Reoviridae,Orthoreovirus,Mammalian orthoreovirus | seg. S3 | GQ468274 |
| Mammalian orthoreovirus 3 | NC_013234 | vertebrates | 12 | Reoviridae,Orthoreovirus,Mammalian orthoreovirus | seg. S4 | GU991678,DQ004471,DQ004472,DQ004473,GU589586,JX486066,GQ468275,DQ004470,DQ004474,EF494444,DQ004475,GU991668 |
| Mammalian orthoreovirus 3 | NC_004274 | vertebrates | 1 | Reoviridae,Orthoreovirus,Mammalian orthoreovirus Dearing orthoreovirus | seg. L3 | HM159615 |
| Mammalian orthoreovirus 3 | NC_004275 | vertebrates | 1 | Reoviridae,Orthoreovirus,Mammalian orthoreovirus Dearing orthoreovirus | seg. L2 | HM159614 |
| Mammalian orthoreovirus 3 | NC_004276 | vertebrates | 4 | Reoviridae,Orthoreovirus,Mammalian orthoreovirus Dearing orthoreovirus | seg. S4 | AF332135,HM159622,AF332136,AF332137 |
| Mammalian orthoreovirus 3 | NC_004277 | vertebrates | 1 | Reoviridae,Orthoreovirus,Mammalian orthoreovirus Dearing orthoreovirus | seg. 51 | HM159619 |
| Mammalian orthoreovirus 3 | NC_004278 | vertebrates | 1 | Reoviridae,Orthoreovirus,Mammalian orthoreovirus Dearing orthoreovirus | seg. M2 | HM159617 |
| Mammalian orthoreovirus 3 | NC_004279 | vertebrates | 1 | Reoviridae,Orthoreovirus,Mammalian orthoreovirus Dearing orthoreovirus | seg. S2 | HM159620 |
| Mammalian orthoreovirus 3 | NC_004280 | vertebrates | 1 | Reoviridae,Orthoreovirus,Mammalian orthoreovirus Dearing orthoreovirus | seg. M1 | HM159616 |
| Mammalian orthoreovirus 3 | NC_004281 | vertebrates | 1 | Reoviridae,Orthoreovirus,Mammalian orthoreovirus Dearing orthoreovirus | seg. M3 | HM159618 |
| Mammalian orthoreovirus 3 | NC_004282 | vertebrates | 1 | Reoviridae,Orthoreovirus,Mammalian orthoreovirus Dearing orthoreovirus | seg. L1 | HM159613 |
| Mammalian orthoreovirus 3 | NC_004283 | vertebrates | 1 | Reoviridae,Orthoreovirus,Mammalian orthoreovirus Dearing orthoreovirus | seg. S3 | HM159621 |
| Mammalian orthoreovirus 3 | NC_013228 | vertebrates | 1 | Reoviridae,Orthoreovirus,Mammalian orthoreovirus Dearing orthoreovirus | seg. M2 | HM159617 |
| Mammalian orthoreovirus 3 | NC_013230 | vertebrates | 1 | Reoviridae,Orthoreovirus,Mammalian orthoreovirus Dearing orthoreovirus | seg. M3 | HM159618 |
| Mammalian orthoreovirus 3 | NC_013232 | vertebrates | 1 | Reoviridae,Orthoreovirus,Mammalian orthoreovirus Dearing orthoreovirus | seg. S2 | HM159620 |

| Taxonomy | NCBI Reference Sequence ID | Host | No. of Genomes | Lineage | Segment Count | Genbank Accession ID |
|---|---|---|---|---|---|---|
| Mammalian orthoreovirus 3 | NC_013234 | vertebrates | 4 | Reoviridae,Orthoreovirus,Mammalian Dearing orthoreovirus | seg. S4 | AF332135,HM159622,AF332136,AF332137 |
| Mammalian orthoreovirus 4 Ndelle | NC_004276 | vertebrates | 1 | Reoviridae,Orthoreovirus,Mammalian orthoreovirus | seg. S4 | AF368037 |
| Mammalian orthoreovirus 4 Ndelle | NC_004277 | vertebrates | 1 | Reoviridae,Orthoreovirus,Mammalian orthoreovirus | seg. S1 | AF368035 |
| Mammalian orthoreovirus 4 Ndelle | NC_004278 | vertebrates | 1 | Reoviridae,Orthoreovirus,Mammalian orthoreovirus | seg. M2 | AF368034 |
| Mammalian orthoreovirus 4 Ndelle | NC_004279 | vertebrates | 1 | Reoviridae,Orthoreovirus,Mammalian orthoreovirus | seg. S2 | AF368036 |
| Mammalian orthoreovirus 4 Ndelle | NC_004282 | vertebrates | 1 | Reoviridae,Orthoreovirus,Mammalian orthoreovirus | seg. L1 | AF368033 |
| Mammalian orthoreovirus 4 Ndelle | NC_013228 | vertebrates | 1 | Reoviridae,Orthoreovirus,Mammalian orthoreovirus | seg. M2 | AF368034 |
| Mammalian orthoreovirus 4 Ndelle | NC_013232 | vertebrates | 1 | Reoviridae,Orthoreovirus,Mammalian orthoreovirus | seg. S2 | AF368036 |
| Mammalian orthoreovirus 4 Ndelle | NC_013234 | vertebrates | 1 | Reoviridae,Orthoreovirus,Mammalian orthoreovirus | seg. S4 | AF368037 |
| Marine birnavirus | NC_008019 | vertebrates | 5 | Birnaviridae,Aquabirnavirus,Marine birnavirus | seg. A | AY283785,AY064396,AY283781,AY283782,AY283784 |
| Marine birnavirus | NC_008026 | vertebrates | 3 | Birnaviridae,Aquabirnavirus,Marine birnavirus | seg. B | AY123970,AY129665,AY129666 |
| Marine birnavirus-H1 | NC_008019 | vertebrates | 1 | Birnaviridae,Aquabirnavirus,Marine birnavirus | seg. A | AY283783 |
| Mason-Pfizer monkey virus | NC_001550 | vertebrates | 2 | Retroviridae,Betaretrovirus,Mason-Pfizer monkey virus | — | AF033815,M12349 |
| Mastomys coucha papillomavirus 2 | NC_008519 | vertebrates | 1 | Papillomaviridae,Pipapillomavirus,Pipapillomavirus 1 | — | DQ664501 |
| Mastomys natalensis papillomavirus | NC_001605 | vertebrates | 1 | Papillomaviridae,Iotapapillomavirus,Iotapapillomavirus 1 | — | U01834 |
| Melaka orthoreovirus | NC_020439 | vertebrates | 1 | Reoviridae,Orthoreovirus,Melaka orthoreovirus | seg. L1 | F342660 |
| Melaka orthoreovirus | NC_020440 | vertebrates | 1 | Reoviridae,Orthoreovirus,Melaka orthoreovirus | seg. L3 | F342662 |
| Melaka orthoreovirus | NC_020441 | vertebrates | 1 | Reoviridae,Orthoreovirus,Melaka orthoreovirus | seg. M1 | F342663 |
| Melaka orthoreovirus | NC_020442 | vertebrates | 1 | Reoviridae,Orthoreovirus,Melaka orthoreovirus | seg. M2 | F342664 |
| Melaka orthoreovirus | NC_020443 | vertebrates | 1 | Reoviridae,Orthoreovirus,Melaka orthoreovirus | seg. M3 | F342665 |
| Melaka orthoreovirus | NC_020444 | vertebrates | 1 | Reoviridae,Orthoreovirus,Melaka orthoreovirus | seg. S2 | EF026044 |
| Melaka orthoreovirus | NC_020445 | vertebrates | 1 | Reoviridae,Orthoreovirus,Melaka orthoreovirus | seg. S3 | EF026045 |
| Melaka orthoreovirus | NC_020446 | vertebrates | 1 | Reoviridae,Orthoreovirus,Melaka orthoreovirus | seg. S4 | EF026046 |
| Melaka orthoreovirus | NC_020447 | vertebrates | 1 | Reoviridae,Orthoreovirus,Melaka orthoreovirus | seg. L2 | F342661 |

| Taxonomy | NCBI Reference Sequence ID | Host | Lineage | No. of Genomes | Segment Count | Genbank Accession ID |
|---|---|---|---|---|---|---|
| Melaka orthoreovirus | NC_020448 | vertebrates | Reoviridae,Orthoreovirus,Melaka orthoreovirus | 1 | seg. S1 | EF026043 |
| Meleagrid herpesvirus 1 | NC_002641 | vertebrates | Herpesviridae,Mardivirus,Meleagrid herpesvirus 1 | 2 | — | AF282130,AF291866 |
| Mengo virus | NC_001479 | vertebrates | Picornaviridae,Cardiovirus,Encephalomyocarditis virus | 2 | — | L22089, DQ294633 |
| Mesocricetus auratus papillomavirus 1 | NC_022647 | vertebrates | Papillomaviridae,Mesocricetus auratus papillomavirus 1 | 1 | — | HG530538 |
| Middle East respiratory syndrome coronavirus | NC_019843 | vertebrates | Coronaviridae,Betacoronavirus,Middle East respiratory syndrome coronavirus | 30 | — | KF600645,KF192507, KJ156944,KJ156952, KJ156869,KF600630, KF600652,KF600634, KJ156934,KF600620, KF600651,KF600644, KF600612,KF600627, KF600628,KF961221, KF961222,KF600613, KF186565,KF745068, KF186564,KF186566, KF600647,KF186567, KJ156910,KJ156874, KF600632,KJ156881, KJ156866,KJ156949 |
| Miniopterus bat coronavirus HKU8 | NC_010438 | vertebrates | Coronaviridae,Alphacoronavirus,Miniopterus bat coronavirus HKU8 | 1 | — | EU420139 |
| Miniopterus polyomavirus | NC_020069 | vertebrates | Polyomaviridae,Polyomavirus,Miniopterus polyomavirus | 1 | — | JX520661 |
| Mink astrovirus | NC_004579 | vertebrates | Astroviridae,Mamastrovirus,Mamastrovirus 10 | 1 | — | GU985458 |
| Mink calicivirus | NC_019712 | vertebrates | Caliciviridae,Vesivirus,Mink calicivirus | 1 | — | JX847605 |
| Minute virus of mice | NC_001510 | vertebrates | Parvoviridae,Parvovirus,Minute virus of mice | 3 | — | M12032,JQ2275,DQ196317 |
| Molluscum contagiosum virus subtype 1 | NC_001731 | vertebrates | Poxviridae,Molluscipoxvirus,Molluscum contagiosum virus | 1 | — | U60315 |
| Moloney murine leukemia virus | NC_001702,NC_0018 19,NC_0013 62,NC_001 501 | vertebrates | Retroviridae,Gammaretrovirus,Murine leukemia virus | 2 | — | AF462057,CS272315 |
| Moloney murine sarcoma virus | NC_001502 | vertebrates | Retroviridae,Gammaretrovirus,Moloney murine sarcoma virus | 4 | — | JQ2266,V01185,V01184,AF033813 |
| Monkey B-lymphotropic papovavirus | NC_004763 | vertebrates | Polyomaviridae,Polyomavirus,African green monkey polyomavirus | 1 | — | M30540 |
| Monkeypox virus | NC_003310 | vertebrates | Poxviridae,Orthopoxvirus,Monkeypox virus | 36 | — | JX878427,AY741551, JX878415,JX878410, JX878416,JX878422, DQ011156,JX878419, HQ857562,JX878840 7,JX878414,DQ0111 |

| Taxonomy | NCBI Reference Sequence ID | Host | No. of Genomes | Lineage | Segment Count | Genbank Accession ID |
|---|---|---|---|---|---|---|
| Monkeypox virus Zaire-96-1-16 | NC_003310 | vertebrates | 1 | Poxviridae,Orthopoxvirus,Monkeypox virus | — | 54,JX878408,JX878428,AY753185,DQ011155,JX878409,JX878420,JX878426,JX878417,JX878429,HM172544,JX878412,JX878423,DQ011157,JX878425,D

| Taxonomy | NCBI Reference Sequence ID | Host | Lineage | No. of Genomes | Segment Count | Genbank Accession ID |
|---|---|---|---|---|---|---|
| Murid herpesvirus 8 | NC_019559 | vertebrates | Herpesviridae,Muromegalovirus,Murid herpesvirus 8 | 1 | — | JX867617 |
| Murine adenovirus 2 | NC_014899 | vertebrates | Adenoviridae,Mastadenovirus,Murine adenovirus B | 1 | — | HM049560 |
| Murine adenovirus 3 | NC_012584 | vertebrates | Adenoviridae,Mastadenovirus,Murine adenovirus C | 1 | — | EU835513 |
| Murine adenovirus A | NC_000942 | vertebrates | Adenoviridae,Mastadenovirus,Murine adenovirus A | 1 | — | M22245 |
| Murine astrovirus | NC_018702 | vertebrates | Astroviridae,Murine astrovirus | 2 | — | JX544744,JX544743 |
| Murine coronavirus | NC_012936,NC_00184 | vertebrates | Coronaviridae, Betacoronavirus, Murine coronavirus | 6 | — | JX169866,KF268338, JX169867,KF268339, KF268337,KF268336,JX169867 |
| Murine coronavirus MHV-1 | NC_012936,NC_00184 6 | vertebrates | Coronaviridae,Betacoronavirus,Murine coronavirus | 1 | — | FJ647223 |
| Murine coronavirus MHV-3 | NC_012936,NC_00184 6 | vertebrates | Coronaviridae,Betacoronavirus,Murine coronavirus | 1 | — | FJ647224 |
| Murine coronavirus MHV-JHM.IA | NC_012936,NC_00184 6 | vertebrates | Coronaviridae,Betacoronavirus,Murine coronavirus | 1 | — | FJ647226 |
| Murine coronavirus RA59/R13 | NC_012936,NC_00184 6 | vertebrates | Coronaviridae,Betacoronavirus,Murine coronavirus | 1 | — | FJ647218 |
| Murine coronavirus RA59/SJHM | NC_012936,NC_00184 6 | vertebrates | Coronaviridae,Betacoronavirus,Murine coronavirus | 1 | — | FJ647220 |
| Murine coronavirus RJHM/A | NC_012936,NC_00184 6 | vertebrates | Coronaviridae,Betacoronavirus,Murine coronavirus | 1 | — | FJ647219 |
| Murine coronavirus SA59/RJHM | NC_012936,NC_00184 6 | vertebrates | Coronaviridae,Betacoronavirus,Murine coronavirus | 1 | — | FJ647222 |
| Murine coronavirus inf-MHV-A59 | NC_012936,NC_00184 6 | vertebrates | Coronaviridae,Betacoronavirus,Murine coronavirus | 1 | — | FJ647225 |
| Murine coronavirus repA59/RJHM | NC_012936,NC_00184 6 | vertebrates coronavirus | Coronaviridae,Betacoronavirus,Murine coronavirus | 1 | — | FJ647221 |
| Murine coronavirus repJHM/RA59 | NC_012936,NC_00184 6 | vertebrates | Coronaviridae,Betacoronavirus,Murine coronavirus | 1 | — | FJ647227 |
| Murine cytomegalovirus (strain K181) | NC_004065 | vertebrates | Herpesviridae,Muromegalovirus,Murid herpesvirus 1 | 1 | — | AM886412 |
| Murine hepatitis virus | NC_012936,NC_00184 6 | vertebrates | Coronaviridae,Betacoronavirus,Murine coronavirus | 5 | — | AY700211,AF208067, AB551247,AF208066, GU593319 |

| Taxonomy | NCBI Reference Sequence ID | Host | No. of Genomes | Lineage | Segment Count | Genbank Accession ID |
|---|---|---|---|---|---|---|
| Murine hepatitis virus strain 2 | NC_012936 NC_00184 6 | vertebrates | 1 | Coronaviridae,Betacoronavirus,Murine coronavirus | — | AF201929 |
| Murine hepatitis virus strain A59 | NC_012936 | vertebrates | 2 | Coronaviridae,Betacoronavirus,Murine coronavirus | — | FJ884686,FJ884687 |
| Murine hepatitis virus strain ML-11 | NC_00184 NC_012936 NC_00184 6 | vertebrates | 1 | Coronaviridae,Betacoronavirus,Murine coronavirus | — | AF207902 |
| Murine hepatitis virus strain S/3239-17 | NC_012936 ,NC_00184 6 | vertebrates | 1 | Coronaviridae,Betacoronavirus,Murine coronavirus | — | JQ173883 |
| Murine leukemia virus | NC_001702 ,NC_00181 9,NC_0013 62,NC_001 501 | vertebrates | 12 | Retroviridae,Gammaretrovirus,Murine leukemia virus | — | AB187566,Y13893,M 87550,DQ366149,AY 252102,AF019230,AB 187565,AY818896,AF 169256,K03363,U137 66,JQ2255 |
| Murine leukemia virus N417 | NC_001702 ,NC_001811 9,NC_0013 62,NC_001 501 | vertebrates | 1 | Retroviridae,Gammaretrovirus,Murine eukemia virus | — | HQ246218 |
| Murine norovirus | NC_008311 | vertebrates | 8 | Caliciviridae,Norovirus,Murine norovirus | — | EF531291,AB435514, AB435515,JXQ48594, DQ911368,EF531290 ,HQ317203,AB60176 9 |
| Murine norovirus 1 | NC_008311 | vertebrates | 13 | Caliciviridae,Norovirus,Murine norovirus | — | EU004660,EU004654 ,EF014462,EU00466 2,EU004661,EU0046 59,AY228235,EU004 656,EU004657,DQ28 5629,EU004655,EU0 04658,KC782764 |
| Murine norovirus 2 | NC_008311 | vertebrates | 1 | Caliciviridae,Norovirus,Murine norovirus | — | DQ223041 |
| Murine norovirus 3 | NC_008311 | vertebrates | 4 | Caliciviridae,Norovirus,Murine norovirus | — | KC792553,DQ223042 ,FJ446720,JQ653875 |
| Murine norovirus 4 | NC_008311 | vertebrates | 2 | Caliciviridae,Norovirus,Murine norovirus | — | DQ223043,FJ446719 |
| Murine norovirus GV/C R1/2005/USA | NC_008311 | vertebrates | 1 | Caliciviridae,Norovirus,Murine norovirus | — | EU004672 |
| Murine norovirus GV/CR10/2005/USA | NC_008311 | vertebrates | 1 | Caliciviridae,Norovirus,Murine norovirus | — | EU004678 |
| Murine norovirus GV/CR11/2005/USA | NC_008311 | vertebrates | 1 | Caliciviridae,Norovirus,Murine norovirus | — | EU004679 |
| Murine norovirus GV/CR13/2005/USA | NC_008311 | vertebrates | 1 | Caliciviridae,Norovirus,Murine norovirus | — | EU004680 |

| Taxonomy | NCBI Reference Sequence ID | Host | No. of Genomes | Lineage | Segment Count | Genbank Accession ID |
|---|---|---|---|---|---|---|
| Murine norovirus GV/CR15/2005/USA | NC_008311 | vertebrates | 1 | Caliciviridae,Norovirus,Murine norovirus | — | EU004681 |
| Murine norovirus GV/CR17/2005/USA | NC_008311 | vertebrates | 1 | Caliciviridae,Norovirus,Murine norovirus | — | EU004682 |
| Murine norovirus GV/CR18/2005/DEU | NC_008311 | vertebrates | 1 | Caliciviridae,Norovirus,Murine norovirus | — | EU004683 |
| Murine norovirus GV/CR3/2005/USA | NC_008311 | vertebrates | 1 | Caliciviridae,Norovirus,Murine norovirus | — | EU004673 |
| Murine norovirus GV/CR4/2005/USA | NC_008311 | vertebrates | 1 | Caliciviridae,Norovirus,Murine norovirus | — | EU004674 |
| Murine norovirus GV/CR5/2005/USA | NC_008311 | vertebrates | 1 | Caliciviridae,Norovirus,Murine norovirus | — | EU004675 |
| Murine norovirus GV/CR6/2005/USA | NC_008311 | vertebrates | 2 | Caliciviridae,Norovirus,Murine norovirus | — | EU004676,JQ237823 |
| Murine norovirus GV/CR7/2005/USA | NC_008311 | vertebrates | 1 | Caliciviridae,Norovirus,Murine norovirus | — | EU004677 |
| Murine norovirus GV/NIH-2409/2005/USA | NC_008311 | vertebrates | 1 | Caliciviridae,Norovirus,Murine norovirus | — | JF320644 |
| Murine norovirus GV/NIH-2410/2005/USA | NC_008311 | vertebrates | 1 | Caliciviridae,Norovirus,Murine norovirus | — | JF320645 |
| Murine norovirus GV/NIH-2411/2005/USA | NC_008311 | vertebrates | 1 | Caliciviridae,Norovirus,Murine norovirus | — | JF320646 |
| Murine norovirus GV/NIH-2747/2005/USA | NC_008311 | vertebrates | 1 | Caliciviridae,Norovirus,Murine norovirus | — | JF320647 |
| Murine norovirus GV/NIH-2750/2005/USA | NC_008311 | vertebrates | 1 | Caliciviridae,Norovirus,Murine norovirus | — | JF320648 |
| Murine norovirus GV/NIH-4421/2005/USA | NC_008311 | vertebrates | 1 | Caliciviridae,Norovirus,Murine norovirus | — | JF320649 |
| Murine norovirus GV/NIH-4428/2005/USA | NC_008311 | vertebrates | 1 | Caliciviridae,Norovirus,Murine norovirus | — | JF320650 |
| Murine norovirus GV/NIH-4431/2005/USA | NC_008311 | vertebrates | 1 | Caliciviridae,Norovirus,Murine norovirus | — | JF320651 |
| Murine norovirus GV/NIH-A114/2006/USA | NC_008311 | vertebrates | 1 | Caliciviridae,Norovirus,Murine norovirus | — | JF320652 |
| Murine norovirus GV/NIH-D220/2007/USA | NC_008311 | vertebrates | 1 | Caliciviridae,Norovirus,Murine norovirus | — | JF320653 |
| Murine norovirus GV/W U11/2005/U SA | NC_008311 | vertebrates | 1 | Caliciviridae,Norovirus,Murine norovirus | — | EU004663 |
| Murine norovirus GV/WU12/2005/USA | NC_008311 | vertebrates | 1 | Caliciviridae,Norovirus,Murine norovirus | — | EU004664 |
| Murine norovirus GV/WU20/2005/USA | NC_008311 | vertebrates | 1 | Caliciviridae,Norovirus,Murine norovirus | — | EU004665 |
| Murine norovirus GV/WU21/2005/USA | NC_008311 | vertebrates | 1 | Caliciviridae,Norovirus,Murine norovirus | — | EU004666 |
| Murine norovirus GV/WU22/2005/USA | NC_008311 | vertebrates | 1 | Caliciviridae,Norovirus,Murine norovirus | — | EU004667 |
| Murine norovirus GV/WU23/2005/USA | NC_008311 | vertebrates | 1 | Caliciviridae,Norovirus,Murine norovirus | — | EU004668 |

| Taxonomy | NCBI Reference Sequence ID | Host | No. of Genomes | Lineage | Segment Count | Genbank Accession ID |
|---|---|---|---|---|---|---|
| Murine norovirus GV/WU24/2005/USA | NC_008311 | vertebrates | 1 | Caliciviridae,Norovirus,Murine norovirus | — | EU004669 |
| Murine norovirus GV/WU25/2005/USA | NC_008311 | vertebrates | 1 | Caliciviridae,Norovirus,Murine norovirus | — | EU004670 |
| Murine norovirus GV/WU26/2005/USA | NC_008311 | vertebrates | 1 | Caliciviridae,Norovirus,Murine norovirus | — | EU004671 |
| Murine osteosarcoma virus | NC_001506 | vertebrates | 1 | Retroviridae,Gammaretrovirus,Murine osteosarcoma virus | — | AF033814 |
| Murine pneumotropic virus | NC_001505 | vertebrates | 2 | Polyomaviridae,Polyomavirus,Murine pneumotropic virus | — | M55904, EF186666 |
| Murine polyomavirus | NC_001515 | vertebrates | 3 | Polyomaviridae,Polyomavirus,Murine polyomavirus | — | U27812,U27813,JQ22 |
| Murine polyomavirus strain A3 | NC_001515 | vertebrates | 1 | Polyomaviridae,Polyomavirus,Murine polyomavirus | — | JQ2289 |
| Murine polyomavirus strain BG | NC_001515 | vertebrates | 1 | Polyomaviridae,Polyomavirus,Murine polyomavirus | — | AF442959 |
| Murine type C retrovirus | NC_001702,NC_00181 9,NC_0013 62,NC_001 501 | vertebrates | 1 | Retroviridae,Gammaretrovirus,Murine leukemia virus | — | X94150 |
| Muromegalovirus C4A | NC_004065 | vertebrates | 1 | Herpesviridae,Muromegalovirus,Murid herpesvirus 1 | — | EU579861 |
| Muromegalovirus G4 | NC_004065 | vertebrates | 1 | Herpesviridae,Muromegalovirus,Murid herpesvirus 1 | — | EU579859 |
| Muromegalovirus WP15B | NC_004065 | vertebrates | 1 | Herpesviridae,Muromegalovirus,Murid herpesvirus 1 | — | EU579860 |
| Mus dunniendogenous virus | NC_001702,NC_00181 9,NC_0013 62,NC_001 501 | vertebrates | 1 | Retroviridae,Gammaretrovirus,Murine leukemia virus | — | AF053745 |
| Muscovy duck circovirus | NC_005053 ,NC_00722 0,NC_0065 61 | vertebrates | 17 | Circoviridae,Circovirus,Duck circovirus | — | GQ423743,GQ86875 7,GQ423746,HQ1802 65,GU 168779,EF370 476,DQ166836,DQ16 6838,GQ423742,DQ1 66837,GQ423744,GQ 334371,FJ554673,G 0423741,EF451157,J X499186,GQ423745 KC171936,X75093,U |
| Muscovy duck parvovirus 22967 | NC_006147 | vertebrates | 3 | Parvoviridae,Dependovirus,Duck parvovirus | — | KC508647,KF306082 |
| Muscovy duck reovirus | NC_015126 | vertebrates | 3 | Reoviridae,Orthoreovirus,Avian orthoreovirus | seg. L1 | JX478260 |
| Muscovy duck reovirus | NC_015127 | vertebrates | 3 | Reoviridae,Orthoreovirus,Avian orthoreovirus | seg. L2 | KC508648,JX478261, KF306083 |

| Taxonomy | NCBI Reference Sequence ID | Host | No. of Genomes | Lineage | Segment Count | Genbank Accession ID |
|---|---|---|---|---|---|---|
| Muscovy duck reovirus | NC_015128 | vertebrates | 3 | Reoviridae,Orthoreovirus,Avian orthoreovirus | seg. L3 | KC508649,JX478262, KF306084 |
| Muscovy duck reovirus | NC_015129 | vertebrates | 3 | Reoviridae,Orthoreovirus,Avian orthoreovirus | seg. M1 | KC508650,KF306085 ,JX478263 |
| Muscovy duck reovirus | NC_015130 | vertebrates | 4 | Reoviridae,Orthoreovirus,Avian orthoreovirus | seg. M2 | KF306086,KC756359 ,KC508651,JX478264 |
| Muscovy duck reovirus | NC_015131 | vertebrates | 3 | Reoviridae,Orthoreovirus,Avian orthoreovirus | seg. M3 | KC508652,JX478265, KF306087 |
| Muscovy duck reovirus | NC_015132 | vertebrates | 4 | Reoviridae,Orthoreovirus,Avian orthoreovirus | seg. S1 | DQ198854,KC508653 ,KF306088,DQ191363 |
| Muscovy duck reovirus | NC_015133 | vertebrates | 4 | Reoviridae,Orthoreovirus,Avian orthoreovirus | seg. S2 | DQ198857,KC508654 ,KF306089,JX478267 |
| Muscovy duck reovirus | NC_015134 | vertebrates | 3 | Reoviridae,Orthoreovirus,Avian orthoreovirus | seg. S3 | KC508655,JX478268, KF306090 |
| Muscovy duck reovirus | NC_015135 | vertebrates | 2 | Reoviridae,Orthoreovirus,Avian orthoreovirus | seg. S4 | KF306091,JX478269 |
| Muscovy duck reovirus 89330 | NC_015131 | vertebrates | 1 | Reoviridae,Orthoreovirus,Avian orthoreovirus | seg. M3 | AJ293969 |
| Muscovy duck reovirus S14 | NC_015130 | vertebrates | 1 | Reoviridae,Orthoreovirus,Avian orthoreovirus | seg. M2 | DQ989557 |
| Myotis polyomavirus VM-2008 | NC_011310 | vertebrates | 1 | Polyomaviridae,Polyomavirus,Bat polyomavirus | — | FJ188392 |
| Myxoma virus | NC_001132 | vertebrates | 34 | Poxviridae,Leporipoxvirus,Myxoma virus | — | JX565567,EU552530, JX565566,JX565573, KC660080,KC660082 ,JX565565,JX565574, JX565568,JX565580, JX565564,JX565569, KC660083,KC660079 ,KC660084,AF170726,KC660081,JX565557 1,JX565570,JX565557 2,KF148065,JX565558 JX565579,GQ4099 69,JX565575,JX5655 78,JX565563,KC6600 85,JX565584,JX5655 77,JX565583,JX5655 62,JX565581,JX5655 76 |
| Night-heron coronavirus HKU19 | NC_016994 | vertebrates | 1 | Coronaviridae, Deltacoronavirus, Night-heron coronavirus H KU19 | — | JQ065047 |
| Nile crocodilepox virus | NC_008030 | vertebrates | 1 | Poxviridae,Crocodylidpoxvirus,Nile crocodilepox virus | — | DQ356948 |
| Old World harvest mouse papillomavirus 6 | NC_008582 ,NC_01432 | vertebrates | 1 | Papillomaviridae,Pipapillomavirus,Pipapilloma virus 2 | — | DQ269468 |

| Taxonomy | NCBI Reference Sequence ID | Host | No. of Genomes | Lineage | Segment Count | Genbank Accession ID |
|---|---|---|---|---|---|---|
| Orange-spotted grouper iridovirus | NC_003494 | vertebrates | 1 | Iridoviridae,Megalocytivirus,Infectious spleen and kidney necrosis virus | — | AY894343 |
| Orangutan polyomavirus | NC_013439 | vertebrates | 2 | Polyomaviridae,Polyomavirus,Orangutan polyomavirus | — | FN356900,FN356901 |
| Orf virus | NC_005336 | vertebrates | 4 | Poxviridae,Parapoxvirus,Orf virus | — | DQ184476,AY386263,HM133903,AY386264 |
| Otomops polyomavirus 1 | NC_020071 | vertebrates | 1 | Polyomaviridae,Polyomavirus,Otomops polyomavirus 1 | — | JX520664 |
| Otomops polyomavirus 2 | NC_020066 | vertebrates | 1 | Polyomaviridae,Polyomavirus,Otomops polyomavirus 2 | — | JX520658 |
| Ovine adenovirus A | NC_002513 | vertebrates | 1 | Adenoviridae,Mastadenovirus,Ovine adenovirus | — | AF252854 |
| Ovine adenovirus D | NC_004037 | vertebrates | 1 | Adenoviridae,Atadenovirus,Ovine adenovirus D | — | U40839 |
| Ovine enterovirus | NC_004441 | vertebrates | 1 | Picornaviridae,Enterovirus,Enterovirus G | — | JQ277724 |
| Ovine enzootic nasal tumor virus | NC_007015 | vertebrates | 6 | Retroviridae,Betaretrovirus,Ovine enzootic nasal tumor virus | — | GU292317,GU292315,KC189895,GU292314,GU292318,GU292316 |
| Ovine enzootic nasal tumour virus | NC_007015 | vertebrates | 1 | Retroviridae,Betaretrovirus,Ovine enzootic nasal tumor virus | — | Y16627 |
| Ovine herpesvirus 2 | NC_007646 | vertebrates | 2 | Herpesviridae,Macavirus,Ovine herpesvirus 2 | — | AY839756,DQ198083 |
| Ovine lentivirus | NC_001511 | vertebrates | 3 | Retroviridae,Lentivirus,Ovine lentivirus | — | AF479638,M31646,M34193 |
| Ovine papillomavirus-1 | NC_001789 | vertebrates | 1 | Papillomaviridae,Deltapapillomavirus,Deltapapillomavirus 3 | — | U83594 |
| Ovine papillomavirus type 2 | NC_001789 | vertebrates | 1 | Papillomaviridae,Deltapapillomavirus,Deltapapillomavirus 3 | — | U83595 |
| PRCV ISU-1 | NC_002306 | vertebrates | 1 | Coronaviridae,Alphacoronavirus,Alphacoronavirus 1 | — | DQ811787 |
| PRRSV HB-1(sh)2002 | NC_001961 | vertebrates | 1 | Arteriviridae,Arterivirus,Porcine reproductive and respiratory syndrome virus | — | AY150312 |
| PRRSV HB-2(sh)2002 | NC_001961 | vertebrates | 1 | Arteriviridae,Arterivirus,Porcine reproductive and respiratory syndrome virus | — | AY262352 |
| PRRSV HN1 | NC_001961 | vertebrates | 1 | Arteriviridae,Arterivirus,Porcine reproductive and respiratory syndrome virus | — | AY457635 |
| PRRSV LV4.2.1 | NC_001961 | vertebrates | 1 | Arteriviridae,Arterivirus,Porcine reproductive and respiratory syndrome virus | — | AY588319 |
| Pan troglodytes schweinfurthi i polyomavirus 2 | NC_019858 | vertebrates | 1 | Polyomaviridae,Polyomavirus,Pan troglodytes schweinfurthii polyomavirus 2 | — | JX159983 |
| Pan troglodytes verus polyomavirus 3 | NC_019855 | vertebrates | 1 | Polyomaviridae,Polyomavirus,Pan troglodytes verus polyomavirus 3 | — | JX159980 |
| Pan troglodytes verus polyomavirus 4 | NC_019856 | vertebrates | 1 | Polyomaviridae,Polyomavirus,Pan troglodytes verus polyomavirus 4 | — | JX159981 |
| Pan troglodytes verus polyomavirus 5 | NC_019857 | vertebrates | 1 | Polyomaviridae,Polyomavirus,Pan troglodytes verus polyomavirus 5 | — | JX159982 |

| Taxonomy | NCBI Reference Sequence ID | Host | No. of Genomes | Lineage | Segment Count | Genbank Accession ID |
|---|---|---|---|---|---|---|
| Panine herpesvirus 2 | NC_003521 | vertebrates | 1 | Herpesviridae,Cytomegalovirus,Panine herpesvirus 2 | — | AF480884 |
| Panthera leo persica papillomavirus type 1 | NC_004765 | vertebrates | 1 | Papillomaviridae,Lambdapapillomavirus,Lambdapapillomavirus 1 | — | AY904724 |
| Papiine herpesvirus 2 | NC_007653 | vertebrates | 1 | Herpesviridae,Simplexvirus,Papiine herpesvirus 2 | — | DQ149153 |
| Papio hamadryas papillomavirus type 1 | NC_017716 | vertebrates | 1 | Papillomaviridae,Papio hamadryas papillomavirus type 1 | — | JF304764 |
| Paralichthys olivaceus birnavirus | NC_009923 | vertebrates | 1 | Birnaviridae,Aquabirnavirus,Paralichthys olivaceus birnavirus | seg. A | EU161285 |
| Paralichthys olivaceus birnavirus | NC_009924 | vertebrates | 1 | Birnaviridae,Aquabirnavirus,Paralichthys olivaceus birnavirus | seg. B | EU161286 |
| Parrot hepatitis B virus | NC_016561 | vertebrates | 19 | Hepadnaviridae,Avihepadnavirus,Parrot hepatitis B virus | — | JX274035,JX274023, JX274021,JX274029, JX274030,JX274019, JN565944,JX274032, JX274034,JX274033, JX274027,JX274026, JX274018,JX274024, JX274020,JX274022, JX274031,JX274028, JX274025 |
| Parvo-like hybrid virus UC1 | NC_022089 | vertebrates | 1 | Parvoviridae, Parvovirus NIH-CQV | — | KF170373 |
| Parvo-like hybrid virus UC11 | NC_022089 | vertebrates | 1 | Parvoviridae,Parvovirus NIH-COV | — | KF214638 |
| Parvo-like hybrid virus UC4 | NC_022089 | vertebrates | 1 | Parvoviridae,Parvovirus NIH-COV | — | KF214645 |
| Parvo-like hybrid virus UC9 | NC_022089 | vertebrates | 1 | Parvoviridae, Parvovirus NIH-COV | — | KF214640 |
| Parvovirus NIH-COV | NC_022089 | vertebrates | 1 | Parvoviridae, Parvovirus NIH-COV | — | KC617868 |
| Pegivirus A | NC_001837 | vertebrates | 1 | Flaviviridae,Pegivirus,Pegivirus A | — | U94421 |
| Penaeus monodon circovirus VN11 | NC_022897 | vertebrates | 1 | Circoviridae,Circovirus,Penaeus monodon circovirus VN11 | — | KF481961 |
| Penaeus monodon hepatopancreatic parvovirus | NC_011545 | vertebrates | 1 | Parvoviridae,Parvovirus,Penaeus monodon hepatopancreatic parvovirus | — | FJ410797 |
| Perch rhabdovirus | NC_020803 | vertebrates | 1 | Rhabdoviridae,Perhabdovirus,Perch rhabdovirus | — | JX679246 |
| Pestivirus Giraffe-1 | NC_003678 | vertebrates | 1 | Flaviviridae,Pestivirus,Pestivirus Giraffe-1 | — | AF144617 |
| Pestivirus reindeer-1 V60-Krefeld | NC_003679 | vertebrates | 1 | Flaviviridae,Pestivirus,Border disease virus | — | AF144618 |
| Pestivirus strain Aydin/04-TR | NC_018713 | vertebrates | 1 | Flaviviridae,Pestivirus,Pestivirus strain Aydin/04-TR | — | JX428945 |
| Phocoena phocoena papillomavirus 1 | NC_018074 | vertebrates | 1 | Papillomaviridae,Phocoena phocoena papillomavirus 1 | — | GU117621 |
| Phocoena phocoena papillomavirus 2 | NC_018075 | vertebrates | 1 | Papillomaviridae,Phocoena phocoena papillomavirus 2 | — | GU117622 |
| Phocoena phocoena papillomavirus 4 | NC_018076 | vertebrates | 1 | Papillomaviridae,Phocoena phocoena papillomavirus 4 | — | GU117623 |

| Taxonomy | NCBI Reference Sequence ID | Host | No. of Genomes | Lineage | Segment Count | Genbank Accession ID |
|---|---|---|---|---|---|---|
| Phocoena spinipinnis papillomavirus 1 | NC_003348 | vertebrates | 1 | Papillomaviridae,Omikronpapillomavirus,Omikronpapillomavirus 1 | — | AJ238373 |
| Pigeon picornavirus B | NC_015626 | vertebrates | 2 | Picornaviridae, Pigeon picornavirus B | — | KC560801,FR727144 |
| Piliocolobus rufomitratus polyomavirus 1 | NC_019850 | vertebrates | 1 | Polyomaviridae,Polyomavirus,Piliocolobus rufomitratus polyomavirus 1 | — | JX159984 |
| Pipistrellus bat coronavirus HKU5 | NC_009020 | vertebrates | 1 | Coronaviridae,Betacoronavirus,Pipistrellus bat coronavirus HKU5 | — | EF065509 |
| Polyomavirus HPyV6 | NC_014406 | vertebrates | 6 | Polyomaviridae,Polyomavirus,Polyomavirus HPyV6 | — | HM011559,HM011558,HM011560,HM011562,HM011561,HM011563 |
| Polyomavirus HPyV7 | NC_014407 | vertebrates | 6 | Polyomaviridae,Polyomavirus,Polyomavirus HPyV7 | — | HM011566,HM011568,HM011565,HM011569,HM011564,HM011567 |
| Porcine adenovirus C | NC_002702 | vertebrates | 1 | Adenoviridae, Mastadenovirus, Porcine adenovirus C | — | AF289262 |
| Porcine astrovirus 3 | NC_019494 | vertebrates | 1 | Astroviridae,Mamastrovirus,Porcine astrovirus 3 | — | JX556691 |
| Porcine bocavirus 3 | NC_016031 | vertebrates | 4 | Parvoviridae,Bocavirus,Porcine bocavirus 3 | — | JF713715,JF429834,JF713714,KC473563 |
| Porcine bocavirus 3C | NC_016031 | vertebrates | 1 | Parvoviridae,Bocavirus,Porcine bocavirus 3 | — | JN681175 |
| Porcine bocavirus 4-1 | NC_016032 | vertebrates | 1 | Parvoviridae,Bocavirus,Porcine bocavirus 4 | — | JF429835 |
| Porcine bocavirus 4-2 | NC_016032 | vertebrates | 1 | Parvoviridae,Bocavirus,Porcine bocavirus 4 | — | JF429836 |
| Porcine bocavirus 5/JS677 | NC_016647 | vertebrates | 1 | Parvoviridae,Bocavirus,Porcine bocavirus 5/JS677 | — | JN831651 |
| Porcine circovirus 1/2a | NC_013774 | vertebrates | 2 | Circoviridae,Circovirus,Porcine circovirus type 1 | — | FJ79425,FJ655419 |
| Porcine circovirus 1 | NC_001792 | vertebrates | 51 | Circoviridae,Circovirus,Porcine circovirus 1 | — | DQ472013,DQ472012,FJ475129,GU79957 5,AY099501,DQ472014,AF012107,KC924 758,FJ159689,JX566507,EF533941,DQ47 2016,DQ659153,GU371908,DQ659154,AY 754012,DQ494787,JN398656,KC878437,J N133302,AY660574,KC527543,AY699796 ,DQ650650,FJ159693,KC733436,FJ159690 ,Y09921,AY184287,KC990120,AY193712, DQ472015,AY754013,AF071879,GU72233 4,FJ159692,EF49384 3,KC89493,KC4474 |

| Taxonomy | NCBI Reference Sequence ID | Host | No. of Genomes | Lineage | Segment Count | Genbank Accession ID |
|---|---|---|---|---|---|---|
| | | | | | | 55,KF732857,AY2198 36,DQ358813,FJ1596 91,JN133303,DQ648 032,AY754015,GQ44 9671,U49186,AY7540 14,HM143844,DQ494 788 |
| Porcine circovirus 2 | NC_005148 | vertebrates | 1115 | Circoviridae,Circovirus,Porcine circovirus 2 | — | JX912914,KC800642, FJ660970,EF524519, DQ910865,KC800640 ,JX948775,FJ870971, FJ948167,EU148504, EF452350,JX982222, FJ905468,EF524528, HQ831529,HM00010 0,EF524517,EF56534 7,AY484409,AY0994 96,EU450590,EF565 343,AY682996,HM00 9338,HQ738639,EF4 21969,DQ220736,JQ 390467,DQ861899,JF 690914,KF850458,G U370064,HQ148879, HM009337,DQ20164 0,AY256459,EF56535 9,KF850460,FJ87096 7,KF027494,JQ80946 3,FJ667585,AF26404 1,KF742549,KC8006 35,EU136718,FJ4263 98,EU274311,AY424 402,JX512853,KF850 466,AY682992,JQ181 586,DQ915586,FJ447 482,HQ202966,EU14 8507,FJ667589,EF67 5238,EU747085,JF69 0911,FN687850,EF42 1970,EF524542,AY59 6823,HM038025,AY3 21986,KC821781,AY 484413,EU521707,FJ 608542,FJ388889,GU 325770,KC688418,H 0395027,JF317567,H M776445,HQ395040, HM038027,HM77644 |

| Taxonomy | NCBI Reference Sequence ID | Host | No. of Genomes | Lineage | Segment Count | Genbank Accession ID |
|---|---|---|---|---|---|---|
| | | | | | 8 | KF850464,KF74254 8,HM038029,FJ5944 71,JF827599,HQ2029 47,AY847748,AY035 820,AY510375,AB07 2301,KC823058,AY1 22275,AY325495,FJ6 60968,GU370063,JX 982227,FJ233905,DQ 195679,AF118095,H 020952,HQ591372, EU727546,JN133304, FJ667588,HQ395030, FJ660971,GU083583, HM776446,KC75376 9,HQ395042,DQ8619 01,HQ395025,GU247 991,JX982221,EF675 240,EF565342,DQ86 1895,HQ831539,EF9 89713,KF732649,HQ 202964,EU547460,A Y556473,AY686765,F J608544,EU521709,H 0395046,EF675229, EU909686,EU450584 ,HQ831530,AF16652 8,HM161711,HQ5913 73,AY188355,AY641 542,GU450330,EF56 5349,EF675233,JF31 7572,JQ956679,FJ21 8002,EF565366,JX94 8779,FN688741,AF40 8635,HQ831535,HQ3 95031,FJ660847,DQ2 20739,JF290418,GUO 49340,GU325762,HM 003569,GQ449670,D 0201639,AF055391, EU503034,AY874168 ,EF524541,HM14289 6,JX512855,FJ66096 7,FJ712215,KC53381 2,FJ667582,EF39477 6,JQ181602,EU1367 19,DQ910866,HQ395 022,KC800638,EU54 |

| Taxonomy | NCBI Reference Sequence ID | Host | No. of Genomes | Lineage | Segment Count | Genbank Accession ID |
|---|---|---|---|---|---|---|
| | | | | | | 5542,AY099500,EU547456,EF565365,EU656143,KF871067,JF317579,EU257516,KC823059,EU257515,EU780074,HQ395019,HQ831534,HQ395023,EF421972,GQ359005,KF742546,JN119251,FJ667592,KC859451,EF524520,JX512860,FJ905461,JF317565,JQ181594,JF682792,GU325766,JX512859,FJ644930,GU450328,HQ395054,HQ831522,FJ158602,AY321997,JX193799,KC800637,HQ378158,EF452352,HQ591370,DQ629118,JX506730,GU325764,EU594440,HM038020,JX948773,HQ591367,KF374705,JX406420,HM641752,EU386606,HQ395037,EU545550,HQ202955,DQ104419,HM776437,JX128857,EF565355,KF850468,AY484412,HQ831521,GU083582,JF272497,HQ395028,GQ358994,EF421973,AF364094,HM102350,EF592576,DQ220729,JX948784,FJ644558,HQ378159,EF394774,FN687857,HM003570,FR823451,EU136711,EF565363,FJ667586,KF850465,AY682990,HM038028,EU148503,EF565350,EF452353,AF264038,EF524530,GQ358992,AY291318,AY682995,EF565344,AY943819,HQ113118,A |

| Taxonomy | NCBI Reference Sequence ID | Host | No. of Genomes | Lineage | Segment Count | Genbank Accession ID |
|---|---|---|---|---|---|---|
| | | | | | | Y536756,EF565364, DQ997816,JF690921, HQ395051,EU909688 ,EF524527,JX406425 ,FN687842,JQ181601 ,HQ202973,HM03801 9,KF695388,FN68785 5,EU391637,EU1367 14,EF524535,JN6398 57,HQ202961,FJ6445 61,JX945575,KC8217 84,EF565351,AB0723 03,HQ202950,AF154 679,AY291316,KF850 467,HM161710,JX94 8770,GQ358999,AY7 13470,KF027497,EF5 24515,JQ809462,AF2 01307,KF742553,GQ 404853,AF520783,AY 484416,JX948771,D 0180392,FJ716704,E F524540,HQ591381, GU808525,HQ59137 9,KF742547,HQ2029 44,FJ905460,JQ1816 05,JX99780,KC7537 71,EF210106,EU545 546,FN398025,EF458 306,EU136715,HQ20 2948,HQ395045,KC8 00643,AY321993,AF3 81177,AY686763,KC 823055,HQ113119,A F264040,AY849938, HQ395026,JQ181593 ,GQ358996,AY39172 9,AY916791,GU3257 67,EU594438,HQ591 366,FJ644562,JF690 923,AY424401,EF524 523,AF201309,FJ660 969,HM038018,KC47 3167,JXQ99781,FJ87 0973,EU503036,DQ3 63860,HQ591380,HQ 591376,EF565356,JX 982223,FN398027,H |

| Taxonomy | NCBI Reference Sequence ID | Host | No. of Genomes | Lineage | Segment Count | Genbank Accession ID |
|---|---|---|---|---|---|---|
| | | | | | | M776439,EU503031, HM038026,GQ35900 9,FJ667593,AY75402 1,KC153106,JX40641 9,HM776447,FJ9054 71,JF690915,JQ1815 87,EF421968,HM038 032,KF742242,HQ83 1519,HQ395041,HQ3 95043,FJ598044,DQ9 15583,FJQ41151,EU1 48505,KC821783,JF6 90920,DQ220738,HM 038024,JF317566,AY 682994,AF381176,KF 926650,JF317571,DQ 629119,HQ831531,JF 690922,JQ002671,E U50303,FJ667584,K C533811,FJ608538,H 0202957,FJ608539,E U450587,DQ870484, JF682794,JF272499, AY874166,JF317581, GQ359006,HQ39506 0,FJ644923,FJ60854 6,GU325753,JX9487 72,AY256458,EF5653 61,EU545548,GQ359 004,HQ378161,FJ158 603,HQ395039,HQ39 5048,JX948783,KF02 7493,EF565358,AY60 4430,AM086384,AY3 21988,FJ48393B,KC7 88504,HM038022,GU 244507,FJ644926,EF 52453l,DQ233257,J 0994268,DQ220732, EF493840,FJ644919, EU921257,JF317577, GU325765,DQ14132 2,DQ478947,AY1469 92,DQ629116,HM623 764,EF524516,KC83 5193,AY099499,EU3 40258,JQ181592,AY3 21999,GQ359007,KC |

| Taxonomy | NCBI Reference Sequence ID | Host | No. of Genomes | Lineage | Segment Count | Genbank Accession ID |
|---|---|---|---|---|---|---|
| | | | | | | 447454,EU921255,FJ644931,HQ202953,EF565345,EU647557,HQ395038,JF928003,HM142895,HM142897,JF682791,HQ202958,JF690912,EU366324,DQ923524,KF850461,DQ220733,FJ905466,AY146991,EU503037,FN687844,FJ644928,EF675235,JXQ99785,FJ712216,DQ206444,FJ644920,EF565362,HQ395032,AY536755,AB426905,HQ402903,AF085695,HQ591368,FJ644925,HQ831524,JF928006,JX948780,AY256457,D0997815,JN639856,DQ915587,DQ64803,1,KF850469,HQ831520,HQ831526,HM038030,EF524529,HQ395029,EU366323,AY146993,FJ158607,FN398022,EU302141,EU418626,IQ181597,AY321985,HQ395036,AY754019,JF272498,AF147751,DQ017036,FJ667594,HQ202965,AY754017,HQ591378,JX948768,FJ501957,KC753770,GU325758,AF264039,AY288134,GQ359008,AY68299,1,HQ202945,KF0274,92,FJ608548,JF682793,EU547458,AY094619,HQ395021,JX982226,HQ395056,AF264043,HM038016,EF675239,EU886637,FJ905469,HQ395052,AY874164,DQ220730,AY484407,FN398023 |

| Taxonomy | NCBI Reference Sequence ID | Host | No. of Genomes | Lineage | Segment Count | Genbank Accession ID |
|---|---|---|---|---|---|---|
| | | | | | | ,AY322002,GU32575 6,EU274310,HM0380 31,KF742551,AY6997 93,AY322000,GU049 341,HQ395020,AY18 0397,HM776452,GU2 52370,JF690919,GU2 33804,HQ395035,AY 484411,HF542107,G U001710,KF027495, HQ831527,FJ905464, AY556475,EU545549 ,JF928004,EF394777 ,EF675242,FJ598045 ,AF538325,KC80064 6,AF465211,JQ18159 8,EF515839,JQ18160 4,EU503038,JX94877 6,AJ293868,JX98222 5,EU366325,DQ8618 96,HQ202954,AY874 165,DQ923523,AY25 6456,EF565352,AY32 2003,KC835192,JQ9 94270,EU450585,AY 291317,FN687845,JX 53237,EF524532,G 0449672,GU938303, EF394779,DQ915588 ,EU257513,JF317585 ,AY488415,HQ39504 9,FJ644555,HQ20296 8,HM776443,JX9455 77,AY682993,AY556 474,AY217743,JF317 586,AY256455,GQ35 8995,JF317582,AY29 4310,AY613854,FN6 87846,JQ692110,FJ6 44924,KC860786,AJ2 23185,KC800645,HQ 395058,JQ413808,AF 201306,DQ629117,H 0831523,FJ870975,K C336418,JQ002672, AY321984,EU257514 ,EU340257,EF52453 7,FJ870968,EU52170 |

| Taxonomy | NCBI Reference Sequence ID | Host | -continued<br>No. of Genomes | Lineage | Segment Count | Genbank Accession ID |
|---|---|---|---|---|---|---|
| | | | | | | 8,KC835194,EU2743<br>9,KC821782,FJ6445<br>57,JN615187,GQ359<br>010,KC800639,HM03<br>8033,KC684978,FN6<br>87843,FJ667587,JX9<br>48786,DQ180393,HQ<br>202956,HM038023,D<br>0104422,AB072302,J<br>0181591,FJ870976,A<br>Y651850,EF524538,<br>DQ915584,AY556477<br>,FN687854,AY69167<br>9,DQ201642,EF5653<br>67,FJ644921,FJ4403<br>38,HQ202960,EF394<br>778,EU545545,EU30<br>2139,AY874167,DQ8<br>61900,AY099498,AF0<br>55393,KF742541,KC<br>788505,EU136713,H<br>020962,FJ667583,A<br>Y754022,AY732494,<br>GU247989,KC907703<br>,EF394775,HQ59137<br>4,FJ644932,EF56535<br>3,EU545543,JX29471<br>7,EU274312,AY1776<br>26,JQ181606,EU547<br>457,EF524533,GU93<br>8304,HQ395061,FJ187<br>0972,AY099497,EF67<br>5236,GU325763,HQ2<br>02959,EU148506,JF9<br>28005,EU302140,EU<br>418627,AY754018,EF<br>675244,HQ202946,H<br>0831540,EF421971,J<br>N660055,AY678532,<br>HQ591369,HM77645<br>3,AY181947,JQ18160<br>3,EU503035,FJ90546<br>7,DQ346683,AY2881<br>33,DQ104421,KF742<br>552,JF317570,JX948<br>777,EF493839,JX982<br>224,KC823054,JX982<br>219,JF718784,HQ395 |

| Taxonomy | NCBI Reference Sequence ID | Host | No. of Genomes | Lineage | Segment Count | Genbank Accession ID |
|---|---|---|---|---|---|---|
| | | | | | | 057,GU001709,FJ667596,AY321982,JX945576,EF565357,EF524534,HQ113120,HQ395034,HQ831525,FN687856,GQ174519,EF524526,AY321991,H0831536,JF317569,JN388690,JF317574,D0355153,FJ667591,HM776438,GQ359002,HQ202970,JQ181590,AF201308,AY969004,HQ113117,HM776450,KF742540,HQ202967,JF493838,JX535297,JF317575,AF381175,JX534236,JX948782,EU503032,FJ233910,KC336417,EU450588,AY874163,JXQ99782,FJ667595,HQ738641,EU136716,JF317580,GU325769,AY484410,DQ861897,KC473168,AY321992,KC835191,EF675230,FN398026,AY874169,G0358998,KC835190,JQ181589,JQ181599,GU247988,AY754016,JEF592575,HQ202949,FJ644559,EF565354,FN687847,AF201897,EF493837,JX948785,FN687849,JX912915,AF201311,AY321994,EF524522,JX948781,AY181948,GU325761,AF055392,GU325757,EF675243,JQ181600,JXQ99786,FJ218000,DQ201641,EU780073,HQ202969,EF675234,JF690916,KC249977,GQ359003,JX948769,JF928002,G040852,JX519293,A |

| Taxonomy | NCBI Reference Sequence ID | Host | No. of Genomes | Lineage | Segment Count | Genbank Accession ID |
|---|---|---|---|---|---|---|
| | | | | | | Y09495,JN176181,KC835189,JQ181585,DQ997817,FJ667590,JX406421,EF675237,GU017735,DQ629113,FJ644556,AY596822,FJ998185,HQ831532,HQ650833,AY484408,FJ608543,JX204386,FJ644922,DQ220731,FN687840,FJ644929,HM027580,KF742550,GU124593,DQ220727,EU450586,KC618389,JF317588,FJ158604,AY181946,FJ608540,FN687851,GQ449669,HQ831533,EU283329,KC800636,AF264042,GQ915288,EU594439,HQ395047,EF421967,JF317584,JQ809464,HQ831537,FJ870969,EU555439,JQ181596,EF675241,JF690917,FN687852,FJ644563,AY321989,KF742543,KF027496,GQ911590,HM776451,HM038021,HQ395050,AY579893,JF317583,EU921254,HM776444,HM776449,EF524524,FJ608541,FJ644560,GQ227412,H0202951,HQ591377,KC788503,JQ181588,JF317587,KF742544,JF899334,HQ202971,JX982228,JX406423,GU247992,AY321996,GQ359011,HQ693092,GQ359000,AF086836,JX274295,EF565346,DQ220737,DQ629115,JQ181595,DQ104420,HM142898,FJ158606,JX982220,HQ |

| Taxonomy | NCBI Reference Sequence ID | Host | No. of Genomes | Lineage | Segment Count | Genbank Accession ID |
|---|---|---|---|---|---|---|
| | | | | | | 202963,AF201310,KC188796,AJ293867,EF524518,AY578327, HQ395053,AJ293869,HQ395024,EU45058 9,AY322001,KC8006 41,DQ861898,HM142 894,KF742245,DQ86 1902,JF317573,HQ59 1371,JF317576,FJ60 8545,EU545551,GU3 25759,EF675231,FN6 87848,JQ994269,EU 095020,EU420015,JX 406422,DQ220728,H M027579,GU325760, HQ591375,EU346945 ,EU594437,AY32199 8,KC751546,EF4938 41,JXQ99783,JQ6534 49,DQ915585,AY686 762,EU589463,HQ39 5059,FJ905462,EU50 3039,GU247990,FJ23 3906,EF565348,EU4 50592,EU547459,HQ 713495,EU257511,A F454546,AF201305, GQ915289,HQ83152 8,GU938302,GQ3589 93,EF675232,KC753 772,FJ233909,AY321 983,EF565360,JX512 858,JXQ99784,EU126 887,KC823056,AY32 2004,EU408780,FJ90 5463,JX406426,EU68 4164,FJ233907,EU54 5547,AY691169,KC7 53768,DQ629114,AY 484414,KC733435,K F850463,HM142899, FJ233908,GQ358997 ,GU252369,KC47316 5,AF118097,AY18039 6,FJ623185,EU13671 2,AY424404,HQ3781 60,KC688419,EF524 |

-continued

| Taxonomy | NCBI Reference Sequence ID | Host | No. of Genomes | Lineage | Segment Count | Genbank Accession ID |
|---|---|---|---|---|---|---|
| | | | | | | 536,KC527542,JX948778,DQ220734,EU136720,KC823053,JX406424,AY288135,EF524521,JX948774,HQ395033,HQ202972,EU450591,EF524539,EF565368,DQ364650,D0151643,DQ322701,FJ608549,GU325754,AY424403,FJ935780,KF027491,HM776442,JF317568,KC821785,KF850462,GU325755,FJ158605,EF619037,JX512856,JF690918,FJ870970,FN398024,EU545544,KC800634,HM142900,AY256460,FJ905465,AY682997,AF027217,FJ644927,HM038034,AY321990,FJ905459,HQ738640,HM776441,AY686764,EU503040,JX512854,FN687853,EFS24525,EU136717,EF452351,GU247987,AF086835,IQ181607,EU909687,KC823057,AY321987,KF850459,HQ113121,JN119257,KF871068,HQ831538,DQ220735,AF086834,KC800644,AY754020,FJ948168,DQ104423,JF317578,AY556476,HQ693093,FJ905470,GU450327,EU921256,HQ591365,AY321995,KC473166,EU257512,GQ996404,GQ359001,EU366326,FJ870974,HQ395055,GU244506,HM776440,EU886638,AF055394,JX535296,JN119256,GU450329,HM038 |

-continued

| Taxonomy | NCBI Reference Sequence ID | Host | No. of Genomes | Lineage | Segment Count | Genbank Accession ID |
|---|---|---|---|---|---|---|
| | | | | | | 017,FJ716703,AF544 024,JF317589,FJ218 001,AY181945,AY42 4405,JF690913,EF49 3842,GU325768,GUO 49342,FJ804417,HQ3 95044,HM009336 |
| Porcine circovirus 2 P0404c/03 | NC_005148 | vertebrates | 1 | Circoviridae,Circovirus,Porcine circovirus 2 | — | EU057185 |
| Porcine circovirus 2 R0255/209/03 | NC_005148 | vertebrates | 1 | Circoviridae,Circovirus,Porcine circovirus 2 | — | EU057189 |
| Porcine circovirus 2 S0255/210/03 | NC_005148 | vertebrates | 1 | Circoviridae,Circovirus,Porcine circovirus 2 | — | EU057188 |
| Porcine circovirus 2 T0181c/03 | NC_005148 | vertebrates | 1 | Circoviridae,Circovirus,Porcine circovirus 2 | — | EU057186 |
| Porcine circovirus 2 U0168/03 | NC_005148 | vertebrates | 1 | Circoviridae,Circovirus,Porcine circovirus 2 | — | EU057187 |
| Porcine circovirus 2 Z0161 b/03 | NC_005148 | vertebrates | 1 | Circoviridae,Circovirus,Porcine circovirus 2 | — | EU057184 |
| Porcine circovirus 2 strain SD3 | NC_005148 | vertebrates | 1 | Circoviridae,Circovirus,Porcine circovirus 2 | — | DQ218419 |
| Porcine circovirus 2 strain SDS | NC_005148 | vertebrates | 1 | Circoviridae,Circovirus,Porcine circovirus 2 | — | DQ218420 |
| Porcine circovirus 2 strain SD6 | NC_005148 | vertebrates | 1 | Circoviridae,Circovirus,Porcine circovirus 2 | — | DQ218421 |
| Porcine circovirus type 1/2a 1/2a | NC_013774 | vertebrates | 1 | Circoviridae,Circovirus,Porcine circovirus type | — | FJ655418 |
| Porcine circovirus type 2-B | NC_005148 | vertebrates | 4 | Circoviridae,Circovirus,Porcine circovirus 2 | — | KC261601,KC261600 ,AF112862,GU79957 6 |
| Porcine circovirus type 2-C | NC_005148 | vertebrates | 1 | Circoviridae,Circovirus,Porcine circovirus 2 | — | AF109398 |
| Porcine circovirus type 2-D | NC_005148 | vertebrates | 1 | Circoviridae,Circovirus,Porcine circovirus 2 | — | AF117753 |
| Porcine circovirus type 2-E | NC_005148 | vertebrates | 1 | Circoviridae,Circovirus,Porcine circovirus 2 | — | AF109399 |
| Porcine coronavirus HKU15 | NC_016990 | vertebrates | 2 | Coronaviridae, Deltacoronavirus, Porcine coronavirus HKU15 | — | JQ065043,JQ065042 |
| Porcine cytomegalovirus | NC_022233 | vertebrates | 1 | H erpesviridae,Cytomegalovirus, Porcine cytomegalovirus | — | KF017583 |
| Porcine encephalomyocarditis virus | NC_001479 | vertebrates | 2 | Picornaviridae,Cardiovirus,Encephalomyocard itis virus | | DQ517424,HM64189 7 |
| Porcine endogenous retrovirus | NC_003059 | vertebrates | 5 | Retroviridae,Gammaretrovirus,Porcine type-C oncovirus | — | EU523109,A66553,A XQ52638,A66552,AX 175461 |
| Porcine endogenous retrovirus C | NC_003059 | vertebrates | 2 | Retroviridae,Gammaretrovirus,Porcine type-C oncovirus | — | EF133960,HM159246 |
| Porcine endogenous retrovirus C/A | NC_003059 | vertebrates | 2 | Retroviridae,Gammaretrovirus,Porcine type-C oncovirus | — | AY953542,AY570980 |
| Porcine endogenous retrovirus E | NC_003059 | vertebrates | 1 | Retroviridae,Gammaretrovirus,Porcine type-C oncovirus | — | AF356697 |

-continued

| Taxonomy | NCBI Reference Sequence ID | Host | No. of Genomes | Lineage | Segment Count | Genbank Accession ID |
|---|---|---|---|---|---|---|
| Porcine enterovirus 10 | NC_004441 | vertebrates | 1 | Picornaviridae,Enterovirus,Enterovirus G | — | AF363455 |
| Porcine enterovirus 15 | NC_004441 | vertebrates | 1 | Picornaviridae,Enterovirus,Enterovirus G | — | JN807387 |
| Porcine enterovirus 3H | NC_004441 | vertebrates | 1 | Picornaviridae,Enterovirus,Enterovirus G | — | HQ702854 |
| Porcine enterovirus 9 | NC_004441 | vertebrates | 2 | Picornaviridae,Enterovirus,Enterovirus G | — | Y14459,HM131607 |
| Porcine enterovirus B | NC_004441 | vertebrates | 2 | Picornaviridae,Enterovirus,Enterovirus G | — | AF363453,JQ818253 |
| Porcine epidemic diarrhea virus | NC_003436 | vertebrates | 32 | Coronaviridae,Alphacoronavirus,Porcine epidemic diarrhea virus | — | KF272920,KF650374,KF650372,KC140102,JQ282909,EF185992,KC210145,KF46875 2,KC210147,KF6503 71,KC109141,JN5472 28,JX112709,KF4687 53,JX524137,JX5607 61,KC196276,KC189 944,JX188454,KC210 146,JX489155,JXQ88 695,KF650370,KF384 500,JX261936,KF650 375,AF353511,KF650 373,KF468754,JN825 712,GU937797,KF26 7450 |
| Porcine kobuvirus | NC_011829,NC_016769 | vertebrates | 9 | Picornaviridae,Kobuvirus,Aichivirus C | — | KC424638,JX401523, JX177612,KC424639, KF695124,KC204684 ,JQ692069,KC42464 0,JX827598 |
| Porcine kobuvirus swine/K-30-HUN/2008/HUN | NC_011829,NC_016769 | vertebrates | 1 | Picornaviridae,Kobuvirus,Aichivirus C | — | GQ249161 |
| Porcine kobuvirus swine/S-1-HUN/2007/H ungary | NC_011829,NC_016769 | vertebrates | 1 | Picornaviridae,Kobuvirus,Aichivirus C | — | EU787450 |
| Porcine partetravirus | NC_022104 | vertebrates | 1 | Parvoviridae,Porcine partetravirus | — | KC992732 |
| Porcine parvovirus | NC_001718 | vertebrates | 26 | Parvoviridae,Parvovirus,Porcine parvovirus | — | KF913346,KF913348, KF429253,AY684869, EU790641,JN872448, M38367,L23427,JX99 2846,KF913345,KF91 3349,U44978,KF9133 47,KF913351,AY5833 18,KF429252,EU790 642,FJ822038,DQ675 456,KF913350,DQ062 3,JN968975,KF42925 5,KF742500,HM9890 09,KF429254 |

| Taxonomy | NCBI Reference Sequence ID | Host | No. of Genomes | Lineage | Segment Count | Genbank Accession ID |
|---|---|---|---|---|---|---|
| Porcine parvovirus 4 | NC_014665 | vertebrates | 9 | Parvoviridae,Parvovirus,Porcine parvovirus 4 | — | GQ387500,GQ97896 5,GU978968,HM0311 34,GU978966,GU978 967,GQ387499,GU97 8964,HM031135 |
| Porcine parvovirus 5 | NC_023020 | vertebrates | 6 | Parvoviridae,Parvovirus,Porcine parvovirus 5 | — | JX896320,KF661535, JX896322,JX896319, JX896321,JX896318 |
| Porcine pestivirus isolate Bungowannah | NC_023176 | vertebrates | 1 | Flaviviridae,Pestivirus,Porcine pestivirus isolate Bungowannah | — | EF100713 |
| Porcine reovirus SHR-A | NC_004274 | vertebrates | 1 | Reoviridae,Orthoreovirus,Mammalian orthoreovirus | seg. L3 | JX415472 |
| Porcine reovirus SHR-A | NC_004275 | vertebrates | 1 | Reoviridae,Orthoreovirus,Mammalian orthoreovirus | seg. L2 | JX415467 |
| Porcine reovirus SHR-A | NC_004276 | vertebrates | 1 | Reoviridae,Orthoreovirus,Mammalian orthoreovirus | seg. S4 | JX415473 |
| Porcine reovirus SHR-A | NC_004277 | vertebrates | 1 | Reoviridae,Orthoreovirus,Mammalian orthoreovirus | seg. S1 | JX415469 |
| Porcine reovirus SHR-A | NC_004278 | vertebrates | 1 | Reoviridae,Orthoreovirus,Mammalian orthoreovirus | seg. M2 | JX415471 |
| Porcine reovirus SHR-A | NC_004279 | vertebrates | 1 | Reoviridae,Orthoreovirus,Mammalian orthoreovirus | seg. S2 | JX415465 |
| Porcine reovirus SHR-A | NC_004280 | vertebrates | 1 | Reoviridae,Orthoreovirus,Mammalian orthoreovirus | seg. M1 | JX415468 |
| Porcine reovirus SHR-A | NC_004281 | vertebrates | 1 | Reoviridae,Orthoreovirus,Mammalian orthoreovirus | seg. M3 | JX415474 |
| Porcine reovirus SHR-A | NC_004282 | vertebrates | 1 | Reoviridae,Orthoreovirus,Mammalian orthoreovirus | seg. L1 | JX415466 |
| Porcine reovirus SHR-A | NC_004283 | vertebrates | 1 | Reoviridae,Orthoreovirus,Mammalian orthoreovirus | seg. S3 | JX415470 |
| Porcine reovirus SHR-A | NC_013228 | vertebrates | 1 | Reoviridae,Orthoreovirus,Mammalian orthoreovirus | seg. M2 | JX415471 |
| Porcine reovirus SHR-A | NC_013230 | vertebrates | 1 | Reoviridae,Orthoreovirus,Mammalian orthoreovirus | seg. M3 | JX415474 |
| Porcine reovirus SHR-A | NC_013232 | vertebrates | 1 | Reoviridae,Orthoreovirus,Mammalian orthoreovirus | seg. S2 | JX415465 |
| Porcine reovirus SHR-A | NC_013234 | vertebrates | 1 | Reoviridae,Orthoreovirus,Mammalian orthoreovirus | seg. S4 | JX415473 |
| Porcine reproductive and respiratory syndrome virus | NC_001961 | vertebrates | 327 | Arteriviridae,Arterivirus,Porcine reproductive and respiratory syndrome virus | — | HQ84178,JQ663542 ,JQ663545,GU73726 4,FJ950746,EU26260 3,KF287142,EF51796 2,EU200962,JQ3098 22,JQ308798,FJ9507 47,HQ699067,KC422 730,KC862570,DQ17 6020,KC862567,HM2 14915,JX192638,GU |

| Taxonomy | NCBI Reference Sequence ID | Host | No. of Genomes | Lineage | Segment Count | Genbank Accession ID |
|---|---|---|---|---|---|---|
| | | | | | | 047344,EU880438,J 032671,KF287133, GU168568,EU187484 ,JN660150,JX192637 ,GU143913,JX31764 8,EU880436,EF5360 00,JQ663561,EU200 961,JF268681,DQ459 471,KC862574,GQ47 5526,HQ315836,EU1 06888,KC492506,JQ 663541,EU864232,E U097707,EF484031, KC422725,GU168567 ,GQ914997,KF28713 4,JN662424,FJ39345 8,AY612613,KF28713 9,JF800911,JQ66355 8,JQ663544,AF32569 1,JQ663563,EU8804 37,EF532802,GU454 850,FJ393456,JQ663 547,JQ663568,FJ349 261,JX215553,JX878 379,EF536001,JX215 554,KC862573,KF28 7135,KF555450,KF28 7137,EU880435,EU7 08726,JF796180,JX2 58843,JQ663546,KF2 87132,EF532805,KC 422729,JQ955657,D 0176021,JQ715698, GU232738,HM18967 6,KC862577,KC4227 28,FJ548855,FJ3934 59,HQ843180,EF532 801,EF484033,EU88 0434,EF535999,JQ66 3566,EU807840,EF5 36002,JQ663567,EU 880442,KC469618,J 0804986,JF268674,E F11245,DQ473474, KC862566,EU109503 ,EF532806,EF641008 ,EU864231,KC49250 5,JQ663553,EU2362 59,EF488739,DQ864 |

-continued

| Taxonomy | NCBI Reference Sequence ID | Host | No. of Genomes | Lineage | Segment Count | Genbank Accession ID |
|---|---|---|---|---|---|---|
| | | | | | | 705,JQ663551,JX192635,EU880431,JQ663549,JX235365,FJ175687,AF184212,JX177644,EU360130,JX317649,KC862579,EU109502,EF112446,EF532810,EF532813,KC862584,AF494042,EF532819,EU939312,AY42471,HM016158,AF066183,KF203132,EF153486,GQ359108,JQ663555,JN864948,GU169411,JF268673,DQ988080,JQ663564,AY032626,KC862575,JF268683,KC862576,FJ895329,AY366525,JQ663540,GQ374441,DQ056373,EU076704,HQ233604,JQ663556,GQ374442,KF632717,JN654459,JQ309823,GU269541,FJ548851,EU678352,JX215552,JX217036,FJ950744,JF268680,JX857698,EU880433,EF075945,JX512910,JX235367,JQ087873,KF555451,JQ663565,KC862583,EF532804,EU360129,EU860249,FJ393457,JN387272,GQ351601,AY150564,KF611905,JQ663562,GU232737,JN626287,HM011104,GU168569,KC862581,EF532807,EF532811,JX192633,HQ233605,GU232735,JN387274,DQ217415,EU860248,JF268676,JQ663543,DQ779791,EF532818,EF532808,KF287138,KF815525,FJ950745,AB |

| Taxonomy | NCBI Reference Sequence ID | Host | No. of Genomes | Lineage | Segment Count | Genbank Accession ID |
|---|---|---|---|---|---|---|
| | | | | | | 288356,GQ461593,G U232736,GU461292, JXQ87437,JQ663560, JX235370,JQ663548, KC862572,HM01615 9,KF287136,FJ54885 4,EU880439,KC8625 69,EF635006,AY5459 85,JX215551,FJ8891 29,DQ489311,JF2686 78,AF159149,JF2686 72,EU880443,KC422 727,GQ499193,AF33 1831,FJ524376,EU86 4233,JN387273,DQ1 76019,JQ663559,HQ 315835,FJ548852,JF 268684,FJ175689,H M853673,KC862585, EU880441,KC527830 ,EF532816,JF268677 ,FJ899592,EF112447 ,HM214913,U87392, KC862568,GQ499919 6,FJ536165,JF26868 2,KC445138,EF5328 09,JF268675,GQ857 656,JF802085,JX878 380,EU825724,JX192 634,JX235366,HQ84 3179,JN256115,KC42 2731,JQ743666,JX19 2639,FJ797690,KC86 2571,HQ315837,FJ88 9130,EU097706,HQ8 43181,FJ548853,EF5 36003,KF287143,GQ 499195,EF532812,K C492504,JN387271,K C862580,JN654458,J X192636,JQ663554,E F532815,JXQ44140,A F176348,GU067771,J 0663550,JF748717,J 0663552,KC422726, EF532817,JX912249, HM214914,JX880029 ,JX192632,JF268679, |

| Taxonomy | NCBI Reference Sequence ID | Host | No. of Genomes | Lineage | Segment Count | Genbank Accession ID |
|---|---|---|---|---|---|---|
| | | | | | | EU144079,JQ955658,EU825723,GQ499919,EF488048,JQ71569 7,EU360128,KF2871 41,AY585241,FJ5243 77,FJ194029,KC8625 78,FJ175688,KC8625 82,EU880432,AF046 869,EF532803,JF748 718,GQ330474,EF53 2814,EU880440,KF2 87140,GU047345,HQ 401282,JQ663557,E U624117 |
| Porcine sapelovirus | NC_003987 | vertebrates | 3 | Picornaviridae,Sapelovirus,Porcine sapelovirus | — | HQ875059,KF539414,JX286666 |
| Porcine sapelovirus 1 | NC_003987 | vertebrates | 1 | Picornaviridae,Sapelovirus,Porcine sapelovirus | — | AF406813 |
| Porcine teschovirus | NC_003985 | vertebrates | 30 | Picornaviridae,Teschovirus, Porcine teschovirus | — | AF296102,GQ914053,AF231769,AF296118,AF296111,AF296112,AF296113,HQ02037 8,AF296107,AF29609 2,AF296103,AF29611 5,KC667563,JQ4294 05,AF296089,AF2960 91,GU446660,AF231 767,AF296090,AF296 109,AF296104,AF231 768,AJQ11380,AF296 100,DQ355222,AF29 6087,AF296088,AF29 6117,KC667562,AF2 96108 |
| Porcine teschovirus 1 | NC_003985 | vertebrates | 1 | Picornaviridae,Teschovirus, Porcine teschovirus | — | AB038528 |
| Porcine teschovirus 10 | NC_003985 | vertebrates | 2 | Picornaviridae,Teschovirus, Porcine teschovirus | — | AF296119,AF296095 |
| Porcine teschovirus 11 | NC_003985 | vertebrates | 1 | Picornaviridae,Teschovirus, Porcine teschovirus | — | AF296096 |
| Porcine teschovirus 4 | NC_003985 | vertebrates | 1 | Picornaviridae,Teschovirus, Porcine teschovirus | — | JQ975417 |
| Porcine teschovirus 8 | NC_003985 | vertebrates | 5 | Picornaviridae,Teschovirus, Porcine teschovirus | — | JQ664746,GQ293092,KC757344,AF29609 3,JN710381 |
| Porcine teschovirus 9 | NC_003985 | vertebrates | 1 | Picornaviridae,Teschovirus, Porcine teschovirus | — | AF296094 |

-continued

| Taxonomy | NCBI Reference Sequence ID | Host | No. of Genomes | Lineage | Segment Count | Genbank Accession ID |
|---|---|---|---|---|---|---|
| Porcine torovirus | NC_022787 | vertebrates | 1 | Coronaviridae,Torovirus,Porcine torovirus | — | JQ860350 |
| Possum enterovirus W1 | NC_008714 | vertebrates | 1 | Picornaviridae,Enterovirus,Possum enterovirus W1 | — | AY462106 |
| Possum enterovirus W6 | NC_008715 | vertebrates | 1 | Picornaviridae,Enterovirus,Possum enterovirus W6 | — | AY462107 |
| PreXMRV-1 | NC_007815 | vertebrates | 1 | Retroviridae,Gammaretrovirus,Murine leukemia-related retroviruses | — | FR871849 |
| Procyon lotor papillomavirus 1 | NC_007150 | vertebrates | 1 | Papillomaviridae,Lambdapapillomavirus,Lambdapapillomavirus 4 | — | AY763115 |
| Pseudocowpox virus | NC_013804 | vertebrates | 2 | Poxviridae,Parapoxvirus,Pseudocowpox virus | — | GQ329670,GQ32966 9 |
| Psittacid herpesvirus 1 | NC_005264 | vertebrates | 1 | Herpesviridae,Iltovirus,Psittacid herpesvirus 1 | — | AY372243 |
| Psittacus erithacus timneh papillomavirus | NC_003973 | vertebrates | 2 | Papillomaviridae,Thetapapillomavirus,Thetapapillomavirus 1 | — | AF502599,AF420235 |
| Pteronotus polyomavirus | NC_020070 | vertebrates | 1 | Polyomaviridae,Polyomavirus,Pteronotus polyomavirus | — | JX520662 |
| Puma concolor papillomavirus type 1 | NC_004765 | vertebrates | 1 | Papillomaviridae,Lambdapapillomavirus,Lambdapapillomavirus 1 | — | AY904723 |
| Pygmy chimpanzee papillomavirus type 1 | NC_001355 | vertebrates | 1 | Papillomaviridae,Alphapapillomavirus,Alphapapillomavirus 10 | — | X62844 |
| Quail picornavirus QPV1/HUN/2010 | NC_016403 | vertebrates | 1 | Picornaviridae, Quail picornavirus QPV1/HUN/2010 | — | JN674502 |
| RD114 retrovirus | NC_009889 | vertebrates | 2 | Retroviridae,Gammaretrovirus,RD114 retrovirus | — | AB559882,EU030001 |
| Rabbit calicivirus Australia 1 MIC-07 | NC_011704 | vertebrates | 1 | Caliciviridae,Lagovirus,Rabbit calicivirus Australia 1 MIC-07 | — | EU871528 |
| Rabbit coronavirus HKU14 | NC_017083 | vertebrates | 4 | Coronaviridae,Betacoronavirus,Rabbit coronavirus HKU14 | — | JN874559,JN874562, JN874561,JN874560 |
| Rabbit fibroma virus | NC_001266 | vertebrates | 1 | Poxviridae,Leporipoxvirus,Rabbit fibroma virus | — | AF170722 |
| Rabbit hemorrhagic disease virus | NC_001543 | vertebrates | 35 | Caliciviridae,Lagovirus,Rabbit hemorrhagic disease virus | — | DQ280493,EF363035 ,FF558586,DQ18907 7,JX886001,AB30069 3,EF558576,EF55858 2,M67473,KC595270, DQ189078,EU003579 ,EF558572,EF558578 ,EF558580,EF558574 ,AF295785,EF558577 ,AY523410,HM62330 9,EU003582,EF5585 85,EU003578,AF258 618,DQ205345,EU00 3581,EF558584,EU0 03580,EF558579,JF4 12629,EF558575,EF5 58581,EF558573,EF5 58583,JX886002 |

| Taxonomy | NCBI Reference Sequence ID | Host | No. of Genomes | Lineage | Segment Count | Genbank Accession ID |
|---|---|---|---|---|---|---|
| Rabbit hemorrhagic disease virus-AST89 | NC_001543 | vertebrates | 1 | Caliciviridae,Lagovirus,Rabbit hemorrhagic disease virus | — | Z49271 |
| Rabbit hemorrhagic disease virus-BS89 | NC_001543 | vertebrates | 1 | Caliciviridae,Lagovirus,Rabbit hemorrhagic disease virus | — | X87607 |
| Rabbit hemorrhagic disease virus-SD | NC_001543 | vertebrates | 1 | Caliciviridae,Lagovirus,Rabbit hemorrhagic disease virus | — | Z29514 |
| Rabbit hemorrhagic disease virus-V351 | NC_001543 | vertebrates | 1 | Caliciviridae,Lagovirus,Rabbit hemorrhagic disease virus | — | U54983 |
| Rabbit oral papillomavirus | NC_002232 | vertebrates | 1 | Papillomaviridae,Kappapillomavirus,Kappapillomavirus 1 | — | AF227240 |
| Rabbit vesivirus | NC_008580 | vertebrates | 1 | Caliciviridae,Vesivirus,Rabbit vesivirus | — | AJ866991 |
| Rana grylio iridovirus | NC_005946 | vertebrates | 1 | Iridoviridae,Ranavirus,Frog virus 3 | — | JQ654586 |
| Rangifer tarandus papillomavirus 2 | NC_021930 | vertebrates | 1 | Papillomaviridae,Rangifer tarandus papillomavirus 2 | — | KC810012 |
| Ranid herpesvirus 1 | NC_008211 | vertebrates | 1 | Alloherpesviridae,Batrachovirus,Ranid herpesvirus 1 | — | DQ665917 |
| Ranid herpesvirus 2 | NC_008210 | vertebrates | 1 | Alloherpesviridae,Batrachovirus,Ranid herpesvirus 2 | — | DQ665652 |
| Raptor adenovirus A | NC_015455 | vertebrates | 1 | Adenoviridae,Siadenovirus,Raptor adenovirus A | — | EU715130 |
| Rat coronavirus | NC_012936,NC_00184 6 | vertebrates | 2 | Coronaviridae,Betacoronavirus,Murine coronavirus | — | JF792616,JF792617 |
| Rat coronavirus Parker | NC_012936,NC_00184 6 | vertebrates | 1 | Coronaviridae,Betacoronavirus,Murine coronavirus | — | FJ938068 |
| Rat theilovirus 1 | NC_009448,NC_00136 6,NC_0108 10 | vertebrates | 2 | Picornaviridae,Cardiovirus,Theilovirus | — | EU542581,EU815052 |
| Rattus norvegicus papillomavirus 1 EES-2009 | NC_008519 | vertebrates | 1 | Papillomaviridae,Pipapillomavirus,Pipapillomavirus 1 | — | GQ180114 |
| Raven circovirus | NC_008375 | vertebrates | 1 | Circoviridae,Circovirus,Raven circovirus | — | DQ146997 |
| Redspotted grouper nervous necrosis virus | NC_008040 | vertebrates | 5 | Nodaviridae,Betanodavirus,Redspotted grouper nervous necrosis virus | seg. RNA 1 | GQ402010,AY324869,AY369136,GQ402012,EF558368 |
| Redspotted grouper nervous necrosis virus | NC_008041 | vertebrates | 6 | Nodaviridae,Betanodavirus,Redspotted grouper nervous necrosis virus | seg. RNA 2 | AY744705,AY324870,GQ402011,EF558369,AY690596,GQ402013 |
| Reindeer papillomavirus | NC_001524 | vertebrates | 1 | Papillomaviridae,Deltapapillomavirus,Deltapapillomavirus 1 | — | AF443292 |
| Reovirus sp.T2W | NC_004276 | vertebrates | 1 | Reoviridae,Orthoreovirus,Mammalian orthoreovirus | seg. S4 | DQ220019 |
| Reovirus sp.T2W | NC_004277 | vertebrates | 1 | Reoviridae,Orthoreovirus,Mammalian orthoreovirus | seg. S1 | DQ220017 |
| Reovirus sp.T2W | NC_004279 | vertebrates | 1 | Reoviridae,Orthoreovirus,Mammalian orthoreovirus | seg. S2 | DQ220020 |

-continued

| Taxonomy | NCBI Reference Sequence ID | Host | No. of Genomes | Lineage | Segment Count | Genbank Accession ID |
|---|---|---|---|---|---|---|
| Reovirus sp.T2W | NC_004283 | vertebrates | 1 | Reoviridae,Orthoreovirus,Mammalian orthoreovirus | seg. S3 | DQ220018 |
| Reovirus sp.T2W | NC_013232 | vertebrates | 1 | Reoviridae,Orthoreovirus,Mammalian orthoreovirus | seg. S2 | DQ220020 |
| Reovirus sp.T2W | NC_013234 | vertebrates | 1 | Reoviridae,Orthoreovirus,Mammalian orthoreovirus | seg. S4 | DQ220019 |
| Reovirus sp.T3C43-MA | NC_004277 | vertebrates | 1 | Reoviridae,Orthoreovirus,Mammalian orthoreovirus | seg. S1 | U74293 |
| Reovirus sp.T3C44-MA | NC_004277 | vertebrates | 1 | Reoviridae,Orthoreovirus,Mammalian orthoreovirus | seg. S1 | U74292 |
| Reovirus sp.T3C84-MA | NC_004277 | vertebrates | 1 | Reoviridae,Orthoreovirus,Mammalian orthoreovirus | seg. S1 | U74291 |
| Reptile vesivirus Cro1 | NC_002551 | vertebrates | 1 | Caliciviridae,Vesivirus,Vesicular exanthema of swine virus | — | JXQ47864 |
| Reticuloendotheliosis virus | NC_006934 | vertebrates | 10 | Retroviridae,Gammaretrovirus,Reticuloendotheliosis virus | — | FJ496333,FJ439119, DQ003591,DQ38745 0,FJ439120,JX91271 0,GQ37584 8,GQ4156 46,KF305089,AY8429 51 |
| Rhesus monkey papillomavirus 1 | NC_001678 | vertebrates | 1 | Papillomaviridae,Alphapapillomavirus,Alphapa pillomavirus 12 | — | M60184 |
| Rhesus monkey rhadinovirus H26-95 | NC_003401 | vertebrates | 1 | Herpesviridae,Rhadinovirus,Macacine herpesvirus 5 | — | AF210726 |
| Rhesus papillomavirus type 1b | NC_001678 | vertebrates | 2 | Papillomaviridae,Alphapapillomavirus,Alphapa pillomavirus 12 | — | EF591300,FJ598133 |
| Rhinolophus bat coronavirus HKU2 | NC_009988 | vertebrates | 4 | Coronaviridae,Alphacoronavirus,Rhinolophus bat coronavirus HKU2 | — | EF203066,EF203065, EF203067,EF203064 |
| Rhinovirus C | NC_009996 | vertebrates | 3 | Picornaviridae,Enterovirus,Rhinovirus C | — | GQ222228,JXQ74056 ,GQ223227 |
| Rock bream iridovirus | NC_003494 | vertebrates | 2 | Iridoviridae,Megalocytivirus,Infectious spleen and kidney necrosis virus | — | KC244182,AY532606 |
| Rodent herpesvirus Peru | NC_015049 | vertebrates | 2 | Herpesviridae,Rodent herpesvirus Peru | — | HQ698924,HQ22196 3 |
| Rodent pegivirus | NC_021154 | vertebrates | 1 | Flaviviridae,Pegivirus,Rodent pegivirus | — | KC815311 |
| Ross's goose hepatitis B virus | NC_005888 ,NC_005950 | vertebrates | 3 | Hepadnaviridae,Ross's goose hepatitis B virus | — | AY494849,AY494848 ,M95589 |
| Rotavirus D chicken/05V0049/DEU/2005 | NC_014511 | vertebrates | 1 | Reoviridae,Rotavirus,Rotavirus D | seg. 1 | GU733443 |
| Rotavirus D chicken/05V0049/DEU/2005 | NC_014512 | vertebrates | 1 | Reoviridae,Rotavirus,Rotavirus D | seg. 2 | GU733444 |
| Rotavirus D chicken/05V0049/DEU/2005 | NC_014513 | vertebrates | 1 | Reoviridae,Rotavirus,Rotavirus D | seg. 3 | GU733445 |
| Rotavirus D chicken/05V0049/DEU/2005 | NC_014514 | vertebrates | 1 | Reoviridae,Rotavirus,Rotavirus D | seg. 4 | GU733446 |
| Rotavirus D chicken/05V0049/DEU/2005 | NC_014515 | vertebrates | 1 | Reoviridae,Rotavirus,Rotavirus D | seg. 5 | GU733447 |

| Taxonomy | NCBI Reference Sequence ID | Host | Lineage | No. of Genomes | Segment Count | Genbank Accession ID |
|---|---|---|---|---|---|---|
| Rotavirus D chicken/05V0049/DEU/2005 | NC_014516 | vertebrates | Reoviridae,Rotavirus,Rotavirus D | 1 | seg. 6 | GU733448 |
| Rotavirus D chicken/05V0049/DEU/2005 | NC_014517 | vertebrates | Reoviridae,Rotavirus,Rotavirus D | 1 | seg. 7 | GU733449 |
| Rotavirus D chicken/05V0049/DEU/2005 | NC_014518 | vertebrates | Reoviridae,Rotavirus,Rotavirus D | 1 | seg. 8 | GU733450 |
| Rotavirus D chicken/05V0049/DEU/2005 | NC_014519 | vertebrates | Reoviridae,Rotavirus,Rotavirus D | 1 | seg. 9 | GU733451 |
| Rotavirus D chicken/05V0049/DEU/2005 | NC_014520 | vertebrates | Reoviridae,Rotavirus,Rotavirus D | 1 | seg. 10 | GU733452 |
| Rotavirus D chicken/05V0049/DEU/2005 | NC_014521 | vertebrates | Reoviridae,Rotavirus,Rotavirus D | 1 | seg. 11 | GU733453 |
| Rous sarcoma virus | NC_001407 | vertebrates | Retroviridae,Alpharetrovirus,Rous sarcoma virus | 3 | — | V01197,X68524,AF03 3808 |
| Rous sarcoma virus-Prague C | NC_001407 | vertebrates | Retroviridae,Alpharetrovirus,Rous sarcoma virus | 1 | — | JQ2342 |
| Rous sarcoma virus-Schmidt-Ruppin B | NC_001407 | vertebrates | Retroviridae,Alpharetrovirus,Rous sarcoma virus | 1 | — | AF052428 |
| Rous sarcoma virus-Schmidt-Ruppin D | NC_001407 | vertebrates | Retroviridae,Alpharetrovirus,Rous sarcoma virus | 1 | — | D10652 |
| Rousettus aegyptiacus papillomavirus type 1 | NC_008298 | vertebrates | Papillomaviridae,Psipapillomavirus,Psipapillomavirus 1 | 1 | — | DQ366842 |
| Rousettus bat coronavirus HKU10 | NC_018871 | vertebrates | Coronaviridae,Alphacoronavirus,Bat coronavirus HKU10 | 2 | — | JQ989271,JQ989270 |
| Rousettus bat coronavirus HKU9 | NC_009021 | vertebrates | Coronaviridae,Betacoronavirus,Rousettus bat coronavirus HKU9 | 1 | — | EF065513 |
| SIVcpz Ptt-04Cam155 | NC_001549,NC_004455 | vertebrates | Retroviridae,Lentivirus,Simian immunodeficiency virus | 1 | — | FR686510 |
| SIVcpz Ptt-09Cam155 | NC_001549,NC_004455 | vertebrates | Retroviridae,Lentivirus,Simian immunodeficiency virus | 1 | — | FR686511 |
| STL polyomavirus | NC_020106 | vertebrates | Polyomaviridae,Polyomavirus,STL polyomavirus | 3 | — | KF525270,JX463184, JX463183 |
| Sable antelope coronavirus US/OH 1/2003 | NC_010327,NC_007732,NC_005147,NC_003045 | vertebrates | Coronaviridae,Betacoronavirus,Betacoronavirus 1 | 1 | — | EF424621 |
| Saffold virus | NC_009448,NC_001366,NC_010810 | vertebrates | Picornaviridae,Cardiovirus,Theilovirus | 11 | — | HM181998,FM20748 7,JF813004,HM1819 97,HM181996,HQ902 242,HM181999,HQ16 2476,EF165067,GU9 43513,FN999911 |
| Saimiriine herpesvirus 1 | NC_014567 | vertebrates | Herpesviridae,Simplexvirus,Saimiriine herpesvirus 1 | 1 | — | HM625781 |

| Taxonomy | NCBI Reference Sequence ID | Host | No. of Genomes | Lineage | Segment Count | Genbank Accession ID |
|---|---|---|---|---|---|---|
| Saimiriine herpesvirus 2 | NC_001350 | vertebrates | 2 | Herpesviridae,Rhadinovirus,Saimiriine herpesvirus 2 | — | AJ410493,X64346 |
| Saimiriine herpesvirus 3 | NC_016448 | vertebrates | 1 | Herpesviridae,Cytomegalovirus,Saimiriine herpesvirus 3 | — | FJ483967 |
| Salivirus | NC_012957,NC_012986 | vertebrates | 1 | Picornaviridae,Salivirus,Salivirus A | — | JN379039 |
| Salivirus A | NC_012957,NC_012986 | vertebrates | 1 | Picornaviridae,Salivirus,Salivirus A | — | GU245894 |
| Salivirus NG-J1 | NC_012957,NC_012986 | vertebrates | 1 | Picornaviridae,Salivirus,Salivirus A | — | GQ179640 |
| Sambar deer coronavirus US/OH-WD388-TC/1994 | NC_010327,NC_007732,NC_00514 7,NC_003045 | vertebrates | 2 | Coronaviridae,Betacoronavirus,Betacoronavirus 1 | — | FJ425188,FJ425190 |
| Sambar deer coronavirus US/OH-W D388/1994 | NC_010327,NC_007732,NC_00514 7,NC_003045 | vertebrates | 1 | Coronaviridae,Betacoronavirus,Betacoronavirus 1 | — | FJ425189 |
| San Miguel sea lion virus | NC_002551 | vertebrates | 1 | Caliciviridae,Vesivirus,Vesicular exanthema of swine virus | — | U15301 |
| Scotophilus bat coronavirus 512 | NC_009657 | vertebrates | 1 | Coronaviridae,Alphacoronavirus,Scotophilus bat coronavirus 512 | — | DQ648858 |
| Sea turtle tornovirus 1 | NC_012094 | vertebrates | 9 | Sea turtle tornovirus 1 | — | EU867817,EU867823,FJ867821,EU867822,EU867816,EU867820,EU867818,EU867824,EU867819 |
| Seal picornavirus type 1 | NC_009891 | vertebrates | 1 | Picornaviridae,Aquamavirus,Aquamavirus A | — | EU142040 |
| Sebokele virus 1 | NC_021482 | vertebrates | 1 | Picornaviridae,Parechovirus,Sebokele virus 1 | — | HF677705 |
| Seneca valley virus | NC_011349 | vertebrates | 2 | Picornaviridae,Senecavirus,Seneca valley virus | — | DQ641257,KC667560 |
| Sevenband grouper nervous necrosis virus | NC_008040 | vertebrates | 1 | Nodaviridae,Betanodavirus,Redspotted grouper nervous necrosis virus | seg. RNA 1 | AB373028 |
| Sevenband grouper nervous necrosis virus | NC_008041 | vertebrates | 1 | Nodaviridae,Betanodavirus,Redspotted grouper nervous necrosis virus | seg. RNA 2 | AB373029 |
| Sheeppox virus | NC_004002 | vertebrates | 1 | Poxviridae,Capripoxvirus,Sheeppox virus | — | AY077832 |
| Sheeppox virus A | NC_004002 | vertebrates | 1 | Poxviridae,Capripoxvirus,Sheeppox virus | — | AY077833 |
| Sheeppox virus NISKHI | NC_004002 | vertebrates | 1 | Poxviridae,Capripoxvirus,Sheeppox virus | — | AY077834 |
| Sheldgoose hepatitis B virus | NC_005890 | vertebrates | 2 | Hepadnaviridae, Sheldgoose hepatitis B virus | — | AY494853,AY494852 |
| Simian T-cell lymphotropic virus 6 | NC_011546 | vertebrates | 1 | Retroviridae,Deltaretrovirus,Simian T-cell lymphotropic virus 6 | — | EU231644 |

| Taxonomy | NCBI Reference Sequence ID | Host | No. of Genomes | Lineage | Segment Count | Genbank Accession ID |
|---|---|---|---|---|---|---|
| Simian T-lymphotropic virus 1 | NC_000858 NC_001436 | vertebrates | 4 | Retroviridae,Deltaretrovirus,Primate T-lymphotropic virus 1 | — | Z46900,AF074966,JX987040,AY590142 |
| Simian T-lymphotropic virus 2 | NC_001815 NC_001488 | vertebrates | 2 | Retroviridae,Deltaretrovirus,Primate T-lymphotropic virus 2 | — | Y14570,U90557 |
| Simian T-lymphotropic virus 3 | NC_003323 | vertebrates | 5 | Retroviridae,Deltaretrovirus,Primate T-lymphotropic virus 3 | — | AY217650,Y07616,AF391797,AF517775,AY222339 |
| Simian adenovirus 1 | NC_006879 | vertebrates | 1 | Adenoviridae,Mastadenovirus,Human adenovirus G | — | AY771780 |
| Simian adenovirus 18 | NC_022266 | vertebrates | 1 | Adenoviridae,Mastadenovirus,Simian adenovirus 18 | — | FJQ25931 |
| Simian adenovirus 20 | NC_020485 | vertebrates | 1 | Adenoviridae,Mastadenovirus,Simian adenovirus 20 | — | HQ605912 |
| Simian adenovirus 22 | NC_003266,NC_017825 | vertebrates | 1 | Adenoviridae,Mastadenovirus,Human adenovirus E | — | AY530876 |
| Simian adenovirus 23 | NC_003266,NC_017825 | vertebrates | 1 | Adenoviridae,Mastadenovirus,Human adenovirus E | — | AY530877 |
| Simian adenovirus 24 | NC_003266,NC_017825 | vertebrates | 1 | Adenoviridae,Mastadenovirus,Human adenovirus E | — | AY530878 |
| Simian adenovirus 25 | NC_003266,NC_017825 | vertebrates | 1 | Adenoviridae,Mastadenovirus,Human adenovirus E | — | AF394196 |
| Simian adenovirus 25.2 | NC_003266,NC_017825 | vertebrates | 1 | Adenoviridae,Mastadenovirus,Human adenovirus E | — | FJQ25918 |
| Simian adenovirus 26 | NC_003266,NC_017825 | vertebrates | 1 | Adenoviridae,Mastadenovirus,Human adenovirus E | — | FJQ25923 |
| Simian adenovirus 3 | NC_006144 | vertebrates | 1 | Adenoviridae,Mastadenovirus,Simian adenovirus A | — | AY598782 |
| Simian adenovirus 30 | NC_003266,NC_017825 | vertebrates | 1 | Adenoviridae,Mastadenovirus,Human adenovirus E | — | FJQ25920 |
| Simian adenovirus 36 | NC_003266,NC_017825 | vertebrates | 1 | Adenoviridae,Mastadenovirus,Human adenovirus E | — | FJQ25917 |
| Simian adenovirus 37.1 | NC_003266,NC_017825 | vertebrates | 1 | Adenoviridae,Mastadenovirus,Human adenovirus E | — | FJQ25921 |
| Simian adenovirus 37.2 | NC_003266,NC_017825 | vertebrates | 1 | Adenoviridae,Mastadenovirus,Human adenovirus E | — | FJQ25919 |

| Taxonomy | NCBI Reference Sequence ID | Host | No. of Genomes | Lineage | Segment Count | Genbank Accession ID |
|---|---|---|---|---|---|---|
| Simian adenovirus 38 | NC_003266,NC_017825 | vertebrates | 1 | Adenoviridae,Mastadenovirus,Human adenovirus E | — | FJQ25922 |
| Simian adenovirus 39 | NC_003266,NC_017825 | vertebrates | 1 | Adenoviridae,Mastadenovirus,Human adenovirus E | — | FJQ25924 |
| Simian adenovirus 49 | NC_015225 | vertebrates | 1 | Adenoviridae,Mastadenovirus,Simian adenovirus B | — | HQ241819 |
| Simian adenovirus 50 | NC_015225 | vertebrates | 1 | Adenoviridae,Mastadenovirus,Simian adenovirus B | — | HQ241820 |
| Simian adenovirus 6 | NC_006144 | vertebrates | 1 | Adenoviridae,Mastadenovirus,Simian adenovirus A | — | JQ776547 |
| Simian adenovirus A1139 | NC_015225 | vertebrates | 1 | Adenoviridae,Mastadenovirus,Simian adenovirus B | — | JN880448 |
| Simian adenovirus A1163 | NC_015225 | vertebrates | 1 | Adenoviridae,Mastadenovirus,Simian adenovirus B | — | JN880449 |
| Simian adenovirus A1173 | NC_015225 | vertebrates | 1 | Adenoviridae,Mastadenovirus,Simian adenovirus B | — | JN880450 |
| Simian adenovirus A1258 | NC_015225 | vertebrates | 1 | Adenoviridae,Mastadenovirus,Simian adenovirus B | — | JN880451 |
| Simian adenovirus A1285 | NC_015225 | vertebrates | 1 | Adenoviridae,Mastadenovirus,Simian adenovirus B | — | JN880452 |
| Simian adenovirus A1296 | NC_015225 | vertebrates | 1 | Adenoviridae,Mastadenovirus,Simian adenovirus B | — | JN880453 |
| Simian adenovirus A1312 | NC_015225 | vertebrates | 1 | Adenoviridae,Mastadenovirus,Simian adenovirus B | — | JN880454 |
| Simian adenovirus A1327 | NC_015225 | vertebrates | 1 | Adenoviridae,Mastadenovirus,Simian adenovirus B | — | JN880455 |
| Simian adenovirus A1335 | NC_015225 | vertebrates | 1 | Adenoviridae,Mastadenovirus,Simian adenovirus B | — | JN880456 |
| Simian adenovirus B | NC_015225 | vertebrates | 1 | Adenoviridae,Mastadenovirus,Simian adenovirus B | — | KC693021 |
| Simian adenovirus C | NC_021168 | vertebrates | 3 | Adenoviridae,Mastadenovirus,Simian adenovirus C | — | KC693024,KC693023,KC693022 |
| Simian endogenous retrovirus vero ATCC CCL-81 | NC_001550 | vertebrates | 1 | Retroviridae,Betaretrovirus,Mason-Pfizer monkey virus | — | JN134185 |
| Simian enterovirus A | NC_003988 | vertebrates | 1 | Picornaviridae,Enterovirus,Enterovirus H | — | AF201894 |
| Simian enterovirus SV4 | NC_003988 | vertebrates | 1 | Picornaviridae,Enterovirus,Enterovirus H | — | AF326759 |
| Simian foamy virus | NC_001364 | vertebrates | 5 | Retroviridae,Spumavirus,Simian foamy virus | — | JQ867465,JQ867462,JQ867464,U04327,J0867463 |
| Simian foamy virus-gorilla | NC_001364 | vertebrates | 1 | Retroviridae,Spumavirus,Simian foamy virus | — | HM245790 |
| Simian foamy virus-orangutan | NC_001364 | vertebrates | 1 | Retroviridae,Spumavirus,Simian foamy virus | — | AJ544579 |
| Simian hemorrhagic fever virus | NC_003092 | vertebrates | 1 | Arteriviridae,Arterivirus,Simian hemorrhagic fever virus | — | AF180391 |

| Taxonomy | NCBI Reference Sequence ID | Host | No. of Genomes | Lineage | Segment Count | Genbank Accession ID |
|---|---|---|---|---|---|---|
| Simian hepatitis A virus | NC_001489 | vertebrates | 2 | Picornaviridae,Hepatovirus,Hepatitis A virus | | EU140838,DQ0924 |
| Simian immunodeficiency virus | NC_001549, NC_004455 | vertebrates | 109 | Retroviridae,Lentivirus,Simian immunodeficiency virus | | JN091690,AY597209, AB253736,AY340700 ,AF328295,DQ37306 3,EU280804,AF0752 69,EF070331,EF5359 93,EF394357,M3132 5,U79412,AY611486, M27470,AY169968,E F070330,AY603959,A Y576480,M19499,EU 280805,AY599198,D 0201174,JN835461, AY611488,AY607702 ,AJ271369,AY599201 ,AY159322,AY52386 6,AY576481,DQ3746 58,AY588945,DQ201 173,AY611494,AB17 7846,AF103818,AM7 13177,EF070329,X52 154,AY588946,M327 41,FJ424863,DQ3746 57,M30931,EF39435 8,JQ866001,AY61149 1,M58410,JQ864084, M33262,M29975,AF3 82829,EF535994,AF0 77017,FR751162,M6 6437,FJ424865,AF46 8658,EU280806,AY6 07703,AY340701,FJ4 24871,FJ424864,FJ4 24866,AY607701,AY 611487,AY611492,AF 468659,AF301156,AY 611489,AY523865,M 76764,JN091691,AY5 99200,JQ864086,EF3 94356,AF131870,M8 3293,AY611495,JQ86 4087,DQ373064,AF1 15393,JN835462,EU2 80803,DQ201172,AY 655744,AY587015,L0 6042,JN835460,AY60 0249,AF334679,U727 48,XQ7805,L03295,A |

-continued

| Taxonomy | NCBI Reference Sequence ID | Host | No. of Genomes | Lineage | Segment Count | Genbank Accession ID |
|---|---|---|---|---|---|---|
| | | | | | | J580407,DQ373066, AY611493,AM745105 ,AY159321,AY52386 7,DQ373065,AY6077 04,AY599199,AM182 197,JQ864085,AF382 828,AY611490,AF447 763 |
| Simian immunodeficiency virus-agm,sab-1 | NC_001549 ,NC_00445 5 | vertebrates | 1 | Retroviridae,Lentivirus,Simian immunodeficiency virus | — | U04005 |
| Simian immunodeficiency virus-agm,tan-1 | NC_001549 ,NC_00445 5 | vertebrates | 1 | Retroviridae,Lentivirus,Simian immunodeficiency virus | — | U58991 |
| Simian immunodeficiency virus 17E-CI | NC_001549 ,NC_00445 5 | vertebrates | 1 | Retroviridae,Lentivirus,Simian immunodeficiency virus | — | AY033233 |
| Simian immunodeficiency virus 17E-Fr | NC_001549 ,NC_00445 5 | vertebrates | 1 | Retroviridae,Lentivirus,Simian immunodeficiency virus | — | AY033146 |
| Simian retrovirus 1 | NC_001550 | vertebrates | 2 | Retroviridae,Betaretrovirus,Mason-Pfizer monkey virus | — | M11841,U85505 |
| Simian retrovirus 2 | NC_001550 | vertebrates | 3 | Retroviridae,Betaretrovirus,Mason-Pfizer monkey virus | — | M16605,AF126467,A F126468 |
| Simian retrovirus 4 | NC_014474 | vertebrates | 3 | Retroviridae,Betaretrovirus,Simian retrovirus 4 | — | FJ979639,FJ971077, FJ979638 |
| Simian sapelovirus 1 | NC_004451 | vertebrates | 1 | Picornaviridae,Sapelovirus,Simian sapelovirus | — | AY064708 |
| Simian virus 12 | NC_007611 | vertebrates | 2 | Polyomaviridae,Polyomavirus,Simian virus 12 | — | DQ435829,AY614708 |
| Singapore grouper iridovirus | NC_006549 | vertebrates | 1 | Incloviridae,Ranavirus,Singapore grouper iridovirus | — | AY521625 |
| Siniperca chuatsi rhabdovirus | NC_008514 | vertebrates | 1 | Rhabdoviridae, Siniperca chuatsi rhabdovirus | — | DQ399789 |
| Small ruminant lentivirus | NC_001463 | vertebrates | 1 | Retroviridae,Lentivirus,Caprine arthritis encephalitis virus | — | HM210570 |
| Snake adenovirus 1 | NC_009989 | vertebrates | 1 | Adenoviridae,Atadenovirus,Snake adenovirus A | — | DQ106414 |
| Snake parvovirus 1 | NC_006148 | vertebrates | 1 | Parvoviridae,Dependovirus,Snake parvovirus 1 | — | AY349010 |
| Snakehead retrovirus | NC_001724 | vertebrates | 1 | Retroviridae, Snakehead retrovirus | — | U26458 |
| Snakehead rhabdovirus | NC_000903 | vertebrates | 1 | Rhabdoviridae,Novirhabdovirus,Snakehead virus | — | AF147498 |
| Snow goose hepatitis B virus | NC_005888 ,NC_00595 0 | vertebrates | 4 | Hepadnaviridae, Ross's goose hepatitis B virus | — | AF110999,AF111000, AF110997,AF110998 |
| Soft-shelled turtle iridovirus | NC_005946 | vertebrates | 1 | Incloviridae,Ranavirus,Frog virus 3 | — | EU627010 |
| South polar skua adenovirus-1 | NC_016437 | vertebrates | 1 | Adenoviridae,Siadenovirus,Skua adenovirus A | — | HM585353 |

| Taxonomy | NCBI Reference Sequence ID | Host | No. of Genomes | Lineage | Segment Count | Genbank Accession ID |
|---|---|---|---|---|---|---|
| Sparrow coronavirus HKU17 | NC_016992 | vertebrates | 1 | Coronaviridae,Deltacoronavirus,Sparrow coronavirus HKU17 | — | JQ065045 |
| Spider monkey foamy virus | NC_001364 | vertebrates | 1 | Retroviridae,Spumavirus,Simian foamy virus | — | EU010385 |
| Spissistilus festinus reovirus | NC_016874 | vertebrates | 1 | Reoviridae,Spissistilus festinus reovirus | seg. 2 | JF773383 |
| Spissistilus festinus reovirus | NC_016875 | vertebrates | 1 | Reoviridae,Spissistilus festinus reovirus | seg. 4 | JF773385 |
| Spissistilus festinus reovirus | NC_016876 | vertebrates | 1 | Reoviridae,Spissistilus festinus reovirus | seg. 6 | JF773387 |
| Spissistilus festinus reovirus | NC_016877 | vertebrates | 1 | Reoviridae,Spissistilus festinus reovirus | seg. 8 | JF773389 |
| Spissistilus festinus reovirus | NC_016878 | vertebrates | 1 | Reoviridae,Spissistilus festinus reovirus | seg. 10 | JF773391 |
| Spissistilus festinus reovirus | NC_016879 | vertebrates | 1 | Reoviridae,Spissistilus festinus reovirus | seg. 1 | JF773382 |
| Spissistilus festinus reovirus | NC_016880 | vertebrates | 1 | Reoviridae,Spissistilus festinus reovirus | seg. 3 | JF773384 |
| Spissistilus festinus reovirus | NC_016881 | vertebrates | 1 | Reoviridae,Spissistilus festinus reovirus | seg. 5 | JF773386 |
| Spissistilus festinus reovirus | NC_016882 | vertebrates | 1 | Reoviridae,Spissistilus festinus reovirus | seg. 7 | JF773388 |
| Spissistilus festinus reovirus | NC_016883 | vertebrates | 1 | Reoviridae,Spissistilus festinus reovirus | seg. 9 | JF773390 |
| Spleen focus-forming virus | NC_001500 | vertebrates | 1 | Retroviridae,Gammaretrovirus,Spleen focus-forming virus | — | K00021 |
| Spring viraemia of carp virus | NC_002803 | vertebrates | 4 | Rhabdoviridae,Vesiculovirus,Spring viraemia of carp virus | — | U18101,AJ318079,E U17782,DQ491000 |
| Spring viremia of carp virus | NC_002803 | vertebrates | 1 | Rhabdoviridae,Vesiculovirus,Spring viraemia of carp virus | — | DQ097384 |
| Squirrel monkey foamy virus | NC_001364 | vertebrates | 1 | Retroviridae,Spumavirus,Simian foamy virus | — | GU356394 |
| Squirrel monkey polyomavirus | NC_009951 | vertebrates | 1 | Polyomaviridae,Polyomavirus,Squirrel monkey polyomavirus | — | AM748741 |
| Squirrel monkey retrovirus | NC_001514 | vertebrates | 1 | Retroviridae,Betaretrovirus,Squirrel monkey retrovirus | — | M23385 |
| Squirrelpox virus | NC_022563 | vertebrates | 1 | Poxviridae,Squirrelpox virus | — | HE601899 |
| St-Valerien swine virus | NC_012699 | vertebrates | 1 | Caliciviridae,St-Valerien swine virus | — | AB863586 |
| Starling circovirus | NC_008033 | vertebrates | 1 | Circoviridae,Circovirus,Starling circovirus | — | DQ172906 |
| Steller sea lion vesivirus | NC_011050 | vertebrates | 2 | Caliciviridae,Vesivirus,Steller sea lion vesivirus | — | EF193004,EF195384 |
| Stork hepatitis B virus | NC_001486 | vertebrates | 4 | Hepadnaviridae,Avihepadnavirus,Heron hepatitis B virus | — | AJ251937,AJ251935, AJ251936,AJ251934 |
| Striped Jack nervous necrosis virus | NC_003448 | vertebrates | 2 | Nodaviridae,Betanodavirus,Striped Jack nervous necrosis virus | seg. RNA 1 | AB025018,AB056571 |
| Striped Jack nervous necrosis virus | NC_003449 | vertebrates | 2 | Nodaviridae,Betanodavirus,Striped Jack nervous necrosis virus | seg. RNA 2 | AB056572,D30814 |

| Taxonomy | NCBI Reference Sequence ID | Host | No. of Genomes | Lineage | Segment Count | Genbank Accession ID |
|---|---|---|---|---|---|---|
| Striped bass reovirus | NC_007588 | vertebrates | 1 | Reoviridae,Aquareovirus,Aquareovirus A | seg. 8 | AF450321 |
| Striped bass reovirus | NC_007590 | vertebrates | 2 | Reoviridae,Aquareovirus,Aquareovirus A | seg. 10 | U83396,AF450322 |
| Suid herpesvirus 1 | NC_006151 | vertebrates | 6 | Herpesviridae,Varicellovirus,Suid herpesvirus 1 | — | JF797217,BK001744, JQ809330,JQ809329, JF797219,JF797218 |
| Sus scrofa papillomavirus type 1 | NC_011280 | vertebrates | 2 | Papillomaviridae,Dyodeltapapillomavirus,Dyod eltapapillomavirus 1 | — | EF395819,EF395818 |
| Swine pasivirus 1 | NC_018226 | vertebrates | 1 | Picornaviridae,Swine pasivirus 1 | — | JQ316470 |
| Swinepox virus | NC_003389 | vertebrates | 1 | Poxviridae,Suipoxvirus,Swinepox virus | — | AF410153 |
| TGEV Miller M6 | NC_002306 | vertebrates | 1 | Coronaviridae,Alphacoronavirus,Alphacoronav irus 1 | — | DQ811785 |
| TGEV Miller M60 | NC_002306 | vertebrates | 1 | Coronaviridae,Alphacoronavirus,Alphacoronav irus 1 | — | DQ811786 |
| TGEV Purdue P115 | NC_002306 | vertebrates | 1 | Coronaviridae,Alphacoronavirus,Alphacoronav irus 1 | — | DQ811788 |
| TGEV virulent Purdue | NC_002306 | vertebrates | 1 | Coronaviridae,Alphacoronavirus,Alphacoronav irus 1 | — | DQ811789 |
| Tanapox virus | NC_002642 ,NC_00988 8 | vertebrates | 1 | Poxviridae,Yatapoxvirus,Tanapox virus | — | EF420157 |
| Taterapox virus | NC_008291 | vertebrates | 1 | Poxviridae,Orthopoxvirus,Taterapox virus | — | DQ437594 |
| Theiler's encephalomyelitis virus | NC_009448 ,NC_00136 6,NC_0108 10 | vertebrates | 9 | Picornaviridae,Cardiovirus,Theilovirus | — | M16020,EU723238,E U718732,HQ652539, EU718733,M20301,D 0401688,M20562,JX 443418 |
| Theiler's-like virus of rats | NC_009448 ,NC_00136 6,NC_0108 10 | vertebrates | 1 | Picornaviridae,Cardiovirus,Theilovirus | — | AB090161 |
| Threadfin reovirus | NC_007590 | vertebrates | 1 | Reoviridae,Aquareovirus,Aquareovirus A | seg. 10 | AY236219 |
| Threadfin reovirus | NC_007591 | vertebrates | 1 | Reoviridae,Aquareovirus,Aquareovirus A | seg. 11 | AF524892 |
| Threadfin reovirus | NC_007592 | vertebrates | 1 | Reoviridae,Aquareovirus,Aquareovirus A | seg. 6 | AY235428 |
| Thrush coronavirus HKU12-600 | NC_011549 | vertebrates | 1 | Coronaviridae,Deltacoronavirus,Thrush coronavirus HKU12 | — | FJ376621 |
| Tiger frog virus | NC_005946 | vertebrates | 1 | Incloviridae,Ranavirus,Frog virus 3 | — | AF389451 |
| Tiger puffer nervous necrosis virus | NC_013460 | vertebrates | 1 | Nodaviridae,Betanodavirus,Tiger puffer nervous necrosis virus | seg. RNA 1 | EU236148 |
| Tiger puffer nervous necrosis virus | NC_013461 | vertebrates | 1 | Nodaviridae,Betanodavirus,Tiger puffer nervous necrosis virus | seg. RNA 2 | EU236149 |
| Titi monkey adenovirus ECC-2011 | NC_020487 | vertebrates | 1 | Adenoviridae, Titi monkey adenovirus ECC-2011 | — | HQ913600 |

-continued

| Taxonomy | NCBI Reference Sequence ID | Host | No. of Genomes | Lineage | Segment Count | Genbank Accession ID |
|---|---|---|---|---|---|---|
| Transmissible gastroenteritis virus | NC_002306 | vertebrates | 10 | Coronaviridae,Alphacoronavirus,Alphacoronavirus 1 | — | HQ462571,DQ20144 7,AJ271965,AX15495 0,KC962433,EU0742 18,C087O486,DQ443 743,HM776941,FJ75 5618 |
| Trichechus manatus latirostris papillomavirus 1 | NC_006563 | vertebrates | 1 | Papillomaviridae,Rhopapillomavirus,Rhopapillomavirus 1 | — | AY609301 |
| Trichechus manatus latirostris papillomavirus 2 | NC_016898 | vertebrates | 1 | Papillomaviridae,Trichechus manatus latirostris papillomavirus 2 | — | JN709473 |
| Trichodysplasia spinulosa-associated polyomavirus | NC_014361 | vertebrates | 3 | Polyomaviridae,Polyomavirus,Trichodysplasia spinulosa-associated polyomavirus | — | GU989205,AB873001 ,JQ723730 |
| Tupaia virus | NC_007020 | vertebrates | 1 | Rhabdoviridae, Tupaia virus | — | AY840978 |
| Tupaiid herpesvirus 1 | NC_002794 | vertebrates | 1 | Herpesviridae, Tupaiid herpesvirus 1 | — | AF281817 |
| Turdivirus 1 | NC_014411 | vertebrates | 2 | Picornaviridae,Orthoturdivirus,Turdivirus 1 | — | GU182406,GU18240 7 |
| Turdivirus 2 | NC_014412 | vertebrates | 2 | Picornaviridae,Paraturdivirus,Turdivirus 2 | — | GU182409,GU18240 8 |
| Turdivirus 3 | NC_014413 | vertebrates | 2 | Picornaviridae,Paraturdivirus,Turdivirus 3 | — | GU18241l,GU18241 0 |
| Turkey adenovirus 1 | NC_014564 | vertebrates | 1 | Adenoviridae,Aviadenovirus,Turkey adenovirus B | — | GU936707 |
| Turkey adenovirus 4 | NC_022612 | vertebrates | 1 | Adenoviridae,Aviadenovirus,Turkey adenovirus 4 | — | KF477312 |
| Turkey adenovirus 5 | NC_022613 | vertebrates | 1 | Adenoviridae,Aviadenovirus,Turkey adenovirus 5 | — | KF477313 |
| Turkey adenovirus A | NC_001958 | vertebrates | 1 | Adenoviridae,Siadenovirus,Turkey adenovirus A | — | AF074946 |
| Turkey astrovirus | NC_002470 | vertebrates | 8 | Astroviridae,Avastrovirus, Turkey astrovirus | — | EU143850,EU143845 ,EU143848,EU14384 9,EU143846,EU1438 47,EU143844,Y15936 |
| Turkey astrovirus 2 | NC_005790 | vertebrates | 2 | Astroviridae,Avastrovirus,Avastrovirus 3 | — | EU143843,AF206663 |
| Turkey coronavirus | NC_010800 ,NC_00145 1 | vertebrates | 7 | Coronaviridae,Gammacoronavirus,Avian coronavirus | — | GQ427175,EU02252 6,GQ427l 74,GQ4271 73,GQ427176,EU022 525,EU095850 |
| Turkey gallivirus | NC_018400 | vertebrates | 1 | Picornaviridae, Turkey gallivirus | — | JQ691613 |
| Turkey hepatitis virus 2993D | NC_021201 | vertebrates | 1 | Picornaviridae,Megrivirus,Melegrivirus A | — | HM751199 |
| Tursiops truncatus papillomavirus 1 | NC_011109 | vertebrates | 1 | Papillomaviridae,Upsilonpapillomavirus,Upsilonpapillomavirus 1 | — | EU240894 |
| Tursiops truncatus papillomavirus 2 | NC_008184 | vertebrates | 1 | Papillomaviridae,Upsilonpapillomavirus,Upsilonpapillomavirus 2 | — | AY956402 |
| Tursiops truncatus papillomavirus type 3 | NC_011109 | vertebrates | 1 | Papillomaviridae,Upsilonpapillomavirus,Upsilonpapillomavirus 1 | — | EU240895 |
| Tylonycteris bat coronavirus HKU4 | NC_009019 | vertebrates | 1 | Coronaviridae,Betacoronavirus,Tylonycteris bat coronavirus HKU4 | — | EF065505 |

-continued

| Taxonomy | NCBI Reference Sequence ID | Host | No. of Genomes | Lineage | Segment Count | Genbank Accession ID |
|---|---|---|---|---|---|---|
| UR2 sarcoma virus | NC_001618 | vertebrates | 1 | Retroviridae,Alpharetrovirus,UR2 sarcoma virus | — | M10455 |
| Uncia uncia papillomavirus type 1 | NC_004765 | vertebrates | 1 | Papillomaviridae,Lambdapapillomavirus,Lambdapapillomavirus 1 | — | DQ180494 |
| Ursus maritimus papillomavirus 1 | NC_010739 | vertebrates | 1 | Papillomaviridae,Omegapapillomavirus,Omegapapillomavirus 1 | — | EF536349 |
| VESV-like calicivirus | NC_002551 | vertebrates | 1 | Caliciviridae,Vesivirus,Vesicular exanthema of swine virus | — | AF091736 |
| Vervet monkey polyomavirus 1 | NC_019844 | vertebrates | 1 | Polyomaviridae,Polyomavirus,Vervet monkey polyomavirus 1 | — | AB767298 |
| Vesicular exanthema of swine virus | NC_002551 | vertebrates | 1 | Caliciviridae,Vesivirus,Vesicular exanthema of swine virus | — | U76874 |
| Viral hemorrhagic septicemia virus | NC_000855 | vertebrates | 16 | Rhabdoviridae,Novirhabdovirus,Viral hemorrhagic septicemia virus | — | AB672614,EU481506,FJ460590,AF143862,AF143863,FJ362510,GQ385941,FN665788,JF792424,Z93412,KF477302,FJ460591,Z93414,AB179621,AB490792,KC778774 |
| Viral hemorrhagic septicemia virus (STRAIN 07-71) | NC_000855 | vertebrates | 1 | Rhabdoviridae,Novirhabdovirus,Viral hemorrhagic septicemia virus | — | AJ233396 |
| Viral hemorrhagic septicemia virus Fil3 | NC_000855 | vertebrates | 1 | Rhabdoviridae,Novirhabdovirus,Viral hemorrhagic septicemia virus | — | Y18263 |
| Visna/Maedi virus | NC_001452 | vertebrates | 7 | Retroviridae,Lentivirus,Visna/maedi virus | — | M10608,M60610,M60609,L06906,M51543,555323,A15114 |
| Visna/maedi virus | NC_001452 | vertebrates | 1 | Retroviridae,Lentivirus,Visna/maedi virus | — | HQ848062 |
| Walleye dermal sarcoma virus | NC_001867 | vertebrates | 3 | Retroviridae,Epsilonretrovirus,Walleye dermal sarcoma virus | — | AF033822,L41838,EF428979 |
| Walrus calicivirus | NC_004541 | vertebrates | 1 | Caliciviridae, Walrus calicivirus | — | AF321298 |
| Waterbuck coronavirus US/OH-WD358-GnC/1994 | NC_010327,NC_007732,NC_005147,NC_003045 | vertebrates | 1 | Coronaviridae,Betacoronavirus,Betacoronavirus 1 | — | FJ425185 |
| Waterbuck coronavirus US/OH-WD358-TC/1994 | NC_010327,NC_007732,NC_005147,NC_003045 | vertebrates | 1 | Coronaviridae,Betacoronavirus,Betacoronavirus 1 | — | FJ425184 |
| Waterbuck coronavirus US/OH-W D358/1994 | NC_010327,NC_007732,NC_005147,NC_003045 | vertebrates | 1 | Coronaviridae,Betacoronavirus,Betacoronavirus 1 | — | FJ425186 |

-continued

| Taxonomy | NCBI Reference Sequence ID | Host | No. of Genomes | Lineage | Segment Count | Genbank Accession ID |
|---|---|---|---|---|---|---|
| White bream virus | NC_008516 | vertebrates | 1 | Coronaviridae,Bafinivirus,White bream virus | — | DQ898157 |
| White-eye coronavirus HKU16 | NC_016991 | vertebrates | 1 | Coronaviridae,Deltacoronavirus,White-eye coronavirus HKU16 | — | JQ065044 |
| White-tailed deer coronavirus US/OH-WD470/1994 | NC_010327,NC_007732,NC_005147,NC_003045 | vertebrates | 1 | Coronaviridae,Betacoronavirus,Betacoronavirus 1 | — | FJ425187 |
| Wigeon coronavirus HKU20 | NC_016995 | vertebrates | 1 | Coronaviridae,Deltacoronavirus,Wigeon coronavirus HKU20 | — | JQ065048 |
| Wood mouse herpesvirus | NC_001826 | vertebrates | 1 | Herpesviridae,Rhadinovirus,Murid herpesvirus 4 | — | GQ169129 |
| Woodchuck hepatitis virus | NC_004107 | vertebrates | 19 | Hepadnaviridae,Orthohepadnavirus,Woodchuck hepatitis virus | — | KF874491,M11082,M19183,M18752,GU734791,JQ4514,AY3340 77,KF874493,AY3340 75,AY334076,AY628 100,JQ2442,AY628097,AY628099,AY6280 98,KF874492,AY6280 95,AY628096,M90520 |
| Woolly monkey sarcoma virus | NC_009424 | vertebrates | 1 | Retroviridae,Gammaretrovirus,Woolly monkey sarcoma virus | — | V01201 |
| XMRV | NC_007815 | vertebrates | 1 | Retroviridae,Gammaretrovirus,Murine leukemia-related retroviruses | — | FR872816 |
| XMRV-like mouse endogenous retrovirus mERV-XL | NC_007815 | vertebrates | 1 | Retroviridae,Gammaretrovirus,Murine leukemia-related retroviruses | — | JF714652 |
| Xenopus laevis endogenous retrovirus Xen1 | NC_010955 | vertebrates | 1 | Retroviridae, Xenopus laevis endogenous retrovirus Xen1 | — | AJ506107 |
| Xenotropic MuLV-related virus | NC_007815 | vertebrates | 4 | Retroviridae,Gammaretrovirus,Murine leukemia-related retroviruses | — | HQ154630,GQ49734 3,GQ497344,FN6920 43 |
| Xenotropic MuLV-related virus VP35 | NC_007815 | vertebrates | 1 | Retroviridae,Gammaretrovirus,Murine leukemia-related retroviruses | — | DQ241301 |
| Xenotropic MuLV-related virus VP42 | NC_007815 | vertebrates | 1 | Retroviridae,Gammaretrovirus,Murine leukemia-related retroviruses | — | DQ241302 |
| Xenotropic MuLV-related virus VP62 | NC_007815 | vertebrates | 2 | Retroviridae,Gammaretrovirus,Murine leukemia-related retroviruses | — | EF185282,DQ399707 |
| Xenotropic murine leukemia virus | NC_001702,NC_001819,NC_001362,NC_001501 | vertebrates | 2 | Retroviridae,Gammaretrovirus,Murine leukemia virus | — | JF908816,JF908815 |

| Taxonomy | NCBI Reference Sequence ID | Host | No. of Genomes | Lineage | Segment Count | Genbank Accession ID |
|---|---|---|---|---|---|---|
| Y73 sarcoma virus | NC_008094 | vertebrates | 2 | Retroviridae,Alpharetrovirus,Y73 sarcoma virus | — | V01170,L21974 |
| Yaba monkey tumor virus | NC_005179 | vertebrates | 1 | Poxviridae,Yatapoxvirus,Yaba monkey tumor virus | — | AY386371 |
| Yaba-like disease virus | NC_002642,NC_009888 | vertebrates | 1 | Poxviridae,Yatapoxvirus,Tanapox virus | — | AJ293568 |
| Yellowtail ascites virus | NC_004168 | vertebrates | 3 | Birnaviridae,Aquabirnavirus,Yellowtail ascites virus RNA | seg. A | AB281673,AB011440,AB006783 |
| Yellowtail ascites virus | NC_004176 | vertebrates | 2 | Birnaviridae,Aquabirnavirus,Yellowtail ascites virus | seg. RNA B | AY129662,AB281674 |
| Yellowtail ascites virus-YT-01A | NC_004176 | vertebrates | 1 | Birnaviridae,Aquabirnavirus,Yellowtail ascites virus | seg. RNA B | AY129663 |
| Yoka poxvirus | NC_015960 | vertebrates | 1 | Poxviridae,Orthopoxvirus,Yoka poxvirus | — | HQ849551 |
| Zalophus californianus papillomavirus 1 | NC_015325 | vertebrates | 1 | Papillomaviridae,Zalophus californianus papillomavirus 1 | — | HQ293213 |
| Zetapapillomavirus 1 | NC_003748 | vertebrates | 1 | Papillomaviridae,Zetapapillomavirus,Zetapapillomavirus 1 | — | AF394740 |
| Adeno-associated virus-2 | NC_001401 | vertebrates,human | 2 | Parvoviridae,Dependovirus,Adeno-associated virus-2 | — | AF043303,JQ1901 |
| Adeno-associated virus-3 | NC_001729 | vertebrates,human | 1 | Parvoviridae,Dependovirus,Adeno-associated virus-3 | — | U48704 |
| Adeno-associated virus-5 | NC_006152 | vertebrates,human | 2 | Parvoviridae,Dependovirus,Adeno-associated virus-5 | — | AF085716,Y18065 |
| Adeno-associated virus 3B | NC_001729 | vertebrates,human | 1 | Parvoviridae,Dependovirus,Adeno-associated virus-3 | — | AF028705 |
| Adeno-associated virus-Go,1 | NC_006152 | vertebrates,human | 1 | Parvoviridae,Dependovirus,Adeno-associated virus-5 | — | DQ335246 |
| Adult diarrheal rotavirus strain J19 | NC_007548 | vertebrates,human | 1 | Reoviridae,Rotavirus,Rotavirus H | seg. 1 | DQ113897 |
| Adult diarrheal rotavirus strain J19 | NC_007549 | vertebrates,human | 1 | Reoviridae,Rotavirus,Rotavirus H | seg. 2 | DQ113898 |
| Adult diarrheal rotavirus strain J19 | NC_007550 | vertebrates,human | 1 | Reoviridae,Rotavirus,Rotavirus H | seg. 4 | DQ113899 |
| Adult diarrheal rotavirus strain J19 | NC_007551 | vertebrates,human | 1 | Reoviridae,Rotavirus,Rotavirus H | seg. 3 | DQ113900 |
| Adult diarrheal rotavirus strain J19 | NC_007552 | vertebrates,human | 1 | Reoviridae,Rotavirus,Rotavirus H | seg. 5 | DQ113901 |
| Adult diarrheal rotavirus strain J19 | NC_007553 | vertebrates,human | 1 | Reoviridae,Rotavirus,Rotavirus H | seg. 6 | DQ113902 |
| Adult diarrheal rotavirus strain J19 | NC_007554 | vertebrates,human | 1 | Reoviridae,Rotavirus,Rotavirus H | seg. 8 | DQ113903 |
| Adult diarrheal rotavirus strain J19 | NC_007555 | vertebrates,human | 1 | Reoviridae,Rotavirus,Rotavirus H | seg. 7 | DQ113904 |
| Adult diarrheal rotavirus strain J19 | NC_007556 | vertebrates,human | 1 | Reoviridae,Rotavirus,Rotavirus H | seg. 9 | DQ113905 |
| Adult diarrheal rotavirus strain J19 | NC_007557 | vertebrates,human | 1 | Reoviridae,Rotavirus,Rotavirus H | seg. 10 | DQ113906 |

-continued

| Taxonomy | NCBI Reference Sequence ID | Host | No. of Genomes | Lineage | Segment Count | Genbank Accession ID |
|---|---|---|---|---|---|---|
| Adult diarrheal rotavirus strain J19 | NC_007558 | vertebrates,human | 1 | Reoviridae,Rotavirus,Rotavirus H | seg. 11 | DQ113907 |
| Allpahuayo virus | NC_010249 | vertebrates,human | 1 | Arenaviridae,Arenavirus,Allpahuayo virus | seg. L | AY216502 |
| Allpahuayo virus | NC_010253,AY012687 | vertebrates,human | 3 | Arenaviridae,Arenavirus,Allpahuayo virus | seg. S | AY012686,AY081210 |
| Alpaca respiratory coronavirus | NC_002645 | vertebrates,human | 1 | Coronaviridae,Alphacoronavirus,Human coronavirus 229E | — | JQ410000 |
| Amapari virus | NC_010247 | vertebrates,human | 2 | Arenaviridae,Arenavirus,Amapari virus | seg. S | AF485256,AF512834 |
| Amapari virus | NC_010251 | vertebrates,human | 2 | Arenaviridae,Arenavirus,Amapari virus | seg. L | AY924389,AY216517 |
| Andes virus | NC_003466 | vertebrates,human | 5 | Bunyaviridae,Hantavirus,Andes virus | seg. S | AF291702,AF004660,AF324902,AY228237,AF325966 |
| Andes virus | NC_003467 | vertebrates,human | 3 | Bunyaviridae,Hantavirus,Andes virus | seg. M | AF291703,AF324901,AY228238 |
| Andes virus | NC_003468 | vertebrates,human | 2 | Bunyaviridae,Hantavirus,Andes virus | seg. L | AY228239,AF291704 |
| Araraquara-like virus strain P5/Cajuru | NC_003466 | vertebrates,human | 1 | Bunyaviridae,Hantavirus,Andes virus | seg. S | EF571895 |
| Aravan virus | NC_020808 | vertebrates,human | 1 | Rhabdoviridae,Lyssavirus,Aravan virus | — | EF614259 |
| Arenavirus AV 96010025 | NC_010700 | vertebrates,human | 1 | Arenaviridae,Arenavirus,Whitewater Arroyo virus | seg. S | EU486820 |
| Arenavirus HQ380005 | NC_010700 | vertebrates,human | 1 | Arenaviridae,Arenavirus,Whitewater Arroyo virus | seg. S | EU910959 |
| Australian bat lyssavirus | NC_003243 | vertebrates,human | 2 | Rhabdoviridae,Lyssavirus,Australian bat lyssavirus | — | AF418014,AF081020 |
| Avian hepatitis E virus | NC_023425 | vertebrates,human | 3 | Hepeviridae,Avian hepatitis E virus | — | AM943646,AY535004,KC454286 |
| Avian metapneumovirus | NC_007652 | vertebrates,human | 10 | Paramyxoviridae,Metapneumovirus,Avian metapneumovirus | — | DQ009484,EF199772,AY640317,JF424833,DQ666911,AB54842 8,EF199771,AY59068 8,FJ977568,AY57978 0 |
| Avian paramyxovirus 4 | NC_019531 | vertebrates,human | 5 | Paramyxoviridae,Avulavirus,Avian paramyxovirus 4 | — | JX987283,EU877976,FJ177514,JN571485,JX133079 |
| Avian paramyxovirus 6 | NC_003043 | vertebrates,human | 7 | Paramyxoviridae,Avulavirus,Avian paramyxovirus 6 | — | EU622637,JX522537,KF267717,AY029299,AB759118,EF569970,GQ406232 |
| Avian rotavirus A | NC_011508 | vertebrates,human | 1 | Reoviridae,Rotavirus,Rotavirus A | seg. 3 | AY277923 |
| Avian rotavirus A | NC_011509 | vertebrates,human | 1 | Reoviridae,Rotavirus,Rotavirus A | seg. 6 | DQ096805 |
| Avian rotavirus CH2 | NC_011509 | vertebrates,human | 1 | Reoviridae,Rotavirus,Rotavirus A | seg. 6 | EF687020 |
| Avian rotavirus P0-13 | NC_011506 | vertebrates,human | 1 | Reoviridae,Rotavirus,Rotavirus A | seg. 2 | AB009630 |
| Avian rotavirus P0-13 | NC_011507 | vertebrates,human | 1 | Reoviridae,Rotavirus,Rotavirus A | seg. 1 | AB009629 |
| Avian rotavirus P0-13 | NC_011508 | vertebrates,human | 1 | Reoviridae,Rotavirus,Rotavirus A | seg. 3 | AB009631 |
| BK polyomavirus | NC_001538 | vertebrates,human | 282 | Polyomaviridae,Polyomavirus,BK polyomavirus | — | KF055891,AB211388,AB269835,AB269836,AB263928,AB29894 |

-continued

| Taxonomy | NCBI Reference Sequence ID | Host | No. of Genomes | Lineage | Segment Count | Genbank Accession ID |
|---|---|---|---|---|---|---|
| | | | | | | 1,AB464960,AB4649 63,JN192434,V01108 ,AB263918,AB26986 4,AB301093,AB2179 18,AB464955,AB365 166,JN192439,JN192 431,AB263925,AB26 3912,AB369091,AB3 65164,AY628237,AB 263926,FR720317,A B485697,AB464957, AB269868,FR720309 ,AB263938,AB26982 3,AB269840,AB2698 31,V01109,AB365163 ,FR720314,AB30109 5,AB369089,AB4856 96,AB269852,AB269 834,FR720312,AB26 9863,AB263934,FR7 20321,AB298944,AB 211371,AB211391,A B298945,FR720322, AB263922,AB269847 ,AB365158,AB36516 1,AB269827,AB3651 48,JN192438,AY6282 29,AB365139,AB301 087,AB263916,AB26 3920,M23122,AY628 235,AB365135,AY62 8233,AB217920,AB2 69855,AB485706,AB 269851,KF055892,AB 36517l,AB365175,A B485709,AB369096, AY628225,AB269866 ,AB365151,AB26984 1,AB485707,AB2698 25,AB211387,AB365 132,AB269832,AY62 8231,AB260029,AB2 69848,AB365170,AB 365130,AB269844,A B269830,AB485712, AB269856,AB269853 ,AB301089,AB26984 5,AB365136,AB3651 |

| Taxonomy | NCBI Reference Sequence ID | Host | No. of Genomes | Lineage | Segment Count | Genbank Accession ID |
|---|---|---|---|---|---|---|
| | | | | | | 55,AB301102,AB263 914,AB485703,JN192 432,FR720318,AB26 9861,AB365174,AB2 63933,AB301091,AB 269865,AB365134,A B301097,AB213487, AB301099,AB369094 ,AY628226,AB36909 3,AB217917,AB3651 69,AB269837,AB365 146,AY628227,JQ713 822,EF376992,AB260 033,AB263936,AB21 1373,AB211389,AB4 64958,AB464953,AB 365137,AB269839,A B211390,AB485698,J N192437,AB260031, AB365167,AB269842 ,FR720319,AB36516 8,AB269829,AB2639 17,AB365159,FR720 320,AB301086,AB26 3937,AB365176,JN19 2440,AB269849,AB2 69838,AB211370,AB 263919,AB365172,A B365144,AB260028, AB485708,JN192435, AB298947,AB269824 ,AB269857,AB26984 3,AB269846,AB3651 33,AB211381,AB365 156,AY628234,AB36 9098,AB211385,AB2 63935,AB369100,AB 365177,FR720323,A B301100,AB464962, AB365157,AB485705 ,AB485711,AB26986 7,FR720311,KF05589 3,AB365141,AB2113 77,AB365173,AB485 701,AB260030,AB48 5700,AB211375,AB3 65140,AB217919,AB 301092,AB369095,A |

-continued

| Taxonomy | NCBI Reference Sequence ID | Host | No. of Genomes | Lineage | Segment Count | Genbank Accession ID |
|---|---|---|---|---|---|---|
| | | | | | | B369087,AB263927, AB211374,AB464956 ,AB301103,AB36516 5,AB269833,AB3651 38,AY628230,AB269 860,AB485699,AB21 1376,AB365147,AB3 69092,AB464954,AB 269826,AB365143,A B365145,FR720310, AB369090,AB263924 ,AB369101,AB30110 1,AY628238,AB2639 13,AB485702,AB298 946,AB365154,AB26 3930,AB301088,AB3 69088,AB365150,AB 464961,AB260032,A B365149,AB211379, AY628228,AY628224 ,AB298940,AB26985 9,AB301098,AB3690 97,AB485710,AB211 382,AB269858,DQ30 5492,AB485695,AB2 63921,AB301094,JN 92433,AB263932,AB 369099,AB365153,A B365131,FR720316, AB301090,AB211372 ,AB211386,AB29894 3,AB365160,AB3651 42,AB263931,AB485 704,AB269862,FR72 0313,AB217921,AB2 69828,AB269854,AB 485694,AB269850,JN 192436,FR720315,JN 192441,AB269822,A B365152,AB298942, AB263915,AB263923 ,AB269869,AB36516 2,AB365178,AY6282 36,AB260034,AB211 383,FR720308,AB21 1384,AY628232,AB2 11378,AB211380,AB |

-continued

| Taxonomy | NCBI Reference Sequence ID | Host | No. of Genomes | Lineage | Segment Count | Genbank Accession ID |
|---|---|---|---|---|---|---|
| Baboon enterovirus | NC_001612 | vertebrates,human | 1 | Picornaviridae,Enterovirus,Enterovirus A | — | 211369,AB464959,A B263929,AB301096 |
| Bat Coy 273/2005 | NC_004718 | vertebrates,human | 1 | Coronaviridae,Betacoronavirus,Severe acute respiratory syndrome-related coronavirus | — | AF326750 DQ648856 |
| Bat Coy 279/2005 | NC_004718 | vertebrates,human | 1 | Coronaviridae,Betacoronavirus,Severe acute respiratory syndrome-related coronavirus | — | DQ648857 |
| Bat Hepatitis B virus | NC_003977 | vertebrates,human | 1 | Hepadnaviridae,Orthohepadnavirus,Hepatitis B virus | — | KC790377 |
| Bat SARS Coy Rf1/2004 | NC_004718 | vertebrates,human | 1 | Coronaviridae,Betacoronavirus,Severe acute respiratory syndrome-related coronavirus | — | DQ412042 |
| Bat SARS Coy Rm1/2004 | NC_004718 | vertebrates,human | 1 | Coronaviridae,Betacoronavirus,Severe acute respiratory syndrome-related coronavirus | — | DQ412043 |
| Bat SARS Coy Rp3/2004 | NC_004718 | vertebrates,human | 1 | Coronaviridae,Betacoronavirus,Severe acute respiratory syndrome-related coronavirus | — | DQ071615 |
| Bat SARS coronavirus HKU3-10 | NC_004718 | vertebrates,human | 1 | Coronaviridae,Betacoronavirus,Severe acute respiratory syndrome-related coronavirus | — | GQ153545 |
| Bat SARS coronavirus HKU3-11 | NC_004718 | vertebrates,human | 1 | Coronaviridae,Betacoronavirus,Severe acute respiratory syndrome-related coronavirus | — | GQ153546 |
| Bat SARS coronavirus HKU3-12 | NC_004718 | vertebrates,human | 1 | Coronaviridae,Betacoronavirus,Severe acute respiratory syndrome-related coronavirus | — | GQ153547 |
| Bat SARS coronavirus HKU3-13 | NC_004718 | vertebrates,human | 1 | Coronaviridae,Betacoronavirus,Severe acute respiratory syndrome-related coronavirus | — | GQ153548 |
| Bat SARS coronavirus HKU3-2 | NC_004718 | vertebrates,human | 1 | Coronaviridae,Betacoronavirus,Severe acute respiratory syndrome-related coronavirus | — | DQ084199 |
| Bat SARS coronavirus HKU3-3 | NC_004718 | vertebrates,human | 1 | Coronaviridae,Betacoronavirus,Severe acute respiratory syndrome-related coronavirus | — | DQ084200 |
| Bat SARS coronavirus HKU3-4 | NC_004718 | vertebrates,human | 1 | Coronaviridae,Betacoronavirus,Severe acute respiratory syndrome-related coronavirus | — | GQ153539 |
| Bat SARS coronavirus HKU3-5 | NC_004718 | vertebrates,human | 1 | Coronaviridae,Betacoronavirus,Severe acute respiratory syndrome-related coronavirus | — | GQ153540 |
| Bat SARS coronavirus HKU3-6 | NC_004718 | vertebrates,human | 1 | Coronaviridae,Betacoronavirus,Severe acute respiratory syndrome-related coronavirus | — | GQ153541 |
| Bat SARS coronavirus HKU3-7 | NC_004718 | vertebrates,human | 1 | Coronaviridae,Betacoronavirus,Severe acute respiratory syndrome-related coronavirus | — | GQ153542 |
| Bat SARS coronavirus HKU3-8 | NC_004718 | vertebrates,human | 1 | Coronaviridae,Betacoronavirus,Severe acute respiratory syndrome-related coronavirus | — | GQ153543 |
| Bat SARS coronavirus HKU3-9 | NC_004718 | vertebrates,human | 1 | Coronaviridae,Betacoronavirus,Severe acute respiratory syndrome-related coronavirus | — | GQ153544 |
| Bat SARS-like coronavirus Rs3367 | NC_004718 | vertebrates,human | 1 | Coronaviridae,Betacoronavirus,Severe acute respiratory syndrome-related coronavirus | — | KC881006 |
| Bat SARS-like coronavirus RsSHC014 | NC_004718 | vertebrates,human | 1 | Coronaviridae,Betacoronavirus,Severe acute respiratory syndrome-related coronavirus | — | KC881005 |
| Bat SARS-like coronavirus WIV1 | NC_004718 | vertebrates,human | 1 | Coronaviridae,Betacoronavirus,Severe acute respiratory syndrome-related coronavirus | — | KF367457 |
| Bat coronavirus HKU3 | NC_004718 | vertebrates,human | 1 | Coronaviridae,Betacoronavirus,Severe acute respiratory syndrome-related coronavirus | — | DQ022305 |

| Taxonomy | NCBI Reference Sequence ID | Host | Lineage | No. of Genomes | Segment Count | Genbank Accession ID |
|---|---|---|---|---|---|---|
| Bat hepevirus | NC_018382 | vertebrates,human | Hepeviridae,Bat hepevirus | 1 | — | JQ001749 |
| Bat sapovirus TLC58/HK | NC_017936 | vertebrates,human | Caliciviridae,Sapovirus,Bat sapovirus TLC58/HK | 1 | — | JN899075 TLC58/HK |
| Bear Canyon virus | NC_010255 | vertebrates,human | Arenaviridae,Arenavirus,Bear Canyon virus | 2 | seg. L | AY924390,AY216503 |
| Bear Canyon virus | NC_010256 | vertebrates,human | Arenaviridae,Arenavirus,Bear Canyon virus | 3 | seg. S | AF512833,AY924392, AY924391 |
| Beilong virus | NC_007803 | vertebrates,human | Paramyxoviridae,Beilong virus | 1 | — | DQ100461 |
| Bermejo virus | NC_003466 | vertebrates,human | Bunyaviridae,Hantavirus,Andes virus | 1 | seg. S | AF482713 |
| Blue River virus | NC_005215 | vertebrates,human | Bunyaviridae,Hantavirus,Sin Nombre virus | 2 | seg. M | AF030551,AF030552 |
| Borna disease virus | NC_001607 | vertebrates,human | Bornaviridae,Bornavirus,Borna disease virus | 13 | — | AF030551,AF030552, AJ311522,AB032031, AJ311523,AY114162, AB258389,AB246670 ,AY114161,L27077,E U781967,U04608,AJ3 11521,AY114163,AJ3 11524 |
| Bovine group C rotavirus | NC_007570 | vertebrates,human | Reoviridae,Rotavirus,Rotavirus C | 1 | seg. 5 | AB108680 |
| Bovine group C rotavirus | NC_007571 | vertebrates,human | Reoviridae,Rotavirus,Rotavirus C | 2 | seg. 8 | AB108681,U31750 |
| Bovine group C rotavirus | NC_007574 | vertebrates,human | Reoviridae,Rotavirus,Rotavirus C | 1 | seg. 4 | U26552 |
| Bovine parainfluenza virus 3 | NC_002161 | vertebrates,human | Paramyxoviridae,Respirovirus,Bovine parainfluenza virus 3 | 11 | — | EU277658,JQ063064 ,AXQ73601,AB77048 4,HQ530153,AF1786 55,JX969001,D84095 ,AXQ73600,AF178654 ,AB770485 |
| Bovine respiratory syncytial virus | NC_001989 | vertebrates,human | Paramyxoviridae,Pneumovirus,Bovine respiratory syncytial virus | 1 | — | AF092942 |
| Bovine respiratory syncytial virus ATCC51908 | NC_001989 | vertebrates,human | Paramyxoviridae,Pneumovirus,Bovine respiratory syncytial virus | 1 | — | AF295543 |
| Bovine rotavirus | NC_011500 | vertebrates,human | Reoviridae,Rotavirus,Rotavirus A | 1 | seg. 5 | HM363560 |
| Bovine rotavirus | NC_011501 | vertebrates,human | Reoviridae,Rotavirus,Rotavirus A | 42 | seg. 7 | FJ206164,EU542719, HM363562,EU54271 6,K02170,FJ206188, EU542714,EU542715 ,FJ206180,FJ206176, EU542718,FJ206174, FJ206181,FJ206184, DQ494403,EU542717 ,FJ206189,FJ206172, FJ206165,FJ206179, FJ206166,FJ206192, FJ206185,FJ206178, DQ494404,FJ206182, FJ206171,FJ206191, FJ206167,FJ206190, FJ206186,FJ206175, FJ206187,FJ206173, FJ206226,FJ206168, |

| Taxonomy | NCBI Reference Sequence ID | Host | No. of Genomes | Lineage | Segment Count | Genbank Accession ID |
|---|---|---|---|---|---|---|
| Bovine rotavirus | NC_011502 | vertebrates,human | 41 | Reoviridae,Rotavirus,Rotavirus A | seg. 8 | FJ206183,JX971577, FJ206193,FJ206169, FJ206170,FJ206177 EU542713,FJ206158, FJ206139,DQ494402, FJ206120,FJ206133, FJ206148,FJ206116, EU542711,FJ206136, HM363561,FJ206118 ,FJ206146,FJ206143, EU542708,FJ206138, FJ206130,FJ206131, FJ206152,FJ206110, FJ206122,FJ206123, FJ206126,FJ206157, FJ206108,FJ206134, JX971576,FJ206128, FJ206141,FJ206114, FJ206125,EU542712, FJ206150,EU542709, FJ206155,EU542710, DQ494401,FJ206154, FJ206160,FJ206145, FJ206112 |
| Bovine rotavirus | NC_011503 | vertebrates,human | 49 | Reoviridae,Rotavirus,Rotavirus A | seg. 9 | FJ206037,FJ217204, FJ206039,EU873014, FJ206073,FJ206082, GQ352366,FJ217205 ,FJ206047,EU143711 ,HQ199897,AB07705 4,FJ206057,FJ20606 8,FJ206079,FJ20605 8,AB077056,FJ20607 7,HM591496,HM2355 10,GQ352364,U5033 2,FJ206055,FJ20608 7,GQ352362,JX9715 74,AB077058,EU873 015,FJ206048,FJ206 072,FJ206085,FJ545 658,DQ494393,X526 50,AB077053,FJ2060 84,EU828784,EU873 013,FJ206088,FJ206 044,DQ494394,AB07 7055,FJ206049,FJ20 6070,AB077057,FJ20 |

| Taxonomy | NCBI Reference Sequence ID | Host | No. of Genomes | Lineage | Segment Count | Genbank Accession ID |
|---|---|---|---|---|---|---|
| Bovine rotavirus | NC_011504 | vertebrates,human | 51 | Reoviridae,Rotavirus,Rotavirus A | seg. 10 | 6041,FJ206064,FJ206080,FJ206075 EU542721,FJ206109, FJ206137,JX971578, FJ206147,AF166354, FJ206117,EU542722, FJ206113,FJ206140, FJ206111,FJ206144, EU542723,DQ494398 ,EU873006,DQ494439 7,FJ206135,EU82878 6,EU542720,FJ206612 7,FJ206151,FJ206610 7,AF166353,FJ206610 1,FJ206103,HM5914 94,FJ206129,EU5427 25,FJ206162,HM363 563,FJ206156,FJ206 115,FJ206132,EU542 724,FJ206161,EU873 007,FJ206119,FJ206 105,FJ206142,HM59 1492,FJ206121,EU87 3008,FJ206124,FJ20 6149,FJ206106,FJ20 6163,HM591493,FJ2 06159,FJ206153,FJ19 72713,FJ206104 |
| Bovine rotavirus | NC_011505 | vertebrates,human | 41 | Reoviridae,Rotavirus,Rotavirus A | seg. 11 | FJ206045,FJ206050, FJ206076,FJ206054, FJ206071,FJ206061, FJ206052,FJ206078, EU542729,EU542731 ,FJ206091,FJ206046, EU542730,FJ206099, FJ206059,FJ206083, HM363564,FJ206096 ,FJ206093,FJ206067, DQ494399,FJ206069, FJ206074,FJ206081, FJ206056,FJ206090, FJ206060,DQ494400, FJ206065,EU542727, FJ206092,EU542726, FJ206089,FJ206100, FJ206097,FJ206086, |

| Taxonomy | NCBI Reference Sequence ID | Host | No. of Genomes | Lineage | Segment Count | Genbank Accession ID |
|---|---|---|---|---|---|---|
| Bovine rotavirus | NC_011506 | vertebrates,human | 2 | Reoviridae,Rotavirus,Rotavirus A | seg. 2 | FJ206063,FJ206094,FJ206098,JX971579,EU542728 |
| Bovine rotavirus | NC_011507 | vertebrates,human | 3 | Reoviridae,Rotavirus,Rotavirus A | seg. 1 | X52589,JX971570 JX971569,X55444,JQ4346 |
| Bovine rotavirus | NC_011508 | vertebrates,human | 1 | Reoviridae,Rotavirus,Rotavirus A | seg. 3 | JX971571 |
| Bovine rotavirus | NC_011509 | vertebrates,human | 5 | Reoviridae,Rotavirus,Rotavirus A | seg. 6 | EU873010,EU873011,EU873012,K02254,JX971573 |
| Bovine rotavirus A | NC_011510 | vertebrates,human | 2 | Reoviridae,Rotavirus,Rotavirus A | seg. 4 | JX971572,EU873009 |
| Bovine rotavirus A | NC_011500 | vertebrates,human | 3 | Reoviridae,Rotavirus,Rotavirus A | seg. 5 | JF693063,JF693041,JF693030 |
| Bovine rotavirus A | NC_011501 | vertebrates,human | 3 | Reoviridae,Rotavirus,Rotavirus A | seg. 7 | JF693065,AB513838,JF693043 |
| Bovine rotavirus A | NC_011502 | vertebrates,human | 2 | Reoviridae,Rotavirus,Rotavirus A | seg. 8 | JF693066,JF693044 |
| Bovine rotavirus A | NC_011503 | vertebrates,human | 26 | Reoviridae,Rotavirus,Rotavirus A | seg. 9 | JX470523,JF720877,JF742652,AB513837,JF693045,JF720878,JX470522,JX470514,JX470516,EF200563,AB454421,JF693067,EF200560,JX470519,EF200549,JF689835,GU144587,EF199501,JX470518,EF200515,JX470521,JX470517,JF720882,JX470520,AB486011,DQ487203 |
| Bovine rotavirus A | NC_011504 | vertebrates,human | 11 | Reoviridae,Rotavirus,Rotavirus A | seg. 10 | JF693046,EF200578,GU18128,EF200575,EF200574,AY293829,EF200576,EF200573,EF592592,JF693068,EF200572 |
| Bovine rotavirus A | NC_011505 | vertebrates,human | 7 | Reoviridae,Rotavirus,Rotavirus A | seg. 11 | JF693047,EF200582,JF693069,EF200580,GU937876,EF200581,EF200579 |
| Bovine rotavirus A | NC_011506 | vertebrates,human | 3 | Reoviridae,Rotavirus,Rotavirus A | seg. 2 | JF693060,JF693027,JF693038 |
| Bovine rotavirus A | NC_011507 | vertebrates,human | 3 | Reoviridae,Rotavirus,Rotavirus A | seg. 1 | JF693059,JF693037,JF693026 |
| Bovine rotavirus A | NC_011508 | vertebrates,human | 4 | Reoviridae,Rotavirus,Rotavirus A | seg. 3 | AY300923,JF693061,JF693039,JF693028 |
| Bovine rotavirus A | NC_011509 | vertebrates,human | 11 | Reoviridae,Rotavirus,Rotavirus A | seg. 6 | JF720875,EF200569,JF693064,JF720873,JF742649,EF200568, |

| Taxonomy | NCBI Reference Sequence ID | Host | No. of Genomes | Lineage | Segment Count | Genbank Accession ID |
|---|---|---|---|---|---|---|
| Bovine rotavirus A | NC_011510 | vertebrates,human | 7 | Reoviridae,Rotavirus,Rotavirus A | seg. 4 | JF693042,JF720879, EF200565,JF742650, EF200567 JF693040,JF693029, AB513836,DQ838596 ,AB454420,AB48601 0,JF693062 |
| Bovine rotavirus B-11 | NC_011510 | vertebrates,human | 1 | Reoviridae,Rotavirus,Rotavirus A | seg. 4 | AY047488 |
| Bovine rotavirus G10 | NC_011504 | vertebrates,human | 1 | Reoviridae,Rotavirus,Rotavirus A | seg. 10 | AY527227 |
| Bovine rotavirus G15P11 | NC_011505 | vertebrates,human | 1 | Reoviridae,Rotavirus,Rotavirus A | seg. 11 | EU682404 |
| Bovine rotavirus G15P21 | NC_011504 | vertebrates,human | 1 | Reoviridae,Rotavirus,Rotavirus A | seg. 10 | AY527226 |
| Bovine rotavirus G6 | NC_011501 | vertebrates,human | 4 | Reoviridae,Rotavirus,Rotavirus A | seg. 7 | AB748598,AB748600 ,AB748597,AB74859 9 |
| Bovine rotavirus G6 | NC_011502 | vertebrates,human | 4 | Reoviridae,Rotavirus,Rotavirus A | seg. 8 | AB748594,AB748595 ,AB748592,AB74859 3 |
| Bovine rotavirus G6 | NC_011504 | vertebrates,human | 4 | Reoviridae,Rotavirus,Rotavirus A | seg. 10 | AB748604,AB748603 ,AB748605,AB74860 2 |
| Bovine rotavirus strain BRV033 | NC_011504 | vertebrates,human | 1 | Reoviridae,Rotavirus,Rotavirus A | seg. 10 | AF144804 |
| Bovine rotavirus strain RF | NC_011504 | vertebrates,human | 1 | Reoviridae,Rotavirus,Rotavirus A | seg. 10 | AY116593 |
| Bovine rotavirus strain RF | NC_011508 | vertebrates,human | 1 | Reoviridae,Rotavirus,Rotavirus A | seg. 3 | AY116592 |
| Buffalo rotavirus A 10733 | NC_011503 | vertebrates,human | 1 | Reoviridae,Rotavirus,Rotavirus A | seg. 9 | AY281360 |
| Buffalo rotavirus A 10733 | NC_011505 | vertebrates,human | 1 | Reoviridae,Rotavirus,Rotavirus A | seg. 11 | EU659853 |
| Bundibugyo ebolavirus | NC_014373 | vertebrates,human | 5 | Filoviridae,Ebolavirus,Bundibugyo ebolavirus | — | KC545394,KC545393 ,KC545396,FJ217161 ,KC545395 |
| CAS virus | NC_018481 | vertebrates,human | 1 | Arenaviridae,CAS virus | seg. S | JQ717262 |
| CAS virus | NC_018484 | vertebrates,human | 1 | Arenaviridae,CAS virus | seg. L | JQ717261 |
| Camberwell virus | NC_001959 | vertebrates,human | 1 | Caliciviridae,Norovirus,Norwalk virus | — | AF145896 |
| Canine distemper virus | NC_001921 | vertebrates,human | 43 | Paramyxoviridae,Morbillivirus,Canine distemper virus | — | AB490680,AB475099 ,EU726268,AB82370 7,AB490672,AB6877 21,AB490674,AX453 976,AB753775,AY46 6011,KF914669,AF01 4953,EU716337,AF3 05419,AB476401,AB 475097,AB490676,A Y386316,JN896331,A B462810,AF164967,A |

-continued

| Taxonomy | NCBI Reference Sequence ID | Host | No. of Genomes | Lineage | Segment Count | Genbank Accession ID |
|---|---|---|---|---|---|---|
| | | | | | | B823706,AB490678,AB476402,AB490681,GU138403,AY443350,AX453975,AB490670,AY386315,AY649446,AB490679,AY445077,HM852904,AY542312,AX453977,HM063009,HM046486,AB753776,AB474397,JN896987,AB687720,KC427278 |
| Canine distemper virus strain Onderstepoort | NC_001921 | vertebrates,human | 1 | Paramyxoviridae,Morbillivirus,Canine distemper virus | — | AF378705 |
| Canine rotavirus A79-10/G3P[3] | NC_011500 | vertebrates,human | 1 | Reoviridae,Rotavirus,Rotavirus A | seg. 5 | EU708940 |
| Canine rotavirus A79-10/G3P[3] | NC_011501 | vertebrates,human | 1 | Reoviridae,Rotavirus,Rotavirus A | seg. 7 | EU708941 |
| Canine rotavirus A79-10/G3P[3] | NC_011502 | vertebrates,human | 1 | Reoviridae,Rotavirus,Rotavirus A | seg. 8 | EU708942 |
| Canine rotavirus A79-10/G3P[3] | NC_011503 | vertebrates,human | 1 | Reoviridae,Rotavirus,Rotavirus A | seg. 9 | EU708939 |
| Canine rotavirus A79-10/G3P[3] | NC_011504 | vertebrates,human | 1 | Reoviridae,Rotavirus,Rotavirus A | seg. 10 | EU708943 |
| Canine rotavirus A79-10/G3P[3] | NC_011505 | vertebrates,human | 1 | Reoviridae,Rotavirus,Rotavirus A | seg. 11 | EU708944 |
| Canine rotavirus A79-10/G3P[3] | NC_011506 | vertebrates,human | 1 | Reoviridae,Rotavirus,Rotavirus A | seg. 2 | EU708935 |
| Canine rotavirus A79-10/G3P[3] | NC_011507 | vertebrates,human | 1 | Reoviridae,Rotavirus,Rotavirus A | seg. 1 | EU708934 |
| Canine rotavirus A79-10/G3P[3] | NC_011508 | vertebrates,human | 1 | Reoviridae,Rotavirus,Rotavirus A | seg. 3 | EU708936 |
| Canine rotavirus A79-10/G3P[3] | NC_011509 | vertebrates,human | 1 | Reoviridae,Rotavirus,Rotavirus A | seg. 6 | EU708938 |
| Canine rotavirus A79-10/G3P[3] | NC_011510 | vertebrates,human | 1 | Reoviridae,Rotavirus,Rotavirus A | seg. 4 | EU708937 |
| Canine rotavirus CU-1 | NC_011500 | vertebrates,human | 1 | Reoviridae,Rotavirus,Rotavirus A | seg. 5 | EU708918 |
| Canine rotavirus CU-1 | NC_011501 | vertebrates,human | 1 | Reoviridae,Rotavirus,Rotavirus A | seg. 7 | EU708919 |
| Canine rotavirus CU-1 | NC_011502 | vertebrates,human | 1 | Reoviridae,Rotavirus,Rotavirus A | seg. 8 | EU708920 |
| Canine rotavirus CU-1 | NC_011503 | vertebrates,human | 1 | Reoviridae,Rotavirus,Rotavirus A | seg. 9 | EU708917 |
| Canine rotavirus CU-1 | NC_011504 | vertebrates,human | 2 | Reoviridae,Rotavirus,Rotavirus A | seg. 10 | AF144806,EU708921 |
| Canine rotavirus CU-1 | NC_011505 | vertebrates,human | 1 | Reoviridae,Rotavirus,Rotavirus A | seg. 11 | EU708922 |
| Canine rotavirus CU-1 | NC_011506 | vertebrates,human | 1 | Reoviridae,Rotavirus,Rotavirus A | seg. 2 | EU708913 |
| Canine rotavirus CU-1 | NC_011507 | vertebrates,human | 1 | Reoviridae,Rotavirus,Rotavirus A | seg. 1 | EU708912 |
| Canine rotavirus CU-1 | NC_011508 | vertebrates,human | 1 | Reoviridae,Rotavirus,Rotavirus A | seg. 3 | EU708914 |
| Canine rotavirus CU-1 | NC_011509 | vertebrates,human | 1 | Reoviridae,Rotavirus,Rotavirus A | seg. 6 | EU708916 |

| Taxonomy | NCBI Reference Sequence ID | Host | No. of Genomes | Lineage | Segment Count | Genbank Accession ID |
|---|---|---|---|---|---|---|
| Canine rotavirus CU-1 | NC_011510 | vertebrates,human | 3 | Reoviridae,Rotavirus,Rotavirus A | seg. 4 | EU708915,D13401,L20876 |
| Canine rotavirus K9 | NC_011500 | vertebrates,human | 2 | Reoviridae,Rotavirus,Rotavirus A | seg. 5 | AF111946,EU708929 |
| Canine rotavirus K9 | NC_011501 | vertebrates,human | 1 | Reoviridae,Rotavirus,Rotavirus A | seg. 7 | EU708930 |
| Canine rotavirus K9 | NC_011502 | vertebrates,human | 1 | Reoviridae,Rotavirus,Rotavirus A | seg. 8 | EU708931 |
| Canine rotavirus K9 | NC_011503 | vertebrates,human | 1 | Reoviridae,Rotavirus,Rotavirus A | seg. 9 | EU708928 |
| Canine rotavirus K9 | NC_011504 | vertebrates,human | 1 | Reoviridae,Rotavirus,Rotavirus A | seg. 10 | EU708932 |
| Canine rotavirus K9 | NC_011505 | vertebrates,human | 1 | Reoviridae,Rotavirus,Rotavirus A | seg. 11 | EU708933 |
| Canine rotavirus K9 | NC_011506 | vertebrates,human | 1 | Reoviridae,Rotavirus,Rotavirus A | seg. 2 | EU708924 |
| Canine rotavirus K9 | NC_011507 | vertebrates,human | 1 | Reoviridae,Rotavirus,Rotavirus A | seg. 1 | EU708923 |
| Canine rotavirus K9 | NC_011508 | vertebrates,human | 1 | Reoviridae,Rotavirus,Rotavirus A | seg. 3 | EU708925 |
| Canine rotavirus K9 | NC_011509 | vertebrates,human | 1 | Reoviridae,Rotavirus,Rotavirus A | seg. 6 | EU708927 |
| Canine rotavirus K9 | NC_011510 | vertebrates,human | 2 | Reoviridae,Rotavirus,Rotavirus A | seg. 4 | EU708926,D13400 |
| Canine rotavirus RV198/95 | NC_011503 | vertebrates,human | 1 | Reoviridae,Rotavirus,Rotavirus A | seg. 9 | AF271089 |
| Canine rotavirus RV52/96 | NC_011503 | vertebrates,human | 1 | Reoviridae,Rotavirus,Rotavirus A | seg. 9 | AF271090 |
| Caprine rotavirus A | NC_011500 | vertebrates,human | 1 | Reoviridae,Rotavirus,Rotavirus A | seg. 5 | GU937883 |
| Caprine rotavirus A | NC_011501 | vertebrates,human | 2 | Reoviridae,Rotavirus,Rotavirus A | seg. 7 | JQ004978,GU937885 |
| Caprine rotavirus A | NC_011502 | vertebrates,human | 2 | Reoviridae,Rotavirus,Rotavirus A | seg. 8 | GU937884,JQ004977 |
| Caprine rotavirus A | NC_011503 | vertebrates,human | 5 | Reoviridae,Rotavirus,Rotavirus A | seg. 9 | GU937882,GU937888,GU937891,JQ004975,AY128708 |
| Caprine rotavirus A | NC_011504 | vertebrates,human | 2 | Reoviridae,Rotavirus,Rotavirus A | seg. 10 | GU937886,JQ004979 |
| Caprine rotavirus A | NC_011505 | vertebrates,human | 2 | Reoviridae,Rotavirus,Rotavirus A | seg. 11 | JQ004980,GU937887 |
| Caprine rotavirus A | NC_011506 | vertebrates,human | 2 | Reoviridae,Rotavirus,Rotavirus A | seg. 2 | JQ004971,GU937878 |
| Caprine rotavirus A | NC_011507 | vertebrates,human | 2 | Reoviridae,Rotavirus,Rotavirus A | seg. 1 | JQ004970,GU937877 |
| Caprine rotavirus A | NC_011508 | vertebrates,human | 2 | Reoviridae,Rotavirus,Rotavirus A | seg. 3 | JQ004972,GU937879 |
| Caprine rotavirus A | NC_011509 | vertebrates,human | 2 | Reoviridae,Rotavirus,Rotavirus A | seg. 6 | GU937881,JQ004974 |
| Caprine rotavirus A | NC_011510 | vertebrates,human | 2 | Reoviridae,Rotavirus,Rotavirus A | seg. 4 | GU937880,JQ004973 |
| Chandipura virus | NC_020805 | vertebrates,human | 2 | Rhabdoviridae,Vesiculovirus,Chandipura virus | | GU212858,GU212856 |
| Chandipura virus Dak AR D 111125 | NC_020805 | vertebrates,human | 1 | Rhabdoviridae,Vesiculovirus,Chandipura virus | | HM627187 |
| Chandipura virus IB An 9978 | NC_020805 | vertebrates,human | 1 | Rhabdoviridae,Vesiculovirus,Chandipura virus | | HM627186 |
| Chapare virus | NC_010562 | vertebrates,human | 1 | Arenaviridae,Arenavirus,Chapare virus | seg. S | EU260463 |
| Chapare virus | NC_010563 | vertebrates,human | 1 | Arenaviridae,Arenavirus,Chapare virus | seg. L | EU260464 |
| Chiba virus | NC_001959 | vertebrates,human | 1 | Caliciviridae,Norovirus,Norwalk virus | | AB042808 |
| Civet SARS Coy 007/2004 | NC_004718 | vertebrates,human | 1 | Coronaviridae,Betacoronavirus,Severe acute respiratory syndrome-related coronavirus | | AY572034 |
| Civet SARS Coy SZ16/2003 | NC_004718 | vertebrates,human | 1 | Coronaviridae,Betacoronavirus,Severe acute respiratory syndrome-related coronavirus | | AY304488 |
| Civet SARS Coy SZ3/2003 | NC_004718 | vertebrates,human | 1 | Coronaviridae,Betacoronavirus,Severe acute respiratory syndrome-related coronavirus | | AY304486

| Taxonomy | NCBI Reference Sequence ID | Host | No. of Genomes | Lineage | Segment Count | Genbank Accession ID |
|---|---|---|---|---|---|---|
| Colobus guereza papillomavirus type 2 | NC_015692 | vertebrates,human | 1 | Papillomaviridae,Betapapillomavirus,Colobus monkey papillomavirus | — | GU014533 |
| Convict Creek 107 virus | NC_005215 | vertebrates,human | 2 | Bunyaviridae,Hantavirus,Sin Nombre virus | seg. M | L33684,L33474 |
| Convict Creek 107 virus | NC_005216 | vertebrates,human | 2 | Bunyaviridae,Hantavirus,Sin Nombre virus | seg. S | U47135,L33816 |
| Convict Creek 107 virus | NC_005217 | vertebrates,human | 1 | Bunyaviridae,Hantavirus,Sin Nombre virus | seg. L | AF425256 |
| Cote d'Ivoire ebolavirus | NC_014372 | vertebrates,human | 1 | Filoviridae,Ebolavirus,Tai Forest ebolavirus | — | FJ217162 |
| Coxsackievirus A16 | NC_001612 | vertebrates,human | 22 | Picornaviridae,Enterovirus,Enterovirus A | — | KC755235,KF193630,KF193622,KF193629,KC755234,KC755222,KF193628,KF193620,KC755232,KF193624,KF193625,KC755230,KF193621,KF193631,KC755233,KC755229,KF193632,KC507895,KF193623,KC755231,KF193627,KF193626 |
| Coxsackievirus A2 | NC_001612 | vertebrates,human | 4 | Picornaviridae,Enterovirus,Enterovirus A | — | JX867332,JX867331,JX867333,JX867330 |
| Coxsackievirus A24 | NC_002058 | vertebrates,human | 1 | Picornaviridae,Enterovirus,Enterovirus C | — | KF725085 |
| Coxsackievirus A7 | NC_001612 | vertebrates,human | 4 | Picornaviridae,Enterovirus,Enterovirus A | — | GU942820,GU94282,GU942821,GU9428222 |
| Cupixi virus | NC_010252 | vertebrates,human | 1 | Arenaviridae,Arenavirus,Cupixi virus | seg. L | AY216519 |
| Cupixi virus | NC_010254 | vertebrates,human | 1 | Arenaviridae,Arenavirus,Cupixi virus | seg. S | AF512832 |
| Cutthroat trout virus | NC_015521 | vertebrates,human | 1 | Hepeviridae,Cutthroat trout virus | — | HQ731075 |
| Dobrava-Belgrade virus | NC_005233 | vertebrates,human | 15 | Bunyaviridae,Hantavirus,Dobrava-Belgrade virus | seg. S | AY961615,AY533120,AY961618,AY53311,8,AJQ09775,JQ026204,AJQ09773,AJ41061,5,AF44622,AJ13167,3,JF920150,AY16857,6,AJ131672,L41916,AJ410619 |
| Dobrava-Belgrade virus | NC_005234 | vertebrates,human | 8 | Bunyaviridae,Hantavirus,Dobrava-Belgrade virus | seg. M | AY961616,AY168577,AIQ09774,AY168578,JQ026205,JF920149,AI410616, L33685 |
| Dobrava-Belgrade virus | NC_005235 | vertebrates,human | 3 | Bunyaviridae,Hantavirus,Dobrava-Belgrade virus | seg. L | AI410617,JQ026206, JF920148 |
| Dolphin morbillivirus | NC_005283 | vertebrates,human | 1 | Paramyxoviridae,Morbillivirus,Cetacean morbillivirus | — | AJ608288 |
| Duvenhage virus | NC_020810 | vertebrates,human | 4 | Rhabdoviridae,Lyssavirus,Duvenhage virus | — | EU293120,EU293119,EU623444,JN986749 |
| Ebola virus-Mayinga, Zaire, 1976 | NC_002549 | vertebrates,human | 1 | Filoviridae,Ebolavirus,Zaire ebolavirus | — | AF086833 |

-continued

| Taxonomy | NCBI Reference Sequence ID | Host | No. of Genomes | Lineage | Segment Count | Genbank Accession ID |
|---|---|---|---|---|---|---|
| Echovirus 1 (strain Farouki ATCC VR-1038) | NC_001472 | vertebrates,human | 1 | Picornaviridae,Enterovirus,Enterovirus B | — | AF029859 |
| Echovirus 9 (strain Barty) | NC_001472 | vertebrates,human | 1 | Picornaviridae,Enterovirus,Enterovirus B | — | X92886 |
| Echovirus 9 (strain Hill) | NC_001472 | vertebrates,human | 1 | Picornaviridae,Enterovirus,Enterovirus B | — | X84981 |
| Echovirus E25 | NC_001472 | vertebrates,human | 1 | Picornaviridae,Enterovirus,Enterovirus B | — | JX976772 |
| Echovirus E30 | NC_001472 | vertebrates,human | 6 | Picornaviridae,Enterovirus,Enterovirus B | — | KC897073,JX854435, JX976773,EF066392, EF066391,AY948442 |
| Echovirus E6 | NC_001472 | vertebrates,human | 9 | Picornaviridae,Enterovirus,Enterovirus B | — | JQ929657,JX976771, KF042343,AB705309, KF042342,AB705311, AB705308,AB705310 ,JQ801 739 |
| Echovirus E9 | NC_001472 | vertebrates,human | 4 | Picornaviridae,Enterovirus,Enterovirus B | — | KC238668,JN596587, KC238669,KC238667 |
| Enterovirus 5666/5in/002209 | NC_001612 | vertebrates,human | 1 | Picornaviridae,Enterovirus,Enterovirus A | — | AF352027 |
| Enterovirus 5865/5in/000009 | NC_001612 | vertebrates,human | 1 | Picornaviridae,Enterovirus,Enterovirus A | — | AF316321 |
| Enterovirus A | NC_001612 | vertebrates,human | 1 | Picornaviridae,Enterovirus,Enterovirus A | — | U05876 |
| Enterovirus A71 | NC_001612 | vertebrates,human | 28 | Picornaviridae,Enterovirus,Enterovirus A | — | AB747374,AB747373 ,KC296444,KF13448 6,KF14412,KF31245 7,KC296445,KF1424 11,KF142413,AB7473 75,KC436270,KF668 443,KC954664,KF15 4355,KC954662,KC4 36271,KC436268,KC 436272,KC570452,K C43269,KC296443, KC436266,KC954663 ,KC570453,KC43626 7,KC436265,JQ5147 85,KF501389 |
| Enterovirus B | NC_001472 | vertebrates,human | 5 | Picornaviridae,Enterovirus,Enterovirus B | — | KC568448,KC568449 ,KC568447,KC56844 6,M16560 |
| Enterovirus B87 | NC_001472 | vertebrates,human | 1 | Picornaviridae,Enterovirus,Enterovirus B | — | KC292019 |
| Enterovirus B97 | NC_001472 | vertebrates,human | 1 | Picornaviridae,Enterovirus,Enterovirus B | — | GU550508 |
| Enterovirus CA55-1988 | NC_001472 | vertebrates,human | 1 | Picornaviridae,Enterovirus,Enterovirus B | — | AF241359 |
| Enterovirus Yanbian 96-83csf | NC_001472 | vertebrates,human | 1 | Picornaviridae,Enterovirus,Enterovirus B | — | AF230973 |
| Equine rotavirus A | NC_011500 | vertebrates,human | 1 | Reoviridae,Rotavirus,Rotavirus A | seg. 5 | JXQ36371 |
| Equine rotavirus A | NC_011501 | vertebrates,human | 6 | Reoviridae,Rotavirus,Rotavirus A | seg. 7 | KC815700,JXQ36373, JQ309143,KC815677 ,KC815688,KC81566 6 |

-continued

| Taxonomy | NCBI Reference Sequence ID | Host | No. of Genomes | Lineage | Segment Count | Genbank Accession ID |
|---|---|---|---|---|---|---|
| Equine rotavirus A | NC_011502 | vertebrates,human | 6 | Reoviridae,Rotavirus,Rotavirus A | seg. 8 | JQ309142,KC815665,KC815687,KC815676,JXQ36372,KC815699 |
| Equine rotavirus A | NC_011503 | vertebrates,human | 14 | Reoviridae,Rotavirus,Rotavirus A | seg. 9 | KC815674,AB595975,AY750925,AB595976,AB595979,AB595978,AB595977,L49042,JXQ36370,L49043,AB595974,AY750924,KC815685,KC815663 |
| Equine rotavirus A | NC_011504 | vertebrates,human | 5 | Reoviridae,Rotavirus,Rotavirus A | seg. 10 | KC815689,KC815667,JXQ36374,KC815701,KC815678 |
| Equine rotavirus A | NC_011505 | vertebrates,human | 3 | Reoviridae,Rotavirus,Rotavirus A | seg. 11 | KC815668,JXQ36375,JQ309144 |
| Equine rotavirus A | NC_011506 | vertebrates,human | 6 | Reoviridae,Rotavirus,Rotavirus A | seg. 2 | KC815681,JXQ36366,JQ309139,KC815695,KC815659,KC815670 |
| Equine rotavirus A | NC_011507 | vertebrates,human | 6 | Reoviridae,Rotavirus,Rotavirus A | seg. 1 | KC815680,JQ309138,KC815694,KC815669,KC815658,JXQ36365 |
| Equine rotavirus A | NC_011508 | vertebrates,human | 7 | Reoviridae,Rotavirus,Rotavirus A | seg. 3 | KC815696,JXQ36367,KC815660,KC815671,KC815682,JQ309140,AY277922 |
| Equine rotavirus A | NC_011509 | vertebrates,human | 5 | Reoviridae,Rotavirus,Rotavirus A | seg. 6 | KC815697,KC815662,JXQ36369,KC815673,KC815684 |
| Equine rotavirus A | NC_011510 | vertebrates,human | 3 | Reoviridae,Rotavirus,Rotavirus A | seg. 4 | KC815672,KC815661,KC815683 |
| European bat lyssavirus 1 | NC_009527 | vertebrates,human | 8 | Rhabdoviridae,Lyssavirus,European bat lyssavirus 1 | — | KF042301,EU626551,KF042302,EF157976,EU293112,KF155003,EU626552,EU293109 |
| European bat lyssavirus 2 | NC_009528 | vertebrates,human | 3 | Rhabdoviridae,Lyssavirus,European bat lyssavirus 2 | — | KF155004,EF157977,EU293114 |
| Fer-de-lance virus | NC_005084 | vertebrates,human | 1 | Paramyxoviridae,Ferlavirus,Fer-de-Lance paramyxovirus | — | AY141760 |
| Ferret hepatitis E virus | NC_001434 | vertebrates,human | 2 | Hepeviridae,Hepevirus,Hepatitis E virus | — | JN998606,JN998607 |
| Flexal virus | NC_010757 | vertebrates,human | 2 | Arenaviridae,Arenavirus,Flexal virus | seg. S | AF512831,AF485257 |
| Flexal virus | NC_010759 | vertebrates,human | 1 | Arenaviridae,Arenavirus,Flexal virus | seg. L | EU627611 |
| GB virus C | NC_001710 | vertebrates,human | 48 | Flaviviridae,Pegivirus,GB virus C | — | KC618398,AB013500,JN127373,D87710,AY949771,U45966,D8 |

| Taxonomy | NCBI Reference Sequence ID | Host | No. of Genomes | Lineage | Segment Count | Genbank Accession ID |
|---|---|---|---|---|---|---|
| GB virus C variant troglodytes | NC_001710 | vertebrates,human | 1 | Flaviviridae,Pegivirus,GB virus C | — | AF070476 |
| Giant panda rotavirus A | NC_011502 | vertebrates,human | 1 | Reoviridae,Rotavirus,Rotavirus A | seg. 8 | GU188281 |
| Giant panda rotavirus A | NC_011504 | vertebrates,human | 1 | Reoviridae,Rotavirus,Rotavirus A | seg. 10 | GU188282 |
| Giant panda rotavirus A | NC_011505 | vertebrates,human | 1 | Reoviridae,Rotavirus,Rotavirus A | seg. 11 | GU329526 |
| Giant panda rotavirus A | NC_011506 | vertebrates,human | 1 | Reoviridae,Rotavirus,Rotavirus A | seg. 2 | HQ641294 |
| Golden Gate virus | NC_018482 | vertebrates,human | 1 | Arenaviridae,Golden Gate virus | seg. L | JQ717263 |
| Golden Gate virus | NC_018483 | vertebrates,human | 1 | Arenaviridae,Golden Gate virus | seg. S | JQ717264 |
| Goose paramyxovirus SF02 | NC_005036 | vertebrates,human | 1 | Paramyxoviridae,Avulavirus,Goose paramyxovirus SF02 | — | AF473851 |
| Guanarito virus | NC_005077 | vertebrates,human | 3 | Arenaviridae,Arenavirus,Guanarito virus | seg. S | AY129247,AY497548,AF485258 |
| Guanarito virus | NC_005082 | vertebrates,human | 2 | Arenaviridae,Arenavirus,Guanarito virus | seg. L | AY216504,AY358024 |
| HBV genotype A | NC_003977 | vertebrates,human | 1 | Hepadnaviridae,Orthohepadnavirus,Hepatitis B virus | — | AP007263 |
| HBV genotype A1 | NC_003977 | vertebrates,human | 6 | Hepadnaviridae,Orthohepadnavirus,Hepatitis B virus | — | HE974375,HE974381,HE974370,HE97436 3,HE974365,HE9743 62 |
| HBV genotype A2 | NC_003977 | vertebrates,human | 6 | Hepadnaviridae,Orthohepadnavirus,Hepatitis B virus | — | HE974383,HE974364,HE974371,HE97437 4,HE974376,HE9743 67 |
| HBV genotype B | NC_003977 | vertebrates,human | 3 | Hepadnaviridae,Orthohepadnavirus,Hepatitis B virus | — | AB602818,AB554017,AB540582 |

Genbank Accession ID (first row, full): 7712,AF031828,U44402,D87263,AB003293,U75356,D90600,AF006500,AB008335,D87711,AF121950,U36380,HQ331233,AB013501,AB003289,AB0O8342,D87708,AF081782,KC618399,AB018667,AB008336,KC618401,AF031827,AF031829,AF104403,AB003288,U63715,HQ331235,AB003292,D87255,D87715,KC618400,U94695,D90601,D87713,AB003290,D87262,HQ331234,AB021287,D87714,D87709,AY196904

| Taxonomy | NCBI Reference Sequence ID | Host | No. of Genomes | Lineage | Segment Count | Genbank Accession ID |
|---|---|---|---|---|---|---|
| HBV genotype C | NC_003977 | vertebrates,human | 19 | Hepadnaviridae,Orthohepadnavirus,Hepatitis B virus | — | AB554020,AB540585,AB644286,AB644287,AB644280,AB554021,AB644281,AB560662,AB644284,AB554014,AB560661,AB554019,AB644283,AB554025,AB540584,AB554022,AB554015,AB540583,AB554018 |
| HBV genotype D | NC_003977 | vertebrates,human | 4 | Hepadnaviridae,Orthohepadnavirus,Hepatitis B virus | — | HE815465,AB554016,AB554024,AB554023 |
| HBV genotype D3 | NC_003977 | vertebrates,human | 2 | Hepadnaviridae,Orthohepadnavirus,Hepatitis B virus | — | HE974377,HE974379 |
| HBV genotype D4 | NC_003977 | vertebrates,human | 4 | Hepadnaviridae,Orthohepadnavirus,Hepatitis B virus | — | HE974372,HE974378,HE974373,HE974382 |
| HBV genotype E | NC_003977 | vertebrates,human | 3 | Hepadnaviridae,Orthohepadnavirus,Hepatitis B virus | — | HE974384,HE974380,AP007262 |
| HBV genotype F2 | NC_003977 | vertebrates,human | 2 | Hepadnaviridae,Orthohepadnavirus,Hepatitis B virus | — | HE974366,HE974369 |
| HBV genotype F4 | NC_003977 | vertebrates,human | 1 | Hepadnaviridae,Orthohepadnavirus,Hepatitis B virus | — | HE974368 |
| HBV genotype G | NC_003977 | vertebrates,human | 1 | Hepadnaviridae,Orthohepadnavirus,Hepatitis B virus | — | AP007264 |
| HBV genotype H | NC_003977 | vertebrates,human | 6 | Hepadnaviridae,Orthohepadnavirus,Hepatitis B virus | — | AB516393,AB516395,AP007261,AB516394,AB846650,AB298362 |
| HBV recombinant B/C | NC_003977 | vertebrates,human | 1 | Hepadnaviridae,Orthohepadnavirus,Hepatitis B virus | — | AB644282 |
| HBV recombinant C/G | NC_003977 | vertebrates,human | 1 | Hepadnaviridae,Orthohepadnavirus,Hepatitis B virus | — | AB644285 |
| HIV-1 CRF03_AB | NC_001802 | vertebrates,human | 1 | Retroviridae,Lentivirus,Human immunodeficiency virus 1 | — | AF193276 |
| HIV-1 CRF04_cpx | NC_001802 | vertebrates,human | 1 | Retroviridae,Lentivirus,Human immunodeficiency virus 1 | — | AF049337 |
| HIV-1 M_02CD,KS069 | NC_001802 | vertebrates,human | 1 | Retroviridae,Lentivirus,Human immunodeficiency virus 1 | — | FM877780 |
| HIV-1 M_02CD,LBTB032 | NC_001802 | vertebrates,human | 1 | Retroviridae,Lentivirus,Human immunodeficiency virus 1 | — | FM877779 |
| HIV-1 M_02CD,LBTB084 | NC_001802 | vertebrates,human | 1 | Retroviridae,Lentivirus,Human immunodeficiency virus 1 | — | FM877781 |
| HIV-1 M_02CD,MBTB047 | NC_001802 | vertebrates,human | 1 | Retroviridae,Lentivirus,Human immunodeficiency virus 1 | — | FM877782 |
| HIV-1 M_97CD,KFE267 | NC_001802 | vertebrates,human | 1 | Retroviridae,Lentivirus,Human immunodeficiency virus 1 | — | FM877778 |

| Taxonomy | NCBI Reference Sequence ID | Host | No. of Genomes | Lineage | Segment Count | Genbank Accession ID |
|---|---|---|---|---|---|---|
| HIV-1 M_97CD,KTB119 | NC_001802 | vertebrates,human | 1 | Retroviridae,Lentivirus,Human immunodeficiency virus 1 | — | FM877777 |
| HIV-1 M_97CD,MBFE250 | NC_001802 | vertebrates,human | 1 | Retroviridae,Lentivirus,Human immunodeficiency virus 1 | — | FM877783 |
| Hantaan virus | NC_005218 | vertebrates,human | 25 | Bunyaviridae,Hantavirus,Hantaan virus | seg. S | AF427322,AF427324, JQ665905,AY748309, AF321094,D25533,A Y017064,U37768,M1 4626,EF595840,HQ6 11981,AF427318,AB6 20031,JQ665906,AF4 27320,AB127998,D25 530,AF427319,AB027 111,AB027097,AF321 095,AB027101,DQ65 8415,AF427323,AY83 9871 |
| Hantaan virus | NC_005219 | vertebrates,human | 16 | Bunyaviridae,Hantavirus,Hantaan virus | seg. M | JQ665881,AB027115, EU074224,AB127995 ,AB030232,AB62003 2,U37729,D25532,Y0 0386,L08753,EU0746 72,U38177,AF345636 ,M14627,D25529,JQ6 65882 |
| Hantaan virus | NC_005222 | vertebrates,human | 6 | Bunyaviridae,Hantavirus,Hantaan virus | seg. L | D25528,AB620033,D 25531,X55901,DQ98 9237,AF336826 |
| Hantaan virus 84FLi | NC_005218 | vertebrates,human | 1 | Bunyaviridae,Hantavirus,Hantaan virus | seg. S | AF366568 |
| Hantaan virus 84FLi | NC_005219 | vertebrates,human | 1 | Bunyaviridae,Hantavirus,Hantaan virus | seg. M | AF366569 |
| Hantaan virus A16 | NC_005218 | vertebrates,human | 1 | Bunyaviridae,Hantavirus,Hantaan virus | seg. S | AF288646 |
| Hantaan virus A16 | NC_005219 | vertebrates,human | 1 | Bunyaviridae,Hantavirus,Hantaan virus | seg. M | AF288645 |
| Hantaan virus A9 | NC_005218 | vertebrates,human | 1 | Bunyaviridae,Hantavirus,Hantaan virus | seg. S | AF035831 |
| Hantaan virus CA09082007 | NC_005218 | vertebrates,human | 1 | Bunyaviridae,Hantavirus,Hantaan virus | seg. S | HQ834499 |
| Hantaan virus CA10081109 | NC_005218 | vertebrates,human | 1 | Bunyaviridae,Hantavirus,Hantaan virus | seg. S | HQ834500 |
| Hantaan virus CA10081113 | NC_005218 | vertebrates,human | 1 | Bunyaviridae,Hantavirus,Hantaan virus | seg. S | HQ834501 |
| Hantaan virus CA10081203 | NC_005218 | vertebrates,human | 1 | Bunyaviridae,Hantavirus,Hantaan virus | seg. S | HQ834502 |
| Hantaan virus CA10081206 | NC_005218 | vertebrates,human | 1 | Bunyaviridae,Hantavirus,Hantaan virus | seg. S | HQ834503 |
| Hantaan virus CA10081708 | NC_005218 | vertebrates,human | 1 | Bunyaviridae,Hantavirus,Hantaan virus | seg. S | HQ834504 |
| Hantaan virus CA10081905 | NC_005218 | vertebrates,human | 1 | Bunyaviridae,Hantavirus,Hantaan virus | seg. S | HQ834505 |
| Hantaan virus E142 | NC_005218 | vertebrates,human | 1 | Bunyaviridae,Hantavirus,Hantaan virus | seg. S | AF288644 |
| Hantaan virus H101S0 | NC_005218 | vertebrates,human | 1 | Bunyaviridae,Hantavirus,Hantaan virus | seg. S | HQ834506 |
| Hantaan virus Lee | NC_005219 | vertebrates,human | 1 | Bunyaviridae,Hantavirus,Hantaan virus | seg. M | DQ0377 |
| Hantaan virus N8 | NC_005218 | vertebrates,human | 1 | Bunyaviridae,Hantavirus,Hantaan virus | seg. S | EF077656 |
| Hantaan virus P09072 | NC_005219 | vertebrates,human | 1 | Bunyaviridae,Hantavirus,Hantaan virus | seg. M | HQ834507 |
| Hantaan virus 032 | NC_005219 | vertebrates,human | 1 | Bunyaviridae,Hantavirus,Hantaan virus | seg. M | DQ371905 |
| Hantaan virus 032 | NC_005222 | vertebrates,human | 1 | Bunyaviridae,Hantavirus,Hantaan virus | seg. L | DQ371906 |
| Hantaanvirus CGAa1011 | NC_005218 | vertebrates,human | 1 | Bunyaviridae,Hantavirus,Hantaan virus | seg. S | EF990913 |

-continued

| Taxonomy | NCBI Reference Sequence ID | Host | No. of Genomes | Lineage | Segment Count | Genbank Accession ID |
|---|---|---|---|---|---|---|
| Hantaanvirus CGAa1011 | NC_005219 | vertebrates,human | 1 | Bunyaviridae,Hantavirus,Hantaan virus | seg. M | EF990927 |
| Hantaanvirus CGAa1015 | NC_005218 | vertebrates,human | 1 | Bunyaviridae,Hantavirus,Hantaan virus | seg. S | EF990912 |
| Hantaanvirus CGAa1015 | NC_005219 | vertebrates,human | 1 | Bunyaviridae,Hantavirus,Hantaan virus | seg. M | EF990926 |
| Hantaanvirus CGAa2 | NC_005218 | vertebrates,human | 1 | Bunyaviridae,Hantavirus,Hantaan virus | seg. S | EU092219 |
| Hantaanvirus CGAa2 | NC_005219 | vertebrates,human | 1 | Bunyaviridae,Hantavirus,Hantaan virus | seg. M | EU092223 |
| Hantaanvirus CGAa31MP7 | NC_005218 | vertebrates,human | 1 | Bunyaviridae,Hantavirus,Hantaan virus | seg. S | EF990911 |
| Hantaanvirus CGAa31MP7 | NC_005219 | vertebrates,human | 1 | Bunyaviridae,Hantavirus,Hantaan virus | seg. M | EF990925 |
| Hantaanvirus CGAa31P9 | NC_005218 | vertebrates,human | 1 | Bunyaviridae,Hantavirus,Hantaan virus | seg. S | EF990910 |
| Hantaanvirus CGAa31P9 | NC_005219 | vertebrates,human | 1 | Bunyaviridae,Hantavirus,Hantaan virus | seg. M | EF990924 |
| Hantaanvirus CGAa4MP9 | NC_005218 | vertebrates,human | 1 | Bunyaviridae,Hantavirus,Hantaan virus | seg. S | EF990915 |
| Hantaanvirus CGAa4MP9 | NC_005219 | vertebrates,human | 1 | Bunyaviridae,Hantavirus,Hantaan virus | seg. M | EF990929 |
| Hantaanvirus CGAa4P15 | NC_005218 | vertebrates,human | 1 | Bunyaviridae,Hantavirus,Hantaan virus | seg. S | EF990914 |
| Hantaanvirus CGAa4P15 | NC_005219 | vertebrates,human | 1 | Bunyaviridae,Hantavirus,Hantaan virus | seg. M | EF990928 |
| Hantaanvirus CGAa75 | NC_005218 | vertebrates,human | 1 | Bunyaviridae,Hantavirus,Hantaan virus | seg. S | EU092220 |
| Hantaanvirus CGAa75 | NC_005219 | vertebrates,human | 1 | Bunyaviridae,Hantavirus,Hantaan virus | seg. M | EU092224 |
| Hantaanvirus CGHu1 | NC_005218 | vertebrates,human | 1 | Bunyaviridae,Hantavirus,Hantaan virus | seg. S | EU092218 |
| Hantaanvirus CGHu1 | NC_005219 | vertebrates,human | 1 | Bunyaviridae,Hantavirus,Hantaan virus | seg. M | EU092222 |
| Hantaanvirus CGHu3612 | NC_005218 | vertebrates,human | 1 | Bunyaviridae,Hantavirus,Hantaan virus | seg. S | EF990909 |
| Hantaanvirus CGHu3612 | NC_005219 | vertebrates,human | 1 | Bunyaviridae,Hantavirus,Hantaan virus | seg. M | EF990923 |
| Hantaanvirus CGHu3614 | NC_005218 | vertebrates,human | 1 | Bunyaviridae,Hantavirus,Hantaan virus | seg. S | EF990908 |
| Hantaanvirus CGHu3614 | NC_005219 | vertebrates,human | 1 | Bunyaviridae,Hantavirus,Hantaan virus | seg. M | EF990922 |
| Hantaanvirus CGRn45 | NC_005218 | vertebrates,human | 1 | Bunyaviridae,Hantavirus,Hantaan virus | seg. S | EU092221 |
| Hantaanvirus CGRn45 | NC_005219 | vertebrates,human | 1 | Bunyaviridae,Hantavirus,Hantaan virus | seg. M | EU092225 |
| Hantaanvirus CGRn53 | NC_005218 | vertebrates,human | 1 | Bunyaviridae,Hantavirus,Hantaan virus | seg. S | EF990907 |
| Hantaanvirus CGRn53 | NC_005219 | vertebrates,human | 1 | Bunyaviridae,Hantavirus,Hantaan virus | seg. M | EF990921 |
| Hantaanvirus CGRn5310 | NC_005218 | vertebrates,human | 1 | Bunyaviridae,Hantavirus,Hantaan virus | seg. S | EF990906 |
| Hantaanvirus CGRn5310 | NC_005219 | vertebrates,human | 1 | Bunyaviridae,Hantavirus,Hantaan virus | seg. M | EF990920 |
| Hantaanvirus CGRn93MP8 | NC_005218 | vertebrates,human | 1 | Bunyaviridae,Hantavirus,Hantaan virus | seg. S | EF990905 |
| Hantaanvirus CGRn93MP8 | NC_005219 | vertebrates,human | 1 | Bunyaviridae,Hantavirus,Hantaan virus | seg. M | EF990919 |
| Hantaanvirus CGRn93P8 | NC_005218 | vertebrates,human | 1 | Bunyaviridae,Hantavirus,Hantaan virus | seg. S | EF990904 |
| Hantaanvirus CGRn93P8 | NC_005219 | vertebrates,human | 1 | Bunyaviridae,Hantavirus,Hantaan virus | seg. M | EF990918 |
| Hantavirus CJAp93 | NC_005218 | vertebrates,human | 1 | Bunyaviridae,Hantavirus,Hantaan virus | seg. S | EF208929 |
| Hantavirus CJAp93 | NC_005219 | vertebrates,human | 1 | Bunyaviridae,Hantavirus,Hantaan virus | seg. M | EF208930 |
| Hantavirus Gou3-v9 | NC_005236 | vertebrates,human | 1 | Bunyaviridae,Hantavirus,Seoul virus | seg. S | AF288651 |
| Hantavirus LR1 | NC_005218 | vertebrates,human | 1 | Bunyaviridae,Hantavirus,Hantaan virus | seg. S | AF288294 |
| Hantavirus LR1 | NC_005219 | vertebrates,human | 1 | Bunyaviridae,Hantavirus,Hantaan virus | seg. M | AF288293 |
| Hantavirus LR1 | NC_005222 | vertebrates,human | 1 | Bunyaviridae,Hantavirus,Hantaan virus | seg. L | AF288292 |
| Hantavirus RG9 | NC_005218 | vertebrates,human | 1 | Bunyaviridae,Hantavirus,Hantaan virus | seg. S | AF288296 |
| Hantavirus S85-46 | NC_005218 | vertebrates,human | 1 | Bunyaviridae,Hantavirus,Hantaan virus | seg. S | AF288659 |
| Hantavirus S85-46 | NC_005219 | vertebrates,human | 1 | Bunyaviridae,Hantavirus,Hantaan virus | seg. M | AF288658 |
| Hantavirus SN7 | NC_005218 | vertebrates,human | 1 | Bunyaviridae,Hantavirus,Hantaan virus | seg. S | AF288657 |
| Hantavirus SN7 | NC_005219 | vertebrates,human | 1 | Bunyaviridae,Hantavirus,Hantaan virus | seg. M | AF288656 |
| Hantavirus Z10 | NC_006433 | vertebrates,human | 2 | Bunyaviridae,Hantavirus,Hantavirus Z10 | seg. S | EF533944,AF184987 |
| Hantavirus Z10 | NC_006435 | vertebrates,human | 1 | Bunyaviridae,Hantavirus,Hantavirus Z10 | seg. L | AF189155 |
| Hantavirus Z10 | NC_006437 | vertebrates,human | 2 | Bunyaviridae,Hantavirus,Hantavirus Z10 | seg. M | AF276987,AF143675 |
| Hantavirus Z37 | NC_005236 | vertebrates,human | 1 | Bunyaviridae,Hantavirus,Seoul virus | seg. S | AF187082 |
| Hantavirus Z37 | NC_005237 | vertebrates,human | 2 | Bunyaviridae,Hantavirus,Seoul virus | seg. M | AF187081,AF190119 |
| Hantavirus Z37 | NC_005238 | vertebrates,human | 1 | Bunyaviridae,Hantavirus,Seoul virus | seg. L | AF285266 |

-continued

| Taxonomy | NCBI Reference Sequence ID | Host | No. of Genomes | Lineage | Segment Count | Genbank Accession ID |
|---|---|---|---|---|---|---|
| Hantavirus strain CJilin93 | NC_005219 | vertebrates,human | 1 | Bunyaviridae,Hantavirus,Hantaan virus | seg. M | AY748307 |
| Hantavirus strain YU61 | NC_005218 | vertebrates,human | 1 | Bunyaviridae,Hantavirus,Hantaan virus | seg. S | AY748308 |
| Hawaii calicivirus | NC_001959 | vertebrates,human | 1 | Caliciviridae,Norovirus,Norwalk virus | | U07611 |
| Hendra virus | NC_001906 | vertebrates,human | 13 | Paramyxoviridae,Henipavirus,Hendra virus | — | HM044318,HM044321,JN255801,HM044320,JN255802,JN255806,JN255800,HM044317,JN255805,HM044319,JN255803,AF017149,JN255804 |
| Hepatitis B virus | NC_003977 | vertebrates,human | 5003 | Hepadnaviridae,Orthohepadnavirus,Hepatitis B virus | — | GQ377610,X59795,J0040171,JN257172, EU306678,EU916228,AB014372,JN040759,GU456658,JXQ26877,AF418690,AY800391,AY738144,AB195942,DQ823093,AB205191,GQ183474,AB330372,JN792915,AB014389,DQ089760,JN642143,AB900109,FJ386642,EU306702,JQ801498,EU306680,HM750150,HQ700441, DQ993702,JN040762,AB287317,AB674411,GU815656,JX507213,AJ627218,KC510656,DQ975273,EU939675,HM750147,FJ349240,JF828932,FN594754,GQ161801,AF223960,JN040772,HM011478,GU456681,AB036918,FJ562245,GU815755,GU815599, GQ161785,DQ463796,GU456648,KC875322,EU564825,AJ131571,HM011497,FJ787447,GU815746,EU579443,JN040805,L13994,AB670307,FJ151413,GQ377584,GQ183468,GQ924621,AB367425,GU815632,EU916204,AB675683,AB |

-continued

| Taxonomy | NCBI Reference Sequence ID | Host | No. of Genomes | Lineage | Segment Count | Genbank Accession ID |
|---|---|---|---|---|---|---|
| | | | | | | 036915,EU871978,D 0448619,JXQ96952,F J904419,EU717212,D 0304551,JN257179,F JQ32334,AY934763,G U815620,GQ377632, EU787444,HQ646553 ,GQ205379,FJ34920 9,AB670273,EU7172 15,EU522067,AB111 113,EU916206,JN664 919,JN257189,AB670 265,HM117851,GQ47 5320,GU456640,AY8 62868,FJ692559,FJ7 87482,GU815726,HM 750136,GQ377556,A B116093,HM585196, AB670244,AF143302, GQ924647,AY040627 ,GQ477455,AB11111 5,JQ429079,AY09045 8,GQ477497,EU8719 95,AB119252,AB270 535,FJ709459,JF440 004,GU815657,DQ08 9794,AB073840,FJ56 2297,GU815565,FJ56 2308,GQ161829,FN5 94763,AM494700,GU 815692,AY167092,E U305540,JX429903,A Y161150,FIQ23659,A B485808,AB900106, HQ603073,JXQ79936 ,DQ089804,FJ386613 ,EU871973,AB48580 9,AB670305,JQ02732 9,AB198081,AY6415 63,AB112408,HQ700 504,FJ349211,FJ904 435,FJ899761,D5052 0,AY217366,HQ7005 18,AB674423,FJ5622 62,GQ377561,AB010 292,FJ692568,AB367 409,X97849,JN63046 3,GU332696,JQ0401 |

-continued

| Taxonomy | NCBI Reference Sequence ID | Host | No. of Genomes | Lineage | Segment Count | Genbank Accession ID |
|---|---|---|---|---|---|---|
| | | | | | | 39,FJ904430,HM363576,JX898690,JN040775,DQ089768,FJ349237,DQ089782,AB014378,FJ562231,JQ687533,AY330913,FJ349222,AB219427,AY89200249,HM363603,FJ562328,EU306694,FJ562320,JX898686,FJ386630,JN040787,AB480041,AB198077,AF418686,AM494716,FJ692598,EU414137,FJ023670,HQ700522,AY738140,AB670261,JF491450,JN792900,JN040758,EF473977,AY090460,JF754611,DQ993697,FJ899785,AB048705,AB367429,HM363573,FJ899764,FJ787471,AB674434,AB453982,EU306681,JX504545,AB246340,GQ377614,EU939632,DQ478885,AB493836,AJ627228,AY641559,GU815575,JQO40132,JN642167,HQ700482,AF461357,GU815627,AB116079,JF491454,KC875342,EU859949,FJ692579,AB105173,FJ904425,HM750156,JN040815,EU366118,EU305544,GQ377585,AB073849,AY596111,AB032431,FJ562220,JX898699,HQ700463,KC494400,EU859899,AY057948,AM494689,AY661792,EU414140,G0183461,EU939593,FJ787465,KF679994,GQ475330,GQ924638,AY217358,EU59448 |

| Taxonomy | NCBI Reference Sequence ID | Host | No. of Genomes | Lineage | Segment Count | Genbank Accession ID |
|---|---|---|---|---|---|---|
| | | | | | | 27,GQ924643,GU815 595,JN792898,GQ18 3459,HQ231885,FJO3 2354,JXQ26882,FJ38 6643,AB086397,GQ3 77517,HM62135,JQ 801483,EU859915,G 0475334,GU815718, GQ183475,GQ37761 1,AB042283,AY2173 76,DQ060827,FJQ236 53,FJ562271,GQ161 824,DQ478894,FJ386 594,AB330367,JQ023 661,EU589344,AB27 0541,EU747320,JF75 4594,JX898689,EU85 9910,AY247032,GU8 15649,JN040797,FJ7 87450,FJ349232,GU8 15559,FJ562339,JN8 27425,GU56561,AM 421534,AY090454,KF 373035,FJ899776,FJ 899787,AJ131568,AY 167099,EU939570,G 0924633,EU919169, AY373429,JN040790, KC875310,JQ040145 ,GQ161787,HM01149 5,AB453989,EU7874 47,FJ787472,AB2987 21,HQ700461,KC875 279,GU815568,FJQ32 342,FJ386586,JF754 629,AB031267,AB03 1265,JQ040174,HQ7 00480,FJ709465,JN2 57204,GQ924614,JF 754613,EU717216,E F464097,AB674429,J N827419,DQ823090, GQ372968,AB014397 ,FJ692611,JN040818, FJ518813,GQ475327 ,EU306728,AB67441 0,GU815623,EU5545 39,EU939555,JF8993 |

| Taxonomy | NCBI Reference Sequence ID | Host | No. of Genomes | Lineage | Segment Count | Genbank Accession ID |
|---|---|---|---|---|---|---|
| | | | | | | 36,JN827420,JQ0236 60,AF121240,GQ377 527,EU594395,GQ37 7618,GQ377588,DQ4 63801,JQ027310,GQ 377534,EU916238,H M011487,Z35717,GQ 227692,GQ475309,E U522075,JX429915,A B270550,FJ692596,A Y090459,AF461363, HQ700445,FN594752 ,GU815686,JN64214 4,AB493840,AJ62721 9,JN400087,AY23327 9,HM066946,JX8986 97,KC875295,GQ924 628,AY741798,AB69 7488,GQ183483,AB1 12066,EU155822,EU 560440,GQ183448,G 0358157,FJ904400, GU815572,JN664942 ,FJ692588,FJQ23641, GQ477460,EU91621 7,AB375159,EU9396 03,GU815679,AB090 268,JN642135,GQ92 4651,HQ833467,DQ3 15777,JN664914,AB3 00365,FJ562334,KC8 75328,DQ993706,EU 939595,FJ562329,KC 494401,AB109479,K C494405,JQ801519, EU859916,HQ700487 ,DQ463791,AB36742 6,EU939565,EU9396 25,AB670269,AY596 110,EU414136,AB69 7502,JN664917,GU8 15634,HQ700497,FJ5 62302,GQ377530,GQ 924636,GQ161832,A B219532,JN040828,J N040774,FJ386597,F J386574,AF462041,A B367410,GU815781, |

| Taxonomy | NCBI Reference Sequence ID | Host | No. of Genomes | Lineage | Segment Count | Genbank Accession ID |
|---|---|---|---|---|---|---|
| | | | | | | JQ040164,KC875318,AB104710,KF495606,JF828938,JQ027333,FJ386579,EU871990,GU563347,AB24111 5,JN040824,GQ9246 60,GU815584,X1419 3,AB367434,EU8720 06,EU678471,GU456 678,AB555500,HQ23 1884,JN040800,GQ1 61757,HM750139,EU 939563,GQ477490,J 0664508,AP011095, EU939644,GQ47534 8,AB670288,DQ0897 92,JN257164,GQ183 462,GU815676,EU66 0233,HM363571,EU7 87443,GU815582,HQ 700495,GU456651,FJ 562279,AY934772,FJ 899773,FJ562310,H M535205,JF440012,J F828923,GQ924639, JN664909,KF679991, FJ562254,AB205190, JX429905,AB111118, HM011490,AB241112 ,AF223965,GU56521 7,FR714493,AY2173 59,FJ787461,GQ377 605,JF754615,JF754 606,DQ463800,AB20 5192,EU872002,JX42 9912,EU306677,GQ3 77540,KC875326,EU 882002,EU594401,A Y902775,FN545823,F J386640,JF440005,A M421529,EU919163, AB367400,AY206390 ,AY148342,DQ99580 5,AJ131572,DQ3157 81,HQ700477,KC875 265,FJ386590,AB106 895,EF103281,EU93 9658,GQ161830,EU9 |

| Taxonomy | NCBI Reference Sequence ID | Host | No. of Genomes | Lineage | Segment Count | Genbank Accession ID |
|---|---|---|---|---|---|---|
| | | | | | | 39598,EU570068,JN792903,AB675682,FJ386578,FJ349208,AM494695,DQ478892,AP011085,EU554535,AB115418,EU872011,AB246338,EU594433,GU815573,EU594432,KF373036,AF143298,FJ386614,AM494707,AB900104,EU305548,JF754618,GU815767,HE981177,FJ562304,GU815580,FJ386637,GU815728,HE981175,FJ787441,FJQ32335,GQ161837,GQ161754,EU871985,AB274970,HQ700536,JF754590,JN664932,GQ377569,JN257175,G0377637,FJ386628,KC875278,EU859924,JN257200,AB300368, AB073837,HQ231882,DQ089795,AM295800,EU589336,HQ603081,EU547563,AB014366,EU939640,JF754586,FJ798095,AJ131133,HQ700459,GU815779,V01460,EU939600,FJ904410,KF373034,AY721608,JF754612,GU815770,GU815555,GU815590,GU815633,GQ377601,GQ183473,FJQ23643,FJ562233,AB106564,AB246336,GQ358140,JN257196,AY233282,KF679993,AB231908,HE981182,JF440017,AY161158,HQ603061,JD23677,JX429900,AB642099,GQ161795,DQ207798,DQ060823,KC875281,HQ8334 |

-continued

| Taxonomy | NCBI Reference Sequence ID | Host | No. of Genomes | Lineage | Segment Count | Genbank Accession ID |
|---|---|---|---|---|---|---|
| | | | | | | 68,GU815729,AB188243,EU306688,FJ899794,HQ231877,GQ377526,EU562218,JQO27319,JX898695,AB036909,DQ377162,EU939543,HQ646554,G0377580,HQ646556,AY161151,FJ692583,AB059659,DQ993684,AB300372,FJ787485,FJ904433,AB365451,JF754604,HE981184,AY796031,EU872001,EU939664,AY163870,JN257201,JN040803,FJQ23646,FJ692582,FJ692574,JN257154,FJ562246,GQ377533,EU330995,JXQ26878,JX869999,HM535200,JN040764,HM363597,GU815631,GQ377523,DQ991753,JF754622,HM750155,AY862869,GU815611,AY161146,AF363961,GU815640,GQ477499,DQ060829,AY217362,AB014369,FN594765,FR714492,JN642152,FJ349214,FJ562293,EU939592,GU815665,FJQ23666,AM494703,AB493846,EU439011,EU916225,AB042282,FJ882618,EU916235,KC510659,GQ161826,AY161141,AY641562,AB198080,KF199901,JQ027331,JQ040131,AB116078,AB117759,JQ801487,JQ801481,AB026812,GU332698,AB014380,AB367412,AB367427,AB900096,AJ627226,AY741796,AB073 |

-continued

| Taxonomy | NCBI Reference Sequence ID | Host | No. of Genomes | Lineage | Segment Count | Genbank Accession ID |
|---|---|---|---|---|---|---|
| | | | | | | 836,EU939642,AB11 1120,FN594758,KC8 75293,GQ161793,AB 367397,EU410080,JX 429907,FJ562307,G 0358151,GQ477474, AB713530,AB642100 ,AB195932,GQ37757 3,EU594385,EF1572 91,AY233291,HM011 498,AB219529,EU87 1974,GQ475351,EUS 94428,AB195930,EU 350409,AB642098,A B674432,GQ358158, AP011089,GU815766 ,GU815682,HM58518 6,GQ377544,JXQ268 81,DQ298162,GQ477 467,EU522070,EF10 3280,AB493837,JF82 8925,KF373038,EF53 6066,GQ477462,EU9 39547,FJQ32350,AJ1 32335,DQ315783,AM 494696,JQ801484,G U815594,AY179735, DQ788727,EU410081 ,HQ700447,HM01147 6,AY217378,EU5943 83,DQ486023,GQ183 486,AB697512,JN182 331,EU594431,GQ16 1828,JX429901,AF09 0840,FIQ23661,EU58 9341,KF061169,EU9 39546,EU155824,HM 363595,EU939599,G 0161768,GQ475307, EF473971,DQ463797 ,GQ358159,AB27054 5,FJQ23632,GQ4774 53,EU919167,AY077 735,AB073827,AY37 3430,Z35716,HQ700 540,JN792899,GU45 6677,AB670253,EU9 39609,FJ589067,KC8 |

| Taxonomy | NCBI Reference Sequence ID | Host | Lineage | No. of Genomes | Segment Count | Genbank Accession ID |
|---|---|---|---|---|---|---|
| | | | | | | 75287,DQ315779,EU589339,EU594416,FN594766,AB048702,KC85305,FJ562306,AF241410,EU185780,GQ161761,KC87526 8,JN257206,FJ89978 6,EU305541,D28880,GU815563,HQ70052 0,GQ924642,JQ0401 35,AB670245,EU859 940,AB670284,AB27 0536,JQ272886,EU8 82004,HM750149,JX 079937,AB697509,JN 257165,EU871992,J 0801494,AY341335, AY161156,AF537371, EU547558,FM199976 ,AY233292,JN664948 ,EU306699,EU43901 8,FJQ32340,HM3635 74,EU564824,AY206 373,JF491448,EU939 556,EU859955,EU52 2069,EU410082,DQ0 89775,GQ477498,AB 367417,D23684,GQ4 75350,FJ562223,AY1 67097,AB640730,GQ 377608,KF679998,FN 594760,AB241109,A B246348,EU859946, AB050018,EU305546 ,JN257197,AB073841 ,GQ184323,AB90009 8,AB287315,DQ0898 00,GU815677,AM421 535,AB033554,JF754 616,FJ562330,JN040 791,GQ161762,EU93 9568,FJ562298,EU93 9574,FJ562287,KF17 0740,AB900108,FJ78 7452,JQ027314,DQ0 89756,AB670239,GU 815625,EU871991,JX 429917,JF828910,EU |

| Taxonomy | NCBI Reference Sequence ID | Host | No. of Genomes | Lineage | Segment Count | Genbank Accession ID |
|---|---|---|---|---|---|---|
| | | | | | | 939569,KF356417,KC836877,FJ386583,GU815662,JQ801489,EU306671,GQ37759 2,FJ709463,AY16709 5,AF143306,FJ89979 6,EU366133,FJ38664 1,GQ47748,KC8752 55,JQ801515,FJ5623 25,KC492739,AB205 120,AF282917,JN182 319,FJ692573,AB670 260,AY781187,GU45 6682,EU939662,DQ8 23089,HM011472,AB 270534,EU939654,G 0377542,FJ349219,D 0448625,KC875300, GU815688,GQ92464 9,EU589335,FJ38663 9,AF121242,AY93476 8,AY220703,DQ9936 94,JN040807,EU9162 24,GU815693,KC494 395,KF679996,GU33 2702,AB674415,JF82 8931,AB115551,GQ1 83467,FJ692578,JQO 40152,FJ386605,AB1 16092,AY862861,AB 670295,HQ603071,FJ 562327,GQ184325,A B670292,FN545822, DQ463802,FR714502 ,FJQ23671,JN257202, AB014388,AF418683, AB042285,FJ787442, GU815598,JF899335, JN664923,FJ386585, EU916237,JN183222, JN792922,GU815592 ,EU939620,FJ899779 ,FJ349212,X80924,G 0377626,AB033550, FJ386632,EU939665, DQ478896,EU678474 ,AB674404,DQ08976 7,X65259,AB670270, |

| Taxonomy | NCBI Reference Sequence ID | Host | No. of Genomes | Lineage | Segment Count | Genbank Accession ID |
|---|---|---|---|---|---|---|
| | | | | | | GQ475346,JN827414,DQ463788,JX870000,EF137802,FJ562314,GQ377539,JN257158,KC875297,KC875263,JN040792,DQ788835,AB033556,EU594424,EU859952,HM011473,GQ922002,AB116550,AF043580,AB118245,JQ801471,FJ904437,EU859951,J0801518,AB274969,EU589338,JN664918,KF425557,FJ386686,AY781180,EU859932,GQ227695,AY817510,FJ386658,FJ798098,AB036919,EF134945,DQ486021,FJ562296,EU414135,EU91629,JF828913,AF242585,AY206381,HM585193,AB014383,GU815725,JQ040161,FJO32332,AB274982,AY721606,EF103279,EU589337,DQ089762,AY596104,AM421530,AB697499,EU939610,HM363581,HQ231879,AF242586,EU48726,GQ161827,AF121247,AF533983,EU331000,AF461362,KC494399,EU859934,FJ904395,GQ377586,HM585200,GQ924656,J0801509,AM421537,GU815761,HM585187,AF297622,EU498227,HQ60305B,GU456672,AB014398,EU882001,AY220701,GU815641,AB642093,EU670261,FJQ32336,FM209512,GU815660,GU456647,HQ833465, |

| Taxonomy | NCBI Reference Sequence ID | Host | No. of Genomes | Lineage | Segment Count | Genbank Accession ID |
|---|---|---|---|---|---|---|
| | | | | | | AF090839,KF485390, EU939669,V00866,H E576988,FJ386636,G 0475338,GQ924620, EU564821,JN182320, FJ899767,EU919162, JF828935,AB116076, HM750142,GQ922200 3,GQ477504,JX8986 91,DQ993707,JQ801 504,DQ776247,FJ562 248,EU678472,EU88 2003,EU439012,AB2 46339,JX154580,AB0 10291,HQ622095,AB 182589,GQ475312,H 070502,AB205122, FJ657519,EU306682, FM209515,GU81561 3,AB246335,AB6702 42,EU859913,GQ924 615,AY206374,JN792 904,AB365446,EU83 3890,GQ477496,GQ3 77563,AY233295,FJQ 32341,AP011094,JQ8 01516,HQ700519,EU 594396,JF828914,JN 257180,KF679992,G 0924637,EU717213, JN182332,JX504546, DQ478901,JN040802 ,FN545834,JN040821 ,JFQ23665,JN642128, EU717211,JX898694, DQ020003,AB032432 ,AB287324,FN54584 2,HQ638218,GQ4753 13,AB330370,GQ161 818,EU239222,GU81 5735,DQ361535,JN2 57155,FJ386680,AB1 11112,FJ709460,GU8 15667,AB302943,AB 362933,AB112348,A B453985,FJ562337,E U859911,FJ692613,J F440016,EU939536,F |

| Taxonomy | NCBI Reference Sequence ID | Host | No. of Genomes | Lineage | Segment Count | Genbank Accession ID |
|---|---|---|---|---|---|---|
| | | | | | | M199979,HQ700542, JF754620,GQ377567 ,FJ386666,AB367424 ,JN664936,FJ386684, AB274980,AB670267 ,AB073822,KC87531 2,EU796070,AY0904 57,AB900097,EU939 601,AB059661,KC87 5252,X97851,EU9162 29,HM750135,FJ386 624,AY220699,EU30 6704,KC875339,GQ3 77631,AB670287,AB 014377,JQ027324,D 0486022,GQ161759, AB246341,JN257173, EU939634,AB642091 ,AY738142,AB05651 6,KF170739,AY16709 3,DQ089773,JF82893 3,AJ131575,JF75458 9,AY373431,AF22396 1,AB014379,DQ3990 06,AF090842,JN2571 88,AB195948,FJ3865 75,GU456663,HM011 465,AB274984,GQ16 1769,FJ386676,GQ3 77521,GQ161803,DQ 986376,JN182321,G 0358144,GU815772, EU916218,JN040801, AB090269,GQ475315 ,HM750154,GU45663 7,AB064311,DQ9937 08,EF494378,EU594 387,FJ709458,DQ298 161,AB453980,GU81 5589,EU594384,AB3 67398,GQ183452,JQ 429080,JQ027311,AB 205119,DQ975272,G 0924629,EU185788, AB073845,EU871988 ,JEF208114,HQ70047 9,HM011471,HQ7004 58,FN594750,DQ089 |

| Taxonomy | NCBI Reference Sequence ID | Host | No. of Genomes | Lineage | Segment Count | Genbank Accession ID |
|---|---|---|---|---|---|---|
| | | | | | | 803,EU158263,GU45 6661,FJ787474,AY20 6388,EU872009,AB0 10290,FJ798099,AM4 94693,EF103285,HM 363580,GU357843,A F411412,GU434374, FJ904406,AB073835, GU815604,FJ386683, X51970,HM363602,H M750134,FJ349210,A B210822,AY373428, GQ161775,GQ18345 4,DQ788726,Z72479, X75658,AB116077,FJ 023651,KC875266,JF 754626,AB201290,AF 143305,DQ377158,J N040783,AB471849, AB073844,GQ358153 ,AB091256,AB54921 3,AB775199,EU8599 18,AB073853,EU306 686,AF286594,GU56 3546,FJQ23668,DQ08 9785,EU939591,FJ69 2591,FN594748,AF22 3957,GU563555,JF82 8917,FJ562263,FJ56 2269,GQ924632,FJ7 98097,DQ089757,GQ 475308,AY077736,A B202072,X75657,JX4 29910,AB116080,GU 563557,EU306698,S7 5184,EU414132,EU9 39558,AB365453,AB 026815,FJ904414,AB 674414,JN040823,G 0161820,GU815616, AB205189,JX504533, FJ562243,AB241111, AY161157,GQ161782 ,GU456674,JX42989 8,,AY161159,AY2063 85,AB031266,FJ7874 39,AB900114,EU881 998,JX504539,EU414 |

| Taxonomy | NCBI Reference Sequence ID | Host | No. of Genomes | Lineage | Segment Count | Genbank Accession ID |
|---|---|---|---|---|---|---|
| | | | | | | 138,AB274978,GU45 6652,GU456638,EU3 06710,EU939631,GQ 924635,DQ089766,K C836879,AB219426, GU815574,JQ000008 ,JQ040167,EU91623 6,GQ161789,GU8156 75,KC774178,FJ8997 93,GQ167302,EU414 142,JN792905,KC875 311,FJ787445,DQ089 784,JN182329,GQ18 3455,KF170742,FJO3 2344,JN257152,GQ1 61819,AB032433,KF3 73040,AF143307,AF4 11409,AJ309370,AF1 43304,GQ377629,AB 195945,JF754605,AB 078031,EF494379,G 0924611,AB036906, KC875336,EU595031 ,AB367392,AY12342 4,JF754598,AM42153 2,AY781183,AB6744 37,JQ040149,HE981 183,GU815727,GQ47 5345,GU815601,AB3 02945,GQ475357,GQ 358147,EU796071,JF 436923,AY161152,KF 679995,FN594753,A B073831,AB697496, AB367404,FJ386623, FJQ32357,HM011474 ,DQ298163,EU30672 9,JQ027328,JN04077 6,GQ377570,AF3053 27,GQ161776,GU815 570,AB116083,FJ386 581,FJ562285,EU787 436,FJ386689,HQ700 534,AB073858,AF330 110,JQ801499,AY217 374,FJ904409,DQ304 550,AY217369,JXQ26 880,FJ904436,JQ023 |

| Taxonomy | NCBI Reference Sequence ID | Host | No. of Genomes | Lineage | Segment Count | Genbank Accession ID |
|---|---|---|---|---|---|---|
| | | | | | | 666,JN642161,IF754 587,AF121245,GU81 5642,KC875288,FJ56 2276,FJ349221,EU78 7440,DQ377164,JN6 64916,JX Q96953,AB1 95950,X68292,EU939 582,EU859945,GQ37 7593,GQ205377,AB1 09477,GU815765,GQ 377627,EU594407,D 50517,FJ787486,GQ 161833,FJ709464,JQ 027318,HM363613,A Y596106,EU916230, AB675677,AY800389 ,JN182334,EU939588 ,JN811655,HQ70048 5,D50522,KC875324, JQ040146,GU815583 ,EU306717,JN642139 ,GQ377519,AY70708 7,GU815744,AB7135 31,JN257198,FJ3866 27,HQ700486,FJ3492 34,GQ161800,DQ922 649,JQ801520,AB064 315,GQ477475,JN82 7422,FN545838,AB2 05129,HQ700537,AB 119253,FJ787469,GU 815606,AB270537,H 0646552,JQ040126, AB675679,GQ477493 ,FJQ32349,AF100309 ,EU919168,DQ99368 5,AB642101,EU3066 72,KC875314,FJ5188 10,HM363575,JN257 174,JQ000009,FN545 836,EF103283,JN257 161,JF754617,AF121 244,FJ904438,EU939 677,AB713529,AB49 3827,FN594756,AB3 67394,JF828929,JQO 40172,FJ692532,JQ8 01485,EF634481,JXQ |

-continued

| Taxonomy | NCBI Reference Sequence ID | Host | No. of Genomes | Lineage | Segment Count | Genbank Accession ID |
|---|---|---|---|---|---|---|
| | | | | | | 96956,JF440000,GU815694,FJ386681,AB287328,FJ562261,FJ562242,AB367405,AY161138,FJQ23676,AB674403,AB198083,AB106885,GQ183478,GU456665,GQ47748 3,GU456653,FJ70946 2,DQ89038 1,AB6702 38,AP0 11102,GU8 15579,FJ562274,EU306 691,JN642153,GU33 2707,AB287318,GQ4 77465,FJ562292,GQ 477461,AB205128,H M585192,EU859947, JX429896,FJ562301, JQ801505,GU815704 ,AF461358,AY206380 ,EU939581,HQ70054 3,GQ161763,HQ7005 35,DQ478886,EF103 284,FJ692563,JN792 914,AB367423,DQ99 3710,FJ562311,GU81 5751,JN257190,GQ9 24625,JN040768,EU9 16231,AM421536,X6 5257,FN594755,FJ90 4408,X97848,AF3843 71,FJ882614,EU9396 28,AB471852,JQ0401 53,GU815722,X7565 6,FJ562278,JN25716 0,EU871986,EU8352 40,X98072,FJQ23634, EU366132,HM36357 8,AB670252,DQ0897 65,AY233285,GU434 372,AB367407,FJ562 266,JXQ26887,GQ37 7600,AB480040,GU8 15768,GU456669,EU 872008,GQ377604,G 0161755,AB110075, GU815643,GU81556 0,GU815630,GQ9246 |

| Taxonomy | NCBI Reference Sequence ID | Host | No. of Genomes | Lineage | Segment Count | Genbank Accession ID |
|---|---|---|---|---|---|---|
| | | | | | | 10,EU564823,JN040808,GQ358150,GQ183471,FJ692577,KC875285,JQ027330,AB367399,DQ980549,AB368296,GU815564,AB014373,AB014370,FN545835,FJ562318,HM363565,AY217377,AB900100,FJ787437,Y18858,AB036920,H0700472,FJ787484,AY862865,AY934764,GQ184322,GU815738,AB330371,GQ205388,GU456676,AB266536,GU815668,GQ377516,GQ924623,EU306693,AY330914,GQ358145,EU331001,GU815681,AB073851,KC875299,GQ475306,AY781184,GU815752,JQ801488,AY796030,AB195952,GU815762,JF754597,EU330992,AB365449,JF754593,EU882000,KC875269,AB014361,DQ975271,EU939651,JN040798,AB367413,FN545839,HM011467,AB365447,GU815648,AB274972,HM363572,AB064316,DQ478883,GU815600,EU939613,AB670277,GQ475332,JF754625,EU871980,AB367395,GQ183477,FJ Q23675,GQ377596,GQ377529,DQ823088,FJ904403,JN664947,GQ205385,FJQ23662,AB555496,AB241114,EU881997,EU919165,DQ089802,JN257194,EU155825,GQ377559,JN664936493 |

| Taxonomy | NCBI Reference Sequence ID | Host | No. of Genomes | Lineage | Segment Count | Genbank Accession ID |
|---|---|---|---|---|---|---|
| | | | | | | 9,AB674407,EU9395 |
| | | | | | | 97,JN040777,GU456 |
| | | | | | | 646,KC494397,JQ68 |
| | | | | | | 7532,GQ377547,FJ3 |
| | | | | | | 86596,HM011492,AB |
| | | | | | | 670282,KC875316,K |
| | | | | | | C875335,AF418685, |
| | | | | | | AB241110,FN545832 |
| | | | | | | ,KC172106,AB21451 |
| | | | | | | 6,FN594764,DQ9805 |
| | | | | | | 50,FJ562319,JN2572 |
| | | | | | | 10,EU939580,FJ6925 |
| | | | | | | 65,AB014363,DQ986 |
| | | | | | | 375,EU439024,AY64 |
| | | | | | | 1560,AB119256,AY2 |
| | | | | | | 06391,FJ657529,KC8 |
| | | | | | | 75280,FJ787480,EF1 |
| | | | | | | 03276,HQ700464,JX |
| | | | | | | 898693,AB670250,E |
| | | | | | | U439015,FJ386673,J |
| | | | | | | F44013,AB073848, |
| | | | | | | GU815645,AY800392 |
| | | | | | | ,EU570075,JQ04014 |
| | | | | | | 2,AB300359,FJQ3235 |
| | | | | | | 9,JF754601,FJ56232 |
| | | | | | | 3,AF241411,GQ4774 |
| | | | | | | 52,EU306709,AB195 |
| | | | | | | 947,AB074756,AB11 |
| | | | | | | 1117,FJ882615,GQ1 |
| | | | | | | 83451,AY721605,EU |
| | | | | | | 939653,JN642165,EU |
| | | | | | | 939607,AB900101,G |
| | | | | | | 0414522,JF491449,J |
| | | | | | | 0411087,FJ899788,A |
| | | | | | | J131573,GQ377525, |
| | | | | | | HM750133,AY738147 |
| | | | | | | ,AY161154,GU56355 |
| | | | | | | 9,FJ151414,KC83688 |
| | | | | | | 0,AB270548,AY7381 |
| | | | | | | 43,EU330993,AF043 |
| | | | | | | 560,GU815731,FJ562 |
| | | | | | | 239,FJ562324,AB670 |
| | | | | | | 271,HM585195,AB20 |
| | | | | | | 6817,GU815635,EU5 |
| | | | | | | 94422,KC875327,GQ |
| | | | | | | 477473,FR714505,G |
| | | | | | | 0161778,HM750144, |
| | | | | | | EU939656,FJ386591, |

| Taxonomy | NCBI Reference Sequence ID | Host | No. of Genomes | Lineage | Segment Count | Genbank Accession ID |
|---|---|---|---|---|---|---|
| | | | | | | JQ027313,EU859933,EU939539,FJ562309,JN040817,AY217357,AB367416,JN257170,FJ787487,FN545821,FJ904413,GQ47534 2,AB073838,EU3067 12,FJ178476,AB1959 57,FJQ23658,EU9395 94,GU332705,JN040 757,AB670296,D2368 1,AB375170,KC8753 17,AY902769,JX5045 35,GQ377557,AJ131 570,AY233288,AJ344 115,EU939643,EU93 9562,AB198079,KC5 10645,GQ205381,GQ 377621,AB073856,G U815776,GQ377591, AY033073,AB493845 ,FJ657525,AB900115 ,DQ993704,EU33099 0,JF828922,JF75463 2,FJ899790,FJ38660 8,AB367414,DQ9937 03,JN257207,AB6702 43,DQ478881,JF7546 23,GQ161797,GU815 709,JF899338,AB375 160,FJ692605,FJ562 225,GQ475352,AB67 5680,AB241116,JQ66 4507,JN642146,KC51 0649,GQ161835,X72 702,GU815708,AY16 7098,FJQ23637,HQ70 0526,GQ377571,AB9 00099,JF828927,AB6 70266,EU939648,GQ 477501,FJ562326,AB 670294,GQ477476,A B046525,GU815651, EU859944,AP011088 ,EF688062,AM42154 3,JF828909,EU93960 5,FJ692570,AB11112 5,JN040750,GQ9246 |

| Taxonomy | NCBI Reference Sequence ID | Host | No. of Genomes | Lineage | Segment Count | Genbank Accession ID |
|---|---|---|---|---|---|---|
| | | | | | | 55,EU916227,AB300369,JQ040144,AB109478,AB471855,AM295798,AB048704,KC875306,JN792917,GQ358155,GQ377568,FJ899795,EU330998,AB219428,JN257211,AB287316,EU939615,JF754624,HM750153,EU589346,JN040827,DQ922651,AF473543,DQ089758,HQ700460,AM421533,KF767452,FJ386672,AB302944,DQ448621,JN257153,HQ603072,AB222710,AP011093,JN040781,JN400089,EU306721,AB036908,HQ603069,HM011504,AF384372,JN040806,D0993692,AB367428,AB219429,HQ231881,FJ692599,GQ924624,FJ562273,EU919175,GQ205380,AF043593,GU456654,GQ377624,JN040804,JQ023665,AY206389,KC510650,HQ700532,EU660229,GQ922000,AB194952,EU859937,AB116081,EU859908,AF418692,AB670279,JQ801491,FJ562305,AB073843,JN040825,KF679990,GQ477472,EU939553,EU547560,AM494690,GU815705,EU871982,DQ089764,X85254,EU554542,DQ478893,GU456641,AY217365,AB453987,AB194947,GU815663,FJ787444,AY781177,GQ475319,D23683,AB900107,AB47 |

| Taxonomy | NCBI Reference Sequence ID | Host | No. of Genomes | Lineage | Segment Count | Genbank Accession ID |
|---|---|---|---|---|---|---|
| | | | | | | 1851,FJ562272,EU911851,FJ562272,EU919197,AB112471,KC875271,FJ562253,AB287314,EU564820,FJ904424,GU815699,AY373432,GU815710,EU594430,GQ377548,AB674426,JN257171,AY090461,GU815716,GU815639,EU871994,AB014371,FJ904427,KC875303,AB471850,JQ664503,AF461361,JF828924,GU815673,KF373033,AB036910,GU456642,EU939649,EU939590,GU815773,FJ386661,EU939663,HQ236014,GU563554,FN545825,EU871983,AB674435,AB064313,EU939639,DQ089774,FJ787489,FJ349224,GQ183472,GU815674,GU8155578,AY161163,FJ904418,FN545826,JF412801,AB042284,FJ349220,HM363591,FJ904416,AB367415,DQ823092,AB270540,FJQ32352,GQ161777,EU594425,EF103282,AY721612,KC494404,D12980,AB205125,AB675674,JX429914,JQ040173,JQ801495,JN664937,AB287329,FN594762,X75664,HQ700491,AB274971,AB697505,GU357845,GQ97161823,FJ562303,DQ377165,EU859925,AJ627215,GQ358143,FJ562333,FJ386617,AB697492,AB674430,JN664911,EU939578,AP011092,JN040813, |

| Taxonomy | NCBI Reference Sequence ID | Host | No. of Genomes | Lineage | Segment Count | Genbank Accession ID |
|---|---|---|---|---|---|---|
| | | | | | | JQ040150,AF418679, EU939538,EU939641 ,FJQ23673,EU594436 ,EU155829,HQ70051 2,JN642137,FJ78745 8,GQ161811,AY2063 82,AB246344,EU306 726,HM011480,DQ08 9776,AB453988,EU9 39573,AY236163,EU 439023,EU330999,FJ 386622,AB471857,E U366116,JN257167,E U939638,KC875258, AB119251,HQ603079 ,AX155589,KC51065 1,FN594761,JN18232 8,JN040765,FJQ2364 9,AB036912,EU5700 74,JN182318,GQ377 551,JQ801475,FJ349 231,FJ562275,DQ060 825,GQ377638,AB01 4387,JN642163,AB11 7758,AB775201,JQ80 1479,DQ993687,FJ56 2240,FN594751,DQ0 89788,KC510643,FJO 23660,GU815666,JF8 28907,EU916216,JN8 27416,AB111122,FJ3 86635,EU872017,GQ 358136,JF444008,EU 439019,EU939660,FJ 562321,JX429906,AB 471848,X75663,HQ6 03067,GQ924648,AF 121249,GU815763,A B073830,HQ700531, DQ995801,FJ904422, JN040770,FJ874470, AB036905,AF223962, FJ386588,FJ692560, JN257208,EU660226, FJ787478,GU815672, FN594749,AP011106 ,AY057947,EU85994 8,GQ183484,FJ5622 |

| Taxonomy | NCBI Reference Sequence ID | Host | No. of Genomes | Lineage | Segment Count | Genbank Accession ID |
|---|---|---|---|---|---|---|
| | | | | | | 82,AB453981,AB330368,AY862864,GQ377574,FJ787477,HM363609,GQ331048,AY206377,GU815553,AY738145,DQ377160,AY233274,EU306711,AB367420,GU815637,FJ562256,EU594390,EU939622,GQ924612,EU562219,FJ904439,AB274975,AB367433,EU871997,FJ562244,AB670249,JQ687530,EU670263,KF061170,GU721029,AB670300,AY741794,AB675676,GU332699,AB014382,JX429897,J0027315,DQ993709,AJ309371,AY739675,GQ377553,G U565553,AM184125,FR714498,JQ801514,AB642096,EU594393,AF297621,GQ477459,JN792897,AY167091,AY161155,AF223959,JN642156,V00867,FN545827,AB074755,EU859928,FJ386606,GQ377628,AM494705,HE981176,EU859914,G0924616,AF411411,GQ183463,AB112065,GQ161831,EU306687,GQ161780,EU589343,GU815654,AM494711,FJ386601,AB219430,JN257212,EF137803,JF439999,FJ692592,KC510655,AY206375,GU815720,JN792921,KC875320,AB270538,GU815741,GU456635,AB493847,DQ377163,JQ040127,AF418691,JQ027323 |

| Taxonomy | NCBI Reference Sequence ID | Host | No. of Genomes | Lineage | Segment Count | Genbank Accession ID |
|---|---|---|---|---|---|---|
| | | | | | | ,HQ700528,DQ899147,HM363567,JXQ96958,GQ377520,AB375168,DQ478899,EU589345,EU155826,AY817512,EU670262,D16667,HM363612,HQ603078,EU939587,JX507210,AY934774,GQ477494,FJ899777,EU871987,AF182804,FJ386660,HM363588,AB70262,EU185786,AF479684,FN545824,AB113876,JN664913,AB205152,EU921418,AF090838,JQ801500,EU560439,U87742,AM494702,GQ358138,DQ089779,FJQ32338,AY934766,JX898696,GQ477458,FJ518812,GQ477486,AM117395,EU859900,EU579441,EU939549,AB300367,EU787442,FJ899775,X98073,AB105172,GQ377576,FJ904431,AB059660,FJ349225,GQ377595,AB194951,EU939619,GQ477491,AP011098,EU939627,AB674504,AB674418,FJ562290,GU815661,GU332703,GU815697,EU562217,JN642133,FJ386645,AB453979,JN792919,H0603075,JN400088,D23680,DQ089787,GU815671,GU563545,HM363605,HM363604,AB270549,JN642147,HQ700483,DQ463792,HQ603076,AB367802,GQ475347,EU871999,AM295796,GQ377528,GQ167301,EU |

| Taxonomy | NCBI Reference Sequence ID | Host | No. of Genomes | Lineage | Segment Count | Genbank Accession ID |
|---|---|---|---|---|---|---|
| | | | | | | 498228,HQ700442,FJ386646,EU939650,GU332700,GU451682,HQ700444,JN257176,JN257215,FJ386638,FJ386675,AB367408,KC012653,EU939584,GQ377558,AB69750,0,AY781185,FJ89976,6,HM59047l,EU67840,AB670297,AB36293l,GQ161809,GQ161817,FJ787463,GQ183485,AB45398,3,AY817514,AY738139,AM494699,FM209513,JQ040140,AB900102,FJ386577,AB670290,KC875331,EU594397,GQ358149,AB073855,JN792911,HQ700507,JN257178,AB116091,AB300373,AB367402,HQ700511,JF440001,AB485810,JQ927384,HQ231878,EU594406,JF491447,HQ700499,AY206393,DQ304548,FJ386664,GQ161770,AY220700,D0315778,JF828906,EU871989,AY161153,EU594388,DQ478900,AB201287,JN642166,JN040789,AB014392,HM011481,JN257157,AP011104,JF828926,EU660231,GQ377602,EU330996,KC875264,JN257187,JN040778,EU939629,FJ562250,GU815652,FM199977,EU589342,FJ386584,FJ562267,GU815562,JF828921,GU815685,FJ562255,EU939681,FJ692569,EU579442,GU815659,AF2 |

| Taxonomy | NCBI Reference Sequence ID | Host | No. of Genomes | Lineage | Segment Count | Genbank Accession ID |
|---|---|---|---|---|---|---|
| | | | | | | 80817,AB697508,EF103275,GU815759,JX470760,FJ787473,KC875334,JQ027325,EU939636,JN827418,KC875304,KC494394,FJ692554,GQ358154,JX429904,GQ377545,JQ801506,JF49145,3,AY211370,DQ975274,AB367431,AY596103,AB493841,GU815717,JX898688,HMO11475,FR714501,JX504538,HM011503,AF182802,HQ700454,H0700469,AB033551,EU522071,EU916219,JN040753,AB116266,FJ562336,FJ349226,EU833889,EU916239,EU939554,JQ801470,AB375163,JF44001087,GQ331046,AY518556,JF439996,GU456664,AB670283,Z72478,HQ700448,FJ692567,DQ361534,FJ692536,AB179747,AB0379 27,AF121243,EU239223,AY766463,AM494710,JN664930,FJ899792,FJ562291,AY233287,FJ899772,EU871969,AM295795,GU815680,AB064310,AY233296,HM590473,FJ562226,EU439025,JN664921,FN545837,GU815758,FJQ32356,AM421546,GQ924606,GQ161804,FJ562335,EU155821,GU434373,EU939672,EF464098,AF297623,EU939617,GQ183453,AB697497,EF536065,AB |

| Taxonomy | NCBI Reference Sequence ID | Host | No. of Genomes | Lineage | Segment Count | Genbank Accession ID |
|---|---|---|---|---|---|---|
| | | | | | | 697507,AY233278,G |
| | | | | | | 0475336,Y18855,EU |
| | | | | | | 570070,FJ899765,AY |
| | | | | | | 217373,HQ700506,G |
| | | | | | | 0922005,GU815609, |
| | | | | | | AP011103,FJQ32339, |
| | | | | | | JN040812,GU815602 |
| | | | | | | ,EU939589,GQ47534 |
| | | | | | | 0,AY903452,GU3327 |
| | | | | | | 06,EU916214,X98076 |
| | | | | | | ,JX504540,DQ08979 |
| | | | | | | 9,JF754614,DQ08977 |
| | | | | | | 8,GQ377555,HQ7004 |
| | | | | | | 98,AY206386,JN6421 |
| | | | | | | 51,AF151735,GU456 |
| | | | | | | 656,AB270544,AY21 |
| | | | | | | 7355,JN040814,DQ8 |
| | | | | | | 23091,AB670241,EU |
| | | | | | | 859954,FJ787462,FJ |
| | | | | | | 787454,JN040826,AB |
| | | | | | | 188242,AB674428,FJ |
| | | | | | | 386595,EF473972,D |
| | | | | | | 0089772,JQ664506, |
| | | | | | | FJ386654,EU306715, |
| | | | | | | JXQ26885,GQ924646 |
| | | | | | | ,GQ161812,GU45668 |
| | | | | | | 0,KC875313,EU9396 |
| | | | | | | 78,FJ904415,EU9395 |
| | | | | | | 75,FJ899791,AP0110 |
| | | | | | | 84,FJ386589,GQ161 |
| | | | | | | 756,EU859905,AB35 |
| | | | | | | 3764,GU815581,AM4 |
| | | | | | | 94718,JQ040157,AB2 |
| | | | | | | 19531,FJ899780,FJ3 |
| | | | | | | 86665,DQ993693,JN |
| | | | | | | 182327,JN642160,FJ |
| | | | | | | 349215,EF494376,G |
| | | | | | | U815777,AY311369, |
| | | | | | | EU594423,FJ386609, |
| | | | | | | GQ183465,KC31539 |
| | | | | | | 9,JN257163,FJ65752 |
| | | | | | | 8,EU939655,EU8352 |
| | | | | | | 42,JF754603,AB2012 |
| | | | | | | 88,EU594399,GU815 |
| | | | | | | 558,XQ4615,AB11194 |
| | | | | | | 6,AB674413,AB7135 |
| | | | | | | 28,AB212626,FJ3492 |
| | | | | | | 39,AB11121,JX5045 |

| Taxonomy | NCBI Reference Sequence ID | Host | No. of Genomes | Lineage | Segment Count | Genbank Accession ID |
|---|---|---|---|---|---|---|
| | | | | | | 34,JX560519,GU815 |
| | | | | | | 690,JQ040151,JQ687 |
| | | | | | | 531,EU871972,HM36 |
| | | | | | | 3596,AB014362,HQ6 |
| | | | | | | 03059,AY167089,GQ |
| | | | | | | 205441,AM410963,H |
| | | | | | | M585191,FJ562340,A |
| | | | | | | Y661793,GU815626, |
| | | | | | | EU560438,JN642155, |
| | | | | | | HM363582,HM36359 |
| | | | | | | 9,DQ536414,AB3751 |
| | | | | | | 65,AB670256,FJ5622 |
| | | | | | | 28,AP011099,M3213 |
| | | | | | | 8,HQ700492,FJ38659 |
| | | | | | | 2,AB670298,AY7811 |
| | | | | | | 82,AB375166,FR714 |
| | | | | | | 506,GQ377546,X756 |
| | | | | | | 65,FJQ23648,AB1094 |
| | | | | | | 75,GU815549,Y0758 |
| | | | | | | 7,EU787434,AB3674 |
| | | | | | | 19,JQ040134,AB6702 |
| | | | | | | 58,JF439997,HQ6030 |
| | | | | | | 63,EU305542,JF4369 |
| | | | | | | 20,EU594435,AB300 |
| | | | | | | 364,JF754610,DQ993 |
| | | | | | | 689,FJ899769,FJ692 |
| | | | | | | 585,AB246337,JN257 |
| | | | | | | 149,GU332701,AJ74 |
| | | | | | | 8098,EU594421,EU7 |
| | | | | | | 96072,FJ562332,EU9 |
| | | | | | | 39668,EU562216,FJ6 |
| | | | | | | 92507,Y18856,FJ904 |
| | | | | | | 396,AM117397,X978 |
| | | | | | | 50,GQ377589,EU939 |
| | | | | | | 542,AB120308,KC51 |
| | | | | | | 0654,AY161144,GQ9 |
| | | | | | | 24619,X80926,GQ47 |
| | | | | | | 7481,AM494713,JQ7 |
| | | | | | | 32168,GU815783,EU |
| | | | | | | 522073,FJ692600,JQ |
| | | | | | | 801482,FJ692556,JF |
| | | | | | | 828919,AB048701,A |
| | | | | | | B113877,FJ356715,A |
| | | | | | | B642097,HQ700471, |
| | | | | | | AF143303,FJ899789, |
| | | | | | | FJ386655,HM585194 |
| | | | | | | ,GQ377609,EU66022 |
| | | | | | | 7,AB073829,GQ1617 |

-continued

| Taxonomy | NCBI Reference Sequence ID | Host | No. of Genomes | Lineage | Segment Count | Genbank Accession ID |
|---|---|---|---|---|---|---|
| | | | | | | 86,JF439994,FJ9044 |
| | | | | | | 28,GU815695,GQ161 |
| | | | | | | 825,FJQ32333,AB367 |
| | | | | | | 396,FJ904401,GU563 |
| | | | | | | 551,HQ700450,KF06 |
| | | | | | | 1167,AB014364,AF41 |
| | | | | | | 8676,GQ183457,HM3 |
| | | | | | | 63590,DQ448627,AY |
| | | | | | | 817509,JN040830,JN |
| | | | | | | 040761,FJ349233,JF |
| | | | | | | 754600,AB195941,E |
| | | | | | | U796067,KC510657, |
| | | | | | | GQ183466,EU85995 |
| | | | | | | 0,FJ562265,AB67024 |
| | | | | | | 6,GQ205384,DQ9937 |
| | | | | | | 05,HM363568,AM421 |
| | | | | | | 542,AY217361,JN257 |
| | | | | | | 182,EU366129,JN315 |
| | | | | | | 779,FJ349229,EU916 |
| | | | | | | 220,GQ477478,DQ30 |
| | | | | | | 4549,AM422939,AB1 |
| | | | | | | 95935,DQ478897,AB |
| | | | | | | 116088,AY233283,E |
| | | | | | | U439021,GQ477454, |
| | | | | | | EU522072,EU306697 |
| | | | | | | ,FJQ23642,GU456649 |
| | | | | | | ,EU919174,DQ99368 |
| | | | | | | 2,AY330916,GU8156 |
| | | | | | | 08,AP011096,AB493 |
| | | | | | | 838,JF828934,EU939 |
| | | | | | | 540,EU859930,KC87 |
| | | | | | | 5262,AY206376,AB3 |
| | | | | | | 67411,FJQ32331,FJ8 |
| | | | | | | 82611,EU547562,AY |
| | | | | | | 781179,AB675681,H |
| | | | | | | 0700524,AY233286,J |
| | | | | | | F754591,EU239218, |
| | | | | | | AY161145,HM011477 |
| | | | | | | ,AJ627223,EU939680 |
| | | | | | | ,JQ040129,JN664922 |
| | | | | | | ,EU939626,AF41868 |
| | | | | | | 1,FN545840,FJ56229 |
| | | | | | | 4,HQ700514,AB3674 |
| | | | | | | 06,FJ386674,FJ8997 |
| | | | | | | 74,HE981172,KC875 |
| | | | | | | 259,KC875325,HQ70 |
| | | | | | | 0503,AF121241,DQ9 |
| | | | | | | 95803,AB674431,GU |

| Taxonomy | NCBI Reference Sequence ID | Host | No. of Genomes | Lineage | Segment Count | Genbank Accession ID |
|---|---|---|---|---|---|---|
| | | | | | | 456673,GU815569,AB20071,EU594434,EU554538,EU939596,EU306724,EU305543,EU717214,AY206387,EU796066,FJ386603,FJ349296,FJ904432,HM011488,FJ787436,HM585188,HQ700470,XQ2496,JF828915,KF679988,AY238972,HQ231883,AM494691,HM363592,JN664925,AB274981,GQ377560,KC492740,GU815778,AB670280,G0161790,DQ486024,FJ386620,HQ700510,AB116551,FJ349205,JQ040155,AB116082,EU859909,HM011502,DQ899149,HE981178,GQ377613,EU239217,AF223954,GU815714,JQ027334,DQ298164,JXQ96954,FJ787438,HQ700440,GU815621,FR714499,AB078033,JN040819,AB014374,EU306700,FJ692558,AB583681,AM494692,HE981174,FJ904399,FJ386625,AB201289,AF182805,HM585190,EU594389,JX504536,HM011494,GQ377639,AY236164,EU939606,JN040793,AB697503,DQ089777,JQ040130,EU086721,GU456667,EU939550,AB367432,AY902776,GQ161802,AJ627216,FJ562260,AB073828,JQ801517,FJQ23667,AB583679,GU357846,EU410079,JF828912,AY206378 |

| Taxonomy | NCBI Reference Sequence ID | Host | No. of Genomes | Lineage | Segment Count | Genbank Accession ID |
|---|---|---|---|---|---|---|
| | | | | | | ,GU815591,DQ44862 2,JX504544,AB67442 2,AB246346,JQ04016 0,FJ386618,GQ3775 77,GU815670,AB115 417,FJ562322,HQ700 505,EU594408,FJ904 398,FJ562281,AB368 295,JN257214,AF121 251,AY167102,FJ709 494,DQ899148,JN25 7177,AM421531,JF75 4621,EU859941,FJ56 2222,AB210818,JN04 0766,FJ386576,AB01 4390,M38454,FN594 771,JN400086,EF473 975,GQ183481,EU93 9557,FJQ32355,AB03 6907,XQ1587,EU2392 25,FM199980,FN545 831,JF754602,GU168 596,AB697489,KF373 041,GU815619,AB77 5200,JQ801486,HQ7 00496,AB219534,JQO 27312,U87747,AB091 255,KC875275,GQ16 1794,DQ315785,GQ1 61773,AB493833,AB 480036,JF828936,AB 697494,JQ040138,K C875292,FJ386653,G 0183479,FJ904446,A M494701,GU815658, HM363589,GQ92464 4,JN642149,GQ3775 99,AB195936,JQ8014 90,JN257166,EF1349 46,GU815629,AY217 360,HQ700500,FJ562 283,FJ386602,DQ993 683,FJ386619,GU815 587,FJ386659,HM36 3579,JN792909,JN04 0820,JF828905,EU93 9671,JX504543,AB03 6916,JN040751,DQ4 |

-continued

| Taxonomy | NCBI Reference Sequence ID | Host | No. of Genomes | Lineage | Segment Count | Genbank Accession ID |
|---|---|---|---|---|---|---|
| | | | | | | 48620,GU815617,HM011466,EU939585,AF418680,EU239220,AB367393,AB375169,EU306695,HQ70050 9,AB674417,GU4566 84,GQ475311,FJ787 481,EU155823,KC87 5270,GU456671,AB1 95954,GQ475331,GU 815715,AB274985,A B205123,GQ475326, JN642134,AM180623 ,FJQ32346,EU522066 ,EU414141,AJQ12207 ,AB195943,DQ82308 7,AY217375,EU3067 20,HM750140,JX154 579,AM421547,AY90 2774,GU357844,GU8 15734,FJQ23633,FJ3 86669,EU670260,FJ3 49235,AB056514,FJ8 99762,AM421539,AB 078032,AB493831,D 0315782,JQ429081, AB222711,AB210819 ,AB036911,FN54584 1,HQ231880,JQ0401 33,AF418675,GQ924 604,AB036913,KC51 0644,EU939623,HQ7 00513,AY206384,GQ 92641,KC875284,A Y233280,GQ358146, AB205010,JQ023664, GU456662,GQ18345 0,JN182325,EU93965 2,FJ787451,FJ56222 9,GU456644,AB9001 10,GQ377536,AB426 467,JN792920,HQ70 0446,AY220704,JF75 4627,FJ386612,AY15 2726,DQ478882,GU1 77079,JN642145,DQ 993680,AY161161,FJ 692255,JX869998,D2 |

| Taxonomy | NCBI Reference Sequence ID | Host | No. of Genomes | Lineage | Segment Count | Genbank Accession ID |
|---|---|---|---|---|---|---|
| | | | | | | 3678,GQ358141,AB2 |
| | | | | | | 46347,GQ161774,GQ |
| | | | | | | 475316,AB113875,JQ |
| | | | | | | 027320,AB362932,G |
| | | | | | | U815653,FJ899781,F |
| | | | | | | J349217,EU872013, |
| | | | | | | GQ377564,GU81556 |
| | | | | | | 6,AB104711,JN04081 |
| | | | | | | 1,AB274983,JQ04014 |
| | | | | | | 1,DQ089763,GQ2276 |
| | | | | | | 94,AF418689,KC510 |
| | | | | | | 646,AY862867,DQ063 |
| | | | | | | 0,JF754595,FJ56223 |
| | | | | | | 0,EU833891,FJ69250 |
| | | | | | | 6,EU155895,EU7960 |
| | | | | | | 69,JF828937,FN5947 |
| | | | | | | 59,JX507080,JN6421 |
| | | | | | | 27,GQ924622,KC875 |
| | | | | | | 286,HM153811,EU66 |
| | | | | | | 0225,AB555499,AB2 |
| | | | | | | 87323,FJQ32361,DQ2 |
| | | | | | | 98165,JQ023662,FJ6 |
| | | | | | | 92584,GU815638,GQ |
| | | | | | | 477489,JQ801508,AY |
| | | | | | | 738146,D50489,GQ1 |
| | | | | | | 84326,DQ922650,HE |
| | | | | | | 981179,AB900112,A |
| | | | | | | Y233284,GQ161810, |
| | | | | | | EU872003,FJ562221, |
| | | | | | | AF223964,EU564826 |
| | | | | | | ,AY217367,JQ801522 |
| | | | | | | ,AM117396,AB03355 |
| | | | | | | 3,KC87S302,AB2227 |
| | | | | | | 15,AY641558,KC875 |
| | | | | | | 296,FJ386633,GQ37 |
| | | | | | | 7515,GQ377582,FJ6 |
| | | | | | | 92609,JN664945,AB5 |
| | | | | | | 55497,EU306689,AB |
| | | | | | | 367435,GQ477487,E |
| | | | | | | U872015,EU787446, |
| | | | | | | GU815702,KC875274 |
| | | | | | | ,KC875329,HQ70047 |
| | | | | | | 4,GU456660,EU7874 |
| | | | | | | 41,JF440002,AY2173 |
| | | | | | | 63,DQ089759,GQ161 |
| | | | | | | 764,EU554540,FJ562 |
| | | | | | | 249,FJQ23652,AB036 |
| | | | | | | 914,HE981181,Y1885 |

-continued

| Taxonomy | NCBI Reference Sequence ID | Host | No. of Genomes | Lineage | Segment Count | Genbank Accession ID |
|---|---|---|---|---|---|---|
| | | | | | | 7,FN594768,GQ3775 |
| | | | | | | 62,FJ904420,HM750 |
| | | | | | | 143,EU306707,AB21 |
| | | | | | | 9530,AF143300,FJO2 |
| | | | | | | 3631,GU168594,GQ1 |
| | | | | | | 61798,AB166850,AB |
| | | | | | | 073850,JN040760,D |
| | | | | | | 0020002,EU678475, |
| | | | | | | EU872004,GU815655 |
| | | | | | | ,EU594405,EU15582 |
| | | | | | | 8,JQ801497,JN79289 |
| | | | | | | 5,GQ924603,AY5961 |
| | | | | | | 08,GU815739,FJ9044 |
| | | | | | | 34,AB246345,AB287 |
| | | | | | | 321,HM011493,FJO2 |
| | | | | | | 3639,FJ692586,EU87 |
| | | | | | | 1993,AB112472,AB4 |
| | | | | | | 80039,JQ801496,GU |
| | | | | | | 456675,AY161143,JN |
| | | | | | | 792902,AB493844,K |
| | | | | | | C494402,JQ040158,J |
| | | | | | | X154581,AB073854, |
| | | | | | | GQ922004,EU33099 |
| | | | | | | 7,AB064314,DQ0608 |
| | | | | | | 28,KF377037,JN6421 |
| | | | | | | 58,FJ787455,AB0738 |
| | | | | | | 39,JF828911,EU3067 |
| | | | | | | 03,AB014385,GU815 |
| | | | | | | 706,GU456670,JN66 |
| | | | | | | 4912,HQ700517,JQO |
| | | | | | | 40162,DQ486025,AB |
| | | | | | | 010289,KC875261,A |
| | | | | | | F418677,HQ603068, |
| | | | | | | HM363601,AB674424 |
| | | | | | | ,EU594426,DQ44862 |
| | | | | | | 4,EU919176,EU9396 |
| | | | | | | 46,JQ801523,HQ684 |
| | | | | | | 848,FJQ32351,JN664 |
| | | | | | | 946,DQ089770,JQ80 |
| | | | | | | 1511,AY293309,EU2 |
| | | | | | | 39219,HM585199,AB |
| | | | | | | 697506,EU859935,G |
| | | | | | | U815605,GQ183460, |
| | | | | | | AB670306,FJQ32360, |
| | | | | | | GU815707,GQ47747 |
| | | | | | | 9,AJ627227,JF75459 |
| | | | | | | 6,AB471854,AF12123 |
| | | | | | | 9,FJ386678,EU57007 |

-continued

| Taxonomy | NCBI Reference Sequence ID | Host | No. of Genomes | Lineage | Segment Count | Genbank Accession ID |
|---|---|---|---|---|---|---|
| | | | | | | 2,AB116089,FJ90442 |
| | | | | | | 3,KF485389,EU4390 |
| | | | | | | 08,GU332693,GQ922 |
| | | | | | | 001,EU859936,FJ692 |
| | | | | | | 610,GQ475317,GQ47 |
| | | | | | | 7471,GQ161813,JQ6 |
| | | | | | | 88405,HM750148,GQ |
| | | | | | | 924631,EU872005,D |
| | | | | | | 0329356,GU357842, |
| | | | | | | EU414143,EU594415 |
| | | | | | | ,FJQ23645,GU815585 |
| | | | | | | ,EU859898,EU93960 |
| | | | | | | 4,AB116549,GU5635 |
| | | | | | | 62,FJ692571,AY7417 |
| | | | | | | 97,AF241407,GQ377 |
| | | | | | | 552,FJ562288,DQ536 |
| | | | | | | 413,JF440014,AB188 |
| | | | | | | 241,KC510641,FJ386 |
| | | | | | | 652,AB375161,DQ08 |
| | | | | | | 9796,JN257186,FJ78 |
| | | | | | | 7449,FJ692603,FJ34 |
| | | | | | | 9206,EU859912,JF75 |
| | | | | | | 4609,AB222714,KF76 |
| | | | | | | 7450,HM011468,GQ1 |
| | | | | | | 83458,AB205188,EU |
| | | | | | | 916209,IQ027322,AB |
| | | | | | | 026813,HM750145,G |
| | | | | | | U815696,AY220698, |
| | | | | | | EU881995,EU859901 |
| | | | | | | ,AB674419,GQ37758 |
| | | | | | | 7,KC836878,EU9191 |
| | | | | | | 64,GU815711,KC875 |
| | | | | | | 289,AB205121,EU93 |
| | | | | | | 9624,EU916226,JN25 |
| | | | | | | 7181,AF418684,AB49 |
| | | | | | | 3828,AB014399,GQ3 |
| | | | | | | 77579,EU939612,AF |
| | | | | | | 068756,HM363611,E |
| | | | | | | U939614,AB674412, |
| | | | | | | AJ131569,AB116086, |
| | | | | | | AY721607,GU815646 |
| | | | | | | ,KC875273,AB07667 |
| | | | | | | 8,AM494697,AB3303 |
| | | | | | | 66,FN545833,JX4299 |
| | | | | | | 16,FJ562316,JN6421 |
| | | | | | | 40,DQ089781,AF143 |
| | | | | | | 308,HQ700516,FJ904 |
| | | | | | | 402,HQ700462,AJ62 |

| Taxonomy | NCBI Reference Sequence ID | Host | No. of Genomes | Lineage | Segment Count | Genbank Accession ID |
|---|---|---|---|---|---|---|
| | | | | | | 7224,D50519,FJ79980 96,GU815610,AB274 973,AB195938,AB11 6094,AY247030,GU4 56668,FJ562258,JN2 57168,AY233290,HM 750141,GQ183476,F J386593,GQ477503, GQ205387,FJ349236 ,KF17074l,JF754619 ,GU815775,JN79289 4,EU859927,EU9162 11,GU168595,AB116 085,JX978431,EU594 394,EU306714,JN792 907,JQ040165,JQ664 505,FR714500,FJ904 417,GQ377575,AY59 6105,EU872012,GU8 15747,AF405706,DQ 683578,AB119255,E U595030,EU916207, GQ475354,JQ687529 ,AY902770,HQ60307 0,GQ477464,EU9396 45,KC875272,EU939 564,FJ692594,AB049 610,GQ377612,JX42 9909,JN792916,FJ38 6682,AF418674,DQ8 99142,AB471853,AY 902773,GU563549,J N040771,JQ801480, EF576808,AB287327, GQ161783,AM42154 0,AP011090,JN18233 3,HQ700456,GQ4753 21,AJ131567,GQ377 541,FJ562237,GU332 704,EU939635,EU93 9611,KC875341,HM7 50152,GQ872211,EU 939586,AY233289,FJ 386615,FJ386626,DQ 089771,AB206816,G 0477466,FN594770, DQ448628,KC494398 ,FJ657522,FJ904412, |

| Taxonomy | NCBI Reference Sequence ID | Host | No. of Genomes | Lineage | Segment Count | Genbank Accession ID |
|---|---|---|---|---|---|---|
| | | | | | | JN664934,JN792913, EU916232,AB674421, FJ562299,AJ627222, X69798,GU815753,GU815622,AB300366, KC875330,FJ787460, GQ924630,KC87525 1,HQ700443,FJ56231 3,FJ692604,GU81573 3,AB014365,JX42990 2,EU939602,AB6703 10,FJ349230,EU8599 03,HM011482,HM011 500,EU564822,JX429 908,GQ161792,GU81 5664,AB493830,JQ80 1524,AB674427,DQO 89786,AB104709,JN0 40785,GQ377607,EU 85921,DQ478884,KC875254,AB674408, AP011097,EU859943 ,AB367803,EU23922 1,GQ205382,AY0904 53,GU815650,FJQ323 48,GU456636,JF7546 30,FJ589066,AB3003 60,GU332695,FJ3866 51,AY862866,HM363 577,FJ78456,FJ386 610,EU871977,HQ60 3066,EU919171,AM4 21541,KC875337,JF8 99337,FJQ32345,AB2 22707,AB365448,GU 815760,FJ386649,AM 494712,AB287320,JN 257151,EU330994,JN 182330,KC875301,J 0664504,HQ700455, FJ899784,GQ477484 ,EU939630,AP01110 8,U46935,AF461359, GU385774,JQ027321 ,AB205126,KC51065 2,EU871971,AB1980 84,GQ377619,M3863 6,DQ089793,HM3635 |

| Taxonomy | NCBI Reference Sequence ID | Host | No. of Genomes | Lineage | Segment Count | Genbank Accession ID |
|---|---|---|---|---|---|---|
| | | | | | | 84,AY330915,GQ924605,AB670281,GQ475337,HQ603082,AY179734,GU815689,AY217372,X65258,FJ386604,JX898692,JX507214,FJ386687,GU456655,AB471856,AF297620,GU456657,EU439020,KC875291,FJ787488,EU306716,X98075,FJ692533,AY161148,HQ833470,EU939661,FJ692564,AF297619,AB900113,FJ562331,GQ477456,AB453984,KF373039,AB555498,GQ183482,EU939579,FJ787467,FM199978,FJ904426,FJ349213,GQ475322,AB198082,AB014381,AB246317,GQ377636,AY233293,EU859929,EU859956,AM421538,JQ801472,EU594382,GU815687,EU594409,EF103277,EU594402,EU939566,DQ377161,DQ089791,FR714496,JN040784,JN257217,AB014376,JN792896,AY781178,GQ377565,EU570073,JQ801512,JQ664502,FJ562264,EU594386,DQ315780,HM363586,JN040755,AB302942,JX507211,AB074047,HQ236016,AJ627221,KF679997,AB014391,AB670263,AB222712,AM421545,FJO23647,JN040754,EU939621,FJ349238,FJ904440,GU815750,AB670257,JXQ26886,JF491452,EU939674,FJ386667,AY236160,GQ924640,HM750131,FJ899783,KF425554,JF828916,HM363593,JN664933,GU332697,AB195940,EU882005,AB4 |

| Taxonomy | NCBI Reference Sequence ID | Host | No. of Genomes | Lineage | Segment Count | Genbank Accession ID |
|---|---|---|---|---|---|---|
| | | | | | | 93842,AB195934,JQ272887,DQ899143,AY800390,AB198078,DQ478888,JN827423,AJ627217,EU835241,D0823095,JXQ26879,DQ993699,FJ562218,AF121250,EU939647,EU594403,HM363608,FJ787479,EU239224,AY817513,AB674406,AB368297,EU554541,FJ692589,EU414134,FJ904407,KC875260,FR714491,JQ801492,FJ386607,EF103278,AB104712,FJ904421,EU939551,EU305547,AB105174,KC875323,JN040767,FJ562234,JQ801503,GQ924627,AB375167,GQ377620,FJ787457,KC875309,KC875283,EU939567,AB014375,JN642164,JQ040136,X52939,AB195931,GU815701,KC875290,JQ027317,GQ358142,KC875282,FJ386582,FJ349228,HE981185,GQ475339,EU859907,JN642141,GQ377572,FJ692557,JN257184,X98077,GQ183449,FM199974,AB241117,GQ227693,FJ386631,FJ692593,JN827415,JN257213,JN792918,FJ787440,HQ646555,GU815756,GQ161766,AB365452,HM590474,EU859922,FJ386668,JQ272888,JN182323,HQ684849,DQ089761,GQ475349,DQ463794,DQ478898,EU305545,EU916208,GQ475328,EU787437,JN642132,AB493843,AF222322,GU168597,DQ089769,AB670247,GU815615,DQ0220,JQ040166,JQ801473,FJ787490,EU939667,GQ377537,AB194949,EU678473,GU815724,HQ700488,DQ448626,DQ304547,JXQ26888,GU815713,EU |

| Taxonomy | NCBI Reference Sequence ID | Host | No. of Genomes | Lineage | Segment Count | Genbank Accession ID |
|---|---|---|---|---|---|---|
| | | | | | | 306705,FJ562286,EU4390 07,GQ161807,GU815737, HM011479,X70185,EU660 230,DQ899146,AB670259, EU594410,HQ378247,GQ1 61760,AB073824,EU93956 0,EU139543,HM363606,JQ 040148,DQ089789,AB670 301,FJ386671,EU859931, HQ700465,L27106,EU919 166,EU939670,M54923,JF 754628,FR714490,AB1959 49,JN792906,AF411408,A Y206392,KC875333,DQ08 9780,AB048703,GQ92465 4,AF121248,GU815754,H M011486,GU815749,FJ90 4441,EU939633,GU56355 0,GQ161772,GU815618,D 23679,AB126580,FJ38658 7,EU939659,GU815607,JX 504531,FJ904405,EU8720 14,GQ161767,JXQ96955,F J562224,EU41413,EU881 999,DQ463799,FJ787466, GQ377524,DQ904357,GU 815712,EU306713,EU9395 71,GU815624,EF208113,F J349216,JN664944,AF223 955,EU939541,GQ184324, JN18324,DQ089801,KF7 67451,HQ603065,JN64216 2,FJ349241,HQ700541,AM 421544,AB073846,GU815 723,AJ131574,GQ183456, GQ227696,FR714504,GU4 56639,GQ183469,GU8157 64,HM363607,DQ478891, AB241113,FJ787475,JN04 0752,FR714503,EU562215 ,GU563556,AY330912,AY1 67100,JQ040159,DQ37715 9,HM585189,AB367401,K C315400,GQ358152,JN04 0780,EU554536,HQ70044 9,AB246342,AB270539,FJ 386685,DQ463787,GU815 719,FJ386677,AB049609,J |

| Taxonomy | NCBI Reference Sequence ID | Host | No. of Genomes | Lineage | Segment Count | Genbank Accession ID |
|---|---|---|---|---|---|---|
| | | | | | | N40637I,DQ315786,JQ040175,EU859942,KC875308,JQ429082,JF754599,GQ377630,GQ475335,AY721610,AB205124,GU815628,EU871970,GQ358156,JX504537,EU872010,JF754634,GU456645,KC510648,EU871998,GU815612,DQ916212,EU594391,DQ993701,EU859917,FJ386644,FJ386688,GQ358148,GQ477485,KC875298,DQ993695,HQ700508,AB111124,JN257148,AY236161,EU557007I,GU815567,FJQ32358,HE576989,GQ161836,EU054331,GQ377622,GQ475323,JN040799,EF473973,HQ700484,GQ475318,AB674416,GQ924634,DQ993181,AB014396,HM011483,EU439022,FJ386648,HQ700478,EU594398,FJ692601,AB697493,JQ040170,AB014393,AB073826,EF208115,DQ111987,AY817515,AB300370,AB367418,AY781186,JX504532,JN792908,FJ386634,AY330911,KF219922,AF223963,GQ924618,JQ801476,EU306723,AB037928,KC875277,AB670254,FJ386650,AF418688,AP011101,JN257203,GQ161822,GQ377623,DQ463793,FJ692587,AB670289,FJ899782,EU871984,GQ161779,EU916223,APO11091,AB713532,JX898687,FJ562289,AF100308,JF754633,DQ993711,AP011087,AB670274,AY233294,EU330989,EU916240,AF143299,FJ692608,JF491451,DQ478895,DQ329357,L08805,EU306719,JN040782,AM494717,JN642159,FJ349 |

-continued

| Taxonomy | NCBI Reference Sequence ID | Host | No. of Genomes | Lineage | Segment Count | Genbank Accession ID |
|---|---|---|---|---|---|---|
| | | | | | | 223,GQ924652,FJ356716, AM295799,GU333692,KC494396,AB674420,FJ669259,GQ377625,AB073842,H0700490,KC875319,EU717217,EF473976,AB900095,GQ924617,GQ924613,AY167101,GU815557,GU815596,AF297624,JF440011,GQ47532S,FJQ23669,JQ040143,AY721609,KC494403,EU306725,GU815636,EU859939,JN040816,DQ089797,EU594400,AJ309369,JN792910,DQ993688,EF634480,AB250109,JQ801521,AB014360,AY220702,AB036917,JQ040128,KC875315,AY236162,AB697498,AB126581,HQ700473,GQ331047,EU916222,JF828930,EU916233,GQ377640,N642148,GU563548,AB493848,AB195955,EU306684,EU859906,JN257199,AF537372,AB674405,EU185787,GQ161814,GQ924607,EU939679,HM750132,EU871979,GQ161815,FJ562268,AB697504,GQ377644,AB300361,GU815736,JX560520,JF440006,FJ562241,AB116087,AB247916,HM750137,AY217356,GU815748,AB195939,GQ475324,GU563552,AY161139,GQ377550,EU439016,EU306683,AB116084,EF494382,DQ246215,AY796032,AY128092,AB210821,GQ377518,EU439010,AY247031,EU882006,GU815769,FJ562257,KC836881,JN642150,AB493834,GQ377554,EU787445,EU594392,FJ386629,HM363570,FJ386629,JN257162,JN664924,JX154582,EU306706,HQ603060,FJQ23656, |

| Taxonomy | NCBI Reference Sequence ID | Host | No. of Genomes | Lineage | Segment Count | Genbank Accession ID |
|---|---|---|---|---|---|---|
| | | | | | | AB583680,AM421548,AB212625,DQ899144,EU306673,AY090455,EF464099,AB03358,FJ899770,FJ692562,AB670309,GU815548,JN827424,FJQ23664,AB330369,DQ060824,FJ562219,GU815745,EU433005,EU859904,GU815603,JX429911,AB014367,AM117394,GU815551,GU815576,GU456683,AB697495,AB270542,AY066028,GU815647,AB670237,KF425553,AB493829,AY233281,JQ040169,JQ040154,M57663,FJ904443,AB274974,HQ700527,JN664935,FJ899778,EU872000,GU815550,JQ040168,JF436919,AF182803,U95551,EU796068,AF090841,AB033555,AF461043,FJ787446,GQ161838,EU919161,GU815780,AB222709,FJ562252,AF498266,AB231909,GQ924653,GQ375590,EU859920,EF473974,DQ089790,AY934770,AB674425,JF440003,EU939572,DQ536411,GQ377583,HM363600,EU939548,JF754592,AB056513,JN642142,GQ205378,AB116654,GQ161781,AB274979,HQ603074,AB194950,JN642131,FJ904397,FN545830,DQ788725,GQ377535,EU439009,HM011496,JF754607,HQ700523,GQ475341,GQ924650,JN04082 9,HQ700466,AB675678,AP011100,D50518,EU939616,AB287319,FJ882617,JN664927,AB014386,JQ040147,GQ205389,KC875294,JN040796,EU916215,JX429918,GQ377594,FJ349227,AY034878,EU306675,HQ700538,GU332691,AY817511, |

| Taxonomy | NCBI Reference Sequence ID | Host | No. of Genomes | Lineage | Segment Count | Genbank Accession ID |
|---|---|---|---|---|---|---|
| | | | | | | EU939608,FJ562270,JX870001,AY233275,GQ475353,DQ823086,AB287326,AB642095,FJQ32337,DQ788729,AB900103,FJ692606,FJ692576,AB287322,GU815678,GQ377633,AB697510,FR714497,JF754588,AB367804,AJ131956,HE981171,EU881996,AB064312,AY934767,AB112063,GQ377598,EU547559,AB900111,AB775198,GU815700,FJ562317,JN664926,JX504542,FJ882612,DQ536412,GQ377617,AB222713,AF363962,KC510660,JN811656,GQ475329,HQ700530,AB367403,JN792912,AB670272,JN664938,AB073834,AJ627225,AF223958,JF439995,AB298720,GU815691,DQ060822,HM011485,AB113878,GQ161799,JN257159,AF411410,AY217364,EU787438,FJ882610,AP011107,GQ924658,EU859919,AJ627220,GQ377642,D16666,AB031262,AY902768,JN827421,DQ060830,DQ899145,EU872007,JQ040125,AB106884,GQ477477,DQ315784,GU815554,DQ463798,GU563560,JN642130,FJ787464,EU871981,HM585198,AF233236,AB670264,AB274976,AB195944,HM363598,G0161805,FJ787468,JN040756,AB670291,HQ603077,DQ899150,DQ993698,JN040786,EU859902,AB033557,GQ377616,AB713527,G0377603,AY596102,GU815742,AY123041,AB697511,AB555501,AB033552,AB073821,GU815593,AB111116,GQ477495,EU660228,JF440009,HM011469,GQ92 |

| Taxonomy | NCBI Reference Sequence ID | Host | No. of Genomes | Lineage | Segment Count | Genbank Accession ID |
|---|---|---|---|---|---|---|
| | | | | | | 4608,AY934765,AM494698,FJ904429,AB275308,FJ692575,AY033072,GU815782,EU939576,JQ801513,FJ562284,JF754635,JN792901,FJ692561,AY739674,AB674433,FJ709457,AB670255,DQ995804,JN257205,KC875267,AB176643,AB222708,GU815703,JX507212,EU859923,GQ205386,H0236015,FJ562251,AY306136,EU939637,EU859953,GU815597,FJ562236,GQ477488,GQ161765,AB0902770,DQ995802,FJQ23672,JN664941,AY090456,DQ536410,GU563558,JN040794,JN257191,GQ477492,GQ377581,AF418682,FJ904394,EF576812,GQ475343,JN257156,AB111114,EU939676,EU939552,FJ562315,GQ377643,JF440015,AY781181,GU815757,FJQ23654,AB195956,GQ475333,HM363566,JN642126,FJ787483,FJ78743,AB375164,HM117850,EU306670,AY161142,GQ377532,JN040773,AB270547,JX429913,HE981173,FJQ23636,AB375162,AB111123,HM363587,JF828920,AP011086,HQ700525,AY862860,AY167094,GQ259588,FJ562232,FJ787443,GQ477469,JN664929,KC875332,EU487257,JQ027326,AB113879,AB195951,FJQ23644,JX504541,D0993681,D50521,HM0114499,FN545828,AB562462,AB367421,EU306674,FJ882613,AJ344117,JQ801502,AB195933,AY935700,AB6770240,AF043594,JF43692,AB073823,AB367430,GU332690,EU306690,JXQ969 |

-continued

| Taxonomy | NCBI Reference Sequence ID | Host | No. of Genomes | Lineage | Segment Count | Genbank Accession ID |
|---|---|---|---|---|---|---|
| | | | | | | 57,GQ377641,JN040810,AB675675,AB116552,JXQ2683,GQ161834,FJ386580,GU456643,X98074,FN594767,JF444007,FJ562338,HM011491,S50225,FJ69259 5,JX898698,EU919172,FN545829,AM494709,GU815 586,GU815669,EU939583,JN040822,AP011105,GU8 15743,EU939577,AB69749 1,JQ027327,AB486012,AB 365445,FJ386656,AF1212 46,JQ801478,JN257209,H M750146,AB670308,GQ20 5383,AF143301,AF241409 ,AB026811,AB670278,AB2 70543,GQ205440,AB6703 11,GQ377543,JF28908,E U554537,JQ040163,JQ801 474,AB300362,EU939537, EU871975,FJQ32353,DQ9 93686,AB493839,EF49438 0,JN040788,AB119254,JQ 023663,AY161149,HQ700 533,GQ475344,JN642129, FJQ23638,FJ349218,AF22 3956,JN664931,HQ833466 ,GQ183464,EU306708,JQO 27332,JF439998,EU78743 5,GU815698,FIQ32347,AY 163869,DQ478889,DQ448 623,FI692590,EU871976, EU717218,DQ980551,AY9 02772,GQ377538,FJ38661 6,AY934769,JN18326,HM 363583,GU456666,GQ475 355,FJ904445,AY862862, AY233276,GQ161816,AB3 02095,FJ562280,JQ02731 6,GU815774,KC510642,H M363610,JQ801477,FJ562 259,AY862863,GQ377635, HQ700501,GQ358139,FJ5 62277,GQ924657,EU1558 27,KC875257,DQ463795,J N642154,JN257183,KC510 653,AY090452,JQ688403, |

-continued

| Taxonomy | NCBI Reference Sequence ID | Host | No. of Genomes | Lineage | Segment Count | Genbank Accession ID |
|---|---|---|---|---|---|---|
| | | | | | | JN257169,GQ924645,JN664943,FJ692572,GU81568 3,EU916234,FJ904442,FJ023635,JN664928,AB07382 5,GU815552,FJQ23655,HM011489,FJQ23674,EU4141 39,AB014384,GU815721,EU306685,AM494694,EU93 9657,GU815644,JN642157,JEF494377,XQ2763,AB194 948,JQ040156,GQ161808, FJ386600,AY167090,AB64 2094,AY596107,EU921419 ,GQ161753,KC875340,GU 815732,DQ089783,AB900 105,AM494706,AY330917, AB493835,AY206379,GQ1 83480,JN827417,FJ56231 2,AB073852,EU916213,AY 596109,FJ349207,AB1160 90,FM209514,AY934771,A Y596112,AB493832,EU93 9545,EU916221,GU81558 8,AB670302,AY311370,AM 494714,AY217371,GQ377 634,AY16147,EU155893, JX50715,AB367801,AF46 1360,EU570069,KF679989 ,GQ475305,AF363963,EU9 19170,HQ833469,JN25719 3,DQ980548,AJ344116,AB 219533,KC875253,AB3678 00,AY721611,KF425556,K C875276,AB246343,DQ47 8890,AB674436,JN664940 ,AF458665,GQ477463,AM 184126,EU594404,FJ9044 11,AB697487,HM585197,E U306722,AF222323,JN257 192,FJ386663,HM011484, JN664915,GQ377566,AB6 42092,FJ562247,FN59475 7,EU560441,KC875307,AB 300371,FJ692580,EU8720 16,GQ161806,GU815684, AB670303,GQ477502,AB1 95953,GQ377522,AY7381 41,JQ040137,FJ692566,E |

| Taxonomy | NCBI Reference Sequence ID | Host | No. of Genomes | Lineage | Segment Count | Genbank Accession ID |
|---|---|---|---|---|---|---|
| | | | | | | U859938,FJ386662,FJ904404,FJ562295,EU306696,HQ603064,FJ386598,AB367422,DQ315776,DQ99369 0,JN040769,AY233277,EU522068,EU306718,AY16 1 70 96,FJ692607,GU456650,A B697501,FJ386611,AB287 325,AB562463,FJ386670, GQ161821,AB014395,AF4 18678,EF494381,AY93477 3,AB205127,HQ700481,FJ 904444,GU332694,AB670 276,AB480038,JQ801510, AB033559,AB195937,DQO 60826,HE981180,FJ386662 1,AB188244,FJQ23663,JN6 42136,GU815561,FJ56230 0,GQ161791,HM750151,E U939666,JF828918,AM494 708,AB365450,DQ993691, EU660224,JF436921,KC51 0647,FR714495,GQ35813 7,JQ429078,AB076679,FJ 023650,EU916210,EU4390 06,KC875256,DQ980547,D 0089798,GQ377615,DQ47 8887,JF754631,JQ801493, AB073857,FJ386679,GQ4 77457,DQ993696,D16665, HM750138,JX429899,DQ9 93700,EU939618,AM4947 15,JQ688404,JF754608,G U815740,JF828928,AF282 918,GQ477500,DQ111986, AB453986,EU158262,F58 9065,EU589340,AB073833 ,GU815771,EU306701,EU 871996,AB300363,AB0738 47,GQ161758,FM209516,A Y741795,EU859926,EU93 9561,AB056515,AB674409 ,FJ899763,AB900116,GQ3 77606,EU306727,GQ1834 70,DQ788728,HQ700521, GQ477468,EU306692,JN0 40763,HM627320,GQ3775 14,JN257216,KC875321,G |

| Taxonomy | NCBI Reference Sequence ID | Host | No. of Genomes | Lineage | Segment Count | Genbank Accession ID |
|---|---|---|---|---|---|---|
| | | | | | | 0475356,FJ787459,AF458664,AB274977,FJ899771,FJ562235,HM363569,JN040795,AY902777,AY206383,EU660232,U87746,GQ924609,AF297625,GU815730,HQ700494,FJ692612,AY217368,HM011470,EU939673,GQ477480,D23682,GQ377597,AB288026,JN040779,FJ562238,GQ475314,JN642138,X80925,GQ475310,EU939559,GU815614,EU547561,JXQ26884,GU456679,JN664910,FJ386647,FJ023640,KF061168,AB073832,EU919173,GQ161771,H060302,AF160501,GQ924626,KC012652,EU239226,GU815556,AB100695,EU570067,GQ161784,JN792893,GQ377578,HQ833471,H0700493,FJ899768,GQ227697,HM011501,JF491455,DQ463789,AB205118,FJ386657,FJ589068,AB697490,AM295797,FJQ32343,GQ377531,JQ801507,AB270546,AB195946,FJ904447,J0801501,FJ518811,EU306679,AB026814,JN257195,KC510658,FJQ23657,FJ882616,AB210820,DQ446379,AB109476,HM363585,KC875338,JQ664509,GU815571,HQ603080,GQ161796,DQ078791,GQ872210,GU815577,FJ692602,AY161162,FJ787448,AY220697,AY945307,HM590472,FM199981,EU522074,HM363594,FR714494,FJ692581,AY161160,EU185789,AB111119,AM494704,AM180624,GU456659,JN040809,EU939544,JF491456,EU9162905,AY161140,FJ562227,G0377549,KF425555,HM14 |

-continued

| Taxonomy | NCBI Reference Sequence ID | Host | No. of Genomes | Lineage | Segment Count | Genbank Accession ID |
|---|---|---|---|---|---|---|
| Hepatitis B virus 146/Thailand | NC_003977 | vertebrates,human | 1 | Hepadnaviridae,Orthohepadnavirus,Hepatitis B virus | — | 6131,AB014394,DQ82309 4,GQ477470,AB198076,AF 241408,AF536524,JN2571 50,FN594769,IN664920,J N257185,AY641561 |
| Hepatitis B virus ayw/Japan/Ehime 22-HS/2005 | NC_003977 | vertebrates,human | 1 | Hepadnaviridae,Orthohepadnavirus,Hepatitis B virus | — | FJ361772 |
| Hepatitis B virus subgenotype A3/genotype E | NC_003977 | vertebrates,human | 1 | Hepadnaviridae,Orthohepadnavirus,Hepatitis B virus | — | AB267090 |
| Hepatitis B virus subtype adr | NC_003977 | vertebrates,human | 1 | Hepadnaviridae,Orthohepadnavirus,Hepatitis B virus | — | HF571060 |
| Hepatitis B virus subtype adr | NC_003977 | vertebrates,human | 2 | Hepadnaviridae,Orthohepadnavirus,Hepatitis B virus | — | AB176642,AB299858 |
| Hepatitis B virus subtype adw | NC_003977 | vertebrates,human | 3 | Hepadnaviridae,Orthohepadnavirus,Hepatitis B virus | — | DQ0331,DQ0330,DQ0 329 |
| Hepatitis B virus subtype adw2 | NC_003977 | vertebrates,human | 1 | Hepadnaviridae,Orthohepadnavirus,Hepatitis B virus | — | AM282986 |
| Hepatitis C virus | NC_009827,NC_00982 6,NC_0098 25,NC_009 824,NC_00 4102,NC_0 09823 | vertebrates,human | 269 | Flaviviridae,Hepacivirus,Hepatitis C virus | — | HQ738645,EU362892 ,EU362907,JXQ14307 ,KC155254,JX183554 ,FJ407092,FJ462433, AB047645,HQ850284 ,AB049096,DQ41878 5,EF407480,JF73511 3,EF407418,AB08029 9,D89815,KC197235, EF407451,EF407438, EU246930,EU362903 ,D13558,EU362881,D 45172,EU246933,DQ 988076,AJQ00009,K 988075,FJ466441,AB 049093,JF735117,AM 408911,KC248196,E U362895,FJ462436,A B049008,EF407460,A B559564,JX183557,D C197227,EU158186, EU362876,EF407465 ,JF735120,AJ278830, KF700370,EF407440, FJ462440,EF407469, AB049094,EU362897 ,D50481,JF735123,E U362893,EF407431, EF632071,KC197236 |

| Taxonomy | NCBI Reference Sequence ID | Host | No. of Genomes | Lineage | Segment Count | Genbank Accession ID |
|---|---|---|---|---|---|---|
| | | | | | | JF735116,EF026073,D11168,EF632069,AB047643,JF735112,KC197232,EU362883,X61596,FJ839869,FN666428,D63857,EF407444,EU362887,EF407482,DQ988077,JF735110,EF407422,AB049099,EU246939,D89872,DQ988073,DQ278892,EF407504,EF407502,EF407428,KC197228,EU362877,D30613,JX183558,D50484,AB049100,EU362885,EU362901,EF407425,AB049101,EU362898,EF407476,EF407488,JX183553,EF407436,EF407457,KC197237,D90208,EF407445,AF511950,FJ462438,KC197238,D85516,D50485,KC197240,EF407471,AB677529,EF407472,FJ462434,HQ850285,DQ988078,AB677527,JX183555,EF407449,JF735115,KC248194,EF407415,KC197229,JQ745651,EU362902,EF407432,JF735114,KC197234,EF407417,EF407427,JX183556,EF407470,EF407456,EF407454,D10750,KC248199,EU362891,JF735119,AB435162,AF511949,EF407447,KC197239,EF407423,AJ851228,AB677531,EF407446,EU362880,JX183551,KC967478,KC197233,EU362900,FJ462439,EF407749 7,AB049090,EU6438 |

| Taxonomy | NCBI Reference Sequence ID | Host | No. of Genomes | Lineage | Segment Count | Genbank Accession ID |
|---|---|---|---|---|---|---|
| | | | | | | 34,JF735122,HQ8502 87,EF407492,EF4074 55,DQ0944,FJQ25855 ,KC197231,KC96747 6,EU246935,,AB0490 92,JF735125,AB0490 89,EU362896,AB016 785,D11355,JF73511 1,AB047644,EF40742 ,1,EF632070,EF40741 3,EF407452,FJ46243 1,EF407479,EF40748 5,DQ437509,AB1913 33,FJ435090,EF4075 03,EF407441,HQ850 290,GU294484,EF40 7483,AB049087,AB4 29050,DQ988074,FJ8 39870,EU643836,D5 0482,EF407487,AB04 9091,HQ850283,HQ8 50282,EF407439,AB0 47640,KC248198,KC 197230,EU362884,E ,F407437,AB622121, D10934,EF407442,K C248195,FJ462432,K C96747,JX183552,E U362894,EF407493, EF407435,EF407414, FJ462437,EF407453, FJ462435,KC197226, HQ850286,AB049088 ,D50480,EF407426,E F407443,EF407501,H M777359,EF407450, DQ988079,EF407461 ,X76918,JF735121,K C248197,EF407448, ,AJ132997,AB677533, D10988,AY651061,A B047641,AB049095, EU408327,FJQ25856, EF407411,EF407434, AB049097,EF407419, EU362886,D10749,H 0850288,D14484,FJO 25854,JF735118,EU3 |

| Taxonomy | NCBI Reference Sequence ID | Host | No. of Genomes | Lineage | Segment Count | Genbank Accession ID |
|---|---|---|---|---|---|---|
| Hepatitis C virus (isolate 6a33) | NC_009827, NC_009826, NC_009825, NC_009824, NC_009823 | vertebrates, human | 1 | Flaviviridae, Hepacivirus, Hepatitis C virus | — | 62890,AJ132996,EF407475,AY587845,KC248193,JX183549,AF511948,EF407424,EU362899,JF735124,EU362879,EU362878,EU362882,KC967477,J -continued

| Taxonomy | NCBI Reference Sequence ID | Host | No. of Genomes | Lineage | Segment Count | Genbank Accession ID |
|---|---|---|---|---|---|---|
| Hepatitis C virus (isolate HC-G9) | NC_009827,NC_009826,NC_009825,NC_009824,NC_004102,NC_009823 | vertebrates,human | 1 | Flaviviridae,Hepacivirus,Hepatitis C virus | — | D14853 |
| Hepatitis C virus (isolate HCV-K3a/650) | NC_009827,NC_009826,NC_009825,NC_009824,NC_004102,NC_009823 | vertebrates,human | 1 | Flaviviridae,Hepacivirus,Hepatitis C virus | — | D28917 |
| Hepatitis C virus (isolate India) | NC_009827,NC_009826,NC_009825,NC_009824,NC_004102,NC_009823 | vertebrates,human | 1 | Flaviviridae,Hepacivirus,Hepatitis C virus | — | AY051292 |
| Hepatitis C virus (isolate JK046) | NC_009827,NC_009826,NC_009825,NC_009824,NC_004102,NC_009823 | vertebrates,human | 1 | Flaviviridae,Hepacivirus,Hepatitis C virus | — | D63822 |
| Hepatitis C virus (isolate JK049) | NC_009827,NC_009826,NC_009825,NC_009824,NC_004102,NC_009823 | vertebrates,human | 1 | Flaviviridae,Hepacivirus,Hepatitis C virus | — | D63821 |
| Hepatitis C virus (isolate JPUT971017) | NC_009827,NC_009826,NC_009825,NC_009824,NC_004102,NC_009823 | vertebrates,human | 1 | Flaviviridae,Hepacivirus,Hepatitis C virus | — | AB030907 |
| Hepatitis C virus (isolate Tr Kj) | NC_009827,NC_009826,NC_009825,NC_009824,NC_004102,NC_009823 | vertebrates,human | 1 | Flaviviridae,Hepacivirus,Hepatitis C virus | — | D49374 |

-continued

| Taxonomy | NCBI Reference Sequence ID | Host | No. of Genomes | Lineage | Segment Count | Genbank Accession ID |
|---|---|---|---|---|---|---|
| Hepatitis C virus (isolate VAT96) | 4102,NC_009823 | vertebrates,human | 1 | Flaviviridae,Hepacivirus,Hepatitis C virus | — | AB031663 |
| Hepatitis C virus (isolate VN004) | NC_009827,NC_009826,NC_009825,NC_009824,NC_009823 | vertebrates,human | 1 | Flaviviridae,Hepacivirus,Hepatitis C virus | — | D84265 |
| Hepatitis C virus (isolate VN235) | NC_009827,NC_009826,NC_009825,NC_009824,NC_009823 | vertebrates,human | 1 | Flaviviridae,Hepacivirus,Hepatitis C virus | — | D84263 |
| Hepatitis C virus (isolate VN405) | NC_009827,NC_009826,NC_009825,NC_009824,NC_009823 | vertebrates,human | 1 | Flaviviridae,Hepacivirus,Hepatitis C virus | — | D84264 |
| Hepatitis C virus ED43 | NC_009827,NC_009826,NC_009825,NC_009824,NC_009823 | vertebrates,human | 1 | Flaviviridae,Hepacivirus,Hepatitis C virus | — | GU814265 |
| Hepatitis C virus JFH-1 | NC_009827,NC_009826,NC_009825,NC_009824,NC_009823 | vertebrates,human | 1 | Flaviviridae,Hepacivirus,Hepatitis C virus | — | AB047639 |
| Hepatitis C virus S52 | NC_009827,NC_009826,NC_009825 | vertebrates,human | 1 | Flaviviridae,Hepacivirus,Hepatitis C virus | — | GU814263 |

| Taxonomy | NCBI Reference Sequence ID | Host | No. of Genomes | Lineage | Segment Count | Genbank Accession ID |
|---|---|---|---|---|---|---|
| Hepatitis C virus SA13 | 824,NC_00 4102,NC_0 09823 | vertebrates,human | 1 | Flaviviridae,Hepacivirus,Hepatitis C virus | — | AF064490 |
| Hepat -continued

| Taxonomy | NCBI Reference Sequence ID | Host | No. of Genomes | Lineage | Segment Count | Genbank Accession ID |
|---|---|---|---|---|---|---|
| | | | | | | U482862,FJQ24280,EU256003,EU660383, EU155349,EU255975,JX463550,EU155314,EU255937,EU255598,JX463563,EU482869,EU255994,FJQ24087,EU255945,EU2560697,EU781781,EU256106,EU482843,EU781790,EU256024,EU482836,EU781767,FJ390394,EU862823,FJ181999,AF271632,EU155297,EU155268,EU155270,JX463640,EU155342,EU155213,EU862836,EU255981,EU255980,JX463599,FJ205867,EU255943,EU781774,EU781813,EU260396,EU7817861,EU862834,EU482841,EU482852,EU155215,EU256105,EU256086,EU256047,EU781818,EU255964,EU255946,EU155273,EU482884,EU781805,EU482287,EU781754,EU482870,EU256096,EU255949,EU155293,EU482838,EU529677,EU781780,EU256036,EU781814,EU256044,EU862826,EU255976,EU862824,EU155238,EU155283,EU482844,EF032886,EU7818189,EU482889,EU155267,EU155243,EU155348,M62321,FJ39039,EU256057,FJ41017,EU862827,EU255592,EU781783,EU781749,EU687193,EU155378,EU482854,EU482863,EU255954,EU |

TABLE -continued

| Taxonomy | NCBI Reference Sequence ID | Host | No. of Genomes | Lineage | Segment Count | Genbank Accession ID |
|---|---|---|---|---|---|---|
| | | | | | | 155350,EU155313,EU256050,EU256021, |
| | | | | | | EU155346,EU781806,EU781810,EU255952,EU482832,EU781762,EU482856,EU255959,EU155245,EU155355,EU781753,EU255938,EU781776,EU155321,EU255929,EF032890,EU482834,EU255998,EU155343,GQ149768,EU155239,EU255934,EU256058,EU255931,EU155266,EU595697,EU260395,EU234064,EU482869,EU256033,EU256071,EU155286,EU155312,EU781820,EU781816,EU256051,EU781760,EU155310,EF621489,EU255985,EU781755,EU482831,EU155244,EU256056,EU255958,EU155250,EU781765,EU781800,EU529680,JX463611,EU781792,EU256049,EU256032,EU256070,EU256025,EU250017,EU155275,EU155248,EU256012,EU155288,EU781809,AF290978,EU482848,JX463547,EU155236,EU781756,EU862839,EU155296,EU256068,EF032900,EU781823,EU482842,JX463549,EU482840,EU482882,EU256052,EU256069,EU482285,EU781775,EU781170,EU155295,EU256038,EU595699,EU862841,JX463596,EU781804,EU781778,EU781789,EU4 |

| Taxonomy | NCBI Reference Sequence ID | Host | No. of Genomes | Lineage | Segment Count | Genbank Accession ID |
|---|---|---|---|---|---|---|
| | | | | | | 82858,EU482865,EU256004,EU781768,AB520610,EU255970,EU155284,EU687194,EU482872,EU482847,EU155271,EU256027,EU781779,EU155354,EU482861,EU155352,EU256029,EU234065,EU256094,EU255997,EU255977,FJ024276,EU862838,EU256008,EU155240,EU862831,EU687195,EU781808,EF032884,EU482878,EU482846,EU781796,EU155233,EU256009,EU255942,EF032888,EU529678,EU255944,EU155274,EU482855,EU155242,U781803,EU155338,EU256014,EU569723,EU482845,EU255992,EU256019,EU255978,EU781794,EU256023,FJ205869,EU781812,EU781822,EU255995,EU155345,EU256087,EU255930,EF032885,EU155353,EU255968,EU255973,EU660387,EU256040,FJ182000,EU155347,EU781777,EU256011,EU781788,FJ205868,EU256107,FJQ24282,EU862832,EU255947,EU482866,EU255967,EU256002,EU255927,EU155216,EU255990,EU256104,EU781782,EF032883,EU155379,EU482835,EU256041,EU482887,EU256006,EU256005,EU255956,EU255966,EU15598 |

| Taxonomy | NCBI Reference Sequence ID | Host | No. of Genomes | Lineage | Segment Count | Genbank Accession ID |
|---|---|---|---|---|---|---|
| | | | | | | 351,EU256037,EU48 2871,EU781784,EU2 56074,EU781769,EU 155339,EU781748,E U781802,EU256034, EU781807,EF032889 ,EU155272,EU48287 3,EU255950,KC8440 49,EU781764,EU255 996,EU781770,EU25 5948,EU256048,EU2 55974,EU781791,EU 155277,EU781817,E U155311,EU781793, EU155291,EU256018 ,EU781747,EU78176 3,EU256017,EU7817 87,EU256010,EU781 766,EU529681,EU78 1801,EU781752,EU2 55951,EU155269,EU 781772,EU256060,E U155251,EU256043, EU255936,EU155265 ,EU781824,EU48286 8,EU256072,EU8628 40,EU155249,EU256 067,EU255928,EU25 5986,EU255939,EU7 81759,EU255941,EU 255982,EU155292,E U482853,FJ182001,E U256055,JX463616,E U155278,EU255935,J X463627,EU256095, EU255987,EU155290 ,EU781746,EU15531 9,EU155340,EU2559 40,EU529679,FJQ242 81,EU781751,EU155 282,EU569722,EU78 1798,EU256031,EU2 34063,EU155320,EU 255955,EU781757,E U239715,FJQ24275,E U781771,EU155380, EU155247,EU255932 ,EU255933,EU15529 |

-continued

| Taxonomy | NCBI Reference Sequence ID | Host | No. of Genomes | Lineage | Segment Count | Genbank Accession ID |
|---|---|---|---|---|---|---|
| | | | | | | 4,EU781786,EF0328 87,EU155276,FJQ242 74,EU239713,EU781 785,EU529676,EU25 6026,EU256035,M67 463,JX463634,JX463 574,EU155322,EU78 1797,EU255957,EU4 82857,EU155299,JX4 63540,EU255963,EU 255953,EU255988,E U256022,EU155341, EU155214,EU255979 ,EU155241,EU78175 0,EU255956,EU4828 64,EU256020,EU256 007,EU781821,EU25 6039,EU482876,EU2 56015,EU255999,EU 482837,EU781758,E U155289,EU155246, EU781811,EU155309 ,EU781815,EU25603 0,EU155287,EU2559 83,EU155298,EU781 799,EU256046,EU25 5969 |
| Hepatitis C virus subtype 1b | NC_009827 ,NC_00982 6,NC_0098 25,NC_009 824,NC_00 4102,NC_0 09823 | vertebrates,human | 269 | Flaviviridae,Hepacivirus,Hepatitis C virus | — | AF356827,AF165060, EU482880,EU155280 ,AF165045,EU15536 2,AB154206,AF17657 3,EU155372,EU1552 20,EU660386,EU256 065,EU155324,EU25 6099,EU155369,AB1 54185,AB154202,EU 155303,M96362,M84 754,EU256103,AB44 2222,EU256092,AB1 54182,AF165063,EU 155307,AB154191,K C844051,AF483269, EU256001,EU155279 ,DQ071885,EU48288 5,EU155360,AB1541 92,AF207753,AB1541 86,EU155308,EU155 229,EU256054,EF03 |

| Taxonomy | NCBI Reference Sequence ID | Host | No. of Genomes | Lineage | Segment Count | Genbank Accession ID |
|---|---|---|---|---|---|---|
| | | | | | | 2893,AF207763,AB15 4203,EU155356,EU2 56081,EU155264,AF 054250,AF207770,AF 165053,EU482886,A B154181,EU256101, EU256102,EU239714 ,FJ155221,AF33332 4,EU256077,EU2560 80,AB442221,EU155 262,AB154190,EU23 4061,EU155359,AF2 07755,EU255962,EU 155375,AF207771,E U155230,EU255961, AF207762,AB154187, AB154200,EU155231 ,AB442219,EU15522 6,EU155331,AF2077 56,EU155326,EU155 334,U16362,EU1553 16,EU256079,AF165 064,EU155367,U890 19,EU482877,AB442 220,AF208024,EU25 6100,EU256061,EU1 55332,AF207758,EU 155325,AY045702,E U155258,AF165046, EU781829,EU256082 ,AF165048,AB154201 ,AF207757,EU78182 6,EU155306,AF0542 48,AB691953,AF1650 54,EU781825,AF207 768,EU234062,EU48 2879,EU862837,EU2 56078,S62220,EU155 357,AF207774,EU25 6075,FJQ24277,AB15 4189,EU155368,AF1 65062,EU155257,AF 207769,EU256062,E U256084,EU155364, AF165050,FN435993, EU155333,EU256090 ,EU155259,AF20776 6,EU155373,AF2077 |

| Taxonomy | NCBI Reference Sequence ID | Host | No. of Genomes | Lineage | Segment Count | Genbank Accession ID |
|---|---|---|---|---|---|---|
| | | | | | | 73,EF032892,AB154173,EU155281,AF207078,EU155219,EU155318,FJ390396,AF182881,EU155366,M565047,EU482849,AF18335,EU256098,EU165051,AF207760,AF482859,EU155222,E165056,EU857431,U256045,AB154179,EU482839,EU155536,AB154177,FJ47845,AF165049,EU155521,AF207754,FJQ240253,AF165052,EU15586,EU529682,EU25329,EU155365,FJQ24279,EU156088,HQ912956,EU45223,AB426117,EU482875,EU256076,E155232,AB154198,U155376,EU155302,EU155260,EU155537,EU256066,L02836,0,EU155337,AB154204,EU155377,EU207761,AB154336,EU155552,EU155317,AF207753,EU155301,AB77767,EU155328,EU19679,AF139594,AF207255234,U45476,EU78765,EU155304,AF01827,EU482883,AF054247,EU256083,EU781831,AF165057,EU482874,GU133617,AF207752,EU155224,AB154194,EU155263,EU155255,AY587844,EU155327,HQ912958,EU255960,EU862835,AF054249,EU155330,EU155358,EU155300,EU155218,U482860,EU155381,EU155228,AF207772 |

-continued

| Taxonomy | NCBI Reference Sequence ID | Host | No. of Genomes | Lineage | Segment Count | Genbank Accession ID |
|---|---|---|---|---|---|---|
| | | | | | | ,EU155261,EU155374,FJ390397,AB154199,EU781830,AF207764,EU155305,AF165058,AY460204,EU256089,EF638081,AF165061,AB154180,EU781832,EU155227,AJ238799,EU155254,EU256085,EU155335,KC844052,EU482888,AJ238800,EU155315,AB154205,EU155363,EU660388,AF165059,EU155371,HQ912959,EU482833,EU155235,AB779562,EU256059,AB154183,EU781828,EU256064,EU155256,EU155217,AB249644,EU256091,U01214,AF165055,FJ390398,EU155382 |
| Hepatitis C virus subtype lc | NC_009827,NC_009826,NC_009825,NC_009824,NC_004102,NC_009823 | vertebrates,human | 1 | Flaviviridae,Hepacivirus,Hepatitis C virus | — | KC844047 |
| Hepatitis C virus subtype 1g | NC_009827,NC_009826,NC_009825,NC_009824,NC_004102,NC_009823 | vertebrates,human | 1 | Flaviviridae,Hepacivirus,Hepatitis C virus | — | AM910652 |
| Hepatitis C virus subtype 2a | NC_009827,NC_009826,NC_009825,NC_009824,NC_004102,NC_009823 | vertebrates,human | 15 | Flaviviridae,Hepacivirus,Hepatitis C virus | — | KF676351,AF169004,AF238484,AB690461,AF238485,AF169003,AF238482,KC844043,AF238481,AB690460,AF238483,AF169002,KF676352,AF169005,AY746460 |
| Hepatitis C virus subtype 2b | NC_009827,NC_009826,NC_0098 | vertebrates,human | 22 | Flaviviridae,Hepacivirus,Hepatitis C virus | — | KC844048,AY232738, ,AY232745,AY23273, 3,AY232746,AY2327 |

| Taxonomy | NCBI Reference Sequence ID | Host | Lineage | No. of Genomes | Segment Count | Genbank Accession ID |
|---|---|---|---|---|---|---|
| | NC_009 825,NC_00 824,NC_0 4102,NC_0 09823 | | | | | ,42,AY232735,AY232 ,749,AY232747,AY23 ,2743,AY232734,AY2 ,32740,AY232737,AF2 38486,AY232732,AY 232731,AY232744,A Y232730,AY232739, AY232741,AY232736 ,AY232748 |
| Hepatitis C virus subtype 2f | NC_009827 ,NC_00982 6,NC_0098 25,NC_009 824,NC_00 4102,NC_0 09823 | vertebrates,human | Flaviviridae,Hepacivirus,Hepatitis C virus | 2 | — | KC844042,KC844050 |
| Hepatitis C virus subtype 3a | NC_009827 ,NC_00982 6,NC_0098 25,NC_009 824,NC_00 4102,NC_0 09823 | vertebrates,human | Flaviviridae,Hepacivirus,Hepatitis C virus | 19 | — | KF035124,AB792683, JQ717255,KF035125, KF035123,KC844041 ,JQ717256,JQ717258 ,GQ275355,JQ71725 9,AF046866,JQ71725 7,JN714194,KF03512 7,JQ717254,KF03512 6,AB691595,AB6915 96,JQ717260 |
| Hepatitis C virus subtype 3b | NC_009827 ,NC_00982 6,NC_0098 25,NC_009 824,NC_00 4102,NC_0 09823 | vertebrates,human | Flaviviridae,Hepacivirus,Hepatitis C virus | 1 | — | KC844044 |
| Hepatitis C virus subtype 4a | NC_009827 ,NC_00982 6,NC_0098 25,NC_009 824,NC_00 4102,NC_0 09823 | vertebrates,human | Flaviviridae,Hepacivirus,Hepatitis C virus | 8 | — | DQ418784,DQ41878 8,DQ418787,DQ5160 84,DQ418789,AB795 432,DQ418783,DQ41 8782 |
| Hepatitis C virus subtype 4d | NC_009827 ,NC_00982 6,NC_0098 25,NC_009 824,NC_00 4102,NC_0 09823 | vertebrates,human | Flaviviridae,Hepacivirus,Hepatitis C virus | 3 | — | KC844045,DQ516083 ,DQ418786 |

| Taxonomy | NCBI Reference Sequence ID | Host | No. of Genomes | Lineage | Segment Count | Genbank Accession ID |
|---|---|---|---|---|---|---|
| Hepatitis C virus subtype 4f | NC_009827,NC_009826,NC_009825,NC_009824,NC_004102,NC_009823 | vertebrates,human | 2 | Flaviviridae,Hepacivirus,Hepatitis C virus | — | EF589161,EF589160 |
| Hepatitis C virus subtype 5a | NC_009827,NC_009826,NC_009825,NC_009824,NC_004102,NC_009823 | vertebrates,human | 1 | Flaviviridae,Hepacivirus,Hepatitis C virus | — | KC844046 |
| Hepatitis C virus subtype 6a | NC_009827,NC_009826,NC_009825,NC_009824,NC_004102,NC_009823 | vertebrates,human | 15 | Flaviviridae,Hepacivirus,Hepatitis C virus | — | DQ480519,DQ480521,DQ480518,DQ480520,KC844037,DQ480515,DQ480512,DQ480514,DQ480523,DQ480513,KC844038,DQ480516,DQ480524,DQ480522,DQ480517 |
| Hepatitis C virus subtype 6c | NC_009827,NC_009826,NC_009825,NC_009824,NC_004102,NC_009823 | vertebrates,human | 1 | Flaviviridae,Hepacivirus,Hepatitis C virus | — | EF424629 |
| Hepatitis C virus subtype 6e | NC_009827,NC_009826,NC_009825,NC_009824,NC_004102,NC_009823 | vertebrates,human | 1 | Flaviviridae,Hepacivirus,Hepatitis C virus | — | DQ314805 |
| Hepatitis C virus subtype 6f,NC_00982 | NC_009827 | vertebrates,human 0 | 2 | Flaviviridae,Hepacivirus,Hepatitis C virus | — | DQ835764,DQ835776 |
| Hepatitis C virus subtype 6g | NC_009827,NC_009826,NC_009825,NC_009824,NC_004102,NC_009823 | vertebrates,human | 1 | Flaviviridae,Hepacivirus,Hepatitis C virus | — | DQ314806 |

-continued

| Taxonomy | NCBI Reference Sequence ID | Host | No. of Genomes | Lineage | Segment Count | Genbank Accession ID |
|---|---|---|---|---|---|---|
| Hepatitis C virus subtype 6i | NC_009827,NC_009826,NC_009825,NC_009824,NC_009823 | vertebrates,human | 2 | Flaviviridae,Hepacivirus,Hepatitis C virus | — | DQ835762,DQ835770 |
| Hepatitis C virus subtype 6j | NC_009827,NC_009826,NC_009825,NC_009824,NC_009823 | vertebrates,human | 2 | Flaviviridae,Hepacivirus,Hepatitis C virus | — | DQ835769,DQ835576 |
| Hepatitis C virus subtype 6k | NC_009827,NC_009826,NC_009825,NC_009824,NC_009823 | vertebrates,human | 4 | Flaviviridae,Hepacivirus,Hepatitis C virus | — | DQ278893,AY878651,DQ278891,AY878650 |
| Hepatitis C virus subtype 6l | NC_009827,NC_009826,NC_009825,NC_009824,NC_009823 | vertebrates,human | 1 | Flaviviridae,Hepacivirus,Hepatitis C virus | — | EF424628 |
| Hepatitis C virus subtype 6m | NC_009827,NC_009826,NC_009825,NC_009824,NC_009823 | vertebrates,human | 4 | Flaviviridae,Hepacivirus,Hepatitis C virus | — | DQ835767,DQ835763,DQ835766,DQ835765 |
| Hepatitis C virus subtype 6n | NC_009827,NC_009826,NC_009825,NC_009824,NC_009823 | vertebrates,human | 3 | Flaviviridae,Hepacivirus,Hepatitis C virus | — | DQ835768,DQ278894,AY878652 |
| Hepatitis C virus subtype 6o | NC_009827,NC_009826,NC_009825,NC_009824,NC_009823 | vertebrates,human | 1 | Flaviviridae,Hepacivirus,Hepatitis C virus | — | EF424627 |

| Taxonomy | NCBI Reference Sequence ID | Host | No. of Genomes | Lineage | Segment Count | Genbank Accession ID |
|---|---|---|---|---|---|---|
| Hepatitis C virus subtype 6p | 824,NC_00 4102,NC_0 09823 | vertebrates,human | 1 | Flaviviridae,Hepacivirus,Hepatitis C virus | — | EF424626 |
| Hepatitis C virus subtype 6q | NC_009827 ,NC_00982 6,NC_0098 25,NC_009 824,NC_00 4102,NC_0 09823 | vertebrates,human | 1 | Flaviviridae,Hepacivirus,Hepatitis C virus | — | EF424625 |
| Hep -continued

| Taxonomy | NCBI Reference Sequence ID | Host | No. of Genomes | Lineage | Segment Count | Genbank Accession ID |
|---|---|---|---|---|---|---|
| | | | | | | ,M80581,AB291952,JF915746,AB630970,AB291959,AB189072,AB369688,AB222182,KC492825,AB291957,AB443625,D11093,JN906975,JN167537,AB602441,AB220975,JN906974,AY575859,L25595,AB780452,AB362839,JQ655733,AB220972,JF443726,AB85 6243,AB369690,AB740221,FJ906895,AB602440,AB189071,AB291954,AB437317,AB220976,AB591733,AF444002,AB074917,AB573435,AB291958,AB197673,JQ740781,HQ709170,DQ459342,HQ389543,EU495148,AB591734,AB425831,JQ953666,JQ655735,AB291962,AF185822,AB369687,FJ527832,AB291965,AY204877,AB089824,HQ634346,AB220978,EU360977,AB740232,AB362842,AF459438,JF443724,AB369691,AB220973,AJ272108,JN167538,EU375463,AB220979,HQ389544,AB291955,AB236320,GU937805,AB091395,AB602439,EU366959,AB108537,AB091394,JF443723,AB222183,AF060669,AB074918,AB290312,D10330,AY575857,AB189075,AF444003,AB443627,AB437318,KC618402,AB193176,GU206559,AB291964,AB074920,AB780453 |

| Taxonomy | NCBI Reference Sequence ID | Host | No. of Genomes | Lineage | Segment Count | Genbank Accession ID |
|---|---|---|---|---|---|---|
| | | | | | | ,AB720035,JQ993308 ,AB248520,AB43731 9,AB080575,JF44372 0,AB780450,AB2485 22,AB200239,AB246 676,JQ655736,JF443 717,FJ906896,JQ768 461,AB291951,L2554 7,AB291968,AB2209 77,FJ956757,AB0978 12,AY230202,AB630 971,FJ457024,AB291 956,AB720034,AB18 9070,FJ763142,JF44 3718,AB253420,AB2 20974,AB521806,AB 362843,AB291960,A B425830,AB740222, AB291961,FJ705359, JF443722,AB362841, AB197674,JN837481, KC618403,AB193178 ,AP003430,X99441,A B443626,JX109834 |
| Hepatitis E virus type 3 | NC_001434 | vertebrates,human | 1 | Hepeviridae,Hepevirus,Hepatitis E virus | — | AB593690 |
| Hepatitis G virus isolate PEI | NC_001710 | vertebrates,human | 1 | Flaviviridae,Pegivirus,GB virus C | — | AF309966 |
| Hepatitis delta virus | NC_001653 | vertebrates,human | 108 | Deltavirus,Hepatitis delta virus | — | HQ005370,AM18332 9,HQ005365,AB0379 49,AB118842,M8491 7,AJ584849,AJ58484 4,HM046802,AB1188 49,AY633627,AB118 821,AB118839,AB11 8837,AB118829,M28 267,M92448,KF6605 98,AM183332,HQ005 364,AB118820,AB11 8832,EF514905,DQ10 75,M58629,AB11881 8,AB118833,AJ30707 7,AB037948,U81989, HQ005366,AB118827 ,AY648956,HQ00537 1,AM183331,HF6794 05,AY648958,AB118 844,HQ005367,AY26 1460,GU177114,AJ5 |

-continued

| Taxonomy | NCBI Reference Sequence ID | Host | No. of Genomes | Lineage | Segment Count | Genbank Accession ID |
|---|---|---|---|---|---|---|
| Hepatitis delta virus dFr2012 | NC_001653 | vertebrates,human | 1 | Deltavirus,Hepatitis delta virus | | 84845,AB118846,AB 118845,AB118826,A B118840,AY648953, X85253,AB037947,A B118836,AB118838, AY648957,AF104263, AY648959,AB118830 ,AB118819,AY64895 5,AB088679,AB1188 41,AJ584848,EF5149 07,AB118843,XQ4451 ,KF660602,AB118822 ,KC590319,EF51490 4,L22066,AF104264, HQ005369,AM18332 7,EF514906,AB11884 8,AM183330,U81988, AB118824,AY261458 ,AJ584847,AB118823 ,M21012,KF660599, M55042,HF679406,A M183333,AB118847, AY261459,HQ005368 ,AB118828,X77627,A M183328,AJ584846, AY261457,AJQ00558, KF660600,AF098261, AM183326,AB118831 ,HQ005372,AB11882 5,AY648952,EF51490 3,AB118835,AF42564 5,HF679404,AY6489 54,KF660601,AB1188 34,AF425644 |
| Hepatitis delta virus dFr2040 | NC_001653 | vertebrates,human | 1 | Deltavirus,Hepatitis delta virus | — | AM902177 |
| Hepatitis delta virus dFr2042 | NC_001653 | vertebrates,human | 1 | Deltavirus,Hepatitis delta virus | — | AM902178 |
| Hepatitis delta virus dFr2043 | NC_001653 | vertebrates,human | 1 | Deltavirus,Hepatitis delta virus | — | AM902179 |
| Hepatitis delta virus dFr2045 | NC_001653 | vertebrates,human | 1 | Deltavirus,Hepatitis delta virus | — | AM902180 |
| Hepatitis delta virus dFr2046 | NC_001653 | vertebrates,human | 1 | Deltavirus,Hepatitis delta virus | — | AM902168 |
| Hepatitis delta virus dFr2067 | NC_001653 | vertebrates,human | 1 | Deltavirus,Hepatitis delta virus | — | AM779580 |
| Hepatitis delta virus dFr2067 | NC_001653 | vertebrates,human | 1 | Deltavirus,Hepatitis delta virus | — | AM902163 |

| Taxonomy | NCBI Reference Sequence ID | Host | No. of Genomes | Lineage | Segment Count | Genbank Accession ID |
|---|---|---|---|---|---|---|
| Hepatitis delta virus dFr2119 | NC_001653 | vertebrates,human | 1 | Deltavirus,Hepatitis delta virus | — | AM779575 |
| Hepatitis delta virus dFr2137 | NC_001653 | vertebrates,human | 1 | Deltavirus,Hepatitis delta virus | — | AM902164 |
| Hepatitis delta virus dFr2172 | NC_001653 | vertebrates,human | 1 | Deltavirus,Hepatitis delta virus | — | AM902165 |
| Hepatitis delta virus dFr2189 | NC_001653 | vertebrates,human | 1 | Deltavirus,Hepatitis delta virus | — | AM902166 |
| Hepatitis delta virus dFr2201 | NC_001653 | vertebrates,human | 1 | Deltavirus,Hepatitis delta virus | — | AM902167 |
| Hepatitis delta virus dFr2210 | NC_001653 | vertebrates,human | 1 | Deltavirus,Hepatitis delta virus | — | AM902181 |
| Hepatitis delta virus dFr2236 | NC_001653 | vertebrates,human | 1 | Deltavirus,Hepatitis delta virus | — | AM902169 |
| Hepatitis delta virus dFr2239b | NC_001653 | vertebrates,human | 1 | Deltavirus,Hepatitis delta virus | — | AM779578 |
| Hepatitis delta virus dFr2244 | NC_001653 | vertebrates,human | 1 | Deltavirus,Hepatitis delta virus | — | AM902170 |
| Hepatitis delta virus dFr2258 | NC_001653 | vertebrates,human | 1 | Deltavirus,Hepatitis delta virus | — | AM902171 |
| Hepatitis delta virus dFr2264 | NC_001653 | vertebrates,human | 1 | Deltavirus,Hepatitis delta virus | — | AM902172 |
| Hepatitis delta virus dFr2284 | NC_001653 | vertebrates,human | 1 | Deltavirus,Hepatitis delta virus | — | AM779577 |
| Hepatitis delta virus dFr2380 | NC_001653 | vertebrates,human | 1 | Deltavirus,Hepatitis delta virus | — | AM902173 |
| Hepatitis delta virus dFr2395 | NC_001653 | vertebrates,human | 1 | Deltavirus,Hepatitis delta virus | — | AM779579 |
| Hepatitis delta virus dFr2404 | NC_001653 | vertebrates,human | 1 | Deltavirus,Hepatitis delta virus | — | AM902174 |
| Hepatitis delta virus dFr2406 | NC_001653 | vertebrates,human | 1 | Deltavirus,Hepatitis delta virus | — | AM902175 |
| Hepatitis delta virus dFr2411 | NC_001653 | vertebrates,human | 1 | Deltavirus,Hepatitis delta virus | — | AM902176 |
| Hepatitis delta virus dFr2544 | NC_001653 | vertebrates,human | 1 | Deltavirus,Hepatitis delta virus | — | AM779576 |
| Hepatitis delta virus dFr508 | NC_001653 | vertebrates,human | 1 | Deltavirus,Hepatitis delta virus | — | AM779574 |
| Hepatitis delta virus dTk1 | NC_001653 | vertebrates,human | 1 | Deltavirus,Hepatitis delta virus | — | AM779581 |
| Hepatitis delta virus dTk10 | NC_001653 | vertebrates,human | 1 | Deltavirus,Hepatitis delta virus | — | AM779583 |
| Hepatitis delta virus dTk12 | NC_001653 | vertebrates,human | 1 | Deltavirus,Hepatitis delta virus | — | AM779595 |
| Hepatitis delta virus dTk13 | NC_001653 | vertebrates,human | 1 | Deltavirus,Hepatitis delta virus | — | AM779593 |
| Hepatitis delta virus dTk2 | NC_001653 | vertebrates,human | 1 | Deltavirus,Hepatitis delta virus | — | AM779597 |
| Hepatitis delta virus dTk21 | NC_001653 | vertebrates,human | 1 | Deltavirus,Hepatitis delta virus | — | AM779596 |
| Hepatitis delta virus dTk27 | NC_001653 | vertebrates,human | 1 | Deltavirus,Hepatitis delta virus | — | AM779594 |
| Hepatitis delta virus dTk28 | NC_001653 | vertebrates,human | 1 | Deltavirus,Hepatitis delta virus | — | AM779586 |
| Hepatitis delta virus dTk3 | NC_001653 | vertebrates,human | 1 | Deltavirus,Hepatitis delta virus | — | AM779589 |
| Hepatitis delta virus dTk34 | NC_001653 | vertebrates,human | 1 | Deltavirus,Hepatitis delta virus | — | AM779582 |

-continued

| Taxonomy | NCBI Reference Sequence ID | Host | No. of Genomes | Lineage | Segment Count | Genbank Accession ID |
|---|---|---|---|---|---|---|
| Hepatitis delta virus dTk35 Hepatitis delta virus dTk38 | NC_001653 | vertebrates,human | 1 | Deltavirus,Hepatitis delta virus | — | AM779590 |
| Hepatitis delta virus dTk4 | NC_001653 | vertebrates,human | 1 | Deltavirus,Hepatitis delta virus | — | AM779584 |
| Hepatitis delta virus dTk5 | NC_001653 | vertebrates,human | 1 | Deltavirus,Hepatitis delta virus | — | AM779591 |
| Hepatitis delta virus dTk6 | NC_001653 | vertebrates,human | 1 | Deltavirus,Hepatitis delta virus | — | AM779585 |
| Hepatitis delta virus dTk7 | NC_001653 | vertebrates,human | 1 | Deltavirus,Hepatitis delta virus | — | AM779587 |
| Hepatitis delta virus dTk8 | NC_001653 | vertebrates,human | 1 | Deltavirus,Hepatitis delta virus | — | AM779592 |
| HoJo virus | NC_005219 | vertebrates,human | 1 | Bunyaviridae,Hantavirus,Hantaan virus | seg. M | DQ0376 |
| Horsepox virus | NC_006998 | vertebrates,human | 1 | Poxviridae,Orthopoxvirus,Vaccinia virus | — | DQ792504 |
| Hu39694 virus | NC_003467 | vertebrates,human | 1 | Bunyaviridae,Hantavirus,Andes virus | seg. M | AF028023 |
| Human Respiratory syncytial virus 9320 | NC_001781 | vertebrates,human | 1 | Paramyxoviridae,Pneumovirus,Human respiratory syncytial virus | — | AY353550 |
| Human adenovirus 1 | NC_001405 | vertebrates,human | 3 | Adenoviridae,Mastadenovirus,Human adenovirus C | — | KF429744,KF268331, AF534906 |
| Human adenovirus 11 | NC_011202 | vertebrates,human | 2 | Adenoviridae,Mastadenovirus,Human adenovirus B | — | FJ643676,AF532578 |
| Human adenovirus 11 | NC_011203 | vertebrates,human | 2 | Adenoviridae,Mastadenovirus,Human adenovirus B | — | FJ643676,AF532578 |
| Human adenovirus 11a | NC_011202 | vertebrates,human | 1 | Adenoviridae,Mastadenovirus,Human adenovirus B | — | FJ597732 |
| Human adenovirus 11a | NC_011203 | vertebrates,human | 1 | Adenoviridae,Mastadenovirus,Human adenovirus B | — | FJ597732 |
| Human adenovirus 14 | NC_011202 | vertebrates,human | 4 | Adenoviridae,Mastadenovirus,Human adenovirus B | — | FJ822614,JX892927, AY803294,JN032132 |
| Human adenovirus 14 | NC_011203 | vertebrates,human | 4 | Adenoviridae,Mastadenovirus,Human adenovirus B | — | FJ822614,JX892927, AY803294,JN032132 |
| Human adenovirus 15 | NC_010956 ,NC_01295 9 | vertebrates,human | 3 | Adenoviridae,Mastadenovirus,Human adenovirus D | — | AB562586,KF268201, KF268329 |
| Human adenovirus 16 | NC_011202 | vertebrates,human | 2 | Adenoviridae,Mastadenovirus,Human adenovirus B | — | JN860680,AY601636 |
| Human adenovirus 16 | NC_011203 | vertebrates,human | 2 | Adenoviridae,Mastadenovirus,Human adenovirus B | — | JN860680,AY601636 |
| Human adenovirus 17 | NC_010956 ,NC_01295 9 | vertebrates,human | 3 | Adenoviridae,Mastadenovirus,Human adenovirus D | — | KF268330,HQ910407 ,AF108105 |
| Human adenovirus 18 | NC_001460 | vertebrates,human | 1 | Adenoviridae,Mastadenovirus,Human adenovirus A | — | GU191019 |
| Human adenovirus 19 | NC_010956 ,NC_01295 9 | vertebrates,human | 7 | Adenoviridae,Mastadenovirus,Human adenovirus D | — | KF268323,EF121005, AB448773,AB448774 ,AB448772,AB44877 1,JQ326209 |
| Human adenovirus 2 | NC_001405 | vertebrates,human | 1 | Adenoviridae,Mastadenovirus,Human adenovirus C | — | KF268310 |
| Human adenovirus 20 | NC_010956 ,NC_01295 9 | vertebrates,human | 1 | Adenoviridae,Mastadenovirus,Human adenovirus D | — | KF268207 |

| Taxonomy | NCBI Reference Sequence ID | Host | No. of Genomes | Lineage | Segment Count | Genbank Accession ID |
|---|---|---|---|---|---|---|
| Human adenovirus 21 | NC_011202 | vertebrates,human | 1 | Adenoviridae,Mastadenovirus,Human adenovirus B | — | AY601633 |
| Human adenovirus 21 | NC_011203 | vertebrates,human | 1 | Adenoviridae,Mastadenovirus,Human adenovirus B | — | AY601633 |
| Human adenovirus 22 | NC_010956,NC_012959 | vertebrates,human | 2 | Adenoviridae,Mastadenovirus,Human adenovirus D | — | FJ619037,FJ404771 |
| Human adenovirus 23 | NC_010956,NC_012959 | vertebrates,human | 1 | Adenoviridae,Mastadenovirus,Human adenovirus D | — | KF279629 |
| Human adenovirus 26 | NC_010956,NC_012959 | vertebrates,human | 1 | Adenoviridae,Mastadenovirus,Human adenovirus D | — | EF153474 |
| Human adenovirus 28 | NC_010956,NC_012959 | vertebrates,human | 2 | Adenoviridae,Mastadenovirus,Human adenovirus D | — | KF268320,FJ824826 |
| Human adenovirus 29 | NC_010956,NC_012959 | vertebrates,human | 1 | Adenoviridae,Mastadenovirus,Human adenovirus D | — | AB562587 |
| Human adenovirus 3 | NC_011202 | vertebrates,human | 7 | Adenoviridae,Mastadenovirus,Human adenovirus B | — | KF268212,KF268210,KF268202,AY599834,AY599836,KF268315,KF429752 |
| Human adenovirus 3 | NC_011203 | vertebrates,human | 7 | Adenoviridae,Mastadenovirus,Human adenovirus B | — | KF268212,KF268210,KF268202,AY599834,AY599836,KF268315,KF429752 |
| Human adenovirus 3+11p | NC_011202 | vertebrates,human | 2 | Adenoviridae,Mastadenovirus,Human adenovirus B | — | EF564600,EF564601 |
| Human adenovirus 3+11p | NC_011203 | vertebrates,human | 2 | Adenoviridae,Mastadenovirus,Human adenovirus B | — | EF564600,EF564601 |
| Human adenovirus 3+7 | NC_011202 | vertebrates,human | 1 | Adenoviridae,Mastadenovirus,Human adenovirus B | — | JN860679 |
| Human adenovirus 3+7 | NC_011203 | vertebrates,human | 1 | Adenoviridae,Mastadenovirus,Human adenovirus B | — | JN860679 |
| Human adenovirus 3-16 | NC_011202 | vertebrates,human | 1 | Adenoviridae,Mastadenovirus,Human adenovirus B | — | JN860678 |
| Human adenovirus 3-16 | NC_011203 | vertebrates,human | 1 | Adenoviridae,Mastadenovirus,Human adenovirus B | — | JN860678 |
| Human adenovirus 30 | NC_010956,NC_012959 | vertebrates,human | 1 | Adenoviridae,Mastadenovirus,Human adenovirus D | — | KF268335 |
| Human adenovirus 31 | NC_001460 | vertebrates,human | 1 | Adenoviridae,Mastadenovirus,Human adenovirus A | — | AM749299 |
| Human adenovirus 32 | NC_010956,NC_012959 | vertebrates,human | 2 | Adenoviridae,Mastadenovirus,Human adenovirus D | — | KF268325,KF268327 |

| Taxonomy | NCBI Reference Sequence ID | Host | No. of Genomes | Lineage | Segment Count | Genbank Accession ID |
|---|---|---|---|---|---|---|
| Human adenovirus 33 | NC_010956, NC_012959 | vertebrates,human | 1 | Adenoviridae,Mastadenovirus,Human adenovirus D | — | KF268322 |
| Human adenovirus 34 | NC_011202 | vertebrates,human | 2 | Adenoviridae,Mastadenovirus,Human adenovirus B | — | KF268328,AY737797 |
| Human adenovirus 34 | NC_011202 | vertebrates,human | 2 | Adenoviridae,Mastadenovirus,Human adenovirus B | — | KF268328,AY737797 |
| Human adenovirus 35 | NC_011203 | vertebrates,human | 2 | Adenoviridae,Mastadenovirus,Human adenovirus B | — | AY128640,AY271307 |
| Human adenovirus 35 | NC_011203 | vertebrates,human | 2 | Adenoviridae,Mastadenovirus,Human adenovirus B | — | AY128640,AY271307 |
| Human adenovirus 36 | NC_010956, NC_012959 | vertebrates,human | 1 | Adenoviridae,Mastadenovirus,Human adenovirus D | — | GQ384080 |
| Human adenovirus 37 | NC_010956, NC_012959 | vertebrates,human | 9 | Adenoviridae,Mastadenovirus,Human adenovirus D | — | AB448775,KF268208, KF268324,AB448778, AB448777,AB448776 ,KF268203,DQ90090 0,KF268334 |
| Human adenovirus 38 | NC_010956, NC_012959 | vertebrates,human | 1 | Adenoviridae,Mastadenovirus,Human adenovirus D | — | KF268312 |
| Human adenovirus 4 | NC_010956, NC_012959 | vertebrates,human | 1 | Adenoviridae,Mastadenovirus,Human adenovirus D | — | KF268313 |
| Human adenovirus 4 | NC_011202 | vertebrates,human | 1 | Adenoviridae,Mastadenovirus,Human adenovirus B | — | KF429748 |
| Human adenovirus 4 | NC_011203 | vertebrates,human | 1 | Adenoviridae,Mastadenovirus,Human adenovirus B | — | KF429748 |
| Human adenovirus 43 | NC_010956, NC_012959 | vertebrates,human | 1 | Adenoviridae,Mastadenovirus,Human adenovirus D | — | KC529648 |
| Human adenovirus 46 | NC_010956, NC_012959 | vertebrates,human | 3 | Adenoviridae,Mastadenovirus,Human adenovirus D | — | KF268332,AY875648, KF268211 |
| Human adenovirus 48 | NC_010956, NC_012959 | vertebrates,human | 1 | Adenoviridae,Mastadenovirus,Human adenovirus D | — | EF153473 |
| Human adenovirus 49 | NC_010956, NC_012959 | vertebrates,human | 1 | Adenoviridae,Mastadenovirus,Human adenovirus D | — | DQ393829 |
| Human adenovirus 5 | NC_001405 | vertebrates,human | 2 | Adenoviridae,Mastadenovirus,Human adenovirus C | — | AY601635,M73260 |
| Human adenovirus 50 | NC_011202 | vertebrates,human | 1 | Adenoviridae,Mastadenovirus,Human adenovirus B | — | AY737798 |
| Human adenovirus 50 | NC_011203 | vertebrates,human | 1 | Adenoviridae,Mastadenovirus,Human adenovirus B | — | AY737798 |

-continued

| Taxonomy | NCBI Reference Sequence ID | Host | No. of Genomes | Lineage | Segment Count | Genbank Accession ID |
|---|---|---|---|---|---|---|
| Human adenovirus 53 | NC_010956,NC_012959 | vertebrates,human | 1 | Adenoviridae,Mastadenovirus,Human adenovirus D | — | FJ169625 |
| Human adenovirus 54 | NC_010956,NC_012959 | vertebrates,human | 1 | Adenoviridae,Mastadenovirus,Human adenovirus D | — | AB448770 |
| Human adenovirus 55 | NC_011202 | vertebrates,human | 3 | Adenoviridae,Mastadenovirus,Human adenovirus B | — | JX123028,JX123029,JX123027 |
| Human adenovirus 55 | NC_011203 | vertebrates,human | 3 | Adenoviridae,Mastadenovirus,Human adenovirus B | — | JX123028,JX123029,JX123027 |
| Human adenovirus 56 | NC_010956,NC_012959 | vertebrates,human | 1 | Adenoviridae,Mastadenovirus,Human adenovirus D | — | KF268209 |
| Human adenovirus 6 | NC_001405 | vertebrates,human | 2 | Adenoviridae,Mastadenovirus,Human adenovirus C | — | FJ349096,HQ413315 |
| Human adenovirus 60 MPW-2011 | NC_010956,NC_012959 | vertebrates,human | 1 | Adenoviridae,Mastadenovirus,Human adenovirus D | — | HQ007053 |
| Human adenovirus 64 | NC_010956,NC_012959 | vertebrates,human | 4 | Adenoviridae,Mastadenovirus,Human adenovirus D | — | JQ326206,JQ326207,JQ326208,KF268213 |
| Human adenovirus 67 | NC_010956,NC_012959 | vertebrates,human | 1 | Adenoviridae,Mastadenovirus,Human adenovirus D | — | AP012302 |
| Human adenovirus 7 | NC_011202 | vertebrates,human | 10 | Adenoviridae,Mastadenovirus,Human adenovirus B | — | AY601634,JF800905,AY594256,HQ659699,KF268314,AY594255,AY495969,KF268316,GQ478341,JX62513 4 |
| Human adenovirus 7 | NC_011203 | vertebrates,human | 10 | Adenoviridae,Mastadenovirus,Human adenovirus B | — | AY601634,JF800905,AY594256,HQ659699,KF268314,AY594255,AY495969,KF268316,GQ478341,JX62513 4 |
| Human adenovirus 7d2 | NC_011202 | vertebrates,human | 1 | Adenoviridae,Mastadenovirus,Human adenovirus B | — | JN860677 |
| Human adenovirus 7d2 | NC_011203 | vertebrates,human | 1 | Adenoviridae,Mastadenovirus,Human adenovirus B | — | JN860677 |
| Human adenovirus 7h | NC_011202 | vertebrates,human | 1 | Adenoviridae,Mastadenovirus,Human adenovirus B | — | JN860676 |
| Human adenovirus 7h | NC_011203 | vertebrates,human | 1 | Adenoviridae,Mastadenovirus,Human adenovirus B | — | JN860676 |
| Human adenovirus 8 | NC_010956,NC_012959 | vertebrates,human | 14 | Adenoviridae,Mastadenovirus,Human adenovirus D | — | KF268333,KF429743,KF429746,AB448768,AB448767,KF429750,KF429747,KF429745, |

| Taxonomy | NCBI Reference Sequence ID | Host | No. of Genomes | Lineage | Segment Count | Genbank Accession ID |
|---|---|---|---|---|---|---|
| Human adenovirus 9 | NC_010956, NC_012959 | vertebrates,human | 1 | Adenoviridae,Mastadenovirus,Human adenovirus D | — | KF429751,KF268205, AB448769,KF429749, KF268321,KF429753 |
| Human adenovirus A | NC_001460 | vertebrates,human | 2 | Adenoviridae,Mastadenovirus,Human adenovirus A | — | KF268119,X73487 |
| Human adenovirus B | NC_011202 | vertebrates,human | 31 | Adenoviridae,Mastadenovirus,Human adenovirus B | — | JX423384,KF633445, AY163756,JX423385, JX491639,JX423386, KF268311,KF268133, JX423380,KF268120, DQ099432,KF268125, KF268124,KF268134, JX423382,KF268121, KF268117,KF268128, KF268196,JX423383, KF268132,KF268123, KF268135,KF268126, JX423388,AY598970, EF011630,JX423387, DQ105654,KF268131, JX423381 |
| Human adenovirus B | NC_011203 | vertebrates,human | 31 | Adenoviridae,Mastadenovirus,Human adenovirus B | — | JX423384,KF633445, JX423385,JX491639, JX423386,KF268311, KF268133,JX423380, KF268120,DQ099432, KF268125,DQ08646 6,KF268124,KF26813 4,JX423382,KF26812 1,KF268117,KF26812 8,KF268196,JX42338 3,KF268132,KF26812 3,KF268135,KF26812 6,JX423388,AY59897 0,EF011630,JX42338 7,DQ105654,KF2681 31,JX423381 |
| Human adenovirus C | NC_001405 | vertebrates,human | 18 | Adenoviridae,Mastadenovirus,Human adenovirus C | — | KF268199,JX173086, JX173085,KF268130, JX173080,JX423389, KF429754,JX173079, JX173083,JQ1917,AY 339865,JX173078,KF 268129,JX173082,KF |

| Taxonomy | NCBI Reference Sequence ID | Host | No. of Genomes | Lineage | Segment Count | Genbank Accession ID |
|---|---|---|---|---|---|---|
| Human adenovirus CR/France/2008 | NC_010956,NC_012959 | vertebrates,human | 1 | Adenoviridae,Mastadenovirus,Human adenovirus D | — | 268127,JX173084,JX173077,JX173081 |
| Human adenovirus D | NC_010956,NC_012959 | vertebrates,human | 15 | Adenoviridae,Mastadenovirus,Human adenovirus D | — | KF268197,JN162672,AB605242,AB605240,KF268122,AB605243,AB605244,AB605245,AB605246,KF268118,AB605241,AJ854486,KF268198,AB562588,JN162671 |
| Human adenovirus D B172/Dhaka City | NC_010956,NC_012959 | vertebrates,human | 1 | Adenoviridae,Mastadenovirus,Human adenovirus D | — | AP012285 |
| Human adenovirus JJS-2010 | NC_001405 | vertebrates,human | 1 | Adenoviridae,Mastadenovirus,Human adenovirus C | — | HQ003817 |
| Human adenovirus MZ | NC_001460 | vertebrates,human | 1 | Adenoviridae,Mastadenovirus,Human adenovirus A | — | JF964962 |
| Human astrovirus | NC_001943 | vertebrates,human | 5 | Astroviridae,Mamastrovirus,Mamastrovirus 1 | — | FJ375759,JF327666,AF141381,AB308374,L13745 |
| Human astrovirus 1 | NC_001943 | vertebrates,human | 5 | Astroviridae,Mamastrovirus,Mamastrovirus 1 | — | L23513,AY720892,H0399856,KF211475,JN887820 |
| Human astrovirus 1 Beijing/128/2005/CH N | NC_001943 | vertebrates,human | 1 | Astroviridae,Mamastrovirus,Mamastrovirus 1 | — | FJ755402 |
| Human astrovirus 1 Beijing/176/2006/CH N | NC_001943 | vertebrates,human | 1 | Astroviridae,Mamastrovirus,Mamastrovirus 1 | — | FJ755403 |
| Human astrovirus 1 Beijing/291/2007/CH N | NC_001943 | vertebrates,human | 1 | Astroviridae,Mamastrovirus,Mamastrovirus 1 | — | FJ755404 |
| Human astrovirus 1 Beijing/293/2007/CH N | NC_001943 | vertebrates,human | 1 | Astroviridae,Mamastrovirus,Mamastrovirus 1 | — | FJ755405 |
| Human astrovirus 2 | NC_001943 | vertebrates,human | 2 | Astroviridae,Mamastrovirus,Mamastrovirus 1 | — | KF039911,KF039910 |
| Human astrovirus 4 | NC_001943 | vertebrates,human | 5 | Astroviridae,Mamastrovirus,Mamastrovirus 1 | — | KF039913,DQ070852,AY720891,DQ344027,KF039912 |
| Human astrovirus 5 | NC_001943 | vertebrates,human | 2 | Astroviridae,Mamastrovirus,Mamastrovirus 1 | — | JQ403108,DQ028633 |
| Human astrovirus 6 | NC_001943 | vertebrates,human | 2 | Astroviridae,Mamastrovirus,Mamastrovirus 1 | — | GQ495608,HM237363 |
| Human astrovirus 8 | NC_001943 | vertebrates,human | 1 | Astroviridae,Mamastrovirus,Mamastrovirus 1 | — | AF260508 |
| Human bocavirus | NC_007455 | vertebrates,human | 123 | Parvoviridae,Bocavirus,Human bocavirus | — | JN387081,EF450736,GQ455987,JF327789,EU984236,JN387079,EF450731,FJ560720,EF450731,EF450722,AB481071,EF450739 |

| Taxonomy | NCBI Reference Sequence ID | Host | No. of Genomes | Lineage | Segment Count | Genbank Accession ID |
|---|---|---|---|---|---|---|
| | | | | | | ,AB481073,EU26297 8,AB480171,EF45072 9,JX887481,AB48108 5,AB480175,JN12895 4,DQ457413,JN1289 55,JN632515,FJ6954 72,DQ988934,JN086 998,JN387083,AB481 084,EF450727,EU98 4239,JQ411251,EF45 0717,JQ964115,EU9 84245,JN387080,EF4 50733,AB481082,EU 984235,EU984243,JN 632514,JN632511,AB 480176,EF450718,JN 632513,EF450724,AB 481077,EF450732,EF 450737,JF699044,HO 585888,DQ000495,E F450738,AB481083,E F450735,EF203921,A B481076,EU984231,J N632519,EF450734, AB480170,EF450726, GQ925675,JQ964116 ,AB480172,JF327788 ,AB480174,AB55103 2,EF450728,EF45072 0,EU984238,EF4507 21,JN387084,EF4507 30,GQ926981,JX887 480,JQ923422,JF327 786,EF203922,EU26 2979,DQ340570,KC8 23115,JN794566,JN3 87085,GQ926983,EU 984233,JN794565,FJ 496754,AB481081,E U984241,AB481074, EU984244,DQ988933 ,JN632518,AB481075 ,EF450723,GU13942 3,GQ455988,EU9842 40,JX887482,EF4507 19,EU984242,EF450 740,EU984237,EF45 0725,GU338055,FJ185 |

| Taxonomy | NCBI Reference Sequence ID | Host | No. of Genomes | Lineage | Segment Count | Genbank Accession ID |
|---|---|---|---|---|---|---|
| | | | | | | 8259,AB481072,JN12 8953,GQ926982,JN6 32516,EF203920,JQ9 64114,JF327787,JN6 32517,DQ000496,JN 387082,AB480173,E U984232,AB481078, AB481079,JN128956, EU984234,JN632512 |
| Human bocavirus 2 | NC_012042 | vertebrates,human | 15 | Parvoviridae,Bocavirus,Human bocavirus 2 | — | FJ973560,FJ170278, FJ948860,GU048664, GU301645,EU082213 ,GU048662,FJ170279 ,FJ170280,EU082214 ,GU301644,FJ973558 ,FJ973559,GQ20073 7,GU048663 |
| Human bocavirus 3 | NC_012564 | vertebrates,human | 7 | Parvoviridae,Bocavirus,Human bocavirus 3 | — | HM132056,GQ86766 7,EU918736,GU0486 65,FJ973562,FJ9488 61,GQ867666 |
| Human bocavirus 4 | NC_012729 | vertebrates,human | 1 | Parvoviridae,Bocavirus,Human bocavirus 4 | — | FJ973561 |
| Human bocavirus WLL-1 | NC_007455 | vertebrates,human | 1 | Parvoviridae,Bocavirus,Human bocavirus | — | DQ778300 |
| Human bocavirus WLL-2 | NC_007455 | vertebrates,human | 1 | Parvoviridae,Bocavirus,Human bocavirus | — | EF441262 |
| Human bocavirus WLL-3 | NC_007455 | vertebrates,human | 1 | Parvoviridae,Bocavirus,Human bocavirus | — | EF584447 |
| Human bocavirus isolate SH1 | NC_007455 | vertebrates,human | 1 | Parvoviridae,Bocavirus,Human bocavirus | — | FJ375127 |
| Human bocavirus isolate SH2 | NC_007455 | vertebrates,human | 1 | Parvoviridae,Bocavirus,Human bocavirus | — | FJ375128 |
| Human bocavirus isolate SH3 | NC_012042 | vertebrates,human | 1 | Parvoviridae,Bocavirus,Human bocavirus 2 | — | FJ375129 |
| Human calicivirus Hu/NLV/G11/MD145-12/1987/US | NC_001959 | vertebrates,human | 1 | Caliciviridae,Norovirus,Norwalk virus | — | AY032605 |
| Human calicivirus Hu/NLV/Oxford/B5522/200 3/UK | NC_001959 | vertebrates,human | 1 | Caliciviridae,Norovirus,Norwalk virus | — | AY581254 |
| Human calicivirus N LV/G11/Langen 1061/2002/ DE | NC_001959 | vertebrates,human | 1 | Caliciviridae,Norovirus,Norwalk virus | — | AY485642 |
| Human calicivirus strain Mc37 | NC_001959 | vertebrates,human | 1 | Caliciviridae,Norovirus,Norwalk virus | — | AY237415 |
| Human coronavirus 229E | NC_002645 | vertebrates,human | 6 | Coronaviridae,Alphacoronavirus,Human coronavirus 229E | — | KF514430,AF304460, JX503060,KF514433, JX503061,KF514432 |
| Human coronavirus HKU1 | NC_006577 | vertebrates,human | 36 | Coronaviridae,Betacoronavirus,Human coronavirus HKU1 | — | KF430202,DQ415901 ,AY597011,KF686343 |

| Taxonomy | NCBI Reference Sequence ID | Host | No. of Genomes | Lineage | Segment Count | Genbank Accession ID |
|---|---|---|---|---|---|---|
| | | | | | | ,HM034837,KF68633 9,AY884001,DQ4159 09,DQ415904,KF686 342,KF686340,DQ41 5907,KF850450,DQ4 15902,KF686344,KF4 30199,DQ415903,KF 68641,DQ415908,D 0415914,DQ339101, DQ415900,DQ41590 6,KF686338,KF68634 6,DQ415905,DQ4158 98,KF430201,DQ415 899,DQ415913,DQ41 5912,KF686345,DQ4 15896,DQ415897,DQ 415911,DQ415910 |
| Human coronavirus NL63 | NC_005831 | vertebrates,human | 24 | Coronaviridae,Alphacoronavirus,Human coronavirus N L63 | — | JQ765572,JX104161, JQ900257,JQ765569, JQ765566,JQ765575, JQ765564,JQ900256, JQ765570,JQ900259, JQ765563,JQ765574, DQ445911,CS124012 ,JQ765565,JX504050 ,JQ765567,DQ44591 2,JQ765573,JX52417 1,JQ765568,AY56748 7,JQ765571,JQ90025 5 |
| Human coxsackievirus A1 | NC_002058 | vertebrates,human | 3 | Picornaviridae,Enterovirus,Enterovirus C | — | JX174177,AF499635, JX174176 |
| Human coxsackievirus A10 | NC_001612 | vertebrates,human | 2 | Picornaviridae,Enterovirus,Enterovirus A | — | AY421767,HQ728262 ,DQ995634,DQ99563 3,JF260917,JF26091 9,AF499637,DQ99 8 |
| Human coxsackievirus A11 | NC_002058 | vertebrates,human | 6 | Picornaviridae,Enterovirus,Enterovirus C | — | |
| Human coxsackievirus A12 | NC_001612 | vertebrates,human | 1 | Picornaviridae,Enterovirus,Enterovirus A | — | AY421768 |
| Human coxsackievirus A13 | NC_002058 | vertebrates,human | 16 | Picornaviridae,Enterovirus,Enterovirus C | — | DQ995642,DQ99564 0,DQ995637,DQ99956 36,DQ995635,DQ995 641,JF260920,AF465 511,AF499637,DQ99 5638,JF260923,JF26 0922,JF260921,DQ99 5644,DQ995639,DQ9 95643 |

| Taxonomy | NCBI Reference Sequence ID | Host | No. of Genomes | Lineage | Segment Count | Genbank Accession ID |
|---|---|---|---|---|---|---|
| Human coxsackievirus A14 | NC_001612 | vertebrates,human | 1 | Picornaviridae,Enterovirus,Enterovirus A | — | AY421769 |
| Human coxsackievirus A15 | NC_002058 | vertebrates,human | 2 | Picornaviridae,Enterovirus,Enterovirus C | — | AF465512,AF499638 |
| Human coxsackievirus A16 | NC_001612 | vertebrates,human | 34 | Picornaviridae,Enterovirus,Enterovirus A | — | JXQ68827,JQ746666, JX481738,JF738003, JX986740,KC695830, JN674176,JF738004, EU812514,JQ316639, KC117318,AF17791 1,JX986741,KC11731 7,KC342228,JQ0341 49,EU262658,JXQ688 30,J XQ68833,JQ7466 60,AY790926,HQ423 141,JXQ68828,JXQ68 832,HQ269389,J XQ6 8829,JX507808,JX83 9965,J XQ68831,GQ2 79368,JQ746661,JX9 86742,FJ198212,GQ 279371 |
| Human coxsackievirus A17 | NC_002058 | vertebrates,human | 6 | Picornaviridae,Enterovirus,Enterovirus C | — | JF260924,DQ995645, JF260925,FM955278, DQ995646,AF499639 |
| Human coxsackievirus A18 | NC_002058 | vertebrates,human | 3 | Picornaviridae,Enterovirus,Enterovirus C | — | AF465513,AB205396, AF499640 |
| Human coxsackievirus A19 | NC_002058 | vertebrates,human | 1 | Picornaviridae,Enterovirus,Enterovirus C | — | AF499641 |
| Human coxsackievirus A2 | NC_001612 | vertebrates,human | 2 | Picornaviridae,Enterovirus,Enterovirus A | — | AY421760,HQ728259 |
| Human coxsackievirus A20 | NC_002058 | vertebrates,human | 3 | Picornaviridae,Enterovirus,Enterovirus C | — | DQ358078,AF499642 ,AF465514 |
| Human coxsackievirus A21 | NC_002058 | vertebrates,human | 2 | Picornaviridae,Enterovirus,Enterovirus C | — | AF546702,AF465515 |
| Human coxsackievirus A21 Coe | NC_002058 | vertebrates,human | 1 | Picornaviridae,Enterovirus,Enterovirus C | — | DQ0538 |
| Human coxsackievirus A22 | NC_002058 | vertebrates,human | 4 | Picornaviridae,Enterovirus,Enterovirus C | — | DQ995647,JN542510 ,AF499643,DQ99564 8 |
| Human coxsackievirus A24 | NC_002058 | vertebrates,human | 19 | Picornaviridae,Enterovirus,Enterovirus C | — | EF026081,JF742578, D90457,AB769160,J N228097,AB769154, DQ443001,AB769159 ,AB769162,AB76916 5,AB769164,JF74257 7,AB769161,JF74257 9,JF742576,AB76916 3,AB769156,DQ4430 02,AB769152 |
| Human coxsackievirus A3 | NC_001612 | vertebrates,human | 1 | Picornaviridae,Enterovirus,Enterovirus A | — | AY421761 |
| Human coxsackievirus A4 | NC_001612 | vertebrates,human | 2 | Picornaviridae,Enterovirus,Enterovirus A | — | HQ728260,AY421762 |

-continued

| Taxonomy | NCBI Reference Sequence ID | Host | No. of Genomes | Lineage | Segment Count | Genbank Accession ID |
|---|---|---|---|---|---|---|
| Human coxsackievirus AS | NC_001612 | vertebrates,human | 2 | Picornaviridae,Enterovirus,Enterovirus A | — | AY421763,HQ728261 |
| Human coxsackievirus A6 | NC_001612 | vertebrates,human | 9 | Picornaviridae,Enterovirus,Enterovirus A | — | JQ946053,AB678778, JQ946051,JQ946054, JQ964234,JQ946055, JQ946052,AY421764, JQ946050 |
| Human coxsackievirus A7 | NC_001612 | vertebrates,human | 2 | Picornaviridae,Enterovirus,Enterovirus A | — | AY421765,JQ041367 |
| Human coxsackievirus A8 | NC_001612 | vertebrates,human | 1 | Picornaviridae,Enterovirus,Enterovirus A | — | AY421766 |
| Human coxsackievirus A9 | NC_001472 | vertebrates,human | 1 | Picornaviridae,Enterovirus,Enterovirus B | — | DQ0627 |
| Human coxsackievirus B1 | NC_001472 | vertebrates,human | 7 | Picornaviridae,Enterovirus,Enterovirus B | — | AY186745,JN596588, AY186748,AY186746 ,AY186747,JX976769 ,EU147493 |
| Human coxsackievirus B2 | NC_001472 | vertebrates,human | 4 | Picornaviridae,Enterovirus,Enterovirus B | — | AF081485,EF174468, AF085363,EF174469 |
| Human coxsackievirus B3 | NC_001472 | vertebrates,human | 20 | Picornaviridae,Enterovirus,Enterovirus B | — | U57056,AF231764,A F231763,JX976770,A Y752945,AY752944, M88483,AY752946,M 16572,GU109481, M3 3854,FJQ00001,FJ35 7838,JN979570,GQ1 41875,EU144042,KC 481610,AY673831,JX 312064,AF231765 |
| Human coxsackievirus B4 | NC_001472 | vertebrates,human | 6 | Picornaviridae,Enterovirus,Enterovirus B | — | AF311939,DQ480420 ,S76772,XQ5690,JX3 08222,AF328683 |
| Human coxsackievirus B5 | NC_001472 | vertebrates,human | 13 | Picornaviridae,Enterovirus,Enterovirus B | — | AY875692,GU376747 ,HQ998851,JXQ1738 0,X67706,JXQ17382,J X276378,JN580070,J N695050,AF114383,J N695051,JXQ17383,J XQ17381 |
| Human coxsackievirus B6 | NC_001472 | vertebrates,human | 4 | Picornaviridae,Enterovirus,Enterovirus B | — | JQ041368,AF114384, AF105342,AF039205 |
| Human echovirus 11 | NC_001472 | vertebrates,human | 6 | Picornaviridae,Enterovirus,Enterovirus B | | EF634316,X80059,AJ 276224,AJ577594,AJ 577590,AJ577589 |
| Human echovirus 12 | NC_001472 | vertebrates,human | 2 | Picornaviridae,Enterovirus,Enterovirus B | — | X79047,X77708 |
| Human echovirus 13 | NC_001472 | vertebrates,human | 5 | Picornaviridae,Enterovirus,Enterovirus B | — | AB501332,AB501329 ,AB501330,AB50133 1,AY302539 |
| Human echovirus 14 | NC_001472 | vertebrates,human | 1 | Picornaviridae,Enterovirus,Enterovirus B | — | AY302540 |
| Human echovirus 15 | NC_001472 | vertebrates,human | 1 | Picornaviridae,Enterovirus,Enterovirus B | — | AY302541 |
| Human echovirus 16 | NC_001472 | vertebrates,human | 1 | Picornaviridae,Enterovirus,Enterovirus B | — | AY302542 |
| Human echovirus 17 | NC_001472 | vertebrates,human | 1 | Picornaviridae,Enterovirus,Enterovirus B | — | AY302543 |

-continued

| Taxonomy | NCBI Reference Sequence ID | Host | No. of Genomes | Lineage | Segment Count | Genbank Accession ID |
|---|---|---|---|---|---|---|
| Human echovirus 18 | NC_001472 | vertebrates,human | 2 | Picornaviridae,Enterovirus,Enterovirus B | — | AF317694,HM777023 |
| Human echovirus 19 | NC_001472 | vertebrates,human | 1 | Picornaviridae,Enterovirus,Enterovirus B | — | AY302544 |
| Human echovirus 2 | NC_001472 | vertebrates,human | 2 | Picornaviridae,Enterovirus,Enterovirus B | — | AY302545,AF465518 |
| Human echovirus 20 | NC_001472 | vertebrates,human | 1 | Picornaviridae,Enterovirus,Enterovirus B | — | AY302546 |
| Human echovirus 21 | NC_001472 | vertebrates,human | 1 | Picornaviridae,Enterovirus,Enterovirus B | — | AY302547 |
| Human echovirus 24 | NC_001472 | vertebrates,human | 1 | Picornaviridae,Enterovirus,Enterovirus B | — | AY302548 |
| Human echovirus 25 | NC_001472 | vertebrates,human | 2 | Picornaviridae,Enterovirus,Enterovirus B | — | AY302549,HM031191 |
| Human echovirus 26 | NC_001472 | vertebrates,human | 1 | Picornaviridae,Enterovirus,Enterovirus B | — | AY302550 |
| Human echovirus 27 | NC_001472 | vertebrates,human | 1 | Picornaviridae,Enterovirus,Enterovirus B | — | AY302551 |
| Human echovirus 29 | NC_001472 | vertebrates,human | 1 | Picornaviridae,Enterovirus,Enterovirus B | — | AY302552 |
| Human echovirus 3 | NC_001472 | vertebrates,human | 13 | Picornaviridae,Enterovirus,Enterovirus B | — | AB647324,AB647318,AB647326,AB647320,AB647325,AB647319,AY302553,AJ849942,AB647322,AB647317,AB647321,AB647323,AB647316 |
| Human echovirus 30 | NC_001472 | vertebrates,human | 5 | Picornaviridae,Enterovirus,Enterovirus B | — | JN704615,DQ246620,AF311938,DQ534205,AF162711 |
| Human echovirus 31 | NC_001472 | vertebrates,human | 1 | Picornaviridae,Enterovirus,Enterovirus B | — | AY302554 |
| Human echovirus 32 | NC_001472 | vertebrates,human | 1 | Picornaviridae,Enterovirus,Enterovirus B | — | AY302555 |
| Human echovirus 33 | NC_001472 | vertebrates,human | 1 | Picornaviridae,Enterovirus,Enterovirus B | — | AY302556 |
| Human echovirus 4 | NC_001472 | vertebrates,human | 2 | Picornaviridae,Enterovirus,Enterovirus B | — | AY302557,FJ172447 |
| Human echovirus 5 | NC_001472 | vertebrates,human | 2 | Picornaviridae,Enterovirus,Enterovirus B | — | HM775882,AF083069 |
| Human echovirus 6 | NC_001472 | vertebrates,human | 5 | Picornaviridae,Enterovirus,Enterovirus B | — | U16283,AY302558,AF465517,HM185055,JQ729993 |
| Human echovirus 7 | NC_001472 | vertebrates,human | 4 | Picornaviridae,Enterovirus,Enterovirus B | — | AY036578,AF465516,AY302559,AY036579 |
| Human echovirus 9 | NC_001472 | vertebrates,human | 2 | Picornaviridae,Enterovirus,Enterovirus B | — | AF524867,AF524866 |
| Human endogenous retrovirus K113 | NC_022518 | vertebrates,human | 1 | Retroviridae,Human endogenous retrovirus K | — | AY037928 |
| Human endogenous retrovirus K115 | NC_022518 | vertebrates,human | 1 | Retroviridae,Human endogenous retrovirus K | — | AY037929 |
| Human enteric coronavirus strain 4408 | NC_012950 | vertebrates,human | 1 | Coronaviridae,Human enteric coronavirus strain 4408 | — | FJ938067 |
| Human enterovirus 100 | NC_001472 | vertebrates,human | 1 | Picornaviridae,Enterovirus,Enterovirus B | — | DQ902713 |
| Human enterovirus 101 | NC_001472 | vertebrates,human | 1 | Picornaviridae,Enterovirus,Enterovirus B | — | AY843308 |
| Human enterovirus 102 | NC_002058 | vertebrates,human | 1 | Picornaviridae,Enterovirus,Enterovirus C | — | EF555645 |
| Human enterovirus 104 | NC_002058 | vertebrates,human | 1 | Picornaviridae,Enterovirus,Enterovirus C | — | AB686524 |
| Human enterovirus 107 | NC_001472 | vertebrates,human | 1 | Picornaviridae,Enterovirus,Enterovirus B | — | AB426609 |
| Human enterovirus 68 | NC_001430 | vertebrates,human | 8 | Picornaviridae,Enterovirus,Enterovirus D | — | JX101846,EF107098,JXQ70222,AB601883,AB601884,AY426531,AB601885,AB601882 |

-continued

| Taxonomy | NCBI Reference Sequence ID | Host | No. of Genomes | Lineage | Segment Count | Genbank Accession ID |
|---|---|---|---|---|---|---|
| Human enterovirus 69 | NC_001472 | vertebrates,human | 1 | Picornaviridae,Enterovirus,Enterovirus B | — | AY302560 |
| Human enterovirus 70 | NC_001430 | vertebrates,human | 1 | Picornaviridae,Enterovirus,Enterovirus D | — | DQ201177 |
| Human enterovirus 71 | NC_001612 | vertebrates,human | 281 | Picornaviridae,Enterovirus,Enterovirus A | — | DQ341365,JX244183,AB575917,HQ882182,HM053669,AF136379,GU396280,JX678880,HM245928,GQ231931,HQ064177,GU366191,JQ074188,AB469182,EU414333,GQ231928,JX678885,JF820315,JQ639384,JX111890,AF176044,D0341362,HQ891928,AB550336,HQ647171,HM807310,EU864507,JQ074190,EU414335,FJ194965,JN964686,JX678875,FJ606448,JX678886,EF373575,HQ694986,HM002486,GU198368,JX244182,GQ231925,JQ280307,HM002489,FJ828519,JQ708209,G0279369,FJ607338,JX986738,AB575935,JN992285,JX111891,GQ231934,HQ325852,AB550339,HQ889192,JN020147,HQ423142,JQ319054,HQ647170,JF738002,JN992284,GU459070,JQ736684,JX678879,HQ694982,FJ607334,JX678883,HQ647176,H0647169,AB575936,AB575913,GU198367,JX111893,EU376004,FJ606449,DQ381846,AM396586,JF738001,GU198369,EU703814,AM396587,JN256064,JQ708210,AF304457,JX244186,HQ891925,HQ828086,GU198370,AB575928,EU3 |

| Taxonomy | NCBI Reference Sequence ID | Host | No. of Genomes | Lineage | Segment Count | Genbank Accession ID |
|---|---|---|---|---|---|---|
| | | | | | | 76005,JXQ25561,JX1 11892,JX678874,FJ6 06450,HM053671,HQ 647174,JQ950555,AY 465356,AB550333,H 0647179,JN544419, AB575937,EU414334 ,HQ647175,HQ64716 8,AB575914,JX67888 2,HQ891927,JX9867 39,GQ231936,FJ360 546,HM003207,JN99 2283,GQ994990,U22 521,AB575918,DQ34 1364,JF738000,HQ18 8292,AB575915,AM3 96588,EU812515,FJ6 07336,GQ231932,JQ 639383,HQ647172,E F063152,GQ231927, JXQ17384,AB550335, JN256060,AB469183, AB550341,U22522,H 0891926,HM002487, HQ647178,JX678877 ,GQ231942,AB57591 1,FJ158601,AF30445 8,DQ341363,HM0024 84,HM245927,AB550 340,DQ060149,DQ34 1358,FJ713137,GQ9 94991,JN256059,HQ 426649,AB550337,A B575916,AF119796,A B57594l,JN992282,H 0129932,HQ825317, JX111888,DQ341367 ,FJ606447,HQ694983 ,JX678884,GQ89283 0,JN256061,FJ17215 9,AB575912,HM0024 85,AB575939,JQ6812 18,FJ158600,FJ6073 35,AB575927,JF8300 07,JN001860,DQ341 357,AM396584,AF30 2996,AB575948,GQ2 31930,JF820314,AM3 |

-continued

| Taxonomy | NCBI Reference Sequence ID | Host | No. of Genomes | Lineage | Segment Count | Genbank Accession ID |
|---|---|---|---|---|---|---|
| | | | | | | 96585,FJ360544,AJ586873,JX678881,HQ407557,DQ341368,JN256063,HQ891929,JX244187,JF894382,HQ891924,JQ742001,DQ341359,GQ994992,AF304459,JQ316638,AB575942,HQ189392,DQ133459,GU198371,JN052925,JQ074189,JN256062,JQ806378,HM053670,GQ231929,AB204853,JF820316,JX678876,JQ074187,EU703812,FJ607337,HM002488,EF373576,AB482183,HQ694985,GU459071,JXQ25559,JF894381,H0998852,GQ231926,FJ194964,AF119795,GQ994989,DQ133458,FJ360545,HQ712020,JQ742002,GQ279370,AB550334,GU196833,JF820313,DQ341360,AB550338,JN835312,JF894383,JX678878,HQ611148,GQ231941,JX986737,GQ231933,HQ647180,DQ341355,EU364841,KC109780,AB575938,DQ452074,GQ231939,GU434678,DQ341361,HQ423143,GQ231940,GQ231935,HQ694984,JF913464,EU703813,DQ341366,JX244184,AB204852,FJ461781,JX244185,GQ994988,HQ647173,EU414331,GQ231938,AB550332,JN544418,HQ647167,JQ804832,AB575923,GQ231943,GQ231937,JX1118 |

| Taxonomy | NCBI Reference Sequence ID | Host | No. of Genomes | Lineage | Segment Count | Genbank Accession ID |
|---|---|---|---|---|---|---|
| Human enterovirus 71 HZ08/Hangzhou/2008 | NC_001612 | vertebrates,human | 1 | Picornaviridae, Enterovirus, Enterovirus A | — | 89,FJ439769,DQ3413 56,JF820312,DQ3413 54,KC414134,EU131 776,JF799986 HQ400942 |
| Human enterovirus 74 | NC_001472 | vertebrates,human | 2 | Picornaviridae, Enterovirus, Enterovirus B | — | JQ397329,AY556057 |
| Human enterovirus 75 | NC_001472 | vertebrates,human | 1 | Picornaviridae,Enterovirus,Enterovirus B | — | AY556070 |
| Human enterovirus 76 | NC_001612 | vertebrates,human | 2 | Picornaviridae,Enterovirus,Enterovirus A | — | JF905564,AY697458 |
| Human enterovirus 77 | NC_001472 | vertebrates,human | 1 | Picornaviridae,Enterovirus,Enterovirus B | — | AY843302 |
| Human enterovirus 79 | NC_001472 | vertebrates,human | 2 | Picornaviridae,Enterovirus,Enterovirus B | — | AY843297,AB426610 |
| Human enterovirus 80 | NC_001472 | vertebrates,human | 2 | Picornaviridae, Enterovirus, Enterovirus B | — | JX644073,AY843298 |
| Human enterovirus 81 | NC_001472 | vertebrates,human | 1 | Picornaviridae,Enterovirus,Enterovirus B | — | AY843299 |
| Human enterovirus 82 | NC_001472 | vertebrates,human | 1 | Picornaviridae,Enterovirus,Enterovirus B | — | AY843300 |
| Human enterovirus 83 | NC_001472 | vertebrates,human | 1 | Picornaviridae,Enterovirus,Enterovirus B | — | AY843301 |
| Human enterovirus 84 | NC_001472 | vertebrates,human | 1 | Picornaviridae,Enterovirus,Enterovirus B | — | DQ902712 |
| Human enterovirus 85 | NC_001472 | vertebrates,human | 6 | Picornaviridae, Enterovirus, Enterovirus B | — | AY843303,JX898905, JX898908,JX898907, JX898906,JX898909 |
| Human enterovirus 86 | NC_001472 | vertebrates,human | 1 | Picornaviridae,Enterovirus,Enterovirus B | — | AY843304 |
| Human enterovirus 87 | NC_001472 | vertebrates,human | 1 | Picornaviridae,Enterovirus,Enterovirus B | — | AY843305 |
| Human enterovirus 88 | NC_001472 | vertebrates,human | 1 | Picornaviridae,Enterovirus,Enterovirus B | — | AY843306 |
| Human enterovirus 89 | NC_001612 | vertebrates,human | 1 | Picornaviridae,Enterovirus,Enterovirus A | — | AY697459 |
| Human enterovirus 90 | NC_001612 | vertebrates,human | 6 | Picornaviridae, Enterovirus, Enterovirus A | — | JX390655,AB192877, JX390654,AY697460, JX390656,AY7773285 |
| Human enterovirus 91 | NC_001612 | vertebrates,human | 1 | Picornaviridae,Enterovirus,Enterovirus A | — | AY697461 |
| Human enterovirus 92 | NC_001612 | vertebrates,human | 1 | Picornaviridae,Enterovirus,Enterovirus A | — | EF667344 |
| Human enterovirus 94 | NC_001430 | vertebrates,human | 2 | Picornaviridae, Enterovirus, Enterovirus D | — | DQ916376,EF107097 |
| Human enterovirus 96 | NC_002058 | vertebrates,human | 1 | Picornaviridae,Enterovirus,Enterovirus C | — | EF015886 |
| Human enterovirus 97 | NC_001472 | vertebrates,human | 2 | Picornaviridae,Enterovirus,Enterovirus B | — | AY843307,AB426611 |
| Human enterovirus 98 | NC_001472 | vertebrates,human | 1 | Picornaviridae,Enterovirus,Enterovirus B | — | AB426608 |
| Human enterovirus 99 | NC_002058 | vertebrates,human | 2 | Picornaviridae,Enterovirus,Enterovirus C | — | EF555644,JF260926 |
| Human enterovirus A | NC_001612 | vertebrates,human | 9 | Picornaviridae, Enterovirus, Enterovirus A | — | HQ456312,HQ45630 7,HQ456313,HQ4563 08,HQ456306,HQ456 309,HQ456311,HQ45 6310,HQ456305 |
| Human enterovirus B | NC_001472 | vertebrates,human | 6 | Picornaviridae, Enterovirus, Enterovirus B | — | AY896765,EF371880, AY896762,AJ493062, AY896763,HM185056 |
| Human enterovirus C | NC_002058 | vertebrates,human | 22 | Picornaviridae,Enterovirus,Enterovirus C | — | HQ738302,HQ73830 1,HQ738290,HQ7382 86,HQ738291,HQ738 298,JX393301,HQ73 8294,HQ738297,V01 149,HQ738300,HQ73 8296,HQ738299,HQ7 |

| Taxonomy | NCBI Reference Sequence ID | Host | Lineage | No. of Genomes | Segment Count | Genbank Accession ID |
|---|---|---|---|---|---|---|
| Human enterovirus C104 | NC_002058 | vertebrates,human | Picornaviridae,Enterovirus,Enterovirus C | 7 | — | 38293,HQ738288,JX39302,HQ738289,H0738292,HQ738287,HQ738303,AB205395,HQ738295 |
| Human enterovirus C105 | NC_002058 | vertebrates,human | Picornaviridae,Enterovirus,Enterovirus C | 1 | — | JX982256,JX982254,JX982253,JX982255,JX982259,JX982258,JX982257 |
| Human enterovirus C109 | NC_002058 | vertebrates,human | Picornaviridae,Enterovirus,Enterovirus C | 1 | — | JX514943 |
| Human enterovirus C116 | NC_002058 | vertebrates,human | Picornaviridae,Enterovirus,Enterovirus C | 1 | — | GQ865517 |
| Human enterovirus C117 | NC_002058 | vertebrates,human | Picornaviridae,Enterovirus,Enterovirus C | 1 | — | JX514942 |
| Human enterovirus C118 | NC_002058 | vertebrates,human | Picornaviridae,Enterovirus,Enterovirus C | 1 | — | JX262382 |
| Human enterovirus C118 | NC_002058 | vertebrates,human | Picornaviridae,Enterovirus,Enterovirus C | 3 | — | JX961709,JX678288,JX961708 |
| Human enterovirus C96 | NC_002058 | vertebrates,human | Picornaviridae,Enterovirus,Enterovirus C | 5 | — | HQ415759,FJ751915,FJ751914,KF495604,HQ415758 |
| Human enterovirus C99 | NC_002058 | vertebrates,human | Picornaviridae,Enterovirus,Enterovirus C | 7 | — | KF129411,EF015012,KF129412,EF015011,EF015010,EF015009,EF015008 |
| Human enterovirus D | NC_001430 | vertebrates,human | Picornaviridae,Enterovirus,Enterovirus D | 1 | — | DQ0820 |
| Human enterovirus Hangzhou13-02 | NC_002058 | vertebrates,human | Picornaviridae,Enterovirus,Enterovirus C | 1 | — | AY876913 |
| Human enterovirus Ningbo3-02 | NC_002058 | vertebrates,human | Picornaviridae,Enterovirus,Enterovirus C | 1 | — | AY876912 |
| Human group 1 coronavirus associated with pneumonia | NC_005831 | vertebrates,human | Coronaviridae,Alphacoronavirus,Human coronavirus NL63 | 1 | — | AY518894 |
| Human herpesvirus 1 | NC_001806 | vertebrates,human | Herpesviridae,Simplexvirus,Human herpesvirus 1 | 8 | — | KF498959,IQ673480,GU734772,X14112,FJ593289,GU734771,JN555585,KF781518 |
| Human herpesvirus 2 | NC_001798 | vertebrates,human | Herpesviridae,Simplexvirus,Human herpesvirus 2 | 2 | — | Z86099,KF781518 |
| Human herpesvirus 3 | NC_001348 | vertebrates,human | Herpesviridae,Varicellovirus,Human herpesvirus 3 | 47 | — | DQ479962,JN704700,DQ479956,DQ45205 0,JN704703,JN70470 5,JN704708,KC84729 0,JN704698,DQ0083 54,AY548171,JN7046 91,JN704695,AB0979 33,DQ674250,DQ479 961,JN704709,JN704 694,DQ479959,JN70 4710,JN704690,DQ4 79958,DQ479957,JN |

-continued

| Taxonomy | NCBI Reference Sequence ID | Host | No. of Genomes | Lineage | Segment Count | Genbank Accession ID |
|---|---|---|---|---|---|---|
| | | | | | | 704706,JN704704,D0008355,JN704696,KC112914,DQ479954,DQ479953,JN704469,7,JN704701,DQ479955,EU154348,DQ479960,JF306641,DQ479963,JN704699,AB097932,DQ457052,JN704707,JN704692,AY548170,JN704702,XQ4370,AJ871403,JN704693 |
| Human herpesvirus 4 | NC_007605 NC_009334 | vertebrates,human | 5 | Herpesviridae,Lymphocryptovirus,Human herpesvirus 4 | — | AJ507799,KC207813,KC207814,AY961628,KF373730 |
| Human herpesvirus 5 | NC_006273 | vertebrates,human | 46 | Herpesviridae,Cytomegalovirus,Human herpesvirus 5 | — | JX512200,GU179290,GU179291,GQ221974,FJ527563,GU937742,GQ396662,KC519319,GU179001,AC146999,JX512204,GQ221973,KF297339,JX512205,AC146906,JX512199,HQ380895,GQ221975,GU179288,JX512203,AY315197,JX512202,KC519321,FJ616285,JX512197,G012041,EF999921,AC146851,JX512208,KC519323,JX512201,AC146904,AY446894,JX512206,JX512207,GQ466044,AC146905,KC519320,GU179289,GQ396663,GU980198,X17403,KC519322,JX512198,AC146907,KF021605 |
| Human herpesvirus 7 | NC_001716 | vertebrates,human | 2 | Herpesviridae,Roseolovirus,Human herpesvirus 7 | — | AF037218,U43400 |
| Human herpesvirus 8 | NC_009333 | vertebrates,human | 3 | Herpesviridae,Rhadinovirus,Human herpesvirus 8 | — | AF148805,HQ404500,JQ619843 |
| Human herpesvirus 8 type P | NC_009333 | vertebrates,human | 1 | Herpesviridae,Rhadinovirus,Human herpesvirus 8 | — | GQ994935 |

| Taxonomy | NCBI Reference Sequence ID | Host | No. of Genomes | Lineage | Segment Count | Genbank Accession ID |
|---|---|---|---|---|---|---|
| Human immunodeficiency virus 1 | NC_001802 | vertebrates,human | 1815 | Retroviridae,Lentivirus,Human immunodeficiency virus 1 | — | K02013,DQ676887,E U697905,GQ372988, AF408631,AF042103, EU110097,DQ020274 ,AB253705,DQ39638 0,DQ314731,AY7795 51,KC899015,FJ6234 91,FJ670519,GU7337 15,AF069140,AB2536 90,AB253679,KC156 213,AB253676,EF637 057,U63632,FJ62349 4,FJ771010,DQ16410 5,GQ999983,AF4430 76,AB253686,AB231 898,AF119820,KC89 8978,AY819715,FJ49 6163,JX574663,AF25 6211,AF10771,KC1 56129,U69585,EF495 062,AB231896,GQ99 9973,DQ487190,AB0 98331,EU110085,AF 490974,AY771591,E U293450,EU735535, AY586542,AB565503 ,AB287003,AB25370 7,AY463229,AF25995 4,AB286863,EF36312 5,AY352655,DQ3512 22,AB565500,DQ011 177,AY331293,FJ495 822,AY536235,AY30 8762,AJ251056,FJ49 5826,AY586544,FJ49 6085,U69589,AB2868 57,FJ623482,EF1783 66,AF197338,FJ4960 82,AY463235,AY835 758,EU616643,AB25 3693,AY878055,AF11 0966,JF804806,KC89 8993,AB287370,AY9 00572,DQ164121,EU 697906,EU735536,A B287363,DQ853445, FJ185228,KC898988, AY455785,AF075701, |

| Taxonomy | NCBI Reference Sequence ID | Host | No. of Genomes | Lineage | Segment Count | Genbank Accession ID |
|---|---|---|---|---|---|---|
| | | | | | | KC156218,HM026460,EU110086,FJ495941,AF005494,AY125894,DQ886003,KC898976,AB485656,DQ093591,JX503074,GU362013,FJ670525,AF067157,DQ220743,U69586,AB254154,FJ185238,AY560108,AY901971,KC522034,AF110961,AY835761,DQ358799,AB565502,EU786675,AY771589,AF190127,AB253640,DQ445635,EU735539,AJ291718,DQ369977,EU743964,GU733713,AF067155,AY781127,DQ396386,AF443077,FJ496189,FJ623485,FJ496156,KC503855,DQ853451,AB253421,FJ670516,DQ854716,AF450098,EU110092,EU786680,DQ351217,EF514699,AF067159,DQ351231,AY771593,AY878064,EU697904,AY835763,GU647197,GQ365652,AB565504,U51190,AY586546,FJ623493,U39362,EU786673,DQ295195,AY463236,AJ866555,AY835751,AB286956,AY586545,FJ496074,EU697908,A07867,DQ886036,DQ912822,AF119819,AF423756,DQ358808,DQ396384,AB253706,AY945709,DQ396369,AY314046,FJ864679,GQ999975,AF289548,FJ853622,DQ990880,AY970950,AB731663,FJ496076,DQ39 |

| Taxonomy | NCBI Reference Sequence ID | Host | No. of Genomes | Lineage | Segment Count | Genbank Accession ID |
|---|---|---|---|---|---|---|
| | | | | | | 6382,AB428555,AB7 |
| | | | | | | 31665,AY586548,AF4 |
| | | | | | | 08630,JQ341411,KC |
| | | | | | | 156215,EU110087,K0 |
| | | | | | | 2007,AY455779,AF44 |
| | | | | | | 3074,AJ276595,FJ67 |
| | | | | | | 0531,DQ164116,FJ18 |
| | | | | | | 5245,DQ007903,AF0 |
| | | | | | | 69671,AY968312,EU |
| | | | | | | 446022,AY455782,FJ |
| | | | | | | 195091,AY332236,A |
| | | | | | | B253712,AY771588, |
| | | | | | | AB253644,DQ164110 |
| | | | | | | ,FJ460501,DQ164112 |
| | | | | | | ,AY779558,AB25364 |
| | | | | | | 9,DQ054367,AY9005 |
| | | | | | | 75,AY772692,JX5030 |
| | | | | | | 75,AY901980,AB231 |
| | | | | | | 895,FJ623479,GU177 |
| | | | | | | 863,KC899011,FJ496 |
| | | | | | | 200,AY463233,HM02 |
| | | | | | | 6459,JQ316136,AY00 |
| | | | | | | 8714,FJ185254,GU73 |
| | | | | | | 3714,DQ358802,AF4 |
| | | | | | | 84515,D10112,DQ88 |
| | | | | | | 6034,DQ351221,AF4 |
| | | | | | | 43099,AB253681,AY |
| | | | | | | 093605,AY773338,FJ |
| | | | | | | 496214,DQ093585,A |
| | | | | | | F107770,DQ085872, |
| | | | | | | KC899007,DQ396400 |
| | | | | | | ,AB098332,DQ85344 |
| | | | | | | 1,FJ496194,AB28737 |
| | | | | | | 7,AB253714,DQ8534 |
| | | | | | | 38,AF443092,FJ6234 |
| | | | | | | 77,FJ185239,AB2873 |
| | | | | | | 67,XQ1762,AF110974 |
| | | | | | | ,DQ351235,DQ32223 |
| | | | | | | 9,DQ085875,AF1109 |
| | | | | | | 75,AM000054,AP005 |
| | | | | | | 206,FJ496181,AY835 |
| | | | | | | 773,GU647196,KC15 |
| | | | | | | 6126,DQ853465,HM4 |
| | | | | | | 69972,JX503080,DQ |
| | | | | | | 396364,AF197341,JN |
| | | | | | | 860764,AY818644,FJ |
| | | | | | | 195088,AF443107,FJ |
| | | | | | | 670521,DQ295193,FJ |

| Taxonomy | NCBI Reference Sequence ID | Host | No. of Genomes | Lineage | Segment Count | Genbank Accession ID |
|---|---|---|---|---|---|---|
| | | | | | | 496151,AB480301,D 0853455,AB746345, AB097868,FJ496183, AY772535,DQ056418 ,AY835770,EU00050 7,DQ676871,D86068, AB485639,AF411967, JQ316130,AB485657, AY314053,AY901976 ,KC898984,JX503076 ,AB286856,EF363124 ,AF075702,AY423384 ,AF290028,FJ496191 ,AY779560,EU03191 3,DQ369997,AF2895 50,AY773340,AF0421 02,AF061642,AF0043 94,EF545108,EU786 671,AB254147,FJ496 193,AY322190,AY87 8067,FJ185233,FJ49 6147,FJ460499,DQ35 8801,AJ866554,AF11 0959,FN392874,U211 35,AB253429,AB565 498,EU000511,KC89 8985,GQ099974,AB0 97867,AY835778,FJ1 85255,FJ495823,AF4 60972,AB253653,U43 141,FJ185249,JF804 808,AF192135,AF110 971,FJ496213,AB253 657,M38429,AB4800 48,AB485637,DQ056 407,FJ21378Z,AB485 635,GU237072,DQ85 3450,KC898979,M22 639,DQ295194,FJ495 938,AB253674,DQ44 5632,EU000510,DQO 56410,AY585264,DQ 854715,FJ496166,AB 480695,DQ886032,A Y314057,DQ676882, AY900571,FJ496202, AY008717,AB547464 ,AY037282,FJ185244 |

| Taxonomy | NCBI Reference Sequence ID | Host | No. of Genomes | Lineage | Segment Count | Genbank Accession ID |
|---|---|---|---|---|---|---|
| | | | | | | ,DQ164120,AJ24548 |
| | | | | | | 1,KC898991,AY1698 |
| | | | | | | 14,U46016,AF184155 |
| | | | | | | ,KF766537,GU59514 |
| | | | | | | 9,AY838567,HM4699 |
| | | | | | | 74,AY331296,DQ369 |
| | | | | | | 979,GQ175881,GQ99 |
| | | | | | | 9981,EU110094,FJ49 |
| | | | | | | 6199,U88826,AY4632 |
| | | | | | | 27,AY500393,FJ4959 |
| | | | | | | 42,DQ164117,FJ6471 |
| | | | | | | 45,AB253721,DQ445 |
| | | | | | | 634,AY772691,KC89 |
| | | | | | | 8977,AF110960,AJ25 |
| | | | | | | 1057,DQ351234,AY9 |
| | | | | | | 00574,EU000516,EU |
| | | | | | | 293444,AB253719,A |
| | | | | | | Y771590,AY773339, |
| | | | | | | AF286365,DQ358812 |
| | | | | | | ,EF029067,DQ85471 |
| | | | | | | 4,FJ495824,DQ35880 |
| | | | | | | 9,FJ496212,AB25369 |
| | | | | | | 2,DQ351232,AB2536 |
| | | | | | | 62,FJ496003,EU6166 |
| | | | | | | 39L31963,AY169807 |
| | | | | | | ,AF067154,U51188,A |
| | | | | | | Y585265,AF443083,A |
| | | | | | | F286236,FJ185259,G |
| | | | | | | Q999980,DQ853457, |
| | | | | | | FJ670515,DQ396396, |
| | | | | | | AB253684,AY322193 |
| | | | | | | ,AY586543,AY83576 |
| | | | | | | 5,U71182,KC898982, |
| | | | | | | DQ369998,DQ36998 |
| | | | | | | 3,DQ358800,JX5030 |
| | | | | | | 82,FJ623484,AY9019 |
| | | | | | | 74,AJ866553,AB2870 |
| | | | | | | 04,AJ508597,AB4800 |
| | | | | | | 47,FJ496073,AB4856 |
| | | | | | | 53,DQ369996,AF484 |
| | | | | | | 480,AY838565,AP00 |
| | | | | | | 5207,AB253697,DQO |
| | | | | | | 11178,AY463217,AB |
| | | | | | | 253659,HM026455,A |
| | | | | | | Y772700,AJ288981,A |
| | | | | | | F450097,KC156115, |
| | | | | | | DQ369978,AB428557 |
| | | | | | | ,AY331297,JQ316127 |

| Taxonomy | NCBI Reference Sequence ID | Host | No. of Genomes | Lineage | Segment Count | Genbank Accession ID |
|---|---|---|---|---|---|---|
| | | | | | | ,DQ396371,FJ623492,A07116,EU293445,KC156220,AF082394,AF443103,AB253685,EU293448,DQ676874,AB253638,AY87805 9,AY049711,AB6049 47,FJ496206,HM026 457,FJ670523,FJ670 522,AB547463,AF443 105,AB070353,AY31 4052,FJ496075,AY77 2696,KC898996,DQ8 53456,AB641836,AY 237167,FJ496148,KC 898992,AY623602,A B221125,AB253708, AY682547,AF423760, EF178405,AY835771, AF484485,AB428560, AF286223,FJ195089, AF516184,EF637055, AY779550,AB485660 ,AF538303,FJ185232 ,DQ164118,AB48564 4,AB070352,KC5038 53,DQ093607,AF042 104,DQ314732,DQ05 6414,FJ185235,DQ82 3367,EU786674,AB7 31669,FJ195087,FJ1 85260,GQ372986,AB 287372,AB480697,D 0445633,AB287379, AY445524,FJ185234, AY169810,DQ396370 ,FJ185230,DQ011180 ,AF110969,FJ213780 ,AB253673,AY83575 6,AF443082,DQ0936 01,AB485659,GQ845 125,AF443108,AY314 055,AF538302,EF178 323,AB286850,AY83 5779,DQ351237,DQ3 66662,DQ093589,FJ4 96006,AB480045,AB 253694,AB253431,D |

| Taxonomy | NCBI Reference Sequence ID | Host | No. of Genomes | Lineage | Segment Count | Genbank Accession ID |
|---|---|---|---|---|---|---|
| | | | | | | 0351219,EF514713, KC156127,GQ099999 0,AF179368,GQ8451 26,DQ093590,EU735 540,DQ207942,AY42 3381,DQ853439,AB0 98333,M17451,FJ495 820,DQ853460,AB25 3639,JQ316126,AY46 3222,FJ496198,AF45 0096,EU000509,AY4 63224,FJ496081,AY8 78068,KC156118,EU 000512,EF514711,AF 443097,AF286237,AB 253672,U51189,DQ3 66665,AY536233,EF6 37056,FJ496164,DQ8 53448,EF637048,FJ4 96178,FJ670518,AY8 35757,DQ366659,AB 485633,AY167123,FJ 496171,AF110970,EF 514704,AB286859,D 0396391,DQ351236, AF408628,EF637050, AY322189,AY169813 ,EU884501,M62320,A Y173955,AB485655, AB220947,KF766538, AY42383,AF004885, AY046058,AJ320484, AF443115,AY227107, EU786670,DQ396393 ,AB253656,L20571,A F193253,JQ316132,A Y352657,JQ429433,A JQ06022,DQ853436,F J771006,EF363127,A Y901966,DQ093592, FJ496195,AB746343, AF110978,DQ164104 ,AY314056,AB42855 4,EF637054,AB25368 8,AB254153,XQ4415, AY835774,AB253720 ,GU595154,AB28736 8,AJ404325,AB42855 |

-continued

| Taxonomy | NCBI Reference Sequence ID | Host | No. of Genomes | Lineage | Segment Count | Genbank Accession ID |
|---|---|---|---|---|---|---|
| | | | | | | 3,EU000514,FJ49615 |
| | | | | | | 2,AY751407,FJ67053 |
| | | | | | | 0,DQ085876,DQ6768 |
| | | | | | | 77,FJ711703,AY0497 |
| | | | | | | 09,JQ316134,AF4086 |
| | | | | | | 27,FJ496197,U37270 |
| | | | | | | ,AB253677,AY32219 |
| | | | | | | 1,FJ670524,FJ49618 |
| | | | | | | 5,DQ912823,AY4632 |
| | | | | | | 21,AF460974,AY7726 |
| | | | | | | 99,AB646691,DQ396 |
| | | | | | | 378,AB253647,AB25 |
| | | | | | | 3682,EF514710,AB48 |
| | | | | | | 5662,DQ396385,DQ8 |
| | | | | | | 45388,Z11530,AB220 |
| | | | | | | 946,AB253703,FJ195 |
| | | | | | | 090,AY878057,AF193 |
| | | | | | | 275,AY772695,AY83 |
| | | | | | | 5754,EF192592,EF51 |
| | | | | | | 4712,GU595158,AB2 |
| | | | | | | 53652,AF110963,KC |
| | | | | | | 156119,EF368372,FJ |
| | | | | | | 623495,EU616649,A |
| | | | | | | F443084,AB253699,A |
| | | | | | | F385935,KC898986, |
| | | | | | | AB286854,AB254156 |
| | | | | | | ,FJ623480,DQ396388 |
| | | | | | | ,AB254155,AB48564 |
| | | | | | | 5,DQ358811,AY9019 |
| | | | | | | 65,AB480694,AY173 |
| | | | | | | 957,DQ351238,AF28 |
| | | | | | | 6238,DQ351223,AB2 |
| | | | | | | 53716,AY455784,EU |
| | | | | | | 448295,AB287371,AF |
| | | | | | | 443112,AB480698,FJ |
| | | | | | | 213781,AY162225,A |
| | | | | | | Y352654,AB485663,F |
| | | | | | | J771007,AB253423,A |
| | | | | | | B253671,AB253635, |
| | | | | | | AY532635,AY835769 |
| | | | | | | ,AB485651,AY87806 |
| | | | | | | 5,AB254149,DQ3512 |
| | | | | | | 30,AB253687,AY536 |
| | | | | | | 237,EF637053,JN860 |
| | | | | | | 767,EF091932,AB604 |
| | | | | | | 951,DQ358805,AY90 |
| | | | | | | 1975,AJ271445,U346 |
| | | | | | | 03,K03454,U26546,A |

| Taxonomy | NCBI Reference Sequence ID | Host | No. of Genomes | Lineage | Segment Count | Genbank Accession ID |
|---|---|---|---|---|---|---|
| | | | | | | B746342,FJ496160,J X503073,KC899009, AF086817,AF286235, FJ495819,AF443086, K03455,AY835767,E U786672,AB220944, FJ623476,GQ999985 ,FF514708,AB286849 ,AY586540,DQ05640 4,DQ396398,AY4557 81,M17449,AB48564 1,AB485634,KC1561 21,AY314049,AF4431 11,KC522033,AB286 860,KC156120,DQ09 3597,DQ164122,AY5 35659,AY331289,AY 560109,DQ230841,K C935957,DQ445637, AF443089,EF192591, AB731667,EU110088 DQ093596,EU78667 8,AB604949,HM4699 83,EU616642,DQ093 600,AY585268,EU61 6641,AY463223,AB2 54143,DQ853454,AY 838568,FJ623488,DQ 853447,AY322187,D 0011175,AY818643,, AF164485,HM215250 DQ056411,AY33128 2,AB731666,AB2536 37,AF224507,DQ011 165,AF443088,KC89 8975,AB253670,AB2 86862,AB286861,AF4 43079,FN392876,DQ 886031,KC852172,A Y703910,DQ093606, FJ771008,DQ853458, AF443075,DQ487191 ,AB287364,AF490973 ,AY779559,HM02645 6,HM469981,GQ9999 78,AY169808,AY423 385,AY901979,AY35 2656,HM776939,AY8 |

| Taxonomy | NCBI Reference Sequence ID | Host | No. of Genomes | Lineage | Segment Count | Genbank Accession ID |
|---|---|---|---|---|---|---|
| | | | | | | 78060,AY772693,AB485642,AY901967,AB731670,AY878054,DQ445636,KC898983,AF423755,AB428556,AB480692,AY531116,AY781126,AF443087,GQ372989,AB22112 6,AF110976,AY314061,AY049710,AB097869,DQ396394,AY314054,GU599153,FJ495937,FJ496174,AB286853,JQ316128,AB565501,AB253709,AB097866,AY835759,GQ999991,DQ295192,D0093602,AF377958,AB485654,AF443114,AJ866558,AY162224,DQ085867,AB480044,AB485647,DQ164129,AF321523,AY162223,AB746344,GQ1758 83,AY455780,FJ185258,AB289589,M27323,HM026458,AF484511,AF286227,AB253689,HM776938,AF290029,DQ383750,FJ496170,KC156130,U86780,AY314063,AB254142,FJ185246,AF110980,FJ496157,U88823,JF804810,AB253648,M15654,DQ853443,FN392877,EF036527,AB253643,FJ460500,GQ999979,GQ999986,FJ185240,KC852174,AF361873,AB253669,AF411964,AB428558,M38431,AB485648,AB253723,DQ234790,DQ164113,FJ185236,AB485632,AB097871,AY173951,KC503852,AF005495,EF0365 |

| Taxonomy | NCBI Reference Sequence ID | Host | No. of Genomes | Lineage | Segment Count | Genbank Accession ID |
|---|---|---|---|---|---|---|
| | | | | | | 31,DQ396399,FJ4962 07,EF420986,AY3140 62,EF175209,JQ3161 31,AF443085,FJ8536 20,EF036532,AF4430 90,DQ396372,AM000 055,AB052867,AB48 0300,AB253651,DQ1 64114,AY835762,AB 289588,AB253717,AJ 276596,AF256205,E U697909,AB253658, AY818641,EU031915 ,AF256206,DQ16410 9,EU00513,AB4856 66,DQ859180,AB254 ,141,GQ372987,AF40 8629,AY588970,DQ1 64127,AY158534,FJ4 95943,DQ837381,DQ 358803,FJ623481,EU 293446,AB231897,AF 110977,DQ011179,A B220948,FJ496001,F J185229,AF407418,A F413987,AY835780,E U786681,AF385934, KC156221,AY838566 ,AB428551,AY87806 6,FJ185253,AB48566 7,DQ396389,GU1115 55,AY314059,DQ093 593,AY901977,AF457 058,AY237165,DQ09 3587,AJ 508596,FJ18 5250,AF256207,AJ86 6557,FJ670527,AF04 9495,DQ011166,K02 083,FJ496188,AY703 908,AY835749,KC89 9014,KC156217,DQ3 69993,AF110964,AY7 51406,FJ496000,KC8 99012,DQ369995,DQ 354118,DQ853452,D Q396387,FJ496149,A Y008718,EU786677, DQ396377,AY331283 |

| Taxonomy | NCBI Reference Sequence ID | Host | No. of Genomes | Lineage | Segment Count | Genbank Accession ID |
|---|---|---|---|---|---|---|
| | | | | | | ,AB023804,AF110981,EF514707,DQ351233,KC156216,AY58654,7U34604,AB287369,U23487,AY779557,FJ496175,AB253428,EF078278,AB049811,FJ623475,DQ676878,FJ670517,DQ886037,AB253691,L39106,AB253680,EU000515,AB485661,DQ978981,EU547186,DQ164106,DQ853449,DQ676880,AF443080,EF420987,AY463230,AB253636,KC898987,AF077336,AB604950,EF637046,AF082395,AY901978,AF003887,KC156123,AY586549,AY878063,AY463228,EF029069,AB097865,AY901969,JX503072,AF286229,AY331292,DQ351228,GQ999982,DQ164111,DQ085870,KC899013,DQ011173,AJ271370,AY901968,FJ853621,KC156125,FJ496159,AY173954,AY835777,DQ853440,AF443110,AB253665,AY169803,AY835750,FJ496187,DQ351218,DQ011171,HM469982,KC156124,EF637051,EU110095,EF368370,AF110962,GU595151,EU786676,AY173953,AY835772,AF042101,DQ445631,AB254144,EU616645,DQ093594,AY878070,GU595150,AF042106,JN571034,FJ496184,AY082968,GU595155,HM215252,G |

-continued

| Taxonomy | NCBI Reference Sequence ID | Host | No. of Genomes | Lineage | Segment Count | Genbank Accession ID |
|---|---|---|---|---|---|---|
| | | | | | | 099976,AY314045, AF290030,AY423386, AB289590,AF423758, JN188292,AY463219, DQ351224,AB485638 ,AJ508595,AY118166 ,AF289549,JN860769 ,AB564746,EF363126 ,DQ396373,KC15611 6,AF067156,KF76654 1,FJ185243,AF06164 0,AF067158,AB25415 2,JX574661,HM4699 75,AY331288,EF0365 29,AB286851,EF5146 98,AB253425,KC492 738,AF443104,KF766 542,AB286864,FJ623 490,DQ853453,EU00 0508,DQ011172,KC1 56211,DQ369990,FJ1 85237,AY169816,DQ 396392,AY779556,A B480299,AY805330, HM469980,AY901973 ,KC156212,AF28623 1,AY779553,AF41196 5,DQ351216,EU2934 47,DQ007902,DQ007 901,AY779564,FJ185 257,AB253424,U6959 0,AB428559,DQ1641 15,AB485650,EF0782 79,AB485643,AY779 561,AF049494,AF407 419,DQ295196,AF07 5703,AY772694,AY0 74891,AB253663,AF0 76475,U12055,GQ99 9988,EU110089,DQ3 96365,AJ237565,EFS 14700,AJ239083,AF2 86226,AY560110,GQ 372990,AF286232,L0 2317,AB253426,DQ3 51227,FJ496196,DQ9 79024,AB731664,AY 463326,EF036533,D |

| Taxonomy | NCBI Reference Sequence ID | Host | No. of Genomes | Lineage | Segment Count | Genbank Accession ID |
|---|---|---|---|---|---|---|
| | | | | | | 0853464,DQ011169, AF414006,AB485664, FJ670526,AB253713, AY352275,FJ185248, EF363122,AB254148, FJ496158,DQ396366, JN860768,AY901972, ,FJ496208,M93259,D 036991,GU595157, AB253642,AY158533 ,EF029066,AB253655 ,DQ487189,AY77269 8,EF514702,AY53623 4,KF766540,HM2152 49,DQ369981,FJ1950 86,AY771592,FJ4960 72,DQ369986,FJ4961 53,AF286233,EU693 240,FJ496007,FJ496 079,JN860766,FJ771 009,FJ496080,AF11097 081,D86069,AF443109 3,FJ185252,U52953, FJ623489,AY169805, DQ369994,AF443109 ,AF468970,JN860762 ,U54771,DQ351229,A F063224,AY093603, DQ369982,FJ623486, AB097870,FJ496192, EU616640,AY093604 ,DQ093599,AB64183 7,AB032740,DQ3699 84,FJ213783,EU2206 98,GQ365649,AF443 081,AY118165,FJ185 241,GU207884,KC89 8994,AB253702,AB7 31668,FJ495939,AY1 73958,FJ496169,AY5 85267,FJ496083,AB4 85669,DQ056408,FJ3 58521,FJ185231,AB2 87378,KC522032,AY 455783,KF766539,D 0358806,DQ369976, EF368371,AB254150, AF286225,AF061641, |

| Taxonomy | NCBI Reference Sequence ID | Host | No. of Genomes | Lineage | Segment Count | Genbank Accession ID |
|---|---|---|---|---|---|---|
| | | | | | | DQ093586,AB253427,DQ487188,AB253370,AB097872,AF110968,HM469977,GQ175882,DQ369988,FJ496201,AY900576,EU735538,DQ017382,AY331284,AB253667,AY463218,AY463237,FJ496005,EF036534,AY878058,EF036536,AB565496,AY835748,AB253432,AB564745,AF443096,HM469973,AY970946,EU110090,DQ853444,AF197339,KC522031,FJ496190,AB646289,EF514701,AB287376,AY97094 7,FJ496176,DQ011170,DQ085873,DD409979,AY331286,EF036535,DQ859178,GQ999989,AY618998,AY970949,AB221005,AB098330,U69591,DQ017383,U69584,AY612637,JF804807,DQ853437,U26942,FJ495818,FJ496177,KC899006,FU786679,AY008715,AB286852,AY536236,AY560107,AB485668,HM469978,AY173956,AB253668,DQO93598,DQ164108,DQ396381,JX503071,FJ496146,DQ093595,L20587,AF193277,AF075719,DQ011167,JF804813,AY586541,FJ496204,AY158535,JF804812,AB097873,EU031914,AY901970,AY878056,AB254146,AF408626,FJ185242,DQ366666,JQ316138,D0164124,AB480696,J |

-continued

| Taxonomy | NCBI Reference Sequence ID | Host | No. of Genomes | Lineage | Segment Count | Genbank Accession ID |
|---|---|---|---|---|---|---|
| | | | | | | X503078,AB253422, AY703909,AJ866556, DQ396390,AB253641 ,AY314050,FJ496150 ,DQ358804,AB28958 7,KC156219,GQ9999 77,JX503083,FJ6234 83,GQ290462,EU293 449,U69587,JN86076 3,DQ056416,AB2536 61,AY314058,AB287 365,DQ164125,AY77 9554,GQ845124,AB4 85652,DQ093605,AY 835781,AF259955,K C852173,GU733717, U88825,AB052995,A Y169802,AY772690,F J496168,KC156214,F J496155,U69588,AB2 86855,KC93959,DQ 400856,JN860765,KC 156114,FR846409,A Y169806,AF286239, GQ999987,AB231894 ,DQ853462,GQ27761 0,AJQ06287,DQ0564 13,AY463232,AF4430 78,AF332867,DQ676 886,AY169809,AF064 699,DQ366661,AB56 5497,FJ496154,AMOO 0053,AF529572,KC8 99008,AB565499,EU 110096,AB220945,FJ 496004,AY835775,F R846408,DQ164107, AY77334l,AB253664 ,DQ676875,FJ185256 ,HM215251,DQ85346 1,AY423382,AB2537 15,U88822,EF637052 ,DQ354116,GQ36565 1,DQ056412,AF0421 05,DQ366663,AY878 062,EF175211,EF175 212,FJ495825,DQ085 871,AY228557,FJ496 |

| Taxonomy | NCBI Reference Sequence ID | Host | No. of Genomes | Lineage | Segment Count | Genbank Accession ID |
|---|---|---|---|---|---|---|
| | | | | | | 161,AF443098,JQ316133,AY308761,DQ396383,JX574662,EU884500,AY314060,AY271690,EU616644,GQ999972,M26727,AB253683,EU743963,GU647198,FJ496084,AB485665,FJ495821,JF719818,GU595148,D0676870,EU697907,JN860761,GU230139,AB604948,AY835766,AF070521,FJ496216,FJ496078,EF175210,AB253650,AF443102,AY169812,DQ369985,DQ358807,FJ496179,AY535660,AY835753,AY314044,JF804814,AB480693,AF443093,AJ288982,AF385936,EF514705,AY818642,AF443100,AY463225,U69592,EF637047,AJ302646,GU230137,U69593,DQ093604,AB564744,AF411966,AB286955,DQ056409,AY779555,AY835760,EU110093,AB253701,JQ316129,DQ676879,KC898990,AB253654,JF719819,AF443094,EF514697,AY779563,DQ369980,AB286858,AB253696,EF514703,DQ979023,EF633445,AF529573,AF076998,AF530576,AF286230,AY308760,FJ670520,AY779552,DQ676872,FJ623478,AF005496,AB428562,AY322185,AB253430,AY835764,AF063223,DQ085869,AY45578,DQ351220,AY008 |

| Taxonomy | NCBI Reference Sequence ID | Host | No. of Genomes | Lineage | Segment Count | Genbank Accession ID |
|---|---|---|---|---|---|---|
| | | | | | | 716,AY314051,AY331285,DQ886038,DQ369987,KC492737,AY878071,HM469979,AY322184,DQ366664,KC898989,AF503396,FJ496162,AB253695,FR846410,DQ396374,FJ496203,AB565478,DQ056417,AY901981,EF029068,AB253675,DQ354123,KC914396,FJ185247,AY781125,DQ164123,DQ396397,EU110091,AF110967,AJ291720,FJ623487,AB254151,AF443113,AB253724,FJ496173,FJ670529,AY878072,AB253711,AB604946,KC156128,AB428561,DQ369992,DQ056405,A04321,AF133821,DQ164126,FJ496002,DQ845386,DQ676873,DQ845387,AB078005,FJ496180,AF286234,EF637049,A34828,DQ083238,AF003888,AF110979,AF443101,JQ316135,FJ670528,DQ093603,AB485658,AB253722,AJ302647,DQ056406,HM100716,AF286224,KC156117,AY331290,DQ676884,AY882421,AY169804,DQ853442,EF363123,AB253700,DQ396375,M93258,EF057102,AY331287,DQ396367,AF286228,EF036530,FJ496145,AB485649,AF033819,EF178358,KC156210,DQ164119,AF197340,AB480046,EU541617,KC503854, |

| Taxonomy | NCBI Reference Sequence ID | Host | No. of Genomes | Lineage | Segment Count | Genbank Accession ID |
|---|---|---|---|---|---|---|
| | | | | | | DQ085874,AF408632 |
| | | | | | | ,KC898981,GU59515 |
| | | | | | | 9,EU448296,AY1739 |
| | | | | | | 52,AY169811,M1992 |
| | | | | | | 1,JQ316137,AB25367 |
| | | | | | | 8,KC156122,AB2536 |
| | | | | | | 98,EU000506,FJ14961 |
| | | | | | | 72,AY463231,DQ011 |
| | | | | | | 174,GQ999984,A071 |
| | | | | | | 08,AY878061,AY180 |
| | | | | | | ,905,AB253660,U4309 |
| | | | | | | 6,EF514709,AB25371 |
| | | | | | | 0,DQ396368,EU8619 |
| | | | | | | 77,DQ853463,DQ853 |
| | | | | | | 446,AY314048,JF804 |
| | | | | | | 805,DQ676883,DQ36 |
| | | | | | | 9989,GU733716,AY4 |
| | | | | | | 23387,FJ496165,DQ3 |
| | | | | | | 58810,AB480298,AF4 |
| | | | | | | 23757,AB565495,AY |
| | | | | | | 585266,AY228556,A |
| | | | | | | B287366,DQ366660, |
| | | | | | | AB253725,AB032741 |
| | | | | | | ,GQ365650,AY83575 |
| | | | | | | 5,DQ676885,JF80481 |
| | | | | | | 1,DQ011168,KC8989 |
| | | | | | | 95,AB485646,AY237 |
| | | | | | | 166,EF469243,AB253 |
| | | | | | | 666,FJ496167,AY463 |
| | | | | | | 220,AY169815,AF316 |
| | | | | | | 544,AB253718,AF290 |
| | | | | | | 027,AB231893,DQ39 |
| | | | | | | 6376,JX503077,FJ49 |
| | | | | | | 6182,FJ495940,FJ49 |
| | | | | | | 6211,DQ011176,HM4 |
| | | | | | | 69976,DQ676876,FN |
| | | | | | | 392875,AF492624,H |
| | | | | | | M067748,AB565479, |
| | | | | | | DQ859179,DQ85345 |
| | | | | | | 9,DQ383746,DQ3512 |
| | | | | | | 25,AB485640,AF1109 |
| | | | | | | 65,JF804809,EF5147 |
| | | | | | | 06,FJ496209,AF0849 |
| | | | | | | 36,AF443095,U88824 |
| | | | | | | ,DQ164128,FJ496077 |
| | | | | | | ,AY049708,AY77956 |
| | | | | | | 2,AJ291719,AF42375 |
| | | | | | | 9,DQ676881,AF4430 |

-continued

| Taxonomy | NCBI Reference Sequence ID | Host | No. of Genomes | Lineage | Segment Count | Genbank Accession ID |
|---|---|---|---|---|---|---|
| | | | | | | 91,KC899010,DQ396395,AB485636,AF076474,DQ979025,DQ351226,AF042100,AB254145,AY588971,AY314047,AY970948,KC935958,AY463234,AY536238,AB253646,DQ056415,FJ185251,DQ886035,DQ093588,FJ496205,AF110972,EU735537,AB253645,AY835776,A14116,AB428552,AY703911,EF036528,AF492623,AY781128,FJ49618,6,GU595152 |
| Human immunodeficiency virus 2 | NC_001722 | vertebrates,human | 41 | Retroviridae,Lentivirus,Human immunodeficiency virus 2 | — | AY509260,M15390,M30895,AB499695,AF208027,EU028345,AB485671,JQ4542,U22047,AB731745,AB731744,AB485670,AB499693,AB731742,AB731743,L36874,U38293,JQ4498,EU980602,AY509259,AB731741,AB731739,L07625,X52223,AY530889,U27200,Z48731,M31113,DQ0835,JQ3654,DQ307022,XQ5291,AB731738,AB499694,A09995,X61240,AB731740,AF082339,AB100245,E02138,M30502 |
| Human metapneumovirus | NC_004148 | vertebrates,human | 69 | Paramyxoviridae,Metapneumovirus,Human metapneumovirus | — | HM197719,KC403972,DQ843659,KF530185,KC403975,KC562219,KC562222,KC403980,KC562228,FJ168778,KC562232,KF530163,AF371337,KC,562221,EF535506,KC403982,JN184400,KC403984,KF530165,KC562223,KC562224,KC562240,JN184399 |

| Taxonomy | NCBI Reference Sequence ID | Host | No. of Genomes | Lineage | Segment Count | Genbank Accession ID |
|---|---|---|---|---|---|---|
| | | | | | | ,KC562230,KF53017 8,KF530183,KC4039 79,KF530177,GQ153 651,KC562229,KC56 2241,KC562231,KC5 62234,KC403981,KF 530171,KC403978,K C562233,KF530179, KC403976,KC562238 ,AY297748,KC40397 3,KC56242,KC4039 74,KC562226,KC562 235,KC562244,JN184 401,KF530166,KC56 2239,KC403977,KF5 30167,C0840316,KC 562220,KF530173,KF 530181,KF530164,JN 184402,KC403971,A Y525843,KC562243, KC562225,KC562227 ,AB03857,AY29774 9,KC403983,F116877 9,DQ843658,KC5622 37 |
| Human papillomavirus | NC_016157 | vertebrates,human | 1 | Papillomaviridae,Human papillomavirus 126-like viruses | — | JX413105 |
| Human papillomavirus | NC_019023 | vertebrates,human | 2 | Papillomaviridae,Human papillomavirus 161-like viruses | — | JX413108,JX413109 |
| Human papillomavirus | NC_022095 | vertebrates,human | 2 | Papillomaviridae,Human papillomavirus | — | JX444073,HG421739 |
| Human papillomavirus FA75/KI88-03 | NC_001596 | vertebrates,human | 1 | Papillomaviridae,Betapapillomavirus,Betapapillomavirus 2 | — | EU410347 |
| Human papillomavirus RTRX7 | NC_001531 | vertebrates,human | 1 | Papillomaviridae,Betapapillomavirus,Betapapillomavirus 1 | — | U85660 |
| Human papillomavirus SIBX-3a | NC_001596 | vertebrates,human | 1 | Papillomaviridae,Betapapillomavirus,Betapapillomavirus 2 | — | FN598907 |
| Human papillomavirus SIBX1 | NC_005134 | vertebrates,human | 1 | Papillomaviridae,Betapapillomavirus,Betapapillomavirus 5 | — | FN677755 |
| Human papillomavirus SIBX2 | NC_001596 | vertebrates,human | 1 | Papillomaviridae,Betapapillomavirus,Betapapillomavirus 2 | — | FN677756 |
| Human papillomavirus SIBX8 | NC_001596 | vertebrates,human | 1 | Papillomaviridae,Betapapillomavirus,Betapapillomavirus 2 | — | HE963025 |
| Human papillomavirus type 100 | NC_001596 | vertebrates,human | 1 | Papillomaviridae,Betapapillomavirus,Betapapillomavirus 2 | — | FM955839 |
| Human papillomavirus type 104 | NC_001596 | vertebrates,human | 1 | Papillomaviridae,Betapapillomavirus,Betapapillomavirus 2 | — | FM955840 |
| Human papillomavirus type 105 | NC_001531 | vertebrates,human | 1 | Papillomaviridae,Betapapillomavirus,Betapapillomavirus 1 | — | FM955841 |

-continued

| Taxonomy | NCBI Reference Sequence ID | Host | No. of Genomes | Lineage | Segment Count | Genbank Accession ID |
|---|---|---|---|---|---|---|
| Human papillomavirus type 107 | NC_001596 | vertebrates,human | 1 | Papillomaviridae,Betapapillomavirus,Betapapillomavirus 2 | — | EF422221 |
| Human papillomavirus type 110 | NC_001596 | vertebrates,human | 1 | Papillomaviridae,Betapapillomavirus,Betapapillomavirus 2 | — | EU410348 |
| Human papillomavirus type 111 | NC_001596 | vertebrates,human | 1 | Papillomaviridae,Betapapillomavirus,Betapapillomavirus 2 | — | EU410349 |
| Human papillomavirus type 113 | NC_001596 | vertebrates,human | 1 | Papillomaviridae,Betapapillomavirus,Betapapillomavirus 2 | — | FM955842 |
| Human papillomavirus type 115 | NC_001591 | vertebrates,human | 1 | Papillomaviridae,Betapapillomavirus,Betapapillomavirus 3 | — | FJ947080 |
| Human papillomavirus type 118 | NC_001531 | vertebrates,human | 1 | Papillomaviridae,Betapapillomavirus,Betapapillomavirus 1 | — | GQ246951 |
| Human papillomavirus type 12 | NC_001531 | vertebrates,human | 1 | Papillomaviridae,Betapapillomavirus,Betapapillomavirus 1 | — | X74466 |
| Human papillomavirus type 120 | NC_001596 | vertebrates,human | 3 | Papillomaviridae,Betapapillomavirus,Betapapillomavirus 2 | — | GQ845442,JQ963484,JQ963485 |
| Human papillomavirus type 122 | NC_001596 | vertebrates,human | 1 | Papillomaviridae,Betapapillomavirus,Betapapillomavirus 2 | — | GQ845444 |
| Human papillomavirus type 124 | NC_001531 | vertebrates,human | 1 | Papillomaviridae,Betapapillomavirus,Betapapillomavirus 1 | — | GQ845446 |
| Human papillomavirus type 126 | NC_016157 | vertebrates,human | 1 | Papillomaviridae,Human papillomavirus 126-like viruses | — | AB646346 |
| Human papillomavirus type 135 | NC_017993 | vertebrates,human | 1 | Papillomaviridae,Human papillomavirus type 135 | — | HM999987 |
| Human papillomavirus type 136 | NC_017994 | vertebrates,human | 1 | Papillomaviridae,Human papillomavirus type 136 | — | HM999988 |
| Human papillomavirus type 137 | NC_017995 | vertebrates,human | 1 | Papillomaviridae,Human papillomavirus type 137 | — | HM999989 |
| Human papillomavirus type 140 | NC_017996 | vertebrates,human | 1 | Papillomaviridae,Human papillomavirus type 140 | — | HM999992 |
| Human papillomavirus type 144 | NC_017997 | vertebrates,human | 1 | Papillomaviridae,Human papillomavirus type 144 | — | HM999996 |
| Human papillomavirus type 14D | NC_001531 | vertebrates,human | 1 | Papillomaviridae,Betapapillomavirus,Betapapillomavirus 1 | — | X74467 |
| Human papillomavirus type 15 | NC_001596 | vertebrates,human | 1 | Papillomaviridae,Betapapillomavirus,Betapapillomavirus 2 | — | X74468 |
| Human papillomavirus type 154 | NC_021483 | vertebrates,human | 1 | Papillomaviridae,Human papillomavirus type 154 | — | JN211193 |
| Human papillomavirus type 166 | NC_019023 | vertebrates,human | 1 | Papillomaviridae,Human papillomavirus 161-like viruses | — | JX413104 |
| Human papillomavirus type 17 | NC_001596 | vertebrates,human | 2 | Papillomaviridae,Betapapillomavirus,Betapapillomavirus 2 | — | X74469,JN211195 |
| Human papillomavirus type 19 | NC_001531 | vertebrates,human | 1 | Papillomaviridae,Betapapillomavirus,Betapapillomavirus 1 | — | X74470 |
| Human papillomavirus type 20 | NC_001531 | vertebrates,human | 1 | Papillomaviridae,Betapapillomavirus,Betapapillomavirus 1 | — | U31778 |
| Human papillomavirus type 21 | NC_001531 | vertebrates,human | 1 | Papillomaviridae,Betapapillomavirus,Betapapillomavirus 1 | — | U31779 |

| Taxonomy | NCBI Reference Sequence ID | Host | No. of Genomes | Lineage | Segment Count | Genbank Accession ID |
|---|---|---|---|---|---|---|
| Human papillomavirus type 22 | NC_001596 | vertebrates,human | 1 | Papillomaviridae,Betapapillomavirus,Betapapillomavirus 2 | — | U31780 |
| Human papillomavirus type 23 | NC_001596 | vertebrates,human | 1 | Papillomaviridae,Betapapillomavirus,Betapapillomavirus 2 | — | U31781 |
| Human papillomavirus type 24 | NC_001531 | vertebrates,human | 1 | Papillomaviridae,Betapapillomavirus,Betapapillomavirus 1 | — | U31782 |
| Human papillomavirus type 25 | NC_001531 | vertebrates,human | 1 | Papillomaviridae,Betapapillomavirus,Betapapillomavirus 1 | — | X74471 |
| Human papillomavirus type 36 | NC_001531 | vertebrates,human | 1 | Papillomaviridae,Betapapillomavirus,Betapapillomavirus 1 | — | U31785 |
| Human papillomavirus type 37 | NC_001596 | vertebrates,human | 1 | Papillomaviridae,Betapapillomavirus,Betapapillomavirus 2 | — | U31786 |
| Human papillomavirus type 38 | NC_001596 | vertebrates,human | 2 | Papillomaviridae,Betapapillomavirus,Betapapillomavirus 2 | — | JN211196,U31787 |
| Human papillomavirus type 38b | NC_001596 | vertebrates,human | 1 | Papillomaviridae,Betapapillomavirus,Betapapillomavirus 2 | — | DQ090005 |
| Human papillomavirus type 47 | NC_001531 | vertebrates,human | 1 | Papillomaviridae,Betapapillomavirus,Betapapillomavirus 1 | — | M32305 |
| Human papillomavirus type 49 | NC_001591 | vertebrates,human | 1 | Papillomaviridae,Betapapillomavirus,Betapapillomavirus 3 | — | X74480 |
| Human papillomavirus type 5 | NC_001531 | vertebrates,human | 3 | Papillomaviridae,Betapapillomavirus,Betapapillomavirus 1 | — | M17463,M22961,JN211194 |
| Human papillomavirus type 5b | NC_001531 | vertebrates,human | 1 | Papillomaviridae,Betapapillomavirus,Betapapillomavirus 1 | — | D90252 |
| Human papillomavirus type 75 | NC_001591 | vertebrates,human | 1 | Papillomaviridae,Betapapillomavirus,Betapapillomavirus 3 | — | Y15173 |
| Human papillomavirus type 76 | NC_001591 | vertebrates,human | 1 | Papillomaviridae,Betapapillomavirus,Betapapillomavirus 3 | — | Y15174 |
| Human papillomavirus type 8 | NC_001531 | vertebrates,human | 1 | Papillomaviridae,Betapapillomavirus,Betapapillomavirus 1 | — | M12737 |
| Human papillomavirus type 80 | NC_001591 | vertebrates,human | 1 | Papillomaviridae,Betapapillomavirus,Betapapillomavirus 3 | — | Y15176 |
| Human papillomavirus type 9 | NC_001596 | vertebrates,human | 1 | Papillomaviridae,Betapapillomavirus,Betapapillomavirus 2 | — | X74464 |
| Human papillomavirus type 92 | NC_004500 | vertebrates,human | 1 | Papillomaviridae,Betapapillomavirus,Betapapillomavirus 4 | — | AF531420 |
| Human papillomavirus type 93 | NC_001531 | vertebrates,human | 1 | Papillomaviridae,Betapapillomavirus,Betapapillomavirus 1 | — | AY382778 |
| Human papillomavirus type 96 | NC_005134 | vertebrates,human | 1 | Papillomaviridae,Betapapillomavirus,Betapapillomavirus 5 | — | AY382779 |
| Human papillomavirus type 98 | NC_001531 | vertebrates,human | 1 | Papillomaviridae,Betapapillomavirus,Betapapillomavirus 1 | — | FM955837 |
| Human papillomavirus type 99 | NC_001531 | vertebrates,human | 1 | Papillomaviridae,Betapapillomavirus,Betapapillomavirus 1 | — | FM955838 |
| Human parainfluenza virus 1 | NC_003461 | vertebrates,human | 21 | Paramyxoviridae,Respirovirus,Human parainfluenza virus 1 | — | KF687315,KF687307, KF687312,KF530217, KF687314,KF530205, KF530215,KF687316, |

| Taxonomy | NCBI Reference Sequence ID | Host | No. of Genomes | Lineage | Segment Count | Genbank Accession ID |
|---|---|---|---|---|---|---|
| Human parainfluenza virus 2 | NC_003443 | vertebrates,human | 5 | Paramyxoviridae,Rubulavirus,Human parainfluenza virus 2 | — | KF530212,KF530220, KF687308,KF530202, KF530221,KF687310, KF530203,KF687311, KF530209,AF457102, KF530198,KF687313, KF687309 X57559,AF533012,A B176531,AF533010,A F533011 |
| Human parainfluenza virus 3 | NC_001796 | vertebrates,human | 47 | Paramyxoviridae,Respirovirus,Human parainfluenza virus 3 | — | KF530242,KF530231, KF530230,KF530228, KF530229,KF530241, KF687355,KF687319, KF687342,KF530234, KF530251,KF530233, KF687338,KF530232, KF687317,AB012132, KF687321,KF530257, KF687356,KF687331, KF687350,KF687318, KF530245,KF530225, KF530253,KF530237, KF687341,U51116,E U424062,KF687329, KF530249,KF530252, KF530256,KF687335, KF687336,KF687340, KF530236,EU326526 ,KF687337,KF530243 ,Z11575,KF530247,K F530239,FJ455842,K F687346,KF530250,K F530226 |
| Human parainfluenza virus 4a | NC_021928 | vertebrates,human | 2 | Paramyxoviridae,Rubulavirus,Human parainfluenza virus 4 | — | KF483663,AB543336 |
| Human parainfluenza virus 4b | NC_021928 | vertebrates,human | 3 | Paramyxoviridae,Rubulavirus,Human parainfluenza virus 4 | — | EU627591,JQ241176 ,AB543337 |
| Human parvovirus B19 | NC_000883 | vertebrates,human | 8 | Parvoviridae,Erythrovirus,Human parvovirus B19 | — | AY504945,FJ591158, AY386330,AY083234 ,AF162273,FN598218 ,FN598217,AB5033 1 |
| Human picobirnavirus | NC_007026 | vertebrates,human | 1 | Picobirnaviridae,Picobirnavirus,Human picobirnavirus | seg. 1 | AB186897 |

-continued

| Taxonomy | NCBI Reference Sequence ID | Host | No. of Genomes | Lineage | Segment Count | Genbank Accession ID |
|---|---|---|---|---|---|---|
| Human picobirnavirus | NC_007027 | vertebrates,human | 1 | Picobirnaviridae,Picobirnavirus,Human picobirnavirus | seg. 2 | AB186898 |
| Human poliovirus 1 | NC_002058 | vertebrates,human | 126 | Picornaviridae,Enterovirus,Enterovirus C | — | AF111984,KC880377,AB180072,AF405667,KC880375,AF405687,EF682358,AB180070,AF405679,AF462419,AJ132960,GQ984141,KF537633,AY928385,AY928387,AF405688,KC880382,KC880370,EF682359,EF682356,AF405683,FJ769379,EF682357,AY278553,FJ859063,AF111961,FJ859059,EU794955,AF111982,EF682345,AJ430385,AF405666,KC880366,AF405673,AF538840,FJ859058,KC880368,AF405677,EU794961,EF682355,FJ769380,EU794960,FJ859062,KC880379,AF405674,V01148,AF111966,FJ76,9381,EF682346,AF405680,AF405669,KC880367,FJ769385,EU794962,AF405676,FJ769383,AF405668,AF416342,EU794954,AF405689,EU794953,KC880378,AF405671,AY560657,AF458333,AF405682,AF405684,FJ859061,FJ769378,FJ769384,EU794964,EF682343,AF405664,KC880369,AF405678,FJ859064,AJ416942,EU794956,EF682348,AF538841,AB180071,EU794958,KC880376,AB180073,KC880373,EF682344,AF405665,EF682354,AF405675,EF682351,AF1119 |

-continued

| Taxonomy | NCBI Reference Sequence ID | Host | No. of Genomes | Lineage | Segment Count | Genbank Accession ID |
|---|---|---|---|---|---|---|
| | | | | | | 83,FJ859060,KC880371,AF111953,AF538843,EU794959,EU794957,KC880380,AY928386,AF538842,EF68,2349,KC880381,AF405685,EF682353,EF682347,EF456706,KC880372,AF405662,EF682350,AF462418,AF405672,AY184219,AF405670,AF405686,KC880365,EF682352,EU794963,KC880374,AF405663,FJ769382,AY928383,AJ132961,AY928384,AF405690,AF405681,AF111981 |
| Human poliovirus 1 strain Sabin | NC_002058 | vertebrates,human | 1 | Picornaviridae,Enterovirus,Enterovirus C | — | V01150 |
| Human poliovirus 2 | NC_002058 | vertebrates,human | 66 | Picornaviridae,Enterovirus,Enterovirus C | — | JX274984,AY278549,JX275380,AM884185,HM107833,JX275085,JX275238,JX275140,JX275147,HM107835,JX275266,AY278552,FJ898290,AM084224,AM040037,AM884184,DQ890388,JX275184,HM107832,HM107834,JX274993,DQ890387,FJ460224,AY184220,DQ205099,M12197,JX274983,AY278550,KC784368,DQ890385,AM084225,FJ460225,AY238473,AM040039,DQ0625,KC784367,DQ890386,AY278551,JX274985,FJ517649,AM040038,XQ0595,JX275015,AM084223,JX274980,AY948201,AM040035,FJ460223,JX274999,JX274991,JX274982,AJ544513,JX275008,JX274995,AY177685, |

| Taxonomy | NCBI Reference Sequence ID | Host | No. of Genomes | Lineage | Segment Count | Genbank Accession ID |
|---|---|---|---|---|---|---|
| Human poliovirus 3 | NC_002058 | vertebrates,human | 18 | Picornaviridae,Enterovirus,Enterovirus C | — | JX275352,AM040036,JX274981,A -continued

| Taxonomy | NCBI Reference Sequence ID | Host | No. of Genomes | Lineage | Segment Count | Genbank Accession ID |
|---|---|---|---|---|---|---|
| | | | | | | JX576743,JX576754,GU591760,JXQ69802,JXQ69799,JQ901454,JQ582844,GU591770,GU591764,JX576755,JF920053,GU591766,JXQ15483,JX576746,JX576734,U50362,FJ948820,JQ901452,JXQ15488,KC978856,JX576758,KF530260,JF920050,JF920047,JQ901451,JF920046,JF920054,JX576762,GU591762,JQ582843,KC731483,AY911262,JX576729,KC731482,U50363,JXQ15493,JF920057,GU591763,JX576752,JF920059,JXQ15482,JXQ15487,JX576747,JF920051,JX576760,JF920069,AF035006,JXQ15497,,JXQ15495,GU591765,JX576744,JX576761,JF920048,JXQ15479,JXQ15492,JX576748 |
| Human respiratory syncytial virus S2 | NC_001781 | vertebrates,human | 1 | Paramyxoviridae,Pneumovirus,Human respiratory syncytial virus | — | U39662 |
| Human rhinovirus 1 | NC_001617 | vertebrates,human | 1 | Picornaviridae,Enterovirus,Rhinovirus A | — | FJ445111 |
| Human rhinovirus 10 | NC_001617 | vertebrates,human | 2 | Picornaviridae,Enterovirus,Rhinovirus A | — | DQ473498,FJ445178 |
| Human rhinovirus 100 | NC_001617 | vertebrates,human | 1 | Picornaviridae,Enterovirus,Rhinovirus A | — | FJ445175 |
| Human rhinovirus 11 | NC_001617 | vertebrates,human | 1 | Picornaviridae,Enterovirus,Rhinovirus A | — | EF173414 |
| Human rhinovirus 12 | NC_001617 | vertebrates,human | 1 | Picornaviridae,Enterovirus,Rhinovirus A | — | EF173415 |
| Human rhinovirus 13 | NC_001617 | vertebrates,human | 2 | Picornaviridae,Enterovirus,Rhinovirus A | — | FJ445116,FJ445117 |
| Human rhinovirus 14 | NC_001490 | vertebrates,human | 2 | Picornaviridae,Enterovirus,Rhinovirus B | — | L05355,K02121 |
| Human rhinovirus 15 | NC_001617 | vertebrates,human | 1 | Picornaviridae,Enterovirus,Rhinovirus A | — | DQ473493 |
| Human rhinovirus 16 | NC_001617 | vertebrates,human | 1 | Picornaviridae,Enterovirus,Rhinovirus A | — | L24917 |
| Human rhinovirus 17 | NC_001490 | vertebrates,human | 1 | Picornaviridae,Enterovirus,Rhinovirus B | — | EF173420 |
| Human rhinovirus 18 | NC_001617 | vertebrates,human | 1 | Picornaviridae,Enterovirus,Rhinovirus A | — | FJ445118 |
| Human rhinovirus 19 | NC_001617 | vertebrates,human | 1 | Picornaviridae,Enterovirus,Rhinovirus A | — | FJ445119 |
| Human rhinovirus 1B | NC_001617 | vertebrates,human | 1 | Picornaviridae,Enterovirus,Rhinovirus A | — | DQ0239 |
| Human rhinovirus 2 | NC_001617 | vertebrates,human | 1 | Picornaviridae,Enterovirus,Rhinovirus A | — | XQ2316 |
| Human rhinovirus 20 | NC_001617 | vertebrates,human | 1 | Picornaviridae,Enterovirus,Rhinovirus A | — | FJ445120 |
| Human rhinovirus 21 | NC_001617 | vertebrates,human | 1 | Picornaviridae,Enterovirus,Rhinovirus A | — | FJ445121 |
| Human rhinovirus 22 | NC_001617 | vertebrates,human | 1 | Picornaviridae,Enterovirus,Rhinovirus A | — | FJ445122 |
| Human rhinovirus 23 | NC_001617 | vertebrates,human | 1 | Picornaviridae,Enterovirus,Rhinovirus A | — | DQ473497 |

-continued

| Taxonomy | NCBI Reference Sequence ID | Host | No. of Genomes | Lineage | Segment Count | Genbank Accession ID |
|---|---|---|---|---|---|---|
| Human rhinovirus 24 | NC_001617 | vertebrates,human | 2 | Picornaviridae,Enterovirus,Rhinovirus A | — | FJ445190,EF173416 |
| Human rhinovirus 25 | NC_001617 | vertebrates,human | 1 | Picornaviridae,Enterovirus,Rhinovirus A | — | FJ445123 |
| Human rhinovirus 26 | NC_001490 | vertebrates,human | 1 | Picornaviridae,Enterovirus,Rhinovirus B | — | FJ445124 |
| Human rhinovirus 27 | NC_001617 | vertebrates,human | 2 | Picornaviridae,Enterovirus,Rhinovirus A | — | FJ445186,EF173421 |
| Human rhinovirus 28 | NC_001617 | vertebrates,human | 1 | Picornaviridae,Enterovirus,Rhinovirus A | — | DQ473508 |
| Human rhinovirus 29 | NC_001617 | vertebrates,human | 1 | Picornaviridae,Enterovirus,Rhinovirus A | — | FJ445125 |
| Human rhinovirus 3 | NC_001490 | vertebrates,human | 2 | Picornaviridae,Enterovirus,Rhinovirus B | — | DQ473485,EF173422 |
| Human rhinovirus 30 | NC_001617 | vertebrates,human | 2 | Picornaviridae,Enterovirus,Rhinovirus A | — | FJ445179,DQ473512 |
| Human rhinovirus 31 | NC_001617 | vertebrates,human | 1 | Picornaviridae,Enterovirus,Rhinovirus A | — | FJ445126 |
| Human rhinovirus 32 | NC_001617 | vertebrates,human | 1 | Picornaviridae,Enterovirus,Rhinovirus A | — | FJ445127 |
| Human rhinovirus 33 | NC_001617 | vertebrates,human | 1 | Picornaviridae,Enterovirus,Rhinovirus A | — | FJ445128 |
| Human rhinovirus 34 | NC_001617 | vertebrates,human | 2 | Picornaviridae,Enterovirus,Rhinovirus A | — | FJ445189,DQ473501 |
| Human rhinovirus 35 | NC_001490 | vertebrates,human | 2 | Picornaviridae,Enterovirus,Rhinovirus B | — | FJ445187,DQ473487 |
| Human rhinovirus 36 | NC_001617 | vertebrates,human | 1 | Picornaviridae,Enterovirus,Rhinovirus A | — | DQ473505 |
| Human rhinovirus 37 | NC_001490 | vertebrates,human | 1 | Picornaviridae,Enterovirus,Rhinovirus B | — | EF173423 |
| Human rhinovirus 38 | NC_001617 | vertebrates,human | 2 | Picornaviridae,Enterovirus,Rhinovirus A | — | DQ473495,FJ445180 |
| Human rhinovirus 39 | NC_001617 | vertebrates,human | 1 | Picornaviridae,Enterovirus,Rhinovirus A | — | AY751783 |
| Human rhinovirus 4 | NC_001490 | vertebrates,human | 1 | Picornaviridae,Enterovirus,Rhinovirus B | — | DQ473490 |
| Human rhinovirus 40 | NC_001617 | vertebrates,human | 1 | Picornaviridae,Enterovirus,Rhinovirus A | — | FJ445129 |
| Human rhinovirus 41 | NC_001617 | vertebrates,human | 1 | Picornaviridae,Enterovirus,Rhinovirus A | — | DQ473491 |
| Human rhinovirus 42 | NC_001617 | vertebrates,human | 1 | Picornaviridae,Enterovirus,Rhinovirus A | — | FJ445130 |
| Human rhinovirus 43 | NC_001490 | vertebrates,human | 1 | Picornaviridae,Enterovirus,Rhinovirus B | — | FJ445131 |
| Human rhinovirus 44 | NC_001617 | vertebrates,human | 1 | Picornaviridae,Enterovirus,Rhinovirus A | — | DQ473499 |
| Human rhinovirus 45 | NC_001617 | vertebrates,human | 1 | Picornaviridae,Enterovirus,Rhinovirus A | — | FJ445132 |
| Human rhinovirus 46 | NC_001617 | vertebrates,human | 1 | Picornaviridae,Enterovirus,Rhinovirus A | — | DQ473506 |
| Human rhinovirus 47 | NC_001617 | vertebrates,human | 1 | Picornaviridae,Enterovirus,Rhinovirus A | — | FJ445133 |
| Human rhinovirus 48 | NC_001490 | vertebrates,human | 1 | Picornaviridae,Enterovirus,Rhinovirus B | — | DQ473488 |
| Human rhinovirus 49 | NC_001617 | vertebrates,human | 2 | Picornaviridae,Enterovirus,Rhinovirus A | — | FJ445134,DQ473496 |
| Human rhinovirus 5 | NC_001490 | vertebrates,human | 1 | Picornaviridae,Enterovirus,Rhinovirus B | — | FJ445112 |
| Human rhinovirus 50 | NC_001617 | vertebrates,human | 1 | Picornaviridae,Enterovirus,Rhinovirus A | — | FJ445135 |
| Human rhinovirus 51 | NC_001617 | vertebrates,human | 1 | Picornaviridae,Enterovirus,Rhinovirus A | — | FJ445136 |
| Human rhinovirus 52 | NC_001490 | vertebrates,human | 3 | Picornaviridae,Enterovirus,Rhinovirus B | — | FJ445137,EF173424,FJ445188 |
| Human rhinovirus 53 | NC_001617 | vertebrates,human | 1 | Picornaviridae,Enterovirus,Rhinovirus A | — | DQ473507 |
| Human rhinovirus 54 | NC_001617 | vertebrates,human | 2 | Picornaviridae,Enterovirus,Rhinovirus A | — | FJ445138,FJ445139 |
| Human rhinovirus 55 | NC_001617 | vertebrates,human | 1 | Picornaviridae,Enterovirus,Rhinovirus A | — | DQ473511 |
| Human rhinovirus 56 | NC_001617 | vertebrates,human | 1 | Picornaviridae,Enterovirus,Rhinovirus A | — | FJ445140 |
| Human rhinovirus 57 | NC_001617 | vertebrates,human | 1 | Picornaviridae,Enterovirus,Rhinovirus A | — | FJ445141 |
| Human rhinovirus 58 | NC_001617 | vertebrates,human | 1 | Picornaviridae,Enterovirus,Rhinovirus A | — | FJ445142 |
| Human rhinovirus 59 | NC_001617 | vertebrates,human | 1 | Picornaviridae,Enterovirus,Rhinovirus A | — | DQ473500 |
| Human rhinovirus 6 | NC_001490 | vertebrates,human | 1 | Picornaviridae,Enterovirus,Rhinovirus B | — | DQ473486 |
| Human rhinovirus 60 | NC_001617 | vertebrates,human | 1 | Picornaviridae,Enterovirus,Rhinovirus A | — | FJ445143 |
| Human rhinovirus 61 | NC_001617 | vertebrates,human | 1 | Picornaviridae,Enterovirus,Rhinovirus A | — | FJ445144 |
| Human rhinovirus 62 | NC_001617 | vertebrates,human | 1 | Picornaviridae,Enterovirus,Rhinovirus A | — | FJ445145 |
| Human rhinovirus 63 | NC_001617 | vertebrates,human | 1 | Picornaviridae,Enterovirus,Rhinovirus A | — | FJ445146 |
| Human rhinovirus 64 | NC_001617 | vertebrates,human | 2 | Picornaviridae,Enterovirus,Rhinovirus A | — | EF173417,FJ445181 |
| Human rhinovirus 65 | NC_001617 | vertebrates,human | 1 | Picornaviridae,Enterovirus,Rhinovirus A | — | FJ445147 |
| Human rhinovirus 66 | NC_001617 | vertebrates,human | 1 | Picornaviridae,Enterovirus,Rhinovirus A | — | FJ445148 |

| Taxonomy | NCBI Reference Sequence ID | Host | Lineage | No. of Genomes | Segment Count | Genbank Accession ID |
|---|---|---|---|---|---|---|
| Human rhinovirus 67 | NC_001617 | vertebrates,human | Picornaviridae,Enterovirus,Rhinovirus A | 1 | — | FJ445149 |
| Human rhinovirus 68 | NC_001617 | vertebrates,human | Picornaviridae,Enterovirus,Rhinovirus A | 1 | — | FJ445150 |
| Human rhinovirus 69 | NC_001490 | vertebrates,human | Picornaviridae,Enterovirus,Rhinovirus B | 1 | — | FJ445151 |
| Human rhinovirus 7 | NC_001617 | vertebrates,human | Picornaviridae,Enterovirus,Rhinovirus A | 2 | — | DQ473503,FJ445176 |
| Human rhinovirus 70 | NC_001490 | vertebrates,human | Picornaviridae,Enterovirus,Rhinovirus B | 1 | — | DQ473489 |
| Human rhinovirus 71 | NC_001617 | vertebrates,human | Picornaviridae,Enterovirus,Rhinovirus A | 1 | — | FJ445152 |
| Human rhinovirus 72 | NC_001490 | vertebrates,human | Picornaviridae,Enterovirus,Rhinovirus B | 1 | — | FJ445153 |
| Human rhinovirus 73 | NC_001617 | vertebrates,human | Picornaviridae,Enterovirus,Rhinovirus A | 1 | — | DQ473492 |
| Human rhinovirus 74 | NC_001617 | vertebrates,human | Picornaviridae,Enterovirus,Rhinovirus A | 1 | — | DQ473494 |
| Human rhinovirus 75 | NC_001617 | vertebrates,human | Picornaviridae,Enterovirus,Rhinovirus A | 1 | — | DQ473510 |
| Human rhinovirus 76 | NC_001617 | vertebrates,human | Picornaviridae,Enterovirus,Rhinovirus A | 2 | — | FJ445182,DQ473502 |
| Human rhinovirus 77 | NC_001617 | vertebrates,human | Picornaviridae,Enterovirus,Rhinovirus A | 1 | — | FJ445154 |
| Human rhinovirus 78 | NC_001617 | vertebrates,human | Picornaviridae,Enterovirus,Rhinovirus A | 2 | — | FJ445183,EF173418 |
| Human rhinovirus 79 | NC_001490 | vertebrates,human | Picornaviridae,Enterovirus,Rhinovirus B | 1 | — | FJ445155 |
| Human rhinovirus 8 | NC_001617 | vertebrates,human | Picornaviridae,Enterovirus,Rhinovirus A | 1 | — | FJ445113 |
| Human rhinovirus 80 | NC_001617 | vertebrates,human | Picornaviridae,Enterovirus,Rhinovirus A | 1 | — | FJ445156 |
| Human rhinovirus 81 | NC_001617 | vertebrates,human | Picornaviridae,Enterovirus,Rhinovirus A | 3 | — | FJ445159,FJ445158, FJ445157 |
| Human rhinovirus 82 | NC_001617 | vertebrates,human | Picornaviridae,Enterovirus,Rhinovirus A | 1 | — | FJ445160 |
| Human rhinovirus 83 | NC_001490 | vertebrates,human | Picornaviridae,Enterovirus,Rhinovirus B | 1 | — | FJ445161 |
| Human rhinovirus 84 | NC_001490 | vertebrates,human | Picornaviridae,Enterovirus,Rhinovirus B | 1 | — | FJ445162 |
| Human rhinovirus 85 | NC_001617 | vertebrates,human | Picornaviridae,Enterovirus,Rhinovirus A | 1 | — | FJ445163 |
| Human rhinovirus 86 | NC_001617 | vertebrates,human | Picornaviridae,Enterovirus,Rhinovirus A | 1 | — | FJ445164 |
| Human rhinovirus 88 | NC_001617 | vertebrates,human | Picornaviridae,Enterovirus,Rhinovirus A | 1 | — | DQ473504 |
| Human rhinovirus 89 | NC_001617 | vertebrates,human | Picornaviridae,Enterovirus,Rhinovirus A | 4 | — | FJ445166,M16248,FJ445165,FJ445184 |
| Human rhinovirus 9 | NC_001617 | vertebrates,human | Picornaviridae,Enterovirus,Rhinovirus A | 3 | — | FJ445114,FJ445177, FJ445115 |
| Human rhinovirus 90 | NC_001617 | vertebrates,human | Picornaviridae,Enterovirus,Rhinovirus A | 1 | — | FJ445167 |
| Human rhinovirus 91 | NC_001490 | vertebrates,human | Picornaviridae,Enterovirus,Rhinovirus B | 1 | — | FJ445168 |
| Human rhinovirus 92 | NC_001617 | vertebrates,human | Picornaviridae,Enterovirus,Rhinovirus A | 1 | — | FJ445169 |
| Human rhinovirus 93 | NC_001617 | vertebrates,human | Picornaviridae,Enterovirus,Rhinovirus A | 1 | — | EF173425 |
| Human rhinovirus 94 | NC_001617 | vertebrates,human | Picornaviridae,Enterovirus,Rhinovirus A | 2 | — | EF173419,FJ445185 |
| Human rhinovirus 95 | NC_001617 | vertebrates,human | Picornaviridae,Enterovirus,Rhinovirus A | 1 | — | FJ445170 |
| Human rhinovirus 96 | NC_001617 | vertebrates,human | Picornaviridae,Enterovirus,Rhinovirus A | 1 | — | FJ445171 |
| Human rhinovirus 97 | NC_001490 | vertebrates,human | Picornaviridae,Enterovirus,Rhinovirus B | 1 | — | FJ445172 |
| Human rhinovirus 98 | NC_001617 | vertebrates,human | Picornaviridae,Enterovirus,Rhinovirus A | 1 | — | FJ445173 |
| Human rhinovirus 99 | NC_001490 | vertebrates,human | Picornaviridae,Enterovirus,Rhinovirus B | 1 | — | FJ445174 |
| Human rhinovirus A | NC_001617 | vertebrates,human | Picornaviridae,Enterovirus,Rhinovirus A | 17 | — | GQ415051,JF285322, JF285324,JN837692, JF285321,JN798589, JN815250,JF285323, JQ747751,DQ473509, JN798583,JN798561, GQ415052,A10937, JN837697,JF285329, JN798556 |

| Taxonomy | NCBI Reference Sequence ID | Host | No. of Genomes | Lineage | Segment Count | Genbank Accession ID |
|---|---|---|---|---|---|---|
| Human rhinovirus B | NC_001490 | vertebrates,human | 9 | Picornaviridae,Enterovirus,Rhinovirus B | — | JN815239,JN798573, JF285330, JF285308, JF285309, JN 798588, JQ994497,JF285331, JQ245969 |
| Human rhinovirus B72 | NC_001490 | vertebrates,human | 1 | Picornaviridae,Enterovirus,Rhinovirus B | — | GU968948 |
| Human rotavirus (SEROTYPE 2/ STRAIN S2) | NC_011504 | vertebrates,human | 1 | Reoviridae,Rotavirus,Rotavirus A | seg. 10 | U59104 |
| Human rotavirus (STRAIN L26) | NC_011500 | vertebrates,human | 1 | Reoviridae,Rotavirus,Rotavirus A | seg. 5 | D38150 |
| Human rotavirus (STRAIN RV5) | NC_011504 | vertebrates,human | 1 | Reoviridae,Rotavirus,Rotavirus A | seg. 10 | U59103 |
| Human rotavirus (strain US1205) | NC_011504 | vertebrates,human | 1 | Reoviridae,Rotavirus,Rotavirus A | seg. 10 | AF079358 |
| Human rotavirus (strain US1205) | NC_011509 | vertebrates,human | 1 | Reoviridae,Rotavirus,Rotavirus A | seg. 6 | AF079357 |
| Human rotavirus (strain US1205) | NC_011510 | vertebrates,human | 1 | Reoviridae,Rotavirus,Rotavirus A | seg. 4 | AF079356 |
| Human rotavirus 1 strain RV4 | NC_011504 | vertebrates,human | 1 | Reoviridae,Rotavirus,Rotavirus A | seg. 10 | U59108 |
| Human rotavirus A | NC_011500 | vertebrates,human | 20 | Reoviridae,Rotavirus,Rotavirus A | seg. 5 | EF672557,JF766584, FJ423117,EF672620, FJ423139,AF190169, GU189555,Z32552, JF766595,EF672613, EF672592,U11492, FJ423156,JF766573, JF421981,L18943, D38151,HM627559, EF672564,FJ423128 |
| Human rotavirus A | NC_011501 | vertebrates,human | 95 | Reoviridae,Rotavirus,Rotavirus A | seg. 7 | JN706641,JF304934, FJ423141 ,EU984100, EF672572,EF672580, JN869275,JF304923, AY787648,EU520416, JN706640,AB741657, JN706620, JX946176,JN706620, FJ747622,JN706624, AF506014,JN706633, DQ005107,GU18955 7,JN706628,JN70662 3,JX946165,JN70663 9,JF766574,EF67258 6,AB748601,KC1397 87,AF506018,KC149 936,EF672579,JQ863 317,EF67622,EF672 |

| Taxonomy | NCBI Reference Sequence ID | Host | No. of Genomes | Lineage | Segment Count | Genbank Accession ID |
|---|---|---|---|---|---|---|
| | | | | | | 615,JN706622,JX416216,AF506293,EF672607,JQ087442,JN869276,EF554133,EF672573,EF672600,HQ641361,JN706638,JQ873650,JQ087431,EF554100,EF672594,EU200800,JN706625,JN869272,AB022770,EF672601,JN706627,JF804986,JX307623,JX307626,EF554089,DQ005118,FJ423151,JF421983,JF766585,G0414548,FJ766766,JF747633,JX567766,JX416224,JX307624,HM627560,KC149929,JQ087453,EF672608,EU520415,FJ423130,JN104617,JN706626,EF672566,JN706634,EF554122,JX307625,JN869274,EF554111,HQ641370,JN869277,JN706637,JX416209,JF766596,JX509932,EF672587,JN869273,EF672559,JN706621,JN706635,JN706631 |
| Human rotavirus A | NC_011502 | vertebrates,human | 113 | Reoviridae,Rotavirus,Rotavirus A | seg. 8 | JX307619,EF554090,JQ715661,AB022771,JF421982,JN706613,JX307621,FJ423120,FJ747621,AF338246,JN706605,JN706619,HQ702225,EF672593,EF672565,JN706614,FJ423131,AF338248,AB748596,JN104624,EF672621,AF190172,HQ025982,HQ641360,EF672614,AF190170,EF554123,HQ702247,FJ423152,JX567765,AF190171,X81435,AB771768,EF554112 |

| Taxonomy | NCBI Reference Sequence ID | Host | No. of Genomes | Lineage | Segment Count | Genbank Accession ID |
|---|---|---|---|---|---|---|
| | | | | | | JN706603,JQ898159,JX416208,HQ02598 1,GU189556,JX9461 75,JQ713649,JX4162 23,JN706606,HQ670 643,HQ702258,HQ64 1369,EU984099,JN70 6598,JN706616,AB77 1753,JN706604,JX94 6164,KC149935,AY7 87649,KC139786,JQ 715664,JF304922,JN 706601,HM622561,J F766597,JN706617,E U200801,AF506015, DQ005117,JN706610 ,JN706602,JX307620 ,JX416215,EU868888 ,DQ005106,JQ86331 6,HQ702236,FJ42314 2,HQ702214,X81428, JF766575,JQ715662, HQ670636,GQ41454 7,JN706611,JN70661 5,AB771770,JN70659 9,JF766586,AB77176 4,X81433,X76645,X8 1425,JN706609,JX30 7622,X81434,JN7066 12,JN706608,JN1046 16,AB741656,EF5541 01,JF304933,EF6725 58,JQ715663,EF5541 34,KC149928,AF506 019,JQ715660,AF338 247,AF541920,X8142 7,FJ747632,JN70660 0,X81437,JX509931,J N706607,JN706618,X 81436 |
| Human rotavirus A | NC_011503 | vertebrates,human | 622 | Reoviridae,Rotavirus,Rotavirus A | seg. 9 | JF965002,JN706202, JX458968,JQ710665, GQ414545,GQ99689 6,JN706564,DQ8736 78,JN706267,AB5345 36,JX946173,FJ4475 67,JN706204,JN7065 54,AF260949,JN7065 |

| Taxonomy | NCBI Reference Sequence ID | Host | No. of Genomes | Lineage | Segment Count | Genbank Accession ID |
|---|---|---|---|---|---|---|
| | | | | | | 66,JXQ88016,JF9650 04,AB527037,JN7062 12,JXQ88013,HQ702 259,AB527030,FJ948 854,JX509940,JN706 275,JXQ88018,AB534 532,JN706251,JN706 346,JN706559,AB527 009,JQ043268,JN706 227,FJ152132,AB527 023,HQ738627,FJ529 386,JN706238,GU37 7172,FJ948849,JN70 6210,JF965010,AB18 0969,JQ043273,JN70 6218,AJ278254,JN70 6352,JN706327,JN70 6334,AB527027,AB5 34530,FJ948843,GQ 996882,JX458962,JN 706215,JN706270,X6 3156,DQ923801,EU6 79389,JN706345,JQO 43276,JX458955,JN7 06377,AB527034,JN7 06299,DQ062126,AB 530270,IQ253576,JN 706230,JN706304,AB 527033,AB527014,JF 965000,DQ440616,G U377151,JXQ88009,J X470504,JQ289117,J X470511,DQ062128, DQ099750,JX567752 ,AB527019,EF672595 ,JN706310,FJ529395, EU791924,AB534535 ,JN706278,AB527029 ,JN706338,AB527029 ,JN706338, JF766605,JQ043267, EF672574,JF813102, AB118024,HQ537522 ,JN706367,JN706563 ,JN706203,JQ043277 ,DQ873679,AF17083 7,AB530268,EF67260 2,JN706336,JN70624 9,JF965005,HQ53751 |

-continued

| Taxonomy | NCBI Reference Sequence ID | Host | No. of Genomes | Lineage | Segment Count | Genbank Accession ID |
|---|---|---|---|---|---|---|
| | | | | | | 7,HQ702237,AY6295 |
| | | | | | | 60,FJ948833,JQ2535 |
| | | | | | | 67,DQ873672,AB527 |
| | | | | | | 015,JQ710675,JN706 |
| | | | | | | 262,AB527035,HQ73 |
| | | | | | | 8621,FJ447570,JN70 |
| | | | | | | 6229,EU679390,JN70 |
| | | | | | | 6351,GU377136,JQ2 |
| | | | | | | 53573,JN706309,AF2 |
| | | | | | | 60939,GQ398012,JF |
| | | | | | | 964999,EF672609,JN |
| | | | | | | 706370,JX470508,JQ |
| | | | | | | 710671,FJ948836,JN |
| | | | | | | 706348,JN706295,AF |
| | | | | | | 260942,JX458964,AF |
| | | | | | | 260941,FJ423132,FJ |
| | | | | | | 423143,AF260958,JN |
| | | | | | | 706224,GU377144,J |
| | | | | | | N706353,FJ747630,E |
| | | | | | | F077484,AB527025,J |
| | | | | | | X458966,AF260943,J |
| | | | | | | N706317,AF170834,J |
| | | | | | | N706306,JQ710662, |
| | | | | | | DQ099748,JX103956 |
| | | | | | | ,JN706302,JN706341 |
| | | | | | | ,AY787646,JN706231 |
| | | | | | | ,JX470510,EF672567 |
| | | | | | | ,EU679391,JN706291 |
| | | | | | | ,JN706556,KC242226 |
| | | | | | | ,GQ117003,AF38691 |
| | | | | | | 5,EU805775,JN70632 |
| | | | | | | 8,AF274971,JF81310 |
| | | | | | | 6,JN706319,JQ25357 |
| | | | | | | 2,AB527041,DQ8736 |
| | | | | | | 73,GQ452924,FJ423 |
| | | | | | | 121,JN706240,JN706 |
| | | | | | | 232,JN706258,JF964 |
| | | | | | | 998,JQ710676,AF260 |
| | | | | | | 936,JN706314,JQ253 |
| | | | | | | 574,DQ099753,GU37 |
| | | | | | | 7148,JX567748,JX47 |
| | | | | | | 0506,AB534526,JN70 |
| | | | | | | 6378,GU377133,JX4 |
| | | | | | | 70513,HQ702248,L21 |
| | | | | | | 666,JN706308,JX103 |
| | | | | | | 957,JQ253564,JN706 |
| | | | | | | 343,HQ738577,JN70 |
| | | | | | | 6361,GQ996884,JQO |

-continued

| Taxonomy | NCBI Reference Sequence ID | Host | No. of Genomes | Lineage | Segment Count | Genbank Accession ID |
|---|---|---|---|---|---|---|
| | | | | | | 43270,AY206861,JN706364,JN706245,FJ948829,JN706558,GQ996892,JF304931,JF965009,JN706239,AF143690,FJ915079,AB527006,GQ996890,KC841471,AB534533, AB530267,JN706255, AB534520,EU679392 ,AB527022,JX567750 ,DQ122400,JXQ8801 9,JN706359,AB52704 0,AF143689,JQ25356 3,JN706329,GU3771 74,AY856443,JXQ880 12,JN706305,DQ099 749,DQ873670,JN70 6199,AF274969,AB52 7043,DQ099751,GQ3 98018,HQ537521,JN 706219,JN706266,JN 706294,JX458958,JQ 710669,JN706344,G 0117005,JN706372,J N706246,AB669005, AB527028,JN706318, JN706326,AY456382, JX470512,AF143688, FJ948838,JXQ88020, JN706248,EF554109, JN706300,JQ818169, DQ017650,JQ710673 ,JN706303,JX567753 ,DQ873676,JQ04327 1,JN706313,JN70636 0,AB527020,JN70623 3,DQ111868,AB5270 21,AF260948,JX4705 05,DQ062123,FJ7476 19,AB534522,JX4589 54,GU377164,JQ253 569,JN706254,JXQ88 015,EF672616,JN706 311,EU200798,AB52 7042,JN706339,HQ7 02226,JF965008,GU3 77142,JN706222,DQ |

-continued

| Taxonomy | NCBI Reference Sequence ID | Host | No. of Genomes | Lineage | Segment Count | Genbank Accession ID |
|---|---|---|---|---|---|---|
| | | | | | | 099746,AB530266,AF260935,JN706366,JN706369,GQ996849,G0452923,JX567751,J0043278,JF742651,JN706574,GQ996891, JN706358,HQ738583,JN706330,JQ710677,JN706337,AB530269,AB530274,JN706312,AB527031,JN706323,HQ537513,JN706373,JN706321,JN706626 8,AB534531,JQ710664,JN706217,AB180970,JN706264,AB741654,AB534523,GQ996867,AF500235,DQ062130,JX458959,JQ863314,JX307591,GQ452926,JN706253,JN706237,HQ702215,JN706206,GU377135,EF088831,AB534521,FJ152121,JN706261,FJ915078,JN706211,GU377166,JN706220,HM627558,JN706247,JF719063,DQ062124,JN706276,FJ948839,JQ253570,GQ996925,JX458965,AF438228,JN706228,JN706208,JN706567,EF159575,JN706242,JN706315,JF965001,JQ710666,HQ537514,EF67256 0,AB534534,JQ71067 4,JF965006,HQ53751 2,JN706292,AB52701 6,FJ915077,AF15961 0,JQ710670,HQ7386 20,FJ948837,AB5270 24,JN706322,JN7063 31,AB527011,JF9650 03,AJ311738,AB5270 17,AB527038,AB530 273,JN706201,JN706 |

| Taxonomy | NCBI Reference Sequence ID | Host | No. of Genomes | Lineage | Segment Count | Genbank Accession ID |
|---|---|---|---|---|---|---|
| | | | | | | 252,DQ099747,AF26 0934,JN706565,AB52 7045,AY631125,GU3 77169,JN706221,JXQ 88014,FJ423153,FJ5 29385,JQ710667,JN7 06560,AB669013,FJ9 48831,JN706307,JN7 06347,AF260959,GQ 996894,AF260957,AF 450293,FJ948853,JN 706374,JN706250,JN 706257,JX307594,G U377145,AB527008,J N706320,JN706223,A F260940,EU984109,J N706362,FJ529383,D 0099754,EF672623, AF260937,JX470507, JN706335,JN706357, JQ253571,AB534527, AB534524,JX458956, JN706333,JN706355, JN706324,JN706236, GQ996883,JN706259 ,JF304920,AB527044 ,GQ996885,JN70620 7,JQ253575,JN70637 9,JN706562,GQ9968 87,JX458960,JN7062 43,JN706214,JN7063 63,EU679394,DQ062 127,JN706575,JN706 568,JX458953,JX307 593,HQ738579,JN70 6296,JN706569,AB53 4528,EF088832,AB52 7007,JN706256,AF50 1580,AB669009,JQ71 0672,GQ996889,AF1 70836,JN706279,FJ9 48845,HQ738622,AF 260946,FJ915094,U0 4350,AB527018,JN70 6350,JN706325,DQ0 62129,AF260933,FJ9 48847,JQ043269,DQ 099752,HQ537519,A |

-continued

| Taxonomy | NCBI Reference Sequence ID | Host | No. of Genomes | Lineage | Segment Count | Genbank Accession ID |
|---|---|---|---|---|---|---|
| | | | | | | F26938,JN706200,JN706293,JN706265,J0253566,GQ996893, |
| | | | | | | GU377155,JN706571,JX567749,AB530271,FJ948832,AB527039,DQ873669,DQ873671,DQ117937,JQ253568,JQ253562,GQ117006,JX110838,JX458967,JN706557,JN706572,JN706356,AB530272,JXQ88011,JN706375,JN706301,GU377159,GQ996886,AB527012,KC139779,JQ710668,JQ713096,JX458961,AB534525,JX470509,AB669017,G0117002,DQ873677,JN706235,AF409087,DQ117938,JN706332,JN706561,JN706371,JN706244,AY003871,GQ996888,JN706205,JN706365,FJ44756 8,JN706213,AF170835,JN706354,JQ34321 9,JQ043274,GQ3980 14,AF260947,JN706368,JF421980,FJ94488 51,AF260944,FJ94488 48,JN706573,JN706570,JF965007,JX3075 92,JN706225,JN706349,AF274970,GQ996926,EF672588,AB180974,JX458957,AB527013,AF260945,JN706263,AJ278257,JN706555,JF766594,FJ152110,M58290,JN706209,JN706226,DQ017649,GQ117004,JX458963,JF766583,GU377143,JXQ88017,EF159576,JN706269,JN706340,HQ738628,EU67 |

| Taxonomy | NCBI Reference Sequence ID | Host | No. of Genomes | Lineage | Segment Count | Genbank Accession ID |
|---|---|---|---|---|---|---|
| | | | | | | 9393,JN706216,DQ117939,AY630924,AB527046,JQ043275,JN706271,JXQ88008,D0062125,JQ710663,JN706376,JQ043272,AF438227,GQ452927,JN706297,AB527010,GQ996895,JQ04326,6,GQ117001,JN706342,JN706198,GU377147,JXQ88010,AB527036,JN706260,DQ923797,HQ537518,JN706316,JN706298,JQ253565,AB527032,AB534529,AB527026,EF672581,GU377134,FJ948830,FJ948855,GU377150,JN706234,G0996847 |
| Human rotavirus A | NC_011504 | vertebrates,human | 294 | Reoviridae,Rotavirus,Rotavirus A | seg. 10 | EF672596,JQ043306,AJ236783,GQ465013,AJ400644,AF469676,AJ236755,AJ311732,GQ465018,GQ46502 4,JX307628,AY78765 0,AJ236750,AB23270 0,JX458984,AB32696 2,GQ465019,AB3612 76,JF766576,AY6015 42,EF554113,EF6725 68,GQ465021,AJ400 634,EF159572,AB196 491,AB741658,GQ46 5037,JQ043300,HQ6 41371,AF170833,AB3 26337,FJ915085,AJ4 27314,AY576006,JQO 43311,JN706655,JF7 66587,AY601545,AJ2 36756,JN706657,AJ2 36784,AJ236749,GQ 465034,JF304935,AF 284778,AB022772,JF 813103,AB748606,JX 458977,AB361279,JX 946177,EF159573,D0996847 |

-continued

| Taxonomy | NCBI Reference Sequence ID | Host | No. of Genomes | Lineage | Segment Count | Genbank Accession ID |
|---|---|---|---|---|---|---|
| | | | | | | 029876,FJ152114,E U679381,AB211988, AJ400636,JN706644, D89873,GQ465020,J X307629,AJ236777,H M235509,GQ465028, JN706646,EU679378, FJ152136,GQ465026 ,AB326336,EF672575 ,JQ043302,AF541921 ,EF672603,DQ92380 3,AB762778,AB1969 59,EU659855,AB0O8 217,FJ423144,JN706 650,JX458980,AF469 679,GU189558,AF26 0928,AF284777,AJ40 0638,AF170831,JQ04 3308,JX458982,JF42 1984,AJ278252,AJ40 0635,JX307630,JF80 4998,JQ898161,GQ4 65015,AJ236775,FJ4 23133,AB196958,AB 201459,GQ465006,J X307627,AB361282, AB326343,HM627562 ,JN706642,AB213392 ,EF159574,JN104626 ,GQ465017,AJ23677 1,GQ465036,AB1964 92,FJ915088,AJ4273 16,JN706653,AF1708 30,JN706660,EU6793 77,AY629562,JX4589 69,GQ465031,AB326 339,AF200225,AY601 540,U59106,AJ23677 6,EF089269,JN10461 8,FJ423154,JN70666 1,JX458975,JX45897 0,GQ465032,JQ8633 18,EF672589,GQ465 007,KC139788,AJ236 778,FJ685615,GQ46 5022,EU791925,AB2 11992,AF506291,JQO 43312,JF81310 7,GQ |

| Taxonomy | NCBI Reference Sequence ID | Host | No. of Genomes | Lineage | Segment Count | Genbank Accession ID |
|---|---|---|---|---|---|---|
| | | | | | | 465005,AJ427313,AB213391,AF506016,JN706648,EU984101,AJ236770,JQ043304,G0414549,AB326334,JX458978,JX416225,AY601544,AJ400637,EF554135,JN706662,GU138211,AB326348,JN706658,AB303218,AB326340,EU679382,FJ152125,JN706645,DQ005116,KC890886,U59107,D88830,GQ465023,EU679379,JX458974,JQ713651,AJ400641,D10772,KC890884,JN706647,HQ641362,EU679380,GQ465035,DQ639954,AF469678,JX458976,JQ043305,AB326297,KC890885,AB211987,JQ898160,FJ915087,GQ465025,GQ465010,EF672624,JX458981,JF766598,AB21199l,AB763972,D88829,GQ465009,JN706663,JX458973,KC890882,JN706651,AY601541,AJ236752,AJ236765,AF260929,AB361284,KC890883,AF200224,FJ747634,EF672561,KC890887,AJ400640,AB326969,JX458983,FJ423122,EF672617,JN706643,AB361289,GQ465016,DQ92379 9,GQ465014,AB326286,JN706659,AF469677,AJ400643,AJ236779,AJ400639,JN706654,JQ043310,AJ236785,EF554091,JN706656,GU592516,JQ043309,GQ465011,JN70 |

| Taxonomy | NCBI Reference Sequence ID | Host | No. of Genomes | Lineage | Segment Count | Genbank Accession ID |
|---|---|---|---|---|---|---|
| | | | | | | 6652,AF284780,AJ42 7315,FJ747623,AJ23 6753,EF672582,AJ23 6781,JX458972,GQ4 65008,GQ465030,DQ 005105,AB326965,AF 260930,JX458971,AB 326338,JX567767,EF 672610,GQ465029,G 0465033,AF284776, AJ400642,GQ465012 ,U59110,AJ236780,G 0465027,JF804987,A J236751,AB211989,A B361288,JQ043303,A B326342,JN706649,A B326345,AY601543, AJ236754,AJ236782, JX458979,EF554124, EF554102,D10771,A B326344,JF805008,A F170832,AB211990,J Q043301,EU200802, JF304924,FJ915086, AB361277,AJ278255, JX946166,JQ043307 |
| Human rotavirus A | NC_011505 | vertebrates,human | 126 | Reoviridae,Rotavirus,Rotavirus A | seg. 11 | EF590982,GQ414550 ,JN872347,AB008659 ,EF590987,JN706677 ,JX946167,EF672569 ,KC139789,AB04521 8,EU200803,AB0086 62,JN706673,HM627 563,U54772,FJ42312 3,JQ043322,EF67259 0,JQ043320,JN70667 5,FJ747635,EF59098 8,EF672576,JF76658 8,JN869288,JQ71568 0,FJ423145,JN70667 8,EF590983,JQ04332 3,KC149937,AB0086 63,JX946178,FJ7476 24,AB035708,EF6725 83,GU189559,AB008 657,EF590981,EF590 680,EF554125,EF590 980,JN706664,JN869 |

| Taxonomy | NCBI Reference Sequence ID | Host | No. of Genomes | Lineage | Segment Count | Genbank Accession ID |
|---|---|---|---|---|---|---|
| | | | | | | 287,AF508732,AB763974,AB008664,AB008656,EF554114,U5473,AY841126,JN706685,AB008658,AY033396,EF554136,JN706679,AB045219,JN706665,AF338245,HQ025986,AY787651,AB008660,KC149930,HQ670638,U96698,FJ423134,EF590990,AF338244,M33607,EF590991,AY803730,AB -continued

| Taxonomy | NCBI Reference Sequence ID | Host | No. of Genomes | Lineage | Segment Count | Genbank Accession ID |
|---|---|---|---|---|---|---|
| | | | | | | 724,DQ005113,EF55 4083,EF583026,HQ6 70633,JX416219,JN7 06469,EF583034,EF5 83022,EF583030,JN7 06487,JF421976,JN7 06477,JX416212,JF7 66590,FJ423114,EF5 83014,EU200794,JX9 46169,EF583038,JN7 06483,JN706478,JN7 06467,EF554116,DQ 862063,AB022766,JX 416205,JN706468,JF 766601,EF583046,FJ 423147,FJ423136,JX 946160,JX509936,EF 583042,EF554127,JN 104612,JN706471,JN 706484,JN706473,JN 706486,EF583018,FJ 747626,JQ713646,JN 706485,JN706480,AY 787652,JN706470,JN 706479,JN706481,EF 554094,AB741650,D 0005124,JN706474, KC139782,JN706466, HQ025975,EF554105 ,JQ863310,JN706475 ,JN706482,JN706472 |
| Human rotavirus A | NC_011507 | vertebrates,human | 81 | Reoviridae,Rotavirus,Rotavirus A | seg. 1 | JX946159,JN706448, EF583017,JQ713645, EF583037,HQ702218 ,JN706449,JX416204 ,JF421975,JN706444, DQ005125,EU200793 ,EU984103,JN706445 ,HQ702229,FJ747625 ,HM627553,JF76658 9,JN706453,JX56776 0,JN706465,EF55412 6,JN706451,HQ7022 51,AY787653,JN7064 61,HQ702240,HQ025 973,JN706462,JN706 454,HQ025974,JF766 578,JN706452,HQ67 |

| Taxonomy | NCBI Reference Sequence ID | Host | No. of Genomes | Lineage | Segment Count | Genbank Accession ID |
|---|---|---|---|---|---|---|
| | | | | -continued | | |
| | | | | | | 0639,JN706457,FJ42 3146,JN706460,FJ42 3113,JF766600,JQ86 3309,KC139781,JN70 6464,AB022765,JN70 6459,HQ702207,JF30 4915,EF554104,JX41 6218,JN104619,JN10 4611,JN706450,DQO 05114,EF583033,JN7 06447,AB741649,FJ4 23135,HQ641355,FJ4 23124,HQ670632,JN 706458,GU189551,E F583041,JX416211,J N706455,FJ747613,E F554082,EF554093,H 0641364,JN706456,J N706446,EF583021, EF583045,GQ414540 ,JX946168,EF554115 ,EF583029,JN706463 ,JX509935,EF583049 ,EF583025,JF304926 |
| Human rotavirus A | NC_011508 | vertebrates,human | 86 | Reoviridae,Rotavirus,Rotavirus A | seg. 3 | EF554117,JN706489, AY277919,JX946170, JF766602,FJ747627, JF421977,EF554095, AY277918,EF583035, JF766591,HQ670634, AB022767,AY277914 ,JQ863311,JX416213 ,JF554084,HQ64135 7,JN104613,AY27791 7,EF583015,DQ0051 12,JN706509,HQ670 641,KC139783,JN706 494,HQ641366,FJ423 115,JN706503,JX946 161,DQ005123,JN70 6491,JN706502,HQ0 25977,FJ423126,EF5 83039,EF583031,JN7 06488,EU984105,EF 583023,JN706493,FJ 747615,AY277915,JN 706496,JN706499,EF 554106,JN706504,EF |

-continued

| Taxonomy | NCBI Reference Sequence ID | Host | No. of Genomes | Lineage | Segment Count | Genbank Accession ID |
|---|---|---|---|---|---|---|
| | | | | | | 583019,JF304917,HQ025978,JN706506,JN104621,JN706490,EF583047,AY277920,EF583051,AB733135,EF583027,JF766580,JX567762,AY277916,EF583043,JN706501,JX416220,AY267335,EF554128,GQ414542,HM627555,JQ713647,JN706498,JF304928,JX416206,EU200795,JN706500,JN706492,JN706497,JX509937,FJ423137,GU189553,JN706495,JN706507,JN706508,FJ423148,AB741651,AY787654,JN706505 |
| Human rotavirus A | NC_011509 | vertebrates,human | 315 | Reoviridae,Rotavirus,Rotavirus A | seg. 6 | JQ818154,JN706538,GU390418,HM627557,JF421979,GU390452,EU372724,JQ230099,JQ230080,FJ152109,JQ043298,GU390443,EU372726,JX307599,JN706544,HQ738601,JQ230065,FJ685614,EU372746,GU390414,EF426129,JQ230082,JQ230070,EF426136,GU390438,AY601554,EF583040,EU556221,EU372748,EF426139,HQ445977,GU390425,KC149926,FJ747617,JF304919,EU372745,GU390453,HQ445975,JQ230083,JN706535,EF583016,JQ230066,HQ611018,AY787645,AY601552,AY601550,JX567763,JQ863313,EU372732,JQ230090,KC890877,EU984108,FJ152120,GU390448, |

| Taxonomy | NCBI Reference Sequence ID | Host | No. of Genomes | Lineage | Segment Count | Genbank Accession ID |
|---|---|---|---|---|---|---|
| | | | | | | AF260931,JQ818153, GU390432,EF426137 ,GU390440,JX94617 2,EF426124,EU3727 25,EU372738,HQ611 009,JX307600,JQ230 086,JQ230101,AF531 912,HQ611032,JN70 6546,GU390423,HQ6 10999,HQ611022,JQ 818168,EF583028,H 0738589,HQ611003, AY601551,HQ611006 ,EU679384,JQ23006 4,JQ230068,GU3904 50,EF426122,JQ0432 94,GU390416,JQ230 072,JQ230061,J

| Taxonomy | NCBI Reference Sequence ID | Host | No. of Genomes | Lineage | Segment Count | Genbank Accession ID |
|---|---|---|---|---|---|---|
| | | | | | | 23009A,JX416207,H Q611017,GU390430, JQ043296,JQ230059, JQ230084,HQ738595 ,JF766604,KC890878 ,JQ818151,HQ61102 7,EU372736,HQ7385 99,HQ611019,HQ611 016,HQ738591,EU67 9388,EU372742,AF3 09652,EU372731,JN7 06550,JN706536,JF3 04930,EU372728,GU 390427,EU679383,A Y601549,JQ230095,J N706542,HQ445978, EU372733,HQ611033 ,JN706551,JQ230085 ,EF426125,HQ61100 0,DQ005121,JQ2300 79,JN706548,HQ738 593,HQ611008,JQ23 0073,JQ230071,GU3 90454,GU390429,EF 426134,HQ611010,G U390449,JQ230062,J N706533,JQ818152, EF583048,JX946162, EU372739,JN706545, JQ818155,HQ611007 ,HQ738594,HQ61099 8,JQ230060,HQ7385 88,EF426132,AB7416 53,KC139784,HQ738 596,GU390433,HQ64 1358,DQ923796,EF5 54108,EU372737,GU 390444,JQ230069,G U390460,X94617,GQ 414544,FJ423140,EU 372741,GU390431,E F426135,GU390447,J 0230087,JN706552,J F766582,GU390428,J 0230096,JQ230074,J N706541,EF426121, HQ611024,EF554119 ,GU390434,EU20079 |

| Taxonomy | NCBI Reference Sequence ID | Host | No. of Genomes | Lineage | Segment Count | Genbank Accession ID |
|---|---|---|---|---|---|---|
| Human rotavirus A | NC_011510 | vertebrates,human | 68 | Reoviridae,Rotavirus,Rotavirus A | seg. 4 | 7,EU372740,HQ7385 92,HQ738585,EF583 044,HQ611002,AY60 1553,GU390455,JN7 06534,EU372729,KC 89088,EF583052,E U372749,U04741,JN 104622,JQ087449,E U372734,JQ230098, EU372735,EU679386 ,EF583032,EF426127 ,GU390446,HQ64136 7,JN706553,FJ74762 9,GU390436,FJ42312 9,JN706540,HQ6110 30,JX307601,GU390 458,HQ611012,JQ23 0091,KC890879,JN70 6549,JQ230067,JQ23 0075,EF554086,EF42 6123,EU791923,EF5 83024,EU556222,EU 556223,FJ152131,JN 706537,JQ043293,H 0738600,GU390457, EF554130,KC890876 ,HQ738590,HQ61100 4,JX307602,EF55409 7,AF531913,GU3904 56,X94618,GU59251 5,FJ423150,HQ61101 5,JQ087438,EU3727 44,EF583020,GU390 435,GU390459,JQ81 8167,JX416221,EF42 6133,EU679387,KC8 90880,JQ230058,HO 445976,GU390437,E U330646,JN706539,J 0230076 AY787644,FJ423116, EF672577,KC139780 ,EU679398,HQ44596 7,EF554118,EF67261 2,HM627556,HQ4459 69,JF766581,EF5541 29,L33895,EU679399 ,L19712,JF421978,D |

| Taxonomy | NCBI Reference Sequence ID | Host | No. of Genomes | Lineage | Segment Count | Genbank Accession ID |
|---|---|---|---|---|---|---|
| Human rotavirus A RMC/G60 | NC_011503 | vertebrates,human | 1 | | | 0887060,JF766592,E U679395,D14032,GQ 398013,EF672591,G U320751,FJ435210,E F672584,JQ863312,U 16299,EF672570,FJ4 23127,EU984107,D3 8054,EF554096,JF76 6603,GU189554,M60 600,L34161,GQ4145 43,FJ747628,GQ453 422,AB741652,FJ435 205,AF531909,FJ423 138,FJ423149,EF672 563,M58292,HM6275 45,D38052,EF672605 ,GQ452950,EF67255 6,EF554107,EU8057 73,FJ747616,EF6725 98,EU984106,HQ445 970,AF260932,EF672 619,U07753,JN70651 0,GQ452951,EU6793 96,AB077766,HQ738 572,AF523677,EU67 9397,EU679400 |
| Human rotavirus A RMC/G66 | NC_011503 | vertebrates,human | 1 | Reoviridae,Rotavirus,Rotavirus A | seg. 9 | AY603151 |
| Human rotavirus A RMC/G7 | NC_011503 | vertebrates,human | 1 | Reoviridae,Rotavirus,Rotavirus A | seg. 9 | AY603152 |
| Human rotavirus A RMC437 | NC_011503 | vertebrates,human | 1 | Reoviridae,Rotavirus,Rotavirus A | seg. 9 | AY603150 |
| Human rotavirus A RMC61 | NC_011503 | vertebrates,human | 1 | Reoviridae,Rotavirus,Rotavirus A | seg. 9 | AY603153 |
| Human rotavirus A strain CMH222 | NC_011504 | vertebrates,human | 1 | Reoviridae,Rotavirus,Rotavirus A | seg. 9 | AY603149 |
| Human rotavirus A strain CMH222 | NC_011509 | vertebrates,human | 1 | Reoviridae,Rotavirus,Rotavirus A | seg. 10 | DQ288660 |
| Human rotavirus A strain RMC100 | NC_011510 | vertebrates,human | 1 | Reoviridae,Rotavirus,Rotavirus A | seg. 6 | DQ288659 |
| Human rotavirus AU-1 | NC_011541 | vertebrates,human | 1 | Reoviridae,Rotavirus,Rotavirus A | seg. 11 | AF373605 |
| Human rotavirus B | NC_021541 | vertebrates,human | 1 | Reoviridae,Rotavirus,Rotavirus B | seg. 4 | D10970 |
| Human rotavirus B | NC_021542 | vertebrates,human | 1 | Reoviridae,Rotavirus,Rotavirus B | seg. 1 | EU490415 |
| Human rotavirus B | NC_021543 | vertebrates,human | 1 | Reoviridae,Rotavirus,Rotavirus B | seg. 9 | AY238385 |
| Human rotavirus B | NC_021544 | vertebrates,human | 1 | Reoviridae,Rotavirus,Rotavirus B | seg. 4 | AY238388 |
| Human rotavirus B | NC_021545 | vertebrates,human | 1 | Reoviridae,Rotavirus,Rotavirus B | seg. 6 | AY238389 |
| Human rotavirus B | NC_021546 | vertebrates,human | 1 | Reoviridae,Rotavirus,Rotavirus B | seg. 2 | AY238390 |
| Human rotavirus B | | vertebrates,human | 1 | Reoviridae,Rotavirus,Rotavirus B | seg. 5 | AY238391 |

-continued

| Taxonomy | NCBI Reference Sequence ID | Host | No. of Genomes | Lineage | Segment Count | Genbank Accession ID |
|---|---|---|---|---|---|---|
| Human rotavirus B | NC_021547 | vertebrates,human | 1 | Reoviridae,Rotavirus,Rotavirus B | seg. 7 | AY238392 |
| Human rotavirus B | NC_021548 | vertebrates,human | 1 | Reoviridae,Rotavirus,Rotavirus B | seg. 8 | AY238393 |
| Human rotavirus B | NC_021549 | vertebrates,human | 1 | Reoviridae,Rotavirus,Rotavirus B | seg. 11 | AY238394 |
| Human rotavirus B | NC_021550 | vertebrates,human | 1 | Reoviridae,Rotavirus,Rotavirus B | seg. 10 | AY238384 |
| Human rotavirus B | NC_021551 | vertebrates,human | 1 | Reoviridae,Rotavirus,Rotavirus B | seg. 3 | EU490418 |
| Human rotavirus C | NC_007543 | vertebrates,human | 3 | Reoviridae,Rotavirus,Rotavirus C | seg. 6 | AY941780,AY941782,AY941781 |
| Human rotavirus C | NC_007544 | vertebrates,human | 3 | Reoviridae,Rotavirus,Rotavirus C | seg. 7 | AY820180,AY770977,AY820181 |
| Human rotavirus C | NC_007545 | vertebrates,human | 4 | Reoviridae,Rotavirus,Rotavirus C | seg. 9 | AY781283,JN969078,AY781284,AY770979 |
| Human rotavirus C | NC_007569 | vertebrates,human | 3 | Reoviridae,Rotavirus,Rotavirus C | seg. 10 | AY803727,AY803729,AY770978 |
| Human rotavirus C | NC_007570 | vertebrates,human | 22 | Reoviridae,Rotavirus,Rotavirus C | seg. 5 | AB499614,AM118019,AF325806,AB008672,AB533509,GU59251 9,AY795898,AY7709 80,AB533508,AF3258 05,AB533510,AB648 915,M94156,AM1180 20,AB533511,M9415 5,EF641110,AY78657 1,AB533512,AB5335 13,AY786570,AM118 018 |
| Human rotavirus C | NC_007571 | vertebrates,human | 44 | Reoviridae,Rotavirus,Rotavirus C | seg. 8 | AB086963,AF225563, AF225557,AB086968, AB086962,AF225555, AY803724,AF225553, AF225554,AF225561, D87543,AB004250,A F225552,AF225558,A B648916,AM118022, AF225556,AB086969, AF225560,AF323982, AF225560,AB281655 ,AB281654,AB281655 ,AY803726,AF225559 ,AM118021,AB08696 6,M61100,AY392446, AY803725,AF323979, AB499615,AB086964 ,AB281652,AB00867 1,AB086967,AF12047 8,EF641111,D87544, AB281651,AB281653 |

-continued

| Taxonomy | NCBI Reference Sequence ID | Host | No. of Genomes | Lineage | Segment Count | Genbank Accession ID |
|---|---|---|---|---|---|---|
| Human rotavirus C | NC_007572 | vertebrates,human | 20 | Reoviridae,Rotavirus,Rotavirus C | seg. 3 | ,AY392447,AF225562,AM118023,AB08696 5 AY395070,AB533526,AB008670,AM11802 5,AB533523,AB6489 17,AB533524,X79441,AB533521,AF323981,AY795897,AM11802 4,AY795896,AF32398 0,AY795895,AY3950 69,AB533525,AB499 613,AB533522,AM11 8026 |
| Human rotavirus C | NC_007573 | vertebrates,human | 6 | Reoviridae,Rotavirus,Rotavirus C | seg. 11 | AB499612,AB008673,AY941784,D88353,A Y770976,AY941783 |
| Human rotavirus G10P11 | NC_011504 | vertebrates,human | 1 | Reoviridae,Rotavirus,Rotavirus A | seg. 10 | AY527229 |
| Human rotavirus G10P[8] | NC_011502 | vertebrates,human | 1 | Reoviridae,Rotavirus,Rotavirus A | seg. 8 | AB714265 |
| Human rotavirus G10P[8] | NC_011506 | vertebrates,human | 1 | Reoviridae,Rotavirus,Rotavirus A | seg. 2 | AB714259 |
| Human rotavirus G10P[8] | NC_011508 | vertebrates,human | 1 | Reoviridae,Rotavirus,Rotavirus A | seg. 3 | AB714260 |
| Human rotavirus G12P[6] | NC_011510 | vertebrates,human | 3 | Reoviridae,Rotavirus,Rotavirus A | seg. 4 | EU839947,EU839946,EU839948 |
| Human rotavirus G1P6 | NC_011504 | vertebrates,human | 22 | Reoviridae,Rotavirus,Rotavirus A | seg. 10 | AF173181,AF173180, AF173182,AF173194, AF173183,AF173184, AF173191,AF173192, AF173179,AF173199, AF173187,AF173197, AF173188,AF173198, AF173193,AF173186, AF173189,AF173190, AF173195,AF173196, AF173200,AF173185 |
| Human rotavirus G1P8 | NC_011504 | vertebrates,human | 7 | Reoviridae,Rotavirus,Rotavirus A | seg. 10 | AF173207,AF173205, AF173201,AF173202, AF173203,AF173204, AF173206 |
| Human rotavirus G1P[8] | NC_011503 | vertebrates,human | 34 | Reoviridae,Rotavirus,Rotavirus A | seg. 9 | GU358423,HQ65087 6,HQ650871,GU3772 04,HQ650886,GU377 203,GU358420,GU35 8446,GU358438,HQ6 50872,GU377196,HQ 650882,GU358422,H Q358441, HQ650878,GU358844 |

| Taxonomy | NCBI Reference Sequence ID | Host | No. of Genomes | Lineage | Segment Count | Genbank Accession ID |
|---|---|---|---|---|---|---|
| Human rotavirus G1P[8] | NC_011510 | vertebrates,human | 4 | Reoviridae,Rotavirus,Rotavirus A | seg. 4 | 0,GU377198,GU358421,GU377201,HQ650881,GU358436,GU358429,GU377200,GU358443,GU358444,GU358442,HQ650879,GU358437,HQ650877,GU358445,GU358439,GU377205,HQ650883 |
| Human rotavirus G1P[8] | NC_011510 | vertebrates,human | 4 | Reoviridae,Rotavirus,Rotavirus A | seg. 4 | EU839957,EU839956,EU839955,EU839958 |
| Human rotavirus G2P4 | NC_011504 | vertebrates,human | 9 | Reoviridae,Rotavirus,Rotavirus A | seg. 10 | AF174298,AF174299,AF174304,AF174300,AF174301,AF174305,AF174302,AY527228,AF174303 |
| Human rotavirus G2P[4] | NC_011510 | vertebrates,human | 4 | Reoviridae,Rotavirus,Rotavirus A | seg. 4 | EU839950,EU839949,EU839951,EU83994 5 |
| Human rotavirus G2P[8] | NC_011510 | vertebrates,human | 1 | Reoviridae,Rotavirus,Rotavirus A | seg. 4 | EU839954 |
| Human rotavirus G3P[6] | NC_011504 | vertebrates,human | 1 | Reoviridae,Rotavirus,Rotavirus A | seg. 10 | EU734177 |
| Human rotavirus G3P[8] | NC_011502 | vertebrates,human | 5 | Reoviridae,Rotavirus,Rotavirus A | seg. 10 | AF173210,AF173212,AF173209,AF173211,AF173208 |
| Human rotavirus G4 strain St, Thomas 3 | NC_011503 | vertebrates,human | 1 | Reoviridae,Rotavirus,Rotavirus A | seg. 9 | X13603 |
| Human rotavirus G4 strain VA70 | NC_011504 | vertebrates,human | 1 | Reoviridae,Rotavirus,Rotavirus A | seg. 10 | U83798 |
| Human rotavirus G4P[8] | NC_011504 | vertebrates,human | 4 | Reoviridae,Rotavirus,Rotavirus A | seg. 10 | AF173214,EF011980,AF173215,AF173213 |
| Human rotavirus G5P[6] | NC_011503 | vertebrates,human | 1 | Reoviridae,Rotavirus,Rotavirus A | seg. 9 | AB257126 |
| Human rotavirus G9P6 | NC_011501 | vertebrates,human | 1 | Reoviridae,Rotavirus,Rotavirus A | seg. 7 | EU753969 |
| Human rotavirus G9P6 | NC_011502 | vertebrates,human | 1 | Reoviridae,Rotavirus,Rotavirus A | seg. 8 | EU753970 |
| Human rotavirus G9P6 | NC_011503 | vertebrates,human | 9 | Reoviridae,Rotavirus,Rotavirus A | seg. 9 | AF529871,AF529869,AF529868,AF529865,AF529870,AF529872,AF529867,AF529866,AF529864 |
| Human rotavirus G9P6 | NC_011504 | vertebrates,human | 1 | Reoviridae,Rotavirus,Rotavirus A | seg. 10 | EU753968 |
| Human rotavirus G9P6 | NC_011505 | vertebrates,human | 1 | Reoviridae,Rotavirus,Rotavirus A | seg. 11 | EU753967 |
| Human rotavirus G9P[6] | NC_011501 | vertebrates,human | 1 | Reoviridae,Rotavirus,Rotavirus A | seg. 7 | FJ183359 |
| Human rotavirus G9P[6] | NC_011502 | vertebrates,human | 1 | Reoviridae,Rotavirus,Rotavirus A | seg. 8 | FJ183361 |

-continued

| Taxonomy | NCBI Reference Sequence ID | Host | No. of Genomes | Lineage | Segment Count | Genbank Accession ID |
|---|---|---|---|---|---|---|
| Human rotavirus G9P[6] | NC_011503 | vertebrates,human | 5 | Reoviridae,Rotavirus,Rotavirus A | seg. 9 | FJ183360,AB364381, AB364371,AB364368 ,AB364372 |
| Human rotavirus G9P[6] | NC_011504 | vertebrates,human | 1 | Reoviridae,Rotavirus,Rotavirus A | seg. 10 | FJ183363 |
| Human rotavirus G9P[6] | NC_011505 | vertebrates,human | 1 | Reoviridae,Rotavirus,Rotavirus A | seg. 11 | FJ183362 |
| Human rotavirus G9P[6] | NC_011506 | vertebrates,human | 1 | Reoviridae,Rotavirus,Rotavirus A | seg. 2 | FJ183354 |
| Human rotavirus G9P[6] | NC_011507 | vertebrates,human | 1 | Reoviridae,Rotavirus,Rotavirus A | seg. 1 | FJ183353 |
| Human rotavirus G9P[6] | NC_011508 | vertebrates,human | 1 | Reoviridae,Rotavirus,Rotavirus A | seg. 3 | FJ183355 |
| Human rotavirus G9P[6] | NC_011509 | vertebrates,human | 1 | Reoviridae,Rotavirus,Rotavirus A | seg. 6 | FJ183358 |
| Human rotavirus G9P[6] | NC_011510 | vertebrates,human | 3 | Reoviridae,Rotavirus,Rotavirus A | seg. 4 | FJ183356,EU839952, EU839953 |
| Human rotavirus G9P[8] | NC_011503 | vertebrates,human | 11 | Reoviridae,Rotavirus,Rotavirus A | seg. 9 | AB364378,AB364370 ,AB364384,AB36438 3,AB364382,AB3643 77,AB364379,AB364 373,AB364374,AB36 4376,AB364375 |
| Human rotavirus G9P[8] | NC_011510 | vertebrates,human | 4 | Reoviridae,Rotavirus,Rotavirus A | seg. 4 | EU839960,EU839961 ,EU839962,EU83995 9 |
| Human rotavirus HCR3A | NC_011500 | vertebrates,human | 1 | Reoviridae,Rotavirus,Rotavirus A | seg. 5 | EU708907 |
| Human rotavirus HCR3A | NC_011501 | vertebrates,human | 1 | Reoviridae,Rotavirus,Rotavirus A | seg. 7 | EU708908 |
| Human rotavirus HCR3A | NC_011502 | vertebrates,human | 1 | Reoviridae,Rotavirus,Rotavirus A | seg. 8 | EU708909 |
| Human rotavirus HCR3A | NC_011503 | vertebrates,human | 1 | Reoviridae,Rotavirus,Rotavirus A | seg. 9 | EU708906 |
| Human rotavirus HCR3A | NC_011504 | vertebrates,human | 1 | Reoviridae,Rotavirus,Rotavirus A | seg. 10 | EU708910 |
| Human rotavirus HCR3A | NC_011505 | vertebrates,human | 1 | Reoviridae,Rotavirus,Rotavirus A | seg. 11 | EU708911 |
| Human rotavirus HCR3A | NC_011506 | vertebrates,human | 1 | Reoviridae,Rotavirus,Rotavirus A | seg. 2 | EU708902 |
| Human rotavirus HCR3A | NC_011507 | vertebrates,human | 1 | Reoviridae,Rotavirus,Rotavirus A | seg. 1 | EU708901 |
| Human rotavirus HCR3A | NC_011508 | vertebrates,human | 1 | Reoviridae,Rotavirus,Rotavirus A | seg. 3 | EU708903 |
| Human rotavirus HCR3A | NC_011509 | vertebrates,human | 1 | Reoviridae,Rotavirus,Rotavirus A | seg. 6 | EU708905 |
| Human rotavirus HCR3A | NC_011510 | vertebrates,human | 1 | Reoviridae,Rotavirus,Rotavirus A | seg. 4 | EU708904 |
| Human rotavirus HMGQ35 | NC_011510 | vertebrates,human | 1 | Reoviridae,Rotavirus,Rotavirus A | seg. 4 | AF361438 |
| Human rotavirus II type 1 | NC_011510 | vertebrates,human | 1 | Reoviridae,Rotavirus,Rotavirus A | seg. 4 | D90260 |
| Human rotavirus MP409 | NC_011510 | vertebrates,human | 1 | Reoviridae,Rotavirus,Rotavirus A | seg. 4 | AF143408 |
| Human rotavirus Ro1845 | NC_011500 | vertebrates,human | 1 | Reoviridae,Rotavirus,Rotavirus A | seg. 5 | EU708896 |
| Human rotavirus Ro1845 | NC_011501 | vertebrates,human | 1 | Reoviridae,Rotavirus,Rotavirus A | seg. 7 | EU708897 |
| Human rotavirus Ro1845 | NC_011502 | vertebrates,human | 1 | Reoviridae,Rotavirus,Rotavirus A | seg. 8 | EU708898 |
| Human rotavirus Ro1845 | NC_011503 | vertebrates,human | 1 | Reoviridae,Rotavirus,Rotavirus A | seg. 9 | EU708895 |
| Human rotavirus Ro1845 | NC_011504 | vertebrates,human | 1 | Reoviridae,Rotavirus,Rotavirus A | seg. 10 | EU708899 |
| Human rotavirus Ro1845 | NC_011505 | vertebrates,human | 1 | Reoviridae,Rotavirus,Rotavirus A | seg. 11 | EU708900 |
| Human rotavirus Ro1845 | NC_011506 | vertebrates,human | 1 | Reoviridae,Rotavirus,Rotavirus A | seg. 2 | EU708891 |
| Human rotavirus Ro1845 | NC_011507 | vertebrates,human | 1 | Reoviridae,Rotavirus,Rotavirus A | seg. 1 | EU708890 |

| Taxonomy | NCBI Reference Sequence ID | Host | No. of Genomes | Lineage | Segment Count | Genbank Accession ID |
|---|---|---|---|---|---|---|
| Human rotavirus Ro1845 | NC_011508 | vertebrates,human | 1 | Reoviridae,Rotavirus,Rotavirus A | seg. 3 | EU708892 |
| Human rotavirus Ro1845 | NC_011509 | vertebrates,human | 1 | Reoviridae,Rotavirus,Rotavirus A | seg. 6 | EU708894 |
| Human rotavirus Ro1845 | NC_011510 | vertebrates,human | 1 | Reoviridae,Rotavirus,Rotavirus A | seg. 4 | EU708893 |
| Human rotavirus serotype 1 strain M37 | NC_011504 | vertebrates,human | 1 | Reoviridae,Rotavirus,Rotavirus A | seg. 10 | U59109 |
| Human rotavirus serotype 2 strain 1076 | NC_011504 | vertebrates,human | 1 | Reoviridae,Rotavirus,Rotavirus A | seg. 10 | U59105 |
| Human rotavirus strain MP409 | NC_011500 | vertebrates,human | 1 | Reoviridae,Rotavirus,Rotavirus A | seg. 5 | AF141916 |
| Human rotavirus strain MP409 | NC_011502 | vertebrates,human | 1 | Reoviridae,Rotavirus,Rotavirus A | seg. 8 | AF141917 |
| Human rotavirus strain MP409 | NC_011503 | vertebrates,human | 1 | Reoviridae,Rotavirus,Rotavirus A | seg. 9 | AF141918 |
| Human rotavirus strain NnB1 | NC_011510 | vertebrates,human | 1 | Reoviridae,Rotavirus,Rotavirus A | seg. 4 | AF076926 |
| Human rotavirus strain S12/85 | NC_011510 | vertebrates,human | 1 | Reoviridae,Rotavirus,Rotavirus A | seg. 4 | AF076925 |
| IDIR agent X16949 | NC_021551 | vertebrates,human | 1 | Reoviridae,Rotavirus,Rotavirus B | seg. 3 | |
| Ikoma lyssavirus | NC_018629 | vertebrates,human | 1 | Rhabdoviridae, Lyssavirus, I koma lyssavirus | seg. 3 | JX193798 |
| Influenza A virus (A/Puerto Rico/8/1934(H 1N1)) | NC_002022 | vertebrates,human | 1 | Orthomyxoviridae,Influenzavirus A,Influenza A virus | seg. 3 | V01106 |
| Influenza A virus (A/Puerto Rico/8/34(H 1N1)) | NC_002016 | vertebrates,human | 1 | Orthomyxoviridae,Influenzavirus A,Influenza A virus | seg. 7 | V01099 |
| Influenza A virus (A/Puerto Rico/8/34(H 1N1)) | NC_002017 | vertebrates,human | 1 | Orthomyxoviridae,Influenzavirus A,Influenza A virus | seg. 4 | V01088 |
| Influenza A virus (A/Puerto Rico/8/34(H 1N1)) | NC_002018 | vertebrates,human | 1 | Orthomyxoviridae,Influenzavirus A,Influenza A virus | seg. 6 | JQ2146 |
| Influenza A virus (A/Puerto Rico/8/34(H 1N1)) | NC_002019 | vertebrates,human | 1 | Orthomyxoviridae,Influenzavirus A,Influenza A virus | seg. 5 | JQ2147 |
| Influenza A virus (A/Puerto Rico/8/34(H 1N1)) | NC_002020 | vertebrates,human | 1 | Orthomyxoviridae,Influenzavirus A,Influenza A virus | seg. 8 | JQ2150 |
| Influenza A virus (A/Puerto Rico/8/34(H 1N1)) | NC_002021 | vertebrates,human | 1 | Orthomyxoviridae,Influenzavirus A,Influenza A virus | seg. 2 | JQ2151 |
| Influenza A virus (A/Puerto Rico/8/34(H 1N1)) | NC_002023 | vertebrates,human | 1 | Orthomyxoviridae,Influenzavirus A,Influenza A virus | seg. 1 | V00603 |
| Influenza B virus | NC_002204 | vertebrates,human | 1 | Orthomyxoviridae,Influenzavirus B,Influenza B virus | seg. RNA 1 | M14880 |
| Influenza B virus | NC_002205 | vertebrates,human | 1 | Orthomyxoviridae,Influenzavirus B,Influenza B virus | seg. RNA 2 | AF101982 |
| Influenza B virus | NC_002206 | vertebrates,human | 1 | Orthomyxoviridae,Influenzavirus B,Influenza B virus | seg. RNA 3 | AF102017 |
| Influenza B virus | NC_002207 | vertebrates,human | 1 | Orthomyxoviridae,Influenzavirus B,Influenza B virus | seg. RNA 4 | K00423 |
| Influenza B virus | NC_002208 | vertebrates,human | 1 | Orthomyxoviridae,Influenzavirus B,Influenza B virus | seg. RNA 5 | K01395 |
| Influenza B virus | NC_002209 | vertebrates,human | 1 | Orthomyxoviridae,Influenzavirus B,Influenza B virus | seg. RNA 6 | JQ2095 |

| Taxonomy | NCBI Reference Sequence ID | Host | No. of Genomes | Lineage | Segment Count | Genbank Accession ID |
|---|---|---|---|---|---|---|
| Influenza B virus | NC_002210 | vertebrates,human | 1 | Orthomyxoviridae,Influenzavirus B,Influenza B virus | seg. RNA 7 | JQ2094 |
| Influenza B virus | NC_002211 | vertebrates,human | 1 | Orthomyxoviridae,Influenzavirus B,Influenza B virus | seg. RNA 8 | JQ2096 |
| Influenza C virus | NC_006306 | vertebrates,human | 29 | Orthomyxoviridae,Influenzavirus C,Influenza C virus | seg. 7 | AB034181,AB034170,AB034165,AB034174,AB034157,DQ00028,AB034161,AB034169,AB034173,AB034180,AB034168,AB034156,AB035367,AB034179,AB034159,AB034166,AB034160,AB034172,AB035366,AB034164,AB034178,AB034158,AB034163,AB034176,AB034177,AB034175,AB034162,AB034167,AB034171 |
| Influenza C virus | NC_006307 | vertebrates,human | 2 | Orthomyxoviridae,Influenzavirus C,Influenza C virus | seg. 1 | M28061,J20228 |
| Influenza C virus | NC_006308 | vertebrates,human | 1 | Orthomyxoviridae,Influenzavirus C,Influenza C virus | seg. 2 | M28060 |
| Influenza C virus | NC_006309 | vertebrates,human | 1 | Orthomyxoviridae,Influenzavirus C,Influenza C virus | seg. 3 | M28062 |
| Influenza C virus | NC_006310 | vertebrates,human | 14 | Orthomyxoviridae, Influenzavirus C, Influenza C virus | seg. 4 | M11643,M11642,M25363,M11639,M11638,M11645,K01689,M11637,M11640,M17868,M25361,M11644,M11641,M25362 |
| Influenza C virus | NC_006312 | vertebrates,human | 2 | Orthomyxoviridae,Influenzavirus C,Influenza C virus | seg. 6 | M17700,M22038 |
| Influenza C virus (C/Aichi/1/81) | NC_006312 | vertebrates,human | 1 | Orthomyxoviridae,Influenzavirus C,Influenza C virus | seg. 6 | D16260 |
| Influenza C virus (C/Ann Arbor/1/50) | NC_006306 | vertebrates,human | 1 | Orthomyxoviridae,Influenzavirus C,Influenza C virus | seg. 7 | AB283001 |
| Influenza C virus (C/Ann Arbor/1/50) | NC_006307 | vertebrates,human | 1 | Orthomyxoviridae,Influenzavirus C,Influenza C virus | seg. 1 | AB126191 |
| Influenza C virus (C/Ann Arbor/1/50) | NC_006308 | vertebrates,human | 1 | Orthomyxoviridae,Influenzavirus C,Influenza C virus | seg. 2 | AB126192 |
| Influenza C virus (C/Ann Arbor/1/50) | NC_006309 | vertebrates,human | 1 | Orthomyxoviridae,Influenzavirus C,Influenza C virus | seg. 3 | AB126193 |
| Influenza C virus (C/Ann Arbor/1/50) | NC_006310 | vertebrates,human | 1 | Orthomyxoviridae,Influenzavirus C,Influenza C virus | seg. 4 | AB126194 |
| Influenza C virus (C/Ann Arbor/1/50) | NC_006311 | vertebrates,human | 1 | Orthomyxoviridae,Influenzavirus C,Influenza C virus | seg. 5 | AB126195 |

| Taxonomy | NCBI Reference Sequence ID | Host | No. of Genomes | Lineage | Segment Count | Genbank Accession ID |
|---|---|---|---|---|---|---|
| Influenza C virus (C/Ann Arbor/1/50) | NC_006312 | vertebrates,human | 1 | Orthomyxoviridae,Influenzavirus C,Influenza C virus | seg. 6 | AB126196 |
| Influenza C virus (C/Aomori/74) | NC_006310 | vertebrates,human | 1 | Orthomyxoviridae,Influenzavirus C,Influenza C virus | seg. 4 | D63469 |
| Influenza C virus (C/Aomori/74) | NC_006312 | vertebrates,human | 1 | Orthomyxoviridae,Influenzavirus C,Influenza C virus | seg. 6 | D16259 |
| Influenza C virus (C/California/78) | NC_006306 | vertebrates,human | 2 | Orthomyxoviridae,Influenzavirus C,Influenza C virus | seg. 7 | M10087,AB099625 |
| Influenza C virus (C/California/78) | NC_006312 | vertebrates,human | 1 | Orthomyxoviridae,Influenzavirus C,Influenza C virus | seg. 6 | AB000608 |
| Influenza C virus (C/England/83) | NC_006312 | vertebrates,human | 1 | Orthomyxoviridae,Influenzavirus C,Influenza C virus | seg. 6 | AB000725 |
| Influenza C virus (C/Greece/79) | NC_006306 | vertebrates,human | 1 | Orthomyxoviridae,Influenzavirus C,Influenza C virus | seg. 7 | AB099627 |
| Influenza C virus (C/Hiroshima/246/2000) | NC_006306 | vertebrates,human | 1 | Orthomyxoviridae,Influenzavirus C,Influenza C virus | seg. 7 | AB099619 |
| Influenza C virus (C/Hiroshima/247/2000) | NC_006306 | vertebrates,human | 1 | Orthomyxoviridae,Influenzavirus C,Influenza C virus | seg. 7 | AB099620 |
| Influenza C virus (C/Hiroshima/248/2000) | NC_006306 | vertebrates,human | 1 | Orthomyxoviridae,Influenzavirus C,Influenza C virus | seg. 7 | AB099621 |
| Influenza C virus (C/Hiroshima/249/2000) | NC_006306 | vertebrates,human | 1 | Orthomyxoviridae,Influenzavirus C,Influenza C virus | seg. 7 | AB099618 |
| Influenza C virus (C/Hiroshima/250/2000) | NC_006306 | vertebrates,human | 1 | Orthomyxoviridae,Influenzavirus C,Influenza C virus | seg. 7 | AB099622 |
| Influenza C virus (C/Hiroshima/251/2000) | NC_006306 | vertebrates,human | 1 | Orthomyxoviridae,Influenzavirus C,Influenza C virus | seg. 7 | AB099623 |
| Influenza C virus (C/Hiroshima/252/99) | NC_006306 | vertebrates,human | 1 | Orthomyxoviridae,Influenzavirus C,Influenza C virus | seg. 7 | AB099617 |
| Influenza C virus (C/Hiroshima/290/99) | NC_006306 | vertebrates,human | 1 | Orthomyxoviridae,Influenzavirus C,Influenza C virus | seg. 7 | AB099616 |
| Influenza C virus (C/Hyogo/1/83) | NC_006312 | vertebrates,human | 1 | Orthomyxoviridae,Influenzavirus C,Influenza C virus | seg. 6 | AB000610 |
| Influenza C virus (C/Johannesburg/66) | NC_006312 | vertebrates,human | 1 | Orthomyxoviridae,Influenzavirus C,Influenza C virus | seg. 6 | AB000604 |
| Influenza C virus (C/Kanagawa/1/76) | NC_006310 | vertebrates,human | 1 | Orthomyxoviridae,Influenzavirus C,Influenza C virus | seg. 4 | D63470 |
| Influenza C virus (C/Kanagawa/1/76) | NC_006312 | vertebrates,human | 1 | Orthomyxoviridae,Influenzavirus C,Influenza C virus | seg. 6 | AB000606 |
| Influenza C virus (C/Kansas/1/79) | NC_006306 | vertebrates,human | 1 | Orthomyxoviridae,Influenzavirus C,Influenza C virus | seg. 7 | AB099626 |
| Influenza C virus (C/Kyoto/1/79) | NC_006310 | vertebrates,human | 1 | Orthomyxoviridae,Influenzavirus C,Influenza C virus | seg. 4 | D63472 |
| Influenza C virus (C/Kyoto/1/79) | NC_006312 | vertebrates,human | 1 | Orthomyxoviridae,Influenzavirus C,Influenza C virus | seg. 6 | AB000609 |
| Influenza C virus (C/Kyoto/41/82) | NC_006312 | vertebrates,human | 1 | Orthomyxoviridae,Influenzavirus C,Influenza C virus | seg. 6 | AB000724 |
| Influenza C virus (C/Mississippi/80) | NC_006312 | vertebrates,human | 1 | Orthomyxoviridae,Influenzavirus C,Influenza C virus | seg. 6 | AB000720 |

-continued

| Taxonomy | NCBI Reference Sequence ID | Host | No. of Genomes | Lineage | Segment Count | Genbank Accession ID |
|---|---|---|---|---|---|---|
| Influenza C virus (C/Miyagi/1/93) | NC_006306 | vertebrates,human | 1 | Orthomyxoviridae,Influenzavirus C,Influenza C virus | seg. 7 | AB086790 |
| Influenza C virus (C/Miyagi/1/94) | NC_006306 | vertebrates,human | 1 | Orthomyxoviridae,Influenzavirus C,Influenza C virus | seg. 7 | AB086797 |
| Influenza C virus (C/Miyagi/1/97) | NC_006306 | vertebrates,human | 1 | Orthomyxoviridae,Influenzavirus C,Influenza C virus | seg. 7 | AB086806 |
| Influenza C virus (C/Miyagi/1/99) | NC_006306 | vertebrates,human | 1 | Orthomyxoviridae,Influenzavirus C,Influenza C virus | seg. 7 | AB086809 |
| Influenza C virus (C/Miyagi/2/2000) | NC_006306 | vertebrates,human | 1 | Orthomyxoviridae,Influenzavirus C,Influenza C virus | seg. 7 | AB099609 |
| Influenza C virus (C/Miyagi/2/92) | NC_006306 | vertebrates,human | 1 | Orthomyxoviridae,Influenzavirus C,Influenza C virus | seg. 7 | AB086789 |
| Influenza C virus (C/Miyagi/2/93) | NC_006306 | vertebrates,human | 1 | Orthomyxoviridae,Influenzavirus C,Influenza C virus | seg. 7 | AB086791 |
| Influenza C virus (C/Miyagi/2/94) | NC_006306 | vertebrates,human | 1 | Orthomyxoviridae,Influenzavirus C,Influenza C virus | seg. 7 | AB086798 |
| Influenza C virus (C/Miyagi/2/96) | NC_006306 | vertebrates,human | 1 | Orthomyxoviridae,Influenzavirus C,Influenza C virus | seg. 7 | AB086800 |
| Influenza C virus (C/Miyagi/2/98) | NC_006306 | vertebrates,human | 1 | Orthomyxoviridae,Influenzavirus C,Influenza C virus | seg. 7 | AB086807 |
| Influenza C virus (C/Miyagi/3/2000) | NC_006306 | vertebrates,human | 1 | Orthomyxoviridae,Influenzavirus C,Influenza C virus | seg. 7 | AB099610 |
| Influenza C virus (C/Miyagi/3/93) | NC_006306 | vertebrates,human | 1 | Orthomyxoviridae,Influenzavirus C,Influenza C virus | seg. 7 | AB086792 |
| Influenza C virus (C/Miyagi/3/94) | NC_006306 | vertebrates,human | 1 | Orthomyxoviridae,Influenzavirus C,Influenza C virus | seg. 7 | AB086799 |
| Influenza C virus (C/Miyagi/3/99) | NC_006306 | vertebrates,human | 1 | Orthomyxoviridae,Influenzavirus C,Influenza C virus | seg. 7 | AB086811 |
| Influenza C virus (C/Miyagi/4/2000) | NC_006306 | vertebrates,human | 1 | Orthomyxoviridae,Influenzavirus C,Influenza C virus | seg. 7 | AB099611 |
| Influenza C virus (C/Miyagi/4/93) | NC_006306 | vertebrates,human | 1 | Orthomyxoviridae,Influenzavirus C,Influenza C virus | seg. 7 | AB086793 |
| Influenza C virus (C/Miyagi/4/96) | NC_006306 | vertebrates,human | 1 | Orthomyxoviridae,Influenzavirus C,Influenza C virus | seg. 7 | AB086801 |
| Influenza C virus (C/Miyagi/4/98) | NC_006306 | vertebrates,human | 1 | Orthomyxoviridae,Influenzavirus C,Influenza C virus | seg. 7 | AB086808 |
| Influenza C virus (C/Miyagi/5/2000) | NC_006306 | vertebrates,human | 1 | Orthomyxoviridae,Influenzavirus C,Influenza C virus | seg. 7 | AB099612 |
| Influenza C virus (C/Miyagi/5/93) | NC_006306 | vertebrates,human | 1 | Orthomyxoviridae,Influenzavirus C,Influenza C virus | seg. 7 | AB086794 |
| Influenza C virus (C/Miyagi/6/93) | NC_006306 | vertebrates,human | 1 | Orthomyxoviridae,Influenzavirus C,Influenza C virus | seg. 7 | AB086795 |
| Influenza C virus (C/Miyagi/6/96) | NC_006306 | vertebrates,human | 1 | Orthomyxoviridae,Influenzavirus C,Influenza C virus | seg. 7 | AB086802 |
| Influenza C virus (C/Miyagi/7/93) | NC_006306 | vertebrates,human | 1 | Orthomyxoviridae,Influenzavirus C,Influenza C virus | seg. 7 | AB086796 |
| Influenza C virus (C/Miyagi/7/96) | NC_006306 | vertebrates,human | 1 | Orthomyxoviridae,Influenzavirus C,Influenza C virus | seg. 7 | AB086803 |

| Taxonomy | NCBI Reference Sequence ID | Host | No. of Genomes | Lineage | Segment Count | Genbank Accession ID |
|---|---|---|---|---|---|---|
| Influenza C virus (C/Miyagi/77) | NC_006310 | vertebrates,human | 1 | Orthomyxoviridae,Influenzavirus C,Influenza C virus | seg. 4 | D63471 |
| Influenza C virus (C/Miyagi/77) | NC_006312 | vertebrates,human | 1 | Orthomyxoviridae,Influenzavirus C,Influenza C virus | seg. 6 | AB000607 |
| Influenza C virus (C/Miyagi/8/96) | NC_006306 | vertebrates,human | 1 | Orthomyxoviridae,Influenzavirus C,Influenza C virus | seg. 7 | AB086804 |
| Influenza C virus (C/Miyagi/9/91) | NC_006312 | vertebrates,human | 1 | Orthomyxoviridae,Influenzavirus C,Influenza C virus | seg. 6 | AB000614 |
| Influenza C virus (C/Miyagi/9/96) | NC_006306 | vertebrates,human | 1 | Orthomyxoviridae,Influenzavirus C,Influenza C virus | seg. 7 | AB086805 |
| Influenza C virus (C/Nara/1/85) | NC_006312 | vertebrates,human | 1 | Orthomyxoviridae,Influenzavirus C,Influenza C virus | seg. 6 | AB000726 |
| Influenza C virus (C/Nara/2/85) | NC_006310 | vertebrates,human | 1 | Orthomyxoviridae,Influenzavirus C,Influenza C virus | seg. 4 | D30697 |
| Influenza C virus (C/Nara/2/85) | NC_006312 | vertebrates,human | 1 | Orthomyxoviridae,Influenzavirus C,Influenza C virus | seg. 6 | AB000727 |
| Influenza C virus (C/Nara/82) | NC_006312 | vertebrates,human | 1 | Orthomyxoviridae,Influenzavirus C,Influenza C virus | seg. 6 | AB000723 |
| Influenza C virus (C/New Jersey/76) | NC_006306 | vertebrates,human | 1 | Orthomyxoviridae,Influenzavirus C,Influenza C virus | seg. 7 | AB099624 |
| Influenza C virus (C/Saitama/1/2000) | NC_006306 | vertebrates,human | 1 | Orthomyxoviridae,Influenzavirus C,Influenza C virus | seg. 7 | AB099613 |
| Influenza C virus (C/Saitama/2/2000) | NC_006306 | vertebrates,human | 1 | Orthomyxoviridae,Influenzavirus C,Influenza C virus | seg. 7 | AB099614 |
| Influenza C virus (C/Saitama/3/2000) | NC_006306 | vertebrates,human | 1 | Orthomyxoviridae,Influenzavirus C,Influenza C virus | seg. 7 | AB099615 |
| Influenza C virus (C/Sapporo/71) | NC_006310 | vertebrates,human | 1 | Orthomyxoviridae,Influenzavirus C,Influenza C virus | seg. 4 | D63468 |
| Influenza C virus (C/Sapporo/71) | NC_006312 | vertebrates,human | 1 | Orthomyxoviridae,Influenzavirus C,Influenza C virus | seg. 6 | AB000605 |
| Influenza C virus (C/Shizuoka/79) | NC_006306 | vertebrates,human | 1 | Orthomyxoviridae,Influenzavirus C,Influenza C virus | seg. 7 | AB086788 |
| Influenza C virus (C/Yamagata/1/86) | NC_006312 | vertebrates,human | 1 | Orthomyxoviridae,Influenzavirus C,Influenza C virus | seg. 6 | AB000611 |
| Influenza C virus (C/Yamagata/1/86) | NC_006306 | vertebrates,human | 1 | Orthomyxoviridae,Influenzavirus C,Influenza C virus | seg. 7 | AB002469 |
| Influenza C virus (C/Yamagata/1/86) | NC_006312 | vertebrates,human | 1 | Orthomyxoviridae,Influenzavirus C,Influenza C virus | seg. 6 | D16261 |
| Influenza C virus (C/Yamagata/10/89) | NC_006312 | vertebrates,human | 1 | Orthomyxoviridae,Influenzavirus C,Influenza C virus | seg. 6 | AB000613 |
| Influenza C virus (C/Yamagata/13/98) | NC_006306 | vertebrates,human | 1 | Orthomyxoviridae,Influenzavirus C,Influenza C virus | seg. 7 | AB064445 |
| Influenza C virus (C/Yamagata/2/2000) | NC_006306 | vertebrates,human | 1 | Orthomyxoviridae,Influenzavirus C,Influenza C virus | seg. 7 | AB099605 |
| Influenza C virus (C/Yamagata/2/98) | NC_006306 | vertebrates,human | 1 | Orthomyxoviridae,Influenzavirus C,Influenza C virus | seg. 7 | AB064443 |
| Influenza C virus (C/Yamagata/2/99) | NC_006306 | vertebrates,human | 1 | Orthomyxoviridae,Influenzavirus C,Influenza C virus | seg. 7 | AB099603 |

| Taxonomy | NCBI Reference Sequence ID | Host | No. of Genomes | Lineage | Segment Count | Genbank Accession ID |
|---|---|---|---|---|---|---|
| Influenza C virus (C/Yamagata/20/96) | NC_006306 | vertebrates,human | 1 | Orthomyxoviridae,Influenzavirus C,Influenza C virus | seg. 7 | AB064442 |
| Influenza C virus (C/Yamagata/26/81) | NC_006312 | vertebrates,human | 1 | Orthomyxoviridae,Influenzavirus C,Influenza C virus | seg. 6 | AB000721 |
| Influenza C virus (C/Yamagata/3/2000) | NC_006306 | vertebrates,human | 1 | Orthomyxoviridae,Influenzavirus C,Influenza C virus | seg. 7 | AB099606 |
| Influenza C virus (C/Yamagata/3/86) | NC_006310 | vertebrates,human | 1 | Orthomyxoviridae,Influenzavirus C,Influenza C virus | seg. 4 | D63473 |
| Influenza C virus (C/Yamagata/3/96) | NC_006306 | vertebrates,human | 1 | Orthomyxoviridae,Influenzavirus C,Influenza C virus | seg. 7 | AB064439 |
| Influenza C virus (C/Yamagata/4/86) | NC_006310 | vertebrates,human | 1 | Orthomyxoviridae,Influenzavirus C,Influenza C virus | seg. 4 | D63503 |
| Influenza C virus (C/Yamagata/6/2000) | NC_006306 | vertebrates,human | 1 | Orthomyxoviridae,Influenzavirus C,Influenza C virus | seg. 7 | AB099607 |
| Influenza C virus (C/Yamagata/6/98) | NC_006306 | vertebrates,human | 1 | Orthomyxoviridae,Influenzavirus C,Influenza C virus | seg. 7 | AB064444 |
| Influenza C virus (C/Yamagata/64) | NC_006310 | vertebrates,human | 1 | Orthomyxoviridae,Influenzavirus C,Influenza C virus | seg. 4 | D63467 |
| Influenza C virus (C/Yamagata/64) | NC_006312 | vertebrates,human | 1 | Orthomyxoviridae,Influenzavirus C,Influenza C virus | seg. 6 | D16258 |
| Influenza C virus (C/Yamagata/8/2000) | NC_006306 | vertebrates,human | 1 | Orthomyxoviridae,Influenzavirus C,Influenza C virus | seg. 7 | AB099608 |
| Influenza C virus (C/Yamagata/8/86) | NC_006312 | vertebrates,human | 1 | Orthomyxoviridae,Influenzavirus C,Influenza C virus | seg. 6 | AB000612 |
| Influenza C virus (C/Yamagata/8/96) | NC_006306 | vertebrates,human | 1 | Orthomyxoviridae,Influenzavirus C,Influenza C virus | seg. 7 | AB064440 |
| Influenza C virus (C/Yamagata/9/2000) | NC_006306 | vertebrates,human | 1 | Orthomyxoviridae,Influenzavirus C,Influenza C virus | seg. 7 | AB099604 |
| Influenza C virus (C/Yamagata/9/86) | NC_006312 | vertebrates,human | 1 | Orthomyxoviridae,Influenzavirus C,Influenza C virus | seg. 6 | AB000728 |
| Influenza C virus (C/Yamagata/9/96) | NC_006306 | vertebrates,human | 1 | Orthomyxoviridae,Influenzavirus C,Influenza C virus | seg. 7 | AB064441 |
| Influenza C virus (C/pig/Beijing/115/81) | NC_006312 | vertebrates,human | 1 | Orthomyxoviridae,Influenzavirus C,Influenza C virus | seg. 6 | AB000722 |
| Influenza C virus (STRAIN C/BERLIN/1/85) | NC_006307 | vertebrates,human | 1 | Orthomyxoviridae,Influenzavirus C,Influenza C virus | seg. 1 | X55992 |
| Influenza C virus (STRAIN C/TAYLOR/1233/47) | NC_006312 | vertebrates,human | 1 | Orthomyxoviridae,Influenzavirus C,Influenza C virus | seg. 6 | D26546 |
| Ippy virus | NC_007905 | vertebrates,human | 1 | Arenaviridae,Arenavirus,Ippy virus | seg. S | DQ328877 |
| Ippy virus | NC_007906 | vertebrates,human | 1 | Arenaviridae,Arenavirus,Ippy virus | seg. L | DQ328878 |
| Irkut virus | NC_020809 | vertebrates,human | 2 | Rhabdoviridae,Lyssavirus,Irkut virus | — | JX442979,EF614260 |
| Italian lapine rotavirus 30/96 | NC_011500 | vertebrates,human | 1 | Reoviridae,Rotavirus,Rotavirus A | seg. 5 | DQ205225 |
| Italian lapine rotavirus 30/96 | NC_011501 | vertebrates,human | 1 | Reoviridae,Rotavirus,Rotavirus A | seg. 7 | DQ205227 |
| Italian lapine rotavirus 30/96 | NC_011502 | vertebrates,human | 1 | Reoviridae,Rotavirus,Rotavirus A | seg. 8 | DQ205228 |

-continued

| Taxonomy | NCBI Reference Sequence ID | Host | No. of Genomes | Lineage | Segment Count | Genbank Accession ID |
|---|---|---|---|---|---|---|
| Italian lapine rotavirus 30/96 | NC_011503 | vertebrates,human | 1 | Reoviridae,Rotavirus,Rotavirus A | seg. 9 | DQ205229 |
| Italian lapine rotavirus 30/96 | NC_011504 | vertebrates,human | 1 | Reoviridae,Rotavirus,Rotavirus A | seg. 10 | DQ205230 |
| Italian lapine rotavirus 30/96 | NC_011505 | vertebrates,human | 1 | Reoviridae,Rotavirus,Rotavirus A | seg. 11 | DQ205231 |
| Italian lapine rotavirus 30/96 | NC_011506 | vertebrates,human | 1 | Reoviridae,Rotavirus,Rotavirus A | seg. 2 | DQ205222 |
| Italian lapine rotavirus 30/96 | NC_011507 | vertebrates,human | 1 | Reoviridae,Rotavirus,Rotavirus A | seg. 1 | DQ205221 |
| Italian lapine rotavirus 30/96 | NC_011508 | vertebrates,human | 1 | Reoviridae,Rotavirus,Rotavirus A | seg. 3 | DQ205223 |
| Italian lapine rotavirus 30/96 | NC_011509 | vertebrates,human | 1 | Reoviridae,Rotavirus,Rotavirus A | seg. 6 | DQ205226 |
| Italian lapine rotavirus 30/96 | NC_011510 | vertebrates,human | 1 | Reoviridae,Rotavirus,Rotavirus A | seg. 4 | DQ205224 |
| J-virus | NC_007454 | vertebrates,human | 1 | Paramyxoviridae, J-virus | — | AY900001 |
| JC polyomavirus | NC_001699 | vertebrates,human | 592 | Polyomaviridae,Polyomavirus,JC polyomavirus | — | AB262401,JF424911,AB092584,AB074591,AB127013,AB113121,AY366359,AB118233,AB127350,AB126983,AB077869,AB183152,AB127346,AY536242,AB077859,JF424922,AB092582,AB081007,JF424869,JF424874,JF424877,AF363833,AB081612,AB127006,AB077864,JF424835,AB048553,AY536239,JF424859,AB362360,AB118652,AB118234,JF424952,JF425504,JF424875,JF424837,AB372036,AB262397,AY121908,AB113142,AY386377,AB038254,JF424958,AB113137,JF425489,AB048568,AF281617,AY121913,AB198946,JF425556,AB038252,AB103404,JF424885,JF424954,AB220941,AB048580,JF425551,AB081654,AB113131,AB077866,AB12 |

-continued

| Taxonomy | NCBI Reference Sequence ID | Host | No. of Genomes | Lineage | Segment Count | Genbank Accession ID |
|---|---|---|---|---|---|---|
| | | | | | | 7011,AB077879,JF42 4909,AB126991,AB2 20940,AB081018,AB 113135,AF396430,AF 300964,AB074581,A B118657,AB198940, AB074588,AY382187 ,AB048572,AB04857 6,AB081608,AB3623 63,AB127023,JF4249 42,JF424855,JF4249 08,AB048569,JF4248 43,AB103421,AB198 947,JF424880,AY121 914,JQ237146,AF363 834,AB048574,JF425 494,AB362351,AB26 2410,AY386376,AB1 27343,AF396435,AB0 92587,AB081604,JF4 24857,AB185020,AF2 81624,JF424923,JF4 25493,JF424939,AB0 81022,AB081013,AB 092579,JF424860,AB 081602,AB103387,A B262399,JF424894,A B048561,AB077873, AB127026,JF424936, AB262413,JF424864, AF300959,AB198944, AB262402,AB081030 ,AB103418,AB26241 2,AB081027,JF42487 6,AB048566,JF42490 0,AB103411,AF00435 0,AB081603,AB1273 42,AF396429,AB1186 53,AB127344,AB118 651,AB113123,AB08 1016,AB038253,AB0 77863,JF424917,AB0 81005,JF425498,AF2 81625,AB198949,JF4 24863,JF424951,JF4 24886,AB077874,JF4 25553,AY536241,JQ8 23124,AB118231,AF3 |

-continued

| Taxonomy | NCBI Reference Sequence ID | Host | No. of Genomes | Lineage | Segment Count | Genbank Accession ID |
|---|---|---|---|---|---|---|
| | | | | | | 00963,JF424926,JF4 24960,JF424910,AB1 03419,AY378084,JF4 24845,AB081015,AB 048577,AB127347,A B198942,AB127352,J F424851,JF424919,A B126994,AB113118,J F424870,AB081021,A B126984,AF300953,J F424883,AB081024,A B127348,JF424892,J F424930,AB113139,A B126403,AB126993, AB127003,JF424918, JF424941,AB127002, AF363832,AB127025, AB126982,JF425490, AB103409,AB048548 ,JF424920,AF300955 ,AB074577,AB08160 5,AB081020,AY3565 39,AB21954,AB113 138,AB113126,JF424 890,JF424937,JF424 953,JF424949,AB074 585,AB113133,AB04 8554,U61771,JF4249 28,JF424938,JF4248 61,AB048557,AB212 953,AB081008,AB12 7345,AB262404,AY3 42299,JF424878,AB2 62405,AF396428,AB0 74576,AB113143,JX2 73163,AF300951,AB1 27000,AY536240,AB 262408,AB118654,AF 281626,JF424856,AB 048558,U73501,AB04 8565,AB362366,JF42 4850,AF281623,AB12 7024,AB081012,AB1 18656,JF424962,JF4 25499,AB126998,JF4 24933,AF396433,AB3 62356,AB081006,AB 074582,AB081613,A |

| Taxonomy | NCBI Reference Sequence ID | Host | No. of Genomes | Lineage | Segment Count | Genbank Accession ID |
|---|---|---|---|---|---|---|
| | | | | | | B074583,AB262396, AB092583,AF300947, AF300952,AB198943, AB081601,AY386373 ,AB081023,AB12701 8,AB198953,AB0778 75,JF425501,AB1273 51,AB126996,AB127 016,AB118235,AB09 2578,AB077860,JF42 4848,AB048575,JF42 4873,AB220943,AY3 76830,AB077872,DQ 875212,AF300954,AB 048582,JF424853,JF 425491,AB103406,JF 424893,JF424913,AY 376831,AB103405,A B077861,AF295732,J F424881,AB127021,J F424842,AB127001,J 02226,AB077857,AB 362352,AB048571,A B048547,AB113124, AB103417,AF004349, JF424945,AB198945, JF424897,AB126988, AB372037,AB048552 ,AB074589,JF424961 ,AF396432,JF424891 ,AB077871,JF424865 ,JF424935,AB126981 ,JF424879,AB081616 ,AF396427,JF424895 ,AF300957,AB127007 ,AY378086,JF424866 ,AB220942,JF424839 ,AY378087,AB10342 2,AB081025,AB1131 19,AF300946,AB1132 17,AB103412,AB081 019,AB113122,AF300 960,JF425554,AB077 855,JF424959,AB104 487,AB081614,AB04 8564,AB103415,AB1 13140,AB092585,AB 198952,AB077877,A |

-continued

| Taxonomy | NCBI Reference Sequence ID | Host | No. of Genomes | Lineage | Segment Count | Genbank Accession ID |
|---|---|---|---|---|---|---|
| | | | | | | B126699,JF424957,AB362357,AB048560, AB198954,AB081611,JF425503,JF424882, AB113129,JF424905,JF424871,JF425552, AB048559,DQ875211,AB118232,AB077867,AB113130,AB1270 22,JF424947,AF3964 24,AB113216,AY121 912,AB048567,AB08 1615,AF300948,AF30 0962,AB362355,AY3 49147,JF424862,AB0 77865,JF424852,AB1 95639,JF424899,JF4 24906,AB126985,AY 382184,JF424844,JF 424925,JF424903,AB 103414,AB127004,A B074575,AB103407, AB118658,AB262406 ,AB103413,JF424916 ,JF42931,AB081017 ,AF363831,JF424944 ,AB103403,AB04856 3,AB077862,AF36383 0,JF424898,AB08101 1,AB127015,JF42492 9,JF424927,AB07786 8,AF396434,AB08101 0,AY328376,AB0485 62,AB038251,U73500 ,AB103402,AB22093 9,AB126990,AB08101 29,JF424902,AF3009 65,JF424849,AB0816 07,JF424921,JF4248 68,AB077858,JF4249 32,JF424872,JF4249 48,AF396426,AB3623 62,AF396423,JF4249 04,AF281615,AF3009 49,JF424896,AB0816 10,AB127008,AY376 828,JF424950,AB081 009,AF300958,AF295 |

-continued

| Taxonomy | NCBI Reference Sequence ID | Host | No. of Genomes | Lineage | Segment Count | Genbank Accession ID |
|---|---|---|---|---|---|---|
| | | | | | | 731,AB262400,AB26 2398,AY376829,AB1 27012,JF425502,AB1 26987,AB081606,AY 386378,AB048570,A B118655,AB048546, AY121915,AB113132 ,AB372038,AB03825 5,AY378085,JF42488 8,AB081618,AB3623 53,AY536243,AB126 992,AB092580,AB07 7856,JF424924,AB36 2364,JF425492,JF42 4955,AB048556,AB0 77870,AB126989,JF4 24907,AY364314,AF0 30085,AB262411,AB 127349,AB126986,A Y121909,AY386374,J F424854,AB074586,J F424847,AY121907,A B074579,JF425555,A B113141,AB077876, AB103423,AB118659 ,AB113144,AB19564 0,AB103420,AB2624 07,JF424901,AF2816 16,JF424858,AB1131 34,JF425500,AY1219 11,AB362359,U73502 ,AB081600,AB11313 6,AB113125,AB1131 45,JF424834,AF3964 22,AY382188,AY386 375,AB092581,AB10 3416,JF425488,JF42 4943,AB198948,AB2 12952,AF300967,AB0 48545,AB081617,AB 113120,EU835194,JF 424841,AB048581,A B074590,JF424956,J F424912,AB048579,A B081028,AB048549, AB074578,AB362361 ,JF425495,AB126997 ,AB198941,AY38218 |

| Taxonomy | NCBI Reference Sequence ID | Host | No. of Genomes | Lineage | Segment Count | Genbank Accession ID |
|---|---|---|---|---|---|---|
| | | | | | | 5,AB038250,JF42549 7,JF424846,JF42491 4,AB198951,AB1270 10,AF300956,JF4248 67,AB362358,AB262 409,AY382186,AB03 8249,JF424934,AB04 8550,JF424884,AB04 8573,JF424838,AB07 4584,AY373463,AB0 74580,AB127

-continued

| Taxonomy | NCBI Reference Sequence ID | Host | No. of Genomes | Lineage | Segment Count | Genbank Accession ID |
|---|---|---|---|---|---|---|
| | | | | | | 58023,FJ969442,DQ854733,JF799984,DQ854732,JF799981,JF799982,JN714129,D10072,DQ854735,JN801476,DQ854734,HQ126701,DQ272266,FJ805380,DQ531486,JN200801 |
| K1 polyomavirus | NC_009238 | vertebrates,human | 6 | Polyomaviridae,Polyomavirus,KI polyomavirus | — | EU358767,EF520287,JEF520288,EU35876 6,EF127906,EF520289 |
| K1 polyomavirus Stockholm 350 | NC_009238 | vertebrates,human | 1 | Polyomaviridae,Polyomavirus,KI polyomavirus | — | EF127907 |
| K1 polyomavirus Stockholm 380 | NC_009238 | vertebrates,human | 1 | Polyomaviridae,Polyomavirus,KI polyomavirus | — | EF127908 |
| Lagos bat virus | NC_020807 | vertebrates,human | 5 | Rhabdoviridae,Lyssavirus,Lagos bat virus | — | EU259198,GU170202,EU293108,EU293110,JX901139 |
| Lake Victoria marburgvirus | NC_001608 | vertebrates,human | 14 | Filoviridae,Marburgvirus,Marburg marburgvirus | — | FJ750954,FJ750953,Z29337,AY358025,Z12132,FJ750956,FJ750957,AY430365,FJ750959,AY430366,DQ217792,FJ750958,FJ750955,GQ433353 |
| Lake Victoria marburgvirus-Angola2005 | NC_001608 | vertebrates,human | 8 | Filoviridae,Marburgvirus,Marburg marburgvirus | — | DQ447658,DQ447659,DQ447654,DQ447660,DQ447656,DQ447653,DQ447657,DQ447655 |
| Lake Victoria marburgvirus-Ci67 | NC_001608 | vertebrates,human | 1 | Filoviridae,Marburgvirus,Marburg marburgvirus | — | EF446132 |
| Lake Victoria marburgvirus-DRC1999 | NC_001608 | vertebrates,human | 3 | Filoviridae,Marburgvirus,Marburg marburgvirus | — | DQ447650,DQ447652,DQ44765 |
| Lake Victoria marburgvirus-Leiden | NC_001608 | vertebrates,human | 1 | Filoviridae,Marburgvirus,Marburg marburgvirus | — | JN408064 |
| Lake Victoria marburgvirus-Ravn | NC_001608 | vertebrates,human | 2 | Filoviridae,Marburgvirus,Marburg marburgvirus | — | DQ447649,EF446131 |
| Lamb rotavirus | NC_011500 | vertebrates,human | 2 | Reoviridae,Rotavirus,Rotavirus A | seg. 5 | HQ834202,FJ031019 |
| Lamb rotavirus | NC_011501 | vertebrates,human | 2 | Reoviridae,Rotavirus,Rotavirus A | seg. 7 | HQ834204,FJ031020 |
| Lamb rotavirus | NC_011502 | vertebrates,human | 3 | Reoviridae,Rotavirus,Rotavirus A | seg. 8 | HQ834203,FJ031021,JQ031147 |
| Lamb rotavirus | NC_011503 | vertebrates,human | 2 | Reoviridae,Rotavirus,Rotavirus A | seg. 9 | HQ834201,FJ031029 |
| Lamb rotavirus | NC_011504 | vertebrates,human | 4 | Reoviridae,Rotavirus,Rotavirus A | seg. 10 | HQ834205,JQ031148,FJ031022,AY219873 |

| Taxonomy | NCBI Reference Sequence ID | Host | No. of Genomes | Lineage | Segment Count | Genbank Accession ID |
|---|---|---|---|---|---|---|
| Lamb rotavirus | NC_011505 | vertebrates,human | 4 | Reoviridae,Rotavirus,Rotavirus A | seg. 11 | FJQ31023,HQ834206,JQ031151,AY622998 |
| Lamb rotavirus | NC_011506 | vertebrates,human | 3 | Reoviridae,Rotavirus,Rotavirus A | seg. 2 | HQ834198,JQ013503,FJQ31025 |
| Lamb rotavirus | NC_011507 | vertebrates,human | 3 | Reoviridae,Rotavirus,Rotavirus A | seg. 1 | JQ013502,HQ834197,FJQ31024 |
| Lamb rotavirus | NC_011508 | vertebrates,human | 3 | Reoviridae,Rotavirus,Rotavirus A | seg. 3 | HQ834207,FJQ31026,JQ013504 |
| Lamb rotavirus | NC_011509 | vertebrates,human | 6 | Reoviridae,Rotavirus,Rotavirus A | seg. 6 | JQ031150,L11602,L11595,HQ834200,FJQ31028, L11596 |
| Lamb rotavirus | NC_011510 | vertebrates,human | 3 | Reoviridae,Rotavirus,Rotavirus A | seg. 4 | HQ834199,FJQ31027,L11599 |
| Lapine rotavirus | NC_011500 | vertebrates,human | 4 | Reoviridae,Rotavirus,Rotavirus A | seg. 5 | AF084549,AF084550,JQ423897,AF084551 |
| Lapine rotavirus | NC_011501 | vertebrates,human | 1 | Reoviridae,Rotavirus,Rotavirus A | seg. 7 | JQ423899 |
| Lapine rotavirus | NC_011502 | vertebrates,human | 1 | Reoviridae,Rotavirus,Rotavirus A | seg. 8 | JQ423898 |
| Lapine rotavirus | NC_011503 | vertebrates,human | 2 | Reoviridae,Rotavirus,Rotavirus A | seg. 9 | U62153,JQ423907 |
| Lapine rotavirus | NC_011504 | vertebrates,human | 1 | Reoviridae,Rotavirus,Rotavirus A | seg. 10 | JQ423900 |
| Lapine rotavirus | NC_011505 | vertebrates,human | 1 | Reoviridae,Rotavirus,Rotavirus A | seg. 11 | JQ423901 |
| Lapine rotavirus | NC_011506 | vertebrates,human | 1 | Reoviridae,Rotavirus,Rotavirus A | seg. 2 | JQ423903 |
| Lapine rotavirus | NC_011507 | vertebrates,human | 1 | Reoviridae,Rotavirus,Rotavirus A | seg. 1 | JQ423902 |
| Lapine rotavirus | NC_011508 | vertebrates,human | 1 | Reoviridae,Rotavirus,Rotavirus A | seg. 3 | JQ423904 |
| Lapine rotavirus | NC_011509 | vertebrates,human | 1 | Reoviridae,Rotavirus,Rotavirus A | seg. 6 | JQ423906 |
| Lapine rotavirus | NC_011510 | vertebrates,human | 5 | Reoviridae,Rotavirus,Rotavirus A | seg. 4 | U62150,JQ423905,U62151,U62152,U621549 |
| Lapine rotavirus strain BAP (wildtype) | NC_011504 | vertebrates,human | 1 | Reoviridae,Rotavirus,Rotavirus A | seg. 10 | AF144796 |
| Lapine rotavirus strain BAP-2 | NC_011504 | vertebrates,human | 1 | Reoviridae,Rotavirus,Rotavirus A | seg. 10 | AF144795 |
| Lapine rotavirus strain C-11 | NC_011504 | vertebrates,human | 1 | Reoviridae,Rotavirus,Rotavirus A | seg. 10 | AF144793 |
| Lapine rotavirus strain R-2 | NC_011504 | vertebrates,human | 1 | Reoviridae,Rotavirus,Rotavirus A | seg. 10 | AF144794 |
| Lassa virus | NC_004296 | vertebrates,human | 16 | Arenaviridae,Arenavirus,Lassa virus | seg. S | AY628208,X52400,AF181854,AY628201,AF333969,AY628207,AY628206,HQ688672,AF246121,AY628205,AY628203,HQ688673,AF181853,JQ4324,AY179173,FR832711 |
| Lassa virus | NC_004297 | vertebrates,human | 11 | Arenaviridae,Arenavirus,Lassa virus | seg. L | HQ688675,AY179172,AY628204,U63094,AY179171,AY179174,F |

-continued

| Taxonomy | NCBI Reference Sequence ID | Host | No. of Genomes | Lineage | Segment Count | Genbank Accession ID |
|---|---|---|---|---|---|---|
| | | | | | | R832710,AY628200,U73034,HQ688674,AY628202 |
| Latino virus | NC_010758 | vertebrates,human | 2 | Arenaviridae,Arenavirus,Latino virus | seg. S | AF485259,AF512830 |
| Latino virus | NC_010760 | vertebrates,human | 1 | Arenaviridae,Arenavirus,Latino virus | seg. L | EU627612 |
| Lechiguanas virus | NC_003466 | vertebrates,human | 1 | Bunyaviridae,Hantavirus,Andes virus | seg. S | AF482714 |
| Lechiguanas virus | NC_003467 | vertebrates,human | 1 | Bunyaviridae,Hantavirus,Andes virus | seg. M | AF028022 |
| Lloviu virus | NC_016144 | vertebrates,human | 1 | Filoviridae,Lloviu virus | — | JF828358 |
| Lordsdale virus | NC_001959 | vertebrates,human | 1 | Caliciviridae,Norovirus,Norwalk virus | — | X86557 |
| Lujo virus | NC_012776 | vertebrates,human | 2 | Arenaviridae,Arenavirus,Lujo virus | seg. S | JXQ17360,FJ952384 |
| Lujo virus | NC_012777 | vertebrates,human | 2 | Arenaviridae,Arenavirus,Lujo virus | seg. L | JXQ17362,FJ952385 |
| Luna virus | NC_016152 | vertebrates,human | 5 | Arenaviridae,Arenavirus,Luna virus | seg. S | AB586644,AB697691,AB586646,AB702940,AB693148 |
| Luna virus | NC_016153 | vertebrates,human | 5 | Arenaviridae,Arenavirus,Luna virus | seg. L | AB693149,AB586645,AB586647,AB702941,AB697692 |
| Lunk virus NKS-1 | NC_018710 | vertebrates,human | 1 | Arenaviridae,Arenavirus,Lunk virus NKS-1 | — | AB693150 |
| Lunk virus NKS-1 | NC_018711 | vertebrates,human | 1 | Arenaviridae,Arenavirus,Lunk virus NKS-1 | — | AB693151 |
| Lymphocytic choriomeningitis virus | NC_004291 | vertebrates,human | 16 | Arenaviridae,Arenavirus,Lymphocytic choriomeningitis virus | seg. L | JN872494,EU480451,DQ868488,EU195889,JQ4331,AB627954,EU480453,DQ868484,DQ286932,DQ868486,AB627956,AB477530,DQ361066,GQ862981,AB627955,AF004519 |
| Lymphocytic choriomeningitis virus | NC_004294 | vertebrates,human | 25 | Arenaviridae,Arenavirus,Lymphocytic choriomeningitis virus | seg. S | JN872495,AY847351,EU480452,AB627952,AB261991,DQ868485,DQ361065,FJ895882,DQ286931,DQ868487,FJ895883,AF325214,AF325215,M22138,FJ895884,AB261990,GQ862982,DQ118959,AB627951,JN687949,AB627953,EU480450,M20869,AY847350,DQ868483 |
| Macaca fascicularis papillomavirus 2 | NC_015691 | vertebrates,human | 1 | Papillomaviridae,Betapapillomavirus,Betapapillomavirus 6 | — | GU014531 |
| Macaca fascicularis papillomavirus type 1 | NC_001531 | vertebrates,human | 1 | Papillomaviridae,Betapapillomavirus,Betapapillomavirus 1 | — | EF028290 |

-continued

| Taxonomy | NCBI Reference Sequence ID | Host | No. of Genomes | Lineage | Segment Count | Genbank Accession ID |
|---|---|---|---|---|---|---|
| Machupo virus | NC_005078 | vertebrates,human | 3 | Arenaviridae,Arenavirus,Machupo virus | seg. S | JN794584,AY129248, JN794586 |
| Machupo virus | NC_005079 | vertebrates,human | 3 | Arenaviridae,Arenavirus,Machupo virus | seg. L | AY358021,JN794583, JN794585 |
| Maciel virus | NC_003466 | vertebrates,human | 1 | Bunyaviridae,Hantavirus,Andes virus | seg. S | AF482716 |
| Mamastrovirus 1 | NC_001943 | vertebrates,human | 1 | Astroviridae,Mamastrovirus,Mamastrovirus 1 | — | Z25771 |
| Maporal virus | NC_003466 | vertebrates,human | 1 | Bunyaviridae,Hantavirus,Andes virus | seg. S | AY267347 |
| Maporal virus | NC_003467 | vertebrates,human | 1 | Bunyaviridae,Hantavirus,Andes virus | seg. M | AY363179 |
| Mapuera virus | NC_009489 | vertebrates,human | 1 | Paramyxoviridae,Rubulavirus,Mapuera virus | — | EF095490 |
| Marburg marburgvirus | NC_001608 | vertebrates,human | 36 | Filoviridae,Marburgvirus,Marburg marburgvirus | — | JX458844,JX458854, JX458858,JX458852, JX458847,JX458827, JX458843,JX458830, JX458833,JX458850, JX458857,JX458849, JX458842,JX458831, JX458835,JX458826, JX458836,JX458851, JX458825,KC545388, JX458856,JX458845, JX458838,JX458834, JX458846,JX458829, JX458848,JX458837, JX458828,JX458832, JX458841,JX458853, JX458839,KC545387, JX458855,JX458840 |
| Measles virus | NC_001498 | vertebrates,human | 50 | Paramyxoviridae,Morbillivirus,Measles virus | — | EU435017,DQ345721 ,AB481088,EU29355 0,K01711,E04903,DQ 227318,BD137596,B D137590,EU293551, AY730614,AB254456 ,FJ416067,AB016162 ,AB046218,DQ22732 1,AB591381,JF72765 0,BD137593,AF2662 88,FJ161211,JF7276 49,FJ211590,DQ3457 22,HM439386,Z6651 7,DQ227320,FJ21158 3,BD137595,AB0129 49,EU293552,DQ211 902,AB481087,GQ37 6027,EU293549,GQ3 76026,BD137592,AB 032167,BD137591,D 0345723,BD137597, |

-continued

| Taxonomy | NCBI Reference Sequence ID | Host | No. of Genomes | Lineage | Segment Count | Genbank Accession ID |
|---|---|---|---|---|---|---|
| | | | | | | FJ416068,S58435,JF791787,EF033071,EU293548,BD137594,DQ227319,AB012948,FJ211589 |
| Measles virus genotype D4 | NC_001498 | vertebrates,human | 1 | Paramyxoviridae,Morbillivirus,Measles virus | — | KC164757 |
| Measles virus genotype G3 | NC_001498 | vertebrates,human | 1 | Paramyxoviridae,Morbillivirus,Measles virus | — | KC164758 |
| Measles virus strain AIK-C | NC_001498 | vertebrates,human | 1 | Paramyxoviridae,Morbillivirus,Measles virus | — | AF266286 |
| Measles virus strain Edmonston-Zagreb | NC_001498 | vertebrates,human | 3 | Paramyxoviridae,Morbillivirus,Measles virus | — | AY486083,AY486084,AF266290 |
| Measles virus strain MVi/Arizona,USA/11,08/2 | NC_001498 | vertebrates,human | 1 | Paramyxoviridae,Morbillivirus,Measles virus | — | JN635406 |
| Measles virus strain MVi/California,USA/16,03 | NC_001498 | vertebrates,human | 1 | Paramyxoviridae,Morbillivirus,Measles virus | — | JN635410 |
| Measles virus strain MVi/California,USA/8,04 | NC_001498 | vertebrates,human | 1 | Paramyxoviridae,Morbillivirus,Measles virus | — | JN635409 |
| Measles virus strain MVi/Florida,USA/19,09 | NC_001498 | vertebrates,human | 1 | Paramyxoviridae,Morbillivirus,Measles virus | — | JN635403 |
| Measles virus strain MVi/New Jersey,USA/45,05 | NC_001498 | vertebrates,human | 1 | Paramyxoviridae,Morbillivirus,Measles virus | — | JN635408 |
| Measles virus strain MVi/New York,USA/26,09/3 | NC_001498 | vertebrates,human | 1 | Paramyxoviridae,Morbillivirus,Measles virus | — | JN635402 |
| Measles virus strain MVi/Pennsylvania,USA/20,09 | NC_001498 | vertebrates,human | 1 | Paramyxoviridae,Morbillivirus,Measles virus | — | JN635411 |
| Measles virus strain MVi/Texas,USA/4,07 | NC_001498 | vertebrates,human | 1 | Paramyxoviridae,Morbillivirus,Measles virus | — | JN635407 |
| Measles virus strain MVi/Virginia,USA/15,09 | NC_001498 | vertebrates,human | 1 | Paramyxoviridae,Morbillivirus,Measles virus | — | JN635404 |
| Measles virus strain MVi/VVashington, USA/18,0 8/1 | NC_001498 | vertebrates,human | 1 | Paramyxoviridae,Morbillivirus,Measles virus | — | JN635405 |
| Measles virus strain Moraten | NC_001498 | vertebrates,human | 1 | Paramyxoviridae,Morbillivirus,Measles virus | — | AF266287 |
| Measles virus strain Rubeovax | NC_001498 | vertebrates,human | 1 | Paramyxoviridae,Morbillivirus,Measles virus | — | AF266289 |
| Measles virus strain Schwarz | NC_001498 | vertebrates,human | 1 | Paramyxoviridae,Morbillivirus,Measles virus | — | AF266291 |
| Menangle virus | NC_007620 | vertebrates,human | 2 | Paramyxoviridae,Rubulavirus,Menangle virus | — | AF326114,JX112711 |
| Merkel cell polyomavirus | NC_010277 | vertebrates,human | 41 | Polyomaviridae,Polyomavirus,Merkel cell polyomavirus | — | HM011552,HM011555,HM011554,KC202810,JN383840,JQ479319,EU375803,HM011557,JN383838,FJ173815,HM011547,HM011542,HM011544,JN3 |

| Taxonomy | NCBI Reference Sequence ID | Host | No. of Genomes | Lineage | Segment Count | Genbank Accession ID |
|---|---|---|---|---|---|---|
| Mobala virus | NC_007903 | vertebrates,human | 1 | Arenaviridae,Arenavirus,Mobala virus | seg. S | 83841,HM01538,EU375804,HM011550,J0479315,HM011556,JF813001,JQ479320,HM355825,JF813000,HM011543,FJ46433,7,HM011546,HM0115 40,JF812999,HM011 548,HM011553,JF81

-continued

| Taxonomy | NCBI Reference Sequence ID | Host | No. of Genomes | Lineage | Segment Count | Genbank Accession ID |
|---|---|---|---|---|---|---|
| | | | | | | 052,AXQ81133,FJ211586,AB040874,AB0O0388,JN635498,AF467767,AF314561,EU370207,FJ556896,EU884413,AF314558,AB827968,JX287389,JX287388,AY669145,JX287386,AY508995,JX287391 |
| Mumps virus strain Jeryl Lynn | NC_002200 | vertebrates,human | 3 | Paramyxoviridae,Rubulavirus,Mumps virus | — | FN431985,AF345290,AF338106 |
| Mumps virus strain L-Zagreb | NC_002200 | vertebrates,human | 2 | Paramyxoviridae,Rubulavirus,Mumps virus | — | AY685920,AY685921 |
| Murine pneumonia virus | NC_006579 | vertebrates,human | 1 | Paramyxoviridae,Pneumovirus,Murine pneumonia virus | — | AY729016 |
| Nariva virus | NC_017937 | vertebrates,human | 1 | Paramyxoviridae, Nariva virus | — | FJ362497 |
| Newcastle disease virus | NC_002617 | vertebrates,human | 216 | Paramyxoviridae,Avulavirus,Newcastle disease virus | — | KC542892,KC152049,JN986838,KC542900,JF966387,KC920893,KC542904,HM117720,JQ979176,HQ412767,JX443519,JX193074,JF343539,FJ430160,GQ338309,GQ849007,KC542897,AY935495,FJ436302,HM357251,HM125898,JQ013039,FJ386392,BD218398,JX532092,JX193081,DQ485231,JF343538,HQ697254,AY562986,GQ994433,KC894391,EU293914,AY935493,KC844235,HQ902590,GQ288378,DQ486859,JX401403,GQ918280,HQ317395,AY935496,HQ717357,FJ766527,JX401404,JN653340,JX193079,AB524406,KC542902,JN800306,FJ754271,JF950510,AY935499,JX390609,D0659677,JQ015296,HM063424,JX316216,AB534205,Y18898,F |

| Taxonomy | NCBI Reference Sequence ID | Host | No. of Genomes | Lineage | Segment Count | Genbank Accession ID |
|---|---|---|---|---|---|---|
| | | | | | | J436305,HM063425, KC542896,AY935494 ,HQ697255,KC55196 7,FJ794269,KC54289 3,JQ993431,KC5429 13,HQ266602,JX193 083,AY225110,AY93 5489,GQ228389,JF8 27027,HM063423,FJ 751918,GU187941,J N599167,GQ288391, FJ872531,GQ994434 ,AY741404,HM06342 2,AY935497,HQ0083 37,GQ338310,JXQ12 096,KC542914,AY93 5492,KC934169,FJ38 6393,JX393313,KF77 1883,HM188399,JF9 50509,EU289028,AY 562987,AY562985,JX 193078,FJ436303,JN 688863,AY865652,JN 400896,KF727980,G 0288390,KC542908, JF893453,AY935498, GU143550,KC152048 ,KC542901,JQ01529 5,JN400895,KC90618 8,JN688862,FJ98619 2,KC542905,EU2890 29,FJ386396,JN6183 49,EU140955,FJ4363 06,GU978777,JX524 203,JX401405,JN653 339,FJ766529,JN682 211,JF827026,JX193 082,JN682210,GQ28 8392,HQ839733,AF0 77761,JN688865,DQ 060053,AB524405,K C542911,KF740478, DQ839397,KC461214 ,KC542906,JQ71394 4,JN986837,GU5643 99,AY562990,GQ288 380,GQ338311,AY56 2989,FJ766526,GU58 |

| Taxonomy | NCBI Reference Sequence ID | Host | No. of Genomes | Lineage | Segment Count | Genbank Accession ID |
|---|---|---|---|---|---|---|
| Newcastle disease virus B1 | NC_002617 | vertebrates,human | 2 | Paramyxoviridae,Avulavirus,Newcastle disease virus | — | AF375823,AF309418 |
| Nipah virus | NC_002728 | vertebrates,human | 11 | Paramyxoviridae,Henipavirus,Nipah virus | — | AJ627196,JN808857, AJ564621,AY029768, F -continued

| Taxonomy | NCBI Reference Sequence ID | Host | No. of Genomes | Lineage | Segment Count | Genbank Accession ID |
|---|---|---|---|---|---|---|
| Norovirus Hu/GI.1/ 8CKII Ic/1974/USA | NC_001959 | vertebrates,human | 1 | Caliciviridae,Norovirus,Norwalk virus | — | KF429773 |
| Norovirus Hu/GI.1/ 8FI 1a/1968/USA | NC_001959 | vertebrates,human | 1 | Caliciviridae,Norovirus,Norwalk virus | — | JXQ23285 |
| Norovirus Hu/GI.1/8K/1979/USA | NC_001959 | vertebrates,human | 1 | Caliciviridae,Norovirus,Norwalk virus | — | KF429783 |
| Norovirus Hu/GI.1/8MC/1978/USA | NC_001959 | vertebrates,human | 1 | Caliciviridae,Norovirus,Norwalk virus | — | KF429789 |
| Norovirus Hu/GI.1/ 8McI11/1973/USA | NC_001959 | vertebrates,human | 1 | Caliciviridae,Norovirus,Norwalk virus | — | KF429770 |
| Norovirus Hu/GI.1/ 8MoII I L/1972/USA | NC_001959 | vertebrates,human | 1 | Caliciviridae,Norovirus,Norwalk virus | — | KF429761 |
| Norovirus Hu/GI,1/8U11If/1973/USA | NC_001959 | vertebrates,human | 1 | Caliciviridae,Norovirus,Norwalk virus | — | KF429774 |
| Norovirus Hu/GI.1/8W/1951/USA | NC_001959 | vertebrates,human | 1 | Caliciviridae,Norovirus,Norwalk virus | — | KF429765 |
| Norovirus Hu/GI.1/CH4XQ533/2009/USA | NC_001959 | vertebrates,human | 1 | Caliciviridae,Norovirus,Norwalk virus | — | KF039731 |
| Norovirus Hu/GI.1/CHA2A014/2008/USA | NC_001959 | vertebrates,human | 1 | Caliciviridae,Norovirus,Norwalk virus | — | KF039728 |
| Norovirus Hu/GI.1/CHA3A007/2008/USA | NC_001959 | vertebrates,human | 1 | Caliciviridae,Norovirus,Norwalk virus | — | KF039735 |
| Norovirus Hu/GI.1/CHA5A010/2009/USA | NC_001959 | vertebrates,human | 1 | Caliciviridae,Norovirus,Norwalk virus | — | KF039732 |
| Norovirus Hu/GI.1/CHA6A003_20091 028/2009/U SA | NC_001959 | vertebrates,human | 1 | Caliciviridae,Norovirus,Norwalk virus | — | KF039727 |
| Norovirus Hu/GI.1/CHA6A003_20091 031/2009/U SA | NC_001959 | vertebrates,human | 1 | Caliciviridae,Norovirus,Norwalk virus | — | KF039726 |
| Norovirus Hu/GI.1/CHA6A003_20091 104/2009/U SA | NC_001959 | vertebrates,human | 1 | Caliciviridae,Norovirus,Norwalk virus | — | KF039737 |
| Norovirus Hu/GI.1/CHA6A007/2010/USA | NC_001959 | vertebrates,human | 1 | Caliciviridae,Norovirus,Norwalk virus | — | KF039729 |
| Norovirus Hu/GI.1/CHA6A014/2009/USA | NC_001959 | vertebrates,human | 1 | Caliciviridae,Norovirus,Norwalk virus | — | KF039734 |
| Norovirus Hu/GI.1/CHA7A009/2010/USA | NC_001959 | vertebrates,human | 1 | Caliciviridae,Norovirus,Norwalk virus | — | KF039725 |

| Taxonomy | NCBI Reference Sequence ID | Host | No. of Genomes | Lineage | Segment Count | Genbank Accession ID |
|---|---|---|---|---|---|---|
| Norovirus Hu/GI.1/CHA7A011/2010/USA | NC_001959 | vertebrates,human | 1 | Caliciviridae,Norovirus,Norwalk virus | — | KF039736 |
| Norovirus Hu/GI.1/CHA9A004_20110419/2011/USA | NC_001959 | vertebrates,human | 1 | Caliciviridae,Norovirus,Norwalk virus | — | KF039730 |
| Norovirus Hu/GI.1/CHA9A004_20110426/2011/USA | NC_001959 | vertebrates,human | 1 | Caliciviridae,Norovirus,Norwalk virus | — | KF039733 |
| Norovirus Hu/GI.2/Jingzhou/2013401/CHN | NC_001959 | vertebrates,human | 1 | Caliciviridae,Norovirus,Norwalk virus | — | KF306212 |
| Norovirus Hu/GI.2/Leuven/2003/BEL | NC_001959 | vertebrates,human | 1 | Caliciviridae,Norovirus,Norwalk virus | — | FJ515294 |
| Norovirus Hu/GI.6/Kingston/ACT160D/2010/AU | NC_001959 | vertebrates,human | 1 | Caliciviridae,Norovirus,Norwalk virus | — | JQ388274 |
| Norovirus Hu/GI/10360/2010/VNM | NC_001959 | vertebrates,human | 1 | Caliciviridae,Norovirus,Norwalk virus | — | JQ911594 |
| Norovirus Hu/GI/30257/2009/VNM | NC_001959 | vertebrates,human | 1 | Caliciviridae,Norovirus,Norwalk virus | — | KC409317 |
| Norovirus Hu/GI/Otofuke/1979/JP | NC_001959 | vertebrates,human | 1 | Caliciviridae,Norovirus,Norwalk virus | — | AB187514 |
| Norovirus Hu/GII-4/Aichi1/2007/JP | NC_001959 | vertebrates,human | 1 | Caliciviridae,Norovirus,Norwalk virus | — | AB541201 |
| Norovirus Hu/GII-4/Aichi1/2008/JP | NC_001959 | vertebrates,human | 1 | Caliciviridae,Norovirus,Norwalk virus | — | AB541202 |
| Norovirus Hu/GII-4/Aichi2/2007/JP | NC_001959 | vertebrates,human | 1 | Caliciviridae,Norovirus,Norwalk virus | — | AB541203 |
| Norovirus Hu/GII-4/Aichi2/2008/JP | NC_001959 | vertebrates,human | 1 | Caliciviridae,Norovirus,Norwalk virus | — | AB541204 |
| Norovirus Hu/GII-4/Aichi3/2006/JP | NC_001959 | vertebrates,human | 1 | Caliciviridae,Norovirus,Norwalk virus | — | AB447446 |
| Norovirus Hu/GII-4/Aichi3/2007/JP | NC_001959 | vertebrates,human | 1 | Caliciviridae,Norovirus,Norwalk virus | — | AB541205 |
| Norovirus Hu/GII-4/Aichi3/2008/JP | NC_001959 | vertebrates,human | 1 | Caliciviridae,Norovirus,Norwalk virus | — | AB541206 |
| Norovirus Hu/GII-4/Aichi4/2006/JP | NC_001959 | vertebrates,human | 1 | Caliciviridae,Norovirus,Norwalk virus | — | AB447447 |
| Norovirus Hu/GII-4/Aichi4/2007/JP | NC_001959 | vertebrates,human | 1 | Caliciviridae,Norovirus,Norwalk virus | — | AB541207 |
| Norovirus Hu/GII-4/Aichi4/2008/JP | NC_001959 | vertebrates,human | 1 | Caliciviridae,Norovirus,Norwalk virus | — | AB541208 |
| Norovirus Hu/GII-4/Aichi5/2007/JP | NC_001959 | vertebrates,human | 1 | Caliciviridae,Norovirus,Norwalk virus | — | AB541209 |
| Norovirus Hu/GII-4/Aichi5/2008/JP | NC_001959 | vertebrates,human | 1 | Caliciviridae,Norovirus,Norwalk virus | — | AB541210 |

| Taxonomy | NCBI Reference Sequence ID | Host | Lineage | No. of Genomes | Segment Count | Genbank Accession ID |
|---|---|---|---|---|---|---|
| Norovirus Hu/GII-4/Akita1/2006/JP | NC_001959 | vertebrates,human | Caliciviridae,Norovirus,Norwalk virus | 1 | — | AB447436 |
| Norovirus Hu/GII-4/Akita1/2007/JP | NC_001959 | vertebrates,human | Caliciviridae,Norovirus,Norwalk virus | 1 | — | AB541211 |
| Norovirus Hu/GII-4/Akita2/2006/JP | NC_001959 | vertebrates,human | Caliciviridae,Norovirus,Norwalk virus | 1 | — | AB447437 |
| Norovirus Hu/GII-4/Akita2/2008/JP | NC_001959 | vertebrates,human | Caliciviridae,Norovirus,Norwalk virus | 1 | — | AB541213 |
| Norovirus Hu/GII-4/Akita3/2007/JP | NC_001959 | vertebrates,human | Caliciviridae,Norovirus,Norwalk virus | 1 | — | AB541214 |
| Norovirus Hu/GII-4/Akita3/2008/JP | NC_001959 | vertebrates,human | Caliciviridae,Norovirus,Norwalk virus | 1 | — | AB541215 |
| Norovirus Hu/GII-4/Akita4/2006/JP | NC_001959 | vertebrates,human | Caliciviridae,Norovirus,Norwalk virus | 1 | — | AB447438 |
| Norovirus Hu/GII-4/Akita4/2008/JP | NC_001959 | vertebrates,human | Caliciviridae,Norovirus,Norwalk virus | 1 | — | AB541216 |
| Norovirus Hu/GII-4/Akita5/2006/JP | NC_001959 | vertebrates,human | Caliciviridae,Norovirus,Norwalk virus | 1 | — | AB541439 |
| Norovirus Hu/GII-4/Akita5/2007/JP | NC_001959 | vertebrates,human | Caliciviridae,Norovirus,Norwalk virus | 1 | — | AB541217 |
| Norovirus Hu/GII-4/Aomori1/2006/JP | NC_001959 | vertebrates,human | Caliciviridae,Norovirus,Norwalk virus | 1 | — | AB447432 |
| Norovirus Hu/GII-4/Aomori1/2007/JP | NC_001959 | vertebrates,human | Caliciviridae,Norovirus,Norwalk virus | 1 | — | AB541218 |
| Norovirus Hu/GII-4/Aomori1/2008/JP | NC_001959 | vertebrates,human | Caliciviridae,Norovirus,Norwalk virus | 1 | — | AB541219 |
| Norovirus Hu/GII-4/Aomori2/2006/JP | NC_001959 | vertebrates,human | Caliciviridae,Norovirus,Norwalk virus | 1 | — | AB447433 |
| Norovirus Hu/GII-4/Aomori2/2006JP | NC_001959 | vertebrates,human | Caliciviridae,Norovirus,Norwalk virus | 1 | — | AB541220 |
| Norovirus Hu/GII-4/Aomori2/2007/JP | NC_001959 | vertebrates,human | Caliciviridae,Norovirus,Norwalk virus | 1 | — | AB541222 |
| Norovirus Hu/GII-4/Aomori3/2007/JP | NC_001959 | vertebrates,human | Caliciviridae,Norovirus,Norwalk virus | 1 | — | AB541223 |
| Norovirus Hu/GII-4/Aomori3/2008/JP | NC_001959 | vertebrates,human | Caliciviridae,Norovirus,Norwalk virus | 1 | — | AB447434 |
| Norovirus Hu/GII-4/Aomori4/2006/JP | NC_001959 | vertebrates,human | Caliciviridae,Norovirus,Norwalk virus | 1 | — | AB541224 |
| Norovirus Hu/GII-4/Aomori4/2007/JP | NC_001959 | vertebrates,human | Caliciviridae,Norovirus,Norwalk virus | 1 | — | AB541225 |
| Norovirus Hu/GII-4/Aomori4/2008/JP | NC_001959 | vertebrates,human | Caliciviridae,Norovirus,Norwalk virus | 1 | — | AB447435 |
| Norovirus Hu/GII-4/Aomori5/2006/JP | NC_001959 | vertebrates,human | Caliciviridae,Norovirus,Norwalk virus | 1 | — | AB541226 |
| Norovirus Hu/GII-4/Aomori5/2007/JP | NC_001959 | vertebrates,human | Caliciviridae,Norovirus,Norwalk virus | 1 | — | AB541227 |
| Norovirus Hu/GII-4/CBNU2/2007/KR | NC_001959 | vertebrates,human | Caliciviridae,Norovirus,Norwalk virus | 1 | — | JQ622197 |

-continued

| Taxonomy | NCBI Reference Sequence ID | Host | No. of Genomes | Lineage | Segment Count | Genbank Accession ID |
|---|---|---|---|---|---|---|
| Norovirus Hu/GII-4/CGMHQ1/2006/TW | NC_001959 | vertebrates,human | 1 | Caliciviridae,Norovirus,Norwalk virus | — | JN400599 |
| Norovirus Hu/GII-4/CGMHQ2/2006/TW | NC_001959 | vertebrates,human | 1 | Caliciviridae,Norovirus,Norwalk virus | — | JN400600 |
| Norovirus Hu/GII-4/CGMHQ3/2006/TW | NC_001959 | vertebrates,human | 1 | Caliciviridae,Norovirus,Norwalk virus | — | JN400601 |
| Norovirus Hu/GII-4/CGMHQ4/2006/TW | NC_001959 | vertebrates,human | 1 | Caliciviridae,Norovirus,Norwalk virus | — | JN400602 |
| Norovirus Hu/GII-4/CGMHQ5/2006/TW | NC_001959 | vertebrates,human | 1 | Caliciviridae,Norovirus,Norwalk virus | — | JN400603 |
| Norovirus Hu/GII-4/CGMHQ6/2006/TW | NC_001959 | vertebrates,human | 1 | Caliciviridae,Norovirus,Norwalk virus | — | JN400604 |
| Norovirus Hu/GII-4/CGMHQ7/2006/TW | NC_001959 | vertebrates,human | 1 | Caliciviridae,Norovirus,Norwalk virus | — | JN400605 |
| Norovirus Hu/GII-4/CGMHQ8/2006/TW | NC_001959 | vertebrates,human | 1 | Caliciviridae,Norovirus,Norwalk virus | — | JN400606 |
| Norovirus Hu/GII-4/CGMHQ9/2006/TW | NC_001959 | vertebrates,human | 1 | Caliciviridae,Norovirus,Norwalk virus | — | JN400607 |
| Norovirus Hu/GII-4/CGMH10/2006/TW | NC_001959 | vertebrates,human | 1 | Caliciviridae,Norovirus,Norwalk virus | — | JN400608 |
| Norovirus Hu/GII-4/CGMH11/2006/TW | NC_001959 | vertebrates,human | 1 | Caliciviridae,Norovirus,Norwalk virus | — | JN400609 |
| Norovirus Hu/GII-4/CGMH12/2007/TW | NC_001959 | vertebrates,human | 1 | Caliciviridae,Norovirus,Norwalk virus | — | JN400610 |
| Norovirus Hu/GII-4/CGMH13/2007/TW | NC_001959 | vertebrates,human | 1 | Caliciviridae,Norovirus,Norwalk virus | — | JN400611 |
| Norovirus Hu/GII-4/CGMH14/2007/TW | NC_001959 | vertebrates,human | 1 | Caliciviridae,Norovirus,Norwalk virus | — | JN400612 |
| Norovirus Hu/GII-4/CGMH15/2007/TW | NC_001959 | vertebrates,human | 1 | Caliciviridae,Norovirus,Norwalk virus | — | JN400613 |
| Norovirus Hu/GII-4/CGMH16/2007/TW | NC_001959 | vertebrates,human | 1 | Caliciviridae,Norovirus,Norwalk virus | — | JN400614 |
| Norovirus Hu/GII-4/CGMH17/2007/TW | NC_001959 | vertebrates,human | 1 | Caliciviridae,Norovirus,Norwalk virus | — | JN400615 |
| Norovirus Hu/GII-4/CGMH18/2008/TW | NC_001959 | vertebrates,human | 1 | Caliciviridae,Norovirus,Norwalk virus | — | JN400616 |
| Norovirus Hu/GII-4/CGMH19/2009/TW | NC_001959 | vertebrates,human | 1 | Caliciviridae,Norovirus,Norwalk virus | — | JN400617 |
| Norovirus Hu/GII-4/CGMH20/2009/TW | NC_001959 | vertebrates,human | 1 | Caliciviridae,Norovirus,Norwalk virus | — | JN400618 |
| Norovirus Hu/GII-4/CGMH21/2010/TW | NC_001959 | vertebrates,human | 1 | Caliciviridae,Norovirus,Norwalk virus | — | JN400619 |
| Norovirus Hu/GII-4/CGMH22/2010/TW | NC_001959 | vertebrates,human | 1 | Caliciviridae,Norovirus,Norwalk virus | — | JN400620 |
| Norovirus Hu/GII-4/CGMH23/2010/TW | NC_001959 | vertebrates,human | 1 | Caliciviridae,Norovirus,Norwalk virus | — | JN400621 |
| Norovirus Hu/GII-4/CGMH24/2010/TW | NC_001959 | vertebrates,human | 1 | Caliciviridae,Norovirus,Norwalk virus | — | JN400622 |

| Taxonomy | NCBI Reference Sequence ID | Host | No. of Genomes | Lineage | Segment Count | Genbank Accession ID |
|---|---|---|---|---|---|---|
| Norovirus Hu/GII-4/CGMH25/2010/TW | NC_001959 | vertebrates,human | 1 | Caliciviridae,Norovirus,Norwalk virus | — | JN400623 |
| Norovirus Hu/GII-4/CGMH26/2010/TW | NC_001959 | vertebrates,human | 1 | Caliciviridae,Norovirus,Norwalk virus | — | JN400624 |
| Norovirus Hu/GII-4/CGMH27/2010/TW | NC_001959 | vertebrates,human | 1 | Caliciviridae,Norovirus,Norwalk virus | — | JN400625 |
| Norovirus Hu/GII-4/CGMH28/2010/TW | NC_001959 | vertebrates,human | 1 | Caliciviridae,Norovirus,Norwalk virus | — | JN400626 |
| Norovirus Hu/GII-4/CUK-3/2008/KR | NC_001959 | vertebrates,human | 1 | Caliciviridae,Norovirus,Norwalk virus | — | FJ514242 |
| Norovirus Hu/GII-4/Chiba1/2007/JP | NC_001959 | vertebrates,human | 1 | Caliciviridae,Norovirus,Norwalk virus | — | AB541228 |
| Norovirus Hu/GII-4/Chiba1/2008/JP | NC_001959 | vertebrates,human | 1 | Caliciviridae,Norovirus,Norwalk virus | — | AB541229 |
| Norovirus Hu/GII-4/Chiba2/2007/JP | NC_001959 | vertebrates,human | 1 | Caliciviridae,Norovirus,Norwalk virus | — | AB541230 |
| Norovirus Hu/GII-4/Chiba2/2008/JP | NC_001959 | vertebrates,human | 1 | Caliciviridae,Norovirus,Norwalk virus | — | AB541231 |
| Norovirus Hu/GII-4/Chiba4/2007/JP | NC_001959 | vertebrates,human | 1 | Caliciviridae,Norovirus,Norwalk virus | — | AB541232 |
| Norovirus Hu/GII-4/Chiba4/2008/JP | NC_001959 | vertebrates,human | 1 | Caliciviridae,Norovirus,Norwalk virus | — | AB541233 |
| Norovirus Hu/GII-4/Chiba5/2007/JP | NC_001959 | vertebrates,human | 1 | Caliciviridae,Norovirus,Norwalk virus | — | AB541234 |
| Norovirus Hu/GII-4/Chiba5/2008/JP | NC_001959 | vertebrates,human | 1 | Caliciviridae,Norovirus,Norwalk virus | — | AB541235 |
| Norovirus Hu/GII-4/Ehime1/2006/JP | NC_001959 | vertebrates,human | 1 | Caliciviridae,Norovirus,Norwalk virus | — | AB447453 |
| Norovirus Hu/GII-4/Ehime1/2007/JP | NC_001959 | vertebrates,human | 1 | Caliciviridae,Norovirus,Norwalk virus | — | AB541236 |
| Norovirus Hu/GII-4/Ehime1/2008/JP | NC_001959 | vertebrates,human | 1 | Caliciviridae,Norovirus,Norwalk virus | — | AB541237 |
| Norovirus Hu/GII-4/Ehime2/2006/JP | NC_001959 | vertebrates,human | 1 | Caliciviridae,Norovirus,Norwalk virus | — | AB447454 |
| Norovirus Hu/GII-4/Ehime2/2007/JP | NC_001959 | vertebrates,human | 1 | Caliciviridae,Norovirus,Norwalk virus | — | AB541238 |
| Norovirus Hu/GII-4/Ehime3/2007/JP | NC_001959 | vertebrates,human | 1 | Caliciviridae,Norovirus,Norwalk virus | — | AB541239 |
| Norovirus Hu/GII-4/Ehime3/2008/JP | NC_001959 | vertebrates,human | 1 | Caliciviridae,Norovirus,Norwalk virus | — | AB541240 |
| Norovirus Hu/GII-4/Ehime4/2007/JP | NC_001959 | vertebrates,human | 1 | Caliciviridae,Norovirus,Norwalk virus | — | AB541241 |
| Norovirus Hu/GII-4/Ehime4/2008/JP | NC_001959 | vertebrates,human | 1 | Caliciviridae,Norovirus,Norwalk virus | — | AB541242 |
| Norovirus Hu/GII-4/Ehime5/2006/JP | NC_001959 | vertebrates,human | 1 | Caliciviridae,Norovirus,Norwalk virus | — | AB447455 |
| Norovirus Hu/GII-4/Ehime5/2008/JP | NC_001959 | vertebrates,human | 1 | Caliciviridae,Norovirus,Norwalk virus | — | AB541243 |

-continued

| Taxonomy | NCBI Reference Sequence ID | Host | No. of Genomes | Lineage | Segment Count | Genbank Accession ID |
|---|---|---|---|---|---|---|
| Norovirus Hu/GII-4/FUMI/2010/JP | NC_001959 | vertebrates,human | 1 | Caliciviridae,Norovirus,Norwalk virus | — | AB543808 |
| Norovirus Hu/GII-4/Fukui1/2008/JP | NC_001959 | vertebrates,human | 1 | Caliciviridae,Norovirus,Norwalk virus | — | AB541244 |
| Norovirus Hu/GII-4/Fukui2/2007/JP | NC_001959 | vertebrates,human | 1 | Caliciviridae,Norovirus,Norwalk virus | — | AB541245 |
| Norovirus Hu/GII-4/Fukui2/2008/JP | NC_001959 | vertebrates,human | 1 | Caliciviridae,Norovirus,Norwalk virus | — | AB541246 |
| Norovirus Hu/GII-4/Fukui4/2007/JP | NC_001959 | vertebrates,human | 1 | Caliciviridae,Norovirus,Norwalk virus | — | AB541247 |
| Norovirus Hu/GII-4/Fukui4/2008/JP | NC_001959 | vertebrates,human | 1 | Caliciviridae,Norovirus,Norwalk virus | — | AB541248 |
| Norovirus Hu/GII-4/Fukui5/2007/JP | NC_001959 | vertebrates,human | 1 | Caliciviridae,Norovirus,Norwalk virus | — | AB541249 |
| Norovirus Hu/GII-4/Fukui5/2008/JP | NC_001959 | vertebrates,human | 1 | Caliciviridae,Norovirus,Norwalk virus | — | AB541250 |
| Norovirus Hu/GII-4/Hiroshima1/2006/JP | NC_001959 | vertebrates,human | 1 | Caliciviridae,Norovirus,Norwalk virus | — | AB447451 |
| Norovirus Hu/GII-4/Hiroshima1/2007/JP | NC_001959 | vertebrates,human | 1 | Caliciviridae,Norovirus,Norwalk virus | — | AB541251 |
| Norovirus Hu/GII-4/Hiroshima1/2008/JP | NC_001959 | vertebrates,human | 1 | Caliciviridae,Norovirus,Norwalk virus | — | AB541252 |
| Norovirus Hu/GII-4/Hiroshima2/2006/JP | NC_001959 | vertebrates,human | 1 | Caliciviridae,Norovirus,Norwalk virus | — | AB447452 |
| Norovirus Hu/GII-4/Hiroshima2/2007/JP | NC_001959 | vertebrates,human | 1 | Caliciviridae,Norovirus,Norwalk virus | — | AB541253 |
| Norovirus Hu/GII-4/Hiroshima2/2008/JP | NC_001959 | vertebrates,human | 1 | Caliciviridae,Norovirus,Norwalk virus | — | AB541254 |
| Norovirus Hu/GII-4/Hiroshima3/2007/JP | NC_001959 | vertebrates,human | 1 | Caliciviridae,Norovirus,Norwalk virus | — | AB541255 |
| Norovirus Hu/GII-4/Hiroshima3/2008/JP | NC_001959 | vertebrates,human | 1 | Caliciviridae,Norovirus,Norwalk virus | — | AB541256 |
| Norovirus Hu/GII-4/Hiroshima4/2007/JP | NC_001959 | vertebrates,human | 1 | Caliciviridae,Norovirus,Norwalk virus | — | AB541257 |
| Norovirus Hu/GII-4/Hiroshima4/2008/JP | NC_001959 | vertebrates,human | 1 | Caliciviridae,Norovirus,Norwalk virus | — | AB541258 |
| Norovirus Hu/GII-4/Hiroshima5/2008/JP | NC_001959 | vertebrates,human | 1 | Caliciviridae,Norovirus,Norwalk virus | — | AB541259 |
| Norovirus Hu/GII-4/Hokkaido1/2006/JP | NC_001959 | vertebrates,human | 1 | Caliciviridae,Norovirus,Norwalk virus | — | AB447427 |
| Norovirus Hu/GII-4/Hokkaido1/2007/JP | NC_001959 | vertebrates,human | 1 | Caliciviridae,Norovirus,Norwalk virus | — | AB541260 |
| Norovirus Hu/GII-4/Hokkaido1/2008/JP | NC_001959 | vertebrates,human | 1 | Caliciviridae,Norovirus,Norwalk virus | — | AB541261 |
| Norovirus Hu/GII-4/Hokkaido2/2006/JP | NC_001959 | vertebrates,human | 1 | Caliciviridae,Norovirus,Norwalk virus | — | AB447428 |
| Norovirus Hu/GII-4/Hokkaido2/2007/JP | NC_001959 | vertebrates,human | 1 | Caliciviridae,Norovirus,Norwalk virus | — | AB541262 |

| Taxonomy | NCBI Reference Sequence ID | Host | No. of Genomes | Lineage | Segment Count | Genbank Accession ID |
|---|---|---|---|---|---|---|
| Norovirus Hu/GII-4/Hokkaido2/2008/JP | NC_001959 | vertebrates,human | 1 | Caliciviridae,Norovirus,Norwalk virus | — | AB541263 |
| Norovirus Hu/GII-4/Hokkaido2/2008/JP | NC_001959 | vertebrates,human | 1 | Caliciviridae,Norovirus,Norwalk virus | — | AB447429 |
| Norovirus Hu/GII-4/Hokkaido3/2006/JP | NC_001959 | vertebrates,human | 1 | Caliciviridae,Norovirus,Norwalk virus | — | AB541264 |
| Norovirus Hu/GII-4/Hokkaido3/2008/JP | NC_001959 | vertebrates,human | 1 | Caliciviridae,Norovirus,Norwalk virus | — | AB447430 |
| Norovirus Hu/GII-4/Hokkaido4/2006/JP | NC_001959 | vertebrates,human | 1 | Caliciviridae,Norovirus,Norwalk virus | — | AB541265 |
| Norovirus Hu/GII-4/Hokkaido4/2007/JP | NC_001959 | vertebrates,human | 1 | Caliciviridae,Norovirus,Norwalk virus | — | AB541266 |
| Norovirus Hu/GII-4/Hokkaido4/2008/JP | NC_001959 | vertebrates,human | 1 | Caliciviridae,Norovirus,Norwalk virus | — | AB447431 |
| Norovirus Hu/GII-4/Hokkaido5/2006/JP | NC_001959 | vertebrates,human | 1 | Caliciviridae,Norovirus,Norwalk virus | — | AB541267 |
| Norovirus Hu/GII-4/Hokkaido5/2007/JP | NC_001959 | vertebrates,human | 1 | Caliciviridae,Norovirus,Norwalk virus | — | AB541268 |
| Norovirus Hu/GII-4/Hokkaido5/2008/JP | NC_001959 | vertebrates,human | 1 | Caliciviridae,Norovirus,Norwalk virus | — | AB541269 |
| Norovirus Hu/GII-4/Iwate1/2008/JP | NC_001959 | vertebrates,human | 1 | Caliciviridae,Norovirus,Norwalk virus | — | AB541270 |
| Norovirus Hu/GII-4/Iwate2/2007/JP | NC_001959 | vertebrates,human | 1 | Caliciviridae,Norovirus,Norwalk virus | — | AB541271 |
| Norovirus Hu/GII-4/Iwate3/2007/JP | NC_001959 | vertebrates,human | 1 | Caliciviridae,Norovirus,Norwalk virus | — | AB541272 |
| Norovirus Hu/GII-4/Iwate3/2008/JP | NC_001959 | vertebrates,human | 1 | Caliciviridae,Norovirus,Norwalk virus | — | AB541273 |
| Norovirus Hu/GII-4/Iwate4/2007/JP | NC_001959 | vertebrates,human | 1 | Caliciviridae,Norovirus,Norwalk virus | — | AB541274 |
| Norovirus Hu/GII-4/Iwate4/2008/JP | NC_001959 | vertebrates,human | 1 | Caliciviridae,Norovirus,Norwalk virus | — | AB541275 |
| Norovirus Hu/GII-4/Iwate5/2007/JP | NC_001959 | vertebrates,human | 1 | Caliciviridae,Norovirus,Norwalk virus | — | AB541276 |
| Norovirus Hu/GII-4/Iwate5/2008/JP | NC_001959 | vertebrates,human | 1 | Caliciviridae,Norovirus,Norwalk virus | — | AB447459 |
| Norovirus Hu/GII-4/Kumamoto1/2006/JP | NC_001959 | vertebrates,human | 1 | Caliciviridae,Norovirus,Norwalk virus | — | AB541277 |
| Norovirus Hu/GII-4/Kumamoto1/2007/JP | NC_001959 | vertebrates,human | 1 | Caliciviridae,Norovirus,Norwalk virus | — | AB447460 |
| Norovirus Hu/GII-4/Kumamoto2/2006/JP | NC_001959 | vertebrates,human | 1 | Caliciviridae,Norovirus,Norwalk virus | — | AB541278 |
| Norovirus Hu/GII-4/Kumamoto2/2007/JP | NC_001959 | vertebrates,human | 1 | Caliciviridae,Norovirus,Norwalk virus | — | AB447461 |
| Norovirus Hu/GII-4/Kumamoto3/2006/JP | NC_001959 | vertebrates,human | 1 | Caliciviridae,Norovirus,Norwalk virus | — | AB541279 |
| Norovirus Hu/GII-4/Kumamoto3/2007/JP | NC_001959 | vertebrates,human | 1 | Caliciviridae,Norovirus,Norwalk virus | — | AB447462 |
| Norovirus Hu/GII-4/Kumamoto4/2006/JP | NC_001959 | vertebrates,human | 1 | Caliciviridae,Norovirus,Norwalk virus | — | |

-continued

| Taxonomy | NCBI Reference Sequence ID | Host | Lineage | No. of Genomes | Segment Count | Genbank Accession ID |
|---|---|---|---|---|---|---|
| Norovirus Hu/GII-4/Kumamoto4/2007/JP | NC_001959 | vertebrates,human | Caliciviridae,Norovirus,Norwalk virus | 1 | — | AB541280 |
| Norovirus Hu/GII-4/Kumamoto4/2007/JP | NC_001959 | vertebrates,human | Caliciviridae,Norovirus,Norwalk virus | 1 | — | AB447463 |
| Norovirus Hu/GII-4/Kumamoto5/2006/JP | NC_001959 | vertebrates,human | Caliciviridae,Norovirus,Norwalk virus | 1 | — | AB541281 |
| Norovirus Hu/GII-4/Miyagi1/2007/JP | NC_001959 | vertebrates,human | Caliciviridae,Norovirus,Norwalk virus | 1 | — | AB447440 |
| Norovirus Hu/GII-4/Miyagi2/2006/JP | NC_001959 | vertebrates,human | Caliciviridae,Norovirus,Norwalk virus | 1 | — | AB541282 |
| Norovirus Hu/GII-4/Miyagi2/2007/JP | NC_001959 | vertebrates,human | Caliciviridae,Norovirus,Norwalk virus | 1 | — | AB541283 |
| Norovirus Hu/GII-4/Miyagi3/2007/JP | NC_001959 | vertebrates,human | Caliciviridae,Norovirus,Norwalk virus | 1 | — | AB447441 |
| Norovirus Hu/GII-4/Miyagi4/2006/JP | NC_001959 | vertebrates,human | Caliciviridae,Norovirus,Norwalk virus | 1 | — | AB447442 |
| Norovirus Hu/GII-4/Miyagi5/2006/JP | NC_001959 | vertebrates,human | Caliciviridae,Norovirus,Norwalk virus | 1 | — | AB541284 |
| Norovirus Hu/GII-4/Miyagi5/2008/JP | NC_001959 | vertebrates,human | Caliciviridae,Norovirus,Norwalk virus | 1 | — | AB541288 |
| Norovirus Hu/GII-4/Miyazaki1/2007/JP | NC_001959 | vertebrates,human | Caliciviridae,Norovirus,Norwalk virus | 1 | — | AB541289 |
| Norovirus Hu/GII-4/Miyazaki1/2008/JP | NC_001959 | vertebrates,human | Caliciviridae,Norovirus,Norwalk virus | 1 | — | AB541285 |
| Norovirus Hu/GII-4/Miyazaki10/2008/JP | NC_001959 | vertebrates,human | Caliciviridae,Norovirus,Norwalk virus | 1 | — | AB541286 |
| Norovirus Hu/GII-4/Miyazaki12/2008/JP | NC_001959 | vertebrates,human | Caliciviridae,Norovirus,Norwalk virus | 1 | — | AB541287 |
| Norovirus Hu/GII-4/Miyazaki13/2008/JP | NC_001959 | vertebrates,human | Caliciviridae,Norovirus,Norwalk virus | 1 | — | AB541290 |
| Norovirus Hu/GII-4/Miyazaki2/2007/JP | NC_001959 | vertebrates,human | Caliciviridae,Norovirus,Norwalk virus | 1 | — | AB541291 |
| Norovirus Hu/GII-4/Miyazaki2/2008/JP | NC_001959 | vertebrates,human | Caliciviridae,Norovirus,Norwalk virus | 1 | — | AB541292 |
| Norovirus Hu/GII-4/Miyazaki3/2007/JP | NC_001959 | vertebrates,human | Caliciviridae,Norovirus,Norwalk virus | 1 | — | AB541293 |
| Norovirus Hu/GII-4/Miyazaki3/2008/JP | NC_001959 | vertebrates,human | Caliciviridae,Norovirus,Norwalk virus | 1 | — | AB541294 |
| Norovirus Hu/GII-4/Miyazaki4/2007/JP | NC_001959 | vertebrates,human | Caliciviridae,Norovirus,Norwalk virus | 1 | — | AB541295 |
| Norovirus Hu/GII-4/Miyazaki4/2008/JP | NC_001959 | vertebrates,human | Caliciviridae,Norovirus,Norwalk virus | 1 | — | AB541296 |
| Norovirus Hu/GII-4/Miyazaki5/2007/JP | NC_001959 | vertebrates,human | Caliciviridae,Norovirus,Norwalk virus | 1 | — | AB541297 |
| Norovirus Hu/GII-4/Miyazaki6/2008/JP | NC_001959 | vertebrates,human | Caliciviridae,Norovirus,Norwalk virus | 1 | — | AB541298 |
| Norovirus Hu/GII-4/Miyazaki7/2008/JP | NC_001959 | vertebrates,human | Caliciviridae,Norovirus,Norwalk virus | 1 | — | AB541299 |
| Norovirus Hu/GII-4/Miyazaki8/2008/JP | NC_001959 | vertebrates,human | Caliciviridae,Norovirus,Norwalk virus | 1 | — | |

| Taxonomy | NCBI Reference Sequence ID | Host | No. of Genomes | Lineage | Segment Count | Genbank Accession ID |
|---|---|---|---|---|---|---|
| Norovirus Hu/GII-4/Nagano1/2007/JP | NC_001959 | vertebrates,human | 1 | Caliciviridae,Norovirus,Norwalk virus | — | AB541301 |
| Norovirus Hu/GII-4/Nagano1/2008/JP | NC_001959 | vertebrates,human | 1 | Caliciviridae,Norovirus,Norwalk virus | — | AB541302 |
| Norovirus Hu/GII-4/Nagano1/2008/JP | NC_001959 | vertebrates,human | 1 | Caliciviridae,Norovirus,Norwalk virus | — | AB541303 |
| Norovirus Hu/GII-4/Nagano2/2007/JP | NC_001959 | vertebrates,human | 1 | Caliciviridae,Norovirus,Norwalk virus | — | AB541304 |
| Norovirus Hu/GII-4/Nagano2/2008/JP | NC_001959 | vertebrates,human | 1 | Caliciviridae,Norovirus,Norwalk virus | — | AB541305 |
| Norovirus Hu/GII-4/Nagano3/2007/JP | NC_001959 | vertebrates,human | 1 | Caliciviridae,Norovirus,Norwalk virus | — | AB541306 |
| Norovirus Hu/GII-4/Nagano3/2008/JP | NC_001959 | vertebrates,human | 1 | Caliciviridae,Norovirus,Norwalk virus | — | AB541307 |
| Norovirus Hu/GII-4/Nagano04/2008/JP | NC_001959 | vertebrates,human | 1 | Caliciviridae,Norovirus,Norwalk virus | — | AB541308 |
| Norovirus Hu/GII-4/Nagano5/2007/JP | NC_001959 | vertebrates,human | 1 | Caliciviridae,Norovirus,Norwalk virus | — | AB541309 |
| Norovirus Hu/GII-4/Niigata1/2007/JP | NC_001959 | vertebrates,human | 1 | Caliciviridae,Norovirus,Norwalk virus | — | AB541310 |
| Norovirus Hu/GII-4/Niigata1/2008/JP | NC_001959 | vertebrates,human | 1 | Caliciviridae,Norovirus,Norwalk virus | — | AB541311 |
| Norovirus Hu/GII-4/Niigata2/2007/JP | NC_001959 | vertebrates,human | 1 | Caliciviridae,Norovirus,Norwalk virus | — | AB541312 |
| Norovirus Hu/GII-4/Niigata2/2008/JP | NC_001959 | vertebrates,human | 1 | Caliciviridae,Norovirus,Norwalk virus | — | AB541313 |
| Norovirus Hu/GII-4/Niigata3/2007/JP | NC_001959 | vertebrates,human | 1 | Caliciviridae,Norovirus,Norwalk virus | — | AB541314 |
| Norovirus Hu/GII-4/Niigata3/2008/JP | NC_001959 | vertebrates,human | 1 | Caliciviridae,Norovirus,Norwalk virus | — | AB541315 |
| Norovirus Hu/GII-4/Niigata4/2007/JP | NC_001959 | vertebrates,human | 1 | Caliciviridae,Norovirus,Norwalk virus | — | AB541316 |
| Norovirus Hu/GII-4/Niigata4/2008/JP | NC_001959 | vertebrates,human | 1 | Caliciviridae,Norovirus,Norwalk virus | — | AB541317 |
| Norovirus Hu/GII-4/Niigata5/2007/JP | NC_001959 | vertebrates,human | 1 | Caliciviridae,Norovirus,Norwalk virus | — | AB541318 |
| Norovirus Hu/GII-4/Niigata5/2008/JP | NC_001959 | vertebrates,human | 1 | Caliciviridae,Norovirus,Norwalk virus | — | AB541319 |
| Norovirus Hu/GII-4/0saka1/2007/JP | NC_001959 | vertebrates,human | 1 | Caliciviridae,Norovirus,Norwalk virus | — | AB541320 |
| Norovirus Hu/GII-4/0saka1/2008/JP | NC_001959 | vertebrates,human | 1 | Caliciviridae,Norovirus,Norwalk virus | — | AB541321 |
| Norovirus Hu/GII-4/0saka2/2007/JP | NC_001959 | vertebrates,human | 1 | Caliciviridae,Norovirus,Norwalk virus | — | AB541322 |
| Norovirus Hu/GII-4/0saka2/2008/JP | NC_001959 | vertebrates,human | 1 | Caliciviridae,Norovirus,Norwalk virus | — | AB541323 |
| Norovirus Hu/GII-4/0saka3/2007/JP | NC_001959 | vertebrates,human | 1 | Caliciviridae,Norovirus,Norwalk virus | — | AB541324 |
| Norovirus Hu/GII-4/0saka3/2008/JP | | | | | | |

| Taxonomy | NCBI Reference Sequence ID | Host | No. of Genomes | Lineage | Segment Count | Genbank Accession ID |
|---|---|---|---|---|---|---|
| Norovirus Hu/GII-4/05aka4/2007/JP | NC_001959 | vertebrates,human | 1 | Caliciviridae,Norovirus,Norwalk virus | — | AB541325 |
| Norovirus Hu/GII-4/05aka4/2008/JP | NC_001959 | vertebrates,human | 1 | Caliciviridae,Norovirus,Norwalk virus | — | AB541326 |
| Norovirus Hu/GII-4/05aka5/2007/JP | NC_001959 | vertebrates,human | 1 | Caliciviridae,Norovirus,Norwalk virus | — | AB541327 |
| Norovirus Hu/GII-4/05aka5/2008/JP | NC_001959 | vertebrates,human | 1 | Caliciviridae,Norovirus,Norwalk virus | — | AB541328 |
| Norovirus Hu/GII-4/0saka5/2008/JP | NC_001959 | vertebrates,human | 1 | Caliciviridae,Norovirus,Norwalk virus | — | AB541329 |
| Norovirus Hu/GII-4/0saka6/2008/JP | NC_001959 | vertebrates,human | 1 | Caliciviridae,Norovirus,Norwalk virus | — | AB447456 |
| Norovirus Hu/GII-4/Saga1/2006/JP | NC_001959 | vertebrates,human | 1 | Caliciviridae,Norovirus,Norwalk virus | — | AB541330 |
| Norovirus Hu/GII-4/Saga1/2007/JP | NC_001959 | vertebrates,human | 1 | Caliciviridae,Norovirus,Norwalk virus | — | AB541331 |
| Norovirus Hu/GII-4/Saga1/2008/JP | NC_001959 | vertebrates,human | 1 | Caliciviridae,Norovirus,Norwalk virus | — | AB541332 |
| Norovirus Hu/GII-4/Saga2/2007/JP | NC_001959 | vertebrates,human | 1 | Caliciviridae,Norovirus,Norwalk virus | — | AB541333 |
| Norovirus Hu/GII-4/Saga2/2008/JP | NC_001959 | vertebrates,human | 1 | Caliciviridae,Norovirus,Norwalk virus | — | AB541334 |
| Norovirus Hu/GII-4/Saga3/2008/JP | NC_001959 | vertebrates,human | 1 | Caliciviridae,Norovirus,Norwalk virus | — | AB447457 |
| Norovirus Hu/GII-4/Saga4/2006/JP | NC_001959 | vertebrates,human | 1 | Caliciviridae,Norovirus,Norwalk virus | — | AB541335 |
| Norovirus Hu/GII-4/Saga4/2007/JP | NC_001959 | vertebrates,human | 1 | Caliciviridae,Norovirus,Norwalk virus | — | AB541336 |
| Norovirus Hu/GII-4/Saga4/2008/JP | NC_001959 | vertebrates,human | 1 | Caliciviridae,Norovirus,Norwalk virus | — | AB447458 |
| Norovirus Hu/GII-4/Saga5/2006/JP | NC_001959 | vertebrates,human | 1 | Caliciviridae,Norovirus,Norwalk virus | — | AB541337 |
| Norovirus Hu/GII-4/Saga5/2007/JP | NC_001959 | vertebrates,human | 1 | Caliciviridae,Norovirus,Norwalk virus | — | AB541338 |
| Norovirus Hu/GII-4/Saga5/2008/JP | NC_001959 | vertebrates,human | 1 | Caliciviridae,Norovirus,Norwalk virus | — | AB541339 |
| Norovirus H u/GII-4/Sakai 1/2007/JP | NC_001959 | vertebrates,human | 1 | Caliciviridae,Norovirus,Norwalk virus | — | AB541340 |
| Norovirus H u/GII-4/Sakai 1/2008/JP | NC_001959 | vertebrates,human | 1 | Caliciviridae,Norovirus,Norwalk virus | — | AB447448 |
| Norovirus H u/GII-4/Sakai2/2006/JP | NC_001959 | vertebrates,human | 1 | Caliciviridae,Norovirus,Norwalk virus | — | AB541341 |
| Norovirus H u/GII-4/Sakai2/2007/JP | NC_001959 | vertebrates,human | 1 | Caliciviridae,Norovirus,Norwalk virus | — | AB447449 |
| Norovirus H u/GII-4/Sakai3/2006/JP | NC_001959 | vertebrates,human | 1 | Caliciviridae,Norovirus,Norwalk virus | — | AB541342 |
| Norovirus H u/GII-4/Sakai3/2007/JP | NC_001959 | vertebrates,human | 1 | Caliciviridae,Norovirus,Norwalk virus | — | AB541343 |
| Norovirus H u/GII-4/Sakai3/2008/JP | NC_001959 | vertebrates,human | 1 | Caliciviridae,Norovirus,Norwalk virus | — | |

-continued

| Taxonomy | NCBI Reference Sequence ID | Host | Lineage | No. of Genomes | Segment Count | Genbank Accession ID |
|---|---|---|---|---|---|---|
| Norovirus H u/GII-4/Sakai4/2006/JP | NC_001959 | vertebrates,human | Caliciviridae,Norovirus,Norwalk virus | 1 | — | AB447450 |
| Norovirus H u/GII-4/Sakai4/2006/JP | NC_001959 | vertebrates,human | Caliciviridae,Norovirus,Norwalk virus | 1 | — | AB541344 |
| Norovirus H u/GII-4/Sakai4/2007/JP | NC_001959 | vertebrates,human | Caliciviridae,Norovirus,Norwalk virus | 1 | — | AB541345 |
| Norovirus H u/GII-4/Sakai4/2008/JP | NC_001959 | vertebrates,human | Caliciviridae,Norovirus,Norwalk virus | 1 | — | AB541346 |
| Norovirus H u/GII-4/Shimane1/2007/JP | NC_001959 | vertebrates,human | Caliciviridae,Norovirus,Norwalk virus | 1 | — | AB541347 |
| Norovirus H u/GII-4/Shimane2/2007/JP | NC_001959 | vertebrates,human | Caliciviridae,Norovirus,Norwalk virus | 1 | — | AB541349 |
| Norovirus H u/GII-4/Shimane3/2007/JP | NC_001959 | vertebrates,human | Caliciviridae,Norovirus,Norwalk virus | 1 | — | AB541350 |
| Norovirus H u/GII-4/Shimane3/2008/JP | NC_001959 | vertebrates,human | Caliciviridae,Norovirus,Norwalk virus | 1 | — | AB541351 |
| Norovirus H u/GII-4/Shimane4/2007/JP | NC_001959 | vertebrates,human | Caliciviridae,Norovirus,Norwalk virus | 1 | — | AB541352 |
| Norovirus H u/GII-4/Shimane5/2007/JP | NC_001959 | vertebrates,human | Caliciviridae,Norovirus,Norwalk virus | 1 | — | AB541353 |
| Norovirus H u/GII-4/Shimane5/2008/JP | NC_001959 | vertebrates,human | Caliciviridae,Norovirus,Norwalk virus | 1 | — | AB447443 |
| Norovirus H u/GII-4/Toyama1/2006/JP | NC_001959 | vertebrates,human | Caliciviridae,Norovirus,Norwalk virus | 1 | — | AB541354 |
| Norovirus H u/GII-4/Toyama1/2007/JP | NC_001959 | vertebrates,human | Caliciviridae,Norovirus,Norwalk virus | 1 | — | AB541355 |
| Norovirus H u/GII-4/Toyama2/2007/JP | NC_001959 | vertebrates,human | Caliciviridae,Norovirus,Norwalk virus | 1 | — | AB541356 |
| Norovirus H u/GII-4/Toyama2/2008/JP | NC_001959 | vertebrates,human | Caliciviridae,Norovirus,Norwalk virus | 1 | — | AB541357 |
| Norovirus H u/GII-4/Toyama3/2007/JP | NC_001959 | vertebrates,human | Caliciviridae,Norovirus,Norwalk virus | 1 | — | AB541358 |
| Norovirus H u/GII-4/Toyama3/2008/JP | NC_001959 | vertebrates,human | Caliciviridae,Norovirus,Norwalk virus | 1 | — | AB447444 |
| Norovirus H u/GII-4/Toyama4/2006/JP | NC_001959 | vertebrates,human | Caliciviridae,Norovirus,Norwalk virus | 1 | — | AB541359 |
| Norovirus H u/GII-4/Toyama4/2007/JP | NC_001959 | vertebrates,human | Caliciviridae,Norovirus,Norwalk virus | 1 | — | AB541360 |
| Norovirus H u/GII-4/Toyama4/2008/JP | NC_001959 | vertebrates,human | Caliciviridae,Norovirus,Norwalk virus | 1 | — | AB447445 |
| Norovirus H u/GII-4/Toyama5/2006/JP | NC_001959 | vertebrates,human | Caliciviridae,Norovirus,Norwalk virus | 1 | — | AB541361 |
| Norovirus H u/GII-4/Toyama5/2007/JP | NC_001959 | vertebrates,human | Caliciviridae,Norovirus,Norwalk virus | 1 | — | AB541362 |
| Norovirus Hu/G11,12/HS206/2010/USA | NC_001959 | vertebrates,human | Caliciviridae,Norovirus,Norwalk virus | 1 | — | HQ664990 |
| Norovirus Hu/G11,12/HS210/2010/USA | NC_001959 | vertebrates,human | Caliciviridae,Norovirus,Norwalk virus | 1 | — | HQ449728 |

-continued

| Taxonomy | NCBI Reference Sequence ID | Host | No. of Genomes | Lineage | Segment Count | Genbank Accession ID |
|---|---|---|---|---|---|---|
| Norovirus Hu/GII,3/ C BN U1/2006/K0R | NC_001959 | vertebrates,human | 1 | Caliciviridae,Norovirus,Norwalk virus | — | GU980585 |
| Norovirus Hu/GII,3/ Jingzhou/ 2013402/CHN | NC_001959 | vertebrates,human | 1 | Caliciviridae,Norovirus,Norwalk virus | — | KF306213 |
| Norovirus Hu/GII,4/5M/USA/2004 | NC_001959 | vertebrates,human | 1 | Caliciviridae,Norovirus,Norwalk virus | — | JQ798158 |
| Norovirus Hu/GII,4/Armidale/ NSW390I/2008/AU | NC_001959 | vertebrates,human | 1 | Caliciviridae,Norovirus,Norwalk virus | — | GQ845369 |
| Norovirus Hu/GII,4/Beecroft/ NSW305P/2009/AUS | NC_001959 | vertebrates,human | 1 | Caliciviridae,Norovirus,Norwalk virus | — | HM748971 |
| Norovirus Hu/G II, 4/ CH DC2094/1974/ US | NC_001959 | vertebrates,human | 1 | Caliciviridae,Norovirus,Norwalk virus | — | FJ537135 |
| Norovirus Hu/G II, 4/ CH DC3967/1988/ US | NC_001959 | vertebrates,human | 1 | Caliciviridae,Norovirus,Norwalk virus | — | FJ537136 |
| Norovirus Hu/GII,4/CHDC4108/1987/ US | NC_001959 | vertebrates,human | 1 | Caliciviridae,Norovirus,Norwalk virus | — | FJ537137 |
| Norovirus Hu/GII,4/CHDC4871/1977/ US | NC_001959 | vertebrates,human | 1 | Caliciviridae,Norovirus,Norwalk virus | — | FJ537138 |
| Norovirus Hu/GII,4/CHDC5191/1974/ US | NC_001959 | vertebrates,human | 1 | Caliciviridae,Norovirus,Norwalk virus | — | FJ537134 |
| Norovirus Hu/GII,4/CHDC5191/1974/ USA | NC_001959 | vertebrates,human | 1 | Caliciviridae,Norovirus,Norwalk virus | — | JXQ23286 |
| Norovirus Hu/GII,4/GP13111/2011/ USA | NC_001959 | vertebrates,human | 1 | Caliciviridae,Norovirus,Norwalk virus | — | KC576912 |
| Norovirus Hu/GII,4/GP2411/2011/ USA | NC_001959 | vertebrates,human | 1 | Caliciviridae,Norovirus,Norwalk virus | — | KC576909 |
| Norovirus Hu/GII,4/HS194/2009/US | NC_001959 | vertebrates,human | 1 | Caliciviridae,Norovirus,Norwalk virus | — | GU325839 |
| Norovirus Hu/GII,4/Hunter504D/ 040/AU | NC_001959 | vertebrates,human | 1 | Caliciviridae,Norovirus,Norwalk virus | — | DQ078814 |
| Norovirus Hu/GII,4/JB-15/KOR/2008 | NC_001959 | vertebrates,human | 1 | Caliciviridae,Norovirus,Norwalk virus | — | HQ009513 |
| Norovirus Hu/GII,4/Jiangsu1/2011/ CHN | NC_001959 | vertebrates,human | 1 | Caliciviridae,Norovirus,Norwalk virus | — | KC577174 |

-continued

| Taxonomy | NCBI Reference Sequence ID | Host | No. of Genomes | Lineage | Segment Count | Genbank Accession ID |
|---|---|---|---|---|---|---|
| Norovirus Hu/GII.4/Jiangsu2/2012/CHN | NC_001959 | vertebrates,human | 1 | Caliciviridae,Norovirus,Norwalk virus | — | KC577175 |
| Norovirus Hu/GII.4/Jingzhou/2013403/CHN | NC_001959 | vertebrates,human | 1 | Caliciviridae,Norovirus,Norwalk virus | — | KF306214 |
| Norovirus Hu/GII.4/Kenepuru/NZ327/2006/NZL | NC_001959 | vertebrates,human | 1 | Caliciviridae,Norovirus,Norwalk virus | — | EF187497 |
| Norovirus Hu/GII.4/MD-2004/2004/US | NC_001959 | vertebrates,human | 1 | Caliciviridae,Norovirus,Norwalk virus | — | DQ658413 |
| Norovirus Hu/GII.4/NIHIC1,16/2012/USA | NC_001959 | vertebrates,human | 1 | Caliciviridae,Norovirus,Norwalk virus | — | KF712499 |
| Norovirus Hu/GII.4/NIHIC11,3/2013/USA | NC_001959 | vertebrates,human | 1 | Caliciviridae,Norovirus,Norwalk virus | — | KF712504 |
| Norovirus Hu/GII.4/NIHIC17,6/2012/USA | NC_001959 | vertebrates,human | 1 | Caliciviridae,Norovirus,Norwalk virus | — | KF712501 |
| Norovirus Hu/GII.4/NIHIC17,8/2013/USA | NC_001959 | vertebrates,human | 1 | Caliciviridae,Norovirus,Norwalk virus | — | KF712491 |
| Norovirus Hu/GII.4/NIHIC17,9/2013/USA | NC_001959 | vertebrates,human | 1 | Caliciviridae,Norovirus,Norwalk virus | — | KF712498 |
| Norovirus Hu/GII.4/NIHIC2,2/2010/USA | NC_001959 | vertebrates,human | 1 | Caliciviridae,Norovirus,Norwalk virus | — | KF712510 |
| Norovirus Hu/GII.4/NIHIC2,3/2010/USA | NC_001959 | vertebrates,human | 1 | Caliciviridae,Norovirus,Norwalk virus | — | KF712496 |
| Norovirus Hu/GII.4/NIHIC27,2/2012/USA | NC_001959 | vertebrates,human | 1 | Caliciviridae,Norovirus,Norwalk virus | — | KF712497 |
| Norovirus Hu/GII.4/NIHIC28,6/2012/USA | NC_001959 | vertebrates,human | 1 | Caliciviridae,Norovirus,Norwalk virus | — | KF712508 |
| Norovirus Hu/GII.4/NIHIC35/2013/USA | NC_001959 | vertebrates,human | 1 | Caliciviridae,Norovirus,Norwalk virus | — | KF712502 |
| Norovirus H u/G II ,4/N SW 123B/2010/AU | NC_001959 | vertebrates,human | 1 | Caliciviridae,Norovirus,Norwalk virus | — | JQ613552 |
| Norovirus Hu/GII,4/New Orleans1805/2009/USA | NC_001959 | vertebrates,human | 1 | Caliciviridae,Norovirus,Norwalk virus | — | GU445325 |

-continued

| Taxonomy | NCBI Reference Sequence ID | Host | Lineage | No. of Genomes | Segment Count | Genbank Accession ID |
|---|---|---|---|---|---|---|
| Norovirus Hu/GII,4/Ohio/7G/2012/USA | NC_001959 | vertebrates,human | Caliciviridae,Norovirus,Norwalk virus | 1 | — | JX126913 |
| Norovirus Hu/GII,4/Ohio/71/2012/USA | NC_001959 | vertebrates,human | Caliciviridae,Norovirus,Norwalk virus | 1 | — | JX126912 |
| Norovirus Hu/GII,4/Orange/NSW001P/2008/AU | NC_001959 | vertebrates,human | Caliciviridae,Norovirus,Norwalk virus | 1 | — | GQ845367 |
| Norovirus 87R/2007/Hu/GII,4/Rathmines/NSW2 AUS | NC_001959 | vertebrates,human | Caliciviridae,Norovirus,Norwalk virus | 1 | — | GQ845024 |
| Norovirus Hu/GII,4/Shellharbour/NSW 696T/2006/AUS | NC_001959 | vertebrates,human | Caliciviridae,Norovirus,Norwalk virus | 1 | — | EF684915 |
| Norovirus Hu/GII,4/Sutherland/NSW5 05G/2007/AUS | NC_001959 | vertebrates,human | Caliciviridae,Norovirus,Norwalk virus | 1 | — | GQ845368 |
| Norovirus Hu/G II ,4/Teralba/NSW8812/2009/AUS | NC_001959 | vertebrates,human | Caliciviridae,Norovirus,Norwalk virus | 1 | — | HM748972 |
| Norovirus Hu/GII,4/Turramurra/NSW892U/2009/AUS | NC_001959 | vertebrates,human | Caliciviridae,Norovirus,Norwalk virus | 1 | — | HM748973 |
| Norovirus Hu/GII,4/Westmead/NSW3 639/2008/AUS | NC_001959 | vertebrates,human | Caliciviridae,Norovirus,Norwalk virus | 1 | — | GQ845366 |
| Norovirus Hu/GII,6/NIHIC34,1/2013/USA | NC_001959 | vertebrates,human | Caliciviridae,Norovirus,Norwalk virus | 1 | — | KF712509 |
| Norovirus Hu/GII,e-GII,12/StGeorge/NSW/2008/AU | NC_001959 | vertebrates,human | Caliciviridae,Norovirus,Norwalk virus 199U | 1 | — | GQ845370 |
| Norovirus Hu/GII/10002/2009/VNM | NC_001959 | vertebrates,human | Caliciviridae,Norovirus,Norwalk virus | 1 | — | JQ911595 |
| Norovirus Hu/GII/10003/2009/VNM | NC_001959 | vertebrates,human | Caliciviridae,Norovirus,Norwalk virus | 1 | — | JQ911596 |
| Norovirus Hu/GII/10012/2009/VNM | NC_001959 | vertebrates,human | Caliciviridae,Norovirus,Norwalk virus | 1 | — | JQ911597 |
| Norovirus Hu/GII/10037/2009/VNM | NC_001959 | vertebrates,human | Caliciviridae,Norovirus,Norwalk virus | 1 | — | JQ911598 |
| Norovirus Hu/GII/10101/2009/VNM | NC_001959 | vertebrates,human | Caliciviridae,Norovirus,Norwalk virus | 1 | — | KC409238 |
| Norovirus Hu/GII/10127/2009/VNM | NC_001959 | vertebrates,human | Caliciviridae,Norovirus,Norwalk virus | 1 | — | KC409239 |
| Norovirus Hu/GII/10370/2010/VNM | NC_001959 | vertebrates,human | Caliciviridae,Norovirus,Norwalk virus | 1 | — | KC409240 |
| Norovirus Hu/GII/10405/2010/VNM | NC_001959 | vertebrates,human | Caliciviridae,Norovirus,Norwalk virus | 1 | — | KC409241 |

| Taxonomy | NCBI Reference Sequence ID | Host | Lineage | No. of Genomes | Segment Count | Genbank Accession ID |
|---|---|---|---|---|---|---|
| Norovirus Hu/GII/10406/2010/VNM | NC_001959 | vertebrates,human | Caliciviridae,Norovirus,Norwalk virus | 1 | — | KC409242 |
| Norovirus Hu/GII/10411/2010/VNM | NC_001959 | vertebrates,human | Caliciviridae,Norovirus,Norwalk virus | 1 | — | KC409243 |
| Norovirus Hu/GII/10420/2010/VNM | NC_001959 | vertebrates,human | Caliciviridae,Norovirus,Norwalk virus | 1 | — | KC409244 |
| Norovirus Hu/GII/20048/2009/VNM | NC_001959 | vertebrates,human | Caliciviridae,Norovirus,Norwalk virus | 1 | — | KC409245 |
| Norovirus Hu/GII/20064/2009/VNM | NC_001959 | vertebrates,human | Caliciviridae,Norovirus,Norwalk virus | 1 | — | KC409246 |
| Norovirus Hu/GII/20079/2009/VNM | NC_001959 | vertebrates,human | Caliciviridae,Norovirus,Norwalk virus | 1 | — | KC409247 |
| Norovirus Hu/GII/20107/2009/VNM | NC_001959 | vertebrates,human | Caliciviridae,Norovirus,Norwalk virus | 1 | — | KC409248 |
| Norovirus Hu/GII/20108/2009/VNM | NC_001959 | vertebrates,human | Caliciviridae,Norovirus,Norwalk virus | 1 | — | KC409249 |
| Norovirus Hu/GII/20144/2009/VNM | NC_001959 | vertebrates,human | Caliciviridae,Norovirus,Norwalk virus | 1 | — | KC409250 |
| Norovirus Hu/GII/20146/2009/VNM | NC_001959 | vertebrates,human | Caliciviridae,Norovirus,Norwalk virus | 1 | — | KC409251 |
| Norovirus Hu/GII/20150/2009/VNM | NC_001959 | vertebrates,human | Caliciviridae,Norovirus,Norwalk virus | 1 | — | KC409252 |
| Norovirus Hu/GII/20151/2009/VNM | NC_001959 | vertebrates,human | Caliciviridae,Norovirus,Norwalk virus | 1 | — | KC409253 |
| Norovirus Hu/GII/20153/2009/VNM | NC_001959 | vertebrates,human | Caliciviridae,Norovirus,Norwalk virus | 1 | — | KC409254 |
| Norovirus Hu/GII/20154/2009/VNM | NC_001959 | vertebrates,human | Caliciviridae,Norovirus,Norwalk virus | 1 | — | KC409255 |
| Norovirus Hu/GII/20156/2009/VNM | NC_001959 | vertebrates,human | Caliciviridae,Norovirus,Norwalk virus | 1 | — | KC409256 |
| Norovirus Hu/GII/20159/2009/VNM | NC_001959 | vertebrates,human | Caliciviridae,Norovirus,Norwalk virus | 1 | — | KC409257 |
| Norovirus Hu/GII/20161/2009/VNM | NC_001959 | vertebrates,human | Caliciviridae,Norovirus,Norwalk virus | 1 | — | KC409258 |
| Norovirus Hu/GII/20162/2009/VNM | NC_001959 | vertebrates,human | Caliciviridae,Norovirus,Norwalk virus | 1 | — | KC409259 |
| Norovirus Hu/GII/20164/2009/VNM | NC_001959 | vertebrates,human | Caliciviridae,Norovirus,Norwalk virus | 1 | — | KC409260 |
| Norovirus Hu/GII/20171/2009/VNM | NC_001959 | vertebrates,human | Caliciviridae,Norovirus,Norwalk virus | 1 | — | KC409261 |
| Norovirus Hu/GII/20172/2009/VNM | NC_001959 | vertebrates,human | Caliciviridae,Norovirus,Norwalk virus | 1 | — | KC409262 |
| Norovirus Hu/GII/20173/2009/VNM | NC_001959 | vertebrates,human | Caliciviridae,Norovirus,Norwalk virus | 1 | — | KC409263 |
| Norovirus Hu/GII/20176/2009/VNM | NC_001959 | vertebrates,human | Caliciviridae,Norovirus,Norwalk virus | 1 | — | KC409264 |
| Norovirus Hu/GII/20180/2009/VNM | NC_001959 | vertebrates,human | Caliciviridae,Norovirus,Norwalk virus | 1 | — | KC409265 |

| Taxonomy | NCBI Reference Sequence ID | Host | No. of Genomes | Lineage | Segment Count | Genbank Accession ID |
|---|---|---|---|---|---|---|
| Norovirus Hu/GII/20182/2009/VNM | NC_001959 | vertebrates,human | 1 | Caliciviridae,Norovirus,Norwalk virus | — | KC409266 |
| Norovirus Hu/GII/20184/2009/VNM | NC_001959 | vertebrates,human | 1 | Caliciviridae,Norovirus,Norwalk virus | — | KC409267 |
| Norovirus Hu/GII/20185/2009/VNM | NC_001959 | vertebrates,human | 1 | Caliciviridae,Norovirus,Norwalk virus | — | KC409268 |
| Norovirus Hu/GII/20187/2009/VNM | NC_001959 | vertebrates,human | 1 | Caliciviridae,Norovirus,Norwalk virus | — | KC409269 |
| Norovirus Hu/GII/20189/2009/VNM | NC_001959 | vertebrates,human | 1 | Caliciviridae,Norovirus,Norwalk virus | — | KC409270 |
| Norovirus Hu/GII/20190/2009/VNM | NC_001959 | vertebrates,human | 1 | Caliciviridae,Norovirus,Norwalk virus | — | KC409271 |
| Norovirus Hu/GII/20192/2009/VNM | NC_001959 | vertebrates,human | 1 | Caliciviridae,Norovirus,Norwalk virus | — | KC409272 |
| Norovirus Hu/GII/20196/2009/VNM | NC_001959 | vertebrates,human | 1 | Caliciviridae,Norovirus,Norwalk virus | — | KC409273 |
| Norovirus Hu/GII/20198/2009/VNM | NC_001959 | vertebrates,human | 1 | Caliciviridae,Norovirus,Norwalk virus | — | KC409274 |
| Norovirus Hu/GII/20202/2009/VNM | NC_001959 | vertebrates,human | 1 | Caliciviridae,Norovirus,Norwalk virus | — | KC409275 |
| Norovirus Hu/GII/20205/2009/VNM | NC_001959 | vertebrates,human | 1 | Caliciviridae,Norovirus,Norwalk virus | — | KC409276 |
| Norovirus Hu/GII/20206/2009/VNM | NC_001959 | vertebrates,human | 1 | Caliciviridae,Norovirus,Norwalk virus | — | KC409277 |
| Norovirus Hu/GII/20208/2009/VNM | NC_001959 | vertebrates,human | 1 | Caliciviridae,Norovirus,Norwalk virus | — | KC409278 |
| Norovirus Hu/GII/20215/2009/VNM | NC_001959 | vertebrates,human | 1 | Caliciviridae,Norovirus,Norwalk virus | — | KC409279 |
| Norovirus Hu/GII/20217/2009/VNM | NC_001959 | vertebrates,human | 1 | Caliciviridae,Norovirus,Norwalk virus | — | KC409280 |
| Norovirus Hu/GII/20229/2009/VNM | NC_001959 | vertebrates,human | 1 | Caliciviridae,Norovirus,Norwalk virus | — | KC409281 |
| Norovirus Hu/GII/20230/2009/VNM | NC_001959 | vertebrates,human | 1 | Caliciviridae,Norovirus,Norwalk virus | — | KC409282 |
| Norovirus Hu/GII/20233/2009/VNM | NC_001959 | vertebrates,human | 1 | Caliciviridae,Norovirus,Norwalk virus | — | KC409283 |
| Norovirus Hu/GII/20248/2009/VNM | NC_001959 | vertebrates,human | 1 | Caliciviridae,Norovirus,Norwalk virus | — | KC409284 |
| Norovirus Hu/GII/20258/2009/VNM | NC_001959 | vertebrates,human | 1 | Caliciviridae,Norovirus,Norwalk virus | — | KC409285 |
| Norovirus Hu/GII/20263/2009/VNM | NC_001959 | vertebrates,human | 1 | Caliciviridae,Norovirus,Norwalk virus | — | KC409286 |
| Norovirus Hu/GII/20271/2009/VNM | NC_001959 | vertebrates,human | 1 | Caliciviridae,Norovirus,Norwalk virus | — | KC409287 |
| Norovirus Hu/GII/20276/2009/VNM | NC_001959 | vertebrates,human | 1 | Caliciviridae,Norovirus,Norwalk virus | — | KC409288 |
| Norovirus Hu/GII/20302/2009/VNM | NC_001959 | vertebrates,human | 1 | Caliciviridae,Norovirus,Norwalk virus | — | KC409289 |

| Taxonomy | NCBI Reference Sequence ID | Host | No. of Genomes | Lineage | Segment Count | Genbank Accession ID |
|---|---|---|---|---|---|---|
| Norovirus Hu/GII/20344/2009/VNM | NC_001959 | vertebrates,human | 1 | Caliciviridae,Norovirus,Norwalk virus | — | KC409290 |
| Norovirus Hu/GII/20350/2009/VNM | NC_001959 | vertebrates,human | 1 | Caliciviridae,Norovirus,Norwalk virus | — | KC409291 |
| Norovirus Hu/GII/20357/2009/VNM | NC_001959 | vertebrates,human | 1 | Caliciviridae,Norovirus,Norwalk virus | — | KC409292 |
| Norovirus Hu/GII/20365/2010/VNM | NC_001959 | vertebrates,human | 1 | Caliciviridae,Norovirus,Norwalk virus | — | KC409293 |
| Norovirus Hu/GII/20373/2010/VNM | NC_001959 | vertebrates,human | 1 | Caliciviridae,Norovirus,Norwalk virus | — | KC409294 |
| Norovirus Hu/GII/20407/2010/VNM | NC_001959 | vertebrates,human | 1 | Caliciviridae,Norovirus,Norwalk virus | — | KC409295 |
| Norovirus Hu/GII/20413/2010/VNM | NC_001959 | vertebrates,human | 1 | Caliciviridae,Norovirus,Norwalk virus | — | KC409296 |
| Norovirus Hu/GII/20424/2010/VNM | NC_001959 | vertebrates,human | 1 | Caliciviridae,Norovirus,Norwalk virus | — | KC409297 |
| Norovirus Hu/GII/20448/2010/VNM | NC_001959 | vertebrates,human | 1 | Caliciviridae,Norovirus,Norwalk virus | — | KC409298 |
| Norovirus Hu/GII/20457/2010/VNM | NC_001959 | vertebrates,human | 1 | Caliciviridae,Norovirus,Norwalk virus | — | KC409299 |
| Norovirus Hu/GII/20460/2010/VNM | NC_001959 | vertebrates,human | 1 | Caliciviridae,Norovirus,Norwalk virus | — | KC409300 |
| Norovirus Hu/GII/20469/2010/VNM | NC_001959 | vertebrates,human | 1 | Caliciviridae,Norovirus,Norwalk virus | — | KC409301 |
| Norovirus Hu/GII/20477/2010/VNM | NC_001959 | vertebrates,human | 1 | Caliciviridae,Norovirus,Norwalk virus | — | KC409302 |
| Norovirus Hu/GII/20478/2010/VNM | NC_001959 | vertebrates,human | 1 | Caliciviridae,Norovirus,Norwalk virus | — | KC409303 |
| Norovirus Hu/GII/30017/2009/VNM | NC_001959 | vertebrates,human | 1 | Caliciviridae,Norovirus,Norwalk virus | — | KC409304 |
| Norovirus Hu/GII/30026/2009/VNM | NC_001959 | vertebrates,human | 1 | Caliciviridae,Norovirus,Norwalk virus | — | KC409305 |
| Norovirus Hu/GII/30040/2009/VNM | NC_001959 | vertebrates,human | 1 | Caliciviridae,Norovirus,Norwalk virus | — | KC409306 |
| Norovirus Hu/GII/30045/2009/VNM | NC_001959 | vertebrates,human | 1 | Caliciviridae,Norovirus,Norwalk virus | — | KC409307 |
| Norovirus Hu/GII/30113/2009/VNM | NC_001959 | vertebrates,human | 1 | Caliciviridae,Norovirus,Norwalk virus | — | KC409309 |
| Norovirus Hu/GII/30129/2009/VNM | NC_001959 | vertebrates,human | 1 | Caliciviridae,Norovirus,Norwalk virus | — | KC409310 |
| Norovirus Hu/GII/30199/2009/VNM | NC_001959 | vertebrates,human | 1 | Caliciviridae,Norovirus,Norwalk virus | — | KC409311 |
| Norovirus Hu/GII/30201/2009/VNM | NC_001959 | vertebrates,human | 1 | Caliciviridae,Norovirus,Norwalk virus | — | KC409312 |
| Norovirus Hu/GII/30206/2009/VNM | NC_001959 | vertebrates,human | 1 | Caliciviridae,Norovirus,Norwalk virus | — | KC409313 |
| Norovirus Hu/GII/30211/2009/VNM | NC_001959 | vertebrates,human | 1 | Caliciviridae,Norovirus,Norwalk virus | — | KC409315 |

| Taxonomy | NCBI Reference Sequence ID | Host | No. of Genomes | Lineage | Segment Count | Genbank Accession ID |
|---|---|---|---|---|---|---|
| Norovirus Hu/GII/30212/2009/VNM | NC_001959 | vertebrates,human | 1 | Caliciviridae,Norovirus,Norwalk virus | — | KC409316 |
| Norovirus Hu/GII/30266/2009/VNM | NC_001959 | vertebrates,human | 1 | Caliciviridae,Norovirus,Norwalk virus | — | KC409318 |
| Norovirus Hu/G11/8610/Saga/2008/JPN | NC_001959 | vertebrates,human | 1 | Caliciviridae,Norovirus,Norwalk virus | — | GU594162 |
| Norovirus Hu/GII/Carlow/2002/Ire | NC_001959 | vertebrates,human | 1 | Caliciviridae,Norovirus,Norwalk virus | — | DQ415279 |
| Norovirus Hu/Guangzhou/NVgz01/CHN | NC_001959 | vertebrates,human | 1 | Caliciviridae,Norovirus,Norwalk virus | — | DQ369797 |
| Norovirus Hu/Houston/TCH186/2002/US | NC_001959 | vertebrates,human | 1 | Caliciviridae,Norovirus,Norwalk virus | — | EU310927 |
| Norovirus Hu/MK04/2004/JP | NC_001959 | vertebrates,human | 1 | Caliciviridae,Norovirus,Norwalk virus | — | DQ456824 |
| Norovirus Hu/NLV/Dresden174/pUS-Nor11/1997/GE | NC_001959 | vertebrates,human | 1 | Caliciviridae,Norovirus,Norwalk virus | — | AY741811 |
| Norovirus Hu/NLV/Neustrelitz260/2000/DE | NC_001959 | vertebrates,human | 1 | Caliciviridae,Norovirus,Norwalk virus | — | AY772730 |
| Norovirus Hu/NLV/Oxford/B2S16/2002/UK | NC_001959 | vertebrates,human | 1 | Caliciviridae,Norovirus,Norwalk virus | — | AY587989 |
| Norovirus Hu/NLV/Oxford/B4S1/2002/UK | NC_001959 | vertebrates,human | 1 | Caliciviridae,Norovirus,Norwalk virus | — | AY587988 |
| Norovirus Hu/NLV/Oxford/B452/2002/UK | NC_001959 | vertebrates,human | 1 | Caliciviridae,Norovirus,Norwalk virus | — | AY587983 |
| Norovirus Hu/NLV/Oxford/B454/2002/UK | NC_001959 | vertebrates,human | 1 | Caliciviridae,Norovirus,Norwalk virus | — | AY587986 |
| Norovirus Hu/NLV/Oxford/B455/2002/UK | NC_001959 | vertebrates,human | 1 | Caliciviridae,Norovirus,Norwalk virus | — | AY587984 |
| Norovirus Hu/NLV/Oxford/B456/2002/UK | NC_001959 | vertebrates,human | 1 | Caliciviridae,Norovirus,Norwalk virus | — | AY587985 |
| Norovirus Hu/NLV/Oxford/B457/2002/UK | NC_001959 | vertebrates,human | 1 | Caliciviridae,Norovirus,Norwalk virus | — | AY587987 |
| Norovirus Hu/OsakaNI/2004/JP | NC_001959 | vertebrates,human | 1 | Caliciviridae,Norovirus,Norwalk virus | — | DQ366347 |
| Norovirus Hu/Pune/PC15/2006/India | NC_001959 | — | 1 | Caliciviridae,Norovirus,Norwalk virus | — | EU921344 |

-continued

| Taxonomy | NCBI Reference Sequence ID | Host | No. of Genomes | Lineage | Segment Count | Genbank Accession ID |
|---|---|---|---|---|---|---|
| Norovirus Hu/Pune/PC51/2007/India | NC_001959 | vertebrates,human | 1 | Caliciviridae,Norovirus,Norwalk virus | — | EU921388 |
| Norovirus Hu/Pune/PC52/2007/India | NC_001959 | — | 1 | Caliciviridae,Norovirus,Norwalk virus | — | EU921389 |
| Norovirus Hu/Texas/TCH04-577/2004/US | NC_001959 | vertebrates,human | 1 | Caliciviridae,Norovirus,Norwalk virus | — | AB365435 |
| Norovirus genogroup 2 | NC_001959 | vertebrates,human | 2 | Caliciviridae,Norovirus,Norwalk virus | — | AY502020,AY502023 |
| Norovirus genogroup 3 | NC_001959 | vertebrates,human | 1 | Caliciviridae,Norovirus,Norwalk virus | — | JX145650 |
| Norovirus mouse/Hannover1/2007/D EU | NC_001959 | vertebrates,human | 1 | Caliciviridae,Norovirus,Norwalk virus | — | EU854589 |
| Norovirus pig/GII/Ch6/China/2009 | NC_001959 | vertebrates,human | 1 | Caliciviridae,Norovirus,Norwalk virus | — | HQ392821 |
| Norovirus swine/GII/OH-QW 125/03/US | NC_001959 | vertebrates,human | 1 | Caliciviridae,Norovirus,Norwalk virus | — | AY823305 |
| North American arenavirus | NC_010700 | vertebrates,human | 3 | Arenaviridae,Arenavirus,Whitewater Arroyo virus | seg. S | EU123331,EU123330,EU123329 |
| Norwalk virus | NC_001959 | vertebrates,human | 3 | Caliciviridae,Norovirus,Norwalk virus | — | AF093797,AF504671,M87661 |
| Norwalk-like virus | NC_001959 | vertebrates,human | 17 | Caliciviridae,Norovirus,Norwalk virus | — | AB039780,AB083780,AB039782,AB03977 9,AY126474,AB0397 77,AB044366,AB126 320,AB039776,AB08 3781,AB081723,AB0 45603,AB039774,AB 039778,AB084071,A B039781,AB039775 |
| Oliveros virus | NC_010248 | vertebrates,human | 1 | Arenaviridae,Arenavirus,Oliveros virus | seg. S | U34248 |
| Oliveros virus | NC_010250 | vertebrates,human | 1 | Arenaviridae,Arenavirus,Oliveros virus | seg. L | AY216514 |
| Oran virus | NC_003466 | vertebrates,human | 1 | Bunyaviridae,Hantavirus,Andes virus | seg. S | AF482715 |
| Oran virus | NC_003467 | vertebrates,human | 1 | Bunyaviridae,Hantavirus,Andes virus | seg. M | AF028024 |
| Orangutan hepadnavirus | NC_003977 | vertebrates,human | 2 | Hepadnaviridae,Orthohepadnavirus,Hepatitis B virus | — | AF193863,AF193864 |
| Parainfluenza virus 5 | NC_006430 | vertebrates,human | 13 | Paramyxoviridae,Rubulavirus,Parainfluenza virus 5 | — | JQ743322,JQ743319,JQ743321,KC852177,JQ743327,JQ743328,JQ743318,JQ743325,JQ743324,JQ743323,AF052755,JQ743326,JQ743320 |
| Parana virus | NC_010756 | vertebrates,human | 2 | Arenaviridae,Arenavirus,Parana virus | seg. S | AF485261,AF512829 |
| Parana virus | NC_010761 | vertebrates,human | 1 | Arenaviridae,Arenavirus,Parana virus | seg. L | EU627613 |
| Pergamino virus | NC_003466 | vertebrates,human | 1 | Bunyaviridae,Hantavirus,Andes virus | seg. S | AF482717 |

-continued

| Taxonomy | NCBI Reference Sequence ID | Host | No. of Genomes | Lineage | Segment Count | Genbank Accession ID |
|---|---|---|---|---|---|---|
| Peste-des-petits-ruminants virus | NC_006383 | vertebrates,human | 11 | Paramyxoviridae,Morbillivirus,Peste-des-petits-ruminants virus | — | HQ197753,JX217850,AJ849636,KF727981,AY560591,EU267274,KC594074,X74443,EU267273,FJ905304,JF939201 |
| Pichinde virus | NC_006439 | vertebrates,human | 3 | Arenaviridae,Arenavirus,Pichinde virus | seg. L | AF427517,EF529745,EF529747 |
| Pichinde virus | NC_006447 | vertebrates,human | 10 | Arenaviridae,Arenavirus,Pichinde virus | seg. S | U77602,EF529746,M16734,EF529744,AF081552,K02734,AF081553,AF081554,AF081555,M16735 |
| Pigeon paramyxovirus 1 | NC_002617 | vertebrates,human | 18 | Paramyxoviridae,Avulavirus,Newcastle disease virus | — | GQ429292,JX486557,JX901121,JX901120,JX486555,JX486556,FJ410145,JX901119,JX486551,FJ410147,JX901110,JX486552,JX486554,JX901123,JX486553,JX901122,JX486550,JX901109 |
| Pigeon paramyxovirus-1 | NC_002617 | vertebrates,human | 1 | Paramyxoviridae,Avulavirus,Newcastle disease virus | — | AJ880277 |
| Pirital virus | NC_005894 | vertebrates,human | 9 | Arenaviridae,Arenavirus,Pirital virus | seg. S | AF485262,AY574571,AF277659,AY573923,AY574572,EU542420,AY574573,AY573921,AY575850 |
| Pirital virus | NC_005897 | vertebrates,human | 2 | Arenaviridae,Arenavirus,Pirital virus | seg. L | AY216505,AY494081 |
| Pneumonia virus of mice 15 | NC_006579 | vertebrates,human | 1 | Paramyxoviridae,Pneumovirus,Murine pneumonia virus | — | AY743910 |
| Pneumonia virus of mice J3666 | NC_006579 | vertebrates,human | 1 | Paramyxoviridae,Pneumovirus,Murine pneumonia virus | — | AY743909 |
| Porcine enteric sapovirus | NC_000940,NC_010624,NC_006269,NC_006554 | vertebrates,human | 3 | Caliciviridae,Sapovirus,Sapporo virus | — | AF182760,AB221130,AY425671 |
| Porcine rotavirus | NC_007543 | vertebrates,human | 3 | Reoviridae,Rotavirus,Rotavirus C | seg. 6 | EU169871,EU169870,EU169869 |
| Porcine rotavirus | NC_007544 | vertebrates,human | 1 | Reoviridae,Rotavirus,Rotavirus C | seg. 7 | X60546 |
| Porcine rotavirus | NC_007545 | vertebrates,human | 2 | Reoviridae,Rotavirus,Rotavirus C | seg. 9 | EU169873,EU169872 |
| Porcine rotavirus | NC_007569 | vertebrates,human | 3 | Reoviridae,Rotavirus,Rotavirus C | seg. | EU169874,DQ003298 10,DQ003299 |

-continued

| Taxonomy | NCBI Reference Sequence ID | Host | No. of Genomes | Lineage | Segment Count | Genbank Accession ID |
|---|---|---|---|---|---|---|
| Porcine rotavirus | NC_007570 | vertebrates,human | 10 | Reoviridae,Rotavirus,Rotavirus C | seg. 5 | L29184,DQ534018,FJ494692,M29287,FJ494691,DQ003294,AB576626,FJ494690,DQ03295,L29186 |
| Porcine rotavirus | NC_007571 | vertebrates,human | 101 | Reoviridae,Rotavirus,Rotavirus C | seg. 8 | EF474079,FJ807879, FJ807796,DQ003292, FJ807870,DQ534015, FJ807815,FJ807854, FJ807868,FJ807873, FJ807840,FJ807874, FJ807844,FJ807793, FJ807823,FJ807817, FJ807792,FJ807819, FJ807803,FJ807797, FJ807871,FJ807788, FJ807790,FJ807836, FJ807820,FJ807843, FJ807829,FJ807863, FJ807798,FJ807837, FJ807839,FJ807825, FJ807794,FJ807853, FJ807808,FJ807842, FJ807869,FJ807838, FJ807809,FJ807867, FJ807795,FJ807816, FJ807806,FJ807822, FJ807801,FJ807855, FJ807833,AF192267, FJ807835,FJ807802, FJ807818,FJ807847, FJ807789,FJ807810, FJ807828,FJ807862, FJ807832,FJ807851, FJ807866,FJ807813, FJ807831,FJ807848, FJ807845,DQ003293, FJ807877,FJ807852, FJ807858,FJ807826, FJ807859,FJ807811, FJ807799,AY766085, FJ807849,FJ807807, FJ807830,FJ807878, FJ807846,FJ807791, FJ807861,FJ807821, FJ807857,FJ807800, FJ807865,FJ807856, FJ807805,FJ807812, |

| Taxonomy | NCBI Reference Sequence ID | Host | Lineage | No. of Genomes | Segment Count | Genbank Accession ID |
|---|---|---|---|---|---|---|
| | | | | | | FJ807860,EU445113, FJ807804,FJ807824, FJ807841,FJ807864, FJ807876,FJ807875, FJ807850,FJ807827, FJ807834,FJ807814, L10361,FJ807872, L10360 |
| Porcine rotavirus | NC_007572 | vertebrates,human | Reoviridae,Rotavirus,Rotavirus C | 8 | seg. 3 | L10358,DQ003290,Li0359,DQ536362,DQ786578,DQ003291,DQ534016,AB576625 |
| Porcine rotavirus | NC_007573 | vertebrates,human | Reoviridae,Rotavirus,Rotavirus C | 6 | seg. 11 | DQ003296,DQ00474,D0003297,AB576628, DQ534017,DQ823416 |
| Porcine rotavirus A | NC_011501 | vertebrates,human | Reoviridae,Rotavirus,Rotavirus A | 7 | seg. 7 | JF796709,JF796698, AB779644,AB779643,JF796720,AB779642,AB779645 |
| Porcine rotavirus A | NC_011502 | vertebrates,human | Reoviridae,Rotavirus,Rotavirus A | 9 | seg. 8 | AB779639,AB779641,JF796719,JF796697, AB779638,JF796708, JF781165,AB779640, JF796730 |
| Porcine rotavirus A | NC_011503 | vertebrates,human | Reoviridae,Rotavirus,Rotavirus A | 26 | seg. 9 | AB176680,AB779619,DQ515961,JF796728,DQ204743,AY70778 8,AB573873,DQ786577,AB176677,AY707787,DQ786576,JF781163,AB176678,DQ256502,AB573875,JF796739,AB573879,AB573877,AB176681,AB176683,JF796706,KC292205,DQ256503,JF796717,AB605258,AB176679 |
| Porcine rotavirus A | NC_011504 | vertebrates,human | Reoviridae,Rotavirus,Rotavirus A | 11 | seg. 10 | JF796699,JF796721, D88831,JF781167,JF796710,JF796732,JN650610,FJ492833,DQ204740,FJ492834,JN650611 |
| Porcine rotavirus A | NC_011505 | vertebrates,human | Reoviridae,Rotavirus,Rotavirus A | 13 | seg. 11 | KC117150,DQ204739,JF796733,JF781168,JF796722,KC117151, |

| Taxonomy | NCBI Reference Sequence ID | Host | No. of Genomes | Lineage | Segment Count | Genbank Accession ID |
|---|---|---|---|---|---|---|
| | | | | | | KC117152,JF796700, KC117147,KC117149 DQ916134,KC117148,JF796711 |
| Porcine rotavirus A | NC_011506 | vertebrates,human | 5 | Reoviridae,Rotavirus,Rotavirus A | seg. 2 | AB779627,JF781159, AB779628,AB779629,AB779626 |
| Porcine rotavirus A | NC_011507 | vertebrates,human | 9 | Reoviridae,Rotavirus,Rotavirus A | seg. 1 | AB779622,JF796712, JF796701,AB779625, JF781158,JF796723, AB779624,JF796734, AB779623 |
| Porcine rotavirus A | NC_011508 | vertebrates,human | 11 | Reoviridae,Rotavirus,Rotavirus A | seg. 3 | AB779632,JF781160, AB779631,JF796714, AB779630,AY300922, AB779633,AY277921,JF796703,JF796725,JF796736 |
| Porcine rotavirus A | NC_011509 | vertebrates,human | 59 | Reoviridae,Rotavirus,Rotavirus A | seg. 6 | EU372751,EU372791, EU372765,EU372753,EU372789,AB779621,EU372776,EU372793,EU372764,EU372795,EU372797,EU372783,EU372774,JF796705,EU372787,KC855062,EU372773,D0119822,EU372756,JF796716,EU372781,EU372755,EU372772,EU372785,JF796727,EU372766,EU372762,EU372761,EU372763,EU372798,EU372786,EU372767,EU372770,KC855061,EU372779,EU372799,EU372768,EU372757,EU372771,EU372796,EU372777,EU372752,EU372782,EU372778,EU372790,KC855060,EU372754,EU372758,EU372794,EU372784,EU372769,EU372760,EU372759,EU372792,AB779620,EU372788,EU372778, |

| Taxonomy | NCBI Reference Sequence ID | Host | No. of Genomes | Lineage | Segment Count | Genbank Accession ID |
|---|---|---|---|---|---|---|
| Porcine rotavirus A | NC_011510 | vertebrates,human | 10 | Reoviridae,Rotavirus,Rotavirus A | seg. 4 | JF781161,JF796737, AB573878,DQ118979 ,AB573876,JF796726 ,JF796715,AB573874 ,JF796704,FJ492835 |
| Porcine rotavirus A A411/G3P[7] | NC_011504 | vertebrates,human | 1 | Reoviridae,Rotavirus,Rotavirus A | seg. 10 | AF144799 |
| Porcine rotavirus A strain 134/04-15 | NC_011503 | vertebrates,human | 1 | Reoviridae,Rotavirus,Rotavirus A | seg. 9 | DQ062572 |
| Porcine rotavirus A strain 134/04-15 | NC_011510 | vertebrates,human | 1 | Reoviridae,Rotavirus,Rotavirus A | seg. 4 | DQ061053 |
| Porcine rotavirus A34 | NC_007573 | vertebrates,human | 1 | Reoviridae,Rotavirus,Rotavirus C | seg. 11 | AF165219 |
| Porcine rotavirus B | NC_021542 | vertebrates,human | 1 | Reoviridae,Rotavirus,Rotavirus B | seg. 9 | AB490417 |
| Porcine rotavirus B | NC_021546 | vertebrates,human | 15 | Reoviridae,Rotavirus,Rotavirus B | seg. 5 | AB646359,AB646363 ,AB646364,AB646635 ,AB646360,AB6463 54,AB646350,AB646 361,AB646353,AB64 6351,AB646352,AB6 46358,AB646357,AB 646356,AB646362 |
| Porcine rotavirus C | NC_007543 | vertebrates,human | 1 | Reoviridae,Rotavirus,Rotavirus C | seg. 6 | M69115 |
| Porcine rotavirus C | NC_007546 | vertebrates,human | 1 | Reoviridae,Rotavirus,Rotavirus C | seg. 2 | M74217 |
| Porcine rotavirus C | NC_007547 | vertebrates,human | 1 | Reoviridae,Rotavirus,Rotavirus C | seg. 1 | M74216 |
| Porcine rotavirus C | NC_007570 | vertebrates,human | 2 | Reoviridae,Rotavirus,Rotavirus C | seg. 5 | HQ323754,M94157 |
| Porcine rotavirus C | NC_007571 | vertebrates,human | 14 | Reoviridae,Rotavirus,Rotavirus C | seg. 8 | EF464648,EF464656, EF464654,EF464651, U31749,EF464652,E F464653,EF464655,E F464650,U31748,HQ 323753,EF464649,M 61101,EF464657 |
| Porcine rotavirus C | NC_007573 | vertebrates,human | 2 | Reoviridae,Rotavirus,Rotavirus C | seg. 11 | AF093202,AF093203 |
| Porcine rotavirus C | NC_007574 | vertebrates,human | 1 | Reoviridae,Rotavirus,Rotavirus C | seg. 4 | M74219 |
| Porcine rotavirus CN86 | NC_007570 | vertebrates,human | 1 | Reoviridae,Rotavirus,Rotavirus C | seg. 5 | U10031 |
| Porcine rotavirus strain 344/04-1 | NC_007571 | vertebrates,human | 1 | Reoviridae,Rotavirus,Rotavirus C | seg. 8 | DQ813658 |
| Porcine rotavirus strain A131 | NC_007573 | vertebrates,human | 1 | Reoviridae,Rotavirus,Rotavirus C | seg. 11 | AF144798 |
| Porcine rotavirus strain A253 | NC_007573 | vertebrates,human | 1 | Reoviridae,Rotavirus,Rotavirus C | seg. 11 | AF144797 |
| Porcine rubulavirus | NC_009640 | vertebrates,human | 1 | Paramyxoviridae,Rubulavirus,Porcine rubulavirus | — | BK005918 |
| Porcine torque teno virus 1 | NC_014070 | vertebrates,human | 2 | Anelloviridae,Iotatorquevirus,Torque teno sus virus 1a | — | JX173482,JX173481 |

-continued

| Taxonomy | NCBI Reference Sequence ID | Host | No. of Genomes | Lineage | Segment Count | Genbank Accession ID |
|---|---|---|---|---|---|---|
| Puumala virus | NC_005223 | vertebrates,human | 25 | Bunyaviridae,Hantavirus,Puumala virus | seg. M | JQ319172,JQ319174,X61034,JQ319173,U14136,AF442617,AF442614,JQ319175,AF367061,AB433850,AF442616,L08754,JN831944,Z49214,M29979,Z84205,AB433852,LO8755,HE801634,JN831948,JN831951,AY526218,AF442615,U22418,AB297666 |
| Puumala virus | NC_005224 | vertebrates,human | 56 | Bunyaviridae,Hantavirus,Puumala virus | seg. S | AJ314597,FN377822,X61035,AF367069,AJ238788,AF367070,HE801633,U22423,AF367068,JQ319170,JN696371,JQ319163,JQ319164,Z30708,JN831943,AB297665,AJ238790,JQ319166,Z69985,JQ319162,Z30705,AB433845,AJ314598,JQ319168,AJ223371,Z30707,Z30706,JQ319171,JN831950,Z30703,AF442613,AJ314599,JQ319161,AF367064,JQ319167,AF367071,JN696376,JN831947,AF367066,AB433843,Z84204,Z30702,J0319169,JN696373,AF367065,AF367067,Z46942,JN696375,AY526219,JQ319165,FN377821,JN696372,Z21497,Z30704,AJ238789,JN696374 |
| Puumala virus | NC_005225 | vertebrates,human | 12 | Bunyaviridae,Hantavirus,Puumala virus | seg. L | JN831945,AB574183,JN831946,M63194,HE801635,AB574184,AY526217,AB297667,JN831952,JN831949,EF405801,Z66548 |
| Puumala-like virus isolate Fusong-Cr-247 | NC_005224 | vertebrates,human | 1 | Bunyaviridae,Hantavirus,Puumala virus | seg. S | EF442087 |

-continued

| Taxonomy | NCBI Reference Sequence ID | Host | No. of Genomes | Lineage | Segment Count | Genbank Accession ID |
|---|---|---|---|---|---|---|
| Rabbit rotavirus | NC_011503 | vertebrates,human | 4 | Reoviridae,Rotavirus,Rotavirus A | seg. 9 | AF528202,AF528201, AF528203,AF528204 |
| Rabbit rotavirus | NC_011504 | vertebrates,human | 4 | Reoviridae,Rotavirus,Rotavirus A | seg. 10 | AF533536,AF533534, AF533537,AF533535 |
| Rabbit rotavirus | NC_011505 | vertebrates,human | 1 | Reoviridae,Rotavirus,Rotavirus A | seg. 11 | JQ4361 |
| Rabbit rotavirus strain Alabama | NC_011504 | vertebrates,human | 1 | Reoviridae,Rotavirus,Rotavirus A | seg. 10 | AF144792 |
| Rabbitpox virus | NC_006998 | vertebrates,human | 1 | Poxviridae,Orthopoxvirus,Vaccinia virus | — | AY484669 |
| Rabies virus | NC_001542 | vertebrates,human | 204 | Rhabdoviridae,Lyssavirus,Rabies virus | — | JQ685916,JQ685948, EU293121,EF437215, AF499686,DQ099525, EU182347,AB085828, JN786878,GU565703, JQ685966,JX473839, KC595283,JQ685962, GU345746,GU647092, EF542830,EF564174, AY956319,GU565704,EU293115,J0685975,JQ685893, KF155000,EU877068, JX473841,JQ685919, JEF206719,KC17164, JEF206720,AB044824, JQ685964,EF206708, KC595281,JQ685959, JQ685926,JQ685892, JQ685897,JQ685905, HQ450386,JQ685963, JQ944709,JQ685942, JN609295,JQ685895, HQ317918,JQ685945, KF154997,JQ685894, AB569299,FJ577895, KC171644,JQ685932, FJ712195,AB685847, HM535790,JQ685930, JQ685940,AB635373, EU293116,D0099524, KC193267,KC169986,JQ685901, FJ913470,FJ959397, JQ685967,FJ712193, JQ685924,JQ685917, JQ685958,JQ685934, GU345747,KC737850, JQ685941,HE80267 |

| Taxonomy | NCBI Reference Sequence ID | Host | No. of Genomes | Lineage | Segment Count | Genbank Accession ID |
|---|---|---|---|---|---|---|
| | | | | | | 5,AY705373,JQ68595 4,JQ685909,EF20671 8,EF206714,M31046, JQ685957,JQ685912, JXQ88694,JQ685973, KF154999,JQ685898, JQ685968,JQ685946, JQ685965,EF206713, DQ875051,GU35865 3,KF154998,GQ9181 39,JQ685951,JQ7306 82,JQ685921,EF2067 09,JQ685902,EU877 071,JQ685937,AB519 642,JQ685910,AB128 149,JQ944707,JQ685 952,KC171643,JQ94 4708,EF206707,AB69 9220,JQ685928,AB51 7660,JQ685931,JQ68 5933,JQ685900,EF20 6710,JQ685974,EU3 11738,JQ423952,AB3 62483,JQ685913,JQ6 85977,JQ685903,AB5 17659,JQ685953,JX2 76550,JQ685914,FJ7 12194,JQ685911,JQ6 85906,JQ685915,AB6 08731,JQ685908,JQ6 85922,JQ685947,JQ6 85935,AB519641,HE 802676,JQ685956,E U182346,JQ685976,J 0685950,EF206712,J 0685925,EU643590, FJ866836,EU293113, FJ866835,JQ685939, AB009663,DQ875050 ,KC595280,EF20671 1,EU877070,JQ6859 44,JQ685955,EF2067 16,JQ685929,EU549 783,EF206717,JQ685 961,JQ944704,JQ685 971,KF155002,GU34 5748,KC762941,JQ6 85918,JQ685920,JQ6 |

| Taxonomy | NCBI Reference Sequence ID | Host | No. of Genomes | Lineage | Segment Count | Genbank Accession ID |
|---|---|---|---|---|---|---|
| Ravn virus-Ravn,Kenya, 1987 | NC_001608 | vertebrates,human | 3 | Filoviridae,Marburgvirus,Marburg marburgvirus | — | 85970,JQ685969,JQ6 85936,HQ891318,JQ 685960,JQ685943,JQ 685896,JQ685927,JQ 685938,EF206715,JQ 647510,KF154996,FJ 712196,EU293111,JX 473840,KC595282,J 0685907,JQ946087, KC196743,JX473838, JN786877,JQ685972, JQ685949,JN234411

-continued

| Taxonomy | NCBI Reference Sequence ID | Host | No. of Genomes | Lineage | Segment Count | Genbank Accession ID |
|---|---|---|---|---|---|---|
| Recombinant Hepatitis C virus DH5-JFH1 | NC_009827,NC_009826,NC_009825,NC_009824,NC_004102,NC_009823 | vertebrates,human | 1 | Flaviviridae,Hepacivirus,Hepatitis C virus | — | HQ852456 |
| Recombinant Hepatitis C virus DH6-JFH1 | NC_009827,NC_009826,NC_009825,NC_009824,NC_004102,NC_009823 | vertebrates,human | 1 | Flaviviridae,Hepacivirus,Hepatitis C virus | — | HQ852454 |
| Recombinant Hepatitis C virus ED43(5'UTR-NS2)/JFH1_T827A,T977S | NC_009827,NC_009826,NC_009825,NC_009824,NC_004102,NC_009823 | vertebrates,human | 1 | Flaviviridae,Hepacivirus,Hepatitis C virus | — | JF343785 |
| Recombinant Hepatitis C virus H77(5'UTR-NS2)/JFH1_V787A,Q1247L | NC_009827,NC_009826,NC_009825,NC_009824,NC_004102,NC_009823 | vertebrates,human | 1 | Flaviviridae,Hepacivirus,Hepatitis C virus | — | JF343780 |
| Recombinant Hepatitis C virus H77C/JFH1 | NC_009827,NC_009826,NC_009825,NC_009824,NC_004102,NC_009823 | vertebrates,human | 1 | Flaviviridae,Hepacivirus,Hepatitis C virus | — | EU363761 |
| Recombinant Hepatitis C virus HK6a(5'UTR-NS2)/JFH1_F350S,N417T | NC_009827,NC_009826,NC_009825,NC_009824,NC_004102,NC_009823 | vertebrates,human | 1 | Flaviviridae,Hepacivirus,Hepatitis C virus | — | JF343787 |
| Recombinant Hepatitis C virus HK6a/JFH-1 | NC_009827,NC_009826,NC_009825,NC_009 | vertebrates,human | 1 | Flaviviridae,Hepacivirus,Hepatitis C virus | — | FJ230883 |

-continued

| Taxonomy | NCBI Reference Sequence ID | Host | No. of Genomes | Lineage | Segment Count | Genbank Accession ID |
|---|---|---|---|---|---|---|
| | 824,NC_004102,NC_009823 | | | | | |
| Recombinant Hepatitis C virus J4(5'UTR-NS2)/JFH1_F886L,01496L | NC_009827,NC_009826,NC_009825,NC_009824,NC_004102,NC_009823 | vertebrates,human | 1 | Flaviviridae,Hepacivirus,Hepatitis C virus | — | JF343781 |
| Recombinant Hepatitis C virus J4/JFH1 | NC_009827,NC_009826,NC_009825,NC_009824,NC_004102,NC_009823 | vertebrates,human | 1 | Flaviviridae,Hepacivirus,Hepatitis C virus | — | FJ230881 |
| Recombinant Hepatitis C virus J6(5'UTR(1b-E1)-NS2)/JFH1 | NC_009827,NC_009826,NC_009825,NC_009824,NC_004102,NC_009823 | vertebrates,human | 1 | Flaviviridae,Hepacivirus,Hepatitis C virus | — | JF343793 |
| Recombinant Hepatitis C virus J6(5'UTR(2a-Dom1/11)-NS2)/JFH1 | NC_009827,NC_009826,NC_009825,NC_009824,NC_004102,NC_009823 | vertebrates,human | 1 | Flaviviridae,Hepacivirus,Hepatitis C virus | — | JF343792 |
| Recombinant Hepatitis C virus J6(5'UTR(Cell-ATAD1)-NS2)/JFH1 | NC_009827,NC_009826,NC_009825,NC_009824,NC_004102,NC_009823 | vertebrates,human | 1 | Flaviviridae,Hepacivirus,Hepatitis C virus | — | JF343791 |
| Recombinant Hepatitis C virus J6(5'UTR(Cell-U3)-NS2)/JFH1 | NC_009827,NC_009826,NC_009825,NC_009824,NC_004102,NC_009823 | vertebrates,human | 1 | Flaviviridae,Hepacivirus,Hepatitis C virus | — | JF343788 |

| Taxonomy | NCBI Reference Sequence ID | Host | No. of Genomes | Lineage | Segment Count | Genbank Accession ID |
|---|---|---|---|---|---|---|
| Recombinant Hepatitis C virus J6(5'UTR(Cell-U3WTS1)-NS2)/JFH1 | NC_009827, NC_009826, NC_009825, NC_009824, NC_004102

-continued

| Taxonomy | NCBI Reference Sequence ID | Host | No. of Genomes | Lineage | Segment Count | Genbank Accession ID |
|---|---|---|---|---|---|---|
| | 824,NC_004102,NC_009823 | | | | | |
| Recombinant Hepatitis C virus J6/JFH1(HK6a-NS5A) | NC_009827,NC_009826,NC_009825,NC_009824,NC_004102,NC_009823 | vertebrates,human | 1 | Flaviviridae,Hepacivirus,Hepatitis C virus | — | HQ852465 |
| Recombinant Hepatitis C virus J6/JFH1(J1-NS5A) | NC_009827,NC_009826,NC_009825,NC_009824,NC_004102,NC_009823 | vertebrates,human | 1 | Flaviviridae,Hepacivirus,Hepatitis C virus | — | HQ852469 |
| Recombinant Hepatitis C virus J6/JFH1(J4-NS5A) | NC_009827,NC_009826,NC_009825,NC_009824,NC_004102,NC_009823 | vertebrates,human | 1 | Flaviviridae,Hepacivirus,Hepatitis C virus | — | HQ852460 |
| Recombinant Hepatitis C virus J6/JFH1(J6-NS5A) | NC_009827,NC_009826,NC_009825,NC_009824,NC_004102,NC_009823 | vertebrates,human | 1 | Flaviviridae,Hepacivirus,Hepatitis C virus | — | HQ852461 |
| Recombinant Hepatitis C virus J6/JFH1(0C69-NS5A) | NC_009827,NC_009826,NC_009825,NC_009824,NC_004102,NC_009823 | vertebrates,human | 1 | Flaviviridae,Hepacivirus,Hepatitis C virus | — | HQ852466 |
| Recombinant Hepatitis C virus J6/JFH1(S52-NS5A) | NC_009827,NC_009826,NC_009825,NC_009824,NC_004102,NC_009823 | vertebrates,human | 1 | Flaviviridae,Hepacivirus,Hepatitis C virus | — | HQ852462 |

-continued

| Taxonomy | NCBI Reference Sequence ID | Host | No. of Genomes | Lineage | Segment Count | Genbank Accession ID |
|---|---|---|---|---|---|---|
| Recombinant Hepatitis C virus J6/JFH1(SA13-NS5A) | NC_009827,NC_009826,NC_009825,NC_009824,NC_004102,NC_009823 | vertebrates,human | 1 | Flaviviridae,Hepacivirus,Hepatitis C virus | — | HQ852464 |
| Recombinant Hepatitis C virus J6/JFH1(TN-NS5A) | NC_009827,NC_009826,NC_009825,NC_009824,NC_004102,NC_009823 | vertebrates,human | 1 | Flaviviridae,Hepacivirus,Hepatitis C virus | — | HQ852459 |
| Recombinant Hepatitis C virus J6/JFH 1-452 | NC_009827,NC_009826,NC_009825,NC_009824,NC_004102,NC_009823 | vertebrates,human | 1 | Flaviviridae,Hepacivirus,Hepatitis C virus | — | JN180456 |
| Recombinant Hepatitis C virus J6/JFH 1-H K6a | NC_009827,NC_009826,NC_009825,NC_009824,NC_004102,NC_009823 | vertebrates,human | 1 | Flaviviridae,Hepacivirus,Hepatitis C virus | — | JN180455 |
| Recombinant Hepatitis C virus J6/JFH 1-J6 | NC_009827,NC_009826,NC_009825,NC_009824,NC_004102,NC_009823 | vertebrates,human | 1 | Flaviviridae,Hepacivirus,Hepatitis C virus | — | JN180452 |
| Recombinant Hepatitis C virus J6/JFH1-JCH2 | NC_009827,NC_009826,NC_009825,NC_009824,NC_004102,NC_009823 | vertebrates,human | 1 | Flaviviridae,Hepacivirus,Hepatitis C virus | — | JN180459 |
| Recombinant Hepatitis C virus J6/JFH1-JCH4 | NC_009827,NC_009826,NC_009825,NC_009 | vertebrates,human | 1 | Flaviviridae,Hepacivirus,Hepatitis C virus | — | JN180460 |

-continued

| Taxonomy | NCBI Reference Sequence ID | Host | No. of Genomes | Lineage | Segment Count | Genbank Accession ID |
|---|---|---|---|---|---|---|
| | 824,NC_004102,NC_009823 | | | | | |
| Recombinant Hepatitis C virus J6/JFH1-K3a,650 | NC_009827,NC_009826,NC_009825,NC_009824,NC_004102,NC_009823 | vertebrates,human | 1 | Flaviviridae,Hepacivirus,Hepatitis C virus | — | JN180457 |
| Recombinant Hepatitis C virus J6/JFH1-NZL1 | NC_009827,NC_009826,NC_009825,NC_009824,NC_004102,NC_009823 | vertebrates,human | 1 | Flaviviridae,Hepacivirus,Hepatitis C virus | — | JN180458 |
| Recombinant Hepatitis C virus J6/JFH 1-S52 | NC_009827,NC_009826,NC_009825,NC_009824,NC_004102,NC_009823 | vertebrates,human | 1 | Flaviviridae,Hepacivirus,Hepatitis C virus | — | JN180453 |
| Recombinant Hepatitis C virus J6/JFH 1-SA13 | NC_009827,NC_009826,NC_009825,NC_009824,NC_004102,NC_009823 | vertebrates,human | 1 | Flaviviridae,Hepacivirus,Hepatitis C virus | — | JN180454 |
| Recombinant Hepatitis C virus J8(5'UTR-NS2)/JFH1 | NC_009827,NC_009826,NC_009825,NC_009824,NC_004102,NC_009823 | vertebrates,human | 1 | Flaviviridae,Hepacivirus,Hepatitis C virus | — | JF343783 |
| Recombinant Hepatitis C virus J8/JFH1 | NC_009827,NC_009826,NC_009825,NC_009824,NC_004102,NC_009823 | vertebrates,human | 1 | Flaviviridae,Hepacivirus,Hepatitis C virus | — | FJ230882 |

-continued

| Taxonomy | NCBI Reference Sequence ID | Host | Lineage | No. of Genomes | Segment Count | Genbank Accession ID |
|---|---|---|---|---|---|---|
| Recombinant Hepatitis C

| Taxonomy | NCBI Reference Sequence ID | Host | No. of Genomes | Lineage | Segment Count | Genbank Accession ID |
|---|---|---|---|---|---|---|
| | | | | | | BDQ81932,BD137602,JX503101,BD137601,BD271636,JN032116,BDQ81931,BD27163 5,BDQ81929,JN03211 7,BD137599,JN03212 0 |
| Reston ebolavirus | NC_004161 | vertebrates,human | 4 | Filoviridae,Ebolavirus,Reston ebolavirus | — | AF522874,JX477166, AY769362,JX477165 |
| Reston ebolavirus-Reston | NC_004161 | vertebrates,human | 4 | Filoviridae,Ebolavirus,Reston ebolavirus | — | AB050936,FJ621585, FJ621583,FJ621584 |
| Retroperitoneal fibromatosis-associated herpesvirus | NC_009333 | vertebrates,human | 1 | Herpesviridae,Rhadinovirus,Human herpesvirus 8 | — | KF703446 |
| Rhesus rotavirus | NC_011500 | vertebrates,human | 8 | Reoviridae,Rotavirus,Rotavirus A | seg. 5 | AY117051,AY117052,AY117049,AY117053,AY117053,0,U08433,AY117053,HQ665465,AY117048 |
| Rhesus rotavirus | NC_011502 | vertebrates,human | 1 | Reoviridae,Rotavirus,Rotavirus A | seg. 8 | AY065842 |
| Rhesus rotavirus | NC_011503 | vertebrates,human | 3 | Reoviridae,Rotavirus,Rotavirus A | seg. 9 | HQ665466,M21650,AF295303 |
| Rhesus rotavirus | NC_011505 | vertebrates,human | 1 | Reoviridae,Rotavirus,Rotavirus A | seg. 11 | HQ665467 |
| Rhesus rotavirus | NC_011510 | vertebrates,human | 2 | Reoviridae,Rotavirus,Rotavirus A | seg. 4 | M18736,AY033150 |
| Rhinovirus A | NC_001617 | vertebrates,human | 2 | Picornaviridae,Enterovirus,Rhinovirus A | — | JXQ74050,GQ223229 |
| Rhinovirus B | NC_001490 | vertebrates,human | 1 | Picornaviridae,Enterovirus,Rhinovirus B | — | JX193795 |
| Rinderpest virus | NC_006296 | vertebrates,human | 7 | Paramyxoviridae,Morbillivirus,Rinderpest virus | — | JN234008,GU168576,JN234010,AB547190,JN234009,AB547189 |
| Rinderpest virus (strain Kabete O) | NC_006296 | vertebrates,human | 1 | Paramyxoviridae,Morbillivirus,Rinderpest virus | — | X98291 |
| Rodent hepacivirus | NC_021153 | vertebrates,human | 1 | Flaviviridae,Hepacivirus,Rodent hepacivirus | — | KC815310 |
| Rotavirus A | NC_011500 | vertebrates,human | 94 | Reoviridae,Rotavirus,Rotavirus A | seg. 5 | JN258352,JN258790,JXQ27770,JN651781,JN258907,JXQ27881,JN651846,JXQ27738,HQ657144,JXQ27782,JXQ27866,JXQ27902,JXQ27662,JXQ27760,JN258407,JN635549,JXQ27837,JN651748,JN258810,JN635538,JN258951,JN635527,JXQ27892,JN827248,JXQ27811,JF521476,JXQ27943,JXQ27815,JN651857,JXQ27847, |

| Taxonomy | NCBI Reference Sequence ID | Host | No. of Genomes | Lineage | Segment Count | Genbank Accession ID |
|---|---|---|---|---|---|---|
| | | | | | | JN258862,JN651813, JXQ27756,HQ657133 ,JN258944,JN651792 ,JN258892,JN258337 ,JN258833,JN872871 ,JN258355,HQ65715 5,JXQ27947,JN25884 5,JXQ27672,JXQ2771 3,JN651879,JXQ2792 4,JN831204,JXQ2772 1,JN258395,JQ68867 7,JXQ27651,GU5650 69,JN831226,JXQ276 95,JN013975,JXQ276 91,JXQ27870,JXQ279 14,FN665692,JN2588 54,GU565047,JXQ27 966,GU827412,JN65 1803,JN651759,JN25 8801,GU565091,GU5 65058,JXQ27832,FN6 65681,JN831215,JXQ 27644,JXQ27726,JN6 51770,JN258377,JN6 51824,JXQ27793,JN6 51835,FJ169857,JN2 58372,JN258821,JN0 13974,JN258878,GU 565080,JN651874,JF 521465,JN258914,JN 258925,DQ838599,J XQ279968,JN651890,J N258887 |
| Rotavirus A | NC_011501 | vertebrates,human | 387 | Reoviridae,Rotavirus,Rotavirus A | seg. 7 | KC443781,KC579550 ,JN258391,KC579943 ,EF990696,KC44292 5,KC443562,KC8346 92,KC580442,FJ17939 79,KC580343,KC580 465,KC443364,KC57 9572,KC443595,KC5 79710,KC443661,KC 580548,JXQ40431,KC 174896,KC580534,K C769324,KC443617, FJ793988,JX406753, KC443342,KC579778 ,KC443683,HQ66113 |

| Taxonomy | NCBI Reference Sequence ID | Host | No. of Genomes | Lineage | Segment Count | Genbank Accession ID |
|---|---|---|---|---|---|---|
| | | | | | | 1,KC579925,JN60545 6,KC443771,KC1752 22,KC580035,KC175 255,EF990692,KC57 9495,EF990710,KC5 79627,KC579991,KC 769302,KC443716,JN 258358,KC580275,K C769445,KC215570, DQ492676,KC443551 ,JN258334,KC175069 ,KC443153,GU82741 4,JN258929,FJ79398 5,KC174940,KC5800 94,JN258840,KC4437 38,JN651750,KC5803 54,KC443529,KC579 957,KC579661,KC44 2971,KC580620,KC8 34691,D

| Taxonomy | NCBI Reference Sequence ID | Host | No. of Genomes | Lineage | Segment Count | Genbank Accession ID |
|---|---|---|---|---|---|---|
| | | | | | | ,KC579506,KC76940 1,JN258871,DQ4905 34,KC174972,KC175 266,HQ657146,KC44 3208,FN665684,GU1 99518,KC215537,KC 579877,JN651761,G U565059,KC175112,J N651881,KC443441,J N258381,KC579811, KC579660,KC580240 ,KC175003,GU56508 1,KC443230,KC1936 20,KC443650,EF554 155,KC579688,KC44 3386,KC443573,JN25 8947,KC215494,FJ79 3973,KC580523,JN65 1868,JN651826,KC44 3639,JN831217,FJ79 3981,KC443252,JN87 2873,KC443296,KC4 43131,KC215516,KC 580207,FJ793969,KC 443285,KC580420,K C175091,KC579822, KC175025,KC443263 ,KC175156,KC17490 7,KC769390,KC1751 67,KC442878,JN6054 45,KC579472,KC443 727,KC579911,KC58 0398,KC443219,KC5 79924,FJ793992,KC7 69379,KC443375,KC 443026,KC579699,K C193609,JN258369,K C580598,KC580276, EF554144,KC580229 ,KC443540,FJ793974 ,GU565070,KC58015 0,FJ793971,JN65179 4,KC580319,KC5798 36,KC580185,KC174 962,GU565092,JN25 8828,KC580431,JX96 5151,KC442993,JN65 1805,KC580409,HQ6 |

| Taxonomy | NCBI Reference Sequence ID | Host | No. of Genomes | Lineage | Segment Count | Genbank Accession ID |
|---|---|---|---|---|---|---|
| | | | | | | 57157,KC443672,KC579616,KC580218,KC579539,FJ169859,KC175102,FJ793980,KC579517,KC580365,JN258859,KC579968, KC174918,JN258896,KC579583,KC580013,JN635540,KC579852,JN258402,HQ846871,KC443749,KC580609,KC174885,JN831206,KC580196,KC580511,EF990700,KC443705,KC443408,KC579721,KC443004,JX271009,JQ988896,JX271006,KC175058,FJ793987,KC174993,JN605434,KC175036,FJ793978,DQ146703,KC443485,DQ146645,EF990688,JN651837,KC442867,KC769346,JN258781,KC443397,KC580547,KC443197,KC579835,JN013979,KC580500,JN651859,KC140595,KC175014,KC769423,GU296415,KC443331,KC174951,FJ793983,KC443496,KC580173,JN827250,JN635551,KC443175,JX965153,KC175080,FJ793984,KC579800,KC580071,JN258938,HQ846882,KC580332,JN258848,KC443142,FJ793972,JN605423,KC580488,KC175178,KC580294,KC442937,KC215474,KC580631,KC579789,FJ793986,JN258806,KC579641,KC769456,KC579677,KC769368,KC579561,JN635528 |

| Taxonomy | NCBI Reference Sequence ID | Host | No. of Genomes | Lineage | Segment Count | Genbank Accession ID |
|---|---|---|---|---|---|---|
| | | | | | | 9,KC443760,JN01398 0,KC579743,GU1995 00,JN651783,KC5804 64,KC175145,KC443 164,KC769412,KC21 5483,FJ793977,KC17 5211,KC769313,KC5 79732,DQ146689,KC 769434,KC580053,K C442900,KC443694,J N651897,KC580453, KC215548,KC215505 ,KC580387,DQ14665 6,FJ793982,KC57988 8,DQ490558,KC5799 80,DQ490541,KC580 083,EF990704,JF835 114,JN605412,KC443 507,KC195757,JN258 918,KC175

| Taxonomy | NCBI Reference Sequence ID | Host | No. of Genomes | Lineage | Segment Count | Genbank Accession ID |
|---|---|---|---|---|---|---|
| | | | | | | 057,KC579482,JXQ27 6640,KC579941,DQ14 6690,JN258782,KC57 9720,KC193608,KC1 75155,KC175133,JN6 51793,KC580206,KC 175232,KC175046,K C443284,KC580161,J F521468,KC175090,J N258365,KC195765, GU565082,KC174950 ,DQ490559,KC44297 0,KC443141,KC5800 23,JXQ27665,KC4431 63,DQ490542,KC443 484,JN258945,JN651 858,KC769466,KC58 0463,JN651771,KC58 0574,JN258902,JN65 1836,KC580184,EF5 54145,JX406754,KC5 80138,KC443374,KC 443295,DQ146697,K C443605,JXQ27956,J X683000,HQ846861, KC442888,KC580149 ,HQ657145,JXQ2775 9,KC580487,JN83121 6,JXQ27715,KC17510 1,KC579639,KC4431 85,GU565093,KC215 536,KC175068,GU56 5071,KC443352,KC1 75013,DQ146704,KC 174884,JX965148,KC 443660,KC579777,JN 605455,KC193629,JX 027781,KC443473,JX 027825,KC443341,K C834693,KC769400, KC443273,GU199489 ,KC442936,JN377717 ,KC580522,KCO2003 3,KC579899,KC4437 37,KC443451,KC443 385,JXQ27967,GU19 9517,KC195754,KC1 74971,KC443003,FJ1 |

| Taxonomy | NCBI Reference Sequence ID | Host | No. of Genomes | Lineage | Segment Count | Genbank Accession ID |
|---|---|---|---|---|---|---|
| | | | | | | 69860,KC174906,FN665694,KC443363,KC174992,JN872872,EF990705,JN635528,KC580342,KC442924,KC175122,KC175276,KC579659,GU199499,DQ146646,EF990689,KC442992,JX682998,KC442866,KC580239,KC579788,KC580375,GU296413,KC579676,JN651891,KC579864,JXQ27836,JN258860,JN651782,KC443014,DQ492677,KC020021,KC579942,KC443726,KC140594,JN651875,JXQ27923,KC443262,JXQ27846,JN258873,KC443407,KC175166,KC769334,KC580585,DQ14667,9,KC579887,JXQ27748,EF990693,KC443429,KC579922,KC175079,JXQ27891,HQ661119,KC580012,KC443440,JN258387,JN258816,KC175177,JN651880,KC580316,JX271008,KC579799,JXQ27698,KC579876,JXQ27737,JXQ27814,KC580475,JXQ27814,KC580317,JN443693,JX965150,JN605422,KC579834,KC579990,JN377719,JN258802,KC579604,JF521479,HQ846883,KC443152,DQ146668,JN377721,KCO20031,KC443561,KC76935,6,JN013977,KC58036,4,JN651847,KC44289,9,JF712584,KC57974,2,KC580273,KC5800,51,KC579753,JN2583 |

-continued

| Taxonomy | NCBI Reference Sequence ID | Host | No. of Genomes | Lineage | Segment Count | Genbank Accession ID |
|---|---|---|---|---|---|---|
| | | | | | | 98,JN258824,KC5804 |
| | | | | | | 30,JN831205,KC4433 |
| | | | | | | 96,KC174939,KC443 |
| | | | | | | 748,KC443229,KC44 |
| | | | | | | 3025,KC580001,KC4 |
| | | | | | | 43196,JN258924,KC4 |
| | | | | | | 43462,KC579979,KC |
| | | | | | | 443759,KC579731,JN |
| | | | | | | 651749,KC443306,K |
| | | | | | | C579810,KC174862, |
| | | | | | | KC175265,GU565060 |
| | | | | | | ,KC443780,JQ98889 |
| | | | | | | 5,KC579494,JXQ2788 |
| | | | | | | 0,JXQ27946,KC58007 |
| | | | | | | 0,KC769323,JN25834 |
| | | | | | | 3,KC579910,KCO200 |
| | | | | | | 20,KC443616,KC443 |
| | | | | | | 638,KC580250,GU29 |
| | | | | | | 6412,KC580082,KC7 |
| | | | | | | 69345,JXQ27687,JXQ |
| | | | | | | 27671,KC443506,JN8 |
| | | | | | | 27252,KC175002,JXQ |
| | | | | | | 27703,KC579821,KC |
| | | | | | | 442947,KC443251,K |
| | | | | | | C174961,KC579833, |
| | | | | | | GU199510,KC769433 |
| | | | | | | ,KC442877,EF13666 |
| | | | | | | 0,KC579549,JN37771 |
| | | | | | | 8,JXQ27858,KC83469 |
| | | | | | | 4,JN651814,KC57985 |
| | | | | | | 1,EF990711,KC4436 |
| | | | | | | 82,KC443517,JX9651 |
| | | | | | | 49,KC579560,KC579 |
| | | | | | | 967,KC580116,JN258 |
| | | | | | | 836,KC769422,EF55 |
| | | | | | | 4156,HQ657156,JXQ |
| | | | | | | 27792,KC579626,JXQ |
| | | | | | | 40429,GU565049,KC |
| | | | | | | 579709,JX682999,JN |
| | | | | | | 258913,JN258354,KC |
| | | | | | | 769455,KC580533,K |
| | | | | | | C174895,KC769411, |
| | | | | | | KC579956,JN651760, |
| | | | | | | JN258794,KC174917, |
| | | | | | | KC175111,KC834695 |
| | | | | | | ,KC580093,KC44341 |
| | | | | | | 8,KC580408,KC7694 |
| | | | | | | 44,KC175024,KC769 |

| Taxonomy | NCBI Reference Sequence ID | Host | No. of Genomes | Lineage | Segment Count | Genbank Accession ID |
|---|---|---|---|---|---|---|
| | | | | | | 378,KC443671,JN258849,KC579863,KC443330,JN258882,KC580386,KC580050,KCO20022,KC580034,KC769301,HQ661130,KC443715,JN651804,EF990697,KC174873,JN651825,GU827413,JN605433,KC769389,KC579471,KC175221,JN258935,KC193619,KC174981,KC579950,5,KC580172,JQ6886 80,JN258376,JN831227,JXQ27913,JN377720,KC580195,KC443649,KC580499,KC579538,KC580510,KC175035,KC443572,KC443704,JN635539,KC443240,KC579766,KC443130,HQ846872,KC175210,KC580261,KC579593,KC443770,KC175199,HQ657134,JF712573,JN013978,JN258891,KC443495,JXQ27769,KC443207,KC579923,KC579571,HQ661141,JN605444,KC580274,JXQ27725,KCO20028,DQ838615,KC580452,KC580127,KC442981,JN013976,KC579527,KC443627,KC580217,KCO20032,KC580597,KC174928,KC175254,KC442910,KC769477,KC443174,JX682997,JN258332,KC580104,KC580630,KC580441,KC443594,KC175188,KC443307,KC579615,KC580228,DQ490535,DQ146657,KC443583,EF990701, |

| Taxonomy | NCBI Reference Sequence ID | Host | No. of Genomes | Lineage | Segment Count | Genbank Accession ID |
|---|---|---|---|---|---|---|
| | | | | | | KC443539,JXQ27803,JF712562,KC580545,KC443319,KC579698,KC443218,JXQ27934,KC579516,KCO2002 7,KC580304,KC5806 19,KC580546,KC580 293,KC175144,KC76 9367,KC580563,KC7 69312,FN665683,KC 580419,JXQ27654,KC 580397,KC215493,JN 605411,JXQ277901,KC 443550,KC579638 |
| Rotavirus A | NC_011503 | vertebrates,human | 429 | Reoviridae,Rotavirus,Rotavirus A | seg. 9 | KC442875,JX841120, JN651889,AB081787, KC580102,GU565068 ,KC579977,KC58063 9,EF079066,KC8346 37,KC580313,KC443 249,KC579696,KC76 9332,JN258874,KC17 5230,KC580473,KC1 75241,KC175000,KC 580595,JN651845,JX 965176,AB081793,A Y773303,HQ846862, KC579613,AB26247 ,KC175033,AB08179 4,KC834638,KC1751 09,GU296431,KC580 237,U26386,AB08179 5,KC580226,KC5795 91,JN258941,KC4436 14,JX965166,JN2589 17,KC579547,JN6518 02,AB081777,U26395 ,KC443172,KC44363 6,KC443361,KC4434 16,KC174871,AB081 790,AB081798,AB08 1792,KC769321,KC4 43394,AB081780,KC 443304,KC580362,JN 258401,EF079069,AB 571046,KC580080,A B081801,KC443227, HQ846884,DQ47858 |

| Taxonomy | NCBI Reference Sequence ID | Host | No. of Genomes | Lineage | Segment Count | Genbank Accession ID |
|---|---|---|---|---|---|---|
| | | | | | | 2,KC443647,KC4436 |
| | | | | | | 03,KC580204,FJ1698 |
| | | | | | | 61,KC579808,KC443 |
| | | | | | | 150,HE646643,JX965 |
| | | | | | | 177,KC174926,JN258 |
| | | | | | | 844,KC443449,JN831 |
| | | | | | | 236,U26388,KC5797 |
| | | | | | | 64,AB526249,JN0139 |
| | | | | | | 98,KC443161,KC580 |
| | | | | | | 170,AB081776,KC44 |
| | | | | | | 3724,AB081774,KC5 |
| | | | | | | 80561,JN258805,KC1 |
| | | | | | | 75208,U26387,KC83 |
| | | | | | | 4641,KC443702,HQ6 |
| | | | | | | 61117,JN635559,KC5 |
| | | | | | | 79751,KC174948,KC |
| | | | | | | 443194,KC580091,K |
| | | | | | | C834635,JN258846, |
| | | | | | | HQ846873,KC580450 |
| | | | | | | ,JF712571,KC769398 |
| | | | | | | ,KC443789,KC58025 |
| | | | | | | 9,KC769475,JN82725 |
| | | | | | | 3,AB081785,KC1957 |
| | | | | | | 63,JN258338,JN6517 |
| | | | | | | 58,KC175285,KC443 |
| | | | | | | 293,DQ492674,JX9 |
| | | | | | | 2886,KC443757,KC44 |
| | | | | | | 65164,KC580182,KC |
| | | | | | | 580485,AB081593,G |
| | | | | | | U565079,KC442968, |
| | | | | | | KC579685,KC443471 |
| | | | | | | ,KC443548,JN605453 |
| | | | | | | ,JX965174,KC174990 |
| | | | | | | ,JN014001,JN258390 |
| | | | | | | ,KC175022,KC44320 |
| | | | | | | 5,KC175044,KC5800 |
| | | | | | | 32,KC443328,JN2587 |
| | | | | | | 91,KC579707,KC174 |
| | | | | | | 915,KC442934,AB57 |
| | | | | | | 3651,KC175077,U26 |
| | | | | | | 389,JX965167,AB081 |
| | | | | | | 775,KC580136,KC58 |
| | | | | | | 0519,KC443183,JQ9 |
| | | | | | | 88904,U26382,KC58 |
| | | | | | | 0125,JX965180,JX96 |
| | | | | | | 5173,KC580340,KC7 |
| | | | | | | 69343,KC579849,AB |
| | | | | | | 081779,KC443023,K |

| Taxonomy | NCBI Reference Sequence ID | Host | No. of Genomes | Lineage | Segment Count | Genbank Accession ID |
|---|---|---|---|---|---|---|
| | | | | | | C769365,KC580351, KC174882,JXQ40425, KC175263,KC769354 ,KC579480,JX841124 ,KC579635,KC44342 7,KC175274,KC4429 8,KC769453,EF121 951,AB621363,KC44 3504,KC443680,JX96 5175,JQ688681,KC5 80531,KC175153,JXQ 40424,KC579503,KC 443592,KC175131,K C580572,EF079065, KC175197,AB081799 ,JN831225,AB081782 ,JN258362,KC579558 ,KC580606,KC17489 3,U26390,KC579965, KC174904,FN665696 ,AB573647,JX841123 ,HQ661139,KC579979 7,JX965160,DQ3214 97,JN651873,KC4435 70,JN605442,JN6054 9,KC443405,U2639 2,JN651780,KC57998 8,DQ321493,GU2964 30,KC443438,JN2588 27,KC443669,JX9651 79,KC579897,JN6355 48,JF521469,JX9651 71,JN258908,AB0817 81,JN651769,AB0817 89,DQ490550,U2638 0,U26393,GU199497, JN872870,KC443034, KC579718,KC579939 ,KC579536,EF07906 8,KC442957,KC1749 37,KC443625,KC215 545,KC442990,JN258 368,KC443515,FN66 5685,AB081797,KC5 80248,KC175088,KC 175142,KC443383,JN 013999,KC443526,K C580079,KC579624, |

| Taxonomy | NCBI Reference Sequence ID | Host | No. of Genomes | Lineage | Segment Count | Genbank Accession ID |
|---|---|---|---|---|---|---|
| | | | | | | KC443282,KC580147,KC174979,JN258813,JX965170,KC443372,KC579514,KC443768,KC579580,KC579885,AB081786,KC443735,KC769387,KC580215,KC443746,KC580021,AB081594,GU565090,KC580302,JN258895,KC579860,GU566057,KC443779,JN635537,KC579999,JN258380,JX841122,KC580068,JN014000,KC443012,DQ478583,KC443658,KC175252,KC769486,HQ657143,KC580159,KC580010,KC443460,KC442919,AB081784,DQ321495,U26383,KC443260,KC443581,JX965181,KC443713,KC579729,KC579674,JX965169,KC443139,AB081791,KC443238,AB573649,JF835112,KC443271,KC580583,KC580291,AB081796,U26381,KC580114,KC215502,JN651856,U36242,JN605420,KC579908,U36241,JN258928,KC579830,KC579919,KC443339,KC769442,KC215513,L14072,JX965178,KC443216,KC580628,JX406755,JN651896,KC580497,KC579491,JF712582,KC579786,KC769464,JN651834,KC443691,KC579525,KC580373,AB081783,AB081800,KC580617,KC175055,KC442897,KC443035,KC76 |

| Taxonomy | NCBI Reference Sequence ID | Host | No. of Genomes | Lineage | Segment Count | Genbank Accession ID |
|---|---|---|---|---|---|---|
| | | | | | | 9310,KC580428,HQ6 57154,GU565046,KC 443350,DQ478584,K C579656,EF079067, KC579819,KC580406 ,KC195774,KC44294 5,KC174959,HQ6571 65,KC442979,JX8411 19,KC579874,KC175 186,KC174969,KC58 0542,JX841121,KC76 9409,KC175164,JX96 5182,U26384,U26394 ,GU199508,AB08178 8,KC175219,JN25834 6,KC580193,KC5797 75,KC443317,KC579 492,U26379,JN37770 9,KC580384,KC7693 76,KC579569,KC580 395,DQ490556,DQ83 8620,HQ661128,KC5 79602,JN831214,AB5 73645,KC769431,JN2 58953,HE646646,KC 140587,KC580417,JN 258786,KC580047,JN 651791,JF521480,KC 443537,EF990708,K C769420,KC580439, KC580461,JN605431, KC443001,KC580270 ,EF079064,KC57974 0,KC580520,JF71256 0,KC443493,HQ8468 51,JN258857,KC5803 29,KC175099,KC443 559,JN651823,JN651 867,KC579954,KC83 4646,KC580508,AB0 81778,JN258879,KC4 43482,GU827411,U2 6385 |
| Rotavirus A | NC_011504 | vertebrates,human | 399 | Reoviridae,Rotavirus,Rotavirus A | seg. 10 | JN605446,KC689359, JN377716,KC443309, JXQ27849,KC580014, EF990712,JN831229, DQ270114,GU19950 |

| Taxonomy | NCBI Reference Sequence ID | Host | No. of Genomes | Lineage | Segment Count | Genbank Accession ID |
|---|---|---|---|---|---|---|
| | | | | | | 1,GU565072,KC5797 68,JN258894,KC5803 06,KC580095,KC579 722,KC175223,KC57 9853,JN258367,KC58 0477,JN258345,KC58 0621,JXQ29832,HQ8 46885,JXQ27817,KC4 43629,KC580524,DQ 490543,KC443497,D 0146658,JN258804, KC174897,KC443332 ,JN258400,KC579867 ,KC580025,KC17527 8,JXQ29831,KC44365 1,KC443354,KC1750 15,KC579912,KC443 607,KC443242,KC17 5037,KC580003,JN25 8339,KC579484,KC5 79473,KC443027,JN0 13982,KC580037,KC 443453,KC579606,K C580174,GU199490, KC174952,KC443508 ,KC193621,KC44287 9,KC443431,JN25892 7,JXQ27904,KC58032 1,KC443563,HQ8468 63,JN635541,KC5803 44,KC579866,DQ492 678,JF521481,KC443 782,JXQ27689,JXQ27 827,KC769457,JN013 984,JXQ27705,KC580 054,KC580535,KC17 5092,KC580466,KC7 69336,KC579678,DQ 146680,JN605457,KC 580599,KC579662,J 0688682,KC443739, DQ270104,KC580333 ,JN605413,KC580295 ,JN258838,KC579790 ,KC175146,JXQ27949 ,KC769314,JXQ29834 ,AF093199,JN258389 ,KC579507,KC17499 |

-continued

| Taxonomy | NCBI Reference Sequence ID | Host | No. of Genomes | Lineage | Segment Count | Genbank Accession ID |
|---|---|---|---|---|---|---|
| | | | | | | 4,JN635552,KC44359 6,KC443154,KC1936 31,KC579733,KC769 347,KC175267,KC57 9969,KC443695,GU5 65050,KC443376,KC 175168,KC580355,K C175081,KC195767, KC443409,KC579992 ,KC174930,KC44290 1,KC579889,KC4437 28,GU827415,KC442 912,JN651860,KC443 398,HQ657147,KC57 9981,KC442983,KC5 79755,KC175113,KC 579901,DQ270108,K C442961,KC769468, KC443750,KC443321 ,KC443297,JXQ29835 ,DQ838625,KC58054 9,KC442949,KC4430 16,KC580197,KC175 004,HQ661132,KC76 9435,DQ270103,KC1 75026,KC443253,KC 580277,KC579643,G U565061,KC443618, KC443275,KC580208 ,JXQ27728,JN258870 ,KC443662,KC17494 1,JXQ27643,JN65177 3,JN651838,JN87287 4,JN651892,JX40675 6,JXQ27700,KC58025 2,JXQ27970,KC68935 8,JN258885,KC76944 6,KC580410,KC5804 43,KC443143,KC442 926,JXQ27883,JF712 586,KC443264,KC68 9361,JXQ27740,JXQ2 7772,JXQ27762,KC58 0278,KC579711,EF5 54146,KC215538,KC 579779,KC579812,K C175212,KC579595, |

| Taxonomy | NCBI Reference Sequence ID | Host | No. of Genomes | Lineage | Segment Count | Genbank Accession ID |
|---|---|---|---|---|---|---|
| | | | | | | KC174973,KC579642,JQ988897,KC76935 8,KC442994,JF52147 0,KC443343,KC5795 29,KC580377,KC769 402,KC443552,JN651 816,HQ661143,KC76 9413,JXQ27958,KC58 0399,EU483088,KC5 79496,KC579837,KC 580512,KC579958,JX 027750,DQ492665,K C580320,KC580241, KC580118,KC580388 ,KC442890,KC57966 3,JN651849,KC17520 1,JN651806,KC17490 8,KC443706,DQ2701 01,FJ169862,JN6517 62,JN651784,DQ146 669,KC443187,JN651 751,KC443640,KC14 0596,KC580501,KC5 80421,JN258852,KC5 80565,JN605435,KC4 43574,FN665697,KC 579838,JXQ27674,JX 965155,KC580576,K C195756,DQ490560, HQ657136,KC175157 ,JF712575,KC769391 ,JXQ277839,JN827254 ,KC579617,KC58058 7,KC769380,KC1751 79,JN635530,HQ661 121,JXQ29836,KC443 365,KC579927,KC57 9801,KC580230,KC5 79573,KC443541,JN2 58357,FN665686,DQ 270102,JXQ27894,D 0270117,KC443486, KC443220,KC175190 ,KC175234,KC44344 2,JN651795,KC17486 4,JN013981,KC57974 4,KC580366,JN25882 0,JX271010,JN25837 |

-continued

| Taxonomy | NCBI Reference Sequence ID | Host | No. of Genomes | Lineage | Segment Count | Genbank Accession ID |
|---|---|---|---|---|---|---|
| | | | | | | 9,KC175070,JXQ2766 7,JXQ27936,JN25891 6,JN258867,JXQ2765 6,KC443585,JXQ2779 5,KC579518,KC1749 19,KC769303,KC579 823,JX965156,KC443 761,KC580151,KC58 0454,JN258904,JN60 5424,GU566094,JN2 58826,KC175059,KC 443005,KC442972,K C175245,KC580432, KC579926,KC580055 ,EF554157,KC17487 5,KC443198,KC4434 64,KC174983,JXQ277 84,JXQ27872,JXQ278 05,KC443475,KC769 424,KC580550,KC58 0036,KC193610,KC4 43519,KC580632,KC 579551,KC689360,K C175135,KC580072, KC443231,KC443530 ,JXQ29833,KC769369 ,KC175048,KC58016 3,KC579584,KC4431 76,JN258785,JN6518 69,KC580140,KC175 124,HQ657158,KC58 0107,GU565083,KC5 79700,KC580489,KC 769479,KC579628,A F093200,KC443209,J N831207,JX965154,K C579945,JN831218,K C580186,KC442938, KC443286,KC443165 ,JXQ27717,KC174963 ,KC175103,JN258952 ,DQ146691,GU19951 2,KC580263,KC5806 10,KC442868,KC443 684,KC580219,KC44 3132,KC443420,JXQ2 7916,JN651827,JXQ2 7926,HQ846874,KC1 |

-continued

| Taxonomy | NCBI Reference Sequence ID | Host | No. of Genomes | Lineage | Segment Count | Genbank Accession ID |
|---|---|---|---|---|---|---|
| | | | | | | 75256,KC580129,JN651882,JN258937,KC443717,DQ146647,KC579689,DQ492655,KC443772,KC580106,KC174886,HQ844852,KC579540,JN013983,KC579562,KC579878,JN258797,KC443673,KC443387 |
| Rotavirus A | NC_011505 | vertebrates,human | 374 | Reoviridae,Rotavirus,Rotavirus A | seg. 11 | KC579679,KC443674,KC195768,DQ838630,JN831219,KC193632,KC580490,KC769337,KC443783,JN605458,KC580334,FJ1794020,KC580400,KC57326,KC140597,KC579959,KC580096,JN258850,KC580323,KC579618,KC442880,KC579530,KC443487,KC769381,KC443188,KC443355,KC769348,DQ492679,KC44291 3,KC175224,JX27101 1,KC443310,KC58007 3,JXQ27948,KC58028 0,JXQ27826,KC58038 67,KC580085,KC443166,KC442995,KC443641,KC443155,JN651828,JXQ27668,KC443421,JX406757,KC579508,KC443586,KC580322,KC443465,KC579868,KC195755,JN605425,KC174876,KC579813,KC175268,DQ146648,JN258333,KC580187,KC580356,KC443696,KC443597,KC443254,KC579723,JN651774,KC174887,KC580455,KC579552,JF521482,JN259803,FJ794021,KC579701,JN258926,KC44 |

| Taxonomy | NCBI Reference Sequence ID | Host | No. of Genomes | Lineage | Segment Count | Genbank Accession ID |
|---|---|---|---|---|---|---|
| | | | | | | 3006,KC442984,FJ79 4025,KC579645,KC4 43575,KC443432,DQ 146670,JXQ27848,JN 605414,KC580038,JN 258936,JN258388,KC 443564,EF990694,K C580264,JN258837,E F554147,KC443399, HQ657137,KC579802 ,KC580220,FJ794017 ,KC580209,KC44376 2,JN258883,KC44333 3,KC579474,KC1750 82,KC579585,KC443 663,HQ657159,KC58 0015,HQ661133,JF71 2587,HQ846864,KC5 79824,KC579946,FJ7 94033,DQ490544,KC 443542,FJ794039,KC 580108,JN827255,KC 579690,JN258869,KC 769315,KC443210,G U565073,JXQ27739, GU827416,JN651817 ,KC442869,KC58050 2,HQ661144,KC4432 87,KC579563,KC769 447,FJ169863,JN872 875,GU565084,KC58 0536,KC443553,KC5 80307,KC579607,JN8 31230,JN651861,KC5 80152,FJ794018,JN8 31208,KC580566,JXQ 27657,KC580345,JXQ 27704,JXQ27771,KC5 79791,EF990702,FJ7 94016,JN258344,KC5 80551,KC443454,JN2 58946,JN258893,FJ7 94019,JXQ27727,KC5 80026,JXQ27761,KC5 79879,KC579596,JF7 12576,FJ794034,KC4 43017,KC580525,KC 443729,KC580198,K |

-continued

| Taxonomy | NCBI Reference Sequence ID | Host | No. of Genomes | Lineage | Segment Count | Genbank Accession ID |
|---|---|---|---|---|---|---|
| | | | | | | C579485,JXQ27816,JN013986,KC769370,KC580600,JXQ27642,KC769425,JXQ27673,GU565095,HQ84685 3,JXQ27804,IF52147 1,JN635542,JN65176 3,KC443133,JN25837 8,KC579734,JXQ2785 9,KC580231,JN60543 6,KC769403,KC4435 09,FJ794027,JXQ278 71,DQ146698,KC579 541,KC442973,KC57 9756,KC443276,KC4 42939,KC580389,KC 580478,KC443344,K C580175,KC443740,J XQ27783,KC769392,J XQ27903,JN651752,J N013985,JXQ27701,J XQ27749,JXQ27969,G U565051,KC443144, KC580253,FJ794022, KC193622,KC579891 ,DQ146681,DQ14670 6,JXQ27690,JN65183 9,KC580119,GU1995 13,KC579970,KC443 718,JXQ27882,KC580 378,JQ988898,FJ794 026,KC579712,KC17 5235,KC769480,KC5 79902,KC443443,FJ7 94036,JN651796,FJ7 94031,KC579928,HQ 661122,KC579745,K C580577,FJ794024,G U199502,KC769414, KC579664,JN258356, JXQ27716,JXQ08870, JXQ27893,FJ794032, KC443685,KC443322 ,KC580422,KC76946 9,GU296418,KC5804 33,KC580279,KC443 298,HQ846875,JN6 2928,HQ846875,JN6 |

| Taxonomy | NCBI Reference Sequence ID | Host | No. of Genomes | Lineage | Segment Count | Genbank Accession ID |
|---|---|---|---|---|---|---|
| | | | | | | 35553,KC580164,KC443652,KC580004,KC579574,JN258818,KC580411,JXQ27915,KC443476,KC443608,KC769458,FJ794035,KC579839,KC579497,DQ146659,JN25836 6,EF990698,KC580 11,KC443751,KC580 039,KC579913,KC44 3232,JXQ27838,KC44 3773,JXQ27925,JN25 8399,KC769359,KC5 80513,EF554158,GU 296419,KC443377,KC174984,KC443366,JX68299 6,KC443265, KC443520,KC579993,DQ490561,KC44322 1,KC769436,KC5797 80,KC442927,JN6054 47,FJ794037,KC4429 50,KC580467,FN665 687,HQ846886,FJ794 029,JN258825,HQ65 7148,FJ794038,JN65 1870,KC580056,KC5 80588,GU565062,KC 580633,KC443177,JN 258915,KC175213,JN 651883,KC580444,KC579929,JN258796,KC579769,KC579854,JF712565,KC443630,FJ794028,KC579519,KC442902,JXQ27935,KC443388,KC579982,KC442891,KC193611,JN651807,JQ688683,KC443410,KC44370 7,JN258903,FN66569 8,KC443199,KC5800 57,JN651893,KC5796 29,KC443531,FJ7940 23,EF990690,JXQ277 94,KC442962,JXQ279 57,JN258864,KC5798 |

| Taxonomy | NCBI Reference Sequence ID | Host | No. of Genomes | Lineage | Segment Count | Genbank Accession ID |
|---|---|---|---|---|---|---|
| | | | | | | 90,JN258784,JXQ404 34,KC443498,KC443 619,KC580141,JN651 850,KC580622,EF99 0713,JN635531,KC57 9644,KC580242,KC5 80296,GU199491,KC 174865,KC580130,K C175125,KC443243,J N651785,KC443028, FJ794030 |
| Rotavirus A | NC_011506 | vertebrates,human | 388 | Reoviridae,Rotavirus,Rotavirus A | seg. 2 | KC443168,KC175062 ,JXQ277660,KC443289 ,KC442893,KC58044 6,KC443643,KC4437 53,KC580121,HQ846 844,KC580347,JN605 438,JN258406,JN831 221,KC580568,KC83 4709,JXQ27680,JN60 5416,KC579648,KC5 79487,KC580028,KC 769372,KC579598,K C580527,KC580061, KC443665,JN013989, KC580255,KC443632 ,KC579782,KC57999 5,KC579842,KC5795 43,EF560616,KC443 500,KC769317,KC21 5563,KC175259,KC4 43698,KC443179,KC 193634,JN258900,KC 175116,KC580017,G U296423,KC580006, KC443434,KC175051 ,JF712567,JN651754, KC443357,KC443731 ,KC579692,KC17522 6,KC579666,GU5650 42,KC580538,DQ838 634,KC579932,JN258 385,KC579620,JXQ27 788,DQ492670,KC57 9949,DQ146661,KC1 74996,KC175193,KC 580060,JXQ277647,KC 443742,KC834708,JN |

| Taxonomy | NCBI Reference Sequence ID | Host | No. of Genomes | Lineage | Segment Count | Genbank Accession ID |
|---|---|---|---|---|---|---|
| | | | | | | 651819,KC769394,KC443157,JXQ27777,KC443522,KC769416,KC443456,KC769306,JN651898,KC443445,KC175171,JXQ27745,DQ146639,JF521462,KC579499,KC58015 4,KC443764,KC4429 52,KC442882,JN2589 49,KC580624,KC579 631,HQ846877,DQ14 6700,KC579725,JN25 8350,KC579565,KC5 79649,JXQ27682,JX2 71002,JXQ27909,JX9 65138,KC174975,KC 579681,KC442941,K C579736,KC580075,J N258831,KC579826,J XQ27855,JN651809,K C580613,JN651877,J N258911,KC442975,J XQ27658,JN258374,K C175248,KC579961, KC769471,KC580166 ,KC769405,KC44354 4,JQ988900,KC1750 95,KC580380,KC579 576,KC443533,DQ87 0486,JX406748,HQ6 61113,KC443346,KC 769427,KC175160,K C769482,JXQ27801,J XQ27693,KC140591, KC44323,KC580391 ,KC769350,KC58018 9,KC175182,FN6656 89,KC442930,KC442 964,KC579804,KC44 3008,KC443146,KC5 80244,KC580110,DQ 490536,EF554149,K C580635,KC580480,J 0688674,EF560622, GU565053,KC442997 ,KC580283,KC17508 4,KC834710,KC5800 |

| Taxonomy | NCBI Reference Sequence ID | Host | No. of Genomes | Lineage | Segment Count | Genbank Accession ID |
|---|---|---|---|---|---|---|
| | | | | | | 41,KC443676,JXQ277 12,KC443019,KC443 212,JXQ27977,JXQ27 863,JXQ277823,KC580 554,KC580435,KC57 9771,KC174933,JN65 1841,DQ870498,JXQ 27878,KC443478,KC 443785,KC579904,K C769460,HQ846855, KC175237,KC579984 ,KC580266,JN831232 ,KC195770,KC44336 8,KC580309,KC5796 67,JN651863,JN6517 76,KC580298,KC443 390,JN258921,KC580 504,KC579476,JN605 405,GU827407,JXQ2 7889,JN872866,EF55 4138,KC195761,KC4 43379,KC443775,KC 443312,EF566019,K C769383,DQ146672, JN258800,KC443335, KC580284,KC193624 ,JXQ27735,JN651765 ,HQ657150,KC17521 5,KC443610,KC1752 81,KC580492,DQ146 683,JN651787,KC443 234,DQ146650,JN63 5533,JX965137,KC58 0336,KC174922,KC4 43300,KC443030,KC 769339,HQ657161,K C579609,KC443201, KC580469,KC175018 ,KC175073,KC58042 4,JN258396,JXQ2783 4,GU199519,KC1752 04,KC443588,KC579 554,JN258943,KC580 098,KC580325,GU19 9515,KC443467,KC4 43566,KC442986,KC 443412,KC175007,K C580178,KC579793, |

-continued

| Taxonomy | NCBI Reference Sequence ID | Host | No. of Genomes | Lineage | Segment Count | Genbank Accession ID |
|---|---|---|---|---|---|---|
| | | | | | | KC579714,KC580602,KC769361,KC580087,KC579587,KC579893,DQ490546,JN258865,JXQ278100,KC443687,JN258789,KC175270,JXQ27754,KC443324,DQ870494,KC174889,KC174965,KC580042,KC443511,KC174944,KC580402,KC580413,JXQ27724,GU565075,KC579747,JN651798,JXQ27768,KC580591,KC443278,KC174986,DQ490552,KC174911,JN258877,KC580369,KC579841,KC579703,KC442904,KC175040,DQ838633,KC442915,KC769449,HQ846866,DQ838631,JN258823,DQ870506,KC174900,GU199504,JXQ27931,KC193613,KC443654,DQ870490,KC442871,JN651852,KC175029,JXQ27921,KC580200,JN827245,KC579521,KC579532,JN635544,JX965136,JN651830,KC443720,JN605449,KC443555,JN258843,KC443245,KC580457,KC443709,FN665678,KC174867,KC175127,JN635555,JX027955,KC580132,JN258889,JF521473,KC769328,KC443621,JF712556,KC443401,GU565086,KC175105,JN605427,KC174955,KC579856,GU199493,JN258932,KC443489,KC443577,KC579815,KC579915,KC44315 |

| Taxonomy | NCBI Reference Sequence ID | Host | No. of Genomes | Lineage | Segment Count | Genbank Accession ID |
|---|---|---|---|---|---|---|
| | | | | | | 90,JN013990,DQ870502,JN258363,KC579510,KC443267,DQ838632,JN258812,KC579972,GU565064,DQ146694,DQ838635,KC580358,FJ169854,KC579933,KC443423,KC769438,KC580233,KC175149,HQ657139,JN258341,JN831210,KC443256,KC580579,JF712578,JN258851,KC580222,KC580211,JXQ27900,JXQ27964,KC443135,JN651885,KC443599,JXQ27942,KC175138,JXQ27845,KC580515,KC579881,KC174878,EF560613 |
| Rotavirus A | NC_011507 | vertebrates,human | 383 | Reoviridae,Rotavirus,Rotavirus A | seg. 1 | JN635532,KC443029,KC580188,KC580005,KC580390,KC580055,KC579665,JN635543,KC443708,KC44283,KC769382,EF554148,KC174899,JN651818,DQ490545,KC580040,KC580058,KC579792,KC175061,JN651829,KC140590,JX406747,KC443576,KC175236,KC580434,KC580601,JN258364,KC579630,KC579803,DQ146671,KC443389,KC580165,KC580479,KC442951,KC579498,KC443189,DQ870493,JN605404,JN258835,JXQ27714,KC443378,DQ870485,KC175159,KC443367,KC580401,JXQ27736,JX965134,KC579647,KC443334,KC580297,GU827406,JXQ27857,K |

| Taxonomy | NCBI Reference Sequence ID | Host | No. of Genomes | Lineage | Segment Count | Genbank Accession ID |
|---|---|---|---|---|---|---|
| | | | | | | C174974,KC443730,J XQ27758,KC579892,J N258386,JN258795,J XQ27681,KC443543, KC579680,KC443167 ,GU565063,JXQ2765 9,KC443222,KC4437 52,JN651775,KC5801 20,HQ657149,GU56 526,KC579619,GU56 5041,KC580254,KC5 80634,JN258950,KC5 80590,JXQ27641,KC5 80109,KC769338,JX9 65133,KC175203,KC 769415,KC769360,JN 827244,DQ838601,J XQ27912,KC443422, GU565052,JN258808 ,KC579553,KC44351 0,KC579691,KC4431 78,JN831209,KC1750 72,JN872865,DQ838 639,JXQ27824,KC769 459,KC579542,KC44 3697,KC579713,KC5 79586,HQ846865,KC 579983,DQ146660,K C579702,KC443784, KC175258,JXQ27692, JN651797,KC175269, KC580176,KC443565 ,JN651876,KC175104 ,KC580086,DQ87049 7,JXQ27747,KC57981 4,JN605448,HQ6611 12,KC443598,KC580 612,KC195769,KC44 3675,KC443763,HQ6 57138,KC579735,KC 580552,KC580503,JX 027965,HQ846876,K C174877,JN258901,F J169853,GU296421,J XQ27974,KC580265, KC834711,KC443288 ,KC443774,JN651894 ,HQ846854,JXQ2793 |

-continued

| Taxonomy | NCBI Reference Sequence ID | Host | No. of Genomes | Lineage | Segment Count | Genbank Accession ID |
|---|---|---|---|---|---|---|
| | | | | | | 0,JF712566,KC44355 4,JN651884,KC76934 9,KC579960,KC7694 48,KC579931,KC579 840,DQ870489,KC44 2892,KC175280,KC1 75225,KC175214,KC 769437,KC443609,K C579509,JN258830,K C443499,JX271001,J XQ27945,KC193633, DQ870505,JN258375 ,KC580059,KC17493 2,KC443200,GU5650 74,KC580537,DQ146 693,KC443477,KC19 5753,DQ870501,EFS 60612,KC580346,JF5 21461,KC443719,KC 579948,KC580623,K C769481,KC443686, KC443411,DQ492669 ,JXQ27648,KC580210 ,JN651764,KC580282 ,KC579869,JXQ27813 ,KC443018,JN258342 ,KC580368,KC44348 8,KC175181,EF5606 21,JXQ27802,KC5802 43,KC579724,KC443 741,JN258853,KC580 357,JXQ27732,KC769 404,JN605426,JN258 912,JXQ27791,KC580 589,JXQ27944,KC579 475,KC579597,JXQ27 780,KC443134,JQ98 8899,KC580221,KC1 74888,GU565085,KC 442985,KC443277,JN 651840,KC175192,JF 521472,KC580412,JN 605437,KC175115,K C580177,EF560615,J N258331,KC580324, KC442903,KC193623 ,JN013988,EF554137 ,KC579746,KC57993 |

-continued

| Taxonomy | NCBI Reference Sequence ID | Host | No. of Genomes | Lineage | Segment Count | Genbank Accession ID |
|---|---|---|---|---|---|---|
| | | | | | | 0,DQ836638,DQ8386 36,KC443642,KC579 971,KC443233,KC58 0074,KC579564,KC4 43311,JF712555,JN6 05415,KC442974,KC 580016,KC443400,K C443356,EF576937,J XQ27890,JN258861,K C193612,KC769470, KC443620,JXQ27908, DQ146682,KC579903 ,JN258868,KC443299 ,KC443444,KC44287 0,JXQ27778,KC58037 9,JX965135,KC44324 4,KC579520,KC8347 12,KC580567,JN8312 31,KC769316,KC442 963,JXQ27670,KC769 327,KC834713,KC44 3433,DQ146699,KC4 42996,HQ661134,KC 443466,KC580456,JN 258934,FN665677,K C443156,DQ146638, KC579947,KC579575 ,JN258397,KC580468 ,KC174866,KC57964 6,DQ490551,KC7693 05,GU199514,DQ838 637,KC443532,KC44 3255,KC580423,KC1 75126,KC443266,KC 580153,KC580232,K C175148,GU199492, JN635554,JN258886, KC579880,DQ838640 ,KC174985,JF712577 ,KC579770,JN258783 ,KC580027,KC44345 5,JN013987,JN25881 7,JXQ27708,KC44352 1,KC442940,KC5798 25,KC579914,DQ490 533,KC579757,JXQ27 868,KC579855,KC44 2929,KC175083,JN65 |

| Taxonomy | NCBI Reference Sequence ID | Host | No. of Genomes | Lineage | Segment Count | Genbank Accession ID |
|---|---|---|---|---|---|---|
| | | | | | | 1851,HQ661123,JN651786,KC443345,HQ846843,HQ657160,KC443587,KC580131,JXQ27856,KC579608,DQ146649,KC443664,JN258353,JN651862,KC580335,KC443631,KC443653,KC44291,KC769393,JN651808,KC580097,DQ490539,KC175039,KC443211,JXQ27835,KC443145,KC580308,DQO05109,EF560618,JN258923,JN651753,KC579531,KC579781,KC769426,KC175028,KC443007,KC580281,JXQ27879,GU199503,KC579994,KC580491,JN831220,KC769371,KC580578,JQ68867 3,KC443323,FN665688,GU296420,KC580445,KC579486,JN258890,KC580199,KC580514 |
| Rotavirus A | NC_011508 | vertebrates,human | 392 | Reoviridae,Rotavirus,Rotavirus A | seg. 3 | JXQ27954,KC175128,KC579844,KC579805,KC580425,JN651777,KC579772,KC443567,JQ688675,KC580088,KC443699,KC580190,KC174868,GU565054,JXQ27844,KC580625,JN258842,KC443501,DQ838641,JXQ27646,JN831222,DQ146640,KC175260,JN258888,KC443402,KC579477,JN013991,KC579588,KC580044,KC443490,KC443479,KC443457,JXQ27694,JN258942,JXQ27746,KC443457,KC580493,DQ14668 4,KC580528,KC4432 |

| Taxonomy | NCBI Reference Sequence ID | Host | No. of Genomes | Lineage | Segment Count | Genbank Accession ID |
|---|---|---|---|---|---|---|
| | | | | | | 02,KC580099,KC769329,KC442942,KC769307,HQ661136,KC579794,KC443633,JXQ27767,KC579816,JN258834,KC443677,JN605428,KC193614,KC579748,KC579650,JX027976,KC580267,KC769461,GU565043,HQ657151,KC579488,KC769384,JXQ27649,JXQ27711,EF554150,EF560620,JN258384,KC442965,JN605439,KC580285,HQ657162,KC580029,KC579651,KC580370,KC580337,KC442953,DQ870499,KC580470,KC580555,JN651831,FN665690,DQ838642,JN651895,KC769318,KC580111,JXQ27833,KC580245,KC580256,KC443721,KC195771,KC443732,KC443180,KC769351,HQ846878,KC174912,KC580179,KC769340,JXQ27922,KC175117,JN258955,KC579843,KC769439,DQ870503,JXQ27962,KC580359,KC579950,JN258405,KC443413,JN258394,KC769395,HQ661125,KC580539,KC174879,KC580286,KC580603,DQ492671,KC580234,KC443688,KC443191,KC580155,KC174956,GU565087,KC174890,KC579871,JN651886,JN013993,JN258822,KC443644,JN635556,KC443391,KC175216,KC580580,KC |

-continued

| Taxonomy | NCBI Reference Sequence ID | Host | No. of Genomes | Lineage | Segment Count | Genbank Accession ID |
|---|---|---|---|---|---|---|
| | | | | | | 579882,KC175238,D0490547,KC195760,KC175205,JXQ27683,KC443743,JN635545,KC580212,KC579632,HQ846856,KC57959 9,JN258910,KC17492 3,KC769472,KC1749 45,JXQ27941,KC5799 35,KC175249,JXQ278 22,KC579610,KC579 682,KC175161,KC44 3347,KC443358,JN87 2867,KC579500,KC5 80447,JXQ27877,KC1 75030,JXQ27790,KC1 93635,KC769483,KC 175074,KC580018,K C443600,KC175052, KC443512,KC769428 ,KC580392,HQ65714 0,KC580614,KC4428 94,KC215499,JXQ277 57,KC579715,KC443 765,EF560614,KC44 3290,DQ146673,KC4 43224,KC579704,KC 174901,KC443776,E F560617,KC580201, KC579934,JXQ27809, KC579737,KC579996 ,KC579533,KC44332 5,JN258931,JQ98890 1,JN827246,KC58004 3,KC580458,KC1752 27,KC443786,KC443 158,KC442998,KC58 0122,KC579962,KC1 75019,KC175063,HQ 846867,JXQ27776,KC 580505,JN651788,KC 443435,KC580133,K C443589,FJ169855,K C443147,KC174934, KC443369,KC579522 ,KC834706,KC57976 0,KC175085,JN25878 8,KC443301,KC5796 |

| Taxonomy | NCBI Reference Sequence ID | Host | No. of Genomes | Lineage | Segment Count | Genbank Accession ID |
|---|---|---|---|---|---|---|
| | | | | | | 21,KC580414,KC579511,KC579974,DQ838645,KC174997,KC175172,KC175150,FN665679,KC443268,KC579857,JN258373,DQ838644,KC175106,JN258811,GU199494,KC443556,KC769406,JXQ27723,KC580348,JN258863,KC579669,KC443020,KC442872,KC580076,GU827408,JXQ27854,KC443622,JF712557,KC443313,JXQ27679,KC769450,KC579916,HQ661114,KC442987,DQ870487,KC579555,JN258799,KC443169,JN258351,JN635534,D0146701,KC443611,DQ870491,KC443523,JN258922,JF712568,JN605450,KC443136,KC175041,KC442905,KC442916,KC580156,JN258856,DQ870495,KC443710,JN605417,KC443534,JN258876,KC579544,GU565065,JN013992,JN651820,KC443468,KC140592,KC580223,KC580556,KC580381,KC443446,KC443336,KC174966,GU296424,DQ838643,KC443246,KC580481,JXQ27867,KC175194,KC580007,KC580636,KC834705,JN258361,KC580592,KC443279,KC580326,KC580516,KC580436,JXQ27899,KC175139,JN651871,JX965140,KC443666,KC769373,EF554139,KC |

| Taxonomy | NCBI Reference Sequence ID | Host | No. of Genomes | Lineage | Segment Count | Genbank Accession ID |
|---|---|---|---|---|---|---|
| | | | | | | 17527I,JN831233,JN605406,KC579985,JX027734,KC174976,JN651810,KC175008,KC579577,KC443655,KC579566,KC579894,JXQ27888,KC580403,JX271003,KC579668,JN831211,KC579827,KC580299,DQ14666 2,KC579905,DQ8386 00,JXQ27932,KC4434 24,JX965139,KC4432 57,HQ846845,JN258 336,KC443380,KC44 2883,KC580569,KC1 75282,JF712579,KC4 42976,DQ490537,GU 296425,KC443754,K C442931,KC769362,J N651853,JN651864,K C579951,DQ490553, KC580167,KC174987 ,KC443545,KC19362 5,JN651766,JXQ2780 0,KC215510,KC4432 35,JX965141,JN6517 99,JX406749,KC5800 62,GU199488,KC579 693,KC580310,KC17 5183,GU565076,EF5 60623,JXQ27669,JN6 51842,KC443578,KC 769417,KC443009,K C579783,KC580063, DQ146651,JF521463, JXQ27910,JN258899, JF521474,KC443213, KC579726,JN651755 |
| Rotavirus A | NC_011509 | vertebrates,human | 366 | Reoviridae,Rotavirus,Rotavirus A | seg. 6 | JX965142,KC443668, KC580192,KC580301 ,AB040055,KC57960 1,KC174925,KC4430 00,KC769353,DQ146 702,KC215544,KC57 9987,KC442907,JN63 5547,HQ846870,KC4 43591,KC580571,KC |

| Taxonomy | NCBI Reference Sequence ID | Host | No. of Genomes | Lineage | Segment Count | Genbank Accession ID |
|---|---|---|---|---|---|---|
| | | | | | | 579774,KC580066,KC193616,JN651768,KC443646,KC579847,JX271005,JN258814,JXQ40422,KC769397,KC443679,KC442874,JN651757,JN258872,HQ846881,KC580605,KC443393,JX84114,JF521466,KC17489,KC443270,KC58057,KC443481,JN60540,KC834700,JN25887,JF712581,KC44298,JN258335,KC4437,KC579976,GU199496,JN831213,DQ492673,AY456527,KC175108,D

| Taxonomy | NCBI Reference Sequence ID | Host | No. of Genomes | Lineage | Segment Count | Genbank Accession ID |
|---|---|---|---|---|---|---|
| | | | | | | ,DQ490538,KC44320 4,KC443149,KC5798 07,KC443492,JN2589 48,KC443316,KC442 944,KC579634,KC44 3303,KC443635,JN25 8392,JN258906,KC58 0078,JF712570,KC44 3657,KC579896,DQ1 46686,KC443404,KC 580616,KC443292,JN 258839,KC579717,H 0661116,KC443448, KC580438,KC580594 ,KC443237,GU56507 8,KC174870,DQ8705 00,KC443701,JN6518 22,KC579654,JF7125 59,KC580541,KC175 119,EF554152,KC58 0427,KC580560,KC1 75284,KC579623,KC 834701,KC580203,K C442956,JN258370, DQ870507,KC580472 ,KC175087,KC19362 7,HQ661127,JX8411 43,JN831224,KC5795 02,KC174914,KC580 046,KC443022,DQ49 0555,KC579590,KC5 79938,KC580405,KC 580225,KC175273,K C580124,KC580394, KC443011,KC443193 ,KC175141,KC17501 0,JN605441,JN83123 5,KC580361,JN60541 9,KC580031,KC5802 36,JN014003,KC5799 64,KC443788,JN2588 97,KC443426,JX9651 44,GU565045,KC443 569,KC443536,FJ169 858,JN651866,KC443 171,KC579655,KC76 9430,KC175185,JN65 1900,KC580484,JF52 |

-continued

| Taxonomy | NCBI Reference Sequence ID | Host | No. of Genomes | Lineage | Segment Count | Genbank Accession ID |
|---|---|---|---|---|---|---|
| | | | | | | 1477,KC442933,KC579907,HQ657142,KC580158,KC579953,KC580269,JN258359,KC579937,KC580518,HQ661138,KC579796,KC579728,KC580113,KC444138,KC444373,KC193637,KC580020,KC443160,JN651801,KC769331,KC579918,KC443226,KC579695,DQ146675,KC579829,KC579490,KC579672,KC175207,KC579750,JN258847,KC443281,JN651779,KC769463,JN651855,KC579524,JN605408,JN258880,KC580090,KC174936,KC580247,KC443338,JN014005,KC580169,JN651888,KC580312,KC443547,DQ870488,JN258919,JQ688678,KC443349,KC579546,KC195773,JX406752,KC174903,JN651872,KC443215,KC175065,JN258348,KC769408,KC769309,HQ657164,KC443382,KC769342,KC175076,KC174881,JN651790,KC443624,KC443415,KC175262,KC579513,KC769452,KC580067,KC443327,KC175218,KC579479,KC175196,KC769364,KC175098,KC580496,KC443712,JN635558,JX841142,KC579673,KC580416,KC580460,AY456528,KC443259,GU565067,KC215501,DQ870496,GU827410,KC580327 |

| Taxonomy | NCBI Reference Sequence ID | Host | No. of Genomes | Lineage | Segment Count | Genbank Accession ID |
|---|---|---|---|---|---|---|
| | | | | | | 8,KC443558,KC5798 48,JN258807,KC5797 39,KC580559,KC175 229,KC443756,KC17 5251,DQ146664,KC4 42885,U36240,EF554 141,KC580530,GU29 6429,KC580495,KC4 43459,FN665682,KC 443723,DQ146642,K C580214,HQ846859, KC175054,KC442989 ,KC579535,KC58025 8,KC580483,JN25882 9,KC580449,KC4430 33,KC769375,KC579 684,FN665693,HQ65 7153,KC580181,KC5 79557,KC442978,KC 443182,DQ146653,K C769386,KC769441, KC215512,JN605452, GU565089,JN014002 ,U85998,DQ490549,J N25838,2,KC579706, KC442967,KC443470 ,DQ838650,KC44361 3,KC580290,KC4433 71,JN258403,KC1751 74,JN258858,KC5800 09,KC175032,KC174 947,KC579884,JN258 930,JN258792,JN651 833,KC443525,KC57 9785,JN258939,KC76 9485,KC769320,KC5 80350,KC579612 |
| Rotavirus A | NC_011510 | vertebrates,human | 352 | Reoviridae,Rotavirus,Rotavirus A | seg. 4 | JN258809,JN605451, JXQ27799,KC175042, JN635546,JN872868, KC443348,KC174988 ,KC579556,KC57969 4,KC580168,KC5802 02,AB526248,JN6518 78,JXQ27744,GU565 044,KC580134,KC57 9895,KC580180,DQ3 21496,KC443546,KC |

| Taxonomy | NCBI Reference Sequence ID | Host | No. of Genomes | Lineage | Segment Count | Genbank Accession ID |
|---|---|---|---|---|---|---|
| | | | | | | 580123,KC579761,KC580581,JN258349,KC174902,KC442906, KC580287,KC769418,KC443021,KC57954 5,KC174967,JXQ2793 3,KC579589,KC4437 87,JN258875,KC1749 13,JN258832,JN6518 65,KC769440,KC443 214,GU565077,AB52 6246,KC443159,KC4 43436,KC193636,KC 443524,JN651887,JX 027702,KC579986,F N665680,JN013997,K C443590,KC580626, KC579762,KC443579 ,KC443733,JN831223 ,KC443667,KC57951 2,KC443370,KC5798 17,KC443315,KC443 414,KC443645,HQ66 1126,JN258383,JN65 1811,KC443568,JN25 8340,JN258360,JXQ2 7887,JN605407,JXQ2 7975,JN635535,KC57 9653,KC443403,KC5 80517,KC175206,KC 579795,KC443634,KC443744,KC769396,J N651767,JN258884,J XQ27953,DQ838602, AB573650,GU565066 ,KC580557,HQ65715 2,KC442943,JXQ2776 6,JN013995,KC57950 1,KC580257,KC4437 66,KC443010,JXQ277 22,KC769385,HQ657 163,KC443032,JN258 787,KC579716,KC44 3225,KC579936,KC5 80448,U65924,KC76 9462,KC580570,KC5 79975,JN258855,KC5 80008,AB573872,JN6 |

| Taxonomy | NCBI Reference Sequence ID | Host | No. of Genomes | Lineage | Segment Count | Genbank Accession ID |
|---|---|---|---|---|---|---|
| | | | | | | 35557,JN258404,AB573648,KC580371,KC579846,KC580349,KC175184,KC580604,KC579611,KC769363,DQ841262,KC579872,KC579534,KC442988,KC442954,JXQ27645,KC580338,KC443236,KC174924,JN258798,KC443148,JXQ27898,GU565055,KC580157,KC443326,JQ688676,JN651756,KC769484,KC580540,KC580482,KC579567,KC443678,KC443623,HQ846857,KC580246,KC579652,KC443469,KC579952,JXQ27821,KC580593,GU565501,JX271004,KC769388,JXQ27789,JXQ2763084,JN651800,KC579749,DQ492672,KC580235,DQ490548,JXQ27831,KC579845,KC579683,KC443557,JXQ27853,JN651854,KC580089,FJ169856,KCS79633,JN258866,JN258954,JF521475,KC193615,JN258371,JN831212,KC579727,KC44347,KC769429,KC44353,JXQ27940,JN258920,JXQ27779,KC443137,KC443337,KC579705,AB571047,DQ838604,JXQ27755,JN258898,KC579489,KC442884,KC443392,KC443689,JXQ2799211,KC442977,JN651778,KC580112,JXQ2797963,KC580100,KC580637,FN665691,JN258819,KC580393,KC17 |

| Taxonomy | NCBI Reference Sequence ID | Host | No. of Genomes | Lineage | Segment Count | Genbank Accession ID |
|---|---|---|---|---|---|---|
| | | | | | | 5020,KC579828,KC579523,KC579738,KC580224,JXQ277661,KC769473,KC580558,KC579963,JN651832,KC580426,KC175097,JXQ27843,EF990707,KC443302,KC579806, KC769308,KC580360,KC579478,JN831234,KC175151,KC580191,KC769451,KC580459,KC579773,KC580382,KC443491,KC580494,KC580415,KC443269,JN258841,JN651789,KC580030,KC443425,KC579917,JN605418,KC174946,KC579671,HQ846879, KC580404,KC443447,JF521464,HQ661137,JXQ27733,KC580506,KC580437,JXQ27812,KC443612,DQ24261,5,KC443170,KC443755, KC443722,KC443513,KC579670,HQ846868,KC442955,KC443777,KC174977,KC580065,JN651821,JX027876, KC442966,KC579906,EF554151, JN258393,KC443181,KC442873,KC443291 KC193626,JXQ27920, KC579622, KC580615,JQ988902,AB573646,KC442917,KC580471, KC174957, DQ490554,JXQ27650,AY773004,EF554140,KC443359,KC769374,KC579578, JN651843,KC579883,KC195759,KC442895,KC580045,DQ321494,JXQ27707, DQ321492,KC579997 |

-continued

| Taxonomy | NCBI Reference Sequence ID | Host | Lineage | No. of Genomes | Segment Count | Genbank Accession ID |
|---|---|---|---|---|---|---|
| | | | | | | ,KC769319,KC44331 4,AB055967,KC7693 41, KC580311 ,JN2589 40, KC579858,KC769 352,JN013994,JN258 933,KC443203,KC44 3700,KC443601 ,KC5 80064, KC443502, HQ 657141 ,KC443280,D Q838603, KC579784, KC443192,KC442999 , DQ838605, J XQ2786 5,KC175195,KC5803 00,JN827247,KC5800 19, KC443711 ,JN6054 40,JX406750,KC5802 88, KC443656,HQ846 846,KC443480,HQ66 1115,GU827409,KC4 42932,KC579600,KC 580077,JN258909,KC 580529, KC443458JX 027678, KC580327,JN 013996, KC443381 ,K C580268,KC580213, KC443258,KC175250 ,JN605429,JN651899 |
| Rotavirus A 1290xU K reassortant (UKg91290) | NC_011500 | vertebrates,human | Reoviridae,Rotavirus,Rotavirus A | 3 | seg. 5 | JF693219,J F693184, JF693118 |
| Rotavirus A 1290xUK reassortant (UKg91290) | NC_011501 | vertebrates,human | Reoviridae,Rotavirus,Rotavirus A | 2 | seg. 7 | JF693121 ,JF693187 |
| Rotavirus A 1290x11 K reassortant (UKg91290) | NC_011502 | vertebrates,human | Reoviridae,Rotavirus,Rotavirus A | 3 | seg. 8 | JF693186,JF693120, JF693220 |
| Rotavirus A 1290xUK reassortant (UKg91290) | NC_011503 | vertebrates,human | Reoviridae,Rotavirus,Rotavirus A | 3 | seg. 9 | JF693188,JF693122, JF693221 |
| Rotavirus A 1290xUK reassortant (UKg91290) | NC_011504 | vertebrates,human | Reoviridae,Rotavirus,Rotavirus A | 2 | seg. 10 | JF693123,JF693189 |
| Rotavirus A 1290xUK reassortant (UKg91290) | NC_011505 | vertebrates,human | Reoviridae,Rotavirus,Rotavirus A | 2 | seg. 11 | JF693124,JF693190 |
| Rotavirus A 1290xUK reassortant (UKg91290) | NC_011506 | vertebrates,human | Reoviridae,Rotavirus,Rotavirus A | 2 | seg. 2 | JF693181 ,JF693115 |
| Rotavirus A 1290xUK reassortant (UKg91290) | NC_011507 | vertebrates,human | Reoviridae,Rotavirus,Rotavirus A | 2 | seg. 1 | JF693180,JF693114 |
| Rotavirus A 1290xUK reassortant (UKg91290) | NC_011508 | vertebrates,hum | Reoviridae,Rotavirus,Rotavirus A | 2 | seg. 3 | JF693182,JF693116 |
| Rotavirus A 1290xUK reassortant (UKg91290) | NC_011500 | vertebrates,human | Reoviridae,Rotavirus,Rotavirus A | 3 | seg. 5 | JF693219,J F693184, JF693118 |

-continued

| Taxonomy | NCBI Reference Sequence ID | Host | No. of Genomes | Lineage | Segment Count | Genbank Accession ID |
|---|---|---|---|---|---|---|
| Rotavirus A 1290xUK reassortant (UKg91290) | NC_011509 | vertebrates,human | 2 | Reoviridae,Rotavirus,Rotavirus A | seg. 6 | JF693119,JF693185 |
| Rotavirus A 1290xUK reassortant (UKg91290) | NC_011510 | vertebrates,human | 3 | Reoviridae,Rotavirus,Rotavirus A | seg. 4 | JF693117,JF693183, JF693218 |
| Rotavirus A AU32xUK reassortant (UKg9AU32) | NC_011500 | vertebrates,human | 3 | Reoviridae,Rotavirus,Rotavirus A | seg. 5 | JF693129,JF693223, JF693195 |
| Rotavirus A AU32xUK reassortant (UKg9AU32) | NC_011501 | vertebrates,human | 2 | Reoviridae,Rotavirus,Rotavirus A | seg. 7 | JF693198,JF693132 |
| Rotavirus A AU32xUK reassortant (UKg9AU32) | NC_011502 | vertebrates,human | 3 | Reoviridae,Rotavirus,Rotavirus A | seg. 8 | JF693131,JF693224, JF693197 |
| Rotavirus A AU32xUK reassortant (UKg9AU32) | NC_011503 | vertebrates,human | 3 | Reoviridae,Rotavirus,Rotavirus A | seg. 9 | JF693199,JF693133, JF693225 |
| Rotavirus A AU32xUK reassortant (UKg9AU32) | NC_011504 | vertebrates,human | 2 | Reoviridae,Rotavirus,Rotavirus A | seg. 10 | JF693134,JF693200 |
| Rotavirus A AU32xUK reassortant (UKg9AU32) | NC_011505 | vertebrates,human | 2 | Reoviridae,Rotavirus,Rotavirus A | seg. 11 | JF693201,JF693135 |
| Rotavirus A AU32xUK reassortant (UKg9AU32) | NC_011506 | vertebrates,human | 2 | Reoviridae,Rotavirus,Rotavirus A | seg. 2 | JF693192,JF693126 |
| Rotavirus A AU32xUK reassortant (UKg9AU32) | NC_011507 | vertebrates,human | 2 | Reoviridae,Rotavirus,Rotavirus A | seg. 1 | JF693191,JF693125 |
| Rotavirus A AU32xUK reassortant (UKg9AU32) | NC_011508 | vertebrates,human | 2 | Reoviridae,Rotavirus,Rotavirus A | seg. 3 | JF693127,JF693193 |
| Rotavirus A AU32xUK reassortant (UKg9AU32) | NC_011509 | vertebrates,human | 2 | Reoviridae,Rotavirus,Rotavirus A | seg. 6 | JF693130,JF693196 |
| Rotavirus A AU32xUK reassortant (UKg9AU32) | NC_011510 | vertebrates,human | 3 | Reoviridae,Rotavirus,Rotavirus A | seg. 4 | JF693194,JF693128, JF693222 |
| Rotavirus A DS-1xUK reassortant (UKg9DS-1) | NC_011500 | vertebrates,human | 3 | Reoviridae,Rotavirus,Rotavirus A | seg. 5 | JF693207,JF693151, JF693085 |
| Rotavirus A DS-1xUK reassortant (UKg9DS-1) | NC_011501 | vertebrates,human | 2 | Reoviridae,Rotavirus,Rotavirus A | seg. 7 | JF693154,JF693088 |
| Rotavirus A DS-1xUK reassortant (UKg9DS-1) | NC_011502 | vertebrates,human | 3 | Reoviridae,Rotavirus,Rotavirus A | seg. 8 | JF693087,JF693208, JF693153 |
| Rotavirus A DS-1xUK reassortant (UKg9DS-1) | NC_011503 | vertebrates,human | 3 | Reoviridae,Rotavirus,Rotavirus A | seg. 9 | JF693089,JF693209, JF693155 |
| Rotavirus A DS-1xUK reassortant (UKg9DS-1) | NC_011504 | vertebrates,human | 2 | Reoviridae,Rotavirus,Rotavirus A | seg. 10 | JF693156,JF693090 |
| Rotavirus A DS-1xUK reassortant (UKg9DS-1) | NC_011505 | vertebrates,human | 2 | Reoviridae,Rotavirus,Rotavirus A | seg. 11 | JF693091,JF693157 |
| Rotavirus A DS-1xUK reassortant (UKg9DS-1) | NC_011506 | vertebrates,human | 2 | Reoviridae,Rotavirus,Rotavirus A | seg. 2 | JF693082,JF693148 |
| Rotavirus A DS-1xUK reassortant (UKg9DS-1) | NC_011507 | vertebrates,human | 2 | Reoviridae,Rotavirus,Rotavirus A | seg. 1 | JF693147,JF693081 |
| Rotavirus A DS-1xUK reassortant (UKg9DS-1) | NC_011508 | vertebrates,human | 2 | Reoviridae,Rotavirus,Rotavirus A | seg. 3 | JF693149,JF693083 |
| Rotavirus A DS-1xUK reassortant (UKg9DS-1) | NC_011509 | vertebrates,human | 2 | Reoviridae,Rotavirus,Rotavirus A | seg. 6 | JF693152,JF693086 |
| Rotavirus A DS-1xUK reassortant (UKg9DS-1) | NC_011510 | vertebrates,human | 3 | Reoviridae,Rotavirus,Rotavirus A | seg. 4 | JF693150,JF693206, JF693084 |

-continued

| Taxonomy | NCBI Reference Sequence ID | Host | No. of Genomes | Lineage | Segment Count | Genbank Accession ID |
|---|---|---|---|---|---|---|
| Rotavirus A DxUK reassortant (UKg9D) | NC_011500 | vertebrates,human | 3 | Reoviridae,Rotavirus,Rotavirus A | seg. 5 | JF693140,JF693203, JF693074 |
| Rotavirus A DxUK reassortant (UKg9D) | NC_011501 | vertebrates,human | 2 | Reoviridae,Rotavirus,Rotavirus A | seg. 7 | JF693143,JF693077 |
| Rotavirus A DxUK reassortant (UKg9D) | NC_011502 | vertebrates,human | 3 | Reoviridae,Rotavirus,Rotavirus A | seg. 8 | JF693142,JF693076, JF693204 |
| Rotavirus A DxUK reassortant (UKg9D) | NC_011503 | vertebrates,human | 3 | Reoviridae,Rotavirus,Rotavirus A | seg. 9 | JF693205,JF693144, JF693078 |
| Rotavirus A DxUK reassortant (UKg9D) | NC_011504 | vertebrates,human | 2 | Reoviridae,Rotavirus,Rotavirus A | seg. 10 | JF693079,JF693145 |
| Rotavirus A DxUK reassortant (UKg9D) | NC_011505 | vertebrates,human | 2 | Reoviridae,Rotavirus,Rotavirus A | seg. 11 | JF693080,JF693146 |
| Rotavirus A DxUK reassortant (UKg9D) | NC_011506 | vertebrates,human | 2 | Reoviridae,Rotavirus,Rotavirus A | seg. 2 | JF693137,JF693071 |
| Rotavirus A DxUK reassortant (UKg9D) | NC_011507 | vertebrates,human | 2 | Reoviridae,Rotavirus,Rotavirus A | seg. 1 | JF693136,JF693070 |
| Rotavirus A DxUK reassortant (UKg9D) | NC_011508 | vertebrates,human | 2 | Reoviridae,Rotavirus,Rotavirus A | seg. 3 | JF693072,JF693138 |
| Rotavirus A DxUK reassortant (UKg9D) | NC_011509 | vertebrates,human | 2 | Reoviridae,Rotavirus,Rotavirus A | seg. 6 | JF693141,JF693075 |
| Rotavirus A DxUK reassortant (UKg9D) | NC_011510 | vertebrates,human | 3 | Reoviridae,Rotavirus,Rotavirus A | seg. 4 | JF693139,JF693202, JF693073 |
| Rotavirus A EC2184/ECU/G11P[6] | NC_011501 | vertebrates,human | 1 | Reoviridae,Rotavirus,Rotavirus A | seg. 7 | GQ149098 |
| Rotavirus A EC2184/ECU/G11P[6] | NC_011502 | vertebrates,human | 1 | Reoviridae,Rotavirus,Rotavirus A | seg. 8 | GQ149101 |
| Rotavirus A EC2184/ECU/G11P[6] | NC_011504 | vertebrates,human | 1 | Reoviridae,Rotavirus,Rotavirus A | seg. 10 | GQ149099 |
| Rotavirus A EC2184/ECU/G11P[6] | NC_011505 | vertebrates,human | 1 | Reoviridae,Rotavirus,Rotavirus A | seg. 11 | GQ149100 |
| Rotavirus A EC2184/ECU/G11P[6] | NC_011509 | vertebrates,human | 1 | Reoviridae,Rotavirus,Rotavirus A | seg. 6 | GQ149095 |
| Rotavirus A Hu/1290/Kenya/1991/G8 | NC_011503 | vertebrates,human | 1 | Reoviridae,Rotavirus,Rotavirus A | seg. 9 | EU488721 |
| Rotavirus A Hu/BE UBE2001/2009/G9P [6] | NC_011502 | vertebrates,human | 1 | Reoviridae,Rotavirus,Rotavirus A | seg. 8 | JQ993325 |
| Rotavirus A Hu/BE UBE2001/2009/G9P [6] | NC_011503 | vertebrates,human | 1 | Reoviridae,Rotavirus,Rotavirus A | seg. 9 | JQ993318 |
| Rotavirus A Hu/BE UBE2001/2009/G9P [6] | NC_011504 | vertebrates,human | 1 | Reoviridae,Rotavirus,Rotavirus A | seg. 10 | JQ993327 |
| Rotavirus A Hu/BE UBE2001/2009/G9P [6] | NC_011506 | vertebrates,human | 1 | Reoviridae,Rotavirus,Rotavirus A | seg. 2 | JQ993322 |

| Taxonomy | NCBI Reference Sequence ID | Host | No. of Genomes | Lineage | Segment Count | Genbank Accession ID |
|---|---|---|---|---|---|---|
| Rotavirus A Hu/BE UBE2001/2009/G9P [6] | NC_011507 | vertebrates,human | 1 | Reoviridae,Rotavirus,Rotavirus A | seg. 1 | JQ993321 |
| Rotavirus A Hu/BE UBE2001/2009/G9P [6] | NC_011508 | vertebrates,human | 1 | Reoviridae,Rotavirus,Rotavirus A | seg. 3 | JQ993323 |
| Rotavirus A Hu/BEUF01322/2009/G3P [6] | NC_011500 | vertebrates,human | 1 | Reoviridae,Rotavirus,Rotavirus A | seg. 5 | JF460829 |
| Rotavirus A Hu/BEUF01322/2009/G3P [6] | NC_011501 | vertebrates,human | 1 | Reoviridae,Rotavirus,Rotavirus A | seg. 7 | JF460831 |
| Rotavirus A Hu/BEUF01322/2009/G3P [6] | NC_011502 | vertebrates,human | 1 | Reoviridae,Rotavirus,Rotavirus A | seg. 8 | JF460830 |
| Rotavirus A Hu/BEUF01322/2009/G3P [6] | NC_011503 | vertebrates,human | 1 | Reoviridae,Rotavirus,Rotavirus A | seg. 9 | JF460828 |
| Rotavirus A Hu/BEUF01322/2009/G3P [6] | NC_011504 | vertebrates,human | 1 | Reoviridae,Rotavirus,Rotavirus A | seg. 10 | JF460832 |
| Rotavirus A Hu/BEUF01322/2009/G3P [6] | NC_011505 | vertebrates,human | 1 | Reoviridae,Rotavirus,Rotavirus A | seg. 11 | JF460833 |
| Rotavirus A Hu/BEUF01322/2009/G3P [6] | NC_011506 | vertebrates,human | 1 | Reoviridae,Rotavirus,Rotavirus A | seg. 2 | JF460824 |
| Rotavirus A Hu/BEUF01322/2009/G3P [6] | NC_011507 | vertebrates,human | 1 | Reoviridae,Rotavirus,Rotavirus A | seg. 1 | JF460823 |
| Rotavirus A Hu/BEUF01322/2009/G3P [6] | NC_011508 | vertebrates,human | 1 | Reoviridae,Rotavirus,Rotavirus A | seg. 3 | JF460825 |
| Rotavirus A Hu/BEUF01322/2009/G3P [6] | NC_011509 | vertebrates,human | 1 | Reoviridae,Rotavirus,Rotavirus A | seg. 6 | JF460827 |
| Rotavirus A Hu/BEUF01322/2009/G3P [6] | NC_011510 | vertebrates,human | 1 | Reoviridae,Rotavirus,Rotavirus A | seg. 4 | JF460826 |
| Rotavirus A Hu/BEUF01498/2009/G3P [6] | NC_011500 | vertebrates,human | 1 | Reoviridae,Rotavirus,Rotavirus A | seg. 5 | JF460840 |
| Rotavirus A Hu/BEUF01498/2009/G3P [6] | NC_011501 | vertebrates,human | 1 | Reoviridae,Rotavirus,Rotavirus A | seg. 7 | JF460842 |
| Rotavirus A Hu/BEUF01498/2009/G3P [6] | NC_011502 | vertebrates,human | 1 | Reoviridae,Rotavirus,Rotavirus A | seg. 8 | JF460841 |

-continued

| Taxonomy | NCBI Reference Sequence ID | Host | No. of Genomes | Lineage | Segment Count | Genbank Accession ID |
|---|---|---|---|---|---|---|
| Rotavirus A Hu/BEUF01498/2009/G3P [6] | NC_011503 | vertebrates,human | 1 | Reoviridae,Rotavirus,Rotavirus A | seg. 9 | JF460839 |
| Rotavirus A Hu/BEUF01498/2009/G3P [6] | NC_011504 | vertebrates,human | 1 | Reoviridae,Rotavirus,Rotavirus A | seg. 10 | JF460843 |
| Rotavirus A Hu/BEUF01498/2009/G3P [6] | NC_011505 | vertebrates,human | 1 | Reoviridae,Rotavirus,Rotavirus A | seg. 11 | JF460844 |
| Rotavirus A Hu/BEUF01498/2009/G3P [6] | NC_011506 | vertebrates,human | 1 | Reoviridae,Rotavirus,Rotavirus A | seg. 2 | JF460835 |
| Rotavirus A Hu/BEUF01498/2009/G3P [6] | NC_011507 | vertebrates,human | 1 | Reoviridae,Rotavirus,Rotavirus A | seg. 1 | JF460834 |
| Rotavirus A Hu/BEUF01498/2009/G3P [6] | NC_011508 | vertebrates,human | 1 | Reoviridae,Rotavirus,Rotavirus A | seg. 3 | JF460836 |
| Rotavirus A Hu/BEUF01498/2009/G3P [6] | NC_011509 | vertebrates,human | 1 | Reoviridae,Rotavirus,Rotavirus A | seg. 6 | JF460838 |
| Rotavirus A Hu/BEUF01498/2009/G3P [6] | NC_011510 | vertebrates,human | 1 | Reoviridae,Rotavirus,Rotavirus A | seg. 4 | JF460837 |
| Rotavirus A Hu/CI-81/2011/KOR | NC_011501 | vertebrates,human | 1 | Reoviridae,Rotavirus,Rotavirus A | seg. 7 | JN887815 |
| Rotavirus A Hu/CI-81/2011/KOR | NC_011503 | vertebrates,human | 1 | Reoviridae,Rotavirus,Rotavirus A | seg. 9 | JN887818 |
| Rotavirus A Hu/CI-81/2011/KOR | NC_011504 | vertebrates,human | 2 | Reoviridae,Rotavirus,Rotavirus A | seg. 10 | JN887814,JN887816 |
| Rotavirus A Hu/CI-81/2011/KOR | NC_011505 | vertebrates,human | 1 | Reoviridae,Rotavirus,Rotavirus A | seg. 11 | JN887813 |
| Rotavirus A Hu/CI-81/2011/KOR | NC_011506 | vertebrates,human | 1 | Reoviridae,Rotavirus,Rotavirus A | seg. 2 | JN887811 |
| Rotavirus A Hu/CI-81/2011/KOR | NC_011507 | vertebrates,human | 1 | Reoviridae,Rotavirus,Rotavirus A | seg. 1 | JN887812 |
| Rotavirus A Hu/CI-81/2011/KOR | NC_011508 | vertebrates,human | 1 | Reoviridae,Rotavirus,Rotavirus A | seg. 3 | JN887810 |
| Rotavirus A Hu/CI-81/2011/KOR | NC_011509 | vertebrates,human | 1 | Reoviridae,Rotavirus,Rotavirus A | seg. 6 | JN887819 |
| Rotavirus A Hu/Cm15/2008/Cuba/G9P [8] | NC_011503 | vertebrates,human | 1 | Reoviridae,Rotavirus,Rotavirus A | seg. 9 | FJ348353 |
| Rotavirus A Hu/Cm42/2008/Cuba/G9P [8] | NC_011503 | vertebrates,human | 1 | Reoviridae,Rotavirus,Rotavirus A | seg. 9 | FJ348352 |

| Taxonomy | NCBI Reference Sequence ID | Host | Lineage | No. of Genomes | Segment Count | Genbank Accession ID |
|---|---|---|---|---|---|---|
| Rotavirus A Hu/DC706/USA/1980/G9 | NC_011503 | vertebrates,human | Reoviridae,Rotavirus,Rotavirus A | 1 | seg. 9 | EU153553 |
| Rotavirus A Hu/Dhaka6/BGD/2001/G11 P25 | NC_011501 | vertebrates,human | Reoviridae,Rotavirus,Rotavirus A | 1 | seg. 7 | EF560709 |
| Rotavirus A Hu/Dhaka6/BGD/2001/G11 P25 | NC_011502 | vertebrates,human | Reoviridae,Rotavirus,Rotavirus A | 1 | seg. 8 | EF560710 |
| Rotavirus A Hu/Dhaka6/BGD/2001/G11 P25 | NC_011504 | vertebrates,human | Reoviridae,Rotavirus,Rotavirus A | 1 | seg. 10 | EF560711 |
| Rotavirus A Hu/Dhaka6/BGD/2001/G11 P25 | NC_011505 | vertebrates,human | Reoviridae,Rotavirus,Rotavirus A | 1 | seg. 11 | EF560712 |
| Rotavirus A Hu/Dhaka6/BGD/2001/G11 P25 | NC_011507 | vertebrates,human | Reoviridae,Rotavirus,Rotavirus A | 1 | seg. 1 | EF560705 |
| Rotavirus A Hu/Dhaka6/BGD/2001/G11 P25 | NC_011508 | vertebrates,human | Reoviridae,Rotavirus,Rotavirus A | 1 | seg. 3 | EF560706 |
| Rotavirus A Hu/Dhaka6/BGD/2001/G11 P25 | NC_011509 | vertebrates,human | Reoviridae,Rotavirus,Rotavirus A | 1 | seg. 6 | EF560707 |
| Rotavirus A Hu/G2275/USA/1980/G9 | NC_011503 | vertebrates,human | Reoviridae,Rotavirus,Rotavirus A | 1 | seg. 9 | EU153554 |
| Rotavirus A Hu/HK69/CN/1978/G5 | NC_011503 | vertebrates,human | Reoviridae,Rotavirus,Rotavirus A | 1 | seg. 9 | JN699034 |
| Rotavirus A Hu/HK75/CN/1978/G9 | NC_011503 | vertebrates,human | Reoviridae,Rotavirus,Rotavirus A | 1 | seg. 9 | JN699033 |
| Rotavirus A Hu/Ha1/2006/Cuba/G1P[6] | NC_011503 | vertebrates,human | Reoviridae,Rotavirus,Rotavirus A | 1 | seg. 9 | FJ348346 |
| Rotavirus A Hu/Ha100/2008/Cuba/G9P[8] | NC_011503 | vertebrates,human | Reoviridae,Rotavirus,Rotavirus A | 1 | seg. 9 | FJ348355 |
| Rotavirus A Hu/Ha16/2006/Cuba/G9P/G9 | NC_011503 | vertebrates,human | Reoviridae,Rotavirus,Rotavirus A | 1 | seg. 9 | FJ348351 |
| Rotavirus A Hu/Ha21/2006/Cuba/G9P[8] | NC_011503 | vertebrates,human | Reoviridae,Rotavirus,Rotavirus A | 1 | seg. 9 | FJ348354 |
| Rotavirus A Hu/Ha45/2006/Cuba/G1P[8] | NC_011503 | vertebrates,human | Reoviridae,Rotavirus,Rotavirus A | 1 | seg. 9 | FJ348348 |
| Rotavirus A Hu/Ha5/2006/Cuba/G1P[6] | NC_011503 | vertebrates,human | Reoviridae,Rotavirus,Rotavirus A | 1 | seg. 9 | FJ348347 |
| Rotavirus A Hu/Ha67/2007/Cuba/G1P[8] | NC_011503 | vertebrates,human | Reoviridae,Rotavirus,Rotavirus A | 1 | seg. 9 | FJ348349 |
| Rotavirus A Hu/Ha95/2008/Cuba/G1P[8] | NC_011503 | vertebrates,human | Reoviridae,Rotavirus,Rotavirus A | 1 | seg. 9 | FJ348350 |

-continued

| Taxonomy | NCBI Reference Sequence ID | Host | No. of Genomes | Lineage | Segment Count | Genbank Accession ID |
|---|---|---|---|---|---|---|
| Rotavirus A Hu/NhaTrang/V141/2006/VNM/G3 | NC_011503 | vertebrates,human | 1 | Reoviridae,Rotavirus,Rotavirus A | seg. 9 | AB525798 |
| Rotavirus A Hu/NhaTrang/V152/2006/VNM/G3 | NC_011503 | vertebrates,human | 1 | Reoviridae,Rotavirus,Rotavirus A | seg. 9 | AB525799 |
| Rotavirus A Hu/NhaTrang/V17/2006/VNM | NC_011503 | vertebrates,human | 1 | Reoviridae,Rotavirus,Rotavirus A | seg. 9 | AB605602 |
| Rotavirus A Hu/NhaTrang/V17/2006/VNM | NC_011509 | vertebrates,human | 1 | Reoviridae,Rotavirus,Rotavirus A | seg. 6 | AB605598 |
| Rotavirus A Hu/NhaTrang/V173/2006/VNM/G3 | NC_011503 | vertebrates,human | 1 | Reoviridae,Rotavirus,Rotavirus A | seg. 9 | AB525800 |
| Rotavirus A Hu/NhaTrang/V182/2006/VNM/G3 | NC_011503 | vertebrates,human | 1 | Reoviridae,Rotavirus,Rotavirus A | seg. 9 | AB525801 |
| Rotavirus A Hu/NhaTrang/V20/2006/VNM | NC_011503 | vertebrates,human | 1 | Reoviridae,Rotavirus,Rotavirus A | seg. 9 | AB605603 |
| Rotavirus A Hu/NhaTrang/V20/2006/VNM | NC_011509 | vertebrates,human | 1 | Reoviridae,Rotavirus,Rotavirus A | seg. 6 | AB605599 |
| Rotavirus A Hu/NhaTrang/V30/2006/VNM | NC_011503 | vertebrates,human | 1 | Reoviridae,Rotavirus,Rotavirus A | seg. 9 | AB605604 |
| Rotavirus A Hu/NhaTrang/V30/2006/VNM | NC_011509 | vertebrates,human | 1 | Reoviridae,Rotavirus,Rotavirus A | seg. 6 | AB605600 |
| Rotavirus A Hu/NhaTrang/V32/2006/VNM | NC_011503 | vertebrates,human | 1 | Reoviridae,Rotavirus,Rotavirus A | seg. 9 | AB605605 |
| Rotavirus A Hu/NhaTrang/V32/2006/VNM | NC_011509 | vertebrates,human | 1 | Reoviridae,Rotavirus,Rotavirus A | seg. 6 | AB605601 |
| Rotavirus A Hu/NhaTrang/V88/2006/VNM/G3 | NC_011503 | vertebrates,human | 1 | Reoviridae,Rotavirus,Rotavirus A | seg. 9 | AB525797 |
| Rotavirus A Hu/SA3426DGM/04/G12P[6] | NC_011503 | vertebrates,human | 1 | Reoviridae,Rotavirus,Rotavirus A | seg. 9 | EU284736 |
| Rotavirus A Hu/USA/06-242/2006/G2P[6] | NC_011500 | vertebrates,human | 1 | Reoviridae,Rotavirus,Rotavirus A | seg. 5 | JF460818 |
| Rotavirus A Hu/USA/06-242/2006/G2P[6] | NC_011501 | vertebrates,human | 1 | Reoviridae,Rotavirus,Rotavirus A | seg. 7 | JF460820 |
| Rotavirus A Hu/USA/06-242/2006/G2P[6] | NC_011502 | vertebrates,human | 1 | Reoviridae,Rotavirus,Rotavirus A | seg. 8 | JF460819 |

-continued

| Taxonomy | NCBI Reference Sequence ID | Host | No. of Genomes | Lineage | Segment Count | Genbank Accession ID |
|---|---|---|---|---|---|---|
| Rotavirus A Hu/USA/06-242/2006/G2P[6] | NC_011503 | vertebrates,human | 1 | Reoviridae,Rotavirus,Rotavirus A | seg. 9 | JF460817 |
| Rotavirus A Hu/USA/06-242/2006/G2P[6] | NC_011504 | vertebrates,human | 1 | Reoviridae,Rotavirus,Rotavirus A | seg. 10 | JF460821 |
| Rotavirus A Hu/USA/06-242/2006/G2P[6] | NC_011505 | vertebrates,human | 1 | Reoviridae,Rotavirus,Rotavirus A | seg. 11 | JF460822 |
| Rotavirus A Hu/USA/06-242/2006/G2P[6] | NC_011506 | vertebrates,human | 1 | Reoviridae,Rotavirus,Rotavirus A | seg. 2 | JF460813 |
| Rotavirus A Hu/USA/06-242/2006/G2P[6] | NC_011507 | vertebrates,human | 1 | Reoviridae,Rotavirus,Rotavirus A | seg. 1 | JF460812 |
| Rotavirus A Hu/USA/06-242/2006/G2P[6] | NC_011508 | vertebrates,human | 1 | Reoviridae,Rotavirus,Rotavirus A | seg. 3 | JF460814 |
| Rotavirus A Hu/USA/06-242/2006/G2P[6] | NC_011509 | vertebrates,human | 1 | Reoviridae,Rotavirus,Rotavirus A | seg. 6 | JF460816 |
| Rotavirus A Hu/USA/06-242/2006/G2P[6] | NC_011510 | vertebrates,human | 1 | Reoviridae,Rotavirus,Rotavirus A | seg. 4 | JF460815 |
| Rotavirus A IAL28xUK reassortant (UKg9IAL28) | NC_011506 | vertebrates,human | 1 | Reoviridae,Rotavirus,Rotavirus A | seg. 2 | JF990818 |
| Rotavirus A IAL28xUK reassortant (UKg9IAL28) | NC_011507 | vertebrates,human | 1 | Reoviridae,Rotavirus,Rotavirus A | seg. 1 | JF990817 |
| Rotavirus A IAL28xUK reassortant (UKg9IAL28) | NC_011508 | vertebrates,human | 1 | Reoviridae,Rotavirus,Rotavirus A | seg. 3 | JF990819 |
| Rotavirus A Ind/Bo/HR/B85 | NC_011502 | vertebrates,human | 1 | Reoviridae,Rotavirus,Rotavirus A | seg. 8 | JF831950 |
| Rotavirus A Ind/Bo/HR/B85 | NC_011505 | vertebrates,human | 1 | Reoviridae,Rotavirus,Rotavirus A | seg. 11 | JF831951 |
| Rotavirus A Ind/HR/B111 | NC_011504 | vertebrates,human | 1 | Reoviridae,Rotavirus,Rotavirus A | seg. 10 | JF831958 |
| Rotavirus A Ind/HR/B91 | NC_011504 | vertebrates,human | 1 | Reoviridae,Rotavirus,Rotavirus A | seg. 10 | JF831955 |
| Rotavirus A Ind/MP/13100 | NC_011503 | vertebrates,human | 1 | Reoviridae,Rotavirus,Rotavirus A | seg. 9 | JF831944 |
| Rotavirus A Ind/MP/Buffalo/6212 | NC_011504 | vertebrates,human | 1 | Reoviridae,Rotavirus,Rotavirus A | seg. 10 | JF831954 |
| Rotavirus A Ind/MP/C1 | NC_011504 | vertebrates,human | 1 | Reoviridae,Rotavirus,Rotavirus A | seg. 10 | JF831956 |
| Rotavirus A Ind/UKD/C5 | NC_011504 | vertebrates,human | 1 | Reoviridae,Rotavirus,Rotavirus A | seg. 10 | JF831947 |
| Rotavirus A Ind/UP/13E4 | NC_011504 | vertebrates,human | 1 | Reoviridae,Rotavirus,Rotavirus A | seg. 10 | JF831945 |
| Rotavirus A PxUK reassortant (UKg9P) | NC_011500 | vertebrates,human | 3 | Reoviridae,Rotavirus,Rotavirus A | seg. 5 | JF693096,JF693162, JF693211 |
| Rotavirus A PxUK reassortant (UKg9P) | NC_011501 | vertebrates,human | 2 | Reoviridae,Rotavirus,Rotavirus A | seg. 7 | JF693099,JF693165 |
| Rotavirus A PxUK reassortant (UKg9P) | NC_011502 | vertebrates,human | 3 | Reoviridae,Rotavirus,Rotavirus A | seg. 8 | JF693212,JF693164, JF693098 |
| Rotavirus A PxUK reassortant (UKg9P) | NC_011503 | vertebrates,human | 3 | Reoviridae,Rotavirus,Rotavirus A | seg. 9 | JF693166,JF693213, JF693100 |
| Rotavirus A PxUK reassortant (UKg9P) | NC_011504 | vertebrates,human | 2 | Reoviridae,Rotavirus,Rotavirus A | seg. 10 | JF693101,JF693167 |

-continued

| Taxonomy | NCBI Reference Sequence ID | Host | No. of Genomes | Lineage | Segment Count | Genbank Accession ID |
|---|---|---|---|---|---|---|
| Rotavirus A PxUK reassortant (UKg9P) | NC_011505 | vertebrates,human | 2 | Reoviridae,Rotavirus,Rotavirus A | seg. 11 | JF693102,JF693168 |
| Rotavirus A PxUK reassortant (UKg9P) | NC_011506 | vertebrates,human | 2 | Reoviridae,Rotavirus,Rotavirus A | seg. 2 | JF693159,JF693093 |
| Rotavirus A PxUK reassortant (UKg9P) | NC_011507 | vertebrates,human | 2 | Reoviridae,Rotavirus,Rotavirus A | seg. 1 | JF693092,JF693158 |
| Rotavirus A PxUK reassortant (UKg9P) | NC_011508 | vertebrates,human | 2 | Reoviridae,Rotavirus,Rotavirus A | seg. 3 | JF693094,JF693160 |
| Rotavirus A PxUK reassortant (UKg9P) | NC_011509 | vertebrates,human | 2 | Reoviridae,Rotavirus,Rotavirus A | seg. 6 | JF693097,JF693163 |
| Rotavirus A PxUK reassortant (UKg9P) | NC_011510 | vertebrates,human | 3 | Reoviridae,Rotavirus,Rotavirus A | seg. 4 | JF693095,JF693161, JF693210 |
| Rotavirus A RVA/Human-tc/USA/DS-1/1976/G2P[4] | NC_011500 | vertebrates,human | 1 | Reoviridae,Rotavirus,Rotavirus A | seg. 5 | HQ650120 |
| Rotavirus A RVA/Human-tc/USA/DS-1/1976/G2P[4] | NC_011501 | vertebrates,human | 1 | Reoviridae,Rotavirus,Rotavirus A | seg. 7 | HQ650122 |
| Rotavirus A RVA/Human-tc/USA/DS-1/1976/G2P[4] | NC_011502 | vertebrates,human | 1 | Reoviridae,Rotavirus,Rotavirus A | seg. 8 | HQ650123 |
| Rotavirus A RVA/Human-tc/USA/DS-1/1976/G2P[4] | NC_011503 | vertebrates,human | 1 | Reoviridae,Rotavirus,Rotavirus A | seg. 9 | HQ650124 |
| Rotavirus A RVA/Human-tc/USA/DS-1/1976/G2P[4] | NC_011504 | vertebrates,human | 1 | Reoviridae,Rotavirus,Rotavirus A | seg. 10 | HQ650125 |
| Rotavirus A RVA/Human-tc/USA/DS-1/1976/G2P[4] | NC_011505 | vertebrates,human | 1 | Reoviridae,Rotavirus,Rotavirus A | seg. 11 | HQ650126 |
| Rotavirus A RVA/Human-tc/USA/DS-1/1976/G2P[4] | NC_011506 | vertebrates,human | 1 | Reoviridae,Rotavirus,Rotavirus A | seg. 2 | HQ650117 |
| Rotavirus A RVA/Human-tc/USA/DS-1/1976/G2P[4] | NC_011507 | vertebrates,human | 1 | Reoviridae,Rotavirus,Rotavirus A | seg. 1 | HQ650116 |
| Rotavirus A RVA/Human-tc/USA/DS-1/1976/G2P[4] | NC_011508 | vertebrates,human | 1 | Reoviridae,Rotavirus,Rotavirus A | seg. 3 | HQ650118 |
| Rotavirus A RVA/Human-tc/USA/DS-1/1976/G2P[4] | NC_011509 | vertebrates,human | 1 | Reoviridae,Rotavirus,Rotavirus A | seg. 6 | HQ650121 |
| Rotavirus A RVA/Human-tc/USA/DS-1/1976/G2P[4] | NC_011510 | vertebrates,human | 1 | Reoviridae,Rotavirus,Rotavirus A | seg. 4 | HQ650119 |
| Rotavirus A RVA/Human-wt/ITA/ASTI23/2007/G9P8 | NC_011501 | vertebrates,human | 1 | Reoviridae,Rotavirus,Rotavirus A | seg. 7 | JX185766 |
| Rotavirus A RVA/Human-wt/ITA/ASTI23/2007/G9P8 | NC_011502 | vertebrates,human | 1 | Reoviridae,Rotavirus,Rotavirus A | seg. 8 | JX185765 |
| Rotavirus A RVA/Human-wt/ITA/ASTI23/2007/G9P8 | NC_011503 | vertebrates,human | 1 | Reoviridae,Rotavirus,Rotavirus A | seg. 9 | JX185763 |
| Rotavirus A RVA/Human-wt/ITA/ASTI23/2007/G9P8 | NC_011504 | vertebrates,human | 1 | Reoviridae,Rotavirus,Rotavirus A | seg. 10 | JX185767 |
| Rotavirus A RVA/Human-wt/ITA/ASTI23/2007/G9P8 | NC_011505 | vertebrates,human | 1 | Reoviridae,Rotavirus,Rotavirus A | seg. 11 | JX185768 |
| Rotavirus A RVA/Human-wt/ITA/ASTI23/2007/G9P8 | NC_011506 | vertebrates,human | 1 | Reoviridae,Rotavirus,Rotavirus A | seg. 2 | JX185759 |
| Rotavirus A RVA/Human-wt/ITA/ASTI23/2007/G9P8 | NC_011507 | vertebrates,human | 1 | Reoviridae,Rotavirus,Rotavirus A | seg. 1 | JX185758 |

-continued

| Taxonomy | NCBI Reference Sequence ID | Host | No. of Genomes | Lineage | Segment Count | Genbank Accession ID |
|---|---|---|---|---|---|---|
| Rotavirus A RVA/Human-wt/ITA/AST123/2007/G9P8 | NC_011508 | vertebrates,human | 1 | Reoviridae,Rotavirus,Rotavirus A | seg. 3 | JX185760 |
| Rotavirus A RVA/Human-wt/ITA/AST123/2007/G9P8 | NC_011509 | vertebrates,human | 1 | Reoviridae,Rotavirus,Rotavirus A | seg. 6 | JX185762 |
| Rotavirus A RVA/Human-wt/ITA/AST123/2007/G9P8 | NC_011510 | vertebrates,human | 1 | Reoviridae,Rotavirus,Rotavirus A | seg. 4 | JX185761 |
| Rotavirus A RVA/Human-wt/ITA/AV21/2010/G9P8 | NC_011501 | vertebrates,human | 1 | Reoviridae,Rotavirus,Rotavirus A | seg. 7 | JX195071 |
| Rotavirus A RVA/Human-wt/ITA/AV21/2010/G9P8 | NC_011502 | vertebrates,human | 1 | Reoviridae,Rotavirus,Rotavirus A | seg. 8 | JX195070 |
| Rotavirus A RVA/Human-wt/ITA/AV21/2010/G9P8 | NC_011503 | vertebrates,human | 1 | Reoviridae,Rotavirus,Rotavirus A | seg. 9 | JX195068 |
| Rotavirus A RVA/Human-wt/ITA/AV21/2010/G9P8 | NC_011504 | vertebrates,human | 1 | Reoviridae,Rotavirus,Rotavirus A | seg. 10 | JX195072 |
| Rotavirus A RVA/Human-wt/ITA/AV21/2010/G9P8 | NC_011505 | vertebrates,human | 1 | Reoviridae,Rotavirus,Rotavirus A | seg. 11 | JX195073 |
| Rotavirus A RVA/Human-wt/ITA/AV21/2010/G9P8 | NC_011506 | vertebrates,human | 1 | Reoviridae,Rotavirus,Rotavirus A | seg. 2 | JX195064 |
| Rotavirus A RVA/Human-wt/ITA/AV21/2010/G9P8 | NC_011507 | vertebrates,human | 1 | Reoviridae,Rotavirus,Rotavirus A | seg. 1 | JX195063 |
| Rotavirus A RVA/Human-wt/ITA/AV21/2010/G9P8 | NC_011508 | vertebrates,human | 1 | Reoviridae,Rotavirus,Rotavirus A | seg. 3 | JX195065 |
| Rotavirus A RVA/Human-wt/ITA/AV21/2010/G9P8 | NC_011509 | vertebrates,human | 1 | Reoviridae,Rotavirus,Rotavirus A | seg. 6 | JX195067 |
| Rotavirus A RVA/Human-wt/ITA/AV21/2010/G9P8 | NC_011510 | vertebrates,human | 1 | Reoviridae,Rotavirus,Rotavirus A | seg. 4 | JX195066 |
| Rotavirus A RVA/Human-wt/ITA/AV28/2010/G9P8 | NC_011501 | vertebrates,human | 1 | Reoviridae,Rotavirus,Rotavirus A | seg. 7 | JX195082 |
| Rotavirus A RVA/Human-wt/ITA/AV28/2010/G9P8 | NC_011502 | vertebrates,human | 1 | Reoviridae,Rotavirus,Rotavirus A | seg. 8 | JX195081 |
| Rotavirus A RVA/Human-wt/ITA/AV28/2010/G9P8 | NC_011503 | vertebrates,human | 1 | Reoviridae,Rotavirus,Rotavirus A | seg. 9 | JX195079 |
| Rotavirus A RVA/Human-wt/ITA/AV28/2010/G9P8 | NC_011504 | vertebrates,human | 1 | Reoviridae,Rotavirus,Rotavirus A | seg. 10 | JX195083 |
| Rotavirus A RVA/Human-wt/ITA/AV28/2010/G9P8 | NC_011505 | vertebrates,human | 1 | Reoviridae,Rotavirus,Rotavirus A | seg. 11 | JX195084 |
| Rotavirus A RVA/Human-wt/ITA/AV28/2010/G9P8 | NC_011506 | vertebrates,human | 1 | Reoviridae,Rotavirus,Rotavirus A | seg. 2 | JX195075 |
| Rotavirus A RVA/Human-wt/ITA/AV28/2010/G9P8 | NC_011507 | vertebrates,human | 1 | Reoviridae,Rotavirus,Rotavirus A | seg. 1 | JX195074 |
| Rotavirus A RVA/Human-wt/ITA/AV28/2010/G9P8 | NC_011508 | vertebrates,human | 1 | Reoviridae,Rotavirus,Rotavirus A | seg. 3 | JX195076 |
| Rotavirus A RVA/Human-wt/ITA/AV28/2010/G9P8 | NC_011509 | vertebrates,human | 1 | Reoviridae,Rotavirus,Rotavirus A | seg. 6 | JX195078 |
| Rotavirus A RVA/Human-wt/ITA/AV28/2010/G9P8 | NC_011510 | vertebrates,human | 1 | Reoviridae,Rotavirus,Rotavirus A | seg. 4 | JX195077 |
| Rotavirus A RVA/Human-wt/ITA/JES11/2010/G9P8 | NC_011501 | vertebrates,human | 1 | Reoviridae,Rotavirus,Rotavirus A | seg. 7 | JX195093 |

-continued

| Taxonomy | NCBI Reference Sequence ID | Host | No. of Genomes | Lineage | Segment Count | Genbank Accession ID |
|---|---|---|---|---|---|---|
| Rotavirus A RVA/Human-wt/ITA/JES11/2010/G9P8 | NC_011502 | vertebrates,human | 1 | Reoviridae,Rotavirus,Rotavirus A | seg. 8 | JX195092 |
| Rotavirus A RVA/Human-wt/ITA/JES11/2010/G9P8 | NC_011503 | vertebrates,human | 1 | Reoviridae,Rotavirus,Rotavirus A | seg. 9 | JX195090 |
| Rotavirus A RVA/Human-wt/ITA/JES11/2010/G9P8 | NC_011504 | vertebrates,human | 1 | Reoviridae,Rotavirus,Rotavirus A | seg. 10 | JX195094 |
| Rotavirus A RVA/Human-wt/ITA/JES11/2010/G9P8 | NC_011505 | vertebrates,human | 1 | Reoviridae,Rotavirus,Rotavirus A | seg. 11 | JX195095 |
| Rotavirus A RVA/Human-wt/ITA/JES11/2010/G9P8 | NC_011506 | vertebrates,human | 1 | Reoviridae,Rotavirus,Rotavirus A | seg. 2 | JX195086 |
| Rotavirus A RVA/Human-wt/ITA/JES11/2010/G9P8 | NC_011507 | vertebrates,human | 1 | Reoviridae,Rotavirus,Rotavirus A | seg. 1 | JX195085 |
| Rotavirus A RVA/Human-wt/ITA/JES11/2010/G9P8 | NC_011508 | vertebrates,human | 1 | Reoviridae,Rotavirus,Rotavirus A | seg. 3 | JX195087 |
| Rotavirus A RVA/Human-wt/ITA/JES11/2010/G9P8 | NC_011509 | vertebrates,human | 1 | Reoviridae,Rotavirus,Rotavirus A | seg. 6 | JX195089 |
| Rotavirus A RVA/Human-wt/ITA/JES11/2010/G9P8 | NC_011510 | vertebrates,human | 1 | Reoviridae,Rotavirus,Rotavirus A | seg. 4 | JX195088 |
| Rotavirus A RVA/Human/NCA/125L/2010/G3P[8] | NC_011500 | vertebrates,human | 1 | Reoviridae,Rotavirus,Rotavirus A | seg. 5 | JN128984 |
| Rotavirus A RVA/Human/NCA/125L/2010/G3P[8] | NC_011501 | vertebrates,human | 1 | Reoviridae,Rotavirus,Rotavirus A | seg. 7 | JN129012 |
| Rotavirus A RVA/Human/NCA/125L/2010/G3P[8] | NC_011502 | vertebrates,human | 1 | Reoviridae,Rotavirus,Rotavirus A | seg. 8 | JN128998 |
| Rotavirus A RVA/Human/NCA/125L/2010/G3P[8] | NC_011503 | vertebrates,human | 1 | Reoviridae,Rotavirus,Rotavirus A | seg. 9 | JN129124 |
| Rotavirus A RVA/Human/NCA/125L/2010/G3P[8] | NC_011504 | vertebrates,human | 1 | Reoviridae,Rotavirus,Rotavirus A | seg. 10 | JN129026 |
| Rotavirus A RVA/Human/NCA/125L/2010/G3P[8] | NC_011505 | vertebrates,human | 1 | Reoviridae,Rotavirus,Rotavirus A | seg. 11 | JN129040 |
| Rotavirus A RVA/Human/NCA/125L/2010/G3P[8] | NC_011506 | vertebrates,human | 1 | Reoviridae,Rotavirus,Rotavirus A | seg. 2 | JN129068 |
| Rotavirus A RVA/Human/NCA/125L/2010/G3P[8] | NC_011507 | vertebrates,human | 1 | Reoviridae,Rotavirus,Rotavirus A | seg. 1 | JN129054 |
| Rotavirus A RVA/Human/NCA/125L/2010/G3P[8] | NC_011508 | vertebrates,human | 1 | Reoviridae,Rotavirus,Rotavirus A | seg. 3 | JN129082 |
| Rotavirus A RVA/Human/NCA/125L/2010/G3P[8] | NC_011509 | vertebrates,human | 1 | Reoviridae,Rotavirus,Rotavirus A | seg. 6 | JN129110 |

-continued

| Taxonomy | NCBI Reference Sequence ID | Host | No. of Genomes | Lineage | Segment Count | Genbank Accession ID |
|---|---|---|---|---|---|---|
| Rotavirus A RVA/Human/NCA/125L/2010/G3P[8] | NC_011510 | vertebrates,human | 1 | Reoviridae,Rotavirus,Rotavirus A | seg. 4 | JN129096 |
| Rotavirus A RVA/Human/NCA/18J/2010/G1P[8] | NC_011500 | vertebrates,human | 1 | Reoviridae,Rotavirus,Rotavirus A | seg. 5 | JN128974 |
| Rotavirus A RVA/Human/NCA/18J/2010/G1P[8] | NC_011501 | vertebrates,human | 1 | Reoviridae,Rotavirus,Rotavirus A | seg. 7 | JN129002 |
| Rotavirus A RVA/Human/NCA/18J/2010/G1P[8] | NC_011502 | vertebrates,human | 1 | Reoviridae,Rotavirus,Rotavirus A | seg. 8 | JN128988 |
| Rotavirus A RVA/Human/NCA/18J/2010/G1P[8] | NC_011503 | vertebrates,human | 1 | Reoviridae,Rotavirus,Rotavirus A | seg. 9 | JN129114 |
| Rotavirus A RVA/Human/NCA/18J/2010/G1P[8] | NC_011504 | vertebrates,human | 1 | Reoviridae,Rotavirus,Rotavirus A | seg. 10 | JN129016 |
| Rotavirus A RVA/Human/NCA/18J/2010/G1P[8] | NC_011505 | vertebrates,human | 1 | Reoviridae,Rotavirus,Rotavirus A | seg. 11 | JN129030 |
| Rotavirus A RVA/Human/NCA/18J/2010/G1P[8] | NC_011506 | vertebrates,human | 1 | Reoviridae,Rotavirus,Rotavirus A | seg. 2 | JN129058 |
| Rotavirus A RVA/Human/NCA/18J/2010/G1P[8] | NC_011507 | vertebrates,human | 1 | Reoviridae,Rotavirus,Rotavirus A | seg. 1 | JN129044 |
| Rotavirus A RVA/Human/NCA/18J/2010/G1P[8] | NC_011508 | vertebrates,human | 1 | Reoviridae,Rotavirus,Rotavirus A | seg. 3 | JN129072 |
| Rotavirus A RVA/Human/NCA/18J/2010/G1P[8] | NC_011509 | vertebrates,human | 1 | Reoviridae,Rotavirus,Rotavirus A | seg. 6 | JN129100 |
| Rotavirus A RVA/Human/NCA/18J/2010/G1P[8] | NC_011510 | vertebrates,human | 1 | Reoviridae,Rotavirus,Rotavirus A | seg. 4 | JN129086 |
| Rotavirus A RVA/Human/NCA/22J/2010/G1P[8] | NC_011500 | vertebrates,human | 1 | Reoviridae,Rotavirus,Rotavirus A | seg. 5 | JN128975 |
| Rotavirus A RVA/Human/NCA/22J/2010/G1P[8] | NC_011501 | vertebrates,human | 1 | Reoviridae,Rotavirus,Rotavirus A | seg. 7 | JN129003 |
| Rotavirus A RVA/Human/NCA/22J/2010/G1P[8] | NC_011502 | vertebrates,human | 1 | Reoviridae,Rotavirus,Rotavirus A | seg. 8 | JN128989 |
| Rotavirus A RVA/Human/NCA/22J/2010/G1P[8] | NC_011503 | vertebrates,human | 1 | Reoviridae,Rotavirus,Rotavirus A | seg. 9 | JN129115 |

| Taxonomy | NCBI Reference Sequence ID | Host | No. of Genomes | Lineage | Segment Count | Genbank Accession ID |
|---|---|---|---|---|---|---|
| Rotavirus A RVA/Human/NCA/22J/2010/G1P[8] | NC_011504 | vertebrates,human | 1 | Reoviridae,Rotavirus,Rotavirus A | seg. 10 | JN129017 |
| Rotavirus A RVA/Human/NCA/22J/2010/G1P[8] | NC_011505 | vertebrates,human | 1 | Reoviridae,Rotavirus,Rotavirus A | seg. 11 | JN129031 |
| Rotavirus A RVA/Human/NCA/22J/2010/G1P[8] | NC_011506 | vertebrates,human | 1 | Reoviridae,Rotavirus,Rotavirus A | seg. 2 | JN129059 |
| Rotavirus A RVA/Human/NCA/22J/2010/G1P[8] | NC_011507 | vertebrates,human | 1 | Reoviridae,Rotavirus,Rotavirus A | seg. 1 | JN129045 |
| Rotavirus A RVA/Human/NCA/22J/2010/G1P[8] | NC_011508 | vertebrates,human | 1 | Reoviridae,Rotavirus,Rotavirus A | seg. 3 | JN129073 |
| Rotavirus A RVA/Human/NCA/22J/2010/G1P[8] | NC_011509 | vertebrates,human | 1 | Reoviridae,Rotavirus,Rotavirus A | seg. 6 | JN129101 |
| Rotavirus A RVA/Human/NCA/22J/2010/G1P[8] | NC_011510 | vertebrates,human | 1 | Reoviridae,Rotavirus,Rotavirus A | seg. 4 | JN129087 |
| Rotavirus A RVA/Human/NCA/22J/2010/G1P[8] | NC_011500 | vertebrates,human | 1 | Reoviridae,Rotavirus,Rotavirus A | seg. 5 | JN128976 |
| Rotavirus A RVA/Human/NCA/22J/2010/G1P[8] | NC_011501 | vertebrates,human | 1 | Reoviridae,Rotavirus,Rotavirus A | seg. 7 | JN129004 |
| Rotavirus A RVA/Human/NCA/22J/2010/G1P[8] | NC_011502 | vertebrates,human | 1 | Reoviridae,Rotavirus,Rotavirus A | seg. 8 | JN128990 |
| Rotavirus A RVA/Human/NCA/24J/2010/G1P[8] | NC_011503 | vertebrates,human | 1 | Reoviridae,Rotavirus,Rotavirus A | seg. 9 | JN129116 |
| Rotavirus A RVA/Human/NCA/24J/2010/G1P[8] | NC_011504 | vertebrates,human | 1 | Reoviridae,Rotavirus,Rotavirus A | seg. 10 | JN129018 |
| Rotavirus A RVA/Human/NCA/24J/2010/G1P[8] | NC_011505 | vertebrates,human | 1 | Reoviridae,Rotavirus,Rotavirus A | seg. 11 | JN129032 |
| Rotavirus A RVA/Human/NCA/24J/2010/G1P[8] | NC_011506 | vertebrates,human | 1 | Reoviridae,Rotavirus,Rotavirus A | seg. 2 | JN129060 |
| Rotavirus A RVA/Human/NCA/24J/2010/G1P[8] | NC_011507 | vertebrates,human | 1 | Reoviridae,Rotavirus,Rotavirus A | seg. 1 | JN129046 |
| Rotavirus A RVA/Human/NCA/24J/2010/G1P[8] | NC_011508 | vertebrates,human | 1 | Reoviridae,Rotavirus,Rotavirus A | seg. 3 | JN129074 |

-continued

| Taxonomy | NCBI Reference Sequence ID | Host | No. of Genomes | Lineage | Segment Count | Genbank Accession ID |
|---|---|---|---|---|---|---|
| Rotavirus A RVA/Human/NCA/24J/2010/G1P[8] | NC_011509 | vertebrates,human | 1 | Reoviridae,Rotavirus,Rotavirus A | seg. 6 | JN129102 |
| Rotavirus A RVA/Human/NCA/24J/2010/G1P[8] | NC_011510 | vertebrates,human | 1 | Reoviridae,Rotavirus,Rotavirus A | seg. 4 | JN129088 |
| Rotavirus A RVA/Human/NCA/24J/2010/G1P[8] | NC_011500 | vertebrates,human | 1 | Reoviridae,Rotavirus,Rotavirus A | seg. 5 | JN128977 |
| Rotavirus A RVA/Human/NCA/25J/2010/G1P[8] | NC_011501 | vertebrates,human | 1 | Reoviridae,Rotavirus,Rotavirus A | seg. 7 | JN129005 |
| Rotavirus A RVA/Human/NCA/25J/2010/G1P[8] | NC_011502 | vertebrates,human | 1 | Reoviridae,Rotavirus,Rotavirus A | seg. 8 | JN128991 |
| Rotavirus A RVA/Human/NCA/25J/2010/G1P[8] | NC_011503 | vertebrates,human | 1 | Reoviridae,Rotavirus,Rotavirus A | seg. 9 | JN129117 |
| Rotavirus A RVA/Human/NCA/25J/2010/G1P[8] | NC_011504 | vertebrates,human | 1 | Reoviridae,Rotavirus,Rotavirus A | seg. 10 | JN129019 |
| Rotavirus A RVA/Human/NCA/25J/2010/G1P[8] | NC_011505 | vertebrates,human | 1 | Reoviridae,Rotavirus,Rotavirus A | seg. 11 | JN129033 |
| Rotavirus A RVA/Human/NCA/25J/2010/G1P[8] | NC_011506 | vertebrates,human | 1 | Reoviridae,Rotavirus,Rotavirus A | seg. 2 | JN129061 |
| Rotavirus A RVA/Human/NCA/25J/2010/G1P[8] | NC_011507 | vertebrates,human | 1 | Reoviridae,Rotavirus,Rotavirus A | seg. 1 | JN129047 |
| Rotavirus A RVA/Human/NCA/25J/2010/G1P[8] | NC_011508 | vertebrates,human | 1 | Reoviridae,Rotavirus,Rotavirus A | seg. 3 | JN129075 |
| Rotavirus A RVA/Human/NCA/25J/2010/G1P[8] | NC_011509 | vertebrates,human | 1 | Reoviridae,Rotavirus,Rotavirus A | seg. 6 | JN129103 |
| Rotavirus A RVA/Human/NCA/25J/2010/G1P[8] | NC_011510 | vertebrates,human | 1 | Reoviridae,Rotavirus,Rotavirus A | seg. 4 | JN129089 |
| Rotavirus A RVA/Human/NCA/26J/2010/G1P[8] | NC_011500 | vertebrates,human | 1 | Reoviridae,Rotavirus,Rotavirus A | seg. 5 | JN128978 |
| Rotavirus A RVA/Human/NCA/26J/2010/G1P[8] | NC_011501 | vertebrates,human | 1 | Reoviridae,Rotavirus,Rotavirus A | seg. 7 | JN129006 |

| Taxonomy | NCBI Reference Sequence ID | Host | No. of Genomes | Lineage | Segment Count | Genbank Accession ID |
|---|---|---|---|---|---|---|
| Rotavirus A RVA/Human/NCA/26J/2010/G1P[8] | NC_011502 | vertebrates,human | 1 | Reoviridae,Rotavirus,Rotavirus A | seg. 8 | JN128992 |
| Rotavirus A RVA/Human/NCA/26J/2010/G1P[8] | NC_011503 | vertebrates,human | 1 | Reoviridae,Rotavirus,Rotavirus A | seg. 9 | JN129118 |
| Rotavirus A RVA/Human/NCA/26J/2010/G1P[8] | NC_011504 | vertebrates,human | 1 | Reoviridae,Rotavirus,Rotavirus A | seg. 10 | JN129020 |
| Rotavirus A RVA/Human/NCA/26J/2010/G1P[8] | NC_011505 | vertebrates,human | 1 | Reoviridae,Rotavirus,Rotavirus A | seg. 11 | JN129034 |
| Rotavirus A RVA/Human/NCA/26J/2010/G1P[8] | NC_011506 | vertebrates,human | 1 | Reoviridae,Rotavirus,Rotavirus A | seg. 2 | JN129062 |
| Rotavirus A RVA/Human/NCA/26J/2010/G1P[8] | NC_011507 | vertebrates,human | 1 | Reoviridae,Rotavirus,Rotavirus A | seg. 1 | JN129048 |
| Rotavirus A RVA/Human/NCA/26J/2010/G1P[8] | NC_011508 | vertebrates,human | 1 | Reoviridae,Rotavirus,Rotavirus A | seg. 3 | JN129076 |
| Rotavirus A RVA/Human/NCA/26J/2010/G1P[8] | NC_011509 | vertebrates,human | 1 | Reoviridae,Rotavirus,Rotavirus A | seg. 6 | JN129104 |
| Rotavirus A RVA/Human/NCA/26J/2010/G1P[8] | NC_011510 | vertebrates,human | 1 | Reoviridae,Rotavirus,Rotavirus A | seg. 4 | JN129090 |
| Rotavirus A RVA/Human/NCA/28J/2010/G1P[8] | NC_011500 | vertebrates,human | 1 | Reoviridae,Rotavirus,Rotavirus A | seg. 5 | JN128979 |
| Rotavirus A RVA/Human/NCA/28J/2010/G1P[8] | NC_011501 | vertebrates,human | 1 | Reoviridae,Rotavirus,Rotavirus A | seg. 7 | JN129007 |
| Rotavirus A RVA/Human/NCA/28J/2010/G1P[8] | NC_011502 | vertebrates,human | 1 | Reoviridae,Rotavirus,Rotavirus A | seg. 8 | JN128993 |
| Rotavirus A RVA/Human/NCA/28J/2010/G1P[8] | NC_011503 | vertebrates,human | 1 | Reoviridae,Rotavirus,Rotavirus A | seg. 9 | JN129119 |
| Rotavirus A RVA/Human/NCA/28J/2010/G1P[8] | NC_011504 | vertebrates,human | 1 | Reoviridae,Rotavirus,Rotavirus A | seg. 10 | JN129021 |
| Rotavirus A RVA/Human/NCA/28J/2010/G1P[8] | NC_011505 | vertebrates,human | 1 | Reoviridae,Rotavirus,Rotavirus A | seg. 11 | JN129035 |
| Rotavirus A RVA/Human/NCA/28J/2010/G1P[8] | NC_011506 | vertebrates,human | 1 | Reoviridae,Rotavirus,Rotavirus A | seg. 2 | JN129063 |

-continued

| Taxonomy | NCBI Reference Sequence ID | Host | No. of Genomes | Lineage | Segment Count | Genbank Accession ID |
|---|---|---|---|---|---|---|
| Rotavirus A RVA/Human/NCA/28J/2010/G1P[8] | NC_011507 | vertebrates,human | 1 | Reoviridae,Rotavirus,Rotavirus A | seg. 1 | JN129049 |
| Rotavirus A RVA/Human/NCA/28J/2010/G1P[8] | NC_011508 | vertebrates,human | 1 | Reoviridae,Rotavirus,Rotavirus A | seg. 3 | JN129077 |
| Rotavirus A RVA/Human/NCA/28J/2010/G1P[8] | NC_011509 | vertebrates,human | 1 | Reoviridae,Rotavirus,Rotavirus A | seg. 6 | JN129105 |
| Rotavirus A RVA/Human/NCA/28J/2010/G1P[8] | NC_011510 | vertebrates,human | 1 | Reoviridae,Rotavirus,Rotavirus A | seg. 4 | JN129091 |
| Rotavirus A RVA/Human/NCA/28J/2010/G1P[8] | NC_011500 | vertebrates,human | 1 | Reoviridae,Rotavirus,Rotavirus A | seg. 5 | JN128980 |
| Rotavirus A RVA/Human/NCA/41J/2010/G1P[8] | NC_011501 | vertebrates,human | 1 | Reoviridae,Rotavirus,Rotavirus A | seg. 7 | JN129008 |
| Rotavirus A RVA/Human/NCA/41J/2010/G1P[8] | NC_011502 | vertebrates,human | 1 | Reoviridae,Rotavirus,Rotavirus A | seg. 8 | JN128994 |
| Rotavirus A RVA/Human/NCA/41J/2010/G1P[8] | NC_011503 | vertebrates,human | 1 | Reoviridae,Rotavirus,Rotavirus A | seg. 9 | JN129120 |
| Rotavirus A RVA/Human/NCA/41J/2010/G1P[8] | NC_011504 | vertebrates,human | 1 | Reoviridae,Rotavirus,Rotavirus A | seg. 10 | JN129022 |
| Rotavirus A RVA/Human/NCA/41J/2010/G1P[8] | NC_011505 | vertebrates,human | 1 | Reoviridae,Rotavirus,Rotavirus A | seg. 11 | JN129036 |
| Rotavirus A RVA/Human/NCA/41J/2010/G1P[8] | NC_011506 | vertebrates,human | 1 | Reoviridae,Rotavirus,Rotavirus A | seg. 2 | JN129064 |
| Rotavirus A RVA/Human/NCA/41J/2010/G1P[8] | NC_011507 | vertebrates,human | 1 | Reoviridae,Rotavirus,Rotavirus A | seg. 1 | JN129050 |
| Rotavirus A RVA/Human/NCA/41J/2010/G1P[8] | NC_011508 | vertebrates,human | 1 | Reoviridae,Rotavirus,Rotavirus A | seg. 3 | JN129078 |
| Rotavirus A RVA/Human/NCA/41J/2010/G1P[8] | NC_011509 | vertebrates,human | 1 | Reoviridae,Rotavirus,Rotavirus A | seg. 6 | JN129106 |
| Rotavirus A RVA/Human/NCA/41J/2010/G1P[8] | NC_011510 | vertebrates,human | 1 | Reoviridae,Rotavirus,Rotavirus A | seg. 4 | JN129092 |
| Rotavirus A RVA/Human/NCA/45J/2010/G1P[8] | NC_011500 | vertebrates,human | 1 | Reoviridae,Rotavirus,Rotavirus A | seg. 5 | JN128981 |

-continued

| Taxonomy | NCBI Reference Sequence ID | Host | No. of Genomes | Lineage | Segment Count | Genbank Accession ID |
|---|---|---|---|---|---|---|
| Rotavirus A RVA/Human/NCA/45J/201 0/G1P[8] | NC_011501 | vertebrates,human | 1 | Reoviridae,Rotavirus,Rotavirus A | seg. 7 | JN129009 |
| Rotavirus A RVA/Human/NCA/45J/201 0/G1P[8] | NC_011502 | vertebrates,human | 1 | Reoviridae,Rotavirus,Rotavirus A | seg. 8 | JN128995 |
| Rotavirus A RVA/Human/NCA/45J/201 0/G1P[8] | NC_011503 | vertebrates,human | 1 | Reoviridae,Rotavirus,Rotavirus A | seg. 9 | JN129121 |
| Rotavirus A RVA/Human/NCA/45J/201 0/G1P[8] | NC_011504 | vertebrates,human | 1 | Reoviridae,Rotavirus,Rotavirus A | seg. 10 | JN129023 |
| Rotavirus A RVA/Human/NCA/45J/201 0/G1P[8] | NC_011505 | vertebrates,human | 1 | Reoviridae,Rotavirus,Rotavirus A | seg. 11 | JN129037 |
| Rotavirus A RVA/Human/NCA/45J/201 0/G1P[8] | NC_011506 | vertebrates,human | 1 | Reoviridae,Rotavirus,Rotavirus A | seg. 2 | JN129065 |
| Rotavirus A RVA/Human/NCA/45J/201 0/G1P[8] | NC_011507 | vertebrates,human | 1 | Reoviridae,Rotavirus,Rotavirus A | seg. 1 | JN129051 |
| Rotavirus A RVA/Human/NCA/45J/201 0/G1P[8] | NC_011508 | vertebrates,human | 1 | Reoviridae,Rotavirus,Rotavirus A | seg. 3 | JN129079 |
| Rotavirus A RVA/Human/NCA/45J/201 0/G1P[8] | NC_011509 | vertebrates,human | 1 | Reoviridae,Rotavirus,Rotavirus A | seg. 6 | JN129107 |
| Rotavirus A RVA/Human/NCA/45J/201 0/G1P[8] | NC_011510 | vertebrates,human | 1 | Reoviridae,Rotavirus,Rotavirus A | seg. 4 | JN129093 |
| Rotavirus A RVA/Human/NCA/64J/201 0/G3P[8] | NC_011500 | vertebrates,human | 1 | Reoviridae,Rotavirus,Rotavirus A | seg. 5 | JN128982 |
| Rotavirus A RVA/Human/NCA/64J/201 0/G3P[8] | NC_011501 | vertebrates,human | 1 | Reoviridae,Rotavirus,Rotavirus A | seg. 7 | JN129010 |
| Rotavirus A RVA/Human/NCA/64J/201 0/G3P[8] | NC_011502 | vertebrates,human | 1 | Reoviridae,Rotavirus,Rotavirus A | seg. 8 | JN128996 |
| Rotavirus A RVA/Human/NCA/64J/201 0/G3P[8] | NC_011503 | vertebrates,human | 1 | Reoviridae,Rotavirus,Rotavirus A | seg. 9 | JN129122 |
| Rotavirus A RVA/Human/NCA/64J/201 0/G3P[8] | NC_011504 | vertebrates,human | 1 | Reoviridae,Rotavirus,Rotavirus A | seg. 10 | JN129024 |
| Rotavirus A RVA/Human/NCA/64J/201 0/G3P[8] | NC_011505 | vertebrates,human | 1 | Reoviridae,Rotavirus,Rotavirus A | seg. 11 | JN129038 |

-continued

| Taxonomy | NCBI Reference Sequence ID | Host | No. of Genomes | Lineage | Segment Count | Genbank Accession ID |
|---|---|---|---|---|---|---|
| Rotavirus A RVA/Human/NCA/64J/2010/G3P[8] | NC_011506 | vertebrates,human | 1 | Reoviridae,Rotavirus,Rotavirus A | seg. 2 | JN129066 |
| Rotavirus A RVA/Human/NCA/64J/2010/G3P[8] | NC_011507 | vertebrates,human | 1 | Reoviridae,Rotavirus,Rotavirus A | seg. 1 | JN129052 |
| Rotavirus A RVA/Human/NCA/64J/2010/G3P[8] | NC_011508 | vertebrates,human | 1 | Reoviridae,Rotavirus,Rotavirus A | seg. 3 | JN129080 |
| Rotavirus A RVA/Human/NCA/64J/2010/G3P[8] | NC_011509 | vertebrates,human | 1 | Reoviridae,Rotavirus,Rotavirus A | seg. 6 | JN129108 |
| Rotavirus A RVA/Human/NCA/64J/2010/G3P[8] | NC_011510 | vertebrates,human | 1 | Reoviridae,Rotavirus,Rotavirus A | seg. 4 | JN129094 |
| Rotavirus A RVA/Human/NCA/64J/2010/G3P[8] | NC_011500 | vertebrates,human | 1 | Reoviridae,Rotavirus,Rotavirus A | seg. 5 | JN128983 |
| Rotavirus A RVA/Human/NCA/72J/2010/G1P[8] | NC_011501 | vertebrates,human | 1 | Reoviridae,Rotavirus,Rotavirus A | seg. 7 | JN129011 |
| Rotavirus A RVA/Human/NCA/72J/2010/G1P[8] | NC_011502 | vertebrates,human | 1 | Reoviridae,Rotavirus,Rotavirus A | seg. 8 | JN128997 |
| Rotavirus A RVA/Human/NCA/72J/2010/G1P[8] | NC_011503 | vertebrates,human | 1 | Reoviridae,Rotavirus,Rotavirus A | seg. 9 | JN129123 |
| Rotavirus A RVA/Human/NCA/72J/2010/G1P[8] | NC_011504 | vertebrates,human | 1 | Reoviridae,Rotavirus,Rotavirus A | seg. 10 | JN129025 |
| Rotavirus A RVA/Human/NCA/72J/2010/G1P[8] | NC_011505 | vertebrates,human | 1 | Reoviridae,Rotavirus,Rotavirus A | seg. 11 | JN129039 |
| Rotavirus A RVA/Human/NCA/72J/2010/G1P[8] | NC_011506 | vertebrates,human | 1 | Reoviridae,Rotavirus,Rotavirus A | seg. 2 | JN129067 |
| Rotavirus A RVA/Human/NCA/72J/2010/G1P[8] | NC_011507 | vertebrates,human | 1 | Reoviridae,Rotavirus,Rotavirus A | seg. 1 | JN129053 |
| Rotavirus A RVA/Human/NCA/72J/2010/G1P[8] | NC_011508 | vertebrates,human | 1 | Reoviridae,Rotavirus,Rotavirus A | seg. 3 | JN129081 |
| Rotavirus A RVA/Human/NCA/72J/2010/G1P[8] | NC_011509 | vertebrates,human | 1 | Reoviridae,Rotavirus,Rotavirus A | seg. 6 | JN129109 |
| Rotavirus A RVA/Human/NCA/72J/2010/G1P[8] | NC_011510 | vertebrates,human | 1 | Reoviridae,Rotavirus,Rotavirus A | seg. 4 | JN129095 |

| Taxonomy | NCBI Reference Sequence ID | Host | No. of Genomes | Lineage | Segment Count | Genbank Accession ID |
|---|---|---|---|---|---|---|
| Rotavirus A RVA/Human/NCA/7J/2010/ G1P[8] | NC_011500 | vertebrates,human | 1 | Reoviridae,Rotavirus,Rotavirus A | seg. 5 | JN128972 |
| Rotavirus A RVA/Human/NCA/7J/2010/ G1P[8] | NC_011501 | vertebrates,human | 1 | Reoviridae,Rotavirus,Rotavirus A | seg. 7 | JN129000 |
| Rotavirus A RVA/Human/NCA/7J/2010/ G1P[8] | NC_011502 | vertebrates,human | 1 | Reoviridae,Rotavirus,Rotavirus A | seg. 8 | JN128986 |
| Rotavirus A RVA/Human/NCA/7J/2010/ G1P[8] | NC_011503 | vertebrates,human | 1 | Reoviridae,Rotavirus,Rotavirus A | seg. 9 | JN129112 |
| Rotavirus A RVA/Human/NCA/7J/2010/ G1P[8] | NC_011504 | vertebrates,human | 1 | Reoviridae,Rotavirus,Rotavirus A | seg. 10 | JN129014 |
| Rotavirus A RVA/Human/NCA/7J/2010/ G1P[8] | NC_011505 | vertebrates,human | 2 | Reoviridae,Rotavirus,Rotavirus A | seg. 11 | JN129028,JN129042 |
| Rotavirus A RVA/Human/NCA/7J/2010/ G1P[8] | NC_011506 | vertebrates,human | 1 | Reoviridae,Rotavirus,Rotavirus A | seg. 2 | JN129056 |
| Rotavirus A RVA/Human/NCA/7J/2010/ G1P[8] | NC_011508 | vertebrates,human | 1 | Reoviridae,Rotavirus,Rotavirus A | seg. 3 | JN129070 |
| Rotavirus A RVA/Human/NCA/7J/2010/ G1P[8] | NC_011509 | vertebrates,human | 1 | Reoviridae,Rotavirus,Rotavirus A | seg. 6 | JN129098 |
| Rotavirus A RVA/Human/NCA/7J/2010/ G1P[8] | NC_011510 | vertebrates,human | 1 | Reoviridae,Rotavirus,Rotavirus A | seg. 4 | JN129084 |
| Rotavirus A RVA/Human/NCA/9J/2010/ G1P[8] | NC_011500 | vertebrates,human | 1 | Reoviridae,Rotavirus,Rotavirus A | seg. 5 | JN128973 |
| Rotavirus A RVA/Human/NCA/9J/2010/ G1P[8] | NC_011501 | vertebrates,human | 1 | Reoviridae,Rotavirus,Rotavirus A | seg. 7 | JN129001 |
| Rotavirus A RVA/Human/NCA/9J/2010/ G1P[8] | NC_011502 | vertebrates,human | 1 | Reoviridae,Rotavirus,Rotavirus A | seg. 8 | JN128987 |
| Rotavirus A RVA/Human/NCA/9J/2010/ G1P[8] | NC_011503 | vertebrates,human | 1 | Reoviridae,Rotavirus,Rotavirus A | seg. 9 | JN129113 |
| Rotavirus A RVA/Human/NCA/9J/2010/ G1P[8] | NC_011504 | vertebrates,human | 1 | Reoviridae,Rotavirus,Rotavirus A | seg. 10 | JN129015 |
| Rotavirus A RVA/Human/NCA/9J/2010/ G1P[8] | NC_011505 | vertebrates,human | 1 | Reoviridae,Rotavirus,Rotavirus A | seg. 11 | JN129029 |

| Taxonomy | NCBI Reference Sequence ID | Host | No. of Genomes | Lineage | Segment Count | Genbank Accession ID |
|---|---|---|---|---|---|---|
| Rotavirus A RVA/Human/NCA/9J/2010/G1P[8] | NC_011506 | vertebrates,human | 1 | Reoviridae,Rotavirus,Rotavirus A | seg. 2 | JN129057 |
| Rotavirus A RVA/Human/NCA/9J/2010/G1P[8] | NC_011507 | vertebrates,human | 1 | Reoviridae,Rotavirus,Rotavirus A | seg. 1 | JN129043 |
| Rotavirus A RVA/Human/NCA/9J/2010/G1P[8] | NC_011508 | vertebrates,human | 1 | Reoviridae,Rotavirus,Rotavirus A | seg. 3 | JN129071 |
| Rotavirus A RVA/Human/NCA/9J/2010/G1P[8] | NC_011509 | vertebrates,human | 1 | Reoviridae,Rotavirus,Rotavirus A | seg. 6 | JN129099 |
| Rotavirus A RVA/Human/NCA/9J/2010/G1P[8] | NC_011510 | vertebrates,human | 1 | Reoviridae,Rotavirus,Rotavirus A | seg. 4 | JN129085 |
| Rotavirus A RVA/Human/NCA/9J/2010/G1P[8] | NC_011500 | vertebrates,human | 1 | Reoviridae,Rotavirus,Rotavirus A | seg. 5 | JN128985 |
| Rotavirus A RVA/Human/NCA/0U2010/G4P[6] | NC_011501 | vertebrates,human | 1 | Reoviridae,Rotavirus,Rotavirus A | seg. 7 | JN129013 |
| Rotavirus A RVA/Human/NCA/0U2010/G4P[6] | NC_011502 | vertebrates,human | 1 | Reoviridae,Rotavirus,Rotavirus A | seg. 8 | JN128999 |
| Rotavirus A RVA/Human/NCA/0U2010/G4P[6] | NC_011503 | vertebrates,human | 1 | Reoviridae,Rotavirus,Rotavirus A | seg. 9 | JN129125 |
| Rotavirus A RVA/Human/NCA/0U2010/G4P[6] | NC_011504 | vertebrates,human | 1 | Reoviridae,Rotavirus,Rotavirus A | seg. 10 | JN129027 |
| Rotavirus A RVA/Human/NCA/0U2010/G4P[6] | NC_011505 | vertebrates,human | 1 | Reoviridae,Rotavirus,Rotavirus A | seg. 11 | JN129041 |
| Rotavirus A RVA/Human/NCA/0U2010/G4P[6] | NC_011506 | vertebrates,human | 1 | Reoviridae,Rotavirus,Rotavirus A | seg. 2 | JN129069 |
| Rotavirus A RVA/Human/NCA/0U2010/G4P[6] | NC_011507 | vertebrates,human | 1 | Reoviridae,Rotavirus,Rotavirus A | seg. 1 | JN129055 |
| Rotavirus A RVA/Human/NCA/0U2010/G4P[6] | NC_011508 | vertebrates,human | 1 | Reoviridae,Rotavirus,Rotavirus A | seg. 3 | JN129083 |
| Rotavirus A RVA/Human/NCA/0U2010/G4P[6] | NC_011509 | vertebrates,human | 1 | Reoviridae,Rotavirus,Rotavirus A | seg. 6 | JN129111 |
| Rotavirus A RVA/Human/NCA/0U2010/G4P[6] | NC_011510 | vertebrates,human | 1 | Reoviridae,Rotavirus,Rotavirus A | seg. 4 | JN129097 |

-continued

| Taxonomy | NCBI Reference Sequence ID | Host | No. of Genomes | Lineage | Segment Count | Genbank Accession ID |
|---|---|---|---|---|---|---|
| Rotavirus A ST3xUK reassortant (UKg9ST3) | NC_011500 | vertebrates,human | 3 | Reoviridae,Rotavirus,Rotavirus A | seg. 5 | JF693215,JF693107, JF693173 |
| Rotavirus A ST3xUK reassortant (UKg9ST3) | NC_011501 | vertebrates,human | 2 | Reoviridae,Rotavirus,Rotavirus A | seg. 7 | JF693176,JF693110 |
| Rotavirus A ST3xUK reassortant (UKg9ST3) | NC_011502 | vertebrates,human | 3 | Reoviridae,Rotavirus,Rotavirus A | seg. 8 | JF693109,JF693175, JF693216 |
| Rotavirus A ST3xUK reassortant (UKg9ST3) | NC_011503 | vertebrates,human | 3 | Reoviridae,Rotavirus,Rotavirus A | seg. 9 | JF693217,JF693111, JF693177 |
| Rotavirus A ST3xUK reassortant (UKg9ST3) | NC_011504 | vertebrates,human | 2 | Reoviridae,Rotavirus,Rotavirus A | seg. 10 | JF693112,JF693178 |
| Rotavirus A ST3xUK reassortant (UKg9ST3) | NC_011505 | vertebrates,human | 2 | Reoviridae,Rotavirus,Rotavirus A | seg. 11 | JF693113,JF693179 |
| Rotavirus A ST3xUK reassortant (UKg9ST3) | NC_011506 | vertebrates,human | 2 | Reoviridae,Rotavirus,Rotavirus A | seg. 2 | JF693104,JF693170 |
| Rotavirus A ST3xUK reassortant (UKg9ST3) | NC_011507 | vertebrates,human | 2 | Reoviridae,Rotavirus,Rotavirus A | seg. 1 | JF693169,JF693103 |
| Rotavirus A ST3xUK reassortant (UKg9ST3) | NC_011508 | vertebrates,human | 2 | Reoviridae,Rotavirus,Rotavirus A | seg. 3 | JF693171,JF693105 |
| Rotavirus A ST3xUK reassortant (UKg9ST3) | NC_011509 | vertebrates,human | 2 | Reoviridae,Rotavirus,Rotavirus A | seg. 6 | JF693174,JF693108 |
| Rotavirus A ST3xUK reassortant (UKg9ST3) | NC_011510 | vertebrates,human | 3 | Reoviridae,Rotavirus,Rotavirus A | seg. 4 | JF693214,JF693106, JF693172 |
| Rotavirus A UK WT BR-3 | NC_011506 | vertebrates,human | 1 | Reoviridae,Rotavirus,Rotavirus A | seg. 2 | JF990806 |
| Rotavirus A UK WT BR-3 | NC_011507 | vertebrates,human | 1 | Reoviridae,Rotavirus,Rotavirus A | seg. 1 | JF990805 |
| Rotavirus A UK WT BR-3 | NC_011508 | vertebrates,human | 1 | Reoviridae,Rotavirus,Rotavirus A | seg. 3 | JF990807 |
| Rotavirus A WaxUK reassortant (UKg4Wa) | NC_011506 | vertebrates,human | 1 | Reoviridae,Rotavirus,Rotavirus A | seg. 2 | JF990829 |
| Rotavirus A WaxUK reassortant (UKg4Wa) | NC_011507 | vertebrates,human | 1 | Reoviridae,Rotavirus,Rotavirus A | seg. 1 | JF990828 |
| Rotavirus A WaxUK reassortant (UKg4Wa) | NC_011508 | vertebrates,human | 1 | Reoviridae,Rotavirus,Rotavirus A | seg. 3 | JF990830 |
| Rotavirus A bovine/Arg/B383/1998 | NC_011501 | vertebrates,human | 1 | Reoviridae,Rotavirus,Rotavirus A | seg. 7 | FJ347119 |
| Rotavirus A bovine/Arg/B383/1998 | NC_011502 | vertebrates,human | 1 | Reoviridae,Rotavirus,Rotavirus A | seg. 8 | FJ347118 |
| Rotavirus A bovine/Arg/B383/1998 | NC_011503 | vertebrates,human | 1 | Reoviridae,Rotavirus,Rotavirus A | seg. 9 | FJ347116 |
| Rotavirus A bovine/Arg/B383/1998 | NC_011504 | vertebrates,human | 1 | Reoviridae,Rotavirus,Rotavirus A | seg. 10 | FJ347120 |
| Rotavirus A bovine/Arg/B383/1998 | NC_011505 | vertebrates,human | 1 | Reoviridae,Rotavirus,Rotavirus A | seg. 11 | FJ347121 |
| Rotavirus A bovine/Arg/B383/1998 | NC_011506 | vertebrates,human | 1 | Reoviridae,Rotavirus,Rotavirus A | seg. 2 | FJ347112 |
| Rotavirus A bovine/Arg/B383/1998 | NC_011507 | vertebrates,human | 1 | Reoviridae,Rotavirus,Rotavirus A | seg. 1 | FJ347111 |
| Rotavirus A bovine/Arg/B383/1998 | NC_011508 | vertebrates,human | 1 | Reoviridae,Rotavirus,Rotavirus A | seg. 3 | FJ347113 |

| Taxonomy | NCBI Reference Sequence ID | Host | No. of Genomes | Lineage | Segment Count | Genbank Accession ID |
|---|---|---|---|---|---|---|
| Rotavirus A bovine/Arg/B383/1998 | NC_011509 | vertebrates,human | 1 | Reoviridae,Rotavirus,Rotavirus A | seg. 6 | FJ347115 |
| Rotavirus A bovine/B223/G10 | NC_011504 | vertebrates,human | 1 | Reoviridae,Rotavirus,Rotavirus A | seg. 10 | AF144805 |
| Rotavirus A guanaco/Arg/Chubut/1999 | NC_011501 | vertebrates,human | 1 | Reoviridae,Rotavirus,Rotavirus A | seg. 7 | FJ347108 |
| Rotavirus A guanaco/Arg/Chubut/1999 | NC_011502 | vertebrates,human | 1 | Reoviridae,Rotavirus,Rotavirus A | seg. 8 | FJ347107 |
| Rotavirus A guanaco/Arg/Chubut/1999 | NC_011503 | vertebrates,human | 1 | Reoviridae,Rotavirus,Rotavirus A | seg. 9 | FJ347105 |
| Rotavirus A guanaco/Arg/Chubut/1999 | NC_011504 | vertebrates,human | 1 | Reoviridae,Rotavirus,Rotavirus A | seg. 10 | FJ347109 |
| Rotavirus A guanaco/Arg/Chubut/1999 | NC_011505 | vertebrates,human | 1 | Reoviridae,Rotavirus,Rotavirus A | seg. 11 | FJ347110 |
| Rotavirus A guanaco/Arg/Chubut/1999 | NC_011506 | vertebrates,human | 1 | Reoviridae,Rotavirus,Rotavirus A | seg. 2 | FJ347101 |
| Rotavirus A guanaco/Arg/Chubut/1999 | NC_011507 | vertebrates,human | 1 | Reoviridae,Rotavirus,Rotavirus A | seg. 1 | FJ347100 |
| Rotavirus A guanaco/Arg/Chubut/1999 | NC_011508 | vertebrates,human | 1 | Reoviridae,Rotavirus,Rotavirus A | seg. 3 | FJ347102 |
| Rotavirus A guanaco/Arg/Chubut/1999 | NC_011509 | vertebrates,human | 1 | Reoviridae,Rotavirus,Rotavirus A | seg. 6 | FJ347104 |
| Rotavirus A guanaco/Arg/Chubut/1999 | NC_011510 | vertebrates,human | 1 | Reoviridae,Rotavirus,Rotavirus A | seg. 4 | FJ347103 |
| Rotavirus A guanaco/Arg/Rio Negro/1998 | NC_011501 | vertebrates,human | 1 | Reoviridae,Rotavirus,Rotavirus A | seg. 7 | FJ347130 |
| Rotavirus A guanaco/Arg/Rio Negro/1998 | NC_011502 | vertebrates,human | 1 | Reoviridae,Rotavirus,Rotavirus A | seg. 8 | FJ347129 |
| Rotavirus A guanaco/Arg/Rio Negro/1998 | NC_011503 | vertebrates,human | 1 | Reoviridae,Rotavirus,Rotavirus A | seg. 9 | FJ347127 |
| Rotavirus A guanaco/Arg/Rio Negro/1998 | NC_011504 | vertebrates,human | 1 | Reoviridae,Rotavirus,Rotavirus A | seg. 10 | FJ347131 |
| Rotavirus A guanaco/Arg/Rio Negro/1998 | NC_011505 | vertebrates,human | 1 | Reoviridae,Rotavirus,Rotavirus A | seg. 11 | FJ347132 |
| Rotavirus A guanaco/Arg/Rio Negro/1998 | NC_011506 | vertebrates,human | 1 | Reoviridae,Rotavirus,Rotavirus A | seg. 2 | FJ347123 |
| Rotavirus A guanaco/Arg/Rio Negro/1998 | NC_011507 | vertebrates,human | 1 | Reoviridae,Rotavirus,Rotavirus A | seg. 1 | FJ347122 |
| Rotavirus A guanaco/Arg/Rio Negro/1998 | NC_011508 | vertebrates,human | 1 | Reoviridae,Rotavirus,Rotavirus A | seg. 3 | FJ347124 |

| Taxonomy | NCBI Reference Sequence ID | Host | No. of Genomes | Lineage | Segment Count | Genbank Accession ID |
|---|---|---|---|---|---|---|
| Rotavirus A guanaco/Arg/Rio Negro/1998 | NC_011509 | vertebrates,human | 1 | Reoviridae,Rotavirus,Rotavirus A | seg. 6 | FJ347126 |
| Rotavirus A guanaco/Arg/Rio Negro/1998 | NC_011510 | vertebrates,human | 1 | Reoviridae,Rotavirus,Rotavirus A | seg. 4 | FJ347125 |
| Rotavirus A human-wt/USA/LB1562/2010/G9P 4 | NC_011503 | vertebrates,human | 1 | Reoviridae,Rotavirus,Rotavirus A | seg. 9 | KC782524 |
| Rotavirus A human-wt/USA/LB1562/2010/G9P 4 | NC_011506 | vertebrates,human | 1 | Reoviridae,Rotavirus,Rotavirus A | seg. 2 | KC782520 |
| Rotavirus A human-wt/USA/LB1562/2010/G9P 4 | NC_011507 | vertebrates,human | 1 | Reoviridae,Rotavirus,Rotavirus A | seg. 1 | KC782519 |
| Rotavirus A human-wt/USA/LB1562/2010/G9P 4 | NC_011508 | vertebrates,human | 1 | Reoviridae,Rotavirus,Rotavirus A | seg. 3 | KC782521 |
| Rotavirus A human/Bethesda/CH5446/ 1991/G3P[8] | NC_011500 | vertebrates,human | 1 | Reoviridae,Rotavirus,Rotavirus A | seg. 5 | FJ947432 |
| Rotavirus A human/Bethesda/CH5446/ 1991/G3P[8] | NC_011501 | vertebrates,human | 1 | Reoviridae,Rotavirus,Rotavirus A | seg. 7 | FJ947434 |
| Rotavirus A human/Bethesda/CH5446/ 1991/G3P[8] | NC_011502 | vertebrates,human | 1 | Reoviridae,Rotavirus,Rotavirus A | seg. 8 | FJ947435 |
| Rotavirus A human/Bethesda/CH5446/ 1991/G3P[8] | NC_011504 | vertebrates,human | 1 | Reoviridae,Rotavirus,Rotavirus A | seg. 10 | FJ947437 |
| Rotavirus A human/Bethesda/CH5446/ 1991/G3P[8] | NC_011505 | vertebrates,human | 1 | Reoviridae,Rotavirus,Rotavirus A | seg. 11 | FJ947438 |
| Rotavirus A human/Bethesda/CH5446/ 1991/G3P[8] | NC_011506 | vertebrates,human | 1 | Reoviridae,Rotavirus,Rotavirus A | seg. 2 | FJ947429 |
| Rotavirus A human/Bethesda/CH5446/ 1991/G3P[8] | NC_011508 | vertebrates,human | 1 | Reoviridae,Rotavirus,Rotavirus A | seg. 3 | FJ947430 |
| Rotavirus A human/Bethesda/CH5446/ 1991/G3P[8] | NC_011509 | vertebrates,human | 1 | Reoviridae,Rotavirus,Rotavirus A | seg. 6 | FJ947433 |
| Rotavirus A human/Bethesda/CH5446/ 1991/G3P[8] | NC_011510 | vertebrates,human | 1 | Reoviridae,Rotavirus,Rotavirus A | seg. 4 | FJ947431 |
| Rotavirus A human/Bethesda/CH5455/ 1991/G3P[8] | NC_011500 | vertebrates,human | 1 | Reoviridae,Rotavirus,Rotavirus A | seg. 5 | FJ947896 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/CH5455/ 1991/G3P[8] | NC_011501 | vertebrates,human | 1 | Reoviridae,Rotavirus,Rotavirus A | seg. 7 | FJ947

| Taxonomy | NCBI Reference Sequence ID | Host | No. of Genomes | Lineage | Segment Count | Genbank Accession ID |
|---|---|---|---|---|---|---|
| Rotavirus A human/Bethesda/CH5470/ 1991/G3P[8] | NC_011501 | vertebrates,human | 1 | Reoviridae,Rotavirus,Rotavirus A | seg. 7 | FJ947909 |
| Rotavirus A human/Bethesda/CH5470/ 1991/G3P[8] | NC_011502 | vertebrates,human | 1 | Reoviridae,Rotavirus,Rotavirus A | seg. 8 | FJ947910 |
| Rotavirus A human/Bethesda/CH5470/ 1991/G3P[8] | NC_011504 | vertebrates,human | 1 | Reoviridae,Rotavirus,Rotavirus A | seg. 10 | FJ947912 |
| Rotavirus A human/Bethesda/CH5470/ 1991/G3P[8] | NC_011505 | vertebrates,human | 1 | Reoviridae,Rotavirus,Rotavirus A | seg. 11 | FJ947913 |
| Rotavirus A human/Bethesda/CH5470/ 1991/G3P[8] | NC_011508 | vertebrates,human | 1 | Reoviridae,Rotavirus,Rotavirus A | seg. 3 | FJ947905 |
| Rotavirus A human/Bethesda/CH5470/ 1991/G3P[8] | NC_011509 | vertebrates,human | 1 | Reoviridae,Rotavirus,Rotavirus A | seg. 6 | FJ947908 |
| Rotavirus A human/Bethesda/CH5470/ 1991/G3P[8] | NC_011510 | vertebrates,human | 1 | Reoviridae,Rotavirus,Rotavirus A | seg. 4 | FJ947906 |
| Rotavirus A human/Bethesda/CH5475/ 1991/G3P[8] | NC_011500 | vertebrates,human | 1 | Reoviridae,Rotavirus,Rotavirus A | seg. 5 | FJ947454 |
| Rotavirus A human/Bethesda/CH5475/ 1991/G3P[8] | NC_011501 | vertebrates,human | 1 | Reoviridae,Rotavirus,Rotavirus A | seg. 7 | FJ947456 |
| Rotavirus A human/Bethesda/CH5475/ 1991/G3P[8] | NC_011502 | vertebrates,human | 1 | Reoviridae,Rotavirus,Rotavirus A | seg. 8 | FJ947457 |
| Rotavirus A human/Bethesda/CH5475/ 1991/G3P[8] | NC_011504 | vertebrates,human | 1 | Reoviridae,Rotavirus,Rotavirus A | seg. 10 | FJ947459 |
| Rotavirus A human/Bethesda/CH5475/ 1991/G3P[8] | NC_011505 | vertebrates,human | 1 | Reoviridae,Rotavirus,Rotavirus A | seg. 11 | FJ947460 |
| Rotavirus A human/Bethesda/CH5475/ 1991/G3P[8] | NC_011508 | vertebrates,human | 1 | Reoviridae,Rotavirus,Rotavirus A | seg. 3 | FJ947452 |
| Rotavirus A human/Bethesda/CH5475/ 1991/G3P[8] | NC_011509 | vertebrates,human | 1 | Reoviridae,Rotavirus,Rotavirus A | seg. 6 | FJ947455 |
| Rotavirus A human/Bethesda/CH5475/ 1991/G3P[8] | NC_011510 | vertebrates,human | 1 | Reoviridae,Rotavirus,Rotavirus A | seg. 4 | FJ947453 |
| Rotavirus A human/Bethesda/CH5477/ 1991/G3P[8] | NC_011501 | vertebrates,human | 1 | Reoviridae,Rotavirus,Rotavirus A | seg. 7 | FJ947467 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/CH5477/1991/G3P[8] | NC_011502 | vertebrates,human | 1 | Reoviridae,Rotavirus,Rotavirus A | seg. 8 | FJ947468 |
| Rotavirus A human/Bethesda/CH5477/1991/G3P[8] | NC_011504 | vertebrates,human | 1 | Reoviridae,Rotavirus,Rotavirus A | seg. 10 | FJ947470 |
| Rotavirus A human/Bethesda/CH5477/1991/G3P[8] | NC_011505 | vertebrates,human | 1 | Reoviridae,Rotavirus,Rotavirus A | seg. 11 | FJ947471 |
| Rotavirus A human/Bethesda/CH5477/1991/G3P[8] | NC_011506 | vertebrates,human | 1 | Reoviridae,Rotavirus,Rotavirus A | seg. 2 | FJ947462 |
| Rotavirus A human/Bethesda/CH5477/1991/G3P[8] | NC_011508 | vertebrates,human | 1 | Reoviridae,Rotavirus,Rotavirus A | seg. 3 | FJ947463 |
| Rotavirus A human/Bethesda/CH5477/1991/G3P[8] | NC_011509 | vertebrates,human | 1 | Reoviridae,Rotavirus,Rotavirus A | seg. 6 | FJ947466 |
| Rotavirus A human/Bethesda/CH5477/1991/G3P[8] | NC_011510 | vertebrates,human | 1 | Reoviridae,Rotavirus,Rotavirus A | seg. 4 | FJ947464 |
| Rotavirus A human/Bethesda/CH5483/1991/G3P[8] | NC_011501 | vertebrates,human | 1 | Reoviridae,Rotavirus,Rotavirus A | seg. 7 | FJ947920 |
| Rotavirus A human/Bethesda/CH5483/1991/G3P[8] | NC_011502 | vertebrates,human | 1 | Reoviridae,Rotavirus,Rotavirus A | seg. 8 | FJ947921 |
| Rotavirus A human/Bethesda/CH5483/1991/G3P[8] | NC_011504 | vertebrates,human | 1 | Reoviridae,Rotavirus,Rotavirus A | seg. 10 | FJ947923 |
| Rotavirus A human/Bethesda/CH5483/1991/G3P[8] | NC_011505 | vertebrates,human | 1 | Reoviridae,Rotavirus,Rotavirus A | seg. 11 | FJ947924 |
| Rotavirus A human/Bethesda/CH5483/1991/G3P[8] | NC_011508 | vertebrates,human | 1 | Reoviridae,Rotavirus,Rotavirus A | seg. 3 | FJ947916 |
| Rotavirus A human/Bethesda/CH5483/1991/G3P[8] | NC_011509 | vertebrates,human | 1 | Reoviridae,Rotavirus,Rotavirus A | seg. 6 | FJ947919 |
| Rotavirus A human/Bethesda/CH5483/1991/G3P[8] | NC_011510 | vertebrates,human | 1 | Reoviridae,Rotavirus,Rotavirus A | seg. 4 | FJ947917 |
| Rotavirus A human/Bethesda/CH5484/1991/G3P[8] | NC_011500 | vertebrates,human | 1 | Reoviridae,Rotavirus,Rotavirus A | seg. 5 | FJ947476 |
| Rotavirus A human/Bethesda/CH5484/1991/G3P[8] | NC_011501 | vertebrates,human | 1 | Reoviridae,Rotavirus,Rotavirus A | seg. 7 | FJ947478 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/CH5484/ 1991/G3P[8] | NC_011502 | vertebrates,human | 1 | Reoviridae,Rotavirus,Rotavirus A | seg. 8 | FJ947479 |
| Rotavirus A human/Bethesda/CH5484/ 1991/G3P[8] | NC_011504 | vertebrates,human | 1 | Reoviridae,Rotavirus,Rotavirus A | seg. 10 | FJ947481 |
| Rotavirus A human/Bethesda/CH5484/ 1991/G3P[8] | NC_011505 | vertebrates,human | 1 | Reoviridae,Rotavirus,Rotavirus A | seg. 11 | FJ947482 |
| Rotavirus A human/Bethesda/CH5484/ 1991/G3P[8] | NC_011508 | vertebrates,human | 1 | Reoviridae,Rotavirus,Rotavirus A | seg. 3 | FJ947474 |
| Rotavirus A human/Bethesda/CH5484/ 1991/G3P[8] | NC_011509 | vertebrates,human | 1 | Reoviridae,Rotavirus,Rotavirus A | seg. 6 | FJ947477 |
| Rotavirus A human/Bethesda/CH5484/ 1991/G3P[8] | NC_011510 | vertebrates,human | 1 | Reoviridae,Rotavirus,Rotavirus A | seg. 4 | FJ947475 |
| Rotavirus A human/Bethesda/CH5488/ 1991/G3P[8] | NC_011500 | vertebrates,human | 1 | Reoviridae,Rotavirus,Rotavirus A | seg. 5 | FJ947487 |
| Rotavirus A human/Bethesda/CH5488/ 1991/G3P[8] | NC_011501 | vertebrates,human | 1 | Reoviridae,Rotavirus,Rotavirus A | seg. 7 | FJ947489 |
| Rotavirus A human/Bethesda/CH5488/ 1991/G3P[8] | NC_011502 | vertebrates,human | 1 | Reoviridae,Rotavirus,Rotavirus A | seg. 8 | FJ947490 |
| Rotavirus A human/Bethesda/CH5488/ 1991/G3P[8] | NC_011504 | vertebrates,human | 1 | Reoviridae,Rotavirus,Rotavirus A | seg. 10 | FJ947492 |
| Rotavirus A human/Bethesda/CH5488/ 1991/G3P[8] | NC_011505 | vertebrates,human | 1 | Reoviridae,Rotavirus,Rotavirus A | seg. 11 | FJ947493 |
| Rotavirus A human/Bethesda/CH5488/ 1991/G3P[8] | NC_011508 | vertebrates,human | 1 | Reoviridae,Rotavirus,Rotavirus A | seg. 3 | FJ947485 |
| Rotavirus A human/Bethesda/CH5488/ 1991/G3P[8] | NC_011509 | vertebrates,human | 1 | Reoviridae,Rotavirus,Rotavirus A | seg. 6 | FJ947488 |
| Rotavirus A human/Bethesda/CH5488/ 1991/G3P[8] | NC_011510 | vertebrates,human | 1 | Reoviridae,Rotavirus,Rotavirus A | seg. 4 | FJ947486 |
| Rotavirus A human/Bethesda/CH5498/ 1991/G3P[8] | NC_011501 | vertebrates,human | 1 | Reoviridae,Rotavirus,Rotavirus A | seg. 7 | FJ947931 |
| Rotavirus A human/Bethesda/CH5498/ 1991/G3P[8] | NC_011502 | vertebrates,human | 1 | Reoviridae,Rotavirus,Rotavirus A | seg. 8 | FJ947932 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/CH5498/1991/G3P[8] | NC_011504 | vertebrates,human | 1 | Reoviridae,Rotavirus,Rotavirus A | seg. 10 | FJ947934 |
| Rotavirus A human/Bethesda/CH5498/1991/G3P[8] | NC_011505 | vertebrates,human | 1 | Reoviridae,Rotavirus,Rotavirus A | seg. 11 | FJ947935 |
| Rotavirus A human/Bethesda/CH5498/1991/G3P[8] | NC_011506 | vertebrates,human | 1 | Reoviridae,Rotavirus,Rotavirus A | seg. 2 | FJ947926 |
| Rotavirus A human/Bethesda/CH5498/1991/G3P[8] | NC_011508 | vertebrates,human | 1 | Reoviridae,Rotavirus,Rotavirus A | seg. 3 | FJ947927 |
| Rotavirus A human/Bethesda/CH5498/1991/G3P[8] | NC_011509 | vertebrates,human | 1 | Reoviridae,Rotavirus,Rotavirus A | seg. 6 | FJ947930 |
| Rotavirus A human/Bethesda/CH5498/1991/G3P[8] | NC_011510 | vertebrates,human | 1 | Reoviridae,Rotavirus,Rotavirus A | seg. 4 | FJ947928 |
| Rotavirus A human/Bethesda/DC1208/1980/G4P[8] | NC_011500 | vertebrates,human | 1 | Reoviridae,Rotavirus,Rotavirus A | seg. 5 | HM773858 |
| Rotavirus A human/Bethesda/DC1208/1980/G4P[8] | NC_011501 | vertebrates,human | 1 | Reoviridae,Rotavirus,Rotavirus A | seg. 7 | HM773860 |
| Rotavirus A human/Bethesda/DC1208/1980/G4P[8] | NC_011502 | vertebrates,human | 1 | Reoviridae,Rotavirus,Rotavirus A | seg. 8 | HM773861 |
| Rotavirus A human/Bethesda/DC1208/1980/G4P[8] | NC_011503 | vertebrates,human | 1 | Reoviridae,Rotavirus,Rotavirus A | seg. 9 | HM773862 |
| Rotavirus A human/Bethesda/DC1208/1980/G4P[8] | NC_011504 | vertebrates,human | 1 | Reoviridae,Rotavirus,Rotavirus A | seg. 10 | HM773863 |
| Rotavirus A human/Bethesda/DC1208/1980/G4P[8] | NC_011505 | vertebrates,human | 1 | Reoviridae,Rotavirus,Rotavirus A | seg. 11 | HM773864 |
| Rotavirus A human/Bethesda/DC1208/1980/G4P[8] | NC_011506 | vertebrates,human | 1 | Reoviridae,Rotavirus,Rotavirus A | seg. 2 | HM773855 |
| Rotavirus A human/Bethesda/DC1208/1980/G4P[8] | NC_011507 | vertebrates,human | 1 | Reoviridae,Rotavirus,Rotavirus A | seg. 1 | HM773854 |
| Rotavirus A human/Bethesda/DC1208/1980/G4P[8] | NC_011508 | vertebrates,human | 1 | Reoviridae,Rotavirus,Rotavirus A | seg. 3 | HM773856 |
| Rotavirus A human/Bethesda/DC1208/1980/G4P[8] | NC_011509 | vertebrates,human | 1 | Reoviridae,Rotavirus,Rotavirus A | seg. 6 | HM773859 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC1208/1980/G4P[8] | NC_011510 | vertebrates,human | 1 | Reoviridae,Rotavirus,Rotavirus A | seg. 4 | HM773857 |
| Rotavirus A human/Bethesda/DC1285/1980/G4P[8] | NC_011500 | vertebrates,human | 1 | Reoviridae,Rotavirus,Rotavirus A | seg. 5 | FJ947168 |
| Rotavirus A human/Bethesda/DC1285/1980/G4P[8] | NC_011501 | vertebrates,human | 1 | Reoviridae,Rotavirus,Rotavirus A | seg. 7 | FJ947170 |
| Rotavirus A human/Bethesda/DC1285/1980/G4P[8] | NC_011502 | vertebrates,human | 1 | Reoviridae,Rotavirus,Rotavirus A | seg. 8 | FJ947171 |
| Rotavirus A human/Bethesda/DC1285/1980/G4P[8] | NC_011503 | vertebrates,human | 1 | Reoviridae,Rotavirus,Rotavirus A | seg. 9 | FJ947172 |
| Rotavirus A human/Bethesda/DC1285/1980/G4P[8] | NC_011504 | vertebrates,human | 1 | Reoviridae,Rotavirus,Rotavirus A | seg. 10 | FJ947173 |
| Rotavirus A human/Bethesda/DC1285/1980/G4P[8] | NC_011505 | vertebrates,human | 1 | Reoviridae,Rotavirus,Rotavirus A | seg. 11 | FJ947174 |
| Rotavirus A human/Bethesda/DC1285/1980/G4P[8] | NC_011506 | vertebrates,human | 1 | Reoviridae,Rotavirus,Rotavirus A | seg. 2 | FJ947165 |
| Rotavirus A human/Bethesda/DC1285/1980/G4P[8] | NC_011507 | vertebrates,human | 1 | Reoviridae,Rotavirus,Rotavirus A | seg. 1 | FJ947164 |
| Rotavirus A human/Bethesda/DC1285/1980/G4P[8] | NC_011508 | vertebrates,human | 1 | Reoviridae,Rotavirus,Rotavirus A | seg. 3 | FJ947166 |
| Rotavirus A human/Bethesda/DC1285/1980/G4P[8] | NC_011509 | vertebrates,human | 1 | Reoviridae,Rotavirus,Rotavirus A | seg. 6 | FJ947169 |
| Rotavirus A human/Bethesda/DC1285/1980/G4P[8] | NC_011510 | vertebrates,human | 1 | Reoviridae,Rotavirus,Rotavirus A | seg. 4 | FJ947167 |
| Rotavirus A human/Bethesda/DC129/1976/G3P[8] | NC_011500 | vertebrates,human | 1 | Reoviridae,Rotavirus,Rotavirus A | seg. 5 | FJ947234 |
| Rotavirus A human/Bethesda/DC129/1976/G3P[8] | NC_011501 | vertebrates,human | 1 | Reoviridae,Rotavirus,Rotavirus A | seg. 7 | FJ947236 |
| Rotavirus A human/Bethesda/DC129/1976/G3P[8] | NC_011502 | vertebrates,human | 1 | Reoviridae,Rotavirus,Rotavirus A | seg. 8 | FJ947237 |
| Rotavirus A human/Bethesda/DC129/1976/G3P[8] | NC_011504 | vertebrates,human | 1 | Reoviridae,Rotavirus,Rotavirus A | seg. 10 | FJ947239 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC129/1976/G3P[8] | NC_011505 | vertebrates,human | 1 | Reoviridae,Rotavirus,Rotavirus A | seg. 11 | FJ947240 |
| Rotavirus A human/Bethesda/DC129/1976/G3P[8] | NC_011506 | vertebrates,human | 1 | Reoviridae,Rotavirus,Rotavirus A | seg. 2 | FJ947231 |
| Rotavirus A human/Bethesda/DC129/1976/G3P[8] | NC_011508 | vertebrates,human | 1 | Reoviridae,Rotavirus,Rotavirus A | seg. 3 | FJ947232 |
| Rotavirus A human/Bethesda/DC129/1976/G3P[8] | NC_011509 | vertebrates,human | 1 | Reoviridae,Rotavirus,Rotavirus A | seg. 6 | FJ947235 |
| Rotavirus A human/Bethesda/DC129/1976/G3P[8] | NC_011510 | vertebrates,human | 1 | Reoviridae,Rotavirus,Rotavirus A | seg. 4 | FJ947233 |
| Rotavirus A human/Bethesda/DC130/1976/G3P[8] | NC_011500 | vertebrates,human | 1 | Reoviridae,Rotavirus,Rotavirus A | seg. 5 | FJ947245 |
| Rotavirus A human/Bethesda/DC130/1976/G3P[8] | NC_011501 | vertebrates,human | 1 | Reoviridae,Rotavirus,Rotavirus A | seg. 7 | FJ947247 |
| Rotavirus A human/Bethesda/DC130/1976/G3P[8] | NC_011502 | vertebrates,human | 1 | Reoviridae,Rotavirus,Rotavirus A | seg. 8 | FJ947248 |
| Rotavirus A human/Bethesda/DC130/1976/G3P[8] | NC_011504 | vertebrates,human | 1 | Reoviridae,Rotavirus,Rotavirus A | seg. 10 | FJ947250 |
| Rotavirus A human/Bethesda/DC130/1976/G3P[8] | NC_011505 | vertebrates,human | 1 | Reoviridae,Rotavirus,Rotavirus A | seg. 11 | FJ947251 |
| Rotavirus A human/Bethesda/DC130/1976/G3P[8] | NC_011506 | vertebrates,human | 1 | Reoviridae,Rotavirus,Rotavirus A | seg. 2 | FJ947242 |
| Rotavirus A human/Bethesda/DC130/1976/G3P[8] | NC_011508 | vertebrates,human | 1 | Reoviridae,Rotavirus,Rotavirus A | seg. 3 | FJ947243 |
| Rotavirus A human/Bethesda/DC130/1976/G3P[8] | NC_011509 | vertebrates,human | 1 | Reoviridae,Rotavirus,Rotavirus A | seg. 6 | FJ947246 |
| Rotavirus A human/Bethesda/DC130/1976/G3P[8] | NC_011510 | vertebrates,human | 1 | Reoviridae,Rotavirus,Rotavirus A | seg. 4 | FJ947244 |
| Rotavirus A human/Bethesda/DC131/1976/G3P[8] | NC_011500 | vertebrates,human | 1 | Reoviridae,Rotavirus,Rotavirus A | seg. 5 | FJ947256 |
| Rotavirus A human/Bethesda/DC131/1976/G3P[8] | NC_011501 | vertebrates,human | 1 | Reoviridae,Rotavirus,Rotavirus A | seg. 7 | FJ947258 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC131/1976/G3P[8] | NC_011502 | vertebrates,human | 1 | Reoviridae,Rotavirus,Rotavirus A | seg. 8 | FJ947259 |
| Rotavirus A human/Bethesda/DC131/1976/G3P[8] | NC_011503 | vertebrates,human | 1 | Reoviridae,Rotavirus,Rotavirus A | seg. 9 | FJ947260 |
| Rotavirus A human/Bethesda/DC131/1976/G3P[8] | NC_011504 | vertebrates,human | 1 | Reoviridae,Rotavirus,Rotavirus A | seg. 10 | FJ947261 |
| Rotavirus A human/Bethesda/DC131/1976/G3P[8] | NC_011505 | vertebrates,human | 1 | Reoviridae,Rotavirus,Rotavirus A | seg. 11 | FJ947262 |
| Rotavirus A human/Bethesda/DC131/1976/G3P[8] | NC_011508 | vertebrates,human | 1 | Reoviridae,Rotavirus,Rotavirus A | seg. 3 | FJ947254 |
| Rotavirus A human/Bethesda/DC131/1976/G3P[8] | NC_011509 | vertebrates,human | 1 | Reoviridae,Rotavirus,Rotavirus A | seg. 6 | FJ947257 |
| Rotavirus A human/Bethesda/DC131/1976/G3P[8] | NC_011510 | vertebrates,human | 1 | Reoviridae,Rotavirus,Rotavirus A | seg. 4 | FJ947255 |
| Rotavirus A human/Bethesda/DC133/1976/G3P[8] | NC_011500 | vertebrates,human | 1 | Reoviridae,Rotavirus,Rotavirus A | seg. 5 | FJ947267 |
| Rotavirus A human/Bethesda/DC133/1976/G3P[8] | NC_011501 | vertebrates,human | 1 | Reoviridae,Rotavirus,Rotavirus A | seg. 7 | FJ947269 |
| Rotavirus A human/Bethesda/DC133/1976/G3P[8] | NC_011502 | vertebrates,human | 1 | Reoviridae,Rotavirus,Rotavirus A | seg. 8 | FJ947270 |
| Rotavirus A human/Bethesda/DC133/1976/G3P[8] | NC_011504 | vertebrates,human | 1 | Reoviridae,Rotavirus,Rotavirus A | seg. 10 | FJ947272 |
| Rotavirus A human/Bethesda/DC133/1976/G3P[8] | NC_011505 | vertebrates,human | 1 | Reoviridae,Rotavirus,Rotavirus A | seg. 11 | FJ947273 |
| Rotavirus A human/Bethesda/DC133/1976/G3P[8] | NC_011506 | vertebrates,human | 1 | Reoviridae,Rotavirus,Rotavirus A | seg. 2 | FJ947264 |
| Rotavirus A human/Bethesda/DC133/1976/G3P[8] | NC_011508 | vertebrates,human | 1 | Reoviridae,Rotavirus,Rotavirus A | seg. 3 | FJ947265 |
| Rotavirus A human/Bethesda/DC133/1976/G3P[8] | NC_011509 | vertebrates,human | 1 | Reoviridae,Rotavirus,Rotavirus A | seg. 6 | FJ947268 |
| Rotavirus A human/Bethesda/DC133/1976/G3P[8] | NC_011510 | vertebrates,human | 1 | Reoviridae,Rotavirus,Rotavirus A | seg. 4 | FJ947266 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC135/1979/G3P[8] | NC_011500 | vertebrates,human | 1 | Reoviridae,Rotavirus,Rotavirus A | seg. 5 | FJ947311

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC1359/1980/G4P[8] | NC_011508 | vertebrates,human | 1 | Reoviridae,Rotavirus,Rotavirus A | seg. 3 | HM773867 |
| Rotavirus A human/Bethesda/DC1359/1980/G4P[8] | NC_011509 | vertebrates,human | 1 | Reoviridae,Rotavirus,Rotavirus A | seg. 6 | HM773870 |
| Rotavirus A human/Bethesda/DC1359/1980/G4P[8] | NC_011510 | vertebrates,human | 1 | Reoviridae,Rotavirus,Rotavirus A | seg. 4 | HM773868 |
| Rotavirus A human/Bethesda/DC139/1976/G3P[8] | NC_011500 | vertebrates,human | 1 | Reoviridae,Rotavirus,Rotavirus A | seg. 5 | FJ947223 |
| Rotavirus A human/Bethesda/DC139/1976/G3P[8] | NC_011501 | vertebrates,human | 1 | Reoviridae,Rotavirus,Rotavirus A | seg. 7 | FJ947225 |
| Rotavirus A human/Bethesda/DC139/1976/G3P[8] | NC_011502 | vertebrates,human | 1 | Reoviridae,Rotavirus,Rotavirus A | seg. 8 | FJ947226 |
| Rotavirus A human/Bethesda/DC139/1976/G3P[8] | NC_011504 | vertebrates,human | 1 | Reoviridae,Rotavirus,Rotavirus A | seg. 10 | FJ947228 |
| Rotavirus A human/Bethesda/DC139/1976/G3P[8] | NC_011505 | vertebrates,human | 1 | Reoviridae,Rotavirus,Rotavirus A | seg. 11 | FJ947229 |
| Rotavirus A human/Bethesda/DC139/1976/G3P[8] | NC_011506 | vertebrates,human | 1 | Reoviridae,Rotavirus,Rotavirus A | seg. 2 | FJ947220 |
| Rotavirus A human/Bethesda/DC139/1976/G3P[8] | NC_011508 | vertebrates,human | 1 | Reoviridae,Rotavirus,Rotavirus A | seg. 3 | FJ947221 |
| Rotavirus A human/Bethesda/DC139/1976/G3P[8] | NC_011509 | vertebrates,human | 1 | Reoviridae,Rotavirus,Rotavirus A | seg. 6 | FJ947224 |
| Rotavirus A human/Bethesda/DC139/1976/G3P[8] | NC_011510 | vertebrates,human | 1 | Reoviridae,Rotavirus,Rotavirus A | seg. 4 | FJ947222 |
| Rotavirus A human/Bethesda/DC140/1975/G3P[8] | NC_011500 | vertebrates,human | 1 | Reoviridae,Rotavirus,Rotavirus A | seg. 5 | FJ947742 |
| Rotavirus A human/Bethesda/DC140/1975/G3P[8] | NC_011501 | vertebrates,human | 1 | Reoviridae,Rotavirus,Rotavirus A | seg. 7 | FJ947744 |
| Rotavirus A human/Bethesda/DC140/1975/G3P[8] | NC_011502 | vertebrates,human | 1 | Reoviridae,Rotavirus,Rotavirus A | seg. 8 | FJ947745 |
| Rotavirus A human/Bethesda/DC140/1975/G3P[8] | NC_011503 | vertebrates,human | 1 | Reoviridae,Rotavirus,Rotavirus A | seg. 9 | FJ947746 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC140/1975/G3P[8] | NC_011504 | vertebrates,human | 1 | Reoviridae,Rotavirus,Rotavirus A | seg. 10 | FJ947747 |
| Rotavirus A human/Bethesda/DC140/1975/G3P[8] | NC_011505 | vertebrates,human | 1 | Reoviridae,Rotavirus,Rotavirus A | seg. 11 | FJ947748 |
| Rotavirus A human/Bethesda/DC140/1975/G3P[8] | NC_011507 | vertebrates,human | 1 | Reoviridae,Rotavirus,Rotavirus A | seg. 1 | FJ947738 |
| Rotavirus A human/Bethesda/DC140/1975/G3P[8] | NC_011508 | vertebrates,human | 1 | Reoviridae,Rotavirus,Rotavirus A | seg. 3 | FJ947740 |
| Rotavirus A human/Bethesda/DC140/1975/G3P[8] | NC_011510 | vertebrates,human | 1 | Reoviridae,Rotavirus,Rotavirus A | seg. 4 | FJ947741 |
| Rotavirus A human/Bethesda/DC1455/1975/G3P[8] | NC_011500 | vertebrates,human | 1 | Reoviridae,Rotavirus,Rotavirus A | seg. 5 | FJ947190 |
| Rotavirus A human/Bethesda/DC1455/1975/G3P[8] | NC_011501 | vertebrates,human | 1 | Reoviridae,Rotavirus,Rotavirus A | seg. 7 | FJ947192 |
| Rotavirus A human/Bethesda/DC1455/1975/G3P[8] | NC_011502 | vertebrates,human | 1 | Reoviridae,Rotavirus,Rotavirus A | seg. 8 | FJ947193 |
| Rotavirus A human/Bethesda/DC1455/1975/G3P[8] | NC_011504 | vertebrates,human | 1 | Reoviridae,Rotavirus,Rotavirus A | seg. 10 | FJ947195 |
| Rotavirus A human/Bethesda/DC1455/1975/G3P[8] | NC_011505 | vertebrates,human | 1 | Reoviridae,Rotavirus,Rotavirus A | seg. 11 | FJ947196 |
| Rotavirus A human/Bethesda/DC1455/1975/G3P[8] | NC_011506 | vertebrates,human | 1 | Reoviridae,Rotavirus,Rotavirus A | seg. 2 | FJ947187 |
| Rotavirus A human/Bethesda/DC1455/1975/G3P[8] | NC_011507 | vertebrates,human | 1 | Reoviridae,Rotavirus,Rotavirus A | seg. 1 | FJ947186 |
| Rotavirus A human/Bethesda/DC1455/1975/G3P[8] | NC_011508 | vertebrates,human | 1 | Reoviridae,Rotavirus,Rotavirus A | seg. 3 | FJ947188 |
| Rotavirus A human/Bethesda/DC1455/1975/G3P[8] | NC_011509 | vertebrates,human | 1 | Reoviridae,Rotavirus,Rotavirus A | seg. 6 | FJ947191 |
| Rotavirus A human/Bethesda/DC1455/1975/G3P[8] | NC_011510 | vertebrates,human | 1 | Reoviridae,Rotavirus,Rotavirus A | seg. 4 | FJ947189 |
| Rotavirus A human/Bethesda/DC1494/1976/G3P[8] | NC_011500 | vertebrates,human | 1 | Reoviridae,Rotavirus,Rotavirus A | seg. 5 | FJ947278 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC1494/ 1976/G3P[8] | NC_011501 | vertebrates,human | 1 | Reoviridae,Rotavirus,Rotavirus A | seg. 7 | FJ947280

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC1496/ 1976/G3P[8] | NC_011510 | vertebrates,human | 1 | Reoviridae,Rotavirus,Rotavirus A | seg. 4 | FJ947288 |
| Rotavirus A human/Bethesda/DC1497/ 1976/G3P[8] | NC_011500 | vertebrates,human | 1 | Reoviridae,Rotavirus,Rotavirus A | seg. 5 | FJ947344 |
| Rotavirus A human/Bethesda/DC1497/ 1976/G3P[8] | NC_011501 | vertebrates,human | 1 | Reoviridae,Rotavirus,Rotavirus A | seg. 7 | FJ947346 |
| Rotavirus A human/Bethesda/DC1497/ 1976/G3P[8] | NC_011502 | vertebrates,human | 1 | Reoviridae,Rotavirus,Rotavirus A | seg. 8 | FJ947347 |
| Rotavirus A human/Bethesda/DC1497/ 1976/G3P[8] | NC_011504 | vertebrates,human | 1 | Reoviridae,Rotavirus,Rotavirus A | seg. 10 | FJ947349 |
| Rotavirus A human/Bethesda/DC1497/ 1976/G3P[8] | NC_011505 | vertebrates,human | 1 | Reoviridae,Rotavirus,Rotavirus A | seg. 11 | FJ947350 |
| Rotavirus A human/Bethesda/DC1497/ 1976/G3P[8] | NC_011507 | vertebrates,human | 1 | Reoviridae,Rotavirus,Rotavirus A | seg. 1 | FJ947340 |
| Rotavirus A human/Bethesda/DC1497/ 1976/G3P[8] | NC_011508 | vertebrates,human | 1 | Reoviridae,Rotavirus,Rotavirus A | seg. 3 | FJ947342 |
| Rotavirus A human/Bethesda/DC1497/ 1976/G3P[8] | NC_011509 | vertebrates,human | 1 | Reoviridae,Rotavirus,Rotavirus A | seg. 6 | FJ947345 |
| Rotavirus A human/Bethesda/DC1497/ 1976/G3P[8] | NC_011510 | vertebrates,human | 1 | Reoviridae,Rotavirus,Rotavirus A | seg. 4 | FJ947343 |
| Rotavirus A human/Bethesda/DC1505/ 1976/G3P[8] | NC_011500 | vertebrates,human | 1 | Reoviridae,Rotavirus,Rotavirus A | seg. 5 | FJ947355 |
| Rotavirus A human/Bethesda/DC1505/ 1976/G3P[8] | NC_011501 | vertebrates,human | 1 | Reoviridae,Rotavirus,Rotavirus A | seg. 7 | FJ947357 |
| Rotavirus A human/Bethesda/DC1505/ 1976/G3P[8] | NC_011502 | vertebrates,human | 1 | Reoviridae,Rotavirus,Rotavirus A | seg. 8 | FJ947358 |
| Rotavirus A human/Bethesda/DC1505/ 1976/G3P[8] | NC_011504 | vertebrates,human | 1 | Reoviridae,Rotavirus,Rotavirus A | seg. 10 | FJ947360 |
| Rotavirus A human/Bethesda/DC1505/ 1976/G3P[8] | NC_011505 | vertebrates,human | 1 | Reoviridae,Rotavirus,Rotavirus A | seg. 11 | FJ947361 |
| Rotavirus A human/Bethesda/DC1505/ 1976/G3P[8] | NC_011507 | vertebrates,human | 1 | Reoviridae,Rotavirus,Rotavirus A | seg. 1 | FJ947351 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC1505/1976/G3P[8] | NC_011508 | vertebrates,human | 1 | Reoviridae,Rotavirus,Rotavirus A | seg. 3 | FJ947353 |
| Rotavirus A human/Bethesda/DC1505/1976/G3P[8] | NC_011509 | vertebrates,human | 1 | Reoviridae,Rotavirus,Rotavirus A | seg. 6 | FJ947356 |
| Rotavirus A human/Bethesda/DC1505/1976/G3P[8] | NC_011510 | vertebrates,human | 1 | Reoviridae,Rotavirus,Rotavirus A | seg. 4 | FJ947354 |
| Rotavirus A human/Bethesda/DC1563/1974/G3P[8] | NC_011500 | vertebrates,human | 1 | Reoviridae,Rotavirus,Rotavirus A | seg. 5 | FJ947179 |
| Rotavirus A human/Bethesda/DC1563/1974/G3P[8] | NC_011501 | vertebrates,human | 1 | Reoviridae,Rotavirus,Rotavirus A | seg. 7 | FJ947181 |
| Rotavirus A human/Bethesda/DC1563/1974/G3P[8] | NC_011502 | vertebrates,human | 1 | Reoviridae,Rotavirus,Rotavirus A | seg. 8 | FJ947182 |
| Rotavirus A human/Bethesda/DC1563/1974/G3P[8] | NC_011504 | vertebrates,human | 1 | Reoviridae,Rotavirus,Rotavirus A | seg. 10 | FJ947184 |
| Rotavirus A human/Bethesda/DC1563/1974/G3P[8] | NC_011505 | vertebrates,human | 1 | Reoviridae,Rotavirus,Rotavirus A | seg. 11 | FJ947185 |
| Rotavirus A human/Bethesda/DC1563/1974/G3P[8] | NC_011506 | vertebrates,human | 1 | Reoviridae,Rotavirus,Rotavirus A | seg. 2 | FJ947176 |
| Rotavirus A human/Bethesda/DC1563/1974/G3P[8] | NC_011508 | vertebrates,human | 1 | Reoviridae,Rotavirus,Rotavirus A | seg. 3 | FJ947177 |
| Rotavirus A human/Bethesda/DC1563/1974/G3P[8] | NC_011509 | vertebrates,human | 1 | Reoviridae,Rotavirus,Rotavirus A | seg. 6 | FJ947180 |
| Rotavirus A human/Bethesda/DC1563/1974/G3P[8] | NC_011510 | vertebrates,human | 1 | Reoviridae,Rotavirus,Rotavirus A | seg. 4 | FJ947178 |
| Rotavirus A human/Bethesda/DC1600/1980/G3P[8] | NC_011500 | vertebrates,human | 1 | Reoviridae,Rotavirus,Rotavirus A | seg. 5 | FJ947775 |
| Rotavirus A human/Bethesda/DC1600/1980/G3P[8] | NC_011501 | vertebrates,human | 1 | Reoviridae,Rotavirus,Rotavirus A | seg. 7 | FJ947777 |
| Rotavirus A human/Bethesda/DC1600/1980/G3P[8] | NC_011502 | vertebrates,human | 1 | Reoviridae,Rotavirus,Rotavirus A | seg. 8 | FJ947778 |
| Rotavirus A human/Bethesda/DC1600/1980/G3P[8] | NC_011504 | vertebrates,human | 1 | Reoviridae,Rotavirus,Rotavirus A | seg. 10 | FJ947780 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC1600/1980/G3P[8] | NC_011505 | vertebrates,human | 1 | Reoviridae,Rotavirus,Rotavirus A | seg. 11 | FJ947781 |
| Rotavirus A human/Bethesda/DC1600/1980/G3P[8] | NC_011506 | vertebrates,human | 1 | Reoviridae,Rotavirus,Rotavirus A | seg. 2 | FJ947772 |
| Rotavirus A human/Bethesda/DC1600/1980/G3P[8] | NC_011507 | vertebrates,human | 1 | Reoviridae,Rotavirus,Rotavirus A | seg. 1 | FJ947771 |
| Rotavirus A human/Bethesda/DC1600/1980/G3P[8] | NC_011508 | vertebrates,human | 1 | Reoviridae,Rotavirus,Rotavirus A | seg. 3 | FJ947773 |
| Rotavirus A human/Bethesda/DC1600/1980/G3P[8] | NC_011509 | vertebrates,human | 1 | Reoviridae,Rotavirus,Rotavirus A | seg. 6 | FJ947776 |
| Rotavirus A human/Bethesda/DC1600/1980/G3P[8] | NC_011510 | vertebrates,human | 1 | Reoviridae,Rotavirus,Rotavirus A | seg. 4 | FJ947774 |
| Rotavirus A human/Bethesda/DC168/1976/G3P[8] | NC_011500 | vertebrates,human | 1 | Reoviridae,Rotavirus,Rotavirus A | seg. 5 | FJ947753 |
| Rotavirus A human/Bethesda/DC168/1976/G3P[8] | NC_011501 | vertebrates,human | 1 | Reoviridae,Rotavirus,Rotavirus A | seg. 7 | FJ947755 |
| Rotavirus A human/Bethesda/DC168/1976/G3P[8] | NC_011502 | vertebrates,human | 1 | Reoviridae,Rotavirus,Rotavirus A | seg. 8 | FJ947756 |
| Rotavirus A human/Bethesda/DC168/1976/G3P[8] | NC_011503 | vertebrates,human | 1 | Reoviridae,Rotavirus,Rotavirus A | seg. 9 | FJ947757 |
| Rotavirus A human/Bethesda/DC168/1976/G3P[8] | NC_011504 | vertebrates,human | 1 | Reoviridae,Rotavirus,Rotavirus A | seg. 10 | FJ947758 |
| Rotavirus A human/Bethesda/DC168/1976/G3P[8] | NC_011505 | vertebrates,human | 1 | Reoviridae,Rotavirus,Rotavirus A | seg. 11 | FJ947759 |
| Rotavirus A human/Bethesda/DC168/1976/G3P[8] | NC_011508 | vertebrates,human | 1 | Reoviridae,Rotavirus,Rotavirus A | seg. 3 | FJ947751 |
| Rotavirus A human/Bethesda/DC168/1976/G3P[8] | NC_011509 | vertebrates,human | 1 | Reoviridae,Rotavirus,Rotavirus A | seg. 6 | FJ947754 |
| Rotavirus A human/Bethesda/DC168/1976/G3P[8] | NC_011510 | vertebrates,human | 1 | Reoviridae,Rotavirus,Rotavirus A | seg. 4 | FJ947752 |
| Rotavirus A human/Bethesda/DC1730/1979/G3P[8] | NC_011500 | vertebrates,human | 1 | Reoviridae,Rotavirus,Rotavirus A | seg. 5 | FJ947322 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC1730/1979/G3P[8] | NC_011501 | vertebrates,human | 1 | Reoviridae,Rotavirus,Rotavirus A | seg. 7 | FJ947324 |
| Rotavirus A human/Bethesda/DC1730/1979/G3P[8] | NC_011502 | vertebrates,human | 1 | Reoviridae,Rotavirus,Rotavirus A | seg. 8 | FJ947325 |
| Rotavirus A human/Bethesda/DC1730/1979/G3P[8] | NC_011504 | vertebrates,human | 1 | Reoviridae,Rotavirus,Rotavirus A | seg. 10 | FJ947327 |
| Rotavirus A human/Bethesda/DC1730/1979/G3P[8] | NC_011505 | vertebrates,human | 1 | Reoviridae,Rotavirus,Rotavirus A | seg. 11 | FJ947328 |
| Rotavirus A human/Bethesda/DC1730/1979/G3P[8] | NC_011509 | vertebrates,human | 1 | Reoviridae,Rotavirus,Rotavirus A | seg. 6 | FJ947323 |
| Rotavirus A human/Bethesda/DC1730/1979/G3P[8] | NC_011510 | vertebrates,human | 1 | Reoviridae,Rotavirus,Rotavirus A | seg. 4 | FJ947321 |
| Rotavirus A human/Bethesda/DC1898/1976/G3P[8] | NC_011500 | vertebrates,human | 1 | Reoviridae,Rotavirus,Rotavirus A | seg. 5 | FJ947300 |
| Rotavirus A human/Bethesda/DC1898/1976/G3P[8] | NC_011501 | vertebrates,human | 1 | Reoviridae,Rotavirus,Rotavirus A | seg. 7 | FJ947302 |
| Rotavirus A human/Bethesda/DC1898/1976/G3P[8] | NC_011502 | vertebrates,human | 1 | Reoviridae,Rotavirus,Rotavirus A | seg. 8 | FJ947303 |
| Rotavirus A human/Bethesda/DC1898/1976/G3P[8] | NC_011504 | vertebrates,human | 1 | Reoviridae,Rotavirus,Rotavirus A | seg. 10 | FJ947305 |
| Rotavirus A human/Bethesda/DC1898/1976/G3P[8] | NC_011505 | vertebrates,human | 1 | Reoviridae,Rotavirus,Rotavirus A | seg. 11 | FJ947306 |
| Rotavirus A human/Bethesda/DC1898/1976/G3P[8] | NC_011508 | vertebrates,human | 1 | Reoviridae,Rotavirus,Rotavirus A | seg. 3 | FJ947298 |
| Rotavirus A human/Bethesda/DC1898/1976/G3P[8] | NC_011509 | vertebrates,human | 1 | Reoviridae,Rotavirus,Rotavirus A | seg. 6 | FJ947301 |
| Rotavirus A human/Bethesda/DC1898/1976/G3P[8] | NC_011510 | vertebrates,human | 1 | Reoviridae,Rotavirus,Rotavirus A | seg. 4 | FJ947299 |
| Rotavirus A human/Bethesda/DC2069/1976/G3P[8] | NC_011500 | vertebrates,human | 1 | Reoviridae,Rotavirus,Rotavirus A | seg. 5 | FJ947808 |
| Rotavirus A human/Bethesda/DC2069/1976/G3P[8] | NC_011501 | vertebrates,human | 1 | Reoviridae,Rotavirus,Rotavirus A | seg. 7 | FJ947810 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC2069/1976/G3P[8] | NC_011502 | vertebrates,human | 1 | Reoviridae,Rotavirus,Rotavirus A | seg. 8 | FJ947811 |
| Rotavirus A human/Bethesda/DC2069/1976/G3P[8] | NC_011504 | vertebrates,human | 1 | Reoviridae,Rotavirus,Rotavirus A | seg. 10 | FJ947813 |
| Rotavirus A human/Bethesda/DC2069/1976/G3P[8] | NC_011505 | vertebrates,human | 1 | Reoviridae,Rotavirus,Rotavirus A | seg. 11 | FJ947814 |
| Rotavirus A human/Bethesda/DC2069/1976/G3P[8] | NC_011507 | vertebrates,human | 1 | Reoviridae,Rotavirus,Rotavirus A | seg. 1 | FJ947804 |
| Rotavirus A human/Bethesda/DC2069/1976/G3P[8] | NC_011508 | vertebrates,human | 1 | Reoviridae,Rotavirus,Rotavirus A | seg. 3 | FJ947806 |
| Rotavirus A human/Bethesda/DC2069/1976/G3P[8] | NC_011509 | vertebrates,human | 1 | Reoviridae,Rotavirus,Rotavirus A | seg. 6 | FJ947809 |
| Rotavirus A human/Bethesda/DC2069/1976/G3P[8] | NC_011510 | vertebrates,human | 1 | Reoviridae,Rotavirus,Rotavirus A | seg. 4 | FJ947807 |
| Rotavirus A human/Bethesda/DC2081/1976/G3P[8] | NC_011500 | vertebrates,human | 1 | Reoviridae,Rotavirus,Rotavirus A | seg. 5 | FJ947819 |
| Rotavirus A human/Bethesda/DC2081/1976/G3P[8] | NC_011501 | vertebrates,human | 1 | Reoviridae,Rotavirus,Rotavirus A | seg. 7 | FJ947821 |
| Rotavirus A human/Bethesda/DC2081/1976/G3P[8] | NC_011502 | vertebrates,human | 1 | Reoviridae,Rotavirus,Rotavirus A | seg. 8 | FJ947822 |
| Rotavirus A human/Bethesda/DC2081/1976/G3P[8] | NC_011504 | vertebrates,human | 1 | Reoviridae,Rotavirus,Rotavirus A | seg. 10 | FJ947824 |
| Rotavirus A human/Bethesda/DC2081/1976/G3P[8] | NC_011505 | vertebrates,human | 1 | Reoviridae,Rotavirus,Rotavirus A | seg. 11 | FJ947825 |
| Rotavirus A human/Bethesda/DC2081/1976/G3P[8] | NC_011508 | vertebrates,human | 1 | Reoviridae,Rotavirus,Rotavirus A | seg. 3 | FJ947817 |
| Rotavirus A human/Bethesda/DC2081/1976/G3P[8] | NC_011509 | vertebrates,human | 1 | Reoviridae,Rotavirus,Rotavirus A | seg. 6 | FJ947820 |
| Rotavirus A human/Bethesda/DC2081/1976/G3P[8] | NC_011510 | vertebrates,human | 1 | Reoviridae,Rotavirus,Rotavirus A | seg. 4 | FJ947818 |
| Rotavirus A human/Bethesda/DC2102/1976/G3P[8] | NC_011500 | vertebrates,human | 1 | Reoviridae,Rotavirus,Rotavirus A | seg. 5 | FJ947830 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC2102/1976/G3P[8] | NC_011501 | vertebrates,human | 1 | Reoviridae,Rotavirus,Rotavirus A | seg. 7 | FJ947832

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC2106/ 1976/G3P[8] | NC_011509 | vertebrates,human | 1 | Reoviridae,Rotavirus,Rotavirus A | seg. 6 | FJ947842 |
| Rotavirus A human/Bethesda/DC2106/ 1976/G3P[8] | NC_011510 | vertebrates,human | 1 | Reoviridae,Rotavirus,Rotavirus A | seg. 4 | FJ947840 |
| Rotavirus A human/Bethesda/DC2109/ 1976/G3P[8] | NC_011500 | vertebrates,human | 1 | Reoviridae,Rotavirus,Rotavirus A | seg. 5 | FJ947377 |
| Rotavirus A human/Bethesda/DC2109/ 1976/G3P[8] | NC_011501 | vertebrates,human | 1 | Reoviridae,Rotavirus,Rotavirus A | seg. 7 | FJ947379 |
| Rotavirus A human/Bethesda/DC2109/ 1976/G3P[8] | NC_011502 | vertebrates,human | 1 | Reoviridae,Rotavirus,Rotavirus A | seg. 8 | FJ947380 |
| Rotavirus A human/Bethesda/DC2109/ 1976/G3P[8] | NC_011504 | vertebrates,human | 1 | Reoviridae,Rotavirus,Rotavirus A | seg. 10 | FJ947382 |
| Rotavirus A human/Bethesda/DC2109/ 1976/G3P[8] | NC_011505 | vertebrates,human | 1 | Reoviridae,Rotavirus,Rotavirus A | seg. 11 | FJ947383 |
| Rotavirus A human/Bethesda/DC2109/ 1976/G3P[8] | NC_011506 | vertebrates,human | 1 | Reoviridae,Rotavirus,Rotavirus A | seg. 2 | FJ947374 |
| Rotavirus A human/Bethesda/DC2109/ 1976/G3P[8] | NC_011509 | vertebrates,human | 1 | Reoviridae,Rotavirus,Rotavirus A | seg. 6 | FJ947378 |
| Rotavirus A human/Bethesda/DC2109/ 1976/G3P[8] | NC_011510 | vertebrates,human | 1 | Reoviridae,Rotavirus,Rotavirus A | seg. 4 | FJ947376 |
| Rotavirus A human/Bethesda/DC2114/ 1976/G3P[8] | NC_011500 | vertebrates,human | 1 | Reoviridae,Rotavirus,Rotavirus A | seg. 5 | FJ947388 |
| Rotavirus A human/Bethesda/DC2114/ 1976/G3P[8] | NC_011501 | vertebrates,human | 1 | Reoviridae,Rotavirus,Rotavirus A | seg. 7 | FJ947390 |
| Rotavirus A human/Bethesda/DC2114/ 1976/G3P[8] | NC_011502 | vertebrates,human | 1 | Reoviridae,Rotavirus,Rotavirus A | seg. 8 | FJ947391 |
| Rotavirus A human/Bethesda/DC2114/ 1976/G3P[8] | NC_011504 | vertebrates,human | 1 | Reoviridae,Rotavirus,Rotavirus A | seg. 10 | FJ947393 |
| Rotavirus A human/Bethesda/DC2114/ 1976/G3P[8] | NC_011505 | vertebrates,human | 1 | Reoviridae,Rotavirus,Rotavirus A | seg. 11 | FJ947394 |
| Rotavirus A human/Bethesda/DC2114/ 1976/G3P[8] | NC_011506 | vertebrates,human | 1 | Reoviridae,Rotavirus,Rotavirus A | seg. 2 | FJ947385 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC2114/1976/G3P[8] | NC_011508 | vertebrates,human | 1 | Reoviridae,Rotavirus,Rotavirus A | seg. 3 | FJ947386 |
| Rotavirus A human/Bethesda/DC2114/1976/G3P[8] | NC_011509 | vertebrates,human | 1 | Reoviridae,Rotavirus,Rotavirus A | seg. 6 | FJ947389 |
| Rotavirus A human/Bethesda/DC2114/1976/G3P[8] | NC_011510 | vertebrates,human | 1 | Reoviridae,Rotavirus,Rotavirus A | seg. 4 | FJ947387 |
| Rotavirus A human/Bethesda/DC2119/1976/G3P[8] | NC_011500 | vertebrates,human | 1 | Reoviridae,Rotavirus,Rotavirus A | seg. 5 | FJ947399 |
| Rotavirus A human/Bethesda/DC2119/1976/G3P[8] | NC_011501 | vertebrates,human | 1 | Reoviridae,Rotavirus,Rotavirus A | seg. 7 | FJ947401 |
| Rotavirus A human/Bethesda/DC2119/1976/G3P[8] | NC_011502 | vertebrates,human | 1 | Reoviridae,Rotavirus,Rotavirus A | seg. 8 | FJ947402 |
| Rotavirus A human/Bethesda/DC2119/1976/G3P[8] | NC_011504 | vertebrates,human | 1 | Reoviridae,Rotavirus,Rotavirus A | seg. 10 | FJ947404 |
| Rotavirus A human/Bethesda/DC2119/1976/G3P[8] | NC_011505 | vertebrates,human | 1 | Reoviridae,Rotavirus,Rotavirus A | seg. 11 | FJ947405 |
| Rotavirus A human/Bethesda/DC2119/1976/G3P[8] | NC_011508 | vertebrates,human | 1 | Reoviridae,Rotavirus,Rotavirus A | seg. 3 | FJ947397 |
| Rotavirus A human/Bethesda/DC2119/1976/G3P[8] | NC_011509 | vertebrates,human | 1 | Reoviridae,Rotavirus,Rotavirus A | seg. 6 | FJ947400 |
| Rotavirus A human/Bethesda/DC2119/1976/G3P[8] | NC_011510 | vertebrates,human | 1 | Reoviridae,Rotavirus,Rotavirus A | seg. 4 | FJ947398 |
| Rotavirus A human/Bethesda/DC2171/1976/G3P[8] | NC_011500 | vertebrates,human | 1 | Reoviridae,Rotavirus,Rotavirus A | seg. 5 | FJ947410 |
| Rotavirus A human/Bethesda/DC2171/1976/G3P[8] | NC_011501 | vertebrates,human | 1 | Reoviridae,Rotavirus,Rotavirus A | seg. 7 | FJ947412 |
| Rotavirus A human/Bethesda/DC2171/1976/G3P[8] | NC_011502 | vertebrates,human | 1 | Reoviridae,Rotavirus,Rotavirus A | seg. 8 | FJ947413 |
| Rotavirus A human/Bethesda/DC2171/1976/G3P[8] | NC_011504 | vertebrates,human | 1 | Reoviridae,Rotavirus,Rotavirus A | seg. 10 | FJ947415 |
| Rotavirus A human/Bethesda/DC2171/1976/G3P[8] | NC_011505 | vertebrates,human | 1 | Reoviridae,Rotavirus,Rotavirus A | seg. 11 | FJ947416 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC2171/1976/G3P[8] | NC_011508 | vertebrates,human | 1 | Reoviridae,Rotavirus,Rotavirus A | seg. 3 | FJ947408 |
| Rotavirus A human/Bethesda/DC2171/1976/G3P[8] | NC_011509 | vertebrates,human | 1 | Reoviridae,Rotavirus,Rotavirus A | seg. 6 | FJ947411 |
| Rotavirus A human/Bethesda/DC2171/1976/G3P[8] | NC_011510 | vertebrates,human | 1 | Reoviridae,Rotavirus,Rotavirus A | seg. 4 | FJ947409 |
| Rotavirus A human/Bethesda/DC2212/1976/G3P[8] | NC_011500 | vertebrates,human | 1 | Reoviridae,Rotavirus,Rotavirus A | seg. 5 | FJ947852 |
| Rotavirus A human/Bethesda/DC2212/1976/G3P[8] | NC_011501 | vertebrates,human | 1 | Reoviridae,Rotavirus,Rotavirus A | seg. 7 | FJ947854 |
| Rotavirus A human/Bethesda/DC2212/1976/G3P[8] | NC_011502 | vertebrates,human | 1 | Reoviridae,Rotavirus,Rotavirus A | seg. 8 | FJ947855 |
| Rotavirus A human/Bethesda/DC2212/1976/G3P[8] | NC_011504 | vertebrates,human | 1 | Reoviridae,Rotavirus,Rotavirus A | seg. 10 | FJ947857 |
| Rotavirus A human/Bethesda/DC2212/1976/G3P[8] | NC_011505 | vertebrates,human | 1 | Reoviridae,Rotavirus,Rotavirus A | seg. 11 | FJ947858 |
| Rotavirus A human/Bethesda/DC2212/1976/G3P[8] | NC_011506 | vertebrates,human | 1 | Reoviridae,Rotavirus,Rotavirus A | seg. 2 | FJ947849 |
| Rotavirus A human/Bethesda/DC2212/1976/G3P[8] | NC_011508 | vertebrates,human | 1 | Reoviridae,Rotavirus,Rotavirus A | seg. 3 | FJ947850 |
| Rotavirus A human/Bethesda/DC2212/1976/G3P[8] | NC_011509 | vertebrates,human | 1 | Reoviridae,Rotavirus,Rotavirus A | seg. 6 | FJ947853 |
| Rotavirus A human/Bethesda/DC2212/1976/G3P[8] | NC_011510 | vertebrates,human | 1 | Reoviridae,Rotavirus,Rotavirus A | seg. 4 | FJ947851 |
| Rotavirus A human/Bethesda/DC2238/1976/G3P[8] | NC_011500 | vertebrates,human | 1 | Reoviridae,Rotavirus,Rotavirus A | seg. 5 | FJ947421 |
| Rotavirus A human/Bethesda/DC2238/1976/G3P[8] | NC_011501 | vertebrates,human | 1 | Reoviridae,Rotavirus,Rotavirus A | seg. 7 | FJ947423 |
| Rotavirus A human/Bethesda/DC2238/1976/G3P[8] | NC_011502 | vertebrates,human | 1 | Reoviridae,Rotavirus,Rotavirus A | seg. 8 | FJ947424 |
| Rotavirus A human/Bethesda/DC2238/1976/G3P[8] | NC_011504 | vertebrates,human | 1 | Reoviridae,Rotavirus,Rotavirus A | seg. 10 | FJ947426 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC2238/1976/G3P[8] | NC_011505 | vertebrates,human | 1 | Reoviridae,Rotavirus,Rotavirus A | seg. 11 | FJ947427 |
| Rotavirus A human/Bethesda/DC2238/1976/G3P[8] | NC_011508 | vertebrates,human | 1 | Reoviridae,Rotavirus,Rotavirus A | seg. 3 | FJ947419 |
| Rotavirus A human/Bethesda/DC2238/1976/G3P[8] | NC_011509 | vertebrates,human | 1 | Reoviridae,Rotavirus,Rotavirus A | seg. 6 | FJ947422 |
| Rotavirus A human/Bethesda/DC2238/1976/G3P[8] | NC_011510 | vertebrates,human | 1 | Reoviridae,Rotavirus,Rotavirus A | seg. 4 | FJ947420 |
| Rotavirus A human/Bethesda/DC2239/1976/G3P[8] | NC_011500 | vertebrates,human | 1 | Reoviridae,Rotavirus,Rotavirus A | seg. 5 | FJ947863 |
| Rotavirus A human/Bethesda/DC2239/1976/G3P[8] | NC_011501 | vertebrates,human | 1 | Reoviridae,Rotavirus,Rotavirus A | seg. 7 | FJ947865 |
| Rotavirus A human/Bethesda/DC2239/1976/G3P[8] | NC_011502 | vertebrates,human | 1 | Reoviridae,Rotavirus,Rotavirus A | seg. 8 | FJ947866 |
| Rotavirus A human/Bethesda/DC2239/1976/G3P[8] | NC_011504 | vertebrates,human | 1 | Reoviridae,Rotavirus,Rotavirus A | seg. 10 | FJ947868 |
| Rotavirus A human/Bethesda/DC2239/1976/G3P[8] | NC_011505 | vertebrates,human | 1 | Reoviridae,Rotavirus,Rotavirus A | seg. 11 | FJ947869 |
| Rotavirus A human/Bethesda/DC2239/1976/G3P[8] | NC_011506 | vertebrates,human | 1 | Reoviridae,Rotavirus,Rotavirus A | seg. 2 | FJ947860 |
| Rotavirus A human/Bethesda/DC2239/1976/G3P[8] | NC_011508 | vertebrates,human | 1 | Reoviridae,Rotavirus,Rotavirus A | seg. 3 | FJ947861 |
| Rotavirus A human/Bethesda/DC2239/1976/G3P[8] | NC_011509 | vertebrates,human | 1 | Reoviridae,Rotavirus,Rotavirus A | seg. 6 | FJ947864 |
| Rotavirus A human/Bethesda/DC2239/1976/G3P[8] | NC_011510 | vertebrates,human | 1 | Reoviridae,Rotavirus,Rotavirus A | seg. 4 | FJ947862 |
| Rotavirus A human/Bethesda/DC2241/1977/G4P[8] | NC_011500 | vertebrates,human | 1 | Reoviridae,Rotavirus,Rotavirus A | seg. 5 | HM773880 |
| Rotavirus A human/Bethesda/DC2241/1977/G4P[8] | NC_011501 | vertebrates,human | 1 | Reoviridae,Rotavirus,Rotavirus A | seg. 7 | HM773882 |
| Rotavirus A human/Bethesda/DC2241/1977/G4P[8] | NC_011502 | vertebrates,human | 1 | Reoviridae,Rotavirus,Rotavirus A | seg. 8 | HM773883 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC2241/1977/G4P[8] | NC_011503 | vertebrates,human | 1 | Reoviridae,Rotavirus,Rotavirus A | seg. 9 | HM773884 |
| Rotavirus A human/Bethesda/DC2241/1977/G4P[8] | NC_011504 | vertebrates,human | 1 | Reoviridae,Rotavirus,Rotavirus A | seg. 10 | HM773885 |
| Rotavirus A human/Bethesda/DC2241/1977/G4P[8] | NC_011505 | vertebrates,human | 1 | Reoviridae,Rotavirus,Rotavirus A | seg. 11 | HM773886 |
| Rotavirus A human/Bethesda/DC2241/1977/G4P[8] | NC_011506 | vertebrates,human | 1 | Reoviridae,Rotavirus,Rotavirus A | seg. 2 | HM773877 |
| Rotavirus A human/Bethesda/DC2241/1977/G4P[8] | NC_011507 | vertebrates,human | 1 | Reoviridae,Rotavirus,Rotavirus A | seg. 1 | HM773876 |
| Rotavirus A human/Bethesda/DC2241/1977/G4P[8] | NC_011508 | vertebrates,human | 1 | Reoviridae,Rotavirus,Rotavirus A | seg. 3 | HM773878 |
| Rotavirus A human/Bethesda/DC2241/1977/G4P[8] | NC_011509 | vertebrates,human | 1 | Reoviridae,Rotavirus,Rotavirus A | seg. 6 | HM773881 |
| Rotavirus A human/Bethesda/DC2241/1977/G4P[8] | NC_011510 | vertebrates,human | 1 | Reoviridae,Rotavirus,Rotavirus A | seg. 4 | HM773879 |
| Rotavirus A human/Bethesda/DC2262/1976/G3P[8] | NC_011500 | vertebrates,human | 1 | Reoviridae,Rotavirus,Rotavirus A | seg. 5 | FJ947874 |
| Rotavirus A human/Bethesda/DC2262/1976/G3P[8] | NC_011501 | vertebrates,human | 1 | Reoviridae,Rotavirus,Rotavirus A | seg. 7 | FJ947876 |
| Rotavirus A human/Bethesda/DC2262/1976/G3P[8] | NC_011502 | vertebrates,human | 1 | Reoviridae,Rotavirus,Rotavirus A | seg. 8 | FJ947877 |
| Rotavirus A human/Bethesda/DC2262/1976/G3P[8] | NC_011504 | vertebrates,human | 1 | Reoviridae,Rotavirus,Rotavirus A | seg. 10 | FJ947879 |
| Rotavirus A human/Bethesda/DC2262/1976/G3P[8] | NC_011505 | vertebrates,human | 1 | Reoviridae,Rotavirus,Rotavirus A | seg. 11 | FJ947880 |
| Rotavirus A human/Bethesda/DC2262/1976/G3P[8] | NC_011506 | vertebrates,human | 1 | Reoviridae,Rotavirus,Rotavirus A | seg. 2 | FJ947871 |
| Rotavirus A human/Bethesda/DC2262/1976/G3P[8] | NC_011508 | vertebrates,human | 1 | Reoviridae,Rotavirus,Rotavirus A | seg. 3 | FJ947872 |
| Rotavirus A human/Bethesda/DC2262/1976/G3P[8] | NC_011509 | vertebrates,human | 1 | Reoviridae,Rotavirus,Rotavirus A | seg. 6 | FJ947875 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC2262/1976/G3P[8] | NC_011510 | vertebrates,human | 1 | Reoviridae,Rotavirus,Rotavirus A | seg. 4 | FJ947873 |
| Rotavirus A human/Bethesda/DC2266/1976/G3P[8] | NC_011500 | vertebrates,human | 1 | Reoviridae,Rotavirus,Rotavirus A | seg. 5 | FJ947885 |
| Rotavirus A human/Bethesda/DC2266/1976/G3P[8] | NC_011501 | vertebrates,human | 1 | Reoviridae,Rotavirus,Rotavirus A | seg. 7 | FJ947887 |
| Rotavirus A human/Bethesda/DC2266/1976/G3P[8] | NC_011502 | vertebrates,human | 1 | Reoviridae,Rotavirus,Rotavirus A | seg. 8 | FJ947888 |
| Rotavirus A human/Bethesda/DC2266/1976/G3P[8] | NC_011504 | vertebrates,human | 1 | Reoviridae,Rotavirus,Rotavirus A | seg. 10 | FJ947890 |
| Rotavirus A human/Bethesda/DC2266/1976/G3P[8] | NC_011505 | vertebrates,human | 1 | Reoviridae,Rotavirus,Rotavirus A | seg. 11 | FJ947891 |
| Rotavirus A human/Bethesda/DC2266/1976/G3P[8] | NC_011508 | vertebrates,human | 1 | Reoviridae,Rotavirus,Rotavirus A | seg. 3 | FJ947883 |
| Rotavirus A human/Bethesda/DC2266/1976/G3P[8] | NC_011509 | vertebrates,human | 1 | Reoviridae,Rotavirus,Rotavirus A | seg. 6 | FJ947886 |
| Rotavirus A human/Bethesda/DC2266/1976/G3P[8] | NC_011510 | vertebrates,human | 1 | Reoviridae,Rotavirus,Rotavirus A | seg. 4 | FJ947884 |
| Rotavirus A human/Bethesda/DC23/1976/G3P[8] | NC_011500 | vertebrates,human | 1 | Reoviridae,Rotavirus,Rotavirus A | seg. 5 | FJ947212 |
| Rotavirus A human/Bethesda/DC23/1976/G3P[8] | NC_011501 | vertebrates,human | 1 | Reoviridae,Rotavirus,Rotavirus A | seg. 7 | FJ947214 |
| Rotavirus A human/Bethesda/DC23/1976/G3P[8] | NC_011502 | vertebrates,human | 1 | Reoviridae,Rotavirus,Rotavirus A | seg. 8 | FJ947215 |
| Rotavirus A human/Bethesda/DC23/1976/G3P[8] | NC_011503 | vertebrates,human | 1 | Reoviridae,Rotavirus,Rotavirus A | seg. 9 | FJ947216 |
| Rotavirus A human/Bethesda/DC23/1976/G3P[8] | NC_011504 | vertebrates,human | 1 | Reoviridae,Rotavirus,Rotavirus A | seg. 10 | FJ947217 |
| Rotavirus A human/Bethesda/DC23/1976/G3P[8] | NC_011505 | vertebrates,human | 1 | Reoviridae,Rotavirus,Rotavirus A | seg. 11 | FJ947218 |
| Rotavirus A human/Bethesda/DC23/1976/G3P[8] | NC_011507 | vertebrates,human | 1 | Reoviridae,Rotavirus,Rotavirus A | seg. 1 | FJ947208 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC23/19 76/G3P[8] | NC_011509 | vertebrates,human | 1 | Reoviridae,Rotavirus,Rotavirus A | seg. 6 | FJ947213 |
| Rotavirus A human/Bethesda/DC23/19 76/G3P[8] | NC_011510 | vertebrates,human | 1 | Reoviridae,Rotavirus,Rotavirus A | seg. 4 | FJ947211 |
| Rotavirus A human/Bethesda/DC4320/ 1988/G4P[8] | NC_011500 | vertebrates,human | 1 | Reoviridae,Rotavirus,Rotavirus A | seg. 5 | HM773891 |
| Rotavirus A human/Bethesda/DC4320/ 1988/G4P[8] | NC_011501 | vertebrates,human | 1 | Reoviridae,Rotavirus,Rotavirus A | seg. 7 | HM773893 |
| Rotavirus A human/Bethesda/DC4320/ 1988/G4P[8] | NC_011502 | vertebrates,human | 1 | Reoviridae,Rotavirus,Rotavirus A | seg. 8 | HM773894 |
| Rotavirus A human/Bethesda/DC4320/ 1988/G4P[8] | NC_011503 | vertebrates,human | 1 | Reoviridae,Rotavirus,Rotavirus A | seg. 9 | HM773895 |
| Rotavirus A human/Bethesda/DC4320/ 1988/G4P[8] | NC_011504 | vertebrates,human | 1 | Reoviridae,Rotavirus,Rotavirus A | seg. 10 | HM773896 |
| Rotavirus A human/Bethesda/DC4320/ 1988/G4P[8] | NC_011505 | vertebrates,human | 1 | Reoviridae,Rotavirus,Rotavirus A | seg. 11 | HM773897 |
| Rotavirus A human/Bethesda/DC4320/ 1988/G4P[8] | NC_011506 | vertebrates,human | 1 | Reoviridae,Rotavirus,Rotavirus A | seg. 2 | HM773888 |
| Rotavirus A human/Bethesda/DC4320/ 1988/G4P[8] | NC_011507 | vertebrates,human | 1 | Reoviridae,Rotavirus,Rotavirus A | seg. 1 | HM773887 |
| Rotavirus A human/Bethesda/DC4320/ 1988/G4P[8] | NC_011508 | vertebrates,human | 1 | Reoviridae,Rotavirus,Rotavirus A | seg. 3 | HM773889 |
| Rotavirus A human/Bethesda/DC4320/ 1988/G4P[8] | NC_011509 | vertebrates,human | 1 | Reoviridae,Rotavirus,Rotavirus A | seg. 6 | HM773892 |
| Rotavirus A human/Bethesda/DC4320/ 1988/G4P[8] | NC_011510 | vertebrates,human | 1 | Reoviridae,Rotavirus,Rotavirus A | seg. 4 | HM773890 |
| Rotavirus A human/Bethesda/DC4608/ 1980/G4P[8] | NC_011500 | vertebrates,human | 1 | Reoviridae,Rotavirus,Rotavirus A | seg. 5 | HM773902 |
| Rotavirus A human/Bethesda/DC4608/ 1980/G4P[8] | NC_011501 | vertebrates,human | 1 | Reoviridae,Rotavirus,Rotavirus A | seg. 7 | HM773904 |
| Rotavirus A human/Bethesda/DC4608/ 1980/G4P[8] | NC_011502 | vertebrates,human | 1 | Reoviridae,Rotavirus,Rotavirus A | seg. 8 | HM773905 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC4608/1980/G4P[8] | NC_011503 | vertebrates,human | 1 | Reoviridae,Rotavirus,Rotavirus A | seg. 9 | HM773906 |
| Rotavirus A human/Bethesda/DC4608/1980/G4P[8] | NC_011504 | vertebrates,human | 1 | Reoviridae,Rotavirus,Rotavirus A | seg. 10 | HM773907 |
| Rotavirus A human/Bethesda/DC4608/1980/G4P[8] | NC_011505 | vertebrates,human | 1 | Reoviridae,Rotavirus,Rotavirus A | seg. 11 | HM773908 |
| Rotavirus A human/Bethesda/DC4608/1980/G4P[8] | NC_011506 | vertebrates,human | 1 | Reoviridae,Rotavirus,Rotavirus A | seg. 2 | HM773899 |
| Rotavirus A human/Bethesda/DC4608/1980/G4P[8] | NC_011507 | vertebrates,human | 1 | Reoviridae,Rotavirus,Rotavirus A | seg. 1 | HM773898 |
| Rotavirus A human/Bethesda/DC4608/1980/G4P[8] | NC_011508 | vertebrates,human | 1 | Reoviridae,Rotavirus,Rotavirus A | seg. 3 | HM773900 |
| Rotavirus A human/Bethesda/DC4608/1980/G4P[8] | NC_011509 | vertebrates,human | 1 | Reoviridae,Rotavirus,Rotavirus A | seg. 6 | HM773903 |
| Rotavirus A human/Bethesda/DC4608/1980/G4P[8] | NC_011510 | vertebrates,human | 1 | Reoviridae,Rotavirus,Rotavirus A | seg. 4 | HM773901 |
| Rotavirus A human/Bethesda/DC4608/1980/G4P[8] | NC_011500 | vertebrates,human | 1 | Reoviridae,Rotavirus,Rotavirus A | seg. 5 | HM773913 |
| Rotavirus A human/Bethesda/DC4613/1980/G4P[8] | NC_011501 | vertebrates,human | 1 | Reoviridae,Rotavirus,Rotavirus A | seg. 7 | HM773915 |
| Rotavirus A human/Bethesda/DC4613/1980/G4P[8] | NC_011502 | vertebrates,human | 1 | Reoviridae,Rotavirus,Rotavirus A | seg. 8 | HM773916 |
| Rotavirus A human/Bethesda/DC4613/1980/G4P[8] | NC_011503 | vertebrates,human | 1 | Reoviridae,Rotavirus,Rotavirus A | seg. 9 | HM773917 |
| Rotavirus A human/Bethesda/DC4613/1980/G4P[8] | NC_011504 | vertebrates,human | 1 | Reoviridae,Rotavirus,Rotavirus A | seg. 10 | HM773918 |
| Rotavirus A human/Bethesda/DC4613/1980/G4P[8] | NC_011505 | vertebrates,human | 1 | Reoviridae,Rotavirus,Rotavirus A | seg. 11 | HM773919 |
| Rotavirus A human/Bethesda/DC4613/1980/G4P[8] | NC_011506 | vertebrates,human | 1 | Reoviridae,Rotavirus,Rotavirus A | seg. 2 | HM773910 |
| Rotavirus A human/Bethesda/DC4613/1980/G4P[8] | NC_011507 | vertebrates,human | 1 | Reoviridae,Rotavirus,Rotavirus A | seg. 1 | HM773909 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC4613/1980/G4P[8] | NC_011508 | vertebrates,human | 1 | Reoviridae,Rotavirus,Rotavirus A | seg. 3 | HM773911 |
| Rotavirus A human/Bethesda/DC4613/1980/G4P[8] | NC_011509 | vertebrates,human | 1 | Reoviridae,Rotavirus,Rotavirus A | seg. 6 | HM773914 |
| Rotavirus A human/Bethesda/DC4613/1980/G4P[8] | NC_011510 | vertebrates,human | 1 | Reoviridae,Rotavirus,Rotavirus A | seg. 4 | HM773912 |
| Rotavirus A human/Bethesda/DC4772/1976/G3P[8] | NC_011500 | vertebrates,human | 1 | Reoviridae,Rotavirus,Rotavirus A | seg. 5 | FJ947366 |
| Rotavirus A human/Bethesda/DC4772/1976/G3P[8] | NC_011501 | vertebrates,human | 1 | Reoviridae,Rotavirus,Rotavirus A | seg. 7 | FJ947368 |
| Rotavirus A human/Bethesda/DC4772/1976/G3P[8] | NC_011502 | vertebrates,human | 1 | Reoviridae,Rotavirus,Rotavirus A | seg. 8 | FJ947369 |
| Rotavirus A human/Bethesda/DC4772/1976/G3P[8] | NC_011504 | vertebrates,human | 1 | Reoviridae,Rotavirus,Rotavirus A | seg. 10 | FJ947371 |
| Rotavirus A human/Bethesda/DC4772/1976/G3P[8] | NC_011505 | vertebrates,human | 1 | Reoviridae,Rotavirus,Rotavirus A | seg. 11 | FJ947372 |
| Rotavirus A human/Bethesda/DC4772/1976/G3P[8] | NC_011506 | vertebrates,human | 1 | Reoviridae,Rotavirus,Rotavirus A | seg. 2 | FJ947363 |
| Rotavirus A human/Bethesda/DC4772/1976/G3P[8] | NC_011507 | vertebrates,human | 1 | Reoviridae,Rotavirus,Rotavirus A | seg. 1 | FJ947362 |
| Rotavirus A human/Bethesda/DC4772/1976/G3P[8] | NC_011508 | vertebrates,human | 1 | Reoviridae,Rotavirus,Rotavirus A | seg. 3 | FJ947364 |
| Rotavirus A human/Bethesda/DC4772/1976/G3P[8] | NC_011509 | vertebrates,human | 1 | Reoviridae,Rotavirus,Rotavirus A | seg. 6 | FJ947367 |
| Rotavirus A human/Bethesda/DC4772/1976/G3P[8] | NC_011510 | vertebrates,human | 1 | Reoviridae,Rotavirus,Rotavirus A | seg. 4 | FJ947365 |
| Rotavirus A human/Bethesda/DC4996/1977/G4P[8] | NC_011500 | vertebrates,human | 1 | Reoviridae,Rotavirus,Rotavirus A | seg. 5 | HM773924 |
| Rotavirus A human/Bethesda/DC4996/1977/G4P[8] | NC_011501 | vertebrates,human | 1 | Reoviridae,Rotavirus,Rotavirus A | seg. 7 | HM773926 |
| Rotavirus A human/Bethesda/DC4996/1977/G4P[8] | NC_011502 | vertebrates,human | 1 | Reoviridae,Rotavirus,Rotavirus A | seg. 8 | HM773927 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC4996/1977/G4P[8] | NC_011503 | vertebrates,human | 1 | Reoviridae,Rotavirus,Rotavirus A | seg. 9 | HM773928 |
| Rotavirus A human/Bethesda/DC4996/1977/G4P[8] | NC_011504 | vertebrates,human | 1 | Reoviridae,Rotavirus,Rotavirus A | seg. 10 | HM773929 |
| Rotavirus A human/Bethesda/DC4996/1977/G4P[8] | NC_011505 | vertebrates,human | 1 | Reoviridae,Rotavirus,Rotavirus A | seg. 11 | HM773930 |
| Rotavirus A human/Bethesda/DC4996/1977/G4P[8] | NC_011506 | vertebrates,human | 1 | Reoviridae,Rotavirus,Rotavirus A | seg. 2 | HM773921 |
| Rotavirus A human/Bethesda/DC4996/1977/G4P[8] | NC_011507 | vertebrates,human | 1 | Reoviridae,Rotavirus,Rotavirus A | seg. 1 | HM773920 |
| Rotavirus A human/Bethesda/DC4996/1977/G4P[8] | NC_011508 | vertebrates,human | 1 | Reoviridae,Rotavirus,Rotavirus A | seg. 3 | HM773922 |
| Rotavirus A human/Bethesda/DC4996/1977/G4P[8] | NC_011509 | vertebrates,human | 1 | Reoviridae,Rotavirus,Rotavirus A | seg. 6 | HM773925 |
| Rotavirus A human/Bethesda/DC4996/1977/G4P[8] | NC_011510 | vertebrates,human | 1 | Reoviridae,Rotavirus,Rotavirus A | seg. 4 | HM773923 |
| Rotavirus A human/Bethesda/DC5064/1977/G4P[8] | NC_011500 | vertebrates,human | 1 | Reoviridae,Rotavirus,Rotavirus A | seg. 5 | HM773935 |
| Rotavirus A human/Bethesda/DC5064/1977/G4P[8] | NC_011501 | vertebrates,human | 1 | Reoviridae,Rotavirus,Rotavirus A | seg. 7 | HM773937 |
| Rotavirus A human/Bethesda/DC5064/1977/G4P[8] | NC_011502 | vertebrates,human | 1 | Reoviridae,Rotavirus,Rotavirus A | seg. 8 | HM773938 |
| Rotavirus A human/Bethesda/DC5064/1977/G4P[8] | NC_011503 | vertebrates,human | 1 | Reoviridae,Rotavirus,Rotavirus A | seg. 9 | HM773939 |
| Rotavirus A human/Bethesda/DC5064/1977/G4P[8] | NC_011504 | vertebrates,human | 1 | Reoviridae,Rotavirus,Rotavirus A | seg. 10 | HM773940 |
| Rotavirus A human/Bethesda/DC5064/1977/G4P[8] | NC_011505 | vertebrates,human | 1 | Reoviridae,Rotavirus,Rotavirus A | seg. 11 | HM773941 |
| Rotavirus A human/Bethesda/DC5064/1977/G4P[8] | NC_011506 | vertebrates,human | 1 | Reoviridae,Rotavirus,Rotavirus A | seg. 2 | HM773932 |
| Rotavirus A human/Bethesda/DC5064/1977/G4P[8] | NC_011507 | vertebrates,human | 1 | Reoviridae,Rotavirus,Rotavirus A | seg. 1 | HM773931 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC5064/1977/G4P[8] | NC_011508 | vertebrates,human | 1 | Reoviridae,Rotavirus,Rotavirus A | seg. 3 | HM773933 |
| Rotavirus A human/Bethesda/DC5064/1977/G4P[8] | NC_011509 | vertebrates,human | 1 | Reoviridae,Rotavirus,Rotavirus A | seg. 6 | HM773936 |
| Rotavirus A human/Bethesda/DC5064/1977/G4P[8] | NC_011510 | vertebrates,human | 1 | Reoviridae,Rotavirus,Rotavirus A | seg. 4 | HM773934 |
| Rotavirus A human/Bethesda/DC5115/1977/G4P[8] | NC_011500 | vertebrates,human | 1 | Reoviridae,Rotavirus,Rotavirus A | seg. 5 | HM773946 |
| Rotavirus A human/Bethesda/DC5115/1977/G4P[8] | NC_011501 | vertebrates,human | 1 | Reoviridae,Rotavirus,Rotavirus A | seg. 7 | HM773948 |
| Rotavirus A human/Bethesda/DC5115/1977/G4P[8] | NC_011502 | vertebrates,human | 1 | Reoviridae,Rotavirus,Rotavirus A | seg. 8 | HM773949 |
| Rotavirus A human/Bethesda/DC5115/1977/G4P[8] | NC_011503 | vertebrates,human | 1 | Reoviridae,Rotavirus,Rotavirus A | seg. 9 | HM773950 |
| Rotavirus A human/Bethesda/DC5115/1977/G4P[8] | NC_011504 | vertebrates,human | 1 | Reoviridae,Rotavirus,Rotavirus A | seg. 10 | HM773951 |
| Rotavirus A human/Bethesda/DC5115/1977/G4P[8] | NC_011505 | vertebrates,human | 1 | Reoviridae,Rotavirus,Rotavirus A | seg. 11 | HM773952 |
| Rotavirus A human/Bethesda/DC5115/1977/G4P[8] | NC_011506 | vertebrates,human | 1 | Reoviridae,Rotavirus,Rotavirus A | seg. 2 | HM773943 |
| Rotavirus A human/Bethesda/DC5115/1977/G4P[8] | NC_011507 | vertebrates,human | 1 | Reoviridae,Rotavirus,Rotavirus A | seg. 1 | HM773942 |
| Rotavirus A human/Bethesda/DC5115/1977/G4P[8] | NC_011508 | vertebrates,human | 1 | Reoviridae,Rotavirus,Rotavirus A | seg. 3 | HM773944 |
| Rotavirus A human/Bethesda/DC5115/1977/G4P[8] | NC_011509 | vertebrates,human | 1 | Reoviridae,Rotavirus,Rotavirus A | seg. 6 | HM773947 |
| Rotavirus A human/Bethesda/DC5115/1977/G4P[8] | NC_011510 | vertebrates,human | 1 | Reoviridae,Rotavirus,Rotavirus A | seg. 4 | HM773945 |
| Rotavirus A human/Bethesda/DC5142/1975/G3P[8] | NC_011500 | vertebrates,human | 1 | Reoviridae,Rotavirus,Rotavirus A | seg. 5 | FJ947201 |
| Rotavirus A human/Bethesda/DC5142/1975/G3P[8] | NC_011501 | vertebrates,human | 1 | Reoviridae,Rotavirus,Rotavirus A | seg. 7 | FJ947203 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC5142/1975/G3P[8] | NC_011502 | vertebrates,human | 1 | Reoviridae,Rotavirus,Rotavirus A | seg. 8 | FJ947204 |
| Rotavirus A human/Bethesda/DC5142/1975/G3P[8] | NC_011503 | vertebrates,human | 1 | Reoviridae,Rotavirus,Rotavirus A | seg. 9 | FJ947205 |
| Rotavirus A human/Bethesda/DC5142/1975/G3P[8] | NC_011504 | vertebrates,human | 1 | Reoviridae,Rotavirus,Rotavirus A | seg. 10 | FJ947206 |
| Rotavirus A human/Bethesda/DC5142/1975/G3P[8] | NC_011505 | vertebrates,human | 1 | Reoviridae,Rotavirus,Rotavirus A | seg. 11 | FJ947207 |
| Rotavirus A human/Bethesda/DC5142/1975/G3P[8] | NC_011507 | vertebrates,human | 1 | Reoviridae,Rotavirus,Rotavirus A | seg. 1 | FJ947197 |
| Rotavirus A human/Bethesda/DC5142/1975/G3P[8] | NC_011508 | vertebrates,human | 1 | Reoviridae,Rotavirus,Rotavirus A | seg. 3 | FJ947199 |
| Rotavirus A human/Bethesda/DC5142/1975/G3P[8] | NC_011509 | vertebrates,human | 1 | Reoviridae,Rotavirus,Rotavirus A | seg. 6 | FJ947202 |
| Rotavirus A human/Bethesda/DC5142/1975/G3P[8] | NC_011510 | vertebrates,human | 1 | Reoviridae,Rotavirus,Rotavirus A | seg. 4 | FJ947200 |
| Rotavirus A human/Bethesda/DC5491/1991/G3P[8] | NC_011500 | vertebrates,human | 1 | Reoviridae,Rotavirus,Rotavirus A | seg. 5 | FJ947498 |
| Rotavirus A human/Bethesda/DC5491/1991/G3P[8] | NC_011501 | vertebrates,human | 1 | Reoviridae,Rotavirus,Rotavirus A | seg. 7 | FJ947500 |
| Rotavirus A human/Bethesda/DC5491/1991/G3P[8] | NC_011502 | vertebrates,human | 1 | Reoviridae,Rotavirus,Rotavirus A | seg. 8 | FJ947501 |
| Rotavirus A human/Bethesda/DC5491/1991/G3P[8] | NC_011504 | vertebrates,human | 1 | Reoviridae,Rotavirus,Rotavirus A | seg. 10 | FJ947503 |
| Rotavirus A human/Bethesda/DC5491/1991/G3P[8] | NC_011505 | vertebrates,human | 1 | Reoviridae,Rotavirus,Rotavirus A | seg. 11 | FJ947504 |
| Rotavirus A human/Bethesda/DC5491/1991/G3P[8] | NC_011506 | vertebrates,human | 1 | Reoviridae,Rotavirus,Rotavirus A | seg. 2 | FJ947495 |
| Rotavirus A human/Bethesda/DC5491/1991/G3P[8] | NC_011508 | vertebrates,human | 1 | Reoviridae,Rotavirus,Rotavirus A | seg. 3 | FJ947496 |
| Rotavirus A human/Bethesda/DC5491/1991/G3P[8] | NC_011509 | vertebrates,human | 1 | Reoviridae,Rotavirus,Rotavirus A | seg. 6 | FJ947499 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC5491/ 1991/G3P[8] | NC_011510 | vertebrates,human | 1 | Reoviridae,Rotavirus,Rotavirus A | seg. 4 | FJ947497 |
| Rotavirus A human/Bethesda/DC5544/ 1991/G3P[8] | NC_011500 | vertebrates,human | 1 | Reoviridae,Rotavirus,Rotavirus A | seg. 5 | FJ947509 |
| Rotavirus A human/Bethesda/DC5544/ 1991/G3P[8] | NC_011501 | vertebrates,human | 1 | Reoviridae,Rotavirus,Rotavirus A | seg. 7 | FJ947511 |
| Rotavirus A human/Bethesda/DC5544/ 1991/G3P[8] | NC_011502 | vertebrates,human | 1 | Reoviridae,Rotavirus,Rotavirus A | seg. 8 | FJ947512 |
| Rotavirus A human/Bethesda/DC5544/ 1991/G3P[8] | NC_011504 | vertebrates,human | 1 | Reoviridae,Rotavirus,Rotavirus A | seg. 10 | FJ947514 |
| Rotavirus A human/Bethesda/DC5544/ 1991/G3P[8] | NC_011505 | vertebrates,human | 1 | Reoviridae,Rotavirus,Rotavirus A | seg. 11 | FJ947515 |
| Rotavirus A human/Bethesda/DC5544/ 1991/G3P[8] | NC_011506 | vertebrates,human | 1 | Reoviridae,Rotavirus,Rotavirus A | seg. 2 | FJ947506 |
| Rotavirus A human/Bethesda/DC5544/ 1991/G3P[8] | NC_011507 | vertebrates,human | 1 | Reoviridae,Rotavirus,Rotavirus A | seg. 1 | FJ947505 |
| Rotavirus A human/Bethesda/DC5544/ 1991/G3P[8] | NC_011508 | vertebrates,human | 1 | Reoviridae,Rotavirus,Rotavirus A | seg. 3 | FJ947507 |
| Rotavirus A human/Bethesda/DC5544/ 1991/G3P[8] | NC_011509 | vertebrates,human | 1 | Reoviridae,Rotavirus,Rotavirus A | seg. 6 | FJ947510 |
| Rotavirus A human/Bethesda/DC5544/ 1991/G3P[8] | NC_011510 | vertebrates,human | 1 | Reoviridae,Rotavirus,Rotavirus A | seg. 4 | FJ947508 |
| Rotavirus A human/Bethesda/DC5549/ 1991/G3P[8] | NC_011500 | vertebrates,human | 1 | Reoviridae,Rotavirus,Rotavirus A | seg. 5 | FJ947520 |
| Rotavirus A human/Bethesda/DC5549/ 1991/G3P[8] | NC_011501 | vertebrates,human | 1 | Reoviridae,Rotavirus,Rotavirus A | seg. 7 | FJ947522 |
| Rotavirus A human/Bethesda/DC5549/ 1991/G3P[8] | NC_011502 | vertebrates,human | 1 | Reoviridae,Rotavirus,Rotavirus A | seg. 8 | FJ947523 |
| Rotavirus A human/Bethesda/DC5549/ 1991/G3P[8] | NC_011504 | vertebrates,human | 1 | Reoviridae,Rotavirus,Rotavirus A | seg. 10 | FJ947525 |
| Rotavirus A human/Bethesda/DC5549/ 1991/G3P[8] | NC_011505 | vertebrates,human | 1 | Reoviridae,Rotavirus,Rotavirus A | seg. 11 | FJ947526 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC5549/1991/G3P[8] | NC_011506 | vertebrates,human | 1 | Reoviridae,Rotavirus,Rotavirus A | seg. 2 | FJ947517 |
| Rotavirus A human/Bethesda/DC5549/1991/G3P[8] | NC_011507 | vertebrates,human | 1 | Reoviridae,Rotavirus,Rotavirus A | seg. 1 | FJ947516 |
| Rotavirus A human/Bethesda/DC5549/1991/G3P[8] | NC_011508 | vertebrates,human | 1 | Reoviridae,Rotavirus,Rotavirus A | seg. 3 | FJ947518 |
| Rotavirus A human/Bethesda/DC5549/1991/G3P[8] | NC_011509 | vertebrates,human | 1 | Reoviridae,Rotavirus,Rotavirus A | seg. 6 | FJ947521 |
| Rotavirus A human/Bethesda/DC5549/1991/G3P[8] | NC_011510 | vertebrates,human | 1 | Reoviridae,Rotavirus,Rotavirus A | seg. 4 | FJ947519 |
| Rotavirus A human/Bethesda/DC5553/1991/G3P[8] | NC_011500 | vertebrates,human | 1 | Reoviridae,Rotavirus,Rotavirus A | seg. 5 | FJ947940 |
| Rotavirus A human/Bethesda/DC5553/1991/G3P[8] | NC_011501 | vertebrates,human | 1 | Reoviridae,Rotavirus,Rotavirus A | seg. 7 | FJ947942 |
| Rotavirus A human/Bethesda/DC5553/1991/G3P[8] | NC_011502 | vertebrates,human | 1 | Reoviridae,Rotavirus,Rotavirus A | seg. 8 | FJ947943 |
| Rotavirus A human/Bethesda/DC5553/1991/G3P[8] | NC_011504 | vertebrates,human | 1 | Reoviridae,Rotavirus,Rotavirus A | seg. 10 | FJ947945 |
| Rotavirus A human/Bethesda/DC5553/1991/G3P[8] | NC_011505 | vertebrates,human | 1 | Reoviridae,Rotavirus,Rotavirus A | seg. 11 | FJ947946 |
| Rotavirus A human/Bethesda/DC5553/1991/G3P[8] | NC_011506 | vertebrates,human | 1 | Reoviridae,Rotavirus,Rotavirus A | seg. 2 | FJ947937 |
| Rotavirus A human/Bethesda/DC5553/1991/G3P[8] | NC_011507 | vertebrates,human | 1 | Reoviridae,Rotavirus,Rotavirus A | seg. 1 | FJ947936 |
| Rotavirus A human/Bethesda/DC5553/1991/G3P[8] | NC_011508 | vertebrates,human | 1 | Reoviridae,Rotavirus,Rotavirus A | seg. 3 | FJ947938 |
| Rotavirus A human/Bethesda/DC5553/1991/G3P[8] | NC_011509 | vertebrates,human | 1 | Reoviridae,Rotavirus,Rotavirus A | seg. 6 | FJ947941 |
| Rotavirus A human/Bethesda/DC5553/1991/G3P[8] | NC_011510 | vertebrates,human | 1 | Reoviridae,Rotavirus,Rotavirus A | seg. 4 | FJ947939 |
| Rotavirus A human/Bethesda/DC5710/1991/G3P[8] | NC_011500 | vertebrates,human | 1 | Reoviridae,Rotavirus,Rotavirus A | seg. 5 | FJ947786 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC5710/1991/G3P[8] | NC_011501 | vertebrates,human | 1 | Reoviridae,Rotavirus,Rotavirus A | seg. 7 | FJ947788 |
| Rotavirus A human/Bethesda/DC5710/1991/G3P[8] | NC_011502 | vertebrates,human | 1 | Reoviridae,Rotavirus,Rotavirus A | seg. 8 | FJ947789 |
| Rotavirus A human/Bethesda/DC5710/1991/G3P[8] | NC_011504 | vertebrates,human | 1 | Reoviridae,Rotavirus,Rotavirus A | seg. 10 | FJ947791 |
| Rotavirus A human/Bethesda/DC5710/1991/G3P[8] | NC_011505 | vertebrates,human | 1 | Reoviridae,Rotavirus,Rotavirus A | seg. 11 | FJ947792 |
| Rotavirus A human/Bethesda/DC5710/1991/G3P[8] | NC_011506 | vertebrates,human | 1 | Reoviridae,Rotavirus,Rotavirus A | seg. 2 | FJ947783 |
| Rotavirus A human/Bethesda/DC5710/1991/G3P[8] | NC_011507 | vertebrates,human | 1 | Reoviridae,Rotavirus,Rotavirus A | seg. 1 | FJ947782 |
| Rotavirus A human/Bethesda/DC5710/1991/G3P[8] | NC_011508 | vertebrates,human | 1 | Reoviridae,Rotavirus,Rotavirus A | seg. 3 | FJ947784 |
| Rotavirus A human/Bethesda/DC5710/1991/G3P[8] | NC_011509 | vertebrates,human | 1 | Reoviridae,Rotavirus,Rotavirus A | seg. 6 | FJ947787 |
| Rotavirus A human/Bethesda/DC5710/1991/G3P[8] | NC_011510 | vertebrates,human | 1 | Reoviridae,Rotavirus,Rotavirus A | seg. 4 | FJ947785 |
| Rotavirus A human/Bethesda/DC5728/1991/G3P[8] | NC_011500 | vertebrates,human | 1 | Reoviridae,Rotavirus,Rotavirus A | seg. 5 | FJ947333 |
| Rotavirus A human/Bethesda/DC5728/1991/G3P[8] | NC_011501 | vertebrates,human | 1 | Reoviridae,Rotavirus,Rotavirus A | seg. 7 | FJ947335 |
| Rotavirus A human/Bethesda/DC5728/1991/G3P[8] | NC_011502 | vertebrates,human | 1 | Reoviridae,Rotavirus,Rotavirus A | seg. 8 | FJ947336 |
| Rotavirus A human/Bethesda/DC5728/1991/G3P[8] | NC_011504 | vertebrates,human | 1 | Reoviridae,Rotavirus,Rotavirus A | seg. 10 | FJ947338 |
| Rotavirus A human/Bethesda/DC5728/1991/G3P[8] | NC_011505 | vertebrates,human | 1 | Reoviridae,Rotavirus,Rotavirus A | seg. 11 | FJ947339 |
| Rotavirus A human/Bethesda/DC5728/1991/G3P[8] | NC_011506 | vertebrates,human | 1 | Reoviridae,Rotavirus,Rotavirus A | seg. 2 | FJ947330 |
| Rotavirus A human/Bethesda/DC5728/1991/G3P[8] | NC_011507 | vertebrates,human | 1 | Reoviridae,Rotavirus,Rotavirus A | seg. 1 | FJ947329 |

-continued

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC5728/1991/G3P[8] | NC_011509 | vertebrates,human | 1 | Reoviridae,Rotavirus,Rotavirus A | seg. 6 | FJ947334 |
| Rotavirus A human/Bethesda/DC5728/1991/G3P[8] | NC_011510 | vertebrates,human | 1 | Reoviridae,Rotavirus,Rotavirus A | seg. 4 | FJ947332 |
| Rotavirus A human/Bethesda/DC5751/1991/G3P[8] | NC_011500 | vertebrates,human | 1 | Reoviridae,Rotavirus,Rotavirus A | seg. 5 | FJ947797 |
| Rotavirus A human/Bethesda/DC5751/1991/G3P[8] | NC_011501 | vertebrates,human | 1 | Reoviridae,Rotavirus,Rotavirus A | seg. 7 | FJ947799 |
| Rotavirus A human/Bethesda/DC5751/1991/G3P[8] | NC_011502 | vertebrates,human | 1 | Reoviridae,Rotavirus,Rotavirus A | seg. 8 | FJ947800 |
| Rotavirus A human/Bethesda/DC5751/1991/G3P[8] | NC_011503 | vertebrates,human | 1 | Reoviridae,Rotavirus,Rotavirus A | seg. 9 | FJ947801 |
| Rotavirus A human/Bethesda/DC5751/1991/G3P[8] | NC_011504 | vertebrates,human | 1 | Reoviridae,Rotavirus,Rotavirus A | seg. 10 | FJ947802 |
| Rotavirus A human/Bethesda/DC5751/1991/G3P[8] | NC_011505 | vertebrates,human | 1 | Reoviridae,Rotavirus,Rotavirus A | seg. 11 | FJ947803 |
| Rotavirus A human/Bethesda/DC5751/1991/G3P[8] | NC_011507 | vertebrates,human | 1 | Reoviridae,Rotavirus,Rotavirus A | seg. 1 | FJ947793 |
| Rotavirus A human/Bethesda/DC5751/1991/G3P[8] | NC_011508 | vertebrates,human | 1 | Reoviridae,Rotavirus,Rotavirus A | seg. 3 | FJ947795 |
| Rotavirus A human/Bethesda/DC5751/1991/G3P[8] | NC_011509 | vertebrates,human | 1 | Reoviridae,Rotavirus,Rotavirus A | seg. 6 | FJ947798 |
| Rotavirus A human/Bethesda/DC5751/1991/G3P[8] | NC_011510 | vertebrates,human | 1 | Reoviridae,Rotavirus,Rotavirus A | seg. 4 | FJ947796 |
| Rotavirus A human/Bethesda/DC792/1980/G3P[8] | NC_011500 | vertebrates,human | 1 | Reoviridae,Rotavirus,Rotavirus A | seg. 5 | FJ947764 |
| Rotavirus A human/Bethesda/DC792/1980/G3P[8] | NC_011501 | vertebrates,human | 1 | Reoviridae,Rotavirus,Rotavirus A | seg. 7 | FJ947766 |
| Rotavirus A human/Bethesda/DC792/1980/G3P[8] | NC_011502 | vertebrates,human | 1 | Reoviridae,Rotavirus,Rotavirus A | seg. 8 | FJ947767 |
| Rotavirus A human/Bethesda/DC792/1980/G3P[8] | NC_011504 | vertebrates,human | 1 | Reoviridae,Rotavirus,Rotavirus A | seg. 10 | FJ947769 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC792/1 980/G3P[8] | NC_011505 | vertebrates,human | 1 | Reoviridae,Rotavirus,Rotavirus A | seg. 11 | FJ947770 |
| Rotavirus A human/Bethesda/DC792/1 980/G3P[8] | NC_011506 | vertebrates,human | 1 | Reoviridae,Rotavirus,Rotavirus A | seg. 2 | FJ947761 |
| Rotavirus A human/Bethesda/DC792/1 980/G3P[8] | NC_011507 | vertebrates,human | 1 | Reoviridae,Rotavirus,Rotavirus A | seg. 1 | FJ947760 |
| Rotavirus A human/Bethesda/DC792/1 980/G3P[8] | NC_011508 | vertebrates,human | 1 | Reoviridae,Rotavirus,Rotavirus A | seg. 3 | FJ947762 |
| Rotavirus A human/Bethesda/DC792/1 980/G3P[8] | NC_011509 | vertebrates,human | 1 | Reoviridae,Rotavirus,Rotavirus A | seg. 6 | FJ947765 |
| Rotavirus A human/Bethesda/DC792/1 980/G3P[8] | NC_011510 | vertebrates,human | 1 | Reoviridae,Rotavirus,Rotavirus A | seg. 4 | FJ947763 |
| Rotavirus A human/Bethesda/DC827/1 978/G4P[8] | NC_011500 | vertebrates,human | 1 | Reoviridae,Rotavirus,Rotavirus A | seg. 5 | HM773957 |
| Rotavirus A human/Bethesda/DC827/1 978/G4P[8] | NC_011501 | vertebrates,human | 1 | Reoviridae,Rotavirus,Rotavirus A | seg. 7 | HM773959 |
| Rotavirus A human/Bethesda/DC827/1 978/G4P[8] | NC_011502 | vertebrates,human | 1 | Reoviridae,Rotavirus,Rotavirus A | seg. 8 | HM773960 |
| Rotavirus A human/Bethesda/DC827/1 978/G4P[8] | NC_011503 | vertebrates,human | 1 | Reoviridae,Rotavirus,Rotavirus A | seg. 9 | HM773961 |
| Rotavirus A human/Bethesda/DC827/1 978/G4P[8] | NC_011504 | vertebrates,human | 1 | Reoviridae,Rotavirus,Rotavirus A | seg. 10 | HM773962 |
| Rotavirus A human/Bethesda/DC827/1 978/G4P[8] | NC_011505 | vertebrates,human | 1 | Reoviridae,Rotavirus,Rotavirus A | seg. 11 | HM773963 |
| Rotavirus A human/Bethesda/DC827/1 978/G4P[8] | NC_011506 | vertebrates,human | 1 | Reoviridae,Rotavirus,Rotavirus A | seg. 2 | HM773954 |
| Rotavirus A human/Bethesda/DC827/1 978/G4P[8] | NC_011507 | vertebrates,human | 1 | Reoviridae,Rotavirus,Rotavirus A | seg. 1 | HM773953 |
| Rotavirus A human/Bethesda/DC827/1 978/G4P[8] | NC_011508 | vertebrates,human | 1 | Reoviridae,Rotavirus,Rotavirus A | seg. 3 | HM773955 |
| Rotavirus A human/Bethesda/DC827/1 978/G4P[8] | NC_011509 | vertebrates,human | 1 | Reoviridae,Rotavirus,Rotavirus A | seg. 6 | HM773958 |

| Taxonomy | NCBI Reference Sequence ID | Host | No. of Genomes | Lineage | Segment Count | Genbank Accession ID |
|---|---|---|---|---|---|---|
| Rotavirus A human/Bethesda/DC827/1978/G4P[8] | NC_011510 | vertebrates,human | 1 | Reoviridae,Rotavirus,Rotavirus A | seg. 4 | HM773956 |
| Rotavirus A human/USA/2007719698/2007/G1P[8] | NC_011500 | vertebrates,human | 1 | Reoviridae,Rotavirus,Rotavirus A | seg. 5 | HM773770 |
| Rotavirus A human/USA/2007719698/2007/G1P[8] | NC_011501 | vertebrates,human | 1 | Reoviridae,Rotavirus,Rotavirus A | seg. 7 | HM773772 |
| Rotavirus A human/USA/2007719698/2007/G1P[8] | NC_011502 | vertebrates,human | 1 | Reoviridae,Rotavirus,Rotavirus A | seg. 8 | HM773773 |
| Rotavirus A human/USA/2007719698/2007/G1P[8] | NC_011503 | vertebrates,human | 1 | Reoviridae,Rotavirus,Rotavirus A | seg. 9 | HM773774 |
| Rotavirus A human/USA/2007719698/2007/G1P[8] | NC_011504 | vertebrates,human | 1 | Reoviridae,Rotavirus,Rotavirus A | seg. 10 | HM773775 |
| Rotavirus A human/USA/2007719698/2007/G1P[8] | NC_011505 | vertebrates,human | 1 | Reoviridae,Rotavirus,Rotavirus A | seg. 11 | HM773776 |
| Rotavirus A human/USA/2007719698/2007/G1P[8] | NC_011506 | vertebrates,human | 1 | Reoviridae,Rotavirus,Rotavirus A | seg. 2 | HM773767 |
| Rotavirus A human/USA/2007719698/2007/G1P[8] | NC_011507 | vertebrates,human | 1 | Reoviridae,Rotavirus,Rotavirus A | seg. 1 | HM773766 |
| Rotavirus A human/USA/2007719698/2007/G1P[8] | NC_011508 | vertebrates,human | 1 | Reoviridae,Rotavirus,Rotavirus A | seg. 3 | HM773768 |
| Rotavirus A human/USA/2007719698/2007/G1P[8] | NC_011509 | vertebrates,human | 1 | Reoviridae,Rotavirus,Rotavirus A | seg. 6 | HM773771 |
| Rotavirus A human/USA/2007719698/2007/G1P[8] | NC_011510 | vertebrates,human | 1 | Reoviridae,Rotavirus,Rotavirus A | seg. 4 | HM773769 |
| Rotavirus A human/USA/2007719739/2007/G1P[8] | NC_011500 | vertebrates,human | 1 | Reoviridae,Rotavirus,Rotavirus A | seg. 5 | HM773759 |
| Rotavirus A human/USA/2007719739/2007/G1P[8] | NC_011501 | vertebrates,human | 1 | Reoviridae,Rotavirus,Rotavirus A | seg. 7 | HM773761 |
| Rotavirus A human/USA/2007719739/2007/G1P[8] | NC_011502 | vertebrates,human | 1 | Reoviridae,Rotavirus,Rotavirus A | seg. 8 | HM773762 |
| Rotavirus A human/USA/2007719739/2007/G1P[8] | NC_011503 | vertebrates,human | 1 | Reoviridae,Rotavirus,Rotavirus A | seg. 9 | HM773763 |

| Taxonomy | NCBI Reference Sequence ID | Host | No. of Genomes | Lineage | Segment Count | Genbank Accession ID |
|---|---|---|---|---|---|---|
| Rotavirus A human/USA/2007719739/2007/G1P[8] | NC_011504 | vertebrates,human | 1 | Reoviridae,Rotavirus,Rotavirus A | seg. 10 | HM773764 |
| Rotavirus A human/USA/2007719739/2007/G1P[8] | NC_011505 | vertebrates,human | 1 | Reoviridae,Rotavirus,Rotavirus A | seg. 11 | HM773765 |
| Rotavirus A human/USA/2007719739/2007/G1P[8] | NC_011506 | vertebrates,human | 1 | Reoviridae,Rotavirus,Rotavirus A | seg. 2 | HM773756 |
| Rotavirus A human/USA/2007719739/2007/G1P[8] | NC_011507 | vertebrates,human | 1 | Reoviridae,Rotavirus,Rotavirus A | seg. 1 | HM773755 |
| Rotavirus A human/USA/2007719739/2007/G1P[8] | NC_011508 | vertebrates,human | 1 | Reoviridae,Rotavirus,Rotavirus A | seg. 3 | HM773757 |
| Rotavirus A human/USA/2007719739/2007/G1P[8] | NC_011509 | vertebrates,human | 1 | Reoviridae,Rotavirus,Rotavirus A | seg. 6 | HM773760 |
| Rotavirus A human/USA/2007719739/2007/G1P[8] | NC_011510 | vertebrates,human | 1 | Reoviridae,Rotavirus,Rotavirus A | seg. 4 | HM773758 |
| Rotavirus A human/USA/2007719825/2007/G1P[8] | NC_011500 | vertebrates,human | 1 | Reoviridae,Rotavirus,Rotavirus A | seg. 5 | HM773748 |
| Rotavirus A human/USA/2007719825/2007/G1P[8] | NC_011501 | vertebrates,human | 1 | Reoviridae,Rotavirus,Rotavirus A | seg. 7 | HM773750 |
| Rotavirus A human/USA/2007719825/2007/G1P[8] | NC_011502 | vertebrates,human | 1 | Reoviridae,Rotavirus,Rotavirus A | seg. 8 | HM773751 |
| Rotavirus A human/USA/2007719825/2007/G1P[8] | NC_011503 | vertebrates,human | 1 | Reoviridae,Rotavirus,Rotavirus A | seg. 9 | HM773752 |
| Rotavirus A human/USA/2007719825/2007/G1P[8] | NC_011504 | vertebrates,human | 1 | Reoviridae,Rotavirus,Rotavirus A | seg. 10 | HM773753 |
| Rotavirus A human/USA/2007719825/2007/G1P[8] | NC_011505 | vertebrates,human | 1 | Reoviridae,Rotavirus,Rotavirus A | seg. 11 | HM773754 |
| Rotavirus A human/USA/2007719825/2007/G1P[8] | NC_011506 | vertebrates,human | 1 | Reoviridae,Rotavirus,Rotavirus A | seg. 2 | HM773745 |
| Rotavirus A human/USA/2007719825/2007/G1P[8] | NC_011507 | vertebrates,human | 1 | Reoviridae,Rotavirus,Rotavirus A | seg. 1 | HM773744 |
| Rotavirus A human/USA/2007719825/2007/G1P[8] | NC_011508 | vertebrates,human | 1 | Reoviridae,Rotavirus,Rotavirus A | seg. 3 | HM773746 |

-continued

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00026/2005/G1P[8] | NC_011508 | vertebrates,human | 1 | Reoviridae,Rotavirus,Rotavirus A | seg. 3 | JF490334 |
| Rotavirus A human/Victoria/CK00026/2005/G1P[8] | NC_011509 | vertebrates,human | 1 | Reoviridae,Rotavirus,Rotavirus A | seg. 6 | JF490332 |
| Rotavirus A human/Victoria/CK00026/2005/G1P[8] | NC_011510 | vertebrates,human | 1 | Reoviridae,Rotavirus,Rotavirus A | seg. 4 | JF490333 |
| Rotavirus A human/Victoria/CK00027/2054/G1P[8] | NC_011500 | vertebrates,human | 1 | Reoviridae,Rotavirus,Rotavirus A | seg. 5 | JF490338 |
| Rotavirus A human/Victoria/CK00027/2054/G1P[8] | NC_011501 | vertebrates,human | 1 | Reoviridae,Rotavirus,Rotavirus A | seg. 7 | JF490342 |
| Rotavirus A human/Victoria/CK00027/2054/G1P[8] | NC_011502 | vertebrates,human | 1 | Reoviridae,Rotavirus,Rotavirus A | seg. 8 | JF490337 |
| Rotavirus A human/Victoria/CK00027/2054/G1P[8] | NC_011503 | vertebrates,human | 1 | Reoviridae,Rotavirus,Rotavirus A | seg. 9 | JF490341 |
| Rotavirus A human/Victoria/CK00027/2054/G1P[8] | NC_011504 | vertebrates,human | 1 | Reoviridae,Rotavirus,Rotavirus A | seg. 10 | JF490340 |
| Rotavirus A human/Victoria/CK00027/2054/G1P[8] | NC_011505 | vertebrates,human | 1 | Reoviridae,Rotavirus,Rotavirus A | seg. 11 | JF490339 |
| Rotavirus A human/Victoria/CK00027/2054/G1P[8] | NC_011506 | vertebrates,human | 1 | Reoviridae,Rotavirus,Rotavirus A | seg. 2 | JF490345 |
| Rotavirus A human/Victoria/CK00027/2054/G1P[8] | NC_011507 | vertebrates,human | 1 | Reoviridae,Rotavirus,Rotavirus A | seg. 1 | JF490336 |
| Rotavirus A human/Victoria/CK00027/2054/G1P[8] | NC_011508 | vertebrates,human | 1 | Reoviridae,Rotavirus,Rotavirus A | seg. 3 | JF490346 |
| Rotavirus A human/Victoria/CK00027/2054/G1P[8] | NC_011509 | vertebrates,human | 1 | Reoviridae,Rotavirus,Rotavirus A | seg. 6 | JF490343 |
| Rotavirus A human/Victoria/CK00027/2054/G1P[8] | NC_011510 | vertebrates,human | 1 | Reoviridae,Rotavirus,Rotavirus A | seg. 4 | JF490344 |
| Rotavirus A human/Victoria/CK00028/2005/G1P[8] | NC_011500 | vertebrates,human | 1 | Reoviridae,Rotavirus,Rotavirus A | seg. 5 | JF490357 |
| Rotavirus A human/Victoria/CK00028/2005/G1P[8] | NC_011501 | vertebrates,human | 1 | Reoviridae,Rotavirus,Rotavirus A | seg. 7 | JF490352 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00028/2 005/G1P[8] | NC_011502 | vertebrates,human | 1 | Reoviridae,Rotavirus,Rotavirus A | seg. 8 | JF490348 |
| Rotavirus A human/Victoria/CK00028/2 005/G1P[8] | NC_011503 | vertebrates,human | 1 | Reoviridae,Rotavirus,Rotavirus A | seg. 9 | JF490351 |
| Rotavirus A human/Victoria/CK00028/2 005/G1P[8] | NC_011504 | vertebrates,human | 1 | Reoviridae,Rotavirus,Rotavirus A | seg. 10 | JF490350 |
| Rotavirus A human/Victoria/CK00028/2 005/G1P[8] | NC_011505 | vertebrates,human | 1 | Reoviridae,Rotavirus,Rotavirus A | seg. 11 | JF490349 |
| Rotavirus A human/Victoria/CK00028/2 005/G1P[8] | NC_011506 | vertebrates,human | 1 | Reoviridae,Rotavirus,Rotavirus A | seg. 2 | JF490356 |
| Rotavirus A human/Victoria/CK00028/2 005/G1P[8] | NC_011507 | vertebrates,human | 1 | Reoviridae,Rotavirus,Rotavirus A | seg. 1 | JF490347 |
| Rotavirus A human/Victoria/CK00028/2 005/G1P[8] | NC_011508 | vertebrates,human | 1 | Reoviridae,Rotavirus,Rotavirus A | seg. 3 | JF490355 |
| Rotavirus A human/Victoria/CK00028/2 005/G1P[8] | NC_011509 | vertebrates,human | 1 | Reoviridae,Rotavirus,Rotavirus A | seg. 6 | JF490353 |
| Rotavirus A human/Victoria/CK00028/2 005/G1P[8] | NC_011510 | vertebrates,human | 1 | Reoviridae,Rotavirus,Rotavirus A | seg. 4 | JF490354 |
| Rotavirus A human/Victoria/CK00028/2 005/G1P[8] | NC_011500 | vertebrates,human | 1 | Reoviridae,Rotavirus,Rotavirus A | seg. 5 | JF490360 |
| Rotavirus A human/Victoria/CK00029/2 006/G1P[8] | NC_011501 | vertebrates,human | 1 | Reoviridae,Rotavirus,Rotavirus A | seg. 7 | JF490363 |
| Rotavirus A human/Victoria/CK00029/2 006/G1P[8] | NC_011502 | vertebrates,human | 1 | Reoviridae,Rotavirus,Rotavirus A | seg. 8 | JF490359 |
| Rotavirus A human/Victoria/CK00029/2 006/G1P[8] | NC_011503 | vertebrates,human | 1 | Reoviridae,Rotavirus,Rotavirus A | seg. 9 | JF490368 |
| Rotavirus A human/Victoria/CK00029/2 006/G1P[8] | NC_011504 | vertebrates,human | 1 | Reoviridae,Rotavirus,Rotavirus A | seg. 10 | JF490362 |
| Rotavirus A human/Victoria/CK00029/2 006/G1P[8] | NC_011505 | vertebrates,human | 1 | Reoviridae,Rotavirus,Rotavirus A | seg. 11 | JF490361 |
| Rotavirus A human/Victoria/CK00029/2 006/G1P[8] | NC_011506 | vertebrates,human | 1 | Reoviridae,Rotavirus,Rotavirus A | seg. 2 | JF490367 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00029/2006/G1P[8] | NC_011507 | vertebrates,human | 1 | Reoviridae,Rotavirus,Rotavirus A | seg. 1 | JF490358 |
| Rotavirus A human/Victoria/CK00029/2006/G1P[8] | NC_011508 | vertebrates,human | 1 | Reoviridae,Rotavirus,Rotavirus A | seg. 3 | JF490366 |
| Rotavirus A human/Victoria/CK00029/2006/G1P[8] | NC_011509 | vertebrates,human | 1 | Reoviridae,Rotavirus,Rotavirus A | seg. 6 | JF490364 |
| Rotavirus A human/Victoria/CK00029/2006/G1P[8] | NC_011510 | vertebrates,human | 1 | Reoviridae,Rotavirus,Rotavirus A | seg. 4 | JF490365 |
| Rotavirus A human/Victoria/CK00030/2006/G1P[8] | NC_011500 | vertebrates,human | 1 | Reoviridae,Rotavirus,Rotavirus A | seg. 5 | JF490371 |
| Rotavirus A human/Victoria/CK00030/2006/G1P[8] | NC_011501 | vertebrates,human | 1 | Reoviridae,Rotavirus,Rotavirus A | seg. 7 | JF490375 |
| Rotavirus A human/Victoria/CK00030/2006/G1P[8] | NC_011502 | vertebrates,human | 1 | Reoviridae,Rotavirus,Rotavirus A | seg. 8 | JF490370 |
| Rotavirus A human/Victoria/CK00030/2006/G1P[8] | NC_011503 | vertebrates,human | 1 | Reoviridae,Rotavirus,Rotavirus A | seg. 9 | JF490374 |
| Rotavirus A human/Victoria/CK00030/2006/G1P[8] | NC_011504 | vertebrates,human | 1 | Reoviridae,Rotavirus,Rotavirus A | seg. 10 | JF490373 |
| Rotavirus A human/Victoria/CK00030/2006/G1P[8] | NC_011505 | vertebrates,human | 1 | Reoviridae,Rotavirus,Rotavirus A | seg. 11 | JF490372 |
| Rotavirus A human/Victoria/CK00030/2006/G1P[8] | NC_011506 | vertebrates,human | 1 | Reoviridae,Rotavirus,Rotavirus A | seg. 2 | JF490379 |
| Rotavirus A human/Victoria/CK00030/2006/G1P[8] | NC_011507 | vertebrates,human | 1 | Reoviridae,Rotavirus,Rotavirus A | seg. 1 | JF490369 |
| Rotavirus A human/Victoria/CK00030/2006/G1P[8] | NC_011508 | vertebrates,human | 1 | Reoviridae,Rotavirus,Rotavirus A | seg. 3 | JF490377 |
| Rotavirus A human/Victoria/CK00030/2006/G1P[8] | NC_011509 | vertebrates,human | 1 | Reoviridae,Rotavirus,Rotavirus A | seg. 6 | JF490376 |
| Rotavirus A human/Victoria/CK00030/2006/G1P[8] | NC_011510 | vertebrates,human | 1 | Reoviridae,Rotavirus,Rotavirus A | seg. 4 | JF490378 |
| Rotavirus A human/Victoria/CK00032/2006/G1P[8] | NC_011500 | vertebrates,human | 1 | Reoviridae,Rotavirus,Rotavirus A | seg. 5 | JF490382 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00032/2006/G1P[8] | NC_011501 | vertebrates,human | 1 | Reoviridae,Rotavirus,Rotavirus A | seg. 7 | JF490386 |
| Rotavirus A human/Victoria/CK00032/2006/G1P[8] | NC_011502 | vertebrates,human | 1 | Reoviridae,Rotavirus,Rotavirus A | seg. 8 | JF490381 |
| Rotavirus A human/Victoria/CK00032/2006/G1P[8] | NC_011503 | vertebrates,human | 1 | Reoviridae,Rotavirus,Rotavirus A | seg. 9 | JF490385 |
| Rotavirus A human/Victoria/CK00032/2006/G1P[8] | NC_011504 | vertebrates,human | 1 | Reoviridae,Rotavirus,Rotavirus A | seg. 10 | JF490384 |
| Rotavirus A human/Victoria/CK00032/2006/G1P[8] | NC_011505 | vertebrates,human | 1 | Reoviridae,Rotavirus,Rotavirus A | seg. 11 | JF490383 |
| Rotavirus A human/Victoria/CK00032/2006/G1P[8] | NC_011506 | vertebrates,human | 1 | Reoviridae,Rotavirus,Rotavirus A | seg. 2 | JF490390 |
| Rotavirus A human/Victoria/CK00032/2006/G1P[8] | NC_011507 | vertebrates,human | 1 | Reoviridae,Rotavirus,Rotavirus A | seg. 1 | JF490380 |
| Rotavirus A human/Victoria/CK00032/2006/G1P[8] | NC_011508 | vertebrates,human | 1 | Reoviridae,Rotavirus,Rotavirus A | seg. 3 | JF490389 |
| Rotavirus A human/Victoria/CK00032/2006/G1P[8] | NC_011509 | vertebrates,human | 1 | Reoviridae,Rotavirus,Rotavirus A | seg. 6 | JF490387 |
| Rotavirus A human/Victoria/CK00032/2006/G1P[8] | NC_011510 | vertebrates,human | 1 | Reoviridae,Rotavirus,Rotavirus A | seg. 4 | JF490388 |
| Rotavirus A human/Victoria/CK00032/2006/G1P[8] | NC_011500 | vertebrates,human | 1 | Reoviridae,Rotavirus,Rotavirus A | seg. 5 | JF490393 |
| Rotavirus A human/Victoria/CK00033/2007/G1P[8] | NC_011501 | vertebrates,human | 1 | Reoviridae,Rotavirus,Rotavirus A | seg. 7 | JF490397 |
| Rotavirus A human/Victoria/CK00033/2007/G1P[8] | NC_011502 | vertebrates,human | 1 | Reoviridae,Rotavirus,Rotavirus A | seg. 8 | JF490392 |
| Rotavirus A human/Victoria/CK00033/2007/G1P[8] | NC_011503 | vertebrates,human | 1 | Reoviridae,Rotavirus,Rotavirus A | seg. 9 | JF490396 |
| Rotavirus A human/Victoria/CK00033/2007/G1P[8] | NC_011504 | vertebrates,human | 1 | Reoviridae,Rotavirus,Rotavirus A | seg. 10 | JF490395 |
| Rotavirus A human/Victoria/CK00033/2007/G1P[8] | NC_011505 | vertebrates,human | 1 | Reoviridae,Rotavirus,Rotavirus A | seg. 11 | JF490394 |

-continued

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00033/2007/G1P[8] | NC_011506 | vertebrates,human | 1 | Reoviridae,Rotavirus,Rotavirus A | seg. 2 | JF490401 |
| Rotavirus A human/Victoria/CK00033/2007/G1P[8] | NC_011507 | vertebrates,human | 1 | Reoviridae,Rotavirus,Rotavirus A | seg. 1 | JF490391 |
| Rotavirus A human/Victoria/CK00033/2007/G1P[8] | NC_011508 | vertebrates,human | 1 | Reoviridae,Rotavirus,Rotavirus A | seg. 3 | JF490400 |
| Rotavirus A human/Victoria/CK00033/2007/G1P[8] | NC_011509 | vertebrates,human | 1 | Reoviridae,Rotavirus,Rotavirus A | seg. 6 | JF490398 |
| Rotavirus A human/Victoria/CK00033/2007/G1P[8] | NC_011510 | vertebrates,human | 1 | Reoviridae,Rotavirus,Rotavirus A | seg. 4 | JF490399 |
| Rotavirus A human/Victoria/CK00034/2007/G1P[8] | NC_011500 | vertebrates,human | 1 | Reoviridae,Rotavirus,Rotavirus A | seg. 5 | JF490410 |
| Rotavirus A human/Victoria/CK00034/2007/G1P[8] | NC_011501 | vertebrates,human | 1 | Reoviridae,Rotavirus,Rotavirus A | seg. 7 | JF490407 |
| Rotavirus A human/Victoria/CK00034/2007/G1P[8] | NC_011502 | vertebrates,human | 1 | Reoviridae,Rotavirus,Rotavirus A | seg. 8 | JF490403 |
| Rotavirus A human/Victoria/CK00034/2007/G1P[8] | NC_011503 | vertebrates,human | 1 | Reoviridae,Rotavirus,Rotavirus A | seg. 9 | JF490406 |
| Rotavirus A human/Victoria/CK00034/2007/G1P[8] | NC_011504 | vertebrates,human | 1 | Reoviridae,Rotavirus,Rotavirus A | seg. 10 | JF490405 |
| Rotavirus A human/Victoria/CK00034/2007/G1P[8] | NC_011505 | vertebrates,human | 1 | Reoviridae,Rotavirus,Rotavirus A | seg. 11 | JF490404 |
| Rotavirus A human/Victoria/CK00034/2007/G1P[8] | NC_011506 | vertebrates,human | 1 | Reoviridae,Rotavirus,Rotavirus A | seg. 2 | JF490412 |
| Rotavirus A human/Victoria/CK00034/2007/G1P[8] | NC_011507 | vertebrates,human | 1 | Reoviridae,Rotavirus,Rotavirus A | seg. 1 | JF490402 |
| Rotavirus A human/Victoria/CK00034/2007/G1P[8] | NC_011508 | vertebrates,human | 1 | Reoviridae,Rotavirus,Rotavirus A | seg. 3 | JF490411 |
| Rotavirus A human/Victoria/CK00034/2007/G1P[8] | NC_011509 | vertebrates,human | 1 | Reoviridae,Rotavirus,Rotavirus A | seg. 6 | JF490408 |
| Rotavirus A human/Victoria/CK00034/2007/G1P[8] | NC_011510 | vertebrates,human | 1 | Reoviridae,Rotavirus,Rotavirus A | seg. 4 | JF490409 |

-continued

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00035/2005/G1P[8] | NC_011500 | vertebrates,human | 1 | Reoviridae,Rotavirus,Rotavirus A | seg. 5 | JF490415 |
| Rotavirus A human/Victoria/CK00035/2005/G1P[8] | NC_011501 | vertebrates,human | 1 | Reoviridae,Rotavirus,Rotavirus A | seg. 7 | JF490419 |
| Rotavirus A human/Victoria/CK00035/2005/G1P[8] | NC_011502 | vertebrates,human | 1 | Reoviridae,Rotavirus,Rotavirus A | seg. 8 | JF490414 |
| Rotavirus A human/Victoria/CK00035/2005/G1P[8] | NC_011503 | vertebrates,human | 1 | Reoviridae,Rotavirus,Rotavirus A | seg. 9 | JF490418 |
| Rotavirus A human/Victoria/CK00035/2005/G1P[8] | NC_011504 | vertebrates,human | 1 | Reoviridae,Rotavirus,Rotavirus A | seg. 10 | JF490417 |
| Rotavirus A human/Victoria/CK00035/2005/G1P[8] | NC_011505 | vertebrates,human | 1 | Reoviridae,Rotavirus,Rotavirus A | seg. 11 | JF490416 |
| Rotavirus A human/Victoria/CK00035/2005/G1P[8] | NC_011506 | vertebrates,human | 1 | Reoviridae,Rotavirus,Rotavirus A | seg. 2 | JF490423 |
| Rotavirus A human/Victoria/CK00035/2005/G1P[8] | NC_011507 | vertebrates,human | 1 | Reoviridae,Rotavirus,Rotavirus A | seg. 1 | JF490413 |
| Rotavirus A human/Victoria/CK00035/2005/G1P[8] | NC_011508 | vertebrates,human | 1 | Reoviridae,Rotavirus,Rotavirus A | seg. 3 | JF490422 |
| Rotavirus A human/Victoria/CK00035/2005/G1P[8] | NC_011509 | vertebrates,human | 1 | Reoviridae,Rotavirus,Rotavirus A | seg. 6 | JF490420 |
| Rotavirus A human/Victoria/CK00035/2005/G1P[8] | NC_011510 | vertebrates,human | 1 | Reoviridae,Rotavirus,Rotavirus A | seg. 4 | JF490421 |
| Rotavirus A human/Victoria/CK00036/2005/G1P[8] | NC_011500 | vertebrates,human | 1 | Reoviridae,Rotavirus,Rotavirus A | seg. 5 | JF490434 |
| Rotavirus A human/Victoria/CK00036/2005/G1P[8] | NC_011501 | vertebrates,human | 1 | Reoviridae,Rotavirus,Rotavirus A | seg. 7 | JF490429 |
| Rotavirus A human/Victoria/CK00036/2005/G1P[8] | NC_011502 | vertebrates,human | 1 | Reoviridae,Rotavirus,Rotavirus A | seg. 8 | JF490425 |
| Rotavirus A human/Victoria/CK00036/2005/G1P[8] | NC_011503 | vertebrates,human | 1 | Reoviridae,Rotavirus,Rotavirus A | seg. 9 | JF490428 |
| Rotavirus A human/Victoria/CK00036/2005/G1P[8] | NC_011504 | vertebrates,human | 1 | Reoviridae,Rotavirus,Rotavirus A | seg. 10 | JF490427 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00036/2005/G1P[8] | NC_011505 | vertebrates,human | 1 | Reoviridae,Rotavirus,Rotavirus A | seg. 11 | JF490426 |
| Rotavirus A human/Victoria/CK00036/2005/G1P[8] | NC_011506 | vertebrates,human | 1 | Reoviridae,Rotavirus,Rotavirus A | seg. 2 | JF490433 |
| Rotavirus A human/Victoria/CK00036/2005/G1P[8] | NC_011507 | vertebrates,human | 1 | Reoviridae,Rotavirus,Rotavirus A | seg. 1 | JF490424 |
| Rotavirus A human/Victoria/CK00036/2005/G1P[8] | NC_011508 | vertebrates,human | 1 | Reoviridae,Rotavirus,Rotavirus A | seg. 3 | JF490432 |
| Rotavirus A human/Victoria/CK00036/2005/G1P[8] | NC_011509 | vertebrates,human | 1 | Reoviridae,Rotavirus,Rotavirus A | seg. 6 | JF490430 |
| Rotavirus A human/Victoria/CK00036/2005/G1P[8] | NC_011510 | vertebrates,human | 1 | Reoviridae,Rotavirus,Rotavirus A | seg. 4 | JF490431 |
| Rotavirus A human/Victoria/CK00037/2006/G1P[8] | NC_011500 | vertebrates,human | 1 | Reoviridae,Rotavirus,Rotavirus A | seg. 5 | JF490443 |
| Rotavirus A human/Victoria/CK00037/2006/G1P[8] | NC_011501 | vertebrates,human | 1 | Reoviridae,Rotavirus,Rotavirus A | seg. 7 | JF490439 |
| Rotavirus A human/Victoria/CK00037/2006/G1P[8] | NC_011502 | vertebrates,human | 1 | Reoviridae,Rotavirus,Rotavirus A | seg. 8 | JF490436 |
| Rotavirus A human/Victoria/CK00037/2006/G1P[8] | NC_011503 | vertebrates,human | 1 | Reoviridae,Rotavirus,Rotavirus A | seg. 9 | JF490444 |
| Rotavirus A human/Victoria/CK00037/2006/G1P[8] | NC_011504 | vertebrates,human | 1 | Reoviridae,Rotavirus,Rotavirus A | seg. 10 | JF490438 |
| Rotavirus A human/Victoria/CK00037/2006/G1P[8] | NC_011505 | vertebrates,human | 1 | Reoviridae,Rotavirus,Rotavirus A | seg. 11 | JF490437 |
| Rotavirus A human/Victoria/CK00037/2006/G1P[8] | NC_011506 | vertebrates,human | 1 | Reoviridae,Rotavirus,Rotavirus A | seg. 2 | JF490445 |
| Rotavirus A human/Victoria/CK00037/2006/G1P[8] | NC_011507 | vertebrates,human | 1 | Reoviridae,Rotavirus,Rotavirus A | seg. 1 | JF490435 |
| Rotavirus A human/Victoria/CK00037/2006/G1P[8] | NC_011508 | vertebrates,human | 1 | Reoviridae,Rotavirus,Rotavirus A | seg. 3 | JF490442 |
| Rotavirus A human/Victoria/CK00037/2006/G1P[8] | NC_011509 | vertebrates,human | 1 | Reoviridae,Rotavirus,Rotavirus A | seg. 6 | JF490440 |

-continued

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00037/2 006/G1P[8] | NC_011510 | vertebrates,human | 1 | Reoviridae,Rotavirus,Rotavirus A | seg. 4 | JF490441 |
| Rotavirus A human/Victoria/CK00039/2 006/G1P[8] | NC_011500 | vertebrates,human | 1 | Reoviridae,Rotavirus,Rotavirus A | seg. 5 | JF490448 |
| Rotavirus A human/Victoria/CK00039/2 006/G1P[8] | NC_011501 | vertebrates,human | 1 | Reoviridae,Rotavirus,Rotavirus A | seg. 7 | JF490452 |
| Rotavirus A human/Victoria/CK00039/2 006/G1P[8] | NC_011502 | vertebrates,human | 1 | Reoviridae,Rotavirus,Rotavirus A | seg. 8 | JF490447 |
| Rotavirus A human/Victoria/CK00039/2 006/G1P[8] | NC_011503 | vertebrates,human | 1 | Reoviridae,Rotavirus,Rotavirus A | seg. 9 | JF490451 |
| Rotavirus A human/Victoria/CK00039/2 006/G1P[8] | NC_011504 | vertebrates,human | 1 | Reoviridae,Rotavirus,Rotavirus A | seg. 10 | JF490450 |
| Rotavirus A human/Victoria/CK00039/2 006/G1P[8] | NC_011505 | vertebrates,human | 1 | Reoviridae,Rotavirus,Rotavirus A | seg. 11 | JF490449 |
| Rotavirus A human/Victoria/CK00039/2 006/G1P[8] | NC_011506 | vertebrates,human | 1 | Reoviridae,Rotavirus,Rotavirus A | seg. 2 | JF490456 |
| Rotavirus A human/Victoria/CK00039/2 006/G1P[8] | NC_011507 | vertebrates,human | 1 | Reoviridae,Rotavirus,Rotavirus A | seg. 1 | JF490446 |
| Rotavirus A human/Victoria/CK00039/2 006/G1P[8] | NC_011508 | vertebrates,human | 1 | Reoviridae,Rotavirus,Rotavirus A | seg. 3 | JF490455 |
| Rotavirus A human/Victoria/CK00039/2 006/G1P[8] | NC_011509 | vertebrates,human | 1 | Reoviridae,Rotavirus,Rotavirus A | seg. 6 | JF490453 |
| Rotavirus A human/Victoria/CK00039/2 006/G1P[8] | NC_011510 | vertebrates,human | 1 | Reoviridae,Rotavirus,Rotavirus A | seg. 4 | JF490454 |
| Rotavirus A human/Victoria/CK00040/2 006/G1P[8] | NC_011500 | vertebrates,human | 1 | Reoviridae,Rotavirus,Rotavirus A | seg. 5 | JF490459 |
| Rotavirus A human/Victoria/CK00040/2 006/G1P[8] | NC_011501 | vertebrates,human | 1 | Reoviridae,Rotavirus,Rotavirus A | seg. 7 | JF490463 |
| Rotavirus A human/Victoria/CK00040/2 006/G1P[8] | NC_011502 | vertebrates,human | 1 | Reoviridae,Rotavirus,Rotavirus A | seg. 8 | JF490458 |
| Rotavirus A human/Victoria/CK00040/2 006/G1P[8] | NC_011503 | vertebrates,human | 1 | Reoviridae,Rotavirus,Rotavirus A | seg. 9 | JF490462 |

-continued

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00040/2 006/G1P[8] | NC_011504 | vertebrates,human | 1 | Reoviridae,Rotavirus,Rotavirus A | seg. 10 | JF490461 |
| Rotavirus A human/Victoria/CK00040/2 006/G1P[8] | NC_011505 | vertebrates,human | 1 | Reoviridae,Rotavirus,Rotavirus A | seg. 11 | JF490460 |
| Rotavirus A human/Victoria/CK00040/2 006/G1P[8] | NC_011506 | vertebrates,human | 1 | Reoviridae,Rotavirus,Rotavirus A | seg. 2 | JF490467 |
| Rotavirus A human/Victoria/CK00040/2 006/G1P[8] | NC_011507 | vertebrates,human | 1 | Reoviridae,Rotavirus,Rotavirus A | seg. 1 | JF490457 |
| Rotavirus A human/Victoria/CK00040/2 006/G1P[8] | NC_011508 | vertebrates,human | 1 | Reoviridae,Rotavirus,Rotavirus A | seg. 3 | JF490466 |
| Rotavirus A human/Victoria/CK00040/2 006/G1P[8] | NC_011509 | vertebrates,human | 1 | Reoviridae,Rotavirus,Rotavirus A | seg. 6 | JF490464 |
| Rotavirus A human/Victoria/CK00040/2 006/G1P[8] | NC_011510 | vertebrates,human | 1 | Reoviridae,Rotavirus,Rotavirus A | seg. 4 | JF490465 |
| Rotavirus A human/Victoria/CK00041/2 006/G1P[8] | NC_011500 | vertebrates,human | 1 | Reoviridae,Rotavirus,Rotavirus A | seg. 5 | JF490470 |
| Rotavirus A human/Victoria/CK00041/2 006/G1P[8] | NC_011501 | vertebrates,human | 1 | Reoviridae,Rotavirus,Rotavirus A | seg. 7 | JF490474 |
| Rotavirus A human/Victoria/CK00041/2 006/G1P[8] | NC_011502 | vertebrates,human | 1 | Reoviridae,Rotavirus,Rotavirus A | seg. 8 | JF490469 |
| Rotavirus A human/Victoria/CK00041/2 006/G1P[8] | NC_011503 | vertebrates,human | 1 | Reoviridae,Rotavirus,Rotavirus A | seg. 9 | JF490473 |
| Rotavirus A human/Victoria/CK00041/2 006/G1P[8] | NC_011504 | vertebrates,human | 1 | Reoviridae,Rotavirus,Rotavirus A | seg. 10 | JF490472 |
| Rotavirus A human/Victoria/CK00041/2 006/G1P[8] | NC_011505 | vertebrates,human | 1 | Reoviridae,Rotavirus,Rotavirus A | seg. 11 | JF490471 |
| Rotavirus A human/Victoria/CK00041/2 006/G1P[8] | NC_011506 | vertebrates,human | 1 | Reoviridae,Rotavirus,Rotavirus A | seg. 2 | JF490478 |
| Rotavirus A human/Victoria/CK00041/2 006/G1P[8] | NC_011507 | vertebrates,human | 1 | Reoviridae,Rotavirus,Rotavirus A | seg. 1 | JF490468 |
| Rotavirus A human/Victoria/CK00041/2 006/G1P[8] | NC_011508 | vertebrates,human | 1 | Reoviridae,Rotavirus,Rotavirus A | seg. 3 | JF490477 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00041/2 006/G1P[8] | NC_011509 | vertebrates,human | 1 | Reoviridae,Rotavirus,Rotavirus A | seg. 6 | JF490475 |
| Rotavirus A human/Victoria/CK00041/2 006/G1P[8] | NC_011510 | vertebrates,human | 1 | Reoviridae,Rotavirus,Rotavirus A | seg. 4 | JF490476 |
| Rotavirus A human/Victoria/CK00043/2 006/G1P[8] | NC_011500 | vertebrates,human | 1 | Reoviridae,Rotavirus,Rotavirus A | seg. 5 | JF490481 |
| Rotavirus A human/Victoria/CK00043/2 006/G1P[8] | NC_011501 | vertebrates,human | 1 | Reoviridae,Rotavirus,Rotavirus A | seg. 7 | JF490485 |
| Rotavirus A human/Victoria/CK00043/2 006/G1P[8] | NC_011502 | vertebrates,human | 1 | Reoviridae,Rotavirus,Rotavirus A | seg. 8 | JF490480 |
| Rotavirus A human/Victoria/CK00043/2 006/G1P[8] | NC_011503 | vertebrates,human | 1 | Reoviridae,Rotavirus,Rotavirus A | seg. 9 | JF490484 |
| Rotavirus A human/Victoria/CK00043/2 006/G1P[8] | NC_011504 | vertebrates,human | 1 | Reoviridae,Rotavirus,Rotavirus A | seg. 10 | JF490483 |
| Rotavirus A human/Victoria/CK00043/2 006/G1P[8] | NC_011505 | vertebrates,human | 1 | Reoviridae,Rotavirus,Rotavirus A | seg. 11 | JF490482 |
| Rotavirus A human/Victoria/CK00043/2 006/G1P[8] | NC_011506 | vertebrates,human | 1 | Reoviridae,Rotavirus,Rotavirus A | seg. 2 | JF490489 |
| Rotavirus A human/Victoria/CK00043/2 006/G1P[8] | NC_011507 | vertebrates,human | 1 | Reoviridae,Rotavirus,Rotavirus A | seg. 1 | JF490479 |
| Rotavirus A human/Victoria/CK00043/2 006/G1P[8] | NC_011508 | vertebrates,human | 1 | Reoviridae,Rotavirus,Rotavirus A | seg. 3 | JF490488 |
| Rotavirus A human/Victoria/CK00043/2 006/G1P[8] | NC_011509 | vertebrates,human | 1 | Reoviridae,Rotavirus,Rotavirus A | seg. 6 | JF490486 |
| Rotavirus A human/Victoria/CK00043/2 006/G1P[8] | NC_011510 | vertebrates,human | 1 | Reoviridae,Rotavirus,Rotavirus A | seg. 4 | JF490487 |
| Rotavirus A human/Victoria/CK00045/2 006/G1P[8] | NC_011500 | vertebrates,human | 1 | Reoviridae,Rotavirus,Rotavirus A | seg. 5 | JF490495 |
| Rotavirus A human/Victoria/CK00045/2 006/G1P[8] | NC_011501 | vertebrates,human | 1 | Reoviridae,Rotavirus,Rotavirus A | seg. 7 | JF490499 |
| Rotavirus A human/Victoria/CK00045/2 006/G1P[8] | NC_011502 | vertebrates,human | 1 | Reoviridae,Rotavirus,Rotavirus A | seg. 8 | JF490494 |

-continued

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00045/2006/G1P[8] | NC_011503 | vertebrates,human | 1 | Reoviridae,Rotavirus,Rotavirus A | seg. 9 | JF490498 |
| Rotavirus A human/Victoria/CK00045/2006/G1P[8] | NC_011504 | vertebrates,human | 1 | Reoviridae,Rotavirus,Rotavirus A | seg. 10 | JF490497 |
| Rotavirus A human/Victoria/CK00045/2006/G1P[8] | NC_011505 | vertebrates,human | 1 | Reoviridae,Rotavirus,Rotavirus A | seg. 11 | JF490496 |
| Rotavirus A human/Victoria/CK00045/2006/G1P[8] | NC_011506 | vertebrates,human | 1 | Reoviridae,Rotavirus,Rotavirus A | seg. 2 | JF490493 |
| Rotavirus A human/Victoria/CK00045/2006/G1P[8] | NC_011507 | vertebrates,human | 1 | Reoviridae,Rotavirus,Rotavirus A | seg. 1 | JF490490 |
| Rotavirus A human/Victoria/CK00045/2006/G1P[8] | NC_011508 | vertebrates,human | 1 | Reoviridae,Rotavirus,Rotavirus A | seg. 3 | JF490492 |
| Rotavirus A human/Victoria/CK00045/2006/G1P[8] | NC_011509 | vertebrates,human | 1 | Reoviridae,Rotavirus,Rotavirus A | seg. 6 | JF490500 |
| Rotavirus A human/Victoria/CK00045/2006/G1P[8] | NC_011510 | vertebrates,human | 1 | Reoviridae,Rotavirus,Rotavirus A | seg. 4 | JF490491 |
| Rotavirus A human/Victoria/CK00046/2006/G1P[8] | NC_011500 | vertebrates,human | 1 | Reoviridae,Rotavirus,Rotavirus A | seg. 5 | JF490503 |
| Rotavirus A human/Victoria/CK00046/2006/G1P[8] | NC_011501 | vertebrates,human | 1 | Reoviridae,Rotavirus,Rotavirus A | seg. 7 | JF490507 |
| Rotavirus A human/Victoria/CK00046/2006/G1P[8] | NC_011502 | vertebrates,human | 1 | Reoviridae,Rotavirus,Rotavirus A | seg. 8 | JF490502 |
| Rotavirus A human/Victoria/CK00046/2006/G1P[8] | NC_011503 | vertebrates,human | 1 | Reoviridae,Rotavirus,Rotavirus A | seg. 9 | JF490506 |
| Rotavirus A human/Victoria/CK00046/2006/G1P[8] | NC_011504 | vertebrates,human | 1 | Reoviridae,Rotavirus,Rotavirus A | seg. 10 | JF490505 |
| Rotavirus A human/Victoria/CK00046/2006/G1P[8] | NC_011505 | vertebrates,human | 1 | Reoviridae,Rotavirus,Rotavirus A | seg. 11 | JF490504 |
| Rotavirus A human/Victoria/CK00046/2006/G1P[8] | NC_011506 | vertebrates,human | 1 | Reoviridae,Rotavirus,Rotavirus A | seg. 2 | JF490511 |
| Rotavirus A human/Victoria/CK00046/2006/G1P[8] | NC_011507 | vertebrates,human | 1 | Reoviridae,Rotavirus,Rotavirus A | seg. 1 | JF490501 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00046/2 006/G1P[8] | NC_011508 | vertebrates,human | 1 | Reoviridae,Rotavirus,Rotavirus A | seg. 3 | JF490510 |
| Rotavirus A human/Victoria/CK00046/2 006/G1P[8] | NC_011509 | vertebrates,human | 1 | Reoviridae,Rotavirus,Rotavirus A | seg. 6 | JF490508 |
| Rotavirus A human/Victoria/CK00046/2 006/G1P[8] | NC_011510 | vertebrates,human | 1 | Reoviridae,Rotavirus,Rotavirus A | seg. 4 | JF490509 |
| Rotavirus A human/Victoria/CK00047/2 006/G1P[8] | NC_011500 | vertebrates,human | 1 | Reoviridae,Rotavirus,Rotavirus A | seg. 5 | JF490514 |
| Rotavirus A human/Victoria/CK00047/2 006/G1P[8] | NC_011501 | vertebrates,human | 1 | Reoviridae,Rotavirus,Rotavirus A | seg. 7 | JF490518 |
| Rotavirus A human/Victoria/CK00047/2 006/G1P[8] | NC_011502 | vertebrates,human | 1 | Reoviridae,Rotavirus,Rotavirus A | seg. 8 | JF490513 |
| Rotavirus A human/Victoria/CK00047/2 006/G1P[8] | NC_011503 | vertebrates,human | 1 | Reoviridae,Rotavirus,Rotavirus A | seg. 9 | JF490517 |
| Rotavirus A human/Victoria/CK00047/2 006/G1P[8] | NC_011504 | vertebrates,human | 1 | Reoviridae,Rotavirus,Rotavirus A | seg. 10 | JF490516 |
| Rotavirus A human/Victoria/CK00047/2 006/G1P[8] | NC_011505 | vertebrates,human | 1 | Reoviridae,Rotavirus,Rotavirus A | seg. 11 | JF490515 |
| Rotavirus A human/Victoria/CK00047/2 006/G1P[8] | NC_011506 | vertebrates,human | 1 | Reoviridae,Rotavirus,Rotavirus A | seg. 2 | JF490522 |
| Rotavirus A human/Victoria/CK00047/2 006/G1P[8] | NC_011507 | vertebrates,human | 1 | Reoviridae,Rotavirus,Rotavirus A | seg. 1 | JF490512 |
| Rotavirus A human/Victoria/CK00047/2 006/G1P[8] | NC_011508 | vertebrates,human | 1 | Reoviridae,Rotavirus,Rotavirus A | seg. 3 | JF490521 |
| Rotavirus A human/Victoria/CK00047/2 006/G1P[8] | NC_011509 | vertebrates,human | 1 | Reoviridae,Rotavirus,Rotavirus A | seg. 6 | JF490519 |
| Rotavirus A human/Victoria/CK00047/2 006/G1P[8] | NC_011510 | vertebrates,human | 1 | Reoviridae,Rotavirus,Rotavirus A | seg. 4 | JF490520 |
| Rotavirus A human/Victoria/CK00048/2 004/G1P[8] | NC_011500 | vertebrates,human | 1 | Reoviridae,Rotavirus,Rotavirus A | seg. 5 | JF490525 |
| Rotavirus A human/Victoria/CK00048/2 004/G1P[8] | NC_011501 | vertebrates,human | 1 | Reoviridae,Rotavirus,Rotavirus A | seg. 7 | JF490529 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00048/2 004/G1P[8] | NC_011502 | vertebrates,human | 1 | Reoviridae,Rotavirus,Rotavirus A | seg. 8 | JF490524 |
| Rotavirus A human/Victoria/CK00048/2 004/G1P[8] | NC_011503 | vertebrates,human | 1 | Reoviridae,Rotavirus,Rotavirus A | seg. 9 | JF490528 |
| Rotavirus A human/Victoria/CK00048/2 004/G1P[8] | NC_011504 | vertebrates,human | 1 | Reoviridae,Rotavirus,Rotavirus A | seg. 10 | JF490527 |
| Rotavirus A human/Victoria/CK00048/2 004/G1P[8] | NC_011505 | vertebrates,human | 1 | Reoviridae,Rotavirus,Rotavirus A | seg. 11 | JF490526 |
| Rotavirus A human/Victoria/CK00048/2 004/G1P[8] | NC_011506 | vertebrates,human | 1 | Reoviridae,Rotavirus,Rotavirus A | seg. 2 | JF490533 |
| Rotavirus A human/Victoria/CK00048/2 004/G1P[8] | NC_011507 | vertebrates,human | 1 | Reoviridae,Rotavirus,Rotavirus A | seg. 1 | JF490523 |
| Rotavirus A human/Victoria/CK00048/2 004/G1P[8] | NC_011508 | vertebrates,human | 1 | Reoviridae,Rotavirus,Rotavirus A | seg. 3 | JF490532 |
| Rotavirus A human/Victoria/CK00048/2 004/G1P[8] | NC_011509 | vertebrates,human | 1 | Reoviridae,Rotavirus,Rotavirus A | seg. 6 | JF490530 |
| Rotavirus A human/Victoria/CK00048/2 004/G1P[8] | NC_011510 | vertebrates,human | 1 | Reoviridae,Rotavirus,Rotavirus A | seg. 4 | JF490531 |
| Rotavirus A human/Victoria/CK00048/2 004/G1P[8] | NC_011500 | vertebrates,human | 1 | Reoviridae,Rotavirus,Rotavirus A | seg. 5 | JF490536 |
| Rotavirus A human/Victoria/CK00049/2 004/G1P[8] | NC_011501 | vertebrates,human | 1 | Reoviridae,Rotavirus,Rotavirus A | seg. 7 | JF490540 |
| Rotavirus A human/Victoria/CK00049/2 004/G1P[8] | NC_011502 | vertebrates,human | 1 | Reoviridae,Rotavirus,Rotavirus A | seg. 8 | JF490535 |
| Rotavirus A human/Victoria/CK00049/2 004/G1P[8] | NC_011503 | vertebrates,human | 1 | Reoviridae,Rotavirus,Rotavirus A | seg. 9 | JF490539 |
| Rotavirus A human/Victoria/CK00049/2 004/G1P[8] | NC_011504 | vertebrates,human | 1 | Reoviridae,Rotavirus,Rotavirus A | seg. 10 | JF490538 |
| Rotavirus A human/Victoria/CK00049/2 004/G1P[8] | NC_011505 | vertebrates,human | 1 | Reoviridae,Rotavirus,Rotavirus A | seg. 11 | JF490537 |
| Rotavirus A human/Victoria/CK00049/2 004/G1P[8] | NC_011506 | vertebrates,human | 1 | Reoviridae,Rotavirus,Rotavirus A | seg. 2 | JF490544 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00049/2004/G1P[8] | NC_011507 | vertebrates,human | 1 | Reoviridae,Rotavirus,Rotavirus A | seg. 1 | JF490534 |
| Rotavirus A human/Victoria/CK00049/2004/G1P[8] | NC_011508 | vertebrates,human | 1 | Reoviridae,Rotavirus,Rotavirus A | seg. 3 | JF490542 |
| Rotavirus A human/Victoria/CK00049/2004/G1P[8] | NC_011509 | vertebrates,human | 1 | Reoviridae,Rotavirus,Rotavirus A | seg. 6 | JF490541 |
| Rotavirus A human/Victoria/CK00049/2004/G1P[8] | NC_011510 | vertebrates,human | 1 | Reoviridae,Rotavirus,Rotavirus A | seg. 4 | JF490543 |
| Rotavirus A human/Victoria/CK00050/2005/G1P[8] | NC_011500 | vertebrates,human | 1 | Reoviridae,Rotavirus,Rotavirus A | seg. 5 | JF490553 |
| Rotavirus A human/Victoria/CK00050/2005/G1P[8] | NC_011501 | vertebrates,human | 1 | Reoviridae,Rotavirus,Rotavirus A | seg. 7 | JF490550 |
| Rotavirus A human/Victoria/CK00050/2005/G1P[8] | NC_011502 | vertebrates,human | 1 | Reoviridae,Rotavirus,Rotavirus A | seg. 8 | JF490546 |
| Rotavirus A human/Victoria/CK00050/2005/G1P[8] | NC_011503 | vertebrates,human | 1 | Reoviridae,Rotavirus,Rotavirus A | seg. 9 | JF490549 |
| Rotavirus A human/Victoria/CK00050/2005/G1P[8] | NC_011504 | vertebrates,human | 1 | Reoviridae,Rotavirus,Rotavirus A | seg. 10 | JF490548 |
| Rotavirus A human/Victoria/CK00050/2005/G1P[8] | NC_011505 | vertebrates,human | 1 | Reoviridae,Rotavirus,Rotavirus A | seg. 11 | JF490547 |
| Rotavirus A human/Victoria/CK00050/2005/G1P[8] | NC_011506 | vertebrates,human | 1 | Reoviridae,Rotavirus,Rotavirus A | seg. 2 | JF490555 |
| Rotavirus A human/Victoria/CK00050/2005/G1P[8] | NC_011507 | vertebrates,human | 1 | Reoviridae,Rotavirus,Rotavirus A | seg. 1 | JF490545 |
| Rotavirus A human/Victoria/CK00050/2005/G1P[8] | NC_011508 | vertebrates,human | 1 | Reoviridae,Rotavirus,Rotavirus A | seg. 3 | JF490552 |
| Rotavirus A human/Victoria/CK00050/2005/G1P[8] | NC_011509 | vertebrates,human | 1 | Reoviridae,Rotavirus,Rotavirus A | seg. 6 | JF490551 |
| Rotavirus A human/Victoria/CK00050/2005/G1P[8] | NC_011510 | vertebrates,human | 1 | Reoviridae,Rotavirus,Rotavirus A | seg. 4 | JF490554 |
| Rotavirus A pheasant-tc/GER/10V0112H5/2010/G23P[37] | NC_011502 | vertebrates,human | 1 | Reoviridae,Rotavirus,Rotavirus A | seg. 8 | JX204816 |

-continued

| Taxonomy | NCBI Reference Sequence ID | Host | No. of Genomes | Lineage | Segment Count | Genbank Accession ID |
|---|---|---|---|---|---|---|
| Rotavirus A pheasant-tc/GER/10V0112H5/2010/G23P[37] | NC_011503 | vertebrates,human | 1 | Reoviridae,Rotavirus,Rotavirus A | seg. 9 | JX204818 |
| Rotavirus A pheasant-tc/GER/10V0112H5/2010/G23P[37] | NC_011506 | vertebrates,human | 1 | Reoviridae,Rotavirus,Rotavirus A | seg. 2 | JX204812 |
| Rotavirus A pheasant-tc/GER/10V0112H5/2010/G23P[37] | NC_011507 | vertebrates,human | 1 | Reoviridae,Rotavirus,Rotavirus A | seg. 1 | JX204811 |
| Rotavirus A pheasant-tc/GER/10V0112H5/2010/G23P[37] | NC_011508 | vertebrates,human | 1 | Reoviridae,Rotavirus,Rotavirus A | seg. 3 | JX204813 |
| Rotavirus A pheasant-tc/GER/10V0112H5/2010/G23P[37] | NC_011509 | vertebrates,human | 1 | Reoviridae,Rotavirus,Rotavirus A | seg. 6 | JX204815 |
| Rotavirus A pheasant-tc/GER/10V0112H5/2010/G23P[37] | NC_011510 | vertebrates,human | 1 | Reoviridae,Rotavirus,Rotavirus A | seg. 4 | JX204814 |
| Rotavirus A pheasant/HUN/2008 | NC_011503 | vertebrates,human | 3 | Reoviridae,Rotavirus,Rotavirus A | seg. 9 | FN393054,FN393055,FN393056 |
| Rotavirus A sable antelope/G6P[14] | NC_011500 | vertebrates,human | 1 | Reoviridae,Rotavirus,Rotavirus A | seg. 5 | FJ495130 |
| Rotavirus A sable antelope/G6P[14] | NC_011501 | vertebrates,human | 1 | Reoviridae,Rotavirus,Rotavirus A | seg. 7 | FJ495134 |
| Rotavirus A sable antelope/G6P[14] | NC_011502 | vertebrates,human | 1 | Reoviridae,Rotavirus,Rotavirus A | seg. 8 | FJ495132 |
| Rotavirus A sable antelope/G6P[14] | NC_011503 | vertebrates,human | 1 | Reoviridae,Rotavirus,Rotavirus A | seg. 9 | FJ495133 |
| Rotavirus A sable antelope/G6P[14] | NC_011504 | vertebrates,human | 1 | Reoviridae,Rotavirus,Rotavirus A | seg. 10 | FJ495135 |
| Rotavirus A sable antelope/G6P[14] | NC_011505 | vertebrates,human | 1 | Reoviridae,Rotavirus,Rotavirus A | seg. 11 | FJ495136 |
| Rotavirus A sable antelope/G6P[14] | NC_011506 | vertebrates,human | 1 | Reoviridae,Rotavirus,Rotavirus A | seg. 2 | FJ495127 |
| Rotavirus A sable antelope/G6P[14] | NC_011507 | vertebrates,human | 1 | Reoviridae,Rotavirus,Rotavirus A | seg. 1 | FJ495126 |
| Rotavirus A sable antelope/G6P[14] | NC_011508 | vertebrates,human | 1 | Reoviridae,Rotavirus,Rotavirus A | seg. 3 | FJ495128 |
| Rotavirus A sable antelope/G6P[14] | NC_011509 | vertebrates,human | 1 | Reoviridae,Rotavirus,Rotavirus A | seg. 6 | FJ495131 |
| Rotavirus A sable antelope/G6P[14] | NC_011510 | vertebrates,human | 1 | Reoviridae,Rotavirus,Rotavirus A | seg. 4 | FJ495129 |
| Rotavirus A strain 116E/AG | NC_011500 | vertebrates,human | 1 | Reoviridae,Rotavirus,Rotavirus A | seg. 5 | FJ361205 |
| Rotavirus A strain 116E/AG | NC_011501 | vertebrates,human | 1 | Reoviridae,Rotavirus,Rotavirus A | seg. 7 | FJ361207 |
| Rotavirus A strain 116E/AG | NC_011502 | vertebrates,human | 1 | Reoviridae,Rotavirus,Rotavirus A | seg. 8 | FJ361208 |
| Rotavirus A strain 116E/AG | NC_011503 | vertebrates,human | 1 | Reoviridae,Rotavirus,Rotavirus A | seg. 9 | FJ361209 |
| Rotavirus A strain 116E/AG 10 | NC_011504 | vertebrates,human | 1 | Reoviridae,Rotavirus,Rotavirus A | seg. | FJ361210 |

| Taxonomy | NCBI Reference Sequence ID | Host | No. of Genomes | Lineage | Segment Count | Genbank Accession ID |
|---|---|---|---|---|---|---|
| Rotavirus A strain 116E/AG 11 | NC_011505 | vertebrates,human | 1 | Reoviridae,Rotavirus,Rotavirus A | seg. | FJ361211 |
| Rotavirus A strain 116E/AG | NC_011506 | vertebrates,human | 1 | Reoviridae,Rotavirus,Rotavirus A | seg. 2 | FJ361202 |
| Rotavirus A strain 116E/AG | NC_011507 | vertebrates,human | 1 | Reoviridae,Rotavirus,Rotavirus A | seg. 1 | FJ361201 |
| Rotavirus A strain 116E/AG | NC_011508 | vertebrates,human | 1 | Reoviridae,Rotavirus,Rotavirus A | seg. 3 | FJ361203 |
| Rotavirus A strain 116E/AG | NC_011509 | vertebrates,human | 1 | Reoviridae,Rotavirus,Rotavirus A | seg. 6 | FJ361206 |
| Rotavirus A strain 116E/AG | NC_011510 | vertebrates,human | 1 | Reoviridae,Rotavirus,Rotavirus A | seg. 4 | FJ361204 |
| Rotavirus A turkey-tc/GER/03V0002E10/2003/G22P[35] | NC_011502 | vertebrates,human | 1 | Reoviridae,Rotavirus,Rotavirus A | seg. 8 | JX204827 |
| Rotavirus A turkey-tc/GER/03V0002E10/2003/G22P[35] | NC_011503 | vertebrates,human | 1 | Reoviridae,Rotavirus,Rotavirus A | seg. 9 | JX204829 |
| Rotavirus A turkey-tc/GER/03V0002E10/2003/G22P[35] | NC_011506 | vertebrates,human | 1 | Reoviridae,Rotavirus,Rotavirus A | seg. 2 | JX204823 |
| Rotavirus A turkey-tc/GER/03V0002E10/2003/G22P[35] | NC_011507 | vertebrates,human | 1 | Reoviridae,Rotavirus,Rotavirus A | seg. 1 | JX204822 |
| Rotavirus A turkey-tc/GER/03V0002E10/2003/G22P[35] | NC_011508 | vertebrates,human | 1 | Reoviridae,Rotavirus,Rotavirus A | seg. 3 | JX204824 |
| Rotavirus A turkey-tc/GER/03V0002E10/2003/G22P[35] | NC_011509 | vertebrates,human | 1 | Reoviridae,Rotavirus,Rotavirus A | seg. 6 | JX204826 |
| Rotavirus A turkey-tc/GER/03V0002E10/2003/G22P[35] | NC_011510 | vertebrates,human | 1 | Reoviridae,Rotavirus,Rotavirus A | seg. 4 | JX204825 |
| Rotavirus B | NC_021541 | vertebrates,human | 1 | Reoviridae,Rotavirus,Rotavirus B | seg. 1 | M97203 |
| Rotavirus B | NC_021544 | vertebrates,human | 1 | Reoviridae,Rotavirus,Rotavirus B | seg. 6 | AF079157 |
| Rotavirus B | NC_021549 | vertebrates,human | 1 | Reoviridae,Rotavirus,Rotavirus B | seg. 11 | AF079158 |
| Rotavirus C | NC_007543 | vertebrates,human | 1 | Reoviridae,Rotavirus,Rotavirus C | seg. 6 | AJ132203 |
| Rotavirus C | NC_007544 | vertebrates,human | 1 | Reoviridae,Rotavirus,Rotavirus C | seg. 7 | AJ132204 |
| Rotavirus C | NC_007545 | vertebrates,human | 1 | Reoviridae,Rotavirus,Rotavirus C | seg. 9 | AJ132205 |
| Rotavirus C | NC_007546 | vertebrates,human | 1 | Reoviridae,Rotavirus,Rotavirus C | seg. 2 | AJ303139 |
| Rotavirus C | NC_007547 | vertebrates,human | 1 | Reoviridae,Rotavirus,Rotavirus C | seg. 1 | AJ304859 |
| Rotavirus C | NC_007569 | vertebrates,human | 1 | Reoviridae,Rotavirus,Rotavirus C | seg. 10 | M81488 |
| Rotavirus C | NC_007570 | vertebrates,human | 4 | Reoviridae,Rotavirus,Rotavirus C | seg. 5 | AF162434,M88768,EF528570,X59843 |
| Rotavirus C | NC_007571 | vertebrates,human | 15 | Reoviridae,Rotavirus,Rotavirus C | seg. 8 | U20990,U20991,U20994,U20989,U20993,X77257,U20992,X77258,EF528571,X77256,AJ549087,U20996,U20987,U20995,U209988 |

| Taxonomy | NCBI Reference Sequence ID | Host | No. of Genomes | Lineage | Segment Count | Genbank Accession ID |
|---|---|---|---|---|---|---|
| Rotavirus C | NC_007572 | vertebrates,human | 1 | Reoviridae,Rotavirus,Rotavirus C | seg. 3 | X79442 |
| Rotavirus C | NC_007573 | vertebrates,human | 1 | Reoviridae,Rotavirus,Rotavirus C | seg. 11 | X83967 |
| Rotavirus C | NC_007574 | vertebrates,human | 1 | Reoviridae,Rotavirus,Rotavirus C | seg. 4 | X96697 |
| Rotavirus F chicken/03V0568/DEU/2003 | NC_021625 | vertebrates,human | 1 | Reoviridae,Rotavirus,Rotavirus F | seg. 1 | JN596591 |
| Rotavirus F chicken/03V0568/DEU/2003 | NC_021626 | vertebrates,human | 1 | Reoviridae,Rotavirus,Rotavirus F | seg. 2 | JQ919995 |
| Rotavirus F chicken/03V0568/DEU/2003 | NC_021627 | vertebrates,human | 1 | Reoviridae,Rotavirus,Rotavirus F | seg. 9 | JQ919998 |
| Rotavirus F chicken/03V0568/DEU/2003 | NC_021628 | vertebrates,human | 1 | Reoviridae,Rotavirus,Rotavirus F | seg. 8 | JQ920000 |
| Rotavirus F chicken/03V0568/DEU/2003 | NC_021629 | vertebrates,human | 1 | Reoviridae,Rotavirus,Rotavirus F | seg. 10 | JQ920003 |
| Rotavirus F chicken/03V0568/DEU/2003 | NC_021630 | vertebrates,human | 1 | Reoviridae,Rotavirus,Rotavirus F | seg. 4 | JQ919996 |
| Rotavirus F chicken/03V0568/DEU/2003 | NC_021631 | vertebrates,human | 1 | Reoviridae,Rotavirus,Rotavirus F | seg. 3 | JQ919997 |
| Rotavirus F chicken/03V0568/DEU/2003 | NC_021632 | vertebrates,human | 1 | Reoviridae,Rotavirus,Rotavirus F | seg. 5 | JQ919999 |
| Rotavirus F chicken/03V0568/DEU/2003 | NC_021633 | vertebrates,human | 1 | Reoviridae,Rotavirus,Rotavirus F | seg. 7 | JQ920001 |
| Rotavirus F chicken/03V0568/DEU/2003 | NC_021634 | vertebrates,human | 1 | Reoviridae,Rotavirus,Rotavirus F | seg. 11 | JQ920002 |
| Rotavirus F chicken/03V0568/DEU/2003 | NC_021635 | vertebrates,human | 1 | Reoviridae,Rotavirus,Rotavirus F | seg. 6 | HQ403603 |
| Rotavirus G chicken/03V0567/DEU/2003 | NC_021580 | vertebrates,human | 1 | Reoviridae,Rotavirus,Rotavirus G | — | JQ920004 |
| Rotavirus G chicken/03V0567/DEU/2003 | NC_021581 | vertebrates,human | 1 | Reoviridae,Rotavirus,Rotavirus G | — | JQ920006 |
| Rotavirus G chicken/03V0567/DEU/2003 | NC_021582 | vertebrates,human | 1 | Reoviridae,Rotavirus,Rotavirus G | — | JQ920007 |
| Rotavirus G chicken/03V0567/DEU/2003 | NC_021583 | vertebrates,human | 1 | Reoviridae,Rotavirus,Rotavirus G | — | JQ920008 |
| Rotavirus G chicken/03V0567/DEU/2003 | NC_021584 | vertebrates,human | 1 | Reoviridae,Rotavirus,Rotavirus G | — | JQ920009 |
| Rotavirus G chicken/03V0567/DEU/2003 | NC_021585 | vertebrates,human | 1 | Reoviridae,Rotavirus,Rotavirus G | — | JQ920010 |
| Rotavirus G chicken/03V0567/DEU/2003 | NC_021586 | vertebrates,human | 1 | Reoviridae,Rotavirus,Rotavirus G | — | JQ920011 |
| Rotavirus G chicken/03V0567/DEU/2003 | NC_021587 | vertebrates,human | 1 | Reoviridae,Rotavirus,Rotavirus G | — | JQ920012 |
| Rotavirus G chicken/03V0567/DEU/2003 | NC_021588 | vertebrates,human | 1 | Reoviridae,Rotavirus,Rotavirus G | — | HQ403604 |
| Rotavirus G chicken/03V0567/DEU/2003 | NC_021589 | vertebrates,human | 1 | Reoviridae,Rotavirus,Rotavirus G | — | JQ920005 |
| Rotavirus G chicken/03V0567/DEU/2003 | NC_021590 | vertebrates,human | 1 | Reoviridae,Rotavirus,Rotavirus G | — | JN596592 |

-continued

| Taxonomy | NCBI Reference Sequence ID | Host | No. of Genomes | Lineage | Segment Count | Genbank Accession ID |
|---|---|---|---|---|---|---|
| Rotavirus G1 | NC_011503 | vertebrates,human | 11 | Reoviridae,Rotavirus,Rotavirus A | seg. 9 | EU839916,EU839911,EU839909,EU839913,EU839912,EU839910,EU839915,EU839908,EU839907,EU839906,EU839914 |
| Rotavirus G1 | NC_011504 | vertebrates,human | 1 | Reoviridae,Rotavirus,Rotavirus A | seg. 10 | AY159645,AY159638,AY159631,AY159636,AY159632,AY159646,AY159633,AY159642,AY159643,AY159634,AY159644,AY159641,AY159640,AY159630,AY159637,AY159639,AY159635,AY159647,AY159648,AY159619 |
| Rotavirus G10 | NC_011503 | vertebrates,human | 7 | Reoviridae,Rotavirus,Rotavirus A | seg. 9 | AY816181,JF681943,AY843333,AY816182,AY855063,JF681941,AY843332 |
| Rotavirus G10 | NC_011504 | vertebrates,human | 1 | Reoviridae,Rotavirus,Rotavirus A | seg. 10 | AY855068 |
| Rotavirus G12 | NC_011501 | vertebrates,human | 2 | Reoviridae,Rotavirus,Rotavirus A | seg. 7 | EU839967,EU839973 |
| Rotavirus G12 | NC_011502 | vertebrates,human | 2 | Reoviridae,Rotavirus,Rotavirus A | seg. 8 | EU839968,EU839974 |
| Rotavirus G12 | NC_011503 | vertebrates,human | 18 | Reoviridae,Rotavirus,Rotavirus A | seg. 9 | AB436818,AB436813,EU839943,EU839993,EU839994,AB436814,EU839944,AB436815,EU839942,EF059916,AB436816,AB306271,AB436817,AB306270,EF059917,AB306268,EU839935,AB306269,AB436819 |
| Rotavirus G12 | NC_011504 | vertebrates,human | 4 | Reoviridae,Rotavirus,Rotavirus A | seg. 10 | EU839969,EF059919,EU839975,EF059918 |
| Rotavirus G12 | NC_011505 | vertebrates,human | 2 | Reoviridae,Rotavirus,Rotavirus A | seg. 11 | EU839970,EU839976 |
| Rotavirus G12 | NC_011509 | vertebrates,human | 2 | Reoviridae,Rotavirus,Rotavirus A | seg. 6 | EU839965,EU839971 |
| Rotavirus G12 | NC_011510 | vertebrates,human | 2 | Reoviridae,Rotavirus,Rotavirus A | seg. 4 | EF059921,EF059920 |
| Rotavirus G2 | NC_011503 | vertebrates,human | 16 | Reoviridae,Rotavirus,Rotavirus A | seg. 9 | AY707784,EU839925,EU839919,EU839992,AY707785,EU839917,EU839926,EU839918,EU839923,DQ478581,EU839924,EU839920,EU839922,EU839922... |

| Taxonomy | NCBI Reference Sequence ID | Host | No. of Genomes | Lineage | Segment Count | Genbank Accession ID |
|---|---|---|---|---|---|---|
| Rotavirus G2 | NC_011504 | vertebrates,human | 3 | Reoviridae,Rotavirus,Rotavirus A | seg. 10 | 839928,AY707786,EU839927 |
| Rotavirus G2 | NC_011509 | vertebrates,human | 1 | Reoviridae,Rotavirus,Rotavirus A | seg. 6 | AY159649,AF401756,EU839964 |
| Rotavirus G3 | NC_011500 | vertebrates,human | 1 | Reoviridae,Rotavirus,Rotavirus A | seg. 5 | AY740735 |
| Rotavirus G3 | NC_011501 | vertebrates,human | 1 | Reoviridae,Rotavirus,Rotavirus A | seg. 7 | AY740734 |
| Rotavirus G3 | NC_011502 | vertebrates,human | 2 | Reoviridae,Rotavirus,Rotavirus A | seg. 8 | JQ358771,AY740733 |
| Rotavirus G3 | NC_011503 | vertebrates,human | 51 | Reoviridae,Rotavirus,Rotavirus A | seg. 9 | EF495119,EF495124,AY707791,D86276,EF495121,EF495127,D0904498,D86264,D86282,6280,D86264,D86269,D JQ358764,D86269,D 86265,AY707789,AY 70792,EF495122,D 0904499,DQ995488, DQ995489,D86283,D 0904503,EF495118, DQ904500,DQ904450 5,AY870661,DQ9045 06,EF495120,D86284 ,D86281,DQ904502, D86279,DQ904501,D 86271,DQ995490,D8 72,AY900173,AY707 794,EF495126,D8627 8,D86268,D86267,D8 6274,EF495123,AY74 0736,DQ904504,AY7 07793,EF495125,D86 275 |
| Rotavirus G3 | NC_011504 | vertebrates,human | 21 | Reoviridae,Rotavirus,Rotavirus A | seg. 10 | AB008240,AB008236,AB008234,AB00824 6,AB008230,AB0082 33,AB008237,AY740 732,AB008242,AB0O 8238,AB008243,AB0 8231,AB008244,AB 08232,AB008245,A B008248,AB008247, AB008241,AB008239 ,AB008229,AB00823 5 |
| Rotavirus G3 | NC_011505 | vertebrates,human | 2 | Reoviridae,Rotavirus,Rotavirus A | seg. 11 | JQ358774,AY740731 |
| Rotavirus G3 | NC_011506 | vertebrates,human | 1 | Reoviridae,Rotavirus,Rotavirus A | seg. 2 | AY740740 |
| Rotavirus G3 | NC_011507 | vertebrates,human | 1 | Reoviridae,Rotavirus,Rotavirus A | seg. 1 | AY740741 |

| Taxonomy | NCBI Reference Sequence ID | Host | No. of Genomes | Lineage | Segment Count | Genbank Accession ID |
|---|---|---|---|---|---|---|
| Rotavirus G3 | NC_011508 | vertebrates,human | 1 | Reoviridae,Rotavirus,Rotavirus A | seg. 3 | AY740739 |
| Rotavirus G3 | NC_011509 | vertebrates,human | 1 | Reoviridae,Rotavirus,Rotavirus A | seg. 6 | AY740737 |
| Rotavirus G3 | NC_011510 | vertebrates,human | 20 | Reoviridae,Rotavirus,Rotavirus A | seg. 4 | AY740738,AB008277,AB008279,AB008278,AB008290,AB008291,AB008282,AB008289,AB008281,AB008272,AB008273,AB008274,AB008285,AB008275,AB008284,AB008286,AB008283,AB008280,AB008276,AB008288 |
| Rotavirus G4 | NC_011503 | vertebrates,human | 33 | Reoviridae,Rotavirus,Rotavirus A | seg. 9 | AB012066,AB012074,AF161822,AB039035,AB012075,AB039026,AB039027,AB012071,AB039025,AB012078,AF161821,AB039029,AF161823,AB012069,AF161817,AB012065,AB012079,AB039028,AB012072,AF161818,AB039032,AB012077,AB012067,AB012076,AB012073,AB039031,AB012068,AB012070,AF161820,AB039030,AF161819,AB039034,AB039033 |
| Rotavirus G4 | NC_011504 | vertebrates,human | 33 | Reoviridae,Rotavirus,Rotavirus A | seg. 10 | AB008255,AB008261,AF161810,AB043069,AF161815,AB043026,AB008251,AB008260,AB008253,AB008262,AB008249,AF161811,AB043072,AB043075,AF161813,AB008258,AB043076,AF161816,AB008259,AB008252,AB008263,AB008252,AB008263,AB008252,AB008263,AB008254,AF161812 |

| Taxonomy | NCBI Reference Sequence ID | Host | No. of Genomes | Lineage | Segment Count | Genbank Accession ID |
|---|---|---|---|---|---|---|
| Rotavirus G6 | NC_011503 | vertebrates,human | 1 | Reoviridae,Rotavirus,Rotavirus A | seg. 9 | AF532202 |
| Rotavirus G8 | NC_011503 | vertebrates,human | 1 | Reoviridae,Rotavirus,Rotavirus A | seg. 9 | AY85064 |
| Rotavirus G8 | NC_011510 | vertebrates,human | 1 | Reoviridae,Rotavirus,Rotavirus A | seg. 4 | AF045228 |
| Rotavirus G9 | NC_011503 | vertebrates,human | 156 | Reoviridae,Rotavirus,Rotavirus A | seg. 9 | AY253834,AJ250544, AB436831,AJ250276, EF199728,AB436820, AY69298,AB436832, AY262748,AY69930 2,AY307092,AY3070 88,AY307094,AB436 833,AY866500,AY87 9296,AY699301,EF19 9729,AY253835,AY6 99291,FJ695604,EF1 99735,AJ250275,AY2 11065,AJ250270,EU8 39936,AJ250269,DQ 647423,EU839929,E U839939,EF199736, AB436821,DQ056298 ,AY699292,AB09175 2,EF532837,AY69929 0,AB436822,EF19973 8,AB091755,EU8399 37,AY262747,AY211 067,AJ250268,AB364 369,EU839933,AY25 3836,AB436834,AJ25 0274,EU839932,AY6 99293,DQ056299,AJ 250277,DQ056300,E F199737,HQ018933,J F703095,DQ096290, AY695811,AY211068 ,HQ018932,AY25383 3,AY866504,EU8399 40,AY699294,AJ4911 79,DQ056297,EF199 730,AB091750,AJ491 177,AB436826,DQ05 6296,AY699297,AJ25 0272,EU839930,AB0 91751,JF703094,DQO 96288,EF199732,EF1 99726,AB091748,EF1 99734,AY253838,DQ 990318,AY262746,A Y253839,EF687001,E |

| Taxonomy | NCBI Reference Sequence ID | Host | No. of Genomes | Lineage | Segment Count | Genbank Accession ID |
|---|---|---|---|---|---|---|
| | | | | | | U839938,AY699296, AY184813,AY307087 ,AB436824,AJ491184 ,AY699299,AB36438 0,AB045372,DQ0962 93,EF199727,AJ2502 73,EF059922,DQ096 292,AB436835,AY30 7086,AB436830,AB0 91754,AY307093,DQ 096289,AY699304,A Y695809,AB091749, AY262749,EF199725, AB091756,DQ990319 ,AY307091,AJ491175 ,AY866502,AB43682 7,AB436825,AB0453 73,HQ018934,DQ096 294,AY699303,DQ99 0317,DQ096291,AB4 36829,AY866505,AY 253837,EU753963,A B436823,AY866501, AY866503,AB091747 ,EU839941,EF19973 1,AB436828,AY3070 85,JF703096,AB0917 53,AF359358,AJ2505 40,AY307090,DQ490 173,EF199733,AB091 746,AY816184,AB04 5374,AJ250271,EU83 9931,AJ491172,AJ25 0545,AY699295,AY 07089,AY699300,AY3 211066,JF703097 |
| Rotavirus G9 | NC_011504 | vertebrates,human | 4 | Reoviridae,Rotavirus,Rotavirus A | seg. 10 | EF033203,EF059924, EF033202,EF033204 |
| Rotavirus G9 | NC_011509 | vertebrates,human | 1 | Reoviridae,Rotavirus,Rotavirus A | seg. 6 | EU753964 |
| Rotavirus G9 | NC_011510 | vertebrates,human | 1 | Reoviridae,Rotavirus,Rotavirus A | seg. 4 | EF059923 |
| Rotavirus RVA/G1/Human/India/UK-HLD/2011/H14 | NC_011503 | vertebrates,human | 1 | Reoviridae,Rotavirus,Rotavirus A | seg. 9 | JX411969 |
| Rotavirus RVA/G1/Human/India/UK-HLD/2011/H180 | NC_011503 | vertebrates,human | 1 | Reoviridae,Rotavirus,Rotavirus A | seg. 9 | JX411970 |

-continued

| Taxonomy | NCBI Reference Sequence ID | Host | No. of Genomes | Lineage | Segment Count | Genbank Accession ID |
|---|---|---|---|---|---|---|
| Rotavirus RVA/G9/Human/India/UK-HLD/2011/H140 | NC_011503 | vertebrates,human | 1 | Reoviridae,Rotavirus,Rotavirus A | seg. 9 | JX411968 |
| Rotavirus str.US1205 | NC_011503 | vertebrates,human | 1 | Reoviridae,Rotavirus,Rotavirus A | seg. 9 | AF060487 |
| Rotavirus strain TUCH | NC_011509 | vertebrates,human | 1 | Reoviridae,Rotavirus,Rotavirus A | seg. 6 | AY594670 |
| Rotavirus strain TUCH | NC_011510 | vertebrates,human | 1 | Reoviridae,Rotavirus,Rotavirus A | seg. 4 | AY596189 |
| Rotavirus subgroup 1 | NC_011503 | vertebrates,human | 2 | Reoviridae,Rotavirus,Rotavirus A | seg. 9 | K02028,L11605 |
| Rotavirus subgroup 1 | NC_011504 10 | vertebrates,human | 1 | Reoviridae,Rotavirus,Rotavirus A | seg. | K03384 |
| Rotavirus subgroup 1 | NC_011505 11 | vertebrates,human | 1 | Reoviridae,Rotavirus,Rotavirus A | seg. | K03385 |
| Rotavirus subgroup 2 | NC_011509 | vertebrates,human | 1 | Reoviridae,Rotavirus,Rotavirus A | seg. 6 | DQ0325 |
| Rotavirus subgroup 2 | NC_011501 | vertebrates,human | 1 | Reoviridae,Rotavirus,Rotavirus A | seg. 7 | X57944 |
| Rotavirus subgroup 2 | NC_011503 | vertebrates,human | 1 | Reoviridae,Rotavirus,Rotavirus A | seg. 9 | K02033 |
| Rotavirus subgroup 2 | NC_011504 10 | vertebrates,human | 1 | Reoviridae,Rotavirus,Rotavirus A | seg. | K02032 |
| Rotavirus subgroup 2 | NC_011509 | vertebrates,human | 2 | Reoviridae,Rotavirus,Rotavirus A | seg. 6 | X57943,K02086 |
| Rubella virus | NC_001545 | vertebrates,human | 47 | Togaviridae,Rubivirus,Rubella virus | — | AY258323,K02086,JN635281,JN635282,JN635292,JN635285,AF435866,JN635296,DQ085341,AB047329,AF435865,AB588193,DQ08534 0,L78917,JN635290,AB588188,AB047330,JN635293,JN635288,AB222608,JN635284,DQ388281,JN635529 1,JF727653,FJ21158 8,JN635287,AB22260 9,KF201674,AB58819 1,JN635295,JN63528 3,AB588192,JN63528 9,AF188704,AY25832 2,AB588189,JN63529 4,DQ388280,JF72765 4,DQ085342,AB5881 90,M15240,DQ08534 3,FJ211587,DQ0853 9,JN635286,DQ0853 38,DQ388279 |
| SARS Coronavirus CDC#200301157 | NC_004718 | vertebrates,human | 1 | Coronaviridae,Betacoronavirus,Severe acute respiratory syndrome-related coronavirus | — | AY714217 |
| SARS coronavirus | NC_004718 | vertebrates,human | 25 | Coronaviridae,Betacoronavirus,Severe acute respiratory syndrome-related coronavirus | — | AY545914,JX163925,AY545917,CS569493,C0918585,DQ89817 4,JX163923,C09185 84,CS079026,CS079 |

| Taxonomy | NCBI Reference Sequence ID | Host | No. of Genomes | Lineage | Segment Count | Genbank Accession ID |
|---|---|---|---|---|---|---|
| | | | | | | 027,JX163924,JX163 926,AY545916,JX163 928,DQ497008,CS07 9029,JX163927,CS07 9028,CS254197,AY5 45918,C0918598,FJ9 59407,AY274119,AY 545919,AY545915 |
| SARS coronavirus A022 | NC_004718 | vertebrates,human | 1 | Coronaviridae,Betacoronavirus,Severe acute respiratory syndrome-related coronavirus | — | AY686863 |
| SARS coronavirus AS | N -continued

| Taxonomy | NCBI Reference Sequence ID | Host | No. of Genomes | Lineage | Segment Count | Genbank Accession ID |
|---|---|---|---|---|---|---|
| SARS coronavirus ExoN1 | NC_004718 | vertebrates,human | 33 | Coronaviridae,Betacoronavirus,Severe acute respiratory syndrome-related coronavirus | — | FJ882956,KF514395, KF514410,FJ882950, FJ882931,KF514412, KF514406,KF514403, FJ882955,KF514401, KF514416,KF514391, FJ882940,KF514417, KF514420,KF514393, KF514389,KF514405, KF514390,KF514402, FJ882926,KF514411, FJ882928,FJ882930, KF514414,FJ882941, FJ882944,KF514407, FJ882954,FJ882960, JF292922,JX162087, FJ882929 |
| SARS coronavirus FRA | NC_004718 | vertebrates,human | 1 | Coronaviridae,Betacoronavirus,Severe acute respiratory syndrome-related coronavirus | — | AY310120 |
| SARS coronavirus Frankfurt 1 | NC_004718 | vertebrates,human | 2 | Coronaviridae,Betacoronavirus,Severe acute respiratory syndrome-related coronavirus | — | AB257344,AY291315 |
| SARS coronavirus GDQ1 | NC_004718 | vertebrates,human | 1 | Coronaviridae,Betacoronavirus,Severe acute respiratory syndrome-related coronavirus | — | AY278489 |
| SARS coronavirus GD69 | NC_004718 | vertebrates,human | 1 | Coronaviridae,Betacoronavirus,Severe acute respiratory syndrome-related coronavirus | — | AY313906 |
| SARS coronavirus GDH-BJHO1 | NC_004718 | vertebrates,human | 1 | Coronaviridae,Betacoronavirus,Severe acute respiratory syndrome-related coronavirus | — | DQ640652 |
| SARS coronavirus GZ-A | NC_004718 | vertebrates,human | 1 | Coronaviridae,Betacoronavirus,Severe acute respiratory syndrome-related coronavirus | — | AY394977 |
| SARS coronavirus GZ-B | NC_004718 | vertebrates,human | 1 | Coronaviridae,Betacoronavirus,Severe acute respiratory syndrome-related coronavirus | — | AY394978 |
| SARS coronavirus GZ-C | NC_004718 | vertebrates,human | 1 | Coronaviridae,Betacoronavirus,Severe acute respiratory syndrome-related coronavirus | — | AY394979 |
| SARS coronavirus GZ-D | NC_004718 | vertebrates,human | 1 | Coronaviridae,Betacoronavirus,Severe acute respiratory syndrome-related coronavirus | — | AY394980 |
| SARS coronavirus GZO2 | NC_004718 | vertebrates,human | 1 | Coronaviridae,Betacoronavirus,Severe acute respiratory syndrome-related coronavirus | — | AY390556 |
| SARS coronavirus GZ0401 | NC_004718 | vertebrates,human | 1 | Coronaviridae,Betacoronavirus,Severe acute respiratory syndrome-related coronavirus | — | AY568539 |
| SARS coronavirus GZ0402 | NC_004718 | vertebrates,human | 1 | Coronaviridae,Betacoronavirus,Severe acute respiratory syndrome-related coronavirus | — | AY613947 |
| SARS coronavirus GZ50 | NC_004718 | vertebrates,human | 1 | Coronaviridae,Betacoronavirus,Severe acute respiratory syndrome-related coronavirus | — | AY304495 |
| SARS coronavirus HC/SZ/61/03 | NC_004718 | vertebrates,human | 1 | Coronaviridae,Betacoronavirus,Severe acute respiratory syndrome-related coronavirus | — | AY515512 |
| SARS coronavirus HGZ8L1-A | NC_004718 | vertebrates,human | 1 | Coronaviridae,Betacoronavirus,Severe acute respiratory syndrome-related coronavirus | — | AY394981 |

-continued

| Taxonomy | NCBI Reference Sequence ID | Host | No. of Genomes | Lineage | Segment Count | Genbank Accession ID |
|---|---|---|---|---|---|---|
| SARS coronavirus HGZ8L1-B | NC_004718 | vertebrates,human | 1 | Coronaviridae,Betacoronavirus,Severe acute respiratory syndrome-related coronavirus | — | AY394982 |
| SARS coronavirus HGZ8L2 | NC_004718 | vertebrates,human | 1 | Coronaviridae,Betacoronavirus,Severe acute respiratory syndrome-related coronavirus | — | AY394993 |
| SARS coronavirus HKU-39849 | NC_004718 | vertebrates,human | 6 | Coronaviridae,Betacoronavirus,Severe acute respiratory syndrome-related coronavirus | — | JQ316196,JN854286, GU553365,AY278491 ,GU553363,GU55336 4 |
| SARS coronavirus HSR 1 | NC_004718 | vertebrates,human | 1 | Coronaviridae,Betacoronavirus,Severe acute respiratory syndrome-related coronavirus | — | AY323977 |
| SARS coronavirus HSZ-A | NC_004718 | vertebrates,human | 1 | Coronaviridae,Betacoronavirus,Severe acute respiratory syndrome-related coronavirus | — | AY394984 |
| SARS coronavirus HSZ-Bb | NC_004718 | vertebrates,human | 1 | Coronaviridae,Betacoronavirus,Severe acute respiratory syndrome-related coronavirus | — | AY394985 |
| SARS coronavirus HSZ-Bc | NC_004718 | vertebrates,human | 1 | Coronaviridae,Betacoronavirus,Severe acute respiratory syndrome-related coronavirus | — | AY394994 |
| SARS coronavirus HSZ-Cb | NC_004718 | vertebrates,human | 1 | Coronaviridae,Betacoronavirus,Severe acute respiratory syndrome-related coronavirus | — | AY394986 |
| SARS coronavirus HSZ-Cc | NC_004718 | vertebrates,human | 1 | Coronaviridae,Betacoronavirus,Severe acute respiratory syndrome-related coronavirus | — | AY394995 |
| SARS coronavirus HSZ2-A | NC_004718 | vertebrates,human | 1 | Coronaviridae,Betacoronavirus,Severe acute respiratory syndrome-related coronavirus | — | AY394983 |
| SARS coronavirus HZS2-Bb | NC_004718 | vertebrates,human | 1 | Coronaviridae,Betacoronavirus,Severe acute respiratory syndrome-related coronavirus | — | AY395004 |
| SARS coronavirus HZS2-C | NC_004718 | vertebrates,human | 1 | Coronaviridae,Betacoronavirus,Severe acute respiratory syndrome-related coronavirus | — | AY394992 |
| SARS coronavirus HZS2-D | NC_004718 | vertebrates,human | 1 | Coronaviridae,Betacoronavirus,Severe acute respiratory syndrome-related coronavirus | — | AY394989 |
| SARS coronavirus HZS2-E | NC_004718 | vertebrates,human | 1 | Coronaviridae,Betacoronavirus,Severe acute respiratory syndrome-related coronavirus | — | AY394990 |
| SARS coronavirus HZS2-Fb | NC_004718 | vertebrates,human | 1 | Coronaviridae,Betacoronavirus,Severe acute respiratory syndrome-related coronavirus | — | AY394987 |
| SARS coronavirus HZS2-Fc | NC_004718 | vertebrates,human | 1 | Coronaviridae,Betacoronavirus,Severe acute respiratory syndrome-related coronavirus | — | AY394991 |
| SARS coronavirus JMD | NC_004718 | vertebrates,human | 1 | Coronaviridae,Betacoronavirus,Severe acute respiratory syndrome-related coronavirus | — | AY394988 |
| SARS coronavirus LC1 | NC_004718 | vertebrates,human | 1 | Coronaviridae,Betacoronavirus,Severe acute respiratory syndrome-related coronavirus | — | AY394998 |
| SARS coronavirus LC2 | NC_004718 | vertebrates,human | 1 | Coronaviridae,Betacoronavirus,Severe acute respiratory syndrome-related coronavirus | — | AY394999 |
| SARS coronavirus LC3 | NC_004718 | vertebrates,human | 1 | Coronaviridae,Betacoronavirus,Severe acute respiratory syndrome-related coronavirus | — | AY395000 |
| SARS coronavirus LC4 | NC_004718 | vertebrates,human | 1 | Coronaviridae,Betacoronavirus,Severe acute respiratory syndrome-related coronavirus | — | AY395001 |
| SARS coronavirus LC5 | NC_004718 | vertebrates,human | 1 | Coronaviridae,Betacoronavirus,Severe acute respiratory syndrome-related coronavirus | — | AY395002 |

-continued

| Taxonomy | NCBI Reference Sequence ID | Host | No. of Genomes | Lineage | Segment Count | Genbank Accession ID |
|---|---|---|---|---|---|---|
| SARS coronavirus LU-2004 | NC_004718 | vertebrates,human | 1 | Coronaviridae,Betacoronavirus,Severe acute respiratory syndrome-related coronavirus | — | AY595412 |
| SARS coronavirus MA15 | NC_004718 | vertebrates,human | 26 | Coronaviridae,Betacoronavirus,Severe acute respiratory syndrome-related coronavirus | — | FJ882958,JF292910, FJ882961,JF292912, FJ882948,JF292914, JF292911,JF292908, FJ882952,JF292915, JF292918,HQ890546, HQ890542,JF292917, FJ882945,JF292913, HQ890543,HQ890544,HQ890545,HQ890541,JF292916,JF292919,JF292909,JF292907,FJ882957,JF292920 |
| SARS coronavirus MA15 ExoN1 | NC_004718 | vertebrates,human | 26 | Coronaviridae,Betacoronavirus,Severe acute respiratory syndrome-related coronavirus | — | FJ882953,HQ890539, JF292904,FJ882942, HQ890527,HQ890529,HQ890538,HQ890536,HQ890540,JF292903,HQ890526,HQ890537,FJ882959,FJ882943,FJ882951,HQ890530,HQ890535,JF292902,HQ890532,HQ890533,HQ890531,HQ890534,HQ890528,JF292906,JF292905,FJ882962 |
| SARS coronavirus NS-1 | NC_004718 | vertebrates,human | 1 | Coronaviridae,Betacoronavirus,Severe acute respiratory syndrome-related coronavirus | — | AY508724 |
| SARS coronavirus P2 | NC_004718 | vertebrates,human | 1 | Coronaviridae,Betacoronavirus,Severe acute respiratory syndrome-related coronavirus | — | FJ882963 |
| SARS coronavirus PC4-13 | NC_004718 | vertebrates,human | 1 | Coronaviridae,Betacoronavirus,Severe acute respiratory syndrome-related coronavirus | — | AY613948 |
| SARS coronavirus PC4-136 | NC_004718 | vertebrates,human | 1 | Coronaviridae,Betacoronavirus,Severe acute respiratory syndrome-related coronavirus | — | AY613949 |
| SARS coronavirus PC4-227 | NC_004718 | vertebrates,human | 1 | Coronaviridae,Betacoronavirus,Severe acute respiratory syndrome-related coronavirus | — | AY613950 |
| SARS coronavirus PUMC01 | NC_004718 | vertebrates,human | 1 | Coronaviridae,Betacoronavirus,Severe acute respiratory syndrome-related coronavirus | — | AY350750 |
| SARS coronavirus PUMCO2 | NC_004718 | vertebrates,human | 1 | Coronaviridae,Betacoronavirus,Severe acute respiratory syndrome-related coronavirus | — | AY357075 |
| SARS coronavirus PUMC03 | NC_004718 | vertebrates,human | 1 | Coronaviridae,Betacoronavirus,Severe acute respiratory syndrome-related coronavirus | — | AY357076 |
| SARS coronavirus Rs_672/2006 | NC_004718 | vertebrates,human | 1 | Coronaviridae,Betacoronavirus,Severe acute respiratory syndrome-related coronavirus | — | FJ588686 |

-continued

| Taxonomy | NCBI Reference Sequence ID | Host | No. of Genomes | Lineage | Segment Count | Genbank Accession ID |
|---|---|---|---|---|---|---|
| SARS coronavirus ShanghaiQXC1 | NC_004718 | vertebrates,human | 1 | Coronaviridae,Betacoronavirus,Severe acute respiratory syndrome-related coronavirus | — | AY463059 |
| SARS coronavirus ShanghaiQXC2 | NC_004718 | vertebrates,human | 1 | Coronaviridae,Betacoronavirus,Severe acute respiratory syndrome-related coronavirus | — | AY463060 |
| SARS coronavirus Sin2500 | NC_004718 | vertebrates,human | 1 | Coronaviridae,Betacoronavirus,Severe acute respiratory syndrome-related coronavirus | — | AY283794 |
| SARS coronavirus Sin2677 | NC_004718 | vertebrates,human | 1 | Coronaviridae,Betacoronavirus,Severe acute respiratory syndrome-related coronavirus | — | AY283795 |
| SARS coronavirus Sin2679 | NC_004718 | vertebrates,human | 1 | Coronaviridae,Betacoronavirus,Severe acute respiratory syndrome-related coronavirus | — | AY283796 |
| SARS coronavirus Sin2748 | NC_004718 | vertebrates,human | 1 | Coronaviridae,Betacoronavirus,Severe acute respiratory syndrome-related coronavirus | — | AY283797 |
| SARS coronavirus Sin2774 | NC_004718 | vertebrates,human | 1 | Coronaviridae,Betacoronavirus,Severe acute respiratory syndrome-related coronavirus | — | AY283798 |
| SARS coronavirus Sin3408 | NC_004718 | vertebrates,human | 1 | Coronaviridae,Betacoronavirus,Severe acute respiratory syndrome-related coronavirus | — | AY559083 |
| SARS coronavirus Sin3408L | NC_004718 | vertebrates,human | 1 | Coronaviridae,Betacoronavirus,Severe acute respiratory syndrome-related coronavirus | — | AY559097 |
| SARS coronavirus Sin3725V | NC_004718 | vertebrates,human | 1 | Coronaviridae,Betacoronavirus,Severe acute respiratory syndrome-related coronavirus | — | AY559087 |
| SARS coronavirus Sin3765V | NC_004718 | vertebrates,human | 1 | Coronaviridae,Betacoronavirus,Severe acute respiratory syndrome-related coronavirus | — | AY559084 |
| SARS coronavirus Sin842 | NC_004718 | vertebrates,human | 1 | Coronaviridae,Betacoronavirus,Severe acute respiratory syndrome-related coronavirus | — | AY559081 |
| SARS coronavirus Sin845 | NC_004718 | vertebrates,human | 1 | Coronaviridae,Betacoronavirus,Severe acute respiratory syndrome-related coronavirus | — | AY559093 |
| SARS coronavirus Sin846 | NC_004718 | vertebrates,human | 1 | Coronaviridae,Betacoronavirus,Severe acute respiratory syndrome-related coronavirus | — | AY559094 |
| SARS coronavirus Sin847 | NC_004718 | vertebrates,human | 1 | Coronaviridae,Betacoronavirus,Severe acute respiratory syndrome-related coronavirus | — | AY559095 |
| SARS coronavirus Sin848 | NC_004718 | vertebrates,human | 1 | Coronaviridae,Betacoronavirus,Severe acute respiratory syndrome-related coronavirus | — | AY559085 |
| SARS coronavirus Sin849 | NC_004718 | vertebrates,human | 1 | Coronaviridae,Betacoronavirus,Severe acute respiratory syndrome-related coronavirus | — | AY559086 |
| SARS coronavirus Sin850 | NC_004718 | vertebrates,human | 1 | Coronaviridae,Betacoronavirus,Severe acute respiratory syndrome-related coronavirus | — | AY559096 |
| SARS coronavirus Sin852 | NC_004718 | vertebrates,human | 1 | Coronaviridae,Betacoronavirus,Severe acute respiratory syndrome-related coronavirus | — | AY559082 |
| SARS coronavirus SinP1 | NC_004718 | vertebrates,human | 1 | Coronaviridae,Betacoronavirus,Severe acute respiratory syndrome-related coronavirus | — | AY559088 |
| SARS coronavirus SinP2 | NC_004718 | vertebrates,human | 1 | Coronaviridae,Betacoronavirus,Severe acute respiratory syndrome-related coronavirus | — | AY559089 |
| SARS coronavirus SinP3 | NC_004718 | vertebrates,human | 1 | Coronaviridae,Betacoronavirus,Severe acute respiratory syndrome-related coronavirus | — | AY559090 |
| SARS coronavirus SinP4 | NC_004718 | vertebrates,human | 1 | Coronaviridae,Betacoronavirus,Severe acute respiratory syndrome-related coronavirus | — | AY559091 |
| SARS coronavirus SinP5 | NC_004718 | vertebrates,human | 1 | Coronaviridae,Betacoronavirus,Severe acute respiratory syndrome-related coronavirus | — | AY559092 |

-continued

| Taxonomy | NCBI Reference Sequence ID | Host | No. of Genomes | Lineage | Segment Count | Genbank Accession ID |
|---|---|---|---|---|---|---|
| SARS coronavirus Sino1-11 | NC_004718 | vertebrates,human | 1 | Coronaviridae,Betacoronavirus,Severe acute respiratory syndrome-related coronavirus | — | AY485277 |
| SARS coronavirus Sino3-11 | NC_004718 | vertebrates,human | 1 | Coronaviridae,Betacoronavirus,Severe acute respiratory syndrome-related coronavirus | — | AY485278 |
| SARS coronavirus SoD | NC_004718 | vertebrates,human | 1 | Coronaviridae,Betacoronavirus,Severe acute respiratory syndrome-related coronavirus | — | AY461660 |
| SARS coronavirus TJF | NC_004718 | vertebrates,human | 1 | Coronaviridae,Betacoronavirus,Severe acute respiratory syndrome-related coronavirus | — | AY654624 |
| SARS coronavirus TW1 | NC_004718 | vertebrates,human | 1 | Coronaviridae,Betacoronavirus,Severe acute respiratory syndrome-related coronavirus | — | AY291451 |
| SARS coronavirus TW10 | NC_004718 | vertebrates,human | 1 | Coronaviridae,Betacoronavirus,Severe acute respiratory syndrome-related coronavirus | — | AY502923 |
| SARS coronavirus TW11 | NC_004718 | vertebrates,human | 1 | Coronaviridae,Betacoronavirus,Severe acute respiratory syndrome-related coronavirus | — | AY502924 |
| SARS coronavirus TW2 | NC_004718 | vertebrates,human | 1 | Coronaviridae,Betacoronavirus,Severe acute respiratory syndrome-related coronavirus | — | AY502925 |
| SARS coronavirus TW3 | NC_004718 | vertebrates,human | 1 | Coronaviridae,Betacoronavirus,Severe acute respiratory syndrome-related coronavirus | — | AY502926 |
| SARS coronavirus TW4 | NC_004718 | vertebrates,human | 1 | Coronaviridae,Betacoronavirus,Severe acute respiratory syndrome-related coronavirus | — | AY502927 |
| SARS coronavirus TW5 | NC_004718 | vertebrates,human | 1 | Coronaviridae,Betacoronavirus,Severe acute respiratory syndrome-related coronavirus | — | AY502928 |
| SARS coronavirus TW6 | NC_004718 | vertebrates,human | 1 | Coronaviridae,Betacoronavirus,Severe acute respiratory syndrome-related coronavirus | — | AY502929 |
| SARS coronavirus TW7 | NC_004718 | vertebrates,human | 1 | Coronaviridae,Betacoronavirus,Severe acute respiratory syndrome-related coronavirus | — | AY502930 |
| SARS coronavirus TW8 | NC_004718 | vertebrates,human | 1 | Coronaviridae,Betacoronavirus,Severe acute respiratory syndrome-related coronavirus | — | AY502931 |
| SARS coronavirus TW9 | NC_004718 | vertebrates,human | 1 | Coronaviridae,Betacoronavirus,Severe acute respiratory syndrome-related coronavirus | — | AY502932 |
| SARS coronavirus TWC | NC_004718 | vertebrates,human | 1 | Coronaviridae,Betacoronavirus,Severe acute respiratory syndrome-related coronavirus | — | AY321118 |
| SARS coronavirus TWC2 | NC_004718 | vertebrates,human | 1 | Coronaviridae,Betacoronavirus,Severe acute respiratory syndrome-related coronavirus | — | AY362698 |
| SARS coronavirus TWC3 | NC_004718 | vertebrates,human | 1 | Coronaviridae,Betacoronavirus,Severe acute respiratory syndrome-related coronavirus | — | AY362699 |
| SARS coronavirus TWH | NC_004718 | vertebrates,human | 1 | Coronaviridae,Betacoronavirus,Severe acute respiratory syndrome-related coronavirus | — | AP006557 |
| SARS coronavirus TWJ | NC_004718 | vertebrates,human | 1 | Coronaviridae,Betacoronavirus,Severe acute respiratory syndrome-related coronavirus | — | AP006558 |
| SARS coronavirus TWK | NC_004718 | vertebrates,human | 1 | Coronaviridae,Betacoronavirus,Severe acute respiratory syndrome-related coronavirus | — | AP006559 |
| SARS coronavirus TWS | NC_004718 | vertebrates,human | 1 | Coronaviridae,Betacoronavirus,Severe acute respiratory syndrome-related coronavirus | — | AP006560 |
| SARS coronavirus TWY | NC_004718 | vertebrates,human | 1 | Coronaviridae,Betacoronavirus,Severe acute respiratory syndrome-related coronavirus | — | AP006561 |
| SARS coronavirus Taiwan TC1 | NC_004718 | vertebrates,human | 1 | Coronaviridae,Betacoronavirus,Severe acute respiratory syndrome-related coronavirus | — | AY338174 |

-continued

| Taxonomy | NCBI Reference Sequence ID | Host | No. of Genomes | Lineage | Segment Count | Genbank Accession ID |
|---|---|---|---|---|---|---|
| SARS coronavirus Taiwan TC2 | NC_004718 | vertebrates,human | 1 | Coronaviridae,Betacoronavirus,Severe acute respiratory syndrome-related coronavirus | — | AY338175 |
| SARS coronavirus Taiwan TC3 | NC_004718 | vertebrates,human | 1 | Coronaviridae,Betacoronavirus,Severe acute respiratory syndrome-related coronavirus | — | AY348314 |
| SARS coronavirus Urbani | NC_004718 | vertebrates,human | 1 | Coronaviridae,Betacoronavirus,Severe acute respiratory syndrome-related coronavirus | — | AY278741 |
| SARS coronavirus W H20 | NC_004718 | vertebrates,human | 1 | Coronaviridae,Betacoronavirus,Severe acute respiratory syndrome-related coronavirus | — | AY772062 |
| SARS coronavirus W HU | NC_004718 | vertebrates,human | 1 | Coronaviridae,Betacoronavirus,Severe acute respiratory syndrome-related coronavirus | — | AY394850 |
| SARS coronavirus ZJO1 | NC_004718 | vertebrates,human | 1 | Coronaviridae,Betacoronavirus,Severe acute respiratory syndrome-related coronavirus | — | AY297028 |
| SARS coronavirus ZJO2 | NC_004718 | vertebrates,human | 1 | Coronaviridae,Betacoronavirus,Severe acute respiratory syndrome-related coronavirus | — | EU371559 |
| SARS coronavirus ZJO301 | NC_004718 | vertebrates,human | 1 | Coronaviridae,Betacoronavirus,Severe acute respiratory syndrome-related coronavirus | — | DQ182595 |
| SARS coronavirus ZMY 1 | NC_004718 | vertebrates,human | 1 | Coronaviridae,Betacoronavirus,Severe acute respiratory syndrome-related coronavirus | — | AY351680 |
| SARS coronavirus ZS-A | NC_004718 | vertebrates,human | 1 | Coronaviridae,Betacoronavirus,Severe acute respiratory syndrome-related coronavirus | — | AY394997 |
| SARS coronavirus ZS-B | NC_004718 | vertebrates,human | 1 | Coronaviridae,Betacoronavirus,Severe acute respiratory syndrome-related coronavirus | — | AY394996 |
| SARS coronavirus ZS-C | NC_004718 | vertebrates,human | 1 | Coronaviridae,Betacoronavirus,Severe acute respiratory syndrome-related coronavirus | — | AY395003 |
| SARS coronavirus civet010 | NC_004718 | vertebrates,human | 1 | Coronaviridae,Betacoronavirus,Severe acute respiratory syndrome-related coronavirus | — | AY572035 |
| SARS coronavirus civet020 | NC_004718 | vertebrates,human | 1 | Coronaviridae,Betacoronavirus,Severe acute respiratory syndrome-related coronavirus | — | AY572038 |
| SARS coronavirus wtic-MB | NC_004718 | vertebrates,human | 31 | Coronaviridae,Betacoronavirus,Severe acute respiratory syndrome-related coronavirus | — | KF514421,FJ882932, FJ882937,KF514413, KF514400,KF514392, KF514399,JF292921, KF514415,FJ882927, KF514398,KF514408, KF514419,FJ882938, KF514423,FJ882934, KF514418,FJ882939, KF514396,KF514397, FJ882936,FJ882949, FJ882946,FJ882933, FJ882947,KF514394, KF514409,KF514422, KF514388,FJ882935, KF514404 |

-continued

| Taxonomy | NCBI Reference Sequence ID | Host | No. of Genomes | Lineage | Segment Count | Genbank Accession ID |
|---|---|---|---|---|---|---|
| Sabia virus | NC_006313 | vertebrates,human | 3 | Arenaviridae,Arenavirus,Sabia virus | seg. L | JN801475,AY358026, AY216506 |
| Sabia virus | NC_006317 | vertebrates,human | 2 | Arenaviridae,Arenavirus,Sabia virus | seg. S | U41071,JN801474 |
| Sapovirus Chanthaburi-74/Thailand | NC_000940,NC_010624,NC_006269,NC_006554 | vertebrates,human | 1 | Caliciviridae,Sapovirus,Sapporo virus | — | AY646854 |
| Sapovirus Ehime1107/2002/JP | NC_000940,NC_010624,NC_006269,NC_006554 | vertebrates,human | 1 | Caliciviridae,Sapovirus,Sapporo virus | — | DQ058829 |
| Sapovirus Hu/Angelholm/SW278/2004/SE | NC_000940,NC_010624,NC_006269,NC_006554 | vertebrates,human | 1 | Caliciviridae,Sapovirus,Sapporo virus | — | DQ125333 |
| Sapovirus Hu/Angelholm/5W314/2004/SE | NC_000940,NC_010624,NC_006269,NC_006554 | vertebrates,human | 1 | Caliciviridae,Sapovirus,Sapporo virus | — | DQ125334 |
| Sapovirus Hu/Bristo1/1998/UK | NC_000940,NC_010624,NC_006269,NC_006554 | vertebrates,human | 1 | Caliciviridae,Sapovirus,Sapporo virus | — | AJ249939 |
| Sapovirus Hu/Chiba/000671/1999/JP | NC_000940,NC_010624,NC_006269,NC_006554 | vertebrates,human | 1 | Caliciviridae,Sapovirus,Sapporo virus | — | AJ786349 |
| Sapovirus Hu/Ehime1596/1999/JP | NC_000940, NC_010624,NC_006269,NC_006554 | vertebrates,human | 1 | Caliciviridae,Sapovirus,Sapporo virus | — | DQ366346 |
| Sapovirus Hu/Ehime475/2004/JP | NC_000940,NC_010624,NC_006269,NC_006554 | vertebrates,human | 1 | Caliciviridae,Sapovirus,Sapporo virus | — | DQ366344 |
| Sapovirus Hu/Ehime643/March 2000/JP | NC_000940,NC_010624,NC_006269,NC_006554 | vertebrates,human | 1 | Caliciviridae,Sapovirus,Sapporo virus | — | DQ366345 |

-continued

| Taxonomy | NCBI Reference Sequence ID | Host | No. of Genomes | Lineage | Segment Count | Genbank Accession ID |
|---|---|---|---|---|---|---|
| Sapovirus Hu/G L2/BR-DF01/BRA/2009 | NC_000940, NC_010624, NC_006269, NC_006554 | vertebrates,human | 1 | Caliciviridae,Sapovirus,Sapporo virus | — | AB614356 |
| Sapovirus Hu/GI/Sapporo/MT-2010/1982 | NC_000940, NC_010624, NC_006269, NC_006554 | vertebrates,human | 1 | Caliciviridae,Sapovirus,Sapporo virus | — | HM002617 |
| Sapovirus Mc114 | NC_000940, NC_010624, NC_006269, NC_006554 | vertebrates,human | 1 | Caliciviridae,Sapovirus,Sapporo virus | — | AY237422 |
| Sapovirus Mc2 | NC_000940, NC_010624, NC_006269, NC_006554 | vertebrates,human | 1 | Caliciviridae,Sapovirus,Sapporo virus | — | AY237419 |
| Sapovirus N21 | NC_000940, NC_010624, NC_006269, NC_006554 | vertebrates,human | 1 | Caliciviridae,Sapovirus,Sapporo virus | — | AY237423 |
| Sapovirus NongKhai-24/Thailand | NC_000940, NC_010624, NC_006269, NC_006554 | vertebrates,human | 1 | Caliciviridae,Sapovirus,Sapporo virus | — | AY646856 |
| Sapovirus NongKhai-50/Thailand | NC_000940, NC_010624, NC_006269, NC_006554 | vertebrates,human | 1 | Caliciviridae,Sapovirus,Sapporo virus | — | AY646853 |
| Sapovirus SaKaeo-15/Thailand | NC_000940, NC_010624, NC_006269, NC_006554 | vertebrates,human | 1 | Caliciviridae,Sapovirus,Sapporo virus | — | AY646855 |
| Sapovirus pig/Gansu/CH430/2012/CHN | NC_000940, NC_010624, NC_006269, NC_006554 | vertebrates,human | 1 | Caliciviridae,Sapovirus,Sapporo virus | — | KF204570 |

-continued

| Taxonomy | NCBI Reference Sequence ID | Host | No. of Genomes | Lineage | Segment Count | Genbank Accession ID |
|---|---|---|---|---|---|---|
| Sapovirus pig/sav1/2008/CHN | NC_000940,NC_010624,NC_006269,NC_006554 | vertebrates,human | 1 | Caliciviridae,Sapovirus,Sapporo virus | — | FJ387164 |
| Sapporo rat virus | NC_005236 | vertebrates,human | 1 | Bunyaviridae,Hantavirus,Seoul virus | seg. S | M34881 |
| Sapporo rat virus | NC_005237 | vertebrates,human | 1 | Bunyaviridae,Hantavirus,Seoul virus | seg. M | M34882 |
| Sapporo virus-Manchester | NC_000940,NC_010624,NC_006269,NC_006554 | vertebrates,human | 1 | Caliciviridae,Sapovirus,Sapporo virus | — | X86560 |
| Seal anellovirus TFFN/USA/2006 | NC_015212 | vertebrates,human | 1 | Anelloviridae,Seal anellovirus TFFN/USA/2006 | — | HQ287751 |
| Sendai virus | NC_001552 | vertebrates,human | 20 | Paramyxoviridae,Respirovirus,Sendai virus | — | AB855653,AB005795,AB005796,AB065187,M69046,M30204,D0219803,AB195967,AB855655,EF679198,AB275417,AB065188,AB855654,AB03965 8,AB195968,AB2754 16,M30203,AB06518 9,AB065186,M30202 |
| Seoul virus | NC_005236 | vertebrates,human | 13 | Bunyaviridae,Hantavirus,Seoul virus | seg. S | AF406965,KC626089,JX853575,JX879769,JQ665912,HQ611980,AY006465,EF192308,AY766368,AY27379 1,JQ898106,JN37755 3,AY750171 |
| Seoul virus | NC_005237 | vertebrates,human | 11 | Bunyaviridae,Hantavirus,Seoul virus | seg. M | D17593,D17592,547 716,JN377554,JQ665 888,JX853576,D1759 4,DQ159911,JX8797 68,AB027521,EF1172 48 |
| Seoul virus | NC_005238 | vertebrates,human | 5 | Bunyaviridae,Hantavirus,Seoul virus | seg. L | JX879770,EF190551,X56492,JX853574,EF581094 |
| Seoul virus 5CSG | NC_005237 | vertebrates,human | 1 | Bunyaviridae,Hantavirus,Seoul virus | seg. M | AB618130 |
| Seoul virus B-1 | NC_005237 | vertebrates,human | 1 | Bunyaviridae,Hantavirus,Seoul virus | seg. M | X53861 |
| Seoul virus BjHDQ1 | NC_005236 | vertebrates,human | 1 | Bunyaviridae,Hantavirus,Seoul virus | seg. S | AY627049 |
| Seoul virus BjHDQ1 | NC_005237 | vertebrates,human | 1 | Bunyaviridae,Hantavirus,Seoul virus | seg. M | DQ133505 |
| Seoul virus CSG5 | NC_005236 | vertebrates,human | 1 | Bunyaviridae,Hantavirus,Seoul virus | seg. S | AB618112 |
| Seoul virus Gou3-e5 | NC_005237 | vertebrates,human | 1 | Bunyaviridae,Hantavirus,Seoul virus | seg. M | AF288650 |
| Seoul virus Hb8610 | NC_005236 | vertebrates,human | 1 | Bunyaviridae,Hantavirus,Seoul virus | seg. S | AF288643 |
| Seoul virus K24-e7 | NC_005236 | vertebrates,human | 1 | Bunyaviridae,Hantavirus,Seoul virus | seg. S | AF288653 |

-continued

| Taxonomy | NCBI Reference Sequence ID | Host | No. of Genomes | Lineage | Segment Count | Genbank Accession ID |
|---|---|---|---|---|---|---|
| Seoul virus K24-e7 | NC_005237 | vertebrates,human | 1 | Bunyaviridae,Hantavirus,Seoul virus | seg. M | AF288652 |
| Seoul virus K24-v2 | NC_005236 | vertebrates,human | 1 | Bunyaviridae,Hantavirus,Seoul virus | seg. S | AF288655 |
| Seoul virus K24-v2 | NC_005237 | vertebrates,human | 1 | Bunyaviridae,Hantavirus,Seoul virus | seg. M | AF288654 |
| Seoulvirus Gou3 | NC_005236 | vertebrates,human | 1 | Bunyaviridae,Hantavirus,Seoul virus | seg. S | AF184988 |
| Seoulvirus Gou3 | NC_005237 | vertebrates,human | 1 | Bunyaviridae,Hantavirus,Seoul virus | seg. M | AF145977 |
| Seoulvirus HB55 | NC_005236 | vertebrates,human | 1 | Bunyaviridae,Hantavirus,Seoul virus | seg. S | AF035832 |
| Seoulvirus IR461 | NC_005237 | vertebrates,human | 1 | Bunyaviridae,Hantavirus,Seoul virus | seg. M | AF329388 |
| Seoulvirus IR461 | NC_005236 | vertebrates,human | 1 | Bunyaviridae,Hantavirus,Seoul virus | seg. S | AF458104 |
| Seoulvirus L99 | NC_005237 | vertebrates,human | 1 | Bunyaviridae,Hantavirus,Seoul virus | seg. M | AF288299 |
| Seoulvirus L99 | NC_005236 | vertebrates,human | 2 | Bunyaviridae,Hantavirus,Seoul virus | seg. S | AF288298,AF035833 |
| Seoulvirus L99 | NC_005238 | vertebrates,human | 1 | Bunyaviridae,Hantavirus,Seoul virus | seg. L | AF288297 |
| Seoulvirus R22 | NC_005236 | vertebrates,human | 2 | Bunyaviridae,Hantavirus,Seoul virus | seg. S | AF488707,AF288295 |
| Seoulvirus tchoupitoulas | NC_005236 | vertebrates,human | 1 | Bunyaviridae,Hantavirus,Seoul virus | seg. S | AF329389 |
| Simian Agent 10 | NC_001796 | vertebrates,human | 1 | Paramyxoviridae,Respirovirus,Human parainfluenza virus 3 | — | HM583801 |
| Simian adenovirus 27.1 | NC_011202 | vertebrates,human | 1 | Adenoviridae,Mastadenovirus,Human adenovirus B | — | FJQ25909 |
| Simian adenovirus 27.1 | NC_011203 | vertebrates,human | 1 | Adenoviridae,Mastadenovirus,Human adenovirus B | — | FJQ25909 |
| Simian adenovirus 27.2 | NC_011202 | vertebrates,human | 1 | Adenoviridae,Mastadenovirus,Human adenovirus B | — | FJQ25928 |
| Simian adenovirus 27.2 | NC_011203 | vertebrates,human | 1 | Adenoviridae,Mastadenovirus,Human adenovirus B | — | FJQ25928 |
| Simian adenovirus 28.1 | NC_011202 | vertebrates,human | 1 | Adenoviridae,Mastadenovirus,Human adenovirus B | — | FJQ25914 |
| Simian adenovirus 28.1 | NC_011203 | vertebrates,human | 1 | Adenoviridae,Mastadenovirus,Human adenovirus B | — | FJQ25914 |
| Simian adenovirus 28.2 | NC_011202 | vertebrates,human | 1 | Adenoviridae,Mastadenovirus,Human adenovirus B | — | FJQ25915 |
| Simian adenovirus 28.2 | NC_011203 | vertebrates,human | 1 | Adenoviridae,Mastadenovirus,Human adenovirus B | — | FJQ25915 |
| Simian adenovirus 29 | NC_011202 | vertebrates,human | 1 | Adenoviridae,Mastadenovirus,Human adenovirus B | — | FJQ25916 |
| Simian adenovirus 29 | NC_011203 | vertebrates,human | 1 | Adenoviridae,Mastadenovirus,Human adenovirus B | — | FJQ25916 |
| Simian adenovirus 31.1 | NC_001405 | vertebrates,human | 1 | Adenoviridae,Mastadenovirus,Human adenovirus C | — | FJQ25906 |
| Simian adenovirus 31.2 | NC_001405 | vertebrates,human | 1 | Adenoviridae,Mastadenovirus,Human adenovirus C | — | FJQ25904 |
| Simian adenovirus 32 | NC_011202 | vertebrates,human | 1 | Adenoviridae,Mastadenovirus,Human adenovirus B | — | FJQ25911 |
| Simian adenovirus 32 | NC_011203 | vertebrates,human | 1 | Adenoviridae,Mastadenovirus,Human adenovirus B | — | FJQ25911 |
| Simian adenovirus 33 | NC_011202 | vertebrates,human | 1 | Adenoviridae,Mastadenovirus,Human adenovirus B | — | FJQ25908 |
| Simian adenovirus 33 | NC_011203 | vertebrates,human | 1 | Adenoviridae,Mastadenovirus,Human adenovirus B | — | FJQ25908 |

| Taxonomy | NCBI Reference Sequence ID | Host | Lineage | No. of Genomes | Segment Count | Genbank Accession ID |
|---|---|---|---|---|---|---|
| Simian adenovirus 34 | NC_001405 | vertebrates,human | Adenoviridae,Mastadenovirus,Human adenovirus C | 1 | — | FJQ25905 |
| Simian adenovirus 35,1 | NC_011202 | vertebrates,human | Adenoviridae,Mastadenovirus,Human adenovirus B | 1 | — | FJQ25912 |
| Simian adenovirus 35,1 | NC_011203 | vertebrates,human | Adenoviridae,Mastadenovirus,Human adenovirus B | 1 | — | FJQ25912 |
| Simian adenovirus 35,2 | NC_011202 | vertebrates,human | Adenoviridae,Mastadenovirus,Human adenovirus B | 1 | — | FJQ25910 |
| Simian adenovirus 35,2 | NC_011203 | vertebrates,human | Adenoviridae,Mastadenovirus,Human adenovirus B | 1 | — | FJQ25910 |
| Simian adenovirus 40,1 | NC_001405 | vertebrates,human | Adenoviridae,Mastadenovirus,Human adenovirus C | 1 | — | FJQ25907 |
| Simian adenovirus 40,2 | NC_001405 | vertebrates,human | Adenoviridae,Mastadenovirus,Human adenovirus C | 1 | — | FJQ25926 |
| Simian adenovirus 41,1 | NC_011202 | vertebrates,human | Adenoviridae,Mastadenovirus,Human adenovirus B | 1 | — | FJQ25913 |
| Simian adenovirus 41,1 | NC_011203 | vertebrates,human | Adenoviridae,Mastadenovirus,Human adenovirus B | 1 | — | FJQ25913 |
| Simian adenovirus 41,2 | NC_011202 | vertebrates,human | Adenoviridae,Mastadenovirus,Human adenovirus B | 1 | — | FJQ25927 |
| Simian adenovirus 41,2 | NC_011203 | vertebrates,human | Adenoviridae,Mastadenovirus,Human adenovirus B | 1 | — | FJQ25927 |
| Simian adenovirus 42,1 | NC_001405 | vertebrates,human | Adenoviridae,Mastadenovirus,Human adenovirus C | 1 | — | FJQ25903 |
| Simian adenovirus 42,2 | NC_001405 | vertebrates,human | Adenoviridae,Mastadenovirus,Human adenovirus C | 1 | — | FJQ25902 |
| Simian adenovirus 42,3 | NC_001405 | vertebrates,human | Adenoviridae,Mastadenovirus,Human adenovirus C | 1 | — | FJQ25925 |
| Simian adenovirus 43 | NC_001405 | vertebrates,human | Adenoviridae,Mastadenovirus,Human adenovirus C | 1 | — | FJQ25900 |
| Simian adenovirus 44 | NC_001405 | vertebrates,human | Adenoviridae,Mastadenovirus,Human adenovirus C | 1 | — | FJQ25899 |
| Simian adenovirus 45 | NC_001405 | vertebrates,human | Adenoviridae,Mastadenovirus,Human adenovirus C | 1 | — | FJQ25901 |
| Simian adenovirus 46 | NC_011202 | vertebrates,human | Adenoviridae,Mastadenovirus,Human adenovirus B | 1 | — | FJQ25930 |
| Simian adenovirus 46 | NC_011203 | vertebrates,human | Adenoviridae,Mastadenovirus,Human adenovirus B | 1 | — | FJQ25930 |
| Simian adenovirus 47 | NC_011202 | vertebrates,human | Adenoviridae,Mastadenovirus,Human adenovirus B | 1 | — | FJQ25929 |
| Simian adenovirus 47 | NC_011203 | vertebrates,human | Adenoviridae,Mastadenovirus,Human adenovirus B | 1 | — | FJQ25929 |
| Simian agents | NC_001472 | vertebrates,human | Picornaviridae,Enterovirus,Enterovirus B | 1 | — | AF326751 |
| Simian enterovirus 19 | NC_001612 | vertebrates,human | Picornaviridae,Enterovirus,Enterovirus A | 1 | — | AF326754 |
| Simian enterovirus 43 | NC_001612 | vertebrates,human | Picornaviridae,Enterovirus,Enterovirus A | 1 | — | AF326761 |

| Taxonomy | NCBI Reference Sequence ID | Host | No. of Genomes | Lineage | Segment Count | Genbank Accession ID |
|---|---|---|---|---|---|---|
| Simian enterovirus 46 | NC_001612 | vertebrates,human | 2 | Picornaviridae,Enterovirus,Enterovirus A | — | EF667343,AF326764 |
| Simian rotavirus | NC_011500 | vertebrates,human | 6 | Reoviridae,Rotavirus,Rotavirus A | seg. 5 | AF290884,AF290883,AF290882,Z32535,AF290881,FJ422135 |
| Simian rotavirus | NC_011501 | vertebrates,human | 2 | Reoviridae,Rotavirus,Rotavirus A | seg. 7 | GU550506,FJ422137 |
| Simian rotavirus | NC_011502 | vertebrates,human | 2 | Reoviridae,Rotavirus,Rotavirus A | seg. 8 | X81426,FJ422138 |
| Simian rotavirus | NC_011503 | vertebrates,human | 4 | Reoviridae,Rotavirus,Rotavirus A | seg. 9 | X66158,V01546,V01190,FJ422139 |
| Simian rotavirus | NC_011504 | vertebrates,human | 2 | Reoviridae,Rotavirus,Rotavirus A | seg. 10 | FJ422140,L41247 |
| Simian rotavirus | NC_011505 | vertebrates,human | 4 | Reoviridae,Rotavirus,Rotavirus A | seg. 11 | AF306493,XQ7831,FJ422141,M28347 |
| Simian rotavirus | NC_011506 | vertebrates,human | 3 | Reoviridae,Rotavirus,Rotavirus A | seg. 2 | AF474406,L33364,FJ422132 |
| Simian rotavirus | NC_011507 | vertebrates,human | 1 | Reoviridae,Rotavirus,Rotavirus A | seg. 1 | FJ422131 |
| Simian rotavirus | NC_011508 | vertebrates,human | 1 | Reoviridae,Rotavirus,Rotavirus A | seg. 3 | FJ422133 |
| Simian rotavirus | NC_011509 | vertebrates,human | 5 | Reoviridae,Rotavirus,Rotavirus A | seg. 6 | L15384,FJ422136,L33365,XQ0421,M27824 |
| Simian rotavirus 4 | NC_011510 | vertebrates,human | 5 | Reoviridae,Rotavirus,Rotavirus A | seg. 4 | M23188,FJ422134,D16345,D16346,X1420 |
| Simian rotavirus A strain RRV | NC_011506 | vertebrates,human | 2 | Reoviridae,Rotavirus,Rotavirus A | seg. 2 | EF583007,EU636925 |
| Simian rotavirus A strain RRV | NC_011507 | vertebrates,human | 2 | Reoviridae,Rotavirus,Rotavirus A | seg. 1 | EU636924,EF583006 |
| Simian rotavirus A strain RRV | NC_011508 | vertebrates,human | 2 | Reoviridae,Rotavirus,Rotavirus A | seg. 3 | EU636926,EF583008 |
| Simian rotavirus A strain TUCH | NC_011509 | vertebrates,human | 1 | Reoviridae,Rotavirus,Rotavirus A | seg. 6 | EF583009 |
| Simian rotavirus A strain TUCH | NC_011500 | vertebrates,human | 1 | Reoviridae,Rotavirus,Rotavirus A | seg. 5 | FJ816612 |
| Simian rotavirus A strain TUCH | NC_011501 | vertebrates,human | 1 | Reoviridae,Rotavirus,Rotavirus A | seg. 7 | FJ816613 |
| Simian rotavirus A strain TUCH | NC_011502 | vertebrates,human | 1 | Reoviridae,Rotavirus,Rotavirus A | seg. 8 | FJ816614 |
| Simian rotavirus A strain TUCH | NC_011503 | vertebrates,human | 1 | Reoviridae,Rotavirus,Rotavirus A | seg. 9 | FJ816615 |
| Simian rotavirus A strain TUCH | NC_011504 | vertebrates,human | 1 | Reoviridae,Rotavirus,Rotavirus A | seg. 10 | FJ816616 |
| Simian rotavirus A strain TUCH | NC_011505 | vertebrates,human | 1 | Reoviridae,Rotavirus,Rotavirus A | seg. 11 | FJ816617 |
| Simian rotavirus A strain TUCH | NC_011506 | vertebrates,human | 1 | Reoviridae,Rotavirus,Rotavirus A | seg. 2 | EF583011 |
| Simian rotavirus A strain TUCH | NC_011507 | vertebrates,human | 1 | Reoviridae,Rotavirus,Rotavirus A | seg. 1 | EF583010 |
| Simian rotavirus A strain TUCH | NC_011508 | vertebrates,human | 1 | Reoviridae,Rotavirus,Rotavirus A | seg. 3 | EF583012 |
| Simian rotavirus A strain TUCH | NC_011509 | vertebrates,human | 1 | Reoviridae,Rotavirus,Rotavirus A | seg. 6 | EF583013 |

| Taxonomy | NCBI Reference Sequence ID | Host | No. of Genomes | Lineage | Segment Count | Genbank Accession ID |
|---|---|---|---|---|---|---|
| Simian rotavirus A strain TUCH | NC_011510 | vertebrates,human | 1 | Reoviridae,Rotavirus,Rotavirus A | seg. 4 | FJ816611 |
| Simian rotavirus A/SA11 | NC_011500 | vertebrates,human | 1 | Reoviridae,Rotavirus,Rotavirus A | seg. 5 | X14914 |
| Simian rotavirus A/SA11 | NC_011501 | vertebrates,human | 1 | Reoviridae,Rotavirus,Rotavirus A | seg. 7 | JQ2353 |
| Simian rotavirus A/SA11 | NC_011502 | vertebrates,human | 1 | Reoviridae,Rotavirus,Rotavirus A | seg. 8 | XQ0355 |
| Simian rotavirus A/SA11 | NC_011504 | vertebrates,human | 2 | Reoviridae,Rotavirus,Rotavirus A | seg. 10 | AF087678,K01138 |
| Simian rotavirus A/SA11 | NC_011506 | vertebrates,human | 1 | Reoviridae,Rotavirus,Rotavirus A | seg. 2 | X16831 |
| Simian rotavirus A/SA11 | NC_011507 | vertebrates,human | 1 | Reoviridae,Rotavirus,Rotavirus A | seg. 1 | X16830 |
| Simian rotavirus A/SA11 | NC_011508 | vertebrates,human | 2 | Reoviridae,Rotavirus,Rotavirus A | seg. 3 | X16062,X16387 |
| Simian rotavirus A/SA11 | NC_011509 | vertebrates,human | 1 | Reoviridae,Rotavirus,Rotavirus A | seg. 6 | AY187029 |
| Simian rotavirus A/SA11 | NC_011510 | vertebrates,human | 1 | Reoviridae,Rotavirus,Rotavirus A | seg. 4 | Y00036 |
| Simian rotavirus A/SA11-C14 | NC_011502 | vertebrates,human | 1 | Reoviridae,Rotavirus,Rotavirus A | seg. 8 | AY065843 |
| Simian rotavirus A/SA11-L2 | NC_011502 | vertebrates,human | 1 | Reoviridae,Rotavirus,Rotavirus A | seg. 8 | EF460843 |
| Simian virus 40 | NC_001669 | vertebrates,human | 35 | Polyomaviridae,Polyomavirus,Simian virus 40 | seg. 8 | EF579662,EF579804, AY271816,EF579661, FN812745,AF155358, AF156105,AY120890, AF345345,JQ2400,AF 316141,EF579665,AF 345344,EF579663,AF 316140,EF579664,AF 156107,EF579659,AY 538779,EF579660,AF 180737,AF156108,AF 271817,AF156108,AF 332562,DQ660375,E F579658,EF579666,A F332699,DQ218418, EF579803,AF155359, AF316139,AF168994, AF038616 |
| Simian virus 41 | NC_006428 | vertebrates,human | 1 | Paramyxoviridae,Rubulavirus,Simian virus 41 | — | X64275 |
| Sin Nombre virus | NC_005215 | vertebrates,human | 6 | Bunyaviridae,Hantavirus,Sin Nombre virus | seg. M | JQ690283,JQ690280, JQ690279,JQ690284, L25783, L37903 |
| Sin Nombre virus | NC_005216 | vertebrates,human | 8 | Bunyaviridae,Hantavirus,Sin Nombre virus | seg. S | L25784,JQ690281,JQ 690277,JQ690282,JQ 690278,JQ690276,AF 281851,L37904 |
| Sin Nombre virus | NC_005217 | vertebrates,human | 2 | Bunyaviridae,Hantavirus,Sin Nombre virus | seg. L | L37902,L37901 |
| Small anellovirus 2 | NC_007014, NC_007013 | vertebrates,human | 1 | Anelloviridae,Small anellovirus | — | AY622909 |

-continued

| Taxonomy | NCBI Reference Sequence ID | Host | No. of Genomes | Lineage | Segment Count | Genbank Accession ID |
|---|---|---|---|---|---|---|
| Snow Mountain virus | NC_001959 | vertebrates,human | 1 | Caliciviridae,Norovirus,Norwalk virus | — | AY134748 |
| Southampton virus | NC_001959 | vertebrates,human | 1 | Caliciviridae,Norovirus,Norwalk virus | — | L07418 |
| Sudan ebolavirus | NC_006432 | vertebrates,human | 9 | Filoviridae,Ebolavirus,Sudan ebolavirus | — | KC545391,EU338380,KC589025,KC242783,FJ968794,KC545390,AY729654,KC545389,KC545392 |
| Sudan ebolavirus-Nakisamata | NC_006432 | vertebrates,human | 1 | Filoviridae,Ebolavirus,Sudan ebolavirus | — | JN638998 |
| Swine hepatitis E virus | NC_001434 | vertebrates,human | 26 | Hepeviridae,Hepevirus,Hepatitis E virus | — | GU361892,FJ998008, GU188851,AB481228,EU723514,AY594199,GU119961,FJ610232,GU119960,KF176351,AB097811,AB073912,AB481227,EU723512,EU676172,EU723515,AY115488,EU723513,AF082843,D0279091,FJ426403,FJ426404,AB481229,JX855794,EU723516, AB481226 |
| Swine vesicular disease virus | NC_001472 | vertebrates,human | 4 | Picornaviridae,Enterovirus,Enterovirus B | — | AY429470,AF268065, D16364,X54521 |
| Swine vesicular disease virus (STRAIN H/3 '76) | NC_001472 | vertebrates,human | 1 | Picornaviridae,Enterovirus,Enterovirus B | — | DQ0435 |
| TT virus 51e1931 | NC_015783 | vertebrates,human | 1 | Anelloviridae,Torque teno virus | — | AM712003 |
| TT virus 51e1932 | NC_015783 | vertebrates,human | 1 | Anelloviridae,Torque teno virus | — | AM712004 |
| TT virus 51e1957 | NC_015783 | vertebrates,human | 1 | Anelloviridae,Torque teno virus | — | AM711976 |
| TT virus 51e2057 | NC_015783 | vertebrates,human | 1 | Anelloviridae,Torque teno virus | — | AM712030 |
| TT virus 51e2058 | NC_015783 | vertebrates,human | 1 | Anelloviridae,Torque teno virus | — | AM712031 |
| TT virus 51e2061 | NC_015783 | vertebrates,human | 1 | Anelloviridae,Torque teno virus | — | AM712033 |
| TT virus 51e2065 | NC_015783 | vertebrates,human | 1 | Anelloviridae,Torque teno virus | — | AM712034 |
| TT virus 51e2072 | NC_015783 | vertebrates,human | 1 | Anelloviridae,Torque teno virus | — | AM712032 |
| TTV-like mini virus | NC_020498 | vertebrates,human | 8 | Anelloviridae,TTV-like mini virus | — | KF764702,JX134046, AB026930,JX134044, AB038628,AB038626,KF764701,JX134045 |
| Tacaribe virus | NC_004292 | vertebrates,human | 1 | Arenaviridae,Arenavirus,Tacaribe virus | seg. L | JQ4340 |
| Tacaribe virus | NC_004293 | vertebrates,human | 1 | Arenaviridae,Arenavirus,Tacaribe virus | seg. S | M20304 |
| Tamiami virus | NC_010701 | vertebrates,human | 3 | Arenaviridae,Arenavirus,Tamiami virus | seg. S | AF512828,AF485263, EU486821 |
| Tamiami virus | NC_010702 | vertebrates,human | 2 | Arenaviridae,Arenavirus,Tamiami virus | seg. L | AY924393,EU627614 |
| Thottapalayam virus | NC_010704 | vertebrates,human | 1 | Bunyaviridae,Hantavirus,Thottapalayam virus | seg. S | AY526097 |
| Thottapalayam virus | NC_010707 | vertebrates,human | 2 | Bunyaviridae,Hantavirus,Thottapalayam virus | seg. L | EU001330,DQ825770 |
| Thottapalayam virus | NC_010708 | vertebrates,human | 2 | Bunyaviridae,Hantavirus,Thottapalayam virus | seg. M | EU001329,DQ825771 |
| Tioman virus | NC_004074 | vertebrates,human | 1 | Paramyxoviridae,Rubulavirus,Tioman virus | — | AF298895 |

| Taxonomy | NCBI Reference Sequence ID | Host | No. of Genomes | Lineage | Segment Count | Genbank Accession ID |
|---|---|---|---|---|---|---|
| Torque teno canis virus | NC_014071 | vertebrates,human | 3 | Anelloviridae,Thetatorquevirus,Torque teno canis virus | — | AB076002,GU951508,HM855265 |
| Torque teno douroucouli virus | NC_014087 | vertebrates,human | 1 | Anelloviridae,Zetatorquevirus,Torque teno douroucouli virus | — | AB041961 |
| Torque teno felis virus | NC_014072 | vertebrates,human | 3 | Anelloviridae,Etatorquevirus,Torque teno felis virus | — | HM142589,HM142588,AB076003 |
| Torque teno midi virus 1 | NC_009225 | vertebrates,human | 2 | Anelloviridae,Gammatorquevirus,Torque teno midi virus 1 | — | AB290918,AB290917 |
| Torque teno midi virus 2 | NC_014093 | vertebrates,human | 1 | Anelloviridae,Gammatorquevirus,Torque teno midi virus 2 | — | AB290919 |
| Torque teno mini virus 1 | NC_014097 | vertebrates,human | 1 | Anelloviridae,Betatorquevirus,Torque teno mini virus 1 | — | AB026931 |
| Torque teno mini virus 2 | NC_014086 | vertebrates,human | 1 | Anelloviridae,Betatorquevirus,Torque teno mini virus 2 | — | AB038629 |
| Torque teno mini virus 3 | NC_014088 | vertebrates,human | 1 | Anelloviridae,Betatorquevirus,Torque teno mini virus 3 | — | AB038630 |
| Torque teno mini virus 4 | NC_014090 | vertebrates,human | 1 | Anelloviridae,Betatorquevirus,Torque teno mini virus 4 | — | AB041963 |
| Torque teno mini virus 5 | NC_014089 | vertebrates,human | 1 | Anelloviridae,Betatorquevirus,Torque teno mini virus 5 | — | AB041962 |
| Torque teno mini virus 6 | NC_014095 | vertebrates,human | 1 | Anelloviridae,Betatorquevirus,Torque teno mini virus 6 | — | AB026929 |
| Torque teno mini virus 7 | NC_014082 | vertebrates,human | 1 | Anelloviridae,Betatorquevirus,Torque teno mini virus 7 | — | AB038627 |
| Torque teno mini virus 8 | NC_014068 | vertebrates,human | 1 | Anelloviridae,Betatorquevirus,Torque teno mini virus 8 | — | AF291073 |
| Torque teno mini virus 9 | NC_002195 | vertebrates,human | 2 | Anelloviridae,Betatorquevirus,Torque teno mini virus 9 | — | AB038631,AB038625 |
| Torque teno sus virus 1 | NC_014070 | vertebrates,human | 13 | Anelloviridae,Iotatorquevirus,Torque teno sus virus 1a | — | HM633256,AB076001,JF937662,JF937660,JF937661,HM633251,JN688927,AY823990,JF694117,HM633249,HM633245,HM633243,JF694116 |
| Torque teno sus virus 1a | NC_014070 | vertebrates,human | 3 | Anelloviridae,Iotatorquevirus,Torque teno sus virus 1a | — | JX535326,JX535327,JQ933527 |
| Torque teno sus virus k2 | NC_014092 | vertebrates,human | 1 | Anelloviridae,Kappatorquevirus,Torque teno sus virus k2 | — | AY823991 |
| Torque teno sus virus k2b | NC_014092 | vertebrates,human | 3 | Anelloviridae,Kappatorquevirus,Torque teno sus virus k2 | — | JQ406846,JQ406844,JQ406845 |
| Torque teno tamarin virus | NC_014085 | vertebrates,human | 1 | Anelloviridae,Epsilontorquevirus,Torque teno tamarin virus | — | AB041960 |
| Torque teno virus | NC_014070 | vertebrates,human | 4 | Anelloviridae,Iotatorquevirus,Torque teno sus virus 1a | — | GQ120664,GU45638 3,GU456384,GU1880 45 |

| Taxonomy | NCBI Reference Sequence ID | Host | No. of Genomes | Lineage | Segment Count | Genbank Accession ID |
|---|---|---|---|---|---|---|
| Torque teno virus | NC_015783 | vertebrates,human | 114 | Anelloviridae,Torque teno virus | — | AF351132,FR751478, AF247138,FR751507, FR751483,FR751485 ,FR751472,AJ620233 ,FR751470,AB028866 9,AB064603,FR7515 06,AF122915,FR7514 71,AB064597,FR751 463,AJ620216,FR751 495,AY823989,FR84 8325,AB054648,AF12 2916,AJ620228,AJ62 0212,FR848327,FR7 51479,FR751500,AF1 22914,AJ620224,FR7 51477,AJ620235,AB0 64599,FR751465,FR 751491,FR848323,F R751502,AB017610, FR751504,AB064606 ,AJ620218,FR751493 ,AJ620227,AF122917 ,AJ620231,FR751480 ,DQ003344,FR751147 5,AY823988,FR7514 69,AJ620219,AB0386 19,AF116842,FR7514 68,FR751490,FR751 501,AB064602,AJ620 221,AF298585,AJ620 226,AB038620,FR75 1503,FR751509,FR7 51481,AJ620214,FR7 51497,DQ003341,DO 00343,FR751476,AJ 620232,AJ620230,FR 751487,AJ620229,AB 064600,AF247137,AF 122921,FR751492,AF 122918,FR751508,AF 122920,FJ426280,FR 751484,AF122913,FR 751511,FR751489,F R751496,AJ620234,A F079173,FR751482,F R751494,AB064601, AB064596,AJ620223, AJ620225,FR751510, |

-continued

| Taxonomy | NCBI Reference Sequence ID | Host | No. of Genomes | Lineage | Segment Count | Genbank Accession ID |
|---|---|---|---|---|---|---|
| Torque teno virus 1 | NC_002076 | vertebrates,human | 2 | Anelloviridae,Alphatorquevirus,Torque teno virus 1 | — | FR751486,AF129887, AJ620213,DQ003342, AJ620220,FR751473, FR848324,AJ620222, FR751105,FR751146, FR848326,FR751474,AB064604,FR751498,FR751467,AJ620215,AJ620217,FR751464,FR751488,FR751499 |
| Torque teno virus 1 | NC_014070 | vertebrates,human | 5 | Anelloviridae,Iotatorquevirus,Torque teno sus virus 1a | — | AB041007,AB008394 |
| Torque teno virus 10 | NC_014076 | vertebrates,human | 2 | Anelloviridae,Alphatorquevirus,Torque teno virus 10 | — | GU570202,GU570198,GU570201,GU570199,GU570200 |
| Torque teno virus 12 | NC_014075 | vertebrates,human | 1 | Anelloviridae,Alphatorquevirus,Torque teno virus 12 | — | AB064607,GU797360 |
| Torque teno virus 14 | NC_014077 | vertebrates,human | 1 | Anelloviridae,Alphatorquevirus,Torque teno virus 14 | — | AB064605 |
| Torque teno virus 15 | NC_014096 | vertebrates,human | 1 | Anelloviridae,Alphatorquevirus,Torque teno virus 15 | — | AB037926 |
| Torque teno virus 16 | NC_014091 | vertebrates,human | 1 | Anelloviridae,Alphatorquevirus,Torque teno virus 16 | — | AB028668 |
| Torque teno virus 19 | NC_014078 | vertebrates,human | 1 | Anelloviridae,Alphatorquevirus,Torque teno virus 19 | — | AB017613 |
| Torque teno virus 2 | NC_014480 | vertebrates,human | 1 | Anelloviridae,Alphatorquevirus,Torque teno virus 2 | — | AB025946 |
| Torque teno virus 25 | NC_014083 | vertebrates,human | 1 | Anelloviridae,Alphatorquevirus,Torque teno virus 25 | — | AB049608 |
| Torque teno virus 26 | NC_014079 | vertebrates,human | 1 | Anelloviridae,Alphatorquevirus,Torque teno virus 26 | — | AB041959 |
| Torque teno virus 27 | NC_014074 | vertebrates,human | 1 | Anelloviridae,Alphatorquevirus,Torque teno virus 27 | — | AB041958 |
| Torque teno virus 28 | NC_014073 | vertebrates,human | 1 | Anelloviridae,Alphatorquevirus,Torque teno virus 28 | — | AB064595 |
| Torque teno virus 3 | NC_014081 | vertebrates,human | 1 | Anelloviridae,Alphatorquevirus,Torque teno virus 3 | — | AB064598 |
| Torque teno virus 4 | NC_014069 | vertebrates,human | 1 | Anelloviridae,Alphatorquevirus,Torque teno virus 4 | — | AY666122 |
| Torque teno virus 6 | NC_014094 | vertebrates,human | 1 | Anelloviridae,Alphatorquevirus,Torque teno virus 6 | — | AB041957 |
| Torque teno virus 7 | NC_014080 | vertebrates,human | 1 | Anelloviridae,Alphatorquevirus,Torque teno virus 7 | — | AF435014 |
| Torque teno virus 8 | NC_014084 | vertebrates,human | 1 | Anelloviridae,Alphatorquevirus,Torque teno virus 8 | — | AF261761 |
| | | | | | | AB054647 |

| Taxonomy | NCBI Reference Sequence ID | Host | No. of Genomes | Lineage | Segment Count | Genbank Accession ID |
|---|---|---|---|---|---|---|
| Torque teno zalophus virus 1 | NC_012126 | vertebrates,human | 1 | Anelloviridae,Lambdatorquevirus,Torque teno zalophus virus 1 | — | FJ459582 |
| Tula virus | NC_005226 | vertebrates,human | 1 | Bunyaviridae,Hantavirus,Tula virus | seg. L | AJQ05637 |
| Tula virus | NC_005227 | vertebrates,human | 18 | Bunyaviridae,Hantavirus,Tula virus | seg. S | AM945877,Z30945,AJ223600,AF164093,Z30942,AF017659,Z30943,Z30944,Y13980,AF164094,AJ223601,AF44261,Z48573,Y13979,Z30941,Z48741,Z48574,Z49915 |
| Rotavirus A human/Victoria/CK00026/2005/G1P[8] | NC_011508 | vertebrates,human | 1 | Reoviridae,Rotavirus,Rotavirus A | seg. 3 | JF490334 |
| Rotavirus A human/Victoria/CK00026/2005/G1P[8] | NC_011509 | vertebrates,human | 1 | Reoviridae,Rotavirus,Rotavirus A | seg. 6 | JF490332 |
| Rotavirus A human/Victoria/CK00026/2005/G1P[8] | NC_011510 | vertebrates,human | 1 | Reoviridae,Rotavirus,Rotavirus A | seg. 4 | JF490333 |
| Rotavirus A human/Victoria/CK00027/2054/G1P[8] | NC_011500 | vertebrates,human | 1 | Reoviridae,Rotavirus,Rotavirus A | seg. 5 | JF490338 |
| Rotavirus A human/Victoria/CK00027/2054/G1P[8] | NC_011501 | vertebrates,human | 1 | Reoviridae,Rotavirus,Rotavirus A | seg. 7 | JF490342 |
| Rotavirus A human/Victoria/CK00027/2054/G1P[8] | NC_011502 | vertebrates,human | 1 | Reoviridae,Rotavirus,Rotavirus A | seg. 8 | JF490337 |
| Rotavirus A human/Victoria/CK00027/2054/G1P[8] | NC_011503 | vertebrates,human | 1 | Reoviridae,Rotavirus,Rotavirus A | seg. 9 | JF490341 |
| Rotavirus A human/Victoria/CK00027/2054/G1P[8] | NC_011504 | vertebrates,human | 1 | Reoviridae,Rotavirus,Rotavirus A | seg. 10 | JF490340 |
| Rotavirus A human/Victoria/CK00027/2054/G1P[8] | NC_011505 | vertebrates,human | 1 | Reoviridae,Rotavirus,Rotavirus A | seg. 11 | JF490339 |
| Rotavirus A human/Victoria/CK00027/2054/G1P[8] | NC_011506 | vertebrates,human | 1 | Reoviridae,Rotavirus,Rotavirus A | seg. 2 | JF490345 |
| Rotavirus A human/Victoria/CK00027/2054/G1P[8] | NC_011507 | vertebrates,human | 1 | Reoviridae,Rotavirus,Rotavirus A | seg. 1 | JF490336 |
| Rotavirus A human/Victoria/CK00027/2054/G1P[8] | NC_011508 | vertebrates,human | 1 | Reoviridae,Rotavirus,Rotavirus A | seg. 3 | JF490346 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00027/2054/G1P[8] | NC_011509 | vertebrates,human | 1 | Reoviridae,Rotavirus,Rotavirus A | seg. 6 | JF490343 |
| Rotavirus A human/Victoria/CK00027/2054/G1P[8] | NC_011510 | vertebrates,human | 1 | Reoviridae,Rotavirus,Rotavirus A | seg. 4 | JF490344 |
| Rotavirus A human/Victoria/CK00028/2005/G1P[8] | NC_011500 | vertebrates,human | 1 | Reoviridae,Rotavirus,Rotavirus A | seg. 5 | JF490357 |
| Rotavirus A human/Victoria/CK00028/2005/G1P[8] | NC_011501 | vertebrates,human | 1 | Reoviridae,Rotavirus,Rotavirus A | seg. 7 | JF490352 |
| Rotavirus A human/Victoria/CK00028/2005/G1P[8] | NC_011502 | vertebrates,human | 1 | Reoviridae,Rotavirus,Rotavirus A | seg. 8 | JF490348 |
| Rotavirus A human/Victoria/CK00028/2005/G1P[8] | NC_011503 | vertebrates,human | 1 | Reoviridae,Rotavirus,Rotavirus A | seg. 9 | JF490351 |
| Rotavirus A human/Victoria/CK00028/2005/G1P[8] | NC_011504 | vertebrates,human | 1 | Reoviridae,Rotavirus,Rotavirus A | seg. 10 | JF490350 |
| Rotavirus A human/Victoria/CK00028/2005/G1P[8] | NC_011505 | vertebrates,human | 1 | Reoviridae,Rotavirus,Rotavirus A | seg. 11 | JF490349 |
| Rotavirus A human/Victoria/CK00028/2005/G1P[8] | NC_011506 | vertebrates,human | 1 | Reoviridae,Rotavirus,Rotavirus A | seg. 2 | JF490356 |
| Rotavirus A human/Victoria/CK00028/2005/G1P[8] | NC_011507 | vertebrates,human | 1 | Reoviridae,Rotavirus,Rotavirus A | seg. 1 | JF490347 |
| Rotavirus A human/Victoria/CK00028/2005/G1P[8] | NC_011508 | vertebrates,human | 1 | Reoviridae,Rotavirus,Rotavirus A | seg. 3 | JF490355 |
| Rotavirus A human/Victoria/CK00028/2005/G1P[8] | NC_011509 | vertebrates,human | 1 | Reoviridae,Rotavirus,Rotavirus A | seg. 6 | JF490353 |
| Rotavirus A human/Victoria/CK00028/2005/G1P[8] | NC_011510 | vertebrates,human | 1 | Reoviridae,Rotavirus,Rotavirus A | seg. 4 | JF490354 |
| Rotavirus A human/Victoria/CK00029/2006/G1P[8] | NC_011500 | vertebrates,human | 1 | Reoviridae,Rotavirus,Rotavirus A | seg. 5 | JF490360 |
| Rotavirus A human/Victoria/CK00029/2006/G1P[8] | NC_011501 | vertebrates,human | 1 | Reoviridae,Rotavirus,Rotavirus A | seg. 7 | JF490363 |
| Rotavirus A human/Victoria/CK00029/2006/G1P[8] | NC_011502 | vertebrates,human | 1 | Reoviridae,Rotavirus,Rotavirus A | seg. 8 | JF490359 |

-continued

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00029/2006/G1P[8] | NC_011503 | vertebrates,human | 1 | Reoviridae,Rotavirus,Rotavirus A | seg. 9 | JF490368 |
| Rotavirus A human/Victoria/CK00029/2006/G1P[8] | NC_011504 | vertebrates,human | 1 | Reoviridae,Rotavirus,Rotavirus A | seg. 10 | JF490362 |
| Rotavirus A human/Victoria/CK00029/2006/G1P[8] | NC_011505 | vertebrates,human | 1 | Reoviridae,Rotavirus,Rotavirus A | seg. 11 | JF490361 |
| Rotavirus A human/Victoria/CK00029/2006/G1P[8] | NC_011506 | vertebrates,human | 1 | Reoviridae,Rotavirus,Rotavirus A | seg. 2 | JF490367 |
| Rotavirus A human/Victoria/CK00029/2006/G1P[8] | NC_011507 | vertebrates,human | 1 | Reoviridae,Rotavirus,Rotavirus A | seg. 1 | JF490358 |
| Rotavirus A human/Victoria/CK00029/2006/G1P[8] | NC_011508 | vertebrates,human | 1 | Reoviridae,Rotavirus,Rotavirus A | seg. 3 | JF490366 |
| Rotavirus A human/Victoria/CK00029/2006/G1P[8] | NC_011509 | vertebrates,human | 1 | Reoviridae,Rotavirus,Rotavirus A | seg. 6 | JF490364 |
| Rotavirus A human/Victoria/CK00029/2006/G1P[8] | NC_011510 | vertebrates,human | 1 | Reoviridae,Rotavirus,Rotavirus A | seg. 4 | JF490365 |
| Rotavirus A human/Victoria/CK00030/2006/G1P[8] | NC_011500 | vertebrates,human | 1 | Reoviridae,Rotavirus,Rotavirus A | seg. 5 | JF490371 |
| Rotavirus A human/Victoria/CK00030/2006/G1P[8] | NC_011501 | vertebrates,human | 1 | Reoviridae,Rotavirus,Rotavirus A | seg. 7 | JF490375 |
| Rotavirus A human/Victoria/CK00030/2006/G1P[8] | NC_011502 | vertebrates,human | 1 | Reoviridae,Rotavirus,Rotavirus A | seg. 8 | JF490370 |
| Rotavirus A human/Victoria/CK00030/2006/G1P[8] | NC_011503 | vertebrates,human | 1 | Reoviridae,Rotavirus,Rotavirus A | seg. 9 | JF490374 |
| Rotavirus A human/Victoria/CK00030/2006/G1P[8] | NC_011504 | vertebrates,human | 1 | Reoviridae,Rotavirus,Rotavirus A | seg. 10 | JF490373 |
| Rotavirus A human/Victoria/CK00030/2006/G1P[8] | NC_011505 | vertebrates,human | 1 | Reoviridae,Rotavirus,Rotavirus A | seg. 11 | JF490372 |
| Rotavirus A human/Victoria/CK00030/2006/G1P[8] | NC_011506 | vertebrates,human | 1 | Reoviridae,Rotavirus,Rotavirus A | seg. 2 | JF490379 |
| Rotavirus A human/Victoria/CK00030/2006/G1P[8] | NC_011507 | vertebrates,human | 1 | Reoviridae,Rotavirus,Rotavirus A | seg. 1 | JF490369 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00030/2006/G1P[8] | NC_011508 | vertebrates,human | 1 | Reoviridae,Rotavirus,Rotavirus A | seg. 3 | JF490

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00033/2007/G1P[8] | NC_011502 | vertebrates,human | 1 | Reoviridae,Rotavirus,Rotavirus A | seg. 8 | JF490392 |
| Rotavirus A human/Victoria/CK00033/2007/G1P[8] | NC_011503 | vertebrates,human | 1 | Reoviridae,Rotavirus,Rotavirus A | seg. 9 | JF490396 |
| Rotavirus A human/Victoria/CK00033/2007/G1P[8] | NC_011504 | vertebrates,human | 1 | Reoviridae,Rotavirus,Rotavirus A | seg. 10 | JF490395 |
| Rotavirus A human/Victoria/CK00033/2007/G1P[8] | NC_011505 | vertebrates,human | 1 | Reoviridae,Rotavirus,Rotavirus A | seg. 11 | JF490394 |
| Rotavirus A human/Victoria/CK00033/2007/G1P[8] | NC_011506 | vertebrates,human | 1 | Reoviridae,Rotavirus,Rotavirus A | seg. 2 | JF490401 |
| Rotavirus A human/Victoria/CK00033/2007/G1P[8] | NC_011507 | vertebrates,human | 1 | Reoviridae,Rotavirus,Rotavirus A | seg. 1 | JF490391 |
| Rotavirus A human/Victoria/CK00033/2007/G1P[8] | NC_011508 | vertebrates,human | 1 | Reoviridae,Rotavirus,Rotavirus A | seg. 3 | JF490400 |
| Rotavirus A human/Victoria/CK00033/2007/G1P[8] | NC_011509 | vertebrates,human | 1 | Reoviridae,Rotavirus,Rotavirus A | seg. 6 | JF490398 |
| Rotavirus A human/Victoria/CK00033/2007/G1P[8] | NC_011510 | vertebrates,human | 1 | Reoviridae,Rotavirus,Rotavirus A | seg. 4 | JF490399 |
| Rotavirus A human/Victoria/CK00034/2007/G1P[8] | NC_011500 | vertebrates,human | 1 | Reoviridae,Rotavirus,Rotavirus A | seg. 5 | JF490410 |
| Rotavirus A human/Victoria/CK00034/2007/G1P[8] | NC_011501 | vertebrates,human | 1 | Reoviridae,Rotavirus,Rotavirus A | seg. 7 | JF490407 |
| Rotavirus A human/Victoria/CK00034/2007/G1P[8] | NC_011502 | vertebrates,human | 1 | Reoviridae,Rotavirus,Rotavirus A | seg. 8 | JF490403 |
| Rotavirus A human/Victoria/CK00034/2007/G1P[8] | NC_011503 | vertebrates,human | 1 | Reoviridae,Rotavirus,Rotavirus A | seg. 9 | JF490406 |
| Rotavirus A human/Victoria/CK00034/2007/G1P[8] | NC_011504 | vertebrates,human | 1 | Reoviridae,Rotavirus,Rotavirus A | seg. 10 | JF490405 |
| Rotavirus A human/Victoria/CK00034/2007/G1P[8] | NC_011505 | vertebrates,human | 1 | Reoviridae,Rotavirus,Rotavirus A | seg. 11 | JF490404 |
| Rotavirus A human/Victoria/CK00034/2007/G1P[8] | NC_011506 | vertebrates,human | 1 | Reoviridae,Rotavirus,Rotavirus A | seg. 2 | JF490412 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00034/2007/G1P[8] | NC_011507 | vertebrates,human | 1 | Reoviridae,Rotavirus,Rotavirus A | seg. 1 | JF490402 |
| Rotavirus A human/Victoria/CK00034/2007/G1P[8] | NC_011508 | vertebrates,human | 1 | Reoviridae,Rotavirus,Rotavirus A | seg. 3 | JF490411 |
| Rotavirus A human/Victoria/CK00034/2007/G1P[8] | NC_011509 | vertebrates,human | 1 | Reoviridae,Rotavirus,Rotavirus A | seg. 6 | JF490408 |
| Rotavirus A human/Victoria/CK00034/2007/G1P[8] | NC_011510 | vertebrates,human | 1 | Reoviridae,Rotavirus,Rotavirus A | seg. 4 | JF490409 |
| Rotavirus A human/Victoria/CK00035/2005/G1P[8] | NC_011500 | vertebrates,human | 1 | Reoviridae,Rotavirus,Rotavirus A | seg. 5 | JF490415 |
| Rotavirus A human/Victoria/CK00035/2005/G1P[8] | NC_011501 | vertebrates,human | 1 | Reoviridae,Rotavirus,Rotavirus A | seg. 7 | JF490419 |
| Rotavirus A human/Victoria/CK00035/2005/G1P[8] | NC_011502 | vertebrates,human | 1 | Reoviridae,Rotavirus,Rotavirus A | seg. 8 | JF490414 |
| Rotavirus A human/Victoria/CK00035/2005/G1P[8] | NC_011503 | vertebrates,human | 1 | Reoviridae,Rotavirus,Rotavirus A | seg. 9 | JF490418 |
| Rotavirus A human/Victoria/CK00035/2005/G1P[8] | NC_011504 | vertebrates,human | 1 | Reoviridae,Rotavirus,Rotavirus A | seg. 10 | JF490417 |
| Rotavirus A human/Victoria/CK00035/2005/G1P[8] | NC_011505 | vertebrates,human | 1 | Reoviridae,Rotavirus,Rotavirus A | seg. 11 | JF490416 |
| Rotavirus A human/Victoria/CK00035/2005/G1P[8] | NC_011506 | vertebrates,human | 1 | Reoviridae,Rotavirus,Rotavirus A | seg. 2 | JF490423 |
| Rotavirus A human/Victoria/CK00035/2005/G1P[8] | NC_011507 | vertebrates,human | 1 | Reoviridae,Rotavirus,Rotavirus A | seg. 1 | JF490413 |
| Rotavirus A human/Victoria/CK00035/2005/G1P[8] | NC_011508 | vertebrates,human | 1 | Reoviridae,Rotavirus,Rotavirus A | seg. 3 | JF490422 |
| Rotavirus A human/Victoria/CK00035/2005/G1P[8] | NC_011509 | vertebrates,human | 1 | Reoviridae,Rotavirus,Rotavirus A | seg. 6 | JF490420 |
| Rotavirus A human/Victoria/CK00035/2005/G1P[8] | NC_011510 | vertebrates,human | 1 | Reoviridae,Rotavirus,Rotavirus A | seg. 4 | JF490421 |
| Rotavirus A human/Victoria/CK00036/2005/G1P[8] | NC_011500 | vertebrates,human | 1 | Reoviridae,Rotavirus,Rotavirus A | seg. 5 | JF490434 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00036/2005/G1P[8] | NC_011501 | vertebrates,human | 1 | Reoviridae,Rotavirus,Rotavirus A | seg. 7 | JF490429 |
| Rotavirus A human/Victoria/CK00036/2005/G1P[8] | NC_011502 | vertebrates,human | 1 | Reoviridae,Rotavirus,Rotavirus A | seg. 8 | JF490425 |
| Rotavirus A human/Victoria/CK00036/2005/G1P[8] | NC_011503 | vertebrates,human | 1 | Reoviridae,Rotavirus,Rotavirus A | seg. 9 | JF490428 |
| Rotavirus A human/Victoria/CK00036/2005/G1P[8] | NC_011504 | vertebrates,human | 1 | Reoviridae,Rotavirus,Rotavirus A | seg. 10 | JF490427 |
| Rotavirus A human/Victoria/CK00036/2005/G1P[8] | NC_011505 | vertebrates,human | 1 | Reoviridae,Rotavirus,Rotavirus A | seg. 11 | JF490426 |
| Rotavirus A human/Victoria/CK00036/2005/G1P[8] | NC_011506 | vertebrates,human | 1 | Reoviridae,Rotavirus,Rotavirus A | seg. 2 | JF490433 |
| Rotavirus A human/Victoria/CK00036/2005/G1P[8] | NC_011507 | vertebrates,human | 1 | Reoviridae,Rotavirus,Rotavirus A | seg. 1 | JF490424 |
| Rotavirus A human/Victoria/CK00036/2005/G1P[8] | NC_011508 | vertebrates,human | 1 | Reoviridae,Rotavirus,Rotavirus A | seg. 3 | JF490432 |
| Rotavirus A human/Victoria/CK00036/2005/G1P[8] | NC_011509 | vertebrates,human | 1 | Reoviridae,Rotavirus,Rotavirus A | seg. 6 | JF490430 |
| Rotavirus A human/Victoria/CK00036/2005/G1P[8] | NC_011510 | vertebrates,human | 1 | Reoviridae,Rotavirus,Rotavirus A | seg. 4 | JF490431 |
| Rotavirus A human/Victoria/CK00036/2005/G1P[8] | NC_011500 | vertebrates,human | 1 | Reoviridae,Rotavirus,Rotavirus A | seg. 5 | JF490443 |
| Rotavirus A human/Victoria/CK00037/2006/G1P[8] | NC_011501 | vertebrates,human | 1 | Reoviridae,Rotavirus,Rotavirus A | seg. 7 | JF490439 |
| Rotavirus A human/Victoria/CK00037/2006/G1P[8] | NC_011502 | vertebrates,human | 1 | Reoviridae,Rotavirus,Rotavirus A | seg. 8 | JF490436 |
| Rotavirus A human/Victoria/CK00037/2006/G1P[8] | NC_011503 | vertebrates,human | 1 | Reoviridae,Rotavirus,Rotavirus A | seg. 9 | JF490444 |
| Rotavirus A human/Victoria/CK00037/2006/G1P[8] | NC_011504 | vertebrates,human | 1 | Reoviridae,Rotavirus,Rotavirus A | seg. 10 | JF490438 |
| Rotavirus A human/Victoria/CK00037/2006/G1P[8] | NC_011505 | vertebrates,human | 1 | Reoviridae,Rotavirus,Rotavirus A | seg. 11 | JF490437 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00037/2006/G1P[8] | NC_011506 | vertebrates,human | 1 | Reoviridae,Rotavirus,Rotavirus A | seg. 2 | JF490445 |
| Rotavirus A human/Victoria/CK00037/2006/G1P[8] | NC_011507 | vertebrates,human | 1 | Reoviridae,Rotavirus,Rotavirus A | seg. 1 | JF490435 |
| Rotavirus A human/Victoria/CK00037/2006/G1P[8] | NC_011508 | vertebrates,human | 1 | Reoviridae,Rotavirus,Rotavirus A | seg. 3 | JF490442 |
| Rotavirus A human/Victoria/CK00037/2006/G1P[8] | NC_011509 | vertebrates,human | 1 | Reoviridae,Rotavirus,Rotavirus A | seg. 6 | JF490440 |
| Rotavirus A human/Victoria/CK00037/2006/G1P[8] | NC_011510 | vertebrates,human | 1 | Reoviridae,Rotavirus,Rotavirus A | seg. 4 | JF490441 |
| Rotavirus A human/Victoria/CK00039/2006/G1P[8] | NC_011500 | vertebrates,human | 1 | Reoviridae,Rotavirus,Rotavirus A | seg. 5 | JF490448 |
| Rotavirus A human/Victoria/CK00039/2006/G1P[8] | NC_011501 | vertebrates,human | 1 | Reoviridae,Rotavirus,Rotavirus A | seg. 7 | JF490452 |
| Rotavirus A human/Victoria/CK00039/2006/G1P[8] | NC_011502 | vertebrates,human | 1 | Reoviridae,Rotavirus,Rotavirus A | seg. 8 | JF490447 |
| Rotavirus A human/Victoria/CK00039/2006/G1P[8] | NC_011503 | vertebrates,human | 1 | Reoviridae,Rotavirus,Rotavirus A | seg. 9 | JF490451 |
| Rotavirus A human/Victoria/CK00039/2006/G1P[8] | NC_011504 | vertebrates,human | 1 | Reoviridae,Rotavirus,Rotavirus A | seg. 10 | JF490450 |
| Rotavirus A human/Victoria/CK00039/2006/G1P[8] | NC_011505 | vertebrates,human | 1 | Reoviridae,Rotavirus,Rotavirus A | seg. 11 | JF490449 |
| Rotavirus A human/Victoria/CK00039/2006/G1P[8] | NC_011506 | vertebrates,human | 1 | Reoviridae,Rotavirus,Rotavirus A | seg. 2 | JF490456 |
| Rotavirus A human/Victoria/CK00039/2006/G1P[8] | NC_011507 | vertebrates,human | 1 | Reoviridae,Rotavirus,Rotavirus A | seg. 1 | JF490446 |
| Rotavirus A human/Victoria/CK00039/2006/G1P[8] | NC_011508 | vertebrates,human | 1 | Reoviridae,Rotavirus,Rotavirus A | seg. 3 | JF490455 |
| Rotavirus A human/Victoria/CK00039/2006/G1P[8] | NC_011509 | vertebrates,human | 1 | Reoviridae,Rotavirus,Rotavirus A | seg. 6 | JF490453 |
| Rotavirus A human/Victoria/CK00039/2006/G1P[8] | NC_011510 | vertebrates,human | 1 | Reoviridae,Rotavirus,Rotavirus A | seg. 4 | JF490454 |

-continued

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00040/2006/G1P[8] | NC_011500 | vertebrates,human | 1 | Reoviridae,Rotavirus,Rotavirus A | seg. 5 | JF490459 |
| Rotavirus A human/Victoria/CK00040/2006/G1P[8] | NC_011501 | vertebrates,human | 1 | Reoviridae,Rotavirus,Rotavirus A | seg. 7 | JF490463 |
| Rotavirus A human/Victoria/CK00040/2006/G1P[8] | NC_011502 | vertebrates,human | 1 | Reoviridae,Rotavirus,Rotavirus A | seg. 8 | JF490458 |
| Rotavirus A human/Victoria/CK00040/2006/G1P[8] | NC_011503 | vertebrates,human | 1 | Reoviridae,Rotavirus,Rotavirus A | seg. 9 | JF490462 |
| Rotavirus A human/Victoria/CK00040/2006/G1P[8] | NC_011504 | vertebrates,human | 1 | Reoviridae,Rotavirus,Rotavirus A | seg. 10 | JF490461 |
| Rotavirus A human/Victoria/CK00040/2006/G1P[8] | NC_011505 | vertebrates,human | 1 | Reoviridae,Rotavirus,Rotavirus A | seg. 11 | JF490460 |
| Rotavirus A human/Victoria/CK00040/2006/G1P[8] | NC_011506 | vertebrates,human | 1 | Reoviridae,Rotavirus,Rotavirus A | seg. 2 | JF490467 |
| Rotavirus A human/Victoria/CK00040/2006/G1P[8] | NC_011507 | vertebrates,human | 1 | Reoviridae,Rotavirus,Rotavirus A | seg. 1 | JF490457 |
| Rotavirus A human/Victoria/CK00040/2006/G1P[8] | NC_011508 | vertebrates,human | 1 | Reoviridae,Rotavirus,Rotavirus A | seg. 3 | JF490466 |
| Rotavirus A human/Victoria/CK00040/2006/G1P[8] | NC_011509 | vertebrates,human | 1 | Reoviridae,Rotavirus,Rotavirus A | seg. 6 | JF490464 |
| Rotavirus A human/Victoria/CK00040/2006/G1P[8] | NC_011510 | vertebrates,human | 1 | Reoviridae,Rotavirus,Rotavirus A | seg. 4 | JF490465 |
| Rotavirus A human/Victoria/CK00041/2006/G1P[8] | NC_011500 | vertebrates,human | 1 | Reoviridae,Rotavirus,Rotavirus A | seg. 5 | JF490470 |
| Rotavirus A human/Victoria/CK00041/2006/G1P[8] | NC_011501 | vertebrates,human | 1 | Reoviridae,Rotavirus,Rotavirus A | seg. 7 | JF490474 |
| Rotavirus A human/Victoria/CK00041/2006/G1P[8] | NC_011502 | vertebrates,human | 1 | Reoviridae,Rotavirus,Rotavirus A | seg. 8 | JF490469 |
| Rotavirus A human/Victoria/CK00041/2006/G1P[8] | NC_011503 | vertebrates,human | 1 | Reoviridae,Rotavirus,Rotavirus A | seg. 9 | JF490473 |
| Rotavirus A human/Victoria/CK00041/2006/G1P[8] | NC_011504 | vertebrates,human | 1 | Reoviridae,Rotavirus,Rotavirus A | seg. 10 | JF490472 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00041/2006/G1P[8] | NC_011505 | vertebrates,human | 1 | Reoviridae,Rotavirus,Rotavirus A | seg. 11 | JF490471 |
| Rotavirus A human/Victoria/CK00041/2006/G1P[8] | NC_011506 | vertebrates,human | 1 | Reoviridae,Rotavirus,Rotavirus A | seg. 2 | JF490478 |
| Rotavirus A human/Victoria/CK00041/2006/G1P[8] | NC_011507 | vertebrates,human | 1 | Reoviridae,Rotavirus,Rotavirus A | seg. 1 | JF490468 |
| Rotavirus A human/Victoria/CK00041/2006/G1P[8] | NC_011508 | vertebrates,human | 1 | Reoviridae,Rotavirus,Rotavirus A | seg. 3 | JF490477 |
| Rotavirus A human/Victoria/CK00041/2006/G1P[8] | NC_011509 | vertebrates,human | 1 | Reoviridae,Rotavirus,Rotavirus A | seg. 6 | JF490475 |
| Rotavirus A human/Victoria/CK00041/2006/G1P[8] | NC_011510 | vertebrates,human | 1 | Reoviridae,Rotavirus,Rotavirus A | seg. 4 | JF490476 |
| Rotavirus A human/Victoria/CK00043/2006/G1P[8] | NC_011500 | vertebrates,human | 1 | Reoviridae,Rotavirus,Rotavirus A | seg. 5 | JF490481 |
| Rotavirus A human/Victoria/CK00043/2006/G1P[8] | NC_011501 | vertebrates,human | 1 | Reoviridae,Rotavirus,Rotavirus A | seg. 7 | JF490485 |
| Rotavirus A human/Victoria/CK00043/2006/G1P[8] | NC_011502 | vertebrates,human | 1 | Reoviridae,Rotavirus,Rotavirus A | seg. 8 | JF490480 |
| Rotavirus A human/Victoria/CK00043/2006/G1P[8] | NC_011503 | vertebrates,human | 1 | Reoviridae,Rotavirus,Rotavirus A | seg. 9 | JF490484 |
| Rotavirus A human/Victoria/CK00043/2006/G1P[8] | NC_011504 | vertebrates,human | 1 | Reoviridae,Rotavirus,Rotavirus A | seg. 10 | JF490483 |
| Rotavirus A human/Victoria/CK00043/2006/G1P[8] | NC_011505 | vertebrates,human | 1 | Reoviridae,Rotavirus,Rotavirus A | seg. 11 | JF490482 |
| Rotavirus A human/Victoria/CK00043/2006/G1P[8] | NC_011506 | vertebrates,human | 1 | Reoviridae,Rotavirus,Rotavirus A | seg. 2 | JF490489 |
| Rotavirus A human/Victoria/CK00043/2006/G1P[8] | NC_011507 | vertebrates,human | 1 | Reoviridae,Rotavirus,Rotavirus A | seg. 1 | JF490479 |
| Rotavirus A human/Victoria/CK00043/2006/G1P[8] | NC_011508 | vertebrates,human | 1 | Reoviridae,Rotavirus,Rotavirus A | seg. 3 | JF490488 |
| Rotavirus A human/Victoria/CK00043/2006/G1P[8] | NC_011509 | vertebrates,human | 1 | Reoviridae,Rotavirus,Rotavirus A | seg. 6 | JF490486 |

-continued

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00043/2006/G1P[8] | NC_011510 | vertebrates,human | 1 | Reoviridae,Rotavirus,Rotavirus A | seg. 4 | JF490487 |
| Rotavirus A human/Victoria/CK00045/2006/G1P[8] | NC_011500 | vertebrates,human | 1 | Reoviridae,Rotavirus,Rotavirus A | seg. 5 | JF490495 |
| Rotavirus A human/Victoria/CK00045/2006/G1P[8] | NC_011501 | vertebrates,human | 1 | Reoviridae,Rotavirus,Rotavirus A | seg. 7 | JF490499 |
| Rotavirus A human/Victoria/CK00045/2006/G1P[8] | NC_011502 | vertebrates,human | 1 | Reoviridae,Rotavirus,Rotavirus A | seg. 8 | JF490494 |
| Rotavirus A human/Victoria/CK00045/2006/G1P[8] | NC_011503 | vertebrates,human | 1 | Reoviridae,Rotavirus,Rotavirus A | seg. 9 | JF490498 |
| Rotavirus A human/Victoria/CK00045/2006/G1P[8] | NC_011504 | vertebrates,human | 1 | Reoviridae,Rotavirus,Rotavirus A | seg. 10 | JF490497 |
| Rotavirus A human/Victoria/CK00045/2006/G1P[8] | NC_011505 | vertebrates,human | 1 | Reoviridae,Rotavirus,Rotavirus A | seg. 11 | JF490496 |
| Rotavirus A human/Victoria/CK00045/2006/G1P[8] | NC_011506 | vertebrates,human | 1 | Reoviridae,Rotavirus,Rotavirus A | seg. 2 | JF490493 |
| Rotavirus A human/Victoria/CK00045/2006/G1P[8] | NC_011507 | vertebrates,human | 1 | Reoviridae,Rotavirus,Rotavirus A | seg. 1 | JF490490 |
| Rotavirus A human/Victoria/CK00045/2006/G1P[8] | NC_011508 | vertebrates,human | 1 | Reoviridae,Rotavirus,Rotavirus A | seg. 3 | JF490492 |
| Rotavirus A human/Victoria/CK00045/2006/G1P[8] | NC_011509 | vertebrates,human | 1 | Reoviridae,Rotavirus,Rotavirus A | seg. 6 | JF490500 |
| Rotavirus A human/Victoria/CK00045/2006/G1P[8] | NC_011510 | vertebrates,human | 1 | Reoviridae,Rotavirus,Rotavirus A | seg. 4 | JF490491 |
| Rotavirus A human/Victoria/CK00046/2006/G1P[8] | NC_011500 | vertebrates,human | 1 | Reoviridae,Rotavirus,Rotavirus A | seg. 5 | JF490503 |
| Rotavirus A human/Victoria/CK00046/2006/G1P[8] | NC_011501 | vertebrates,human | 1 | Reoviridae,Rotavirus,Rotavirus A | seg. 7 | JF490507 |
| Rotavirus A human/Victoria/CK00046/2006/G1P[8] | NC_011502 | vertebrates,human | 1 | Reoviridae,Rotavirus,Rotavirus A | seg. 8 | JF490502 |
| Rotavirus A human/Victoria/CK00046/2006/G1P[8] | NC_011503 | vertebrates,human | 1 | Reoviridae,Rotavirus,Rotavirus A | seg. 9 | JF490506 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00046/2006/G1P[8] | NC_011504 | vertebrates,human | 1 | Reoviridae,Rotavirus,Rotavirus A | seg. 10 | J

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00047/2 006/G1P[8] | NC_011509 | vertebrates,human | 1 | Reoviridae,Rotavirus,Rotavirus A | seg. 6 | JF490519 |
| Rotavirus A human/Victoria/CK00047/2 006/G1P[8] | NC_011510 | vertebrates,human | 1 | Reoviridae,Rotavirus,Rotavirus A | seg. 4 | JF490520 |
| Rotavirus A human/Victoria/CK00048/2 004/G1P[8] | NC_011500 | vertebrates,human | 1 | Reoviridae,Rotavirus,Rotavirus A | seg. 5 | JF490525 |
| Rotavirus A human/Victoria/CK00048/2 004/G1P[8] | NC_011501 | vertebrates,human | 1 | Reoviridae,Rotavirus,Rotavirus A | seg. 7 | JF490529 |
| Rotavirus A human/Victoria/CK00048/2 004/G1P[8] | NC_011502 | vertebrates,human | 1 | Reoviridae,Rotavirus,Rotavirus A | seg. 8 | JF490524 |
| Rotavirus A human/Victoria/CK00048/2 004/G1P[8] | NC_011503 | vertebrates,human | 1 | Reoviridae,Rotavirus,Rotavirus A | seg. 9 | JF490528 |
| Rotavirus A human/Victoria/CK00048/2 004/G1P[8] | NC_011504 | vertebrates,human | 1 | Reoviridae,Rotavirus,Rotavirus A | seg. 10 | JF490527 |
| Rotavirus A human/Victoria/CK00048/2 004/G1P[8] | NC_011505 | vertebrates,human | 1 | Reoviridae,Rotavirus,Rotavirus A | seg. 11 | JF490526 |
| Rotavirus A human/Victoria/CK00048/2 004/G1P[8] | NC_011506 | vertebrates,human | 1 | Reoviridae,Rotavirus,Rotavirus A | seg. 2 | JF490533 |
| Rotavirus A human/Victoria/CK00048/2 004/G1P[8] | NC_011507 | vertebrates,human | 1 | Reoviridae,Rotavirus,Rotavirus A | seg. 1 | JF490523 |
| Rotavirus A human/Victoria/CK00048/2 004/G1P[8] | NC_011508 | vertebrates,human | 1 | Reoviridae,Rotavirus,Rotavirus A | seg. 3 | JF490532 |
| Rotavirus A human/Victoria/CK00048/2 004/G1P[8] | NC_011509 | vertebrates,human | 1 | Reoviridae,Rotavirus,Rotavirus A | seg. 6 | JF490530 |
| Rotavirus A human/Victoria/CK00048/2 004/G1P[8] | NC_011510 | vertebrates,human | 1 | Reoviridae,Rotavirus,Rotavirus A | seg. 4 | JF490531 |
| Rotavirus A human/Victoria/CK00049/2 004/G1P[8] | NC_011500 | vertebrates,human | 1 | Reoviridae,Rotavirus,Rotavirus A | seg. 5 | JF490536 |
| Rotavirus A human/Victoria/CK00049/2 004/G1P[8] | NC_011501 | vertebrates,human | 1 | Reoviridae,Rotavirus,Rotavirus A | seg. 7 | JF490540 |
| Rotavirus A human/Victoria/CK00049/2 004/G1P[8] | NC_011502 | vertebrates,human | 1 | Reoviridae,Rotavirus,Rotavirus A | seg. 8 | JF490535 |

| Taxonomy | NCBI Reference Sequence ID | Host | No. of Genomes | Lineage | Segment Count | Genbank Accession ID |
|---|---|---|---|---|---|---|
| Rotavirus A human/Victoria/CK00049/2 004/G1P[8] | NC_011503 | vertebrates,human | 1 | Reoviridae,Rotavirus,Rotavirus A | seg. 9 | JF490539 |
| Rotavirus A human/Victoria/CK00049/2 004/G1P[8] | NC_011504 | vertebrates,human | 1 | Reoviridae,Rotavirus,Rotavirus A | seg. 10 | JF490538 |
| Rotavirus A human/Victoria/CK00049/2 004/G1P[8] | NC_011505 | vertebrates,human | 1 | Reoviridae,Rotavirus,Rotavirus A | seg. 11 | JF490537 |
| Rotavirus A human/Victoria/CK00049/2 004/G1P[8] | NC_011506 | vertebrates,human | 1 | Reoviridae,Rotavirus,Rotavirus A | seg. 2 | JF490544 |
| Rotavirus A human/Victoria/CK00049/2 004/G1P[8] | NC_011507 | vertebrates,human | 1 | Reoviridae,Rotavirus,Rotavirus A | seg. 1 | JF490534 |
| Rotavirus A human/Victoria/CK00049/2 004/G1P[8] | NC_011508 | vertebrates,human | 1 | Reoviridae,Rotavirus,Rotavirus A | seg. 3 | JF490542 |
| Rotavirus A human/Victoria/CK00049/2 004/G1P[8] | NC_011509 | vertebrates,human | 1 | Reoviridae,Rotavirus,Rotavirus A | seg. 6 | JF490541 |
| Rotavirus A human/Victoria/CK00049/2 004/G1P[8] | NC_011510 | vertebrates,human | 1 | Reoviridae,Rotavirus,Rotavirus A | seg. 4 | JF490543 |
| Rotavirus A human/Victoria/CK00050/2 005/G1P[8] | NC_011500 | vertebrates,human | 1 | Reoviridae,Rotavirus,Rotavirus A | seg. 5 | JF490553 |
| Rotavirus A human/Victoria/CK00050/2 005/G1P[8] | NC_011501 | vertebrates,human | 1 | Reoviridae,Rotavirus,Rotavirus A | seg. 7 | JF490550 |
| Rotavirus A human/Victoria/CK00050/2 005/G1P[8] | NC_011502 | vertebrates,human | 1 | Reoviridae,Rotavirus,Rotavirus A | seg. 8 | JF490546 |
| Rotavirus A human/Victoria/CK00050/2 005/G1P[8] | NC_011503 | vertebrates,human | 1 | Reoviridae,Rotavirus,Rotavirus A | seg. 9 | JF490549 |
| Rotavirus A human/Victoria/CK00050/2 005/G1P[8] | NC_011504 | vertebrates,human | 1 | Reoviridae,Rotavirus,Rotavirus A | seg. 10 | JF490548 |
| Rotavirus A human/Victoria/CK00050/2 005/G1P[8] | NC_011505 | vertebrates,human | 1 | Reoviridae,Rotavirus,Rotavirus A | seg. 11 | JF490547 |
| Rotavirus A human/Victoria/CK00050/2 005/G1P[8] | NC_011506 | vertebrates,human | 1 | Reoviridae,Rotavirus,Rotavirus A | seg. 2 | JF490555 |
| Rotavirus A human/Victoria/CK00050/2 005/G1P[8] | NC_011507 | vertebrates,human | 1 | Reoviridae,Rotavirus,Rotavirus A | seg. 1 | JF490545 |

| Taxonomy | NCBI Reference Sequence ID | Host | Lineage | No. of Genomes | Segment Count | Genbank Accession ID |
|---|---|---|---|---|---|---|
| Rotavirus A human/Victoria/CK00050/2 005/G1P[8] | NC_011508 | vertebrates,human | Reoviridae,Rotavirus,Rotavirus A | 1 | seg. 3 | JF490552

| Taxonomy | NCBI Reference Sequence ID | Host | No. of Genomes | Lineage | Segment Count | Genbank Accession ID |
|---|---|---|---|---|---|---|
| Rotavirus A sable antelope/G6P[14] | NC_011508 | vertebrates,human | 1 | Reoviridae,Rotavirus,Rotavirus A | seg. 3 | FJ495128 |
| Rotavirus A sable antelope/G6P[14] | NC_011509 | vertebrates,human | 1 | Reoviridae,Rotavirus,Rotavirus A | seg. 6 | FJ495131 |
| Rotavirus A sable antelope/G6P[14] | NC_011510 | vertebrates,human | 1 | Reoviridae,Rotavirus,Rotavirus A | seg. 4 | FJ495129 |
| Rotavirus A strain 116E/AG | NC_011500 | vertebrates,human | 1 | Reoviridae,Rotavirus,Rotavirus A | seg. 5 | FJ361205 |
| Rotavirus A strain 116E/AG | NC_011501 | vertebrates,human | 1 | Reoviridae,Rotavirus,Rotavirus A | seg. 7 | FJ361207 |
| Rotavirus A strain 116E/AG | NC_011502 | vertebrates,human | 1 | Reoviridae,Rotavirus,Rotavirus A | seg. 8 | FJ361208 |
| Rotavirus A strain 116E/AG | NC_011503 | vertebrates,human | 1 | Reoviridae,Rotavirus,Rotavirus A | seg. 9 | FJ361209 |
| Rotavirus A strain 116E/AG | NC_011504 | vertebrates,human | 1 | Reoviridae,Rotavirus,Rotavirus A | seg. 10 | FJ361210 |
| Rotavirus A strain 116E/AG | NC_011505 | vertebrates,human | 1 | Reoviridae,Rotavirus,Rotavirus A | seg. 11 | FJ361211 |
| Rotavirus A strain 116E/AG | NC_011506 | vertebrates,human | 1 | Reoviridae,Rotavirus,Rotavirus A | seg. 2 | FJ361202 |
| Rotavirus A strain 116E/AG | NC_011507 | vertebrates,human | 1 | Reoviridae,Rotavirus,Rotavirus A | seg. 1 | FJ361201 |
| Rotavirus A strain 116E/AG | NC_011508 | vertebrates,human | 1 | Reoviridae,Rotavirus,Rotavirus A | seg. 3 | FJ361203 |
| Rotavirus A strain 116E/AG | NC_011509 | vertebrates,human | 1 | Reoviridae,Rotavirus,Rotavirus A | seg. 6 | FJ361206 |
| Rotavirus A strain 116E/AG | NC_011510 | vertebrates,human | 1 | Reoviridae,Rotavirus,Rotavirus A | seg. 4 | FJ361204 |
| Rotavirus A turkey-tc/GER/03V0002E10/2003/G22P[35] | NC_011502 | vertebrates,human | 1 | Reoviridae,Rotavirus,Rotavirus A | seg. 8 | JX204827 |
| Rotavirus A turkey-tc/GER/03V0002E10/2003/G22P[35] | NC_011503 | vertebrates,human | 1 | Reoviridae,Rotavirus,Rotavirus A | seg. 9 | JX204829 |
| Rotavirus A turkey-tc/GER/03V0002E10/2003/G22P[35] | NC_011506 | vertebrates,human | 1 | Reoviridae,Rotavirus,Rotavirus A | seg. 2 | JX204823 |
| Rotavirus A turkey-tc/GER/03V0002E10/2003/G22P[35] | NC_011507 | vertebrates,human | 1 | Reoviridae,Rotavirus,Rotavirus A | seg. 1 | JX204822 |
| Rotavirus A turkey-tc/GER/03V0002E10/2003/G22P[35] | NC_011508 | vertebrates,human | 1 | Reoviridae,Rotavirus,Rotavirus A | seg. 3 | JX204824 |
| Rotavirus A turkey-tc/GER/03V0002E10/2003/G22P[35] | NC_011509 | vertebrates,human | 1 | Reoviridae,Rotavirus,Rotavirus A | seg. 6 | JX204826 |
| Rotavirus A turkey-tc/GER/03V0002E10/2003/G22P[35] | NC_011510 | vertebrates,human | 1 | Reoviridae,Rotavirus,Rotavirus A | seg. 4 | JX204825 |
| Rotavirus B | NC_021541 | vertebrates,human | 1 | Reoviridae,Rotavirus,Rotavirus B | seg. 1 | M97203 |
| Rotavirus B | NC_021544 | vertebrates,human | 1 | Reoviridae,Rotavirus,Rotavirus B | seg. 6 | AF079157 |
| Rotavirus B | NC_021549 | vertebrates,human | 1 | Reoviridae,Rotavirus,Rotavirus B | seg. 11 | AF079158 |
| Rotavirus C | NC_007543 | vertebrates,human | 1 | Reoviridae,Rotavirus,Rotavirus C | seg. 6 | AJ132203 |
| Rotavirus C | NC_007544 | vertebrates,human | 1 | Reoviridae,Rotavirus,Rotavirus C | seg. 7 | AJ132204 |
| Rotavirus C | NC_007545 | vertebrates,human | 1 | Reoviridae,Rotavirus,Rotavirus C | seg. 9 | AJ132205 |
| Rotavirus C | NC_007546 | vertebrates,human | 1 | Reoviridae,Rotavirus,Rotavirus C | seg. 2 | AJ303139 |

| Taxonomy | NCBI Reference Sequence ID | Host | No. of Genomes | Lineage | Segment Count | Genbank Accession ID |
|---|---|---|---|---|---|---|
| Rotavirus C | NC_007547 | vertebrates,human | 1 | Reoviridae,Rotavirus,Rotavirus C | seg. 1 | AJ304859 |
| Rotavirus C | NC_007569 | vertebrates,human | 1 | Reoviridae,Rotavirus,Rotavirus C | seg. 10 | M81488 |
| Rotavirus C | NC_007570 | vertebrates,human | 4 | Reoviridae,Rotavirus,Rotavirus C | seg. 5 | AF162434,M8768,EF528570,X59843 |
| Rotavirus C | NC_007571 | vertebrates,human | 15 | Reoviridae,Rotavirus,Rotavirus C | seg. 8 | U20990,U20989,U20994,U20991,U20993,X77257,U20992,X7758,EF528571,X77256,AJ549087,U20996,U20987,U20995,U20988 |
| Rotavirus C | NC_007572 | vertebrates,human | 1 | Reoviridae,Rotavirus,Rotavirus C | seg. 3 | X79442 |
| Rotavirus C | NC_007573 | vertebrates,human | 1 | Reoviridae,Rotavirus,Rotavirus C | seg. 11 | X83967 |
| Rotavirus C | NC_007574 | vertebrates,human | 1 | Reoviridae,Rotavirus,Rotavirus C | seg. 4 | X96697 |
| Rotavirus F chicken/03V0568/DEU/2003 | NC_021625 | vertebrates,human | 1 | Reoviridae,Rotavirus,Rotavirus F | seg. 1 | JN596591 |
| Rotavirus F chicken/03V0568/DEU/2003 | NC_021626 | vertebrates,human | 1 | Reoviridae,Rotavirus,Rotavirus F | seg. 2 | JQ919995 |
| Rotavirus F chicken/03V0568/DEU/2003 | NC_021627 | vertebrates,human | 1 | Reoviridae,Rotavirus,Rotavirus F | seg. 9 | JQ919998 |
| Rotavirus F chicken/03V0568/DEU/2003 | NC_021628 | vertebrates,human | 1 | Reoviridae,Rotavirus,Rotavirus F | seg. 8 | JQ920000 |
| Rotavirus F chicken/03V0568/DEU/2003 | NC_021629 | vertebrates,human | 1 | Reoviridae,Rotavirus,Rotavirus F | seg. 10 | JQ920003 |
| Rotavirus F chicken/03V0568/DEU/2003 | NC_021630 | vertebrates,human | 1 | Reoviridae,Rotavirus,Rotavirus F | seg. 4 | JQ919996 |
| Rotavirus F chicken/03V0568/DEU/2003 | NC_021631 | vertebrates,human | 1 | Reoviridae,Rotavirus,Rotavirus F | seg. 3 | JQ919997 |
| Rotavirus F chicken/03V0568/DEU/2003 | NC_021632 | vertebrates,human | 1 | Reoviridae,Rotavirus,Rotavirus F | seg. 5 | JQ919999 |
| Rotavirus F chicken/03V0568/DEU/2003 | NC_021633 | vertebrates,human | 1 | Reoviridae,Rotavirus,Rotavirus F | seg. 7 | JQ920001 |
| Rotavirus F chicken/03V0568/DEU/2003 | NC_021634 | vertebrates,human | 1 | Reoviridae,Rotavirus,Rotavirus F | seg. 11 | JQ920002 |
| Rotavirus F chicken/03V0568/DEU/2003 | NC_021635 | vertebrates,human | 1 | Reoviridae,Rotavirus,Rotavirus F | seg. 6 | HQ403603 |
| Rotavirus G chicken/03V0567/DEU/2003 | NC_021580 | vertebrates,human | 1 | Reoviridae,Rotavirus,Rotavirus G | — | JQ920004 |
| Rotavirus G chicken/03V0567/DEU/2003 | NC_021581 | vertebrates,human | 1 | Reoviridae,Rotavirus,Rotavirus G | — | JQ920006 |
| Rotavirus G chicken/03V0567/DEU/2003 | NC_021582 | vertebrates,human | 1 | Reoviridae,Rotavirus,Rotavirus G | — | JQ920007 |
| Rotavirus G chicken/03V0567/DEU/2003 | NC_021583 | vertebrates,human | 1 | Reoviridae,Rotavirus,Rotavirus G | — | JQ920008 |
| Rotavirus G chicken/03V0567/DEU/2003 | NC_021584 | vertebrates,human | 1 | Reoviridae,Rotavirus,Rotavirus G | — | JQ920009 |

| Taxonomy | NCBI Reference Sequence ID | Host | No. of Genomes | Lineage | Segment Count | Genbank Accession ID |
|---|---|---|---|---|---|---|
| Rotavirus G chicken/03V0567/DEU/2003 | NC_021585 | vertebrates,human | 1 | Reoviridae,Rotavirus,Rotavirus G | — | JQ920010 |
| Rotavirus G chicken/03V0567/DEU/2003 | NC_021586 | vertebrates,human | 1 | Reoviridae,Rotavirus,Rotavirus G | — | JQ920011 |
| Rotavirus G chicken/03V0567/DEU/2003 | NC_021587 | vertebrates,human | 1 | Reoviridae,Rotavirus,Rotavirus G | — | JQ920012 |
| Rotavirus G chicken/03V0567/DEU/2003 | NC_021588 | vertebrates,human | 1 | Reoviridae,Rotavirus,Rotavirus G | — | HQ403604 |
| Rotavirus G chicken/03V0567/DEU/2003 | NC_021589 | vertebrates,human | 1 | Reoviridae,Rotavirus,Rotavirus G | — | JQ920005 |
| Rotavirus G chicken/03V0567/DEU/2003 | NC_021590 | vertebrates,human | 1 | Reoviridae,Rotavirus,Rotavirus G | — | JN596592 |
| Rotavirus G1 | NC_011503 | vertebrates,human | 11 | Reoviridae,Rotavirus,Rotavirus A | seg. 9 | EU839916,EU839911,EU839909,EU839913,EU839912,EU839910,EU839915,EU839908,EU839907,EU839906,EU839914 |
| Rotavirus G1 | NC_011504 | vertebrates,human | 1 | Reoviridae,Rotavirus,Rotavirus A | seg. 10 | AY159645,AY159638,AY159631,AY159636,AY159632,AY159646,AY159633,AY159642,AY159643,AY159634,AY159644,AY159641,AY159640,AY159630,AY159637,AY159639,AY159648,AY159635,AY159647 |
| Rotavirus G10 | NC_011503 | vertebrates,human | 7 | Reoviridae,Rotavirus,Rotavirus A | seg. 9 | AY816181,JF681943,AY843333,AY816182,AY855063,JF681941,AY843332 |
| Rotavirus G10 | NC_011504 | vertebrates,human | 1 | Reoviridae,Rotavirus,Rotavirus A | seg. 10 | AY855068 |
| Rotavirus G12 | NC_011501 | vertebrates,human | 2 | Reoviridae,Rotavirus,Rotavirus A | seg. 7 | EU839967,EU839973 |
| Rotavirus G12 | NC_011502 | vertebrates,human | 2 | Reoviridae,Rotavirus,Rotavirus A | seg. 8 | EU839968,EU839974 |
| Rotavirus G12 | NC_011503 | vertebrates,human | 18 | Reoviridae,Rotavirus,Rotavirus A | seg. 9 | AB436818,AB436813,EU839943,EU839993,EU839944,AB436814,EU839944,AB436815,EU839942,EF059916,AB436816,AB306271,AB436817,AB306270,EF059917,AB306268,EU839935,AB306269,AB436819 |

| Taxonomy | NCBI Reference Sequence ID | Host | No. of Genomes | Lineage | Segment Count | Genbank Accession ID |
|---|---|---|---|---|---|---|
| Rotavirus G12 | NC_011504 | vertebrates,human | 4 | Reoviridae,Rotavirus,Rotavirus A | seg. 10 | EU839969,EF059919,EU839975,EF059918 |
| Rotavirus G12 | NC_011505 | vertebrates,human | 2 | Reoviridae,Rotavirus,Rotavirus A | seg. 11 | EU839970,EU839976 |
| Rotavirus G12 | NC_011509 | vertebrates,human | 2 | Reoviridae,Rotavirus,Rotavirus A | seg. 6 | EU839965,EU839971 |
| Rotavirus G12 | NC_011510 | vertebrates,human | 2 | Reoviridae,Rotavirus,Rotavirus A | seg. 4 | EF059921,EF059920 |
| Rotavirus G2 | NC_011503 | vertebrates,human | 16 | Reoviridae,Rotavirus,Rotavirus A | seg. 9 | AY707784,EU839925,EU839919,EU839921,AY707785,EU839917,EU839926,EU839918,EU839923,DQ478581,EU839924,EU839920,EU839922,EU839928,AY707786,EU839927 |
| Rotavirus G2 | NC_011504 | vertebrates,human | 3 | Reoviridae,Rotavirus,Rotavirus A | seg. 10 | AY159649,AF401756,EU839964 |
| Rotavirus G3 | NC_011509 | vertebrates,human | 1 | Reoviridae,Rotavirus,Rotavirus A | seg. 6 | EU839963 |
| Rotavirus G3 | NC_011500 | vertebrates,human | 1 | Reoviridae,Rotavirus,Rotavirus A | seg. 5 | AY740735 |
| Rotavirus G3 | NC_011501 | vertebrates,human | 1 | Reoviridae,Rotavirus,Rotavirus A | seg. 7 | AY740734 |
| Rotavirus G3 | NC_011502 | vertebrates,human | 2 | Reoviridae,Rotavirus,Rotavirus A | seg. 8 | JQ358771,AY740733 |
| Rotavirus G3 | NC_011503 | vertebrates,human | 51 | Reoviridae,Rotavirus,Rotavirus A | seg. 9 | EF495119,EF495124,AY707791,D86276,EF495121,EF495127,D80904498,D86266,D86280,D86264,D86282,JQ358764,D86269,D86265,AY707789,AY707792,EF495122,D0904499,DQ995488,DQ995489,D86283,D0904503,EF495118,DQ904500,DQ904504,AY870661,DQ904506,EF495120,D86284,D86281,DQ904502,D86279,DQ904501,D86271,DQ995490,D86272,AY900173,AY707794,EF495126,D86278,D86268,D86267,D86274,EF495123,AY740736,DQ904504,AY707793,EF495125,D86275 |

| Taxonomy | NCBI Reference Sequence ID | Host | No. of Genomes | Lineage | Segment Count | Genbank Accession ID |
|---|---|---|---|---|---|---|
| Rotavirus G3 | NC_011504 | vertebrates,human | 21 | Reoviridae,Rotavirus,Rotavirus A | seg. 10 | AB008240,AB008236,AB008234,AB008246,AB008230,AB008233,AB008237,AY740732,AB008242,AB008238,AB008243,AB008231,AB008244,AB008232,AB008245,AB008248,AB008247,AB008241,AB008239,AB008229,AB008235 |
| Rotavirus G3 | NC_011505 | vertebrates,human | 2 | Reoviridae,Rotavirus,Rotavirus A | seg. 11 | JQ358774,AY740731 |
| Rotavirus G3 | NC_011506 | vertebrates,human | 1 | Reoviridae,Rotavirus,Rotavirus A | seg. 2 | AY740740 |
| Rotavirus G3 | NC_011507 | vertebrates,human | 1 | Reoviridae,Rotavirus,Rotavirus A | seg. 1 | AY740741 |
| Rotavirus G3 | NC_011508 | vertebrates,human | 1 | Reoviridae,Rotavirus,Rotavirus A | seg. 3 | AY740739 |
| Rotavirus G3 | NC_011509 | vertebrates,human | 1 | Reoviridae,Rotavirus,Rotavirus A | seg. 6 | AY740737 |
| Rotavirus G3 | NC_011510 | vertebrates,human | 20 | Reoviridae,Rotavirus,Rotavirus A | seg. 4 | AY740738,AB008277,AB008279,AB008278,AB008290,AB008282,AB008291,AB008281,AB008289,AB008272,AB008273,AB008274,AB008285,AB008275,AB008284,AB008286,AB008283,AB008280,AB008276,AB008288 |
| Rotavirus G4 | NC_011503 | vertebrates,human | 33 | Reoviridae,Rotavirus,Rotavirus A | seg. 9 | AB012066,AB012074,AF161822,AB039035,AB012075,AB03902 6,AB039027,AB012071,AB039025,AB012078,AF161821,AB039029,AF161823,AB012069,AF161817,AB012065,AB012079,AB039028,AB012072,AF161818,AB039032,AB012077,AB012067,AB012076,AB012073,AB012070,AF161820,AB039031,AB012068,AB039030,AF161819,AB039034,AB039033 |

| Taxonomy | NCBI Reference Sequence ID | Host | No. of Genomes | Lineage | Segment Count | Genbank Accession ID |
|---|---|---|---|---|---|---|
| Rotavirus G4 | NC_011504 | vertebrates,human | 33 | Reoviridae,Rotavirus,Rotavirus A | seg. 10 | AB008255,AB008261,AF161810,AB043069,AF161815,AB043026,AB008251,AB008260,AB008253,AB008262,AB008249,AF161818,11,AB043072,AB043075,AF161813,AB008258,AB043076,AF161816,AB008259,AB008252,AB008263,AB043077,AB008256,AB043073,AB043070,AB043078,AB043074,AF161814,AB008250,AB043071,AB008257,AB008254,AF161812 |
| Rotavirus G6 | NC_011503 | vertebrates,human | 1 | Reoviridae,Rotavirus,Rotavirus A | seg. 9 | AF532202 |
| Rotavirus G8 | NC_011503 | vertebrates,human | 1 | Reoviridae,Rotavirus,Rotavirus A | seg. 9 | AY855064 |
| Rotavirus G8 | NC_011510 | vertebrates,human | 1 | Reoviridae,Rotavirus,Rotavirus A | seg. 4 | AF045228 |
| Rotavirus G9 | NC_011503 | vertebrates,human | 156 | Reoviridae,Rotavirus,Rotavirus A | seg. 9 | AY253834,AJ250544,AB436831,AJ250276,EF199728,AB436820,AY699298,AB436832,AY262748,AY69930 2,AY307092,AY3070 88,AY307094,AB436 833,AY866500,AY87 9296,AY699301,EF19 9729,AY255835,AY6 99291,FJ695604,EF1 99735,AJ250275,AY2 11065,AJ250270,EU8 39936,AJ250269,DQ 647423,EU839929,E U839939,EF199736, AB436821,DQ056298,AY699292,AB09175 2,EF532837,AY69929 0,AB436822,EF19997 3 8,AB091755,EU8399 37,AY262747,AY211 067,AJ250268,AB364 369,EU839933,AY25 3836,AB436834,AJ25 0274,EU839932,AY6 99293,DQ056299,AJ 250277,DQ056300,E |

| Taxonomy | NCBI Reference Sequence ID | Host | No. of Genomes | Lineage | Segment Count | Genbank Accession ID |
|---|---|---|---|---|---|---|
| | | | | | | F199737,HQ018933,JF703095,DQ096290, AY695811,AY211068, HQ018932,AY253833,AY866504,EU839940,AY699294,AJ491179,DQ056297,EF199730,AB091750,AJ491177,AB436826,DQ056296,AY699297,AJ250272,EU839930,AB091751,JF703094,DQO96288,EF199732,EF199726,AB091748,EF199734,AY253838,DQ990318,AY262746,AY253839,EF687001,EU839938,AY699296,AY184813,AY307087,AB436824,AJ491184,AY699299,AB364380,AB045372,DQ096293,EF199727,AJ502292,AB436835,AY307086,AB436830,AB091754,AY307093,DQ096289,AY699304,AY695809,AB091749,AY262749,EF199725,AB091756,DQ990319,AY307091,AJ491175,AY866502,AB436827,AB436825,AB045373,HQ018934,DQ096294,AY699303,DQ990317,DQ096291,AB436829,AY866505,AY253837,EU753963,AB436823,AY866501,AY866503,AB091747,EU839941,EF199731,AB436828,AY307085,JF703096,AB091753,AF359358,AJ250540,AY307090,DQ490173,EF199733,AB091746,AY816184,AB04 |

| Taxonomy | NCBI Reference Sequence ID | Host | No. of Genomes | Lineage | Segment Count | Genbank Accession ID |
|---|---|---|---|---|---|---|
| Rotavirus G9 | NC_011504 | vertebrates,human | 4 | Reoviridae,Rotavirus,Rotavirus A | seg. 10 | 5374,AJ250271,EU839931,AJ491172,AJ250545,AY699300,AY307089,AY699295,AY211066,JF703097 |
| Rotavirus G9 | NC_011509 | vertebrates,human | 1 | Reoviridae,Rotavirus,Rotavirus A | seg. 6 | EF033203,EF059924,EF033202,EF033204 |
| Rotavirus G9 | NC_011510 | vertebrates,human | 1 | Reoviridae,Rotavirus,Rotavirus A | seg. 4 | EU753964 |
| Rotavirus | NC_011503 | vertebrates,human | 1 | Reoviridae,Rotavirus,Rotavirus A | seg. 9 | EF059923 |
| RVA/G1/Human/India/UK-HLD/2011/H14 | | | | | | JX411969 |
| Rotavirus RVA/G1/Human/India/UK-HLD/2011/H180 | NC_011503 | vertebrates,human | 1 | Reoviridae,Rotavirus,Rotavirus A | seg. 9 | JX411970 |
| Rotavirus RVA/G9/Human/India/UK-HLD/2011/H140 | NC_011503 | vertebrates,human | 1 | Reoviridae,Rotavirus,Rotavirus A | seg. 9 | JX411968 |
| Rotavirus str.US1205 | NC_011503 | vertebrates,human | 1 | Reoviridae,Rotavirus,Rotavirus A | seg. 9 | AF060487 |
| Rotavirus strain TUCH | NC_011509 | vertebrates,human | 1 | Reoviridae,Rotavirus,Rotavirus A | seg. 6 | AY594670 |
| Rotavirus strain TUCH | NC_011510 | vertebrates,human | 1 | Reoviridae,Rotavirus,Rotavirus A | seg. 4 | AY596189 |
| Rotavirus subgroup 1 | NC_011503 | vertebrates,human | 2 | Reoviridae,Rotavirus,Rotavirus A | seg. 9 | K02028,L11605 |
| Rotavirus subgroup 1 | NC_011504 | vertebrates,human | 1 | Reoviridae,Rotavirus,Rotavirus A | seg. 10 | K03384 |
| Rotavirus subgroup 1 | NC_011505 | vertebrates,human | 1 | Reoviridae,Rotavirus,Rotavirus A | seg. 11 | K03385 |
| Rotavirus subgroup 1 | NC_011509 | vertebrates,human | 1 | Reoviridae,Rotavirus,Rotavirus A | seg. 6 | DQ0325 |
| Rotavirus subgroup 2 | NC_011501 | vertebrates,human | 1 | Reoviridae,Rotavirus,Rotavirus A | seg. 7 | X57944 |
| Rotavirus subgroup 2 | NC_011503 | vertebrates,human | 1 | Reoviridae,Rotavirus,Rotavirus A | seg. 9 | K02033 |
| Rotavirus subgroup 2 | NC_011504 | vertebrates,human | 1 | Reoviridae,Rotavirus,Rotavirus A | seg. 10 | K02032 |
| Rotavirus subgroup 2 | NC_011509 | vertebrates,human | 2 | Reoviridae,Rotavirus,Rotavirus A | seg. 6 | X57943,K02086 |
| Rubella virus | NC_001545 | vertebrates,human | 47 | Togaviridae,Rubivirus,Rubella virus | — | AY258323,JN635281,JN635282,JN635292,JN635285,AF435866,JN635296,DQ085341,AB047329,AF435865,AB588193,DQ08534 0,L78917,JN635290,AB588188,AB047330,JN635293,JN635288,AB222608,JN635284,DQ388281,JN635291,JF727653,FJ21158 8,JN635287,AB222609,KF201674,AB588192,JN635281,JN635295,JN635283,AB588192,JN635283 |

-continued

| Taxonomy | NCBI Reference Sequence ID | Host | No. of Genomes | Lineage | Segment Count | Genbank Accession ID |
|---|---|---|---|---|---|---|
| | | | | | | 9,AF188704,AY258322,AB588189,JN635294,DQ388280,JF727654,DQ085342,AB588190,M15240,DQ085343,FJ211587,DQ085339,JN635286,DQ085338,DQ388279 |
| SARS Coronavirus CDC#200301157 | NC_004718 | vertebrates,human | 1 | Coronaviridae,Betacoronavirus,Severe acute respiratory syndrome-related coronavirus | — | AY714217 |
| SARS coronavirus | NC_004718 | vertebrates,human | 25 | Coronaviridae,Betacoronavirus,Severe acute respiratory syndrome-related coronavirus | — | AY545914,JX163925,AY545917,CS569493,C0918585,DQ898174,JX163923,C0918584,CS079026,CS079027,JX163924,JX163926,AY545916,JX163928,DQ497008,CS079029,JX163927,CS079028,CS254197,AY545918,C0918598,FJ959407,AY274119,AY545919,AY545915 |
| SARS coronavirus A022 | NC_004718 | vertebrates,human | 1 | Coronaviridae,Betacoronavirus,Severe acute respiratory syndrome-related coronavirus | — | AY686863 |
| SARS coronavirus AS | NC_004718 | vertebrates,human | 1 | Coronaviridae,Betacoronavirus,Severe acute respiratory syndrome-related coronavirus | — | AY427439 |
| SARS coronavirus B039 | NC_004718 | vertebrates,human | 1 | Coronaviridae,Betacoronavirus,Severe acute respiratory syndrome-related coronavirus | — | AY686864 |
| SARS coronavirus BJQ1 | NC_004718 | vertebrates,human | 1 | Coronaviridae,Betacoronavirus,Severe acute respiratory syndrome-related coronavirus | — | AY278488 |
| SARS coronavirus BJQ2 | NC_004718 | vertebrates,human | 1 | Coronaviridae,Betacoronavirus,Severe acute respiratory syndrome-related coronavirus | — | AY278487 |
| SARS coronavirus BJQ3 | NC_004718 | vertebrates,human | 1 | Coronaviridae,Betacoronavirus,Severe acute respiratory syndrome-related coronavirus | — | AY278490 |
| SARS coronavirus BJQ4 | NC_004718 | vertebrates,human | 1 | Coronaviridae,Betacoronavirus,Severe acute respiratory syndrome-related coronavirus | — | AY279354 |
| SARS coronavirus BJ162 | NC_004718 | vertebrates,human | 1 | Coronaviridae,Betacoronavirus,Severe acute respiratory syndrome-related coronavirus | — | AY864805 |
| SARS coronavirus BJ182-12 | NC_004718 | vertebrates,human | 1 | Coronaviridae,Betacoronavirus,Severe acute respiratory syndrome-related coronavirus | — | EU371564 |
| SARS coronavirus BJ182-4 | NC_004718 | vertebrates,human | 1 | Coronaviridae,Betacoronavirus,Severe acute respiratory syndrome-related coronavirus | — | EU371562 |
| SARS coronavirus BJ182-8 | NC_004718 | vertebrates,human | 1 | Coronaviridae,Betacoronavirus,Severe acute respiratory syndrome-related coronavirus | — | EU371563 |
| SARS coronavirus BJ182a | NC_004718 | vertebrates,human | 1 | Coronaviridae,Betacoronavirus,Severe acute respiratory syndrome-related coronavirus | — | EU371560 |

-continued

| Taxonomy | NCBI Reference Sequence ID | Host | No. of Genomes | Lineage | Segment Count | Genbank Accession ID |
|---|---|---|---|---|---|---|
| SARS coronavirus BJ182b | NC_004718 | vertebrates,human | 1 | Coronaviridae,Betacoronavirus,Severe acute respiratory syndrome-related coronavirus | — | EU371561 |
| SARS coronavirus BJ202 | NC_004718 | vertebrates,human | 1 | Coronaviridae,Betacoronavirus,Severe acute respiratory syndrome-related coronavirus | — | AY864806 |
| SARS coronavirus CUHK-AGO1 | NC_004718 | vertebrates,human | 1 | Coronaviridae,Betacoronavirus,Severe acute respiratory syndrome-related coronavirus | — | AY345986 |
| SARS coronavirus CUHK-AGO2 | NC_004718 | vertebrates,human | 1 | Coronaviridae,Betacoronavirus,Severe acute respiratory syndrome-related coronavirus | — | AY345987 |
| SARS coronavirus CUHK-AGO3 | NC_004718 | vertebrates,human | 1 | Coronaviridae,Betacoronavirus,Severe acute respiratory syndrome-related coronavirus | — | AY345988 |
| SARS coronavirus CUHK-Sul 0 | NC_004718 | vertebrates,human | 1 | Coronaviridae,Betacoronavirus,Severe acute respiratory syndrome-related coronavirus | — | AY282752 |
| SARS coronavirus CUHK-W1 | NC_004718 | vertebrates,human | 1 | Coronaviridae,Betacoronavirus,Severe acute respiratory syndrome-related coronavirus | — | AY278554 |
| SARS coronavirus ExoN1 | NC_004718 | vertebrates,human | 33 | Coronaviridae,Betacoronavirus,Severe acute respiratory syndrome-related coronavirus | — | FJ882956,KF514395, KF514410,FJ882950, FJ882931,KF514412, KF514406,KF514403, FJ882955,KF514401, KF514416,KF514391, FJ882940,KF514417, KF514420,KF514393, KF514389,KF514405, KF514390,KF514402, FJ882926,KF514411, FJ882928,FJ882930, KF514414,FJ882941, FJ882944,KF514407, FJ882954,FJ882960, JF292922,JX162087, FJ882929 |
| SARS coronavirus FRA | NC_004718 | vertebrates,human | 1 | Coronaviridae,Betacoronavirus,Severe acute respiratory syndrome-related coronavirus | — | AY310120 |
| SARS coronavirus Frankfurt 1 | NC_004718 | vertebrates,human | 2 | Coronaviridae,Betacoronavirus,Severe acute respiratory syndrome-related coronavirus | — | AB257344,AY291315 |
| SARS coronavirus GDQ1 | NC_004718 | vertebrates,human | 1 | Coronaviridae,Betacoronavirus,Severe acute respiratory syndrome-related coronavirus | — | AY278489 |
| SARS coronavirus GD69 | NC_004718 | vertebrates,human | 1 | Coronaviridae,Betacoronavirus,Severe acute respiratory syndrome-related coronavirus | — | AY313906 |
| SARS coronavirus GDH-BJHO1 | NC_004718 | vertebrates,human | 1 | Coronaviridae,Betacoronavirus,Severe acute respiratory syndrome-related coronavirus | — | DQ640652 |
| SARS coronavirus GZ-A | NC_004718 | vertebrates,human | 1 | Coronaviridae,Betacoronavirus,Severe acute respiratory syndrome-related coronavirus | — | AY394977 |
| SARS coronavirus GZ-B | NC_004718 | vertebrates,human | 1 | Coronaviridae,Betacoronavirus,Severe acute respiratory syndrome-related coronavirus | — | AY394978 |
| SARS coronavirus GZ-C | NC_004718 | vertebrates,human | 1 | Coronaviridae,Betacoronavirus,Severe acute respiratory syndrome-related coronavirus | — | AY394979 |

-continued

| Taxonomy | NCBI Reference Sequence ID | Host | No. of Genomes | Lineage | Segment Count | Genbank Accession ID |
|---|---|---|---|---|---|---|
| SARS coronavirus GZ-D | NC_004718 | vertebrates,human | 1 | Coronaviridae,Betacoronavirus,Severe acute respiratory syndrome-related coronavirus | — | AY394980 |
| SARS coronavirus GZO2 | NC_004718 | vertebrates,human | 1 | Coronaviridae,Betacoronavirus,Severe acute respiratory syndrome-related coronavirus | — | AY390556 |
| SARS coronavirus GZ0401 | NC_004718 | vertebrates,human | 1 | Coronaviridae,Betacoronavirus,Severe acute respiratory syndrome-related coronavirus | — | AY568539 |
| SARS coronavirus GZ0402 | NC_004718 | vertebrates,human | 1 | Coronaviridae,Betacoronavirus,Severe acute respiratory syndrome-related coronavirus | — | AY613947 |
| SARS coronavirus GZ50 | NC_004718 | vertebrates,human | 1 | Coronaviridae,Betacoronavirus,Severe acute respiratory syndrome-related coronavirus | — | AY304495 |
| SARS coronavirus HC/SZ/61/03 | NC_004718 | vertebrates,human | 1 | Coronaviridae,Betacoronavirus,Severe acute respiratory syndrome-related coronavirus | — | AY515512 |
| SARS coronavirus HGZ8L1-A | NC_004718 | vertebrates,human | 1 | Coronaviridae,Betacoronavirus,Severe acute respiratory syndrome-related coronavirus | — | AY394981 |
| SARS coronavirus HGZ8L1-B | NC_004718 | vertebrates,human | 1 | Coronaviridae,Betacoronavirus,Severe acute respiratory syndrome-related coronavirus | — | AY394982 |
| SARS coronavirus HGZ8L2 | NC_004718 | vertebrates,human | 1 | Coronaviridae,Betacoronavirus,Severe acute respiratory syndrome-related coronavirus | — | AY394993 |
| SARS coronavirus HKU-39849 | NC_004718 | vertebrates,human | 6 | Coronaviridae,Betacoronavirus,Severe acute respiratory syndrome-related coronavirus | — | JQ316196,JN854286, GU553365,AY278491 ,GU553363,GU553364 |
| SARS coronavirus HSR 1 | NC_004718 | vertebrates,human | 1 | Coronaviridae,Betacoronavirus,Severe acute respiratory syndrome-related coronavirus | — | AY323977 |
| SARS coronavirus HSZ-A | NC_004718 | vertebrates,human | 1 | Coronaviridae,Betacoronavirus,Severe acute respiratory syndrome-related coronavirus | — | AY394984 |
| SARS coronavirus HSZ-Bb | NC_004718 | vertebrates,human | 1 | Coronaviridae,Betacoronavirus,Severe acute respiratory syndrome-related coronavirus | — | AY394985 |
| SARS coronavirus HSZ-Bc | NC_004718 | vertebrates,human | 1 | Coronaviridae,Betacoronavirus,Severe acute respiratory syndrome-related coronavirus | — | AY394994 |
| SARS coronavirus HSZ-Cb | NC_004718 | vertebrates,human | 1 | Coronaviridae,Betacoronavirus,Severe acute respiratory syndrome-related coronavirus | — | AY394986 |
| SARS coronavirus HSZ-Cc | NC_004718 | vertebrates,human | 1 | Coronaviridae,Betacoronavirus,Severe acute respiratory syndrome-related coronavirus | — | AY394995 |
| SARS coronavirus HZS2-A | NC_004718 | vertebrates,human | 1 | Coronaviridae,Betacoronavirus,Severe acute respiratory syndrome-related coronavirus | — | AY394983 |
| SARS coronavirus HZS2-Bb | NC_004718 | vertebrates,human | 1 | Coronaviridae,Betacoronavirus,Severe acute respiratory syndrome-related coronavirus | — | AY395004 |
| SARS coronavirus HZS2-C | NC_004718 | vertebrates,human | 1 | Coronaviridae,Betacoronavirus,Severe acute respiratory syndrome-related coronavirus | — | AY394992 |
| SARS coronavirus HZS2-D | NC_004718 | vertebrates,human | 1 | Coronaviridae,Betacoronavirus,Severe acute respiratory syndrome-related coronavirus | — | AY394989 |
| SARS coronavirus HZS2-E | NC_004718 | vertebrates,human | 1 | Coronaviridae,Betacoronavirus,Severe acute respiratory syndrome-related coronavirus | — | AY394990 |
| SARS coronavirus HZS2-Fb | NC_004718 | vertebrates,human | 1 | Coronaviridae,Betacoronavirus,Severe acute respiratory syndrome-related coronavirus | — | AY394987 |
| SARS coronavirus HZS2-Fc | NC_004718 | vertebrates,human | 1 | Coronaviridae,Betacoronavirus,Severe acute respiratory syndrome-related coronavirus | — | AY394991 |

-continued

| Taxonomy | NCBI Reference Sequence ID | Host | No. of Genomes | Lineage | Segment Count | Genbank Accession ID |
|---|---|---|---|---|---|---|
| SARS coronavirus JMD | NC_004718 | vertebrates,human | 1 | Coronaviridae,Betacoronavirus,Severe acute respiratory syndrome-related coronavirus | — | AY394988 |
| SARS coronavirus LC1 | NC_004718 | vertebrates,human | 1 | Coronaviridae,Betacoronavirus,Severe acute respiratory syndrome-related coronavirus | — | AY394998 |
| SARS coronavirus LC2 | NC_004718 | vertebrates,human | 1 | Coronaviridae,Betacoronavirus,Severe acute respiratory syndrome-related coronavirus | — | AY394999 |
| SARS coronavirus LC3 | NC_004718 | vertebrates,human | 1 | Coronaviridae,Betacoronavirus,Severe acute respiratory syndrome-related coronavirus | — | AY395000 |
| SARS coronavirus LC4 | NC_004718 | vertebrates,human | 1 | Coronaviridae,Betacoronavirus,Severe acute respiratory syndrome-related coronavirus | — | AY395001 |
| SARS coronavirus LC5 | NC_004718 | vertebrates,human | 1 | Coronaviridae,Betacoronavirus,Severe acute respiratory syndrome-related coronavirus | — | AY395002 |
| SARS coronavirus LU-2004 | NC_004718 | vertebrates,human | 1 | Coronaviridae,Betacoronavirus,Severe acute respiratory syndrome-related coronavirus | — | AY595412 |
| SARS coronavirus MA15 | NC_004718 | vertebrates,human | 26 | Coronaviridae,Betacoronavirus,Severe acute respiratory syndrome-related coronavirus | — | FJ882958,JF292910, FJ882961,JF292912, FJ882948,JF292914, JF292911,JF292908, FJ882952,JF292915, JF292918,HQ890546, HQ890542,JF292917, FJ882945,JF292913, HQ890543,HQ890544,HQ890545,HQ890541,JF292916,JF292919,JF292909,JF292907,FJ882957,JF292920 |
| SARS coronavirus MA15 ExoN1 | NC_004718 | vertebrates,human | 26 | Coronaviridae,Betacoronavirus,Severe acute respiratory syndrome-related coronavirus | — | FJ882953,HQ890539, JF292904,FJ882942, HQ890527,HQ890529,HQ890538,HQ890536,HQ890540,JF292903,HQ890526,HQ890537,FJ882959,FJ882943,FJ882951,HQ890530,HQ890535,JF292902,HQ890532,HQ890533,HQ890531,HQ890534,HQ890528,JF292906,JF292905,FJ882962 |
| SARS coronavirus NS-1 | NC_004718 | vertebrates,human | 1 | Coronaviridae,Betacoronavirus,Severe acute respiratory syndrome-related coronavirus | — | AY508724 |
| SARS coronavirus P2 | NC_004718 | vertebrates,human | 1 | Coronaviridae,Betacoronavirus,Severe acute respiratory syndrome-related coronavirus | — | FJ882963 |
| SARS coronavirus PC4-13 | NC_004718 | vertebrates,human | 1 | Coronaviridae,Betacoronavirus,Severe acute respiratory syndrome-related coronavirus | — | AY613948 |

-continued

| Taxonomy | NCBI Reference Sequence ID | Host | No. of Genomes | Lineage | Segment Count | Genbank Accession ID |
|---|---|---|---|---|---|---|
| SARS coronavirus PC4-136 | NC_004718 | vertebrates,human | 1 | Coronaviridae,Betacoronavirus,Severe acute respiratory syndrome-related coronavirus | — | AY613949 |
| SARS coronavirus PC4-227 | NC_004718 | vertebrates,human | 1 | Coronaviridae,Betacoronavirus,Severe acute respiratory syndrome-related coronavirus | — | AY613950 |
| SARS coronavirus PUMC01 | NC_004718 | vertebrates,human | 1 | Coronaviridae,Betacoronavirus,Severe acute respiratory syndrome-related coronavirus | — | AY350750 |
| SARS coronavirus PUMCO2 | NC_004718 | vertebrates,human | 1 | Coronaviridae,Betacoronavirus,Severe acute respiratory syndrome-related coronavirus | — | AY357075 |
| SARS coronavirus PUMC03 | NC_004718 | vertebrates,human | 1 | Coronaviridae,Betacoronavirus,Severe acute respiratory syndrome-related coronavirus | — | AY357076 |
| SARS coronavirus Rs_672/2006 | NC_004718 | vertebrates,human | 1 | Coronaviridae,Betacoronavirus,Severe acute respiratory syndrome-related coronavirus | — | FJ588686 |
| SARS coronavirus ShanghaiQXC1 | NC_004718 | vertebrates,human | 1 | Coronaviridae,Betacoronavirus,Severe acute respiratory syndrome-related coronavirus | — | AY463059 |
| SARS coronavirus ShanghaiQXC2 | NC_004718 | vertebrates,human | 1 | Coronaviridae,Betacoronavirus,Severe acute respiratory syndrome-related coronavirus | — | AY463060 |
| SARS coronavirus Sin2500 | NC_004718 | vertebrates,human | 1 | Coronaviridae,Betacoronavirus,Severe acute respiratory syndrome-related coronavirus | — | AY283794 |
| SARS coronavirus Sin2677 | NC_004718 | vertebrates,human | 1 | Coronaviridae,Betacoronavirus,Severe acute respiratory syndrome-related coronavirus | — | AY283795 |
| SARS coronavirus Sin2679 | NC_004718 | vertebrates,human | 1 | Coronaviridae,Betacoronavirus,Severe acute respiratory syndrome-related coronavirus | — | AY283796 |
| SARS coronavirus Sin2748 | NC_004718 | vertebrates,human | 1 | Coronaviridae,Betacoronavirus,Severe acute respiratory syndrome-related coronavirus | — | AY283797 |
| SARS coronavirus Sin2774 | NC_004718 | vertebrates,human | 1 | Coronaviridae,Betacoronavirus,Severe acute respiratory syndrome-related coronavirus | — | AY283798 |
| SARS coronavirus Sin3408 | NC_004718 | vertebrates,human | 1 | Coronaviridae,Betacoronavirus,Severe acute respiratory syndrome-related coronavirus | — | AY559083 |
| SARS coronavirus Sin3408L | NC_004718 | vertebrates,human | 1 | Coronaviridae,Betacoronavirus,Severe acute respiratory syndrome-related coronavirus | — | AY559097 |
| SARS coronavirus Sin3725V | NC_004718 | vertebrates,human | 1 | Coronaviridae,Betacoronavirus,Severe acute respiratory syndrome-related coronavirus | — | AY559087 |
| SARS coronavirus Sin3765V | NC_004718 | vertebrates,human | 1 | Coronaviridae,Betacoronavirus,Severe acute respiratory syndrome-related coronavirus | — | AY559084 |
| SARS coronavirus Sin842 | NC_004718 | vertebrates,human | 1 | Coronaviridae,Betacoronavirus,Severe acute respiratory syndrome-related coronavirus | — | AY559081 |
| SARS coronavirus Sin845 | NC_004718 | vertebrates,human | 1 | Coronaviridae,Betacoronavirus,Severe acute respiratory syndrome-related coronavirus | — | AY559093 |
| SARS coronavirus Sin846 | NC_004718 | vertebrates,human | 1 | Coronaviridae,Betacoronavirus,Severe acute respiratory syndrome-related coronavirus | — | AY559094 |
| SARS coronavirus Sin847 | NC_004718 | vertebrates,human | 1 | Coronaviridae,Betacoronavirus,Severe acute respiratory syndrome-related coronavirus | — | AY559095 |
| SARS coronavirus Sin848 | NC_004718 | vertebrates,human | 1 | Coronaviridae,Betacoronavirus,Severe acute respiratory syndrome-related coronavirus | — | AY559085 |
| SARS coronavirus Sin849 | NC_004718 | vertebrates,human | 1 | Coronaviridae,Betacoronavirus,Severe acute respiratory syndrome-related coronavirus | — | AY559086 |
| SARS coronavirus Sin850 | NC_004718 | vertebrates,human | 1 | Coronaviridae,Betacoronavirus,Severe acute respiratory syndrome-related coronavirus | — | AY559096 |

-continued

| Taxonomy | NCBI Reference Sequence ID | Host | No. of Genomes | Lineage | Segment Count | Genbank Accession ID |
|---|---|---|---|---|---|---|
| SARS coronavirus Sin852 | NC_004718 | vertebrates,human | 1 | Coronaviridae,Betacoronavirus,Severe acute respiratory syndrome-related coronavirus | — | AY559082 |
| SARS coronavirus SinP1 | NC_004718 | vertebrates,human | 1 | Coronaviridae,Betacoronavirus,Severe acute respiratory syndrome-related coronavirus | — | AY559088 |
| SARS coronavirus SinP2 | NC_004718 | vertebrates,human | 1 | Coronaviridae,Betacoronavirus,Severe acute respiratory syndrome-related coronavirus | — | AY559089 |
| SARS coronavirus SinP3 | NC_004718 | vertebrates,human | 1 | Coronaviridae,Betacoronavirus,Severe acute respiratory syndrome-related coronavirus | — | AY559090 |
| SARS coronavirus SinP4 | NC_004718 | vertebrates,human | 1 | Coronaviridae,Betacoronavirus,Severe acute respiratory syndrome-related coronavirus | — | AY559091 |
| SARS coronavirus SinP5 | NC_004718 | vertebrates,human | 1 | Coronaviridae,Betacoronavirus,Severe acute respiratory syndrome-related coronavirus | — | AY559092 |
| SARS coronavirus Sino1-11 | NC_004718 | vertebrates,human | 1 | Coronaviridae,Betacoronavirus,Severe acute respiratory syndrome-related coronavirus | — | AY485277 |
| SARS coronavirus Sino3-11 | NC_004718 | vertebrates,human | 1 | Coronaviridae,Betacoronavirus,Severe acute respiratory syndrome-related coronavirus | — | AY485278 |
| SARS coronavirus SoD | NC_004718 | vertebrates,human | 1 | Coronaviridae,Betacoronavirus,Severe acute respiratory syndrome-related coronavirus | — | AY461660 |
| SARS coronavirus TJF | NC_004718 | vertebrates,human | 1 | Coronaviridae,Betacoronavirus,Severe acute respiratory syndrome-related coronavirus | — | AY654624 |
| SARS coronavirus TW1 | NC_004718 | vertebrates,human | 1 | Coronaviridae,Betacoronavirus,Severe acute respiratory syndrome-related coronavirus | — | AY291451 |
| SARS coronavirus TW10 | NC_004718 | vertebrates,human | 1 | Coronaviridae,Betacoronavirus,Severe acute respiratory syndrome-related coronavirus | — | AY502923 |
| SARS coronavirus TW11 | NC_004718 | vertebrates,human | 1 | Coronaviridae,Betacoronavirus,Severe acute respiratory syndrome-related coronavirus | — | AY502924 |
| SARS coronavirus TW2 | NC_004718 | vertebrates,human | 1 | Coronaviridae,Betacoronavirus,Severe acute respiratory syndrome-related coronavirus | — | AY502925 |
| SARS coronavirus TW3 | NC_004718 | vertebrates,human | 1 | Coronaviridae,Betacoronavirus,Severe acute respiratory syndrome-related coronavirus | — | AY502926 |
| SARS coronavirus TW4 | NC_004718 | vertebrates,human | 1 | Coronaviridae,Betacoronavirus,Severe acute respiratory syndrome-related coronavirus | — | AY502927 |
| SARS coronavirus TW5 | NC_004718 | vertebrates,human | 1 | Coronaviridae,Betacoronavirus,Severe acute respiratory syndrome-related coronavirus | — | AY502928 |
| SARS coronavirus TW6 | NC_004718 | vertebrates,human | 1 | Coronaviridae,Betacoronavirus,Severe acute respiratory syndrome-related coronavirus | — | AY502929 |
| SARS coronavirus TW7 | NC_004718 | vertebrates,human | 1 | Coronaviridae,Betacoronavirus,Severe acute respiratory syndrome-related coronavirus | — | AY502930 |
| SARS coronavirus TW8 | NC_004718 | vertebrates,human | 1 | Coronaviridae,Betacoronavirus,Severe acute respiratory syndrome-related coronavirus | — | AY502931 |
| SARS coronavirus TW9 | NC_004718 | vertebrates,human | 1 | Coronaviridae,Betacoronavirus,Severe acute respiratory syndrome-related coronavirus | — | AY502932 |
| SARS coronavirus TWC | NC_004718 | vertebrates,human | 1 | Coronaviridae,Betacoronavirus,Severe acute respiratory syndrome-related coronavirus | — | AY321118 |
| SARS coronavirus TWC2 | NC_004718 | vertebrates,human | 1 | Coronaviridae,Betacoronavirus,Severe acute respiratory syndrome-related coronavirus | — | AY362698 |
| SARS coronavirus TWC3 | NC_004718 | vertebrates,human | 1 | Coronaviridae,Betacoronavirus,Severe acute respiratory syndrome-related coronavirus | — | AY362699 |

-continued

| Taxonomy | NCBI Reference Sequence ID | Host | No. of Genomes | Lineage | Segment Count | Genbank Accession ID |
|---|---|---|---|---|---|---|
| SARS coronavirus TWH | NC_004718 | vertebrates,human | 1 | Coronaviridae,Betacoronavirus,Severe acute respiratory syndrome-related coronavirus | — | AP006557 |
| SARS coronavirus TWJ | NC_004718 | vertebrates,human | 1 | Coronaviridae,Betacoronavirus,Severe acute respiratory syndrome-related coronavirus | — | AP006558 |
| SARS coronavirus TWK | NC_004718 | vertebrates,human | 1 | Coronaviridae,Betacoronavirus,Severe acute respiratory syndrome-related coronavirus | — | AP006559 |
| SARS coronavirus TWS | NC_004718 | vertebrates,human | 1 | Coronaviridae,Betacoronavirus,Severe acute respiratory syndrome-related coronavirus | — | AP006560 |
| SARS coronavirus TWY | NC_004718 | vertebrates,human | 1 | Coronaviridae,Betacoronavirus,Severe acute respiratory syndrome-related coronavirus | — | AP006561 |
| SARS coronavirus Taiwan TC1 | NC_004718 | vertebrates,human | 1 | Coronaviridae,Betacoronavirus,Severe acute respiratory syndrome-related coronavirus | — | AY338174 |
| SARS coronavirus Taiwan TC2 | NC_004718 | vertebrates,human | 1 | Coronaviridae,Betacoronavirus,Severe acute respiratory syndrome-related coronavirus | — | AY338175 |
| SARS coronavirus Taiwan TC3 | NC_004718 | vertebrates,human | 1 | Coronaviridae,Betacoronavirus,Severe acute respiratory syndrome-related coronavirus | — | AY348314 |
| SARS coronavirus Urbani | NC_004718 | vertebrates,human | 1 | Coronaviridae,Betacoronavirus,Severe acute respiratory syndrome-related coronavirus | — | AY278741 |
| SARS coronavirus W H20 | NC_004718 | vertebrates,human | 1 | Coronaviridae,Betacoronavirus,Severe acute respiratory syndrome-related coronavirus | — | AY772062 |
| SARS coronavirus W HU | NC_004718 | vertebrates,human | 1 | Coronaviridae,Betacoronavirus,Severe acute respiratory syndrome-related coronavirus | — | AY394850 |
| SARS coronavirus ZJO1 | NC_004718 | vertebrates,human | 1 | Coronaviridae,Betacoronavirus,Severe acute respiratory syndrome-related coronavirus | — | AY297028 |
| SARS coronavirus ZJO2 | NC_004718 | vertebrates,human | 1 | Coronaviridae,Betacoronavirus,Severe acute respiratory syndrome-related coronavirus | — | EU371559 |
| SARS coronavirus ZJO301 | NC_004718 | vertebrates,human | 1 | Coronaviridae,Betacoronavirus,Severe acute respiratory syndrome-related coronavirus | — | DQ182595 |
| SARS coronavirus ZMY 1 | NC_004718 | vertebrates,human | 1 | Coronaviridae,Betacoronavirus,Severe acute respiratory syndrome-related coronavirus | — | AY351680 |
| SARS coronavirus ZS-A | NC_004718 | vertebrates,human | 1 | Coronaviridae,Betacoronavirus,Severe acute respiratory syndrome-related coronavirus | — | AY394997 |
| SARS coronavirus ZS-B | NC_004718 | vertebrates,human | 1 | Coronaviridae,Betacoronavirus,Severe acute respiratory syndrome-related coronavirus | — | AY394996 |
| SARS coronavirus ZS-C | NC_004718 | vertebrates,human | 1 | Coronaviridae,Betacoronavirus,Severe acute respiratory syndrome-related coronavirus | — | AY395003 |
| SARS coronavirus civet010 | NC_004718 | vertebrates,human | 1 | Coronaviridae,Betacoronavirus,Severe acute respiratory syndrome-related coronavirus | — | AY572035 |
| SARS coronavirus civet020 | NC_004718 | vertebrates,human | 1 | Coronaviridae,Betacoronavirus,Severe acute respiratory syndrome-related coronavirus | — | AY572038 |
| SARS coronavirus wtic-MB | NC_004718 | vertebrates,human | 31 | Coronaviridae,Betacoronavirus,Severe acute respiratory syndrome-related coronavirus | — | KF514421,FJ882932, FJ882937,KF514413, KF514400,KF514392, KF514399,JF292921, KF514415,FJ882927, KF514398,KF514408, KF514419,FJ882938, KF514423,FJ882934, |

-continued

| Taxonomy | NCBI Reference Sequence ID | Host | No. of Genomes | Lineage | Segment Count | Genbank Accession ID |
|---|---|---|---|---|---|---|
| | | | | | | KF514418,FJ882939, KF514396,KF514397, FJ882936,FJ882949, FJ882946,FJ882933, FJ882947,KF514394, KF514409,KF514422, KF514388,FJ882935, KF514404 |
| Sabia virus | NC_006313 | vertebrates,human | 3 | Arenaviridae,Arenavirus,Sabia virus | seg. L | JN801475,AY358026, AY216506 |
| Sabia virus | NC_006317 | vertebrates,human | 2 | Arenaviridae,Arenavirus,Sabia virus | seg. S | U41071,JN801474 |
| Sapovirus Chanthaburi-74/Thailand | NC_000940,NC_010624,NC_006269,NC_006554 | vertebrates,human | 1 | Caliciviridae,Sapovirus,Sapporo virus | — | AY646854 |
| Sapovirus Ehime1107/2002/JP | NC_000940,NC_010624,NC_006269,NC_006554 | vertebrates,human | 1 | Caliciviridae,Sapovirus,Sapporo virus | — | DQ058829 |
| Sapovirus Hu/Angelholm/SW278/2004/SE | NC_000940,NC_01062 an 4,NC_006269,NC_006554 | vertebrates,human | 1 | Caliciviridae,Sapovirus,Sapporo virus | — | DQ125333 |
| Sapovirus Hu/Angelholm/5W314/2004/SE | NC_000940,NC_010624,NC_006269,NC_006554 | vertebrates,human | 1 | Caliciviridae,Sapovirus,Sapporo virus | — | DQ125334 |
| Sapovirus Hu/Bristo1/1998/UK | NC_000940,NC_010624,NC_006269,NC_006554 | vertebrates,human | 1 | Caliciviridae,Sapovirus,Sapporo virus | — | AJ249939 |
| Sapovirus Hu/Chiba/000671/1999/JP | NC_000940,NC_010624,NC_006269,NC_006554 | vertebrates,human | 1 | Caliciviridae,Sapovirus,Sapporo virus | — | AJ786349 |
| Sapovirus Hu/Ehime1596/1999/JP | NC_000940, NC_010624,NC_006269,NC_006554 | vertebrates,human | 1 | Caliciviridae,Sapovirus,Sapporo virus | — | DQ366346 |

-continued

| Taxonomy | NCBI Reference Sequence ID | Host | No. of Genomes | Lineage | Segment Count | Genbank Accession ID |
|---|---|---|---|---|---|---|
| Sapovirus Hu/Ehime475/2004/JP | NC_000940,NC_01062 4,NC_0062 69,NC_006 554 | vertebrates,human | 1 | Caliciviridae,Sapovirus,Sapporo virus | — | DQ366344 |
| Sapovirus Hu/Ehime643/March 2000/JP | NC_000940,NC_01062 4,NC_0062 69,NC_006 554 | vertebrates,human | 1 | Caliciviridae,Sapovirus,Sapporo virus | — | DQ366345 |
| Sapovirus Hu/G I,2/BR-DF01/BRA/2009 | NC_000940,NC_01062 4,NC_0062 69,NC_006 554 | vertebrates,human | 1 | Caliciviridae,Sapovirus,Sapporo virus | — | AB614356 |
| Sapovirus Hu/GI/Sapporo/MT-2010/1982 | NC_000940,NC_01062 4,NC_0062 69,NC_006 554 | vertebrates,human | 1 | Caliciviridae,Sapovirus,Sapporo virus | — | HM002617 |
| Sapovirus Mc114 | NC_000940,NC_01062 4,NC_0062 69,NC_006 554 | vertebrates,human | 1 | Caliciviridae,Sapovirus,Sapporo virus | — | AY237422 |
| Sapovirus Mc2 | NC_000940,NC_01062 4,NC_0062 69,NC_006 554 | vertebrates,human | 1 | Caliciviridae,Sapovirus,Sapporo virus | — | AY237419 |
| Sapovirus N21 | NC_000940,NC_01062 4,NC_0062 69,NC_006 554 | vertebrates,human | 1 | Caliciviridae,Sapovirus,Sapporo virus | — | AY237423 |
| Sapovirus NongKhai-24/Thailand | NC_000940,NC_01062 4,NC_0062 69,NC_006 554 | vertebrates,human | 1 | Caliciviridae,Sapovirus,Sapporo virus | — | AY646856 |
| Sapovirus NongKhai-50/Thailand | NC_000940,NC_01062 4,NC_0062 69,NC_006 554 | vertebrates,human | 1 | Caliciviridae,Sapovirus,Sapporo virus | — | AY646853 |

| Taxonomy | NCBI Reference Sequence ID | Host | No. of Genomes | Lineage | Segment Count | Genbank Accession ID |
|---|---|---|---|---|---|---|
| Sapovirus SaKaeo-15/Thailand | NC_000940,NC_010624,NC_006269,NC_006554 | vertebrates,human | 1 | Caliciviridae,Sapovirus,Sapporo virus | — | AY646855 |
| Sapovirus pig/Gansu/CH430/2012/CHN | NC_000940,NC_010624,NC_006269,NC_006554 | vertebrates,human | 1 | Caliciviridae,Sapovirus,Sapporo virus | — | KF204570 |
| Sapovirus pig/sav1/2008/CHN | NC_000940,NC_010624,NC_006269,NC_006554 | vertebrates,human | 1 | Caliciviridae,Sapovirus,Sapporo virus | — | FJ387164 |
| Sapporo rat virus | NC_005236 | vertebrates,human | 1 | Bunyaviridae,Hantavirus,Seoul virus | seg. S | M34881 |
| Sapporo rat virus | NC_005237 | vertebrates,human | 1 | Bunyaviridae,Hantavirus,Seoul virus | seg. M | M34882 |
| Sapporo virus-Manchester | NC_000940,NC_010624,NC_006269,NC_006554 | vertebrates,human | 1 | Caliciviridae,Sapovirus,Sapporo virus | — | X86560 |
| Seal anellovirus TFFN/USA/2006 | NC_015212 | vertebrates,human | 1 | Anelloviridae,Seal anellovirus TFFN/USA/2006 | — | HQ287751 |
| Sendai virus | NC_001552 | vertebrates,human | 20 | Paramyxoviridae,Respirovirus,Sendai virus | — | AB855653,AB005795,AB005796,AB065187,M69046,M30204,D0219803,AB195967,AB855655,EF679198,AB275417,AB065188,AB855654,AB039658,AB195968,AB275416,M30203,AB065189,AB065186,M30202 |
| Seoul virus | NC_005236 | vertebrates,human | 13 | Bunyaviridae,Hantavirus,Seoul virus | seg. S | AF406965,KC626089,JX853575,JX879769,JQ665912,HQ611980,AY006465,EF192308,AY766368,AY273791,JQ898106,JN377553,AY750171 |
| Seoul virus | NC_005237 | vertebrates,human | 11 | Bunyaviridae,Hantavirus,Seoul virus | seg. M | D17593,D17592,S47716,JN377554,JQ665888,JX853576,D1759174,DQ159911,JX879768,AB027521,EF117248 |

-continued

| Taxonomy | NCBI Reference Sequence ID | Host | No. of Genomes | Lineage | Segment Count | Genbank Accession ID |
|---|---|---|---|---|---|---|
| Seoul virus | NC_005238 | vertebrates,human | 5 | Bunyaviridae,Hantavirus,Seoul virus | seg. L | JX879770,EF190551, X56492,JX853574,EF 581094 |
| Seoul virus 5CSG | NC_005237 | vertebrates,human | 1 | Bunyaviridae,Hantavirus,Seoul virus | seg. M | AB618130 |
| Seoul virus B-1 | NC_005237 | vertebrates,human | 1 | Bunyaviridae,Hantavirus,Seoul virus | seg. M | X53861 |
| Seoul virus BjHDQ1 | NC_005236 | vertebrates,human | 1 | Bunyaviridae,Hantavirus,Seoul virus | seg. S | AY627049 |
| Seoul virus BjHDQ1 | NC_005237 | vertebrates,human | 1 | Bunyaviridae,Hantavirus,Seoul virus | seg. M | DQ133505 |
| Seoul virus CSG5 | NC_005236 | vertebrates,human | 1 | Bunyaviridae,Hantavirus,Seoul virus | seg. S | AB618112 |
| Seoul virus Gou3-e5 | NC_005237 | vertebrates,human | 1 | Bunyaviridae,Hantavirus,Seoul virus | seg. M | AF288650 |
| Seoul virus Hb8610 | NC_005236 | vertebrates,human | 1 | Bunyaviridae,Hantavirus,Seoul virus | seg. S | AF288643 |
| Seoul virus K24-e7 | NC_005236 | vertebrates,human | 1 | Bunyaviridae,Hantavirus,Seoul virus | seg. S | AF288653 |
| Seoul virus K24-e7 | NC_005237 | vertebrates,human | 1 | Bunyaviridae,Hantavirus,Seoul virus | seg. M | AF288652 |
| Seoul virus K24-v2 | NC_005236 | vertebrates,human | 1 | Bunyaviridae,Hantavirus,Seoul virus | seg. S | AF288655 |
| Seoul virus K24-v2 | NC_005237 | vertebrates,human | 1 | Bunyaviridae,Hantavirus,Seoul virus | seg. M | AF288654 |
| Seoulvirus Gou3 | NC_005236 | vertebrates,human | 1 | Bunyaviridae,Hantavirus,Seoul virus | seg. S | AF184988 |
| Seoulvirus Gou3 | NC_005237 | vertebrates,human | 1 | Bunyaviridae,Hantavirus,Seoul virus | seg. M | AF145977 |
| Seoulvirus HB55 | NC_005236 | vertebrates,human | 1 | Bunyaviridae,Hantavirus,Seoul virus | seg. S | AF035832 |
| Seoulvirus HB55 | NC_005237 | vertebrates,human | 1 | Bunyaviridae,Hantavirus,Seoul virus | seg. M | AF329388 |
| Seoulvirus IR461 | NC_005236 | vertebrates,human | 1 | Bunyaviridae,Hantavirus,Seoul virus | seg. S | AF458104 |
| Seoulvirus IR461 | NC_005237 | vertebrates,human | 1 | Bunyaviridae,Hantavirus,Seoul virus | seg. M | AF288299 |
| Seoulvirus L99 | NC_005236 | vertebrates,human | 2 | Bunyaviridae,Hantavirus,Seoul virus | seg. S | AF288298,AF035833 |
| Seoulvirus L99 | NC_005237 | vertebrates,human | 1 | Bunyaviridae,Hantavirus,Seoul virus | seg. M | AF288297 |
| Seoulvirus R22 | NC_005238 | vertebrates,human | 2 | Bunyaviridae,Hantavirus,Seoul virus | seg. L | AF488707,AF288295 |
| Seoulvirus tchoupitoulas | NC_005236 | vertebrates,human | 1 | Bunyaviridae,Hantavirus,Seoul virus | seg. S | AF329389 |
| Simian Agent 10 | NC_001796 | vertebrates,human | 1 | Paramyxoviridae,Respirovirus,Human parainfluenza virus 3 | — | HM583801 |
| Simian adenovirus 27.1 | NC_011202 | vertebrates,human | 1 | Adenoviridae,Mastadenovirus,Human adenovirus B | — | FJQ25909 |
| Simian adenovirus 27.1 | NC_011203 | vertebrates,human | 1 | Adenoviridae,Mastadenovirus,Human adenovirus B | — | FJQ25909 |
| Simian adenovirus 27.2 | NC_011202 | vertebrates,human | 1 | Adenoviridae,Mastadenovirus,Human adenovirus B | — | FJQ25928 |
| Simian adenovirus 27.2 | NC_011203 | vertebrates,human | 1 | Adenoviridae,Mastadenovirus,Human adenovirus B | — | FJQ25928 |
| Simian adenovirus 28.1 | NC_011202 | vertebrates,human | 1 | Adenoviridae,Mastadenovirus,Human adenovirus B | — | FJQ25914 |
| Simian adenovirus 28.1 | NC_011203 | vertebrates,human | 1 | Adenoviridae,Mastadenovirus,Human adenovirus B | — | FJQ25914 |
| Simian adenovirus 28.2 | NC_011202 | vertebrates,human | 1 | Adenoviridae,Mastadenovirus,Human adenovirus B | — | FJQ25915 |
| Simian adenovirus 28.2 | NC_011203 | vertebrates,human | 1 | Adenoviridae,Mastadenovirus,Human adenovirus B | — | FJQ25915 |
| Simian adenovirus 29 | NC_011202 | vertebrates,human | 1 | Adenoviridae,Mastadenovirus,Human adenovirus B | — | FJQ25916 |
| Simian adenovirus 29 | NC_011203 | vertebrates,human | 1 | Adenoviridae,Mastadenovirus,Human adenovirus B | — | FJQ25916 |
| Simian adenovirus 31.1 | NC_001405 | vertebrates,human | 1 | Adenoviridae,Mastadenovirus,Human adenovirus C | — | FJQ25906 |

| Taxonomy | NCBI Reference Sequence ID | Host | Lineage | No. of Genomes | Segment Count | Genbank Accession ID |
|---|---|---|---|---|---|---|
| Simian adenovirus 31,2 | NC_001405 | vertebrates,human | Adenoviridae,Mastadenovirus,Human adenovirus C | 1 | — | FJQ25904 |
| Simian adenovirus 32 | NC_011202 | vertebrates,human | Adenoviridae,Mastadenovirus,Human adenovirus B | 1 | — | FJQ25911 |
| Simian adenovirus 32 | NC_011203 | vertebrates,human | Adenoviridae,Mastadenovirus,Human adenovirus B | 1 | — | FJQ25911 |
| Simian adenovirus 33 | NC_011202 | vertebrates,human | Adenoviridae,Mastadenovirus,Human adenovirus B | 1 | — | FJQ25908 |
| Simian adenovirus 33 | NC_011203 | vertebrates,human | Adenoviridae,Mastadenovirus,Human adenovirus B | 1 | — | FJQ25908 |
| Simian adenovirus 34 | NC_001405 | vertebrates,human | Adenoviridae,Mastadenovirus,Human adenovirus C | 1 | — | FJQ25905 |
| Simian adenovirus 35,1 | NC_011202 | vertebrates,human | Adenoviridae,Mastadenovirus,Human adenovirus B | 1 | — | FJQ25912 |
| Simian adenovirus 35,1 | NC_011203 | vertebrates,human | Adenoviridae,Mastadenovirus,Human adenovirus B | 1 | — | FJQ25912 |
| Simian adenovirus 35,2 | NC_011202 | vertebrates,human | Adenoviridae,Mastadenovirus,Human adenovirus B | 1 | — | FJQ25910 |
| Simian adenovirus 35,2 | NC_011203 | vertebrates,human | Adenoviridae,Mastadenovirus,Human adenovirus B | 1 | — | FJQ25910 |
| Simian adenovirus 40,1 | NC_001405 | vertebrates,human | Adenoviridae,Mastadenovirus,Human adenovirus C | 1 | — | FJQ25907 |
| Simian adenovirus 40,2 | NC_011202 | vertebrates,human | Adenoviridae,Mastadenovirus,Human adenovirus B | 1 | — | FJQ25926 |
| Simian adenovirus 41,1 | NC_001405 | vertebrates,human | Adenoviridae,Mastadenovirus,Human adenovirus C | 1 | — | FJQ25913 |
| Simian adenovirus 41,1 | NC_011202 | vertebrates,human | Adenoviridae,Mastadenovirus,Human adenovirus B | 1 | — | FJQ25913 |
| Simian adenovirus 41,2 | NC_011203 | vertebrates,human | Adenoviridae,Mastadenovirus,Human adenovirus B | 1 | — | FJQ25927 |
| Simian adenovirus 41,2 | NC_001405 | vertebrates,human | Adenoviridae,Mastadenovirus,Human adenovirus C | 1 | — | FJQ25927 |
| Simian adenovirus 42,1 | NC_011202 | vertebrates,human | Adenoviridae,Mastadenovirus,Human adenovirus B | 1 | — | FJQ25903 |
| Simian adenovirus 42,2 | NC_001405 | vertebrates,human | Adenoviridae,Mastadenovirus,Human adenovirus C | 1 | — | FJQ25902 |
| Simian adenovirus 42,3 | NC_001405 | vertebrates,human | Adenoviridae,Mastadenovirus,Human adenovirus C | 1 | — | FJQ25925 |
| Simian adenovirus 43 | NC_001405 | vertebrates,human | Adenoviridae,Mastadenovirus,Human adenovirus C | 1 | — | FJQ25900 |
| Simian adenovirus 44 | NC_001405 | vertebrates,human | Adenoviridae,Mastadenovirus,Human adenovirus C | 1 | — | FJQ25899 |
| Simian adenovirus 45 | NC_001405 | vertebrates,human | Adenoviridae,Mastadenovirus,Human adenovirus C | 1 | — | FJQ25901 |
| Simian adenovirus 46 | NC_011202 | vertebrates,human | Adenoviridae,Mastadenovirus,Human adenovirus B | 1 | — | FJQ25930 |
| Simian adenovirus 46 | NC_011203 | vertebrates,human | Adenoviridae,Mastadenovirus,Human adenovirus B | 1 | — | FJQ25930 |

| Taxonomy | NCBI Reference Sequence ID | Host | No. of Genomes | Lineage | Segment Count | Genbank Accession ID |
|---|---|---|---|---|---|---|
| Simian adenovirus 47 | NC_011202 | vertebrates,human | 1 | Adenoviridae,Mastadenovirus,Human adenovirus B | — | FJQ25929 |
| Simian adenovirus 47 | NC_011203 | vertebrates,human | 1 | Adenoviridae,Mastadenovirus,Human adenovirus B | — | FJQ25929 |
| Simian agents | NC_001472 | vertebrates,human | 1 | Picornaviridae,Enterovirus,Enterovirus B | — | AF326751 |
| Simian enterovirus 19 | NC_001612 | vertebrates,human | 1 | Picornaviridae,Enterovirus,Enterovirus A | — | AF326754 |
| Simian enterovirus 43 | NC_001612 | vertebrates,human | 1 | Picornaviridae,Enterovirus,Enterovirus A | — | AF326761 |
| Simian enterovirus 46 | NC_001612 | vertebrates,human | 2 | Picornaviridae,Enterovirus,Enterovirus A | — | EF667343,AF326764 |
| Simian rotavirus | NC_011500 | vertebrates,human | 6 | Reoviridae,Rotavirus,Rotavirus A | seg. 5 | AF290884,AF290883,AF290882,Z32535,AF290881,FJ422135 |
| Simian rotavirus | NC_011501 | vertebrates,human | 2 | Reoviridae,Rotavirus,Rotavirus A | seg. 7 | GU550506,FJ422137 |
| Simian rotavirus | NC_011502 | vertebrates,human | 2 | Reoviridae,Rotavirus,Rotavirus A | seg. 8 | X81426,FJ422138 |
| Simian rotavirus | NC_011503 | vertebrates,human | 4 | Reoviridae,Rotavirus,Rotavirus A | seg. 9 | X66158,V01546,V01190,FJ422139 |
| Simian rotavirus | NC_011504 | vertebrates,human | 2 | Reoviridae,Rotavirus,Rotavirus A | seg. 10 | FJ422140,L41247 |
| Simian rotavirus | NC_011505 | vertebrates,human | 4 | Reoviridae,Rotavirus,Rotavirus A | seg. 11 | AF306493,XQ7831,FJ422141,M28347 |
| Simian rotavirus | NC_011506 | vertebrates,human | 3 | Reoviridae,Rotavirus,Rotavirus A | seg. 2 | AF474406,L33364,FJ422132 |
| Simian rotavirus | NC_011507 | vertebrates,human | 1 | Reoviridae,Rotavirus,Rotavirus A | seg. 1 | FJ422131 |
| Simian rotavirus | NC_011508 | vertebrates,human | 1 | Reoviridae,Rotavirus,Rotavirus A | seg. 3 | FJ422133 |
| Simian rotavirus | NC_011509 | vertebrates,human | 5 | Reoviridae,Rotavirus,Rotavirus A | seg. 6 | L15384,FJ422136,L33365,XQ0421,M27824 |
| Simian rotavirus A strain 4 | NC_011510 | vertebrates,human | 5 | Reoviridae,Rotavirus,Rotavirus A | seg. 4 | M23188,FJ422134,D16345,D16346,X1420 |
| Simian rotavirus A strain RRV | NC_011506 | vertebrates,human | 2 | Reoviridae,Rotavirus,Rotavirus A | seg. 2 | EF583007,EU636925 |
| Simian rotavirus A strain RRV | NC_011507 | vertebrates,human | 2 | Reoviridae,Rotavirus,Rotavirus A | seg. 1 | EU636924,EF583006 |
| Simian rotavirus A strain RRV | NC_011508 | vertebrates,human | 2 | Reoviridae,Rotavirus,Rotavirus A | seg. 3 | EU636926,EF583008 |
| Simian rotavirus A strain RRV | NC_011509 | vertebrates,human | 1 | Reoviridae,Rotavirus,Rotavirus A | seg. 6 | EF583009 |
| Simian rotavirus A strain TUCH | NC_011500 | vertebrates,human | 1 | Reoviridae,Rotavirus,Rotavirus A | seg. 5 | FJ816612 |
| Simian rotavirus A strain TUCH | NC_011501 | vertebrates,human | 1 | Reoviridae,Rotavirus,Rotavirus A | seg. 7 | FJ816613 |
| Simian rotavirus A strain TUCH | NC_011502 | vertebrates,human | 1 | Reoviridae,Rotavirus,Rotavirus A | seg. 8 | FJ816614 |
| Simian rotavirus A strain TUCH | NC_011503 | vertebrates,human | 1 | Reoviridae,Rotavirus,Rotavirus A | seg. 9 | FJ816615 |
| Simian rotavirus A strain TUCH | NC_011504 | vertebrates,human | 1 | Reoviridae,Rotavirus,Rotavirus A | seg. 10 | FJ816616 |
| Simian rotavirus A strain TUCH | NC_011505 | vertebrates,human | 1 | Reoviridae,Rotavirus,Rotavirus A | seg. 11 | FJ816617 |

-continued

| Taxonomy | NCBI Reference Sequence ID | Host | No. of Genomes | Lineage | Segment Count | Genbank Accession ID |
|---|---|---|---|---|---|---|
| Simian rotavirus A strain TUCH | NC_011506 | vertebrates,human | 1 | Reoviridae,Rotavirus,Rotavirus A | seg. 2 | EF583011 |
| Simian rotavirus A strain TUCH | NC_011507 | vertebrates,human | 1 | Reoviridae,Rotavirus,Rotavirus A | seg. 1 | EF583010 |
| Simian rotavirus A strain TUCH | NC_011508 | vertebrates,human | 1 | Reoviridae,Rotavirus,Rotavirus A | seg. 3 | EF583012 |
| Simian rotavirus A strain TUCH | NC_011509 | vertebrates,human | 1 | Reoviridae,Rotavirus,Rotavirus A | seg. 6 | EF583013 |
| Simian rotavirus A strain TUCH | NC_011510 | vertebrates,human | 1 | Reoviridae,Rotavirus,Rotavirus A | seg. 4 | FJ816611 |
| Simian rotavirus A/SA11 | NC_011500 | vertebrates,human | 1 | Reoviridae,Rotavirus,Rotavirus A | seg. 5 | X14914 |
| Simian rotavirus A/SA11 | NC_011501 | vertebrates,human | 1 | Reoviridae,Rotavirus,Rotavirus A | seg. 7 | JQ2353 |
| Simian rotavirus A/SA11 | NC_011502 | vertebrates,human | 1 | Reoviridae,Rotavirus,Rotavirus A | seg. 8 | XQ0355 |
| Simian rotavirus A/SA11 | NC_011504 | vertebrates,human | 2 | Reoviridae,Rotavirus,Rotavirus A | seg. 10 | AF087678,K01138 |
| Simian rotavirus A/SA11 | NC_011506 | vertebrates,human | 1 | Reoviridae,Rotavirus,Rotavirus A | seg. 2 | X16831 |
| Simian rotavirus A/SA11 | NC_011507 | vertebrates,human | 1 | Reoviridae,Rotavirus,Rotavirus A | seg. 1 | X16830 |
| Simian rotavirus A/SA11 | NC_011508 | vertebrates,human | 2 | Reoviridae,Rotavirus,Rotavirus A | seg. 3 | X16062,X16387 |
| Simian rotavirus A/SA11 | NC_011509 | vertebrates,human | 1 | Reoviridae,Rotavirus,Rotavirus A | seg. 6 | AY187029 |
| Simian rotavirus A/SA11 | NC_011510 | vertebrates,human | 1 | Reoviridae,Rotavirus,Rotavirus A | seg. 4 | Y00336 |
| Simian rotavirus A/SA11 | NC_011502 | vertebrates,human | 1 | Reoviridae,Rotavirus,Rotavirus A | seg. 8 | AY065843 |
| Simian rotavirus A/SA11-C14 | NC_011502 | vertebrates,human | 1 | Reoviridae,Rotavirus,Rotavirus A | seg. 8 | EF460843 |
| Simian virus 40 | NC_001669 | vertebrates,human | 35 | Polyomaviridae,Polyomavirus,Simian virus 40 | seg. 8 | EF579662,EF579804, EF579662,EF579661, AY271816,AF155358, FN812745,AY120890, AF156105,JQ2400,AF AF345345,EF579665,AF 316141,EF579663,AF 345344,EF579664,AF 316140,EF579659,AY 156107,EF579660,AF 538779,EF579667,AY 180737,AF156108,AF 271817,DQ660375,E 332562,EF579666,A F579658,DQ218418, F332699,AF155359, EF579803,AF168994, AF316139,AF038616 |
| Simian virus 41 | NC_006428 | vertebrates,human | 1 | Paramyxoviridae,Rubulavirus,Simian virus 41 | — | X64275 |
| Sin Nombre virus | NC_005215 | vertebrates,human | 6 | Bunyaviridae,Hantavirus,Sin Nombre virus | seg. M | JQ690283,JQ690280, JQ690279,JQ690284, L25783, L37903 |

-continued

| Taxonomy | NCBI Reference Sequence ID | Host | No. of Genomes | Lineage | Segment Count | Genbank Accession ID |
|---|---|---|---|---|---|---|
| Sin Nombre virus | NC_005216 | vertebrates,human | 8 | Bunyaviridae,Hantavirus,Sin Nombre virus | seg. S | L25784,JQ690281,JQ690277,JQ690282,JQ690278,JQ690276,AF281851,L37904 |
| Sin Nombre virus | NC_005217 | vertebrates,human | 2 | Bunyaviridae,Hantavirus,Sin Nombre virus | seg. L | L37902,L37901 |
| Small anellovirus 2 | NC_007014,NC_007013 | vertebrates,human | 1 | Anelloviridae,Small anellovirus | — | AY622909 |
| Snow Mountain virus | NC_001959 | vertebrates,human | 1 | Caliciviridae,Norovirus,Norwalk virus | — | AY134748 |
| Southampton virus | NC_001959 | vertebrates,human | 1 | Caliciviridae,Norovirus,Norwalk virus | — | L07418 |
| Sudan ebolavirus | NC_006432 | vertebrates,human | 9 | Filoviridae,Ebolavirus,Sudan ebolavirus | — | KC545391,EU338380,KC589025,KC242783,FJ968794,KC545390,AY729654,KC545389,KC545392 |
| Sudan ebolavirus-Nakisamata | NC_006432 | vertebrates,human | 1 | Filoviridae,Ebolavirus,Sudan ebolavirus | — | JN638998 |
| Swine hepatitis E virus | NC_001434 | vertebrates,human | 26 | Hepeviridae,Hepevirus,Hepatitis E virus | — | GU361892,FJ998008,GU188851,AB481228,EU723514,AY594199,GU119961,FJ610232,GU119960,KF176351,AB097811,AB073912,AB481227,EU723512,EU676172,EU723515,AY115488,EU723513,AF082843,D0279091,FJ426403,FJ426404,AB481229,JX855794,EU723516,AB481226 |
| Swine vesicular disease virus | NC_001472 | vertebrates,human | 4 | Picornaviridae,Enterovirus,Enterovirus B | — | AY429470,AF268065,D16364,X54521 |
| Swine vesicular disease virus (STRAIN H/3 '76) | NC_001472 | vertebrates,human | 1 | Picornaviridae,Enterovirus,Enterovirus B | — | DQ0435 |
| TT virus 51e1931 | NC_015783 | vertebrates,human | 1 | Anelloviridae,Torque teno virus | — | AM712003 |
| TT virus 51e1932 | NC_015783 | vertebrates,human | 1 | Anelloviridae,Torque teno virus | — | AM712004 |
| TT virus 51e1957 | NC_015783 | vertebrates,human | 1 | Anelloviridae,Torque teno virus | — | AM711976 |
| TT virus 51e2057 | NC_015783 | vertebrates,human | 1 | Anelloviridae,Torque teno virus | — | AM712030 |
| TT virus 51e2058 | NC_015783 | vertebrates,human | 1 | Anelloviridae,Torque teno virus | — | AM712031 |
| TT virus 51e2061 | NC_015783 | vertebrates,human | 1 | Anelloviridae,Torque teno virus | — | AM712033 |
| TT virus 51e2065 | NC_015783 | vertebrates,human | 1 | Anelloviridae,Torque teno virus | — | AM712034 |
| TT virus 51e2072 | NC_015783 | vertebrates,human | 1 | Anelloviridae,Torque teno virus | — | AM712032 |
| TTV-like mini virus | NC_020498 | vertebrates,human | 8 | Anelloviridae,TTV-like mini virus | — | KF764702,JX134046,AB026930,JX134044,AB038628,AB038626,KF764701,JX134045 |

| Taxonomy | NCBI Reference Sequence ID | Host | No. of Genomes | Lineage | Segment Count | Genbank Accession ID |
|---|---|---|---|---|---|---|
| Tacaribe virus | NC_004292 | vertebrates,human | 1 | Arenaviridae,Arenavirus,Tacaribe virus | seg. L | JQ4340 |
| Tacaribe virus | NC_004293 | vertebrates,human | 1 | Arenaviridae,Arenavirus,Tacaribe virus | seg. S | M20304 |
| Tamiami virus | NC_010701 | vertebrates,human | 3 | Arenaviridae,Arenavirus,Tamiami virus | seg. S | AF512828,AF485263, EU486821 |
| Tamiami virus | NC_010702 | vertebrates,human | 2 | Arenaviridae,Arenavirus,Tamiami virus | seg. L | AY924393,EU627614 |
| Thottapalayam virus | NC_010704 | vertebrates,human | 1 | Bunyaviridae,Hantavirus,Thottapalayam virus | seg. S | AY526097 |
| Thottapalayam virus | NC_010707 | vertebrates,human | 2 | Bunyaviridae,Hantavirus,Thottapalayam virus | seg. L | EU001330,DQ825770 |
| Thottapalayam virus | NC_010708 | vertebrates,human | 2 | Bunyaviridae,Hantavirus,Thottapalayam virus | seg. M | EU001329,DQ825771 |
| Tioman virus | NC_004074 | vertebrates,human | 1 | Paramyxoviridae,Rubulavirus,Tioman virus | — | AF298895 |
| Torque teno canis virus | NC_014071 | vertebrates,human | 3 | Anelloviridae,Thetatorquevirus,Torque teno canis virus | — | AB076002,GU951508,HM855265 |
| Torque teno douroucouli virus | NC_014087 | vertebrates,human | 1 | Anelloviridae,Zetatorquevirus,Torque teno douroucouli virus | — | AB041961 |
| Torque teno felis virus | NC_014072 | vertebrates,human | 3 | Anelloviridae,Etatorquevirus,Torque teno felis virus | — | HM142589,HM142588,AB076003 |
| Torque teno midi virus 1 | NC_009225 | vertebrates,human | 2 | Anelloviridae,Gammatorquevirus,Torque teno midi virus 1 | — | AB290918,AB290917 |
| Torque teno midi virus 2 | NC_014093 | vertebrates,human | 1 | Anelloviridae,Gammatorquevirus,Torque teno midi virus 2 | — | AB290919 |
| Torque teno mini virus 1 | NC_014097 | vertebrates,human | 1 | Anelloviridae,Betatorquevirus,Torque teno mini virus 1 | — | AB026931 |
| Torque teno mini virus 2 | NC_014086 | vertebrates,human | 1 | Anelloviridae,Betatorquevirus,Torque teno mini virus 2 | — | AB038629 |
| Torque teno mini virus 3 | NC_014088 | vertebrates,human | 1 | Anelloviridae,Betatorquevirus,Torque teno mini virus 3 | — | AB038630 |
| Torque teno mini virus 4 | NC_014090 | vertebrates,human | 1 | Anelloviridae,Betatorquevirus,Torque teno mini virus 4 | — | AB041963 |
| Torque teno mini virus 5 | NC_014089 | vertebrates,human | 1 | Anelloviridae,Betatorquevirus,Torque teno mini virus 5 | — | AB041962 |
| Torque teno mini virus 6 | NC_014095 | vertebrates,human | 1 | Anelloviridae,Betatorquevirus,Torque teno mini virus 6 | — | AB026929 |
| Torque teno mini virus 7 | NC_014082 | vertebrates,human | 1 | Anelloviridae,Betatorquevirus,Torque teno mini virus 7 | — | AB038627 |
| Torque teno mini virus 8 | NC_014068 | vertebrates,human | 1 | Anelloviridae,Betatorquevirus,Torque teno mini virus 8 | — | AF291073 |
| Torque teno mini virus 9 | NC_002195 | vertebrates,human | 2 | Anelloviridae,Betatorquevirus,Torque teno mini virus 9 | — | AB038631,AB038625 |
| Torque teno sus virus 1 | NC_014070 | vertebrates,human | 13 | Anelloviridae,Iotatorquevirus,Torque teno sus virus 1a | — | HM633256,AB076001,JF937662,JF937660,JF937661,HM633251,JN688927,AY823990,JF694117,HM63324 9,HM633245,HM6332 43,JF694116 |
| Torque teno sus virus 1a | NC_014070 | vertebrates,human | 3 | Anelloviridae,Iotatorquevirus,Torque teno sus virus 1a | — | JX535326,JX535327,JQ933527 |
| Torque teno sus virus k2 | NC_014092 | vertebrates,human | 1 | Anelloviridae,Kappatorquevirus,Torque teno sus virus k2 | — | AY823991 |

-continued

| Taxonomy | NCBI Reference Sequence ID | Host | No. of Genomes | Lineage | Segment Count | Genbank Accession ID |
|---|---|---|---|---|---|---|
| Torque teno sus virus k2b | NC_014092 | vertebrates,human | 3 | Anelloviridae,Kappatorquevirus,Torque teno sus virus k2 | — | JQ406846,JQ406844, JQ406845 |
| Torque teno tamarin virus | NC_014085 | vertebrates,human | 1 | Anelloviridae,Epsilontorquevirus,Torque teno tamarin virus | — | AB041960 |
| Torque teno virus | NC_014070 | vertebrates,human | 4 | Anelloviridae,Iotatorquevirus,Torque teno sus virus 1a | — | GQ120664,GU45638 3,GU456384,GU1880 45 |
| Torque teno virus | NC_015783 | vertebrates,human | 114 | Anelloviridae,Torque teno virus | — | AF351132,FR751478, AF247138,FR751507, FR751483,FR751485 ,FR751472,AJ620233 ,FR751470,AB02866 9,AB064603,FR75151 06,AF122915,FR7514 71,AB064597,FR751 463,AJ620216,FR751 495,AY823989,FR84 8325,AB054648,AF12 2916,AJ620228,AJ62 0212,FR848327,FR7 51479,FR751500,AF1 22914,AJ620224,FR7 51477,AJ620235,AB0 64599,FR751465,FR 751491,FR848323,F R751502,AB017610, FR751504,AB064606 ,AJ620218,FR751493 ,AJ620227,AF122917 ,AJ620231,FR751480 ,DQ003344,FR75147 5,AY823988,FR7514 69,AJ620219,AB0386 19,AF116842,FR7514 68,FR751490,FR751 501,AB064602,AJ620 221,AF298585,AJ620 226,AB038620,FR75 1503,FR751509,FR7 51481,AJ620214,FR7 51497,DQ003341,DQ 003343,FR751476,AJ 620232,AJ620230,FR 751487,AJ620229,AB 064600,AF247137,AF 122921,FR751492,AF 122918,FR751508,AF 122920,FJ426280,FR |

| Taxonomy | NCBI Reference Sequence ID | Host | No. of Genomes | Lineage | Segment Count | Genbank Accession ID |
|---|---|---|---|---|---|---|
| Torque teno virus 1 | NC_002076 | vertebrates,human | 2 | Anelloviridae,Alphatorquevirus,Torque teno virus 1 | — | 751484,AF122913,FR751511,FR751489,FR751496,AJ620234,AF079173,FR751482,FR751494,AB064601,AB064596,AJ620223,AJ620225,FR751510,FR751486,AF129887,AJ620213,DQ003342,AJ620220,FR751473,FR848324,AJ620222,FR751505,FR751146,FR848326,FR751474,AB064604,FR751498,FR751467,AJ620215,AJ620217,FR751464,FR751488,FR751499 |
| Torque teno virus 1 | NC_014070 | vertebrates,human | 5 | Anelloviridae,Iotatorquevirus,Torque teno sus virus 1a | — | GU570202,GU570198,GU570201,GU570199,GU570200 |
| Torque teno virus 10 | NC_014076 | vertebrates,human | 2 | Anelloviridae,Alphatorquevirus,Torque teno virus 10 | — | AB064607,GU797360 |
| Torque teno virus 12 | NC_014075 | vertebrates,human | 1 | Anelloviridae,Alphatorquevirus,Torque teno virus 12 | — | AB064605 |
| Torque teno virus 14 | NC_014077 | vertebrates,human | 1 | Anelloviridae,Alphatorquevirus,Torque teno virus 14 | — | AB037926 |
| Torque teno virus 15 | NC_014096 | vertebrates,human | 1 | Anelloviridae,Alphatorquevirus,Torque teno virus 15 | — | AB028668 |
| Torque teno virus 16 | NC_014091 | vertebrates,human | 1 | Anelloviridae,Alphatorquevirus,Torque teno virus 16 | — | AB017613 |
| Torque teno virus 19 | NC_014078 | vertebrates,human | 1 | Anelloviridae,Alphatorquevirus,Torque teno virus 19 | — | AB025946 |
| Torque teno virus 2 | NC_014480 | vertebrates,human | 1 | Anelloviridae,Alphatorquevirus,Torque teno virus 2 | — | AB049608 |
| Torque teno virus 25 | NC_014083 | vertebrates,human | 1 | Anelloviridae,Alphatorquevirus,Torque teno virus 25 | — | AB041959 |
| Torque teno virus 26 | NC_014079 | vertebrates,human | 1 | Anelloviridae,Alphatorquevirus,Torque teno virus 26 | — | AB041958 |
| Torque teno virus 27 | NC_014074 | vertebrates,human | 1 | Anelloviridae,Alphatorquevirus,Torque teno virus 27 | — | AB064595 |
| Torque teno virus 28 | NC_014073 | vertebrates,human | 1 | Anelloviridae,Alphatorquevirus,Torque teno virus 28 | — | AB064598 |
| Torque teno virus 3 | NC_014081 | vertebrates,human | 1 | Anelloviridae,Alphatorquevirus,Torque teno virus 3 | — | AY666122 |

| Taxonomy | NCBI Reference Sequence ID | Host | No. of Genomes | Lineage | Segment Count | Genbank Accession ID |
|---|---|---|---|---|---|---|
| Torque teno virus 4 | NC_014069 | vertebrates,human | 1 | Anelloviridae,Alphatorquevirus,Torque teno virus 4 | — | AB041957 |
| Torque teno virus 6 | NC_014094 | vertebrates,human | 1 | Anelloviridae,Alphatorquevirus,Torque teno virus 6 | — | AF435014 |
| Torque teno virus 7 | NC_014080 | vertebrates,human | 1 | Anelloviridae,Alphatorquevirus,Torque teno virus 7 | — | AF261761 |
| Torque teno virus 8 | NC_014084 | vertebrates,human | 1 | Anelloviridae,Alphatorquevirus,Torque teno virus 8 | — | AB054647 |
| Torque teno zalophus virus 1 | NC_012126 | vertebrates,human zalophus virus 1 | 1 | Anelloviridae,Lambdatorquevirus,Torque teno | — | FJ459582 |
| Tula virus | NC_005226 | vertebrates,human | 1 | Bunyaviridae,Hantavirus,Tula virus | seg. L | AJQ05637 |
| Tula virus | NC_005227 | vertebrates,human | 18 | Bunyaviridae,Hantavirus,Tula virus | seg. S | AM945877,Z30945,AJ223600,AF164093,Z30942,AF017659,Z30943,Z30944,Y13980,AF164094,AJ223601,AF44621,Z48573,Y13979,Z30941,Z48741,Z48574,Z49915 |
| Bluetongue virus 1 | NC_006014 | vertebrates,invertebrates | 11 | Reoviridae,Orbivirus,Bluetongue virus | seg. 3 | DQ186807,JN848761,JN881987,DQ186822,DQ186811,AF529048,DQ186818,AF529044,DQ186816,DQ186792,DQ186820 |
| Bluetongue virus 1 | NC_006015 | vertebrates,invertebrates | 13 | Reoviridae,Orbivirus,Bluetongue virus | seg. 10 | AF512912,JX272388,AF512911,JN848768,KJQ19214,KC879624,AF529057,FJ437561,JN881994,AF135223,AF529049,AF529052,AF512910 |
| Bluetongue virus 1 | NC_006022 | vertebrates,invertebrates | 6 | Reoviridae,Orbivirus,Bluetongue virus | seg. 7 | AY789967,AY776331,FJ437558,FJ437562,JN881991,JN848765 |
| Bluetongue virus 1 | NC_006023 | vertebrates,invertebrates | 2 | Reoviridae,Orbivirus,Bluetongue virus | seg. 1 | JN881985,JN848759 |
| Bluetongue virus 1 | NC_006024 | vertebrates,invertebrates | 2 | Reoviridae,Orbivirus,Bluetongue virus | seg. 4 | JN881988,JN848762 |
| Bluetongue virus 1 | NC_006025 | vertebrates,invertebrates | 4 | Reoviridae,Orbivirus,Bluetongue virus | seg. 5 | JN881989,AM778437,AM778438,JN848763 |
| Bluetongue virus 10 | NC_006007 | vertebrates,invertebrates | 1 | Reoviridae,Orbivirus,Bluetongue virus | seg. 8 | JQ740778 |
| Bluetongue virus 10 | NC_006010 | vertebrates,invertebrates | 3 | Reoviridae,Orbivirus,Bluetongue virus | seg. 6 | JQ740776,AJ586709,JN704635 |
| Bluetongue virus 10 | NC_006013 | vertebrates,invertebrates | 2 | Reoviridae,Orbivirus,Bluetongue virus | seg. 2 | AJ585131,JQ740772 |
| Bluetongue virus 10 | NC_006014 | vertebrates,invertebrates | 1 | Reoviridae,Orbivirus,Bluetongue virus | seg. 3 | JQ740773 |
| Bluetongue virus 10 | NC_006015 | vertebrates,invertebrates | 2 | Reoviridae,Orbivirus,Bluetongue virus | seg. 10 | JQ740780,JX272528 |

-continued

| Taxonomy | NCBI Reference Sequence ID | Host | No. of Genomes | Lineage | Segment Count | Genbank Accession ID |
|---|---|---|---|---|---|---|
| Bluetongue virus 10 | NC_006022 | vertebrates,invertebrates | 1 | Reoviridae,Orbivirus,Bluetongue virus | seg. 7 | JQ740777 |
| Bluetongue virus 10 | NC_006023 | vertebrates,invertebrates | 1 | Reoviridae,Orbivirus,Bluetongue virus | seg. 1 | JQ740771 |
| Bluetongue virus 10 | NC_006024 | vertebrates,invertebrates | 2 | Reoviridae,Orbivirus,Bluetongue virus | seg. 4 | L13726,JQ740774 |
| Bluetongue virus 10 | NC_006025 | vertebrates,invertebrates | 1 | Reoviridae,Orbivirus,Bluetongue virus | seg. 5 | JQ740775 |
| Bluetongue virus 11 | NC_006007 | vertebrates,invertebrates | 4 | Reoviridae,Orbivirus,Bluetongue virus | seg. 8 | JQ972838,JQ972858, JQ972868,JQ972848 |
| Bluetongue virus 11 | NC_006008 | vertebrates,invertebrates | 4 | Reoviridae,Orbivirus,Bluetongue virus | seg. 9 | JQ972869,JQ972859, JQ972849,JQ972839 |
| Bluetongue virus 11 | NC_006010 | vertebrates,invertebrates | 5 | Reoviridae,Orbivirus,Bluetongue virus | seg. 6 | JQ972866,JQ972856, JQ972846,JQ972836, AJ586710 |
| Bluetongue virus 11 | NC_006013 | vertebrates,invertebrates | 5 | Reoviridae,Orbivirus,Bluetongue virus | seg. 2 | AJ585132,JQ972832, JQ972862,JQ972852, JQ972842 |
| Bluetongue virus 11 | NC_006014 | vertebrates,invertebrates | 5 | Reoviridae,Orbivirus,Bluetongue virus | seg. 3 | L19968,JQ972833,JQ972853,JQ972843,JQ972863 |
| Bluetongue virus 11 | NC_006015 | vertebrates,invertebrates | 8 | Reoviridae,Orbivirus,Bluetongue virus | seg. 10 | JQ972870,AF512923, JX272518,JQ972860, AF512921,JQ972850, JQ972840,AF512922 |
| Bluetongue virus 11 | NC_006022 | vertebrates,invertebrates | 4 | Reoviridae,Orbivirus,Bluetongue virus | seg. 7 | JQ972847,JQ972867, JQ972837,JQ972857 |
| Bluetongue virus 11 | NC_006023 | vertebrates,invertebrates | 5 | Reoviridae,Orbivirus,Bluetongue virus | seg. 1 | JQ972841,L20445,JQ972831,JQ972851,JQ972861 |
| Bluetongue virus 11 | NC_006024 | vertebrates,invertebrates | 5 | Reoviridae,Orbivirus,Bluetongue virus | seg. 4 | JQ972854,JQ972864, JQ972844,JQ972834, L08638 |
| Bluetongue virus 11 | NC_006025 | vertebrates,invertebrates | 5 | Reoviridae,Orbivirus,Bluetongue virus | seg. 5 | JQ972835,M97681,J0972865,JQ972845,J0972855 |
| Bluetongue virus 12 | NC_006010 | vertebrates,invertebrates | 2 | Reoviridae,Orbivirus,Bluetongue virus | seg. 6 | AJ586711,AJ586712 |
| Bluetongue virus 12 | NC_006015 | vertebrates,invertebrates | 3 | Reoviridae,Orbivirus,Bluetongue virus | seg. 10 | KC662621,JX272508,AF135227 |
| Bluetongue virus 13 | NC_006007 | vertebrates,invertebrates | 1 | Reoviridae,Orbivirus,Bluetongue virus | seg. 8 | AY855289 |
| Bluetongue virus 13 | NC_006010 | vertebrates,invertebrates | 2 | Reoviridae,Orbivirus,Bluetongue virus | seg. 6 | AY855280,AJ586713 |
| Bluetongue virus 13 | NC_006013 | vertebrates,invertebrates | 2 | Reoviridae,Orbivirus,Bluetongue virus | seg. 2 | L11874,L11741 |
| Bluetongue virus 13 | NC_006014 | vertebrates,invertebrates | 1 | Reoviridae,Orbivirus,Bluetongue virus | seg. 3 | L19969 |
| Bluetongue virus 13 | NC_006015 | vertebrates,invertebrates | 1 | Reoviridae,Orbivirus,Bluetongue virus | seg. 10 | JX272498 |
| Bluetongue virus 13 | NC_006022 | vertebrates,invertebrates | 1 | Reoviridae,Orbivirus,Bluetongue virus | seg. 7 | AY855283 |
| Bluetongue virus 13 | NC_006023 | vertebrates,invertebrates | 2 | Reoviridae,Orbivirus,Bluetongue virus | seg. 1 | L20446,JX272489 |
| Bluetongue virus 13 | NC_006024 | vertebrates,invertebrates | 2 | Reoviridae,Orbivirus,Bluetongue virus | seg. 4 | AY855274,L08640 |
| Bluetongue virus 13 | NC_006025 | vertebrates,invertebrates | 1 | Reoviridae,Orbivirus,Bluetongue virus | seg. 5 | M97762 |
| Bluetongue virus 14 | NC_006010 | vertebrates,invertebrates | 2 | Reoviridae,Orbivirus,Bluetongue virus | seg. 6 | AJ586714,AJ586715 |
| Bluetongue virus 14 | NC_006015 | vertebrates,invertebrates | 1 | Reoviridae,Orbivirus,Bluetongue virus | seg. 10 | JX272488 |

| Taxonomy | NCBI Reference Sequence ID | Host | No. of Genomes | Lineage | Segment Count | Genbank Accession ID |
|---|---|---|---|---|---|---|
| Bluetongue virus 15 | NC_006007 | vertebrates,invertebrates | 2 | Reoviridae,Orbivirus,Bluetongue virus | seg. 8 | JQ086228,AM900379 |
| Bluetongue virus 15 | NC_006008 | vertebrates,invertebrates | 1 | Reoviridae,Orbivirus,Bluetongue virus | seg. 9 | JQ086229 |
| Bluetongue virus 15 | NC_006010 | vertebrates,invertebrates | 4 | Reoviridae,Orbivirus,Bluetongue virus | seg. 6 | AJ586716,AJ586717,AJ586718,JQ086226 |
| Bluetongue virus 15 | NC_006013 | vertebrates,invertebrates | 1 | Reoviridae,Orbivirus,Bluetongue virus | seg. 2 | JQ086222 |
| Bluetongue virus 15 | NC_006014 | vertebrates,invertebrates | 1 | Reoviridae,Orbivirus,Bluetongue virus | seg. 3 | JQ086223 |
| Bluetongue virus 15 | NC_006015 | vertebrates,invertebrates | 3 | Reoviridae,Orbivirus,Bluetongue virus | seg. 10 | AF135228,JX272478,JQ086230 |
| Bluetongue virus 15 | NC_006022 | vertebrates,invertebrates | 2 | Reoviridae,Orbivirus,Bluetongue virus | seg. 7 | L11724,JQ086227 |
| Bluetongue virus 15 | NC_006023 | vertebrates,invertebrates | 1 | Reoviridae,Orbivirus,Bluetongue virus | seg. 1 | JQ086221 |
| Bluetongue virus 15 | NC_006024 | vertebrates,invertebrates | 1 | Reoviridae,Orbivirus,Bluetongue virus | seg. 4 | JQ086224 |
| Bluetongue virus 15 | NC_006025 | vertebrates,invertebrates | 1 | Reoviridae,Orbivirus,Bluetongue virus | seg. 5 | JQ086225 |
| Bluetongue virus 16 | NC_006007 | vertebrates,invertebrates | 3 | Reoviridae,Orbivirus,Bluetongue virus | seg. 8 | JQ086238,AM900386,JQ924827 |
| Bluetongue virus 16 | NC_006008 | vertebrates,invertebrates | 2 | Reoviridae,Orbivirus,Bluetongue virus | seg. 9 | JQ086239,JQ924828 |
| Bluetongue virus 16 | NC_006010 | vertebrates,invertebrates | 10 | Reoviridae,Orbivirus,Bluetongue virus | seg. 6 | AJ586693,AJ586691,AJ586692,AJ586689,JQ924825,AJ586694,JN572918,AJ586690,AJ586719,JQ086236 |
| Bluetongue virus 16 | NC_006013 | vertebrates,invertebrates | 4 | Reoviridae,Orbivirus,Bluetongue virus | seg. 2 | JQ086232,DQ191260,JQ924821,DQ191259 |
| Bluetongue virus 16 | NC_006014 | vertebrates,invertebrates | 11 | Reoviridae,Orbivirus,Bluetongue virus | seg. 3 | DQ186821,DQ186798,DQ186828,DQ186827,DQ186812,DQ186814,DQ186819,JQ086233,JQ924822,DQ186796,DQ186791 |
| Bluetongue virus 16 | NC_006015 | vertebrates,invertebrates | 5 | Reoviridae,Orbivirus,Bluetongue virus | seg. 10 | JQ924829,JX272468,KF387530,AF135229,JQ086240 |
| Bluetongue virus 16 | NC_006022 | vertebrates,invertebrates | 2 | Reoviridae,Orbivirus,Bluetongue virus | seg. 7 | JQ086237,JQ924826 |
| Bluetongue virus 16 | NC_006023 | vertebrates,invertebrates | 2 | Reoviridae,Orbivirus,Bluetongue virus | seg. 1 | JQ086231,JQ924820 |
| Bluetongue virus 16 | NC_006024 | vertebrates,invertebrates | 2 | Reoviridae,Orbivirus,Bluetongue virus | seg. 4 | JQ924823,JQ086234 |
| Bluetongue virus 16 | NC_006025 | vertebrates,invertebrates | 8 | Reoviridae,Orbivirus,Bluetongue virus | seg. 5 | AM773694,JQ086235,AM773692,AM773696,JQ924824,AM773695,KF387525,AM773693 |
| Bluetongue virus 17 | NC_006007 | vertebrates,invertebrates | 1 | Reoviridae,Orbivirus,Bluetongue virus | seg. 8 | AY855290 |
| Bluetongue virus 17 | NC_006010 | vertebrates,invertebrates | 8 | Reoviridae,Orbivirus,Bluetongue virus | seg. 6 | DQ080914,AJ586720,DQ080913,AY85528 1,DQ080912,DQ080809,DQ080911,DQ080915 |
| Bluetongue virus 17 | NC_006013 | vertebrates,invertebrates | 3 | Reoviridae,Orbivirus,Bluetongue virus | seg. 2 | AJ585138,AY855269,S72158 |

-continued

| Taxonomy | NCBI Reference Sequence ID | Host | No. of Genomes | Lineage | Segment Count | Genbank Accession ID |
|---|---|---|---|---|---|---|
| Bluetongue virus 17 | NC_006015 | vertebrates,invertebrates | 1 | Reoviridae,Orbivirus,Bluetongue virus | seg. 10 | JX272458 |
| Bluetongue virus 17 | NC_006022 | vertebrates,invertebrates | 1 | Reoviridae,Orbivirus,Bluetongue virus | seg. 7 | AY855284 |
| Bluetongue virus 17 | NC_006023 | vertebrates,invertebrates | 1 | Reoviridae,Orbivirus,Bluetongue virus | seg. 1 | L20447 |
| Bluetongue virus 17 | NC_006024 | vertebrates,invertebrates | 2 | Reoviridae,Orbivirus,Bluetongue virus | seg. 4 | L08639,AY855275 |
| Bluetongue virus 18 | NC_006010 | vertebrates,invertebrates | 1 | Reoviridae,Orbivirus,Bluetongue virus | seg. 6 | AJ586721 |
| Bluetongue virus 18 | NC_006015 | vertebrates,invertebrates | 3 | Reoviridae,Orbivirus,Bluetongue virus | seg. 10 | JX272448,AF512915, AF512914 |
| Bluetongue virus 18 | NC_006022 | vertebrates,invertebrates | 1 | Reoviridae,Orbivirus,Bluetongue virus | seg. 7 10 | AY606206 |
| Bluetongue virus 2 | NC_006007 | vertebrates,invertebrates | 12 | Reoviridae,Orbivirus,Bluetongue virus | seg. 8 | AM900382,AY855288 ,AY138896,JN255879 ,JN255869,JQ086248 ,JN255939,AY855286 ,JN255929,AY855287 ,AY855285,JQ240328 |
| Bluetongue virus 2 | NC_006008 | vertebrates,invertebrates | 6 | Reoviridae,Orbivirus,Bluetongue virus | seg. 9 | JN255880,JN255930, JN255870,JQ086249, JN255940,JQ713562 |
| Bluetongue virus 2 | NC_006010 | vertebrates,invertebrates | 27 | Reoviridae,Orbivirus,Bluetongue virus | seg. 6 | AY129084,AY855277 ,AY855279,AJ586674 ,JN255877,JN255927 ,AJ586673,AJ586669, AJ586666,AJ586665, JN255937,AY129083, AJ586671,AJ586668, AJ586675,JN255867, AJ586672,JQ086246, AJ783906,AY189951, JQ240326,AJ586670, AJ586696,AY855276, AJ586667,AJ783904, AY855278 |
| Bluetongue virus 2 | NC_006013 | vertebrates,invertebrates | 23 | Reoviridae,Orbivirus,Bluetongue virus | seg. 2 | DQ191275,JN255873 ,DQ191273,JN25592 3,DQ191272,DQ1912 70, M21946,JQ08624 2,JN255933,DQ1912 66,DQ191263,AF481 096,DQ191267,DQ19 1274,DQ191261,DQ1 91265,AF356601,DQ 191264,DQ191271,D 0191268,DQ191262, JN255863,DQ191269 |
| Bluetongue virus 2 | NC_006014 | vertebrates,invertebrates | 11 | Reoviridae,Orbivirus,Bluetongue virus | seg. 3 | L19967,JN255864,D 0186826,JN255934,J N255924,JQ086243, |

| Taxonomy | NCBI Reference Sequence ID | Host | No. of Genomes | Lineage | Segment Count | Genbank Accession ID |
|---|---|---|---|---|---|---|
| Bluetongue virus 2 | NC_006015 | vertebrates,invertebrates | 15 | Reoviridae,Orbivirus,Bluetongue virus | seg. 10 | DQ186815,JN255874,JQ713558,DQ186793,S378452 AF512913,JN255881,AY438033,AF512916,AF481094,AF135224,JN255941,AF135230,JQ240330,JQ086250,JQ713563,JN255931,AF512920,JX272608,JN255871 |
| Bluetongue virus 2 | NC_006022 | vertebrates,invertebrates | 10 | Reoviridae,Orbivirus,Bluetongue virus | seg. 7 | JQ086247,M64997,D0399837,JN255938,JN255868,JN255878,AY855282,JN255928,J0713561,AF481095 |
| Bluetongue virus 2 | NC_006023 | vertebrates,invertebrates | 8 | Reoviridae,Orbivirus,Bluetongue virus | seg. 1 | JN255872,JQ713557,JQ240321,JQ086241,L20508,JN255922,JN255932,JN255862 |
| Bluetongue virus 2 | NC_006024 | vertebrates,invertebrates | 14 | Reoviridae,Orbivirus,Bluetongue virus | seg. 4 | AY855272,AY134477,AY855271,L08637,JN255865,JN255875,J0240324,AY855273,JN255925,JQ086244,AY855270,JQ713559,AY129085,JN255935 |
| Bluetongue virus 2 | NC_006025 | vertebrates,invertebrates | 15 | Reoviridae,Orbivirus,Bluetongue virus | seg. 5 | AM773687,AY138895,AM773686,JQ24032 5,JQ086245,JQ71356 0,AM773689,M97680,AM773685,JN255866,JN255936,AM77368 4,JN255876,AM77736 88,JN255926 |
| Bluetongue virus 20 | NC_006007 | vertebrates,invertebrates | 2 | Reoviridae,Orbivirus,Bluetongue virus | seg. 8 | JQ086258,AM900380 |
| Bluetongue virus 20 | NC_006008 | vertebrates,invertebrates | 1 | Reoviridae,Orbivirus,Bluetongue virus | seg. 9 | JQ086259 |
| Bluetongue virus 20 | NC_006010 | vertebrates,invertebrates | 2 | Reoviridae,Orbivirus,Bluetongue virus | seg. 6 | AJ586723,JQ086256 |
| Bluetongue virus 20 | NC_006013 | vertebrates,invertebrates | 2 | Reoviridae,Orbivirus,Bluetongue virus | seg. 2 | JQ086252,AJ585141 |
| Bluetongue virus 20 | NC_006014 | vertebrates,invertebrates | 1 | Reoviridae,Orbivirus,Bluetongue virus | seg. 3 | JQ086253 |
| Bluetongue virus 20 | NC_006015 | vertebrates,invertebrates | 4 | Reoviridae,Orbivirus,Bluetongue virus | seg. 10 | AF529055,JQ086260,AF529056,JX272428 |
| Bluetongue virus 20 | NC_006022 | vertebrates,invertebrates | 1 | Reoviridae,Orbivirus,Bluetongue virus | seg. 7 | JQ086257 |
| Bluetongue virus 20 | NC_006023 | vertebrates,invertebrates | 1 | Reoviridae,Orbivirus,Bluetongue virus | seg. 1 | JQ086251 |
| Bluetongue virus 20 | NC_006024 | vertebrates,invertebrates | 1 | Reoviridae,Orbivirus,Bluetongue virus | seg. 4 | JQ086254 |
| Bluetongue virus 20 | NC_006025 | vertebrates,invertebrates | 1 | Reoviridae,Orbivirus,Bluetongue virus | seg. 5 | JQ086255 |
| Bluetongue virus 21 | NC_006007 | vertebrates,invertebrates | 2 | Reoviridae,Orbivirus,Bluetongue virus | seg. 8 | JQ086268,AM900390 |

| Taxonomy | NCBI Reference Sequence ID | Host | No. of Genomes | Lineage | Segment Count | Genbank Accession ID |
|---|---|---|---|---|---|---|
| Bluetongue virus 21 | NC_006008 | vertebrates,invertebrates | 1 | Reoviridae,Orbivirus,Bluetongue virus | seg. 9 | JQ086269 |
| Bluetongue virus 21 | NC_006010 | vertebrates,invertebrates | 3 | Reoviridae,Orbivirus,Bluetongue virus | seg. 6 | JQ086266,AJ586724, JN572916 |
| Bluetongue virus 21 | NC_006013 | vertebrates,invertebrates | 1 | Reoviridae,Orbivirus,Bluetongue virus | seg. 2 | JQ086262 |
| Bluetongue virus 21 | NC_006014 | vertebrates,invertebrates | 3 | Reoviridae,Orbivirus,Bluetongue virus | seg. 3 | AF529046,AF529047, JQ086263 |
| Bluetongue virus 21 | NC_006015 | vertebrates,invertebrates | 6 | Reoviridae,Orbivirus,Bluetongue virus | seg. 10 | AB473808,JQ086270, AF529053,AF529054, AF529058,JX272418 |
| Bluetongue virus 21 | NC_006022 | vertebrates,invertebrates | 2 | Reoviridae,Orbivirus,Bluetongue virus | seg. 7 | AB473807,JQ086267 |
| Bluetongue virus 21 | NC_006023 | vertebrates,invertebrates | 1 | Reoviridae,Orbivirus,Bluetongue virus | seg. 1 | JQ086261 |
| Bluetongue virus 21 | NC_006024 | vertebrates,invertebrates | 1 | Reoviridae,Orbivirus,Bluetongue virus | seg. 4 | JQ086264 |
| Bluetongue virus 21 | NC_006025 | vertebrates,invertebrates | 1 | Reoviridae,Orbivirus,Bluetongue virus | seg. 5 | JQ086265 |
| Bluetongue virus 22 | NC_006010 | vertebrates,invertebrates | 2 | Reoviridae,Orbivirus,Bluetongue virus | seg. 6 | AJ586725,AJ586726 |
| Bluetongue virus 22 | NC_006015 | vertebrates,invertebrates | 1 | Reoviridae,Orbivirus,Bluetongue virus | seg. 10 | JX272398 |
| Bluetongue virus 23 | NC_006007 | vertebrates,invertebrates | 4 | Reoviridae,Orbivirus,Bluetongue virus | seg. 8 | JQ771829,JQ086278, AM900387,AM900381 |
| Bluetongue virus 23 | NC_006008 | vertebrates,invertebrates | 2 | Reoviridae,Orbivirus,Bluetongue virus | seg. 9 | JQ086279,JQ771830 |
| Bluetongue virus 23 | NC_006010 | vertebrates,invertebrates | 5 | Reoviridae,Orbivirus,Bluetongue virus | seg. 6 | AJ586729,AJ586728, JQ086276,AJ586727, AJ783907 |
| Bluetongue virus 23 | NC_006013 | vertebrates,invertebrates | 2 | Reoviridae,Orbivirus,Bluetongue virus | seg. 2 | JQ086272,L46685 |
| Bluetongue virus 23 | NC_006014 | vertebrates,invertebrates | 3 | Reoviridae,Orbivirus,Bluetongue virus | seg. 3 | JQ086273,JQ771825, DQ186810 |
| Bluetongue virus 23 | NC_006015 | vertebrates,invertebrates | 5 | Reoviridae,Orbivirus,Bluetongue virus | seg. 10 | JX272408,AF529059, JQ086280,AF529051, JQ771831 |
| Bluetongue virus 23 | NC_006022 | vertebrates,invertebrates | 3 | Reoviridae,Orbivirus,Bluetongue virus | seg. 7 | AJ277802,JQ771828, JQ086277 |
| Bluetongue virus 23 | NC_006023 | vertebrates,invertebrates | 2 | Reoviridae,Orbivirus,Bluetongue virus | seg. 1 | JQ771823,JQ086271 |
| Bluetongue virus 23 | NC_006024 | vertebrates,invertebrates | 2 | Reoviridae,Orbivirus,Bluetongue virus | seg. 4 | JQ086274,JQ771826 |
| Bluetongue virus 23 | NC_006025 | vertebrates,invertebrates | 2 | Reoviridae,Orbivirus,Bluetongue virus | seg. 5 | JQ771827,JQ086275 |
| Bluetongue virus 24 | NC_006010 | vertebrates,invertebrates | 1 | Reoviridae,Orbivirus,Bluetongue virus | seg. 6 | AJ586730 |
| Bluetongue virus 24 | NC_006013 | vertebrates,invertebrates | 2 | Reoviridae,Orbivirus,Bluetongue virus | seg. 2 | AJ585145 |
| Bluetongue virus 24 | NC_006015 | vertebrates,invertebrates | 1 | Reoviridae,Orbivirus,Bluetongue virus | seg. 10 | JX272378 |
| Bluetongue virus 3 | NC_006007 | vertebrates,invertebrates | 1 | Reoviridae,Orbivirus,Bluetongue virus | seg. 8 | JQ086288 |
| Bluetongue virus 3 | NC_006008 | vertebrates,invertebrates | 1 | Reoviridae,Orbivirus,Bluetongue virus | seg. 9 | JQ086289 |
| Bluetongue virus 3 | NC_006010 | vertebrates,invertebrates | 3 | Reoviridae,Orbivirus,Bluetongue virus | seg. 6 | AJ586698,JQ086286, AJ586697 |
| Bluetongue virus 3 | NC_006013 | vertebrates,invertebrates | 2 | Reoviridae,Orbivirus,Bluetongue virus | seg. 2 | JQ086282,L42168 |
| Bluetongue virus 3 | NC_006014 | vertebrates,invertebrates | 2 | Reoviridae,Orbivirus,Bluetongue virus | seg. 3 | JQ086283,AF529045 |
| Bluetongue virus 3 | NC_006015 | vertebrates,invertebrates | 7 | Reoviridae,Orbivirus,Bluetongue virus | seg. 10 | AF135225,AF512917, AF512918,JQ086290, AF529050,JX272598, AF512906 |

| Taxonomy | NCBI Reference Sequence ID | Host | No. of Genomes | Lineage | Segment Count | Genbank Accession ID |
|---|---|---|---|---|---|---|
| Bluetongue virus 3 | NC_006022 | vertebrates,invertebrates | 1 | Reoviridae,Orbivirus,Bluetongue virus | seg. 7 | JQ086287 |
| Bluetongue virus 3 | NC_006023 | vertebrates,invertebrates | 1 | Reoviridae,Orbivirus,Bluetongue virus | seg. 1 | JQ086281 |
| Bluetongue virus 3 | NC_006024 | vertebrates,invertebrates | 1 | Reoviridae,Orbivirus,Bluetongue virus | seg. 4 | JQ086284 |
| Bluetongue virus 3 | NC_006025 | vertebrates,invertebrates | 1 | Reoviridae,Orbivirus,Bluetongue virus | seg. 5 | JQ086285 |
| Bluetongue virus 4 | NC_006007 | vertebrates,invertebrates | 5 | Reoviridae,Orbivirus,Bluetongue virus | seg. 8 | JN255889,JN255899, AM900373,JN255949 ,AM900372 |
| Bluetongue virus 4 | NC_006008 | vertebrates,invertebrates | 3 | Reoviridae,Orbivirus,Bluetongue virus | seg. 9 | JN255900,JN255950, JN255890 |
| Bluetongue virus 4 | NC_006010 | vertebrates,invertebrates | 13 | Reoviridae,Orbivirus,Bluetongue virus | seg. 6 | JN255887,AJ586680, AJ586682,AJ586677, AJ586679,AJ586699, AJ783909,AJ586678, AJ783908,JN255947, AJ586676,AJ586681, JN255897 |
| Bluetongue virus 4 | NC_006013 | vertebrates,invertebrates | 11 | Reoviridae,Orbivirus,Bluetongue virus | seg. 2 | EF434176,JN255943, DQ191276,JN255883 ,DQ191281,DQ191127 7,AJ585125,DQ191912 80,DQ191279,DQ191 278,JN255893 |
| Bluetongue virus 4 | NC_006014 | vertebrates,invertebrates | 17 | Reoviridae,Orbivirus,Bluetongue virus | seg. 3 | JN255894,DQ186803 ,DQ186801,DQ18681 3,DQ186806,DQ18681 00,DQ186809,DQ186 794,DQ186804,DQ18 6799,DQ186824,DQ1 86825,DQ186802,DQ 186817,JN255884,D 0186823,JN255944 |
| Bluetongue virus 4 | NC_006015 | vertebrates,invertebrates | 11 | Reoviridae,Orbivirus,Bluetongue virus | seg. 10 | JN255901,AF512908, JN255951,JX272588, JN255891,AJ783911, AF512907,AF512909, AJ783910,AF135226, AF512905 |
| Bluetongue virus 4 | NC_006022 | vertebrates,invertebrates | 3 | Reoviridae,Orbivirus,Bluetongue virus | seg. 7 | JN255898,JN255888, JN255948 |
| Bluetongue virus 4 | NC_006023 | vertebrates,invertebrates | 3 | Reoviridae,Orbivirus,Bluetongue virus | seg. 1 | JN255942,JN255882, JN255892 |
| Bluetongue virus 4 | NC_006024 | vertebrates,invertebrates | 3 | Reoviridae,Orbivirus,Bluetongue virus | seg. 4 | JN255895,JN255945, JN255885 |
| Bluetongue virus 4 | NC_006025 | vertebrates,invertebrates | 6 | Reoviridae,Orbivirus,Bluetongue virus | seg. 5 | AM778440,JN255886 ,AM778439,JN255594 6,JN255896,AM7784 41 |

| Taxonomy | NCBI Reference Sequence ID | Host | No. of Genomes | Lineage | Segment Count | Genbank Accession ID |
|---|---|---|---|---|---|---|
| Bluetongue virus 5 | NC_006007 | vertebrates,invertebrates | 1 | Reoviridae,Orbivirus,Bluetongue virus | seg. 8 | AM900378 |
| Bluetongue virus 5 | NC_006010 | vertebrates,invertebrates | 3 | Reoviridae,Orbivirus,Bluetongue virus | seg. 6 | AJ586702,AJ586700,AJ586701 |
| Bluetongue virus 5 | NC_006015 | vertebrates,invertebrates | 1 | Reoviridae,Orbivirus,Bluetongue virus | seg. 10 | JX272578 |
| Bluetongue virus 6 | NC_006010 | vertebrates,invertebrates | 1 | Reoviridae,Orbivirus,Bluetongue virus | seg. 6 | AJ586703 |
| Bluetongue virus 6 | NC_006015 | vertebrates,invertebrates | 1 | Reoviridae,Orbivirus,Bluetongue virus | seg. 10 | JX272568 |
| Bluetongue virus 7 | NC_006007 | vertebrates,invertebrates | 1 | Reoviridae,Orbivirus,Bluetongue virus | seg. 8 | JQ086298 |
| Bluetongue virus 7 | NC_006008 | vertebrates,invertebrates | 1 | Reoviridae,Orbivirus,Bluetongue virus | seg. 9 | JQ086299 |
| Bluetongue virus 7 | NC_006010 | vertebrates,invertebrates | 2 | Reoviridae,Orbivirus,Bluetongue virus | seg. 6 | JQ086296,AJ586704 |
| Bluetongue virus 7 | NC_006013 | vertebrates,invertebrates | 1 | Reoviridae,Orbivirus,Bluetongue virus | seg. 2 | JQ086292 |
| Bluetongue virus 7 | NC_006014 | vertebrates,invertebrates | 1 | Reoviridae,Orbivirus,Bluetongue virus | seg. 3 | JQ086293 |
| Bluetongue virus 7 | NC_006015 | vertebrates,invertebrates | 2 | Reoviridae,Orbivirus,Bluetongue virus | seg. 10 | JQ086300,JX272558 |
| Bluetongue virus 7 | NC_006022 | vertebrates,invertebrates | 1 | Reoviridae,Orbivirus,Bluetongue virus | seg. 7 | JQ086297 |
| Bluetongue virus 7 | NC_006023 | vertebrates,invertebrates | 1 | Reoviridae,Orbivirus,Bluetongue virus | seg. 1 | JQ086291 |
| Bluetongue virus 7 | NC_006024 | vertebrates,invertebrates | 1 | Reoviridae,Orbivirus,Bluetongue virus | seg. 4 | JQ086294 |
| Bluetongue virus 7 | NC_006025 | vertebrates,invertebrates | 1 | Reoviridae,Orbivirus,Bluetongue virus | seg. 5 | JQ086295 |
| Bluetongue virus 8 | NC_006007 | vertebrates,invertebrates | 3 | Reoviridae,Orbivirus,Bluetongue virus | seg. 8 | FJ183381,AM900389,AM498058 |
| Bluetongue virus 8 | NC_006008 | vertebrates,invertebrates | 2 | Reoviridae,Orbivirus,Bluetongue virus | seg. 9 | FJ183382,AM498059 |
| Bluetongue virus 8 | NC_006010 | vertebrates,invertebrates | 4 | Reoviridae,Orbivirus,Bluetongue virus | seg. 6 | FJ183379,AJ586707,AJ586706,AJ586705 |
| Bluetongue virus 8 | NC_006013 | vertebrates,invertebrates | 1 | Reoviridae,Orbivirus,Bluetongue virus | seg. 2 | AM498052 |
| Bluetongue virus 8 | NC_006014 | vertebrates,invertebrates | 2 | Reoviridae,Orbivirus,Bluetongue virus | seg. 3 | AM498053,FJ183376 |
| Bluetongue virus 8 | NC_006015 | vertebrates,invertebrates | 6 | Reoviridae,Orbivirus,Bluetongue virus | seg. 10 | AY120938,AF512924,FJ183383,JX272548,AF512919,AM498060 |
| Bluetongue virus 8 | NC_006022 | vertebrates,invertebrates | 2 | Reoviridae,Orbivirus,Bluetongue virus | seg. 7 | AM498057,FJ183380 |
| Bluetongue virus 8 | NC_006023 | vertebrates,invertebrates | 2 | Reoviridae,Orbivirus,Bluetongue virus | seg. 1 | AM498051,FJ183374 |
| Bluetongue virus 8 | NC_006024 | vertebrates,invertebrates | 3 | Reoviridae,Orbivirus,Bluetongue virus | seg. 4 | FJ183377,AM498054,JX680450 |
| Bluetongue virus 8 | NC_006025 | vertebrates,invertebrates | 3 | Reoviridae,Orbivirus,Bluetongue virus | seg. 5 | FJ183378,AM498055,AM498056 |
| Bluetongue virus 9 | NC_006007 | vertebrates,invertebrates | 12 | Reoviridae,Orbivirus,Bluetongue virus | seg. 8 | JN255919,AM900375,AM900374,JQ086308,JF443164,JN255596,9,AM900388,JN2559 09,AM900377,AM900 385,JN255959,AM900 376 |
| Bluetongue virus 9 | NC_006008 | vertebrates,invertebrates | 11 | Reoviridae,Orbivirus,Bluetongue virus | seg. 9 | JF443161,JQ086309,JN255960,JN2565970,JN255910,JN255920 |
| Bluetongue virus 9 | NC_006010 | vertebrates,invertebrates | 14 | Reoviridae,Orbivirus,Bluetongue virus | seg. 6 | AJ586685,JN255967,AJ586686,JF443160,JQ086306,JN255957, |

-continued

| Taxonomy | NCBI Reference Sequence ID | Host | No. of Genomes | Lineage | Segment Count | Genbank Accession ID |
|---|---|---|---|---|---|---|
| Bluetongue virus 9 | NC_006013 | vertebrates,invertebrates | 13 | Reoviridae,Orbivirus,Bluetongue virus | seg. 2 | AJ586688,JN255917, JN579709,AJ586683, JN255907,AJ586684, AJ586687,AJ586708 JF443157,JN255953, DQ19128,DQ19128 4,JQ086302,JF44315 6,JN255913,DQ1912 82,JF443167,JN2559 63,JF443155,DQ1912 83,JN255903 |
| Bluetongue virus 9 | NC_006014 | vertebrates,invertebrates | 11 | Reoviridae,Orbivirus,Bluetongue virus | seg. 3 | DQ186797,DQ18680 5,JN255954,DQ1867 95,JQ086303,JN2559 04,JN255964,JF4431 58,DQ186808,DQ186 790,JN255914 |
| Bluetongue virus 9 | NC_006015 | vertebrates,invertebrates | 8 | Reoviridae,Orbivirus,Bluetongue virus | seg. 10 | JQ086310,JF443165, AY438034,JN255961, JX272538,JN255911, JN255971,JN255921 |
| Bluetongue virus 9 | NC_006022 | vertebrates,invertebrates | 6 | Reoviridae,Orbivirus,Bluetongue virus | seg. 7 | JN255908,JQ086307, JN255968,JN255918, JN255958,JF443162 |
| Bluetongue virus 9 | NC_006023 | vertebrates,invertebrates | 6 | Reoviridae,Orbivirus,Bluetongue virus | seg. 1 | JN255902,JQ086301, JN255952,JN255962, JN255912,JF443166 |
| Bluetongue virus 9 | NC_006024 | vertebrates,invertebrates | 6 | Reoviridae,Orbivirus,Bluetongue virus | seg. 4 | JN255965,JN255905, JN255955,JQ086304, JN255915,JF443159 |
| Bluetongue virus 9 | NC_006025 | vertebrates,invertebrates | 10 | Reoviridae,Orbivirus,Bluetongue virus | seg. 5 | AM778443,JN255916 ,AM778444,JN255595 6,JF443163,AM77844 2,JN255906,JQ08630 5,JN255966,AM7784 45 |
| Boolarra virus | NC_004142 | vertebrates,invertebrates | 1 | Nodaviridae,Alphanodavirus,Boolarra virus | seg. 2 | AF329080 |
| Boolarra virus | NC_004145 | vertebrates,invertebrates | 1 | Nodaviridae,Alphanodavirus,Boolarra virus | RNA 2 | X15960 |
| Buggy Creek virus | NC_013528 | vertebrates,invertebrates | 1 | Togaviridae,Alphavirus,Fort Morgan virus | — | HM147986 |
| Changuinola virus | NC_022633 | vertebrates,invertebrates | 1 | Reoviridae,Orbivirus,Changuinola virus | seg. 2 | KF624615 |
| Changuinola virus | NC_022634 | vertebrates,invertebrates | 1 | Reoviridae,Orbivirus,Changuinola virus | seg. 3 | KF624616 |
| Changuinola virus | NC_022635 | vertebrates,invertebrates | 1 | Reoviridae,Orbivirus,Changuinola virus | seg. 5 | KF624618 |
| Changuinola virus | NC_022636 | vertebrates,invertebrates | 1 | Reoviridae,Orbivirus,Changuinola virus | seg. 7 | KF624620 |
| Changuinola virus | NC_022637 | vertebrates,invertebrates | 1 | Reoviridae,Orbivirus,Changuinola virus | seg. 8 | KF624621 |
| Changuinola virus | NC_022638 | vertebrates,invertebrates | 1 | Reoviridae,Orbivirus,Changuinola virus | seg. 10 | KF624623 |

| Taxonomy | NCBI Reference Sequence ID | Host | No. of Genomes | Lineage | Segment Count | Genbank Accession ID |
|---|---|---|---|---|---|---|
| Changuinola virus | NC_022639 | vertebrates,invertebrates | 1 | Reoviridae,Orbivirus,Changuinola virus | seg. 1 | KF624614 |
| Changuinola virus | NC_022640 | vertebrates,invertebrates | 1 | Reoviridae,Orbivirus,Changuinola virus | seg. 4 | KF624617 |
| Changuinola virus | NC_022641 | vertebrates,invertebrates | 1 | Reoviridae,Orbivirus,Changuinola virus | seg. 6 | KF624619 |
| Changuinola virus | NC_022642 | vertebrates,invertebrates | 1 | Reoviridae,Orbivirus,Changuinola virus | seg. 9 | KF624622 |
| Chuzan virus | NC_005986 | vertebrates,invertebrates | 4 | Reoviridae,Orbivirus,Palyam virus | seg. 2 | AB177635,AB177632,AB177634,AB177637 |
| Chuzan virus | NC_005988 | vertebrates,invertebrates | 2 | Reoviridae,Orbivirus,Palyam virus | seg. 7 | AY078469,AY078470 |
| Corsican bluetongue virus | NC_006007 | vertebrates,invertebrates | 1 | Reoviridae,Orbivirus,Bluetongue virus | seg. 8 | AY124372 |
| Corsican bluetongue virus | NC_006008 | vertebrates,invertebrates | 1 | Reoviridae,Orbivirus,Bluetongue virus | seg. 9 | AY124373 |
| Corsican bluetongue virus | NC_006014 | vertebrates,invertebrates | 1 | Reoviridae,Orbivirus,Bluetongue virus | seg. 3 | AY124371 |
| Corsican bluetongue virus | NC_006015 | vertebrates,invertebrates | 2 | Reoviridae,Orbivirus,Bluetongue virus | seg. 10 | AF481092,AF481093 |
| Corsican bluetongue virus | NC_006022 | vertebrates,invertebrates | 1 | Reoviridae,Orbivirus,Bluetongue virus | seg. 7 | AY079124 |
| Corsican bluetongue virus | NC_006023 | vertebrates,invertebrates | 1 | Reoviridae,Orbivirus,Bluetongue virus | seg. 1 | AY154458 |
| Eastern equine encephalitis virus | NC_003899 | vertebrates,invertebrates | 10 | Togaviridae,Alphavirus,Eastern equine encephalitis virus | — | DQ241303,DQ24130 4,EF151503,AY70524 0,AY722102,U01034, EF151502,AY705241, X63135,EF568607 |
| Eilat virus | NC_018615 | vertebrates,invertebrates | 1 | Togaviridae,Alphavirus,Eilat virus | — | JX678730 |
| Epizootic hemorrhagic disease of deer virus | NC_013398 | vertebrates,invertebrates | 1 | Reoviridae,Orbivirus,Epizootic hemorrhagic disease virus | seg. 3 | S68010 |
| Epizootic hemorrhagic disease of deer virus | NC_013402 | vertebrates,invertebrates | 3 | Reoviridae,Orbivirus,Epizootic hemorrhagic disease virus | seg. 7 | AY386683,U43560,AF188643 |
| Epizootic hemorrhagic disease virus | NC_013396 | vertebrates,invertebrates | 3 | Reoviridae,Orbivirus,Epizootic hemorrhagic disease virus | seg. 1 | HM641772,HM63689 7,HM636907 |
| Epizootic hemorrhagic disease virus NC_013397 | | vertebrates,invertebrates | 3 | Reoviridae,Orbivirus,Epizootic hemorrhagic disease virus | seg. 2 | AB030735,HM641773 |
| Epizootic hemorrhagic disease virus | NC_013398 | vertebrates,invertebrates | 6 | Reoviridae,Orbivirus,Epizootic hemorrhagic disease virus | seg. 3 | D10767 X61589,HM636909,H M641774,AB041933, EU856069,HM63689 |
| Epizootic hemorrhagic disease virus | NC_013399 | vertebrates,invertebrates | 9 | Reoviridae,Orbivirus,Epizootic hemorrhagic disease virus | seg. 4 | HM641775,HM63690 0,HM636910 |
| Epizootic hemorrhagic disease virus | NC_013400 | vertebrates,invertebrates | 3 | Reoviridae,Orbivirus,Epizootic hemorrhagic disease virus | seg. 5 | HM641776,AB030736 ,X55782 |
| Epizootic hemorrhagic disease virus | NC_013401 | vertebrates,invertebrates | 2 | Reoviridae,Orbivirus,Epizootic hemorrhagic disease virus | seg. 6 | X59000,HM641777 |
| Epizootic hemorrhagic disease virus | NC_013402 | vertebrates,invertebrates | 9 | Reoviridae,Orbivirus,Epizootic hemorrhagic disease virus | seg. 7 | EF213556,D10766,E U856070,HM641778, AF484250,AY351653, AB041934,HM636913 ,HM636903 |
| Epizootic hemorrhagic disease virus | NC_013403 | vertebrates,invertebrates | 3 | Reoviridae,Orbivirus,Epizootic hemorrhagic disease virus | seg. 8 | HM636914,HM64177 9,HM636904 |
| Epizootic hemorrhagic disease virus | NC_013404 | vertebrates,invertebrates | 1 | Reoviridae,Orbivirus,Epizootic hemorrhagic disease virus | seg. 9 | HM641780 |

-continued

| Taxonomy | NCBI Reference Sequence ID | Host | No. of Genomes | Lineage | Segment Count | Genbank Accession ID |
|---|---|---|---|---|---|---|
| Epizootic hemorrhagic disease virus | NC_013405 | vertebrates,invertebrates | 4 | Reoviridae,Orbivirus,Epizootic hemorrhagic disease virus | seg. 10 | AY351654,HM636906,HM641781,HM636916 |
| Epizootic hemorrhagic disease virus (serotype 1/ strain IbAr22619) | NC_013396 | vertebrates,invertebrates | 2 | Reoviridae,Orbivirus,Epizootic hemorrhagic disease virus | seg. 1 | AM745007,AM745010 |
| Epizootic hemorrhagic disease virus (serotype 1/ strain IbAr22619) | NC_013397 | vertebrates,invertebrates | 1 | Reoviridae,Orbivirus,Epizootic hemorrhagic disease virus | seg. 2 | AM745008 |
| Epizootic hemorrhagic disease virus (serotype 1/ strain IbAr22619) | NC_013398 | vertebrates,invertebrates | 1 | Reoviridae,Orbivirus,Epizootic hemorrhagic disease virus | seg. 3 | AM745009 |
| Epizootic hemorrhagic disease virus (serotype 1/ strain IbAr22619) | NC_013400 | vertebrates,invertebrates | 1 | Reoviridae,Orbivirus,Epizootic hemorrhagic disease virus | seg. 5 | AM745011 |
| Epizootic hemorrhagic vertebrates,invertebrates disease virus (serotype 1/ strain IbAr22619) | NC_013401 | vertebrates,invertebrates | 1 | Reoviridae,Orbivirus,Epizootic hemorrhagic disease virus | seg. 6 | AM745012 |
| Epizootic hemorrhagic disease virus (serotype 1/ strain IbAr22619) | NC_013402 | vertebrates,invertebrates | 1 | Reoviridae,Orbivirus,Epizootic hemorrhagic disease virus | seg. 7 | AM745013 |
| Epizootic hemorrhagic disease virus (serotype 1/ strain IbAr22619) | NC_013403 | vertebrates,invertebrates | 1 | Reoviridae,Orbivirus,Epizootic hemorrhagic disease virus | seg. 8 | AM745014 |
| Epizootic hemorrhagic disease virus (serotype 1/ strain IbAr22619) | NC_013404 | vertebrates,invertebrates | 1 | Reoviridae,Orbivirus,Epizootic hemorrhagic disease virus | seg. 9 | AM745015 |
| Epizootic hemorrhagic disease virus (serotype 1/ strain IbAr22619) | NC_013405 | vertebrates,invertebrates | 1 | Reoviridae,Orbivirus,Epizootic hemorrhagic disease virus | seg. 10 | AM745016 |
| Epizootic hemorrhagic disease virus (serotype 1/ strain New Jersey) | NC_013396 | vertebrates,invertebrates | 1 | Reoviridae,Orbivirus,Epizootic hemorrhagic disease virus | seg. 1 | AM744977 |
| Epizootic hemorrhagic disease virus (serotype 1/ strain New Jersey) | NC_013397 | vertebrates,invertebrates | 1 | Reoviridae,Orbivirus,Epizootic hemorrhagic disease virus | seg. 2 | AM744978 |
| Epizootic hemorrhagic disease virus (serotype 1/ strain New Jersey) | NC_013398 | vertebrates,invertebrates | 1 | Reoviridae,Orbivirus,Epizootic hemorrhagic disease virus | seg. 3 | AM744979 |
| Epizootic hemorrhagic disease virus (serotype 1/ strain New Jersey) | NC_013399 | vertebrates,invertebrates | 1 | Reoviridae,Orbivirus,Epizootic hemorrhagic disease virus | seg. 4 | AM744980 |
| Epizootic hemorrhagic disease virus (serotype 1/ strain New Jersey) | NC_013400 | vertebrates,invertebrates | 1 | Reoviridae,Orbivirus,Epizootic hemorrhagic disease virus | seg. 5 | AM744981 |

| Taxonomy | NCBI Reference Sequence ID | Host | No. of Genomes | Lineage | Segment Count | Genbank Accession ID |
|---|---|---|---|---|---|---|
| Epizootic hemorrhagic disease virus (serotype 1/ strain New Jersey) | NC_013401 | vertebrates,invertebrates | 1 | Reoviridae,Orbivirus,Epizootic hemorrhagic disease virus | seg. 6 | AM744982 |
| Epizootic hemorrhagic disease virus (serotype 1/ strain New Jersey) | NC_013402 | vertebrates,invertebrates | 1 | Reoviridae,Orbivirus,Epizootic hemorrhagic disease virus | seg. 7 | AM744983 |
| Epizootic hemorrhagic disease virus (serotype 1/ strain New Jersey) | NC_013403 | vertebrates,invertebrates | 1 | Reoviridae,Orbivirus,Epizootic hemorrhagic disease virus | seg. 8 | AM744984 |
| Epizootic hemorrhagic disease virus (serotype 1/ strain New Jersey) | NC_013404 | vertebrates,invertebrates | 1 | Reoviridae,Orbivirus,Epizootic hemorrhagic disease virus | seg. 9 | AM744985 |
| Epizootic hemorrhagic disease virus (serotype 1/ strain New Jersey) | NC_013405 | vertebrates,invertebrates | 1 | Reoviridae,Orbivirus,Epizootic hemorrhagic disease virus | seg. 10 | AM744986 |
| Epizootic hemorrhagic disease virus (serotype 2/ strain 439) | NC_013396 | vertebrates,invertebrates | 1 | Reoviridae,Orbivirus,Epizootic hemorrhagic disease virus | seg. 1 | AM744987 |
| Epizootic hemorrhagic disease virus (serotype 2/ strain 439) | NC_013397 | vertebrates,invertebrates | 1 | Reoviridae,Orbivirus,Epizootic hemorrhagic disease virus | seg. 2 | AM744988 |
| Epizootic hemorrhagic disease virus (serotype 2/ strain 439) | NC_013398 | vertebrates,invertebrates | 1 | Reoviridae,Orbivirus,Epizootic hemorrhagic disease virus | seg. 3 | AM744989 |
| Epizootic hemorrhagic disease virus (serotype 2/ strain 439) | NC_013399 | vertebrates,invertebrates | 1 | Reoviridae,Orbivirus,Epizootic hemorrhagic disease virus | seg. 4 | AM744990 |
| Epizootic hemorrhagic disease virus (serotype 2/ strain 439) | NC_013400 | vertebrates,invertebrates | 1 | Reoviridae,Orbivirus,Epizootic hemorrhagic disease virus | seg. 5 | AM744991 |
| Epizootic hemorrhagic disease virus (serotype 2/ strain 439) | NC_013401 | vertebrates,invertebrates | 1 | Reoviridae,Orbivirus,Epizootic hemorrhagic disease virus | seg. 6 | AM744992 |
| Epizootic hemorrhagic disease virus (serotype 2/ strain 439) | NC_013402 | vertebrates,invertebrates | 1 | Reoviridae,Orbivirus,Epizootic hemorrhagic disease virus | seg. 7 | AM744993 |
| Epizootic hemorrhagic disease virus (serotype 2/ strain 439) | NC_013403 | vertebrates,invertebrates | 1 | Reoviridae,Orbivirus,Epizootic hemorrhagic disease virus | seg. 8 | AM744994 |
| Epizootic hemorrhagic disease virus (serotype 2/ strain 439) | NC_013404 | vertebrates,invertebrates | 1 | Reoviridae,Orbivirus,Epizootic hemorrhagic disease virus | seg. 9 | AM744995 |
| Epizootic hemorrhagic disease virus (serotype 2/ strain 439) | NC_013405 | vertebrates,invertebrates | 1 | Reoviridae,Orbivirus,Epizootic hemorrhagic disease virus | seg. 10 | AM744996 |
| Epizootic hemorrhagic disease virus (serotype 2/ strain Alberta) | NC_013396 | vertebrates,invertebrates | 1 | Reoviridae,Orbivirus,Epizootic hemorrhagic disease virus | seg. 1 | AM744997 |

-continued

| Taxonomy | NCBI Reference Sequence ID | Host | No. of Genomes | Lineage | Segment Count | Genbank Accession ID |
|---|---|---|---|---|---|---|
| Epizootic hemorrhagic disease virus (serotype 2/strain Alberta) | NC_013397 | vertebrates,invertebrates | 1 | Reoviridae,Orbivirus,Epizootic hemorrhagic disease virus | seg. 2 | AM744998 |
| Epizootic hemorrhagic disease virus (serotype 2/strain Alberta) | NC_013398 | vertebrates,invertebrates | 1 | Reoviridae,Orbivirus,Epizootic hemorrhagic disease virus | seg. 3 | AM744999 |
| Epizootic hemorrhagic disease virus (serotype 2/strain Alberta) | NC_013399 | vertebrates,invertebrates | 1 | Reoviridae,Orbivirus,Epizootic hemorrhagic disease virus | seg. 4 | AM745000 |
| Epizootic hemorrhagic disease virus (serotype 2/strain Alberta) | NC_013400 | vertebrates,invertebrates | 1 | Reoviridae,Orbivirus,Epizootic hemorrhagic disease virus | seg. 5 | AM745001 |
| Epizootic hemorrhagic disease virus (serotype 2/strain Alberta) | NC_013401 | vertebrates,invertebrates | 1 | Reoviridae,Orbivirus,Epizootic hemorrhagic disease virus | seg. 6 | AM745002 |
| Epizootic hemorrhagic disease virus (serotype 2/strain Alberta) | NC_013402 | vertebrates,invertebrates | 1 | Reoviridae,Orbivirus,Epizootic hemorrhagic disease virus | seg. 7 | AM745003 |
| Epizootic hemorrhagic disease virus (serotype 2/strain Alberta) | NC_013403 | vertebrates,invertebrates | 1 | Reoviridae,Orbivirus,Epizootic hemorrhagic disease virus | seg. 8 | AM745004 |
| Epizootic hemorrhagic disease virus (serotype 2/strain Alberta) | NC_013404 | vertebrates,invertebrates | 1 | Reoviridae,Orbivirus,Epizootic hemorrhagic disease virus | seg. 9 | AM745005 |
| Epizootic hemorrhagic disease virus (serotype 2/strain Alberta) | NC_013405 | vertebrates,invertebrates | 1 | Reoviridae,Orbivirus,Epizootic hemorrhagic disease virus | seg. 10 | AM745006 |
| Epizootic hemorrhagic disease virus (serotype 2/strain Ibaraki) | NC_013396 | vertebrates,invertebrates | 1 | Reoviridae,Orbivirus,Epizootic hemorrhagic disease virus | seg. 1 | AM745077 |
| Epizootic hemorrhagic disease virus (serotype 2/strain Ibaraki) | NC_013397 | vertebrates,invertebrates | 1 | Reoviridae,Orbivirus,Epizootic hemorrhagic disease virus | seg. 2 | AM745078 |
| Epizootic hemorrhagic disease virus (serotype 2/strain Ibaraki) | NC_013398 | vertebrates,invertebrates | 1 | Reoviridae,Orbivirus,Epizootic hemorrhagic disease virus | seg. 3 | AM745079 |
| Epizootic hemorrhagic disease virus (serotype 2/strain Ibaraki) | NC_013399 | vertebrates,invertebrates | 1 | Reoviridae,Orbivirus,Epizootic hemorrhagic disease virus | seg. 4 | AM745080 |
| Epizootic hemorrhagic disease virus (serotype 2/strain Ibaraki) | NC_013400 | vertebrates,invertebrates | 1 | Reoviridae,Orbivirus,Epizootic hemorrhagic disease virus | seg. 5 | AM745081 |
| Epizootic hemorrhagic disease virus (serotype 2/strain Ibaraki) | NC_013401 2/ | vertebrates,invertebrates | 1 | Reoviridae,Orbivirus,Epizootic hemorrhagic disease virus | seg. 6 | AM745082 |
| Epizootic hemorrhagic disease virus (serotype 2/strain Ibaraki) | NC_013402 | vertebrates,invertebrates | 1 | Reoviridae,Orbivirus,Epizootic hemorrhagic disease virus | seg. 7 | AM745083 |

| Taxonomy | NCBI Reference Sequence ID | Host | No. of Genomes | Lineage | Segment Count | Genbank Accession ID |
|---|---|---|---|---|---|---|
| Epizootic hemorrhagic disease virus (serotype 2/ strain Ibaraki) | NC_013403 | vertebrates,invertebrates | 1 | Reoviridae,Orbivirus,Epizootic hemorrhagic disease virus | seg. 8 | AM745084 |
| Epizootic hemorrhagic disease virus (serotype 2/ strain Ibaraki) | NC_013404 | vertebrates,invertebrates | 1 | Reoviridae,Orbivirus,Epizootic hemorrhagic disease virus | seg. 9 | AM745085 |
| Epizootic hemorrhagic disease virus (serotype 2/ strain Ibaraki) | NC_013405 | vertebrates,invertebrates | 1 | Reoviridae,Orbivirus,Epizootic hemorrhagic disease virus | seg. 10 | AM745086 |
| Epizootic hemorrhagic disease virus (serotype 4/ strain IbAr 33853) | NC_013396 | vertebrates,invertebrates | 1 | Reoviridae,Orbivirus,Epizootic hemorrhagic disease virus | seg. 1 | AM745017 |
| Epizootic hemorrhagic disease virus (serotype 4/ strain IbAr 33853) | NC_013397 | vertebrates,invertebrates | 1 | Reoviridae,Orbivirus,Epizootic hemorrhagic disease virus | seg. 2 | AM745018 |
| Epizootic hemorrhagic disease virus (serotype 4/ strain IbAr 33853) | NC_013398 | vertebrates,invertebrates | 1 | Reoviridae,Orbivirus,Epizootic hemorrhagic disease virus | seg. 3 | AM745019 |
| Epizootic hemorrhagic disease virus (serotype 4/ strain IbAr 33853) | NC_013399 | vertebrates,invertebrates | 1 | Reoviridae,Orbivirus,Epizootic hemorrhagic disease virus | seg. 4 | AM745020 |
| Epizootic hemorrhagic disease virus (serotype 4/ strain IbAr 33853) | NC_013400 | vertebrates,invertebrates | 1 | Reoviridae,Orbivirus,Epizootic hemorrhagic disease virus | seg. 5 | AM745021 |
| Epizootic hemorrhagic disease virus (serotype 4/ strain IbAr 33853) | NC_013401 | vertebrates,invertebrates | 1 | Reoviridae,Orbivirus,Epizootic hemorrhagic disease virus | seg. 6 | AM745022 |
| Epizootic hemorrhagic disease virus (serotype 4/ strain IbAr 33853) | NC_013402 | vertebrates,invertebrates | 1 | Reoviridae,Orbivirus,Epizootic hemorrhagic disease virus | seg. 7 | AM745023 |
| Epizootic hemorrhagic disease virus (serotype 4/ strain IbAr 33853) | NC_013403 | vertebrates,invertebrates | 1 | Reoviridae,Orbivirus,Epizootic hemorrhagic disease virus | seg. 8 | AM745024 |
| Epizootic hemorrhagic disease virus (serotype 4/ strain IbAr 33853) | NC_013404 | vertebrates,invertebrates | 1 | Reoviridae,Orbivirus,Epizootic hemorrhagic disease virus | seg. 9 | AM745025 |
| Epizootic hemorrhagic disease virus (serotype 4/ strain IbAr 33853) | NC_013405 | vertebrates,invertebrates | 1 | Reoviridae,Orbivirus,Epizootic hemorrhagic disease virus | seg. 10 | AM745026 |
| Epizootic hemorrhagic disease virus (serotype 5/ strain CSIRO 157) | NC_013396 | vertebrates,invertebrates | 2 | Reoviridae,Orbivirus,Epizootic hemorrhagic disease virus | seg. 1 | AM745028,AM745027 |
| Epizootic hemorrhagic disease virus (serotype 5/ strain CSIRO 157) | NC_013397 | vertebrates,invertebrates | 1 | Reoviridae,Orbivirus,Epizootic hemorrhagic disease virus | seg. 2 | AM745029 |
| Epizootic hemorrhagic disease virus (serotype 5/ strain CSIRO 157) | NC_013398 | vertebrates,invertebrates | 1 | Reoviridae,Orbivirus,Epizootic hemorrhagic disease virus | seg. 3 | AM745030 |

| Taxonomy | NCBI Reference Sequence ID | Host | No. of Genomes | Lineage | Segment Count | Genbank Accession ID |
|---|---|---|---|---|---|---|
| Epizootic hemorrhagic disease virus (serotype 5/strain CSIRO 157) | NC_013400 | vertebrates,invertebrates | 1 | Reoviridae,Orbivirus,Epizootic hemorrhagic disease virus | seg. 5 | AM745031 |
| Epizootic hemorrhagic disease virus (serotype 5/strain CSIRO 157) | NC_013401 | vertebrates,invertebrates | 1 | Reoviridae,Orbivirus,Epizootic hemorrhagic disease virus | seg. 6 | AM745032 |
| Epizootic hemorrhagic disease virus (serotype 5/strain CSIRO 157) | NC_013402 | vertebrates,invertebrates | 1 | Reoviridae,Orbivirus,Epizootic hemorrhagic disease virus | seg. 7 | AM745033 |
| Epizootic hemorrhagic disease virus (serotype 5/strain CSIRO 157) | NC_013403 | vertebrates,invertebrates | 1 | Reoviridae,Orbivirus,Epizootic hemorrhagic disease virus | seg. 8 | AM745034 |
| Epizootic hemorrhagic disease virus (serotype 5/strain CSIRO 157) | NC_013404 | vertebrates,invertebrates | 1 | Reoviridae,Orbivirus,Epizootic hemorrhagic disease virus | seg. 9 | AM745035 |
| Epizootic hemorrhagic disease virus (serotype 5/strain CSIRO 157) | NC_013405 | vertebrates,invertebrates | 1 | Reoviridae,Orbivirus,Epizootic hemorrhagic disease virus | seg. 10 | AM745036 |
| Epizootic hemorrhagic disease virus (serotype 6/strain 318) | NC_013396 | vertebrates,invertebrates | 1 | Reoviridae,Orbivirus,Epizootic hemorrhagic disease virus | seg. 1 | AM745067 |
| Epizootic hemorrhagic disease virus (serotype 6/strain 318) | NC_013397 | vertebrates,invertebrates | 1 | Reoviridae,Orbivirus,Epizootic hemorrhagic disease virus | seg. 2 | AM745068 |
| Epizootic hemorrhagic disease virus (serotype 6/strain 318) | NC_013398 | vertebrates,invertebrates | 1 | Reoviridae,Orbivirus,Epizootic hemorrhagic disease virus | seg. 3 | AM745069 |
| Epizootic hemorrhagic disease virus (serotype 6/strain 318) | NC_013399 | vertebrates,invertebrates | 1 | Reoviridae,Orbivirus,Epizootic hemorrhagic disease virus | seg. 4 | AM745070 |
| Epizootic hemorrhagic disease virus (serotype 6/strain 318) | NC_013400 | vertebrates,invertebrates | 1 | Reoviridae,Orbivirus,Epizootic hemorrhagic disease virus | seg. 5 | AM745071 |
| Epizootic hemorrhagic disease virus (serotype 6/strain 318) | NC_013401 | vertebrates,invertebrates | 1 | Reoviridae,Orbivirus,Epizootic hemorrhagic disease virus | seg. 6 | AM745072 |
| Epizootic hemorrhagic disease virus (serotype 6/strain 318) | NC_013402 | vertebrates,invertebrates | 1 | Reoviridae,Orbivirus,Epizootic hemorrhagic disease virus | seg. 7 | AM745073 |
| Epizootic hemorrhagic disease virus (serotype 6/strain 318) | NC_013403 | vertebrates,invertebrates | 1 | Reoviridae,Orbivirus,Epizootic hemorrhagic disease virus | seg. 8 | AM745074 |
| Epizootic hemorrhagic disease virus (serotype 6/strain 318) | NC_013404 | vertebrates,invertebrates | 1 | Reoviridae,Orbivirus,Epizootic hemorrhagic disease virus | seg. 9 | AM745075 |
| Epizootic hemorrhagic disease virus (serotype 6/strain 318) | NC_013405 | vertebrates,invertebrates | 1 | Reoviridae,Orbivirus,Epizootic hemorrhagic disease virus | seg. 10 | AM745076 |

| Taxonomy | NCBI Reference Sequence ID | Host | No. of Genomes | Lineage | Segment Count | Genbank Accession ID |
|---|---|---|---|---|---|---|
| Epizootic hemorrhagic disease virus (serotype 6/strain CSIRO 753) | NC_013396 | vertebrates,invertebrates | 2 | Reoviridae,Orbivirus,Epizootic hemorrhagic disease virus | seg. 1 7 | AM745038,AM745503 |
| Epizootic hemorrhagic disease virus (serotype 6/strain CSIRO 753) | NC_013397 | vertebrates,invertebrates | 1 | Reoviridae,Orbivirus,Epizootic hemorrhagic disease virus | seg. 2 | AM745039 |
| Epizootic hemorrhagic disease virus (serotype 6/strain CSIRO 753) | NC_013398 | vertebrates,invertebrates | 1 | Reoviridae,Orbivirus,Epizootic hemorrhagic disease virus | seg. 3 | AM745040 |
| Epizootic hemorrhagic disease virus (serotype 6/strain CSIRO 753) | NC_013400 | vertebrates,invertebrates | 1 | Reoviridae,Orbivirus,Epizootic hemorrhagic disease virus | seg. 5 | AM745041 |
| Epizootic hemorrhagic disease virus (serotype 6/strain CSIRO 753) | NC_013401 | vertebrates,invertebrates | 1 | Reoviridae,Orbivirus,Epizootic hemorrhagic disease virus | seg. 6 | AM745042 |
| Epizootic hemorrhagic disease virus (serotype 6/strain CSIRO 753) | NC_013402 | vertebrates,invertebrates | 1 | Reoviridae,Orbivirus,Epizootic hemorrhagic disease virus | seg. 7 | AM745043 |
| Epizootic hemorrhagic disease virus (serotype 6/strain CSIRO 753) | NC_013403 | vertebrates,invertebrates | 1 | Reoviridae,Orbivirus,Epizootic hemorrhagic disease virus | seg. 8 | AM745044 |
| Epizootic hemorrhagic disease virus (serotype 6/strain CSIRO 753) | NC_013404 | vertebrates,invertebrates | 1 | Reoviridae,Orbivirus,Epizootic hemorrhagic disease virus | seg. 9 | AM745045 |
| Epizootic hemorrhagic disease virus (serotype 6/strain CSIRO 753) | NC_013405 | vertebrates,invertebrates | 1 | Reoviridae,Orbivirus,Epizootic hemorrhagic disease virus | seg. 10 | AM745046 |
| Epizootic hemorrhagic disease virus (serotype 7/strain CSIRO 775) | NC_013396 | vertebrates,invertebrates | 1 | Reoviridae,Orbivirus,Epizootic hemorrhagic disease virus | seg. 1 | AM745047 |
| Epizootic hemorrhagic disease virus (serotype 7/strain CSIRO 775) | NC_013397 | vertebrates,invertebrates | 1 | Reoviridae,Orbivirus,Epizootic hemorrhagic disease virus | seg. 2 | AM745048 |
| Epizootic hemorrhagic disease virus (serotype 7/strain CSIRO 775) | NC_013398 | vertebrates,invertebrates | 1 | Reoviridae,Orbivirus,Epizootic hemorrhagic disease virus | seg. 3 | AM745049 |
| Epizootic hemorrhagic disease virus (serotype 7/strain CSIRO 775) | NC_013399 | vertebrates,invertebrates | 1 | Reoviridae,Orbivirus,Epizootic hemorrhagic disease virus | seg. 4 | AM745050 |
| Epizootic hemorrhagic disease virus (serotype 7/strain CSIRO 775) | NC_013400 | vertebrates,invertebrates | 1 | Reoviridae,Orbivirus,Epizootic hemorrhagic disease virus | seg. 5 | AM745051 |
| Epizootic hemorrhagic disease virus (serotype 7/strain CSIRO 775) | NC_013401 | vertebrates,invertebrates | 1 | Reoviridae,Orbivirus,Epizootic hemorrhagic disease virus | seg. 6 | AM745052 |
| Epizootic hemorrhagic disease virus (serotype 7/strain CSIRO 775) | NC_013402 | vertebrates,invertebrates | 1 | Reoviridae,Orbivirus,Epizootic hemorrhagic disease virus | seg. 7 | AM745053 |

| Taxonomy | NCBI Reference Sequence ID | Host | No. of Genomes | Lineage | Segment Count | Genbank Accession ID |
|---|---|---|---|---|---|---|
| Epizootic hemorrhagic disease virus (serotype 7/ strain CSIRO 775) | NC_013403 | vertebrates,invertebrates | 1 | Reoviridae,Orbivirus,Epizootic hemorrhagic disease virus | seg. 8 | AM745054 |
| Epizootic hemorrhagic disease virus (serotype 7/ strain CSIRO 775) | NC_013404 | vertebrates,invertebrates | 1 | Reoviridae,Orbivirus,Epizootic hemorrhagic disease virus | seg. 9 | AM745055 |
| Epizootic hemorrhagic disease virus (serotype 7/ strain CSIRO 775) | NC_013405 | vertebrates,invertebrates | 1 | Reoviridae,Orbivirus,Epizootic hemorrhagic disease virus | seg. 10 | AM745056 |
| Epizootic hemorrhagic disease virus (serotype 8/ strain CPR 3961A) | NC_013396 | vertebrates,invertebrates | 1 | Reoviridae,Orbivirus,Epizootic hemorrhagic disease virus | seg. 1 | AM745057 |
| Epizootic hemorrhagic disease virus (serotype 8/ strain CPR 3961A) | NC_013397 | vertebrates,invertebrates | 1 | Reoviridae,Orbivirus,Epizootic hemorrhagic disease virus | seg. 2 | AM745058 |
| Epizootic hemorrhagic disease virus (serotype 8/ strain CPR 3961A) | NC_013398 | vertebrates,invertebrates | 1 | Reoviridae,Orbivirus,Epizootic hemorrhagic disease virus | seg. 3 | AM745059 |
| Epizootic hemorrhagic disease virus (serotype 8/ strain CPR 3961A) | NC_013399 | vertebrates,invertebrates | 1 | Reoviridae,Orbivirus,Epizootic hemorrhagic disease virus | seg. 4 | AM745060 |
| Epizootic hemorrhagic disease virus (serotype 8/ strain CPR 3961A) | NC_013400 | vertebrates,invertebrates | 1 | Reoviridae,Orbivirus,Epizootic hemorrhagic disease virus | seg. 5 | AM745061 |
| Epizootic hemorrhagic disease virus (serotype 8/ strain CPR 3961A) | NC_013401 | vertebrates,invertebrates | 1 | Reoviridae,Orbivirus,Epizootic hemorrhagic disease virus | seg. 6 | AM745062 |
| Epizootic hemorrhagic disease virus (serotype 8/ strain CPR 3961A) | NC_013402 | vertebrates,invertebrates | 1 | Reoviridae,Orbivirus,Epizootic hemorrhagic disease virus | seg. 7 | AM745063 |
| Epizootic hemorrhagic disease virus (serotype 8/ strain CPR 3961A) | NC_013403 | vertebrates,invertebrates | 1 | Reoviridae,Orbivirus,Epizootic hemorrhagic disease virus | seg. 8 | AM745064 |
| Epizootic hemorrhagic disease virus (serotype 8/ strain CPR 3961A) | NC_013404 | vertebrates,invertebrates | 1 | Reoviridae,Orbivirus,Epizootic hemorrhagic disease virus | seg. 9 | AM745065 |
| Epizootic hemorrhagic disease virus (serotype 8/ strain CPR 3961A) | NC_013405 | vertebrates,invertebrates | 1 | Reoviridae,Orbivirus,Epizootic hemorrhagic disease virus | seg. 10 | AM745066 |
| Epizootic hemorrhagic disease virus 1 | NC_013398 | vertebrates,invertebrates | 1 | Reoviridae,Orbivirus,Epizootic hemorrhagic disease virus | seg. 3 | M76616 |
| Epizootic hemorrhagic disease virus 1 | NC_013401 | vertebrates,invertebrates | 1 | Reoviridae,Orbivirus,Epizootic hemorrhagic disease virus | seg. 6 | L27647 |
| Epizootic hemorrhagic disease virus 1 | NC_013402 | vertebrates,invertebrates | 6 | Reoviridae,Orbivirus,Epizootic hemorrhagic disease virus | seg. 7 | AY261511,AY261510,AY261509,AY261507,AY261508,AY261506 |

-continued

| Taxonomy | NCBI Reference Sequence ID | Host | No. of Genomes | Lineage | Segment Count | Genbank Accession ID |
|---|---|---|---|---|---|---|
| Epizootic hemorrhagic disease virus 1 | NC_013403 | vertebrates,invertebrates | 1 | Reoviridae,Orbivirus,Epizootic hemorrhagic disease virus | seg. 8 | L31764 |
| Epizootic hemorrhagic disease virus 1 | NC_013405 | vertebrates,invertebrates disease virus | 1 10 | Reoviridae,Orbivirus,Epizootic hemorrhagic | seg. | L29023 |
| Epizootic hemorrhagic disease virus 2 | NC_013397 | vertebrates,invertebrates | 11 | Reoviridae,Orbivirus,Epizootic hemorrhagic disease virus | seg. 2 | AB078624,L33824,L33821,L33825,AB078632,L33823,AB078620,L33818,AB078628,L33822,L33826 |
| Epizootic hemorrhagic disease virus 2 | NC_013398 | vertebrates,invertebrates | 5 | Reoviridae,Orbivirus,Epizootic hemorrhagic disease virus | seg. 3 | AB078629,L33820,L33819,AB078621,AB078625 |
| Epizootic hemorrhagic disease virus 2 | NC_013400 | vertebrates,invertebrates | 1 | Reoviridae,Orbivirus,Epizootic hemorrhagic disease virus | seg. 5 | AB078633 |
| Epizootic hemorrhagic disease virus 2 | NC_013401 | vertebrates,invertebrates | 5 | Reoviridae,Orbivirus,Epizootic hemorrhagic disease virus | seg. 6 | AB078626,L27648,M69085,AB078622,AB078630 |
| Epizootic hemorrhagic disease virus 2 | NC_013402 | vertebrates,invertebrates | 40 | Reoviridae,Orbivirus,Epizootic hemorrhagic disease virus | seg. 7 | AY261505,AY261492,AY261480,AY261498,AY261500,AY261496,AY261491,AY261486,AB078623,AY261489,AY261485,AY261490,AY261502,AY261494,AB078631,AY261475,AY261497,AY261487,AY261495,AY261476,AY261469,AY261504,AY261503,AY261488,AY261482,AY261477,AY261479,AY261471,AY261483,AY261473,AY261481,AY261478,AY261499,AY261470,AY261472,AB078627,AY261474,AY261493,AY261501,AY261484 |
| Epizootic hemorrhagic disease virus 2 | NC_013403 | vertebrates,invertebrates | 3 | Reoviridae,Orbivirus,Epizootic hemorrhagic disease virus | seg. 8 | M69091,AB084285,L31765 |
| Epizootic hemorrhagic disease virus 2 | NC_013405 | vertebrates,invertebrates | 1 | Reoviridae,Orbivirus,Epizootic hemorrhagic disease virus | seg. 10 | L29022 |
| Epizootic hemorrhagic disease virus 6 | NC_013398 | vertebrates,invertebrates | 1 | Reoviridae,Orbivirus,Epizootic hemorrhagic disease virus | seg. 3 | KC986825 |
| Epizootic hemorrhagic disease virus 6 | NC_013401 | vertebrates,invertebrates | 1 | Reoviridae,Orbivirus,Epizootic hemorrhagic disease virus | seg. 6 | KC986823 |

-continued

| Taxonomy | NCBI Reference Sequence ID | Host | No. of Genomes | Lineage | Segment Count | Genbank Accession ID |
|---|---|---|---|---|---|---|
| Epizootic hemorrhagic disease virus 6 | NC_013402 | vertebrates,invertebrates | 1 | Reoviridae,Orbivirus,Epizootic hemorrhagic disease virus | seg. 7 | KC986824 |
| Fort Morgan virus | NC_013528 | vertebrates,invertebrates | 1 | Togaviridae,Alphavirus,Fort Morgan virus | — | GQ281603 |
| Getah virus | NC_006558 | vertebrates,invertebrates | 7 | Togaviridae,Alphavirus,Getah virus | — | EU015061,AY702913,EF631998,EU01506 2,AB859822,EU0150 63,EF631999 |
| Highlands J virus | NC_012561 | vertebrates,invertebrates | 3 | Togaviridae,Alphavirus,Highlands J virus | — | GU167952,GQ22778 9,FJ827631 |
| Ibaraki virus | NC_013396 | vertebrates,invertebrates | 1 | Reoviridae,Orbivirus,Epizootic hemorrhagic disease virus | seg. 1 | AB186040 |
| Midway virus | NC_012702 | vertebrates,invertebrates | 1 | Midway virus | — | FJ554525 |
| Mobuck virus | NC_022620 | vertebrates,invertebrates | 1 | Reoviridae,Orbivirus,Mobuck virus | segment n2 | KF296323 |
| Mobuck virus | NC_022621 | vertebrates,invertebrates | 1 | Reoviridae,Orbivirus,Mobuck virus | seg. n4 | KF296325 |
| Mobuck virus | NC_022622 | vertebrates,invertebrates | 1 | Reoviridae,Orbivirus,Mobuck virus | seg. n6 | KF296327 |
| Mobuck virus | NC_022623 | vertebrates,invertebrates | 1 | Reoviridae,Orbivirus,Mobuck virus | segment n7 | KF296328 |
| Mobuck virus | NC_022624 | vertebrates,invertebrates | 1 | Reoviridae,Orbivirus,Mobuck virus | seg. segment n9 | KF296330 |
| Mobuck virus | NC_022625 | vertebrates,invertebrates | 1 | Reoviridae,Orbivirus,Mobuck virus | seg. 10 | KF296331 |
| Mobuck virus | NC_022626 | vertebrates,invertebrates | 1 | Reoviridae,Orbivirus,Mobuck virus | seg. segment n1 | KF296322 |
| Mobuck virus | NC_022627 | vertebrates,invertebrates | 1 | Reoviridae,Orbivirus,Mobuck virus | seg. segment n3 | KF296324 |
| Mobuck virus | NC_022628 | vertebrates,invertebrates | 1 | Reoviridae,Orbivirus,Mobuck virus | seg. segment n5 | KF296326 |
| Mobuck virus | NC_022629 | vertebrates,invertebrates | 1 | Reoviridae,Orbivirus,Mobuck virus | seg. segment n8 | KF296329 |
| Ndumu virus | NC_016959 | vertebrates,invertebrates | 1 | Togaviridae,Alphavirus,Ndumu virus | — | HM147989 |
| Nodamura virus | NC_002690 | vertebrates,invertebrates | 1 | Nodaviridae,Alphanodavirus,Nodamura virus | — | AF174533 |
| Nodamura virus | NC_002691 | vertebrates,invertebrates | 2 | Nodaviridae,Alphanodavirus,Nodamura virus | seg. RNA | AF174534,X15961 |
| Nyamanini virus | NC_012703 | vertebrates,invertebrates | 1 | Nyamanini virus | seg. RNA 2 | FJ554526 |
| Ockelbo virus | NC_001547 | vertebrates,invertebrates | 1 | Togaviridae,Alphavirus,Sindbis virus | — | M69205 |
| Palyam virus | NC_005986 | vertebrates,invertebrates | 1 | Reoviridae,Orbivirus,Palyam virus | seg. 2 | AB014725 |

-continued

| Taxonomy | NCBI Reference Sequence ID | Host | No. of Genomes | Lineage | Segment Count | Genbank Accession ID |
|---|---|---|---|---|---|---|
| Palyam virus | NC_005987 | vertebrates,invertebrates | 1 | Reoviridae,Orbivirus,Palyam virus | seg. 6 | AB014726 |
| Palyam virus | NC_005988 | vertebrates,invertebrates | 1 | Reoviridae,Orbivirus,Palyam virus | seg. 7 | AB014727 |
| Palyam virus | NC_005989 | vertebrates,invertebrates | 1 | Reoviridae,Orbivirus,Palyam virus | seg. 3 | AB014728 |
| Palyam virus | NC_005990 | vertebrates,invertebrates | 1 | Reoviridae,Orbivirus,Palyam virus | seg. 1 | AB018086 |
| Palyam virus | NC_005991 | vertebrates,invertebrates | 1 | Reoviridae,Orbivirus,Palyam virus | seg. 4 | AB018087 |
| Palyam virus | NC_005992 | vertebrates,invertebrates | 1 | Reoviridae,Orbivirus,Palyam virus | seg. 9 | AB018088 |
| Palyam virus | NC_005993 | vertebrates,invertebrates | 1 | Reoviridae,Orbivirus,Palyam virus | seg. 5 | AB018089 |
| Palyam virus | NC_005994 | vertebrates,invertebrates | 1 | Reoviridae,Orbivirus,Palyam virus | seg. 8 | AB018090 |
| Palyam virus | NC_005995 | vertebrates,invertebrates | 1 | Reoviridae,Orbivirus,Palyam virus | seg. 10 | AB018091 |
| Peruvian horse sickness virus | NC_007748 | vertebrates,invertebrates | 1 | Reoviridae,Orbivirus,Peruvian horse sickness virus | seg. 1 | DQ248057 |
| Peruvian horse sickness virus | NC_007749 | vertebrates,invertebrates | 1 | Reoviridae,Orbivirus,Peruvian horse sickness virus | seg. 2 | DQ248058 |
| Peruvian horse sickness virus | NC_007750 | vertebrates,invertebrates | 1 | Reoviridae,Orbivirus,Peruvian horse sickness virus | seg. 3 | DQ248059 |
| Peruvian horse sickness virus | NC_007751 | vertebrates,invertebrates | 1 | Reoviridae,Orbivirus,Peruvian horse sickness virus | seg. 4 | DQ248060 |
| Peruvian horse sickness virus | NC_007752 | vertebrates,invertebrates | 1 | Reoviridae,Orbivirus,Peruvian horse sickness virus | seg. 6 | DQ248061 |
| Peruvian horse sickness virus | NC_007753 | vertebrates,invertebrates | 2 | Reoviridae,Orbivirus,Peruvian horse sickness virus | seg. 9 | DQ248062,FJ225398 |
| Peruvian horse sickness virus | NC_007754 | vertebrates,invertebrates | 1 | Reoviridae,Orbivirus,Peruvian horse sickness virus | seg. 8 | DQ248063 |
| Peruvian horse sickness virus | NC_007755 | vertebrates,invertebrates | 1 | Reoviridae,Orbivirus,Peruvian horse sickness virus | seg. 5 | DQ248064 |
| Peruvian horse sickness virus | NC_007756 | vertebrates,invertebrates | 1 | Reoviridae,Orbivirus,Peruvian horse sickness virus | seg. 7 | DQ248065 |
| Peruvian horse sickness virus | NC_007757 | vertebrates,invertebrates | 2 | Reoviridae,Orbivirus,Peruvian horse sickness virus | seg. 10 | FJ225399,DQ248066 |
| Salmon pancreas disease virus | NC_003930,NC_003343 | vertebrates,invertebrates | 1 | Togaviridae,Alphavirus,Salmon pancreas disease virus | — | AJ316244 |
| Salmonid alphavirus subtype 3 | NC_003930,NC_003343 | vertebrates,invertebrates | 9 | Togaviridae,Alphavirus,Salmon pancreas disease virus | — | KC122926,KC122919,KC122923,KC122918,KC122920,KC122925,KC122922,KC122924,KC122921 |
| Semliki forest virus | NC_003215 | vertebrates,invertebrates | 7 | Togaviridae,Alphavirus,Semliki forest virus | — | DQ189084,XQ4129,DQ189086,Z48163,DQ189082,EU350586,AY112987 |
| Sindbjs virus | NC_001547 | vertebrates,invertebrates | 14 | Togaviridae,Alphavirus,Sindbjs virus | — | AF429428,KF737350,JQ771793,JQ771797,JQ771798,JQ771795,JX570540,GU361116,JQ2363,GU361118,A |

-continued

| Taxonomy | NCBI Reference Sequence ID | Host | No. of Genomes | Lineage | Segment Count | Genbank Accession ID |
|---|---|---|---|---|---|---|
| Sindbjs-like virus | NC_001547 | vertebrates,invertebrates | 2 | Togaviridae,Alphavirus,Sindbjs virus | — | F10378,JQ771794,JQ771799,JQ771796 |
| Sindbjs-like virus YN87448 | NC_001547 | vertebrates,invertebrates | 1 | Togaviridae,Alphavirus,Sindbjs virus | — | U38304,U38305 |
| Southern elephant seal virus | NC_016960 | vertebrates,invertebrates | 1 | Togaviridae,Alphavirus,Southern elephant seal virus | — | AF103734 HM147990 |
| St Croix River virus | NC_005997 | vertebrates,invertebrates | 1 | Reoviridae,Orbivirus,St Croix River virus | seg. 1 | AF133431 |
| St Croix River virus | NC_005998 | vertebrates,invertebrates | 1 | Reoviridae,Orbivirus,St Croix River virus | seg. 2 | AF133432 |
| St Croix River virus | NC_005999 | vertebrates,invertebrates | 1 | Reoviridae,Orbivirus,St Croix River virus | seg. 3 | AF145400 |
| St Croix River virus | NC_006000 | vertebrates,invertebrates | 1 | Reoviridae,Orbivirus,St Croix River virus | seg. 4 | AF145401 |
| St Croix River virus | NC_006001 | vertebrates,invertebrates | 1 | Reoviridae,Orbivirus,St Croix River virus | seg. 5 | AF145402 |
| St Croix River virus | NC_006002 | vertebrates,invertebrates | 1 | Reoviridae,Orbivirus,St Croix River virus | seg. 6 | AF145403 |
| St Croix River virus | NC_006003 | vertebrates,invertebrates | 1 | Reoviridae,Orbivirus,St Croix River virus | seg. 7 | AF145404 |
| St Croix River virus | NC_006004 | vertebrates,invertebrates | 1 | Reoviridae,Orbivirus,St Croix River virus | seg. 8 | AF145405 |
| St Croix River virus | NC_006005 | vertebrates,invertebrates | 1 | Reoviridae,Orbivirus,St Croix River virus | seg. 9 | AF145406 |
| St Croix River virus | NC_006006 | vertebrates,invertebrates | 1 | Reoviridae,Orbivirus,St Croix River virus | seg. 10 | AF145407 |
| Stretch Lagoon orbivirus | NC_012754 | vertebrates,invertebrates | 1 | Reoviridae,Orbivirus,Stretch Lagoon orbivirus | seg. 1 | EU718676 |
| Stretch Lagoon orbivirus | NC_012755 | vertebrates,invertebrates | 1 | Reoviridae,Orbivirus,Stretch Lagoon orbivirus | seg. 2 | EU718677 |
| Venezuelan equine encephalitis virus | NC_001449 | vertebrates,invertebrates | 132 | Togaviridae,Alphavirus,Venezuelan equine encephalitis virus | — | U55362,KC344436,U55360,KC344447,AF075255,AF375051,KC344446,L01442,KC344510,KC344519,KC344449,U55345,JQ4332,KC344475,AF075251,KC344501,KC344471,AF069903,KC344491,KC344490,KC344430,U55350,KC344455,KC344431,KC344469,KC344478,KC344446,KC344509,KC344482,KC344462,AF075254,AF100566,AF004472,KC344526,KC344438,KC344429,KC344498,KC344458,AF075259,KC344433,KC344450,KC344444,KC344522,KC344439,KC344485,KC344483,U55347,KC344467,AF075252,KC344466,KC344441,KC344484,KC344524,KC344503,KC344493,AY823299,KC344 |

| Taxonomy | NCBI Reference Sequence ID | Host | No. of Genomes | Lineage | Segment Count | Genbank Accession ID |
|---|---|---|---|---|---|---|
| | | | | | | 495,KC344465,KC34 4474,AF004458,KC3 44513,KC344525,KC 344461,KC344442,K C344473,KC344440, KC344487,AF075257 ,AF075258,KC34450 5,KC344437,KC3445 27,AF075256,KC344 489,KC344457,KC34 4445,KC344502,KC3 44460,KC344518,KC 344528,KC344453,K C344515,KC344506, AY986475,KC344444 ,KC344468,KC34447 9,KC344464,KC3444 72,L04653,KC344463 ,U55342,AY741139,D 0390224,KC344435, AF075253,KC344432 ,KC344499,KC34445 1,L01443,KC344452, KC344496,KC344481 ,KC344508,KC34445 6,KC344517,KC3444 88,KC344494,KC344 511,KC344494,KC34 4448,KC344514,KC3 44507,KC344480,AY 973944,KC344504,K C344521,KC344470, KC344492,KC344454 ,KC344476,KC34450 0,KC344512,KC3445 20,AF004459,KC344 459,KC344516,KC34 4497,KC344477,KC3 44434,KF985959,L00 930 |
| Wallal virus | NC_022553 | vertebrates,invertebrates | 1 | Reoviridae,Orbivirus,Wallal virus | seg. 1 | KF234259 |
| Wallal virus | NC_022554 | vertebrates,invertebrates | 1 | Reoviridae,Orbivirus,Wallal virus | seg. 2 | KF234260 |
| Wallal virus | NC_022555 | vertebrates,invertebrates | 1 | Reoviridae,Orbivirus,Wallal virus | seg. 3 | KF234261 |
| Wallal virus | NC_022556 | vertebrates,invertebrates | 1 | Reoviridae,Orbivirus,Wallal virus | segment 5 | KF234263 |

-continued

| Taxonomy | NCBI Reference Sequence ID | Host | No. of Genomes | Lineage | Segment Count | Genbank Accession ID |
|---|---|---|---|---|---|---|
| Wallal virus | NC_022557 | vertebrates,invertebrates | 1 | Reoviridae,Orbivirus,Wallal virus | seg. segmen7 | KF234265 |
| Wallal virus | NC_022558 | vertebrates,invertebrates | 1 | Reoviridae,Orbivirus,Wallal virus | seg. segmen9 | KF234267 |
| Wallal virus | NC_022559 | vertebrates,invertebrates | 1 | Reoviridae,Orbivirus,Wallal virus | seg. 10 | KF234268 |
| Wallal virus | NC_022560 | vertebrates,invertebrates | 1 | Reoviridae,Orbivirus,Wallal virus | seg. segmen4 | KF234262 |
| Wallal virus | NC_022561 | vertebrates,invertebrates | 1 | Reoviridae,Orbivirus,Wallal virus | seg. segmen6 | KF234264 |
| Wallal virus | NC_022562 | vertebrates,invertebrates | 1 | Reoviridae,Orbivirus,Wallal virus | seg. segmen8 | KF234266 |
| Western equine encephalomyelitis virus | NC_003908 | vertebrates,invertebrates | 9 | Togaviridae,Alphavirus,Western equine encephalitis virus | — | AF214040,GQ287640,GQ287641,GQ287645,GQ287643,GQ287644,GQ287642,GQ287647,GQ287646 |
| Whataroa virus | NC_016961 | vertebrates,invertebrates | 1 | Togaviridae,Alphavirus,Whataroa virus | — | HM147993 |
| Yunnan orbivirus | NC_007656 | vertebrates,invertebrates | 1 | Reoviridae,Orbivirus,Yunnan orbivirus | seg. 1 | AY701509 |
| Yunnan orbivirus | NC_007657 | vertebrates,invertebrates | 1 | Reoviridae,Orbivirus,Yunnan orbivirus | seg. 2 | AY701510 |
| Yunnan orbivirus | NC_007658 | vertebrates,invertebrates | 1 | Reoviridae,Orbivirus,Yunnan orbivirus | seg. 3 | AY701511 |
| Yunnan orbivirus | NC_007659 | vertebrates,invertebrates | 1 | Reoviridae,Orbivirus,Yunnan orbivirus | seg. 4 | AY701512 |
| Yunnan orbivirus | NC_007660 | vertebrates,invertebrates | 1 | Reoviridae,Orbivirus,Yunnan orbivirus | seg. 5 | AY701513 |
| Yunnan orbivirus | NC_007661 | vertebrates,invertebrates | 1 | Reoviridae,Orbivirus,Yunnan orbivirus | seg. 6 | AY701514 |
| Yunnan orbivirus | NC_007662 | vertebrates,invertebrates | 1 | Reoviridae,Orbivirus,Yunnan orbivirus | seg. 7 | AY701515 |
| Yunnan orbivirus | NC_007663 | vertebrates,invertebrates | 1 | Reoviridae,Orbivirus,Yunnan orbivirus | seg. 8 | AY701516 |
| Yunnan orbivirus | NC_007664 | vertebrates,invertebrates | 2 | Reoviridae,Orbivirus,Yunnan orbivirus | seg. 9 | AY701517,FJ225402 |
| Yunnan orbivirus | NC_007665 | vertebrates,invertebrates | 1 | Reoviridae,Orbivirus,Yunnan orbivirus | seg. 10 | AY701518 |
| Aedes flavivirus | NC_012932 | vertebrates,invertebrates, human | 2 | Flaviviridae,Flavivirus,Aedes flavivirus | — | KC181923,AB488408 |
| Aguacate virus | NC_015450 | vertebrates,invertebrates, human | 1 | Bunyaviridae,Phlebovirus,Aguacate virus | seg. M | HM566137 |
| Aguacate virus | NC_015451 | vertebrates,invertebrates, human | 1 | Bunyaviridae,Phlebovirus,Aguacate virus | seg. L | HM566138 |
| Aguacate virus | NC_015452 | vertebrates,invertebrates, human | 1 | Bunyaviridae,Phlebovirus,Aguacate virus | seg. S | HM566139 |
| Aino virus | NC_018459 | vertebrates,invertebrates, human | 1 | Bunyaviridae,Orthobunyavirus,Shuni virus | seg. M | HE795088 |
| Aino virus | NC_018460 | vertebrates,invertebrates, human | 1 | Bunyaviridae,Orthobunyavirus,Shuni virus | seg. S | HE795089 |
| Aino virus | NC_018465 | vertebrates,invertebrates, human | 1 | Bunyaviridae,Orthobunyavirus,Shuni virus | seg. L | HE795087 |

-continued

| Taxonomy | NCBI Reference Sequence ID | Host | No. of Genomes | Lineage | Segment Count | Genbank Accession ID |
|---|---|---|---|---|---|---|
| Akabane virus | NC_009894 | vertebrates,invertebrates,human | 2 | Bunyaviridae,Orthobunyavirus,Akabane virus | seg. L | JQ308779,AB190458 |
| Akabane virus | NC_009895 | vertebrates,invertebrates,human | 42 | Bunyaviridae,Orthobunyavirus,Akabane virus | seg. M | AB297833,AB289324,AB297822,AB297837,AB297831,AB297819,AB297844,AB297839,AB426282,AB297834,AB297827,AB297821,AB297841,AB297838,AB297824,AB297842,AB297823,B297842,AB297823,AB297825,AB297845,AB297829,AB297785,AB436954,AB297835,AB297828,AB297850,AB297826,AB297832,AB297840,AB297873233,AB297847,AB297843,AB289323,AB426281,AB100604,AB297820,AB297846,AB297836,AB297781,AB297849,AB289322,AB297848,AB297830 |
| Akabane virus | NC_009896 | vertebrates,invertebrates,human | 21 | Bunyaviridae,Orthobunyavirus,Akabane virus | seg. S | AB289319,AB426275,AB426277,AB426274,AB289320,AB000851,AB426278,AB426272,AF034939,AB373232,AB373234,AB426279,AB426276,AF529883,AB426273,AB426271,AB426280,AF034942,AF034941,AF034940,AB289321 |
| Alenquer virus | NC_015373 | vertebrates,invertebrates,human | 1 | Bunyaviridae,Phlebovirus,Candiru virus | seg. M | HM119402 |
| Alenquer virus | NC_015374 | vertebrates,invertebrates,human | 1 | Bunyaviridae,Phlebovirus,Candiru virus | seg. L | HM119401 |
| Alenquer virus | NC_015375 | vertebrates,invertebrates,human | 1 | Bunyaviridae,Phlebovirus,Candiru virus | seg. S | HM119403 |
| Alfuy virus | NC_000943 | vertebrates,invertebrates,human | 1 | Flaviviridae,Flavivirus,Murray Valley encephalitis virus | — | AY898809 |
| Alkhurma hemorrhagic fever virus | NC_004355 | vertebrates,invertebrates,human | 19 | Flaviviridae,Flavivirus,Kyasanur forest disease virus | — | JF416955,JF416950,JF416963,JF416956,JX271893,JF416954,JF416951,JN860200, |

-continued

| Taxonomy | NCBI Reference Sequence ID | Host | No. of Genomes | Lineage | Segment Count | Genbank Accession ID |
|---|---|---|---|---|---|---|
| | | | | | | JF416961,JF416964, JF416957,JF416967, JF416949,JF416966, JF416953,JF416965, JX271892,JF416962, JF416952 |
| Alkhurma hemorrhagic fever virus | NC_004355 | vertebrates,invertebrates, human | 1 | Flaviviridae,Flavivirus,Kyasanur forest disease virus | — | AF331718 |
| Alphavirus M1 | NC_001544 | vertebrates,invertebrates, human | 1 | Togaviridae,Alphavirus,Ross River virus | — | EF011023 |
| Apoi virus | NC_003676 | vertebrates,invertebrates, human | 1 | Flaviviridae,Flavivirus,Apoi virus | — | AF160193 |
| Ariquemes virus | NC_015373 | vertebrates,invertebrates, human | 1 | Bunyaviridae,Phlebovirus,Candiru virus | seg. M | HM119405 |
| Ariquemes virus | NC_015374 | vertebrates,invertebrates, human | 1 | Bunyaviridae,Phlebovirus,Candiru virus | seg. L | HM119404 |
| Ariquemes virus | NC_015375 | vertebrates,invertebrates, human | 1 | Bunyaviridae,Phlebovirus,Candiru virus | seg. S | HM119406 |
| Armero virus | NC_015450 | vertebrates,invertebrates, human | 1 | Bunyaviridae,Phlebovirus,Aguacate virus | seg. M | HQ661806 |
| Armero virus | NC_015451 | vertebrates,invertebrates, human | 2 5 | Bunyaviridae,Phlebovirus,Aguacate virus | seg. L | HM566140,HQ66180 |
| Armero virus | NC_015452 | vertebrates,invertebrates, human | 2 7 | Bunyaviridae,Phlebovirus,Aguacate virus | seg. S | HM566142,HQ66180 |
| Aroa virus | NC_009026 | vertebrates,invertebrates, human | 1 | Flaviviridae,Flavivirus,Aroa virus | — | AY632536 |
| Bagaza virus | NC_012534 | vertebrates,invertebrates, human | 4 | Flaviviridae,Flavivirus,Bagaza virus | — | AY632545,EU684972 ,HQ644143,HQ64414 4 |
| Banna virus | NC_004211 | vertebrates,invertebrates, human | 2 | Reoviridae,Seadornavirus,Banna virus | seg. 1 | AF133430,AF168005 |
| Banna virus | NC_004217 | vertebrates,invertebrates, human | 3 | Reoviridae,Seadornavirus,Banna virus | seg. 2 | AF134528,AF134526, AF134514 |
| Banna virus | NC_004218 | vertebrates,invertebrates, human | 2 | Reoviridae,Seadornavirus,Banna virus | seg. 3 | AF134515,AY549307 |
| Banna virus | NC_004219 | vertebrates,invertebrates, human | 3 | Reoviridae,Seadornavirus,Banna virus | seg. 4 | EU265698,AY549308 ,AF134516 |
| Banna virus | NC_004220 | vertebrates,invertebrates, human | 2 | Reoviridae,Seadornavirus,Banna virus | seg. 5 | AF134517,AY549309 |
| Banna virus 5 AF134518 | NC_004221 | vertebrates,invertebrates, human | 1 | Reoviridae,Seadornavirus,Banna virus | seg. 6 | AF134521,AF168006, AF134527,AF134524, |
| Batai virus | NC_001926 | vertebrates,invertebrates, human | 1 | Bunyaviridae,Orthobunyavirus,Bunyamwera virus | seg. M | DQ436460 |
| Batai virus | NC_001927 | vertebrates,invertebrates, human | 1 | Bunyaviridae,Orthobunyavirus,Bunyamwera virus | seg. S | X73464 |

-continued

| Taxonomy | NCBI Reference Sequence ID | Host | No. of Genomes | Lineage | Segment Count | Genbank Accession ID |
|---|---|---|---|---|---|---|
| Birao virus | NC_001927 | vertebrates,invertebrates, human | 1 | Bunyaviridae,Orthobunyavirus,Bunyamwera virus | seg. S | AM711131 |
| Bozo virus | NC_001927 | vertebrates,invertebrates, human | 1 | Bunyaviridae,Orthobunyavirus,Bunyamwera virus | seg. S | AM711132 |
| Brazoran virus | NC_022037 | vertebrates,invertebrates, human | 1 | Bunyaviridae,Orthobunyavirus,Brazoran virus | seg. S | KC854416 |
| Brazoran virus | NC_022038 | vertebrates,invertebrates, human | 1 | Bunyaviridae,Orthobunyavirus,Brazoran virus | seg. M | KC854417 |
| Brazoran virus | NC_022039 | vertebrates,invertebrates, human | 1 | Bunyaviridae,Orthobunyavirus,Brazoran virus | seg. L | KC854418 |
| Bunyamwera virus | NC_001925 | vertebrates,invertebrates, human | 1 | Bunyaviridae,Orthobunyavirus,Bunyamwera virus | seg. L | X14383 |
| Bunyamwera virus | NC_001926 | vertebrates,invertebrates, human | 1 | Bunyaviridae,Orthobunyavirus,Bunyamwera virus | seg. M | M11852 |
| Bunyamwera virus | NC_001927 | vertebrates,invertebrates, human | 4 | Bunyaviridae,Orthobunyavirus,Bunyamwera virus | seg. S | DQ0353,AM711130,AM709778,AF325122 |
| Cache Valley virus | NC_001926 | vertebrates,invertebrates, human | 2 | Bunyaviridae,Orthobunyavirus,Bunyamwera virus | seg. M | AF082739,AF082576 |
| Cache Valley virus | NC_001927 | vertebrates,invertebrates, human | 1 | Bunyaviridae,Orthobunyavirus,Bunyamwera virus | seg. S | X73465 |
| California encephalitis virus | NC_004109 | vertebrates,invertebrates, human | 1 | Bunyaviridae,Orthobunyavirus,California encephalitis virus | seg. M | AF123483 |
| California encephalitis virus | NC_004110 | vertebrates,invertebrates, human | 2 | Bunyaviridae,Orthobunyavirus,California encephalitis virus | seg. S | U12797,U12800 |
| Candiru virus | NC_015373 | vertebrates,invertebrates, human | 1 | Bunyaviridae,Phlebovirus,Candiru virus | seg. M | HM119408 |
| Candiru virus | NC_015374 | vertebrates,invertebrates, human | 1 | Bunyaviridae,Phlebovirus,Candiru virus | seg. L | HM119407 |
| Candiru virus | NC_015375 | vertebrates,invertebrates, human | 1 | Bunyaviridae,Phlebovirus,Candiru virus | seg. S | HM119409 |
| Cell fusing agent virus | NC_001564 | vertebrates,invertebrates, human | 1 | Flaviviridae,Flavivirus,Cell fusing agent virus | — | M91671 |
| Chaoyang virus | NC_017086 | vertebrates,invertebrates, human | 2 | Flaviviridae,Flavivirus,Chaoyang virus | — | JQ068102,JQ308185 |
| Chatanga virus | NC_004108 | vertebrates,invertebrates, human | 1 | Bunyaviridae,Orthobunyavirus,California encephalitis virus | seg. L | EU616903 |
| Chatanga virus | NC_004109 | vertebrates,invertebrates, human | 1 | Bunyaviridae,Orthobunyavirus,California encephalitis virus | seg. M | EU621834 |
| Chikungunya virus | NC_004162 | vertebrates,invertebrates, human | 161 | Togaviridae,Alphavirus,Chikungunya virus | — | GQ42821 1,FR717336,HM045789,JQ067624,FJ445510,FJ513654,GU301781,GU199351,FN295485,HM045819,FJ445463,HM045787,HM045796,JQ861256,AM258994,FJ807899,HM045812,HM045814,HE806461,J |

| Taxonomy | NCBI Reference Sequence ID | Host | No. of Genomes | Lineage | Segment Count | Genbank Accession ID |
|---|---|---|---|---|---|---|
| | | | | | | 0861253,HQ456253, HM045803,EF027137 ,EF027139,HM04579 0,FJ513637,AY72673 2,AM258991,EU7037 60,HM045820,GU301 780,JF274082,HM04 5816,FJ445431,HQ84 6357,HM045802,EU5 64335,GU301779,HM 045821,GU199350,H 0846356,FJQ00066,F J513632,FJ445428,F JQ00069,KC862329,J 0861260,FJ445433,F J513629,HM045811, HM045807,GU01352 9,FR717337,HM0458 13,HM045797,AM258 995,GU199352,FJ513 635,AM258992,HM04 5798,FJ513645,HQ84 6358,FJ445427,DQ44 3544,EF027136,EU7 03759,HQ456251,AF 369024,FJ513628,EF 452493,FJ445432,FN 295483,FJQ00062,GU 189061,HM045795,E U703761,HQ846359, FJQ00067,GQ428214 ,HQ456252,GU19935 3,FJQ00064,HM0458 10,HM045822,HM045 823,FJ513673,FN295 487,JQ861254,EF210 157,HM045791,JQ86 1257,FJ445443,EF02 7141,JN558836,HMO 45805,FJQ00063,HM 045806,HM045786,E F027135,GQ428215, HM045817,HM04581 5,FN295484,FJ80789 8,EU372006,GQ4282 13,EF452494,FJ5136 75,HM045818,JN558 835,HM045801,GQ42 |

-continued

| Taxonomy | NCBI Reference Sequence ID | Host | No. of Genomes | Lineage | Segment Count | Genbank Accession ID |
|---|---|---|---|---|---|---|
| | | | | | | 8212,GQ905863,HMO45784,AF490259,EFO27134,HQ456255,GU013528,FJ959103,JQ861258,FJ513679,HM045793,EU703762,HM045785,FJQ00068,FJQ00065,FJ445430,HM045804,FJ445426,HM045809,AM258993,FJ807896,HM045799,HM045808,L37661,FJ445502,FJ445484,FJ807897,JN558834,AB455493,EF012359,EU244823,HM045800,FJ445511,HQ456254,HM045792,FJ513657,GQ428210,HMO45788,GU908223,FJ445445,EF027140,KF318729,AM258990,EU564334,GU013530,JX088705,HM045794,EF027138,AB455494,J0861255 |
| Chikungunya virus Wuerzburg | NC_004162 | vertebrates,invertebrates, human | 1 | Togaviridae,Alphavirus,Chikungunya virus | | EU037962 |
| Chize virus | NC_005214 | vertebrates,invertebrates, human | 1 | Bunyaviridae,Phlebovirus,Uukuniemi virus | seg. L | JF838324 |
| Chize virus | NC_005220 | vertebrates,invertebrates, human | 1 | Bunyaviridae,Phlebovirus,Uukuniemi virus | seg. M | JF838325 |
| Chize virus | NC_005221 | vertebrates,invertebrates, human | 1 | Bunyaviridae,Phlebovirus,Uukuniemi virus | seg. S | JF838326 |
| Colorado tick fever virus | NC_004180 | vertebrates,invertebrates, human | 1 | Reoviridae,Coltivirus,Colorado tick fever virus | seg. 9 | AF000720 |
| Colorado tick fever virus | NC_004181 | vertebrates,invertebrates, human | 1 | Reoviridae,Coltivirus,Colorado tick fever virus | seg. 1 | AF133428 |
| Colorado tick fever virus | NC_004182 | vertebrates,invertebrates, human | 1 | Reoviridae,Coltivirus,Colorado tick fever virus | seg. 2 | AF139758 |
| Colorado tick fever virus | NC_004183 | vertebrates,invertebrates, human | 1 | Reoviridae,Coltivirus,Colorado tick fever virus | seg. 3 | AF139759 |
| Colorado tick fever virus | NC_004184 | vertebrates,invertebrates, human | 1 | Reoviridae,Coltivirus,Colorado tick fever virus | seg. 4 | AF139760 |
| Colorado tick fever virus | NC_004185 | vertebrates,invertebrates, human | 1 | Reoviridae,Coltivirus,Colorado tick fever virus | seg. 5 | AF139761 |
| Colorado tick fever virus | NC_004186 | vertebrates,invertebrates, human | 1 | Reoviridae,Coltivirus,Colorado tick fever virus | seg. 6 | AF139762 |

-continued

| Taxonomy | NCBI Reference Sequence ID | Host | No. of Genomes | Lineage | Segment Count | Genbank Accession ID |
|---|---|---|---|---|---|---|
| Colorado tick fever virus | NC_004187 | vertebrates,invertebrates, human | 1 | Reoviridae,Coltivirus,Colorado tick fever virus | seg. 7 | AF139763 |
| Colorado tick fever virus | NC_004188 | vertebrates,invertebrates, human | 1 | Reoviridae,Coltivirus,Colorado tick fever virus | seg. 8 | AF139764 |
| Colorado tick fever virus | NC_004189 | vertebrates,invertebrates, human | 1 | Reoviridae,Coltivirus,Colorado tick fever virus | seg. 10 | AF139765 |
| Colorado tick fever virus | NC_004190 | vertebrates,invertebrates, human | 1 | Reoviridae,Coltivirus,Colorado tick fever virus | seg. 12 | U53227 |
| Colorado tick fever virus | NC_004191 | vertebrates,invertebrates, human | 1 | Reoviridae,Coltivirus,Colorado tick fever virus | seg. 11 | U72694 |
| Crimean-Congo Hemorrhagic Fever virus strain China | NC_005302 | vertebrates,invertebrates, human | 4 | Bunyaviridae,Nairovirus,Crimean-Congo hemorrhagic fever virus | seg. S | AF358784,AF354296, AF362080,AY029157 |
| Crimean-Congo hemorrhagic fever virus | NC_005300 | vertebrates,invertebrates, human | 50 | Bunyaviridae,Nairovirus,Crimean-Congo hemorrhagic fever virus | seg. M | DQ211634,DQ211637,DQ206448,HQ378185,HQ378187,AB069675,AF350448,AB069672,DQ094832,AB069670,JN572085,AF467769,DQ157174,DQ211625,AY900145,AJ538199,AB069673,DQ211631,AY900144,AB069671,DQ211630, AB069669,DQ157175,AY900143,AY223476,DQ211635,AY900141,DQ211632,AF467768,AF350449,AY900142,DQ21 1626,DQ446216,JN572086,AB069674,DQ211627,EU037902,DQ211628,JN572084,AJ538197,JN572083,DQ21 1633,U39455,AY675511,AY179962,HQ378184,AY179961,DQ211636, DQ446215,DQ211629 |
| Crimean-Congo hemorrhagic fever virus | NC_005301 | vertebrates,invertebrates, human | 32 | Bunyaviridae,Nairovirus,Crimean-Congo hemorrhagic fever virus | seg. L | HQ378182,DQ211621,EU044832,AY389508,AY947890,DQ076412,DQ21 1620,DQ211616,DQ211613,AY947891,DQ211614,DQ211617,AY675240,AY995166,DQ211615, |

| Taxonomy | NCBI Reference Sequence ID | Host | No. of Genomes | Lineage | Segment Count | Genbank Accession ID |
|---|---|---|---|---|---|---|
| | | | | | | HQ378180,DQ211162 2,KC344855,DQ2116 24,DQ076417,DQ211 619,DQ211612,HQ37 8183,DQ099335,DQ2 11623,AY389361,AY 720893,AY422209,D 0076414,HQ378181, DQ211618,AY422208 |
| Crimean-Congo hemorrhagic fever virus | NC_005302 | vertebrates,invertebrates, human

| Taxonomy | NCBI Reference Sequence ID | Host | No. of Genomes | Lineage | Segment Count | Genbank Accession ID |
|---|---|---|---|---|---|---|
| Deer tick virus | NC_003687 | vertebrates, invertebrates, human | 1 | Flaviviridae,Flavivirus,Powassan virus | — | 8190,AB262759,AB7 01773,JQ308188,FJ5 02995 |
| Dengue virus | NC_002640, NC_001475, NC_001474, NC_001477 | vertebrates, invertebrates, human | 22 | Flaviviridae,Flavivirus,Dengue virus | — | AF311056 CS805346,CS479167, CS477304,CS477305, CS477264,CS479203, JN054255,CS805343, JN054256,CS477263, CS477302,CS477265, CS479165,CS479202, CS479204,CS805344, CS479206,CS479205, CS805348,CS805345, CS477306, CS805347 |
| Dengue virus 1 | NC_002640 ,NC_001475 ,NC_001474 NC_001477 | vertebrates, invertebrates, human | 1456 | Flaviviridae,Flavivirus,Dengue virus | — | EU482708,GU131721, HM181969,FJQ24443, FJ744701,GU056031, HM488255,FJ8984 12, FJ410186,FJ6398 02, EU081229,KJ1893 62, JQ045632,GQ199 842, EU081244,FJ639 682, JN638340,GU13 1827, JQ915079,EUO 81254, FJ410274,GU1 31834, GQ868505,GQ 199800, FJ432746,FJ 410206, FJ410213,EU 482789, GU 131695,G U131839, GU131820,FJQ24447, FJ639683,FJQ24439, GQ 199849 , F J850099, F J898408, GU131716, GU13175 6,JQ915077, GU1319 26,DQ672557, GU131 749,JQ045664, GQ19 9772,FJ410201, FJ89 8418, JQ045642, FJ46 1340,FJ432727, HM1 81953,FJ639806, JQ0 45658,GU131835, FJ8 82531 ,AY732480, KJ1 89303, FJ898420, KF9 21911 ,JQ048541 , FJ8 50114,GQ199823, HM 181949,AY732482, |

| Taxonomy | NCBI Reference Sequence ID | Host | No. of Genomes | Lineage | Segment Count | Genbank Accession ID |
|---|---|---|---|---|---|---|
| | | | | | | JN819417,AY145122,EU482615,GU131863,EU081248,FJ639693,FJ687433,FJ882533,FJ882557,JQ045650,FJ410204,EU482529,AV732476,FJ882558,FJ410179,GQ199797,FJ410267,GU131770,EF025110,FJ410194,HQ891315,HM181936,JQ045628,FJ37329 7,FJ639812,EU66039 7,GQ868539,EU66604 18,GQ868633,FJ639 685,EU596501,FJ461 308,JF937606,FJ205 874,AB195673,EU08 1241,AB608787,EU0 81276,KJ189354,FJ4 10181,KJ189336,JN6 97058,GQ199840,JQ 045631,EF457905,AF 514889,DQ285558,G 0199806,FJ882579,F J882543,GQ868520, EU081251,GU131893 ,EU482795,EU08125 7,GU131751,FJ41023 6,GQ199814,GQ8686 12,EU677161,EU677 152,GU131681,KJ18 9321,GU131718,FJ18 5 0071,EU081250,GU1 31971,EU677160,GU 131779,HM63185 0,E U482480,GQ199788, FJQ24 55,FJQ24472, FJ432737,HM18194 5 ,EU081263,GU13168 5,EU482534,FJQ2443 4,KF184975,FJ88255 4,FJ461324,EU48281 0,HM181965,EU0812 28,FJ906963,GU1319 79,FJ384655,GQ199 832,EU482478,GU13 1792,JF937598,KJ18 |

| Taxonomy | NCBI Reference Sequence ID | Host | No. of Genomes | Lineage | Segment Count | Genbank Accession ID |
|---|---|---|---|---|---|---|
| | | | | | | 9325,FJ176780,FJ410254,FJ410214,GQ199785,GU131742,FJ182003,HQ332177,GU131748,FJ898433,FJ850073,FJ410209,EU482804,GU131895,D0672560,GQ199853,GU131773,FJ810419,FJ882528,FJ205881,GQ199815,FJ432719,JN205310,AB189120,GU131782,FJQ244333,GQ868632,FJ41021 6,GU131713,GU131319 58,GU131734,FJ898984 28,FJ410225,HG3164 82,FJ410180,KJ1893 68,GQ868537,HM181 937,FJ469908,EU660 419,KJ189302,FJQ24 431,EU482527,FJ410 248,FJ410175,FJ882 522,FJ547088,EU081 274,GU131964,EU48 2616,FJ410187,JN63 8341,EU482711,FJ41 0207,GU131833,EU6 77155,GQ868506,GQ 199808,EU081267,FJ 410238,KJ189342,EU 677164,FJ898384,KJ 189357,EU482528,G U131706,KJ189335,F J410220,GU131831, EU081240,JQ045656 ,FJ882555,FJQ24425, FJ882536,GU056033, GU131890,FJ182024, JF937645,FJ882524, EU081232,JQ045666 ,HQ624983,GU13178 8,GU131762,EU4827 14,FJ461317,FJ8825 49,GU131961,GU131 714,HM469968,EU67 7170,EU482801,GU1 31772,GU131760,DQ |

| Taxonomy | NCBI Reference Sequence ID | Host | No. of Genomes | Lineage | Segment Count | Genbank Accession ID |
|---|---|---|---|---|---|---|
| | | | | | | 285562,GU131694,AF311956,AY726552,FJ410230,FJ850103,J0287662,GQ199802,JF937597,EU596503,JF937603,FJ182036,FJ461307,HQ332182,GU131682,EU482493,FJ882518,HM181968,FJ205875,AY713473,GU131811,HM181955,FJQ24423,AY732479,FJ850090,FJ898431,FJ410253,EU677139,FJ410276,EU081249,GU131755,GU131746,GQ868529,FJ882529,JQ915076,FJ882521,GU131704,FJ639677,AB608788,JF937612,GQ199851,FJ410182,FJ373305,FJ850102,DQ672562,FJO24435,EU677174,GU131806,EF122231,EU482536,HM181966,FJ410245,JF937651,AY732481,GU131740,KJ189334,FJ205882,GU131744,AF350498,KJ189341,EU482797,GQ199833,GQ199811,DQ672558,FJ410264,FJ882534,JQ045652,FJ898398,FJ390382,JF937618,KJ189304,EU677150,GQ868567,FJ410240,FJQ24448,FJ882559,GQ868510,GQ868610,FJ410235,EU677176,EU482790,GU131699,EU482824,JQ045662,AF514883,FJ882538,HM181944,GQ199786,GQ199828,GU131957,EU596502,GQ868686,02,JN819423,FJ8983 |

| Taxonomy | NCBI Reference Sequence ID | Host | No. of Genomes | Lineage | Segment Count | Genbank Accession ID |
|---|---|---|---|---|---|---|
| | | | | | | 87,FJ432744,FJ4613 10,KJ189322,GQ199 839,FJ182022,GQ19 9812,AY722803,FJO2 4444,GU131697,FJ89 8383,FJ182034,GU05 6032,HM181947,EU4 82812,GQ868561,FJ 639673,FJ410231,GU 131790,AF298808,H G316481,FJ898382, GQ868607,EU48248 7,FJ639687,EU48279 8,FJ547068,HQ33218 1,FJ410289,GU13168 0,FJ639691,GU13196 5,JF937602,AF51311 0,JN819415,GU1317 66,JQ675358,FJ4327 36,EU482591,AB178 040,FJ898416,GU131 803,FJ461327,FJ410 239,FJ898430,KF955 446,FJ639821,KJ189 367,JQ045648,FJ873 810,EU081246,GU13 1759,EU482715,FJ88 2526,GQ868605,GU1 31715,FJ185077,GU1 31810,FJ639688,FJ4 32732,GU131977,FJ4 61339,EU081226,GU 131817,GU131778,FJ 898429,EU482507,A Y713476,FJ390383,H M181961,JQ287663, FJ639797,EU677172, FJ898379,GQ199859 ,FJ850100,GU131750 ,HM469966,FJ54706 5,GQ199777,JF9376 14,GU131757,FJ4613 06,GQ868524,GU131 894,GQ199844,EU08 1270,FJ461336,JN63 8344,GQ199807,EU6 77154,GU131727,DQ 285559,EU660403,E |

| Taxonomy | NCBI Reference Sequence ID | Host | No. of Genomes | Lineage | Segment Count | Genbank Accession ID |
|---|---|---|---|---|---|---|
| | | | | | | U677163,FJ205873,F JQ24480,GU131919,F JQ24445,EU482540, GQ199816,FJ461316 ,FJ898388,EU482793 ,EU081231,JQ04566 7,GU131805,GU1317 84,FJ461313,FJ4102 34,JQ045638,EU081 265,FJ410188,AY835 999,FJ898413,HM18 1950,GQ199850,GU1 31722,KF921935,FJ8 98419,FJQ24436,FJ3 90381,FJQ24479,EU4 82491,AB074760,FJ8 98392,JF937650,KC1 31141,JQ915075,GU 131796,EU687251,E U677173,GQ199781, EU482809,FJ898397, AF514885,EU677171 ,FJ478458,FJ410275, GU131783,EU482511 ,GU131826,GQ86851 4,FJ410281,JQ04566 0,FJ882556,GU13170 8,GQ868535,HM4699 67,GQ199783,FJ432 723,FJ898422,EU482 828,GU131693,FJ562 106,GQ199771,GU13 1753,EU726779,GQ1 99846,FJ882515,FJ4 10174,GQ199792,EU 280167,FJ850093,HQ 166035,GQ199829,G 0868500,GU131728, KJ189346,FJ432734, FJ390374,JQ045636, DQ672563,JQ045647 ,FJ898376,FJQ24441, GQ868618,JN638342 ,GU131696,FJ882520 ,FJ639735,HM18196 7,EU482817,GQ1998 31,JF937611,FJ4699 09,GQ199775,FJ410 |

| Taxonomy | NCBI Reference Sequence ID | Host | No. of Genomes | Lineage | Segment Count | Genbank Accession ID |
|---|---|---|---|---|---|---|
| | | | | | | 192,JQ045626,FJ410263,KJ189318,FJ182027,GU131822,GQ868637,GQ868522,JF937619,FJ687428,GU131921,FJ410290,EU482592,FJ898374,GQ868502,EU677140,GU131764,EU482520,GQ199824,GQ199821,FJ882516,GQ8686814,GU131836,FJ898426,JF937609,EU482531,JQ915072,FJ639679,GU131980,GQ868512,FJQ24485,KJ189329,GU131687,FJ639820,FJ410262,JQ045649,AF514878,EU726777,JQ045668,EU081234,GQ199773,FJ639678,FJ410198,KJ189359,GU131963,GU0868525,FJ432739,GQ199827,AB519681,AY713475,FJ882563,JQ045643,FJ639811,FJQ24427,EU482820,KJ189338,EU081262,FJ410232,FJ461303,FJ639672,FJ687430,AY732474,JN903581,FJ410279,GQ868639,FJ461332,GU056029,EU482476,GQ199979,GU131889,GQ199843,JQ287664,EU081260,KJ189332,FJ906965,JQ045644,GU131769,EU249492,EU482516,JN819411,GQ199799,JQ287660,JF937613,AY726551,FJ182031,DQ285560,GU131798,GU131922,GQ199836,KJ189327,KJ189339,EU482796,GQ199798,AY72280 |

| Taxonomy | NCBI Reference Sequence ID | Host | No. of Genomes | Lineage | Segment Count | Genbank Accession ID |
|---|---|---|---|---|---|---|
| | | | | | | 2,FJ639676,GU13195 6,EU482823,EU4828 03,GU131774,HM181 954,AY708047,EU66 0394,EU482619,GQ1 99793,JN000935,GQ 868519,FJ410227,G 868532,GQ868517, GQ868560,FJ410255 ,KJ189344,EU482537 ,EU081271,FJ410185 ,GQ868564,EU72678 1,KJ189337,FJ87380 9,EU081253,GU1318 18,HM181948,JQ045 665,FJ639694,FJ410 286,GU131887,GU13 1829,FJ882570,FJ63 9823,FJ461312,FJ88 2568,EU482501,FJ41 0273,JQ045630,GQ1 99805,GQ868513,FJ 410282,EU482819,FJ 410197,GU131786,K J189345,GU131733,F J898403,HQ891314,F JQ24457,EU081238,K J189348,FJ898377,E U726780,HQ166036, FJ898411,FJ410242, FJ882540,GQ199810 ,FJ882517,KJ189364, JF937610,GU131812

| Taxonomy | NCBI Reference Sequence ID | Host | No. of Genomes | Lineage | Segment Count | Genbank Accession ID |
|---|---|---|---|---|---|---|
| | | | | | | FJQ24429,GQ868563,FJ898423,GU131966,GU131741,GU131823,GU131730,FJQ244451,EU179860,KJ1189358,EU249494,JN697056,FJ547060,GU131842,GU131752,EU482806,GU131802,DQ672559,EU482521,EU482815,KJ189366,KJ189347,EU081264,FJ882551,GU131809,FJ205876,GU131720,FJ205883,KC759167,GU131972,GQ868619,GU131703,HM631855,KC131140,HM181959,AF514876,FJ432725,JN638343,GQ199787,EU482811,FJQ244437,EF032590,FJ882542,FJ461325,EU482525,GU131799,JF937616,FJ639681,DQ672556,FJ182020,FJ898401,IQ287661,FJ410247,EU482822,EU482517,EU660412,JQ004563,FJ859029,HM631852,JN903580,GQ199803,EU081259,EU081273,HQ332178,FJ182033,GU131725,GU131808,KJ189349,FJ547063,AB189121,EU482483,FJQ244463,GU131692,GQ199852,FJ639675,GU131819,JF937608,EU081279,GQ199819,FJ882548,EU482518,FJ410261,GU131981,FJ687426,EU677165,FJQ244432,GQ868499,KJ189316,GU131777,KJ189356,FJ639796,FJ410278,FJ182025,KJ189393 |

| Taxonomy | NCBI Reference Sequence ID | Host | No. of Genomes | Lineage | Segment Count | Genbank Accession ID |
|---|---|---|---|---|---|---|
| | | | | | | 52,EU081233,GQ868 611,EU482538,GU13 1962,KF955427,JN81 9405,AF309641,HQ8 91313,FJ898381,EU4 82712,GU131960,AB 608786,GU131723,E U081277,EU482800, FJ850104,EU081252, FJQ24430,EU726782, KJ189331,FJ898417, EU596504,GU131678 ,GU131838,EU48250 0,HQ332183,GU1319 67,JF937604,FJ4613 18,FJ182030,FJ1820 18,FJ432729,FJ4102 50,GU131739,AY726 550,KF921942,JN819 410,KF921933,EU48 2530,GQ199796,GU1 31712,AY726554,FJO 24440,FJ461319,EU2 49491,EU482509,GQ 868536,FJQ24426,GU 131795,GU131781,E U60393,KJ189343, GU131735,EU482713 ,EU482482,FJ410226 ,EU081239,GQ86851 1,FJQ24453,HM1819 63,FJ882560,JF9376 44,FJ547086,FJ8825 44,GQ199834,GQ199 779,EU482514,GQ86 8508,EF122232,FJ89 8391,EU482505,JN81 9425,FJ639670,FJ20 5884,GU131804,FJ89 8404,FJ410190,FJ41 0196,GU131732,AY1 45123,FJ687431,EU0 81278,FJ810415,EU4 82503,FJ873814,FJ8 98410,FJ882525,EU0 81235,GQ199809,FJ 639680,FJ410257,KF 955444,JF937635,EU |

| Taxonomy | NCBI Reference Sequence ID | Host | No. of Genomes | Lineage | Segment Count | Genbank Accession ID |
|---|---|---|---|---|---|---|
| | | | | | | 48717,FJQ24481,FJ882539,JF937617,FJ410243,AF180818,JQ045661,GQ199873,J0045640,FJ882530,FJ182002,FJ882562,JN819412,GU131828,JN819402,GU131738,HM181958,EU671751,GU131888,JQ045654,EU482526,EU482535,KJ189317,FJQ24438,EU677167,EU482489,KJ189365,GQ868601,FJ898407,HM181951,EU081275,AY732478,JQ287667,FJ410277,AY762084,FJ639696,FJ410283,EU482502,JQ045653,FJ639674,EU482610,FJ898414,FJ882535,GU131710,FJQ24462,FJ898373,GQ868538,EU482807,EU482827,FJQ24449,AY75711,EU482484,FJQ24446,FJ898375,KJ189313,FJ882569,GQ868570,AY732477,EU081280,FEU482805,E

| Taxonomy | NCBI Reference Sequence ID | Host | No. of Genomes | Lineage | Segment Count | Genbank Accession ID |
|---|---|---|---|---|---|---|
| | | | | | | 6,GU131691,JN6383 38,JQ915074,GU131 982,GQ868528,FJ41 0244,EU482792,HM1 81957,FJ850081,GU1 31785,FJ188219,JQO 45641,GU131700,FJ8 98406,FJ373296,GU1 31825,AY726555,EU 179861,FJ410260,FJ 461330,FJ882565,FJ 432733,GU131736,G 0199856,FJ390379,F J882537,KJ189333,E U081243,FJ410210,A Y145121,GQ199801, JN903579,K

| Taxonomy | NCBI Reference Sequence ID | Host | No. of Genomes | Lineage | Segment Count | Genbank Accession ID |
|---|---|---|---|---|---|---|
| | | | | | | 0191,GQ199820,AB204803,GU056030,HM181939,FJQ24482,GU131717,FJ687429,FJ410258,GU131747,GU199774,FJ182028,EU482512,EU482532,FJQ24456,KJ189323,JN819413,AF180817,FJ639740,GQ199835,GQ199789,FJ63974 3,EU677166,JQ045639,FJ882550,JQ045634,EU482496,KJ189369,AY726549,EU482488,KF921949,GQ199841,GQ868609,GQ868569,EU482709,FJ850087,GQ868509,GU131686,FJ898396,EU482821,JQ915071,EU848545,FJ461333,GU868565,EU677169,EU726778,FJ639824,EU482617,FJQ24484,FJ850084,FJ410268,FJ898395,GQ199790,GU131719,JQ045645,GQ199825,GU131801,JQ287665,EU677175,FJ882564,EU482826,FJ410265,EU249493,FJ461320,FJ882546,GU131813,EU359008,GU131684,FJ639813,HM181938,FJQ24428,FJ850069,HQ624984,AF311957,GU131688,EU482477,EU482492,EU482707,FJ461328,GU131925,FJ410249,GQ868531,FJ850075,FJ898409,FJ390378,JN903578,GU131767,AF298807,EU482710,FJ882547,FJ898390,EU482485,GQ868527,FJ410027 |

| Taxonomy | NCBI Reference Sequence ID | Host | No. of Genomes | Lineage | Segment Count | Genbank Accession ID |
|---|---|---|---|---|---|---|
| | | | | | | 2,GQ199847,EU0812 |
| | | | | | | 68,JN697057,HM631 |
| | | | | | | 851,GQ199817,FJ41 |
| | | | | | | 0287,FJ432747,EU67 |
| | | | | | | 7178,JQ915073,GU1 |
| | | | | | | 31983,GU131729,GU |
| | | | | | | 131683,KF921934,FJ |
| | | | | | | 898425,FJ639815,EU |
| | | | | | | 482508,EU677158,FJ |
| | | | | | | 390380,KJ189314,FJ |
| | | | | | | 882553,HM181956,G |
| | | | | | | 0199855,AB074761, |
| | | | | | | FJ182023,FJ898415, |
| | | | | | | KJ189326,EU482618, |
| | | | | | | EU482499,EU660391 |
| | | | | | | ,FJ898378,FJ639695, |
| | | | | | | GU131814,FJ898402, |
| | | | | | | HM181943,GU13179 |
| | | | | | | 1,FJ882566,DQ19357 |
| | | | | | | 2,GU131840,JN8194 |
| | | | | | | 14,GU131832,EU482 |
| | | | | | | 524,EU482706,GU13 |
| | | | | | | 1775,HM181960,FJ7 |
| | | | | | | 44702,FJ906964,EU4 |
| | | | | | | 82818,AF226686,EU |
| | | | | | | 482497,IQ045629,G |
| | | | | | | 0868635,JF937600,E |
| | | | | | | U081237,GU131824, |
| | | | | | | FJQ24450,GU131701, |
| | | | | | | FJ410252,GQ199794 |
| | | | | | | ,EU660395,AY27766 |
| | | | | | | 4,GQ868498,KJ1893 |
| | | | | | | 19,HQ166037,FJ8825 |
| | | | | | | 27,GQ868534,GQ868 |
| | | | | | | 503,KJ189315,GQ19 |
| | | | | | | 9875,EU482825,GU1 |
| | | | | | | 31737,FJ390388,FJ8 |
| | | | | | | 98421,FJ850068,FJ5 |
| | | | | | | 62101,GU131800,KJ |
| | | | | | | 189330,FJ410211,FJ |
| | | | | | | 432745,AB608789,E |
| | | | | | | U081266,AY732475, |
| | | | | | | AY277666,GQ199838 |
| | | | | | | ,GU131776,FJ882552 |
| | | | | | | ,GU131743,GU13197 |
| | | | | | | 8,FJ410246,EU48249 |
| | | | | | | 5,AF311958,EU4825 |
| | | | | | | 15,FJ639671,AY7134 |

| Taxonomy | NCBI Reference Sequence ID | Host | No. of Genomes | Lineage | Segment Count | Genbank Accession ID |
|---|---|---|---|---|---|---|
| | | | | | | 74,JN638337,GQ868608,FJ882532,FJQ24483,GU131689,EU660401,FJ898405,HM181940,KF955442,GU131973,EU482814,FJ898437,EU482791,AY206457,FJ687427,FJ898385,FJ639669,G0199818,KJ189355,U88537,FJ639692,EU081227,KJ189324,FJ898372,GQ398255,GQ868606,EU482716,AY726553,GQ199804,JQ287666,FJ898424,GU131821,FJ182026,HM181952,GU131797,FJ461341,JQ045663,FJ410183,EU482486,JQ045663,EU081245,AF226685,EU482799,FJ432735,JQO45646,GQ199837,FJ390386,FJ562105,EU482718,GU131968,FJ639690,FJ906728,FJ410269,EU677168,H0332180,GQ868562,FJ547087,FJ432730,JQ045657,GQ199845,EU249490,GU131711,EU863650,GQ199795,FJ898394,EU081247,FJ639684,GQ199782,GU131920,FJ410251,FJ410203,FJ432721,FJ469907,GU131969,FJ882561,FJ410266,GU131841,EU677159,HQ332179,EU482498,KJ189328,GQ199813,GU131754,G0199858,FJ850101,KJ189351,FJ850113,GU131794,EU081230,HM181962,GU131892,FJ410205,KJ189362 |

| Taxonomy | NCBI Reference Sequence ID | Host | No. of Genomes | Lineage | Segment Count | Genbank Accession ID |
|---|---|---|---|---|---|---|
| | | | | | | 3,GU131837,EU4825 06,JF937607,FJ1820 29,FJ410285,FJ6398 19,HM181941,GU131 709,GQ199776,FJ41 0173,EU482479,EU4 82510,GU131731,FJ4 10222,EU687247,GQ 868518,FJ461323,EU 482504,GU131679,G Q868613,GU131984, EU482609,GU131970 ,FJ882567,GQ19982 6,FJQ24464,FJ17677 9,EU677153,GU1319 48,GU131724,HM181 942,FJ432720,FJ639 741,FJ410270,FJ562 104,FJ898448,GQ19 9877,JF937596,EU48 2802,FJ410212,GQ8 68507,EU677177,KJ1 89312,EU081242,FJ4 78457,GU131793,GU 131787,GU131816,FJ 410184,GU131705,E U081258,GQ199830, EU677156,GU131765 ,GQ199872,FJ41021 8,EU482522,JN81940 3,AY732483,EU0812 36,JF937615,EU4824 81,JF459993,GU1318 15,KJ189307,GU131 789,FJ410199,AY277 665,FJ461315,HM48 8256,FJ898427,FJ63 9808,FJ639689,JQ04 5655,FJ432740,GQ8 68615,FJ639686,GU1 31745,DQ672564,EU 482533,FJ639794,G 0868568,GQ199857, EU482808 |

-continued

| Taxonomy | NCBI Reference Sequence ID | Host | No. of Genomes | Lineage | Segment Count | Genbank Accession ID |
|---|---|---|---|---|---|---|
| Dengue virus 2 | NC_002640,NC_001475,NC_001474,NC_001477 | vertebrates,invertebrates, human | 1024 | Flaviviridae,Flavivirus,Dengue virus | — | FJ850074,JF730051, EU596490,EU482725,EU482622,JN819407,GU131931,EU482762,FM210226,GU131864,GU131896,EU677148,EU687246,EU596500,EU482444,EU529701,GQ868552,EU660398,GQ398270,FJ744716,EU482675,FJ744705,EU482548,FJ639718,GQ868557, EU569695,EU569699,GQ868604,GQ868646,KC294212,EU482590,EU596488,FJQ24474,FM210237,EU482772,GQ398296,JN819408,GQ398299,GU131900,EU482761,EF105381,EU920836,EU482647,FJ639709,H0541788,AF100459, FJ882602,EU482606, KF041237,EU482573,FJ898454,EU482560,JXQ79688,HQ332185,EU920834,FJ182014,EU482679,FJ898467,AB479042,FJ906958,EU920849,EU569702,EU596489,EU596498,FJ898435,EU482623,HM582103,EU482643,EU687225,HQ705624,EU482569,EU482472,FJ906969,FJ850119,FJ639700,EU482673,EU482664,FJ024452,GQ398310,EU677142,GU131902, KF041235,FJ639837, FJ410215,AB122022, AF022439,FM210223,EF105387,JN819418,FJ687439,GQ868550,AF038402,FJ43272 |

| Taxonomy | NCBI Reference Sequence ID | Host | No. of Genomes | Lineage | Segment Count | Genbank Accession ID |
|---|---|---|---|---|---|---|
| | | | | | | 6,FJ639828,EU48265 7,GQ86859I,EU4827 48,EU482585,FJ6397 88,FJ639710,EU4825 72,AF169679,EF1053 84,HM582109,FJ850 085,EU482554,EU48 2542,EU482691,GQ3 98285,AF359579,KC 294206,FJ461321,EU 482759,AF204178,D 0181800,KF955360, FJ205885,FJ850064, GQ868515,EU48258 4,EU687242,FJ74471 0,FJ687445,FJ63983 1,EU482694,FJ89845 0,FJ744721,EU48254 4,EU482698,EU4826 29,FJ205880,EU4824 64,GU131959,EU596 487,GQ398261,EU48 2579,GU131899,GQ1 99894,GQ199890,GU 131880,GU131883,E U687228,EU482471,J X96638O,FJ898460,G Q398268,GU131974, FJ744719,EU569694, EU482631,GQ39827 5,FJ639705,FJ89843 8,GQ199866,EU6771 38,GQ868603,EU920 845,EU482665,GU13 1885,EU660406,EU5 96499,FJ744709,JN8 19421,JX286525,AY7 44147,FJ906967,AY0 37116,JF733045,FM2 10227,KF041232,JF3 57906,EU677149,EU 482697,GQ398259,A F169685,EU482734,F J639699,.AB479041,E U482449,EU660404, EU482742,GQ86855 8,EU677144,KC2942 18,GQ398295,FM210 |

| Taxonomy | NCBI Reference Sequence ID | Host | No. of Genomes | Lineage | Segment Count | Genbank Accession ID |
|---|---|---|---|---|---|---|
| | | | | | | 221,KF955359,GQ868631,EU920840,KC294215,FJ850076,M19197,EU482670,JF327392,GQ252677,FJ744704,EU482550,JN819416,EU482752,JQO45684,GQ398265,EU482787,GQ868588,AF100464,GQ868545,EU482553,GQ398300,EU920835,EU482571,GQ252676,GQ868600,EU482722,FJ850121,EU920838,JXQ79690,EU482660,GQ398308,GQ398258,EU482668,GU131884,FJ639698,HQ332184,KF360005,KC294213,AF100460,AF169682,GQ398314,FJ687434,GQ868624,AY702035,FJ687438,FJ898434,EU482620,EU482463,EU482650,EU179858,KJ189309,EU482751,HM582113,EU482754,HQ332190,KF955362,KJ189308,AY702034,FJ810418,DQ181797,EU854294,GQ39829,FM210216,AF100466,EU482784,FJ390391,EU482758,EU529706,GQ398289,FJ639704,AF169688,HQ733861,FJ639834,GQ398271,KJ189311,GU131886,GQ868540,FJ898432,FM210225,HQ634199,EU482599,FJ373301,EU687241,GQ868549,FM210245,GQ199899,FJ744714,GU131901,FJ906956,FJ850067,EU482474,EU482729,EU4 |

| Taxonomy | NCBI Reference Sequence ID | Host | No. of Genomes | Lineage | Segment Count | Genbank Accession ID |
|---|---|---|---|---|---|---|
| | | | | | | 82628,EU687214,FJ8 10409,EU482705,FJ8 50105,EU482700,FM 210210,GU131975,G 0868598,JX475906,F J744712,EF105383,E U596497,FJ639706,G 039829B,FJ639734, GQ398260,EU92082 9,EU482782,EU4827 21,HQ541794,KC294 210,EU482704,AB12 2021,EU920847,GQ1 99895,EU677145,FJ4 61305,EU482576,EU 726776,FJ410228,EU 482666,EU482582,F M210233,GU131929, JQ045686,FJ850117, EU482773,EU482723 ,FM210220,EU48268 5,AY702037,FJ43272 4,FJ850112,U87412, AB122020,FJQ24461, EU569715,DQ181801 ,EU482446,GQ86855 1,GQ199898,KC2942 21,EU482658,FJ8500 53,JX286526,FJ6874 44,EU687240,EU920 846,M84727,KC2942 02,AF100463,FJ8501 06,EU482669,FJ3903 90,EU569718,EU726 767,EU482785,HQ54 1798,EU482601,EU5 96496,FJ850088,EU5 69713,JX470186,FJ4 10224,FJ687443,EU4 82547,FJ687447,EU6 60416,FJ906962,DQ4 48231,GQ199892,FJ 906968,JF730046,G 0868599,FJ182012,E U482763,KC294205, EU569698,EU482625 ,FJ547067,JF730053, FJQ24477,EU482775, |

| Taxonomy | NCBI Reference Sequence ID | Host | No. of Genomes | Lineage | Segment Count | Genbank Accession ID |
|---|---|---|---|---|---|---|
| | | | | | | EU482781,FJ850091, EU569720,EU482737, DQ181798,EU660399, EU569706,EU687249, GQ398272,JX286521, FJ461314,DQ181802, GQ398305,EU482568, GQ868620,EU920839, HM582114,FJ898453, FJ687437,EU482473, GQ868625,FJ850120, EU726775,EU482634, EU179859,FJ850082, FJ410221,EU482770, FJ639732,HM631867, GQ868596,FM210207, HM582111,FM210224, GQ398266,GQ398278, FM210215,KC294219, EU687217,EU482451, FM210218,EU726770, EU482468,GQ868556, EU482788,EU569708, GU131927,EU482580, EU482637,EU482743, KC294209,AF169680, FJ850054,GQ398280, FJ639809,FJ390384, FJQ24475,GQ398293, GU369819,EU482570, AY858035,EU569721, FJ410219,EU056812, HQ541787,EF105382, EU482726,EU482672, EU687245,FJ687435, AF169686,EU569703, KJ189370,KC294222, KC294207,EU920843, FJ850108,JF357905, GQ868543,EU482638, EU482541,FM210211, GQ398309,AF100461, EU687238,FJ373300, KC294201,GQ868590, EU596495,EU482701, KF955369,AB543624, |

| Taxonomy | NCBI Reference Sequence ID | Host | No. of Genomes | Lineage | Segment Count | Genbank Accession ID |
|---|---|---|---|---|---|---|
| | | | | | | JX286517,EU003591,EU482769,EU482749,EF051521,EF105385,EU482688,FJ639697,JF730050,GQ398288,FJ410200,GU131928,JN796245,FJ410208,FJ850118,DQ181798,FJ850060,FJ373299,GQ398311,GQ868542,EU482552,EU482760,FJ639836,EU687236,EU482602,GQ398273,EU482577,FM210208,KF955364,DQ181805,EU687212,FJ850065,EU920844,FJ478459,EU687224,EU482662,AY702040,EU920833,GQ199896,GQ398302,HQ541799,EU482624,FJ205879,JQ955623,AF022437,FJ639703,AB189123,GQ868555,EU482699,EU179857,GQ868516,EU482583,FJ744706,EU482450,EU482603,EU920831,FJ687436,EU569701,EU482243,GQ398284,EU660414,FJ744722,GU131882,FJ410233,EU482695,FJ390385,KC131142,JN819420,FM210219,EU482730,GQ398279,EU677141,EU482475,GQ868638,FM210244,HM488257,FJ639717,FJ639833,EU482696,EU482744,FJ906957,HM582107,EU482587,KF955372,FJQ24454,EU677147,FJ744720,EU482633,EU687216,FJ898461,EU677137,GQ398290,GQ398276, |

| Taxonomy | NCBI Reference Sequence ID | Host | No. of Genomes | Lineage | Segment Count | Genbank Accession ID |
|---|---|---|---|---|---|---|
| | | | | | | EU687237,EU056810,HM631868,FJ56209 8,GU131930,GQ3982 63,EU482739,EU482 465,HM582101,FJ89 8479,EU482741,FJ68 7441,GQ868641,FJ7 44723,EF457904,EU 482702,EU482671,E U596486,EU482467, EU482551,EU482667 ,HQ999999,GQ39828 1,EU482656,KC9640 94,EU677143,EU569 707,EU482755,HM63 1865,EU482632,FM2 10231,GQ199868,FJ 744718,FJ639707,AJ 968413,FJ410217,EU 920841,HM582116,A F169681,EU482687,F J744743,KC294214,K C964093,EU687235, FJ226066,FJ205877, FJ810410,FJ850116, FJ639711,GQ398283 ,EU482649,FJ744724 ,FM210240,GQ39831 2,EU920832,GQ3983 01,KC294217,FJ6397 02,AF100465,FJ8500 63,KC294223,KF955 363,FJQ24458,AY776 328,GU131881,JQ04 5670,FJ850061,GU28 9914,FJ898477,EU08 1179,GQ868554,AF0 22435,FJ410241,EU5 69716,EU569711,EU 482783,M84728,KC2 94211,FJ898436,EU4 82466,GQ398257,EU 44713,GQ398257,EU 660413,AY85036,E U482642,EU621672, GU131947,EU482779 ,GQ199897,EU48273 5,FJ744715,AB18912 |

| Taxonomy | NCBI Reference Sequence ID | Host | No. of Genomes | Lineage | Segment Count | Genbank Accession ID |
| --- | --- | --- | --- | --- | --- | --- |
| | | | | | | 4,KC294200,EU5696 |
| | | | | | | 96,AF169683,EU596 |
| | | | | | | 483,FJ906959,KF955 |
| | | | | | | 366,GQ199900,EU48 |
| | | | | | | 2682,GQ398304,HQ5 |
| | | | | | | 41792,EU482678,FJ8 |
| | | | | | | 98439,EU596485,EF |
| | | | | | | 105389,DQ181806,F |
| | | | | | | M210232,EU482674, |
| | | | | | | FM210213,EU359009 |
| | | | | | | ,EU482626,KC29420 |
| | | | | | | 3,GU131879,HQ7056 |
| | | | | | | 25,EU482757,JX2865 |
| | | | | | | 23,EU687222,AB189 |
| | | | | | | 122,EU482684,HQ02 |
| | | | | | | 6763,EU482605,GQ8 |
| | | | | | | 68592,FJ850051,GU1 |
| | | | | | | 31924,EU482581,EU |
| | | | | | | 482646,HM582106,E |
| | | | | | | U482445,EF105386, |
| | | | | | | EU920830,JX286519, |
| | | | | | | EU482676,EU482644 |
| | | | | | | ,FJ547064,FJ410288, |
| | | | | | | EU569700,GQ39828 |
| | | | | | | 2,GQ398297,FJ4101 |
| | | | | | | 93,EU687215,EU482 |
| | | | | | | 689,GU131898,FM21 |
| | | | | | | 0238,FJ639708,JX28 |
| | | | | | | 6518,FJQ24473,KC29 |
| | | | | | | 4216,AF204177,FJ89 |
| | | | | | | 8465,JF730049,EU48 |
| | | | | | | 2724,HM582104,EU4 |
| | | | | | | 82659,EU482720,AF |
| | | | | | | 100467,KF955373,G |
| | | | | | | 0199893,FJ687446,E |
| | | | | | | U482586,FJ744725,E |
| | | | | | | U482641,EU660417, |
| | | | | | | KF041234,EU569697 |
| | | | | | | ,FJ906960,EU687227 |
| | | | | | | ,EU482747,FJ390389 |
| | | | | | | ,FJ639701,EU482776 |
| | | | | | | ,HM582108,FM21023 |
| | | | | | | 9,GQ868622,EU4827 |
| | | | | | | 80,FJ744708,EU5296 |
| | | | | | | 93,KF041236,GQ868 |
| | | | | | | 621,EU482556,GQ86 |
| | | | | | | 8640,EU687231,FJ20 |
| | | | | | | 5878,EU482774,FJ85 |

| Taxonomy | NCBI Reference Sequence ID | Host | No. of Genomes | Lineage | Segment Count | Genbank Accession ID |
|---|---|---|---|---|---|---|
| | | | | | | 0072,KF955401,EU6 |
| | | | | | | 87243,FJ639829,EU4 |
| | | | | | | 82654,FJ744703,AF0 |
| | | | | | | 38403,EU482578,EU |
| | | | | | | 482766,AF169678,G |
| | | | | | | 0398262,GQ868595, |
| | | | | | | AF208496,EU482777 |
| | | | | | | ,EU687250,GQ86855 |
| | | | | | | 3,KF955365,EU4824 |
| | | | | | | 70,JF730054,EU6871 |
| | | | | | | 99,GQ398267,EU482 |
| | | | | | | 594,HQ332188,EU92 |
| | | | | | | 0850,HM582115,EU4 |
| | | | | | | 82745,FM210202,FJ6 |
| | | | | | | 39822,FJ850050,FJ4 |
| | | | | | | 78455,JX286524,EU4 |
| | | | | | | 82627,FJ390387,EF1 |
| | | | | | | 05378,FJ687440,AF0 |
| | | | | | | 22436,EF105390,HM |
| | | | | | | 582112,EU569705,JX |
| | | | | | | 286520,EU482719,JX |
| | | | | | | 286516,EU482448,E |
| | | | | | | F105379,FM210217, |
| | | | | | | FJ850066,JF730044, |
| | | | | | | EU482630,HQ541793 |
| | | | | | | ,EU482645,EU05681 |
| | | | | | | 1,EU482469,EU4827 |
| | | | | | | 33,EU482636,FJ4102 |
| | | | | | | 91,GQ199901,JX286 |
| | | | | | | 522,GU131932,FJ898 |
| | | | | | | 451,JF730047,EU482 |
| | | | | | | 557,KJ189310,AY702 |
| | | | | | | 039,EU482639,FM21 |
| | | | | | | 0212,EU482683,GQ1 |
| | | | | | | 99874,FM210209,FJ6 |
| | | | | | | 39832,HM582102,KC |
| | | | | | | 294204,KF041233,H |
| | | | | | | M582105,EU687248, |
| | | | | | | FJ461311,FJ744745, |
| | | | | | | FM210228,AF022441 |
| | | | | | | ,KF955395,EU56971 |
| | | | | | | 9,FM210246,JF73004 |
| | | | | | | 8,EU482588,EU6604 |
| | | | | | | 05,HQ891023,GQ398 |
| | | | | | | 292,AF100468,GQ39 |
| | | | | | | 8274,FM210242,KC2 |
| | | | | | | 94208,GQ398294,EU |
| | | | | | | 482652,EU482690,H |

| Taxonomy | NCBI Reference Sequence ID | Host | No. of Genomes | Lineage | Segment Count | Genbank Accession ID |
|---|---|---|---|---|---|---|
| | | | | | | M582099,JX966379, EU081180,JN819422, EU482600,JN819424, HQ332187,HQ89102 4,EU482562,EU6872 32,FJ906966,EU6604 15,EU687213,HM181 971,EU482546,KF95 5402,GQ398264,EU6 8724,AY702036,EU 482753,EU482621,FJ 547090,AY702038,F M210206,EU529694, FM210229,JQ955624 ,FJ898478,EU482640 ,FJ882594,EU482661 ,FJ744741,GQ86862 3,EU482608,GQ3983 07,FJ859028,JXQ796 94,AF169687,GU131 897,EU569692,AJ487 271,EU920828,EU48 2593,GQ868589,FJ7 44707,FM210203,FJ6 39783,EU482655,EU 482728,FJ639835,DQ 181804,M29095,EU6 87223,EU920837,FM 210234,FJ898466,EU 482750,GQ398303,F M210243,EU569709, EU854293,EU482653 ,EU482746,FJ410259 ,EU081177,EU48265 1,FJ850062,GQ8685 44,HQ332189,EU677 146,EU482736,EU68 7230,GQ868597,EU4 82575,EU482738,EU 482740,FM210236,E U482604,AF489932,F J898449,HQ541786, EU482731,EU569704 ,FJ687442,EF105380 ,FJ639733,EU781135 ,FJ850078,FJ410202, JF730052,FJ410195, EU529700,AF022438 |

| Taxonomy | NCBI Reference Sequence ID | Host | No. of Genomes | Lineage | Segment Count | Genbank Accession ID |
|---|---|---|---|---|---|---|
| | | | | | | ,AF100469,EU48270 3,GQ398269,FJ7447 17,EU482598,JN3684 76,HM582100,FM210 230,FM210241,AF11 9661,HM631866,EU4 82680,GU131843,EU 482589,FM210204,E U687220,GQ199869, EU596484,AF100462 ,GU131955,EU48266 3,EU482607,FJ87380 8,EU482686,GQ3982 87,GQ868541,FJ906 961,EU569714,EU48 2549,EU482447,EU4 82574,EU920848,EU 920842,FJ410223,EU 482648,FM210235,E U529695,EU081178, KC294220,FM210214 ,EU482756,FJ410237 ,EU482692,FJ744742 ,JF357907,EU569717 ,FJ850107,FJ461309, EU482786,EU482732 ,EU482693,FJ744744 ,DQ181803,AF27661 9,EU569710,EU5964 91,FJ850115,EU4826 35,EU569712,HQ332 186,FJ639830,HM58 2117,EU482597,EU6 60400,FJ873811,HM 582110,FJ467493,JF 730055,GQ868497,F J810412,EU482565, GQ398286,FM21020 5,GQ398277,EU4825 45,GQ398313,GQ398 306,M20558,EU4827 78,EU482727,EU482 681,EU687229,AF16 9684,FJ810411,AF02 2434,EU569693,EU4 82561,JN819419,FJ8 82593,KC964095,FJ8 98452,FJ744711,EF1 |

-continued

| Taxonomy | NCBI Reference Sequence ID | Host | No. of Genomes | Lineage | Segment Count | Genbank Accession ID |
|---|---|---|---|---|---|---|
| | | | | | | 05388,EU482771,FM210222,AF022440 |
| Dengue virus 3 | NC_002640,NC_001475,NC_001474,NC_001477 | vertebrates,invertebrates, human | 785 | Flaviviridae,Flavivirus,Dengue virus | — | HQ705619,KF955479,GQ199887,EU482558,EU081202,FJ882578,FJ639714,KJ189293,EU081219,FJ461338,KF955457,EU687239,GU131954,FJ639724,EU660407,EU529704,AB214882,FJ639779,KF041258,FJ850080,AB189125,FJ639760,EU687221,GQ868617,EU482460,HM631859,JF937624,FJ182040,KF955463,GQ868572,GU131867,FJ850086,HM181977,AY676351,EU660408,EU081221,AY858043,HQ541791,EU482457,JF937643,FJ182005,JF937631,JF937633,FJ639789,M93130,FJ547074,JQ045691,GU131933,FJ432743,FJ547069,FJ373302,GQ868629,KJ189299,JQ045693,FJ639762,JF808126,GU131873,EU482596,JF920408,FJ432731,FJ744726,KF955333,FJ639758,FJ639803,GU131859,HQ705611,FJ432741,FJ205871,JF937636,FJ639798,KJ189265,JQ920482,FJ639793,EU529692,FJ639713,EU529705,AY662691,GU131937,FJ850049,JF937625,KF955473,AY676348,EF629370,EU529688,AY679147,JF937648,AY496871,EU081214,AY858047,HG316483,JQ920 |

| Taxonomy | NCBI Reference Sequence ID | Host | No. of Genomes | Lineage | Segment Count | Genbank Accession ID |
|---|---|---|---|---|---|---|
| | | | | | | 484,FJ882571,GQ86 8627,KJ189296,FJ54 7081,FJ182041,FJ63 9801,FJ547083,GQ8 68574,EU081190,KF 955461,EF629368,FJ 547062,GU131907,H M631864,EU482563, FJ639769,JN000936, FI410229,FJ182015, FJ639761,KJ189283, HQ705621,KJ189273 ,KJ189269,GU13195 3,FJ639795,FJ63972 3,FJ182038,KJ18925 8,HQ671178,JQ0456 92, FJ898459,GU1319 11,HM756277,GU131 870,GU131905,FJ882 572,KJ189262,FJ8501 098,GQ199862,JF93 7630,JF920399,JF80 8121,HM756282,JF8 08118,JF808119,HQ5 41789,FJ639720,EU0 81220,JQ920485,KF9 55458,KJ189280,EU4 82453,GU131857,EU 08181,DQ675519,E U660411,JQ920488,F J547076,AY770511,J Q920487,JF937634,J F937637,GU131872, EU081189,EU726774 ,JF873813,HM18193 5,FJ547066,GU13194 4,FJ639731,FJ54707 7,EU482461,FJ85007 9,HM631854,GQ8685 78,JF937646,FJQ244 65,EU081215,AY858 041,FJ913015,HQ705 615,AY496873,GU13 1853,KF824902,GU1 31862,JQ920476,FJ5 62107,KJ189263,FJ7 44740,EU687219,KJ1 89292,AY744682,KJ1 |

| Taxonomy | NCBI Reference Sequence ID | Host | No. of Genomes | Lineage | Segment Count | Genbank Accession ID |
|---|---|---|---|---|---|---|
| | | | | | | 89277,JN093517,EU482454,FJ562102,EU081223,EU081203,FJ639774,GU131869,EU529703, HQ705623,FJ744727,JF937626,AB214881,AY858044,EF629369,EF629373,FJ390375,FJ898470,KJ189268,JN093515,FJ898445,JQ920478,HM631861,HM756281,EU529690,GU131904,KJ189298,FJ639750,FJ547061,KJ189256,FJ882577,DQ675528,FJ562097,KJ189278,FJ898446,GU131951,KJ189271,GU131848,FJ898462,EU081195,DQ675520, HQ705622,EU529698,KJ189266,FJ639784,FJ639792,GQ868593,AY744683,FJ898444,GU131876,FJ639778,FJ432722,FJ639755,EU081186,HQ705617,GU131847,FJ639770,EU529699,EU726769,FJ850097,JQ920480,EU596494,EU081192,KF955466,FJ898472,AB214880,HQ166032,KF921916,JF808122,DQ863638,FJ744734,GU131915,JF937647,JF295012,GQ199886,FJ850094,JF808120,EU482613,EU529686,JF920404,FJ639768,H016033,HQ332170,JF920396,FJ744729,DQ675525,EU081196,KJ189274,EU529683,EU482559,HM181933,HM181934,FJ5470 78,EU081194,FJ6397 |

| Taxonomy | NCBI Reference Sequence ID | Host | No. of Genomes | Lineage | Segment Count | Genbank Accession ID |
|---|---|---|---|---|---|---|
| | | | | | | 76,GQ868548,FJ461334,KJ189291,HQ705610,GQ252678,GU131913,GU131871,JF808124,FJ639805,GQ868577,GU131934,EU081206,HQ705613,JQ045694,AB189127,FJ639756,FJ744735,EU482566,GU131941,EU081208,EU726772,JF937638,FJ882574,EU854298,DQ40169 0,EU687218,HM181975,FJ461326,FJ898457,HM631857,JF937620,FJ644564,FJ744737,GU131939,KF955471,AY744677,HM631869,FJ562099,KJ189288,FJ898475,G0466079,JF937623,J0920486,EU081205,GU131855,GU131856,FJQ24466,GQ868547,AY744684,FJ461337,HM631862,AY676352,GU131952,HM181972,FJ182006,GU131877,GU131846,HM631860,JF920402,KJ189270,FJ205870,KJ189285,GU131938,JF937632,FJ182013,FJ882575,AY923865,HM631858,JQ045690,EU482614,JF920405,FJ639751,FJ898469,FJ744731,KJ189260,AY496874,FJ432728,DQ675531,EU482452,EF643017,EU482595,EU596493,EU660409,EU726773,FJ850096,FJ898464,EU569691,FJ810416,FJ898463,GU131861,KF955476,FJ547085,EU0812 |

| Taxonomy | NCBI Reference Sequence ID | Host | No. of Genomes | Lineage | Segment Count | Genbank Accession ID |
|---|---|---|---|---|---|---|
| | | | | | | 25,JF920409,GU1318 66,EU854291,EU932 688,JF808127,JQ045 689,AY858042,EU08 1212,GQ199891,JF9 37639,FJ898476,DQ4 01692,AY744679,DQ 675527,JF808128,JF 920393,FJ639763,FJ 461322,FJ547079,G 0868626,KJ189289,J F920407,HQ541796, FJ182037,KJ189259, EU687198,GQ86854 6,GQ199861,EU5297 02,FJ898458,JF5046 79,HQ705609,AY676 350,HM61863,FJ74 4732,AY099337,FJ63 9817,JF937621,KJ18 9261,EU482612,EU4 82564,GU131874,EU 482459,KJ189300,AY 496879,JF937640,JF 920401,FJ850056,KJ 189290,EU081201,FJ 898441,FJ390377,H M756276,EU081204, GU131903,GQ19988 9,EU569690,GQ1998 63,JN662391,FJ8500 89,DQ401693,JF9203 98,FJ639826,GQ199 870,FJ898468,EU081 198,FJ639721,KJ189 282,KF955332,DQ67 5523,EU781136,FJ54 7072,FJ373306,GQ8 68587,EU482455,FJ5 62103,AY744685,FJ6 39827,FJ898456,EU6 60410,FJ390376,GU1 31860,GU131852,GU 131850,FJ898474,EU 932687,GU131878,H M181978,EU081182, GU131942,FJ182007, EU081210,KF041257 |

| Taxonomy | NCBI Reference Sequence ID | Host | No. of Genomes | Lineage | Segment Count | Genbank Accession ID |
|---|---|---|---|---|---|---|
| | | | | | | ,EU081224,KJ189276,FJ639730,HQ166031,KF955487,EU08118 4,GU131844,EU4824 58,JN093513,JQ0456 88,JF920406,EU5296 96,FJ873812,AY8580 38,KF955472,GQ199 864,KJ189272,HQ54 1806,EU596492,DQ6 75529,FJ850109,KF9 55465,AY858040,FJ5 47075,FJ744700,EU5 69689,JF937641,FJ5 47082,EU687197,HQ 671177,FJ639804,AY 858045,HQ541797,K F824903,HQ705618, FJ639753,FJ390372, JF937629,GU131908, FJ639716,GU131865, JQ411814,FJ639790, KF041254,EU529684 ,KJ189301,HM18197 6,FJ639725,FJ89845 5,FJ639754,FJ63981 6,FJ639759,GQ8686 28,HQ332171,JQ920 483,FJ182008,AY858 039,EU081197,AY67 6353,DQ675524,FJ63 9799,AY744681,EU6 87233,KF955451,JF8 08129,HQ891025,FJ6 39727,EU081191,JF9 37652,HQ705612,FJ8 50111,FJ639787,HM 756279,JQ920489,H 0166030,FJ898440, GU131943,JF920395, FJ182011,FJ639782, AY858046,FJ850048, FJ639786,GU131916, HQ705614,EU687196 ,EU529697,JF920400 ,FJ639757,EU081207 ,FJ744736,KC425219 ,FJ373303,EU529685 |

| Taxonomy | NCBI Reference Sequence ID | Host | No. of Genomes | Lineage | Segment Count | Genbank Accession ID |
|---|---|---|---|---|---|---|
| | | | | | | ,KJ189297,EU081209 |
| | | | | | | ,FJ639752,KF955453 |
| | | | | | | ,FJ639749,EU726771 |
| | | | | | | ,HQ166034,KF95550 |
| | | | | | | 7,DQ67521,FJQ2447 |
| | | | | | | 0,EU081185,KJ18925 |
| | | | | | | 7,JQ920481,FJQ2446 |
| | | | | | | 8,GU131854,EU3679 |
| | | | | | | 62,AY766104,FJ6397 |
| | | | | | | 19,FJ639722,EU5296 |
| | | | | | | 87,DQ675526,JF8081 |
| | | | | | | 25,FJQ24467,HQ5417 |
| | | | | | | 85,GU131918,GU131 |
| | | | | | | 945,GU131912,GU13 |
| | | | | | | 1946,HQ705620,HM7 |
| | | | | | | 56274,HM756278,FJ |
| | | | | | | 850083,GQ868571,J |
| | | | | | | N183884,EF629367, |
| | | | | | | DQ401695,KF955454 |
| | | | | | | ,FJ744738,EU660420 |
| | | | | | | ,DQ401691,GU13191 |
| | | | | | | 4,AY744678,HQ6711 |
| | | | | | | 76,FJ461329,FJ6397 |
| | | | | | | 15,AY776329,FJ7447 |
| | | | | | | 30,FJ687448,KF9554 |
| | | | | | | 77,GU131851,FJ3733 |
| | | | | | | 04,KF955456,KJ1892 |
| | | | | | | 95,FJ639766,JF9204 |
| | | | | | | 03,FJ639781,DQ6755 |
| | | | | | | 30,JN368477,FJ8500 |
| | | | | | | 55,AY858048,HM181 |
| | | | | | | 973,FJ562100,FJ850 |
| | | | | | | 052,KF041255,JF808 |
| | | | | | | 123,GQ252674,EU68 |
| | | | | | | 7234,FJ639726,FJ63 |
| | | | | | | 9772,FJ410176,EU48 |
| | | | | | | 2555,GU131868,JF92 |
| | | | | | | 0394,JF937622,FJ47 |
| | | | | | | 8456,FJ639780,EU48 |
| | | | | | | 2462,FJ182010,KJ18 |
| | | | | | | 9284,KF955505,EU5 |
| | | | | | | 69688,AY648961,KF9 |
| | | | | | | 55468,GU131849,EU |
| | | | | | | 081188,EU687226,G |
| | | | | | | U131950,JF937628,J |
| | | | | | | N00938,KF955459,F |
| | | | | | | J547080,FJ898442,F |
| | | | | | | J182039,GU189648,F |

| Taxonomy | NCBI Reference Sequence ID | Host | No. of Genomes | Lineage | Segment Count | Genbank Accession ID |
| --- | --- | --- | --- | --- | --- | --- |
| | | | | | | J547084,EU854292,KJ189267,EU081216, GQ868616,EU081213,FJ639785,EF62936 6,FJ810413,JN40651 5,KJ189286,GU1319 40,EU529691,FJ1820 09,FJ639746,KJ1892 64,AY744680,FJ15470 71,FJQ24469,CS8053 42,FJ898473,GU1318 58,FJ744733,KF0412 59,FJ639765,FJ7447 39,JQ045687,EU529 689,FJ898471,FJ639 728,EU081211,EU78 1137,FJ639800,GQ1 99860,JN093514,AY6 76349,KF955460,EU 081218,FJ390373,KJ 189294,HM756280,K F041256,GQ868586, GU131906,KJ189279 ,GQ199888,JQ92047 9,EU081222,GU3635 49,AY496877,FJ6397 67,JN000937,DQ675 532,FJ410178,EU081 187,DQ675522,HQ54 1790,EU081199,GQ1 99871,GQ868634,FJ 882576,FJ547073,AF 317645,GU131910,FJ 898443,AY855037,JQ 920477,FJ1639807,FJ 639771,FJ850110,AY 876494,KF955464,G U131909,HQ705616, FJ810414,HM756275 ,EU081193,AB21487 9,GU131935,AB1891 28,JF937627,FJ6397 91,JF920397,FJ6398 25,KF955462,FJ6397 75,GQ868573,FJ639 747,GQ199865,HM63 1856,FJ182004,FJO2 4471,EU081183,FJ54 |

-continued

| Taxonomy | NCBI Reference Sequence ID | Host | No. of Genomes | Lineage | Segment Count | Genbank Accession ID |
|---|---|---|---|---|---|---|
| | | | | | | 7070,EU482456,EU7 26768,DQ401694,GU 131845,GU131875,FJ 744728,JF937642,JQ 045695,KJ189287,G U131936,JN406514,K F955474,HQ235027, KF955449,EU081217 ,KJ189275,KJ189281, FJ898447,FJ639810, FJ639712,EU081200, FJ850092,DQ401689, GQ868575,FJ639777 ,FJ882573,KF955486 ,FJ639729,FJ390371, HM181974,JN697379 ,FJ410177,DQ675533 ,GQ868576,HG3164 ,AB189126,GU13191 84,HQ541795 |
| Dengue virus 4 | NC_002640 ,NC_00147 5,NC_0014 74,NC_001 477 | vertebrates,invertebrates, human | 134 | Flaviviridae,Flavivirus,Dengue virus | | FJ882587,FJQ24476, FJ882589,AY618992, EU854295,KF041260 ,JQ513333,FJ639745 ,GQ199880,JQ51334 5,JN819409,AY61899 1,JQ513339,JN55974 0,JQ915087,FJ81041 7,JQ513332,JQ51333 7,FJ882581,JQ51334 0,JN819406,JQ51334 2,JF262780,FJ63973 6,FJ882583,GQ1998 79,GQ398256,GQ868 585,JQ513344,FJ882 595,JQ915089,FJ882 592,JQ513341,HQ33 2176,JQ915082,FJ63 9738,JQ513331,JQ51 3343,AF375822,EF45 7906,JXQ24758,FJ88 2585,FJQ24424,GQ8 68594,GQ868581,AY 947539,EU854297,G 0199885,FJ882591, GQ868579,FJ882598 ,EU854301,GQ86858 0,AY618990,FJ22606 |

| Taxonomy | NCBI Reference Sequence ID | Host | No. of Genomes | Lineage | Segment Count | Genbank Accession ID |
|---|---|---|---|---|---|---|
| | | | | | | 7,HQ332172,JQ9150 84,AF326825,FJ8500 59,GQ199882,KC333 651,JQ513338,FJ639 744,GQ199884,AY85 8050,FJ882584,FJ63 9773,JQ513330,JF74 1967,FJ882588,FJ63 9737,JF262782,GQ8 68584,FJ882590,FJ8 50095,H

| Taxonomy | NCBI Reference Sequence ID | Host | No. of Genomes | Lineage | Segment Count | Genbank Accession ID |
|---|---|---|---|---|---|---|
| Douglas virus | NC_018466 | vertebrates,invertebrates, human | 1 | Bunyaviridae,Orthobunyavirus,Sathuperi virus | seg. M | HE

| Taxonomy | NCBI Reference Sequence ID | Host | No. of Genomes | Lineage | Segment Count | Genbank Accession ID |
|---|---|---|---|---|---|---|
| Eyach virus | NC_003703 | v -continued

| Taxonomy | NCBI Reference Sequence ID | Host | No. of Genomes | Lineage | Segment Count | Genbank Accession ID |
|---|---|---|---|---|---|---|
| Huaiyangshan virus | NC_018136 | vertebrates,invertebrates, human | 1 | Bunyaviridae,Phlebovirus,Severe fever with thrombocytopenia syndrome virus | seg. L | JF906056 |
| Huaiyangshan virus | NC_018137 | vertebrates,invertebrates, human | 1 | Bunyaviridae,Phlebovirus,Severe fever with thrombocytopenia syndrome virus | seg. S | JF906058 |
| Huaiyangshan virus | NC_018138 | vertebrates,invertebrates, human | 3 | Bunyaviridae,Phlebovirus,Severe fever with thrombocytopenia syndrome virus | seg. M | JF951394,JF906057, JF951393 |
| Igbo Ora virus | NC_001512 | vertebrates,invertebrates, human | 1 | Togaviridae,Alphavirus,O'nyong-nyong virus | — | AF079457 |
| Iguape virus | NC_009026 | vertebrates,invertebrates, human | 1 | Flaviviridae,Flavivirus,Aroa virus | — | AY632538 |
| Ilesha virus | NC_001926 | vertebrates,invertebrates, human | 1 | Bunyaviridae,Orthobunyavirus,Bunyamwera virus | seg. M | AY859372 |
| Ilesha virus | NC_001927 | vertebrates,invertebrates, human | 3 | Bunyaviridae,Orthobunyavirus,Bunyamwera virus | seg. S | AM709780,AM70977 9,AY729651 |
| Ilheus virus | NC_009028 | vertebrates,invertebrates, human | 2 | Flaviviridae,Flavivirus,Ilheus virus | | KC481679,AY632539 |
| Inkoo virus | NC_004108 | vertebrates,invertebrates, human | 1 | Bunyaviridae,Orthobunyavirus,California encephalitis virus | seg. L | EU789573 |
| Inkoo virus | NC_004109 | vertebrates,invertebrates, human | 2 | Bunyaviridae,Orthobunyavirus,California encephalitis virus | seg. M | U88059,U88060 |
| Inkoo virus | NC_004110 | vertebrates,invertebrates, human | 2 | Bunyaviridae,Orthobunyavirus,California encephalitis virus | seg. S | U47137,U47138 |
| Israel turkey meningoencephalomyelitis virus | NC_012534 | vertebrates,invertebrates, human | 5 | Flaviviridae,Flavivirus,Bagaza virus | seg. M | KC734553,KC734550 ,KC734552,KC73454 9,KC734551 |
| Itaituba virus | NC_015373 | vertebrates,invertebrates, human | 1 | Bunyaviridae,Phlebovirus,Candiru virus | seg. M | HM119417 |
| Itaituba virus | NC_015374 | vertebrates,invertebrates, human | 1 | Bunyaviridae,Phlebovirus,Candiru virus | seg. L | HM119416 |
| Itaituba virus | NC_015375 | vertebrates,invertebrates, human | 1 | Bunyaviridae,Phlebovirus,Candiru virus | seg. S | HM119418 |
| Ixcanal virus | NC_015450 | vertebrates,invertebrates, human | 1 | Bunyaviridae,Phlebovirus,Aguacate virus | seg. M | HM566163 |
| Ixcanal virus | NC_015451 | vertebrates,invertebrates, human | 1 | Bunyaviridae,Phlebovirus,Aguacate virus | seg. L | HM566162 |
| Ixcanal virus | NC_015452 | vertebrates,invertebrates, human | 1 | Bunyaviridae,Phlebovirus,Aguacate virus | seg. S | HM566161 |
| Jacunda virus | NC_015373 | vertebrates,invertebrates, human | 1 | Bunyaviridae,Phlebovirus,Candiru virus | seg. M | HM466935 |
| Jacunda virus | NC_015374 | vertebrates,invertebrates, human | 1 | Bunyaviridae,Phlebovirus,Candiru virus | seg. L | HM466934 |
| Jacunda virus | NC_015375 | vertebrates,invertebrates, human | 1 | Bunyaviridae,Phlebovirus,Candiru virus | seg. S | HM466936 |
| Jamestown Canyon virus | NC_004109 | vertebrates,invertebrates, human | 1 | Bunyaviridae,Orthobunyavirus,California encephalitis virus | seg. M | U88058 |
| Jamestown Canyon virus | NC_004110 | vertebrates,invertebrates, human | 1 | Bunyaviridae,Orthobunyavirus,California encephalitis virus | seg. S | U12796 |

-continued

| Taxonomy | NCBI Reference Sequence ID | Host | No. of Genomes | Lineage | Segment Count | Genbank Accession ID |
| --- | --- | --- | --- | --- | --- | --- |
| Japanese encephalitis virus | NC_001437 | vertebrates,invertebrates, human | 171 | Flaviviridae,Flavivirus,Japanese encephalitis virus | — | JN381857,JF706274, AB551990,AF254452, JN381837,M18370,KF297915,JQ086763,JN381858,KC915016,JN381855,JN381861,JXQ72965,JF706281,JN381862,D90195,JF706278,FJ185037,JXQ50179,U14163,AY849939,JN381869,JN381832,AB698906,AB698907,JF706269,AB051292,JN381849,JN381870,EF571853,JN381859,JF499790,JF706282,JN381831,M55506,JN381851,JF706280,JN711458,AY585242,JN381844,GQ902061,JN381863,AY303798,JF706272,HQ652538,AF075723,JF706270,JF706283,AY508813,JN381840,JN381830,JN381850,AF221500,AY303792,AB241118,AF254453,AB551991,AY508812,JN644310,AB241119,AF486638,AB830335,JN381864,JN381847,KF297916,HM228921,JF706284,AF315119,JF706277,JN381860,AF416457,AF069076,GU205163,GQ918133,AF221499,JF706267,JN381833,JN381843,JN381871,JF706286,AB698905,JN381854,JN381873,JN381848,JF706275,FJ495189,AY316157,EF623987,JF706268,HM366552, AF014161,GU556217,JN381834,JN381842,AY303794,JN381853 |

| Taxonomy | NCBI Reference Sequence ID | Host | No. of Genomes | Lineage | Segment Count | Genbank Accession ID |
|---|---|---|---|---|---|---|
| Jerry Slough virus | NC_004109 | vertebrates,invertebrates, human | 1 | Bunyaviridae,Orthobunyavirus,California encephalitis virus | seg. M | JF499788,JX131374, AF014160,HMS96272, AY585243,JN711459, AF098735,AF045551, AF098737,GQ90205 9,AB196926,JN60498 6,AY303796,AF21762 0,AY303797,EF62398 8,JN381841,GQ9020 60,JN381856,JN3818 52,JF706273,JQ0867 62,JF706276,D90194 ,EU429297,AY30379 1,AB196925,KC5174 97,JN381866,JN8640 64,JF706279,AB5948 29,L48961,FJ185036, AB698908,JN381846, AB853904,AF080251, JF499789,JN381845, JN381867,AB196924, JN381872,HE861351, GQ902062,EF623989 ,EU880214,HQ89354 5,GQ199609,AY3037 93,JN381836,KC1961 15,JN381835,U15763 ,AB196923,EF543861 ,AB698909,EU69389 9,JF706271,JF70628 5,JN381838,L78128,J N381839,GU187972, AY303795,U47032,G 090205,EF107523,J F915894,AB551992, GQ902063,JN381868 ,AY184212,JN381865 ,AF098736 |
| Kadipiro virus | NC_004199 | vertebrates,invertebrates, human | 2 | Reoviridae,Seadornavirus,Kadipiro virus | seg. 12 | AF123487 |
| Kadipiro virus | NC_004205 | vertebrates,invertebrates, human | 1 | Reoviridae,Seadornavirus,Kadipiro virus | seg. 11 | AF019909,FJ159105 |
| Kadipiro virus | NC_004206 | vertebrates,invertebrates, human | 1 | Reoviridae,Seadornavirus,Kadipiro virus | seg. 10 | AF052019 |
| Kadipiro virus | NC_004207 | vertebrates,invertebrates, human | 1 | Reoviridae,Seadornavirus,Kadipiro virus | seg. 9 | AF052020 |
|  |  |  |  |  |  | AF052021 |

-continued

| Taxonomy | NCBI Reference Sequence ID | Host | No. of Genomes | Lineage | Segment Count | Genbank Accession ID |
|---|---|---|---|---|---|---|
| Kadipiro virus | NC_004208 | vertebrates,invertebrates, human | 1 | Reoviridae,Seadornavirus,Kadipiro virus | seg. 8 | AF052022 |
| Kadipiro virus | NC_004209 | vertebrates,invertebrates, human | 1 | Reoviridae,Seadornavirus,Kadipiro virus | seg. 7 | AF052023 |
| Kadipiro virus | NC_004210 | vertebrates,invertebrates, human | 1 | Reoviridae,Seadornavirus,Kadipiro virus | seg. 1 | AF133429 |
| Kadipiro virus | NC_004212 | vertebrates,invertebrates, human | 1 | Reoviridae,Seadornavirus,Kadipiro virus | seg. 2 | AF134509 |
| Kadipiro virus | NC_004213 | vertebrates,invertebrates, human | 1 | Reoviridae,Seadornavirus,Kadipiro virus | seg. 3 | AF134510 |
| Kadipiro virus | NC_004214 | vertebrates,invertebrates, human | 1 | Reoviridae,Seadornavirus,Kadipiro virus | seg. 4 | AF134511 |
| Kadipiro virus | NC_004215 | vertebrates,invertebrates, human | 1 | Reoviridae,Seadornavirus,Kadipiro virus | seg. 5 | AF134512 |
| Kadipiro virus | NC_004216 | vertebrates,invertebrates, human | 1 | Reoviridae,Seadornavirus,Kadipiro virus | seg. 6 | AF134513 |
| Kama virus | NC_023439 | vertebrates,invertebrates, human | 1 | Flaviviridae,Flavivirus,Kama virus | — | KF815940 |
| Kamiti River virus | NC_005064 | vertebrates,invertebrates, human | 2 | Flaviviridae,Flavivirus,Kamiti River virus | — | AY149905,AY149904 |
| Karshi virus | NC_006947 | vertebrates,invertebrates, human | 3 | Flaviviridae,Flavivirus,Royal Farm virus | — | DQ235147,AY863002 ,DQ462443 |
| Kedougou virus | NC_012533 | vertebrates,invertebrates, human | 1 | Flaviviridae,Flavivirus,Kedougou virus | — | AY632540 |
| Kemerovo virus | NC_014522 | vertebrates,invertebrates, human | 2 | Reoviridae,Orbivirus,Great Island virus | seg. 1 | HQ266591,HM54348 1 |
| Kemerovo virus | NC_014523 | vertebrates,invertebrates, human | 2 2 | Reoviridae,Orbivirus,Great Island virus | seg. 2 | HQ266592,HM54348 |
| Kemerovo virus | NC_014524 | vertebrates,invertebrates, human | 1 | Reoviridae,Orbivirus,Great Island virus | seg. 3 | HQ266593 |
| Kemerovo virus | NC_014525 | vertebrates,invertebrates, human | 1 | Reoviridae,Orbivirus,Great Island virus | seg. 4 | HQ266594 |
| Kemerovo virus | NC_014526 | vertebrates,invertebrates, human | 2 5 | Reoviridae,Orbivirus,Great Island virus | seg. 5 | HQ266596,HQ26659 |
| Kemerovo virus | NC_014527 | vertebrates,invertebrates, human | 1 | Reoviridae,Orbivirus,Great Island virus | seg. 6 | HM543483 |
| Kemerovo virus | NC_014528 | vertebrates,invertebrates, human | 1 | Reoviridae,Orbivirus,Great Island virus | seg. 7 | HQ266597 |
| Kemerovo virus | NC_014529 | vertebrates,invertebrates, human | 1 | Reoviridae,Orbivirus,Great Island virus | seg. 8 | HQ266598 |
| Kemerovo virus | NC_014530 | vertebrates,invertebrates, human | 1 | Reoviridae,Orbivirus,Great Island virus | seg. 9 | HQ266599 |
| Kemerovo virus | NC_014531 | vertebrates,invertebrates, human | 1 | Reoviridae,Orbivirus,Great Island virus | seg. 10 | HQ266600 |
| Keystone virus | NC_004109 | vertebrates,invertebrates, human | 1 | Bunyaviridae,Orthobunyavirus,California encephalitis virus | seg. M | AF123489 |
| Keystone virus | NC_004110 | vertebrates,invertebrates, human | 1 | Bunyaviridae,Orthobunyavirus,California encephalitis virus | seg. S | U12801 |

| Taxonomy | NCBI Reference Sequence ID | Host | No. of Genomes | Lineage | Segment Count | Genbank Accession ID |
|---|---|---|---|---|---|---|
| Kokobera virus | NC_009029 | vertebrates,invertebrates, human | 1 | Flaviviridae,Flavivirus,Kokobera virus | — | AY632541 |
| Kunjin virus | NC_001563 | vertebrates,invertebrates, human | 3 | Flaviviridae,Flavivirus,West Nile virus | — | DQ0246,AY274505,AY274504 |
| Kunjin virus | NC_009942 | vertebrates,invertebrates, human | 3 | Flaviviridae,Flavivirus,West Nile virus | — | DQ0246,AY274505,AY274504 |
| Kyasanur forest disease virus | NC_004355 | vertebrates,invertebrates, human | 6 | Flaviviridae,Flavivirus,Kyasanur forest disease virus | — | EU480689,JF416960, AY323490,JF416959, JF416958,HM055369 |
| La Crosse virus | NC_004108 | vertebrates,invertebrates, human | 7 | Bunyaviridae,Orthobunyavirus,California encephalitis virus | seg. L | AF525489,EF485038, EF485055,AF528165, U12396,EF485032, D0196118 |
| La Crosse virus | NC_004109 | vertebrates,invertebrates, human | 13 | Bunyaviridae,Orthobunyavirus,California encephalitis virus | seg. M | EF485031,DQ196119 ,U70207,EF485037,U 70205,U 18980,U 7020 8,EF485034,M87664, D10370,U70206,U18 979,AF528166 |
| La Crosse virus | NC_004110 | vertebrates,invertebrates, human | 7 | Bunyaviridae,Orthobunyavirus,California encephalitis virus | seg. S | DQ196120,EF485030 ,EF485036,AF528167 ,K00610,EF485033,K 00108 |
| Langat virus | NC_003690 | vertebrates,invertebrates, human | 3 | Flaviviridae,Flavivirus,Langat virus | — | EU790644,AF253420 ,AF253419 |
| Liao ning virus | NC_007736 | vertebrates,invertebrates, human | 1 | Reoviridae,Seadornavirus,Liao ning virus | seg. 1 | AY701339 |
| Liao ning virus | NC_007737 | vertebrates,invertebrates, human | 1 | Reoviridae,Seadornavirus,Liao ning virus | seg. 2 | AY701340 |
| Liao ning virus | NC_007738 | vertebrates,invertebrates, human | 1 | Reoviridae,Seadornavirus,Liao ning virus | seg. 3 | AY701341 |
| Liao ning virus | NC_007739 | vertebrates,invertebrates, human | 1 | Reoviridae,Seadornavirus,Liao ning virus | seg. 4 | AY701342 |
| Liao ning virus | NC_007740 | vertebrates,invertebrates, human | 1 | Reoviridae,Seadornavirus,Liao ning virus | seg. 5 | AY701343 |
| Liao ning virus | NC_007741 | vertebrates,invertebrates, human | 1 | Reoviridae,Seadornavirus,Liao ning virus | seg. 6 | AY701344 |
| Liao ning virus | NC_007742 | vertebrates,invertebrates, human | 1 | Reoviridae,Seadornavirus,Liao ning virus | seg. 7 | AY701345 |
| Liao ning virus | NC_007743 | vertebrates,invertebrates, human | 1 | Reoviridae,Seadornavirus,Liao ning virus | seg. 8 | AY701346 |
| Liao ning virus | NC_007744 | vertebrates,invertebrates, human | 1 | Reoviridae,Seadornavirus,Liao ning virus | seg. 9 | AY701347 |
| Liao ning virus | NC_007745 | vertebrates,invertebrates, human | 1 | Reoviridae,Seadornavirus,Liao ning virus | seg. 10 | AY701348 |
| Liao ning virus | NC_007746 | vertebrates,invertebrates, human | 1 | Reoviridae,Seadornavirus,Liao ning virus | seg. 11 | AY701349 |

-continued

| Taxonomy | NCBI Reference Sequence ID | Host | No. of Genomes | Lineage | Segment Count | Genbank Accession ID |
|---|---|---|---|---|---|---|
| Liao ning virus | NC_007747 | vertebrates,invertebrates, human | 1 | Reoviridae,Seadornavirus,Liao ning virus | seg. 12 | AY701350 |
| Lipovnik virus | NC_014522 | vertebrates,invertebrates, human | 1 | Reoviridae,Orbivirus,Great Island virus | seg. 1 | HM543475 |
| Lipovnik virus | NC_014523 | vertebrates,invertebrates, human | 1 | Reoviridae,Orbivirus,Great Island virus | seg. 2 | HM543476 |
| Louping ill virus | NC_001809 | vertebrates,invertebrates, human | 2 | Flaviviridae,Flavivirus,Louping ill virus | — | Y07863,KF056331 |
| Lumbo virus | NC_004109 | vertebrates,invertebrates, human | 1 | Bunyaviridae,Orthobunyavirus,California encephalitis virus | seg. M | AF123484 |
| Lumbo virus | NC_004110 | vertebrates,invertebrates, human | 1 | Bunyaviridae,Orthobunyavirus,California encephalitis virus | seg. S | X73468 |
| Maguari virus | NC_001926 | vertebrates,invertebrates, human | 4 | Bunyaviridae,Orthobunyavirus,Bunyamwera virus | seg. M | AY286444,AY286443 ,AY286445,AY28644 6 |
| Maldonado virus | NC_015373 | vertebrates,invertebrates, human | 1 | Bunyaviridae,Phlebovirus,Candiru virus | seg. M | HM119414 |
| Maldonado virus | NC_015374 | vertebrates,invertebrates, human | 1 | Bunyaviridae,Phlebovirus,Candiru virus | seg. L | HM119413 |
| Maldonado virus | NC_015375 | vertebrates,invertebrates, human | 1 | Bunyaviridae,Phlebovirus,Candiru virus | seg. S | HM119415 |
| Massilia virus | NC_006318 | vertebrates,invertebrates, human | 1 | Bunyaviridae,Phlebovirus,Sandfly fever Naples virus | seg. S | EU725773 |
| Massilia virus | NC_006319 | vertebrates,invertebrates, human | 1 | Bunyaviridae,Phlebovirus,Sandfly fever Naples virus | seg. L | EU725771 |
| Massilia virus | NC_006320 | vertebrates,invertebrates, human | 1 | Bunyaviridae,Phlebovirus,Sandfly fever Naples virus | seg. M | EU725772 |
| Mayaro virus | NC_003417 | vertebrates,invertebrates, human | 2 | Togaviridae,Alphavirus,Mayaro virus | — | DQ001069,AF237947 |
| Mboke virus | NC_001927 | vertebrates,invertebrates, human | 1 | Bunyaviridae,Orthobunyavirus,Bunyamwera virus | seg. S | AY593727 |
| Melao virus | NC_004109 | vertebrates,invertebrates, human | 1 | Bunyaviridae,Orthobunyavirus,California encephalitis virus | seg. M | U88057 |
| Modoc virus | NC_003635 | vertebrates,invertebrates, human | 1 | Flaviviridae,Flavivirus,Modoc virus | — | AJ242984 |
| Montana myotis leukoencephalitis virus | NC_004119 | vertebrates,invertebrates, human | 1 | Flaviviridae,Flavivirus,Montana myotis leukoencephalitis virus | — | AJ299445 |
| Morro Bay virus | NC_004110 | vertebrates,invertebrates, human | 1 | Bunyaviridae,Orthobunyavirus,California encephalitis virus | seg. S | U31989 |
| Morumbi virus | NC_015373 | vertebrates,invertebrates, human | 1 | Bunyaviridae,Phlebovirus,Candiru virus | seg. M | HM119423 |
| Morumbi virus | NC_015374 | vertebrates,invertebrates, human | 1 | Bunyaviridae,Phlebovirus,Candiru virus | seg. L | HM119422 |
| Morumbi virus | NC_015375 | vertebrates,invertebrates, human | 1 | Bunyaviridae,Phlebovirus,Candiru virus | seg. S | HM119424 |
| Mosquito flavivirus | NC_021069 | vertebrates,invertebrates, 1 human | | Flaviviridae,Flavivirus,Mosquito flavivirus | — | KC464457 |

-continued

| Taxonomy | NCBI Reference Sequence ID | Host | No. of Genomes | Lineage | Segment Count | Genbank Accession ID |
|---|---|---|---|---|---|---|
| Mucura virus | NC_015373 | vertebrates,invertebrates, human | 1 | Bunyaviridae,Phlebovirus,Candiru virus | seg. M | HM119420 |
| Mucura virus | NC_015374 | vertebrates,invertebrates, human | 1 | Bunyaviridae,Phlebovirus,Candiru virus | seg. L | HM119419 |
| Mucura virus | NC_015375 | vertebrates,invertebrates, human | 1 | Bunyaviridae,Phlebovirus,Candiru virus | seg. S | HM119421 |
| Murray Valley encephalitis virus | NC_000943 | vertebrates,invertebrates, human | 10 | Flaviviridae,Flavivirus,Murray Valley encephalitis virus | — | KC852193,JX123032, AF161266,KC852192 ,KC852194,KC85219 5,KC852189,KC8521 90,KC852191,KC852 196 |
| Murre virus | NC_005214 | vertebrates,invertebrates, human | 1 | Bunyaviridae,Phlebovirus,Uukuniemi virus | seg. L | JF838330 |
| Murre virus | NC_005220 | vertebrates,invertebrates, human | 1 | Bunyaviridae,Phlebovirus,Uukuniemi virus | seg. M | JF838331 |
| Ngari virus | NC_001926 | vertebrates,invertebrates, human | 1 | Bunyaviridae,Orthobunyavirus,Bunyamwera virus | seg. M | AY593725 |
| Ngari virus | NC_001927 | vertebrates,invertebrates, human | 1 | Bunyaviridae,Orthobunyavirus,Bunyamwera virus | seg. S | AY593729 |
| Nique virus | NC_015373 | vertebrates,invertebrates, human | 1 | Bunyaviridae,Phlebovirus,Candiru virus | seg. M | HM119426 |
| Nique virus | NC_015374 | vertebrates,invertebrates, human | 1 | Bunyaviridae,Phlebovirus,Candiru virus | seg. L | HM119425 |
| Nique virus | NC_015375 | vertebrates,invertebrates, human | 1 | Bunyaviridae,Phlebovirus,Candiru virus | seg. S | HM119427 |
| Northway virus | NC_001927 | vertebrates,invertebrates, human | 1 | Bunyaviridae,Orthobunyavirus,Bunyamwera virus | seg. S | X73470 |
| Ntaya virus | NC_018705 | vertebrates,invertebrates, human | 1 | Flaviviridae,Flavivirus,Ntaya virus | — | JX236040 |
| O'nyong-nyong virus | NC_001512 | vertebrates,invertebrates, human | 2 | Togaviridae,Alphavirus,O'nyong-nyong virus | — | AF079456,M20303 |
| Omsk hemorrhagic fever virus | NC_005062 | vertebrates,invertebrates, human | 4 | Flaviviridae,Flavivirus,Omsk hemorrhagic fever virus | — | AY323489,AB507800 ,AY438626,AY19380 5 |
| Oriximina virus | NC_015373 | vertebrates,invertebrates, human | 1 | Bunyaviridae,Phlebovirus,Candiru virus | seg. M | HM119435 |
| Oriximina virus | NC_015374 | vertebrates,invertebrates, human | 1 | Bunyaviridae,Phlebovirus,Candiru virus | seg. L | HM119434 |
| Oriximina virus | NC_015375 | vertebrates,invertebrates, human | 1 | Bunyaviridae,Phlebovirus,Candiru virus | seg. S | HM119436 |
| Oropouche virus | NC_005775 | vertebrates,invertebrates, human | 2 | Bunyaviridae,Orthobunyavirus,Oropouche virus | seg. M | AF312381,AF441119 |
| Oropouche virus | NC_005776 | vertebrates,invertebrates, human | 1 | Bunyaviridae,Orthobunyavirus,Oropouche virus | seg. L | AF484424 |
| Oropouche virus | NC_005777 | vertebrates,invertebrates, human | 2 | Bunyaviridae,Orthobunyavirus,Oropouche virus | seg. S | AY237111,AY117135 |

-continued

| Taxonomy | NCBI Reference Sequence ID | Host | No. of Genomes | Lineage | Segment Count | Genbank Accession ID |
|---|---|---|---|---|---|---|
| Orthobunyavirus BX-2010/Henan/CHN | NC_018136 | vertebrates,invertebrates, human | 3 | Bunyaviridae,Phlebovirus,Severe fever with thrombocytopenia syndrome virus | seg. L | HQ642766,JF682773, JF682776 |
| Orthobunyavirus BX-2010/Henan/CHN | NC_018137 | vertebrates,invertebrates, human | 3 | Bunyaviridae,Phlebovirus,Severe fever with thrombocytopenia syndrome virus | seg. S | HQ642768,JF682778, JF682775 |
| Orthobunyavirus BX-2010/Henan/CHN | NC_018138 | vertebrates,invertebrates, human | 3 | Bunyaviridae,Phlebovirus,Severe fever with thrombocytopenia syndrome virus | seg. M | JF682774,JF682777, HQ642767 |
| Peaton virus | NC_018463 | vertebrates,invertebrates, human | 1 | Bunyaviridae,Orthobunyavirus,Shamonda virus | seg. L | HE795093 |
| Peaton virus | NC_018464 | vertebrates,invertebrates, human | 1 | Bunyaviridae,Orthobunyavirus,Shamonda virus | seg. S | HE795095 |
| Peaton virus | NC_018467 | vertebrates,invertebrates, human | 1 | Bunyaviridae,Orthobunyavirus,Shamonda virus | seg. M | HE795094 |
| Phlebovirus J52007-01 | NC_018136 | vertebrates,invertebrates, human | 1 | Bunyaviridae,Phlebovirus,Severe fever with thrombocytopenia syndrome virus | seg. L | JF837593 |
| Phlebovirus J52007-01 | NC_018138 | vertebrates,invertebrates, human | 1 | Bunyaviridae,Phlebovirus,Severe fever with thrombocytopenia syndrome virus | seg. M | JF837594 |
| Phlebovirus J52010-014 | NC_018136 | vertebrates,invertebrates, human | 1 | Bunyaviridae,Phlebovirus,Severe fever with thrombocytopenia syndrome virus | seg. L | JQ317169 |
| Phlebovirus J52010-014 | NC_018137 | vertebrates,invertebrates, human | 1 | Bunyaviridae,Phlebovirus,Severe fever with thrombocytopenia syndrome virus | seg. S | JQ317171 |
| Phlebovirus J52010-014 | NC_018138 | vertebrates,invertebrates, human | 1 | Bunyaviridae,Phlebovirus,Severe fever with thrombocytopenia syndrome virus | seg. M | JQ317170 |
| Phlebovirus J52010-015 | NC_018136 | vertebrates,invertebrates, human | 1 | Bunyaviridae,Phlebovirus,Severe fever with thrombocytopenia syndrome virus | seg. L | JQ317172 |
| Phlebovirus J52010-015 | NC_018137 | vertebrates,invertebrates, human | 1 | Bunyaviridae,Phlebovirus,Severe fever with thrombocytopenia syndrome virus | seg. S | JQ317174 |
| Phlebovirus J52010-015 | NC_018138 | vertebrates,invertebrates, human | 1 | Bunyaviridae,Phlebovirus,Severe fever with thrombocytopenia syndrome virus | seg. M | JQ317173 |
| Phlebovirus J52010-018 | NC_018136 | vertebrates,invertebrates, human | 1 | Bunyaviridae,Phlebovirus,Severe fever with thrombocytopenia syndrome virus | seg. L | JQ317175 |
| Phlebovirus JS2010-018 | NC_018137 | vertebrates,invertebrates, human | 1 | Bunyaviridae,Phlebovirus,Severe fever with thrombocytopenia syndrome virus | seg. S | JQ317177 |
| Phlebovirus JS2010-018 | NC_018138 | vertebrates,invertebrates, human | 1 | Bunyaviridae,Phlebovirus,Severe fever with thrombocytopenia syndrome virus | seg. M | JQ317176 |
| Phlebovirus JS2010-019 | NC_018136 | vertebrates,invertebrates, human | 1 | Bunyaviridae,Phlebovirus,Severe fever with thrombocytopenia syndrome virus | seg. L | JQ317178 |
| Phlebovirus JS2010-019 | NC_018137 | vertebrates,invertebrates, human | 1 | Bunyaviridae,Phlebovirus,Severe fever with thrombocytopenia syndrome virus | seg. S | JQ317180 |
| Phlebovirus JS2010-019 | NC_018138 | vertebrates,invertebrates, human | 1 | Bunyaviridae,Phlebovirus,Severe fever with thrombocytopenia syndrome virus | seg. M | JQ317179 |
| Phlebovirus JS24 | NC_018136 | vertebrates,invertebrates, human | 1 | Bunyaviridae,Phlebovirus,Severe fever with thrombocytopenia syndrome virus | seg. L | HQ830163 |
| Phlebovirus JS24 | NC_018137 | vertebrates,invertebrates, human | 1 | Bunyaviridae,Phlebovirus,Severe fever with thrombocytopenia syndrome virus | seg. S | HQ830165 |
| Phlebovirus JS24 | NC_018138 | vertebrates,invertebrates, human | 1 | Bunyaviridae,Phlebovirus,Severe fever with thrombocytopenia syndrome virus | seg. M | HQ830164 |
| Phlebovirus JS26 | NC_018136 | vertebrates,invertebrates, human | 1 | Bunyaviridae,Phlebovirus,Severe fever with thrombocytopenia syndrome virus | seg. L | HQ830166 |

-continued

| Taxonomy | NCBI Reference Sequence ID | Host | No. of Genomes | Lineage | Segment Count | Genbank Accession ID |
|---|---|---|---|---|---|---|
| Phlebovirus JS26 | NC_018137 | vertebrates,invertebrates, human | 1 | Bunyaviridae,Phlebovirus,Severe fever with thrombocytopenia syndrome virus | seg. S | HQ830168 |
| Phlebovirus JS26 | NC_018138 | vertebrates,invertebrates, human | 1 | Bunyaviridae,Phlebovirus,Severe fever with thrombocytopenia syndrome virus | seg. M | HQ830167 |
| Phlebovirus JS6 | NC_018136 | vertebrates,invertebrates, human | 1 | Bunyaviridae,Phlebovirus,Severe fever with thrombocytopenia syndrome virus | seg. L | HQ830169 |
| Phlebovirus JS6 | NC_018137 | vertebrates,invertebrates, human | 1 | Bunyaviridae,Phlebovirus,Severe fever with thrombocytopenia syndrome virus | seg. S | HQ830171 |
| Phlebovirus JS6 | NC_018138 | vertebrates,invertebrates, human | 1 | Bunyaviridae,Phlebovirus,Severe fever with thrombocytopenia syndrome virus | seg. M | HQ830170 |
| Powassan virus | NC_003687 | vertebrates,invertebrates, human | 12 | Flaviviridae,Flavivirus,Powassan virus | — | HM440560,HM440563,HM440559,HM440558,HQ231415,EU770575,EU543649,L06436,HQ231414,HM440562,HM440561,EU670438 |
| Precarious point virus | NC_005214 | vertebrates,invertebrates, human | 1 | Bunyaviridae,Phlebovirus,Uukuniemi virus | seg. L | HM566181 |
| Precarious point virus | NC_005220 | vertebrates,invertebrates, human | 1 | Bunyaviridae,Phlebovirus,Uukuniemi virus | seg. M | HM566179 |
| Precarious point virus | NC_005221 | vertebrates,invertebrates, human | 1 | Bunyaviridae,Phlebovirus,Uukuniemi virus | seg. S | HM566180 |
| Quang Binh virus | NC_012671 | vertebrates,invertebrates, human | 1 | Flaviviridae,Flavivirus,Quang Binh virus | — | FJ644291 |
| RML-105355 virus | NC_005214 | vertebrates,invertebrates, human | 1 | Bunyaviridae,Phlebovirus,Uukuniemi virus | seg. L | JF838333 |
| RML-105355 virus | NC_005220 | vertebrates,invertebrates, human | 1 | Bunyaviridae,Phlebovirus,Uukuniemi virus | seg. M | JF838334 |
| Razdan virus | NC_022630 | vertebrates,invertebrates, human | 1 | Bunyaviridae,Phlebovirus,Razdan virus | seg. L | KC335496 |
| Razdan virus | NC_022631 | vertebrates,invertebrates, human | 1 | Bunyaviridae,Phlebovirus,Razdan virus | seg. M | KC335497 |
| Razdan virus | NC_022632 | vertebrates,invertebrates, human | 1 | Bunyaviridae,Phlebovirus,Razdan virus | seg. S | KC335498 |
| Rift Valley fever virus | NC_014395 | vertebrates,invertebrates, human | 50 | Bunyaviridae,Phlebovirus,Rift Valley fever virus | seg. S | DQ380155,DQ380159,DQ380143,DQ380150,JF311390,DQ380174,DQ380161,DQ380158,DQ380182,DQ380171,DQ380170,JF311389,JF311393,DQ380178,JF311394,JF311388,DQ380172,DQ380169,DQ380145,DQ380163,DQ380144,DQ380147,JF311387,DQ380152,DQ380165, |

| Taxonomy | NCBI Reference Sequence ID | Host | No. of Genomes | Lineage | Segment Count | Genbank Accession ID |
|---|---|---|---|---|---|---|
| Rift Valley fever virus | NC_014396 | vertebrates,invertebrates, human | 56 | Bunyaviridae,Phlebovirus,Rift Valley fever virus | seg. M | DQ380149,DQ380014 6,DQ380168,DQ380 160,DQ380154,DQ380 175,DQ380173,DQ38 0181,DQ380148,DQ3 80176,DQ380156,DQ 380153,JF311391,JF 311392,DQ380164,JF 311386,X53771,DQ3 80179,DQ380162,DQ 380157,DQ380151,D 380177,DQ380180, DQ380166,DQ38016 7 |
| Rift Valley fever virus | NC_014396 | vertebrates,invertebrates, human | 56 | Bunyaviridae,Phlebovirus,Rift Valley fever virus | seg. M | DQ380204,DQ38020 9,JF311382,JF31137 9,JF311384,DQ38018 9,DQ380203,DQ3801 98,DQ380220,DQ380 206,DQ380195,DQ38 0184,JF311385,DQ38 0202,DQ380188,M25 276,DQ380196,JF309 200,DQ380208,DQ38 0218,DQ380185,JF31 1377,JF311381,DQ38 0193,DQ380214,DQ3 80187,JF311380,DQ3 80186,DQ380190,JF3 11378,DQ380197,DQ 380199,DQ380200,D 0380183,M11157,DQ 380219,DQ380221,D 0380210,DQ380215, DQ380201,DQ38021 6,DQ380207,JF31138 3,DQ380211,EF4671 77,DQ3801 94,DQ380 212,DQ380192,DQ38 0222,DQ380191,EF4 67178,DQ380217,EF 460404,HQ00951 2,D 0380213,DQ380205 |
| Rift Valley fever virus | NC_014397 | vertebrates,invertebrates, human | 50 | Bunyaviridae,Phlebovirus,Rift Valley fever virus | seg. L | DQ375400,DQ37542 6,DQ375421,DQ3754 07,DQ375431,DQ375 398,DQ375397,JF311 371,JF311373,DQ375 |

| Taxonomy | NCBI Reference Sequence ID | Host | No. of Genomes | Lineage | Segment Count | Genbank Accession ID |
|---|---|---|---|---|---|---|
| | | | | | | 419,DQ375409,DQ37 5399,JF311368,DQ37 5406,DQ375403,DQ3 75410,DQ375429,DQ 375414,JF311375,DQ 375401,DQ375417,D 0375425,JF311369,D 0375420,DQ375424, DQ375395,DQ37541 5,DQ375432,DQ3754 22,DQ375412,DQ375 418,X56464,DQ3754 05,DQ375423,DQ375 413,DQ375427,DQ37 5434,JF311376,JF31 1372,DQ375408,DQ3 75396,JF311370,JF3 11374,DQ375433,DQ 375416,DQ375404,D 0375411,DQ375428, DQ375402,DQ37543 0 |
| Rio Bravo virus | NC_003675 | vertebrates,invertebrates, human | 2 | Flaviviridae,Flavivirus,Rio Bravo virus | — | JQ582840,AF144692 |
| Rocio virus | NC_009028 | vertebrates,invertebrates, human | 1 | Flaviviridae,Flavivirus,Ilheus virus | — | AY632542 |
| Ross River virus | NC_001544 | vertebrates,invertebrates, human | 9 | Togaviridae,Alphavirus,Ross River virus | — | GQ433355,GQ43335 7,GQ433359,GQ4333 54,GQ433356,DQ226 993,GQ433360,M201 62,GQ433358 |
| Royal Farm virus | NC_006947 | vertebrates,invertebrates, human | 1 | Flaviviridae,Flavivirus,Royal Farm virus | — | DQ235149 |
| SFTS virus AH12 | NC_018136 | vertebrates,invertebrates, human | 1 | Bunyaviridae,Phlebovirus,Severe fever with thrombocytopenia syndrome virus | seg. L | HQ116417 |
| SFTS virus AH12 | NC_018137 | vertebrates,invertebrates, human | 1 | Bunyaviridae,Phlebovirus,Severe fever with thrombocytopenia syndrome virus | seg. S | HQ141591 |
| SFTS virus AH12 | NC_018138 | vertebrates,invertebrates, human | 1 | Bunyaviridae,Phlebovirus,Severe fever with thrombocytopenia syndrome virus | seg. M | HQ141590 |
| SFTS virus AH15 | NC_018136 | vertebrates,invertebrates, human | 1 | Bunyaviridae,Phlebovirus,Severe fever with thrombocytopenia syndrome virus | seg. L | HQ141592 |
| SFTS virus AH15 | NC_018137 | vertebrates,invertebrates, human | 1 | Bunyaviridae,Phlebovirus,Severe fever with thrombocytopenia syndrome virus | seg. S | HQ141594 |
| SFTS virus AH15 | NC_018138 | vertebrates,invertebrates, human | 1 | Bunyaviridae,Phlebovirus,Severe fever with thrombocytopenia syndrome virus | seg. M | HQ141593 |
| SFTS virus HB29 | NC_018136 | vertebrates,invertebrates, human | 1 | Bunyaviridae,Phlebovirus,Severe fever with thrombocytopenia syndrome virus | seg. L | HM745930 |

-continued

| Taxonomy | NCBI Reference Sequence ID | Host | No. of Genomes | Lineage | Segment Count | Genbank Accession ID |
|---|---|---|---|---|---|---|
| SFTS virus HB29 | NC_018137 | vertebrates,invertebrates, human | 1 | Bunyaviridae,Phlebovirus,Severe fever with thrombocytopenia syndrome virus | seg. S | HM745932 |
| SFTS virus HB29 | NC_018138 | vertebrates,invertebrates, human | 1 | Bunyaviridae,Phlebovirus,Severe fever with thrombocytopenia syndrome virus | seg. M | HM745931 |
| SFTS virus HN13 | NC_018136 | vertebrates,invertebrates, human | 1 | Bunyaviridae,Phlebovirus,Severe fever with thrombocytopenia syndrome virus | seg. L | HQ141598 |
| SFTS virus HN13 | NC_018137 | vertebrates,invertebrates, human | 1 | Bunyaviridae,Phlebovirus,Severe fever with thrombocytopenia syndrome virus | seg. S | HQ141600 |
| SFTS virus HN13 | NC_018138 | vertebrates,invertebrates, human | 1 | Bunyaviridae,Phlebovirus,Severe fever with thrombocytopenia syndrome virus | seg. M | HQ141599 |
| SFTS virus HN6 | NC_018136 | vertebrates,invertebrates, human | 1 | Bunyaviridae,Phlebovirus,Severe fever with thrombocytopenia syndrome virus | seg. L | HQ141595 |
| SFTS virus HN6 | NC_018137 | vertebrates,invertebrates, human | 1 | Bunyaviridae,Phlebovirus,Severe fever with thrombocytopenia syndrome virus | seg. S | HQ141597 |
| SFTS virus HN6 | NC_018138 | vertebrates,invertebrates, human | 1 | Bunyaviridae,Phlebovirus,Severe fever with thrombocytopenia syndrome virus | seg. M | HQ141596 |
| SFTS virus HNXY_115 | NC_018136 | vertebrates,invertebrates, human | 1 | Bunyaviridae,Phlebovirus,Severe fever with thrombocytopenia syndrome virus | seg. L | KC292338 |
| SFTS virus HNXY_115 | NC_018137 | vertebrates,invertebrates, human | 1 | Bunyaviridae,Phlebovirus,Severe fever with thrombocytopenia syndrome virus | seg. S | KC292285 |
| SFTS virus HNXY_115 | NC_018138 | vertebrates,invertebrates, human | 1 | Bunyaviridae,Phlebovirus,Severe fever with thrombocytopenia syndrome virus | seg. M | KC292312 |
| SFTS virus HNXY_130 | NC_018136 | vertebrates,invertebrates, human | 1 | Bunyaviridae,Phlebovirus,Severe fever with thrombocytopenia syndrome virus | seg. L | KC292342 |
| SFTS virus HNXY_130 | NC_018137 | vertebrates,invertebrates/ human | 1 | Bunyaviridae,Phlebovirus,Severe fever with thrombocytopenia syndrome virus | seg. S | KC292289 |
| SFTS virus HNXY_130 | NC_018138 | vertebrates,invertebrates, human | 1 | Bunyaviridae,Phlebovirus,Severe fever with thrombocytopenia syndrome virus | seg. M | KC292316 |
| SFTS virus HNXY_144 | NC_018136 | vertebrates,invertebrates, human | 1 | Bunyaviridae,Phlebovirus,Severe fever with thrombocytopenia syndrome virus | seg. L | KC292333 |
| SFTS virus HNXY_144 | NC_018137 | vertebrates,invertebrates, human | 1 | Bunyaviridae,Phlebovirus,Severe fever with thrombocytopenia syndrome virus | seg. S | KC292280 |
| SFTS virus HNXY_144 | NC_018138 | vertebrates,invertebrates, human | 1 | Bunyaviridae,Phlebovirus,Severe fever with thrombocytopenia syndrome virus | seg. M | KC292307 |
| SFTS virus HNXY_157 | NC_018136 | vertebrates,invertebrates, human | 1 | Bunyaviridae,Phlebovirus,Severe fever with thrombocytopenia syndrome virus | seg. L | KC292331 |
| SFTS virus HNXY_157 | NC_018137 | vertebrates,invertebrates, human | 1 | Bunyaviridae,Phlebovirus,Severe fever with thrombocytopenia syndrome virus | seg. S | KC292278 |
| SFTS virus HNXY_157 | NC_018138 | vertebrates,invertebrates, human | 1 | Bunyaviridae,Phlebovirus,Severe fever with thrombocytopenia syndrome virus | seg. M | KC292305 |
| SFTS virus HNXY_164 | NC_018136 | vertebrates,invertebrates, human | 1 | Bunyaviridae,Phlebovirus,Severe fever with thrombocytopenia syndrome virus | seg. L | KC292340 |
| SFTS virus HNXY_164 | NC_018137 | vertebrates,invertebrates, human | 1 | Bunyaviridae,Phlebovirus,Severe fever with thrombocytopenia syndrome virus | seg. S | KC292287 |
| SFTS virus HNXY_164 | NC_018138 | vertebrates,invertebrates, human | 1 | Bunyaviridae,Phlebovirus,Severe fever with thrombocytopenia syndrome virus | seg. M | KC292314 |
| SFTS virus HNXY_170 | NC_018136 | vertebrates,invertebrates, human | 1 | Bunyaviridae,Phlebovirus,Severe fever with thrombocytopenia syndrome virus | seg. L | KC292353 |

| Taxonomy | NCBI Reference Sequence ID | Host | No. of Genomes | Lineage | Segment Count | Genbank Accession ID |
|---|---|---|---|---|---|---|
| SFTS virus HNXY_170 | NC_018137 | vertebrates,invertebrates, human | 1 | Bunyaviridae,Phlebovirus,Severe fever with thrombocytopenia syndrome virus | seg. S | KC292277 |
| SFTS virus HNXY_170 | NC_018138 | vertebrates,invertebrates, human | 1 | Bunyaviridae,Phlebovirus,Severe fever with thrombocytopenia syndrome virus | seg. M | KC292304 |
| SFTS virus HNXY_174 | NC_018136 | vertebrates,invertebrates, human | 1 | Bunyaviridae,Phlebovirus,Severe fever with thrombocytopenia syndrome virus | seg. L | KC292332 |
| SFTS virus HNXY_174 | NC_018137 | vertebrates,invertebrates, human | 1 | Bunyaviridae,Phlebovirus,Severe fever with thrombocytopenia syndrome virus | seg. S | KC292279 |
| SFTS virus HNXY_174 | NC_018138 | vertebrates,invertebrates, human | 1 | Bunyaviridae,Phlebovirus,Severe fever with thrombocytopenia syndrome virus | seg. M | KC292306 |
| SFTS virus HNXY_182 | NC_018136 | vertebrates,invertebrates, human | 1 | Bunyaviridae,Phlebovirus,Severe fever with thrombocytopenia syndrome virus | seg. L | KC292350 |
| SFTS virus HNXY_182 | NC_018137 | vertebrates,invertebrates, human | 1 | Bunyaviridae,Phlebovirus,Severe fever with thrombocytopenia syndrome virus | seg. S | KC292297 |
| SFTS virus HNXY_182 | NC_018138 | vertebrates,invertebrates, human | 1 | Bunyaviridae,Phlebovirus,Severe fever with thrombocytopenia syndrome virus | seg. M | KC292324 |
| SFTS virus HNXY_186 | NC_018136 | vertebrates,invertebrates, human | 1 | Bunyaviridae,Phlebovirus,Severe fever with thrombocytopenia syndrome virus | seg. L | KC292334 |
| SFTS virus HNXY_186 | NC_018137 | vertebrates,invertebrates, human | 1 | Bunyaviridae,Phlebovirus,Severe fever with thrombocytopenia syndrome virus | seg. S | KC292281 |
| SFTS virus HNXY_186 | NC_018138 | vertebrates,invertebrates, human | 1 | Bunyaviridae,Phlebovirus,Severe fever with thrombocytopenia syndrome virus | seg. M | KC292308 |
| SFTS virus HNXY_188 | NC_018136 | vertebrates,invertebrates, human | 1 | Bunyaviridae,Phlebovirus,Severe fever with thrombocytopenia syndrome virus | seg. L | KC292328 |
| SFTS virus HNXY_188 | NC_018137 | vertebrates,invertebrates, human | 1 | Bunyaviridae,Phlebovirus,Severe fever with thrombocytopenia syndrome virus | seg. S | KC292274 |
| SFTS virus HNXY_188 | NC_018138 | vertebrates,invertebrates, human | 1 | Bunyaviridae,Phlebovirus,Severe fever with thrombocytopenia syndrome virus | seg. M | KC292301 |
| SFTS virus HNXY_191 | NC_018136 | vertebrates,invertebrates, human | 1 | Bunyaviridae,Phlebovirus,Severe fever with thrombocytopenia syndrome virus | seg. L | KC292349 |
| SFTS virus HNXY_191 | NC_018137 | vertebrates,invertebrates, human | 1 | Bunyaviridae,Phlebovirus,Severe fever with thrombocytopenia syndrome virus | seg. S | KC292296 |
| SFTS virus HNXY_191 | NC_018138 | vertebrates,invertebrates, human | 1 | Bunyaviridae,Phlebovirus,Severe fever with thrombocytopenia syndrome virus | seg. M | KC292323 |
| SFTS virus HNXY_195 | NC_018136 | vertebrates,invertebrates, human | 1 | Bunyaviridae,Phlebovirus,Severe fever with thrombocytopenia syndrome virus | seg. L | KC292352 |
| SFTS virus HNXY_195 | NC_018137 | vertebrates,invertebrates, human | 1 | Bunyaviridae,Phlebovirus,Severe fever with thrombocytopenia syndrome virus | seg. S | KC292299 |
| SFTS virus HNXY_195 | NC_018138 | vertebrates,invertebrates, human | 1 | Bunyaviridae,Phlebovirus,Severe fever with thrombocytopenia syndrome virus | seg. M | KC292326 |
| SFTS virus HNXY_2 | NC_018136 | vertebrates,invertebrates, human | 1 | Bunyaviridae,Phlebovirus,Severe fever with thrombocytopenia syndrome virus | seg. L | KC292344 |
| SFTS virus HNXY_2 | NC_018137 | vertebrates,invertebrates, human | 1 | Bunyaviridae,Phlebovirus,Severe fever with thrombocytopenia syndrome virus | seg. S | KC292291 |
| SFTS virus HNXY_2 | NC_018138 | vertebrates,invertebrates, human | 1 | Bunyaviridae,Phlebovirus,Severe fever with thrombocytopenia syndrome virus | seg. M | KC292318 |
| SFTS virus HNXY_202 | NC_018136 | vertebrates,invertebrates, human | 1 | Bunyaviridae,Phlebovirus,Severe fever with thrombocytopenia syndrome virus | seg. L | KC292351 |

| Taxonomy | NCBI Reference Sequence ID | Host | No. of Genomes | Lineage | Segment Count | Genbank Accession ID |
|---|---|---|---|---|---|---|
| SFTS virus HNXY_202 | NC_018137 | vertebrates,invertebrates, human | 1 | Bunyaviridae,Phlebovirus,Severe fever with thrombocytopenia syndrome virus | seg. S | KC292298 |
| SFTS virus HNXY_202 | NC_018138 | vertebrates,invertebrates, human | 1 | Bunyaviridae,Phlebovirus,Severe fever with thrombocytopenia syndrome virus | seg. M | KC292325 |
| SFTS virus HNXY_206 | NC_018136 | vertebrates,invertebrates, human | 1 | Bunyaviridae,Phlebovirus,Severe fever with thrombocytopenia syndrome virus | seg. L | KC292329 |
| SFTS virus HNXY_206 | NC_018137 | vertebrates,invertebrates, human | 1 | Bunyaviridae,Phlebovirus,Severe fever with thrombocytopenia syndrome virus | seg. S | KC292275 |
| SFTS virus HNXY_206 | NC_018138 | vertebrates,invertebrates, human | 1 | Bunyaviridae,Phlebovirus,Severe fever with thrombocytopenia syndrome virus | seg. M | KC292302 |
| SFTS virus HNXY_207 | NC_018136 | vertebrates,invertebrates, human | 1 | Bunyaviridae,Phlebovirus,Severe fever with thrombocytopenia syndrome virus | seg. L | KC292341 |
| SFTS virus HNXY_207 | NC_018137 | vertebrates,invertebrates, human | 1 | Bunyaviridae,Phlebovirus,Severe fever with thrombocytopenia syndrome virus | seg. S | KC292288 |
| SFTS virus HNXY_207 | NC_018138 | vertebrates,invertebrates, human | 1 | Bunyaviridae,Phlebovirus,Severe fever with thrombocytopenia syndrome virus | seg. M | KC292315 |
| SFTS virus HNXY_212 | NC_018136 | vertebrates,invertebrates, human | 1 | Bunyaviridae,Phlebovirus,Severe fever with thrombocytopenia syndrome virus | seg. L | KC292327 |
| SFTS virus HNXY_212 | NC_018137 | vertebrates,invertebrates, human | 1 | Bunyaviridae,Phlebovirus,Severe fever with thrombocytopenia syndrome virus | seg. S | KC292273 |
| SFTS virus HNXY_212 | NC_018138 | vertebrates,invertebrates, human | 1 | Bunyaviridae,Phlebovirus,Severe fever with thrombocytopenia syndrome virus | seg. M | KC292300 |
| SFTS virus HNXY_224 | NC_018136 | vertebrates,invertebrates, human | 1 | Bunyaviridae,Phlebovirus,Severe fever with thrombocytopenia syndrome virus | seg. L | KC292343 |
| SFTS virus HNXY_224 | NC_018137 | vertebrates,invertebrates, human | 1 | Bunyaviridae,Phlebovirus,Severe fever with thrombocytopenia syndrome virus | seg. S | KC292290 |
| SFTS virus HNXY_224 | NC_018138 | vertebrates,invertebrates, human | 1 | Bunyaviridae,Phlebovirus,Severe fever with thrombocytopenia syndrome virus | seg. M | KC292317 |
| SFTS virus HNXY_231 | NC_018136 | vertebrates,invertebrates, human | 1 | Bunyaviridae,Phlebovirus,Severe fever with thrombocytopenia syndrome virus | seg. L | KC292339 |
| SFTS virus HNXY_231 | NC_018137 | vertebrates,invertebrates, human | 1 | Bunyaviridae,Phlebovirus,Severe fever with thrombocytopenia syndrome virus | seg. S | KC292286 |
| SFTS virus HNXY_231 | NC_018138 | vertebrates,invertebrates, human | 1 | Bunyaviridae,Phlebovirus,Severe fever with thrombocytopenia syndrome virus | seg. M | KC292313 |
| SFTS virus HNXY_245 | NC_018136 | vertebrates,invertebrates, human | 1 | Bunyaviridae,Phlebovirus,Severe fever with thrombocytopenia syndrome virus | seg. L | KC292346 |
| SFTS virus HNXY_245 | NC_018137 | vertebrates,invertebrates, human | 1 | Bunyaviridae,Phlebovirus,Severe fever with thrombocytopenia syndrome virus | seg. S | KC292293 |
| SFTS virus HNXY_245 | NC_018138 | vertebrates,invertebrates, human | 1 | Bunyaviridae,Phlebovirus,Severe fever with thrombocytopenia syndrome virus | seg. M | KC292320 |
| SFTS virus HNXY_262 | NC_018136 | vertebrates,invertebrates, human | 1 | Bunyaviridae,Phlebovirus,Severe fever with thrombocytopenia syndrome virus | seg. L | KC292335 |
| SFTS virus HNXY_262 | NC_018137 | vertebrates,invertebrates, human | 1 | Bunyaviridae,Phlebovirus,Severe fever with thrombocytopenia syndrome virus | seg. S | KC292282 |
| SFTS virus HNXY_262 | NC_018138 | vertebrates,invertebrates, human | 1 | Bunyaviridae,Phlebovirus,Severe fever with thrombocytopenia syndrome virus | seg. M | KC292309 |
| SFTS virus HNXY_278 | NC_018136 | vertebrates,invertebrates, human | 1 | Bunyaviridae,Phlebovirus,Severe fever with thrombocytopenia syndrome virus | seg. L | KC292348 |

| Taxonomy | NCBI Reference Sequence ID | Host | No. of Genomes | Lineage | Segment Count | Genbank Accession ID |
|---|---|---|---|---|---|---|
| SFTS virus HNXY_278 | NC_018137 | vertebrates,invertebrates, human | 1 | Bunyaviridae,Phlebovirus,Severe fever with thrombocytopenia syndrome virus | seg. S | KC292295 |
| SFTS virus HNXY_278 | NC_018138 | vertebrates,invertebrates, human | 1 | Bunyaviridae,Phlebovirus,Severe fever with thrombocytopenia syndrome virus | seg. M | KC292322 |
| SFTS virus HNXY_293 | NC_018136 | vertebrates,invertebrates, human | 1 | Bunyaviridae,Phlebovirus,Severe fever with thrombocytopenia syndrome virus | seg. L | KC292330 |
| SFTS virus HNXY_293 | NC_018137 | vertebrates,invertebrates, human | 1 | Bunyaviridae,Phlebovirus,Severe fever with thrombocytopenia syndrome virus | seg. S | KC292276 |
| SFTS virus HNXY_293 | NC_018138 | vertebrates,invertebrates, human | 1 | Bunyaviridae,Phlebovirus,Severe fever with thrombocytopenia syndrome virus | seg. M | KC292303 |
| SFTS virus HNXY_31 | NC_018136 | vertebrates,invertebrates, human | 1 | Bunyaviridae,Phlebovirus,Severe fever with thrombocytopenia syndrome virus | seg. L | KC292336 |
| SFTS virus HNXY_31 | NC_018137 | vertebrates,invertebrates, human | 1 | Bunyaviridae,Phlebovirus,Severe fever with thrombocytopenia syndrome virus | seg. S | KC292283 |
| SFTS virus HNXY_31 | NC_018138 | vertebrates,invertebrates, human | 1 | Bunyaviridae,Phlebovirus,Severe fever with thrombocytopenia syndrome virus | seg. M | KC292310 |
| SFTS virus HNXY_319 | NC_018136 | vertebrates,invertebrates, human | 1 | Bunyaviridae,Phlebovirus,Severe fever with thrombocytopenia syndrome virus | seg. L | KC292345 |
| SFTS virus HNXY_319 | NC_018137 | vertebrates,invertebrates, human | 1 | Bunyaviridae,Phlebovirus,Severe fever with thrombocytopenia syndrome virus | seg. S | KC292292 |
| SFTS virus HNXY_319 | NC_018138 | vertebrates,invertebrates, human | 1 | Bunyaviridae,Phlebovirus,Severe fever with thrombocytopenia syndrome virus | seg. M | KC292319 |
| SFTS virus HNXY_327 | NC_018136 | vertebrates,invertebrates, human | 1 | Bunyaviridae,Phlebovirus,Severe fever with thrombocytopenia syndrome virus | seg. L | KC292347 |
| SFTS virus HNXY_327 | NC_018137 | vertebrates,invertebrates, human | 1 | Bunyaviridae,Phlebovirus,Severe fever with thrombocytopenia syndrome virus | seg. S | KC292294 |
| SFTS virus HNXY_327 | NC_018138 | vertebrates,invertebrates, human | 1 | Bunyaviridae,Phlebovirus,Severe fever with thrombocytopenia syndrome virus | seg. M | KC292321 |
| SFTS virus HNXY_93 | NC_018136 | vertebrates,invertebrates, human | 1 | Bunyaviridae,Phlebovirus,Severe fever with thrombocytopenia syndrome virus | seg. L | KC292337 |
| SFTS virus HNXY_93 | NC_018137 | vertebrates,invertebrates, human | 1 | Bunyaviridae,Phlebovirus,Severe fever with thrombocytopenia syndrome virus | seg. S | KC292284 |
| SFTS virus HNXY_93 | NC_018138 | vertebrates,invertebrates, human | 1 | Bunyaviridae,Phlebovirus,Severe fever with thrombocytopenia syndrome virus | seg. M | KC292311 |
| SFTS virus JS3 | NC_018136 | vertebrates,invertebrates, human | 1 | Bunyaviridae,Phlebovirus,Severe fever with thrombocytopenia syndrome virus | seg. L | HQ141601 |
| SFTS virus JS3 | NC_018137 | vertebrates,invertebrates, human | 1 | Bunyaviridae,Phlebovirus,Severe fever with thrombocytopenia syndrome virus | seg. S | HQ141603 |
| SFTS virus JS3 | NC_018138 | vertebrates,invertebrates, human | 1 | Bunyaviridae,Phlebovirus,Severe fever with thrombocytopenia syndrome virus | seg. M | HQ141602 |
| SFTS virus JS4 | NC_018136 | vertebrates,invertebrates, human | 1 | Bunyaviridae,Phlebovirus,Severe fever with thrombocytopenia syndrome virus | seg. L | HQ141604 |
| SFTS virus JS4 | NC_018137 | vertebrates,invertebrates, human | 1 | Bunyaviridae,Phlebovirus,Severe fever with thrombocytopenia syndrome virus | seg. S | HQ141606 |
| SFTS virus JS4 | NC_018138 | vertebrates,invertebrates, human | 1 | Bunyaviridae,Phlebovirus,Severe fever with thrombocytopenia syndrome virus | seg. M | HQ141605 |
| SFTS virus LN2 | NC_018136 | vertebrates,invertebrates, human | 1 | Bunyaviridae,Phlebovirus,Severe fever with thrombocytopenia syndrome virus | seg. L | HQ141607 |

| Taxonomy | NCBI Reference Sequence ID | Host | No. of Genomes | Lineage | Segment Count | Genbank Accession ID |
|---|---|---|---|---|---|---|
| SFTS virus LN2 | NC_018137 | vertebrates,inv -continued

| Taxonomy | NCBI Reference Sequence ID | Host | No. of Genomes | Lineage | Segment Count | Genbank Accession ID |
|---|---|---|---|---|---|---|
| Sandfly fever Naples virus | NC_006318 | vertebrates,invertebrates, human | 8 | Bunyaviridae,Phlebovirus,Sandfly fever Naples virus | seg. S | EF201831,HM566170,HM566168,EF201828,EF201832,X53794,EF201829,EF201830 |
| Sandfly fever Naples virus | NC_006319 | vertebrates,invertebrates, human | 3 | Bunyaviridae,Phlebovirus,Sandfly fever Naples virus | seg. L | HM566172,X68414,HM566167 |
| Sandfly fever Naples virus | NC_006320 | vertebrates,invertebrates, human | 3 | Bunyaviridae,Phlebovirus,Sandfly fever Naples virus | seg. M | HM566171,HM566169,X89628 |
| Sandfly fever sicilian virus | NC_015411 | vertebrates,invertebrates, human | 1 | Bunyaviridae,Phlebovirus,Sandfly fever Sicilian virus | seg. M | U30500 |
| Sandfly fever sicilian virus | NC_015413 | vertebrates,invertebrates, human | 9 | Bunyaviridae,Phlebovirus,Sandfly fever Sicilian virus | seg. S | EF201826,AJ811547,EF201825,EF201822,JQ4418,EF201824,EF201823,EF201827,GU119908 |
| Sango virus | NC_018463 | vertebrates,invertebrates, human | 1 | Bunyaviridae,Orthobunyavirus,Shamonda virus | seg. L | HE795099 |
| Sango virus | NC_018464 | vertebrates,invertebrates, human | 1 | Bunyaviridae,Orthobunyavirus,Shamonda virus | seg. S | HE795101 |
| Sango virus | NC_018467 | vertebrates,invertebrates, human | 1 | Bunyaviridae,Orthobunyavirus,Shamonda virus | seg. M | HE795100 |
| Sathuperi virus | NC_018461 | vertebrates,invertebrates, human | 1 | Bunyaviridae,Orthobunyavirus,Sathuperi virus | seg. L | HE795102 |
| Sathuperi virus | NC_018462 | vertebrates,invertebrates, human | 1 | Bunyaviridae,Orthobunyavirus,Sathuperi virus | seg. S | HE795104 |
| Sathuperi virus | NC_018466 | vertebrates,invertebrates, human | 1 | Bunyaviridae,Orthobunyavirus,Sathuperi virus | seg. M | HE795103 |
| Sepik virus | NC_008719 | vertebrates,invertebrates, human | 2 | Flaviviridae,Flavivirus,Sepik virus | — | DQ837642,AY632543 |
| Serra Norte virus | NC_015373 | vertebrates,invertebrates, human | 1 | Bunyaviridae,Phlebovirus,Candiru virus | seg. M | HM119429 |
| Serra Norte virus | NC_015374 | vertebrates,invertebrates, human | 1 | Bunyaviridae,Phlebovirus,Candiru virus | seg. L | HM119428 |
| Serra Norte virus | NC_015375 | vertebrates,invertebrates, human | 1 | Bunyaviridae,Phlebovirus,Candiru virus | seg. S | HM119430 |
| Serra do Navio virus | NC_004110 | vertebrates,invertebrates, human | 1 | Bunyaviridae,Orthobunyavirus,California encephalitis virus | seg. S | U47140 |
| Severe fever with thrombocytopenia syndrome virus | NC_018136 | vertebrates,invertebrates, human | 24 | Bunyaviridae,Phlebovirus,Severe fever with thrombocytopenia syndrome virus | seg. L | KC505123,JQ733561,KC505126,AB817985,AB817984,JQ733564,JQ733567,JQ670934,KC505129,AB817983,KC473540,JQ684871,KC505135,KC505132,AB817982,AB817979,AB817981,KC |

| Taxonomy | NCBI Reference Sequence ID | Host | No. of Genomes | Lineage | Segment Count | Genbank Accession ID |
|---|---|---|---|---|---|---|
| Severe fever with thrombocytopenia syndrome virus | NC_018137 | vertebrates,invertebrates, human | 36 | Bunyaviridae,Phlebovirus,Severe fever with thrombocytopenia syndrome virus | seg. S | 505138,JQ670929,KC50141,AB817980,KC505144,KC473537,AB817986,AB817997,KC505131,JQ693005,JQ693008,AB817996,KC505134,JQ670933,AB818002,KC505146,JQ693006,KC473539,JQ670932,KC505140,KC505125,JQ733565,JQ693007,AB817998,JQ733562,AB818000,JQ733568,KC473542,JQ693010,AB817995,AB93010,AB817995,AB818001,JQ693011,JQ693002,KC505128,JQ693009,KC505143,JQ693003,JQ693001,JQ693012,AB817999,JQ684873,JQ693004,JQ693013 |
| Severe fever with thrombocytopenia syndrome virus | NC_018138 | vertebrates,invertebrates, human | 24 | Bunyaviridae,Phlebovirus,Severe fever with thrombocytopenia syndrome virus | seg. M | KC473538,KC505136,KC505145,JQ733356,KC473541,KC505139,AB817992,AB817994,JQ670930,AB817990,AB817988,KC505142,AB817993,AB817989,JQ684872,JQ733563,KC505127,KC505130,JQ733560,AB817987,AB817991,KC505133,KC505124,JQ670931 |
| Shamonda virus | NC_018463 | vertebrates,invertebrates, human | 1 | Bunyaviridae,Orthobunyavirus,Shamonda virus | seg. L | HE795105 |
| Shamonda virus | NC_018464 | vertebrates,invertebrates, human | 1 | Bunyaviridae,Orthobunyavirus,Shamonda virus | seg. S | HE795107 |
| Shamonda virus | NC_018467 | vertebrates,invertebrates, human | 1 | Bunyaviridae,Orthobunyavirus,Shamonda virus | seg. M | HE795106 |
| Shokwe virus | NC_001927 | vertebrates,invertebrates, human | 1 | Bunyaviridae,Orthobunyavirus,Bunyamwera virus | seg. S | EU564831 |
| Simbu virus | NC_018476 | vertebrates,invertebrates, human | 1 | Bunyaviridae,Orthobunyavirus,Simbu virus | seg. L | HE795108 |
| Simbu virus | NC_018477 | vertebrates,invertebrates, human | 1 | Bunyaviridae,Orthobunyavirus,Simbu virus | seg. S | HE795110 |

-continued

| Taxonomy | NCBI Reference Sequence ID | Host | No. of Genomes | Lineage | Segment Count | Genbank Accession ID |
|---|---|---|---|---|---|---|
| Simbu virus | NC_018478 | vertebrates,invertebrates,human | 1 | Bunyaviridae,Orthobunyavirus,Simbu virus | seg. M | HE795109 |
| Sitiawan virus | NC_015843 | vertebrates,invertebrates,human | 1 | Flaviviridae,Flavivirus,Tembusu virus | — | JX477686 |
| Snowshoe hare virus | NC_004108 | vertebrates,invertebrates,human | 1 | Bunyaviridae,Orthobunyavirus,California encephalitis virus | seg. L | EU203678 |
| Snowshoe hare virus | NC_004109 | vertebrates,invertebrates,human | 2 | Bunyaviridae,Orthobunyavirus,California encephalitis virus | seg. M | K02539,EU262553 |
| Snowshoe hare virus | NC_004110 | vertebrates,invertebrates,human | 2 | Bunyaviridae,Orthobunyavirus,California encephalitis virus | seg. S | EU294510,JQ2390 |
| South River virus | NC_004109 | vertebrates,invertebrates,human | 1 | Bunyaviridae,Orthobunyavirus,California encephalitis virus | seg. M | AF123488 |
| St.Louis encephalitis virus | NC_007580 | vertebrates,invertebrates,human | 9 | Flaviviridae,Flavivirus,St.Louis encephalitis virus | — | JQ957868,FJ753287, FJ753286,JF460774, DQ359217,JQ957869, EU566860,AY63254 4,DQ525916 |
| Tahyna virus | NC_004109 | vertebrates,invertebrates,human | 2 | Bunyaviridae,Orthobunyavirus,California encephalitis virus | seg. M | AF123485,AF229129 |
| Tahyna virus | NC_004110 | vertebrates,invertebrates,human | 2 | Bunyaviridae,Orthobunyavirus,California encephalitis virus | seg. S | U47142,Z68497 |
| Tamana bat virus | NC_003996 | vertebrates,invertebrates,human | 2 | Flaviviridae,Flavivirus,Tamana bat virus | — | AF285080,AF346759 |
| Tembusu virus | NC_015843 | vertebrates,invertebrates,human | 18 | Flaviviridae,Flavivirus,Tembusu virus | — | KF557894,KF192951, JQ595407,JX477685, JQ314464,JF895923, KC333867,JX549382, JX965381,JQ928189, JN811558,JX273153, JF270480,JF459991, JQ314465,KF557893, KC136210,JN811559 |
| Thogoto virus | NC_006495 | vertebrates,invertebrates,human | 1 | Orthomyxoviridae,Thogotovirus,Thogoto virus | seg. 2 | AF004985 |
| Thogoto virus | NC_006496 | vertebrates,invertebrates,human | 2 | Orthomyxoviridae,Thogotovirus,Thogoto virus | seg. 3 | AF006073,DQ0540 |
| Thogoto virus | NC_006504 | vertebrates,invertebrates,human | 4 | Orthomyxoviridae,Thogotovirus,Thogoto virus | seg. 6 | AF527531,AF527529, AF236794,AF527530 |
| Thogoto virus | NC_006506 | vertebrates,invertebrates,human | 1 | Orthomyxoviridae,Thogotovirus,Thogoto virus | seg. 4 | M77280 |
| Thogoto virus | NC_006507 | vertebrates,invertebrates,human | 1 | Orthomyxoviridae,Thogotovirus,Thogoto virus | seg. 5 | X96872 |
| Thogoto virus | NC_006508 | vertebrates,invertebrates,human | 1 | Orthomyxoviridae,Thogotovirus,Thogoto virus | seg. 1 | Y17873 |
| Tick-borne encephalitis virus | NC_001672 | vertebrates,invertebrates,human | 78 | Flaviviridae,Flavivirus,Tick-borne encephalitis virus | — | JQ825149,FJ402886, EU816454,EU816452, JQ825163,JF316707, GQ228395,EU81645 |

| Taxonomy | NCBI Reference Sequence ID | Host | No. of Genomes | Lineage | Segment Count | Genbank Accession ID |
|---|---|---|---|---|---|---|
| | | | | | | 3,U27495,KC422663, EU816451,JQ825160 ,FJ572210,GU183383 ,KC414090,JQ825215 0,AY169390,AF52741 5,JQ654701,HM1208 75,HM533611,JN229 223,JQ650522,FJ968 751,GU183379,JQ82 5161,AB062064

-continued

| Taxonomy | NCBI Reference Sequence ID | Host | No. of Genomes | Lineage | Segment Count | Genbank Accession ID |
|---|---|---|---|---|---|---|
| Toscana virus | NC_006320 | vertebrates,invertebrates, human | 12 | Bunyaviridae,Phlebovirus,Sandfly fever Naples virus | seg. M | JF330280,EU003178, EU003175,EU003179 ,EU003180,EU00317 7,EU003174,JF33027 9,EU003176,KC7762 15,EU003173,JX8675 35 |
| Tribec virus | NC_014522 | vertebrates,invertebrates,, human | 2 | Reoviridae,Orbivirus,Great Island virus | seg. 1 | HQ266581,HM54347 8 |
| Tribec virus | NC_014523 | vertebrates,invertebrates, human | 2 | Reoviridae,Orbivirus,Great Island virus | seg. 2 | HQ266582,HM54347 9 |
| Tribec virus | NC_014524 | vertebrates,invertebrates, human | 1 | Reoviridae,Orbivirus,Great Island virus | seg. 3 | HQ266583 |
| Tribec virus | NC_014525 | vertebrates,invertebrates, human | 1 | Reoviridae,Orbivirus,Great Island virus | seg. 4 | HQ266584 |
| Tribec virus | NC_014526 | vertebrates,invertebrates, human | 1 | Reoviridae,Orbivirus,Great Island virus | seg. 5 | HQ266585 |
| Tribec virus | NC_014527 | vertebrates,invertebrates, human | 2 | Reoviridae,Orbivirus,Great Island virus | seg. 6 | HM543480,HQ26658 6 |
| Tribec virus | NC_014528 | vertebrates,invertebrates, human | 1 | Reoviridae,Orbivirus,Great Island virus | seg. 7 | HQ266587 |
| Tribec virus | NC_014529 | vertebrates,invertebrates, human | 1 | Reoviridae,Orbivirus,Great Island virus | seg. 8 | HQ266588 |
| Tribec virus | NC_014530 | vertebrates,invertebrates, human | 1 | Reoviridae,Orbivirus,Great Island virus | seg. 9 | HQ266589 |
| Tribec virus | NC_014531 | vertebrates,invertebrates, human | 1 | Reoviridae,Orbivirus,Great Island virus | seg. 10 | HQ266590 |
| Trivittatus virus | NC_004109 | vertebrates,invertebrates, human | 1 | Bunyaviridae,Orthobunyavirus,California encephalitis virus | seg. M | AF123491 |
| Trivittatus virus | NC_004110 | vertebrates,invertebrates, human | 1 | Bunyaviridae,Orthobunyavirus,California encephalitis virus | seg. S | U12803 |
| Turuna virus | NC_015373 | vertebrates,invertebrates, human | 1 | Bunyaviridae,Phlebovirus,Candiru virus | seg. M | HM119432 |
| Turuna virus | NC_015374 | vertebrates,invertebrates, human | 1 | Bunyaviridae,Phlebovirus,Candiru virus | seg. L | HM119431 |
| Turuna virus | NC_015375 | vertebrates,invertebrates, human | 1 | Bunyaviridae,Phlebovirus,Candiru virus | seg. S | HM119433 |
| Tyuleniy virus | NC_023424 | vertebrates,invertebrates, human | 1 | Flaviviridae,Flavivirus,Tyuleniy virus | | KF815939 |
| Usutu virus | NC_006551 | vertebrates,invertebrates, human | 10 | Flaviviridae,Flavivirus,Usutu virus | | KC754957,EF206350 ,KC754955,JF266698 ,KC754958,AY45341 1,AY453412,JQ21984 3,KC754954,KC7549 56 |
| Uukuniemi virus | NC_005214 | vertebrates,invertebrates, human | 1 | Bunyaviridae,Phlebovirus,Uukuniemi virus | seg. L | D10759 |

-continued

| Taxonomy | NCBI Reference Sequence ID | Host | No. of Genomes | Lineage | Segment Count | Genbank Accession ID |
|---|---|---|---|---|---|---|
| Uukuniemi virus | NC_005220 | vertebrates,invertebrates,human | 1 | Bunyaviridae,Phlebovirus,Uukuniemi virus | seg. M | M17417 |
| Uukuniemi virus | NC_005221 | vertebrates,invertebrates,human | 1 | Bunyaviridae,Phlebovirus,Uukuniemi virus | seg. S | M33551 |
| Wesselsbron virus | NC_012735 | vertebrates,invertebrates,human | 2 | Flaviviridae,Flavivirus,Wesselsbron virus | — | EU707555,JN226796 |
| West Nile virus | NC_001563 | vertebrates,invertebrates,human | 681 | Flaviviridae,Flavivirus,West Nile virus | — | JN819317,FJ425721,HQ671721,JN858069,DQ080059,HQ67169 9,HM488219,JX5030 87,GQ507482,JF899 537,CS568918,JX503 084,HM488220,HM48 8126,DQ080062,DQ4 31701,JF957169,JF9 20749,EU068667,DQ 164187,JQ928174,H M488211,JF920754,J F415922,KF647249,J F957167,HQ671688, DQ080070,JF957180, JF357960,JF899530, KF588365,JF920746, JF415927,HQ671670, DQ411030,AF196835 ,JF488096,HM48820 1,HQ671673,JF48808 7,HM488165,AF4047 56,GQ379156,JF730 043,HM488173,JF48 8086,HQ671718,HQ6 71720,KC736498,HM 488129,KC736486,M 12294,JF415919,HM 488181,AY262283,JF 920752,HQ671679,JF 920759,KC711059,H M488132,GQ903680, KC711057,GQ37915 8,HM756672,JF9571 62,DQ080067,JF9207 33,HM488156,DQ431 712,HM488135,JN81 9311,HM756649,HM4 88160,HQ705670,JF8 99534,JN819319,JF9 57182,JF920307,DQ4 31693,KC736493,HM |

| Taxonomy | NCBI Reference Sequence ID | Host | No. of Genomes | Lineage | Segment Count | Genbank Accession ID |
|---|---|---|---|---|---|---|
| | | | | | | 756656,JX503092,H M488235,HM756663, JN183885,JF415930, JN819323,JXQ41628, HM756664,HM75665 1,DQ080069,JF41592 6,JQ700439,HM4881 79,JF957185,KC7364 89,KJ145832,HM488 209,DQ411035,AB18 5916,JXQ15520,HQ6 71722,JF920747,HM 488207,HQ705671,H M488170,GQ379161, KC736487,HM48825 0,DQ374653,JF92073 8,JN819320,HQ6716 96,DQ411032,HQ671 700,HM488164,HQ67 1707,HQ671687,GQ5 07473,KC736492,DQ 080065,HQ705674,JF 415918,JX503093,H M488233,HM488218, AY795965,HQ671692 ,HM488172,DQ37717 8,FJ151394,HM7566 57,AF260967,KC407 673,DQ431694,HQ67 1691,JF415929,HM4 88185,DQ116961,HM 488195,JF488089,JF 957171,HM756677,F J527738,HQ671702,J F899532,HM488197, GQ507484,JF357958 ,HM488159,DQ37718 0,HM488144,JQ7004 41,HQ671731,DQ431 708,DQ411031,JF957 176,JN183886,JXQ15 519,HM488131,KF64 7251,HM488230,DQO 80068,HM488232,DO 983578,HM756671,H M488124,JF415925, HQ671727,DQ37465 0,KC736501,DQ0800 |

| Taxonomy | NCBI Reference Sequence ID | Host | No. of Genomes | Lineage | Segment Count | Genbank Accession ID |
|---|---|---|---|---|---|---|
| | | | | | | 51,JN819310,AF4047 53,HM488148,JF703 162,HM488134,DQ43 1703,HM756660,HM7 56648,JF730042,JF7 19068,HM488182,JF 415924,JF957184,H M448163,HQ705675, AY712945,JF920735, HM488251,HM48824 5,JF920729,HQ70567 2,JN716371,HM1478 23,JF920739,HM488 189,HM488242,HM48 8246,DQ164204,HQ7 05660,HQ617719,GQ 507472,JF719067,JX 015521,FJ159129,JF 957175,HQ671671,D 0164198,HQ671695, DQ411034,KC407666 ,GQ507470,GQ50747 8,HM488217,HM4881 71,JX123031,HQ671 708,AF206518,HQ67 1681,HM488118,JF9 20731,DQ374652,DQ 164200,HQ671684,E U081844,JN819305,J F920744,AY278442,J XQ15516,JF899536,K C736495,DQ431702, HM488137,DQ43171 0,HM488213,AY5326 65,HM488125,JX503 088,HM756654,JF41 5915,HQ705669,JF95 7179,HQ671728,JN8 19307,GQ507477,JN 183887,KC736500,H 0891013,HM488149, HQ537483,JQ700438 ,GQ507481,JF73004 0,AY277252,JF95716 4,HM488123,EF5718 54,HM756668,HQ671 732,JF957186,HM48 8130,AY268132,DQ1 |

| Taxonomy | NCBI Reference Sequence ID | Host | No. of Genomes | Lineage | Segment Count | Genbank Accession ID |
|---|---|---|---|---|---|---|
| | | | | | | 64206,DQ431707,HQ671677,HM147822,AF404757,HQ671680,GU828002,JF920740,HM756670,EF657887,JF957168,JXQ41632,HQ671705,AY701413,AY660002,GU011992,AF404755,HM488210,JF784158,HM488154,HQ671694,JF920757,HM488150,JX503089,CS568919,DQO80054,JF920750,AY712946,AF260969,HM488192,CS568917,HM488147,KF179639,DQ411033,HM488183,HQ671689,HM488205,HM488252,JF920745,HQ671711,EF530047,GU828000,HQ671682,KF647253,HQ671683,JN183888,HQ671742,JF415920,HM488157,AY277251,JF957161,HM488216,JF411043,GQ507480,JX503094,JF957181,HQ891012,HM756667,HQ671713,HM488136,HQ671733,JF488091,HM488187,HQ671674,AB185915,JF488093,GQ379159,HQ705677,DQ164195,HM488248,KC736502,D0164202,JF957165,HM488184,HQ671730,JF899533,DQ164186,JQ700442,HM488228,DQ176637,AF404754,JXQ15522,DQ176636,HM488146,AB185917,KC601756,HM488222,HM756675,GU828003,HM756665,HM488151,HM488115,H |

| Taxonomy | NCBI Reference Sequence ID | Host | No. of Genomes | Lineage | Segment Count | Genbank Accession ID |
|---|---|---|---|---|---|---|
| | | | | | | 0671706,GQ507474, GU828001,EU249803 ,AF533540,JXQ41631 ,AF260968,KC73649 0,DQ431699,DQ0800 64,HM488234,DQ164 190,JN183896,HM48 8198,HM488253,JF7 07789,JF920737,HM 488208,JXQ70655,H Q671717,JN183892, HQ671693,FJ159131, HM756652,DQ41102 9,DQ080060,KF1796 40,DQ666449,JX556 213,HQ891010,HM48 8249,HM488119,JN1 83894,HM488204,DQ 080052,HM488145,J 0700440,HM488193, HM488116,HM48817 4,JF920753,DQ08007 2,DQ377179,HM7566 66,GU827999,AY289 214,HM488229,HM48 8186,CS568914,HM7 56661,HM756678,JF 703161,HM488227,H M756659,AF202541, EU155484,DQ431695 ,HQ671716,AF31720 3,DQ431709,JF92074 1,DQ431697,HM4881 77,HM488221,JX503 099,GQ507475,JXQ1 5523,DQ164194,HQ6 71703,HM488140,HQ 671669,HM488231,D 0164205,FJ159130,H M488196,DQ164189, HM488190,JF920748 ,HQ671724,JN81931 6,HM488141,JX5030 95,DQ080061,JF9203 06,HQ671698,JN819 309,HM488226,HM48 8247,JF920728,JF89 9529,HM488254,DQ3 |

| Taxonomy | NCBI Reference Sequence ID | Host | No. of Genomes | Lineage | Segment Count | Genbank Accession ID |
|---|---|---|---|---|---|---|
| | | | | | | 18020,JF920758,HM488202,JF415914,HQ671678,JF957166,DQ431706,HQ671685,HM488127,JF488088,HM488117,JF488090,HM488212,KF647250,JF357959,JF957174,JF920755,GQ507479,KC736497,JN183897,AY701412,HM488139,HM488239,DQ080056,DQ256376,HM488152,JF488095,DQ666450,GQ507469,KC736499,HQ671672,JF920743,HM488120,D0164188,JN819321,JF920734,JXQ15515,D0164192,JF899535,HM488180,JN858070,DQ786573,GU82799 8,JX503090,AY68894 8,JN393308,HQ6717 04,KF234080,JN8193 24,DQ080066,JF9207 42,JF703164,JXQ416 34,AY278441,HM756 662,DQ666452,HM48 8240,HM488199,KC7 36494,DQ786572,JF9 57183,HM756658,HM 488162,JN183889,H M488155,JF920756,J F899528,DQ666448,J N183893,HM488225, JN819313,HM488169 ,GQ379160,HQ67166 8,DQ318019,JF48880 9 7,HM488167,HM4881 38,HQ671723,CS543 188,JN819315,HM75 6673,HM488153,HQ6 71690,HQ671697,HM 488238,HM488194,F J483549,JX503091,H M488158,JF719065,J F415917,DQ080057, |

| Taxonomy | NCBI Reference Sequence ID | Host | No. of Genomes | Lineage | Segment Count | Genbank Accession ID |
|---|---|---|---|---|---|---|
| | | | | | | HQ671729,DQ080055,JXQ41629,JX503096,DQ374651,HM051416,KC407667,DQ431705,JF957170,JF957178,JF920751,DQ431711,HM488121,HM488191,HM488215,HQ671726,HQ891011,JF719069,DQ005530,DQ164193,GQ507483,HM0671714,JF703163,DQ066451,HM488114,JF488094,HM488142,AB185914,HM488237,HQ671675,DQ164197,GQ507468,JF415928,HQ671701,JX503085,AY765264,HM488223,JN183891,JF730041,DQ164203,JF957173,HM488241,AY268133,KC736488,HM488176,HQ671686,JXQ15518,HM147824,JF957177,HM488188,DQ164201,AY490240,KF647252,AY603654,HM756676,HM488200,JF972636,HM488243,HM488178,HQ705678,CS568916,JN367277,HM488166,JF957172,HQ705676,D0431700,AY712947,J0700437,AY712948,JF415923,DQ080058,JN819312,JF719066,JF415916,HM488122,JN183895,JX503098,HM488244,JXQ41630,JX123030,HQ705659,GQ507471,HM756653,KC736491,DQ164191,HQ891009,HQ671710,JF920732,HM488168,JQ928175,DQ080063,JF415921,DQ |

| Taxonomy | NCBI Reference Sequence ID | Host | No. of Genomes | Lineage | Segment Count | Genbank Accession ID |
|---|---|---|---|---|---|---|
| West Nile virus | NC_009942 | vertebrates,invertebrates, human | 681 | Flaviviridae,Flavivirus,West Nile virus | — | 16419,JF899531,HQ671712,HQ705673,JF488092,FJ483548,JF920730,DQ431704,JF920760,HM488206,D0164196,HQ671709, JX503097,JX503086, AF481864,HQ671676, JF957163,JXQ15517, JN819306,HM488133 ,GQ379157,HQ67172 5,DQ080053,HM4882 03,KC736496,KF647 248,DQ118127,HM75 6650,KC954092,HM4 88214,HM488175,JN 183890,DQ080071,D 0431696,DQ431698, GU828004,GQ50747 6,HM488236,HM4882 24,HM488143,HQ671 715,HQ596519,HQ70 5663,JF920736,HM4 88161,AY646354,HM 488128,HM756669,J N819318 JN819317,FJ425721, HQ671721,JN858069 ,DQ080059,HQ67169 9,HM488219,JX5030 87,GQ507482,JF899 537,CS568918,JX503 084,HM488220,HM48 8126,DQ080062,DQ4 31701,JF957169,JF9 20749,EU068667,DQ 164187,JQ928174,H M448211,JF920754,J F415922,KF647249,J F957167,HQ671688, DQ080070,JF957180, JF357960,JF899530, KF588365,JF920746, JF415927,HQ671670, DQ411030,AF196835 ,JF488096,HM48820 1,HQ671673,JF48808 7,HM488165,AF4047 |

| Taxonomy | NCBI Reference Sequence ID | Host | No. of Genomes | Lineage | Segment Count | Genbank Accession ID |
|---|---|---|---|---|---|---|
| | | | | | | 56,GQ379156,JF730043,HM488173,JF488086,HQ671718,HQ671720,KC736498,HM488129,KC736486,JF415919,HM488181,AY262283,JF920752,H0671679,JF920759,KC711059,HM488132,GQ903680,KC711057,GQ379158,HM756672,JF957162,DQ080067,JF920733,HM488156,DQ431712,HM488135,JN819311,HM756649,HM488160,HQ705670,JF899534,JN819319,JF957182,JF920307,DQ431693,KC736493,HM756656,JX503092,HM488235,HM756663,JN183885,JF415930,JN819323,JXQ41628,HM756664,HM756651,DQ080069,JF415926,JQ700439,HM488179,JF957185,KC736489,KJ145832,HM488209,DQ411035,AB185916,JXQ15520,HQ671722,JF920747,HM488207,HQ705671,HM488170,G0379161,KC736487,HM488250,DQ374653,JF920738,JN819320,HQ671696,DQ411032,HQ671700,HM488164,HQ671707,HQ671687,GQ507473,KC736492,DQ080065,HQ705674,JF415918,JX503093,HM488233,HM488218,AY795965,HQ671692,HM488172,DQ377178,FJ151394,HM756657,AF260967,KC407673,DQ431 |

| Taxonomy | NCBI Reference Sequence ID | Host | No. of Genomes | Lineage | Segment Count | Genbank Accession ID |
|---|---|---|---|---|---|---|
| | | | | | | 694,HQ671691,JF415929,HM488185,DQ116961,HM488195,JF488089,JF957171,HM756677,FJ527738,HQ671702,JF899532,HM488197,GQ507484,JF357958,HM488159,DQ377180,HM488814,JQ700441,HQ67174,DQ431708,DQ411031,JF957176,JN183886,JXQ15519,HM488131,KF647251,HM488230,DQ080068,HM488232,DQ983578,HM756671,HM488124,JF415925,HQ671727,DQ374650,KC736501,DQ080051,JN81931 0,AF404753,HM488148,JF703162,HM488134,DQ431703,HM756660,HM756648,JF730042,JF719068,HM488182,JF415924,JF957184,HM488163,HQ705675,AY712945,JF920735,HM488251,HM488245,JF920729,HQ705672,JN716371,HM147823,JF920739,HM488189,HM488242,HM488246,DQ164204,HQ705660,HQ671719,GQ507472,JF719067,JXQ15521,FJ159129,JF957175,HQ671671,DQ164198,HM671695,DQ411034,KC407666,GQ507470,GQ507478,HM488217,HM488171,JX123031,HQ671708,AF206518,HQ671681,HM488118,JF920731,DQ374652,DQ164200,HQ671684,EU081844,JN |

| Taxonomy | NCBI Reference Sequence ID | Host | No. of Genomes | Lineage | Segment Count | Genbank Accession ID |
|---|---|---|---|---|---|---|
| | | | | | | 819305,JF920744,AY278442,JXQ15516,JF899536,KC736495,D0431702,HM488137,DQ431710,HM488213,AY532665,HM48812,JX503088,HM756654,JF415915,HQ705669,JF957179,HQ671728,JN819307,GQ507477,JN183887,KC736500,HQ891013,HM488149,HQ537483,JQ700438,GQ507481,JF730040,AY277252,JF957164,HM488123,EF571854,HM756668,HQ671732,JF957186,HM488130,AY268132,DQ164206,DQ43172,DQ164206,DQ431707,HQ671677,HM147822,AF404757,HQ671680,GU828002,JF921740,HM756670,EF657887,JF957168,JXQ41632,HQ671705,AY701413,AY660002,GU011992,AF404755,HM488210,JF784158,HM488154,HQ671694,JF920757,HM488150,JX503089,CS568919,DQ080054,JF920750,AY712946,AF260969,HM488192,CS568917,HM488147,KF179639,DQ411033,HM488183,HQ671689,HM488205,HM488252,JF920745,HQ671711,EF530047,GU828000,HQ671682,KF64725,3,HQ671683,JN183888,HQ671742,JF415920,HM488157,AY277251,JF957161,HM488216,FJ411043,GQ507480,JX503094,JF9 |

| Taxonomy | NCBI Reference Sequence ID | Host | No. of Genomes | Lineage | Segment Count | Genbank Accession ID |
|---|---|---|---|---|---|---|
| | | | | | | 57181,HQ891012,HM756667,HQ671713,HM488136,HQ671733,M488091,HM488187,JF488091,HM488187,HQ671674,AB18591 5,JF488093,GQ3791 59,HQ705677,DQ164 195,HM488248,KC73 6502,DQ164202,JF95 7165,HM488184,HQ6 71730,JF899533,DQ1 64186,JQ700442,HM 488228,DQ176637,A F404754,JXQ15522,D 0176636,HM488146, AB185917,KC601756 ,HM488222,HM75667 5,GU828003,HM7566 65,HM488151,HM488 115,HQ671706,GQ50 7474,GU828001,EU2 49803,AF533540,JXQ 41631,AF260968,KC 736490,DQ431699,D 0080064,HM488234, DQ164190,JN183896 ,HM488198,HM48825 3,JF707789,JF92073 7,HM488208,JXQ706 55,HQ671717,JN183 892,HQ671693,FJ159 131,HM756652,DQ41 1029,DQ080060,KF1 79640,DQ666449,JX 556213,HQ891010,H M488249,HM488119, JN183894,HM488204 ,DQ080052,HM48814 5,JQ700440,HM4881 93,HM488116,HM488 174,JF920753,DQ080 072,DQ377179,HM75 6666,GU827999,AY2 89214,HM488229,HM 488186,CS568914,H M756661,HM756678, JF703161,HM488227 ,HM756659,AF20254 |

| Taxonomy | NCBI Reference Sequence ID | Host | No. of Genomes | Lineage | Segment Count | Genbank Accession ID |
|---|---|---|---|---|---|---|
| | | | | | | 1,EU155484,DQ4316 |
| | | | | | | 95,HQ671716,AF317 |
| | | | | | | 203,DQ431709,JF920 |
| | | | | | | 741,DQ431697,HM48 |
| | | | | | | 8177,HM488221,JX5 |
| | | | | | | 03099,GQ507475,JX |
| | | | | | | 015523,DQ164194,H |
| | | | | | | 0671703,HM488140, |
| | | | | | | HQ671669,HM48823 |
| | | | | | | 1,DQ164205,FJ15913 |
| | | | | | | 0,HM488196,DQ1641 |
| | | | | | | 89,HM488190,JF920 |
| | | | | | | 748,HQ671724,JN81 |
| | | | | | | 9316,HM488141,JX5 |
| | | | | | | 03095,DQ080061,JF9 |
| | | | | | | 20306,HQ671698,JN |
| | | | | | | 819309,HM488226,H |
| | | | | | | M488247,JF920728,J |
| | | | | | | F899529,HM488254, |
| | | | | | | DQ318020,JF920758, |
| | | | | | | HM488202,JF415914 |
| | | | | | | ,HQ671678,JF957166 |
| | | | | | | ,DQ431706,HQ67168 |
| | | | | | | 5,HM488127,JF4880 |
| | | | | | | 88,HM488117,JF488 |
| | | | | | | 090,HM488212,KF64 |
| | | | | | | 7250,JF357959,JF95 |
| | | | | | | 7174,JF920755,GQ5 |
| | | | | | | 07479,KC736497,JN1 |
| | | | | | | 83897,AY701412,HM |
| | | | | | | 488139,HM488239,D |
| | | | | | | Q080056,DQ256376, |
| | | | | | | HM488152,JF488095 |
| | | | | | | ,DQ666450,GQ50746 |
| | | | | | | 9,KC736499,HQ6716 |
| | | | | | | 72,JF920743,HM488 |
| | | | | | | 120,DQ164188,JN81 |
| | | | | | | 9321,JF920734,JXQ1 |
| | | | | | | 5515,DQ164192,JF89 |
| | | | | | | 9535,HM488180,JN8 |
| | | | | | | 58070,DQ786573,GU |
| | | | | | | 827998,JX503090,AY |
| | | | | | | 688948,JN399308,H |
| | | | | | | 0671704,KF234080,J |
| | | | | | | N819324,DQ080066, |
| | | | | | | JF920742,JF703164, |
| | | | | | | JXQ41634,AY278441, |
| | | | | | | HM756662,DQ66645 |

| Taxonomy | NCBI Reference Sequence ID | Host | No. of Genomes | Lineage | Segment Count | Genbank Accession ID |
|---|---|---|---|---|---|---|
| | | | | | | 2,HM488240,HM4881 99,KC736494,DQ786 572,JF957183,HM75 6658,HM488162,JN1 83889,HM488155,JF 920756,JF899528,DO 666448,JN183893,H M488225,JN819313, HM488169,GQ37916 0,HQ671668,DQ3180 19,JF488097,HM488 167,HM488138,HQ67 1723,CS543188,JN81 9315,HM756673,HM4 88153,HQ671690,HQ 671697,HM488238,H M488194,FJ483549,J X503091,HM488158, JF719065,JF415917, DQ080057,HQ67172 9,DQ080055,JXQ416 29,JX503096,DQ374 651,HM051416,KC40 7667,DQ431705,JF95 7170,JF957178,JF92 0751,DQ431711,HM4 88121,HM488191,DQ 211652,HM488215,H 0671726,HQ891011, JF719069,DQ005530, DQ164193,GQ50748 3,HQ671714,JF70316 3,DQ666451,HM4881 14,JF488094,HM488 142,AB185914,HM48 8237,HQ671675,DQ1 64197,GQ507468,JF 415928,HQ671701,J X503085,AY765264, HM488223,JN183891 ,JF730041,DQ164203 ,JF957173,HM48824 1,AY268133,KC7364 88,HM488176,HQ671 686,JXQ155518,HM14 7824,JF957177,HM4 88188,DQ164201,AY 490240,KF647252,AY |

| Taxonomy | NCBI Reference Sequence ID | Host | No. of Genomes | Lineage | Segment Count | Genbank Accession ID |
|---|---|---|---|---|---|---|
| | | | | | | 603654,HM756676,HM488200,JF972636, HM488243,HM488178,HQ705678,CS56891 6,JN367277,HM488166,JF957172,HQ705 676,DQ431700,AY712947,JQ700437,AY71 2948,JF415923,DQ080058,JN819312,JF71 9066,JF415916,HM488122,JN183895,JX5 03098,HM488244,JX041630,JX123030,H 0705659,GQ507471, HM756653,KC736491,DQ164191,HQ89101 09,HQ671710,JF920732,HM488168,JQ928 175,DQ080063,JF415921,DQ164199,JF899 531,HQ671712,HQ705673,JF488092,FJ483 548,JF920730,DQ431704,JF920760,HM488206,DQ164196,HQ671709,JX503097,JX503086,AF481864,H0671676,JF957163,JXQ15517,JN819306,HM488133,GQ379157,HQ671725,DQ080053,HM488203,KC736496,KF64248,DQ118127,HM756650,KC954092,HM488214,HM488175,JN183890,DQ080071,DQ431696,DQ431698,GU828004, GQ507476,HM488236,HM488224,HM488143,HQ671715,HQ596519,HQ705663,JF920736,HM488161,AY646354,HM488128,HM756669,JN819318 |

-continued

| Taxonomy | NCBI Reference Sequence ID | Host | No. of Genomes | Lineage | Segment Count | Genbank Accession ID |
|---|---|---|---|---|---|---|
| West Nile virus H442 | NC_001563 | vertebrates,invertebrates, human | 1 | Flaviviridae,Flavivirus,West Nile virus | — | EF429200 |
| West Nile virus H442 | NC_009942 | vertebrates,invertebrates, human | 1 | Flaviviridae,Flavivirus,West Nile virus | — | EF429200 |
| West Nile virus SA381/00 | NC_001563 | vertebrates,invertebrates, human | 1 | Flaviviridae,Flavivirus,West Nile virus | — | EF429199 |
| West Nile virus SA381/00 | NC_009942 | vertebrates,invertebrates, human | 1 | Flaviviridae,Flavivirus,West Nile virus | — | EF429199 |
| West Nile virus SA93/01 | NC_001563 | vertebrates,invertebrates, human | 1 | Flaviviridae,Flavivirus,West Nile virus | — | EF429198 |
| West Nile virus SA93/01 | NC_009942 | vertebrates,invertebrates, human | 1 | Flaviviridae,Flavivirus,West Nile virus | — | EF429198 |
| West Nile virus SPU116/89 | NC_001563 | vertebrates,invertebrates, human | 1 | Flaviviridae,Flavivirus,West Nile virus | — | EF429197 |
| West Nile virus SPU116/89 | NC_009942 | vertebrates,invertebrates, human | 1 | Flaviviridae,Flavivirus,West Nile virus | — | EF429197 |
| West Nile virus strain 385-99 | NC_001563 | vertebrates,invertebrates, human | 5 | Flaviviridae,Flavivirus,West Nile virus | — | DQ066423,AY848695,AY842931,AY848696,AY848697 |
| West Nile virus strain 385-99 | NC_009942 | vertebrates,invertebrates, human | 5 | Flaviviridae,Flavivirus,West Nile virus | — | DQ066423,AY848695,AY842931,AY848696,AY848697 |
| West Nile virus strain PT5,2 | NC_001563 | vertebrates,invertebrates, human | 1 | Flaviviridae,Flavivirus,West Nile virus | — | AJ965628 |
| West Nile virus strain PT5,2 | NC_009942 | vertebrates,invertebrates, human | 1 | Flaviviridae,Flavivirus,West Nile virus | — | AJ965628 |
| West Nile virus strain PT6,16 | NC_001563 | vertebrates,invertebrates, human | 1 | Flaviviridae,Flavivirus,West Nile virus | — | AJ965626 |
| West Nile virus strain PT6,16 | NC_009942 | vertebrates,invertebrates, human | 1 | Flaviviridae,Flavivirus,West Nile virus | — | AJ965626 |
| West Nile virus strain PTRoxo | NC_001563 | vertebrates,invertebrates, human | 1 | Flaviviridae,Flavivirus,West Nile virus | — | AM404308 |
| West Nile virus strain PTRoxo | NC_009942 | vertebrates,invertebrates, human | 1 | Flaviviridae,Flavivirus,West Nile virus | — | AM404308 |
| Yaba-7 virus | NC_009896 | vertebrates,invertebrates, human | 1 | Bunyaviridae,Orthobunyavirus,Akabane virus | seg. S | AF362392 |
| Yellow fever virus | NC_002031 | vertebrates,invertebrates, human | 61 | Flaviviridae,Flavivirus,Yellow fever virus | — | JN811143,JF912190,JF912189,AY968064,JX898877,JF912186,U21056,JF912182,JF912181,JN811142,JF912179,AY968065,JF912180,JX898875,JX898880,JF912183,JX898870,U17066,JN628281,JX898872,DQ118157,JX503529,AF052439,U21055,JX898 |

-continued

| Taxonomy | NCBI Reference Sequence ID | Host | No. of Genomes | Lineage | Segment Count | Genbank Accession ID |
|---|---|---|---|---|---|---|
| | | | | | | 871,JF912188,JF912 187,KF769015,DQ23 5229,JX898868,AF05 2444,JF912184,JX89 8874,JX898879,GQ3 79162,JN811140,JX8 98876,JX898878,AF0 52438,JF912185,JN8 11141,JN628280,AY6 03338,GQ379163,JX 898881,AF052446,D 0100292,X15062,KF 769016,AF052437,AY 640589,XQ3700,JN62 0362,JX898869,U547 98,AF052445,JN6282 79,U17067,AY572535 ,JX898873,AF094612 |
| Yellow fever virus 17D/Tiantan | NC_002031 | vertebrates,invertebrates, human | 1 | Flaviviridae,Flavivirus,Yellow fever virus | — | FJ654700 |
| Yokose virus | NC_005039 | vertebrates,invertebrates, human | 1 | Flaviviridae,Flavivirus,Yokose virus | — | AB114858 |
| Zaliv Terpenia virus | NC_005214 | vertebrates,invertebrates, human | 1 | Bunyaviridae,Phlebovirus,Uukuniemi virus | seg. L | HM566191 |
| Zaliv Terpenia virus | NC_005220 | vertebrates,invertebrates, human | 1 | Bunyaviridae,Phlebovirus,Uukuniemi virus | seg. M | HM566193 |
| Zaliv Terpenia virus | NC_005221 | vertebrates,invertebrates, human | 1 | Bunyaviridae,Phlebovirus,Uukuniemi virus | seg. S | HM566192 |
| Zika virus | NC_012532 | vertebrates,invertebrates, human. | 1 | Flaviviridae,Flavivirus,Zika virus | — | AY632535 |

2. The kit of claim 1, wherein the probes are contained on a microarray.

3. The kit of claim 1, wherein the probes are 50-105 nucleotides in length.

* * * * *

SEQUENCE LISTING

<160> NUMBER OF SEQ ID NOS: 1

<210> SEQ ID NO 1
<211> LENGTH: 17
<212> TYPE: DNA
<213> ORGANISM: Artificial Sequence
<220> FEATURE:
<223> OTHER INFORMATION: SYNTHESIZED

```
<400> SEQUENCE: 1
gtttcccagt cacgata                                                17
```